US012559467B2

(12) United States Patent
Lee et al.

(10) Patent No.: US 12,559,467 B2
(45) Date of Patent: Feb. 24, 2026

(54) ORGANIC LIGHT EMITTING DEVICE

(71) Applicant: LG CHEM, LTD., Seoul (KR)

(72) Inventors: Hojung Lee, Daejeon (KR); Wanpyo Hong, Daejeon (KR); Jae Seung Ha, Daejeon (KR); Ji Young Choi, Daejeon (KR); Woochul Lee, Daejeon (KR); Joo Ho Kim, Daejeon (KR); Hoon Jun Kim, Daejeon (KR); Seonwoo Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 1066 days.

(21) Appl. No.: 17/617,579

(22) PCT Filed: Nov. 30, 2020

(86) PCT No.: PCT/KR2020/017338
§ 371 (c)(1),
(2) Date: Dec. 8, 2021

(87) PCT Pub. No.: WO2021/107744
PCT Pub. Date: Jun. 3, 2021

(65) Prior Publication Data

US 2023/0084250 A1 Mar. 16, 2023

(30) Foreign Application Priority Data

Nov. 29, 2019 (KR) ........................ 10-2019-0157386
Nov. 29, 2019 (KR) ........................ 10-2019-0157398
Nov. 29, 2019 (KR) ........................ 10-2019-0157427

(51) Int. Cl.
*H01L 51/54* (2006.01)
*C07C 15/28* (2006.01)
(Continued)

(52) U.S. Cl.
CPC ............ *C07D 307/91* (2013.01); *C07C 15/28* (2013.01); *C07F 5/027* (2013.01); *C07F 7/0812* (2013.01);
(Continued)

(58) Field of Classification Search
None
See application file for complete search history.

(56) References Cited

U.S. PATENT DOCUMENTS 9,634,254 B2 4/2017 Hamada
2010/0187983 A1 7/2010 Herron et al.
(Continued)

FOREIGN PATENT DOCUMENTS

CN 110492009 A 11/2019
CN 111647010 A 9/2020
(Continued)

*Primary Examiner* — Andrew K Bohaty
(74) *Attorney, Agent, or Firm* — Bryan Cave Leighton Paisner LLP

(57) ABSTRACT

An organic light emitting device including a light emitting layer, which comprises one or more of compounds represented by Formulae 1-1 to 1-3; and a compound represented by Formula 2.

[Formula 1-1]

[Formula 1-2]

[Formula 1-3]

(Continued)

-continued

[Formula 2]

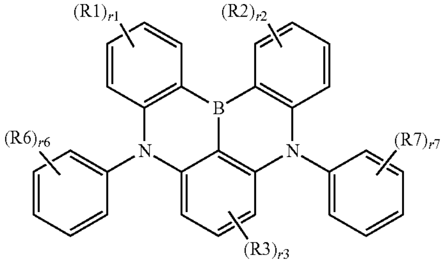

12 Claims, 1 Drawing Sheet

(51) Int. Cl.

| | |
|---|---|
| ***C07D 307/91*** | (2006.01) |
| ***C07F 5/02*** | (2006.01) |
| ***C07F 7/08*** | (2006.01) |
| ***C09K 11/06*** | (2006.01) |
| ***H10K 85/00*** | (2023.01) |
| ***H10K 85/40*** | (2023.01) |
| ***H10K 85/60*** | (2023.01) |
| *H10K 50/11* | (2023.01) |
| *H10K 50/12* | (2023.01) |
| *H10K 101/00* | (2023.01) |

(52) U.S. Cl.

CPC .............. *C09K 11/06* (2013.01); *H10K 85/00* (2023.02); *H10K 85/40* (2023.02); *H10K 85/615* (2023.02); *H10K 85/626* (2023.02); *H10K 85/657* (2023.02); *H10K 85/6572* (2023.02); *H10K 85/6574* (2023.02); *H10K 85/658* (2023.02); *C07B 2200/05* (2013.01); *C07C 2603/24* (2017.05); *C09K 2211/1007* (2013.01); *C09K 2211/1011* (2013.01); *C09K 2211/1018* (2013.01); *H10K 50/11* (2023.02); *H10K 50/12* (2023.02); *H10K 2101/90* (2023.02)

(56) References Cited

U.S. PATENT DOCUMENTS

| | | | |
|---|---|---|---|
| 2015/0108448 | A1 | 4/2015 | Dai et al. |
| 2015/0236274 | A1 | 8/2015 | Hatakeyama et al. |
| 2017/0025608 | A1 | 1/2017 | Herron et al. |
| 2018/0094000 | A1 | 4/2018 | Hatakeyama et al. |
| 2018/0301629 | A1 | 10/2018 | Hatakeyama et al. |
| 2019/0115538 | A1 | 4/2019 | Lim et al. |
| 2019/0181350 | A1 | 6/2019 | Hatakeyama et al. |
| 2019/0207112 | A1 | 7/2019 | Hatakeyama et al. |
| 2019/0305227 | A1 | 10/2019 | Yoon et al. |
| 2020/0052212 | A1 | 2/2020 | Tasaki et al. |
| 2020/0058885 | A1 | 2/2020 | Hong et al. |
| 2020/0176679 | A1 | 6/2020 | Jeong et al. |
| 2020/0185626 | A1 | 6/2020 | Yuuki |
| 2020/0220083 | A1 | 7/2020 | Hatakeyama et al. |
| 2021/0036233 | A1 | 2/2021 | Joo et al. |
| 2021/0050547 | A1 | 2/2021 | Li et al. |
| 2021/0167293 | A1 | 6/2021 | Joo et al. |
| 2021/0184121 | A1 | 6/2021 | Suh et al. |
| 2022/0006019 | A1 | 1/2022 | Kim et al. |

FOREIGN PATENT DOCUMENTS

| | | | | | |
|---|---|---|---|---|---|
| JP | 2018-043984 | A | | 3/2018 | |
| KR | 10-2011-0126950 | A | | 11/2011 | |
| KR | 10-2012-0058602 | A | | 6/2012 | |
| KR | 10-2015-0011347 | A | | 1/2015 | |
| KR | 10-2018-0112721 | A | | 10/2018 | |
| KR | 10-2019-0051867 | A | | 5/2019 | |
| KR | 10-2019-0078541 | A | | 7/2019 | |
| KR | 10-2019-0101900 | A | | 9/2019 | |
| KR | 10-2019-0113498 | A | | 10/2019 | |
| KR | 10-2019-0127529 | A | | 11/2019 | |
| KR | 10-2020-0003741 | A | | 1/2020 | |
| KR | 10-2020-0090158 | A | | 7/2020 | |
| WO | 2019/102936 | A1 | | 5/2019 | |
| WO | 2019/218969 | A1 | | 11/2019 | |
| WO | 2020/054676 | A1 | | 3/2020 | |
| WO | 2020080872 | A | | 4/2020 | |
| WO | WO-2020085829 | A1 | * | 4/2020 | ............. C09K 11/06 |

* cited by examiner

ORGANIC LIGHT EMITTING DEVICE

CROSS-REFERENCE TO RELATED APPLICATION(S)

This application is a National Phase entry pursuant to 35 U.S.C § 371 of International Application No. PCT/KR2020/017338 filed on Nov. 30, 2020, and claims priority to and the benefit of Korean Patent Application Nos. 10-2019-0157398, 10-2019-0157386, and 10-2019-0157427 filed on Nov. 29, 2019, the disclosures of which are incorporated herein by reference in their entireties.

FIELD OF DISCLOSURE

The present specification relates to an organic light emitting device.

BACKGROUND ART

In general, an organic light emitting phenomenon refers to a phenomenon in which electric energy is converted into light energy by using an organic material.

An organic light emitting device using the organic light emitting phenomenon usually has a structure including an anode, a cathode, and an organic material layer interposed therebetween. Here, the organic material layer has in many cases a multi-layered structure composed of different materials in order to improve the efficiency and stability of the organic light emitting device, and for example, may be composed of a hole injection layer, a hole transport layer, a light emitting layer, an electron transport layer, an electron injection layer, and the like. In such a structure of the organic light emitting device, if a voltage is applied between the two electrodes, holes are injected from the anode into the organic material layer and electrons are injected from the cathode into the organic material layer, and when the injected holes and electrons meet each other, an exciton is formed, and light is emitted when the exciton falls down again to a ground state.

There is a continuous need for developing a new material for the aforementioned organic light emitting device.

RELATED ARTS (Patent Document 1) Korean Patent Application Laid-Open No. 10-2015-0011347

SUMMARY

The present specification provides an organic light emitting device.

The present specification provides an organic light emitting device including: an anode; a cathode; and an organic material layer including a light emitting layer provided between the anode and the cathode, wherein the light emitting layer includes one or more of compounds represented by any one of the following Formulae 1-1 to 1-3 and a compound represented by the following Formula 2.

[Formula 1-1]

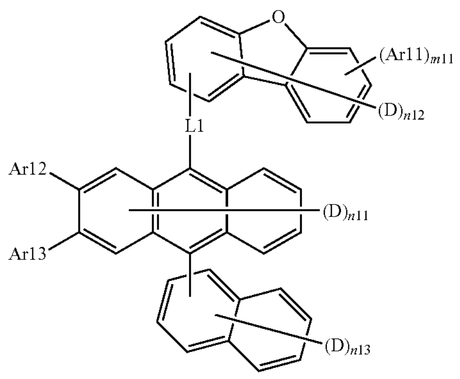

[Formula 1-2]

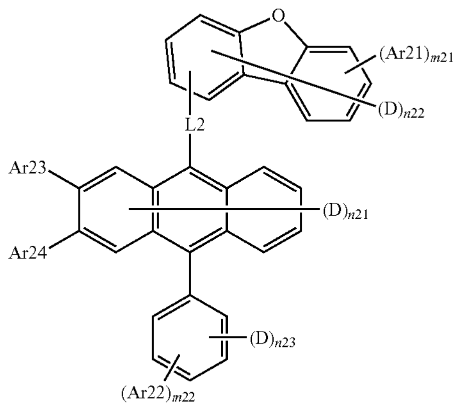

[Formula 1-3]

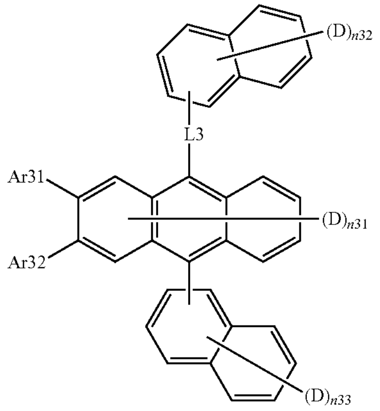

[Formula 2]

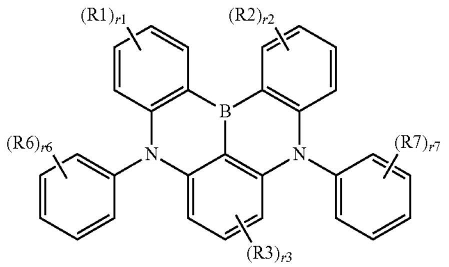

In Formulae 1-1 to 1-3 and 2,

L1 to L3 are the same as or different from each other, and are each independently a direct bond; or a substituted or unsubstituted arylene group, D is deuterium, n11, n21, and n31 are each an integer from 0 to 6, n12, n13, n22, n32, and n33 are each an integer from 0 to 7, and n23 is an integer from 0 to 5, Ar11, Ar21, and Ar22 are the same as or different from each other, and are each independently a substituted or unsubstituted aryl group, Ar12, Ar13, Ar23, Ar24, Ar31, and Ar32 are the same as or different from each other, and are each independently hydrogen; deuterium; a substituted or unsubstituted aryl group; or a substituted or unsubstituted heteroaryl group, m11 and m21 are an integer from 0 to 4, m22 is an integer from 0 to 5, and when m11, m21, and m22 are each 2 or higher, substituents in the parenthesis are the same as or different from each other, the compounds of Formulae 1-1 to 1-3 each have at least one or more deuteriums, R1 to R3, R6, and R7 are the same as or different from each other, and are each independently hydrogen; deuterium; a halogen group; a cyano group; a substituted or unsubstituted alkyl group; a substituted or unsubstituted cycloalkyl group; a substituted or unsubstituted silyl group; a substituted or unsubstituted alkenyl group; a substituted or unsubstituted aryl group; a substituted or unsubstituted heterocyclic group; a substituted or unsubstituted alkoxy group; a substituted or unsubstituted aryloxy group; a substituted or unsubstituted alkylthio group; a substituted or unsubstituted arylthio group; or a substituted or unsubstituted amine group, or a group represented by the following Formula 2-A or 2-B, or are bonded to an adjacent substituent to form a substituted or unsubstituted ring, r1 and r2 are an integer from 0 to 4, r3 is an integer from 0 to 3, r6 and r7 are an integer from 0 to 5, and when r1 to r3, r6, and r7 are each 2 or higher, substituents in the parenthesis are the same as or different from each other,

[Formula 2-A]

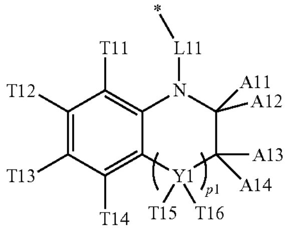

[Formula 2-B]

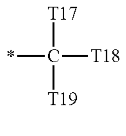

in Formulae 2-A and 2-B,

* is a bonding site,

T11 to T19 are the same as or different from each other, and are each independently hydrogen; deuterium; a halogen group; a cyano group; a substituted or unsubstituted alkyl group; a substituted or unsubstituted cycloalkyl group; a substituted or unsubstituted silyl group; a substituted or unsubstituted alkenyl group; a substituted or unsubstituted aryl group; a substituted or unsubstituted heterocyclic group; a substituted or unsubstituted alkoxy group; a substituted or unsubstituted aryloxy group; a substituted or unsubstituted alkylthio group; a substituted or unsubstituted arylthio group; or a substituted or unsubstituted amine group, or are bonded to an adjacent substituent to form a substituted or unsubstituted ring, at least one of T17 to T19 is a substituted or unsubstituted aryl group, A11 to A14 are the same as or different from each other, and are each independently hydrogen; deuterium; a halogen group; a cyano group; a substituted or unsubstituted alkyl group; a substituted or unsubstituted cycloalkyl group; a substituted or unsubstituted silyl group; a substituted or unsubstituted alkenyl group; a substituted or unsubstituted aryl group; a substituted or unsubstituted heterocyclic group; a substituted or unsubstituted alkoxy group; a substituted or unsubstituted aryloxy group; a substituted or unsubstituted alkylthio group; a substituted or unsubstituted arylthio group; or a substituted or unsubstituted amine group, or are bonded to an adjacent substituent to form a substituted or unsubstituted aliphatic hydrocarbon ring, L11 is a direct bond; or a substituted or unsubstituted arylene group, p1 is 0 or 1, and Y1 is C or Si.

Advantageous Effects

The organic light emitting device described in the present specification has a low driving voltage and has excellent efficiency characteristics and an excellent service life by including one or more of compounds represented by any one of Formulae 1-1 to 1-3 and a compound represented by Formula 2 in a light emitting layer.

DESCRIPTION OF REFERENCE NUMERALS

Figure 1:
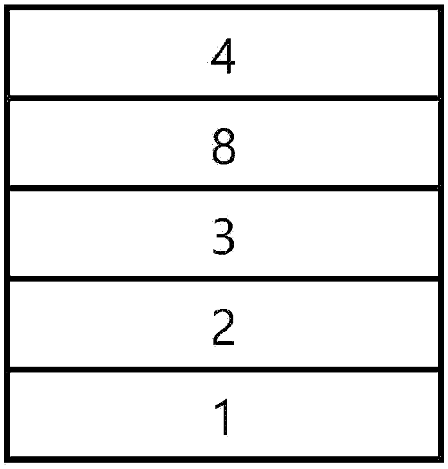
FIGS. 1 and 2 illustrate an organic light emitting device according to an exemplary embodiment of the present specification.

1: Substrate
2: Anode
3: Light emitting layer
4: Cathode
5: Hole injection layer
6: Hole transport layer
7: Electron blocking layer
8: Electron transport layer
9: Electron injection layer

DETAILED DESCRIPTION

Hereinafter, the present specification will be described in more detail.

The present specification provides an organic light emitting device including a light emitting layer including compounds represented by any one of Formulae 1-1 to 1-3 and a compound represented by Formula 2. Specifically, the compounds represented by any one of Formulae 1-1 to 1-3 and the compound represented by Formula 2 are included as a host and a dopant, respectively.

The compound represented by Formula 2 has excellent light emission characteristics due to a narrow full-width at half-maximum, but the service life performance thereof is slightly insufficient.

Since the structures of Formulae 1-1 to 1-3 have good movement and injection of holes and electrons, the driving voltage is stabilized, so that the compounds represented by Formulae 1-1 to 1-3 have low voltage and high efficiency characteristics when used as a host of a light emitting layer of an organic light emitting device.

Further, Formulae 1-1 to 1-3 include deuterium. When the compounds of Formulae 1-1 to 1-3 include deuterium, the service life of a device is improved. Specifically, when hydrogen is replaced with deuterium, chemical properties of the compound are rarely changed. However, since the atomic weight of deuterium is twice that of hydrogen, physical properties of a deuterated compound may be changed. As an example, a compound substituted with deuterium has a lower level of vibrational energy. Quantum calculations revealed changes in the vibrational energy according to the deuterium substitution rate of the compound, but a vibrational energy of about 2 kcal/mol was decreased constantly for each number of deuterium substitutions. Accordingly, the compound substituted with deuterium may prevent a decrease in quantum efficiency caused by a decrease in intermolecular Van der Waals force or a collision due to intermolecular vibration. In addition, the stability of the compound may be improved by a C-D bond, which is stronger than a C—H bond.

The organic light emitting device of the present invention may include compounds represented by Formulae 1-1 to 1-3 and a compound represented by Formula 2 together, thereby improving a service life problem while maintaining excellent light emission characteristics of the compound of Formula 2.

The compounds of Formulae 1-1 to 1-3 including deuterium may be prepared by a publicly-known deuteration reaction. According to an exemplary embodiment of the present specification, the compounds represented by Formulae 1-1 to 1-3 may be formed using a deuterated compound as a precursor, or deuterium may also be introduced into a compound via a hydrogen-deuterium exchange reaction in the presence of an acid catalyst using a deuterated solvent.

In the present specification, N % substitution with deuterium means that N % of hydrogen available in the corresponding structure is substituted with deuterium. For example, 25% substitution of dibenzofuran with deuterium means that two of eight hydrogens of dibenzofuran are substituted with deuteriums.

In the present specification, the degree of deuteration may be confirmed by a publicly-known method such as nuclear magnetic resonance spectroscopy ($^1$H NMR) or GC/MS.

In Formulae 1-1 to 1-3 and 2 of the present specification, the substitution includes being substituted with deuterium even when the substituted substituent is not specified.

In the present specification, * or

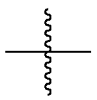

means a moiety that is fused or linked.

In the present specification, Cn means n carbon atoms.

In the present specification, "Cn-Cm" means "n to m carbon atoms".

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a cyano group (—CN); a silyl group; a boron group; an alkyl group; a cycloalkyl group; an aryl group; and a heterocyclic group, being substituted with a substituent to which two or more substituents among the exemplified substituents are linked, or having no substituent. For example, "the substituent to which two or more substituents are linked" may be a biphenyl group. That is, the biphenyl group may also be an aryl group, and may be interpreted as a substituent to which two phenyl groups are linked.

In an exemplary embodiment of the present invention, the "substituted or unsubstituted" means being substituted with one or more substituents selected from the group consisting of deuterium; a halogen group; a cyano group (—CN); a silyl group; a C1-C20 alkyl group; a C3-C60 cycloalkyl group; a C6-C60 aryl group; and a C2-C60 heterocyclic group, being substituted with a substituent to which two or more groups selected from the above group are linked, or having no substituent.

In an exemplary embodiment of the present invention, the "substituted or unsubstituted" means being substituted with one or more substituents selected from the group consisting of deuterium; a halogen group; a cyano group (—CN); a silyl group; a C1-C10 alkyl group; a C3-C30 cycloalkyl group; a C6-C30 aryl group; and a C2-C30 heterocyclic group, being substituted with a substituent to which two or more groups selected from the above group are linked, or having no substituent.

In an exemplary embodiment of the present invention, the "substituted or unsubstituted" means being substituted with one or more substituents selected from the group consisting of deuterium; a halogen group; a cyano group (—CN); a silyl group; a C1-C6 alkyl group; a C3-C20 cycloalkyl group; a C6-C20 aryl group; and a C2-C20 heterocyclic group, being substituted with a substituent to which two or more groups selected from the above group are linked, or having no substituent.

In the present specification, the fact that two or more substituents are linked indicates that hydrogen of any one substituent is changed into another substituent. For example, an isopropyl group and a phenyl group may be linked to each other to become a substituent of

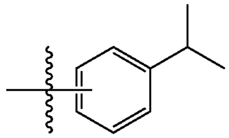

or

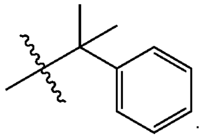

.

In the present specification, the case where three substituents are linked to one another includes not only a case where (Substituent 1)-(Substituent 2)-(Substituent 3) are consecutively linked to one another, but also a case where (Substituent 2) and (Substituent 3) are linked to (Substituent 1). For example, two phenyl groups and an isopropyl group may be linked to each other to become a substituent of

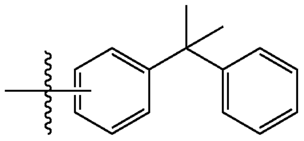

or

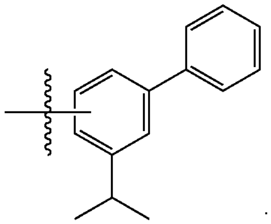

.

The same also applies to the case where four or more substituents are linked to one another.

In the present specification, "substituted with A or B" includes not only the case of being substituted with A alone or with B alone, but also the case of being substituted with A and B.

In the present specification, an alkyl group may be straight-chained or branched, and the number of carbon atoms thereof is not particularly limited, but is preferably 1 to 20. Specifically, the number of carbon atoms is more preferably 1 to 10; or 1 to 6. Specific examples thereof include: a methyl group; an ethyl group; a propyl group; an n-propyl group; an isopropyl group; a butyl group; an n-butyl group; an isobutyl group; a tert-butyl group; a sec-butyl group; a 1-methylbutyl group; a 2-methylbutyl group; a 1-ethylbutyl group; a pentyl group; an n-pentyl group; an isopentyl group; a neopentyl group; a tert-pentyl group; a hexyl group; an n-hexyl group; a 1-methylpentyl group; a 2-methylpentyl group; a 4-methylpentyl group; a 3,3-dimethylbutyl group; a 2-ethylbutyl group; a heptyl group; an n-heptyl group; a 1-methylhexyl group; a cyclopentylmethyl group; a cyclohexylmethyl group; an octyl group; an n-octyl group; a tert-octyl group; a 1-methylheptyl group; a 2-ethylhexyl group; a 2-propylpentyl group; an n-nonyl group; a 2,2-dimethylheptyl group; a 1-ethylpropyl group; a tert-amyl group (a 1,1-dimethylpropyl group); an isohexyl group; a 2-methylpentyl group; a 4-methylhexyl group; a 5-methylhexyl group; and the like, but are not limited thereto.

In the present specification, the alkoxy group is one in which an alkyl group is linked to an oxygen atom, the alkylthio group is one in which an alkyl group is linked to a sulfur atom, and the above-described description on the alkyl group may be applied to the alkyl group of the alkoxy group and the alkylthio group.

In the present specification, an alkenyl group may be straight-chained or branched, and the number of carbon atoms thereof is not particularly limited, but is preferably 2 to 30; 2 to 20; 2 to 10; or 2 to 5. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but has preferably 3 to 60 carbon atoms, and according to an exemplary embodiment, the number of carbon atoms of the cycloalkyl group is 3 to 30. According to another exemplary embodiment, the number of carbon atoms of the cycloalkyl group is 3 to 20. According to yet another exemplary embodiment, the number of carbon atoms of the cycloalkyl group is 3 to 6. The cycloalkyl group includes not only a single ring group, but also a double ring group such as a bridgehead, a fused ring, and a spiro ring. Specific examples thereof include a cyclopropyl group, a cyclobutyl group, a cyclopentyl group, a cyclohexyl group, a cycloheptyl group, a cyclooctyl group, an adamantyl group, and the like, but are not limited thereto.

In the present specification, cycloalkene is a ring group which has a double bond present in a hydrocarbon ring, but is not aromatic, and the number of carbon atoms thereof is not particularly limited, but may be 3 to 60, and may be 3 to 30 according to an exemplary embodiment. The cycloalkene includes not only a single ring group, but also a double ring group such as a bridgehead, a fused ring, and a spiro ring. Examples of the cycloalkene include cyclopropene, cyclobutene, cyclopentene, cyclohexene, and the like, but are not limited thereto.

In the present specification, a silyl group may be represented by a formula of $—SiY_{11}Y_{12}Y_{13}$, and the $Y_{11}$, $Y_{12}$, and $Y_{13}$ may be each hydrogen; a substituted or unsubstituted alkyl group; or a substituted or unsubstituted aryl group. Specific examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, an amine group may be selected from the group consisting of $—NH_2$; an alkylamine group; an alkylarylamine group; an arylamine group; an arylheteroarylamine group; an alkylheteroarylamine group; and a heteroarylamine group, and the number of carbon atoms thereof is not particularly limited, but is preferably 1 to 60. In the case of an arylamine group, the number of carbon atoms thereof is 6 to 60. According to another exemplary embodiment, the number of carbon atoms of the arylamine group is 6 to 40. Specific examples of the amine group include a methylamine group; a dimethylamine group; an ethylamine group; a diethylamine group; a phenylamine group; a naphthylamine group; a biphenylamine group; an anthracenylamine group; a 9-methylanthracenylamine group; a diphenylamine group; an N-phenylnaphthylamine group; a ditolylamine group; an N-phenyltolylamine group; a triphenylamine group; an N-phenylbiphenylamine group; an N-phenylnaphthylamine group; an N-biphenylnaphthylamine group; an N-naphthylfluorenylamine group; an N-phenylphenanthrenylamine group; an N-biphenylphenanthrenylamine group; an N-phenylfluorenylamine group; an N-phenylterphenylamine group; an N-phenanthrenylfluorenylamine group; an N-biphenylfluorenylamine group; an N-(4-(tert-butyl)phenyl)-N-phenylamine group; an N,N-bis(4-(tert-butyl)phenyl)amine group; an N,N-bis(3-(tert-butyl)phenyl)amine group, and the like, but are not limited thereto.

In the present specification, the alkylamine group means an amine group in which an alkyl group is substituted with N of the amine group, and includes a dialkylamine group, an alkylarylamine group, and an alkylheteroarylamine group.

In the present specification, the arylamine group means an amine group in which an aryl group is substituted with N of the amine group, and includes a diarylamine group, an arylheteroarylamine group, and an alkylarylamine group.

In the present specification, the heteroarylamine group means an amine group in which a heteroaryl group is substituted with N of the amine group, and includes a diheteroarylamine group, an arylheteroarylamine group, and an alkylheteroarylamine group.

In the present specification, an alkylarylamine group means an amine group in which an alkyl group and an aryl group are substituted with N of the amine group.

In the present specification, an arylheteroarylamine group means an amine group in which an aryl group and a heteroaryl group are substituted with N of the amine group.

In the present specification, an alkylheteroarylamine group means an amine group in which an alkyl group and a heteroaryl group are substituted with N of the amine group.

In the present specification, an aryl group is not particularly limited, but has preferably 6 to 60 carbon atoms, and may be a monocyclic aryl group or a polycyclic aryl group. According to an exemplary embodiment, the number of carbon atoms of the aryl group is 6 to 30. According to an exemplary embodiment, the number of carbon atoms of the aryl group is 6 to 20. Examples of a monocyclic aryl group as the aryl group include a phenyl group, a biphenyl group, a terphenyl group, and the like, but are not limited thereto. Examples of the polycyclic aryl group include a naphthyl group, an anthracenyl group, a phenanthrenyl group, a pyrenyl group, a perylenyl group, a triphenyl group, a chrysenyl group, a fluorenyl group, and the like, but are not limited thereto.

In the present specification, No. 9 carbon atom (C) of a fluorenyl group may be substituted with an alkyl group, an aryl group, or the like, and two substituents may be bonded to each other to form a spiro structure such as cyclopentane or fluorene.

In the present specification, the substituted aryl group may also include a form in which an aliphatic ring is fused to the aryl group. For example, a tetrahydronaphthalene group, a dihydroindene group and a dihydroanthracene group having the following structures are included in the substituted aryl group. In the following structure, one of the carbons of a benzene ring may be linked to another position.

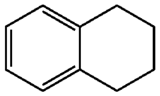
tetrahydronaphthalene

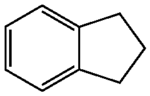
dihydroindene

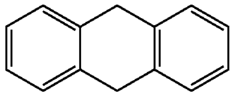
dihydroanthracene

In the present specification, a fused hydrocarbon ring group means a fused ring group of an aromatic hydrocarbon ring and an aliphatic hydrocarbon ring, and is a form in which the aromatic hydrocarbon ring and the aliphatic hydrocarbon ring are fused. Examples of the fused ring group of the aromatic hydrocarbon ring and the aliphatic hydrocarbon ring include a tetrahydronaphthalene group, a dihydroindene group, and a dihydroanthracene group, but are not limited thereto.

In the present specification, the alkylaryl group means an aryl group substituted with an alkyl group, and a substituent other than the alkyl group may be further linked.

In the present specification, an arylalkyl group means an alkyl group substituted with an aryl group, and a substituent other than the aryl group may be further linked.

In the present specification, the aryloxy group is one in which an aryl group is linked to an oxygen atom, the arylthio group is one in which an aryl group is linked to a sulfur atom, and the above-described description on the aryl group may be applied to the aryl group of the aryloxy group and the arylthio group. An aryl group of an aryloxy group is the same as the above-described examples of the aryl group. Specifically, examples of the aryloxy group include a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group, and the like, and examples of the arylthioxy group include a phenylthioxy group, a 2-methylphenylthioxy group, a 4-tert-butylphenylthioxy group, and the like, but the examples are not limited thereto.

In the present specification, a heterocyclic group is a cyclic group including one or more of N, O, P, S, Si, and Se as a heteroatom, and the number of carbon atoms thereof is not particularly limited, but is preferably 2 to 60. According to an exemplary embodiment, the number of carbon atoms of the heterocyclic group is 2 to 30. According to an exemplary embodiment, the number of carbon atoms of the heterocyclic group is 2 to 20. Examples of the heterocyclic group include a pyridyl group; a quinoline group; a thiophene group; a dibenzothiophene group; a furan group; a dibenzofuran group; a naphthobenzofuran group; a carbazole group; a benzocarbazole group; a naphthobenzothiophene group; a dibenzosilole group; a naphthobenzosilole group; a hexahydrocarbazole group; dihydroacridine group; a dihydrodibenzoazasiline group; a phenoxazine group; a phenothiazine group; a dihydrodibenzoazasiline group; a spiro(dibenzosilole-dibenzoazasiline) group; a spiro(acridine-fluorene) group, and the like, but are not limited thereto.

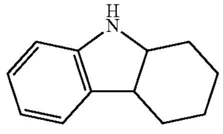
hexahydrocarbazole

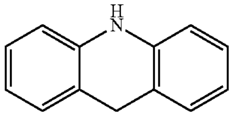
dihydroacridine

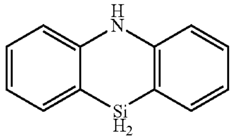
dibenzoazasiline

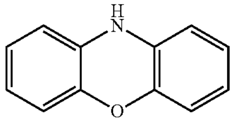
phenoxazine

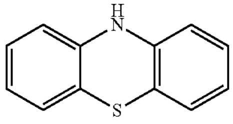
phenothiazine

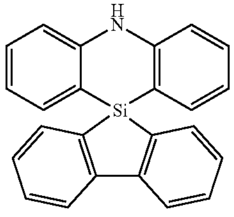
splro[dlbenzosllole-dlbenzoazaslllne]

-continued

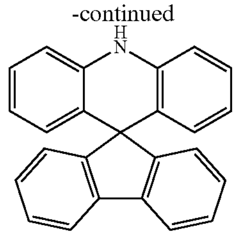

splro[acrldlne-fluorene]

In the present specification, the above-described description on the heterocyclic group may be applied to a heteroaryl group except for being aromatic.

In the present specification, an aromatic hydrocarbon ring means a hydrocarbon ring in which pi electrons are completely conjugated and are planar, and the description on the aryl group may be applied to an aromatic hydrocarbon ring except for being divalent. The number of carbon atoms of the aromatic hydrocarbon ring may be 6 to 60; 6 to 30; 6 to 20; or 6 to 10.

In the present specification, an aliphatic hydrocarbon ring has a cyclically bonded structure, and means a non-aromatic ring. Examples of the aliphatic hydrocarbon ring include cycloalkane or cycloalkene, and the above-described description on the cycloalkyl group or cycloalkenyl group may be applied to the aliphatic hydrocarbon ring except for being divalent. The number of carbon atoms of the aliphatic hydrocarbon ring may be 3 to 60; 3 to 30; 3 to 20; 3 to 10; 5 to 50; 5 to 30; 5 to 20; 5 to 10; or 5 to 6. Further, a substituted aliphatic hydrocarbon ring also includes an aliphatic hydrocarbon ring in which aromatic rings are fused.

In the present specification, a fused ring of an aromatic hydrocarbon ring and an aliphatic hydrocarbon ring means that an aromatic hydrocarbon ring and an aliphatic hydrocarbon ring form a fused ring. Examples of the fused ring of the aromatic ring and the aliphatic ring include a 1,2,3,4-tetrahydronaphthalene group, a 2,3-dihydro-1H-indene group, and the like, but are not limited thereto.

In the present specification, the "adjacent" group may mean a substituent substituted with an atom directly linked to an atom in which the corresponding substituent is substituted, a substituent disposed to be sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other. In addition, substituents (four in total) linked to two consecutive carbons in an aliphatic ring may be interpreted as "adjacent" groups.

In the present specification, the "adjacent groups are bonded to each other to form a ring" among the substituents means that a substituent is bonded to an adjacent group to form a substituted or unsubstituted hydrocarbon ring; or a substituted or unsubstituted hetero ring.

In the present specification, "a five-membered or six-membered ring formed by bonding adjacent groups" means that a ring including a substituent participating in the ring formation is five-membered or six-membered. It is possible to include an additional ring fused to the ring including the substituent participating in the ring formation.

In the present specification, when a substituent of an aromatic hydrocarbon ring or an aryl group is bonded to an adjacent substituent to form an aliphatic hydrocarbon ring, the aliphatic hydrocarbon ring includes two pi electrons (carbon-carbon double bond) of an aromatic hydrocarbon ring or an aryl group, even though a double bond is not specified.

In the present specification, the above-described description on the aryl group may be applied to an arylene group except for being divalent.

In the present specification, the above-described description on the cycloalkyl group may be applied to a cycloalkylene group except for being divalent.

Hereinafter, the following Formulae 1-1 to 1-3 will be described.

[Formula 1-1]

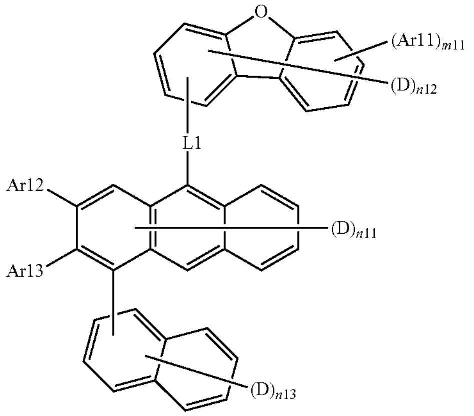

[Formula 1-2]

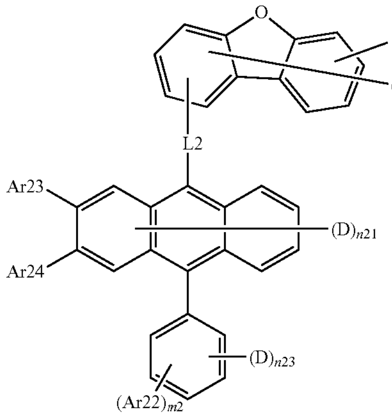

[Formula 1-3]

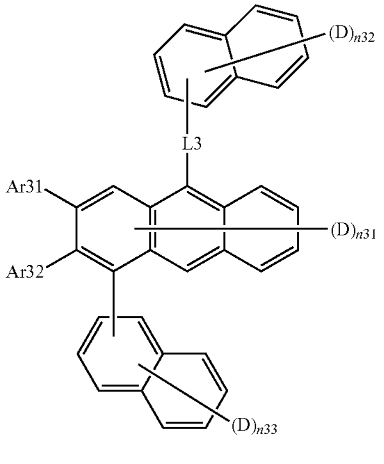

In an exemplary embodiment of the present specification, Formulae 1-1 to 1-3 each include at least one or more deuteriums.

In an exemplary embodiment of the present specification, Ar11, Ar21, and Ar22 are the same as or different from each other, and are each independently a substituted or unsubstituted aryl group.

In an exemplary embodiment of the present application, Ar11, Ar21, and Ar22 are the same as or different from each other, and are each independently a substituted or unsubstituted C6-C30 aryl group.

In an exemplary embodiment of the present specification, Ar11, Ar21, and Ar22 are the same as or different from each other, and are each independently a C6-C20 aryl group which is unsubstituted or substituted with deuterium or a C1-C10 alkyl group.

In an exemplary embodiment of the present specification, Ar11, Ar21, and Ar22 are the same as or different from each other, and are each independently a C6-C13 aryl group which is unsubstituted or substituted with deuterium or a C1-C6 alkyl group.

In an exemplary embodiment of the present specification, Ar11, Ar21, and Ar22 are the same as or different from each other, and are each independently a C6-C10 aryl group which is unsubstituted or substituted with deuterium.

In an exemplary embodiment of the present specification, Ar11, Ar21, and Ar22 are the same as or different from each other, and are each independently a phenyl group which is unsubstituted or substituted with deuterium; a biphenyl group which is unsubstituted or substituted with deuterium; a naphthyl group which is unsubstituted or substituted with deuterium; or a fluorenyl group which is unsubstituted or substituted with deuterium or a methyl group.

In an exemplary embodiment of the present specification, Ar11, Ar21, and Ar22 are the same as or different from each other, and are each independently a phenyl group which is unsubstituted or substituted with deuterium; a 1-naphthyl group which is unsubstituted or substituted with deuterium; or a 2-naphthyl group which is unsubstituted or substituted with deuterium.

In an exemplary embodiment of the present specification, Ar11 is a phenyl group which is unsubstituted or substituted with deuterium; a biphenyl group which is unsubstituted or substituted with deuterium; or a naphthyl group which is unsubstituted or substituted with deuterium.

In an exemplary embodiment of the present specification, Ar11 is a phenyl group which is unsubstituted or substituted with deuterium; a 1-naphthyl group which is unsubstituted or substituted with deuterium; or a 2-naphthyl group which is unsubstituted or substituted with deuterium.

In an exemplary embodiment of the present specification, Ar21 and Ar22 are the same as or different from each other, and are each independently a phenyl group which is unsubstituted or substituted with deuterium; a biphenyl group which is unsubstituted or substituted with deuterium; a naphthyl group which is unsubstituted or substituted with deuterium; or a fluorenyl group which is unsubstituted or substituted with deuterium or a methyl group.

In an exemplary embodiment of the present specification, Ar21 and Ar22 are the same as or different from each other, and are each independently a phenyl group which is unsubstituted or substituted with deuterium; a 1-naphthyl group which is unsubstituted or substituted with deuterium; or a 2-naphthyl group which is unsubstituted or substituted with deuterium.

In an exemplary embodiment of the present specification, one of Ar12 and Ar13 is hydrogen; or deuterium, and the other is a substituted or unsubstituted aryl group.

In an exemplary embodiment of the present specification, one of Ar12 and Ar13 is hydrogen; or deuterium, and the other is a substituted or unsubstituted C6-C30 aryl group.

In an exemplary embodiment of the present specification, one of Ar12 and Ar13 is hydrogen; or deuterium, and the other is a C6-C20 aryl group which is unsubstituted or substituted with deuterium.

In an exemplary embodiment of the present specification, one of Ar12 and Ar13 is hydrogen; or deuterium, and the other is a C6-C10 aryl group which is unsubstituted or substituted with deuterium.

In an exemplary embodiment of the present specification, one of Ar12 and Ar13 is hydrogen; or deuterium, and the other is a phenyl group which is unsubstituted or substituted with deuterium; a biphenyl group which is unsubstituted or substituted with deuterium; or a naphthyl group which is unsubstituted or substituted with deuterium.

In an exemplary embodiment of the present specification, Ar12 and Ar13 are each hydrogen; or deuterium.

In an exemplary embodiment of the present specification, one of Ar23 and Ar24 is hydrogen; or deuterium, and the other is a substituted or unsubstituted aryl group.

In an exemplary embodiment of the present specification, one of Ar23 and Ar24 is hydrogen; or deuterium, and the other is a substituted or unsubstituted C6-C30 aryl group.

In an exemplary embodiment of the present specification, one of Ar23 and Ar24 is hydrogen; or deuterium, and the other is a C6-C20 aryl group which is unsubstituted or substituted with deuterium or a C1-C10 alkyl group.

In an exemplary embodiment of the present specification, one of Ar23 and Ar24 is hydrogen; or deuterium, and the other is a C6-C13 aryl group which is unsubstituted or substituted with deuterium or a C1-C6 alkyl group.

In an exemplary embodiment of the present specification, one of Ar23 and Ar24 is hydrogen; or deuterium, and the other is a C6-C10 aryl group which is unsubstituted or substituted with deuterium.

In an exemplary embodiment of the present specification, one of Ar23 and Ar24 is hydrogen; or deuterium, and the other is a phenyl group which is unsubstituted or substituted with deuterium; a biphenyl group which is unsubstituted or substituted with deuterium; a naphthyl group unsubstituted or substituted with deuterium; or a fluorenyl group which is unsubstituted or substituted with deuterium or a methyl group.

In an exemplary embodiment of the present specification, Ar23 and Ar24 are each hydrogen; or deuterium.

In an exemplary embodiment of the present specification, one of Ar31 and Ar32 is hydrogen; or deuterium, and the other is a substituted or unsubstituted aryl group.

In an exemplary embodiment of the present specification, one of Ar31 and Ar32 is hydrogen; or deuterium, and the other is a substituted or unsubstituted C6-C30 aryl group.

In an exemplary embodiment of the present specification, one of Ar31 and Ar32 is hydrogen; or deuterium, and the other is a C6-C20 aryl group which is unsubstituted or substituted with deuterium.

In an exemplary embodiment of the present specification, one of Ar31 and Ar32 is hydrogen; or deuterium, and the other is a C6-C10 aryl group which is unsubstituted or substituted with deuterium.

In an exemplary embodiment of the present specification, one of Ar31 and Ar32 is hydrogen; or deuterium, and the other is a phenyl group which is unsubstituted or substituted with deuterium; a biphenyl group which is unsubstituted or substituted with deuterium; or a naphthyl group which is unsubstituted or substituted with deuterium.

In an exemplary embodiment of the present specification, Ar31 and Ar32 are each hydrogen; or deuterium.

In an exemplary embodiment of the present specification, L1 to L3 are the same as or different from each other, and are each independently a direct bond; or a substituted or unsubstituted arylene group having 6 to 30 carbon atoms.

In an exemplary embodiment of the present specification, L1 to L3 are the same as or different from each other, and are each independently a direct bond; or an arylene group having 6 to 20 carbon atoms, which is unsubstituted or substituted with deuterium.

In an exemplary embodiment of the present specification, L1 to L3 are the same as or different from each other, and are each independently a direct bond; or an arylene group having 6 to 10 carbon atoms, which is unsubstituted or substituted with deuterium.

In an exemplary embodiment of the present specification, L1 to L3 are the same as or different from each other, and are each independently a direct bond; a substituted or unsubstituted phenylene group; a substituted or unsubstituted biphenylene group; a substituted or unsubstituted terphenylene group; or a substituted or unsubstituted naphthylene group.

In an exemplary embodiment of the present specification, L1 to L3 are the same as or different from each other, and are each independently a direct bond; a phenylene group which is unsubstituted or substituted with deuterium; or a naphthylene group which is unsubstituted or substituted with deuterium.

In an exemplary embodiment of the present specification, L1 to L3 are the same as or different from each other, and are each independently a direct bond or any one selected from the following structures.

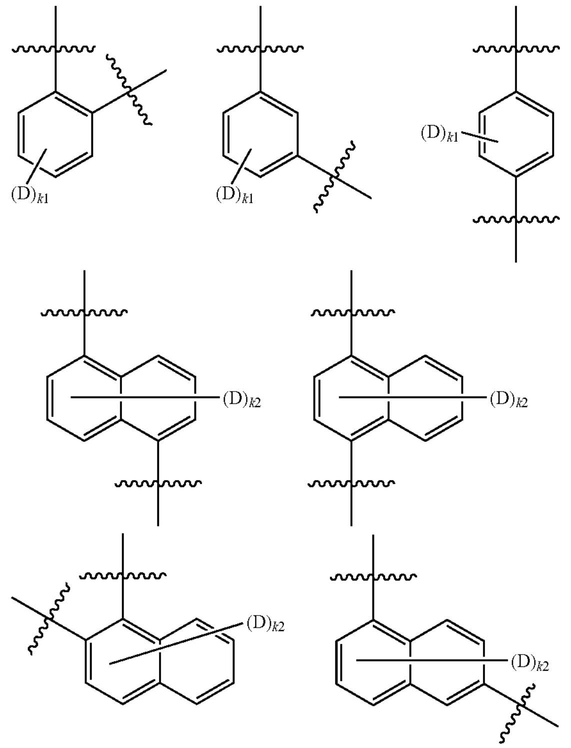

-continued

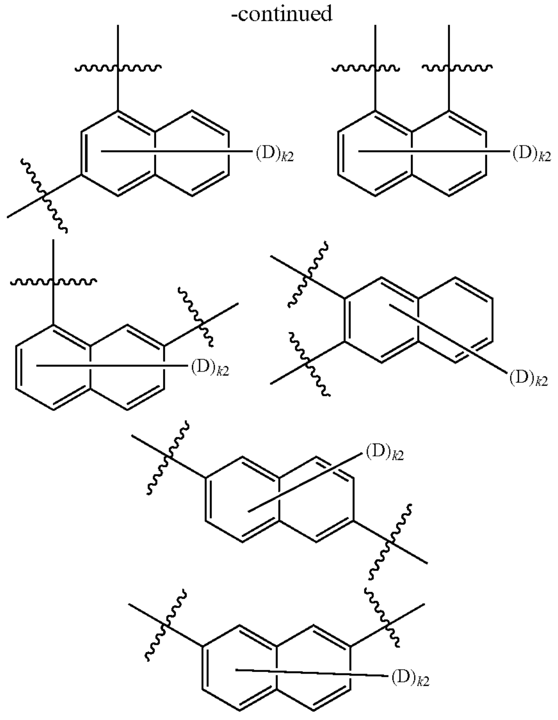

In the structures, D means deuterium, k1 is an integer from 0 to 4, and k2 is an integer from 0 to 6.

In an exemplary embodiment of the present specification, k1 is an integer from 1 to 4.

In an exemplary embodiment of the present specification, k2 is an integer from 1 to 6.

In an exemplary embodiment of the present specification, k1 is 1 or higher. In another exemplary embodiment, k1 is 2 or higher. In still another exemplary embodiment, k1 is 3 or higher. In yet another exemplary embodiment, k1 is 4.

In an exemplary embodiment of the present specification, k2 is 1 or higher. In another exemplary embodiment, k2 is 2 or higher. In still another exemplary embodiment, k2 is 3 or higher. In yet another exemplary embodiment, k2 is 4 or higher. In yet another exemplary embodiment, k2 is 5 or higher. In yet another exemplary embodiment, k2 is 6.

In an exemplary embodiment of the present specification, m11 is 0.

In an exemplary embodiment of the present specification, m11 is 1.

In an exemplary embodiment of the present specification, m21 is 1 or higher.

In an exemplary embodiment of the present specification, m21 is 1.

In an exemplary embodiment of the present specification, m22 is 0.

In an exemplary embodiment of the present specification, m22 is 1 or higher.

In an exemplary embodiment of the present specification, m22 is 1.

In an exemplary embodiment of the present specification, m11+n12 is an integer from 0 to 7.

In an exemplary embodiment of the present specification, m21+n22 is an integer from 0 to 7.

In an exemplary embodiment of the present specification, m22+n23 is an integer from 0 to 5.

In an exemplary embodiment of the present specification, n11 is 1 or higher. In another exemplary embodiment, n11 is 2 or higher. In still another exemplary embodiment, n11 is 3 or higher. In yet another exemplary embodiment, n11 is 4 or higher. In yet another exemplary embodiment, n11 is 5 or higher. In yet another exemplary embodiment, n11 is 6.

In an exemplary embodiment of the present specification, n12 is 1 or higher. In another exemplary embodiment, n12 is 2 or higher. In still another exemplary embodiment, n12 is 3 or higher. In yet another exemplary embodiment, n12 is 4 or higher. In yet another exemplary embodiment, n12 is 5 or higher. In yet another exemplary embodiment, n12 is 6 or higher. In yet another exemplary embodiment, n12 is 7.

In an exemplary embodiment of the present specification, n13 is 1 or higher. In another exemplary embodiment, n13 is 2 or higher. In still another exemplary embodiment, n13 is 3 or higher. In yet another exemplary embodiment, n13 is 4 or higher. In yet another exemplary embodiment, n13 is 5 or higher. In yet another exemplary embodiment, n13 is 6 or higher. In yet another exemplary embodiment, n13 is 7.

In an exemplary embodiment of the present specification, n11+n12+n13 is 2 or higher. In another exemplary embodiment, n11+n12+n13 is 4 or higher. In still another exemplary embodiment, n11+n12+n13 is 6 or higher. In yet another exemplary embodiment, n11+n12+n13 is 8 or higher. In yet another exemplary embodiment, n11+n12+n13 is 10 or higher. In yet another exemplary embodiment, n11+n12+n13 is 12 or higher. In yet another exemplary embodiment, n11+n12+n13 is 14 or higher. In yet another exemplary embodiment, n11+n12+n13 is 16 or higher. In yet another exemplary embodiment, n11+n12+n13 is 18 or higher. In yet another exemplary embodiment, n11+n12+n13 is 20.

In an exemplary embodiment of the present specification, n11+n12+n13 is 19 or lower. In another exemplary embodiment, n11+n12+n13 is 17 or lower. In still another exemplary embodiment, n11+n12+n13 is 15 or lower. In yet another exemplary embodiment, n11+n12+n13 is 13 or lower. In yet another exemplary embodiment, n11+n12+n13 is 11 or lower. In yet another exemplary embodiment, n11+n12+n13 is 9 or lower. In yet another exemplary embodiment, n11+n12+n13 is 7 or lower. In yet another exemplary embodiment, n11+n12+n13 is 5 or lower.

In an exemplary embodiment of the present specification, n11+n12+n13+k1 is 2 or higher. In another exemplary embodiment, n11+n12+n13+k1 is 4 or higher. In yet another exemplary embodiment, n11+n12+n13+k1 is 6 or higher. In yet another exemplary embodiment, n11+n12+n13+k1 is 8 or higher. In yet another exemplary embodiment, n11+n12+n13+k1 is 10 or higher. In yet another exemplary embodiment, n11+n12+n13+k1 is 12 or higher. In yet another exemplary embodiment, n11+n12+n13+k1 is 14 or higher. In yet another exemplary embodiment, n11+n12+n13+k1 is 16 or higher. In yet another exemplary embodiment, n11+n12+n13+k1 is 18 or higher. In yet another exemplary embodiment, n11+n12+n13+k1 is 20 or higher. In yet another exemplary embodiment, n11+n12+n13+k1 is 22 or higher. In yet another exemplary embodiment, n11+n12+n13+k1 is 24.

In an exemplary embodiment of the present specification, n11+n12+n13+k1 is 23 or lower. In yet another exemplary embodiment, n11+n12+n13+k1 is 21 or lower. In still another exemplary embodiment, n11+n12+n13+k1 is 19 or lower. In yet another exemplary embodiment, n11+n12+n13+k1 is 17 or lower. In yet another exemplary embodiment, n11+n12+n13+k1 is 15 or lower. In yet another exemplary embodiment, n11+n12+n13+k1 is 13 or lower. In yet another exemplary embodiment, n11+n12+n13+k1 is 11 or lower. In yet another exemplary embodiment, n11+n12+n13+k1 is 9 or lower. In yet another exemplary embodiment, n11+n12+n13+k1 is 7 or lower. In yet another exemplary embodiment, n11+n12+n13+k1 is 5 or lower.

In an exemplary embodiment of the present specification, n11+n12+n13+k2 is 2 or higher. In another exemplary embodiment, n11+n12+n13+k2 is 4 or higher. In still another exemplary embodiment, n11+n12+n13+k2 is 6 or higher. In yet another exemplary embodiment, n11+n12+n13+k2 is 8 or higher. In yet another exemplary embodiment, n11+n12+n13+k2 is 10 or higher. In yet another exemplary embodiment, n11+n12+n13+k2 is 12 or higher. In yet another exemplary embodiment, n11+n12+n13+k2 is 14 or higher. In yet another exemplary embodiment, n11+n12+n13+k2 is 16 or higher. In yet another exemplary embodiment, n11+n12+n13+k2 is 18 or higher. In yet another exemplary embodiment, n11+n12+n13+k2 is 20 or higher. In yet another exemplary embodiment, n11+n12+n13+k2 is 22 or higher. In yet another exemplary embodiment, n11+n12+n13+k2 is 24 or higher. In yet another exemplary embodiment, n11+n12+n13+k2 is 26.

In an exemplary embodiment of the present specification, n11+n12+n13+k2 is 25 or lower. In another exemplary embodiment, n11+n12+n13+k2 is 23 or lower. In still another exemplary embodiment, n11+n12+n13+k2 is 21 or lower. In yet another exemplary embodiment, n11+n12+n13+k2 is 19 or lower. In yet another exemplary embodiment, n11+n12+n13+k2 is 17 or lower. In yet another exemplary embodiment, n11+n12+n13+k2 is 15 or lower. In yet another exemplary embodiment, n11+n12+n13+k2 is 13 or lower. In yet another exemplary embodiment, n11+n12+n13+k2 is 11 or lower. In yet another exemplary embodiment, n11+n12+n13+k2 is 9 or lower. In yet another exemplary embodiment, n11+n12+n13+k2 is 7 or lower.

In an exemplary embodiment of the present specification, n21 is 1 or higher. In another exemplary embodiment, n21 is 2 or higher. In still another exemplary embodiment, n21 is 3 or higher. In yet another exemplary embodiment, n21 is 4 or higher. In yet another exemplary embodiment, n21 is 5 or higher. In yet another exemplary embodiment, n21 is 6.

In an exemplary embodiment of the present specification, n22 is 1 or higher. In another exemplary embodiment, n22 is 2 or higher. In still another exemplary embodiment, n22 is 3 or higher. In yet another exemplary embodiment, n22 is 4 or higher. In yet another exemplary embodiment, n22 is 5 or higher. In yet another exemplary embodiment, n22 is 6 or higher. In yet another exemplary embodiment, n22 is 7.

In an exemplary embodiment of the present specification, n23 is 1 or higher. In another exemplary embodiment, n23 is 2 or higher. In still another exemplary embodiment, n23 is 3 or higher. In yet another exemplary embodiment, n23 is 4 or higher. In yet another exemplary embodiment, n23 is 5.

In an exemplary embodiment of the present specification, n21+n22+n23 is 2 or higher. In another exemplary embodiment, n21+n22+n23 is 4 or higher. In still another exemplary embodiment, n21+n22+n23 is 6 or higher. In yet another exemplary embodiment, n21+n22+n23 is 8 or higher. In yet another exemplary embodiment, n21+n22+n23 is 10 or higher. In yet another exemplary embodiment, n21+n22+n23 is 12 or higher. In yet another exemplary embodiment, n21+n22+n23 is 14 or higher. In yet another exemplary embodiment, n21+n22+n23 is 16 or higher. In yet another exemplary embodiment, n21+n22+n23 is 18.

In an exemplary embodiment of the present specification, n21+n22+n23 is 17 or lower. In another exemplary embodiment, n21+n22+n23 is 15 or lower. In still another exemplary embodiment, n21+n22+n23 is 13 or lower. In yet another exemplary embodiment, n21+n22+n23 is 11 or lower. In yet another exemplary embodiment, n21+n22+n23 is 9 or lower. In yet another exemplary embodiment, n21+n22+n23 is 7 or lower. In yet another exemplary embodiment, n21+n22+n23 is 5 or lower.

In an exemplary embodiment of the present specification, n21+n22+n23+k1 is 2 or higher. In another exemplary embodiment, n21+n22+n23+k1 is 4 or higher. In still another exemplary embodiment, n21+n22+n23+k1 is 6 or higher. In yet another exemplary embodiment, n21+n22+n23+k1 is 8 or higher. In yet another exemplary embodiment, n21+n22+n23+k1 is 10 or higher. In yet another exemplary embodiment, n21+n22+n23+k1 is 12 or higher. In yet another exemplary embodiment, n21+n22+n23+k1 is 14 or higher. In yet another exemplary embodiment, n21+n22+n23+k1 is 16 or higher. In yet another exemplary embodiment, n21+n22+n23+k1 is 18 or higher. In yet another exemplary embodiment, n21+n22+n23+k1 is 20 or higher. In yet another exemplary embodiment, n21+n22+n23+k1 is 22. In an exemplary embodiment of the present specification, n21+n22+n23+k1 is 21 or lower. In still another exemplary embodiment, n21+n22+n23+k1 is 19 or lower. In yet another exemplary embodiment, n21+n22+n23+k1 is 17 or lower. In yet another exemplary embodiment, n21+n22+n23+k1 is 15 or lower. In yet another exemplary embodiment, n21+n22+n23+k1 is 13 or lower. In yet another exemplary embodiment, n21+n22+n23+k1 is 11 or lower. In yet another exemplary embodiment, n21+n22+n23+k1 is 9 or lower. In yet another exemplary embodiment, n21+n22+n23+k1 is 7 or lower. In yet another exemplary embodiment, n21+n22+n23+k1 is 5 or lower.

In an exemplary embodiment of the present specification, n21+n22+n23+k2 is 2 or higher. In another exemplary embodiment, n21+n22+n23+k2 is 4 or higher. In still another exemplary embodiment, n21+n22+n23+k2 is 6 or higher. In yet another exemplary embodiment, n21+n22+n23+k2 is 8 or higher. In yet another exemplary embodiment, n21+n22+n23+k2 is 10 or higher. In yet another exemplary embodiment, n21+n22+n23+k2 is 12 or higher. In yet another exemplary embodiment, n21+n22+n23+k2 is 14 or higher. In yet another exemplary embodiment, n21+n22+n23+k2 is 16 or higher. In yet another exemplary embodiment, n21+n22+n23+k2 is 18 or higher. In yet another exemplary embodiment, n21+n22+n23+k2 is 20 or higher. In yet another exemplary embodiment, n21+n22+n23+k2 is 22 or higher. In yet another exemplary embodiment, n21+n22+n23+k2 is 24.

In an exemplary embodiment of the present specification, n21+n22+n23+k2 is 23 or lower. In still another exemplary embodiment, n21+n22+n23+k2 is 21 or lower. In yet another exemplary embodiment, n21+n22+n23+k2 is 19 or lower. In yet another exemplary embodiment, n21+n22+n23+k2 is 17 or lower. In yet another exemplary embodiment, n21+n22+n23+k2 is 15 or lower. In yet another exemplary embodiment, n21+n22+n23+k2 is 13 or lower. In yet another exemplary embodiment, n21+n22+n23+k2 is 11 or lower. In yet another exemplary embodiment, n21+n22+n23+k2 is 9 or lower. In yet another exemplary embodiment, n21+n22+n23+k2 is 7 or lower. In yet another exemplary embodiment, n21+n22+n23+k2 is 5 or lower.

In an exemplary embodiment of the present specification, n31 is 1 or higher. In another exemplary embodiment, n31 is 2 or higher. In still another exemplary embodiment, n31 is 3 or higher. In yet another exemplary embodiment, n31 is 4 or higher. In yet another exemplary embodiment, n31 is 5 or higher. In yet another exemplary embodiment, n31 is 6.

In an exemplary embodiment of the present specification, n32 is 1 or higher. In another exemplary embodiment, n32 is 2 or higher. In still another exemplary embodiment, n32 is 3 or higher. In yet another exemplary embodiment, n32 is 4 or higher. In yet another exemplary embodiment, n32 is 5 or higher. In yet another exemplary embodiment, n32 is 6 or higher. In yet another exemplary embodiment, n32 is 7.

In an exemplary embodiment of the present specification, n33 is 1 or higher. In another exemplary embodiment, n33 is 2 or higher. In still another exemplary embodiment, n33 is 3 or higher. In yet another exemplary embodiment, n33 is 4 or higher. In yet another exemplary embodiment, n33 is 5 or higher. In yet another exemplary embodiment, n33 is 6 or higher. In yet another exemplary embodiment, n33 is 7.

In an exemplary embodiment of the present specification, n31+n32+n33 is 2 or higher. In another exemplary embodiment, n31+n32+n33 is 4 or higher. In still another exemplary embodiment, n31+n32+n33 is 6 or higher. In yet another exemplary embodiment, n31+n32+n33 is 8 or higher. In yet another exemplary embodiment, n31+n32+n33 is 10 or higher. In yet another exemplary embodiment, n31+n32+n33 is 12 or higher. In yet another exemplary embodiment, n31+n32+n33 is 14 or higher. In yet another exemplary embodiment, n31+n32+n33 is 16 or higher. In yet another exemplary embodiment, n31+n32+n33 is 18 or higher. In yet another exemplary embodiment, n31+n32+n33 is 20.

In an exemplary embodiment of the present specification, n31+n32+n33 is 19 or lower. In another exemplary embodiment, n31+n32+n33 is 17 or lower. In still another exemplary embodiment, n31+n32+n33 is 15 or lower. In yet another exemplary embodiment, n31+n32+n33 is 13 or lower. In yet another exemplary embodiment, n31+n32+n33 is 11 or lower. In yet another exemplary embodiment, n31+n32+n33 is 9 or lower. In yet another exemplary embodiment, n31+n32+n33 is 7 or lower. In yet another exemplary embodiment, n31+n32+n33 is 5 or lower.

In an exemplary embodiment of the present specification, n31+n32+n33+k1 is 2 or higher. In another exemplary embodiment, n31+n32+n33+k1 is 4 or higher. In still another exemplary embodiment, n31+n32+n33+k1 is 6 or higher. In yet another exemplary embodiment, n31+n32+n33+k1 is 8 or higher. In yet another exemplary embodiment, n31+n32+n33+k1 is 10 or higher. In yet another exemplary embodiment, n31+n32+n33+k1 is 12 or higher. In yet another exemplary embodiment, n31+n32+n33+k1 is 14 or higher. In yet another exemplary embodiment, n31+n32+n33+k1 is 16 or higher. In yet another exemplary embodiment, n31+n32+n33+k1 is 18 or higher. In yet another exemplary embodiment, n31+n32+n33+k1 is 20 or higher. In yet another exemplary embodiment, n31+n32+n33+k1 is 22 or higher. In yet another exemplary embodiment, n31+n32+n33+k1 is 24.

In an exemplary embodiment of the present specification, n31+n32+n33+k1 is 23 or lower. In another exemplary embodiment, n31+n32+n33+k1 is 21 or lower. In still another exemplary embodiment, n31+n32+n33+k1 is 19 or lower. In yet another exemplary embodiment, n31+n32+n33+k1 is 17 or lower. In yet another exemplary embodiment, n31+n32+n33+k1 is 15 or lower. In yet another exemplary embodiment, n31+n32+n33+k1 is 13 or lower. In yet another exemplary embodiment, n31+n32+n33+k1 is 11 or lower. In yet another exemplary embodiment, n31+n32+n33+k1 is 9 or lower. In yet another exemplary embodiment, n31+n32+n33+k1 is 7 or lower. In yet another exemplary embodiment, n31+n32+n33+k1 is 5 or lower.

In an exemplary embodiment of the present specification, 30% or more of Formulae 1-1 to 1-3 are substituted with deuterium. In another exemplary embodiment, 40% or more of Formulae 1-1 to 1-3 are substituted with deuterium. In still another exemplary embodiment, 60% or more of Formulae 1-1 to 1-3 are substituted with deuterium. In yet another exemplary embodiment, 80% or more of Formulae 1-1 to 1-3 are substituted with deuterium. In yet another exemplary embodiment, 100% of Formulae 1-1 to 1-3 are substituted with deuterium.

In Formulae 1-1 to 1-3, the higher the deuterium substitution rate is, the more conspicuous the long service life characteristics of a device are.

In an exemplary embodiment of the present specification, n11 is 6, and Ar12 and Ar13 are deuterium.

In an exemplary embodiment of the present specification, n21 is 6, and Ar23 and Ar24 are deuterium.

In an exemplary embodiment of the present specification, n31 is 6, and Ar31 and Ar32 are deuterium.

When deuterium is linked to anthracene, the long service life effect of a device is enhanced as compared to the case where deuterium is linked to other substituents.

In an exemplary embodiment of the present specification, Formulae 1-1 to 1-3 include at least one hydrogen. That is, the compounds of Formulae 1-1 to 1-3 are deuterated to less than 100%.

In an exemplary embodiment of the present specification, the compound of Formula 1-1 is represented by any one selected from the following Formulae 101 to 104.

[Formula 101]

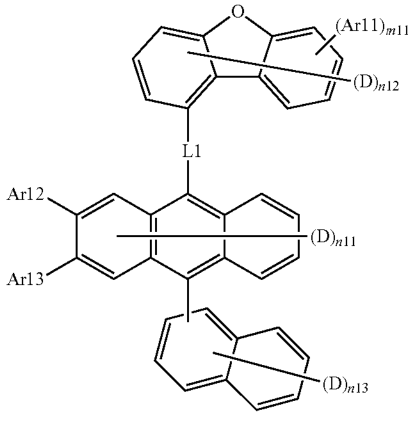

[Formula 102]

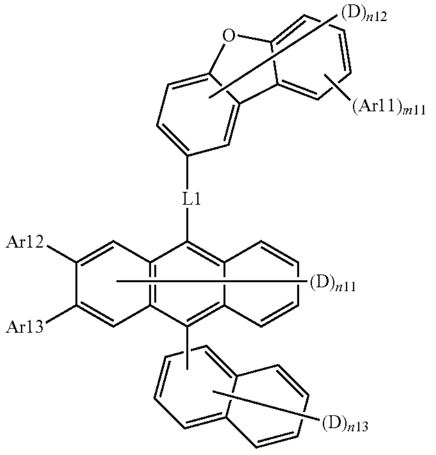

-continued

[Formula 103]

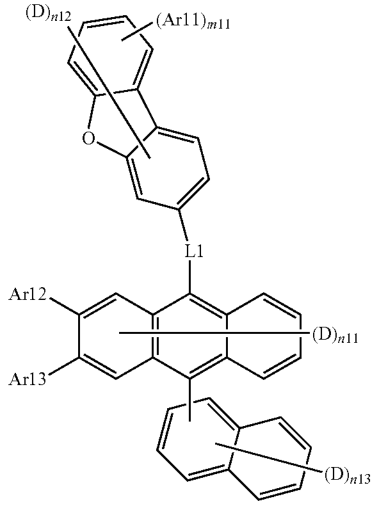

[Formula 104]

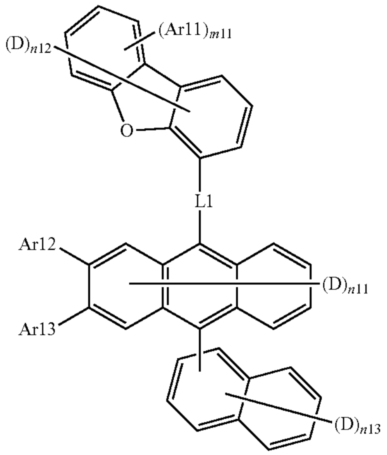

In Formulae 101 to 104, definitions of Ar11 to Ar13, D, n11 to n13, m11, and L1 are the same as those defined in Formula 1-1.

In an exemplary embodiment of the present specification, the compound of Formula 1-2 is represented by any one selected from the following Formulae 111 to 114.

[Formula 111]

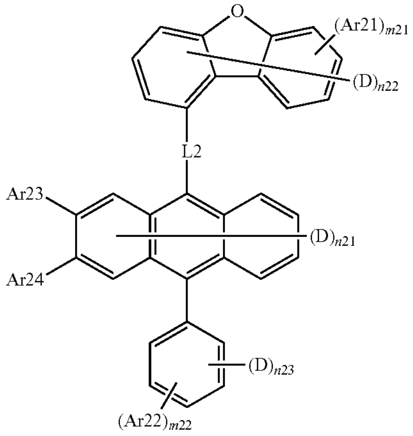

-continued
[Formula 112]
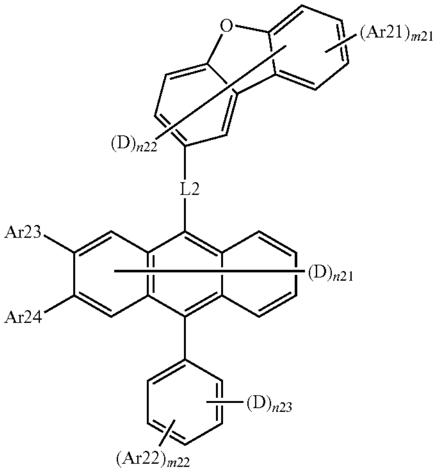
[Formula 113]
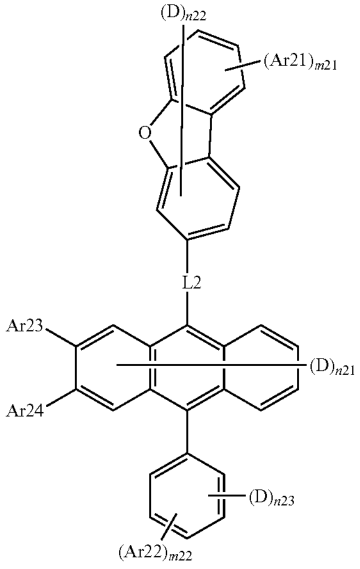
[Formula 114]
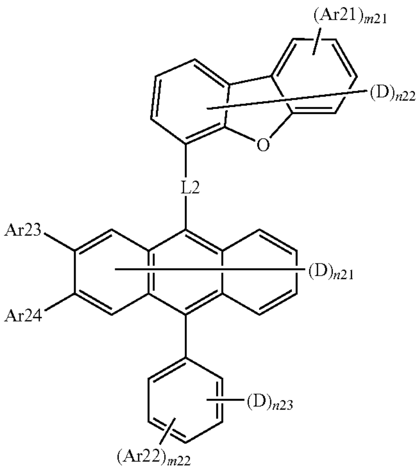
In Formulae 111 to 114, definitions of D, n21 to n23, Ar21 to Ar24, m21, m22, and L2 are the same as those defined in Formula 1-2.
In an exemplary embodiment of the present specification, the compound of Formula 1-3 is represented by any one selected from the following Formulae 121 to 124.
[Formula 121]
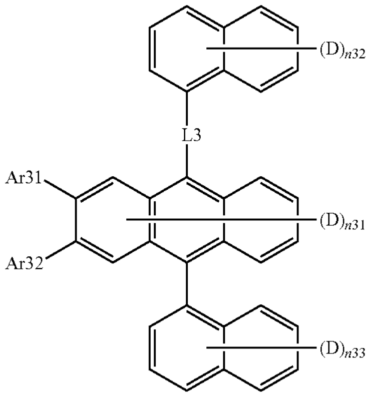
[Formula 122]
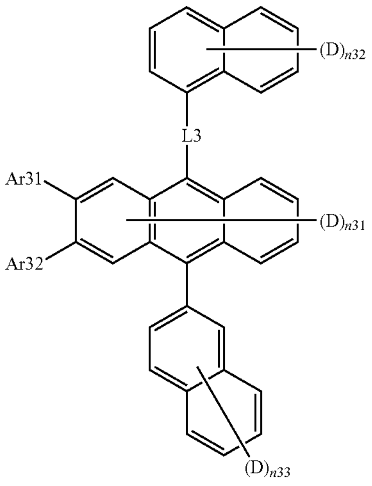
[Formula 123]
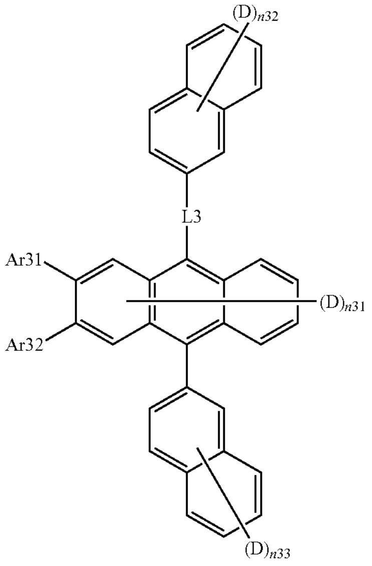

-continued

[Formula 124]

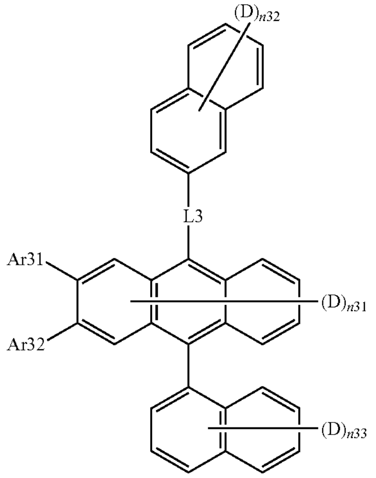

In Formulae 121 to 124, definitions of Ar31, Ar32, D, n31 to n33, and L3 are the same as those defined in Formula 1-3.

In an exemplary embodiment of the present specification, Formulae 1-1 and 1-2 are represented by Formula 101, 102, 111, or 112. When deuterium is linked to anthracene via No. 1 or No. 2 carbon of dibenzofuran as in Formula 101, 102, 111, or 112, the driving voltage of the device is low, which is advantageous in constructing a highly efficient device.

In an exemplary embodiment of the present specification, the compound represented by Formula 1-1 is any one selected from the following compounds.

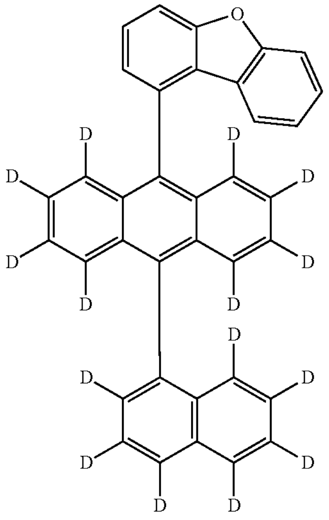

-continued

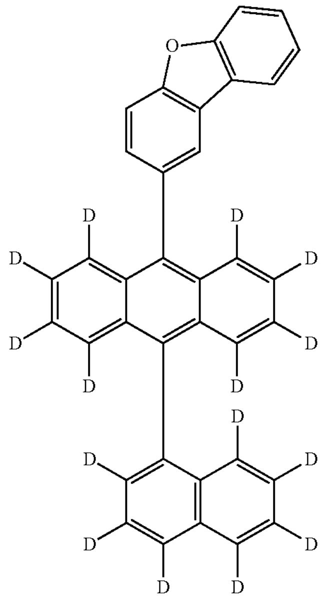

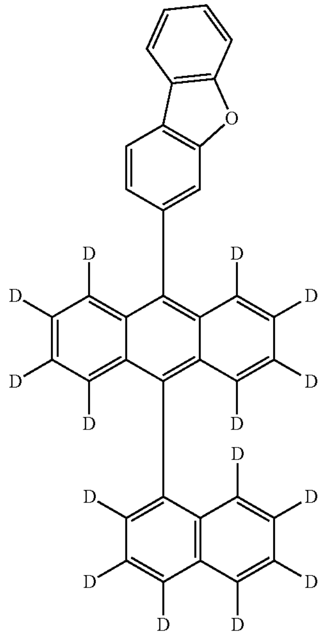

-continued
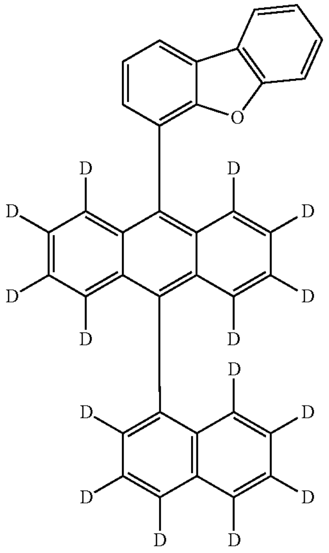
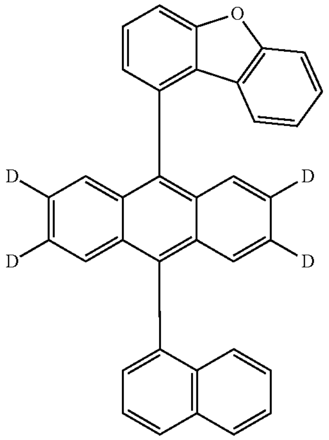
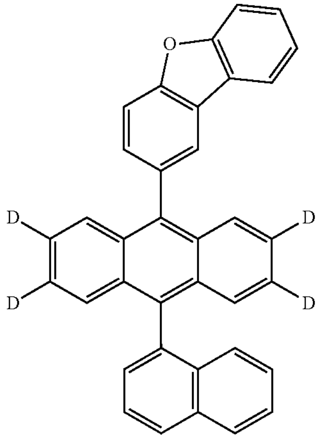
-continued
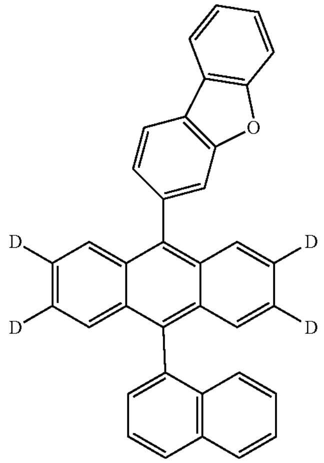
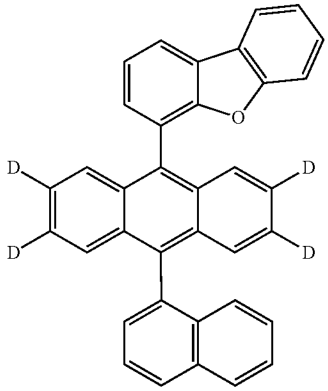
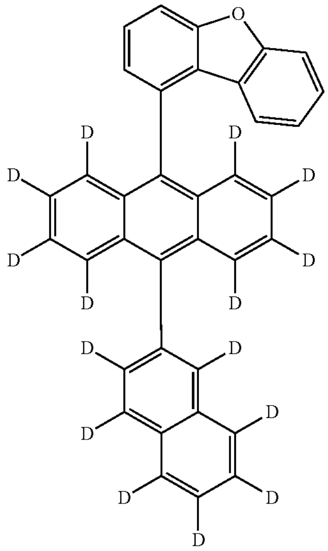

-continued
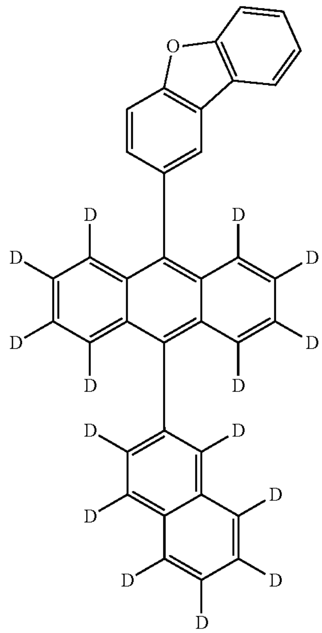
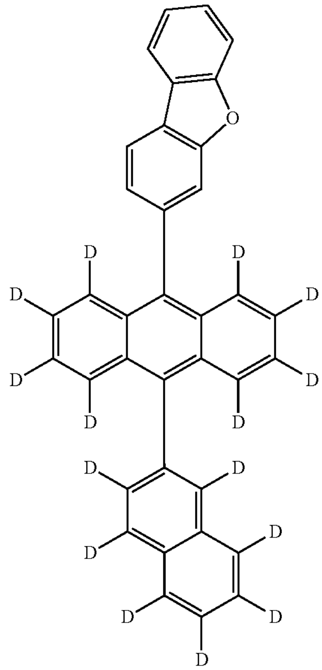
-continued
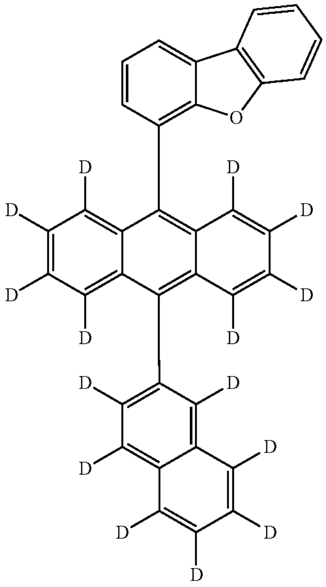
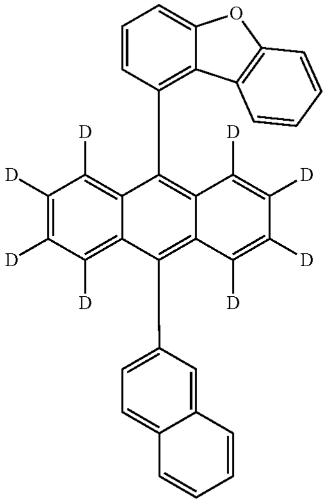
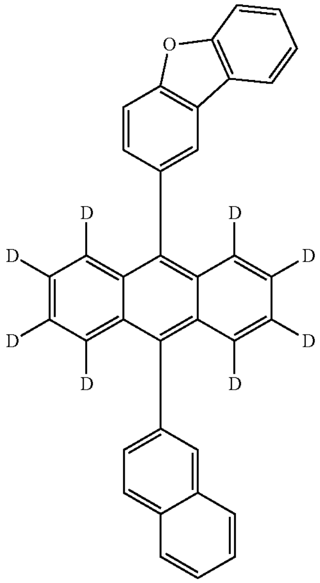

-continued
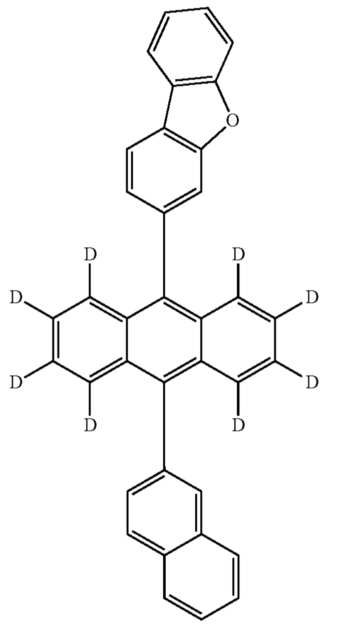
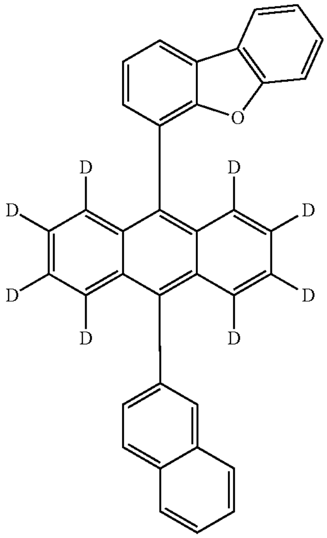
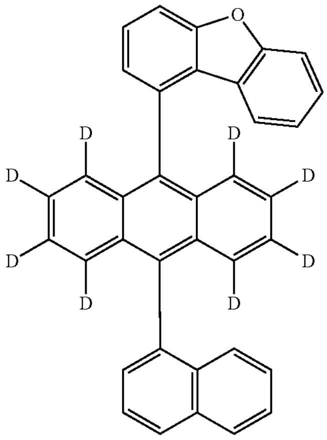
-continued
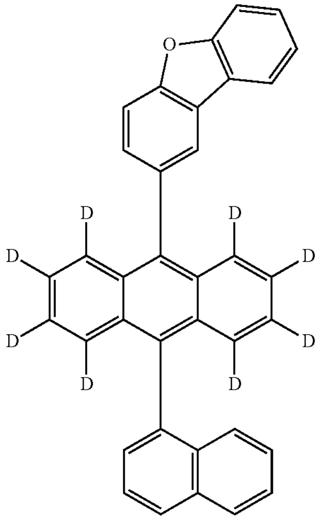
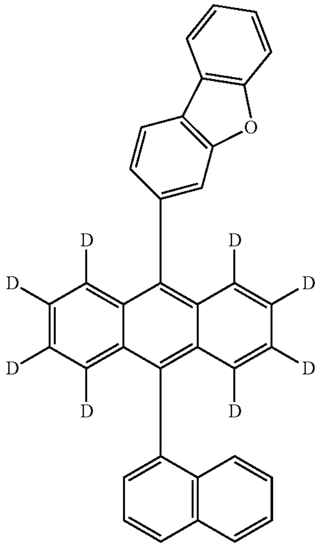
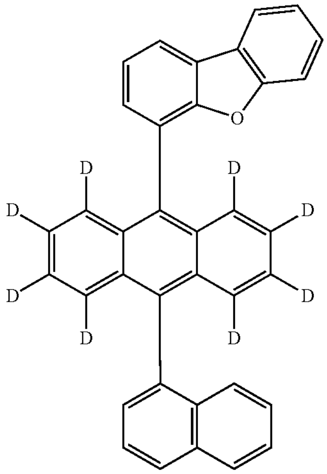

-continued
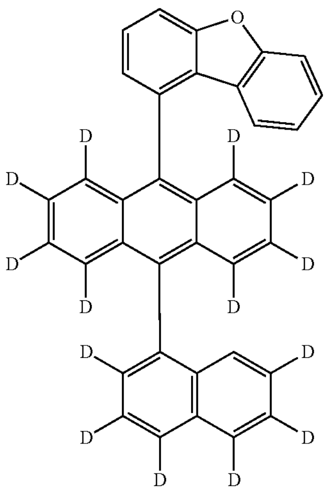
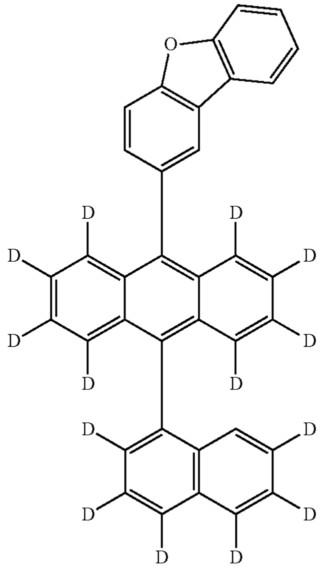
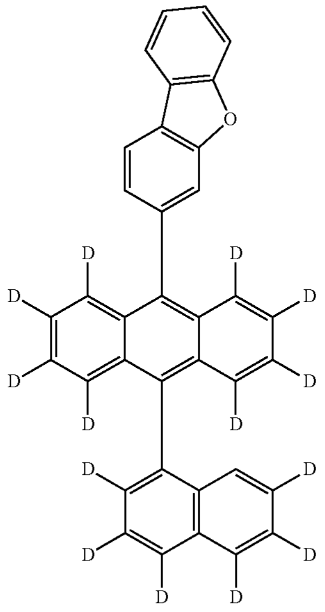
-continued
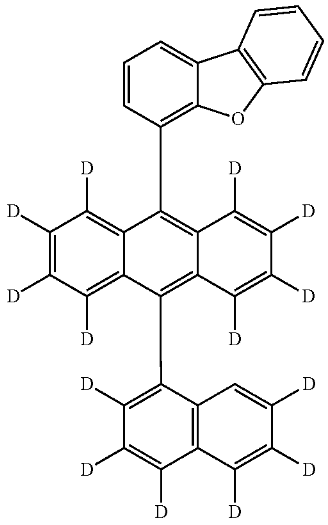
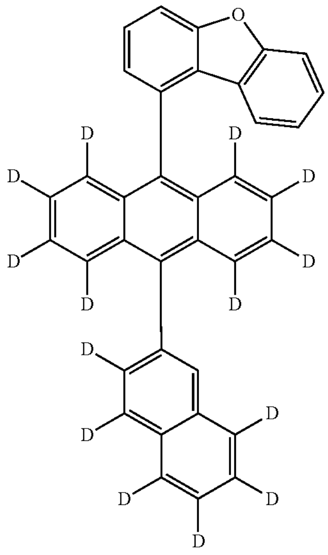
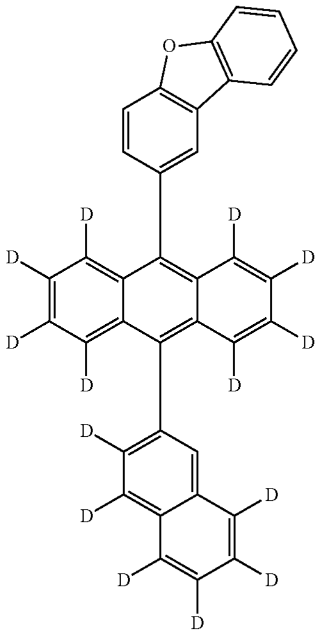

-continued
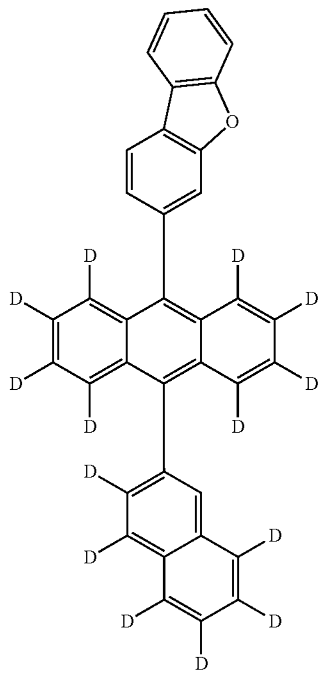
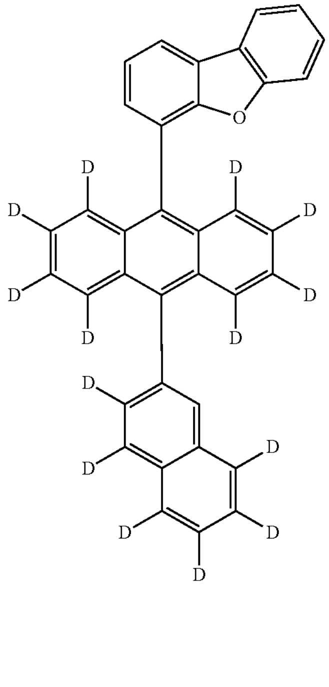
-continued
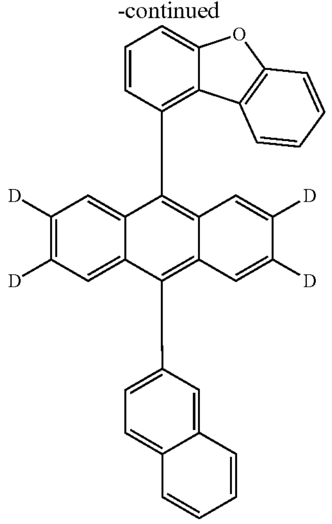
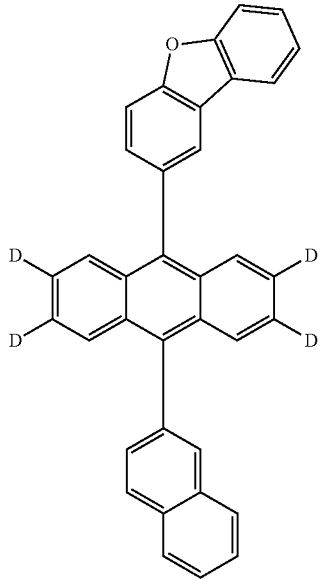
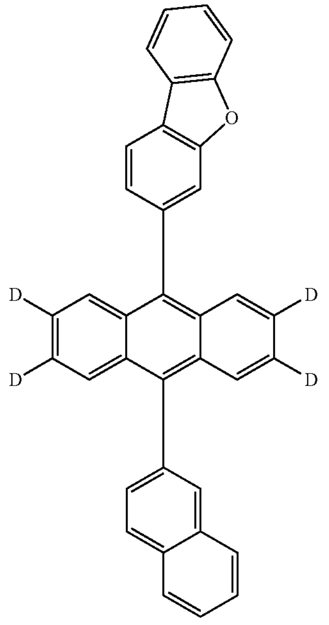

-continued
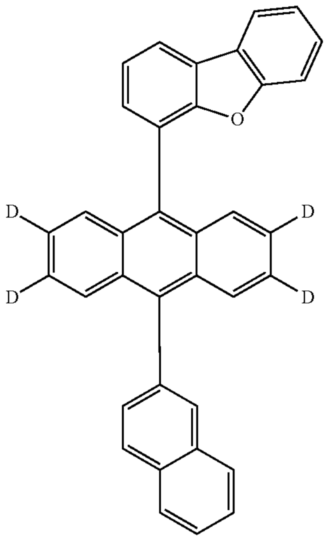
-continued
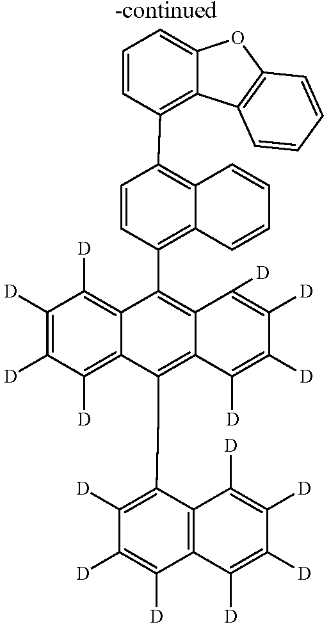
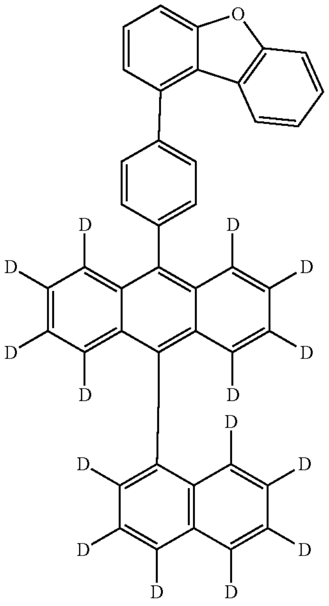
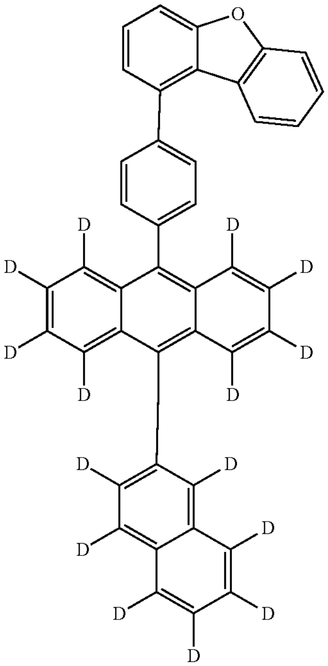

-continued
-continued
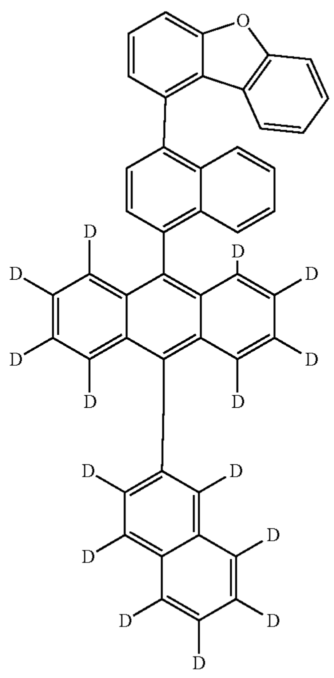
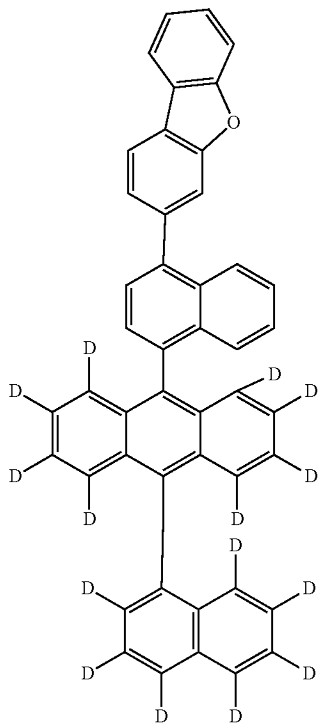
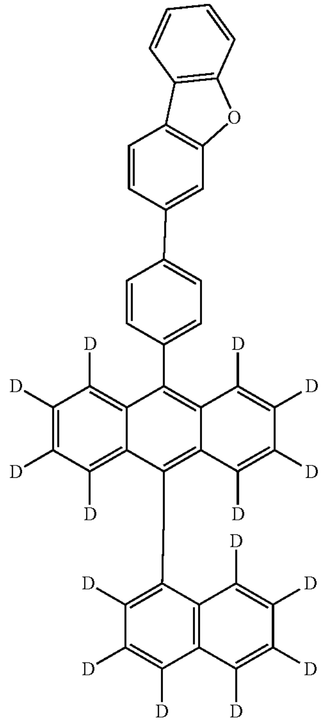
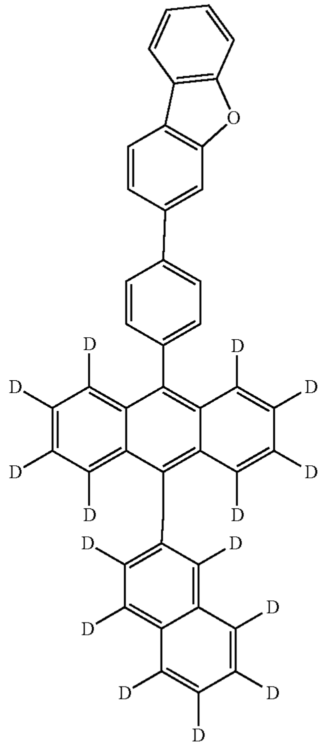

-continued
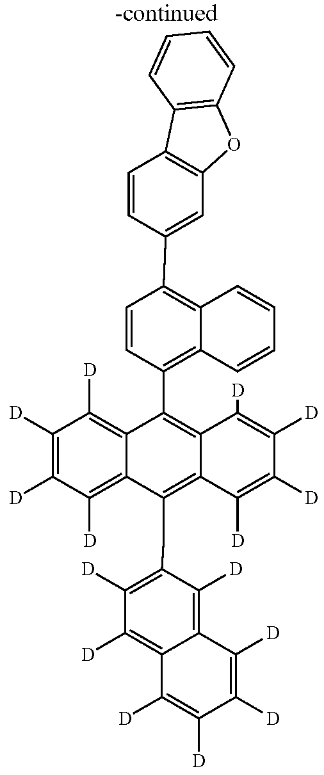
-continued
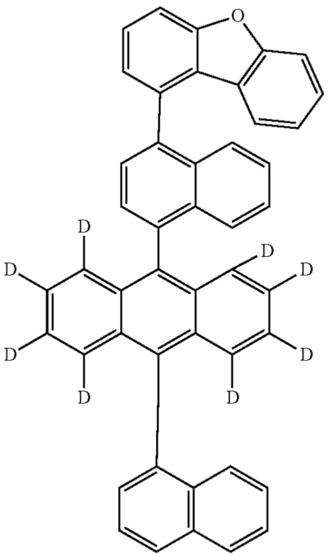
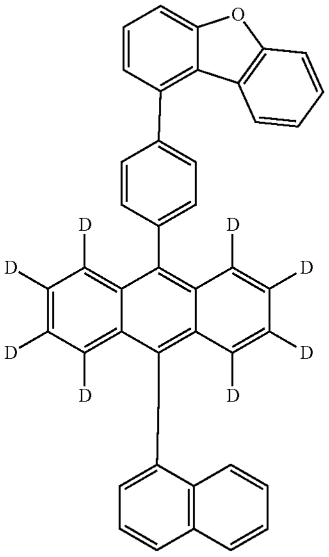
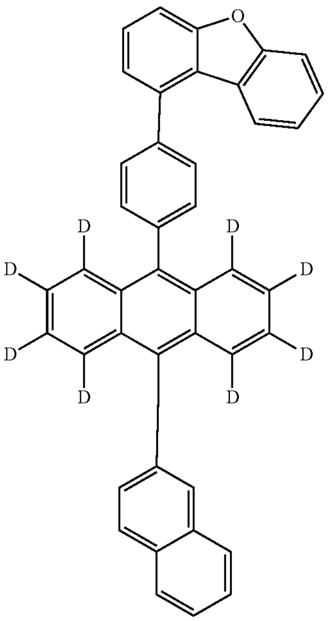

-continued
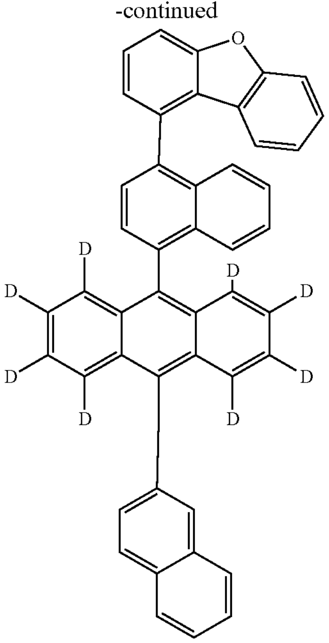
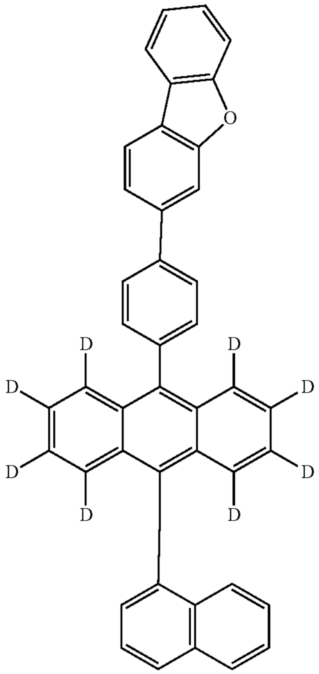
-continued
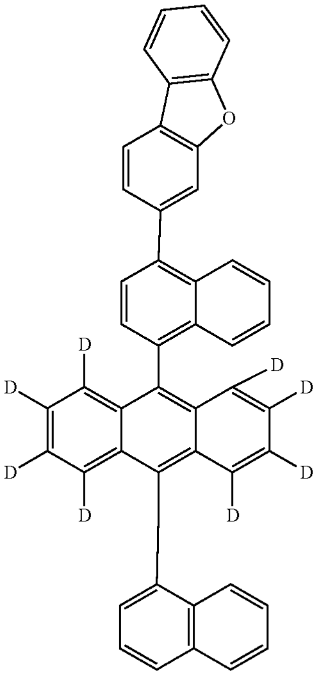
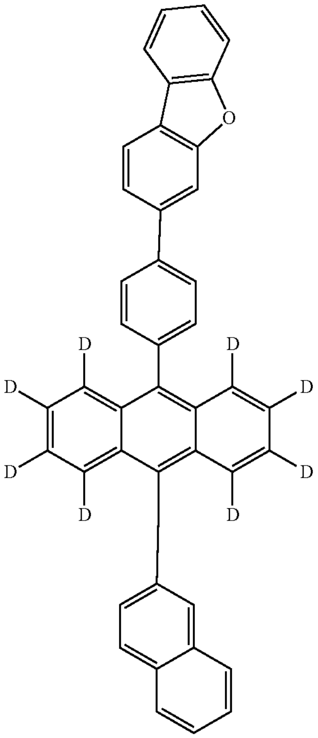

-continued
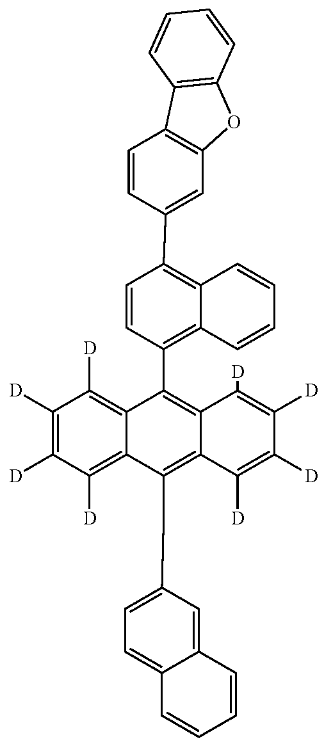
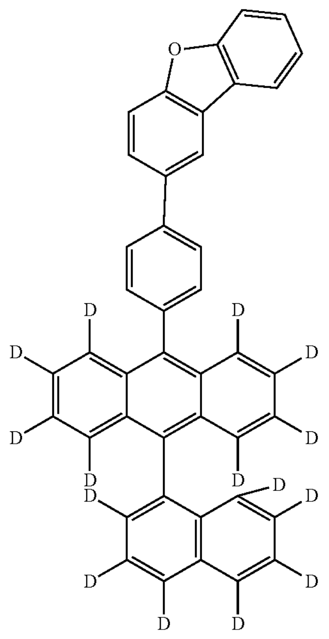
-continued
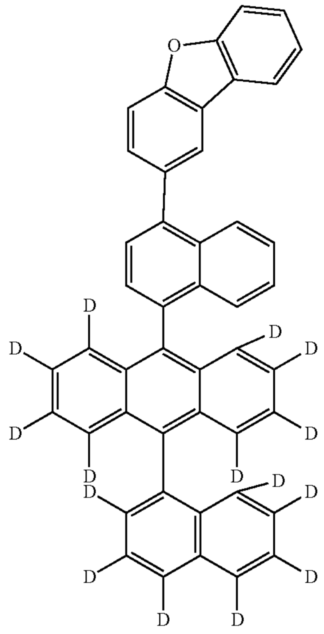
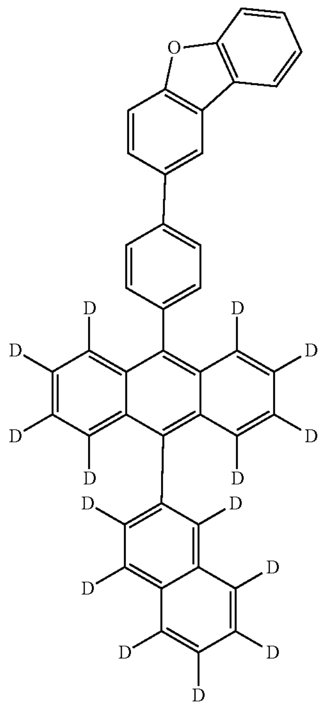

-continued
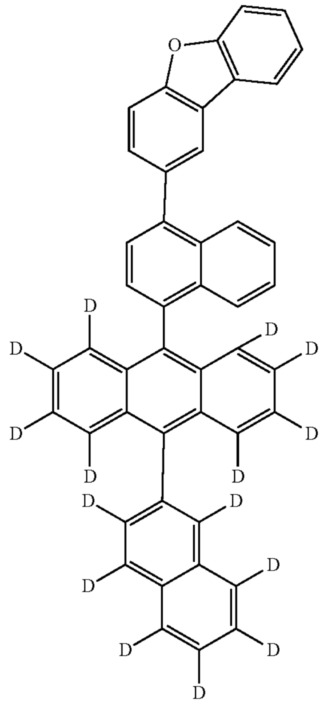
-continued
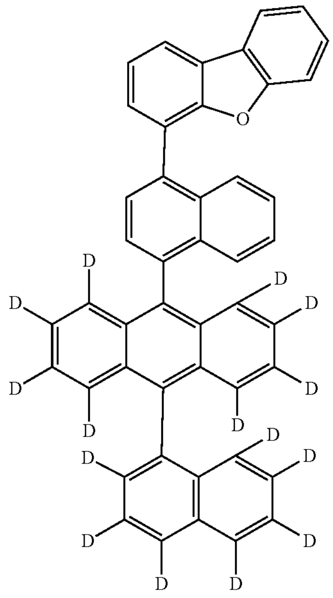
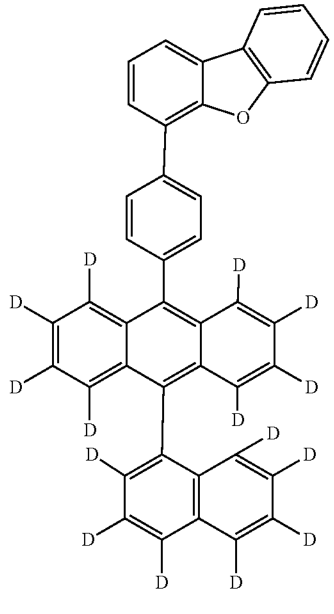
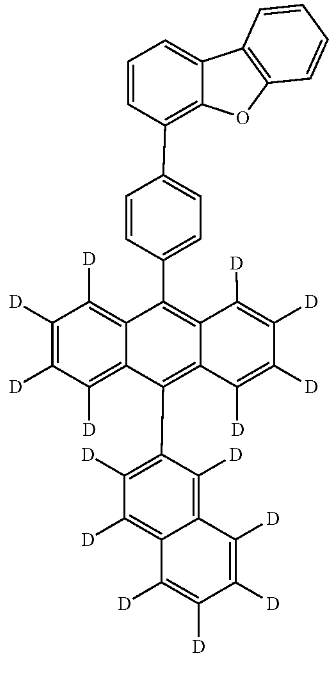

-continued
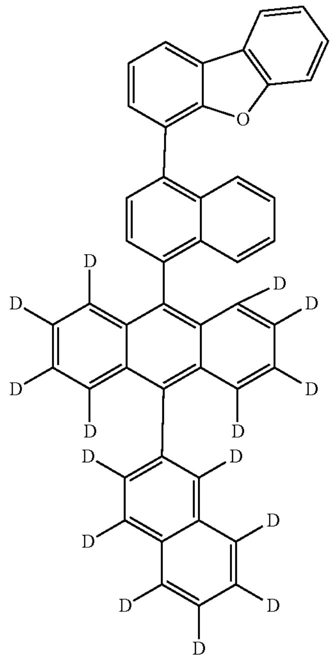
-continued
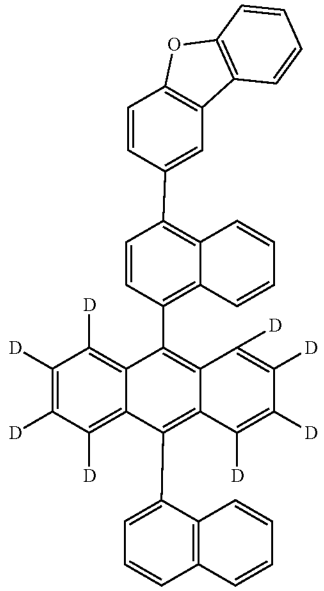
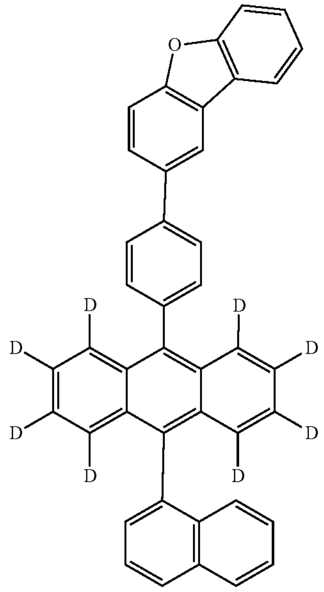
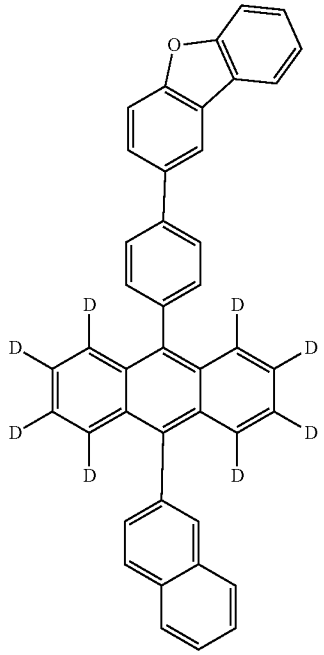

-continued
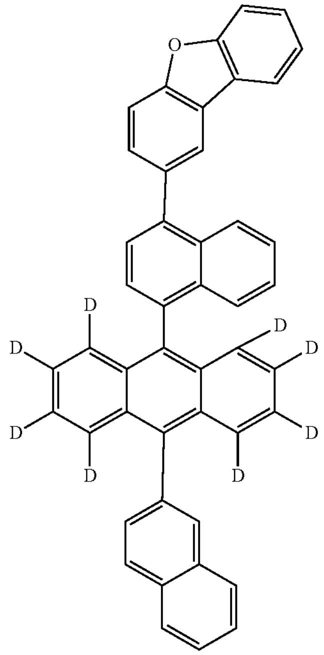
-continued
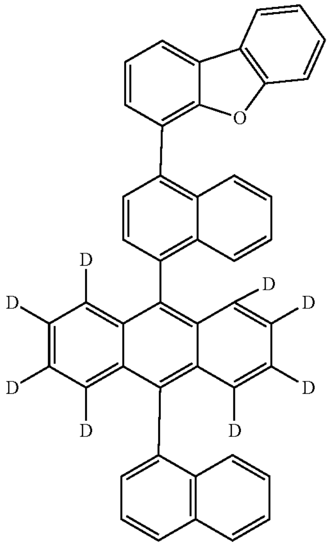
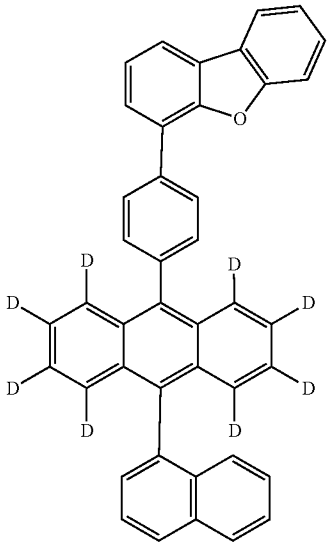
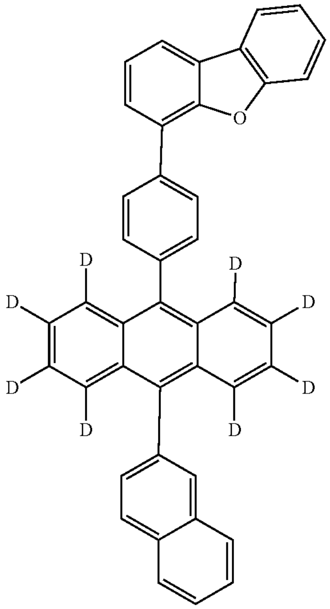

-continued
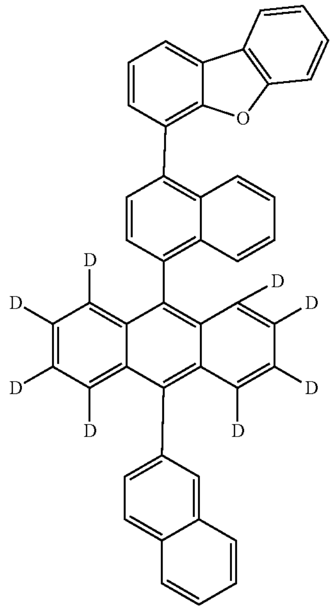
-continued
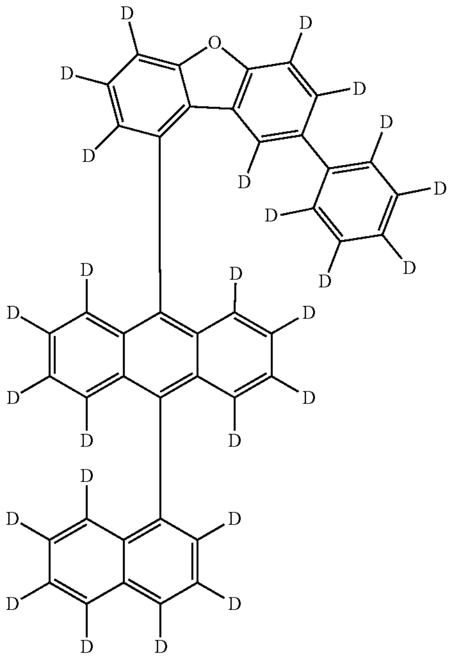
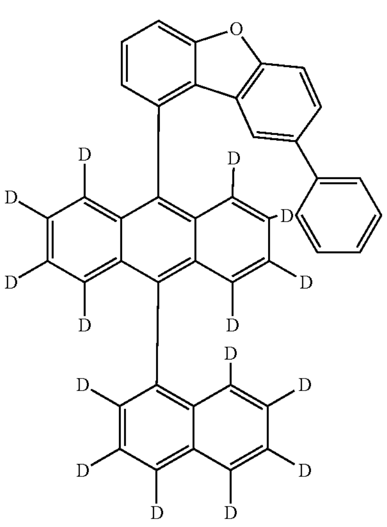
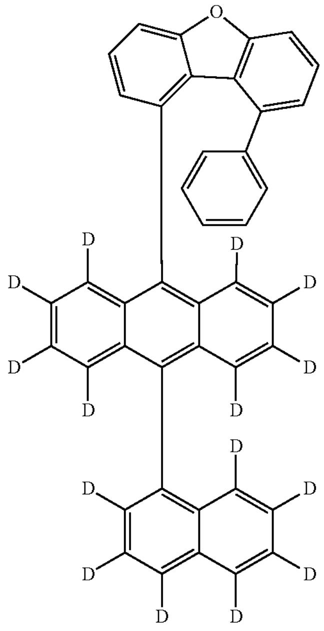

-continued
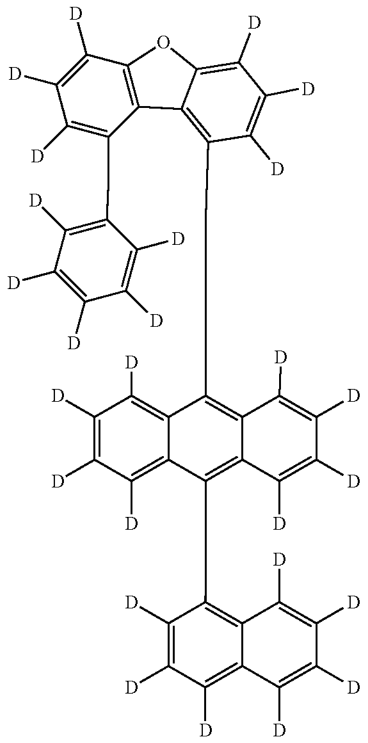
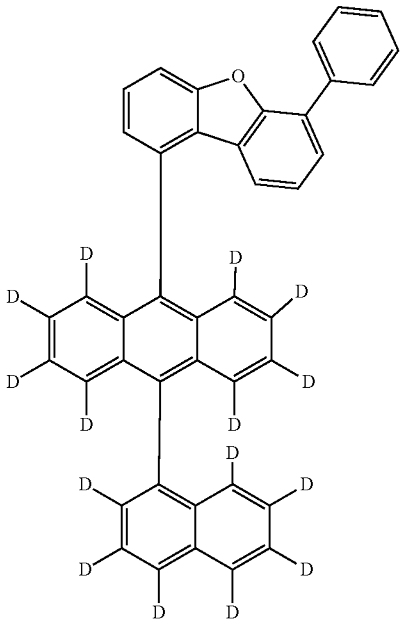
-continued
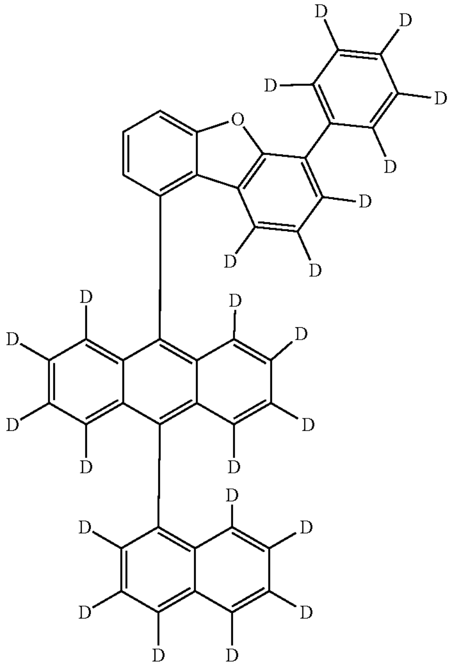
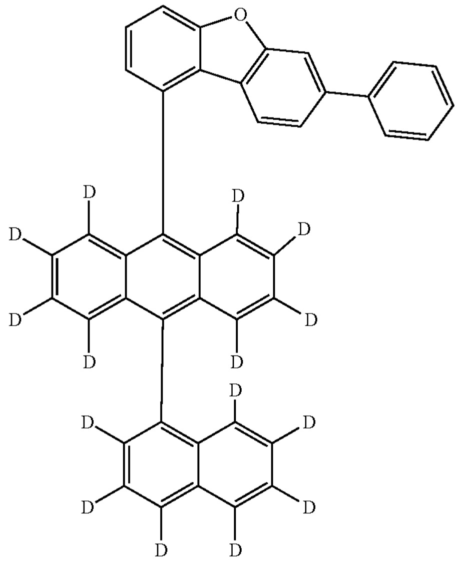

-continued
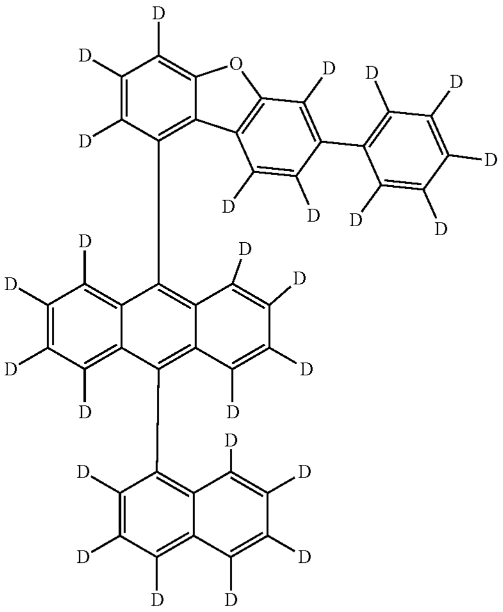
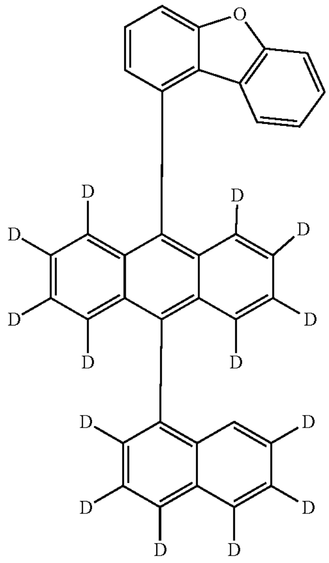
-continued
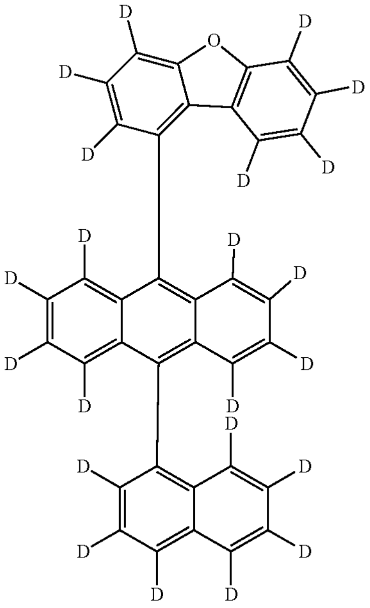
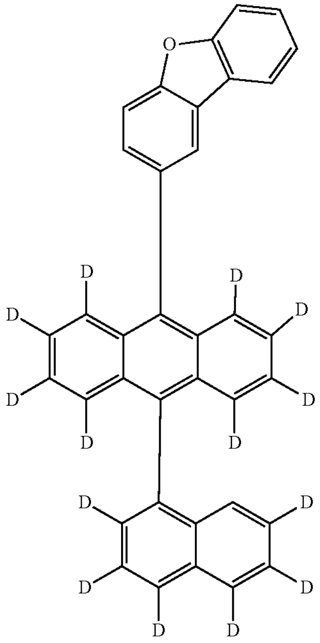

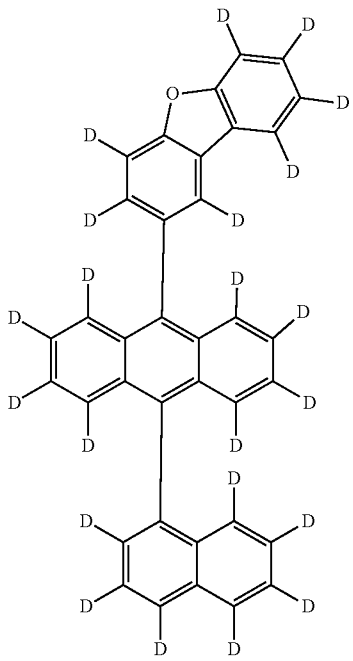
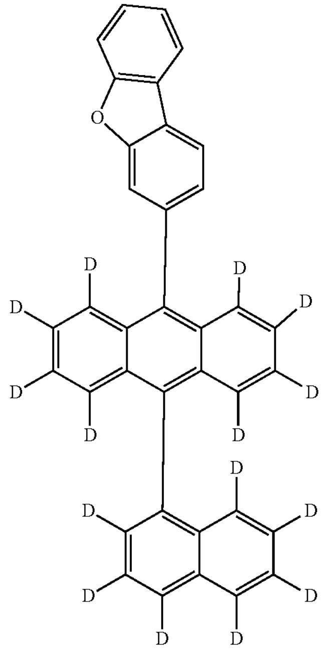
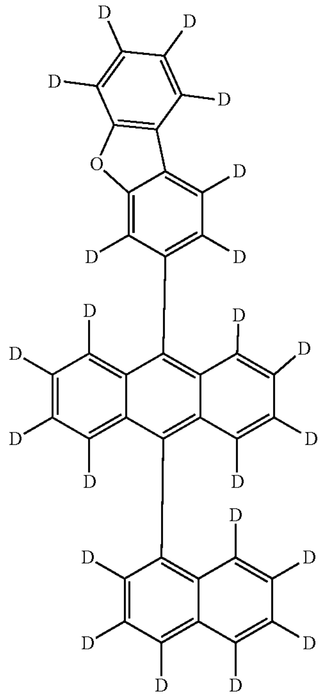
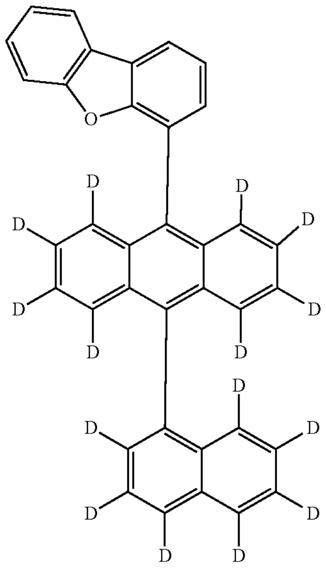

-continued
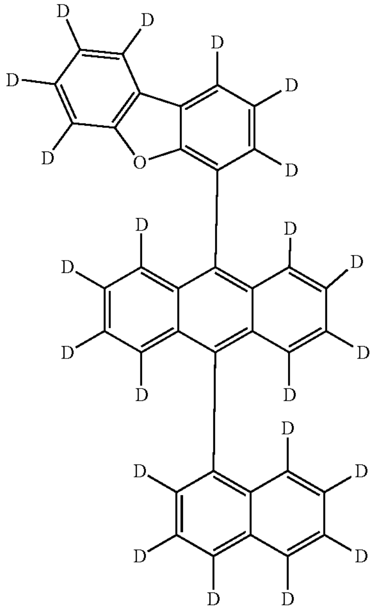
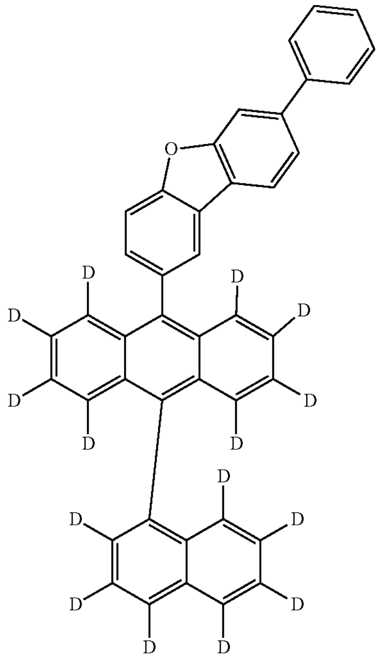
-continued
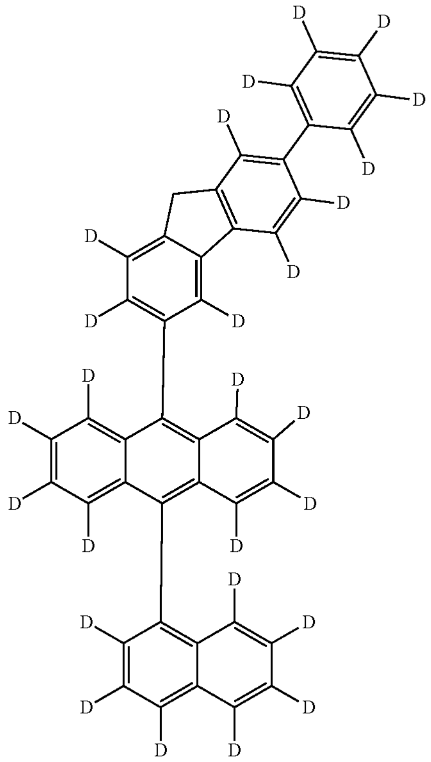
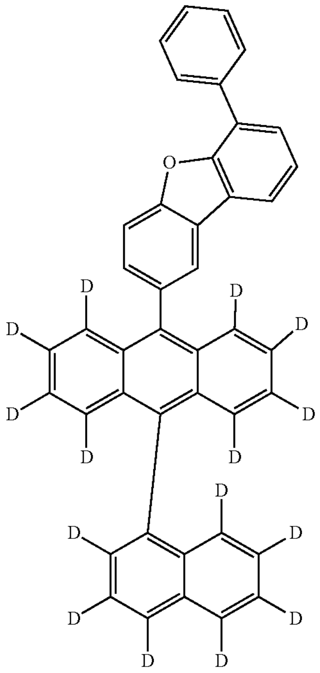

-continued
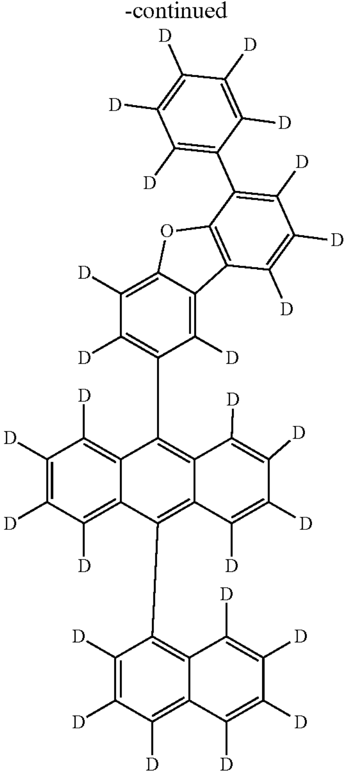
-continued
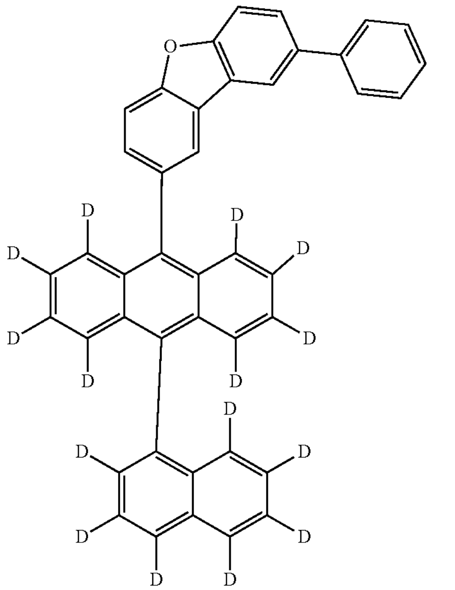
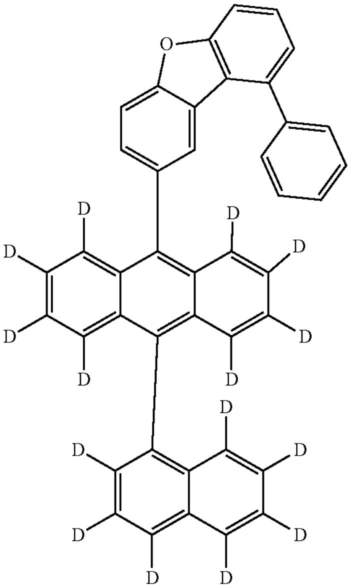
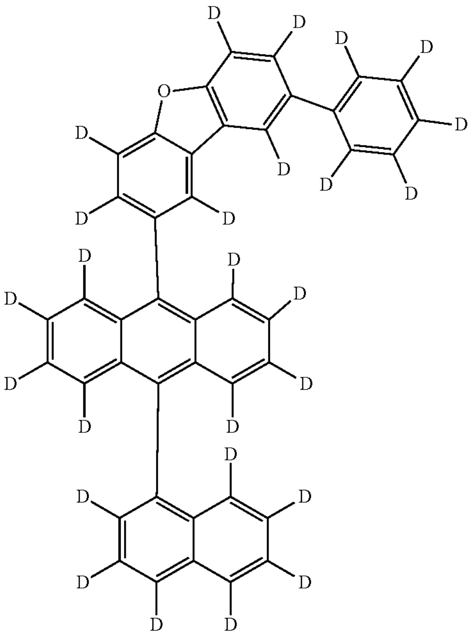

-continued
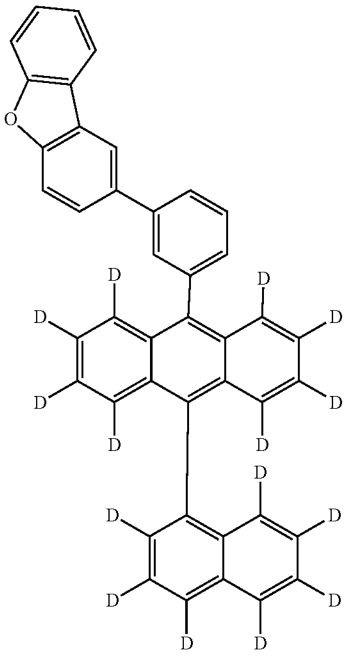
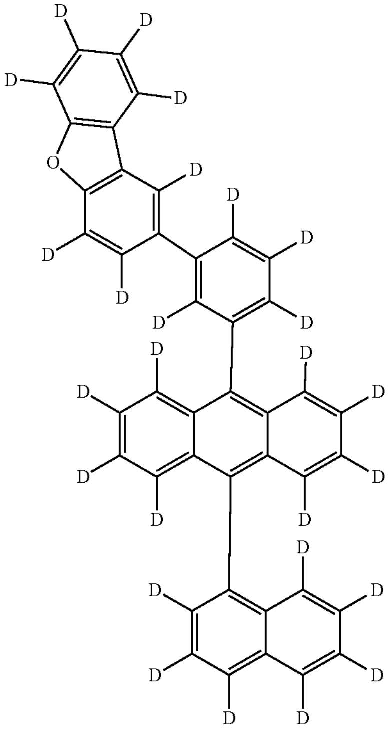
-continued
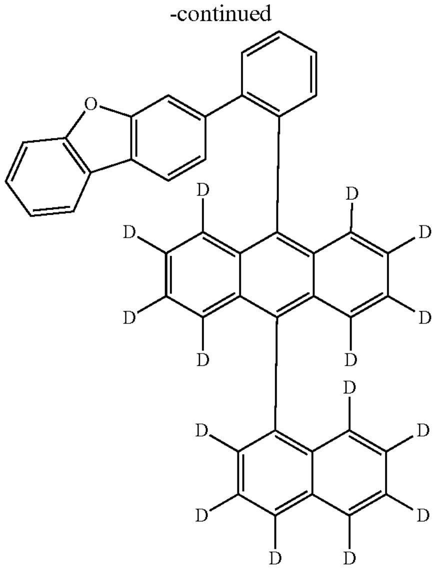
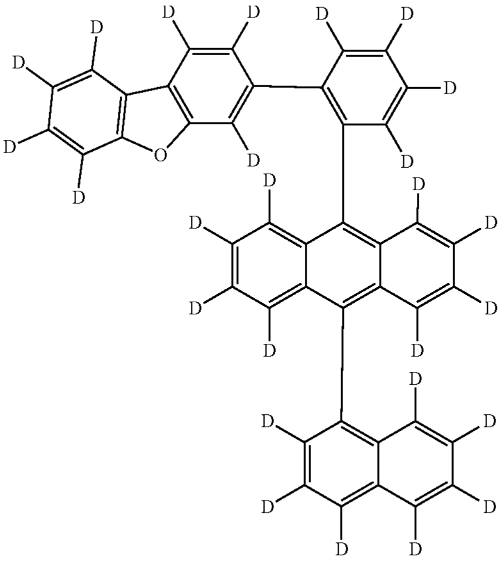

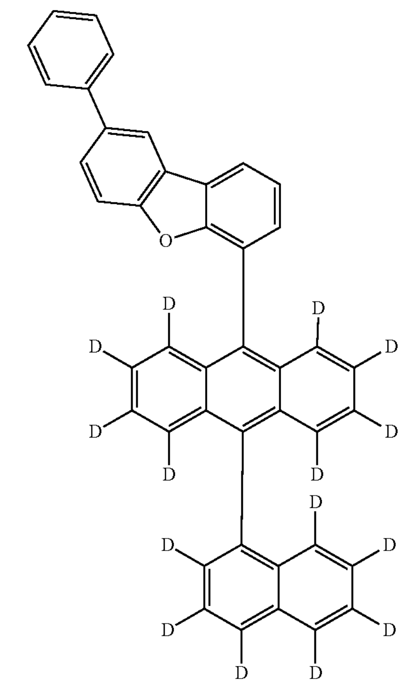
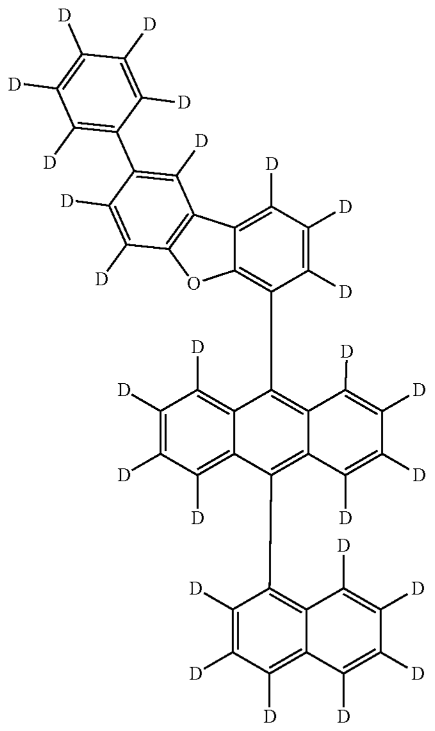
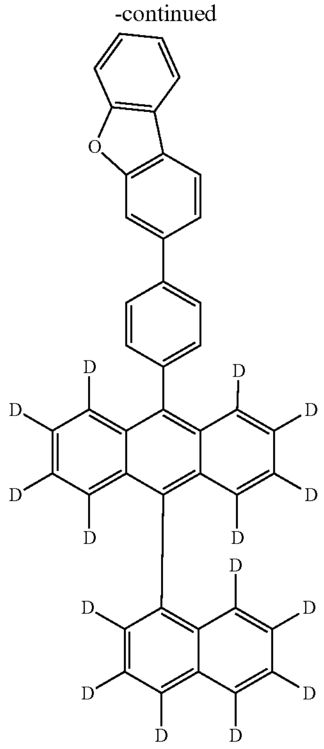
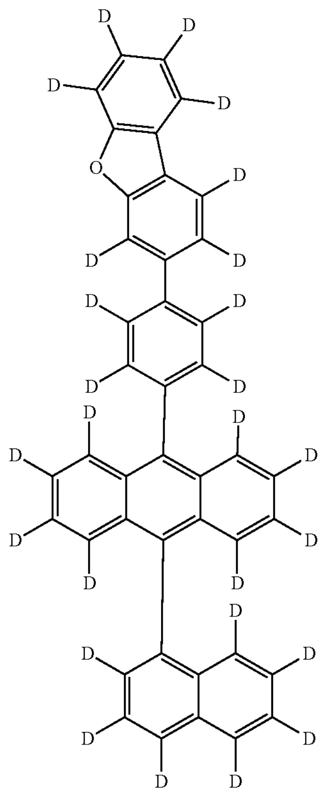

-continued
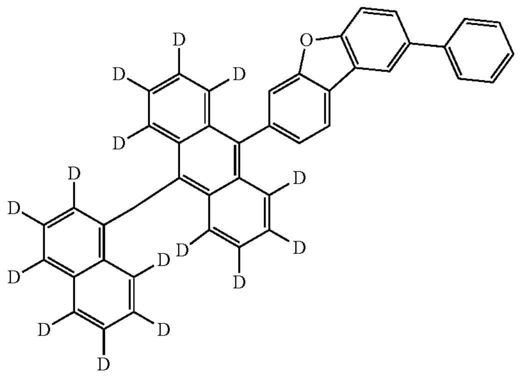
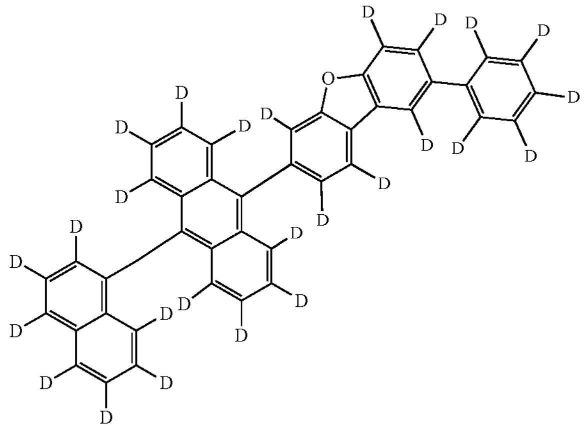
-continued
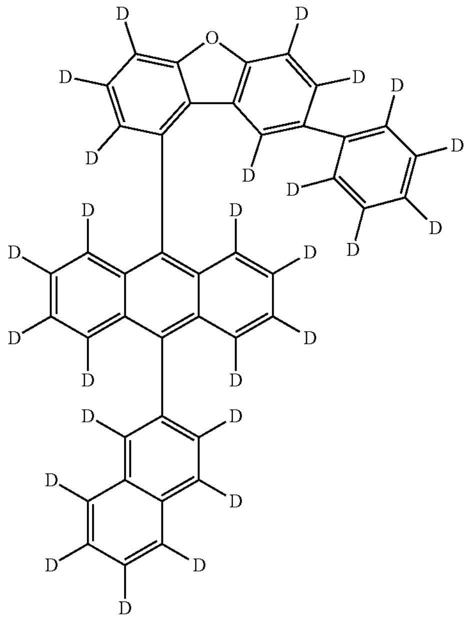
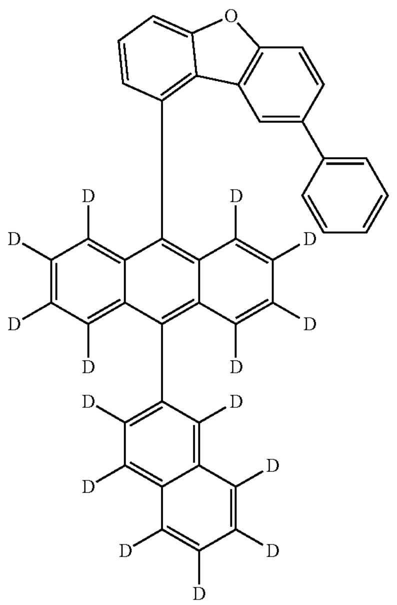
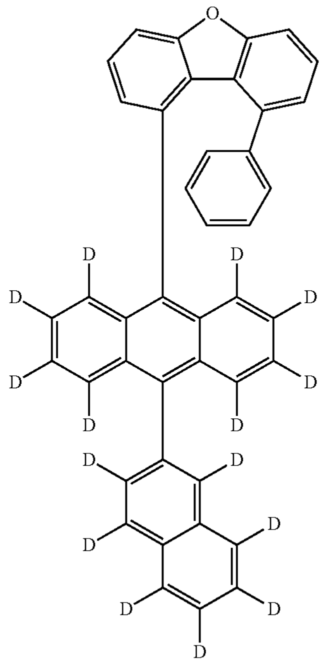

-continued
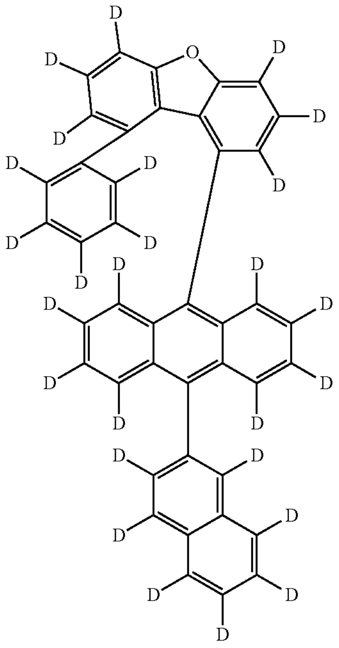
-continued
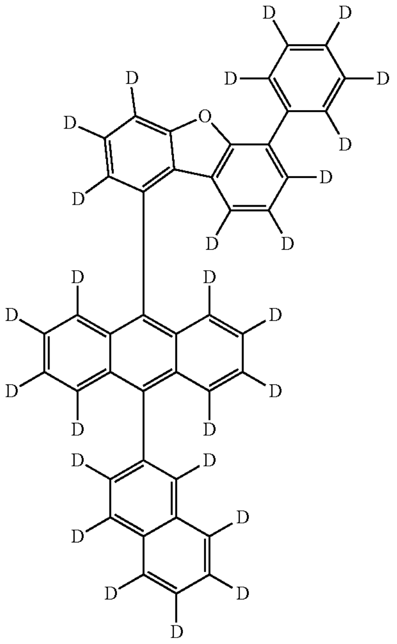
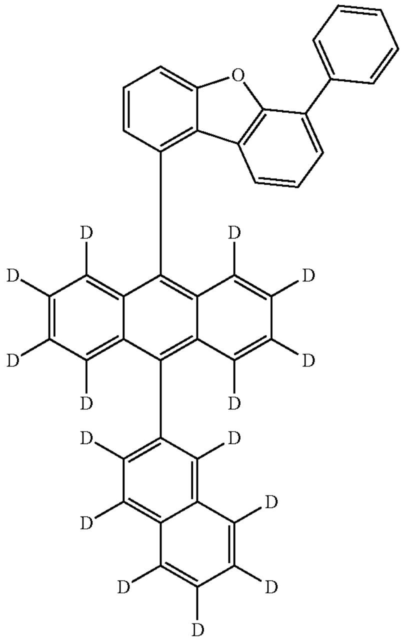
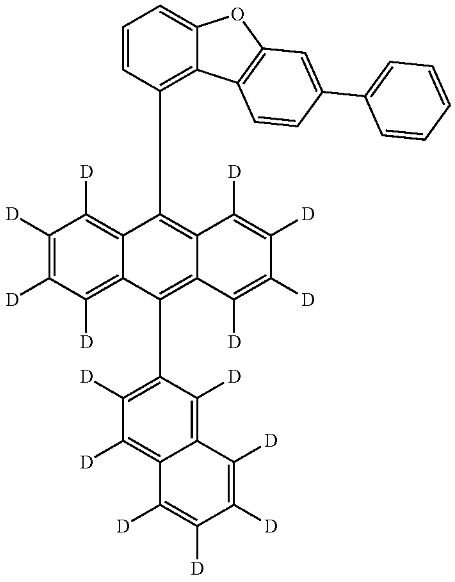

-continued
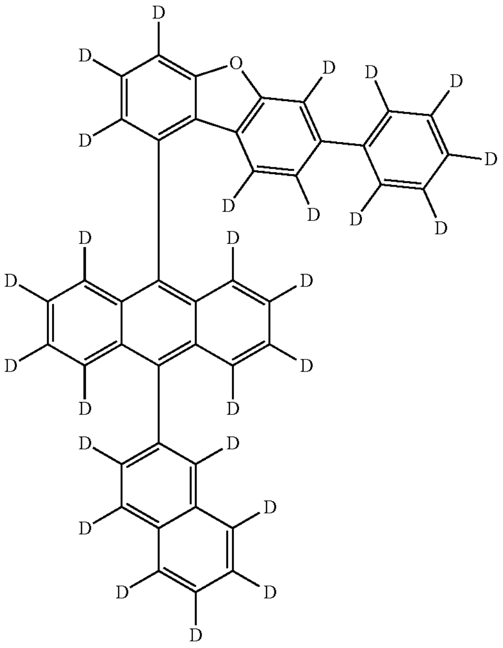
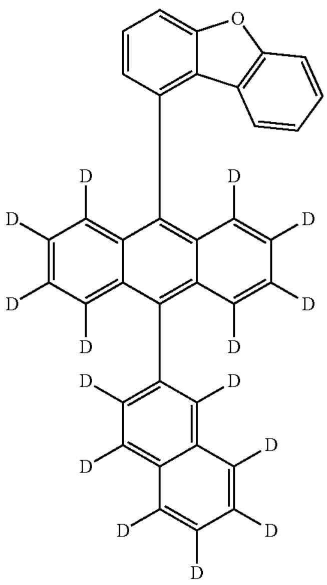
-continued
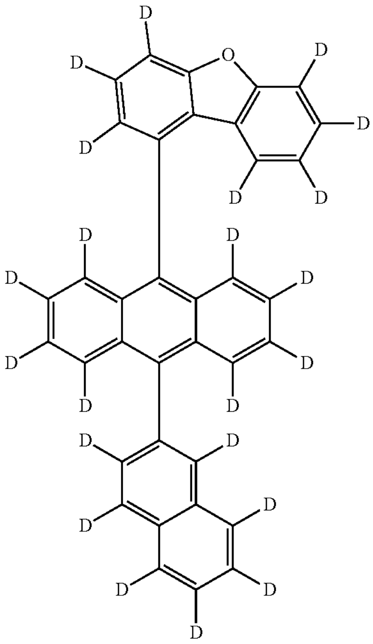
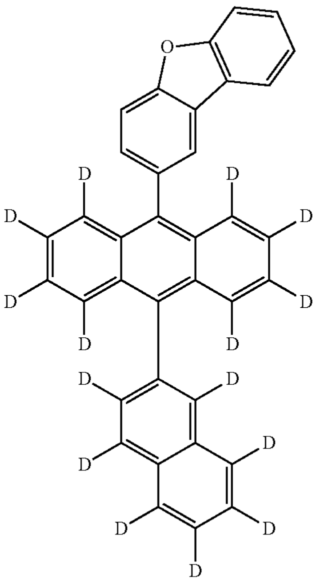

-continued
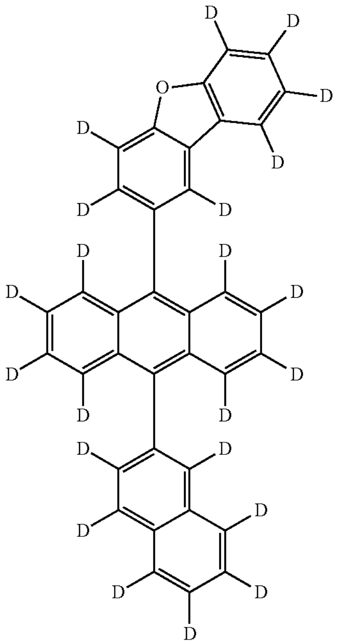
-continued
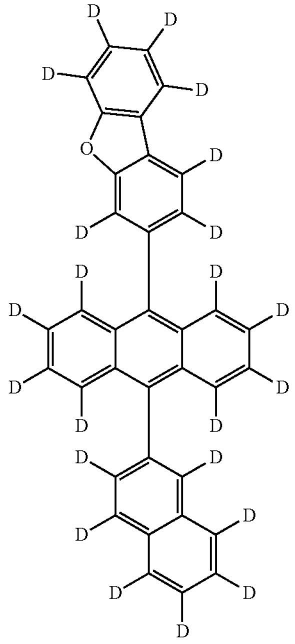
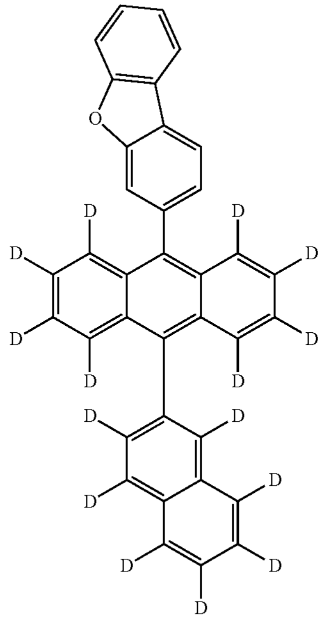
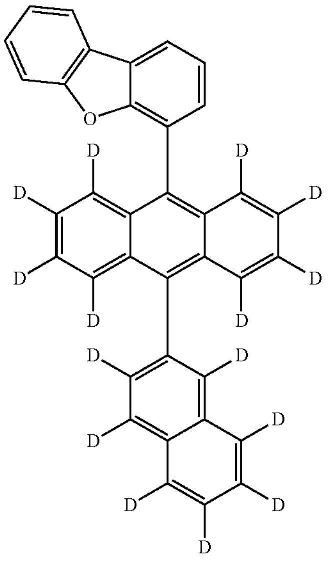

-continued
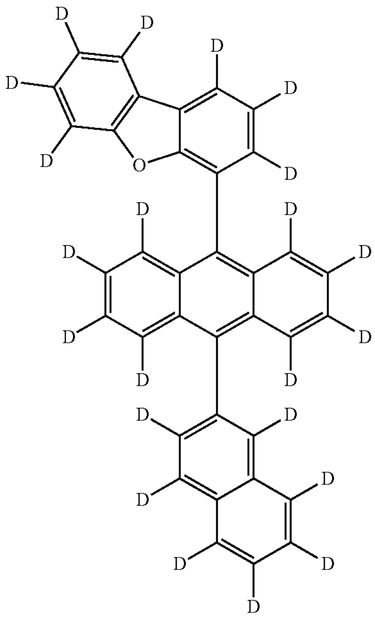
-continued
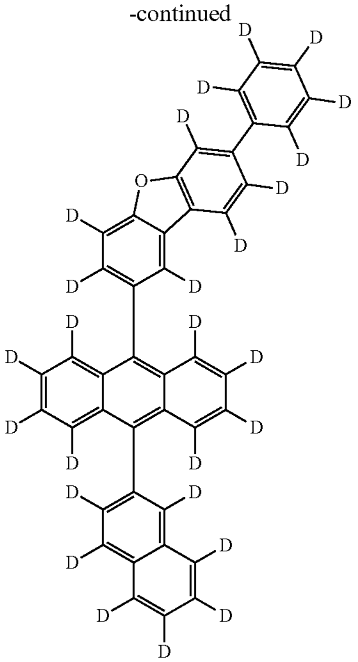
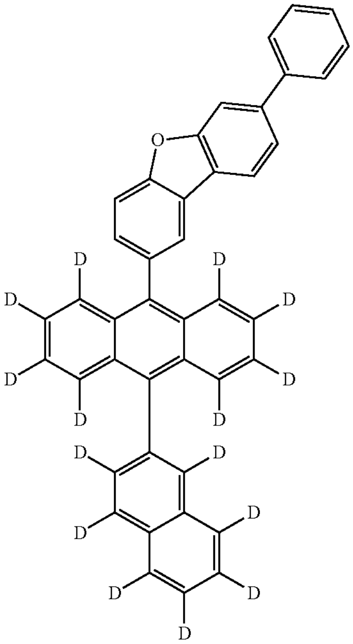
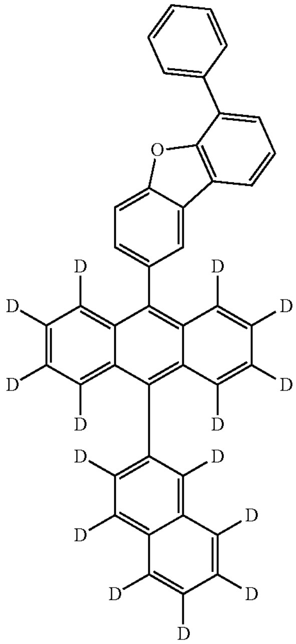

-continued
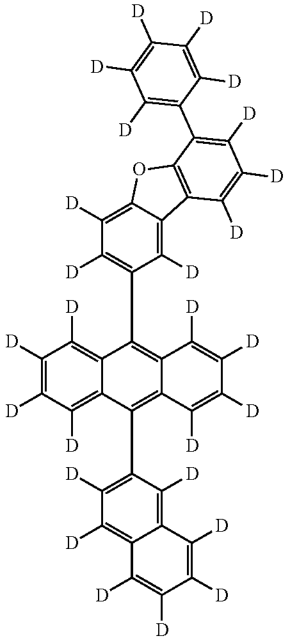
-continued
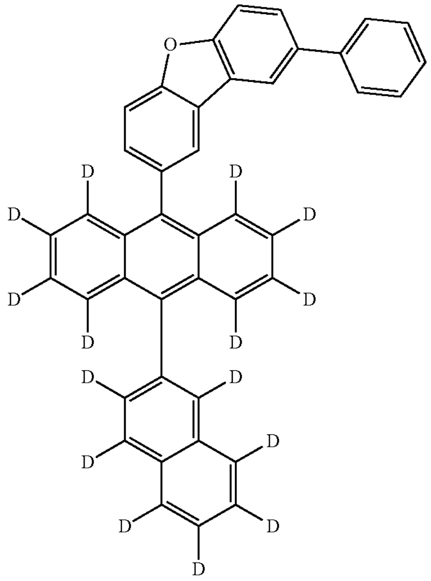
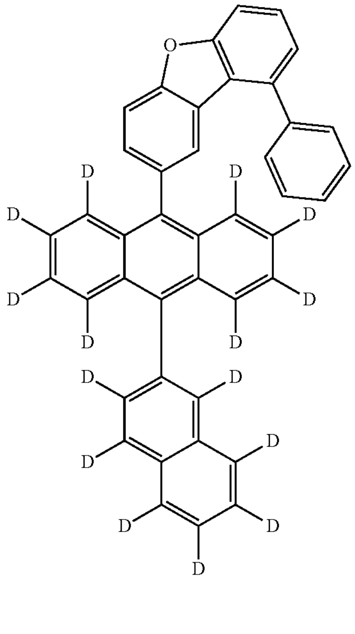
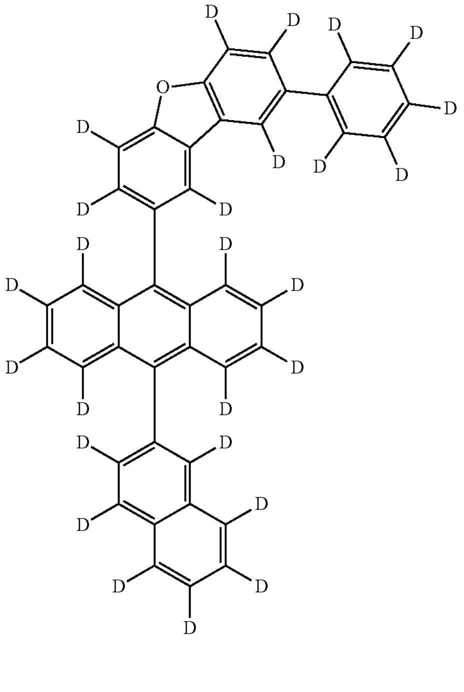 [SMILES: [2H]c1c([2H])c([2H])c(-c2c([2H])c([2H])c3oc4c([2H])c([2H])c(-c5c6c([2H])c([2H])c([2H])c([2H])c6c(-c6c([2H])c([2H])c7c([2H])c([2H])c([2H])c([2H])c7c6[2H])c6c([2H])c([2H])c([2H])c([2H])c56)c([2H])c4c3c2[2H])c([2H])c1[2H]]

-continued
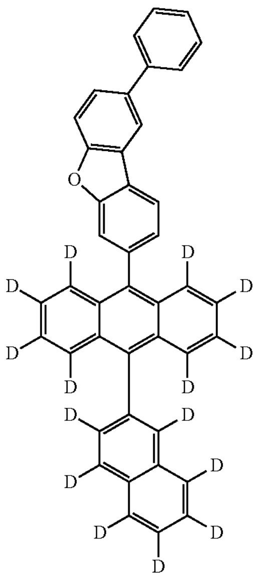
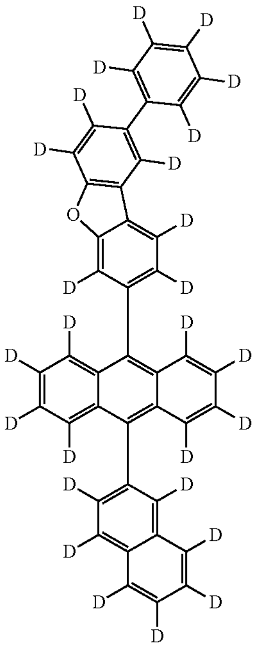
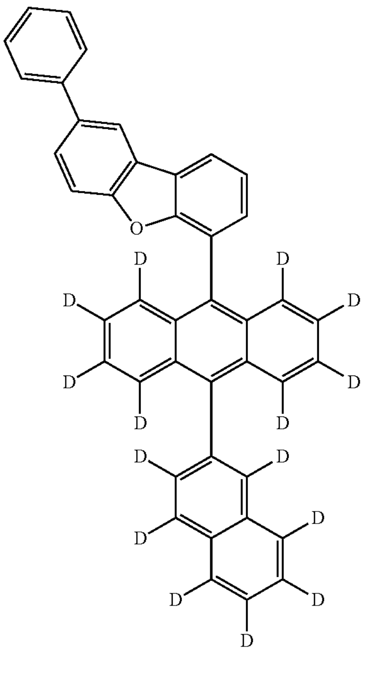
-continued
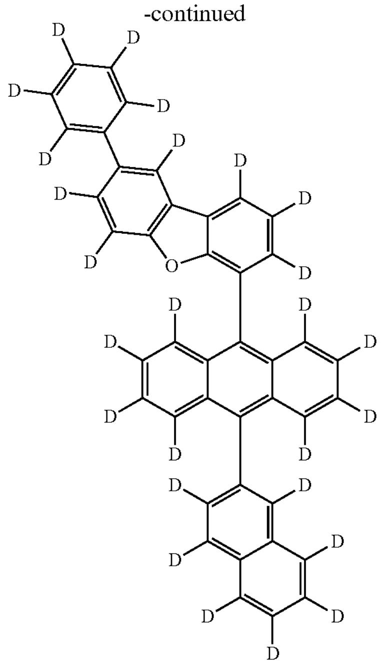
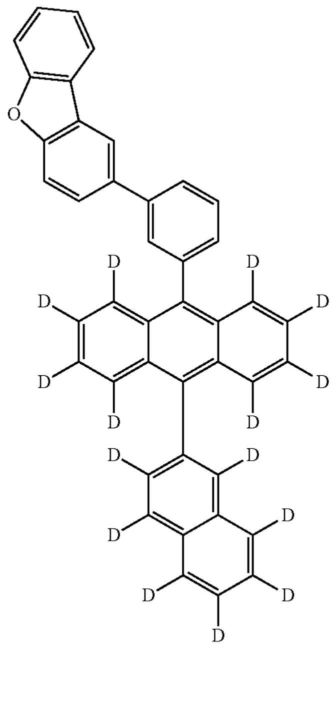

-continued
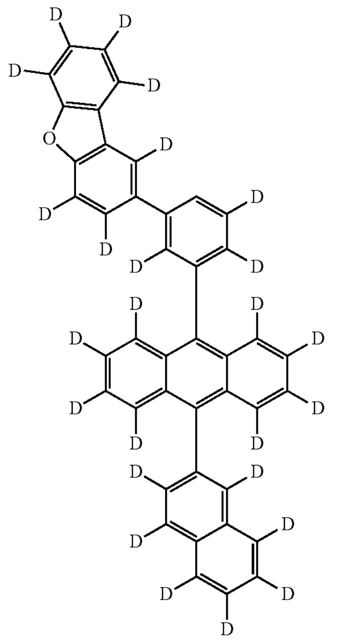
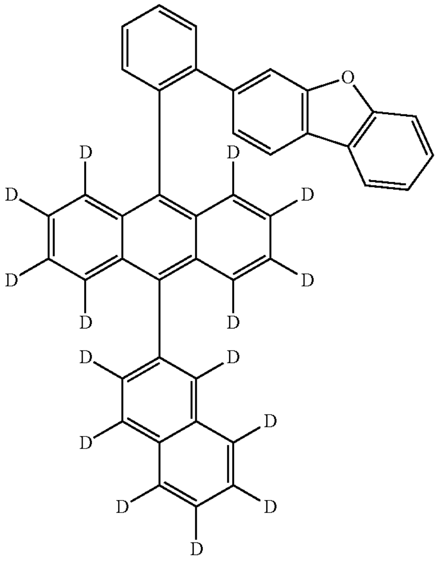
-continued
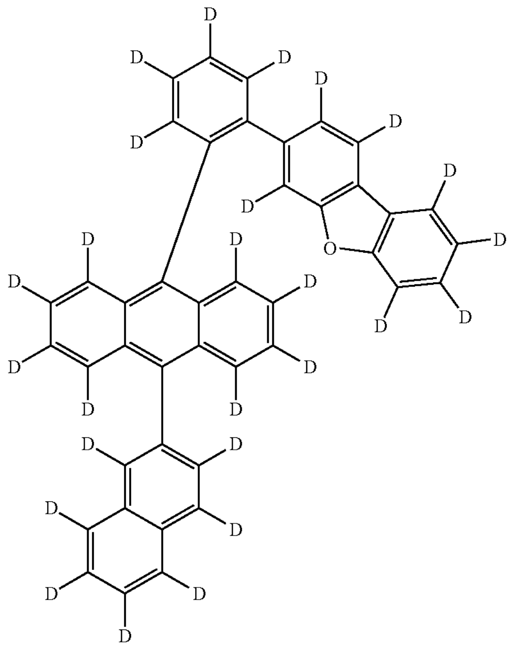
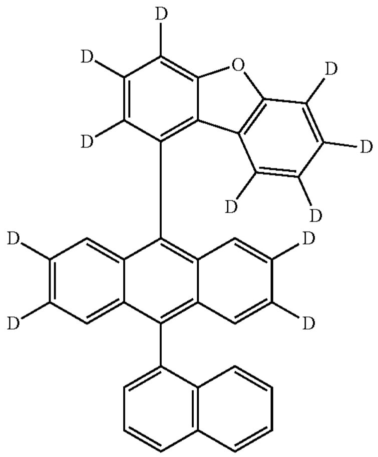
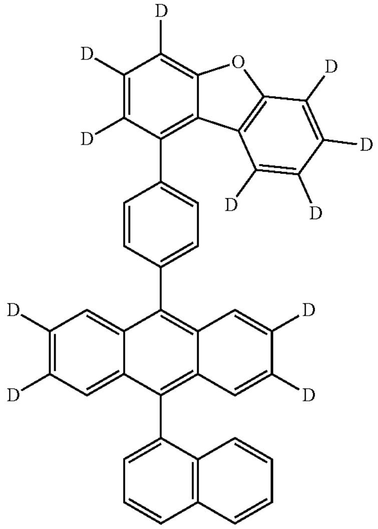

-continued
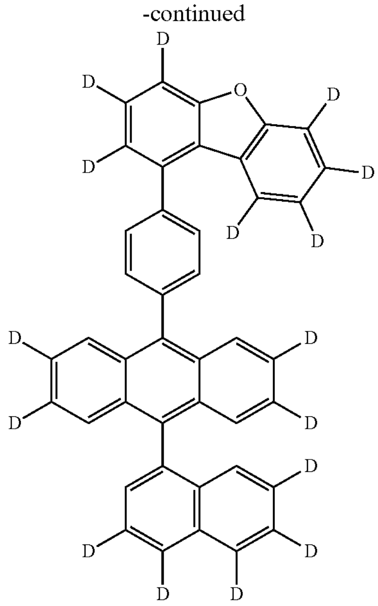
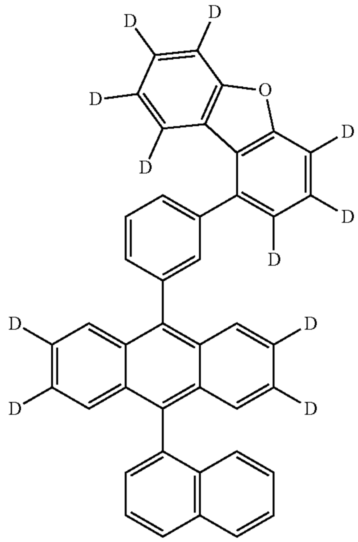
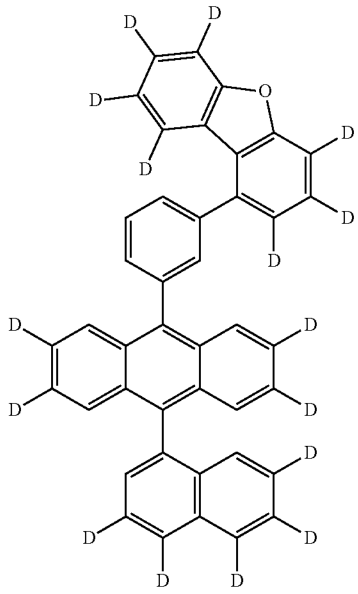
-continued
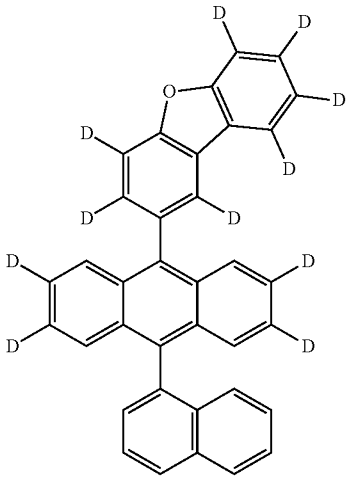
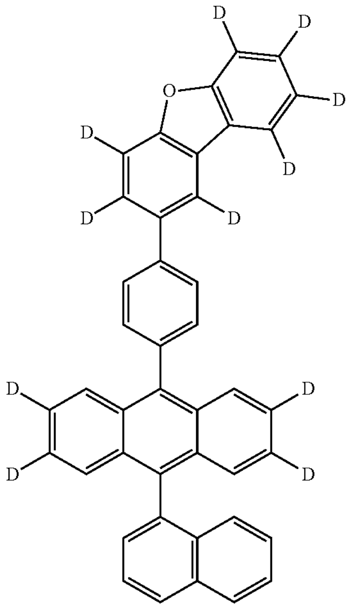

-continued
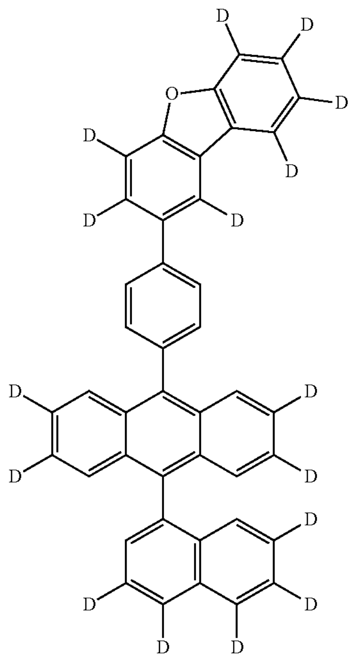
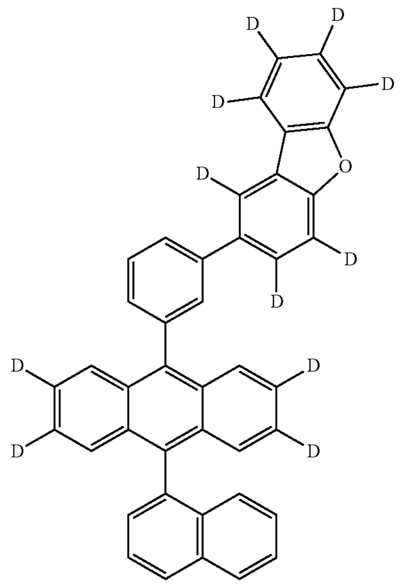
-continued
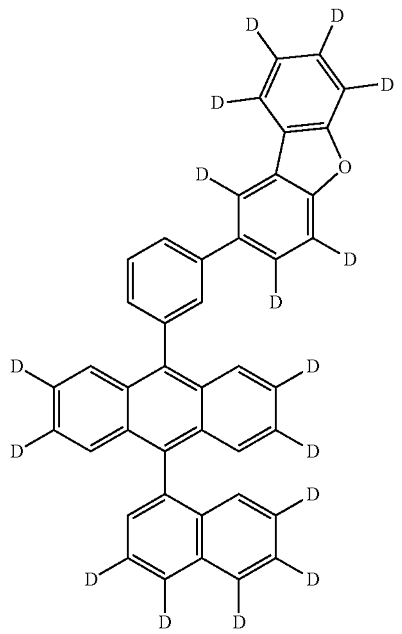
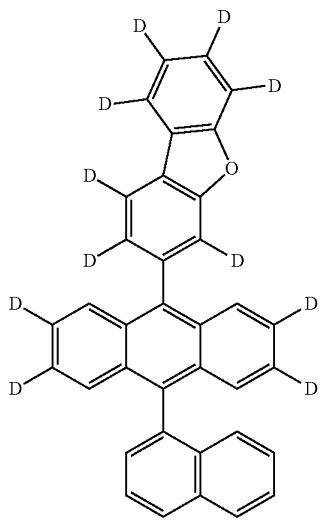

-continued
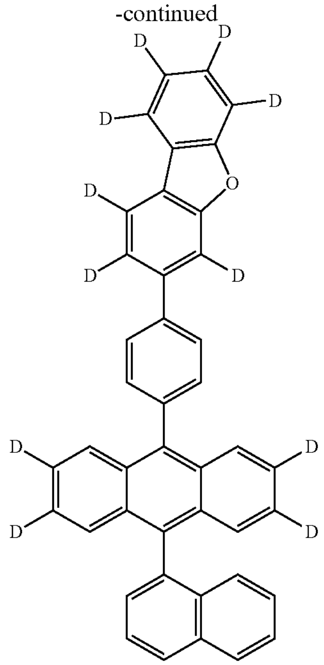
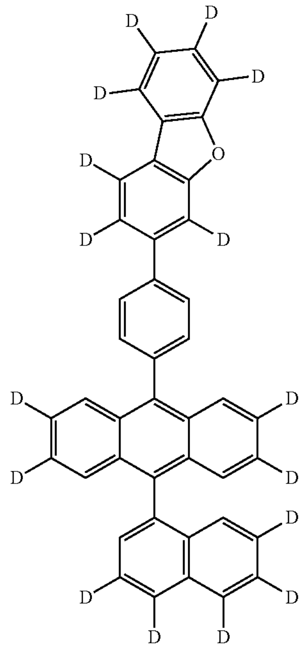
-continued
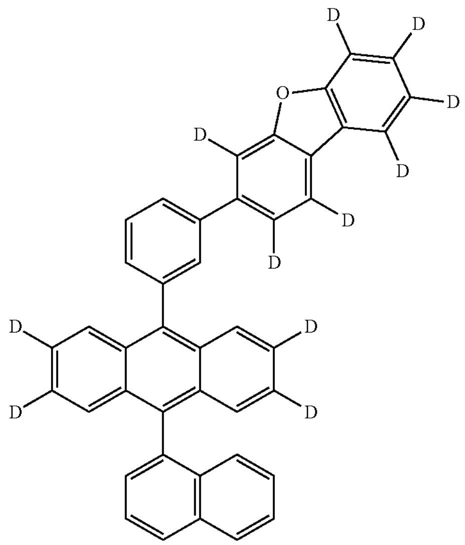
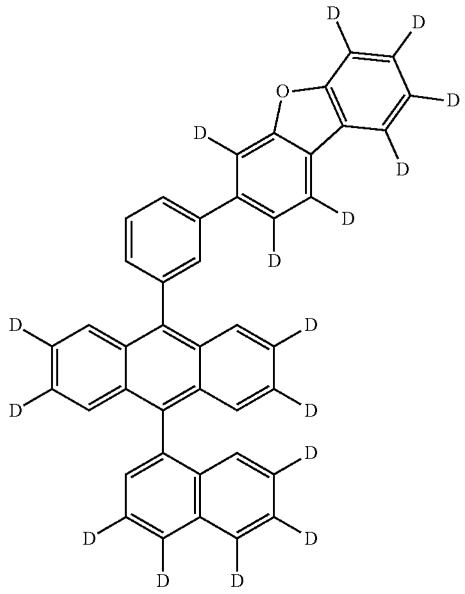
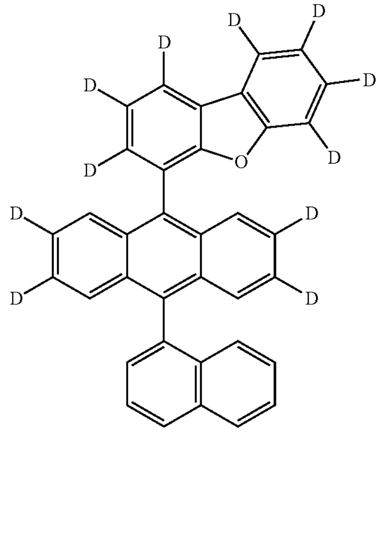

-continued
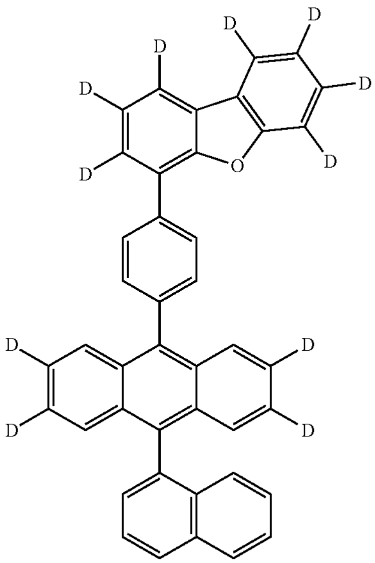
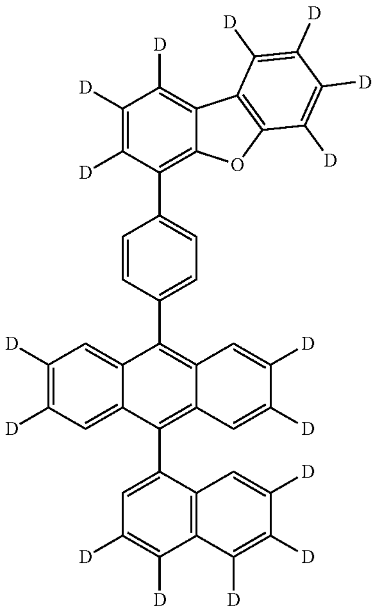
-continued
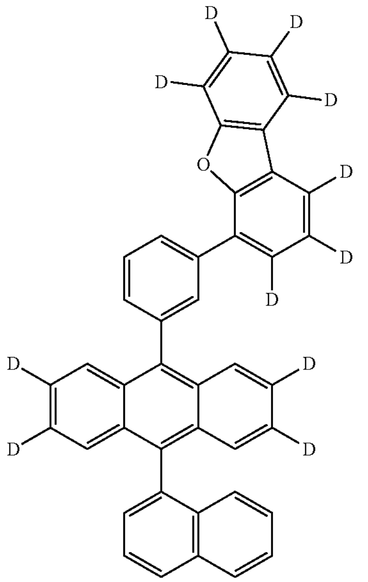
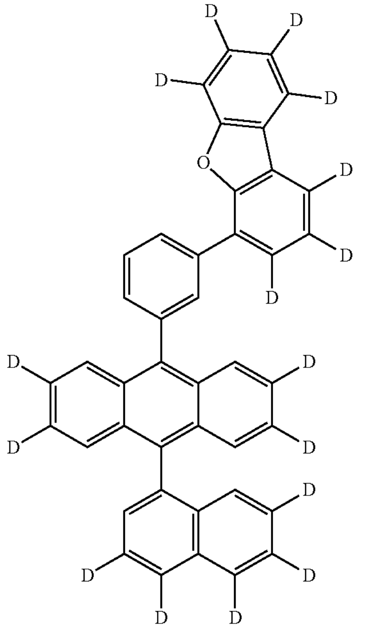
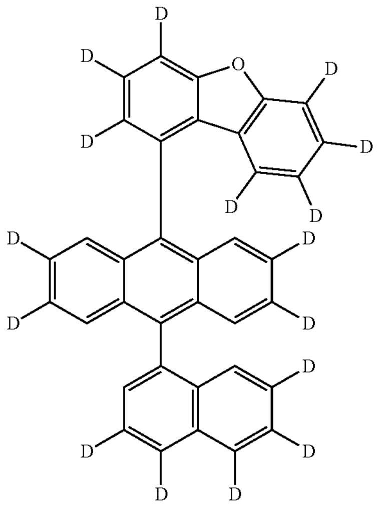

-continued
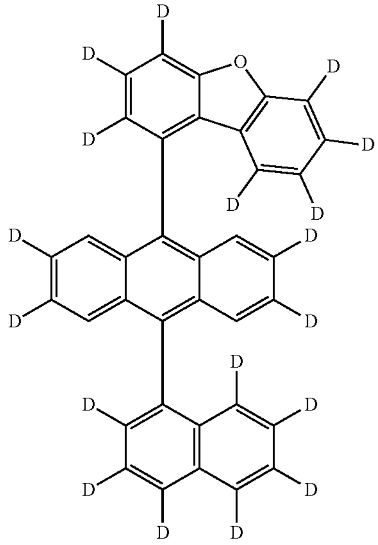
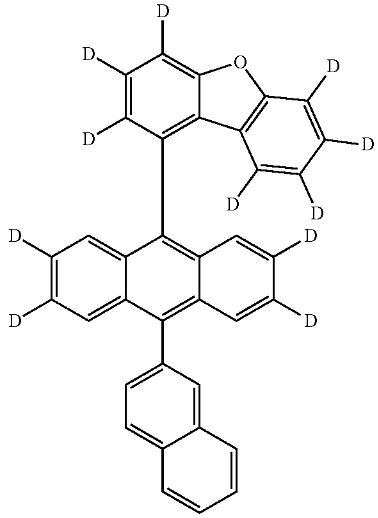
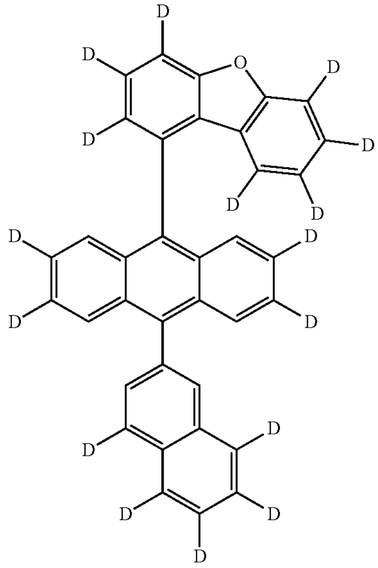
-continued
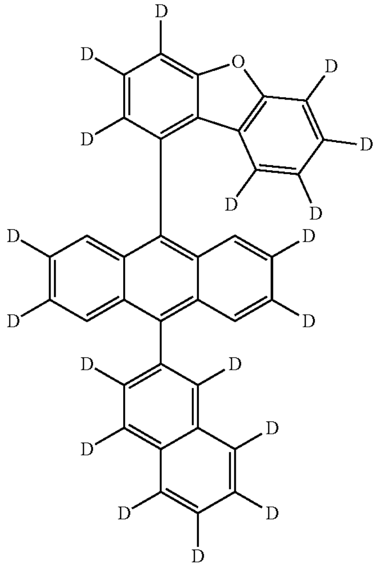
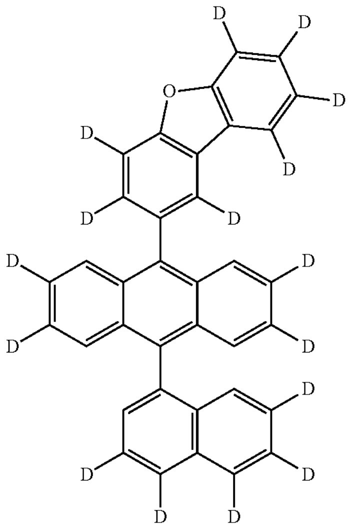
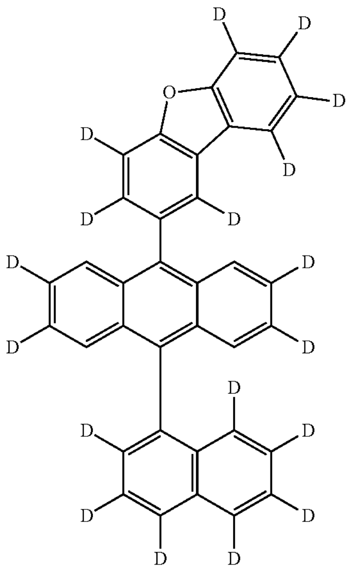

-continued
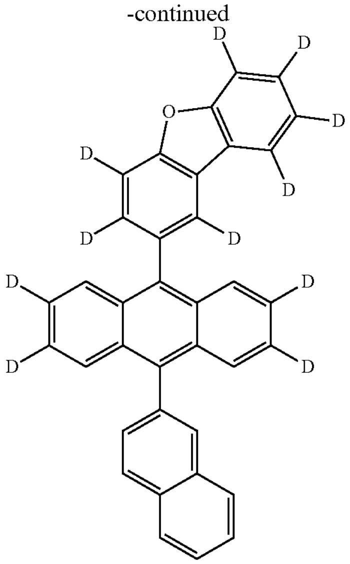
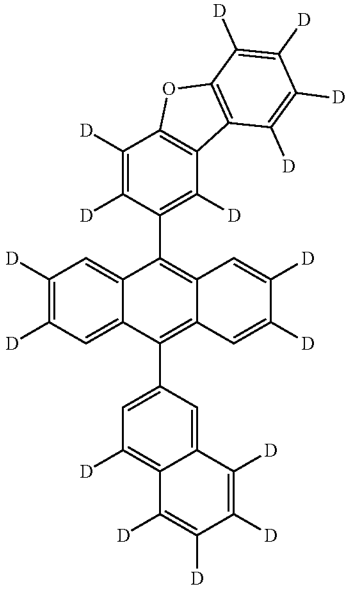
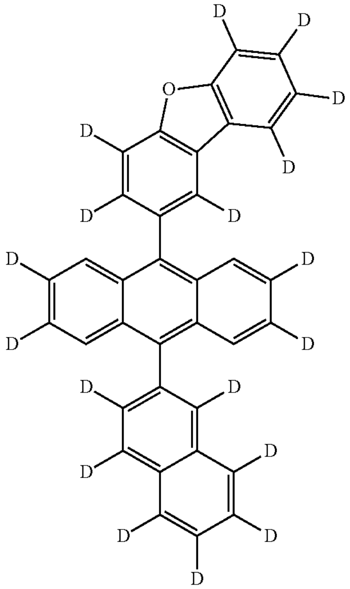
-continued
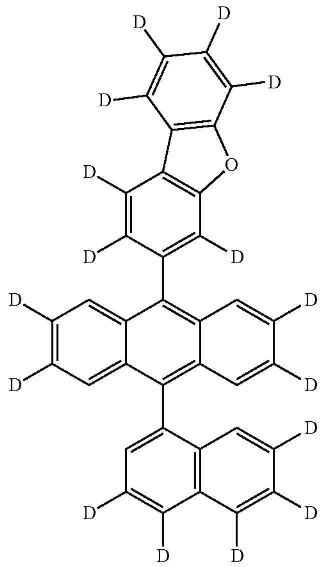
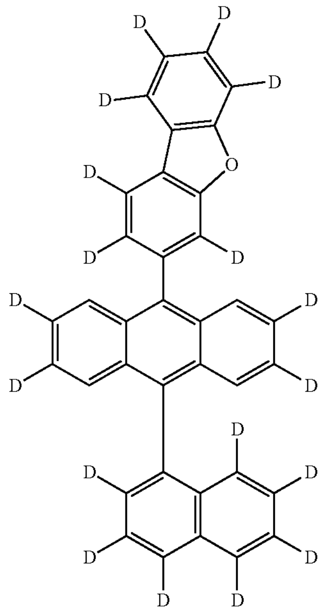

-continued
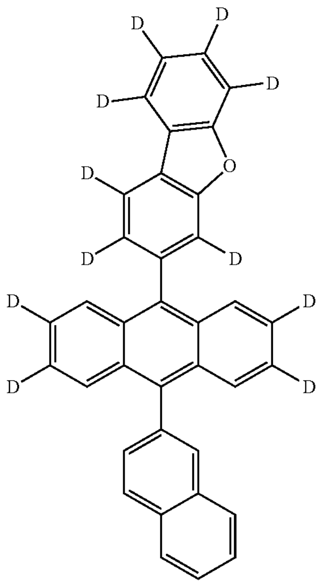
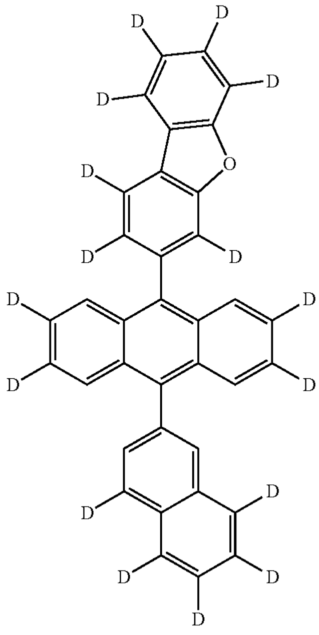
-continued
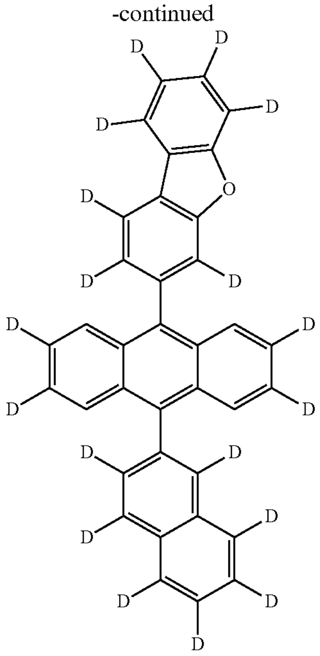
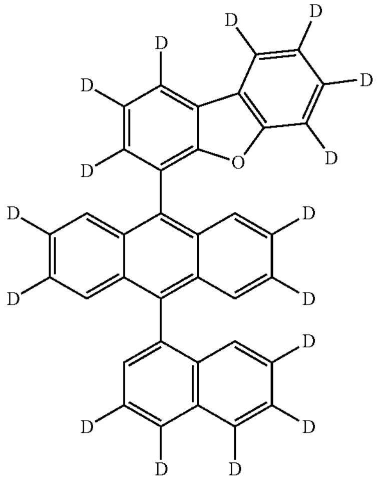
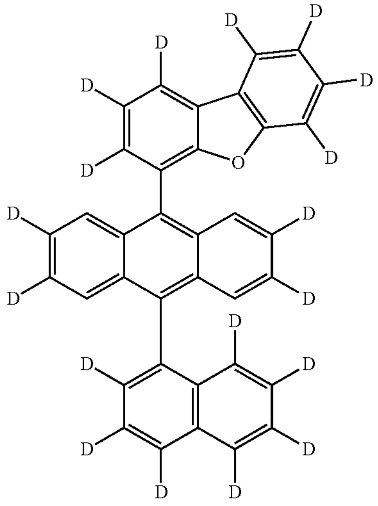

-continued
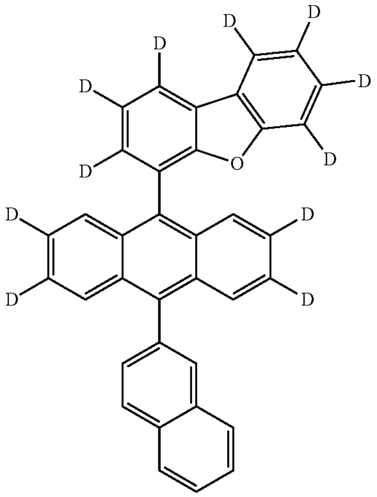
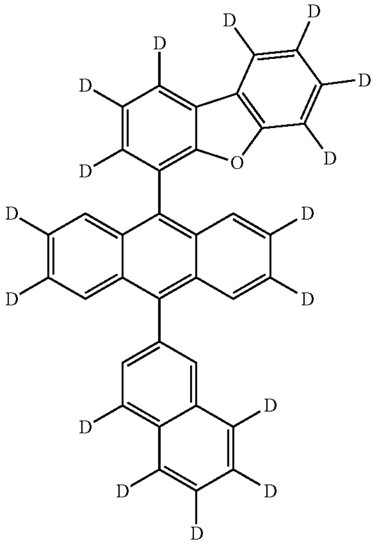
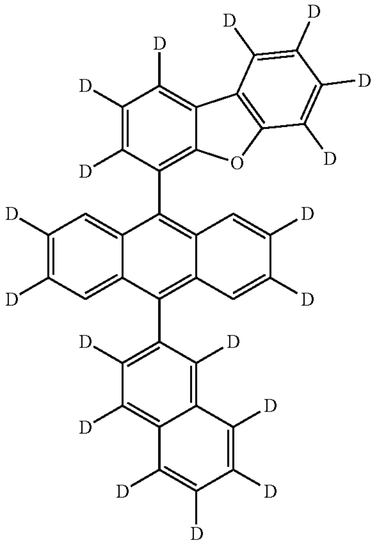
-continued
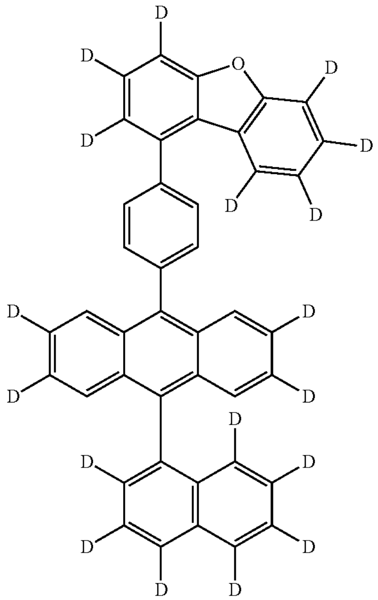
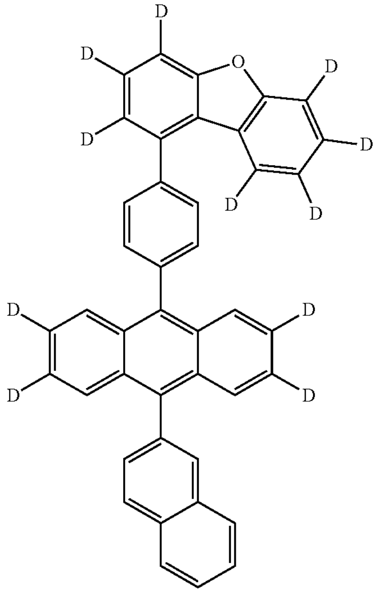

-continued
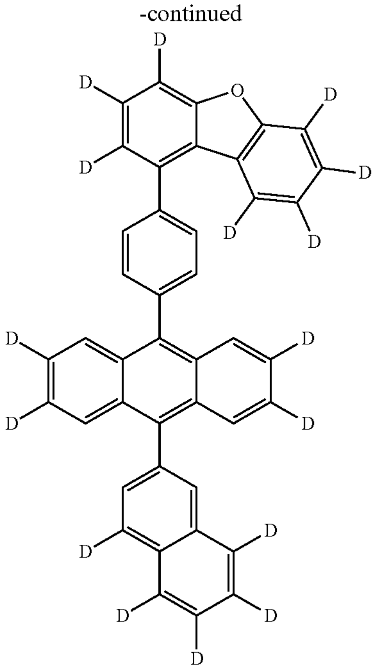
-continued
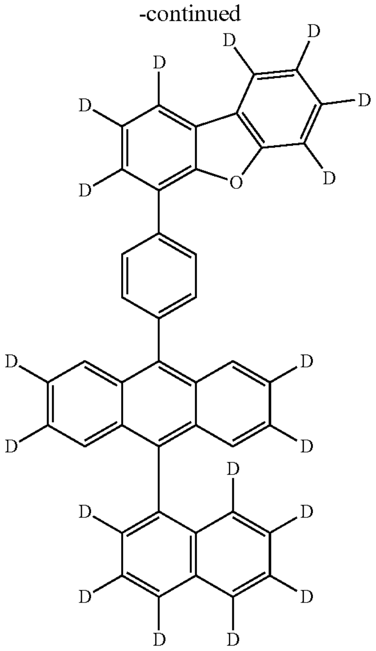
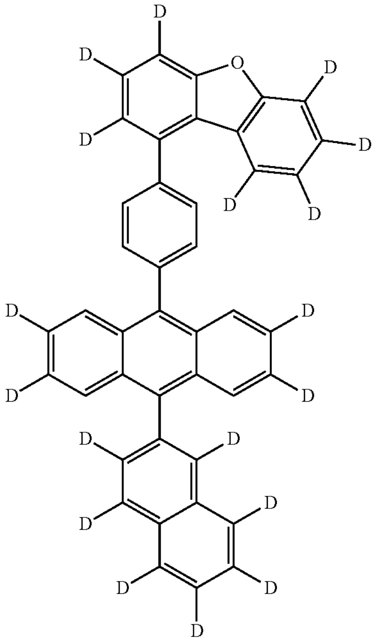
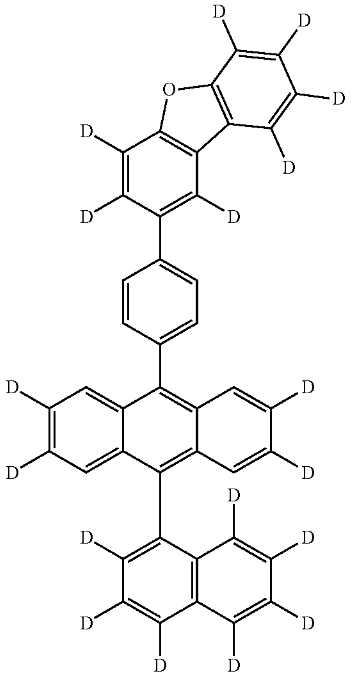

-continued
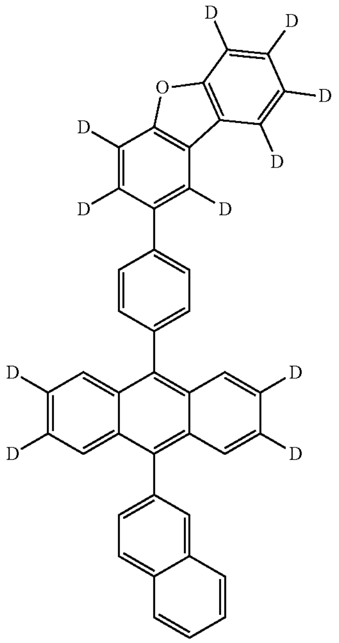
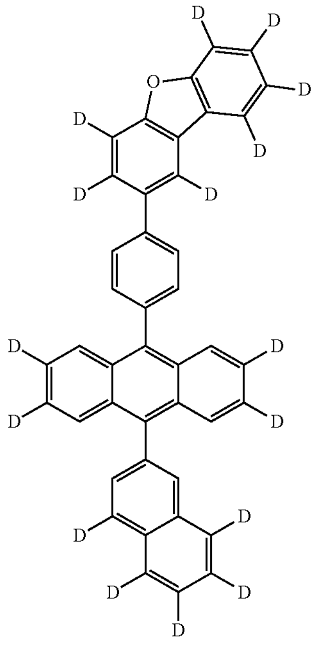
-continued
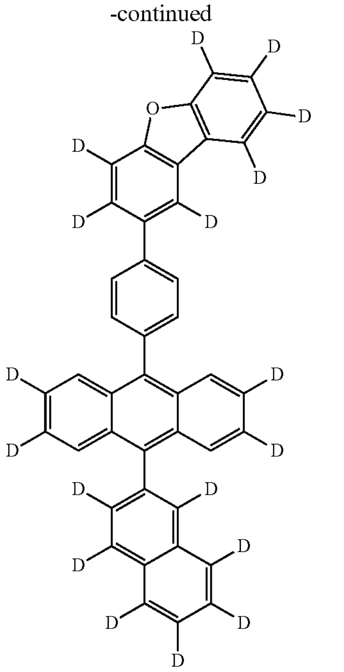
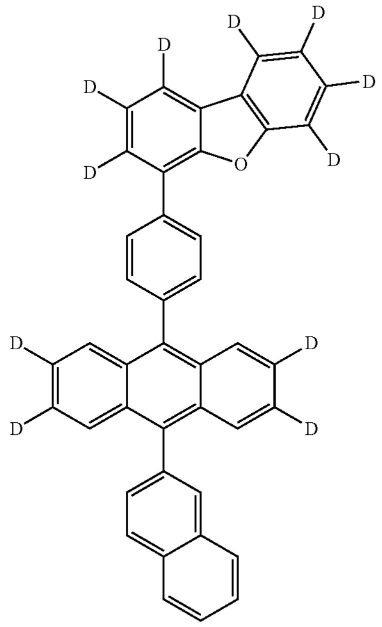

-continued
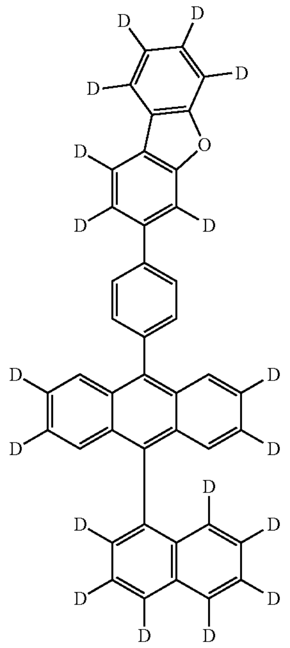
-continued
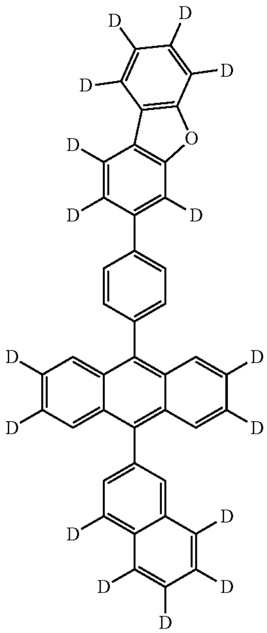
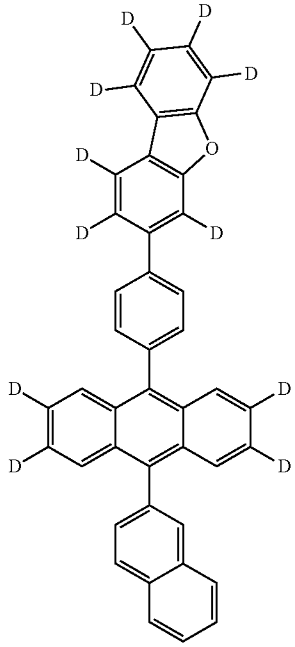
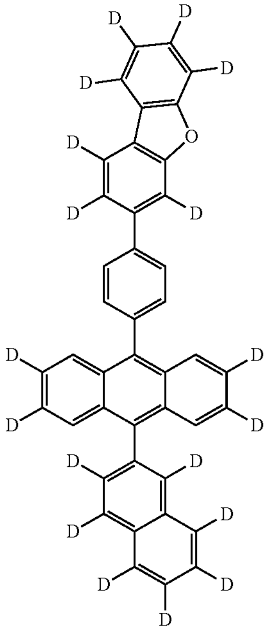

-continued
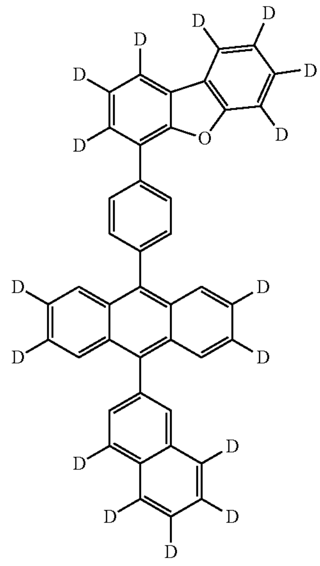
-continued
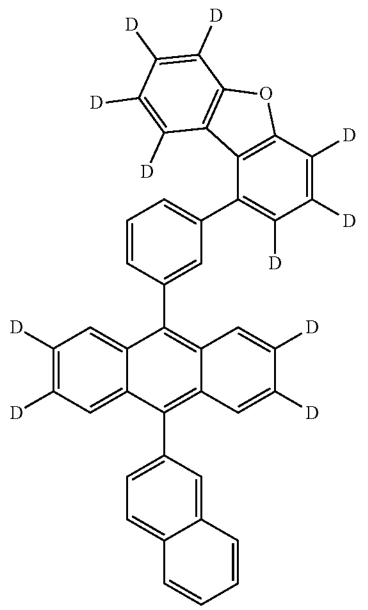
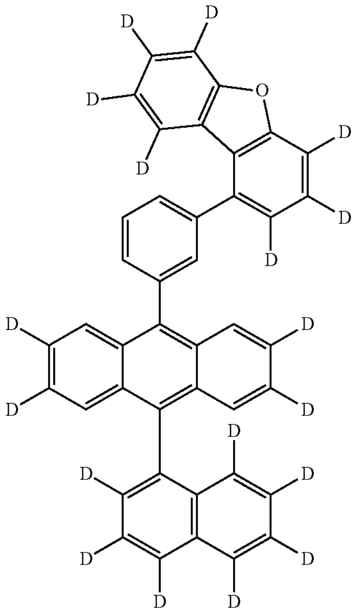
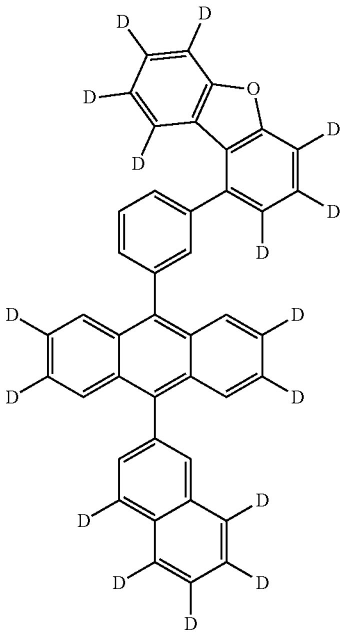

-continued
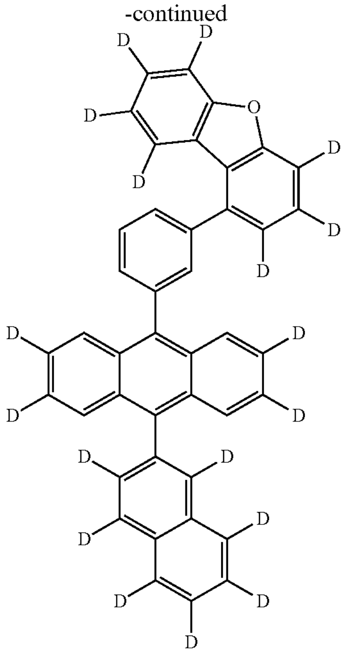
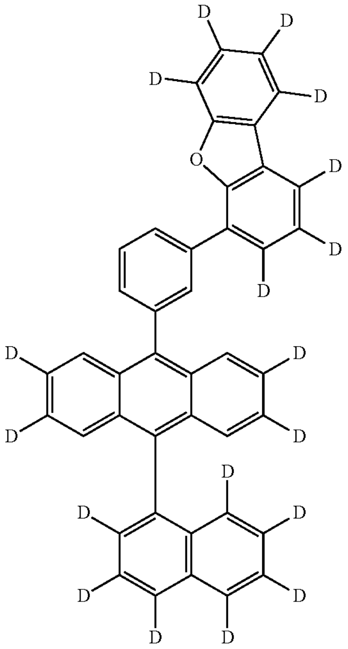
-continued
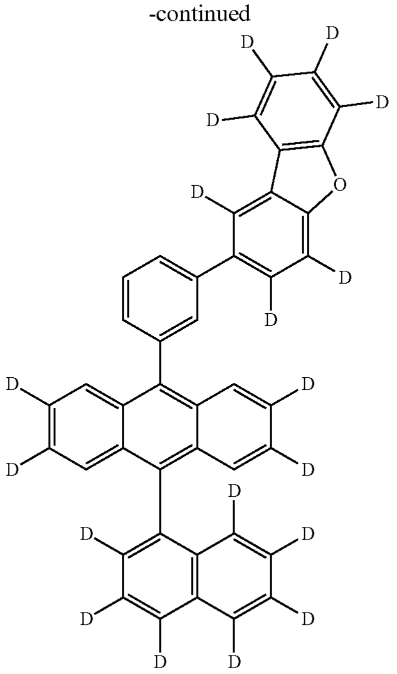
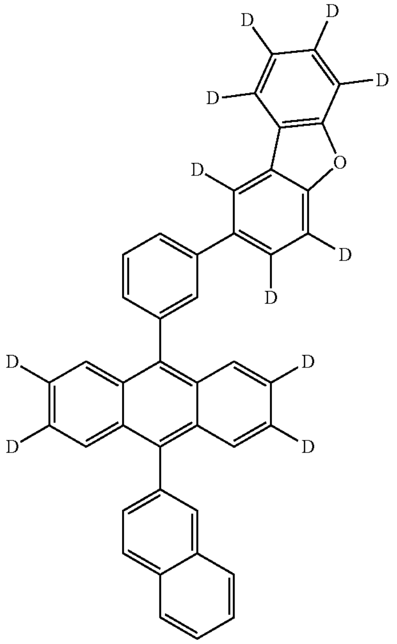

-continued
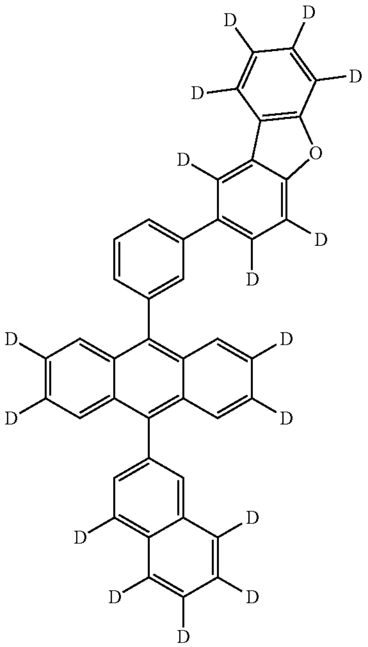
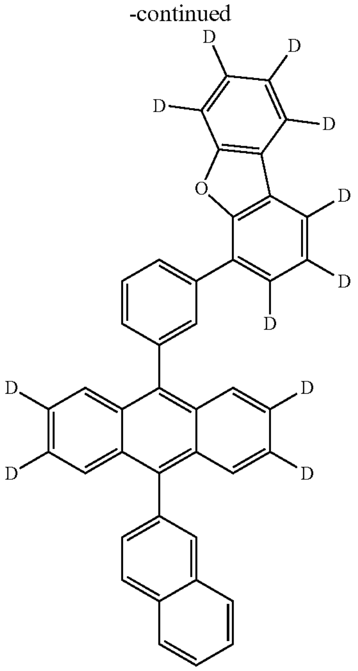
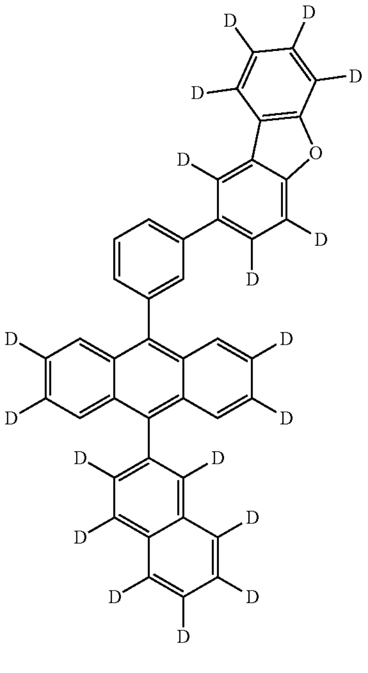
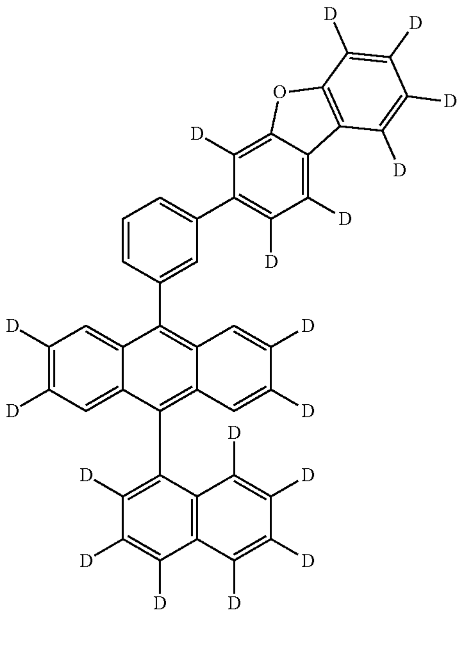
-continued

-continued
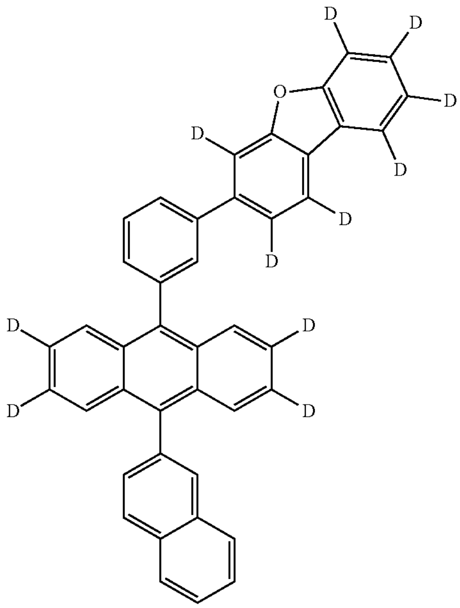
-continued
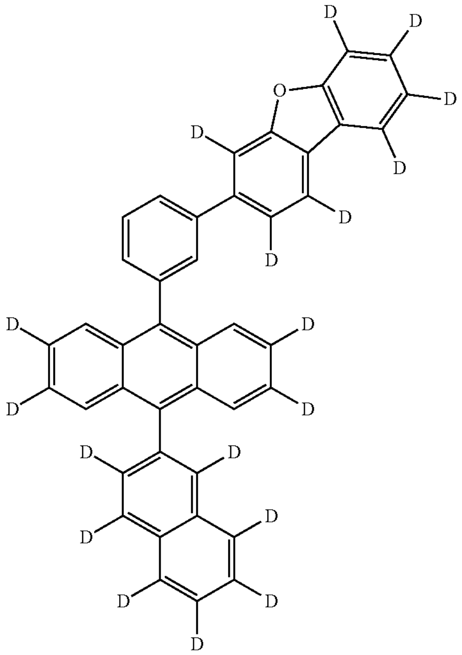
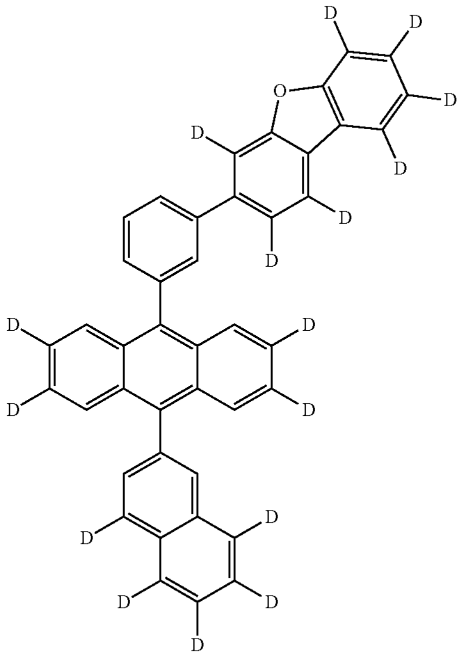
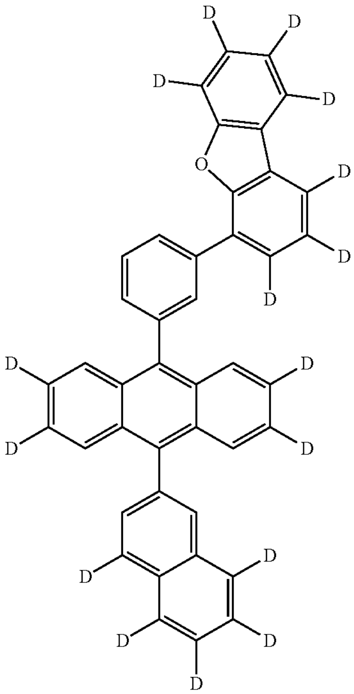

-continued
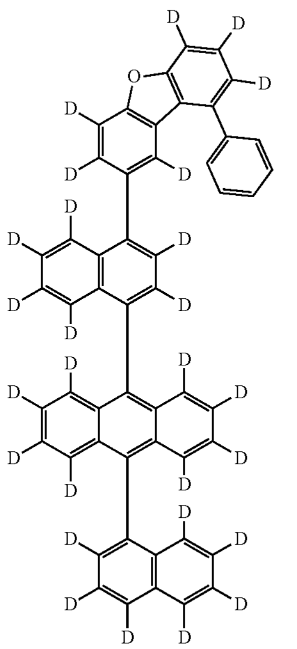
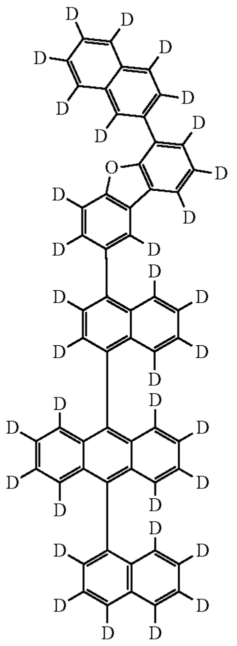
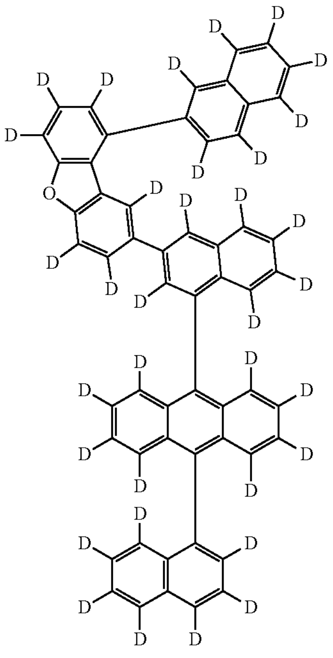
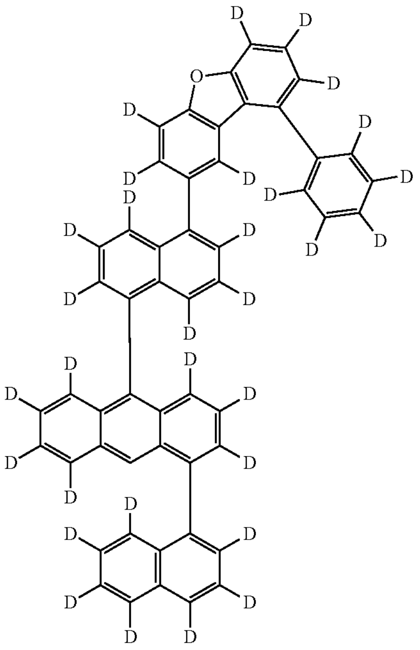

-continued
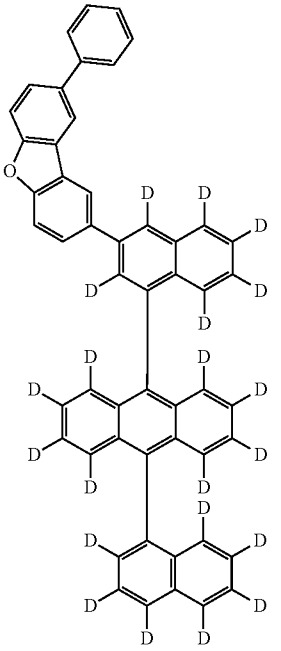
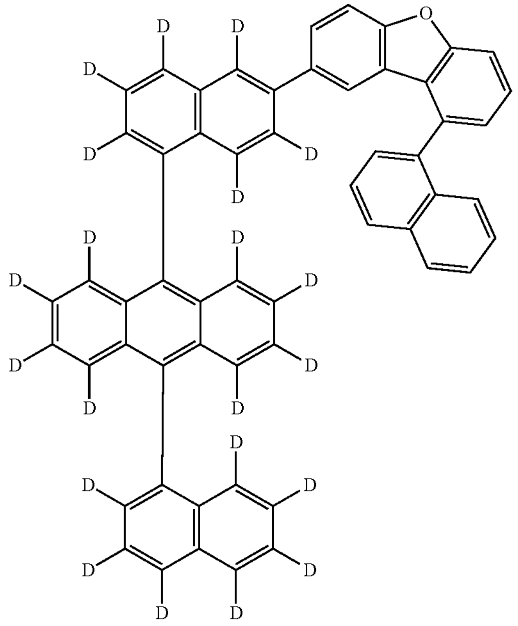
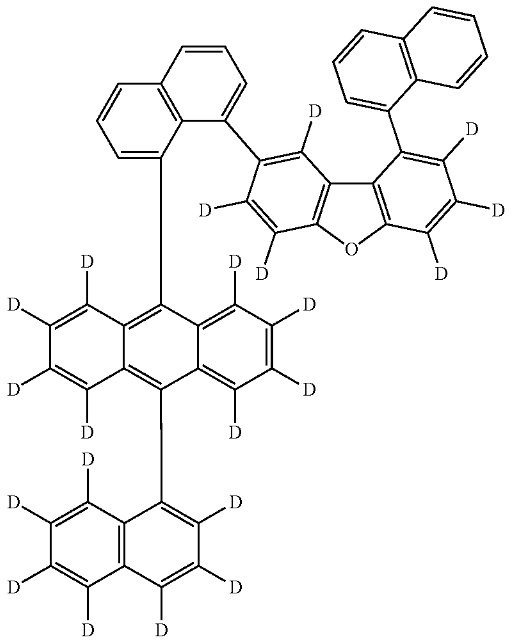
-continued
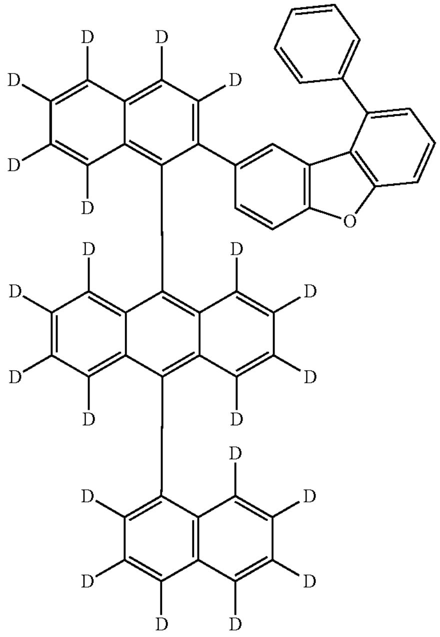

-continued
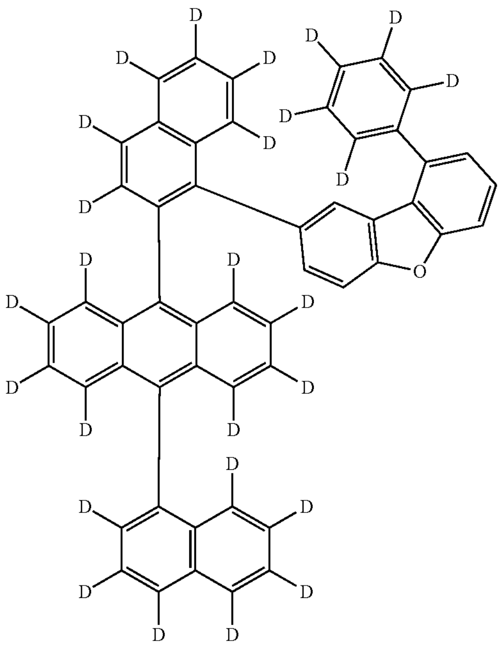
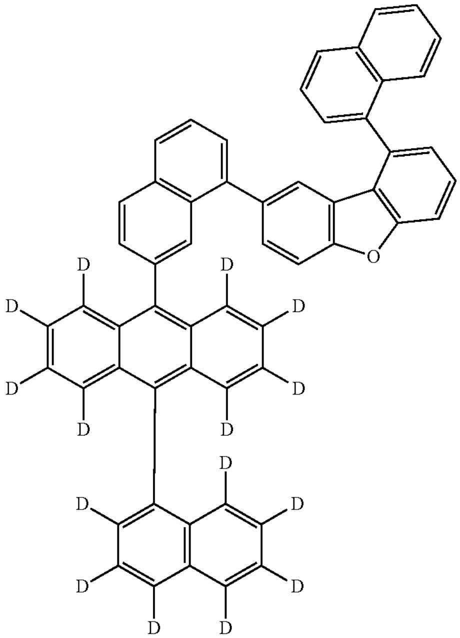
-continued
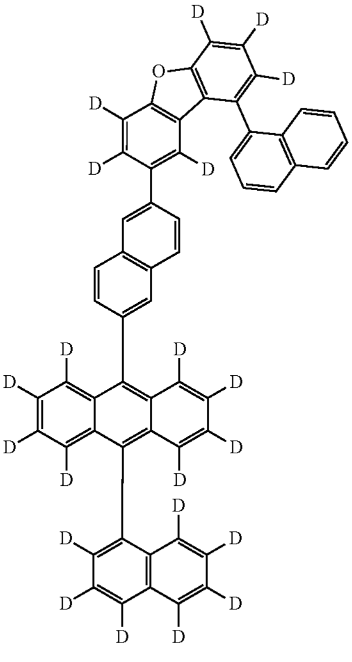
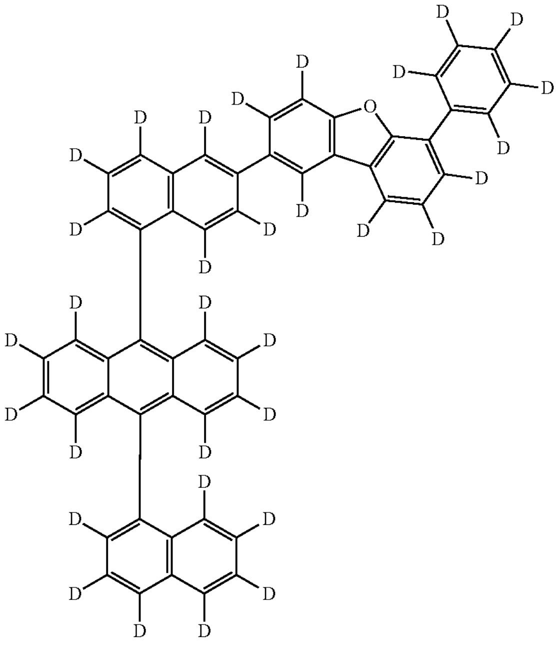

-continued
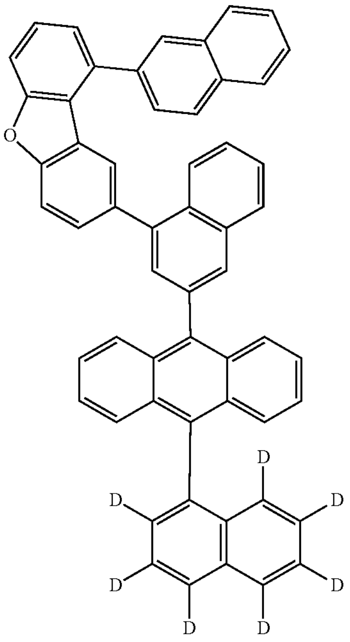
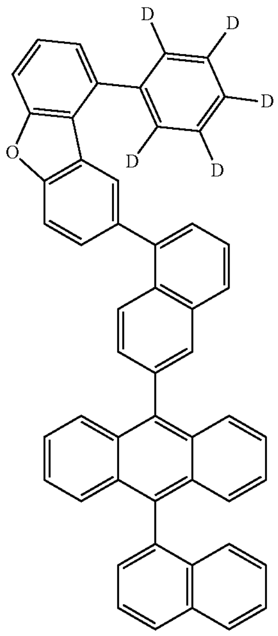
-continued
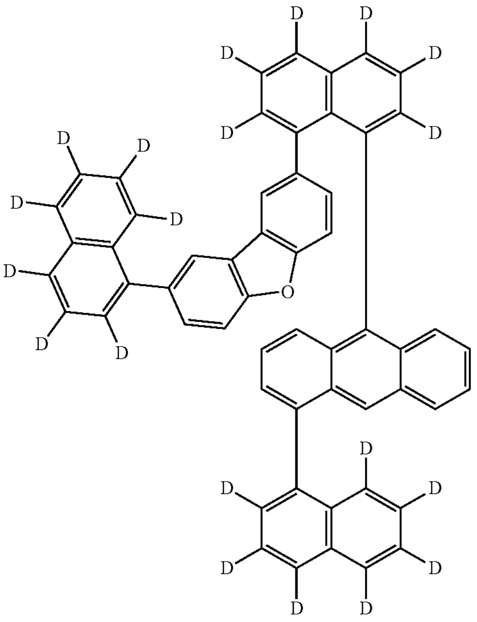
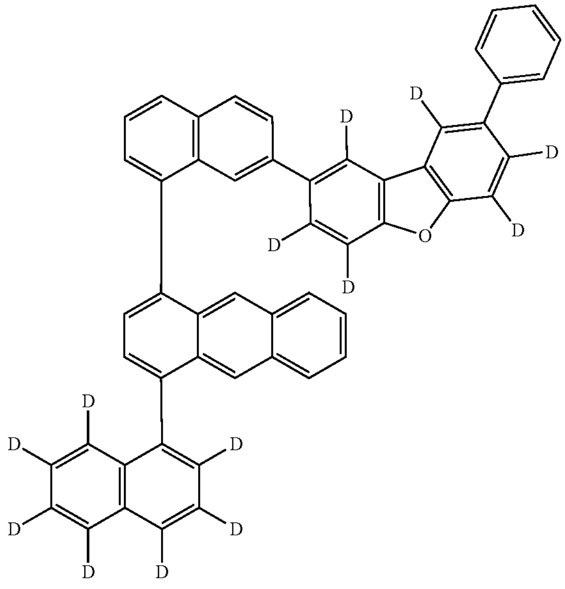
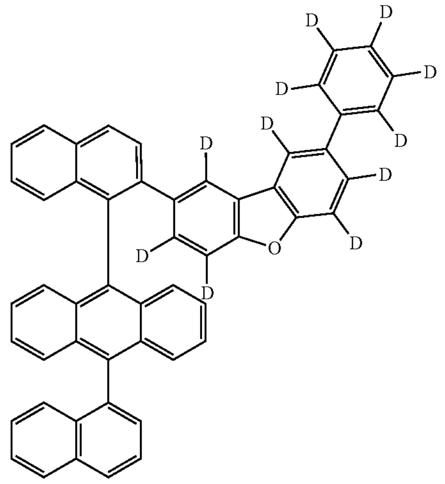

-continued
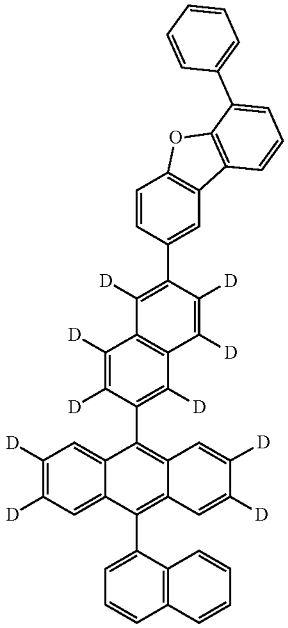
-continued
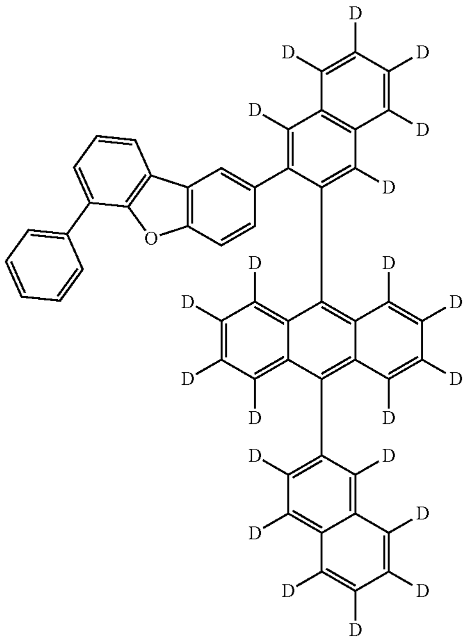
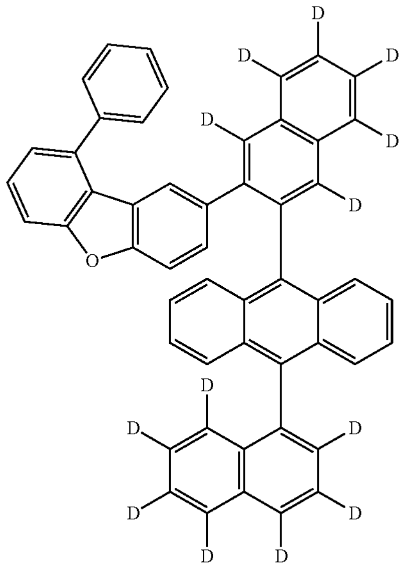
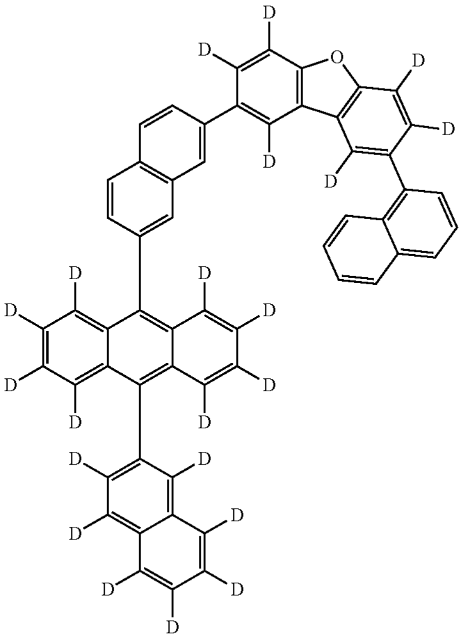

-continued
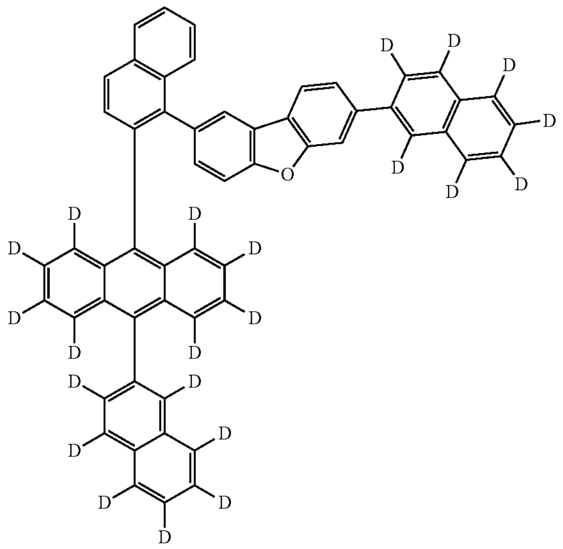
-continued
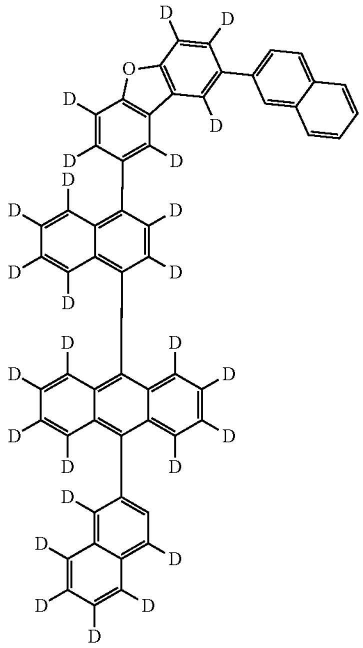
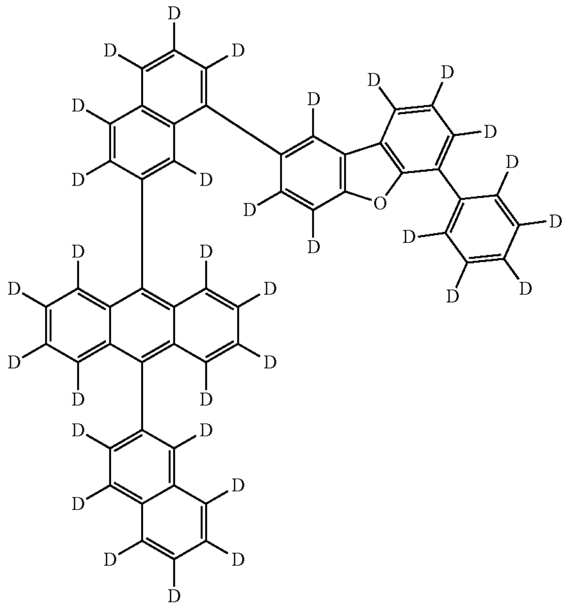
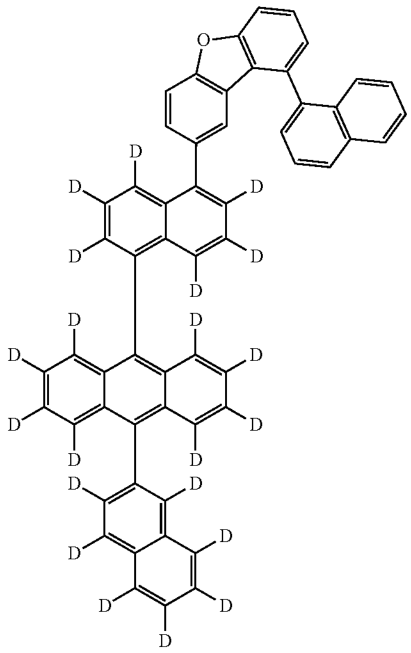

-continued
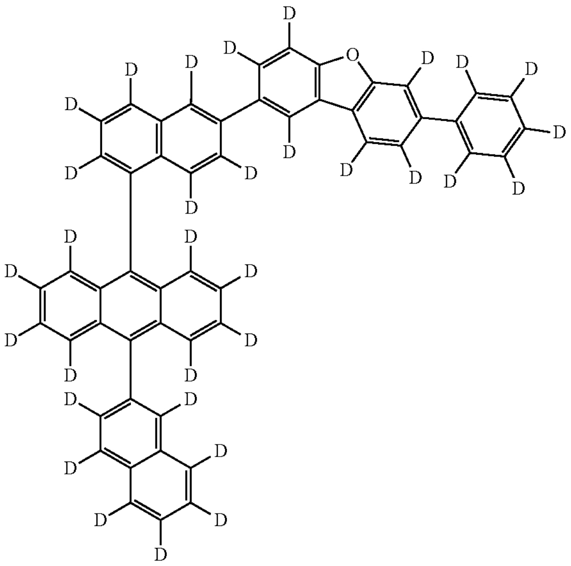
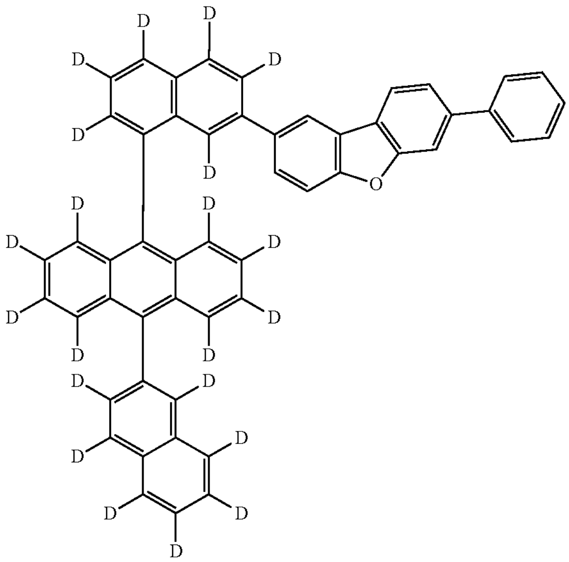
-continued
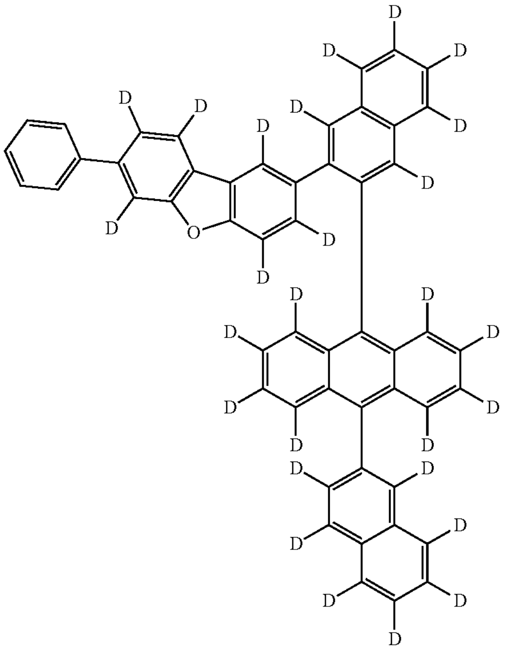
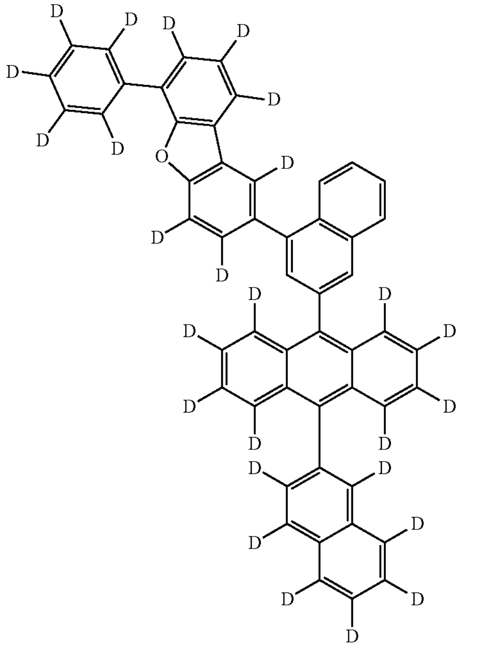

-continued
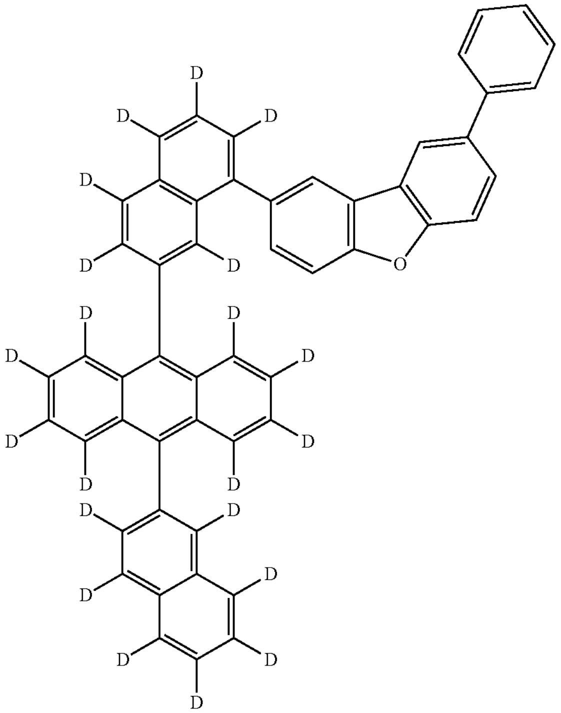
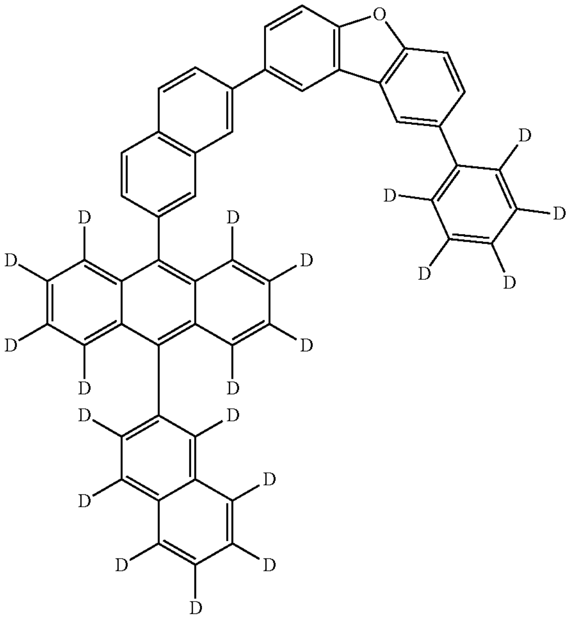
-continued
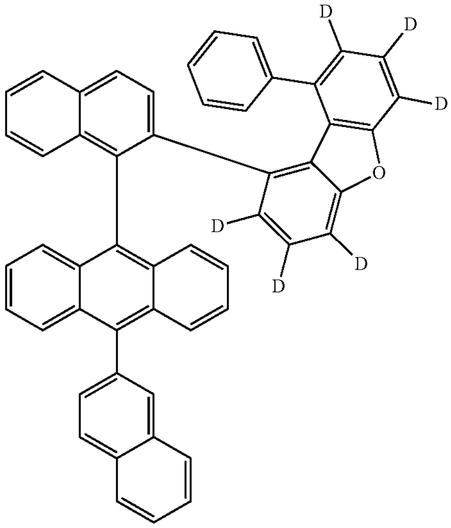
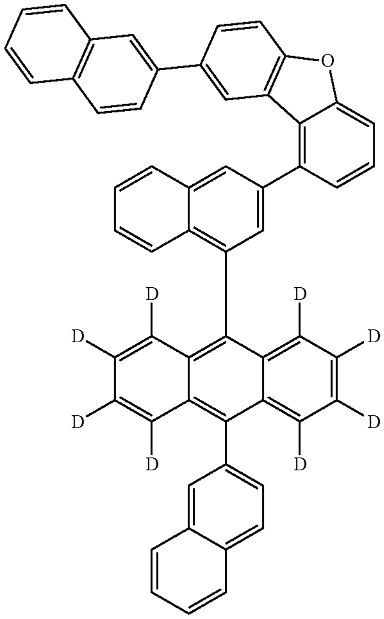

-continued
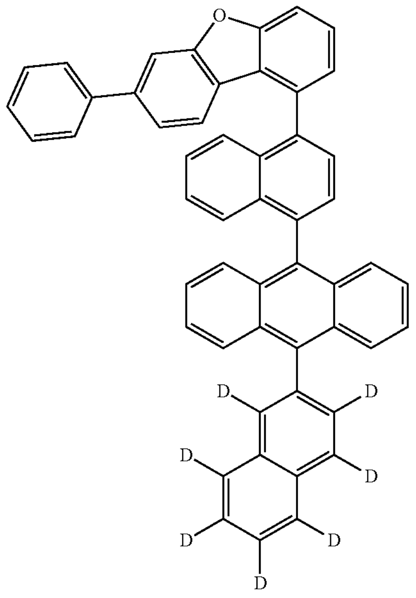
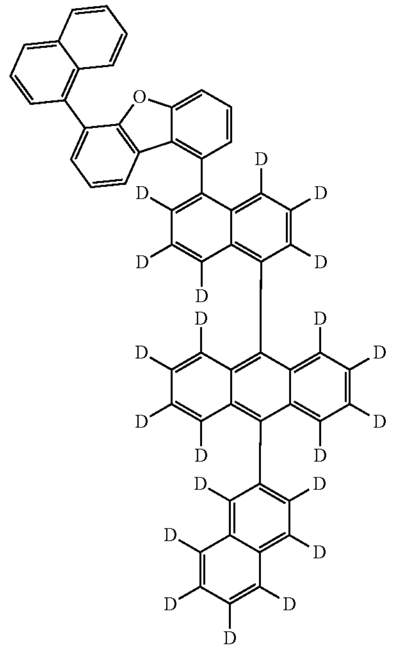
-continued
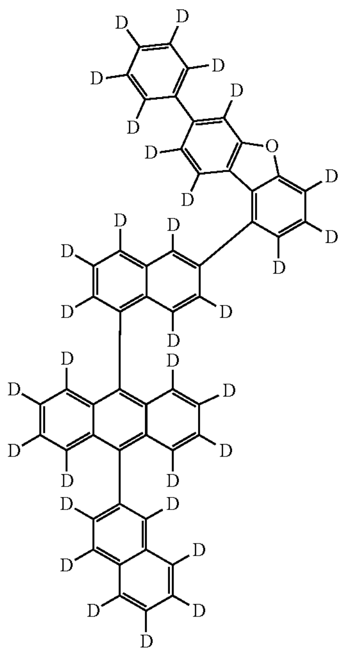
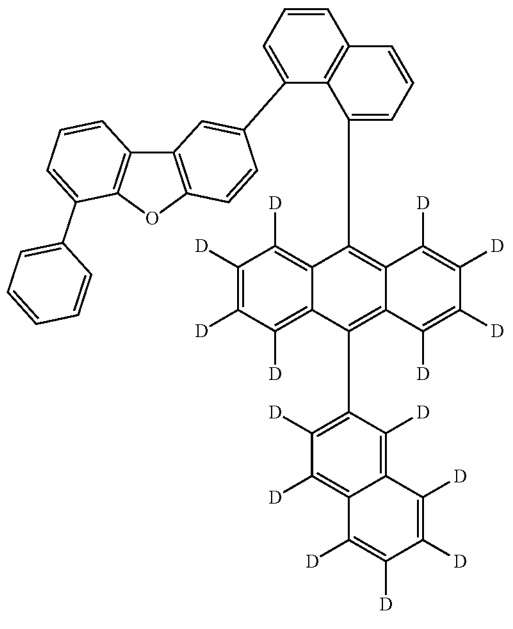

-continued
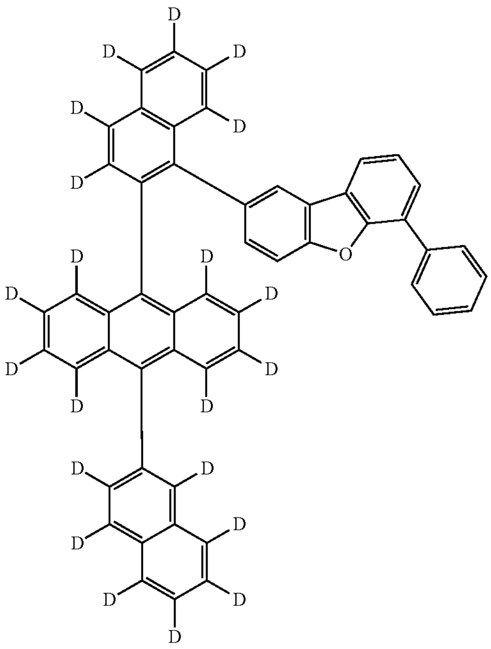
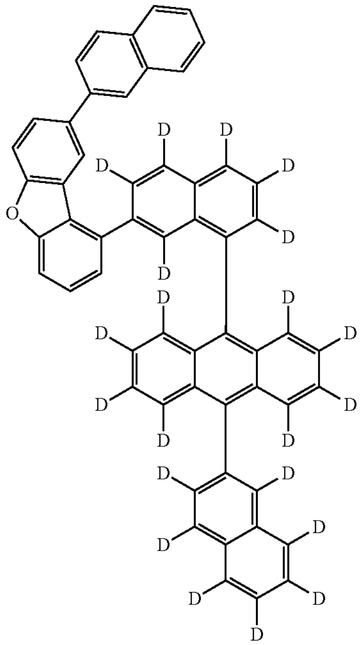
-continued
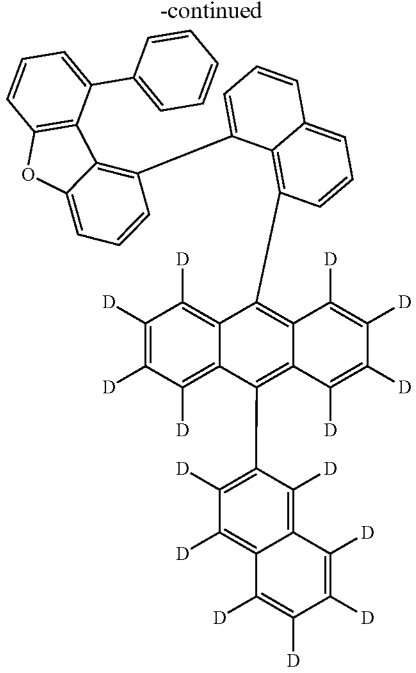
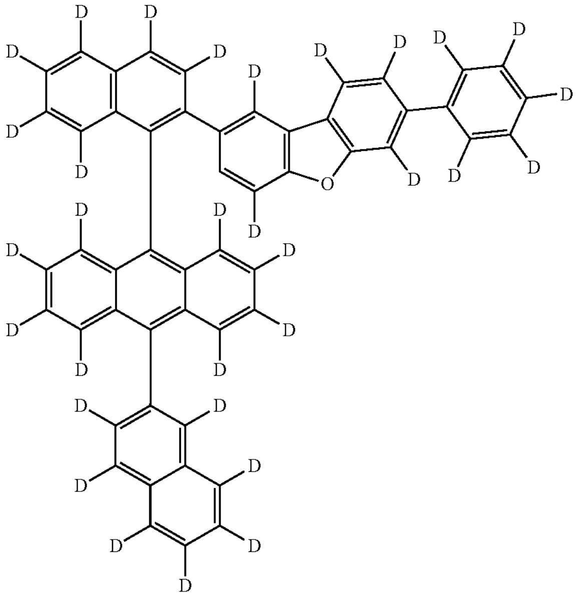
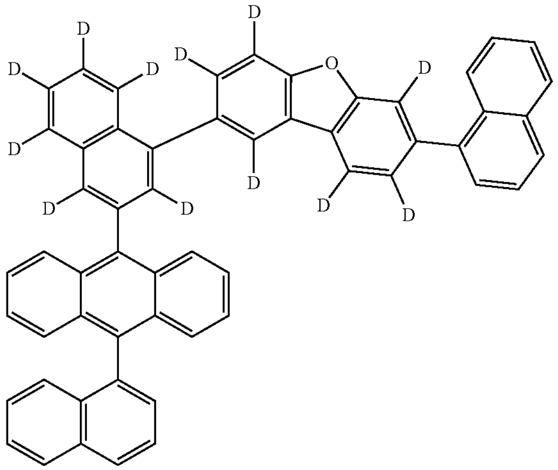

-continued
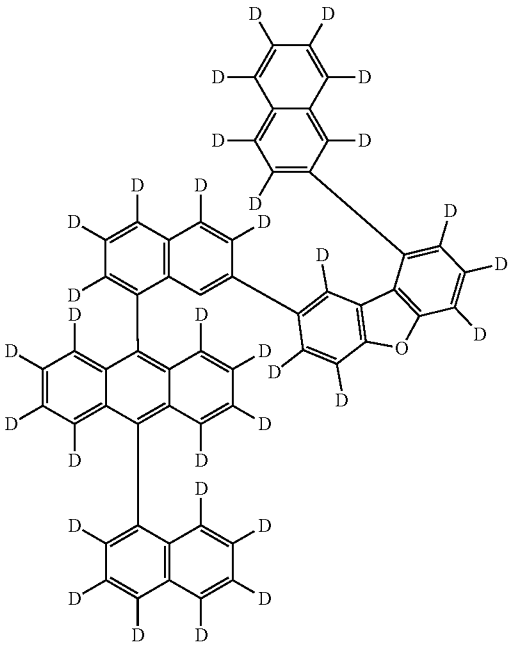
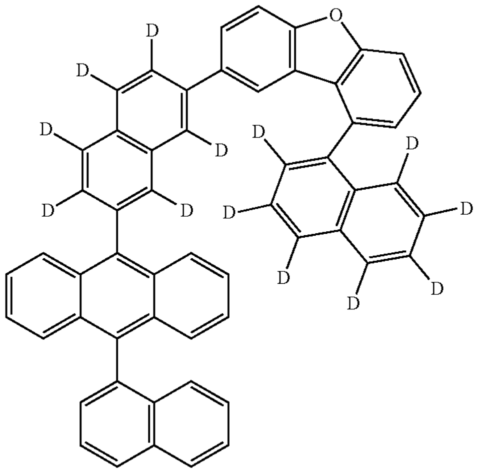
-continued
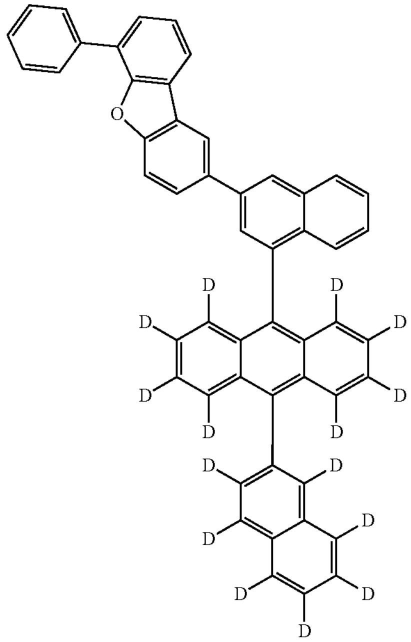
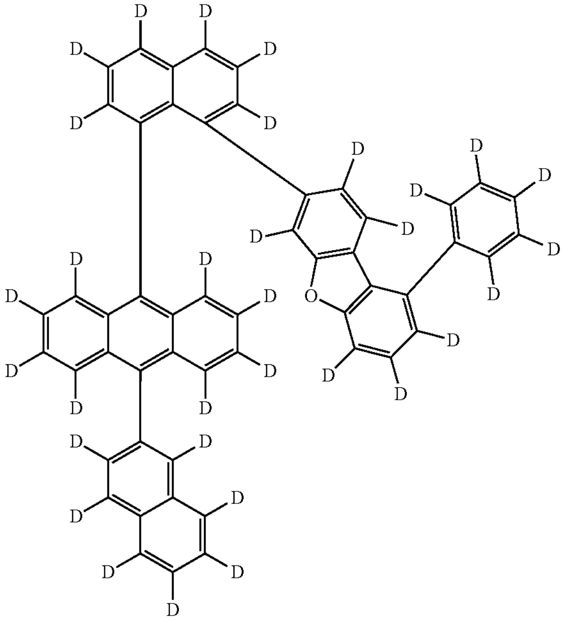

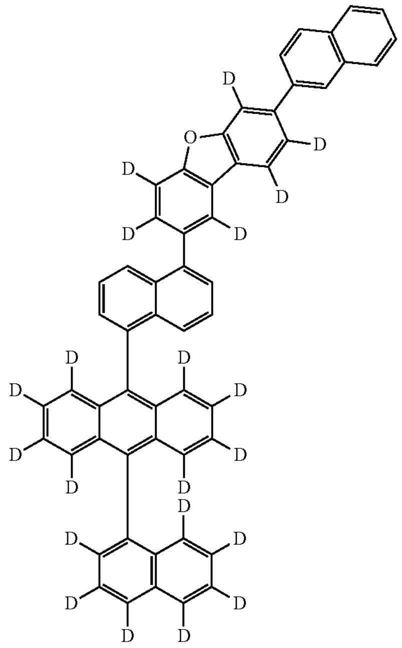
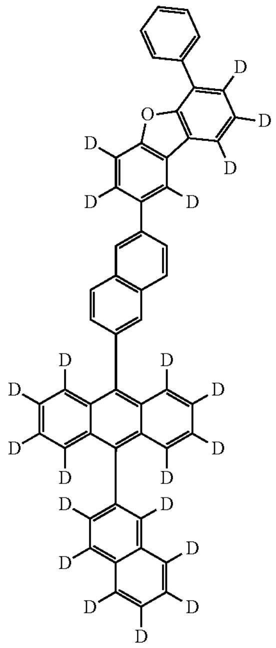
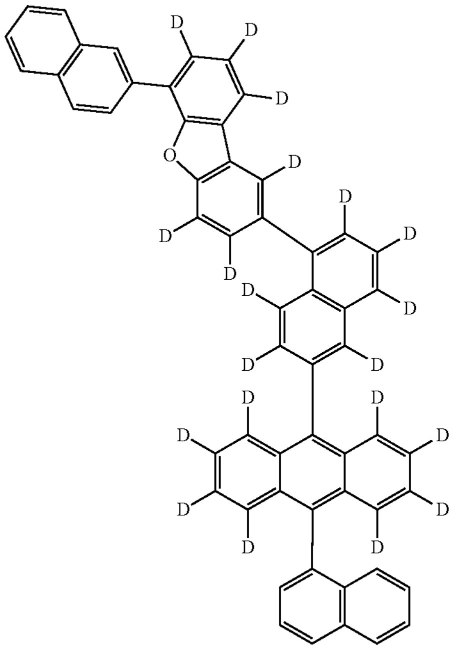
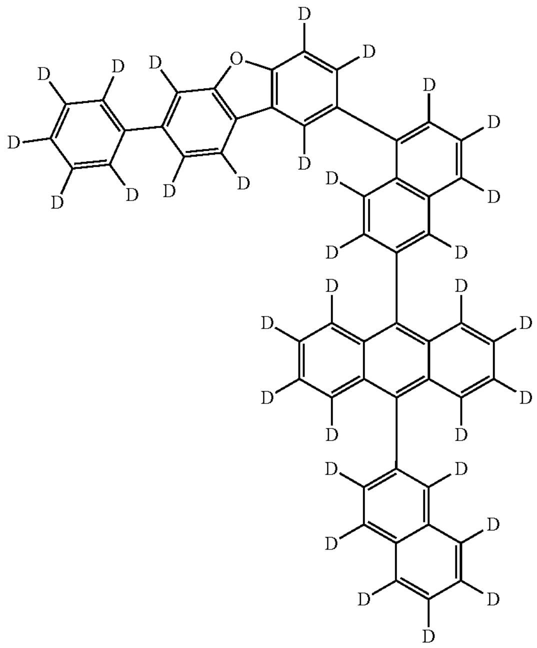

-continued
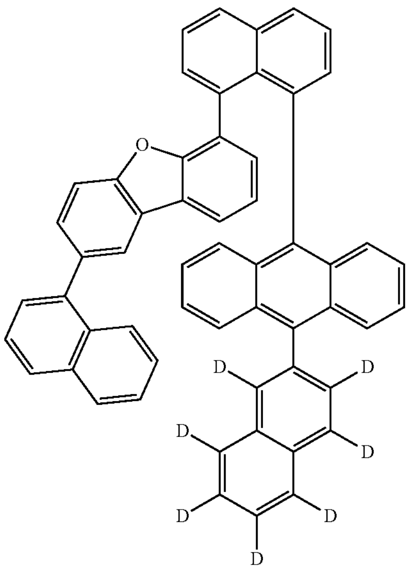
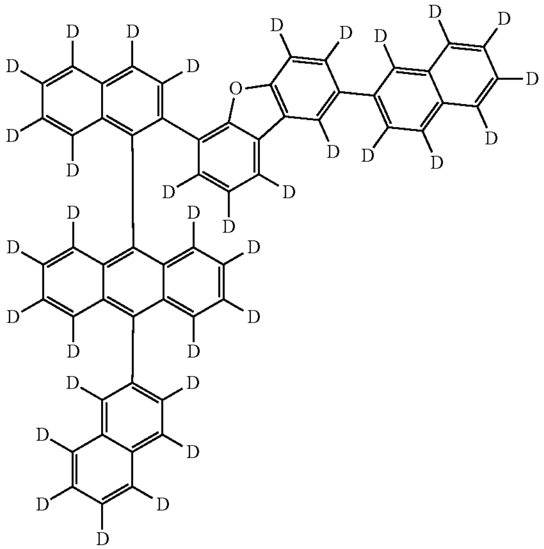
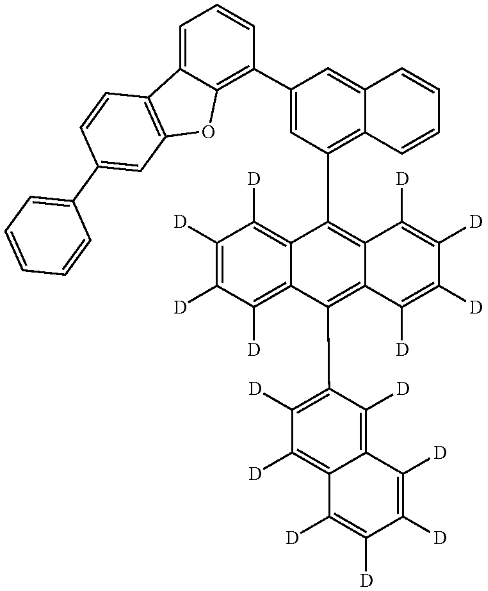
-continued
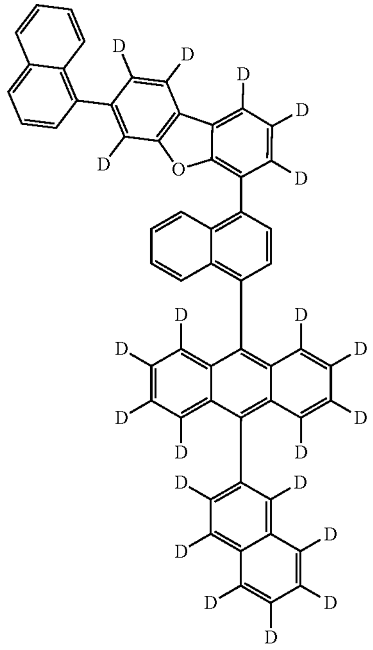
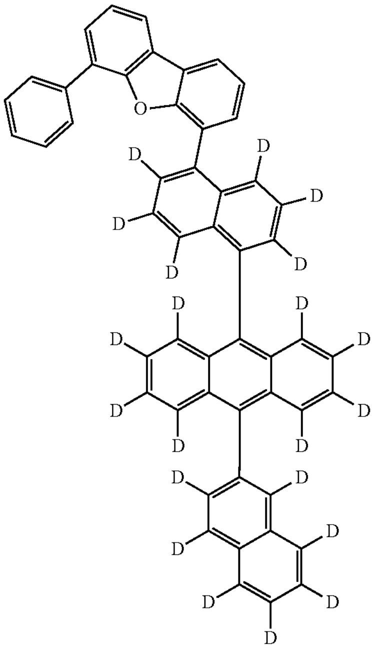

-continued
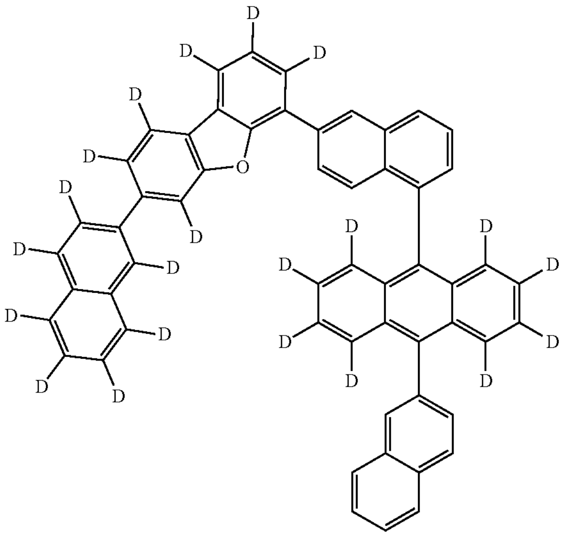
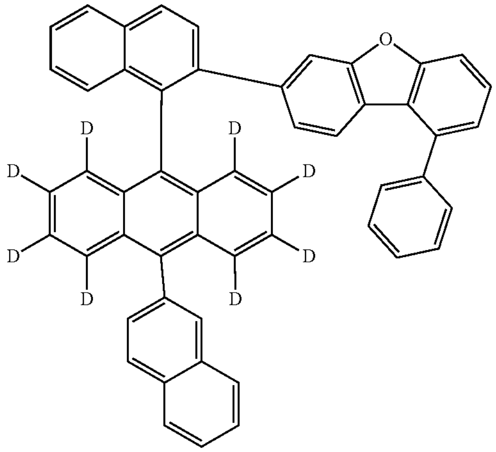
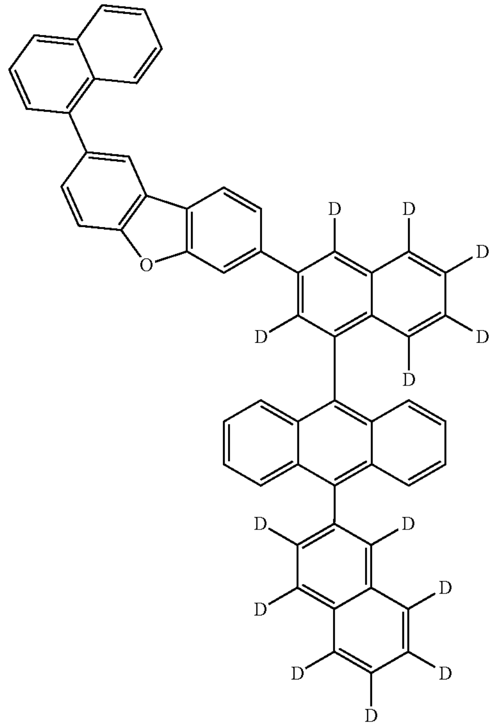
-continued
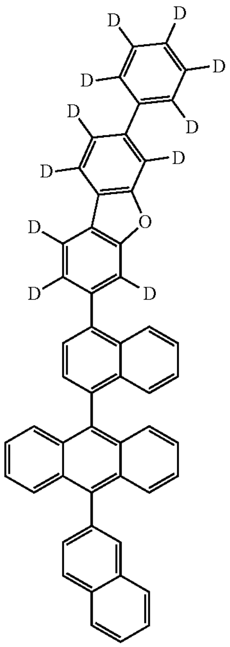 [SMILES: [2H]c1c([2H])c([2H])c(-c2c([2H])c([2H])c3c(oc4c([2H])c(-c5ccc(-c6c7ccccc7c(-c7ccc8ccccc8c7)c7ccccc67)c6ccccc56)c([2H])c([2H])c43)c2[2H])c([2H])c1[2H]]
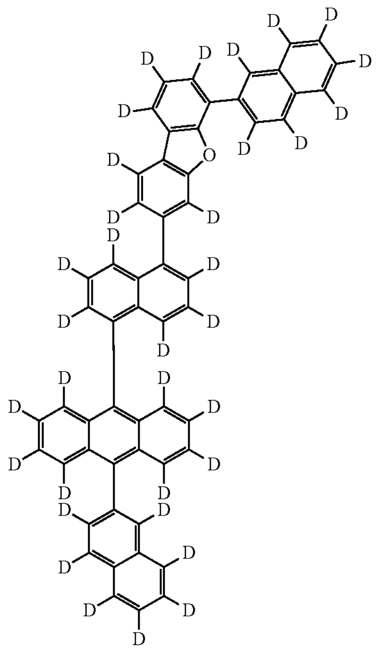

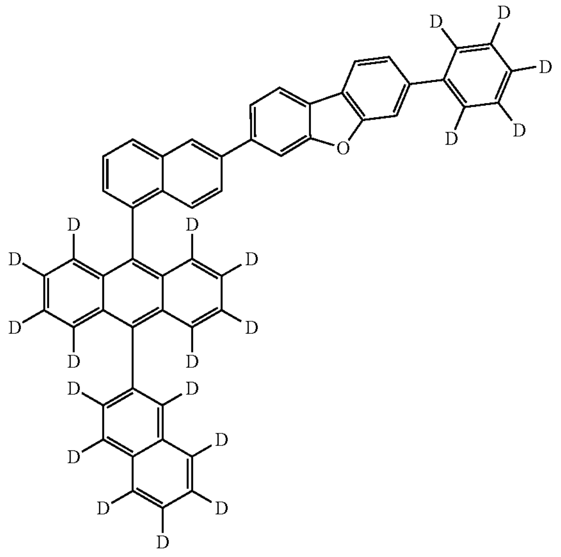
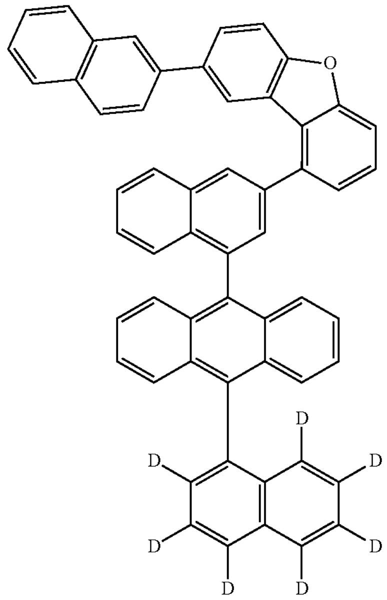
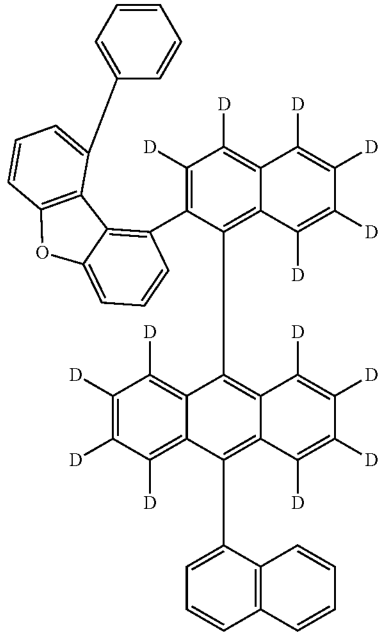
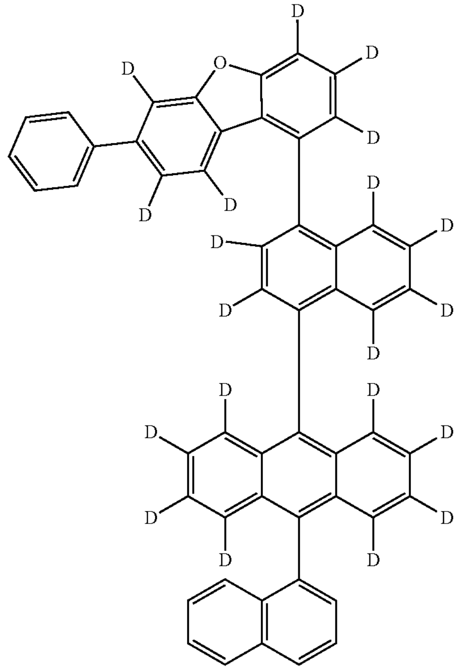 [SMILES: [2H]c1c([2H])c(-c2c([2H])c([2H])c(-c3c4c([2H])c([2H])c([2H])c([2H])c4c(-c4cccc5ccccc45)c4c([2H])c([2H])c([2H])c([2H])c34)c3c([2H])c([2H])c([2H])c([2H])c23)c2c(oc3c([2H])c(-c4ccccc4)c([2H])c([2H])c32)c1[2H]]

-continued
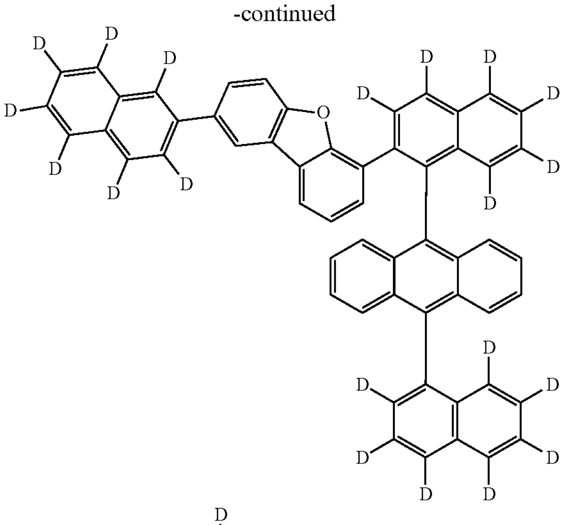
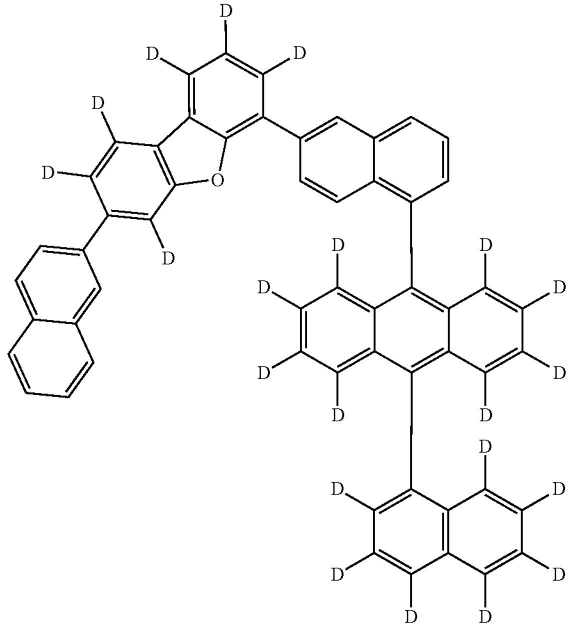
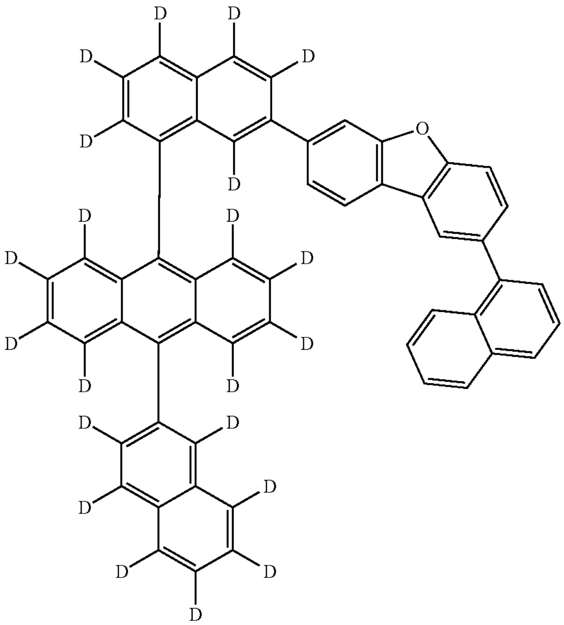
-continued
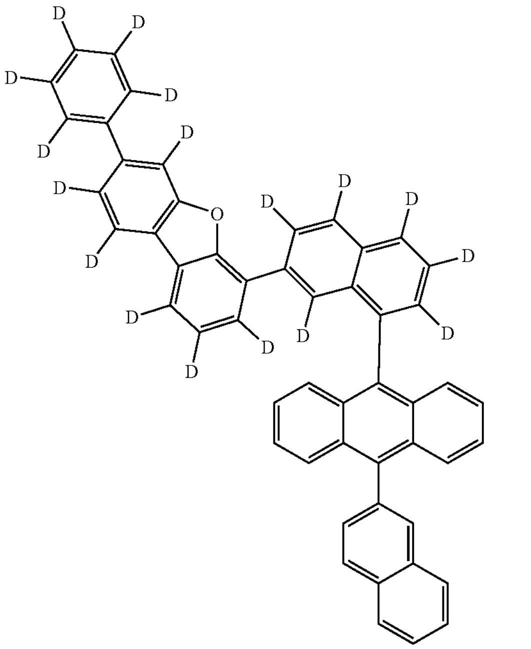
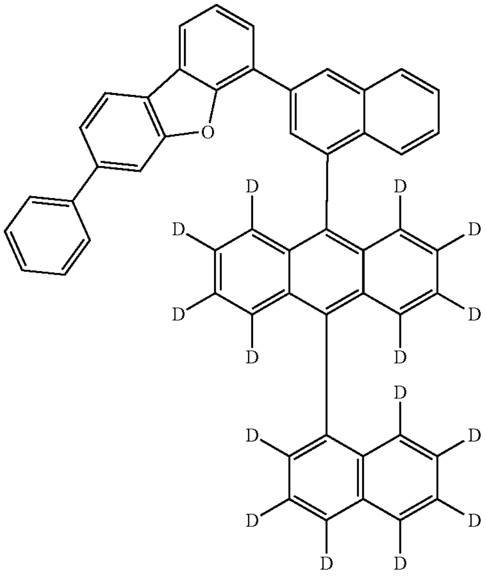

-continued
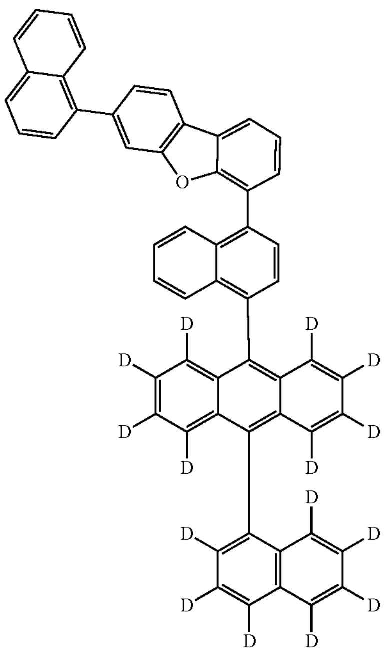
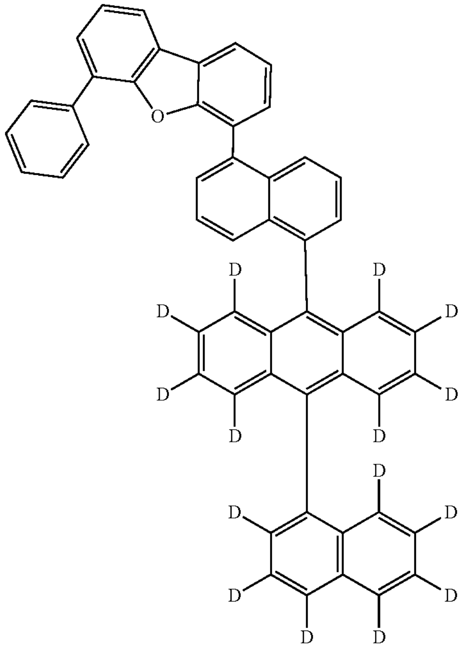
-continued
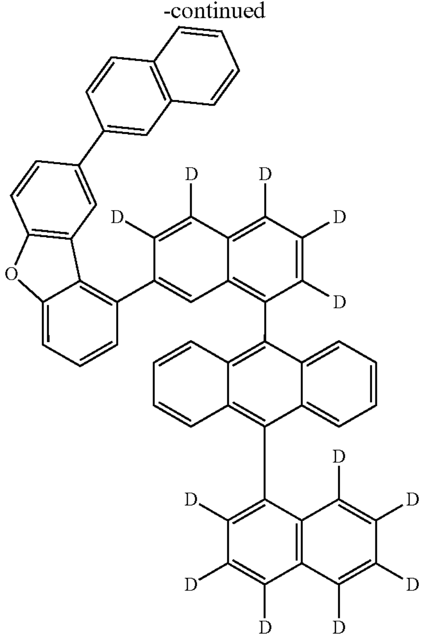
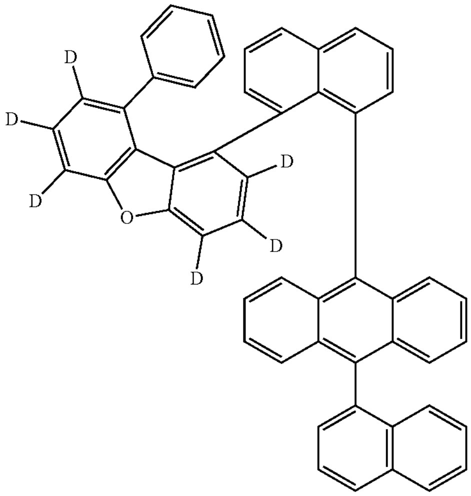
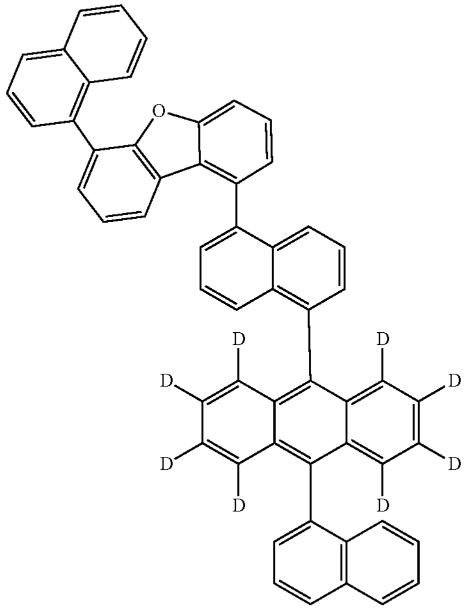

-continued
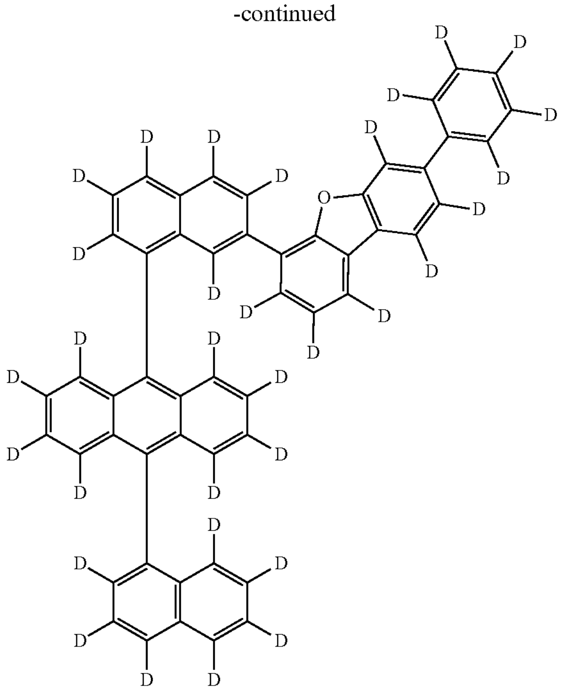
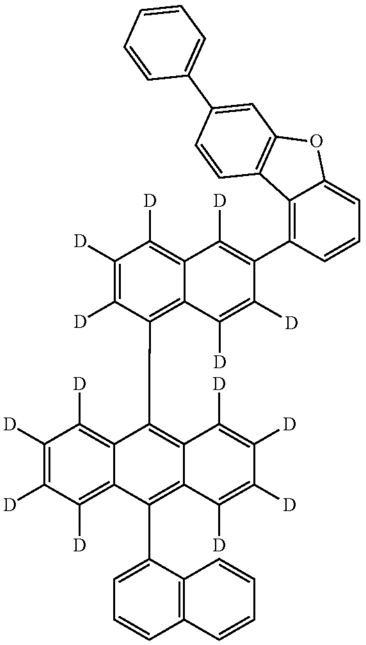
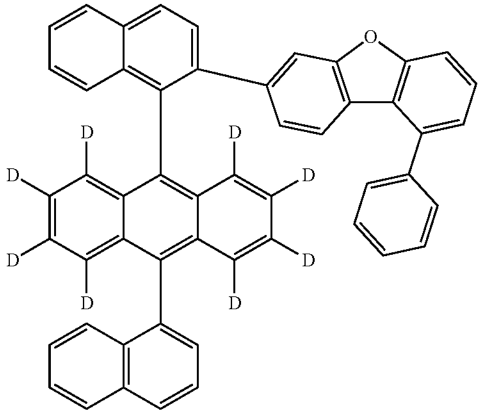
-continued
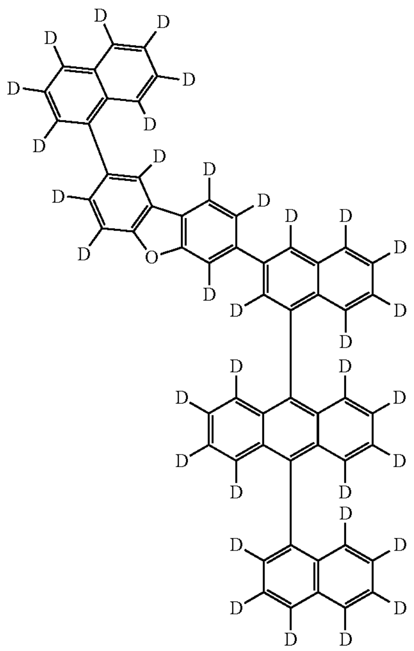
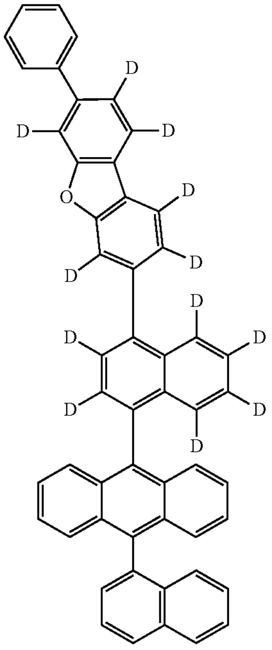

-continued
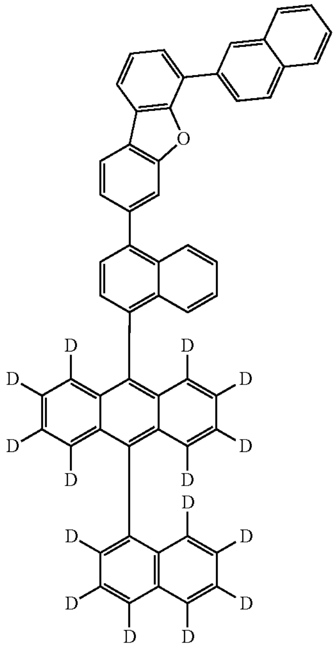 [SMILES: [2H]c1c([2H])c([2H])c2c(-c3c4c([2H])c([2H])c([2H])c([2H])c4c(-c4ccc(-c5ccc6c(c5)oc5c(-c7ccc8ccccc8c7)cccc56)c5ccccc45)c4c([2H])c([2H])c([2H])c([2H])c34)c([2H])c([2H])c([2H])c2c1[2H]]
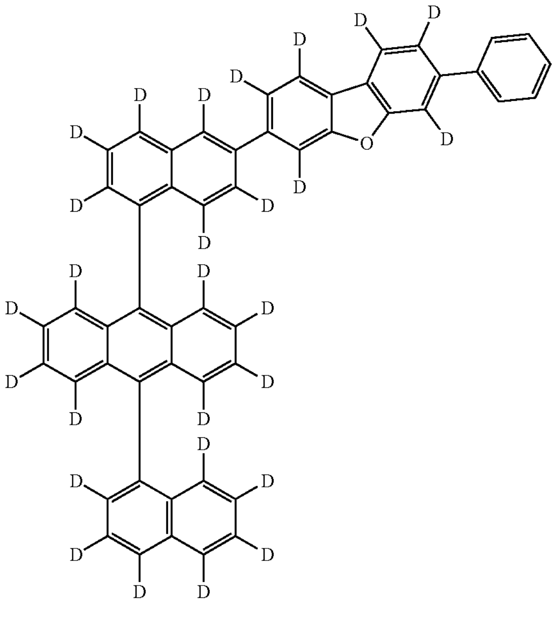
-continued
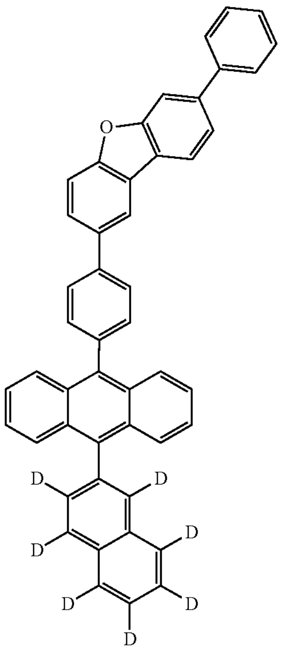
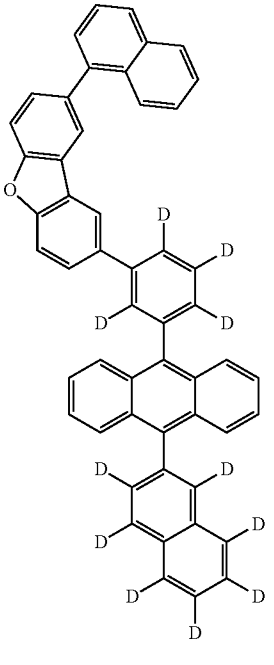

-continued
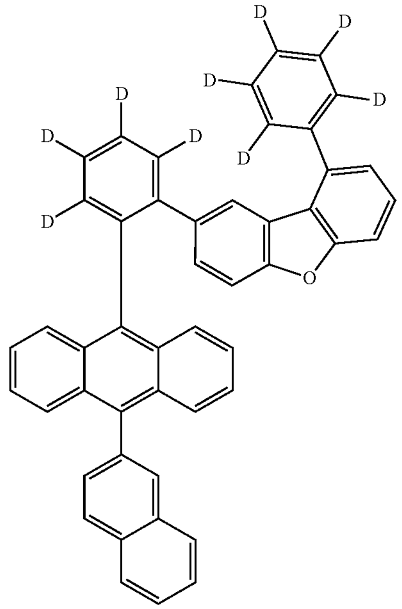
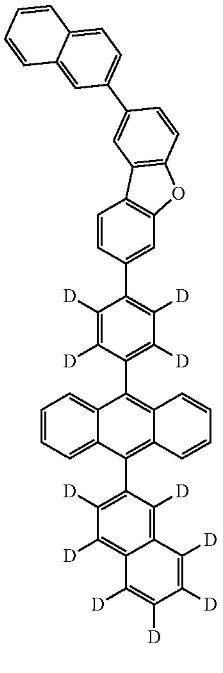
-continued
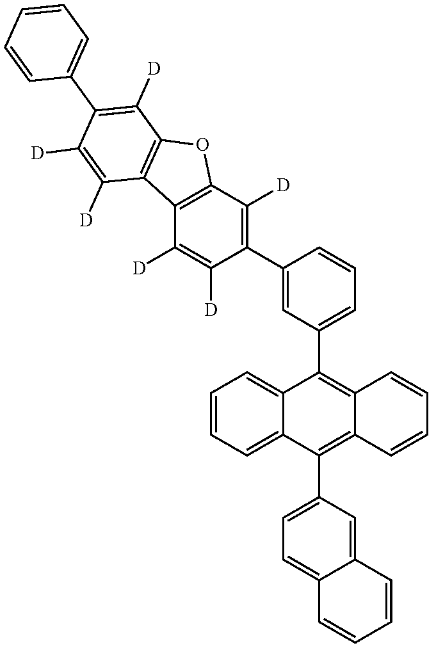
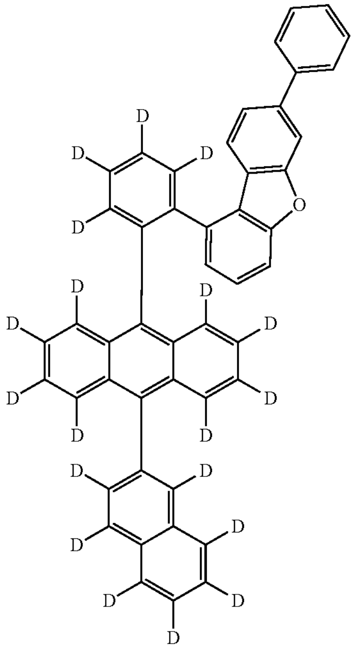

-continued
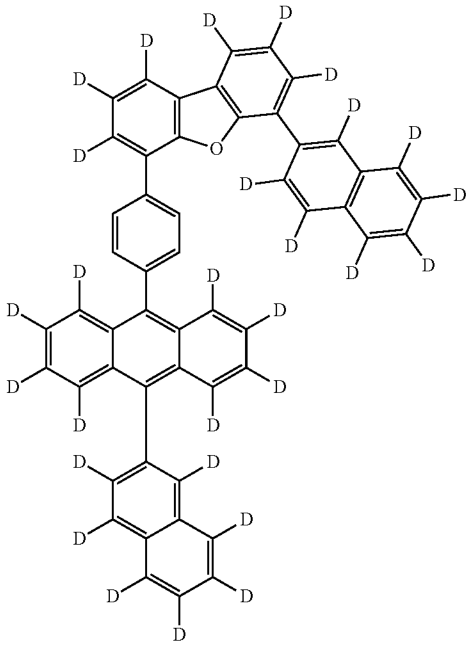
-continued
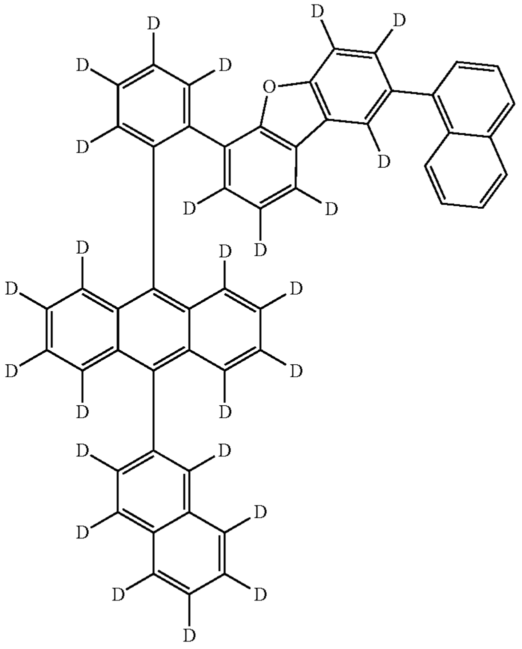
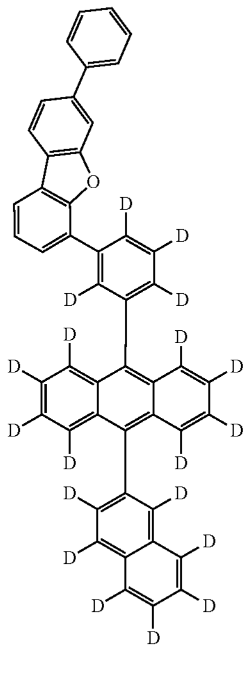
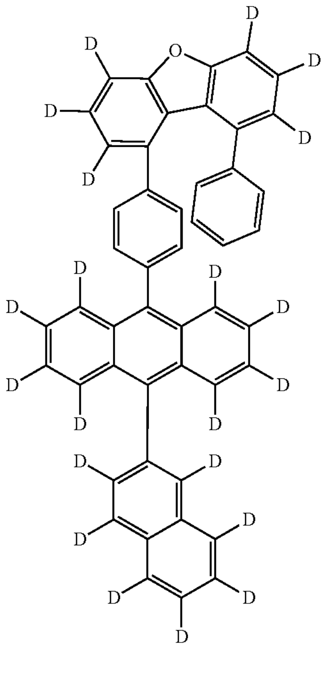

-continued
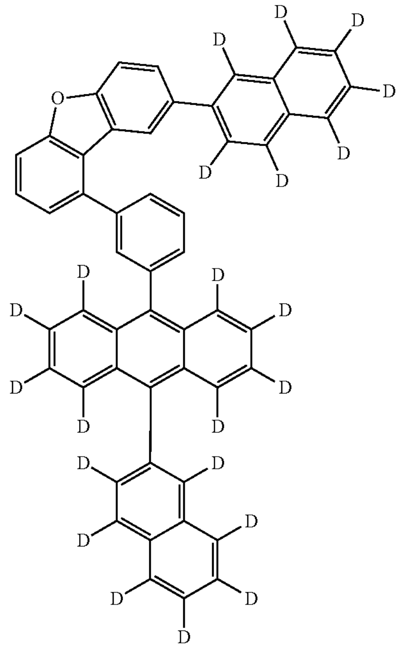
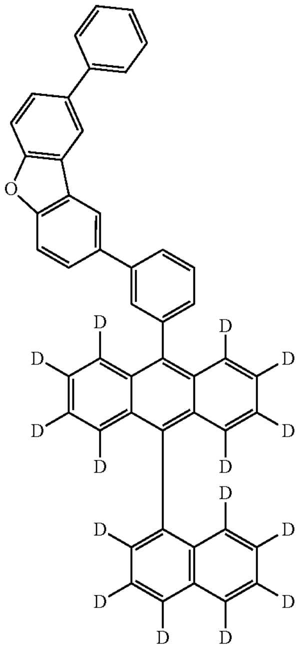
-continued
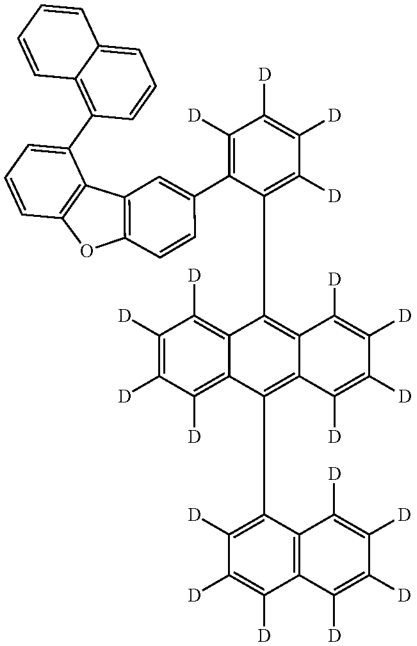
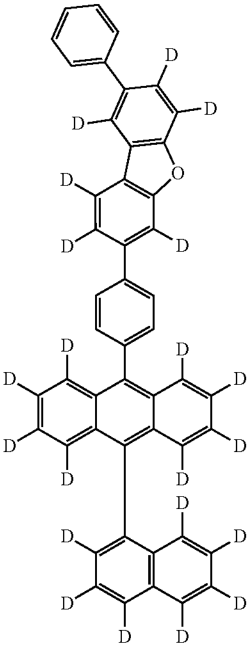

-continued
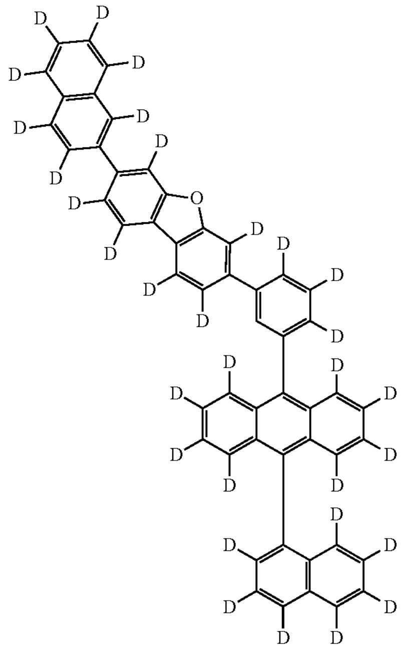
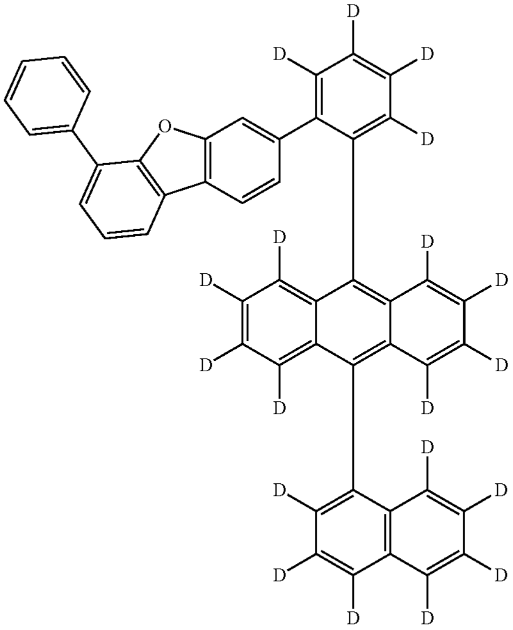
-continued
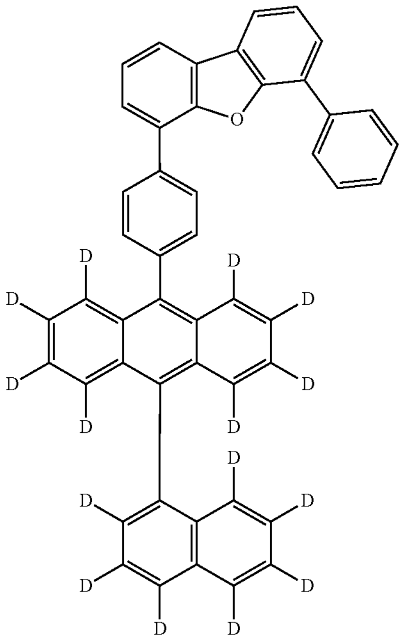
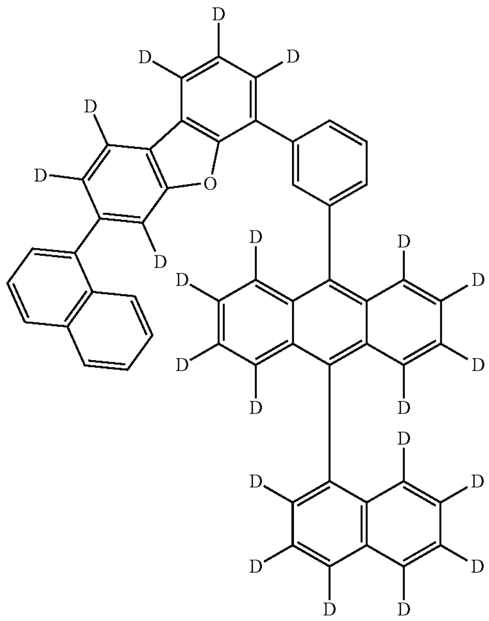 [SMILES: [2H]c1c([2H])c([2H])c2c(oc3c([2H])c(-c4cccc5ccccc45)c([2H])c([2H])c32)c1-c1cccc(-c2c3c([2H])c([2H])c([2H])c([2H])c3c(-c3c([2H])c([2H])c([2H])c4c([2H])c([2H])c([2H])c([2H])c34)c3c([2H])c([2H])c([2H])c([2H])c23)c1]

-continued
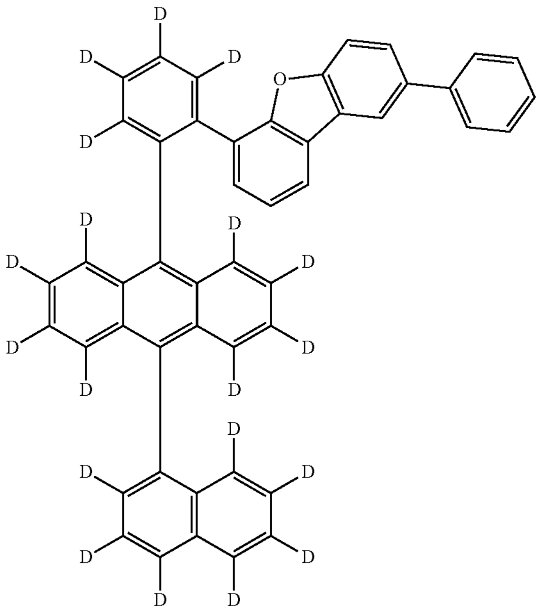
-continued
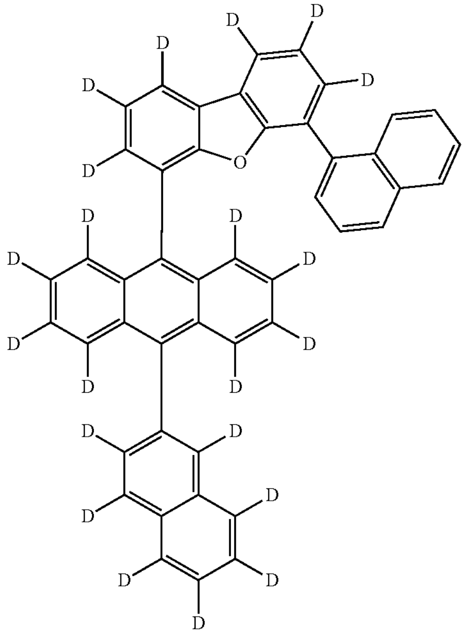
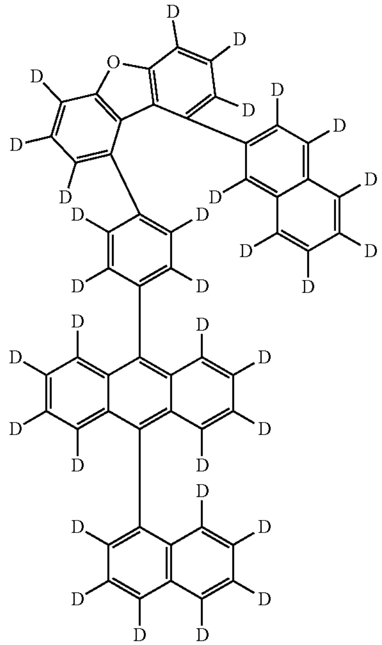
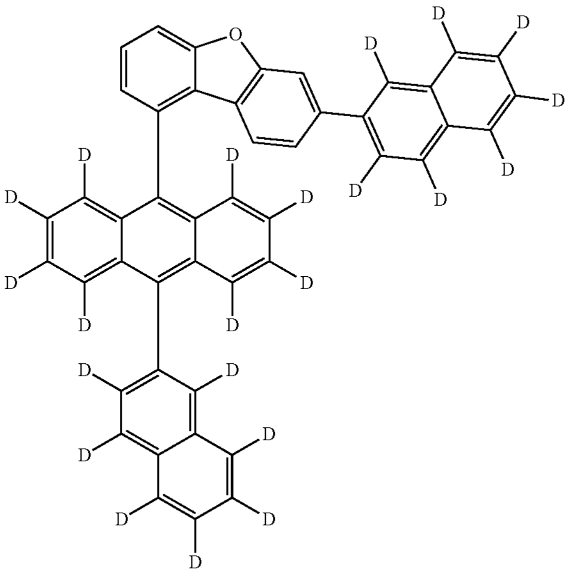

-continued
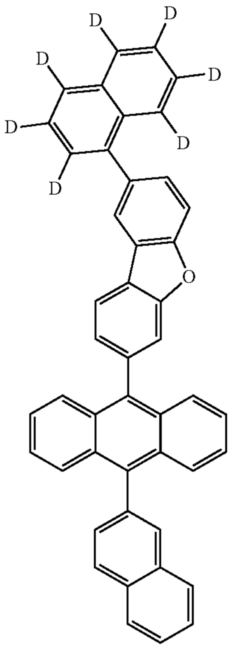
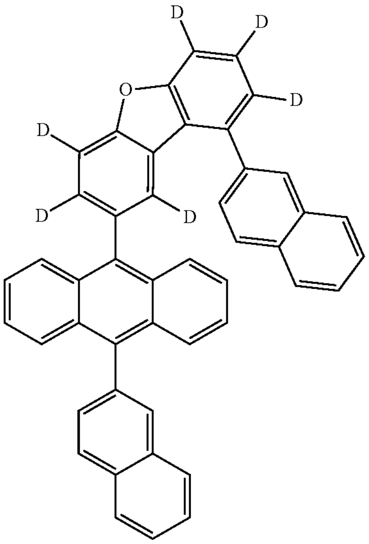
-continued
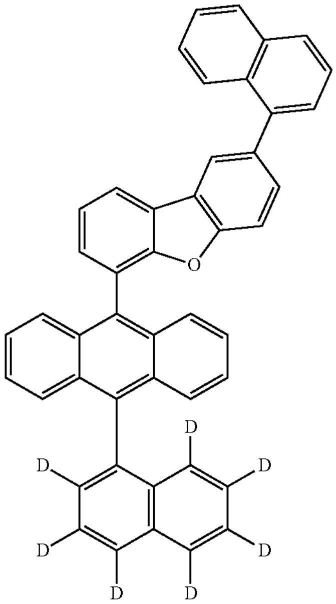
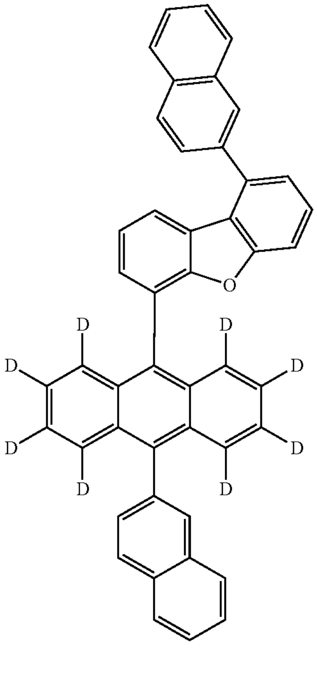

-continued
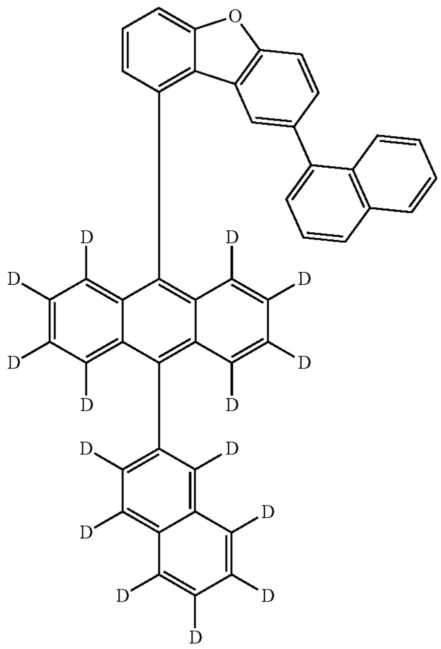
-continued
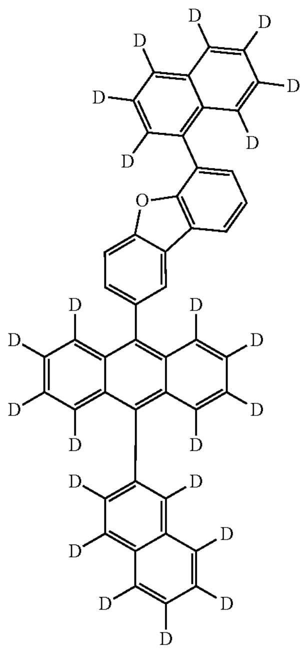
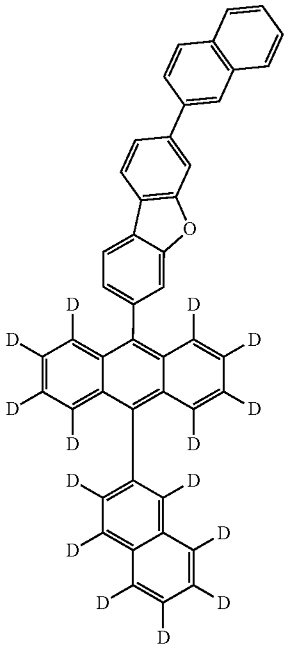
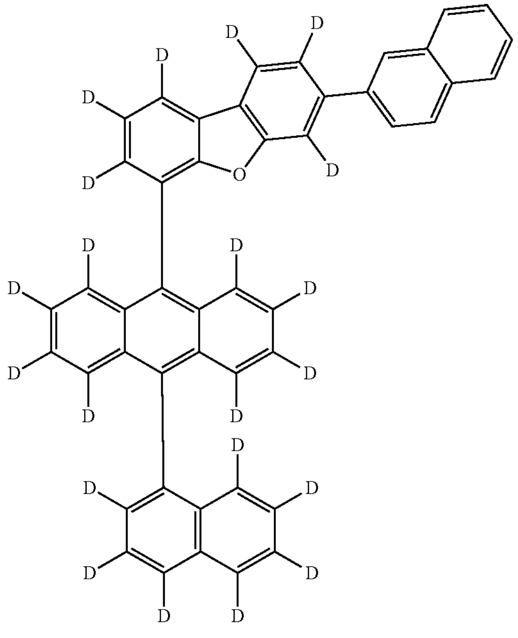

-continued
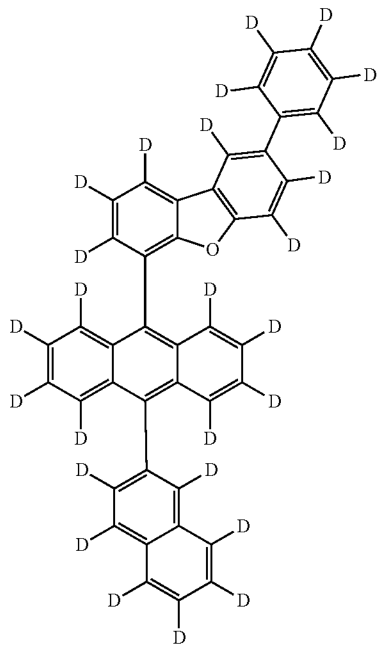
-continued
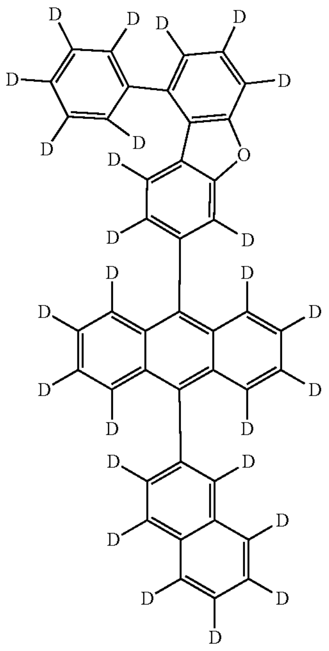
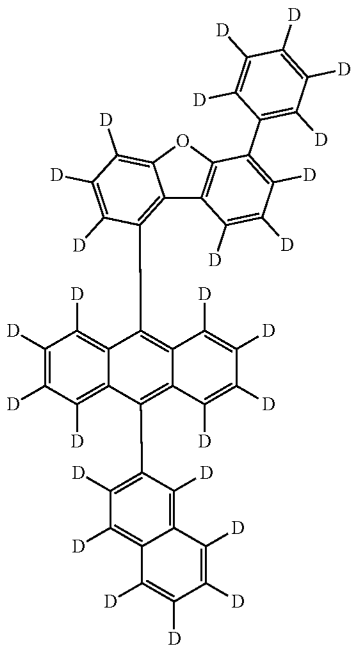
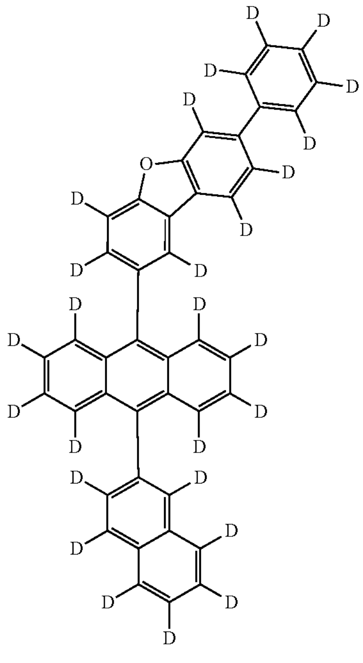

-continued
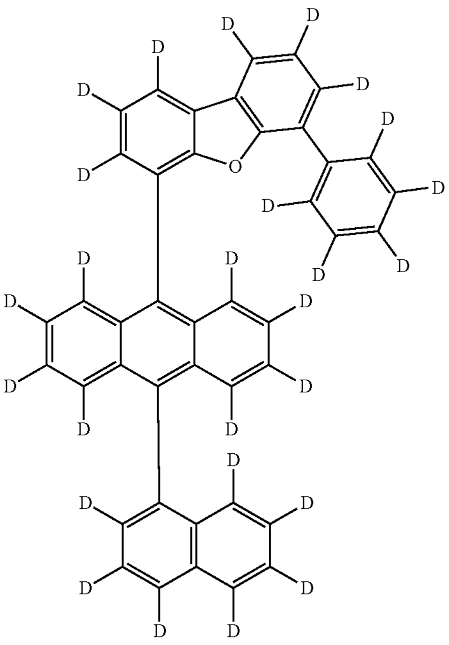
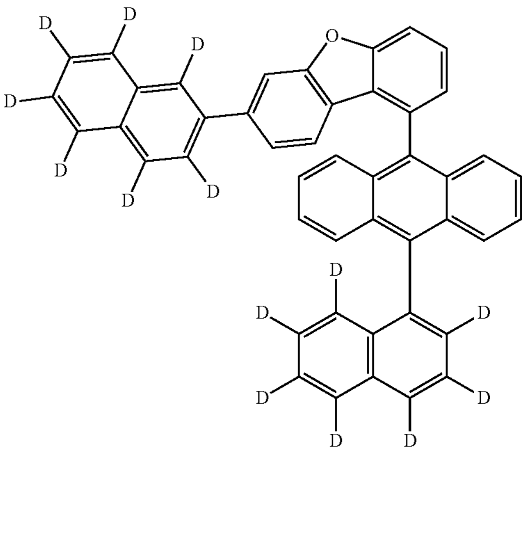
-continued
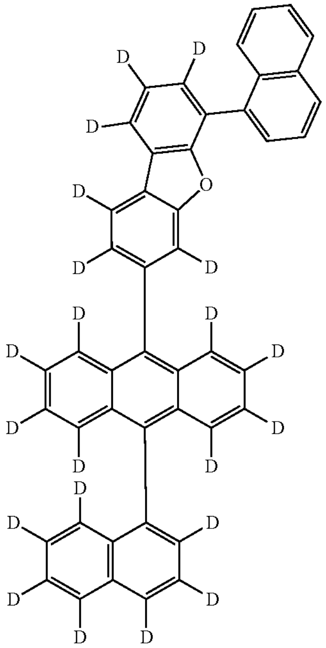
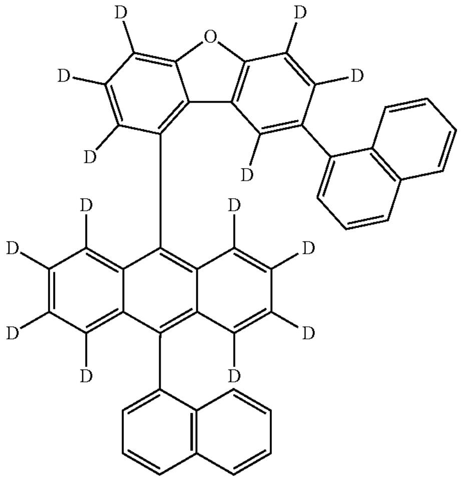
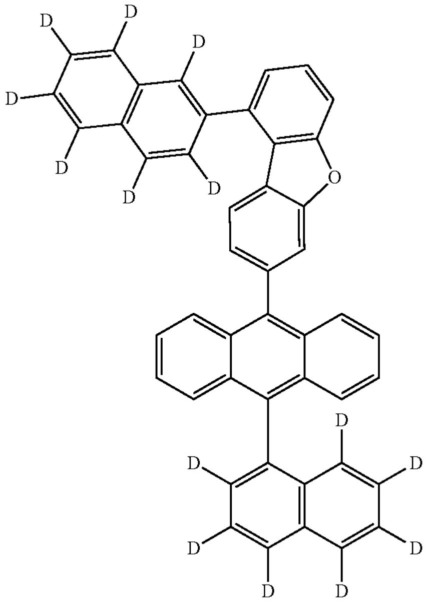

-continued
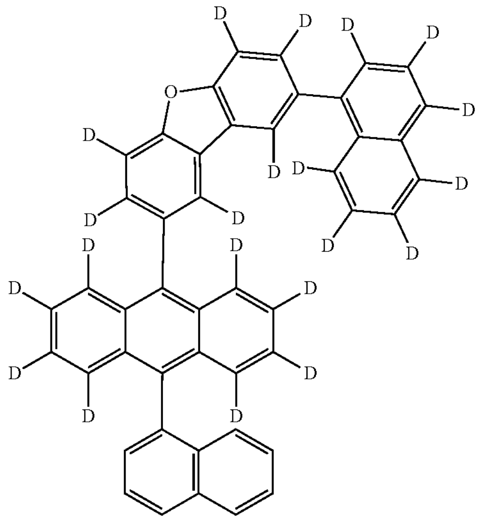
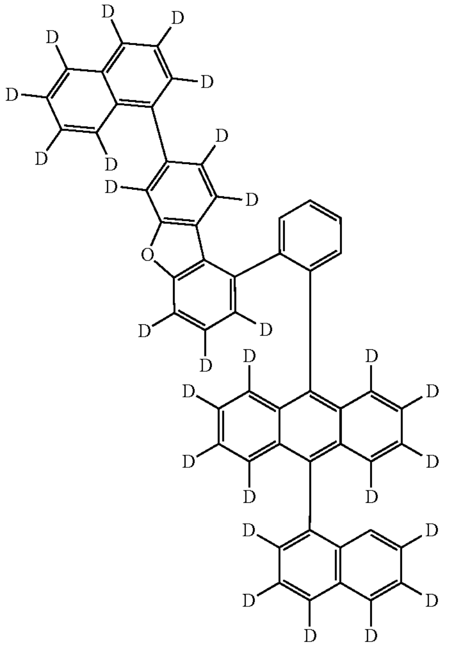
-continued
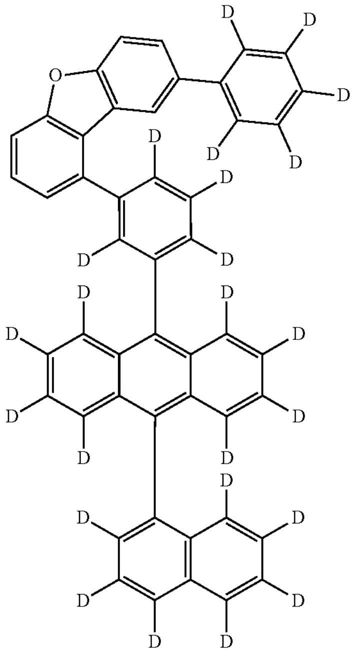
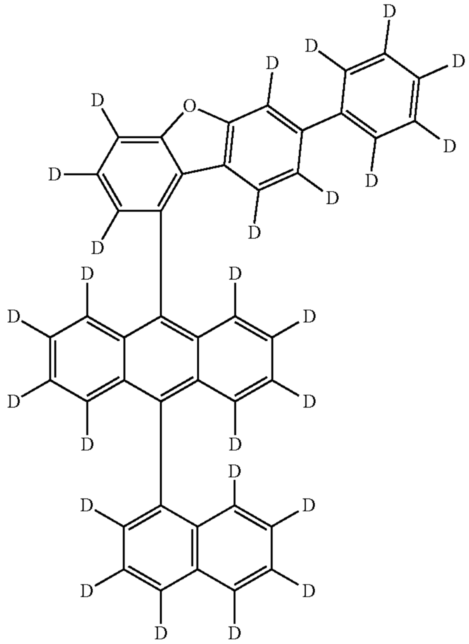

-continued
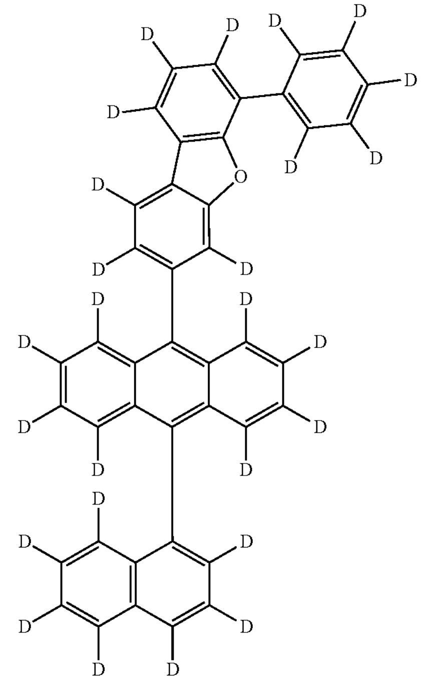
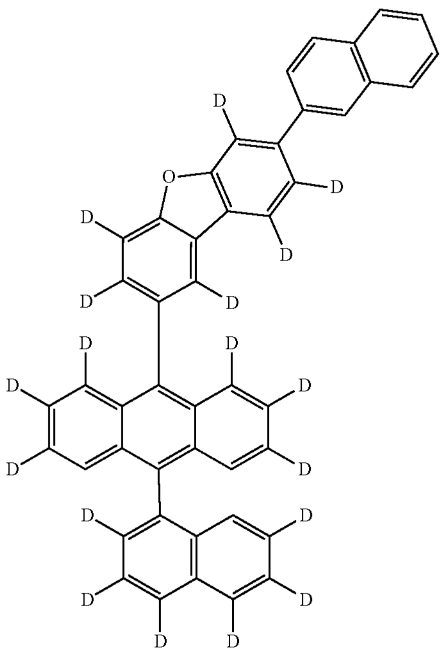
-continued
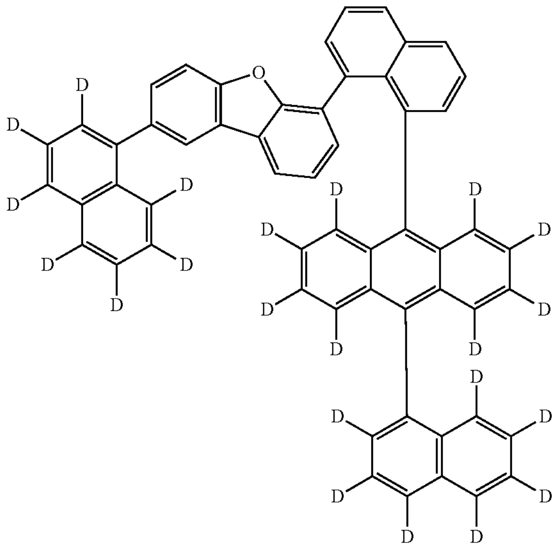
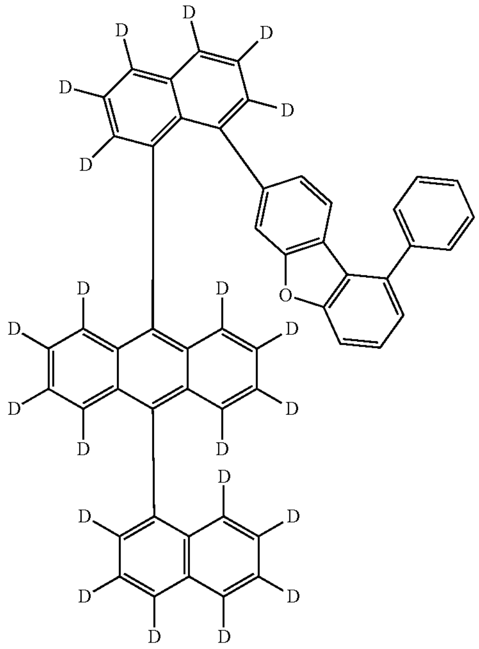

-continued
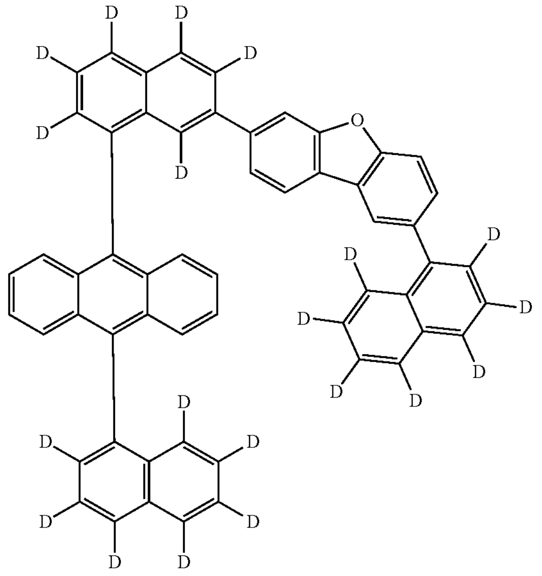
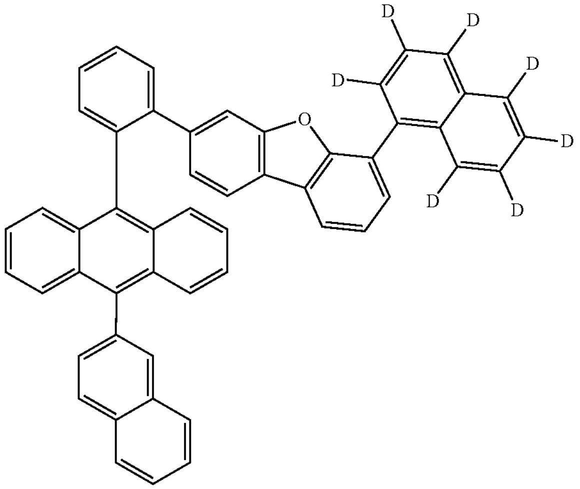
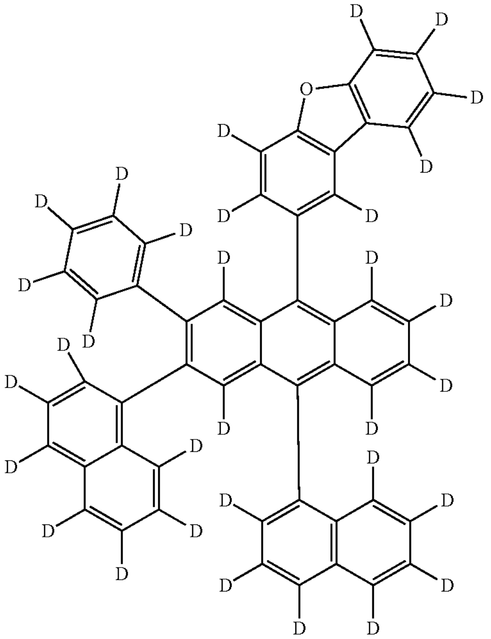
-continued
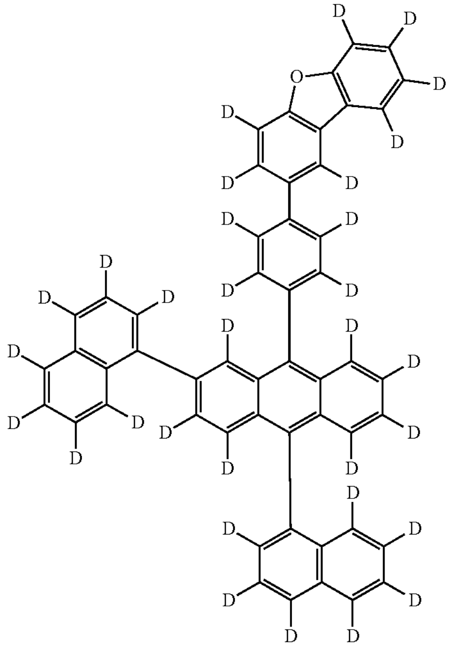
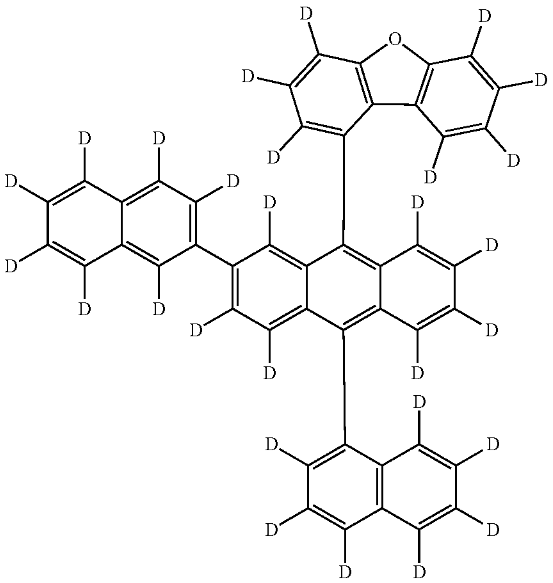

-continued
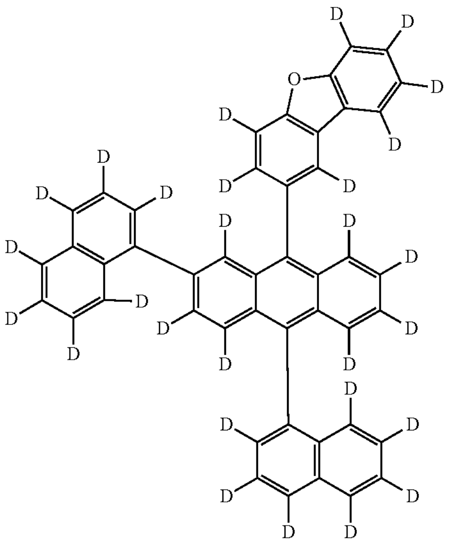
-continued
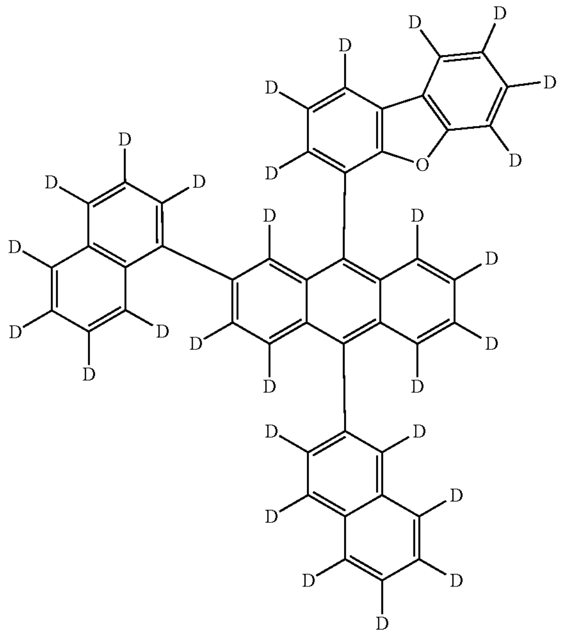
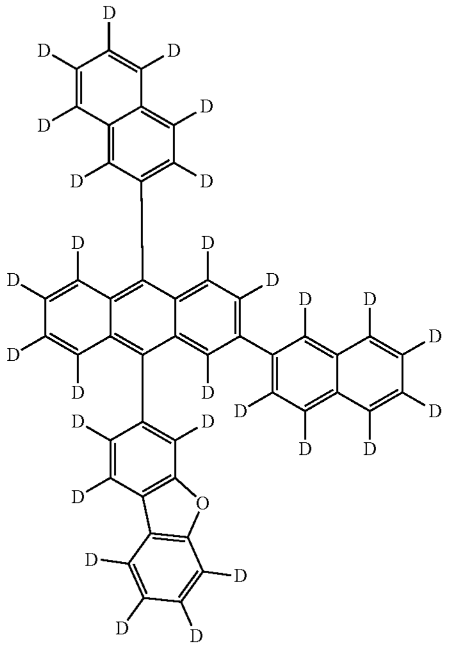
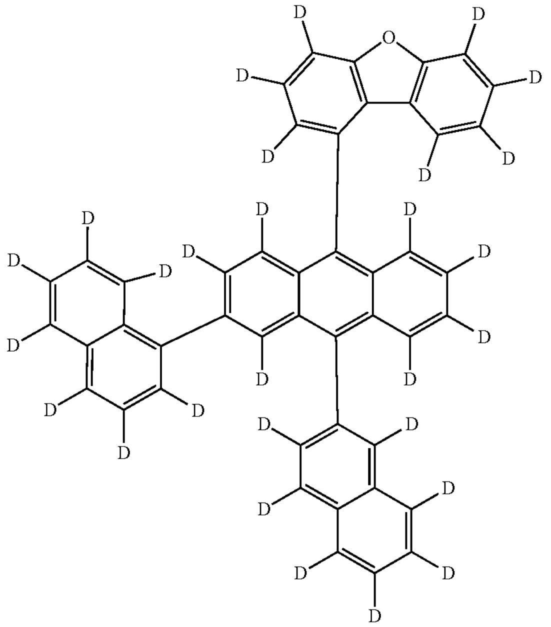

-continued
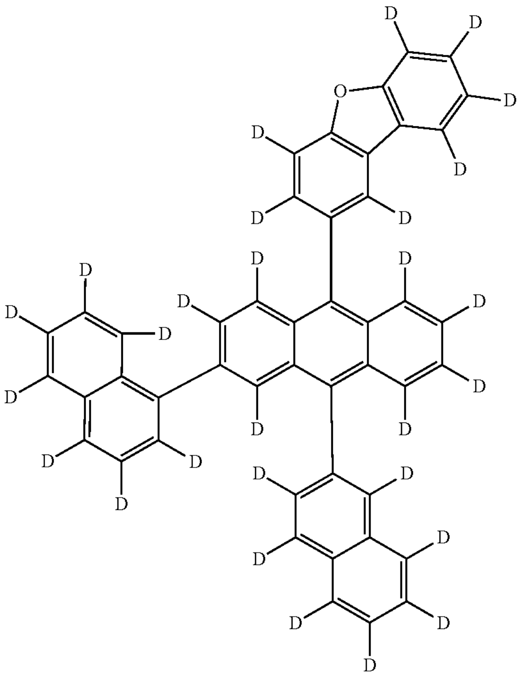
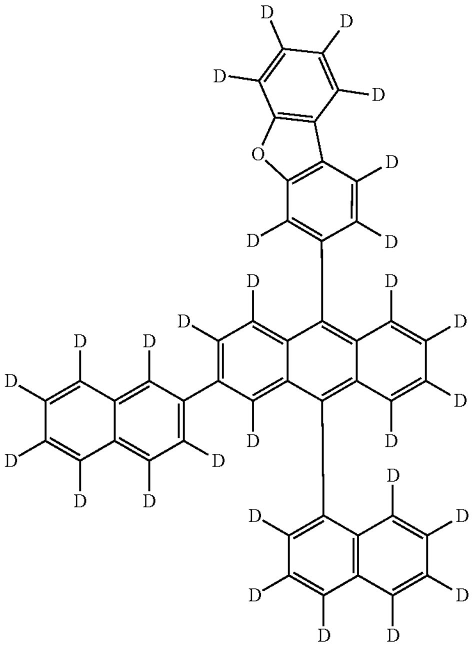
-continued
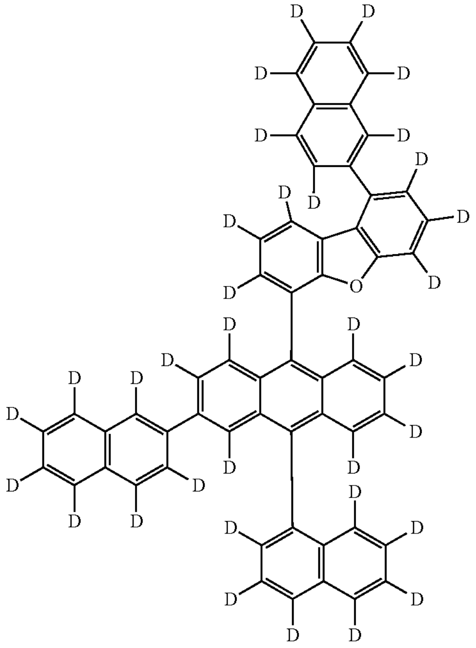
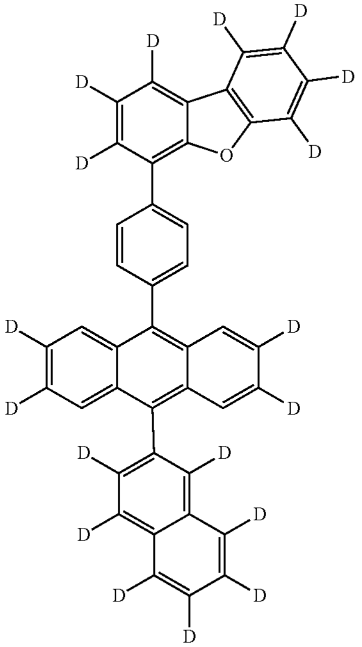

-continued
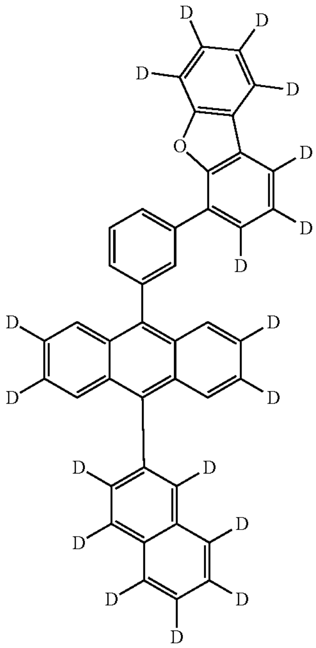
-continued
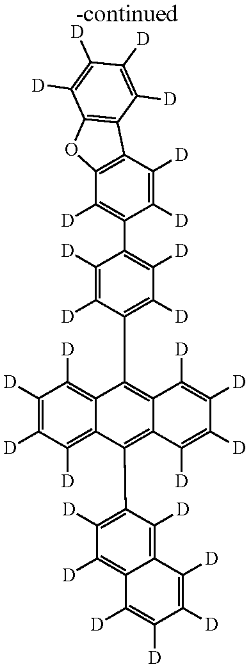
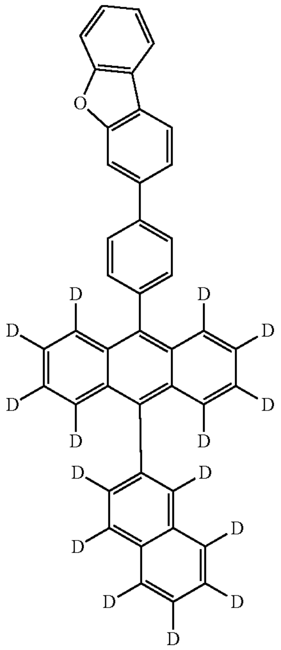
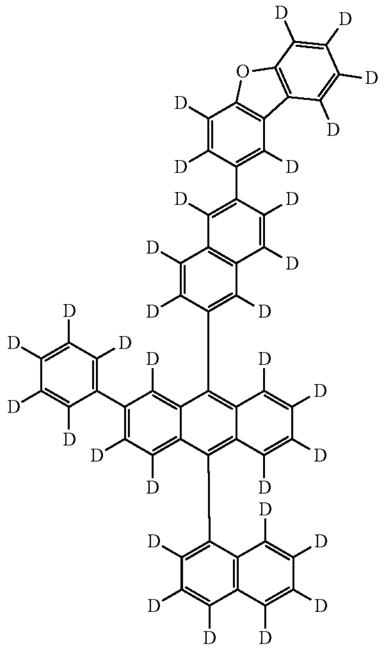
In an exemplary embodiment of the present specification, the compound represented by Formula 1-2 is any one selected from the following compounds.

-continued
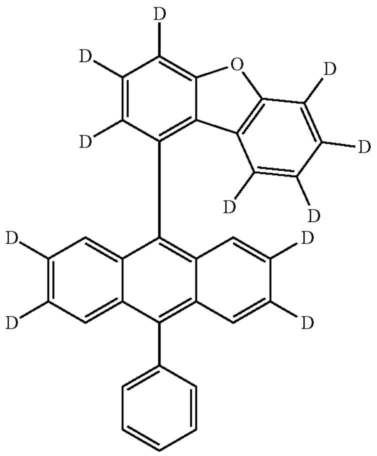
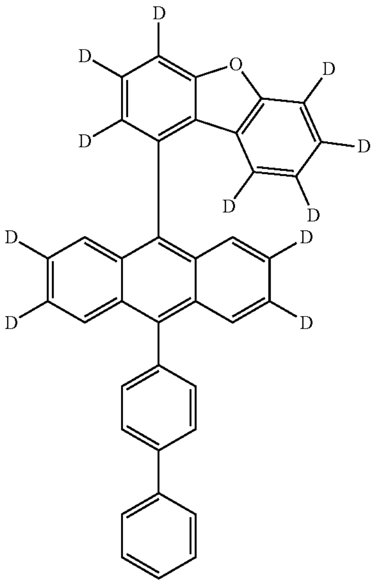
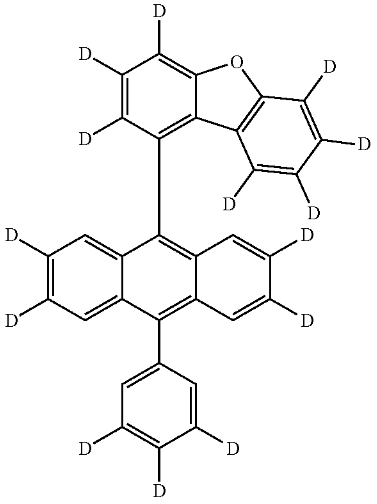
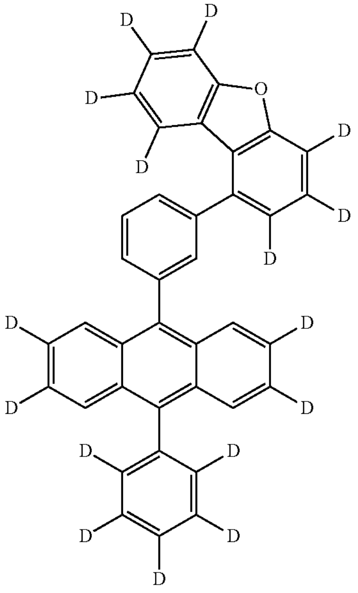
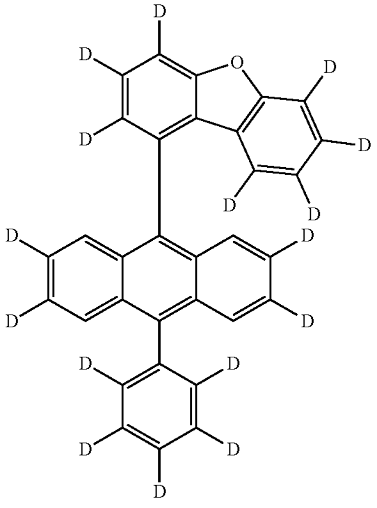
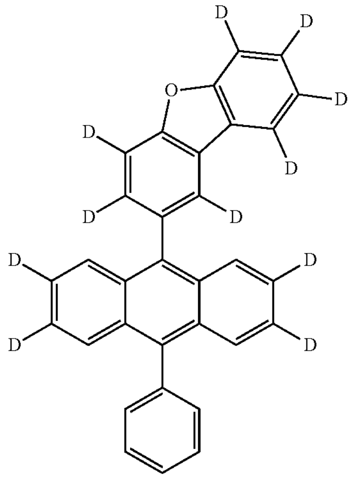

-continued
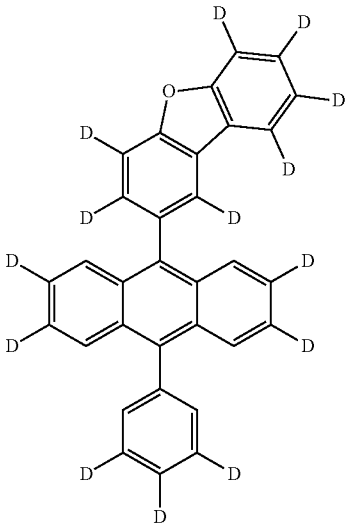
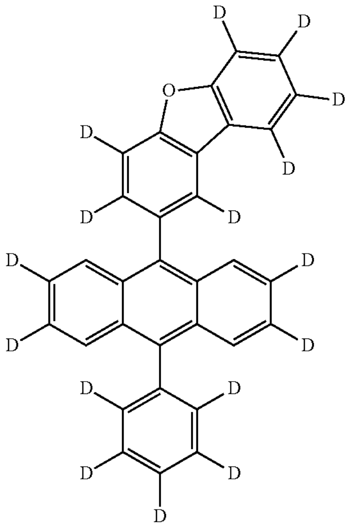
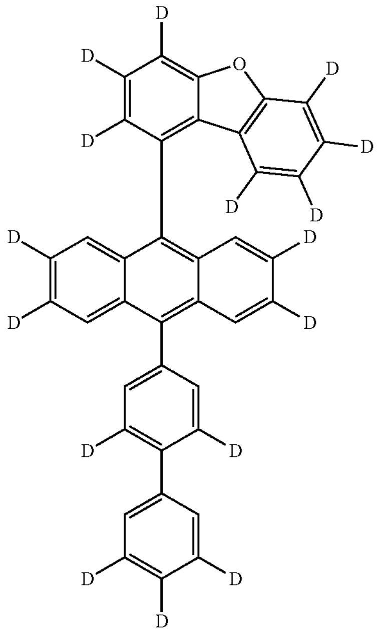
-continued
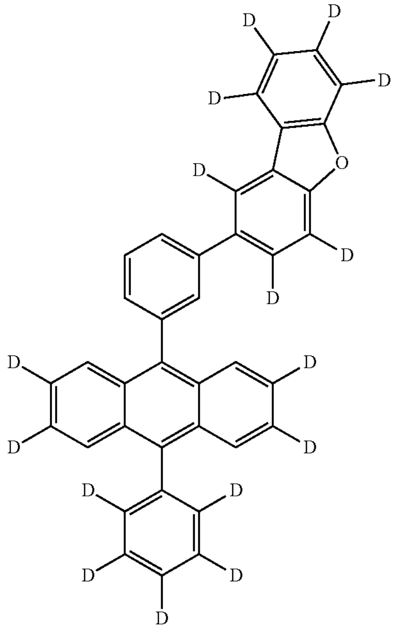
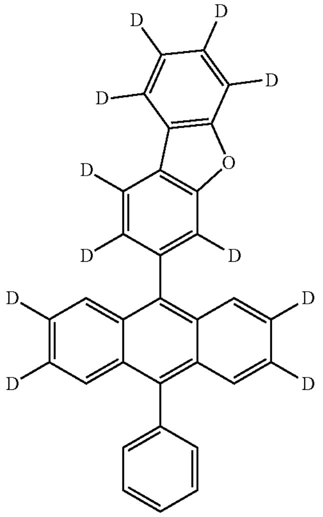
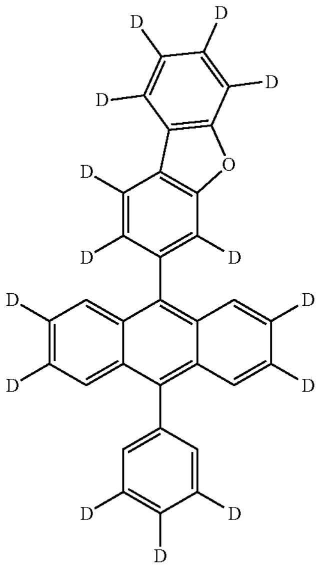

-continued
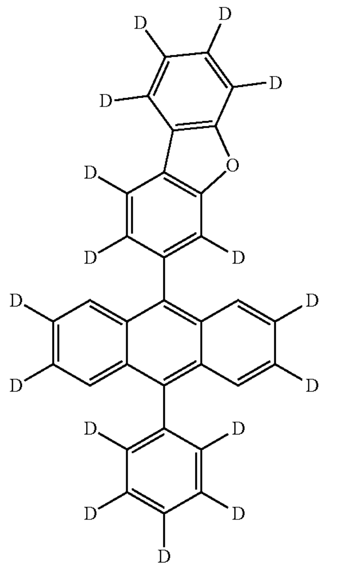
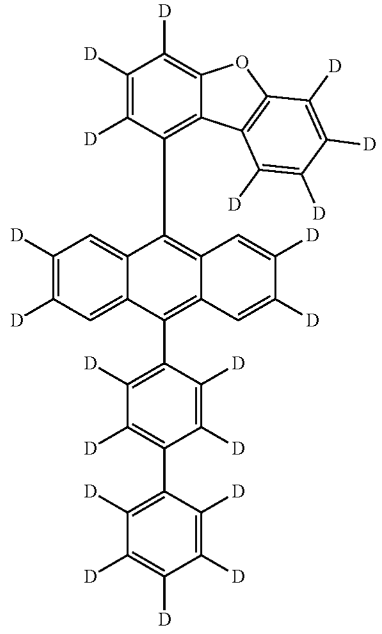
-continued
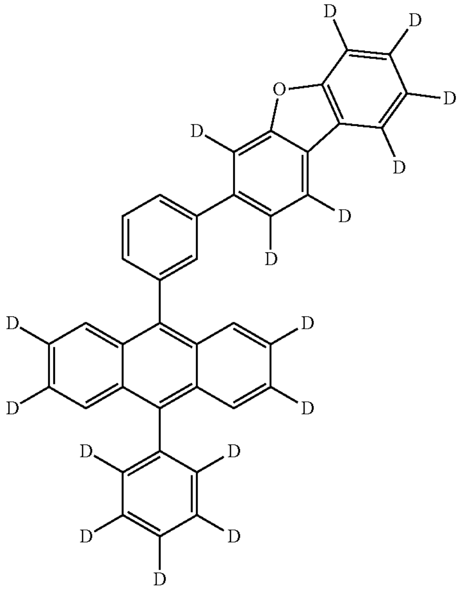
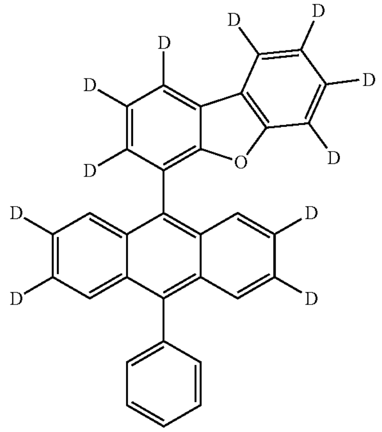
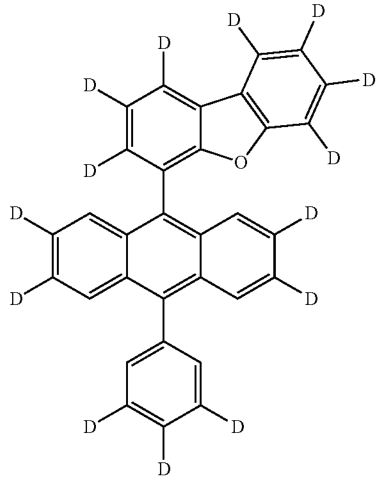

-continued
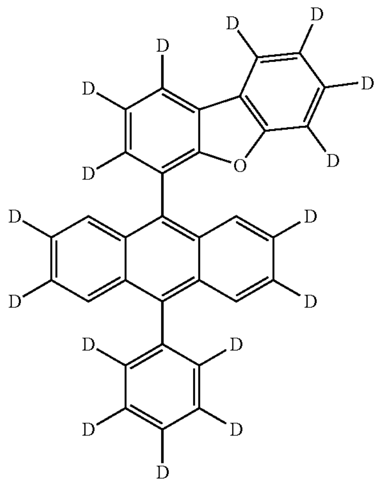
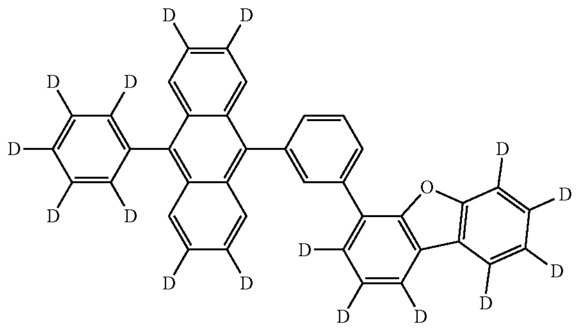
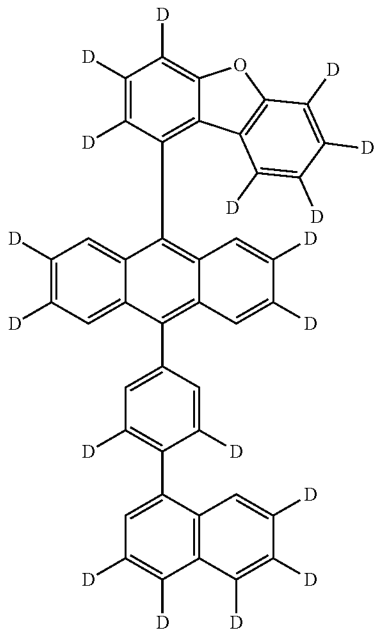
-continued
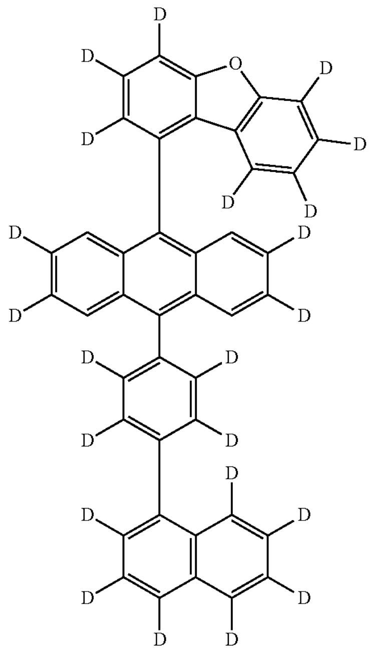
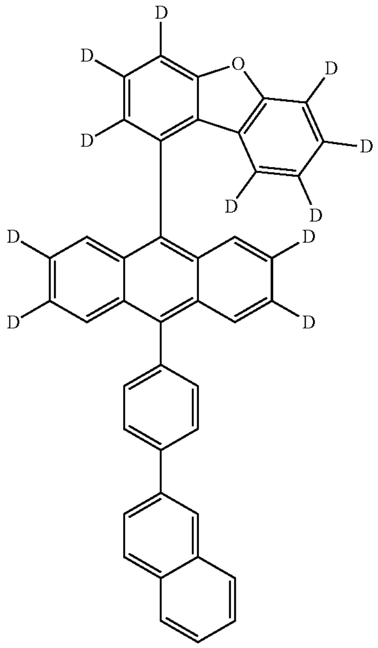

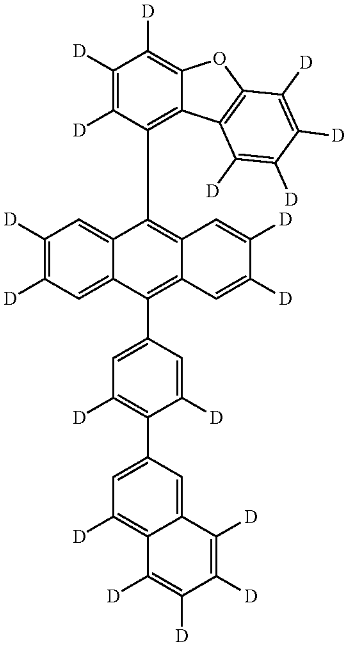
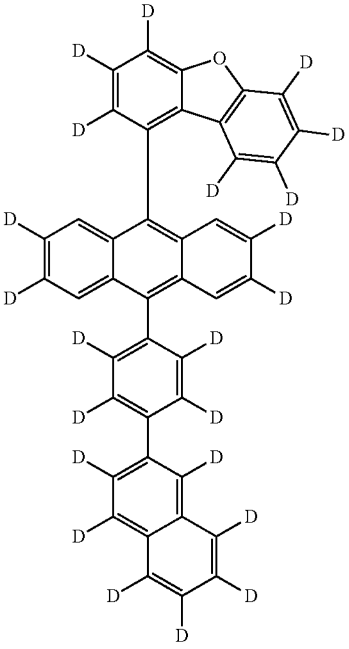
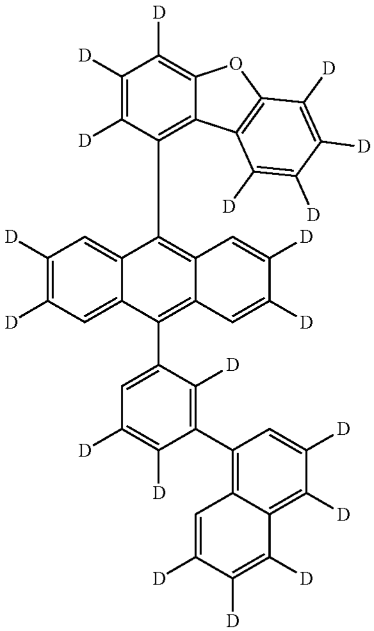
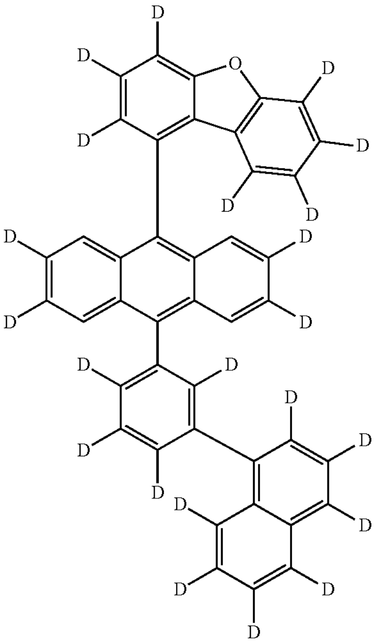

-continued
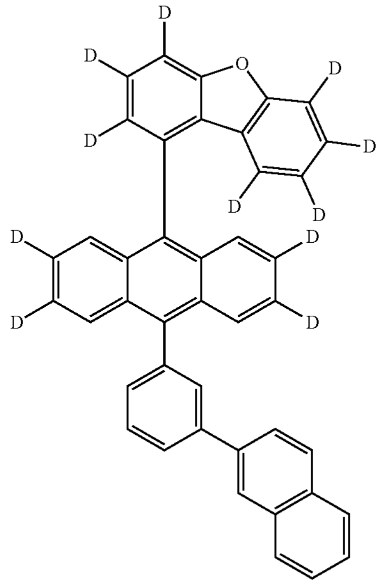
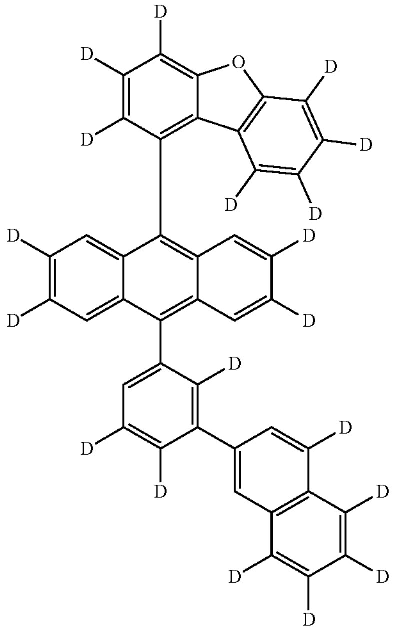
-continued
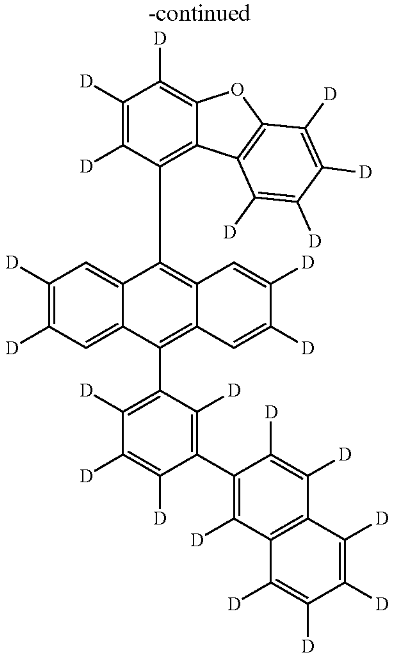
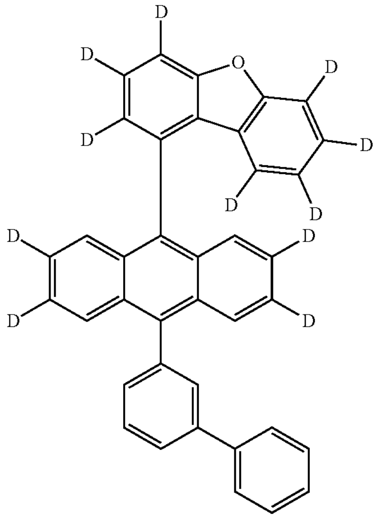
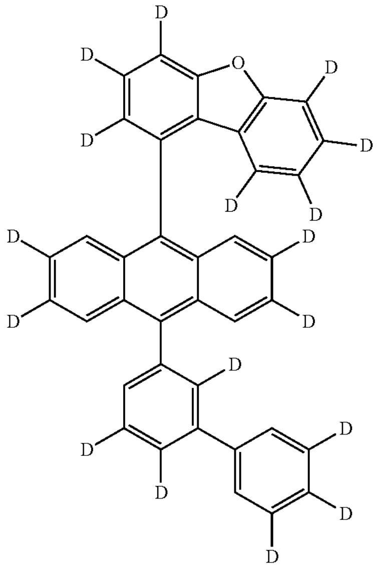

-continued
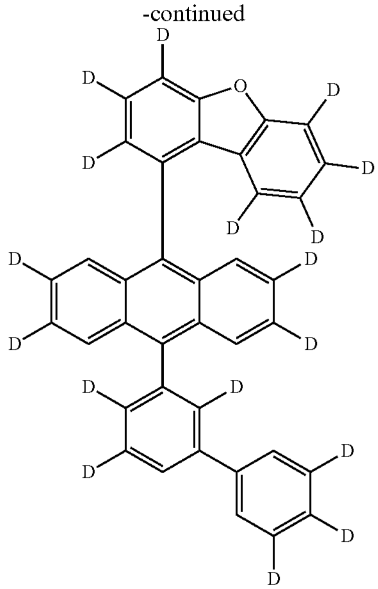
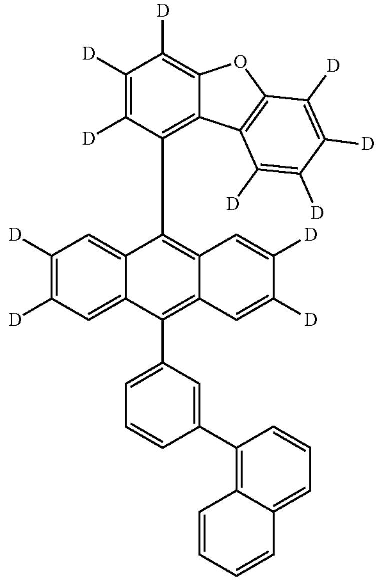
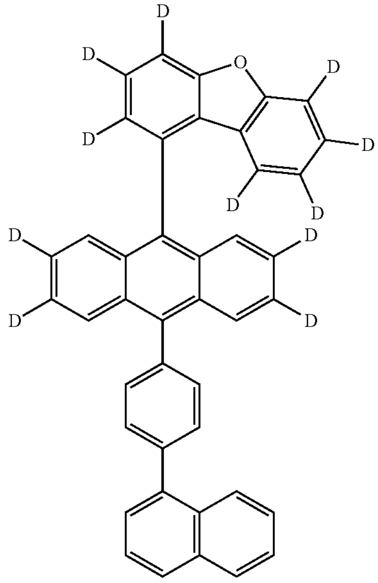
-continued
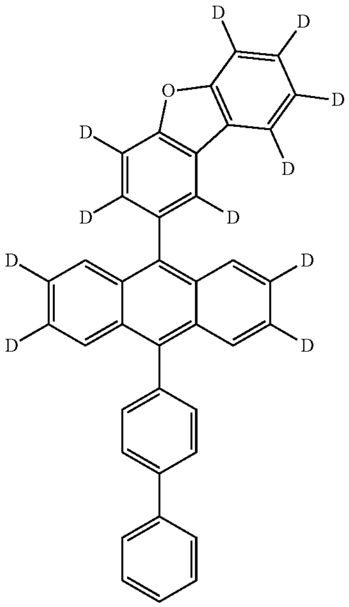
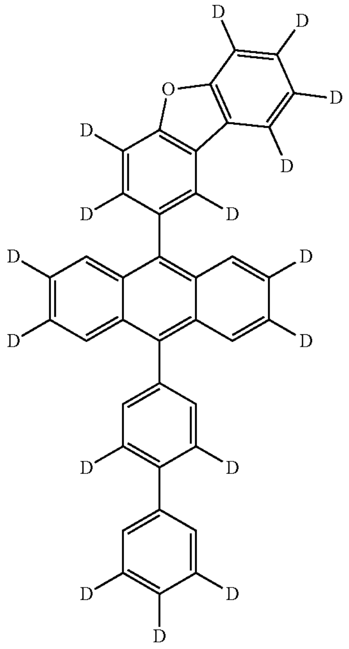

-continued
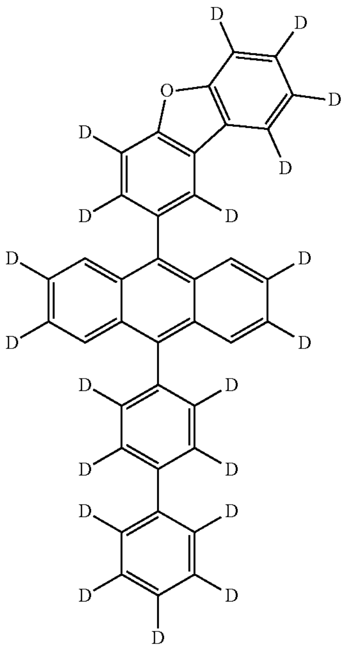
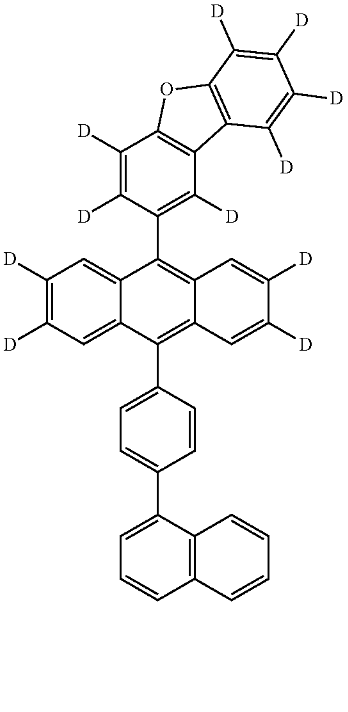
-continued
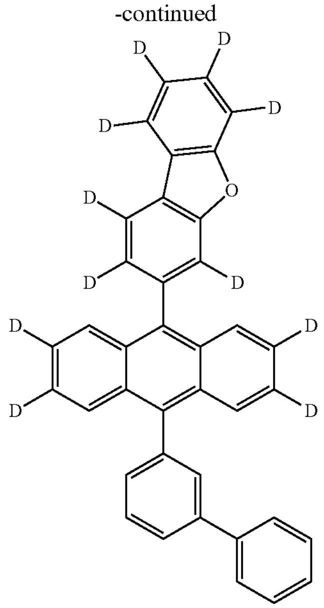
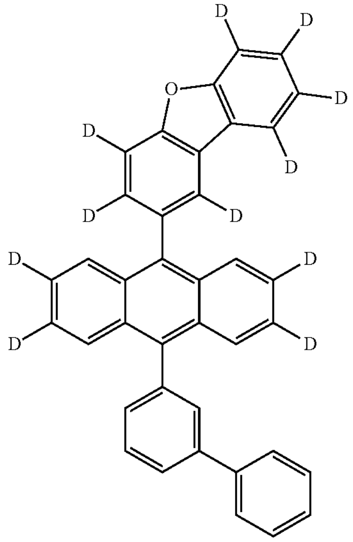
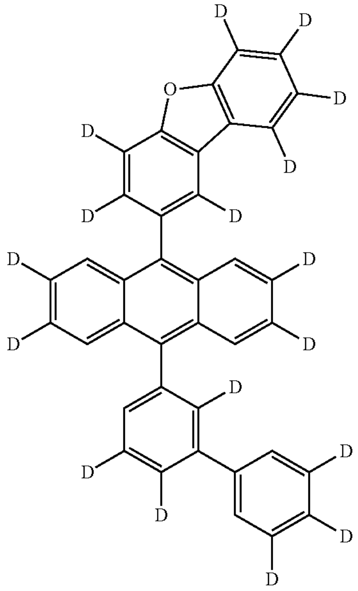

-continued
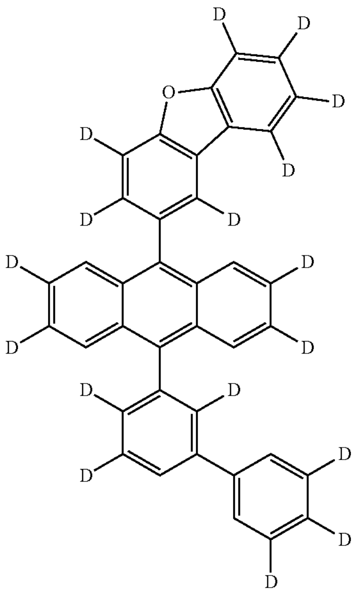
-continued
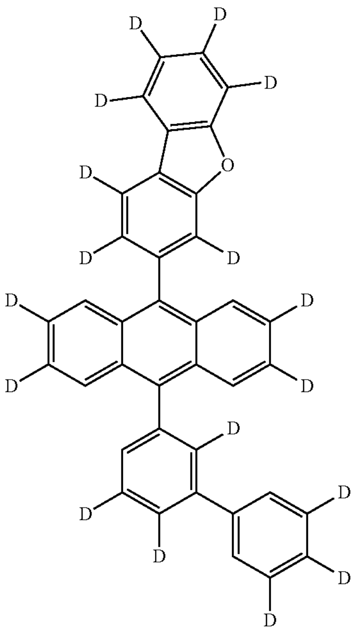
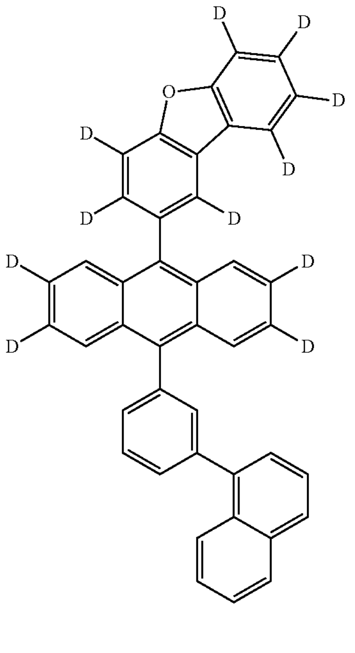
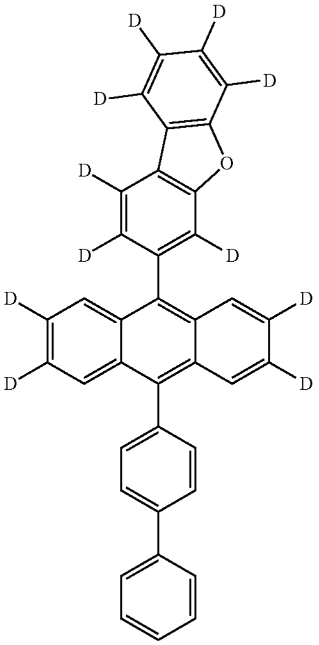

-continued
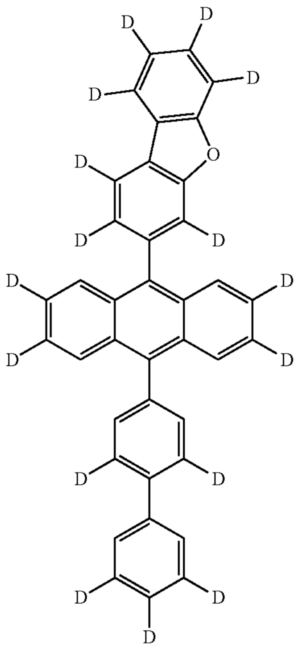
-continued
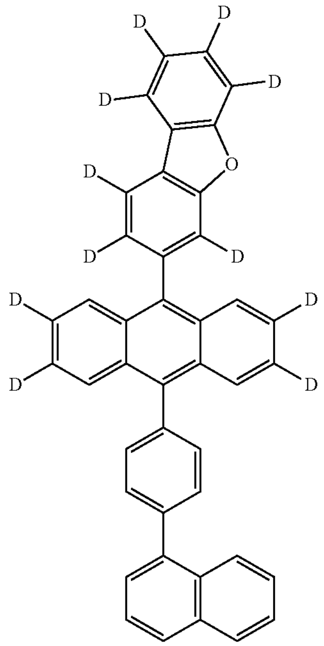
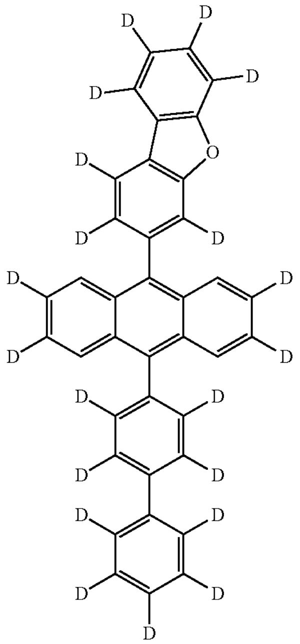
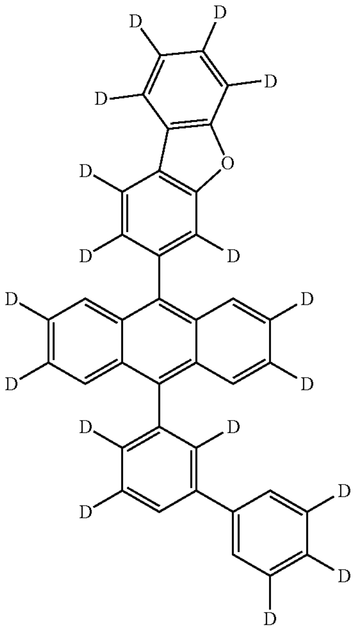

-continued
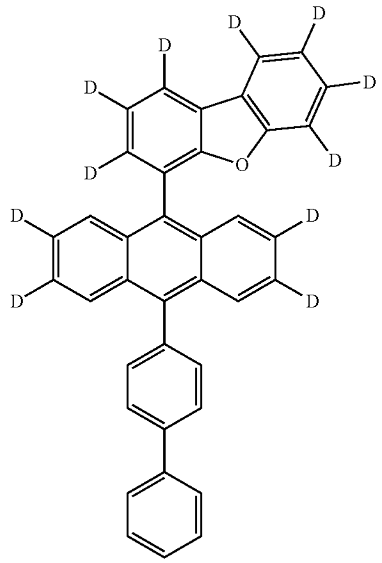
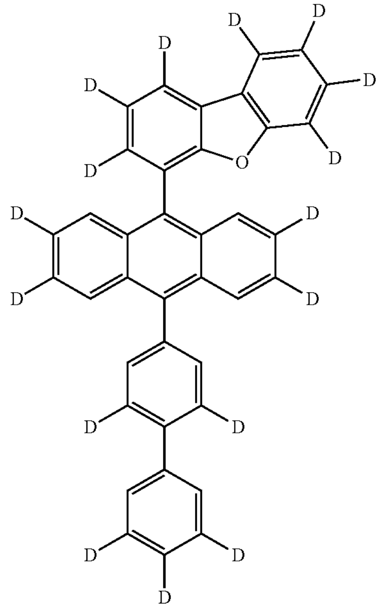
-continued
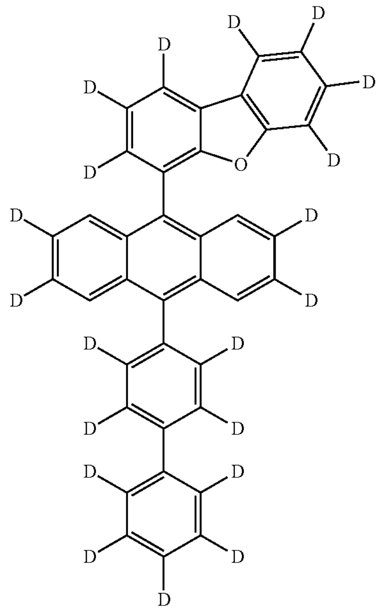
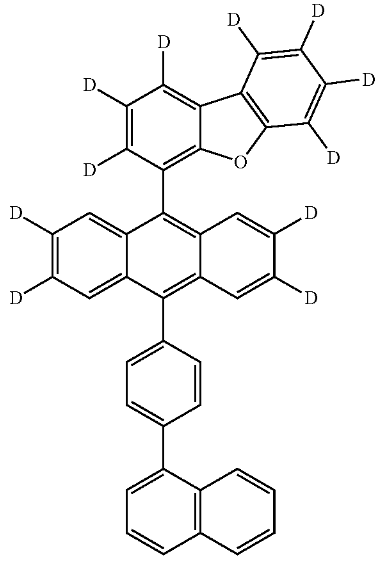

-continued
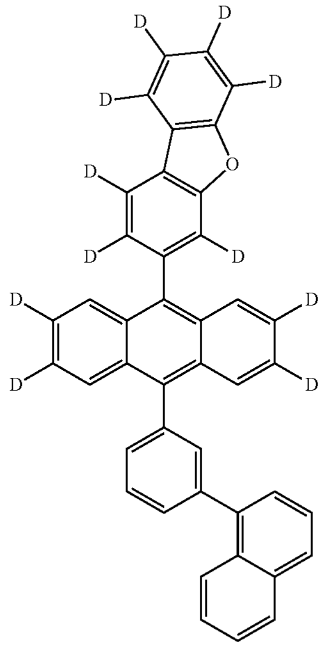
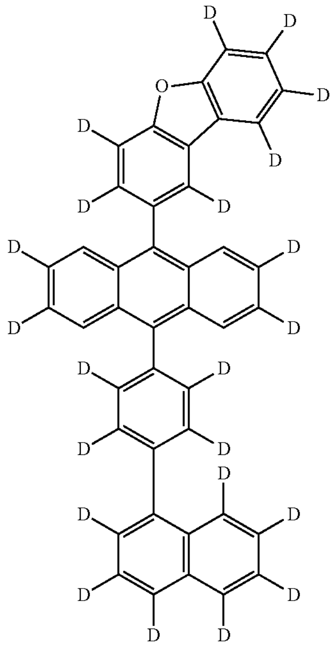
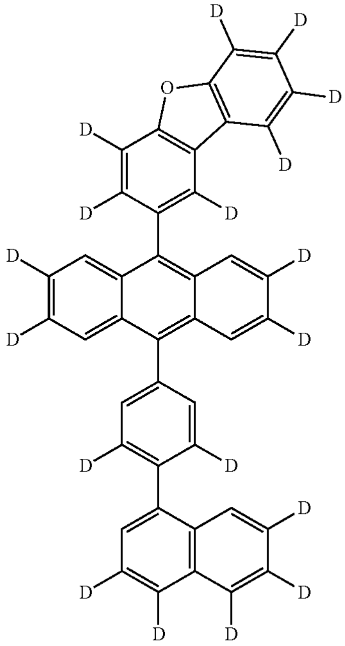
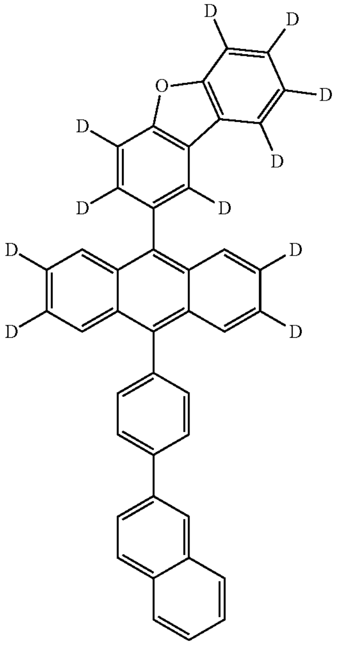

-continued
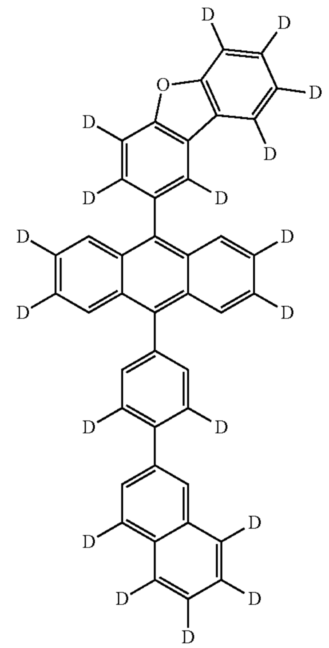
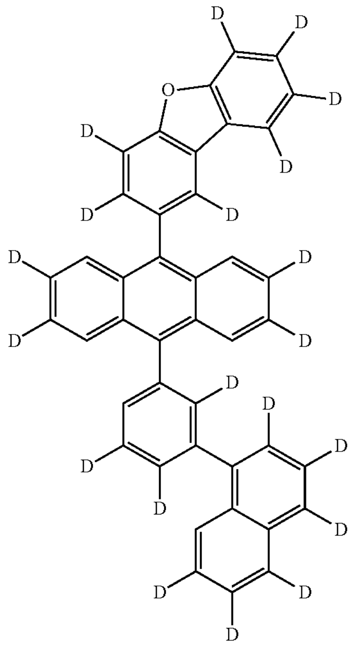
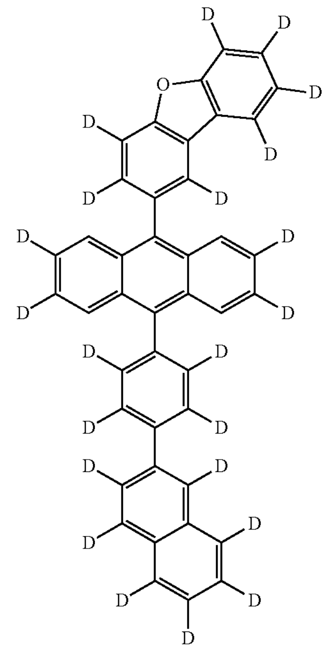
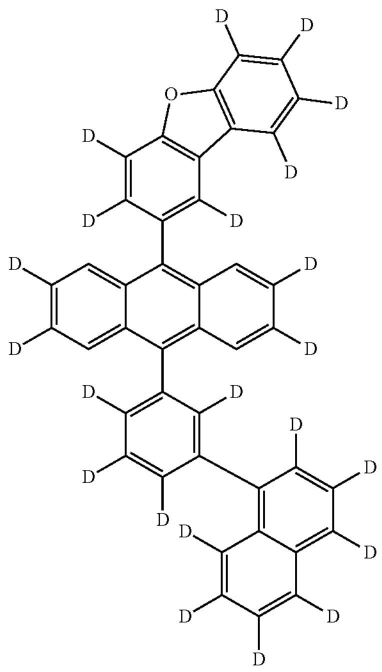
-continued

-continued
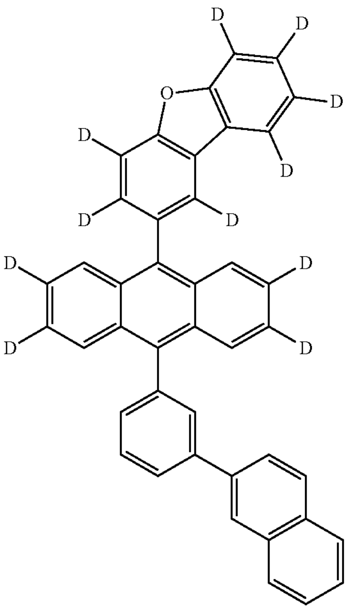
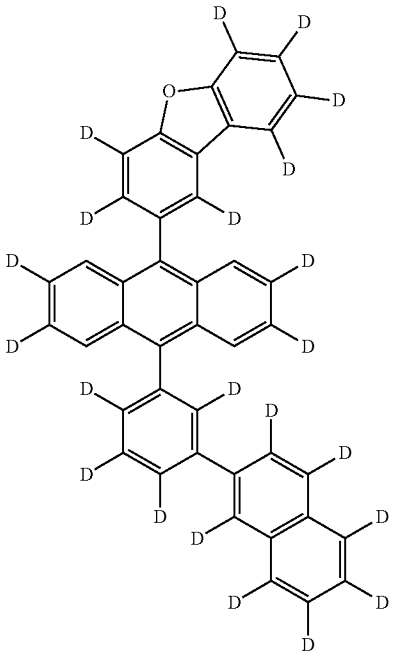
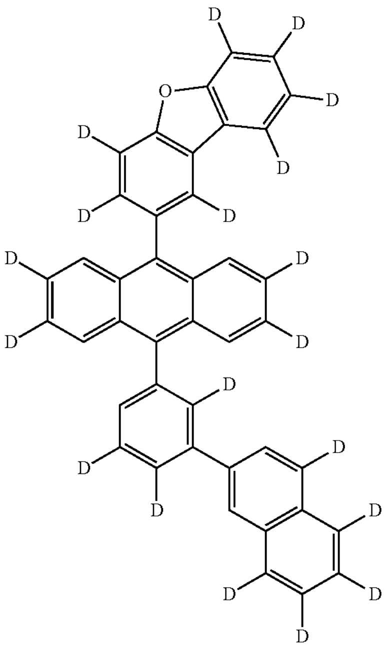
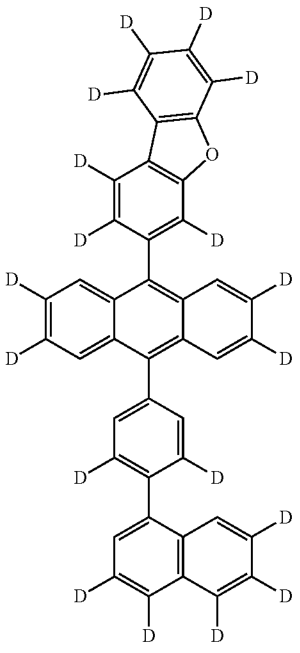
-continued

-continued
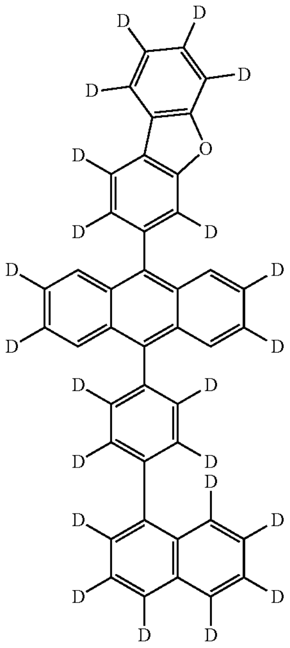
-continued
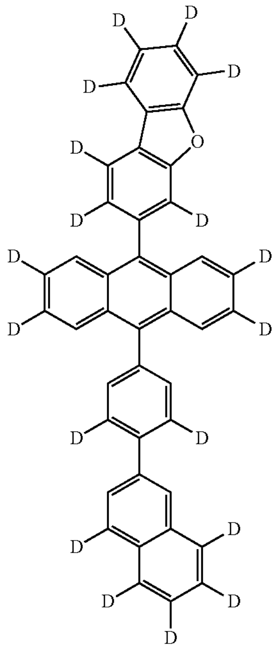
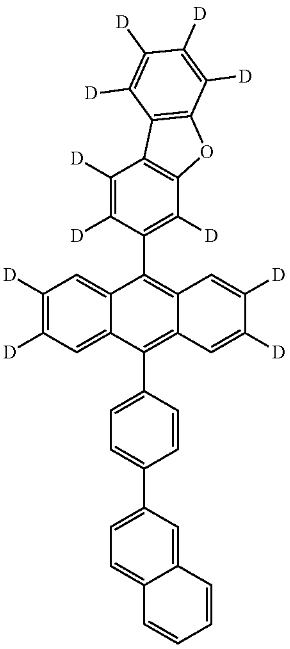
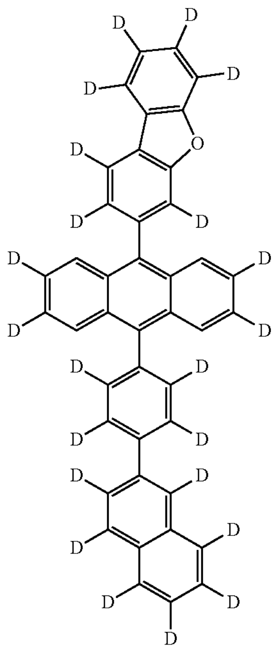

-continued
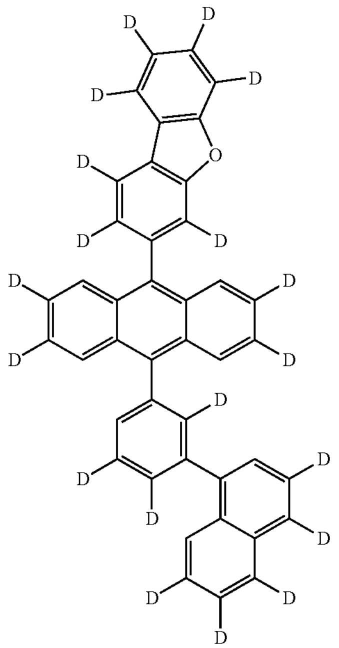
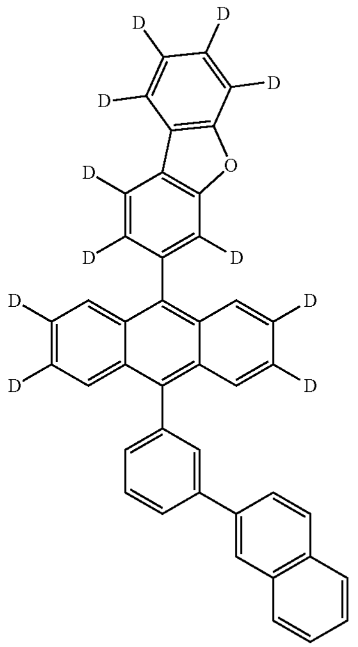
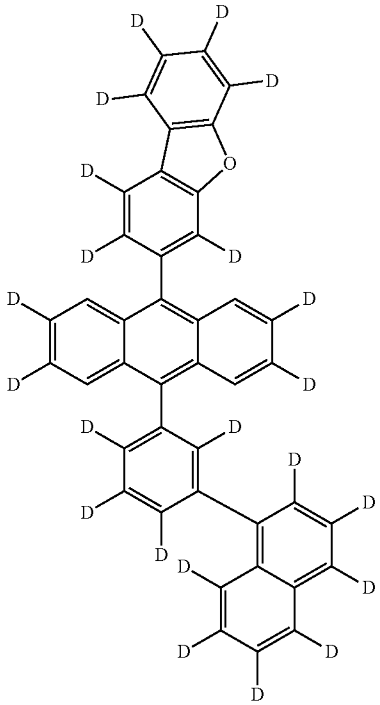
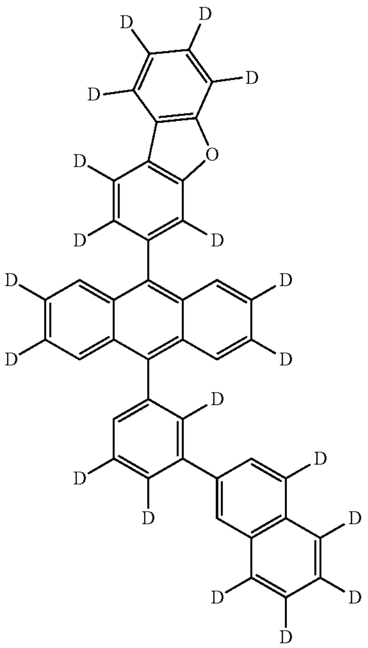

-continued
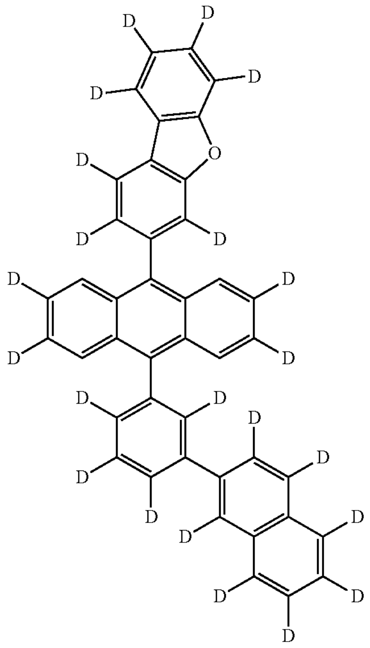
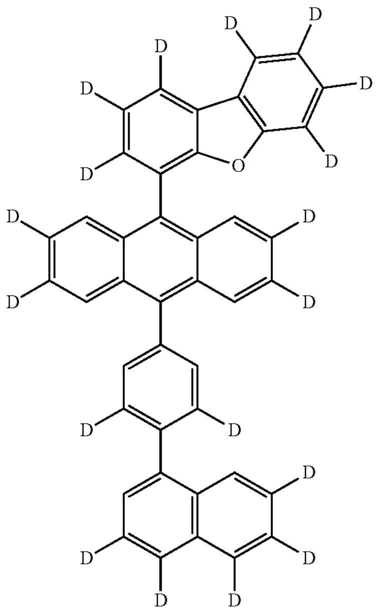
-continued
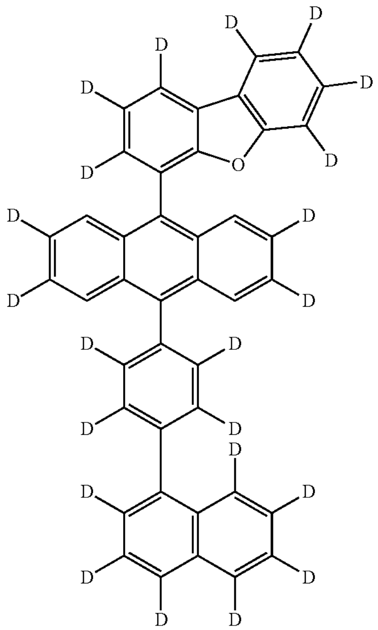
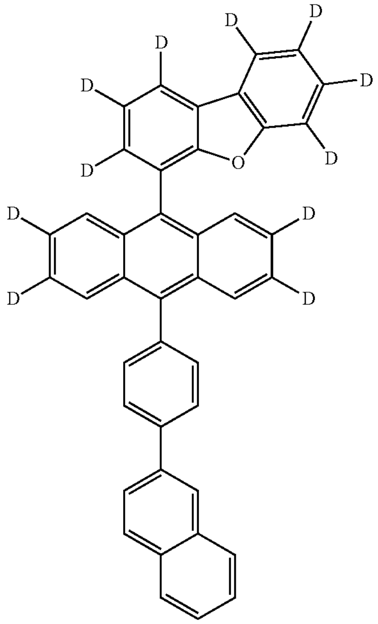

-continued
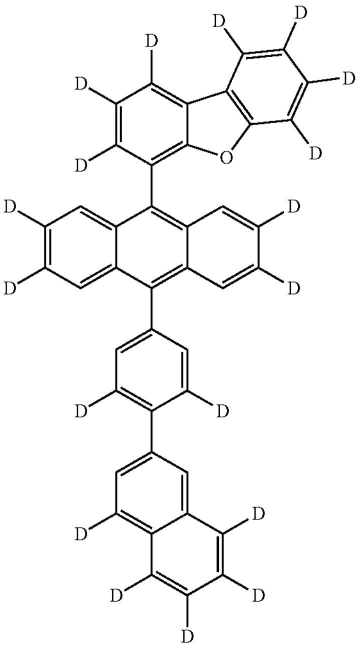
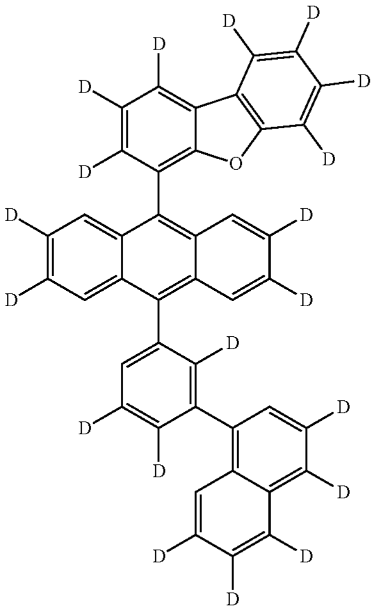
-continued
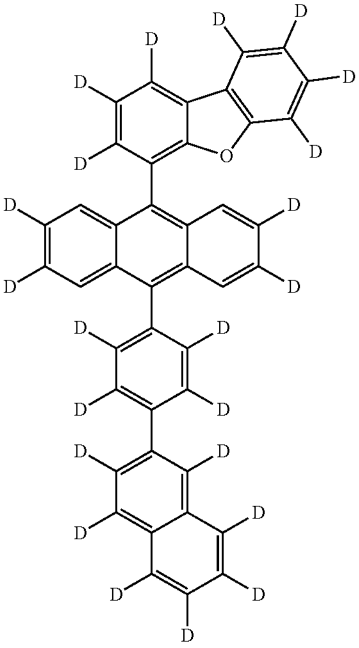
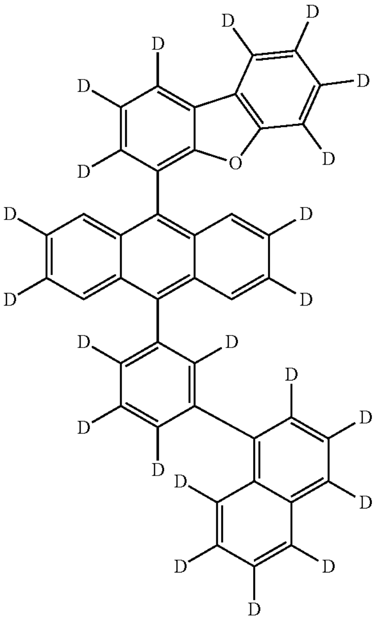

-continued
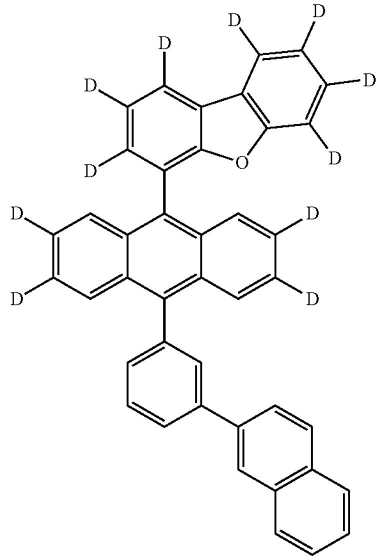
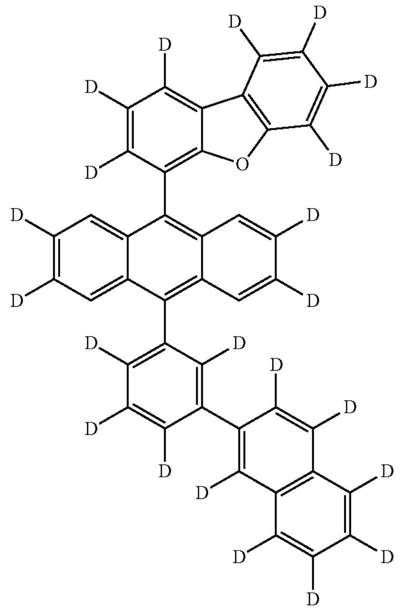
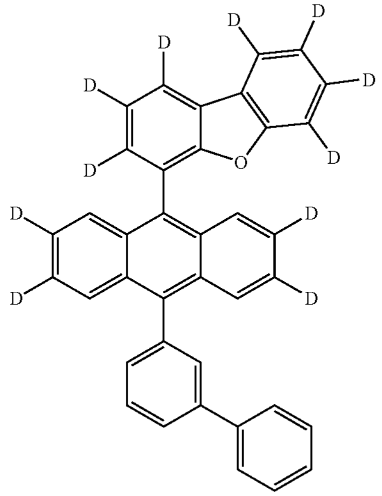
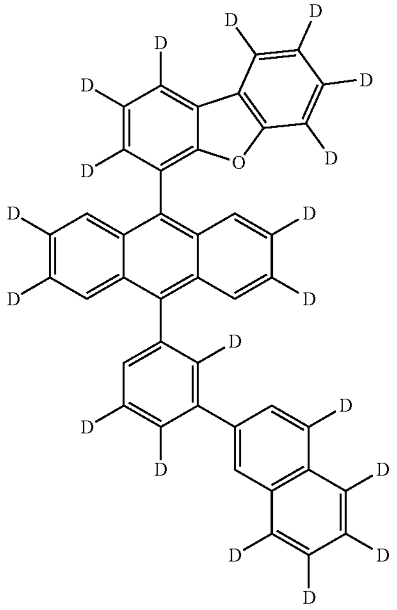
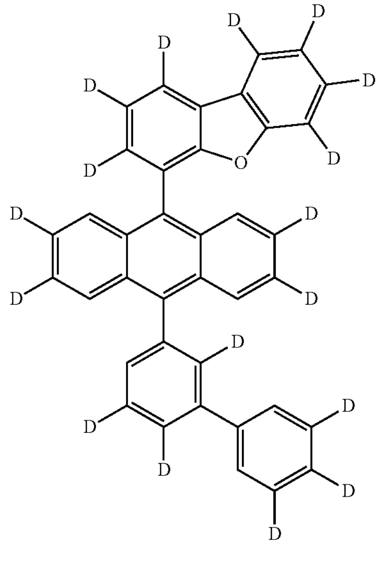

-continued
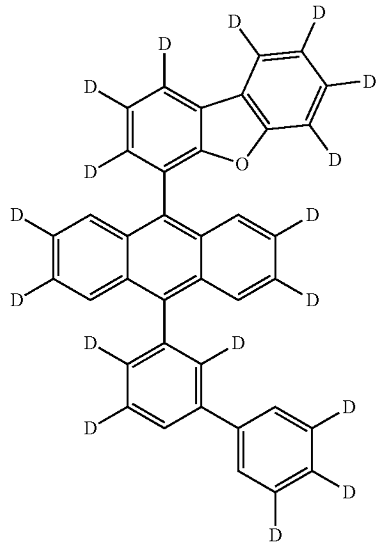
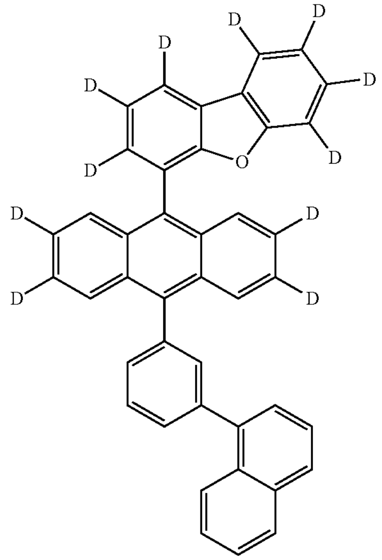
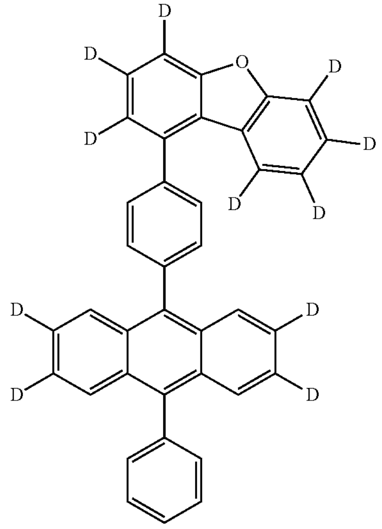
-continued
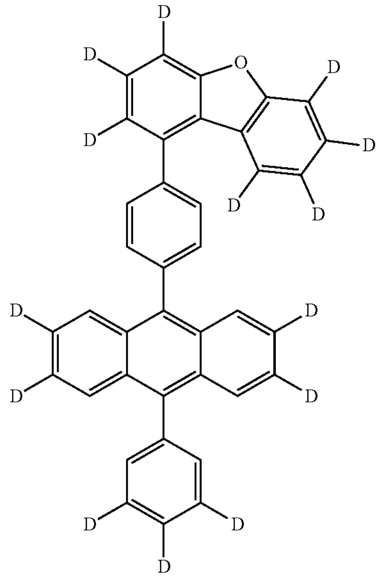
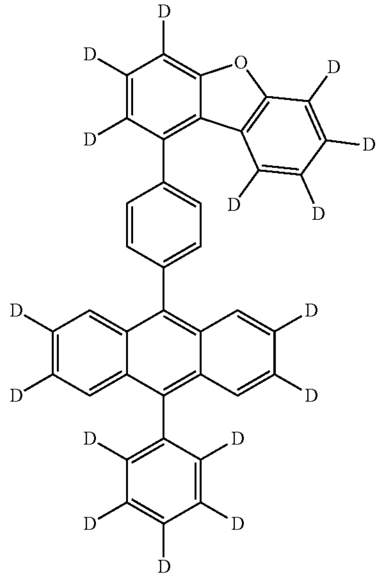
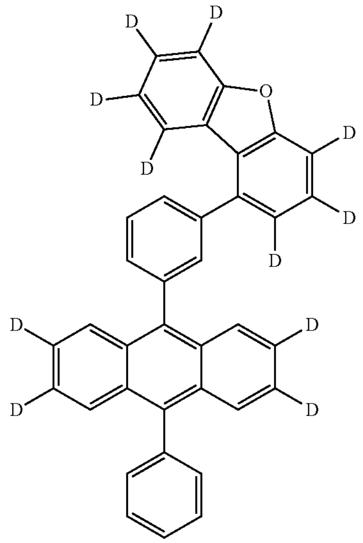

-continued
-continued
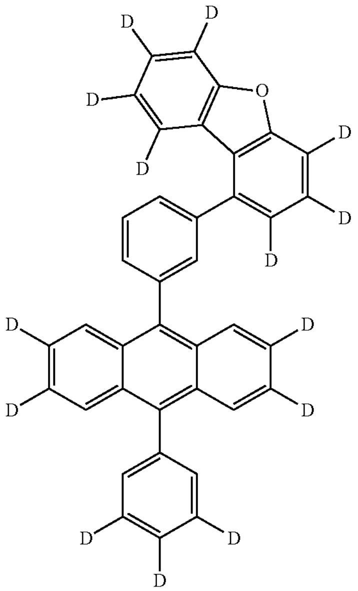
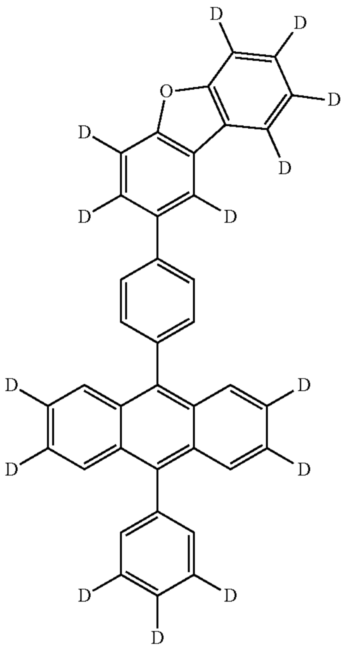
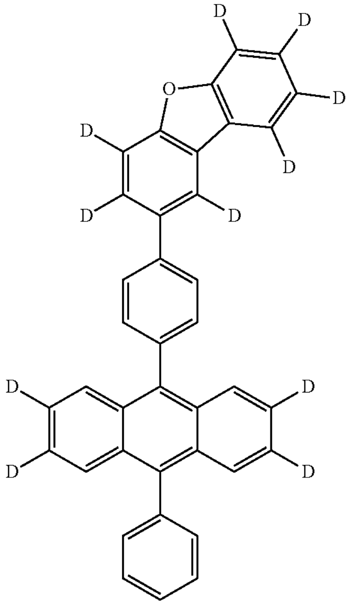
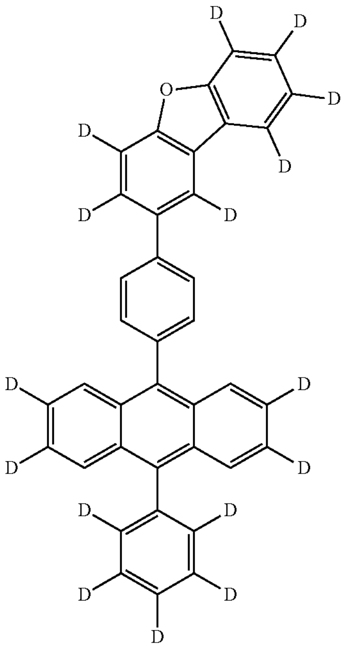

-continued
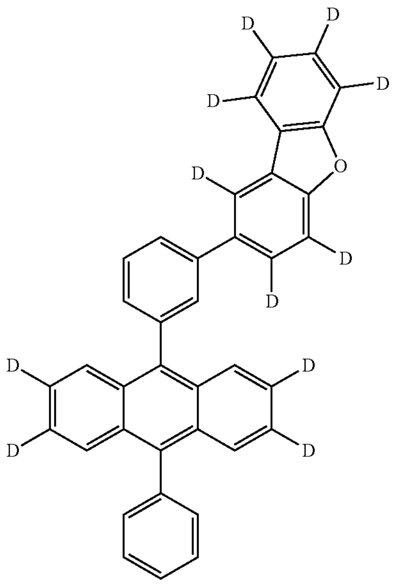
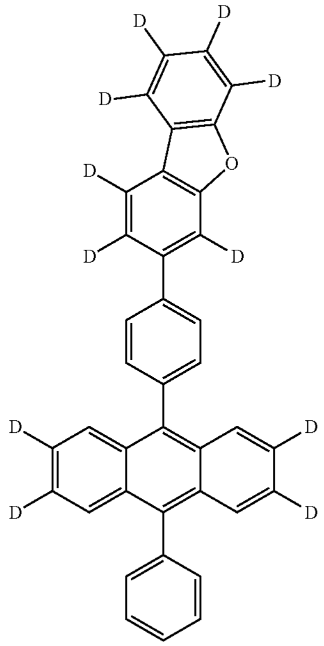
-continued
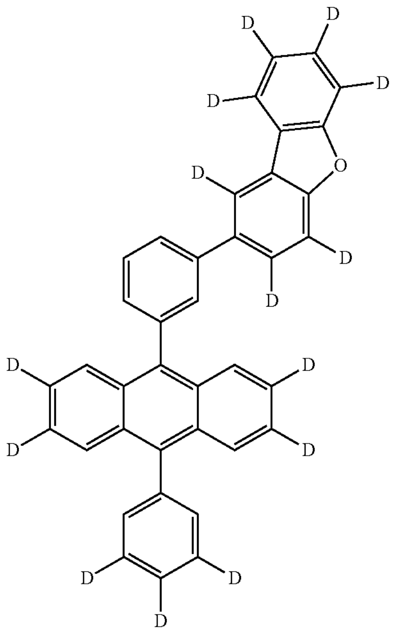
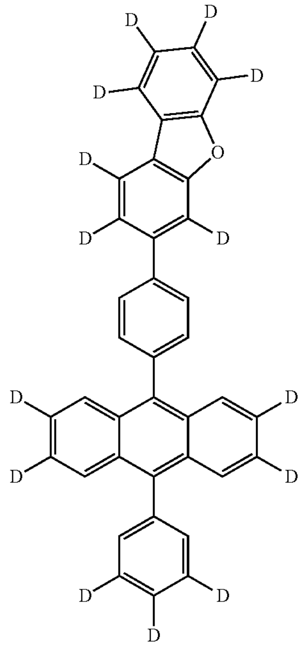

-continued
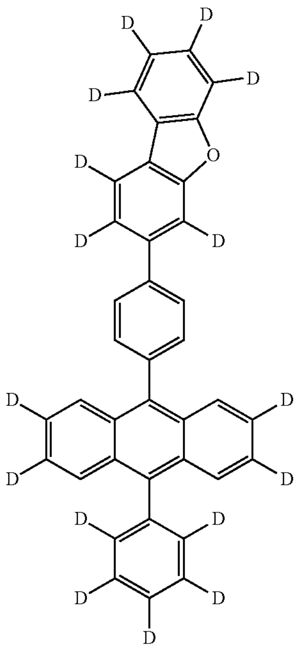
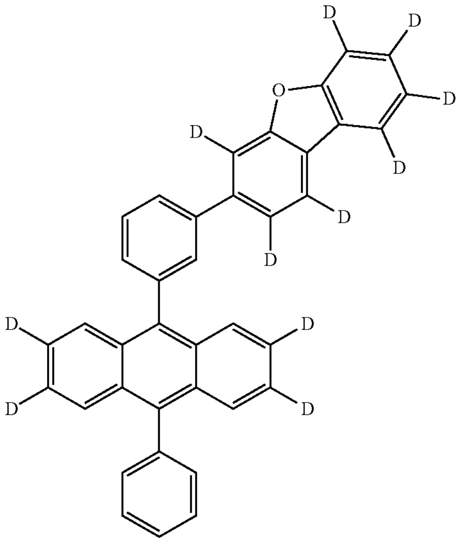
-continued
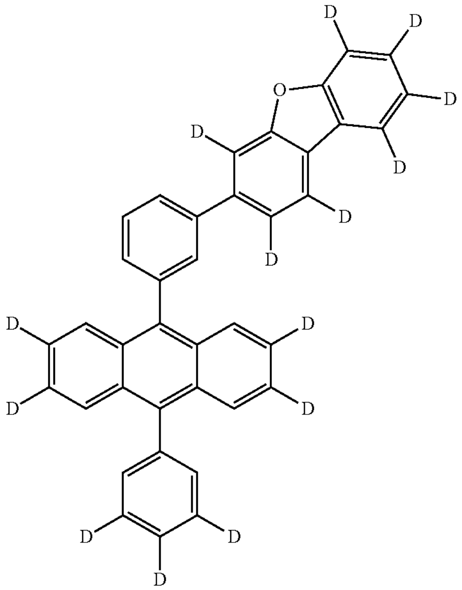
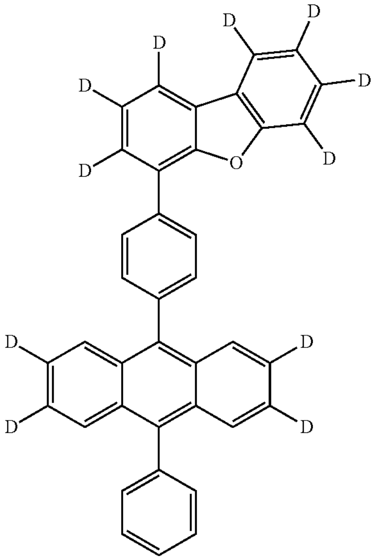

-continued
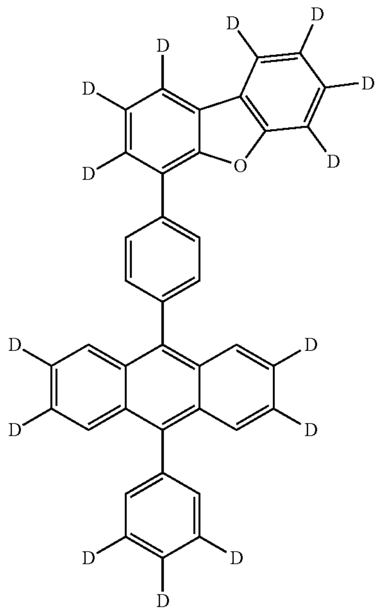
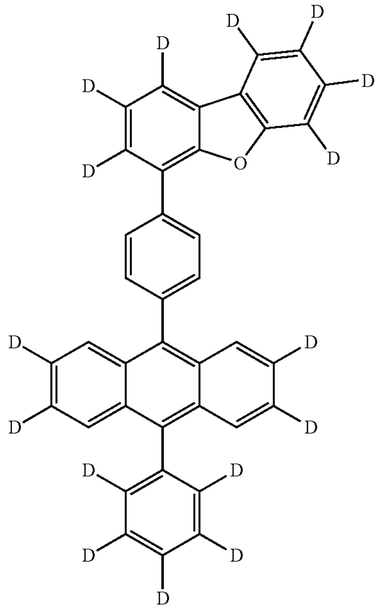
-continued
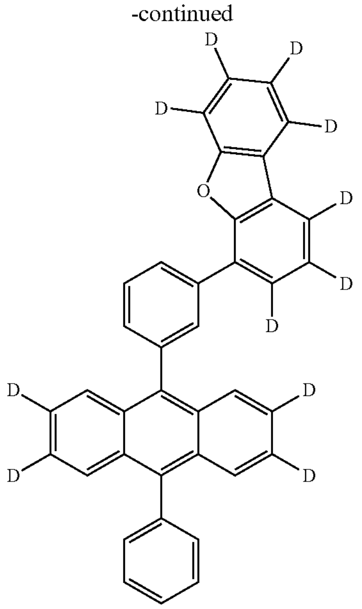
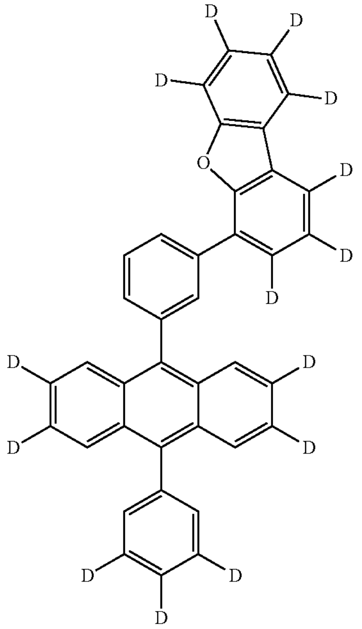
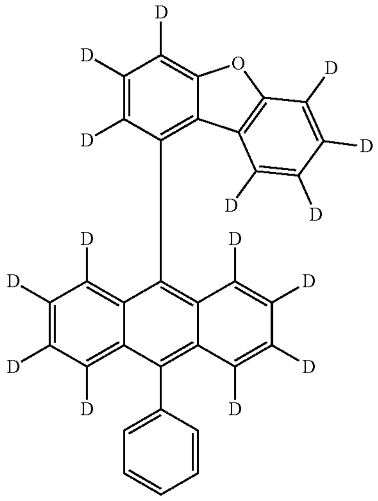

-continued
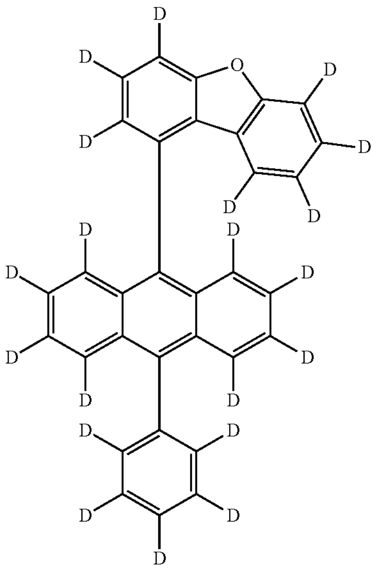
-continued
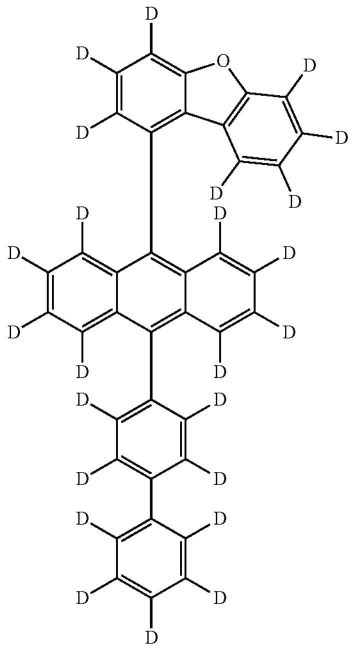
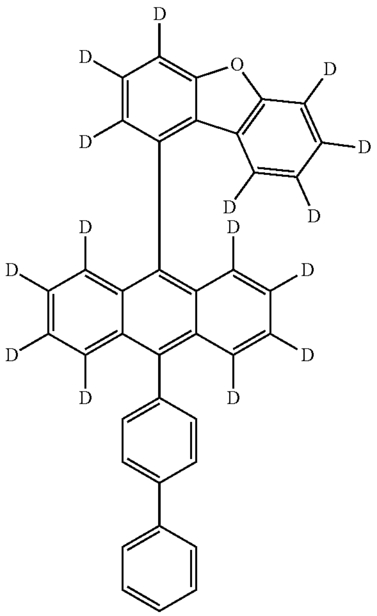
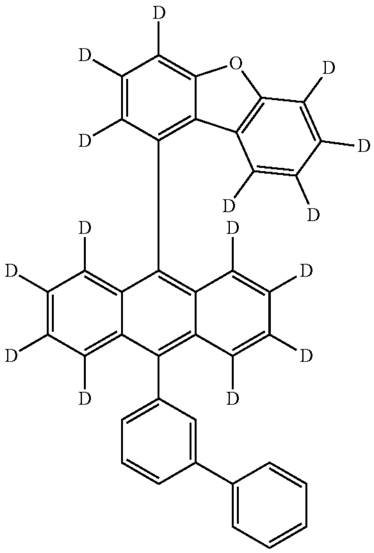

-continued
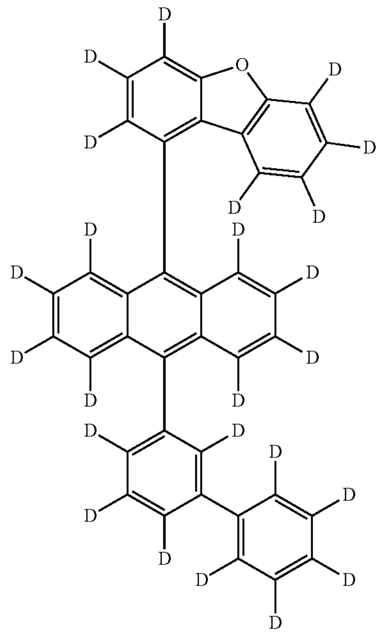
-continued
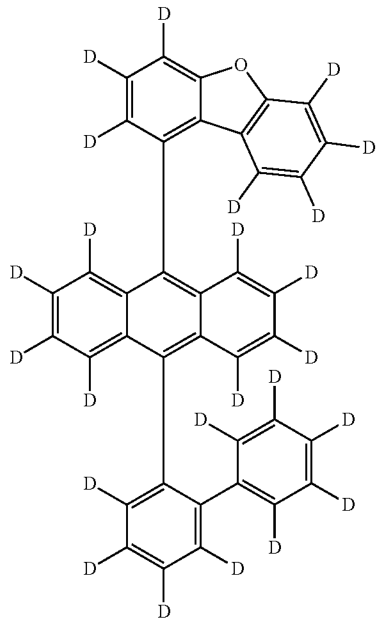
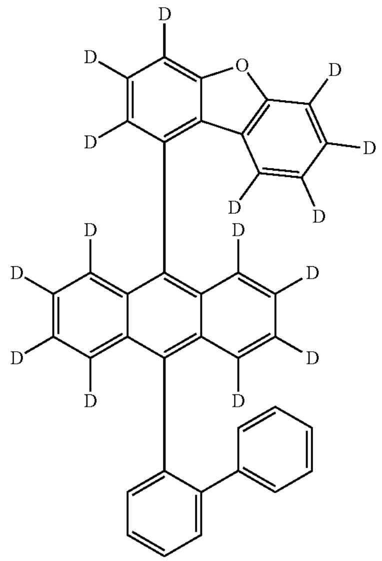
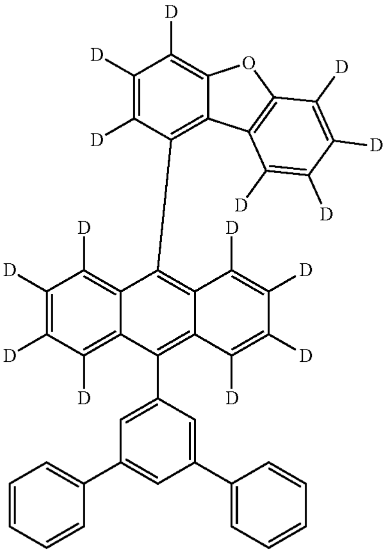

-continued
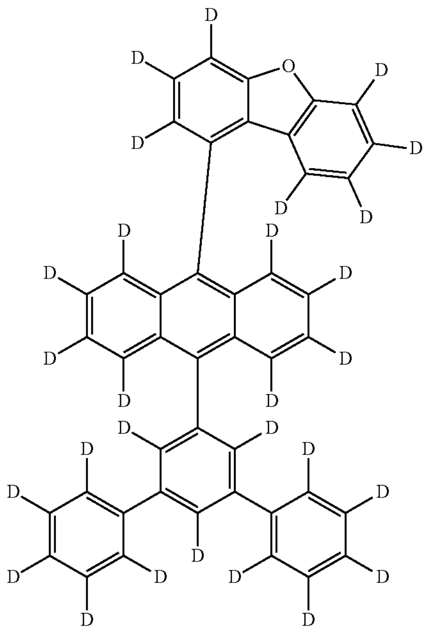
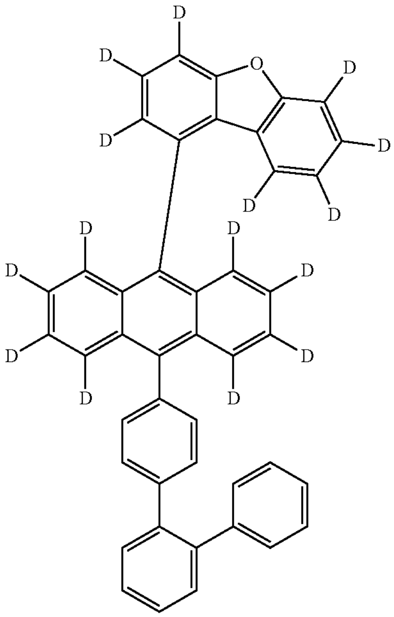
-continued
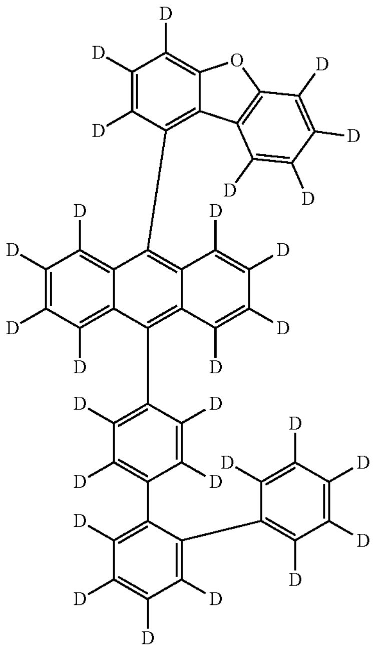
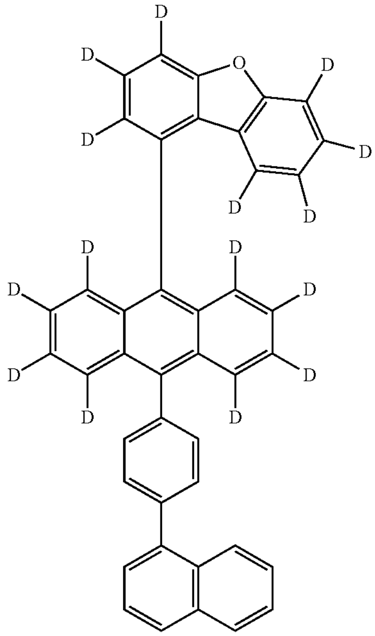

-continued
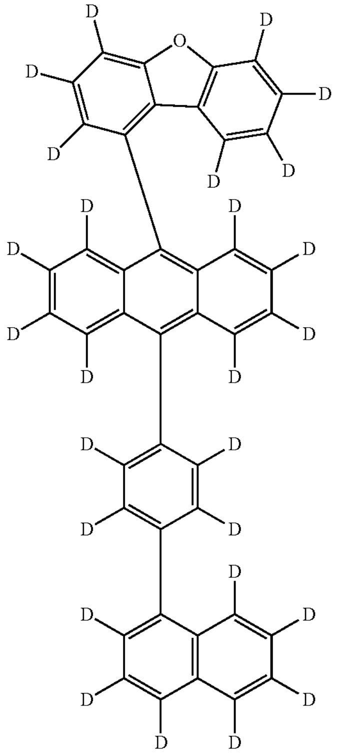
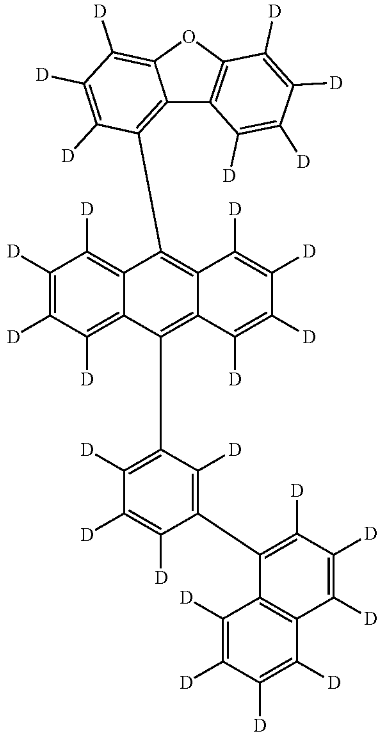
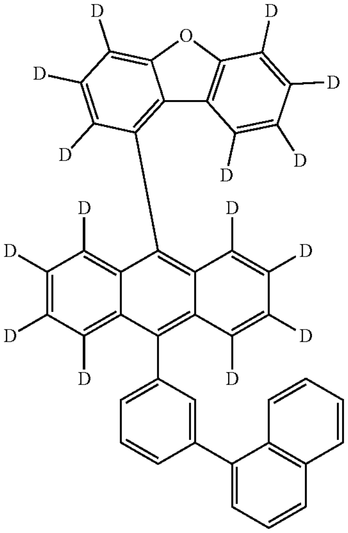
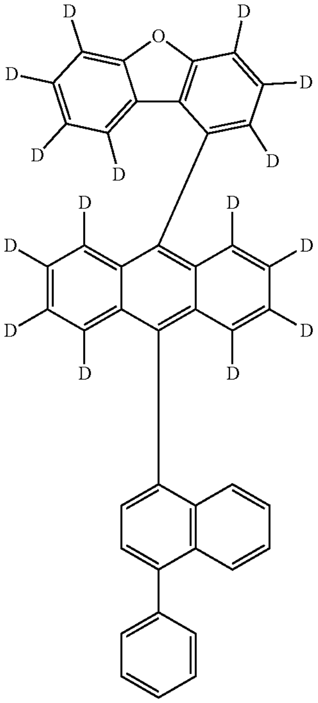
-continued

-continued
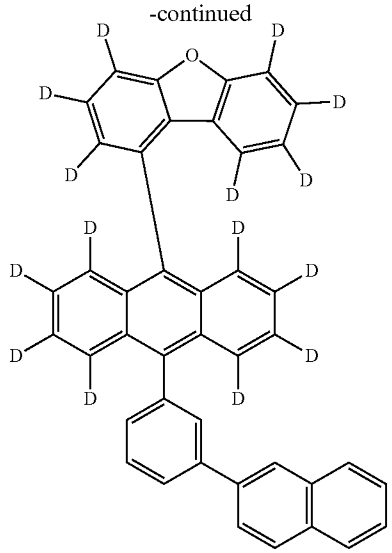
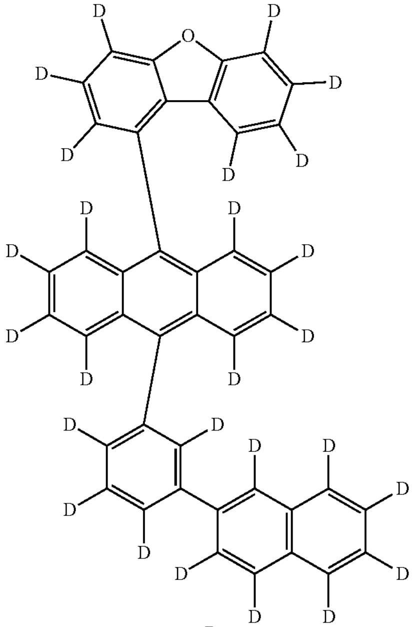
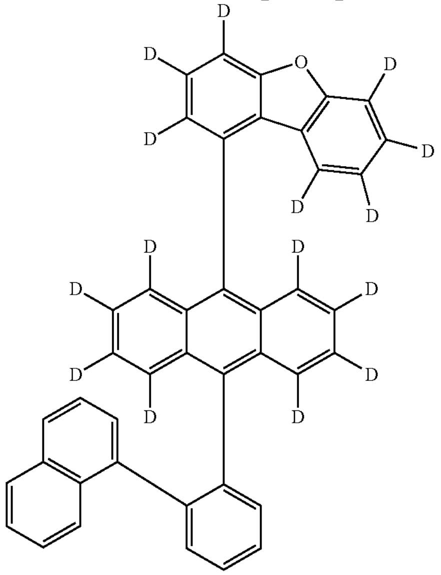
-continued
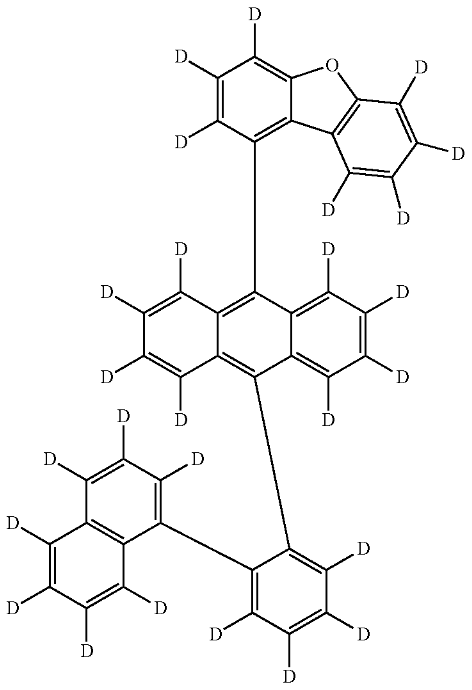
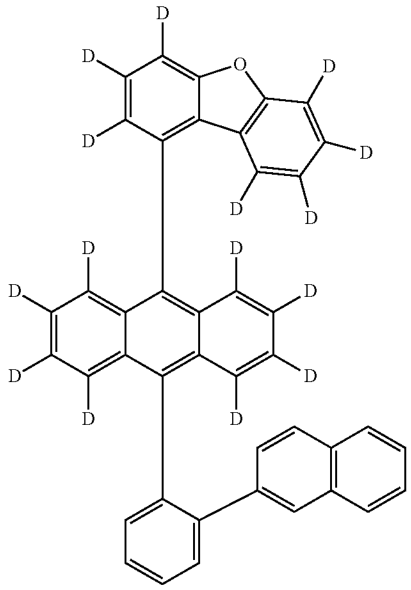

-continued
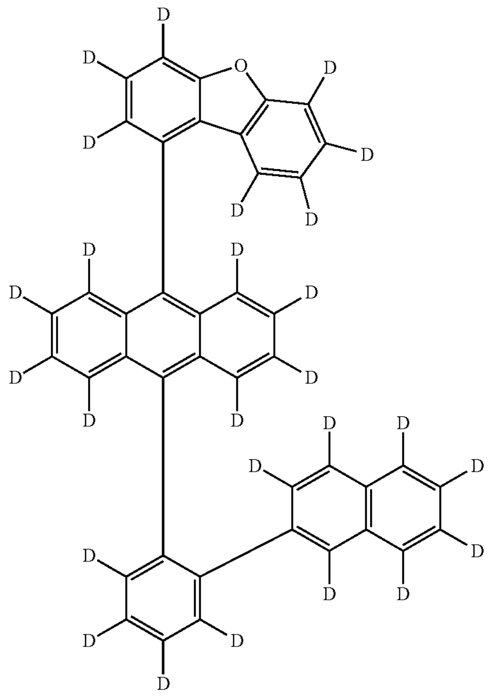
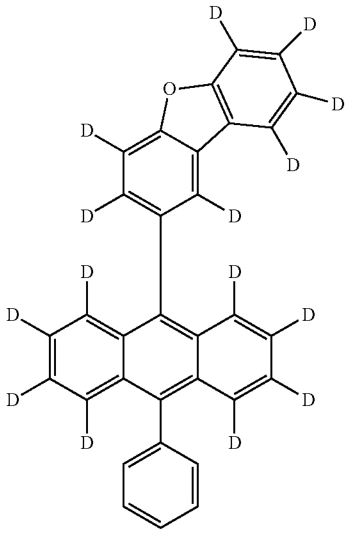
-continued
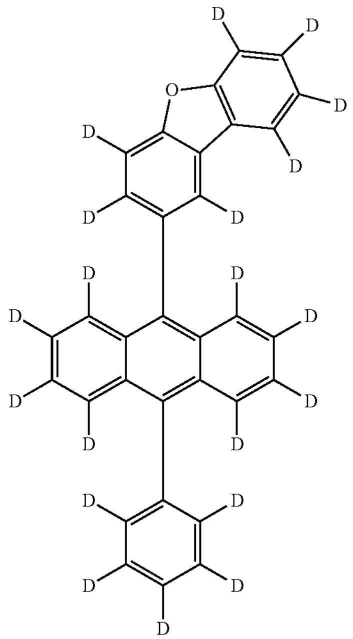
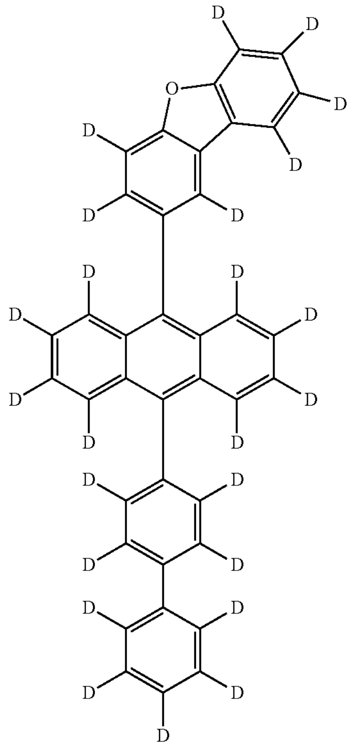

-continued
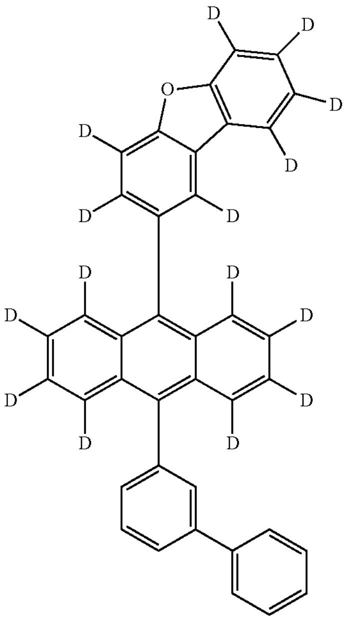
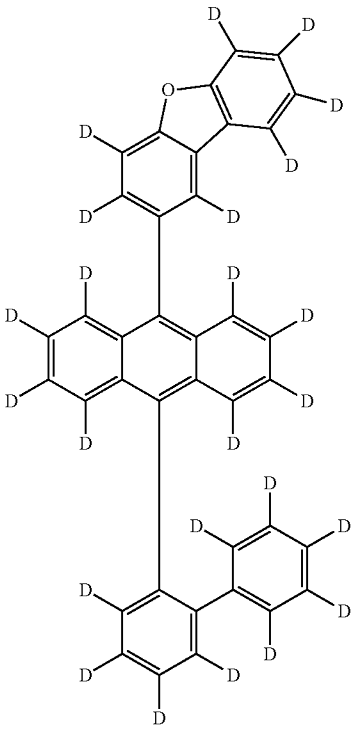
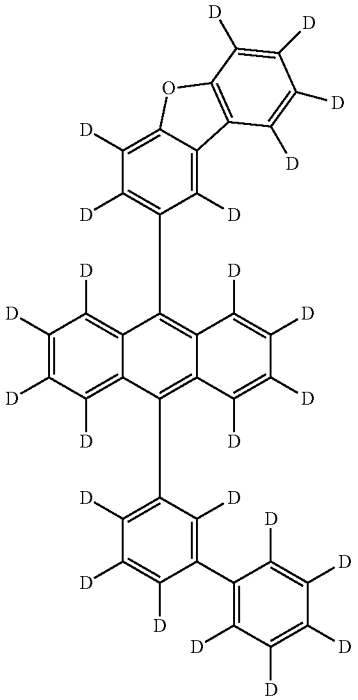
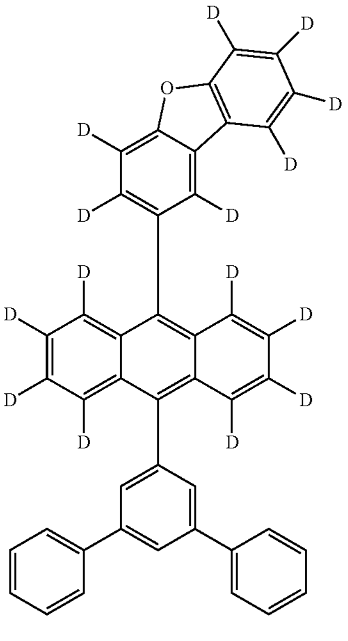

-continued
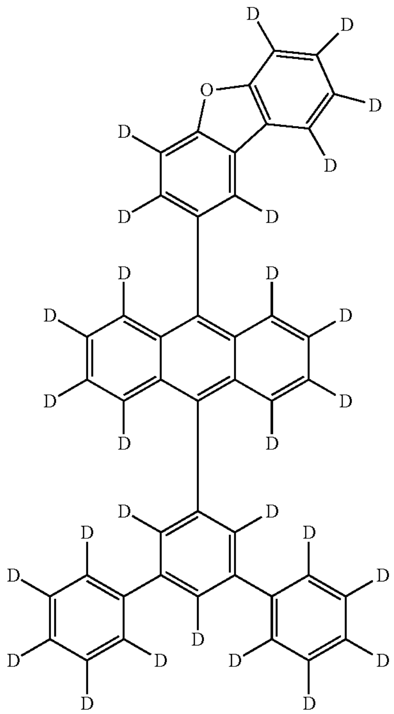
-continued
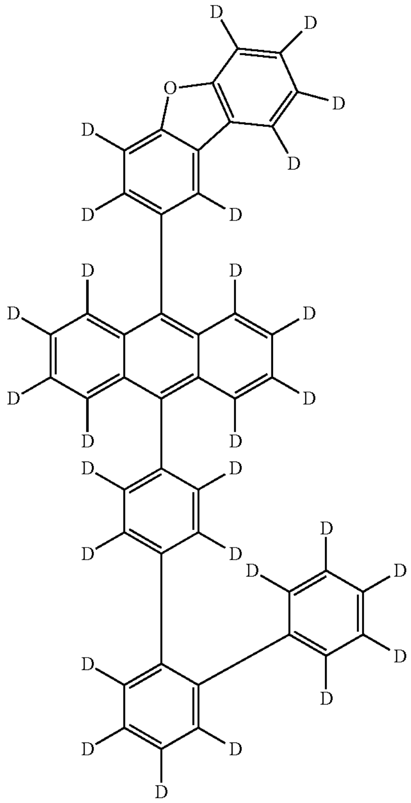
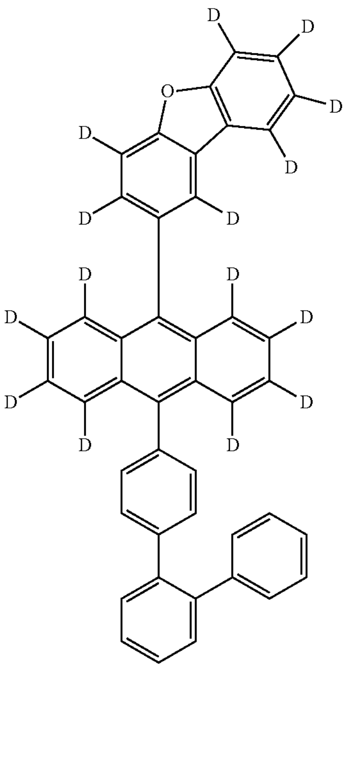
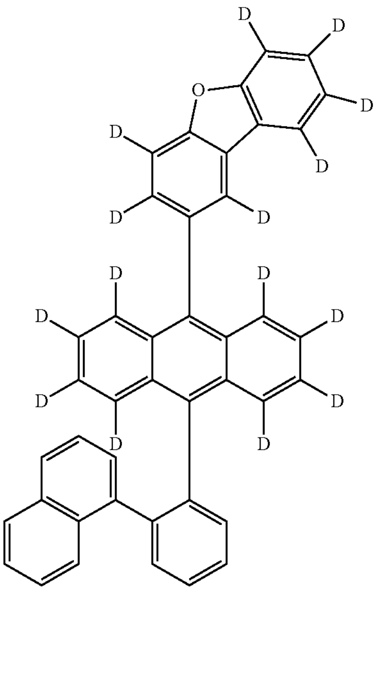

-continued
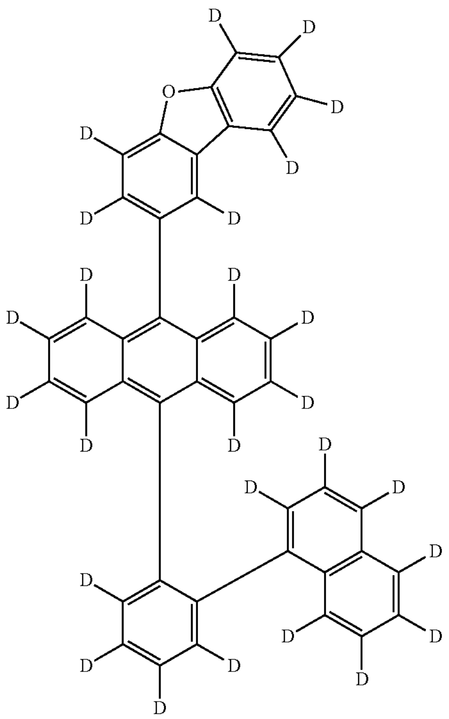
-continued
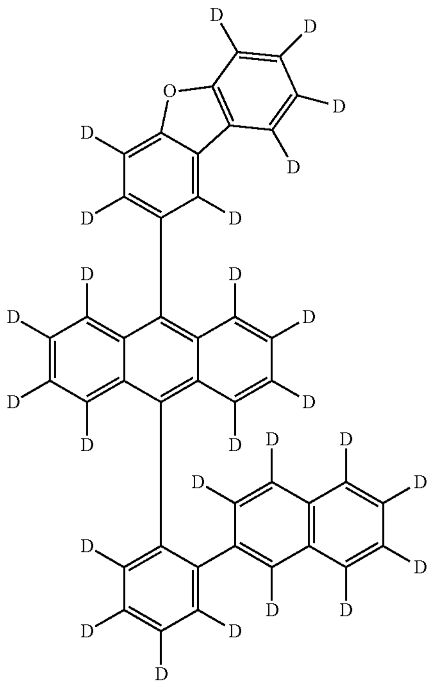
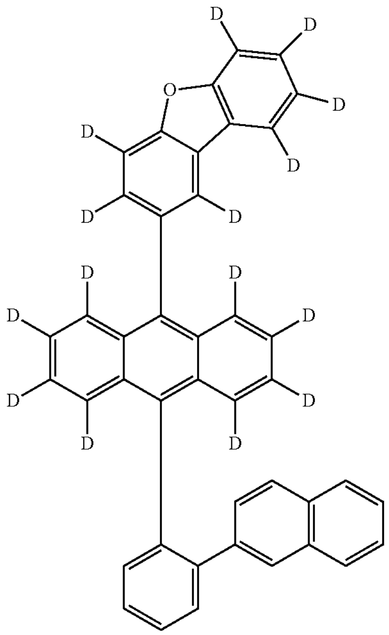
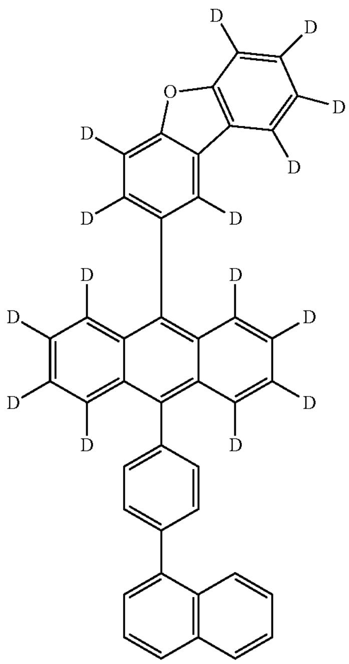

-continued
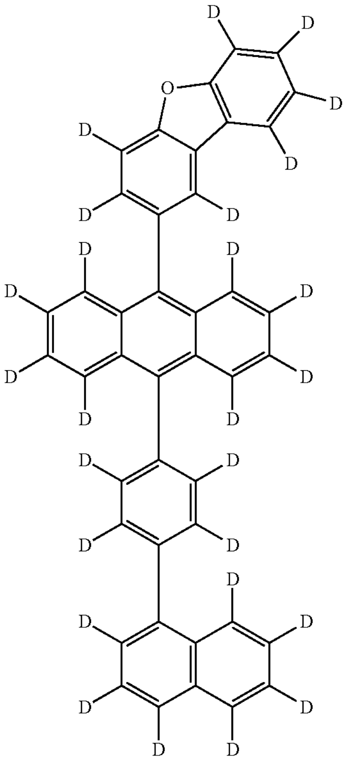
-continued
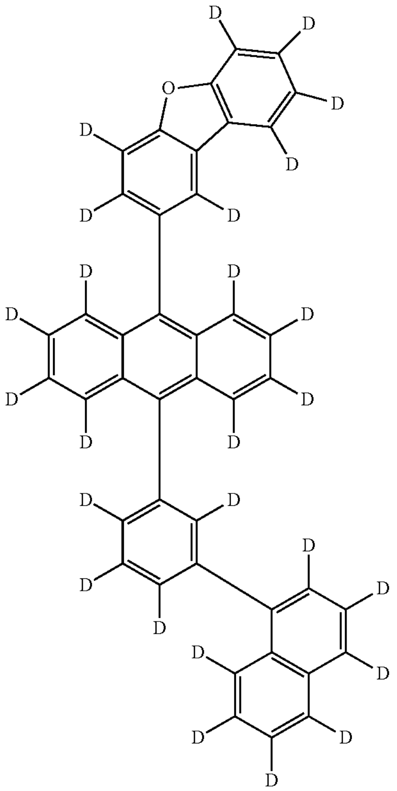
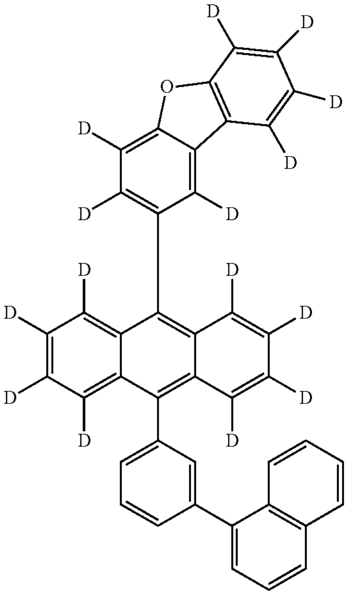
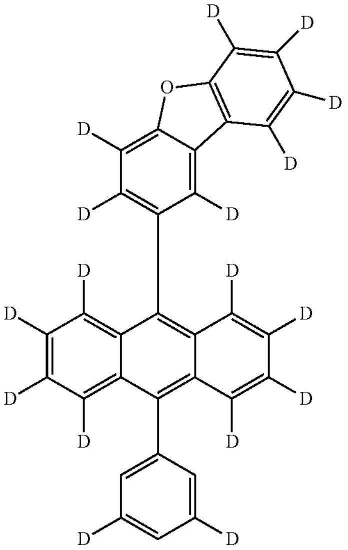

-continued
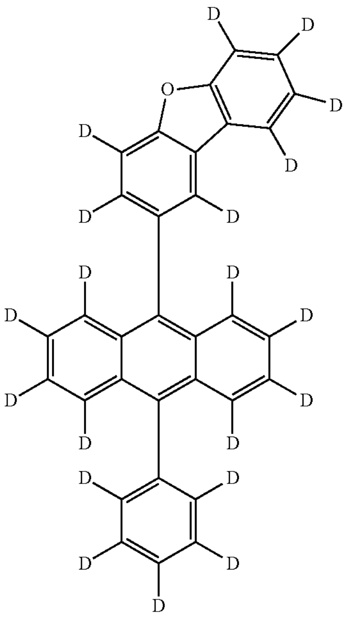
-continued
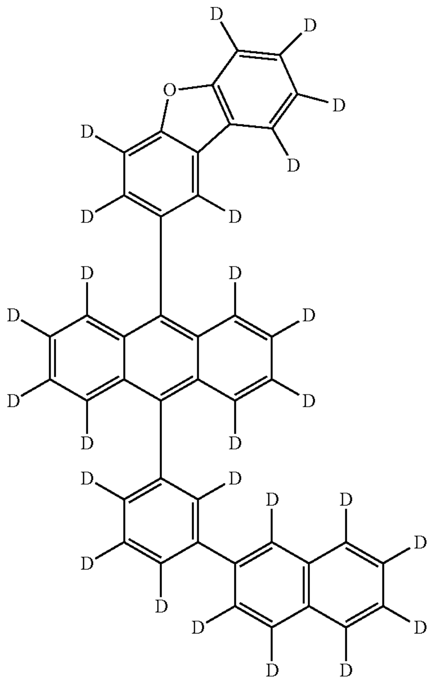
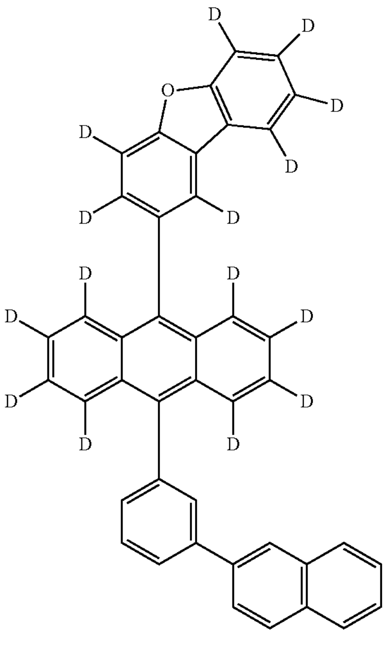
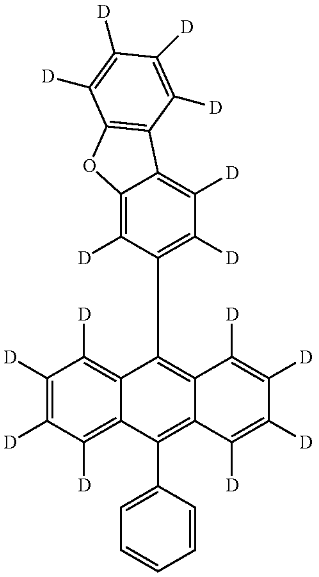

-continued
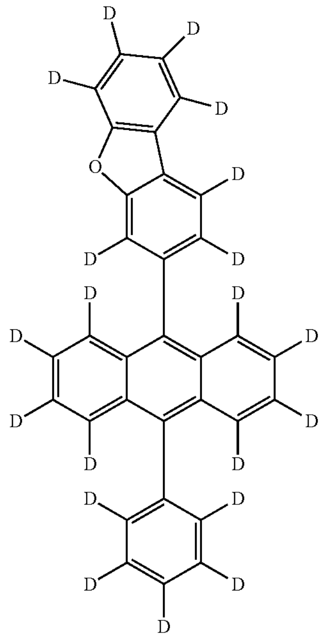
-continued
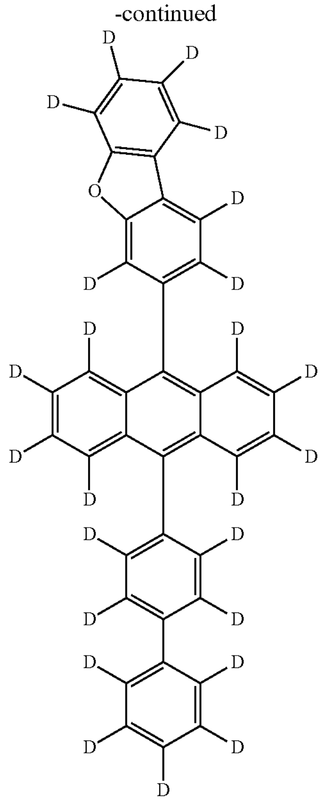
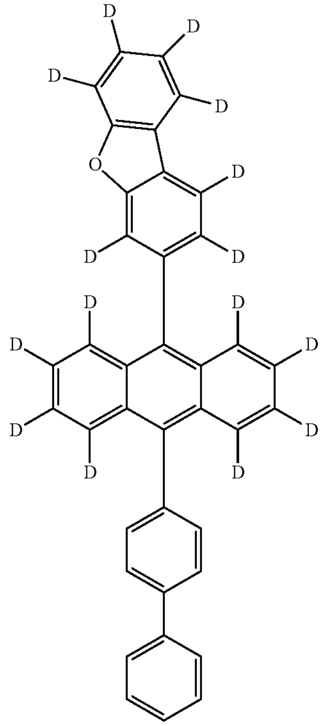
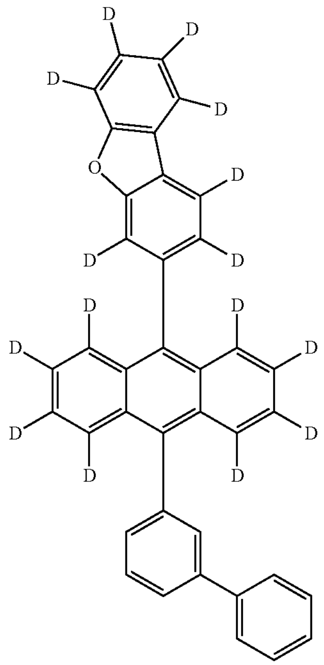

-continued
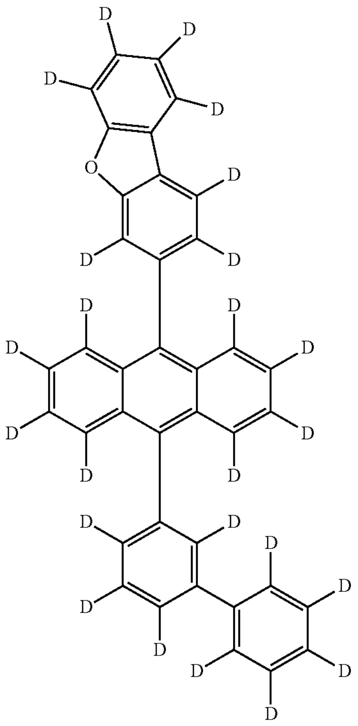
-continued
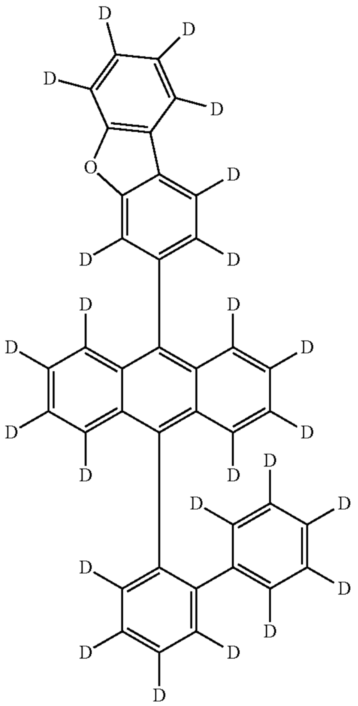
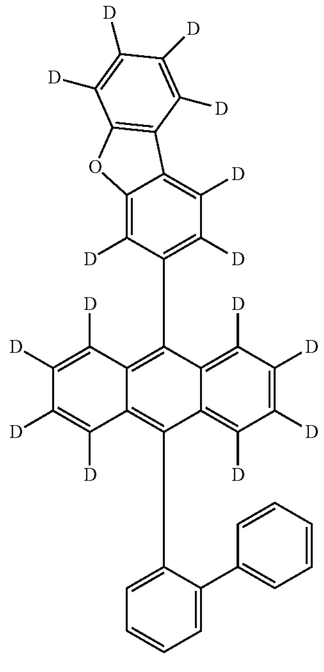
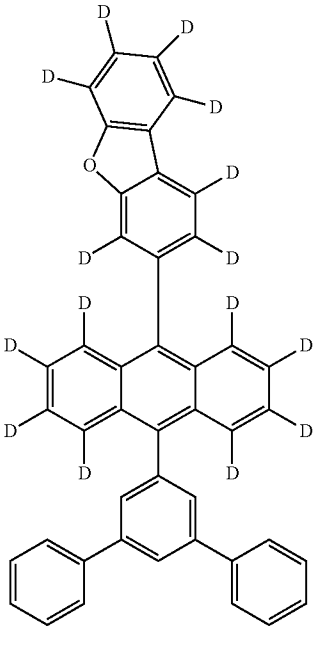

-continued
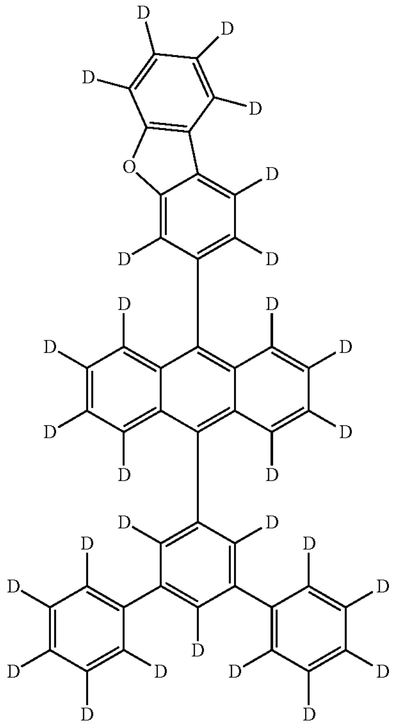
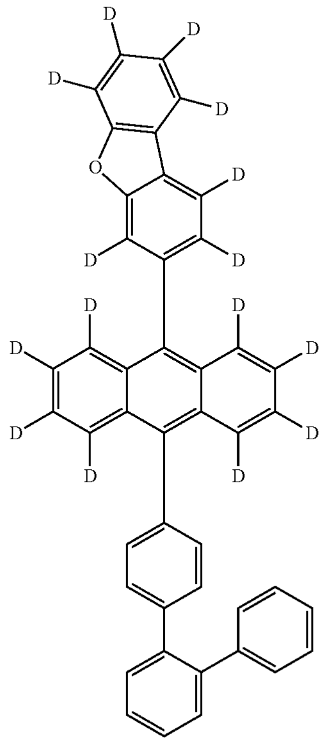
-continued
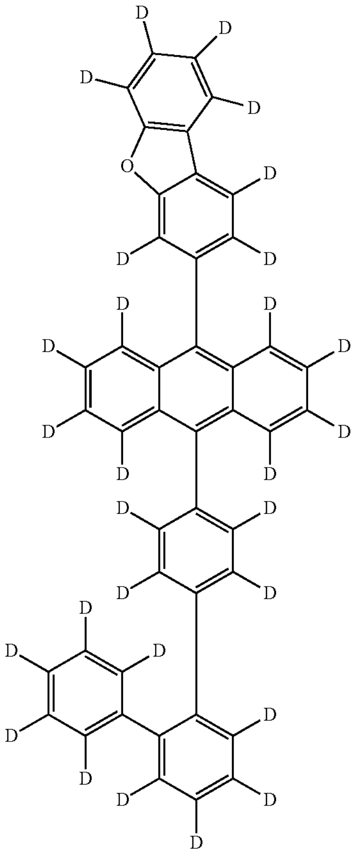
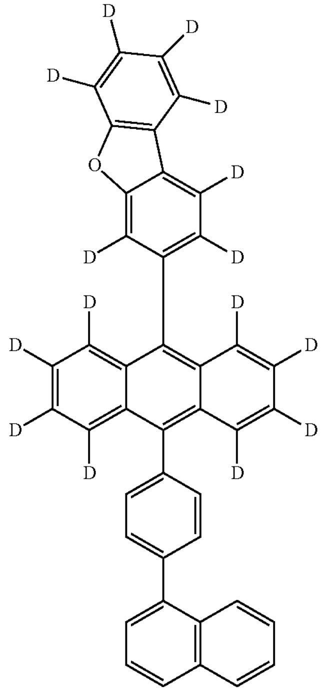

-continued
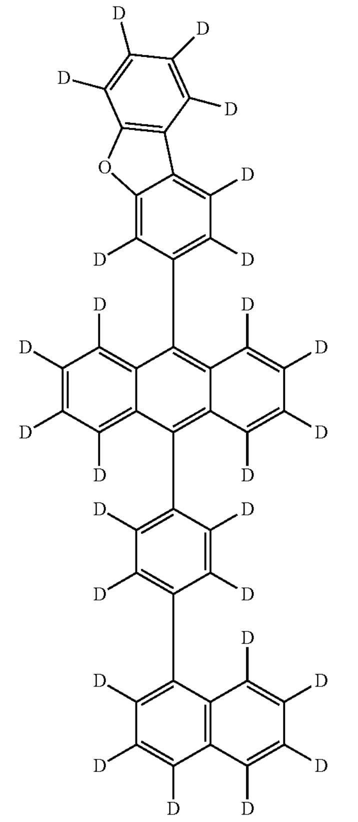
-continued
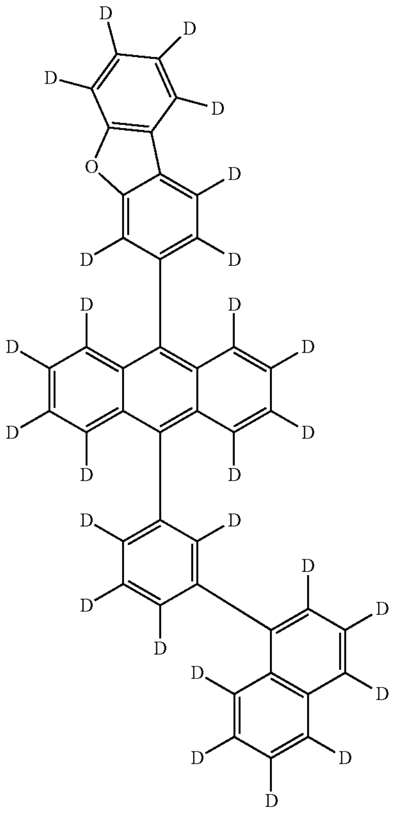
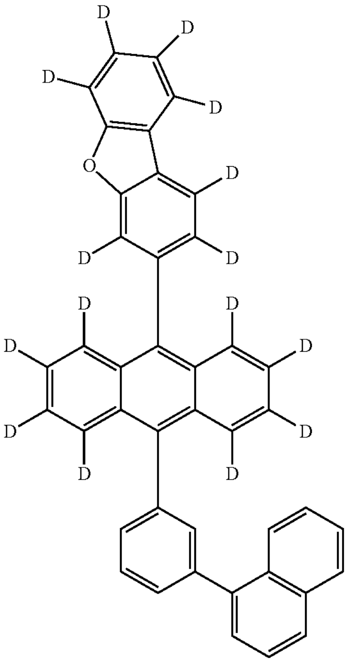
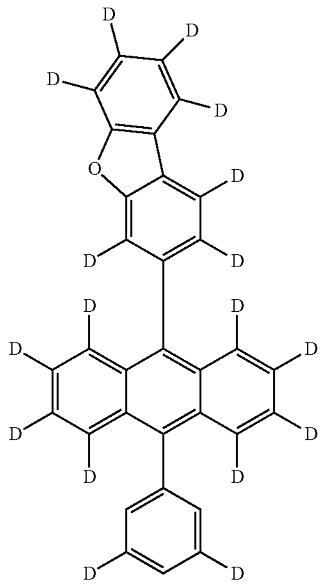

-continued
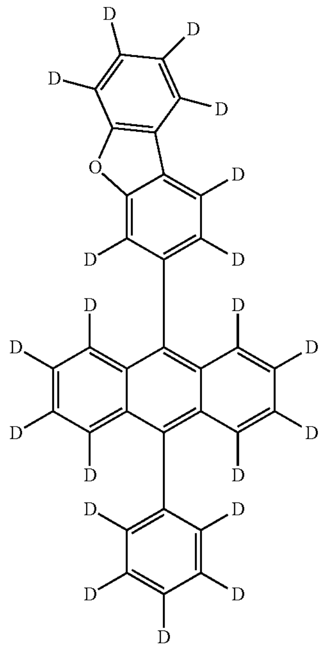
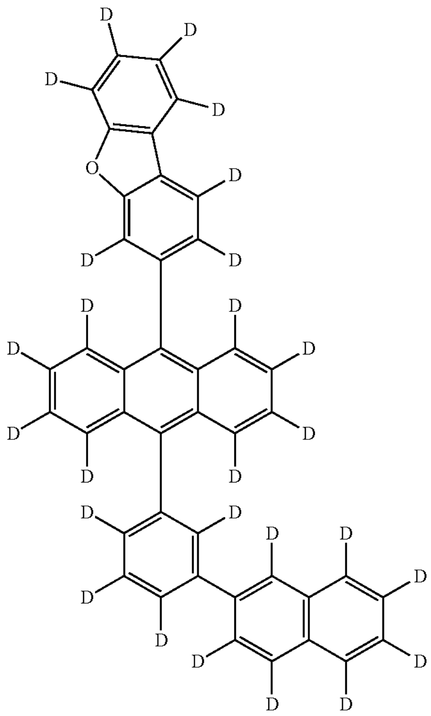
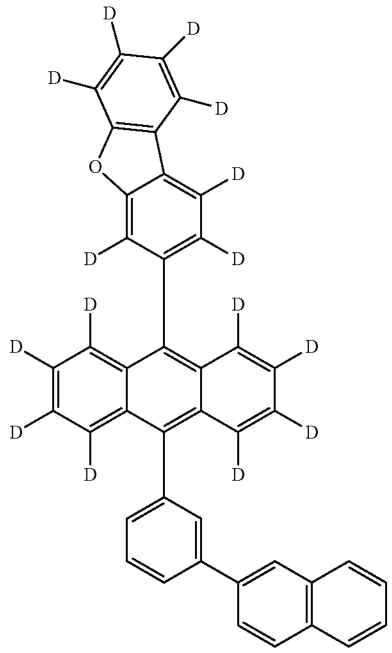
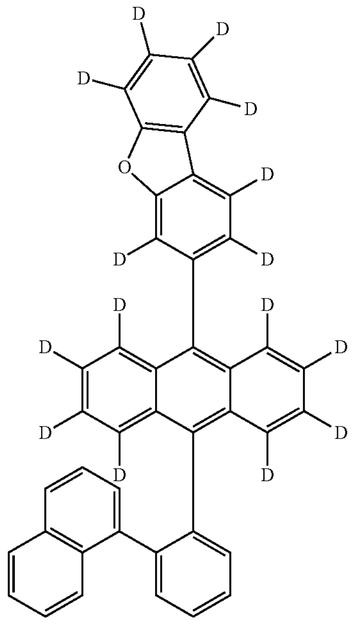

-continued
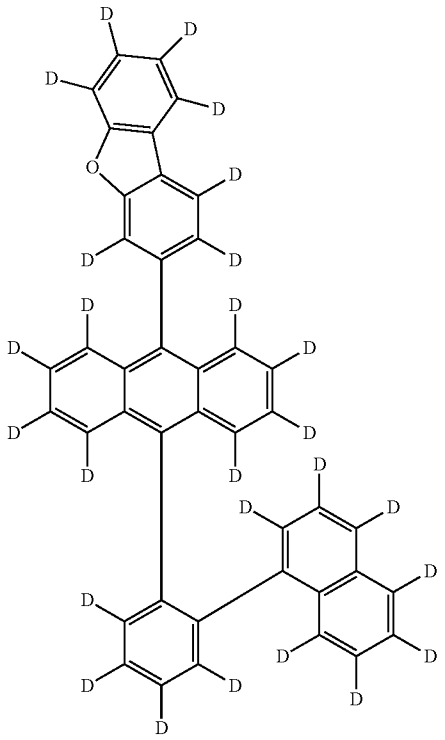
-continued
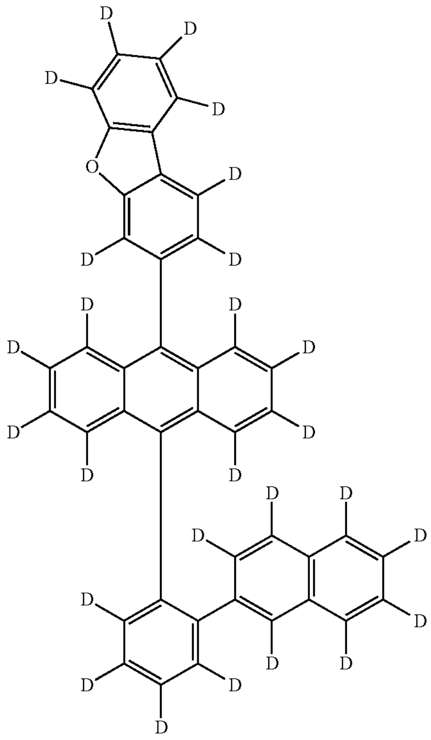
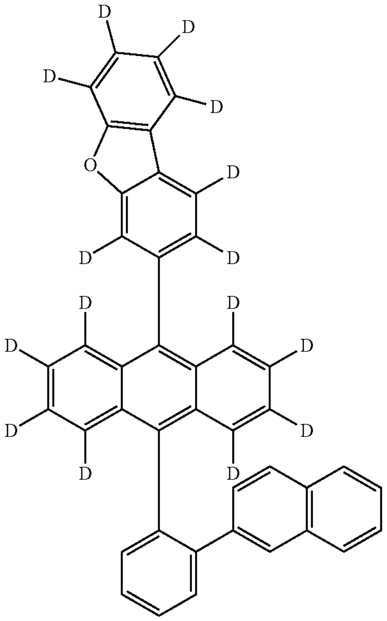
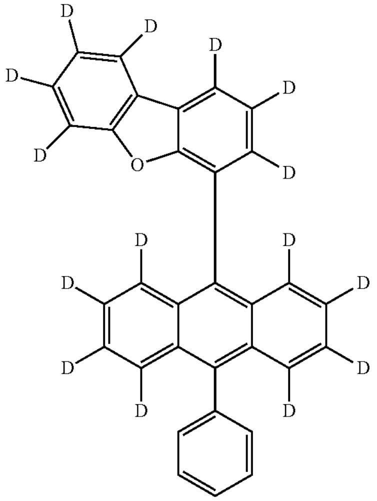

-continued
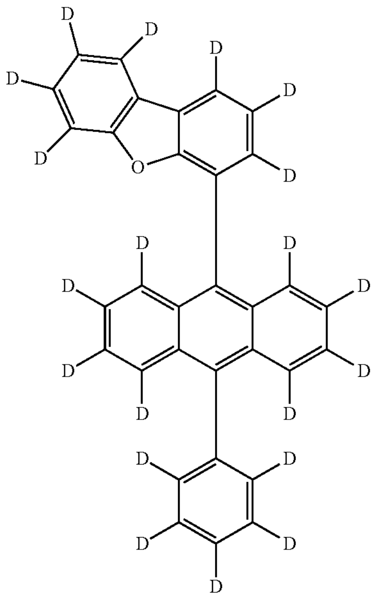
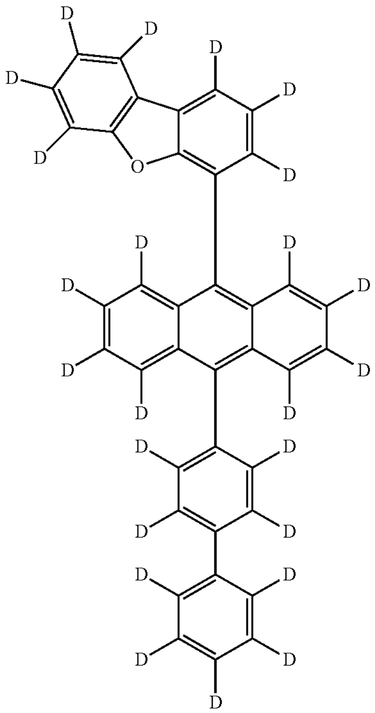
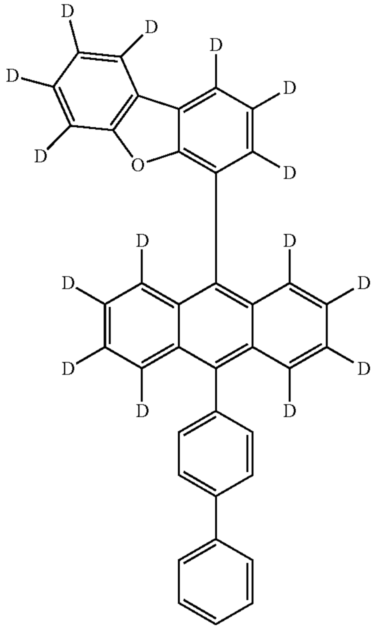
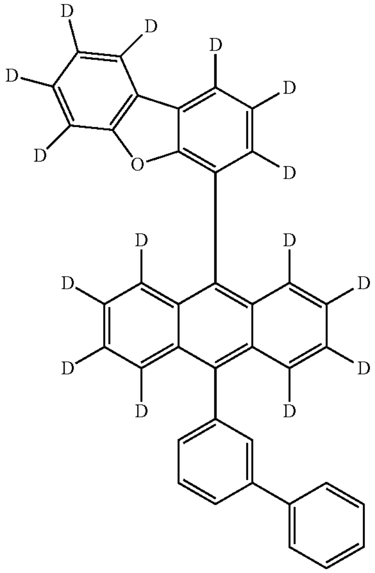
-continued

268
-continued
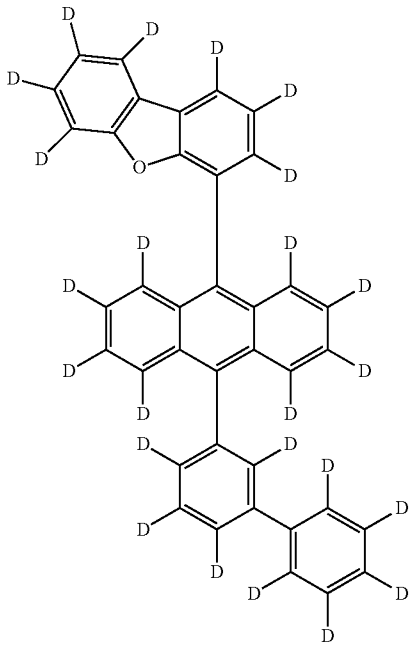
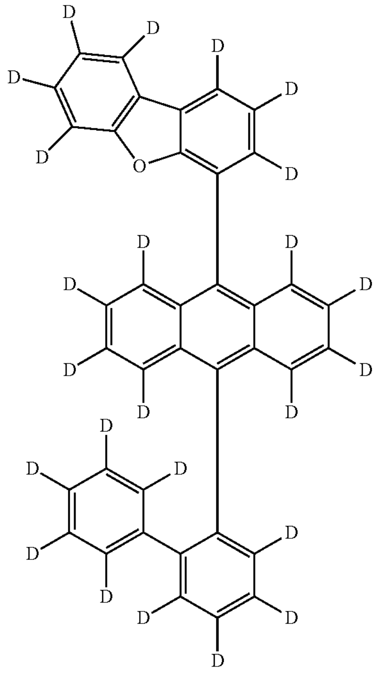
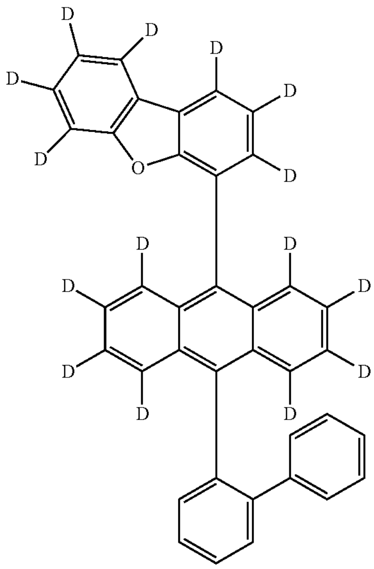
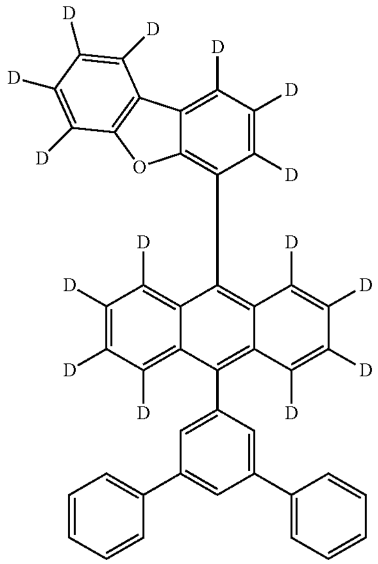

-continued
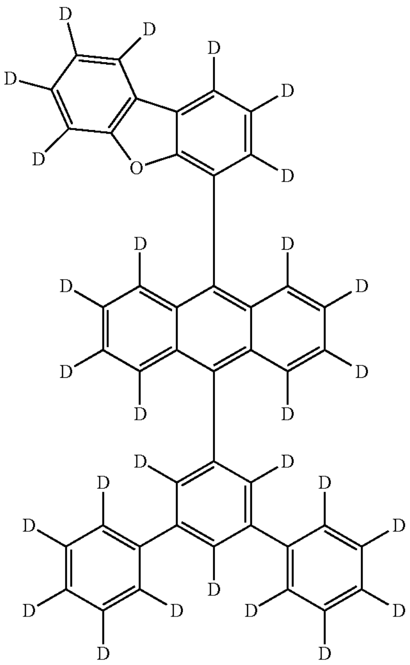
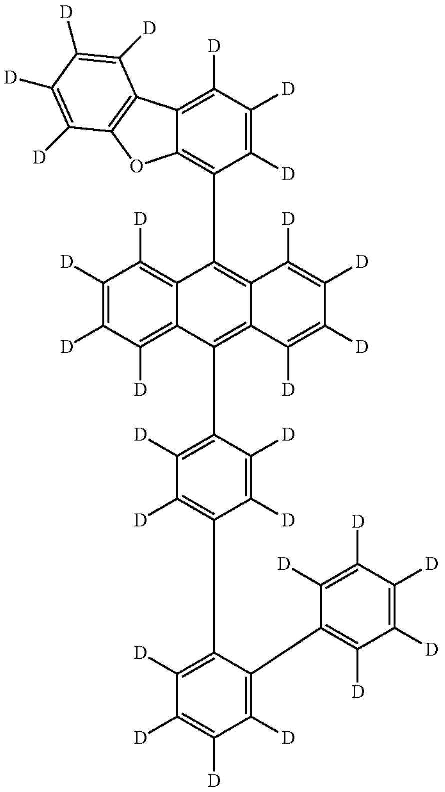
-continued
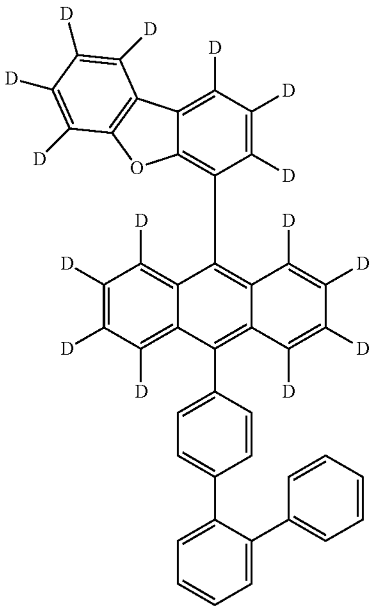
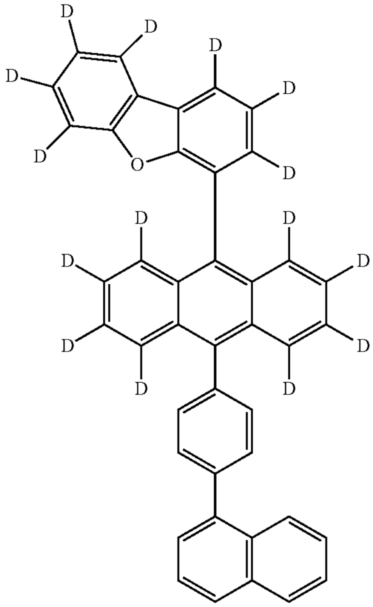

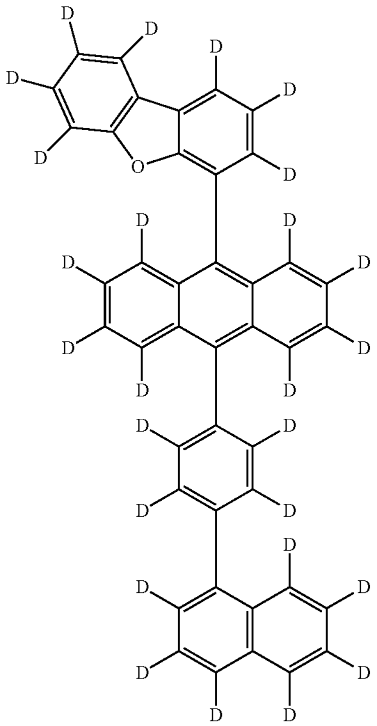
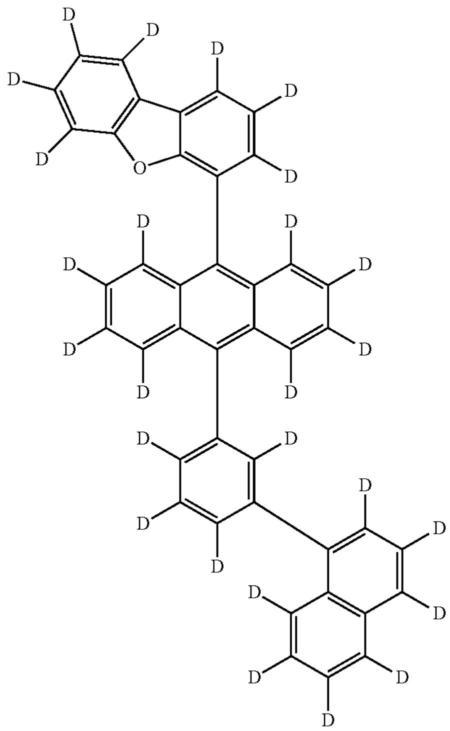
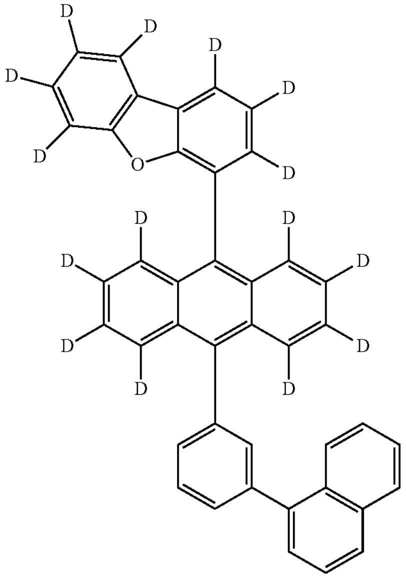
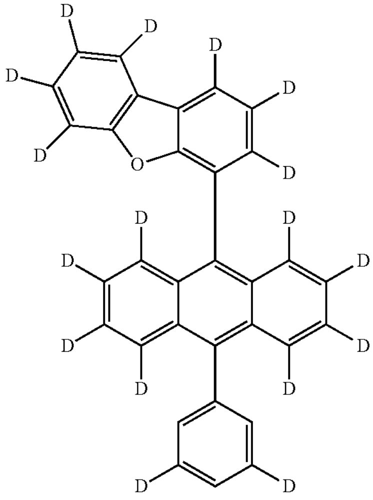

-continued
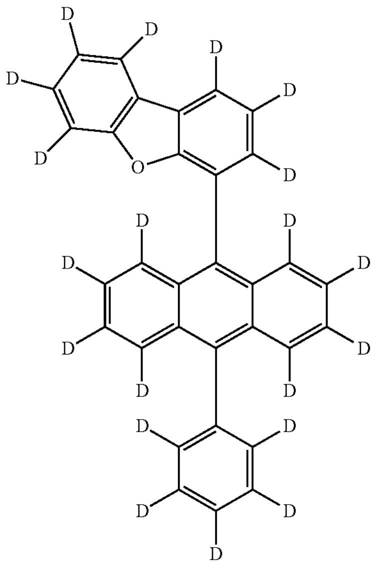
-continued
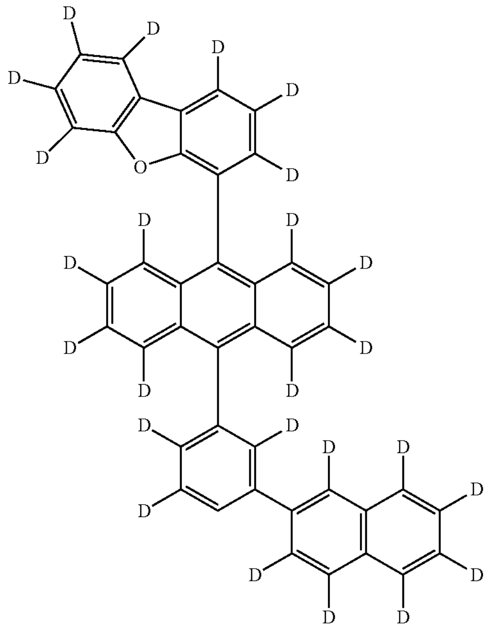
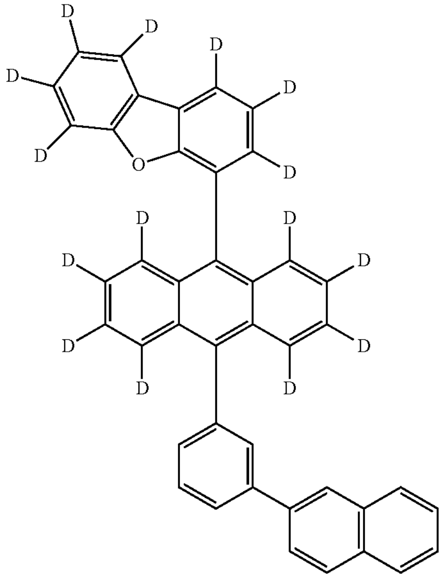
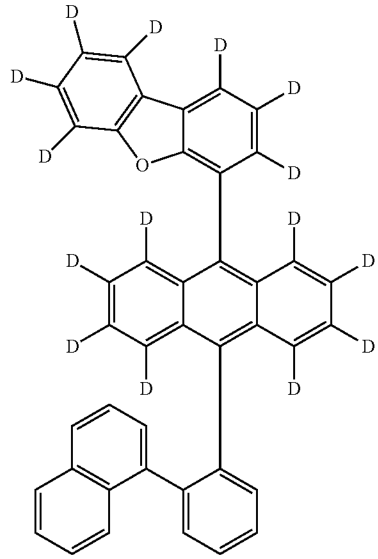

-continued
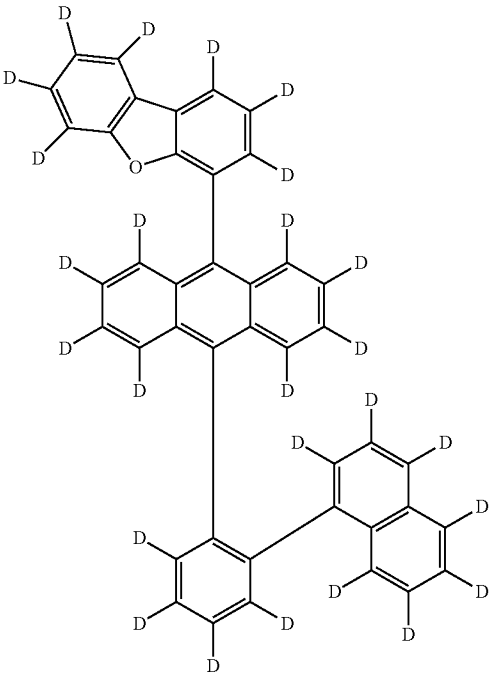
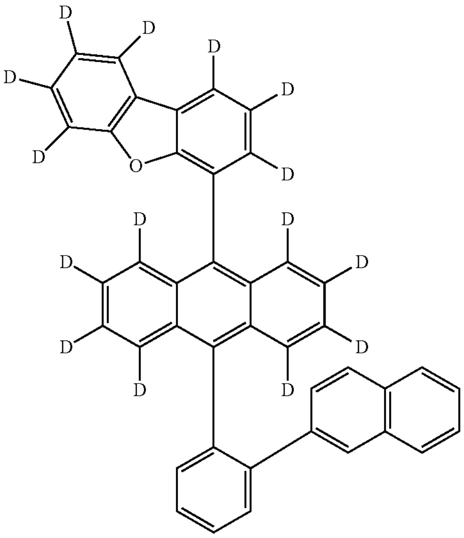
-continued
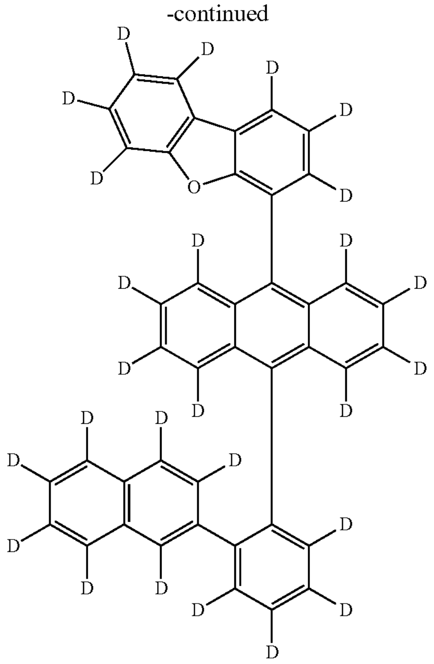
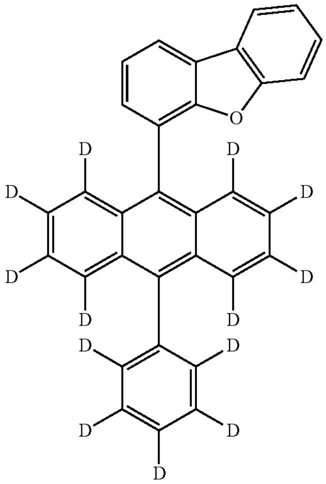
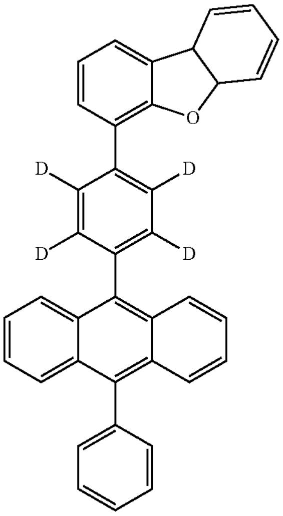

-continued
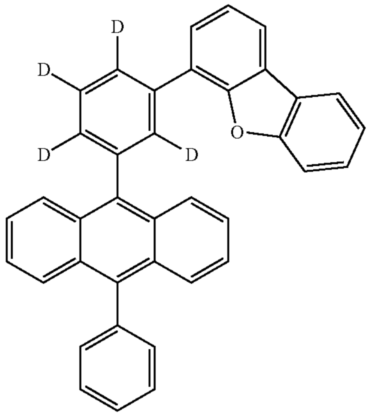
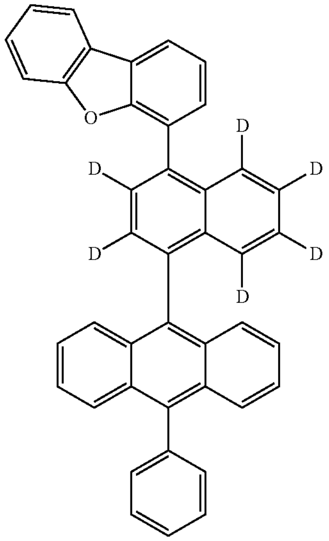
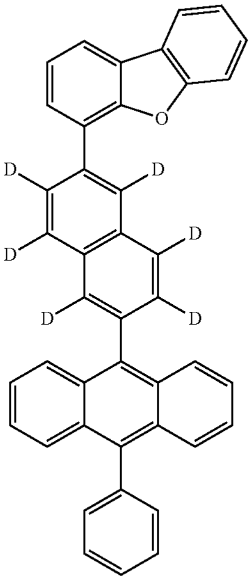
-continued
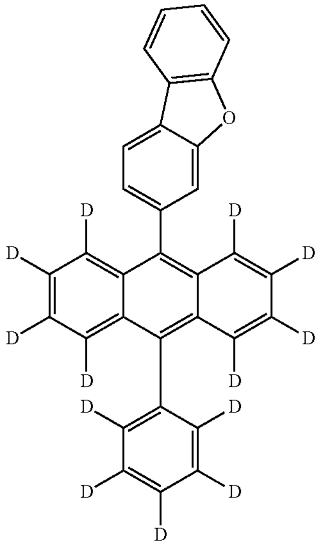
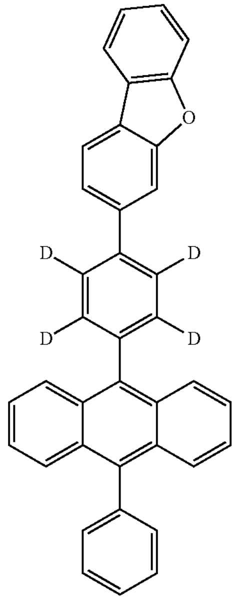
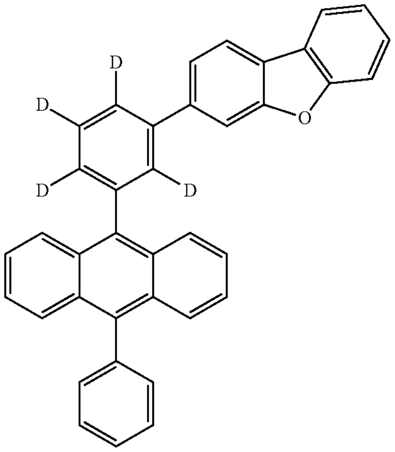

-continued
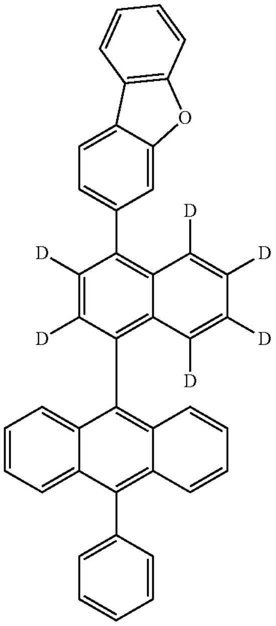
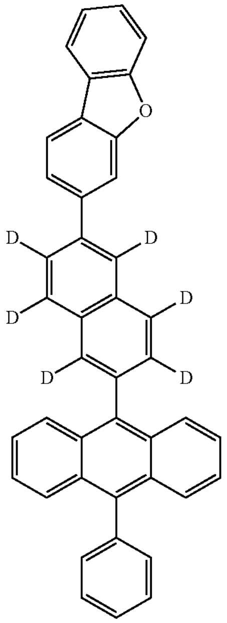
-continued
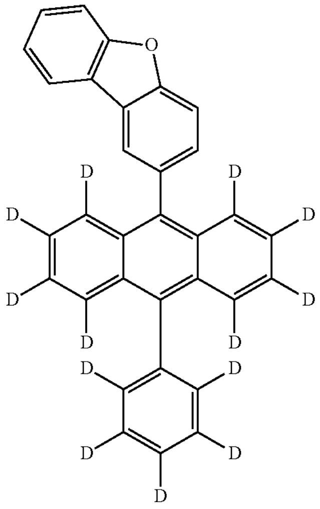
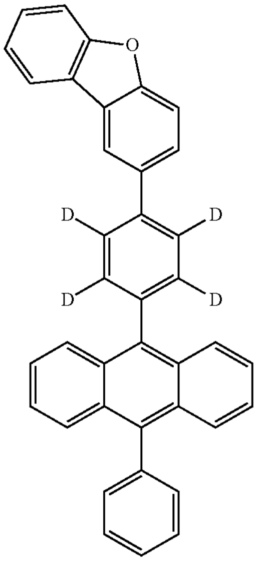
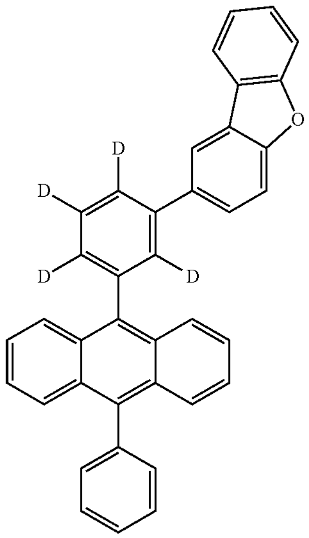

-continued
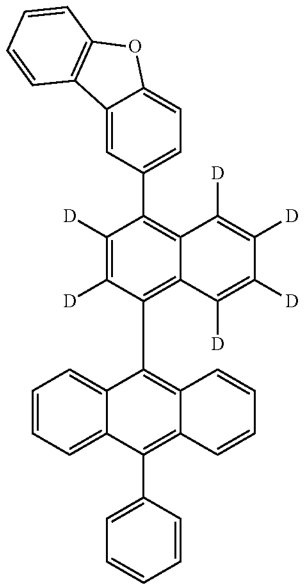
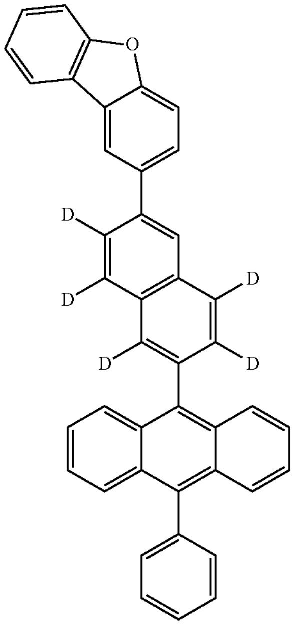
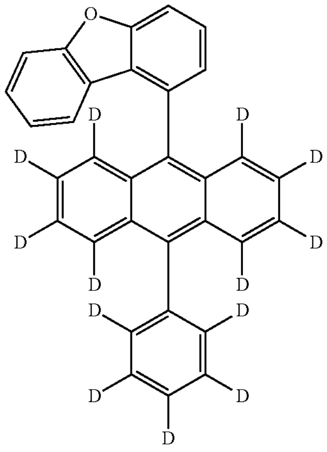
-continued
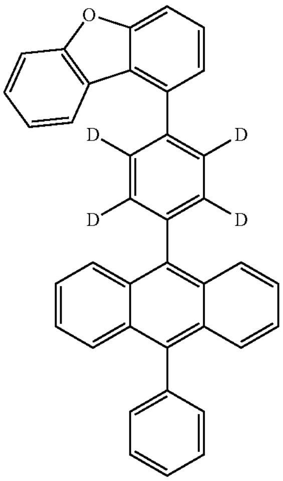
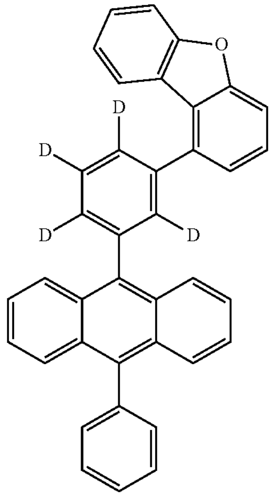
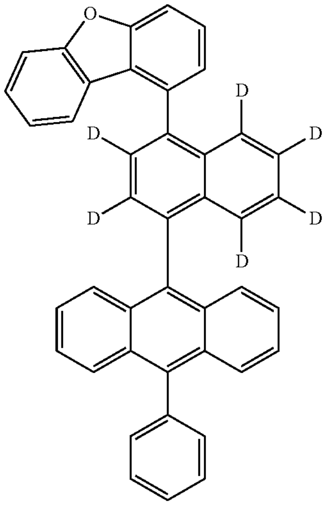

-continued
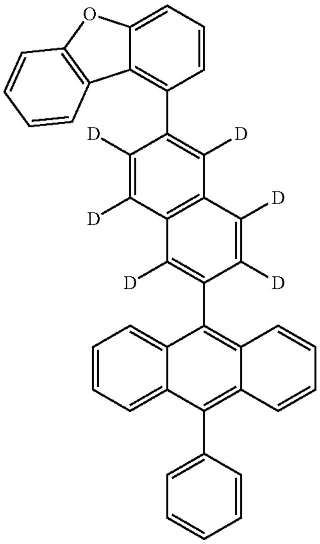
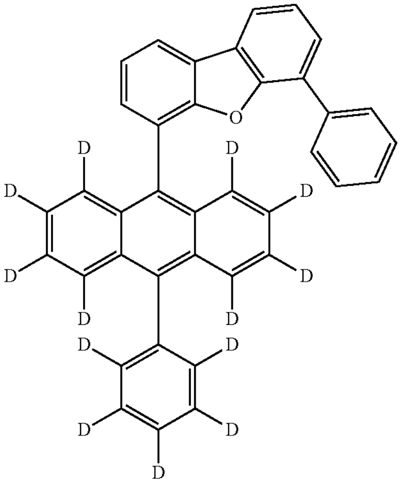
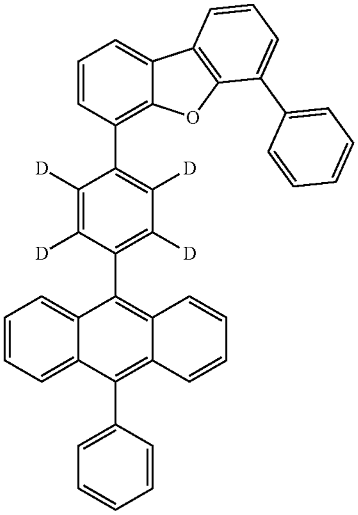
-continued
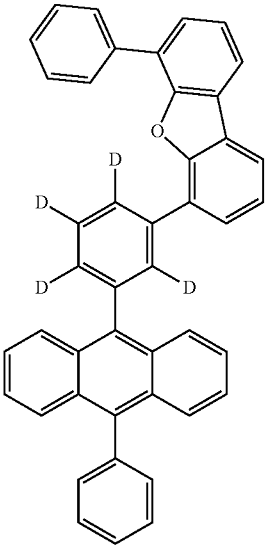
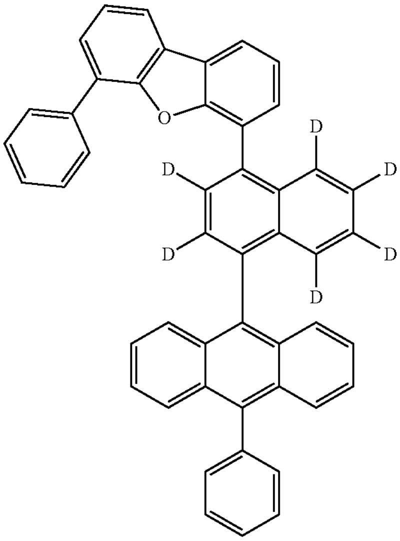
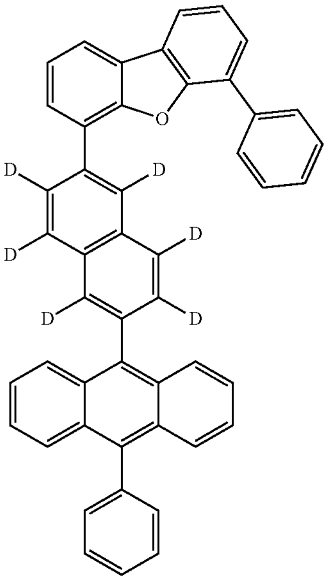

-continued
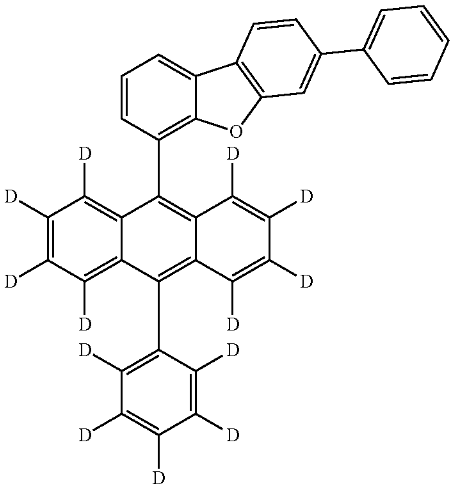
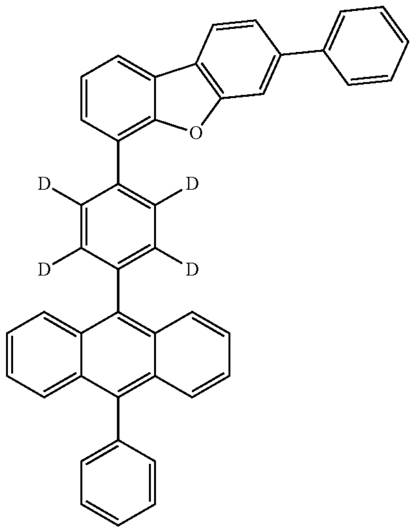
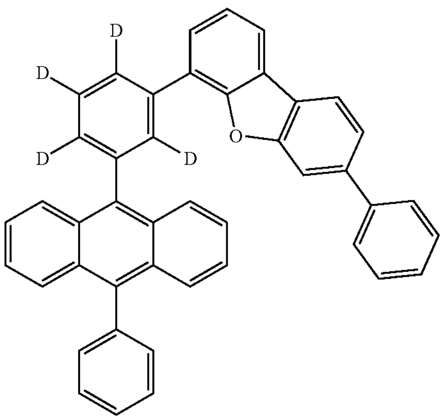
-continued
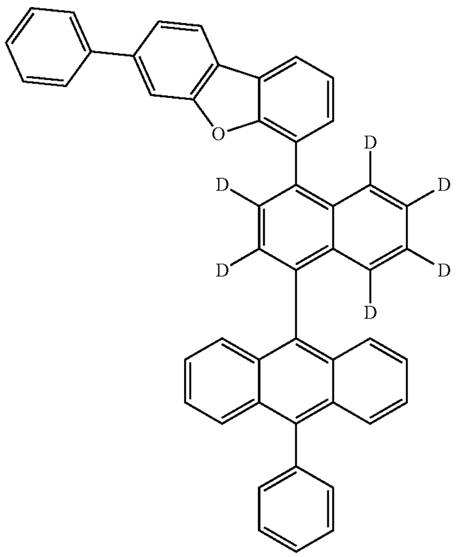
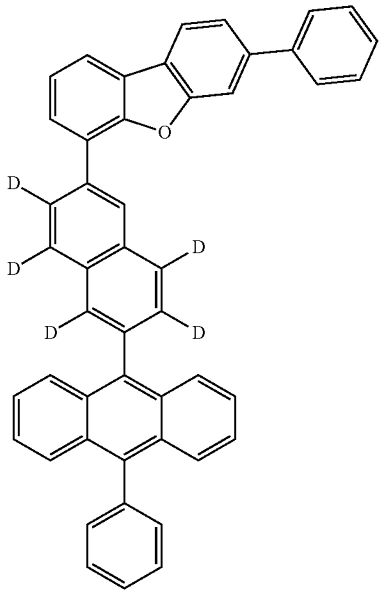

-continued
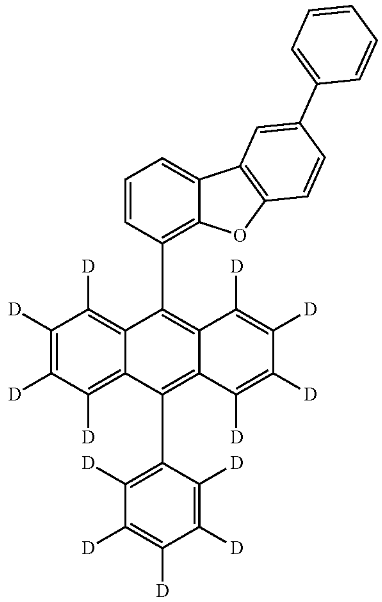
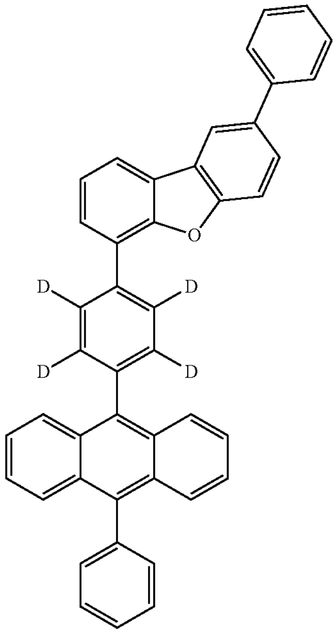
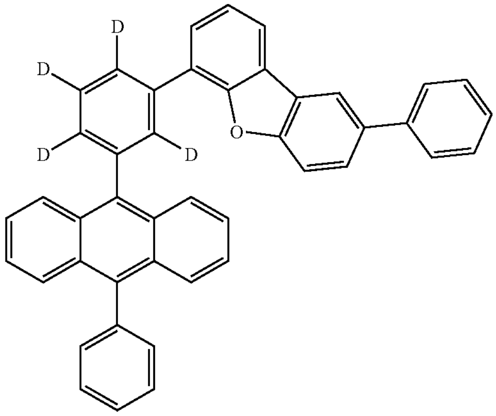
-continued
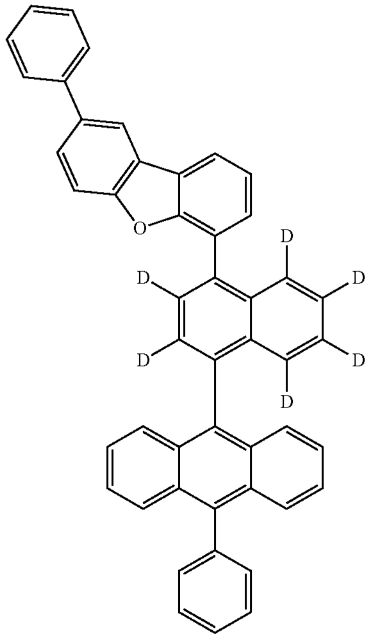
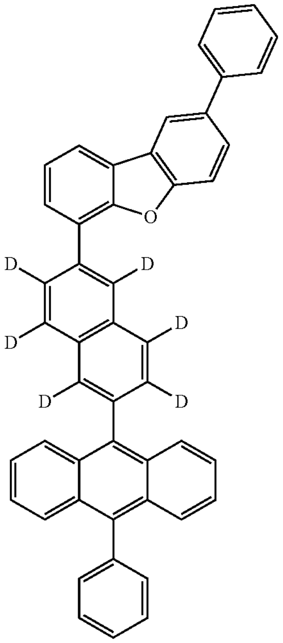

-continued
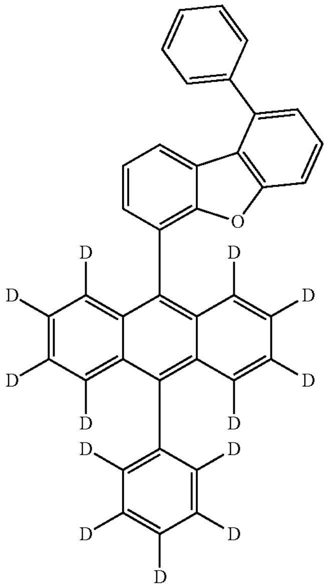
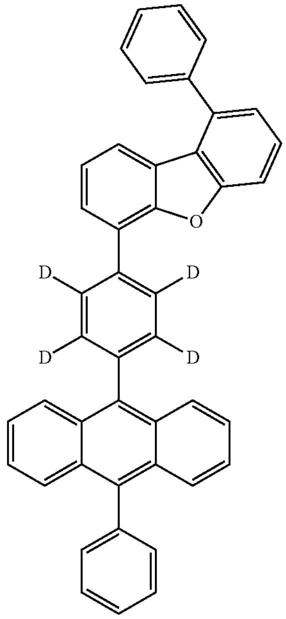
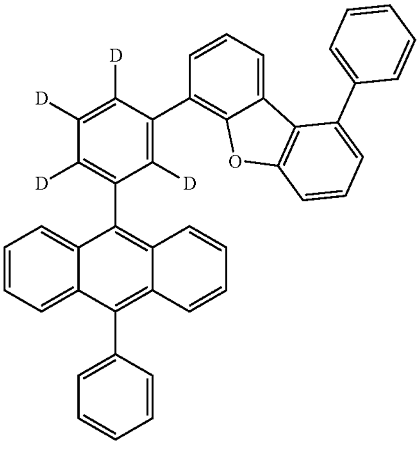
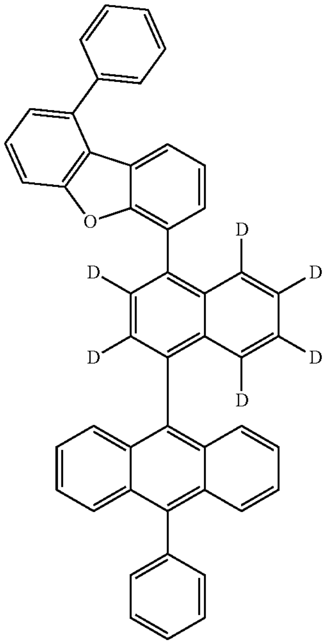
-continued
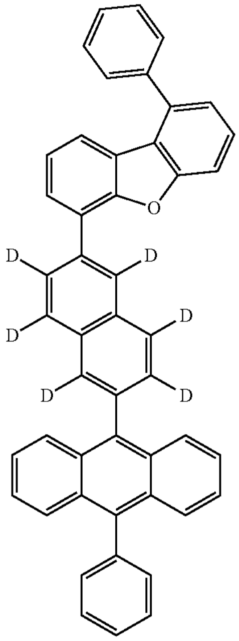

-continued
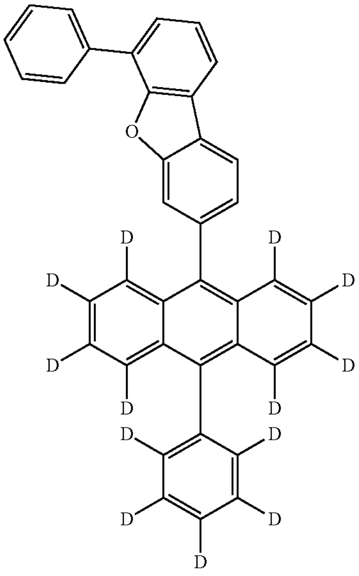
-continued
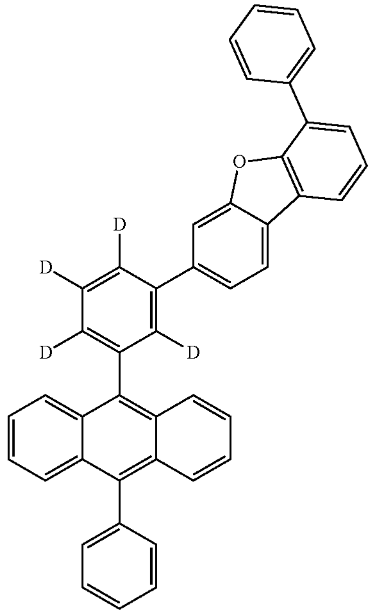
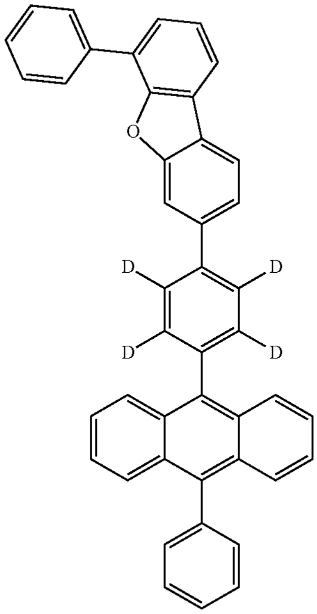
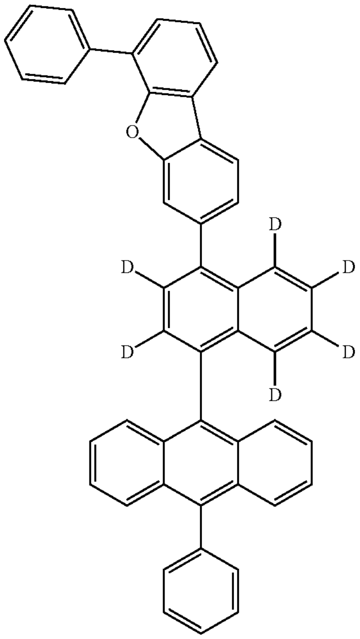

-continued
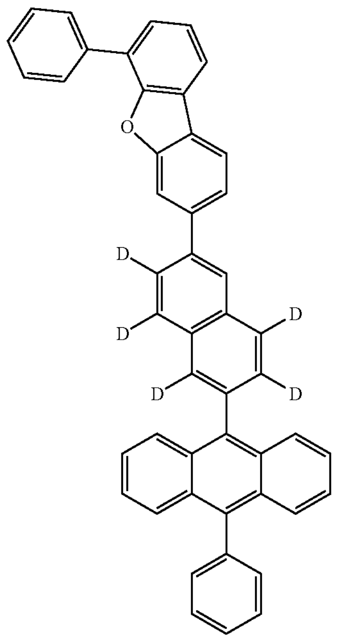
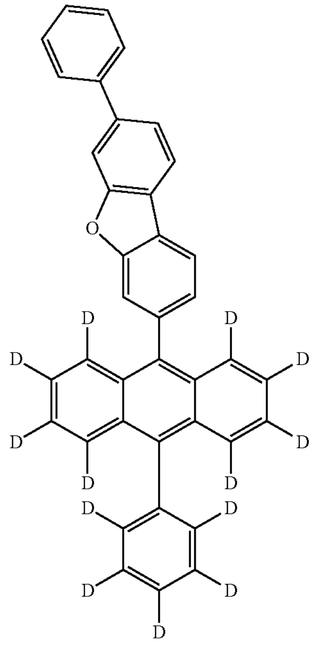
-continued
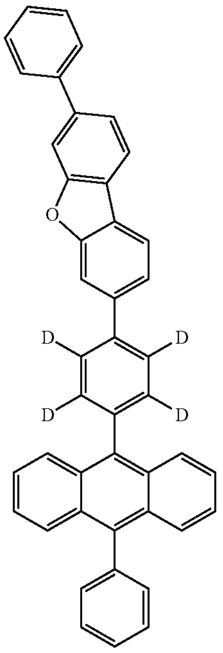
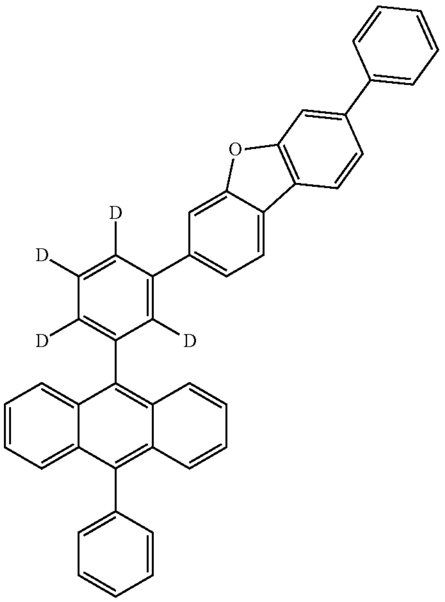

-continued
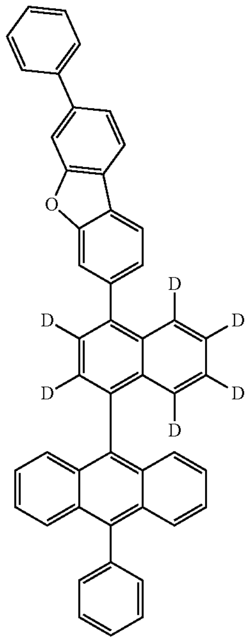
-continued
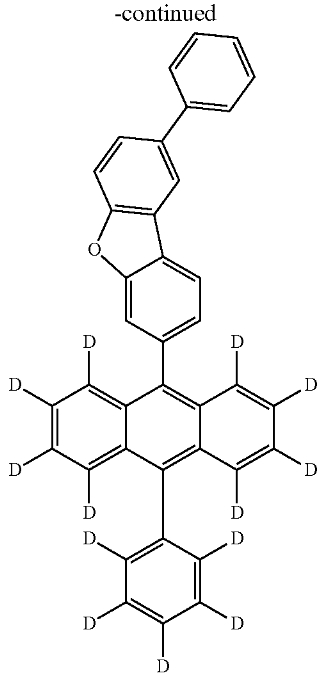
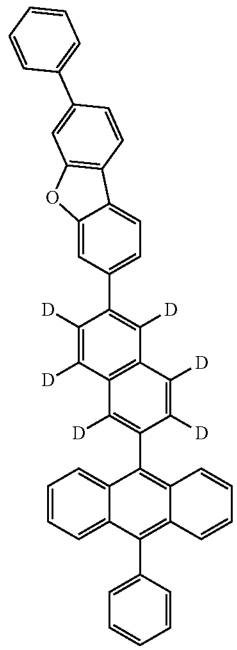
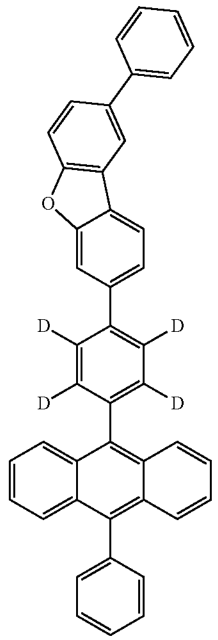

-continued
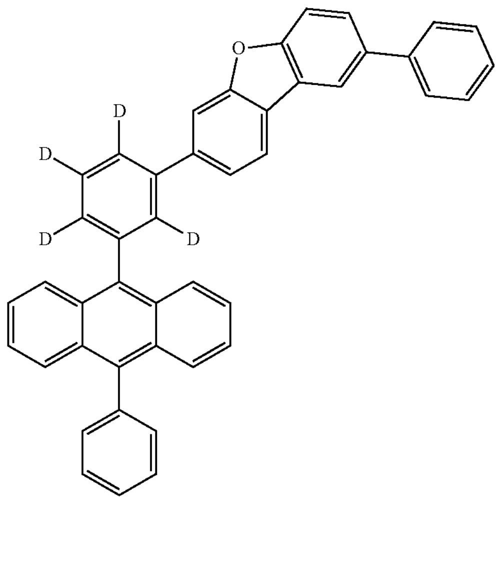
-continued
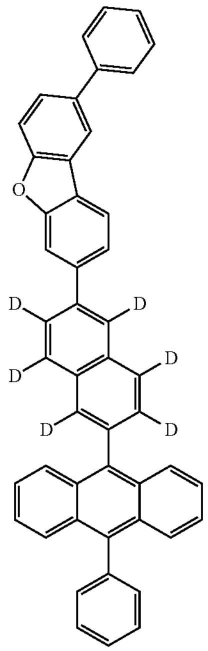
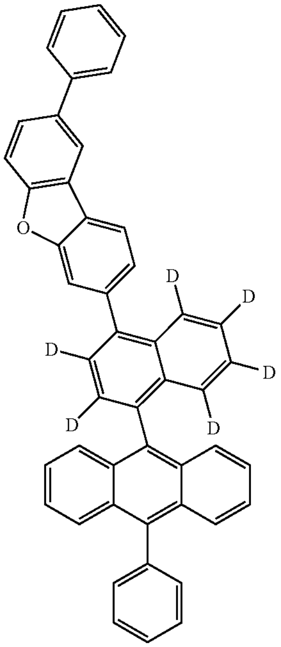
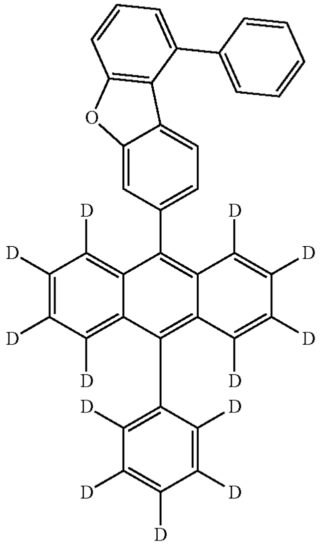

-continued
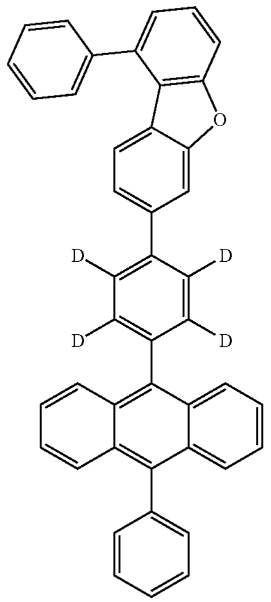
-continued
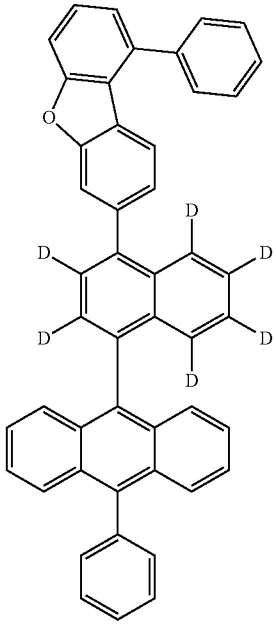
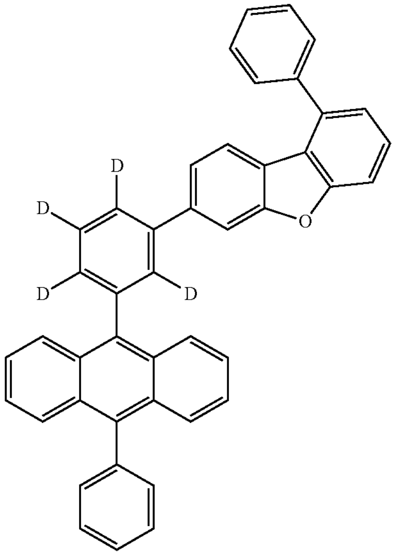
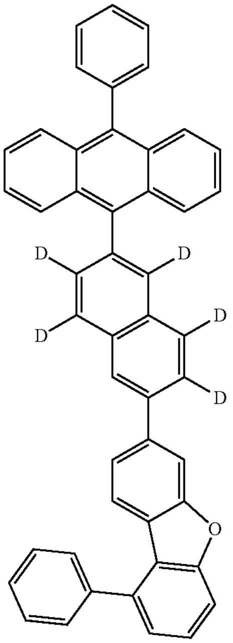

-continued
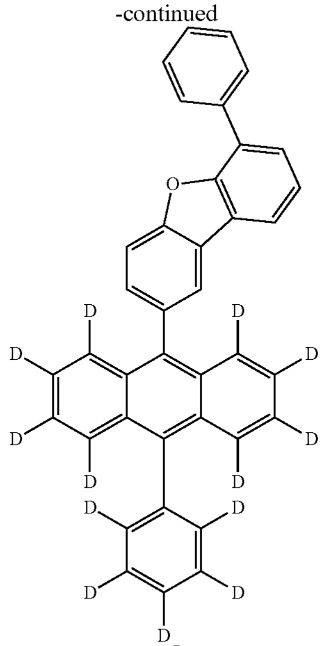
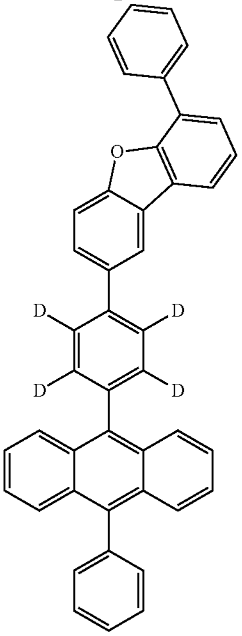
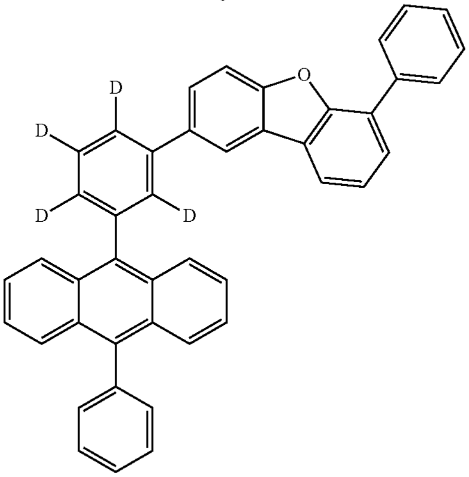
-continued
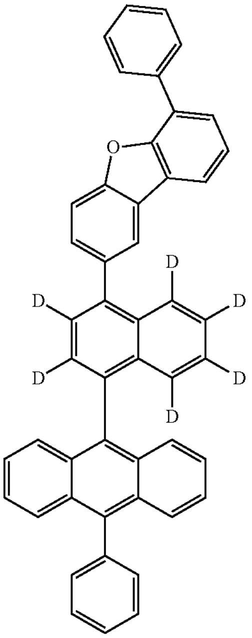
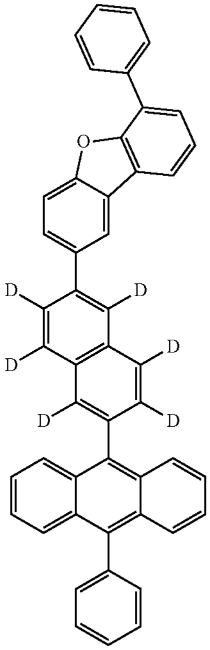

-continued
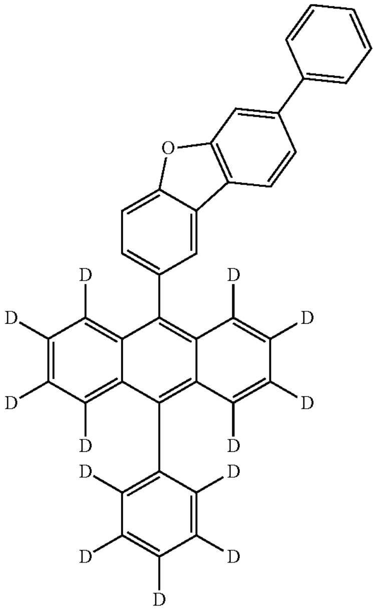
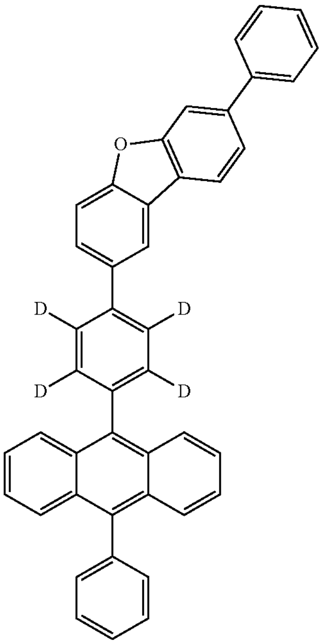
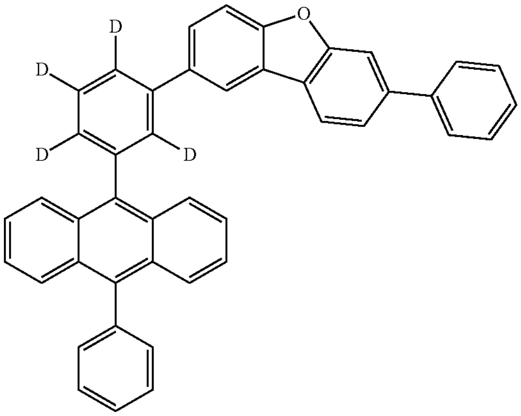
-continued
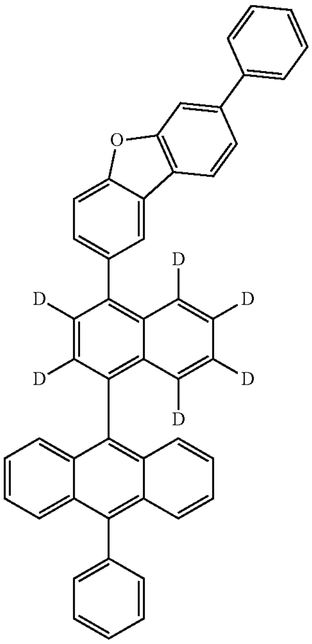
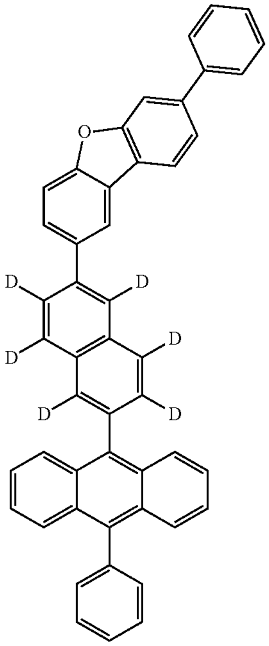

-continued
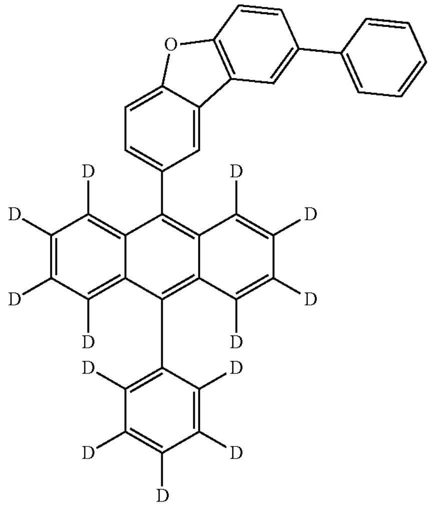
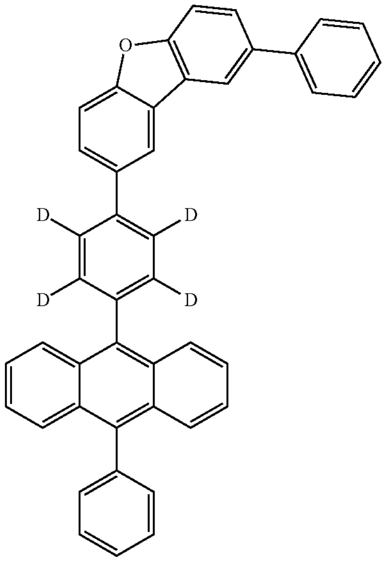
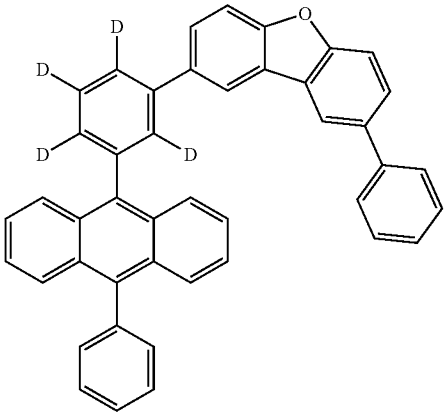
-continued
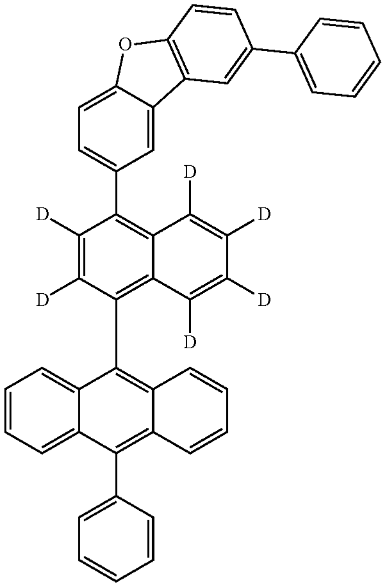
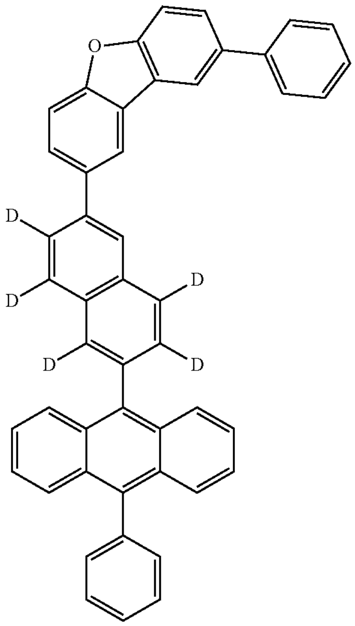

-continued
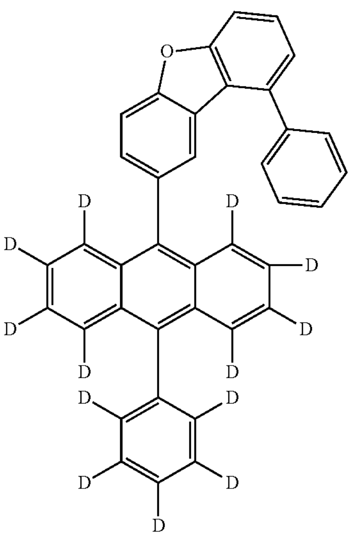
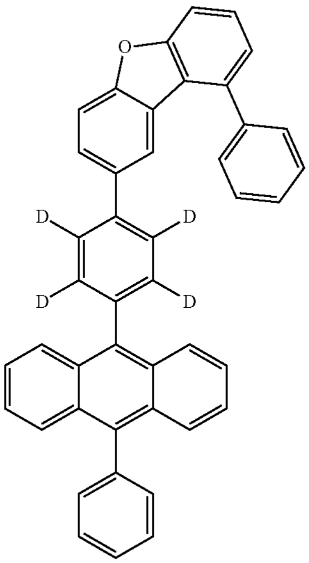
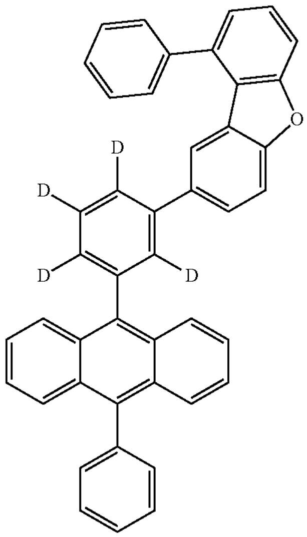
-continued
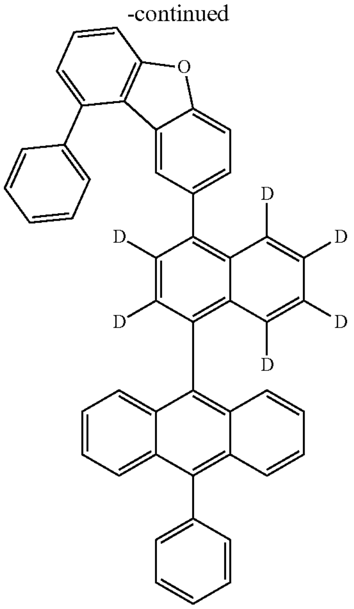
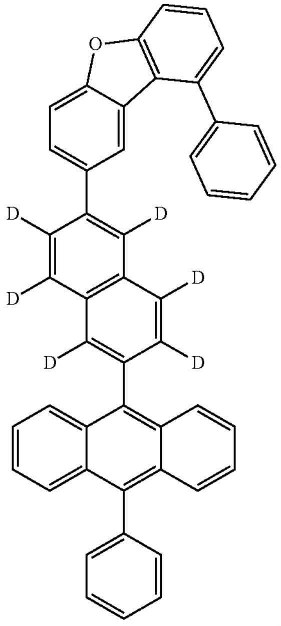
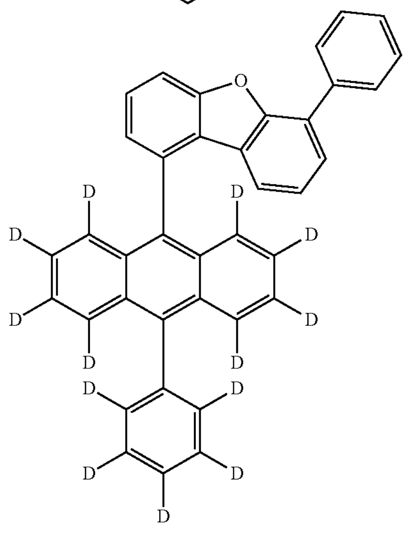

-continued
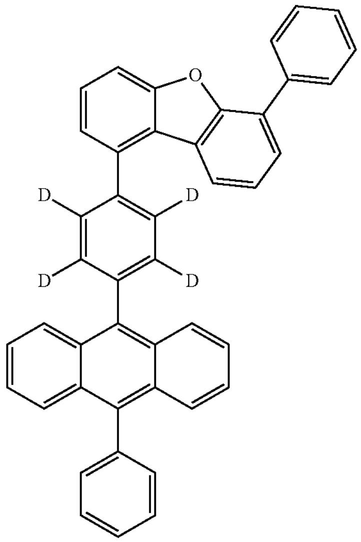
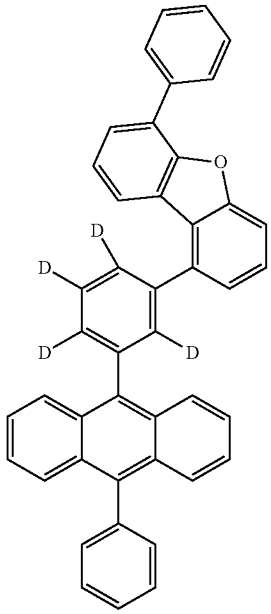
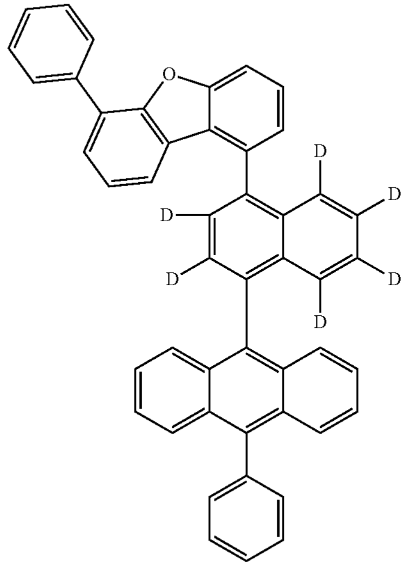
-continued
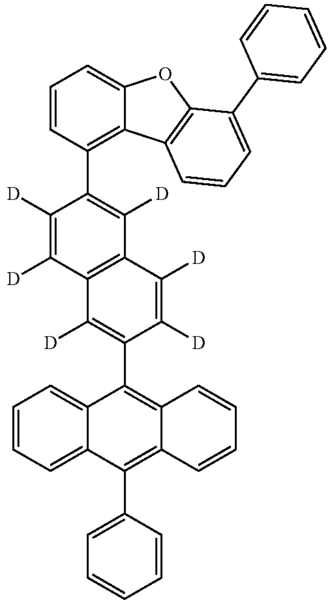
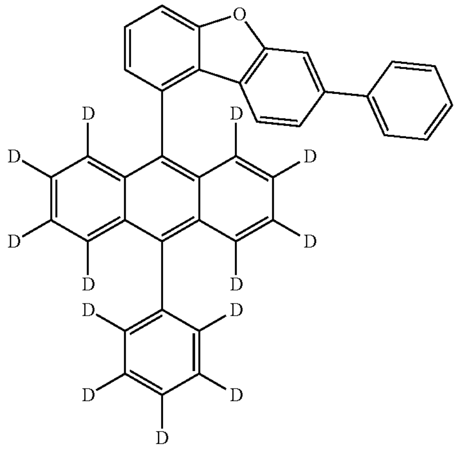
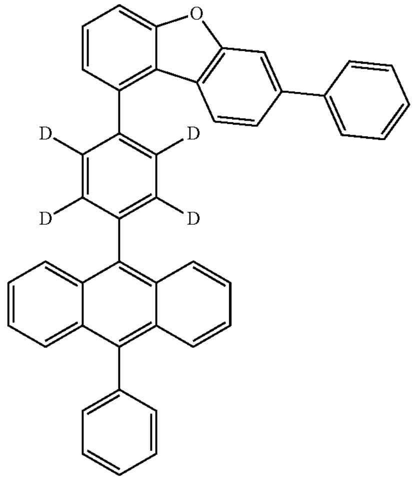

-continued
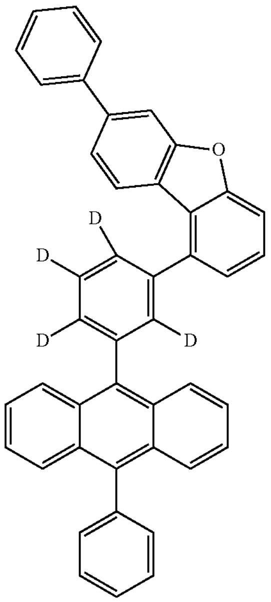
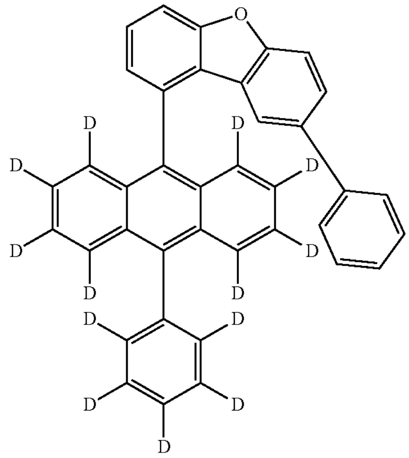
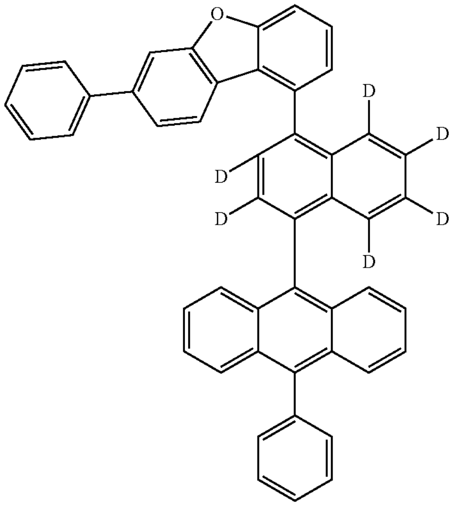
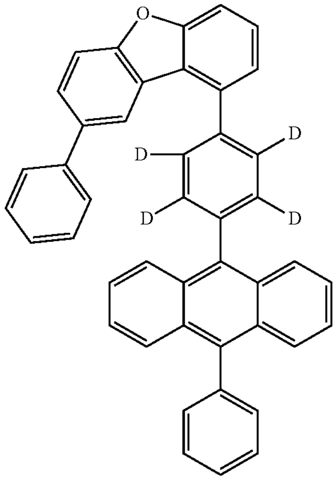
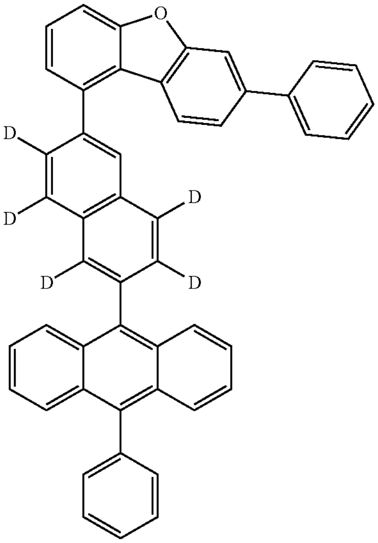
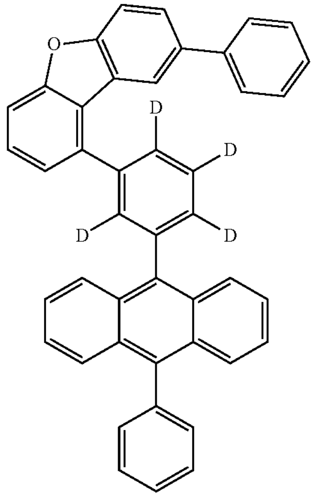
-continued -continued
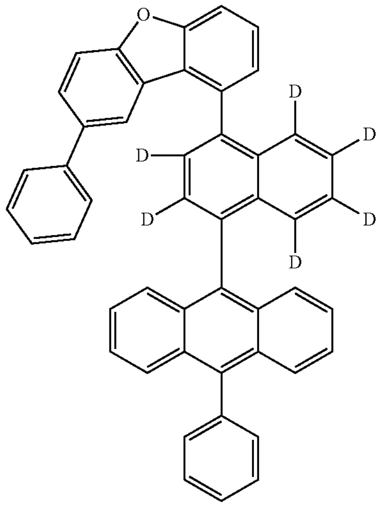
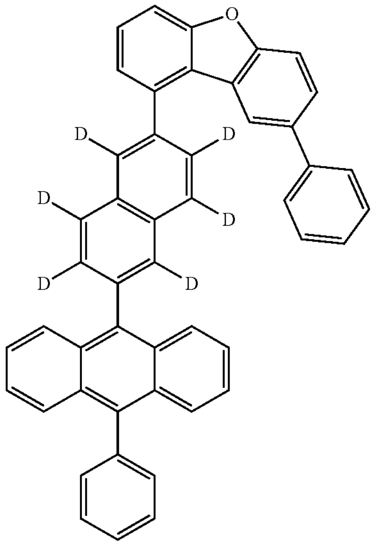
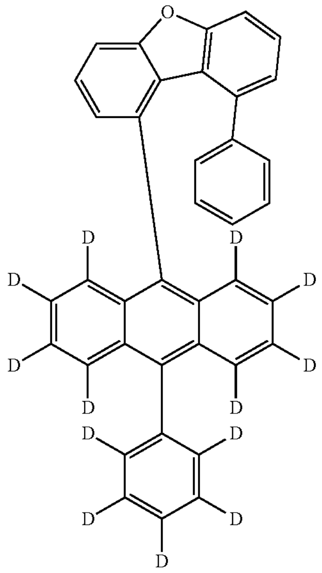
-continued
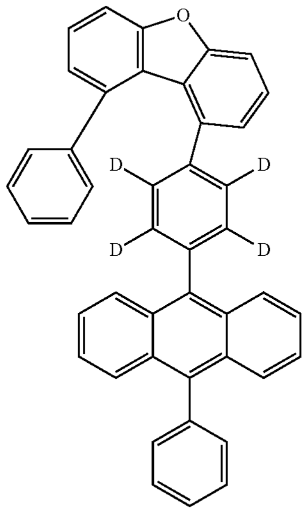
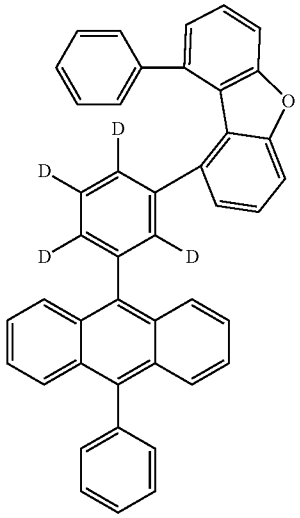
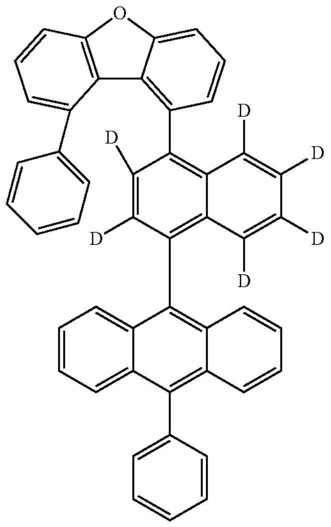

-continued
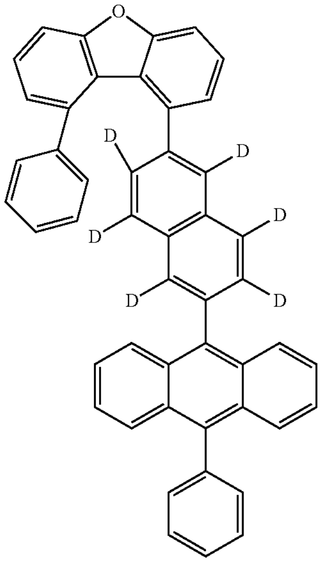 [SMILES: [2H]c1c(-c2cccc3oc4cccc(-c5ccccc5)c4c23)c([2H])c2c([2H])c([2H])c(-c3c4ccccc4c(-c4ccccc4)c4ccccc34)c([2H])c2c1[2H]]
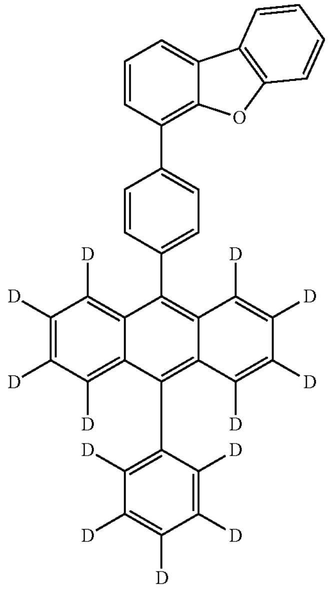
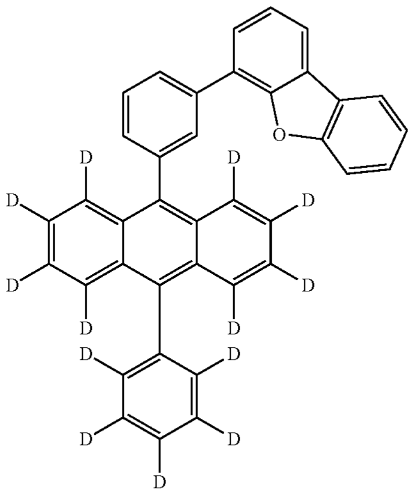
-continued
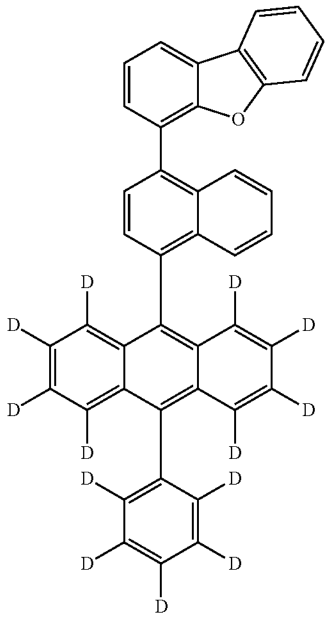
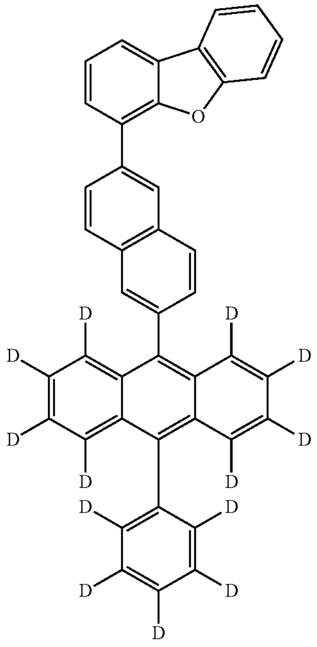

-continued
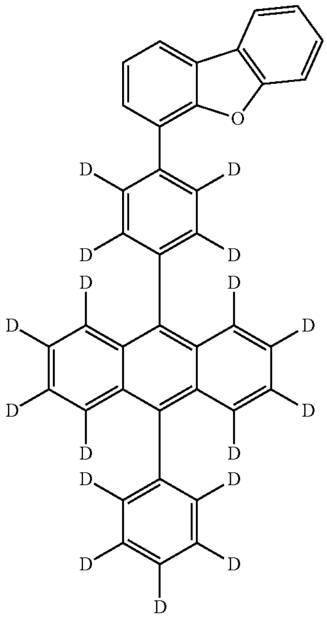
-continued
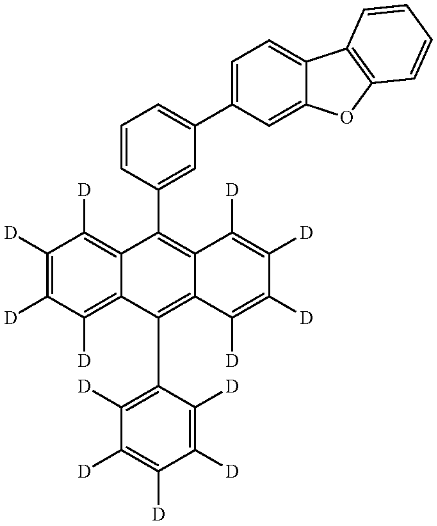
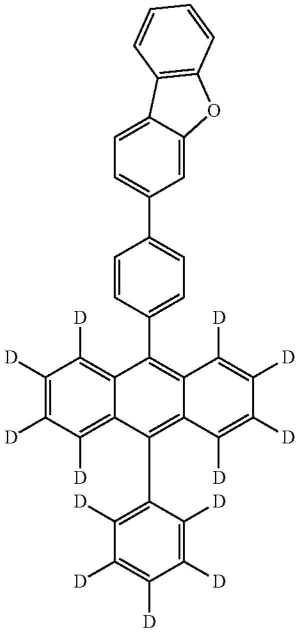
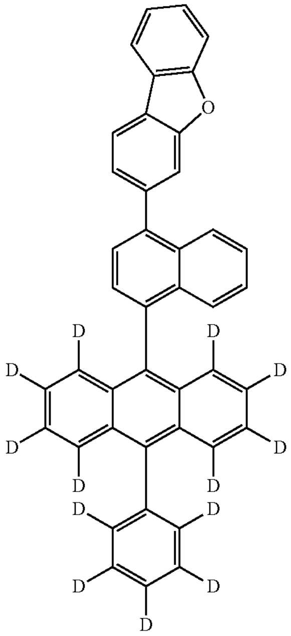

-continued
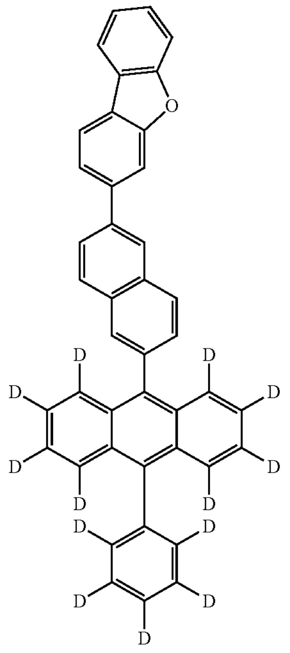
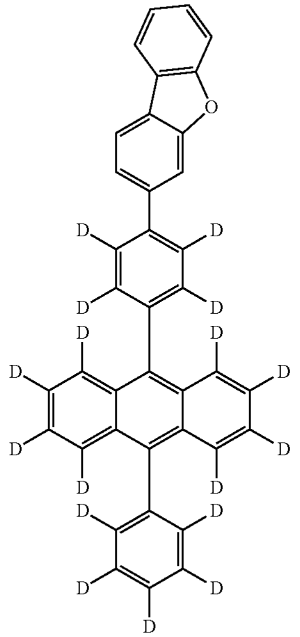
-continued
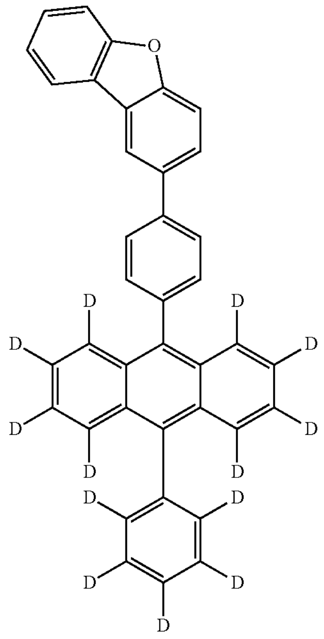
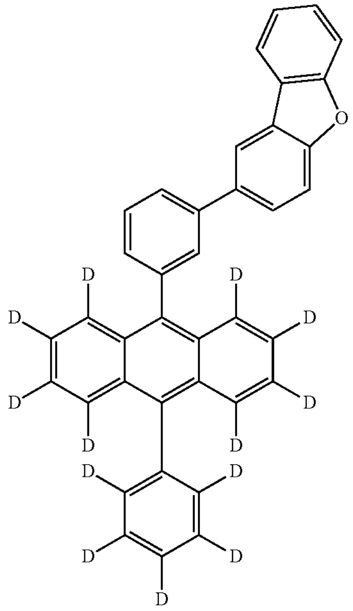

-continued
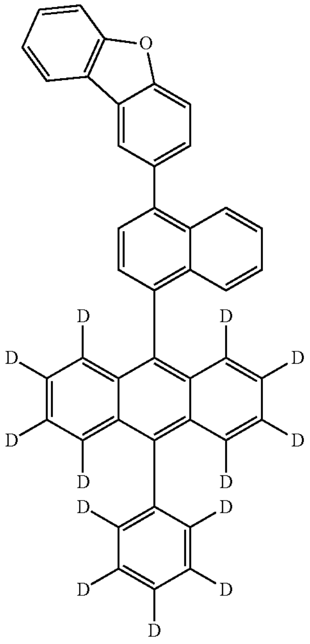
-continued
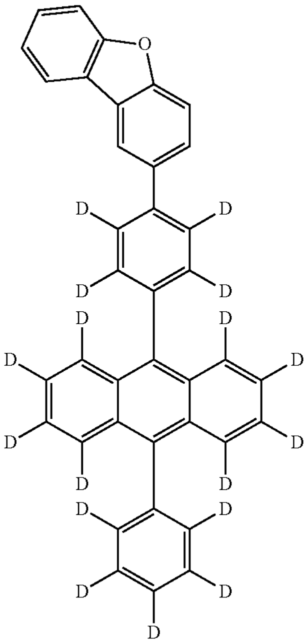
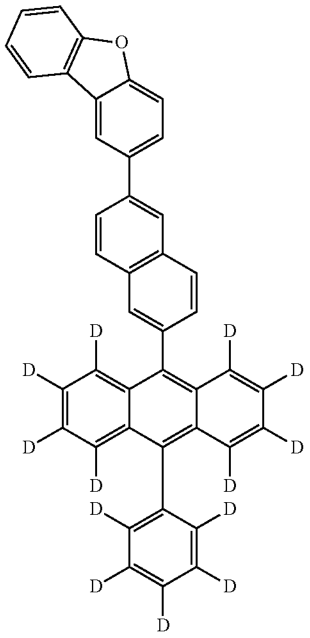
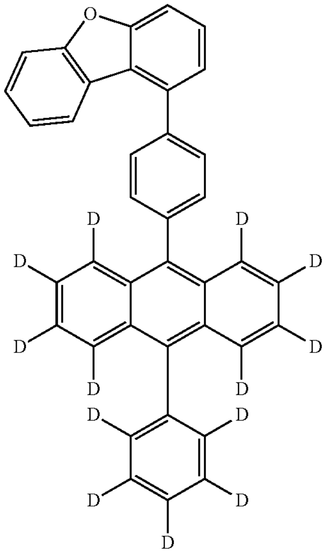

-continued
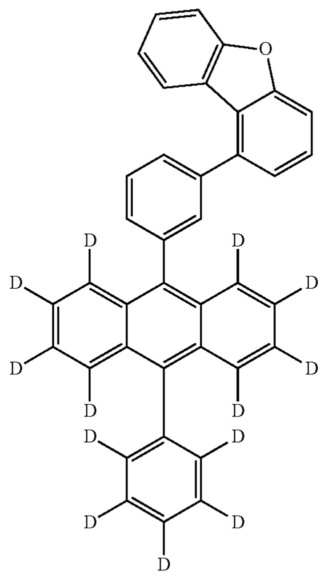
-continued
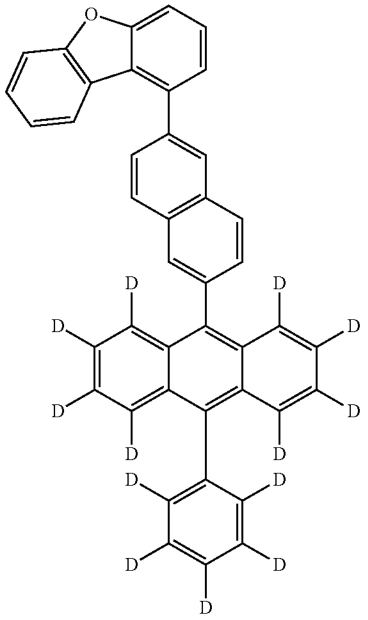
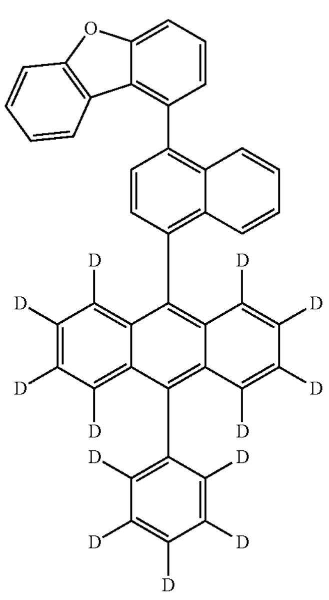
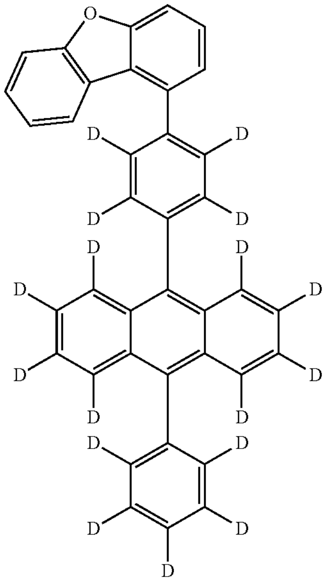

-continued
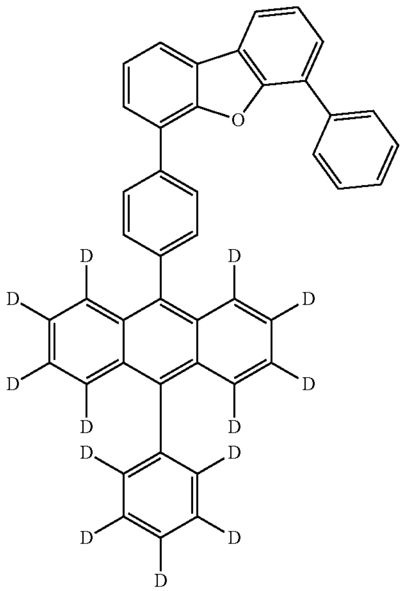
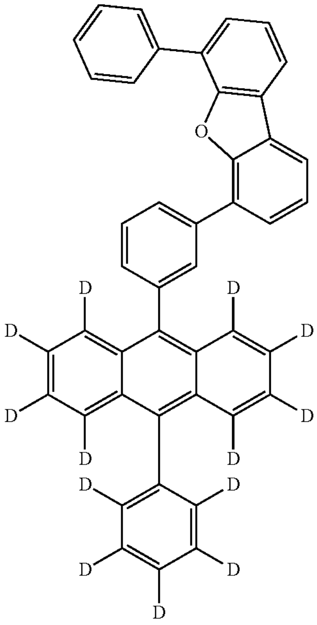
-continued
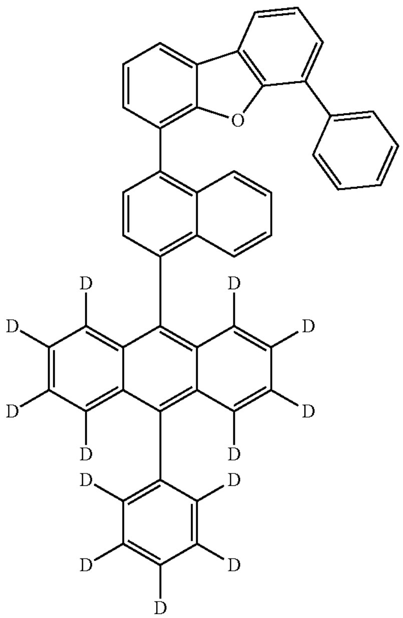
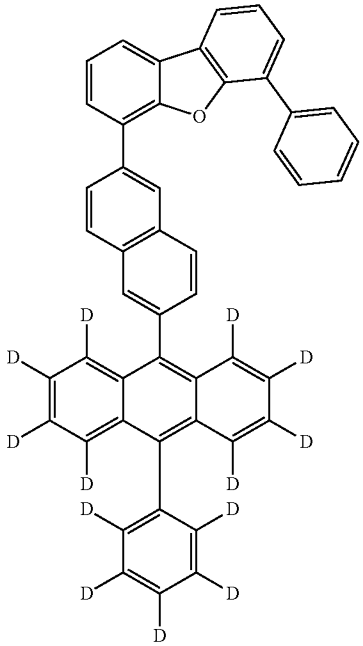

-continued
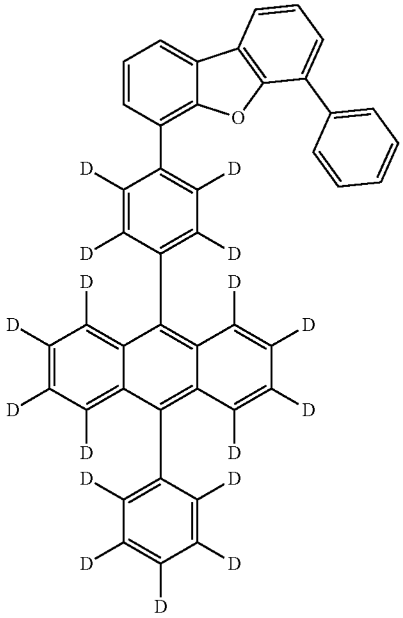
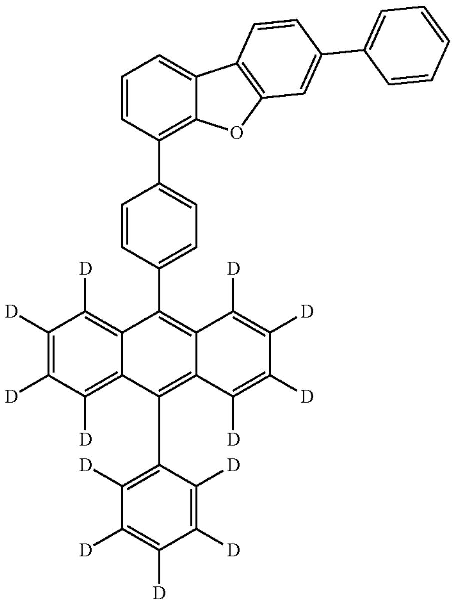
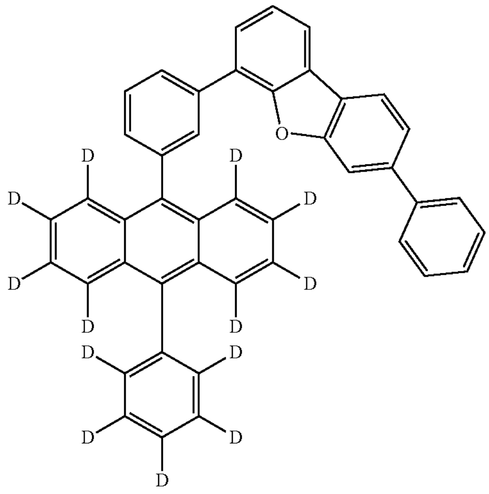
-continued
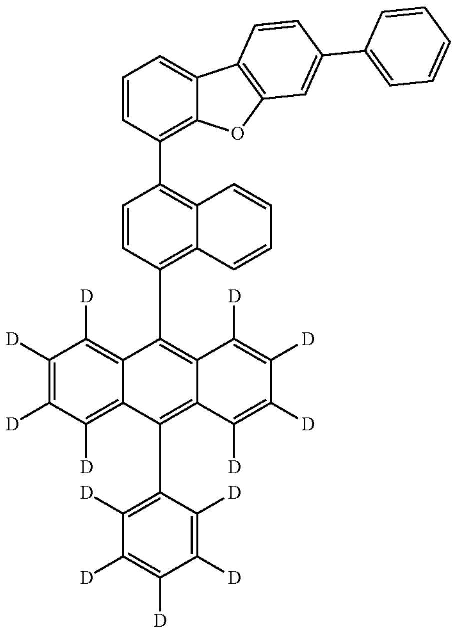
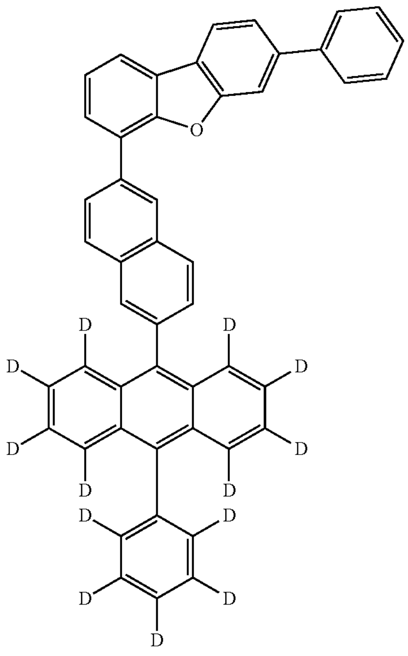

-continued
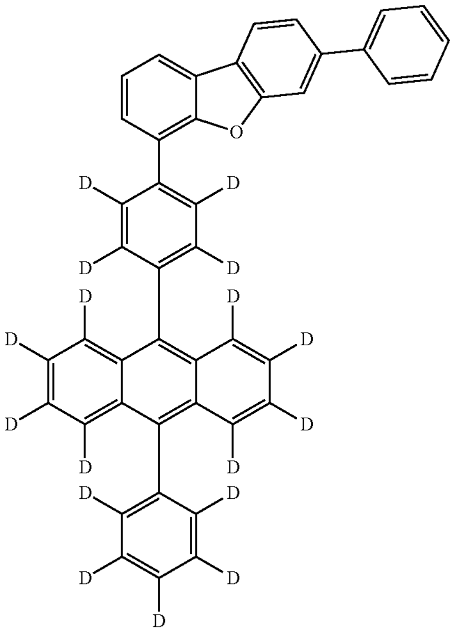
-continued
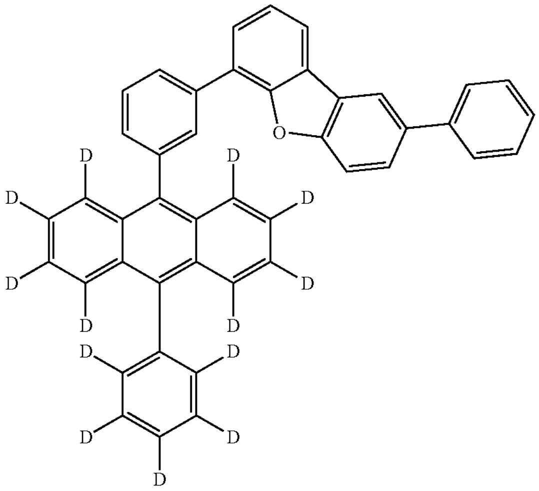
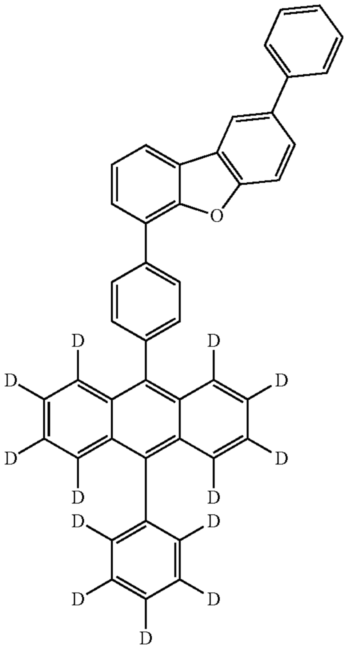
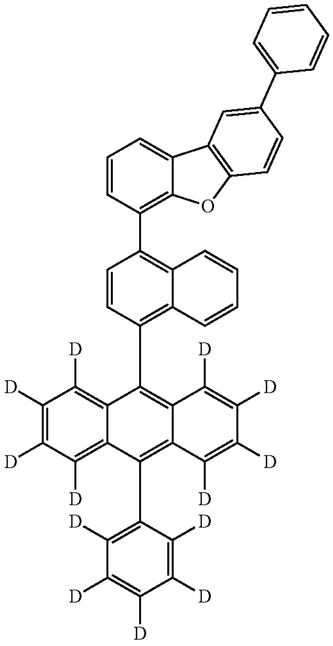

-continued
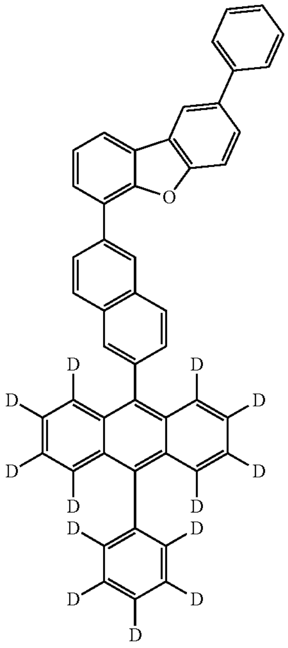
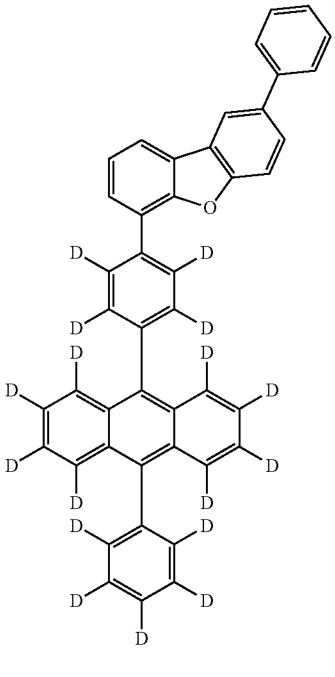
-continued
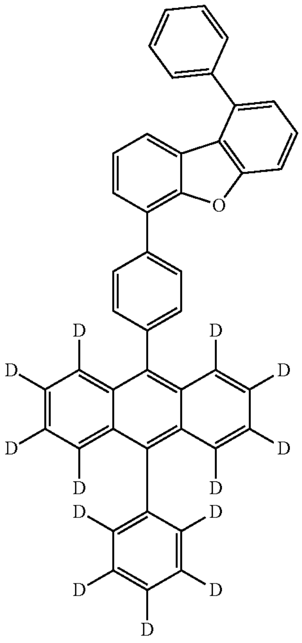
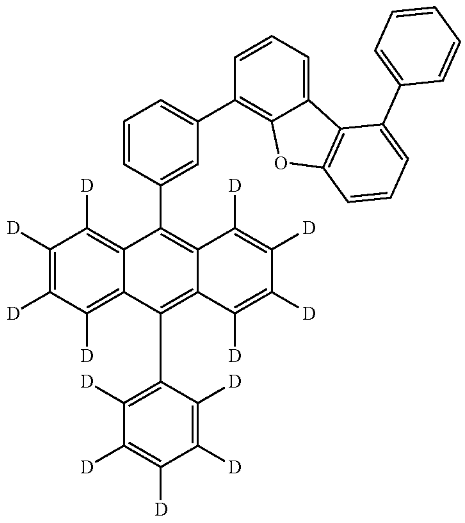

-continued
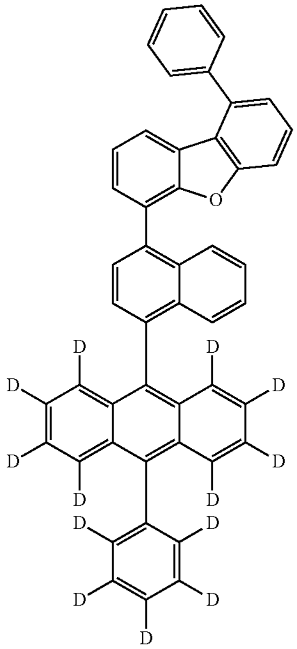
-continued
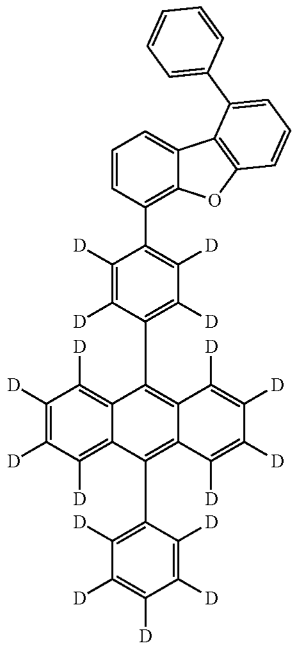
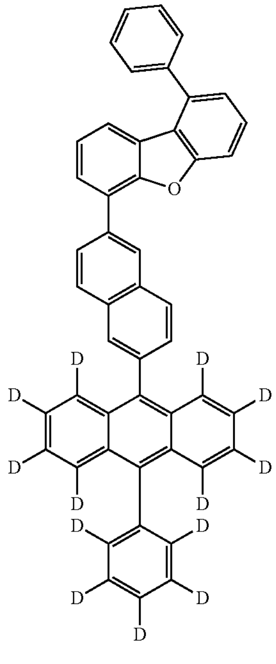
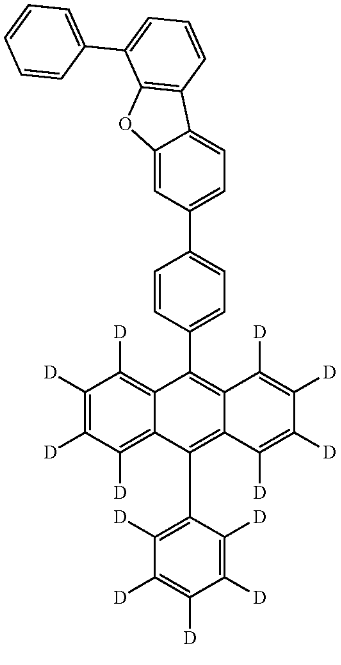

-continued
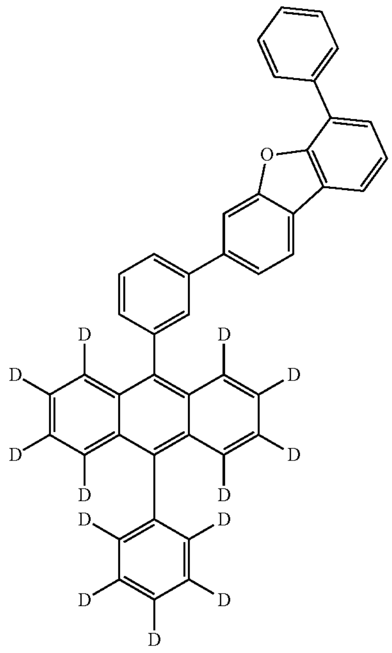
-continued
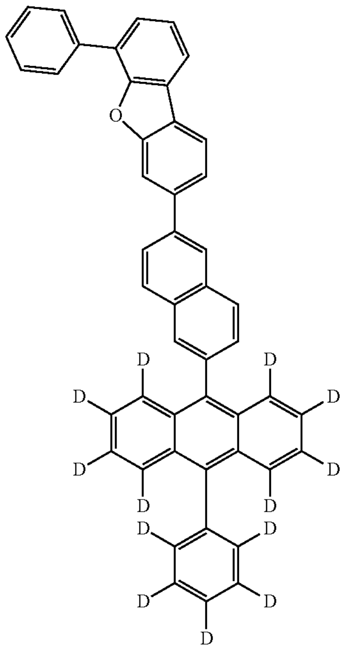
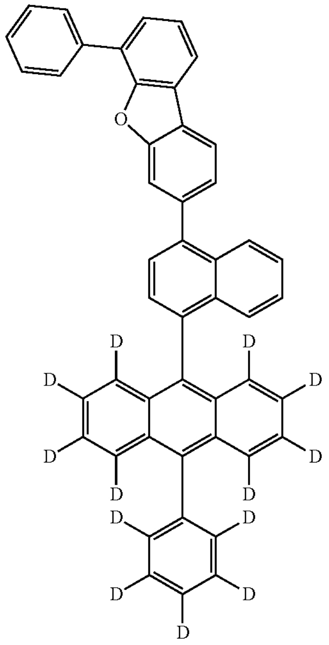
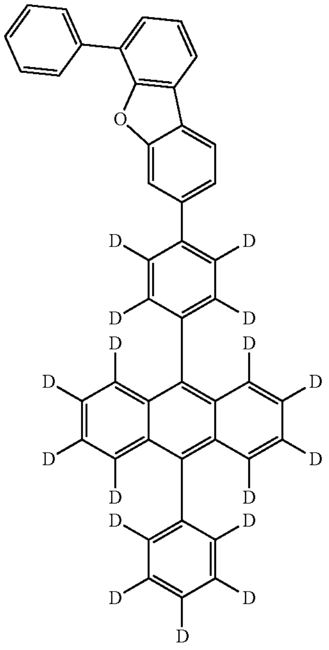

-continued
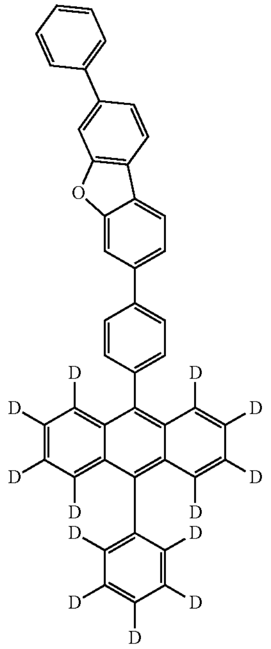
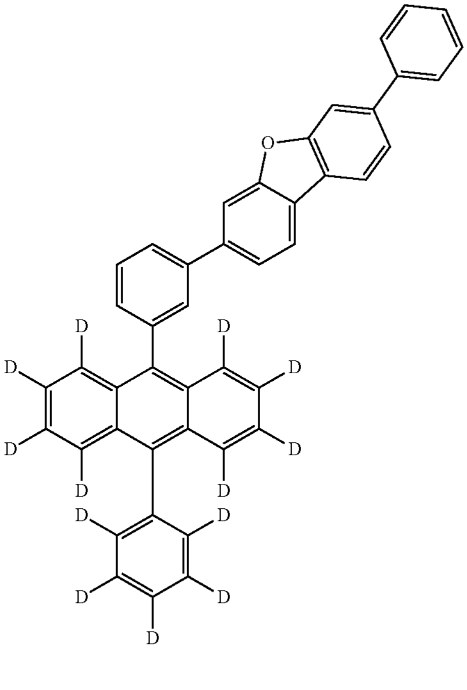
-continued
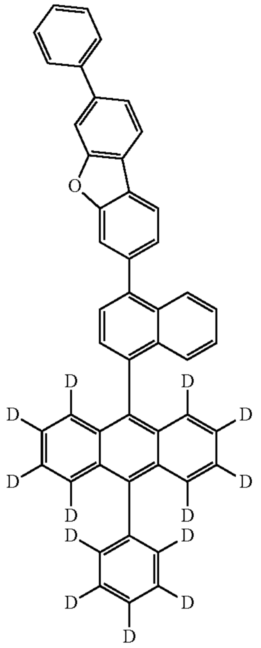
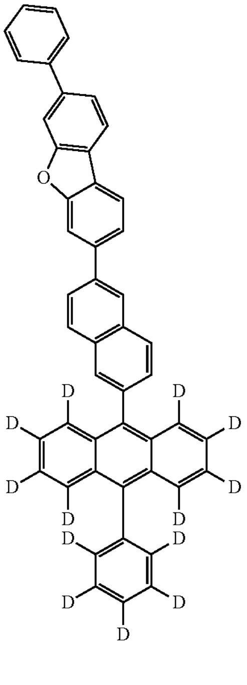

-continued
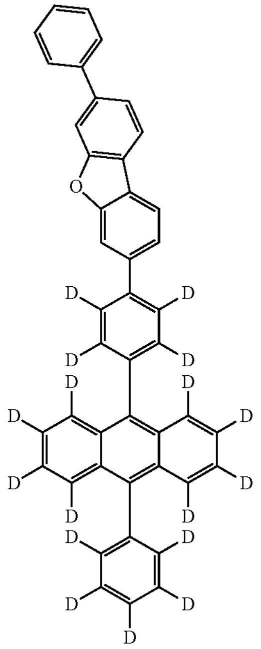
-continued
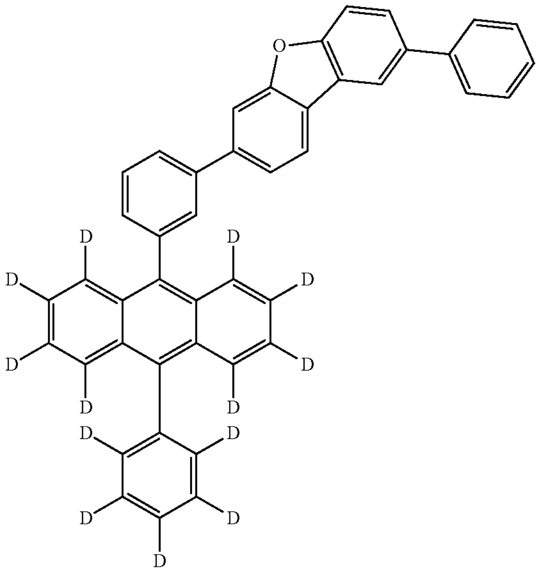
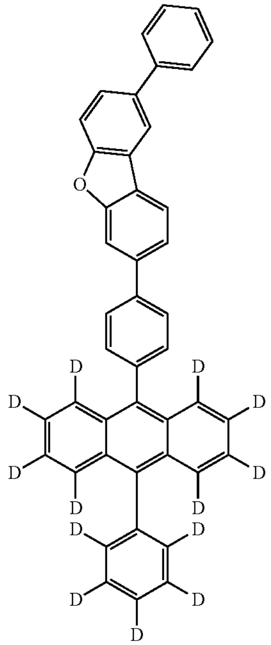
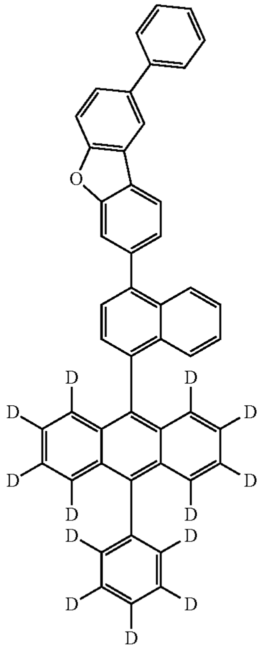

-continued
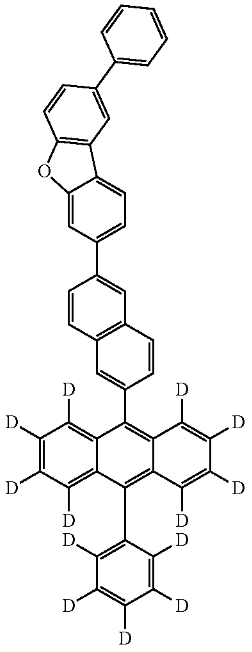
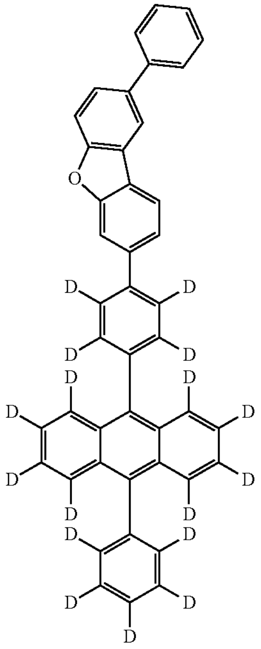
-continued
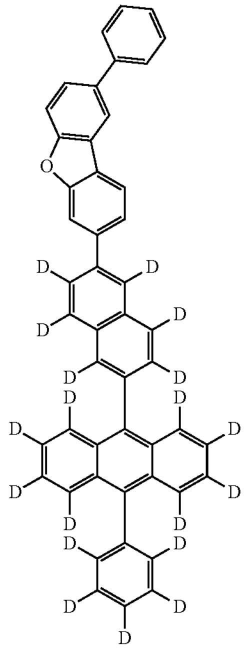
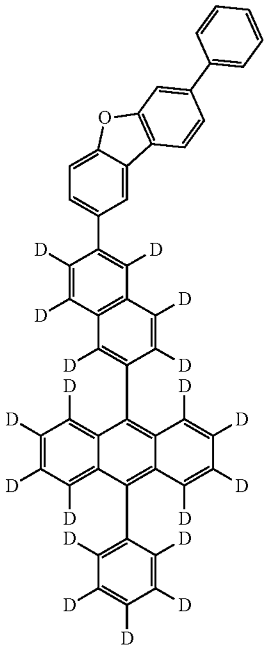

-continued
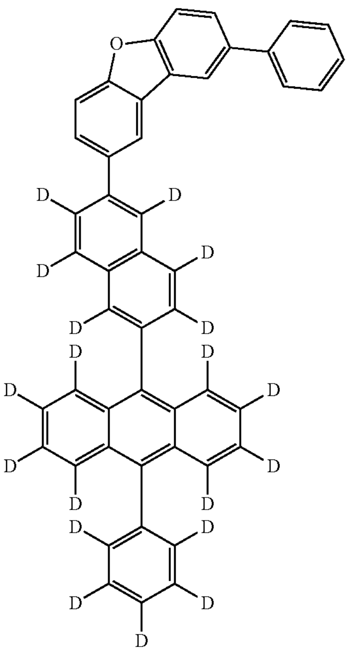
-continued
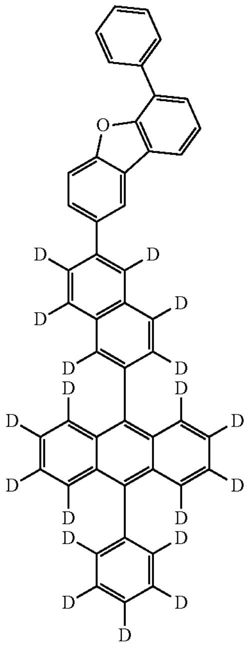
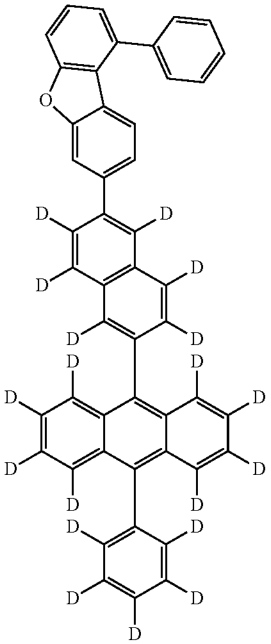
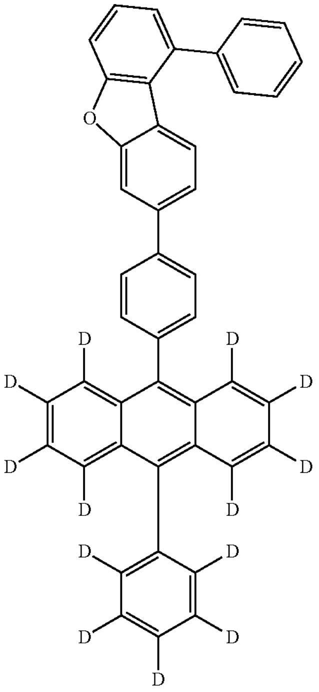

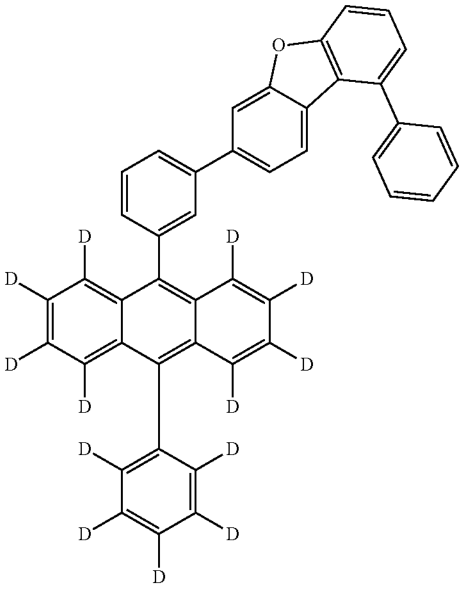
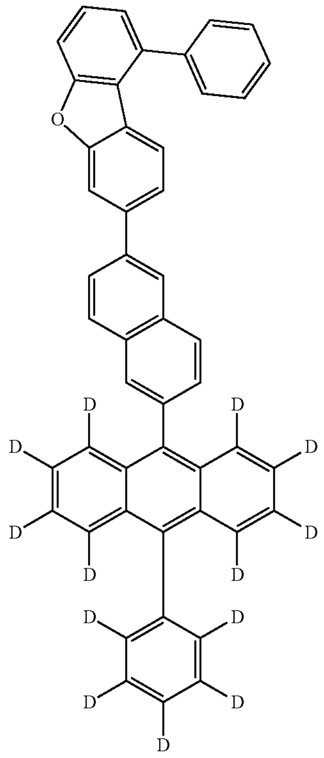
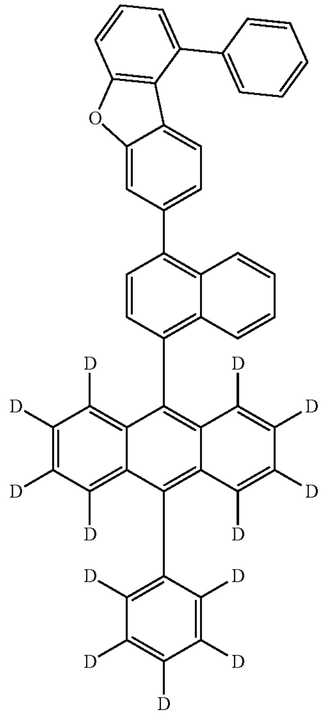
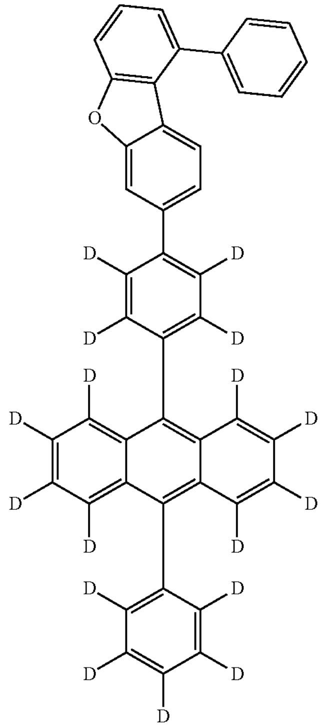

-continued
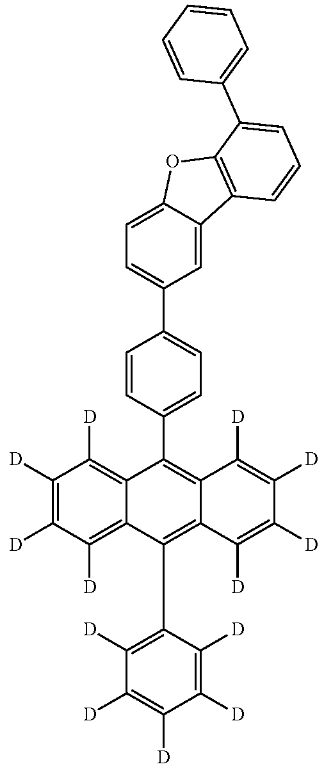
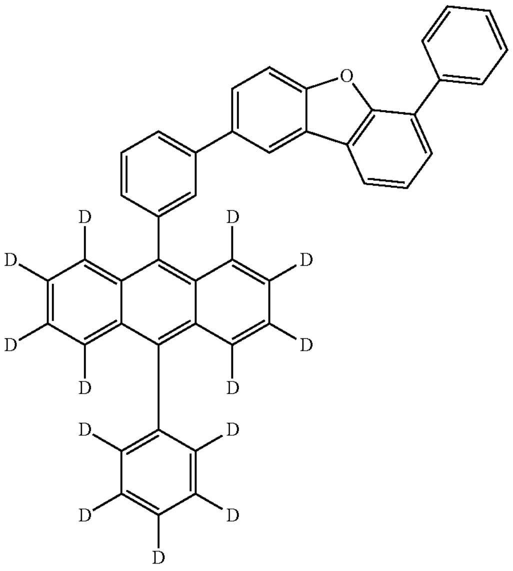
-continued
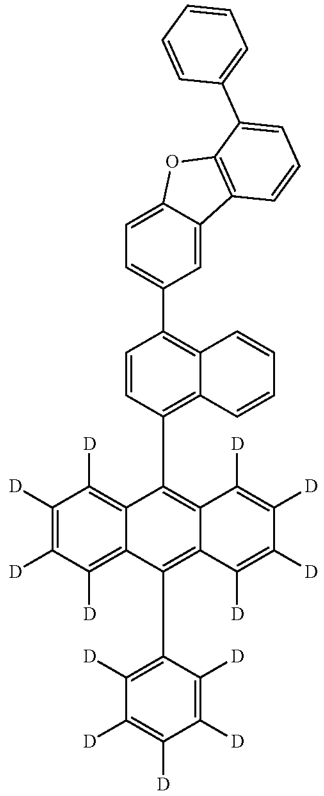
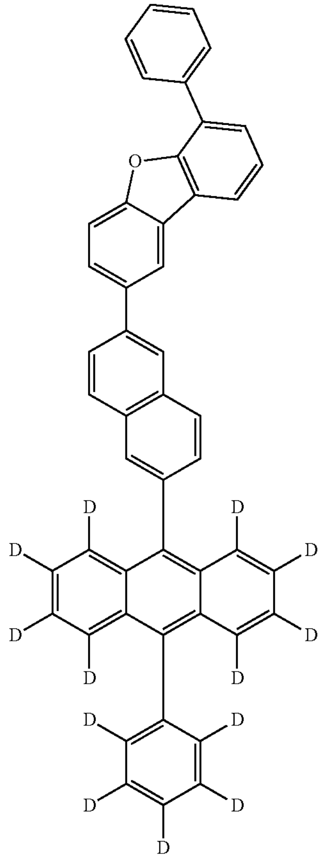

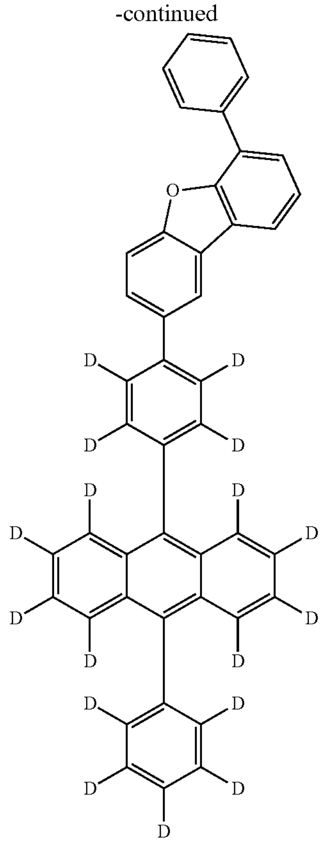
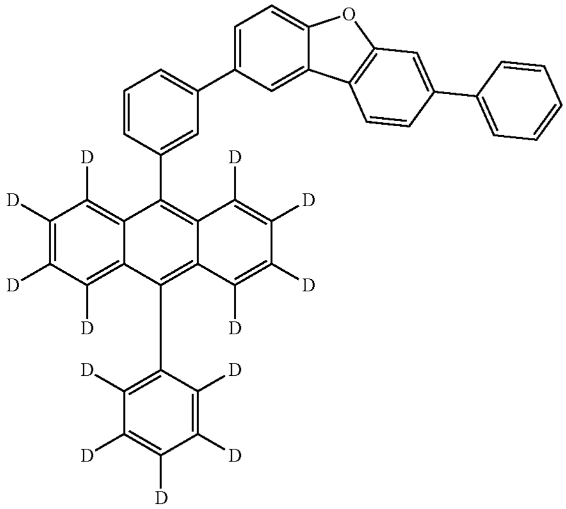
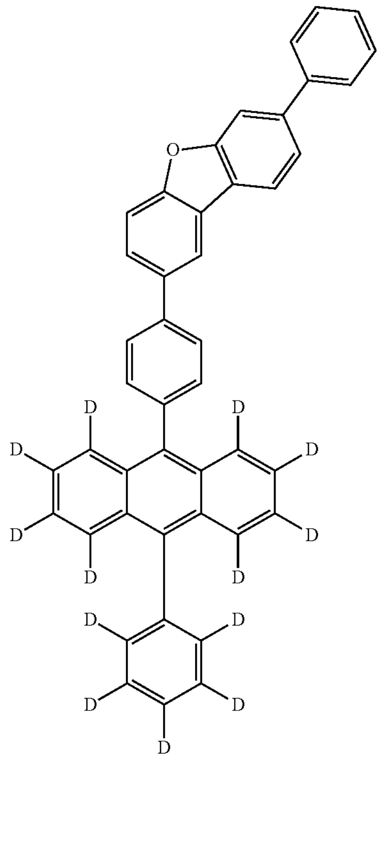
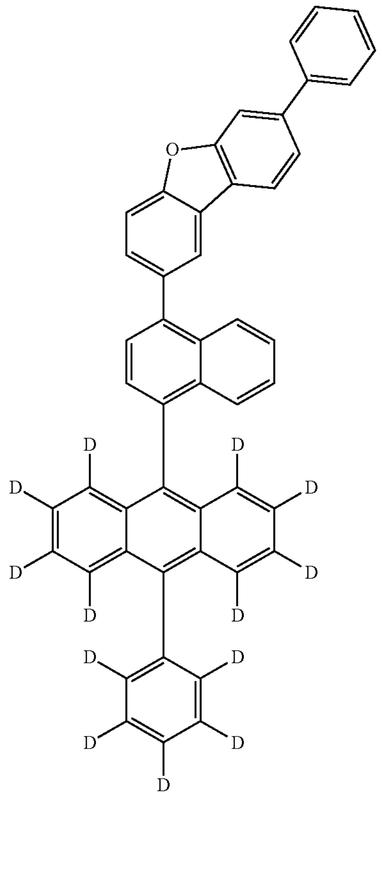

-continued
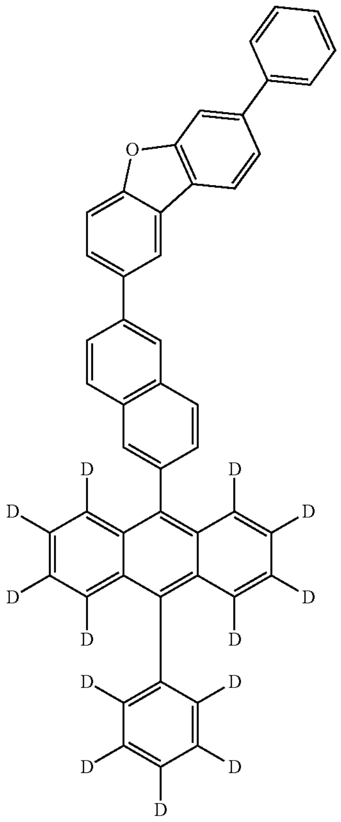
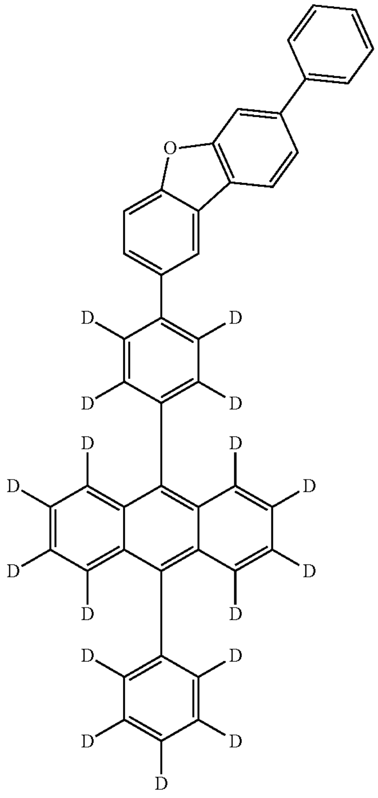
-continued
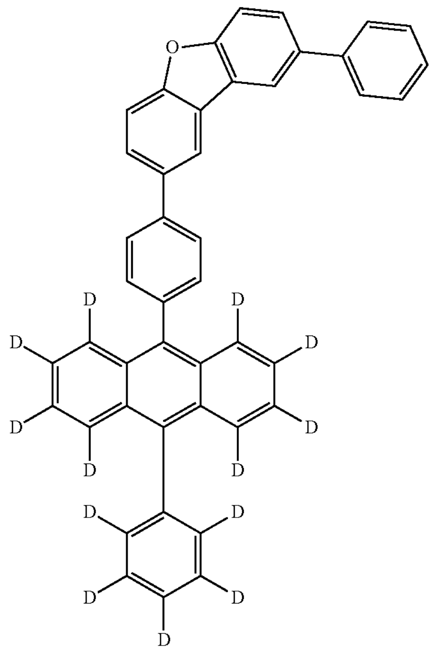
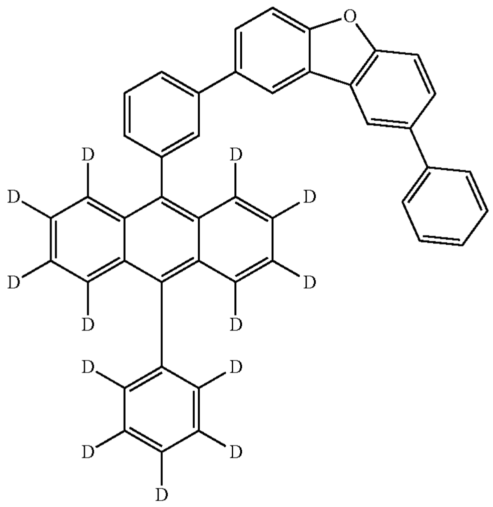

-continued
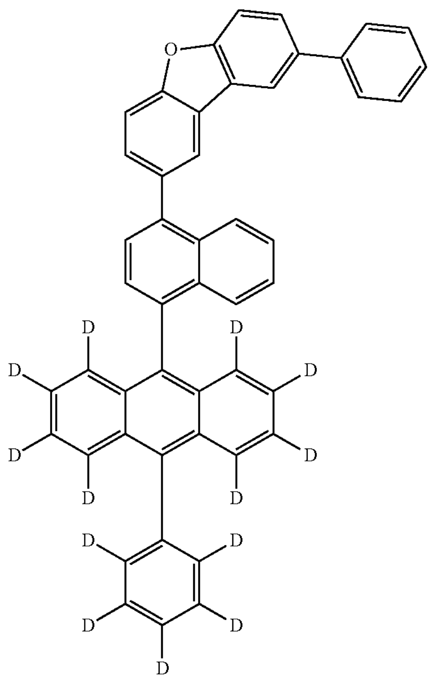
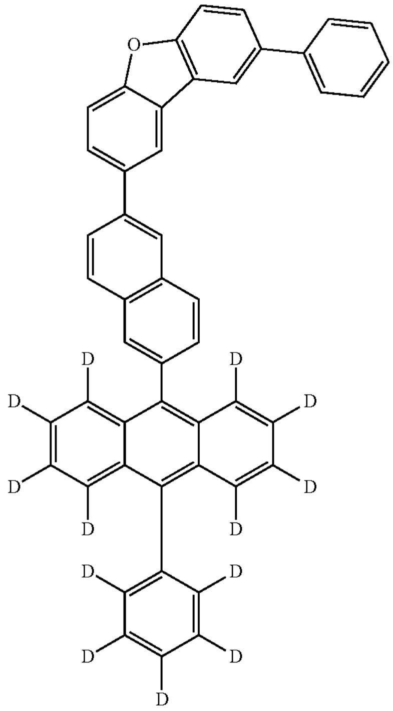
-continued
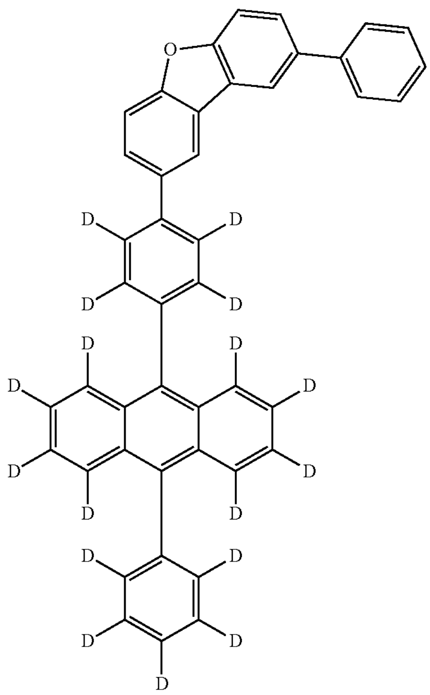
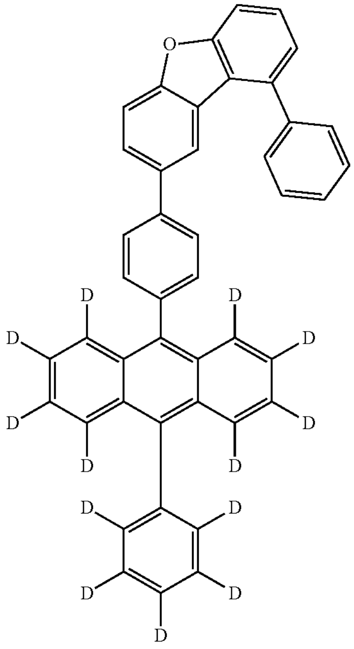

-continued
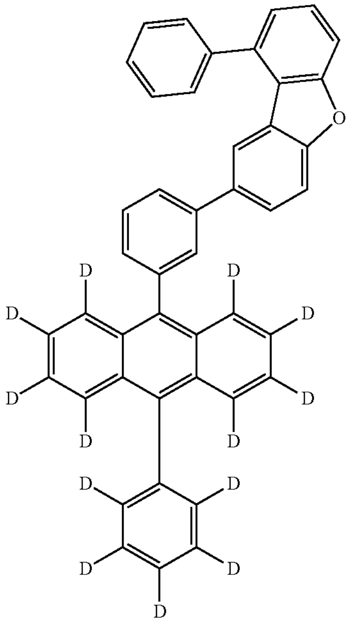
-continued
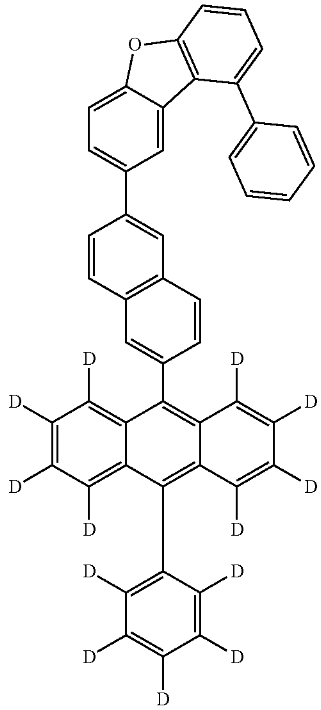
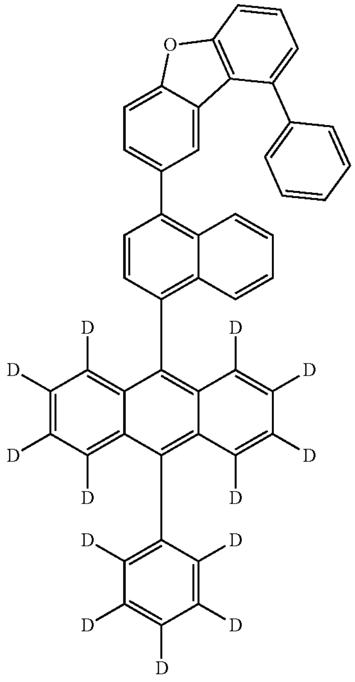
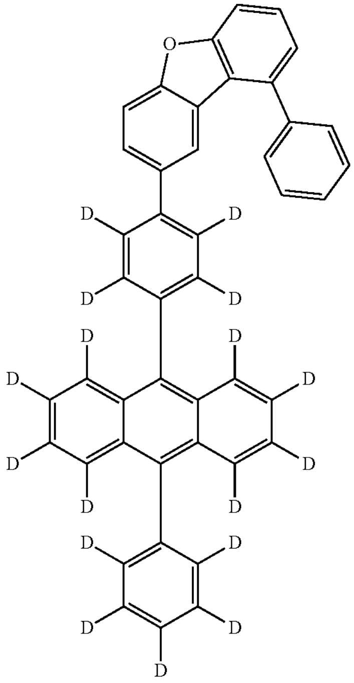

-continued
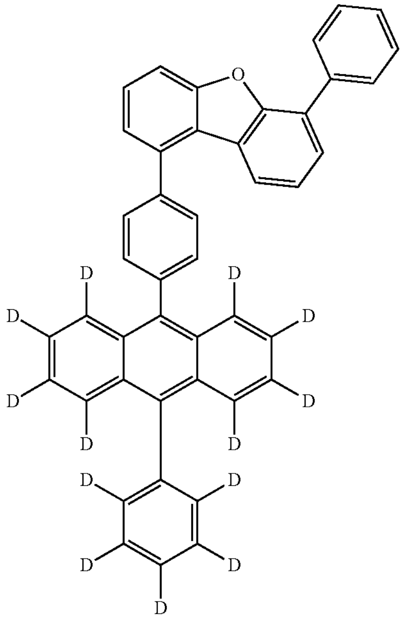
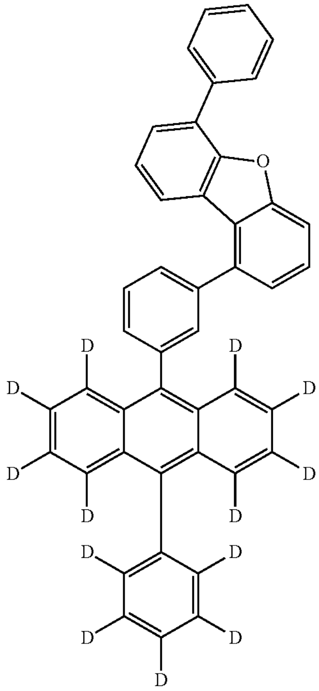
-continued
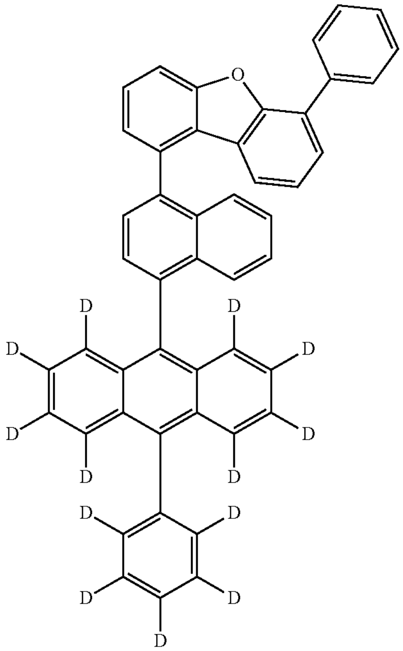
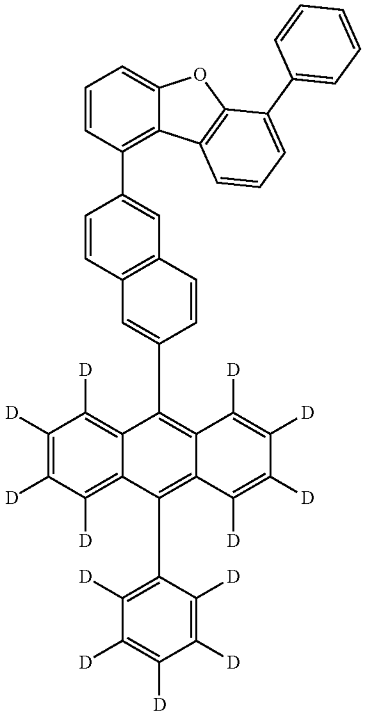

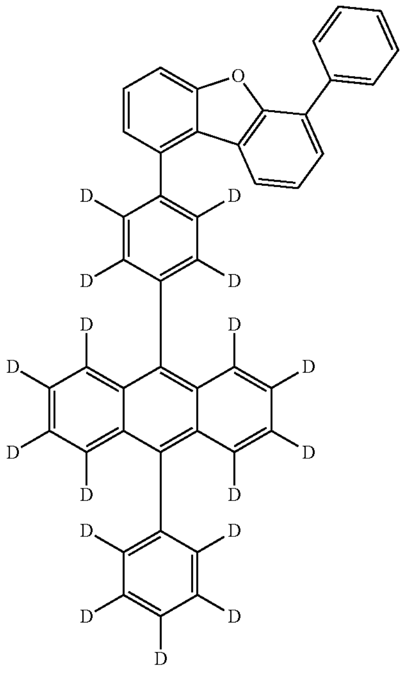
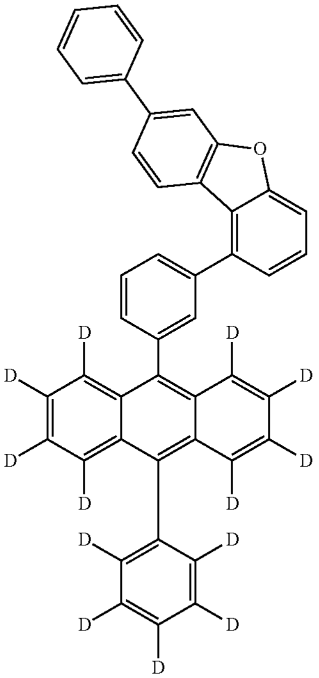
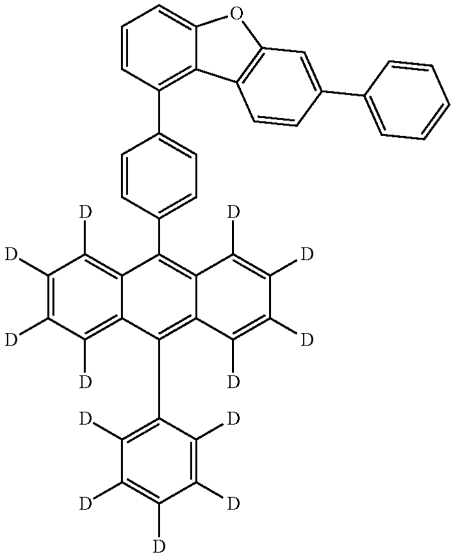
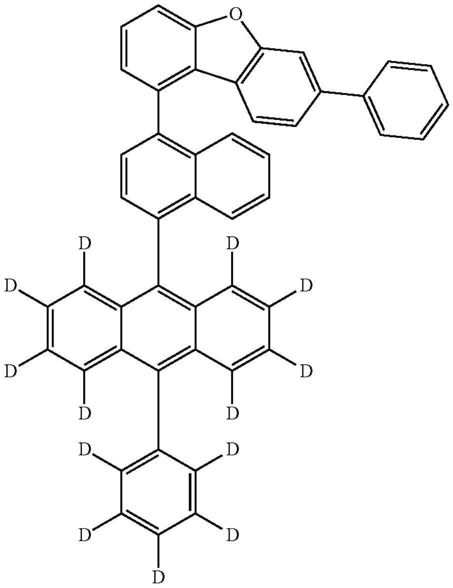

-continued
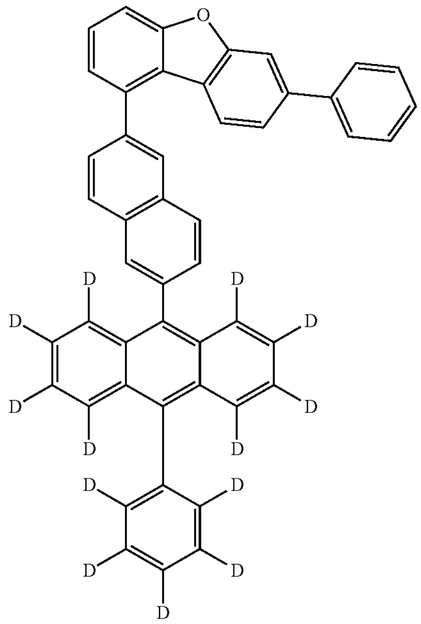
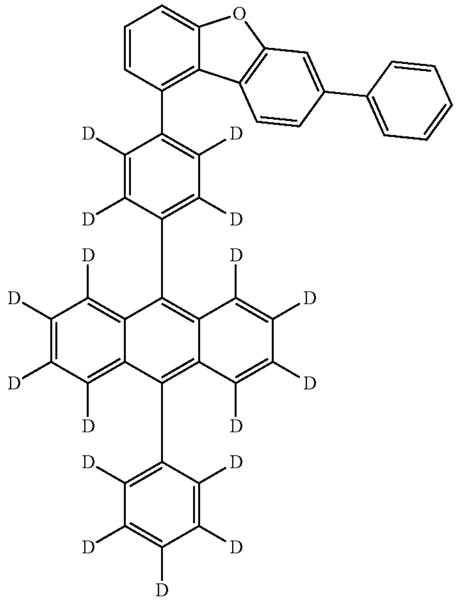
-continued
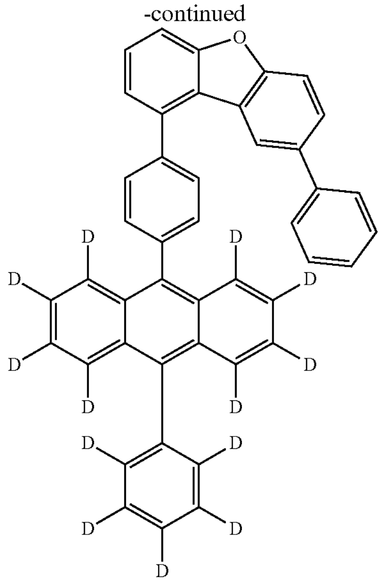
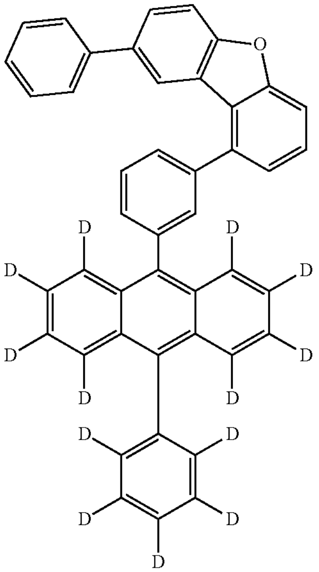
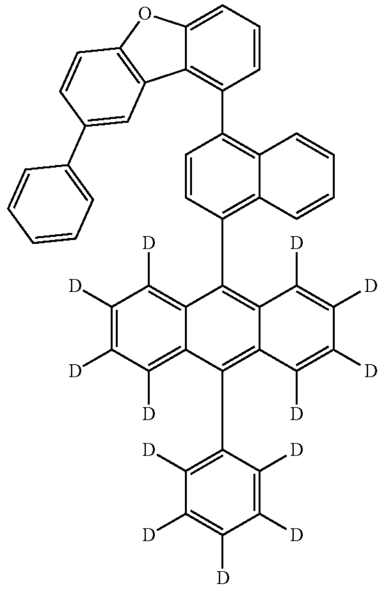

-continued
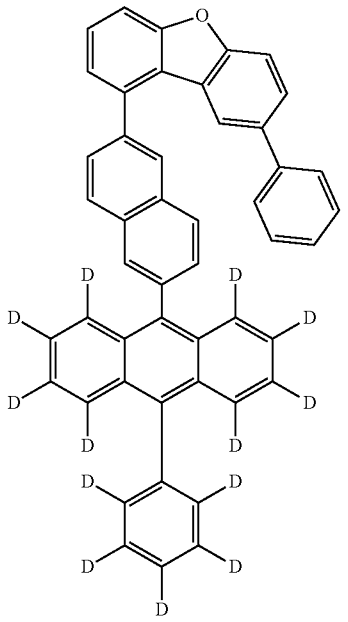
-continued
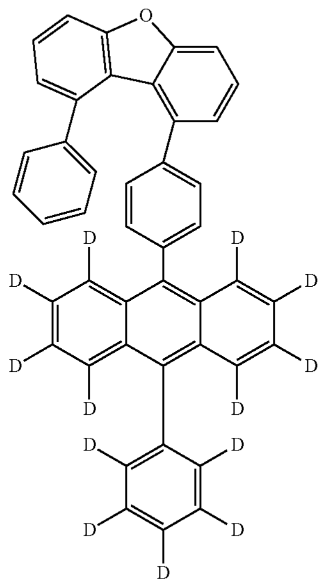
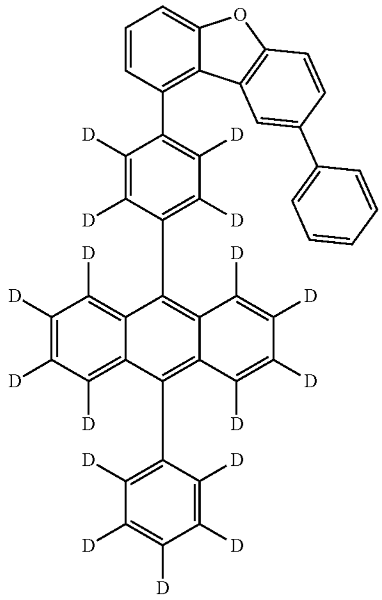
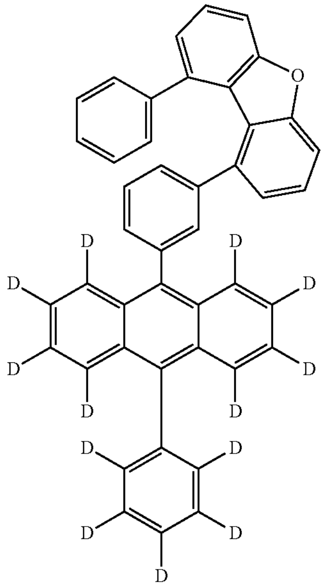

-continued
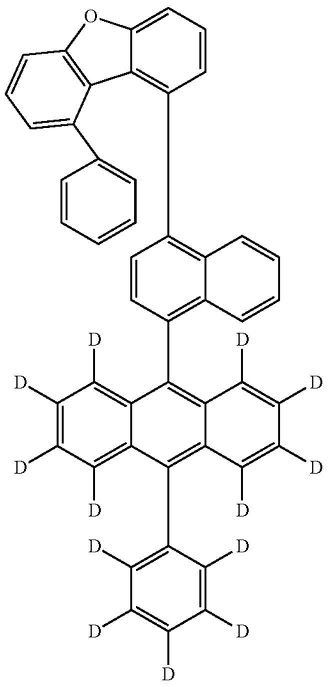
-continued
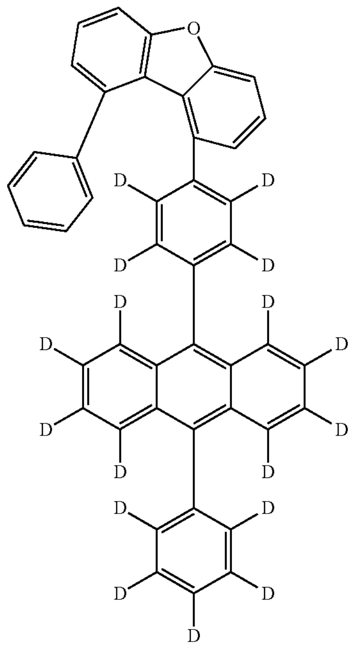
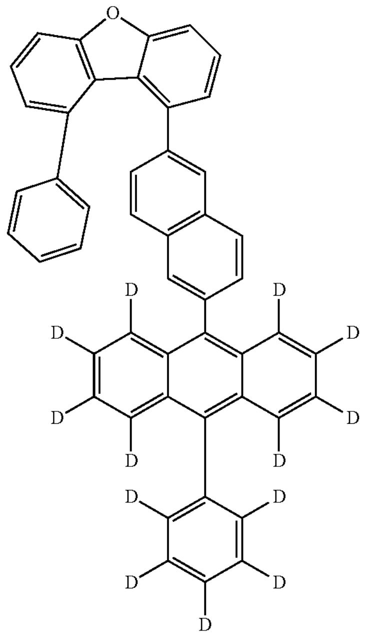
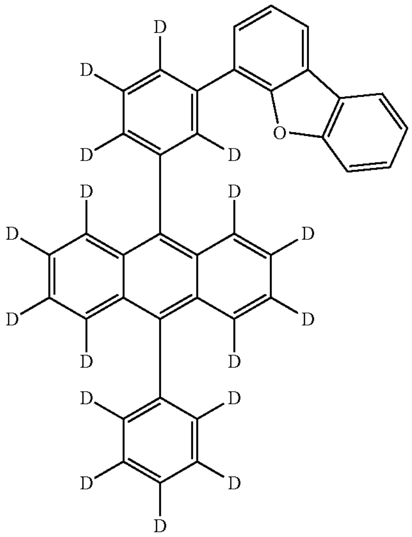

-continued
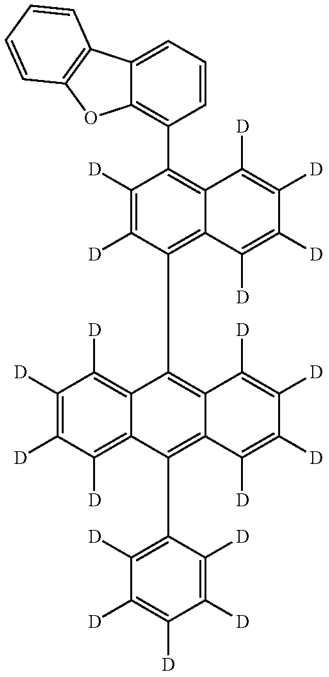
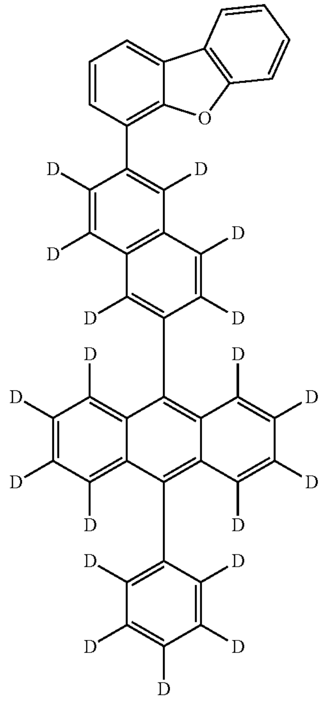
-continued
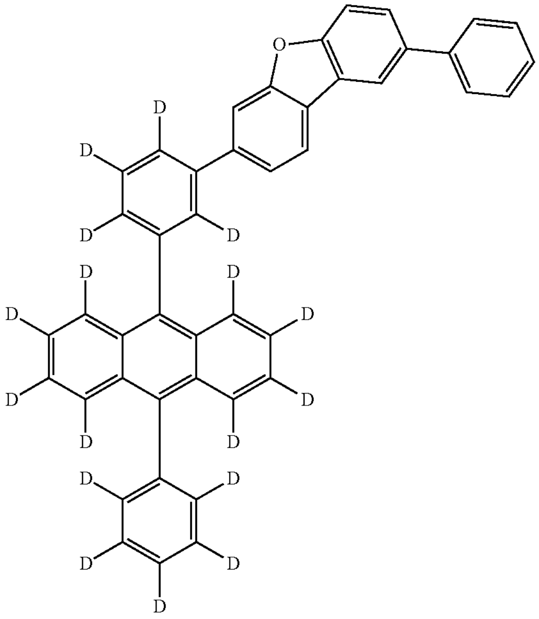
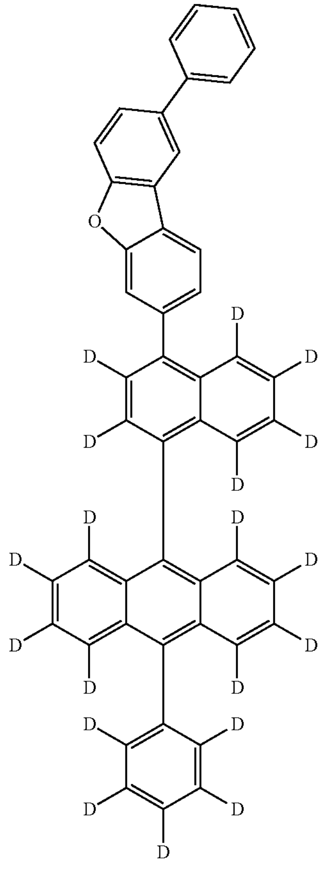

-continued
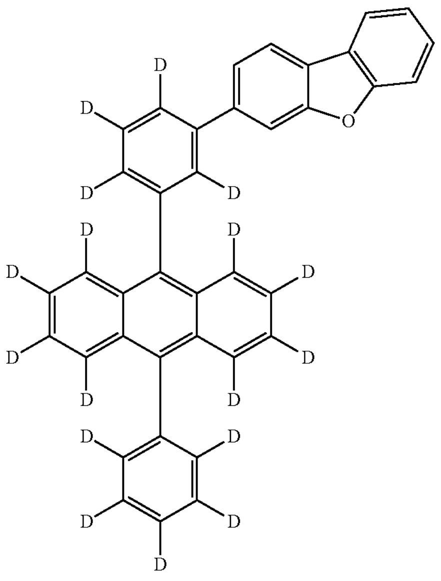
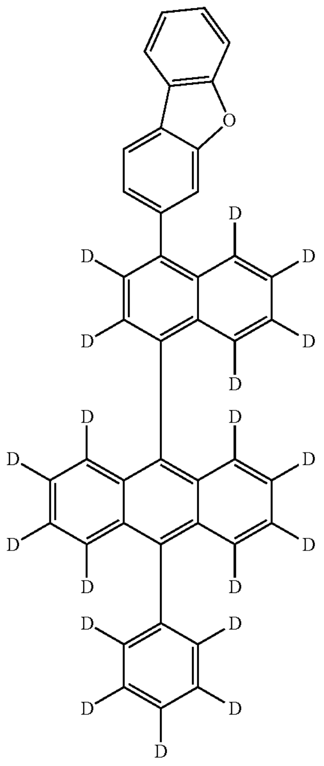
-continued
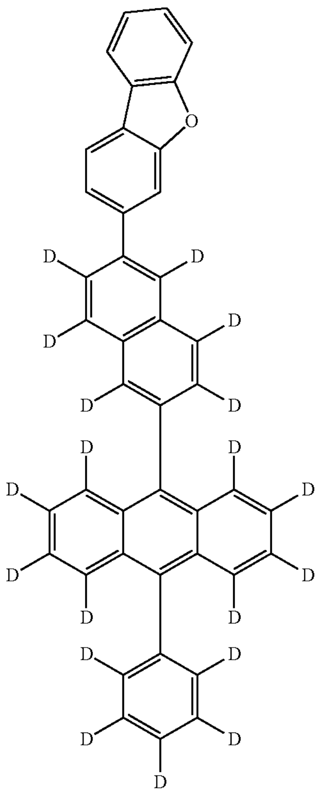
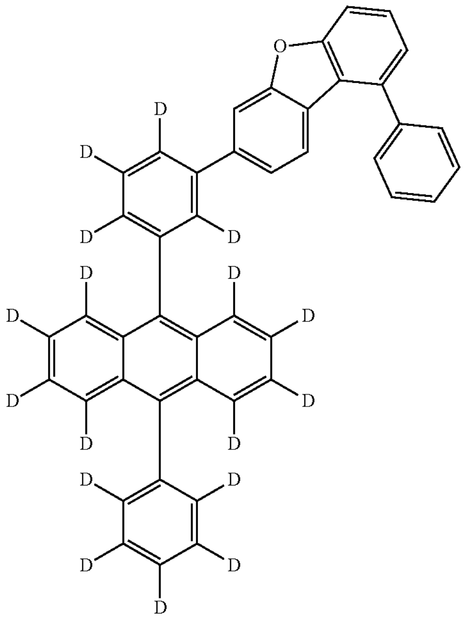

-continued
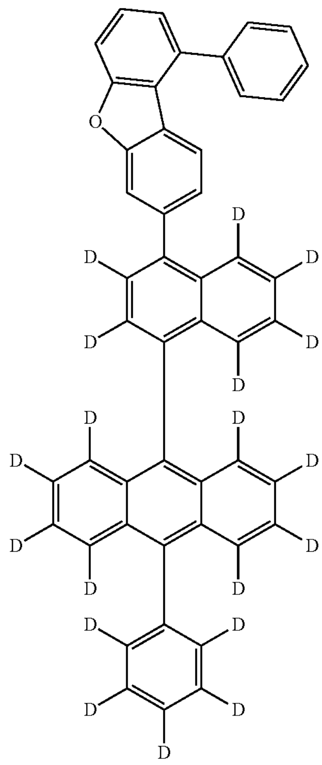
-continued
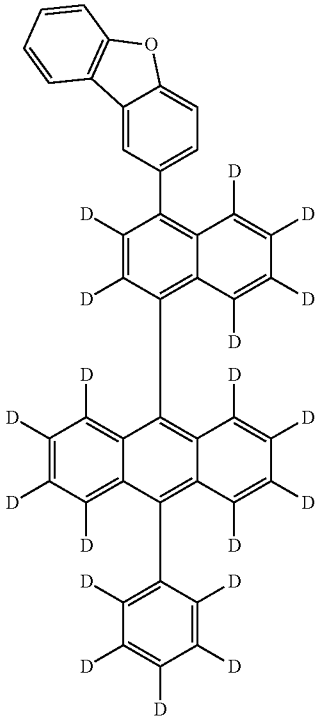
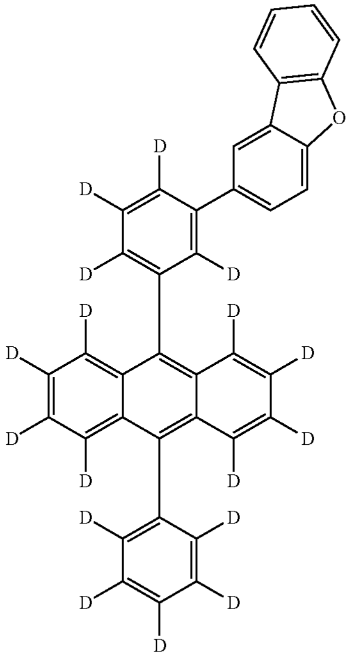
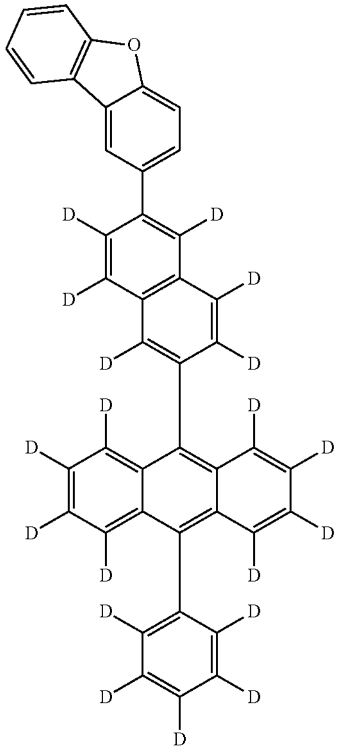

-continued
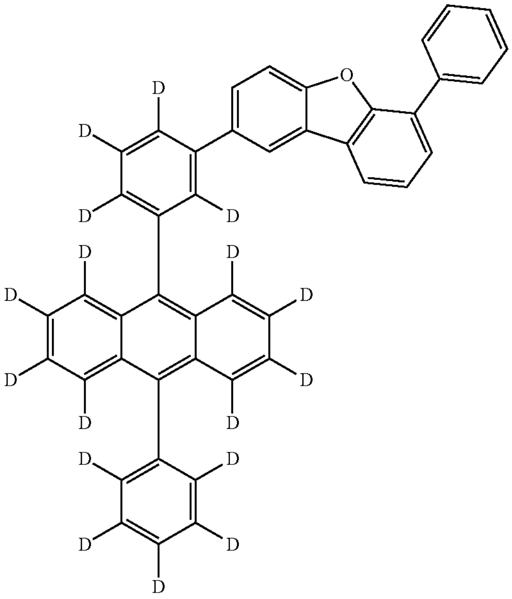
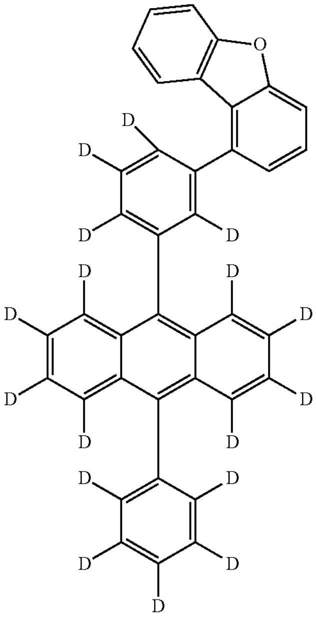
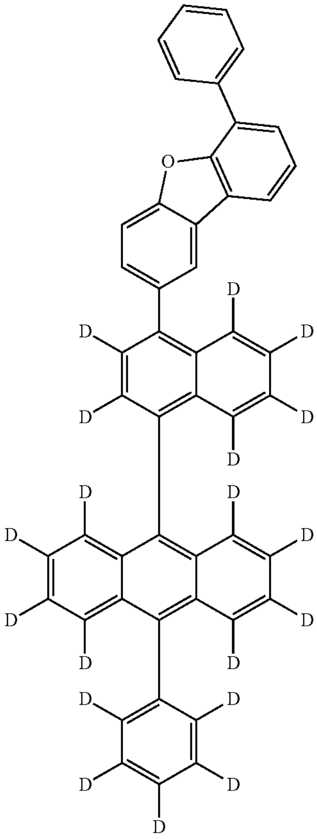
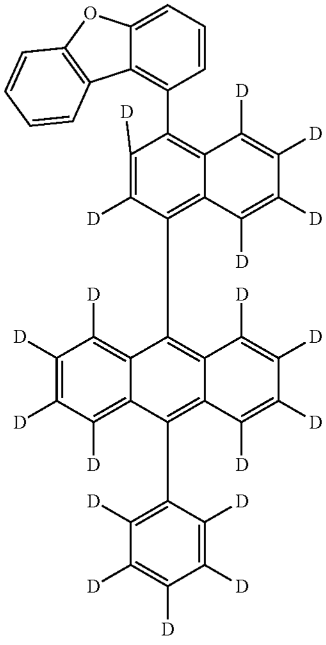

-continued
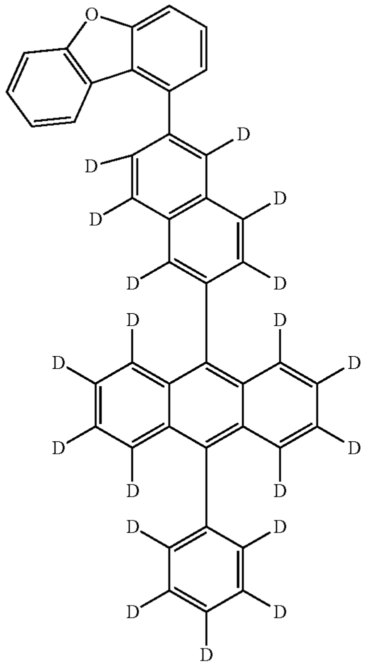
-continued
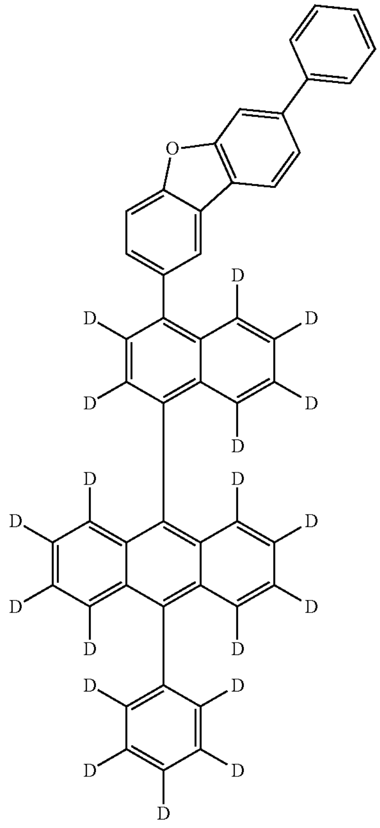
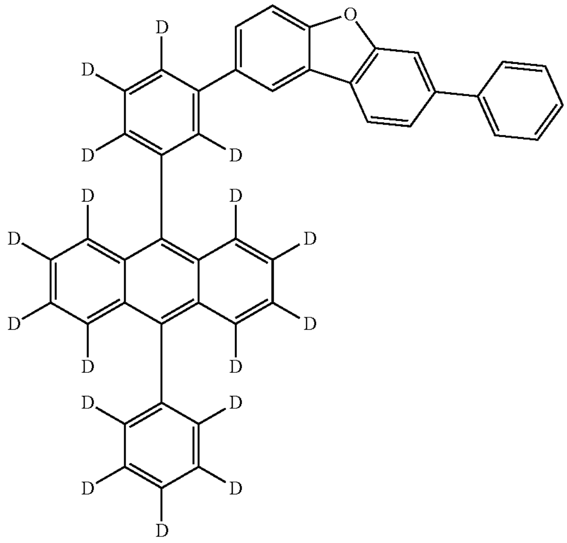
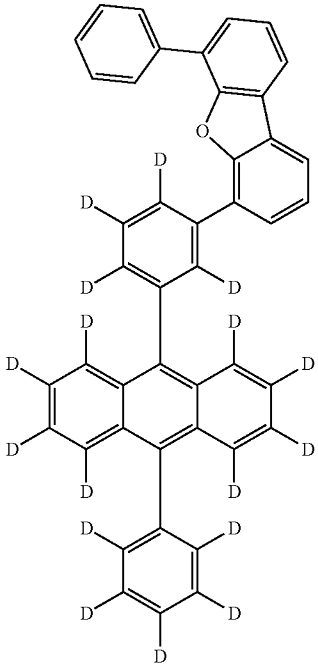

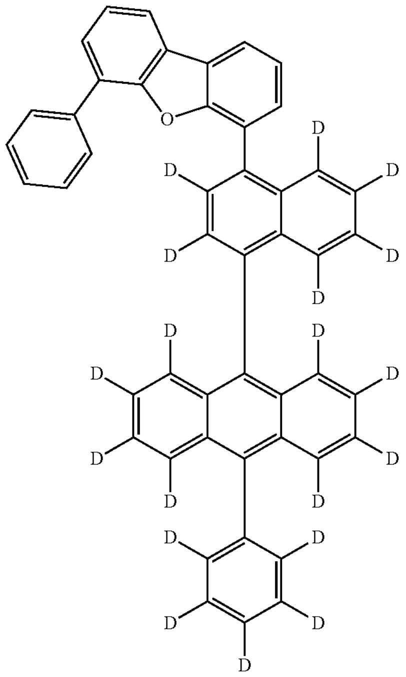
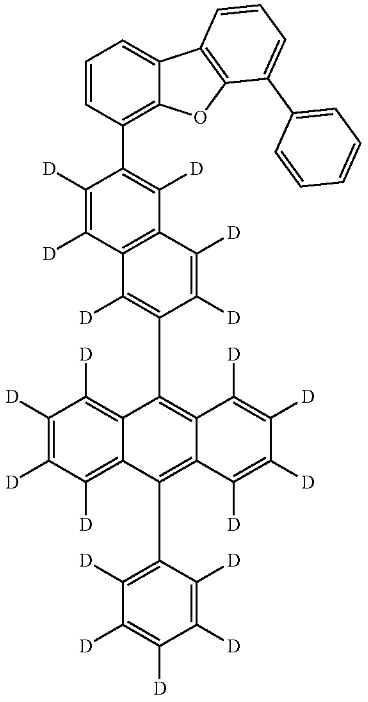
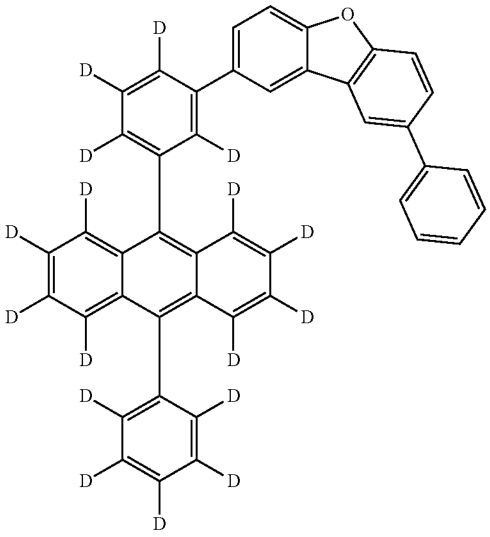
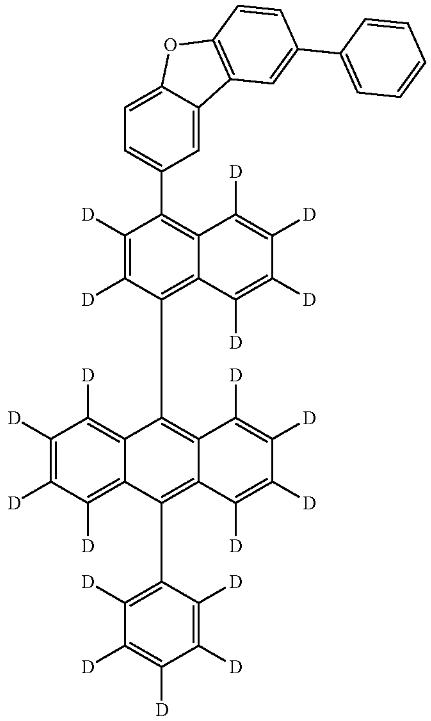

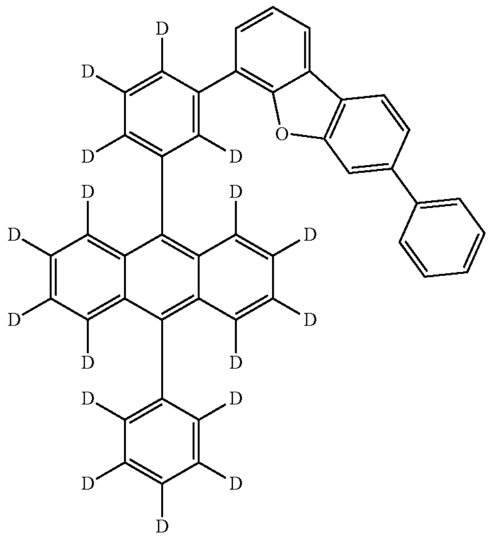
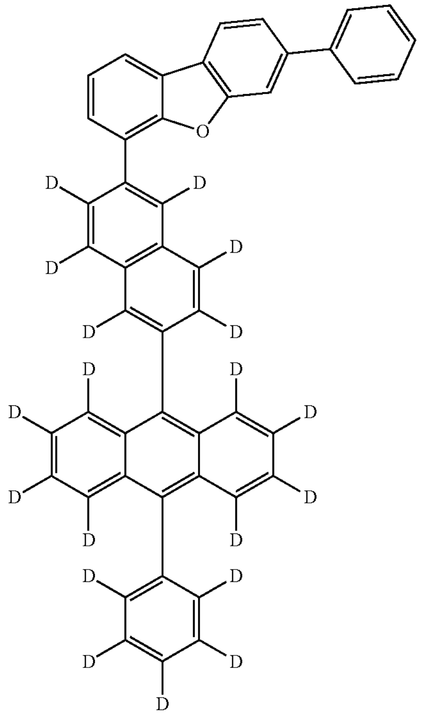
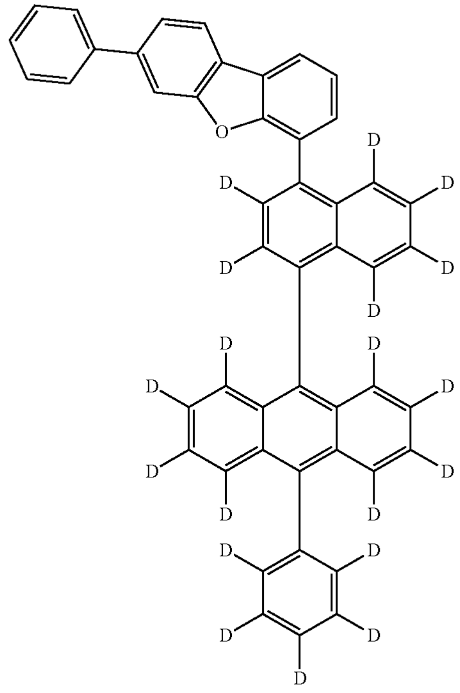
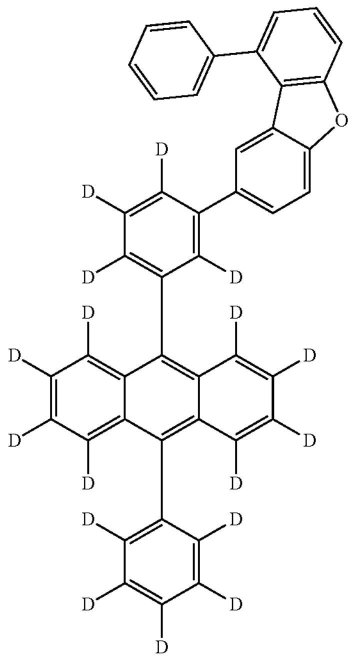

-continued
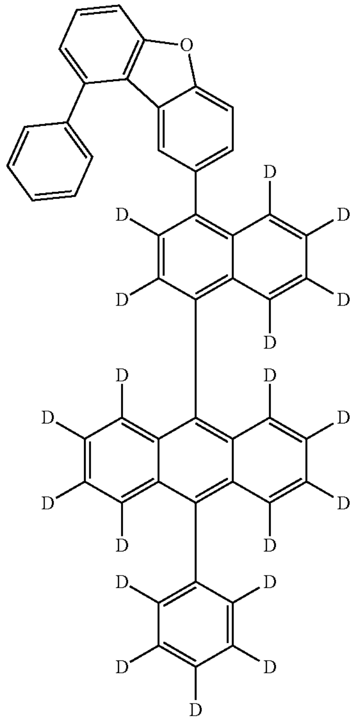
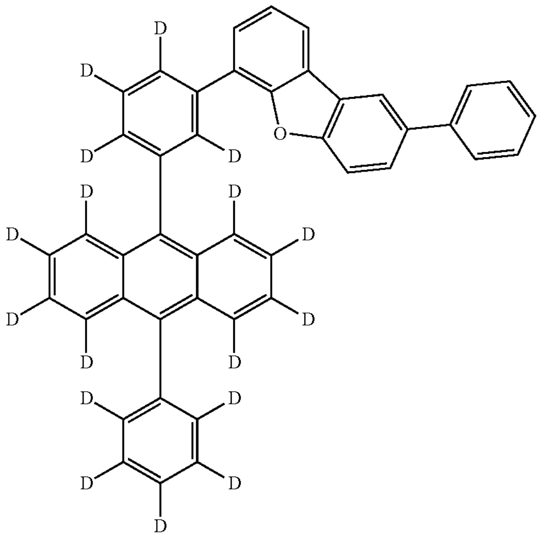
-continued
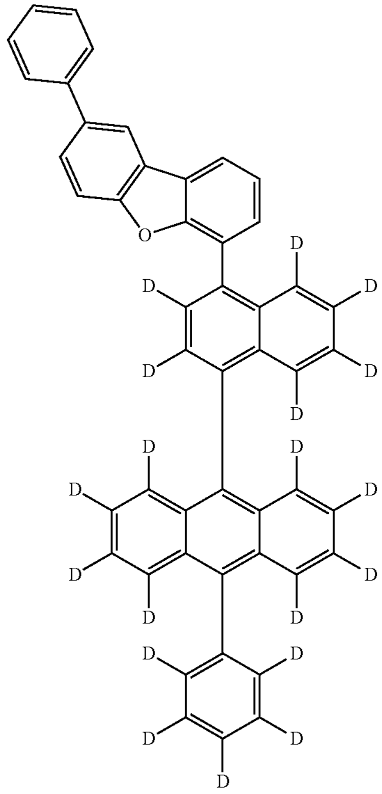
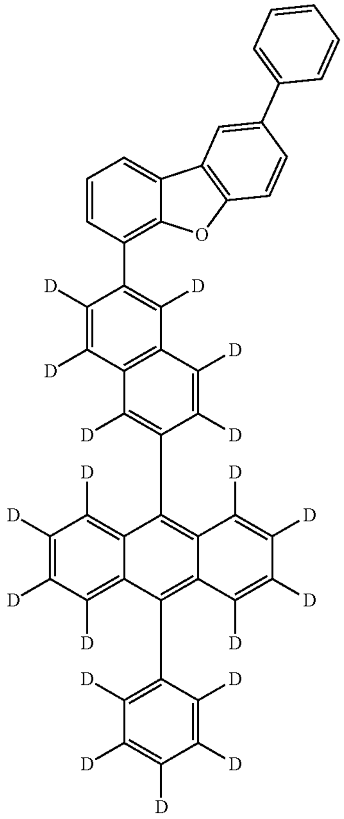

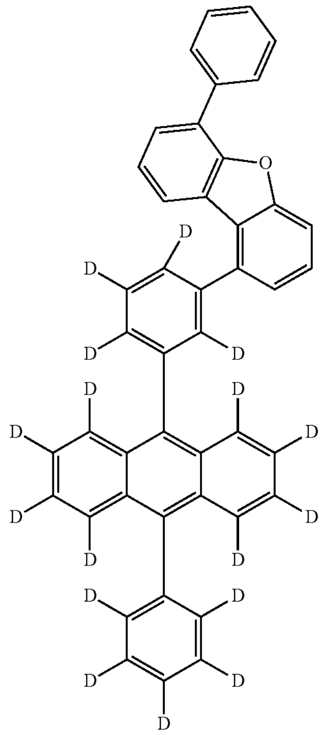
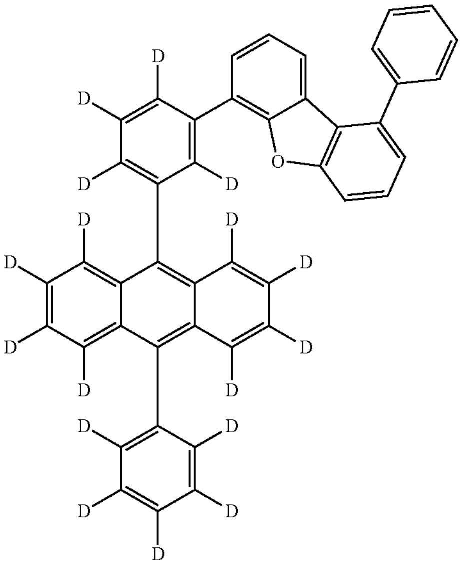
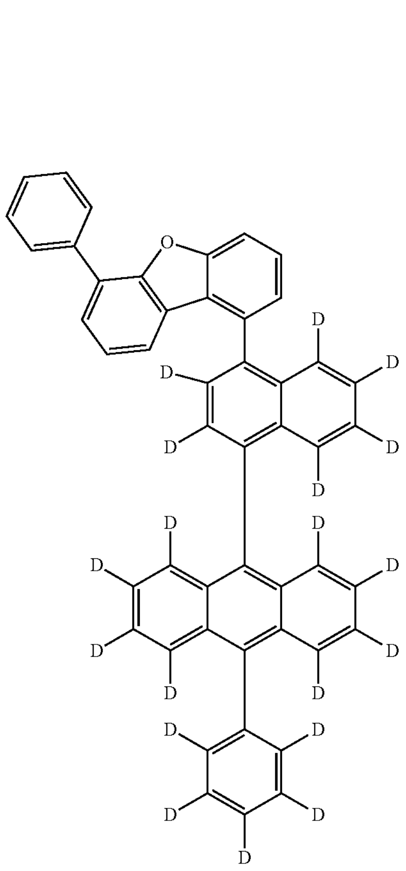
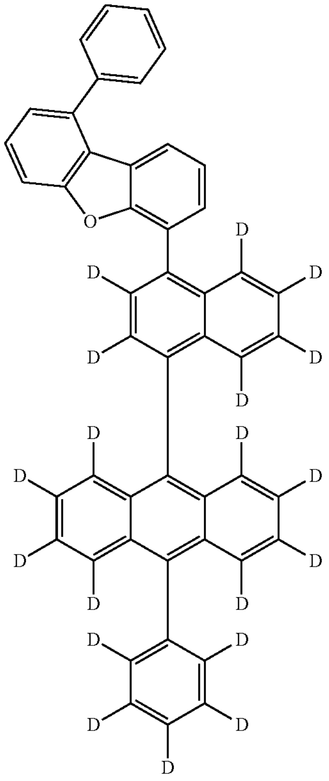

-continued
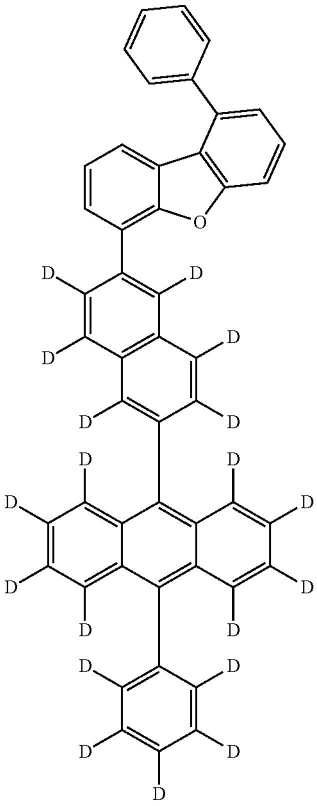
-continued
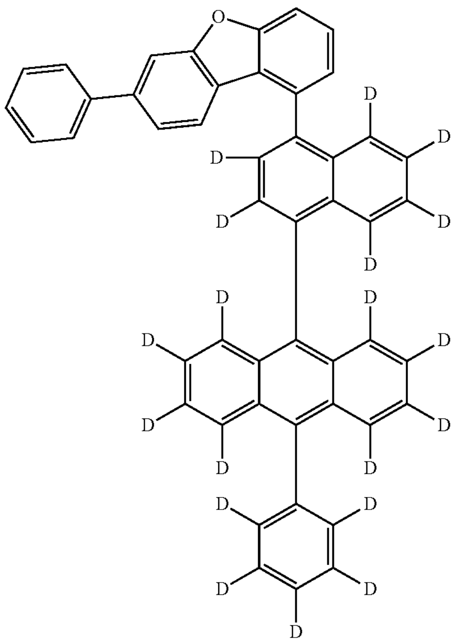
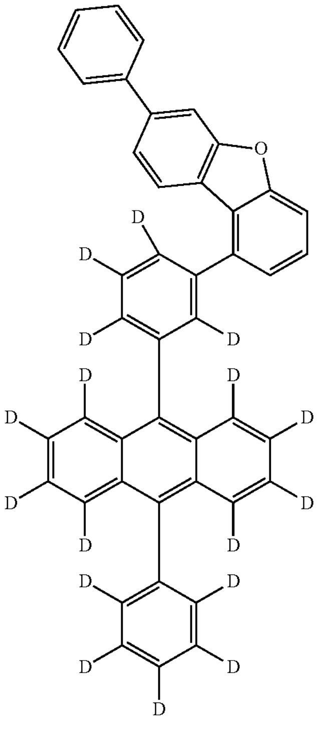
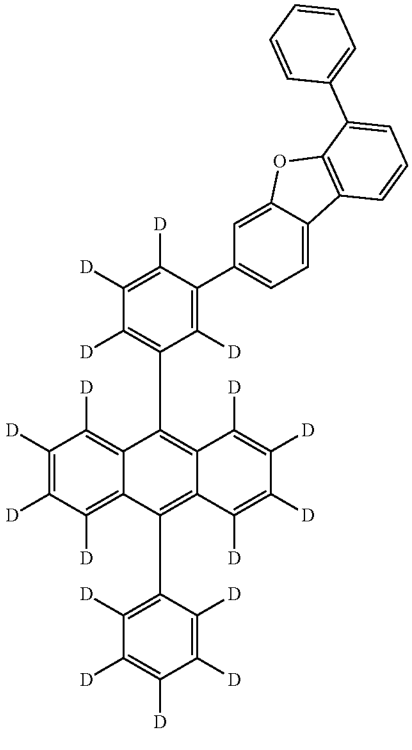

-continued
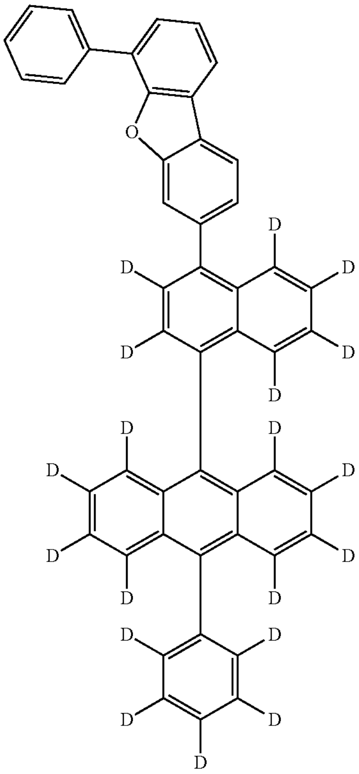
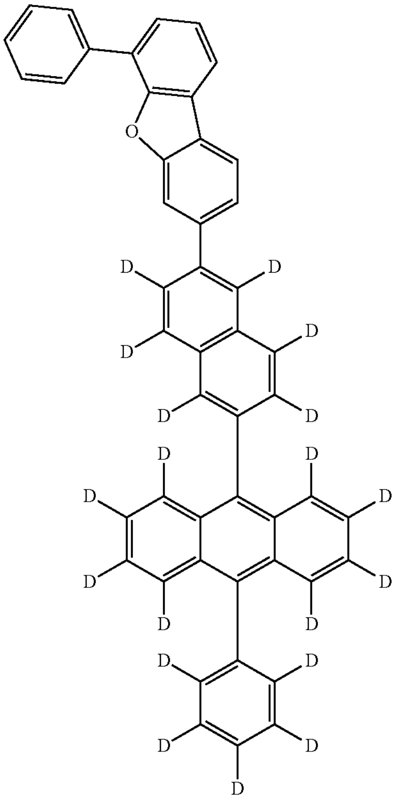
-continued
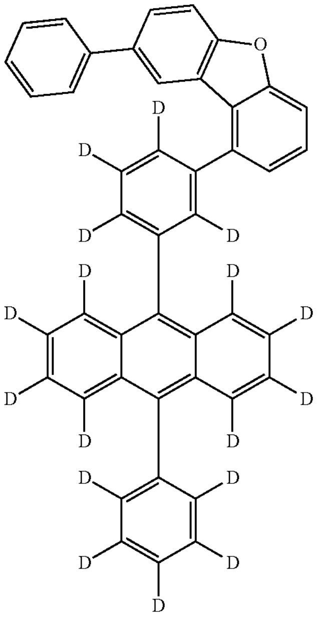
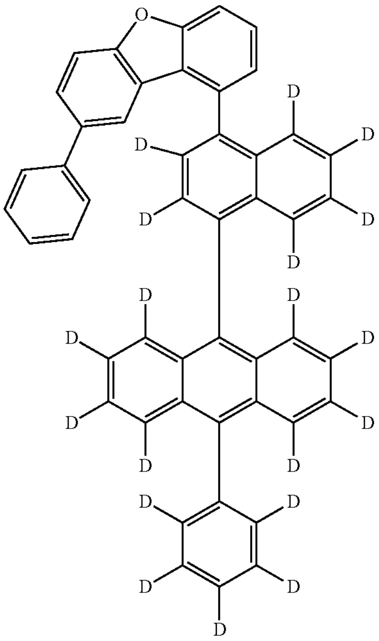

-continued
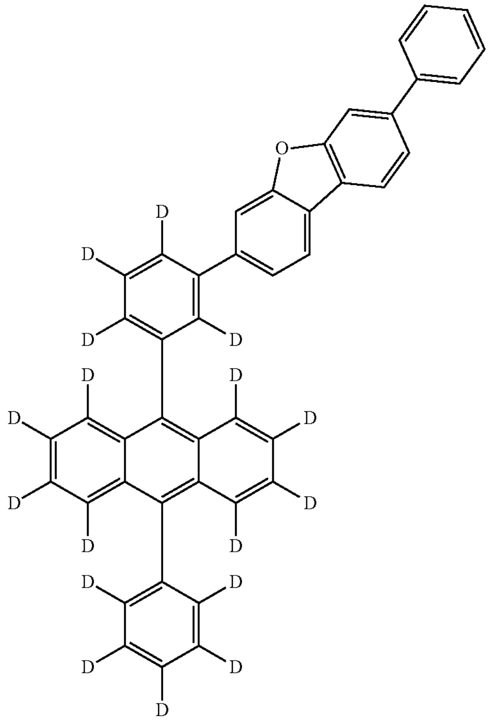
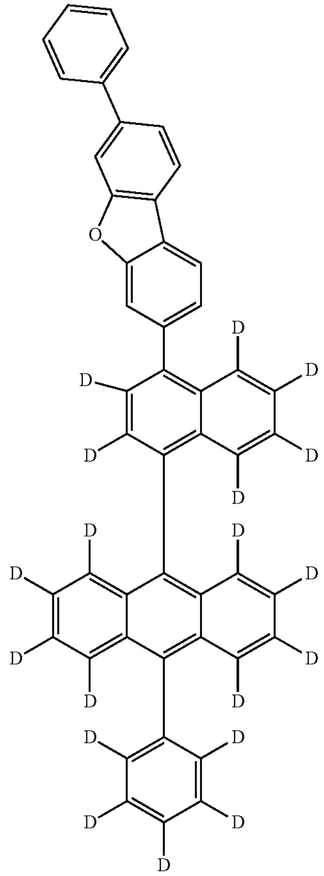
-continued
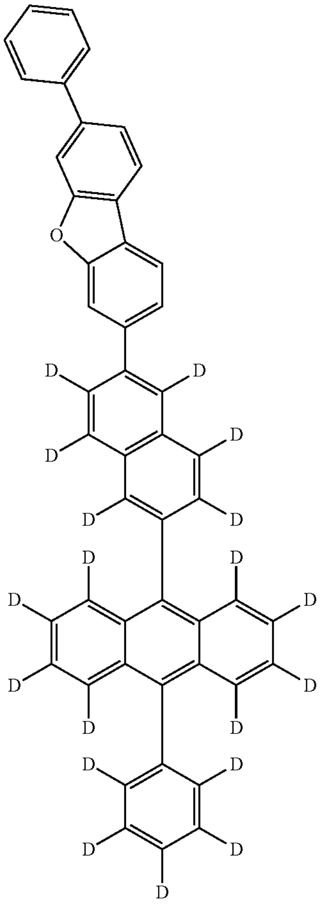
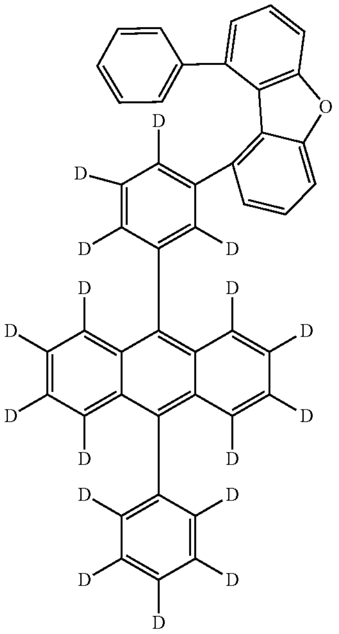

-continued
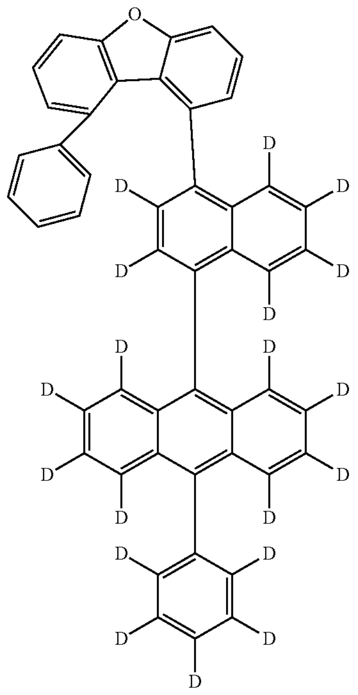
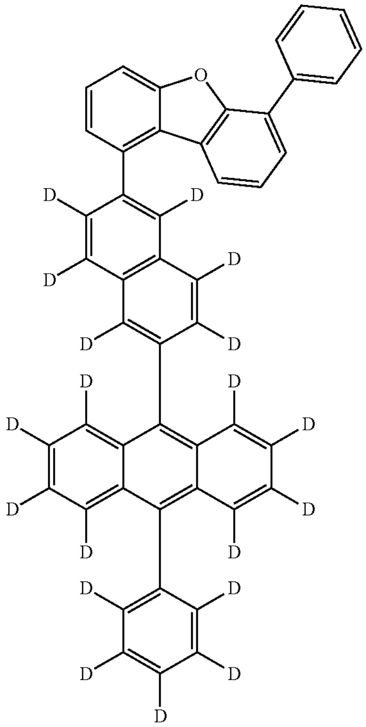
-continued
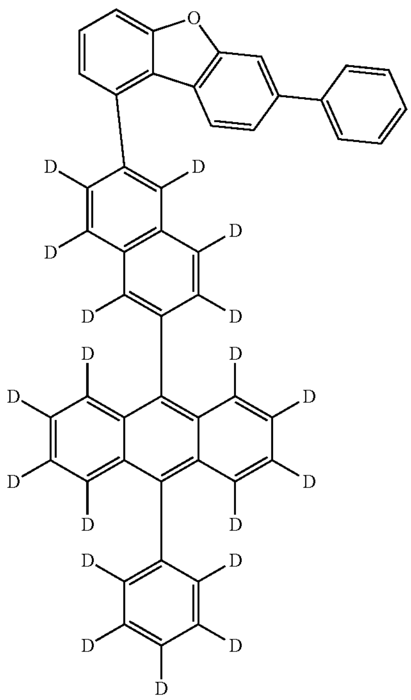
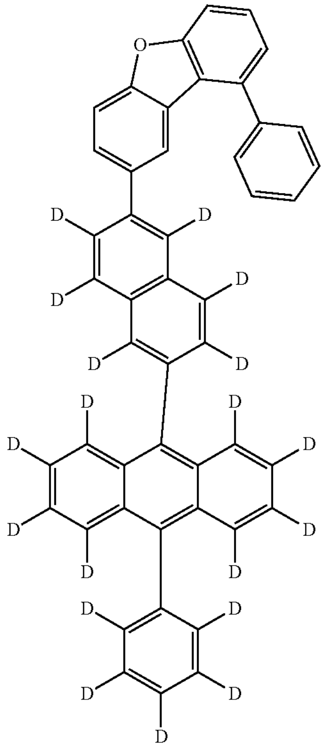

-continued
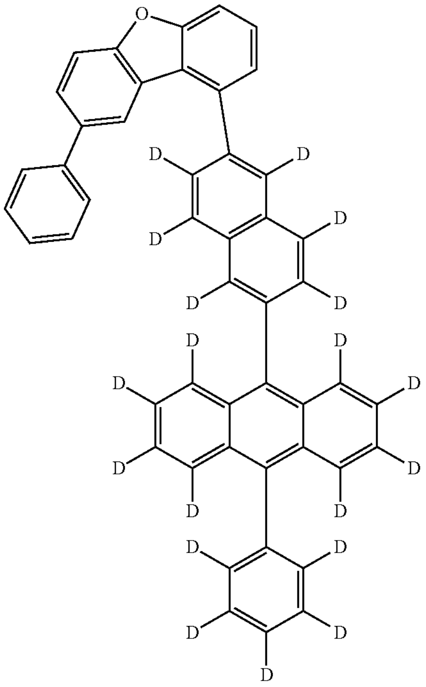
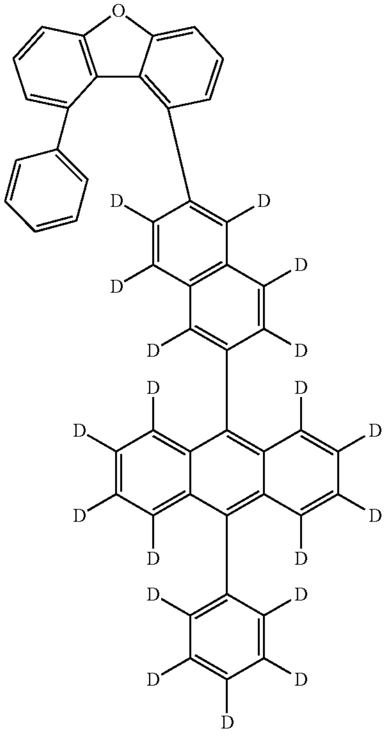
-continued
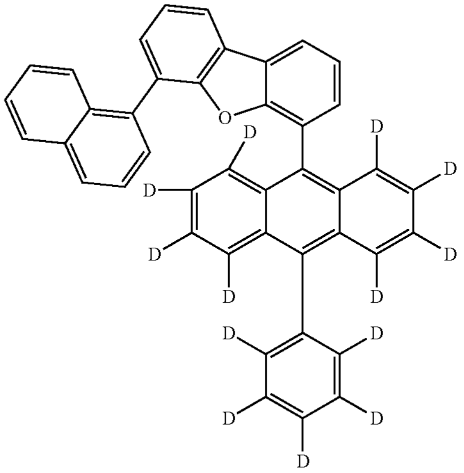
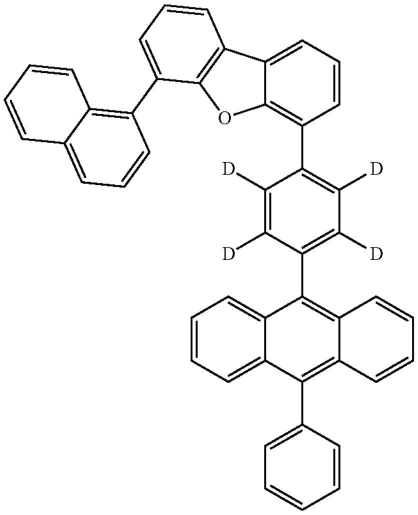
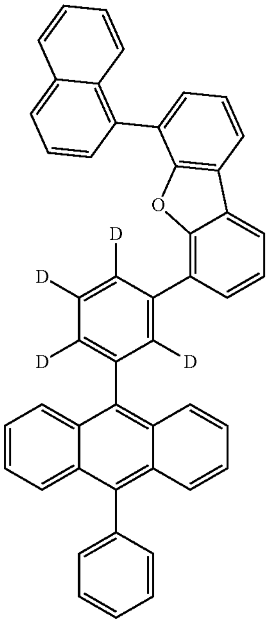

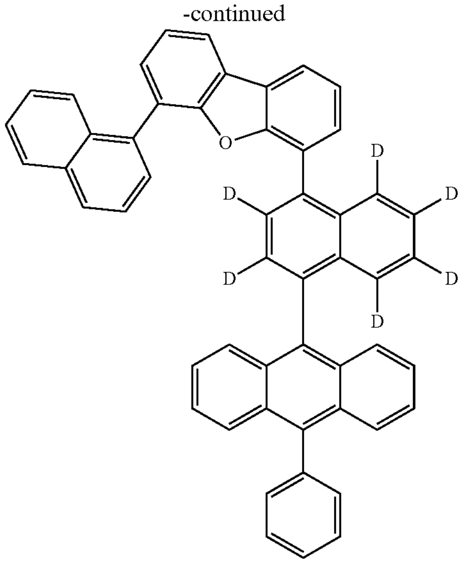
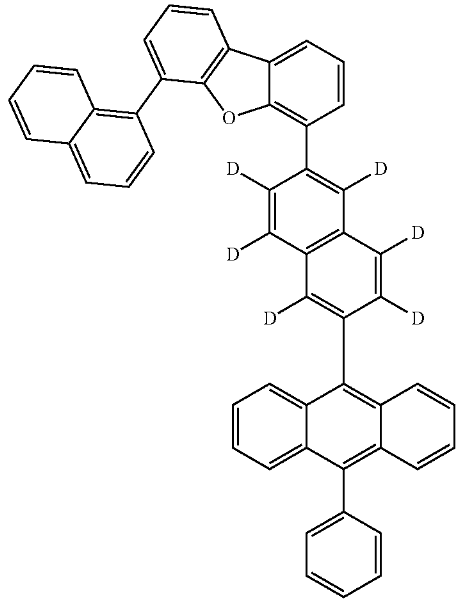
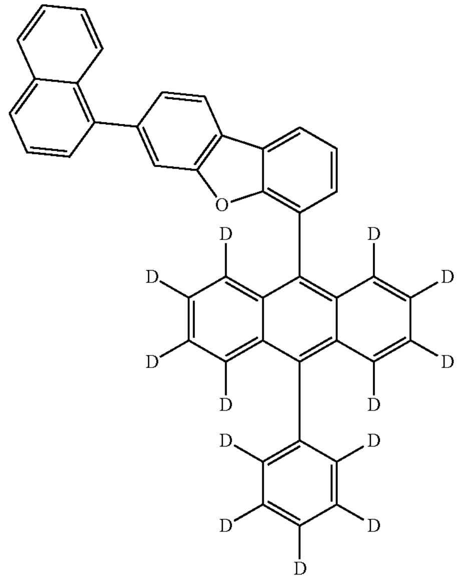
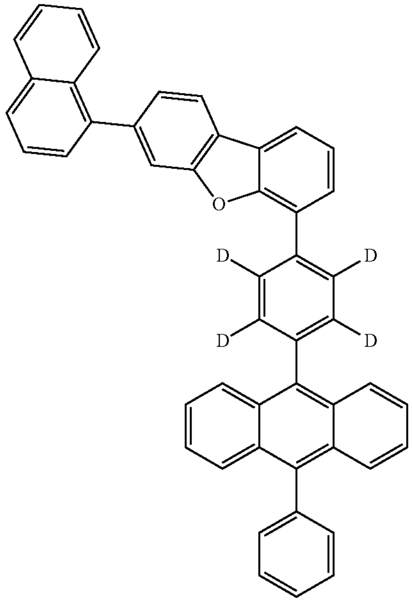
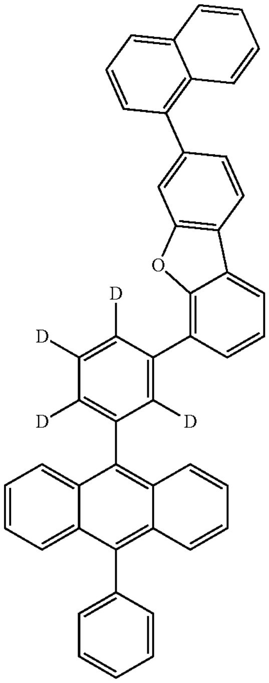

-continued
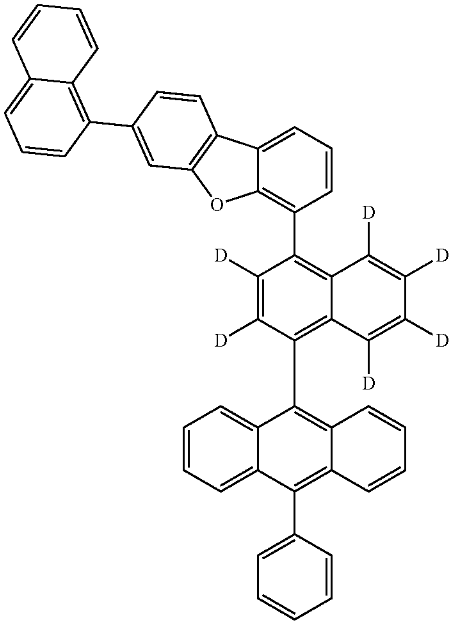
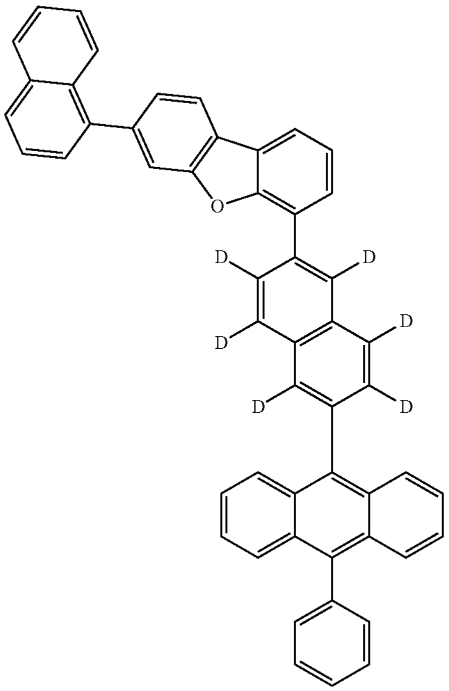 [SMILES: [2H]c1c(-c2cccc3c2oc2cc(-c4cccc5ccccc45)ccc23)c([2H])c2c([2H])c([2H])c(-c3c4ccccc4c(-c4ccccc4)c4ccccc34)c([2H])c2c1[2H]]
-continued
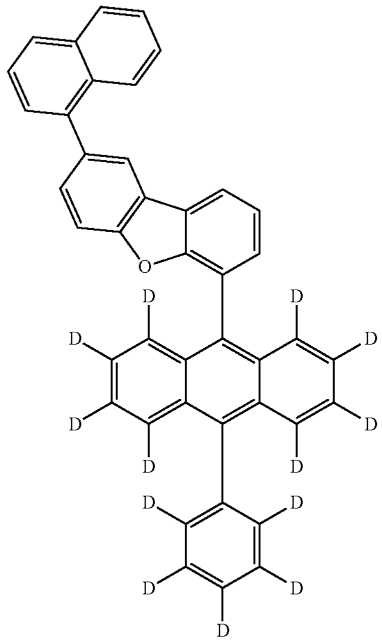
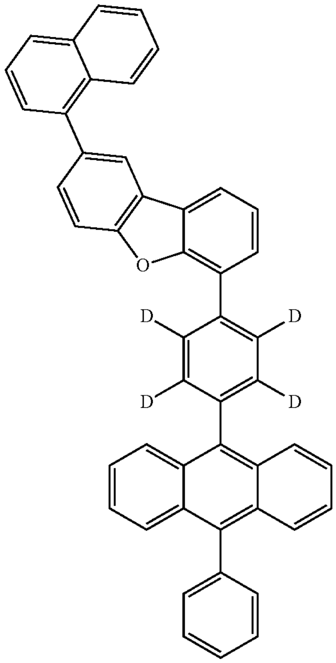

-continued
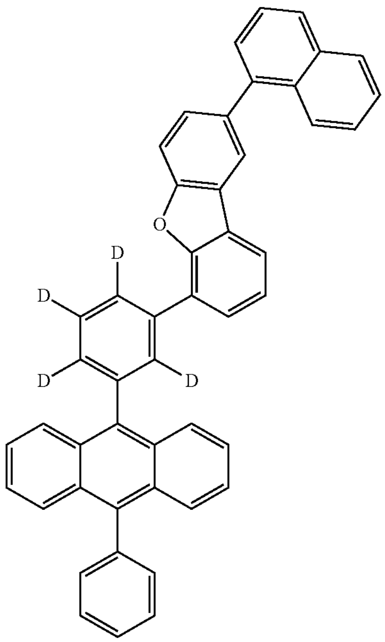
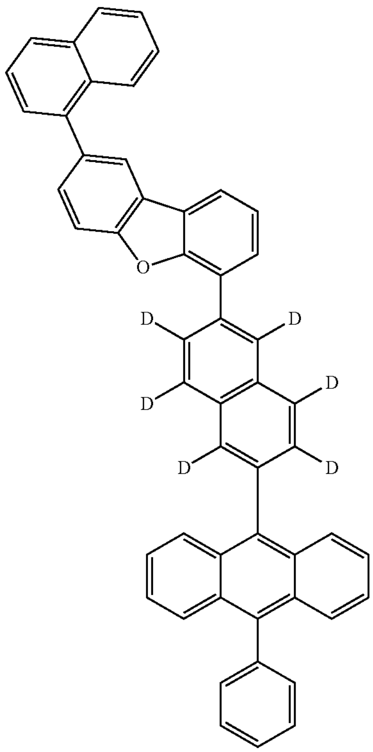
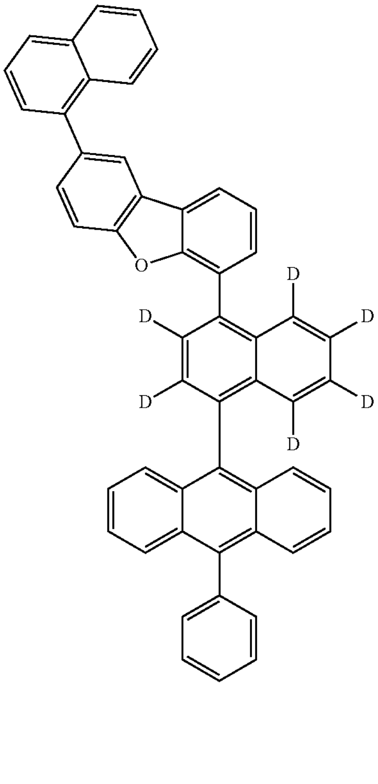
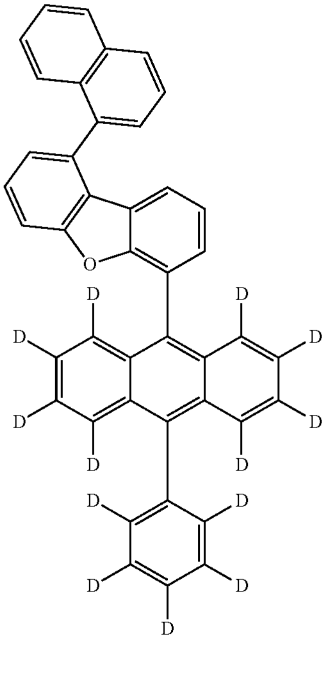

-continued
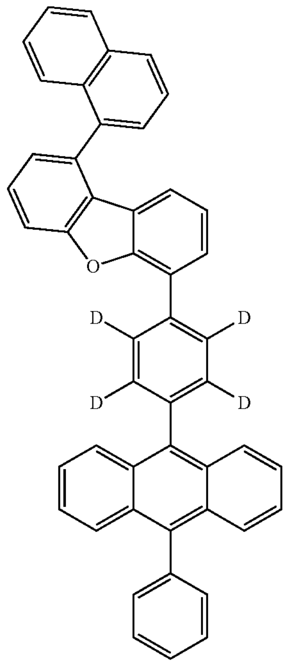
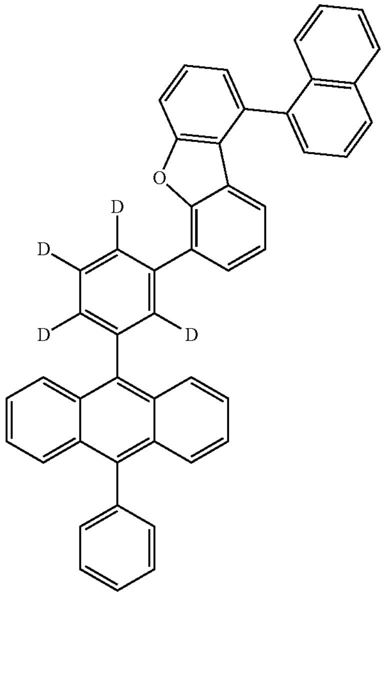
-continued
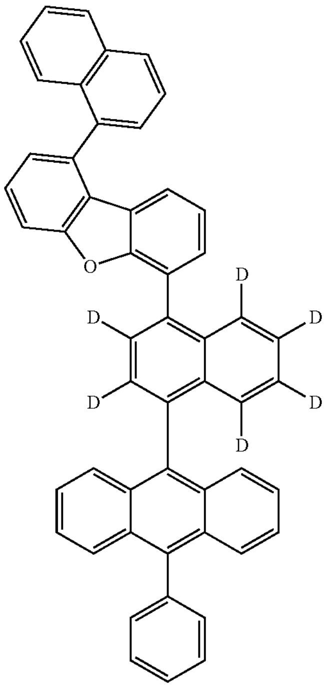
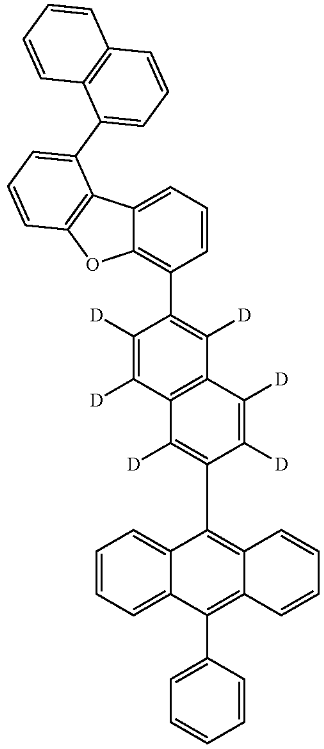

-continued
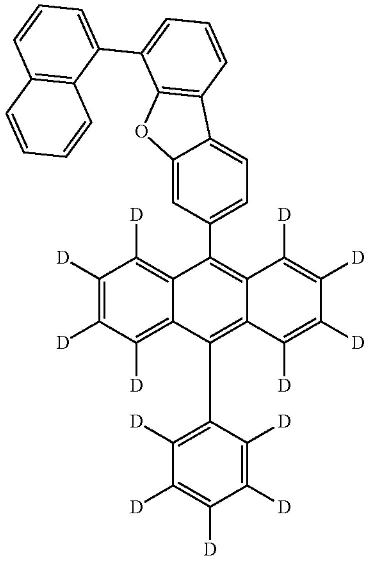
-continued
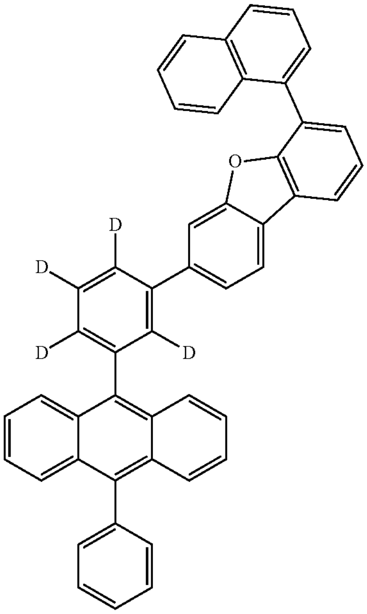
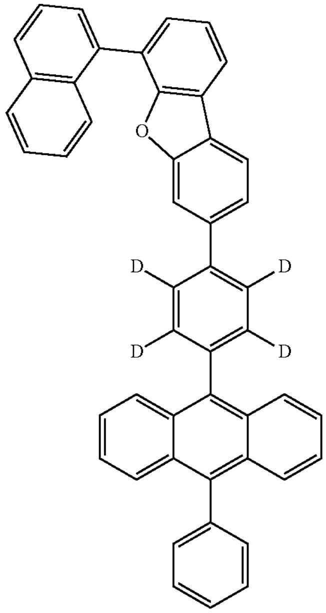
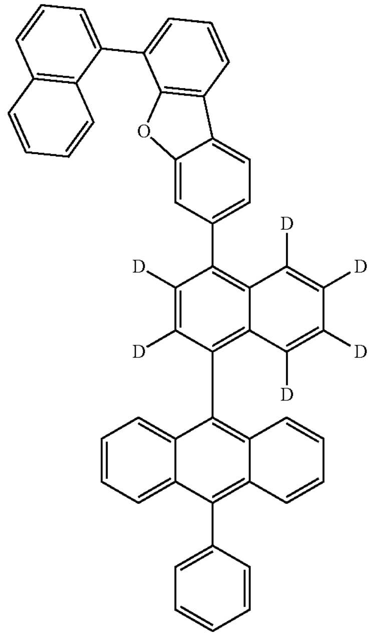

-continued
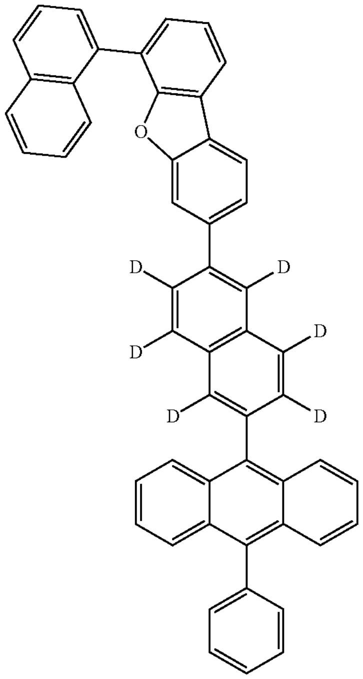
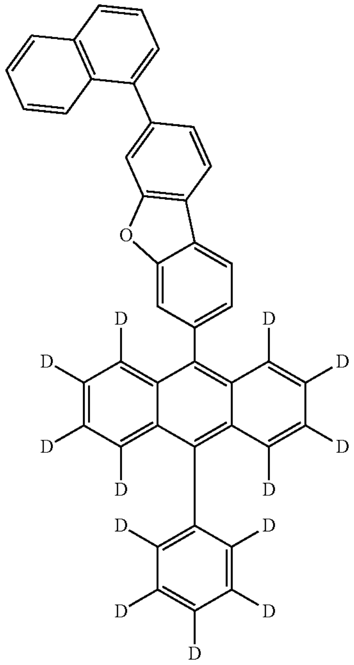
-continued
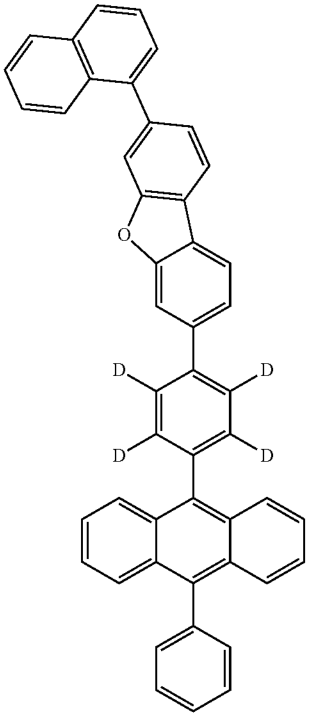
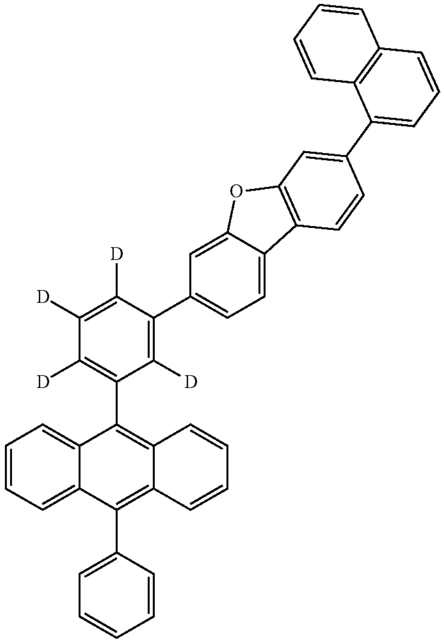

-continued
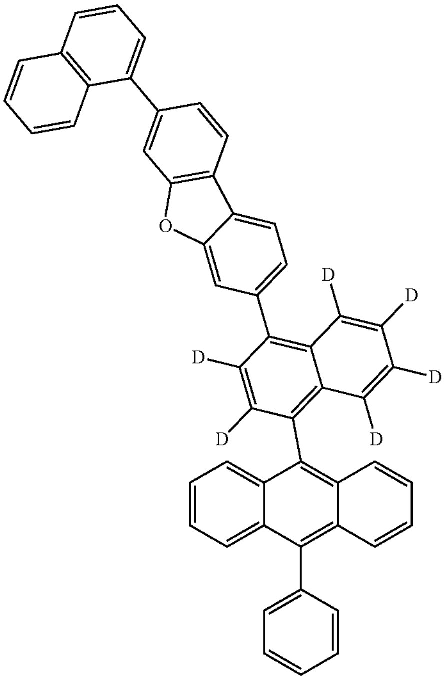
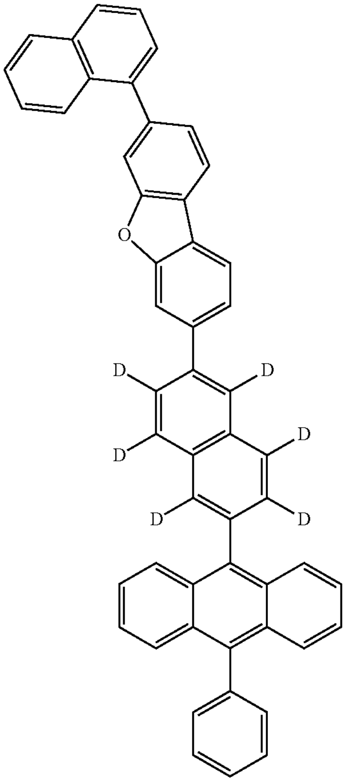
-continued
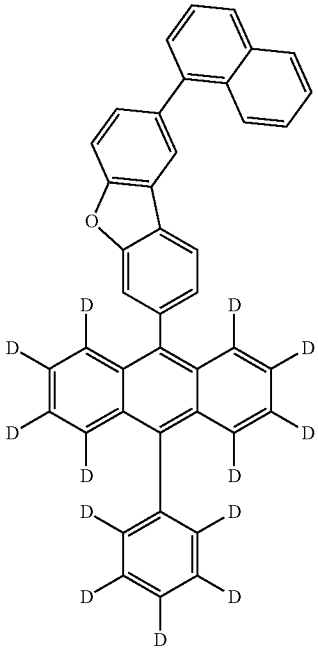
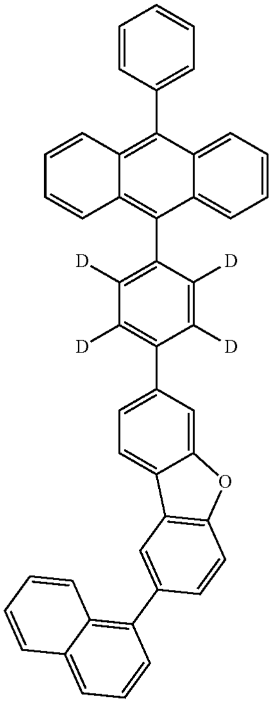

-continued
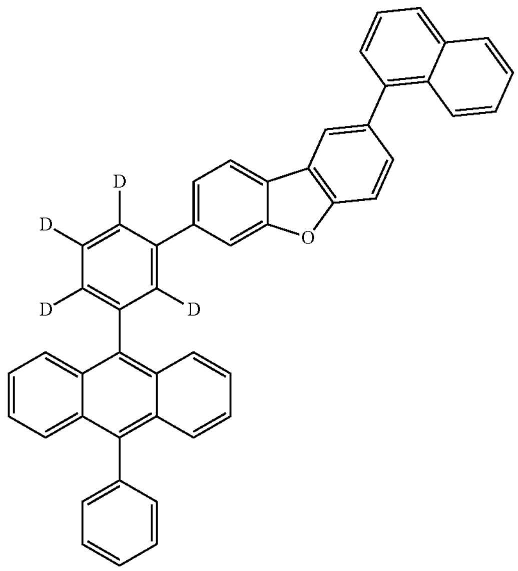
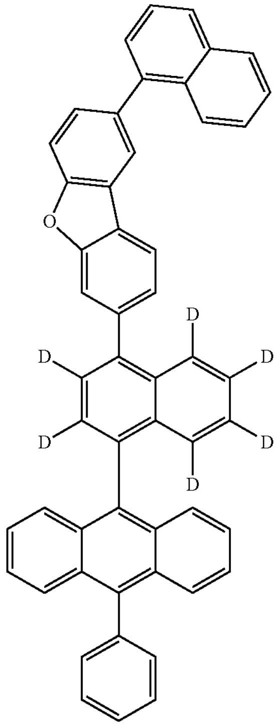
-continued
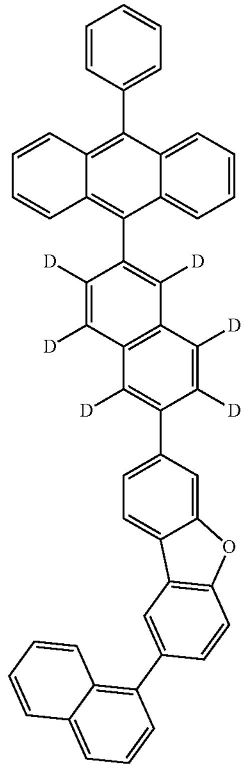
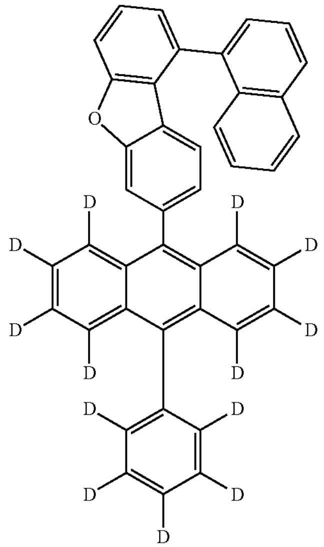

-continued
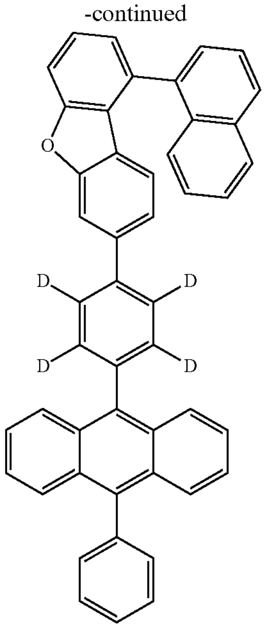
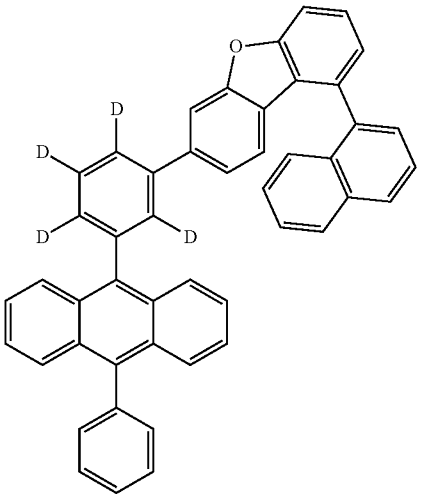
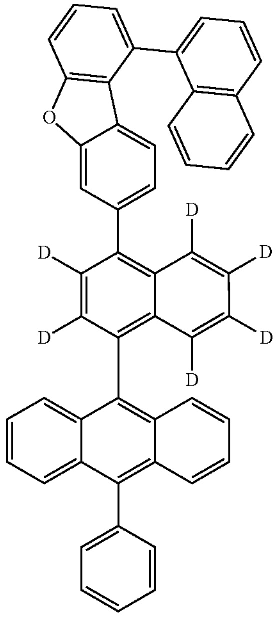
-continued
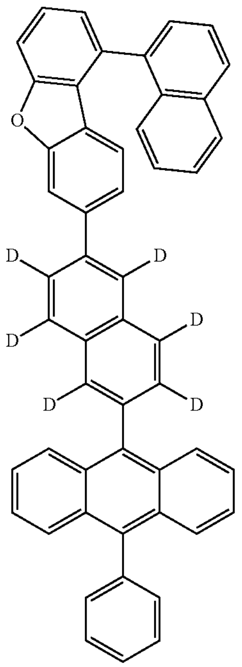
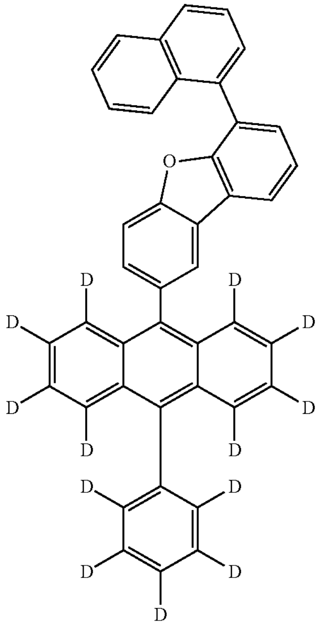

-continued
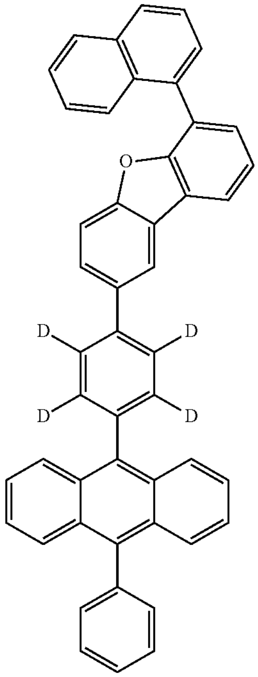
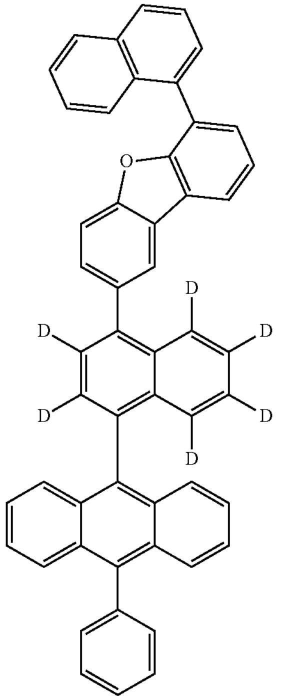
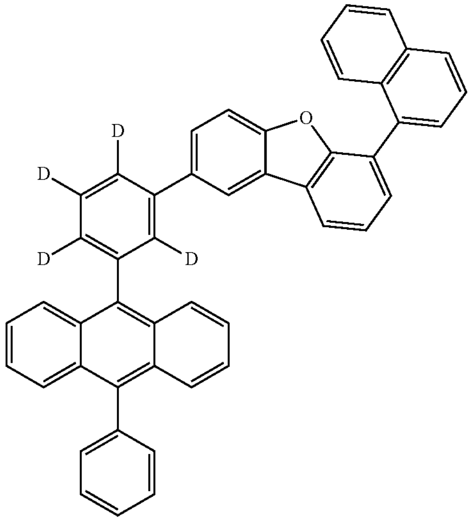
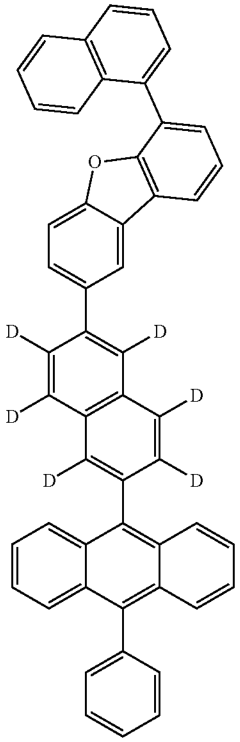

-continued
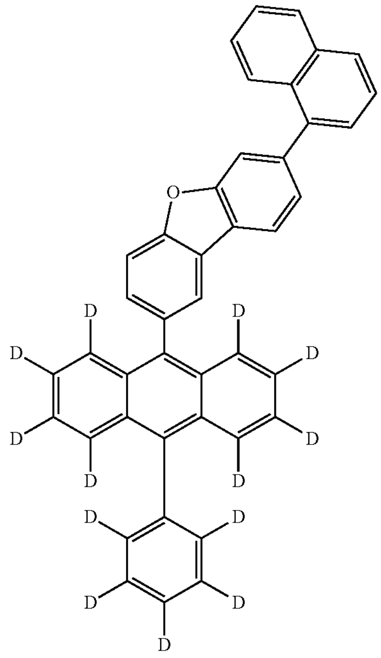
-continued
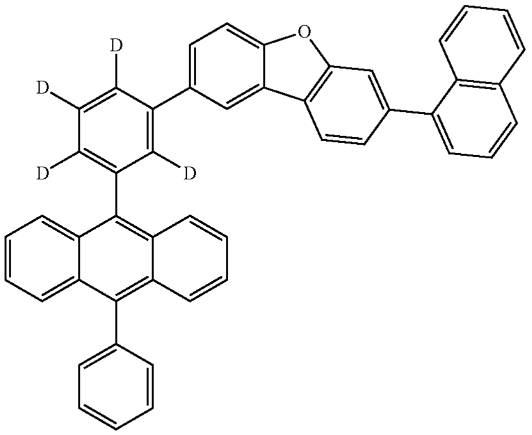
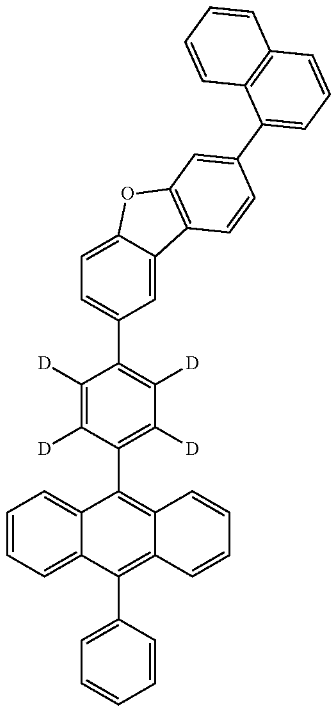
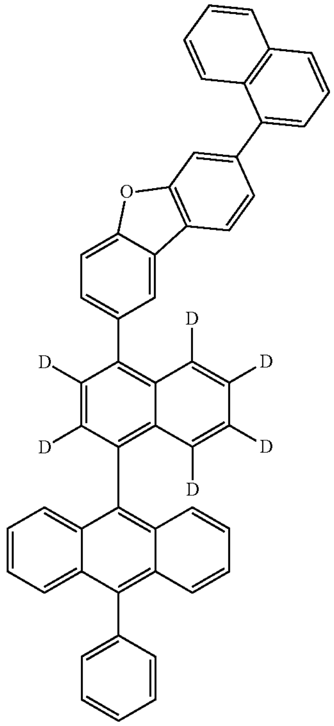

-continued
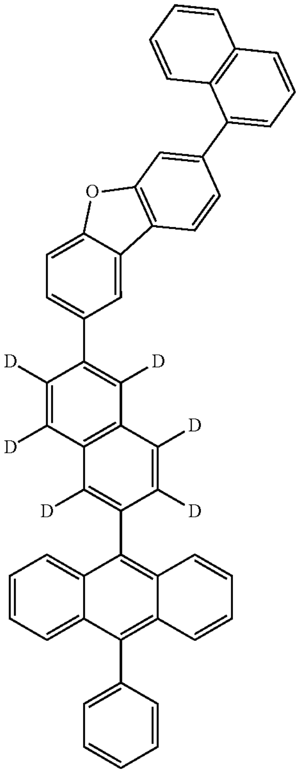
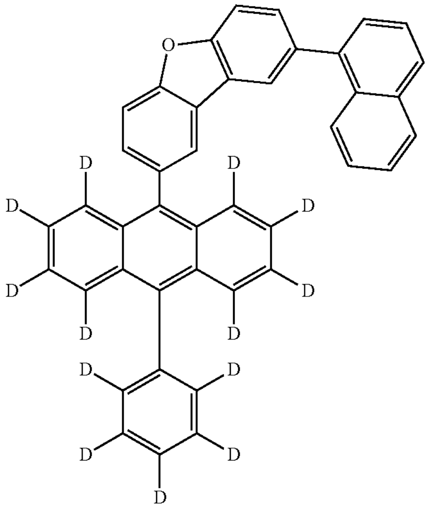
-continued
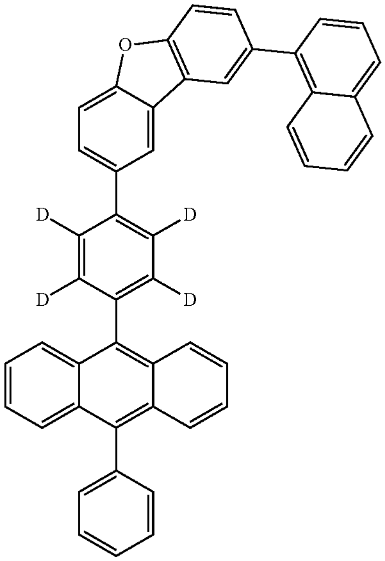
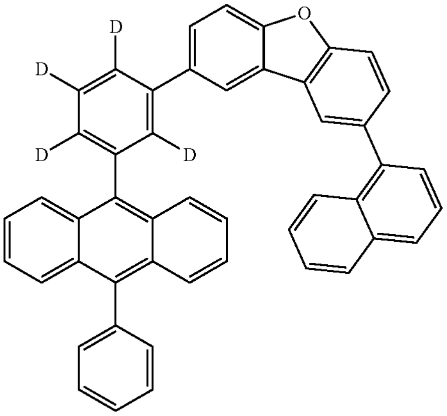
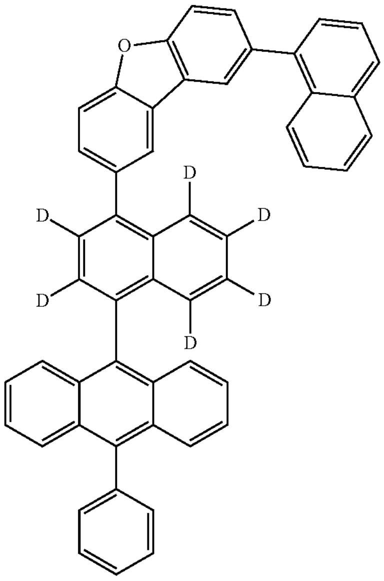

-continued
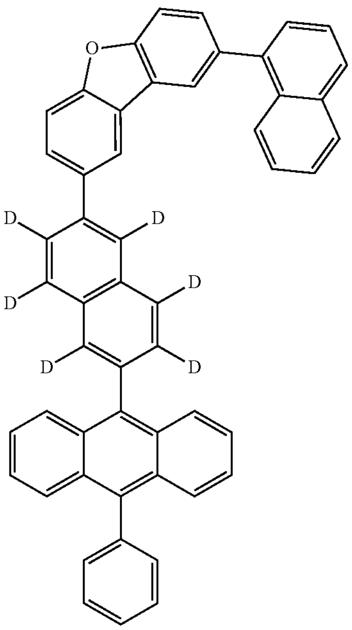
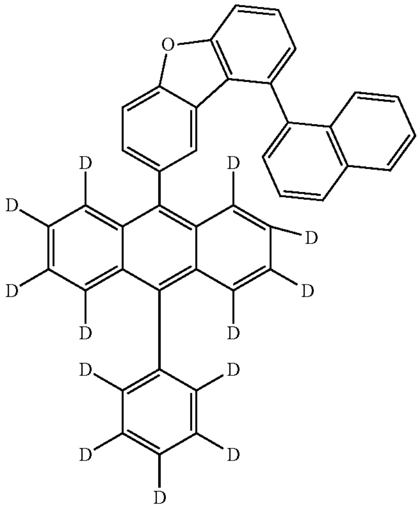
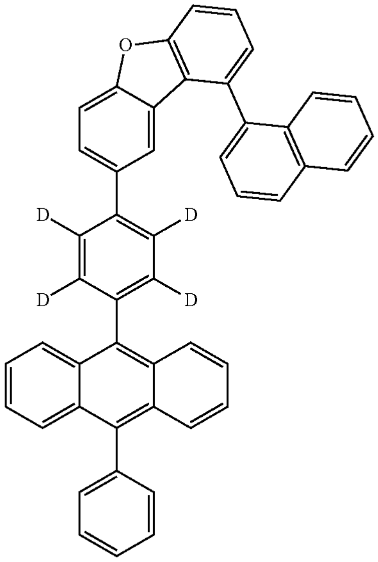
-continued
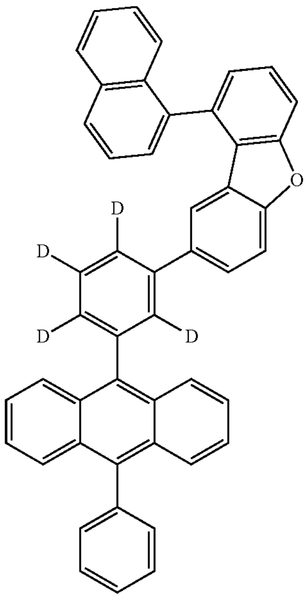
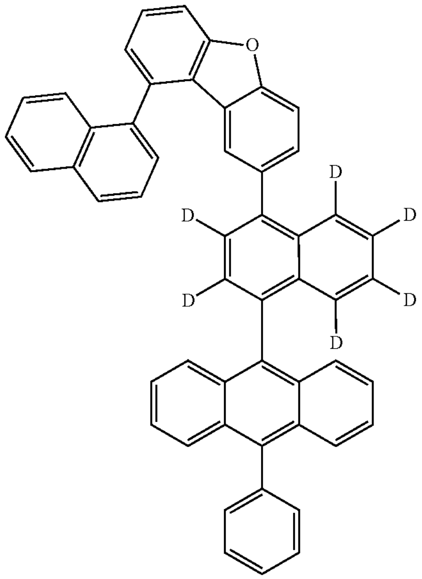

-continued
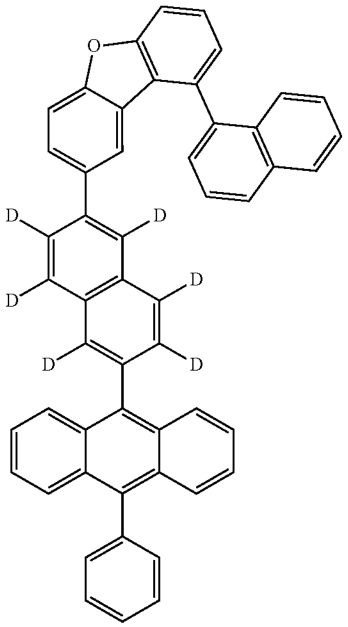
-continued
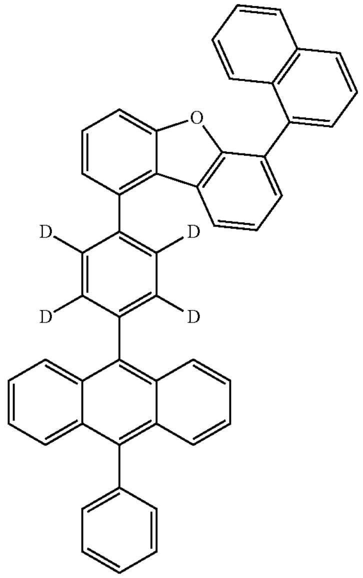
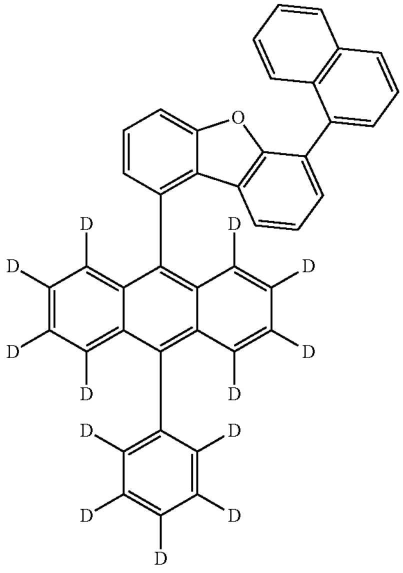
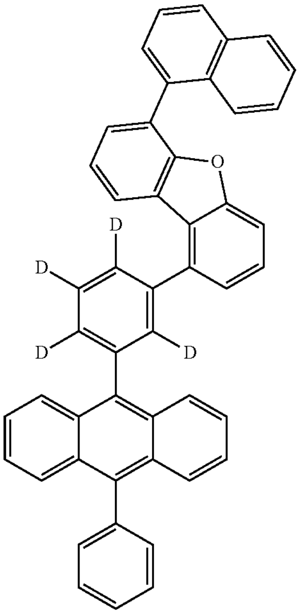

-continued
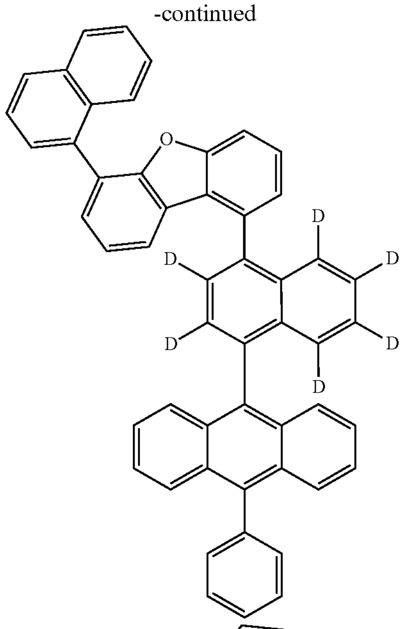
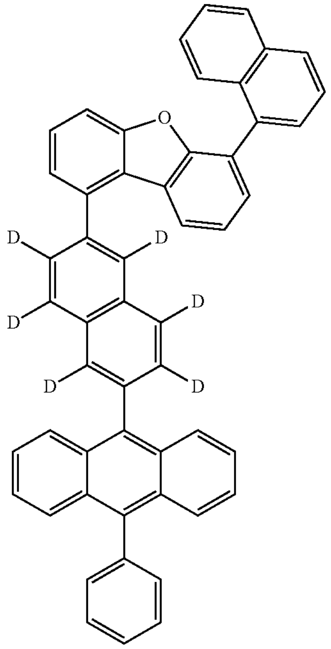
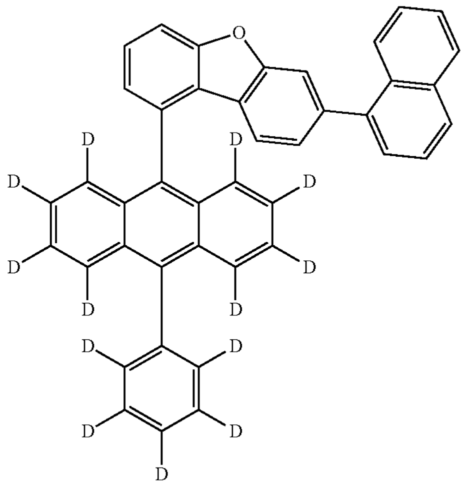
-continued
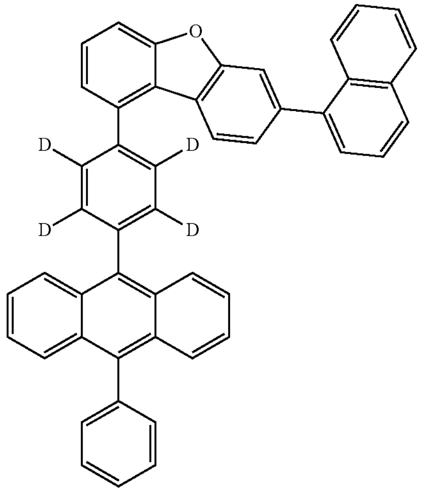
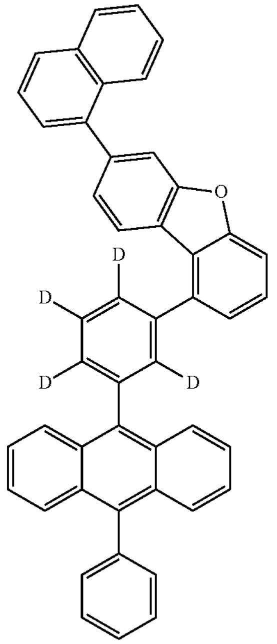
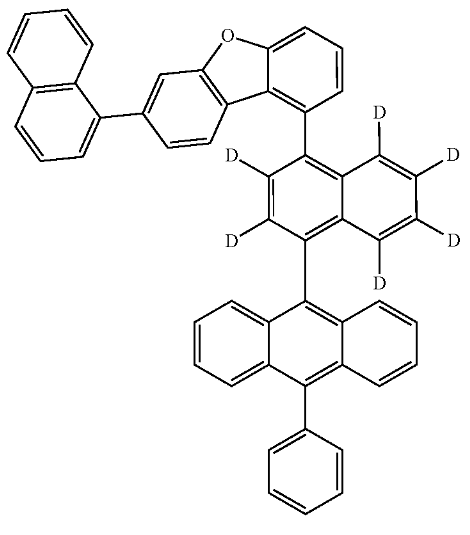

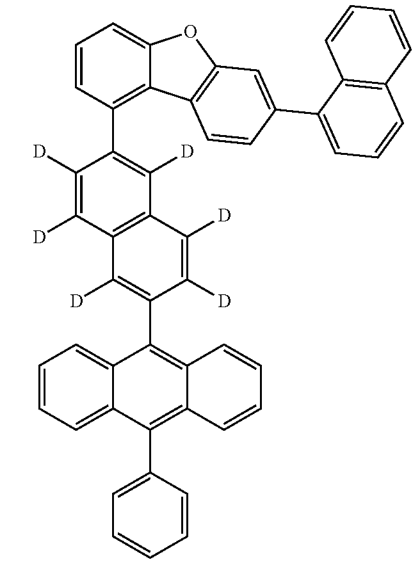
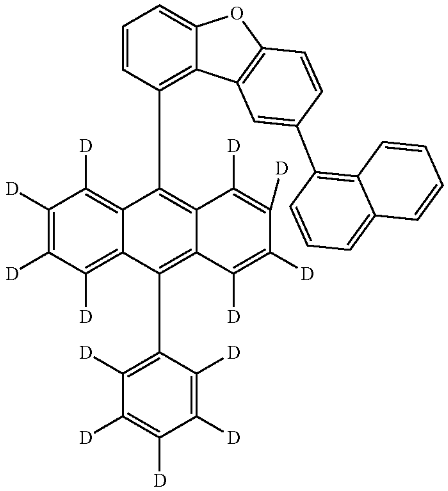
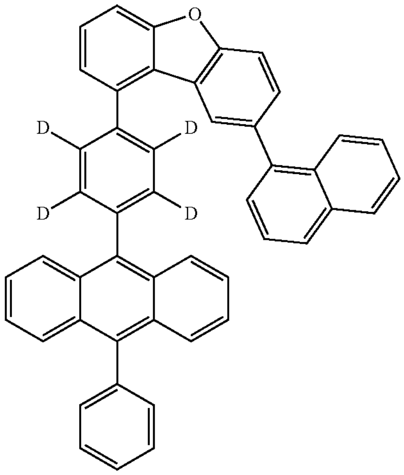
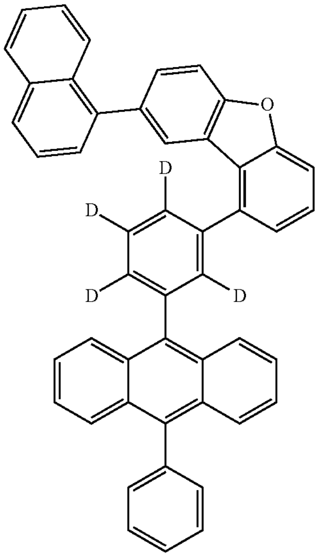
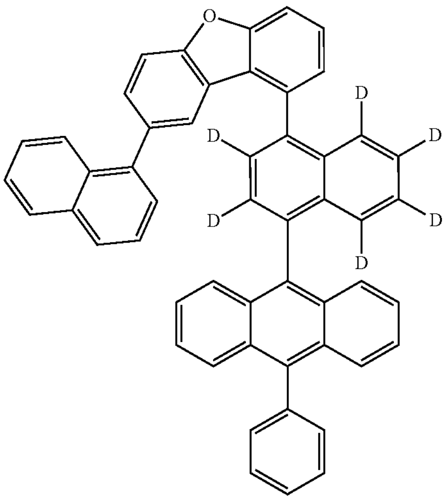
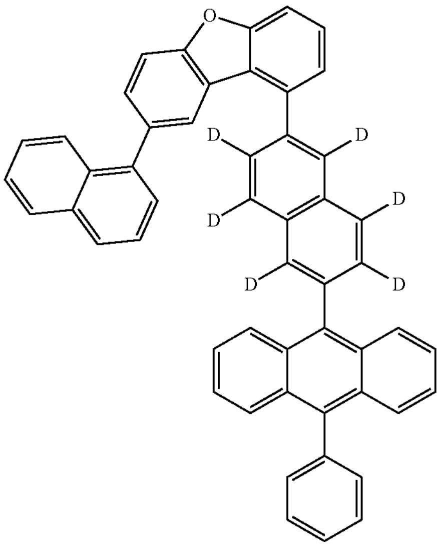

-continued
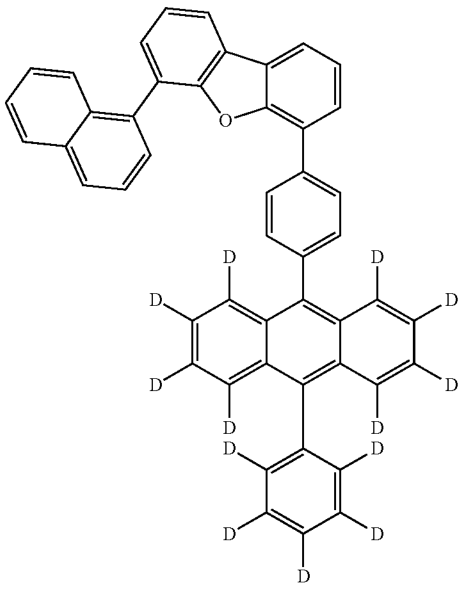
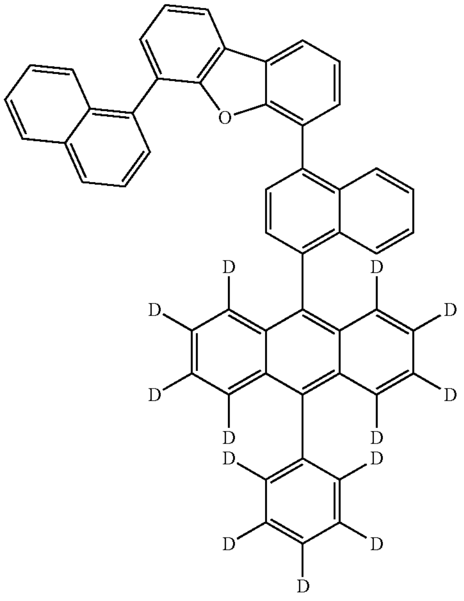
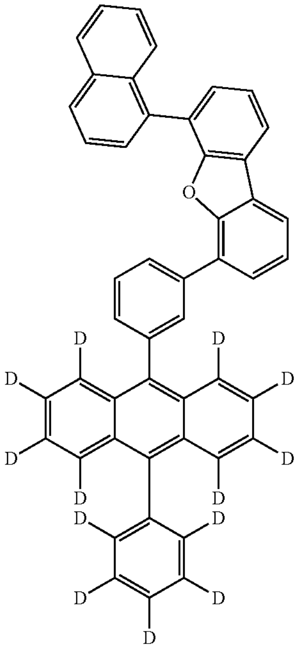
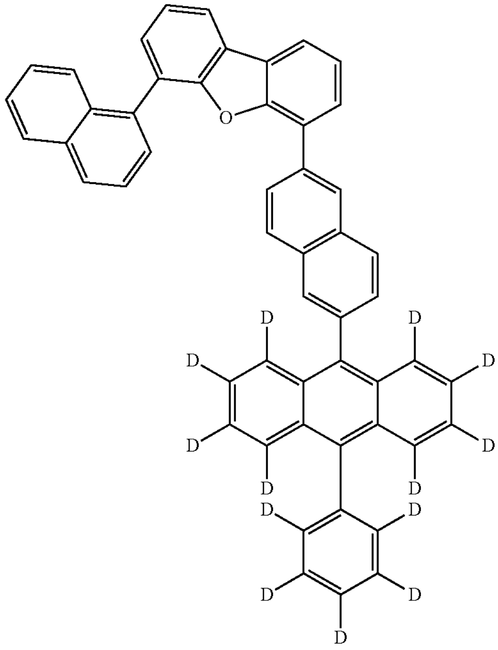

-continued
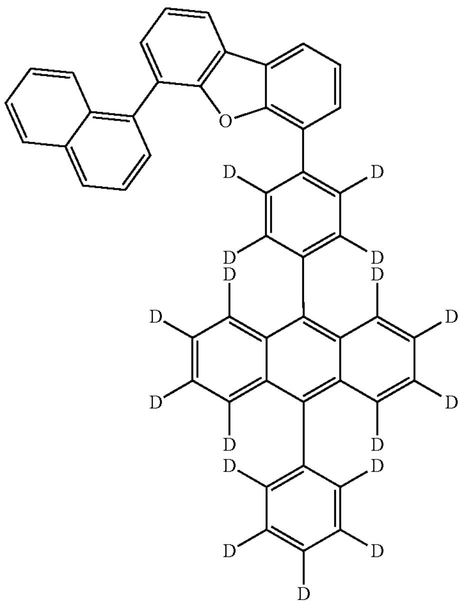
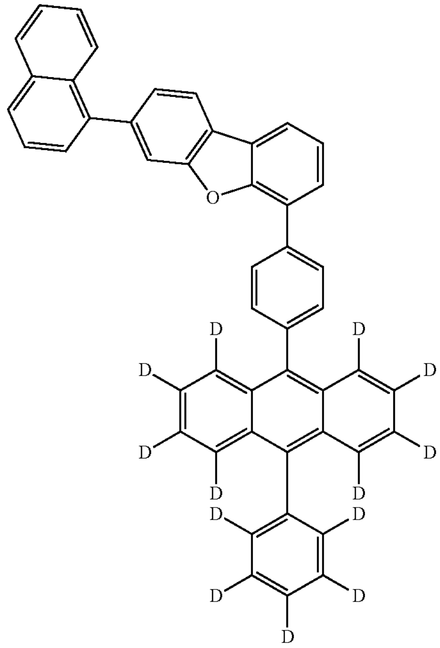
-continued
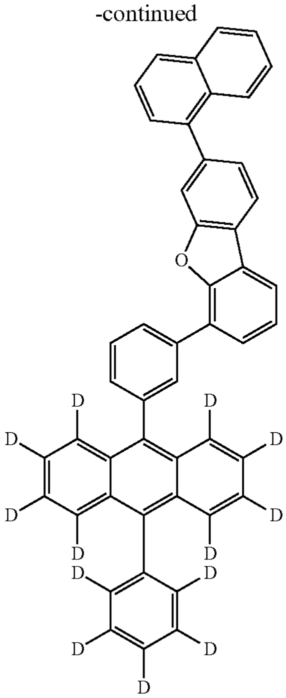
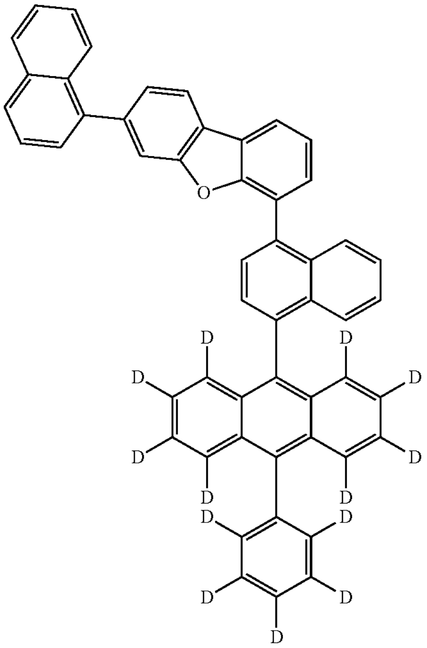

-continued
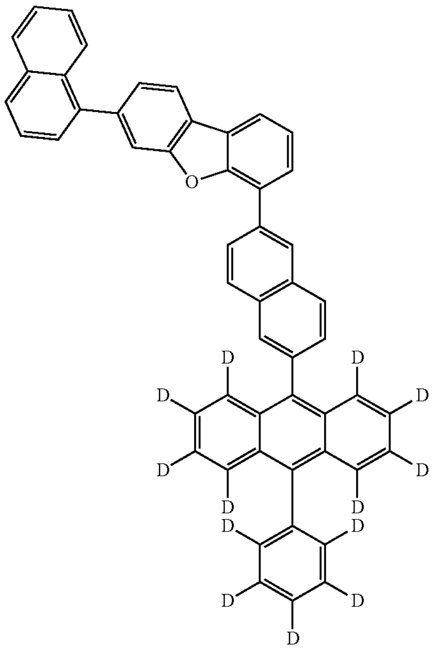
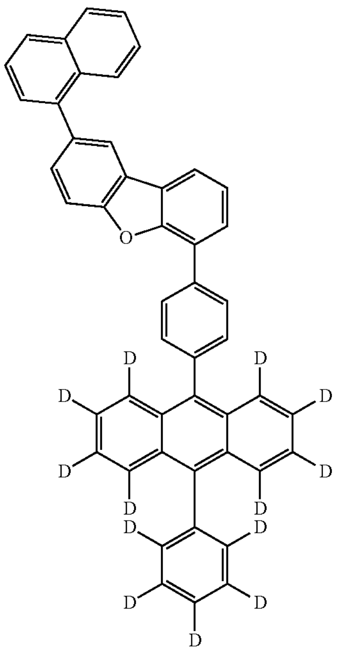
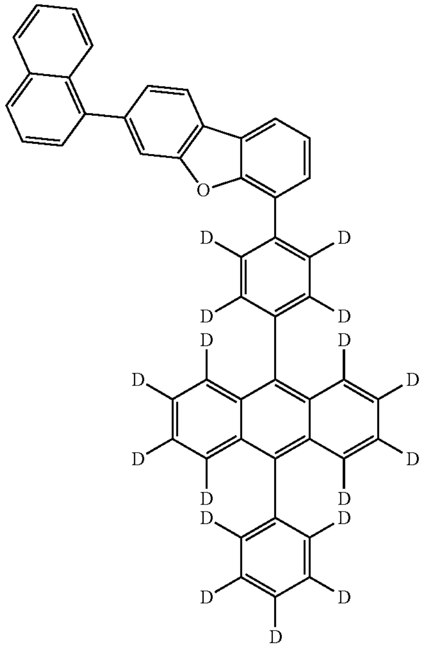
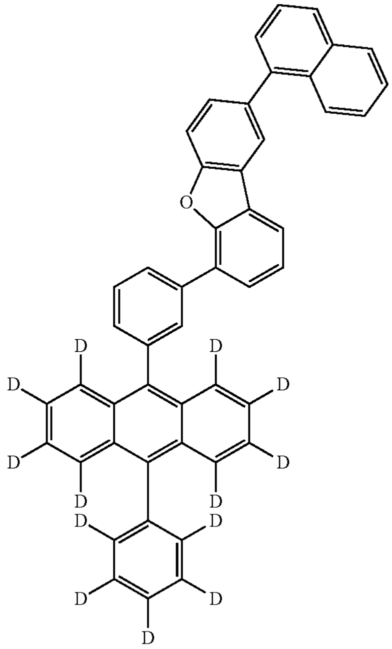

-continued
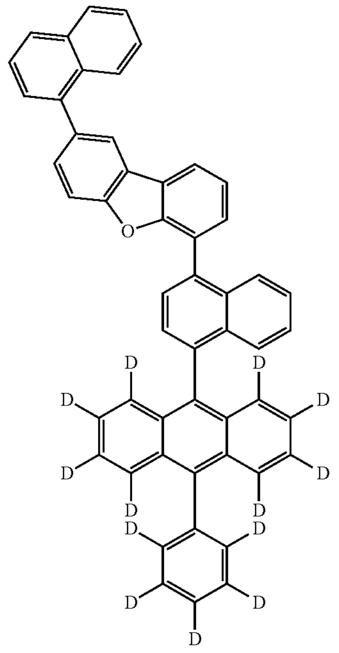
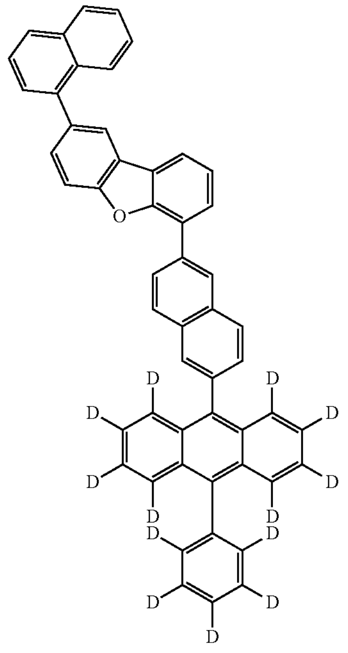
-continued
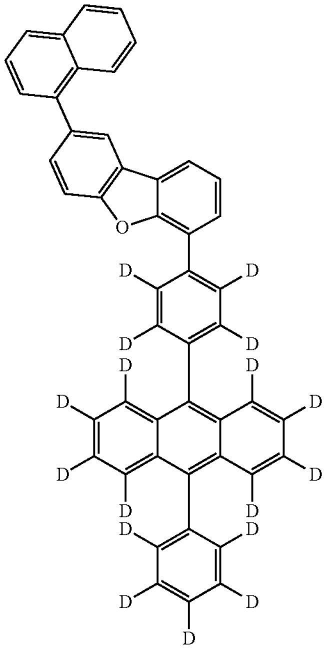
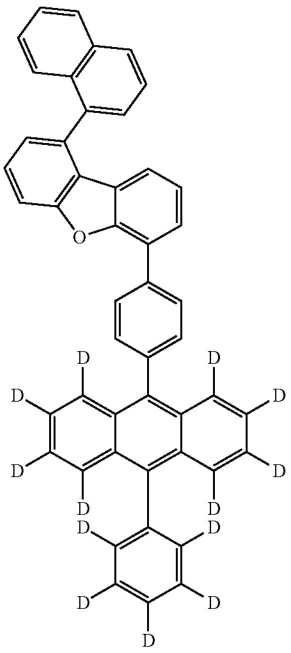

-continued
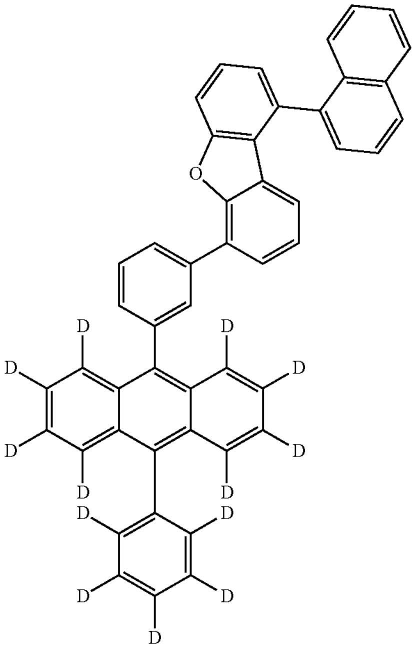
-continued
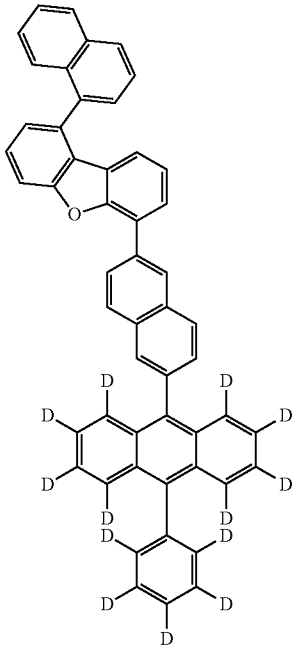
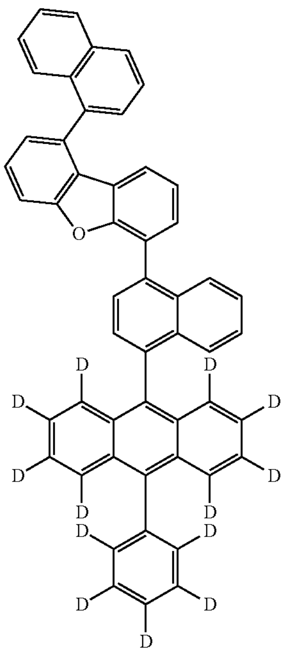
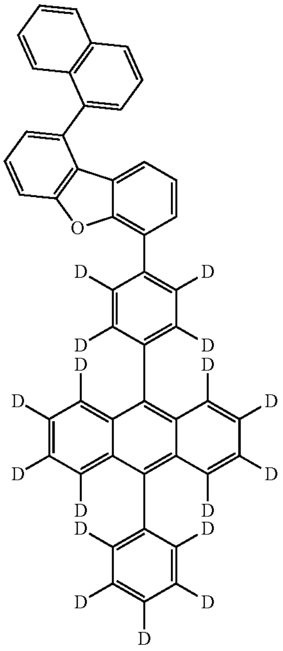

-continued
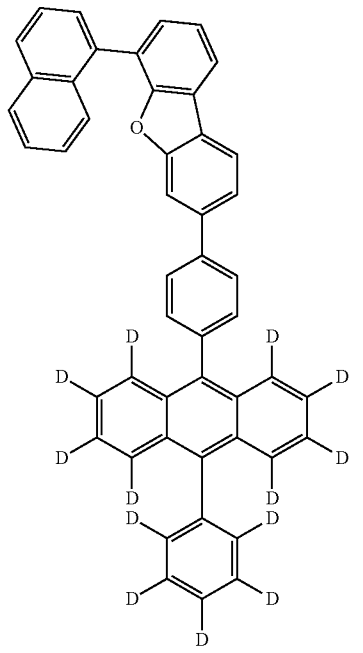
-continued
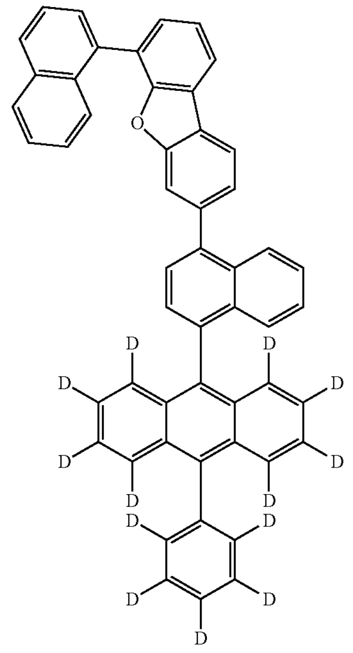
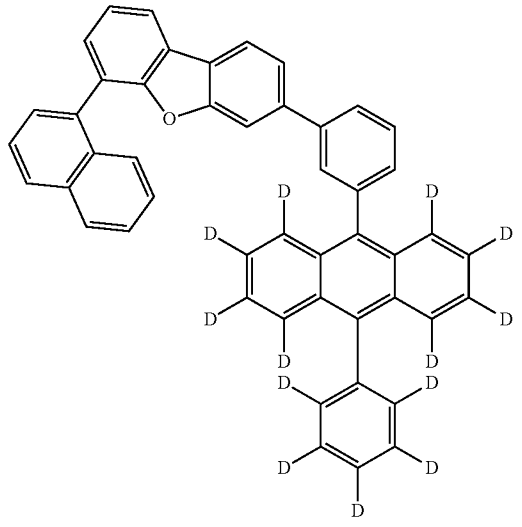
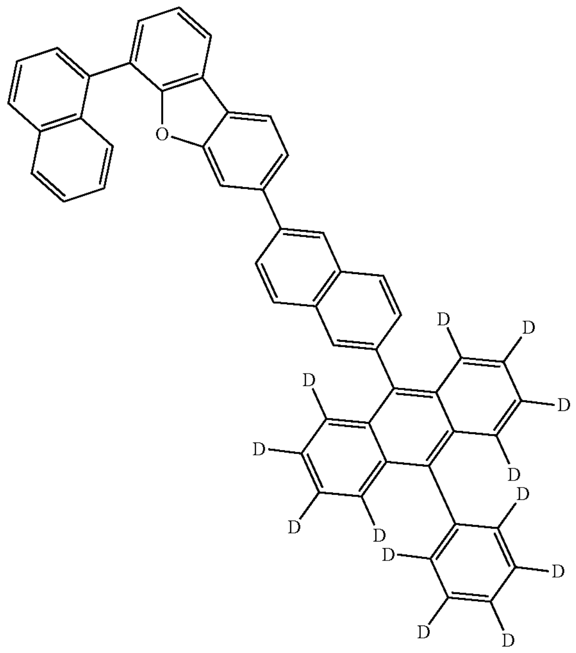

-continued
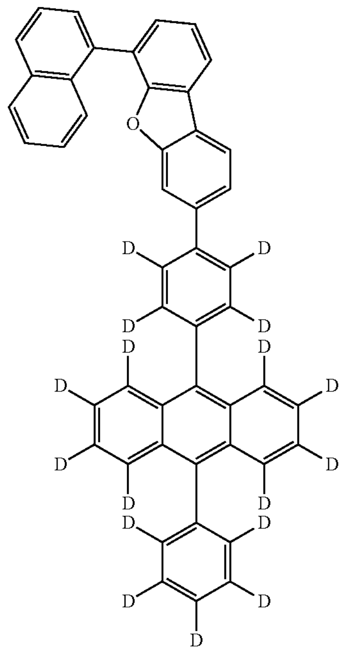
-continued
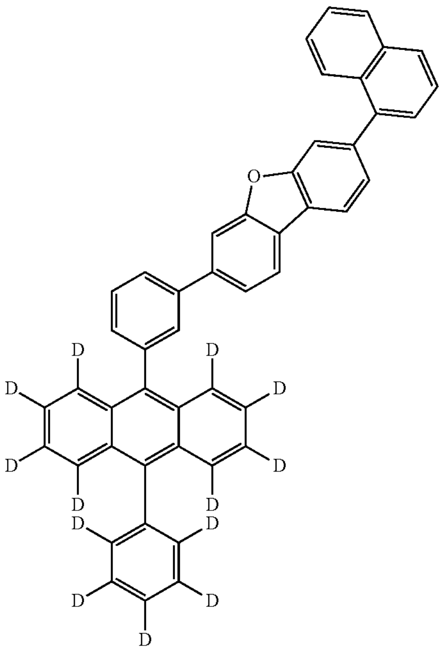
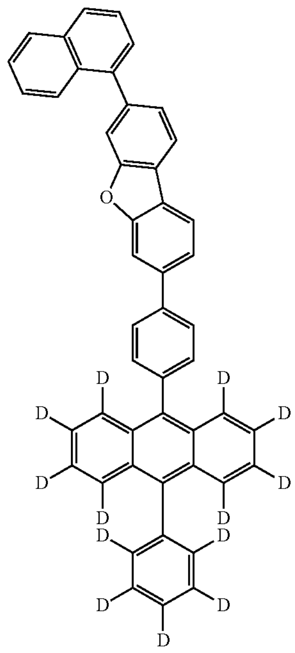
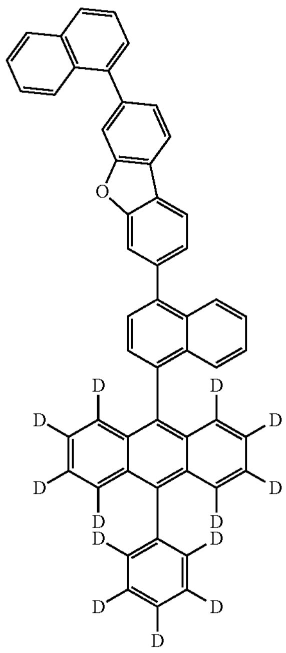

-continued
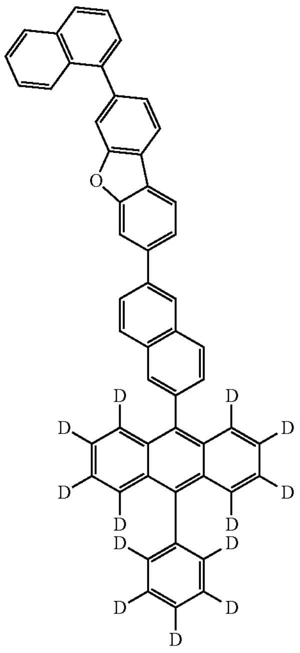
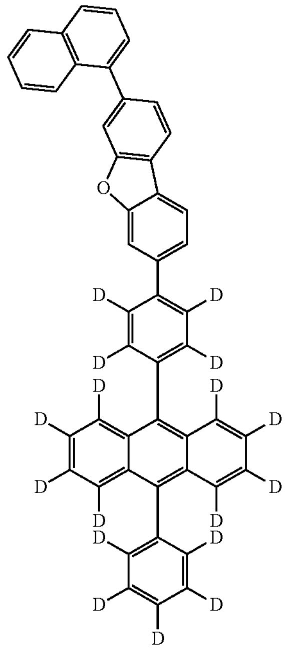
-continued
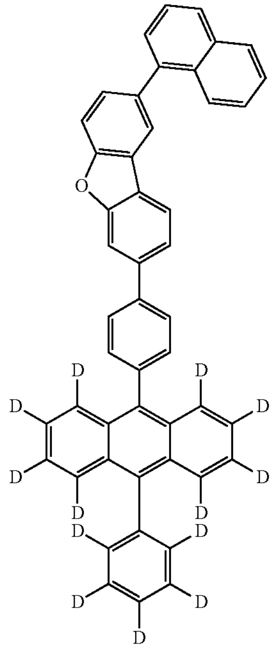
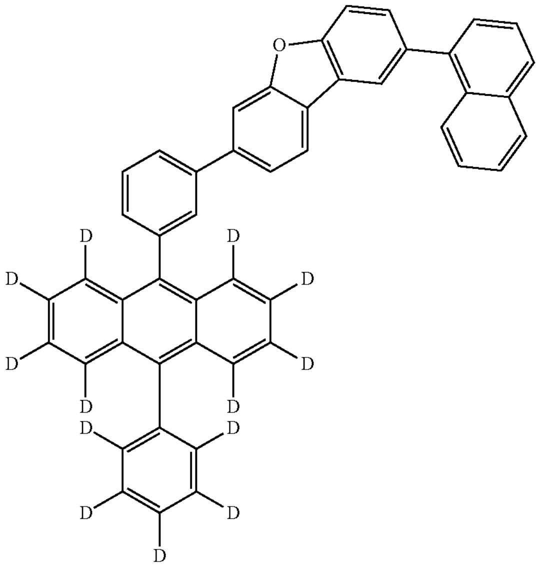

-continued
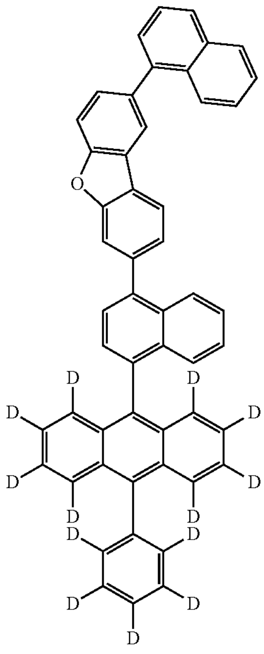
-continued
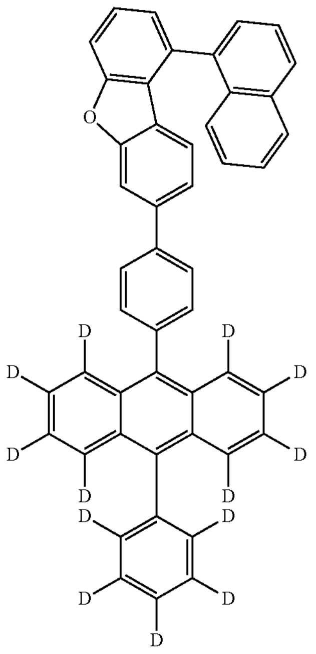
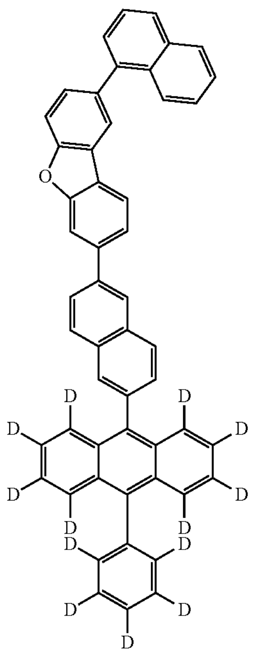
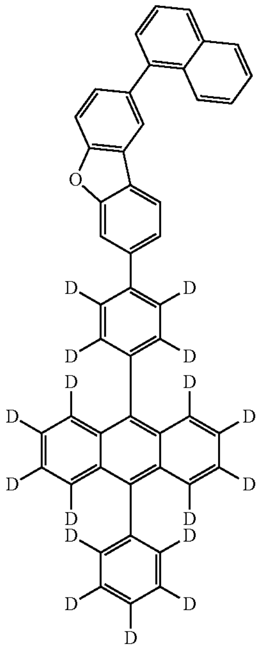
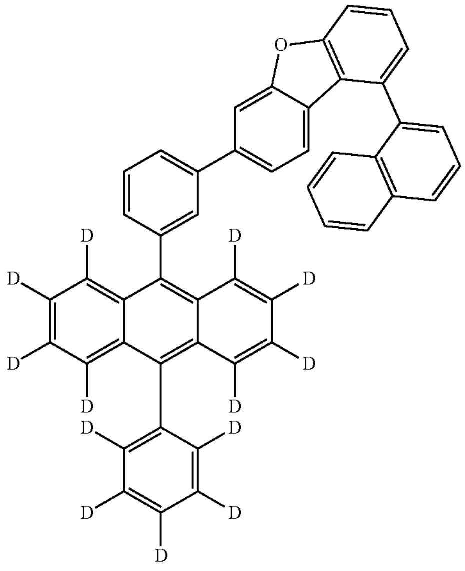

-continued
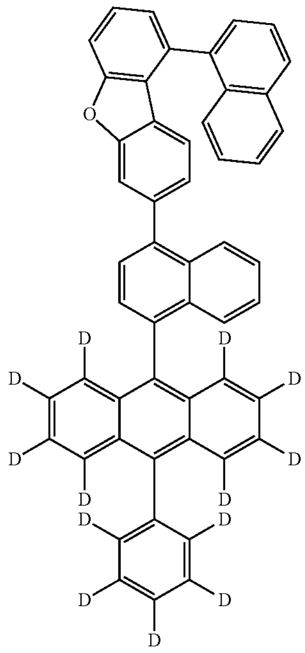
-continued
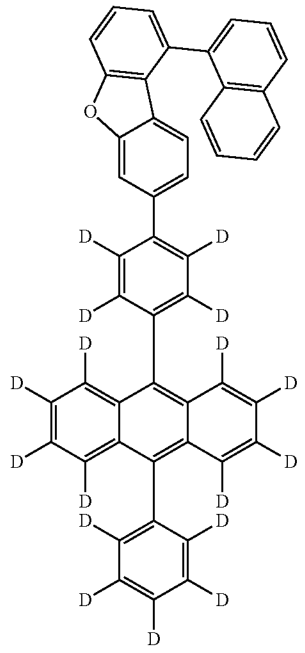
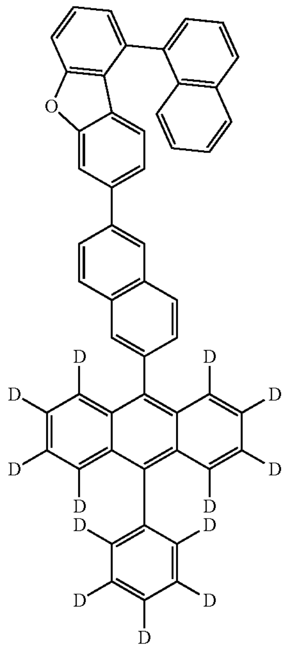
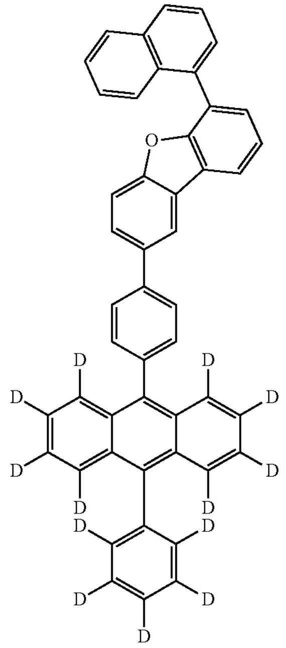

-continued
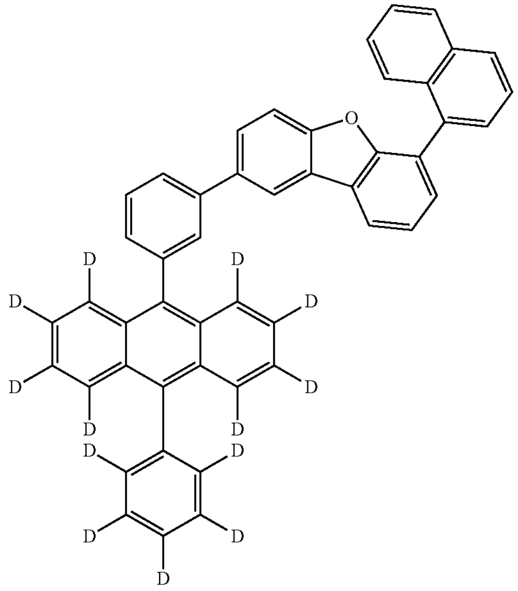
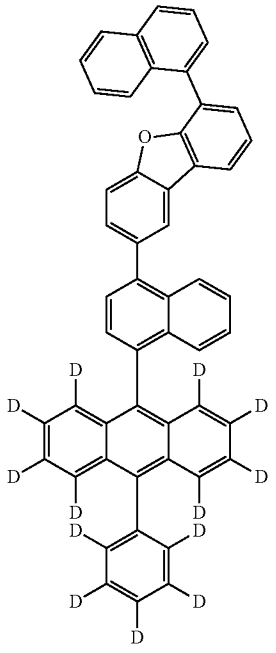
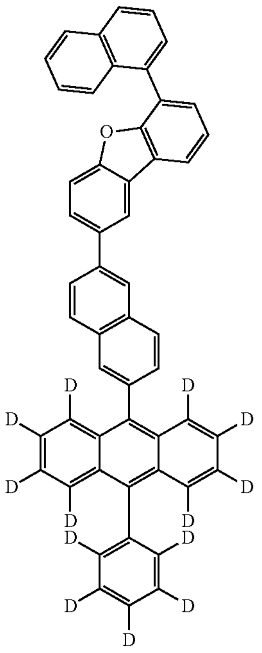
-continued
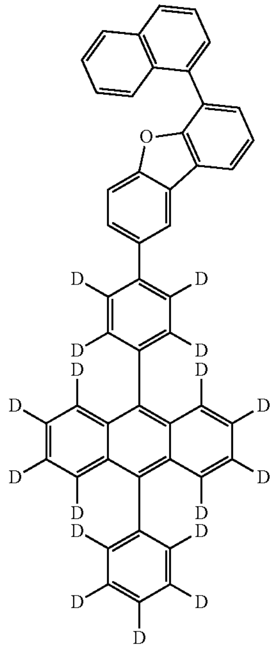
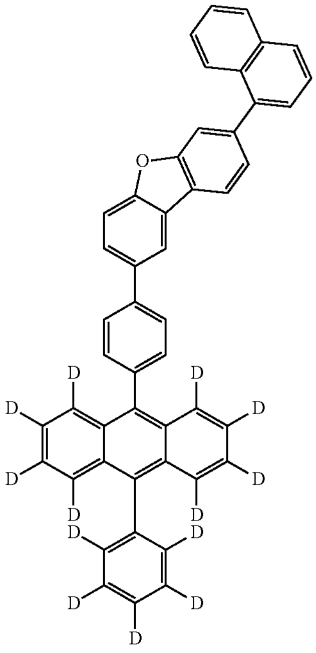

-continued
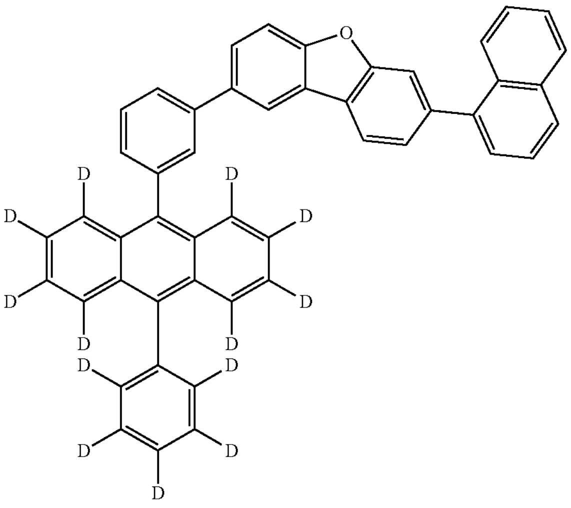
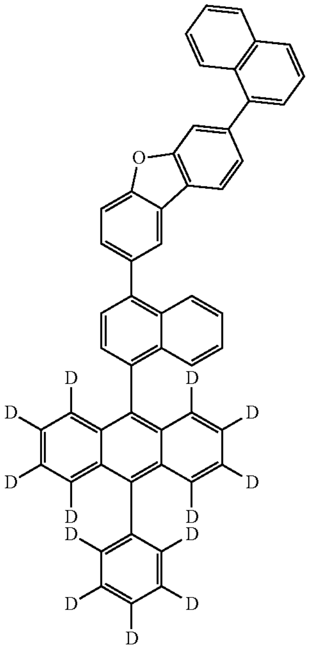
-continued
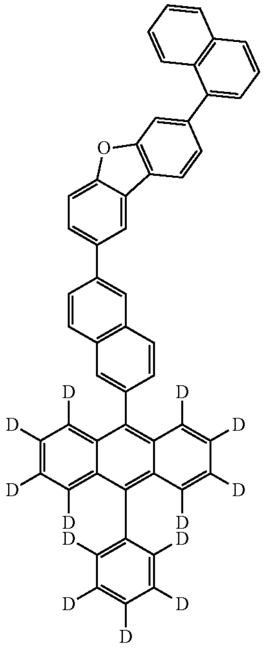
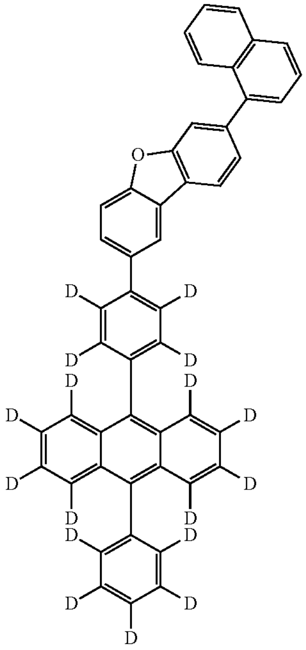
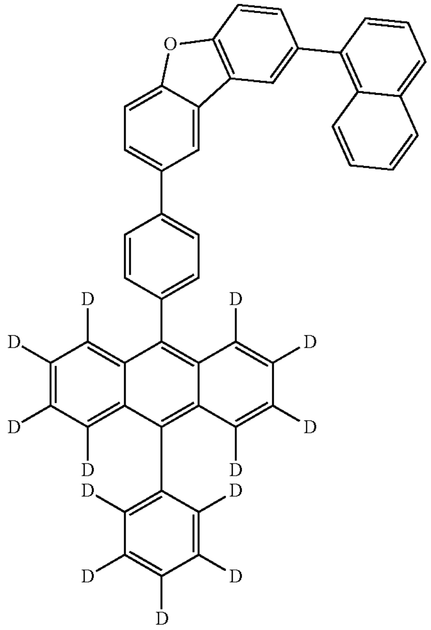

-continued
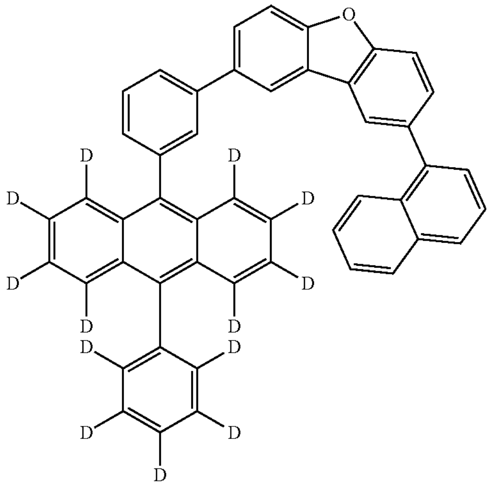
-continued
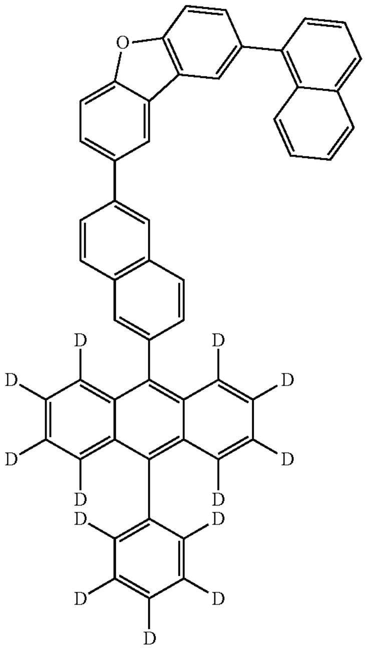
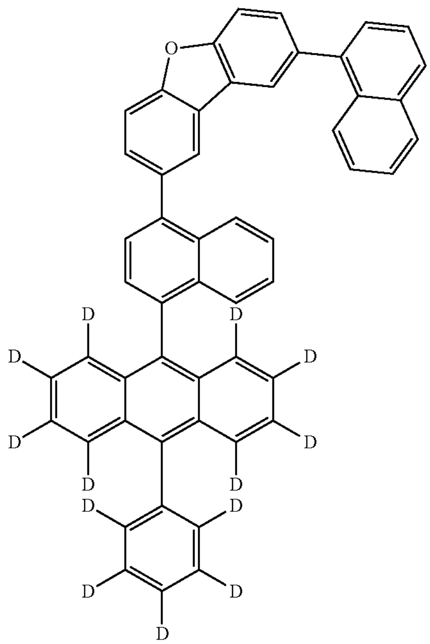
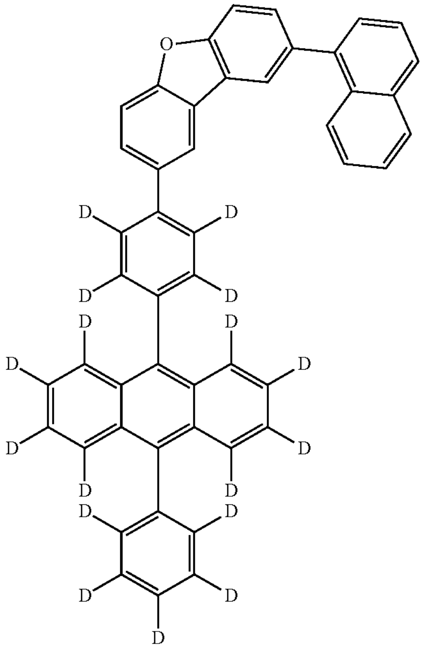

-continued
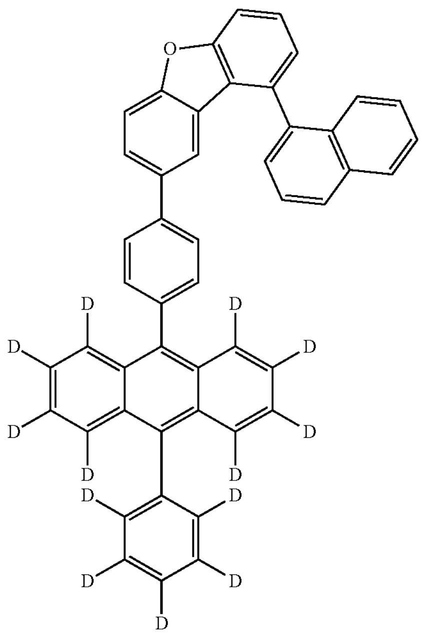
-continued
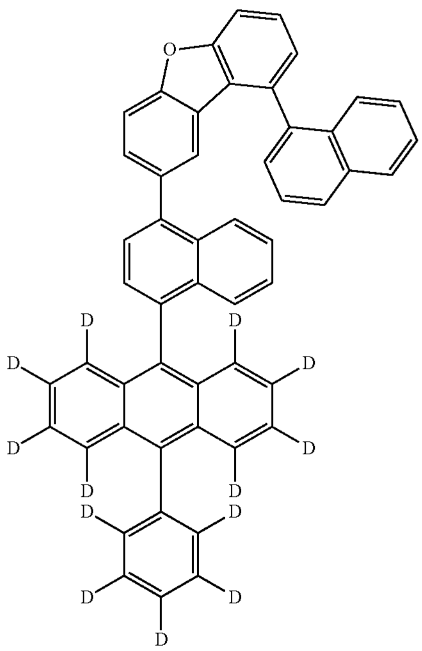
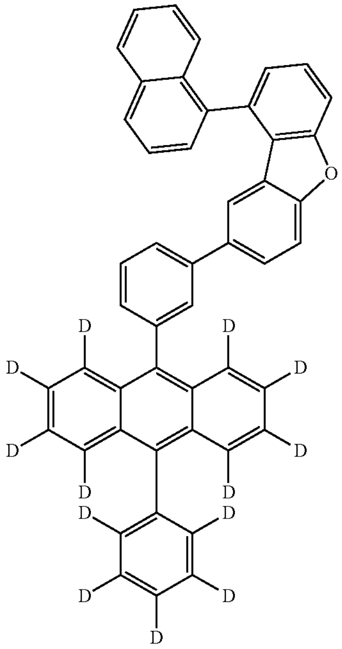
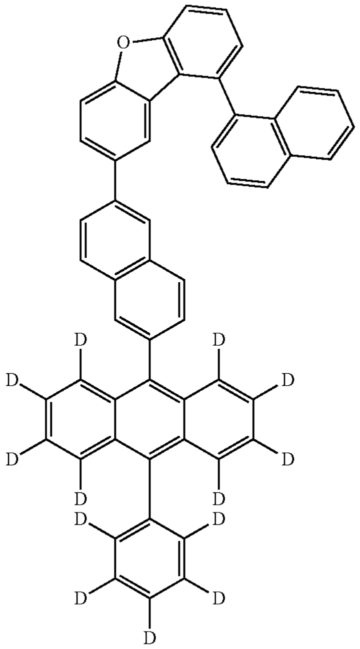

-continued
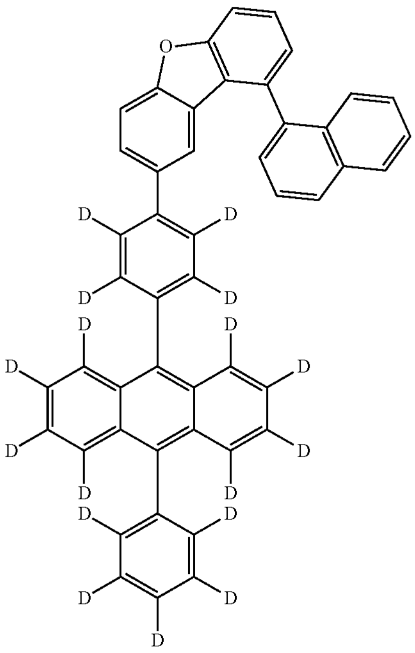
-continued
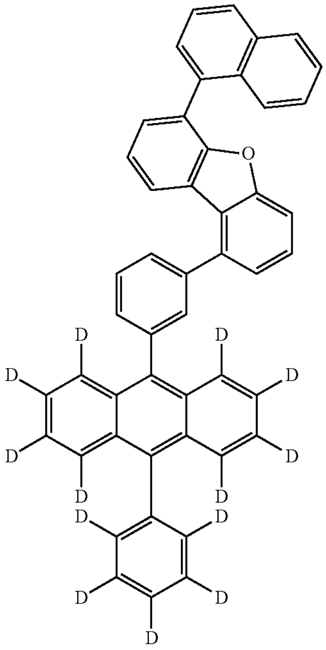
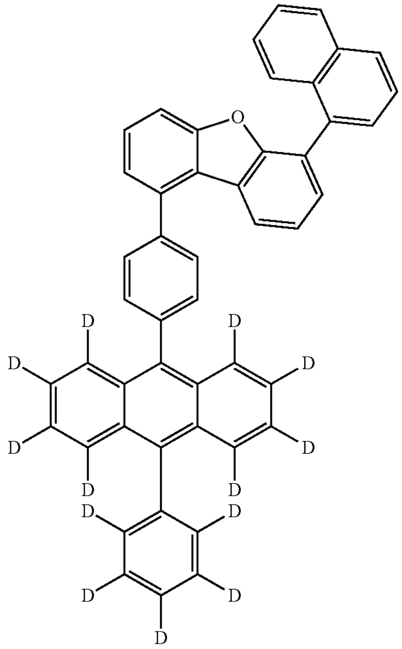
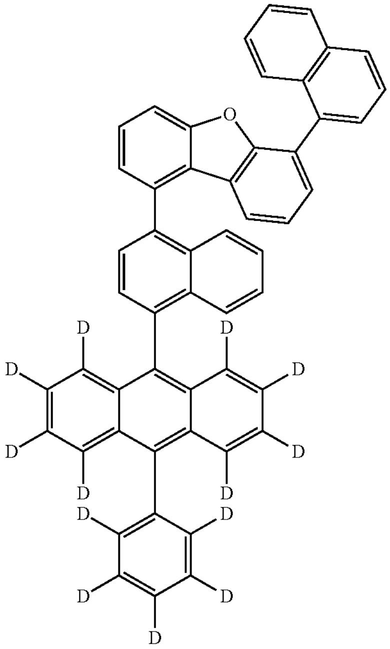

-continued
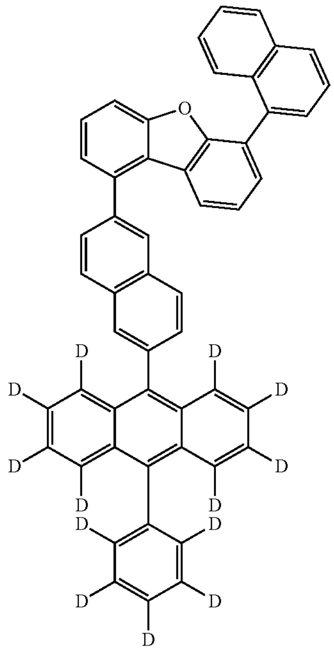
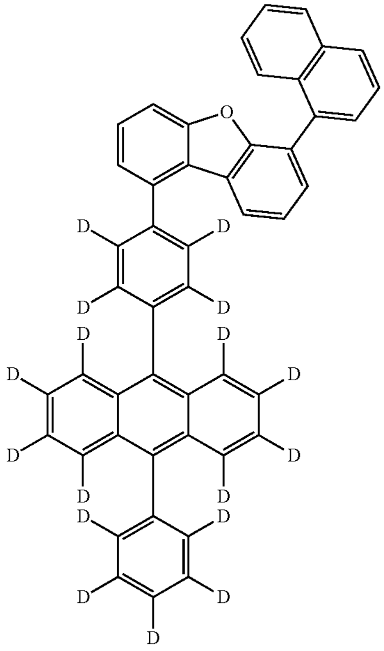
-continued
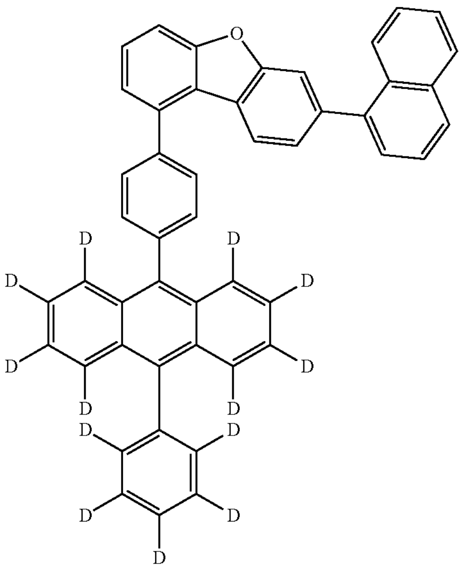
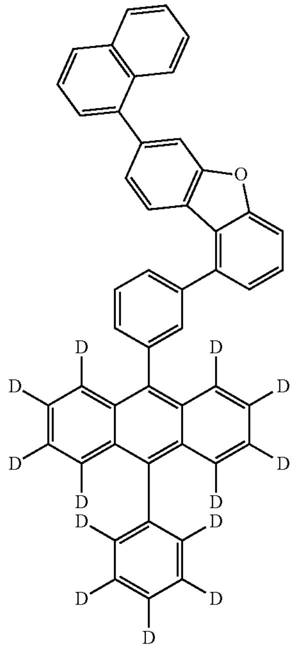

-continued
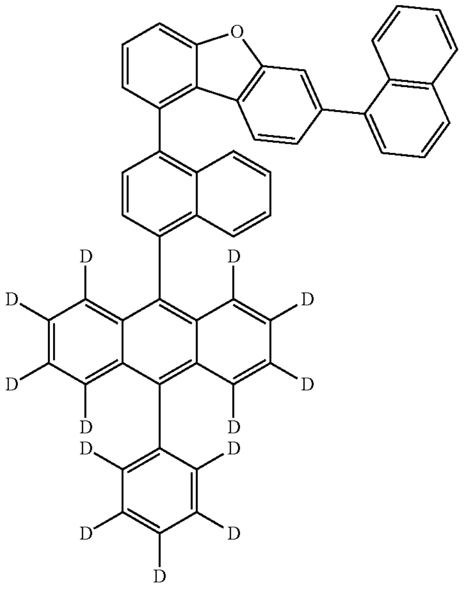
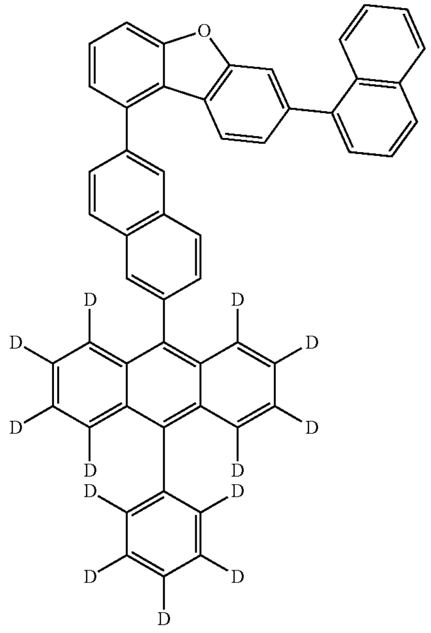
-continued
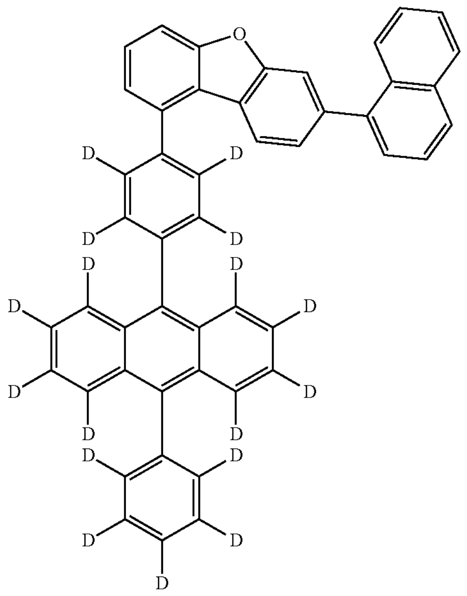
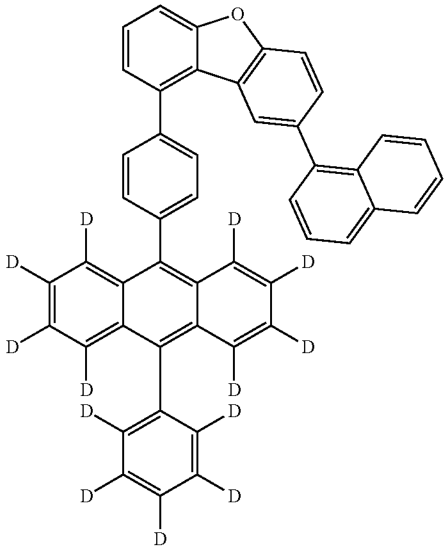
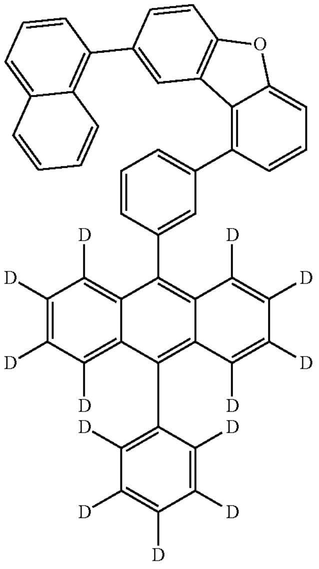

-continued
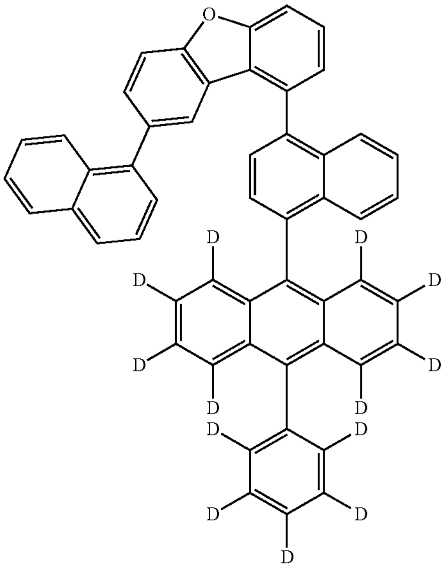
-continued
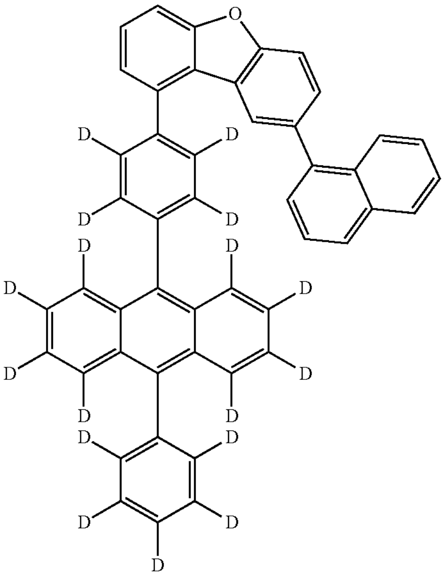
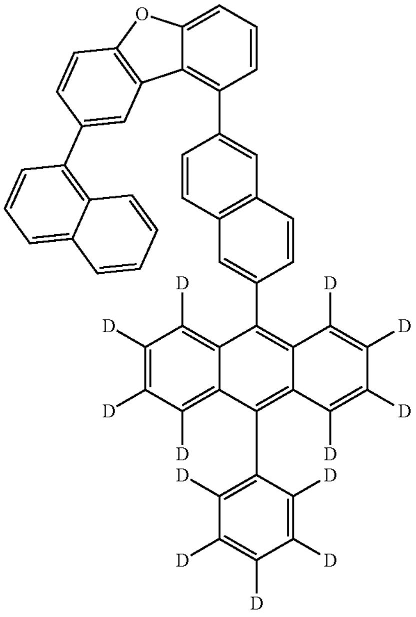
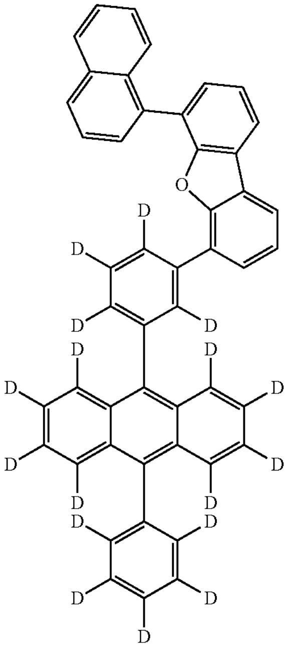

-continued
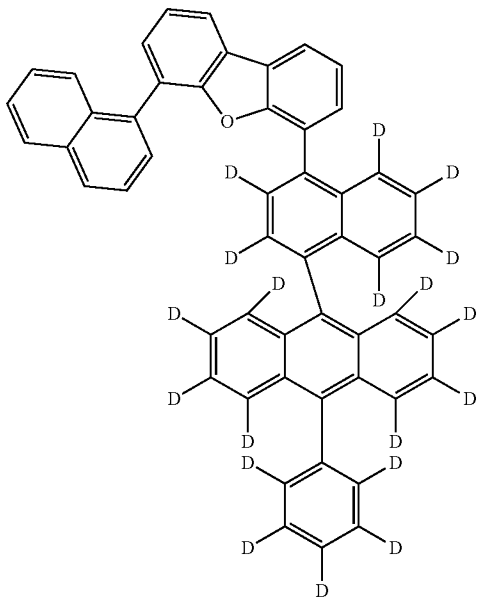
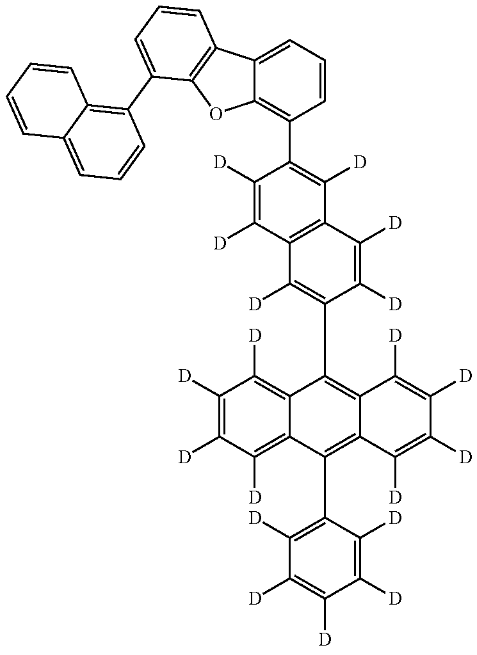
-continued
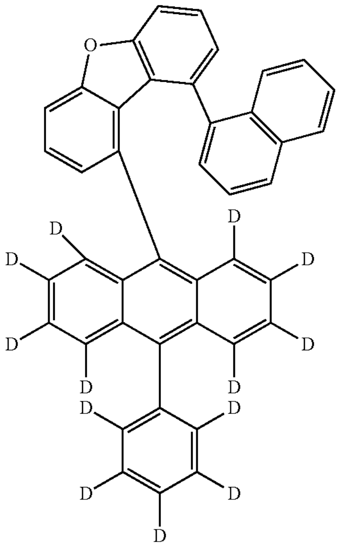
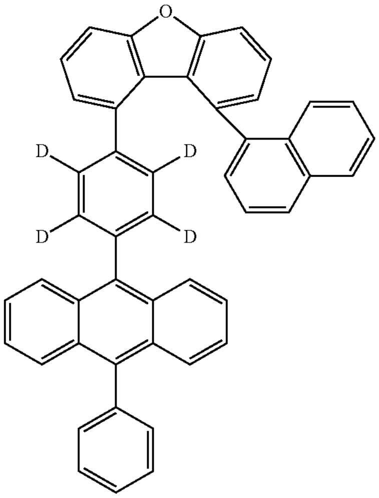
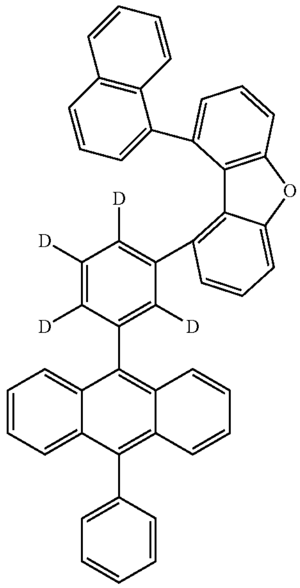
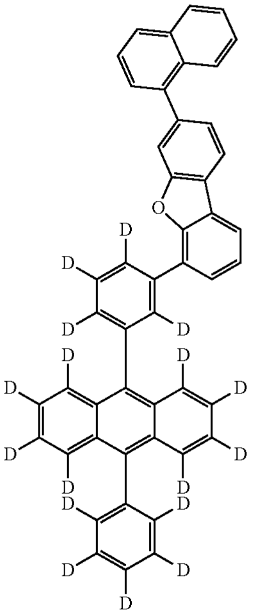

-continued
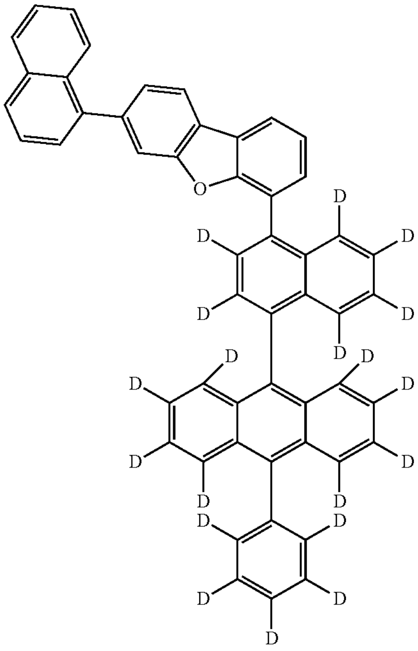
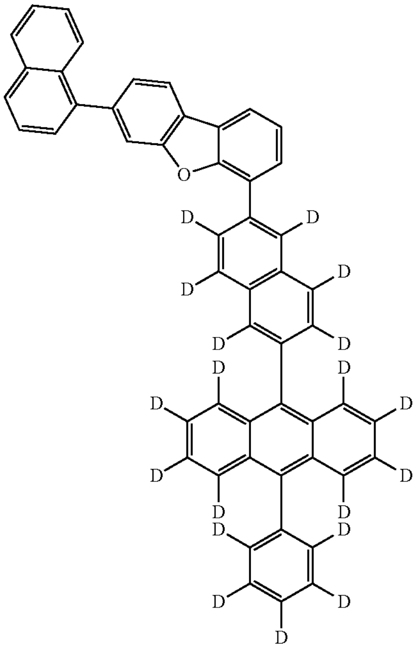
-continued
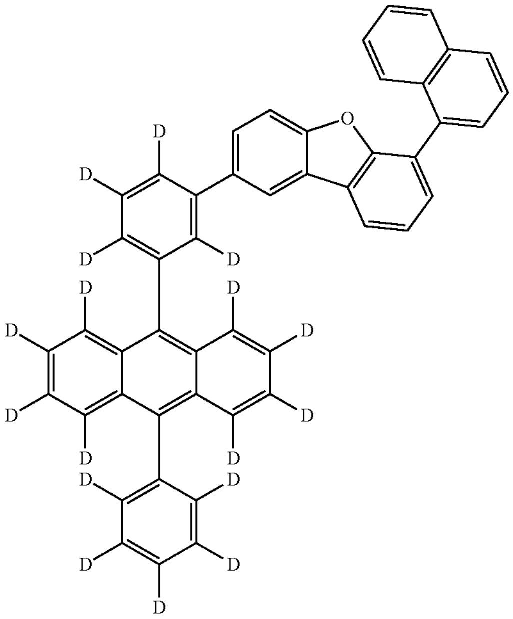
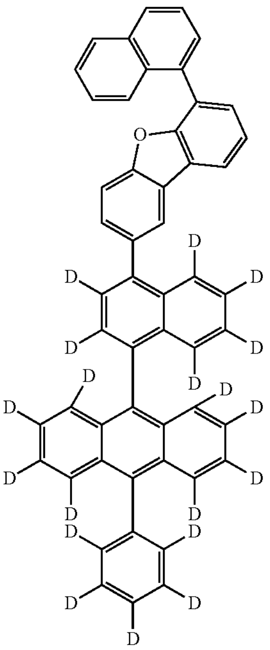
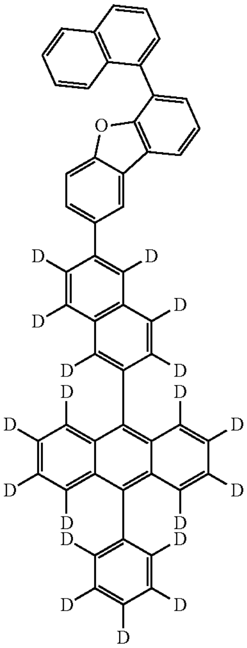

-continued
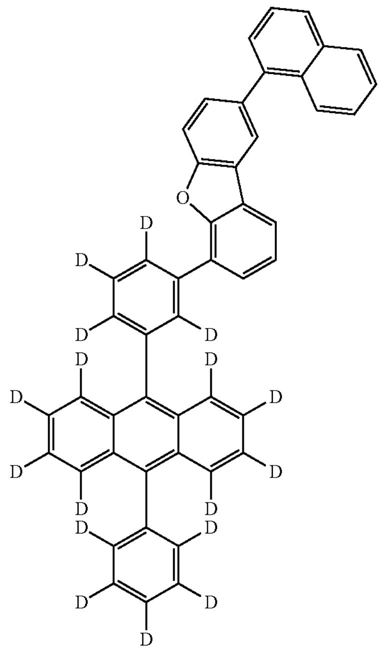
-continued
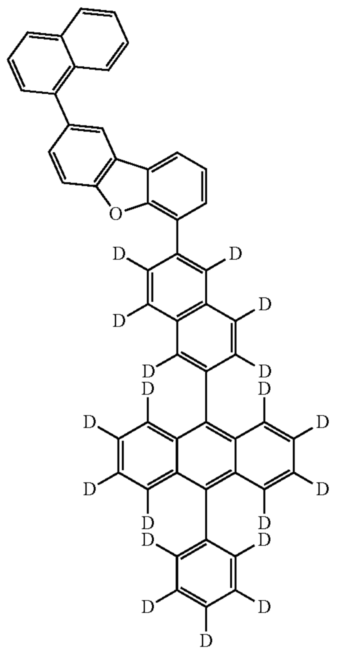
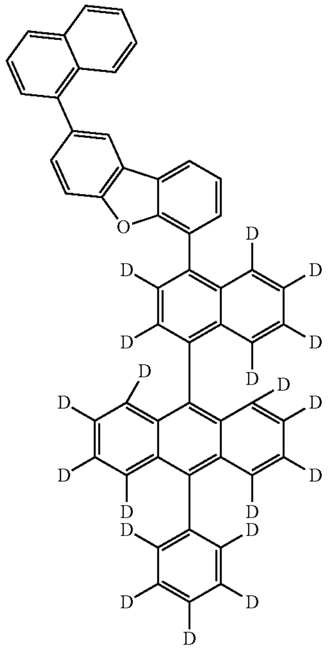
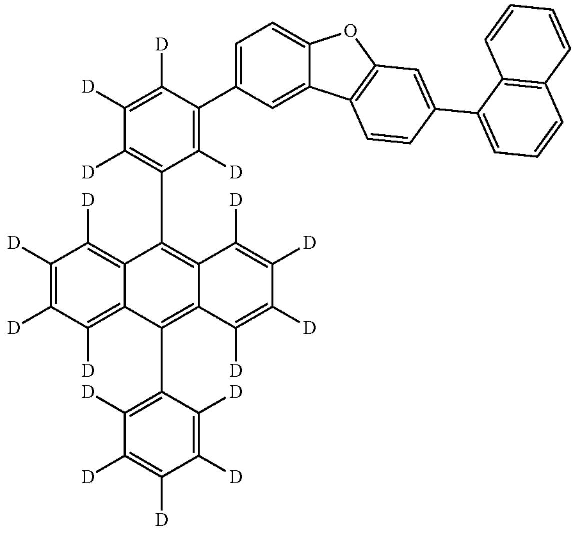

-continued
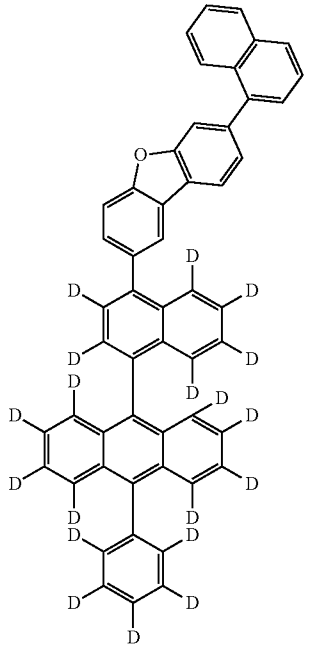
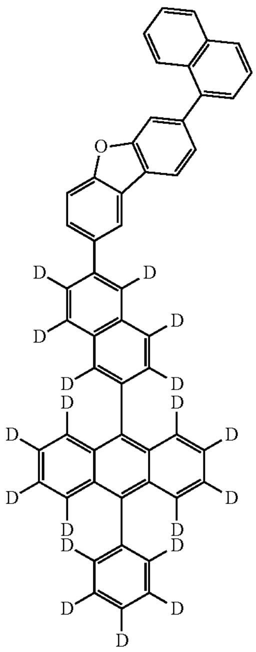
-continued
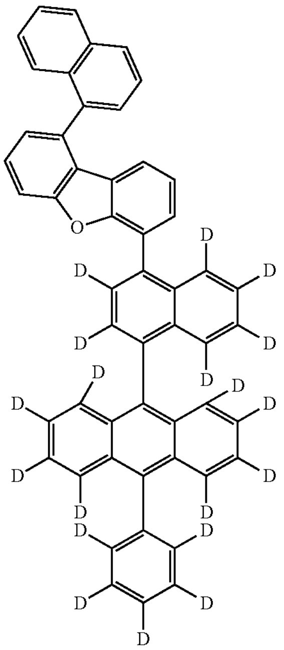
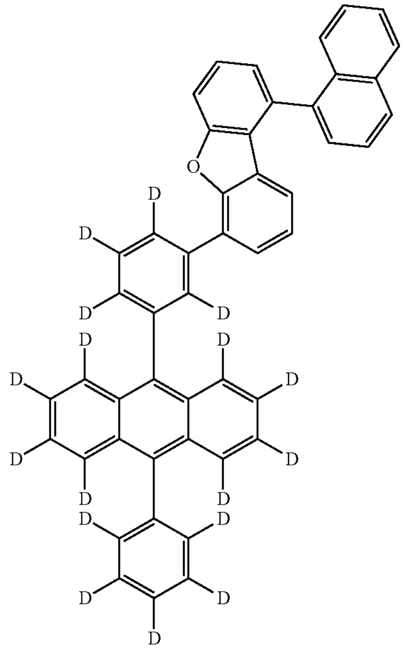
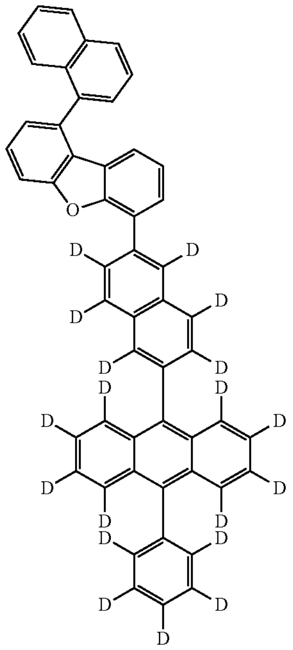

-continued
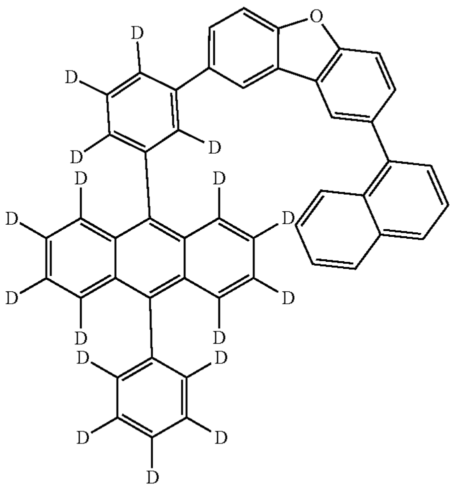
-continued
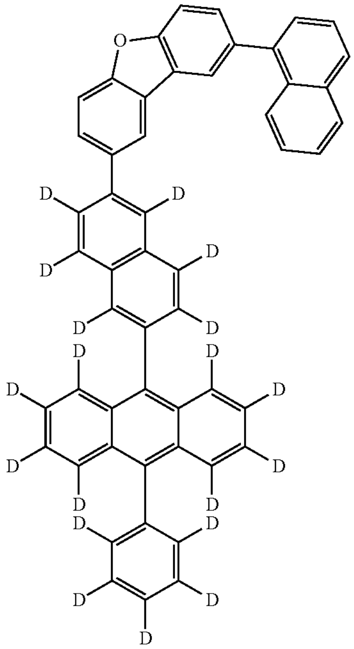
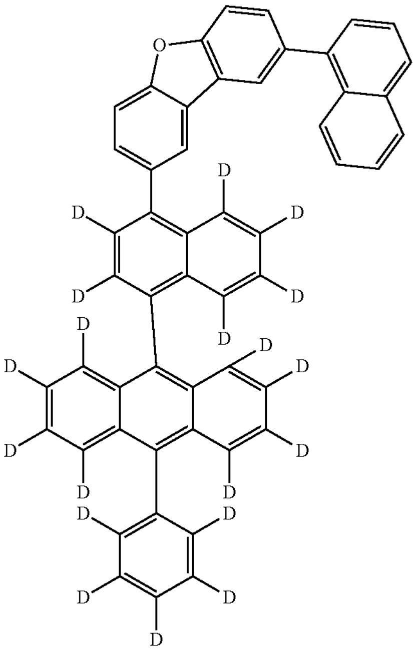
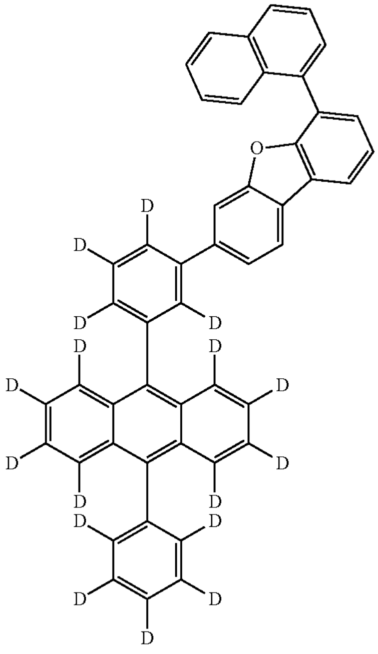

-continued
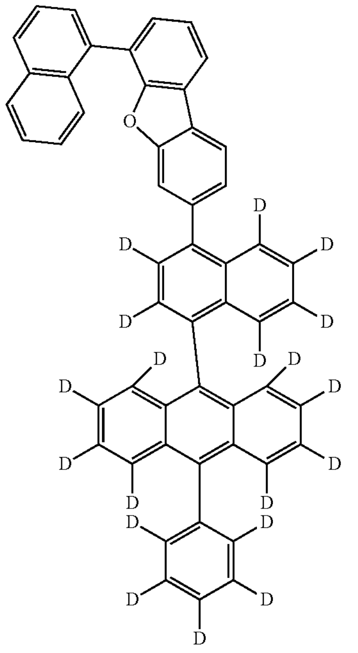
-continued
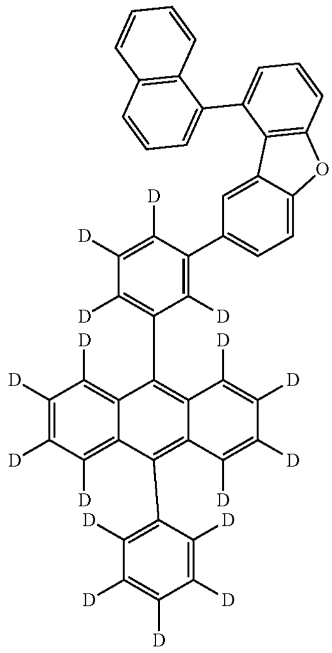
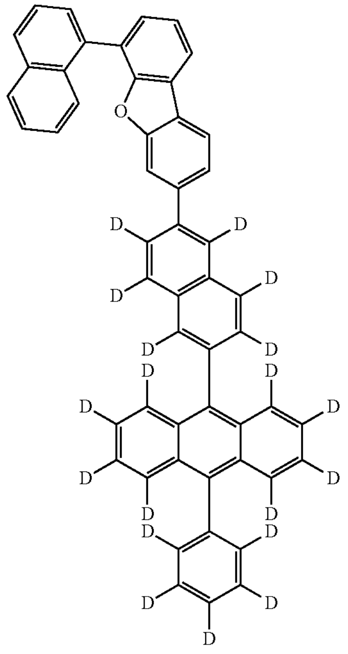
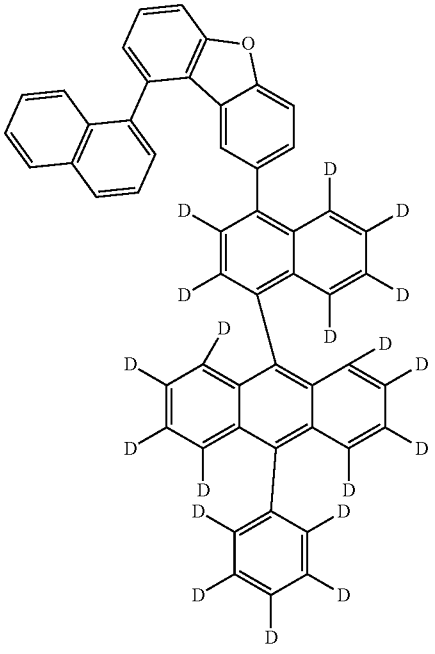

-continued
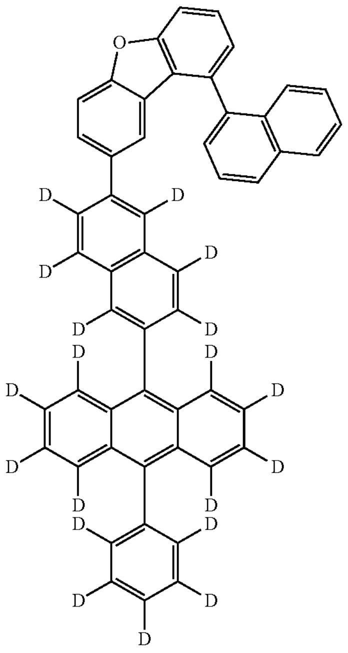
-continued
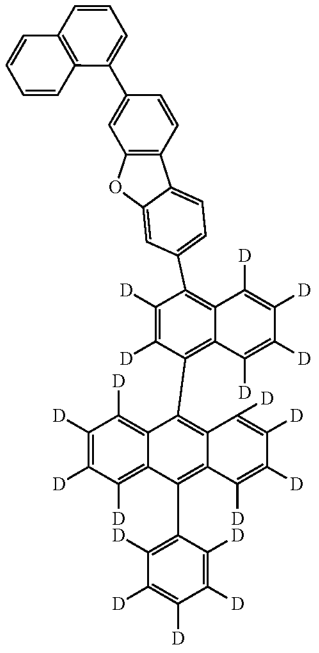
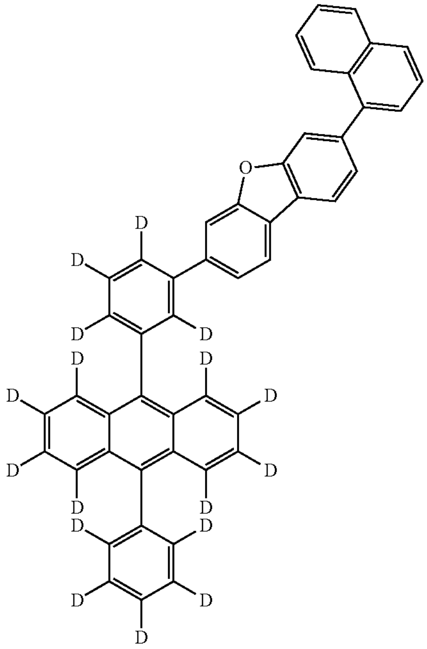
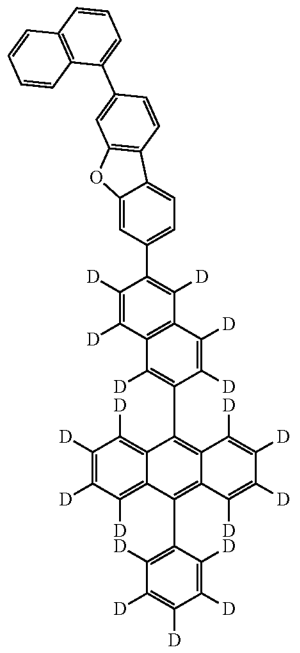

-continued
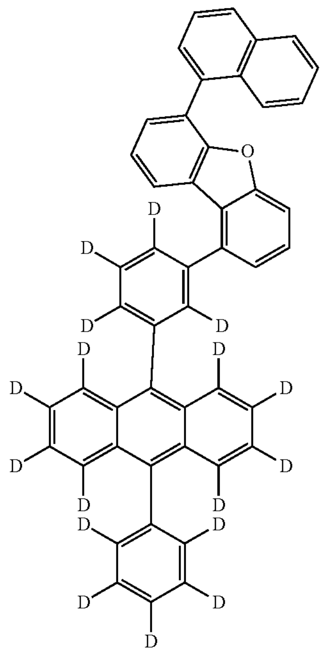
-continued
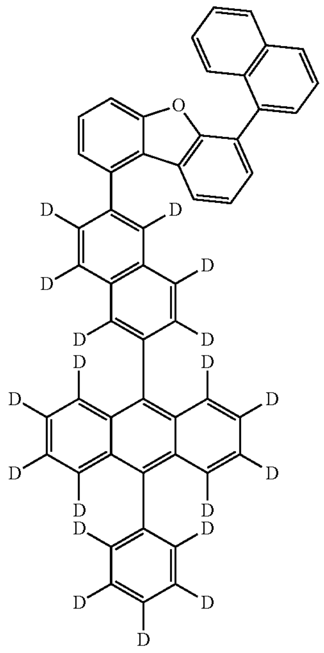
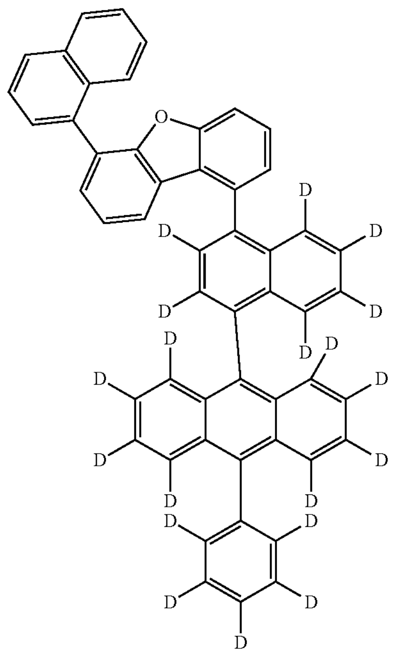
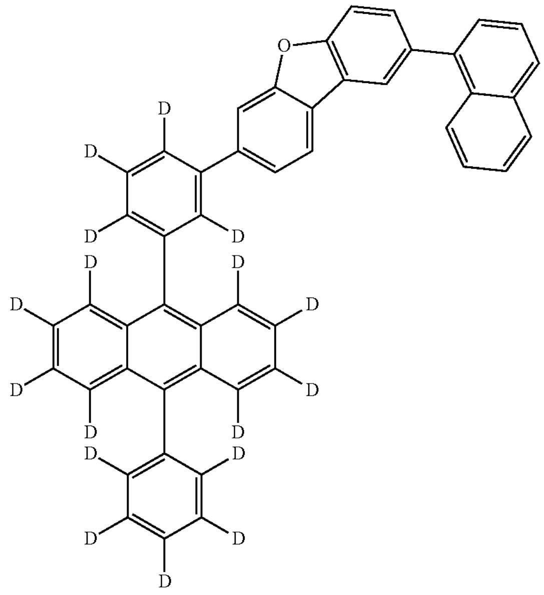

-continued
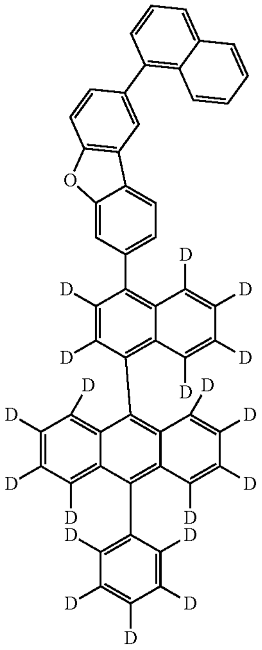
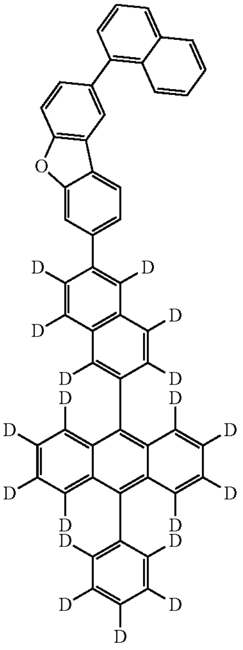
-continued
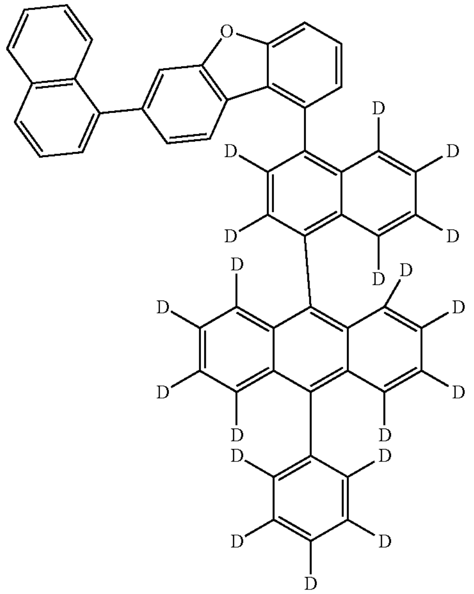
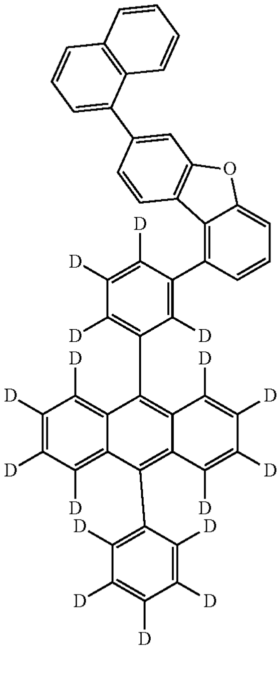
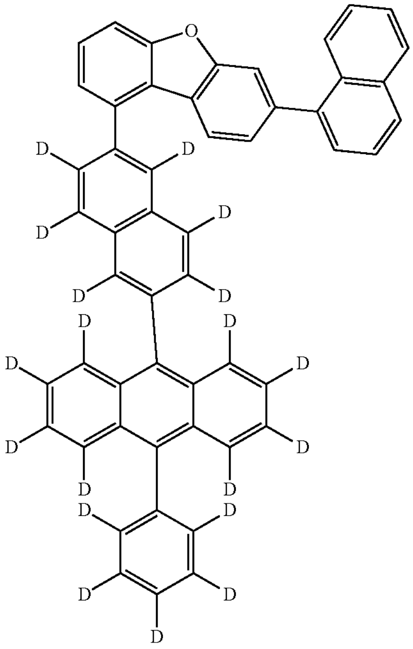

-continued
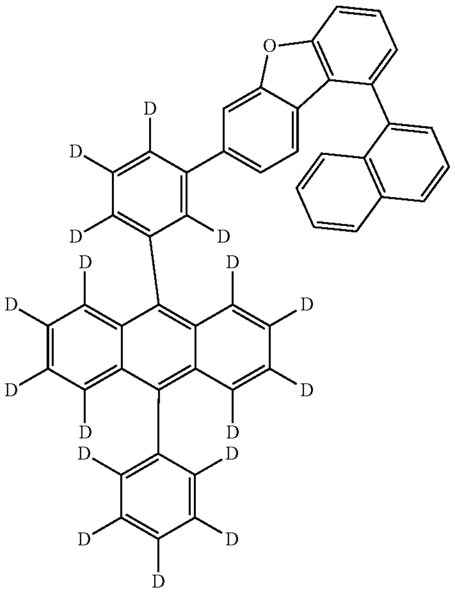
-continued
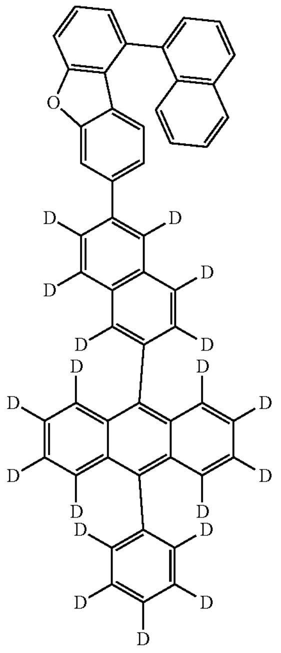
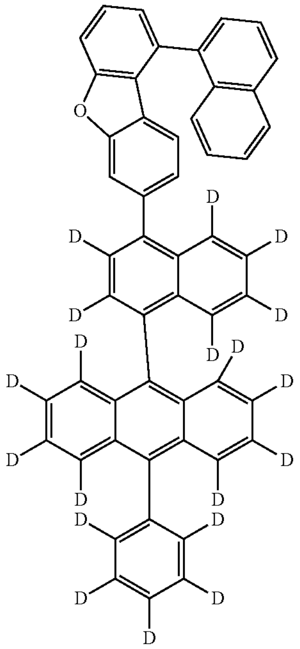
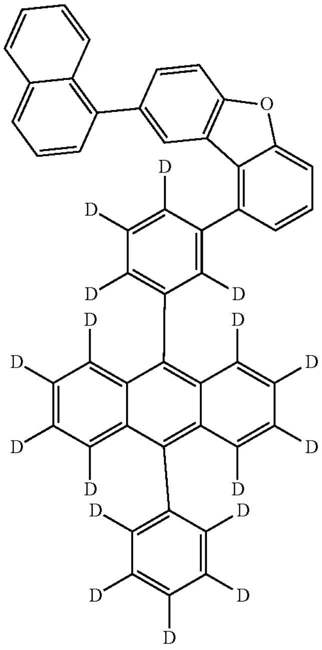

-continued
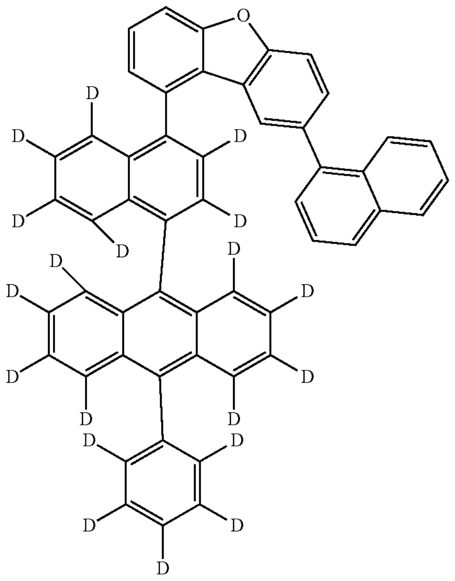
-continued
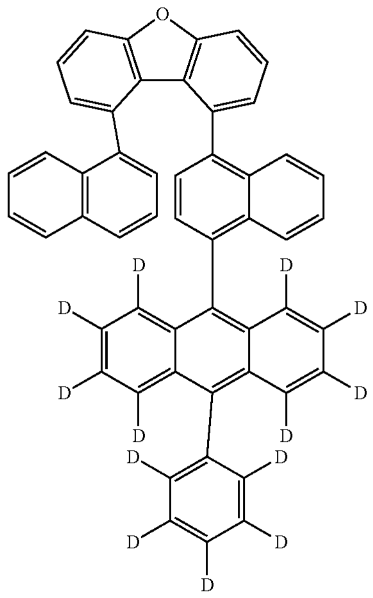
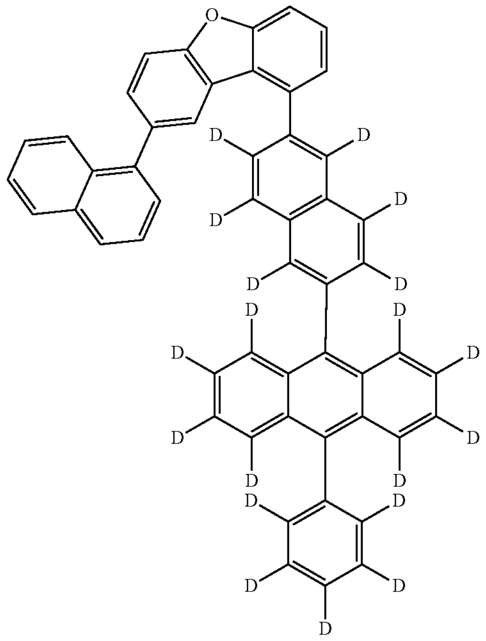
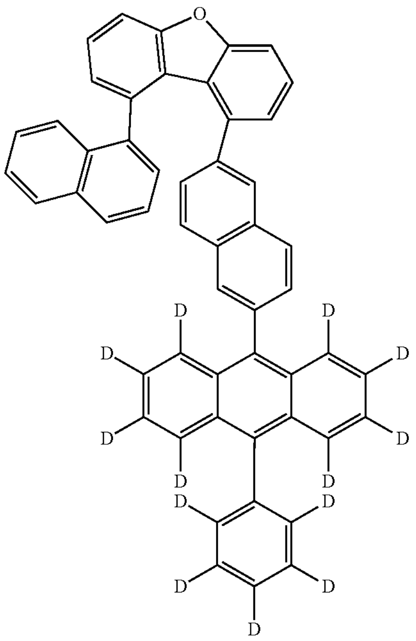

-continued
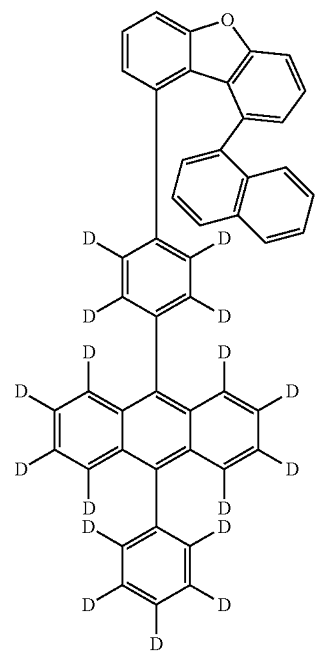
-continued
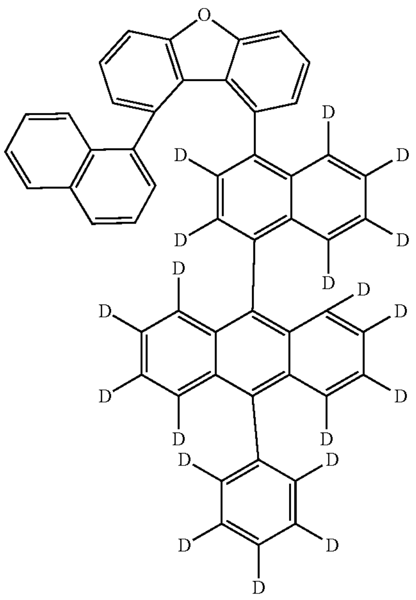
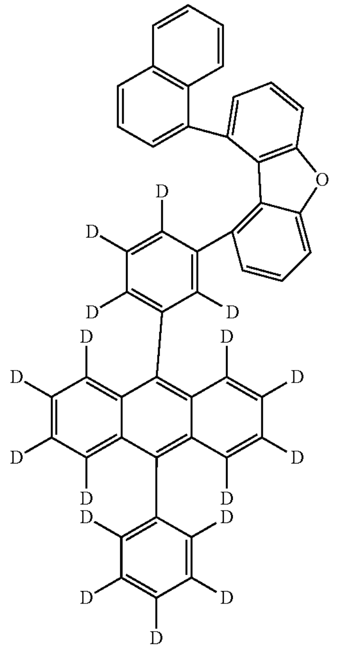
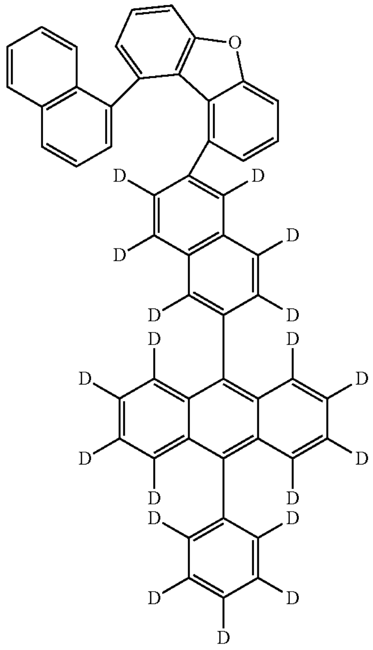

-continued
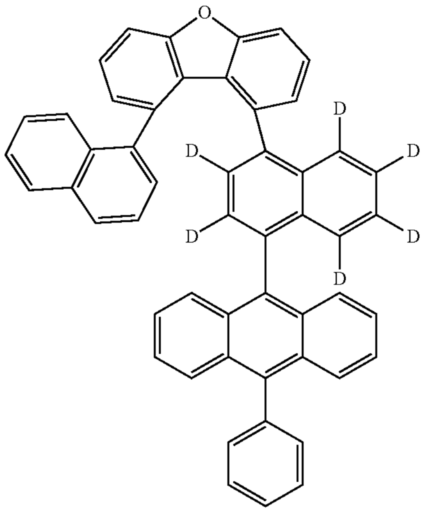
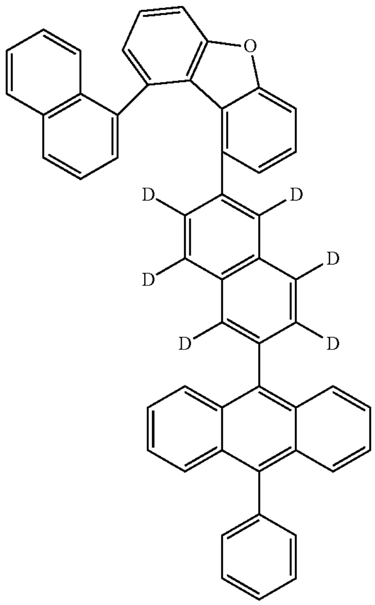
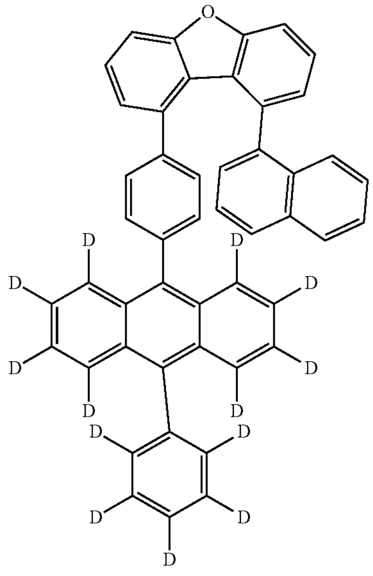
-continued
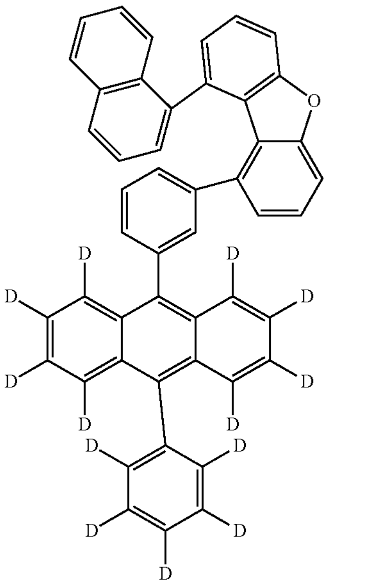
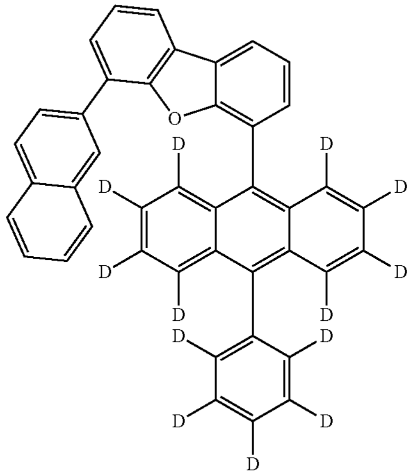
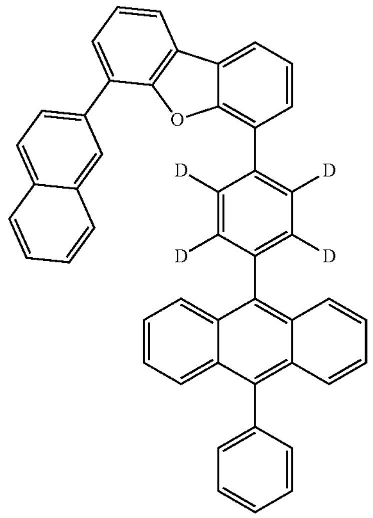

-continued
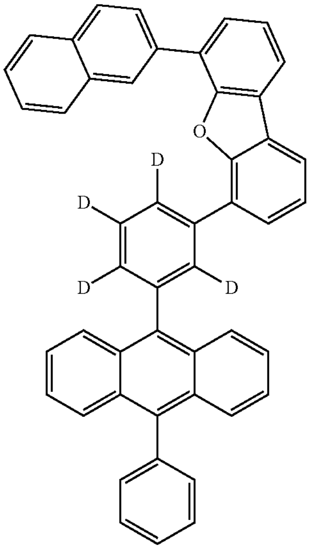
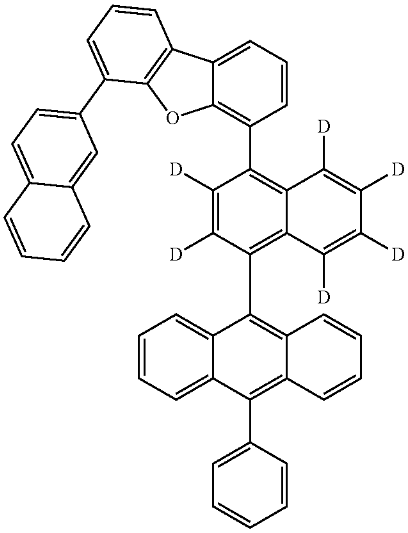
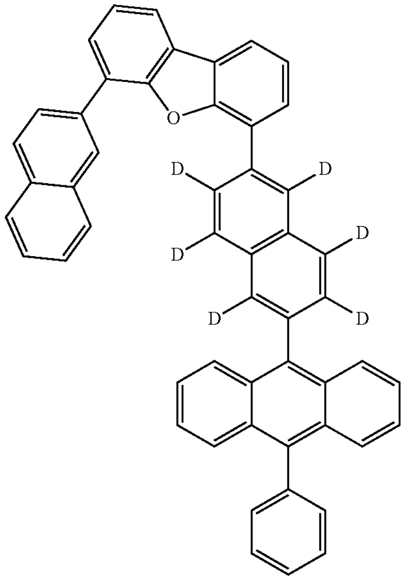
-continued
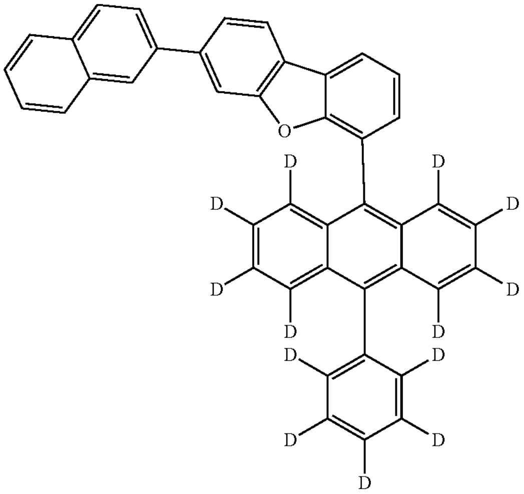
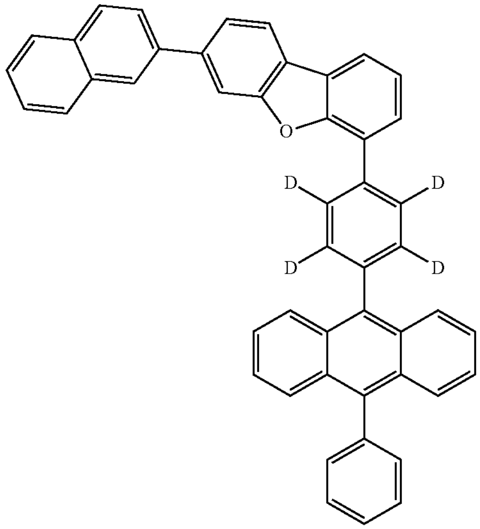
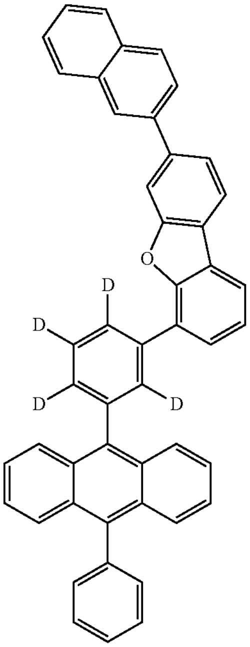

-continued
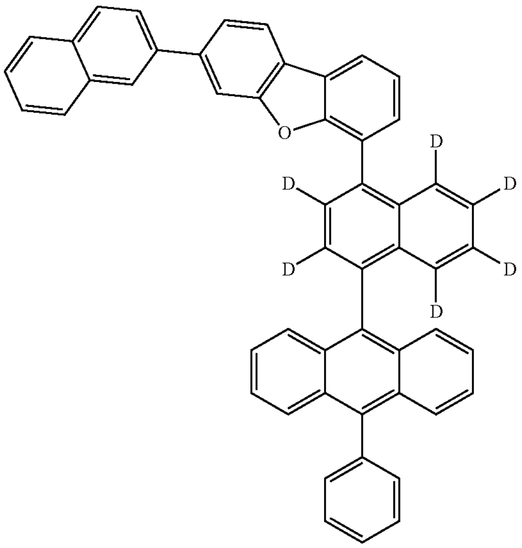
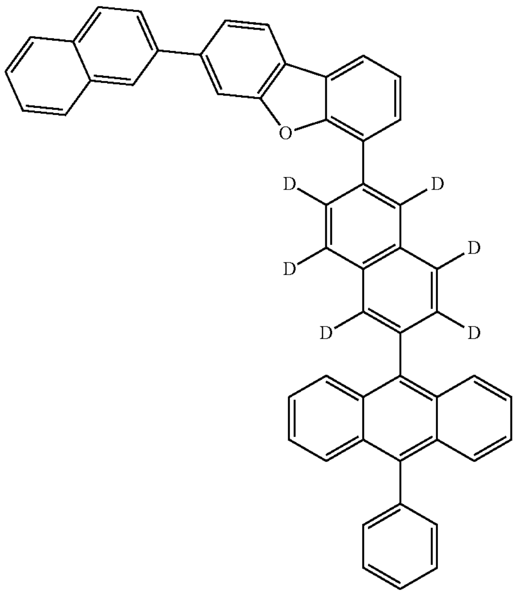
-continued
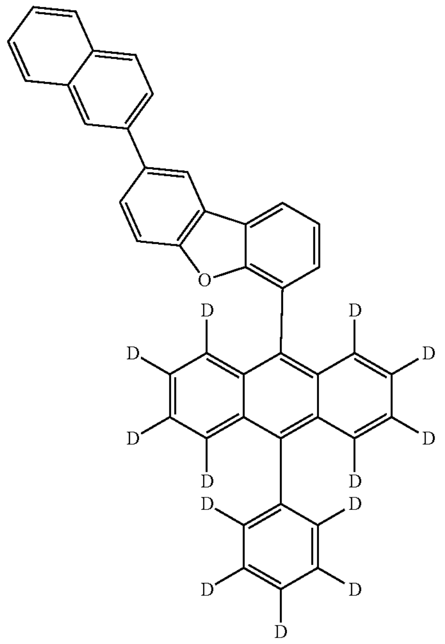
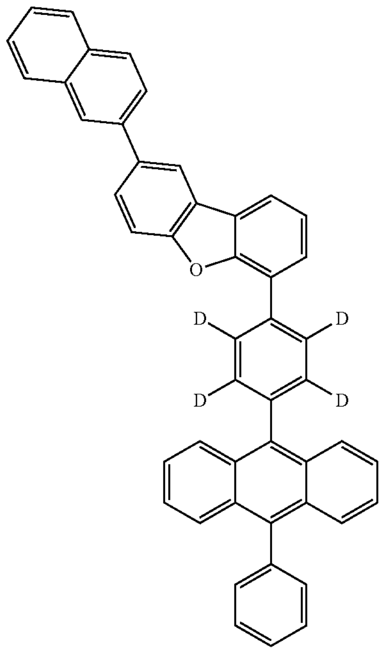

-continued
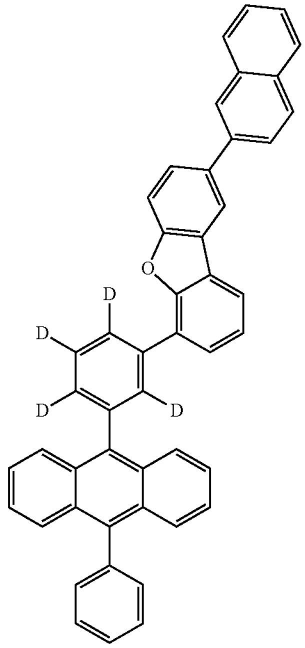
-continued
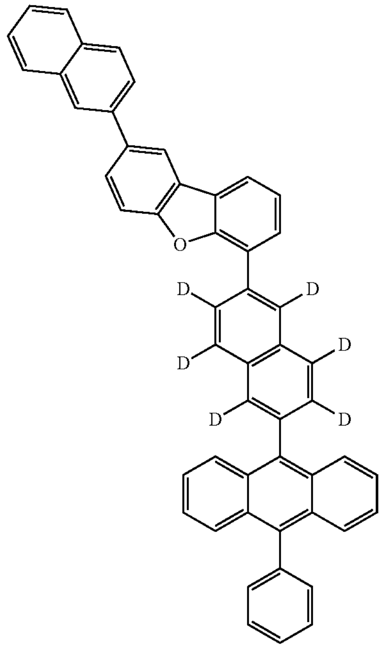
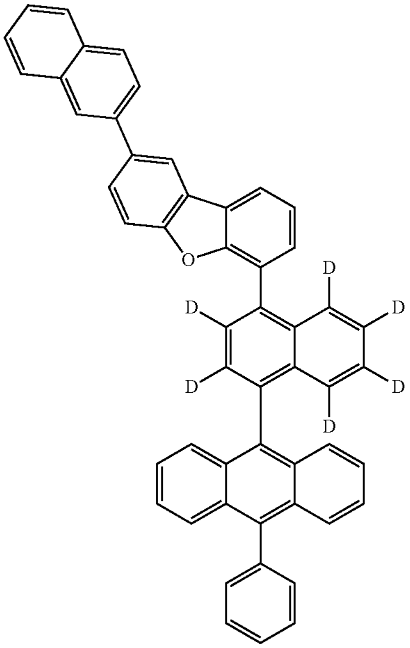
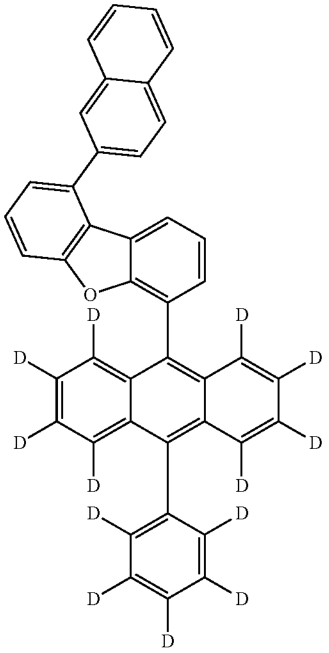

-continued
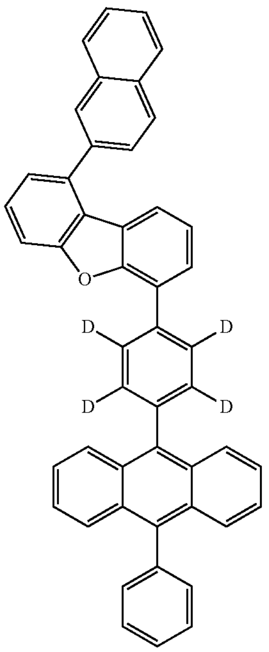
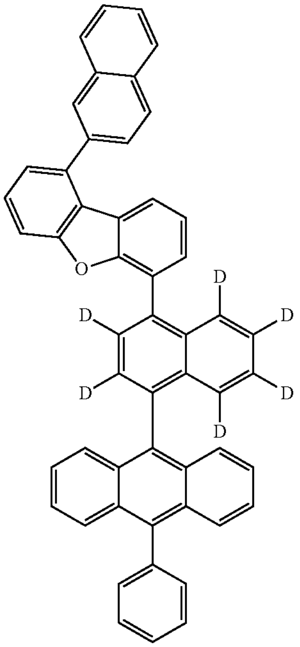
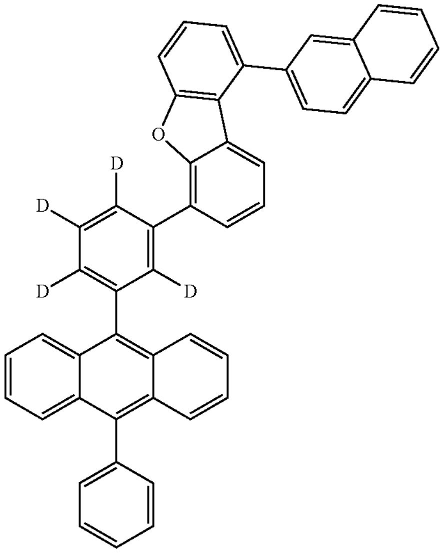
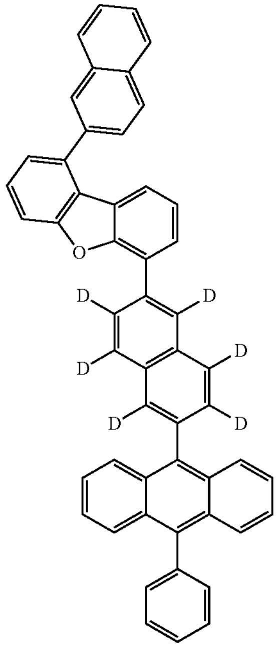

-continued
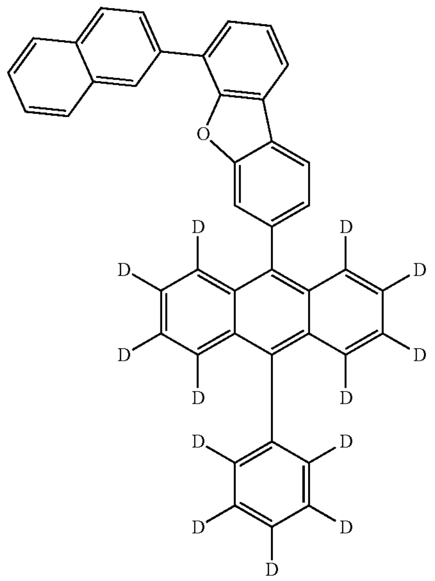
-continued
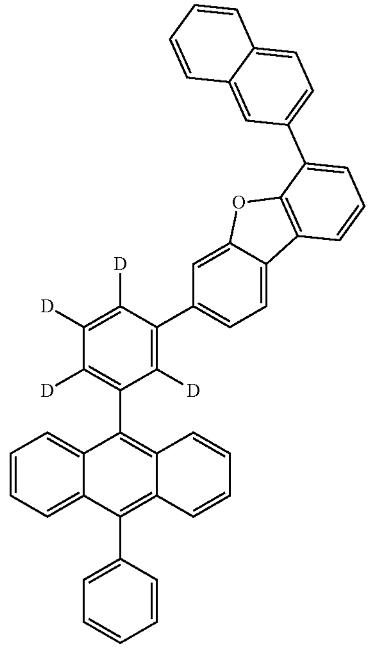
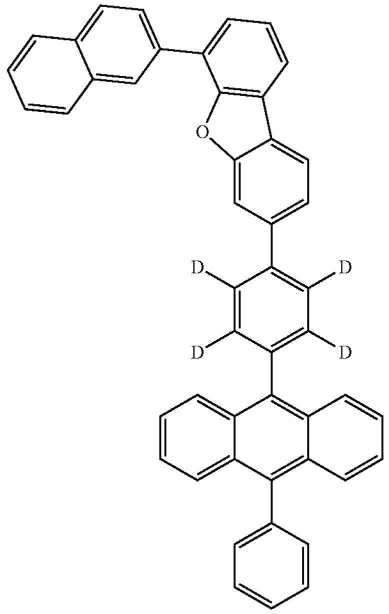
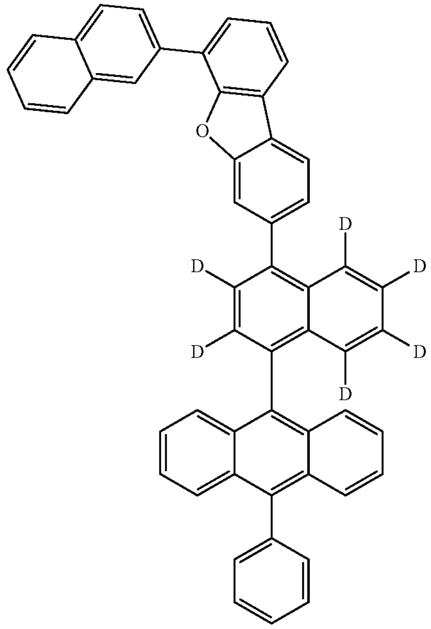

-continued
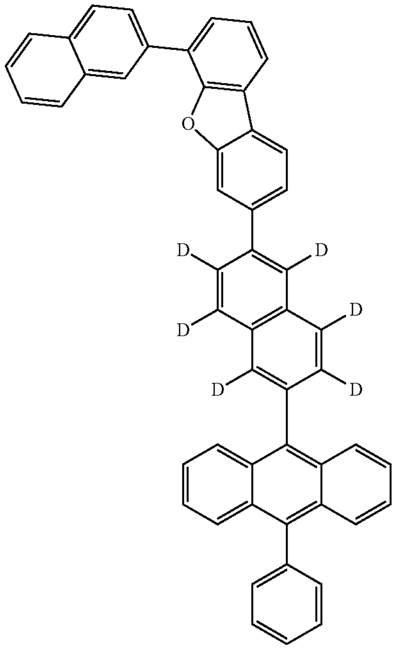
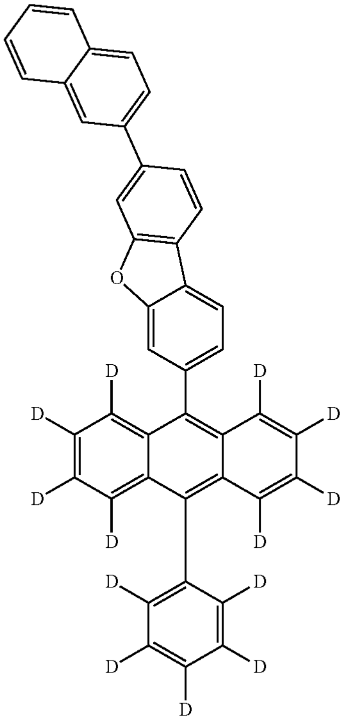
-continued
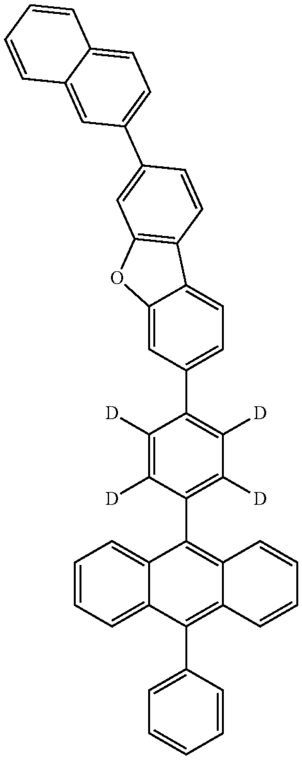
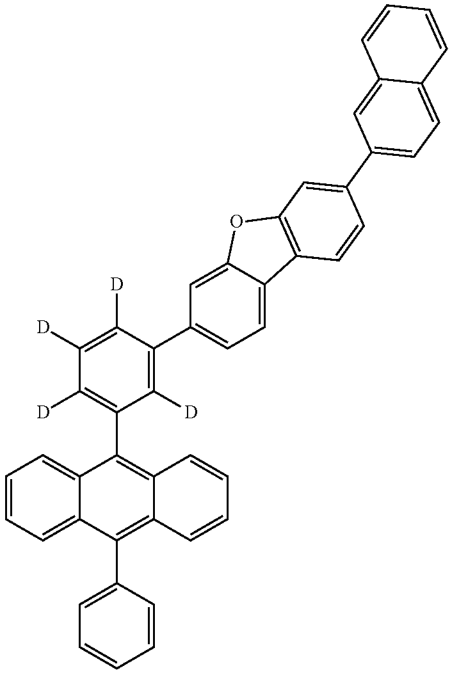

-continued
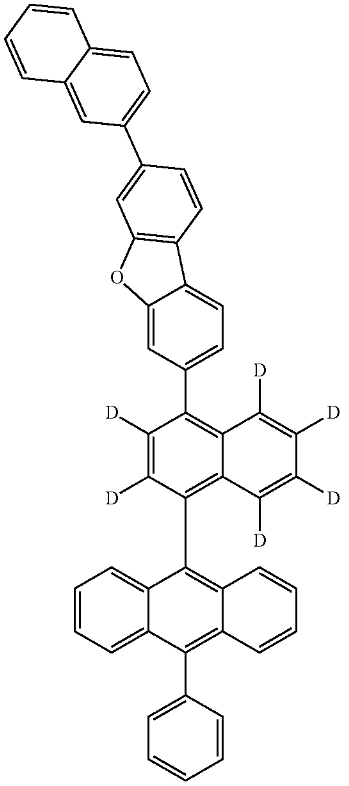
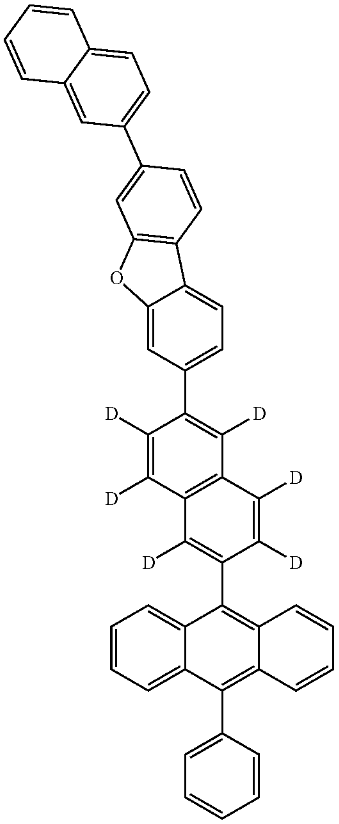
-continued
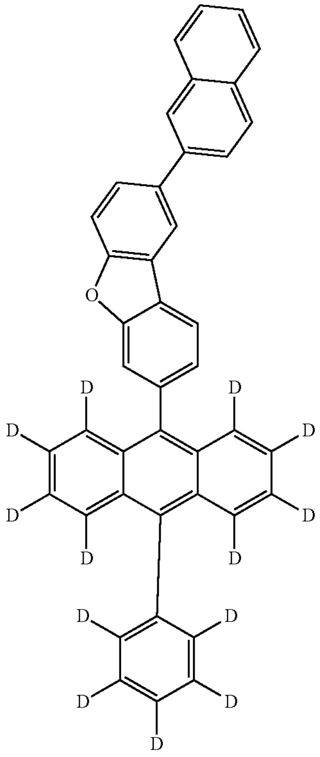
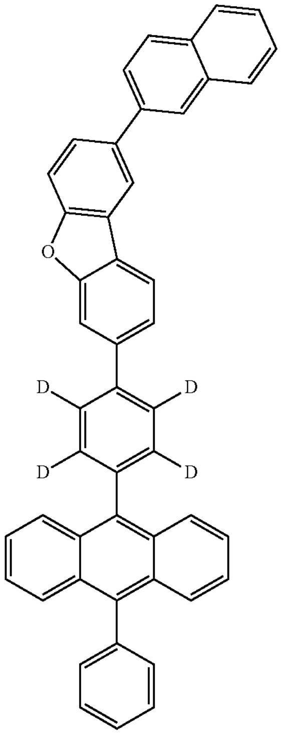

-continued
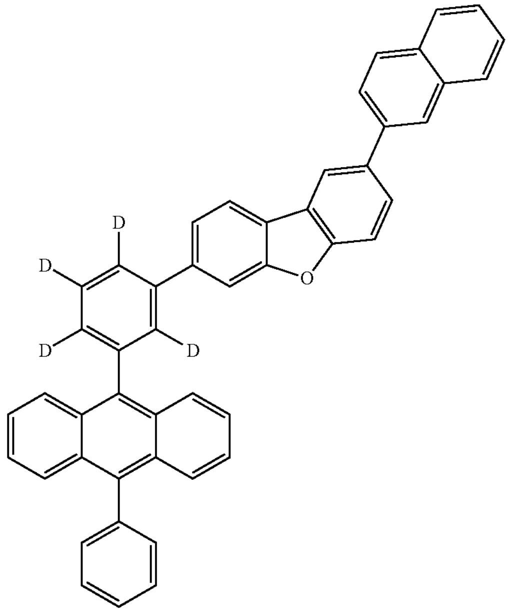
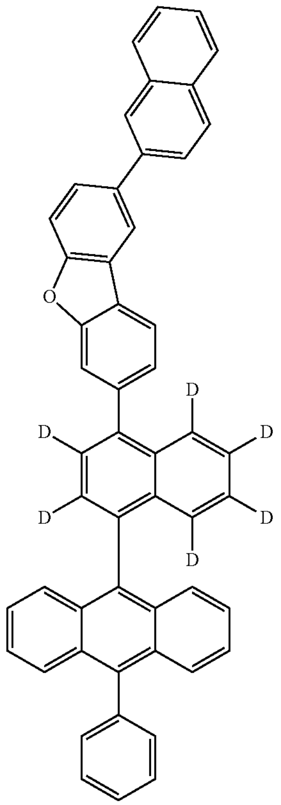
-continued
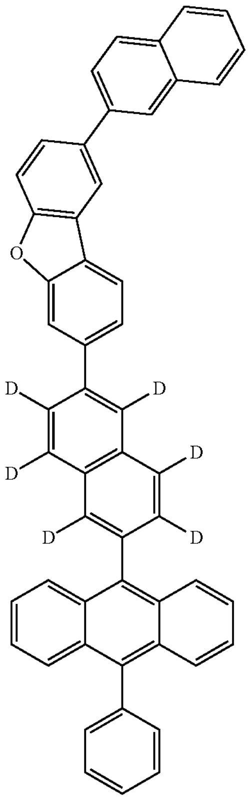
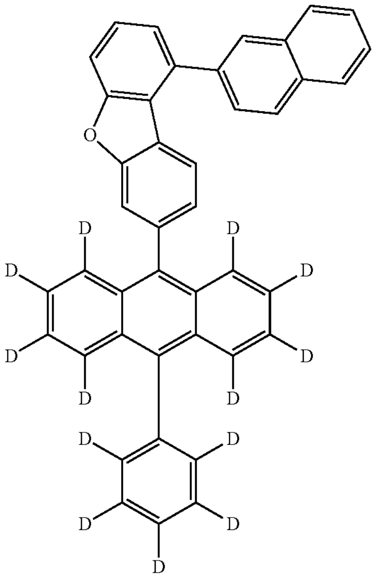

-continued
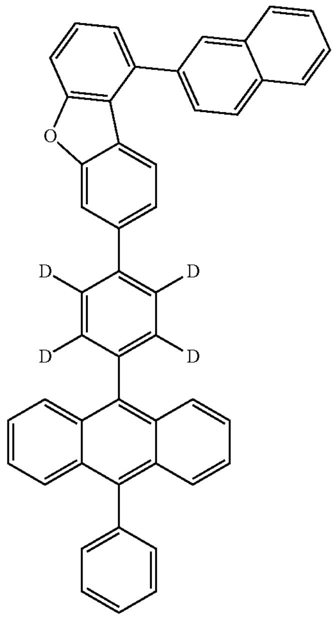
-continued
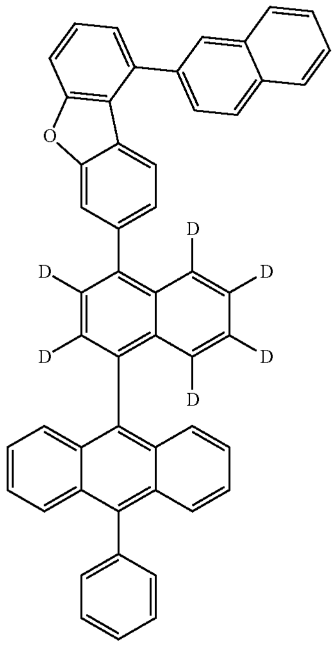
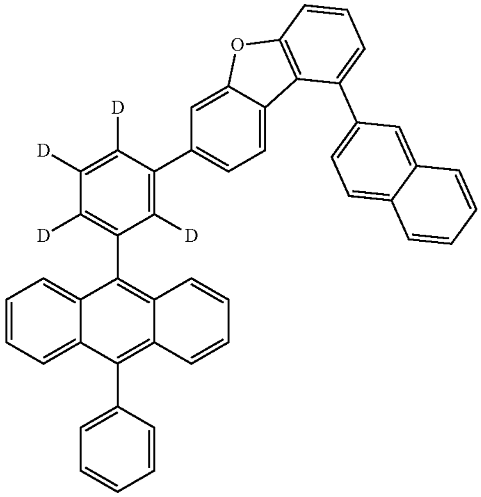
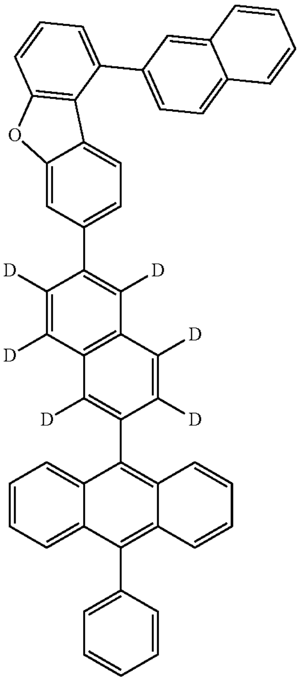

-continued
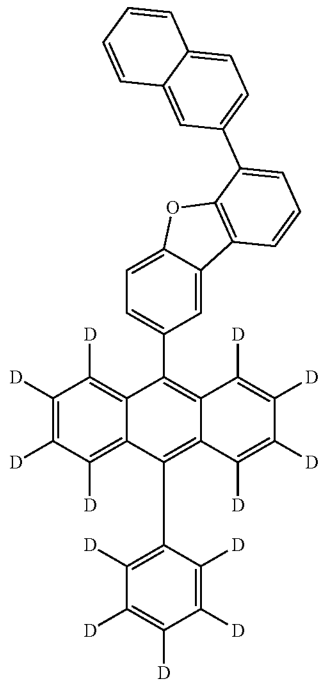
-continued
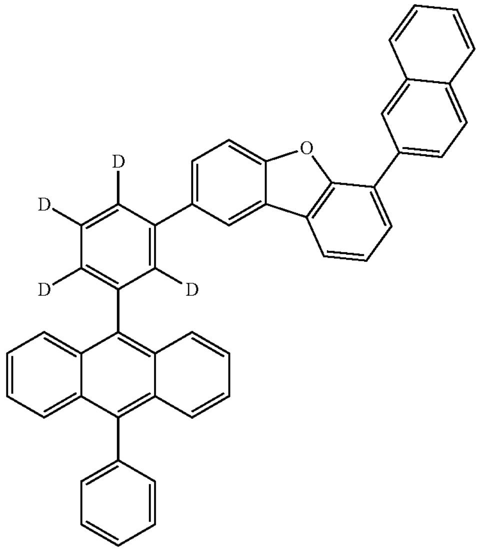
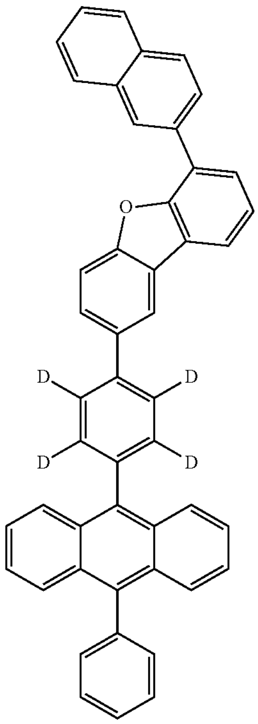
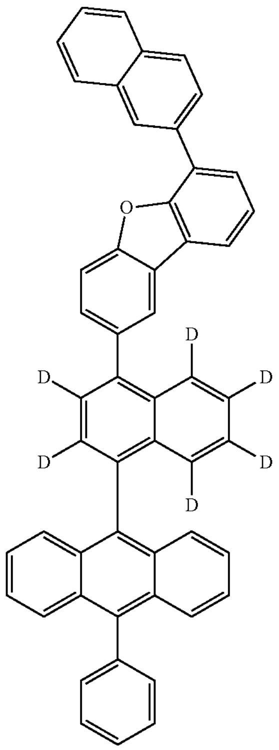

-continued
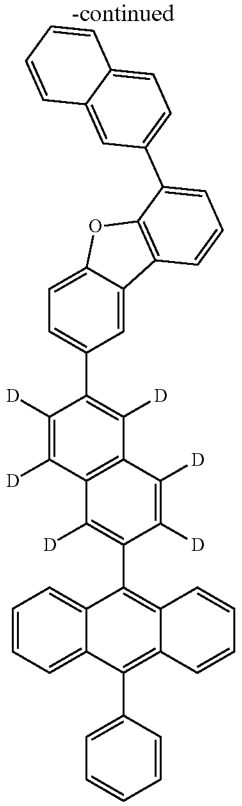
-continued
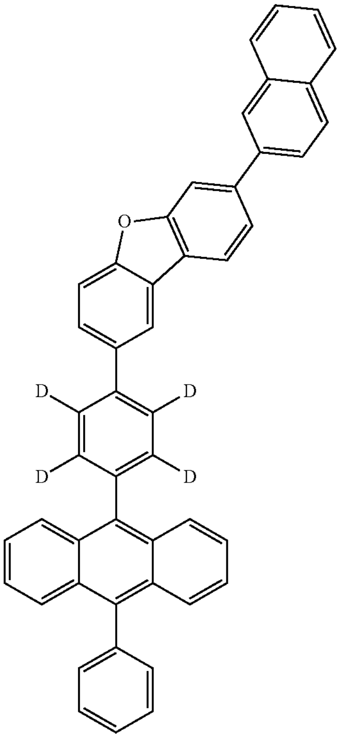
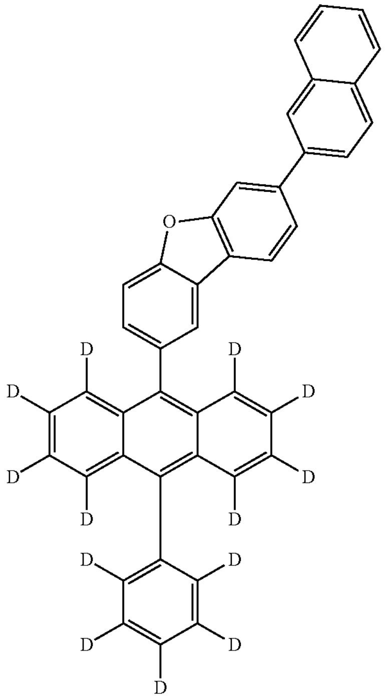
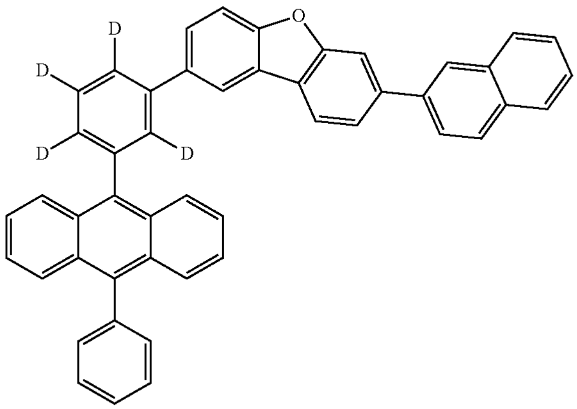

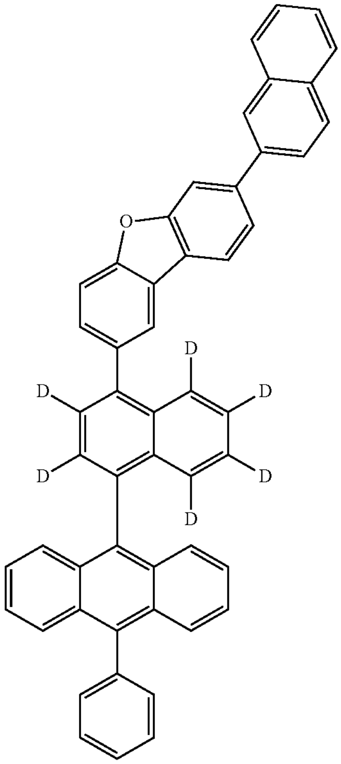
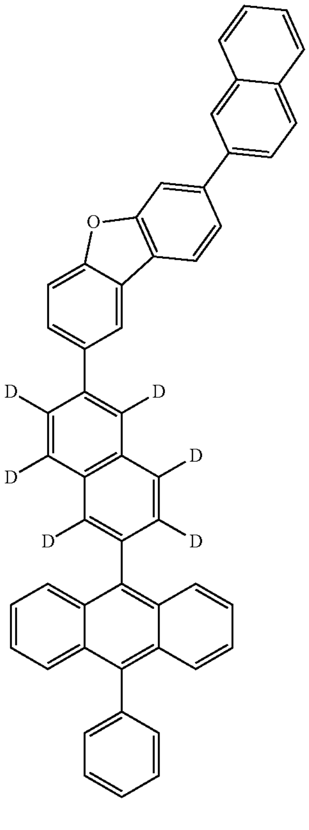
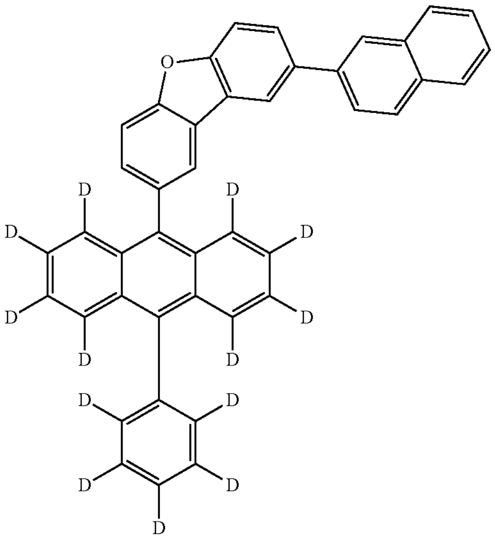
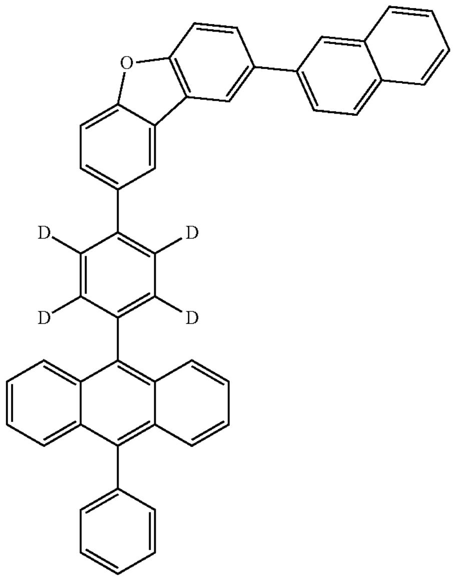
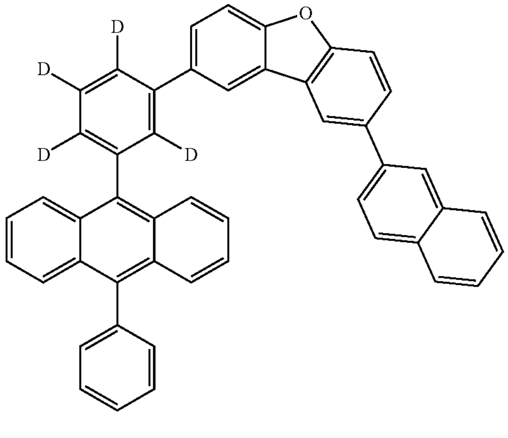

-continued
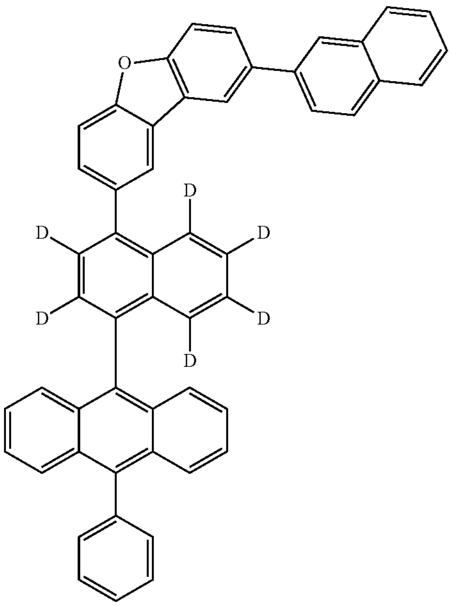
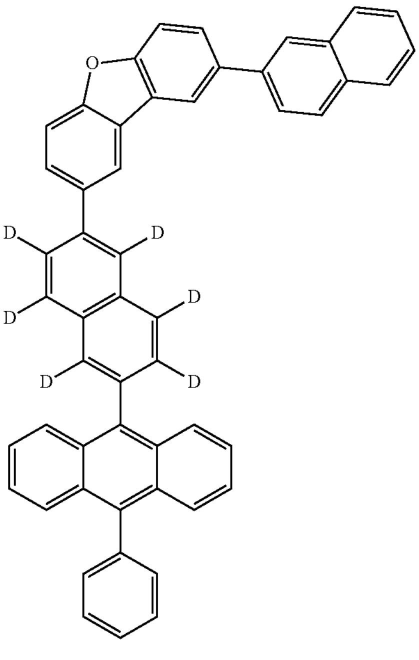
-continued
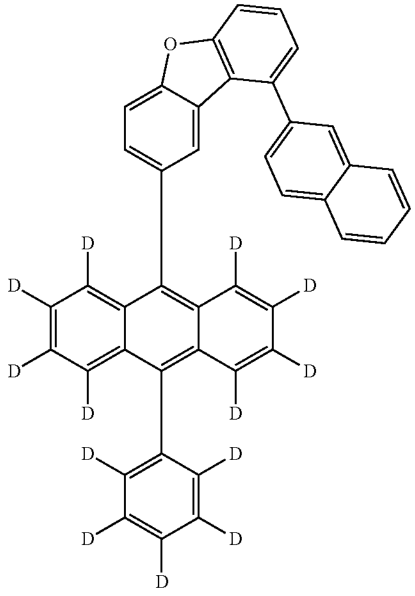
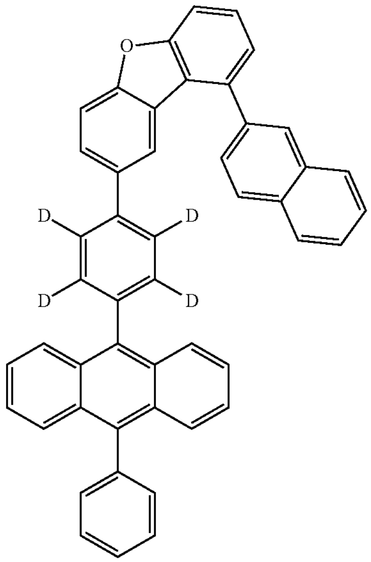
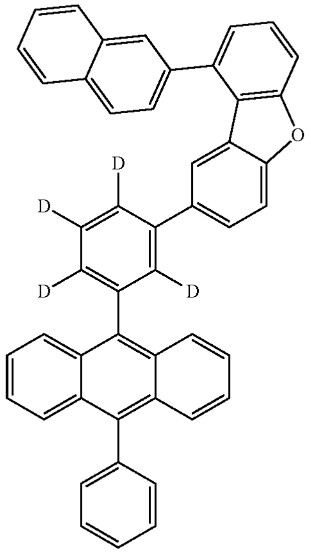

-continued
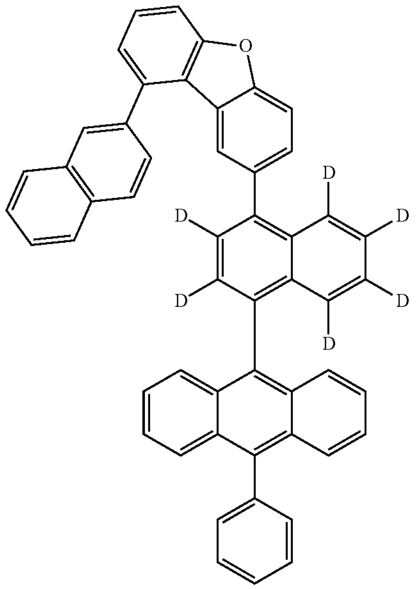
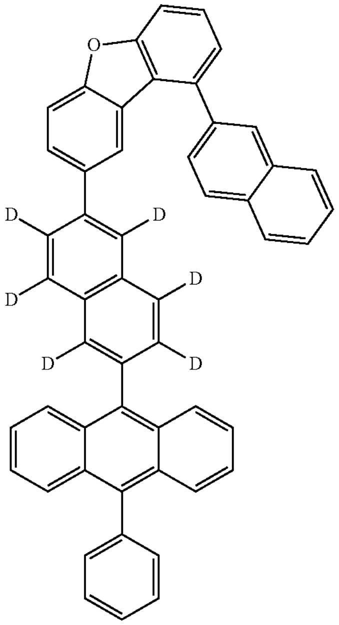
-continued
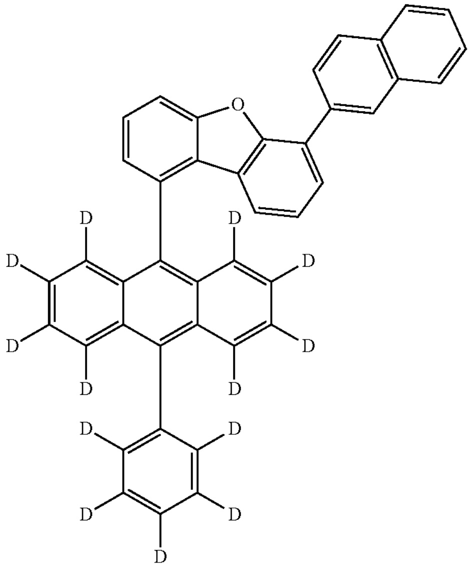
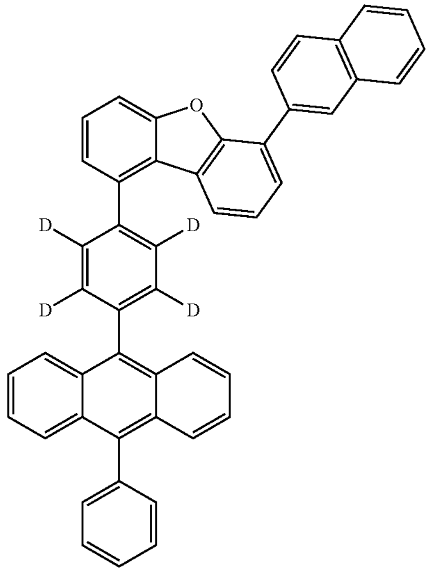

-continued
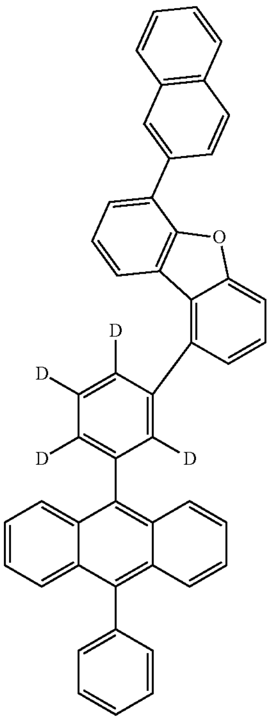
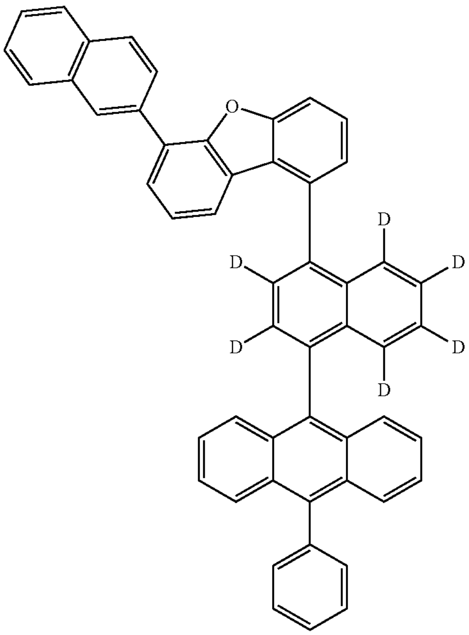
-continued
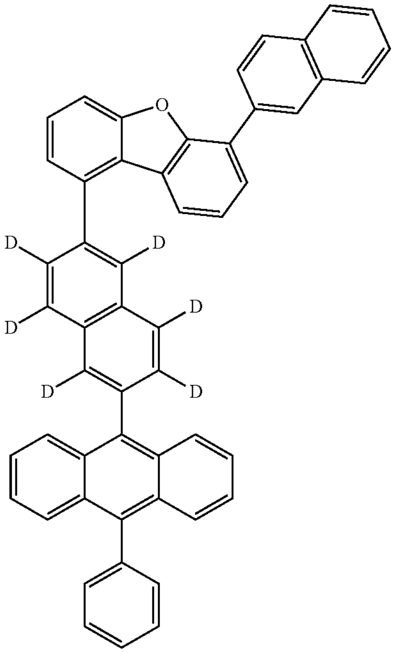
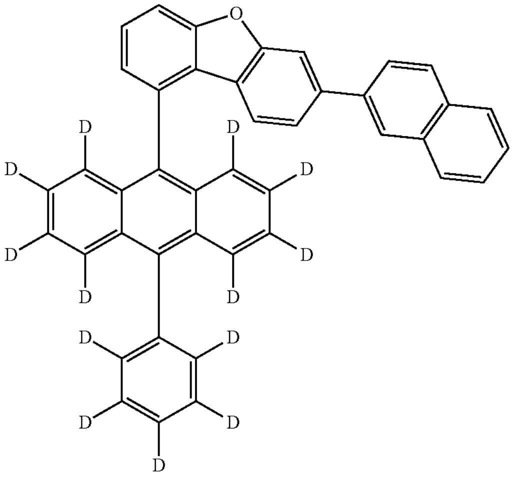
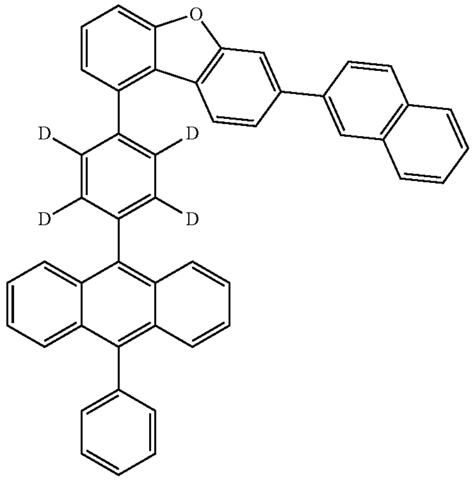

-continued
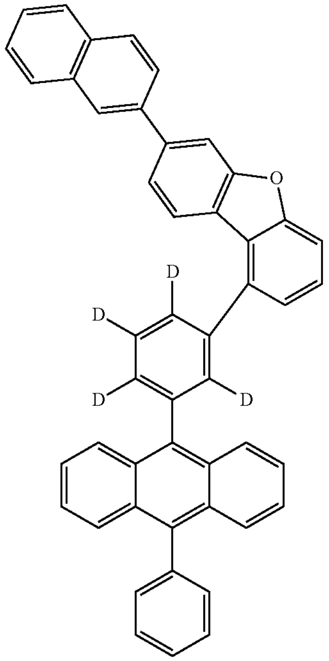
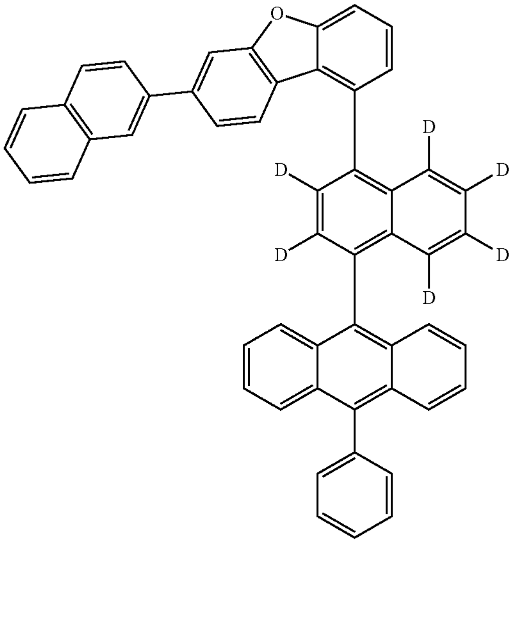
-continued
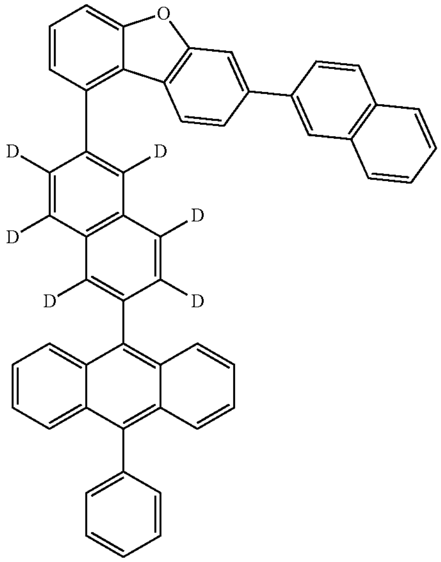
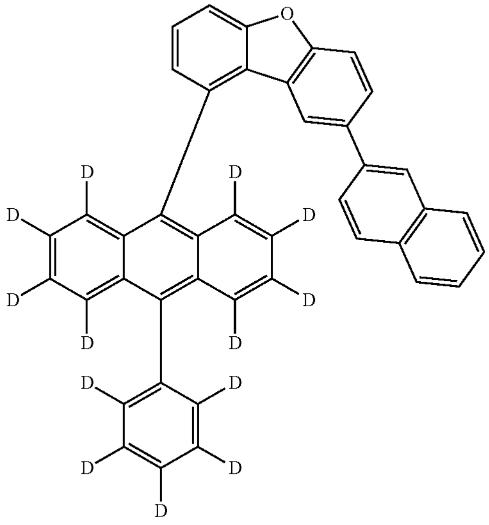
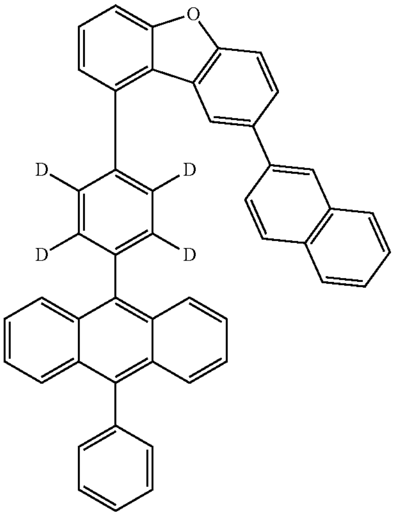

-continued
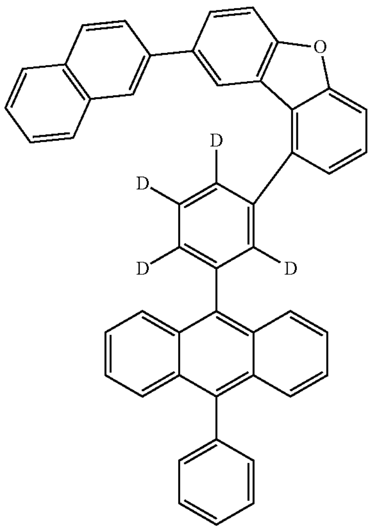
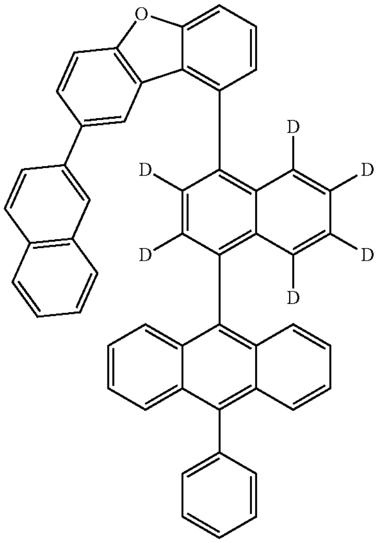
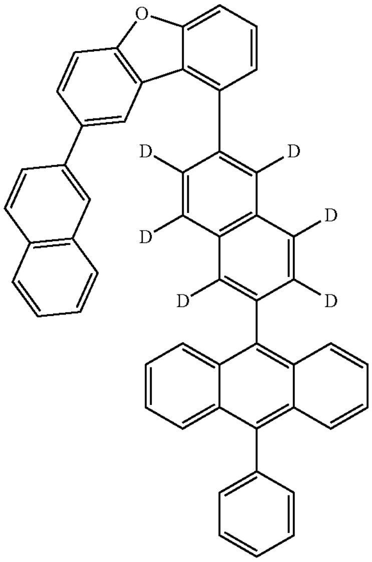
-continued
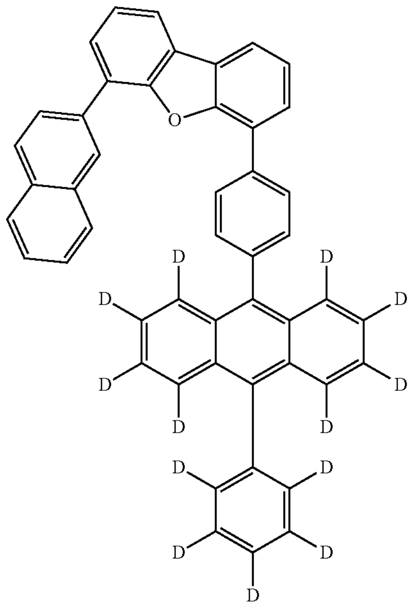
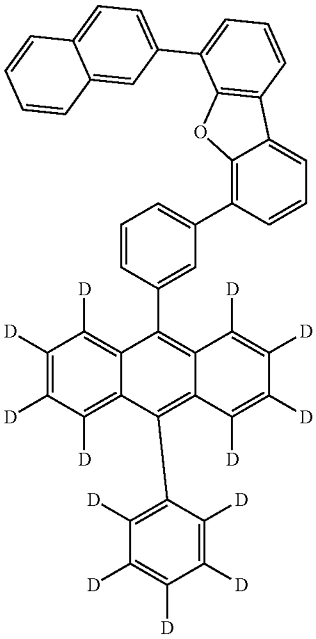

-continued
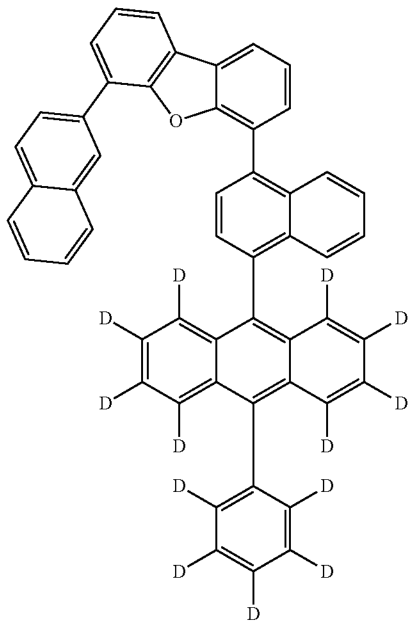
-continued
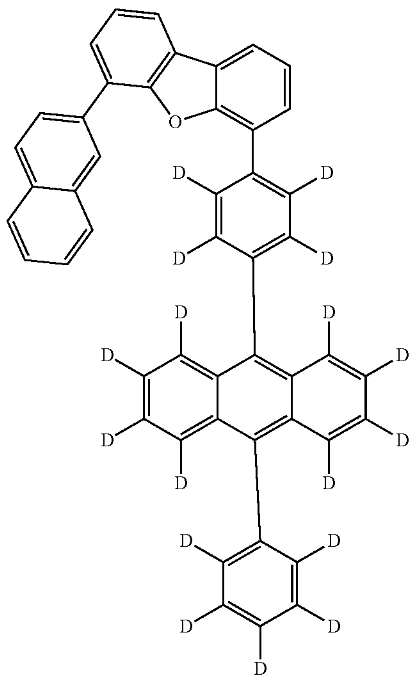
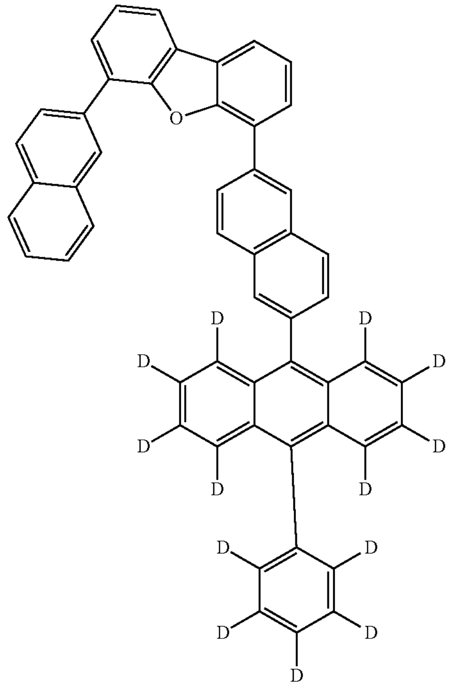
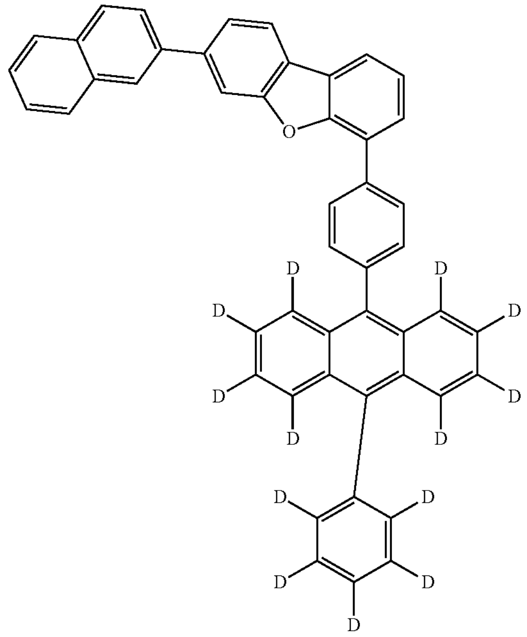

-continued
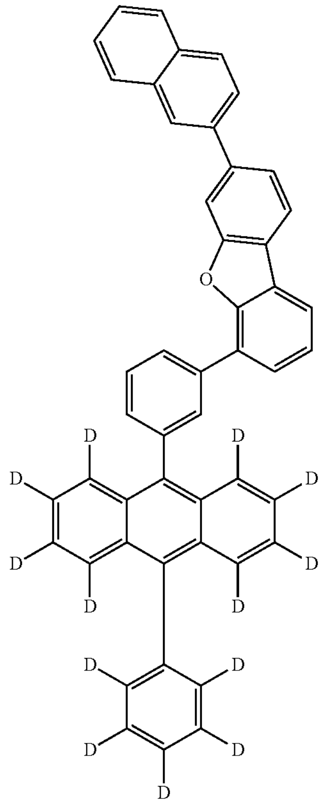
-continued
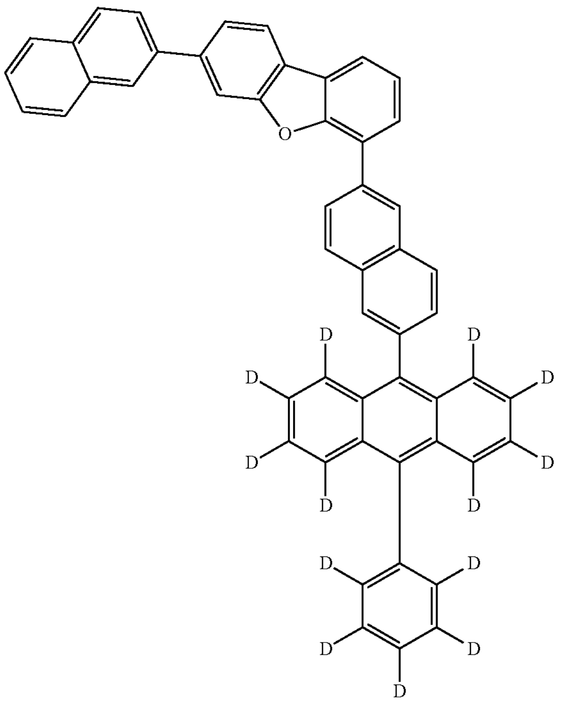
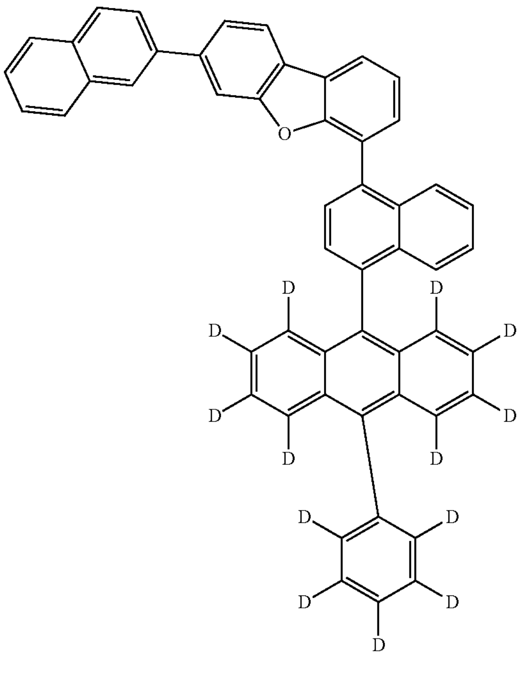
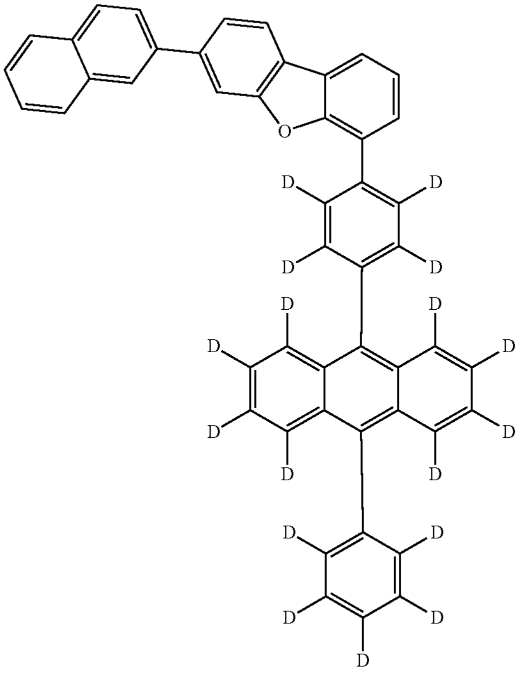

-continued
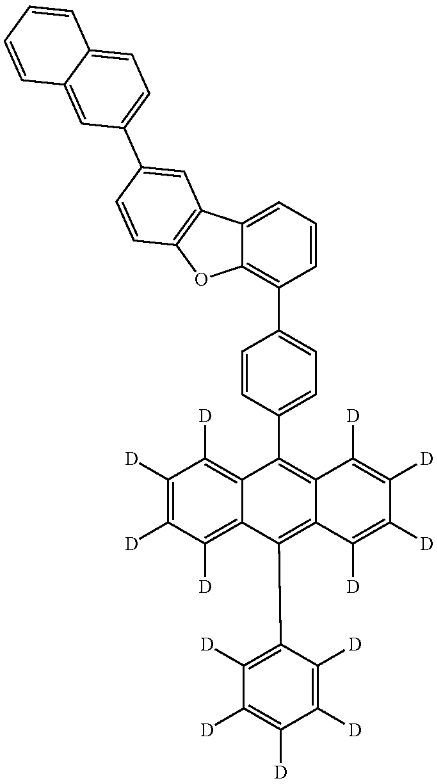
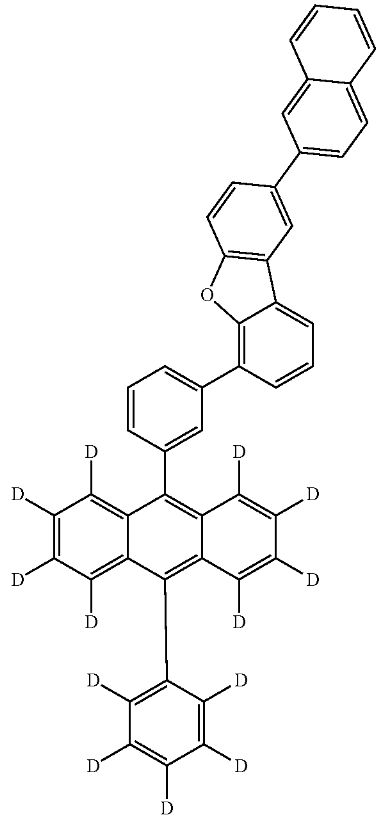
-continued
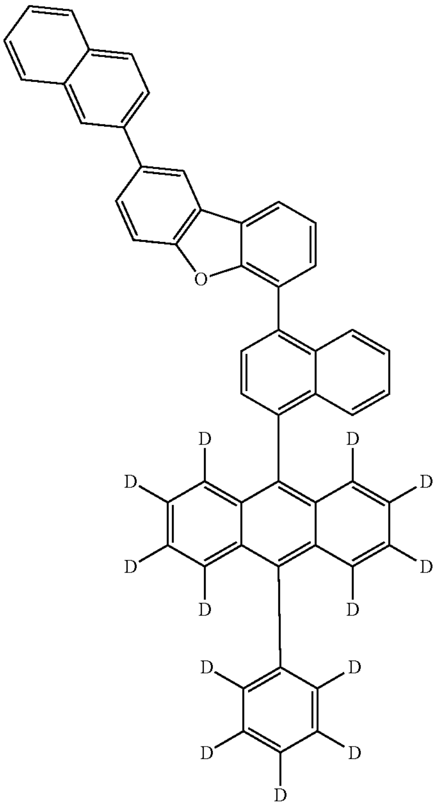
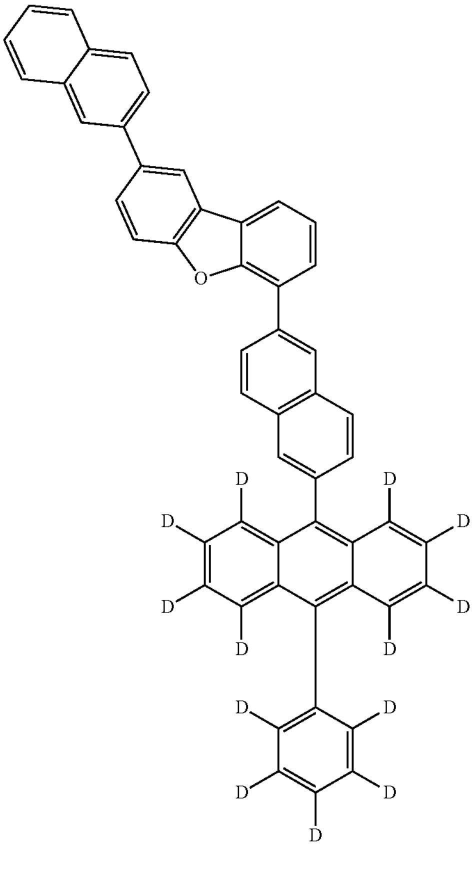

-continued
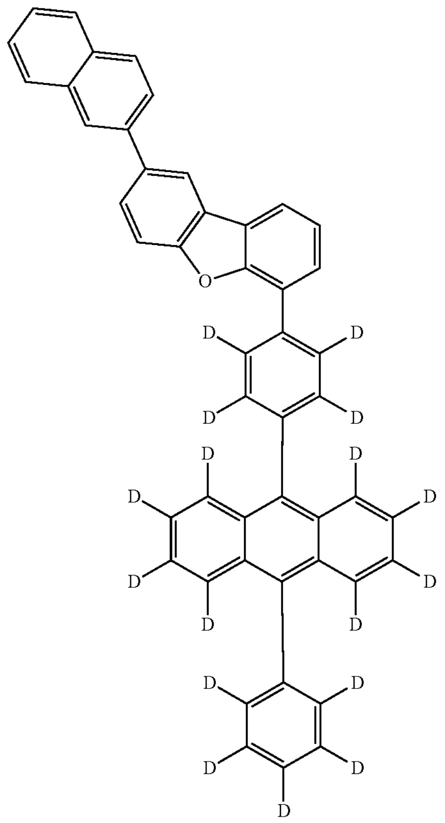
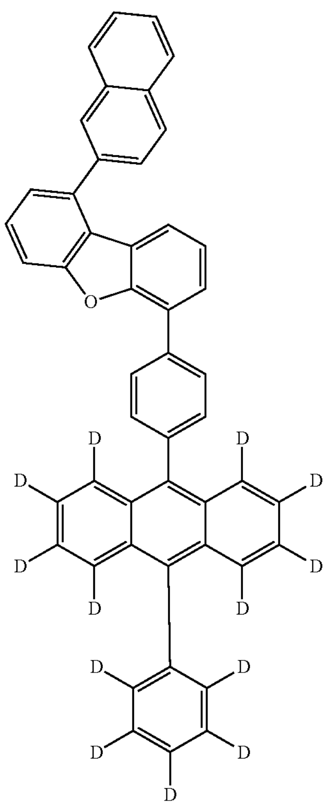
-continued
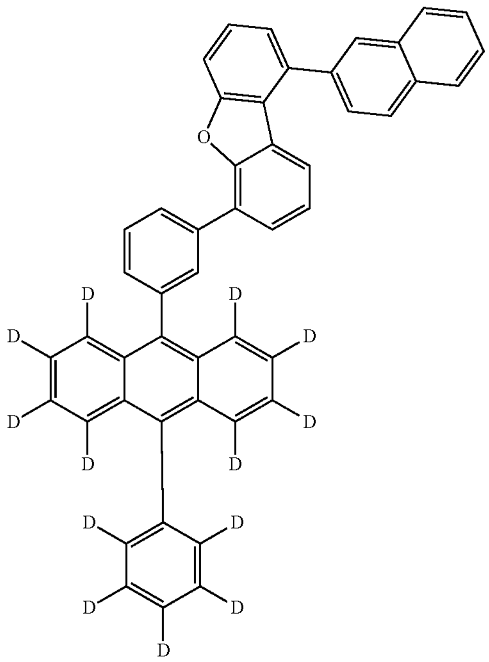
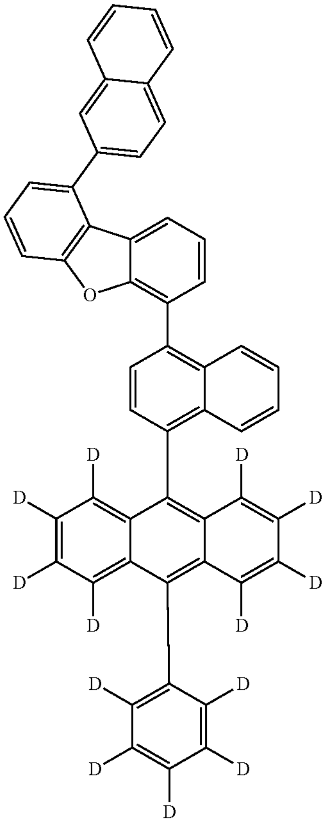

-continued
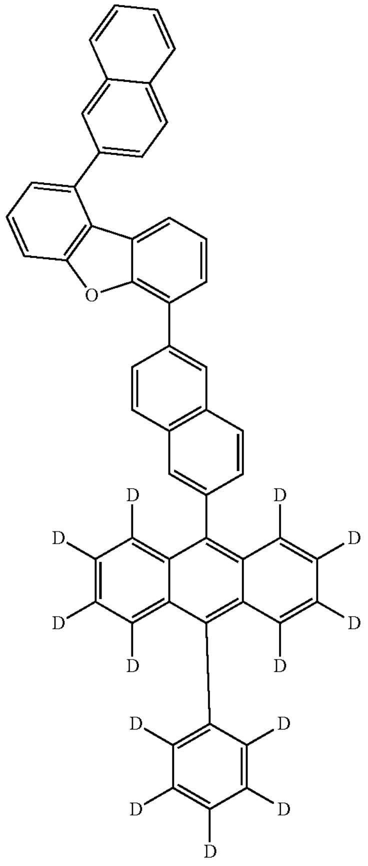
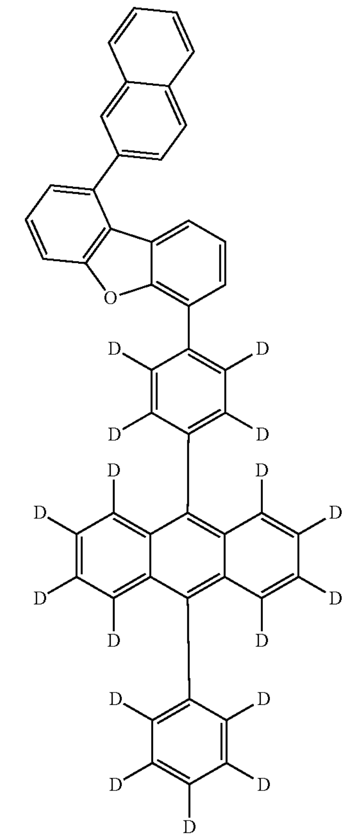
-continued
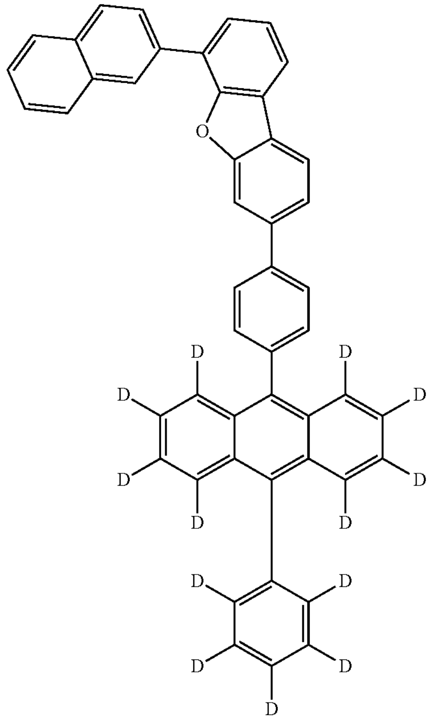
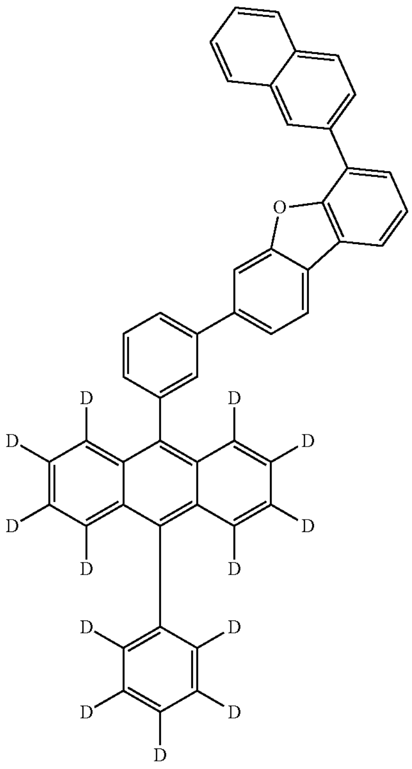

-continued
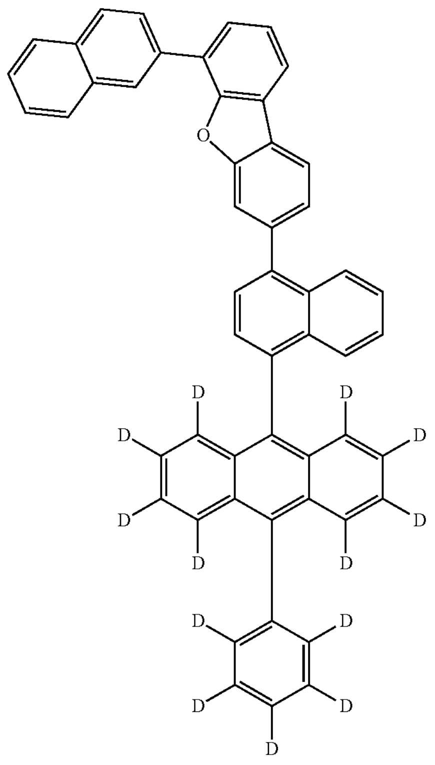
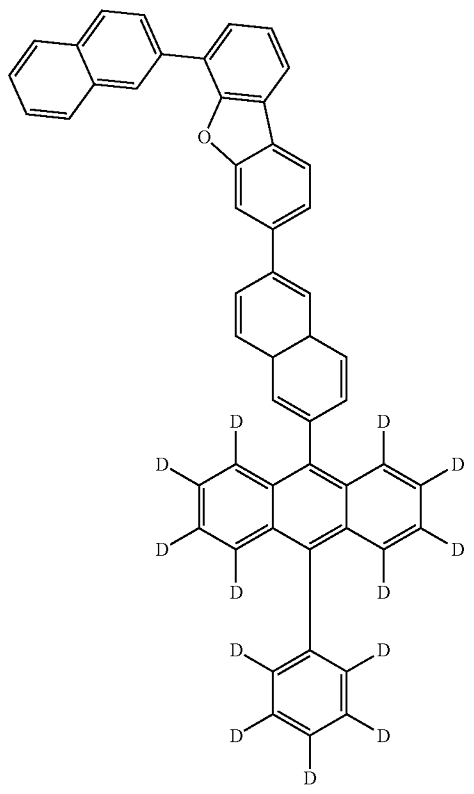
-continued
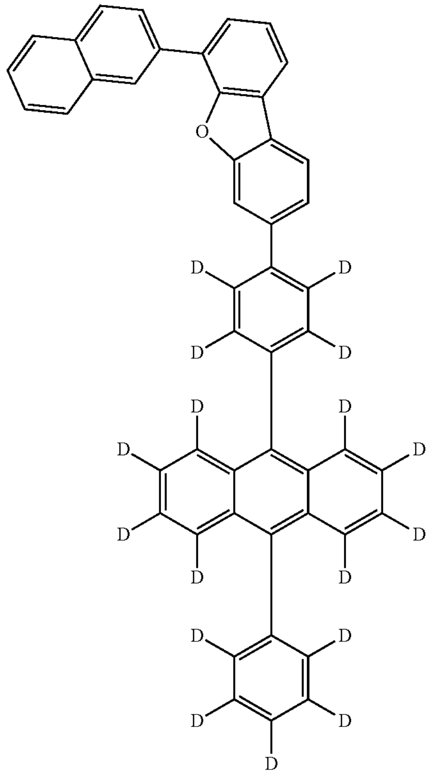
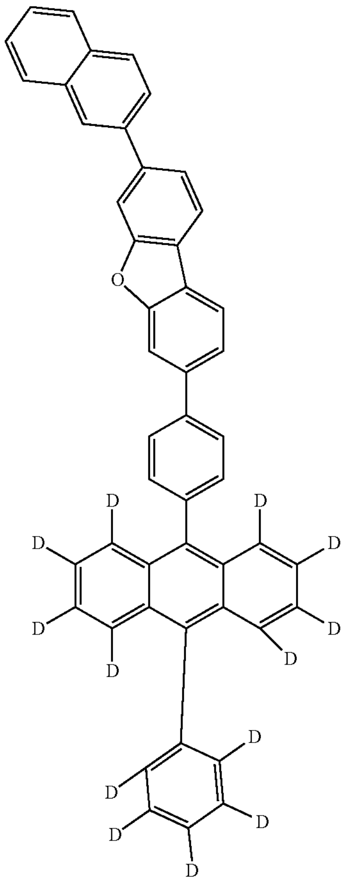

-continued
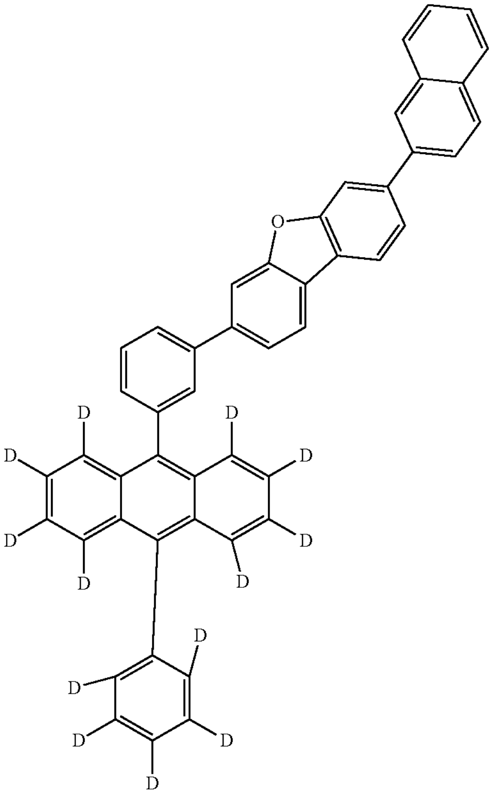
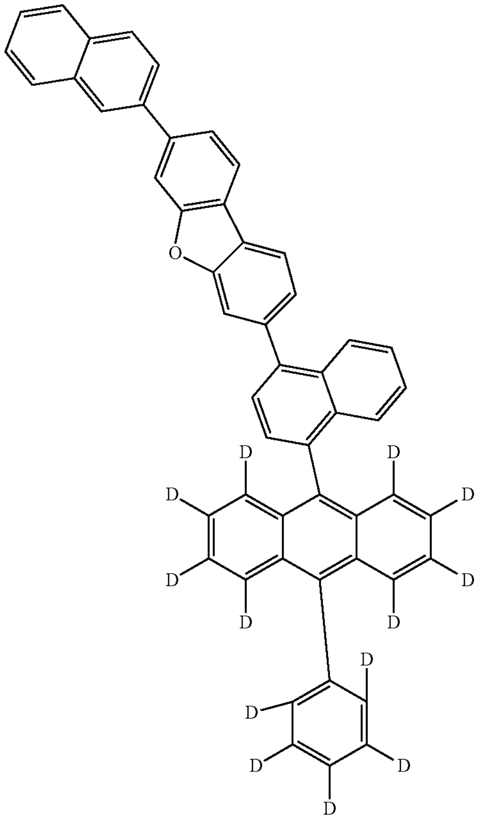
-continued
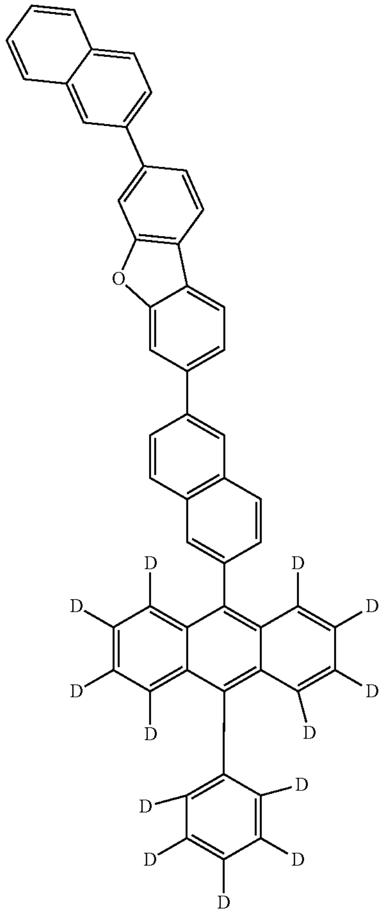

-continued
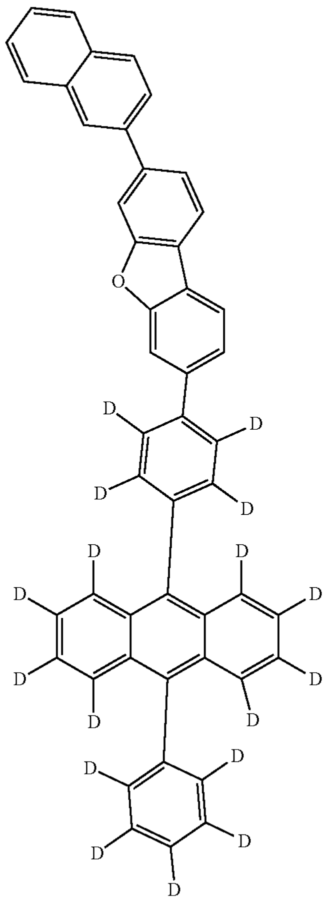
-continued
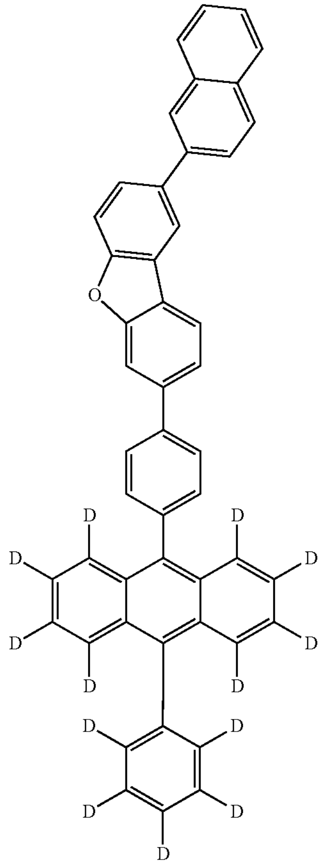
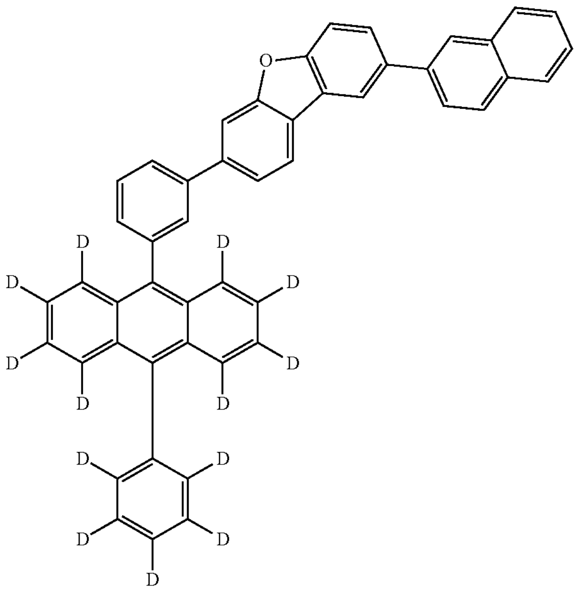

-continued
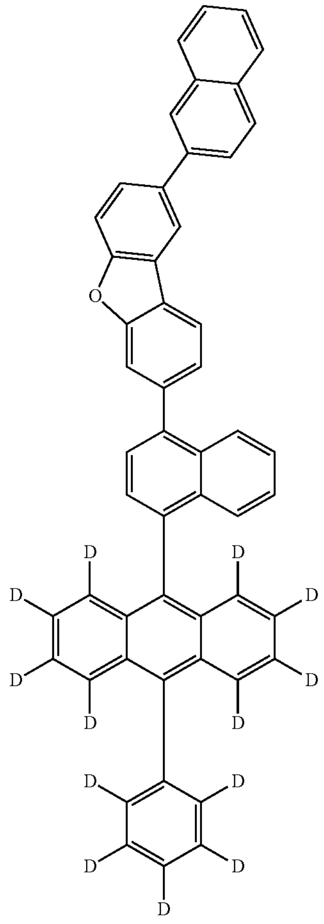
-continued
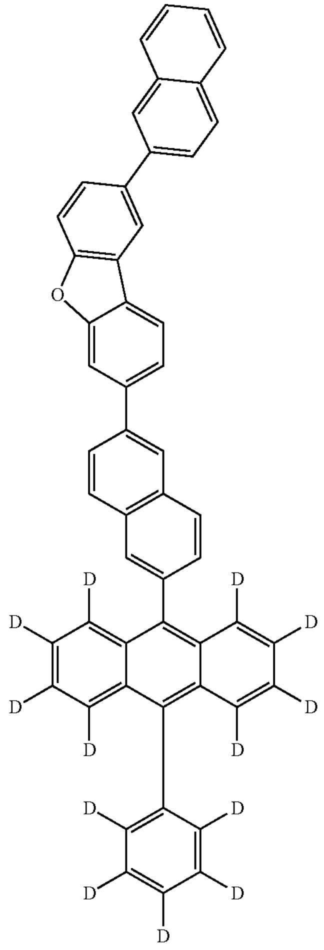

-continued
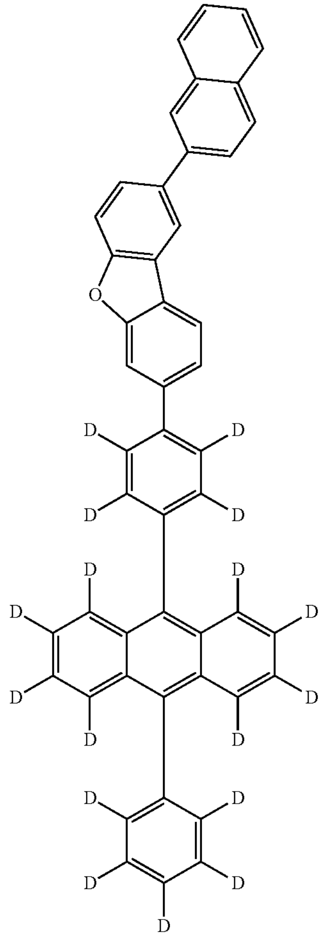
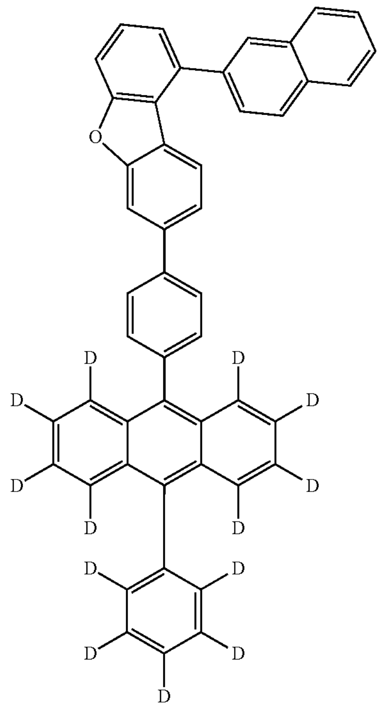
-continued
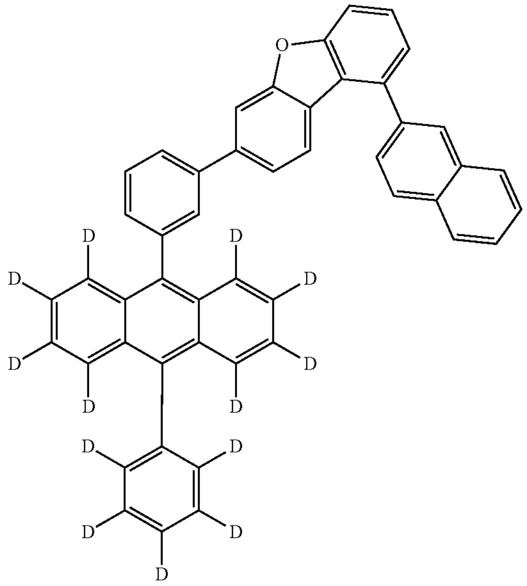
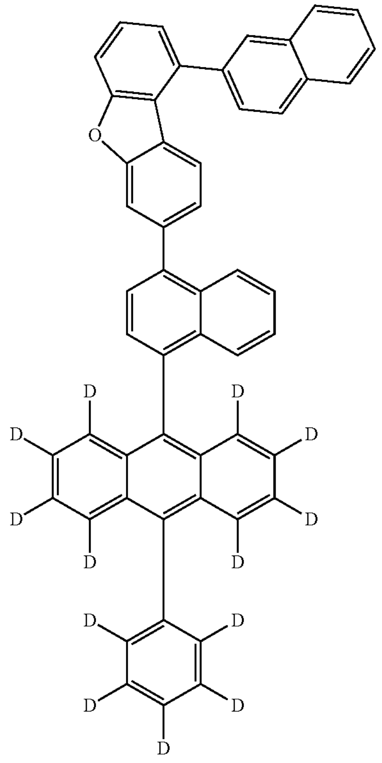

-continued
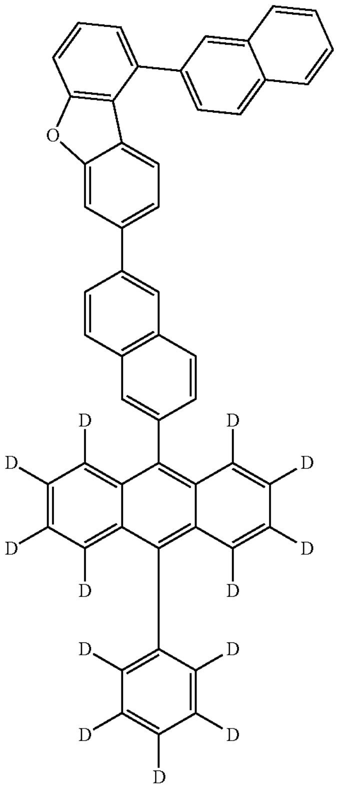
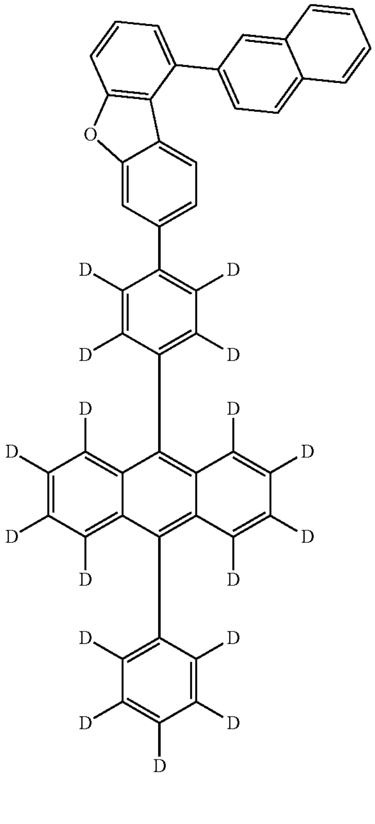
-continued
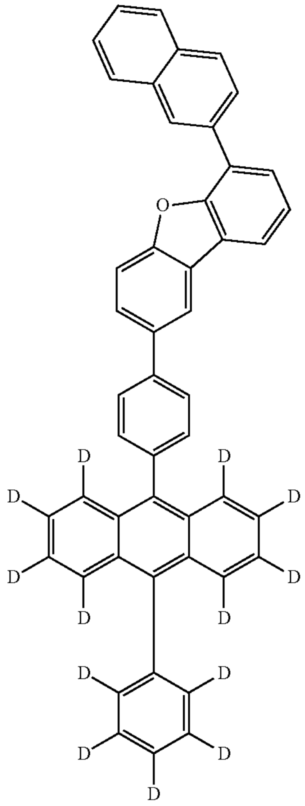
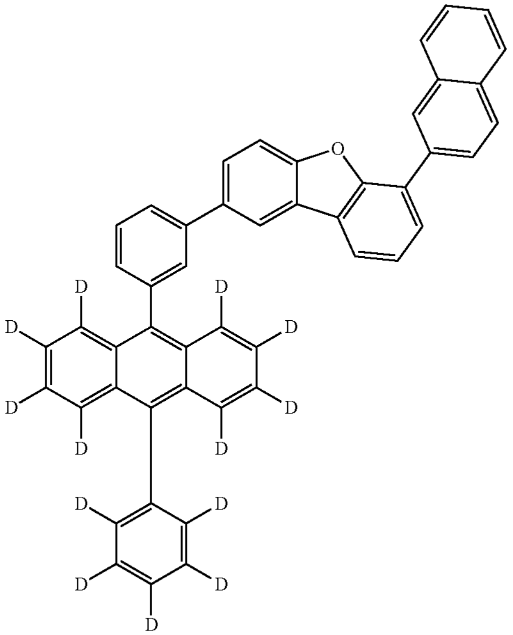

-continued
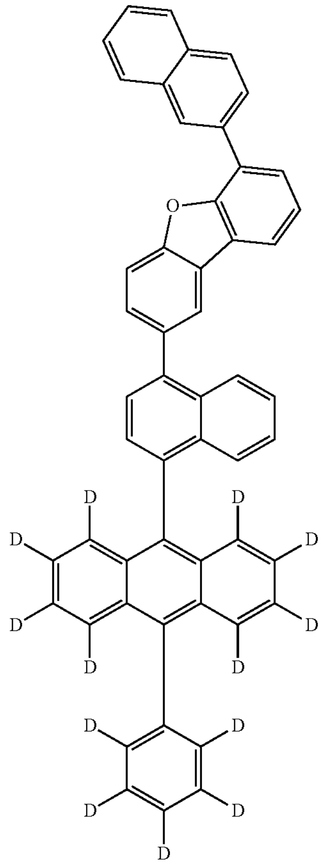
-continued
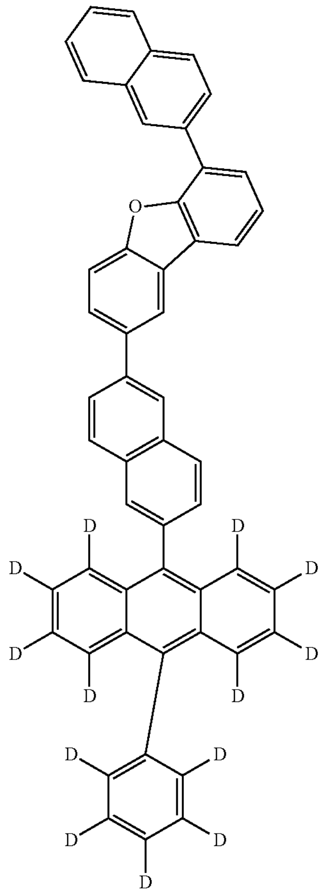

-continued
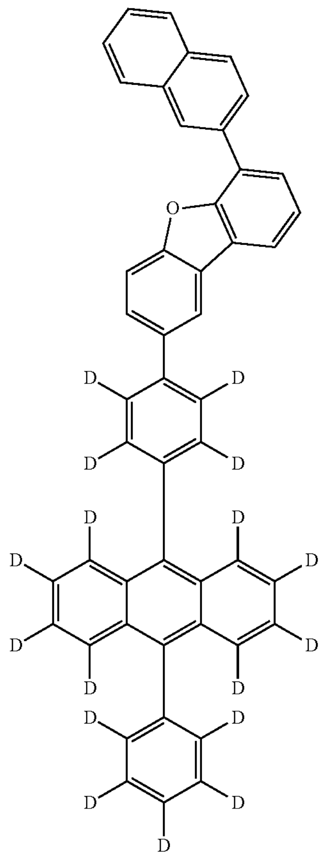
-continued
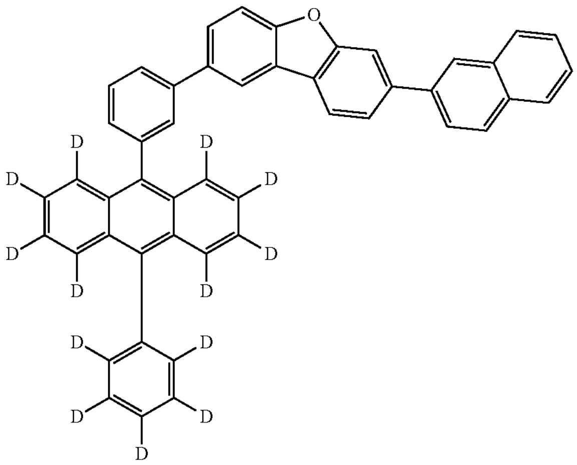
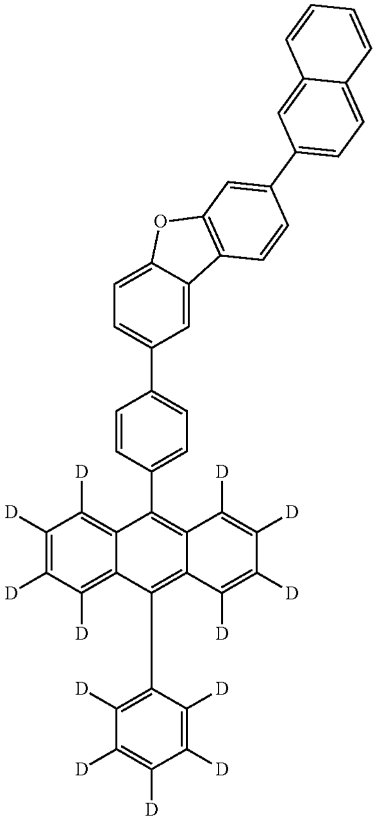
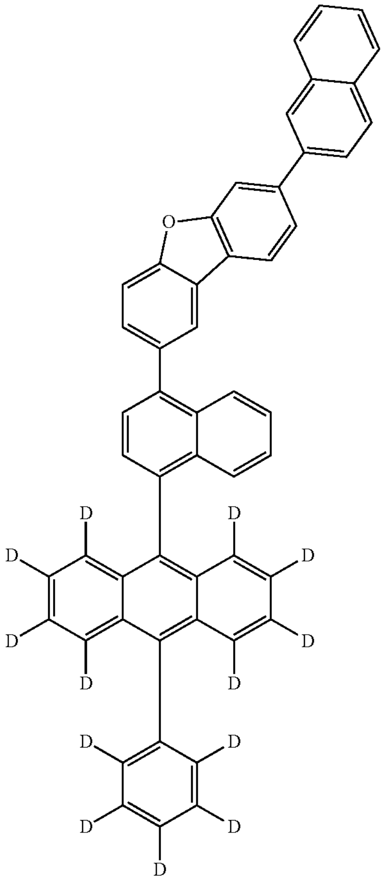

-continued
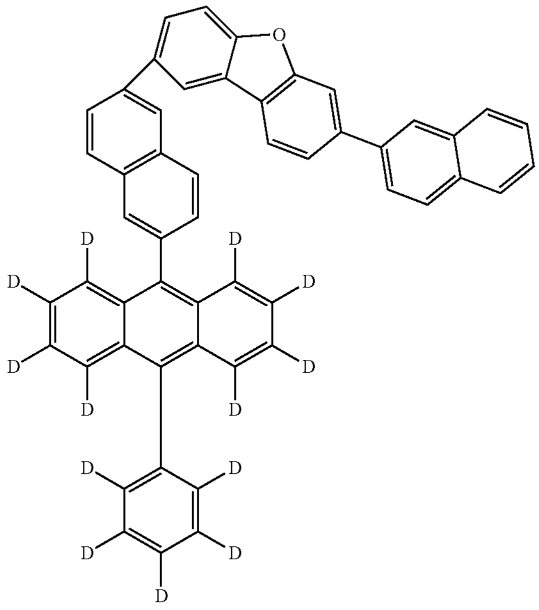
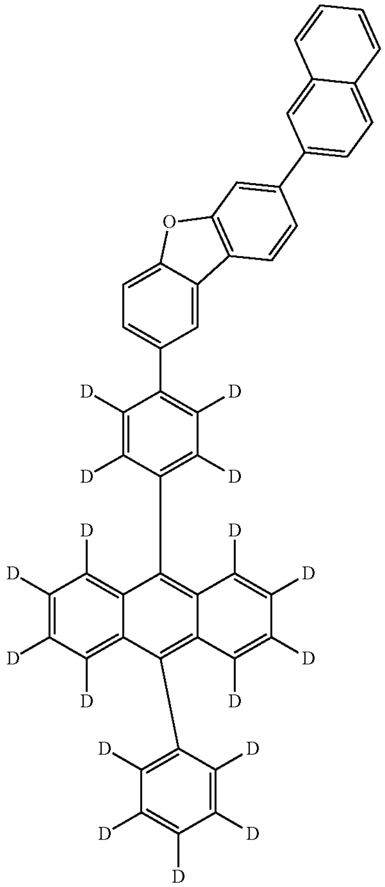
-continued
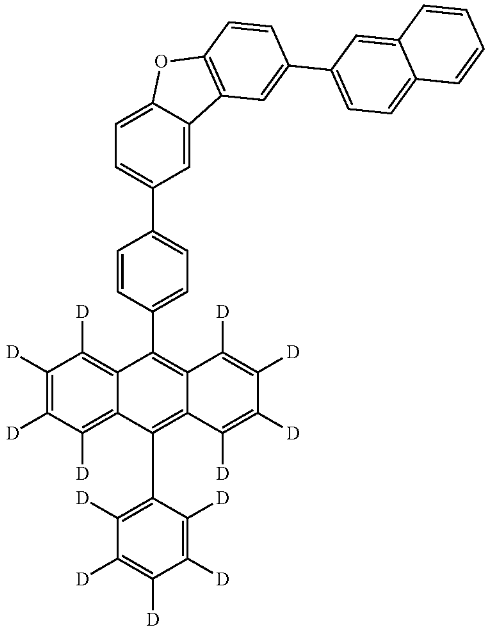
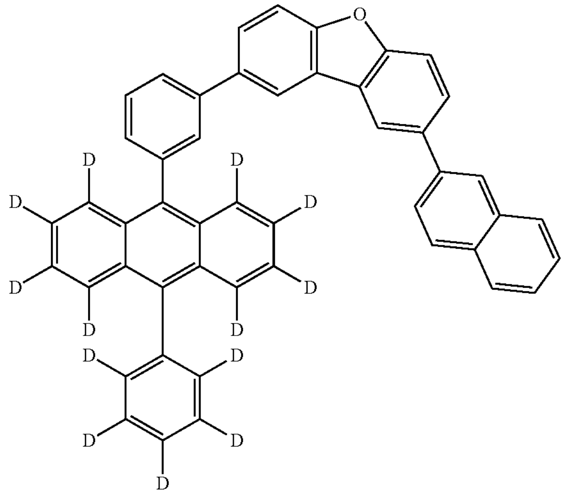

-continued
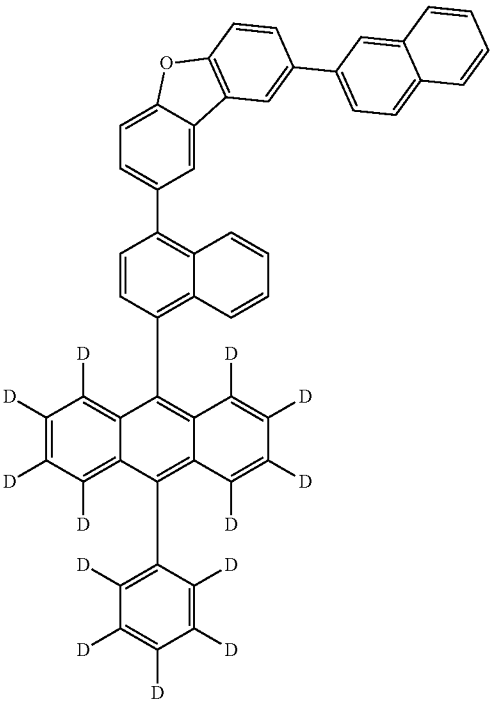
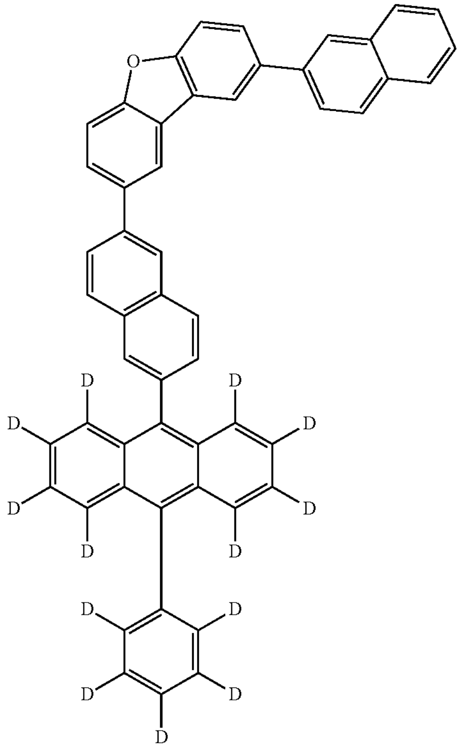
-continued
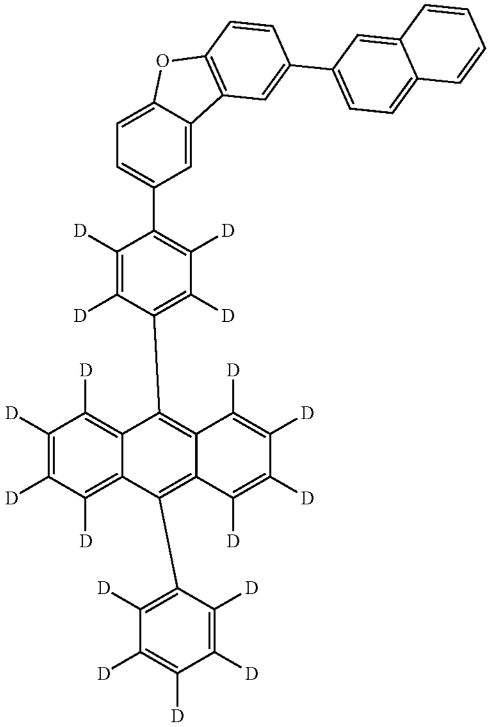
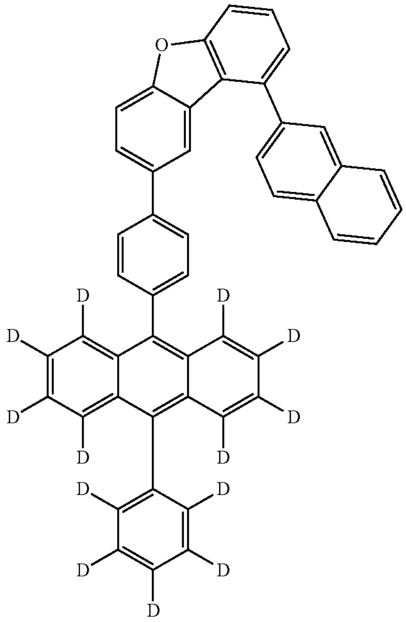

-continued
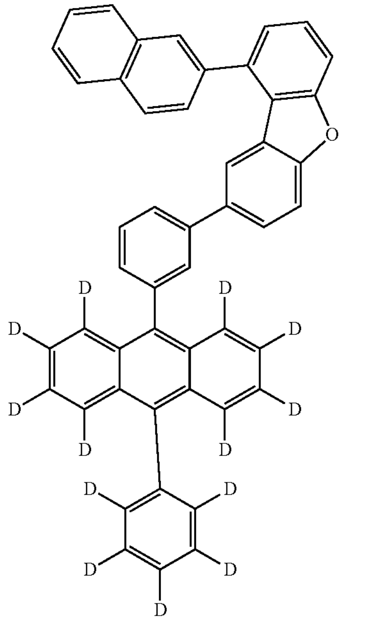
-continued
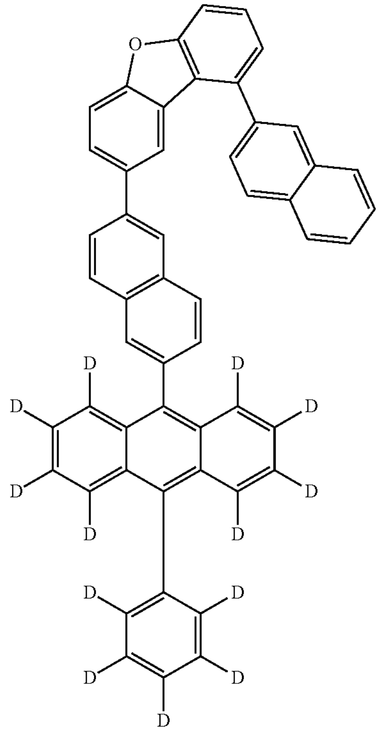
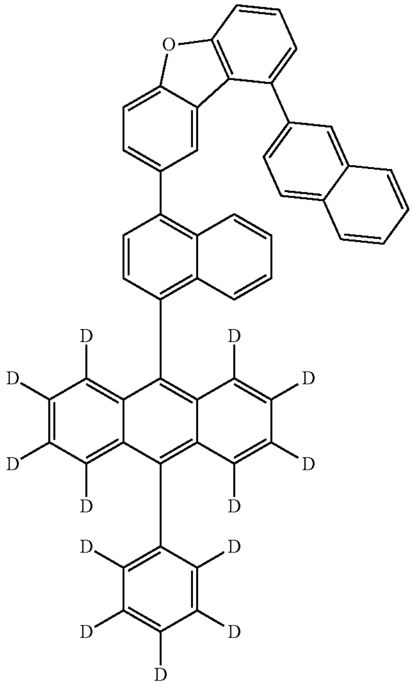
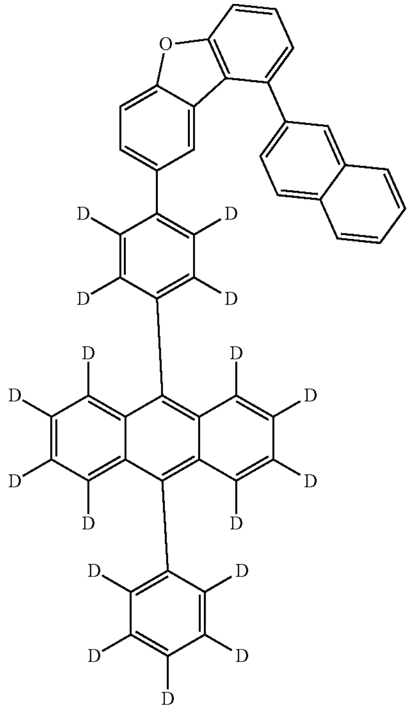

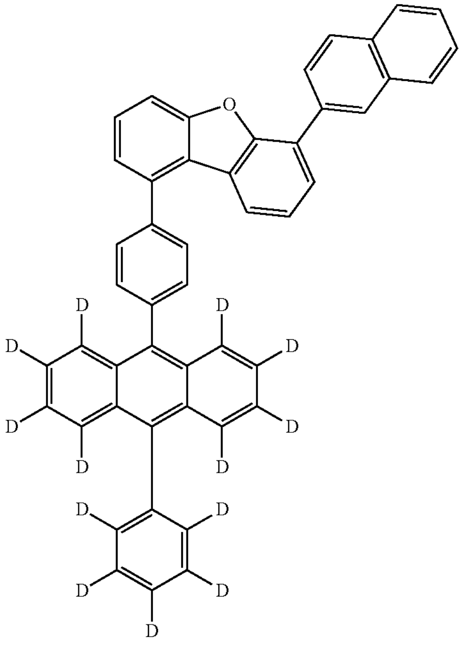
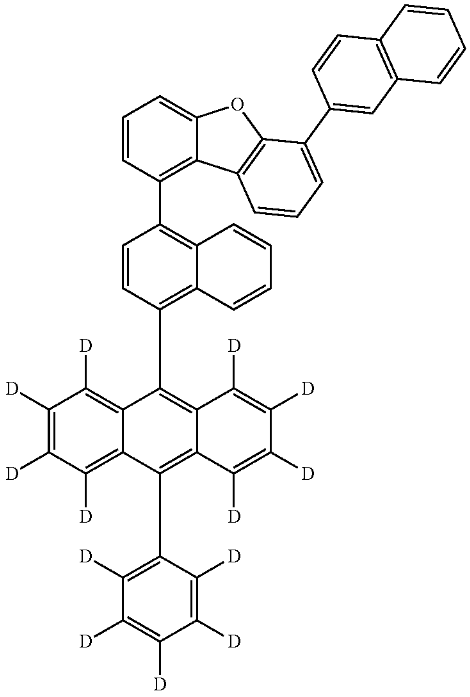
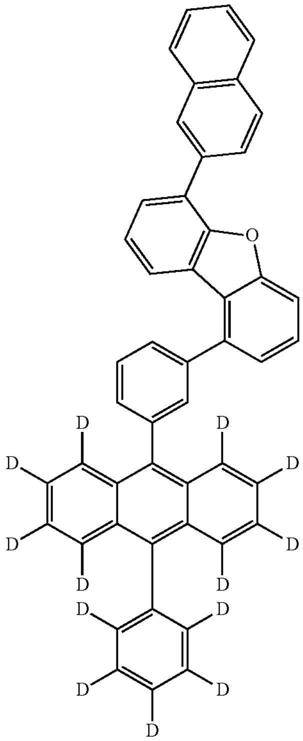
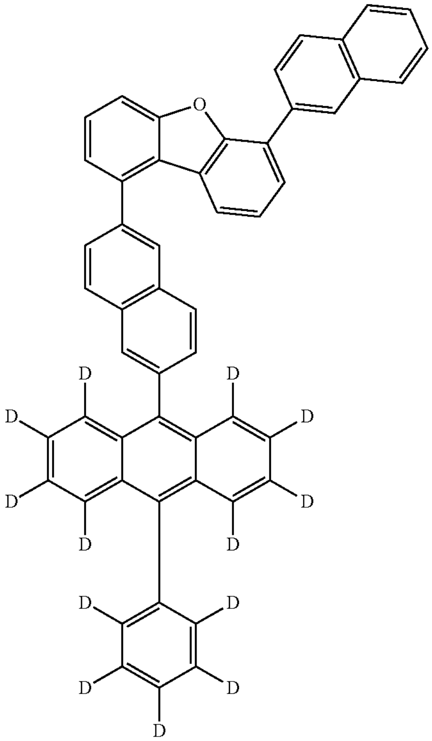

-continued
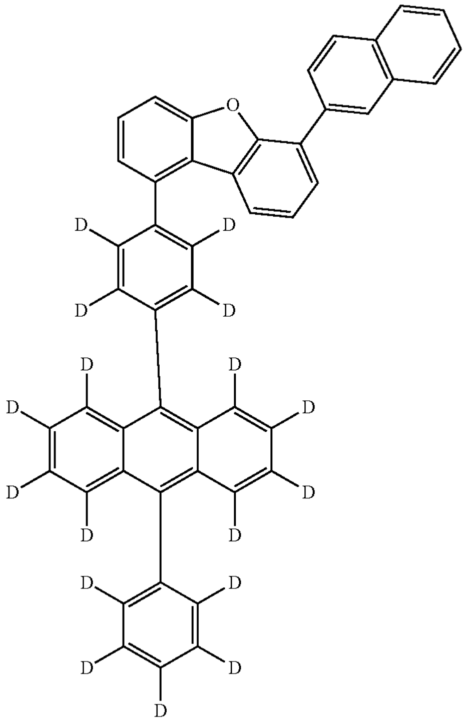
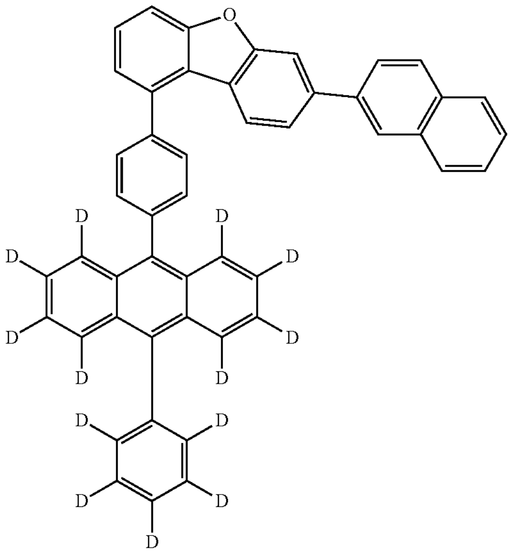
-continued
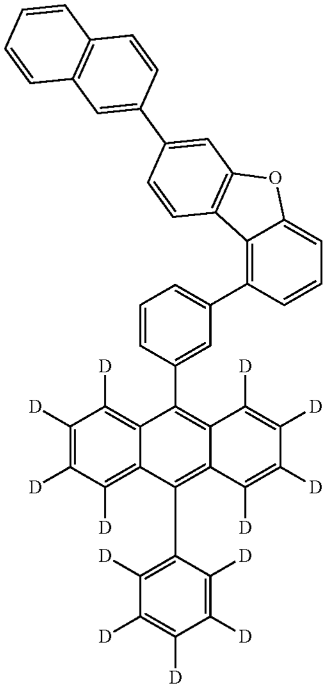
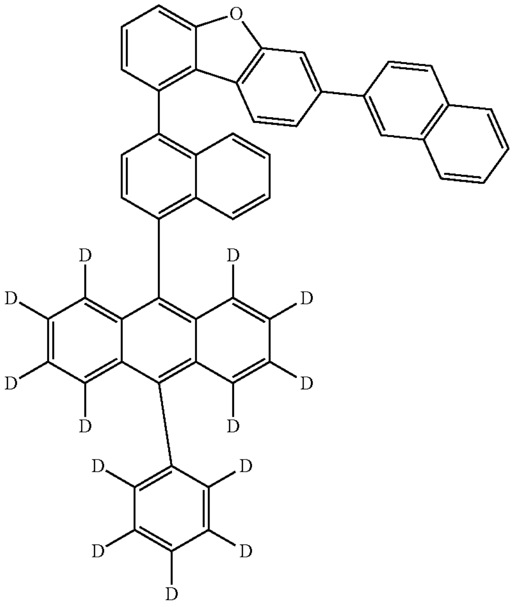

-continued
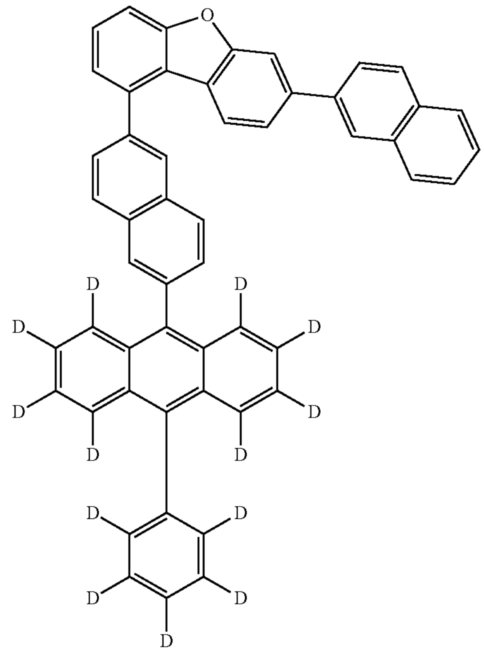
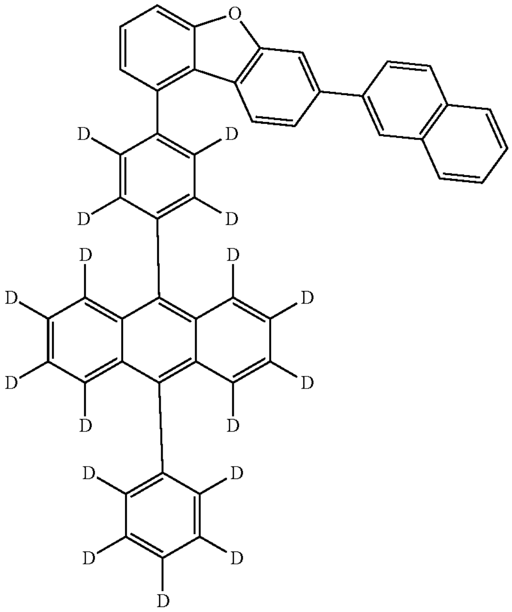
-continued
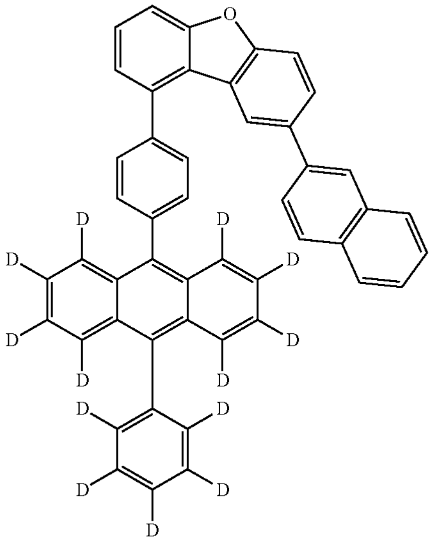
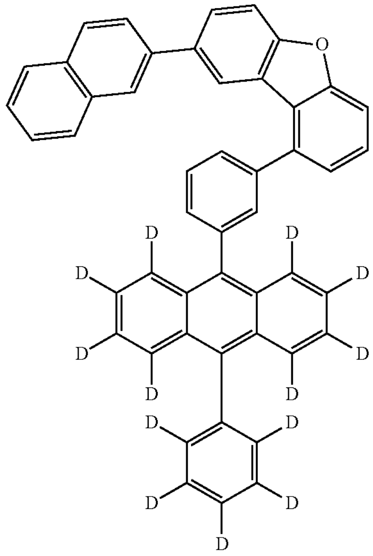
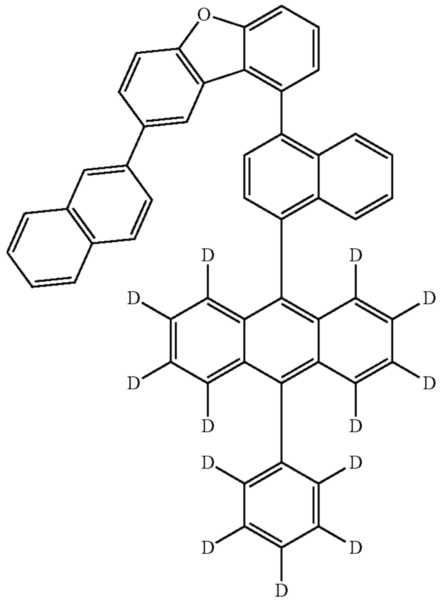

-continued
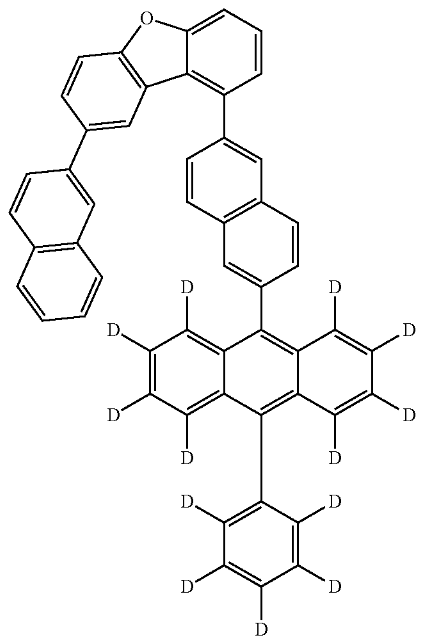
-continued
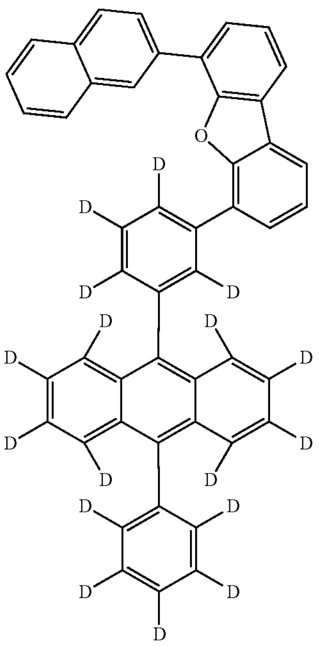
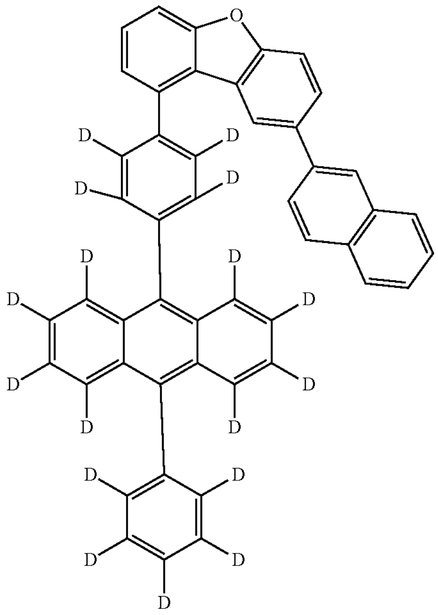
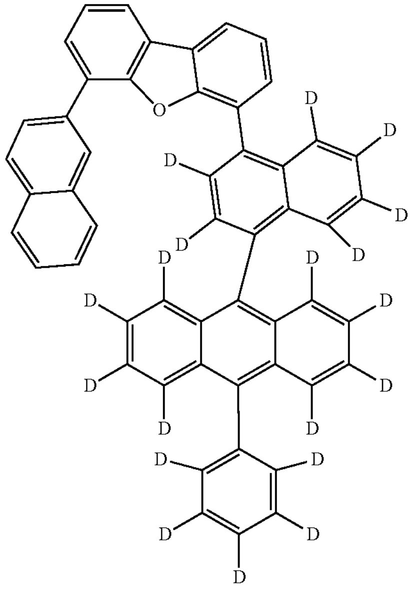

-continued
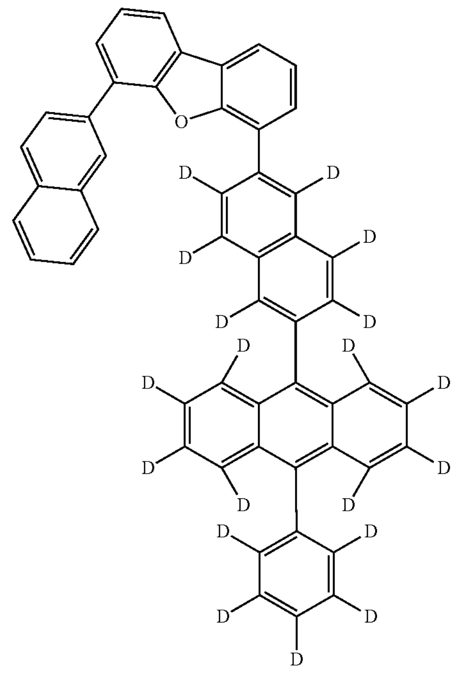
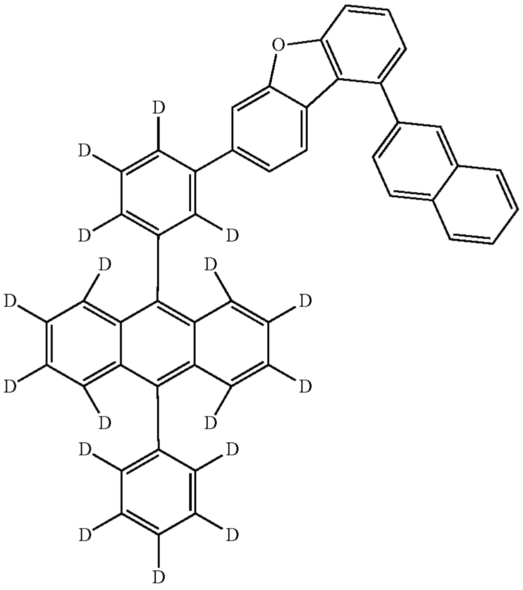
-continued
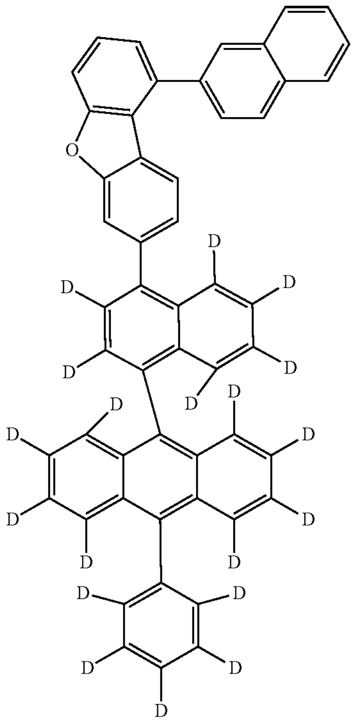
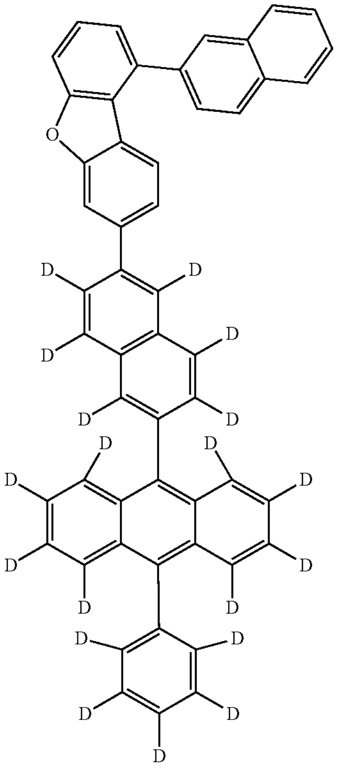

-continued
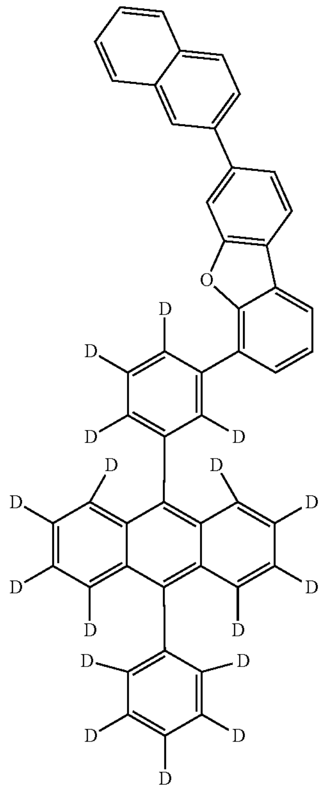
-continued
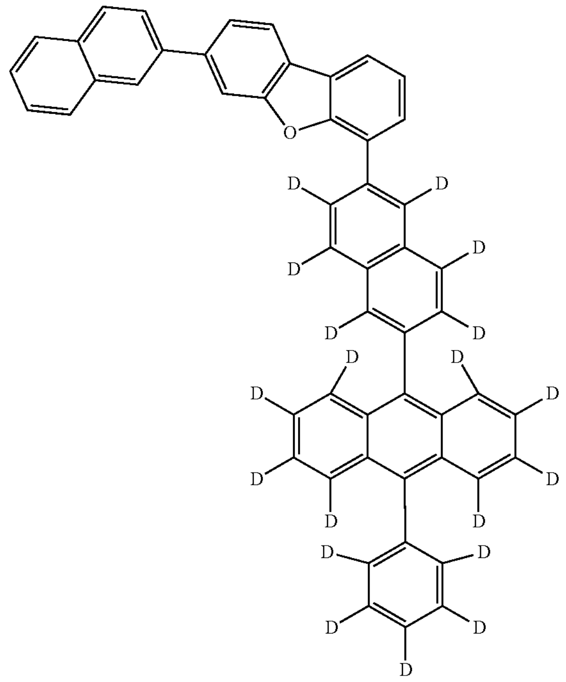
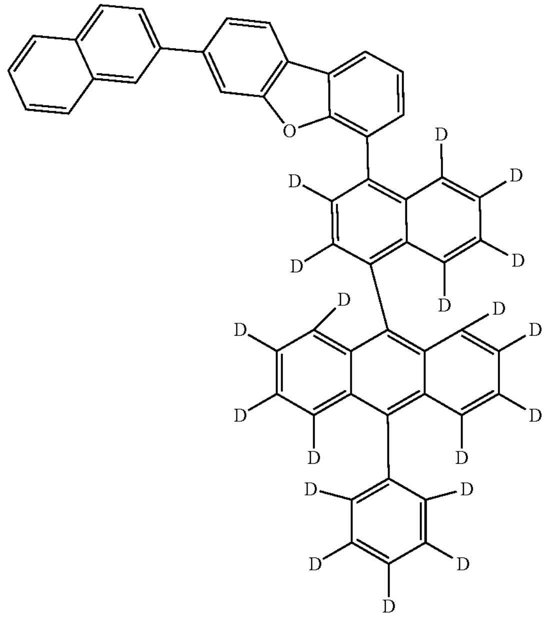
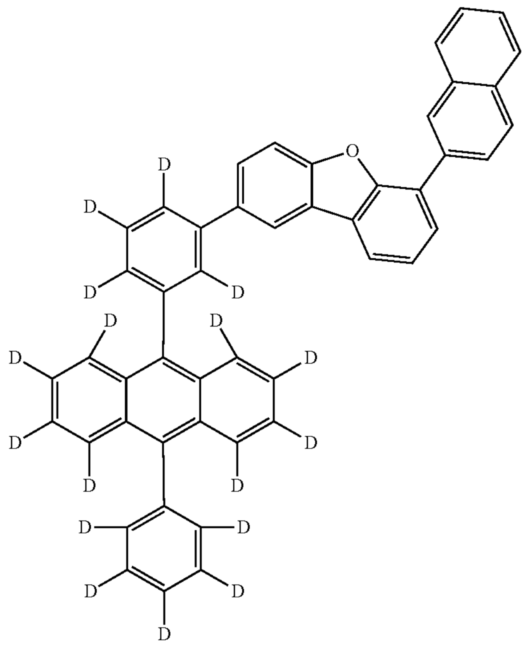

-continued
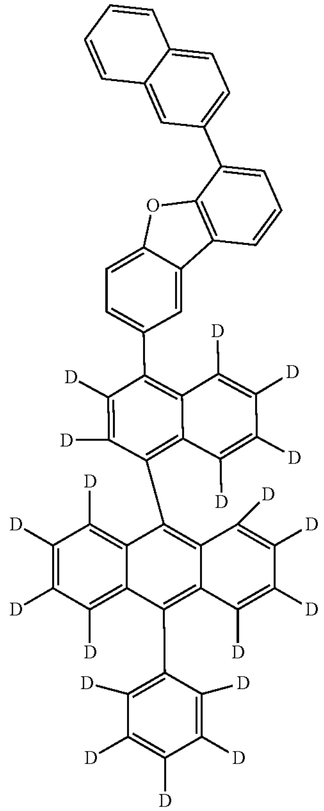
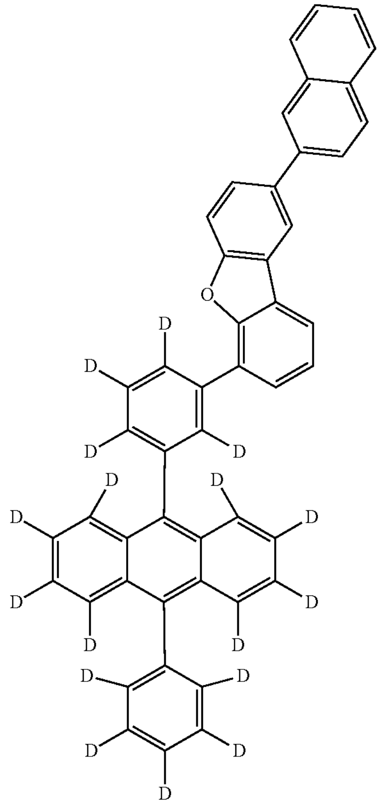
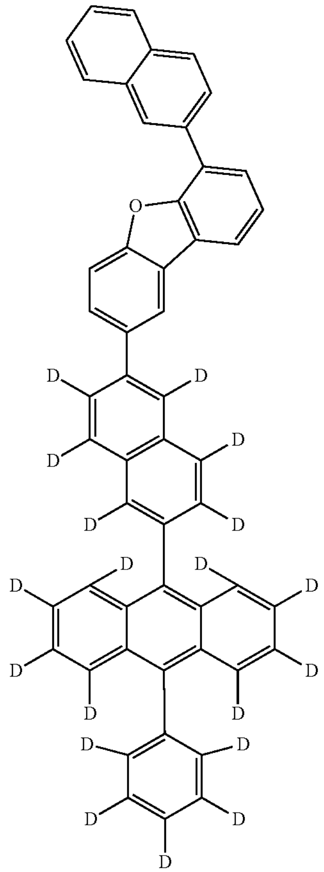
-continued
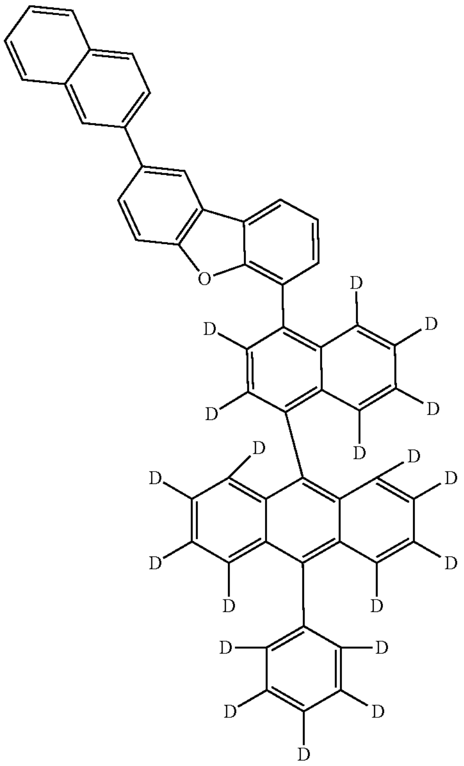

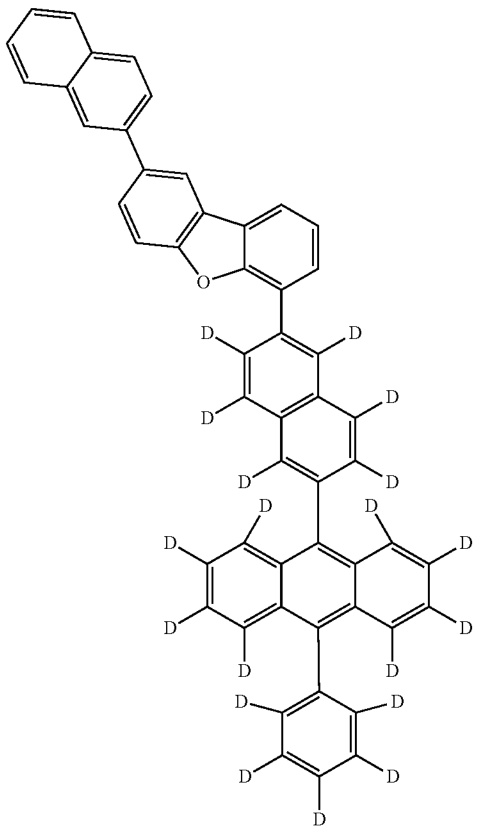
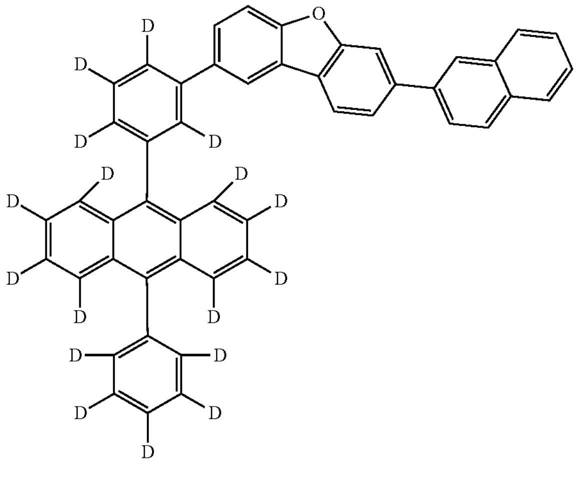
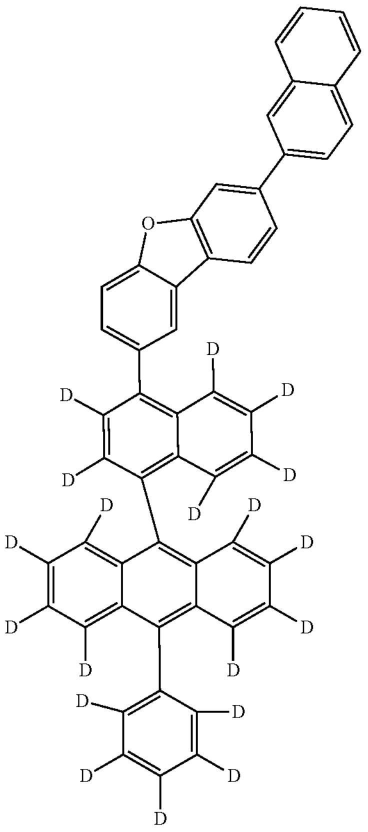
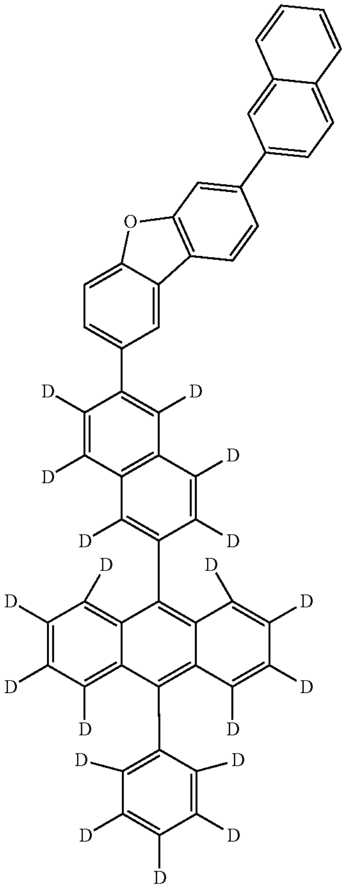

-continued
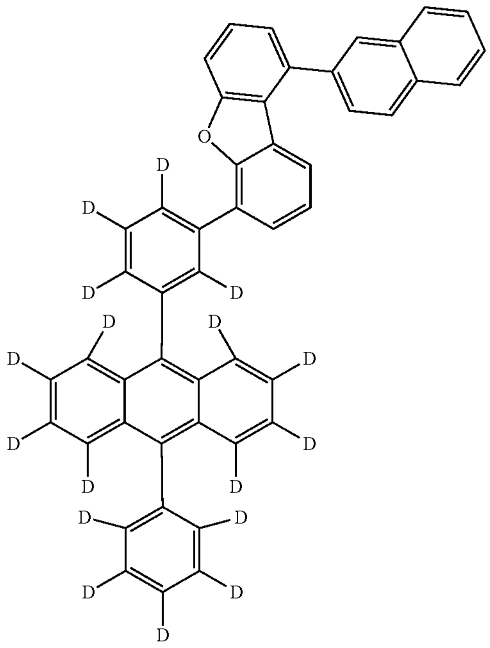
-continued
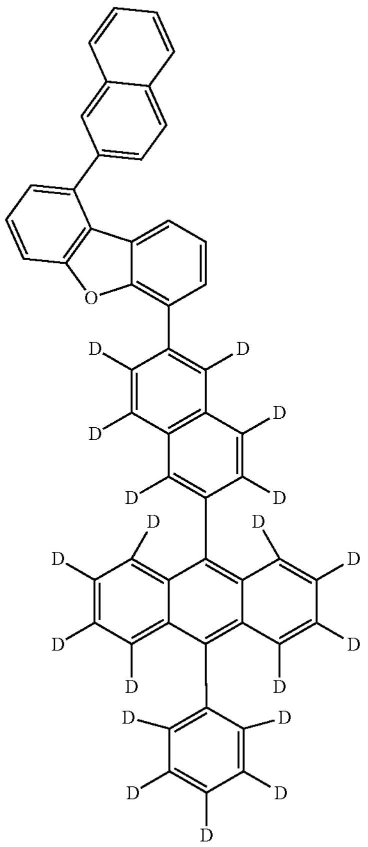
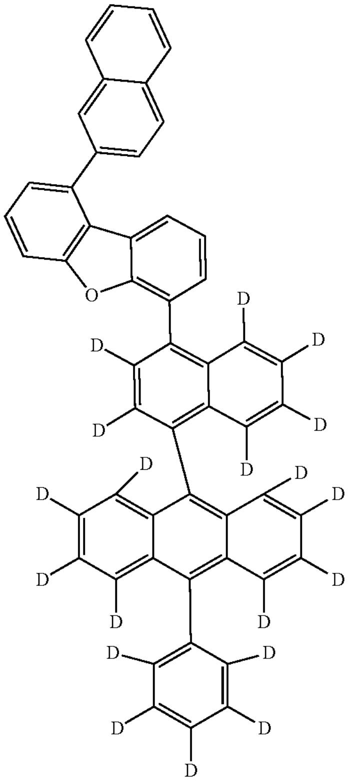
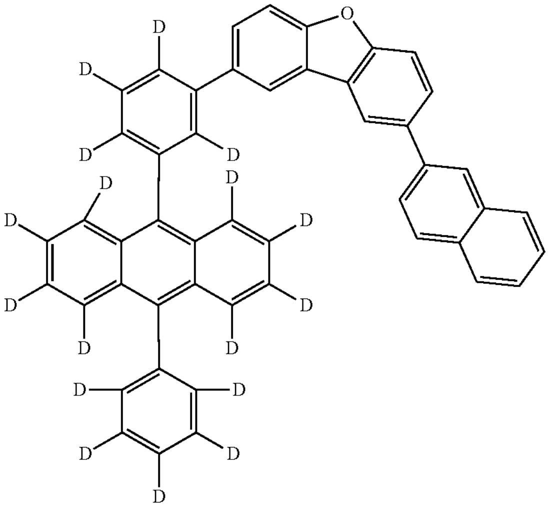

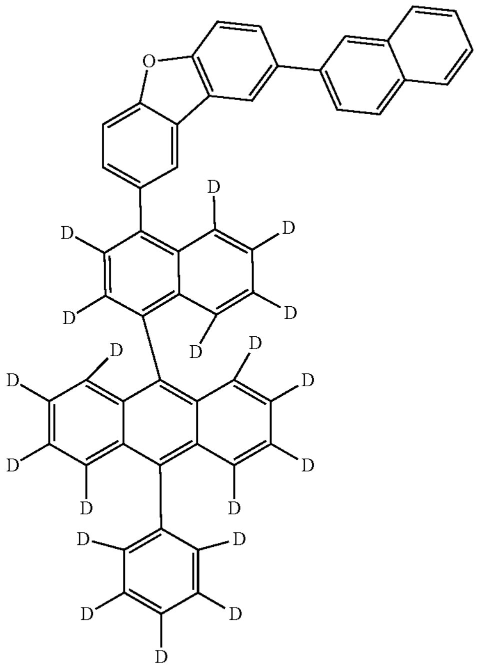
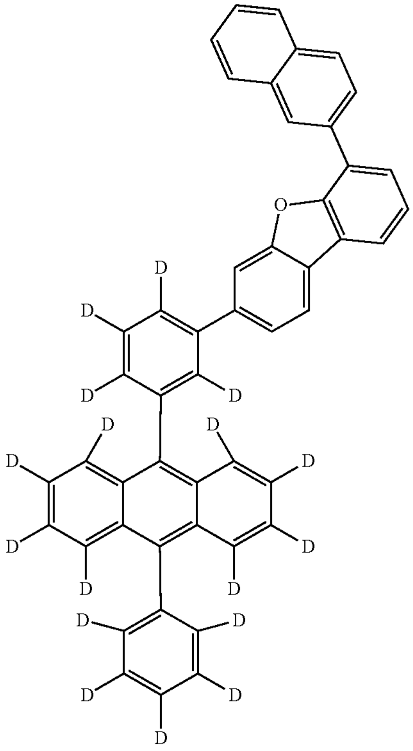
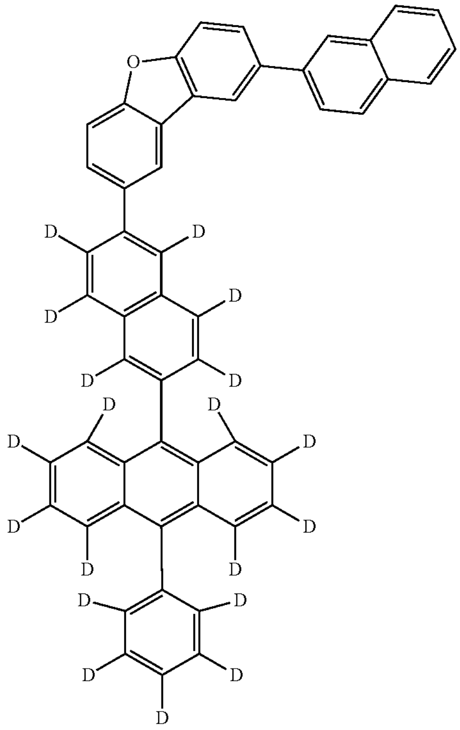
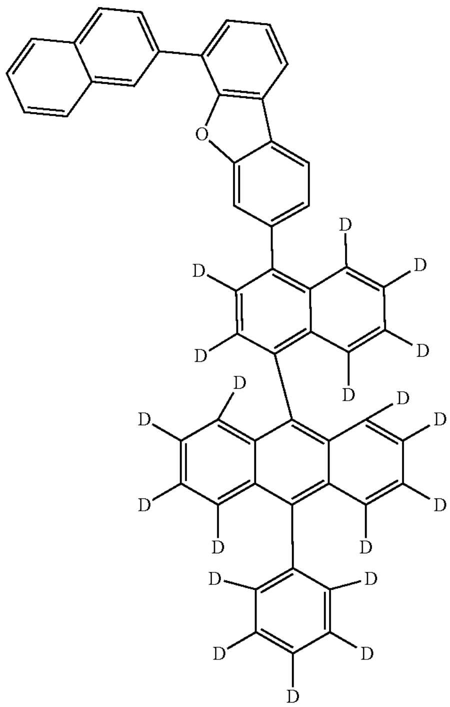

-continued
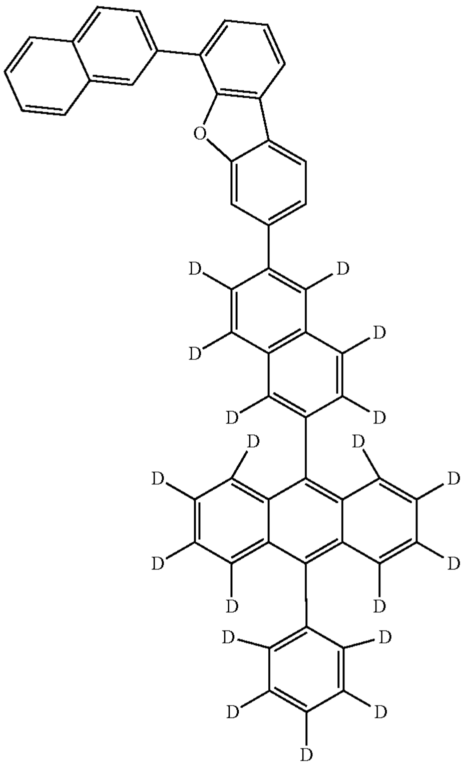
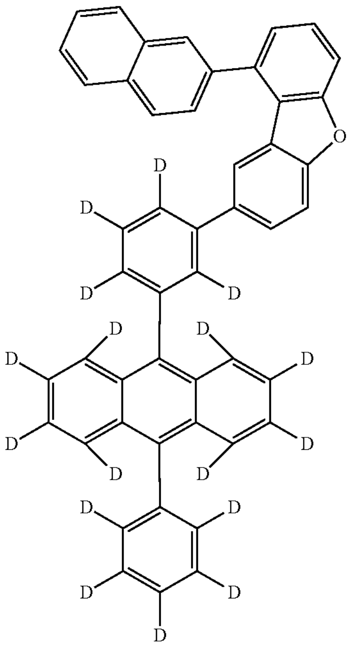
-continued
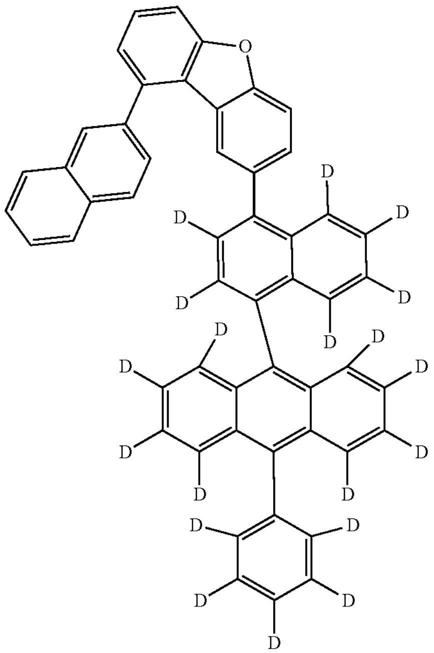
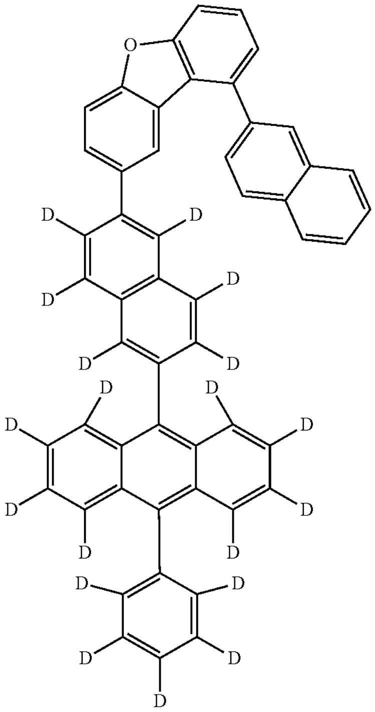

-continued
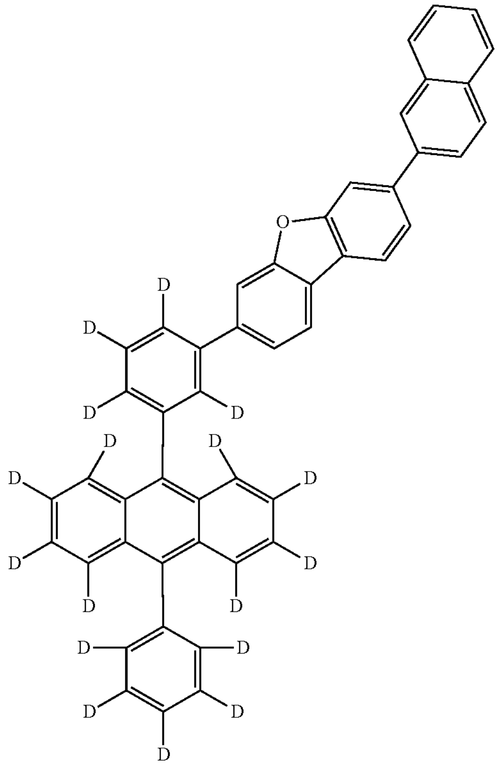
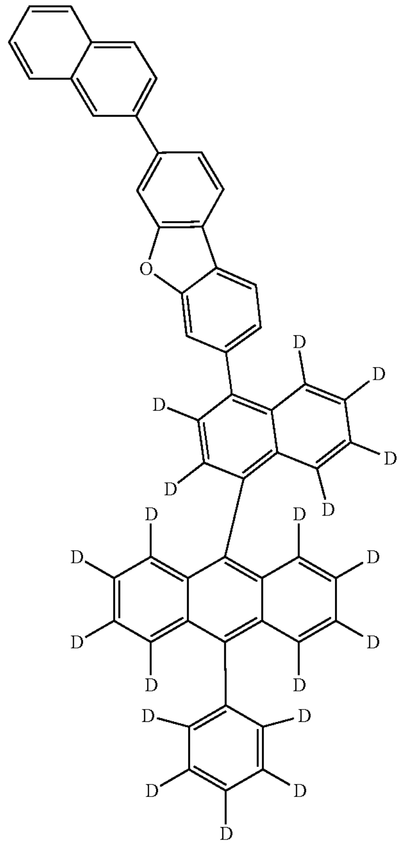
-continued
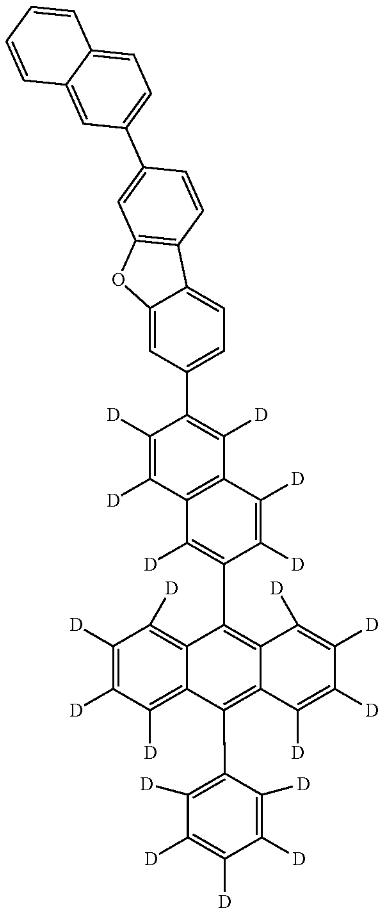
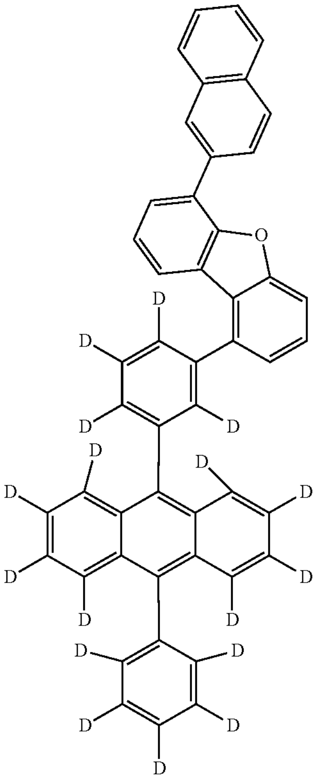

-continued
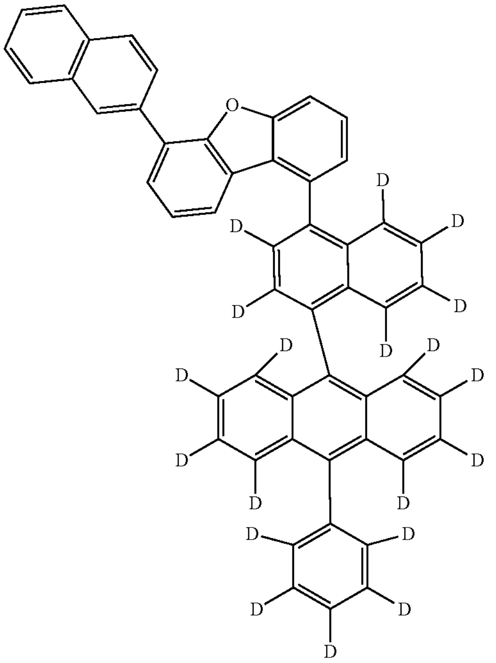
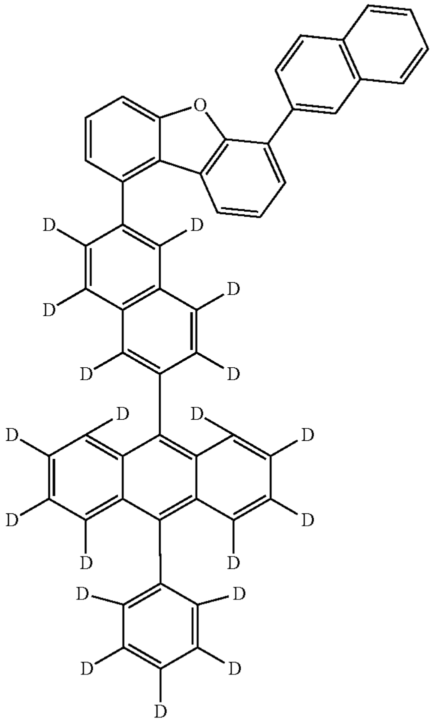
-continued
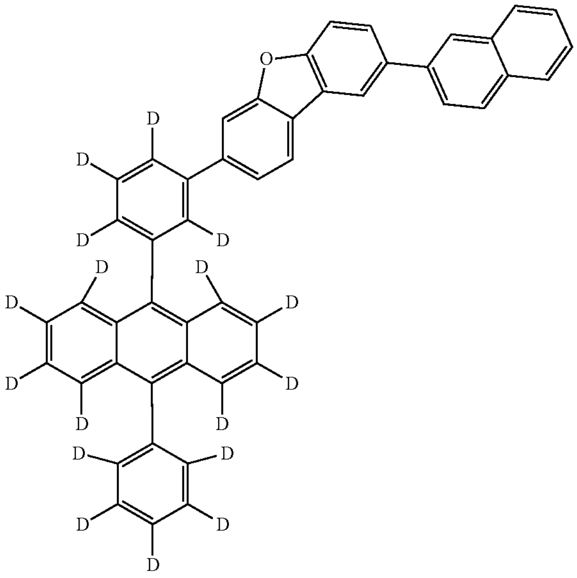
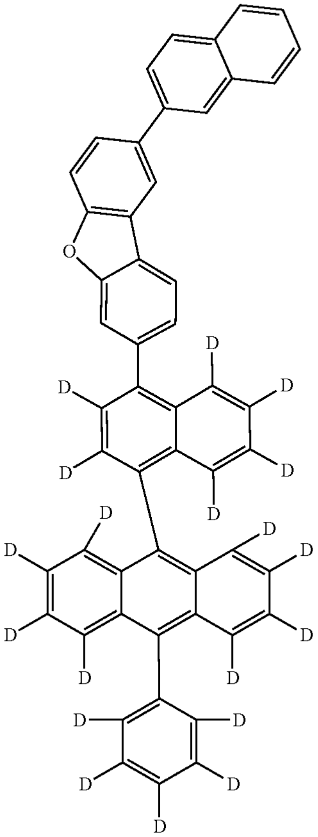

-continued
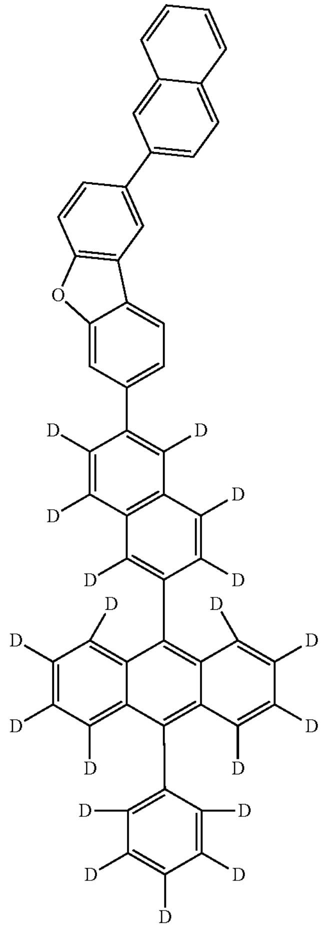
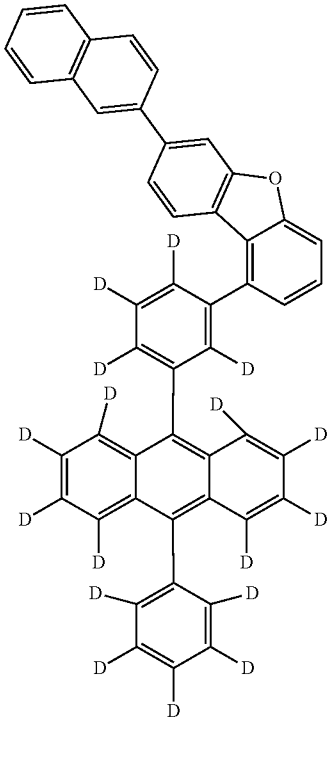
-continued
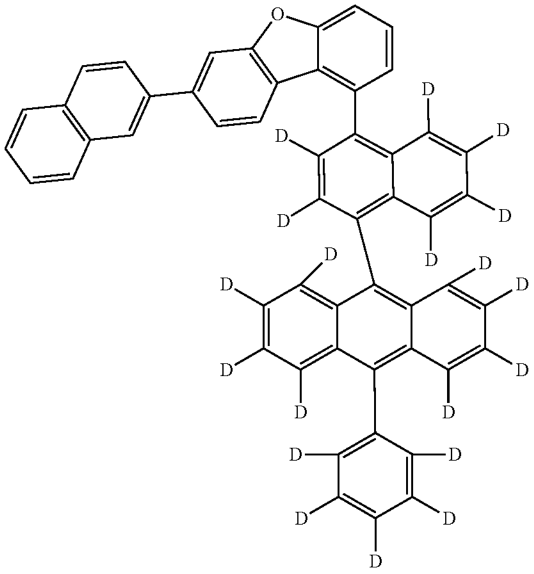
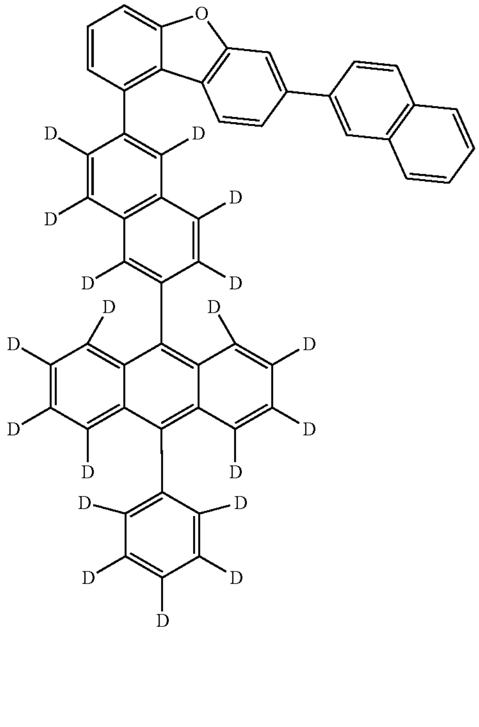

-continued
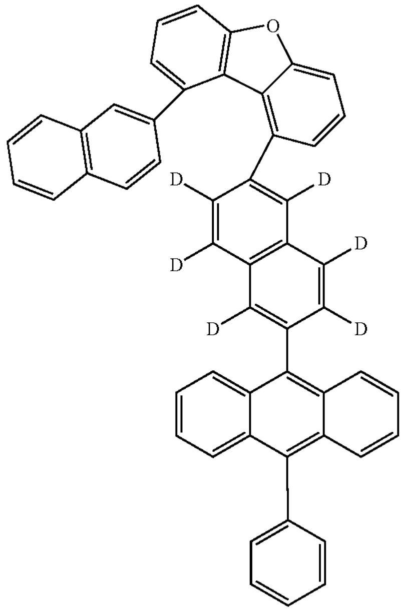
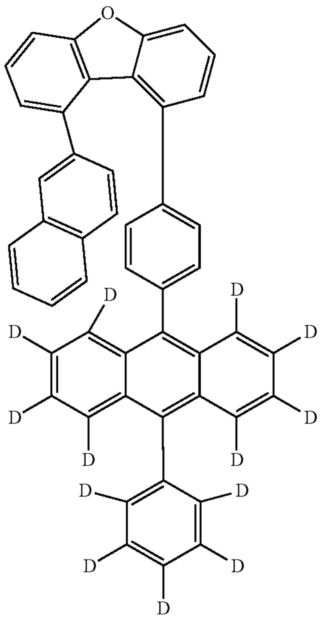
-continued
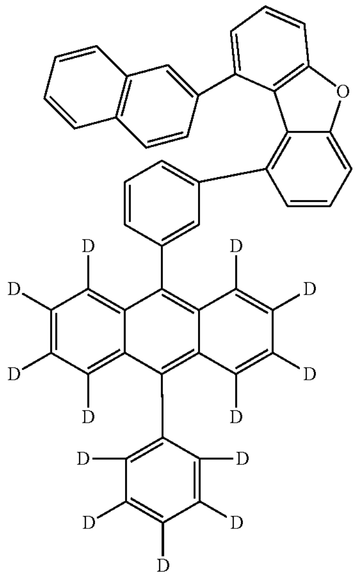
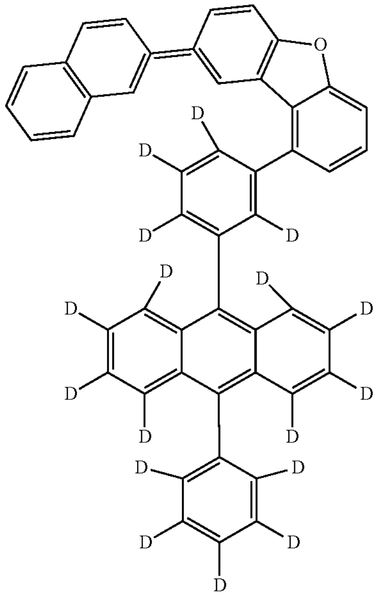

-continued
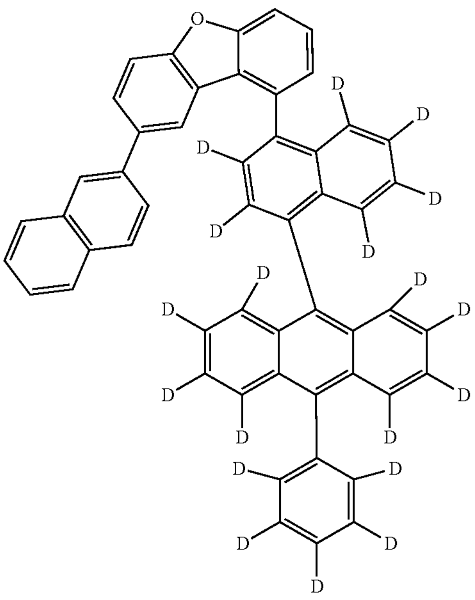
-continued
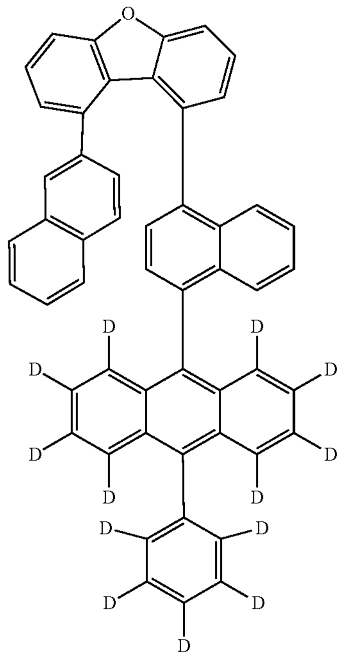
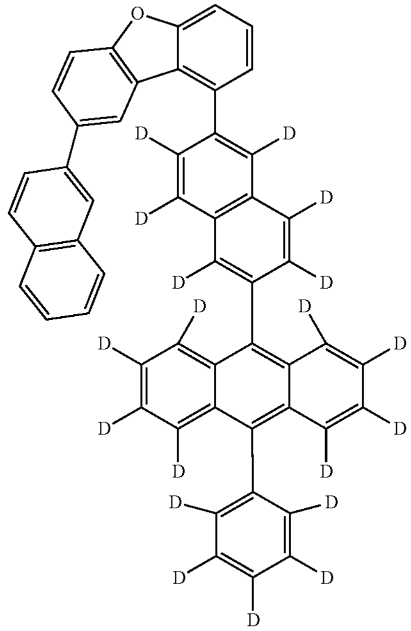
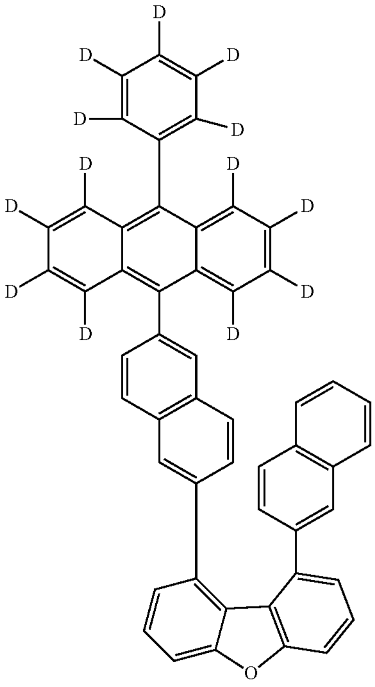

-continued
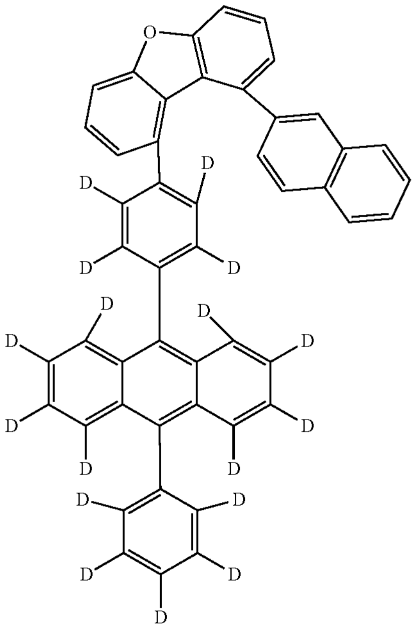
-continued
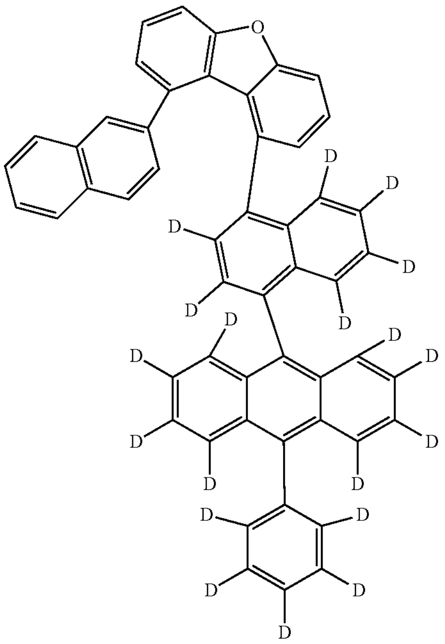
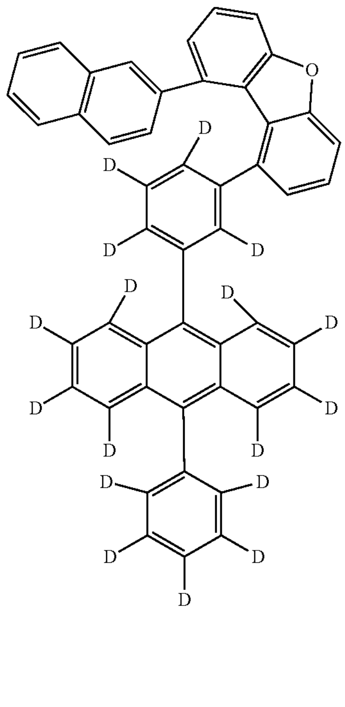
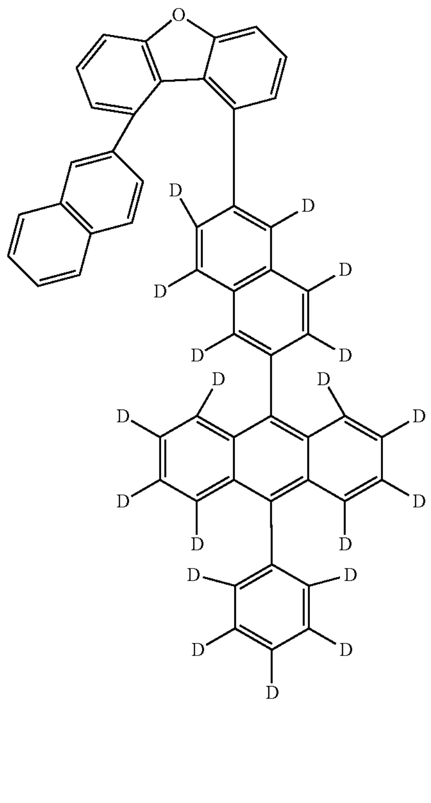

-continued
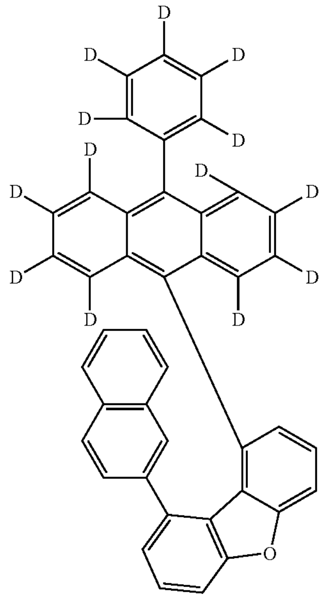
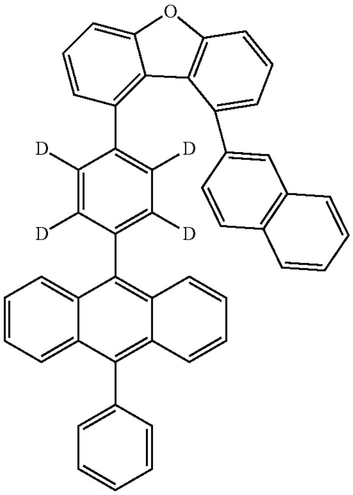
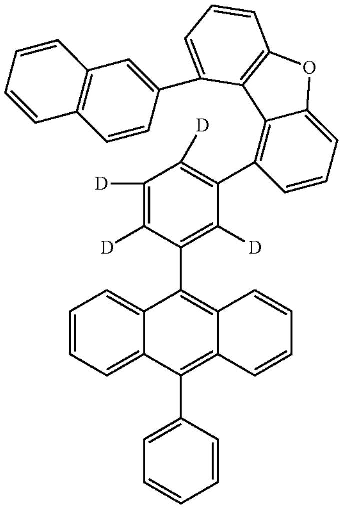
-continued
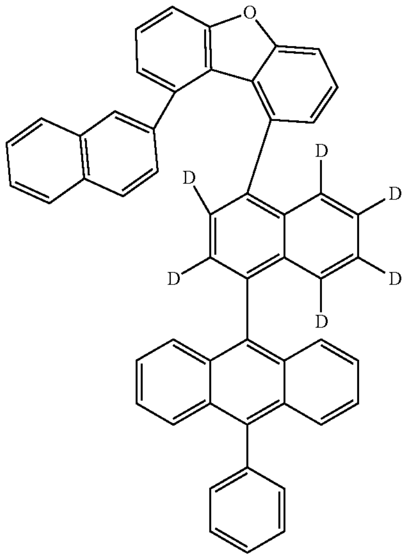 [SMILES: [2H]c1c([2H])c([2H])c2c(-c3cccc4oc5cccc(-c6ccc7ccccc7c6)c5c34)c([2H])c([2H])c(-c3c4ccccc4c(-c4ccccc4)c4ccccc34)c2c1[2H]]
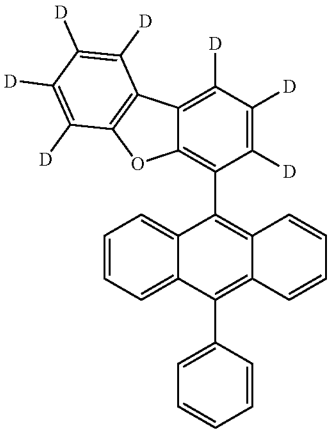
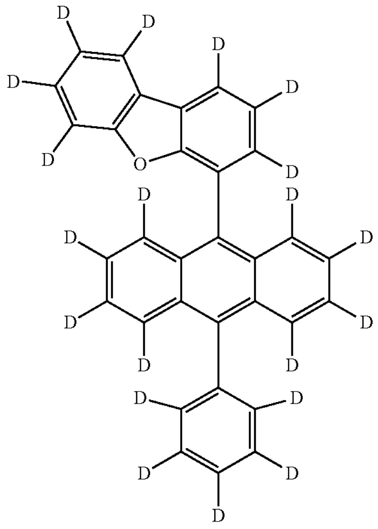

-continued
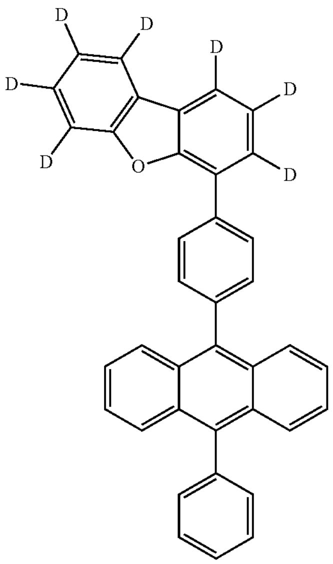
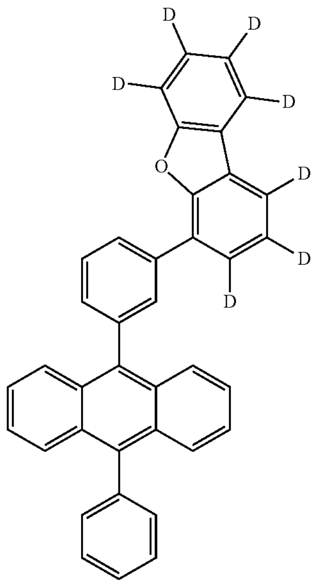
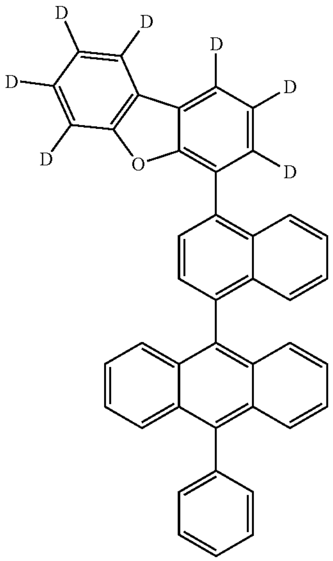
-continued
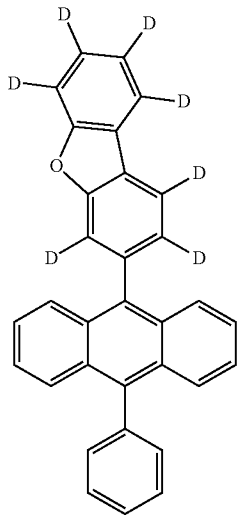
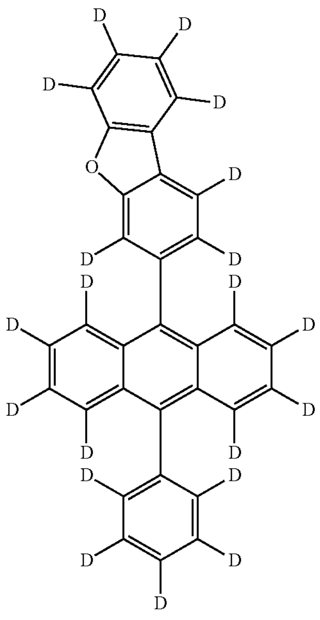

-continued
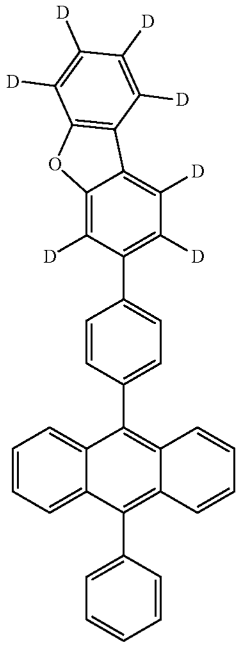
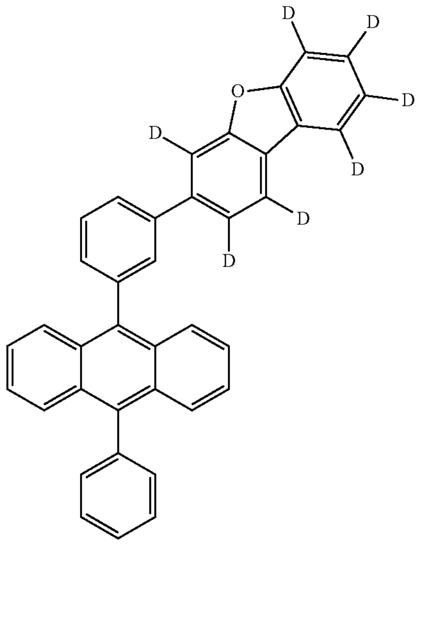
-continued
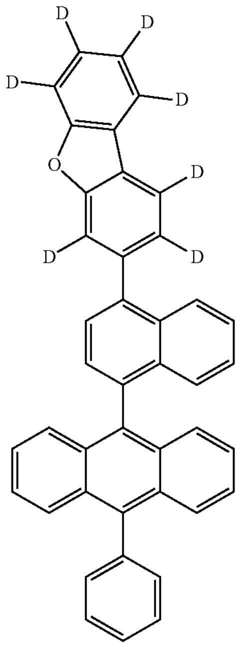
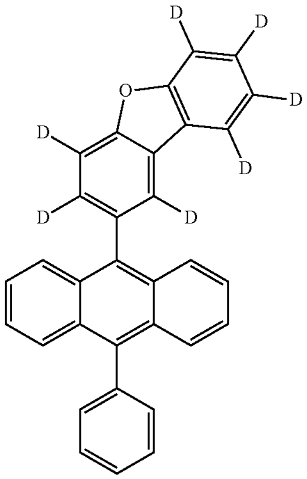
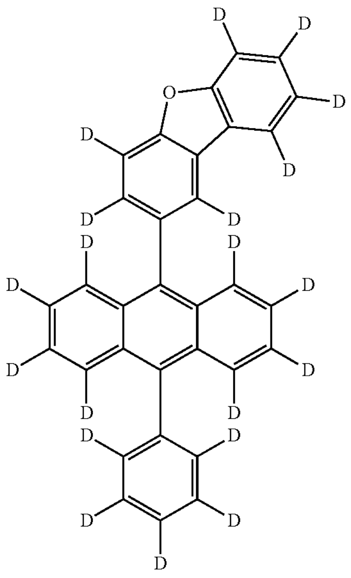

-continued
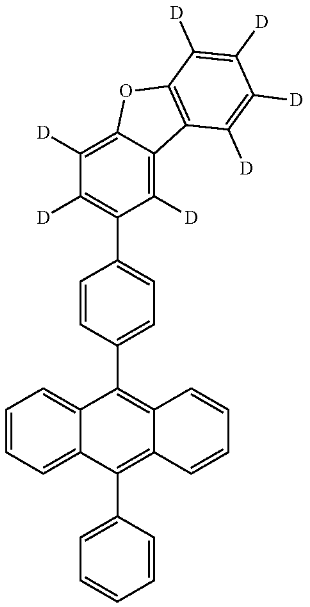
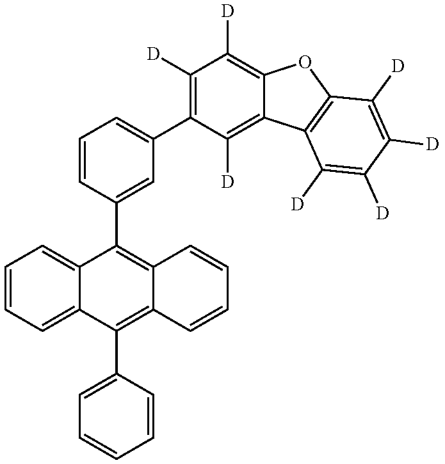
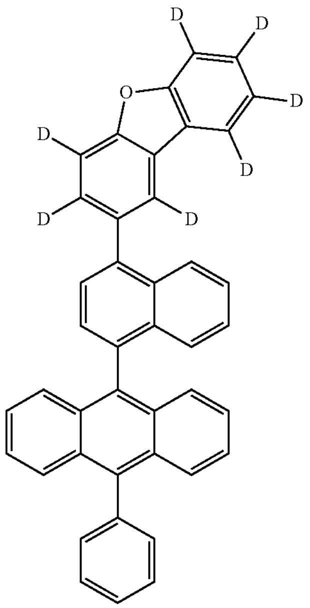
-continued
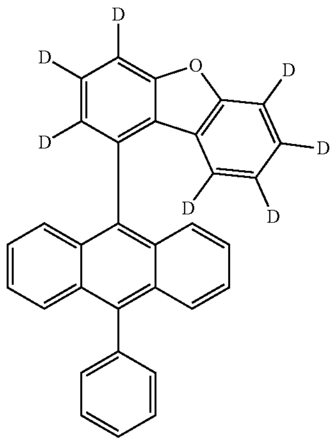
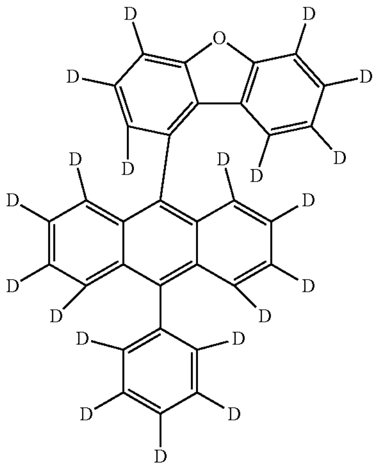
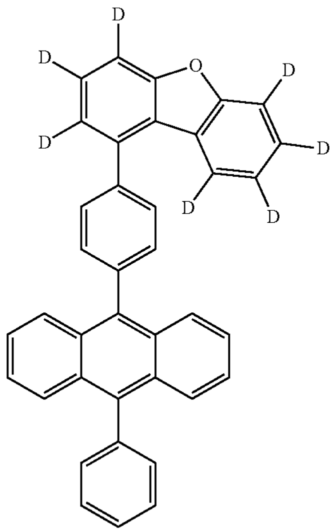

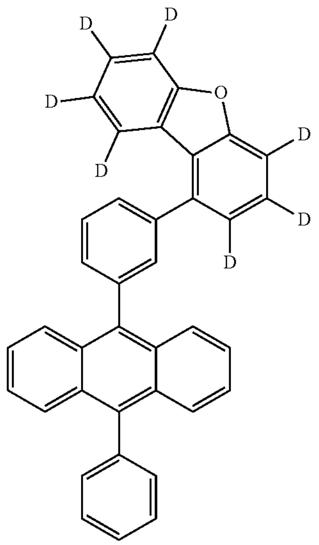
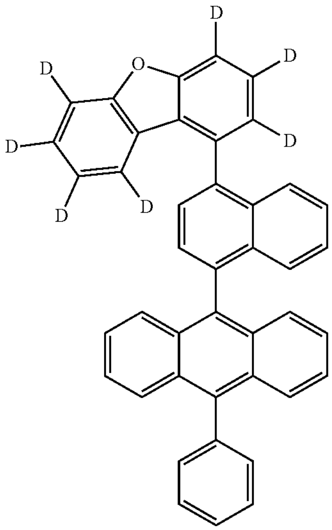
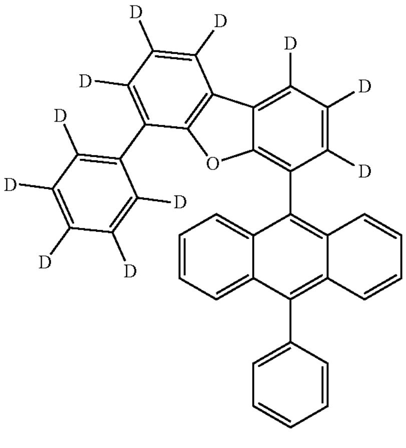
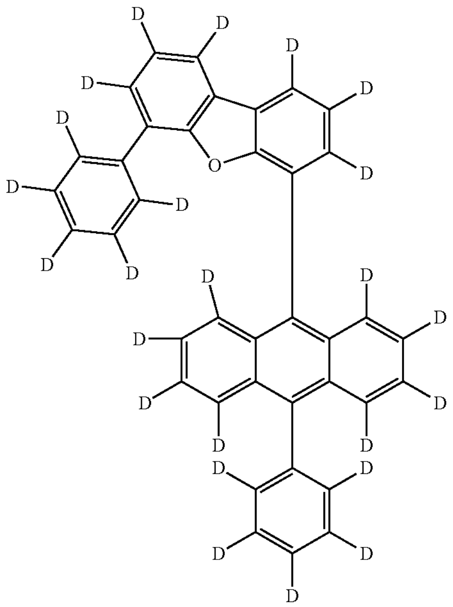
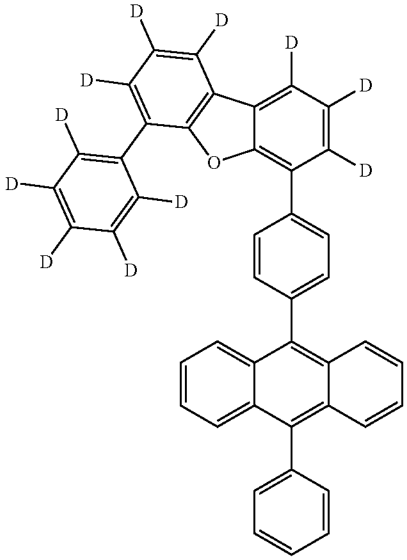

-continued
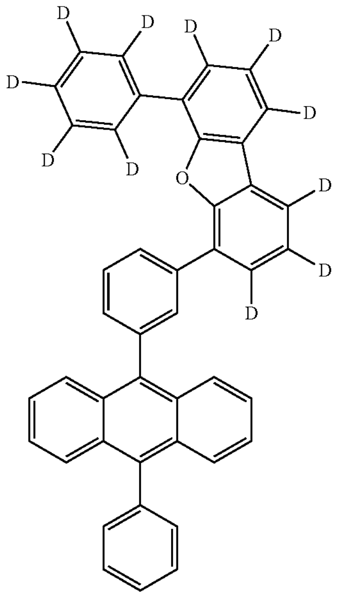
-continued
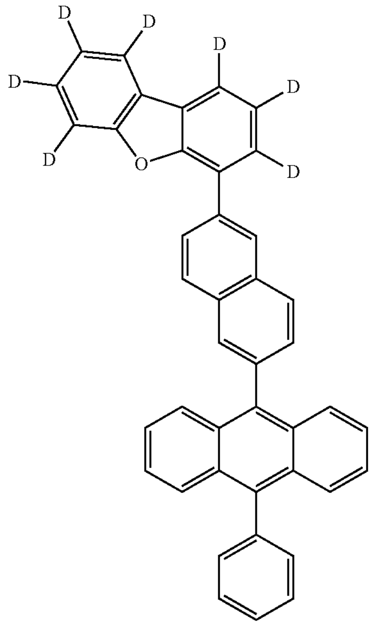
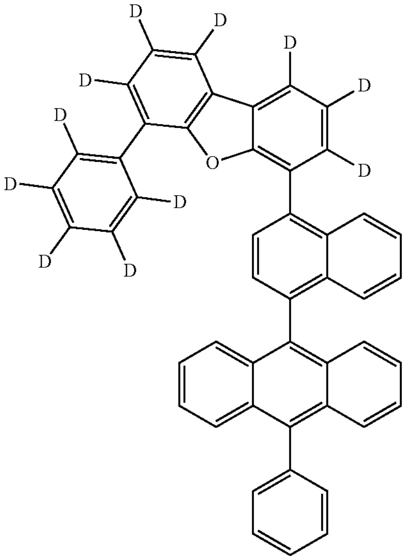
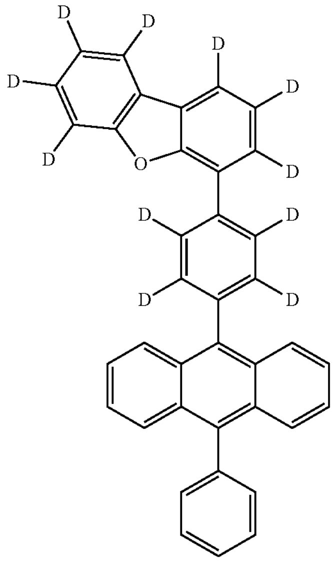

-continued
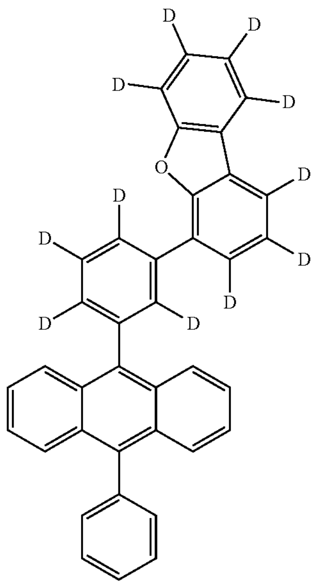
-continued
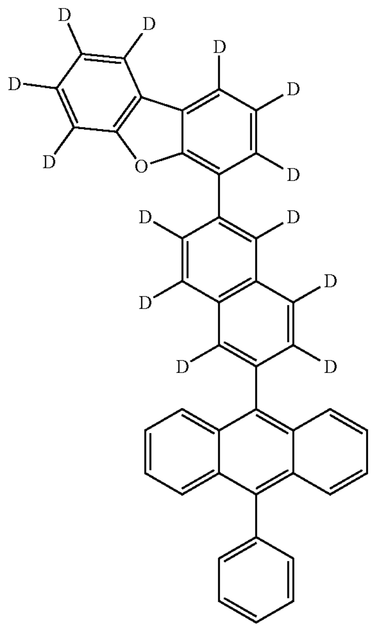
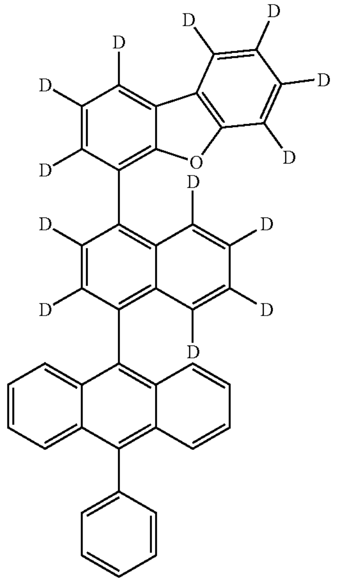
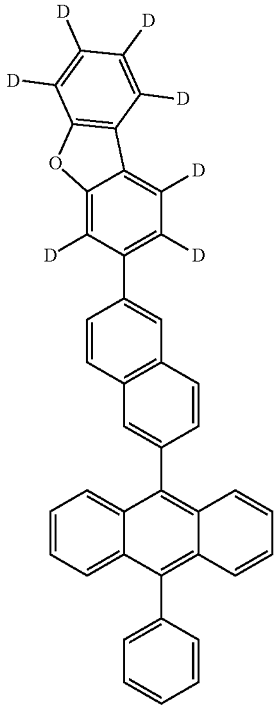

-continued
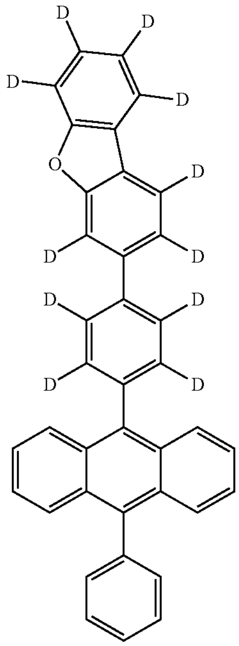
-continued
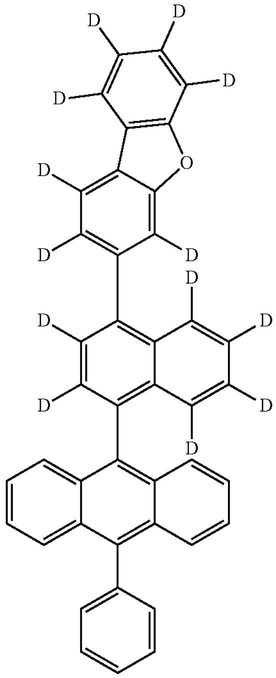
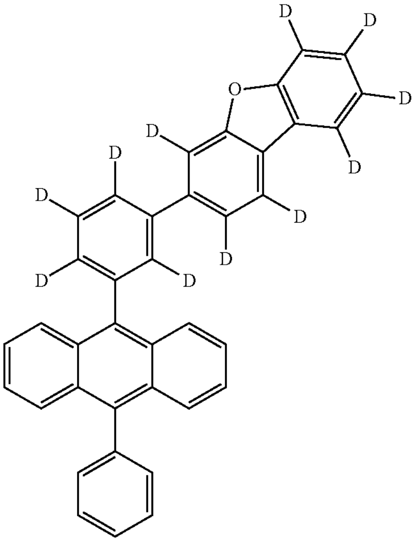
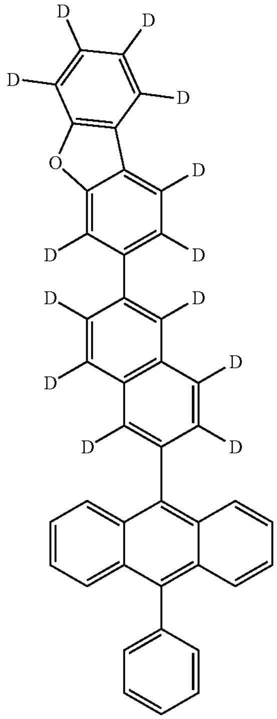

-continued
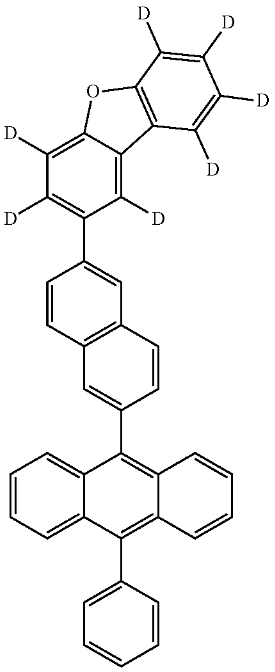
-continued
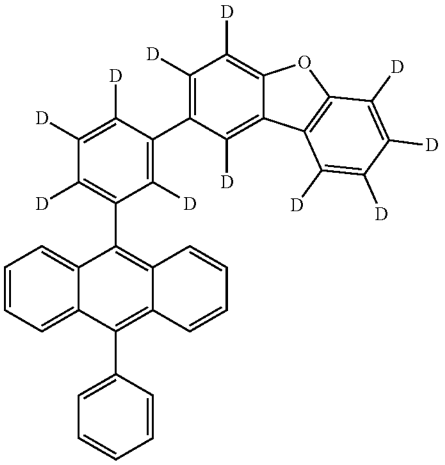
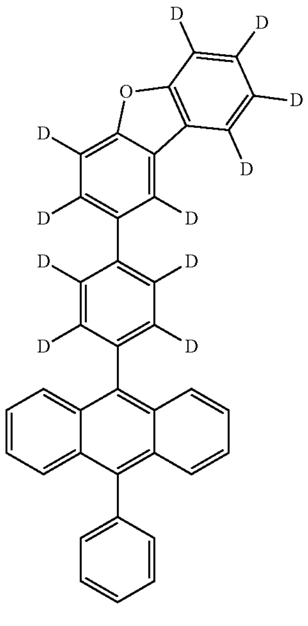
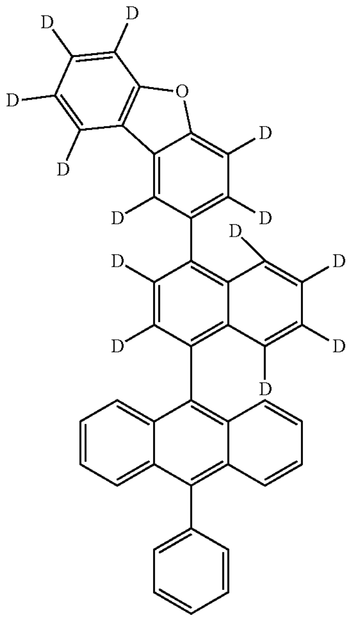

-continued
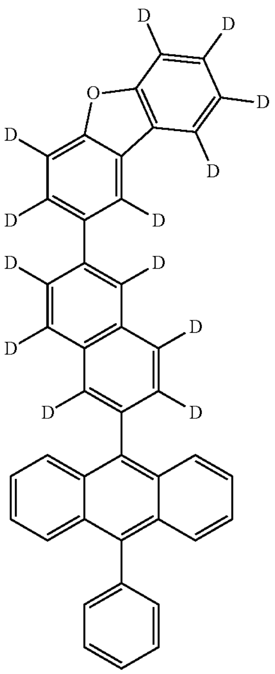
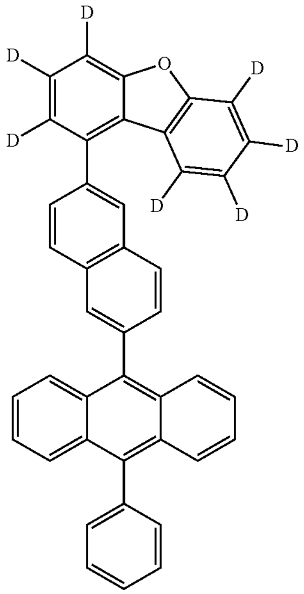
-continued
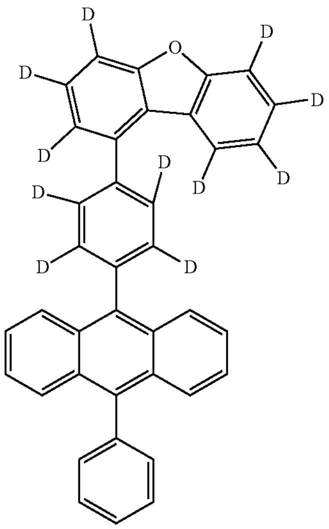
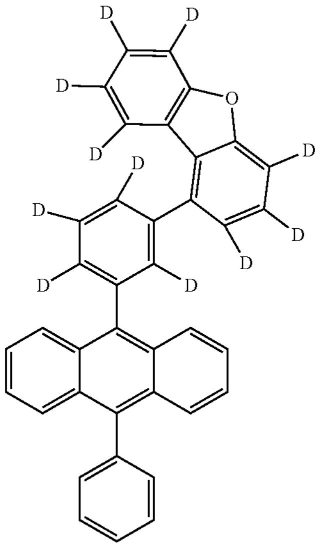
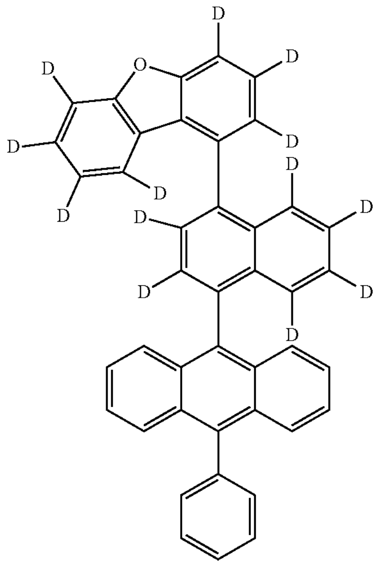

-continued
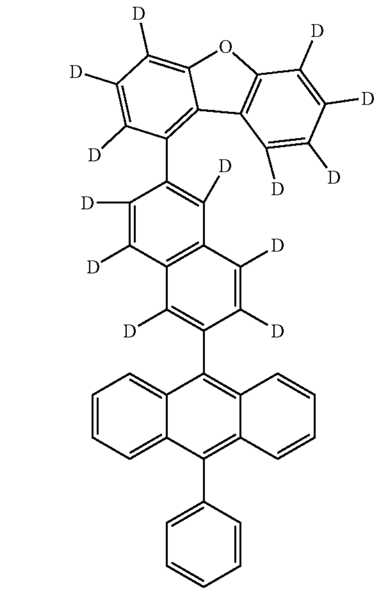
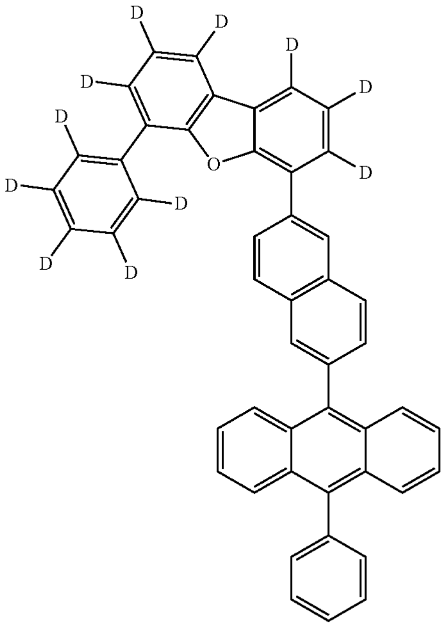
-continued
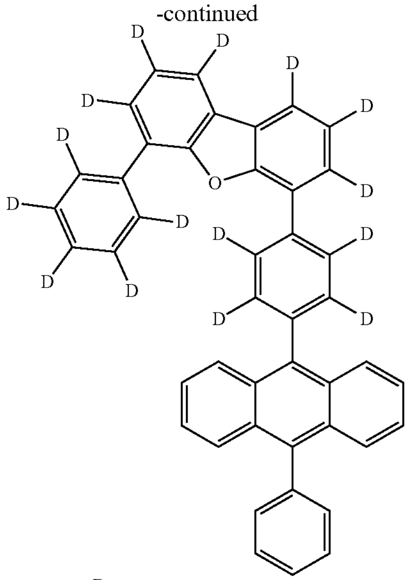
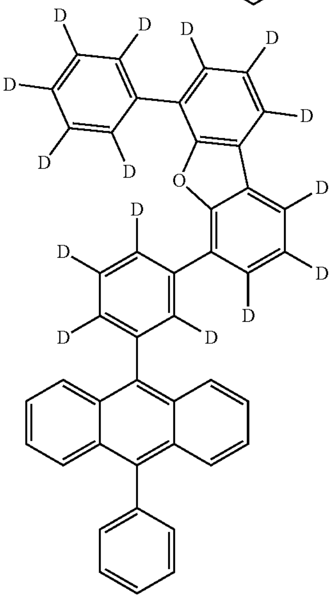
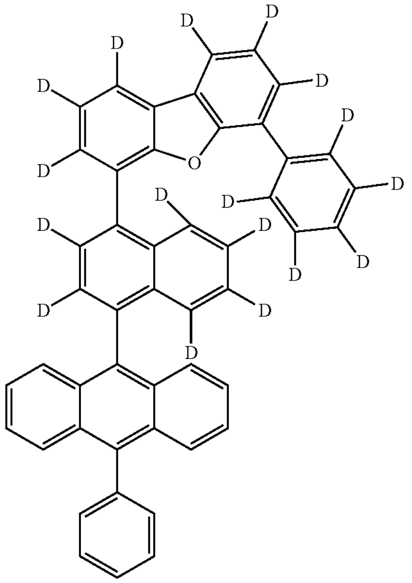

-continued
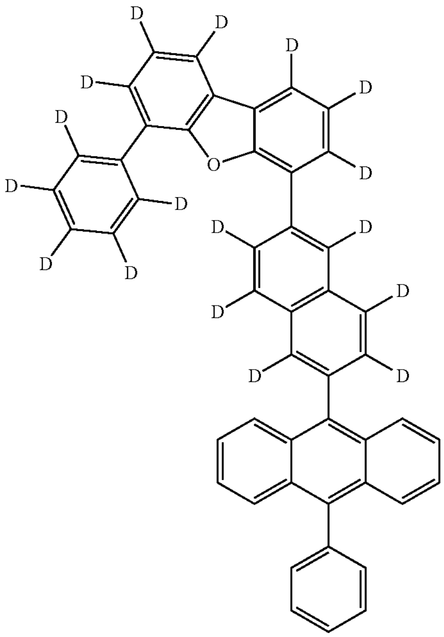
-continued
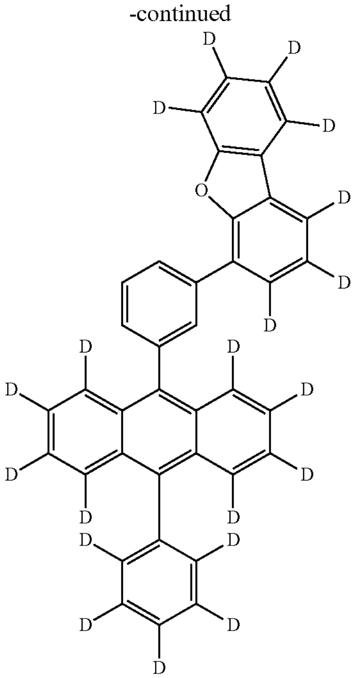
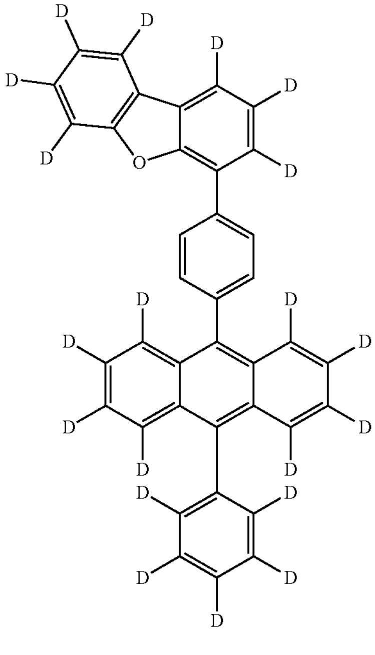
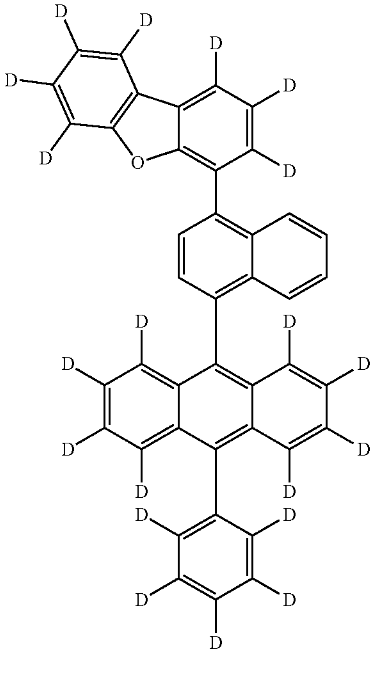

-continued
-continued
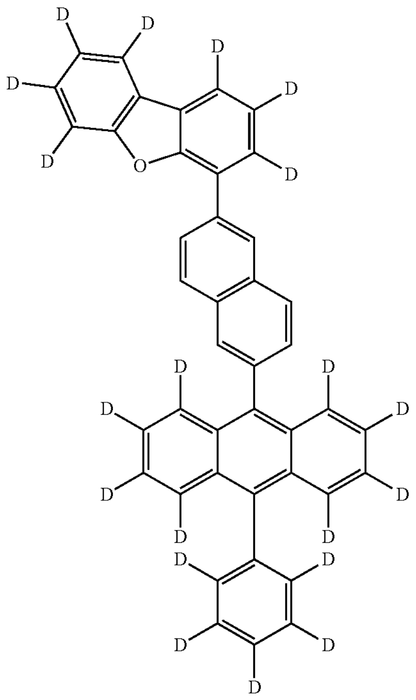
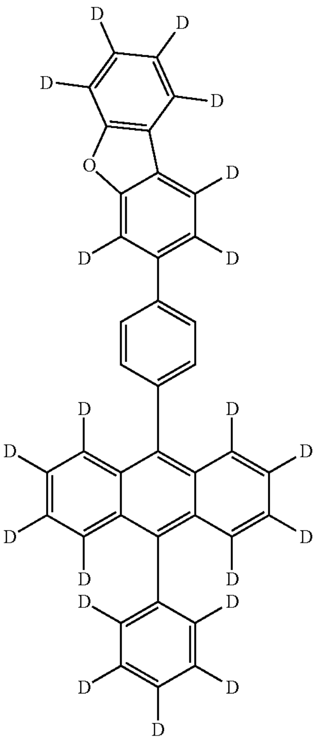
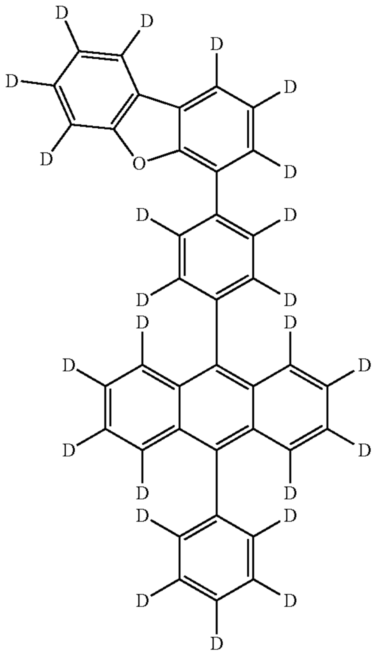
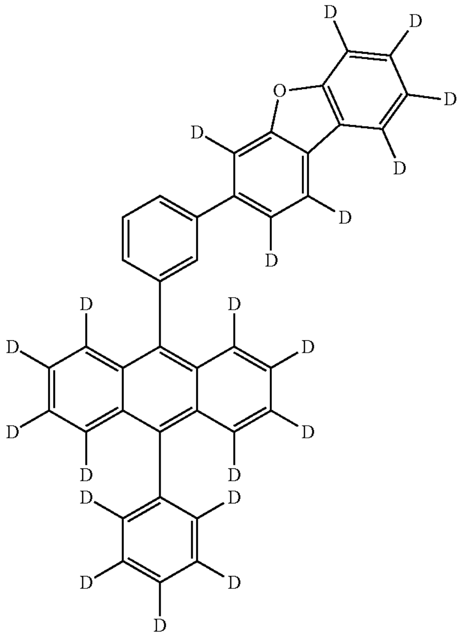

-continued
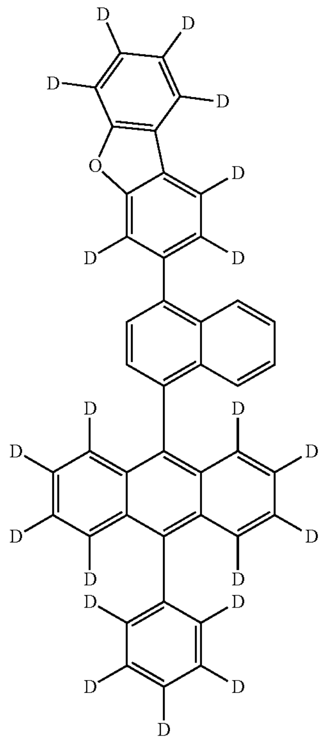
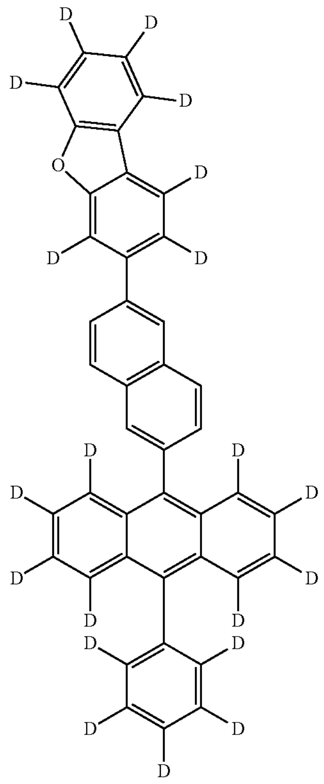
-continued
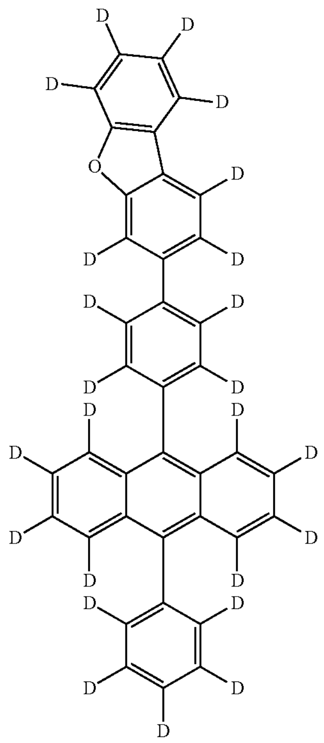
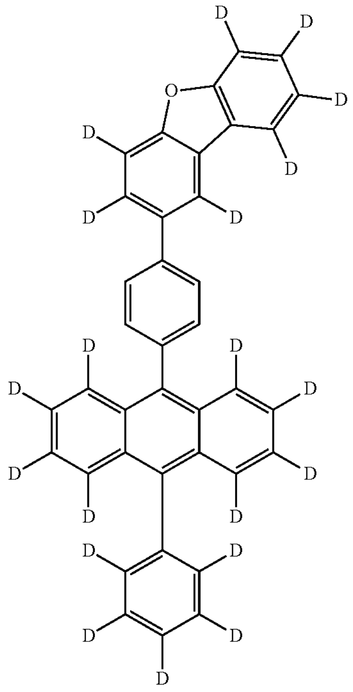

-continued
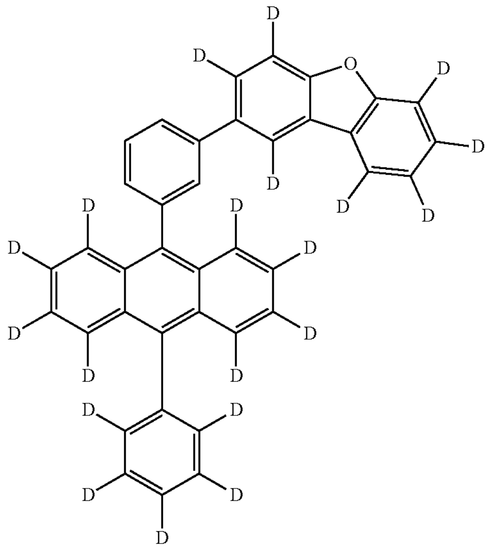
-continued
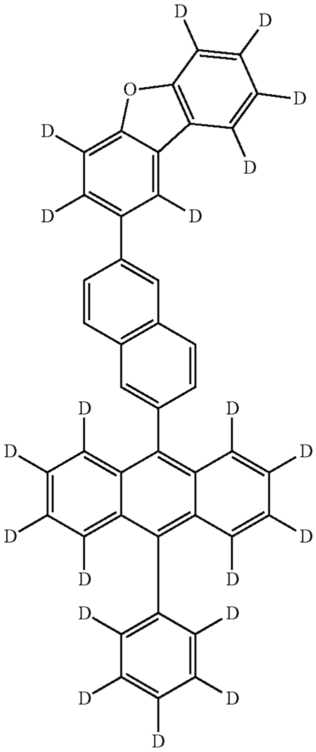
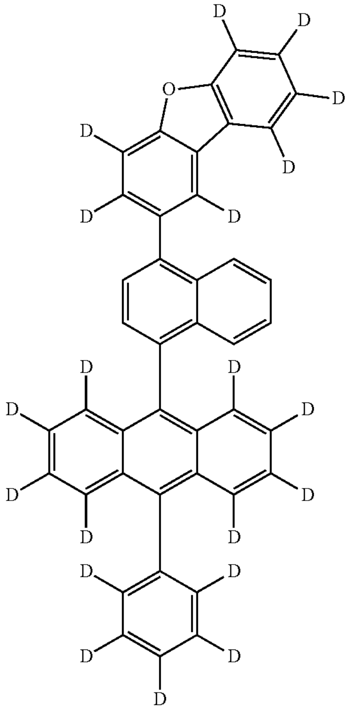
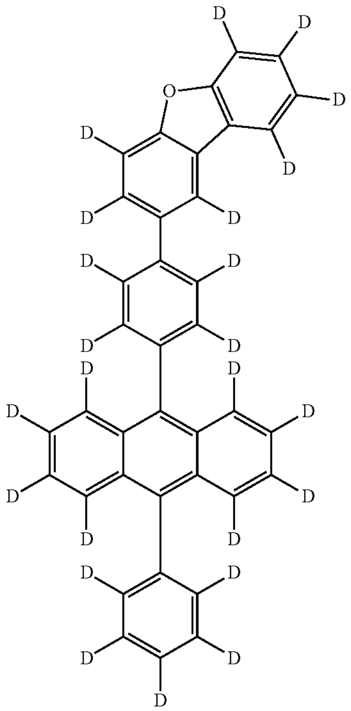

-continued
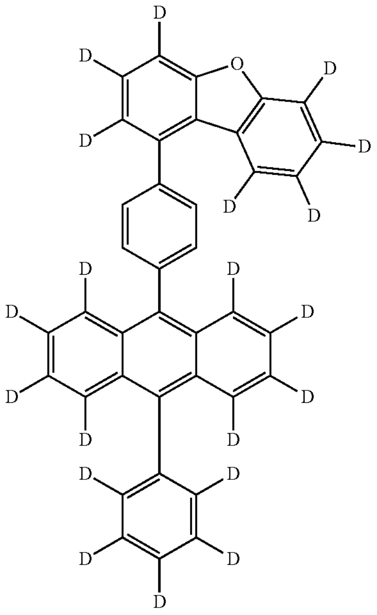
-continued
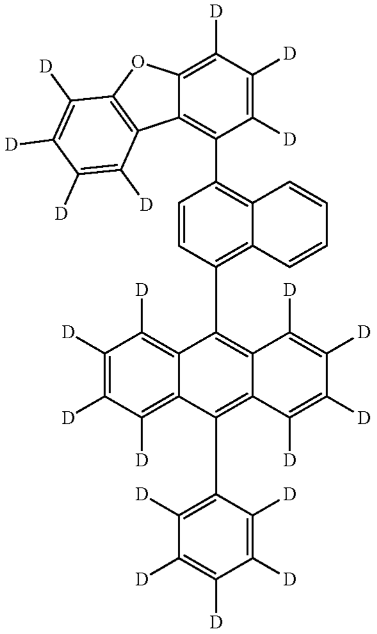
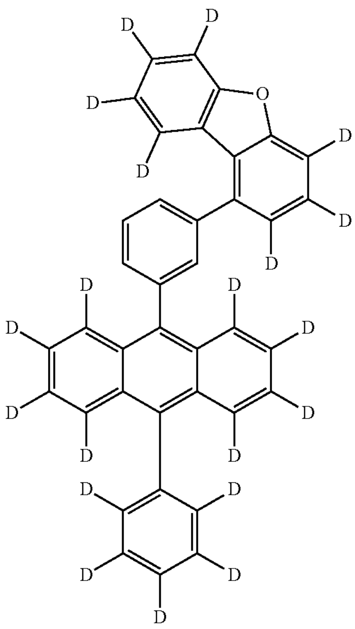
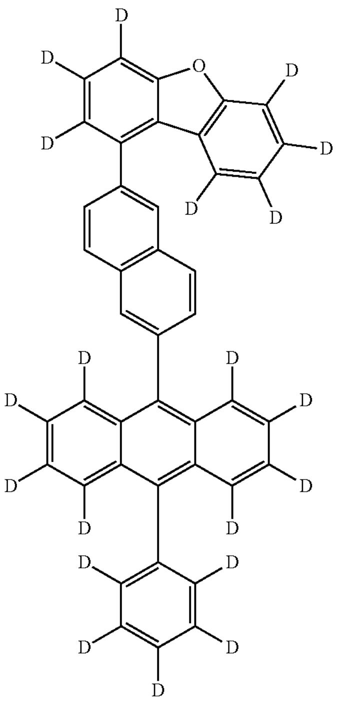

-continued
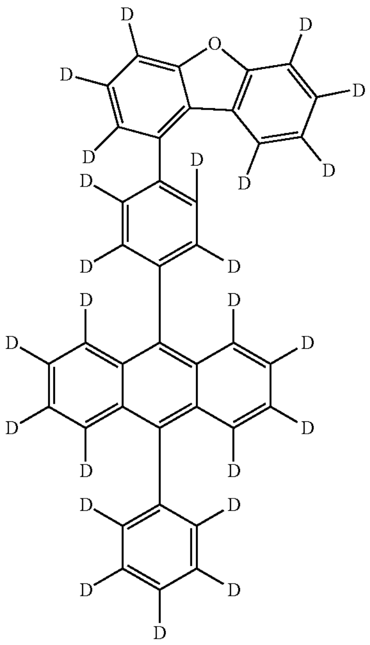
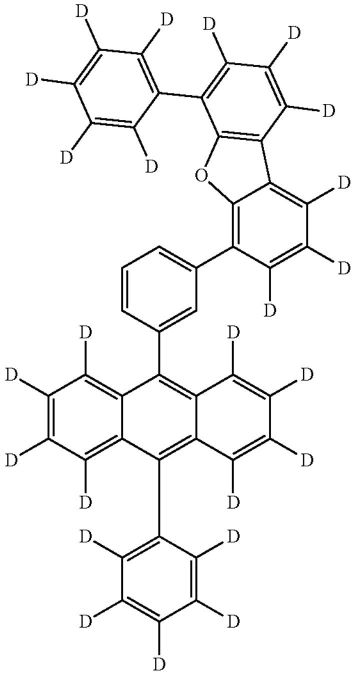
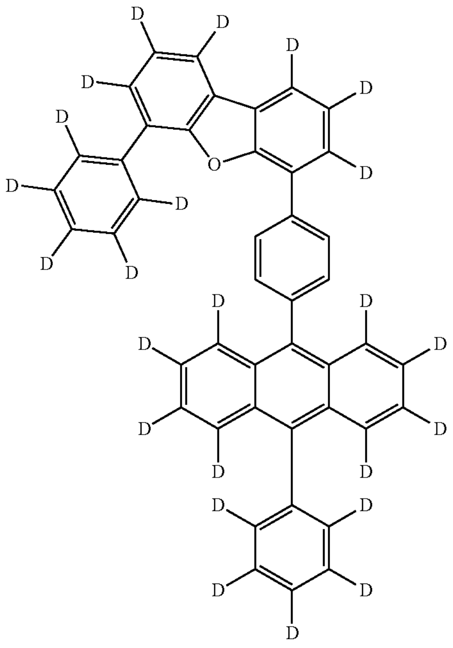
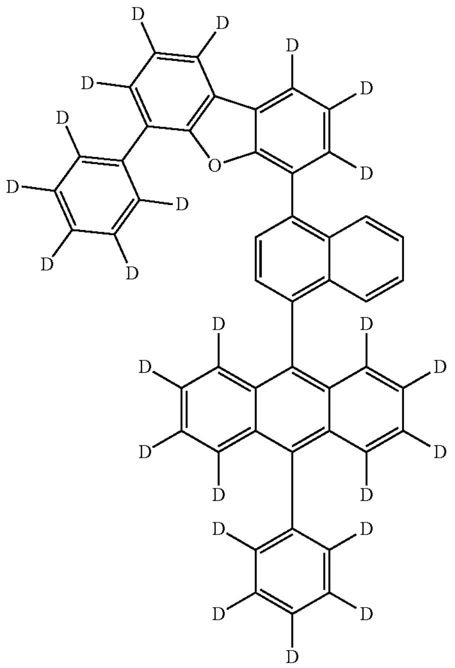
-continued

-continued
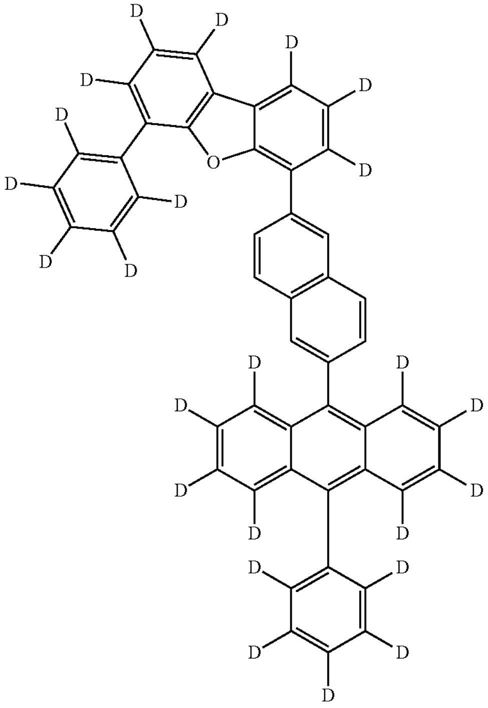
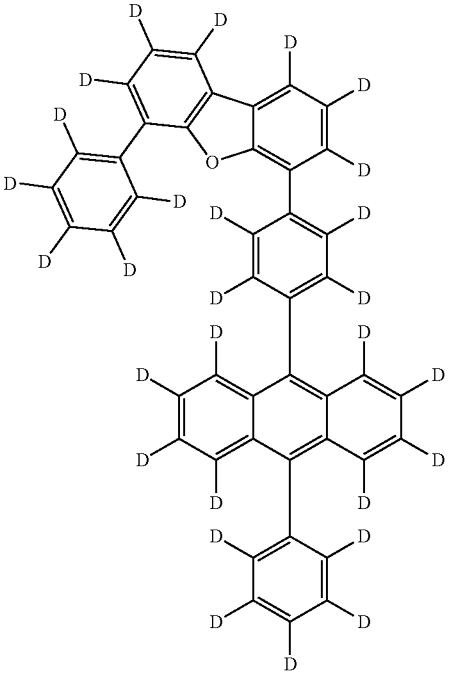
-continued
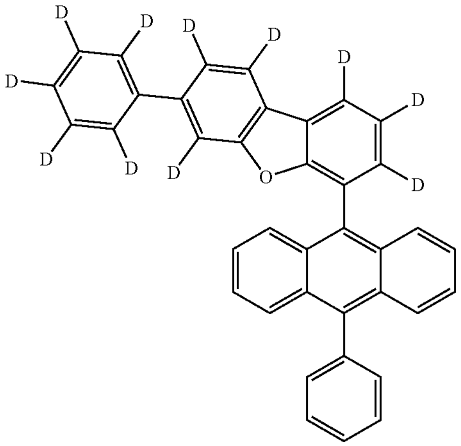
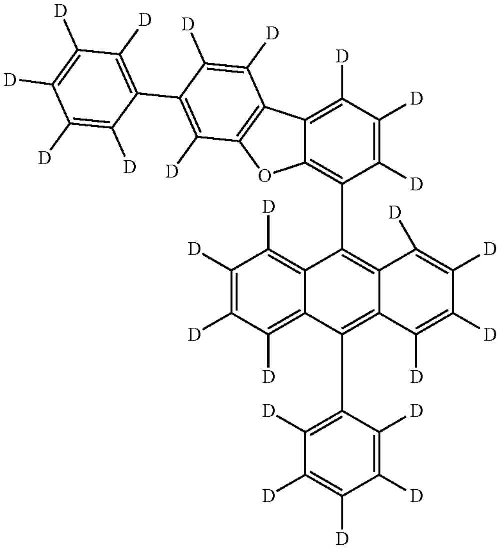
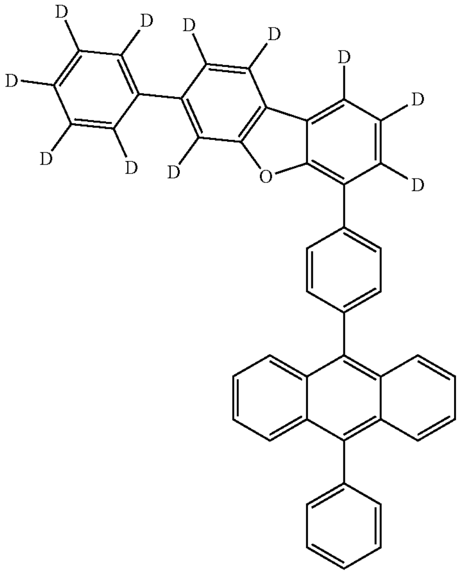

-continued
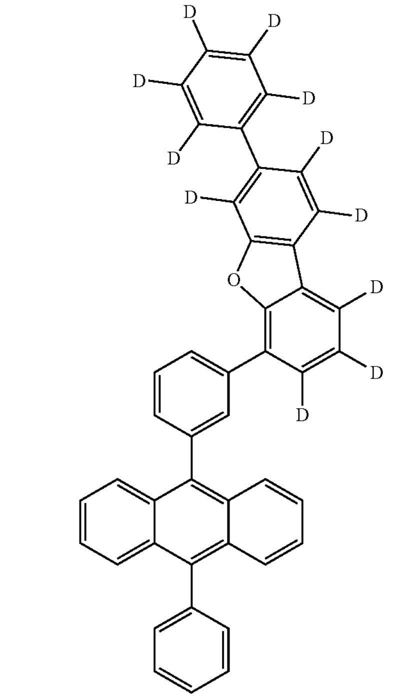
-continued
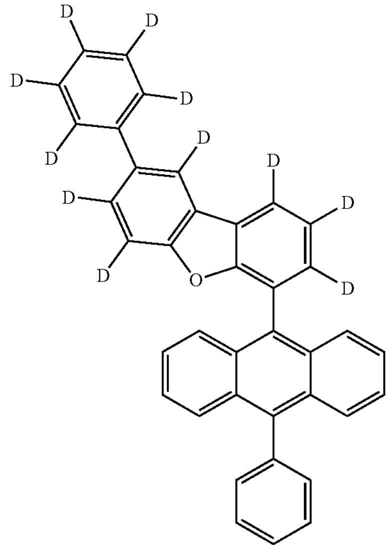
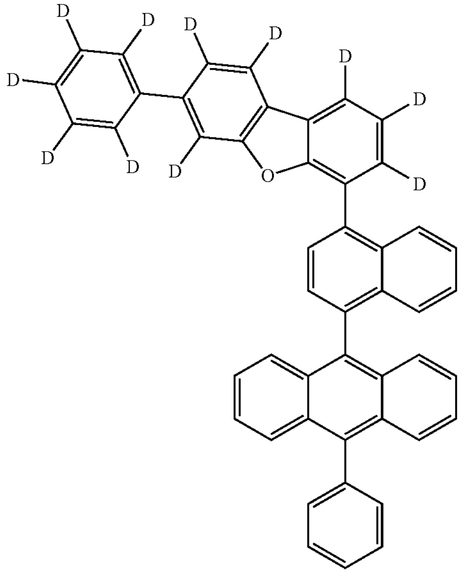
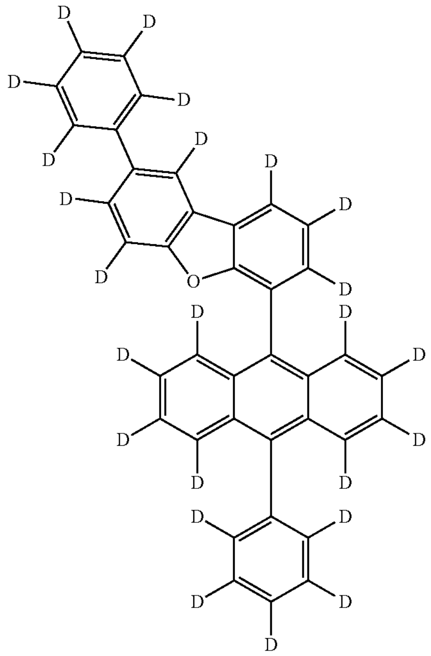

-continued
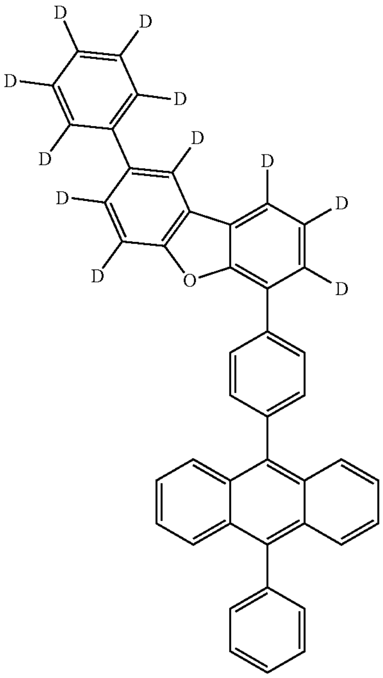
-continued
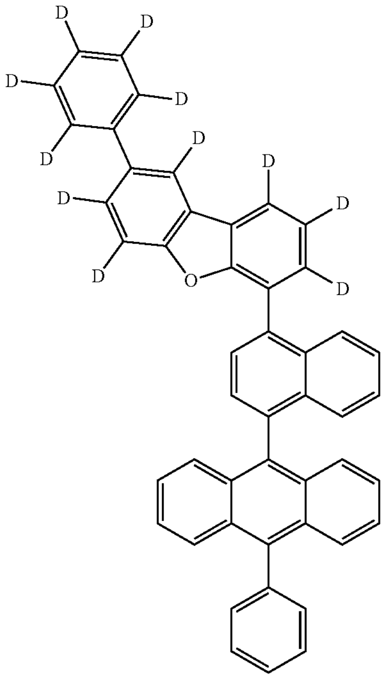
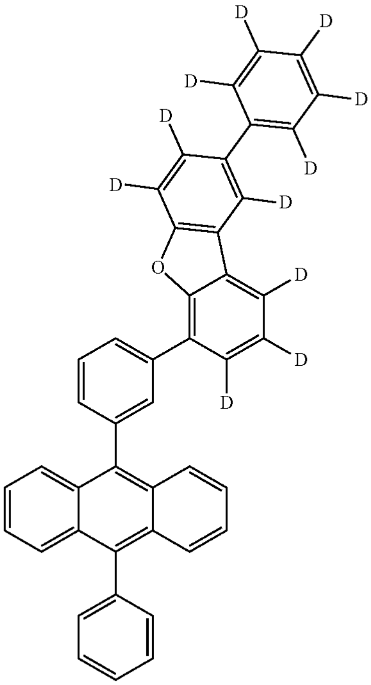
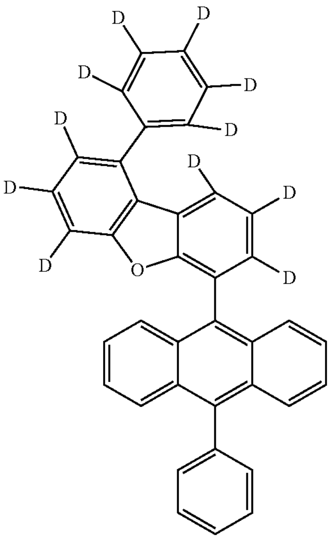

-continued
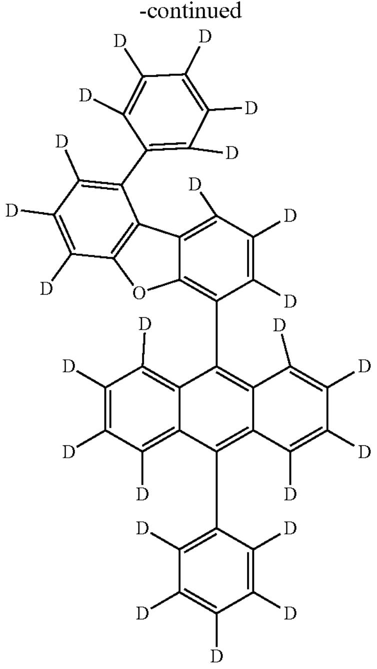
-continued
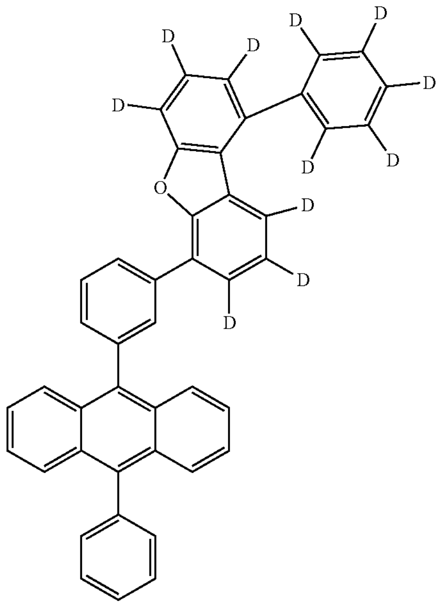
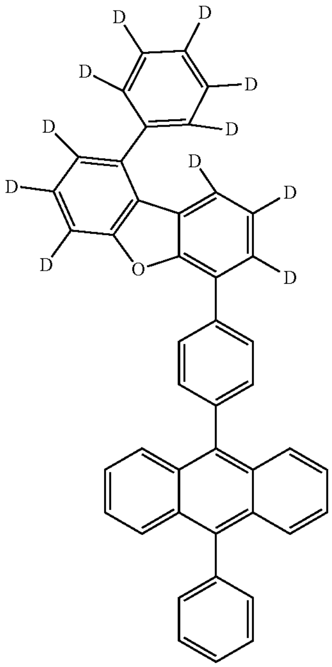
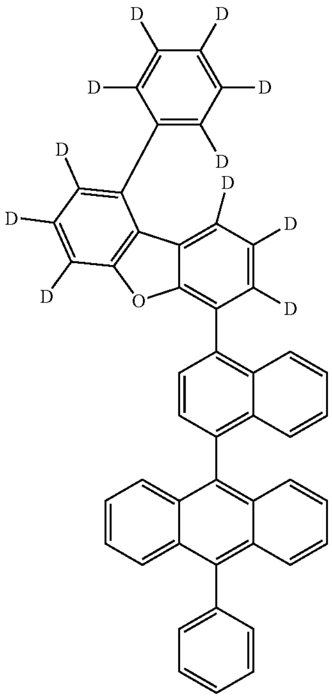

-continued
-continued
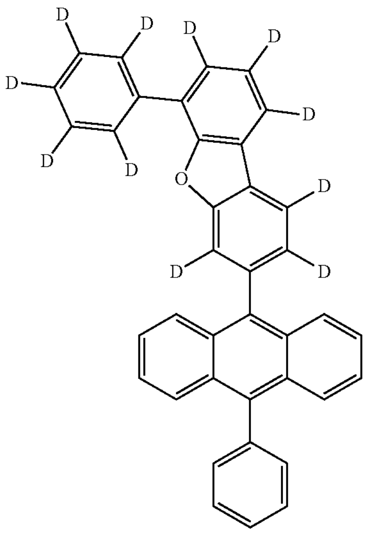
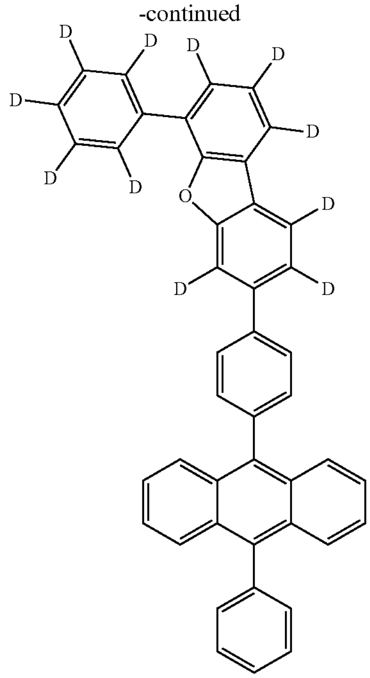
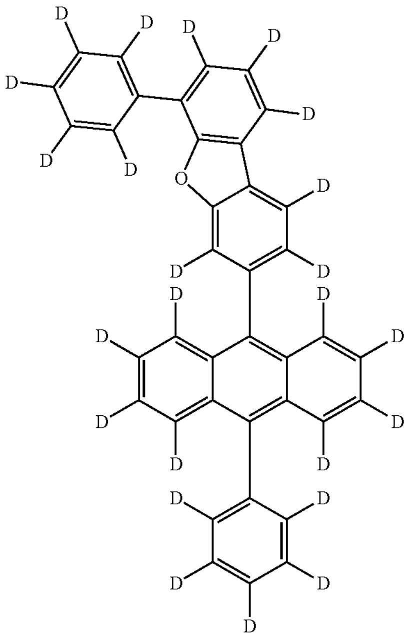
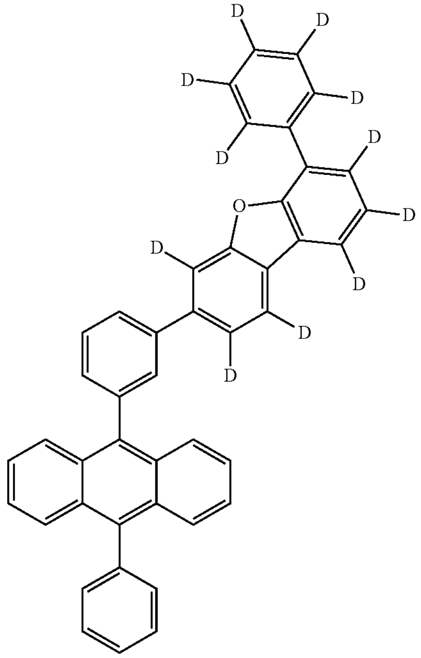

-continued
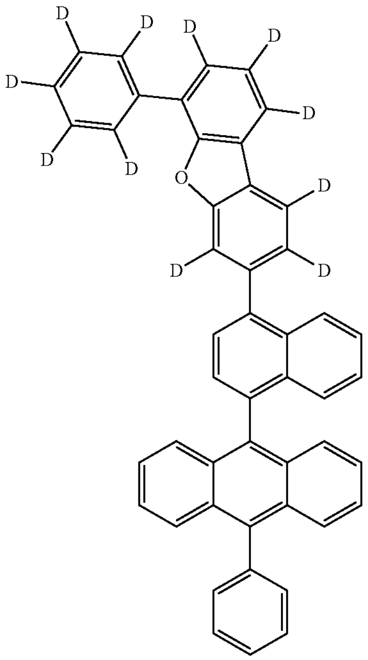
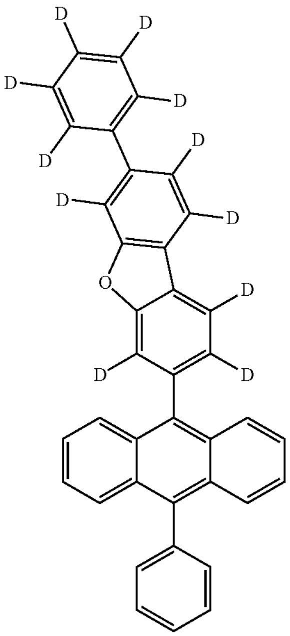
-continued
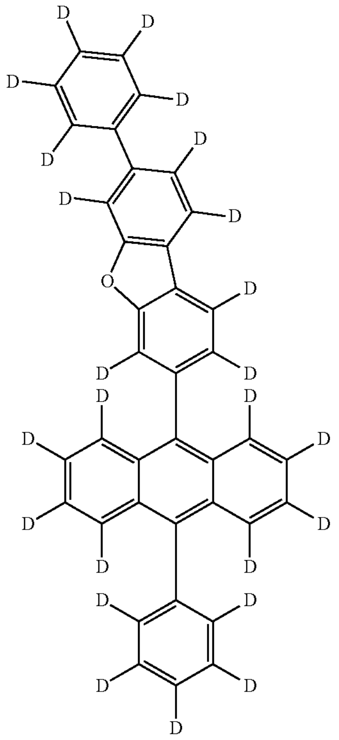
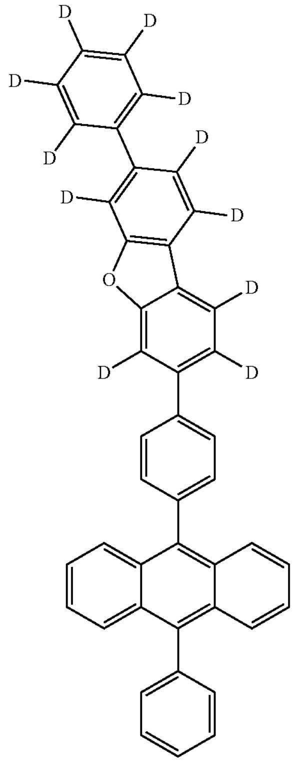

-continued
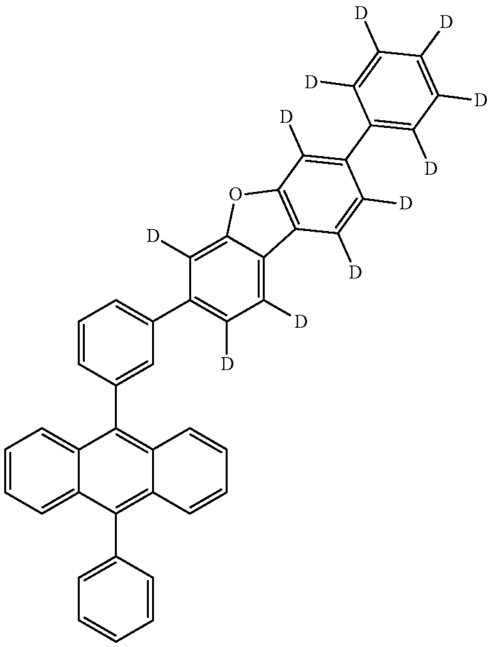
-continued
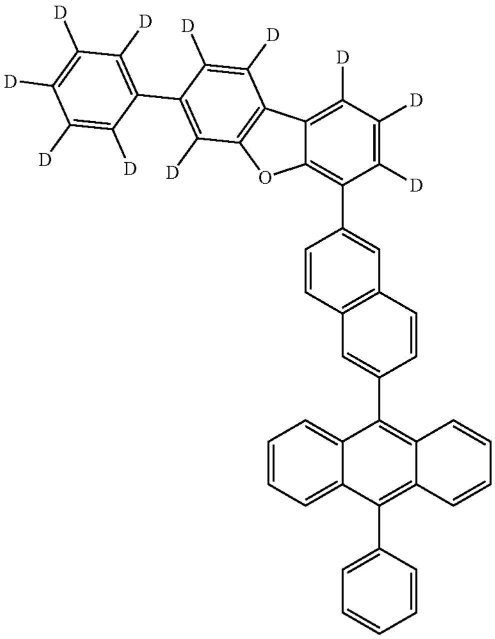
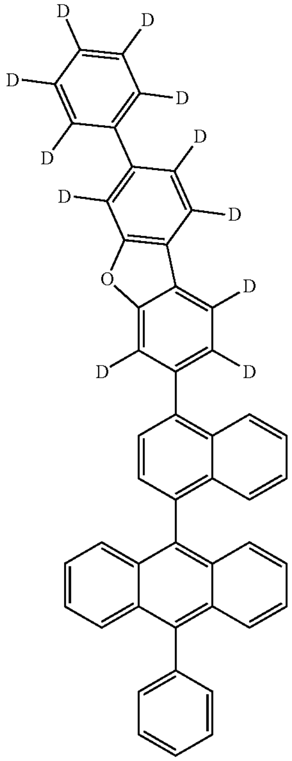
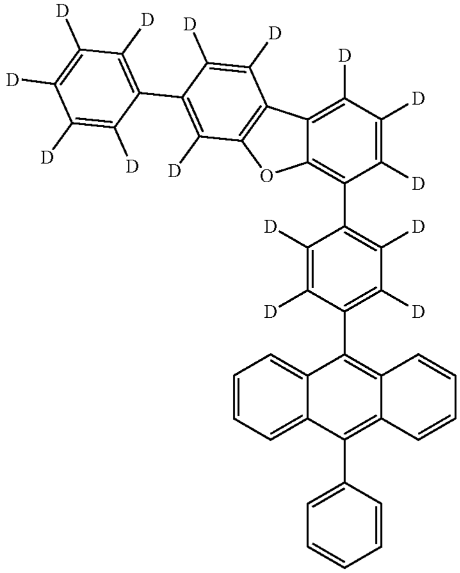

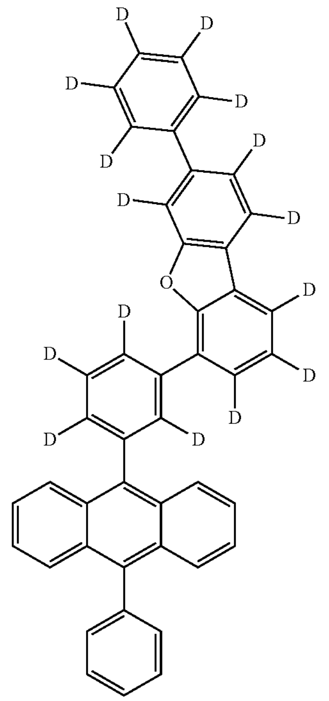
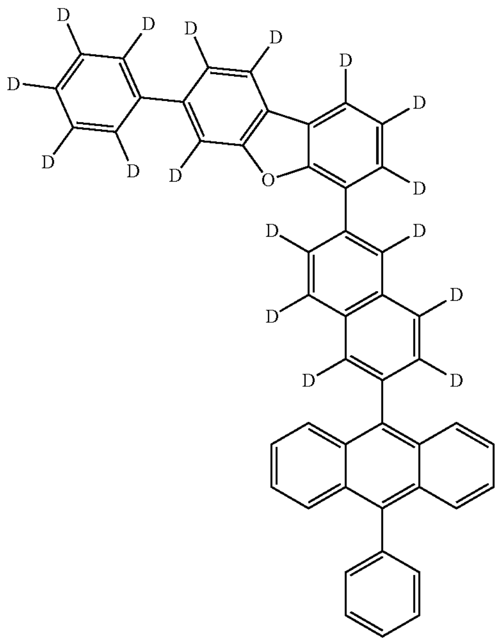
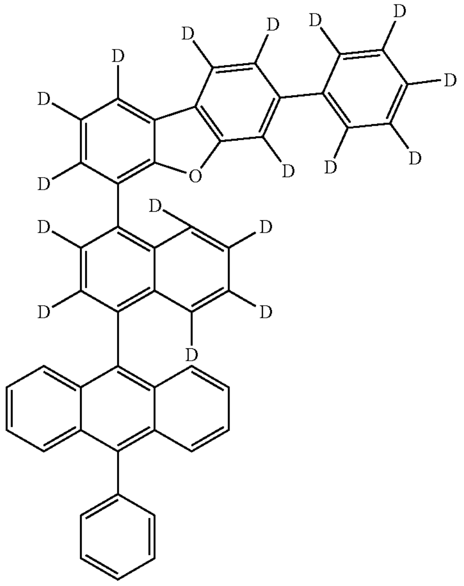
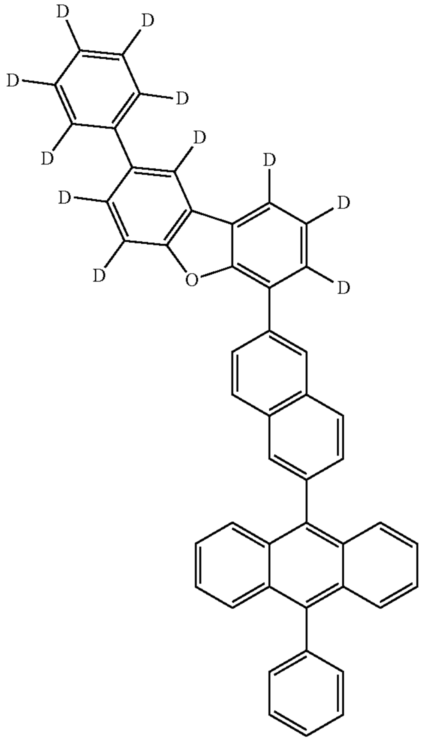

-continued
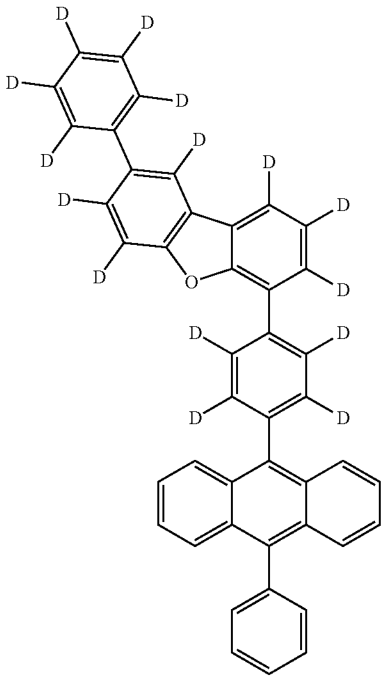
-continued
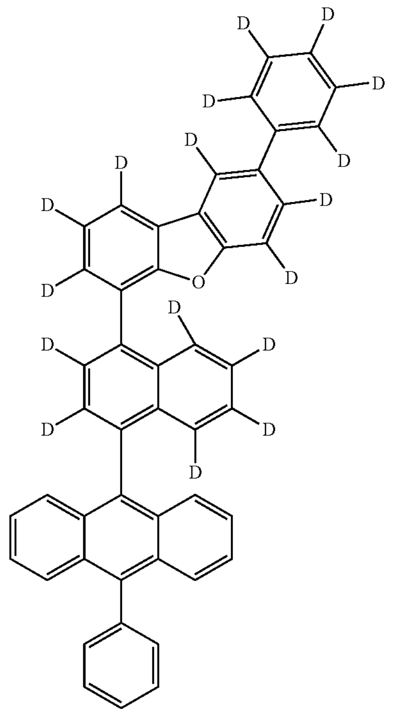
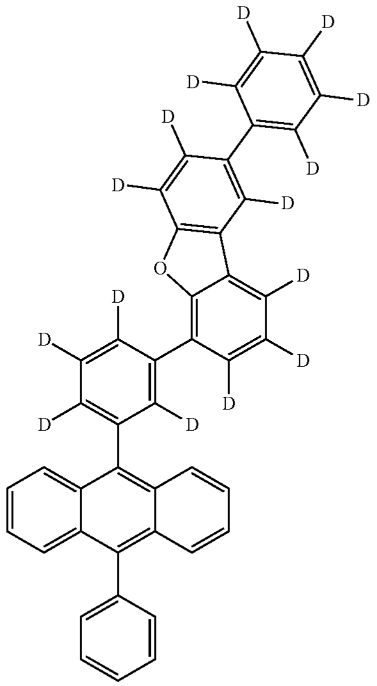
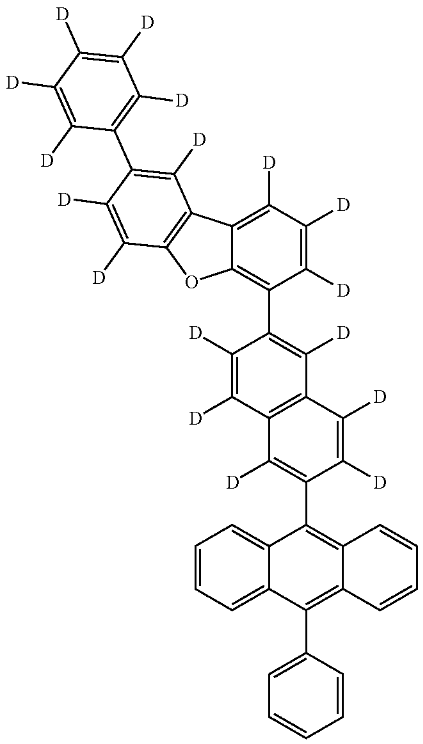

-continued
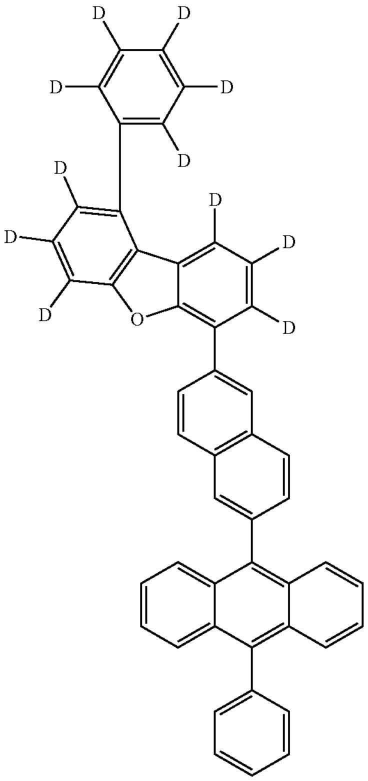
-continued
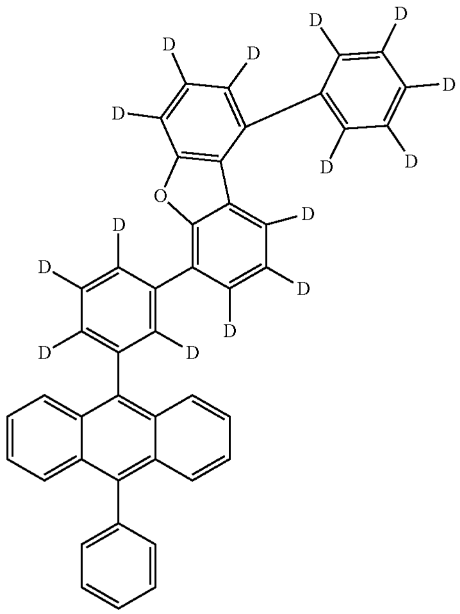
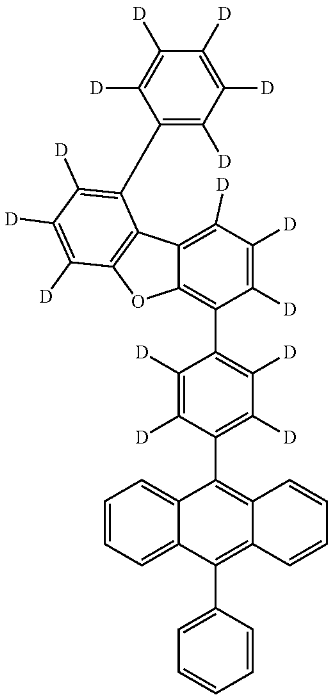
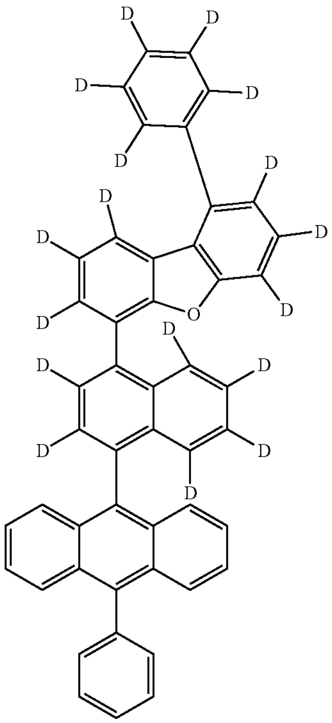

-continued
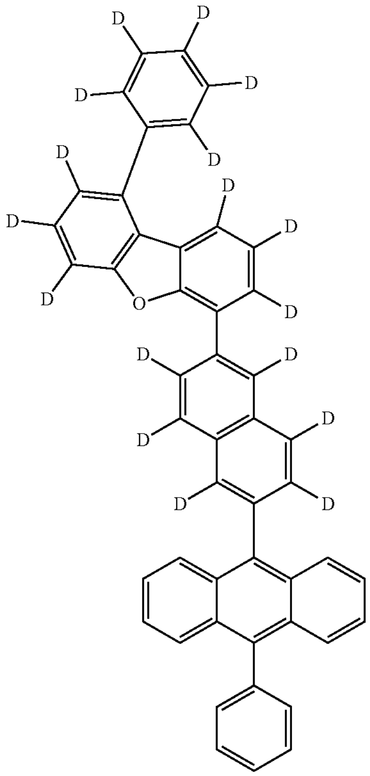
-continued
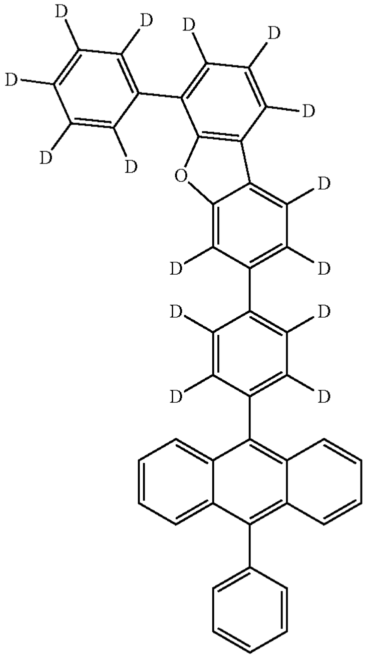
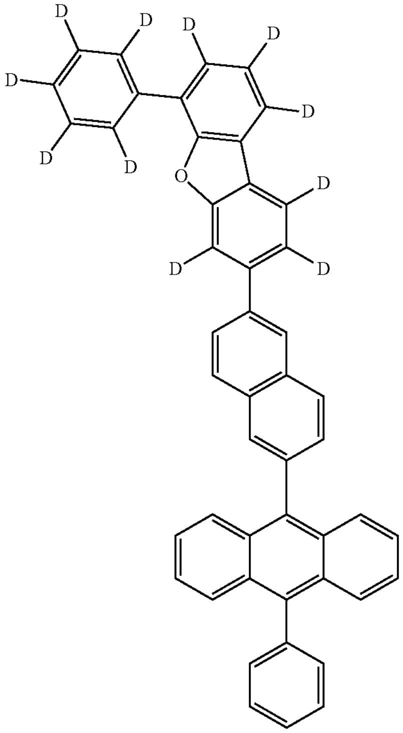
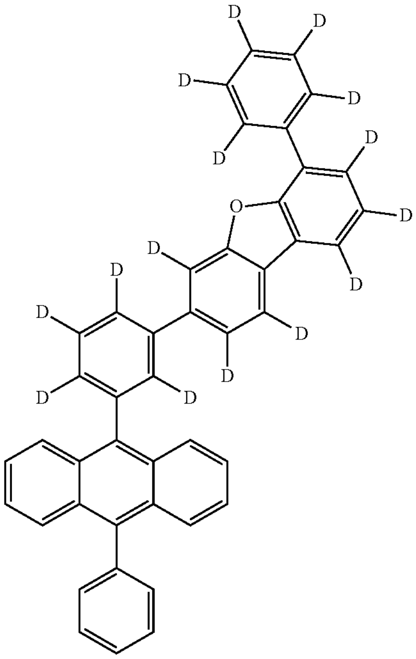

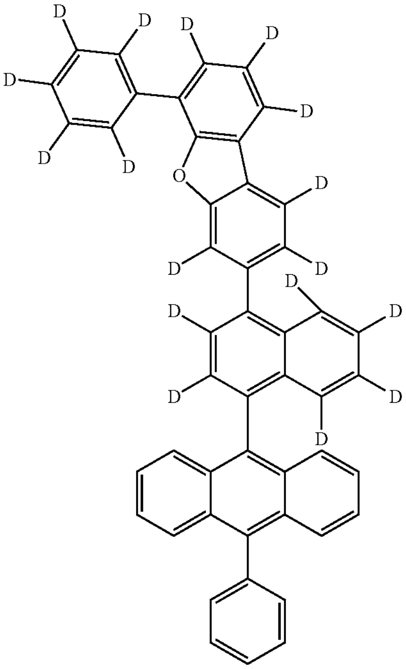
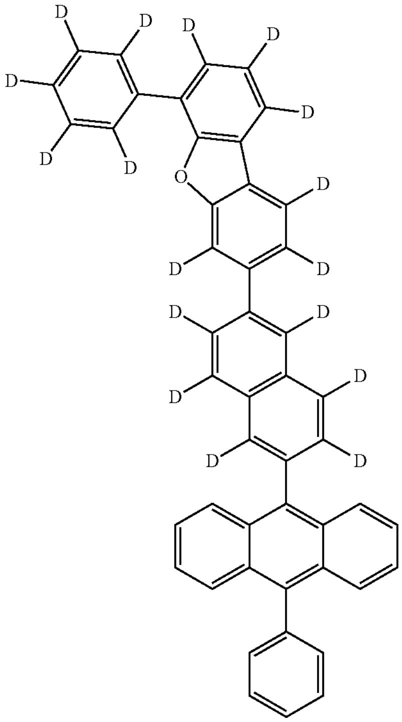
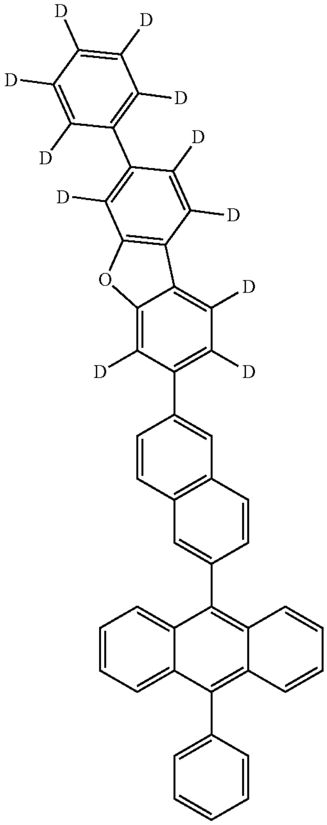
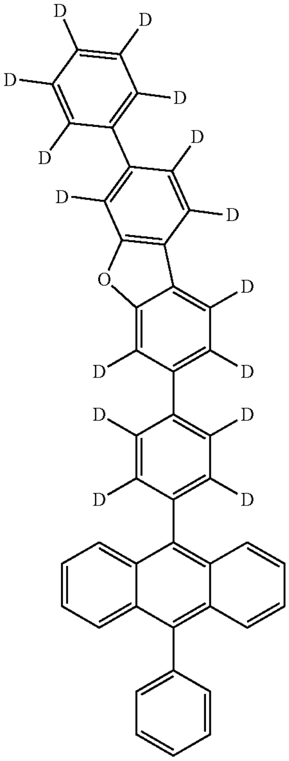

-continued
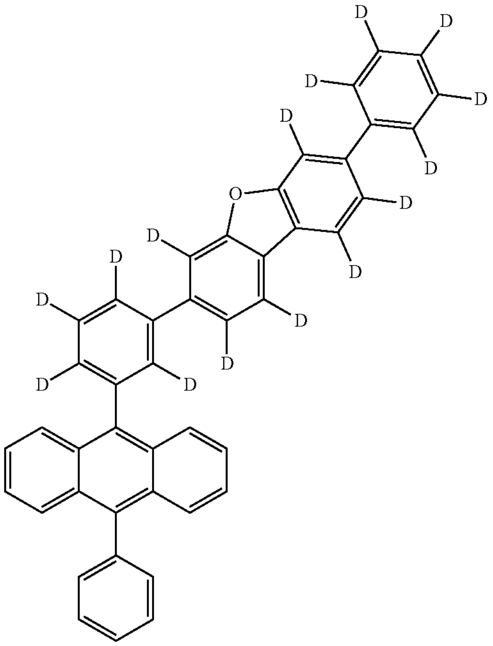
-continued
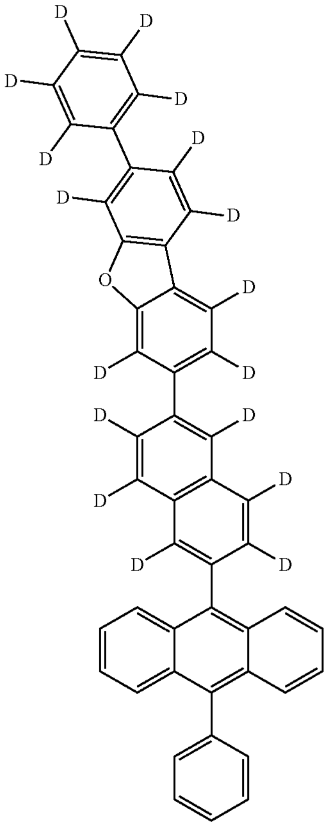
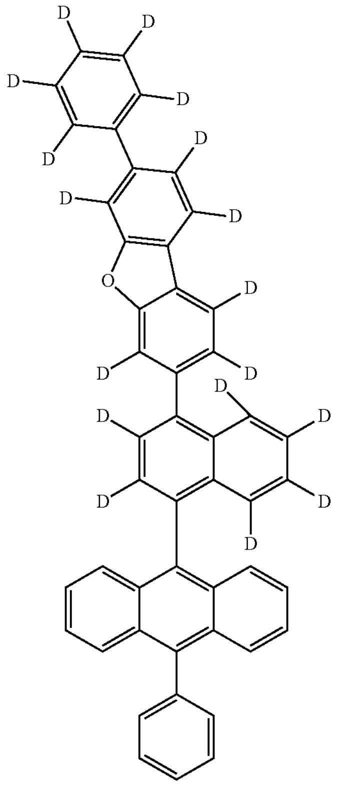
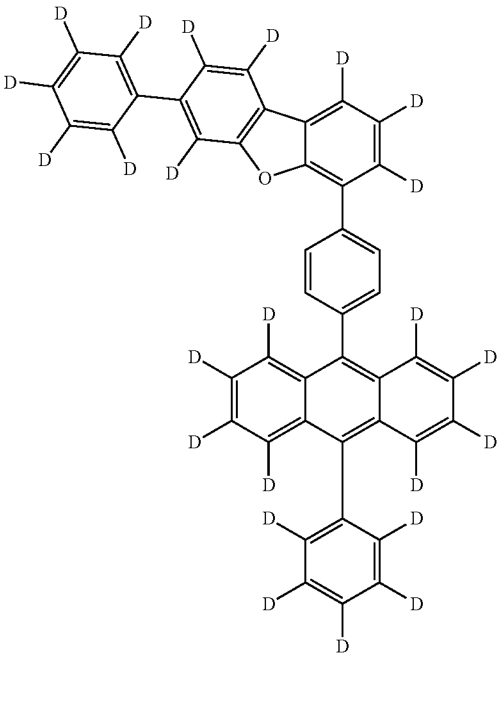

-continued
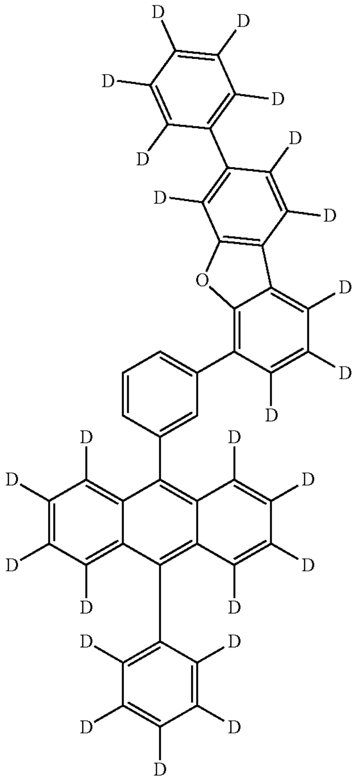
-continued
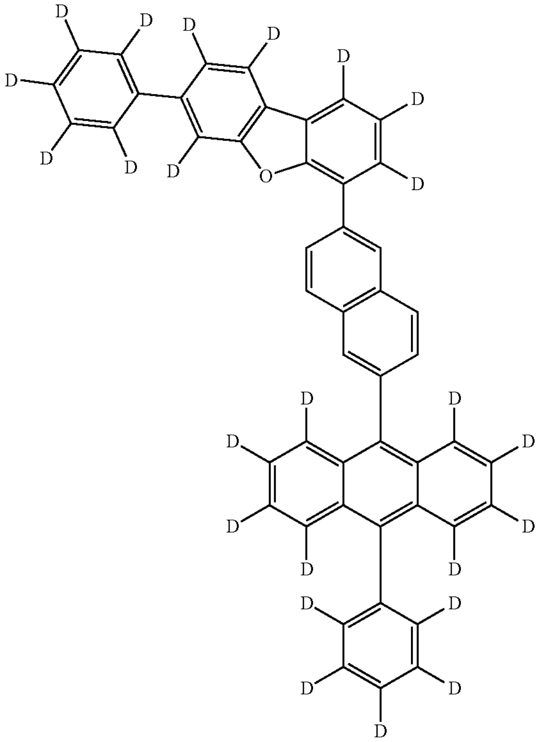
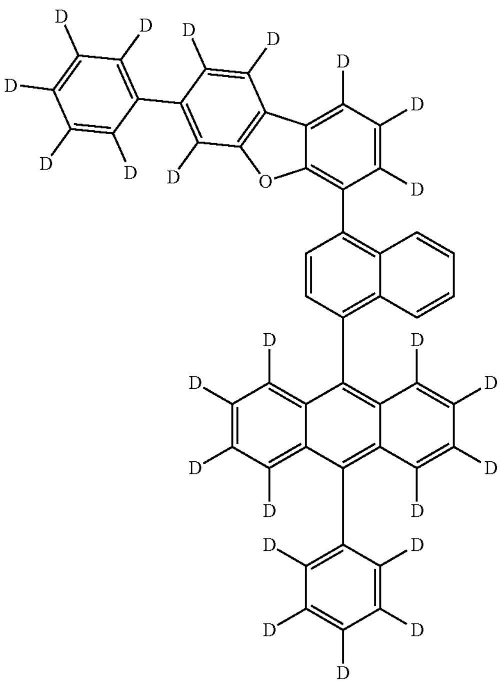
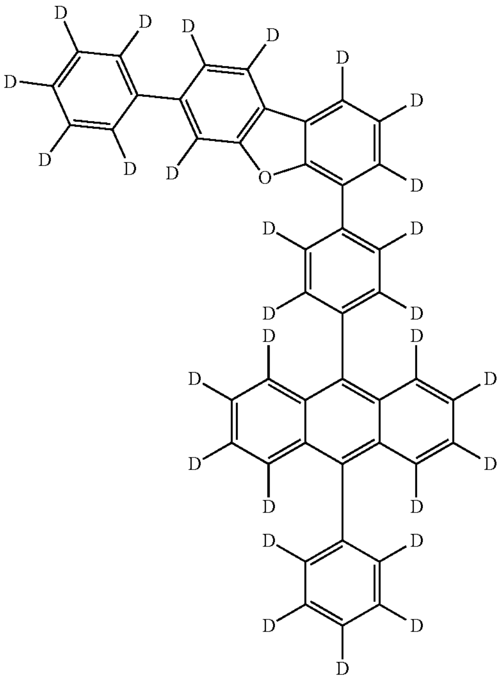

-continued
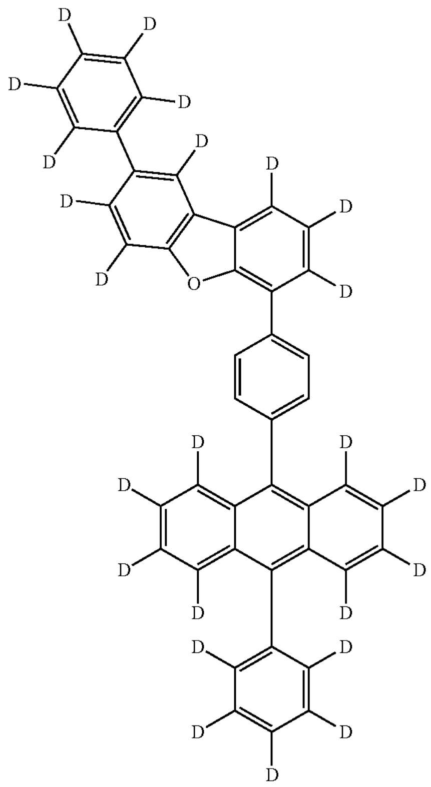
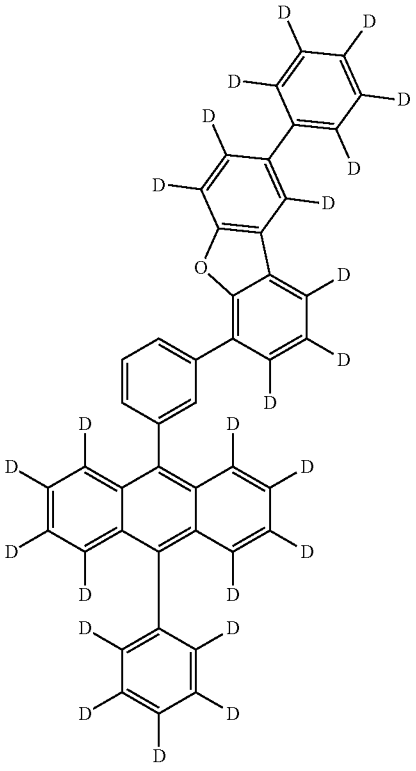
-continued
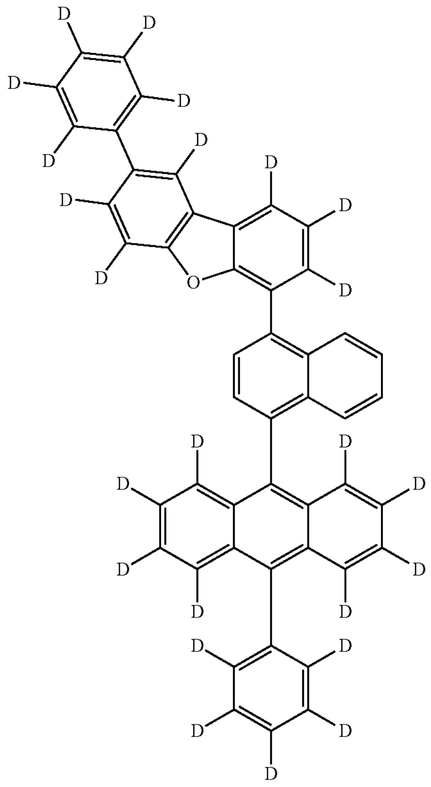
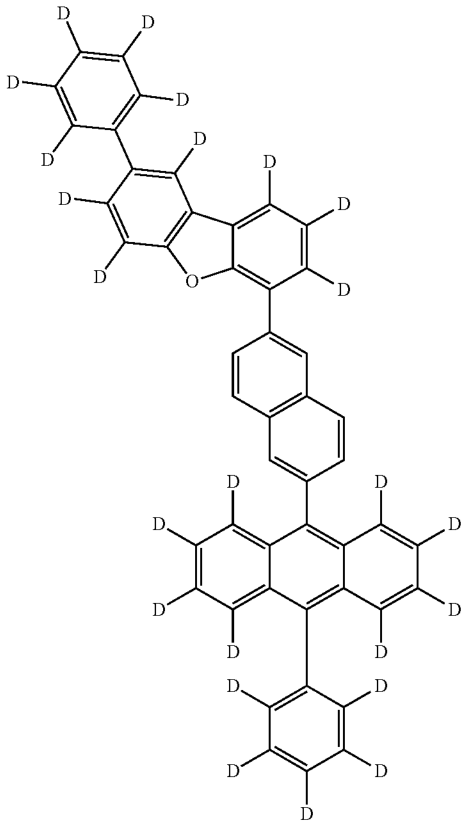

-continued
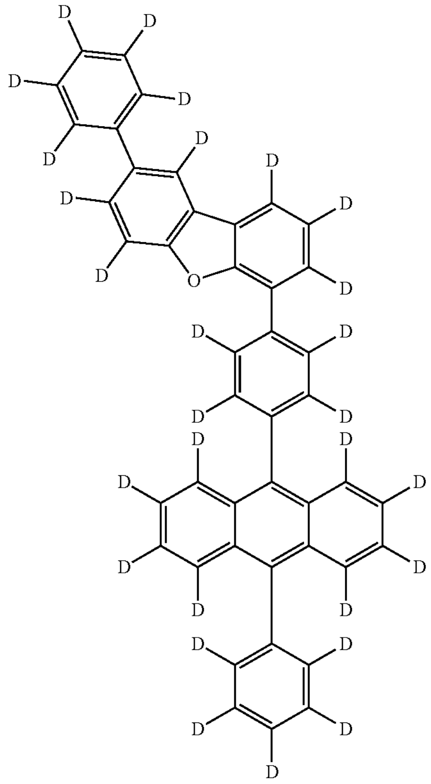
-continued
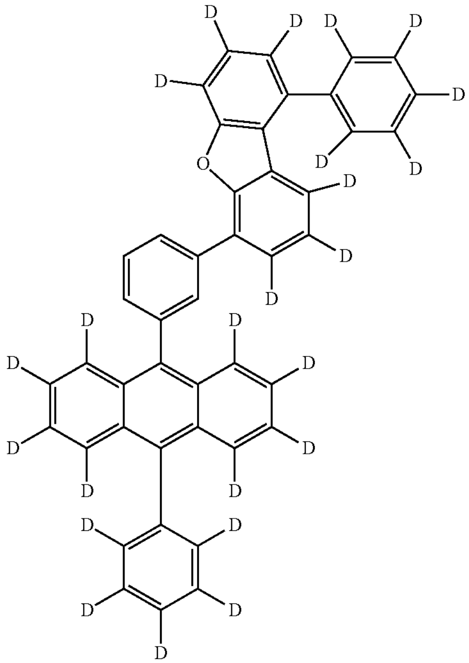
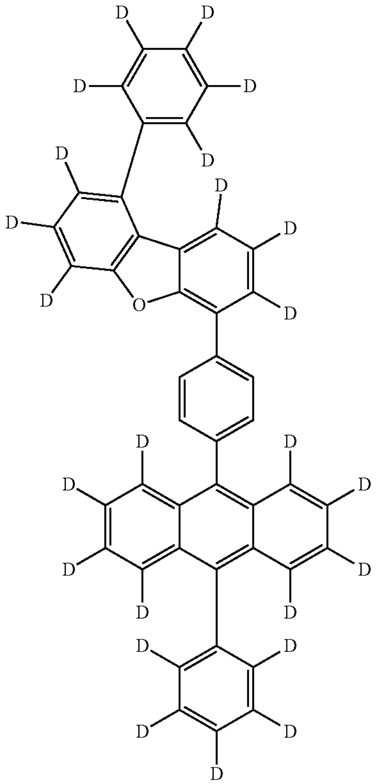
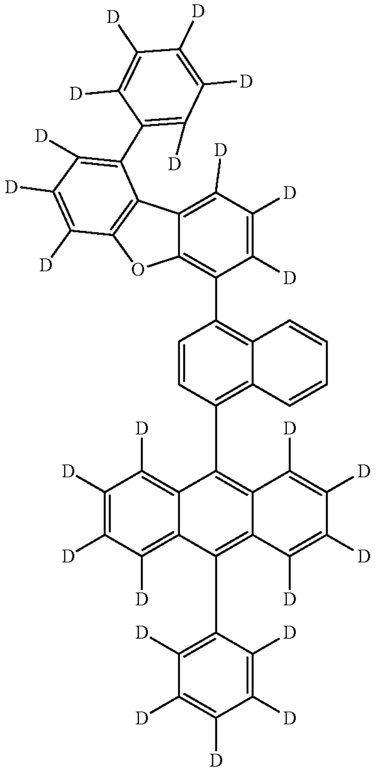

-continued
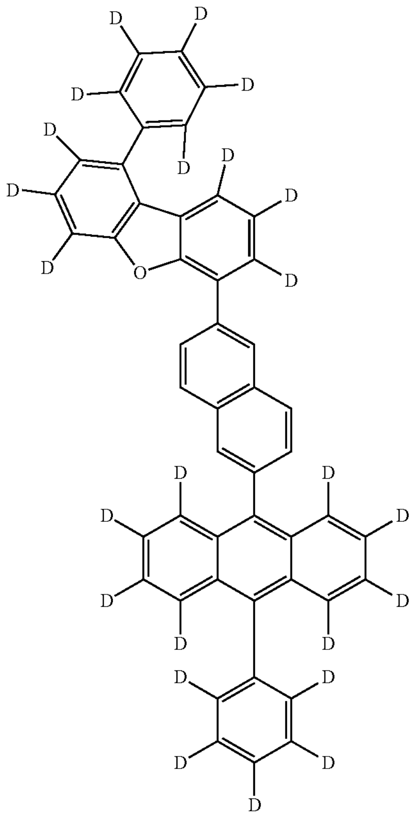
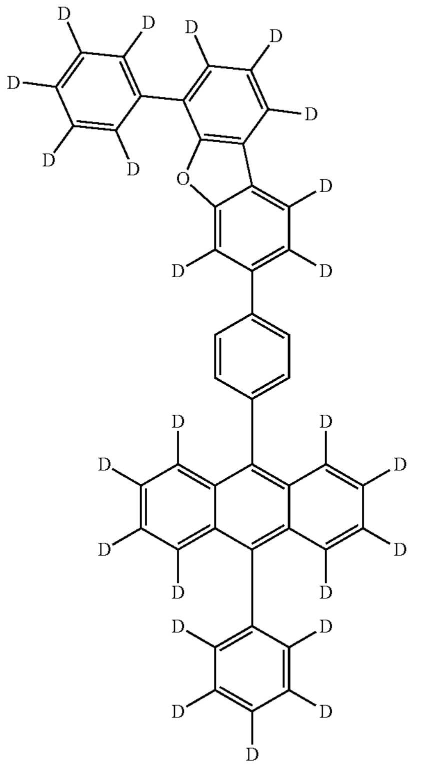
-continued
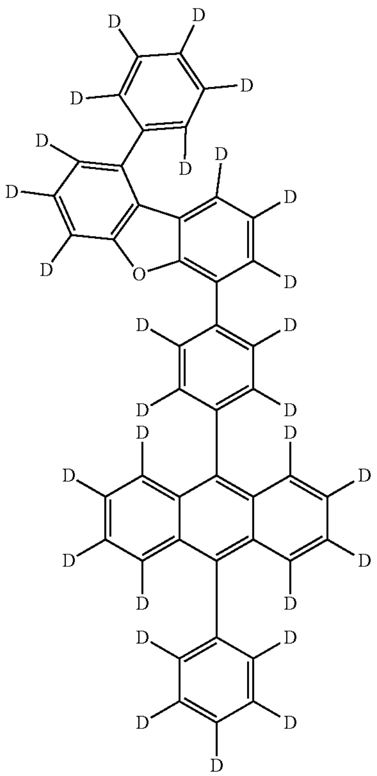
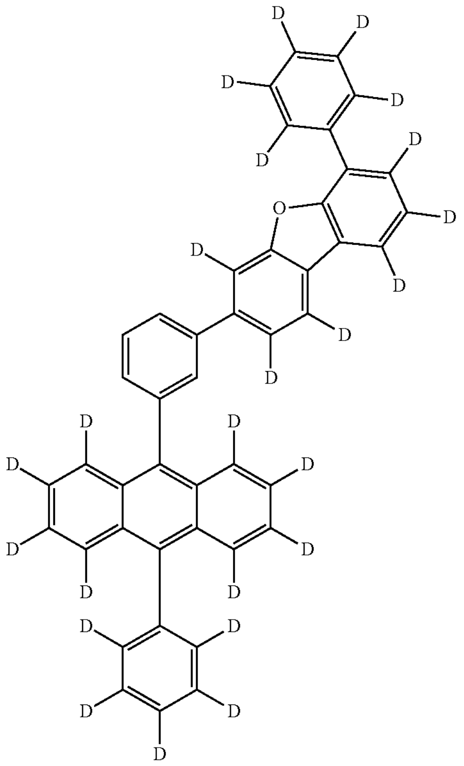

-continued
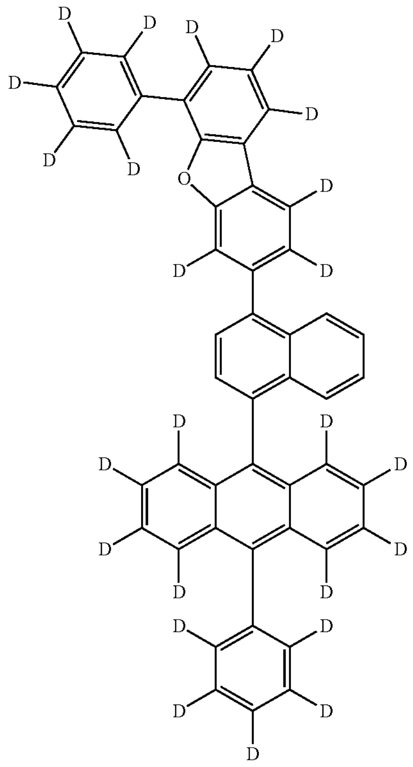
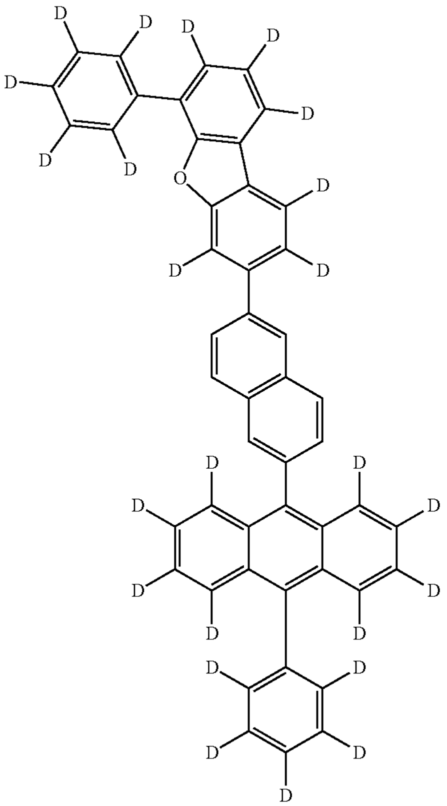
-continued
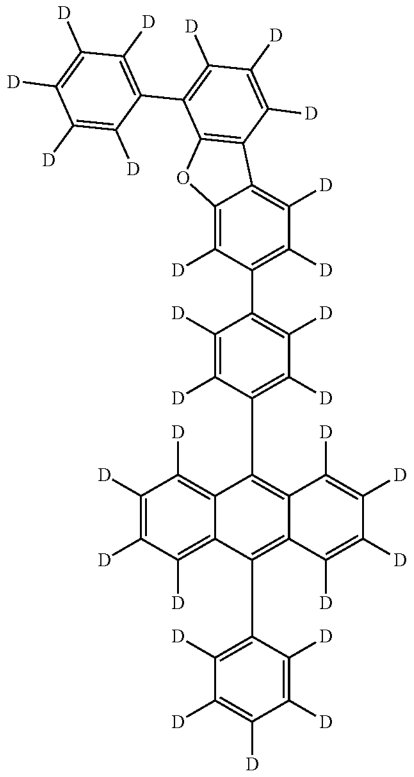
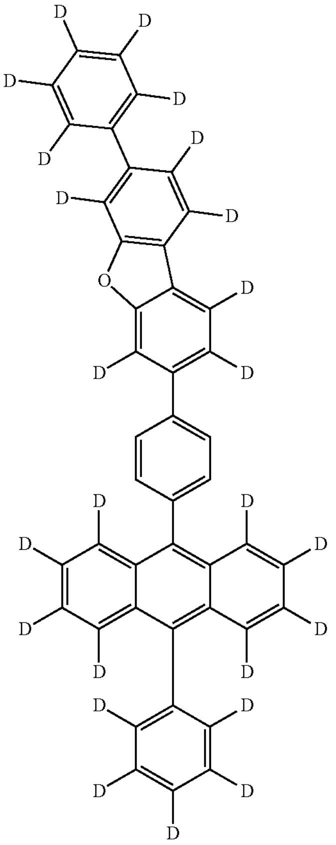

-continued
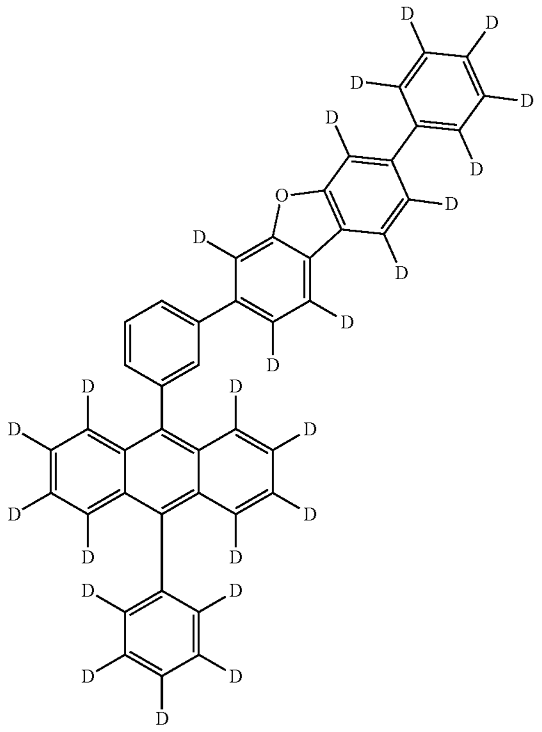
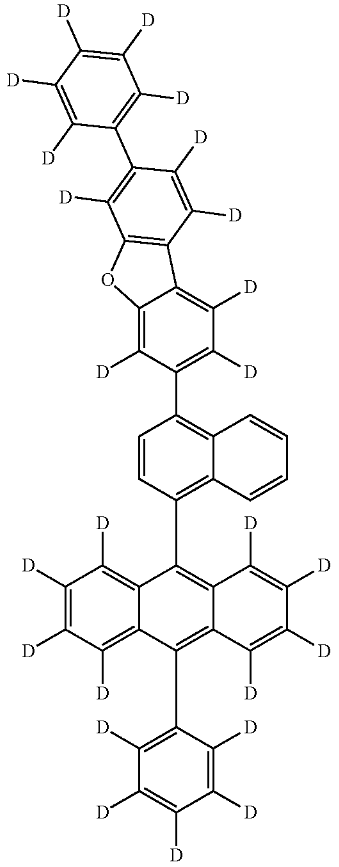
-continued
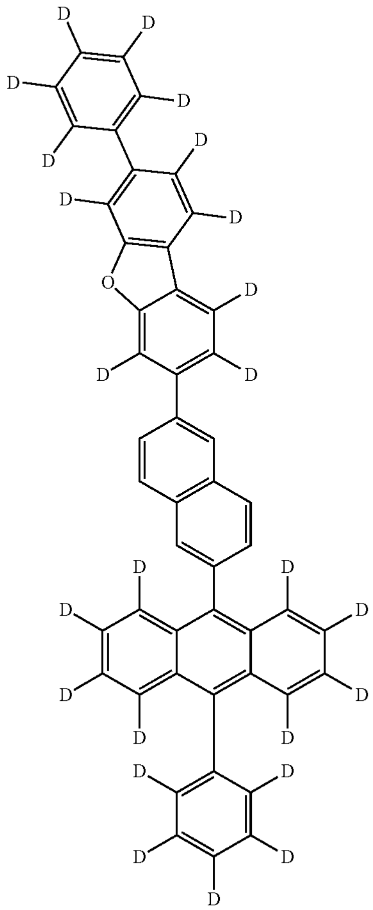

-continued
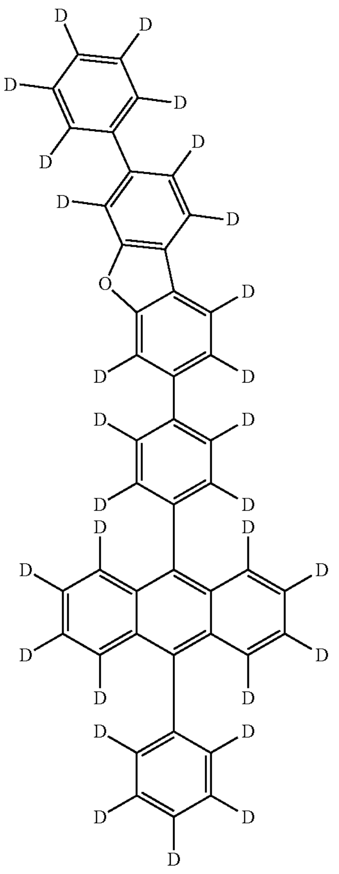
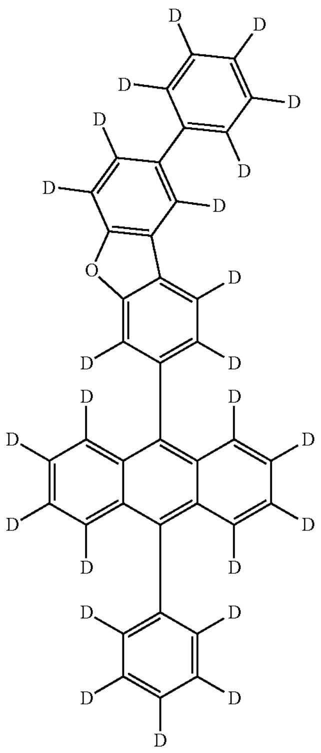
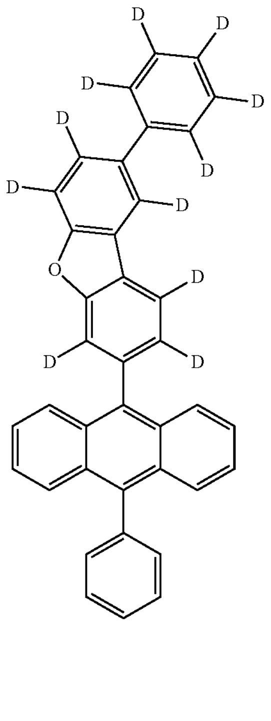
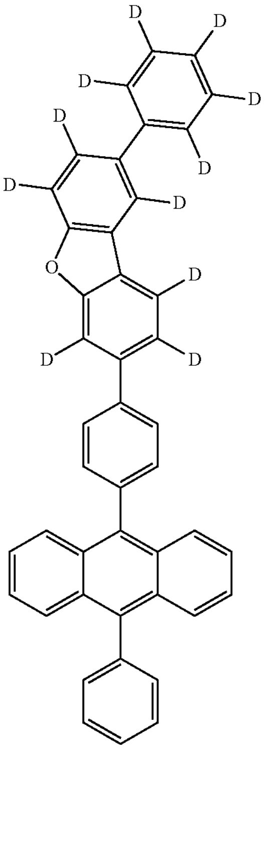
-continued

-continued
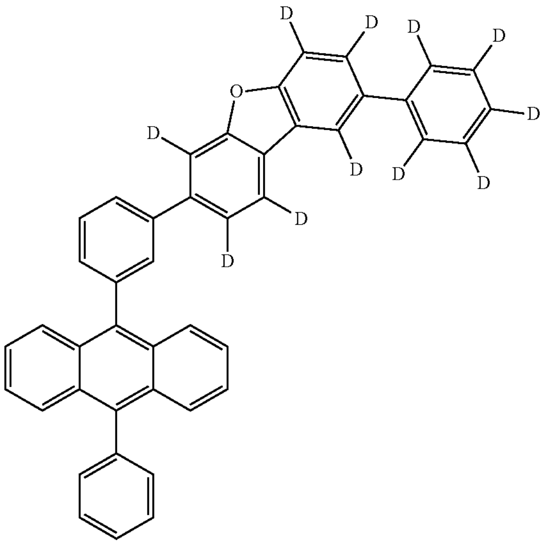
-continued
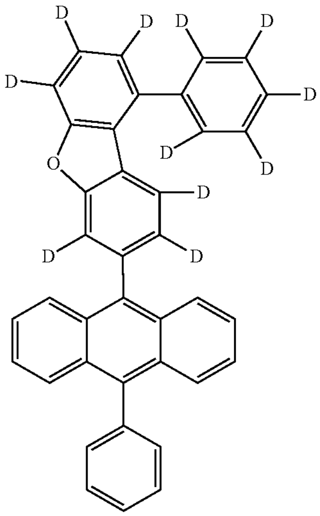
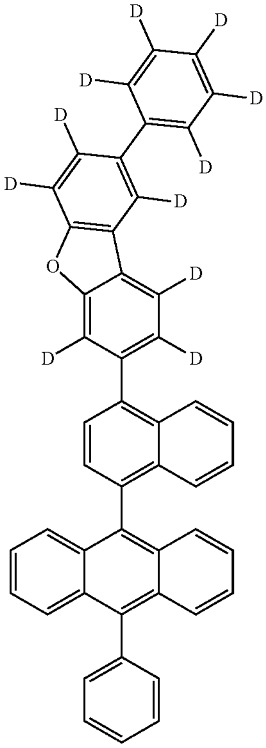
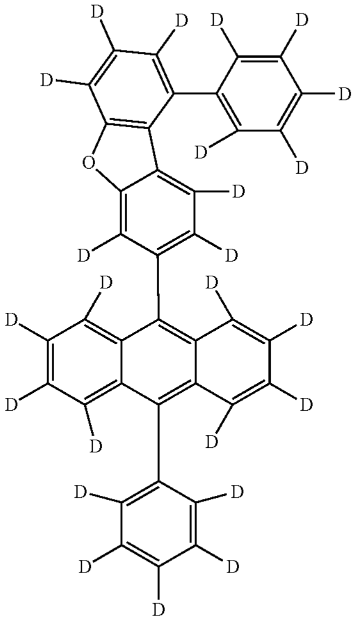

-continued
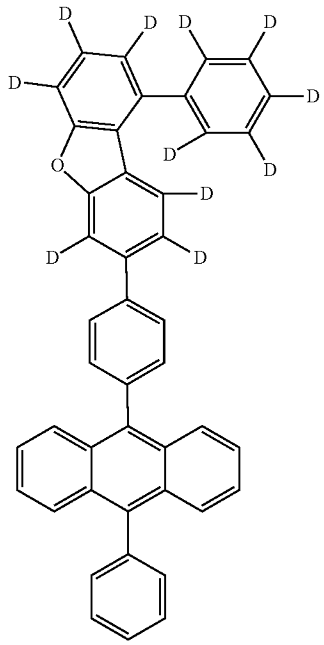
-continued
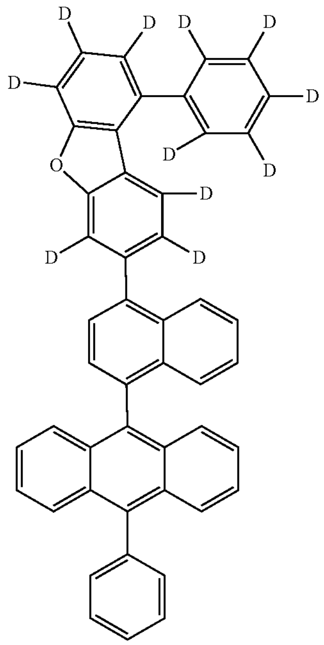
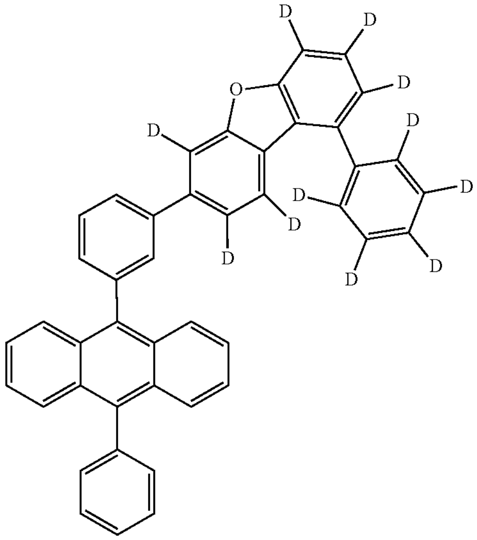
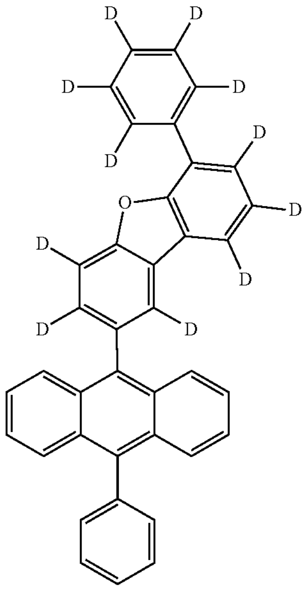

-continued
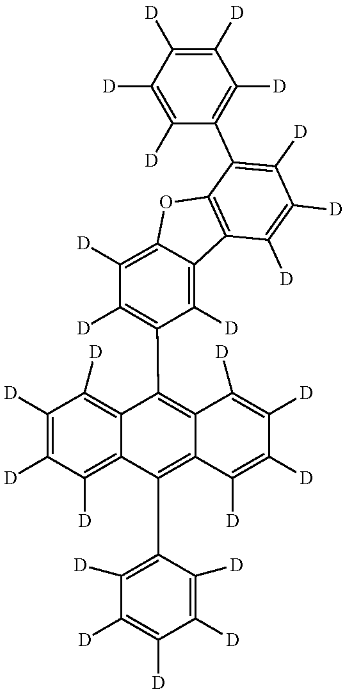
-continued
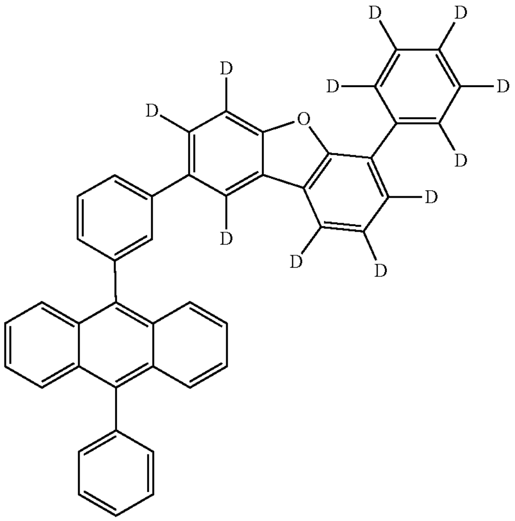
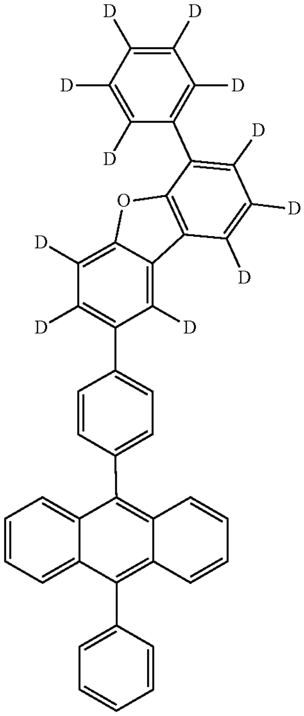
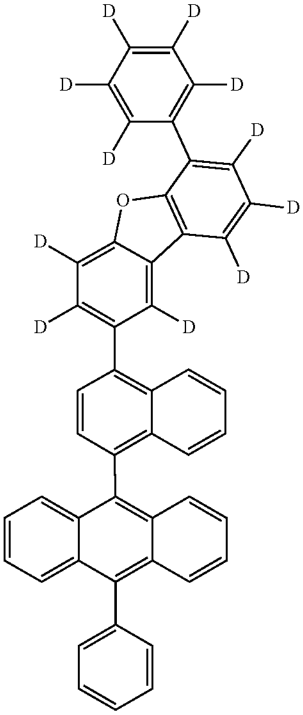

-continued
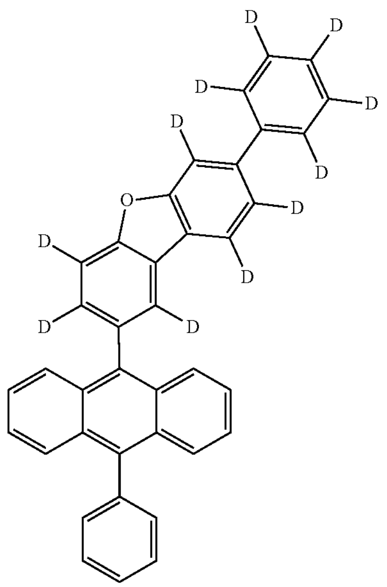
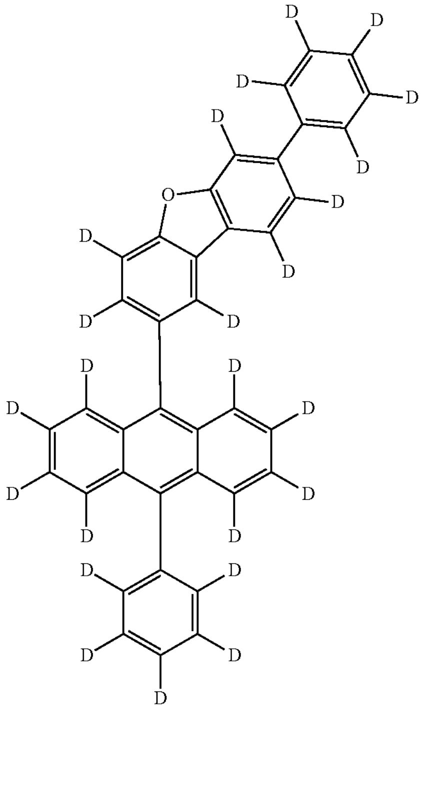
-continued
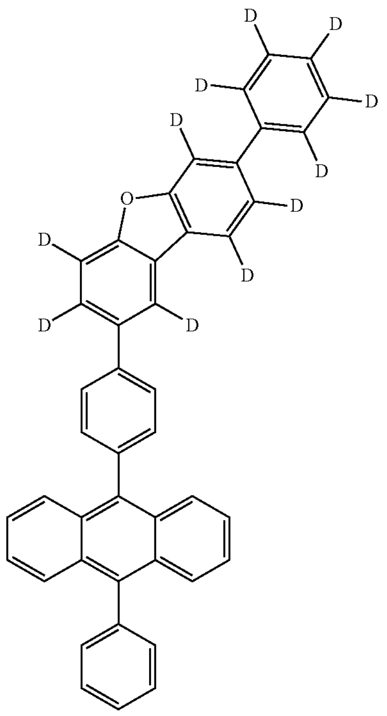
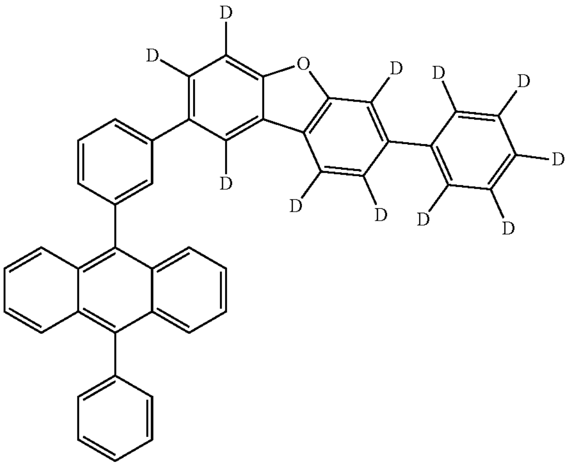

-continued
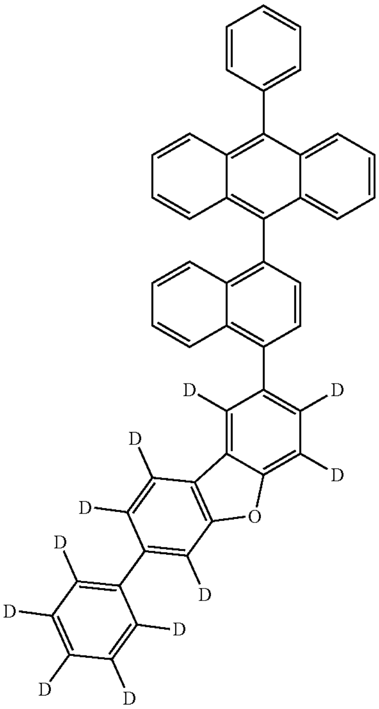
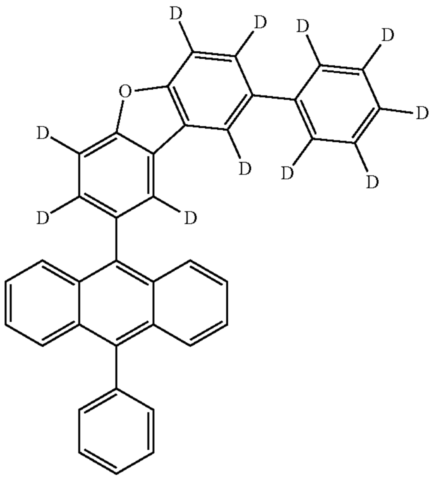
-continued
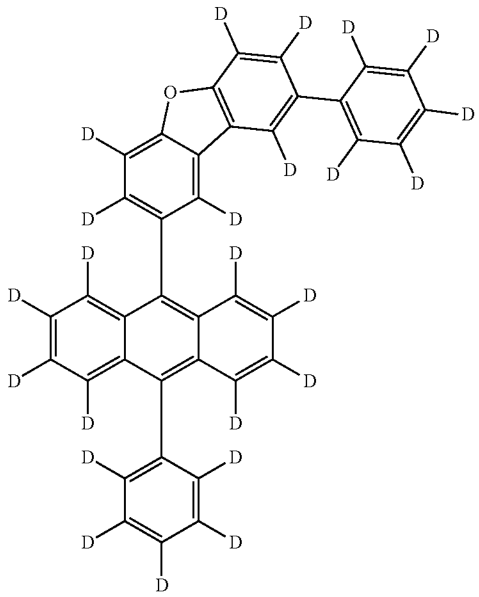
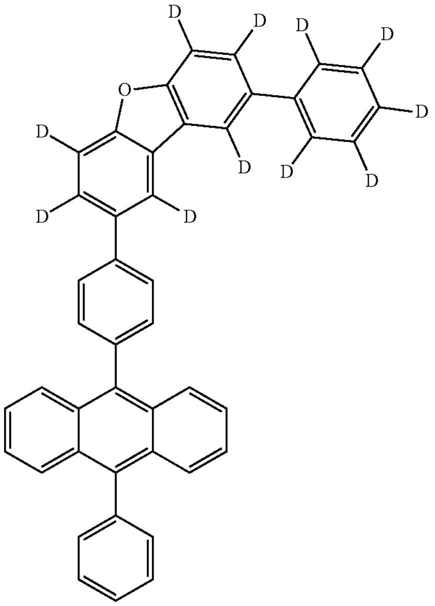
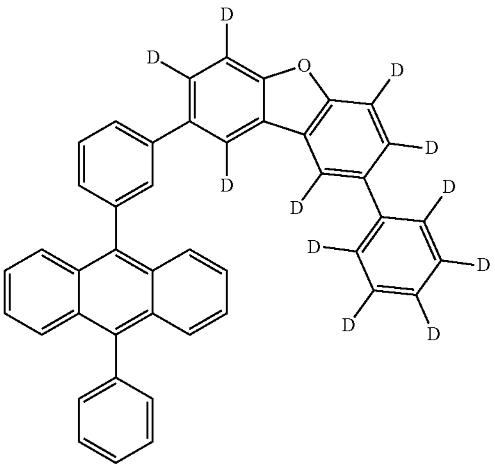

-continued
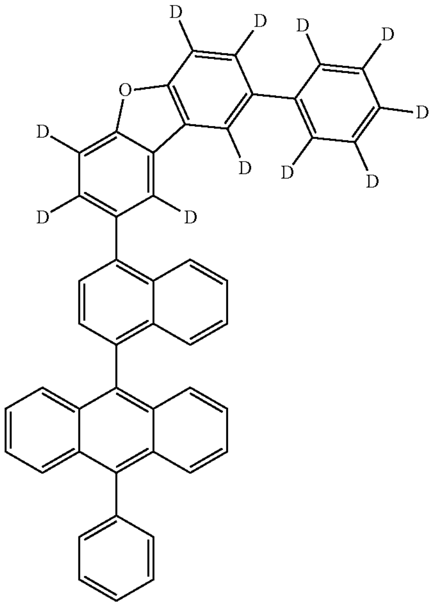 [SMILES: [2H]c1c([2H])c([2H])c(-c2c([2H])c([2H])c3oc4c([2H])c([2H])c(-c5ccc(-c6c7ccccc7c(-c7ccccc7)c7ccccc67)c6ccccc56)c([2H])c4c3c2[2H])c([2H])c1[2H]]
-continued
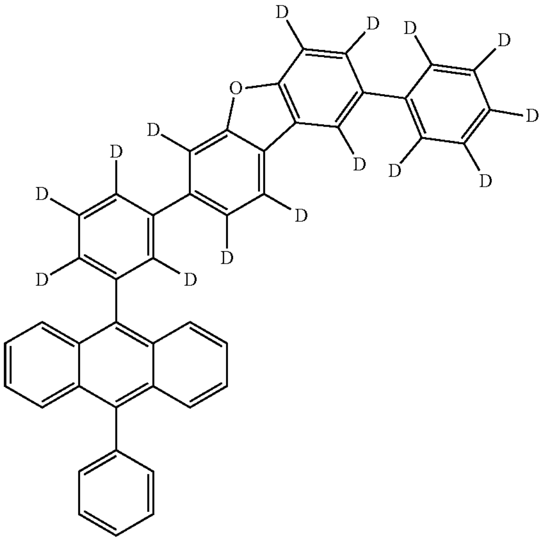
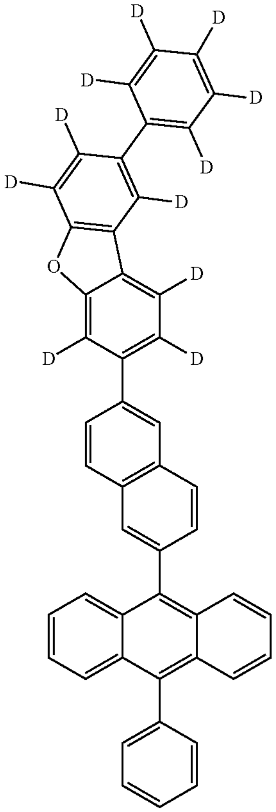
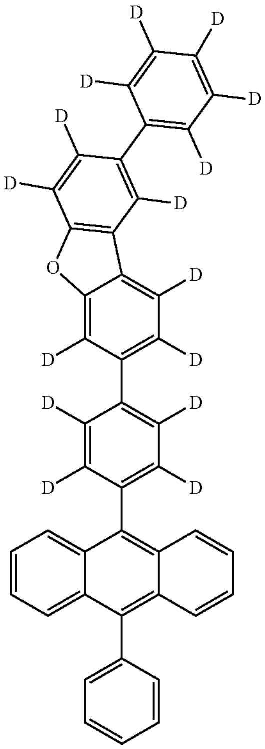
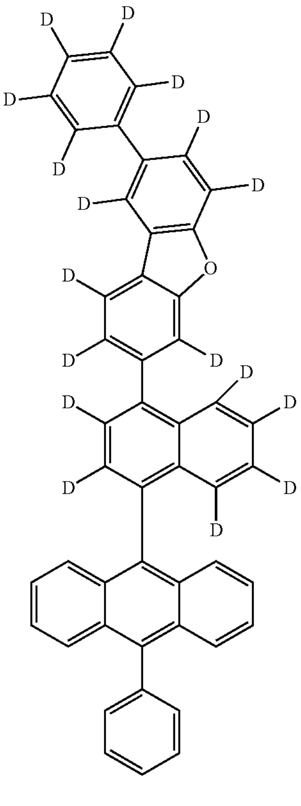

-continued
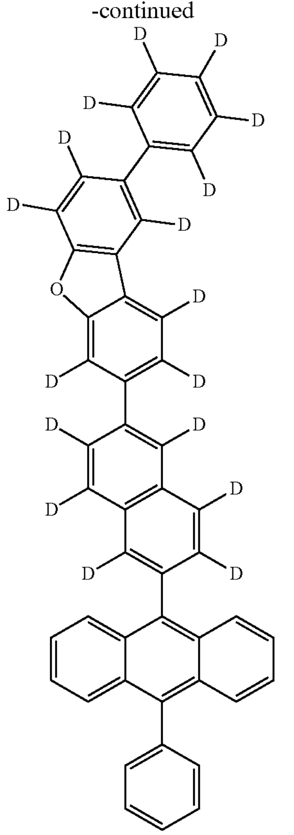
-continued
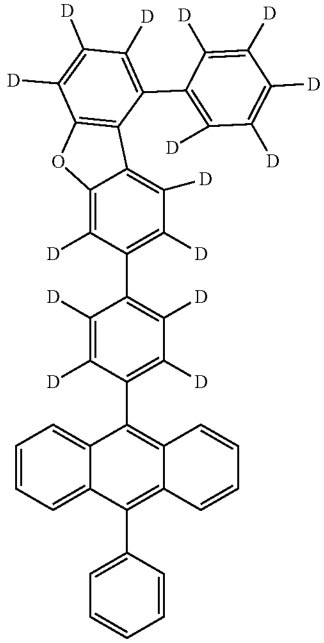
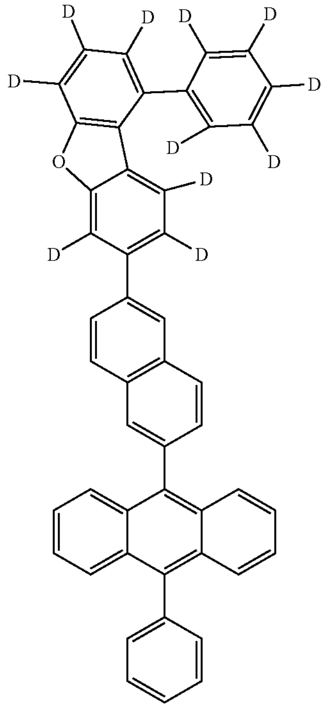
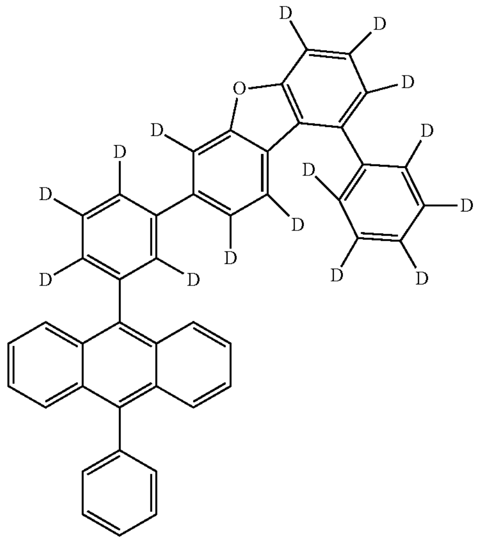

-continued
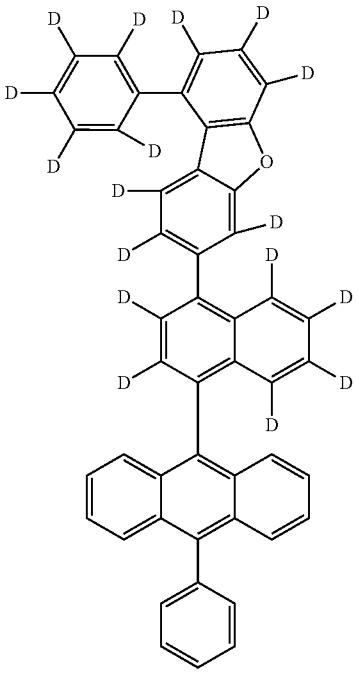
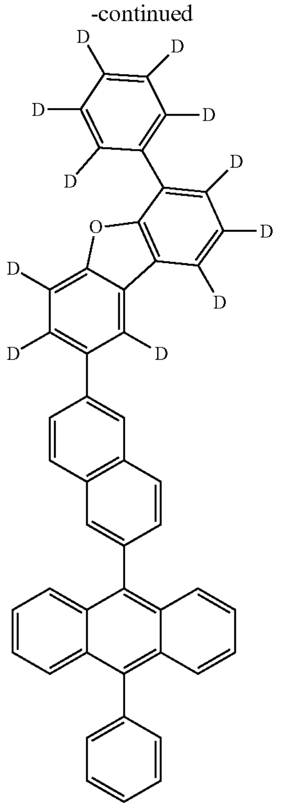
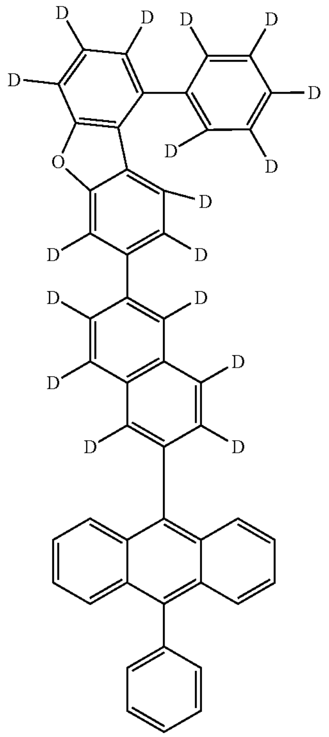
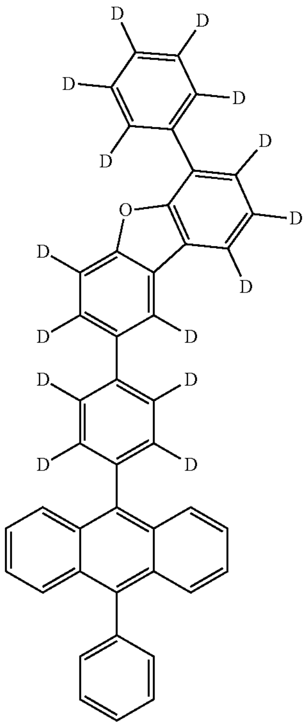

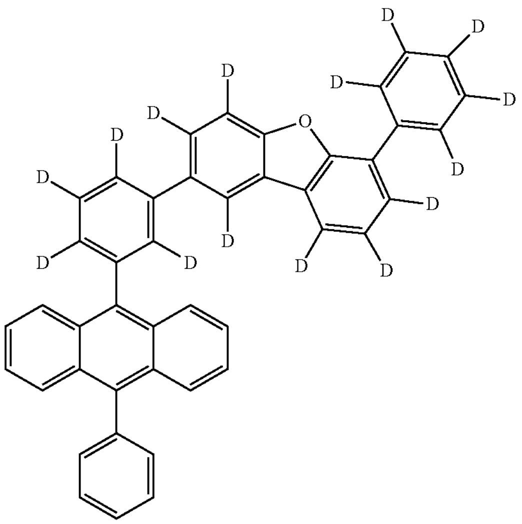
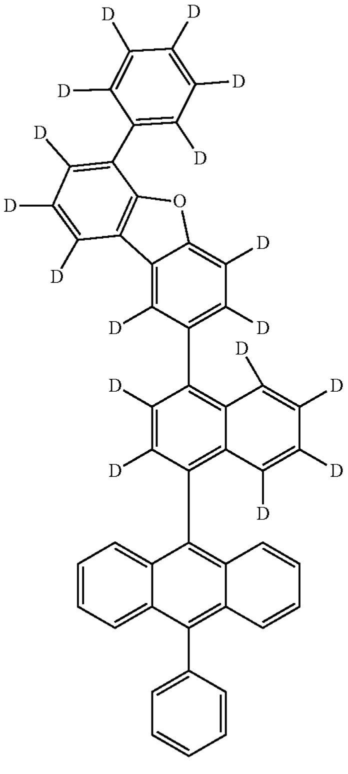
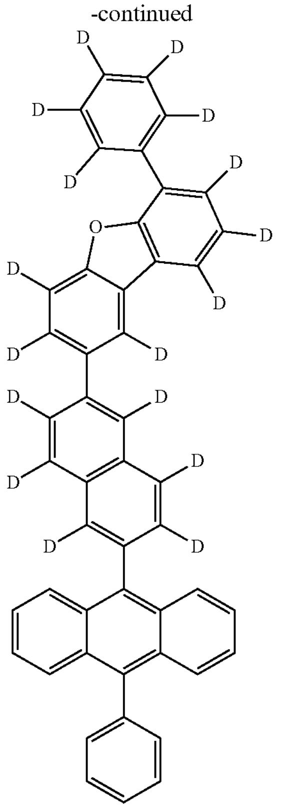
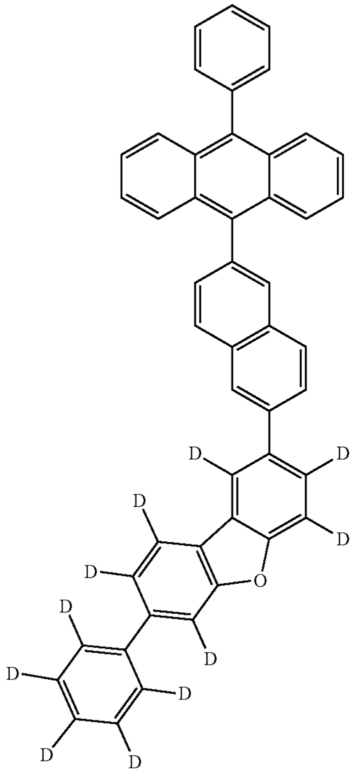

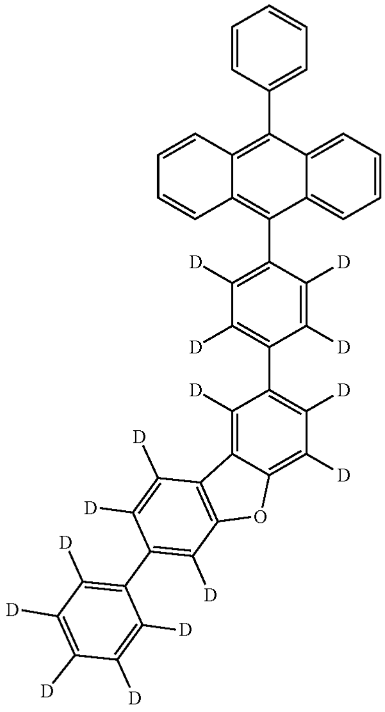
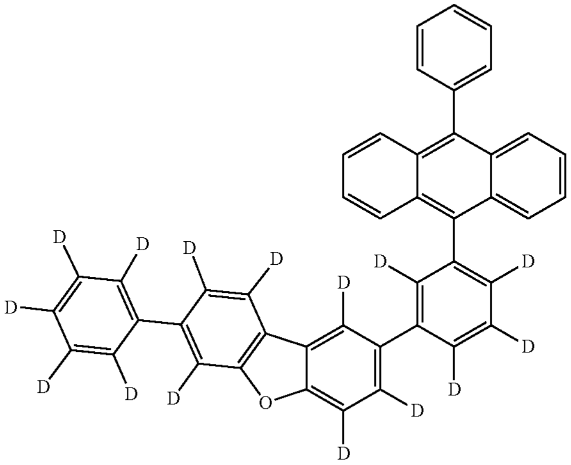
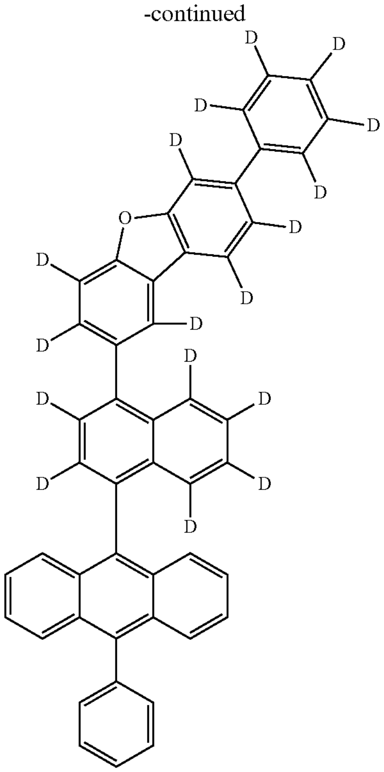
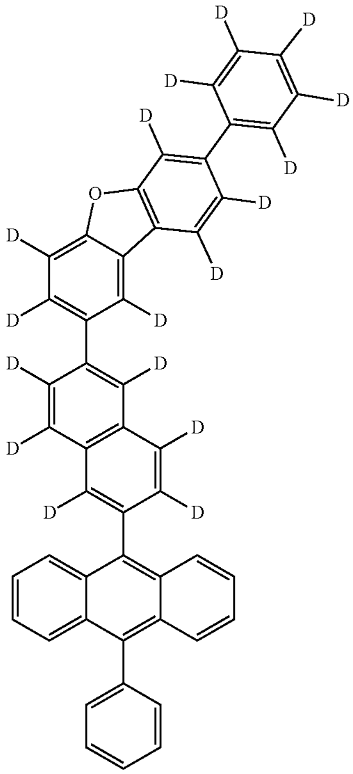

-continued
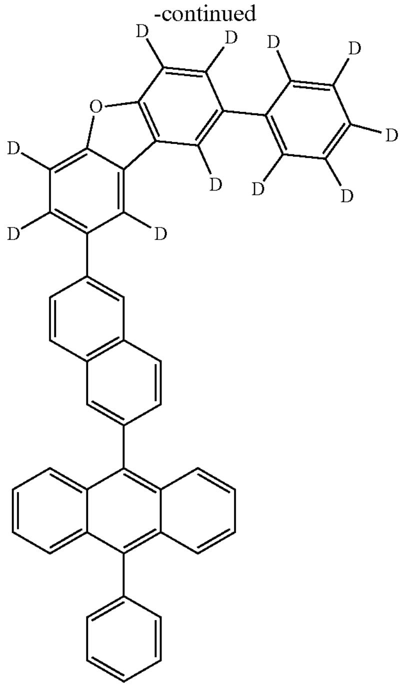
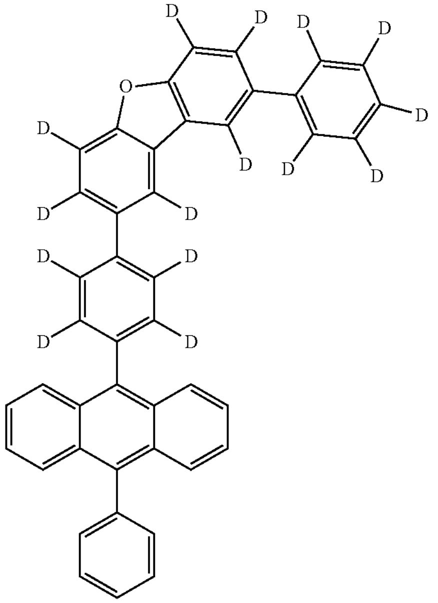
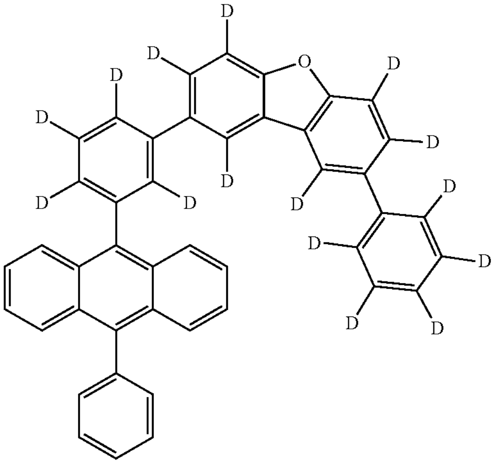
-continued
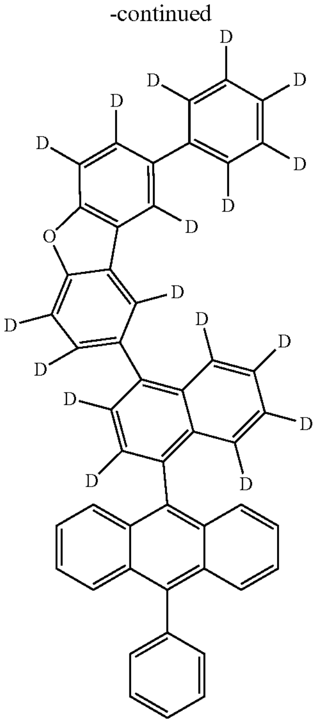
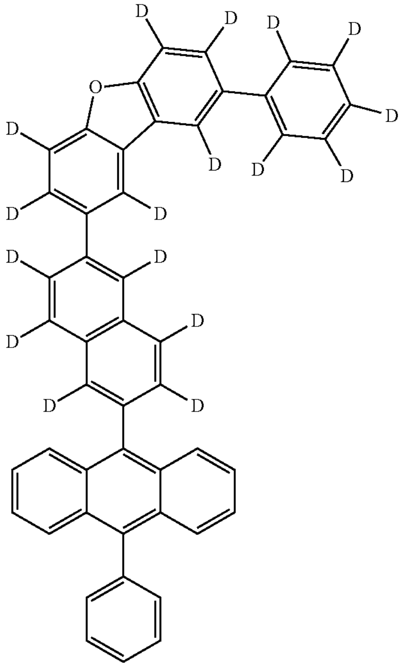

-continued
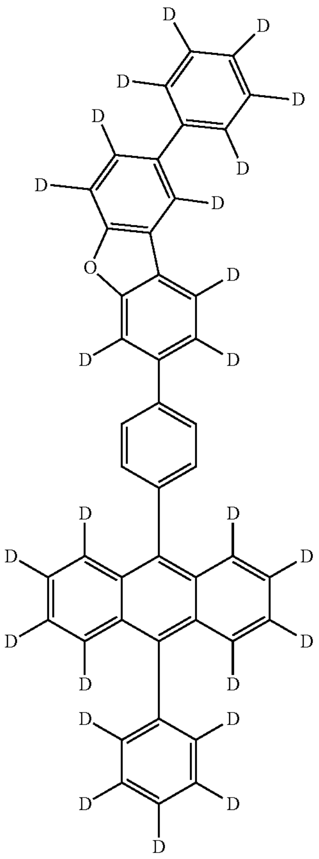
-continued
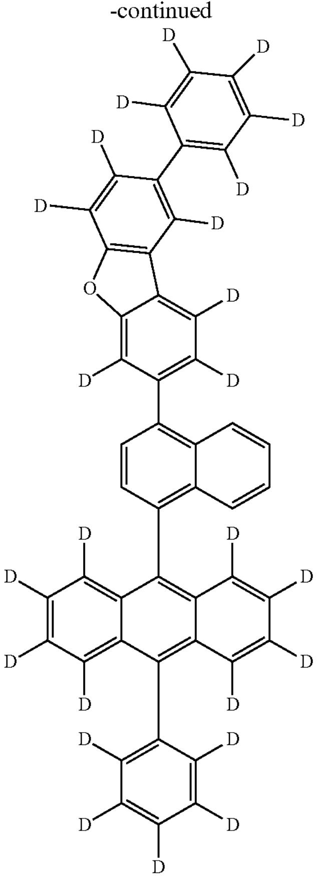
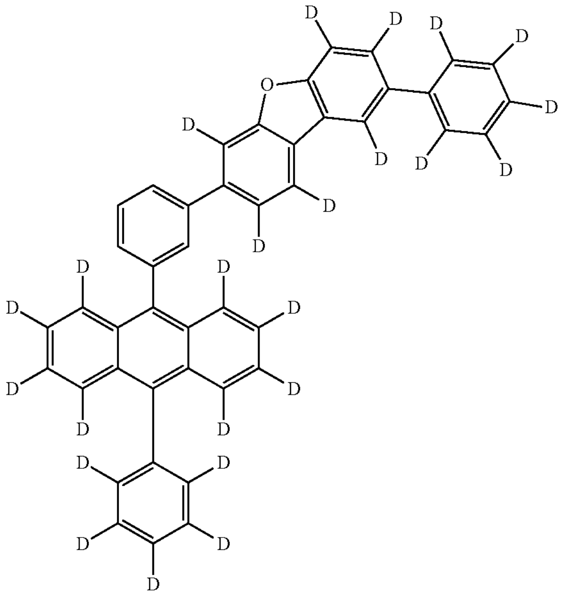

-continued
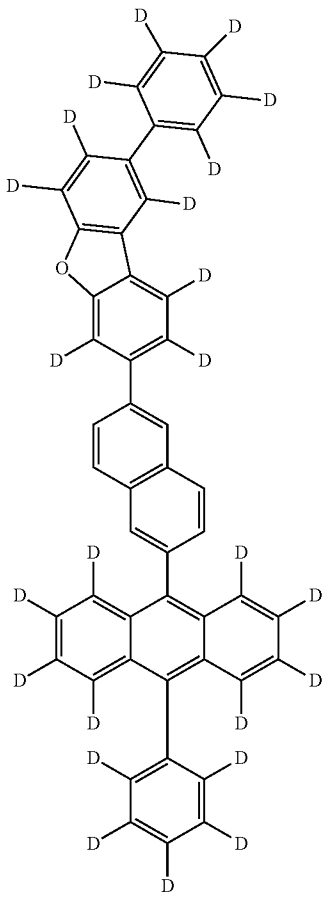
-continued
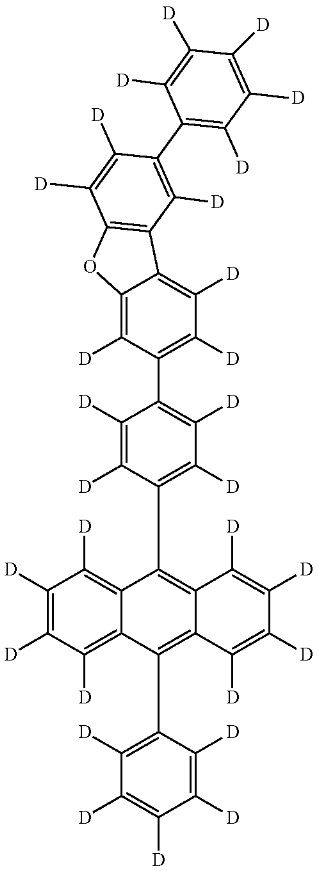
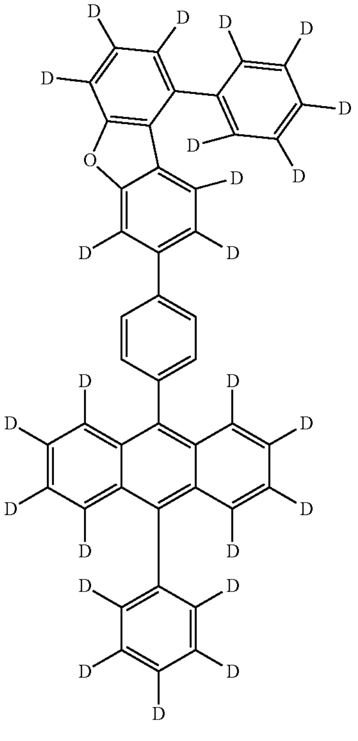

-continued
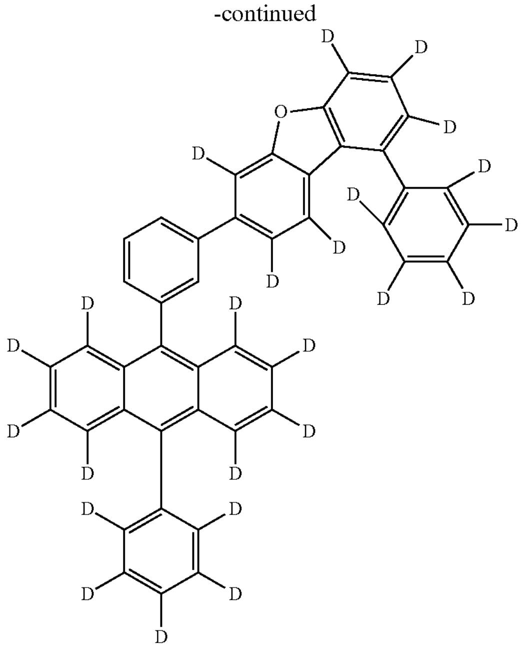
-continued
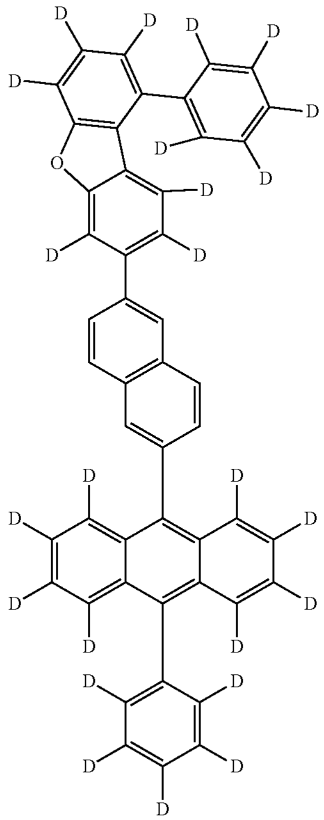
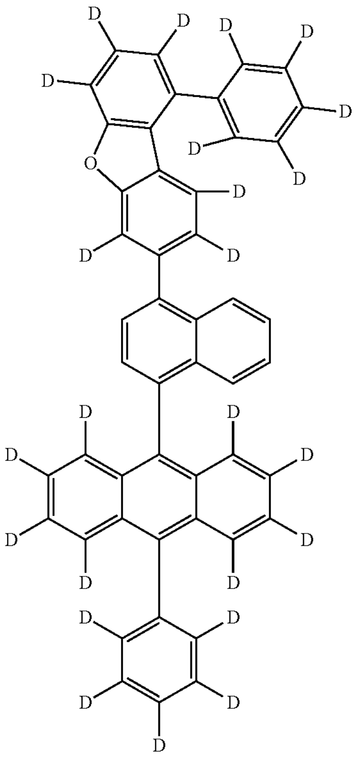
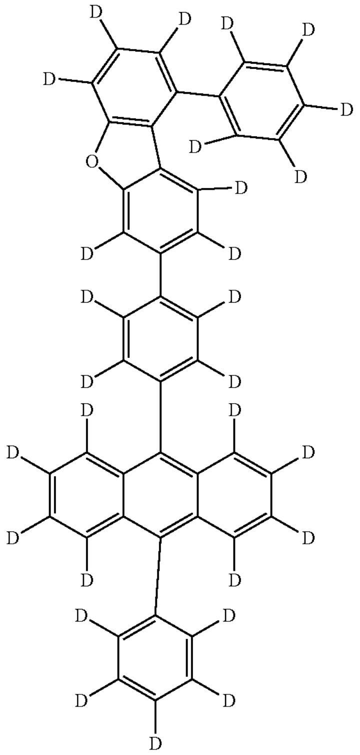

-continued
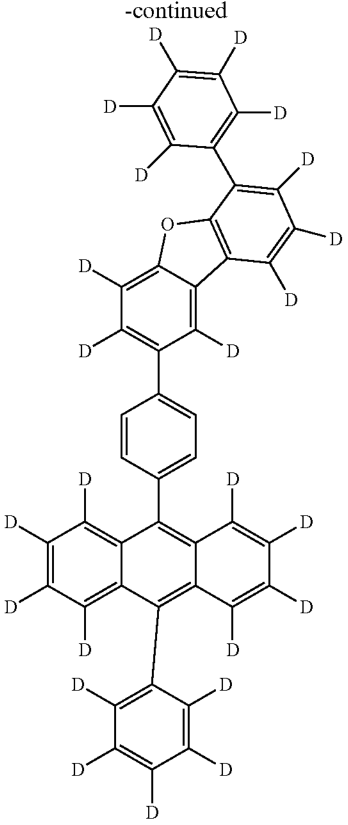
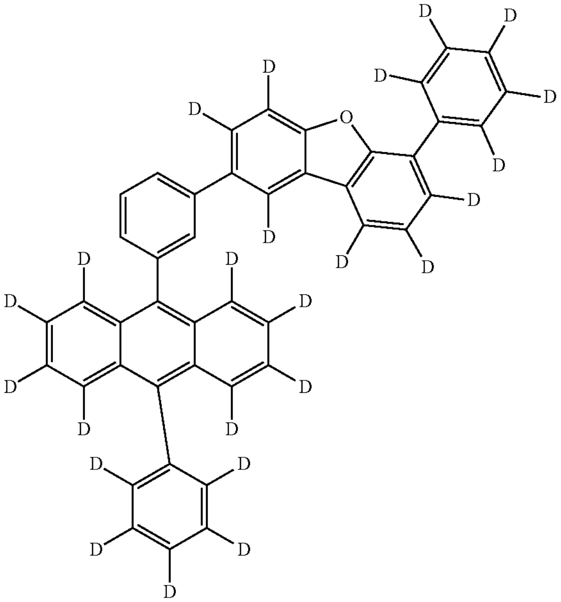
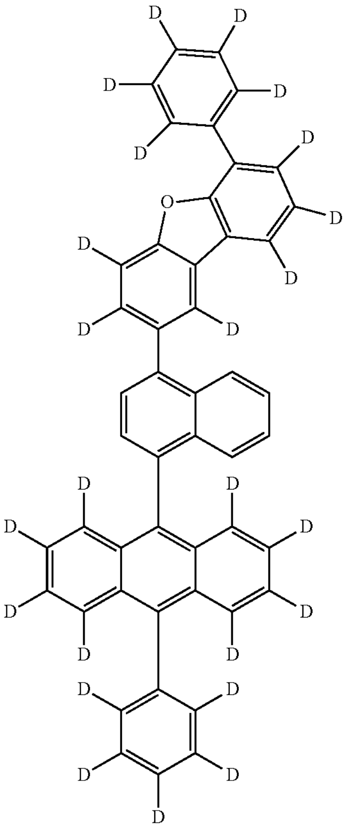
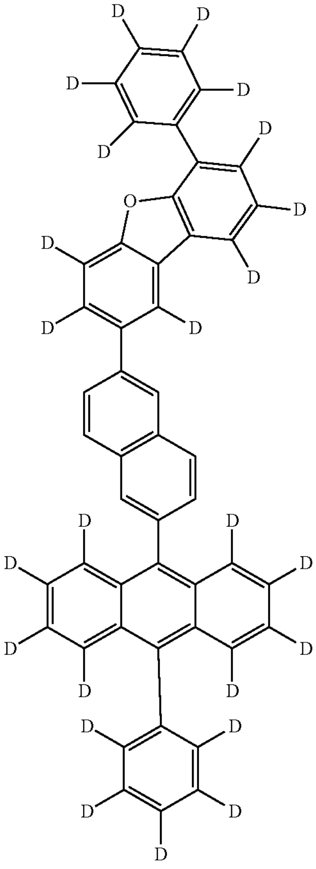

-continued
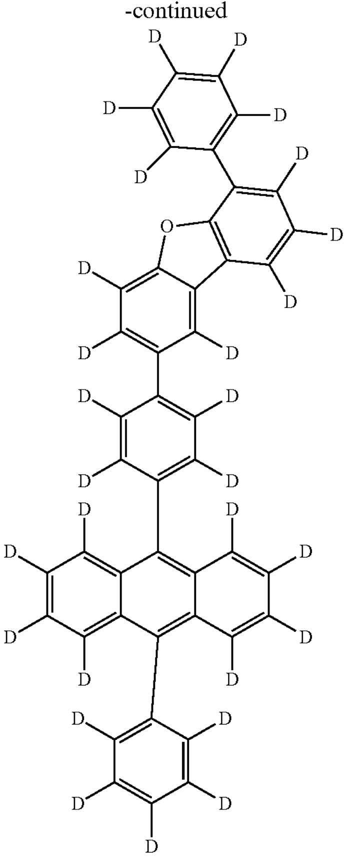
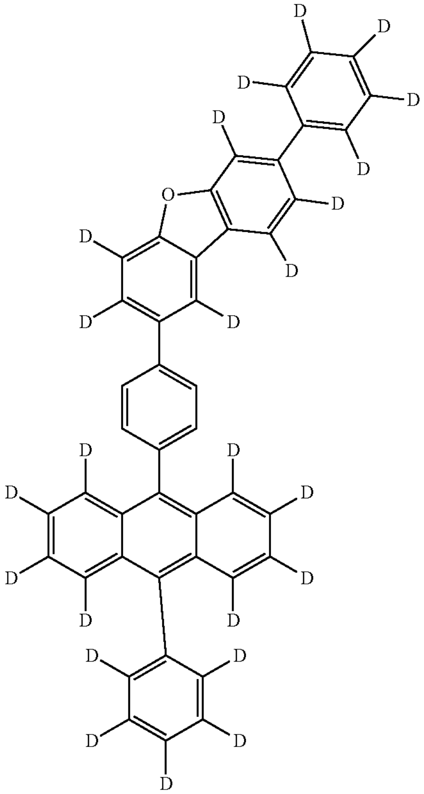
-continued
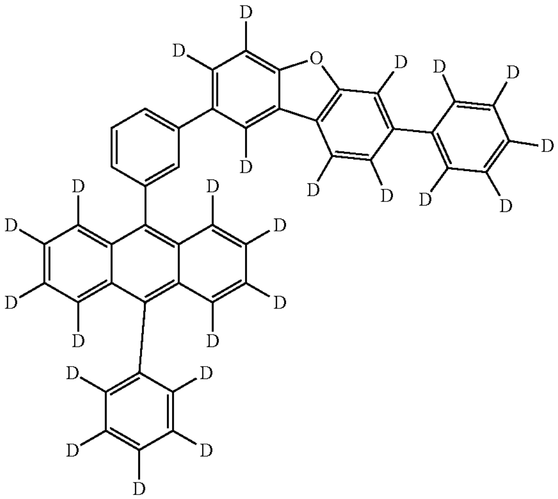
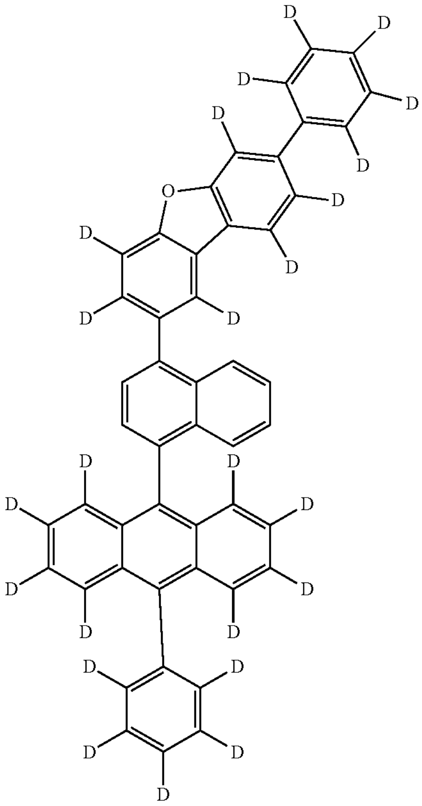

-continued
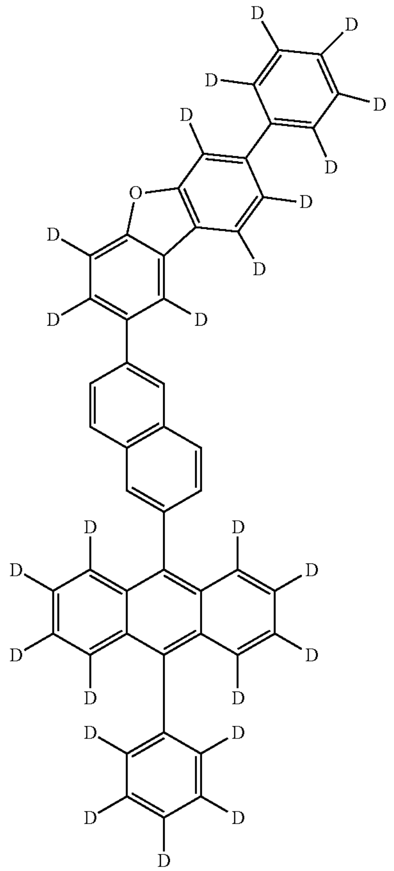
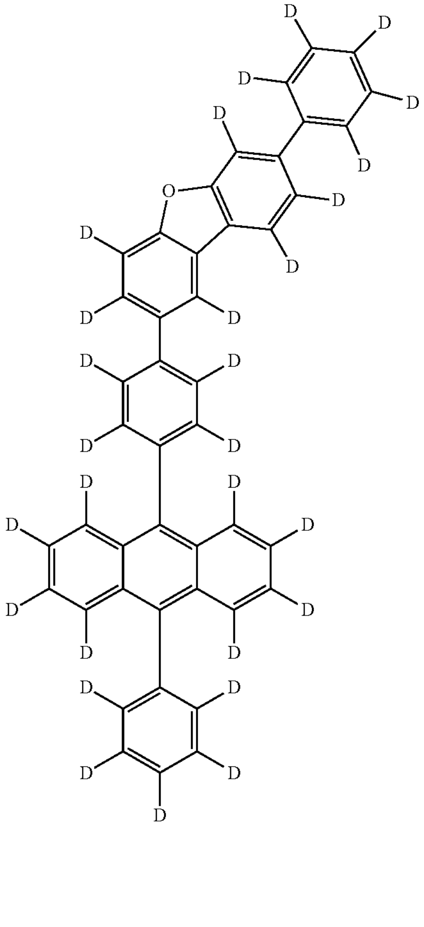
-continued
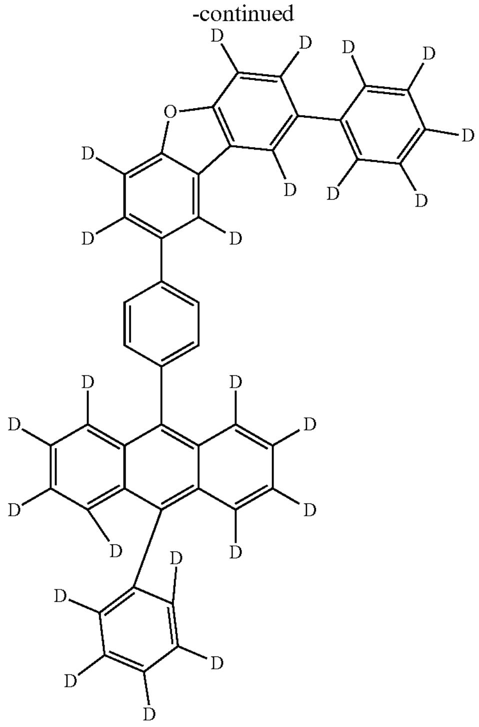
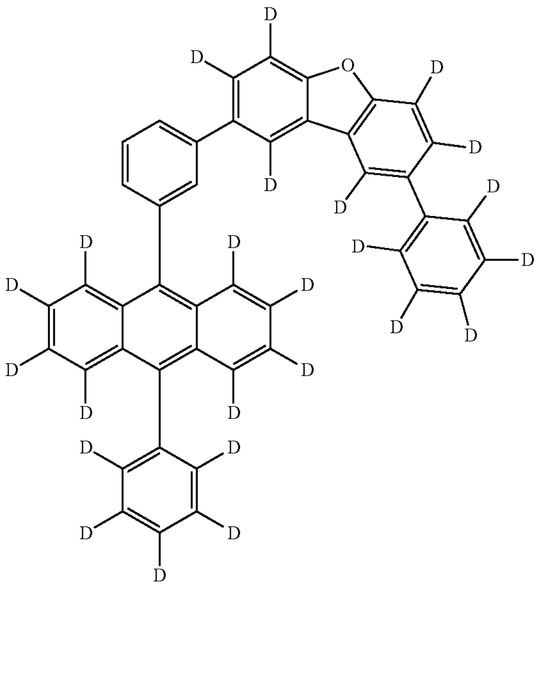

-continued
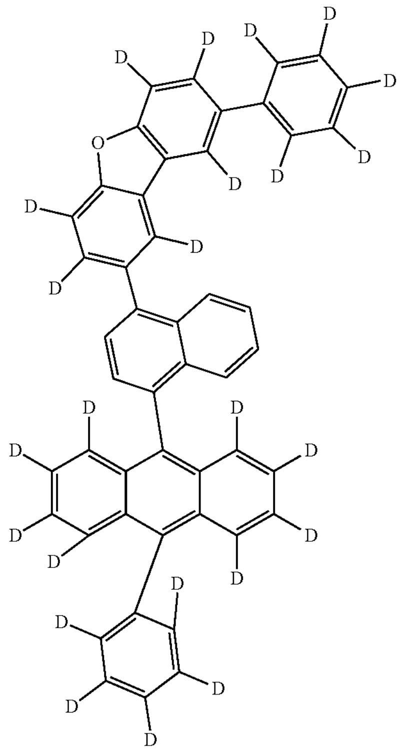
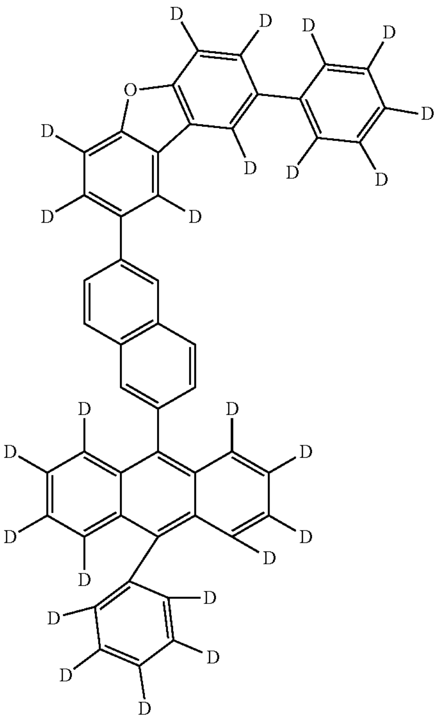
-continued
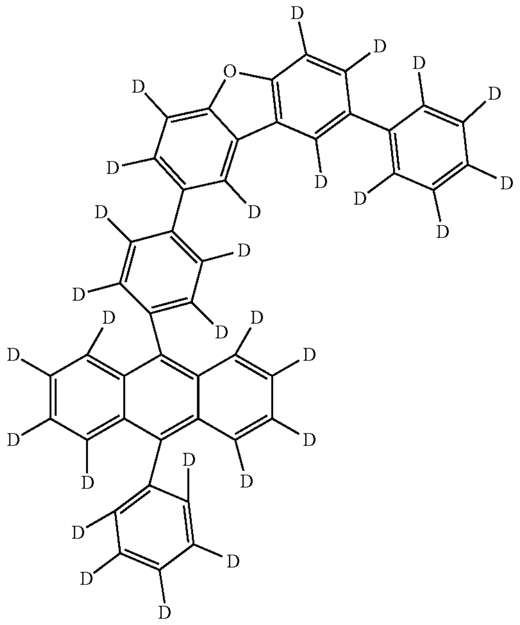
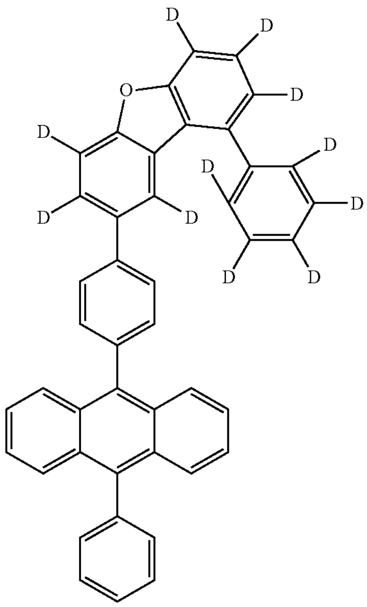

-continued
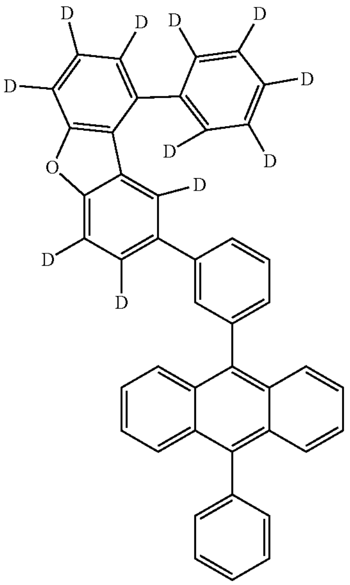
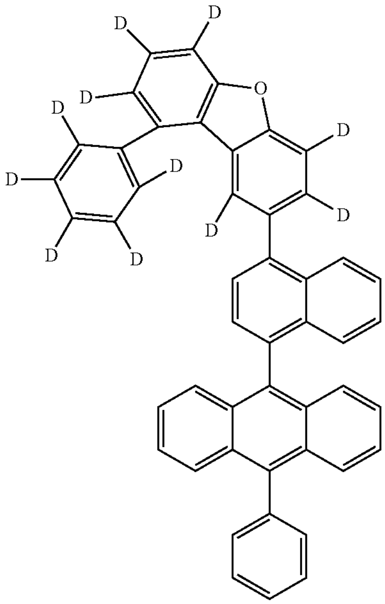
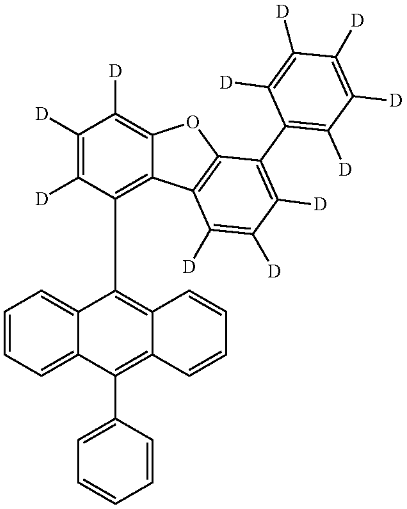
-continued
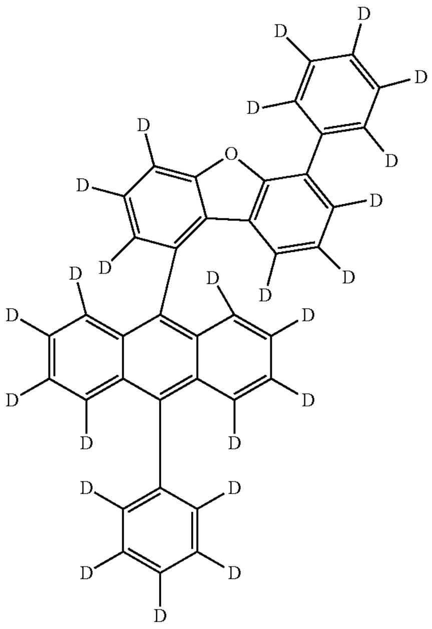
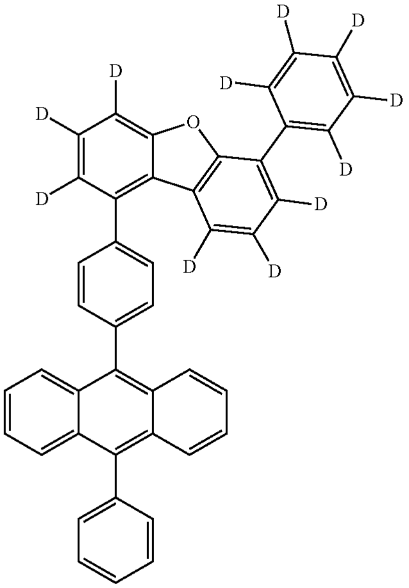

-continued
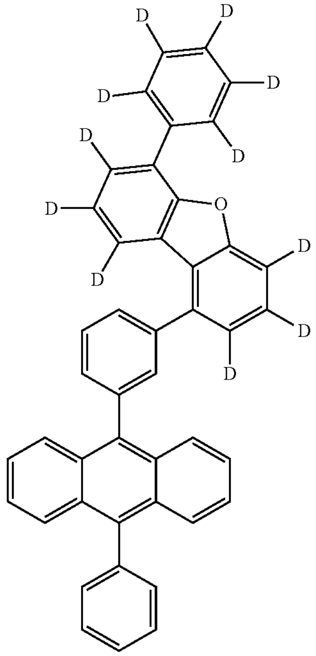
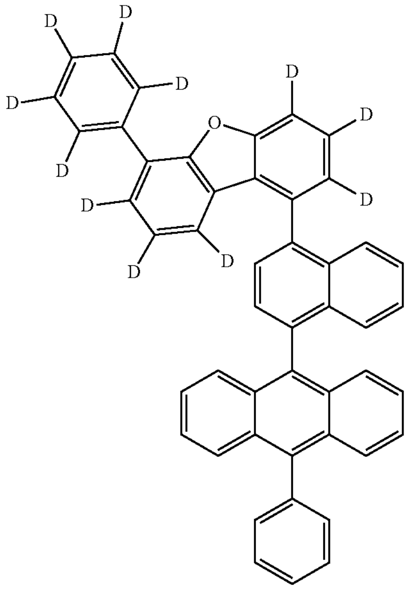
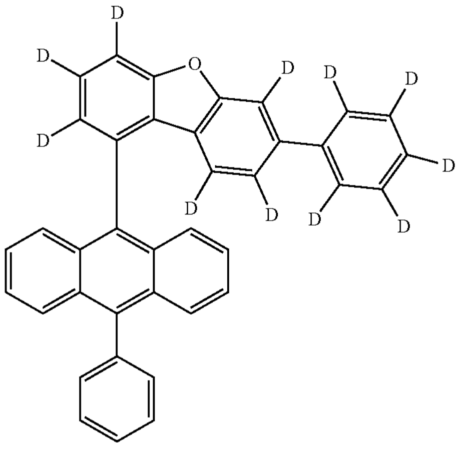
-continued
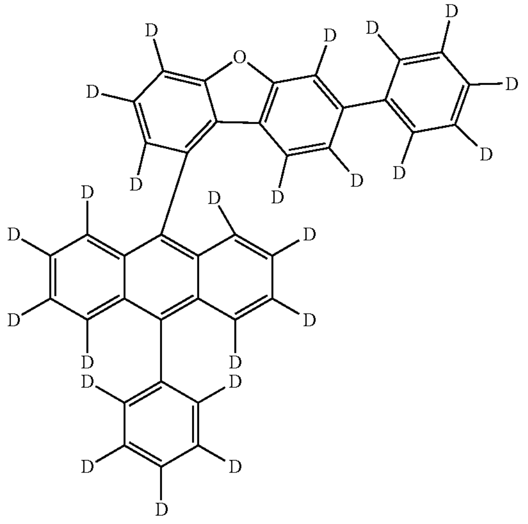
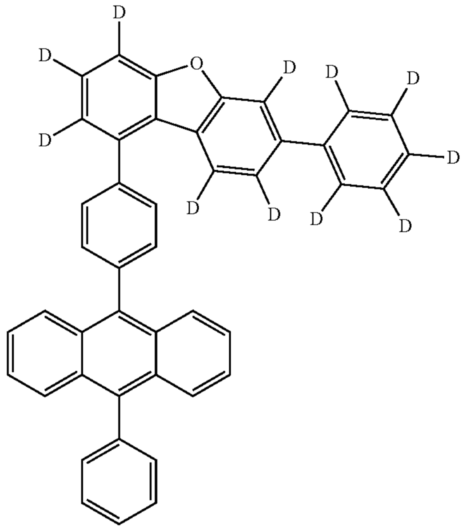
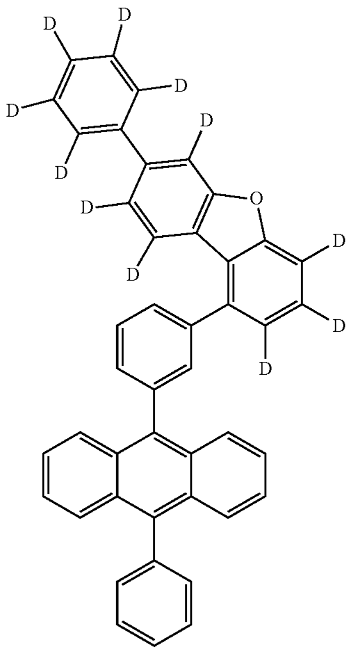

-continued
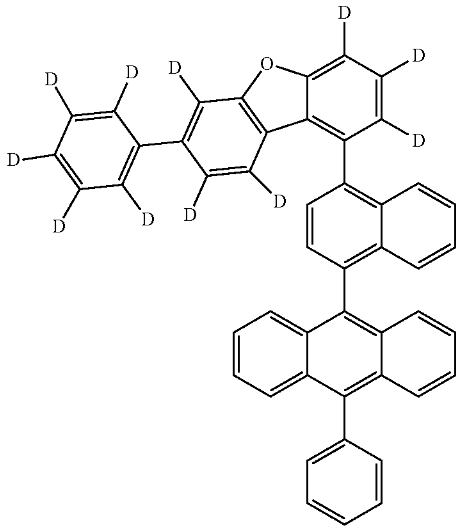
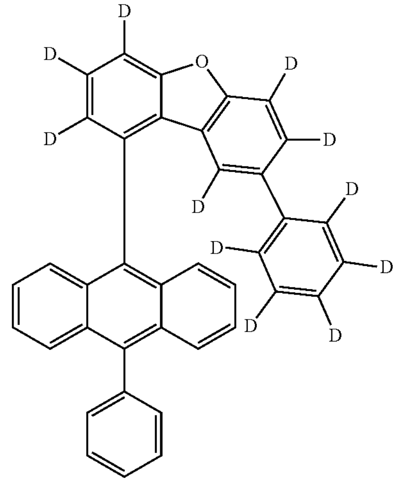
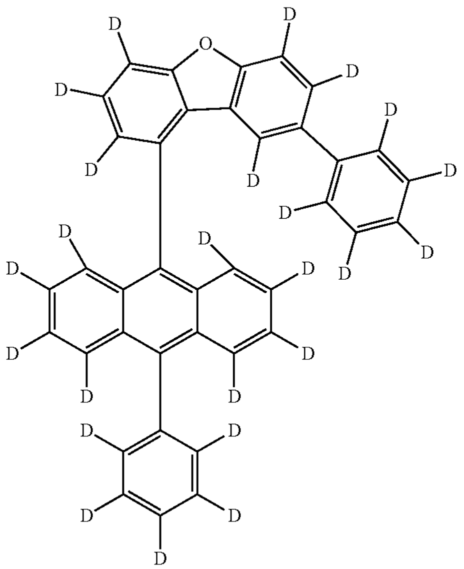
-continued
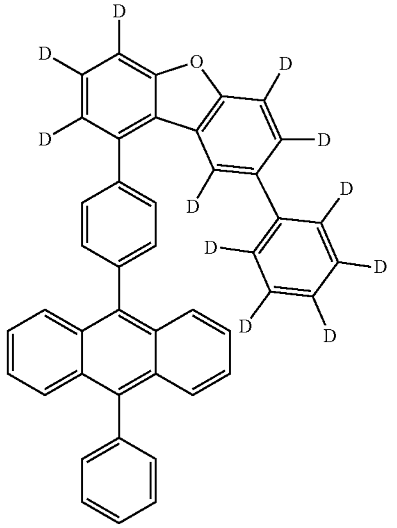
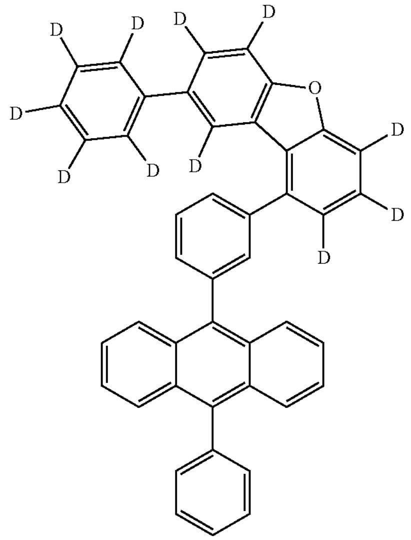
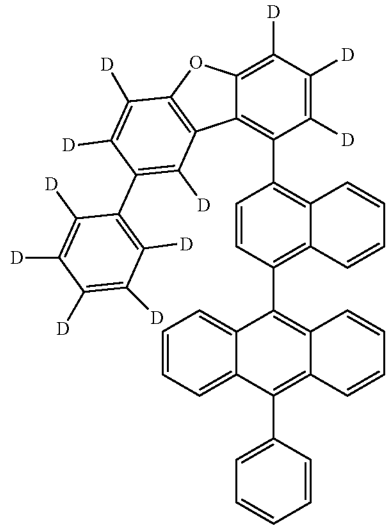

-continued
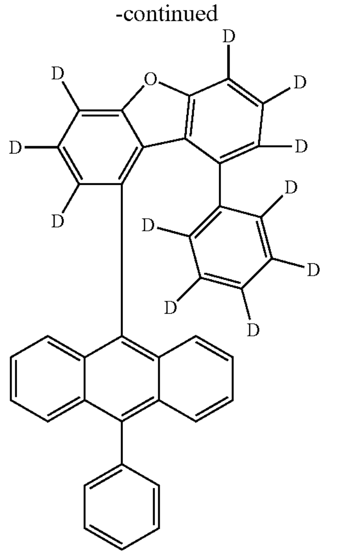
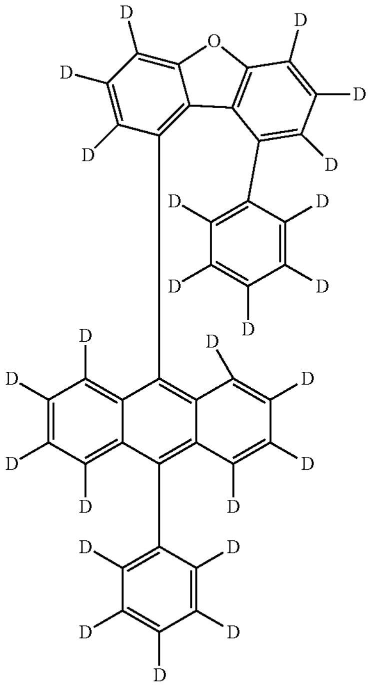
-continued
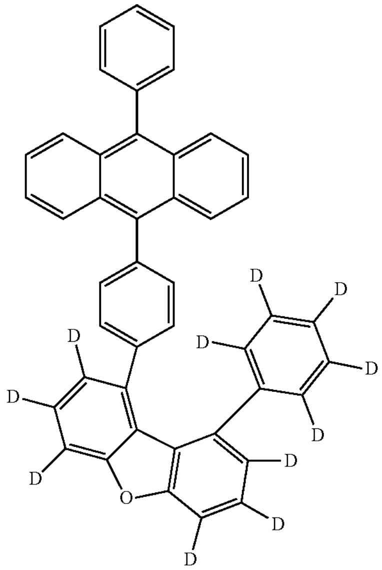
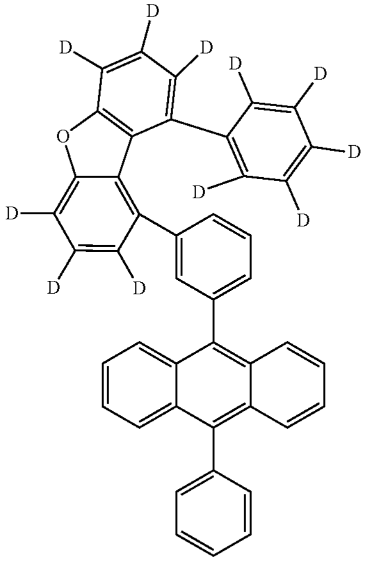

-continued
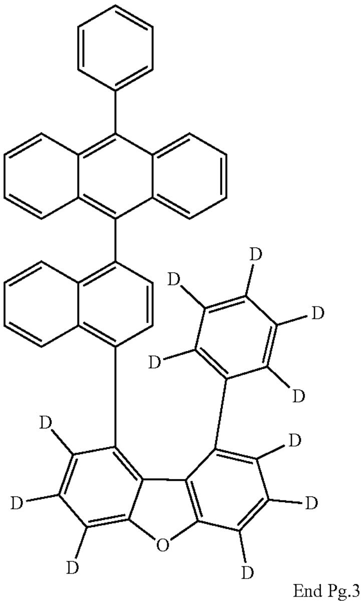
End Pg.3
-continued
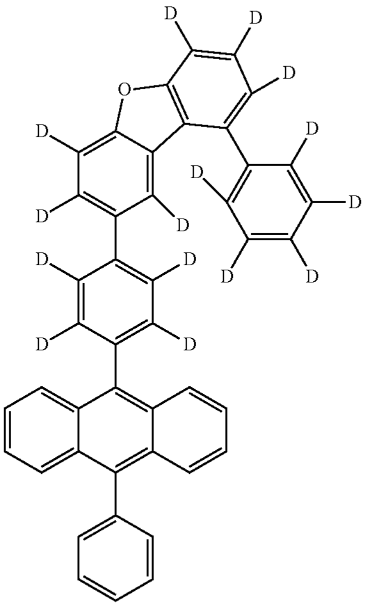
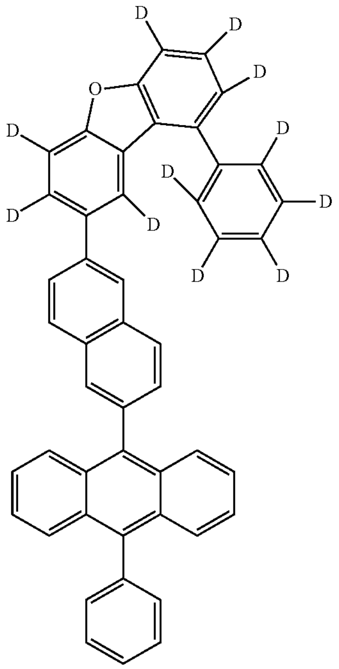
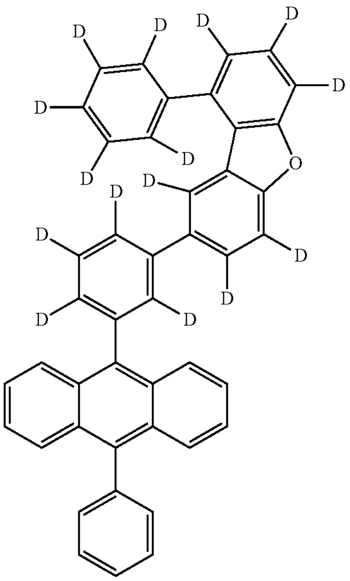

-continued
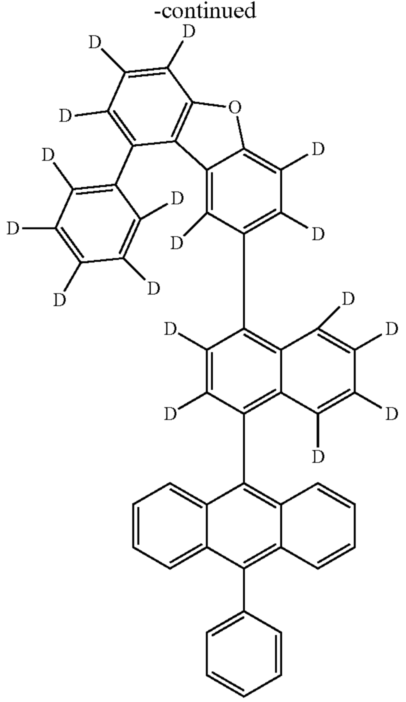
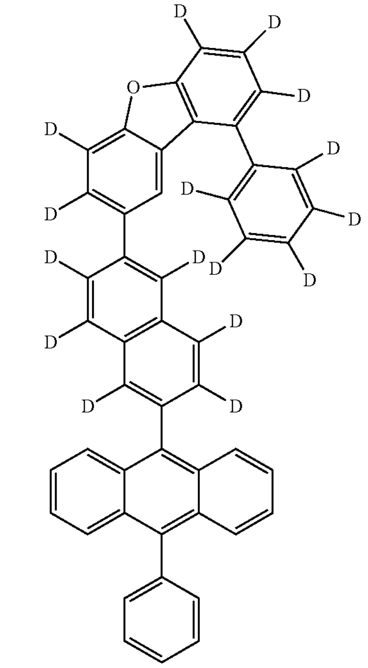
-continued
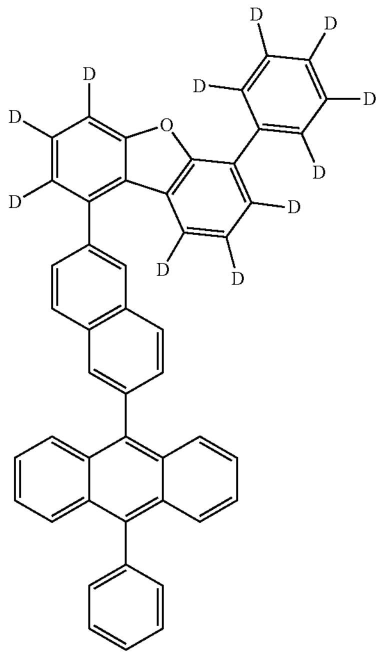
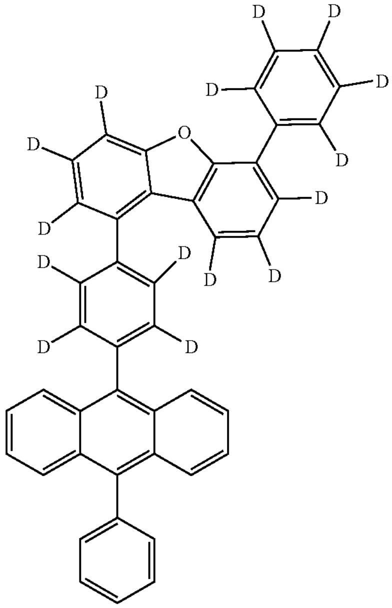

-continued
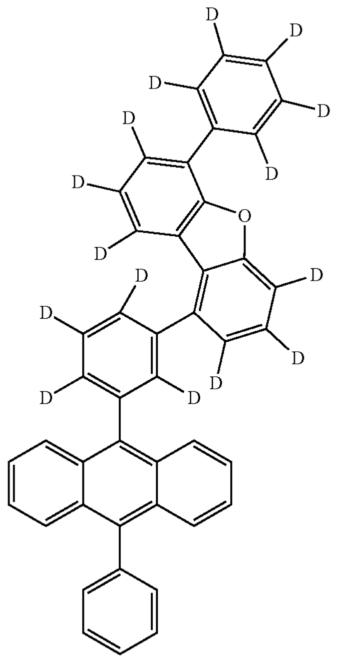
-continued
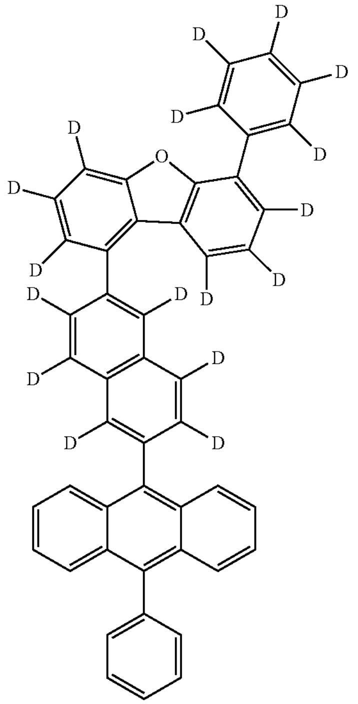
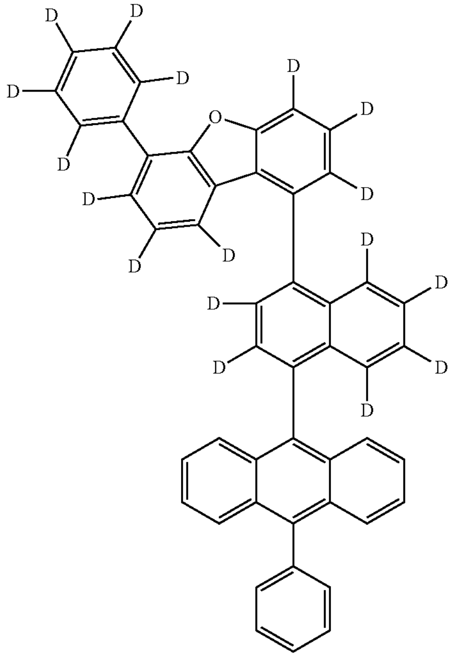
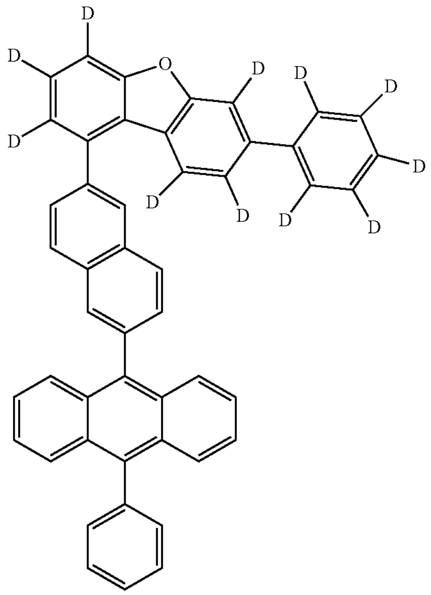

-continued
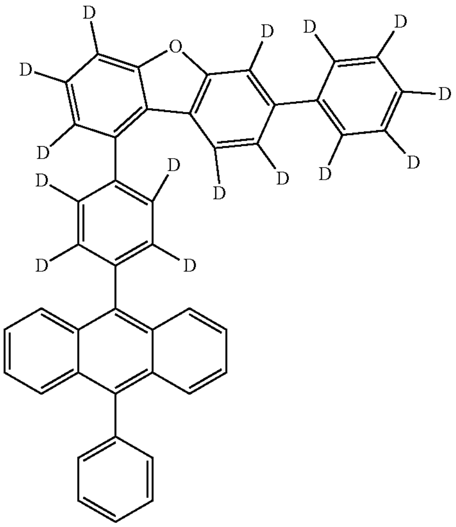
-continued
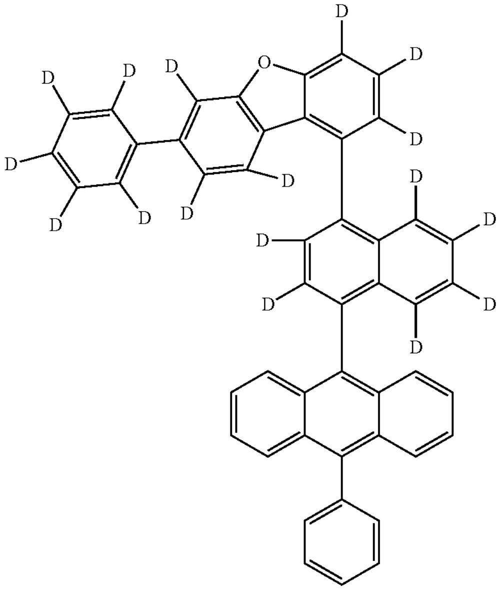
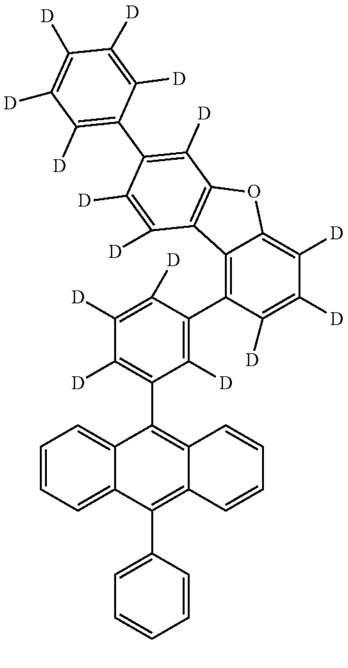
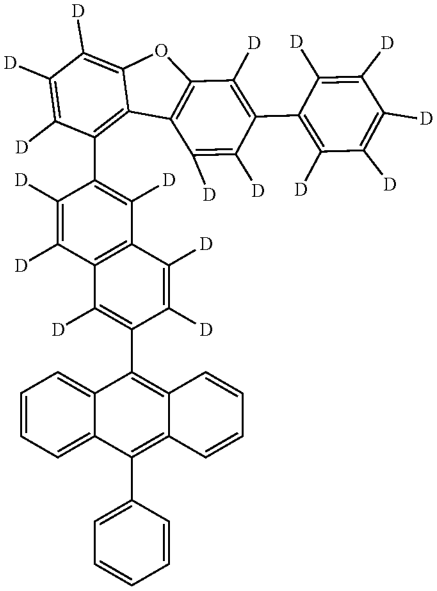

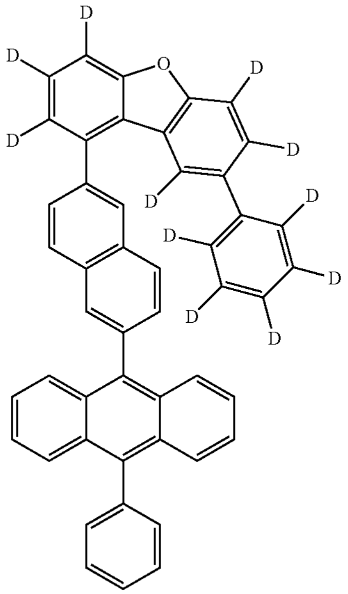
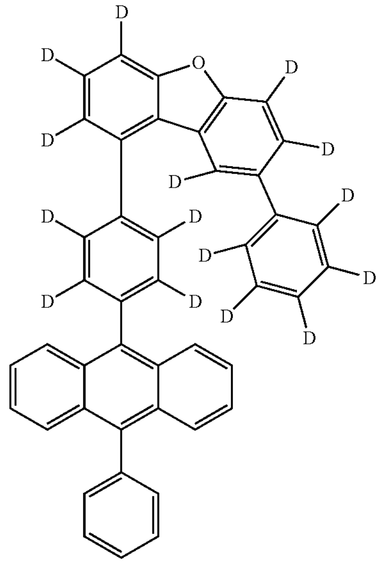
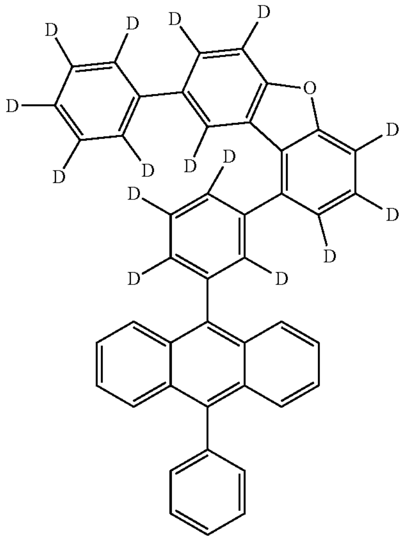
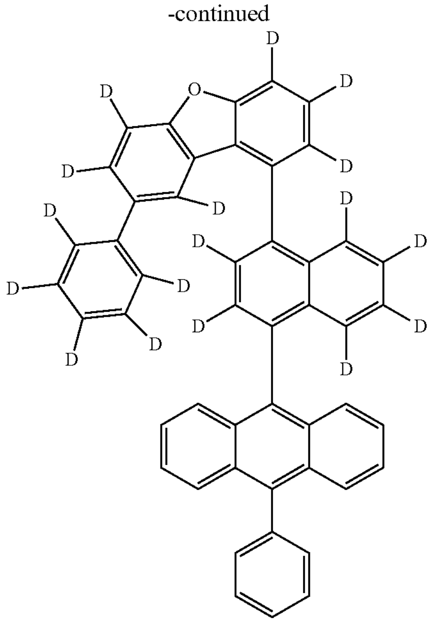
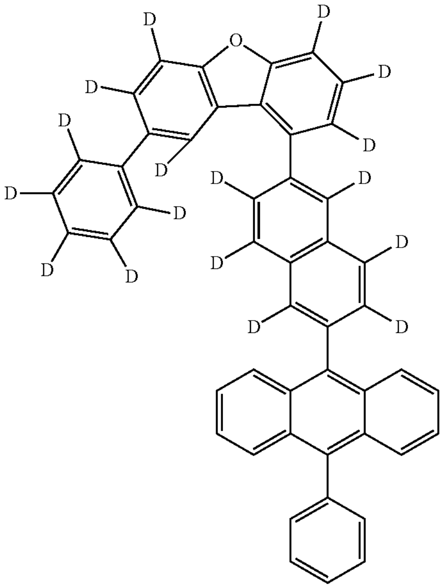

-continued
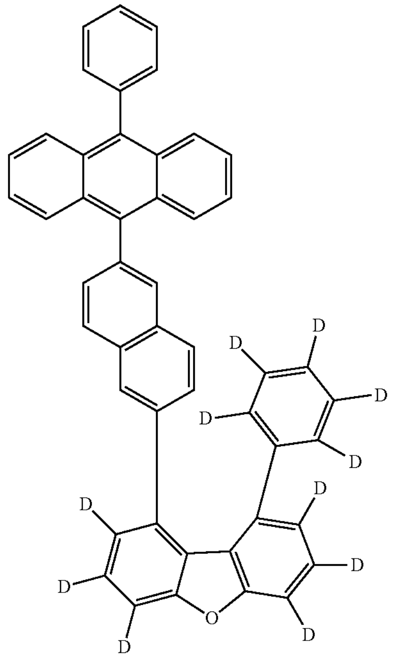
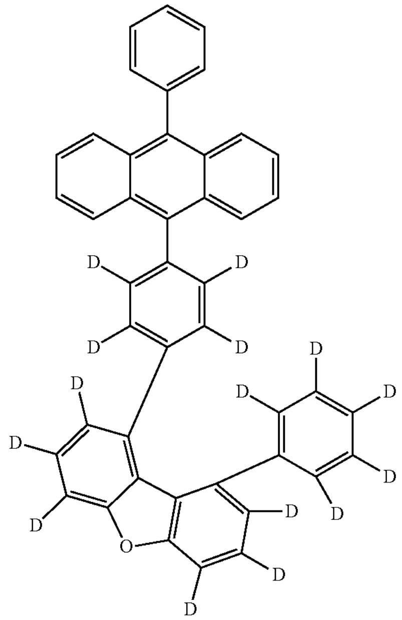
-continued
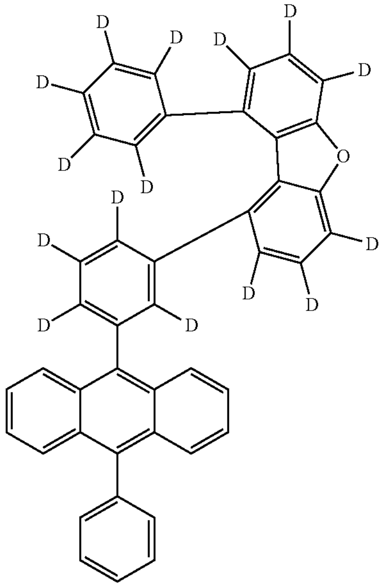
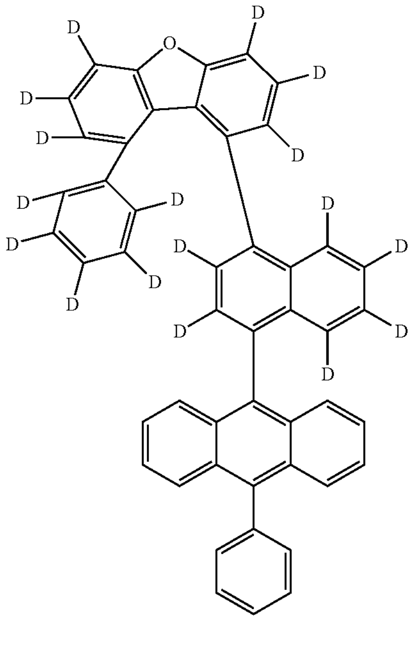

-continued
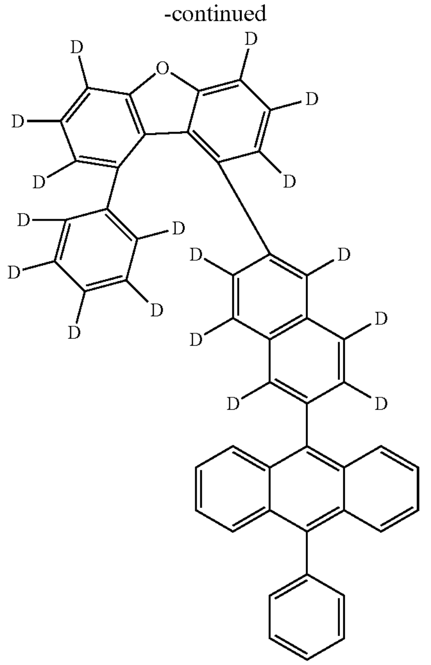
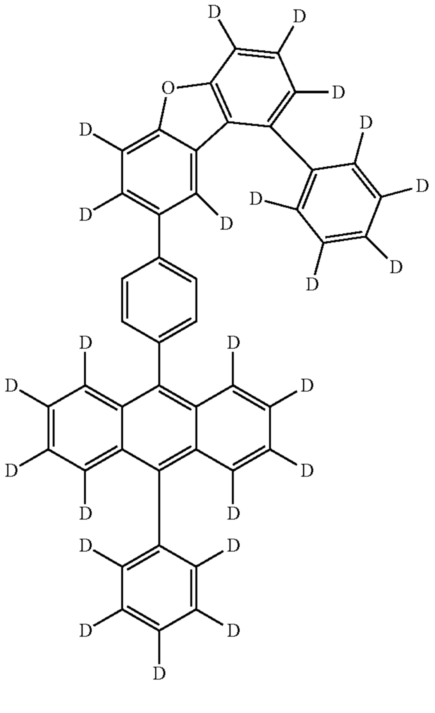
-continued
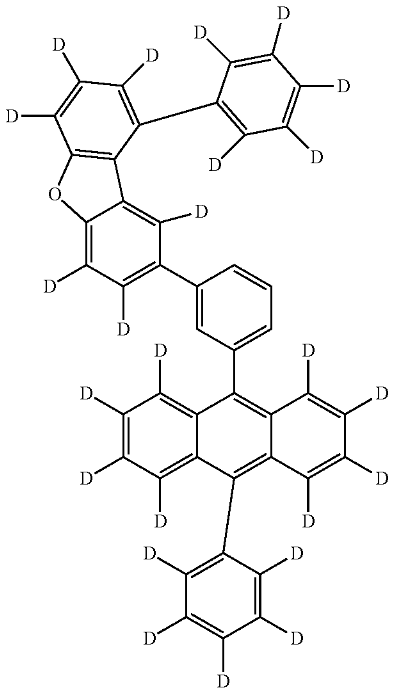
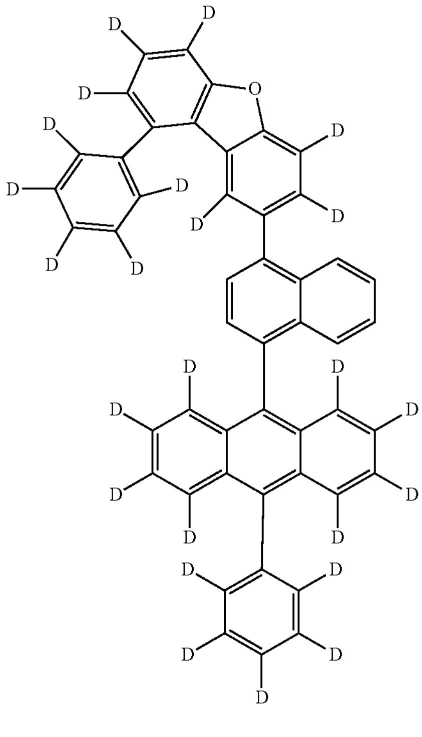

-continued
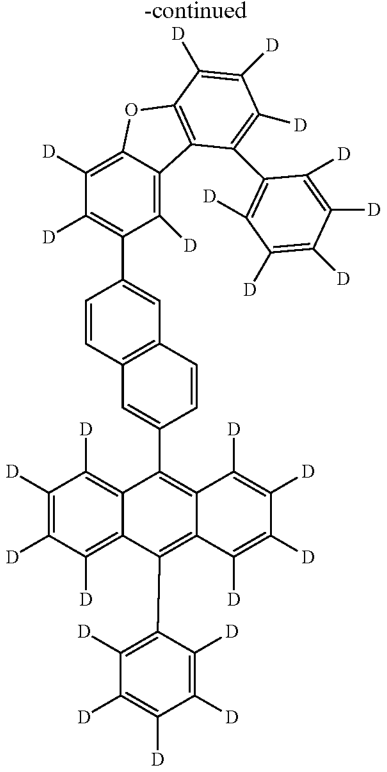
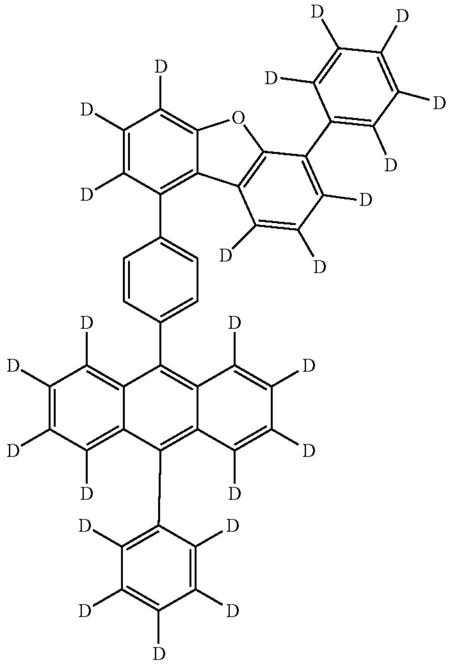
-continued
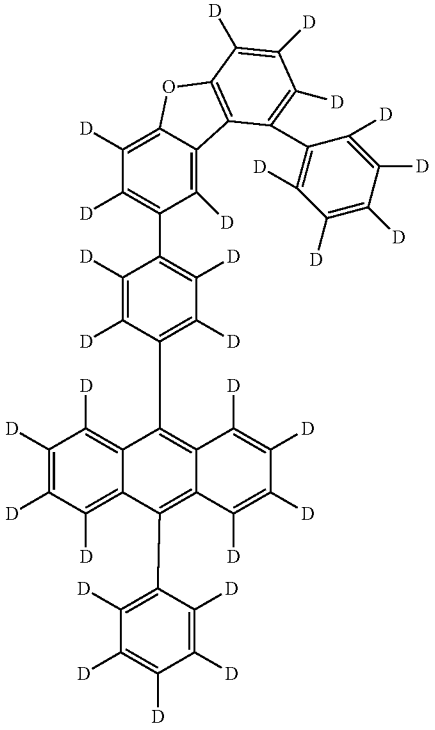
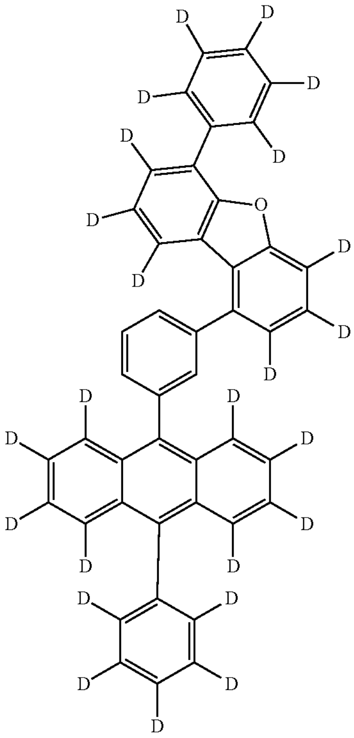

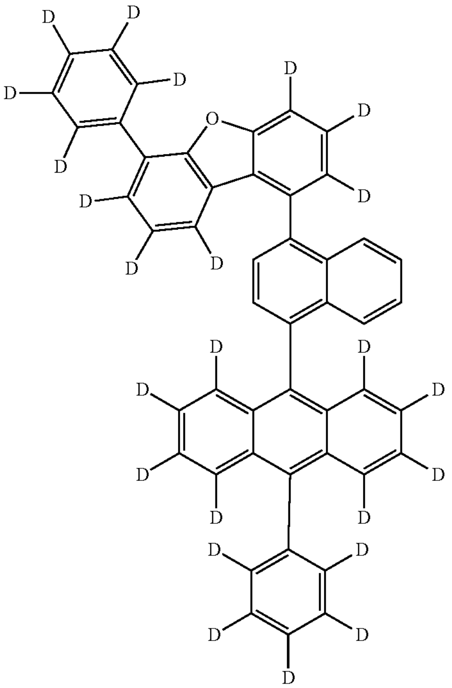
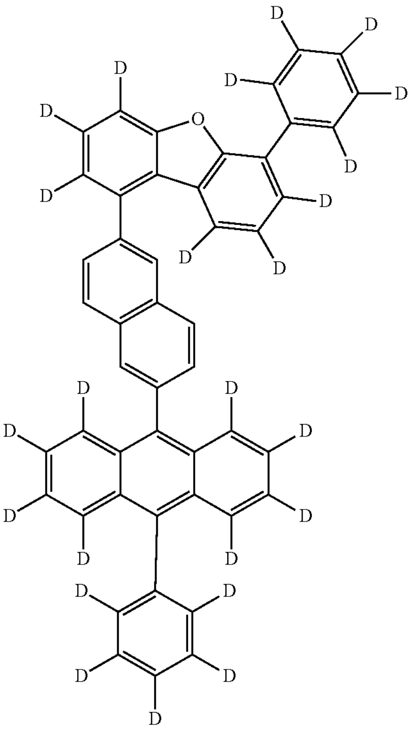
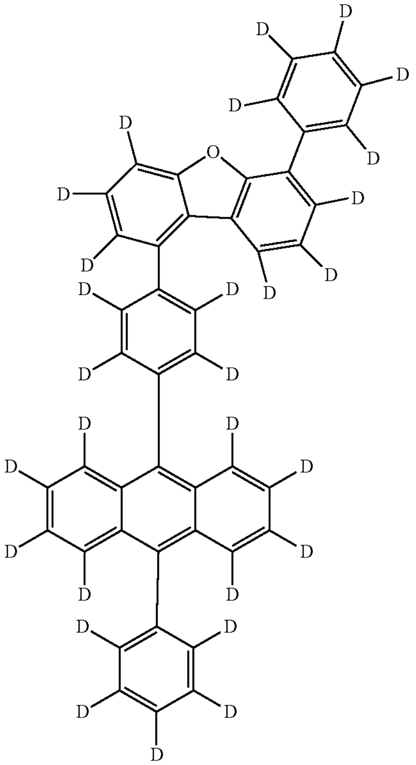
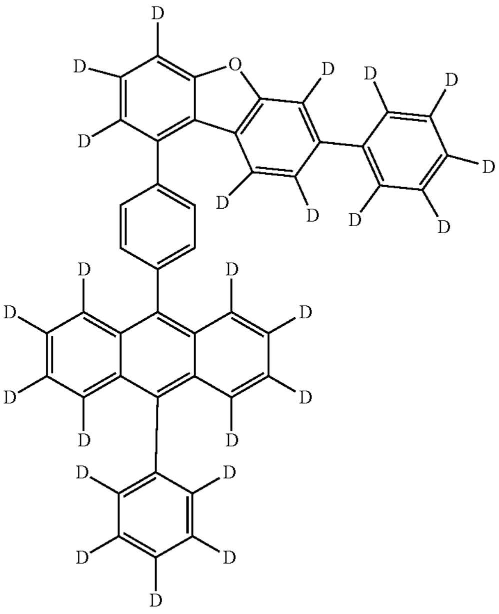

-continued
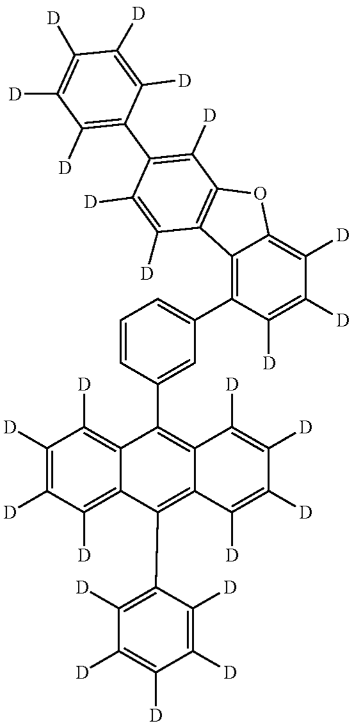
-continued
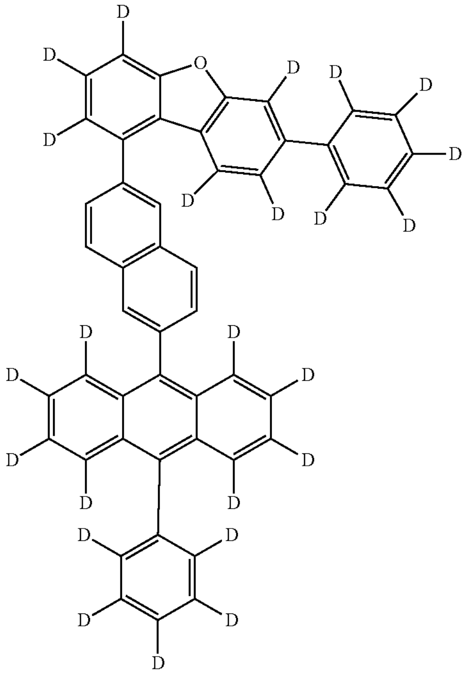
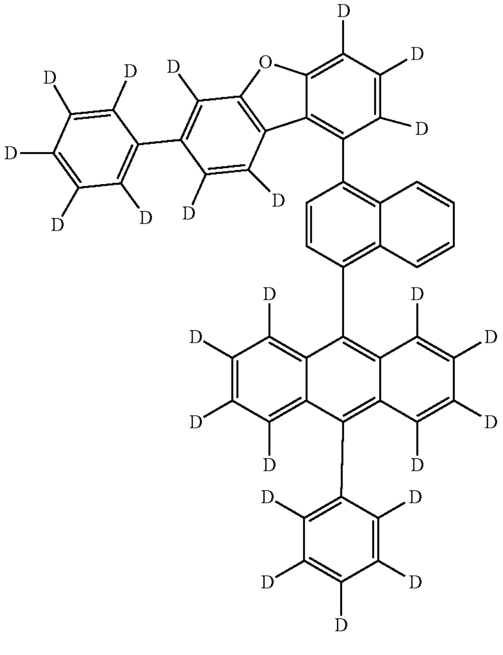
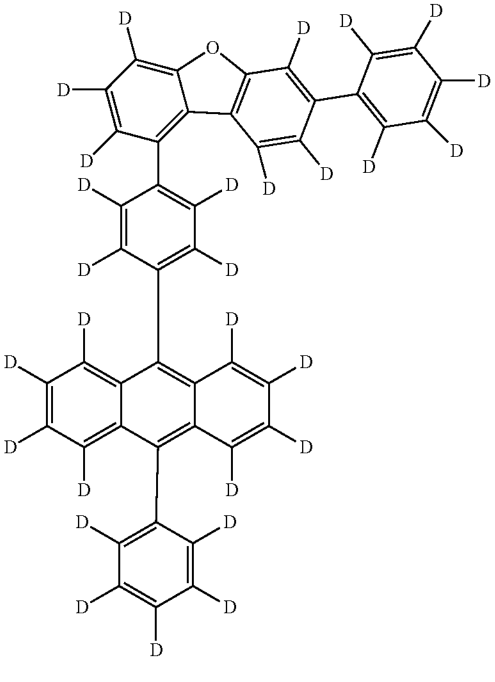

-continued
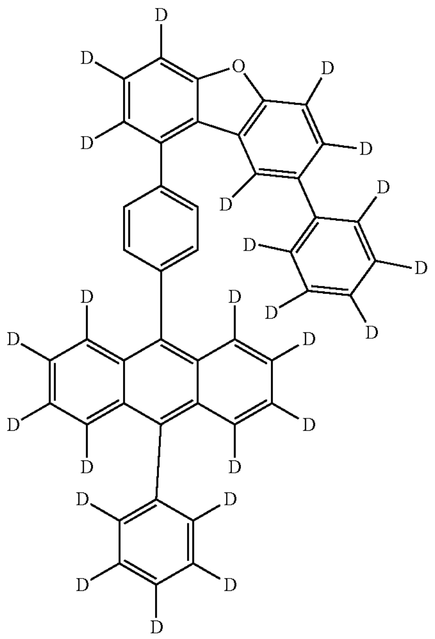
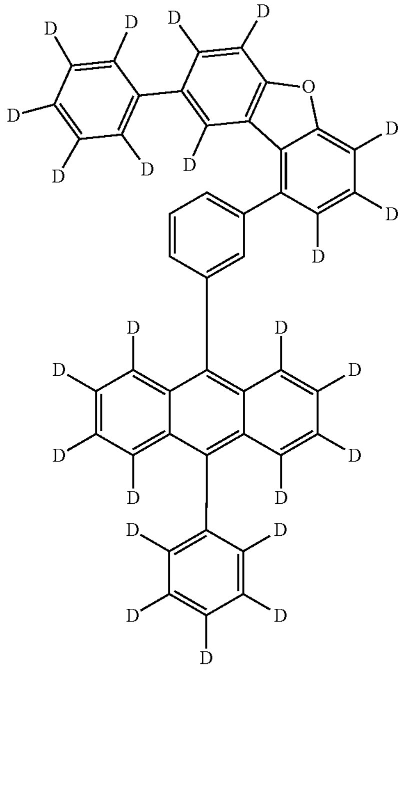
-continued
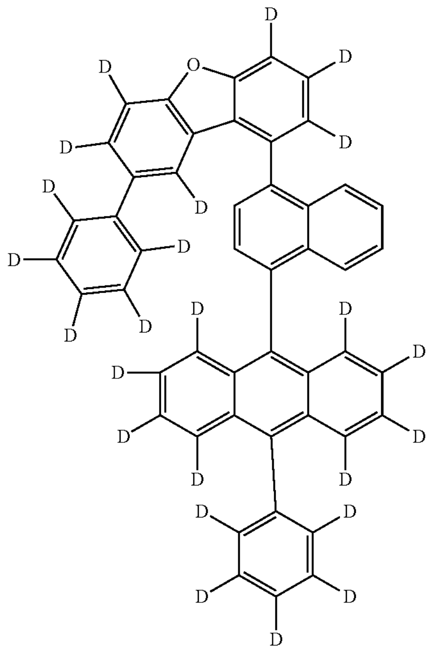
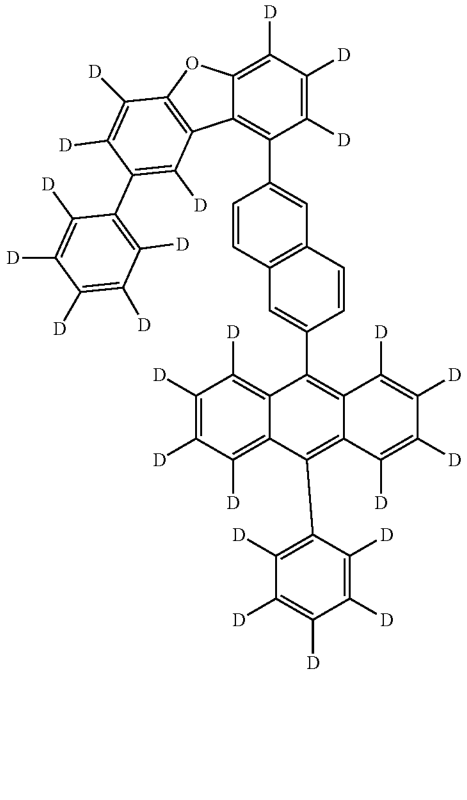

-continued
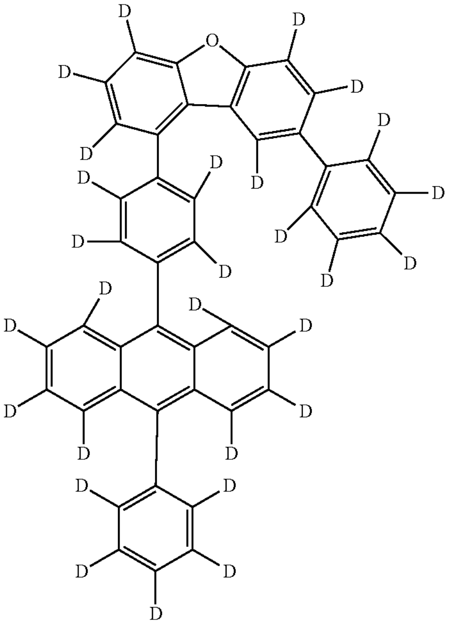
-continued
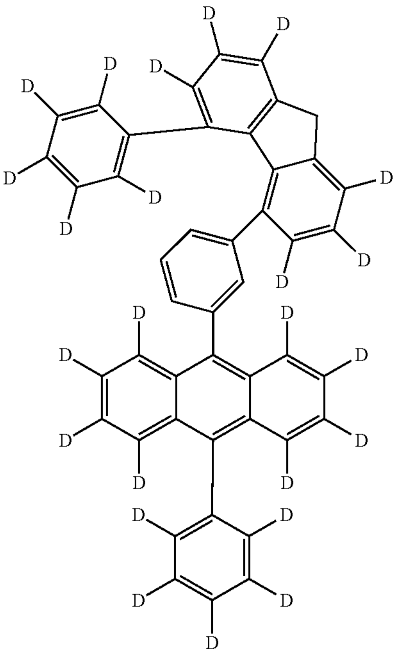
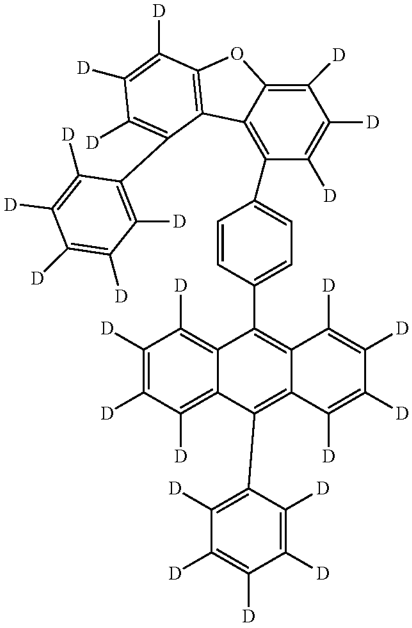
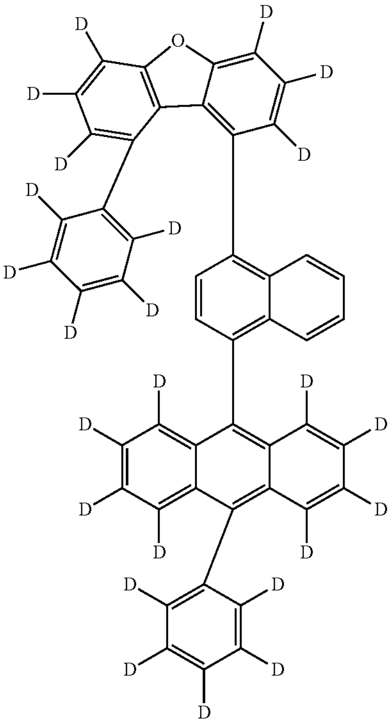

-continued
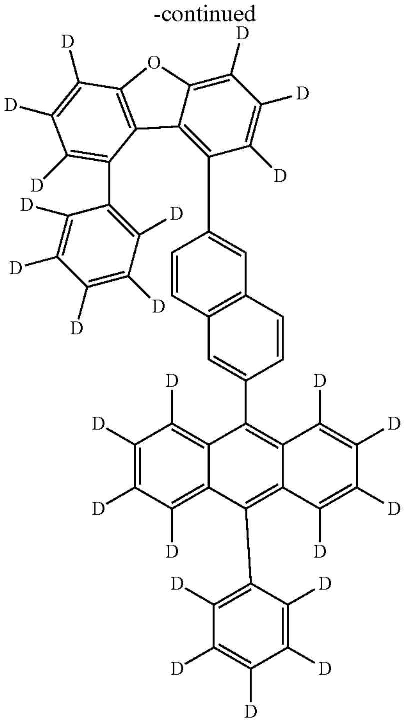
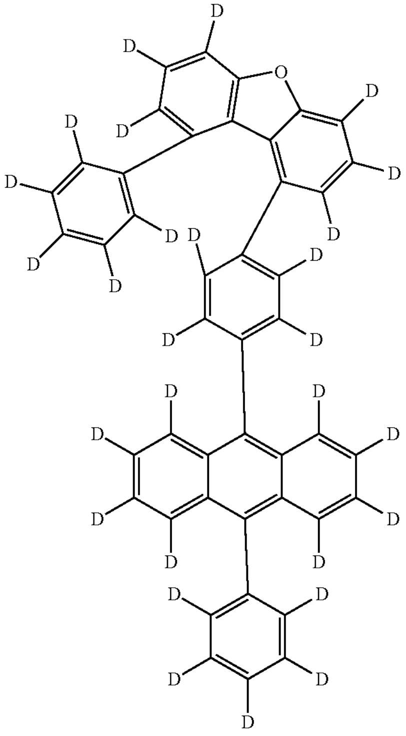
-continued
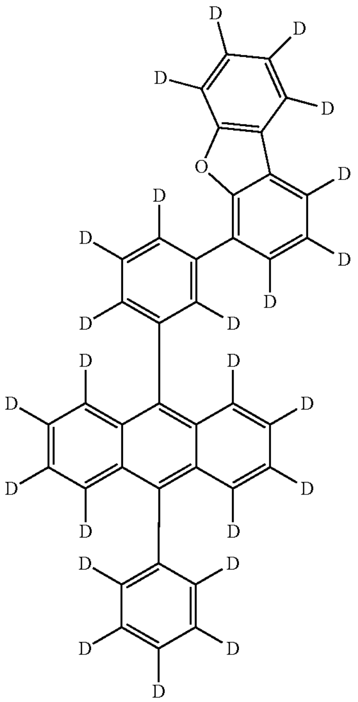
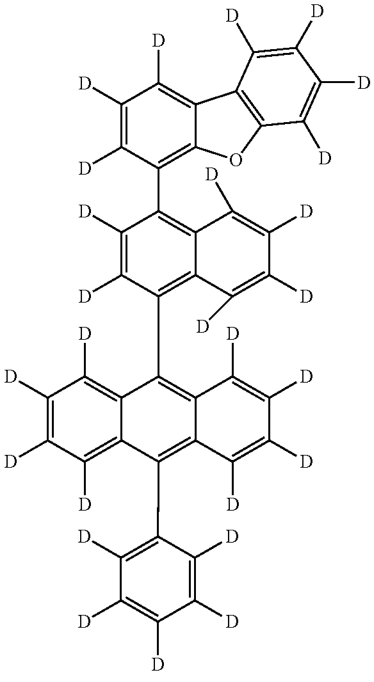

-continued
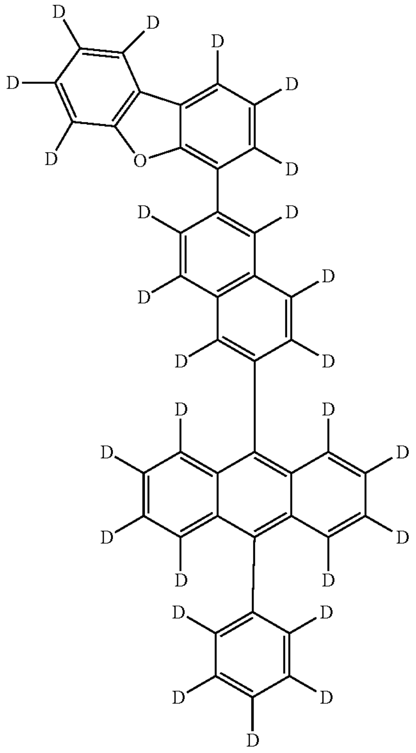
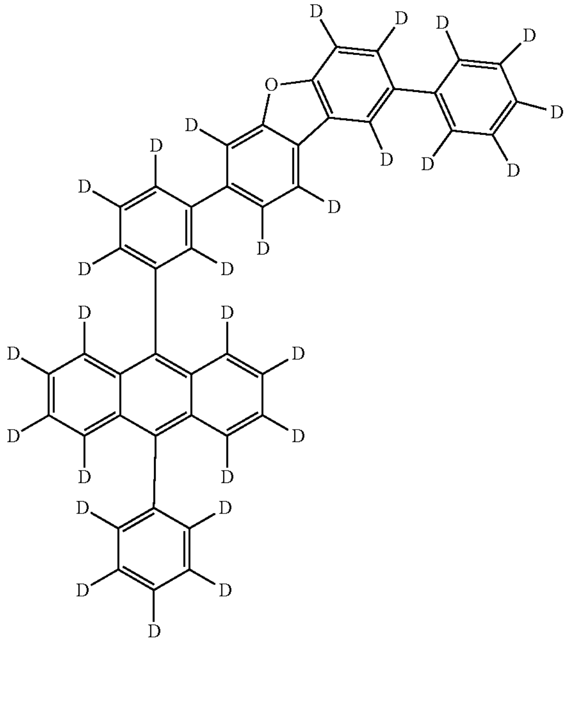
-continued
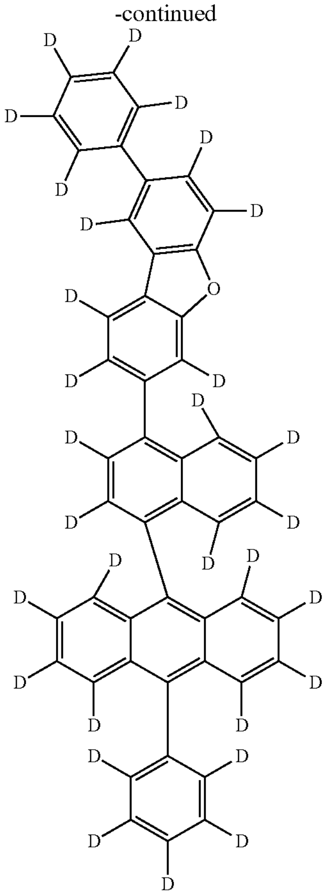

-continued
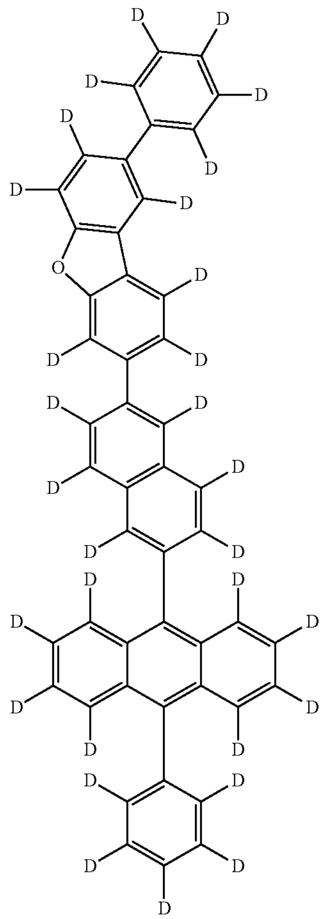
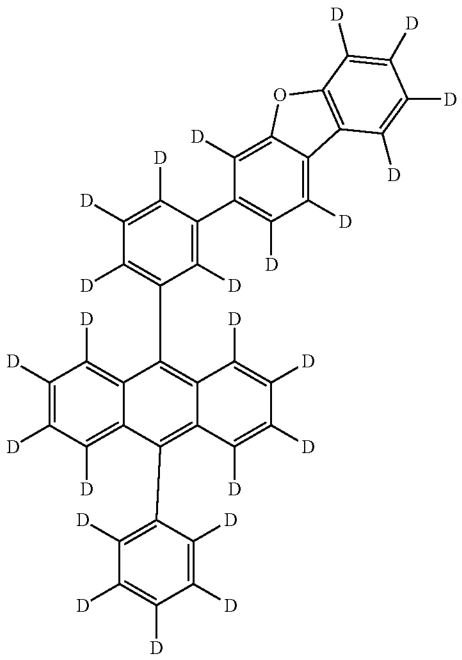
-continued
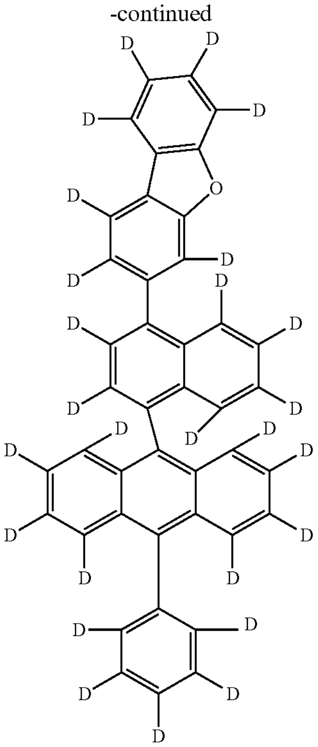
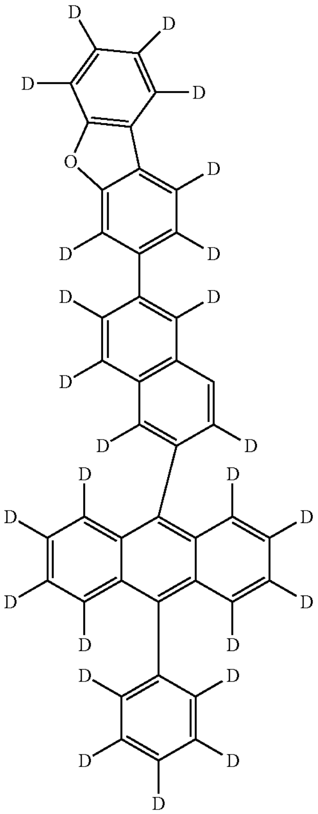

-continued
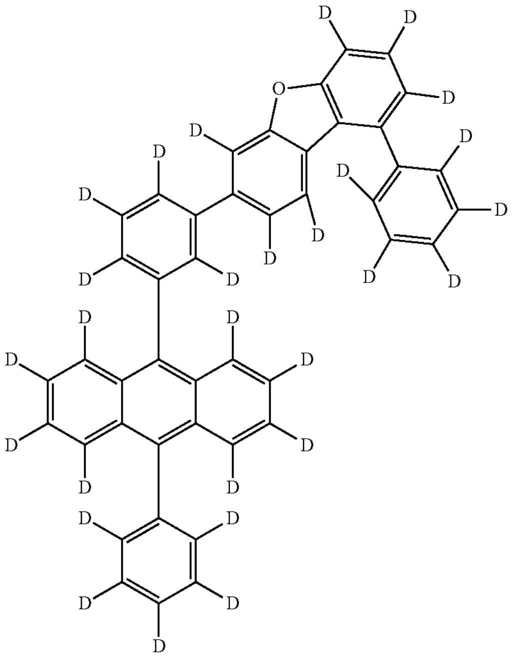
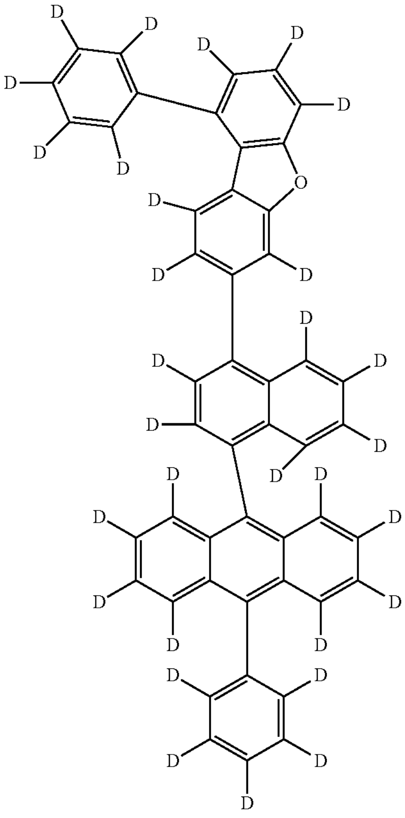
-continued
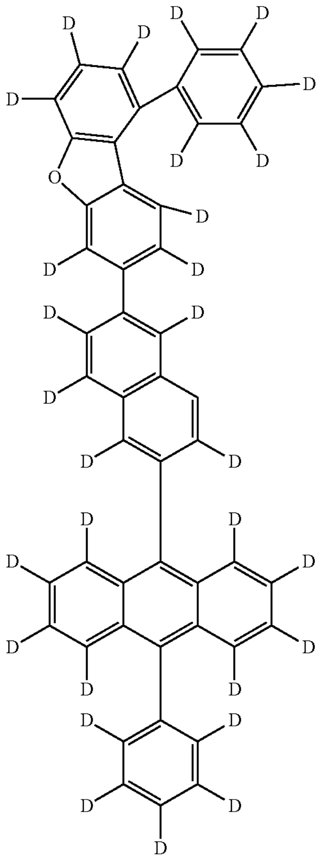
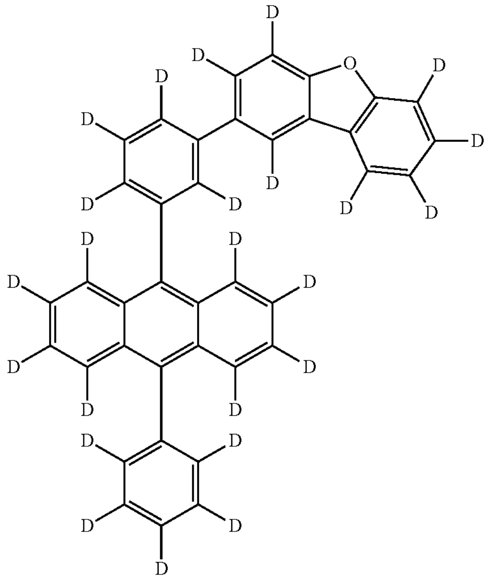

-continued
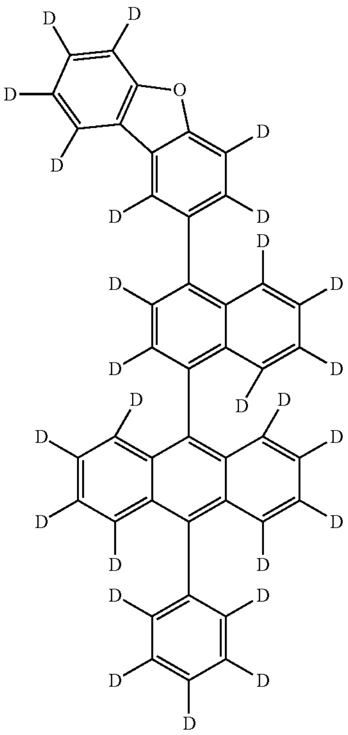
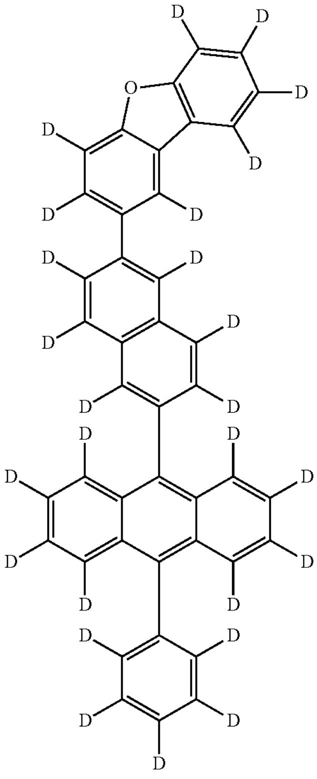
-continued
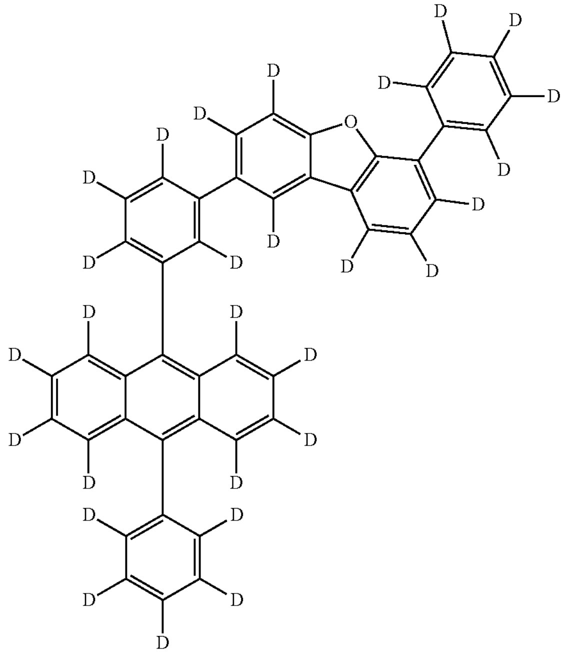
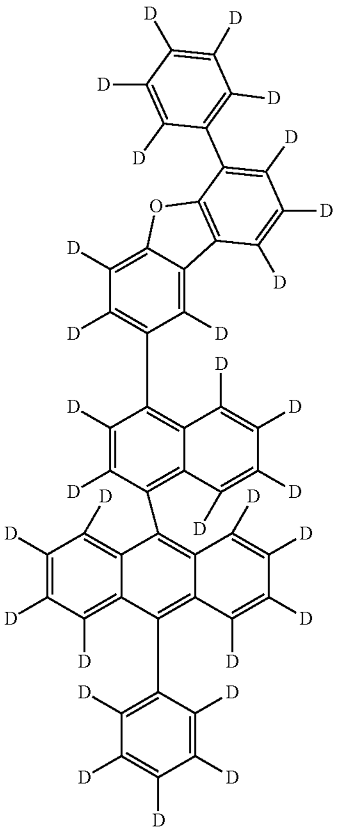

-continued
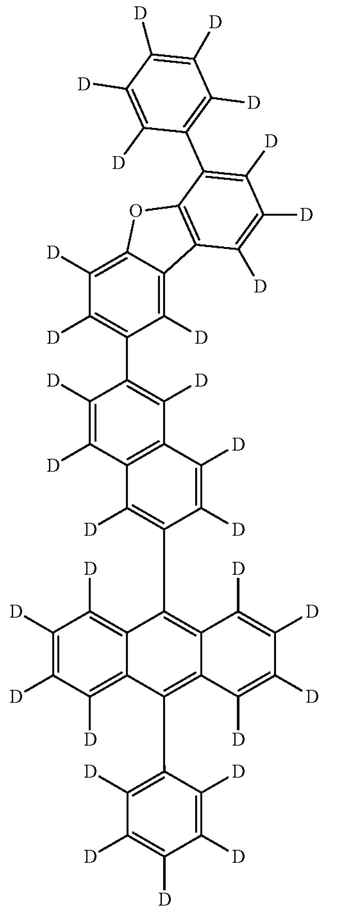
-continued
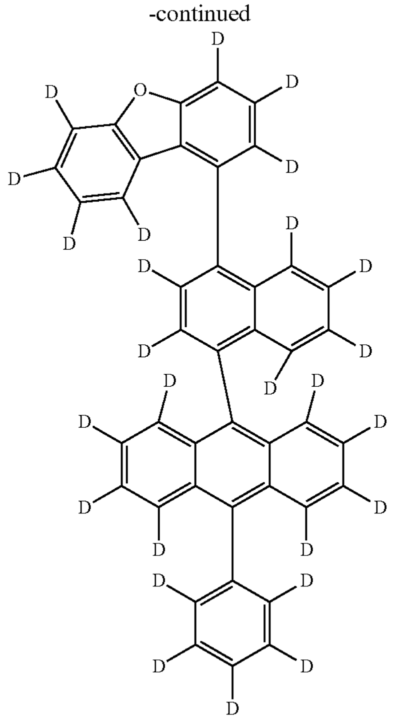
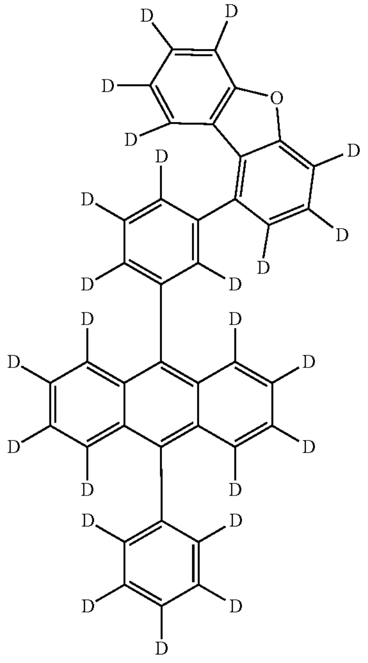
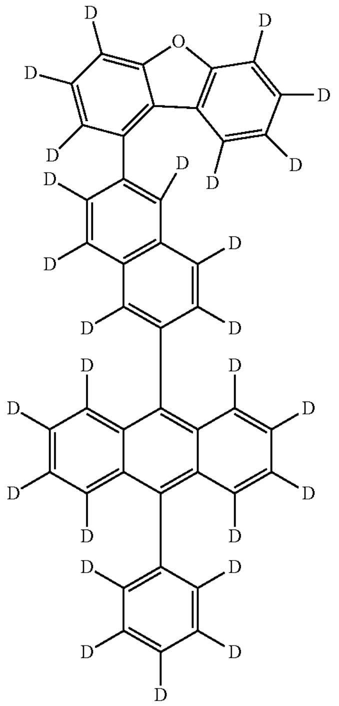

-continued
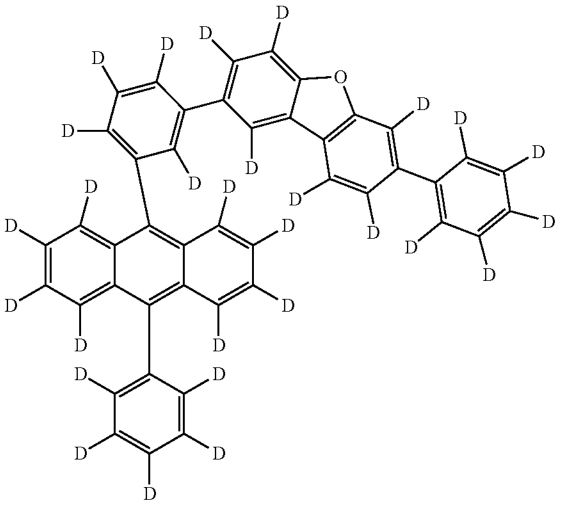
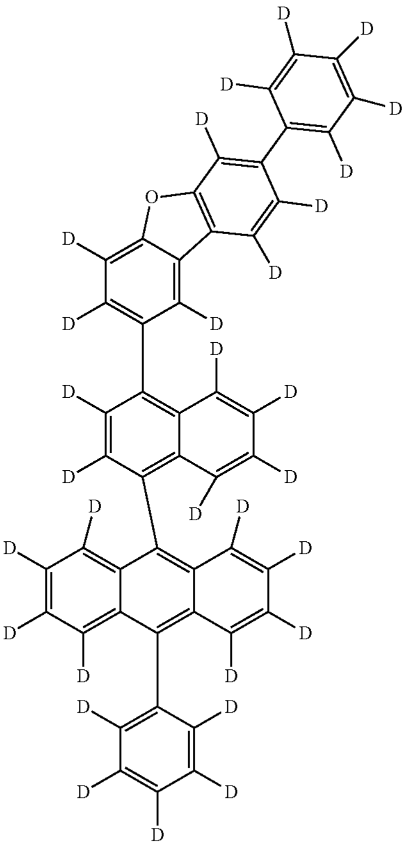
-continued
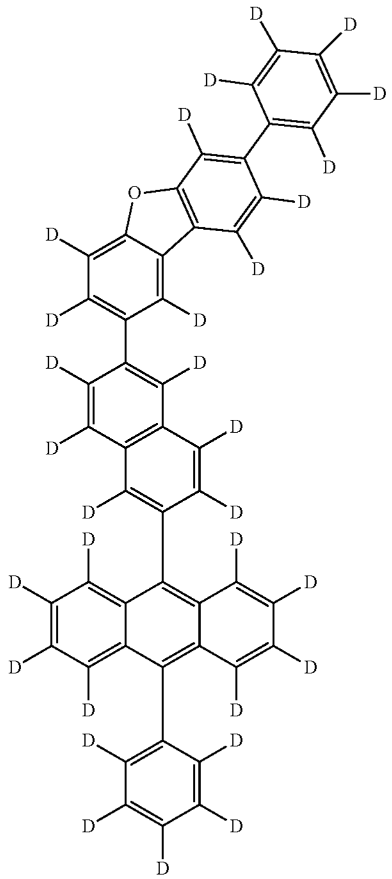
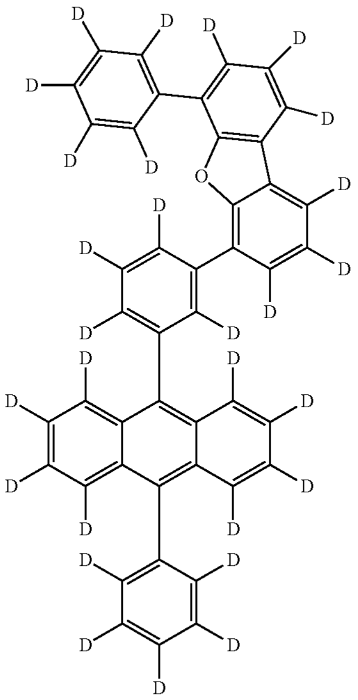

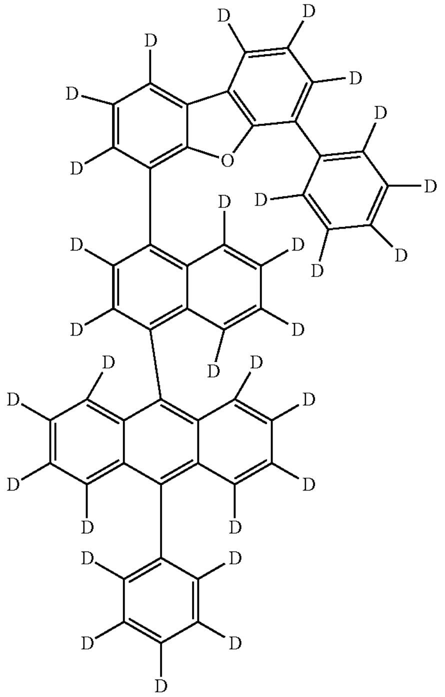
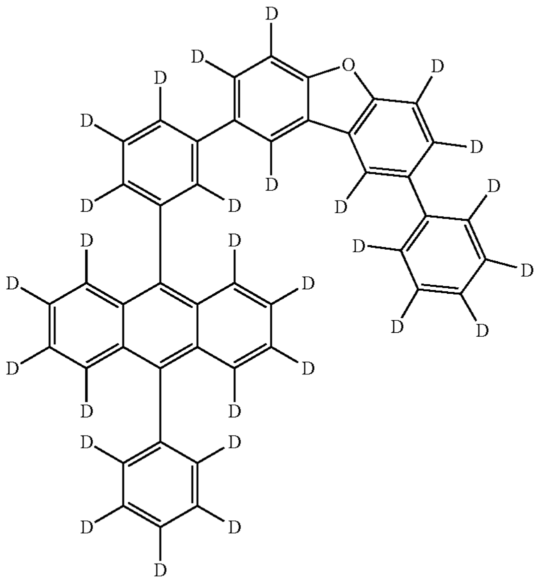
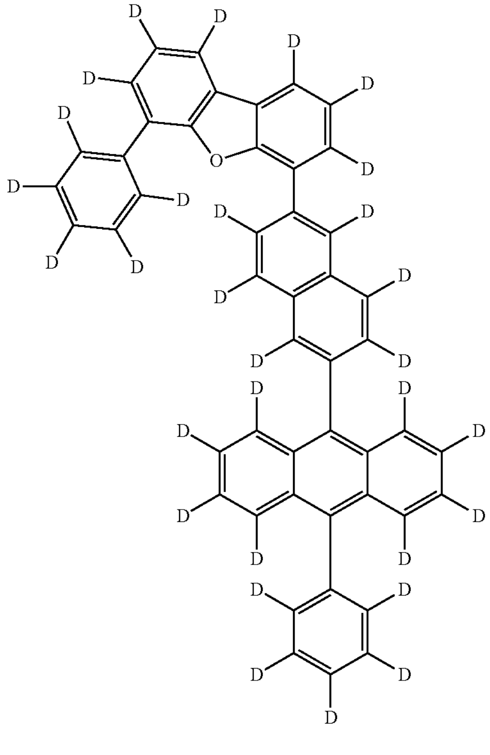
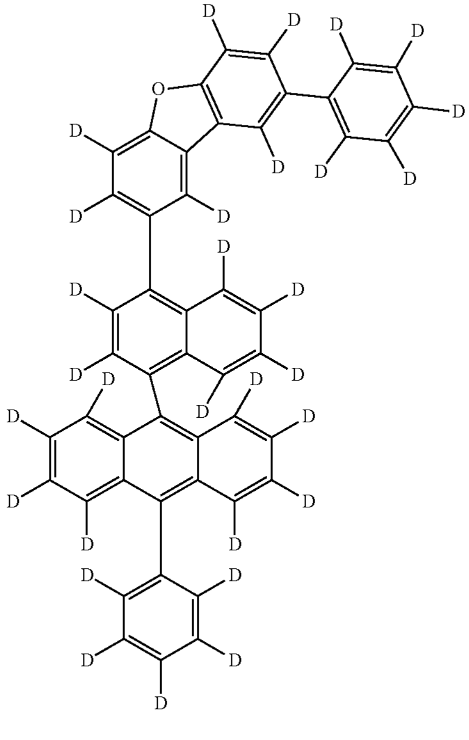

-continued
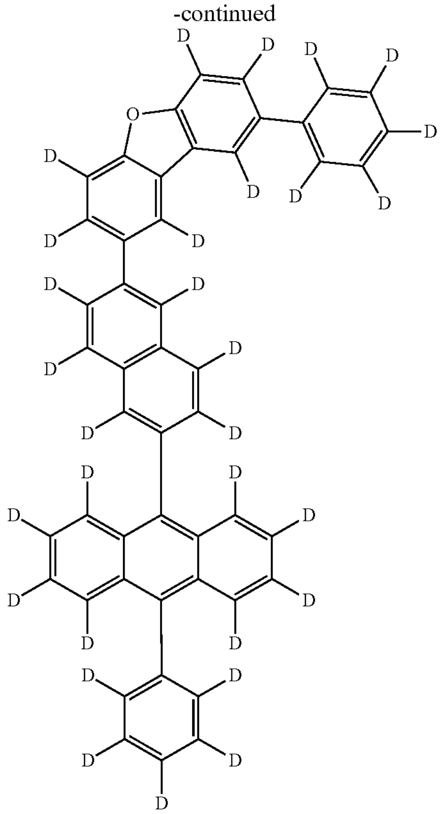
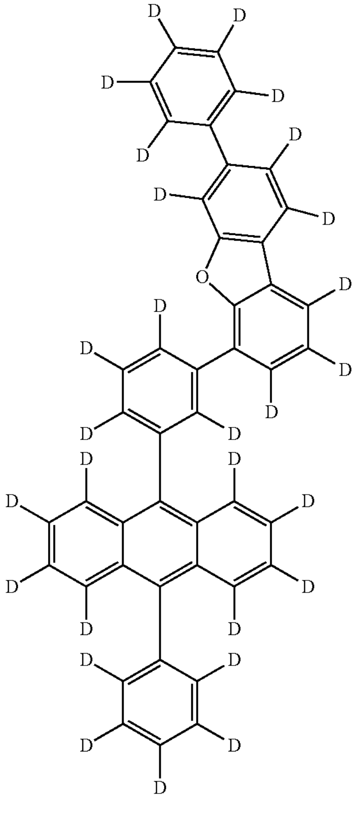
-continued
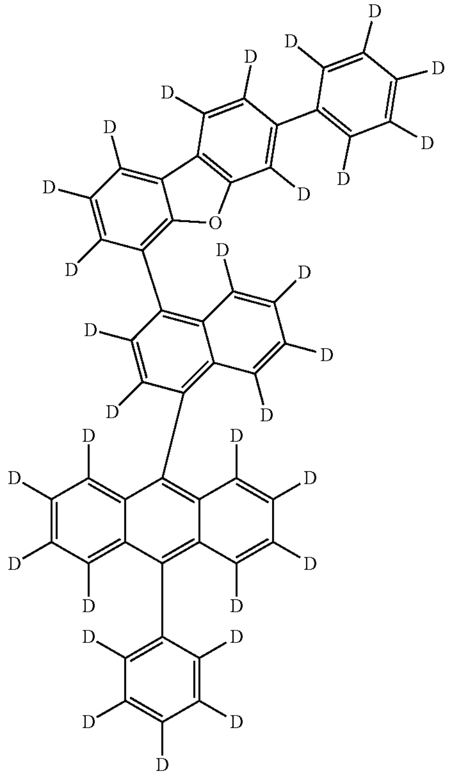
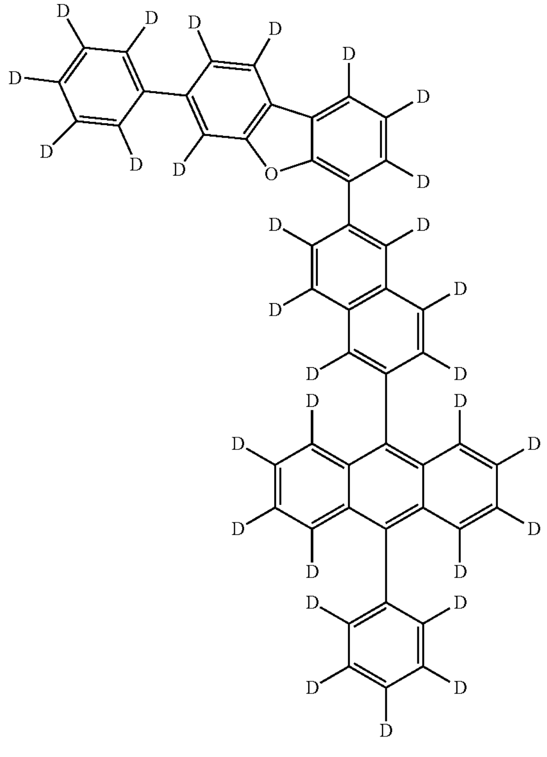

-continued
-continued
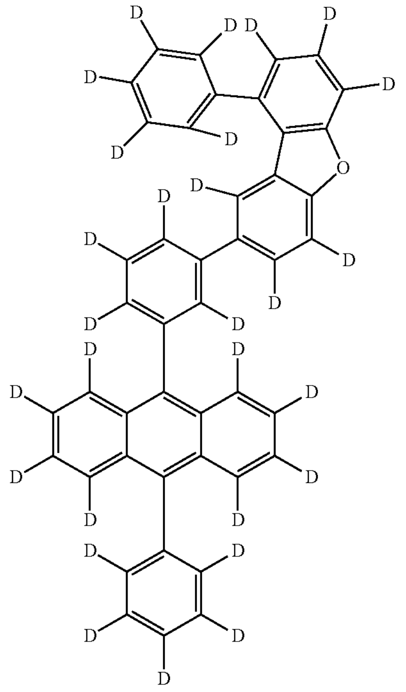
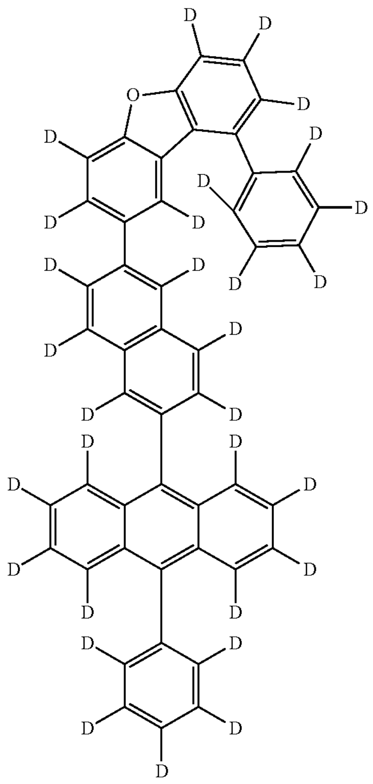
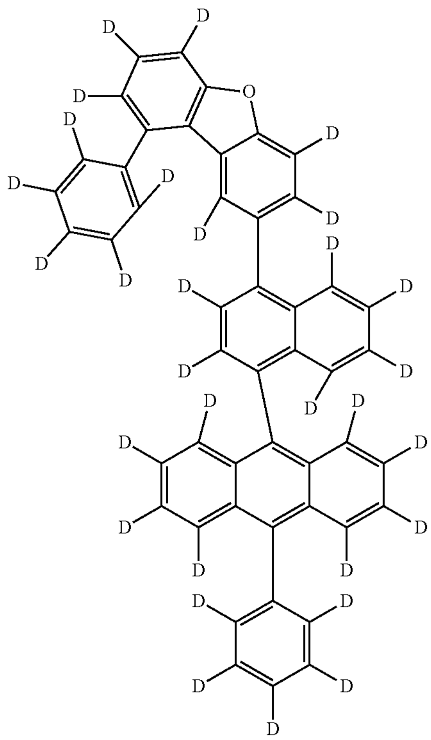
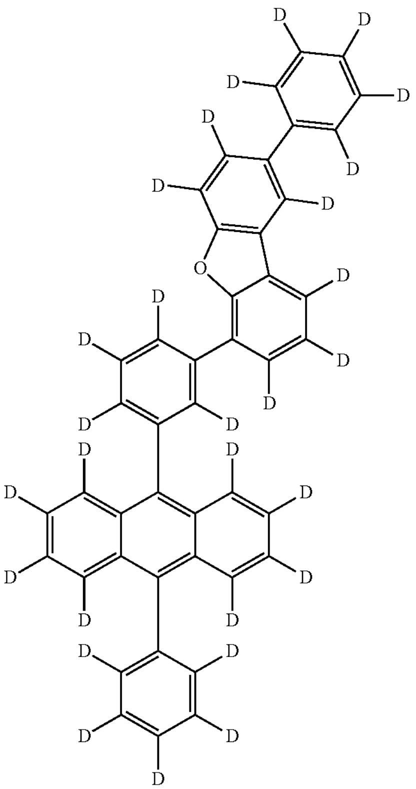

-continued
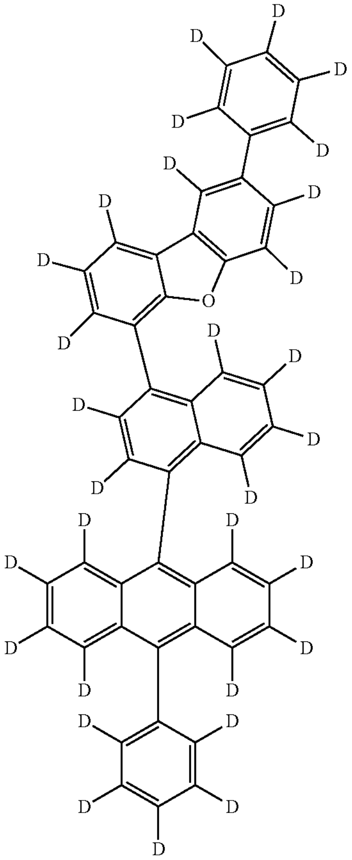
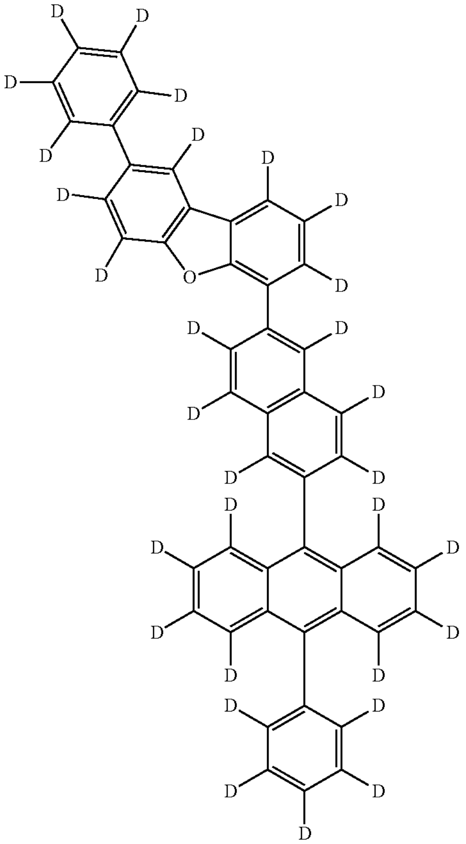
-continued
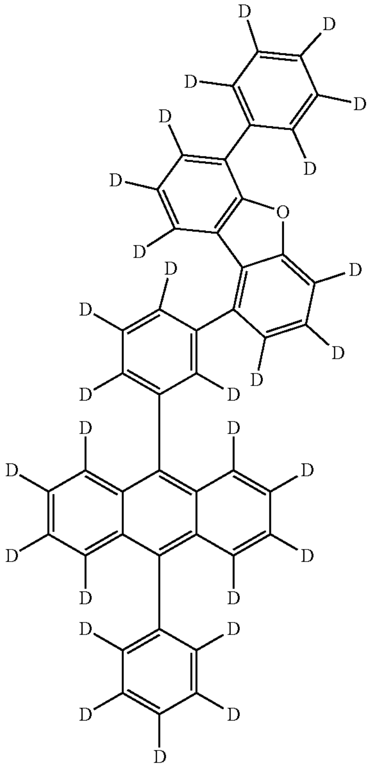
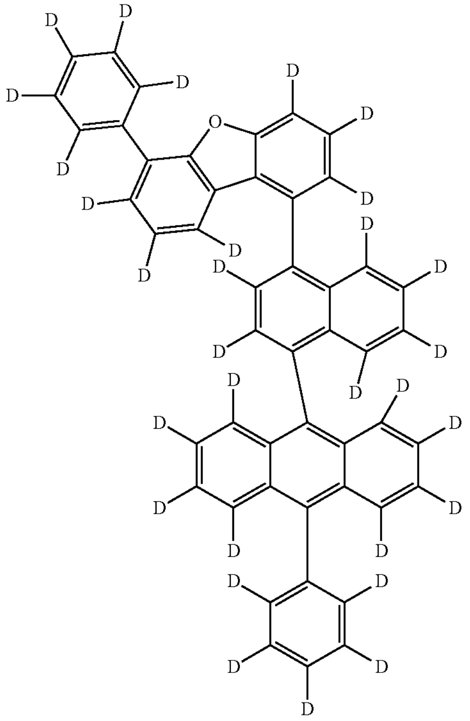

-continued
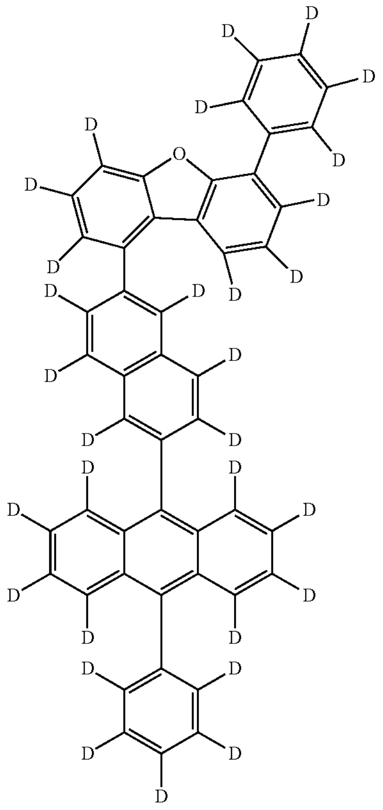
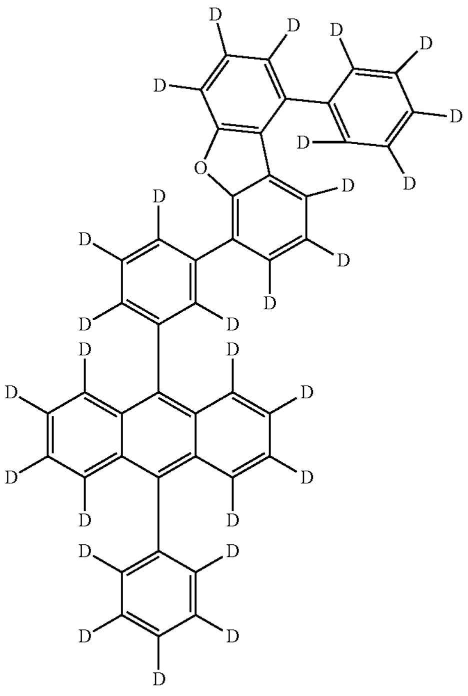
-continued
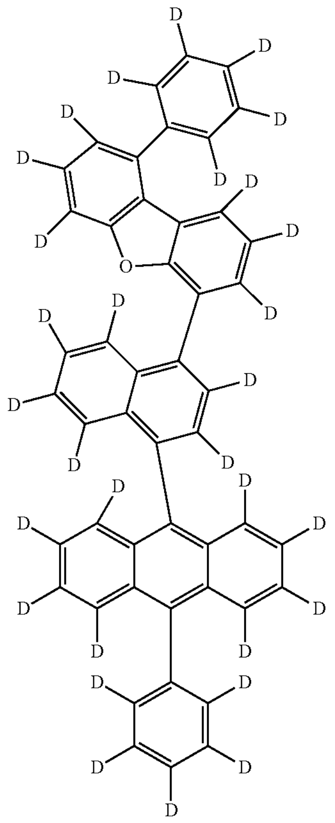
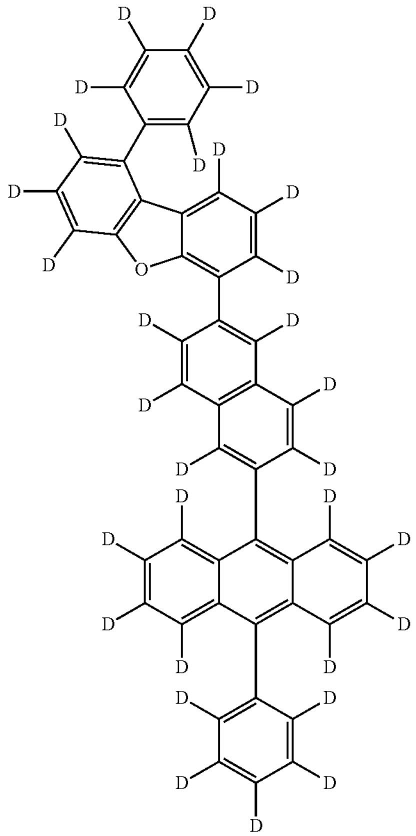

-continued
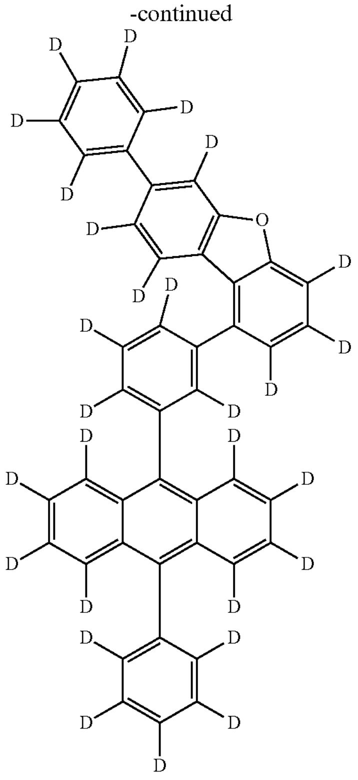
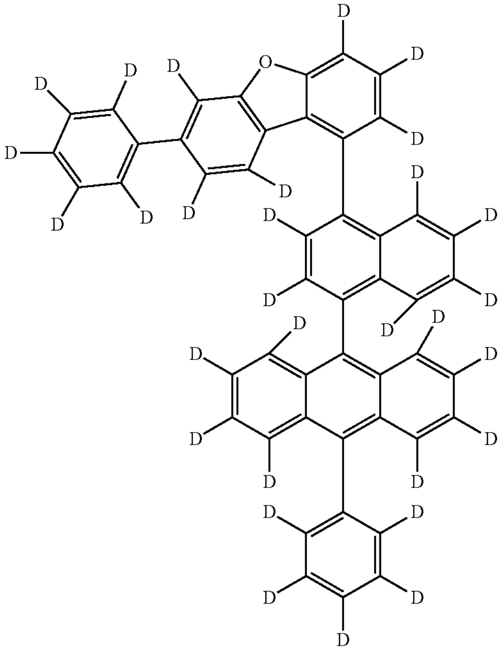
-continued
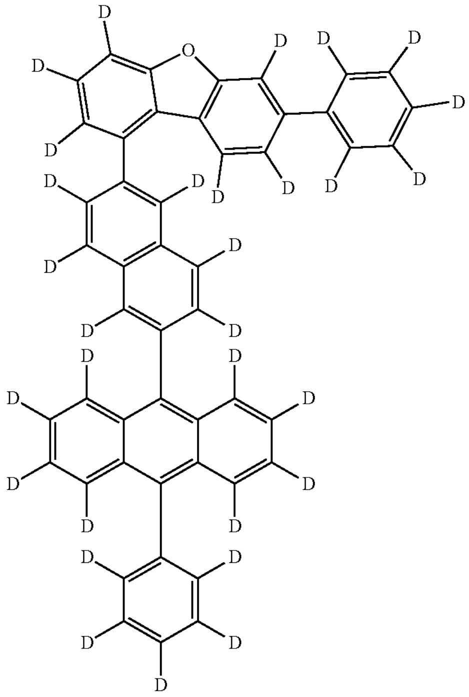
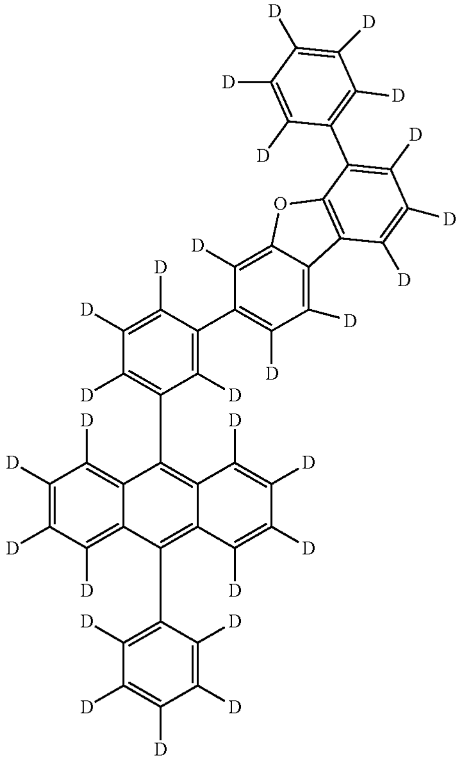

-continued
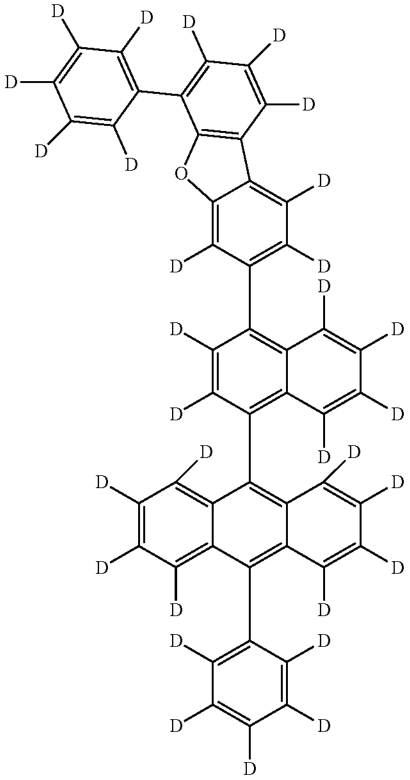
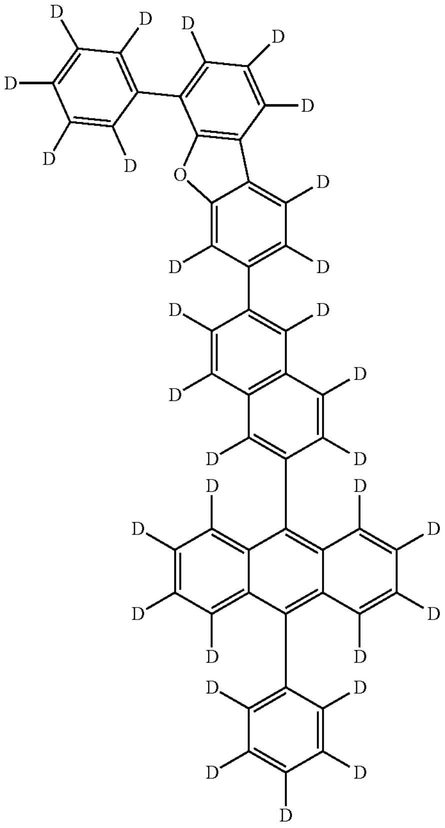
-continued
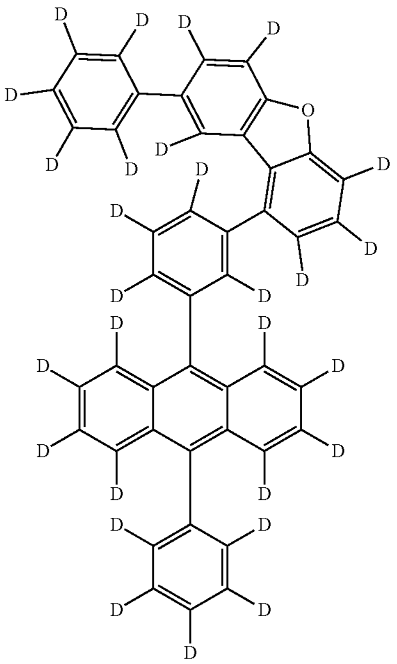
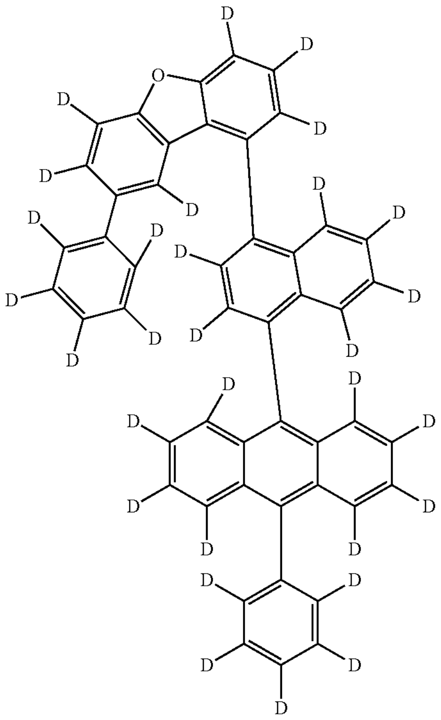

-continued
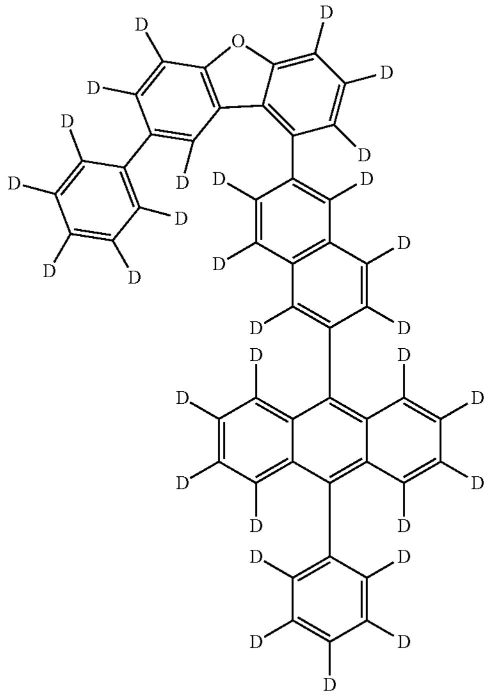
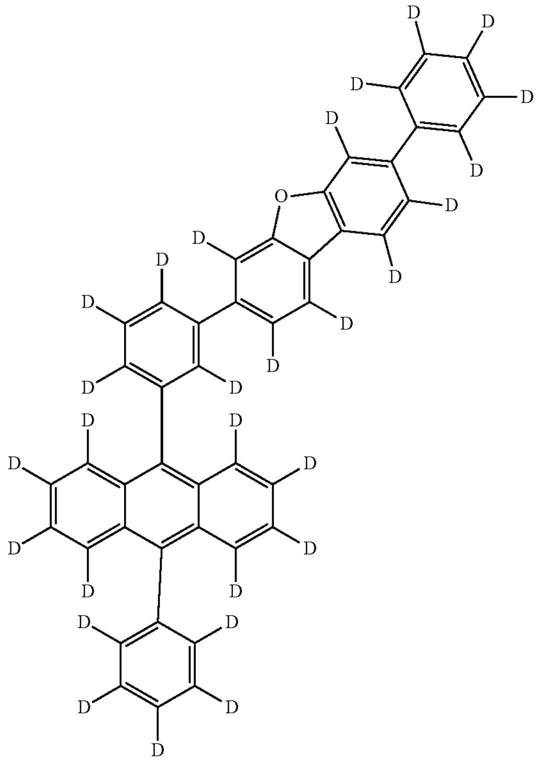
-continued
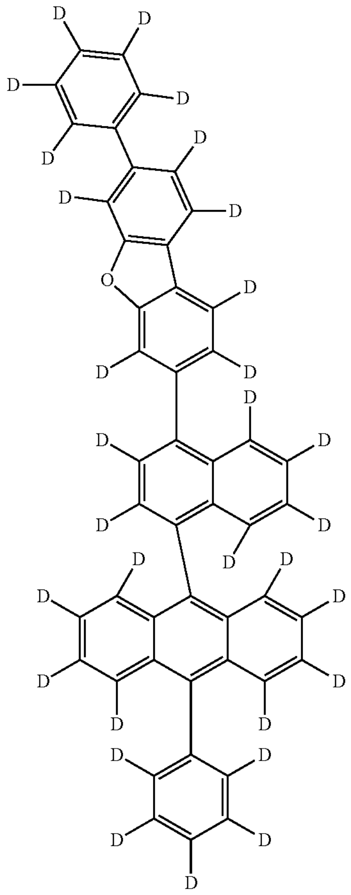

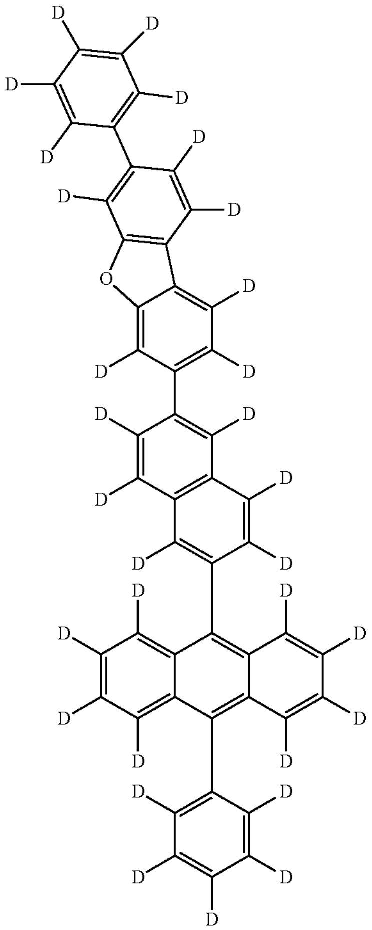
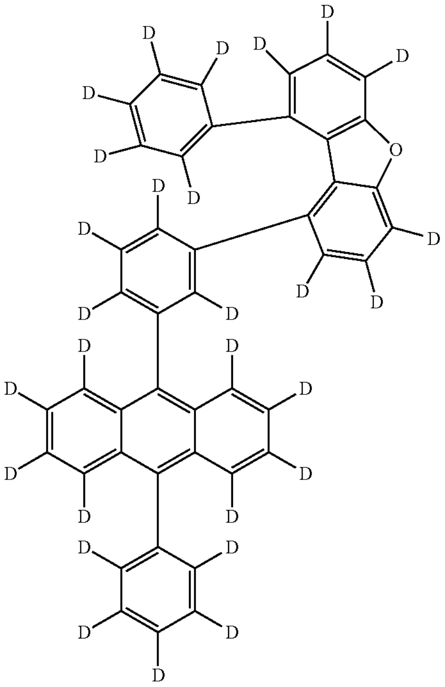
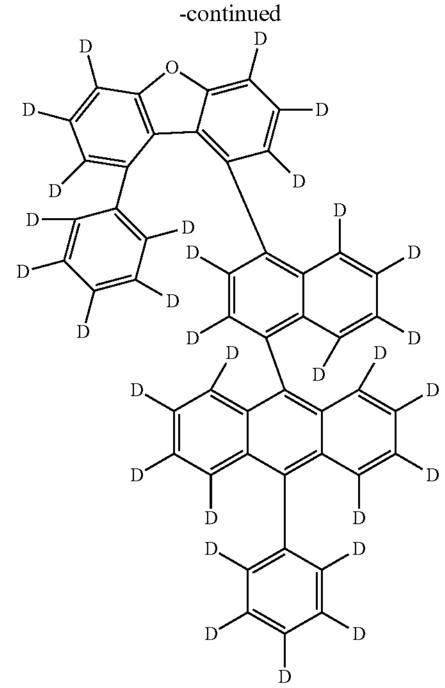
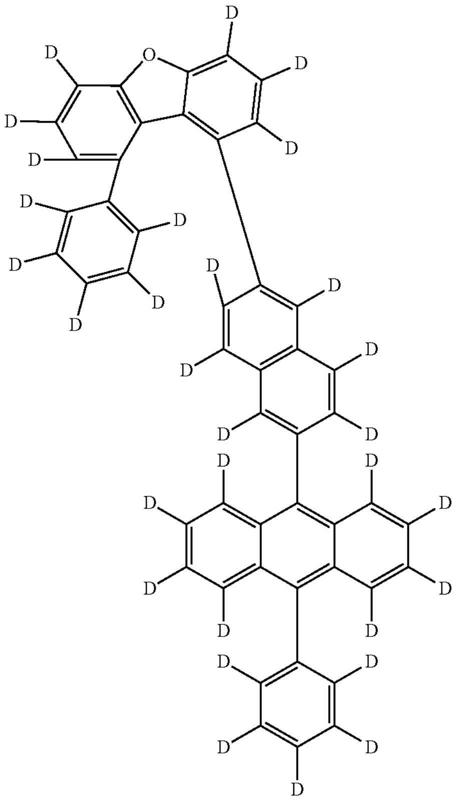 [SMILES: [2H]c1c([2H])c([2H])c(-c2c3c([2H])c([2H])c([2H])c([2H])c3c(-c3c([2H])c([2H])c4c([2H])c(-c5c([2H])c([2H])c([2H])c6oc7c([2H])c([2H])c([2H])c(-c8c([2H])c([2H])c([2H])c([2H])c8[2H])c7c56)c([2H])c([2H])c4c3[2H])c3c([2H])c([2H])c([2H])c([2H])c23)c([2H])c1[2H]]

-continued
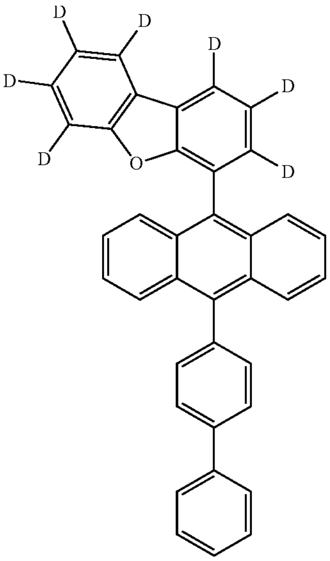
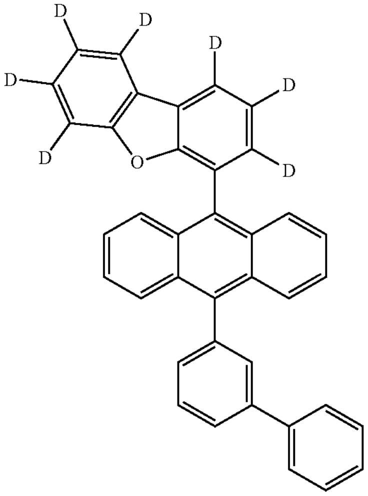
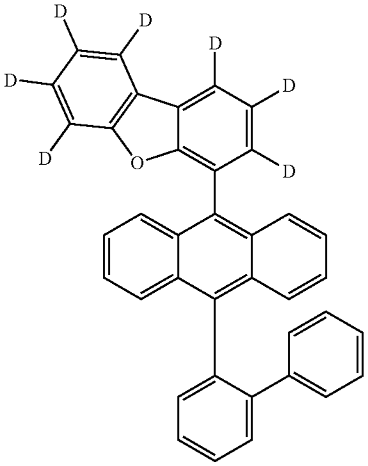
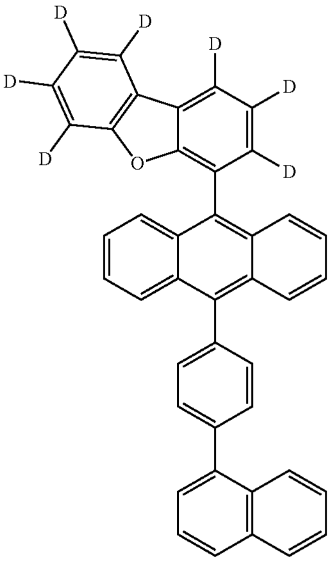
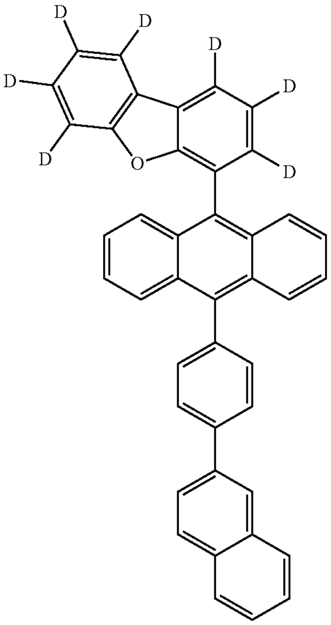

-continued
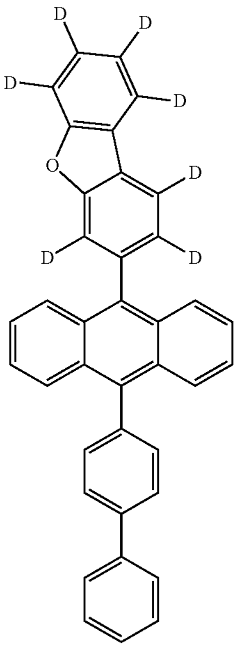
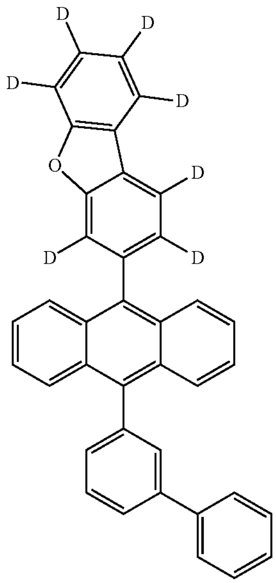
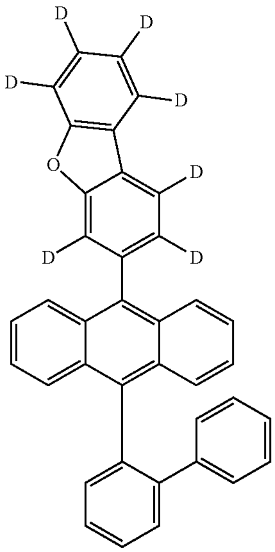
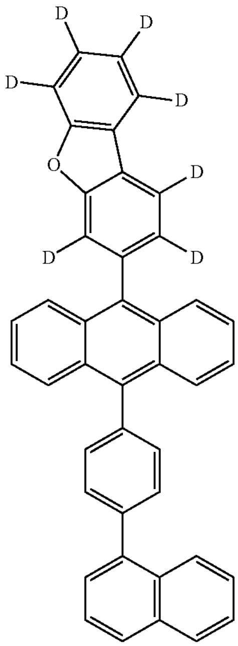
-continued
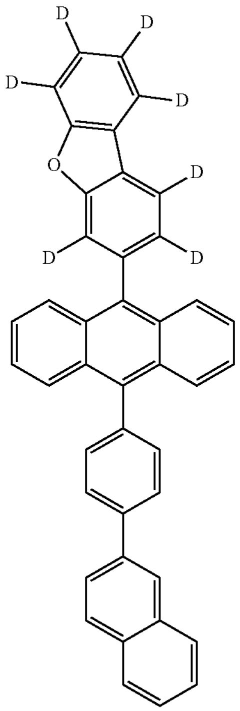
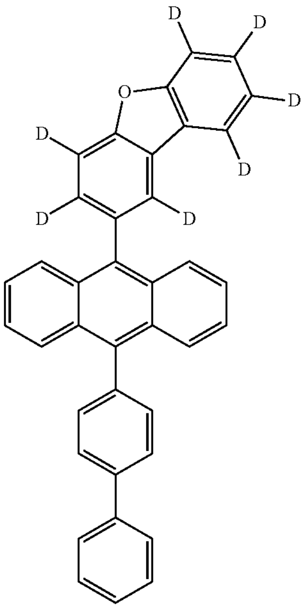
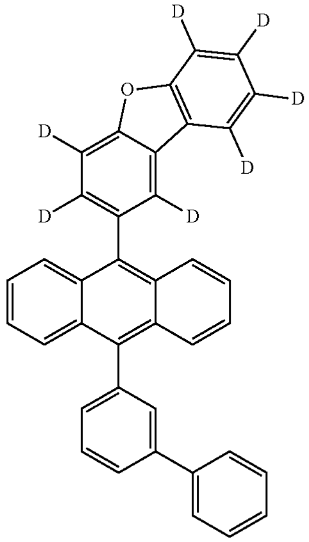

-continued
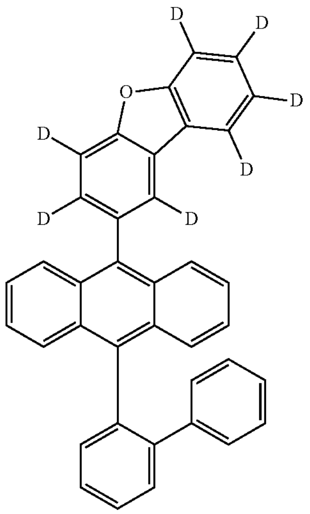
-continued
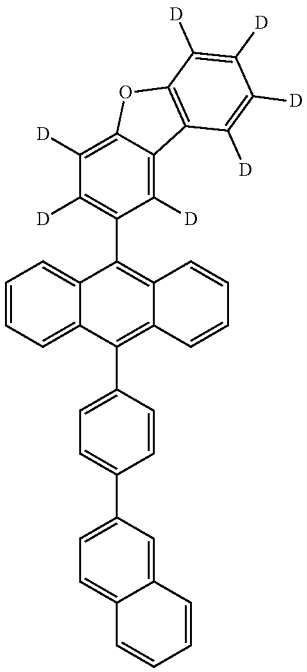
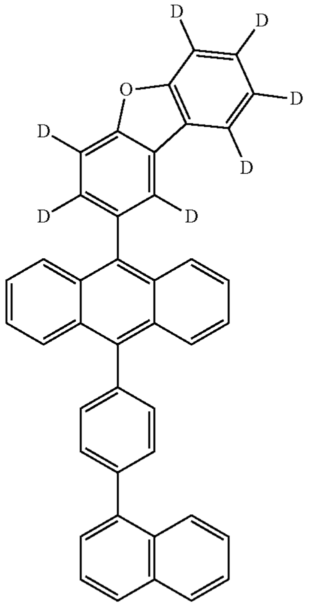
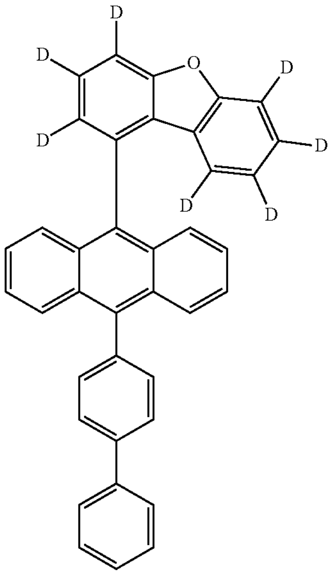

-continued
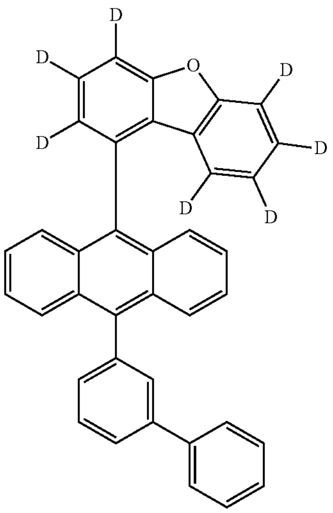
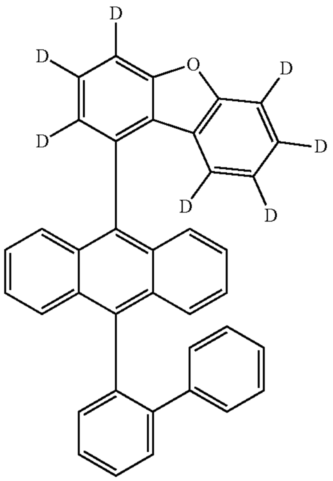
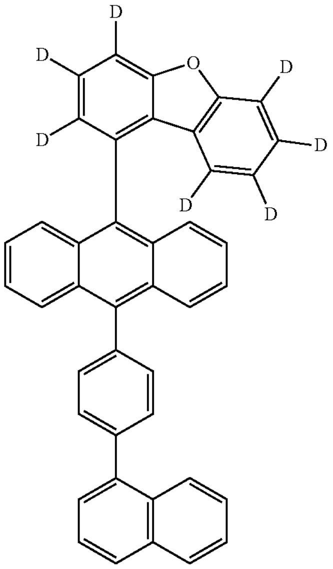
-continued
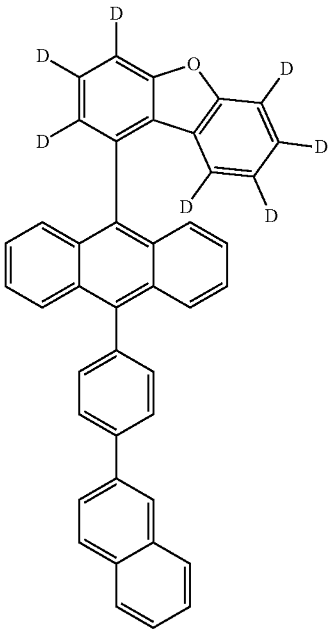
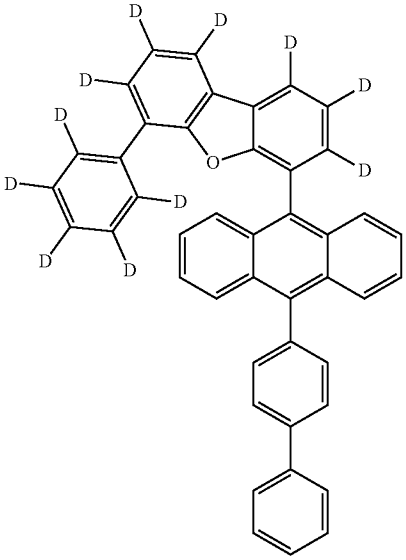
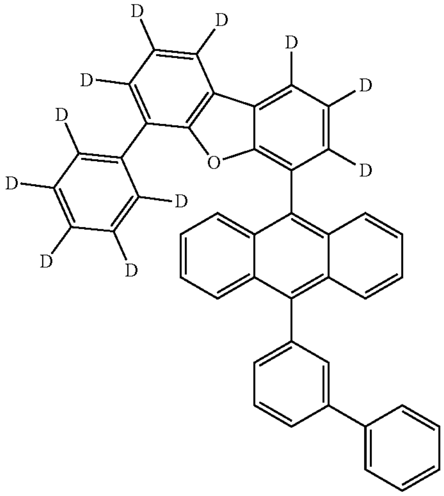

-continued
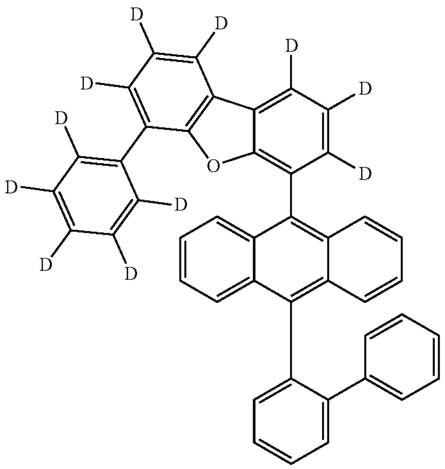
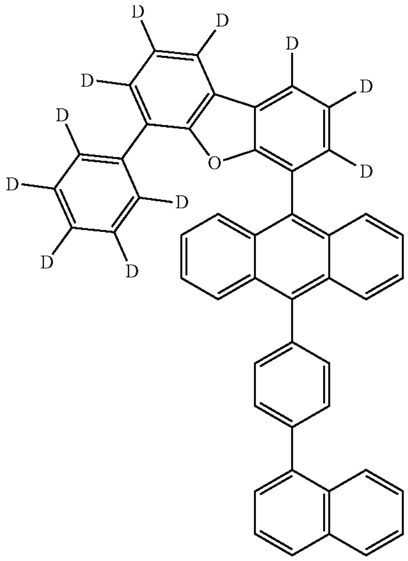
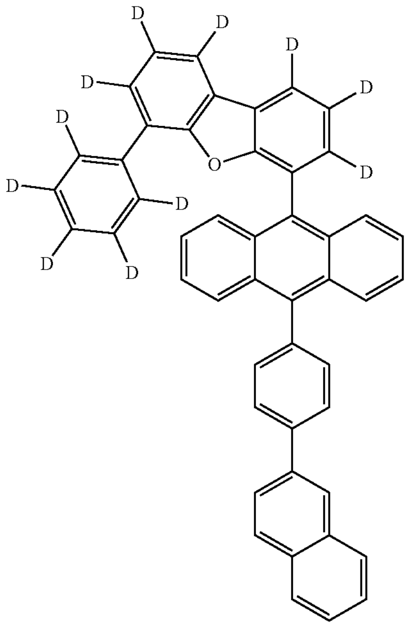
-continued
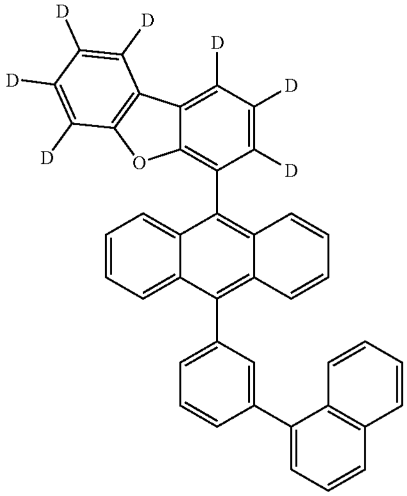
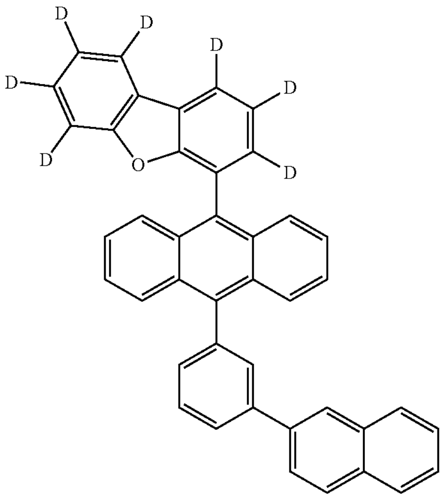
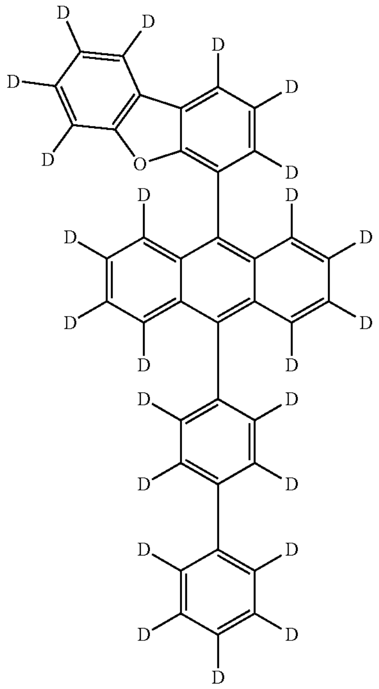

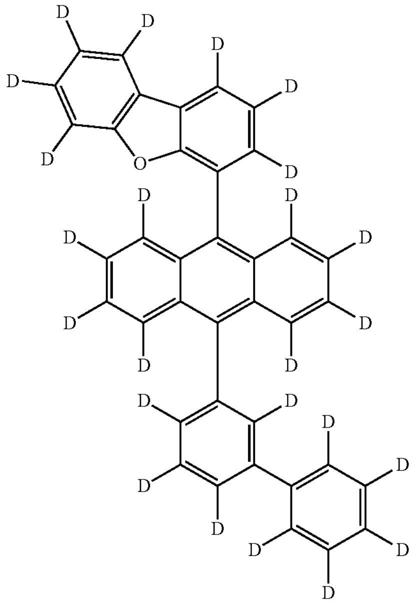
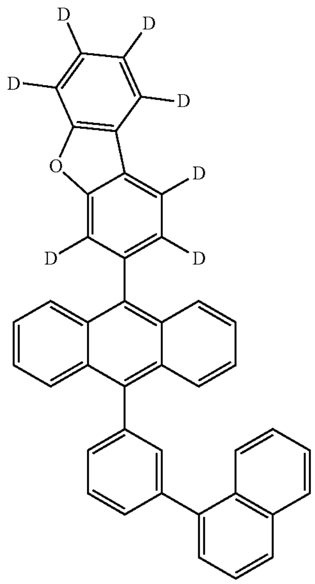
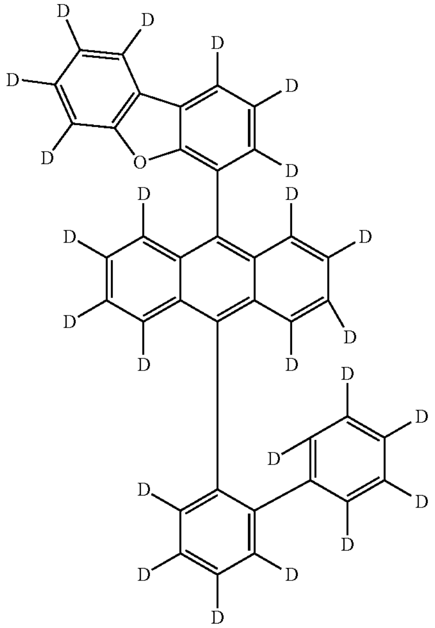
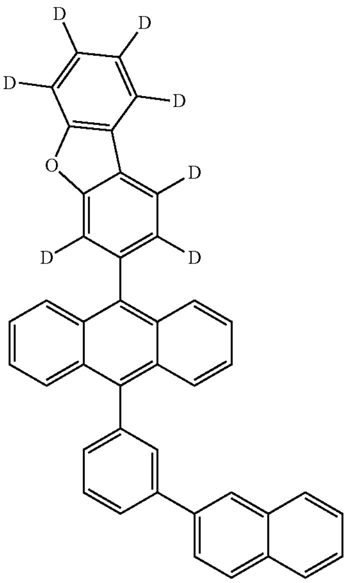

-continued
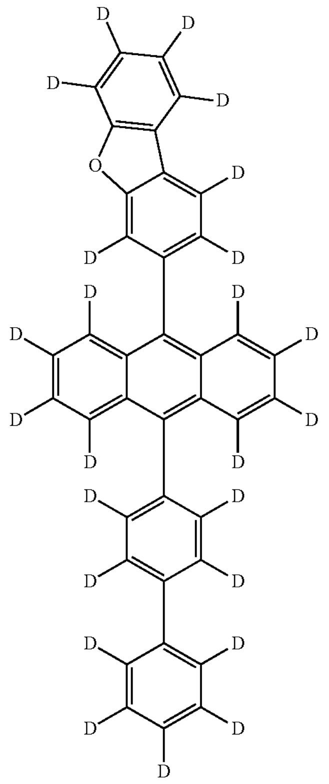
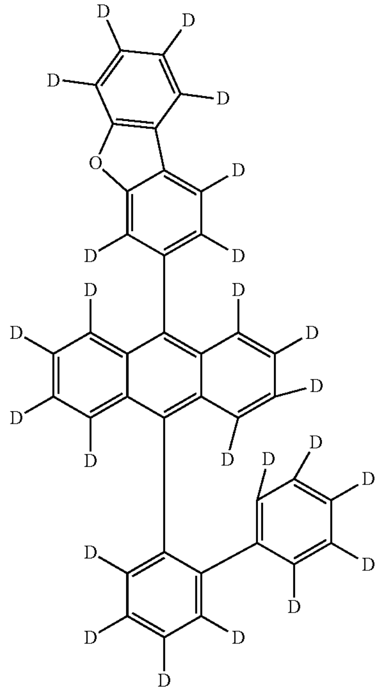 [SMILES: [2H]c1c([2H])c([2H])c(-c2c([2H])c([2H])c([2H])c([2H])c2-c2c3c([2H])c([2H])c([2H])c([2H])c3c(-c3c([2H])c([2H])c4c(oc5c([2H])c([2H])c([2H])c([2H])c54)c3[2H])c3c([2H])c([2H])c([2H])c([2H])c23)c([2H])c1[2H]]
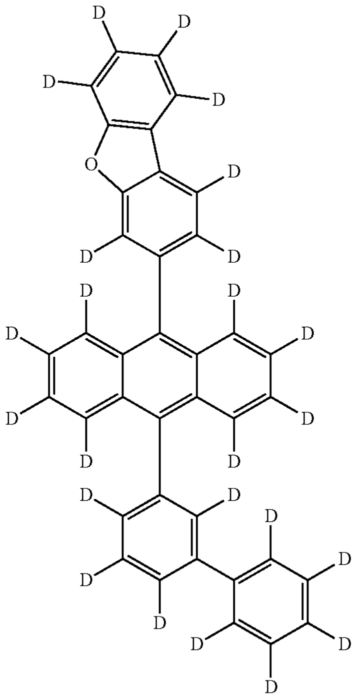
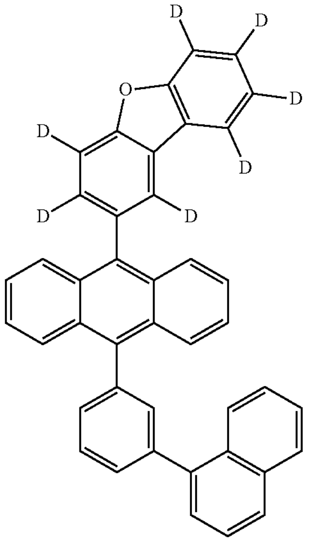

-continued
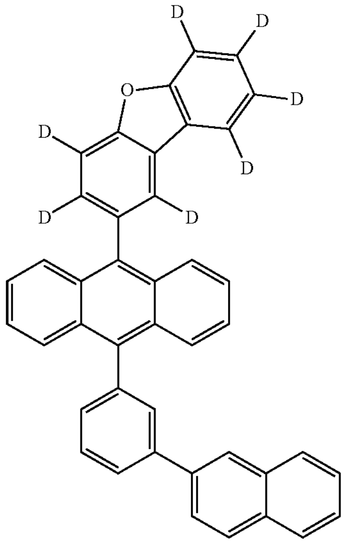
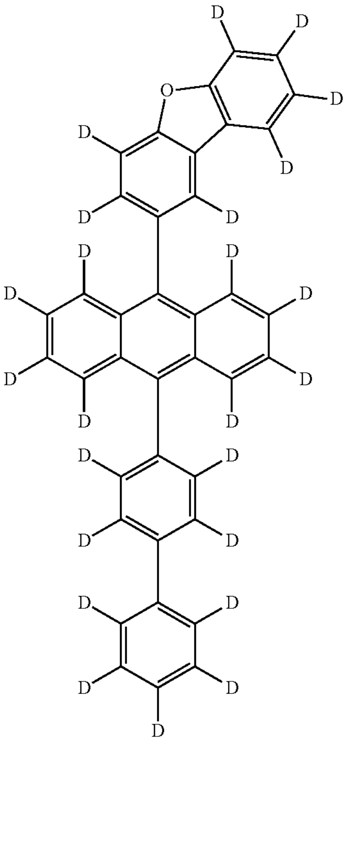
-continued
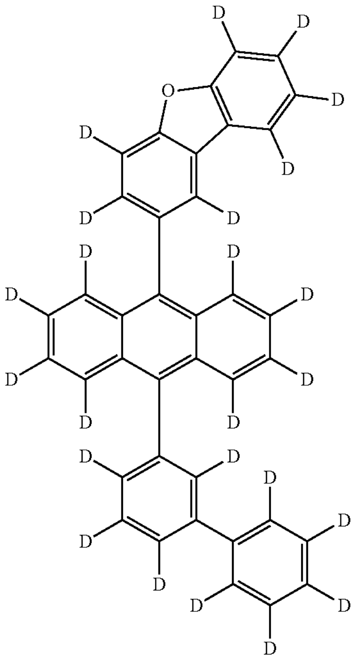
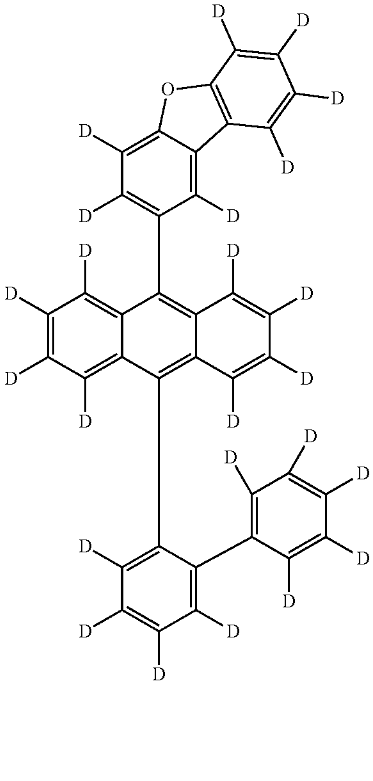 [SMILES: [2H]c1c([2H])c([2H])c(-c2c([2H])c([2H])c([2H])c([2H])c2-c2c3c([2H])c([2H])c([2H])c([2H])c3c(-c3c([2H])c([2H])c4oc5c([2H])c([2H])c([2H])c([2H])c5c4c3[2H])c3c([2H])c([2H])c([2H])c([2H])c23)c([2H])c1[2H]]

-continued
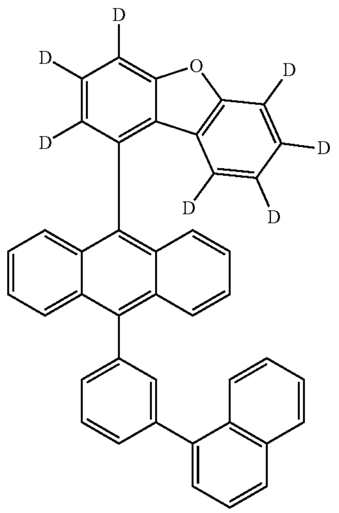
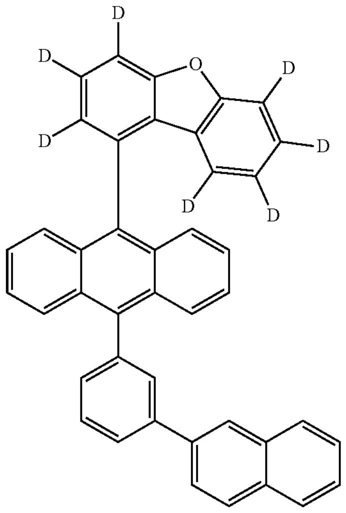
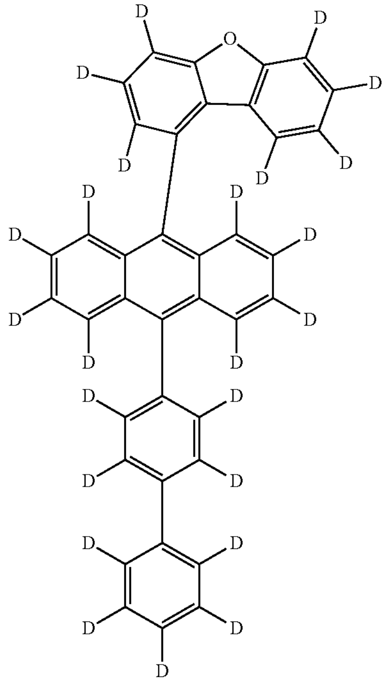
-continued
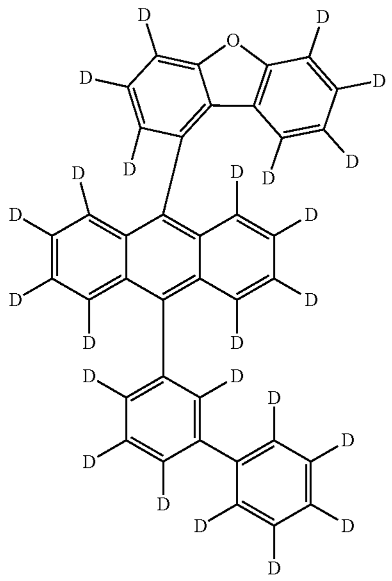
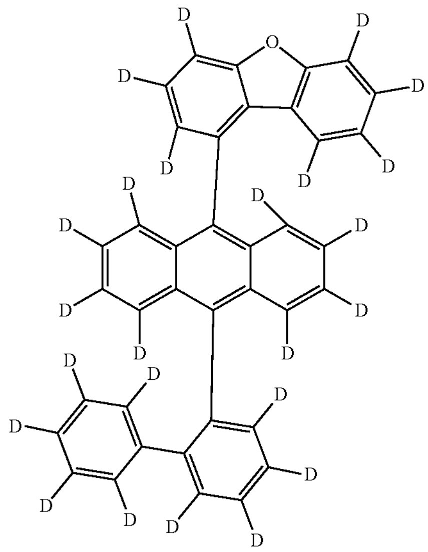
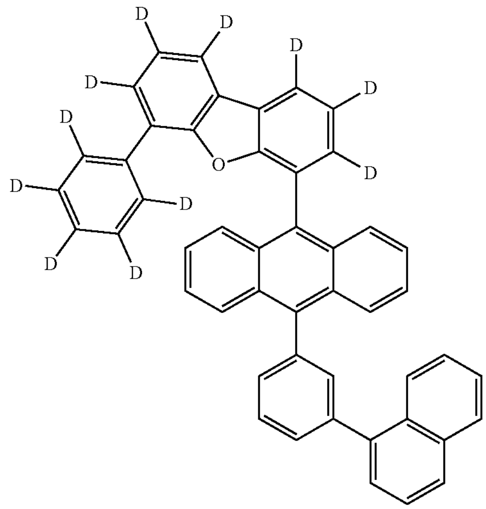

-continued
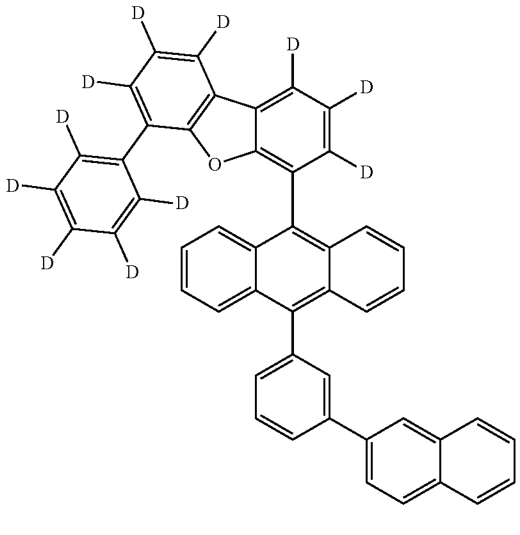
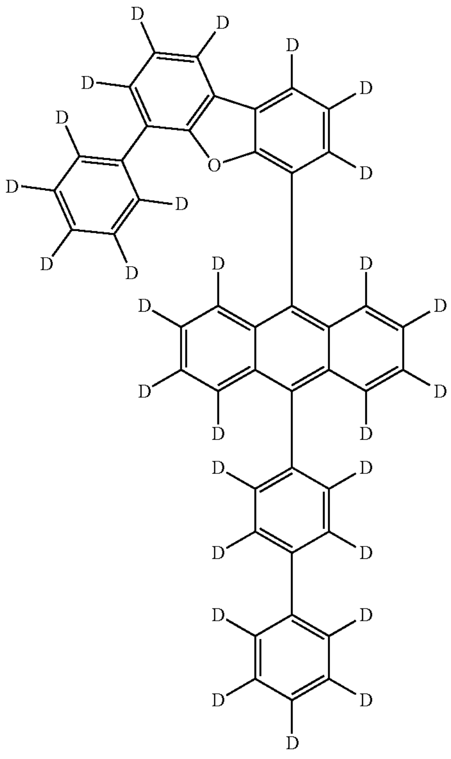
-continued
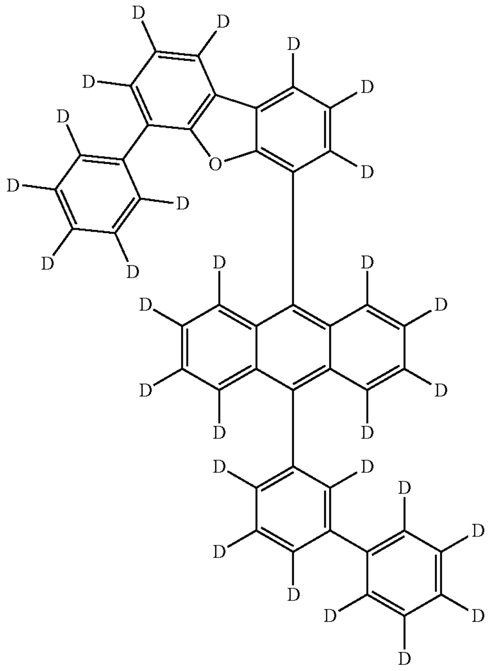
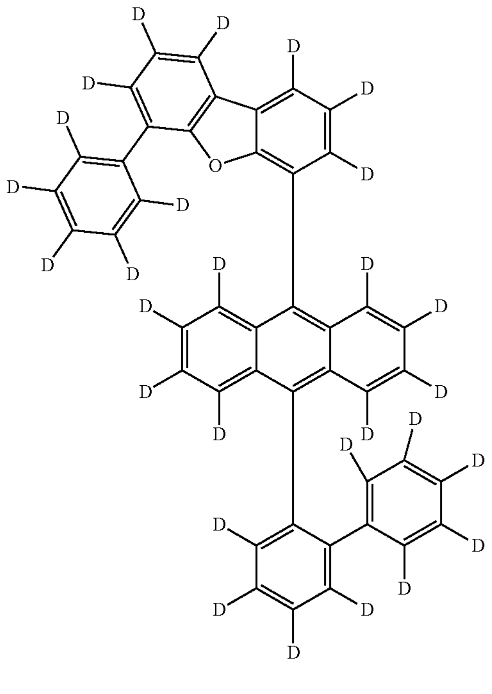 [SMILES: [2H]c1c([2H])c([2H])c(-c2c([2H])c([2H])c([2H])c([2H])c2-c2c3c([2H])c([2H])c([2H])c([2H])c3c(-c3c([2H])c([2H])c([2H])c4c3oc3c(-c5c([2H])c([2H])c([2H])c([2H])c5[2H])c([2H])c([2H])c([2H])c34)c3c([2H])c([2H])c([2H])c([2H])c23)c([2H])c1[2H]]

-continued
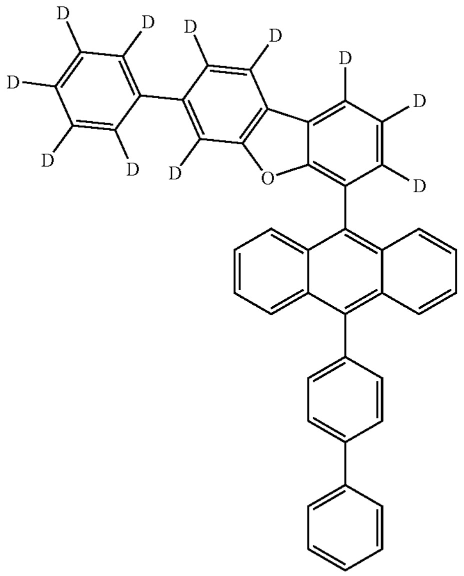
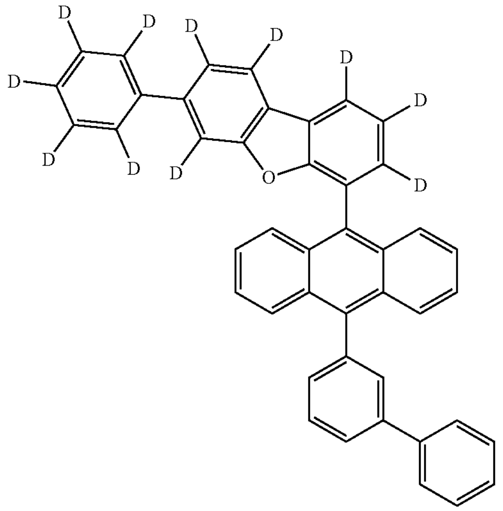
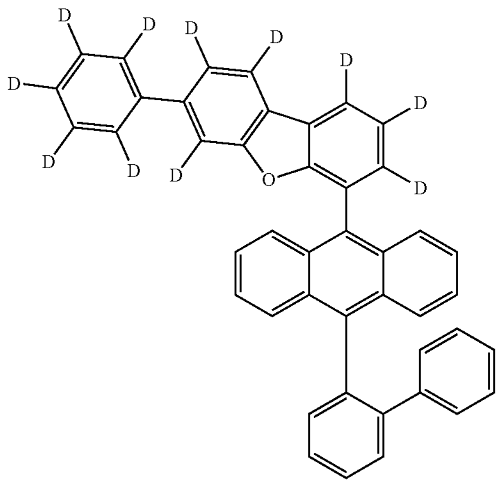
-continued
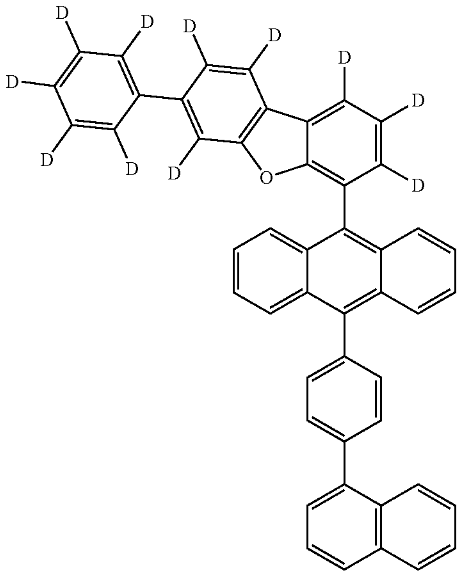
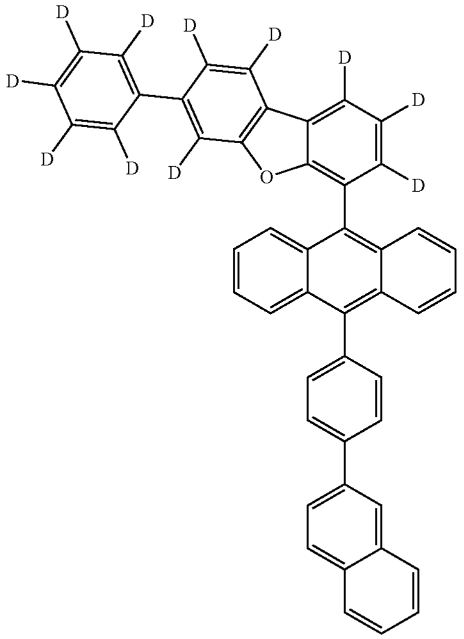

-continued
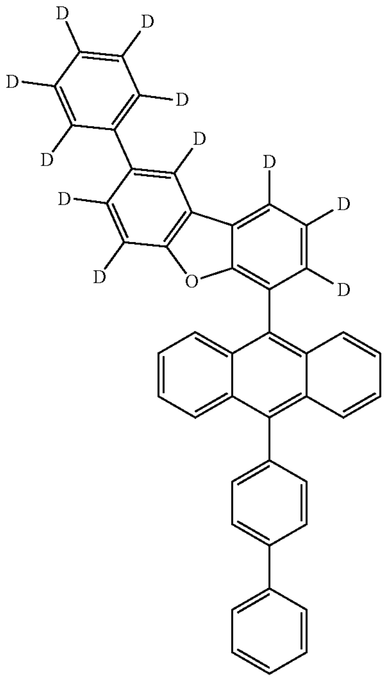
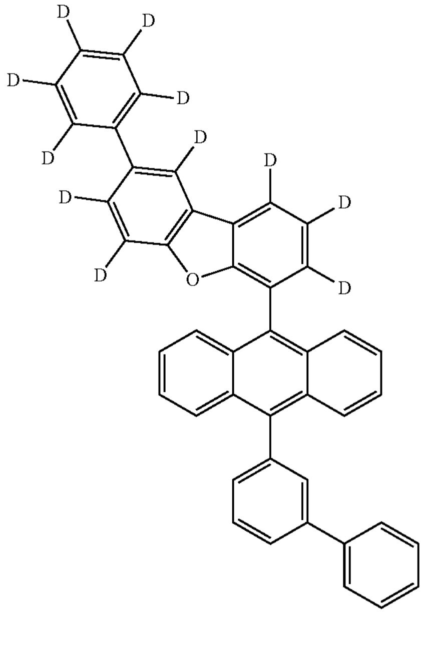
-continued
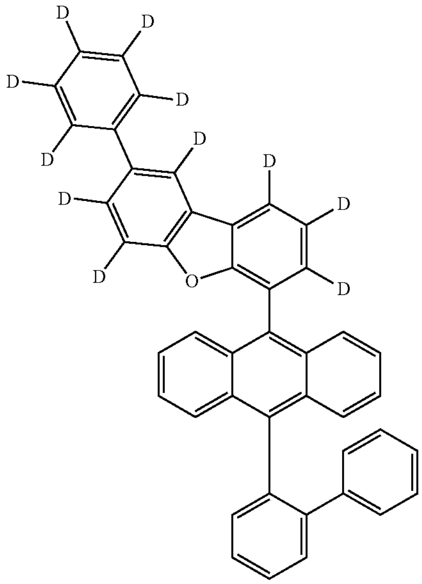
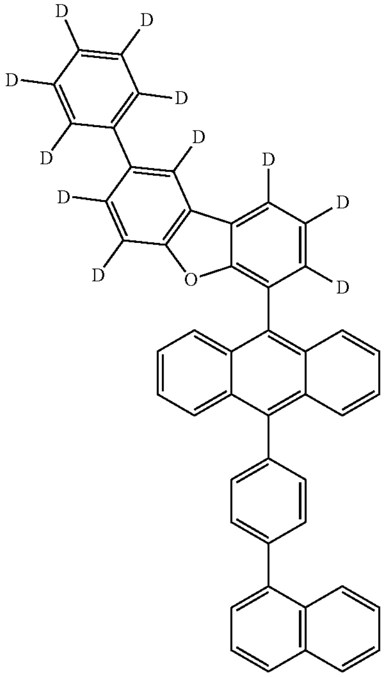

-continued
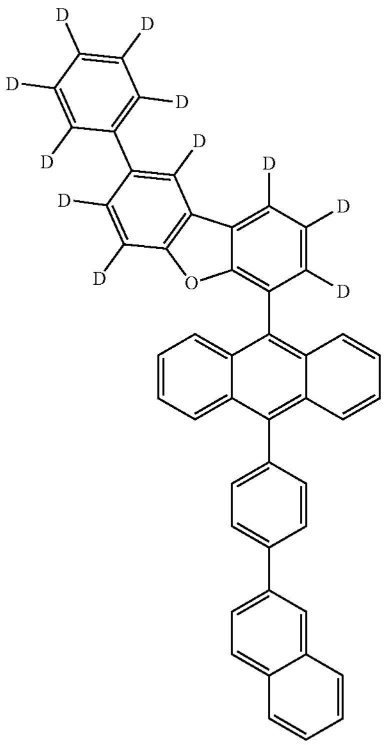 [SMILES: [2H]c1c([2H])c([2H])c(-c2c([2H])c([2H])c3oc4c(-c5c6ccccc6c(-c6ccc(-c7ccc8ccccc8c7)cc6)c6ccccc56)c([2H])c([2H])c([2H])c4c3c2[2H])c([2H])c1[2H]]
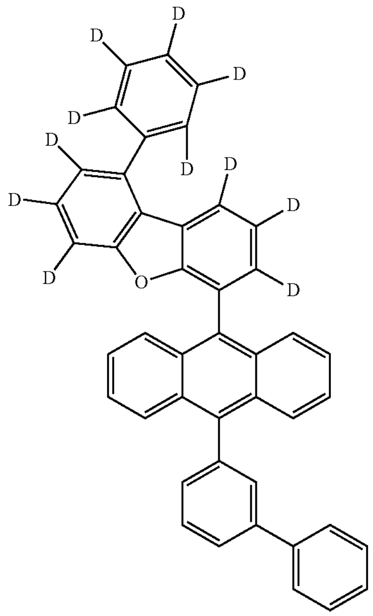
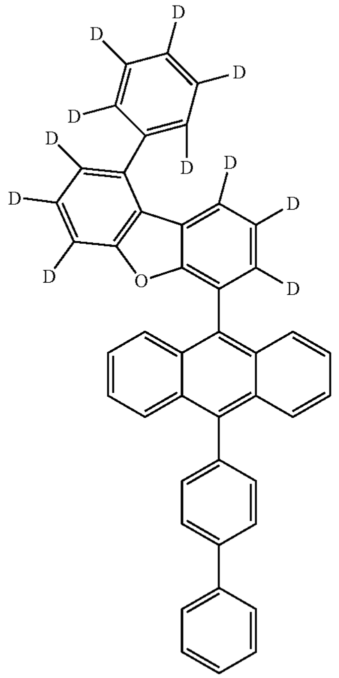
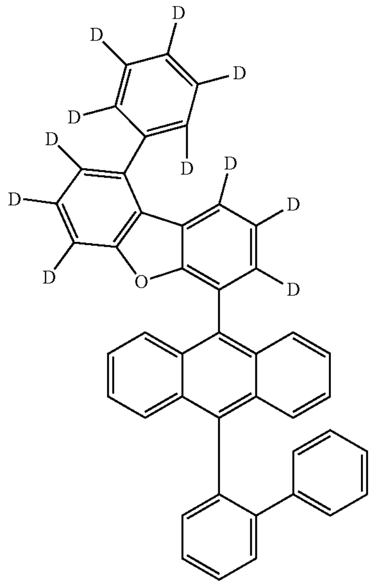

-continued
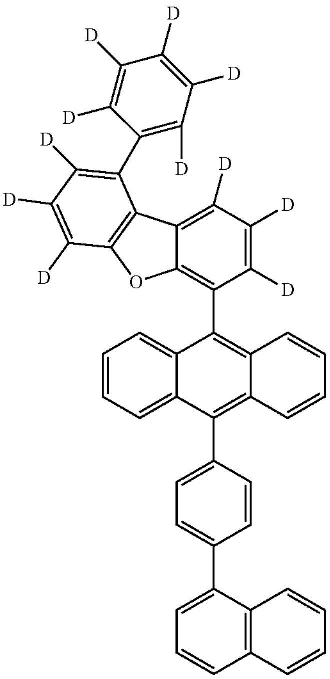
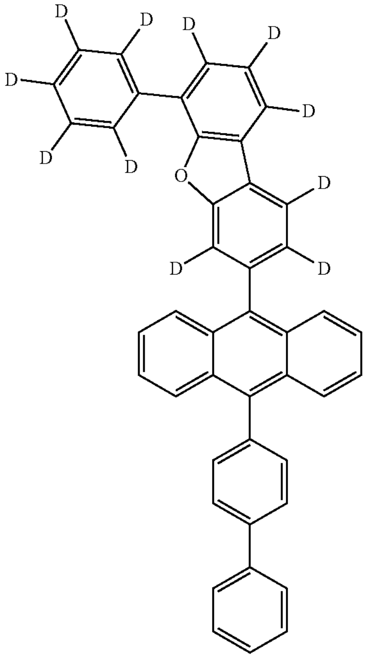
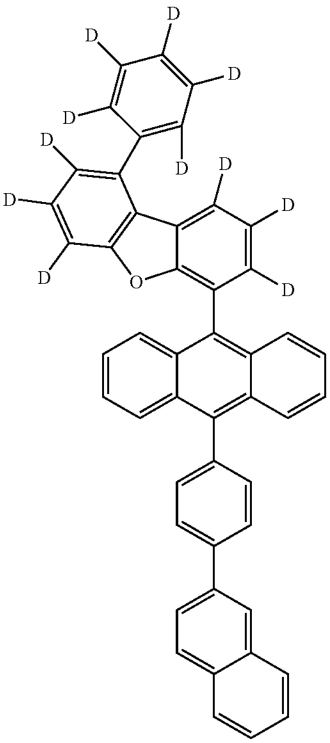 [SMILES: [2H]c1c([2H])c([2H])c(-c2c([2H])c([2H])c([2H])c3oc4c(-c5c6ccccc6c(-c6ccc(-c7ccc8ccccc8c7)cc6)c6ccccc56)c([2H])c([2H])c([2H])c4c23)c([2H])c1[2H]]
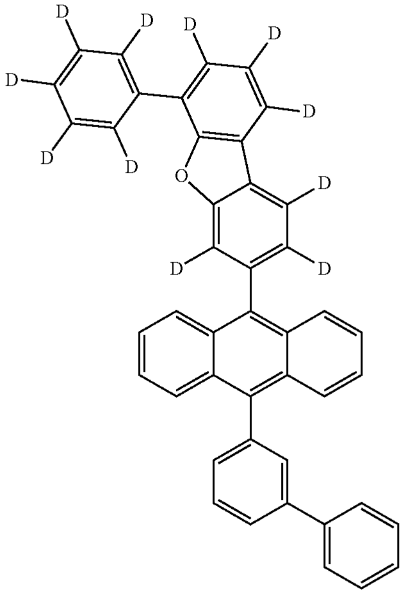

-continued
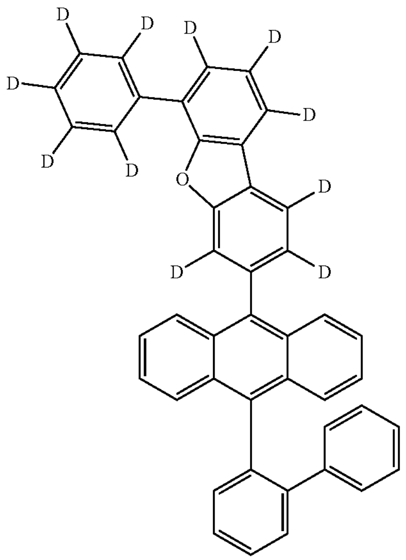
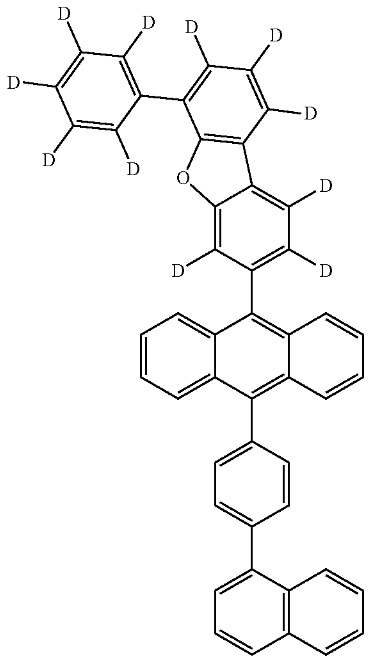
-continued
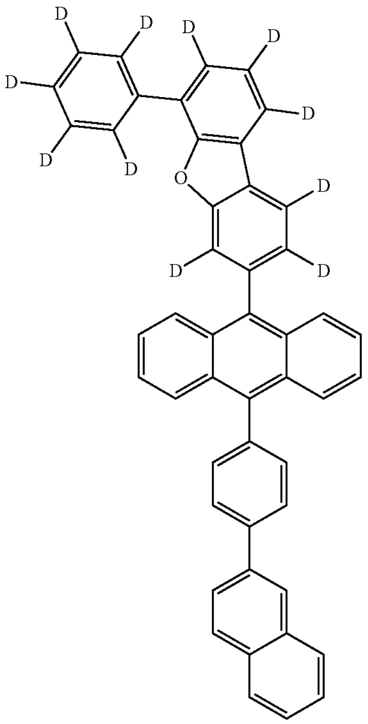
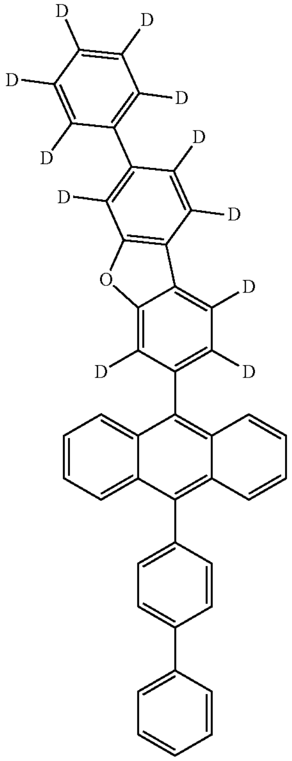

-continued
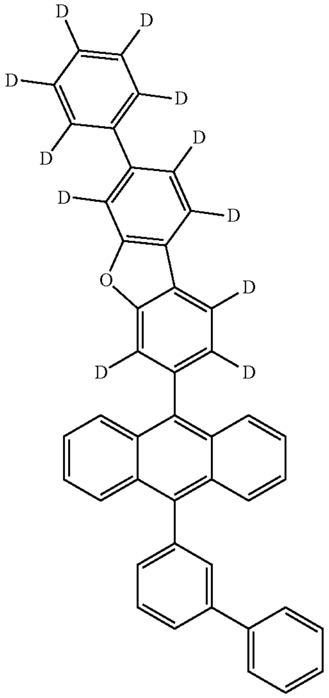
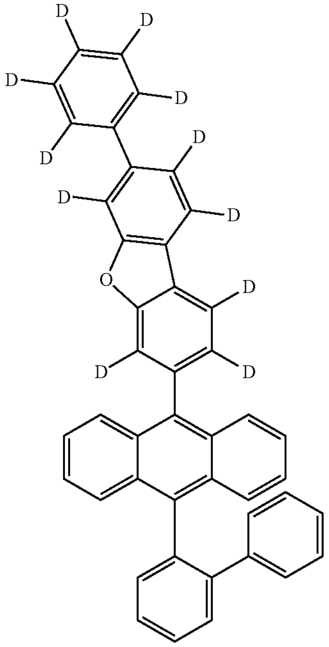
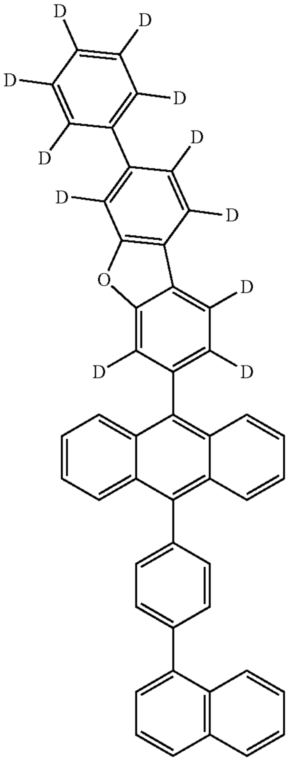
-continued
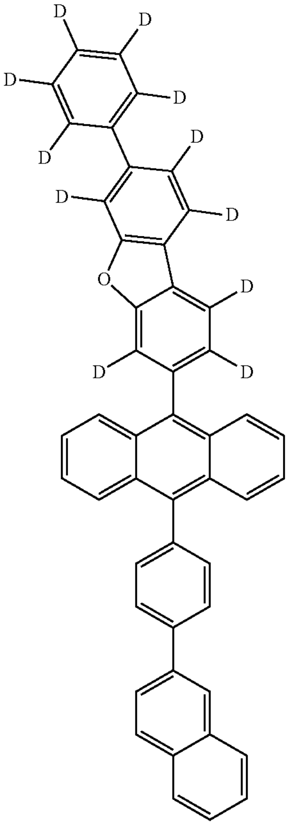 [SMILES: [2H]c1c([2H])c([2H])c(-c2c([2H])c([2H])c3c(oc4c([2H])c(-c5c6ccccc6c(-c6ccc(-c7ccc8ccccc8c7)cc6)c6ccccc56)c([2H])c([2H])c43)c2[2H])c([2H])c1[2H]]

-continued
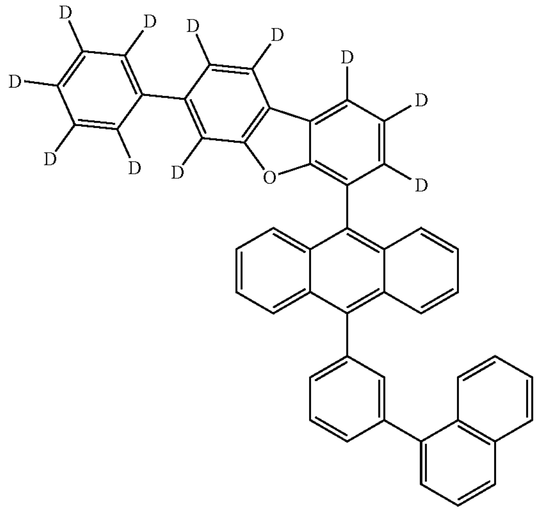
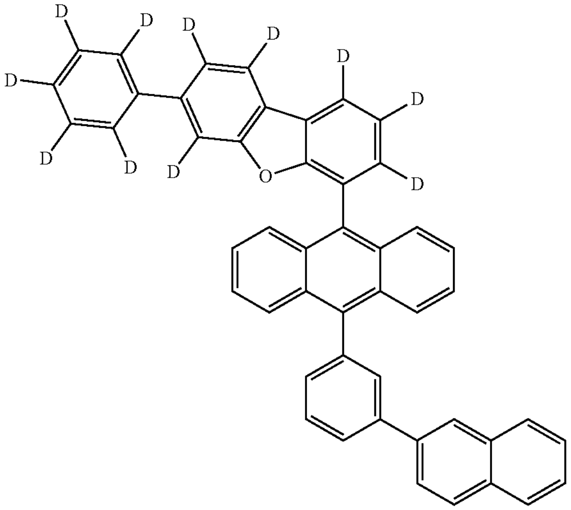
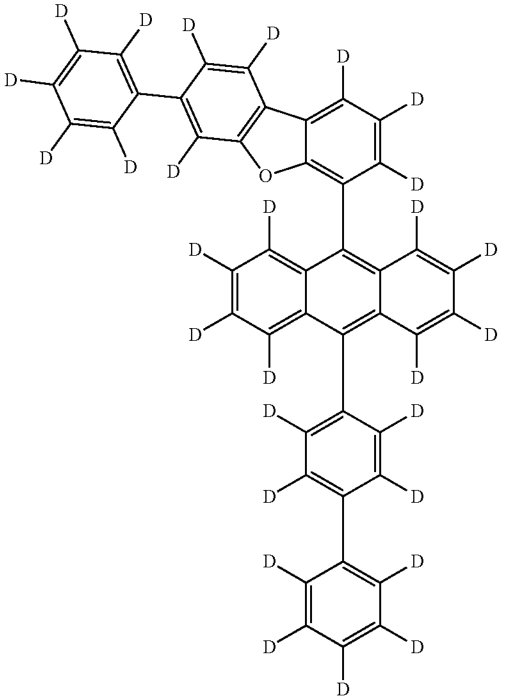
-continued
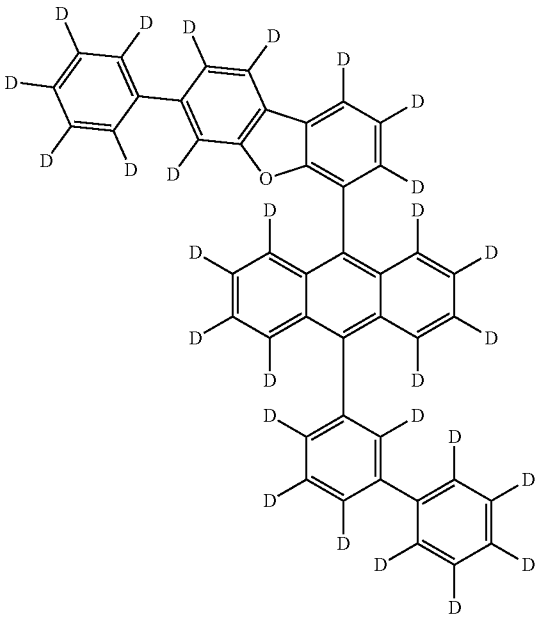
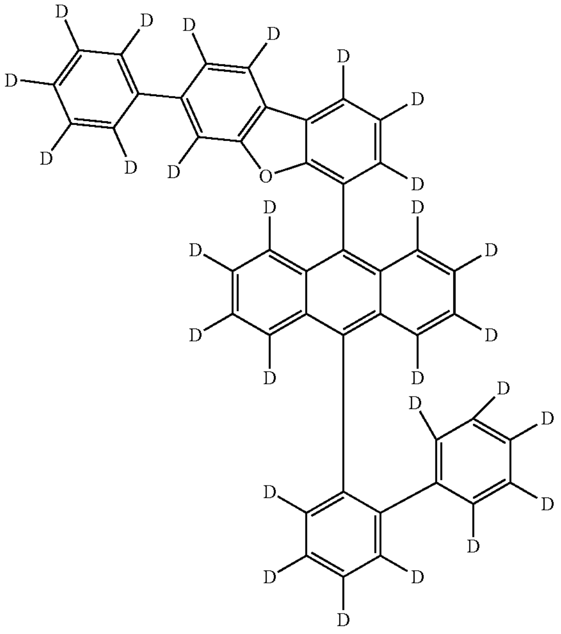

-continued
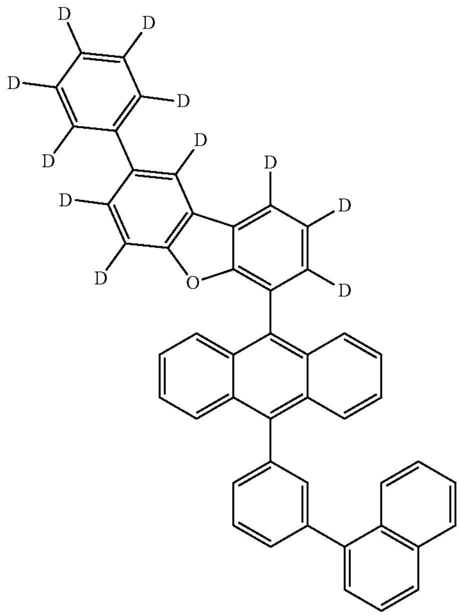
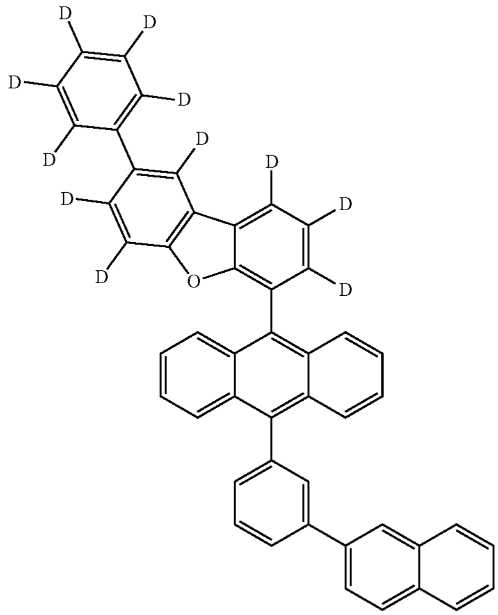
-continued
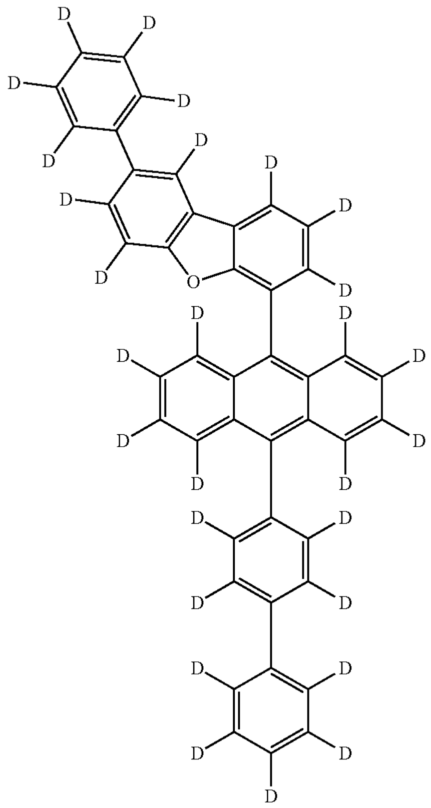
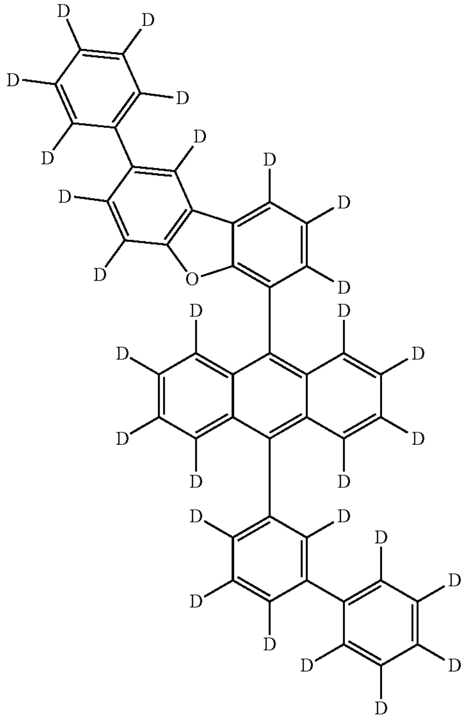

-continued
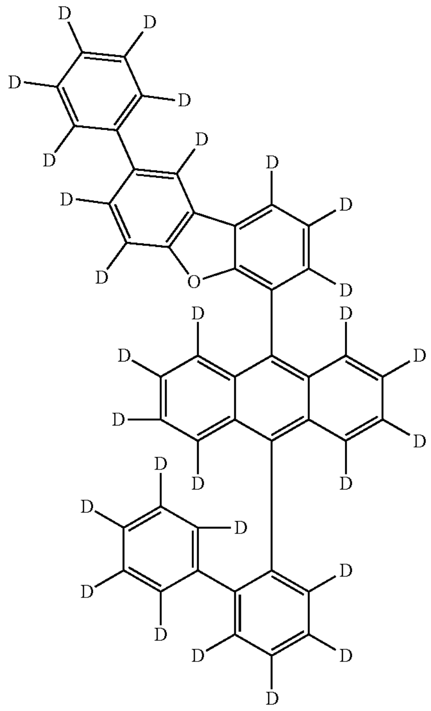 [SMILES: [2H]c1c([2H])c([2H])c(-c2c([2H])c([2H])c([2H])c([2H])c2-c2c3c([2H])c([2H])c([2H])c([2H])c3c(-c3c([2H])c([2H])c([2H])c4c3oc3c([2H])c([2H])c(-c5c([2H])c([2H])c([2H])c([2H])c5[2H])c([2H])c34)c3c([2H])c([2H])c([2H])c([2H])c23)c([2H])c1[2H]]
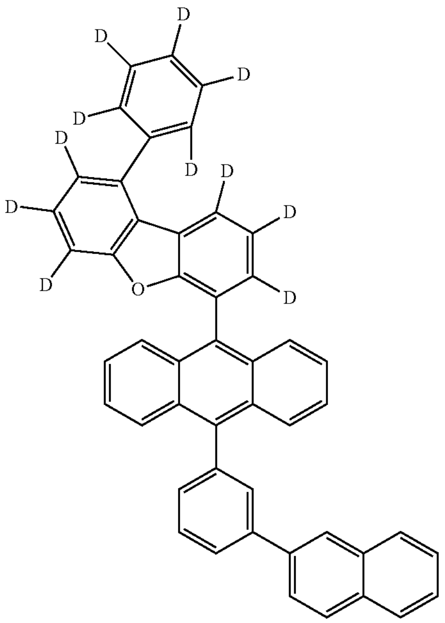
-continued
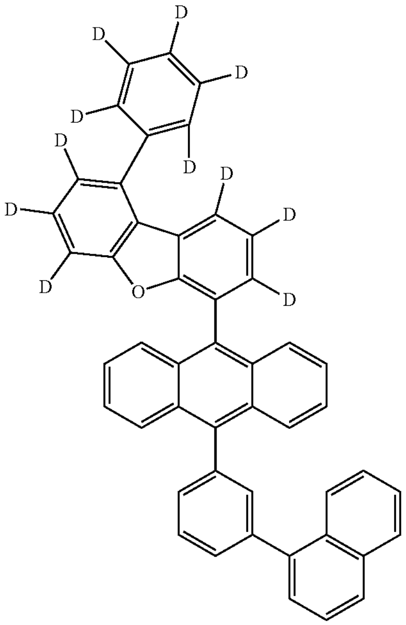
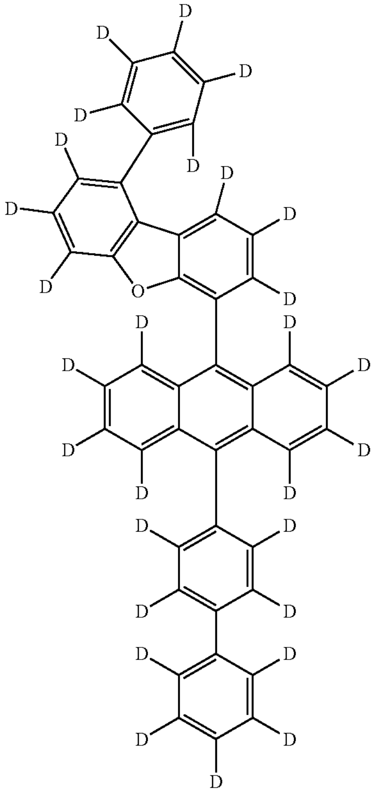

-continued
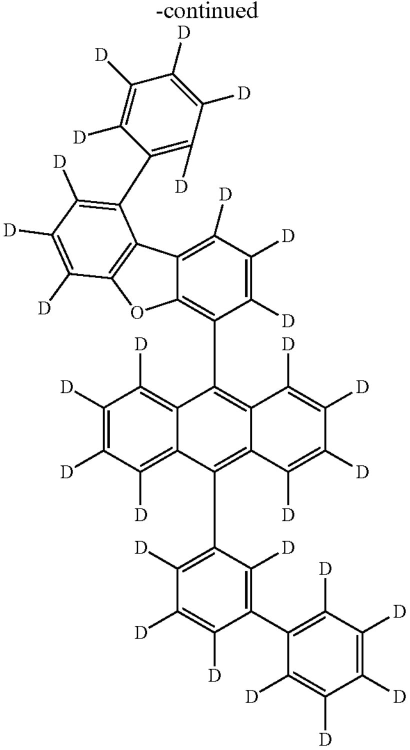
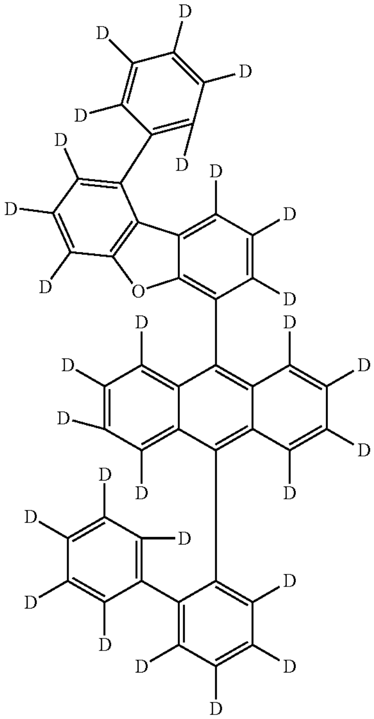 [SMILES: [2H]c1c([2H])c([2H])c(-c2c([2H])c([2H])c([2H])c([2H])c2-c2c3c([2H])c([2H])c([2H])c([2H])c3c(-c3c([2H])c([2H])c([2H])c4c3oc3c([2H])c([2H])c([2H])c(-c5c([2H])c([2H])c([2H])c([2H])c5[2H])c34)c3c([2H])c([2H])c([2H])c([2H])c23)c([2H])c1[2H]]
-continued
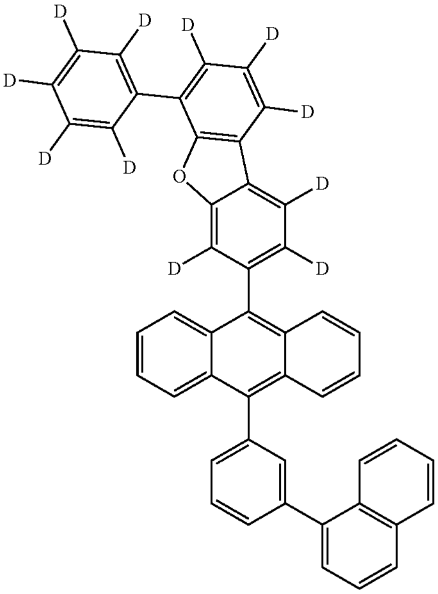
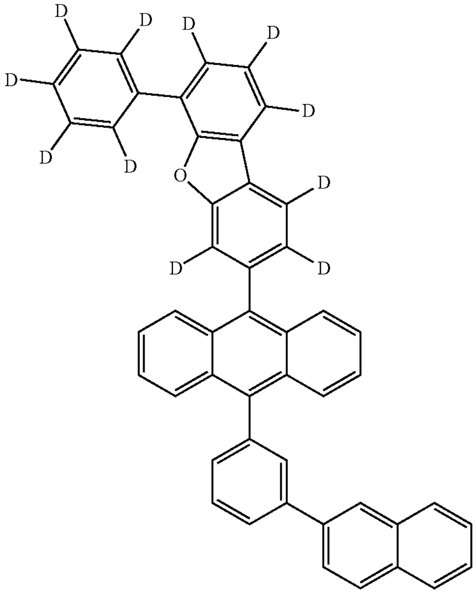

-continued
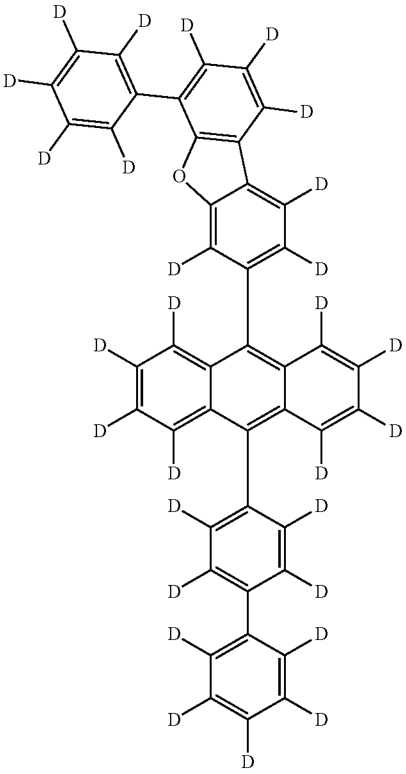
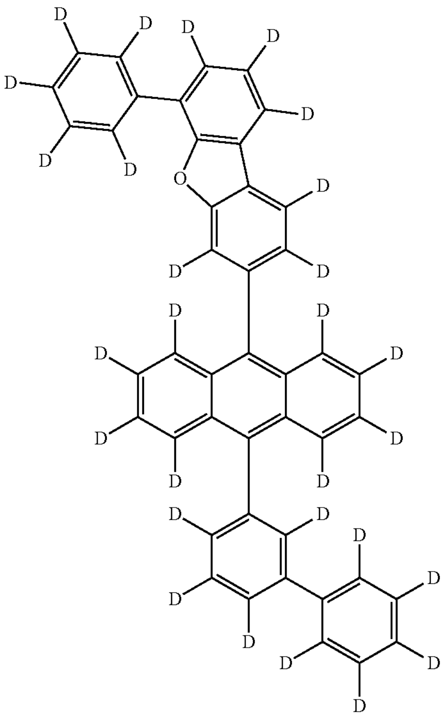
-continued
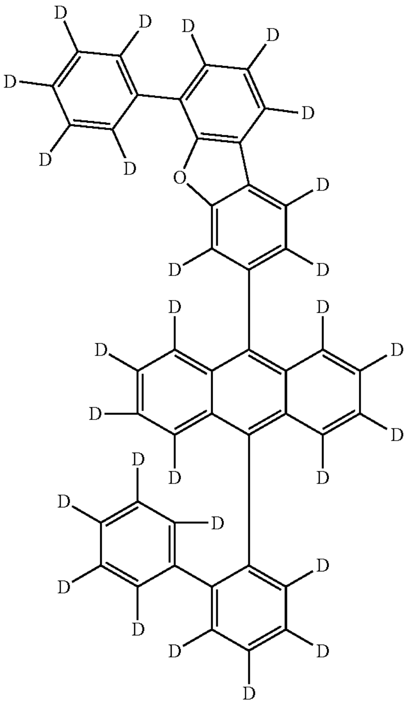 [SMILES: [2H]c1c([2H])c([2H])c(-c2c([2H])c([2H])c([2H])c([2H])c2-c2c3c([2H])c([2H])c([2H])c([2H])c3c(-c3c([2H])c([2H])c4c(oc5c(-c6c([2H])c([2H])c([2H])c([2H])c6[2H])c([2H])c([2H])c([2H])c54)c3[2H])c3c([2H])c([2H])c([2H])c([2H])c23)c([2H])c1[2H]]
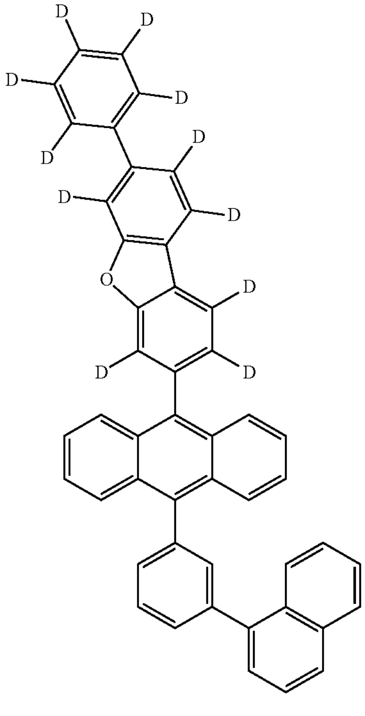

-continued
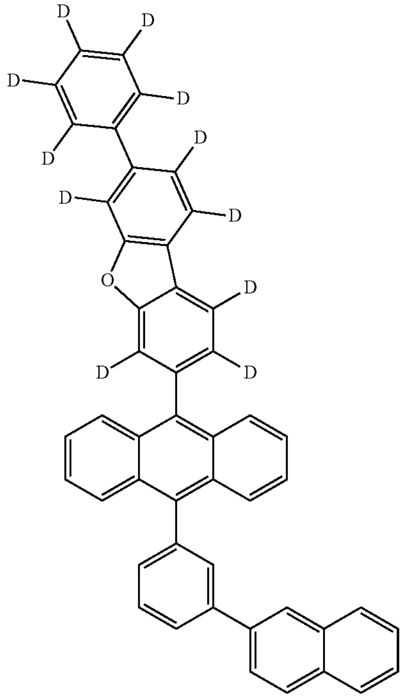
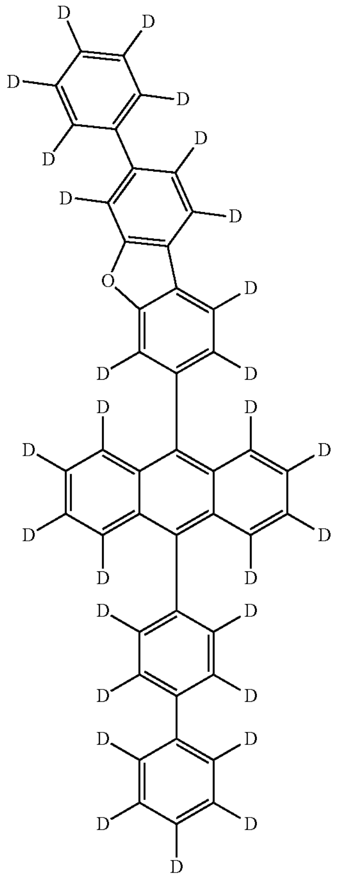
-continued
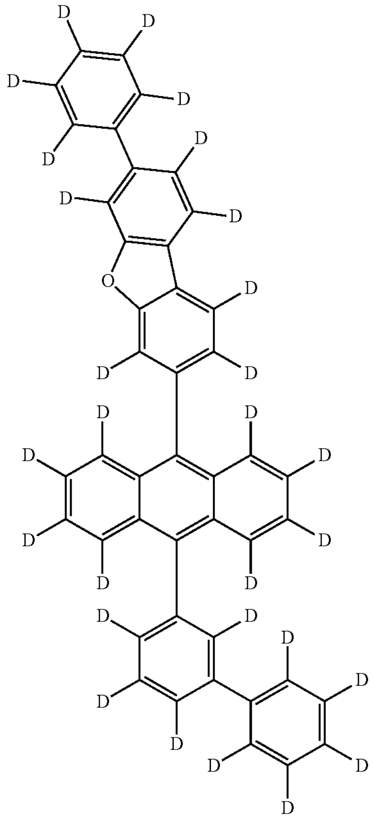
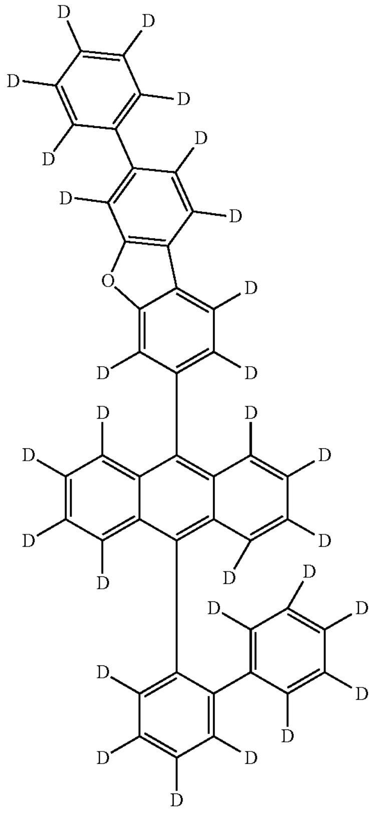 [SMILES: [2H]c1c([2H])c([2H])c(-c2c([2H])c([2H])c([2H])c([2H])c2-c2c3c([2H])c([2H])c([2H])c([2H])c3c(-c3c([2H])c([2H])c4c(oc5c([2H])c(-c6c([2H])c([2H])c([2H])c([2H])c6[2H])c([2H])c([2H])c54)c3[2H])c3c([2H])c([2H])c([2H])c([2H])c23)c([2H])c1[2H]]

-continued
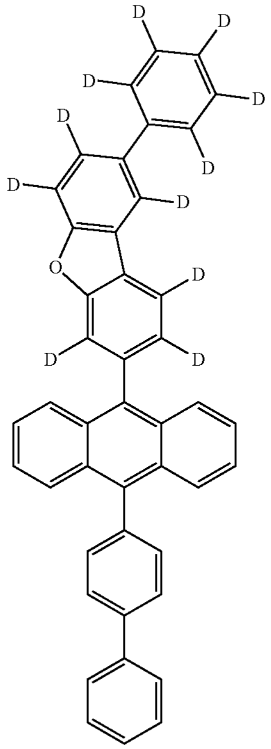
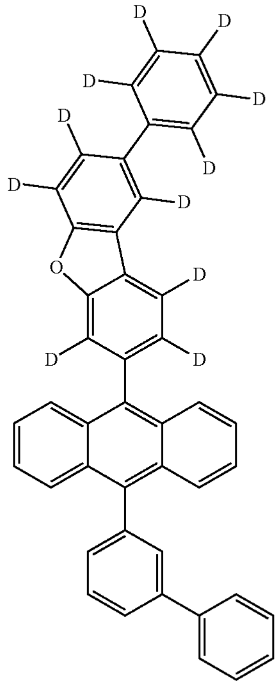
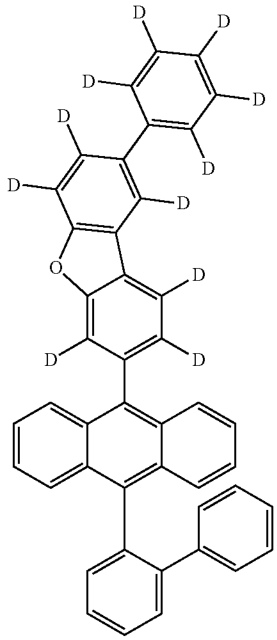
-continued
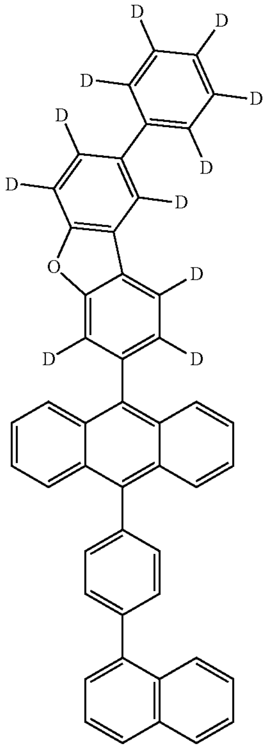
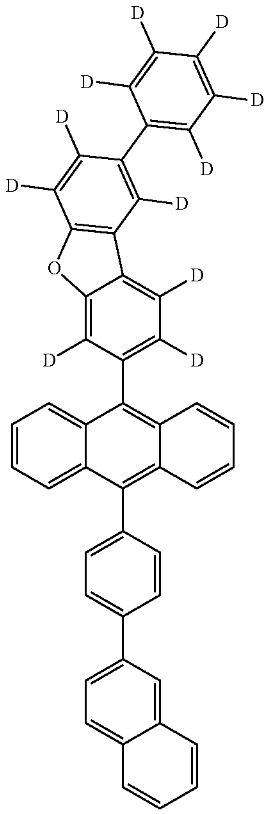
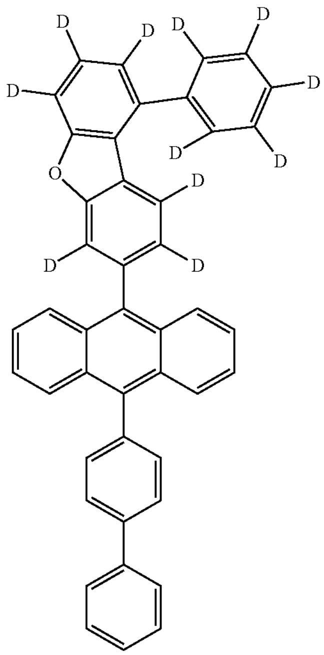

-continued
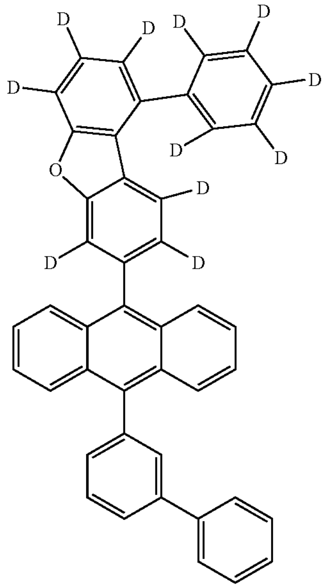
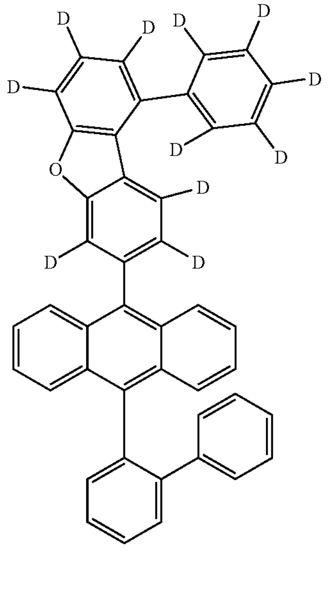
-continued
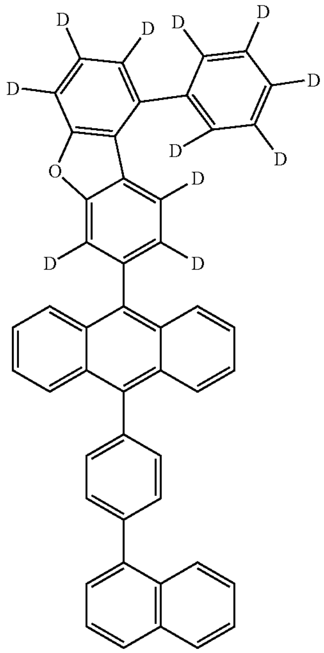
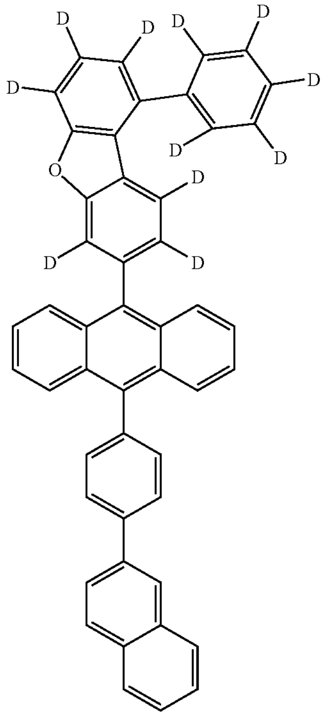

-continued
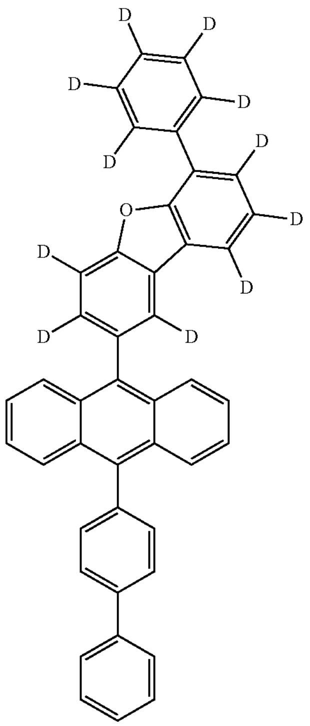
-continued
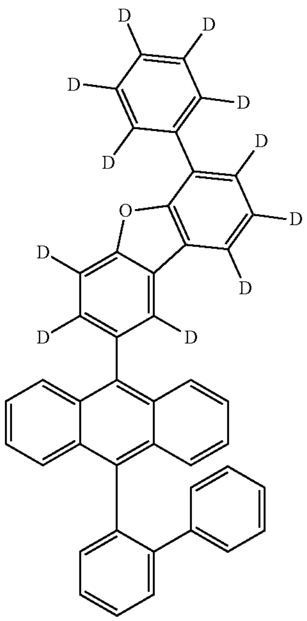
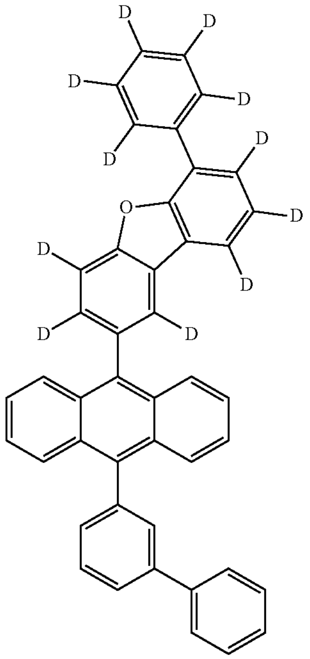
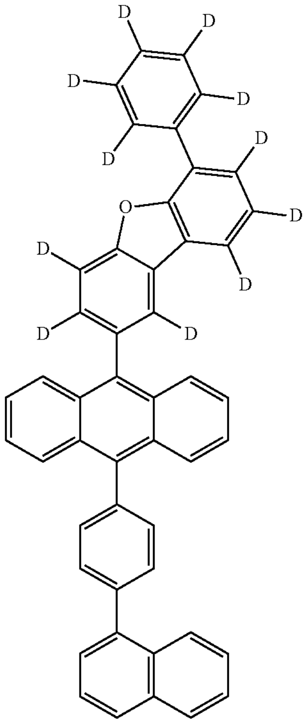

-continued
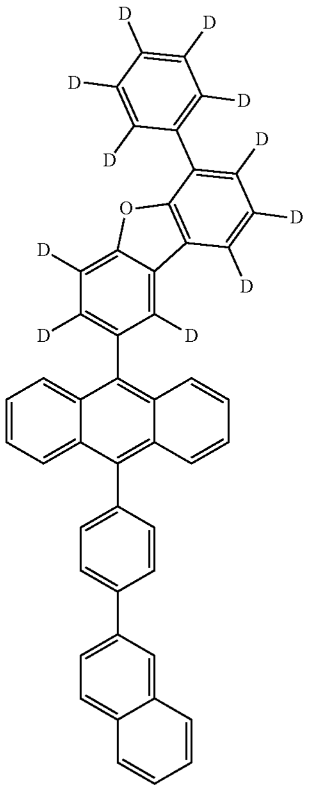
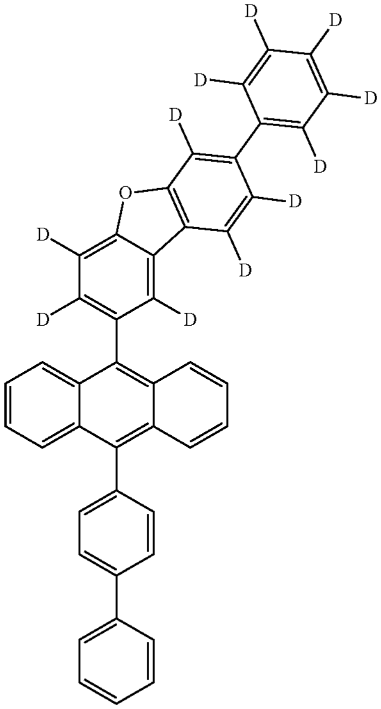
-continued
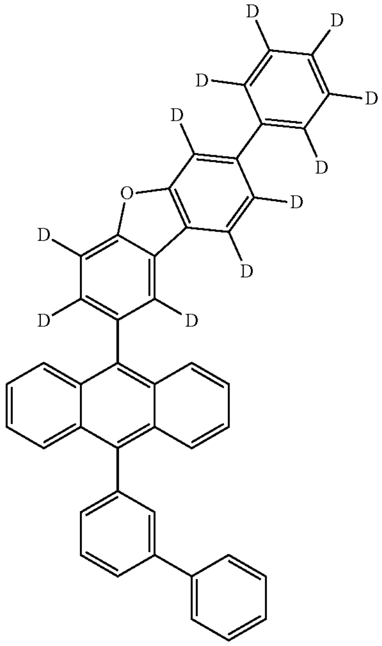
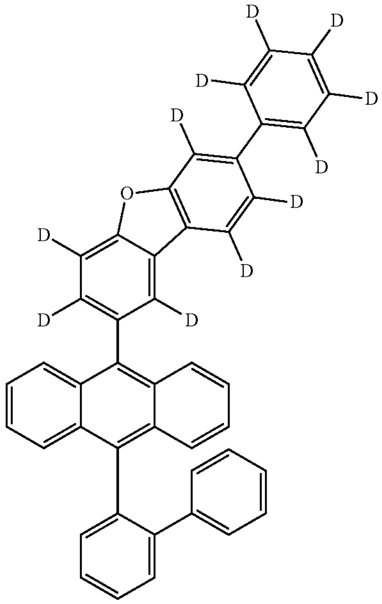

-continued
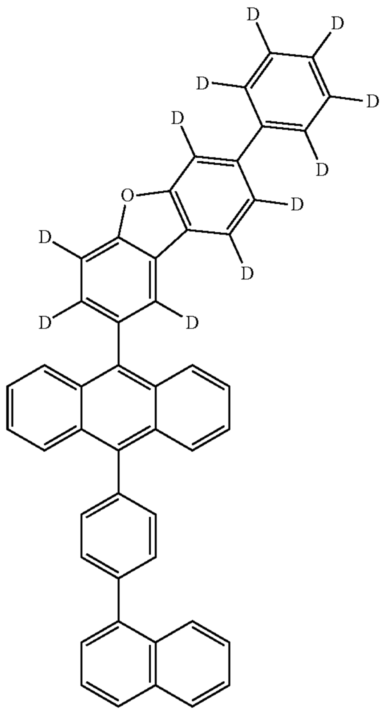
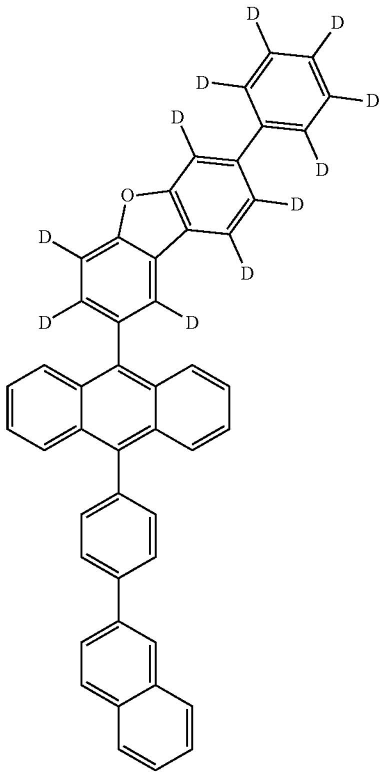
-continued
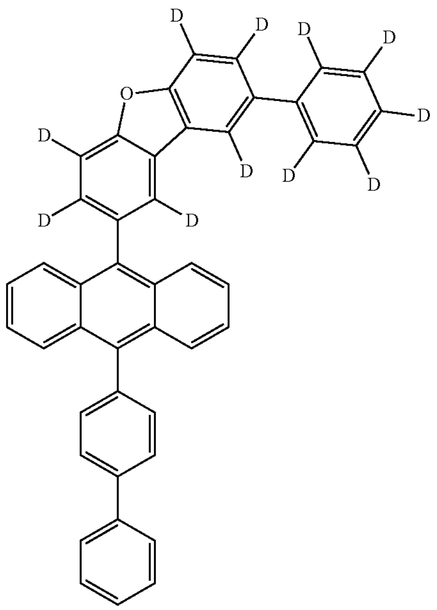
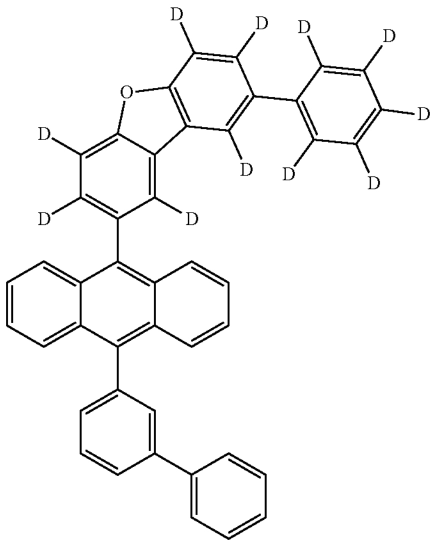
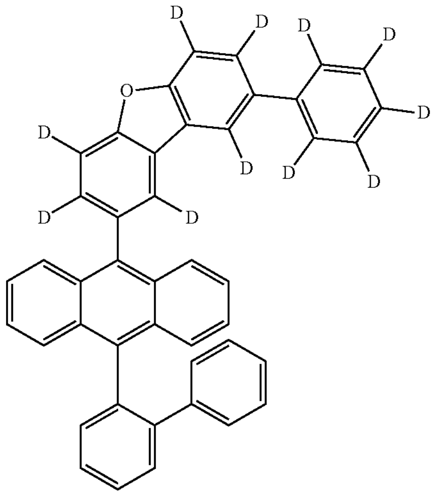

-continued
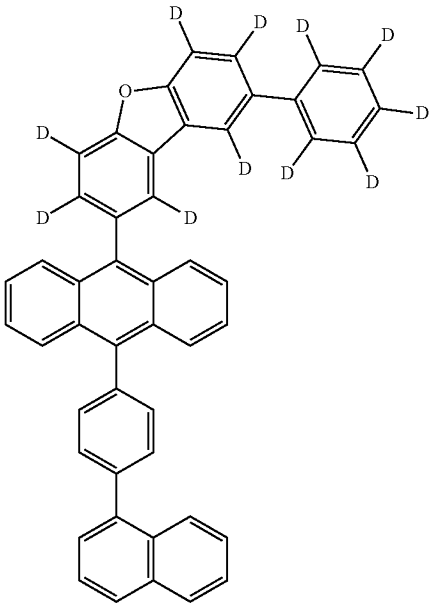
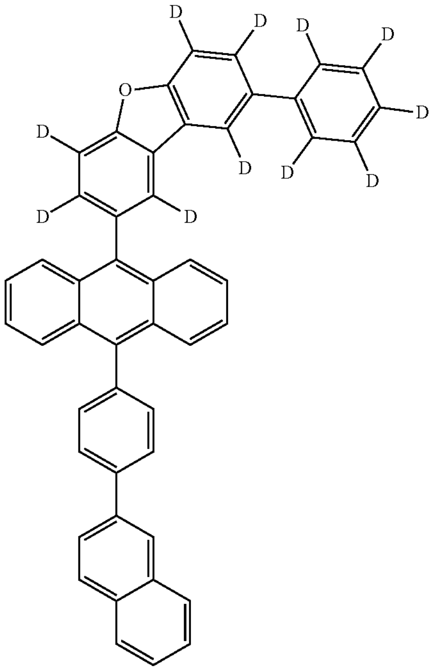
-continued
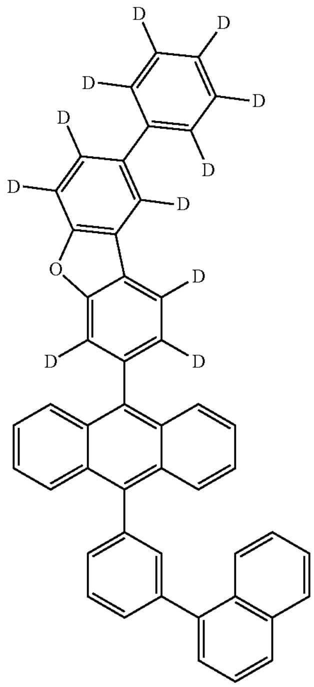
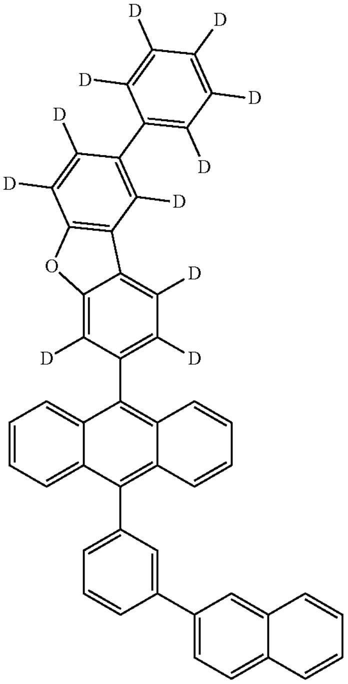

-continued
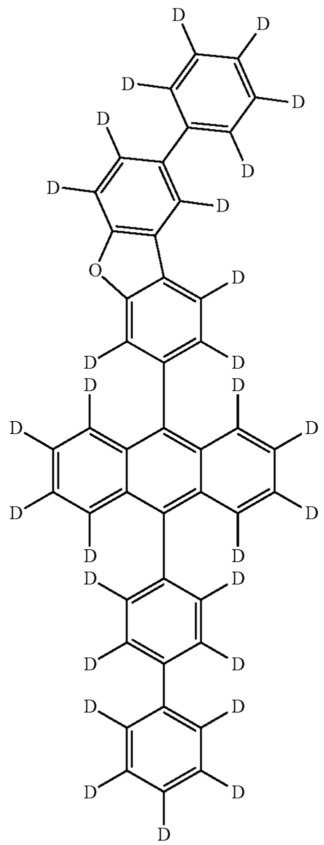
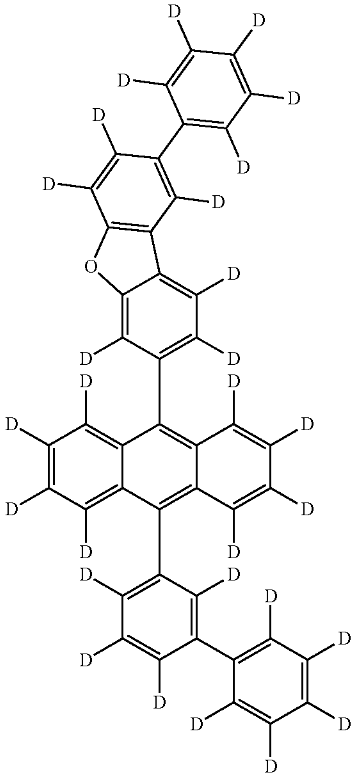
-continued
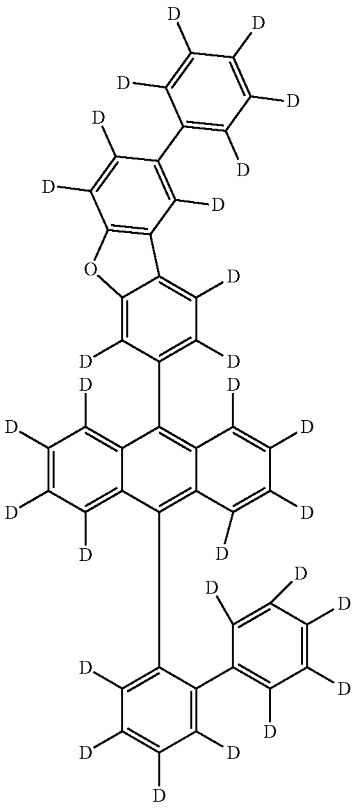 [SMILES: [2H]c1c([2H])c([2H])c(-c2c([2H])c([2H])c([2H])c([2H])c2-c2c3c([2H])c([2H])c([2H])c([2H])c3c(-c3c([2H])c([2H])c4c(oc5c([2H])c([2H])c(-c6c([2H])c([2H])c([2H])c([2H])c6[2H])c([2H])c54)c3[2H])c3c([2H])c([2H])c([2H])c([2H])c23)c([2H])c1[2H]]
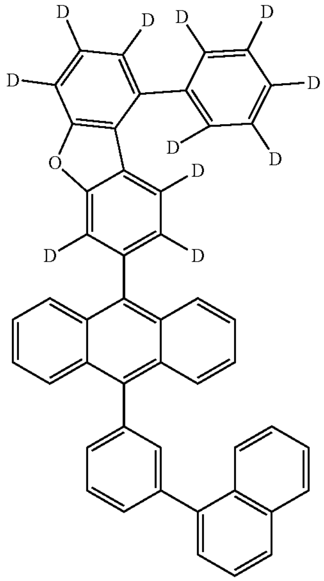

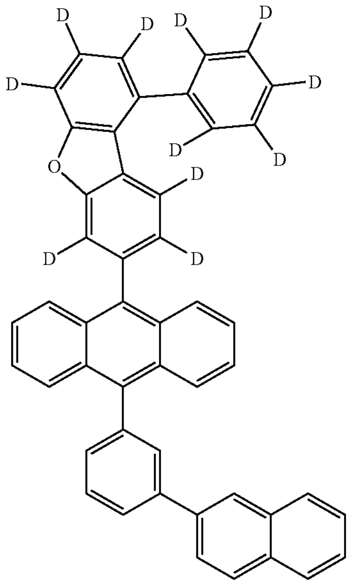
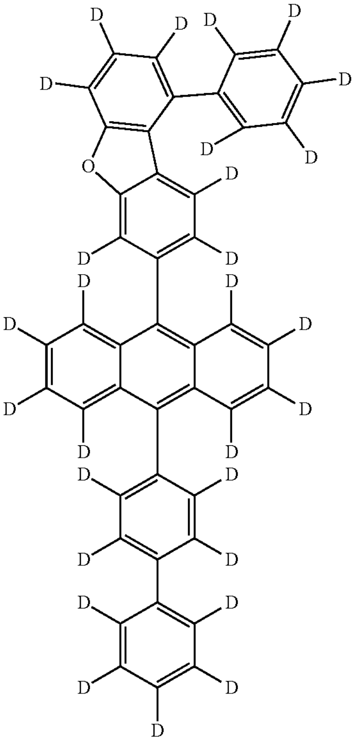
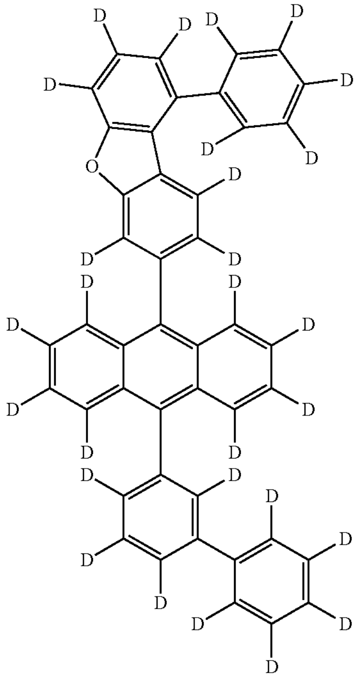
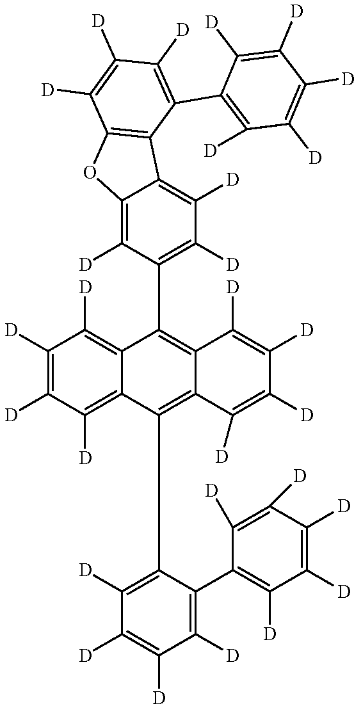 [SMILES: [2H]c1c([2H])c([2H])c(-c2c([2H])c([2H])c([2H])c([2H])c2-c2c3c([2H])c([2H])c([2H])c([2H])c3c(-c3c([2H])c([2H])c4c(oc5c([2H])c([2H])c([2H])c(-c6c([2H])c([2H])c([2H])c([2H])c6[2H])c54)c3[2H])c3c([2H])c([2H])c([2H])c([2H])c23)c([2H])c1[2H]]

-continued
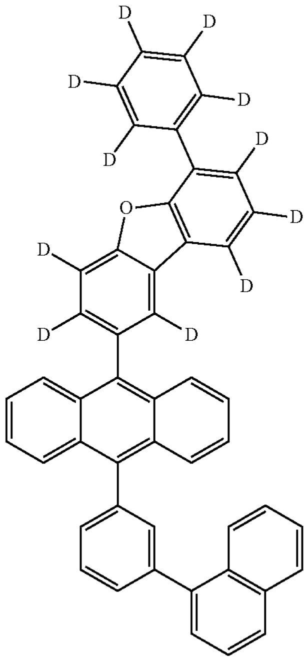
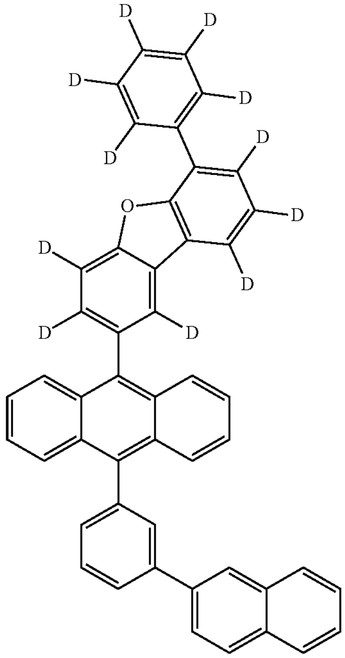
-continued
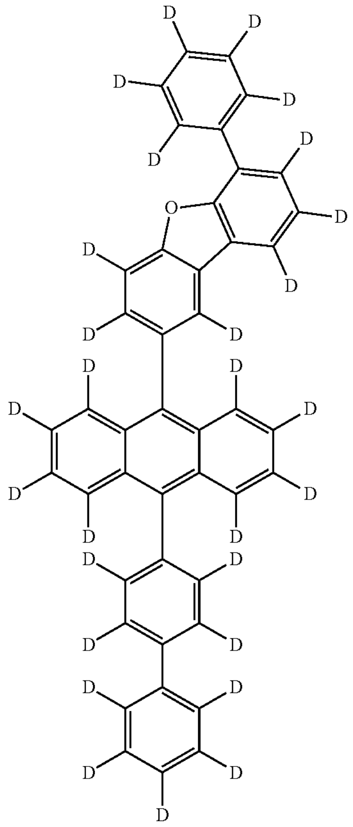
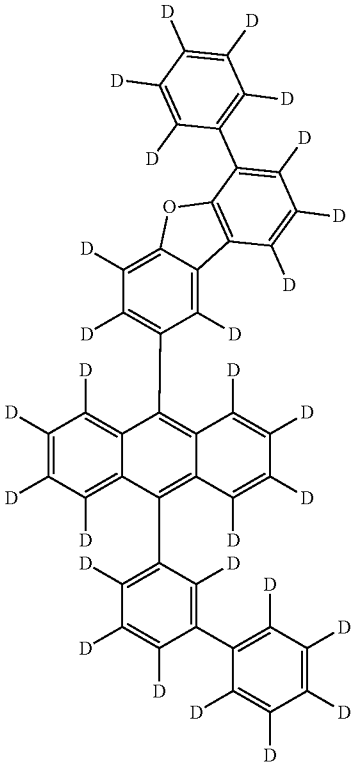

-continued
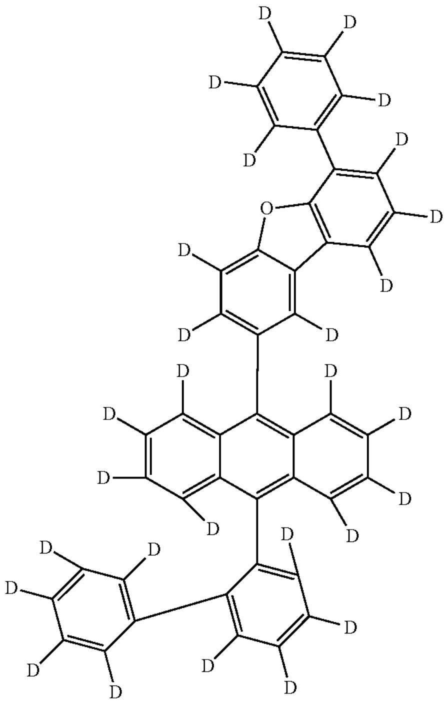 [SMILES: [2H]c1c([2H])c([2H])c(-c2c([2H])c([2H])c([2H])c([2H])c2-c2c3c([2H])c([2H])c([2H])c([2H])c3c(-c3c([2H])c([2H])c4oc5c(-c6c([2H])c([2H])c([2H])c([2H])c6[2H])c([2H])c([2H])c([2H])c5c4c3[2H])c3c([2H])c([2H])c([2H])c([2H])c23)c([2H])c1[2H]]
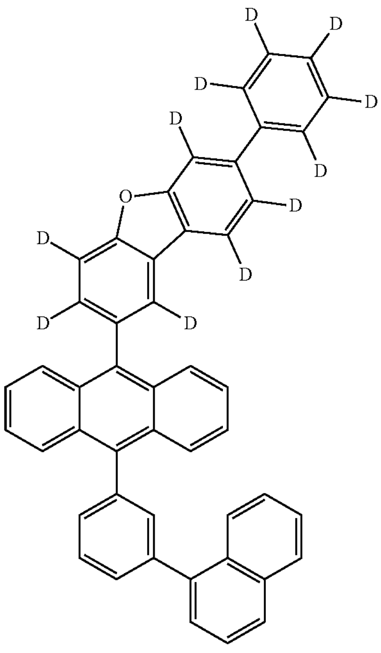
-continued
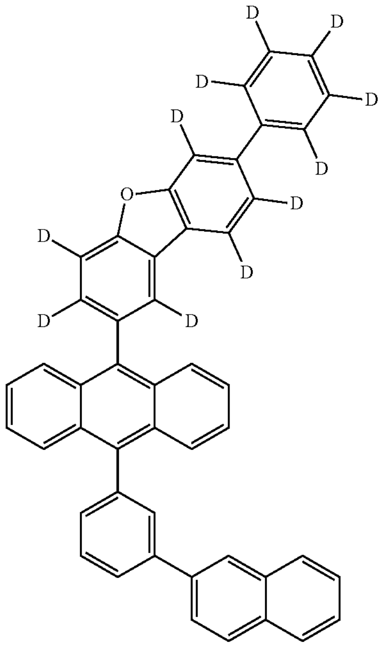
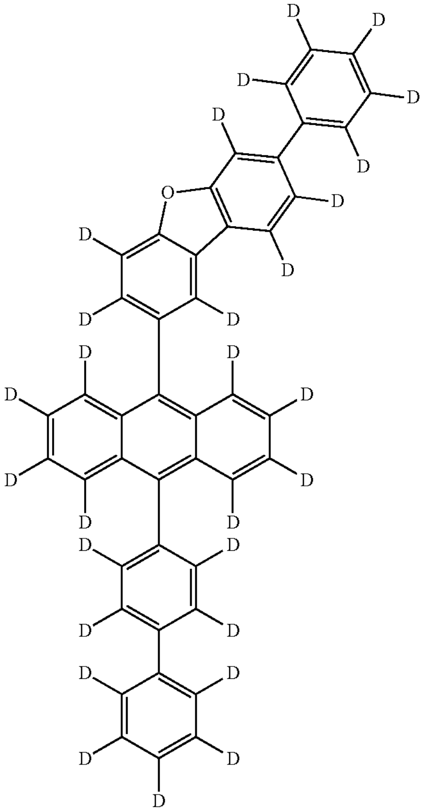

-continued
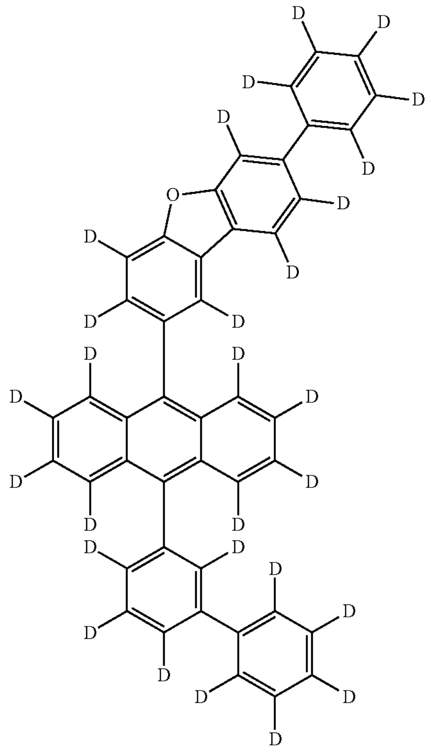
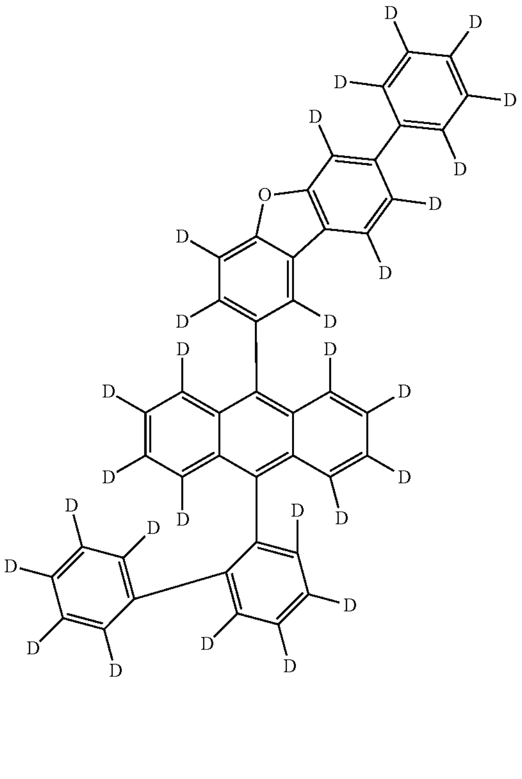 [SMILES: [2H]c1c([2H])c([2H])c(-c2c([2H])c([2H])c([2H])c([2H])c2-c2c3c([2H])c([2H])c([2H])c([2H])c3c(-c3c([2H])c([2H])c4oc5c([2H])c(-c6c([2H])c([2H])c([2H])c([2H])c6[2H])c([2H])c([2H])c5c4c3[2H])c3c([2H])c([2H])c([2H])c([2H])c23)c([2H])c1[2H]]
-continued
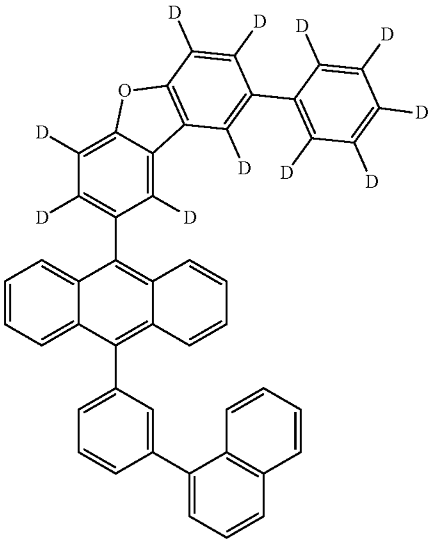
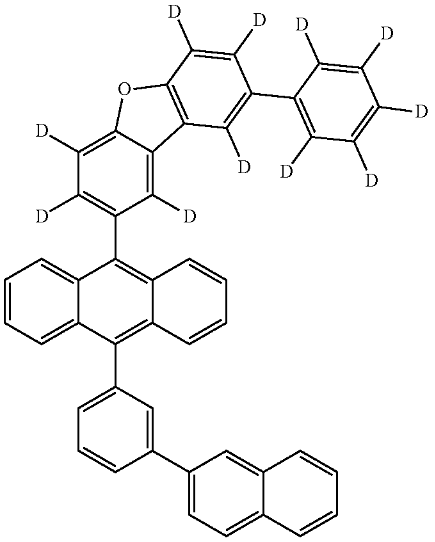

-continued
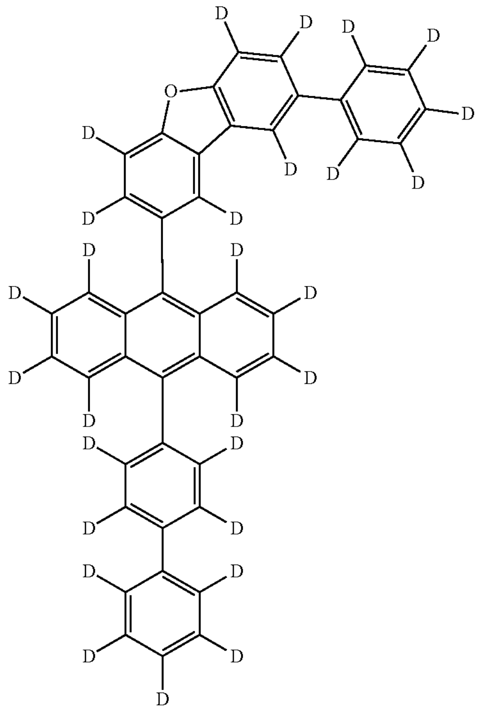
-continued
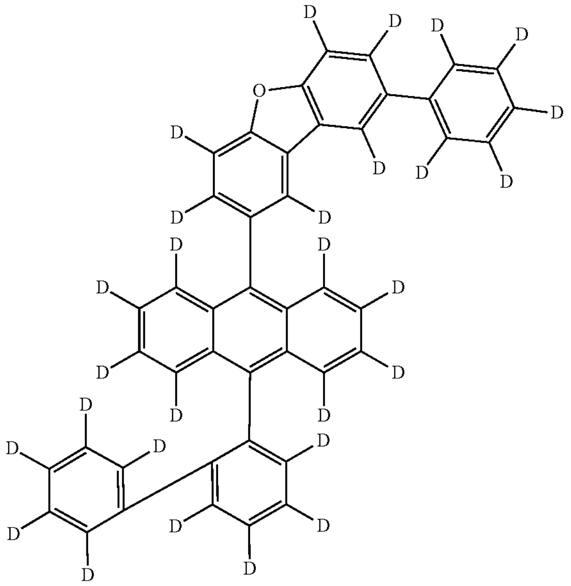 [SMILES: [2H]c1c([2H])c([2H])c(-c2c([2H])c([2H])c([2H])c([2H])c2-c2c3c([2H])c([2H])c([2H])c([2H])c3c(-c3c([2H])c([2H])c4oc5c([2H])c([2H])c(-c6c([2H])c([2H])c([2H])c([2H])c6[2H])c([2H])c5c4c3[2H])c3c([2H])c([2H])c([2H])c([2H])c23)c([2H])c1[2H]]
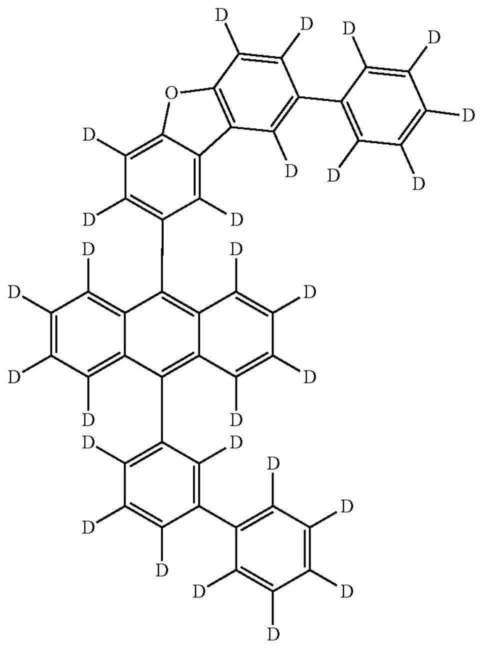
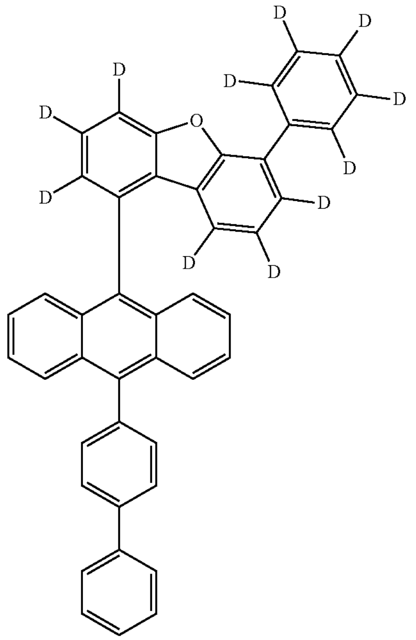

-continued
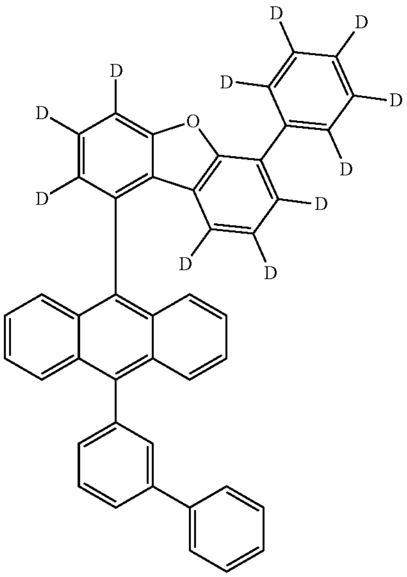
-continued
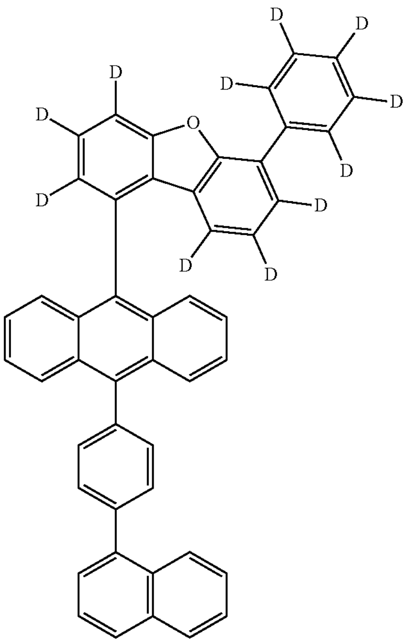
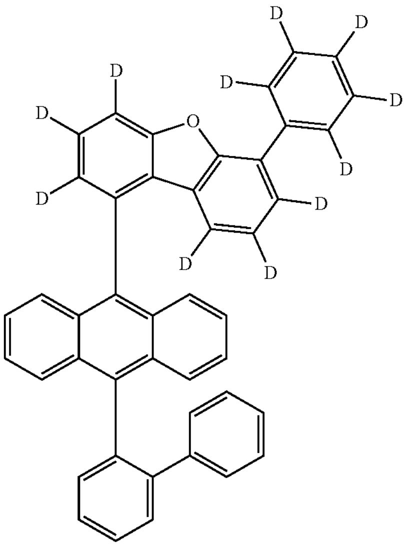
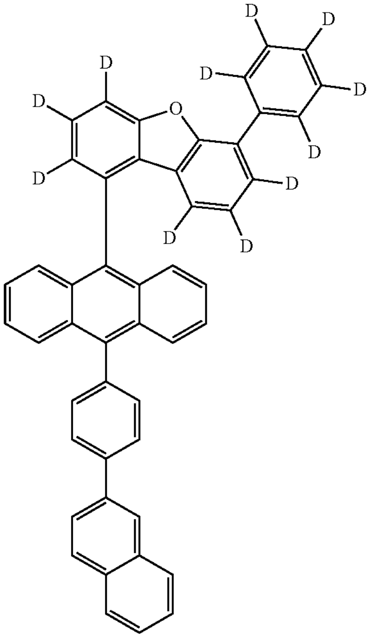

-continued
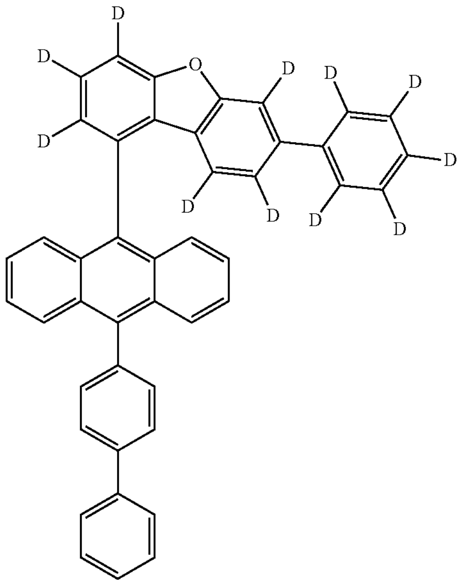
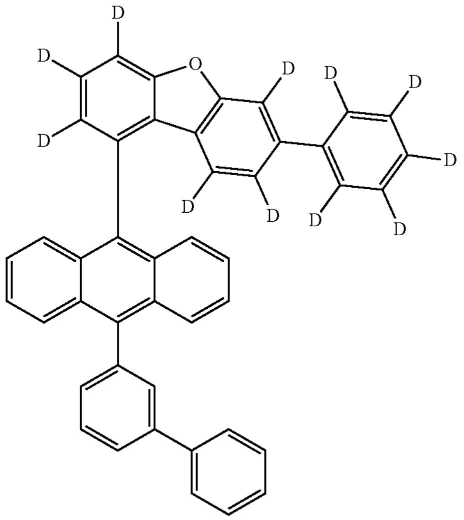
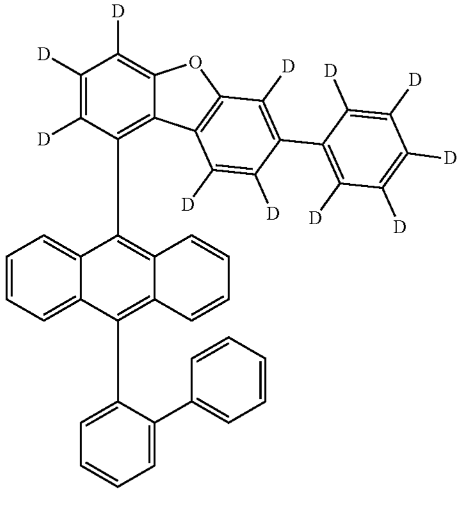
-continued
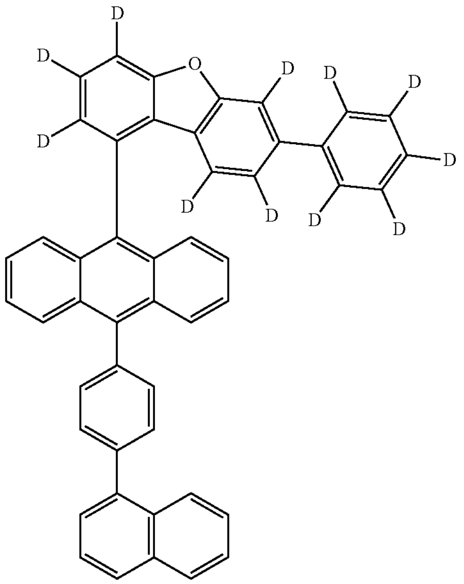
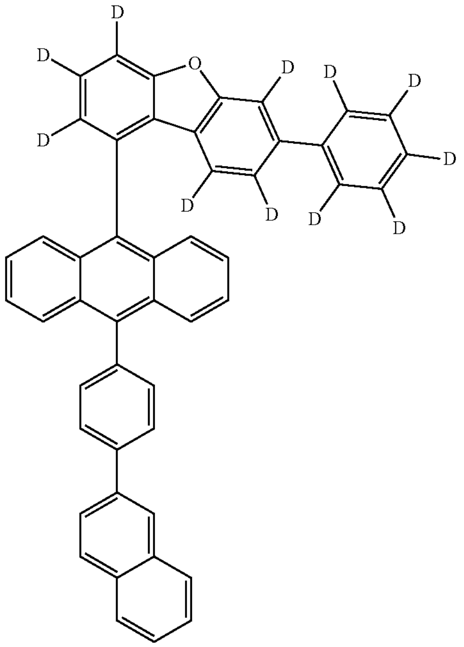

-continued
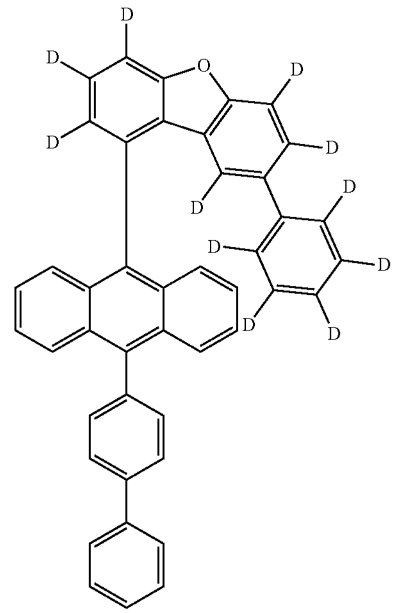
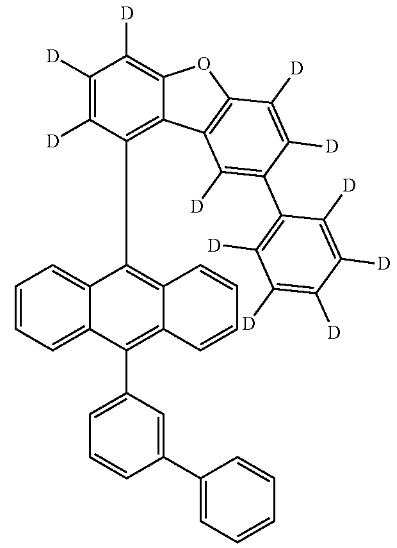
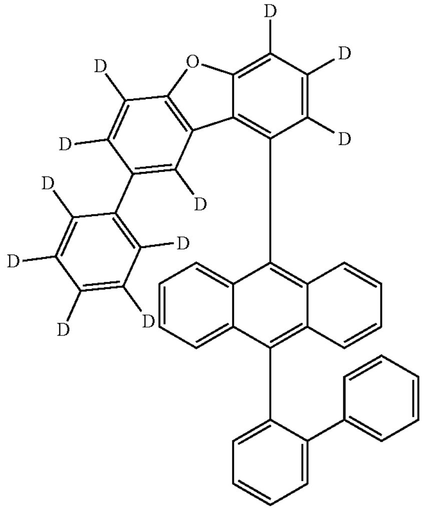
-continued
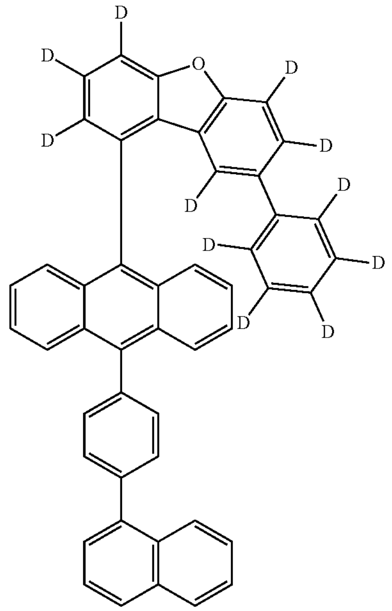
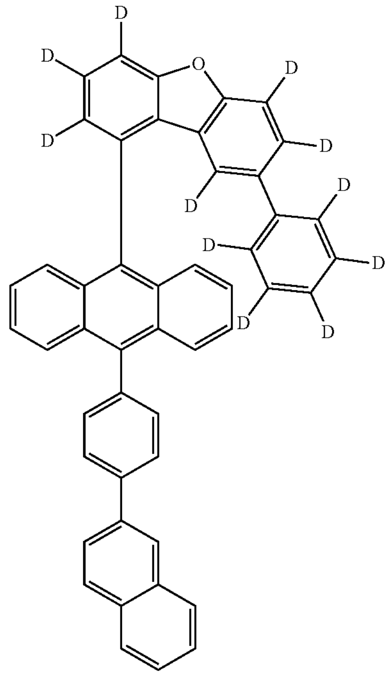

-continued
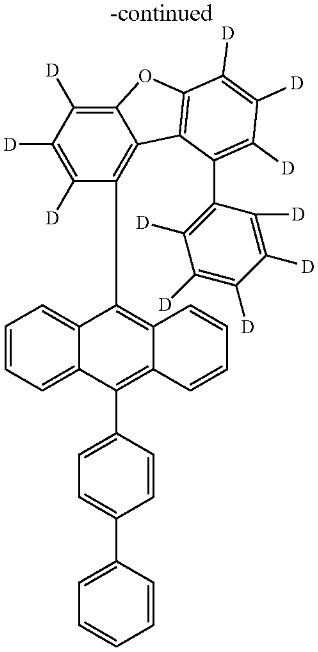
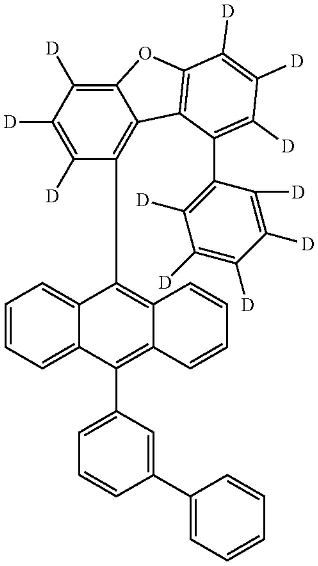
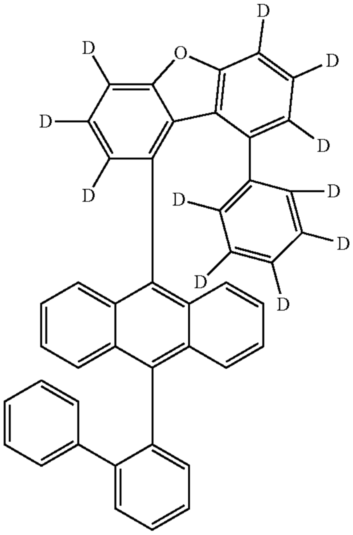
-continued
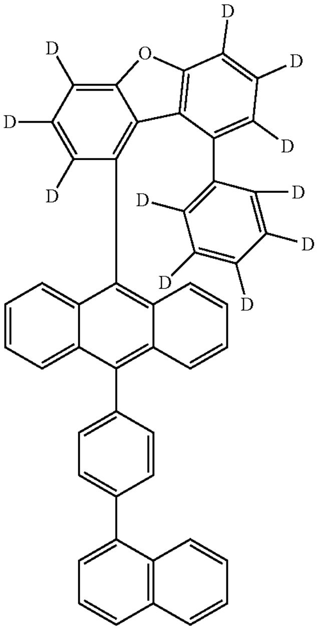
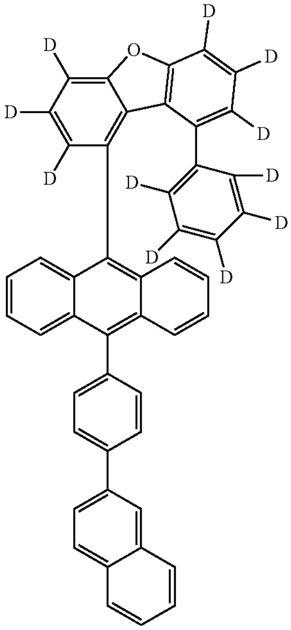

-continued
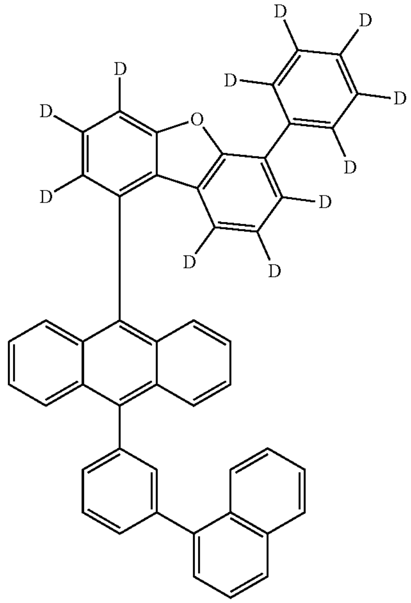
-continued
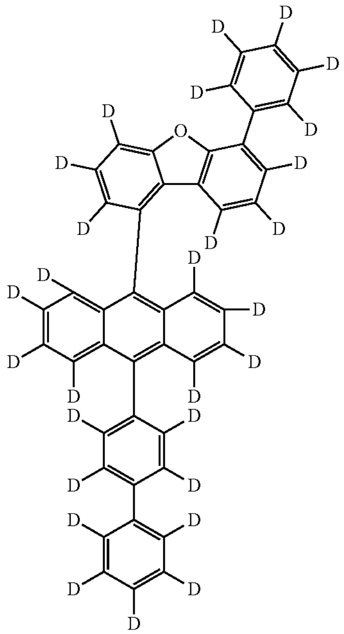
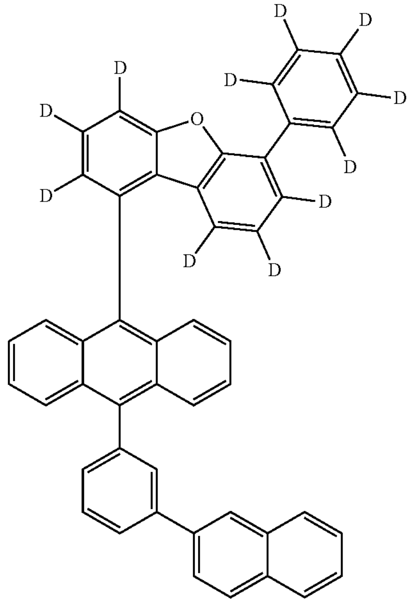
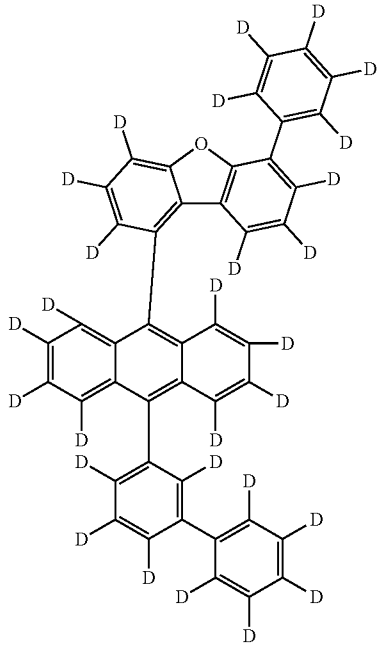

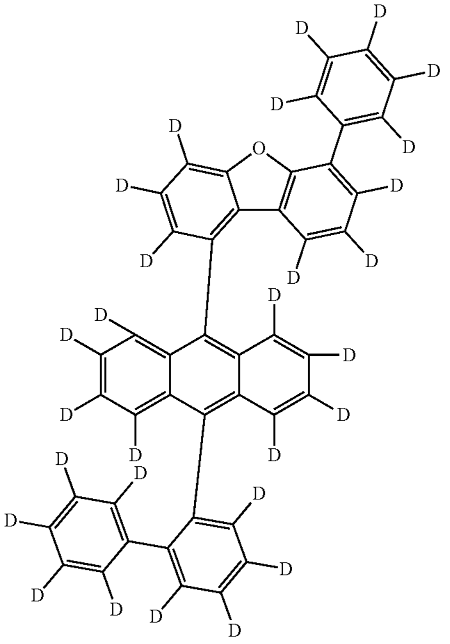
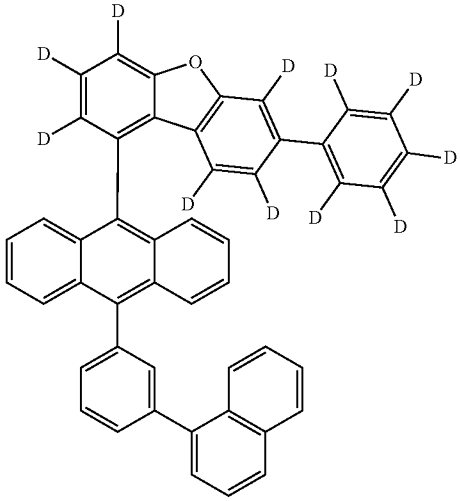
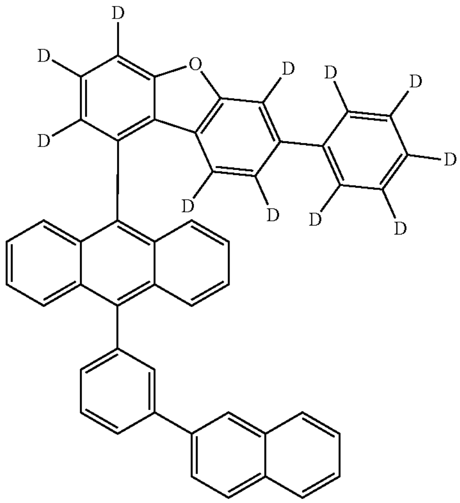
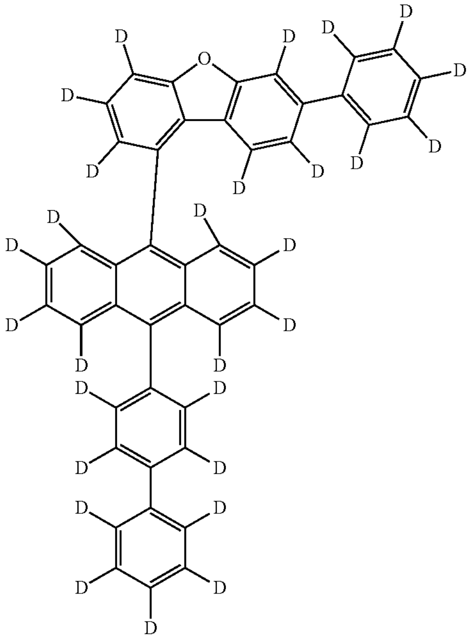
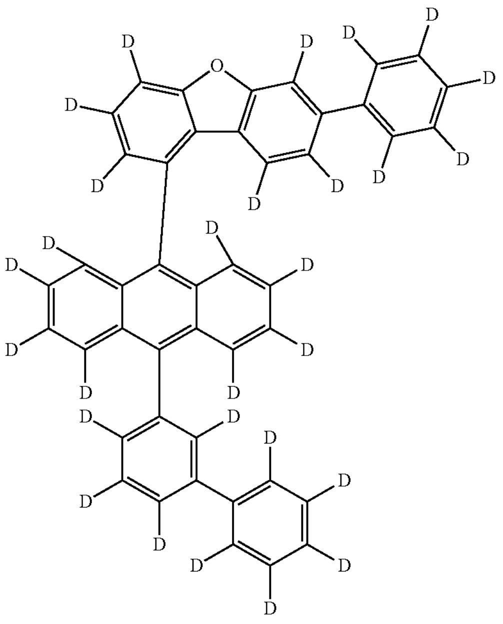

-continued
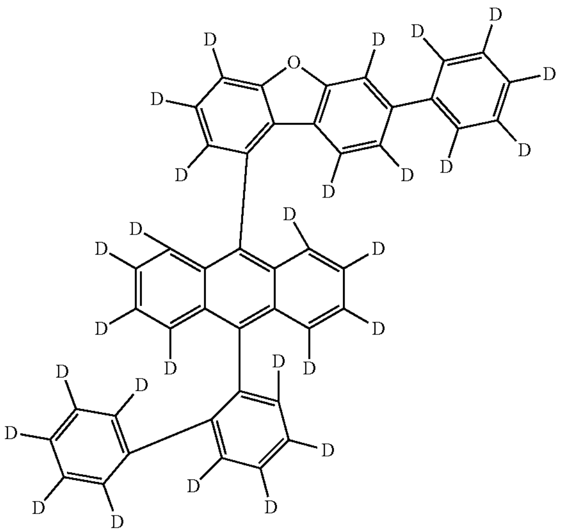
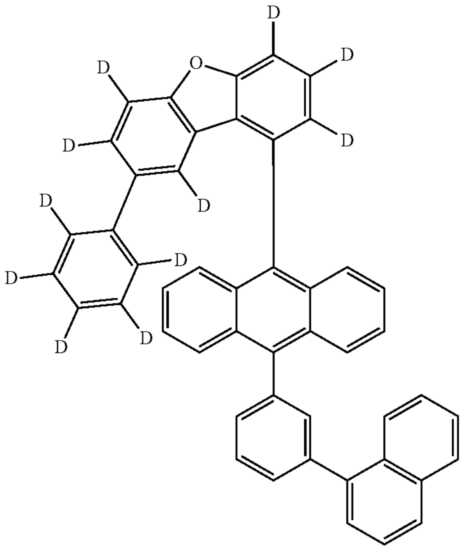
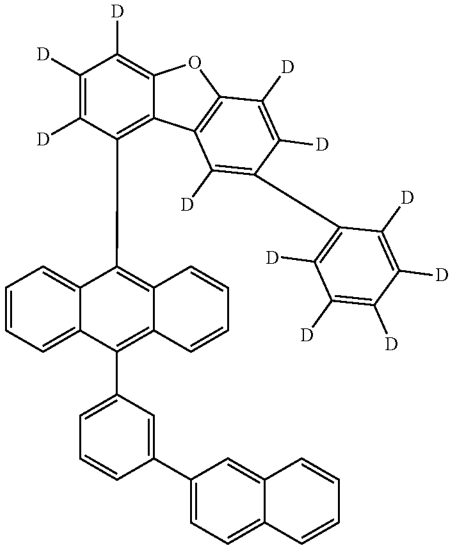
-continued
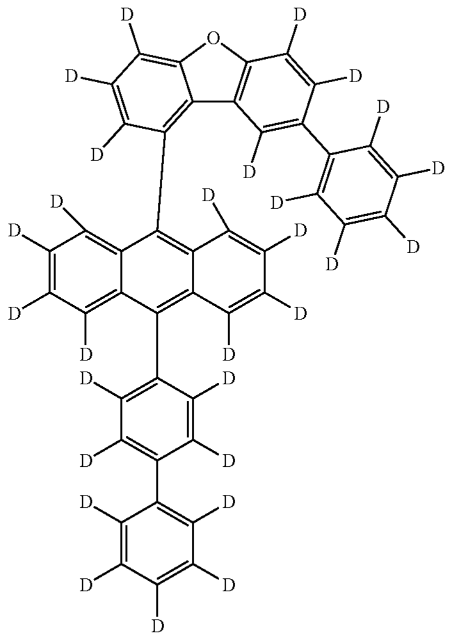
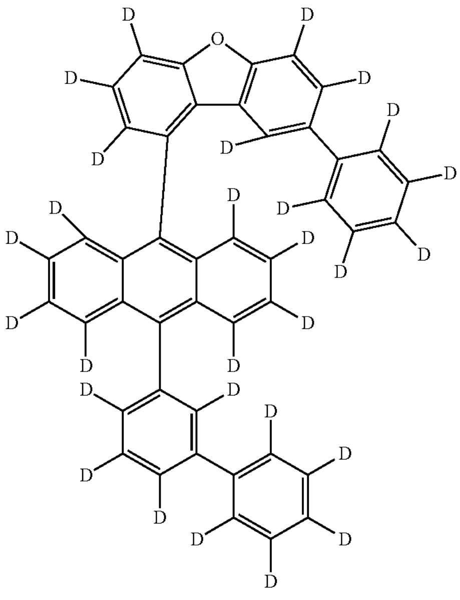

-continued
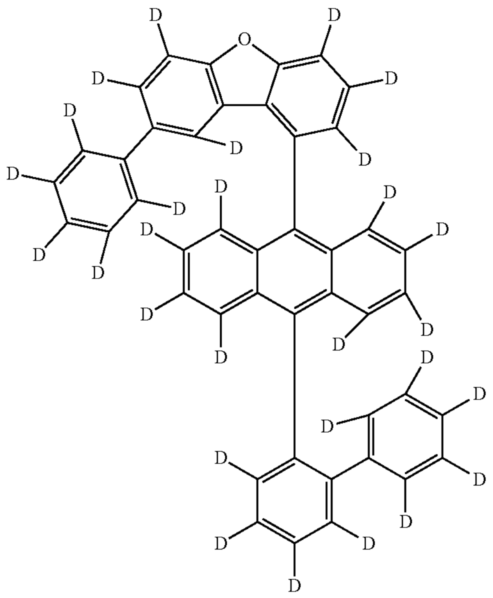
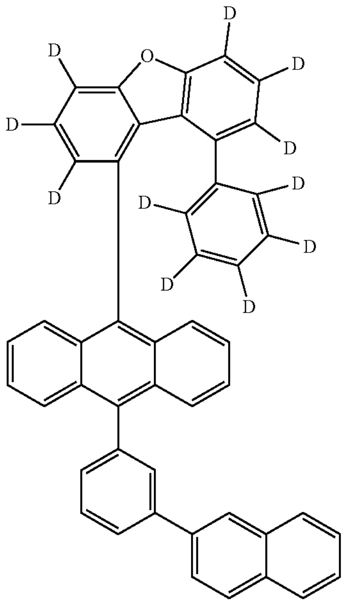
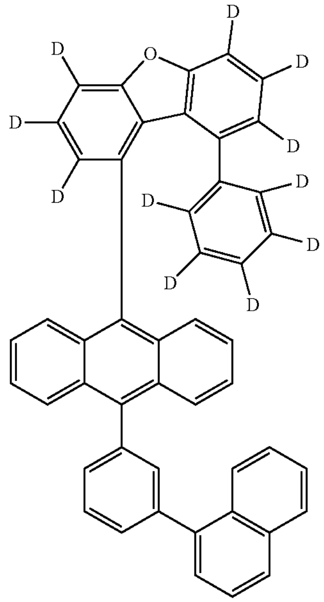
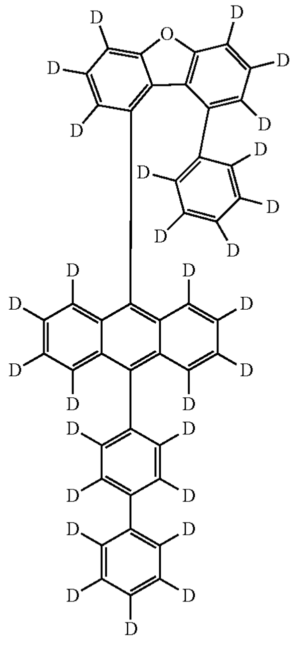

-continued
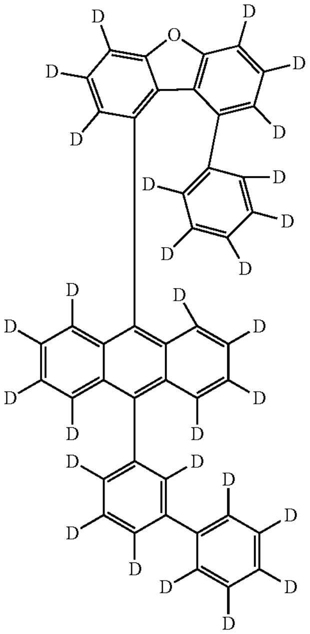
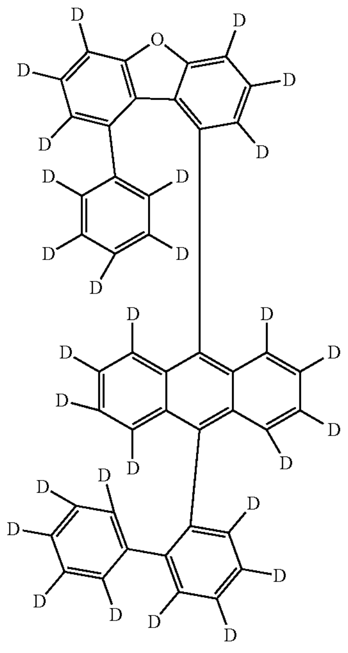
-continued
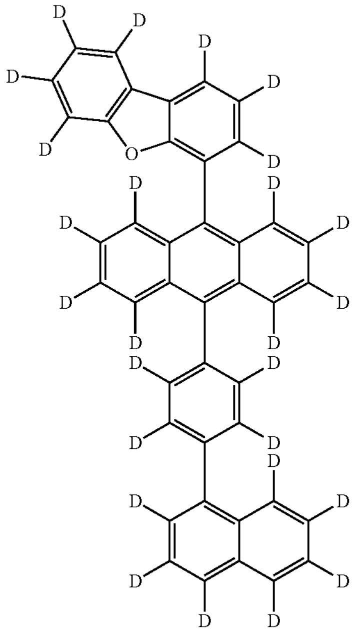
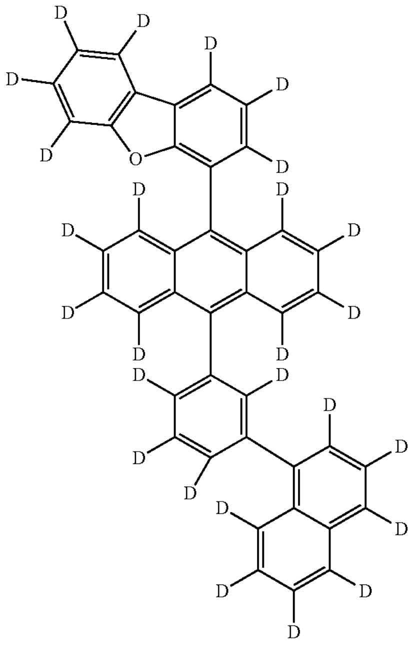

-continued
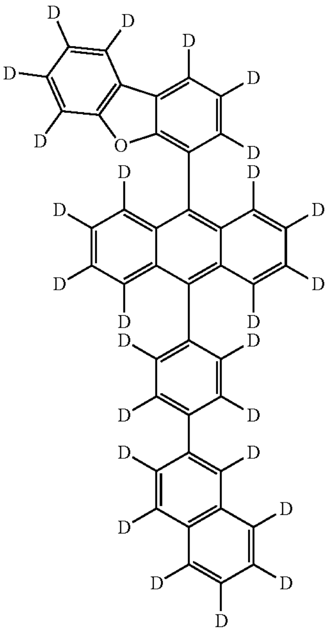
-continued
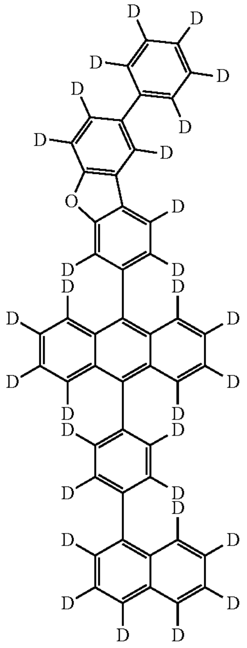
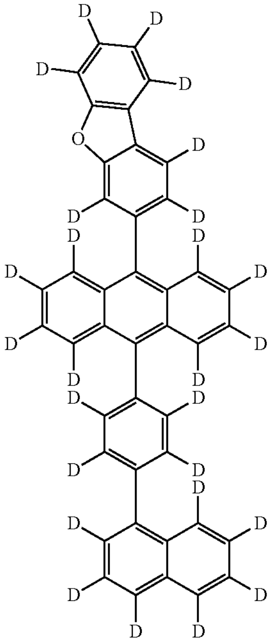
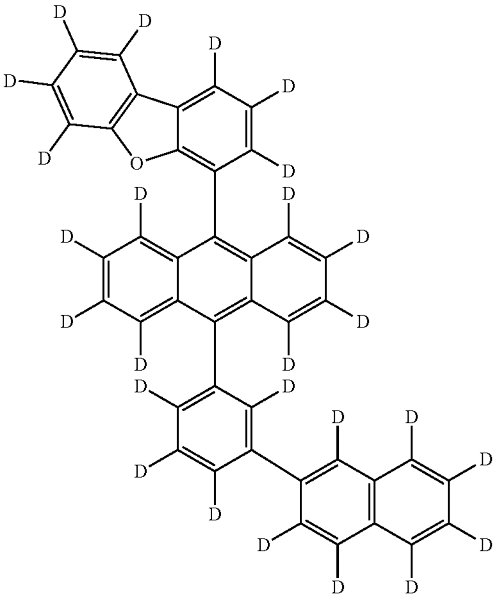
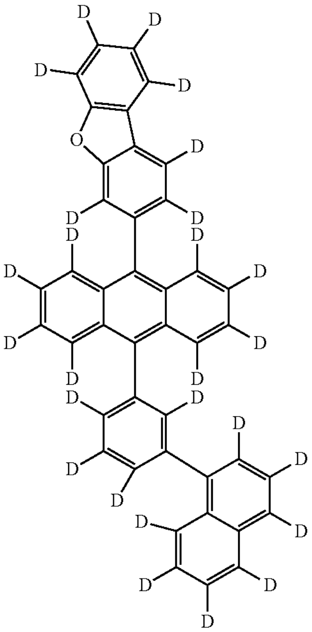

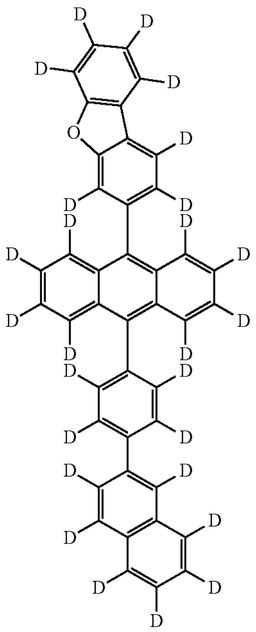
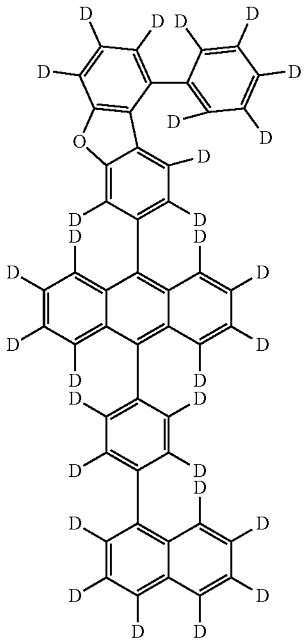
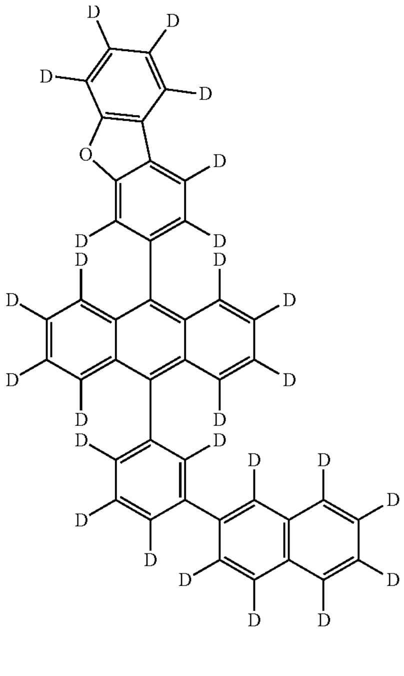
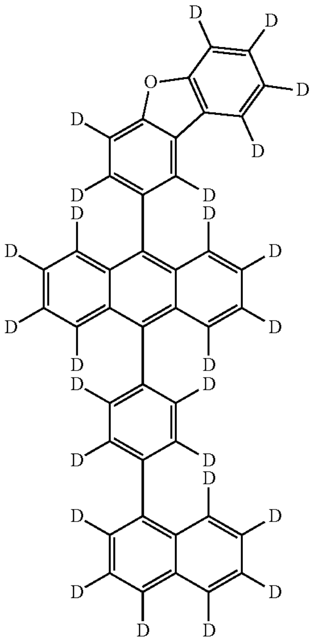

-continued
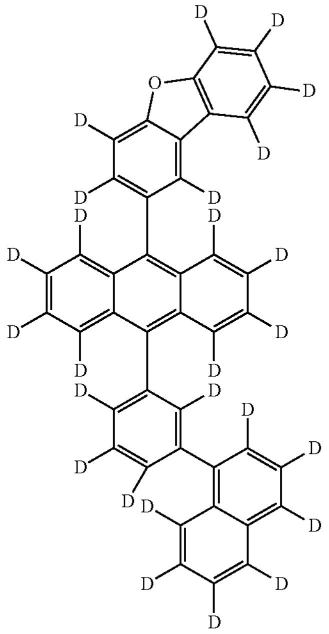
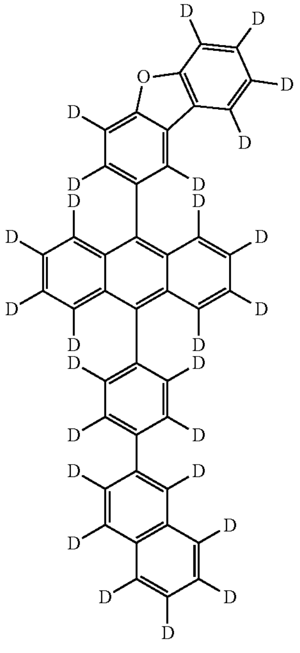
-continued
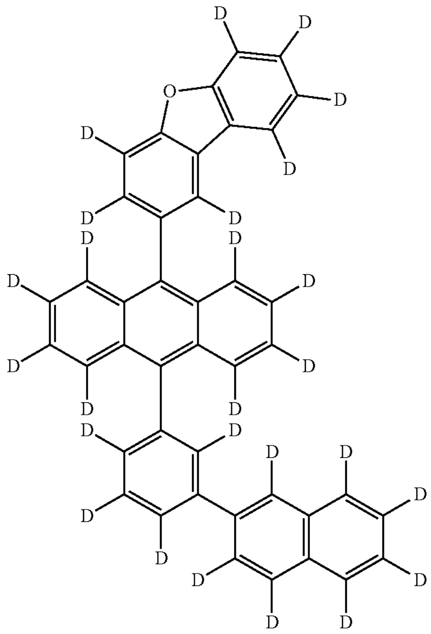
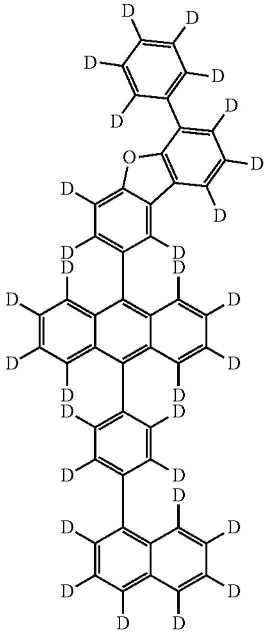

-continued
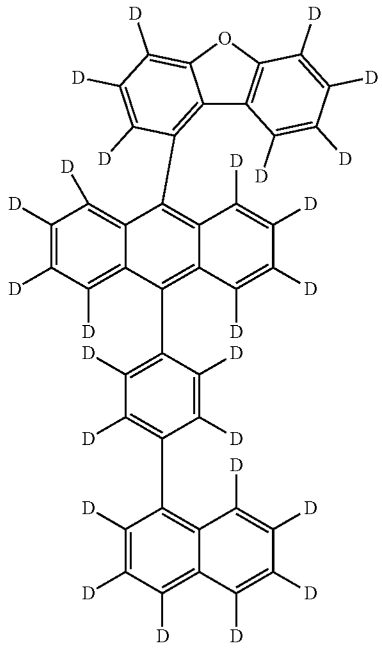
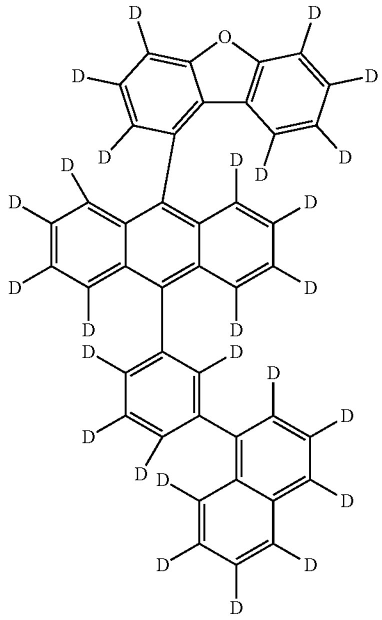
-continued
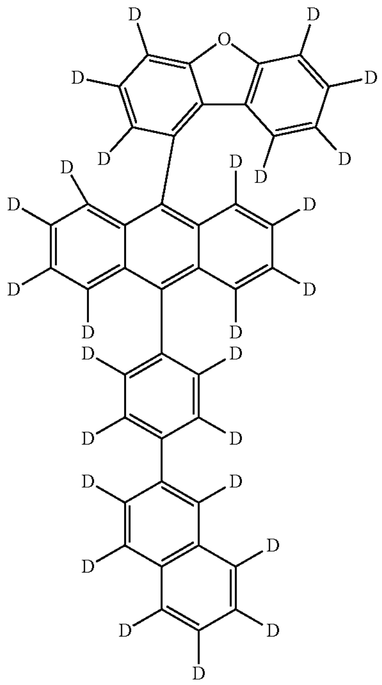
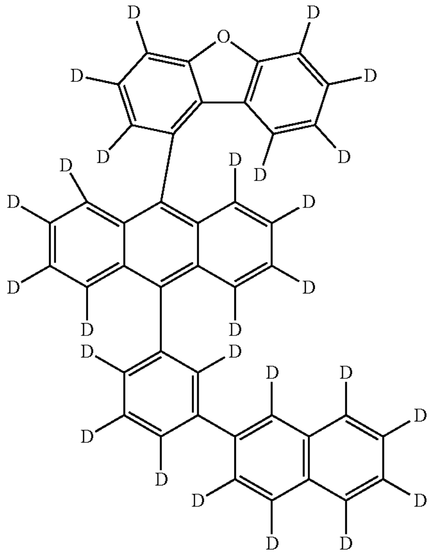

-continued
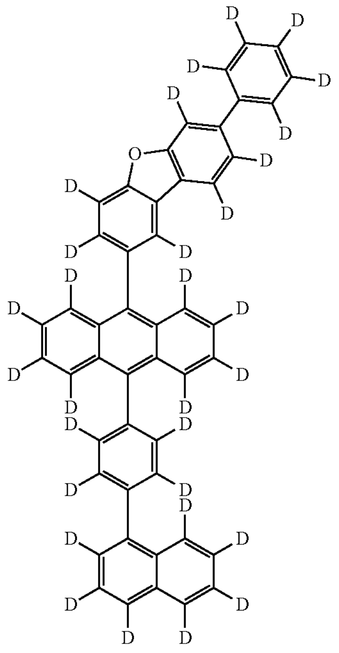
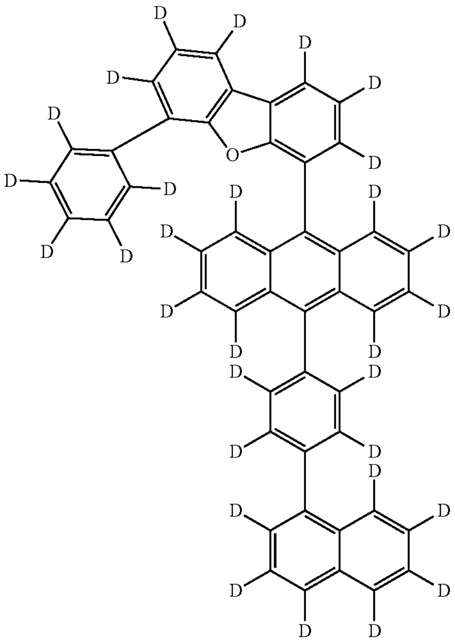
-continued
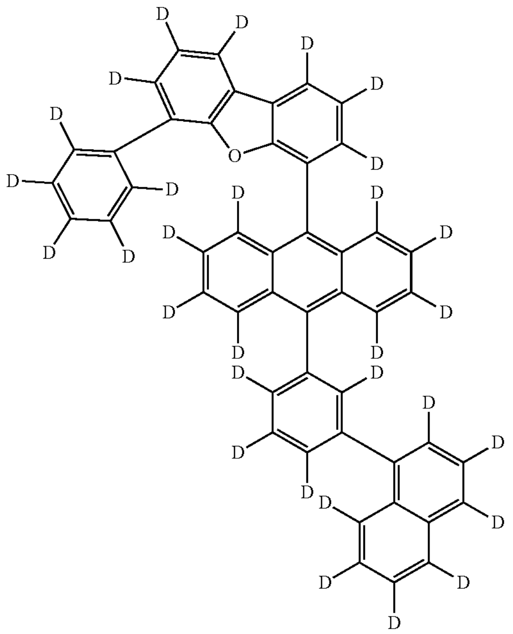
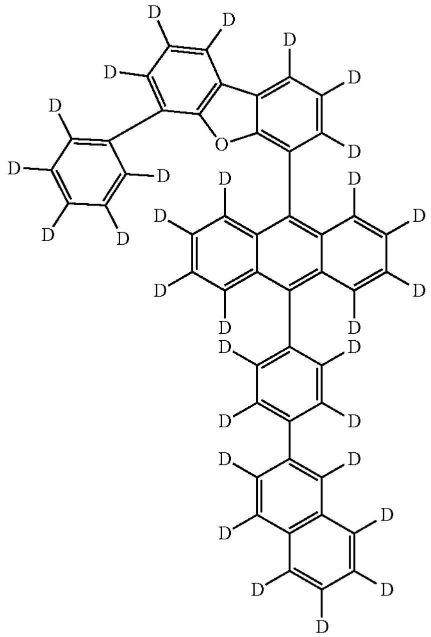

-continued
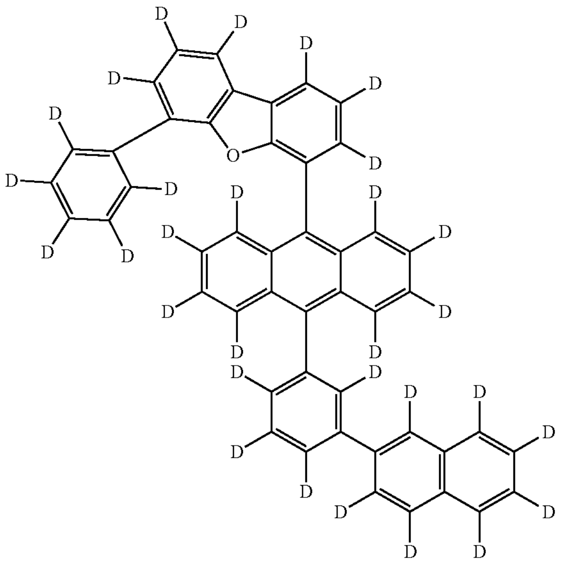
-continued
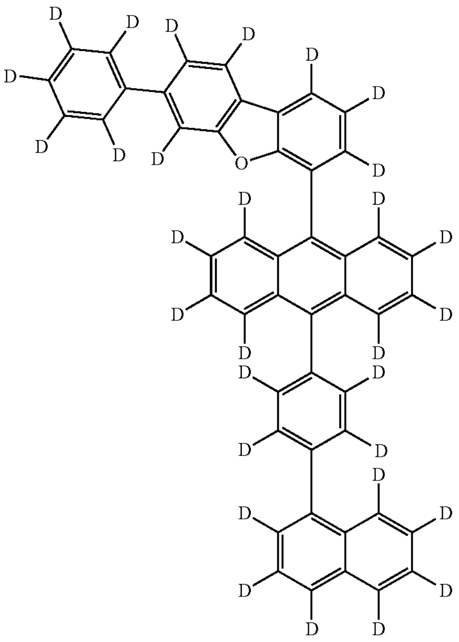
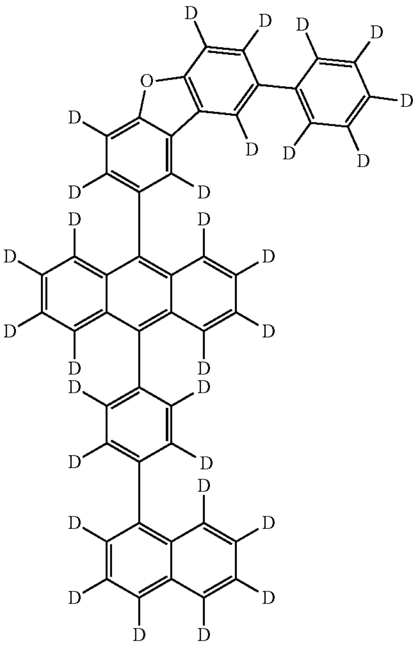
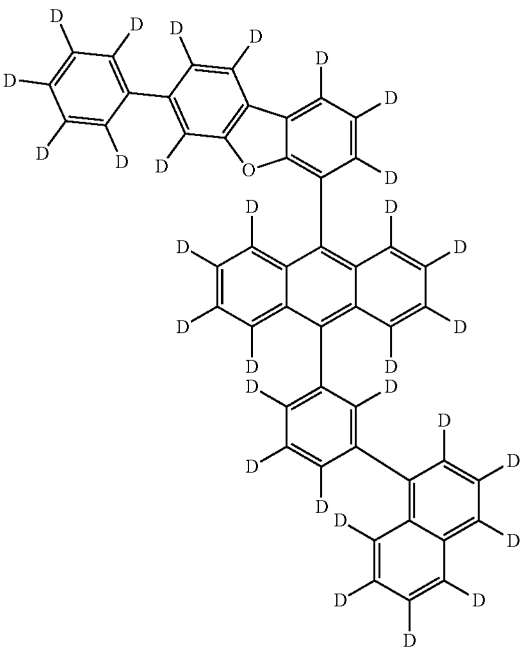

-continued
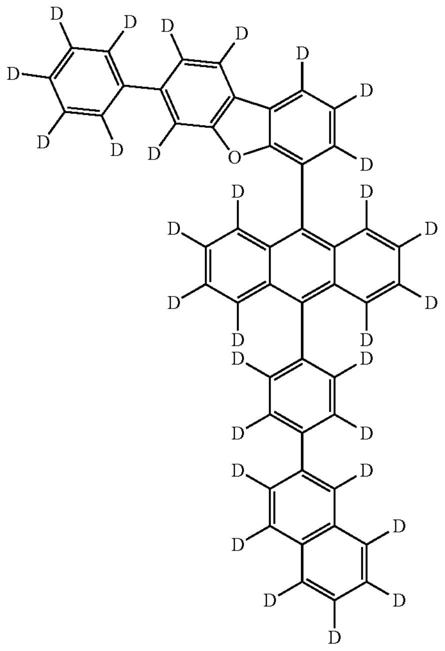
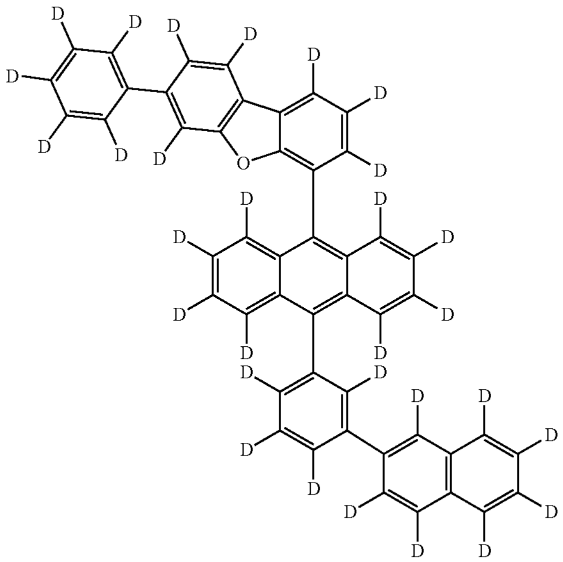
-continued
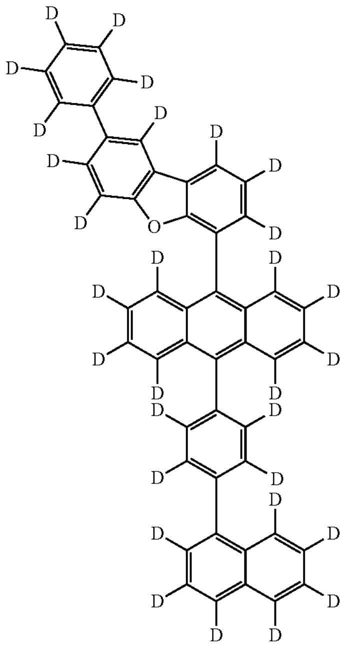
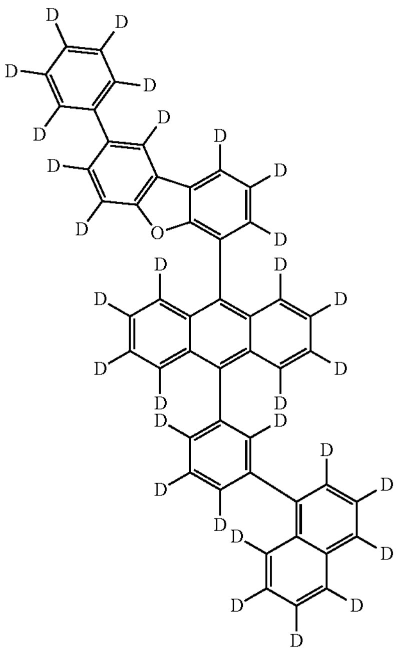

-continued
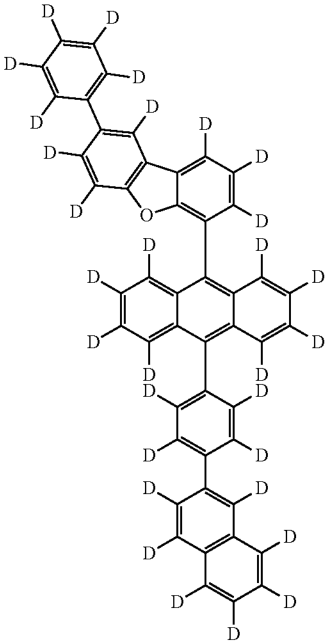
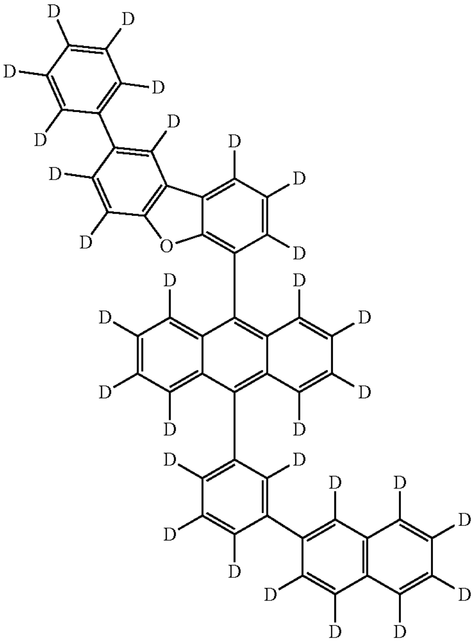
-continued
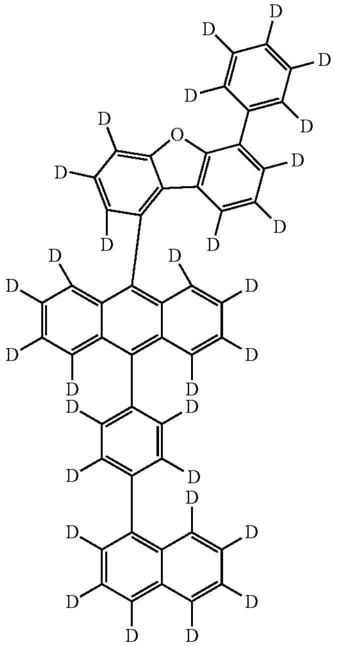
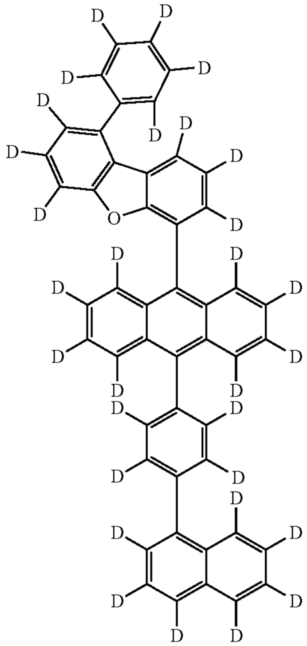

-continued
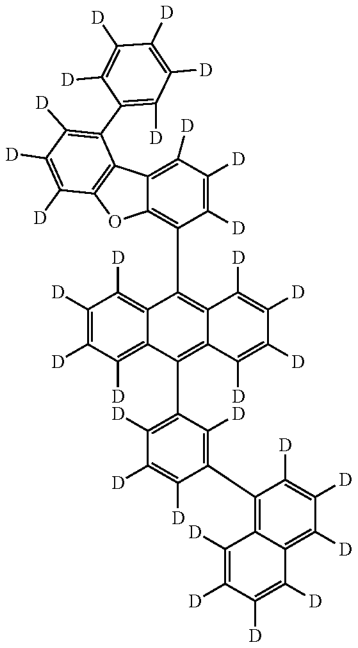
-continued
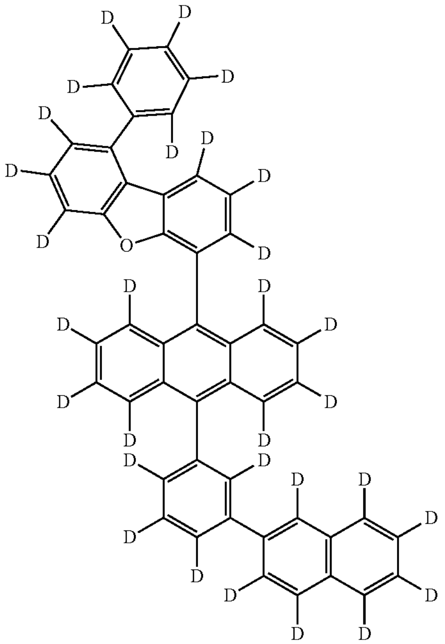
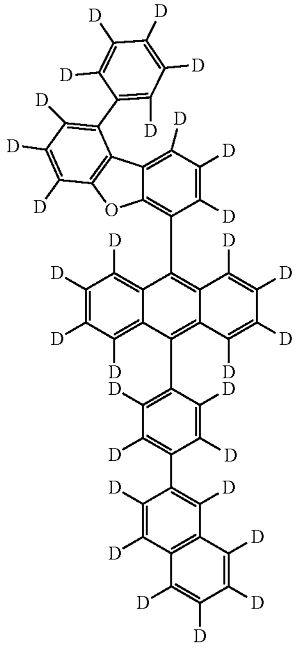
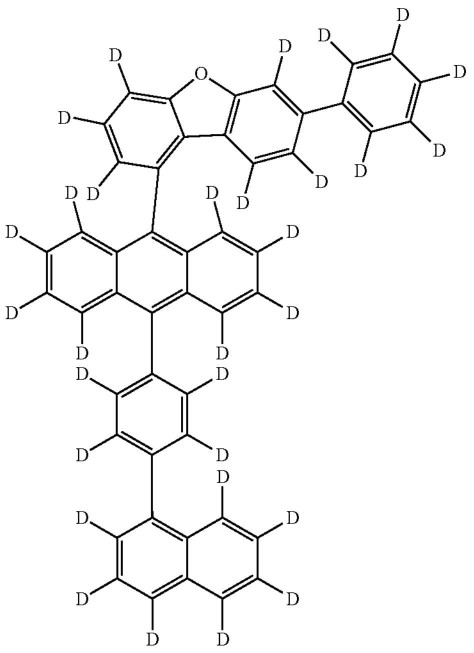

-continued
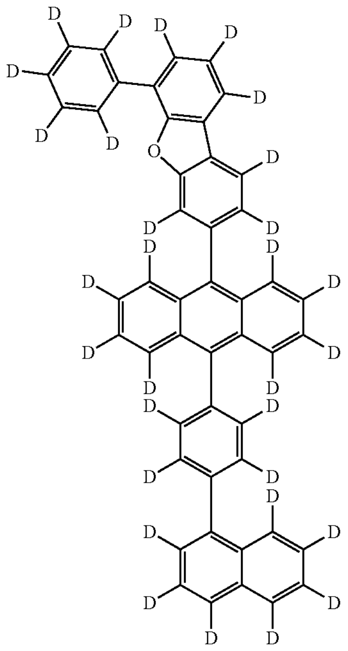
-continued
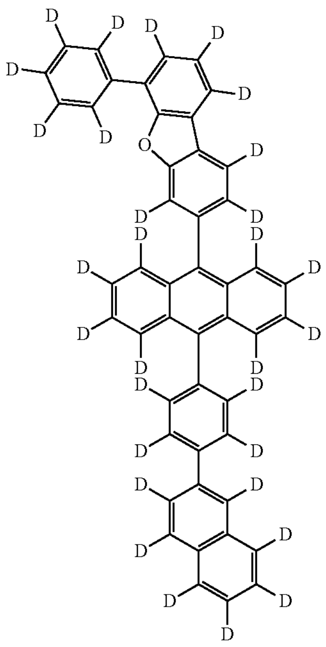
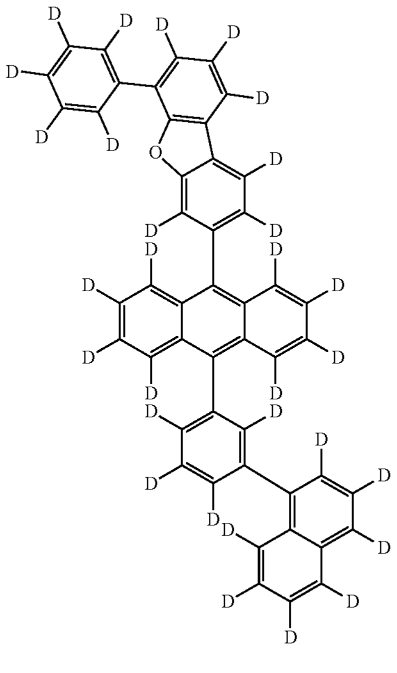
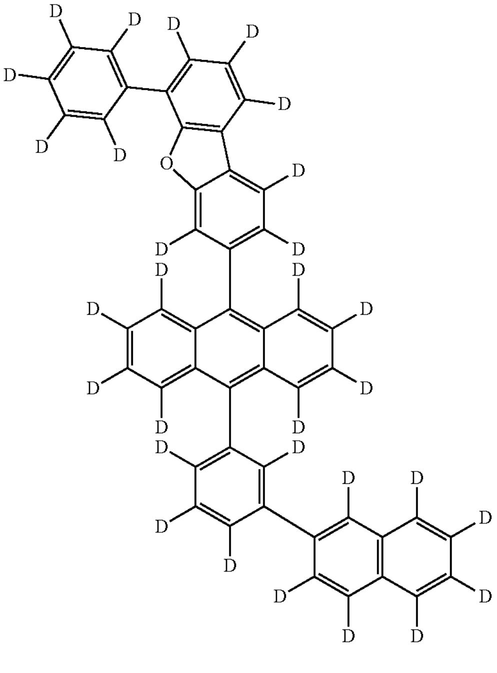

-continued
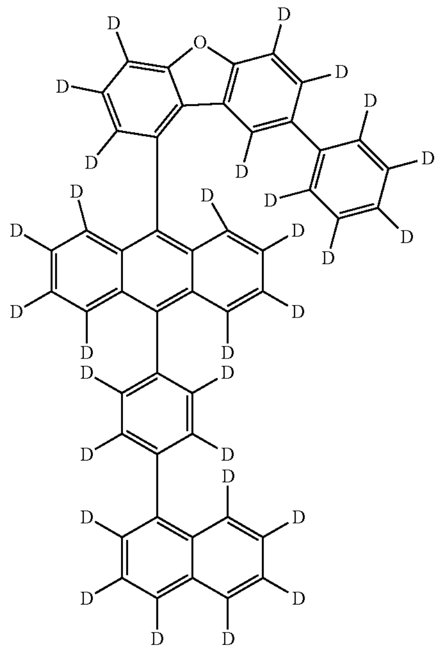
-continued
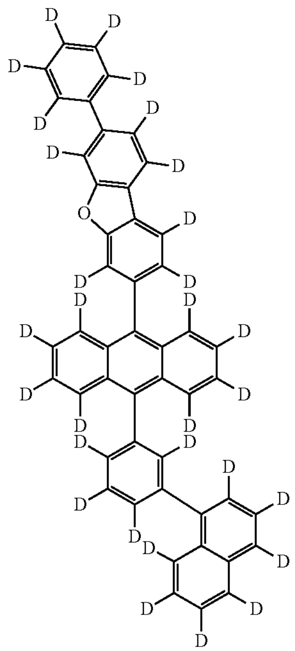
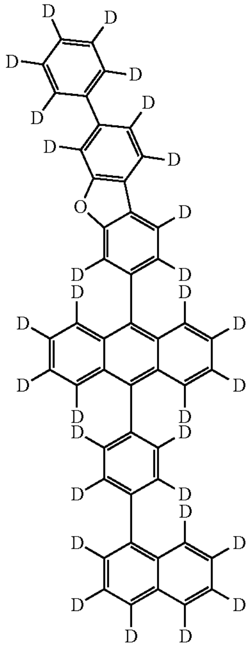
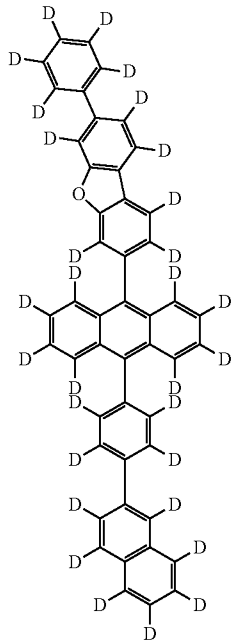

-continued
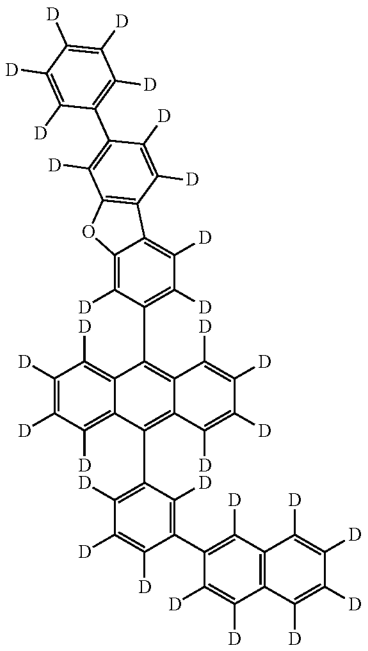
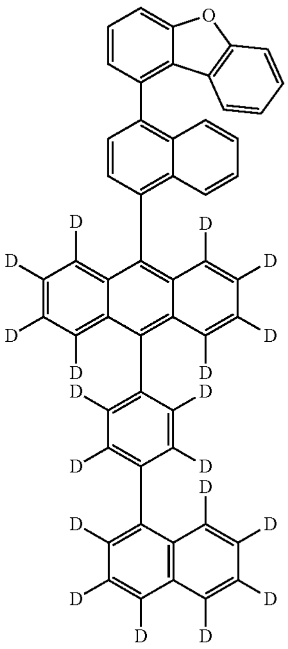
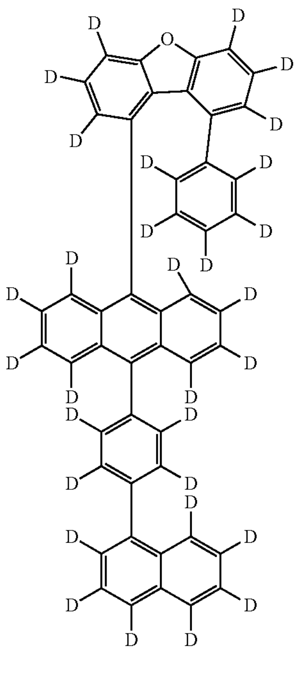
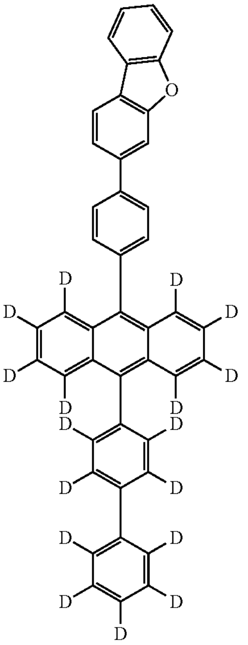
-continued

-continued
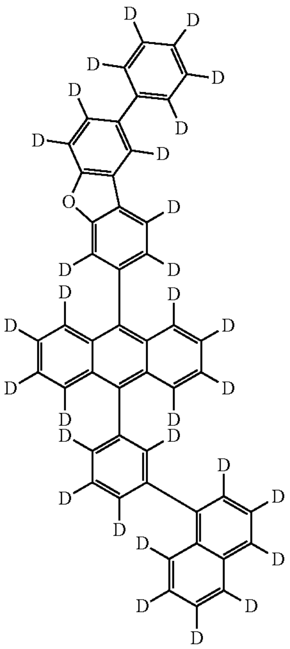
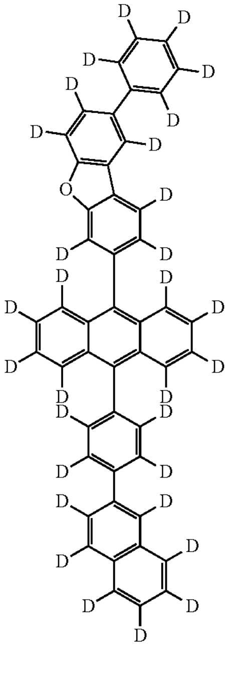
-continued
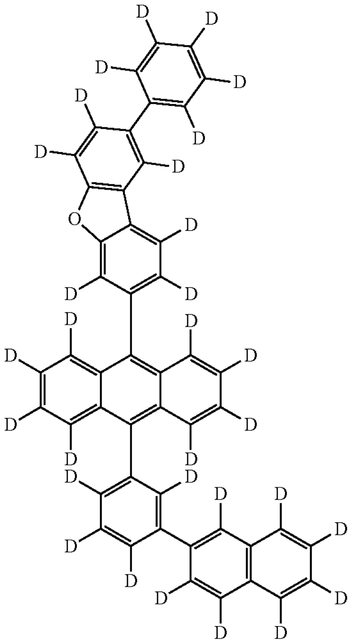
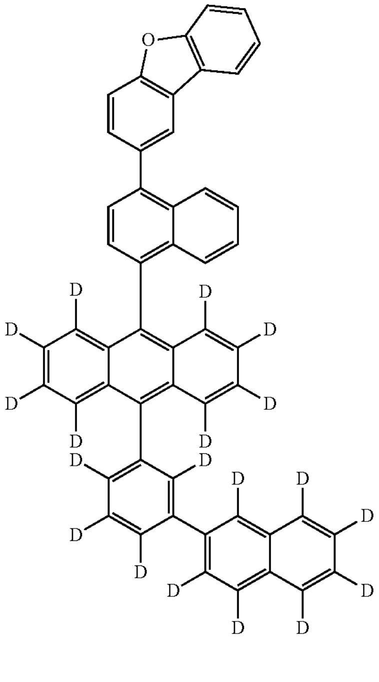

-continued
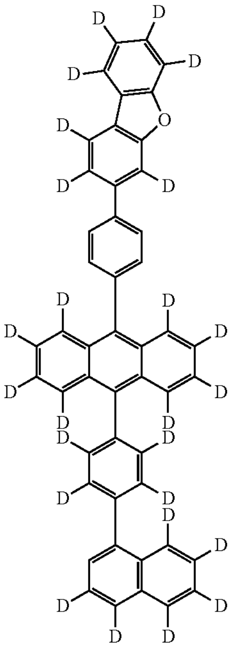
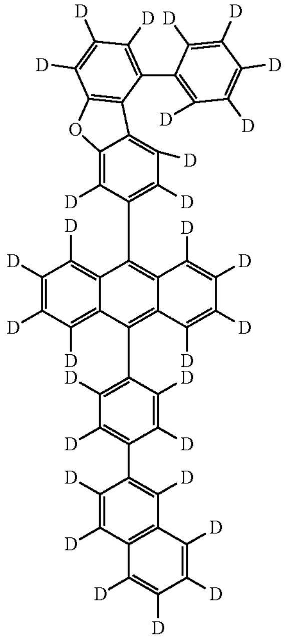
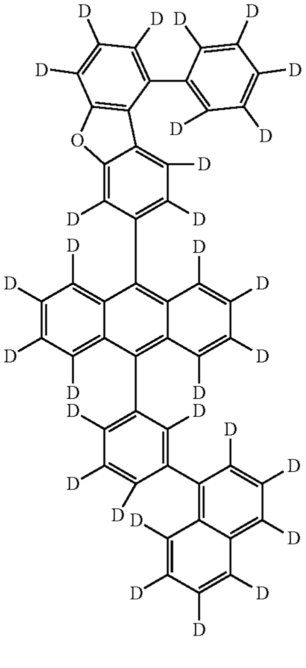
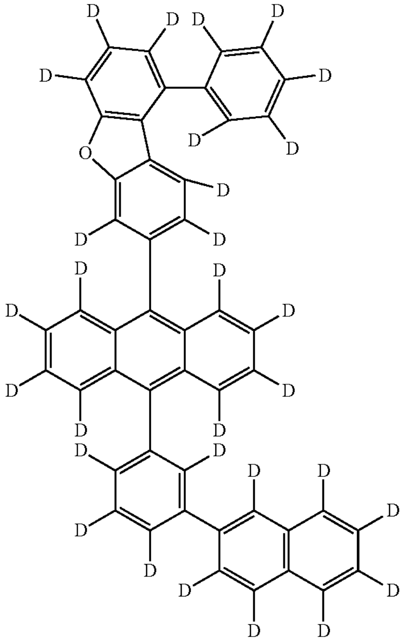
-continued

-continued
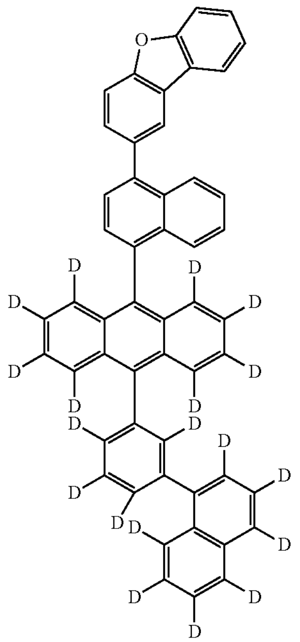
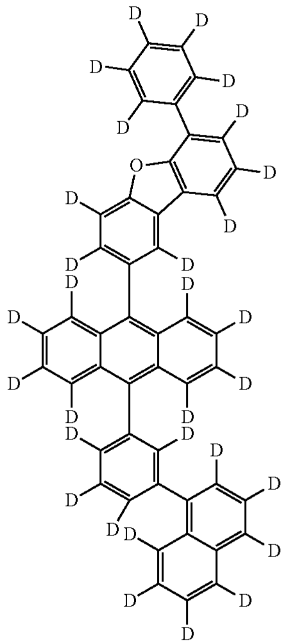
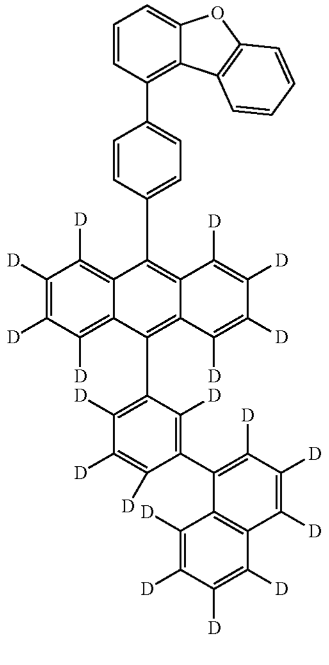
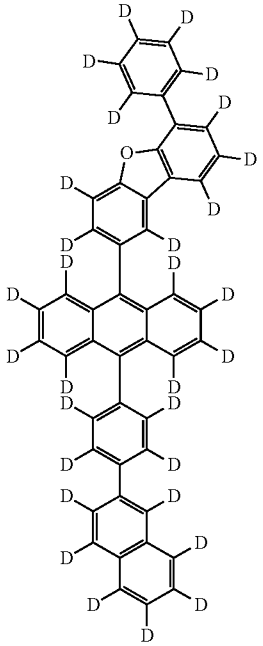
-continued

-continued
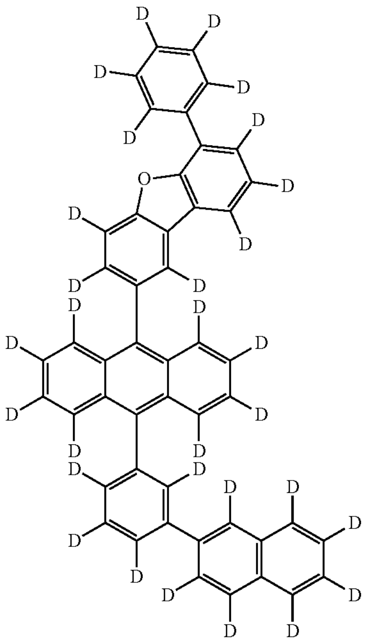
-continued
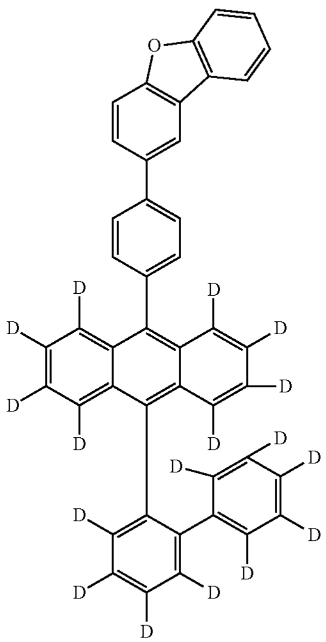
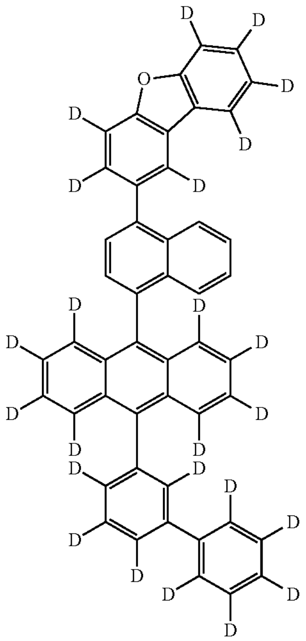
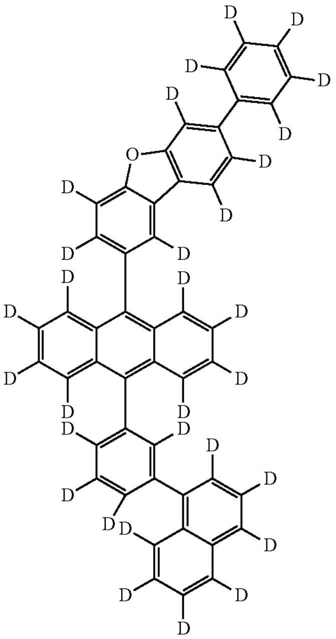

-continued
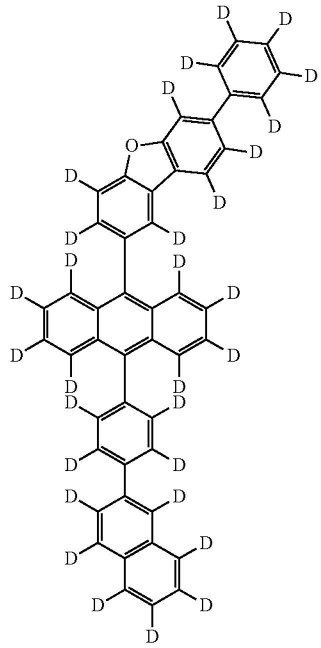
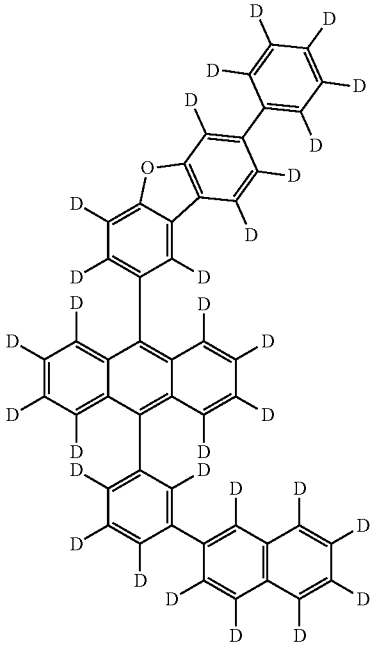
-continued
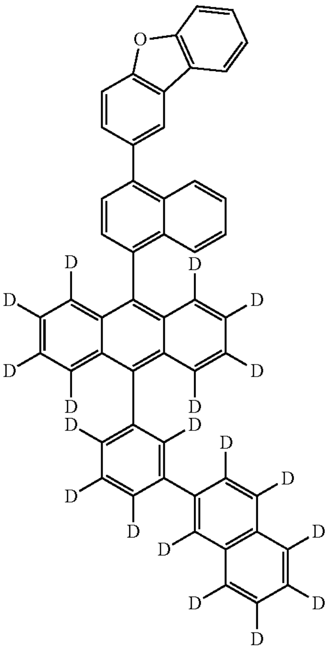
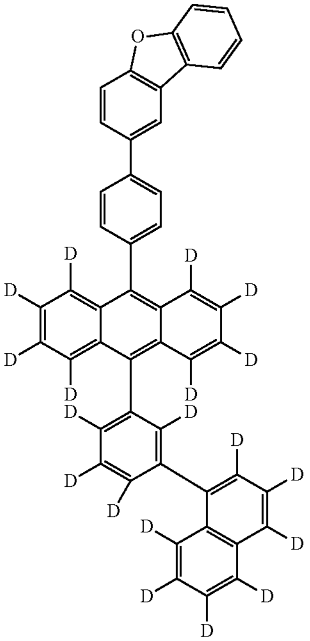

-continued
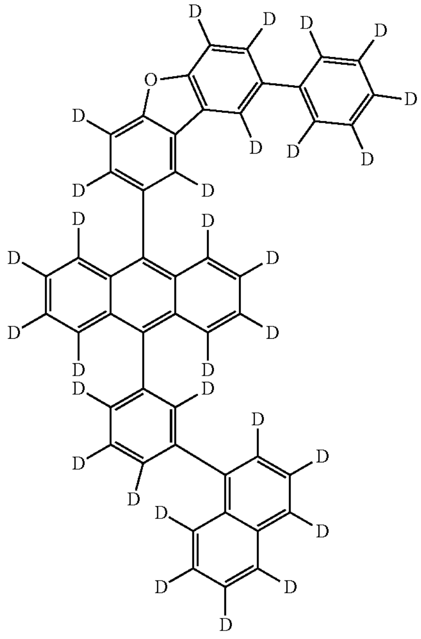
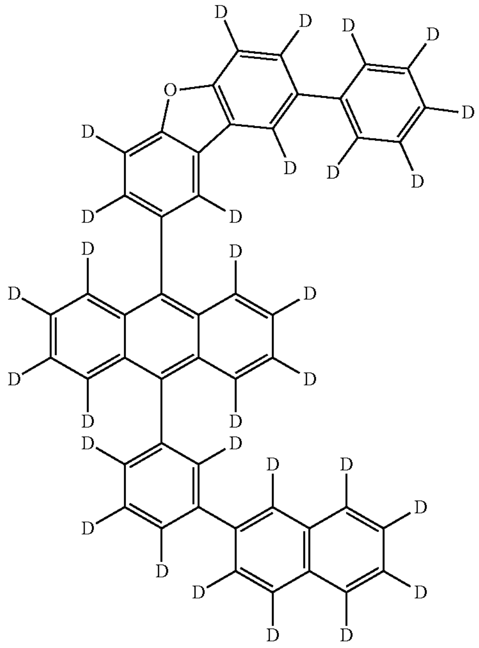
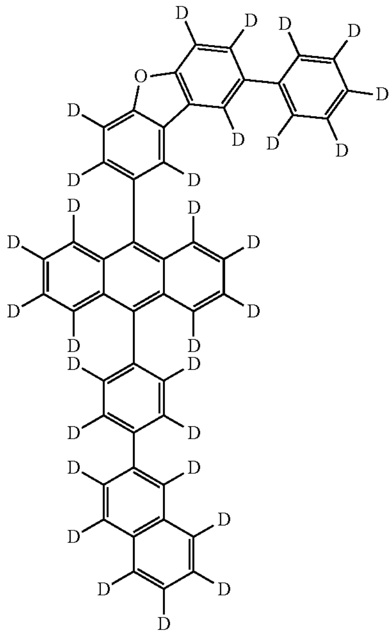
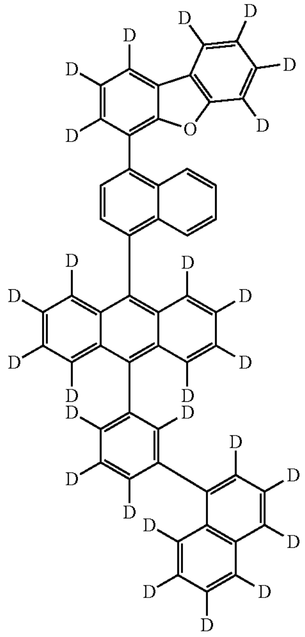

-continued
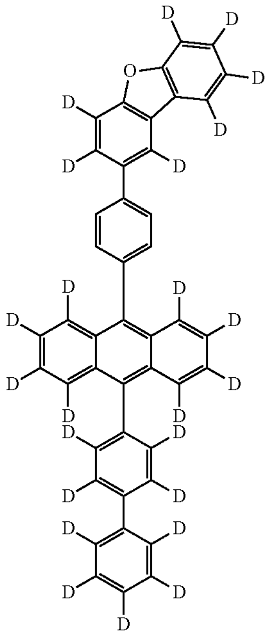
-continued
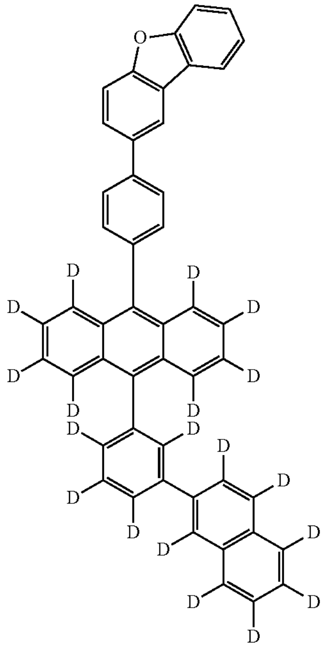
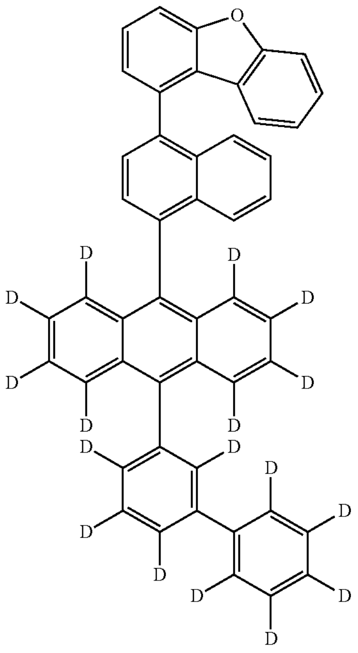
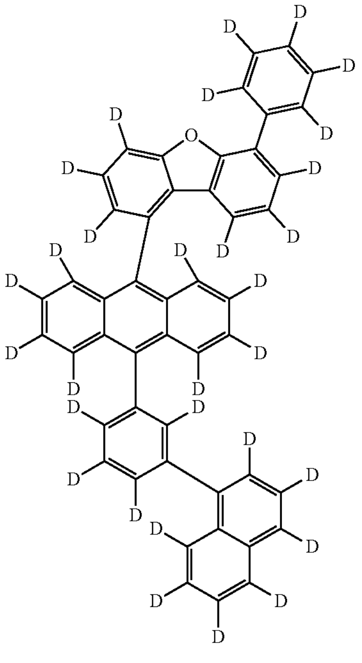

-continued
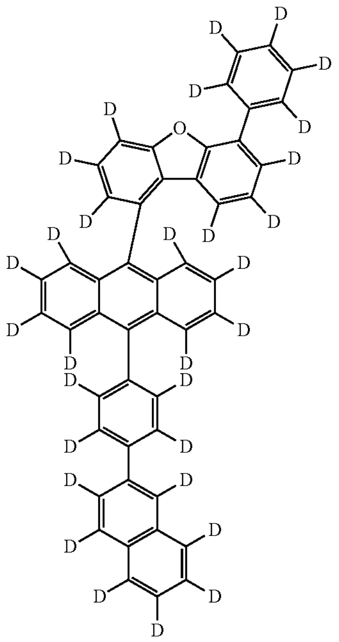
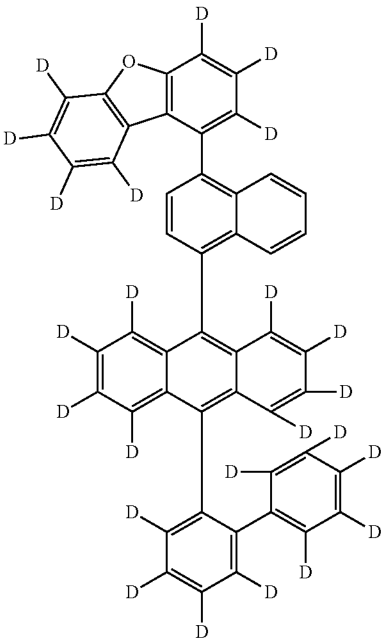
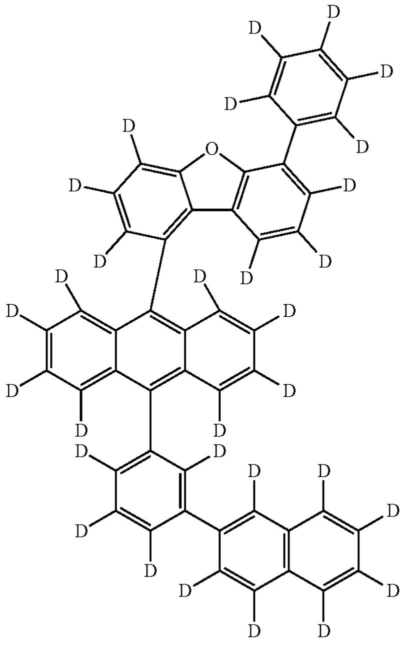
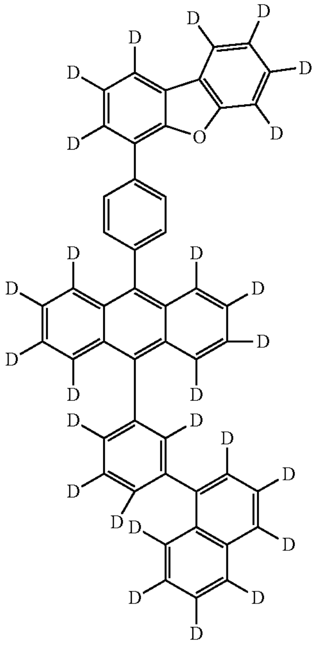

-continued
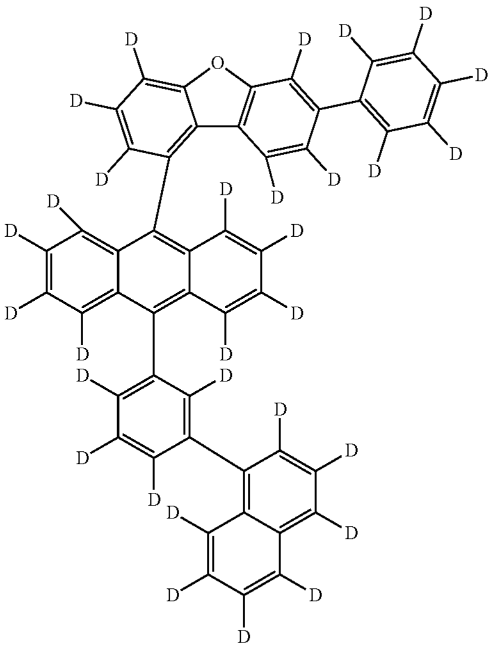
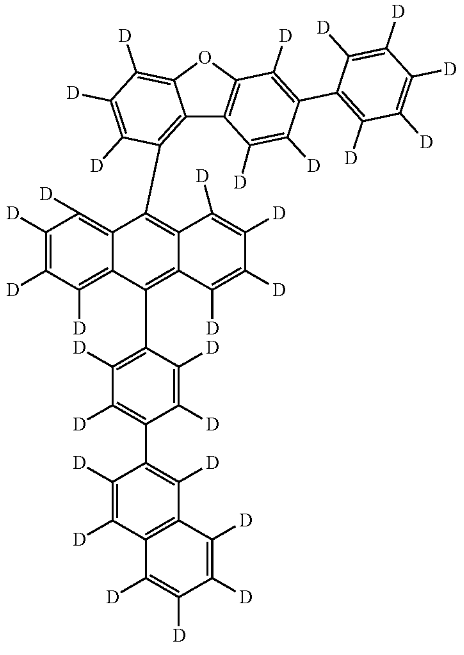
-continued
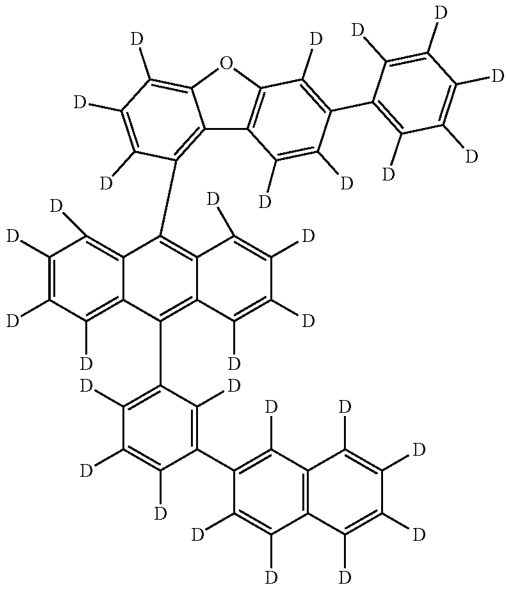
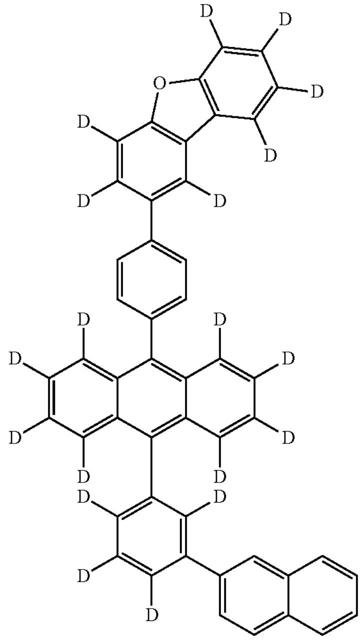

-continued
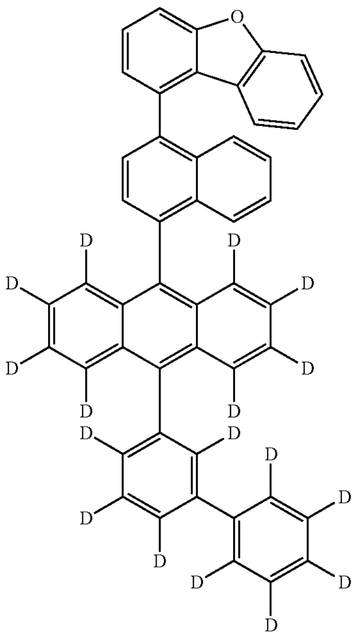
-continued
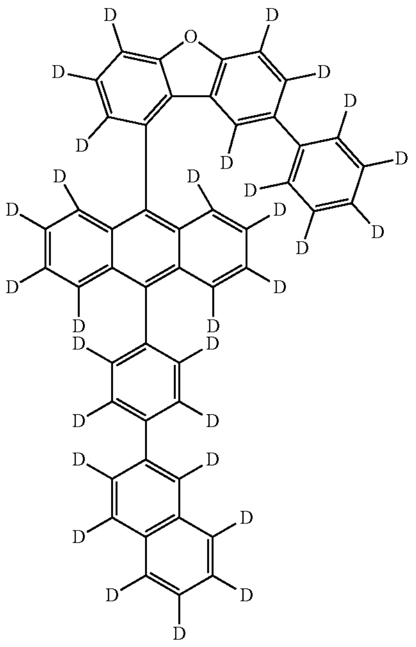
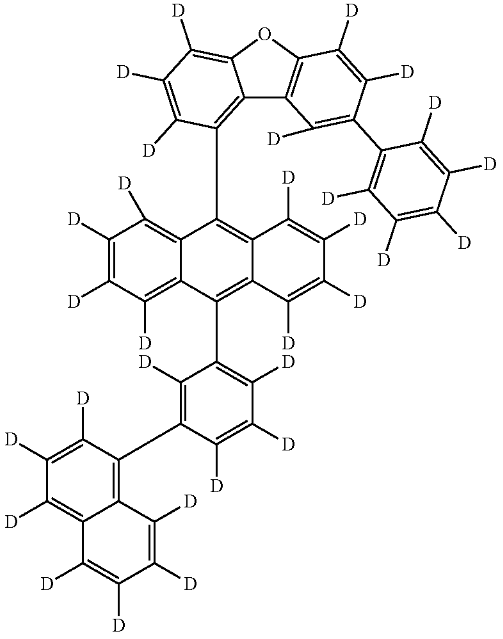
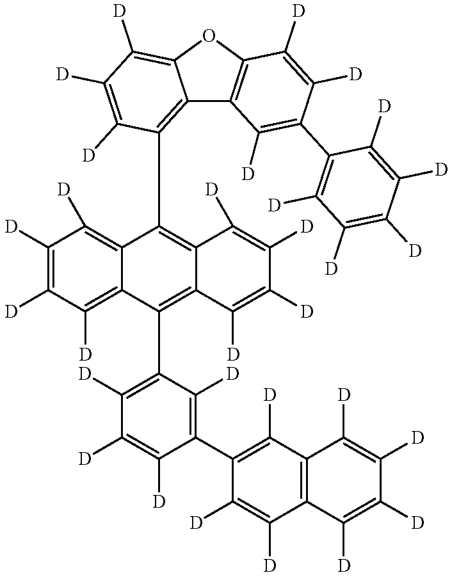

-continued
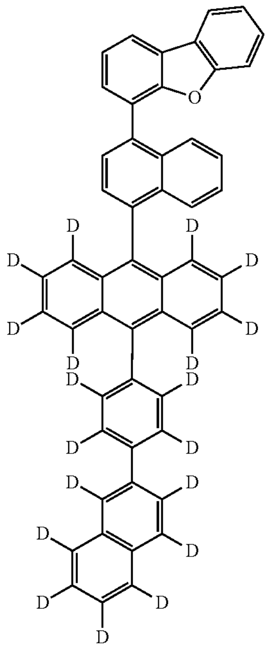
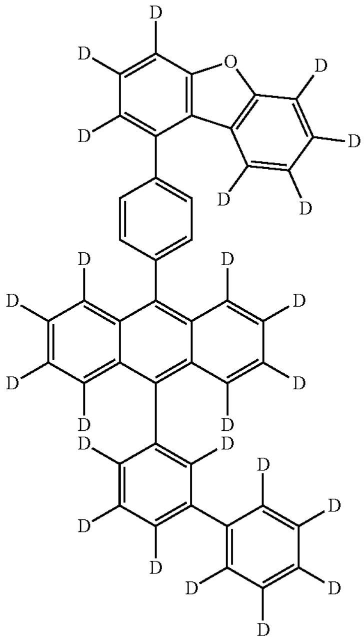
-continued
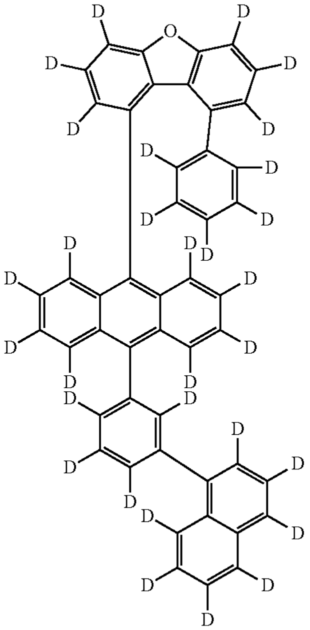
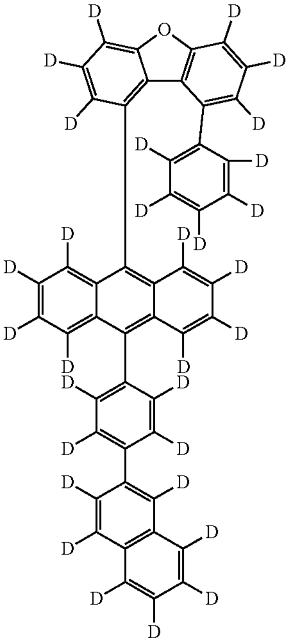

-continued
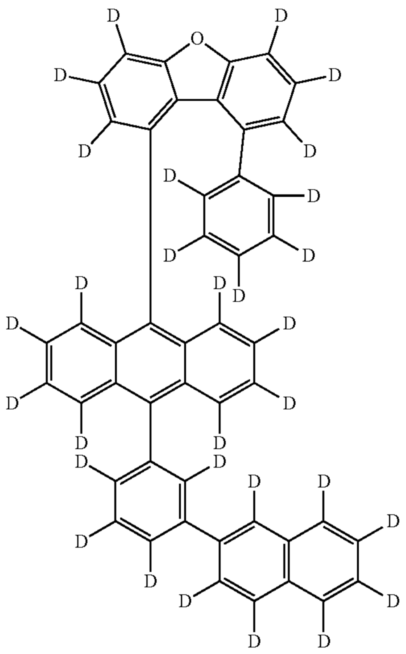
-continued
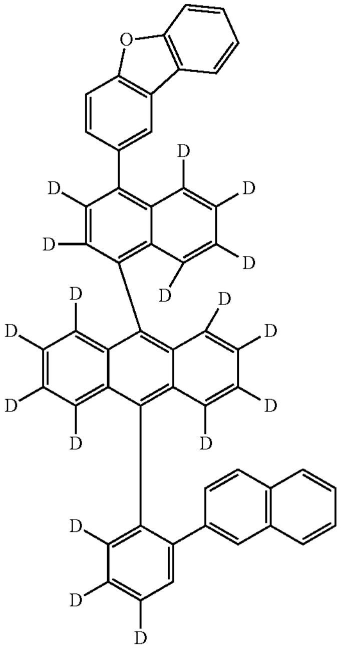
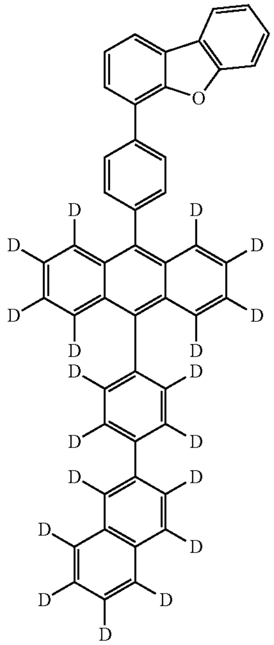
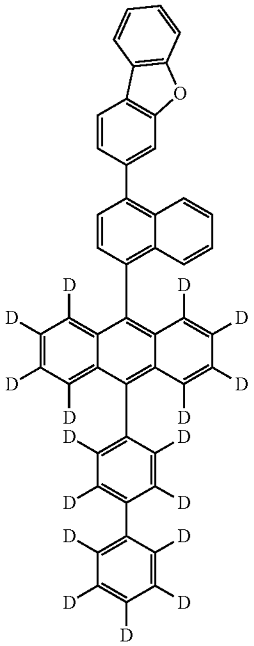
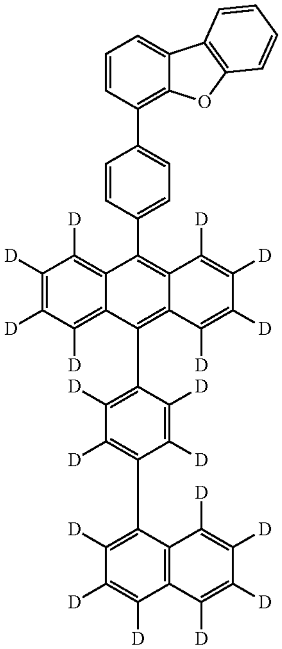
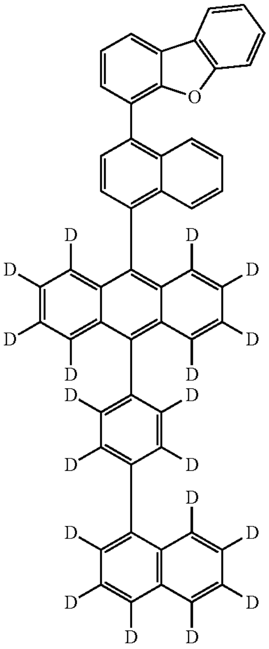

-continued
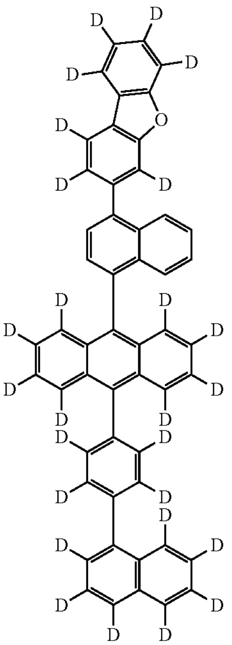 [SMILES: [2H]c1c([2H])c(-c2c3c([2H])c([2H])c([2H])c([2H])c3c(-c3ccc(-c4c([2H])c([2H])c5c(oc6c([2H])c([2H])c([2H])c([2H])c65)c4[2H])c4ccccc34)c3c([2H])c([2H])c([2H])c([2H])c23)c([2H])c([2H])c1-c1c([2H])c([2H])c([2H])c2c([2H])c([2H])c([2H])c([2H])c12]
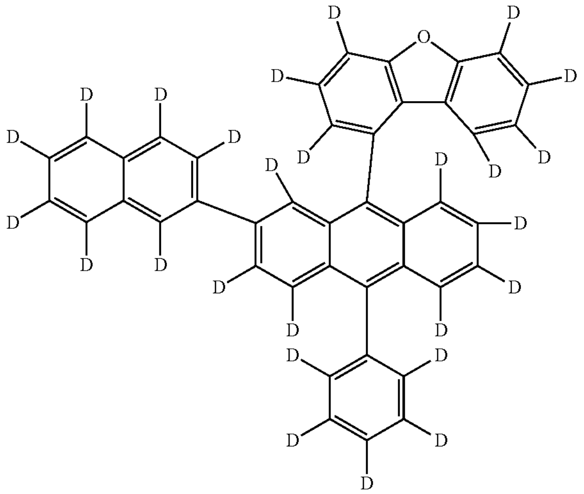
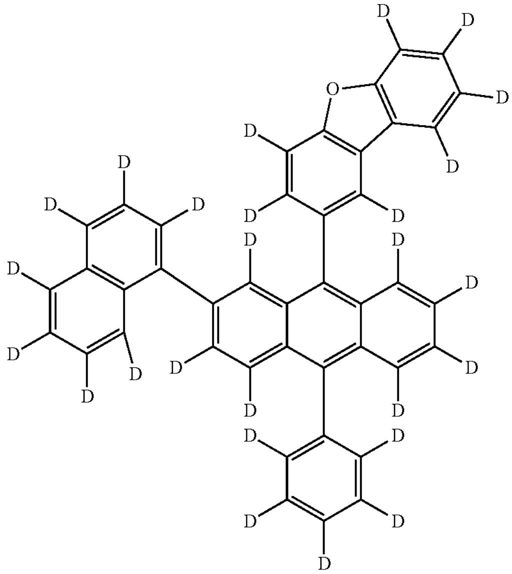
-continued
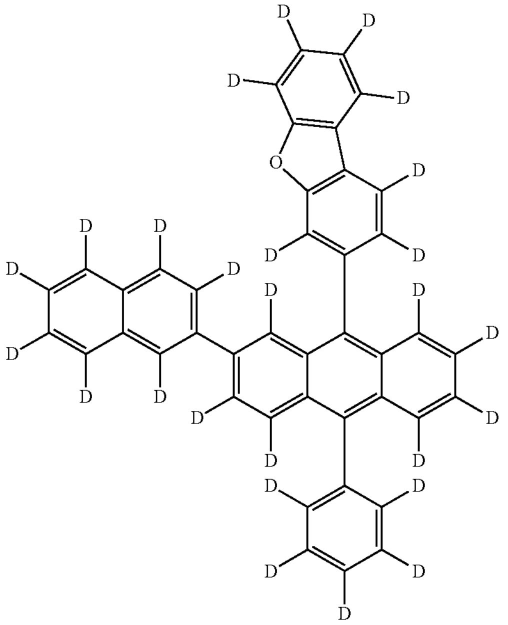
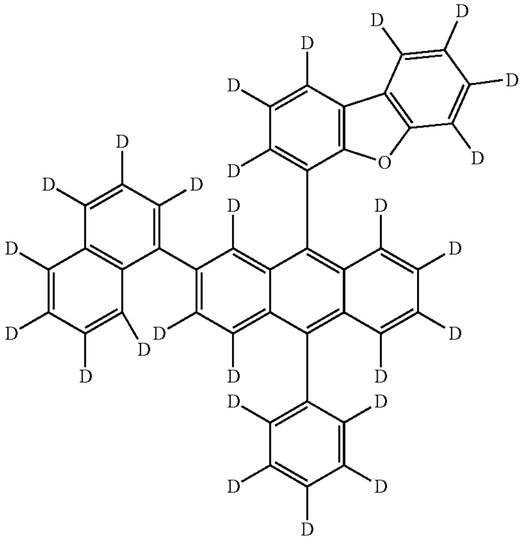

-continued
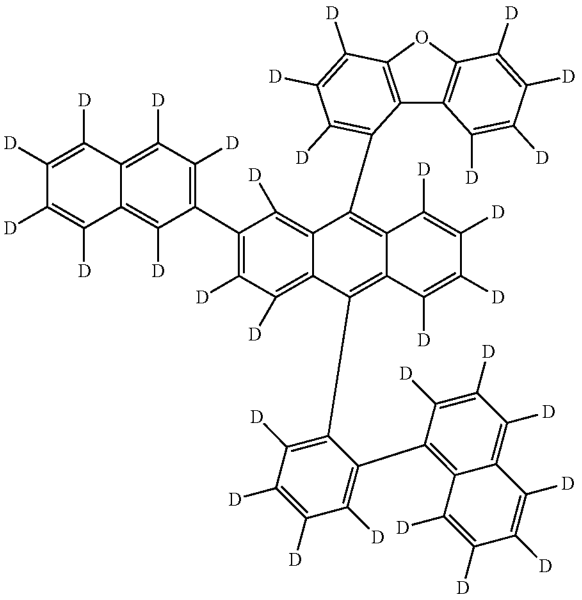
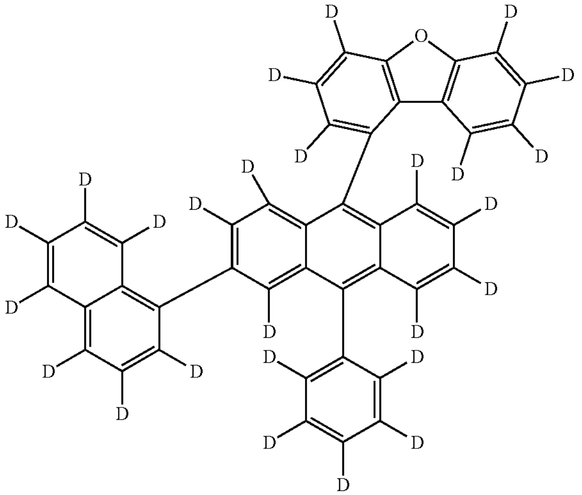
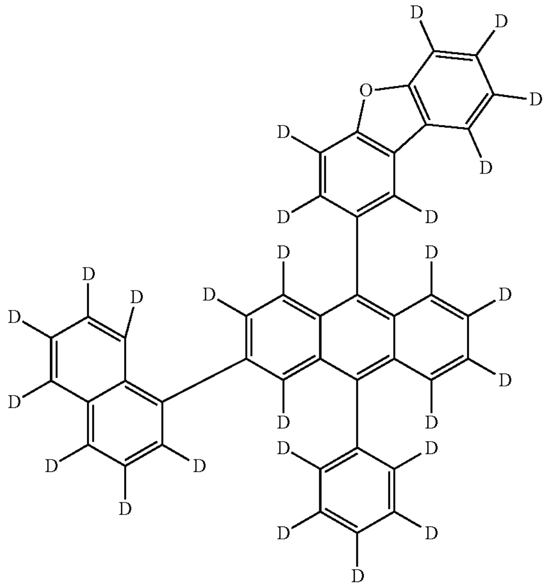
-continued
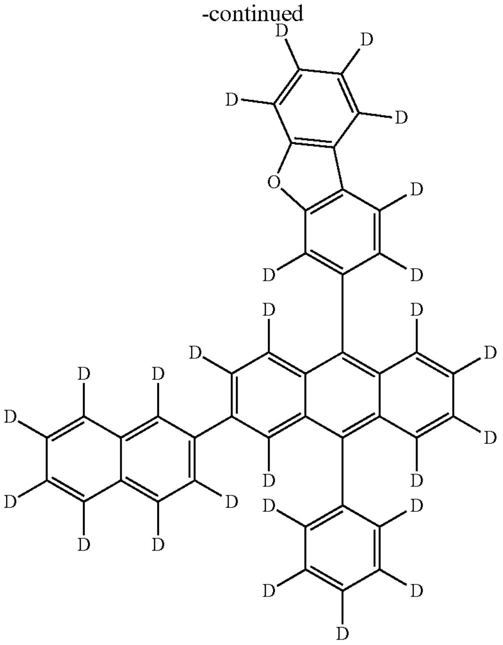
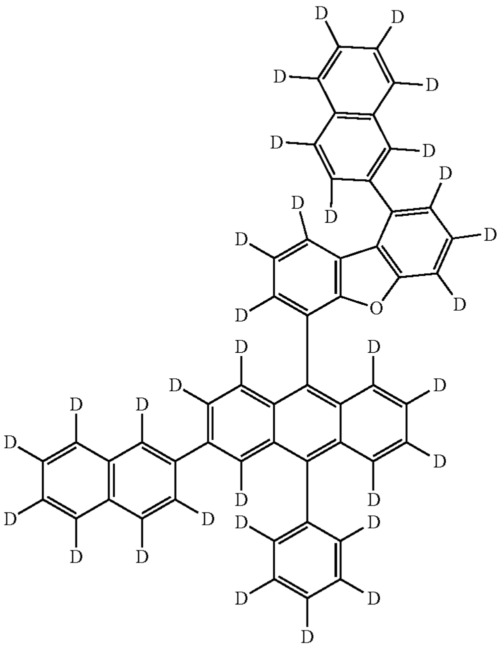

-continued
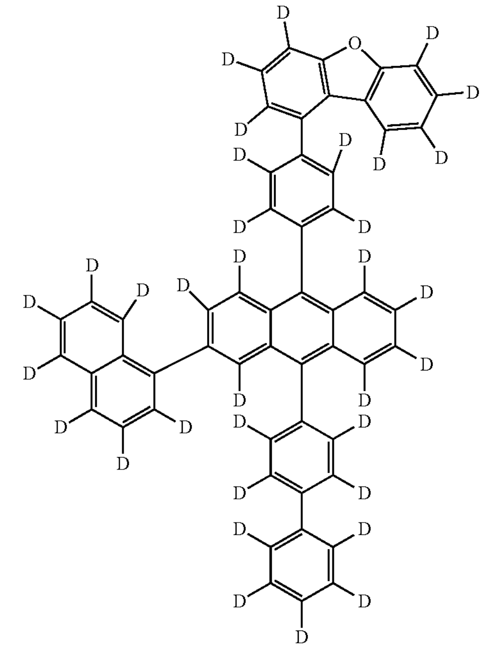
-continued
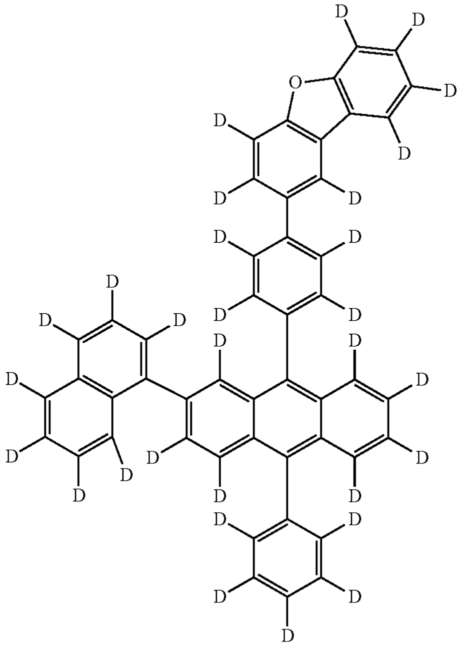
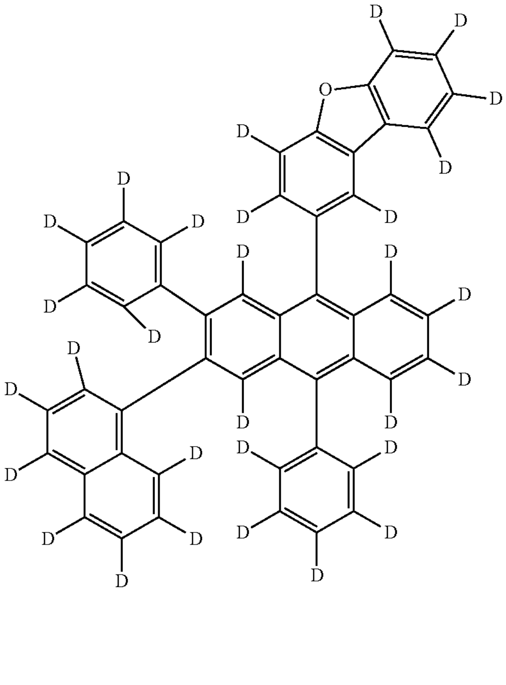
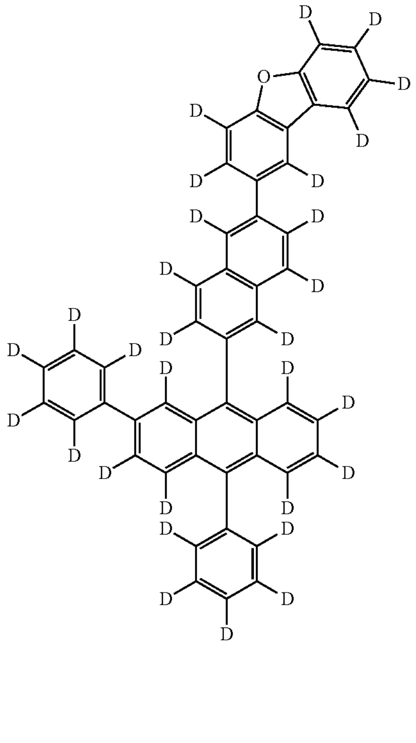 [SMILES: [2H]c1c([2H])c([2H])c(-c2c([2H])c([2H])c3c(-c4c([2H])c([2H])c([2H])c([2H])c4[2H])c4c([2H])c([2H])c([2H])c([2H])c4c(-c4c([2H])c([2H])c5c([2H])c(-c6c([2H])c([2H])c7oc8c([2H])c([2H])c([2H])c([2H])c8c7c6[2H])c([2H])c([2H])c5c4[2H])c3c2[2H])c([2H])c1[2H]]

-continued
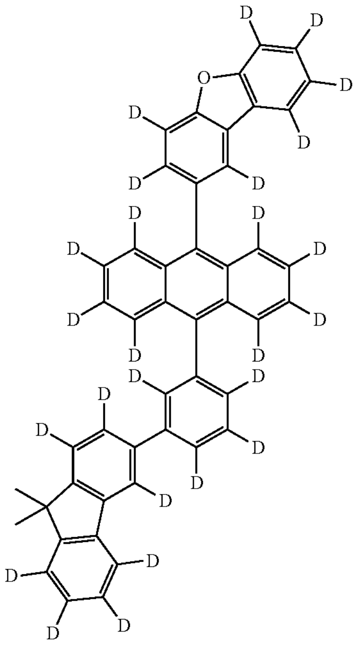
-continued
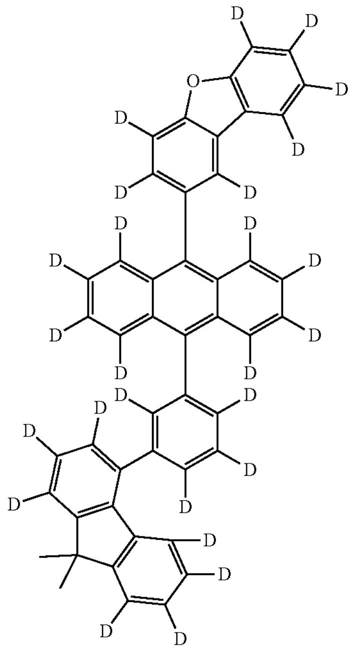
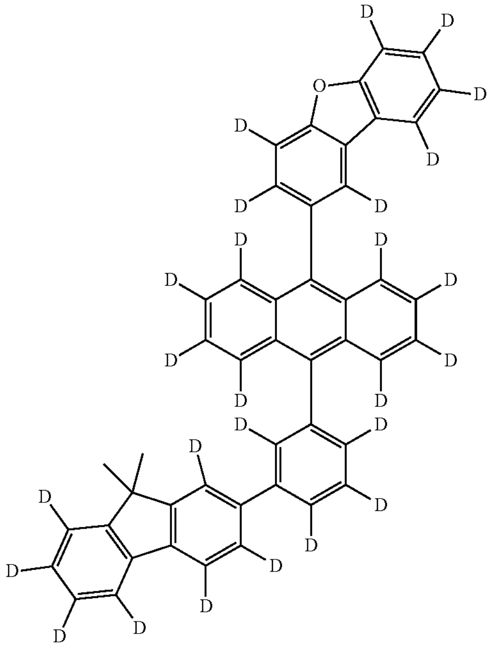
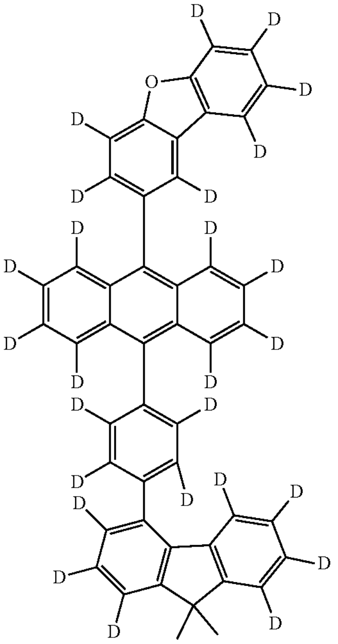

-continued
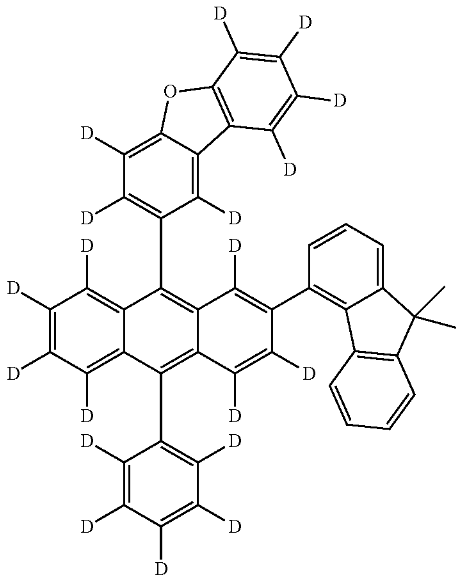
-continued
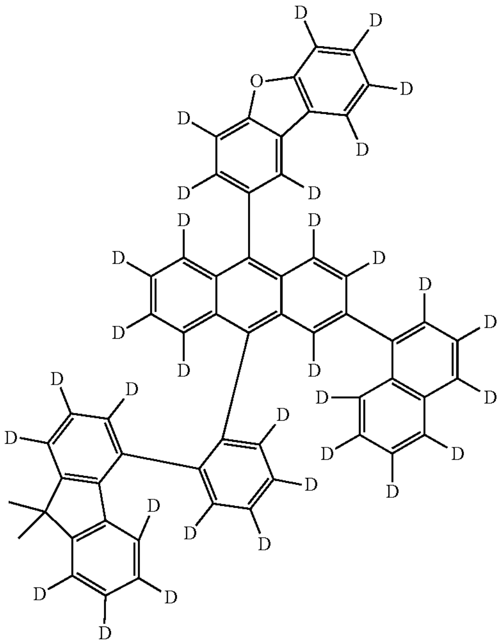
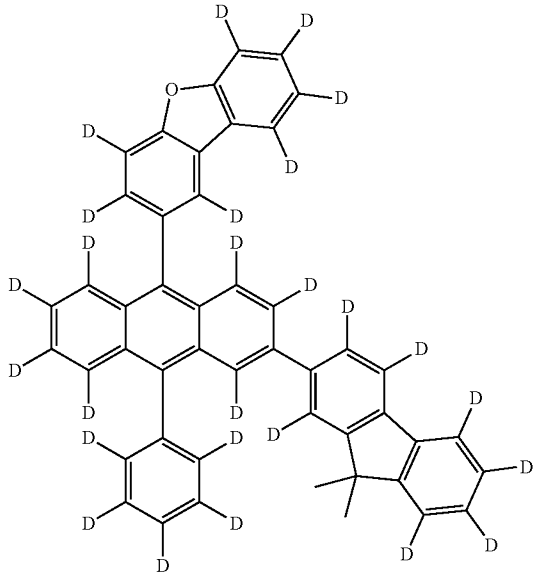
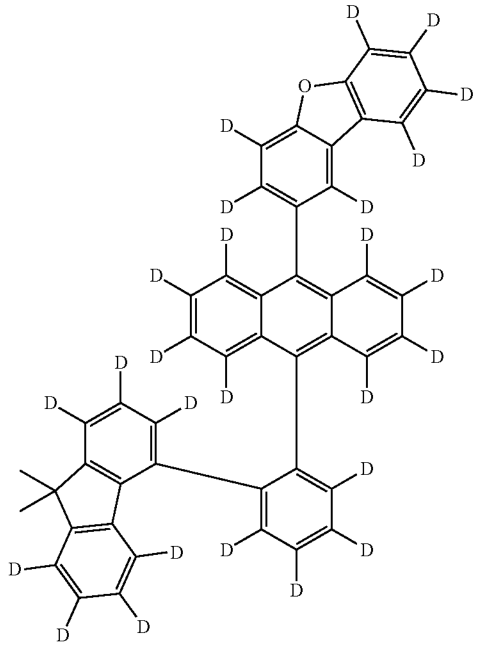
In an exemplary embodiment of the present specification, the compound represented by Formula 1-3 is any one selected from the following compounds.

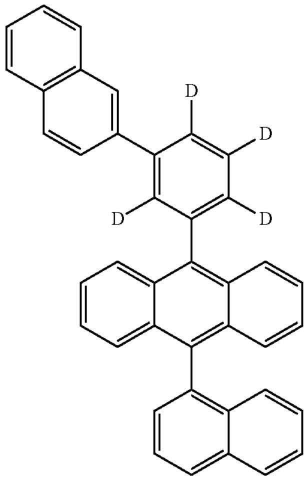
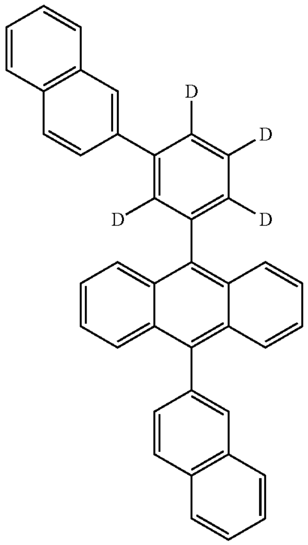
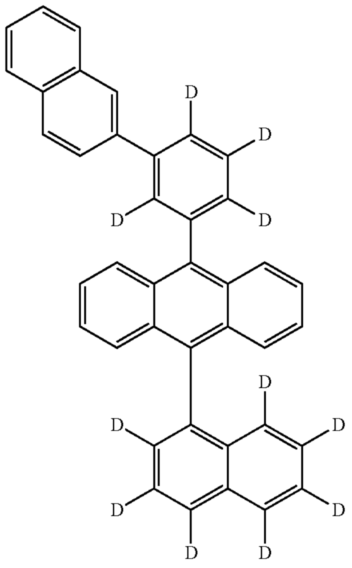
-continued
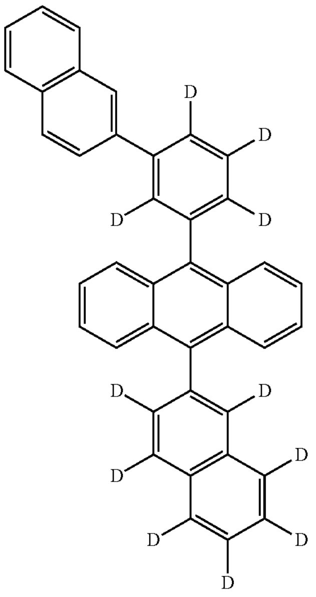
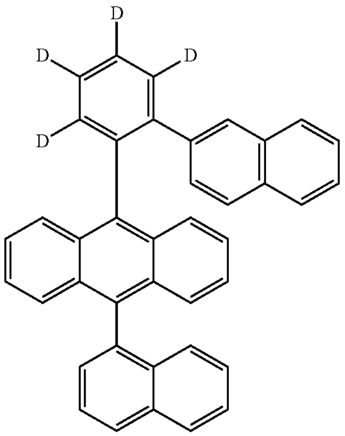
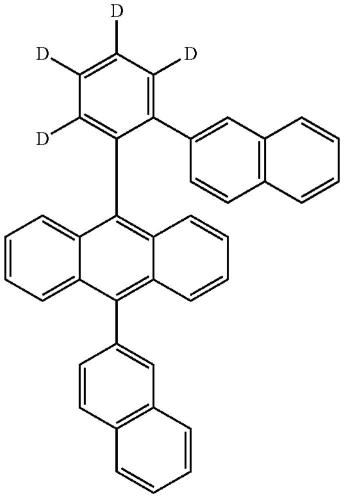

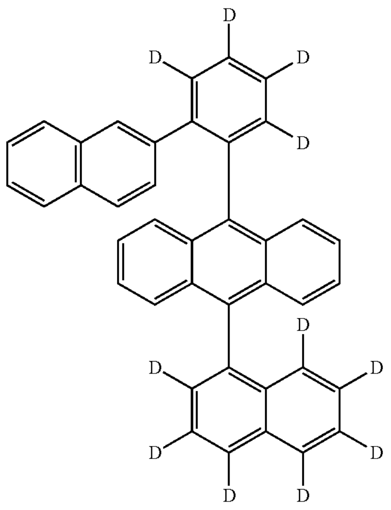
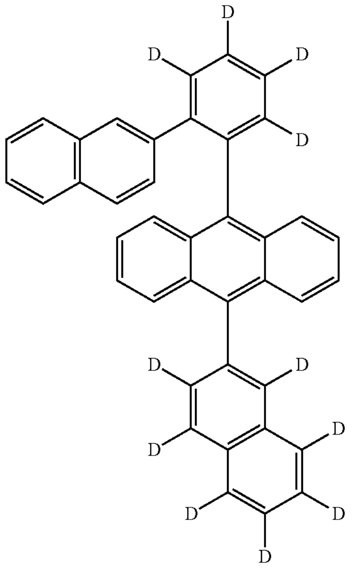
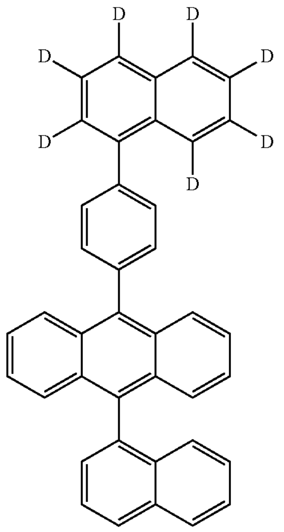
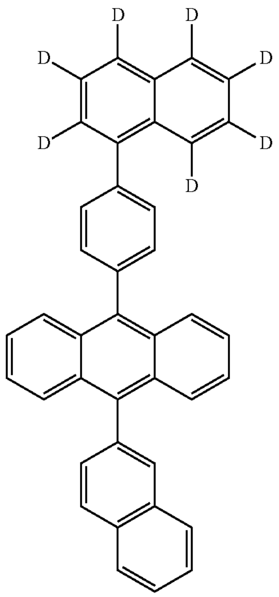
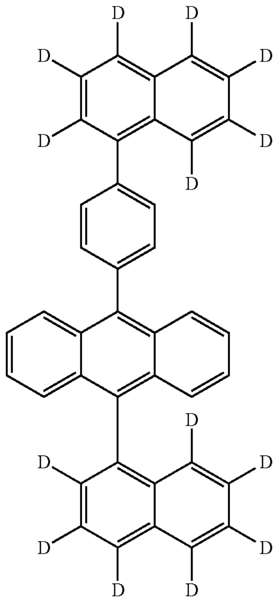

-continued
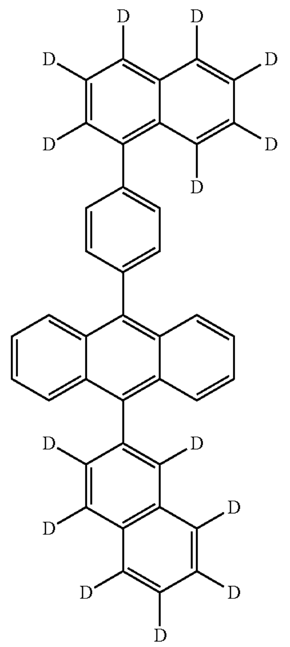
-continued
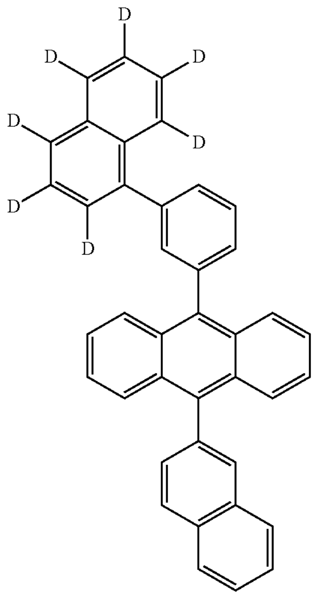
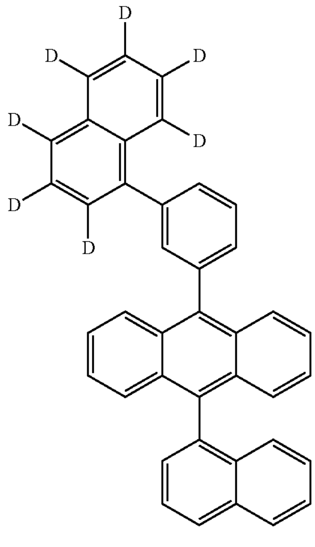
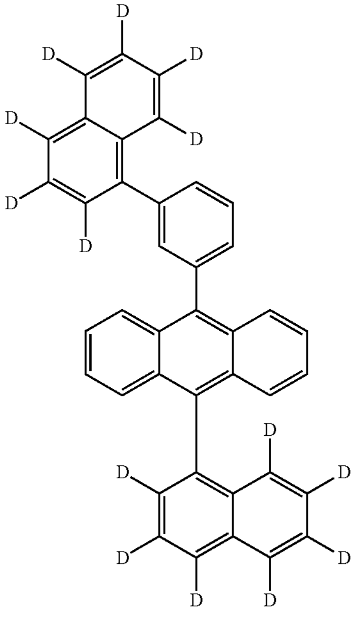

-continued
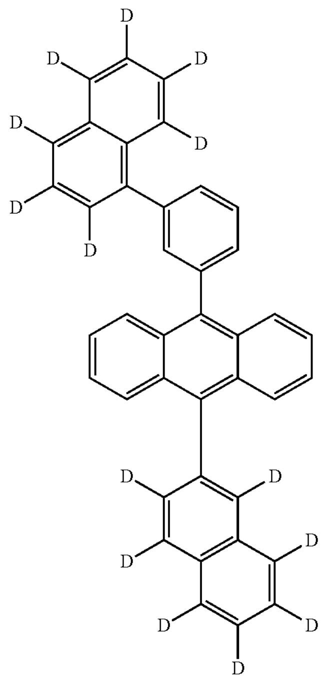
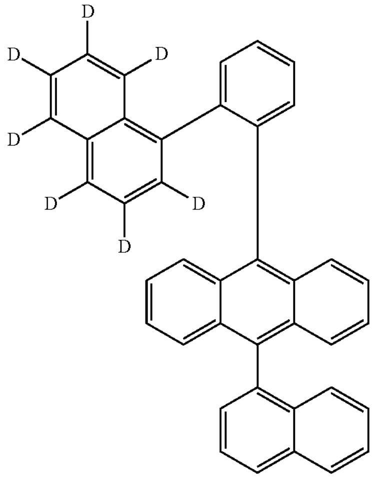
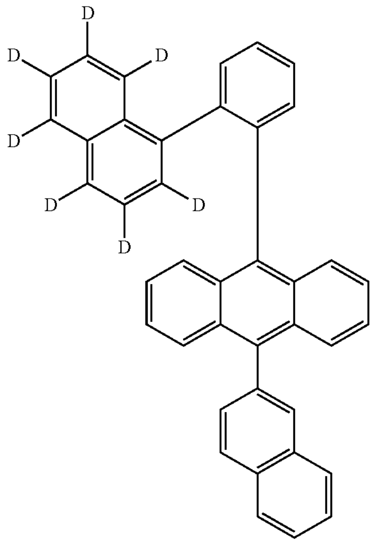
-continued
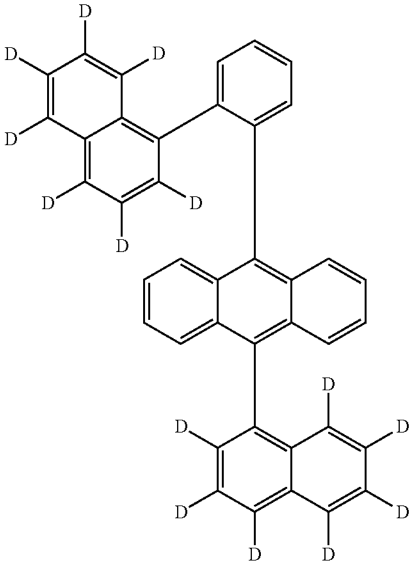
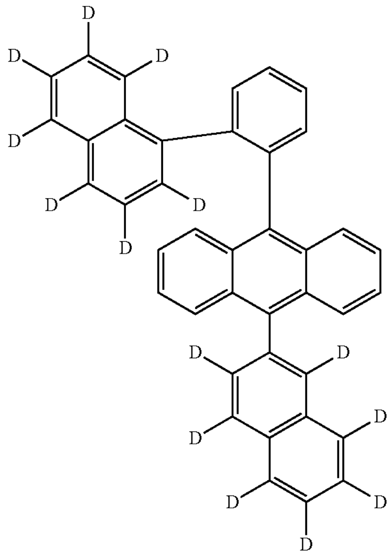
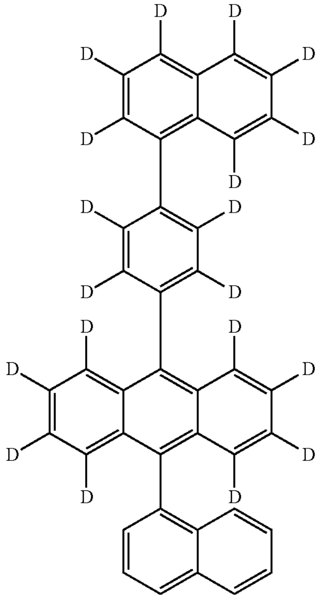

-continued
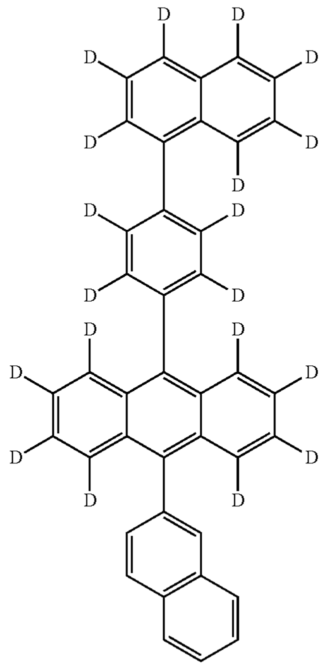
-continued
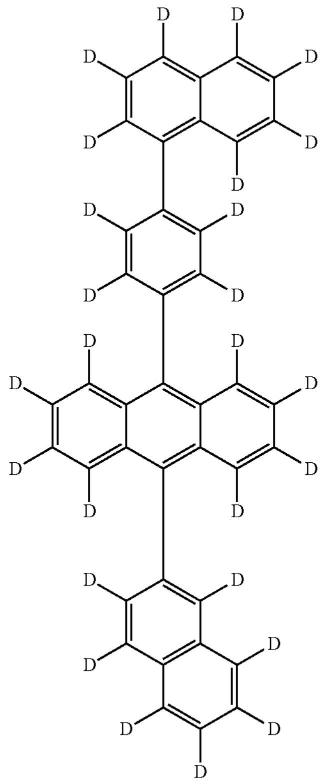
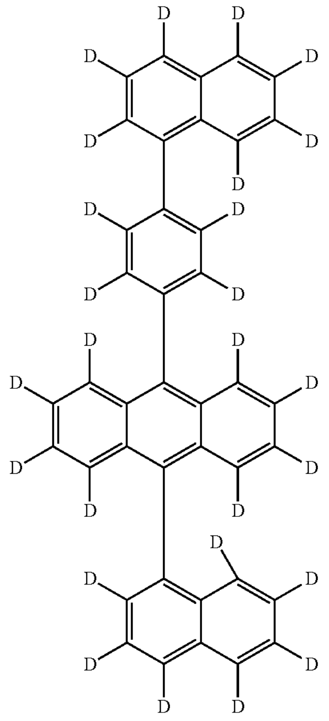
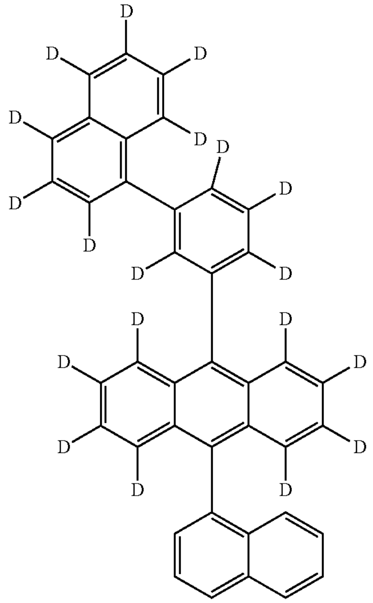

-continued
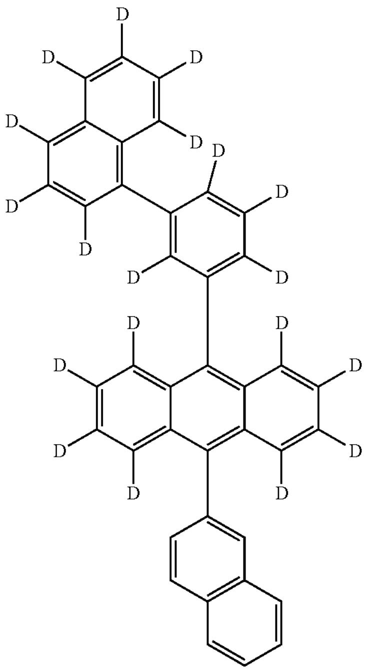
-continued
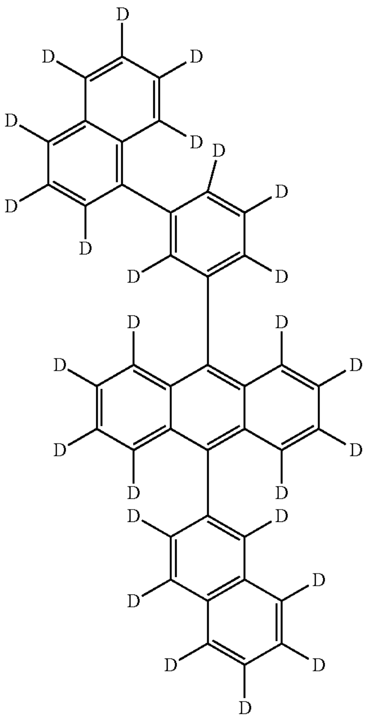
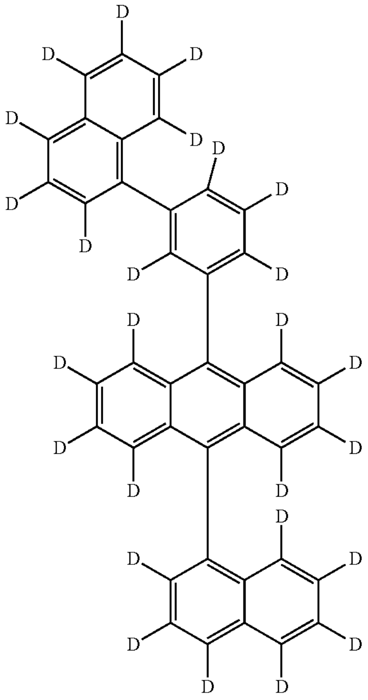
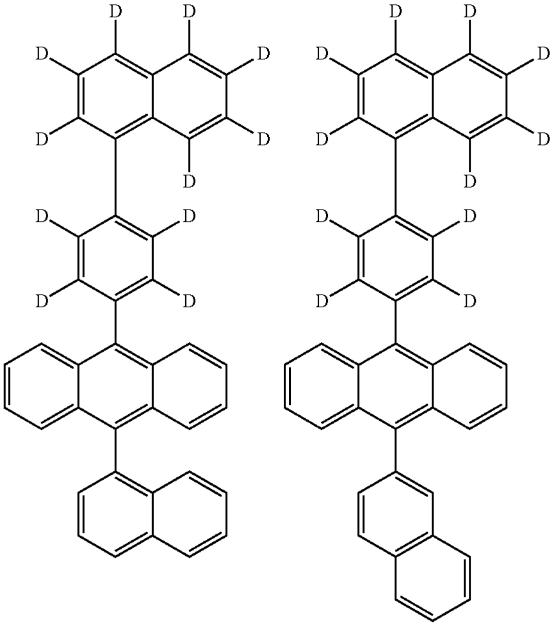

-continued
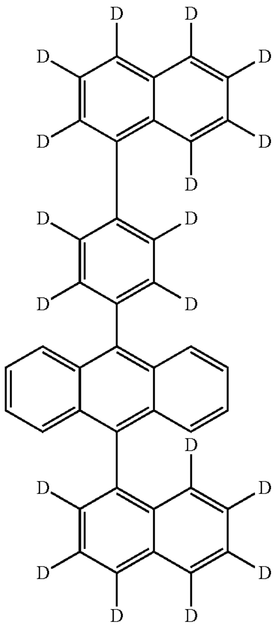
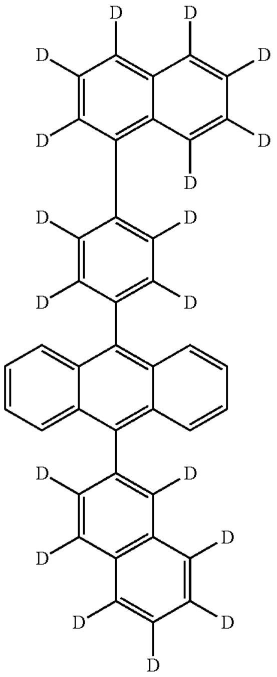
-continued
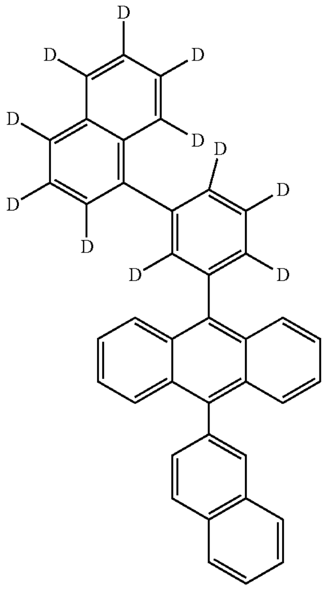
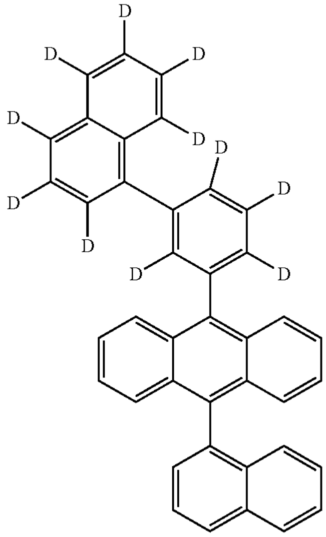
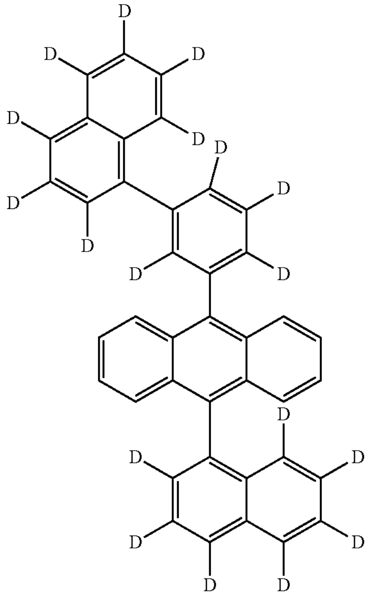

-continued
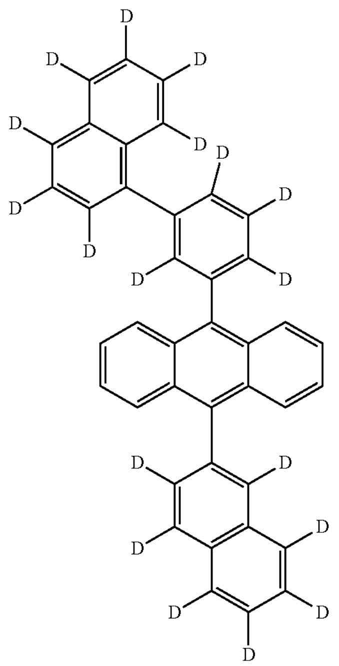
-continued
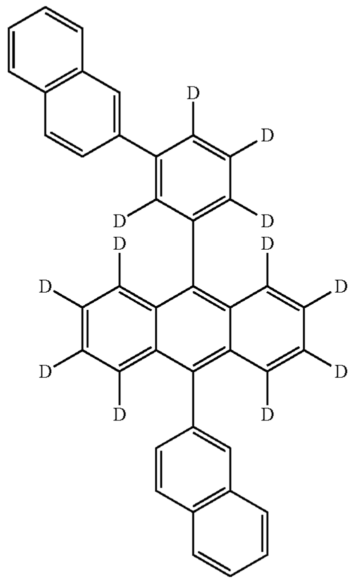
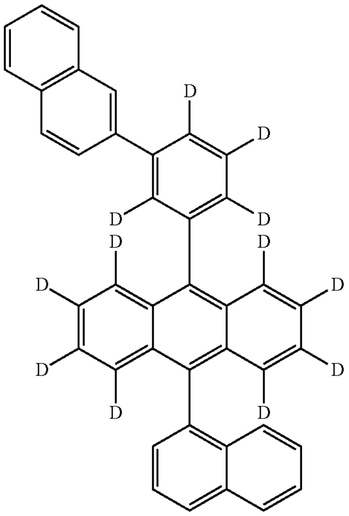
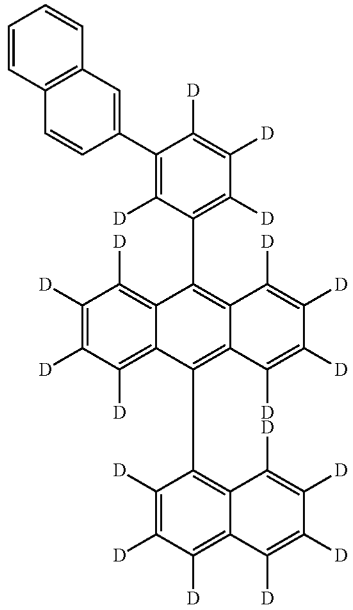

-continued
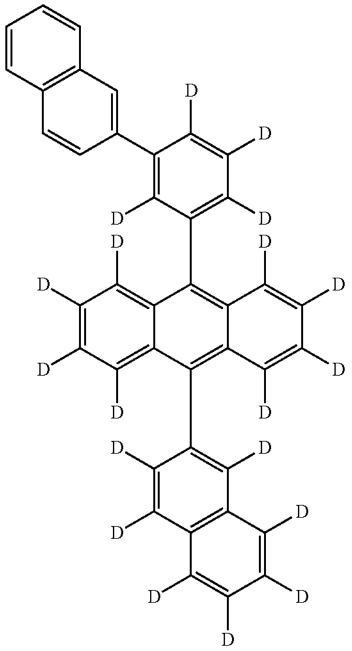
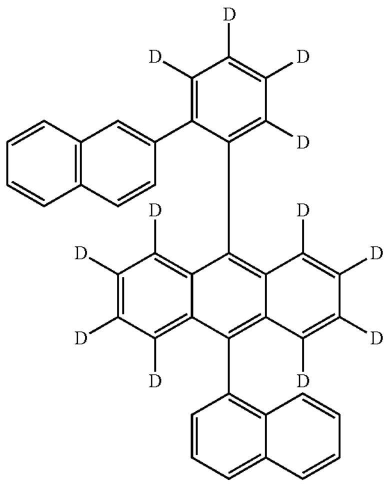
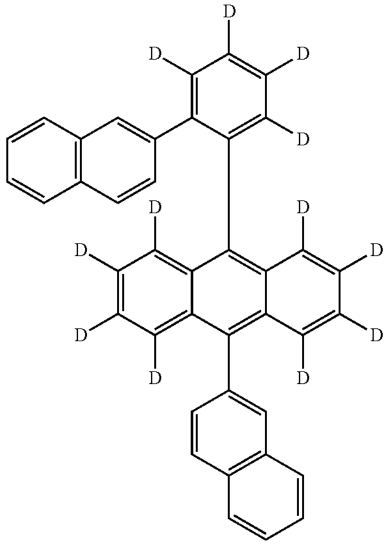
-continued
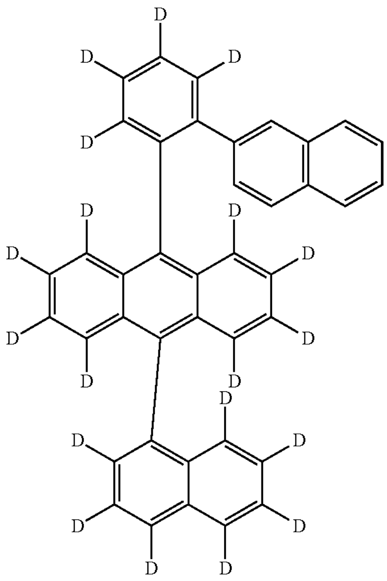
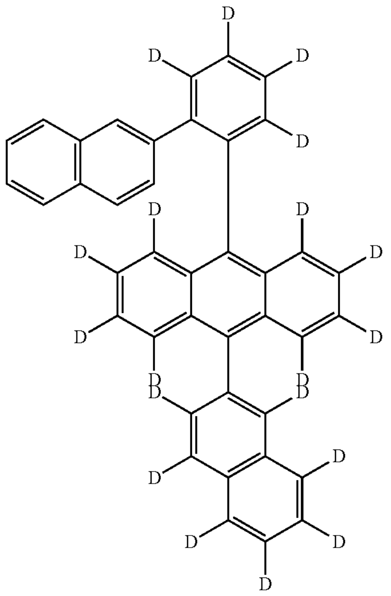
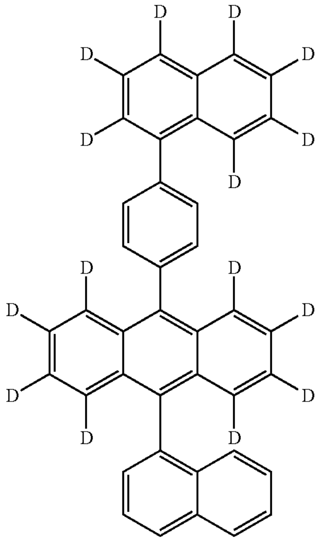

-continued
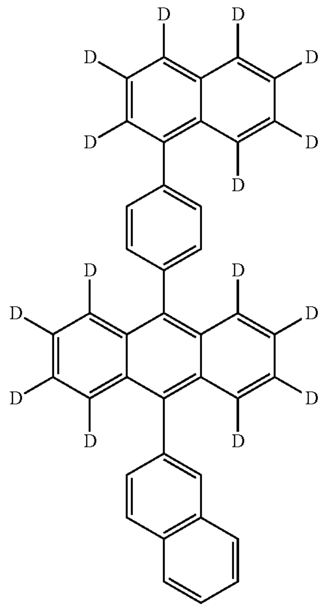
-continued
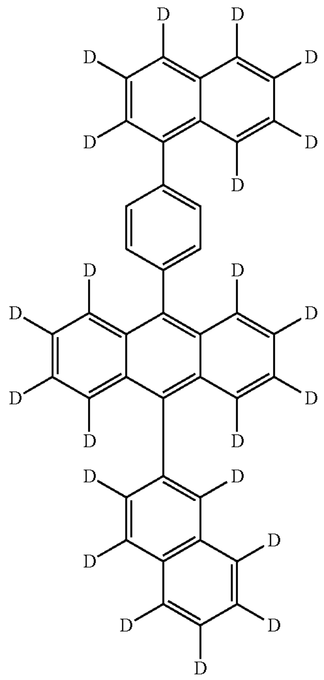
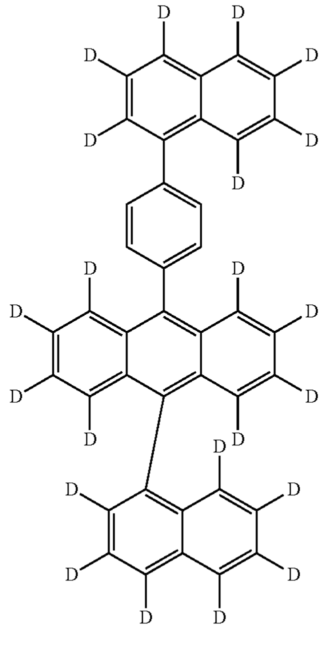
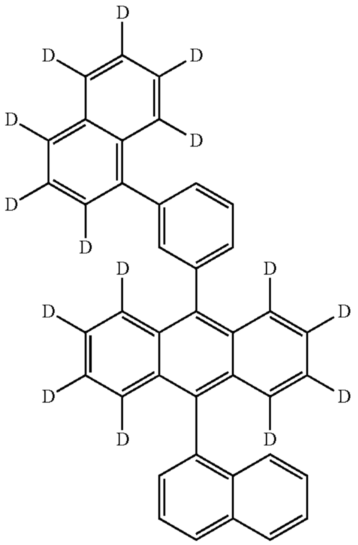

-continued
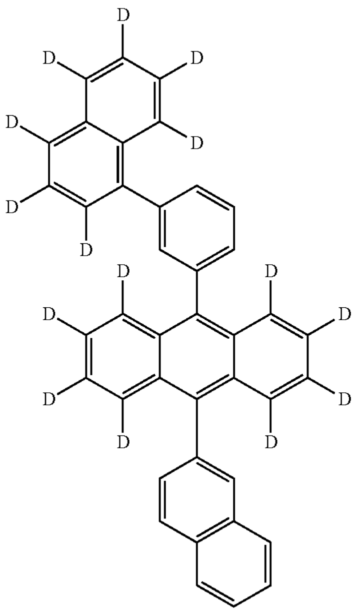
-continued
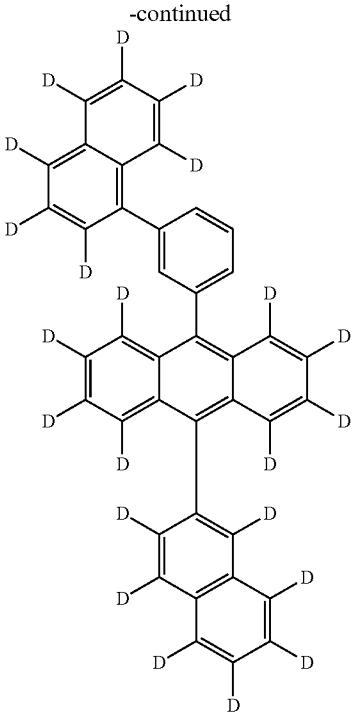
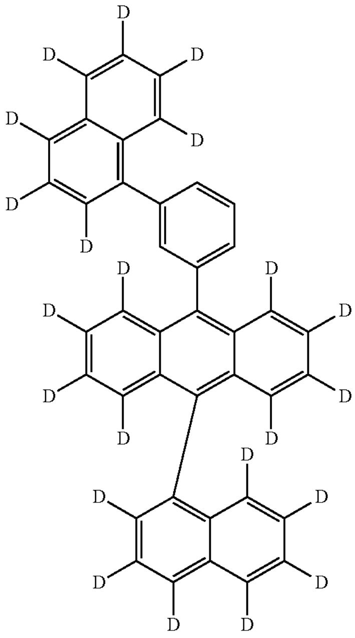
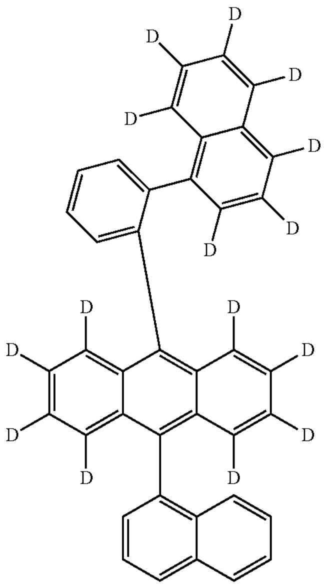

-continued
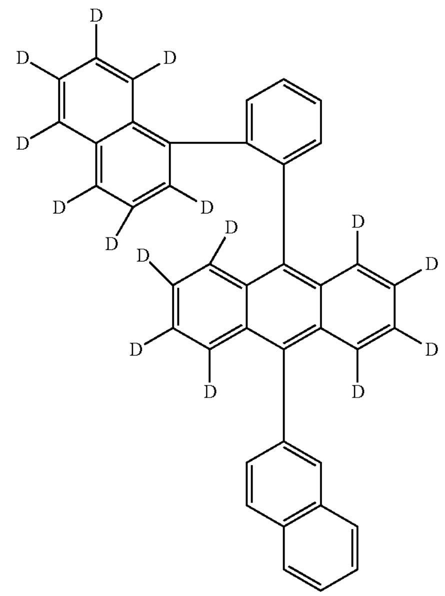
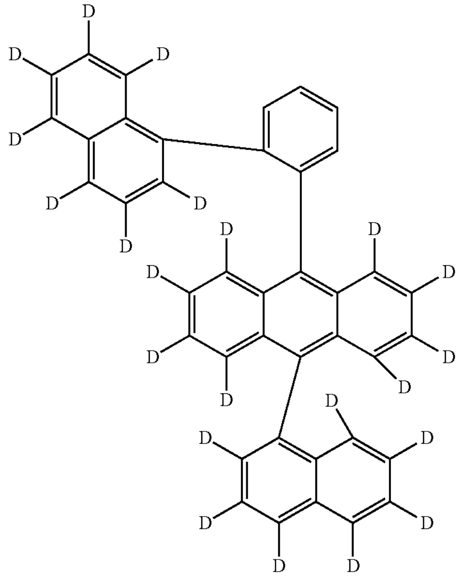
-continued
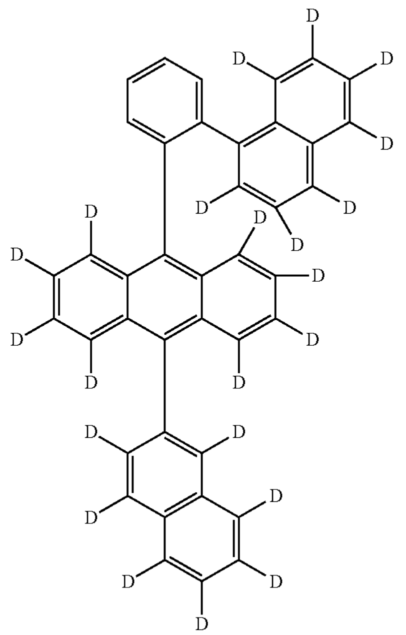
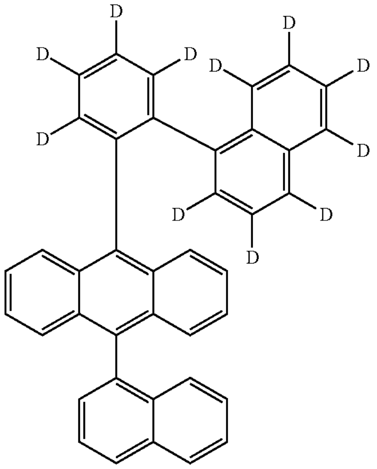
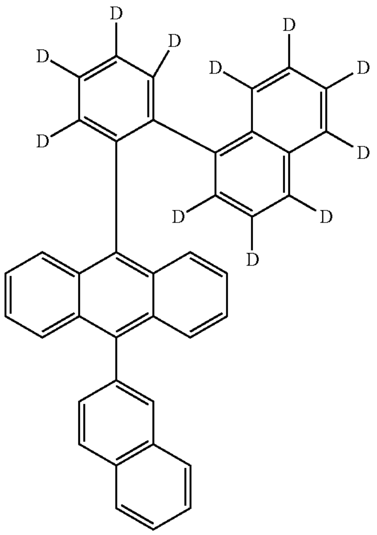

-continued
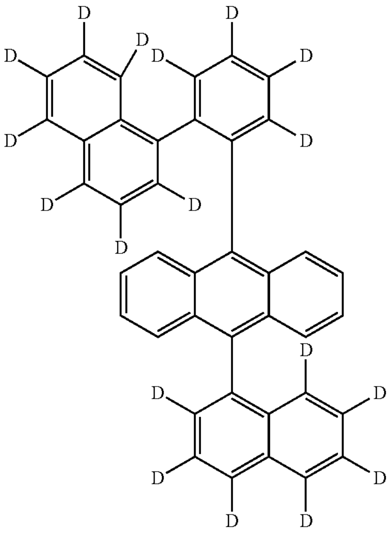
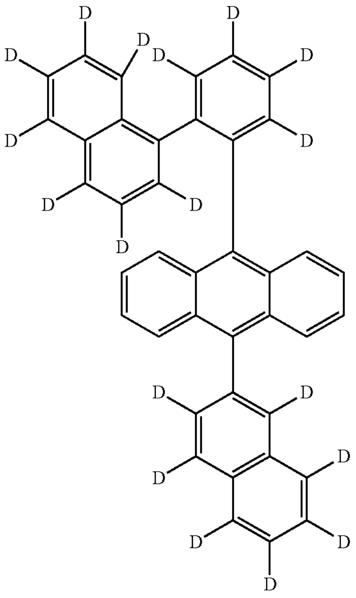
-continued
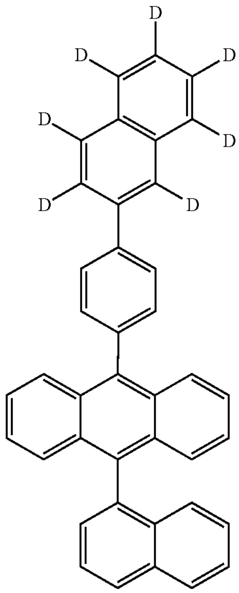
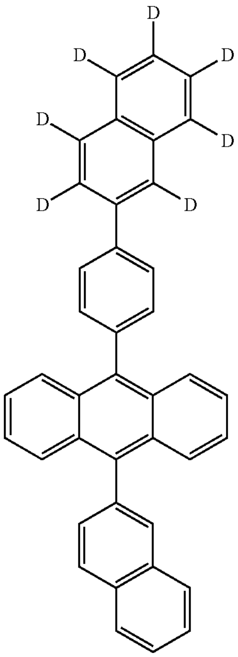
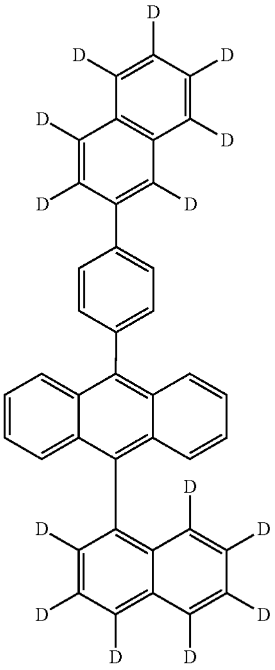
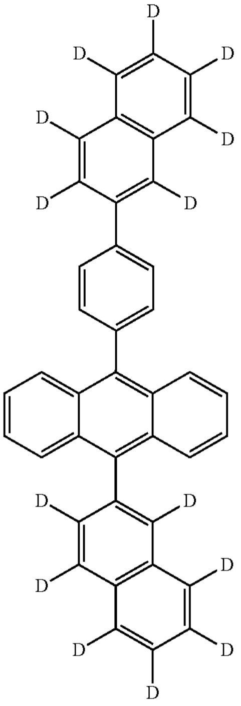

-continued
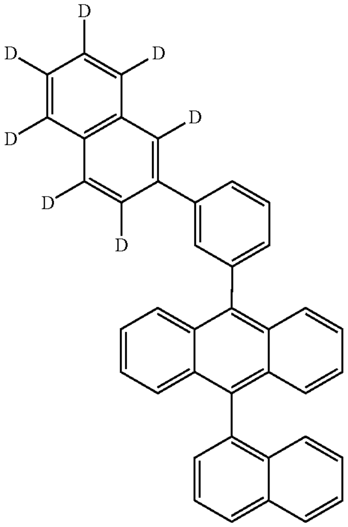
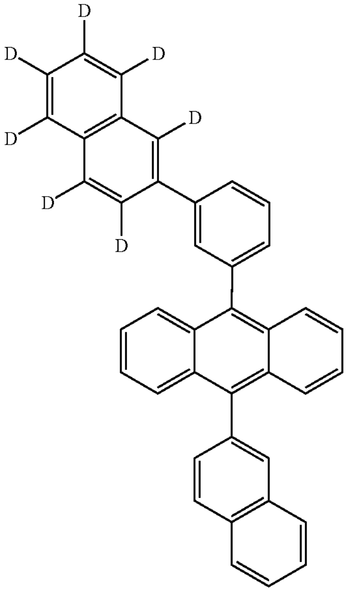
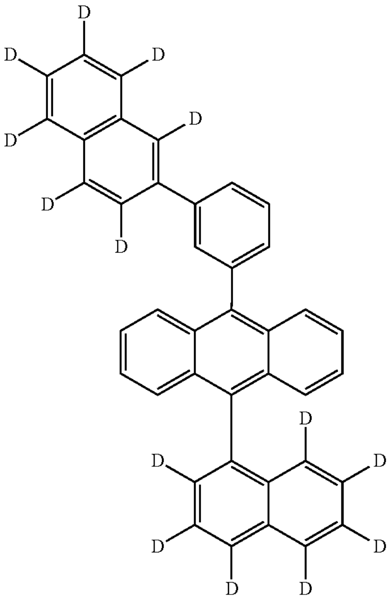
-continued
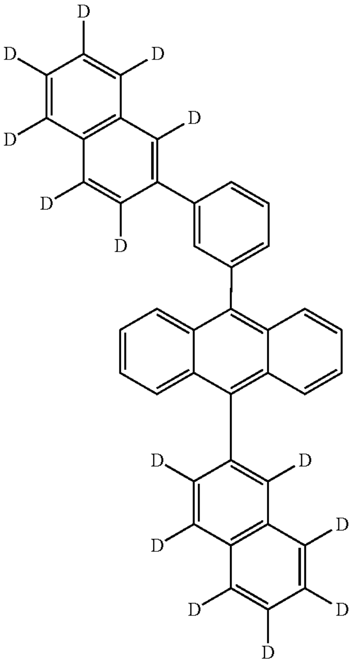
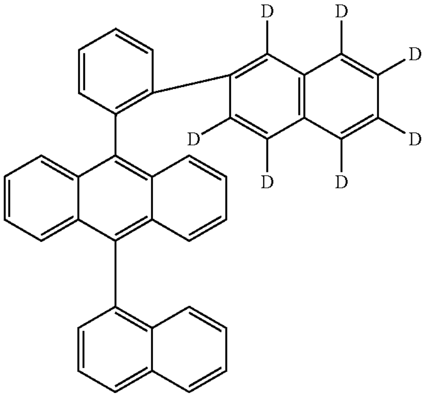
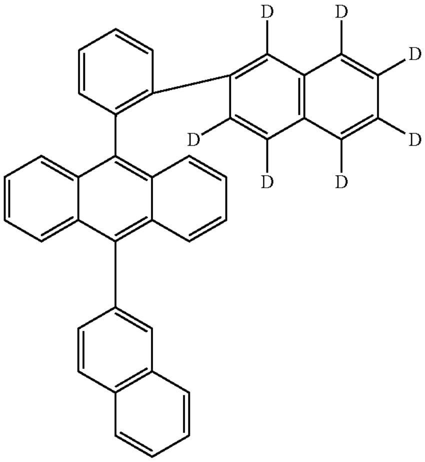

-continued
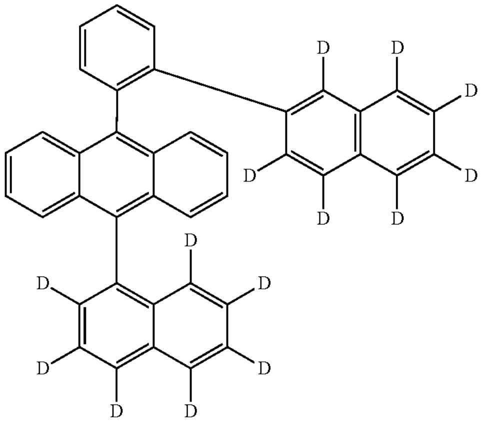
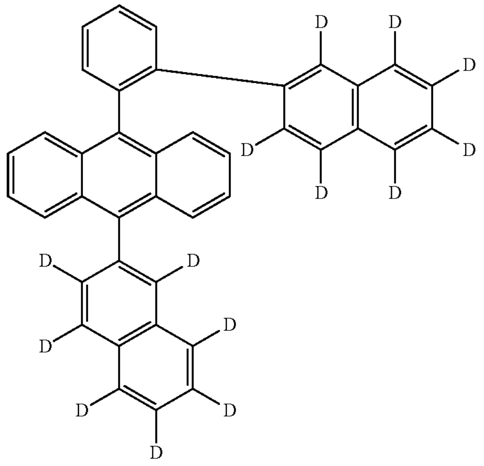
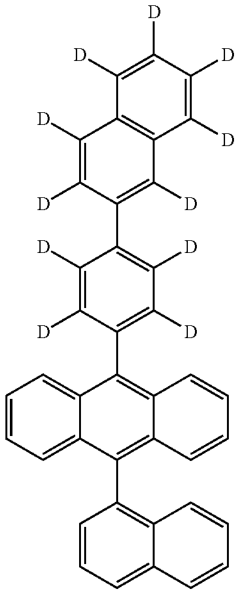
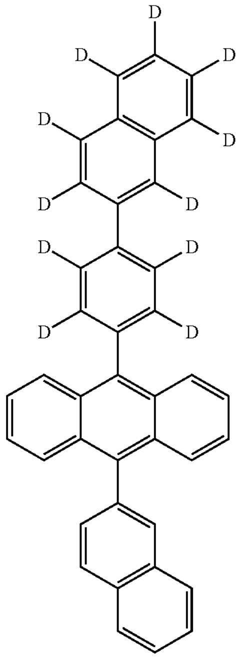
-continued
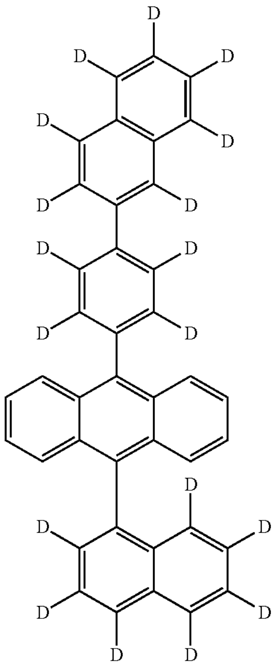
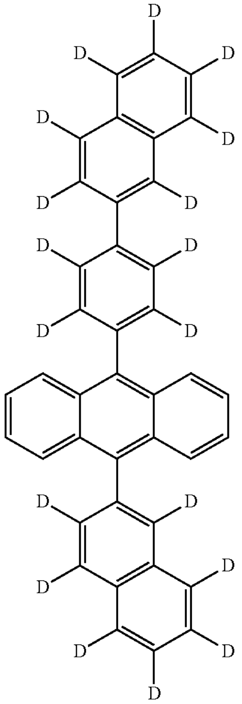
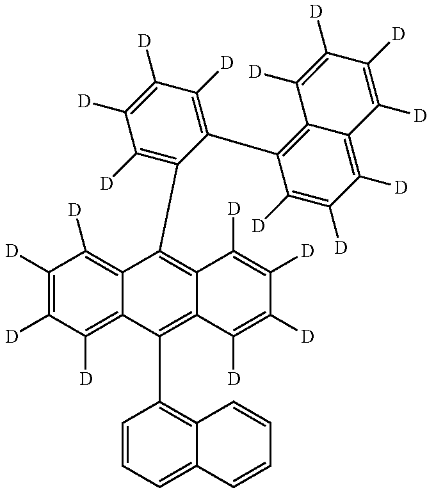

-continued
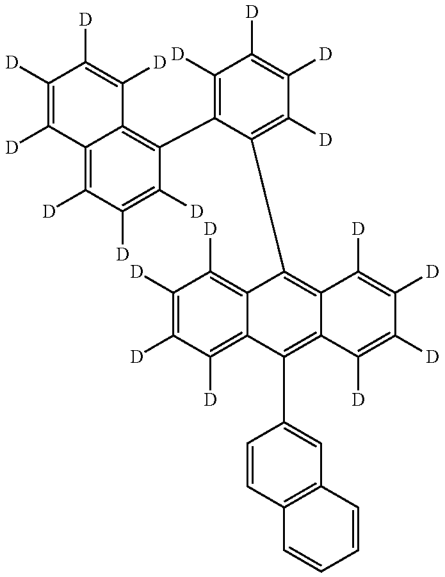
-continued
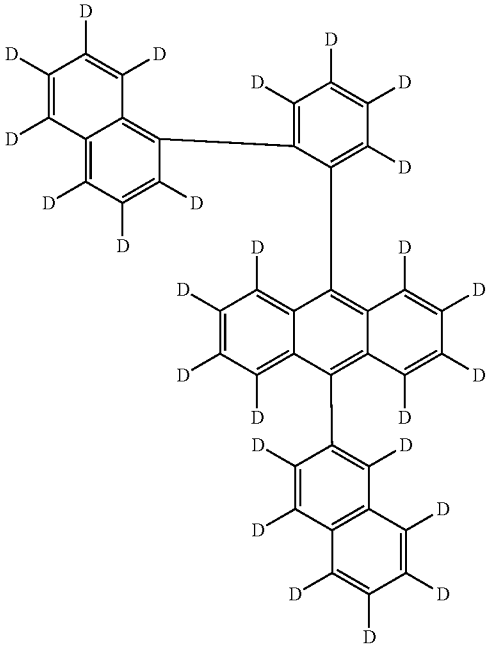
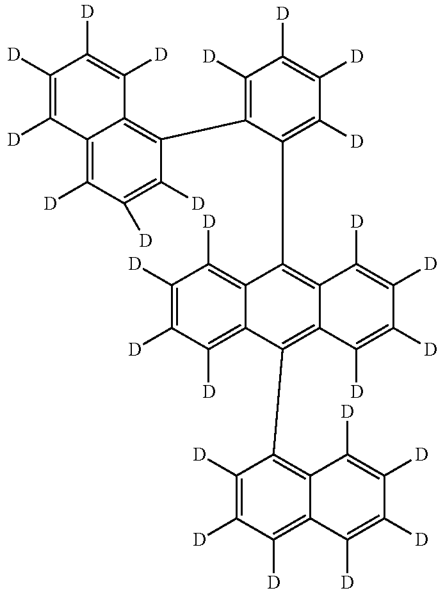
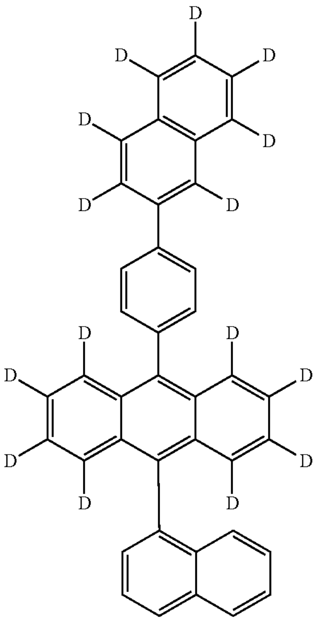

-continued
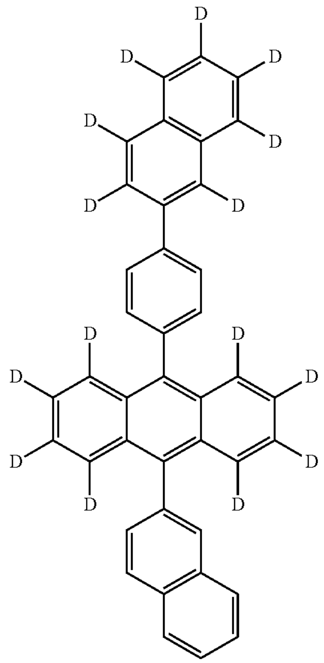
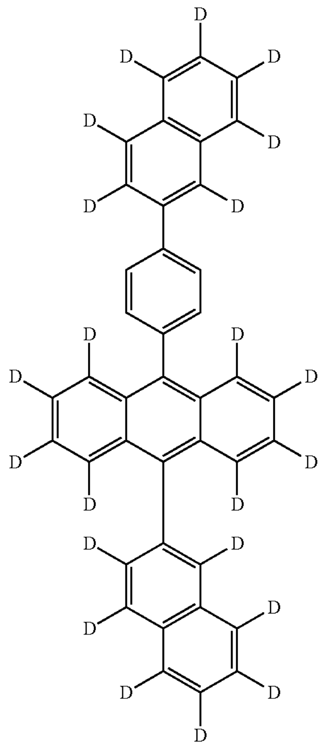
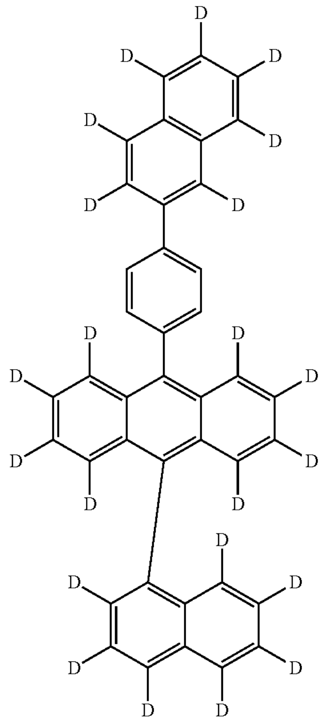
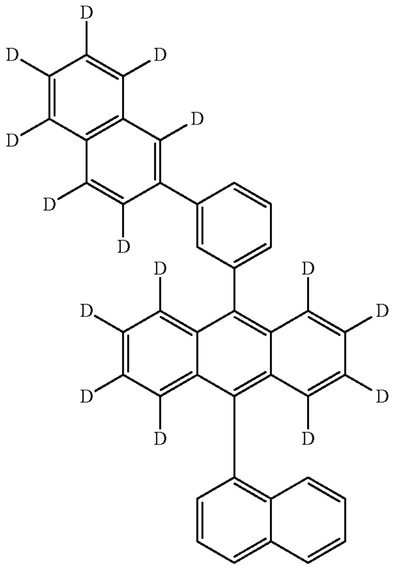

-continued
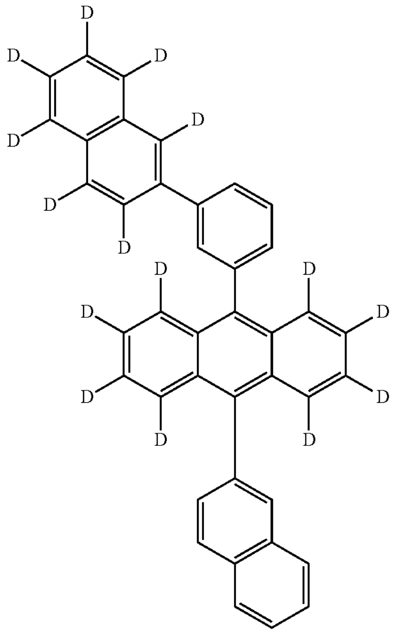
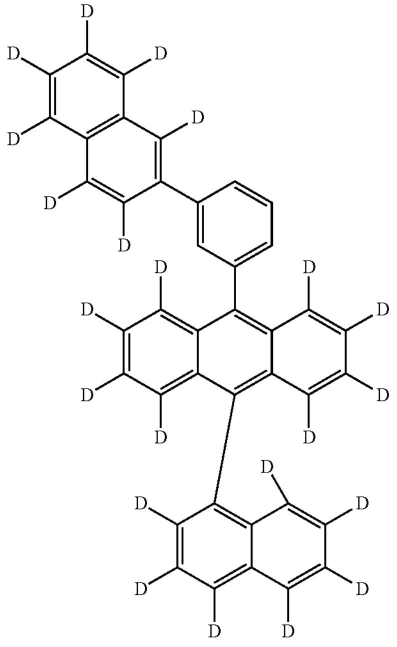
-continued
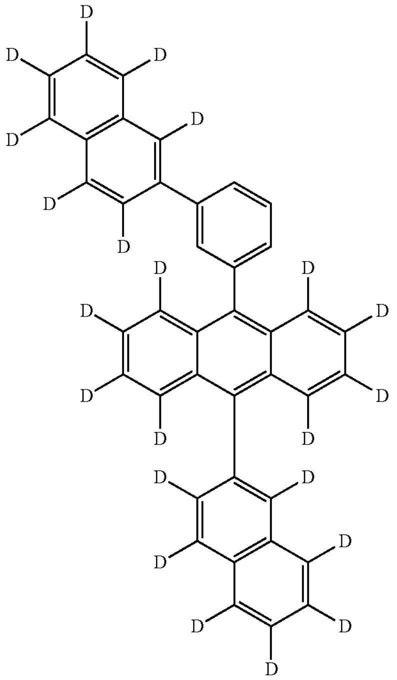
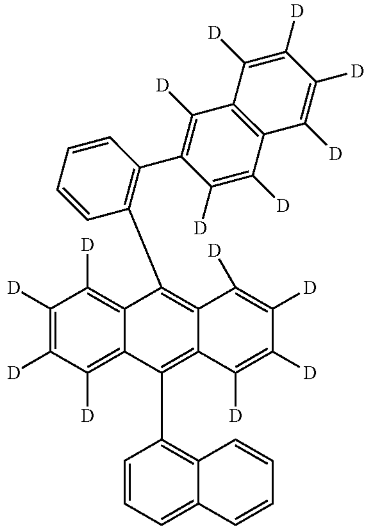

-continued
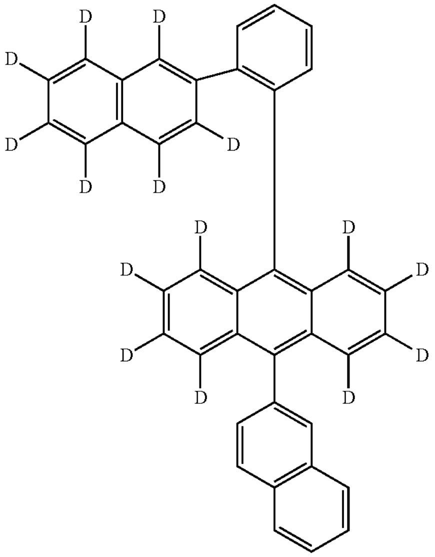
-continued
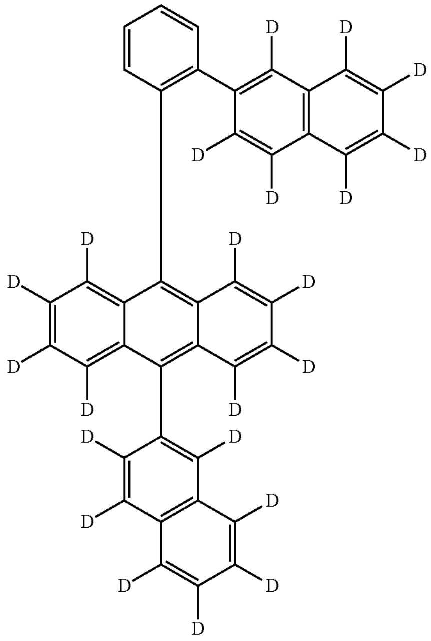
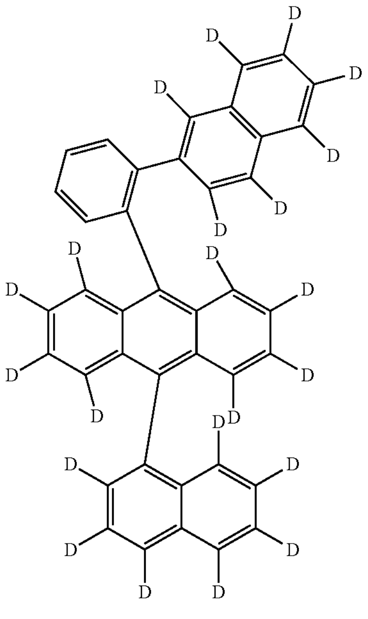
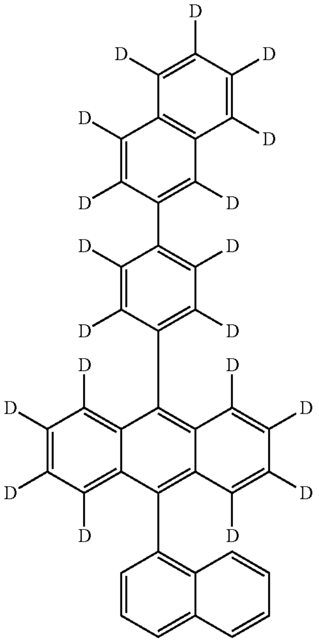

-continued
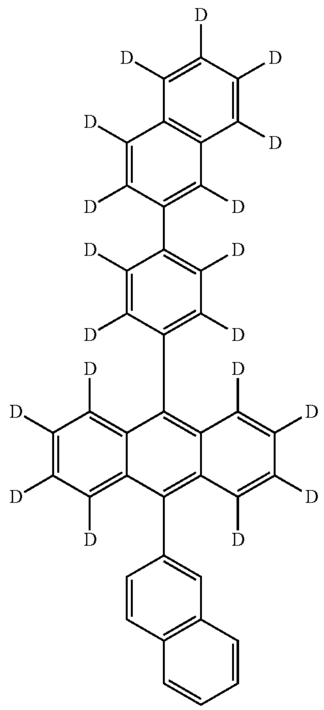
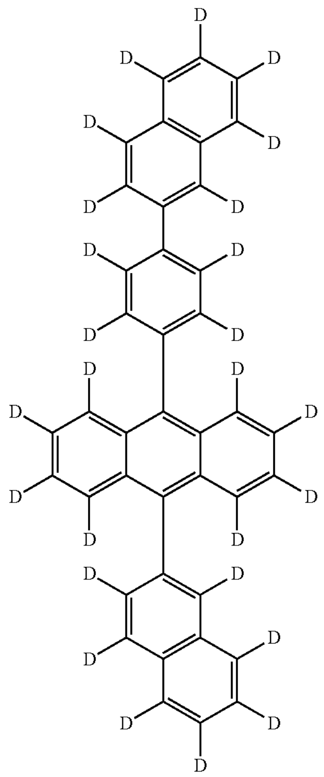
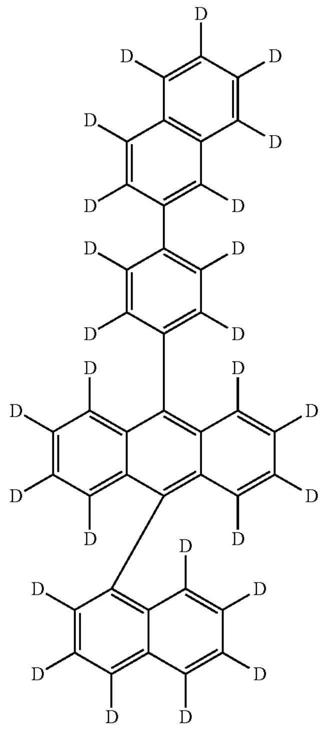
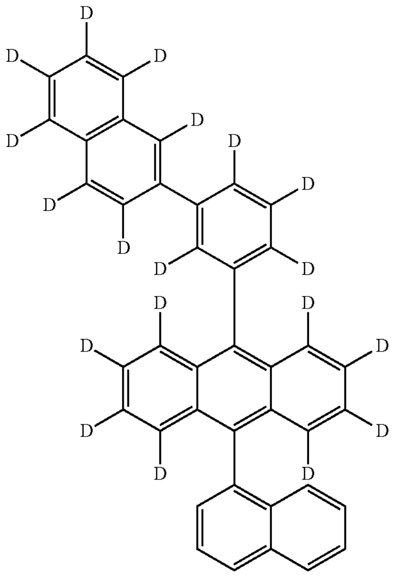

-continued
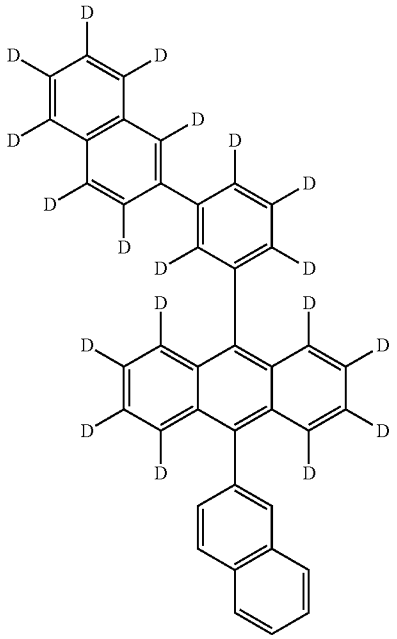
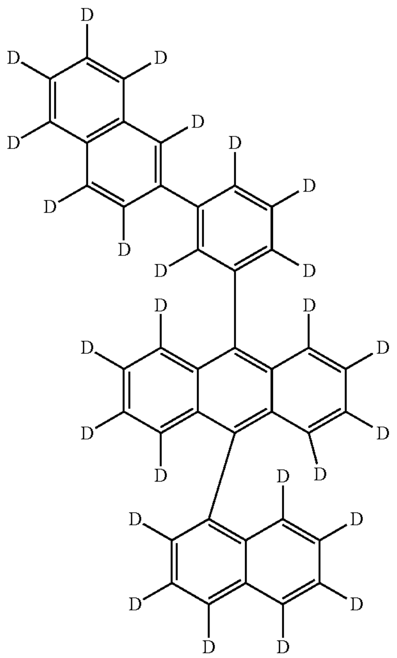
-continued
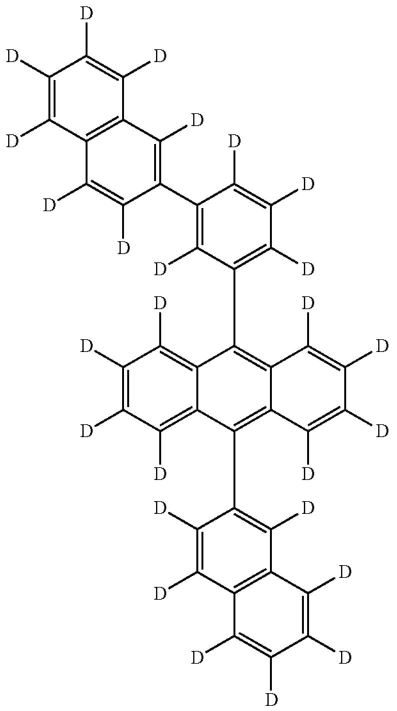
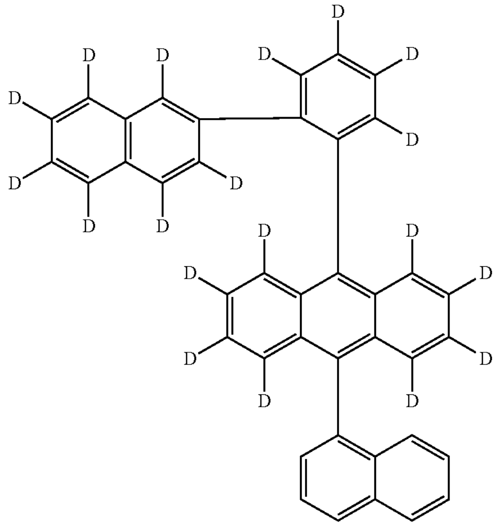

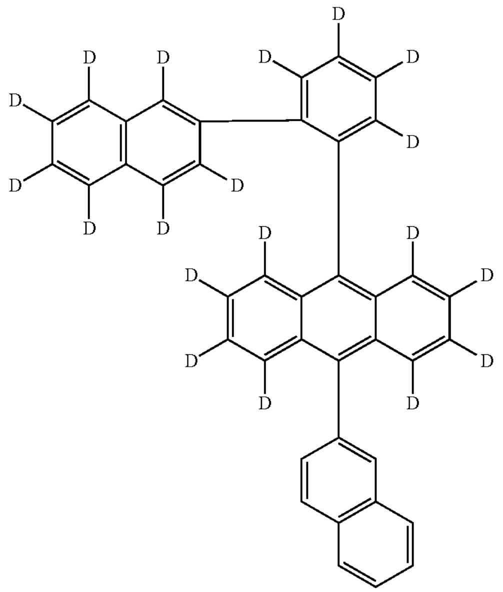
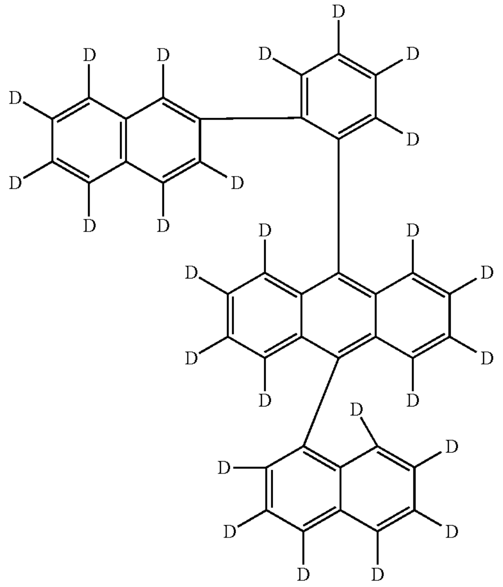
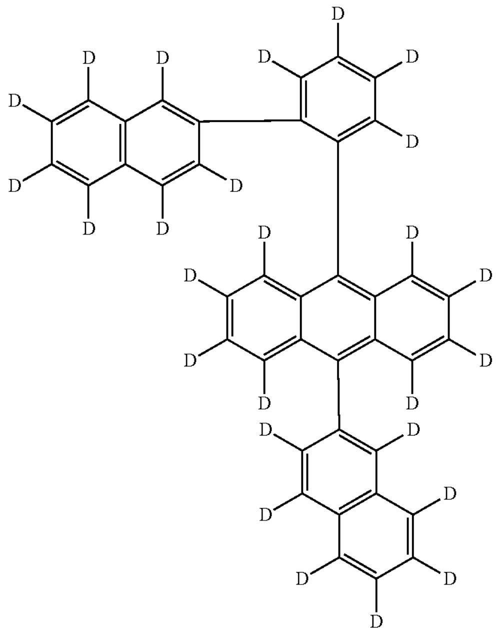
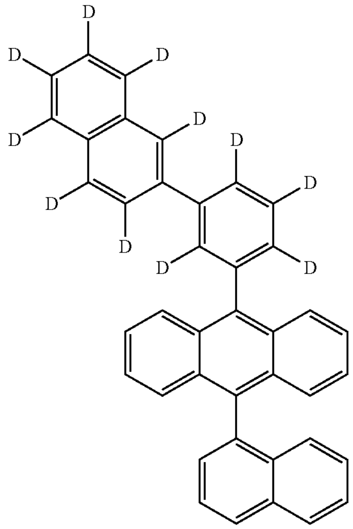

-continued
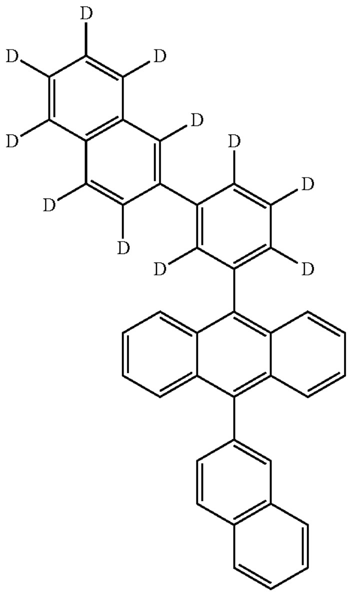
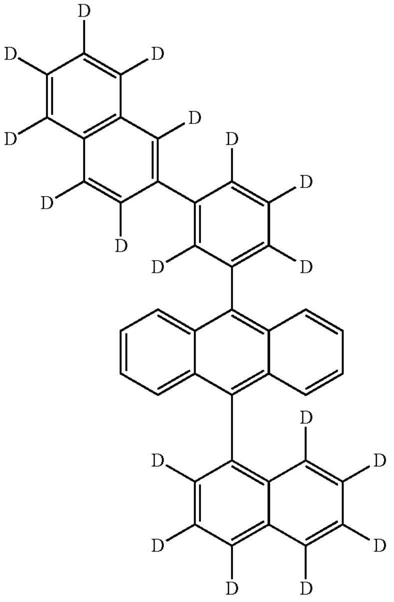
-continued
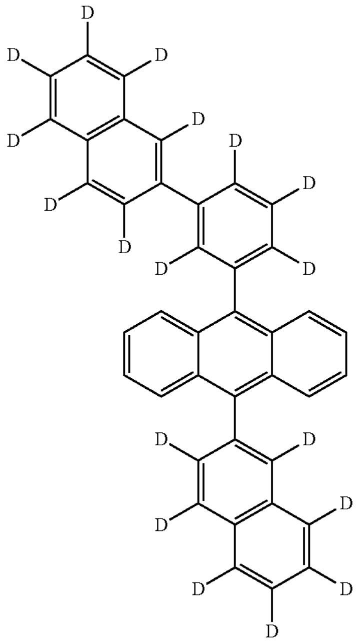
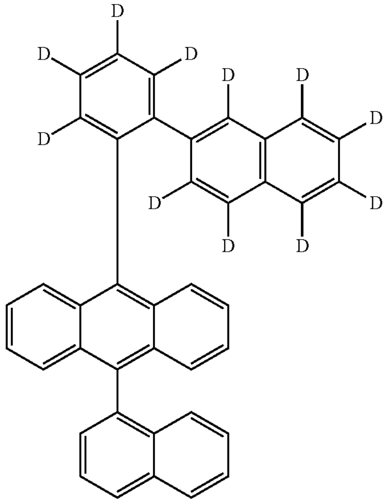
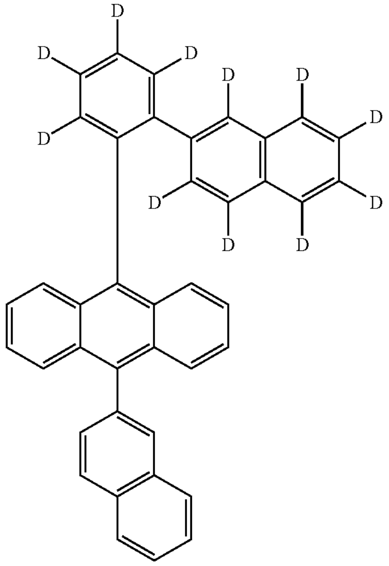

-continued
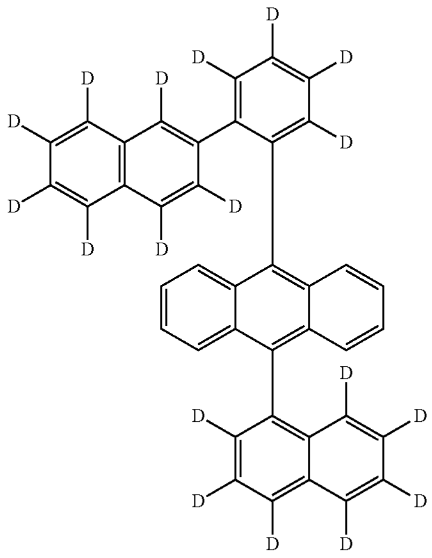
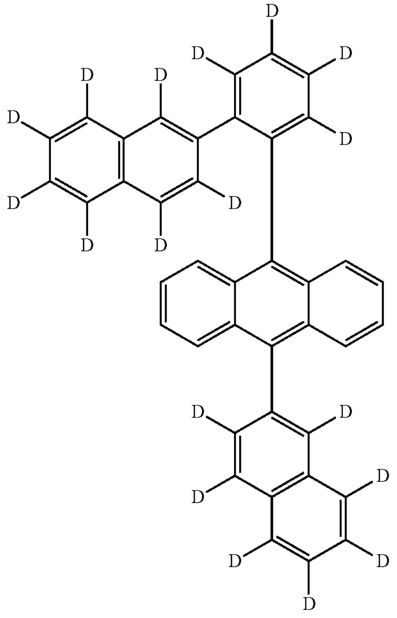
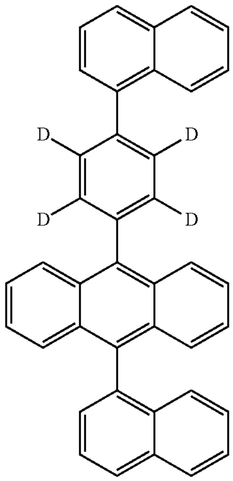
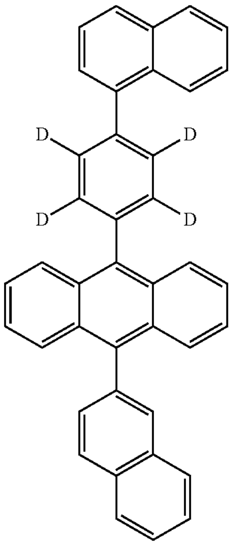
-continued
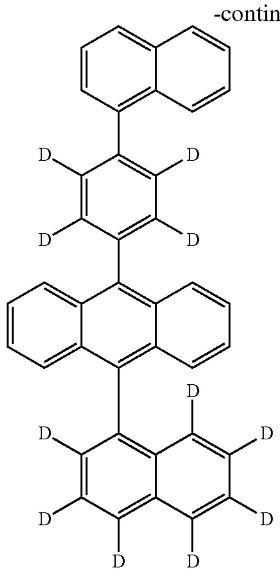
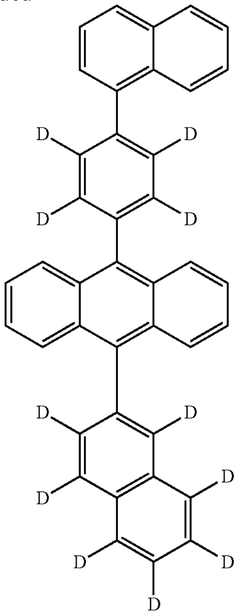
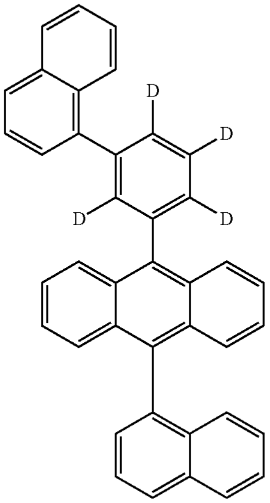
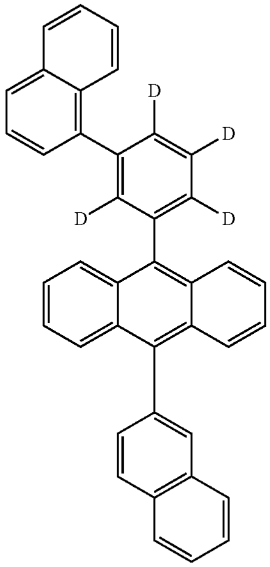
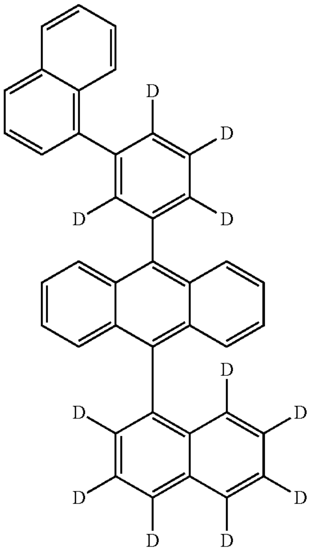

-continued
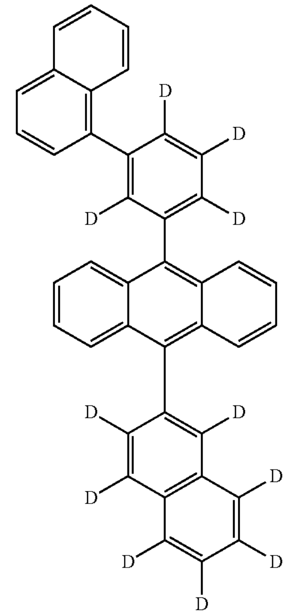
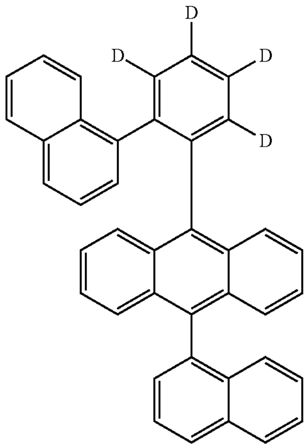
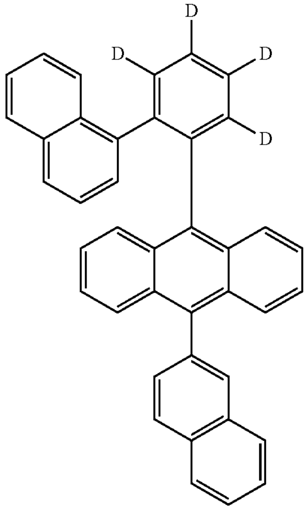
-continued
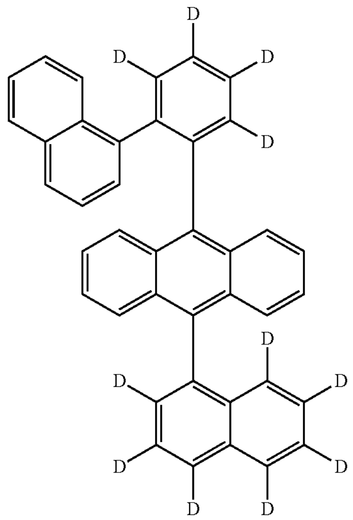
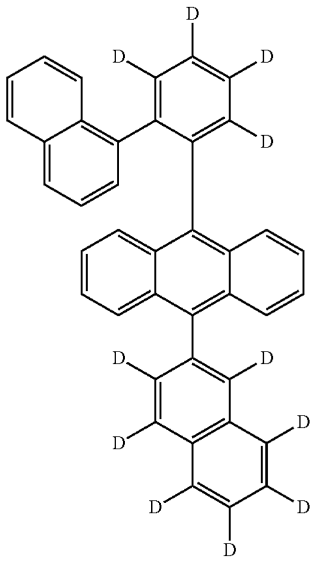
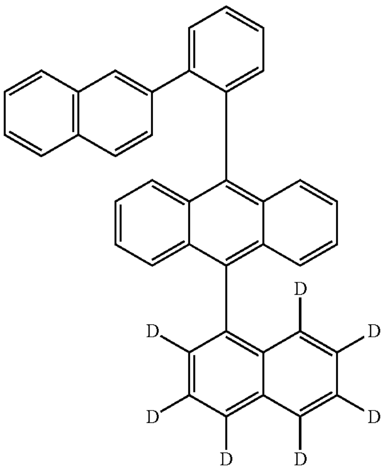

-continued
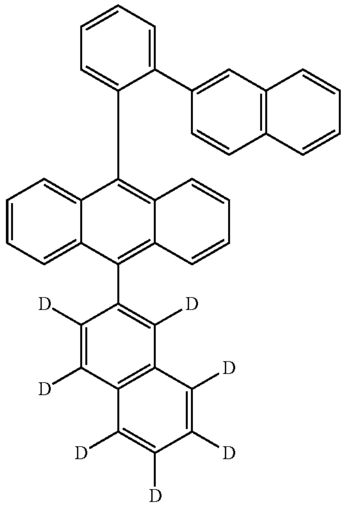
-continued
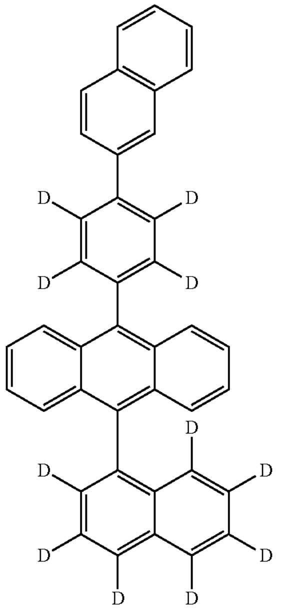
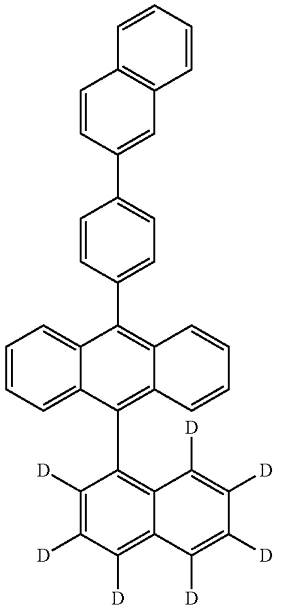
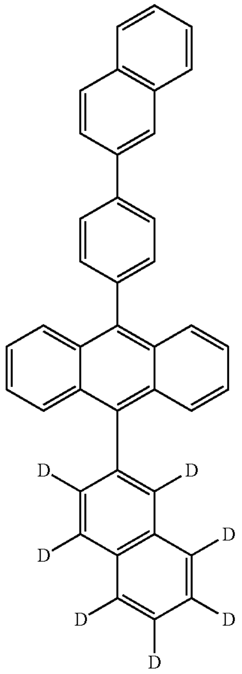
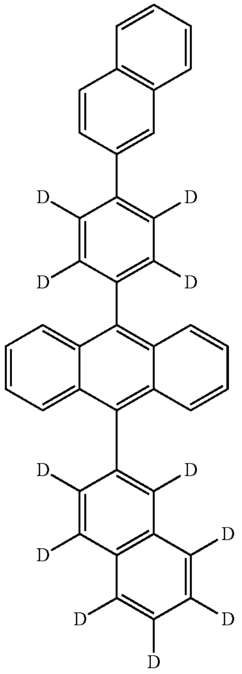

-continued
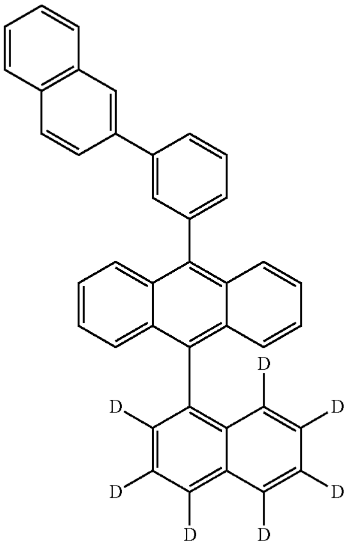
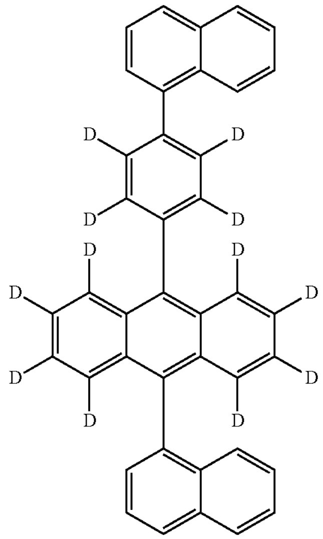
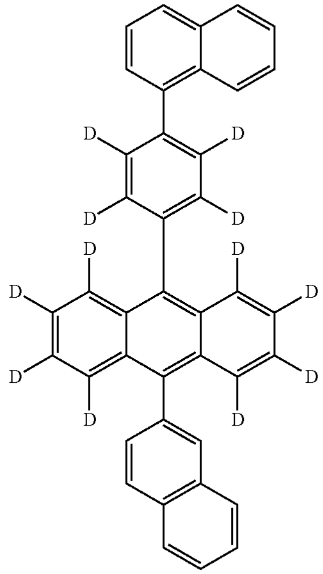
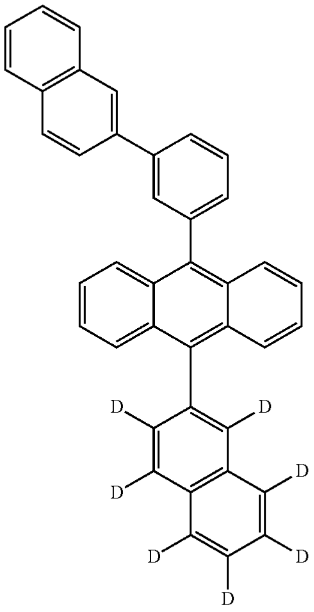
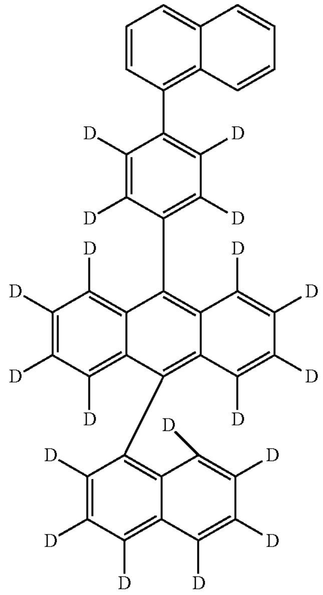

-continued
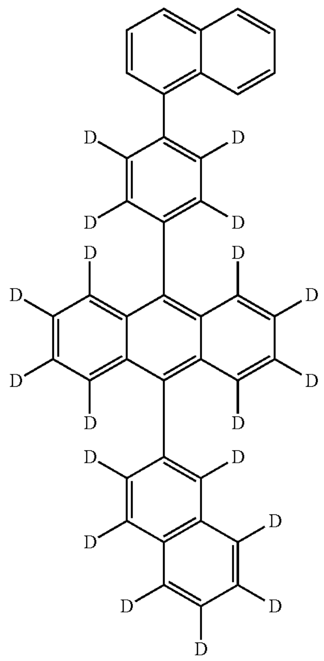
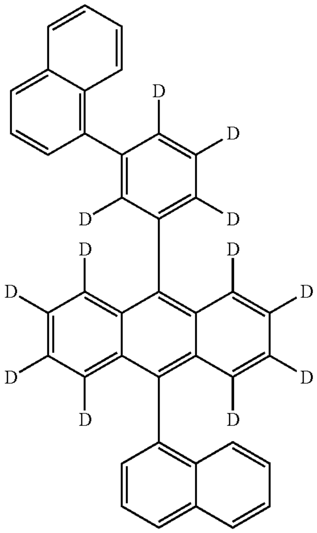
-continued
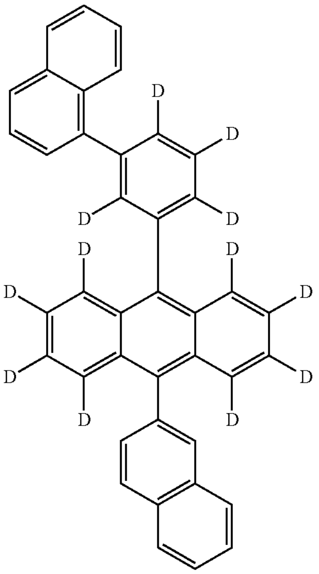
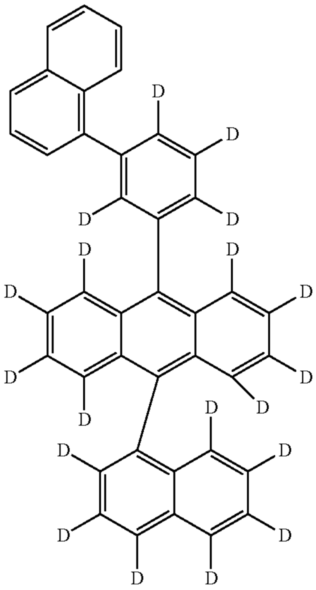

-continued
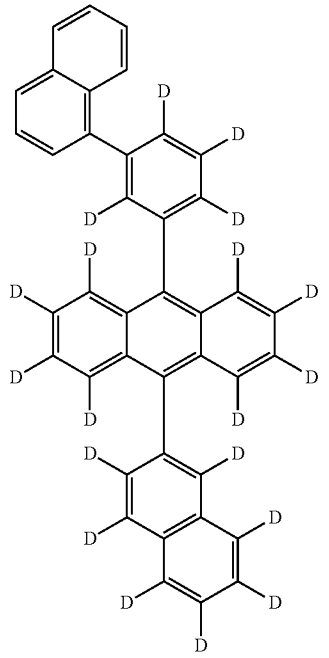
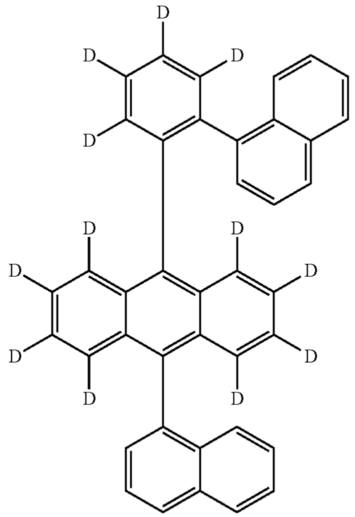
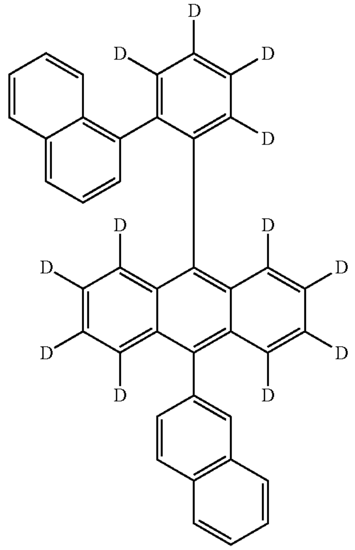
-continued
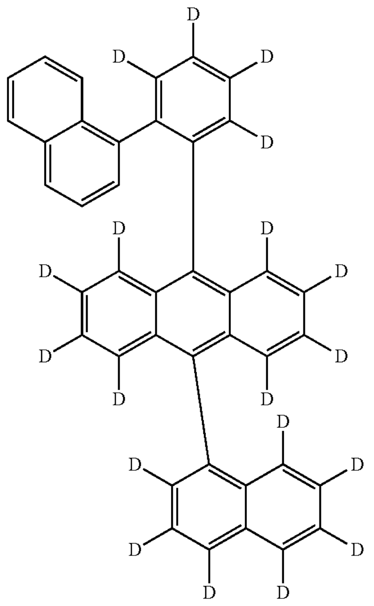
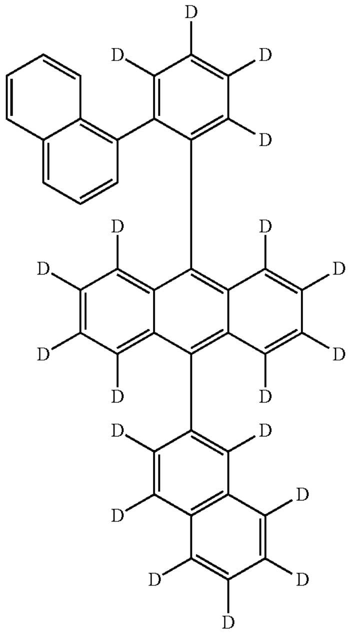

-continued
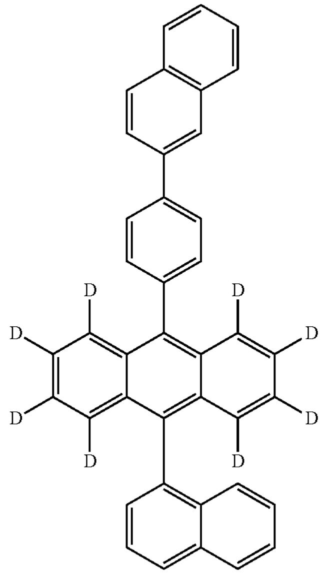
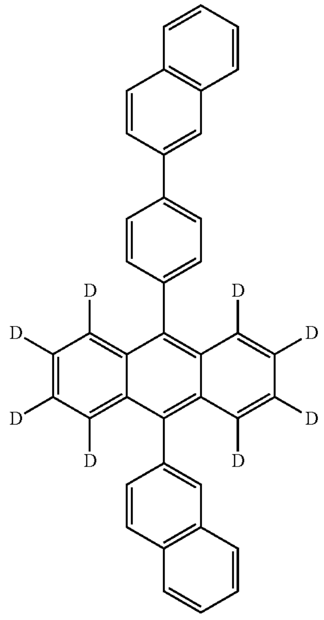
-continued
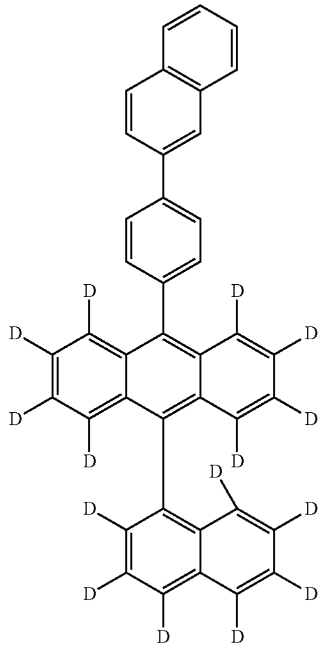
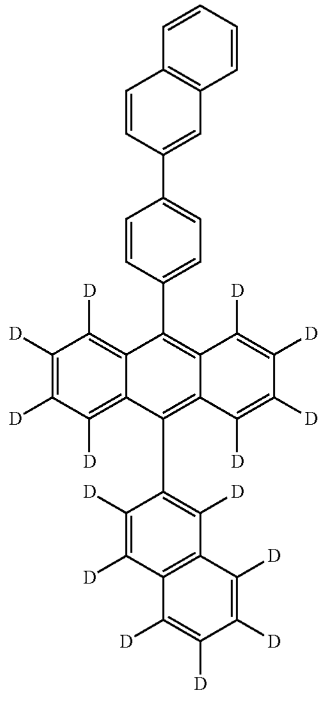

-continued
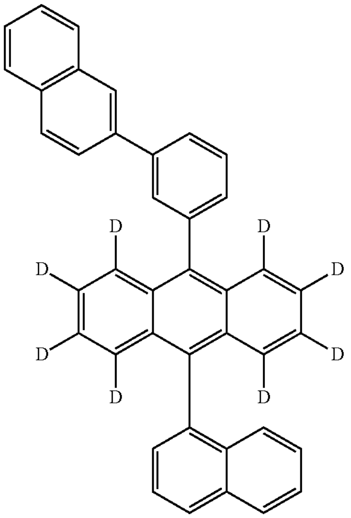
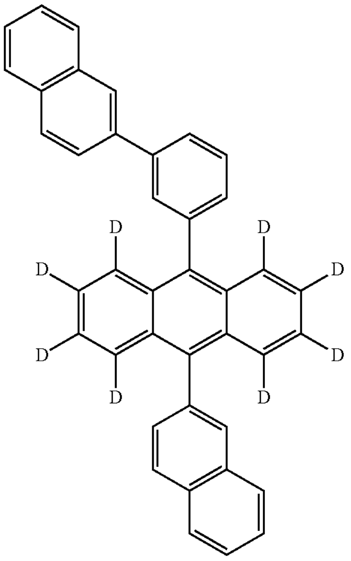
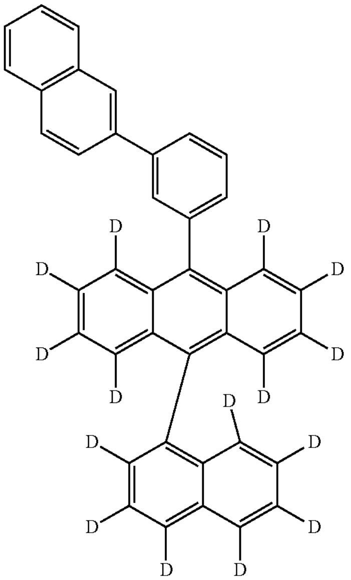
-continued
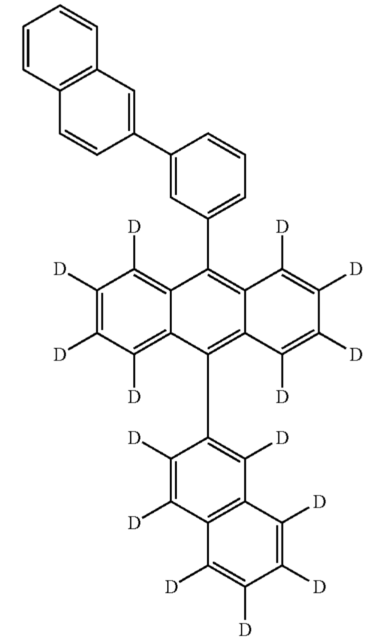
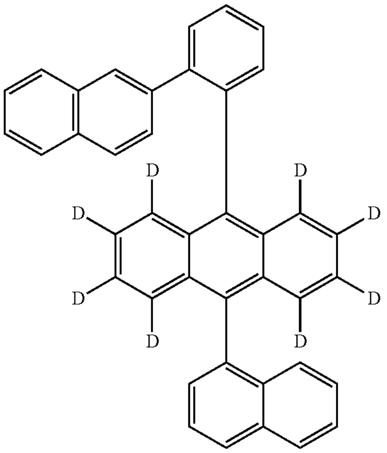
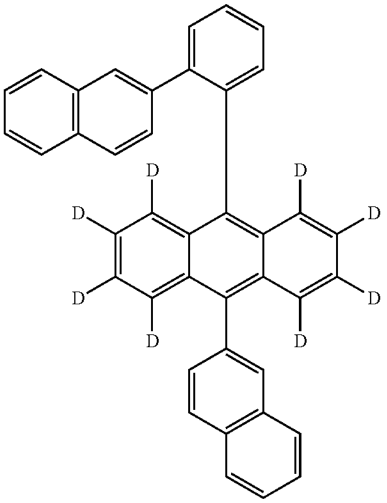

-continued
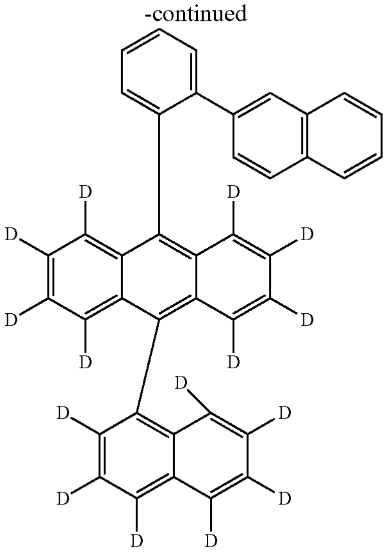
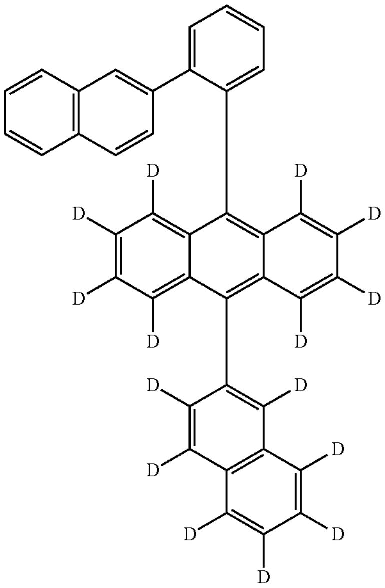
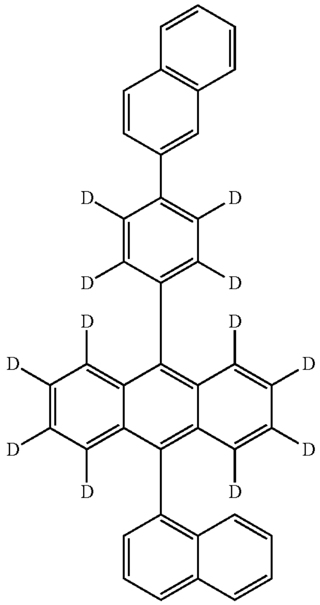
-continued
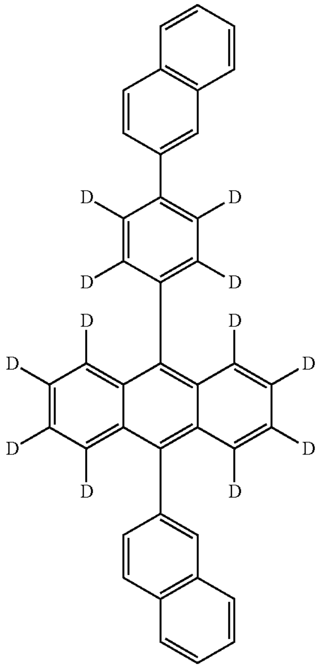
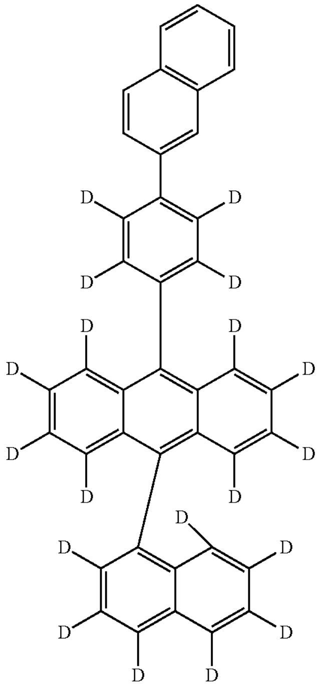

-continued
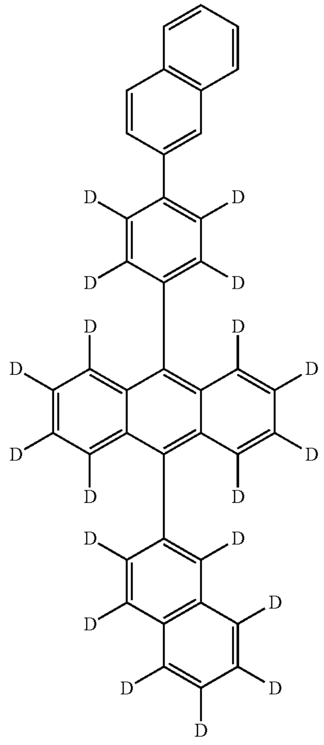
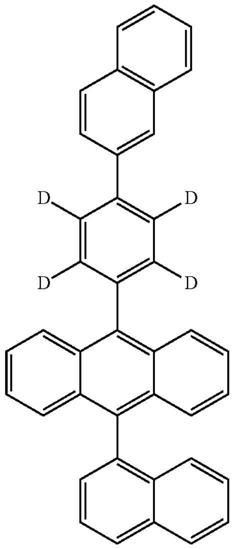
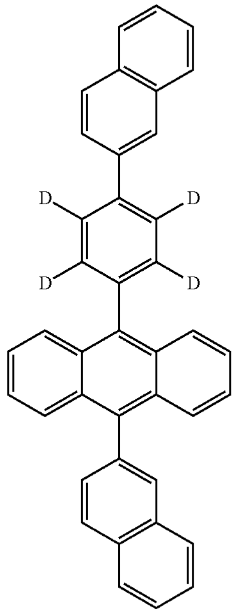
-continued
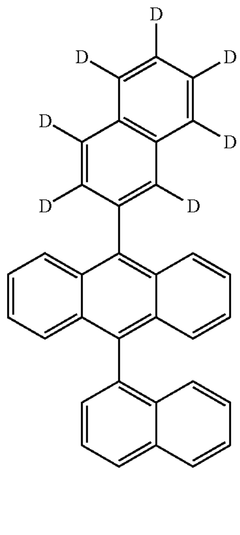
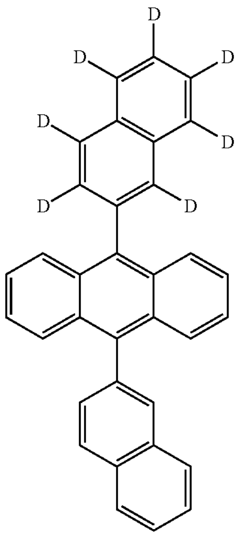
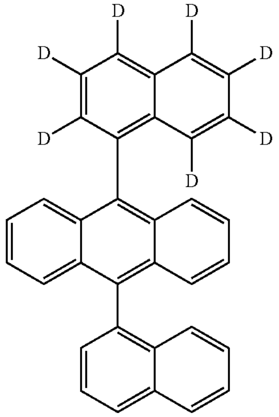
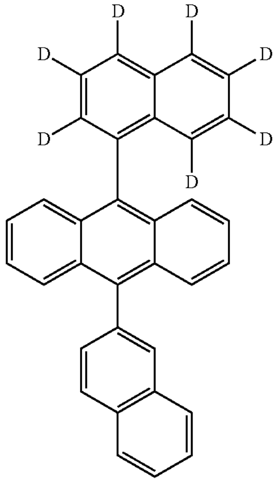

-continued
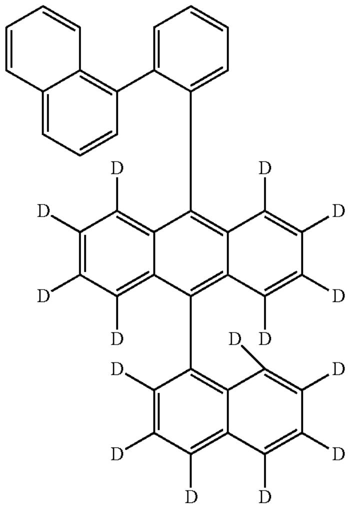
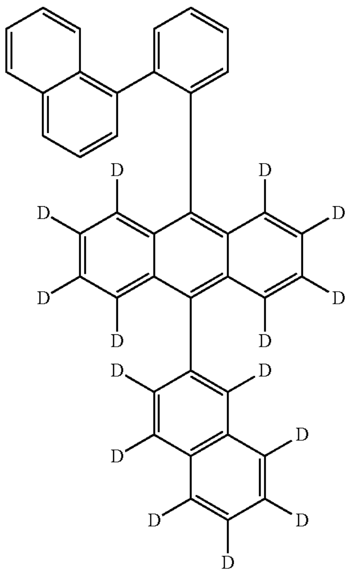
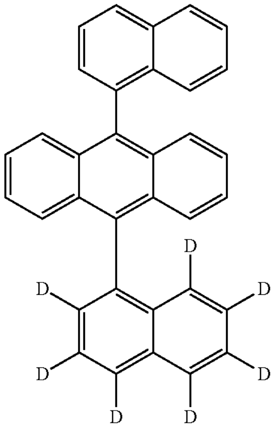
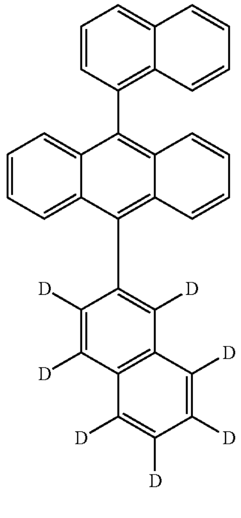
-continued
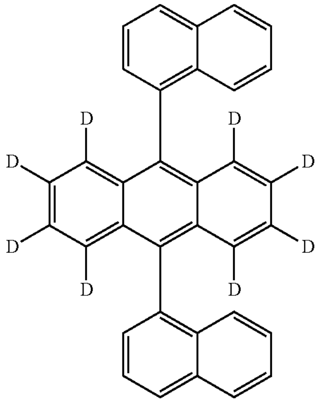
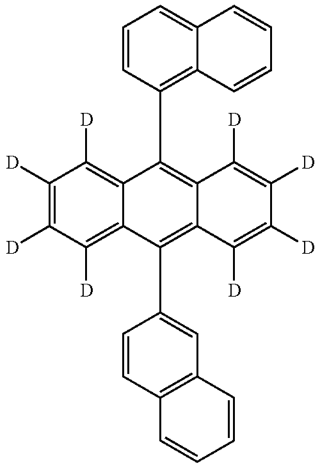
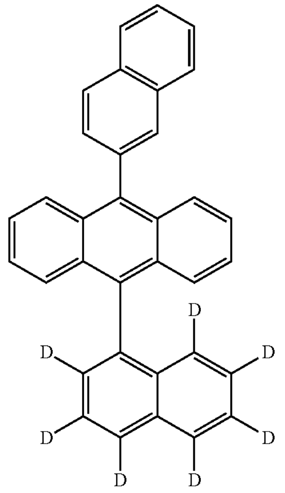
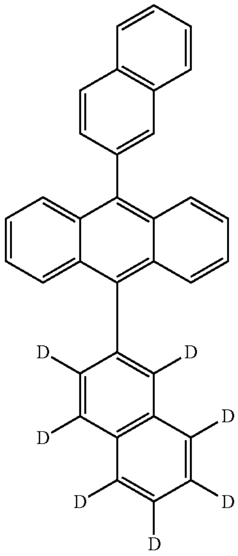

-continued
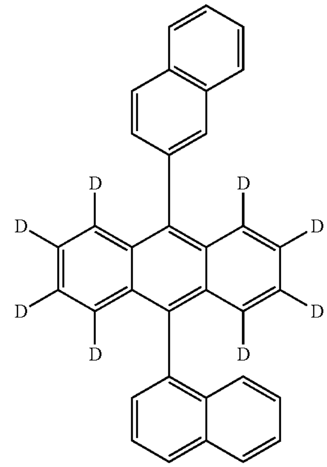
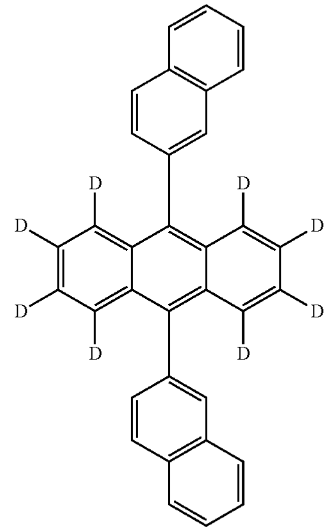
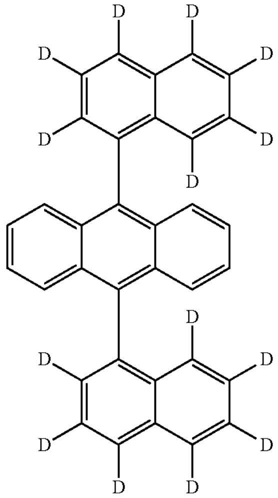
-continued
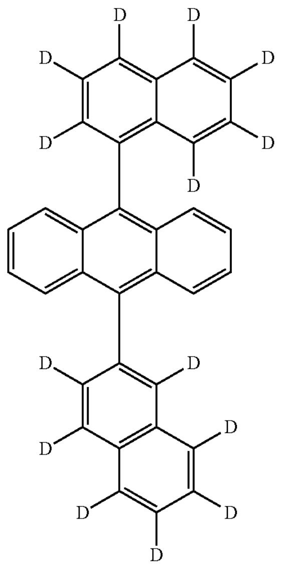
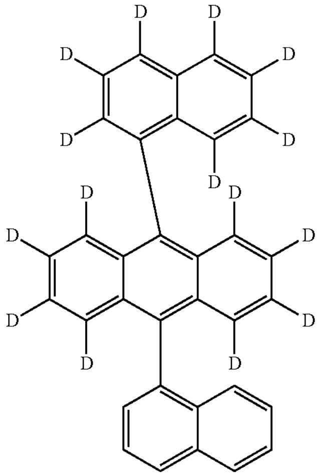
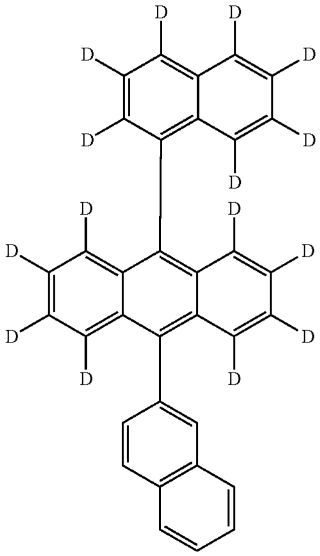

-continued
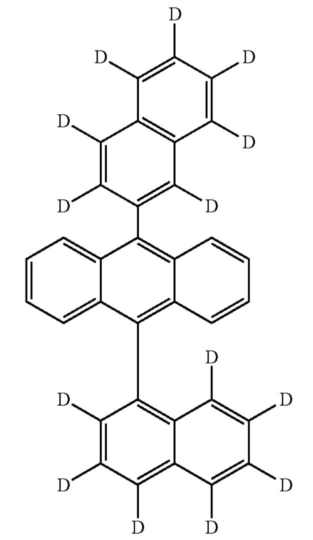
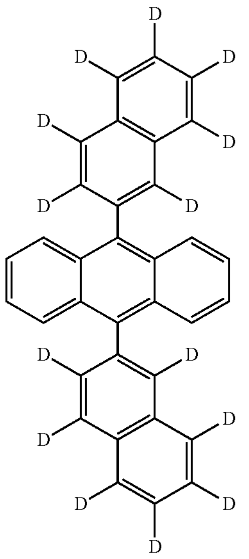
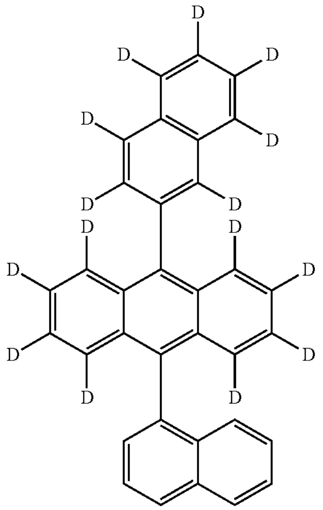
-continued
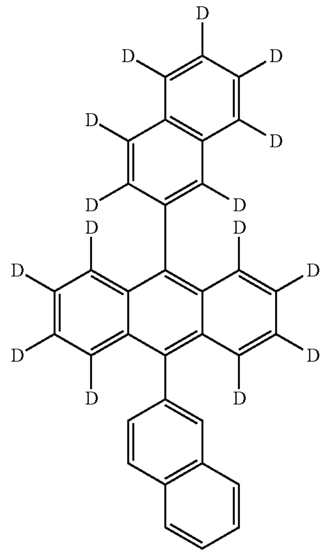
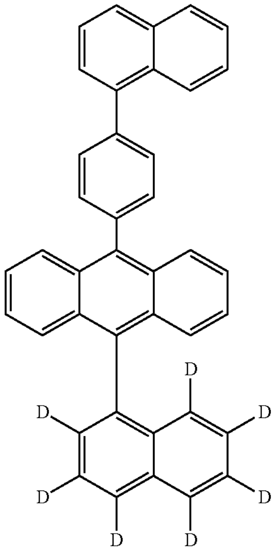
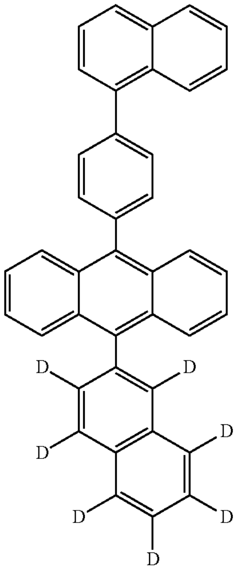
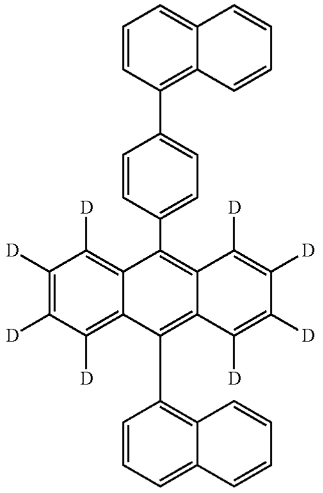

-continued
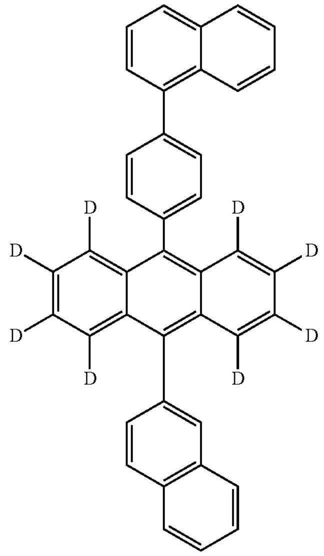
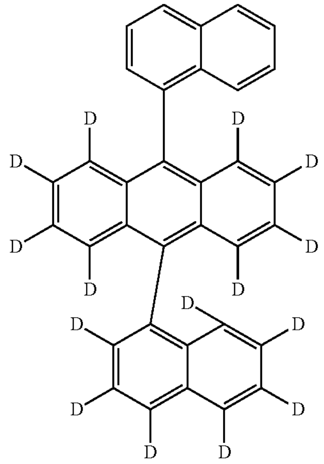
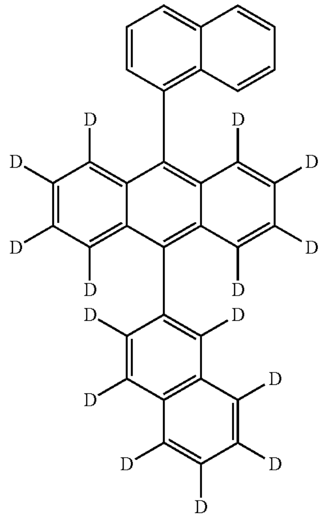
-continued
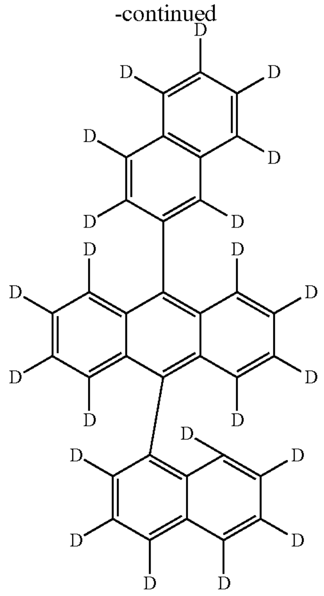
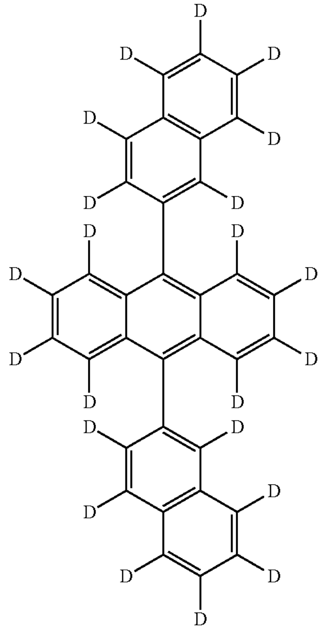
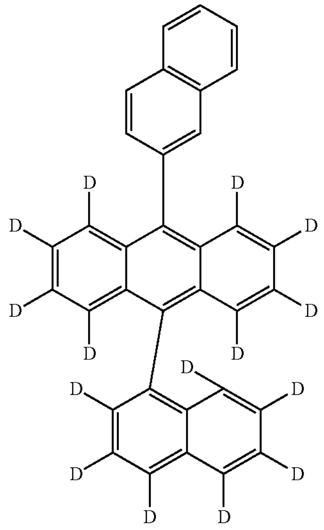

-continued
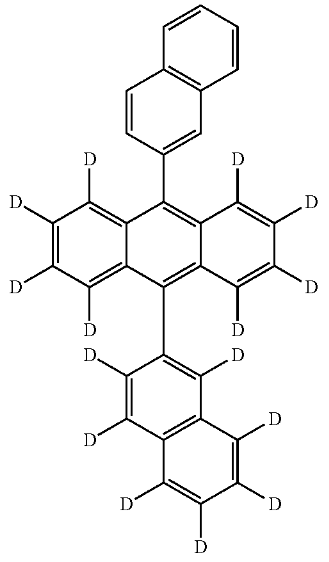
-continued
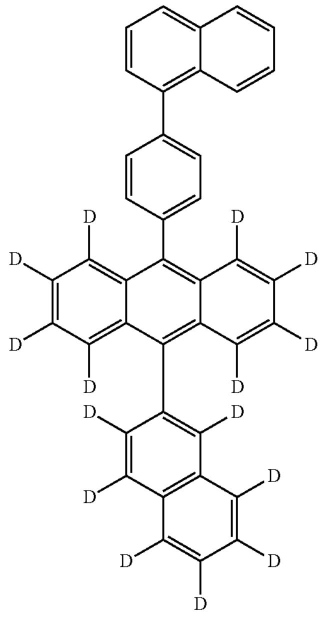
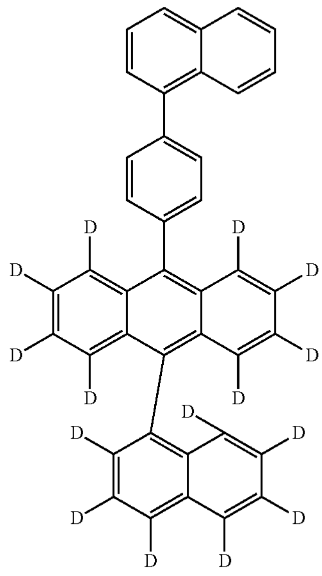
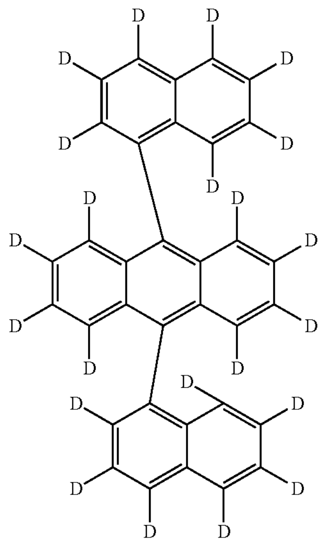

-continued
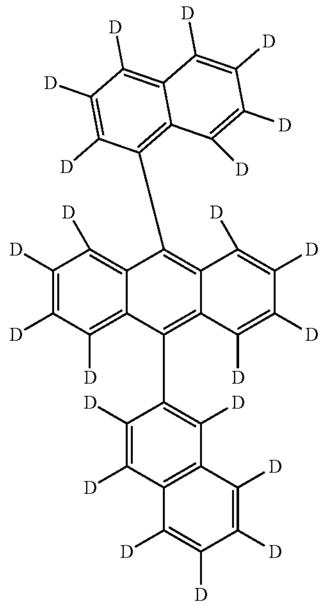
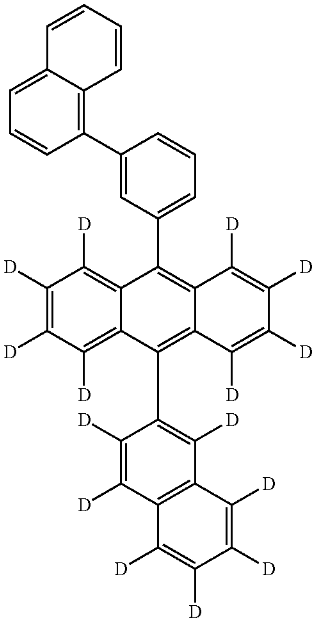
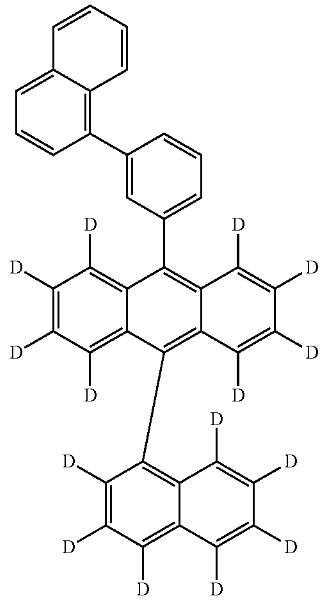
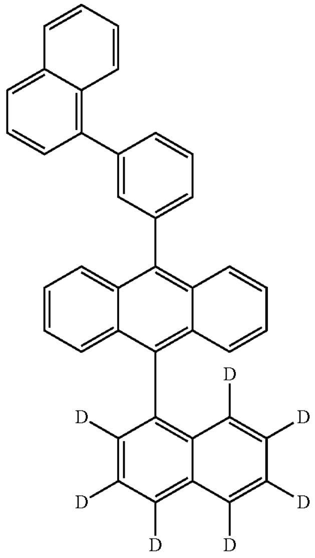

-continued
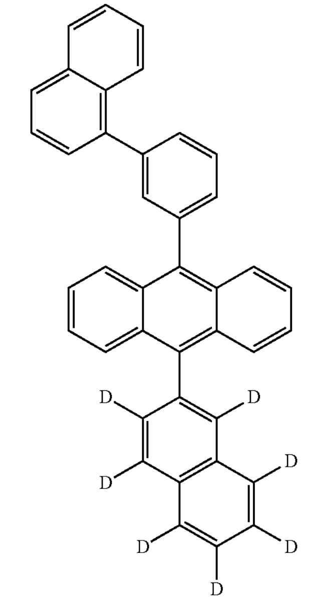
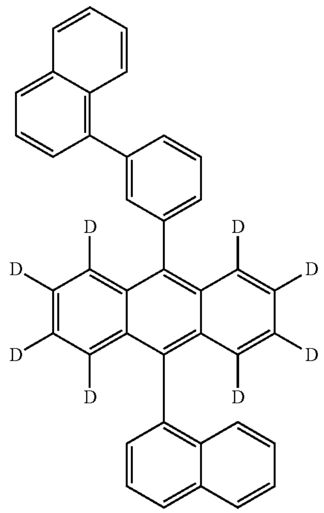
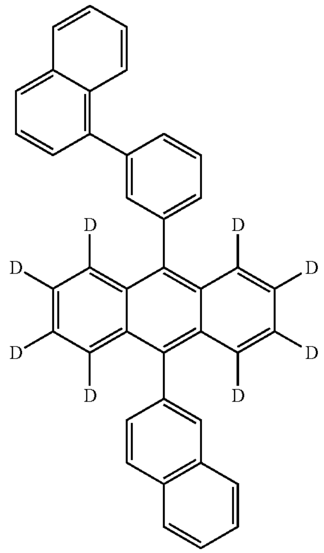
-continued
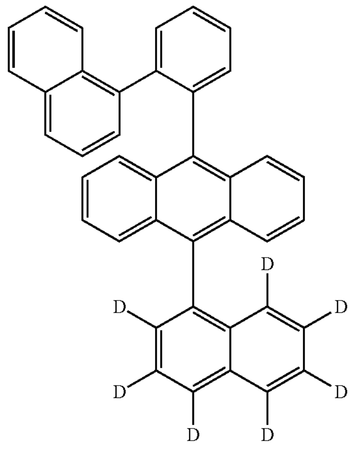
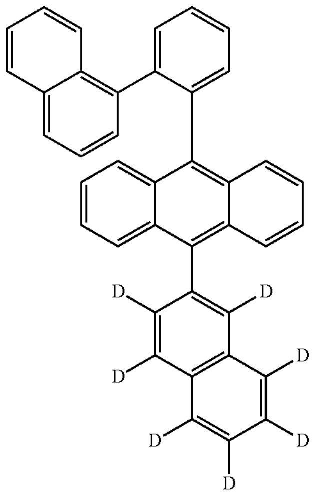
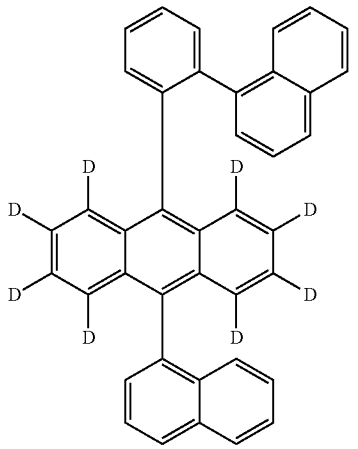

-continued
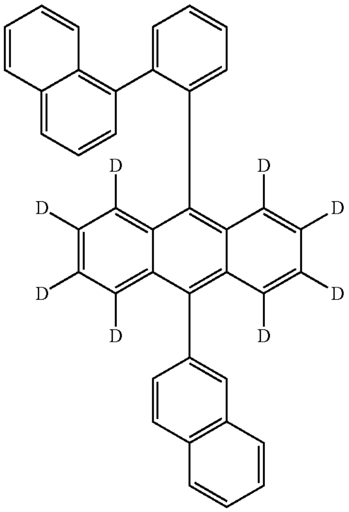
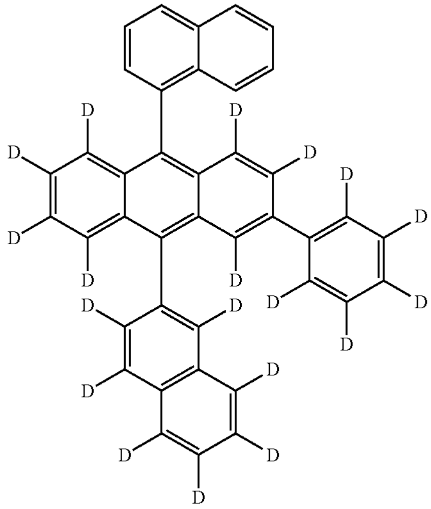
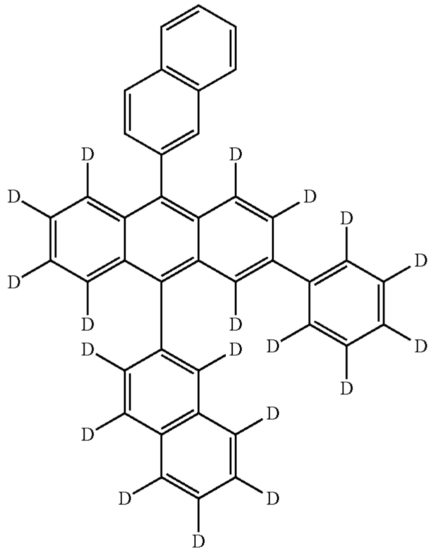
-continued
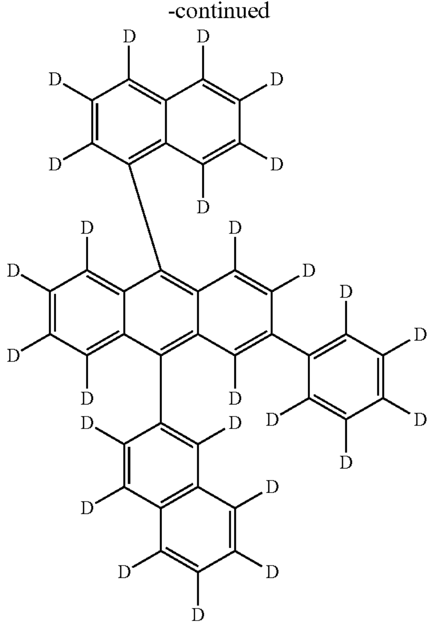
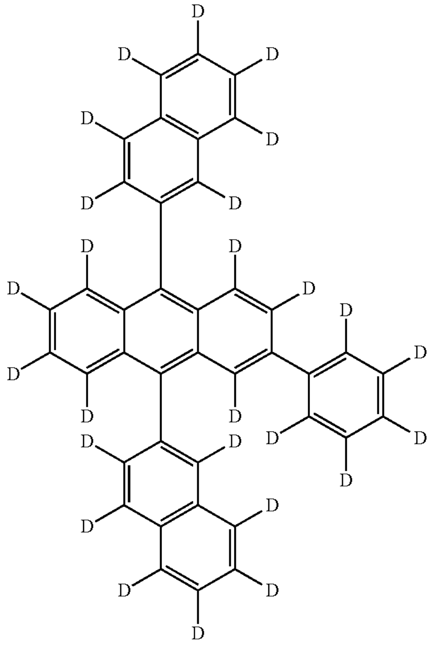

-continued
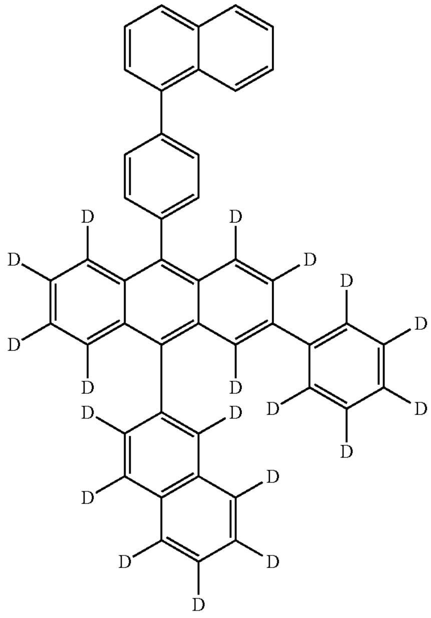
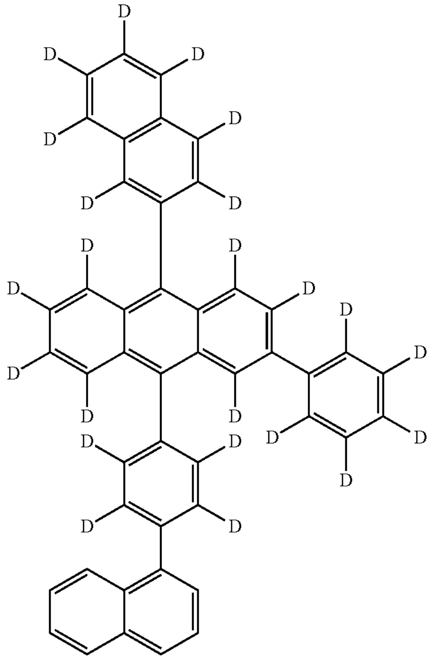
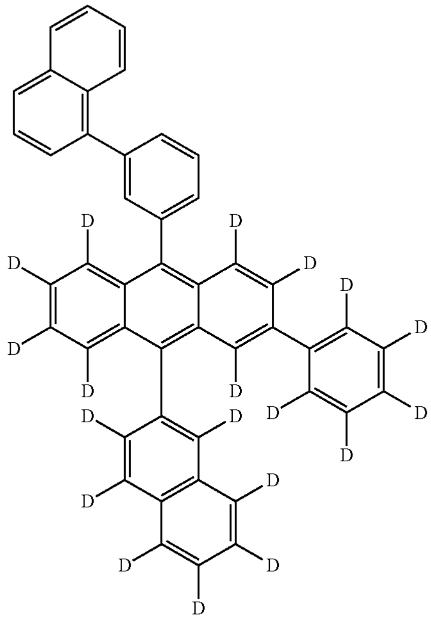
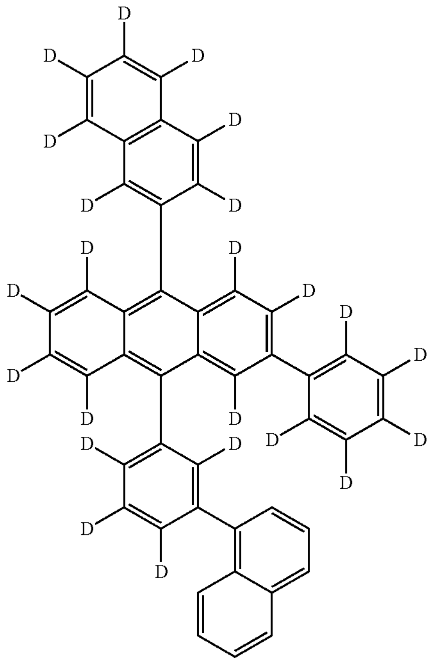

-continued
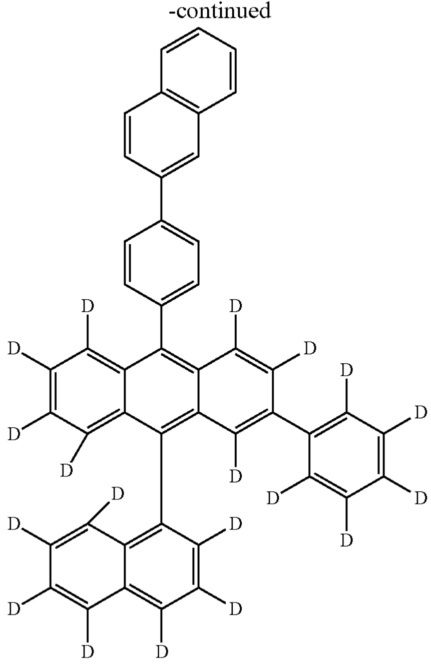
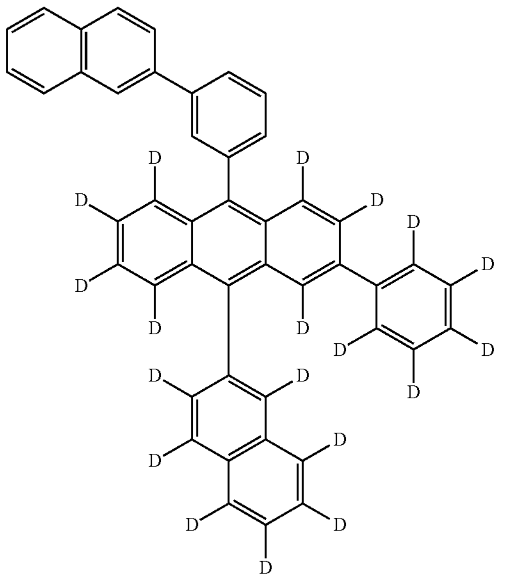
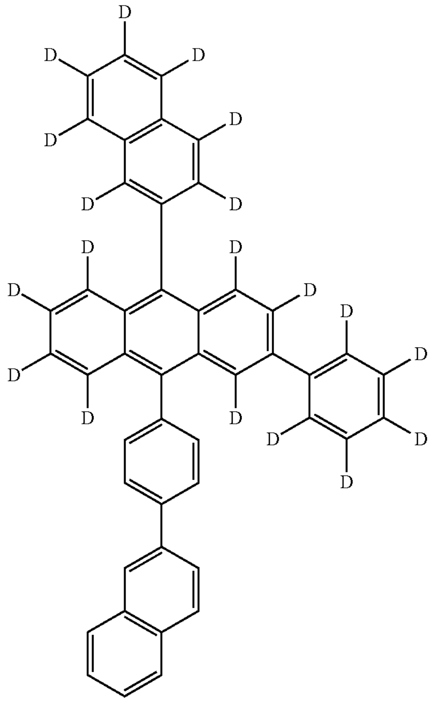
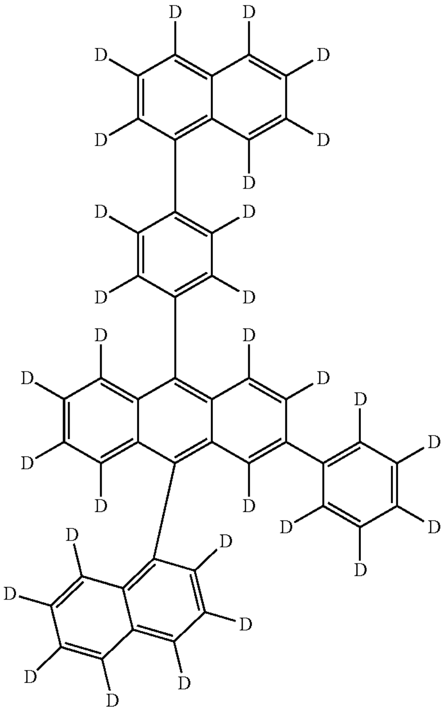

-continued
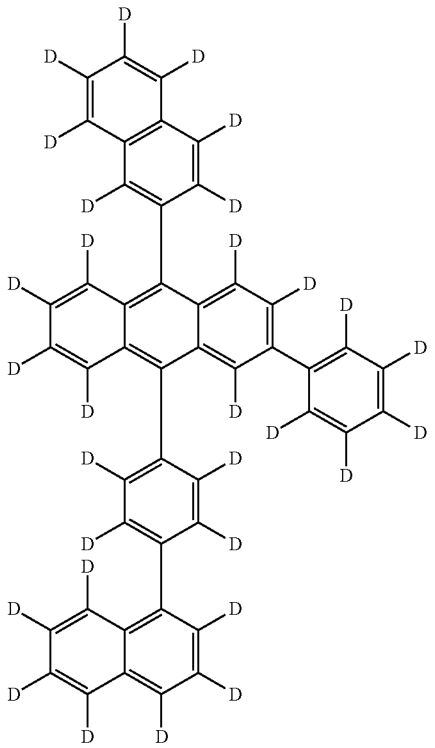
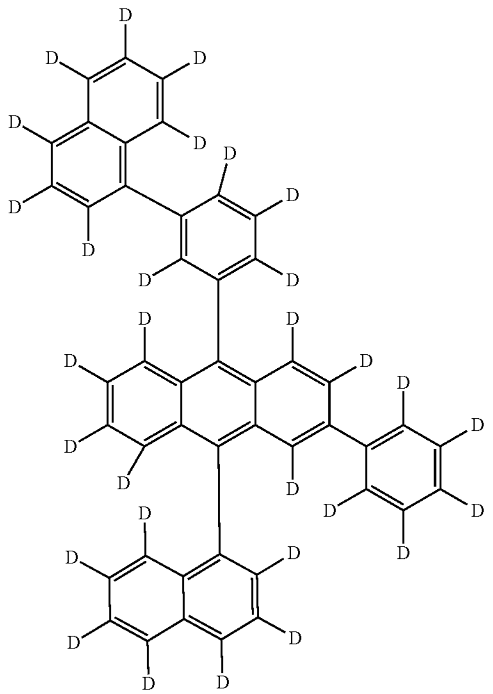
-continued
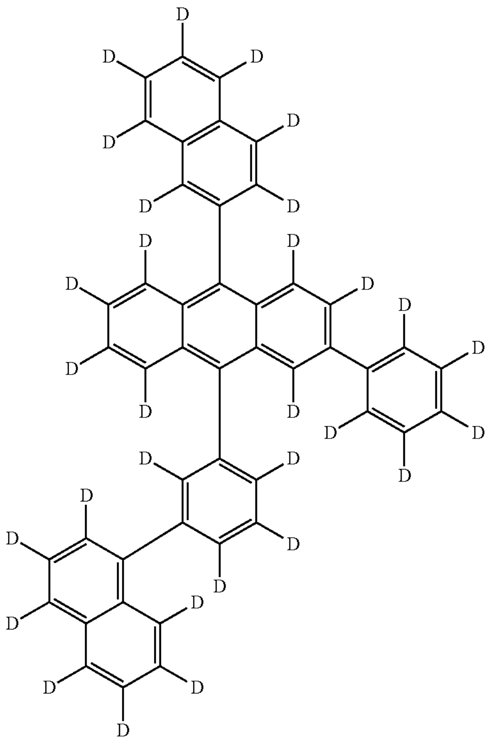
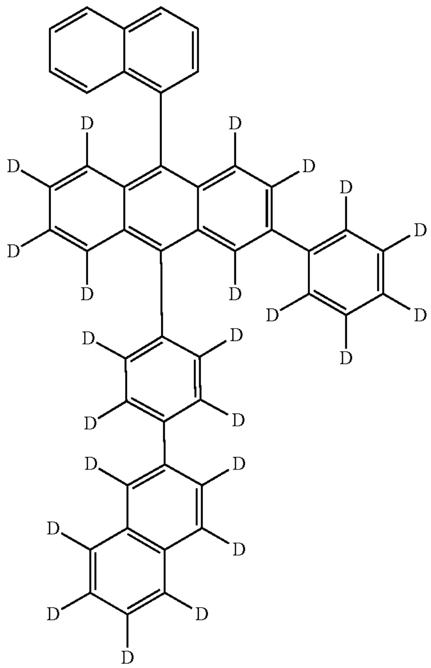

-continued
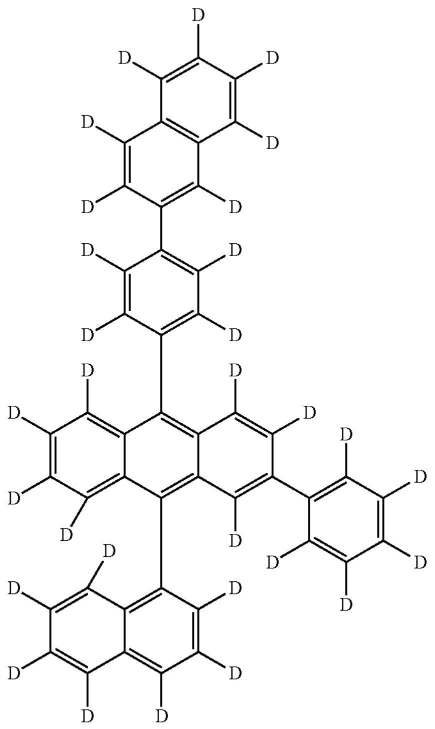
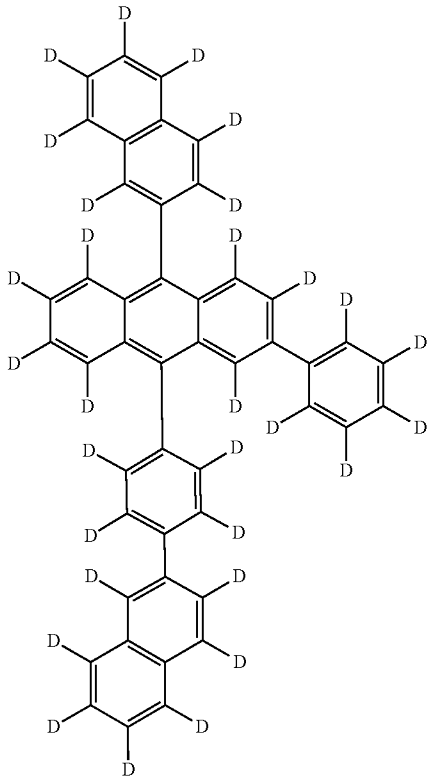
-continued
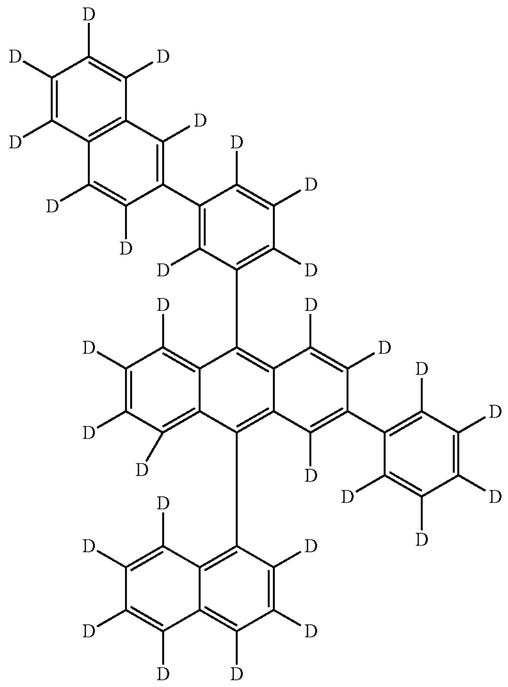
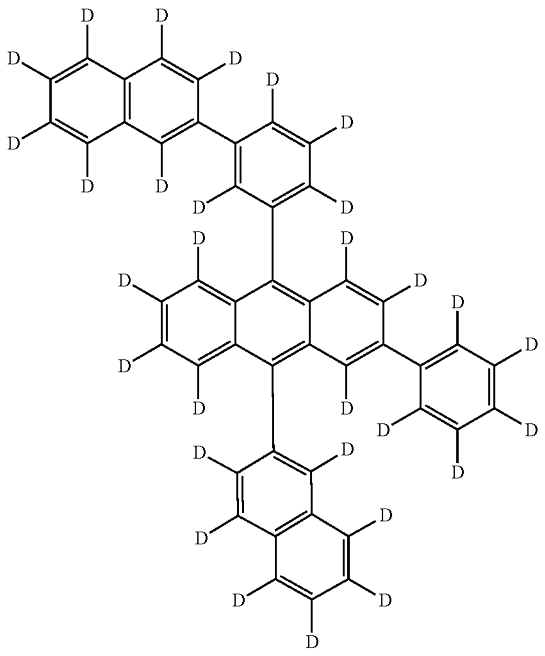 [SMILES: [2H]c1c([2H])c([2H])c(-c2c([2H])c([2H])c3c(-c4c([2H])c([2H])c([2H])c(-c5c([2H])c([2H])c6c([2H])c([2H])c([2H])c([2H])c6c5[2H])c4[2H])c4c([2H])c([2H])c([2H])c([2H])c4c(-c4c([2H])c([2H])c5c([2H])c([2H])c([2H])c([2H])c5c4[2H])c3c2[2H])c([2H])c1[2H]]

-continued
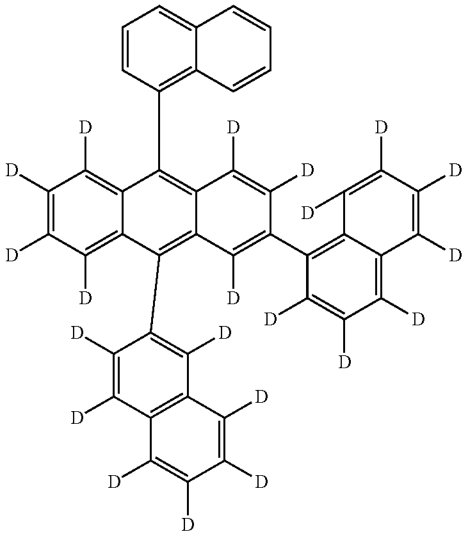
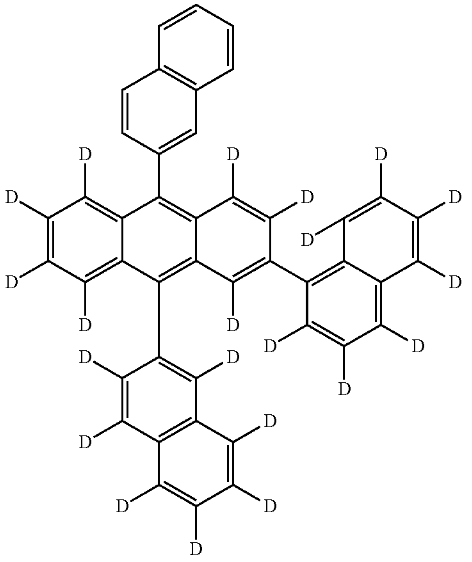
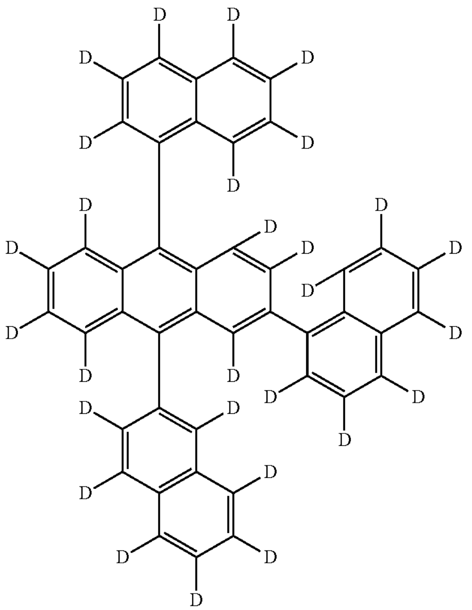
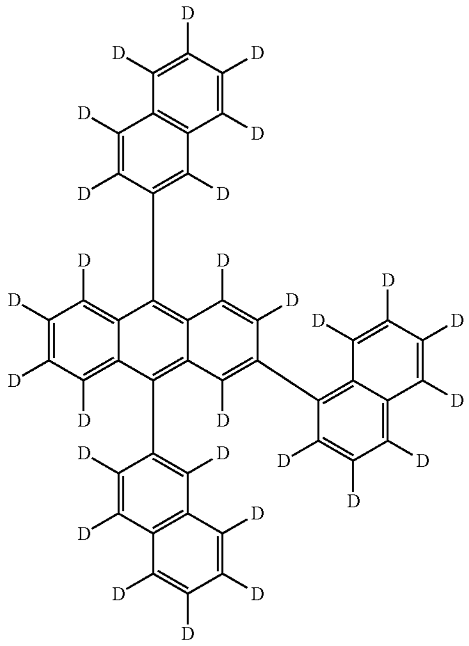
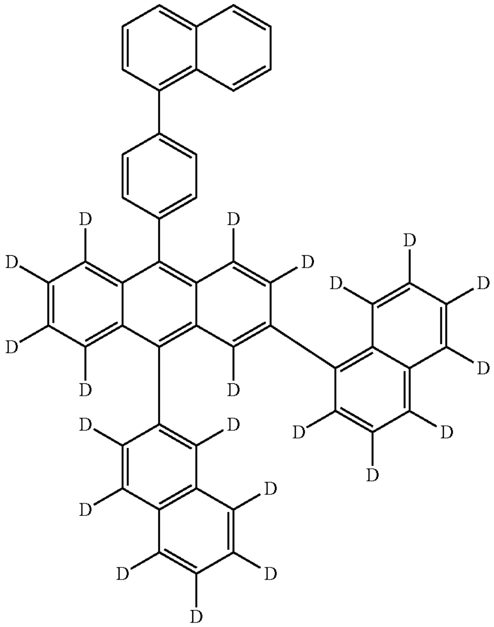

-continued
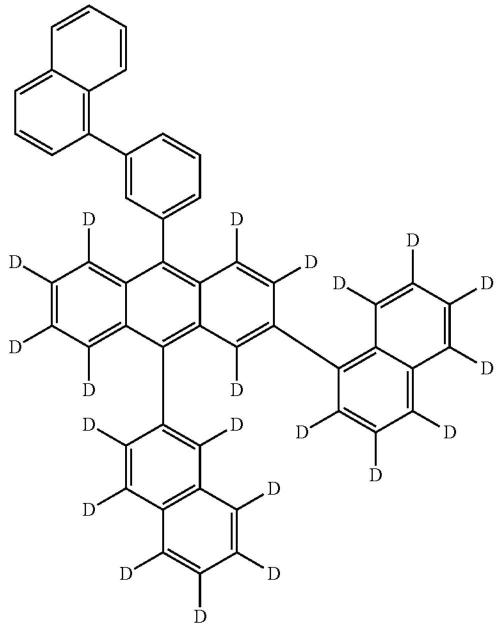
-continued
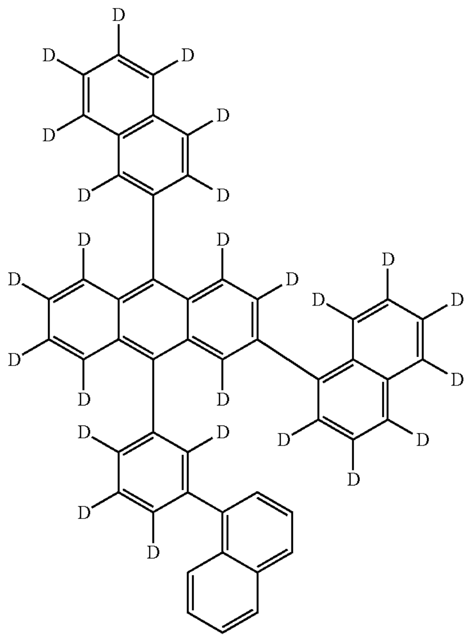
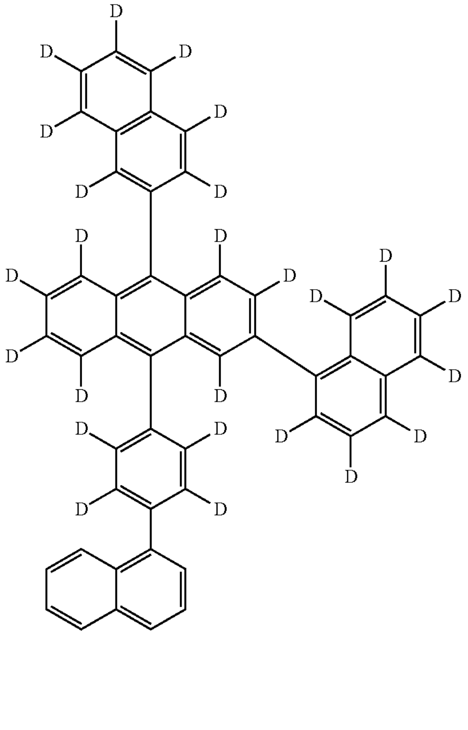
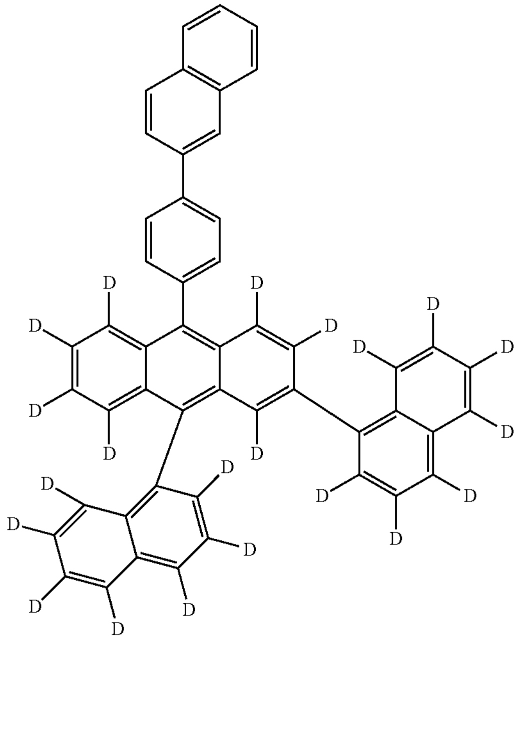

-continued
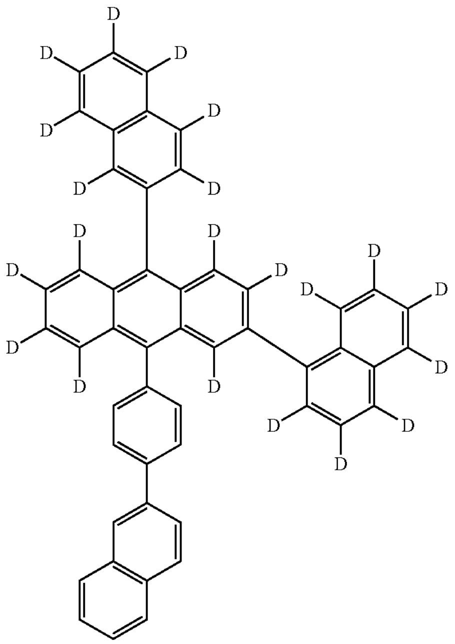
-continued
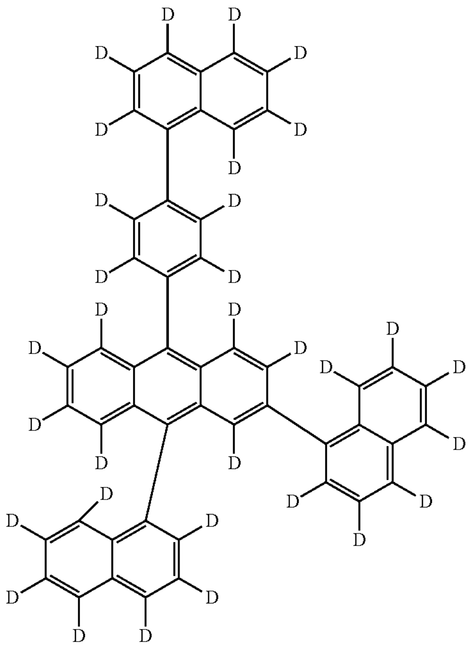
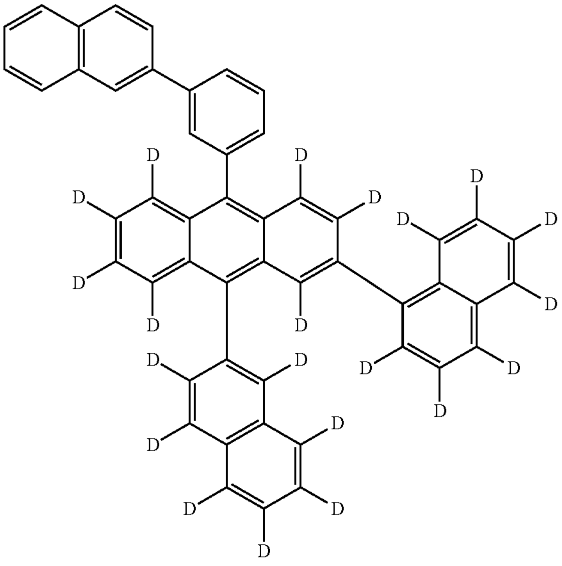
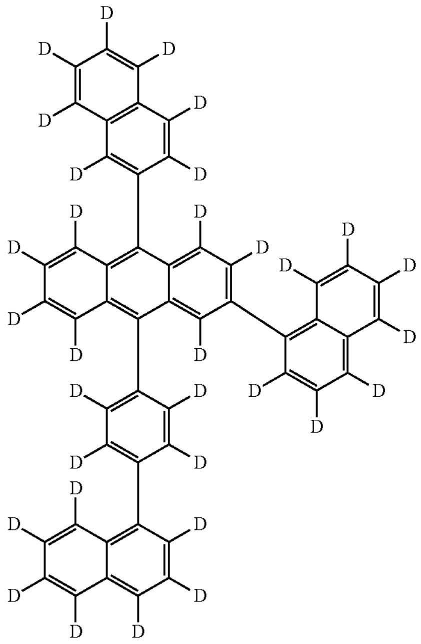

-continued
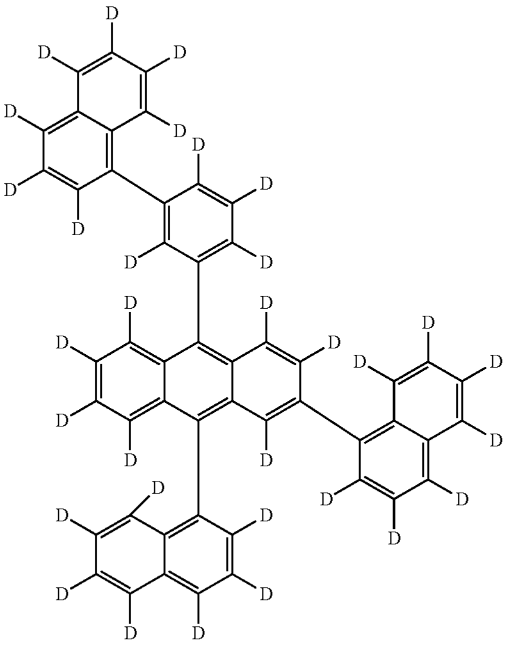
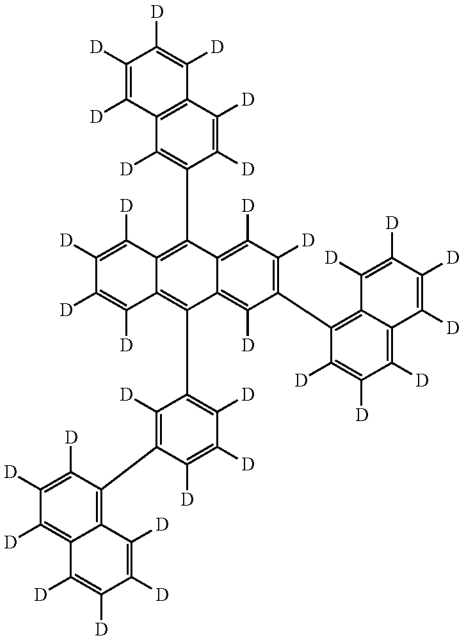
-continued
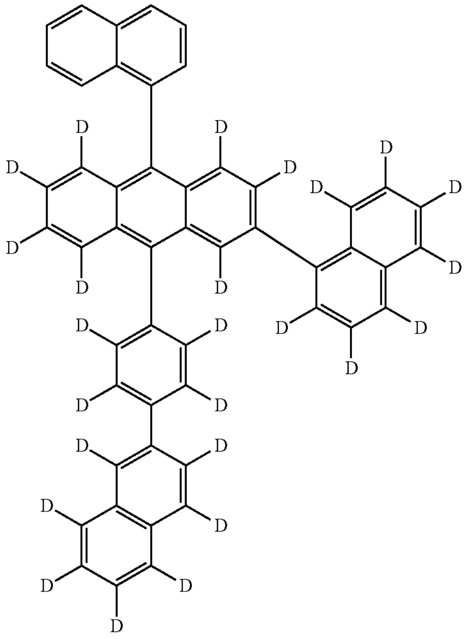
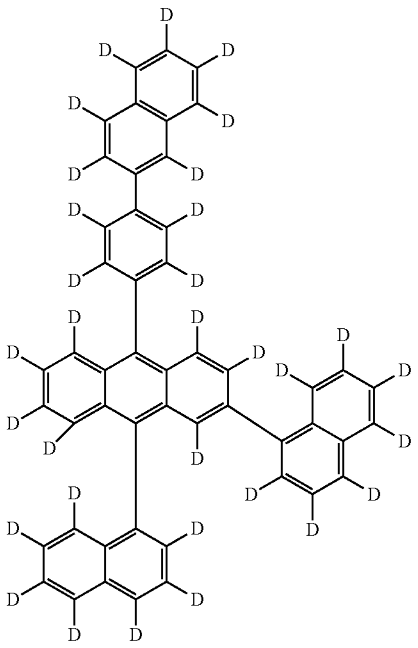

-continued
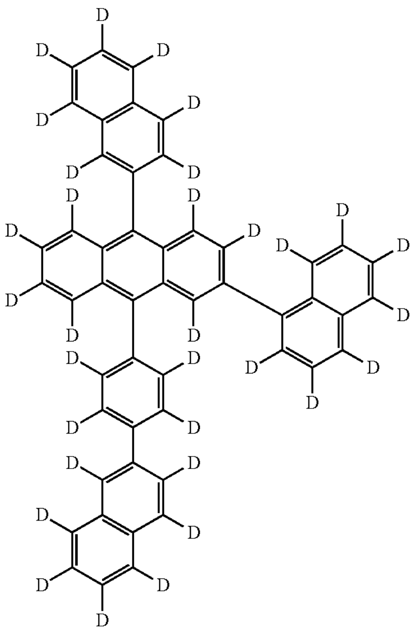
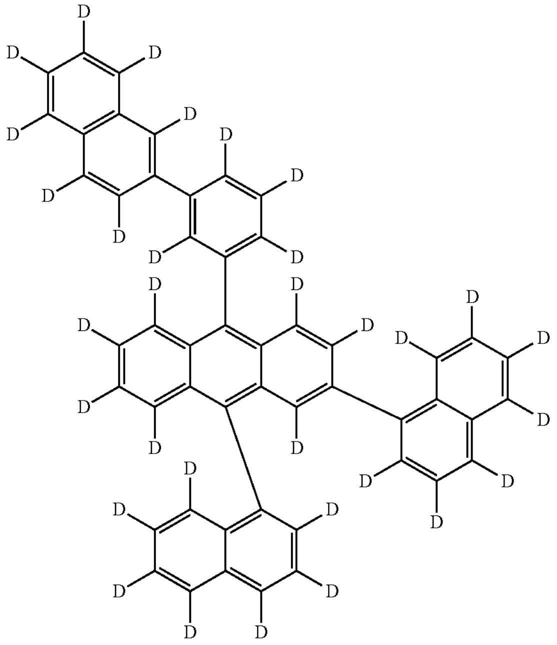
-continued
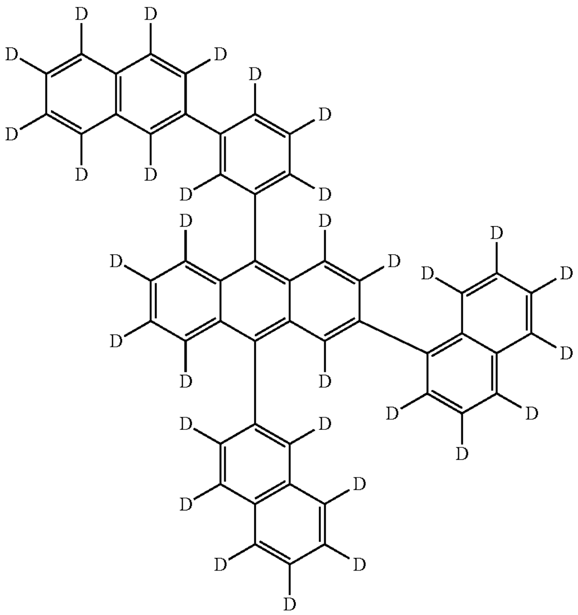
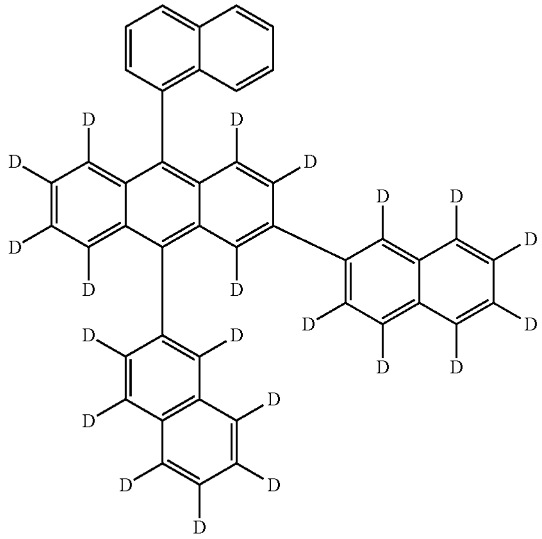

-continued
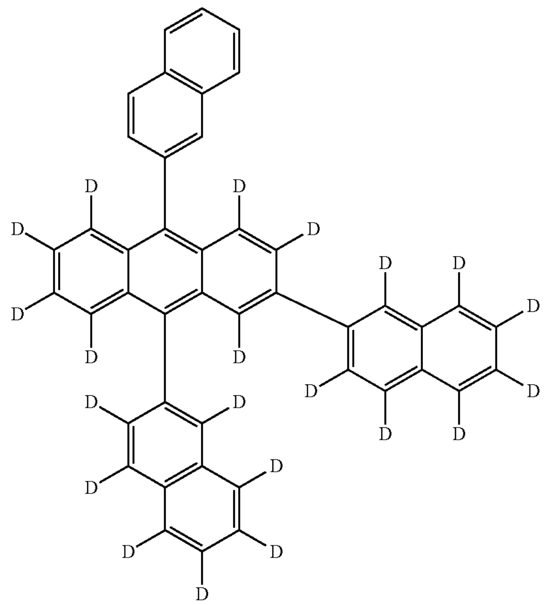
-continued
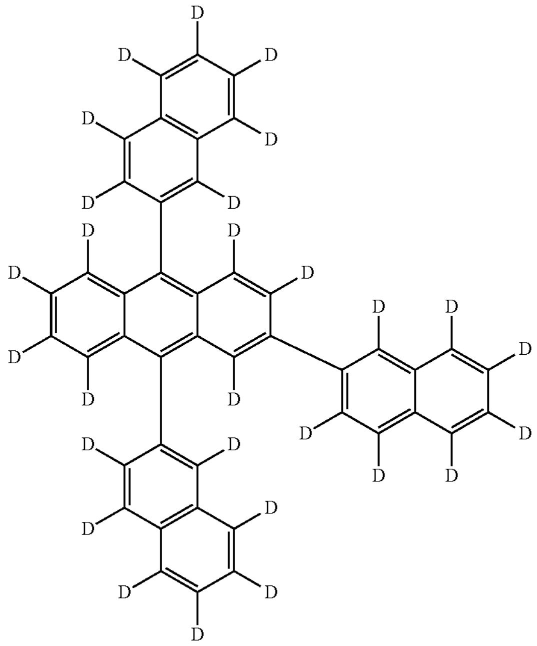
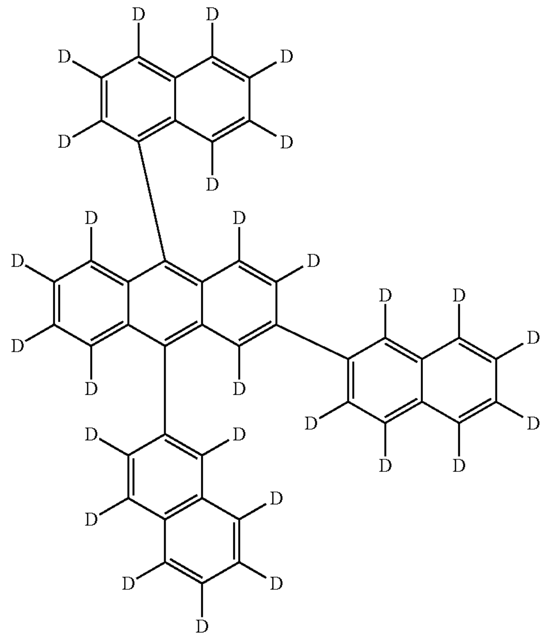
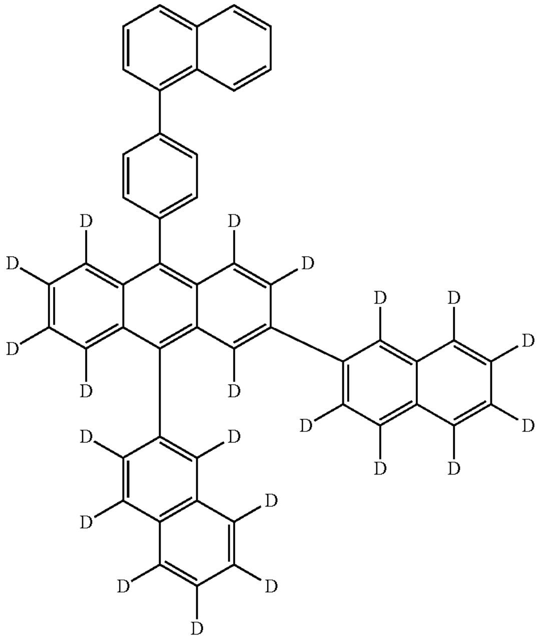

-continued
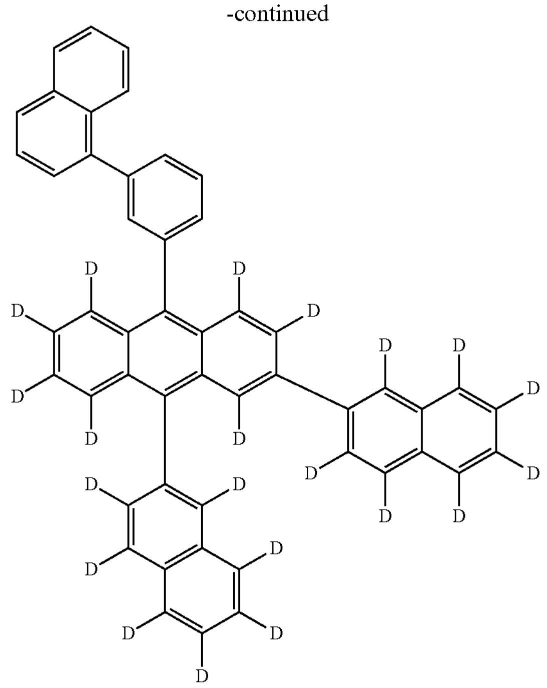
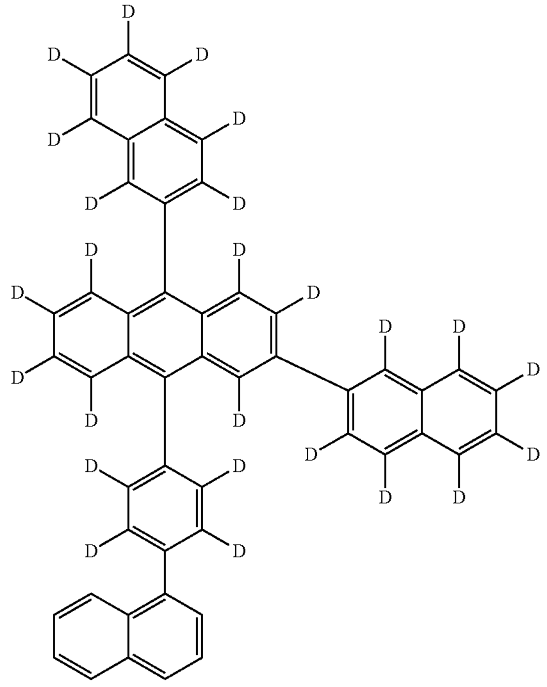
-continued
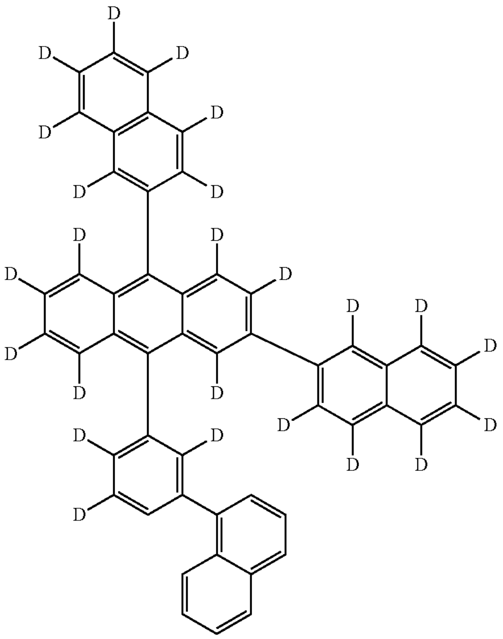
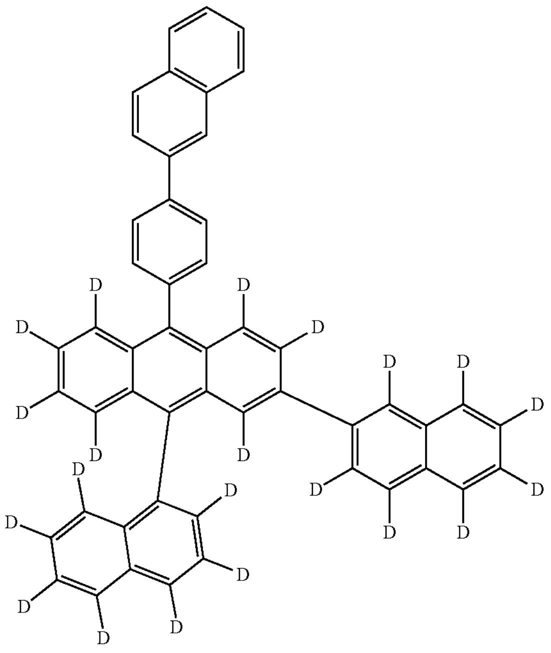

-continued
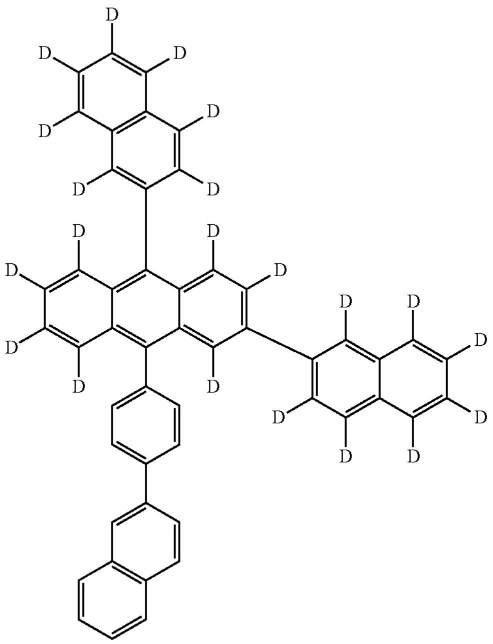
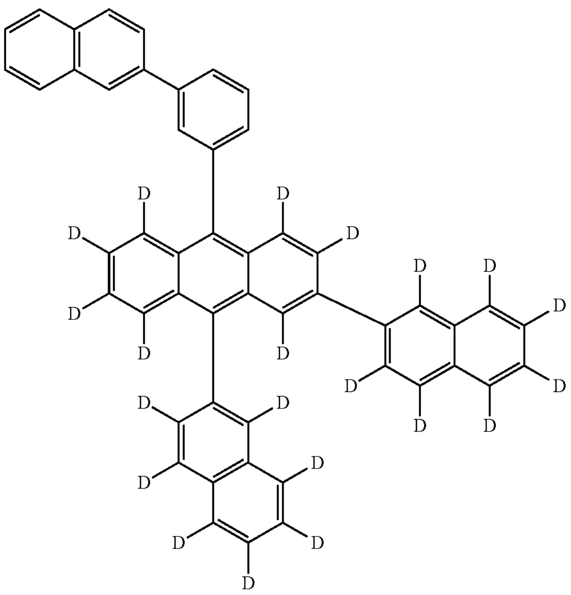
-continued
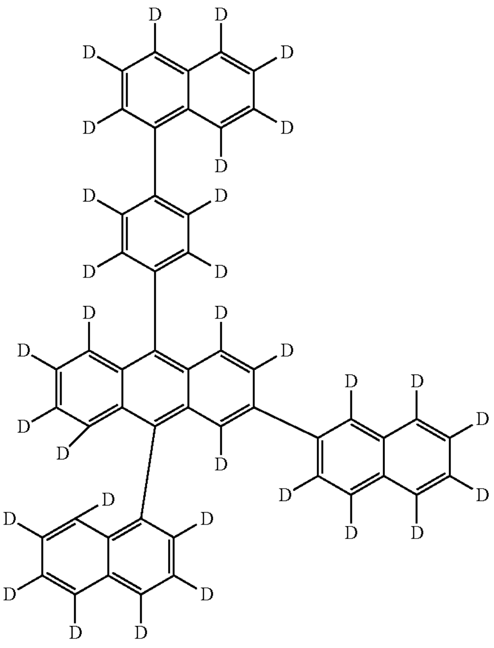
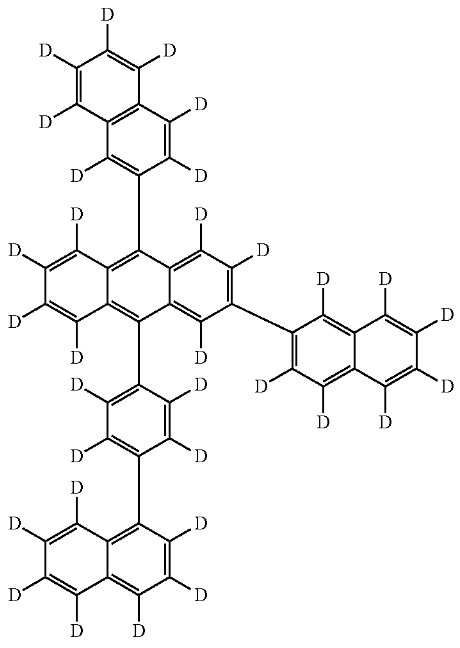

-continued
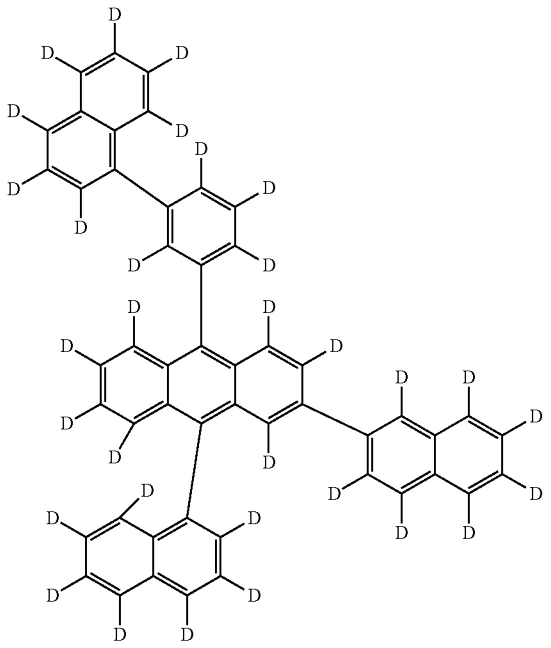
-continued
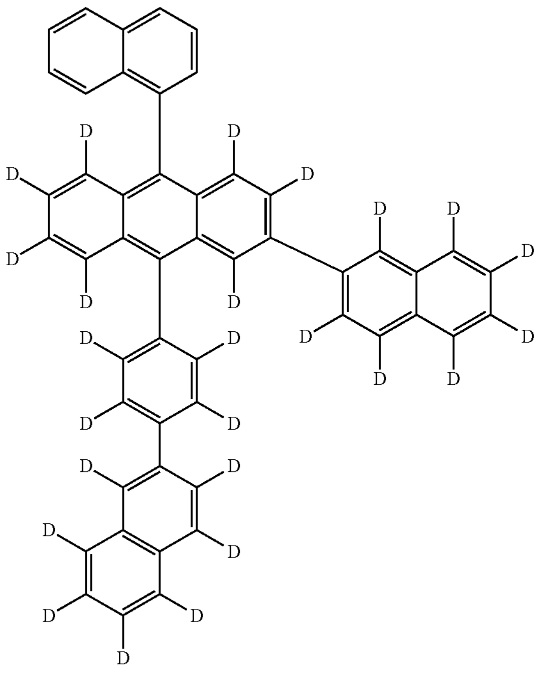
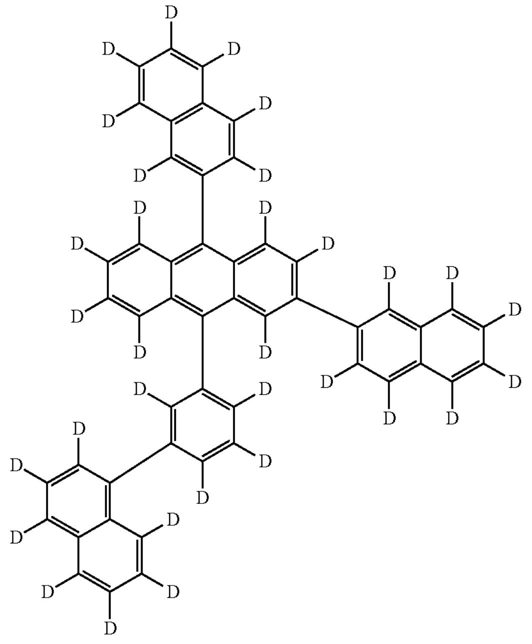
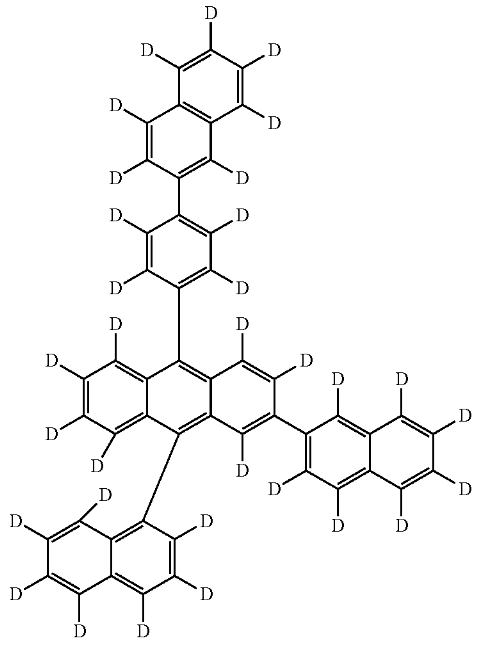

-continued
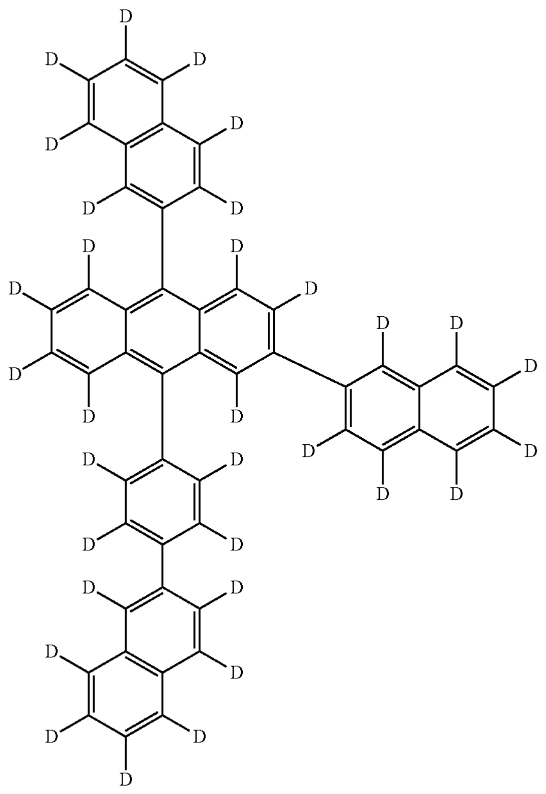
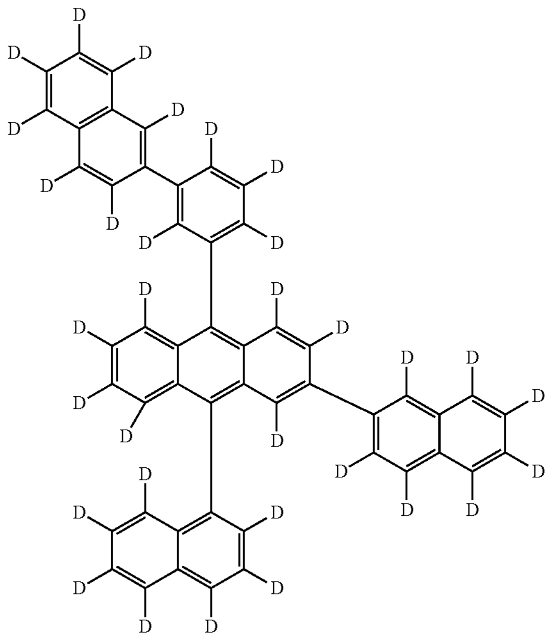
-continued
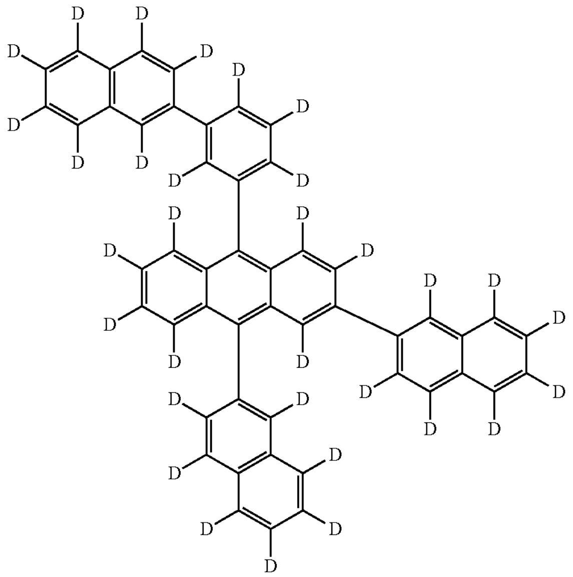
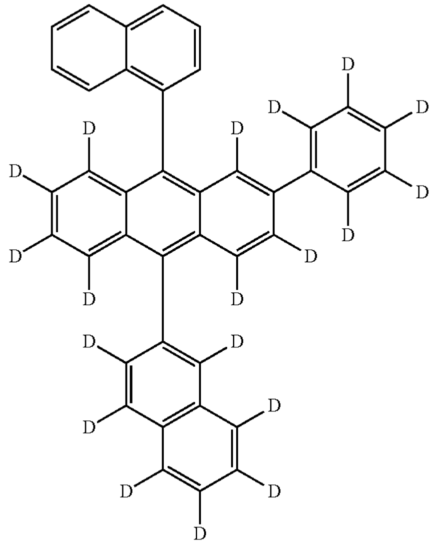
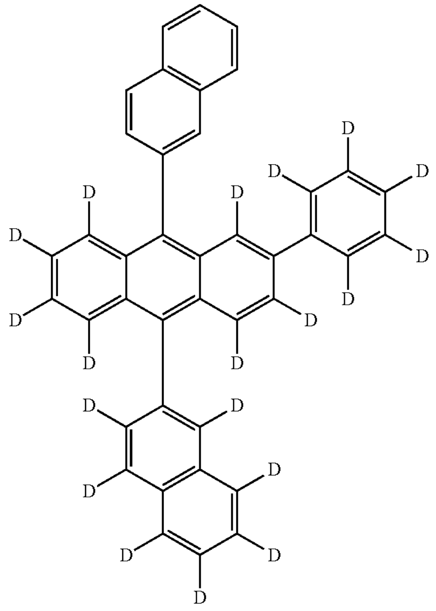

-continued
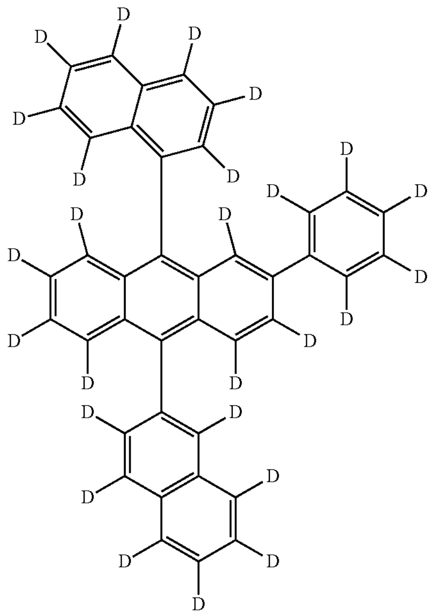
-continued
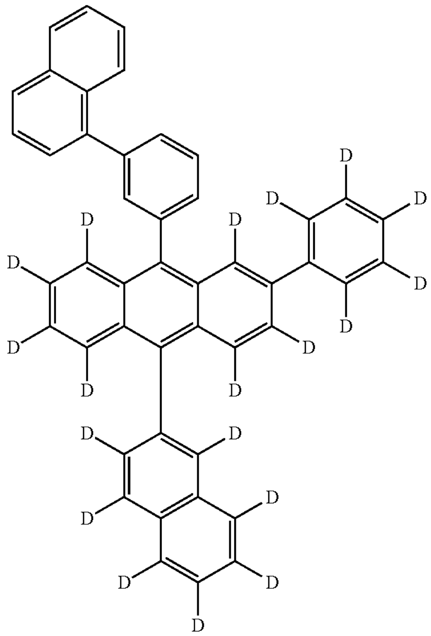
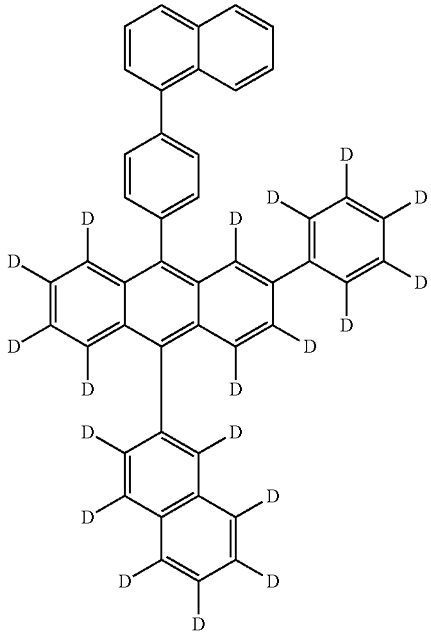
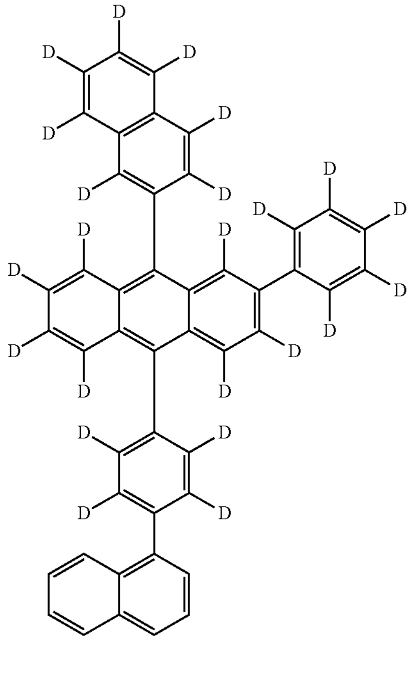

-continued
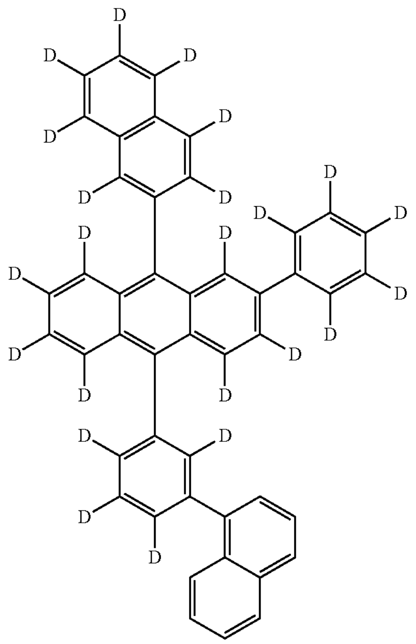
-continued
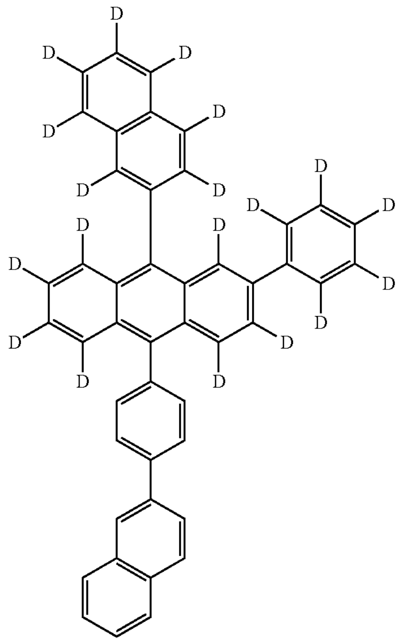
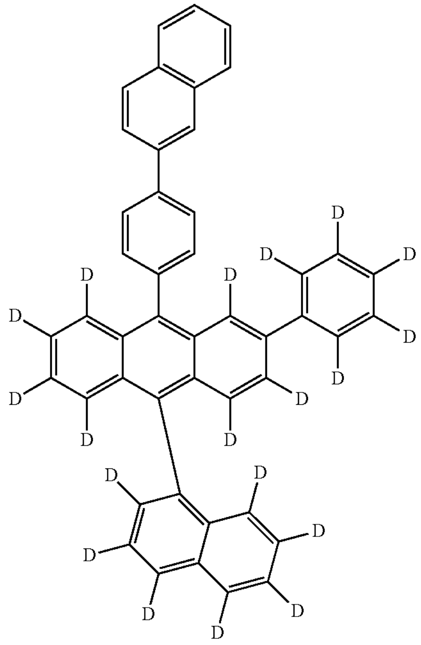
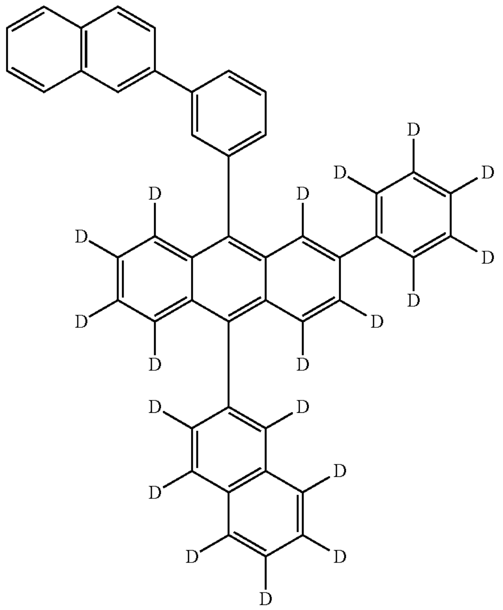

-continued
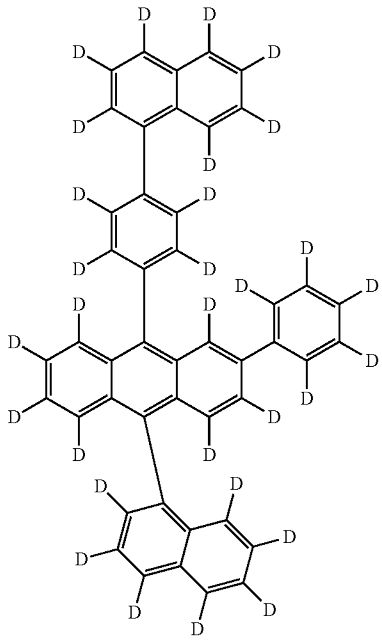
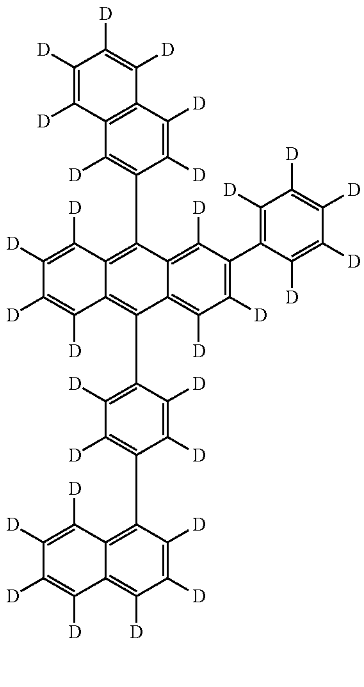
-continued
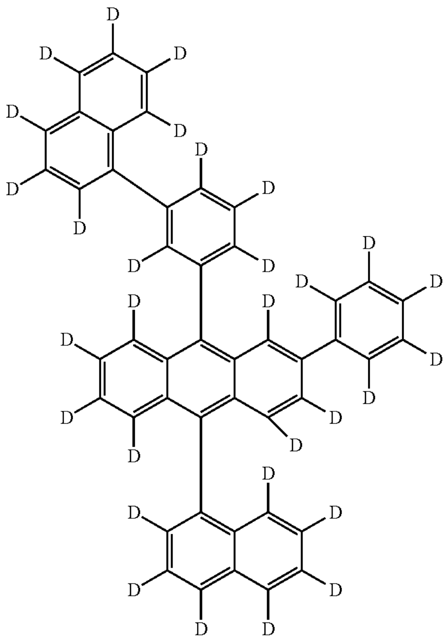
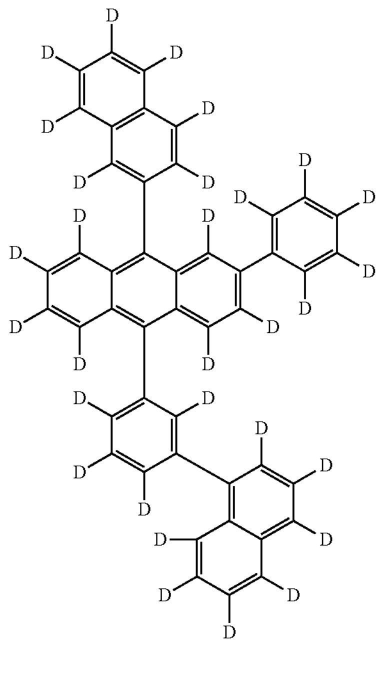

-continued
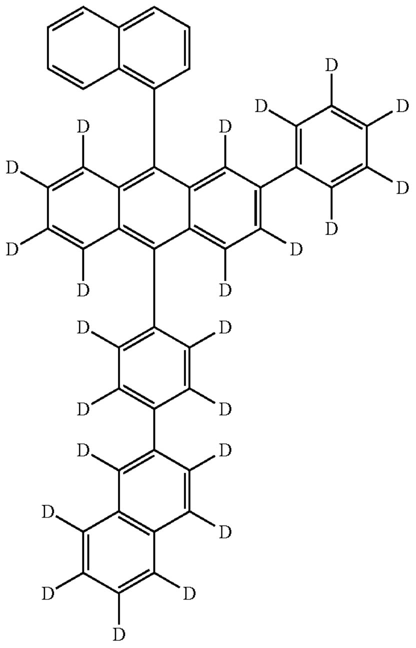
-continued
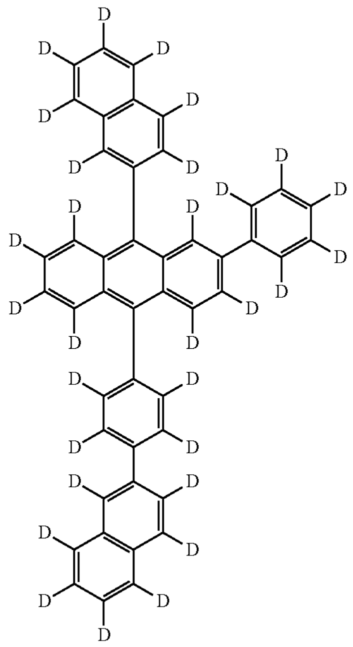
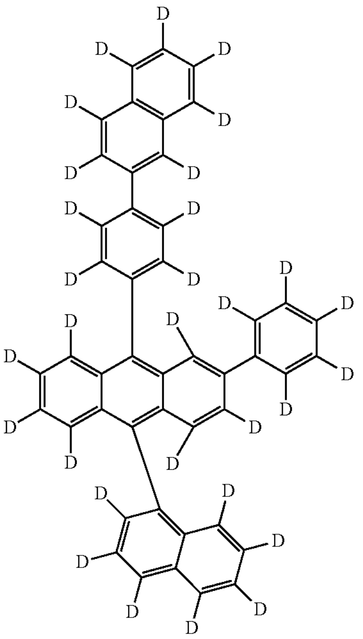
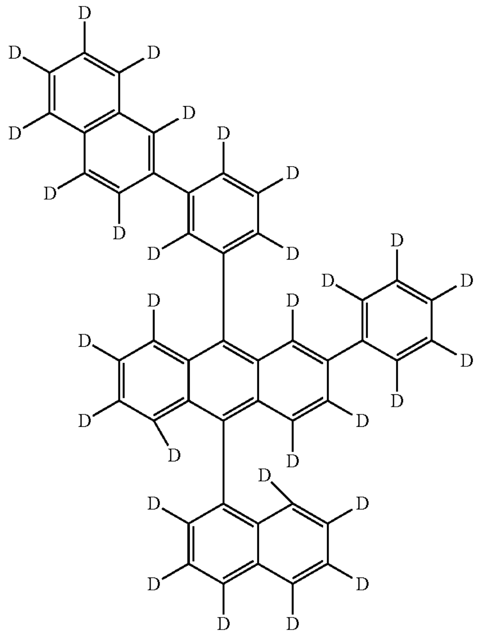

-continued
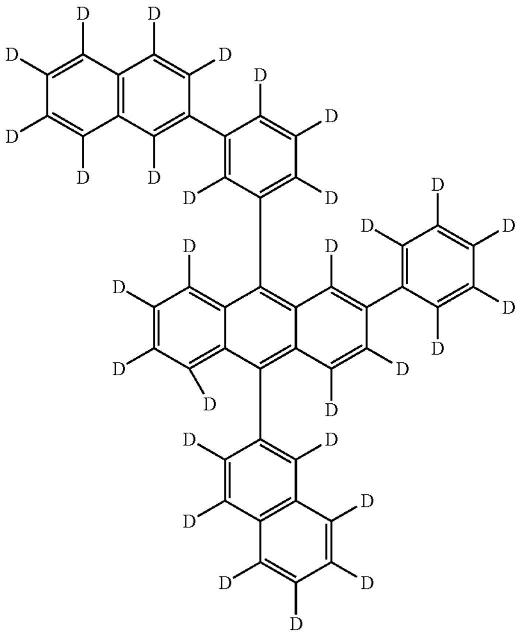
-continued
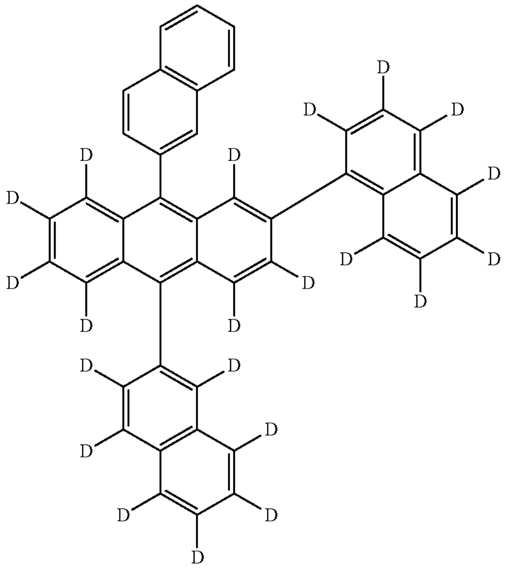
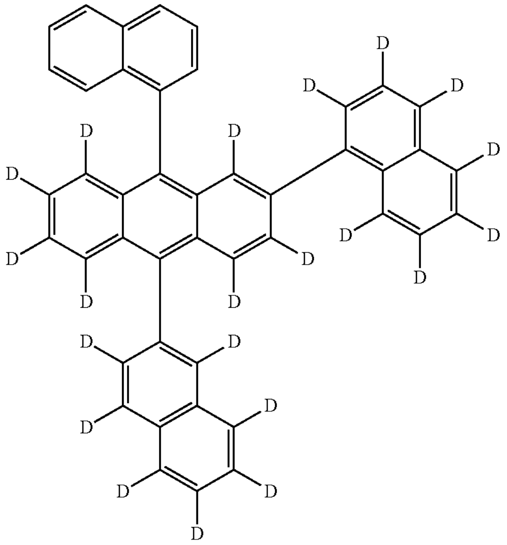
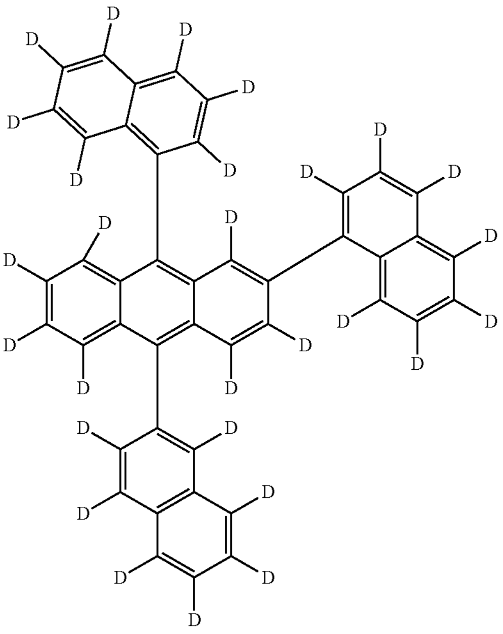

-continued
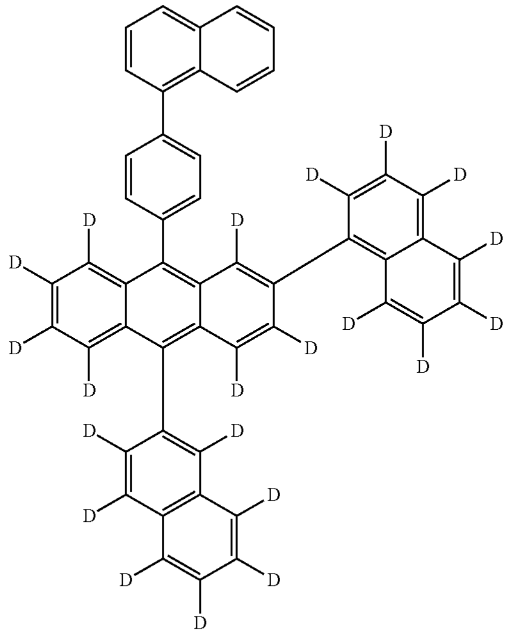
-continued
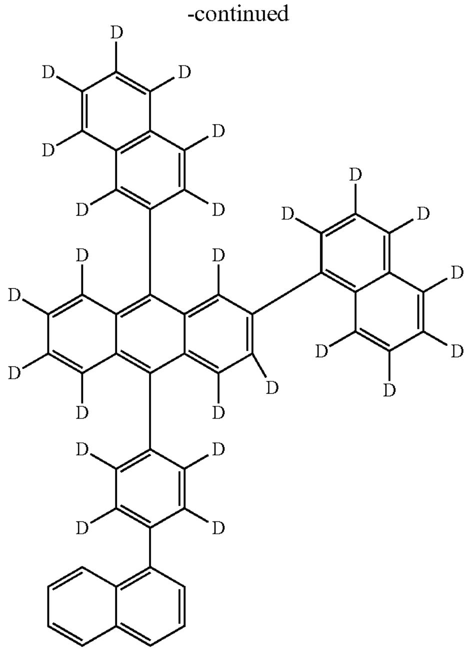
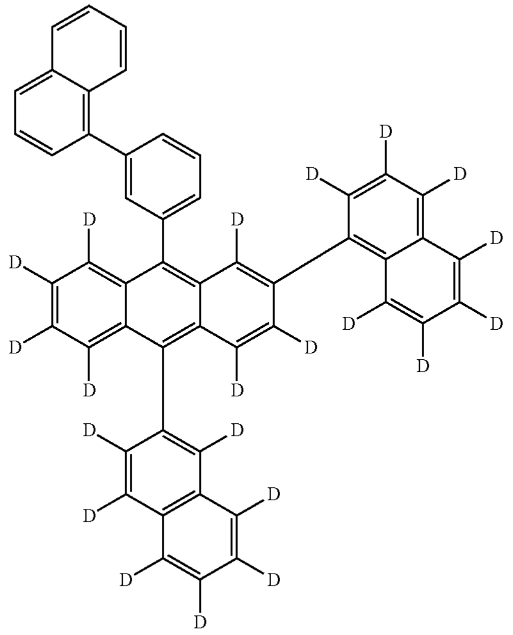
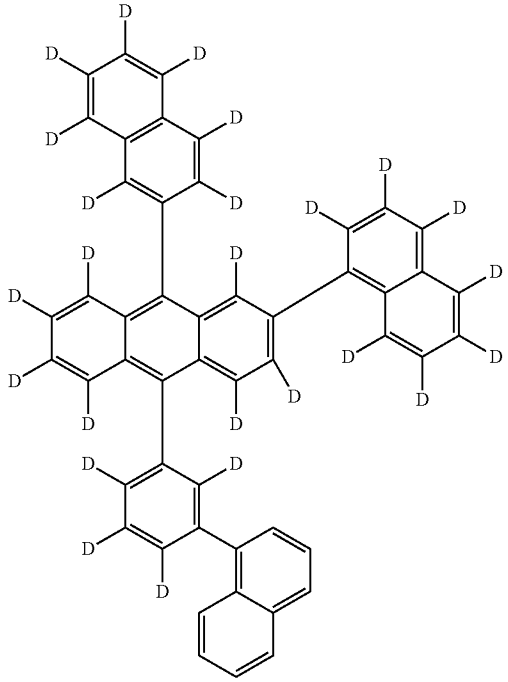

-continued
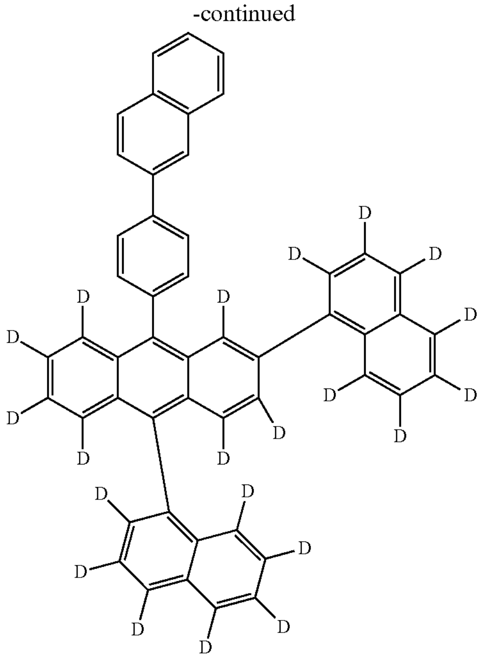
-continued
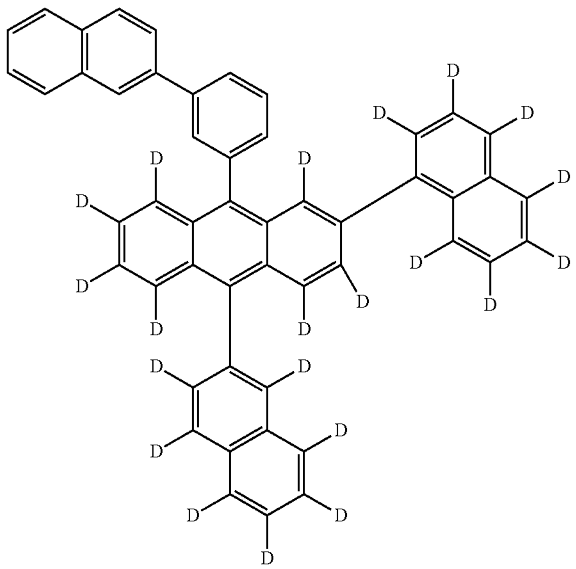
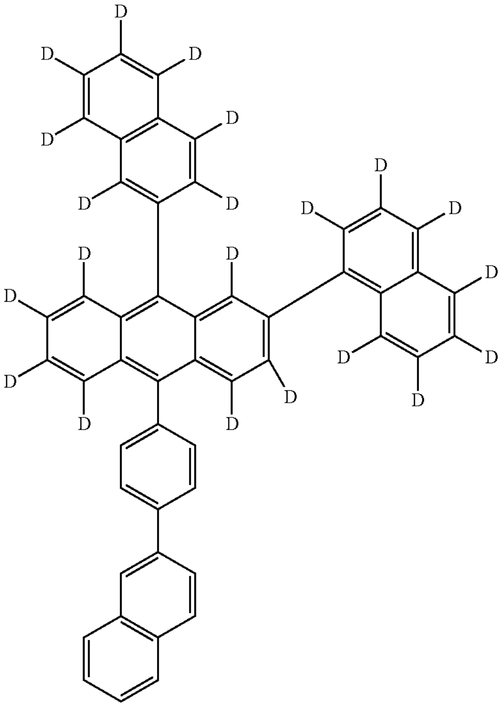
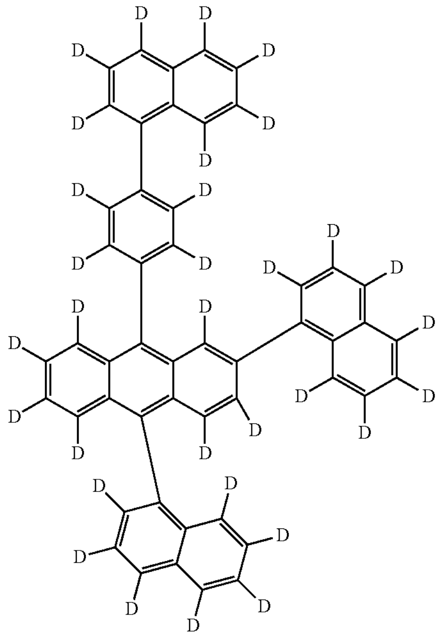

-continued
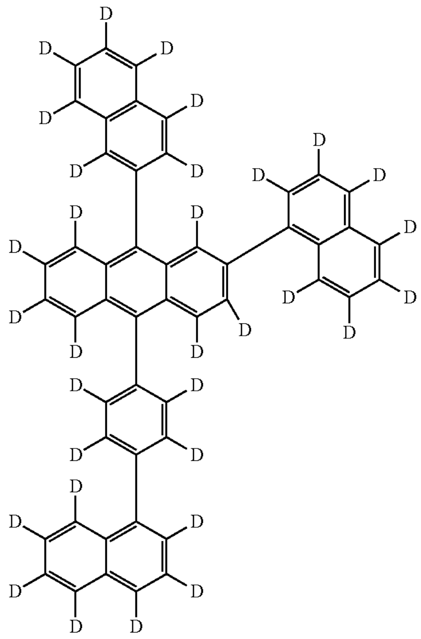
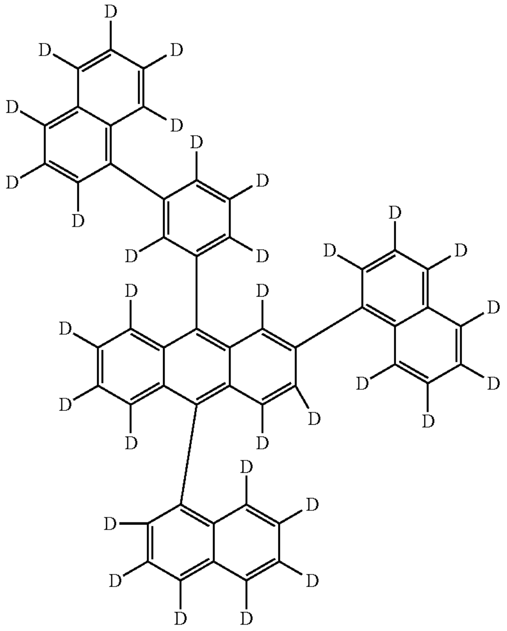
-continued
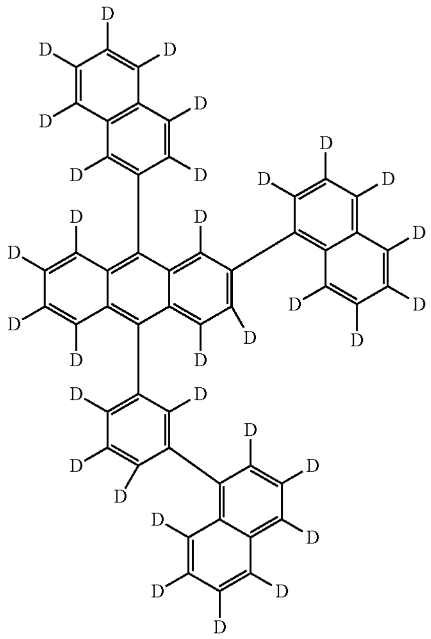
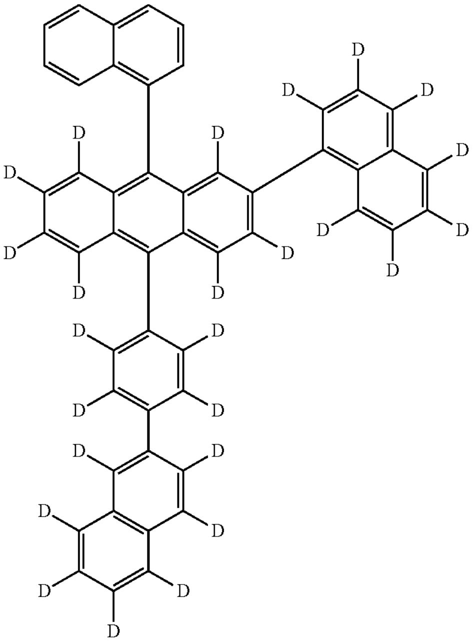

-continued
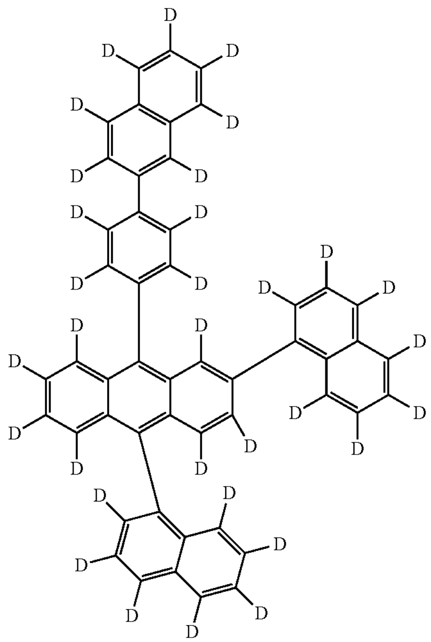
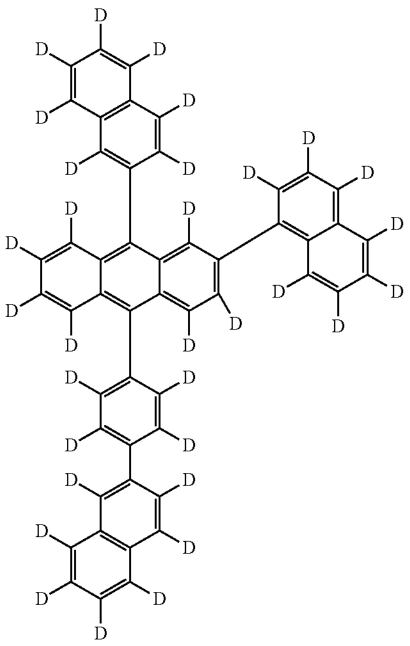
-continued
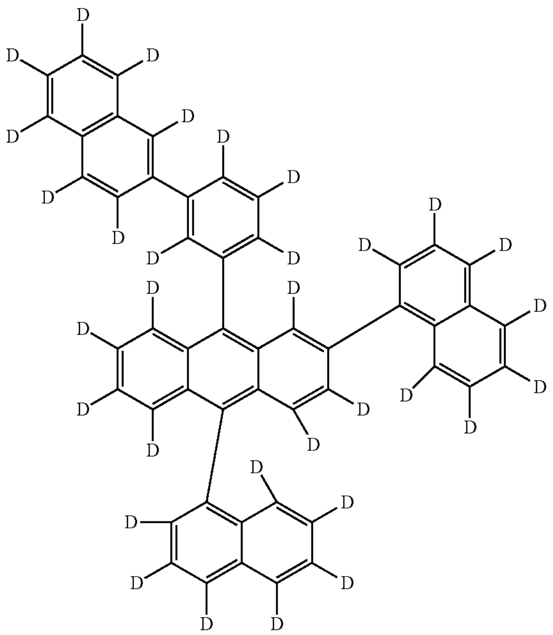
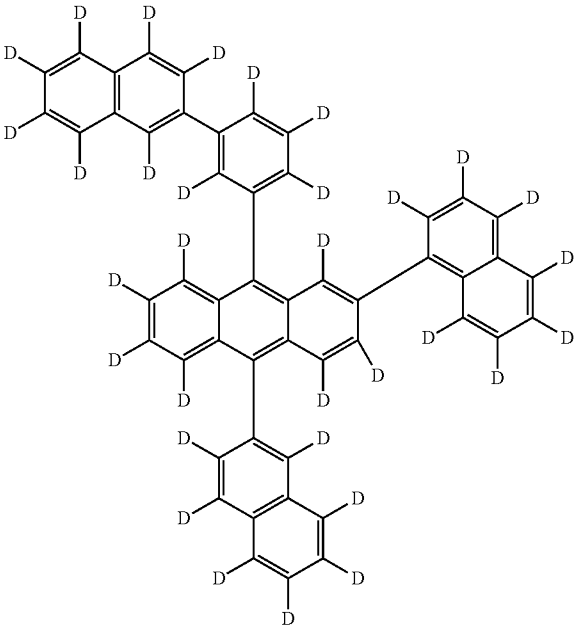

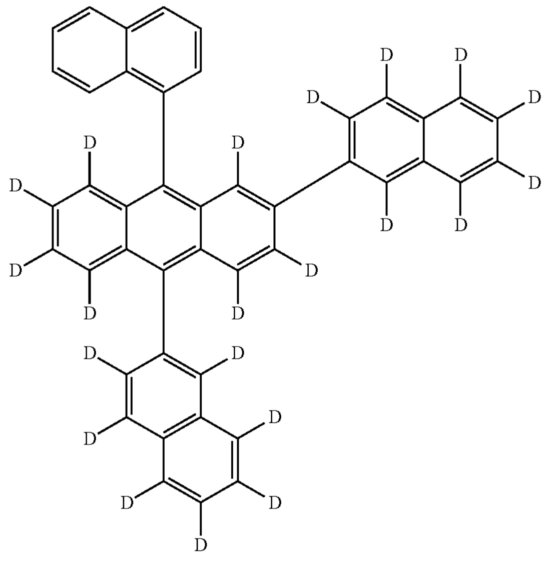
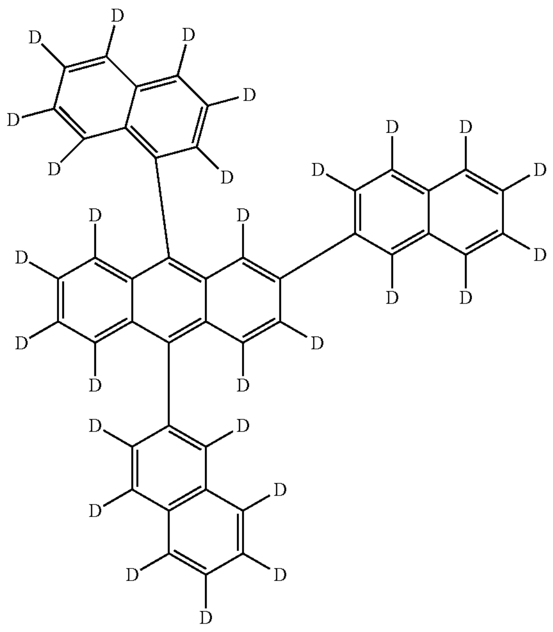
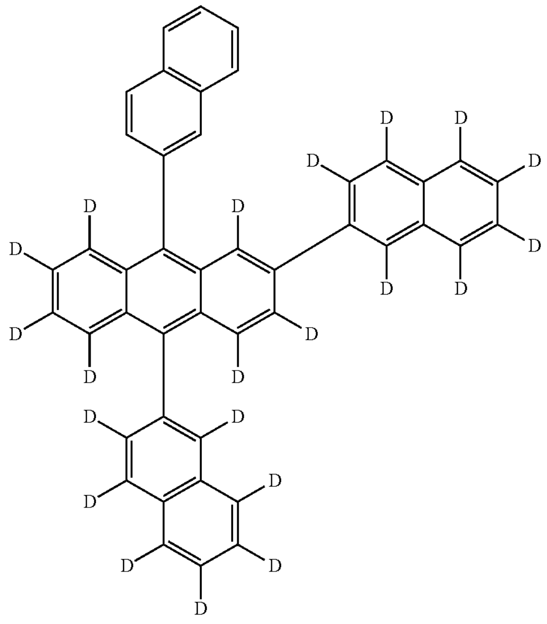
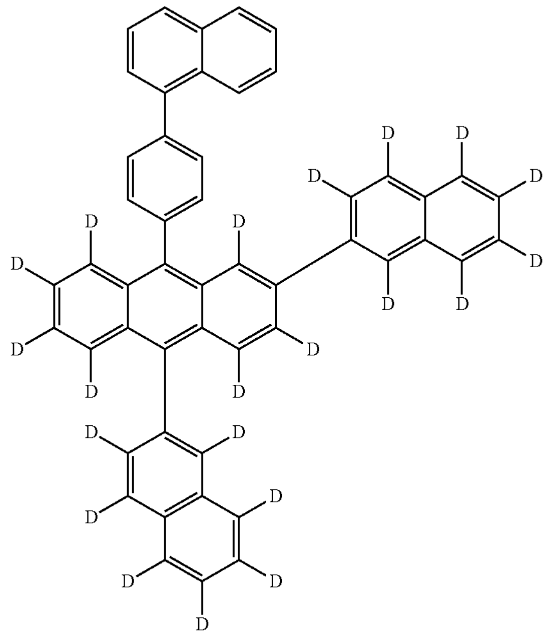

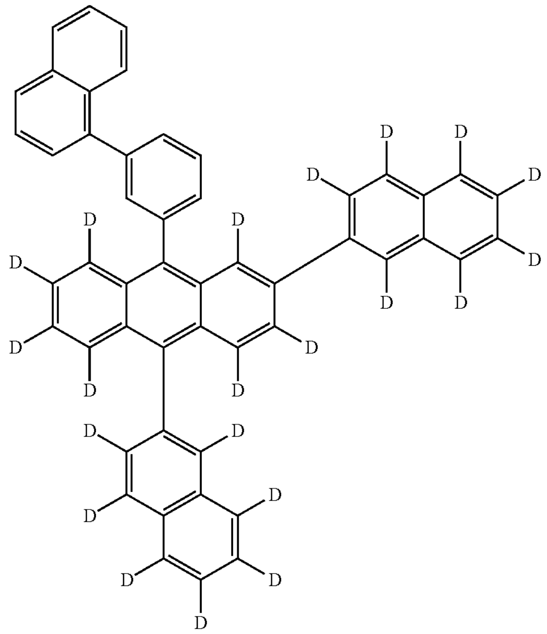
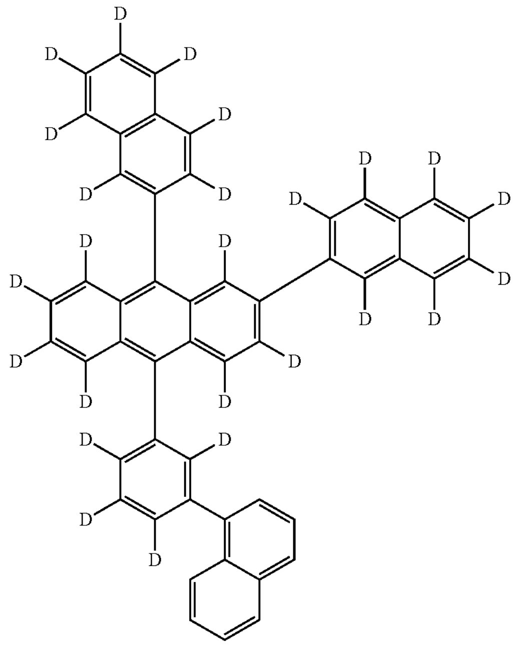
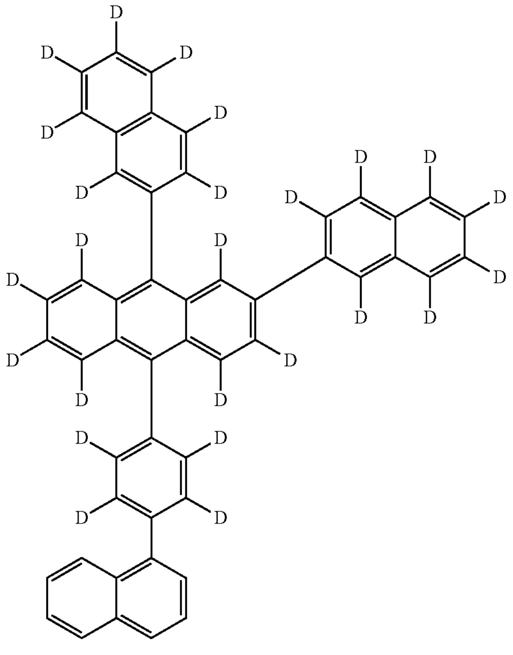
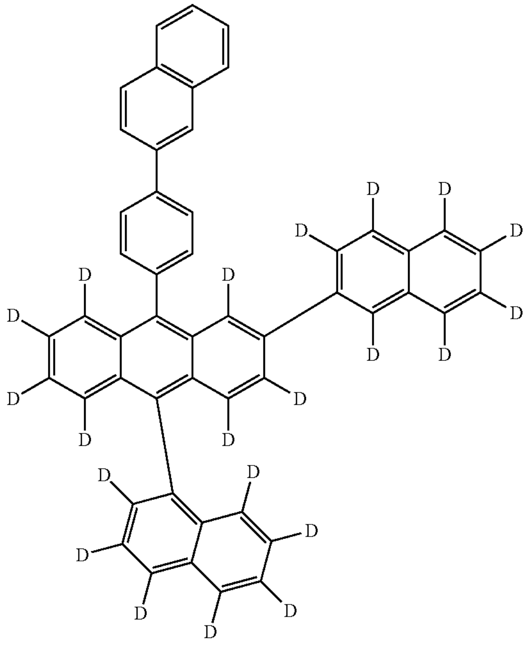

-continued
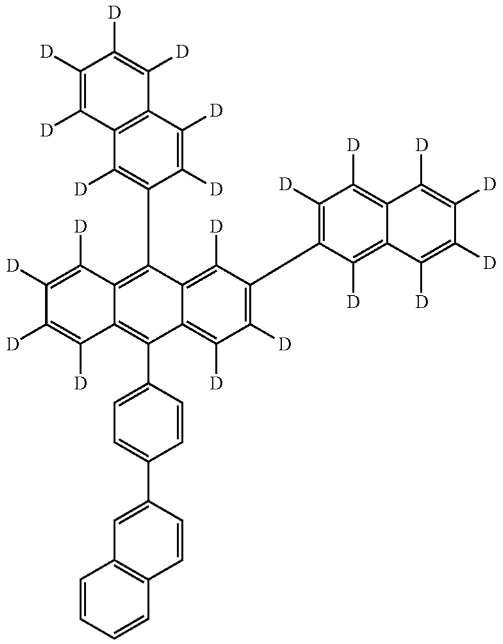
-continued
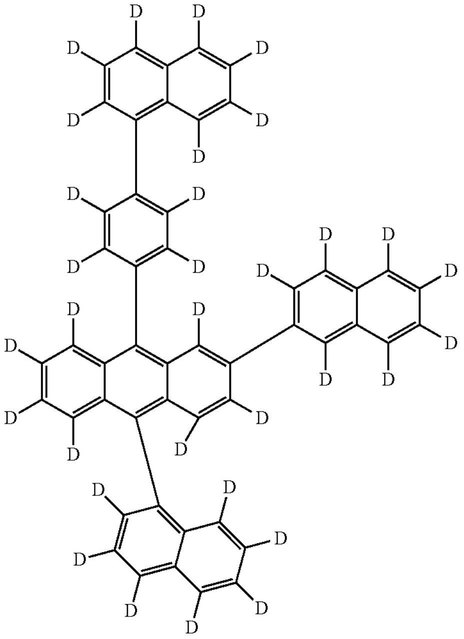
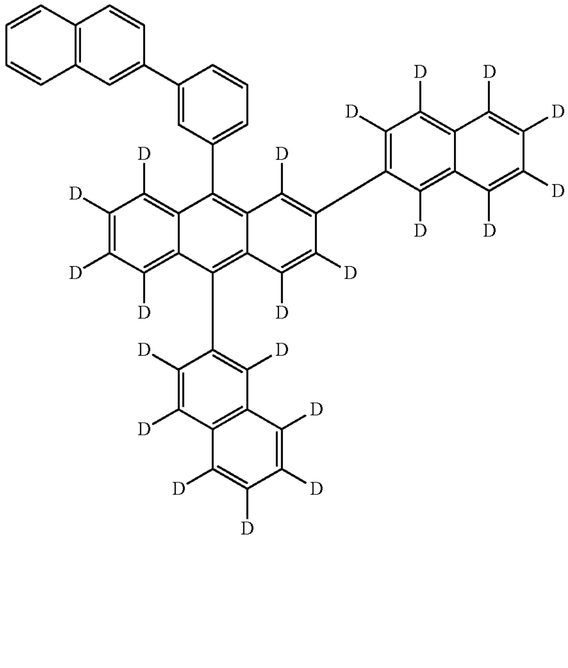
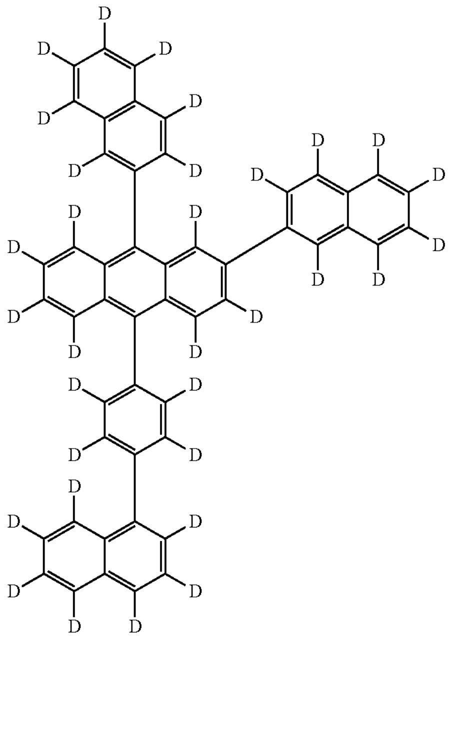

-continued
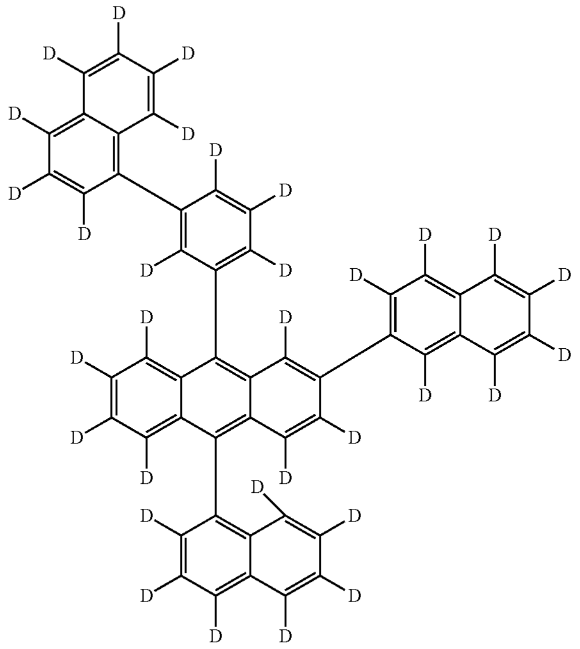
-continued
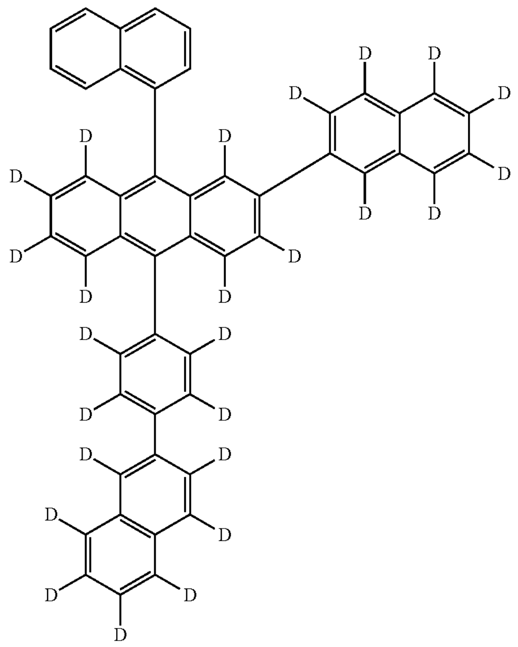
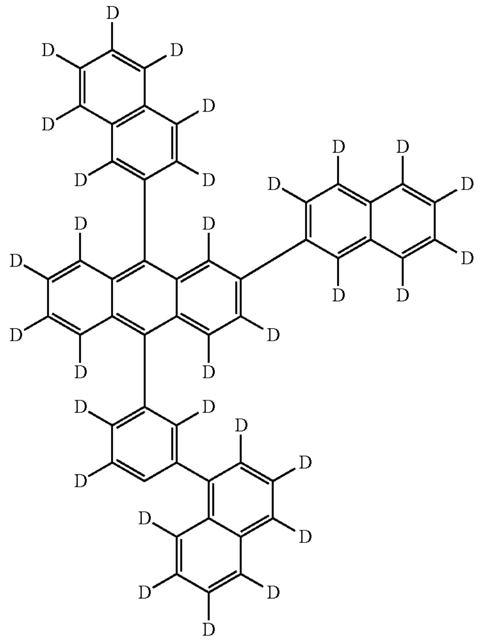
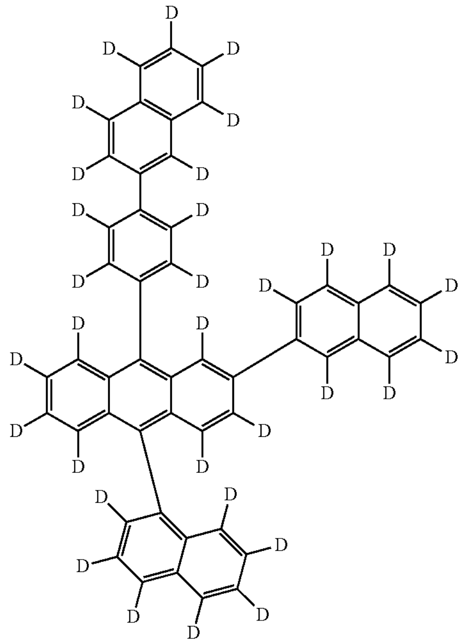

-continued

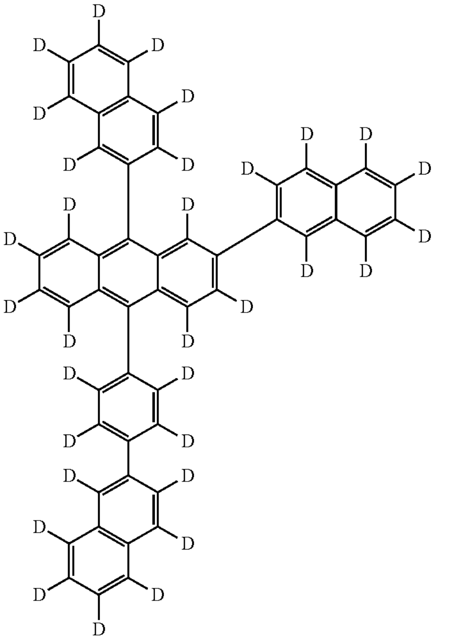

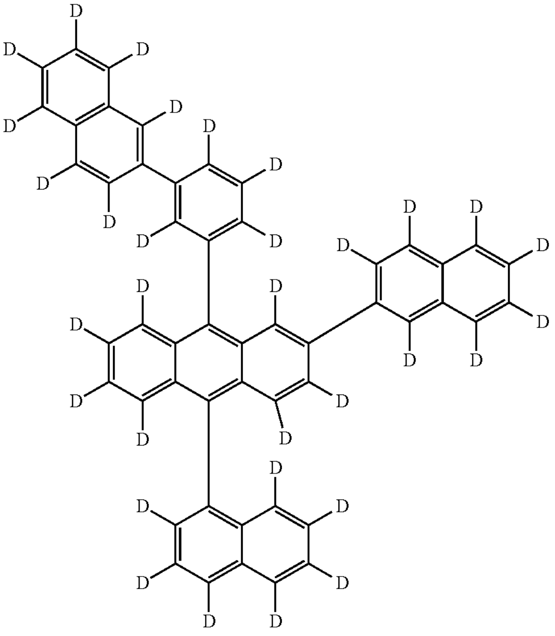

-continued

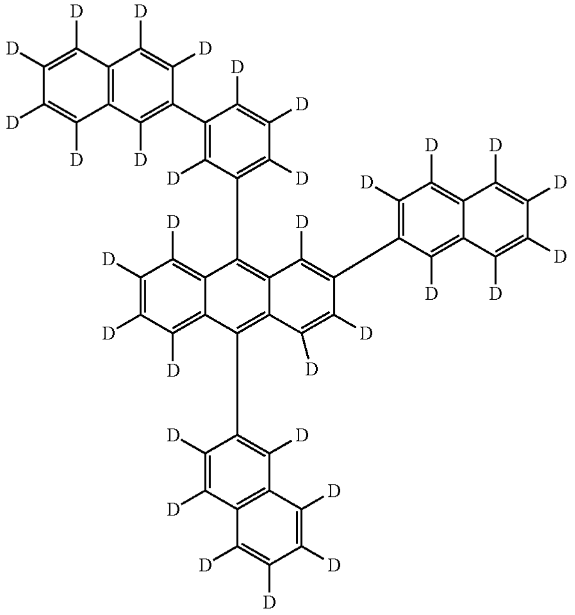

Hereinafter, Formula 2 will be described.

The present specification provides a compound represented by the following Formula 2.

[Formula 2]

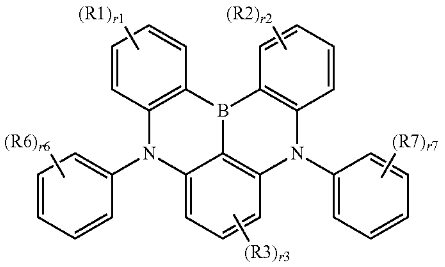

In Formula 2,

R1 to R3, R6, and R7 are the same as or different from each other, and are each independently hydrogen; deuterium; a halogen group; a cyano group; a substituted or unsubstituted alkyl group; a substituted or unsubstituted cycloalkyl group; a substituted or unsubstituted silyl group; a substituted or unsubstituted alkenyl group; a substituted or unsubstituted aryl group; a substituted or unsubstituted heterocyclic group; a substituted or unsubstituted alkoxy group; a substituted or unsubstituted aryloxy group; a substituted or unsubstituted alkylthio group; a substituted or unsubstituted arylthio group; or a substituted or unsubstituted amine group, or a group represented by the following Formula 2-A or 2-B, or are bonded to an adjacent substituent to form a substituted or unsubstituted ring, r1 and r2 are an integer from 0 to 4, r3 is an integer from 0 to 3, r6 and r7 are an integer from 0 to 5, and when r1 to r3, r6, and r7 are each 2 or higher, substituents in the parenthesis are the same as or different from each other,

[Formula 2-A]

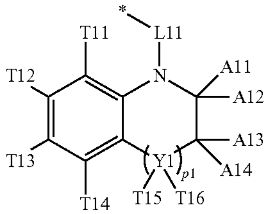

[Formula 2-B]

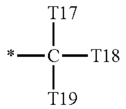

in Formulae 2-A and 2-B,

* is a bonding site,

T11 to T19 are the same as or different from each other, and are each independently hydrogen; deuterium; a halogen group; a cyano group; a substituted or unsubstituted alkyl group; a substituted or unsubstituted cycloalkyl group; a substituted or unsubstituted silyl group; a substituted or unsubstituted alkenyl group; a substituted or unsubstituted aryl group; a substituted or unsubstituted heterocyclic group; a substituted or unsubstituted alkoxy group; a substituted or unsubstituted aryloxy group; a substituted or unsubstituted alkylthio group; a substituted or unsubstituted arylthio group; or a substituted or unsubstituted amine group, or are bonded to an adjacent substituent to form a substituted or unsubstituted ring, at least one of T17 to T19 is a substituted or unsubstituted aryl group, A11 to A14 are the same as or different from each other, and are each independently hydrogen; deuterium; a halogen group; a cyano group; a substituted or unsubstituted alkyl group; a substituted or unsubstituted cycloalkyl group; a substituted or unsubstituted silyl group; a substituted or unsubstituted alkenyl group; a substituted or unsubstituted aryl group; a substituted or unsubstituted heterocyclic group; a substituted or unsubstituted alkoxy group; a substituted or unsubstituted aryloxy group; a substituted or unsubstituted alkylthio group; a substituted or unsubstituted arylthio group; or a substituted or unsubstituted amine group, or are bonded to an adjacent substituent to form a substituted or unsubstituted aliphatic hydrocarbon ring, L11 is a direct bond; or a substituted or unsubstituted arylene group, p1 is 0 or 1, and Y1 is C or Si.

In an exemplary embodiment of the present specification, Formula 2 includes at least one deuterium.

In an exemplary embodiment of the present specification, when r1 is 2 or higher, a plurality of R1's are the same as or different from each other. In another exemplary embodiment, when r2 is 2 or higher, a plurality of R2's are the same as or different from each other. In still another exemplary embodiment, when r3 is 2 or higher, a plurality of R3's are the same as or different from each other. In yet another exemplary embodiment, when r6 is 2 or higher, a plurality of R6's are the same as or different from each other. In yet another exemplary embodiment, when r7 is 2 or higher, a plurality of R7's are the same as or different from each other.

In an exemplary embodiment of the present specification, one or more of R1 to R3, R6, and R7 are represented by Formula 2-A or 2-B.

In an exemplary embodiment of the present specification, two of adjacent R1's, two of adjacent R2's, two of adjacent R3's, two of adjacent R6's, or two of adjacent R7's are bonded to each other to form a substituted or unsubstituted aliphatic hydrocarbon ring. Specifically, two of adjacent R1's, two of adjacent R2's, two of adjacent R3's, two of adjacent R6's, or two of adjacent R7's are bonded to each other to form the following ring Cy1 to be described below. In this case, one of the rings formed by bonding R1 to R7 to an adjacent substituent may be an aliphatic hydrocarbon ring, and the case of further forming an aromatic hydrocarbon ring, an aromatic hetero ring or an aliphatic hetero ring is not excluded.

In an exemplary embodiment of the present specification, R1 to R3, R6, and R7 are the same as or different from each other, and are each independently hydrogen; deuterium; a halogen group; a cyano group; a substituted or unsubstituted alkyl group; a substituted or unsubstituted cycloalkyl group; a substituted or unsubstituted silyl group; a substituted or unsubstituted alkenyl group; a substituted or unsubstituted aryl group; a substituted or unsubstituted heterocyclic group; a substituted or unsubstituted alkoxy group; a substituted or unsubstituted aryloxy group; a substituted or unsubstituted alkylthio group; a substituted or unsubstituted arylthio group; or a substituted or unsubstituted amine group, or a group represented by the following Formula 2-A or 2-B, or are bonded to an adjacent substituent to form a substituted or unsubstituted ring.

In an exemplary embodiment of the present specification, R1 to R3, R6 and R7 are the same as or different from each other, and are each independently hydrogen; deuterium; a halogen group; a cyano group; a substituted or unsubstituted C1-C10 alkyl group; a substituted or unsubstituted C3-C30 cycloalkyl group; a substituted or unsubstituted C1-C30 alkylsilyl group; a substituted or unsubstituted C6-C60 arylsilyl group; a substituted or unsubstituted C6-C30 aryl group; a substituted or unsubstituted C2-C30 heterocyclic group; a substituted or unsubstituted C6-C60 arylamine group; or a substituted or unsubstituted heteroarylamine group, or are bonded to an adjacent substituent to form a substituted or unsubstituted C2-C30 ring.

In an exemplary embodiment of the present specification, R1 to R3, R6, and R7 are the same as or different from each other, and are each independently hydrogen; deuterium; a halogen group; a cyano group; a C1-C10 alkyl group which is unsubstituted or substituted with one or more substituents selected from the group consisting of deuterium, a C1-C10 alkyl group, and a C6-C30 aryl group or a substituent to which two or more groups selected from the above group are linked; a C3-C30 cycloalkyl group; a C1-C30 alkylsilyl group; a C6-C60 arylsilyl group; a C6-C30 aryl group which is unsubstituted or substituted with one or more substituents selected from the group consisting of deuterium, a halogen group, a cyano group, a C1-C10 alkyl group, a silyl group, a C6-C30 aryl group, and a C9-C30 fused ring group or a substituent to which two or more groups selected from the above group are linked; a C9-C30 fused hydrocarbon ring group which is unsubstituted or substituted with one or more substituents selected from the group consisting of deuterium and a C1-C10 alkyl group or a substituent to which two or more groups selected from the above group are linked; a C2-C30 heterocyclic group which is unsubstituted or substituted with one or more substituents selected from the group consisting of deuterium, a halogen group, a cyano group, a C1-C10 alkyl group, a silyl group, and a C6-C30 aryl group or a substituent to which two or more groups selected from the above group are linked; or an amine group which is unsubstituted or substituted with one or more substituents selected from the group consisting of deuterium, a halogen group, a cyano group, a C1-C10 alkyl group, a silyl group, a C6-C30 aryl group, and a C9-C30 fused hydrocarbon ring group or a substituent to which two or more groups selected from the above group are linked, or are bonded to an adjacent substituent to form a C2-C30 ring which is unsubstituted or substituted with one or more substituents selected from the group consisting of deuterium, a C1-C10 alkyl group, a silyl group, and a C6-C30 aryl group or a substituent to which two or more groups selected from the above group are linked.

In an exemplary embodiment of the present specification, R1 to R3, R6, and R7 are the same as or different from each other, and are each independently hydrogen; deuterium; a halogen group; a cyano group; an alkyl group which is unsubstituted or substituted with deuterium or a C6-C30 aryl group; a C3-C30 cycloalkyl group; a C1-C30 alkylsilyl group; a C6-C60 arylsilyl group; a C6-C30 aryl group which is unsubstituted or substituted with deuterium, a halogen group, a cyano group, a C1-C10 alkyl group, a C1-C10 alkyl group substituted with deuterium, a C1-C10 haloalkyl group, a C9-C30 fused hydrocarbon ring group, a C9-C30 fused hydrocarbon ring group substituted with a C1-C10 alkyl group, or a C1-C30 alkylsilyl group; a C2-C30 heterocyclic group which is unsubstituted or substituted with deuterium, a C1-C10 alkyl group, a C1-C10 alkyl group substituted with deuterium, a C6-C30 aryl group, a C6-C30 aryl group substituted with deuterium, or a C1-C30 alkylsilyl group; or a C6-C60 arylamine group which is unsubstituted or substituted with deuterium, a C1-C10 alkyl group, a C1-C10 alkyl group substituted with deuterium, or a C1-C30 alkylsilyl group, and which is unfused or fused with a C5-C30 aliphatic hydrocarbon ring, or are bonded to an adjacent substituent to form a C2-C30 ring which is unsubstituted or substituted with deuterium, a C1-C10 alkyl group, a C1-C10 alkyl group substituted with deuterium, a C6-C30 aryl group, or a C6-C30 aryl group substituted with deuterium, or a C1-C30 alkylsilyl group.

In an exemplary embodiment of the present specification, R1 to R3, R6, and R7 are the same as or different from each other, and are each independently hydrogen; deuterium; a fluoro group; a cyano group; a methyl group which is unsubstituted or substituted with deuterium; an ethyl group; an isopropyl group; a tert-butyl group; an isopropyl group substituted with a phenyl group; a cyclohexyl group; an adamantyl group; a trimethylsilyl group; a triphenylsilyl group; a phenyl group which is unsubstituted or substituted with deuterium, a fluoro group, a cyano group, a methyl group, an isopropyl group, a tert-butyl group, $CD_3$, $CF_3$, a trimethylsilyl group, a tert-butyldimethylsilyl group, a tetramethyltetrahydronaphthalene group, a dimethyldihydroindene group, or a tetramethyldihydroindene group; a biphenyl group which is unsubstituted or substituted with deuterium, a fluoro group, a cyano group, a methyl group, an isopropyl group, a tert-butyl group, $CD_3$, $CF_3$, a trimethylsilyl group, a tert-butyldimethylsilyl group, a tetramethyltetrahydronaphthalene group, a dimethyldihydroindene group, or a tetramethyldihydroindene group; a naphthyl group; a fluorene group which is unsubstituted or substituted with a methyl group or a phenyl group; a benzofluorene group which is unsubstituted or substituted with a methyl group or a phenyl group; a hydronaphthalene group which is unsubstituted or substituted with a methyl group; a dihydroindene group which is unsubstituted or substituted with a methyl group; a diphenylamine group which is unsubstituted or substituted with deuterium, a methyl group, an isopropyl group, a tert-butyl group, $CD_3$, a trimethylsilyl group, or a phenyl group, and which is unfused or fused with a cyclopentene ring or a cyclohexene ring; a dibenzofuran group which is unsubstituted or substituted with a methyl group, a tert-butyl group, or a phenyl group; a naphthobenzofuran group; a dibenzothiophene group which is unsubstituted or substituted with a methyl group, a tert-butyl group, or a phenyl group; a naphthobenzothiophene group; a dibenzosilole group which is unsubstituted or substituted with a methyl group or a phenyl group; a naphthobenzosilole group which is unsubstituted or substituted with a methyl group or a phenyl group; a group represented by Formula 2-A or 2-B; or a group represented by one of Formulae 2-A-3 to 2-A-6 to be described below.

In an exemplary embodiment of the present specification, R1 to R3, R6, and R7 are bonded to an adjacent substituent to form a substituted or unsubstituted aromatic hydrocarbon ring; a substituted or unsubstituted aliphatic hydrocarbon ring; a substituted or unsubstituted aromatic hetero ring; or a substituted or unsubstituted aliphatic hetero ring.

In an exemplary embodiment of the present specification, R1 is bonded to adjacent R1 to form a substituted or unsubstituted ring. In another exemplary embodiment, R2 is bonded to adjacent R2 to form a substituted or unsubstituted ring. In still another exemplary embodiment, R3 is bonded to adjacent R3 to form a substituted or unsubstituted ring. In yet another exemplary embodiment, R6 is bonded to adjacent R6 to form a substituted or unsubstituted ring. In yet another exemplary embodiment, R7 is bonded to adjacent R7 to form a substituted or unsubstituted ring.

"An aliphatic hydrocarbon ring formed by bonding two of adjacent R1's, two of adjacent R2's, two of adjacent R3's, two of adjacent R6's, or two of adjacent R7's to each other" may become a C5-C20 aliphatic hydrocarbon ring. Specifically, the aliphatic hydrocarbon ring may be a cyclohexene ring; a cyclopentene ring; a bicyclo[2.2.1]heptene ring; or a bicyclo[2.2.2]octene ring, and the ring is unsubstituted or substituted with a methyl group.

Further, "an aromatic hydrocarbon ring formed by bonding two of adjacent R1's, two of adjacent R2's, two of adjacent R3's, two of adjacent R6's, or two of adjacent R7's to each other" may become a C6-C20 aromatic hydrocarbon ring. Specifically, the aromatic hydrocarbon ring may be an indene ring; or a spiro[indene-fluorene]ring, and the ring is unsubstituted or substituted with a methyl group, an isopropyl group, a tert-butyl group, or a phenyl group.

In addition, "an aromatic hetero ring formed by bonding two of adjacent R1's, two of adjacent R2's, two of adjacent R3's, two of adjacent R6's, or two of adjacent R7's to each other" may be a C5-C20 aromatic hetero ring including one or more of O, S, Si, and N. Specifically, the aromatic hetero ring may be a furan ring; a dihydrofuran ring; a benzofuran ring; a naphthofuran ring; a thiophene ring; a dihydrothiophene ring; a benzothiophene ring; a naphthofuran ring; an indole ring; a benzoindole ring; a silole ring; a benzosilole ring; or a naphthosilole ring, and the ring is unsubstituted or substituted with a methyl group, an isopropyl group, a tert-butyl group, or a phenyl group.

In an exemplary embodiment of the present specification, two of adjacent R1's, two of adjacent R2's, two of adjacent R3's, two of adjacent R6's, or two of adjacent R7's are bonded to each other to form one ring of Cy1 to Cy3 to be described below.

In an exemplary embodiment of the present specification, L11 is a direct bond; or a substituted or unsubstituted C6-C20 arylene group.

In an exemplary embodiment of the present specification, L11 is a direct bond; or a phenylene group. In an exemplary embodiment of the present specification, L11 is a direct bond.

In an exemplary embodiment of the present specification, T11 to T14 are the same as or different from each other, and are each independently hydrogen; deuterium; a substituted or unsubstituted alkyl group; a substituted or unsubstituted aryl group; a substituted or unsubstituted alkylsilyl group; or a substituted or unsubstituted arylsilyl group, or are bonded to an adjacent substituent to form a ring.

In an exemplary embodiment of the present specification, T11 to T14 are the same as or different from each other, and are each independently hydrogen; deuterium; a substituted or unsubstituted C1-C10 alkyl group; a substituted or unsubstituted C6-C30 aryl group; a substituted or unsubstituted C1-C30 alkylsilyl group; or a substituted or unsubstituted C6-C60 arylsilyl group, or are bonded to an adjacent substituent to form a substituted or unsubstituted C6-C30 aromatic hydrocarbon ring.

In an exemplary embodiment of the present specification, T11 to T14 are the same as or different from each other, and are each independently hydrogen; deuterium; a C1-C6 alkyl group which is unsubstituted or substituted with deuterium; a C6-C20 aryl group which is unsubstituted or substituted with deuterium or a C1-C6 alkyl group; or a C1-C30 alkylsilyl group, or are bonded to an adjacent substituent to form a C6-C30 aromatic hydrocarbon ring which is unsubstituted or substituted with deuterium or a C1-C6 alkyl group.

In an exemplary embodiment of the present specification, T11 to T14 are the same as or different from each other, and are each independently hydrogen; deuterium; a methyl group which is unsubstituted or substituted with deuterium; an isopropyl group; a tert-butyl group; or a phenyl group which is unsubstituted or substituted with deuterium, a methyl group, an isopropyl group, or a tert-butyl group, or are bonded to an adjacent substituent to form a benzene ring which is unsubstituted or substituted with deuterium, a methyl group, an isopropyl group, or a tert-butyl group.

In an exemplary embodiment of the present specification, T15 and T16 are the same as or different from each other, and are each independently hydrogen; deuterium; a substituted or unsubstituted alkyl group; or a substituted or unsubstituted aryl group, or are bonded to each other to form a substituted or unsubstituted hydrocarbon ring.

In an exemplary embodiment of the present specification, T15 and T16 are the same as or different from each other, and are each independently hydrogen; deuterium; a substituted or unsubstituted C1-C6 alkyl group; or a substituted or unsubstituted C6-C20 aryl group, or are bonded to each other to form a substituted or unsubstituted C5-C20 hydrocarbon ring.

In an exemplary embodiment of the present specification, T15 and T16 are the same as or different from each other, and are each independently hydrogen; deuterium; or a methyl group, or are bonded to each other to form a fluorene ring while being a phenyl group.

In an exemplary embodiment of the present specification, Y1 is C.

In an exemplary embodiment of the present specification, Y1 is Si.

In an exemplary embodiment of the present specification, when p1 is 0, a site including Y1 is a direct bond.

In an exemplary embodiment of the present specification, A11 to A14 are the same as or different from each other, and are each independently hydrogen; deuterium; or a substituted or unsubstituted alkyl group, or are bonded to an adjacent substituent to form a substituted or unsubstituted aliphatic hydrocarbon ring.

In an exemplary embodiment of the present specification, A11 to A14 are the same as or different from each other, and are each independently hydrogen; deuterium; or a C1-C6 alkyl group which is unsubstituted or substituted with deuterium, or are bonded to an adjacent substituent to form a substituted or unsubstituted C5-C20 aliphatic hydrocarbon ring.

In an exemplary embodiment of the present specification, two of A11 to A14 are bonded to each other to form a substituted or unsubstituted aliphatic hydrocarbon ring, and the other two are hydrogen; deuterium; or a substituted or unsubstituted alkyl group.

In an exemplary embodiment of the present specification, two of A11 to A14 are bonded to each other to form a cyclopentane ring; a cyclohexane ring; or a cycloheptane ring, and the other two are hydrogen; deuterium; or a methyl group.

In an exemplary embodiment of the present specification, two of A11 to A14 are bonded to each other to form a cyclohexane ring, and the other two are hydrogen; deuterium; or a methyl group.

In an exemplary embodiment of the present specification, Formula 2-A is represented by the following Formula 2-A-1 or 2-A-2.

[Formula 2-A-1]

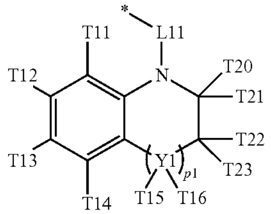

[Formula 2-A-2]

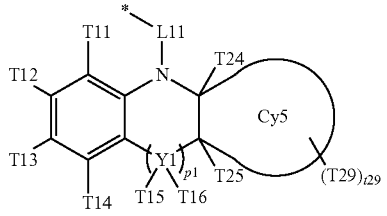

In Formulae 2-A-1 and 2-A-2,

* is a bonding site, definitions of L11, T11 to T16, Y1, and p1 are the same as those defined in Formula 2-A, T20 to T25, and T29 are the same as or different from each other, and are each independently hydrogen; deuterium; a substituted or unsubstituted alkyl group; or a substituted or unsubstituted aryl group, Cy5 is an aliphatic hydrocarbon ring, and t29 is an integer from 0 to 10, and when t29's are each 2 or higher, T29's are the same as or different from each other.

In an exemplary embodiment of the present specification, the heterocyclic group of R1 to R3, R6, and R7 includes one or more of N, O, S, and Si as a heteroatom.

In an exemplary embodiment of the present specification, the O-containing heterocyclic group of R1 to R3, R6, and R7 may be a benzofuran group; a dibenzofuran group; or a naphthobenzofuran group, and is unsubstituted or substituted with deuterium, a C1-C6 alkyl group, or a C6-C20 aryl group.

In an exemplary embodiment of the present specification, the S-containing heterocyclic group of R1 to R3, R6, and R7 may be a benzothiophene group; a dibenzothiophene group; or a naphthobenzothiophene group, and is unsubstituted or substituted with deuterium, a C1-C6 alkyl group, or a C6-C20 aryl group.

In an exemplary embodiment of the present specification, the Si-containing heterocyclic group of R1 to R3, R6, and R7 may be a benzosilole group; a dibenzosilole group; or a naphthobenzosilole group, and is unsubstituted or substituted with deuterium, a C1-C6 alkyl group, or a C6-C20 aryl group.

In an exemplary embodiment of the present specification, the N-containing heterocyclic group of R1 to R3, R6, and R7 is represented by Formula 2-A-1 or 2-A-2; or one of the following Formulae 2-A-3 to 2-A-6.

[Formula 2-A-3]

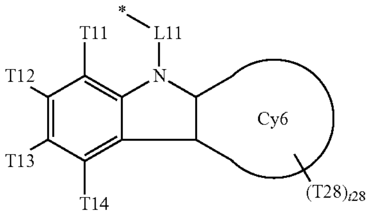

[Formula 2-A-4]

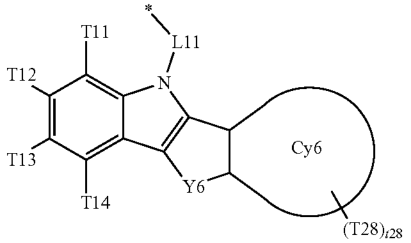

[Formula 2-A-5]

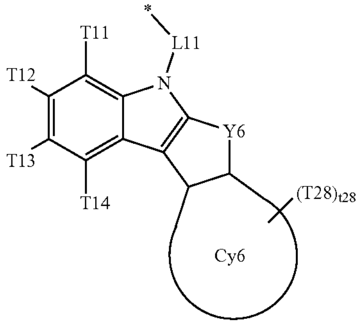

[Formula 2-A-6]

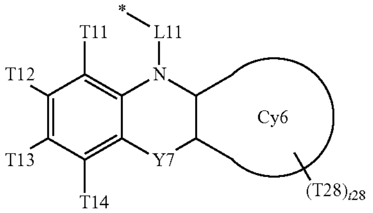

In Formulae 2-A-3 to 2-A-6,

* is a bonding site, definitions of L11 and T11 to T16 are the same as those defined in Formula 2-A, Y6 and Y7 are the same as or different from each other, and are each independently O; S; C(T26) (T27); or Si(T26) (T27), T26 to T28 are the same as or different from each other, and are each independently hydrogen; deuterium; a substituted or unsubstituted alkyl group; or a substituted or unsubstituted aryl group, Cy6 is an aromatic hydrocarbon ring, and t28 is an integer from 0 to 10, and when t28's are each 2 or higher, T28's are the same as or different from each other.

In an exemplary embodiment of the present specification, Y6 is O; or S.

In an exemplary embodiment of the present specification, Y6 is C (T26) (T27); or Si (T26) (T27). In an exemplary embodiment of the present specification, Y6 is C(T26) (T27).

In an exemplary embodiment of the present specification, Y7's are the same as or different from each other, and are each independently O; S; or C(T26) (T27).

In an exemplary embodiment of the present specification, t28 is an integer from 0 to 6, and when t28 is 2 or higher, a plurality of T28's are the same as or different from each other.

In an exemplary embodiment of the present specification, t29 is an integer 0 to 10, and when t29 is 2 or higher, a plurality of T29's are the same as or different from each other.

In an exemplary embodiment of the present specification, T20 to T27 are the same as or different from each other, and are each independently hydrogen; deuterium; a substituted or unsubstituted C1-C6 alkyl group; or a substituted or unsubstituted C6-C20 aryl group.

In an exemplary embodiment of the present specification, T20 to T27 are the same as or different from each other, and are each independently hydrogen; deuterium; or a C1-C6 alkyl group which is unsubstituted or substituted with deuterium.

In an exemplary embodiment of the present specification, T20 to T27 are the same as or different from each other, and are each independently hydrogen; deuterium; or a methyl group.

In an exemplary embodiment of the present specification, T26 and T27 are each a methyl group.

In an exemplary embodiment of the present specification, T20 to T27 are each a methyl group.

In an exemplary embodiment of the present specification, T28 and T29 are the same as or different from each other, and are each independently hydrogen; deuterium; a substituted or unsubstituted C1-C6 alkyl group; or a substituted or unsubstituted C6-C20 aryl group.

In an exemplary embodiment of the present specification, T28 and T29 are the same as or different from each other, and are each independently hydrogen; deuterium; a C1-C6 alkyl group which is unsubstituted or substituted with deuterium; or a C6-C20 aryl group which is unsubstituted or substituted with deuterium.

In an exemplary embodiment of the present specification, T28 and T29 are the same as or different from each other, and are each independently hydrogen; deuterium; a tert-butyl group; or a phenyl group.

In an exemplary embodiment of the present specification, T28 and T29 are the same as or different from each other, and are each independently hydrogen; deuterium; or a tert-butyl group.

In an exemplary embodiment of the present specification, T28 is hydrogen; deuterium; a tert-butyl group; or a phenyl group.

In an exemplary embodiment of the present specification, T28 is hydrogen; deuterium; or a tert-butyl group.

In an exemplary embodiment of the present specification, T28 is hydrogen; or deuterium.

In an exemplary embodiment of the present specification, T29 is hydrogen; or deuterium.

In an exemplary embodiment of the present specification, Cy5 is a C5-C20 aliphatic hydrocarbon ring.

In an exemplary embodiment of the present specification, Cy5 is a cyclopentane ring; a cyclohexane ring; or a cycloheptane ring.

In an exemplary embodiment of the present specification, Cy5 is a cyclohexane ring.

In an exemplary embodiment of the present specification, Cy6 is a C6-C20 aromatic hydrocarbon ring.

In an exemplary embodiment of the present specification, Cy6 is a benzene ring; or a naphthalene ring.

In an exemplary embodiment of the present specification, Cy6 is a benzene ring.

In an exemplary embodiment of the present specification, T17 to T19 are the same as or different from each other, and are each independently a substituted or unsubstituted alkyl group; or a substituted or unsubstituted aryl group, and at least one of T17 to T19 is a substituted or unsubstituted aryl group.

In an exemplary embodiment of the present specification, T17 to T19 are the same as or different from each other, and are each independently a substituted or unsubstituted C1-C10 alkyl group; or a substituted or unsubstituted C6-C30 aryl group, and at least one of T17 to T19 is a substituted or unsubstituted C6-C30 aryl group.

In an exemplary embodiment of the present specification, T17 to T19 are the same as or different from each other, and are each independently a C1-C6 alkyl group which is unsubstituted or substituted with deuterium; or a C6-C20 aryl group which is unsubstituted or substituted with deuterium, and at least one of T17 to T19 is a C6-C20 aryl group which is unsubstituted or substituted with deuterium.

In an exemplary embodiment of the present specification, one of T17 to T19 is a C6-C20 aryl group which is unsubstituted or substituted with deuterium, and two of T17 to T19 are a C1-C6 alkyl group which is unsubstituted or substituted with deuterium.

In an exemplary embodiment of the present specification, T17 to T19 are the same as or different from each other, and are each independently a C1-C6 alkyl group; or a C6-C20 aryl group, and at least one of T17 to T19 is a C6-C20 aryl group.

In an exemplary embodiment of the present specification, T17 is a substituted or unsubstituted aryl group, T18 is a substituted or unsubstituted alkyl group, and T19 is a substituted or unsubstituted alkyl group or a substituted or unsubstituted aryl group.

In an exemplary embodiment of the present specification, T17 to T19 are the same as or different from each other, and are each independently a methyl group which is unsubstituted or substituted with deuterium; or a phenyl group which is unsubstituted or substituted with deuterium, and at least one of T17 to T19 is a phenyl group which is unsubstituted or substituted with deuterium.

In an exemplary embodiment of the present specification, one of T17 to T19 is a phenyl group which is unsubstituted or substituted with deuterium, and two of T17 to T19 are a methyl group which is unsubstituted or substituted with deuterium.

In an exemplary embodiment of the present specification, T17 to T19 are the same as or different from each other, and are each independently a methyl group; or a phenyl group, and at least one of T17 to T19 is a phenyl group.

In an exemplary embodiment of the present specification, one of T17 to T19 is a phenyl group, and the other two are a methyl group.

In an exemplary embodiment of the present specification, R6 is linked to the ortho position with respect to nitrogen (N) while being a substituent other than hydrogen. Specifically, in the following formula, a substituent other than hydrogen (R6 of a halogen group, a cyano group, an alkyl group, an alkoxy group, an alkylthio group, an aryl group, an aryloxy group, an arylthio group, a heterocyclic group, a cycloalkyl group, an alkylsilyl group, an arylsilyl group, an arylalkyl group, an alkylamine group, an arylamine group, a heteroarylamine group, and the like) is linked to one or two of the positions represented by a dotted line. In this case, a substituent may be further linked to or a ring may be formed at the meta or para position with respect to nitrogen (N).

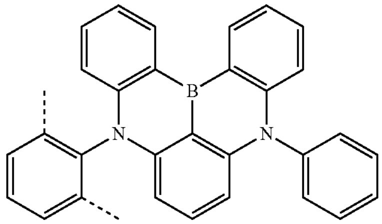

In an exemplary embodiment of the present specification, R7 is linked to the ortho position with respect to nitrogen (N) while being a substituent other than hydrogen. Specifically, in the following formula, a substituent other than hydrogen (R7 of a halogen group, a cyano group, an alkyl group, an alkoxy group, an alkylthio group, an aryl group, an aryloxy group, an arylthio group, a heterocyclic group, a cycloalkyl group, an alkylsilyl group, an arylsilyl group, an arylalkyl group, an alkylamine group, an arylamine group, a heteroarylamine group, and the like) is linked to one or two of the positions represented by a dotted line. In this case, a substituent may be further linked to or a ring may be formed at the meta or para position with respect to nitrogen (N).

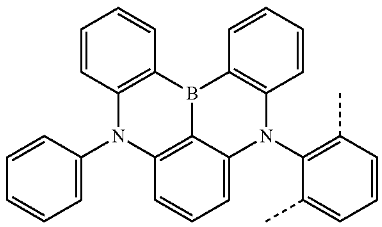

In an exemplary embodiment of the present specification, a ring formed by bonding two of adjacent R1's, two of adjacent R2's, two of adjacent R3's, two of adjacent R6's, or two of adjacent R7's to each other is one of the following rings Cy1 to Cy3.

[Cy1]

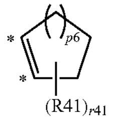

[Cy2]

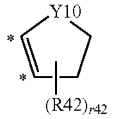

[Cy3]

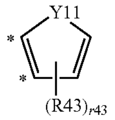

In Cy1 to Cy3,

* is a carbon that participates in the formation of a ring among R1 to R3, R6, and R7, Y10 is O; S; Si(Ra3) (Ra4); or N(Ra5), Y11 is O; S; Si(Ra3) (Ra4); C(Ra3) (Ra4); or N(Ra5), R41 to R43 and Ra3 to Ra5 are the same as or different from each other, and are each independently hydrogen; deuterium; a substituted or unsubstituted alkyl group; or a substituted or unsubstituted aryl group, and are bonded to an adjacent substituent to form a substituted or unsubstituted ring, p6 is an integer from 1 to 3, and r41 is an integer from 0 to 10, r42 is an integer from 0 to 4, r43 is an integer from 0 to 2, and when r41 to r43 are each 2 or higher, substituents in the parenthesis are the same as or different from each other.

In an exemplary embodiment of the present specification, when r41 is 2 or higher, a plurality of R41's are the same as or different from each other. In another exemplary embodiment, when r42 is 2 or higher, a plurality of R42's are the same as or different from each other. In still another exemplary embodiment, when r43 is 2 or higher, a plurality of R43's are the same as or different from each other.

In the structures, * is a position in which a substituent is fused with Formula 2.

In an exemplary embodiment of the present specification, p6 is 1 or 2.

In an exemplary embodiment of the present specification, R41 to R43 and Ra3 to Ra5 are the same as or different from each other, and are each independently hydrogen; deuterium; a substituted or unsubstituted C1-C10 alkyl group; a substituted or unsubstituted C6-C30 aryl group, or are bonded to an adjacent substituent to form a substituted or unsubstituted ring.

In an exemplary embodiment of the present specification, R41 to R43 and Ra3 to Ra5 are the same as or different from each other, and are each independently hydrogen; deuterium; a C1-C6 alkyl group which is unsubstituted or substituted with deuterium; or a C6-C20 aryl group which is unsubstituted or substituted with deuterium or a C1-C6 alkyl group, and are bonded to an adjacent substituent to form a C5-C20 hydrocarbon ring which is unsubstituted or substituted with deuterium, a C1-C6 alkyl group, or a C6-C20 aryl group; or a C2-C20 hetero ring which is unsubstituted or substituted with deuterium, a C1-C6 alkyl group, or a C6-C20 aryl group.

In an exemplary embodiment of the present specification, R41 to R43 are the same as or different from each other, and are each independently hydrogen; deuterium; a methyl group which is unsubstituted or substituted with deuterium; an isopropyl group; a tert-butyl group; or a phenyl group.

In an exemplary embodiment of the present specification, R41 is bonded to R41 which is not adjacent to make a form in which a Cy1 ring is a double ring (a bicycloalkane ring or a bicycloalkene ring), such as a bridgehead, or a fused ring. Specifically, the Cy1 is a bicyclo[2.2.2]octene ring; or a bicyclo[2.2.1]heptene ring, and the ring is unsubstituted or substituted with R41.

In an exemplary embodiment of the present specification, R42 is bonded to adjacent R42 to form a substituted or unsubstituted aliphatic hydrocarbon ring.

In an exemplary embodiment of the present specification, R42 is bonded to adjacent R42 to form a C5-C30 aliphatic hydrocarbon ring which is unsubstituted or substituted with deuterium, a C1-C10 alkyl group, or a C1-C10 alkyl group substituted with deuterium.

In an exemplary embodiment of the present specification, R42 is bonded to adjacent R42 to form a C5-C20 aliphatic hydrocarbon ring which is unsubstituted or substituted with deuterium, a C1-C6 alkyl group, or a C1-C6 alkyl group substituted with deuterium.

In an exemplary embodiment of the present specification, R43 is bonded to adjacent R43 to form a substituted or unsubstituted C6-C30 aromatic hydrocarbon ring; or a substituted or unsubstituted C5-C30 aliphatic hydrocarbon ring.

In an exemplary embodiment of the present specification, R43 is bonded to adjacent R43 to form a benzene ring; a naphthalene ring; a cyclopentene ring; a cyclohexene ring; a tetrahydronaphthalene ring; a bicyclo[2.2.2]octene ring; or a bicyclo[2.2.1]heptene ring, and the ring is unsubstituted or substituted with one or more substituents selected from the group consisting of deuterium, a C1-C6 alkyl group, and a C6-C20 aryl group or a substituent to which two or more groups selected from the above group are linked.

In an exemplary embodiment of the present specification, Ra3 to Ra5 are the same as or different from each other, and are each independently a substituted or unsubstituted C1-C10 alkyl group; a substituted or unsubstituted C6-C30 aryl group, or are bonded to an adjacent substituent to form a substituted or unsubstituted C5-C30 hydrocarbon ring.

In an exemplary embodiment of the present specification, Ra3 to Ra5 are the same as or different from each other, and are each independently a C1-C6 alkyl group which is unsubstituted or substituted with deuterium; a C6-C20 aryl group which is unsubstituted or substituted with deuterium or a C1-C6 alkyl group, or are bonded to an adjacent substituent to form a C5-C20 hydrocarbon ring which is unsubstituted or substituted with deuterium or a C1-C6 alkyl group.

In an exemplary embodiment of the present specification, Ra3 and Ra4 are the same as or different from each other, and are each independently a methyl group; or a phenyl group, or are bonded to each other to form a fluorene ring which is unsubstituted or substituted with a methyl group, an isopropyl group, or a tert-butyl group. In an exemplary embodiment of the present specification, Ra5 is a phenyl group.

In an exemplary embodiment of the present specification, Y10 is O; S; Si(Ra3) (Ra4); or N(Ra5).

In an exemplary embodiment of the present specification, an aliphatic hydrocarbon ring formed by bonding two of adjacent R1's, two of adjacent R2's, two of adjacent R3's, two of adjacent R6's, or two of adjacent R7's to each other is Cy1.

In an exemplary embodiment of the present specification, Cy1 is one selected from the following structures.

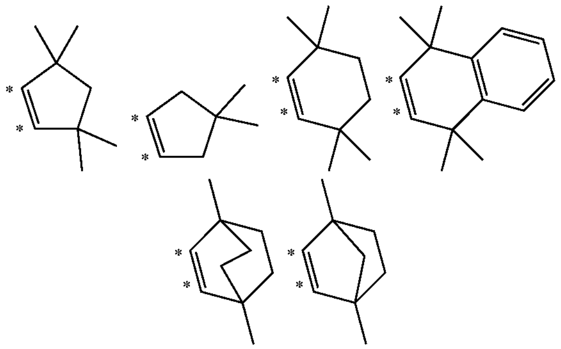

In an exemplary embodiment of the present specification, Cy2 is one selected from the following structures, and Y10 is the same as that described above.

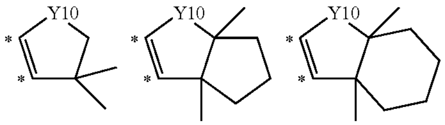

In an exemplary embodiment of the present specification, Cy3 is one selected from the following structures.

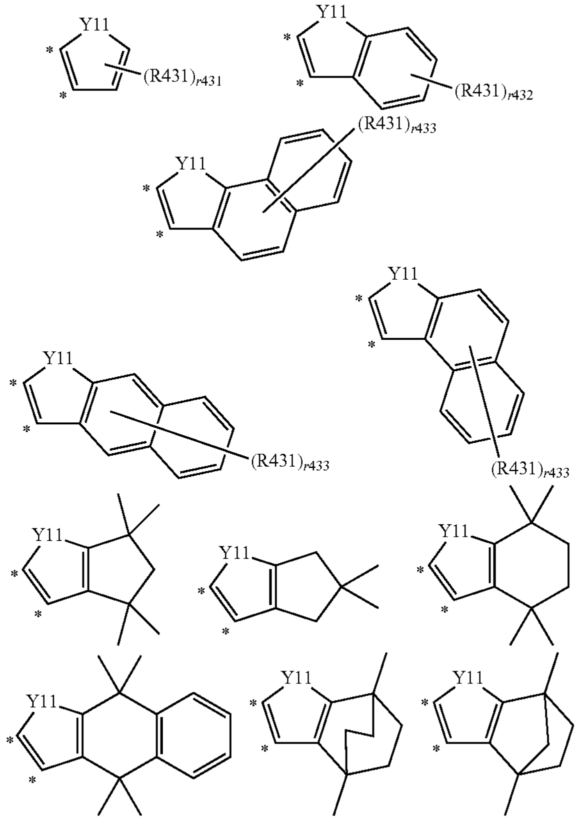

In the structures,

Y11 is the same as that described above, R431 is hydrogen; deuterium; a substituted or unsubstituted alkyl group; or a substituted or unsubstituted aryl group, r431 is an integer from 0 to 2, r432 is an integer from 0 to 4, and r433 is an integer from 0 to 6, and when r431 is 2 or r432 and r433 are 2 or higher, R431's are the same as or different from each other.

In an exemplary embodiment of the present specification, R431 is the same except that R431 forms a ring in the above-described definition of R43.

In an exemplary embodiment of the present specification, R43 is hydrogen; deuterium; a methyl group; an isopropyl group; a tert-butyl group; or a phenyl group.

In an exemplary embodiment of the present specification, Formula 2 is asymmetric with respect to a center line. In this case, the center line is a line penetrating B of a mother nucleus structure and a benzene ring at the bottom. That is, in the following structure, the left and right substituents or structures are different with respect to the dotted line.

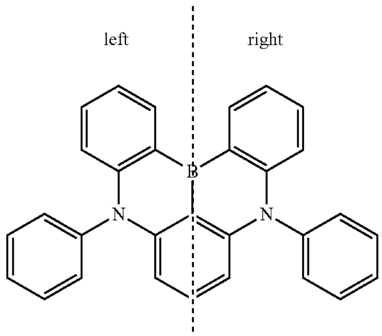

In an exemplary embodiment of the present specification, Formula 2 excludes the following Group Z compounds.

[Group Z]

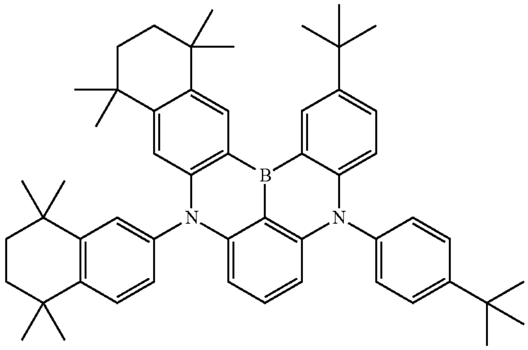

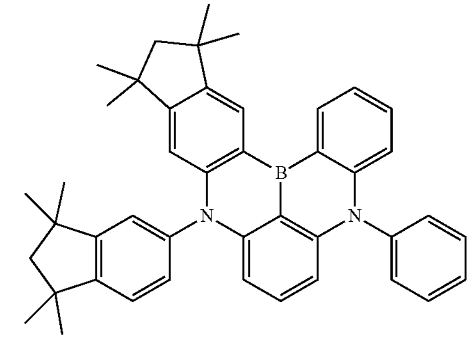

-continued

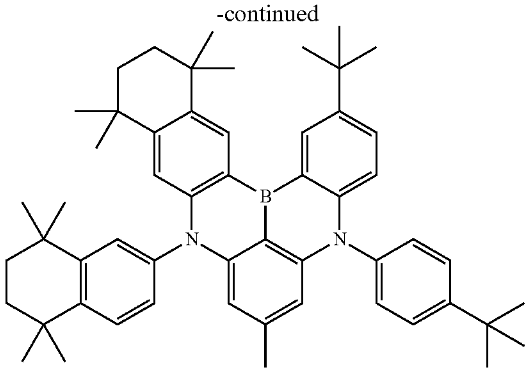

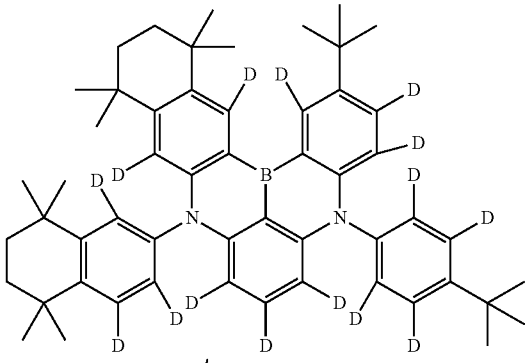

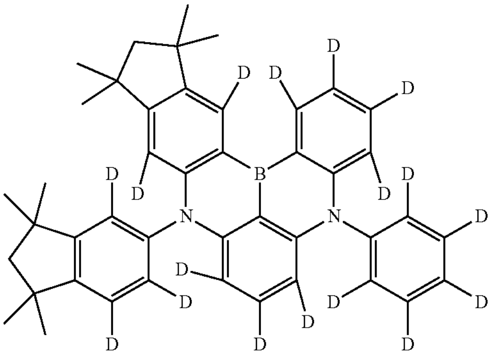

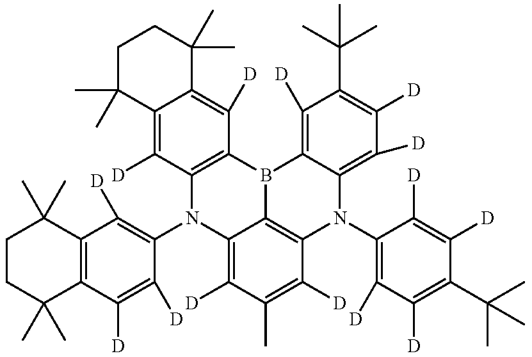 [SMILES: [2H]c1c([2H])c(C(C)(C)C)c([2H])c([2H])c1N1c2c([2H])c([2H])c(C(C)(C)C)c([2H])c2B2c3c([2H])c4c(c([2H])c3N(c3c([2H])c([2H])c5c(c3[2H])C(C)(C)CCC5(C)C)c3c([2H])c(C)c([2H])c1c32)C(C)(C)CCC4(C)C]

In an exemplary embodiment of the present specification, when Formula 2 is one compound of Group Z, Formulae 1-1 to 1-3 include one or more hydrogens.

In an exemplary embodiment of the present specification, when Formula 2 is one compound of Group Z, one or more of Ar11 to Ar13 of Formula 1-1, one or more of Ar21 to Ar24 of Formula 1-2, and one or more of Ar31 and Ar32 of Formula 1-3 are a substituent other than hydrogen and deuterium.

In an exemplary embodiment of the present specification, when Formula 2 is one compound of Group Z, one or more of Ar12 and Ar13 of Formula 1-1, one or more of Ar23 and Ar24 of Formula 1-2, and one or more of Ar31 and Ar32 of Formula 1-3 are an aryl group which is unsubstituted or substituted with deuterium.

In an exemplary embodiment of the present specification, when Formula 2 is one compound of Group Z, one or more of Ar12 and Ar13 of formula 1-1, one or more of Ar23 and Ar24 of Formula 1-2, and one or more of Ar31 and Ar32 of Formula 1-3 are a phenyl group which is unsubstituted or substituted with deuterium; a biphenyl group which is unsubstituted or substituted with deuterium; or a naphthyl group which is unsubstituted or substituted with deuterium.

In an exemplary embodiment of the present specification, the compound represented by Formula 2 is any one selected from the following compounds.

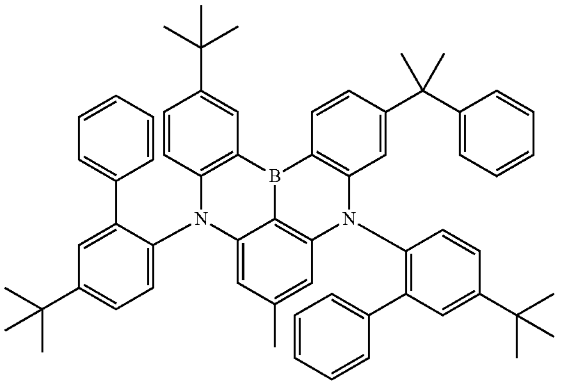

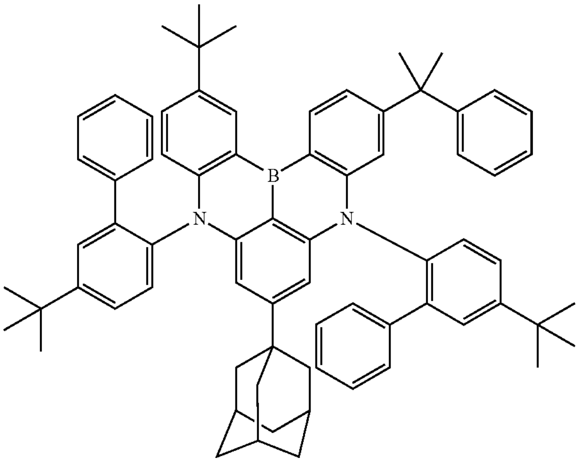

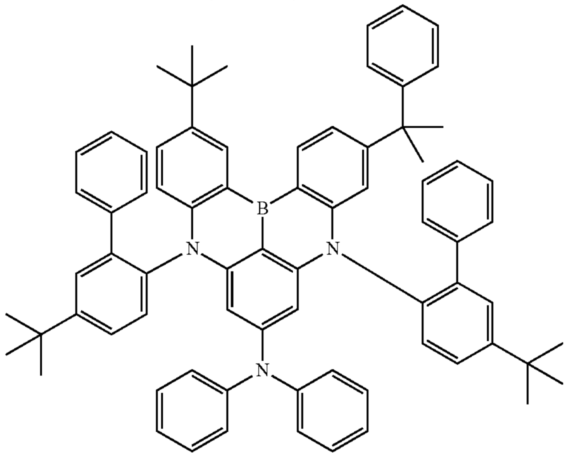

1061
-continued
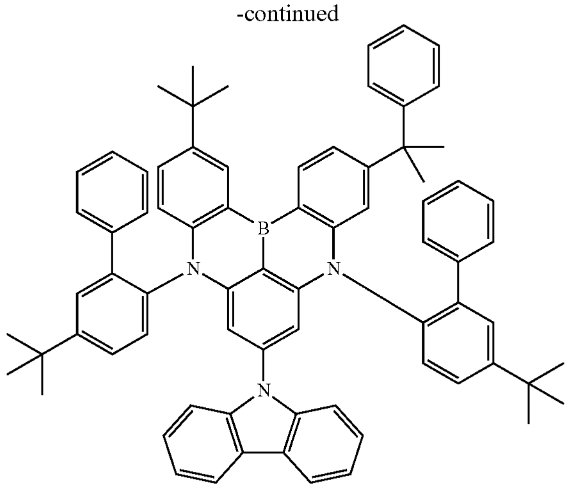
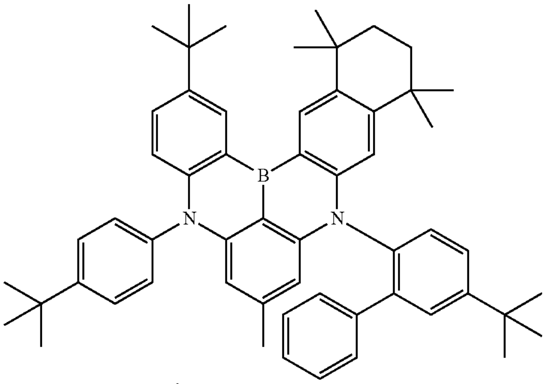
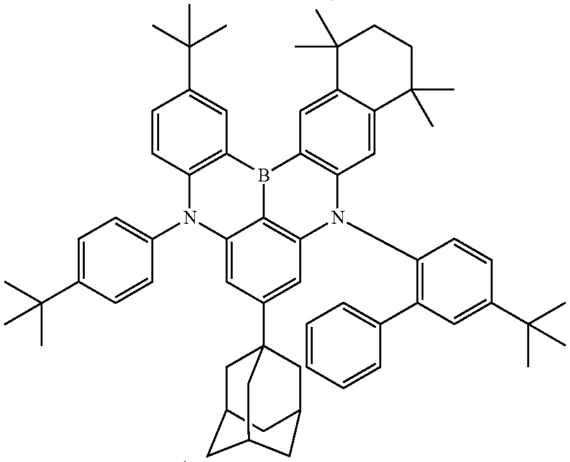
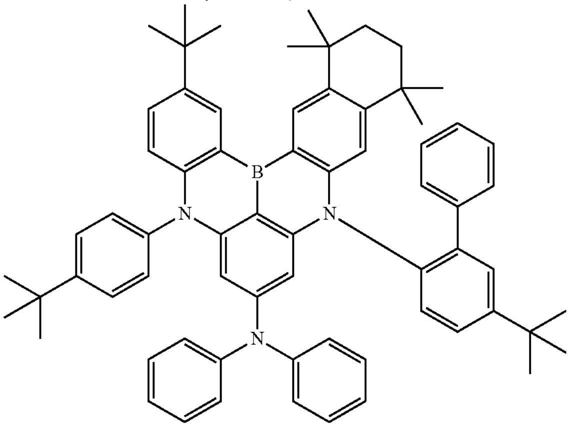
1062
-continued
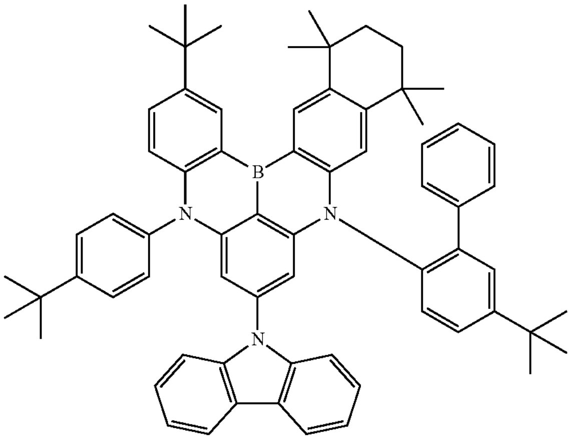
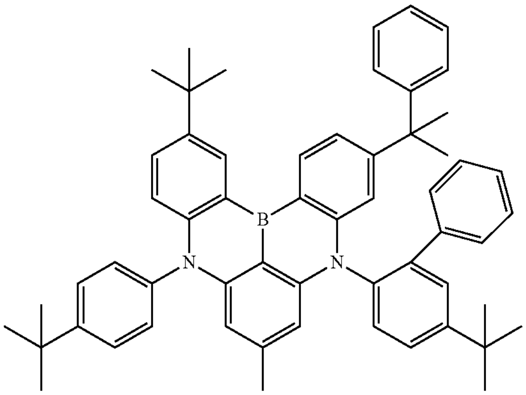
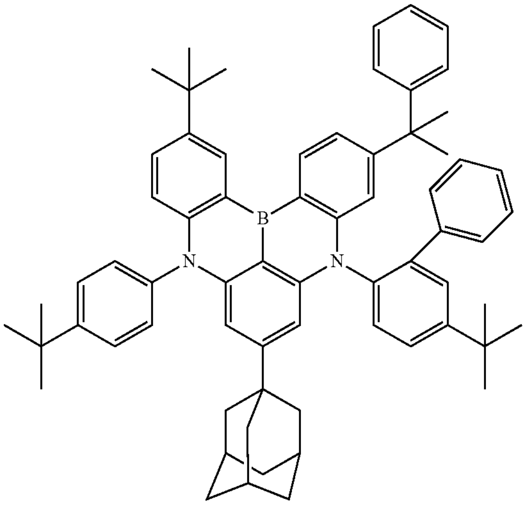

-continued
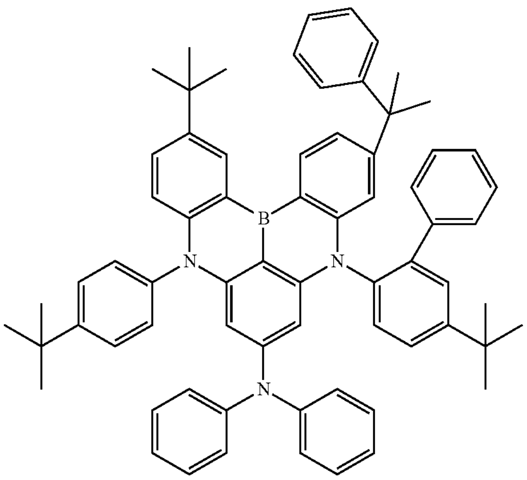
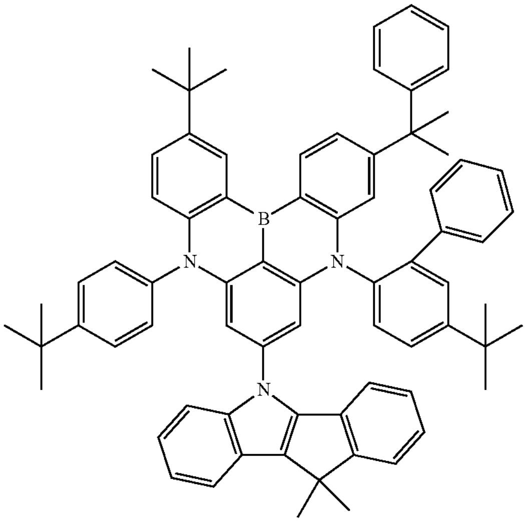
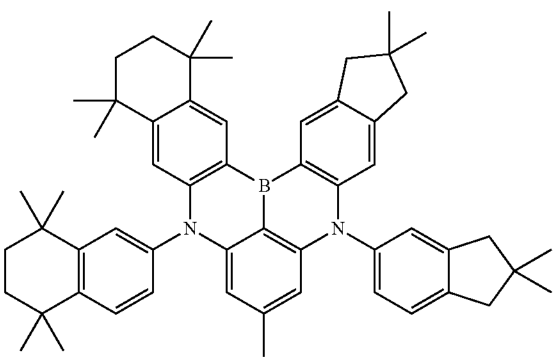
-continued
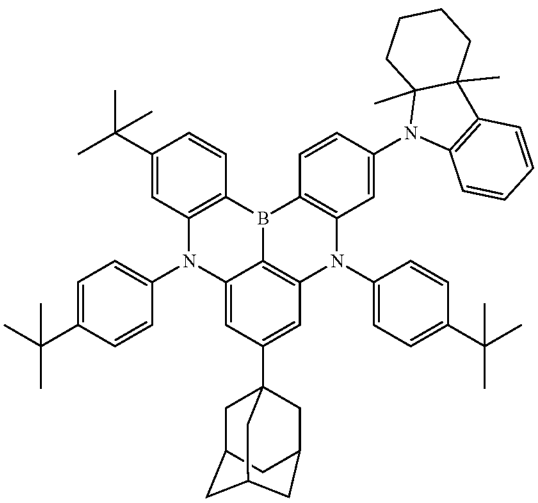
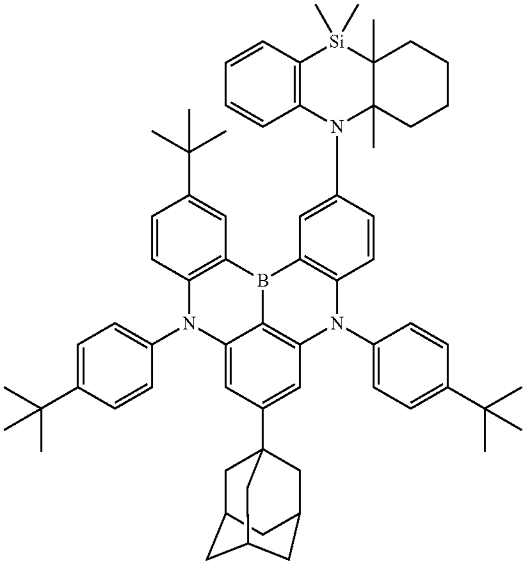
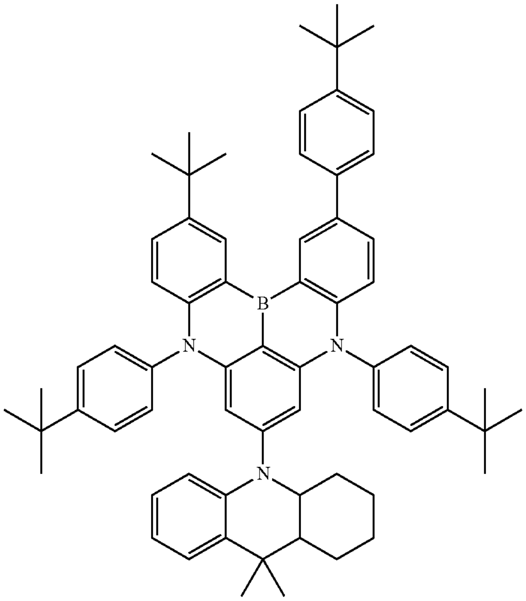 [SMILES: CC(C)(C)c1ccc(-c2ccc3c(c2)B2c4cc(C(C)(C)C)ccc4N(c4ccc(C(C)(C)C)cc4)c4cc(N5c6ccccc6C(C)(C)C6CCCCC65)cc(c42)N3c2ccc(C(C)(C)C)cc2)cc1]

-continued
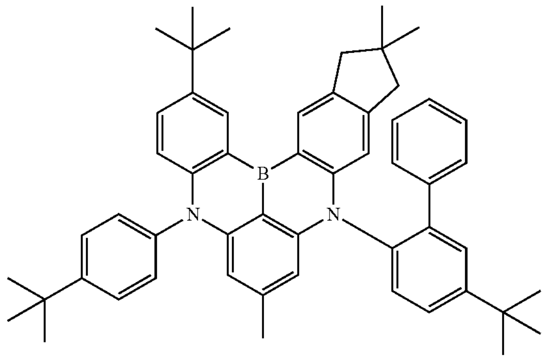
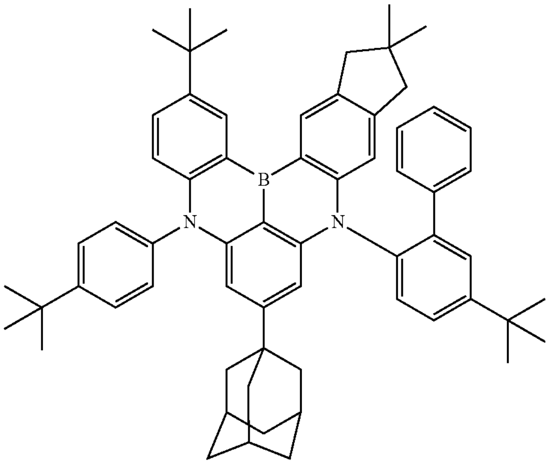
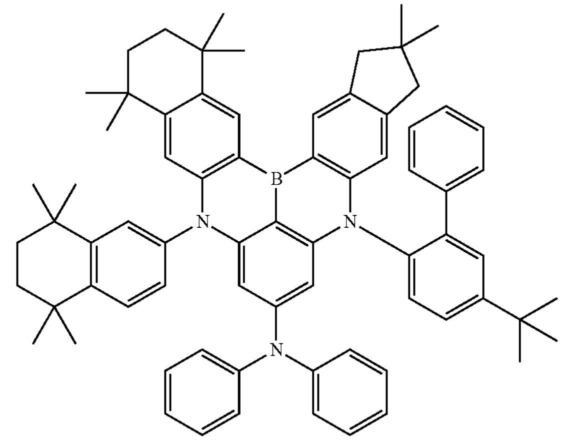
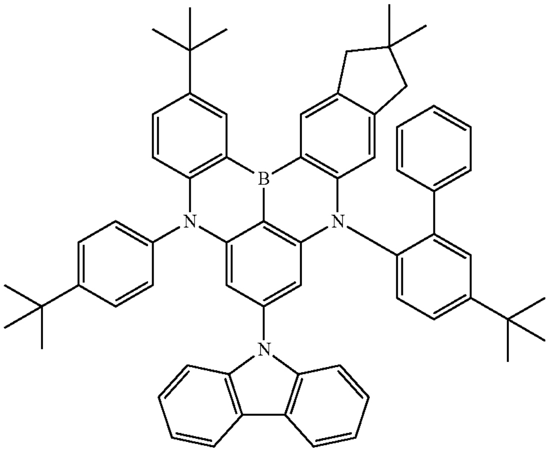
-continued
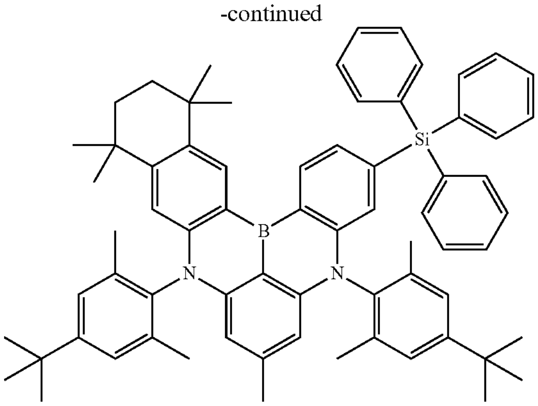
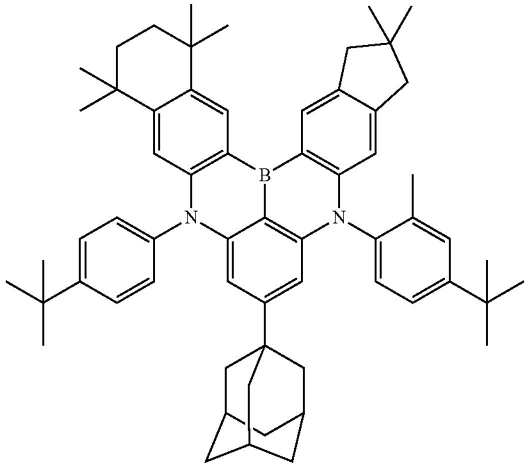
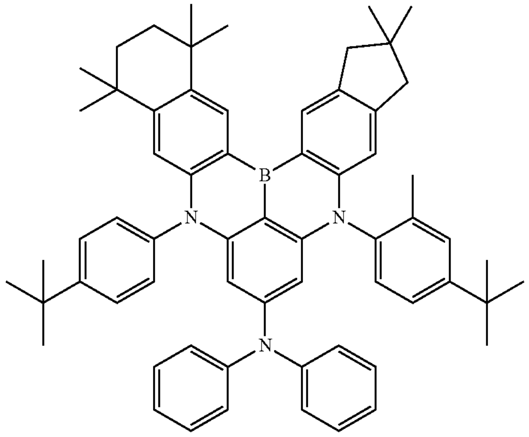
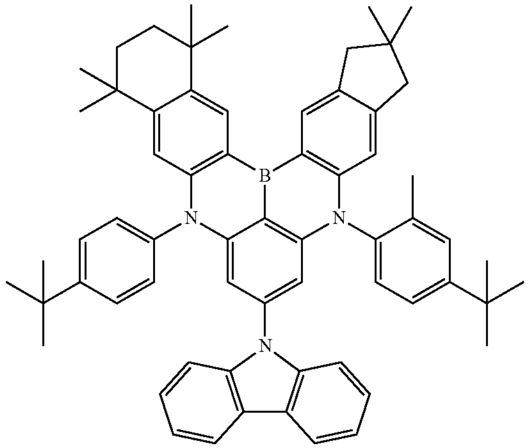

-continued
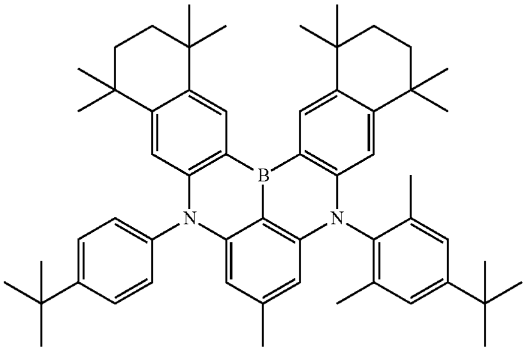
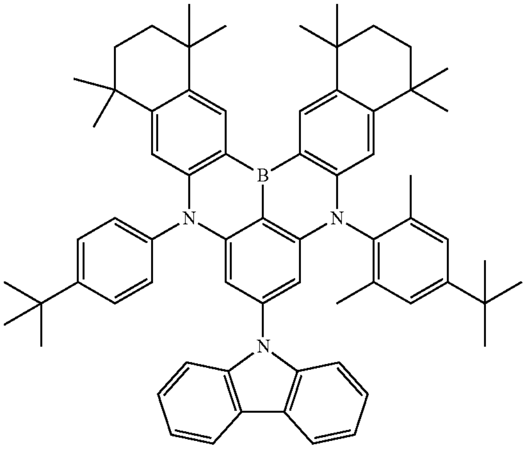
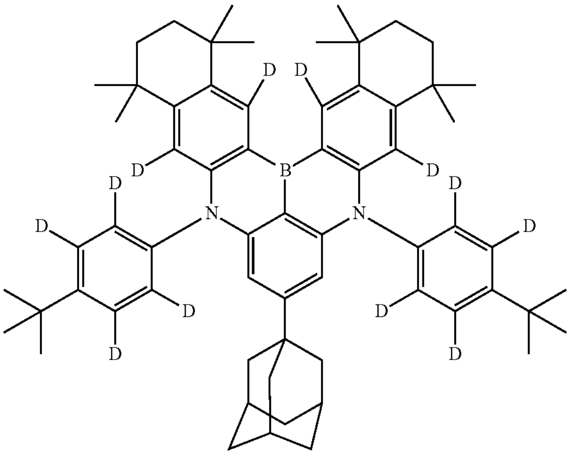
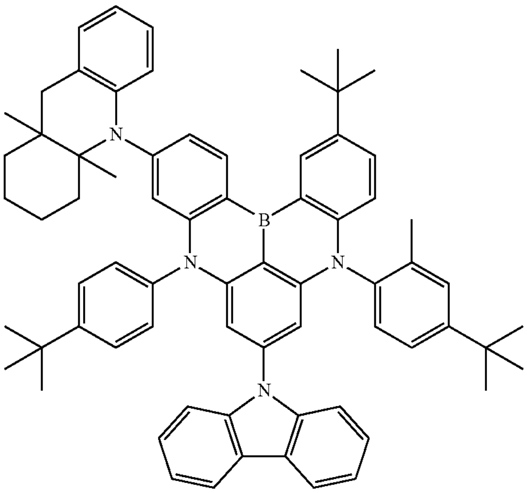
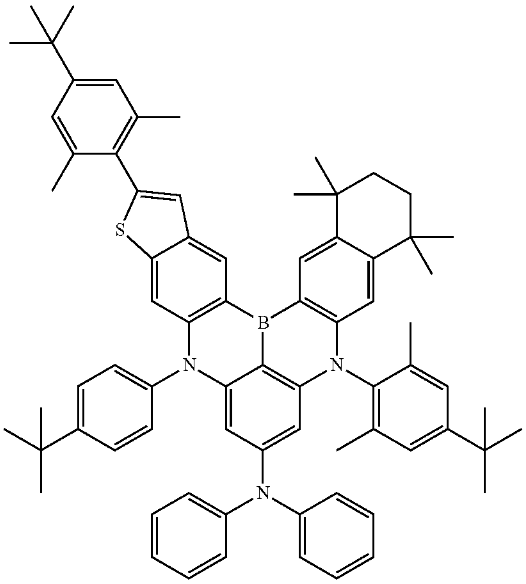
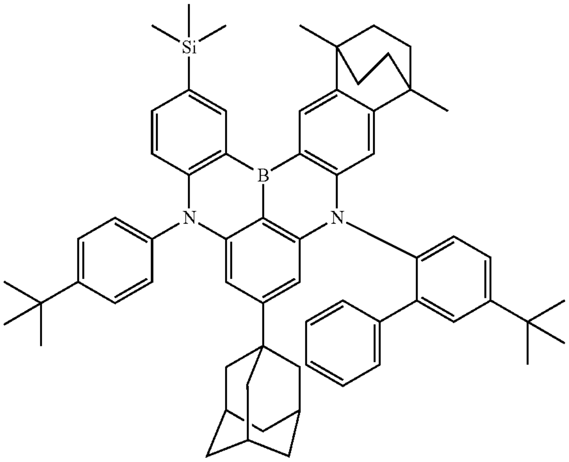
-continued -continued
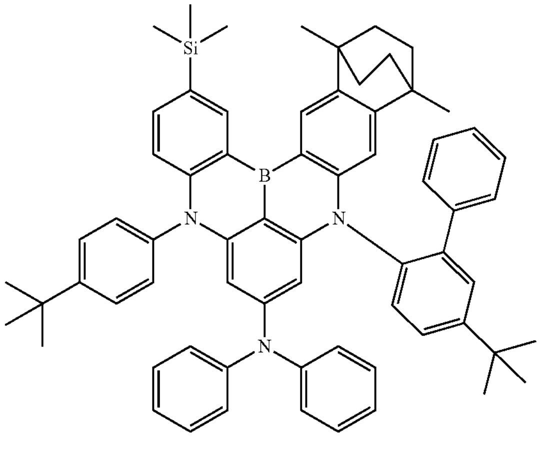
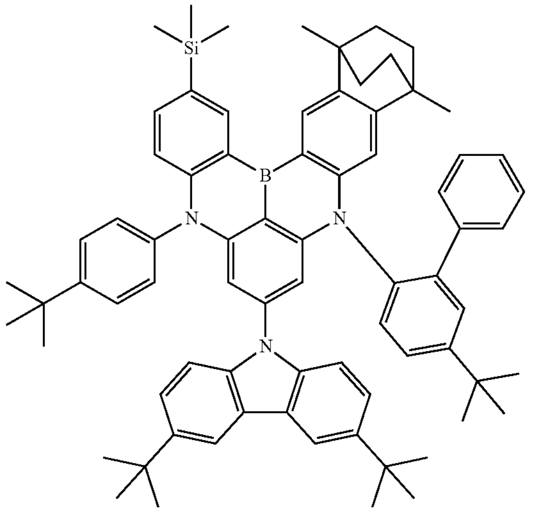
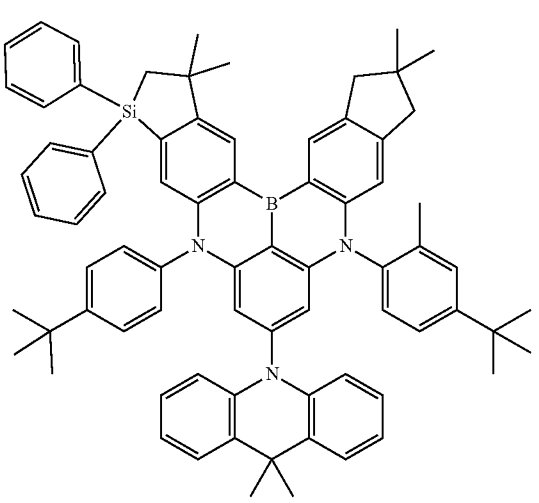
-continued
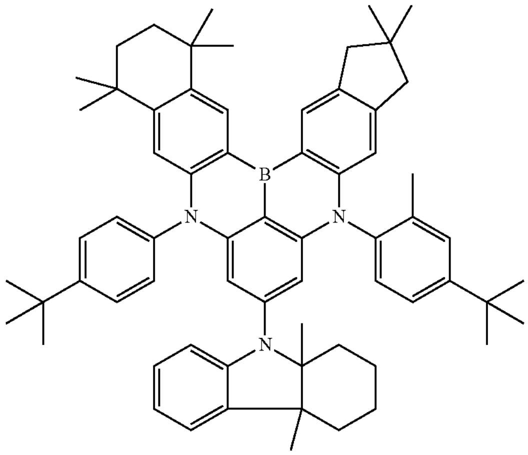
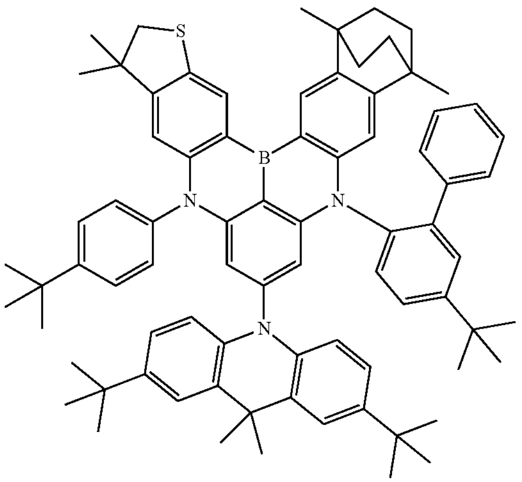
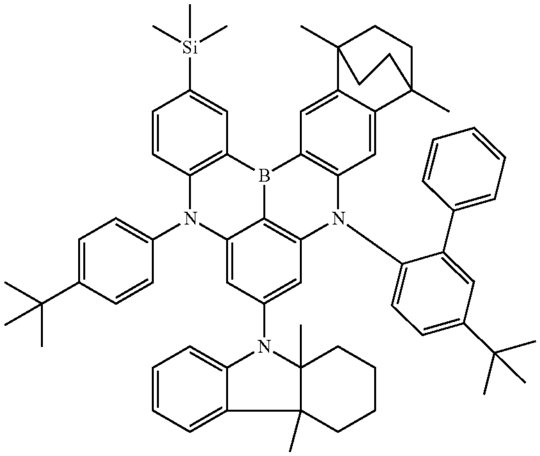

-continued
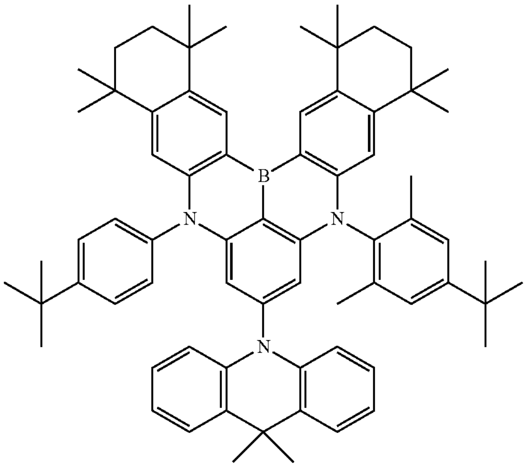
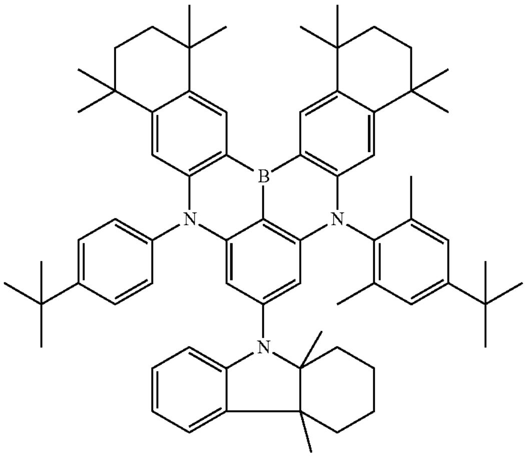
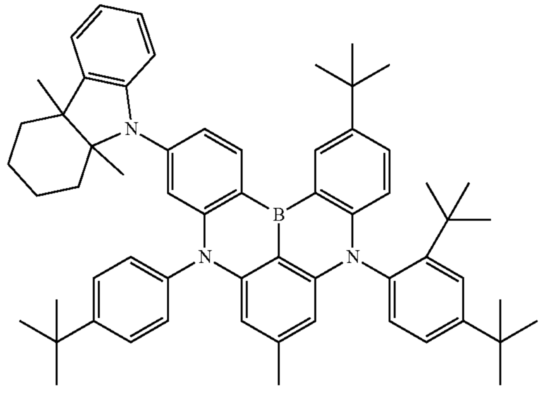
-continued
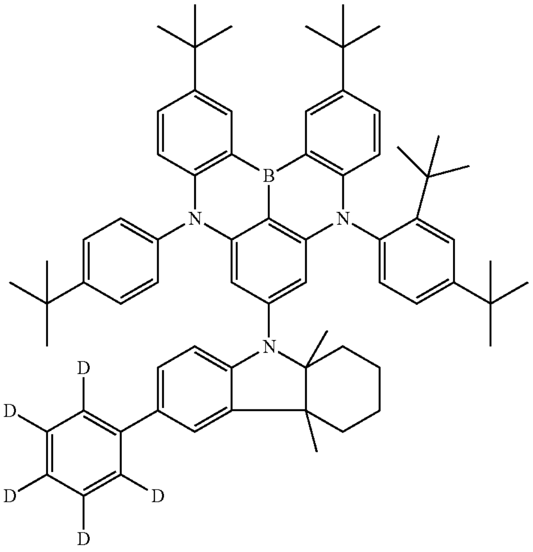
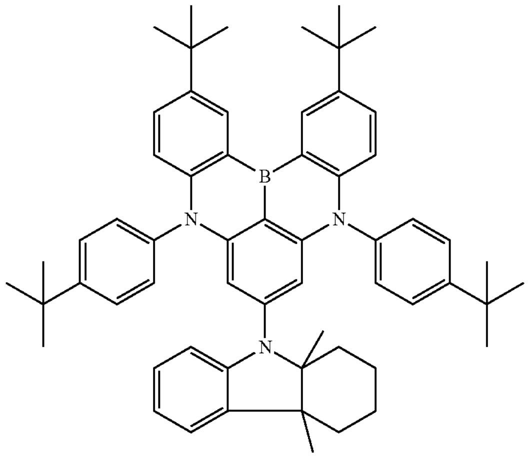
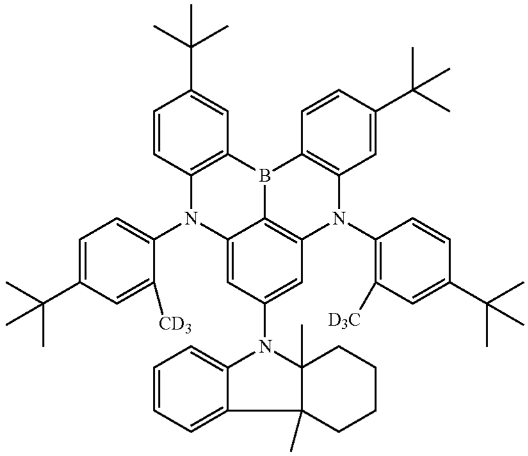

-continued
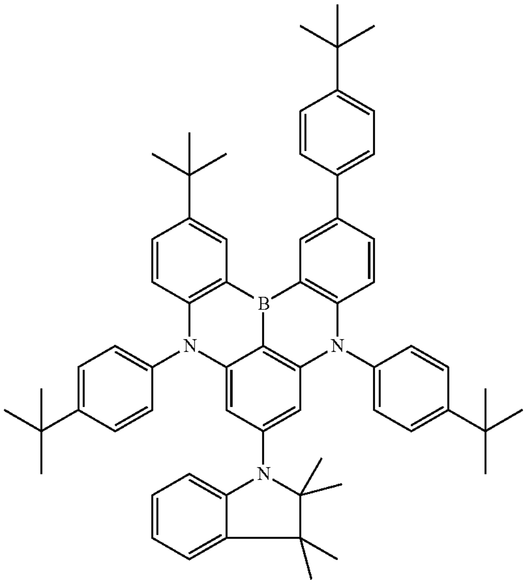
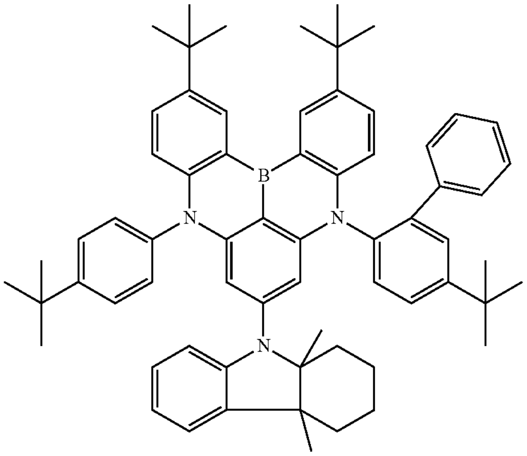 [SMILES: CC(C)(C)c1ccc(N2c3ccc(C(C)(C)C)cc3B3c4cc(C(C)(C)C)ccc4N(c4ccc(C(C)(C)C)cc4-c4ccccc4)c4cc(N5c6ccccc6C6(C)CCCCC56C)cc2c43)cc1]
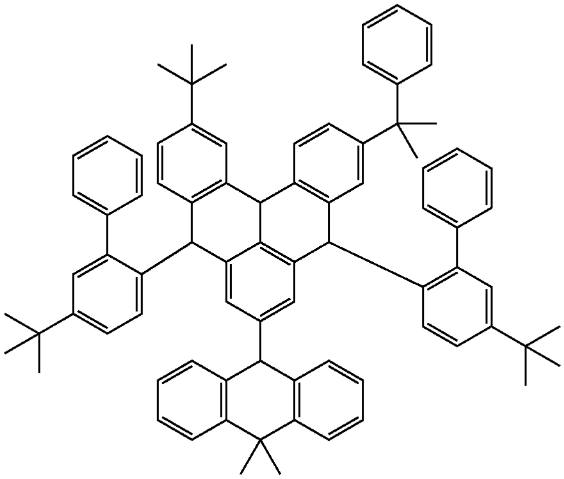
-continued
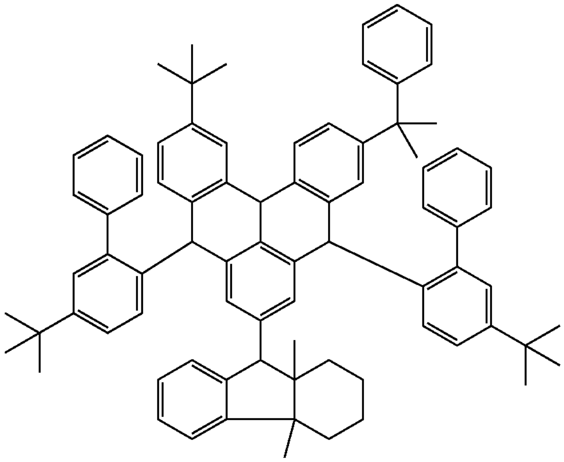
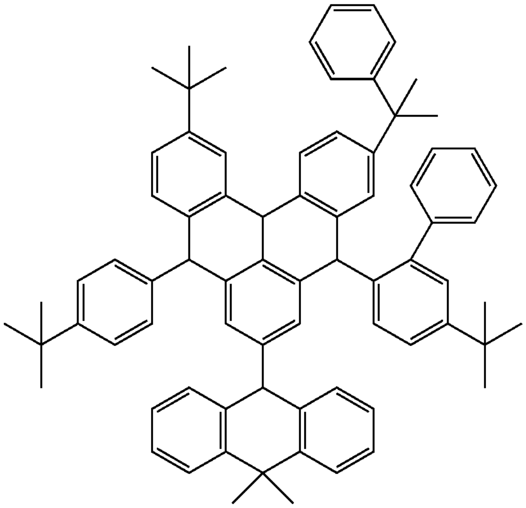
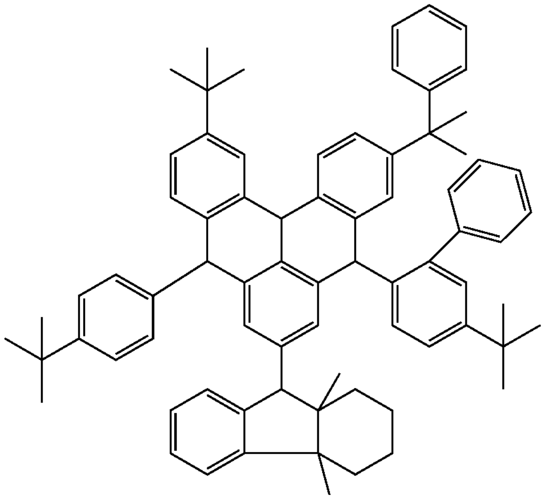 [SMILES: CC(C)(C)c1ccc(C2c3ccc(C(C)(C)C)cc3C3c4ccc(C(C)(C)c5ccccc5)cc4C(c4ccc(C(C)(C)C)cc4-c4ccccc4)c4cc(C5c6ccccc6C6(C)CCCCC56C)cc2c43)cc1]

-continued
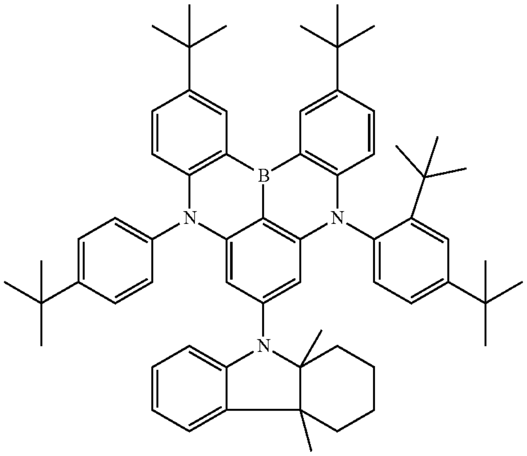
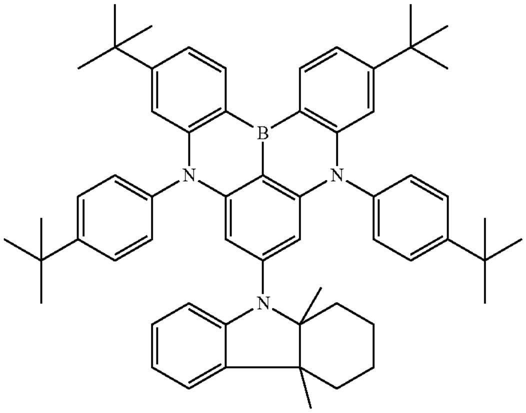
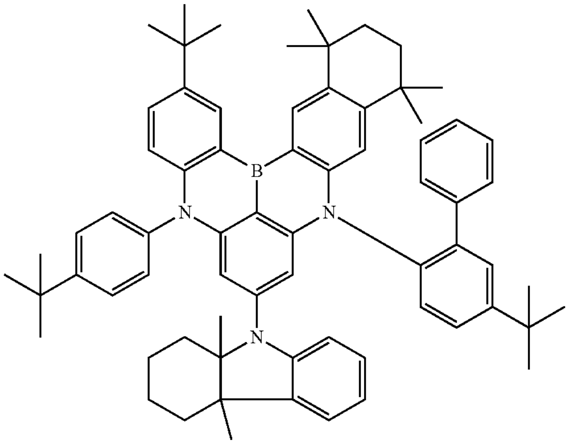
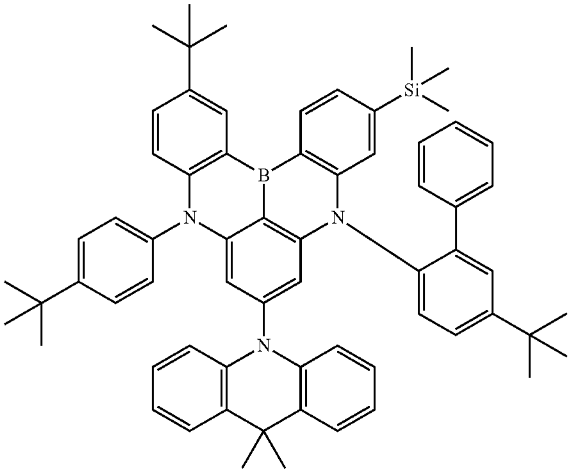
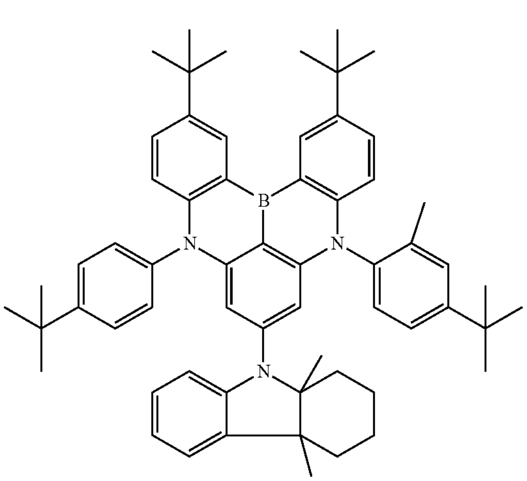
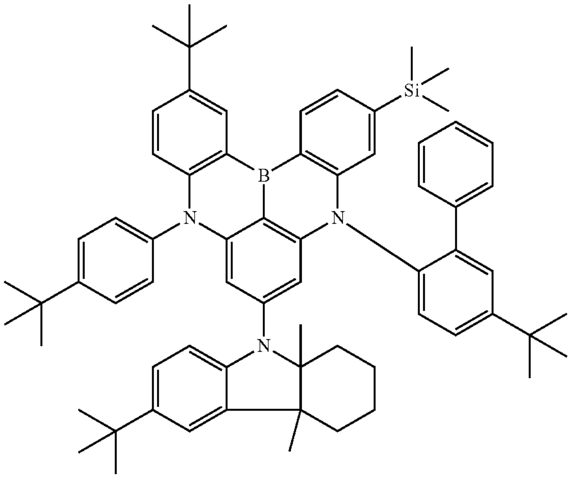
-continued -continued
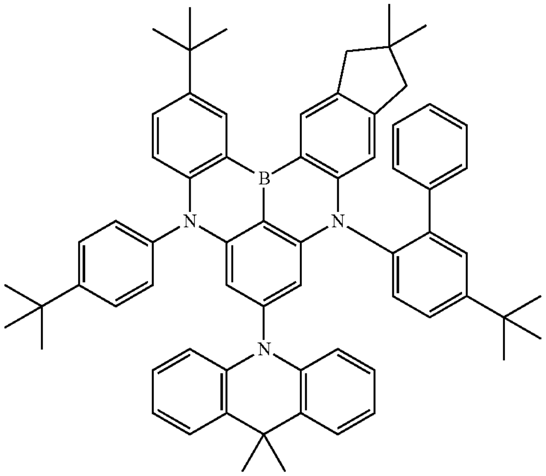
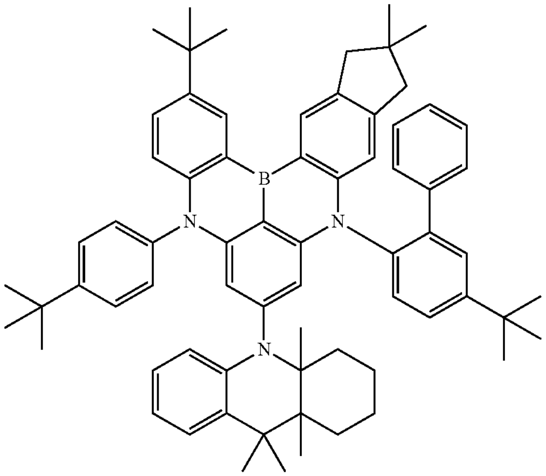
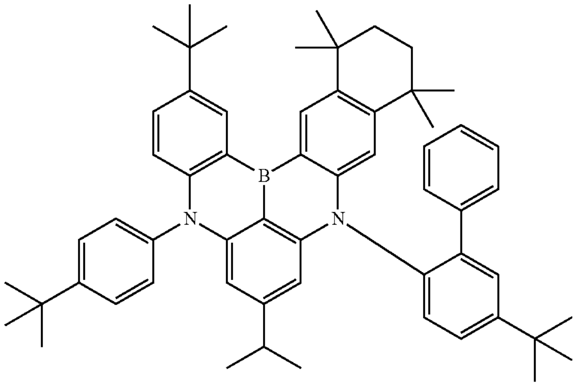
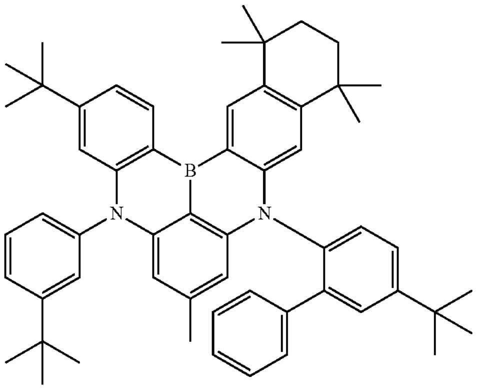
-continued
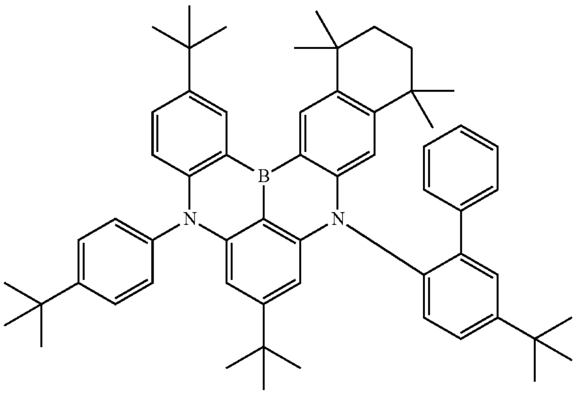
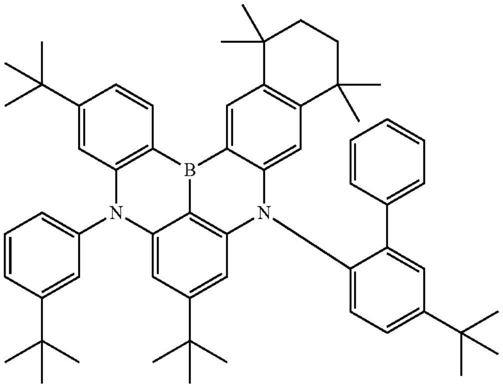
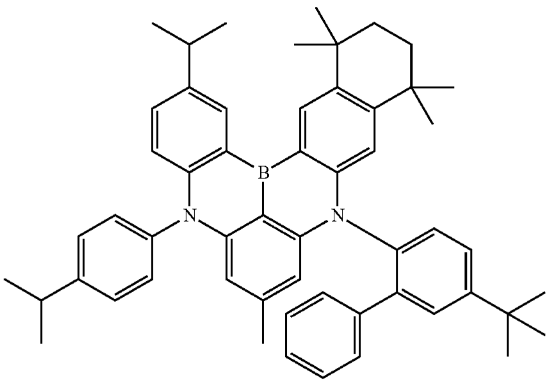
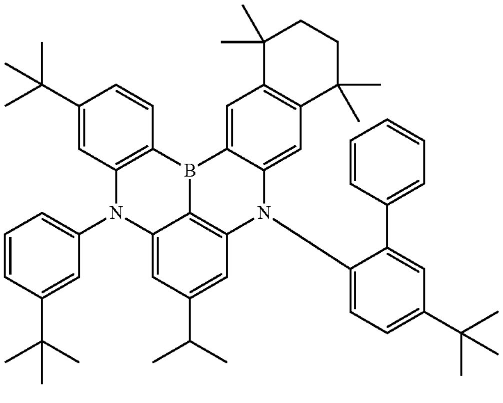

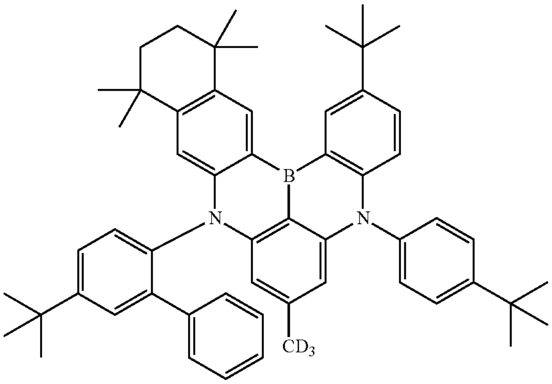
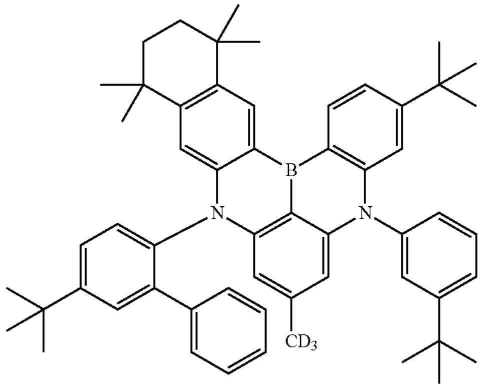
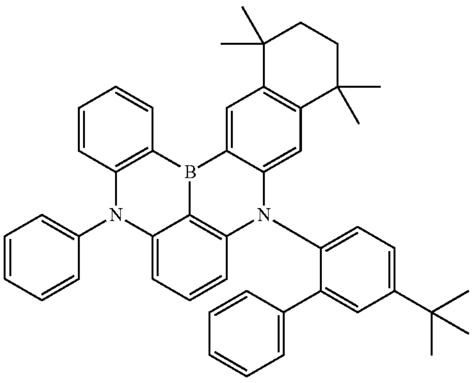
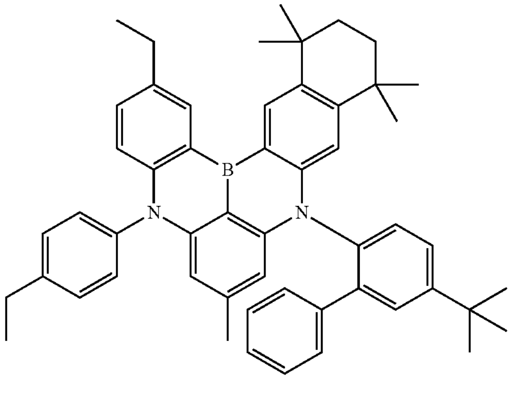
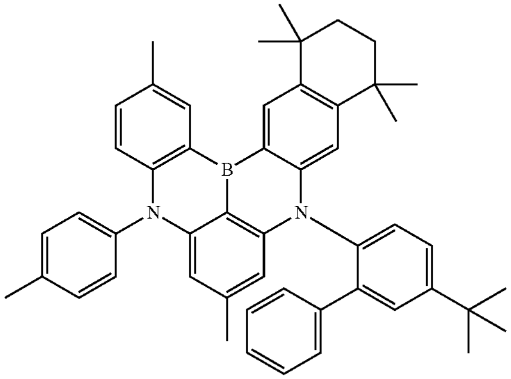
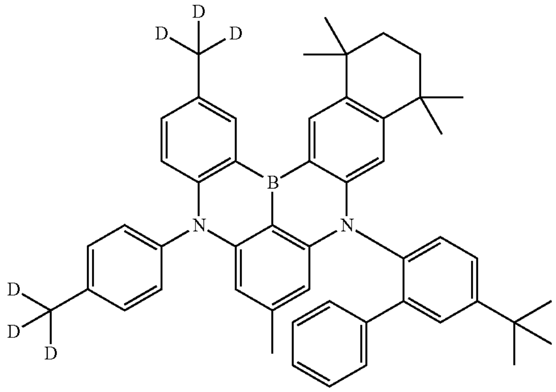
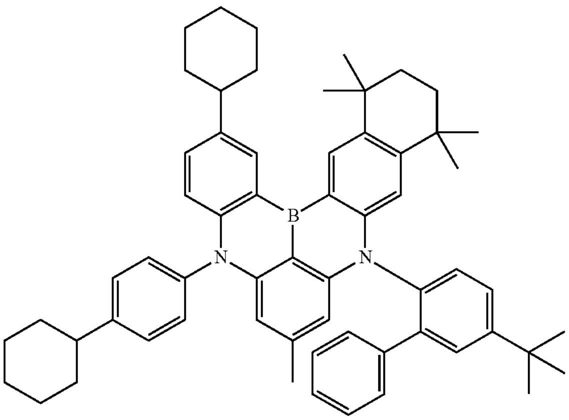
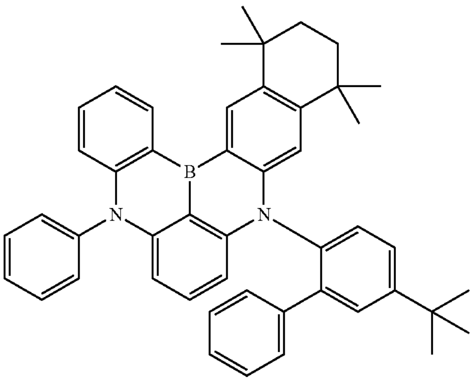

-continued
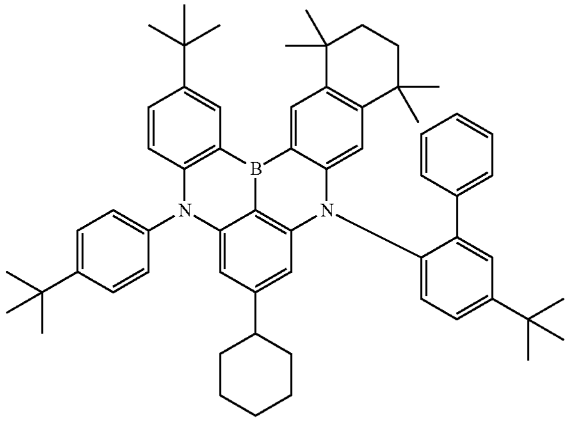
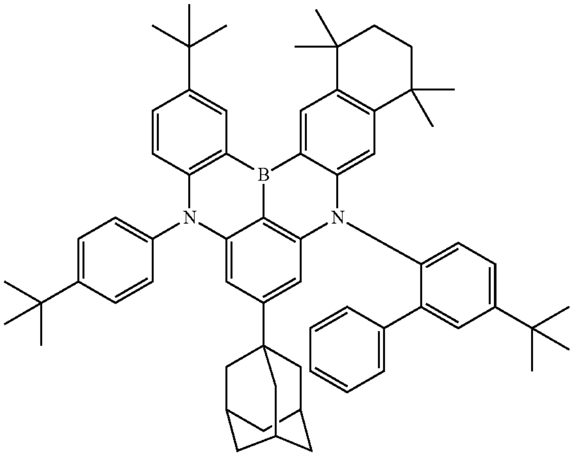
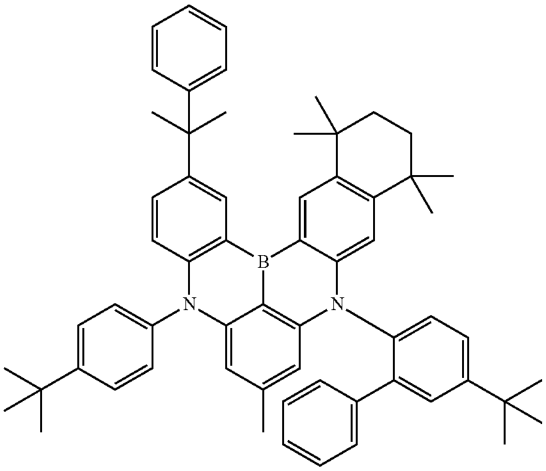
-continued
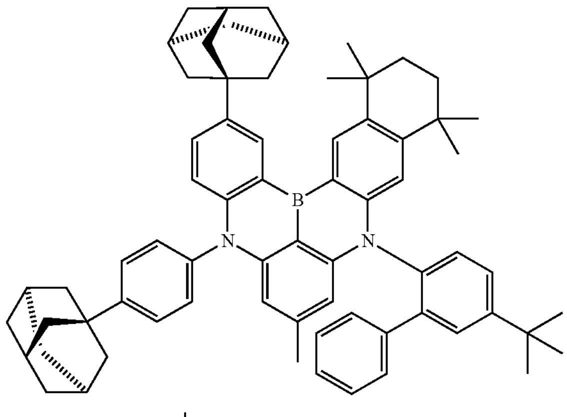
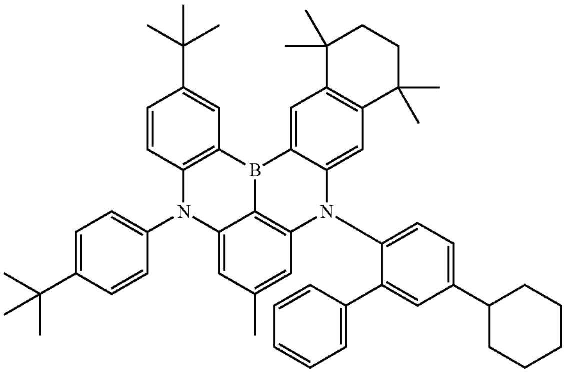
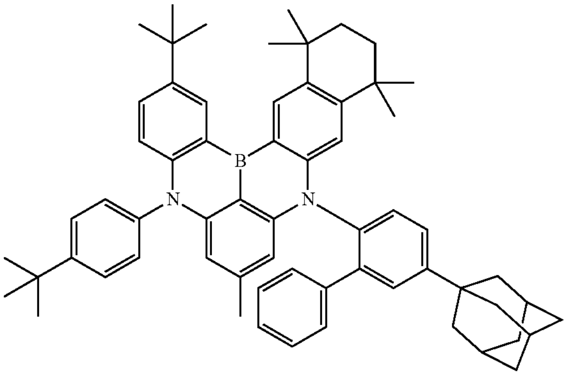
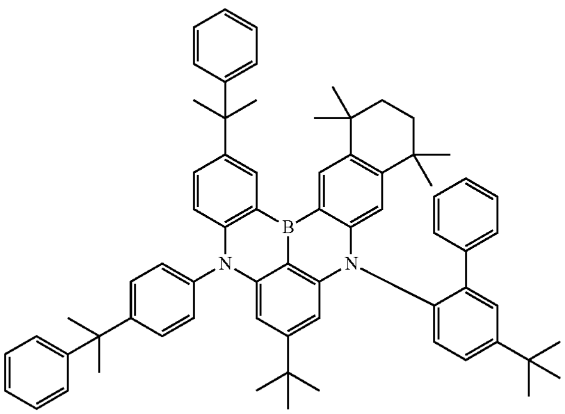

-continued
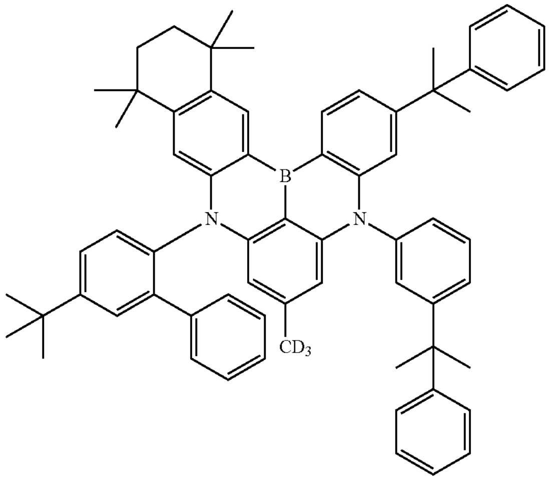
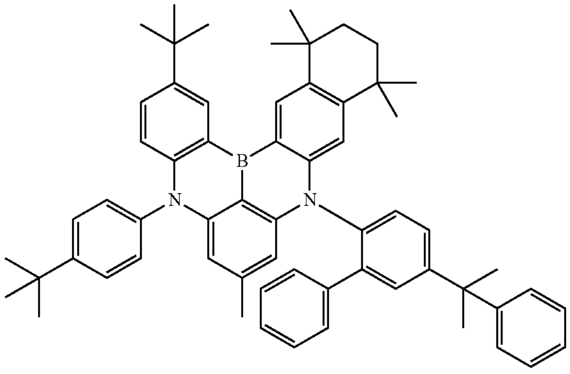
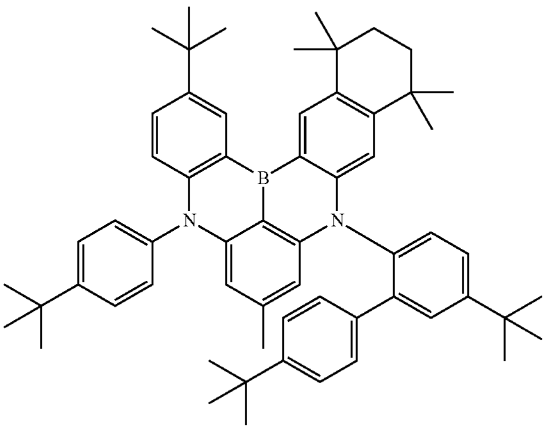
-continued
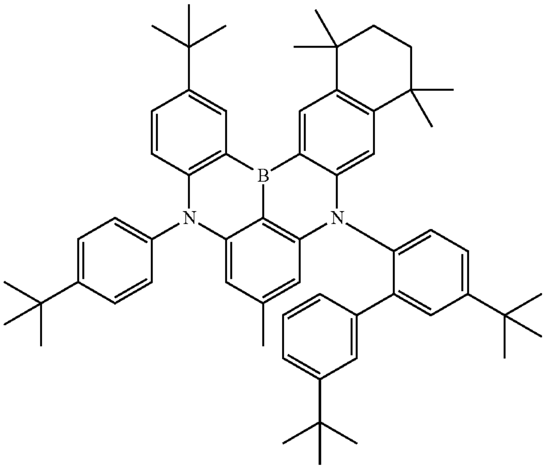
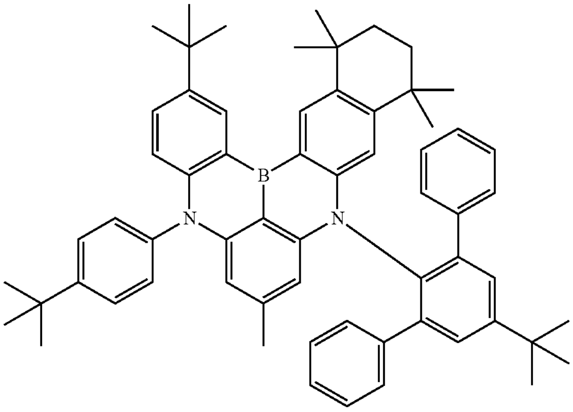
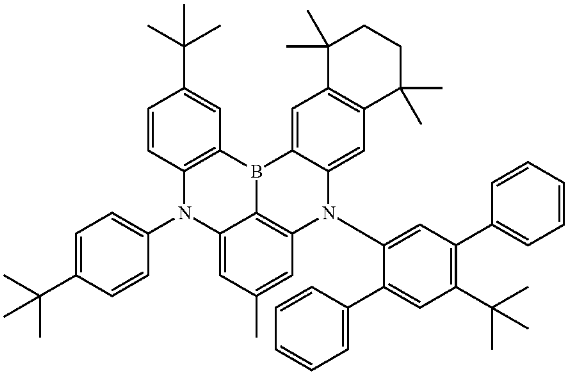
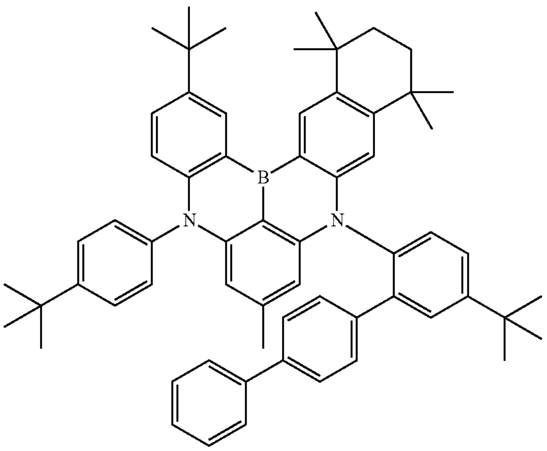

-continued
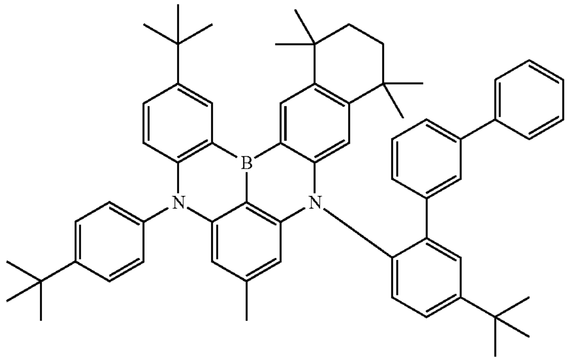
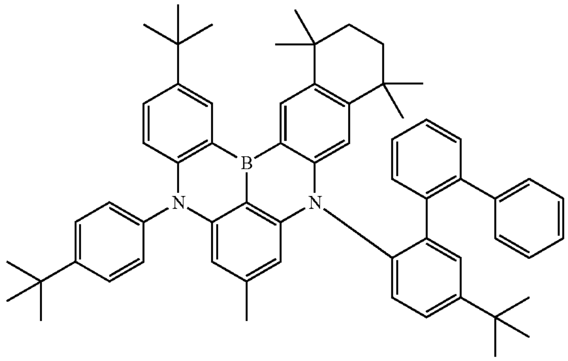
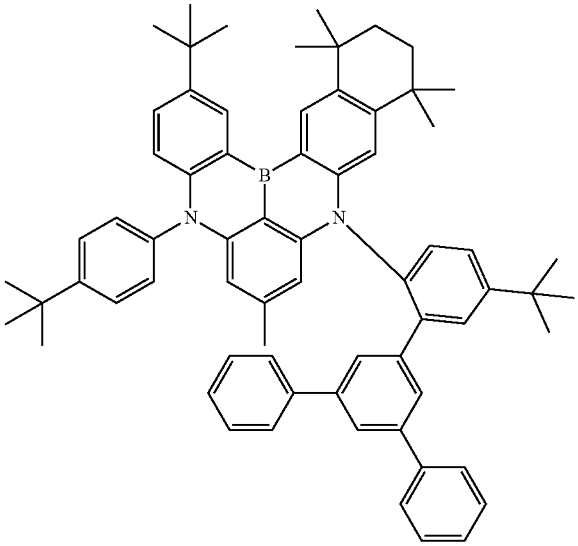
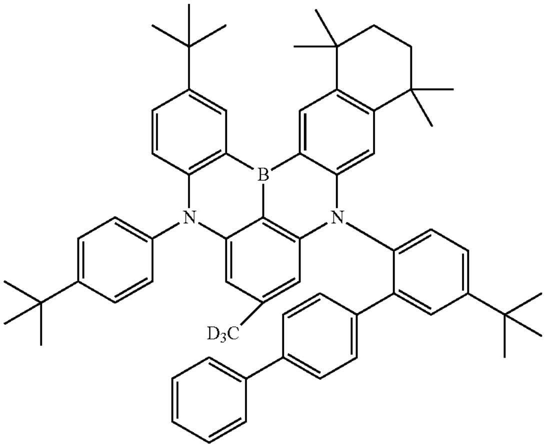
-continued
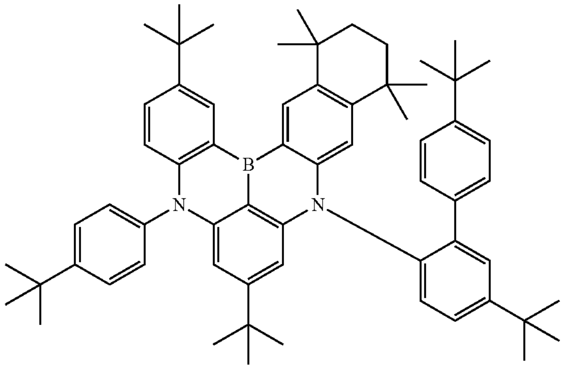
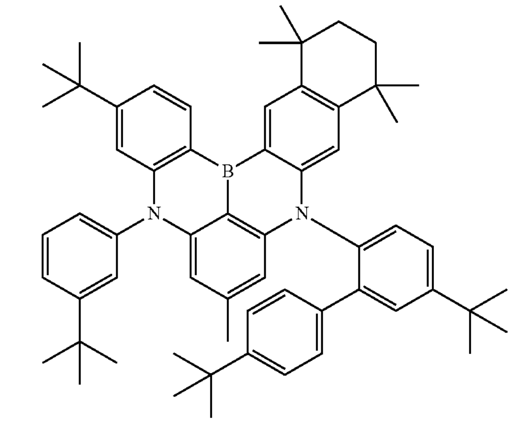
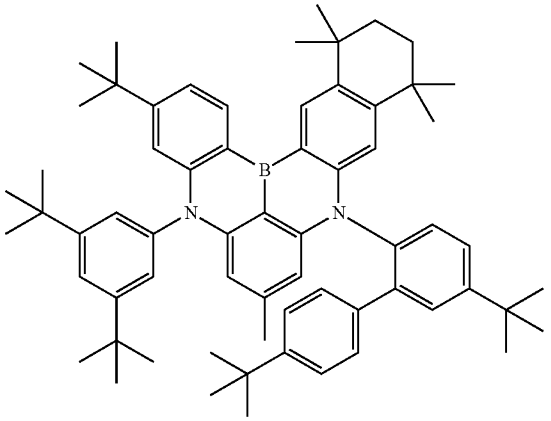
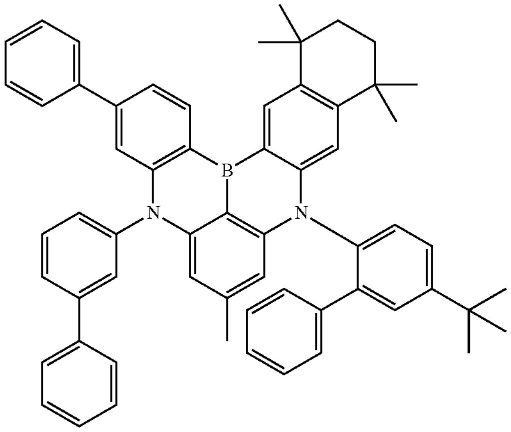

-continued
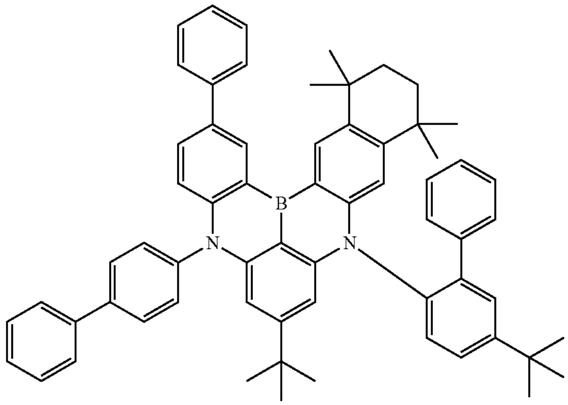
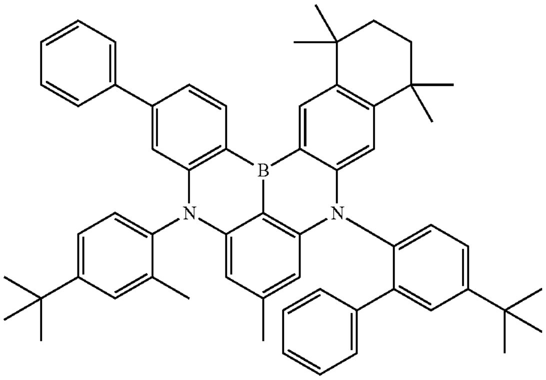
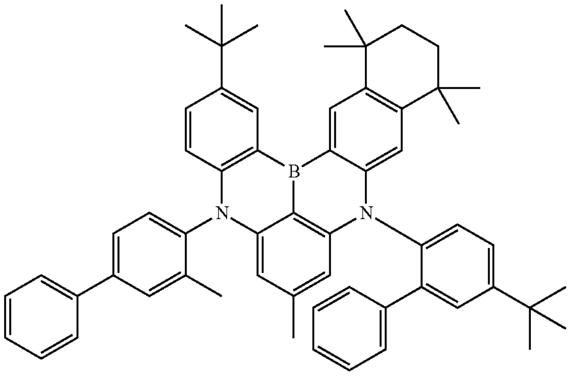
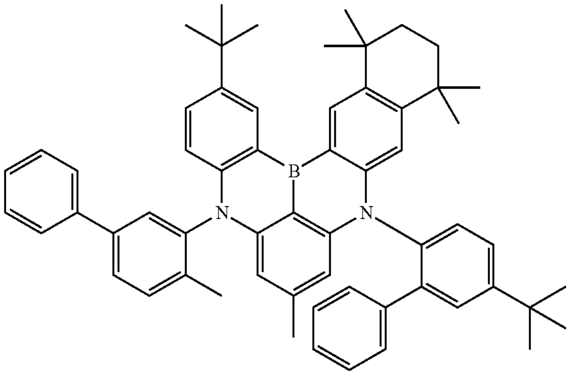
-continued
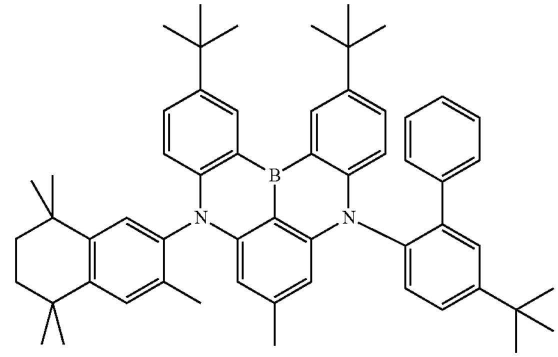
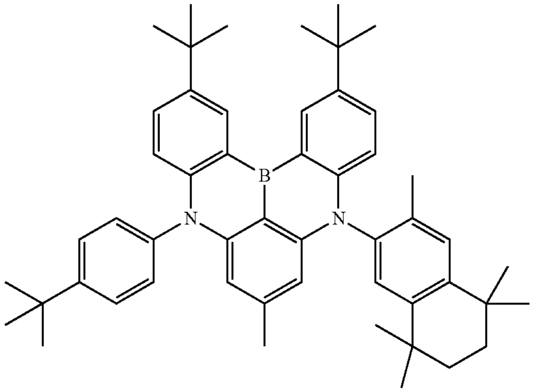
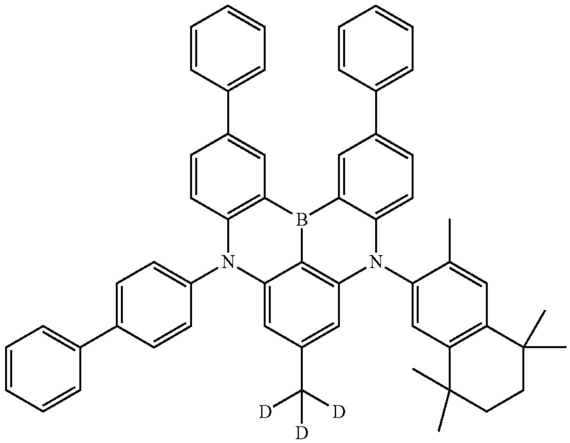
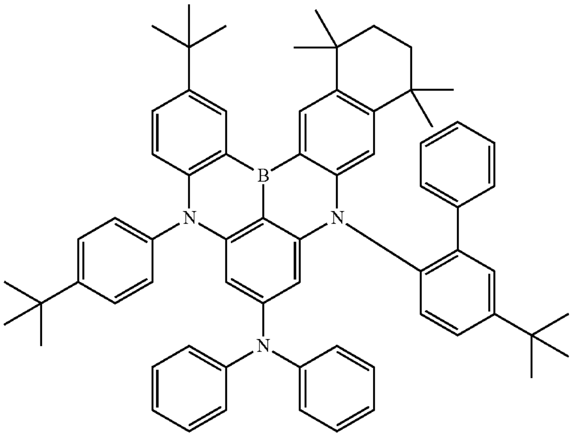

-continued
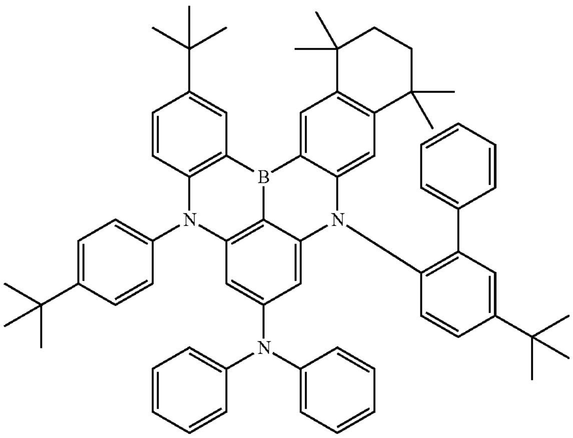
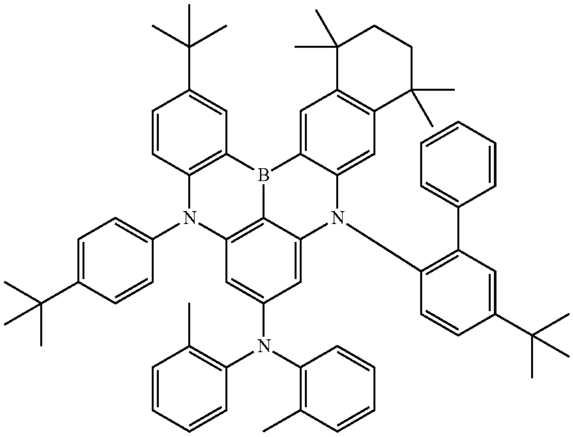
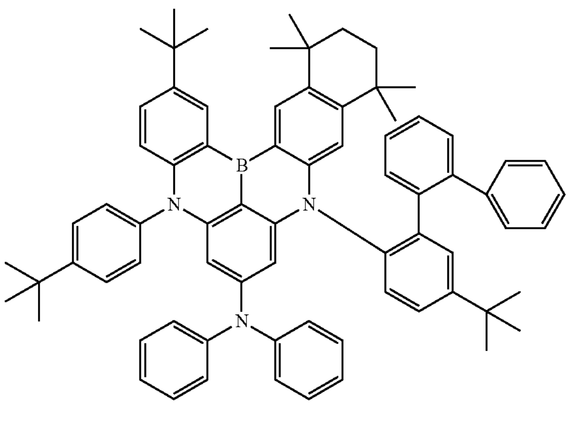
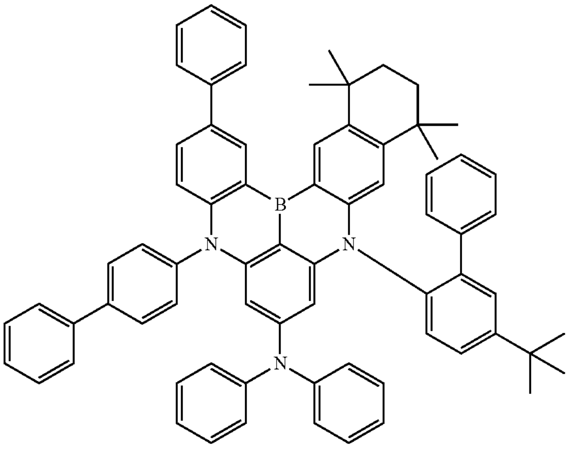
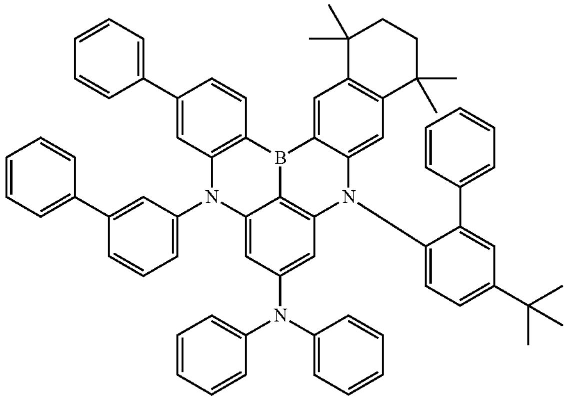
-continued
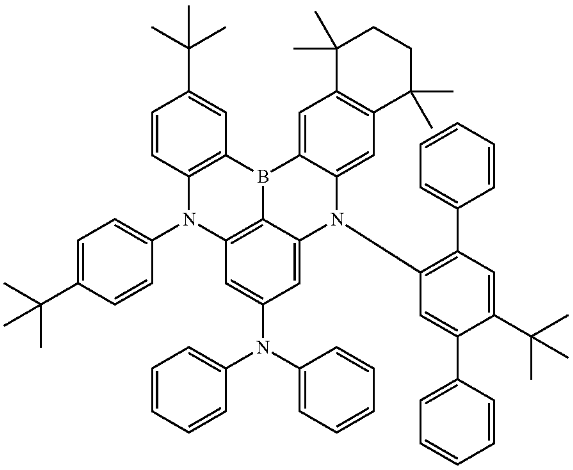

-continued
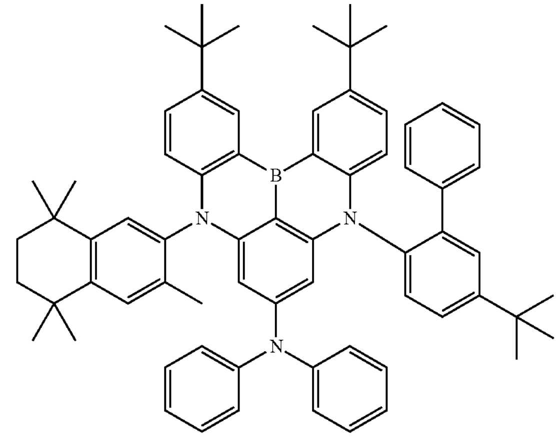
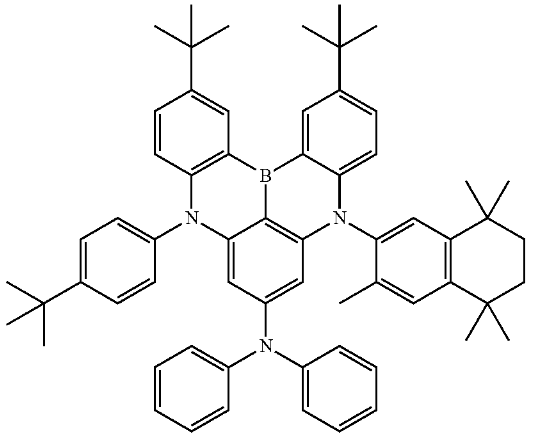
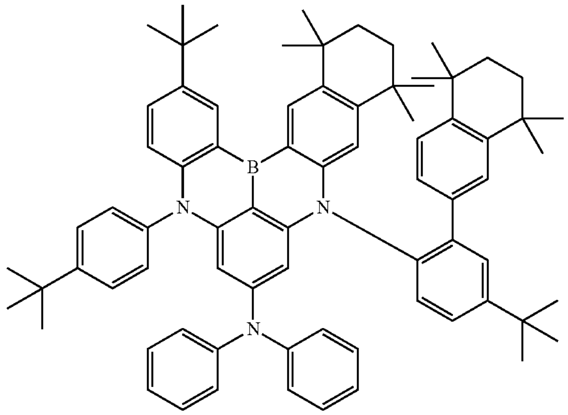
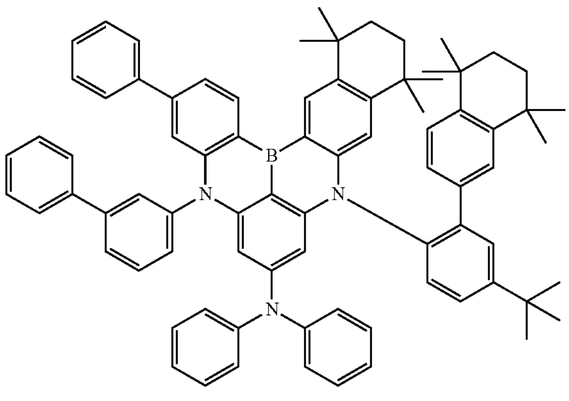
-continued
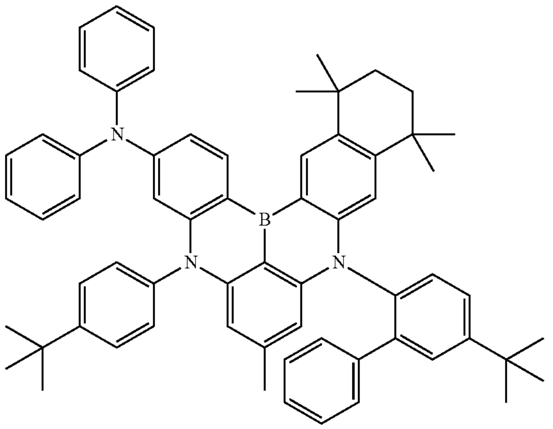
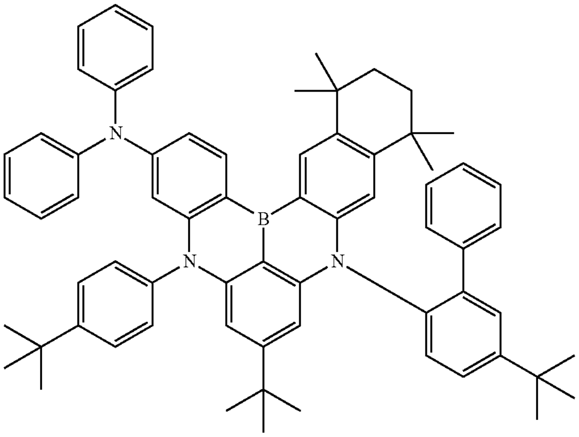
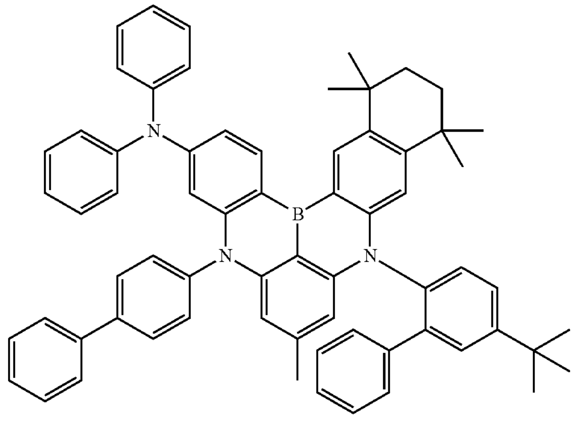
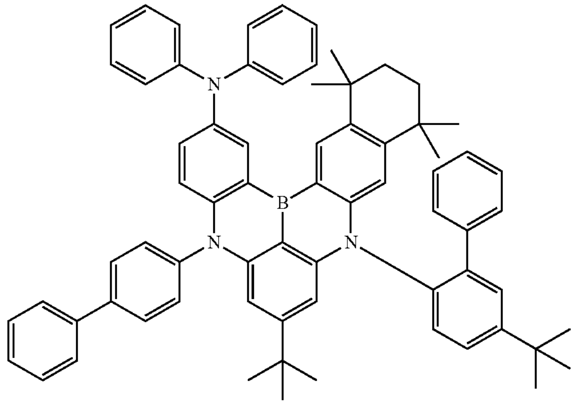

-continued
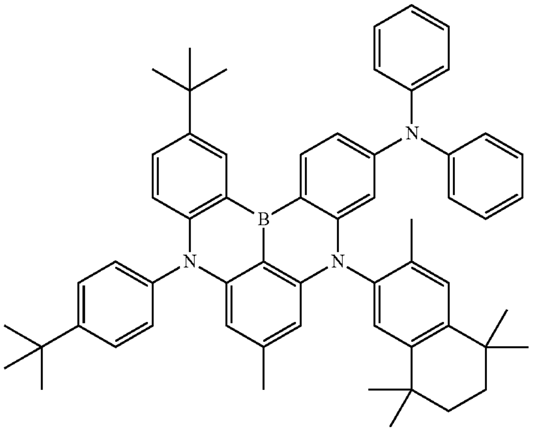
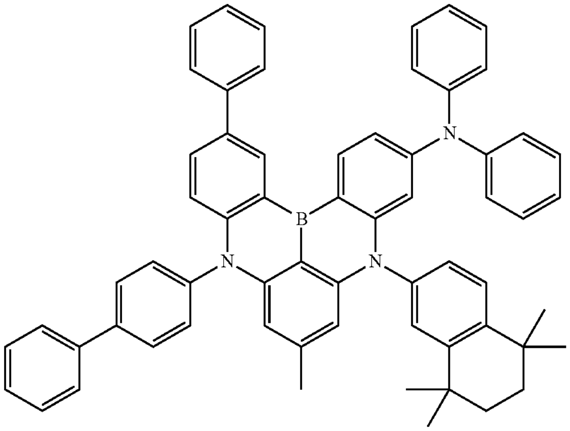
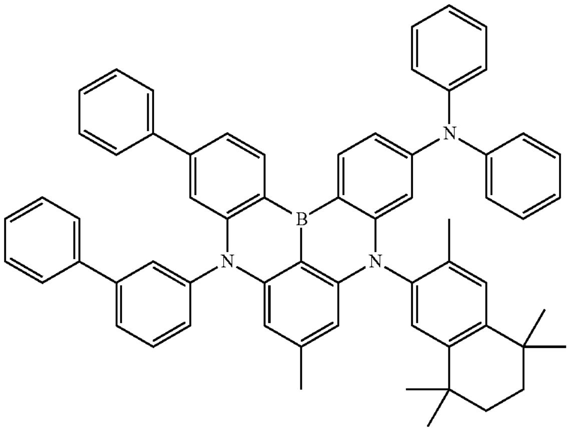
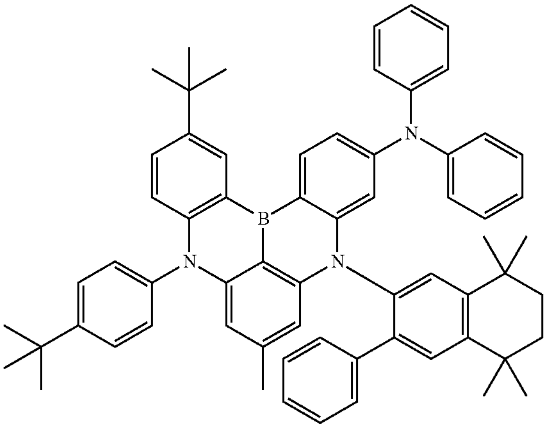
-continued
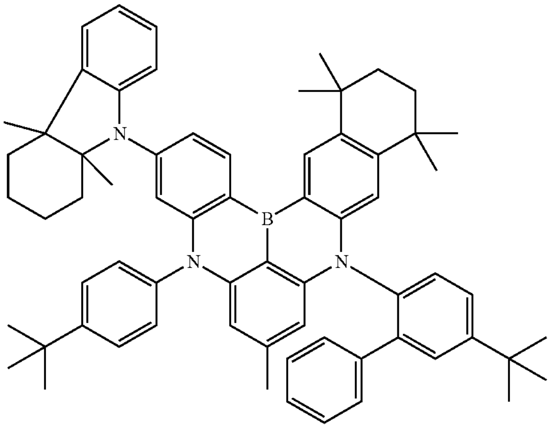
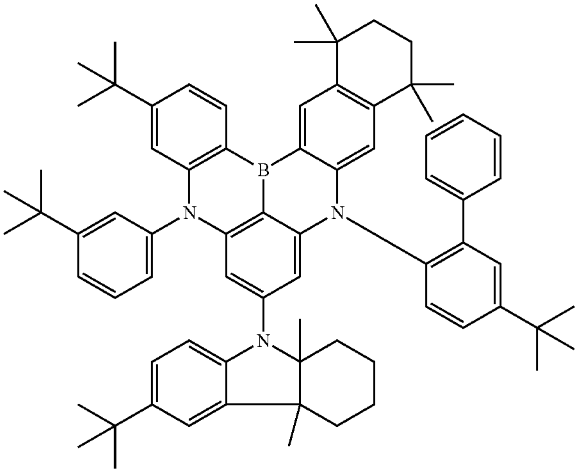
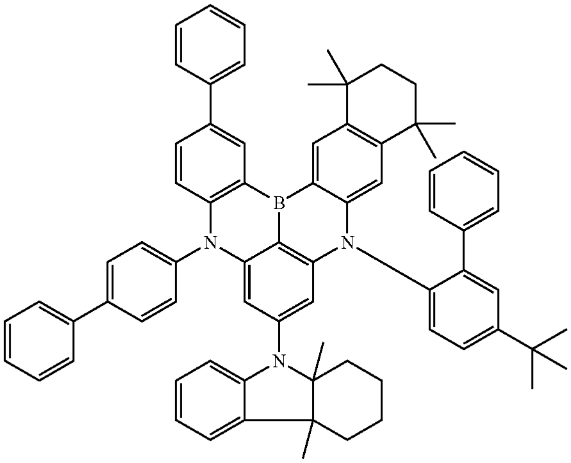

-continued
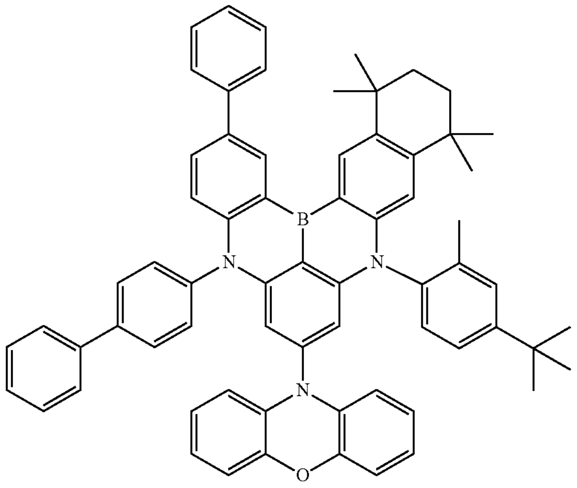
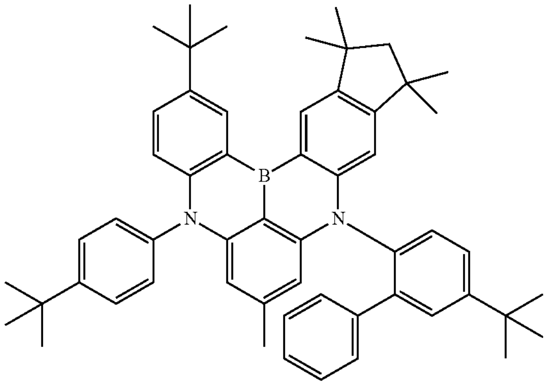
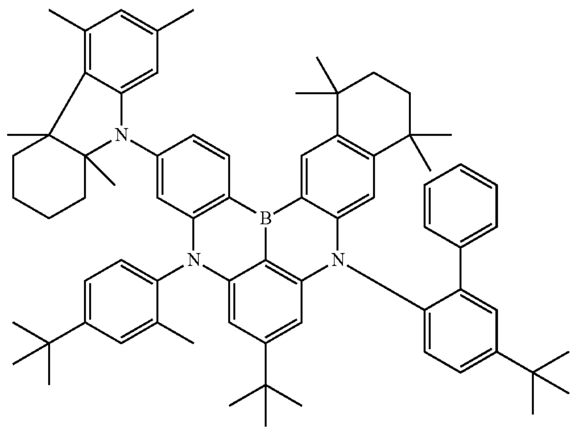
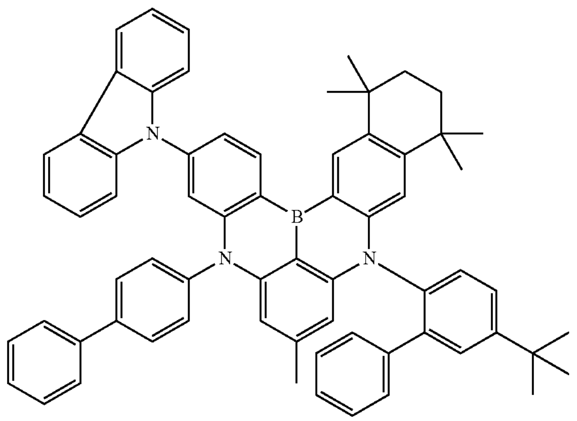
-continued
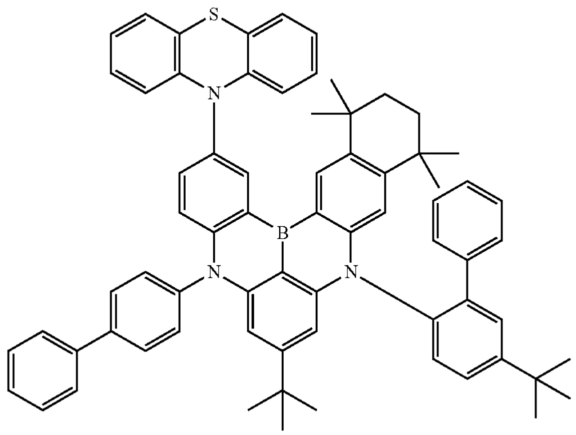
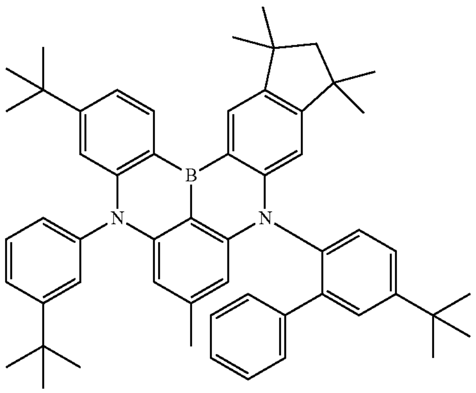
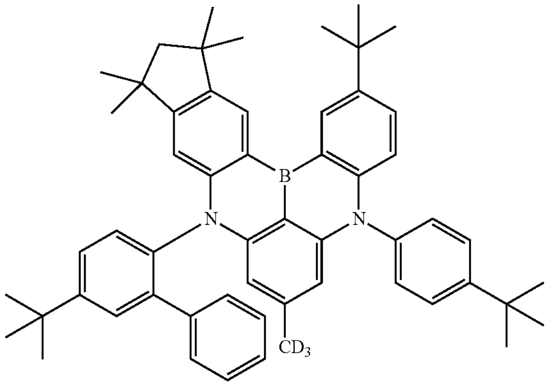
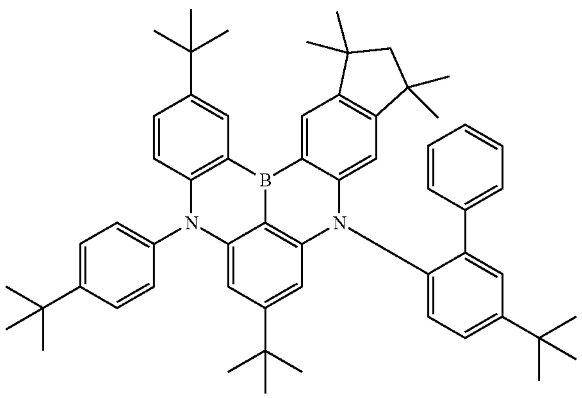

-continued
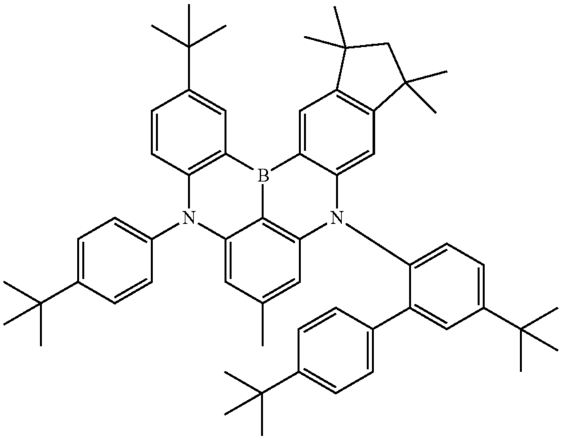
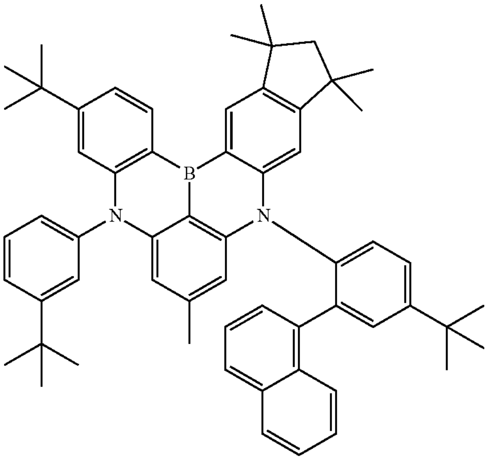
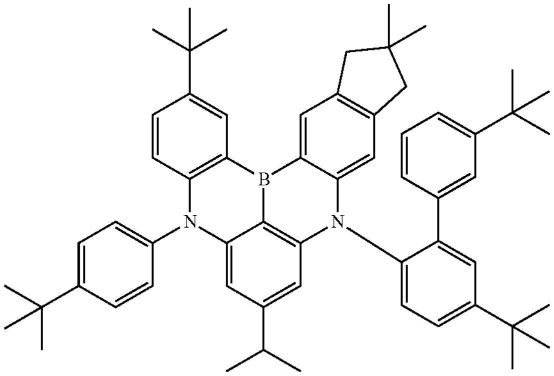
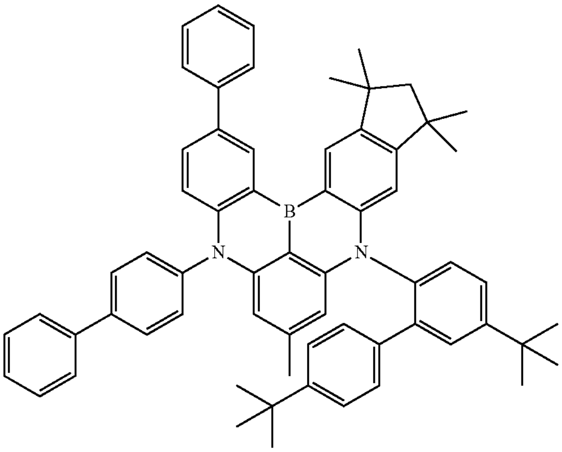
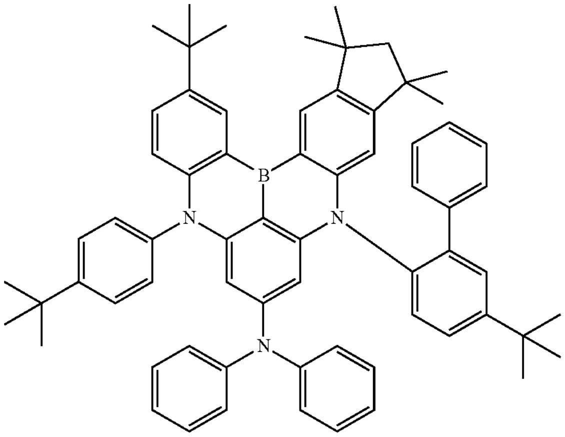
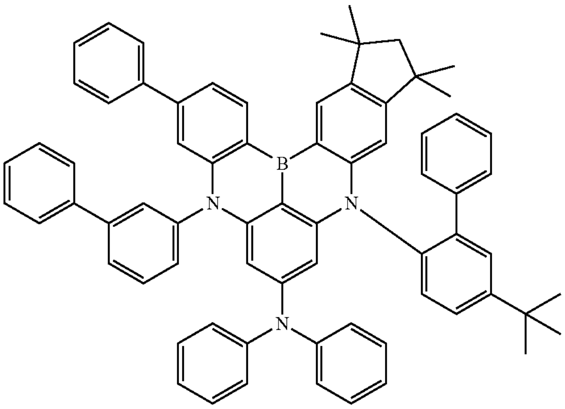
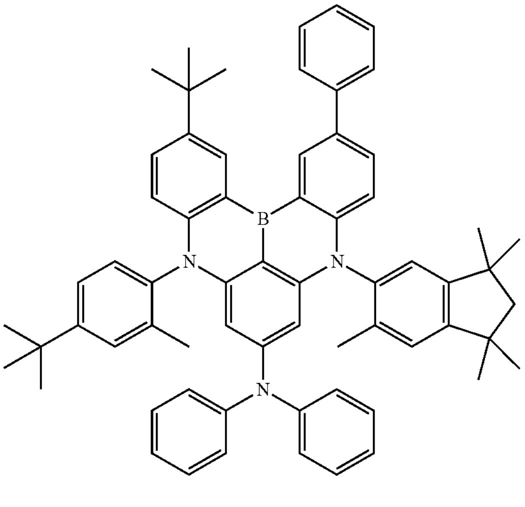

-continued
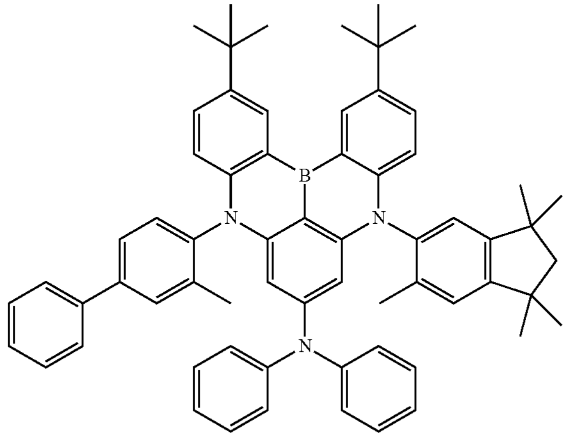
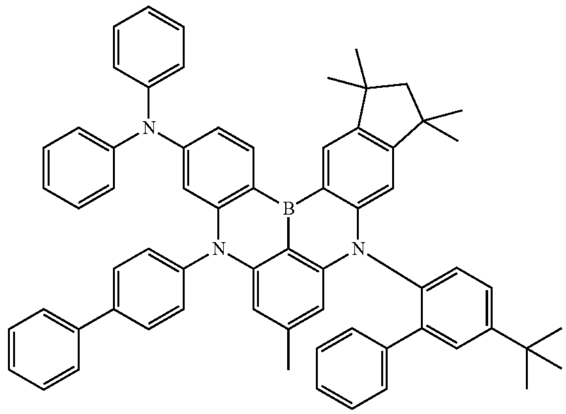
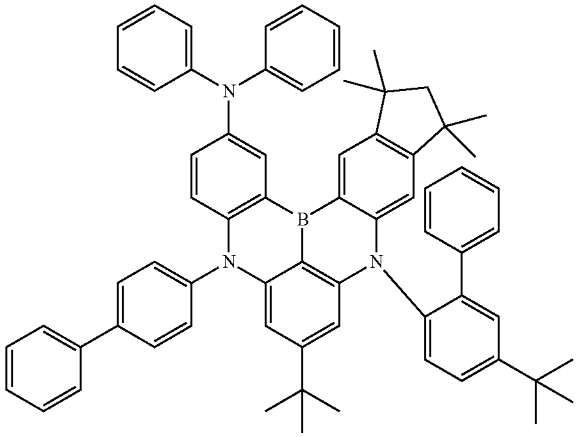
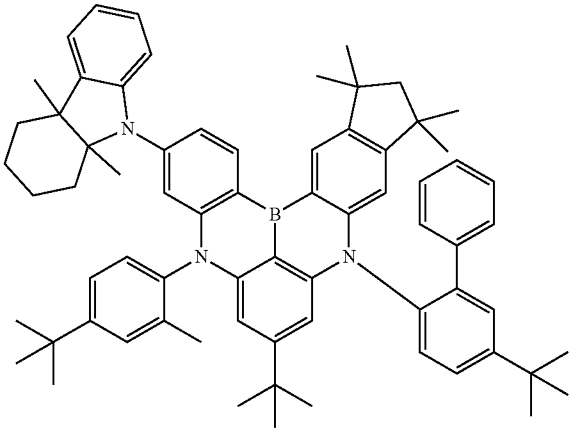
-continued
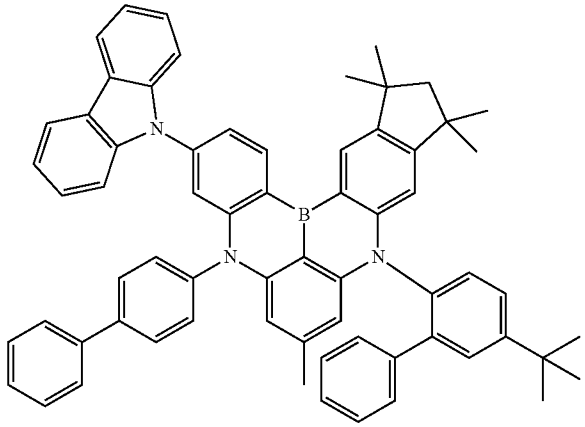
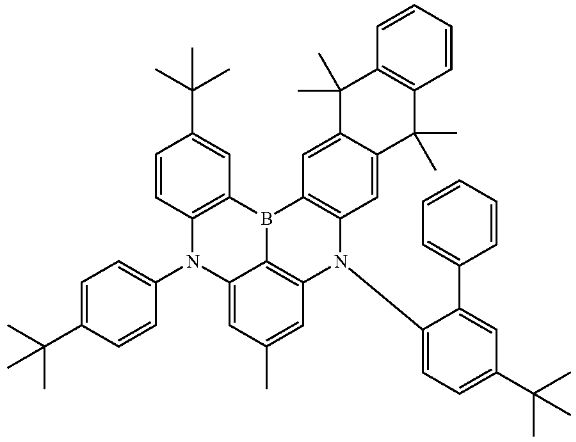
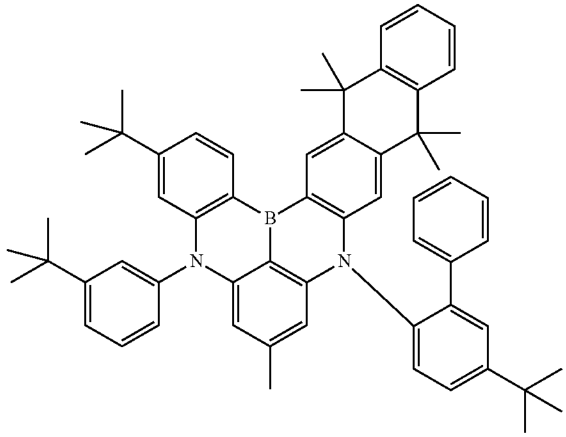

-continued
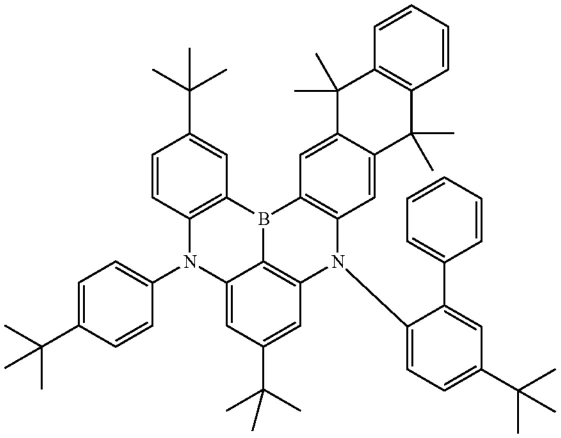
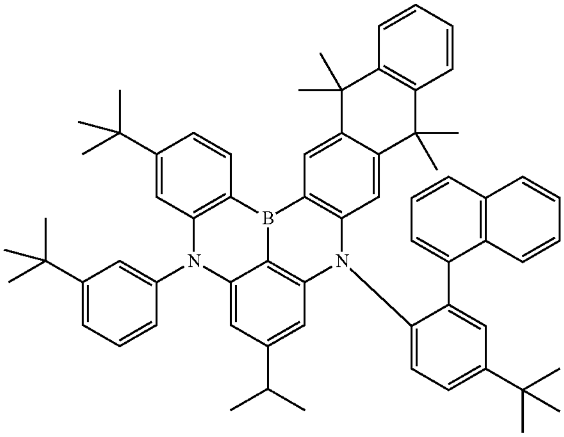
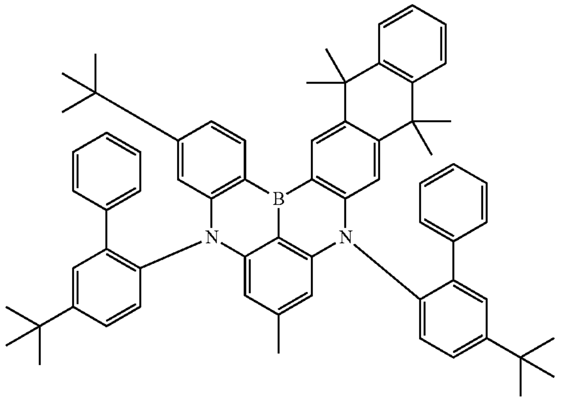
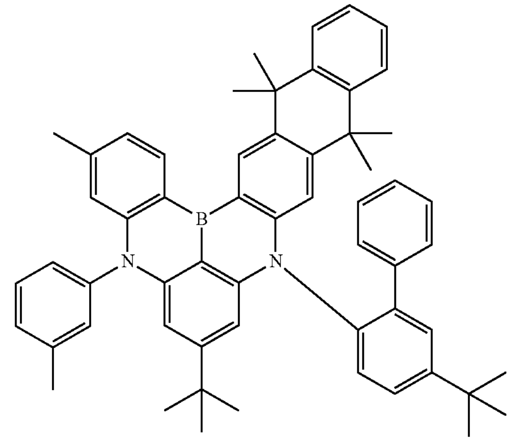
-continued
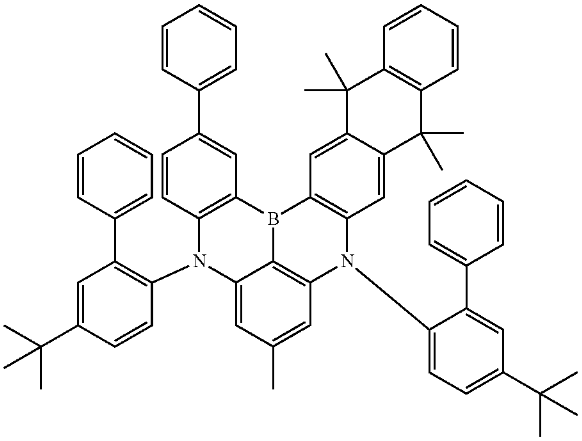
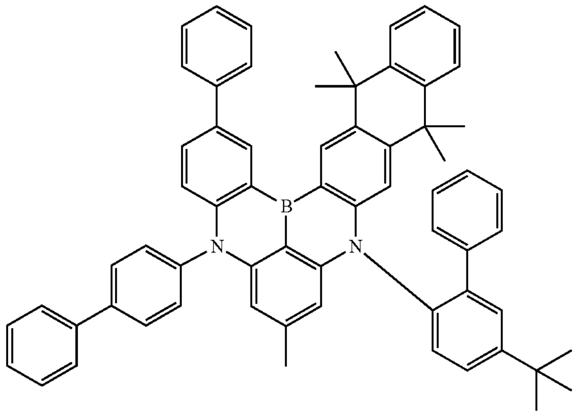
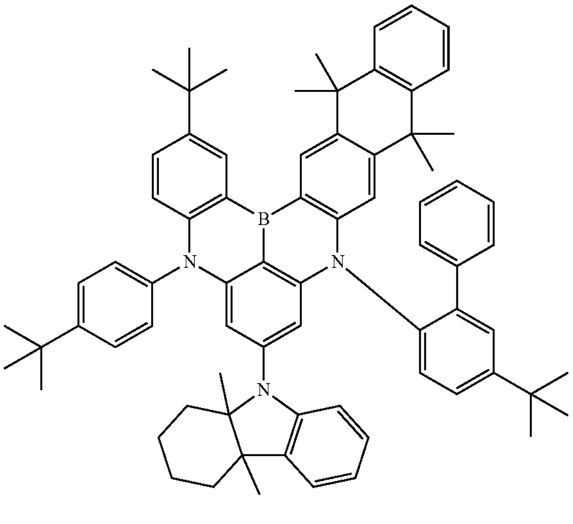

-continued
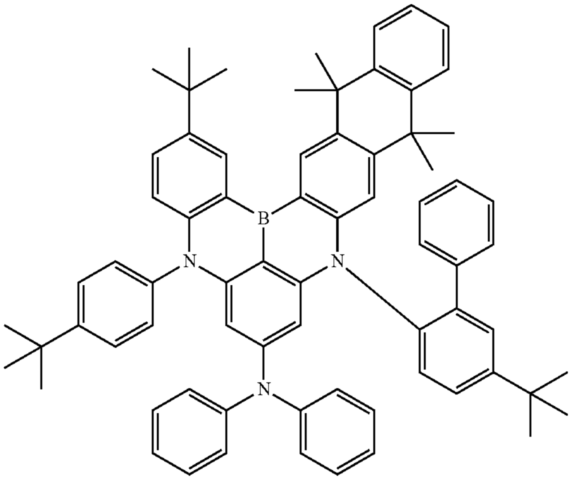
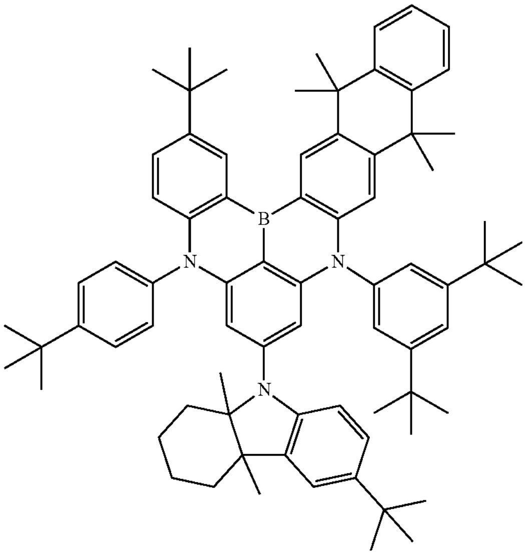
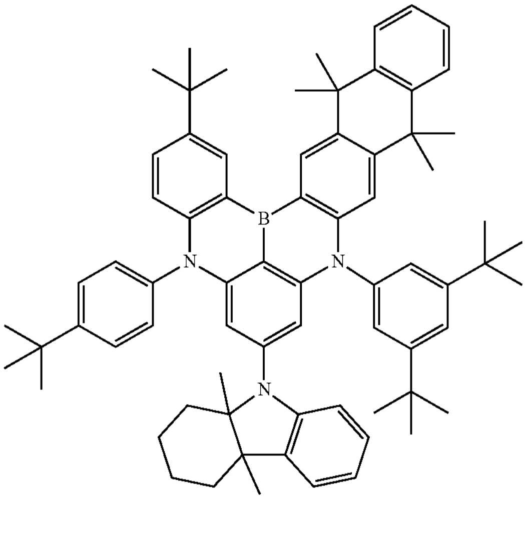
-continued
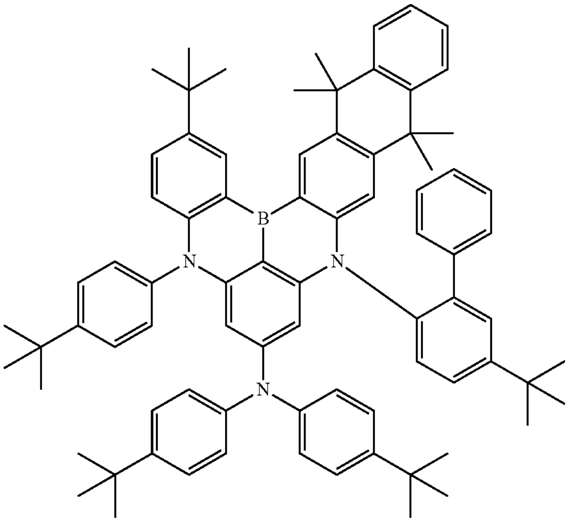
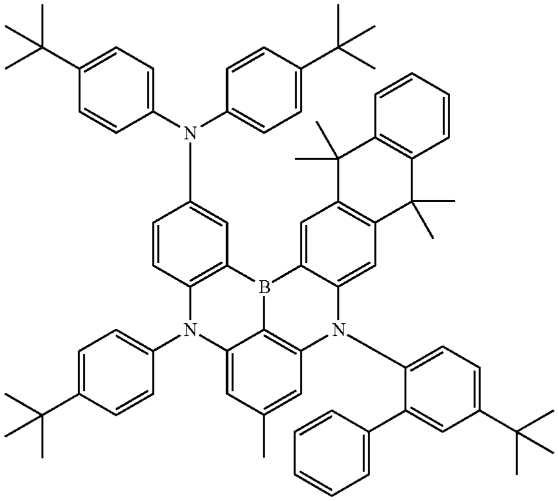
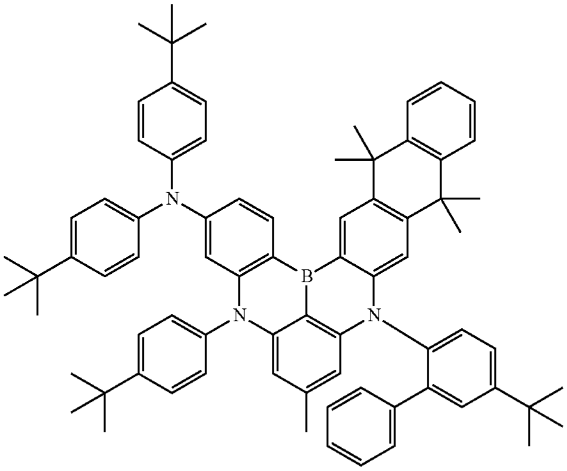 [SMILES: Cc1cc2c3c(c1)N(c1ccc(C(C)(C)C)cc1-c1ccccc1)c1cc4c(cc1B3c1ccc(N(c3ccc(C(C)(C)C)cc3)c3ccc(C(C)(C)C)cc3)cc1N2c1ccc(C(C)(C)C)cc1)C(C)(C)c1ccccc1C4(C)C]

-continued
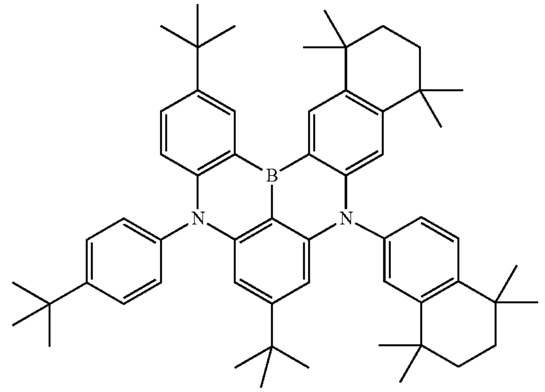
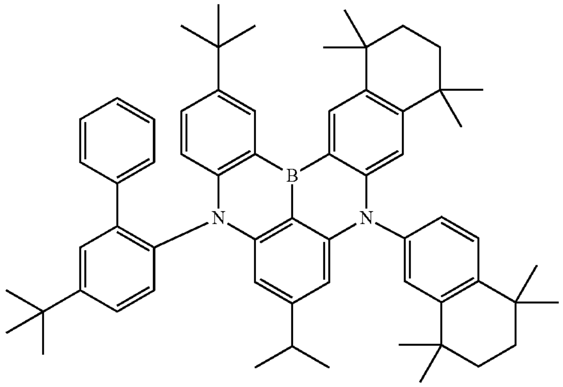
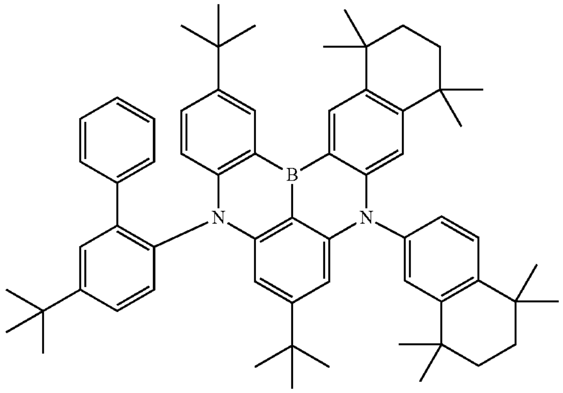
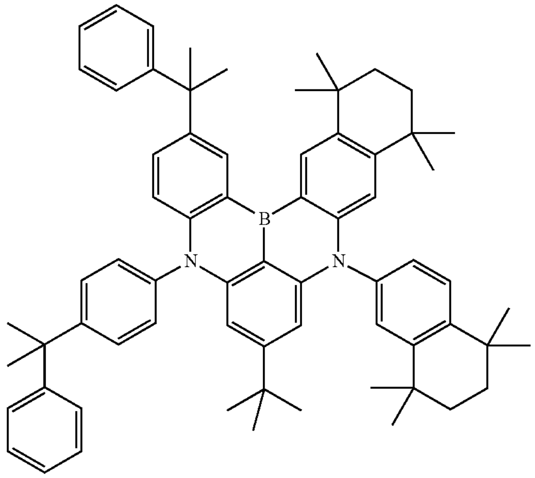
-continued
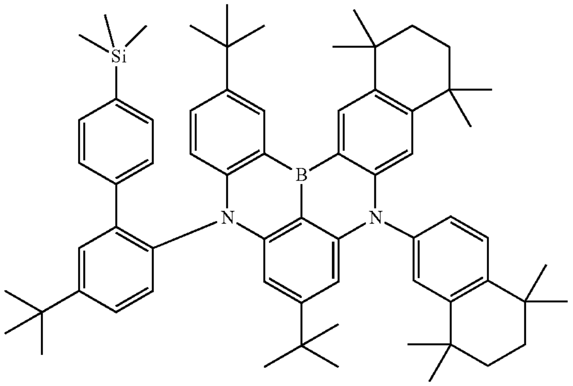
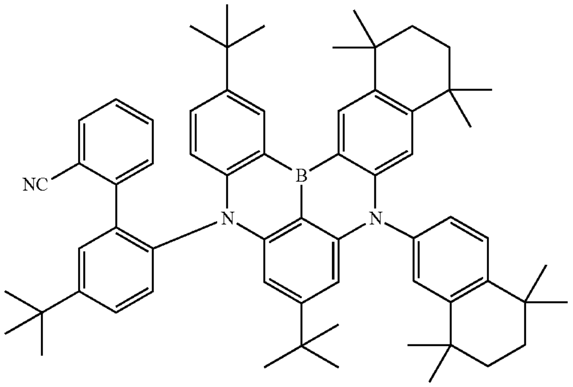
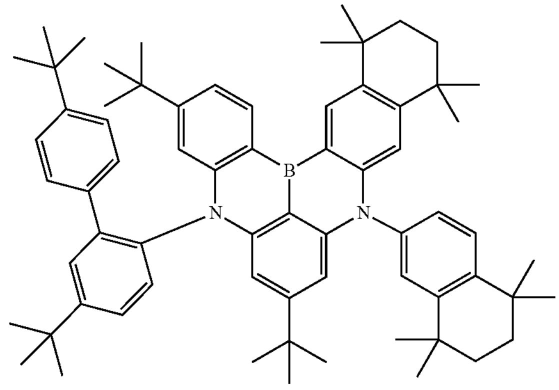
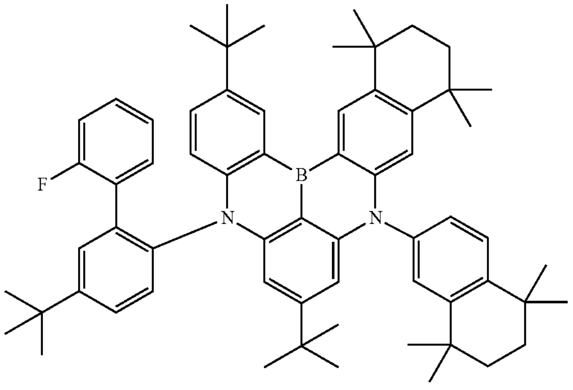

-continued
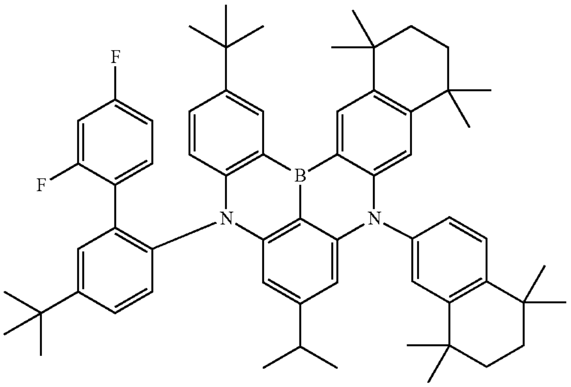
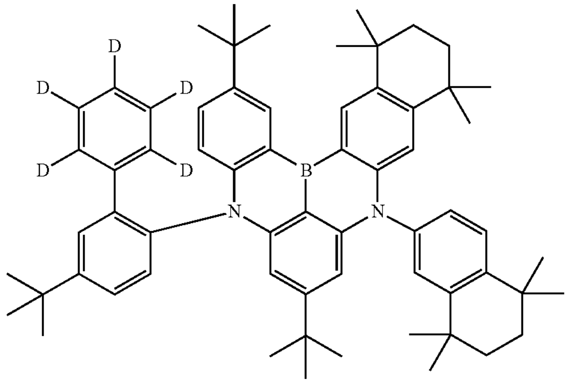
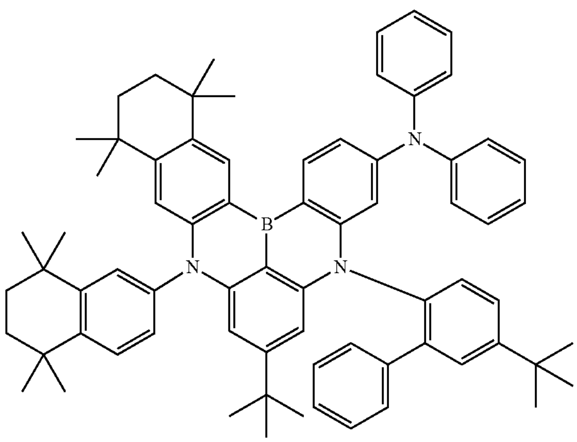
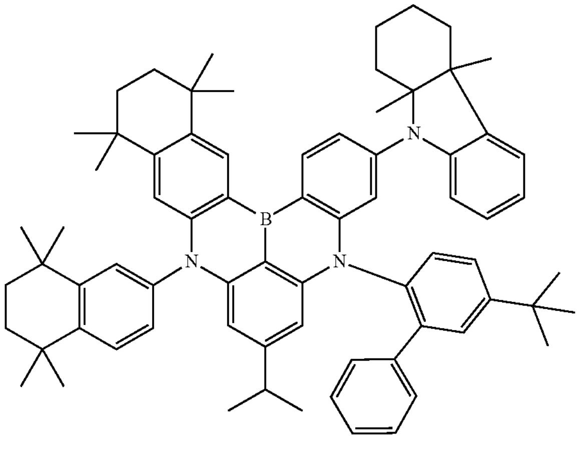
-continued
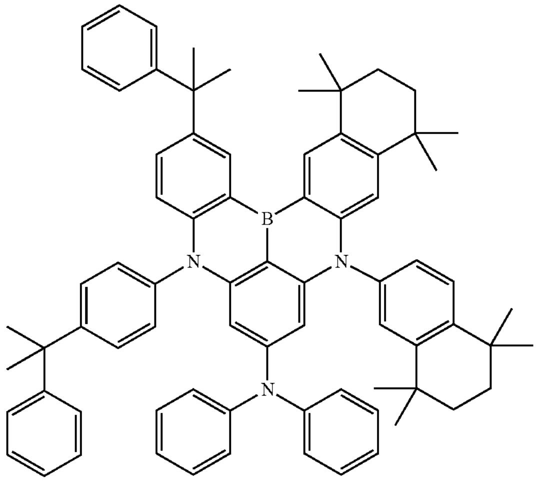
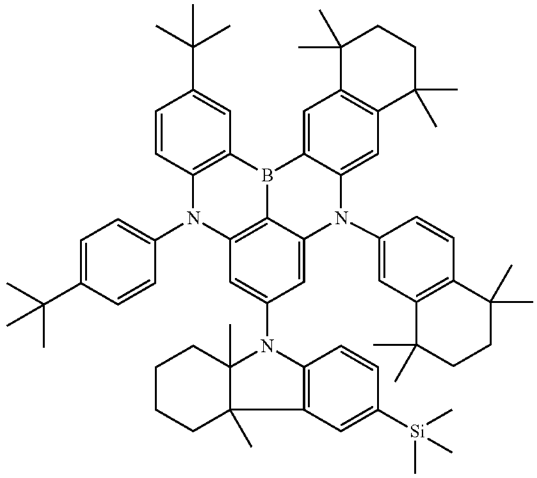
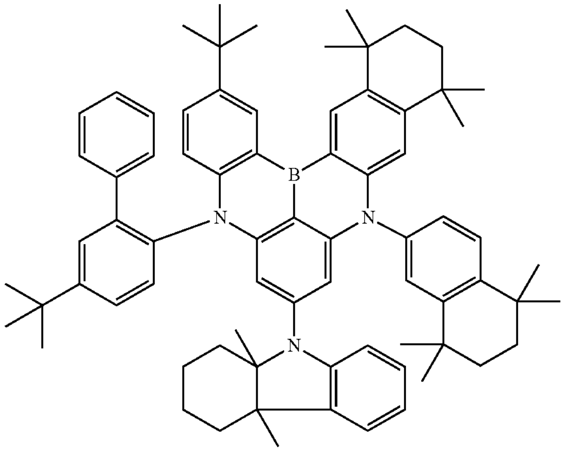

-continued
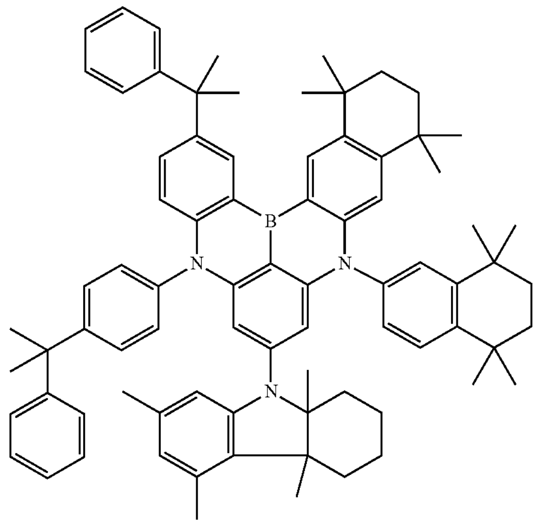
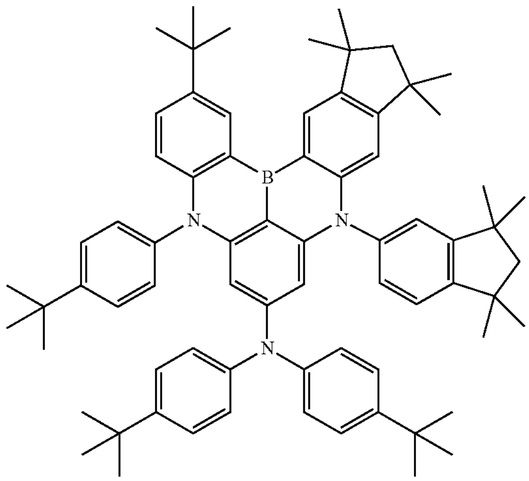
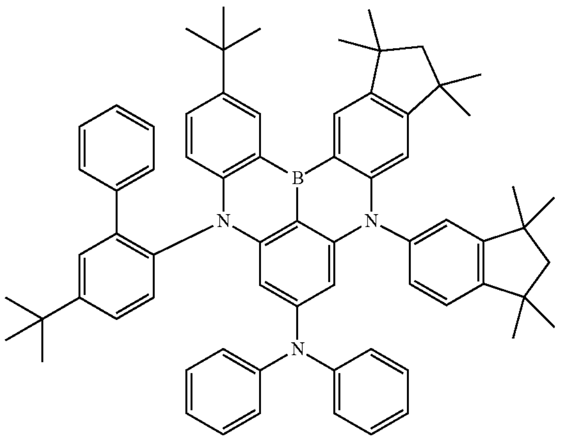
-continued
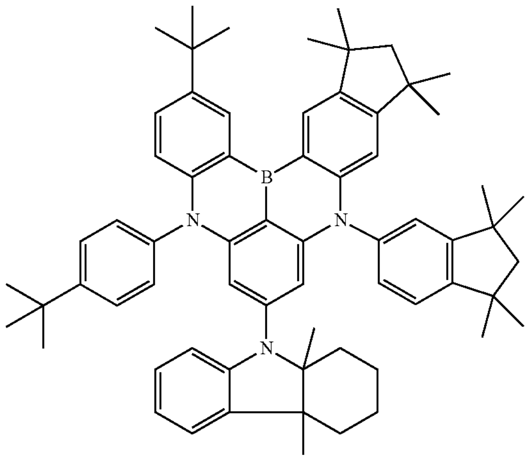
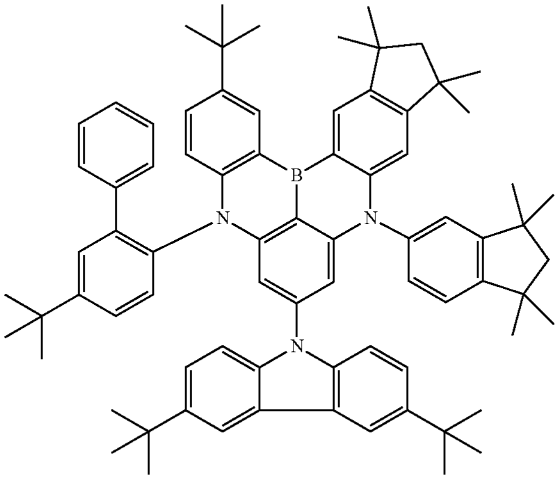
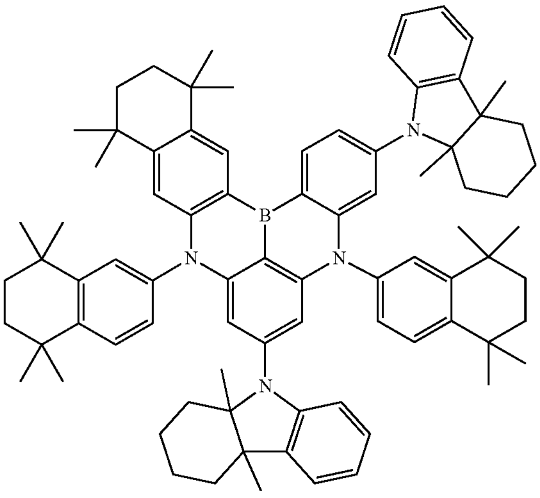

-continued
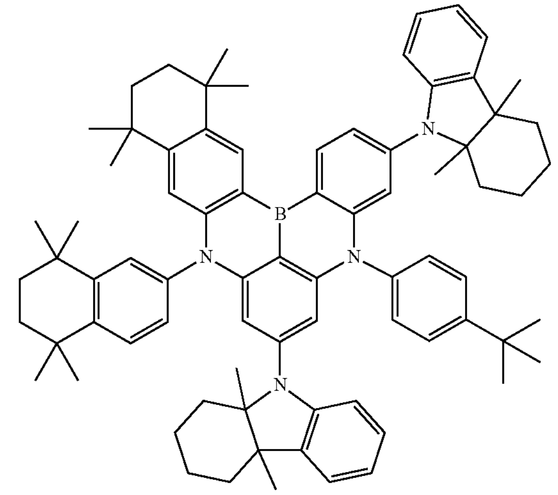
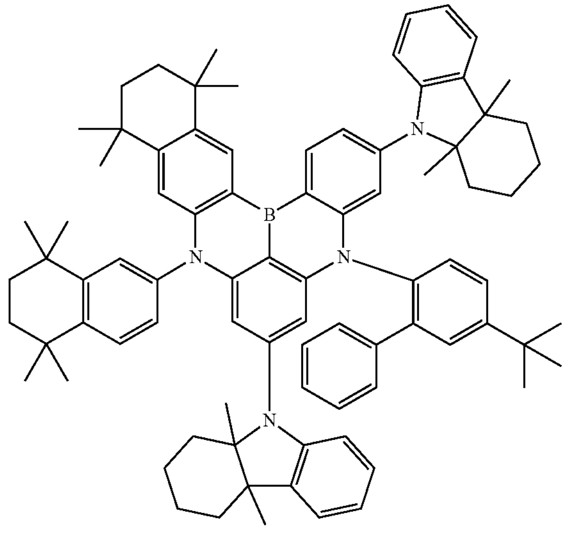
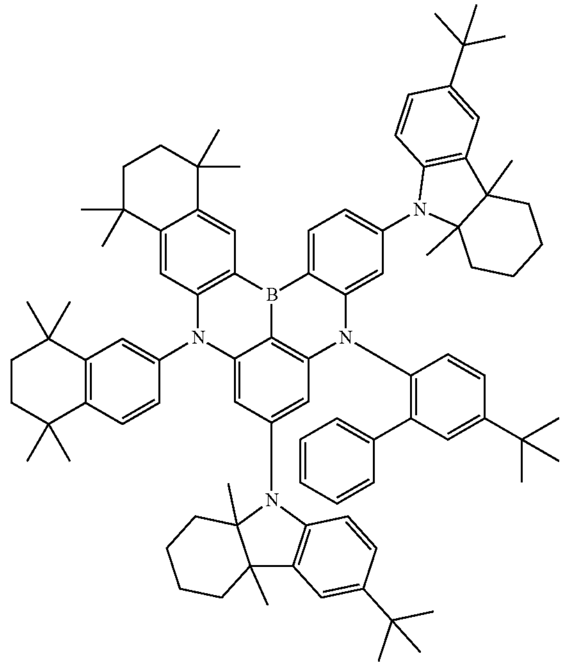
-continued
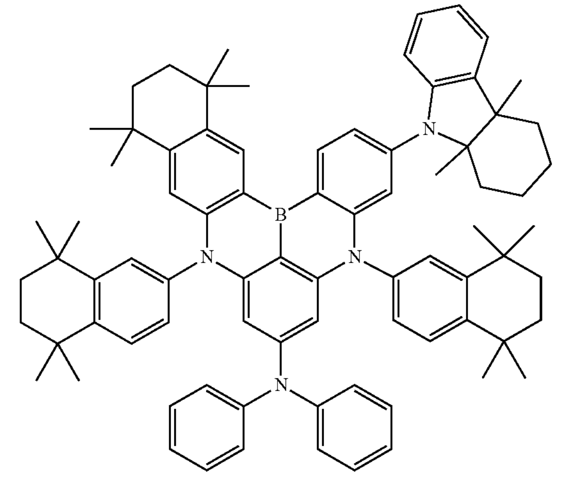
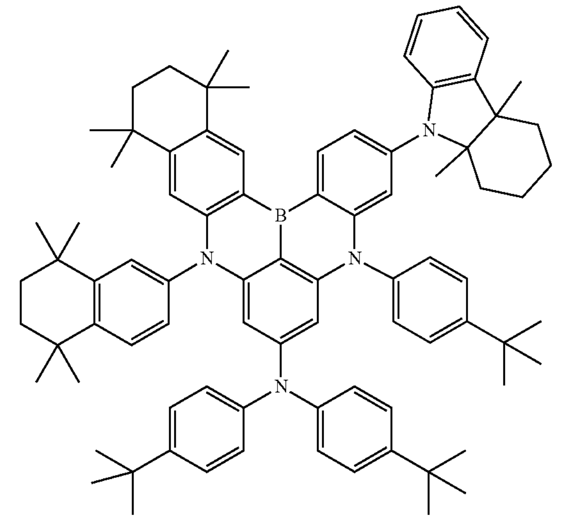
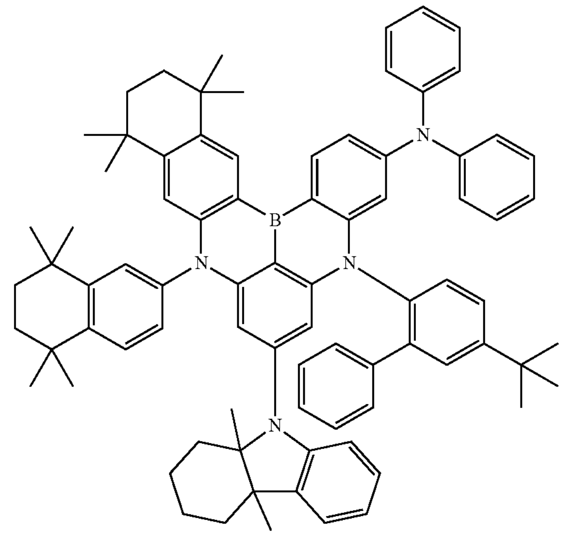

-continued
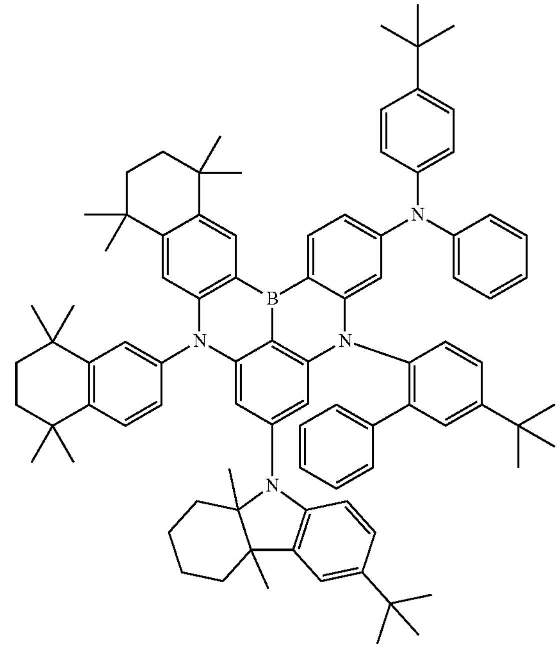 [SMILES: CC(C)(C)c1ccc(N(c2ccccc2)c2ccc3c(c2)N(c2ccc(C(C)(C)C)cc2-c2ccccc2)c2cc(N4c5ccc(C(C)(C)C)cc5C5(C)CCCCC45C)cc4c2B3c2cc3c(cc2N4c2ccc4c(c2)C(C)(C)CCC4(C)C)C(C)(C)CCC3(C)C)cc1]
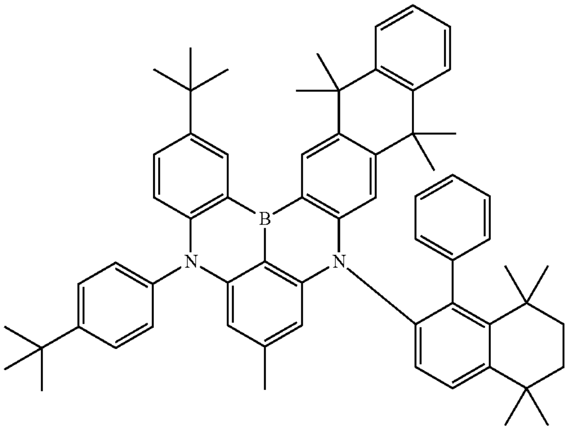
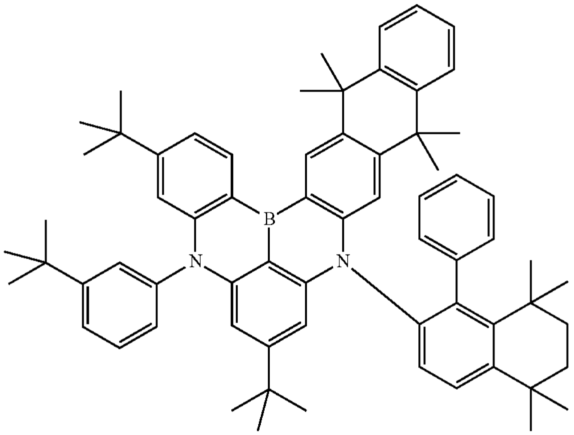
-continued
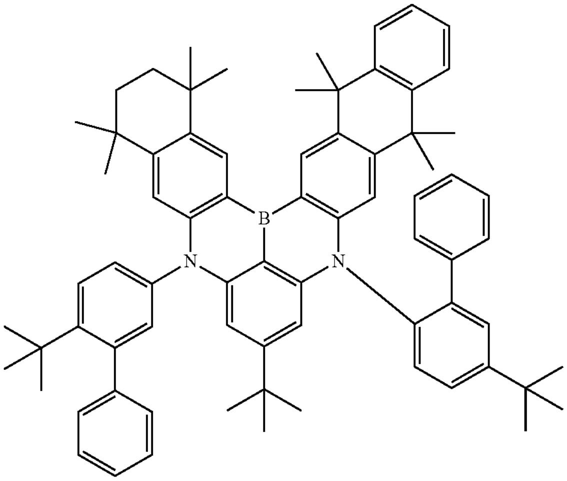
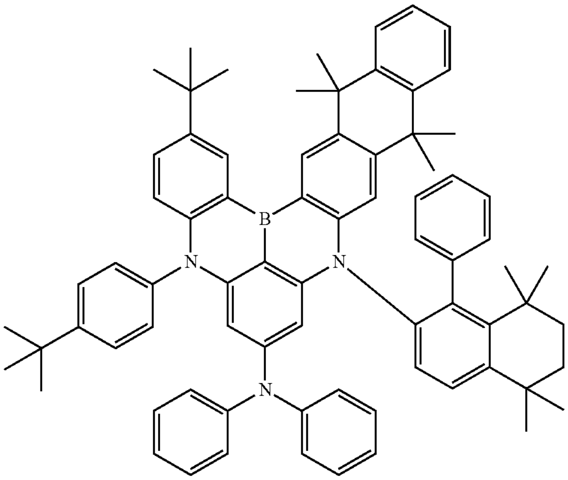
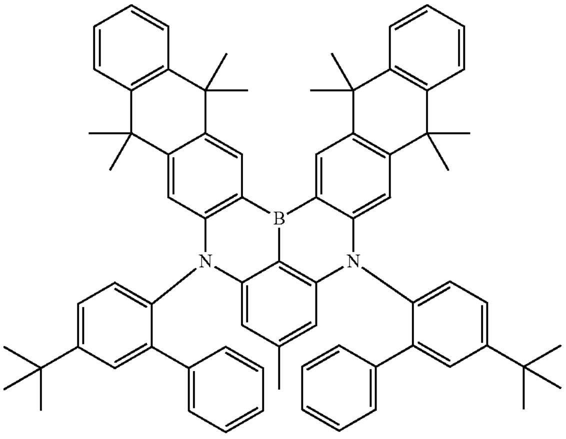

-continued
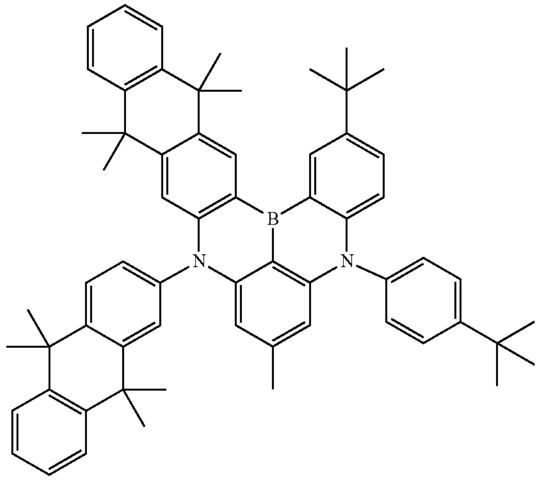
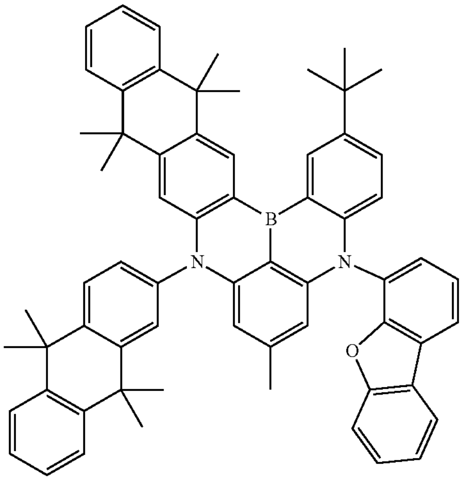
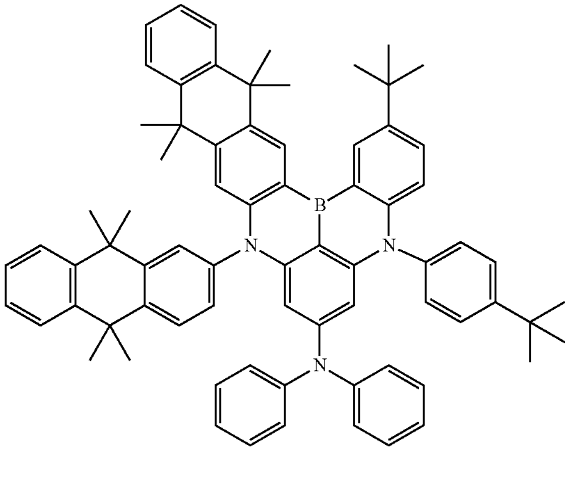
-continued
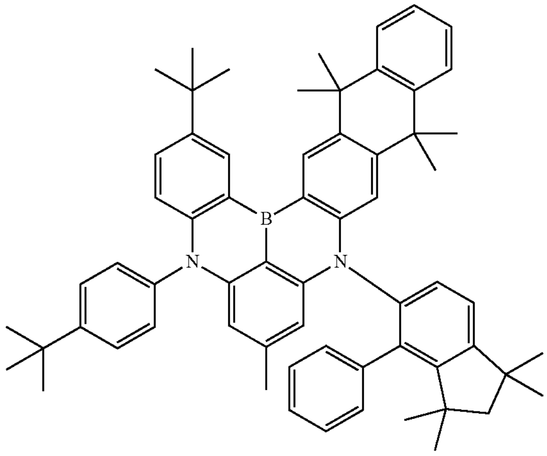
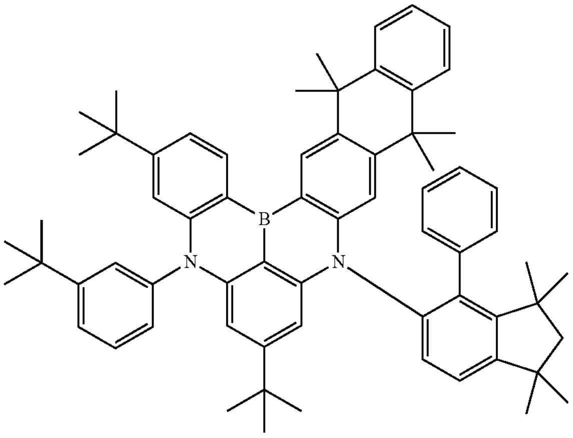
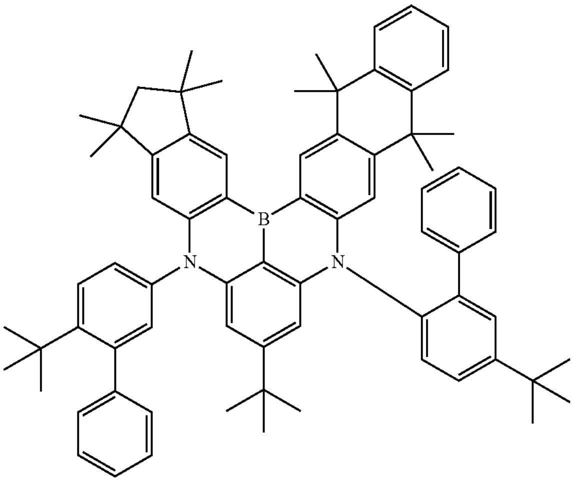

-continued
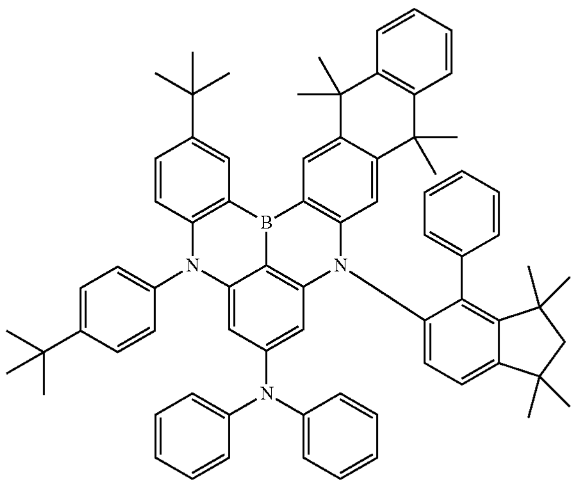
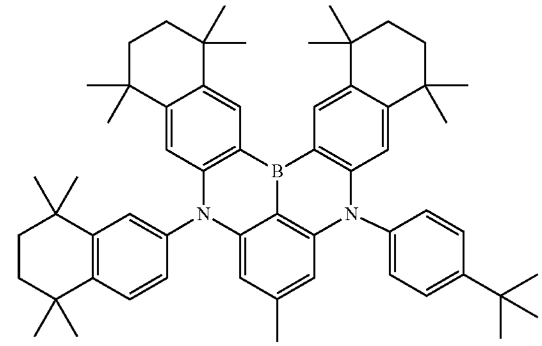
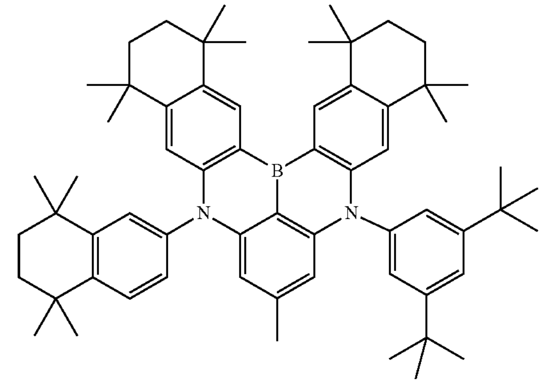
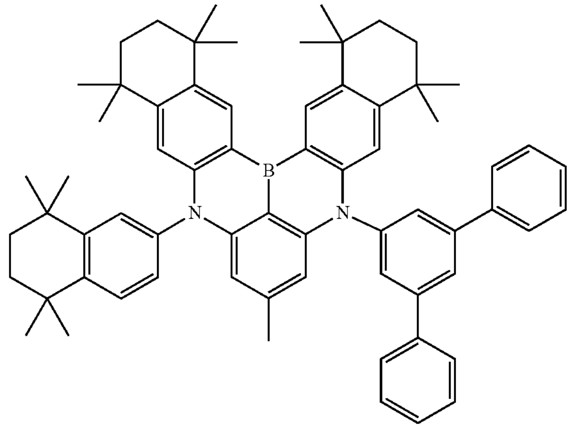
-continued
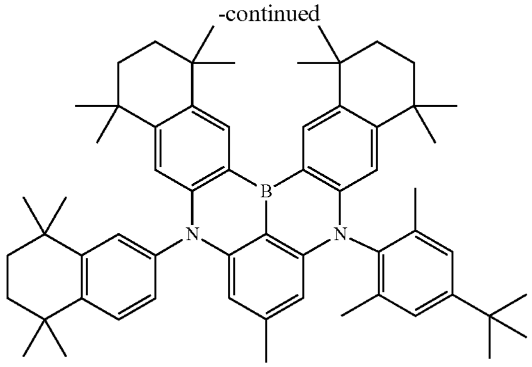
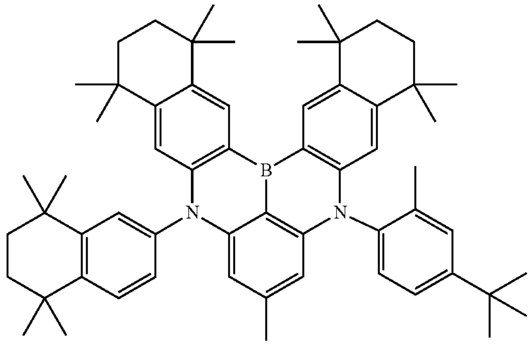
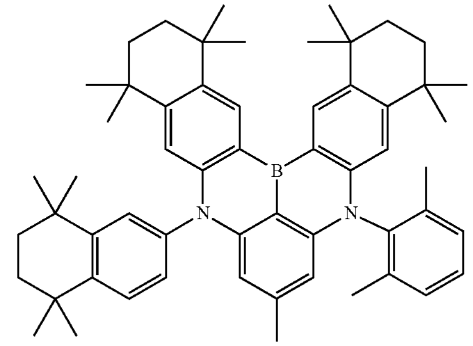
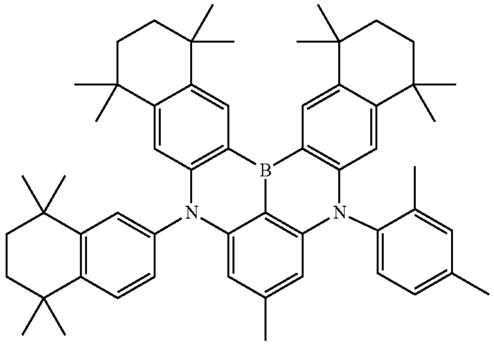
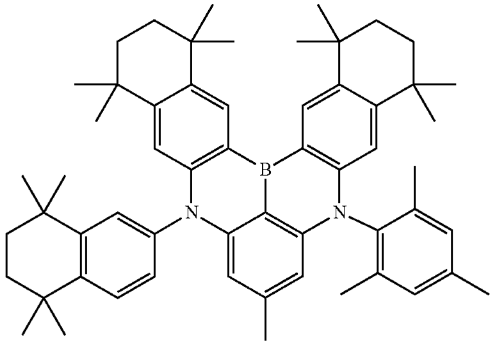

-continued
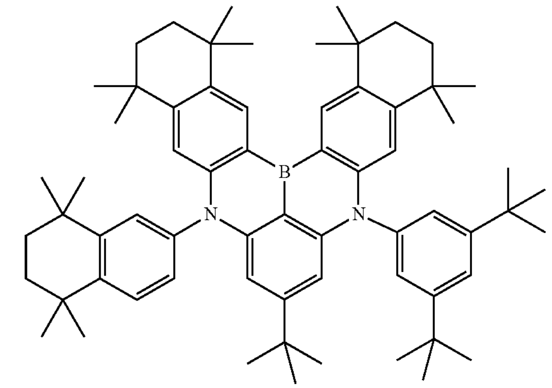
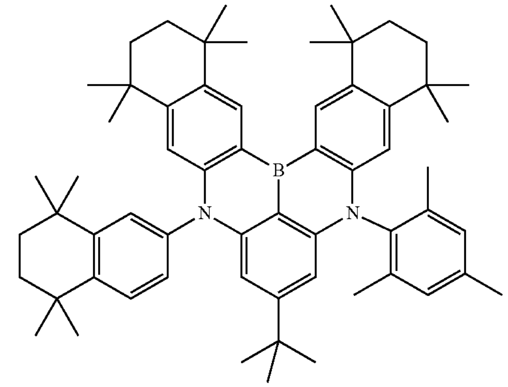
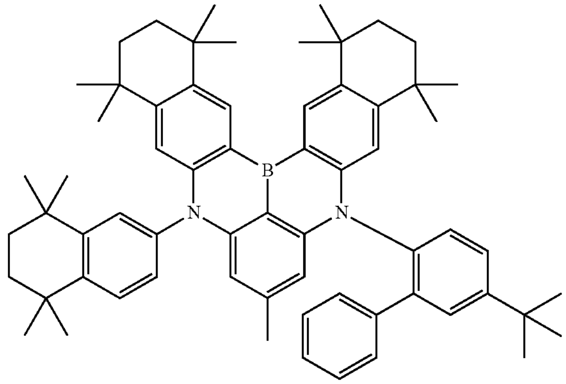
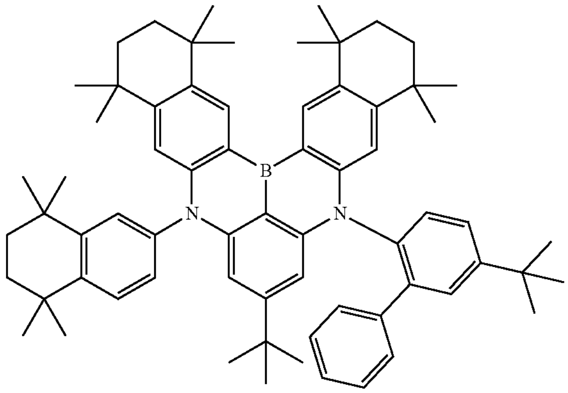
-continued
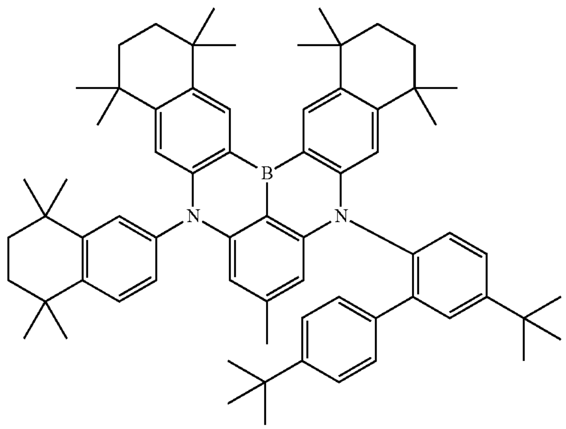
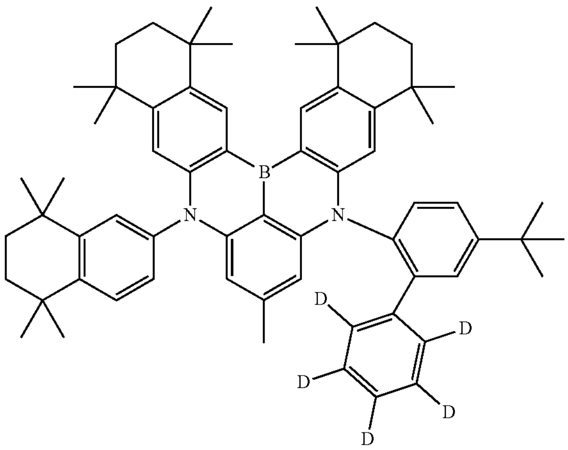
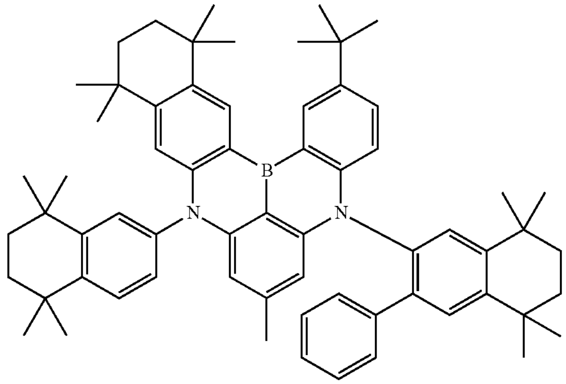
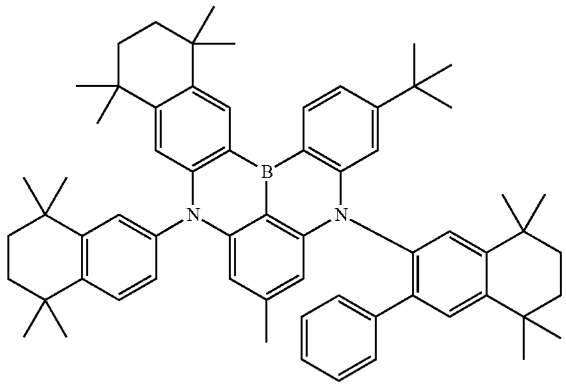

-continued
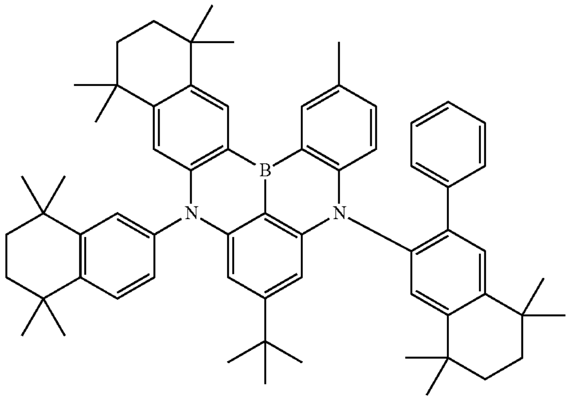
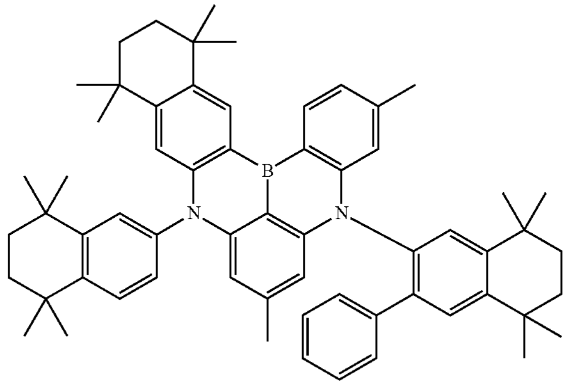
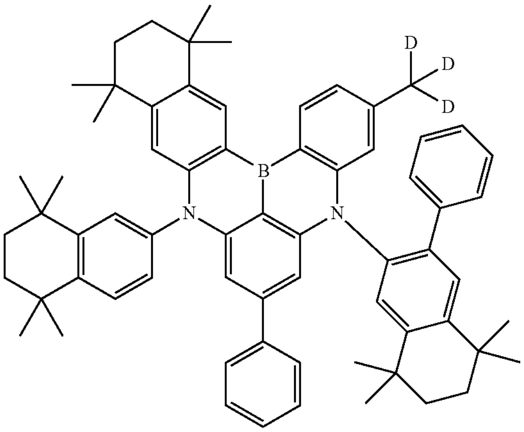
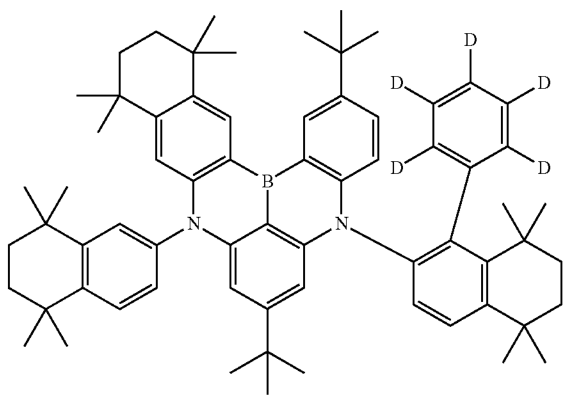
-continued
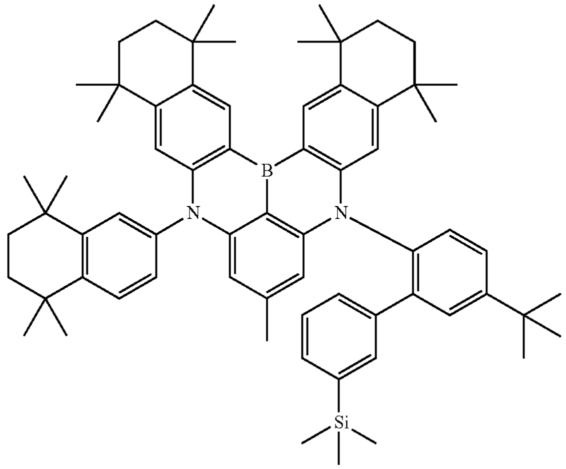
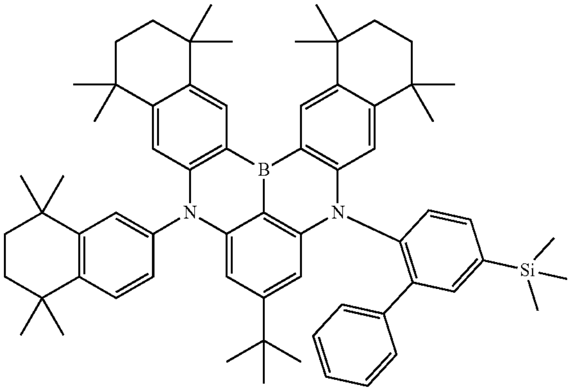
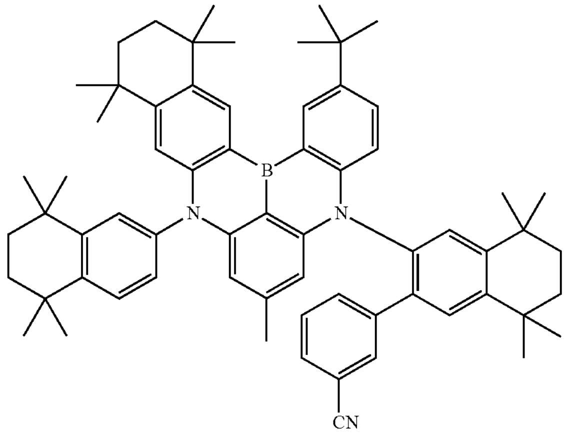

-continued
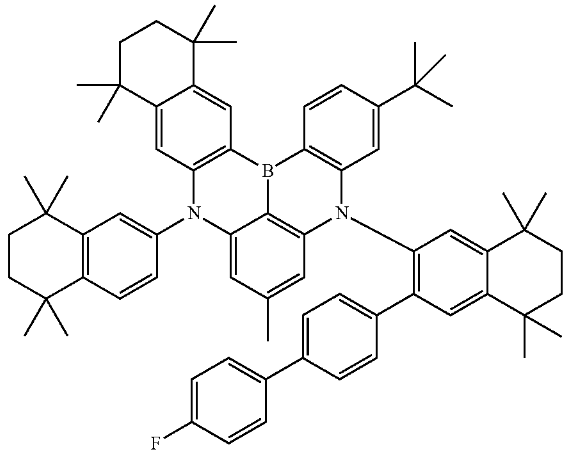
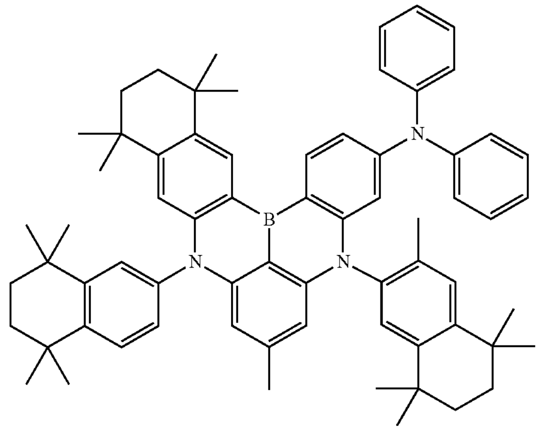
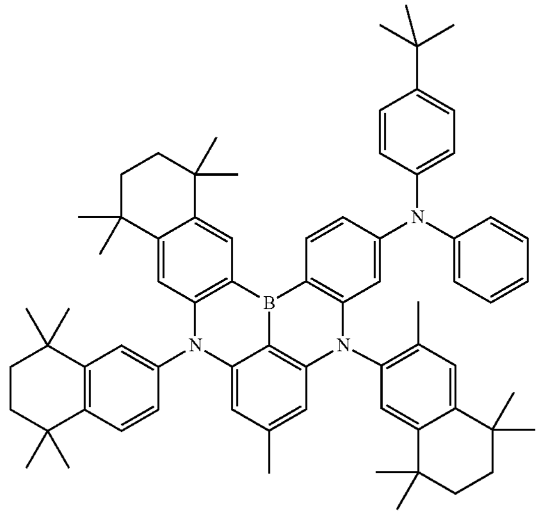
-continued
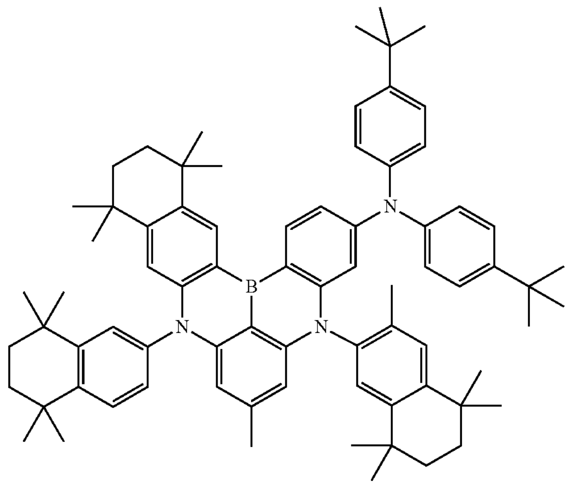
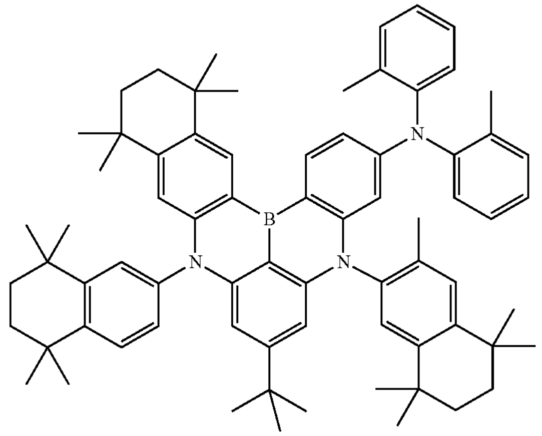
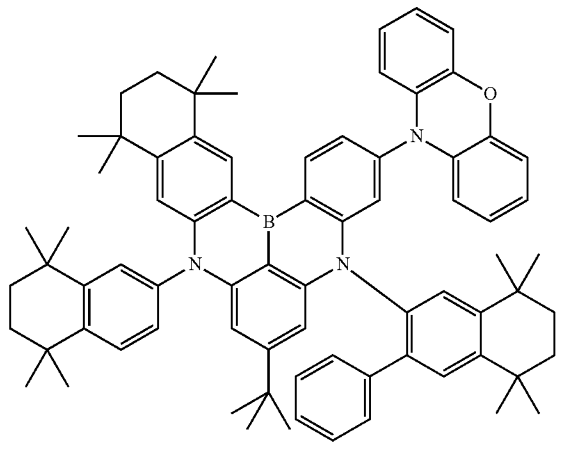

-continued
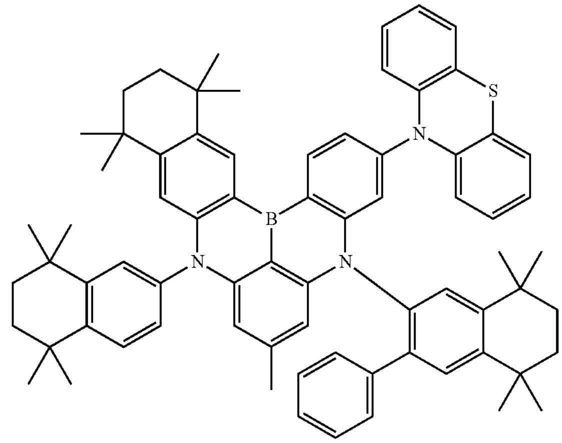
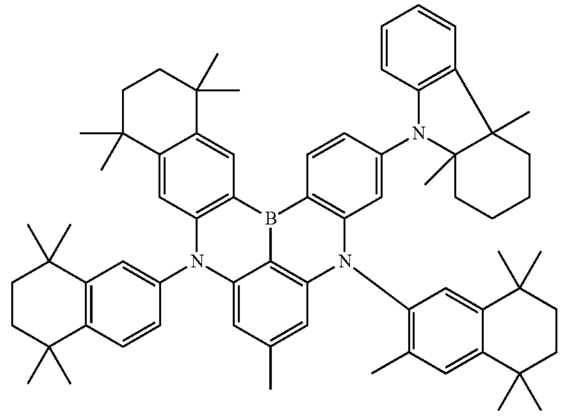
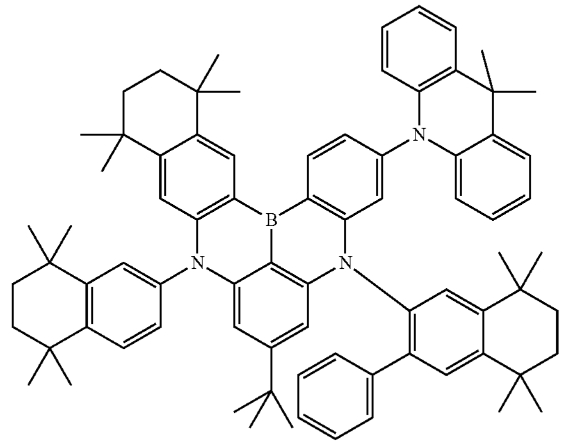
-continued
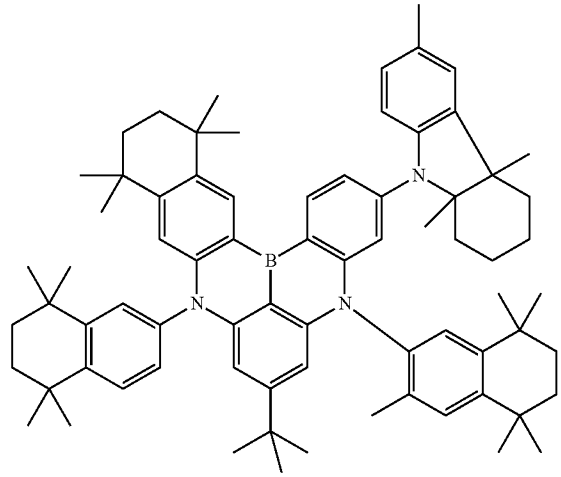
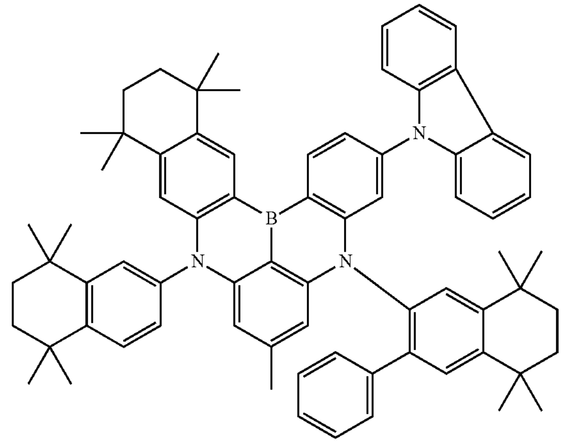
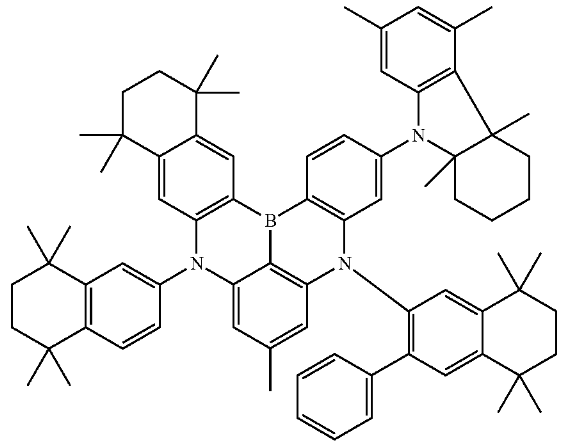

-continued
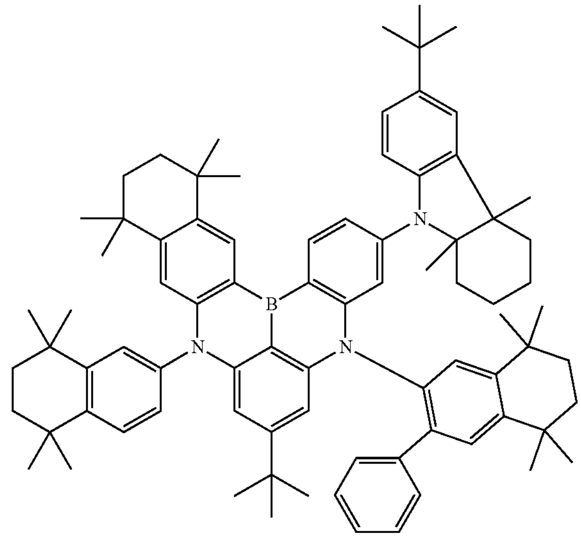
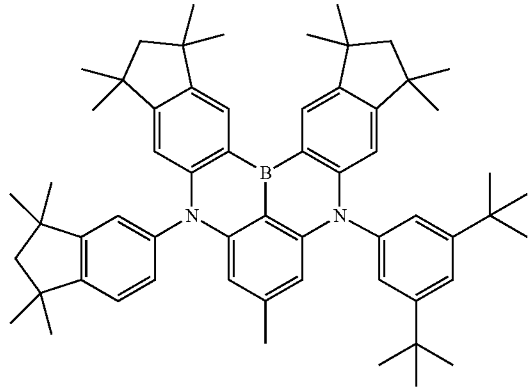
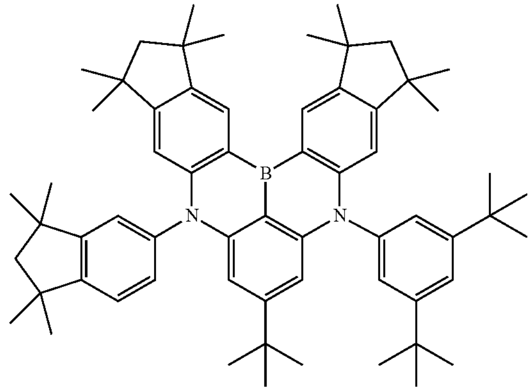
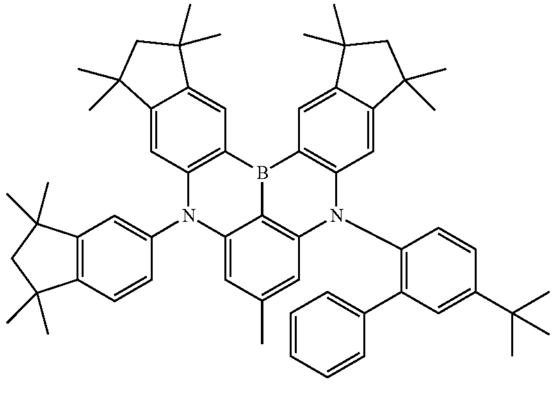
-continued
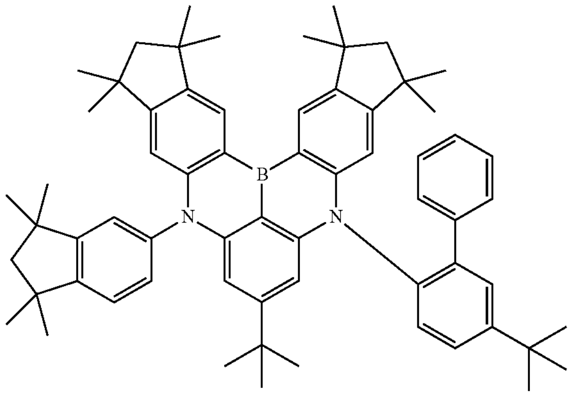
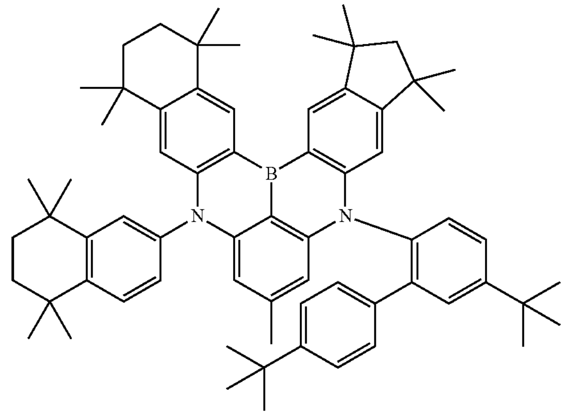
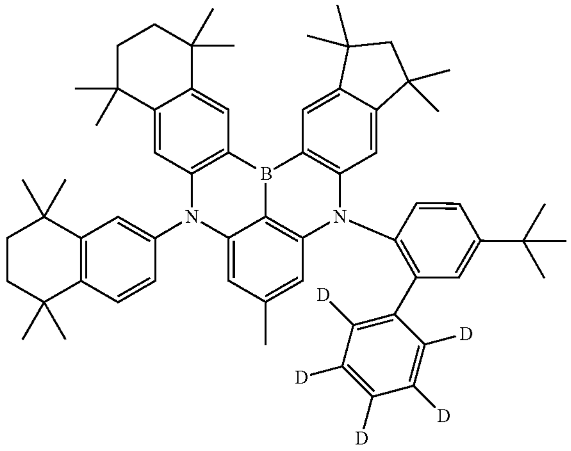
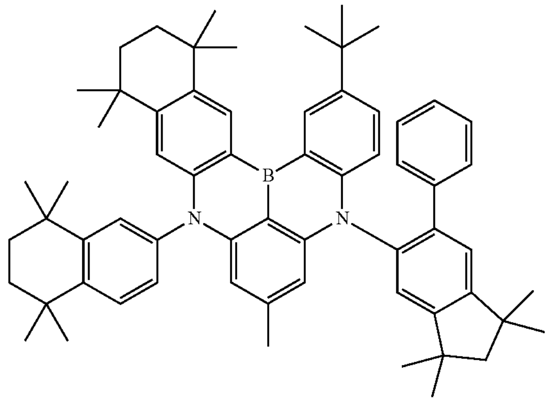

-continued
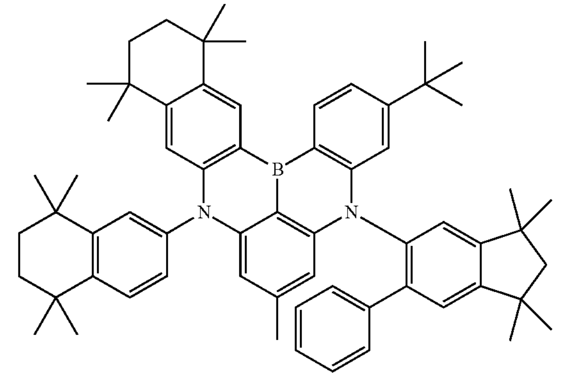
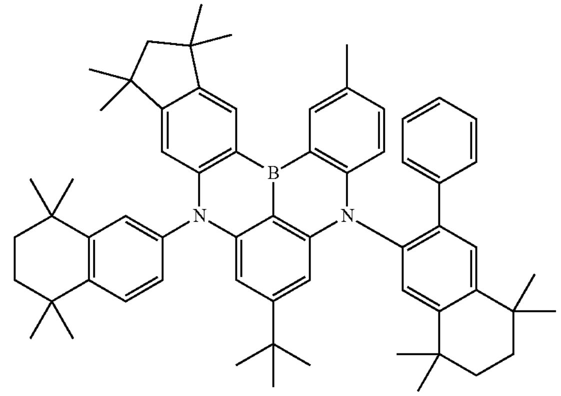
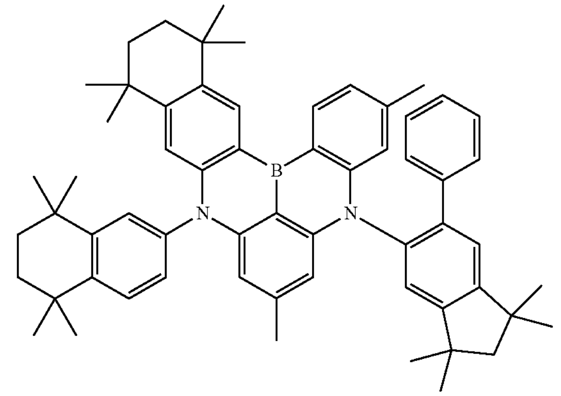
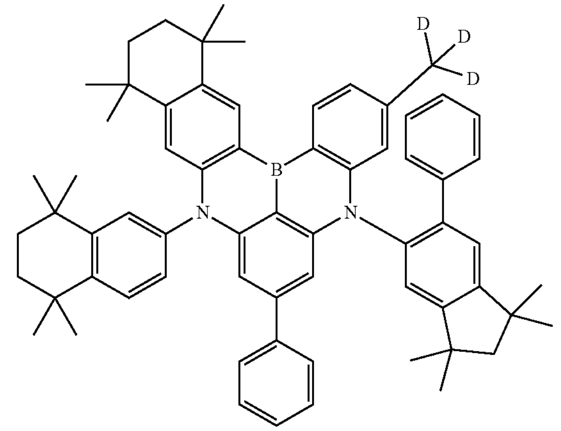
-continued
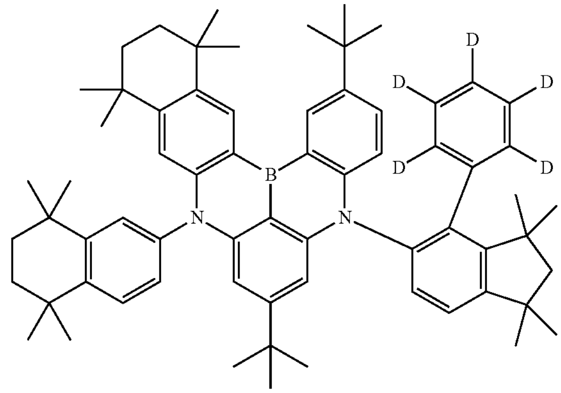
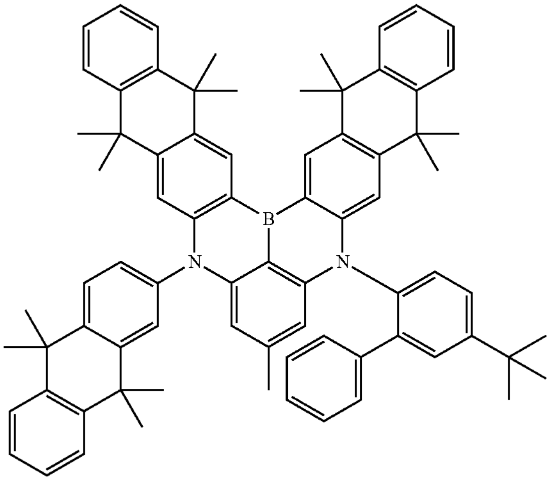
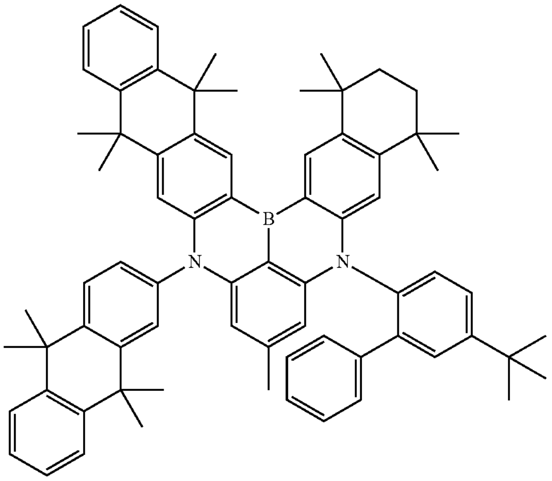

-continued
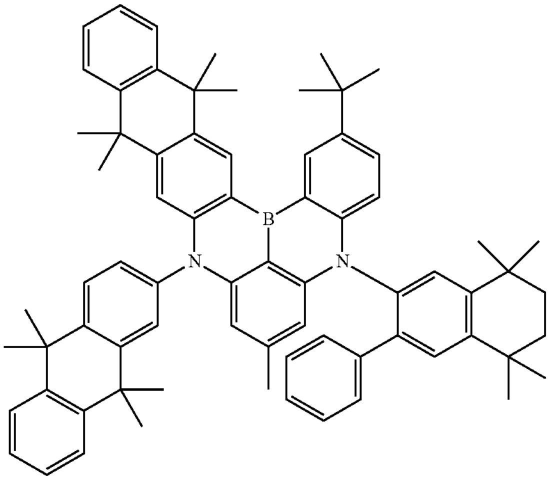
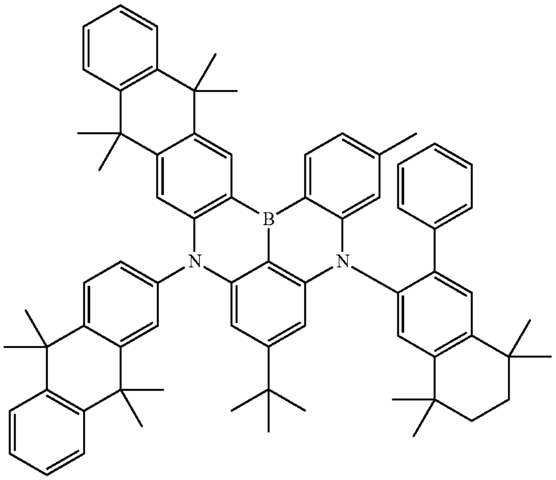
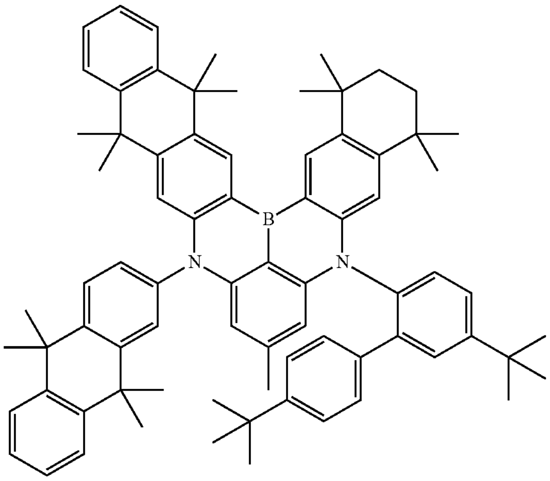
-continued
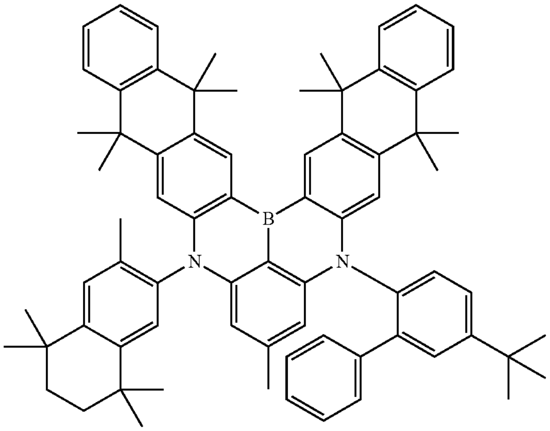
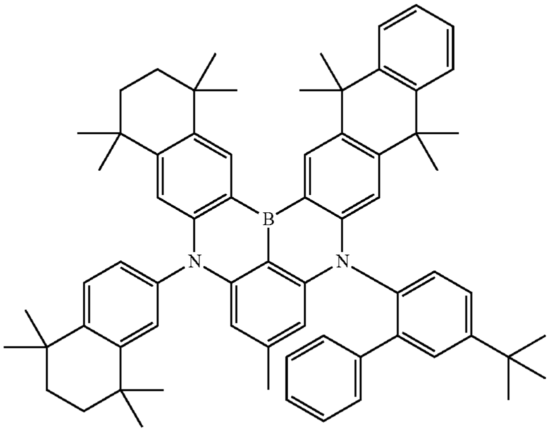
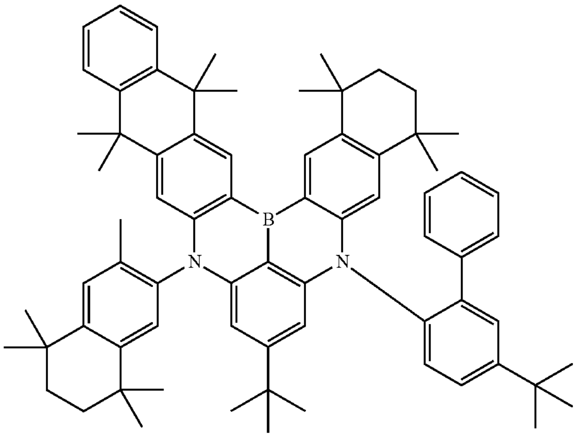

-continued
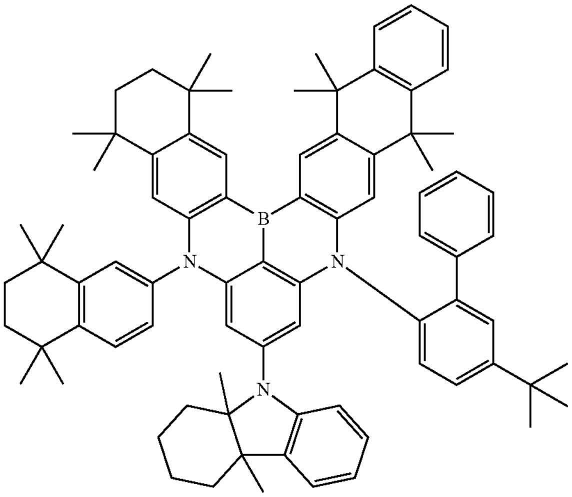
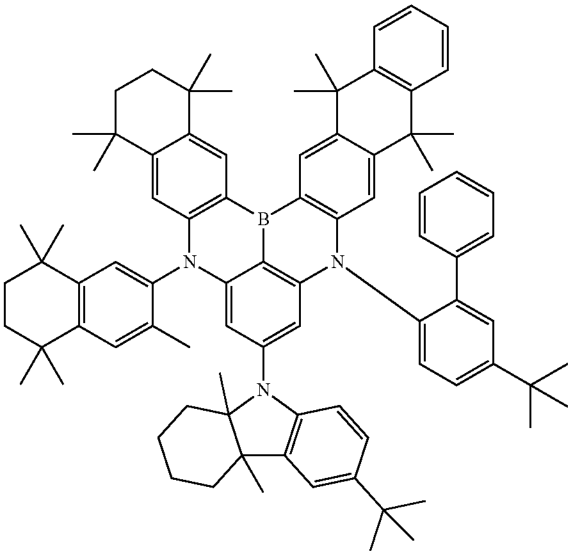
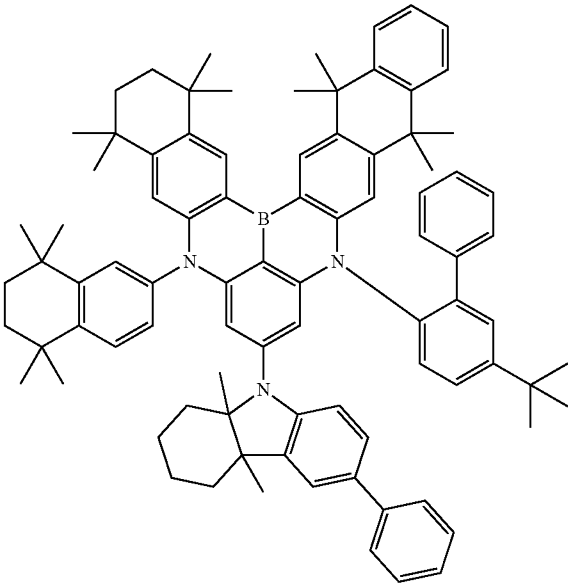
-continued
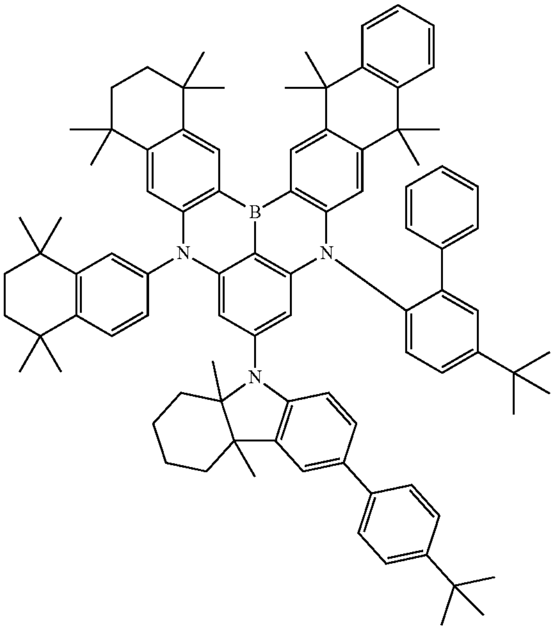
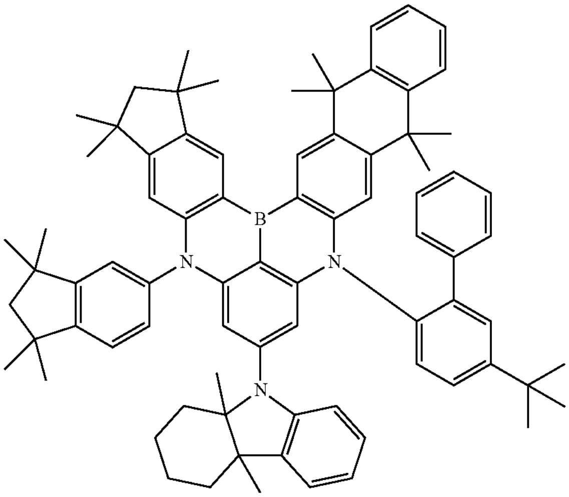 [SMILES: CC(C)(C)c1ccc(N2c3cc4c(cc3B3c5cc6c(cc5N(c5ccc7c(c5)C(C)(C)CC7(C)C)c5cc(N7c8ccccc8C8(C)CCCCC78C)cc2c53)C(C)(C)CC6(C)C)C(C)(C)c2ccccc2C4(C)C)c(-c2ccccc2)c1]
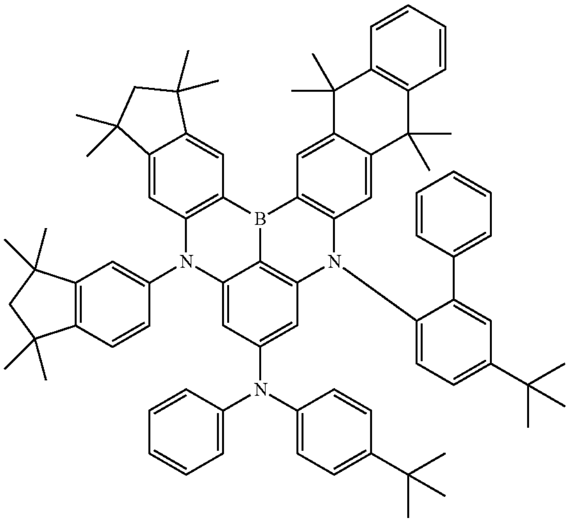

-continued
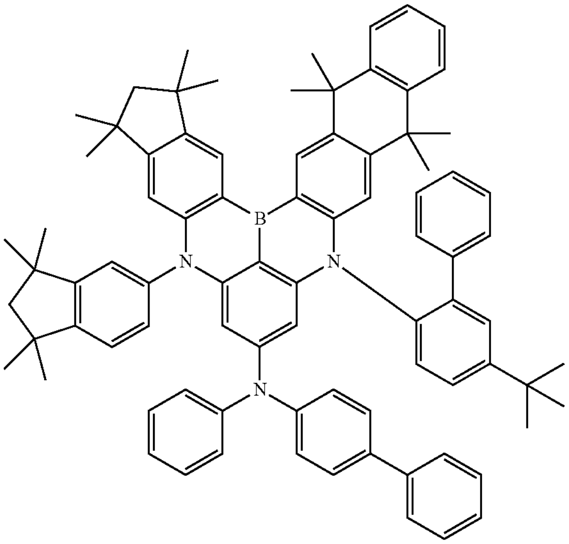
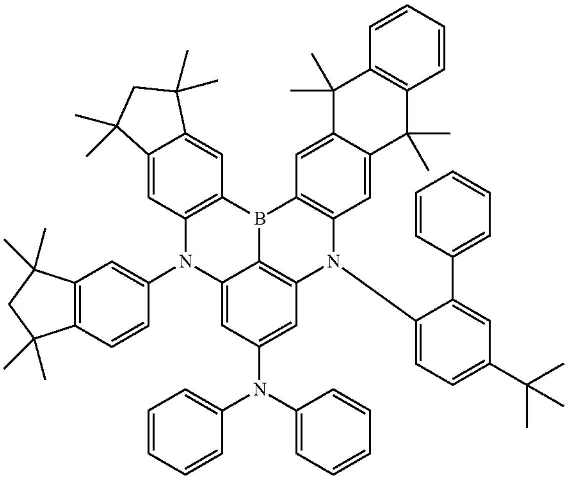
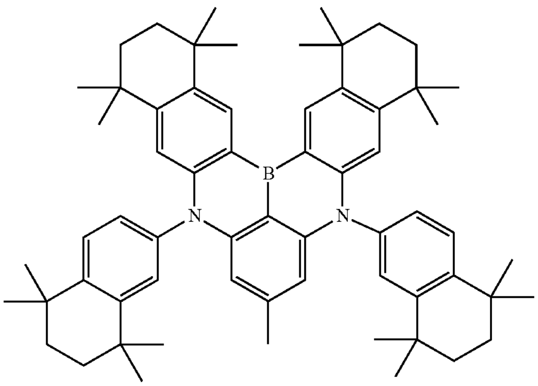
-continued
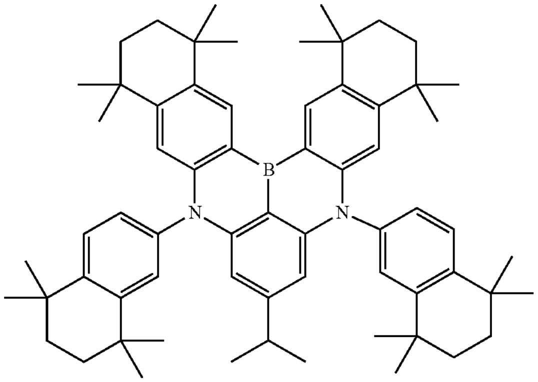
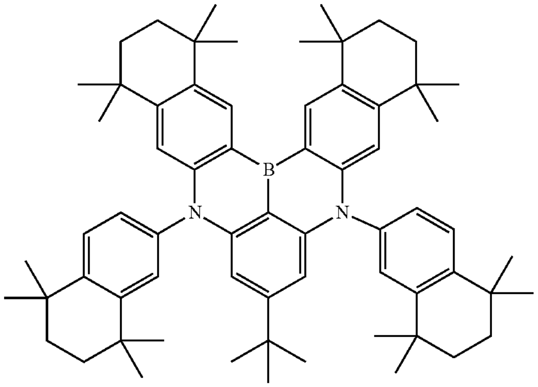
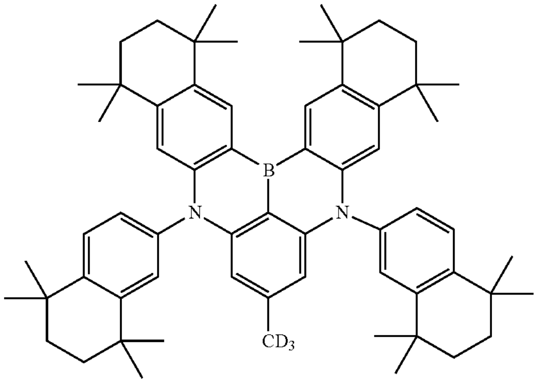
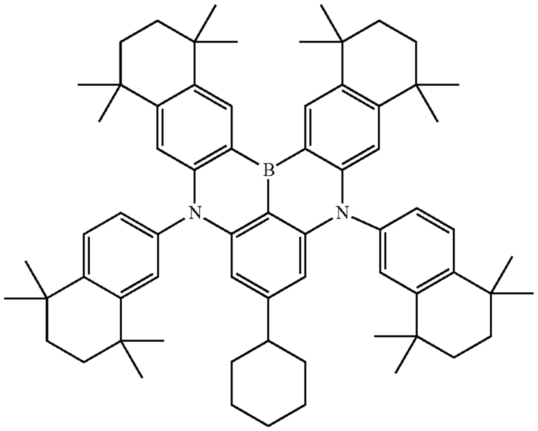

-continued
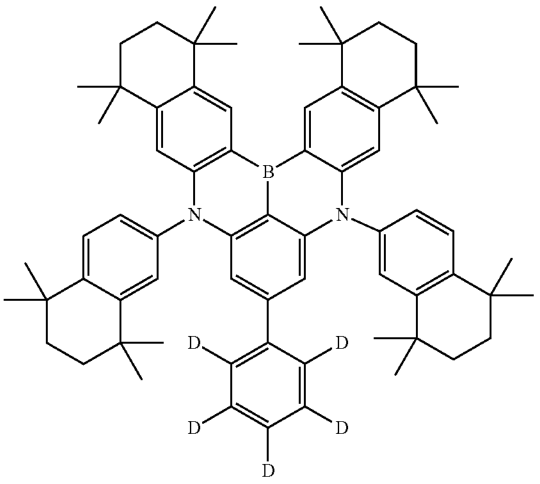
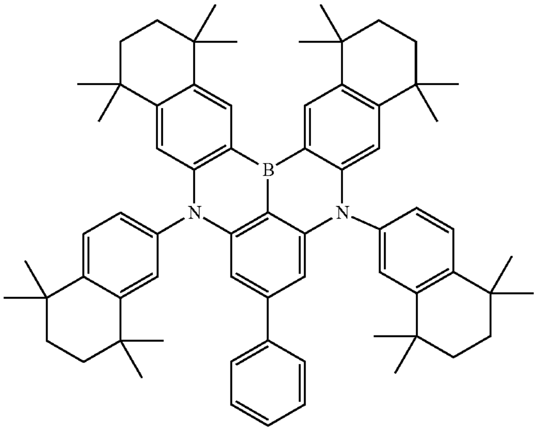
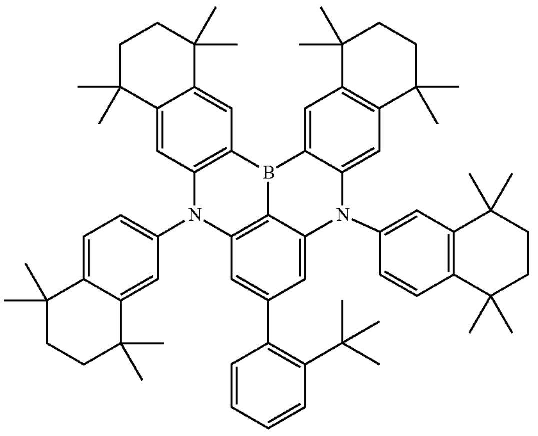
-continued
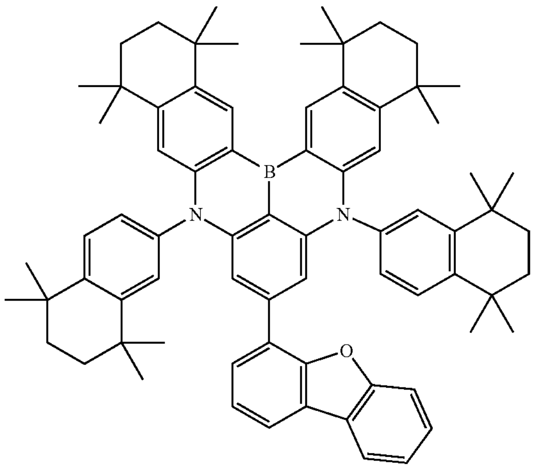
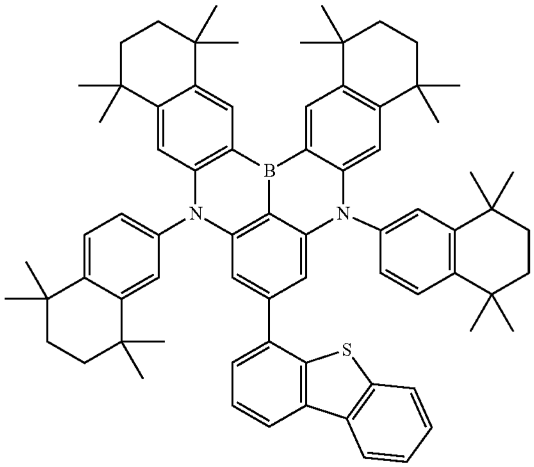
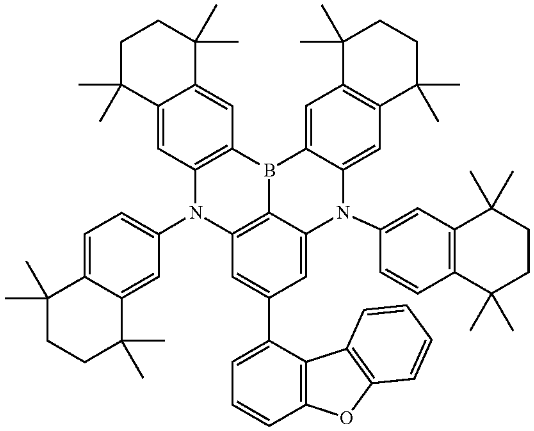

-continued
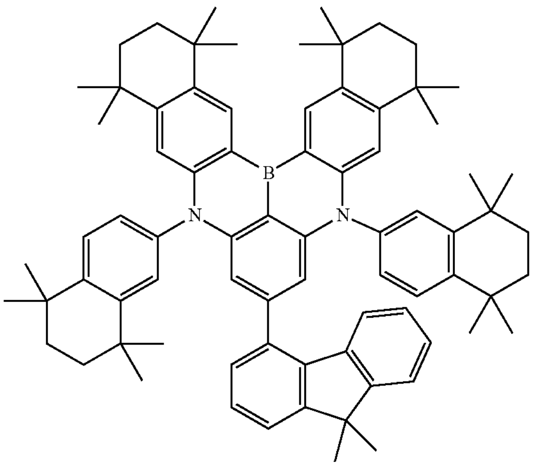
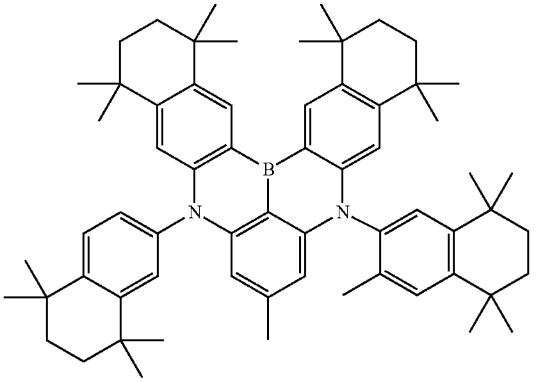
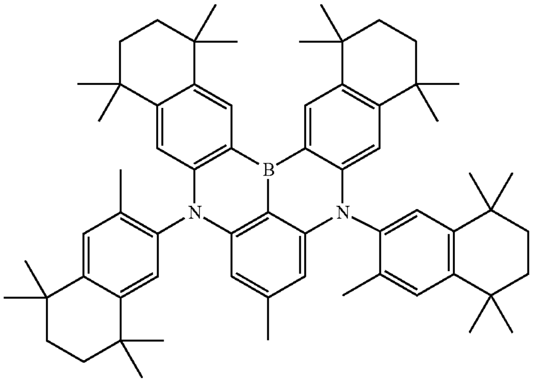
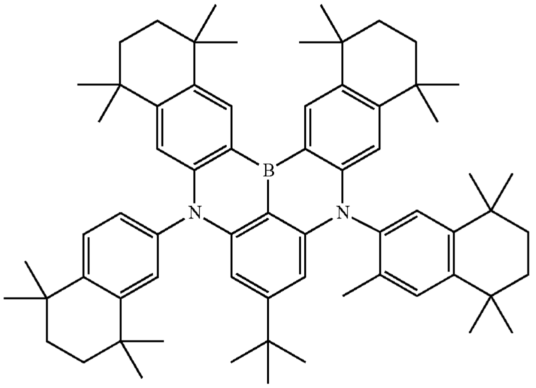
-continued
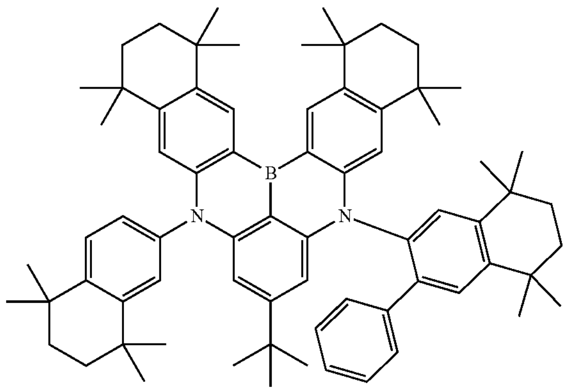
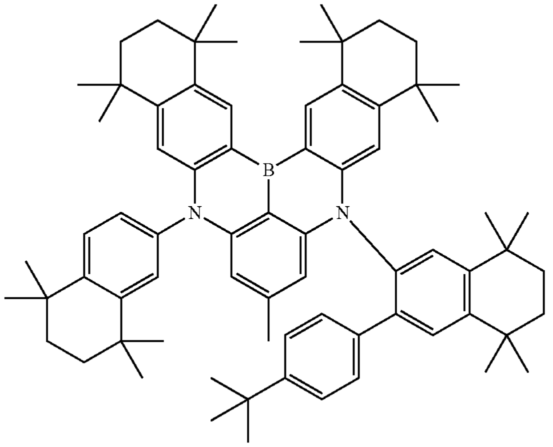
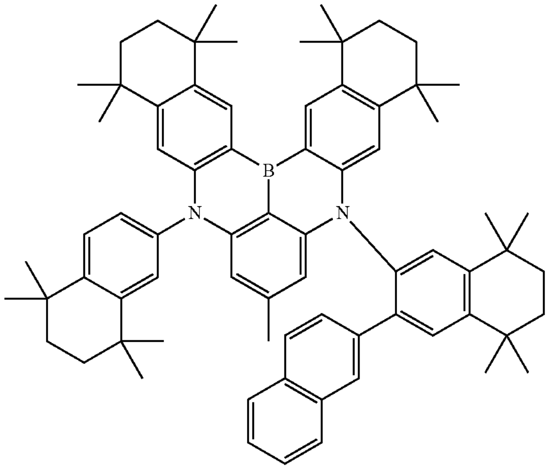
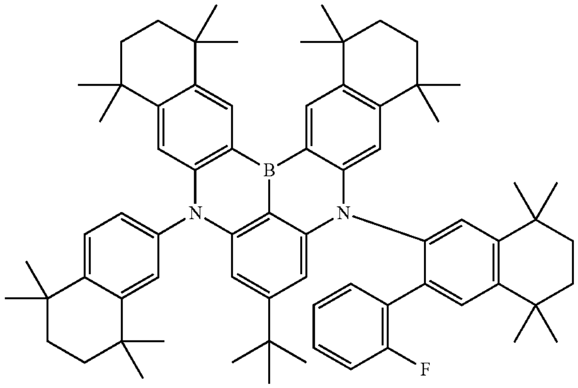

-continued
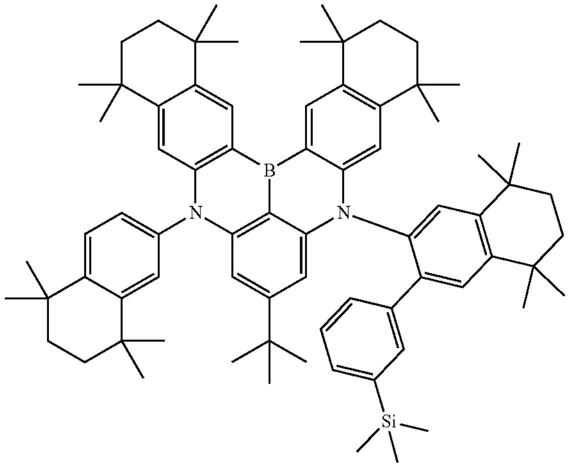
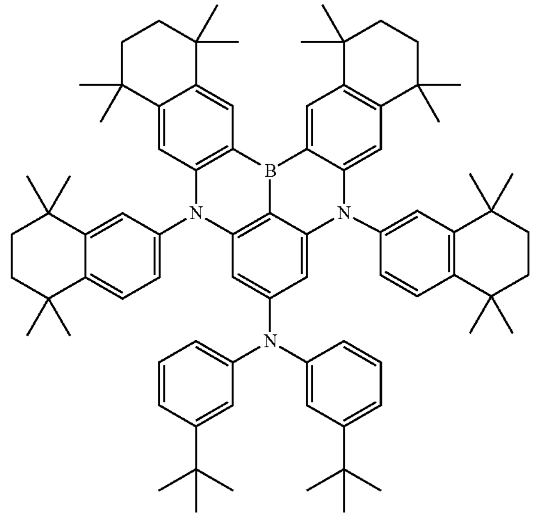
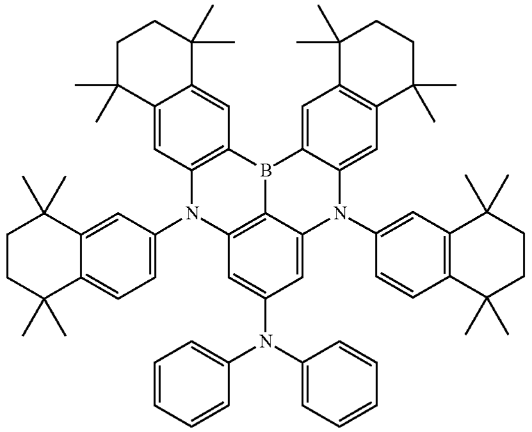
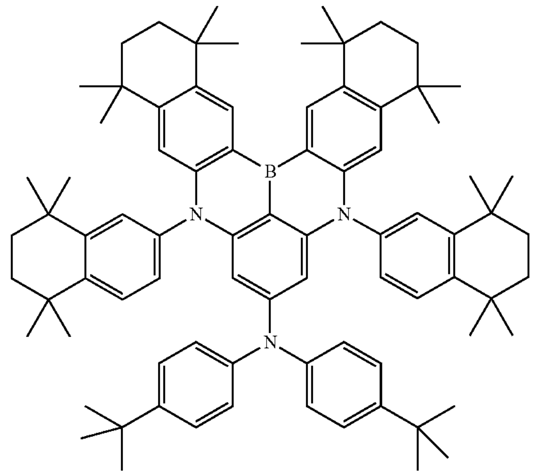
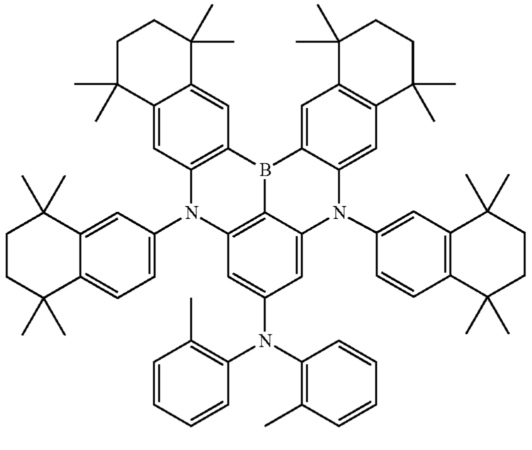
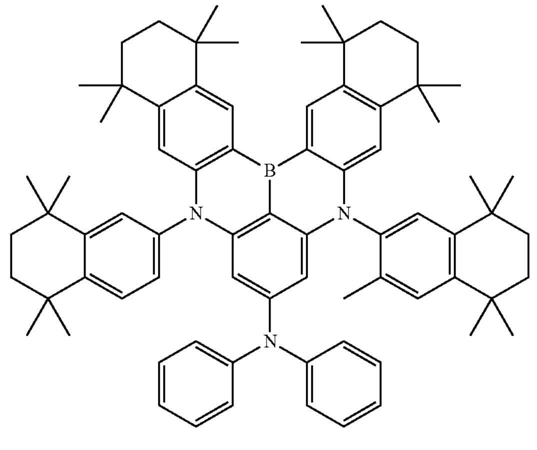

-continued
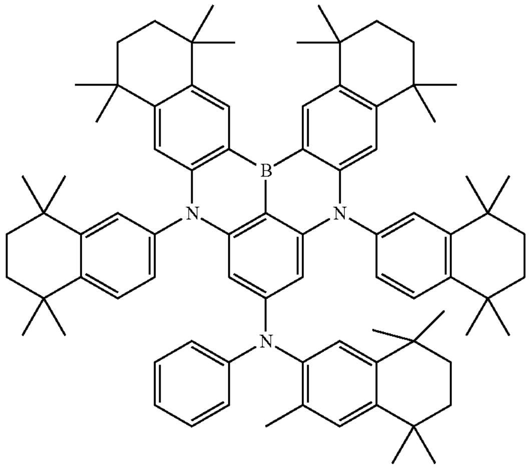
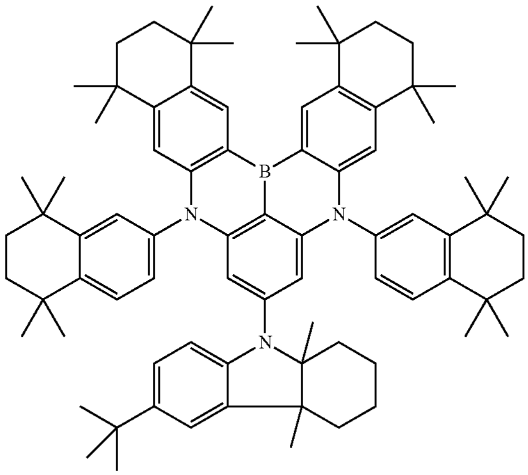
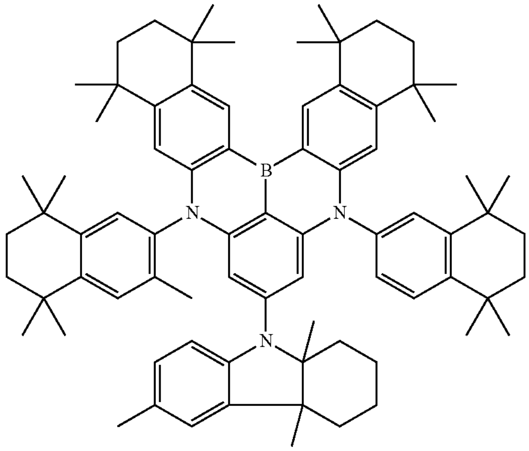
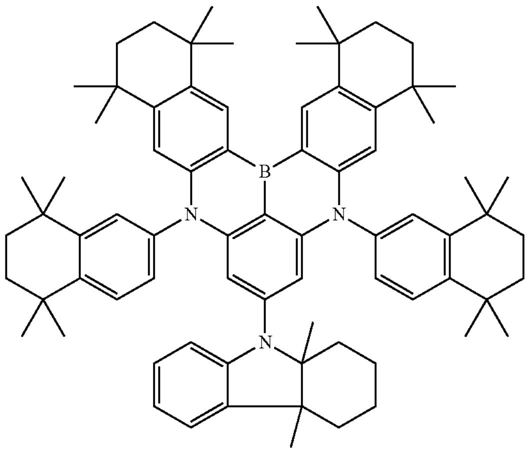
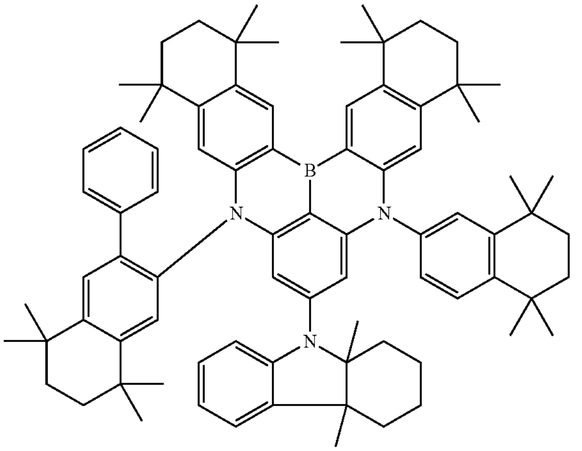
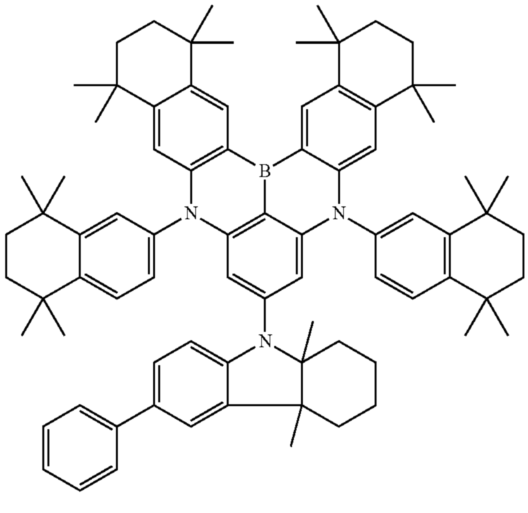
-continued -continued
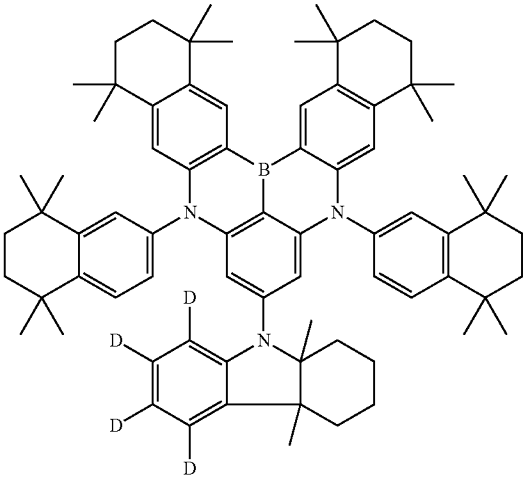
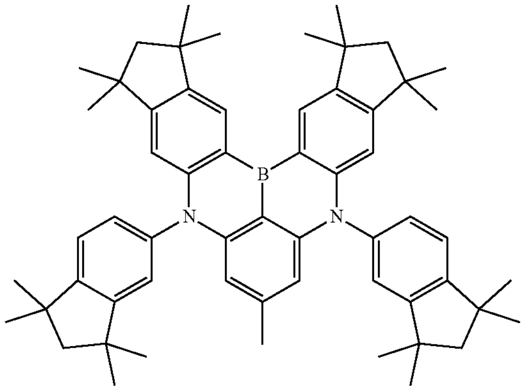
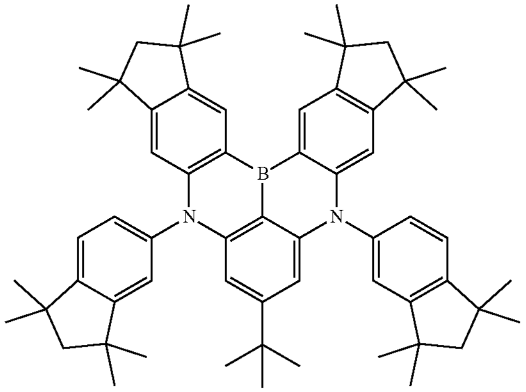
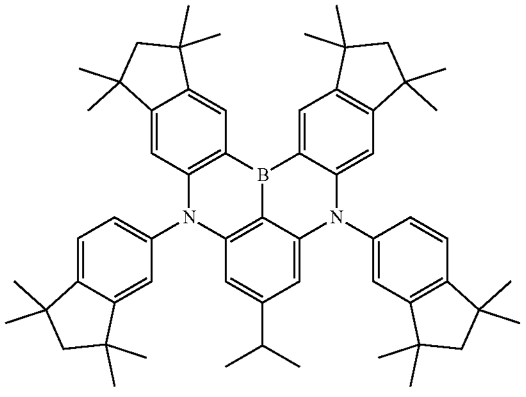
-continued
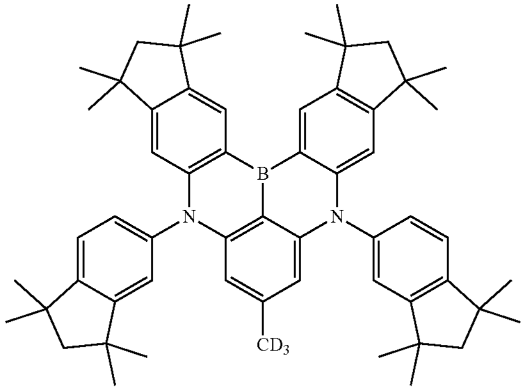
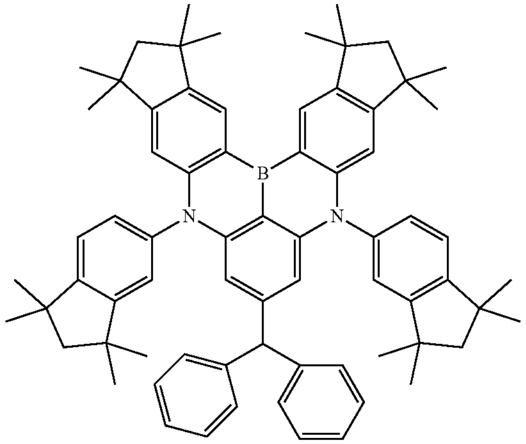
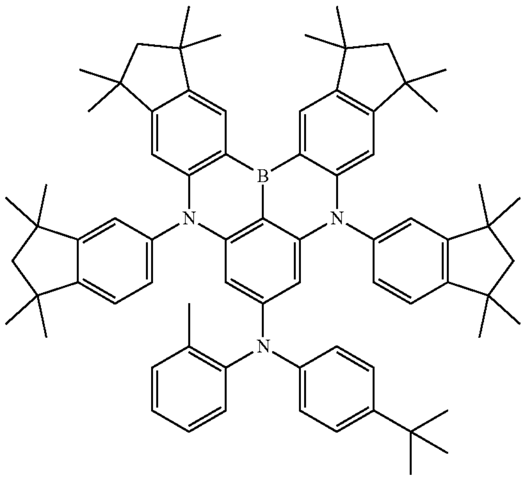

-continued
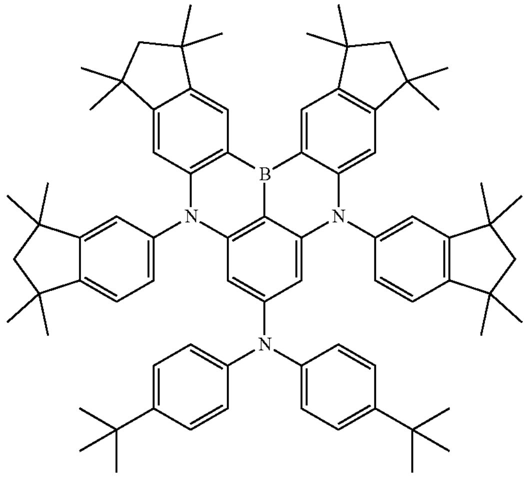
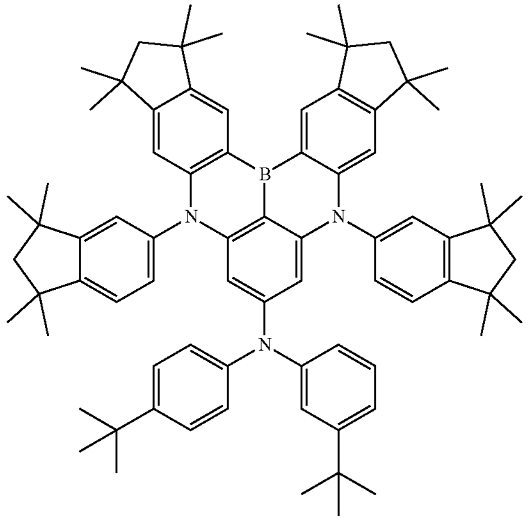
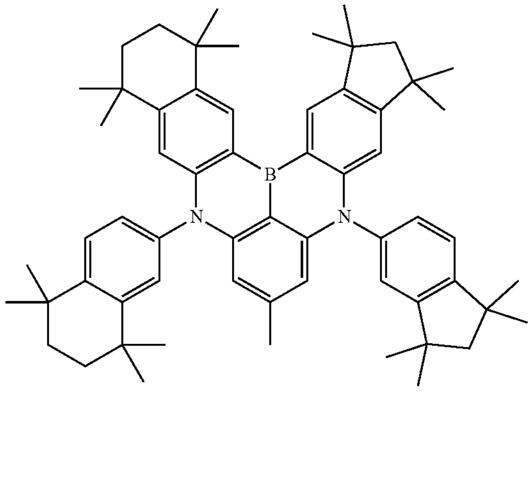
-continued
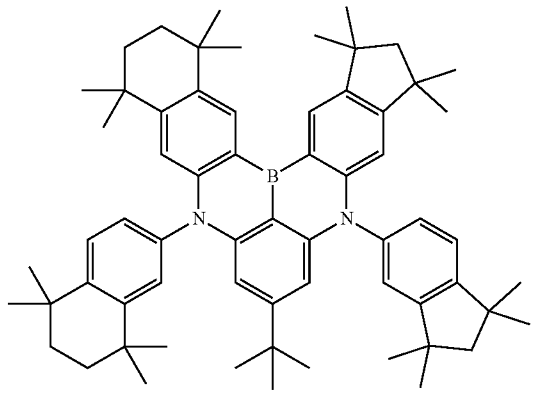
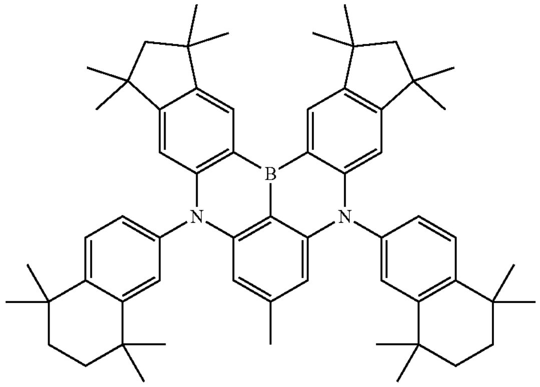
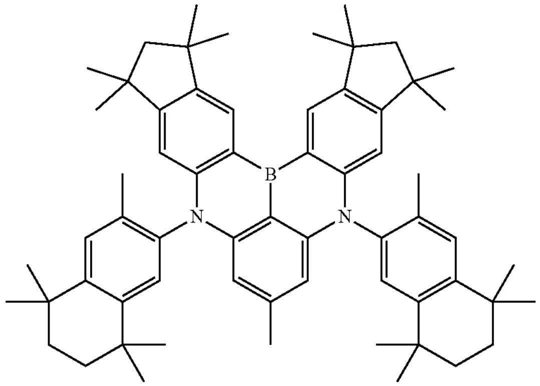
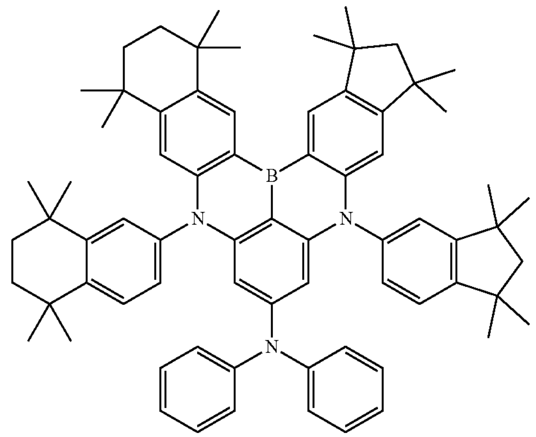

-continued
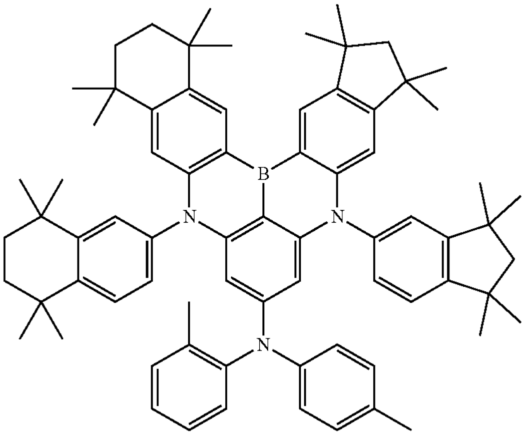
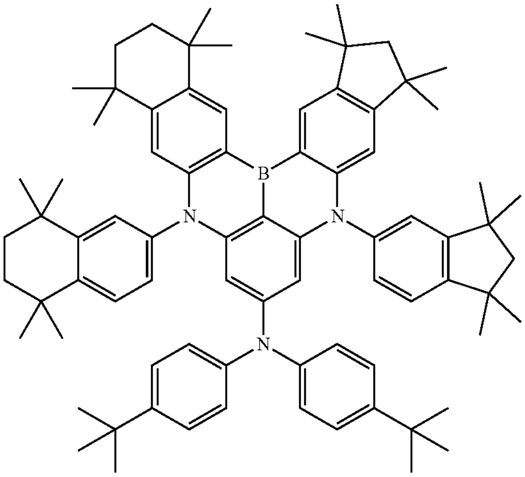
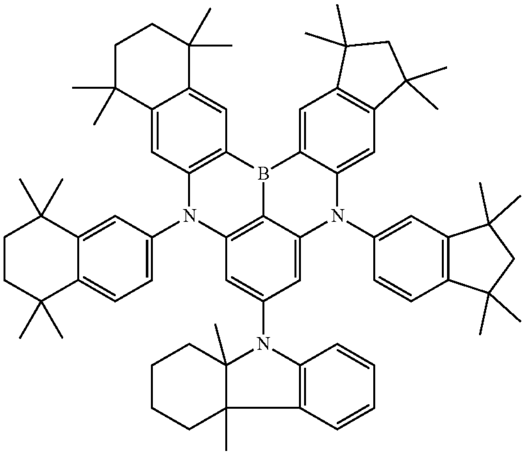 [SMILES: CC1(C)CCC(C)(C)c2cc(N3c4cc5c(cc4B4c6cc7c(cc6N(c6ccc8c(c6)C(C)(C)CC8(C)C)c6cc(N8c9ccccc9C9(C)CCCCC89C)cc3c64)C(C)(C)CC7(C)C)C(C)(C)CCC5(C)C)ccc21]
-continued
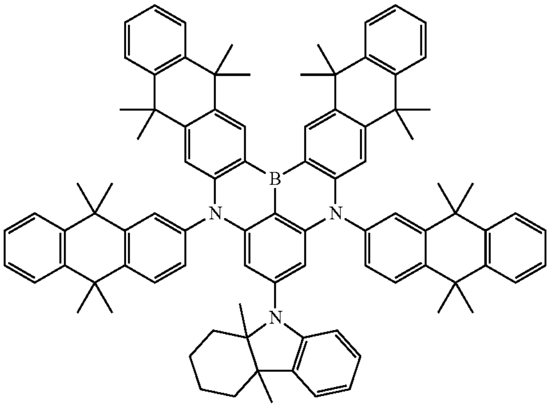
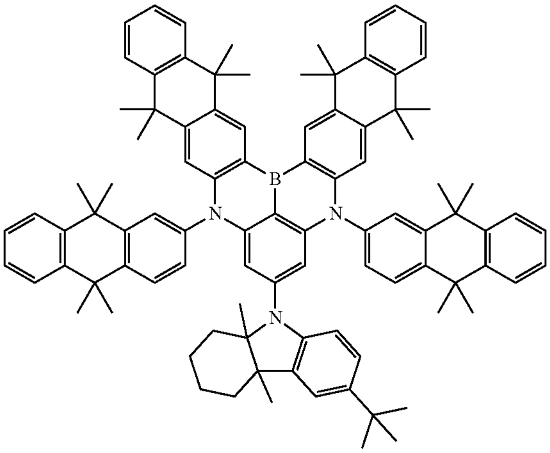
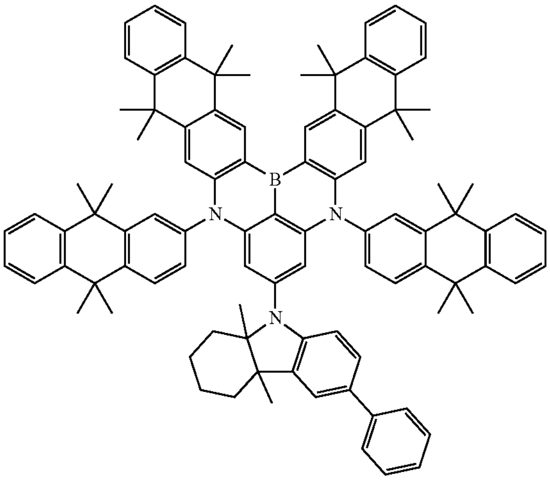

-continued
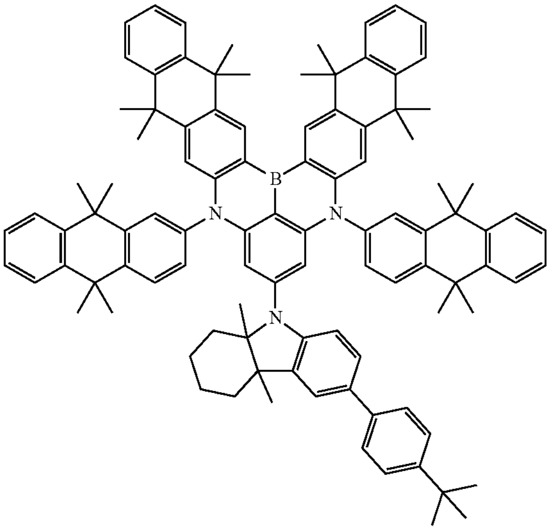 [SMILES: CC(C)(C)c1ccc(-c2ccc3c(c2)C2(C)CCCCC2(C)N3c2cc3c4c(c2)N(c2ccc5c(c2)C(C)(C)c2ccccc2C5(C)C)c2cc5c(cc2B4c2cc4c(cc2N3c2ccc3c(c2)C(C)(C)c2ccccc2C3(C)C)C(C)(C)c2ccccc2C4(C)C)C(C)(C)c2ccccc2C5(C)C)cc1]
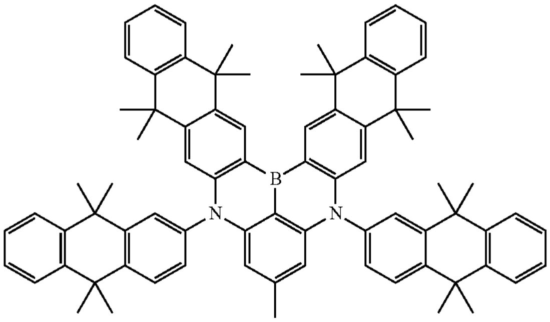
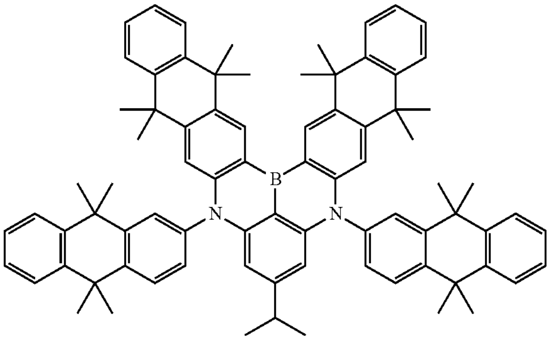
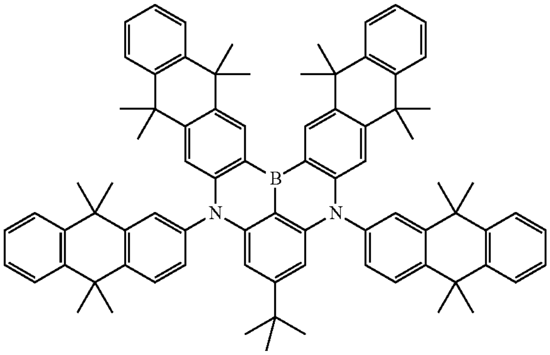
-continued
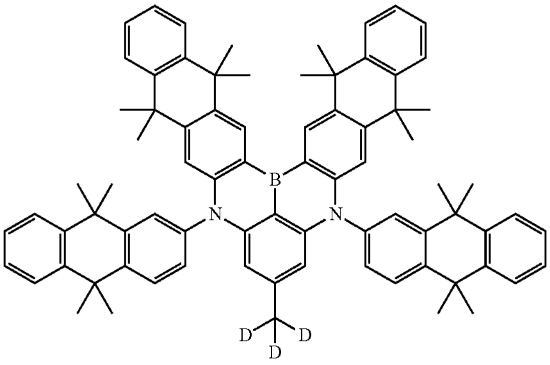
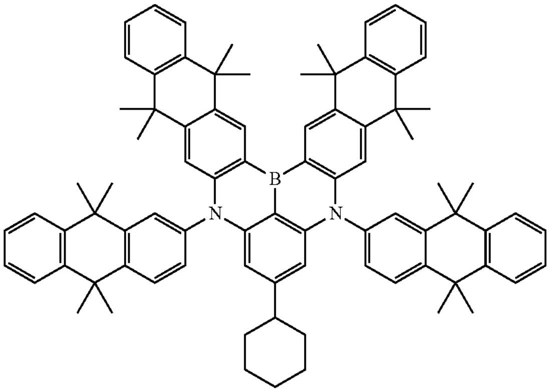
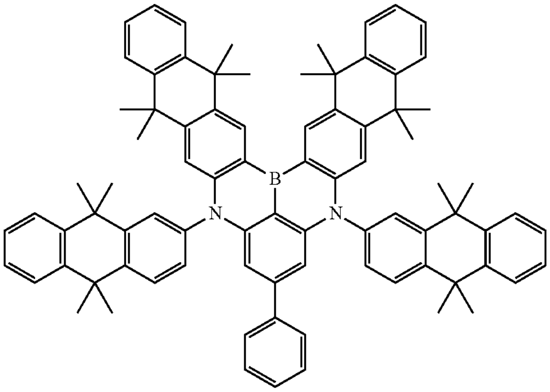
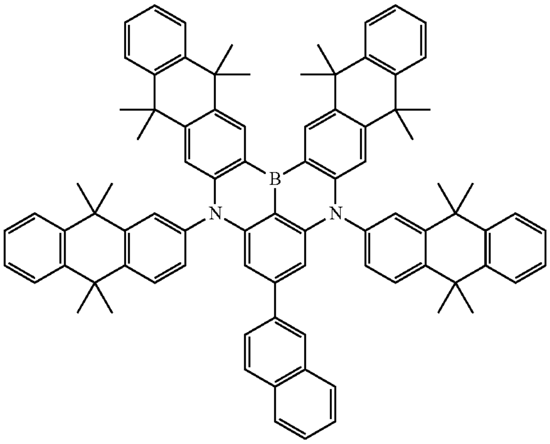

-continued
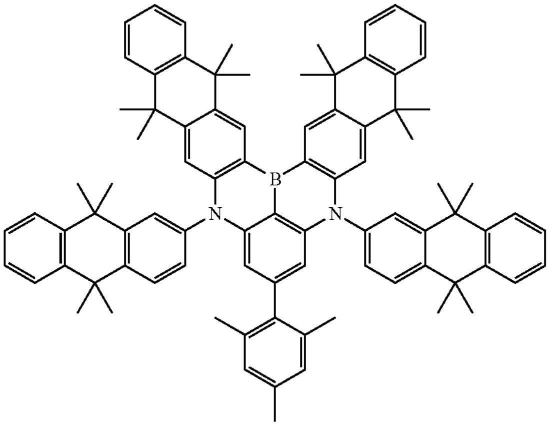
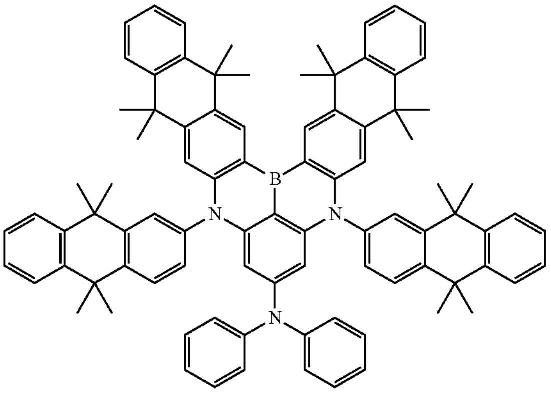
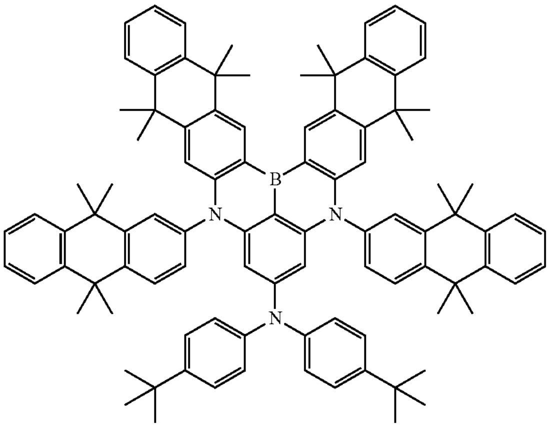
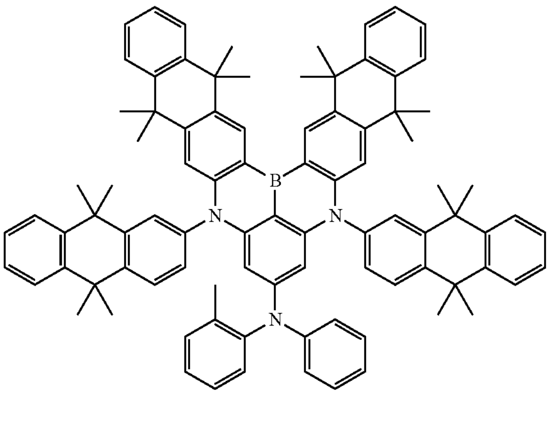
-continued
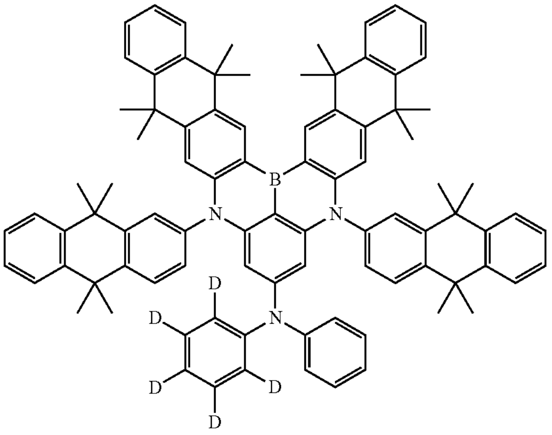
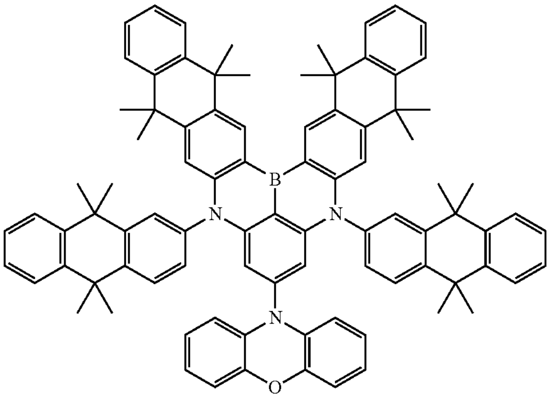
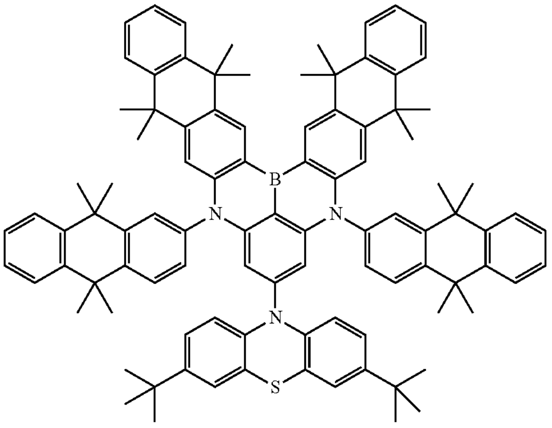
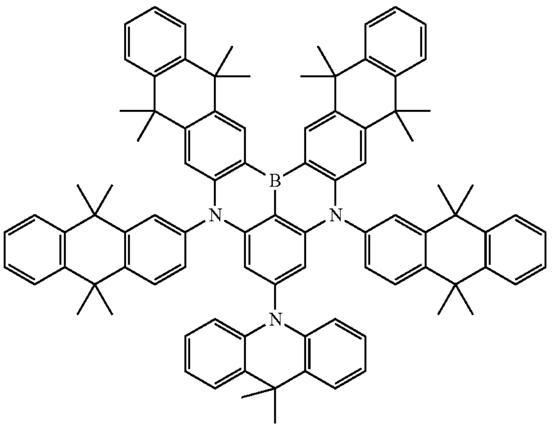

-continued
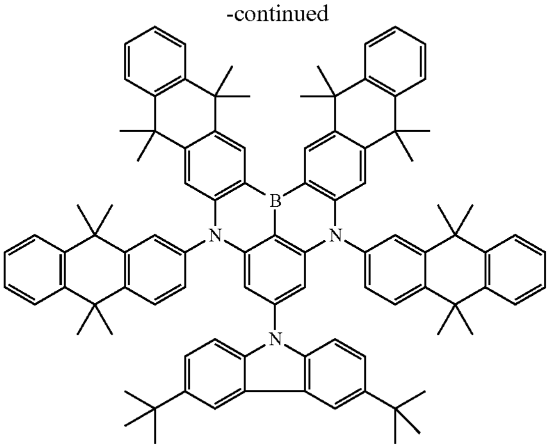
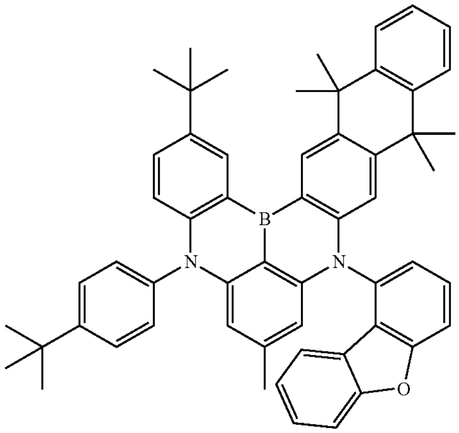
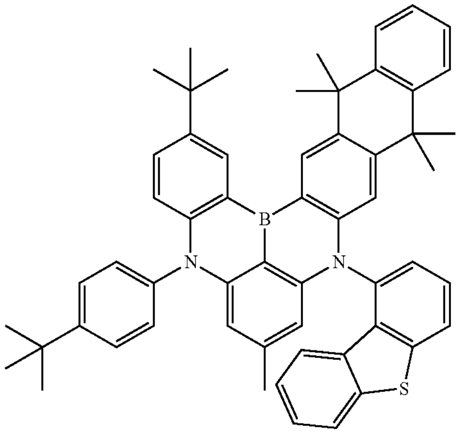
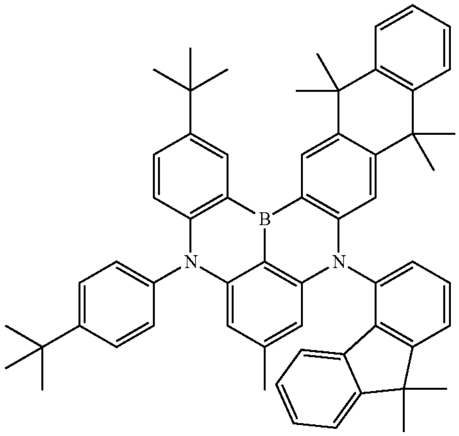
-continued
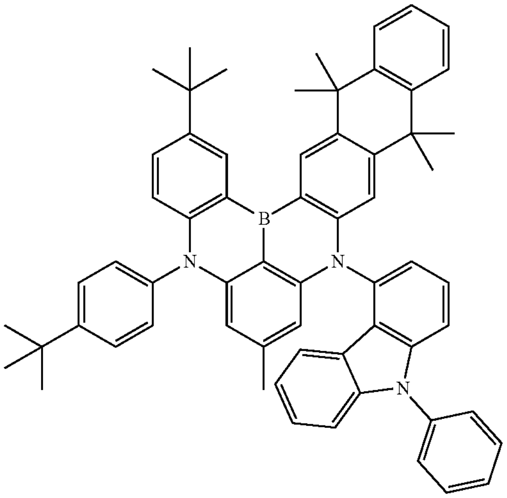
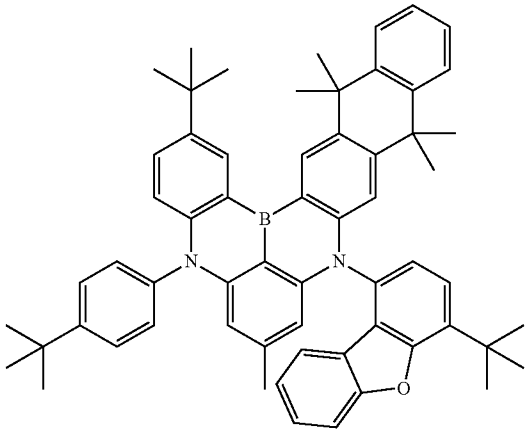
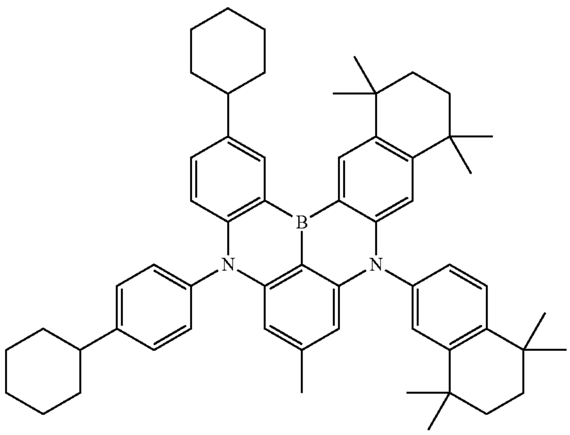

-continued
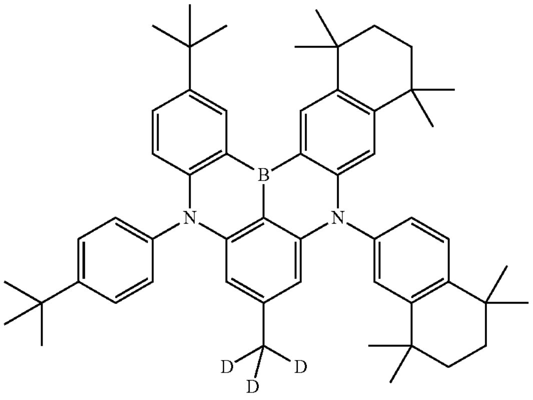
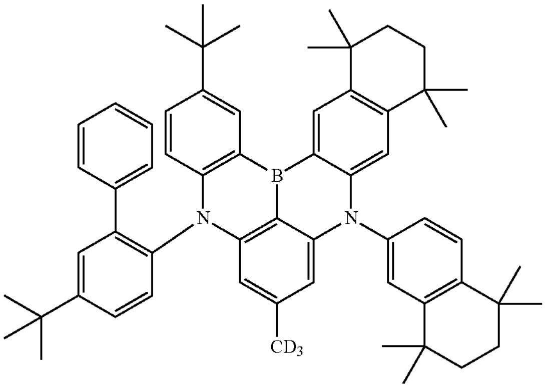
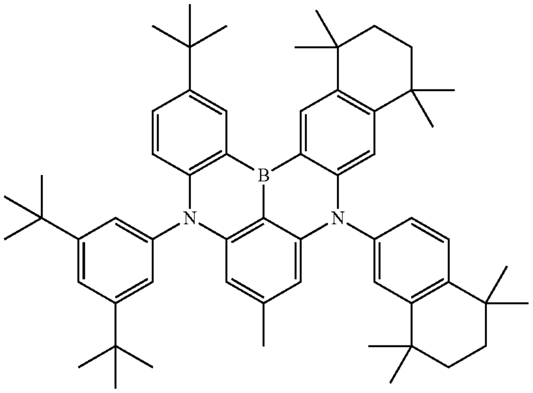
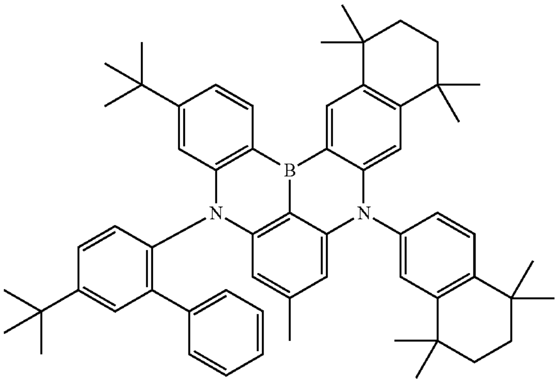
-continued
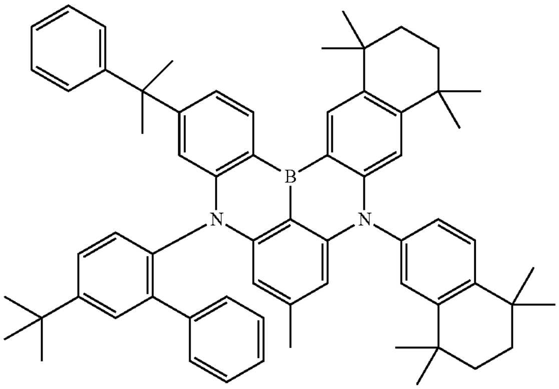
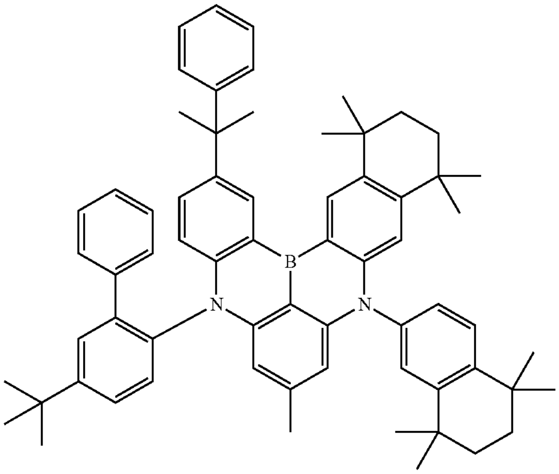
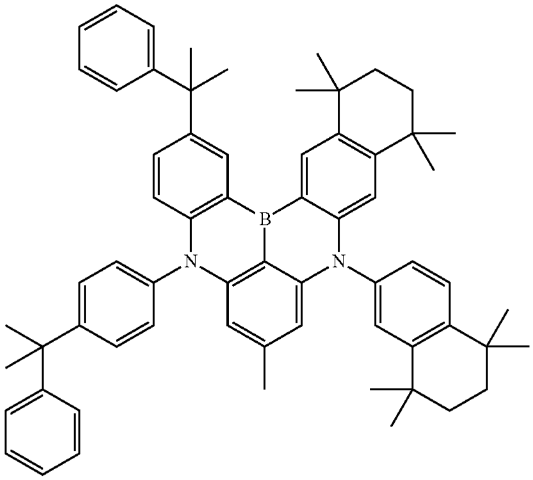

-continued
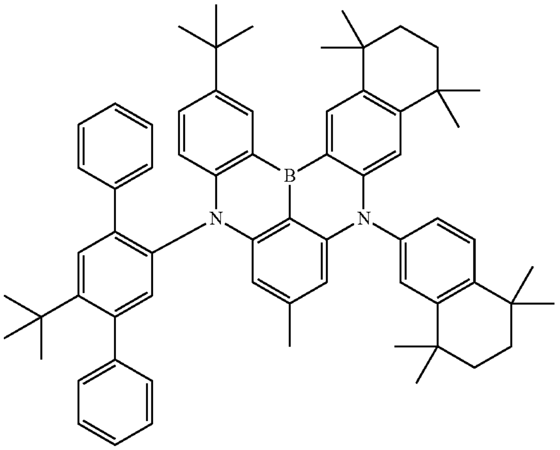
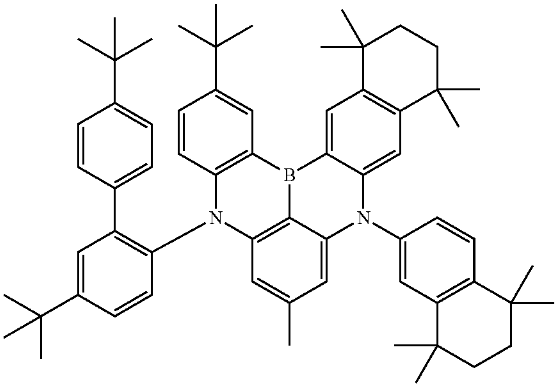
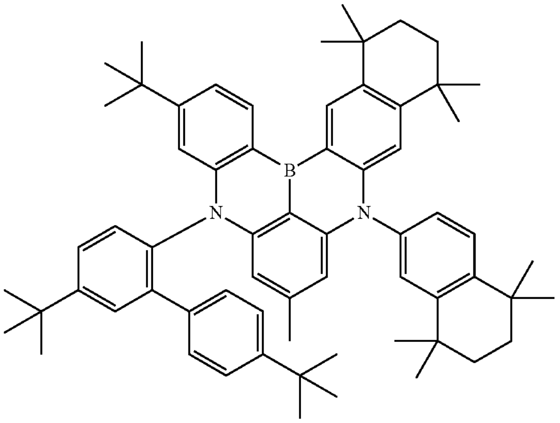
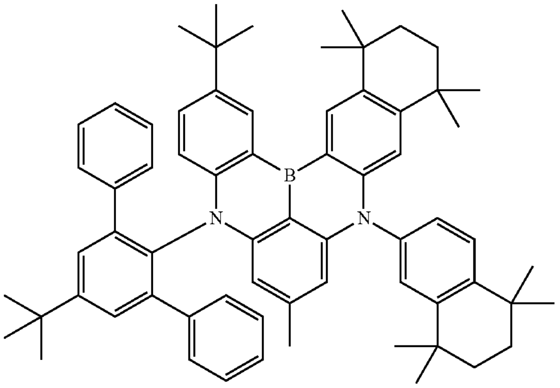
-continued
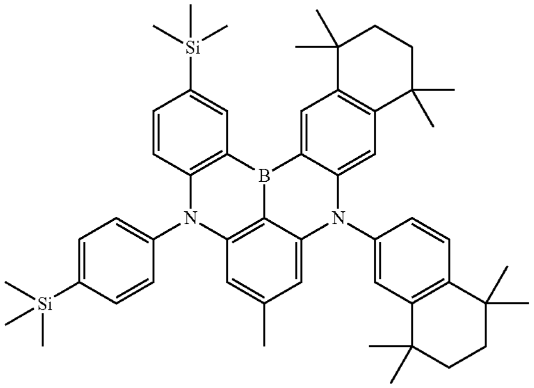
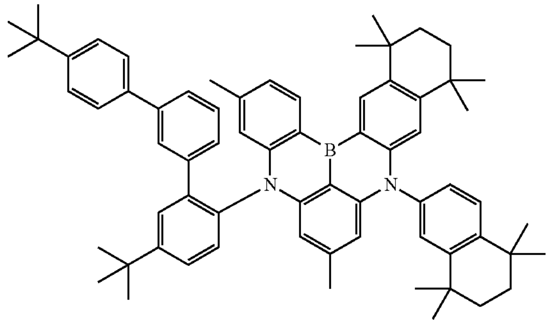
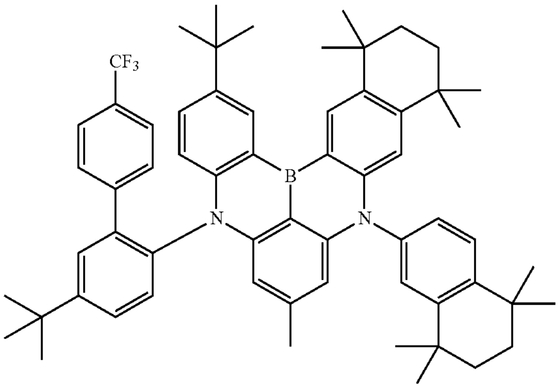
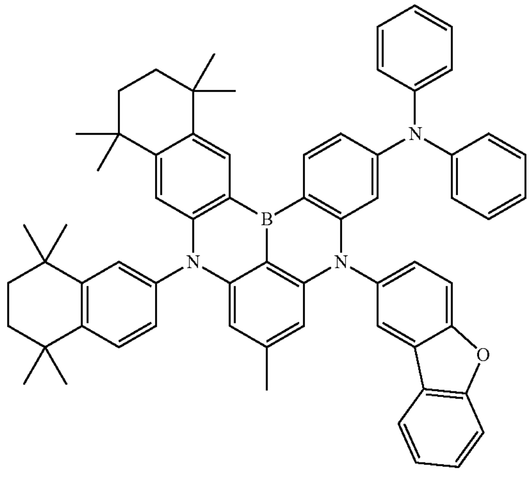

-continued
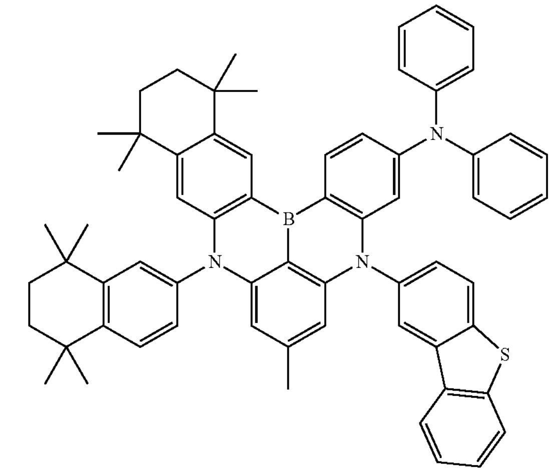
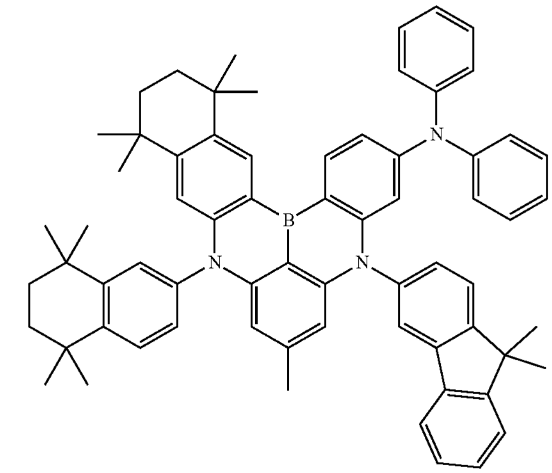
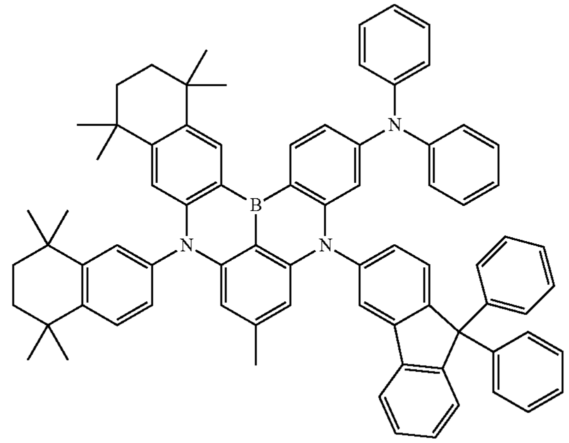 [SMILES: Cc1cc2c3c(c1)N(c1ccc4c(c1)C(C)(C)CCC4(C)C)c1cc4c(cc1B3c1ccc(N(c3ccccc3)c3ccccc3)cc1N2c1ccc2c(c1)-c1ccccc1C2(c1ccccc1)c1ccccc1)C(C)(C)CCC4(C)C]
-continued
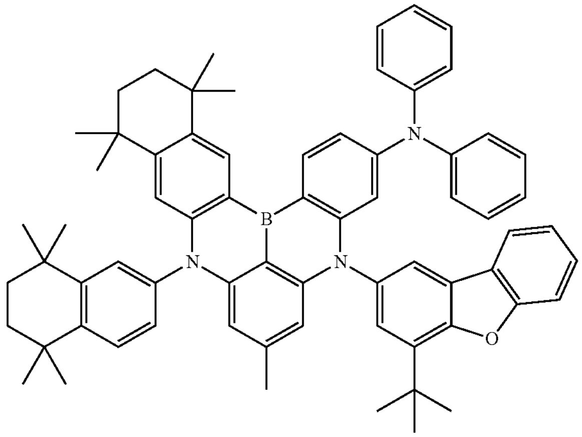
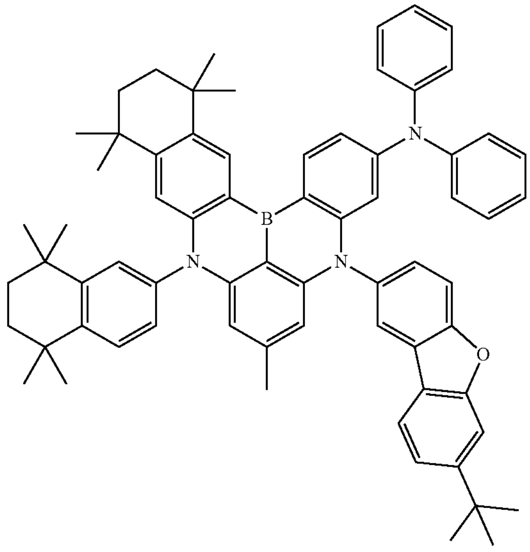
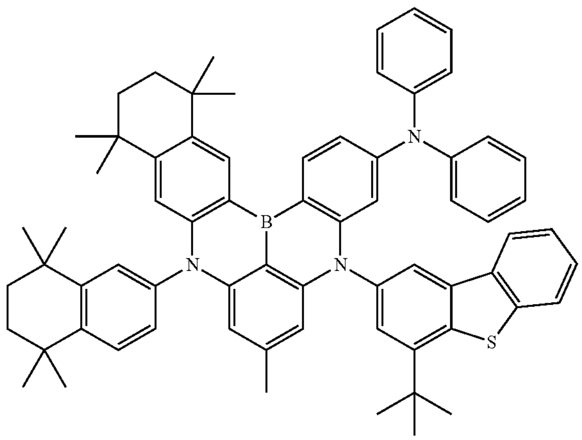

-continued
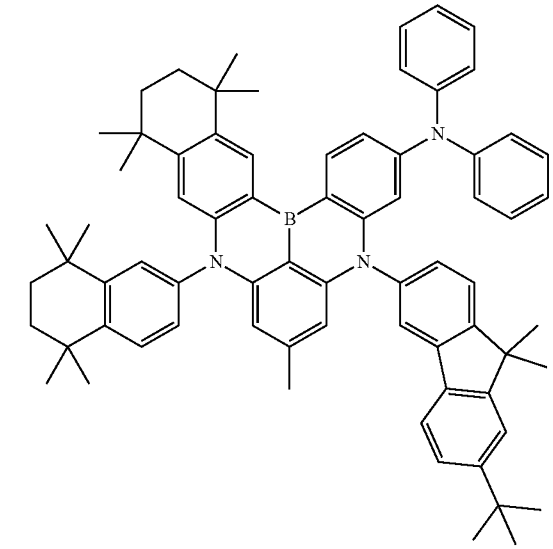 [SMILES: Cc1cc2c3c(c1)N(c1ccc4c(c1)C(C)(C)CCC4(C)C)c1cc4c(cc1B3c1ccc(N(c3ccccc3)c3ccccc3)cc1N2c1ccc2c(c1)-c1ccc(C(C)(C)C)cc1C2(C)C)C(C)(C)CCC4(C)C]
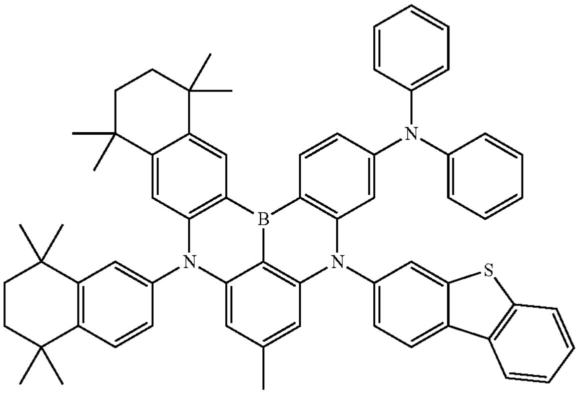
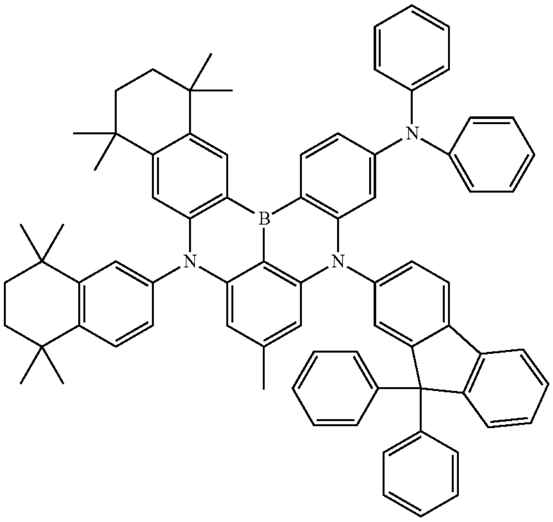 [SMILES: Cc1cc2c3c(c1)N(c1ccc4c(c1)C(C)(C)CCC4(C)C)c1cc4c(cc1B3c1ccc(N(c3ccccc3)c3ccccc3)cc1N2c1ccc2c(c1)C(c1ccccc1)(c1ccccc1)c1ccccc1-2)C(C)(C)CCC4(C)C]
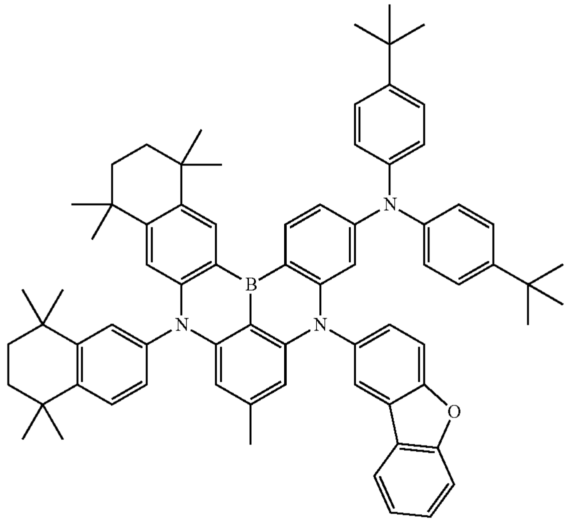
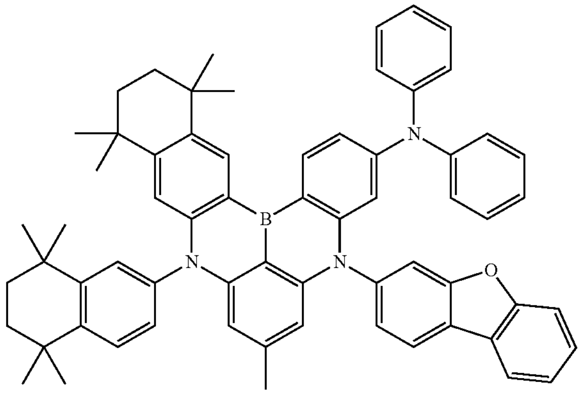
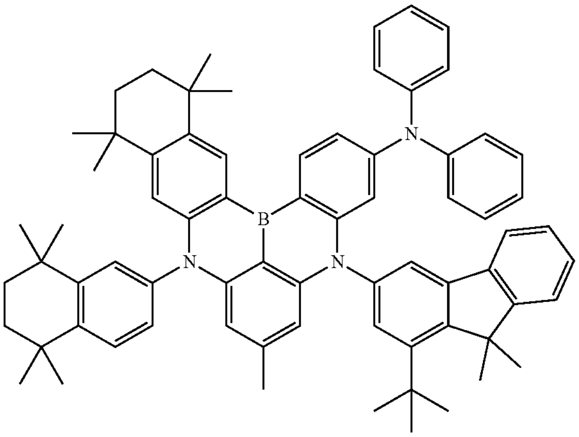

-continued
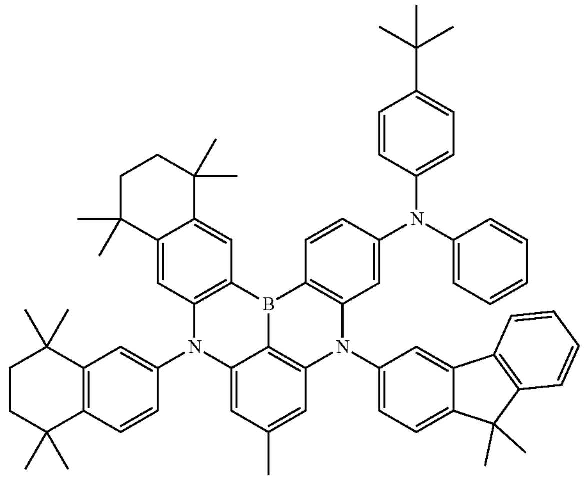
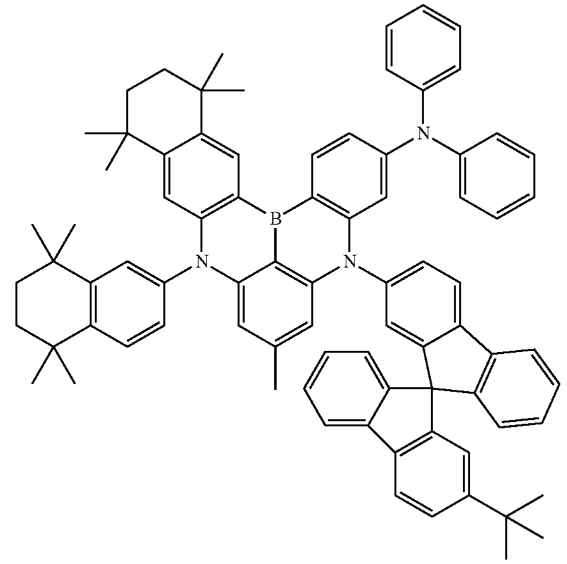
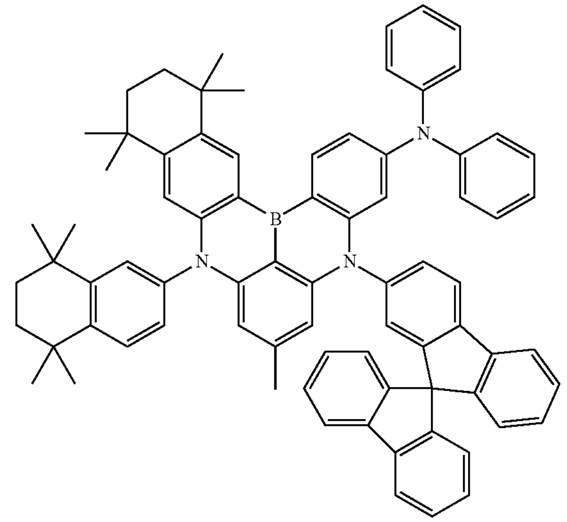 [SMILES: Cc1cc2c3c(c1)N(c1ccc4c(c1)C(C)(C)CCC4(C)C)c1cc4c(cc1B3c1ccc(N(c3ccccc3)c3ccccc3)cc1N2c1ccc2c(c1)C1(c3ccccc3-c3ccccc31)c1ccccc1-2)C(C)(C)CCC4(C)C]
-continued
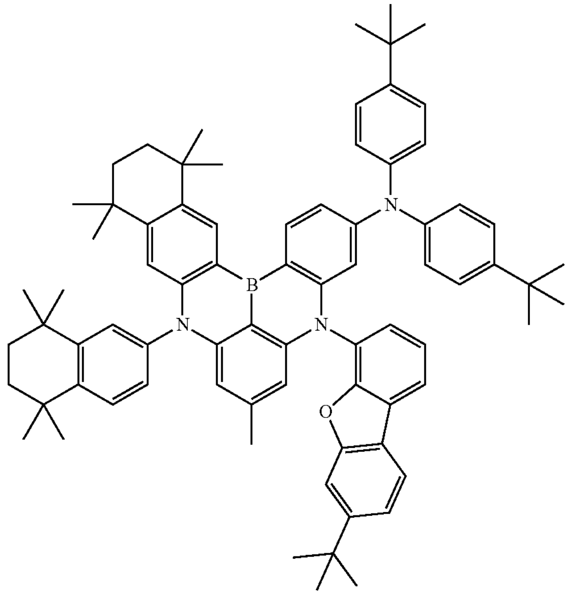
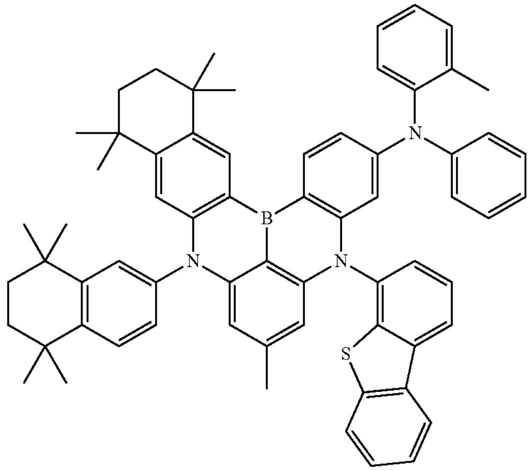
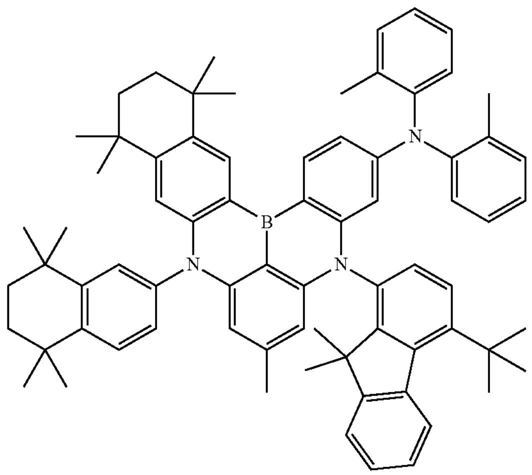

-continued
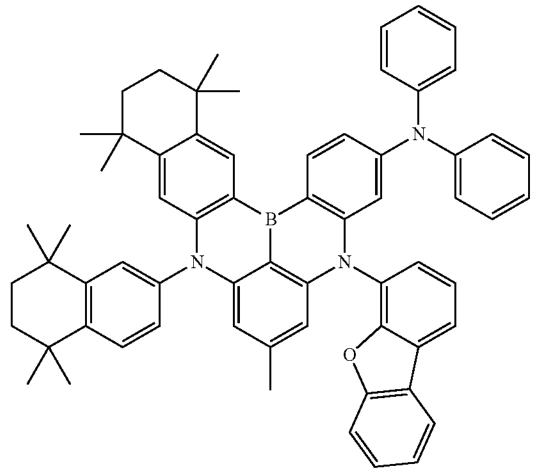 [SMILES: Cc1cc2c3c(c1)N(c1cccc4c1oc1ccccc14)c1cc(N(c4ccccc4)c4ccccc4)ccc1B3c1cc3c(cc1N2c1ccc2c(c1)C(C)(C)CCC2(C)C)C(C)(C)CCC3(C)C]
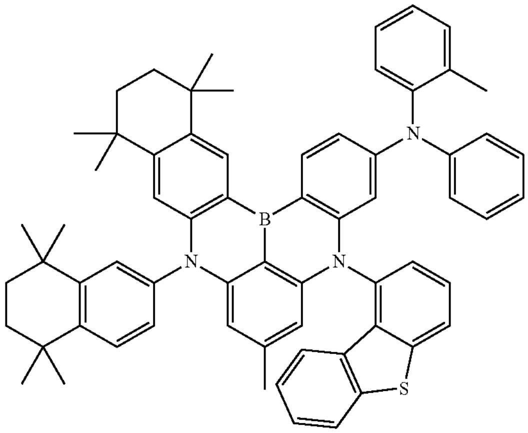
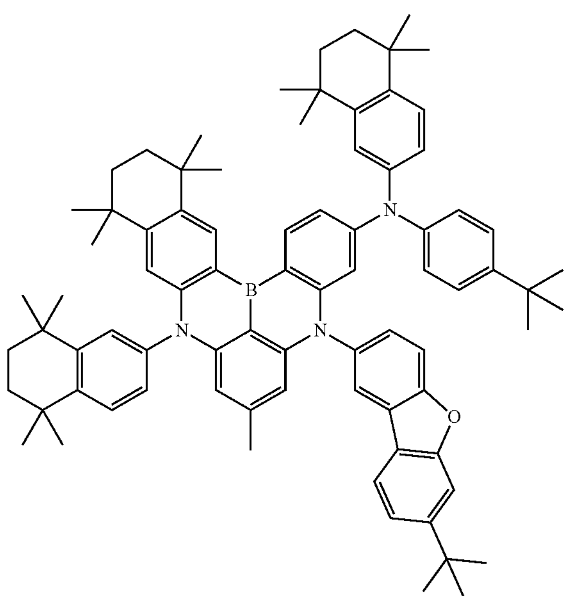
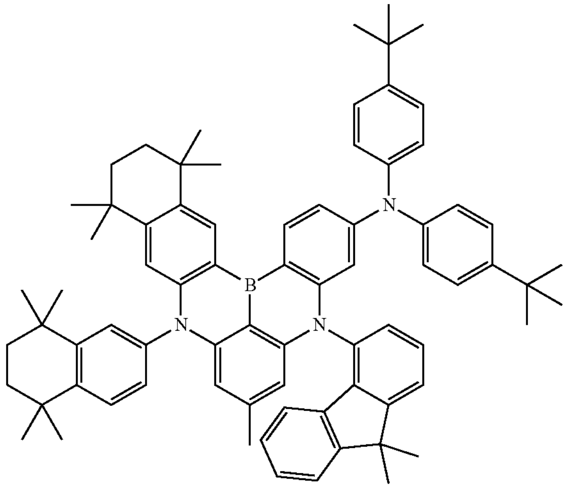 [SMILES: Cc1cc2c3c(c1)N(c1cccc4c1-c1ccccc1C4(C)C)c1cc(N(c4ccc(C(C)(C)C)cc4)c4ccc(C(C)(C)C)cc4)ccc1B3c1cc3c(cc1N2c1ccc2c(c1)C(C)(C)CCC2(C)C)C(C)(C)CCC3(C)C]
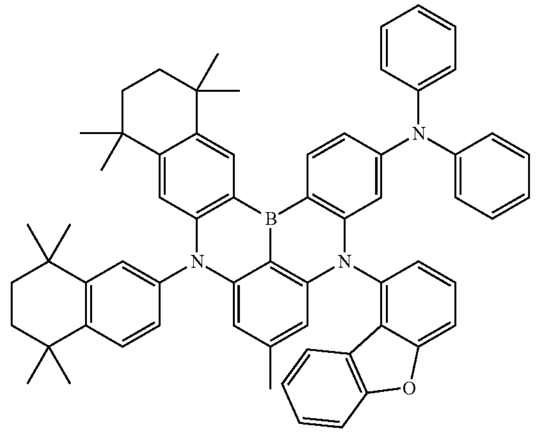
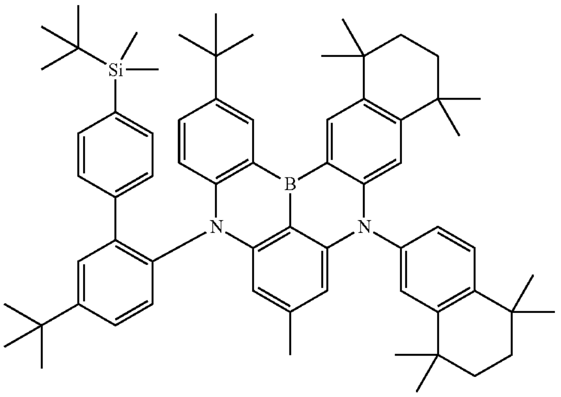
-continued -continued
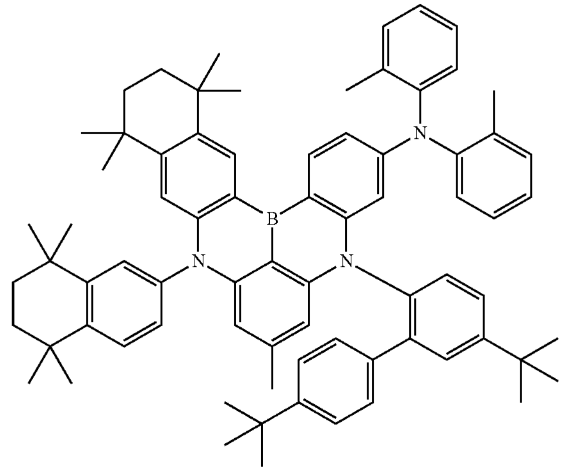
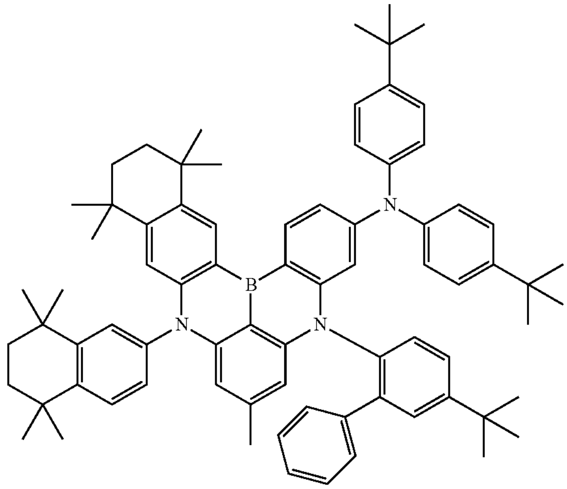
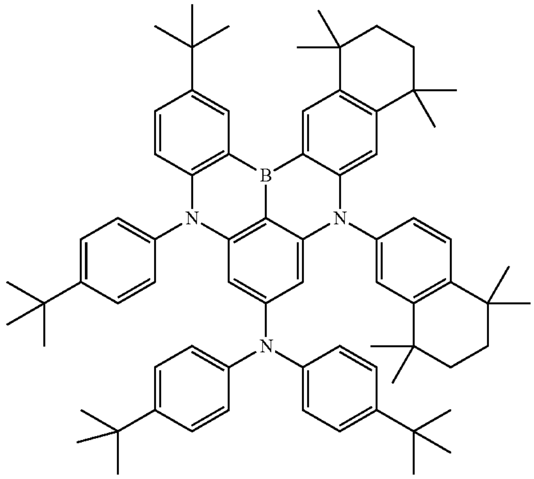 [SMILES: CC(C)(C)c1ccc(N(c2ccc(C(C)(C)C)cc2)c2cc3c4c(c2)N(c2ccc5c(c2)C(C)(C)CCC5(C)C)c2cc5c(cc2B4c2cc(C(C)(C)C)ccc2N3c2ccc(C(C)(C)C)cc2)C(C)(C)CCC5(C)C)cc1]
-continued
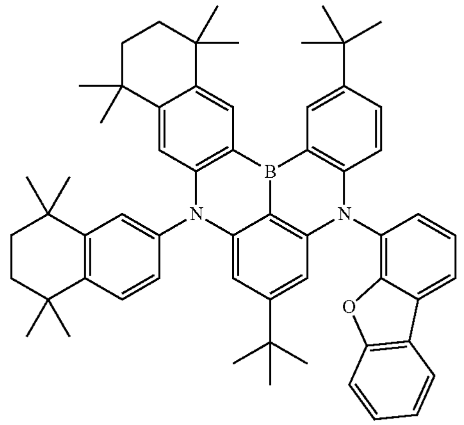
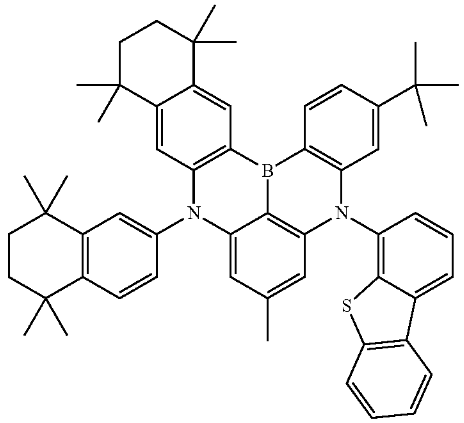
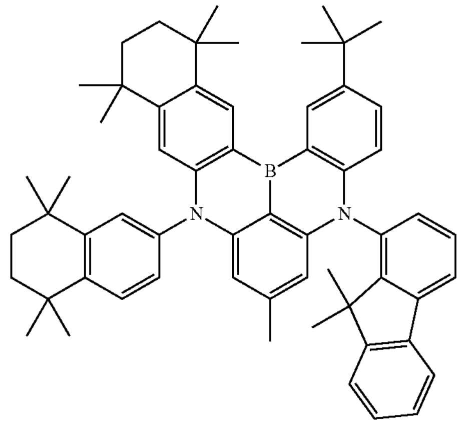
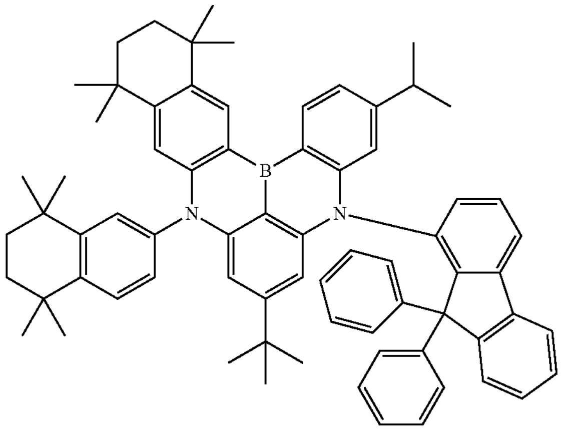

-continued
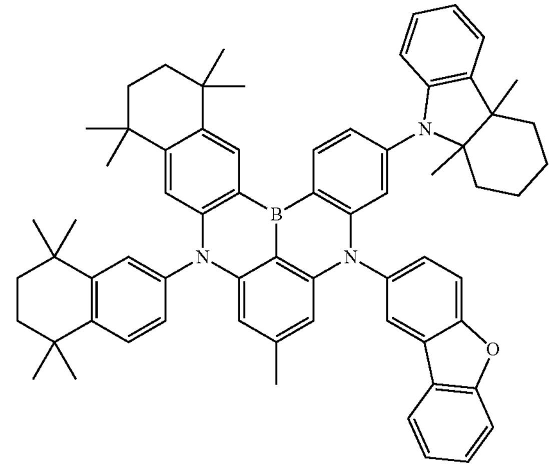
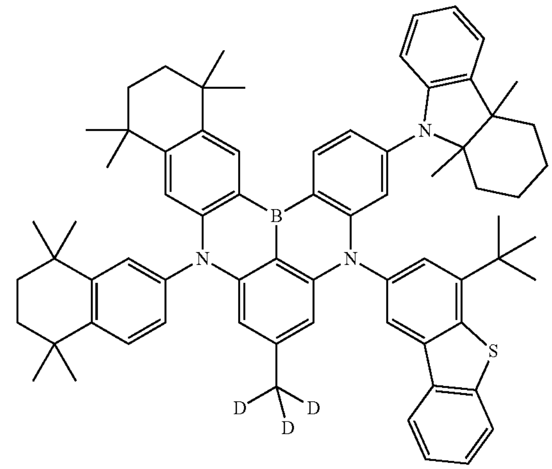
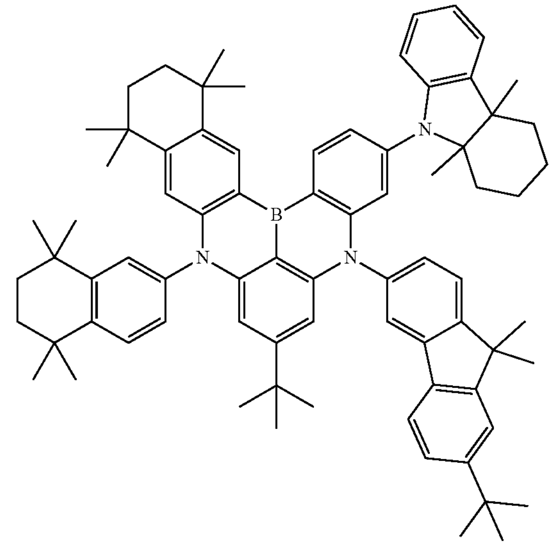
-continued
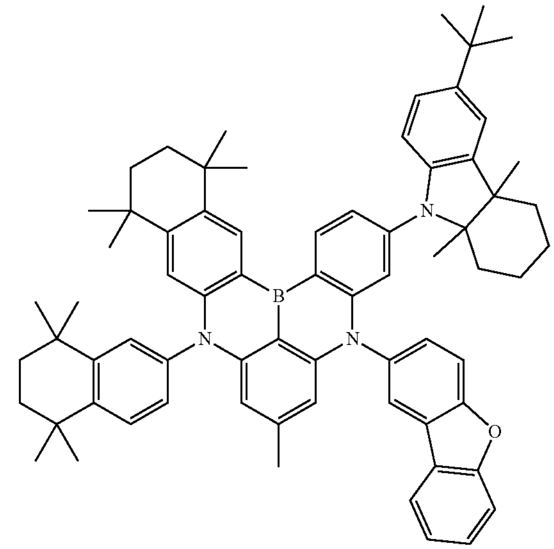 [SMILES: Cc1cc2c3c(c1)N(c1ccc4c(c1)C(C)(C)CCC4(C)C)c1cc4c(cc1B3c1ccc(N3c5ccc(C(C)(C)C)cc5C5(C)CCCCC35C)cc1N2c1ccc2oc3ccccc3c2c1)C(C)(C)CCC4(C)C]
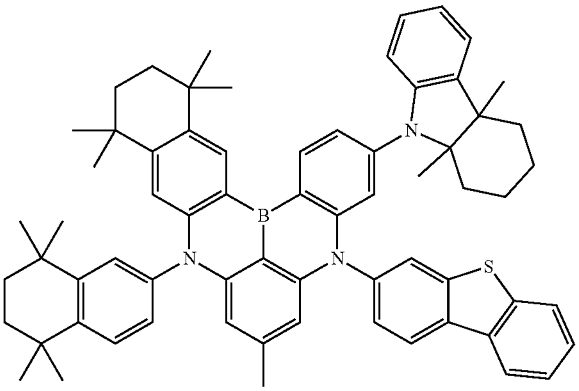
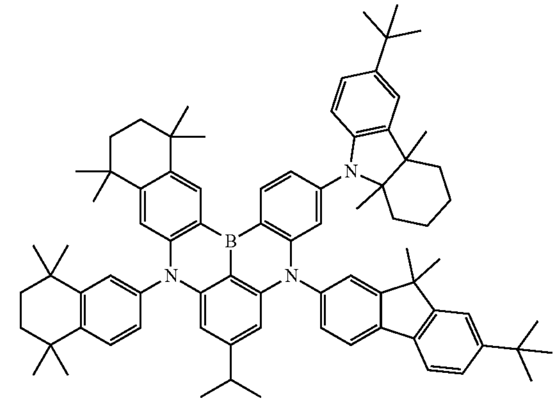

-continued
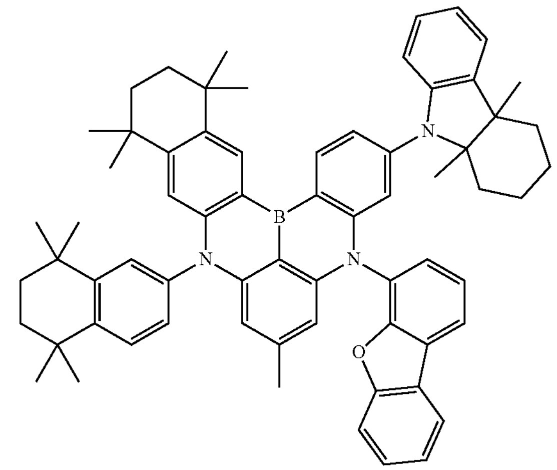
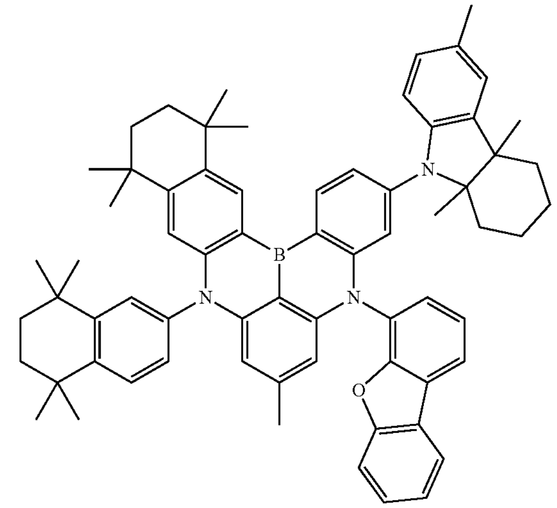
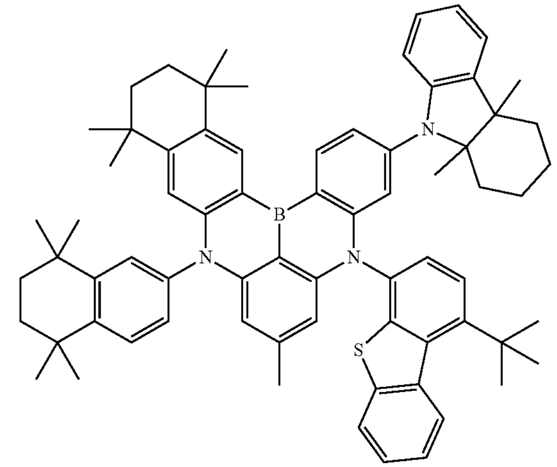
-continued
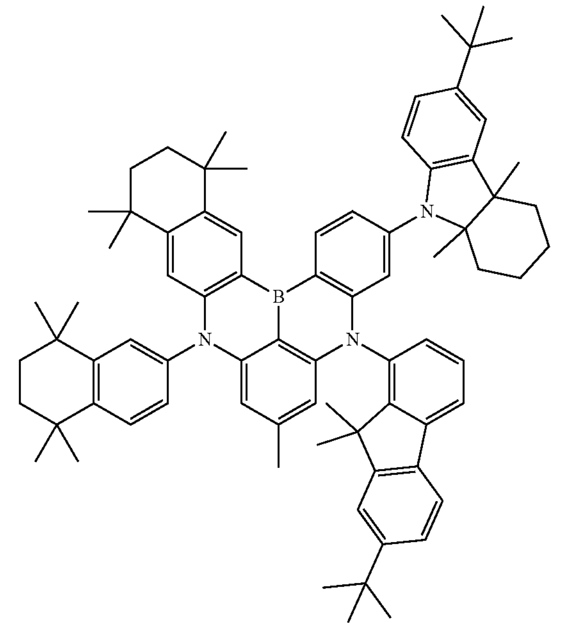
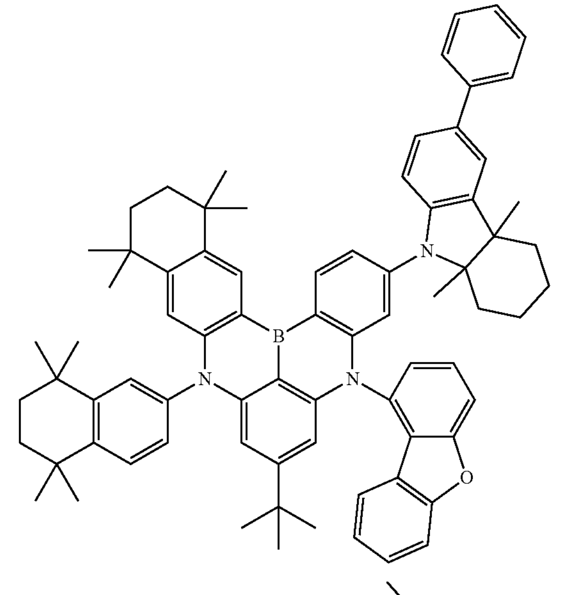
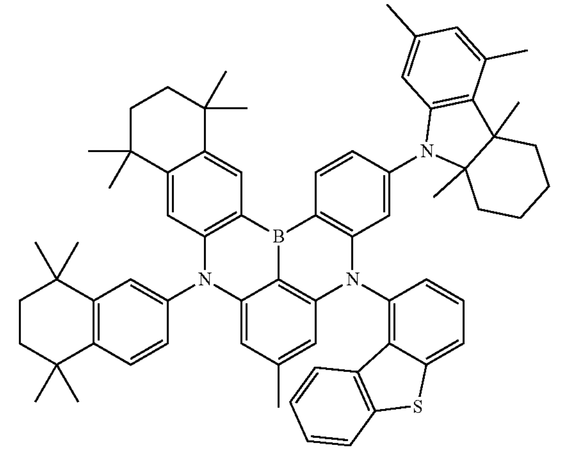 [SMILES: Cc1cc2c3c(c1)N(c1cccc4sc5ccccc5c14)c1cc(N4c5cc(C)cc(C)c5C5(C)CCCCC45C)ccc1B3c1cc3c(cc1N2c1ccc2c(c1)C(C)(C)CCC2(C)C)C(C)(C)CCC3(C)C]

-continued
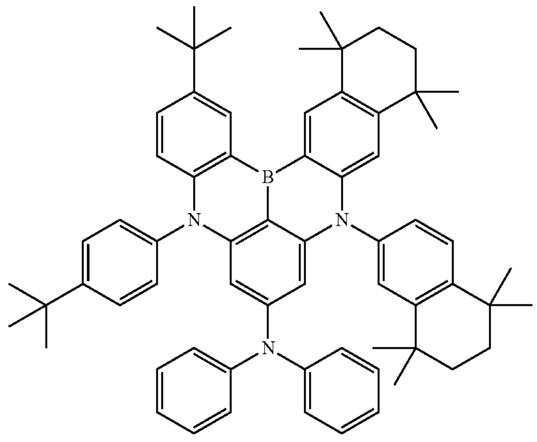
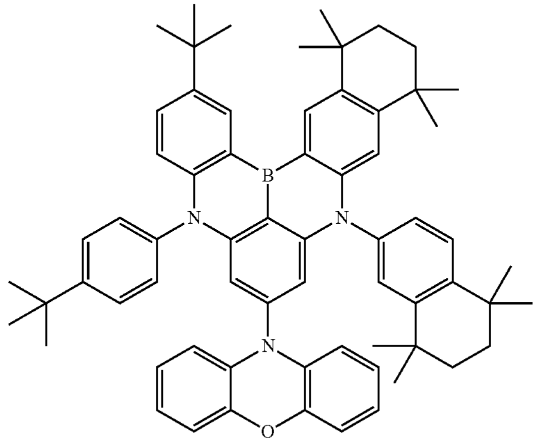
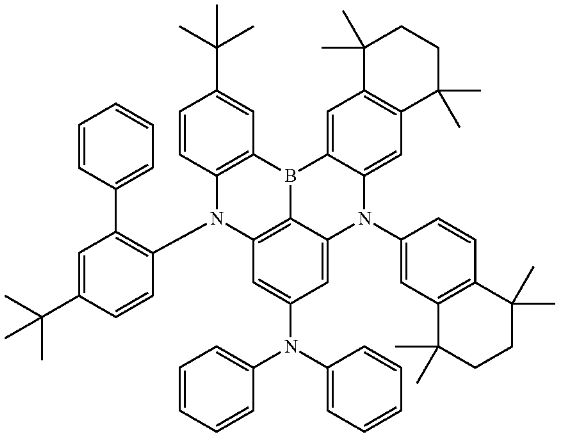
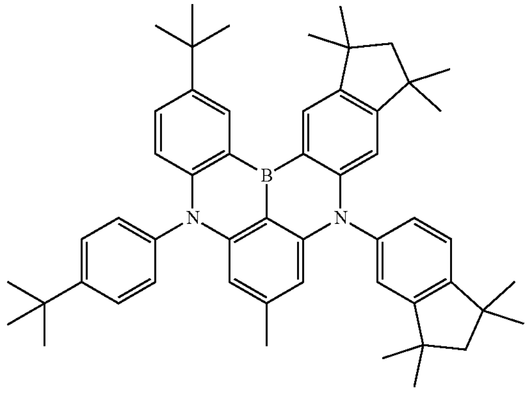
-continued
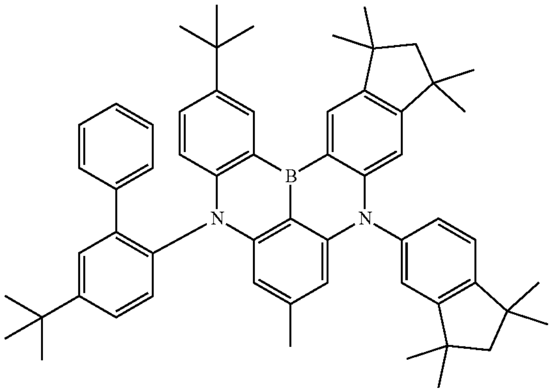
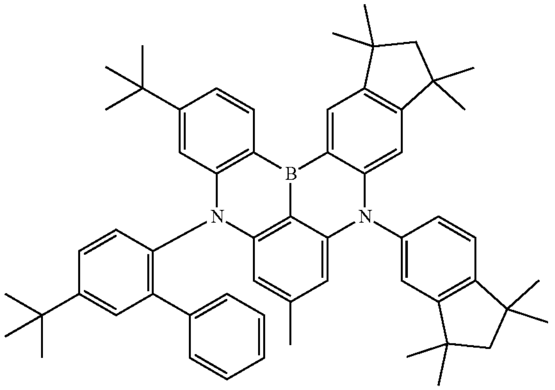
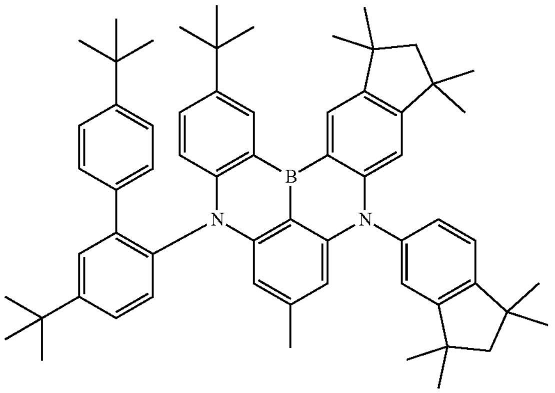
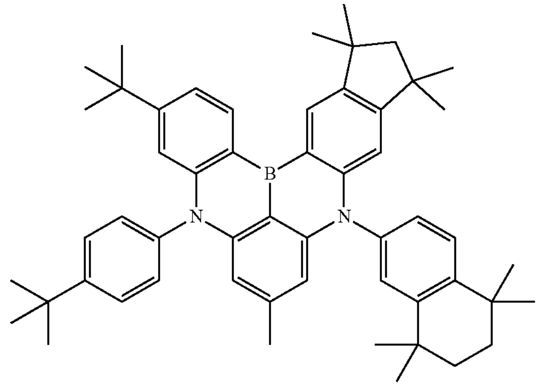

-continued
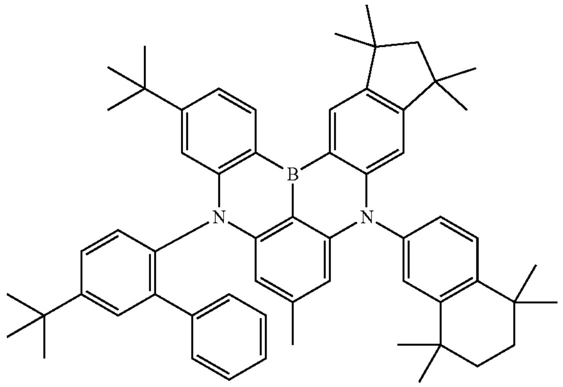
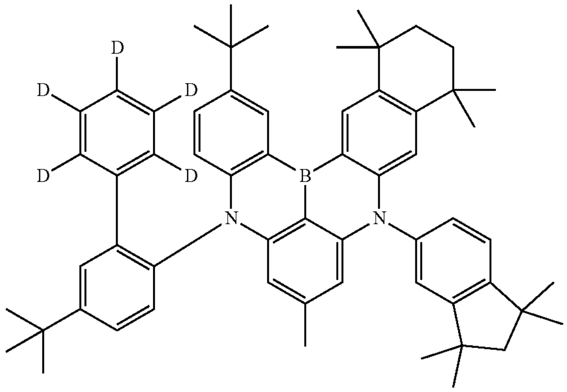
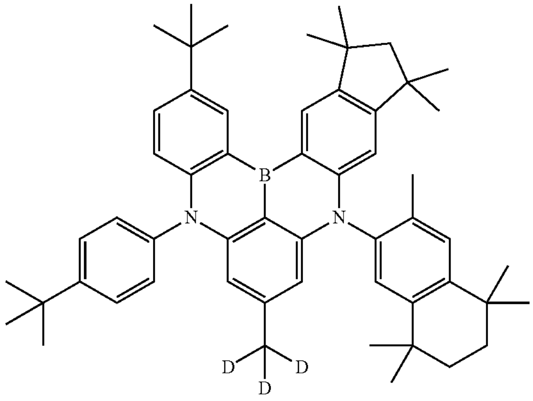
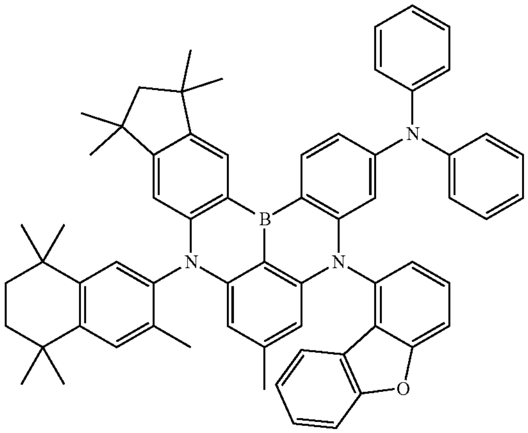
-continued
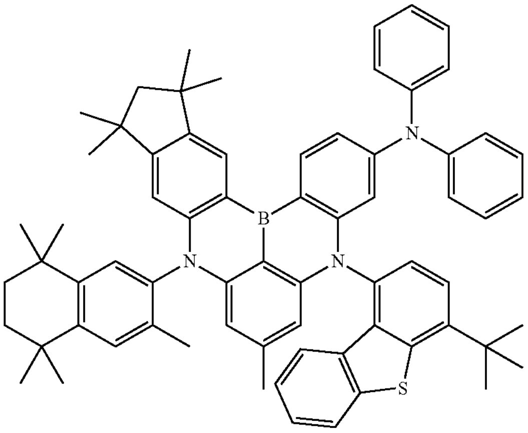
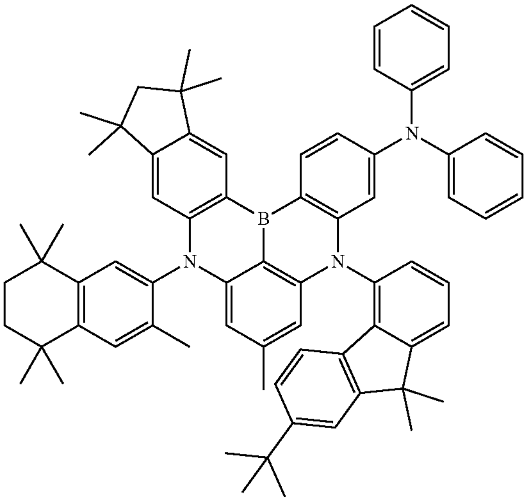
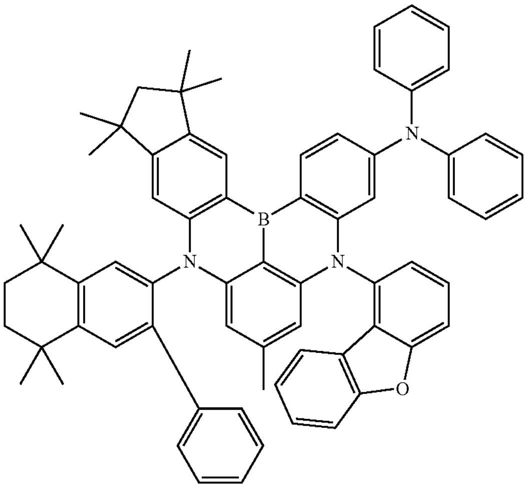 [SMILES: Cc1cc2c3c(c1)N(c1cccc4oc5ccccc5c14)c1cc(N(c4ccccc4)c4ccccc4)ccc1B3c1cc3c(cc1N2c1cc2c(cc1-c1ccccc1)C(C)(C)CCC2(C)C)C(C)(C)CC3(C)C]

-continued
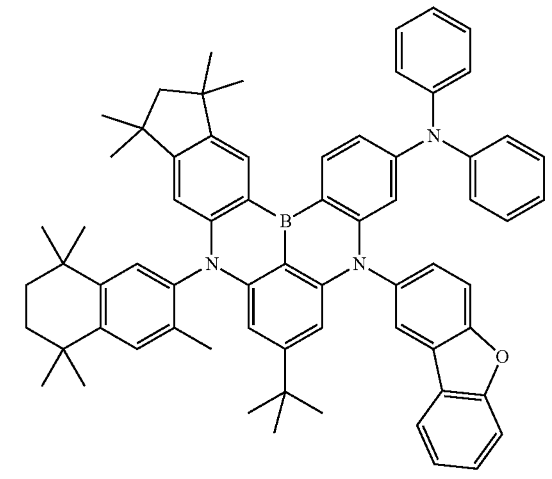
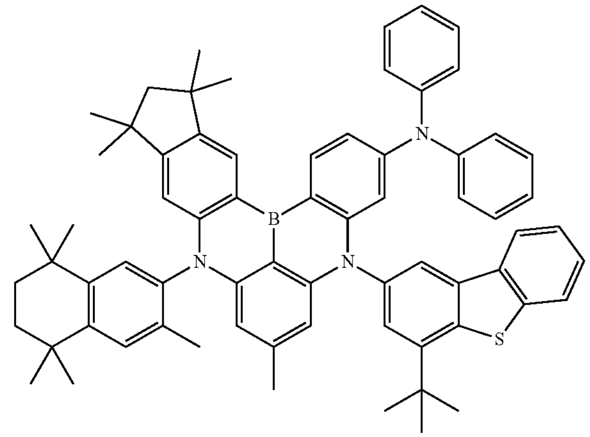
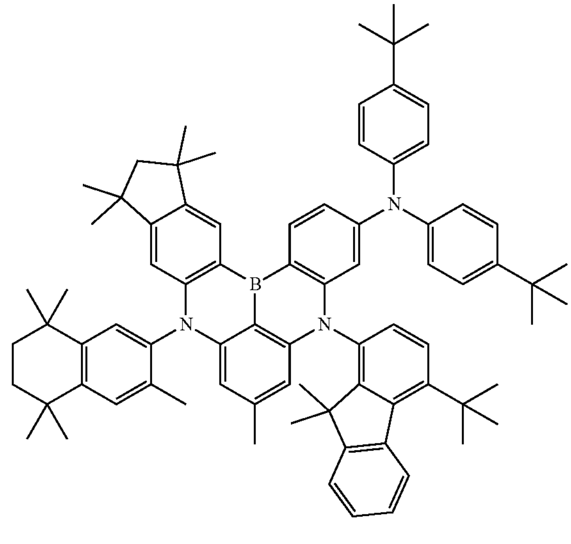
-continued
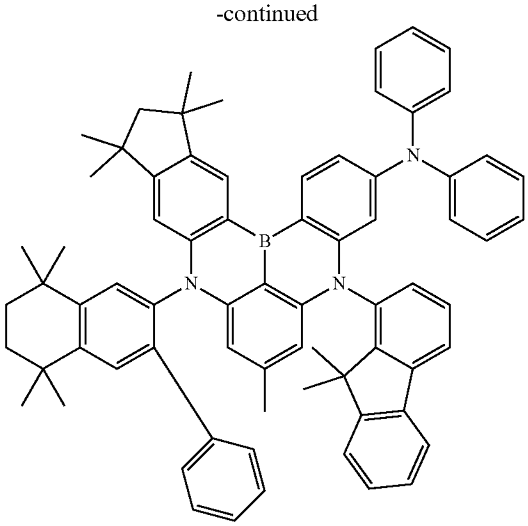
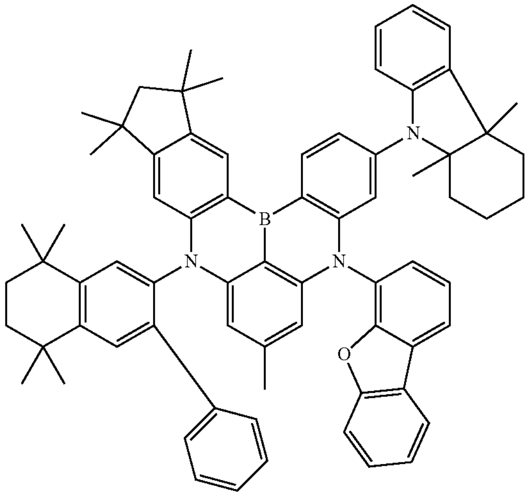
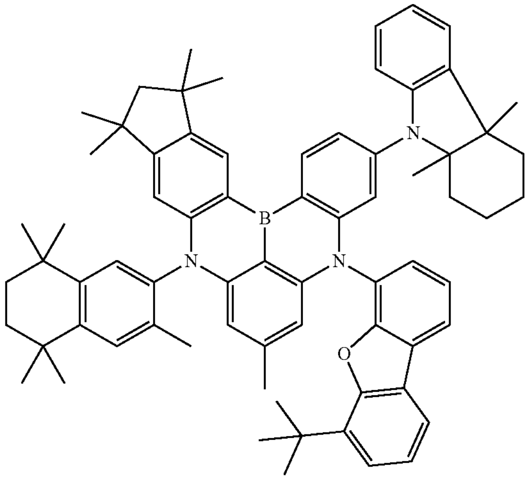

-continued
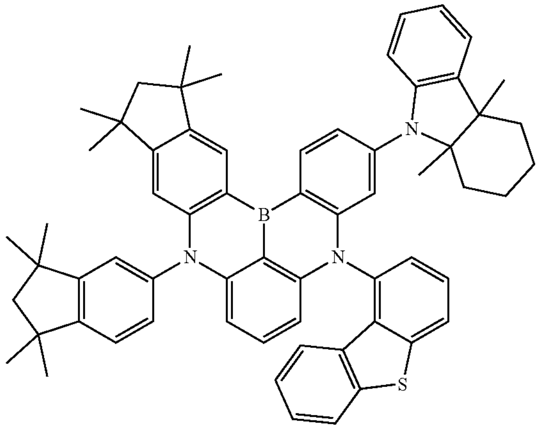
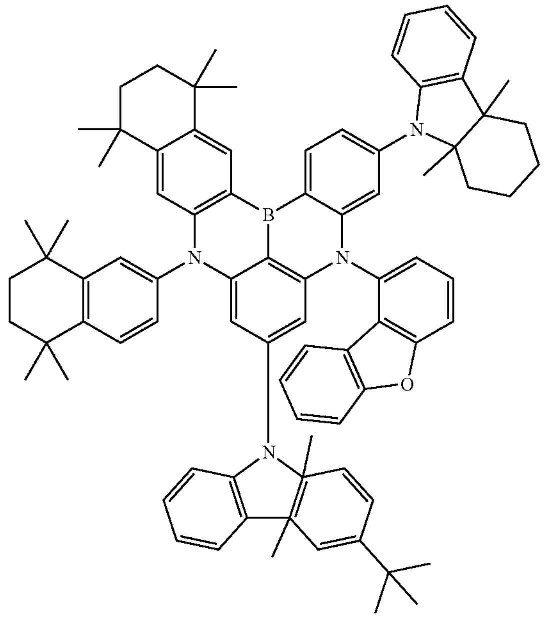
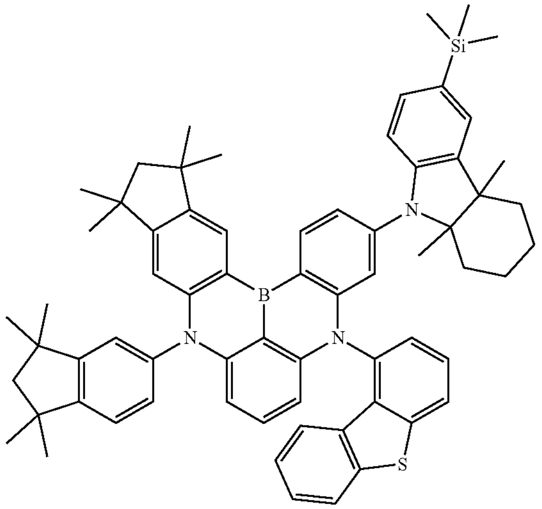 [SMILES: CC1(C)CC(C)(C)c2cc(N3c4cc5c(cc4B4c6ccc(N7c8ccc([Si](C)(C)C)cc8C8(C)CCCCC78C)cc6N(c6cccc7sc8ccccc8c67)c6cccc3c64)C(C)(C)CC5(C)C)ccc21]
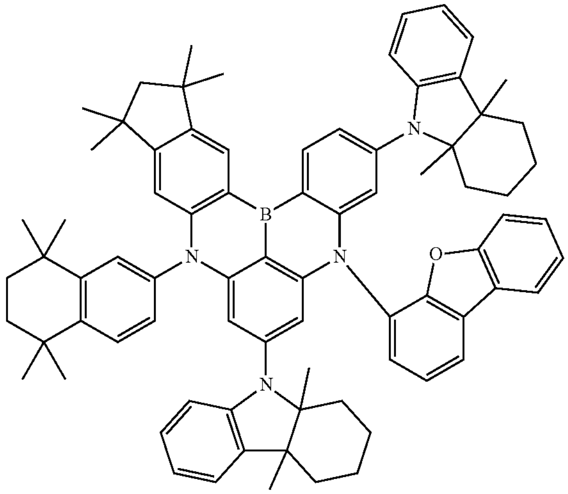
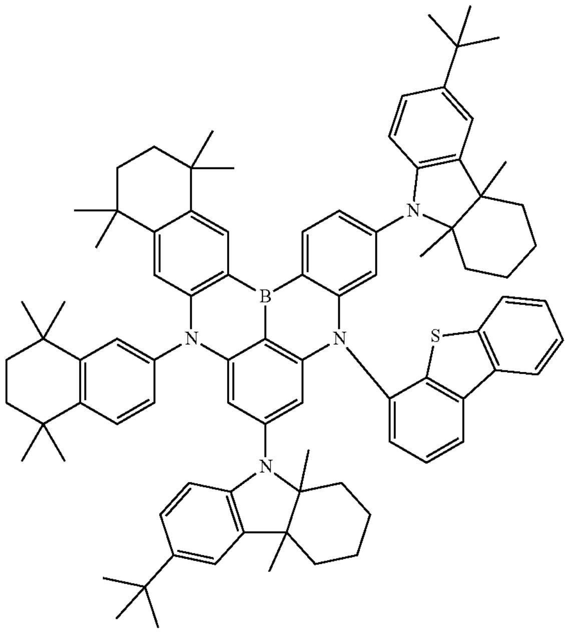
-continued -continued
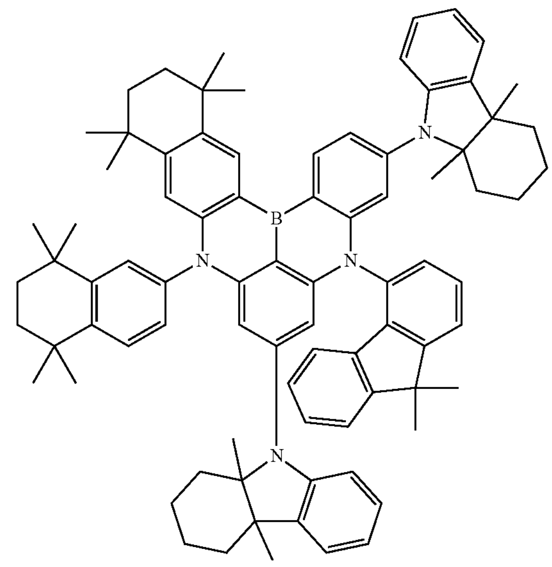 [SMILES: CC1(C)CCC(C)(C)c2cc(N3c4cc5c(cc4B4c6ccc(N7c8ccccc8C8(C)CCCCC78C)cc6N(c6cccc7c6-c6ccccc6C7(C)C)c6cc(N7c8ccccc8C8(C)CCCCC78C)cc3c64)C(C)(C)CCC5(C)C)ccc21]
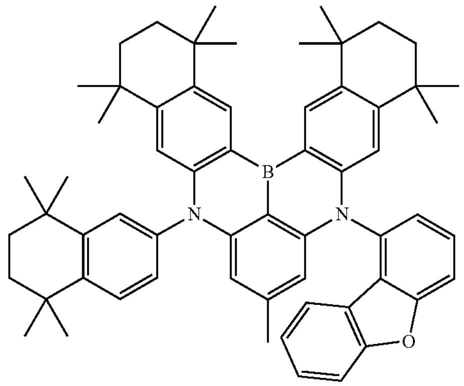
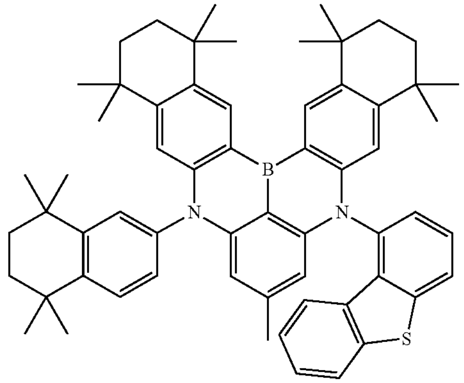
-continued
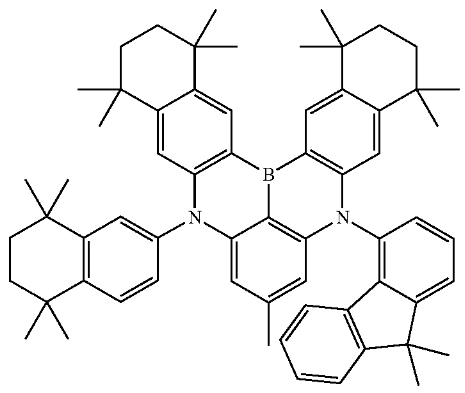
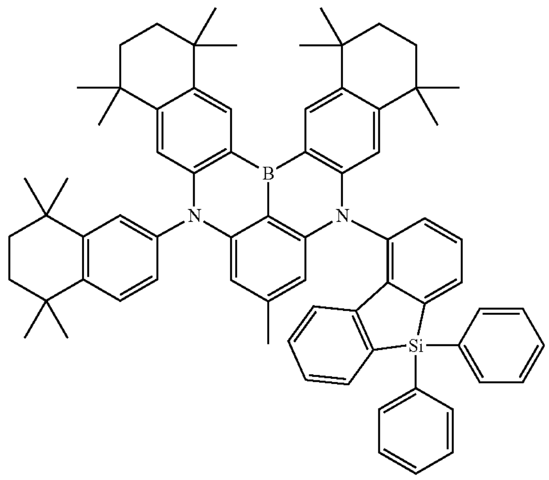
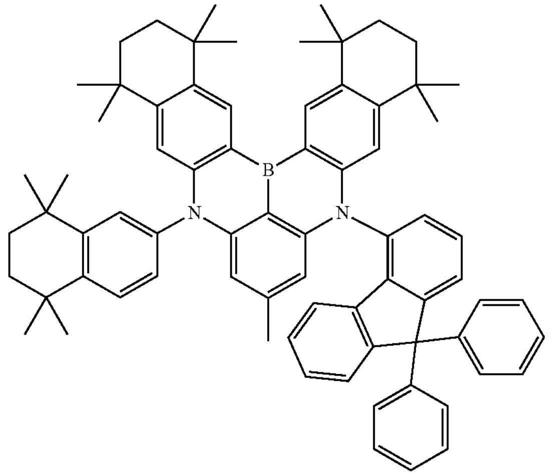

-continued
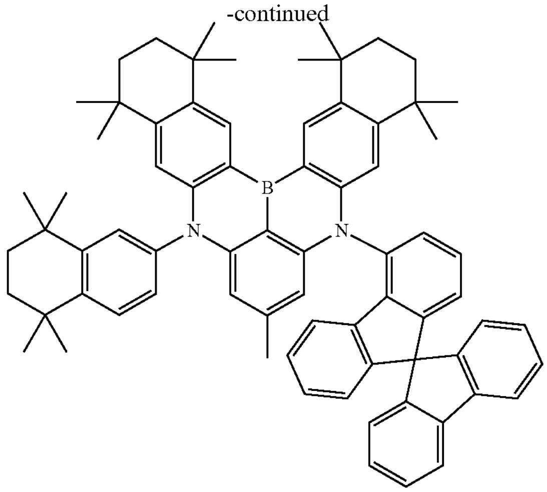
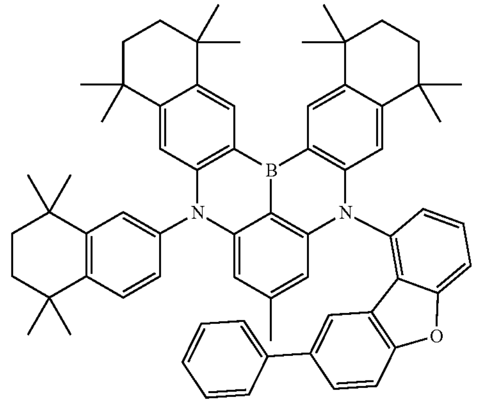
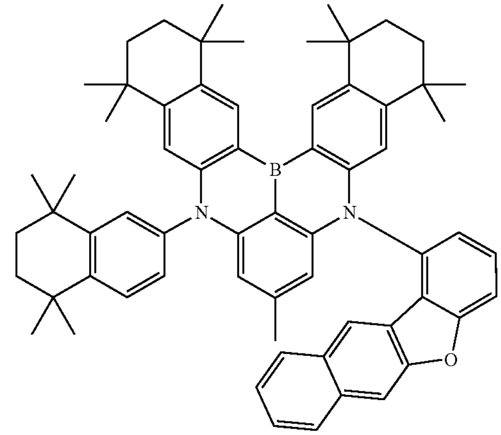
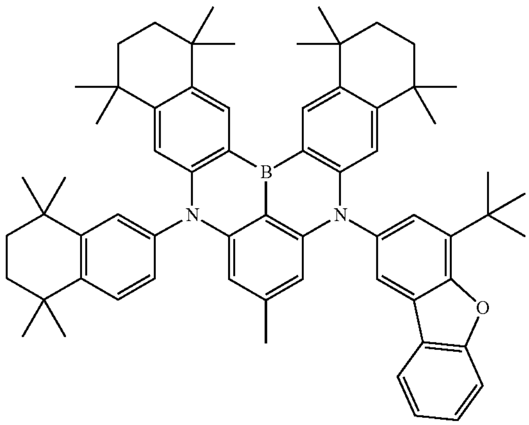
-continued
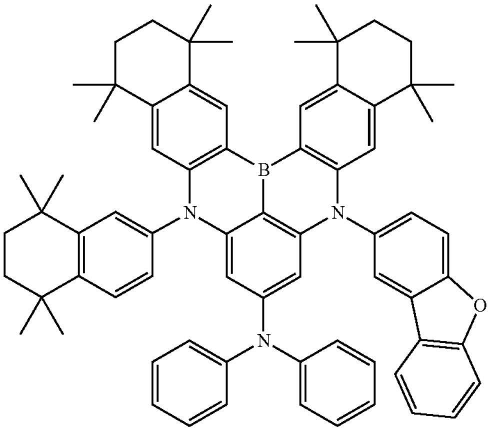
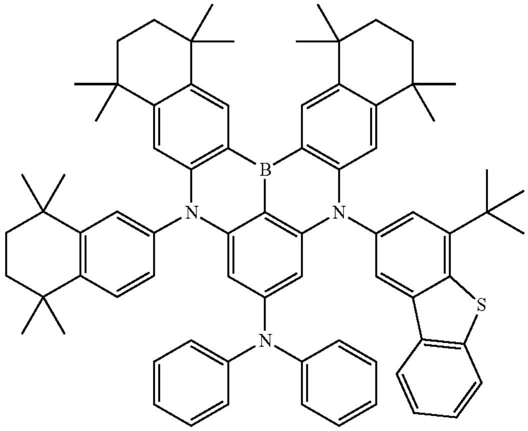
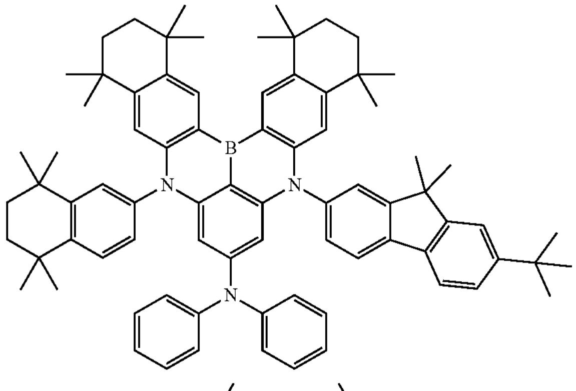
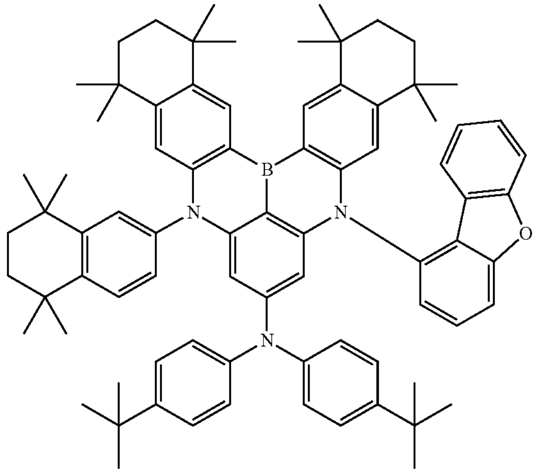

-continued
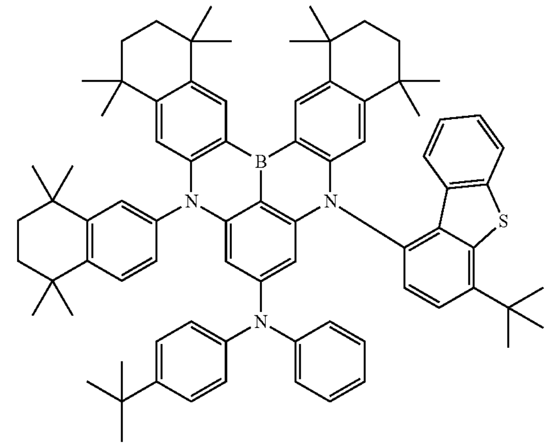
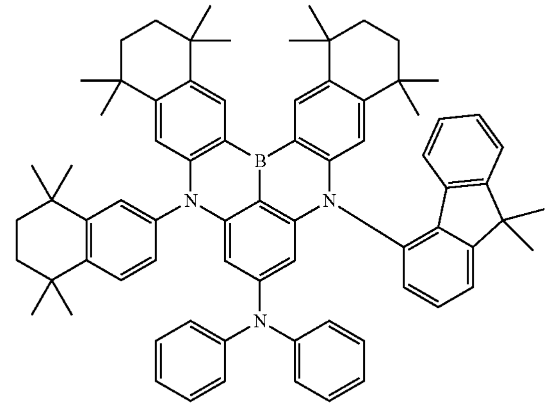
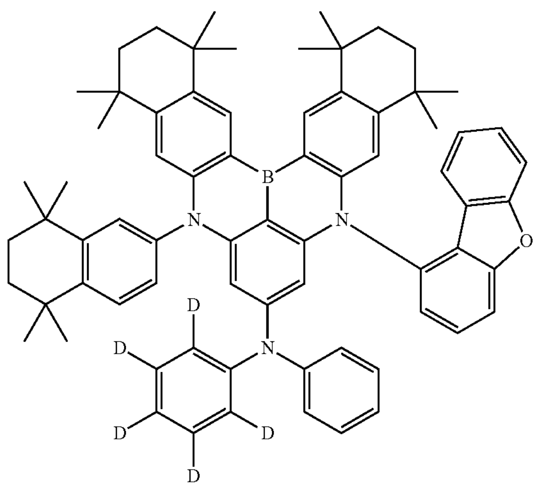
-continued
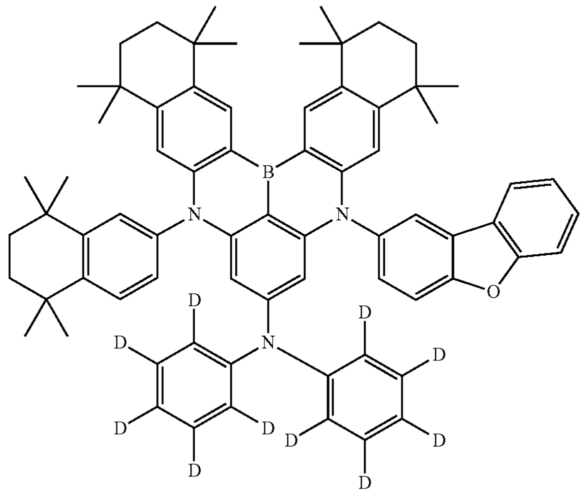
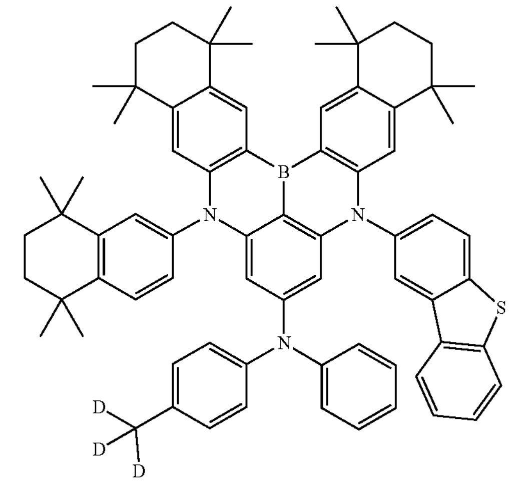
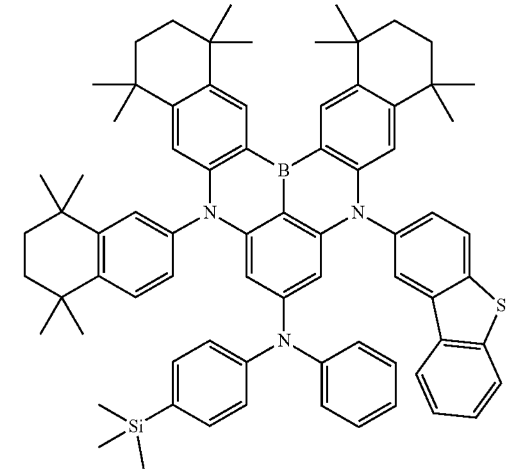

-continued
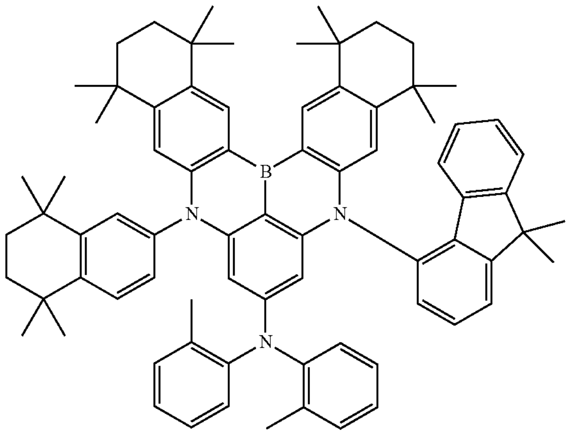
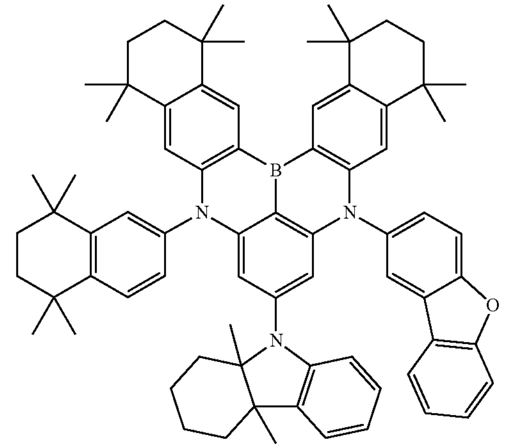
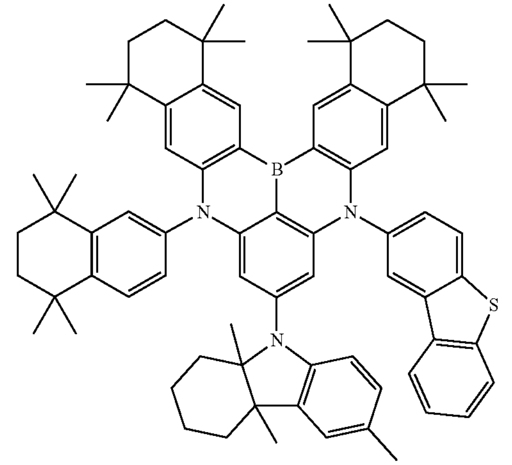
-continued
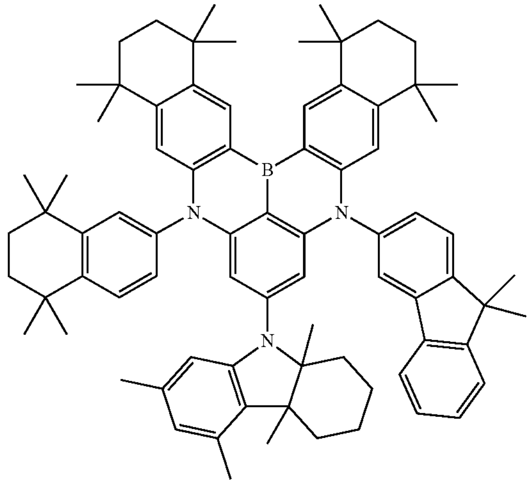
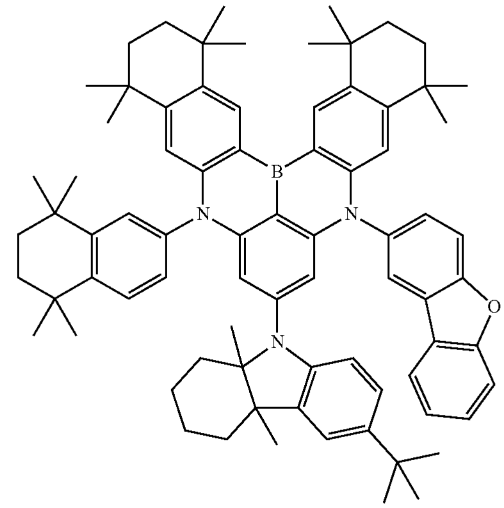
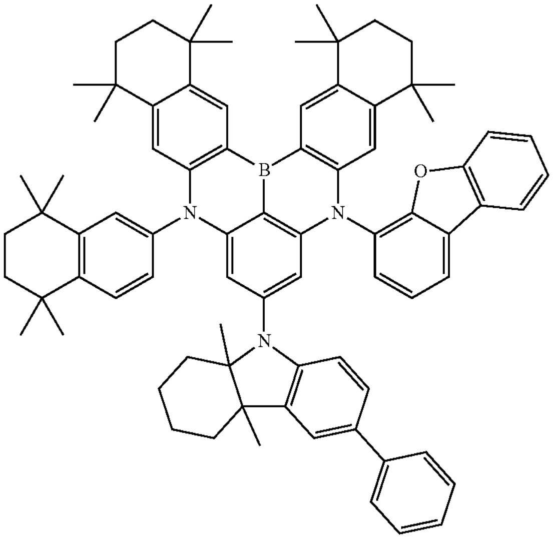

-continued
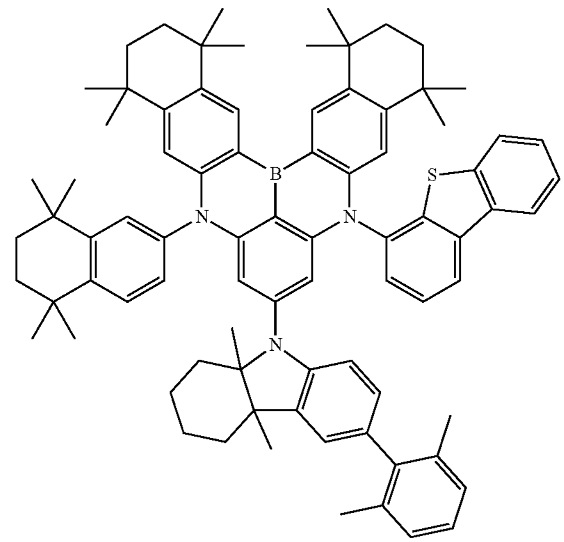
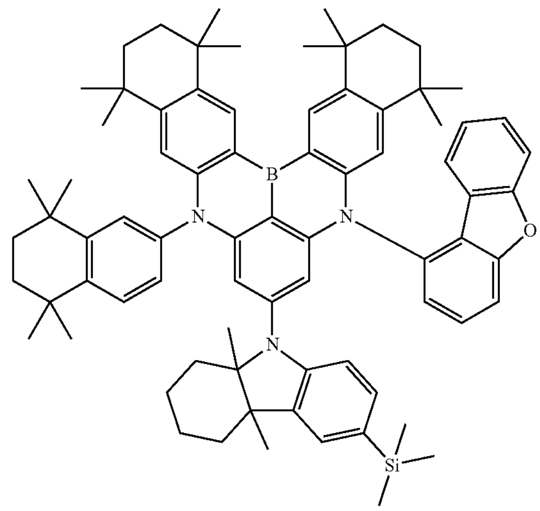
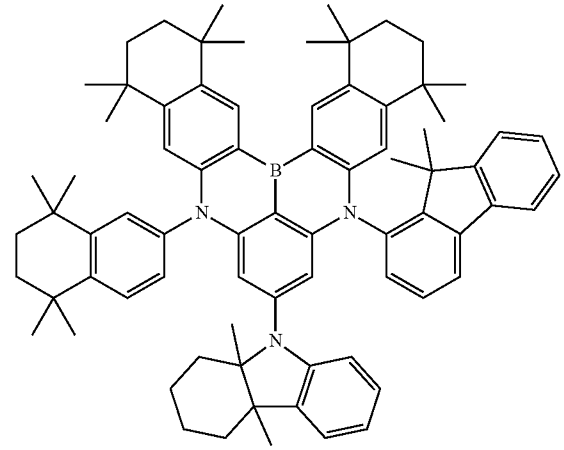
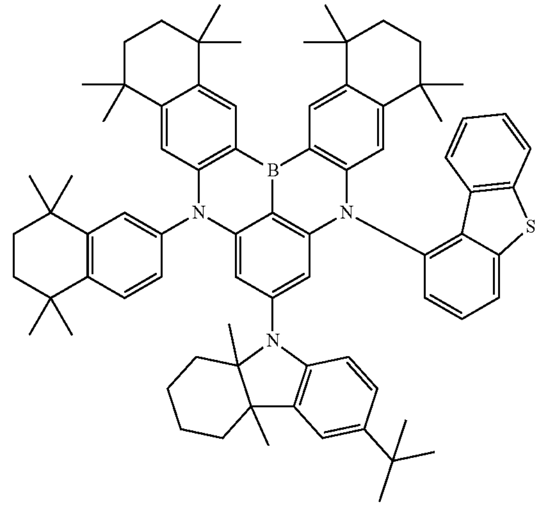
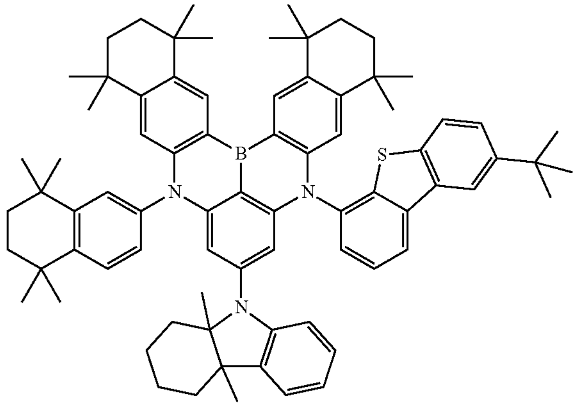
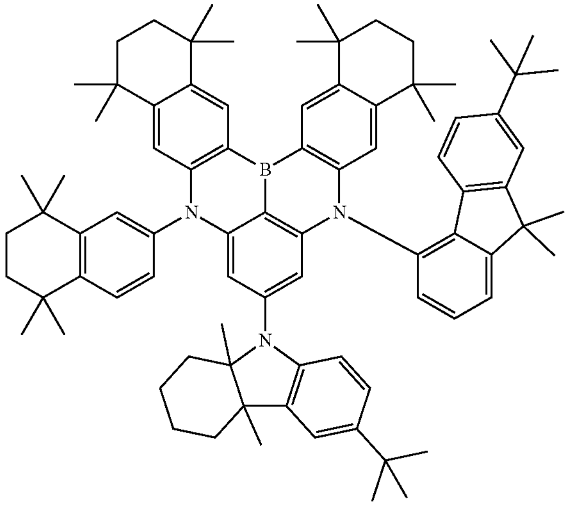
-continued -continued
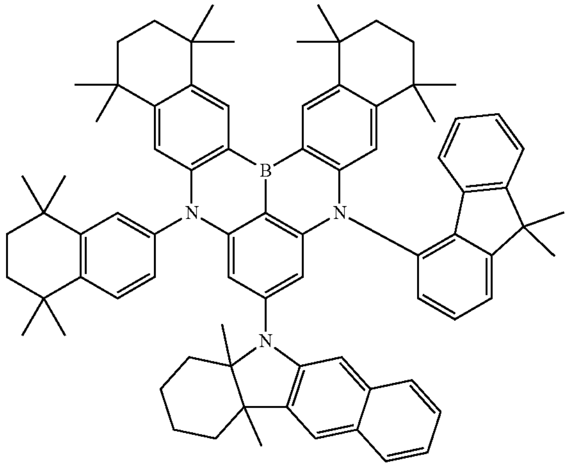
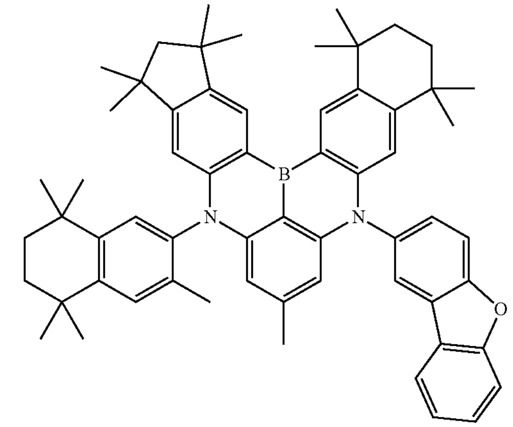
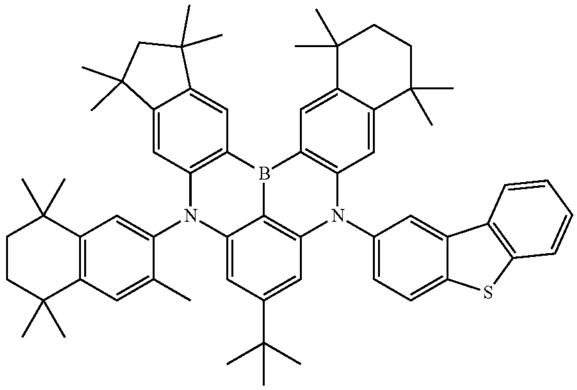
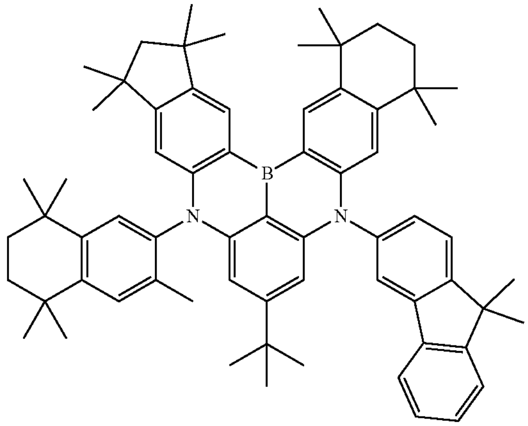
-continued
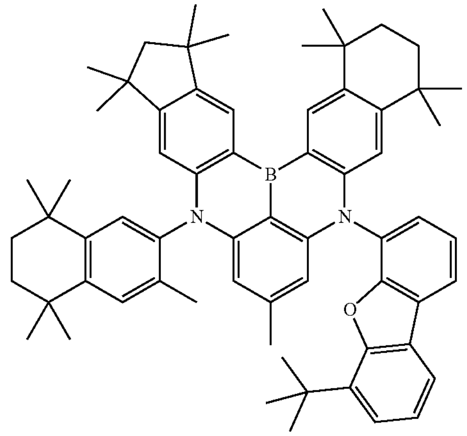
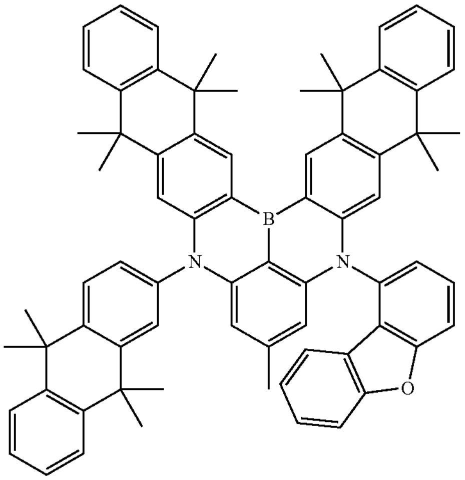
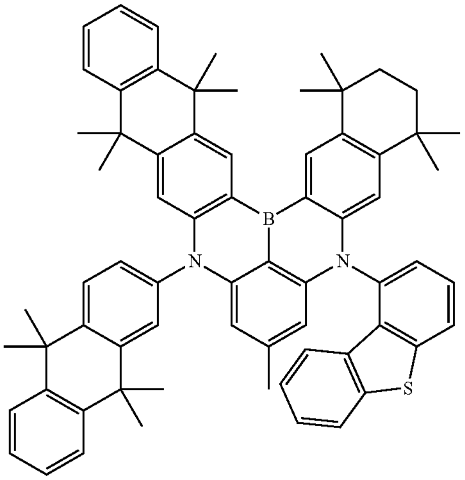

-continued
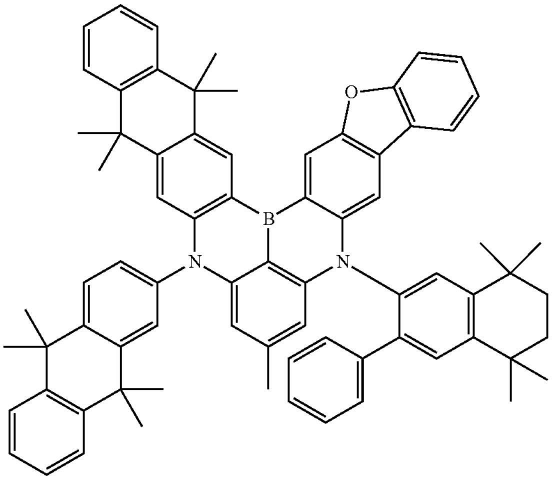
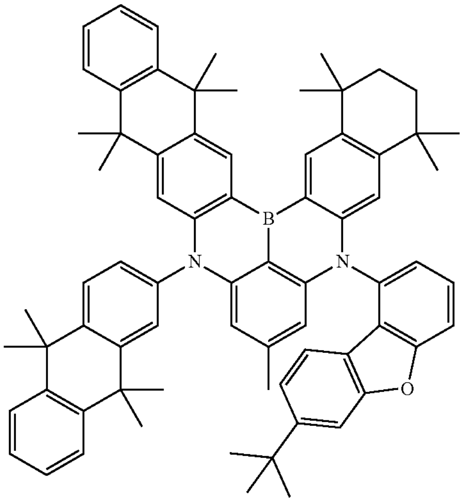
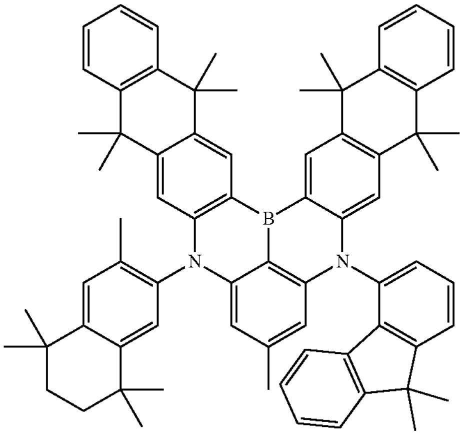
-continued
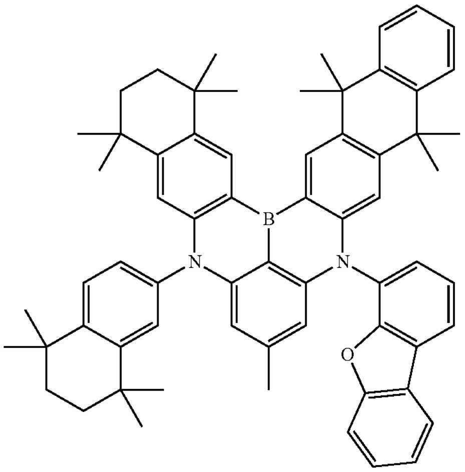
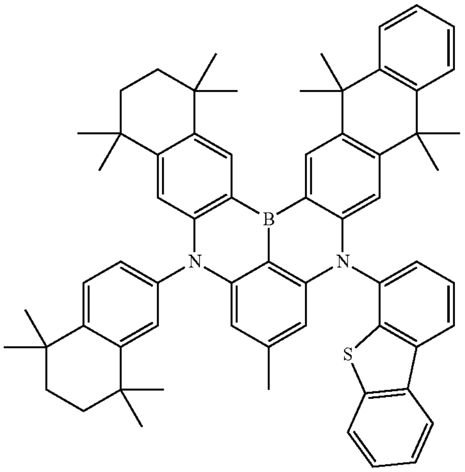
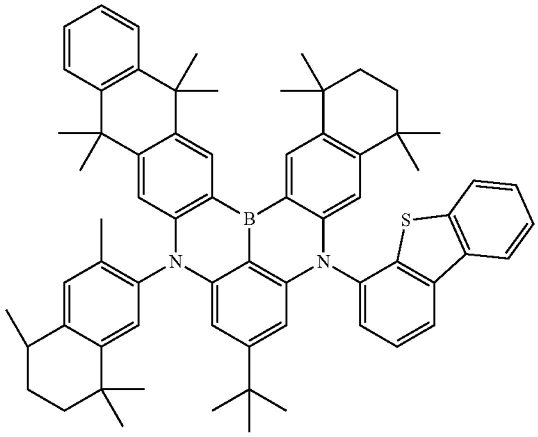

-continued
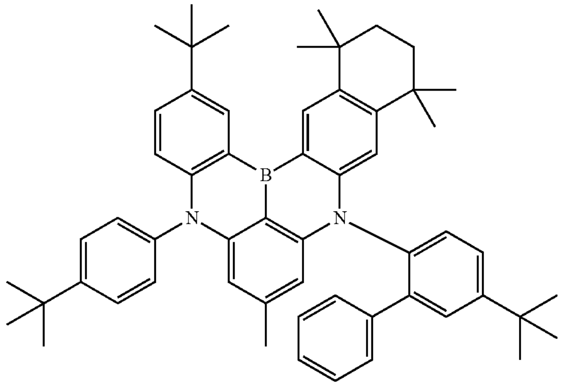
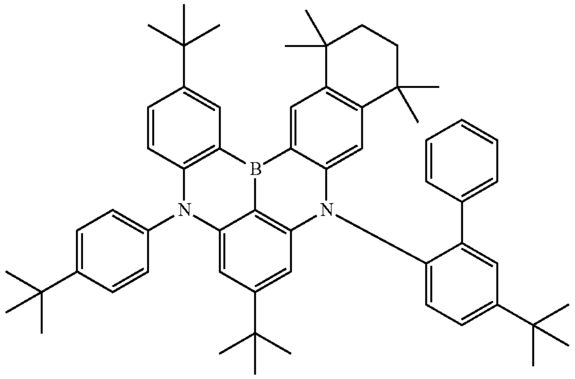
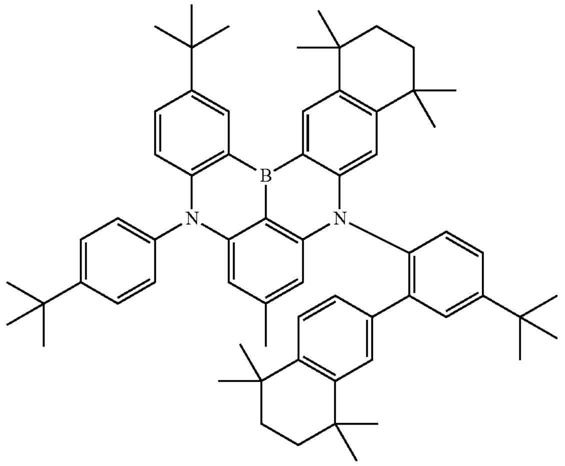
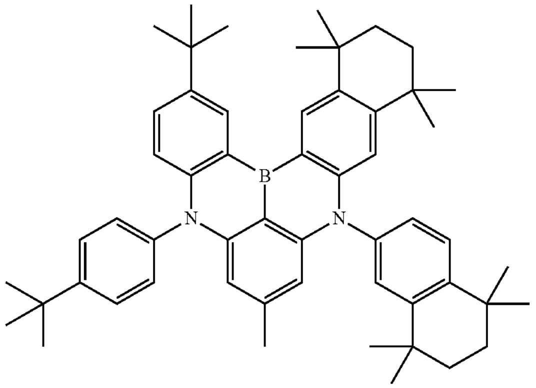
-continued
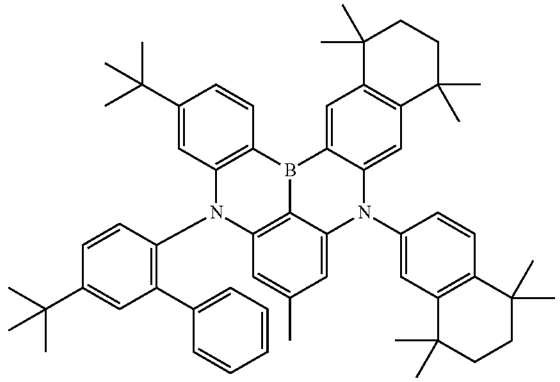
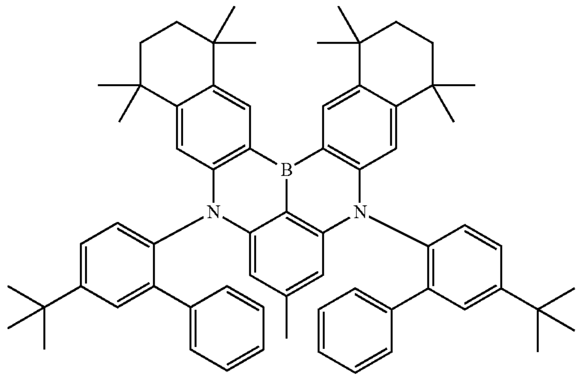
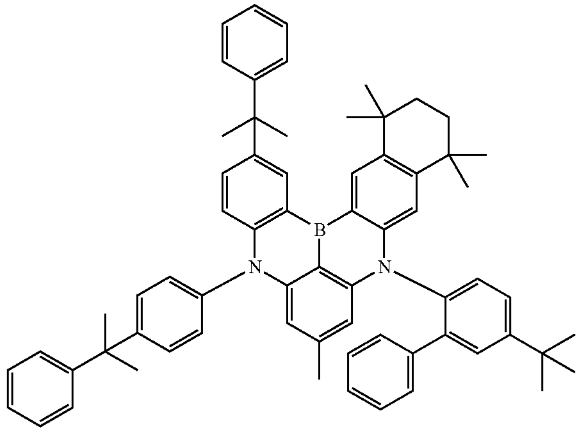
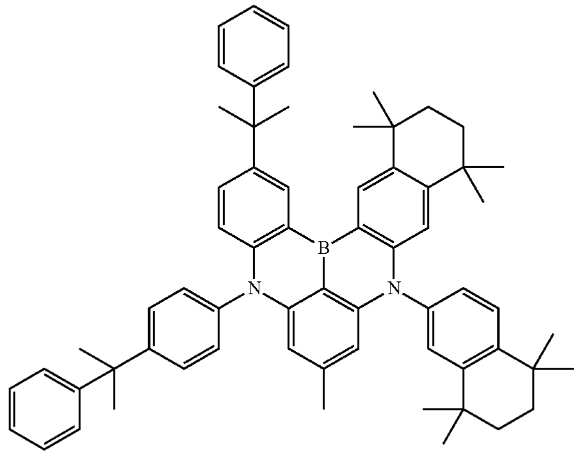

-continued
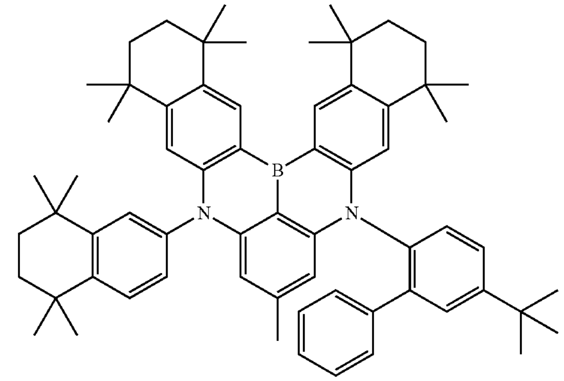
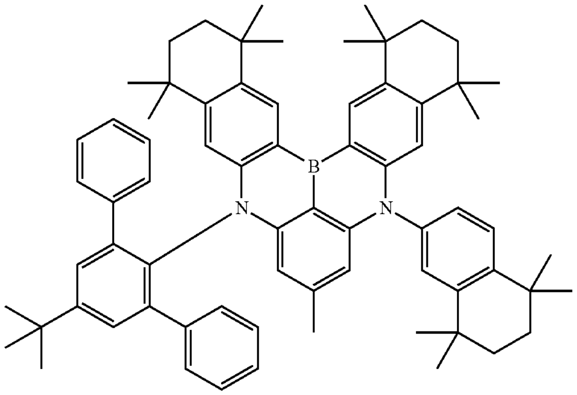
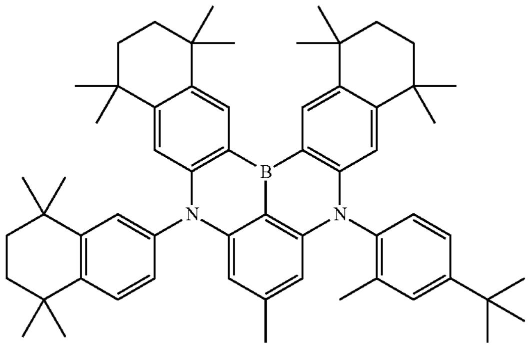
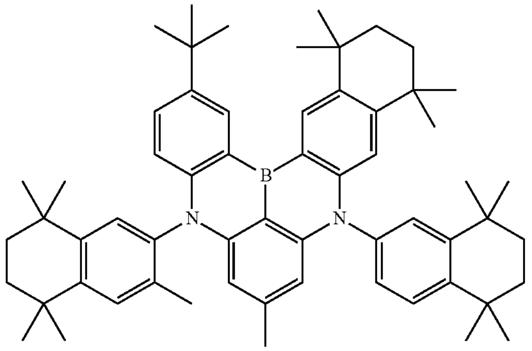
-continued
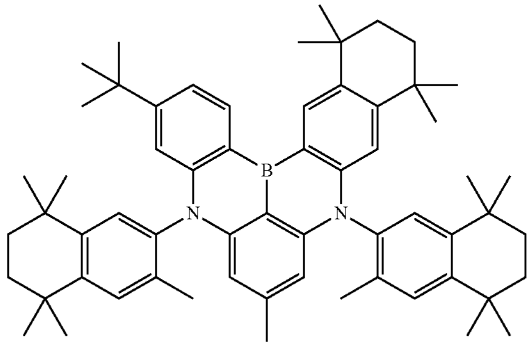
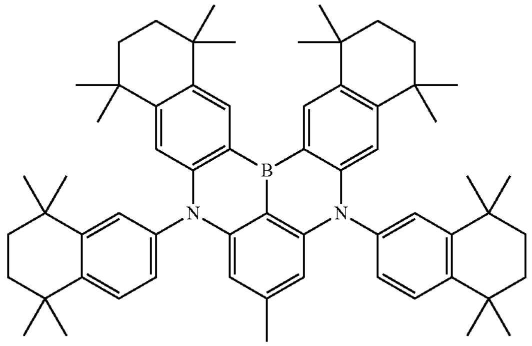
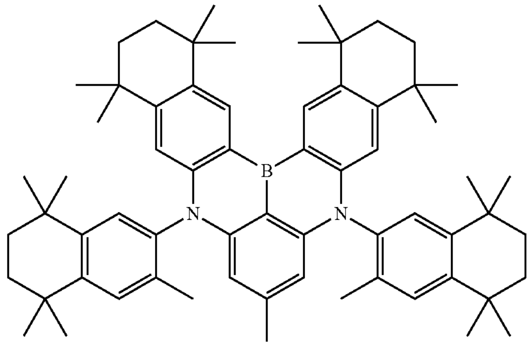
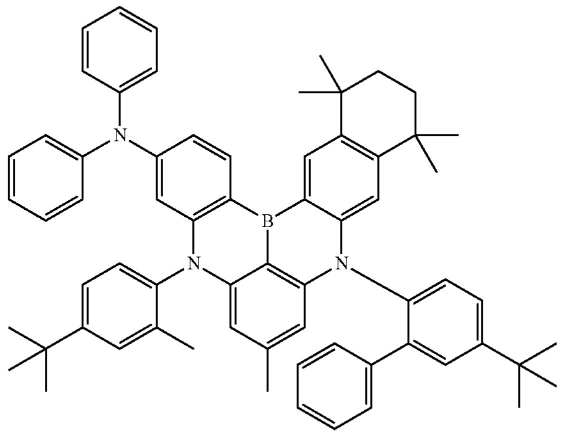

-continued
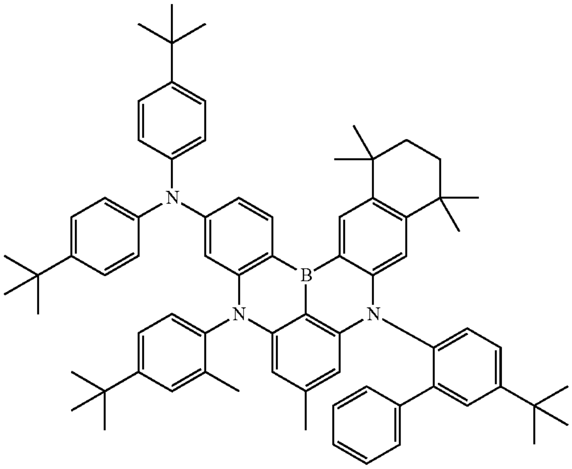
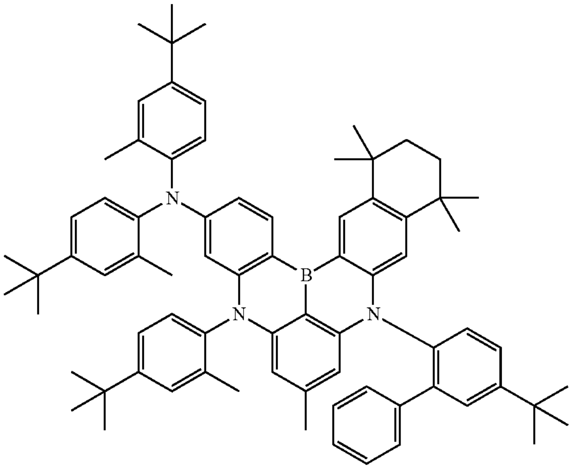
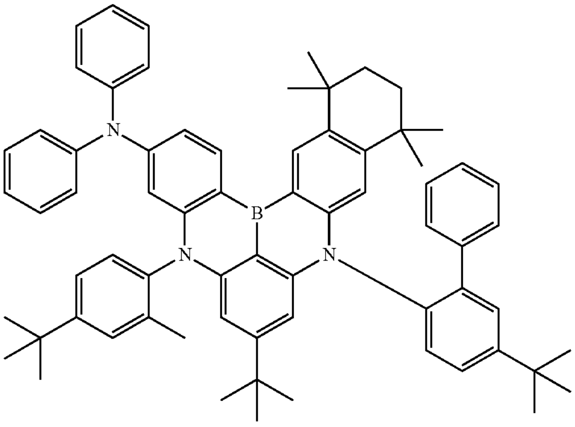
-continued
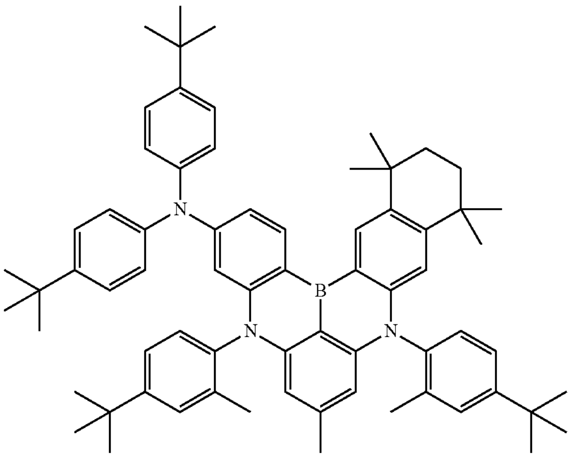
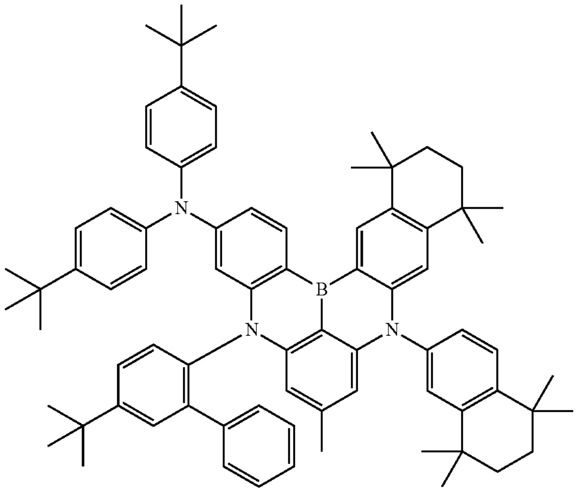
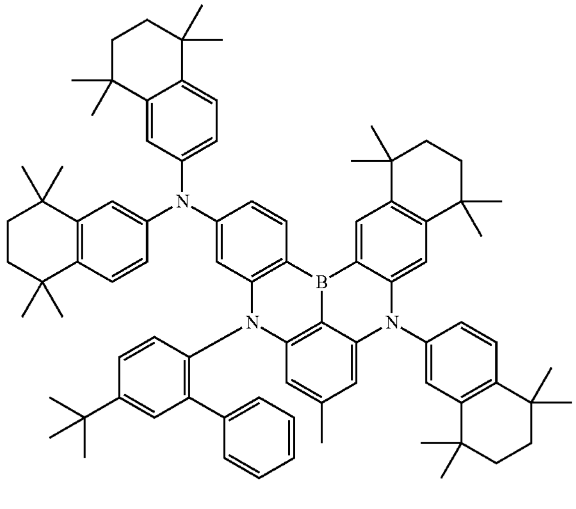

-continued
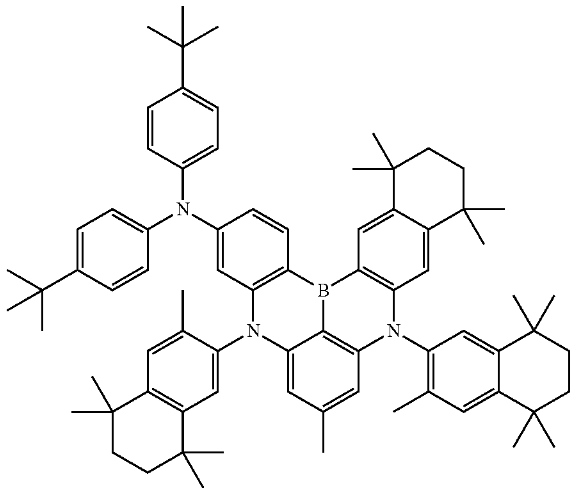
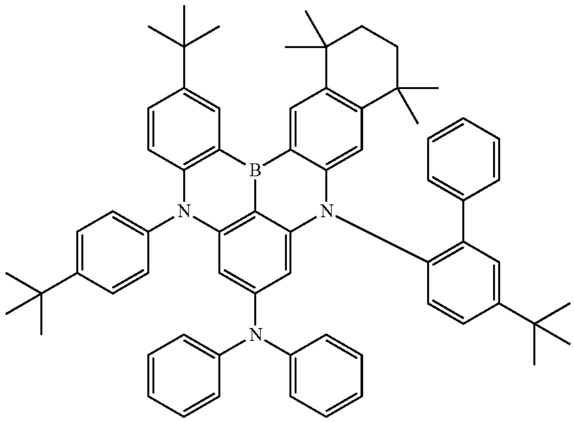
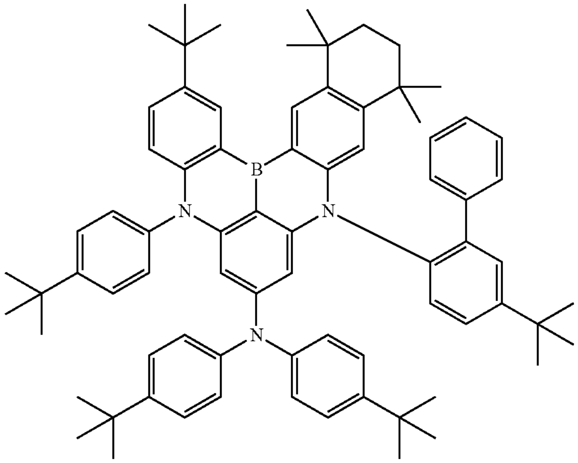
-continued
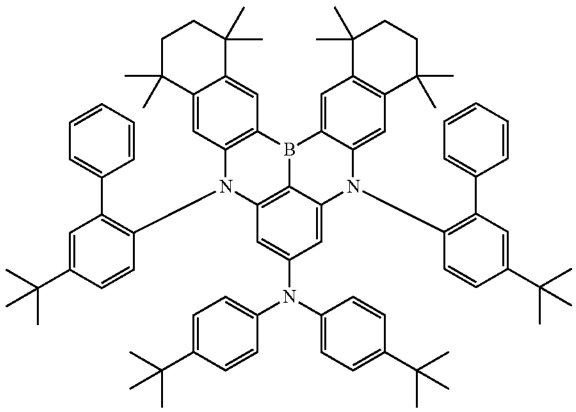
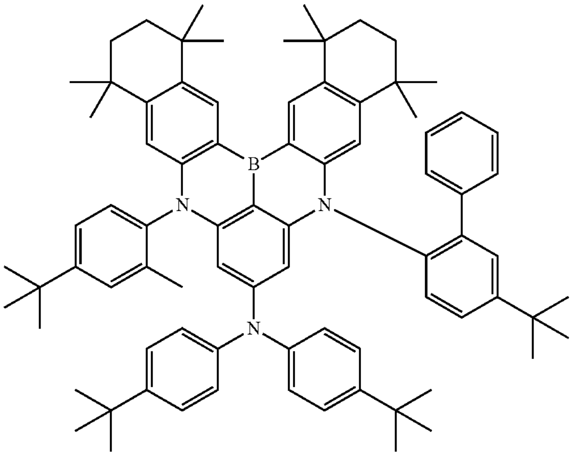
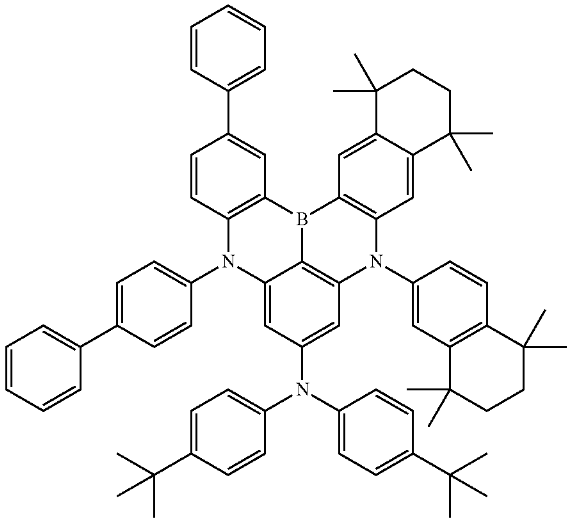

-continued
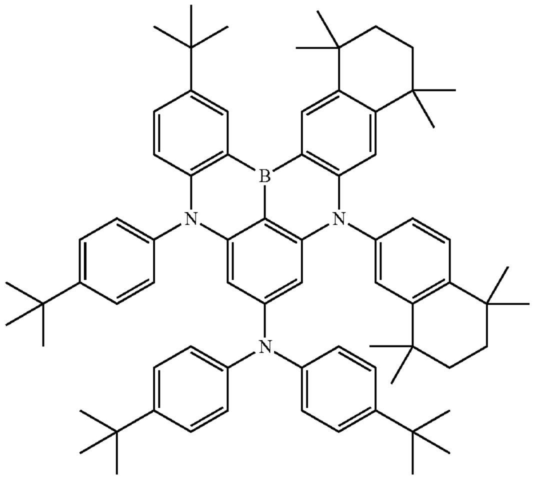
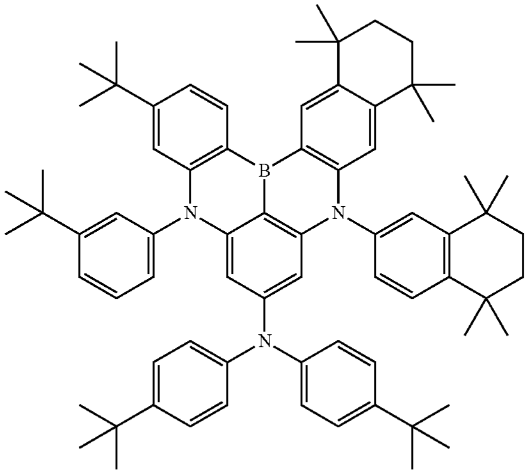
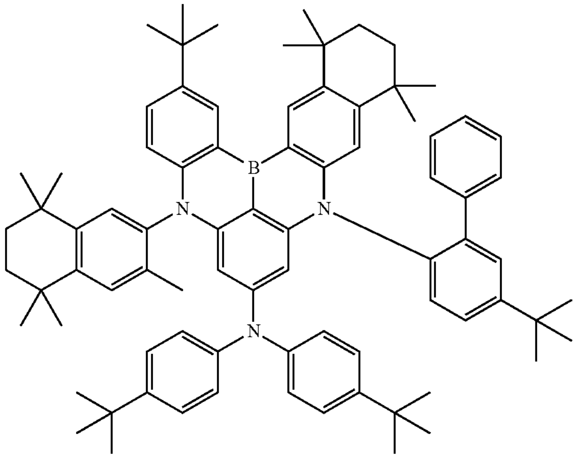
-continued
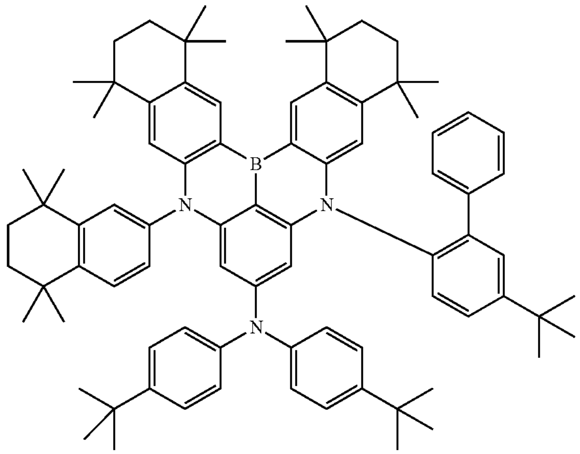
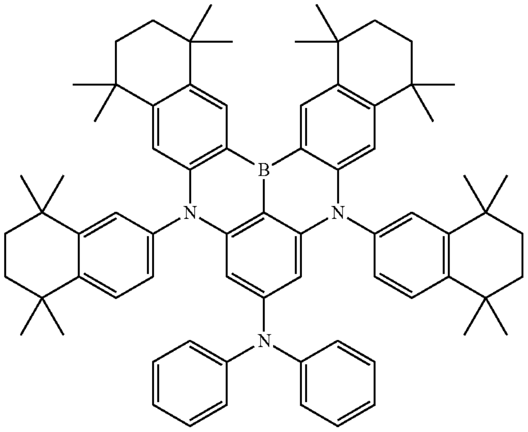
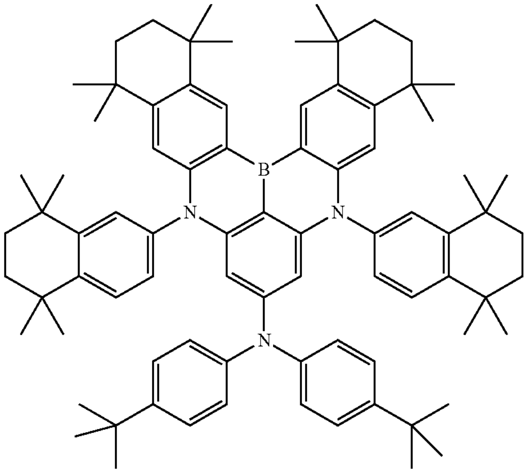

-continued
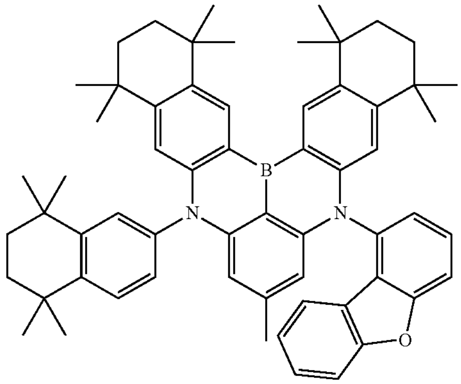
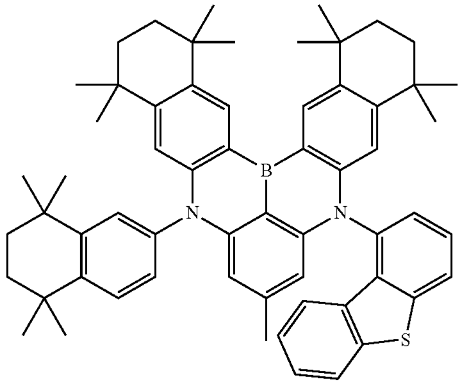
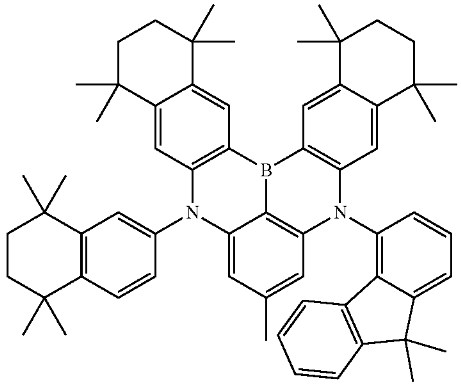
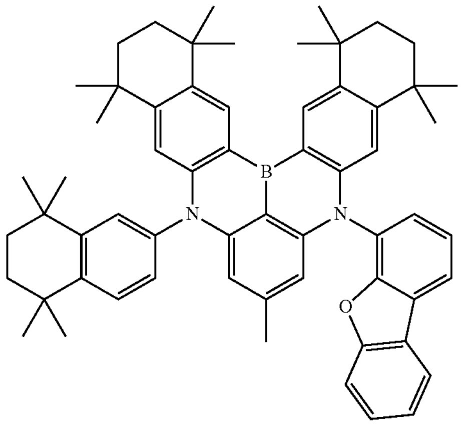
-continued
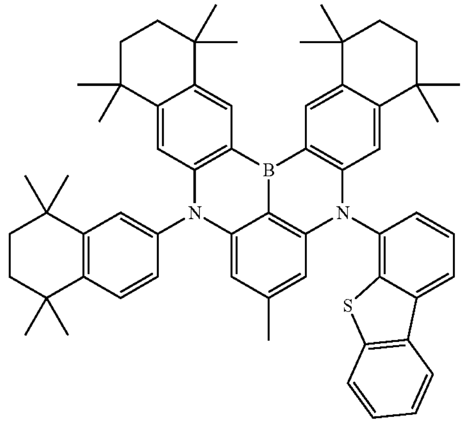
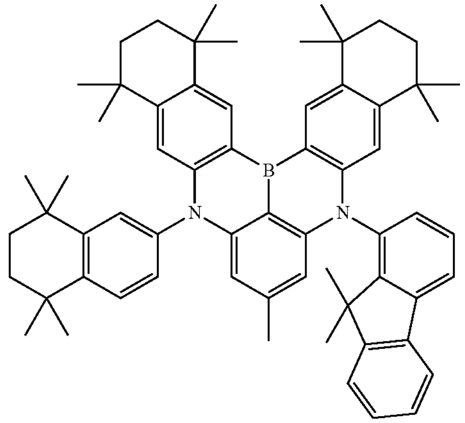
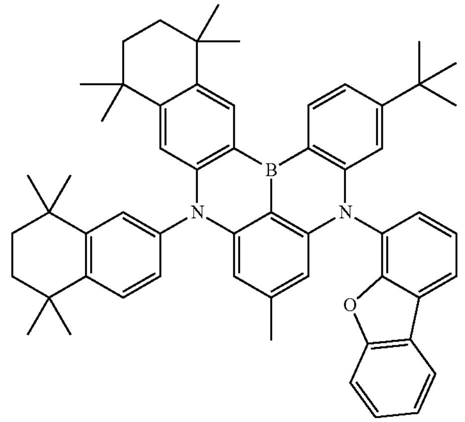

-continued
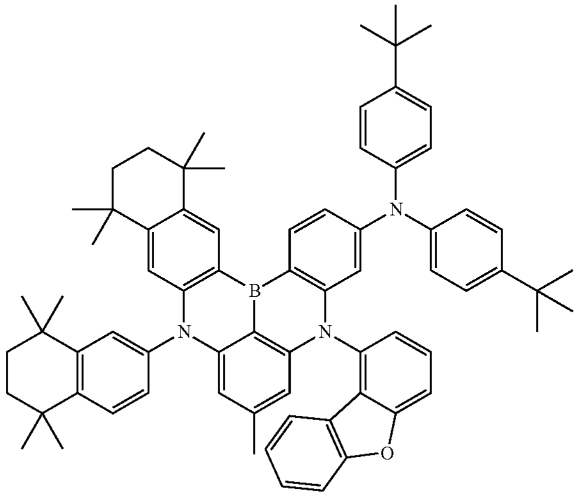
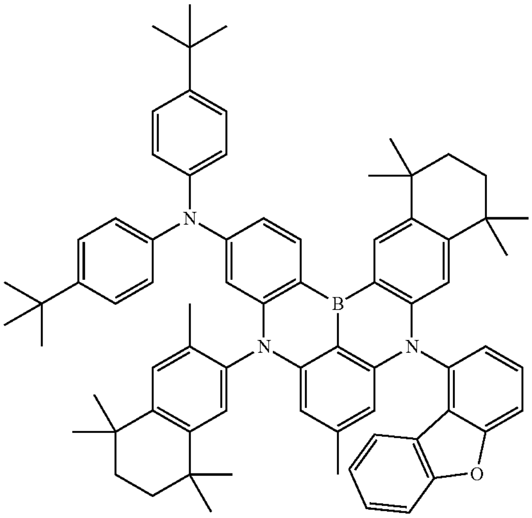
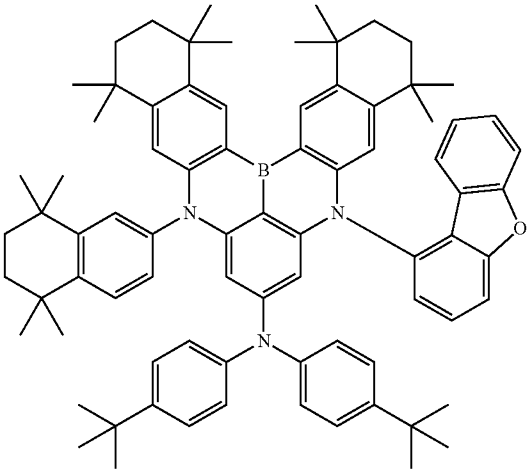
-continued
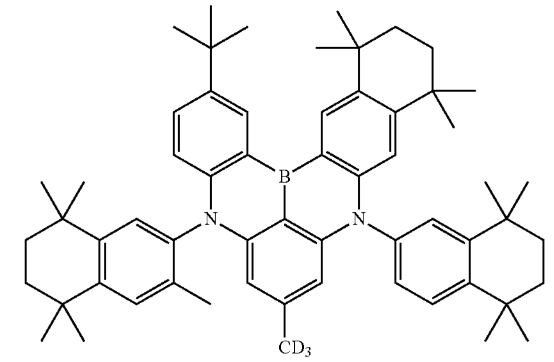
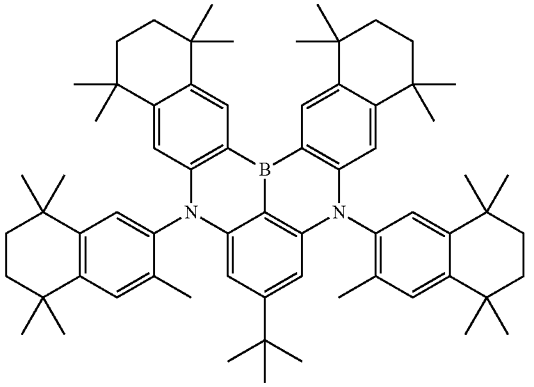
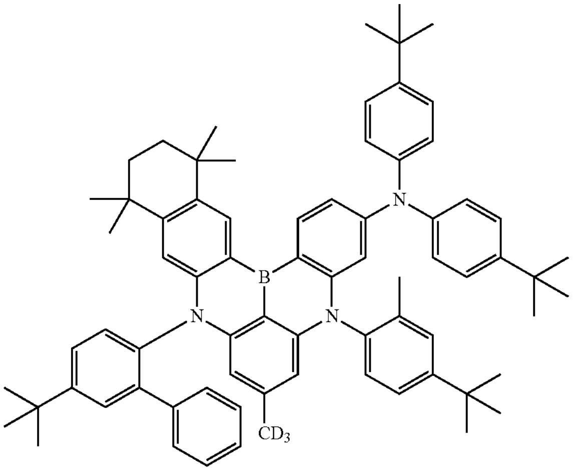
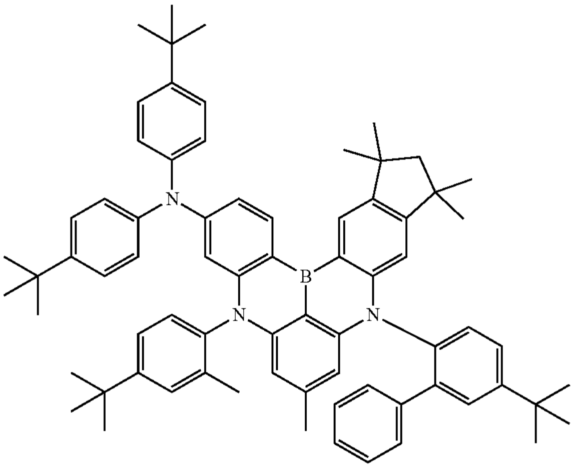

-continued
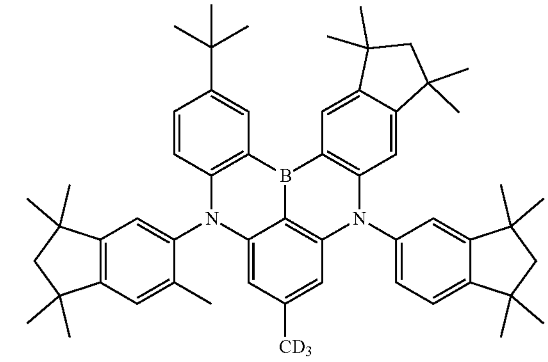
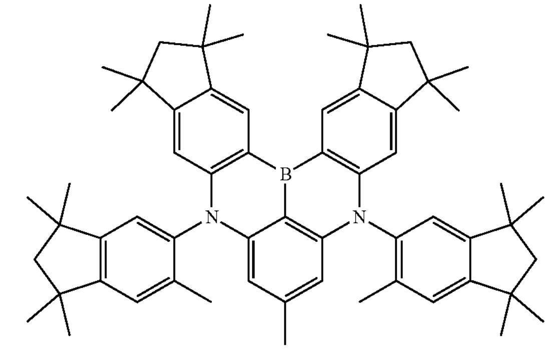
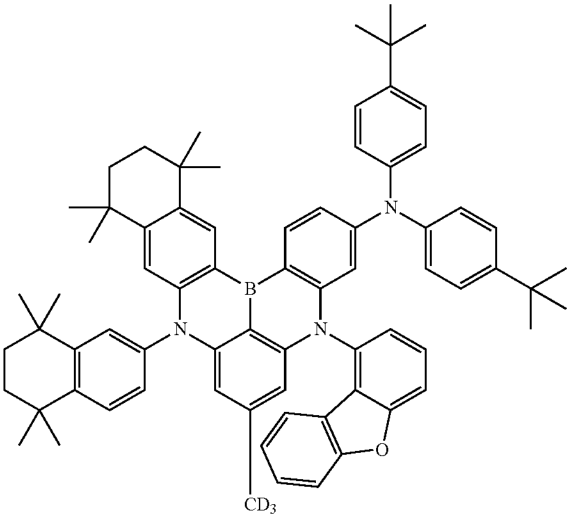
-continued
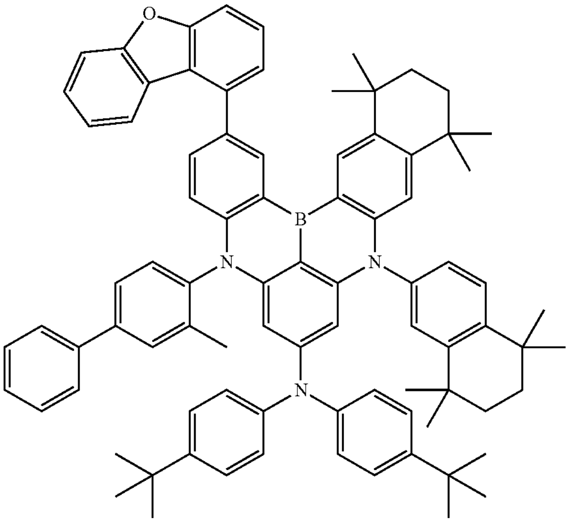
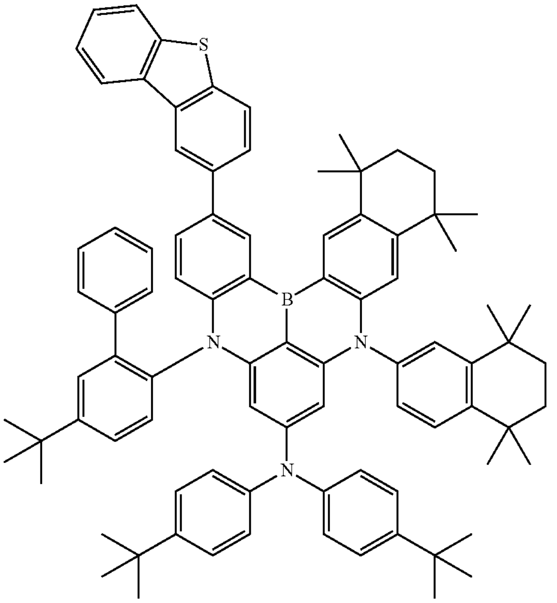
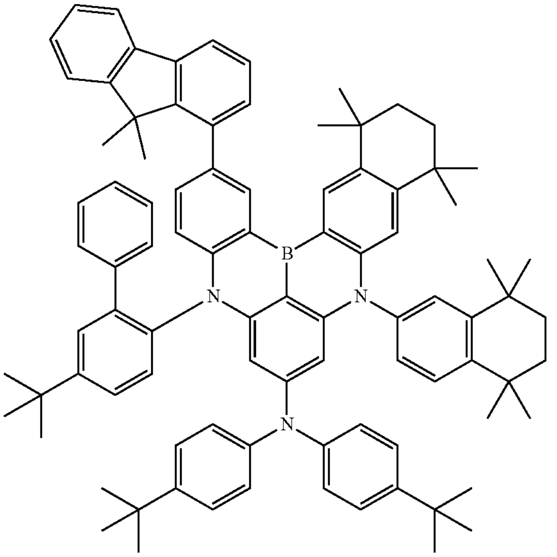

-continued
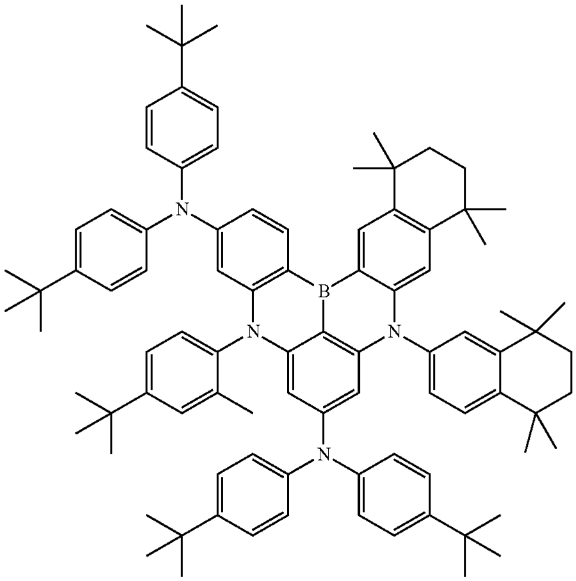
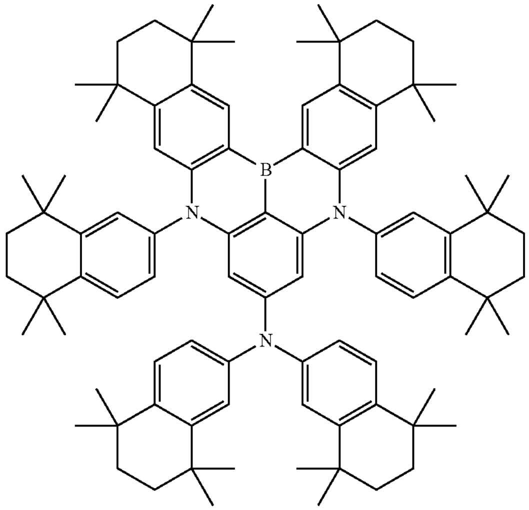
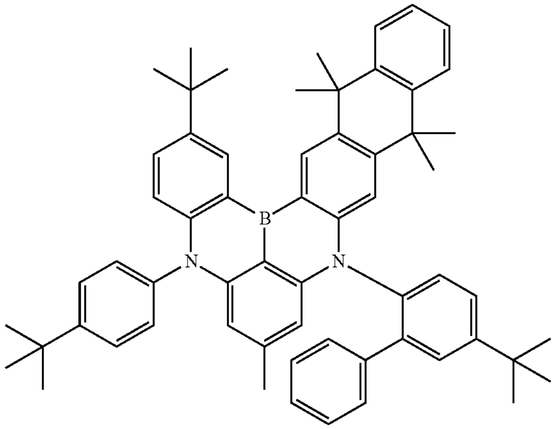
-continued
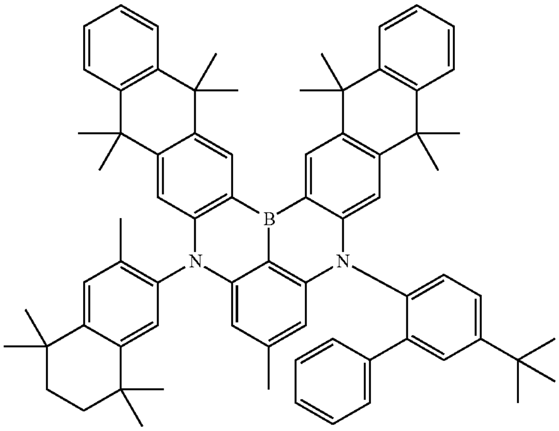
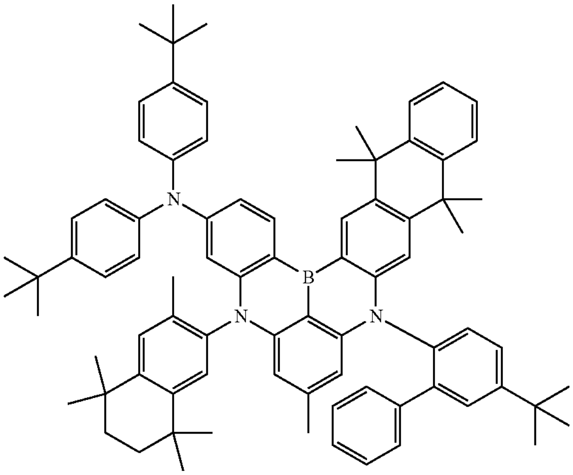
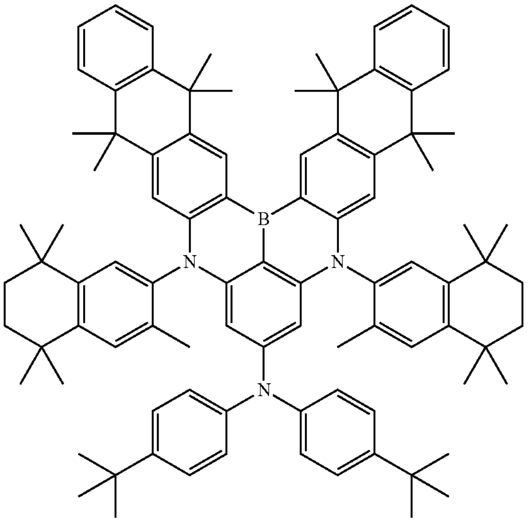

-continued

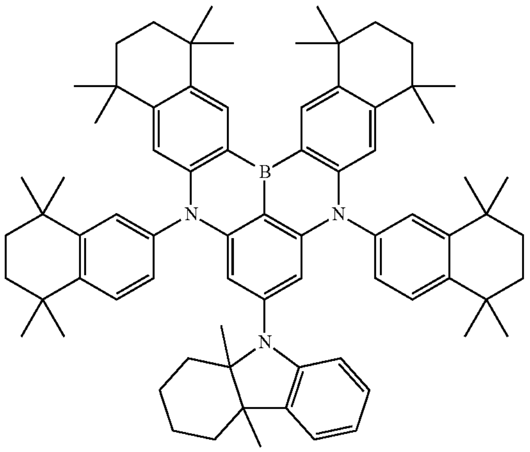

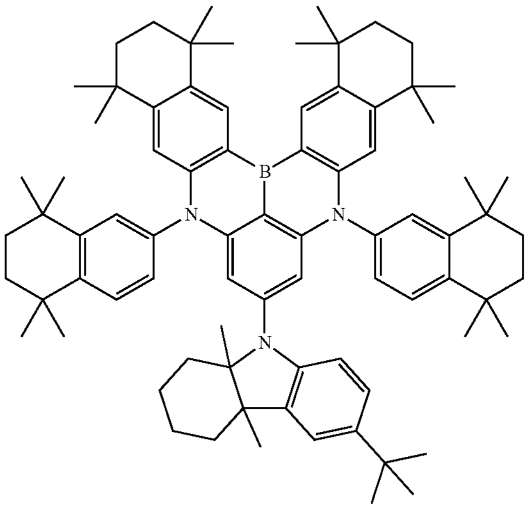

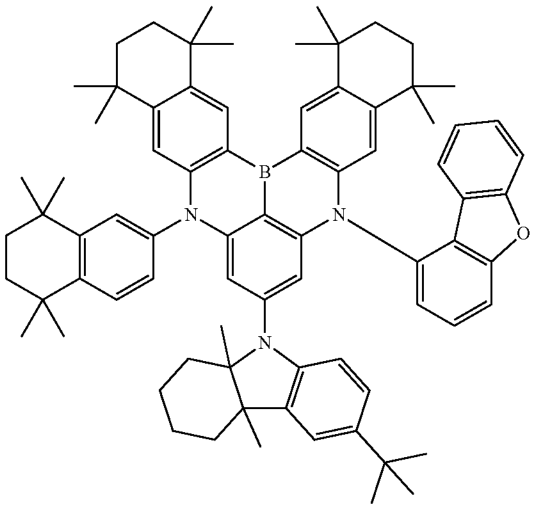

-continued

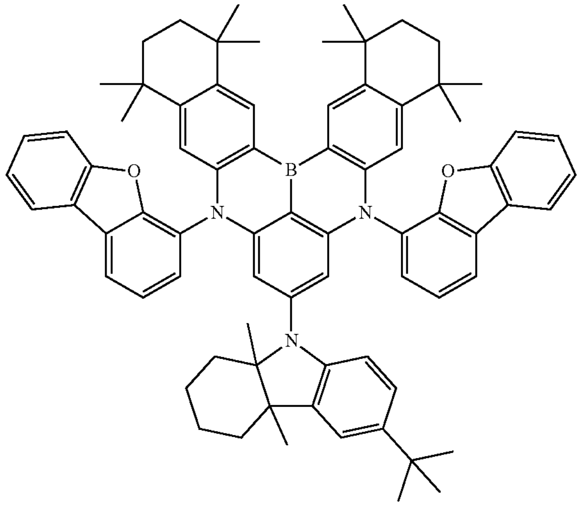

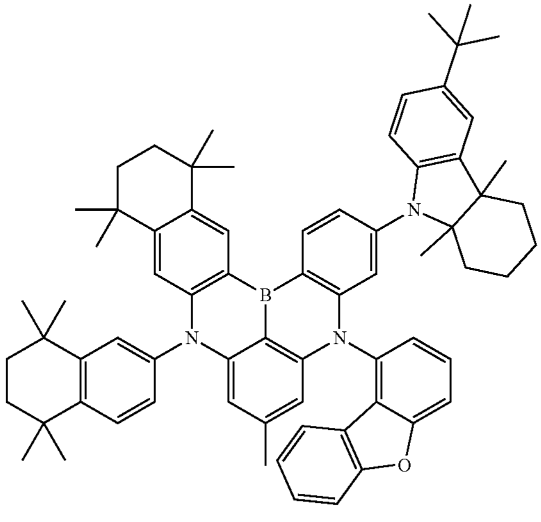

According to an exemplary embodiment of the present invention, the compounds of Formulae 1-1 to 1-3 may be prepared as in the following Reaction Schemes 1 to 6, and the compound of Formula 2 may be prepared as in the following Reaction Scheme 7. The following Reaction Schemes 1 to 7 describe synthesis procedures of partial compounds corresponding to Formulae 1-1 to 1-3 and 2 of the present application, but various compounds corresponding to Formulae 1-1 to 1-3 and 2 of the present application may be synthesized using the synthesis procedures as in the following Reaction Schemes 1 to 7, a substituent may be bonded by methods known in the art, and the type and position of substituent and the number of substituents may be changed according to the technology known in the art.

[Reaction Scheme 1]
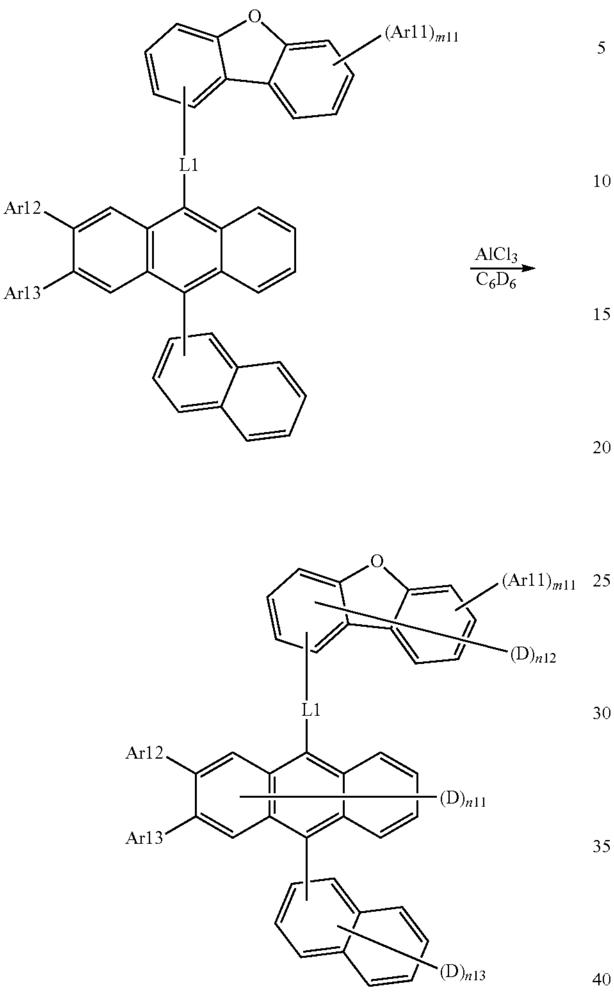
[Reaction Scheme 2]
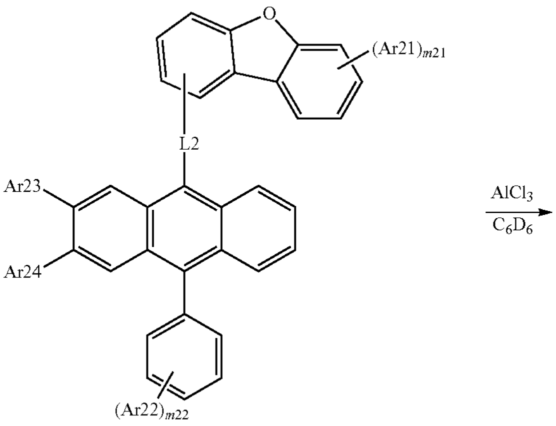
-continued
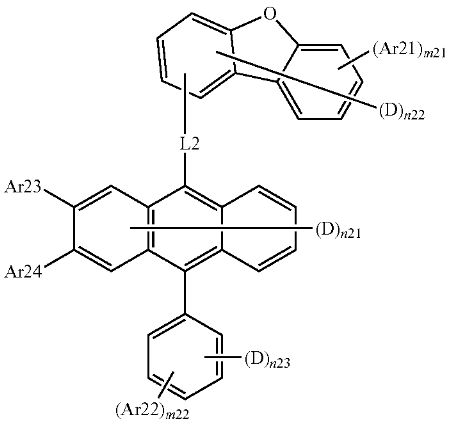
[Reaction Scheme 3]
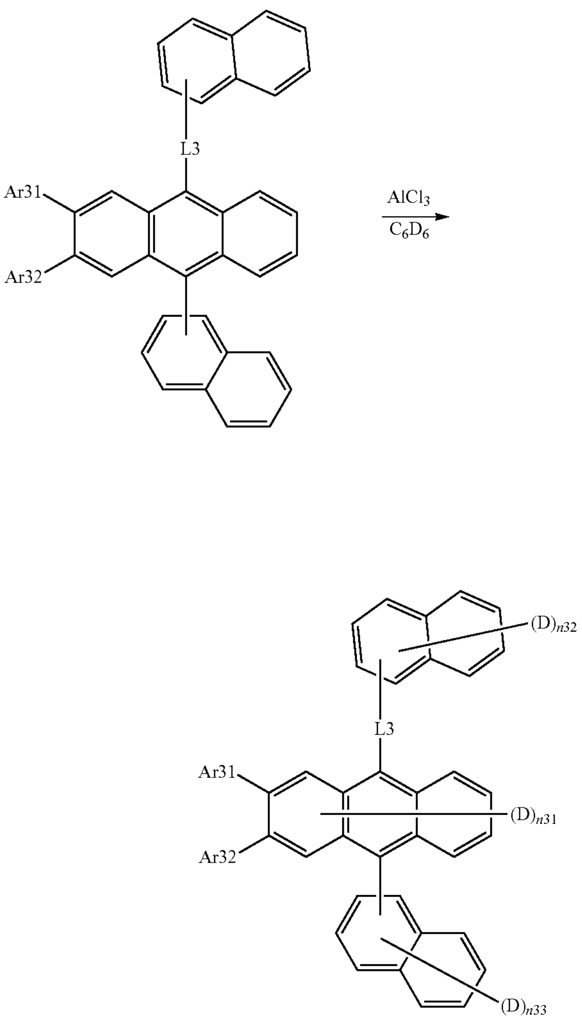

[Reaction Scheme 4]
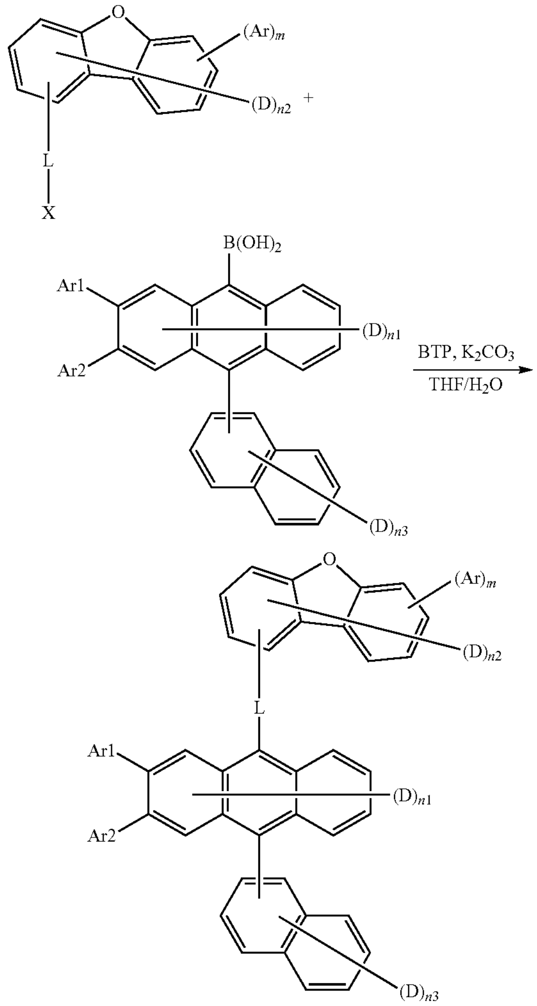
X = halogen
[Reaction Scheme 5]
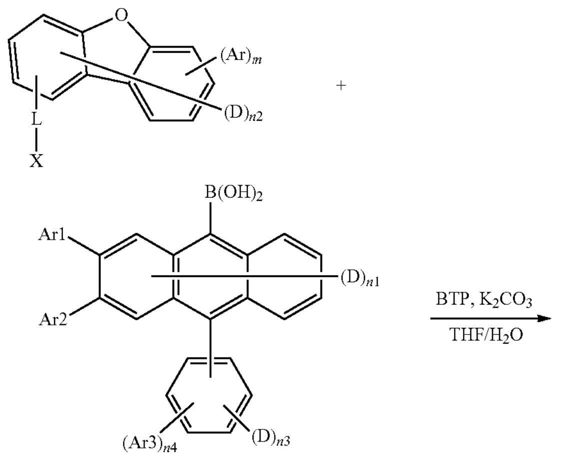
-continued
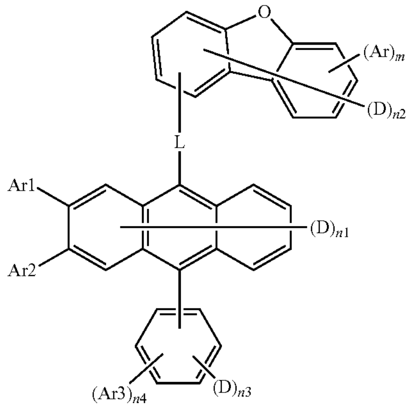
X = halogen
[Reaction Scheme 6]
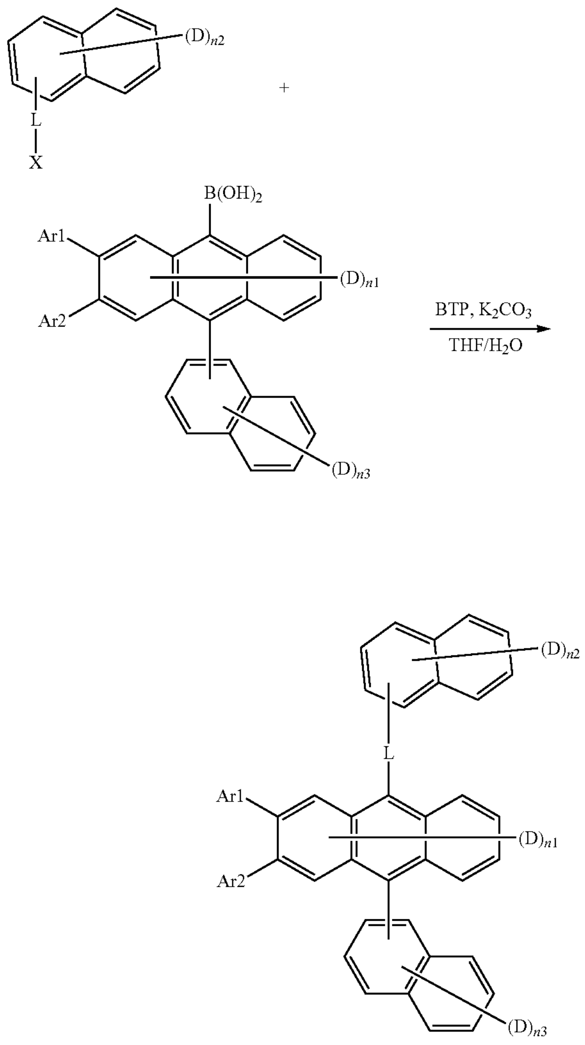
X = halogen

[Reaction Scheme 7]

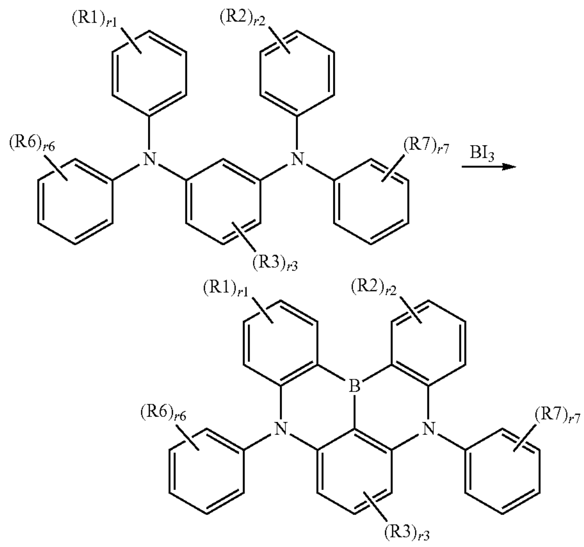

The organic light emitting device of the present specification may be manufactured by typical methods and materials for manufacturing an organic light emitting device, except that a light emitting layer is formed using one or more of the compounds represented by any one of Formulae 1-1 to 1-3 and the compound represented by Formula 2.

A light emitting layer including one or more of the compounds represented by any one of Formulae 1-1 to 1-3 and the compound represented by Formula 2 may be formed as an organic material layer by not only a vacuum deposition method, but also a solution application method. Here, the solution application method means spin coating, dip coating, inkjet printing, screen printing, a spray method, roll coating, and the like, but is not limited thereto.

The organic material layer of the organic light emitting device of the present specification may also be composed of a structure including the light emitting layer, but may be composed of a structure further including an additional organic material layer. The additional organic material layer may be one or more layers of a hole injection layer, a hole transport layer, a layer which simultaneously transports and injects holes, an electron blocking layer, a light emitting layer, an electron transport layer, an electron injection layer, a layer which simultaneously transports and injects electrons, and a hole blocking layer. However, the structure of the organic light emitting device is not limited thereto, and may include a fewer or greater number of organic material layers.

In the organic light emitting device according to an exemplary embodiment of the present specification, the light emitting layer includes one or more of the compounds represented by any one of Formulae 1-1 to 1-3 as a host, and includes the compound represented by Formula 2 as a dopant.

In an exemplary embodiment of the present specification, the light emitting layer includes one of the compounds represented by any one of Formulae 1-1 to 1-3 as a host.

In an exemplary embodiment of the present specification, the light emitting layer includes two of the compounds represented by any one of Formulae 1-1 to 1-3 as a host. In this case, one of the compounds represented by any one of Formulae 1-1 to 1-3 is referred to as a first host, and the other compound is referred to as a second host.

In an exemplary embodiment of the present specification, a weight ratio of the first host and the second host is 1:9 to 9:1, preferably 3:7 to 7:3.

In the organic light emitting device according to an exemplary embodiment of the present specification, the dopant in the light emitting layer may be included in an amount of 0.1 part by weight to 50 parts by weight, preferably 1 part by weight to 30 parts by weight, and more preferably 1 part by weight to 10 parts by weight, based on 100 parts by weight of the host. Within the above range, energy transfer from the host to the dopant occurs efficiently.

According to an exemplary embodiment of the present invention, the maximum light emission peak of the light emitting layer including one or more of the compounds represented by any one of Formulae 1-1 to 1-3 and the compound represented by Formula 2 is present within 400 nm to 500 nm. That is, the light emitting layer is a blue light emitting layer.

Figure 2:
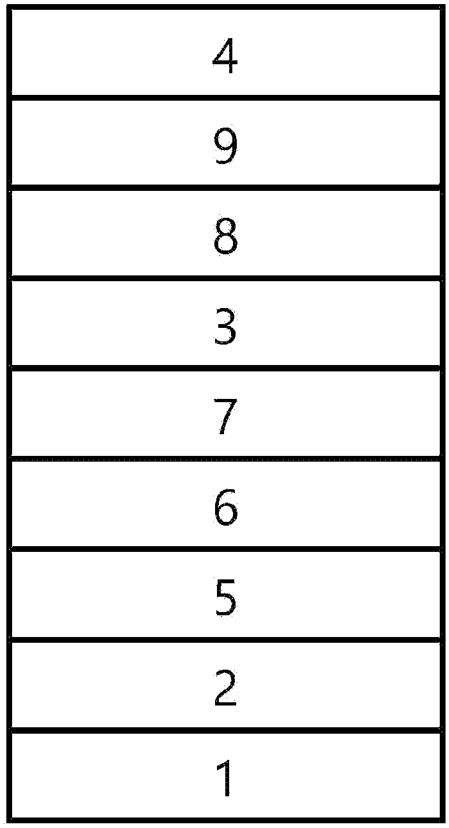

The structure of the organic light emitting device of the present specification may have a structure as illustrated in FIGS. 1 and 2, but is not limited thereto.

FIG. 1 illustrates the structure of an organic light emitting device in which an anode 2, a light emitting layer 3, an electron transporting layer 8, and a cathode 4 are sequentially stacked on a substrate 1. In this case, the light emitting layer 3 may include one or more of the compounds represented by any one of Formulae 1-1 to 1-3 and the compound represented by Formula 2.

FIG. 2 exemplifies a structure of an organic light emitting device in which an anode 2, a hole injection layer 5, a hole transport layer 6, an electron blocking layer 7, a light emitting layer 3, an electron transport layer 8, an electron injection layer 9, and a cathode 4 are sequentially stacked on a substrate 1. In this case, the light emitting layer 3 may include one or more of the compounds represented by any one of Formulae 1-1 to 1-3 and the compound represented by Formula 2.

The organic light emitting device according to the present specification may be manufactured by depositing a metal or a metal oxide having conductivity, or an alloy thereof on a substrate to form an anode, forming an organic material layer including the first organic material layer and the second organic material layer described above thereon, and then depositing a material, which may be used as a cathode, thereon, by using a physical vapor deposition (PVD) method such as sputtering or e-beam evaporation. In addition to the method described above, an organic electronic device may also be made by sequentially depositing a cathode material, an organic material layer, and an anode material on a substrate.

The organic material layer may also have a multi-layered structure further including a hole injection layer, a hole transport layer, a layer which simultaneously injects and transports electrons, an electron blocking layer, a light emitting layer, an electron transport layer, an electron injection layer, a layer which simultaneously injects and transports electrons, a hole blocking layer, and the like. Further, the organic material layer may be manufactured to include a fewer number of layers by a method such as a solvent process, for example, spin coating, dip coating, doctor blading, screen printing, inkjet printing, or a thermal transfer method instead of a deposition method, using various polymer materials.

The anode is an electrode which injects holes, and as an anode material, materials having a high work function are usually preferred so as to facilitate the injection of holes into an organic material layer. Specific examples of the anode material which may be used in the present invention include: a metal, such as vanadium, chromium, copper, zinc, and gold, or an alloy thereof; a metal oxide, such as zinc oxide, indium oxide, indium tin oxide (ITO), and indium zinc oxide (IZO); a combination of a metal and an oxide, such as ZnO:Al or $SnO_2$:Sb; a conductive polymer, such as poly(3-methylthiophene), poly[3,4-(ethylene-1,2-dioxy)thiophene] (PEDOT), polypyrrole, and polyaniline; and the like, but are not limited thereto.

The cathode is an electrode which injects electrons, and as a cathode material, materials having a low work function are usually preferred so as to facilitate the injection of electrons into an organic material layer.

Specific examples of the cathode material include: a metal such as magnesium, calcium, sodium, potassium, titanium, indium, yttrium, lithium, gadolinium, aluminum, silver, tin, and lead, or an alloy thereof; a multi-layer structured material, such as LiF/Al or $LiO_2$/Al; and the like, but are not limited thereto.

The hole injection layer is a layer serving to facilitate the injection of holes from the anode to the light emitting layer, and may have a single-layered or multi-layered structure. A hole injection material is a material which may proficiently receive holes from an anode at low voltage, and the highest occupied molecular orbital (HOMO) of the hole injection material is preferably a value between the work function of the anode material and the HOMO of the neighboring organic material layer. Specific examples of the hole injection material include metal porphyrin, oligothiophene, arylamine-based organic materials, hexanitrile hexaazatriphenylene-based organic materials, quinacridone-based organic materials, perylene-based organic materials, anthraquinone, polyaniline-based and polythiophene-based conductive polymers, and the like, but are not limited thereto.

In an exemplary embodiment of the present specification, a hole injection layer has a multi-layered structure of two or more layers, and each layer includes a material different from each other.

The hole transport layer may serve to facilitate the transport of holes. A hole transport material is suitably a material having high hole mobility which may receive holes from an anode or a hole injection layer and transfer the holes to a light emitting layer. Specific examples thereof include arylamine-based organic materials, conductive polymers, block copolymers having both conjugated portions and non-conjugated portions, and the like, but are not limited thereto.

As the layer which simultaneously transports and injects holes, a hole transport layer material and/or a hole injection layer material known in the art may be used.

As the layer which simultaneously transports and injects electrons, an electron transport layer material and/or an electron injection layer material known in the art may be used.

An electron blocking layer may be provided between the hole transport layer and the light emitting layer. For the electron blocking layer, materials known in the art may be used.

The light emitting layer may emit red, green, or blue light, and may be composed of a phosphorescent material or a fluorescent material. The light emitting material is a material which may accept holes and electrons from a hole transport layer and an electron transport layer, respectively, and combine the holes and the electrons to emit light in a visible ray region, and is preferably a material having high quantum efficiency for fluorescence or phosphorescence. Specific examples thereof include: 8-hydroxy-quinoline aluminum complexes ($Alq_3$); carbazole-based compounds; dimerized styryl compounds; BAlq; 10-hydroxybenzoquinoline-metal compounds; benzoxazole-based, benzthiazole-based and benzimidazole-based compounds; poly(p-phenylenevinylene) (PPV)-based polymers; spiro compounds; polyfluorene, lubrene, and the like, but are not limited thereto.

Examples of the host material for the light emitting layer include fused aromatic ring derivatives, or hetero ring-containing compounds, and the like. Specifically, examples of the fused aromatic ring derivative include anthracene derivatives, pyrene derivatives, naphthalene derivatives, pentacene derivatives, phenanthrene compounds, fluoranthene compounds, and the like, and examples of the hetero ring-containing compound include carbazole derivatives, dibenzofuran derivatives, ladder-type furan compounds, pyrimidine derivatives, and the like, but the examples thereof are not limited thereto.

When the light emitting layer emits red light, it is possible to use a phosphorescent material such as bis(1-phenylisoquinoline)acetylacetonate iridium (PIQIr(acac)), bis(1-phenylquinoline)acetylacetonate iridium (PQIr(acac)), tris(1-phenylquinoline)iridium (PQIr), or octaethylporphyrin platinum (PtOEP), or a fluorescent material such as tris(8-hydroxyquinolino)aluminum ($Alq_3$) as a light emitting dopant, but the light emitting dopant is not limited thereto. When the light emitting layer emits green light, it is possible to use a phosphorescent material such as fac tris(2-phenylpyridine)iridium ($Ir(ppy)_3$), or a fluorescent material such as tris(8-hydroxyquinolino)aluminum ($Alq_3$), as the light emitting dopant, but the light emitting dopant is not limited thereto. When the light emitting layer emits blue light, it is possible to use a phosphorescent material such as $(4,6\text{-}F_2ppy)_2Irpic$, or a fluorescent material such as spiro-DPVBi, spiro-6P, distyryl benzene (DSB), distyryl arylene (DSA), a PFO-based polymer or a PPV-based polymer as the light emitting dopant, but the light emitting dopant is not limited thereto.

A hole blocking layer may be provided between the electron transport layer and the light emitting layer, and materials known in the art may be used.

The electron transport layer serves to facilitate the transport of electrons, and has a single-layered or multi-layered structure. An electron transport material is suitably a material having high electron mobility which may proficiently accept electrons from a cathode and transfer the electrons to a light emitting layer. Specific examples thereof include: Al complexes of 8-hydroxyquinoline; complexes including $Alq_3$; organic radical compounds; hydroxyflavone-metal complexes; and the like, but are not limited thereto.

In an exemplary embodiment of the present specification, an electron transport layer has a multi-layered structure of two or more layers, and each layer includes a material different from each other.

The electron injection layer serves to facilitate the injection of electrons. An electron injection material is preferably a compound which has a capability of transporting electrons, an effect of injecting electrons from a cathode, and an excellent effect of injecting electrons into a light emitting layer or a light emitting material, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, metal complex compounds, nitrogen-containing 5-membered ring derivatives, and the like, but are not limited thereto.

Examples of the metal complex compounds include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris (2-methyl-8-hydroxyquinolinato) aluminum, tris(8-hydroxyquinolinato) gallium, bis(10-hydroxybenzo[h] quinolinato) beryllium, bis(10-hydroxybenzo[h] quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The organic light emitting device according to the present specification may be a top emission type, a bottom emission type, or a dual emission type according to the material to be used.

Examples and Comparative Examples Hereinafter, the present specification will be described in detail with reference to Examples, Comparative Examples, and the like for specifically describing the present specification. However, the Examples and the Comparative Examples according to the present specification may be modified in various forms, and it is not interpreted that the scope of the present specification is limited to the Examples and the Comparative Examples described below in detail. The Examples and the Comparative Examples of the present specification are provided to more completely explain the present specification to a person with ordinary skill in the art.

Synthesis Example 1. Synthesis of BH-1

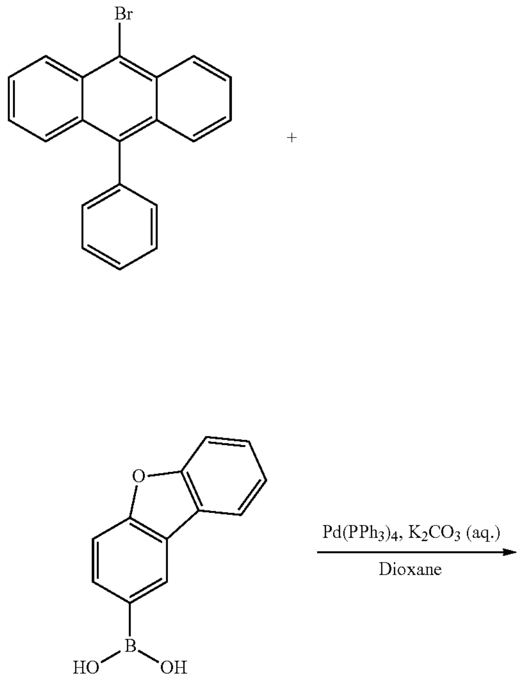

-continued

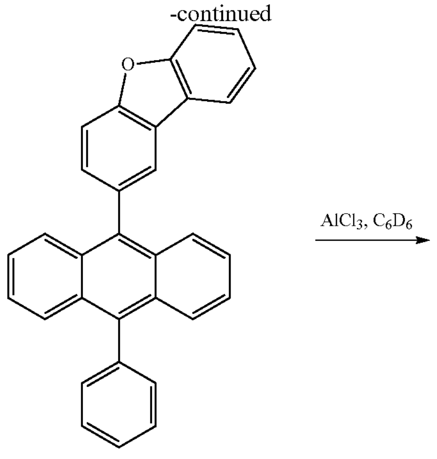

BH-1-a

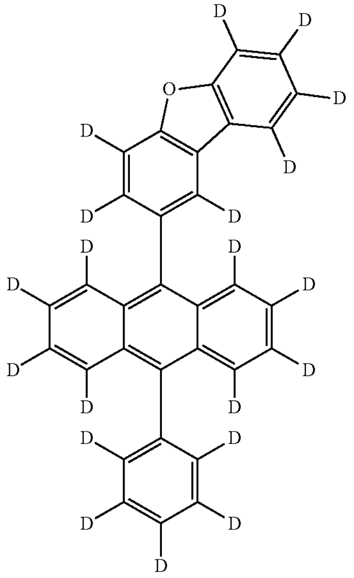

BH-1

<1-a> Preparation of Compound BH-1-a

After 9-bromo-10-phenylanthracene (50 g, 150 mmol) and dibenzo[b,d]furan-2-ylboronic acid (31.8 g, 150 mmol) were dissolved in Dioxane (500 ml), $Pd(PPh_3)_4$ (8.7 g, 7.5 mmol) and 100 ml of an aqueous 2M $K_2CO_3$ solution were added thereto, and the resulting solution was refluxed for 24 hours. The reaction solution was cooled, and the organic layer was extracted with ethyl acetate, and then dried over anhydrous magnesium sulfate. The organic solvent was removed under reduced pressure, and the residue was purified using column chromatography to obtain Compound BH-1-a (39.1 g, yield 62%). MS: [M+H]+=421

<1-b> Preparation of Compound BH-1

Compound BH-1-a (45 g) and $AlCl_3$ (9 g) were put into $C_6D_6$ (900 ml), and the resulting solution was stirred for 2 hours. After the reaction was completed, $D_2O$ (60 ml) was added thereto, the resulting solution was stirred for 30 minutes, and then trimethylamine (6 ml) was added dropwise thereto. The reaction solution was transferred to a separatory funnel, and an extraction with water and toluene was performed. The extract was dried over $MgSO_4$, and then the residue was recrystallized with ethyl acetate to obtain BH-1 at a yield of 67%. MS: [M+H]+=441

Synthesis Example 2. Synthesis of BH-2

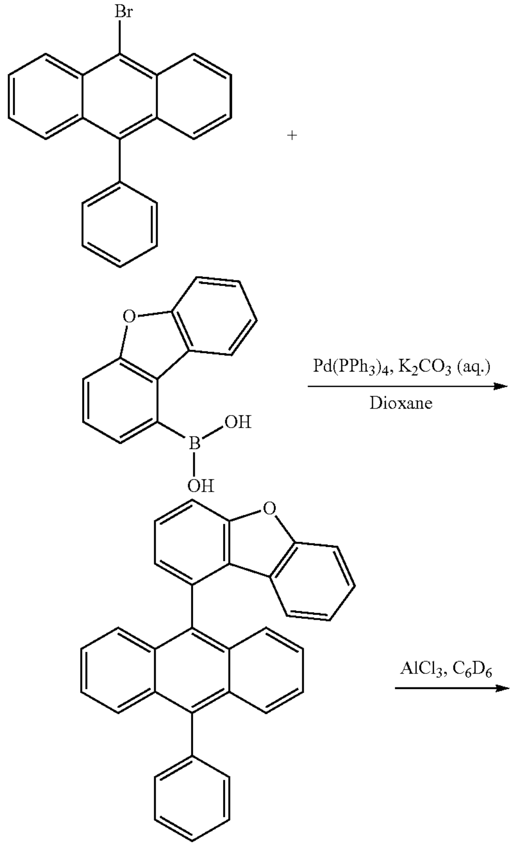

BH-2-a

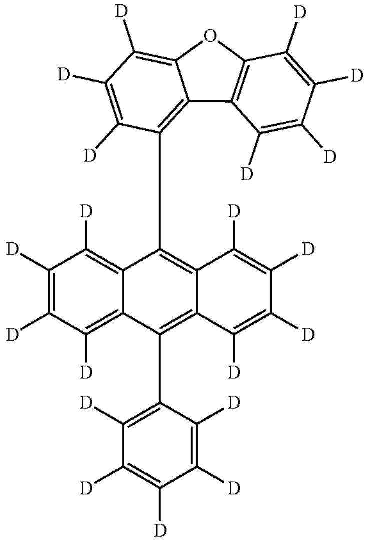

BH-2

<2-a> Preparation of Compound BH-2-a

Compound BH-2-a was obtained by performing synthesis and purification in the same manner as in Synthesis Example 1-a, except that dibenzo[b,d]furan-2-ylboronic acid was changed into dibenzo[b,d]furan-1-ylboronic acid. MS: [M+H]+=421

<2-b> Preparation of Compound BH-2

Compound BH-2 was obtained by performing synthesis and purification in the same manner as in Synthesis Example 1-b, except that Compound BH-1-a was changed into Compound BH-2-a. MS: [M+H]+=441

Synthesis Example 3. Synthesis of BH-3

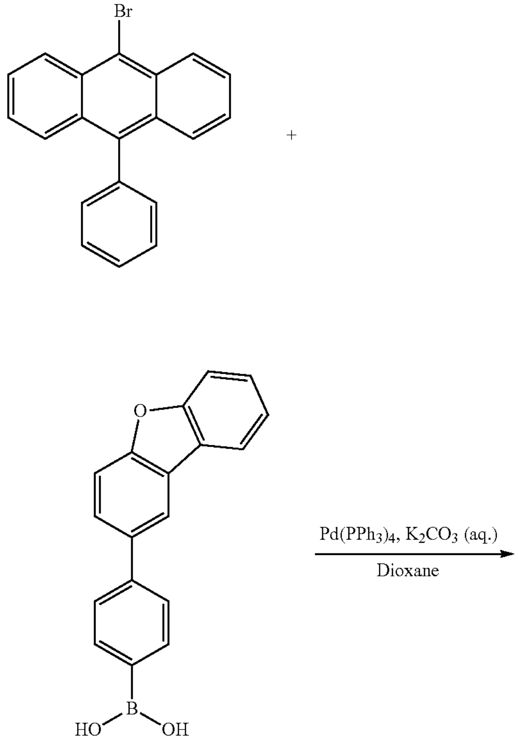

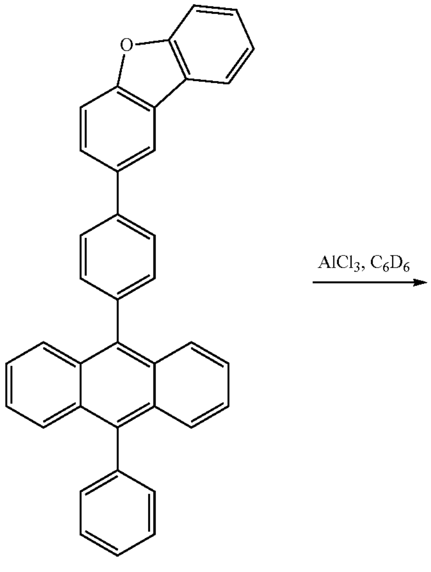

BH-3-a

-continued

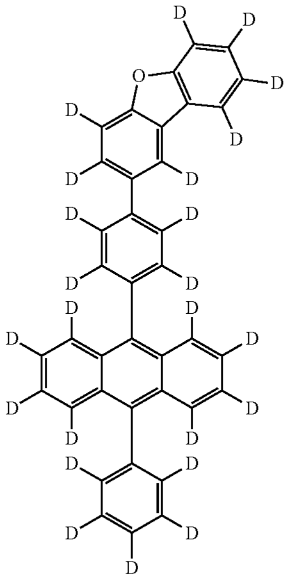

BH-3

<3-a> Preparation of Compound BH-3-a

Compound BH-3-a was obtained by performing synthesis and purification in the same manner as in Synthesis Example 1-a, except that dibenzo[b,d]furan-2-ylboronic acid was changed into (4-dibenzo[b,d]furan-2-yl)phenyl)boronic acid. MS: [M+H]+=497

<3-b> Preparation of Compound BH-3

Compound BH-3 was obtained by performing synthesis and purification in the same manner as in Synthesis Example 1-b, except that Compound BH-1-a was changed into Compound BH-3-a. MS: [M+H]+=521

Synthesis Example 4. Synthesis of BH-4

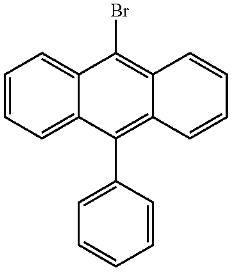

+

-continued

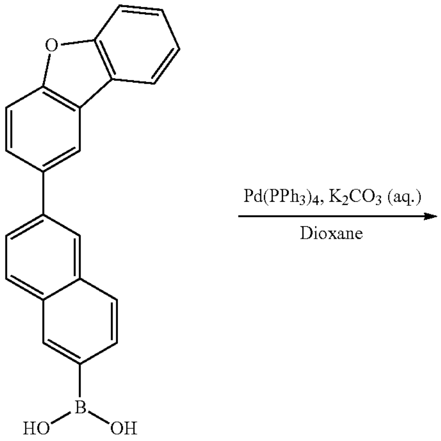

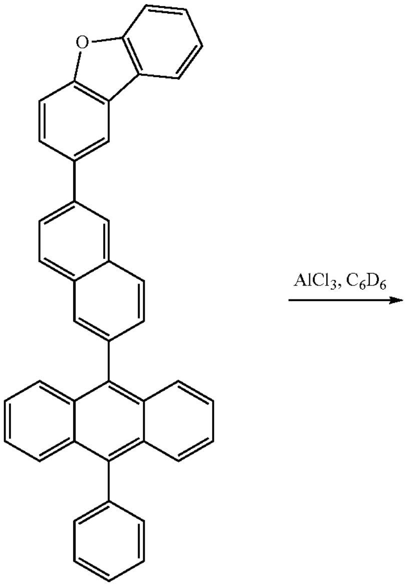

BH-4-a

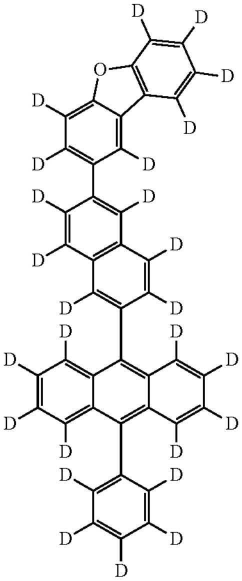

BH-4

<4-a> Preparation of Compound BH-4-a

Compound BH-4-a was obtained by performing synthesis and purification in the same manner as in Synthesis Example 1-a, except that dibenzo[b,d]furan-2-ylboronic acid was changed into (6-dibenzo[b,d]furan-2-yl)naphthalen-2-yl)boronic acid. MS: [M+H]+=547

<4-b> Preparation of Compound BH-4

Compound BH-4 was obtained by performing synthesis and purification in the same manner as in Synthesis Example 1-b, except that Compound BH-1-a was changed into Compound BH-4-a. MS: [M+H]+=573

Synthesis Example 5. Synthesis of BH-5

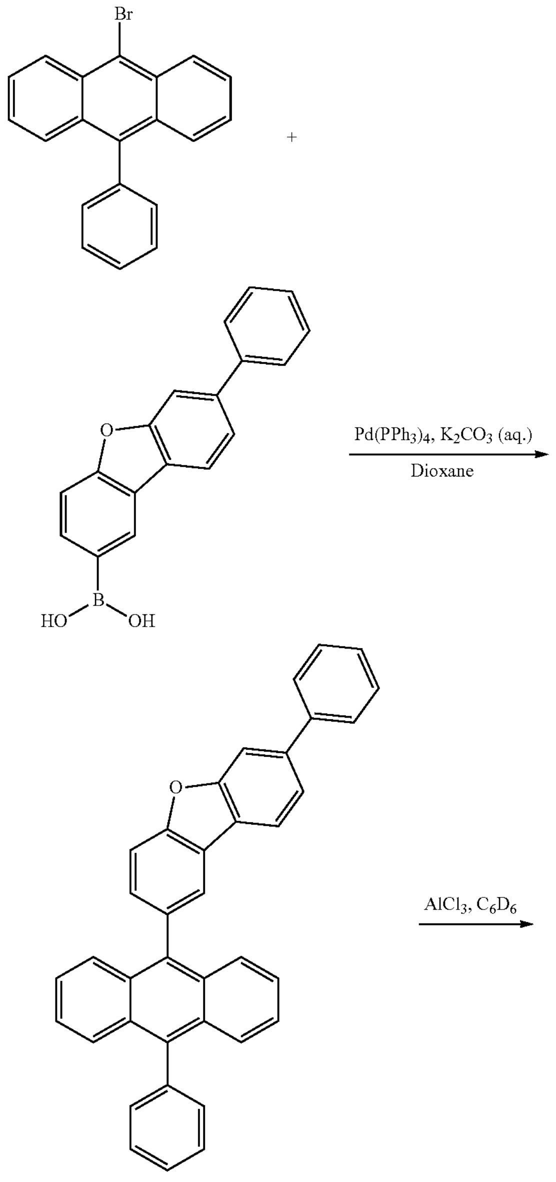

BH-5-a

-continued

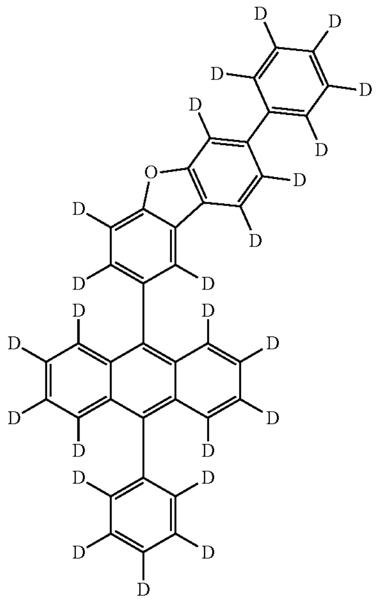

BH-5

<5-a> Preparation of Compound BH-5-a

Compound BH-5-a was obtained by performing synthesis and purification in the same manner as in Synthesis Example 1-a, except that dibenzo[b,d]furan-2-ylboronic acid was changed into (7-phenyldibenzo[b,d]furan-2-yl)boronic acid. MS: [M+H]+=497

<5-b> Preparation of Compound BH-5

Compound BH-5 was obtained by performing synthesis and purification in the same manner as in Synthesis Example 1-b, except that Compound BH-1-a was changed into Compound BH-5-a. MS: [M+H]+=521

Synthesis Example 6. Synthesis of BH-6

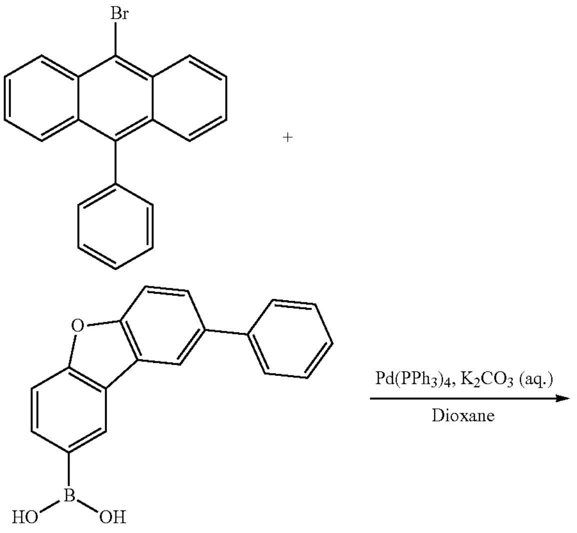

-continued

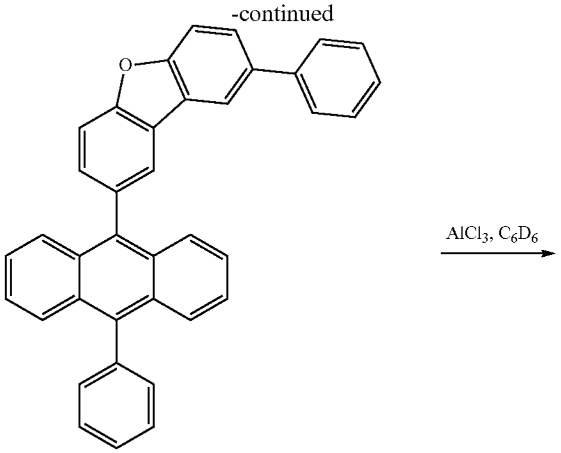

BH-6-a

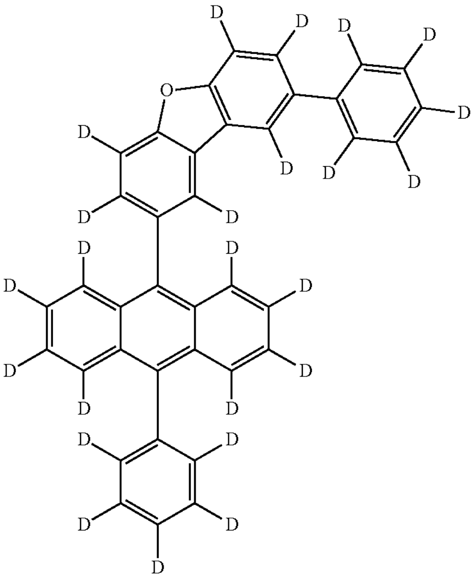

BH-6

<6-a> Preparation of Compound BH-6-a

Compound BH-6-a was obtained by performing synthesis and purification in the same manner as in Synthesis Example 1-a, except that dibenzo[b,d]furan-2-ylboronic acid was changed into (8-phenyldibenzo[b,d]furan-2-yl)boronic acid. MS: [M+H]+=497

<6-b> Preparation of Compound BH-6

Compound BH-6 was obtained by performing synthesis and purification in the same manner as in Synthesis Example 1-b, except that Compound BH-1-a was changed into Compound BH-6-a. MS: [M+H]+=521

Synthesis Example 8. Synthesis of BH-8

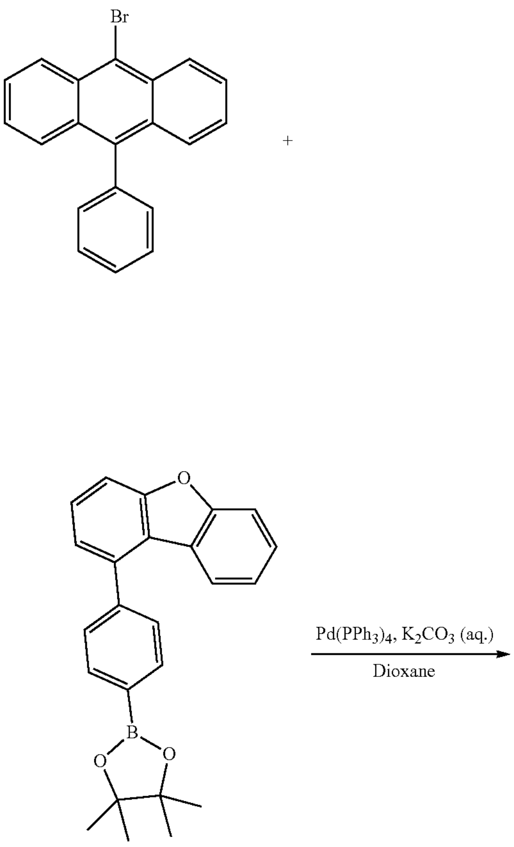

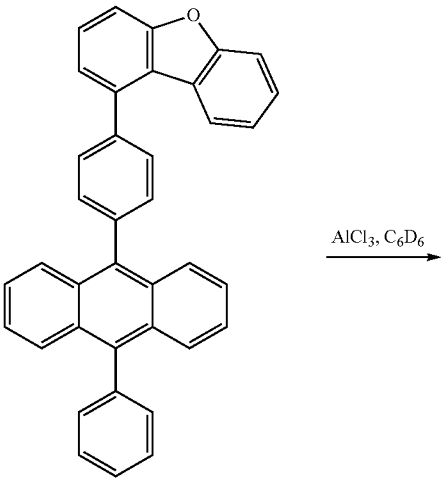

BH-8-a

-continued

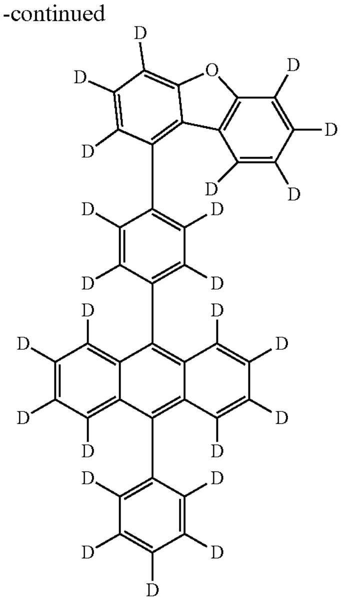

BH-8

<8-a> Preparation of Compound BH-8-a

Compound BH-8-a was obtained by performing synthesis and purification in the same manner as in Synthesis Example 1-a, except that dibenzo[b,d]furan-2-ylboronic acid was changed into 2-(4-(dibenzo[b,d]furan-1-yl)phenyl)-4,4,5,5-tetramethyl-1,3,2-dioxaborolane. MS: [M+H]+=497

<8-b> Preparation of Compound BH-8

Compound BH-8 was obtained by performing synthesis and purification in the same manner as in Synthesis Example 1-b, except that Compound BH-1-a was changed into Compound BH-8-a. MS: [M+H]+=521

Synthesis Example 9. Synthesis of BH-9

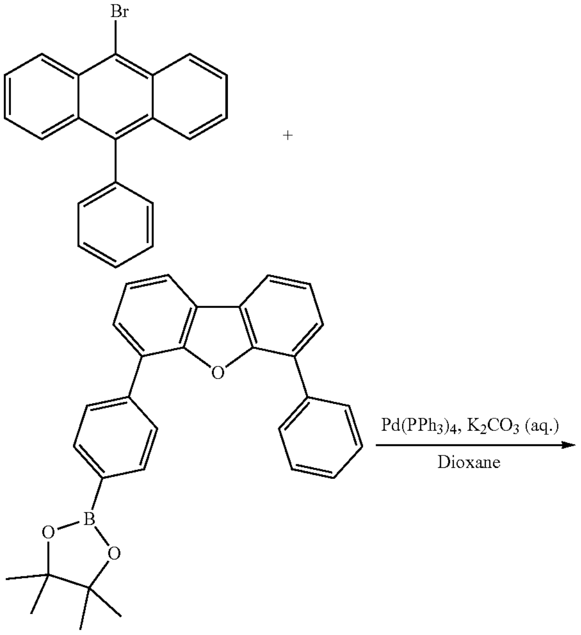

-continued

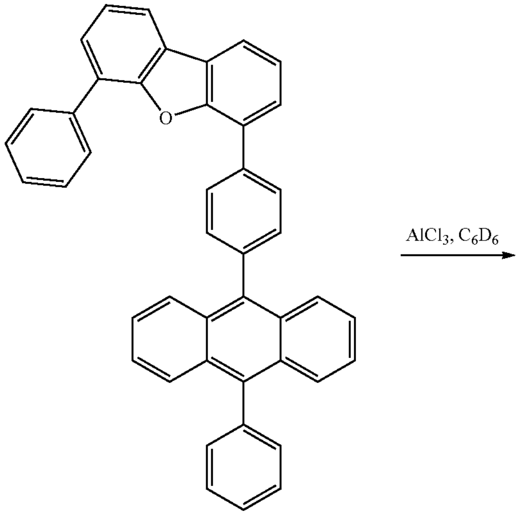

BH-9-a

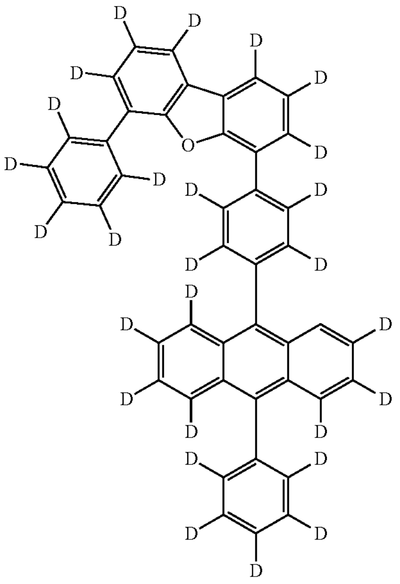

BH-9

<9-a> Preparation of Compound BH-9-a

Compound BH-9-a was obtained by performing synthesis and purification in the same manner as in Synthesis Example 1-a, except that dibenzo[b,d]furan-2-ylboronic acid was changed into 4,4,5,5-tetramethyl-2-(4-(6-phenyldibenzo[b,d]furan-4-yl)phenyl)-1,3,2-dioxaborolane. MS: [M+H]+=573

<9-b> Preparation of Compound BH-9

Compound BH-9 was obtained by performing synthesis and purification in the same manner as in Synthesis Example 1-b, except that Compound BH-1-a was changed into Compound BH-9-a. MS: [M+H]+=601

Synthesis Example 10. Synthesis of BH-10

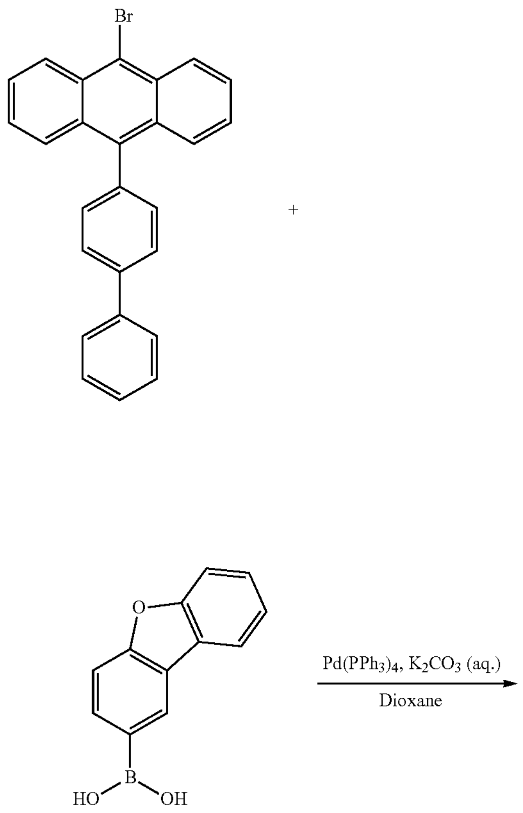

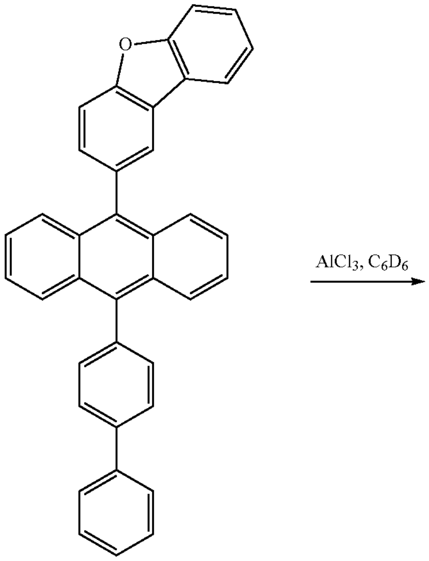

BH-10-a

-continued

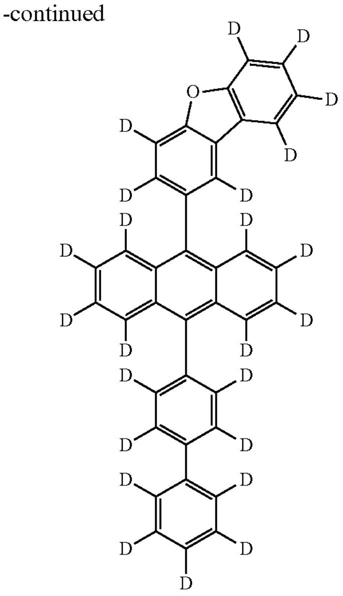

BH-10

<10-a> Preparation of Compound BH-10-a

Compound BH-10-a was obtained by performing synthesis and purification in the same manner as in Synthesis Example 1-a, except that 9-bromo-10-phenylanthracene was changed into 9-([1,1'-biphenyl]-4-yl)-10-bromoanthracene. MS: [M+H]+=497

<10-b> Preparation of Compound BH-10

Compound BH-10 was obtained by performing synthesis and purification in the same manner as in Synthesis Example 1-b, except that Compound BH-1-a was changed into Compound BH-10-a. MS: [M+H]+=521

Synthesis Example 11. Synthesis of BH-11

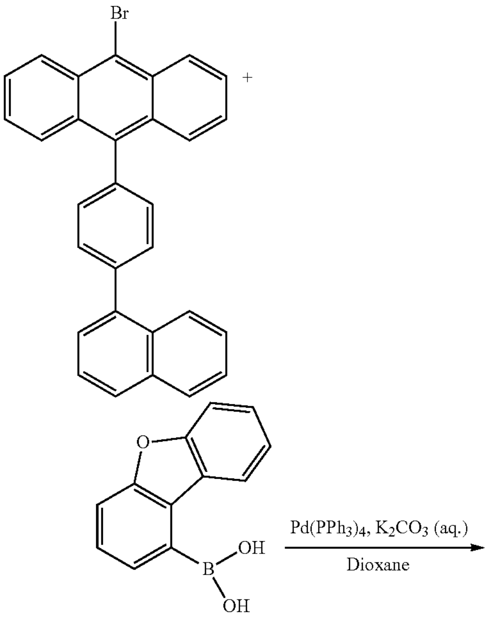

-continued

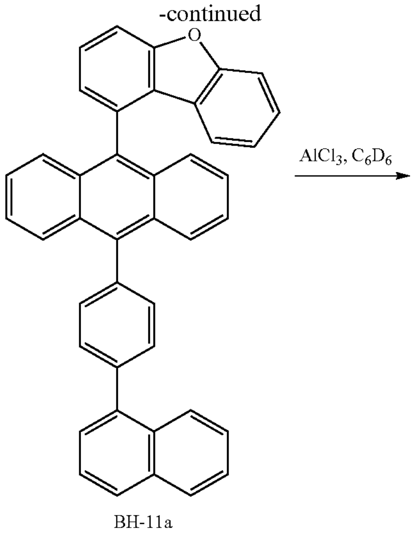

BH-11a

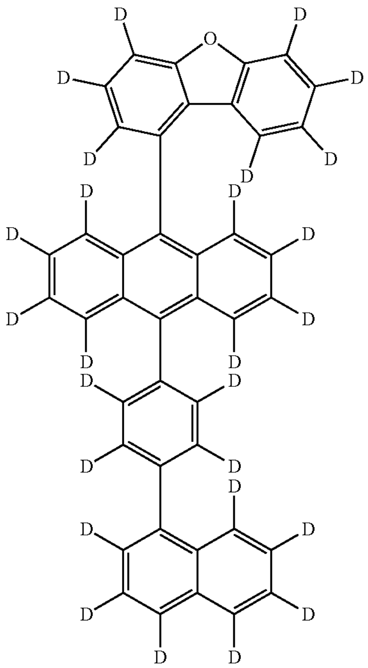

BH-11

<11-a> Preparation of Compound BH-11-a

Compound BH-11-a was obtained by performing synthesis and purification in the same manner as in Synthesis Example 1-a, except that 9-bromo-10-phenylanthracene was changed into 9-bromo-10-(4-(naphthalen-1-yl)phenyl)anthracene and dibenzo[b,d]furan-2-ylboronic acid was changed into dibenzo[b,d]furan-1-ylboronic acid. MS: [M+H]+=547

<11-b> Preparation of Compound BH-11

Compound BH-11 was obtained by performing synthesis and purification in the same manner as in Synthesis Example 1-b, except that Compound BH-1-a was changed into Compound BH-11-a. MS: [M+H]+=573

Synthesis Example 12. Synthesis of BH-12

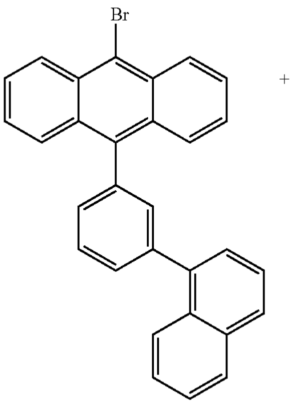

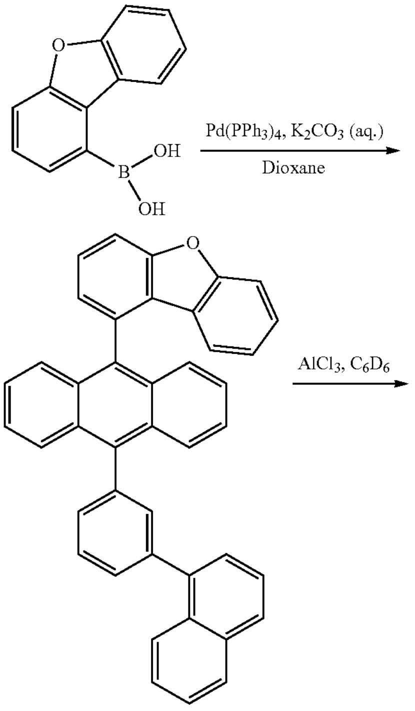

BH-12-a

-continued

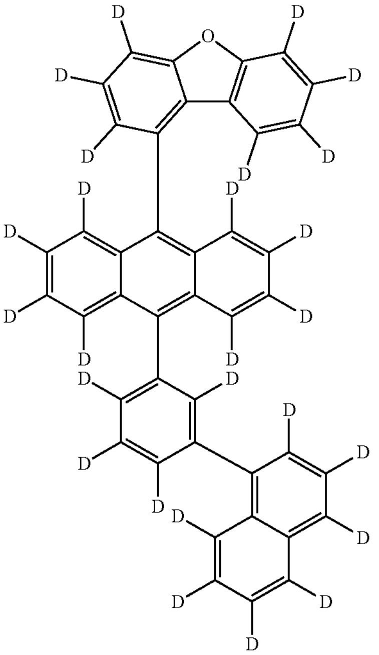

BH-12

<12-a> Preparation of Compound BH-12-a

Compound BH-12-a was obtained by performing synthesis and purification in the same manner as in Synthesis Example 1-a, except that 9-bromo-10-phenylanthracene was changed into 9-bromo-10-(3-(naphthalen-1-yl)phenyl)anthracene, and dibenzo[b,d]furan-2-ylboronic acid was changed into dibenzo[b,d]furan-1-ylboronic acid. MS: [M+H]+=547

<12-b> Preparation of Compound BH-12

Compound BH-12 was obtained by performing synthesis and purification in the same manner as in Synthesis Example 1-b, except that Compound BH-1-a was changed into Compound BH-12-a. MS: [M+H]+=573

Synthesis Example 13. Synthesis of BH-13

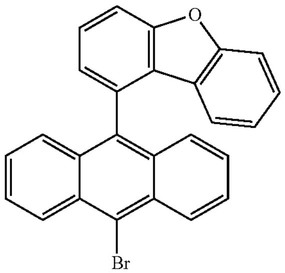

+

-continued

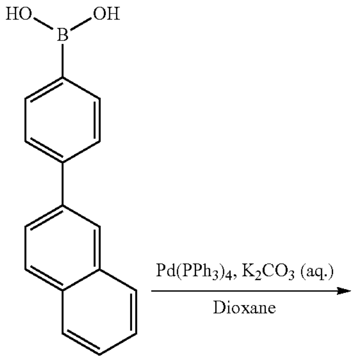

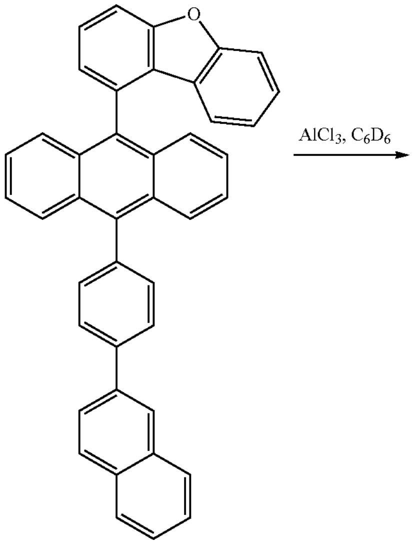

BH-13-a

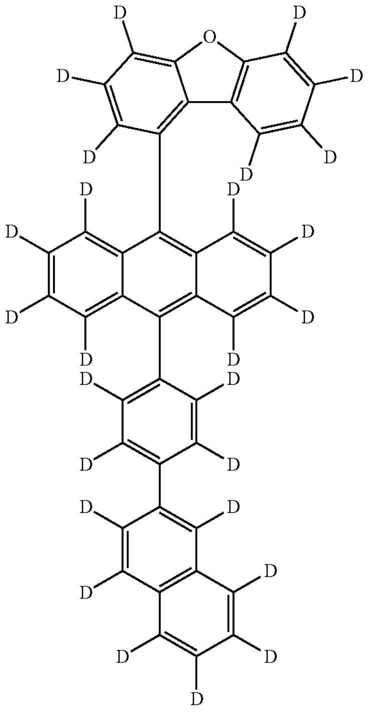

BH-13

<13-a> Preparation of Compound BH-13-a

Compound BH-13-a was obtained by performing synthesis and purification in the same manner as in Synthesis Example 1-a, except that 9-bromo-10-phenylanthracene was changed into 1-(10-bromoanthracen-9-yl)dibenzo[b,d]furan, and dibenzo[b,d]furan-2-ylboronic acid was changed into (4-(naphthalen-2-yl)phenyl)boronic acid. MS: [M+H]+=547

<13-b> Preparation of BH-13

Compound BH-13 was obtained by performing synthesis and purification in the same manner as in Synthesis Example 1-b, except that Compound BH-1-a was changed into Compound BH-13-a. MS: [M+H]+=573

Synthesis Example 14. Synthesis of BH-14

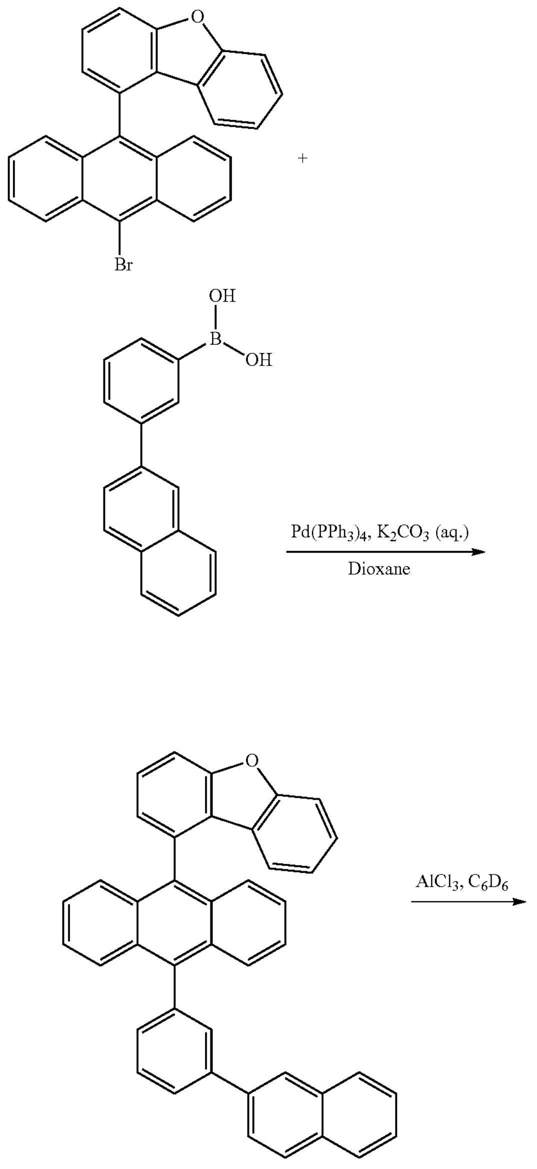

BH-14-a

-continued

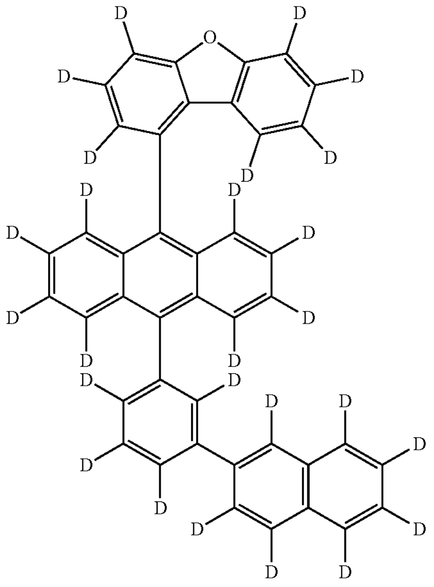

BH-14

<14-a> Preparation of Compound BH-14-a

Compound BH-14-a was obtained by performing synthesis and purification in the same manner as in Synthesis Example 1-a, except that 9-bromo-10-phenylanthracene was changed into 1-(10-bromoanthracen-9-yl)dibenzo[b,d]furan, and dibenzo[b,d]furan-2-ylboronic acid was changed into (3-(naphthalen-2-yl)phenyl)boronic acid. MS: [M+H]+=547

<14-b> Preparation of BH-14

Compound BH-14 was obtained by performing synthesis and purification in the same manner as in Synthesis Example 1-b, except that Compound BH-1-a was changed into Compound BH-14-a. MS: [M+H]+=573

Synthesis Example 15. Synthesis of BH-15

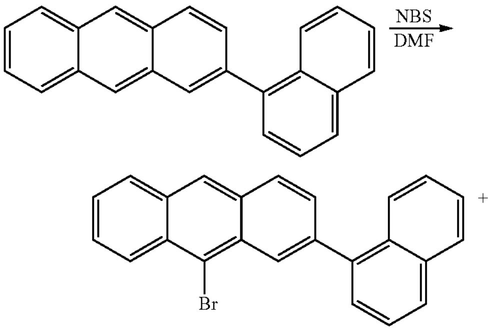

BH-15-a

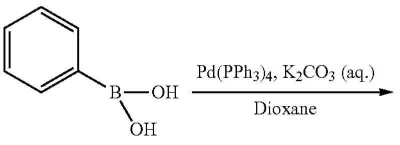

-continued

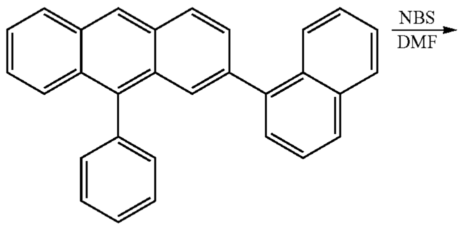

BH-15-b

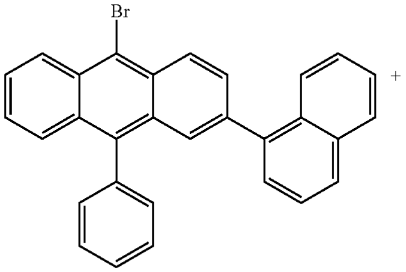

BH-15-c

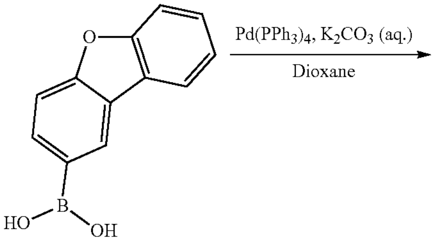

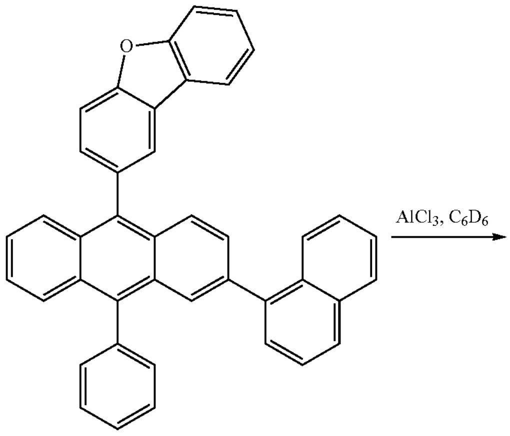

BH-15-d

-continued

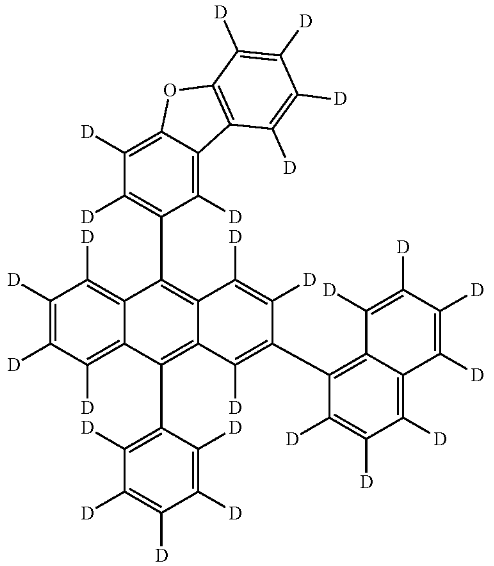

BH-15

<15-a> Preparation of Compound BH-15-a

After 2-(1-naphthyl)anthracene (50 g, 164 mmol) was dispersed in 500 ml of dimethylformamide, a solution of n-bromosuccinimide (29.2 g, 164 mmol) dissolved in 50 ml of dimethylformamide was slowly added dropwise thereto. After reaction at room temperature for 2 hours, 1 L of water was added dropwise thereto. When a solid was produced, the solid was filtered, and then dissolved in ethyl acetate, and the resulting solution was put into a separatory funnel, and then washed several times with distilled water.

The resulting product was recrystallized in ethyl acetate to obtain Compound BH-15-a (56 g, yield 89%). MS: [M+H]+= 383

<15-b> Preparation of Compound BH-15-b

Compound BH-15-b was obtained by performing synthesis and purification in the same manner as in Synthesis Example 1-a, except that 9-bromo-10-phenylanthracene was changed into 9-bromo-2-phenylanthracene, and dibenzo[b, d]furan-2-ylboronic acid was changed into phenylboronic acid. MS: [M+H]+=381

<15-c> Preparation of Compound BH-15-c

Compound BH-15-c was obtained by performing synthesis and purification in the same manner as in Synthesis Example 15-a, except that 2-(1-naphthyl)anthracene was changed into Compound BH-15-b. MS: [M+H]+=459

<15-d> Preparation of Compound BH-15-d

Compound BH-15-d was obtained by performing synthesis and purification in the same manner as in Synthesis Example 1-a, except that 9-bromo-10-phenylanthracene was changed into Compound BH-15-c. MS: [M+H]+=547

<15-e> Preparation of Compound BH-15

Compound BH-15 was obtained by performing synthesis and purification in the same manner as in Synthesis Example 1-b, except that Compound BH-1-a was changed into Compound BH-15-d. MS: [M+H]+=573

Synthesis Example 16. Synthesis of BH-16

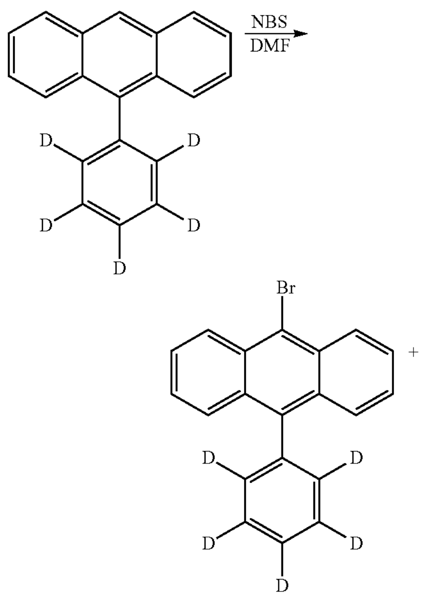

BH-16-a

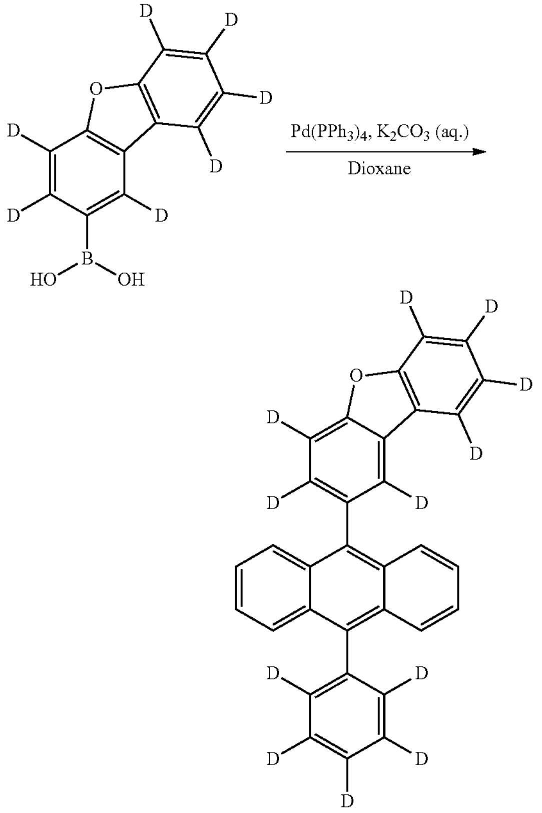

BH-16

<16-a> Preparation of Compound BH-16-a

Compound BH-16-a was obtained by performing synthesis and purification in the same manner as in Synthesis Example 15-a, except that 2-(1-naphthyl)anthracene was changed into Compound 9-(phenyl-$d_5$)anthracene. MS: [M+H]+=338

<16-b> Preparation of Compound BH-16

Compound BH-16 was obtained by performing synthesis and purification in the same manner as in Synthesis Example 1-b, except that Compound BH-1-a was changed into Compound BH-16-a. MS: [M+H]+=433

Synthesis Example 17. Synthesis of BH-17

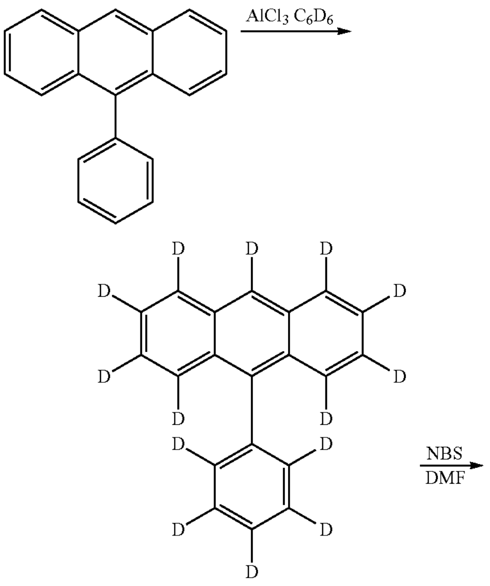

BH-17-a

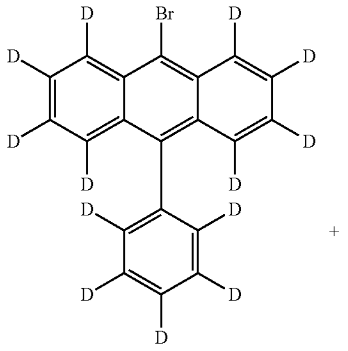

BH-17-b

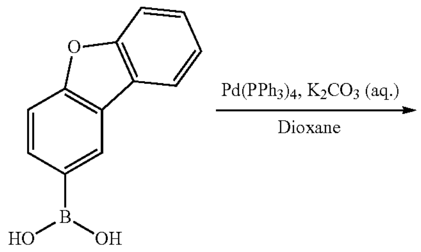

-continued

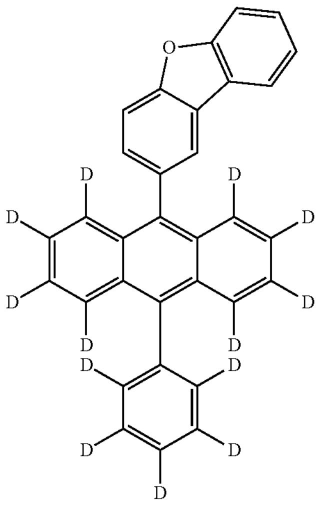

BH-17

<17-a> Preparation of Compound BH-17-a

Compound BH-17-a was obtained by performing synthesis and purification in the same manner as in Synthesis Example 1-b, except that Compound BH-1-a was changed into 9-phenylanthracene. MS: [M+H]+=269

<17-b> Preparation of Compound BH-17-b

Compound BH-17-b was obtained by performing synthesis and purification in the same manner as in Synthesis Example 15-a, except that 2-phenylanthracene was changed into Compound BH-17-a. MS: [M+H]+=346

<17-c> Preparation of Compound BH-17

Compound BH-17 was obtained by performing synthesis and purification in the same manner as in Synthesis Example 1-a, except that 9-bromo-10-phenylanthracene was changed into Compound BH-17-b. MS: [M+H]+=454

Synthesis Example 18. Synthesis of BH-18

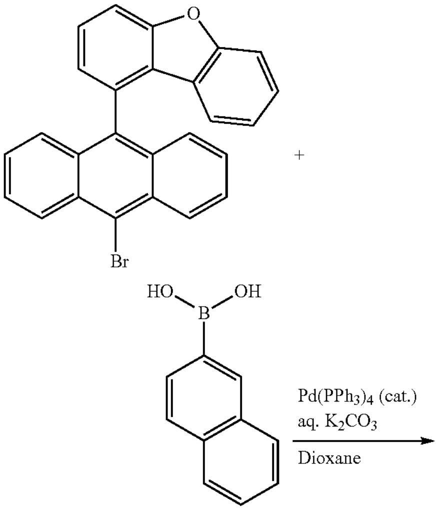

-continued

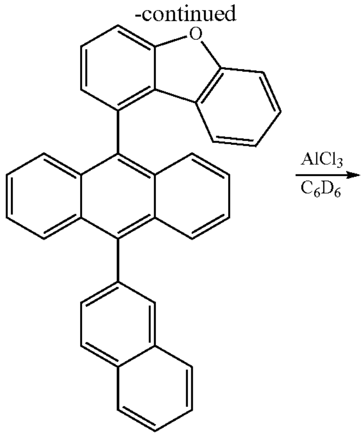

BH-18-H

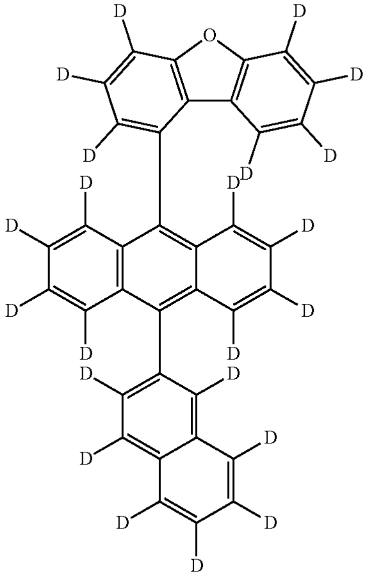

BH-18

<18-a> Preparation of Compound BH-18-H

After 1-(10-bromoanthracen-9-yl)dibenzo[b,d]furan (50 g, 118 mmol) and 2-naphthylboronic acid (20.3 g, 118 mmol) were dissolved in THF (600 ml), $Pd(PPh_3)_4$ (6.82 g, 5.9 mmol) and 120 ml of an aqueous 2M $K_2CO_3$ solution were added thereto, and the resulting solution was refluxed for 24 hours. The reaction solution was cooled, and the organic layer was extracted with ethyl acetate, and then dried over anhydrous magnesium sulfate. The organic solvent was removed under reduced pressure, and the residue was purified using column chromatography to obtain Compound BH-18-H (45 g, yield 81%). (MS[M+H]+=471)

<18-b> Preparation of Compound BH-18

The synthesized Compound BH-18-H (45 g) and $AlCl_3$ (9 g) were put into $C_6D_6$ (900 ml), and the resulting solution was stirred for 2 hours. After the reaction was completed, $D_2O$ (60 ml) was added thereto, the resulting solution was stirred for 30 minutes, and then trimethylamine (6 ml) was added dropwise thereto. The reaction solution was transferred to a separatory funnel, and an extraction with water and toluene was performed. The extract was dried over $MgSO_4$, and then the residue was recrystallized with ethyl acetate to obtain BH-18 at a yield of 60%. (MS[M+H]+=493)

Synthesis Example 19. Synthesis of BH-19

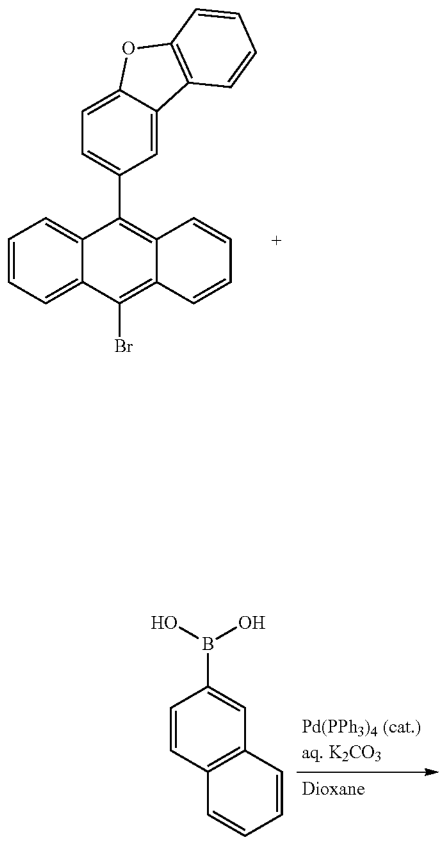

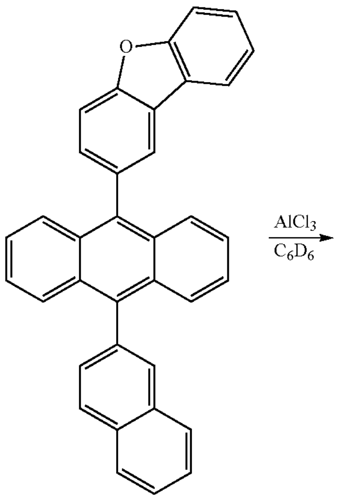

BH-19-H

-continued

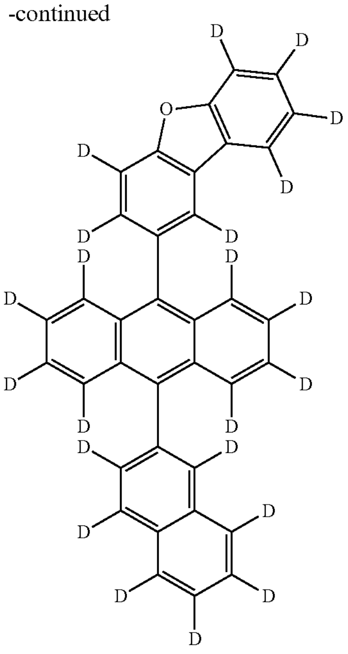

BH-19

<19-a> Preparation of Compound BH-19-H

BH-19-H was obtained by reacting 2-(10-bromoanthracen-9-yl)dibenzo[b,d]furan with 2-naphthylboronic acid in the same manner as in Synthesis Example <18-a>. (Yield 78%, MS[M+H]+=471)

<19-b> Preparation of Compound BH-19

BH-19 was obtained from BH-19-H in the same manner as in Synthesis Example <18-b>. (Yield 62%, MS[M+H]+=493)

Synthesis Example 20. Synthesis of BH-20

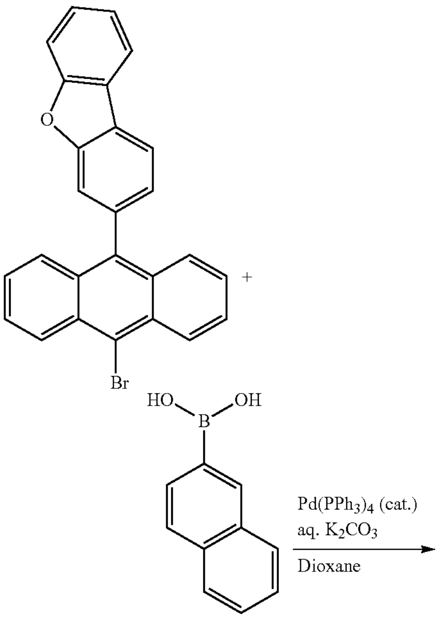

-continued
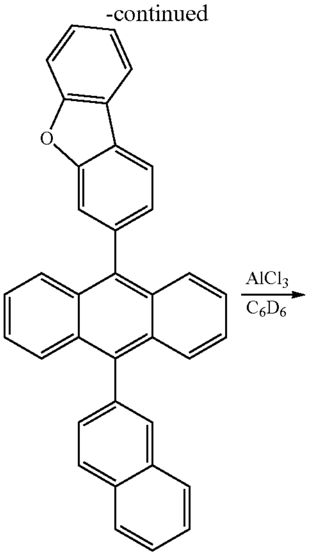
BH-20-H
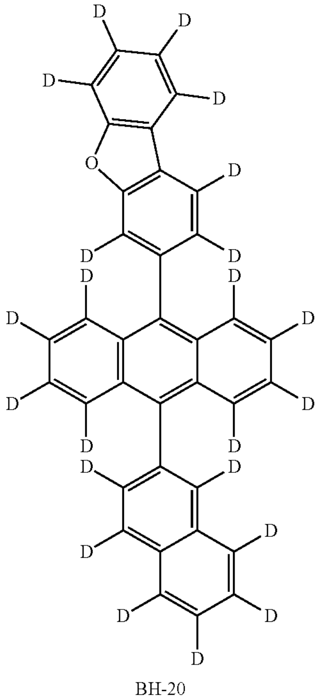
BH-20
<20-a> Preparation of Compound BH-20-H
BH-20-H was obtained by reacting 3-(10-bromoanthracen-9-yl)dibenzo[b,d]furan with 2-naphthylboronic acid in the same manner as in Synthesis Example <18-a>. (Yield 69%, MS[M+H]+=471)
<20-b> Preparation of Compound BH-20
BH-20 was obtained from BH-20-H in the same manner as in Synthesis Example <18-b>. (Yield 65%, MS[M+H]+=493)
Synthesis Example 21. Synthesis of BH-21
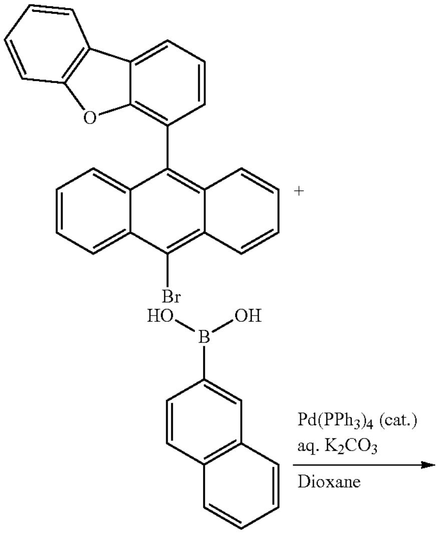
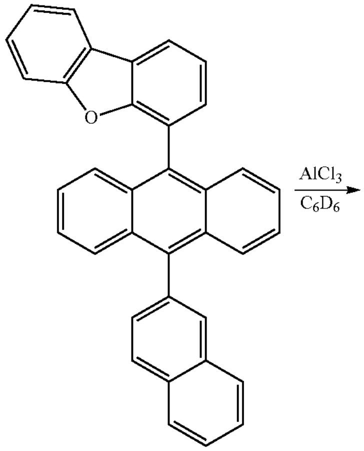
BH-21-H
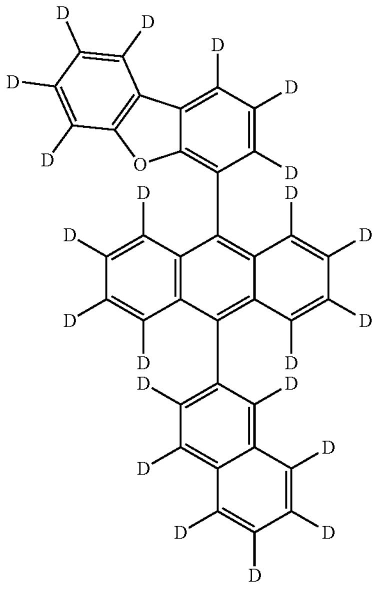
BH-21

<21-a> Preparation of Compound BH-21-H

BH-21-H was obtained by reacting 4-(10-bromoanthracen-9-yl)dibenzo[b,d]furan with 2-naphthylboronic acid in the same manner as in Synthesis Example <18-a>. (Yield 71%, MS[M+H]+=471, Dipole moment=0.58 D)

<21-b> Preparation of Compound BH-21

BH-21 was obtained from BH-21-H in the same manner as in Synthesis Example <18-b>. (Yield 55%, MS[M+H]+=493)

Synthesis Example 22. Synthesis of BH-22

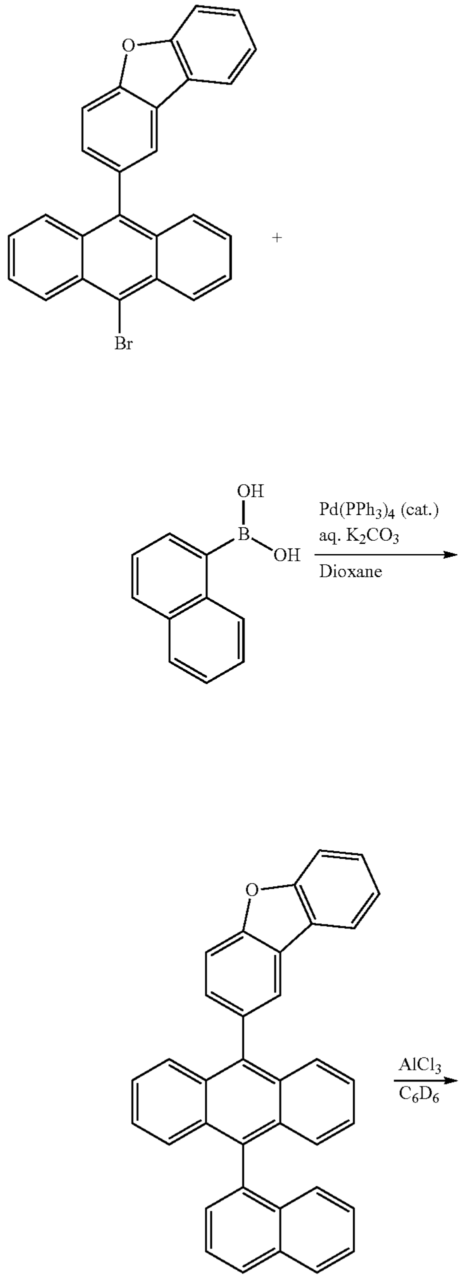

BH-22-H

-continued

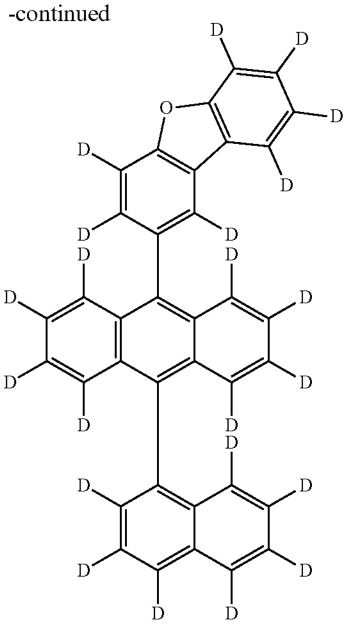

BH-22

<22-a> Preparation of Compound BH-22-H

BH-22-H was obtained by reacting 2-(10-bromoanthracen-9-yl)dibenzo[b,d]furan with 1-naphthylboronic acid in the same manner as in Synthesis Example <18-a>. (Yield 82%, MS[M+H]+=471)

<22-b> Preparation of Compound BH-22

BH-22 was obtained from BH-22-H in the same manner as in Synthesis Example <18-b>. (Yield 68%, MS[M+H]+=493)

Synthesis Example 23. Synthesis of BH-23

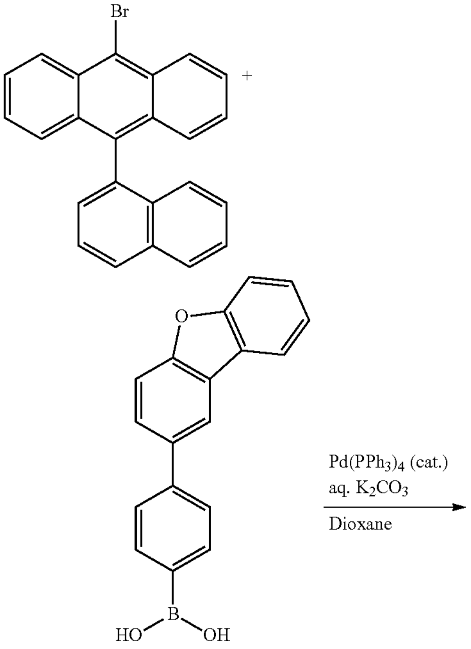

-continued

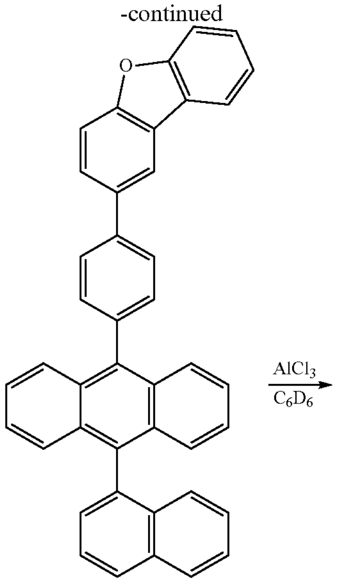

BH-23-H

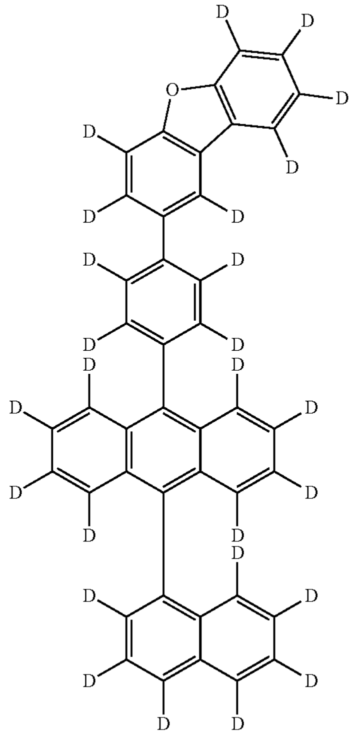

BH-23

<23-a> Preparation of Compound BH-23-H

BH-23-H was obtained by reacting 9-bromo-10-(naphthalen-1-yl)anthracene with (4-(dibenzo[b,d]furan-2-yl)phenyl)boronic acid in the same manner as in Synthesis Example <18-a>. (Yield 73%, MS[M+H]+=547)

<23-b> Preparation of Compound BH-23

BH-23 was obtained from BH-23-H in the same manner as in Synthesis Example <18-b>. (Yield 60%, MS[M+H]+=573)

Synthesis Example 24. Synthesis of BH-24

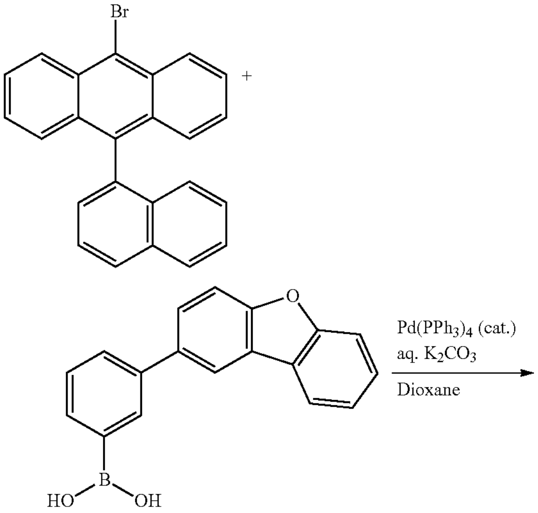

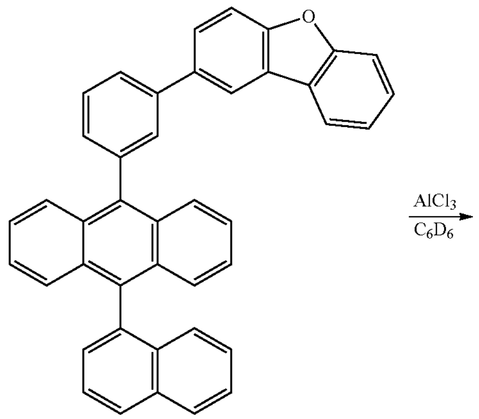

BH-24-H

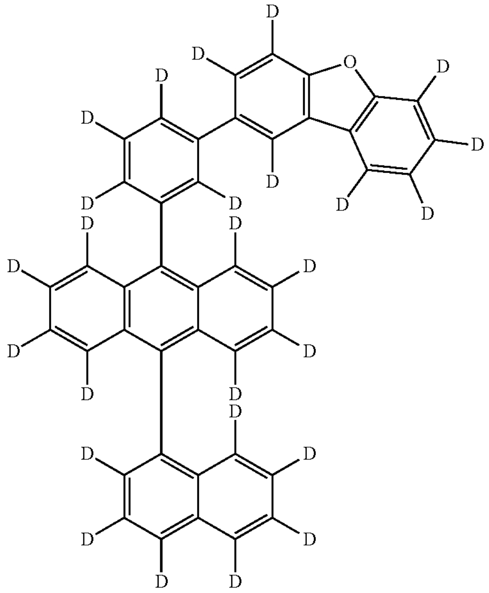

BH-24

<24-a> Preparation of Compound BH-24-H

BH-24-H was obtained by reacting 9-bromo-10-(naphthalen-1-yl)anthracene with (3-(dibenzo[b,d]furan-2-yl)phenyl)boronic acid in the same manner as in Synthesis Example <18-a>. (Yield 70%, MS[M+H]+=547)

<24-b> Preparation of Compound BH-24

BH-24 was obtained from BH-24-H in the same manner as in Synthesis Example <18-b>. (Yield 66%, MS[M+H]+=573)

Synthesis Example 25. Synthesis of BH-25

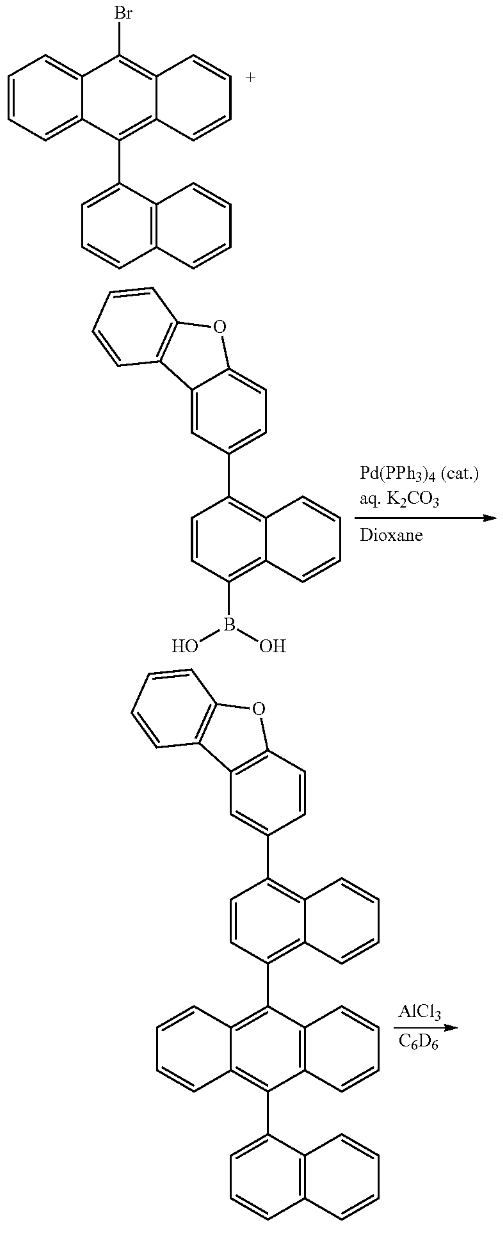

BH-25-H

-continued

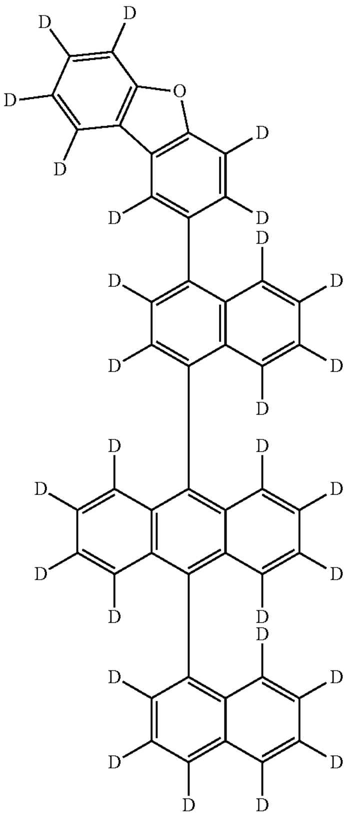

BH-25

<25-a> Preparation of Compound BH-25-H

BH-25-H was obtained by reacting 9-bromo-10-(naphthalen-1-yl)anthracene with (4-(dibenzo[b,d]furan-2-yl)naphthalen-1-yl)boronic acid in the same manner as in Synthesis Example <18-a>. (Yield 73%, MS[M+H]+=597)

<25-b> Preparation of Compound BH-25

BH-25 was obtained from BH-25-H in the same manner as in Synthesis Example <18-b>. (Yield 64%, MS[M+H]+=625)

Synthesis Example 26. Synthesis of BH-26

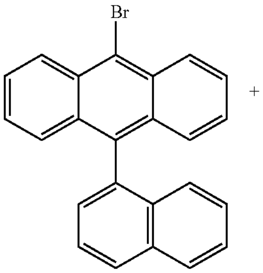

-continued

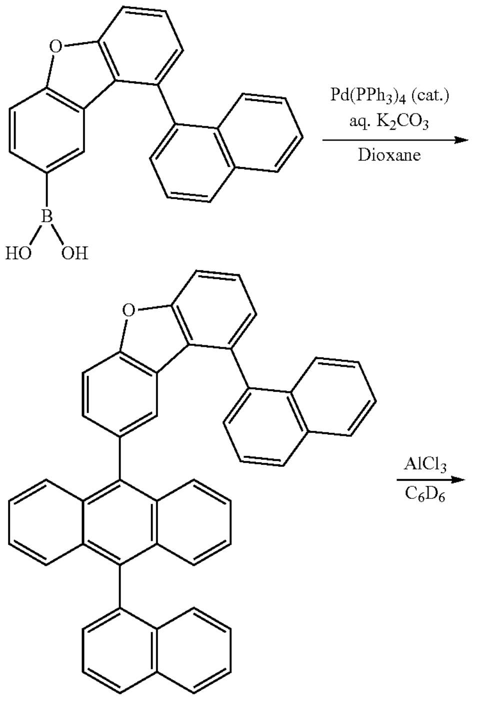

BH-27-H

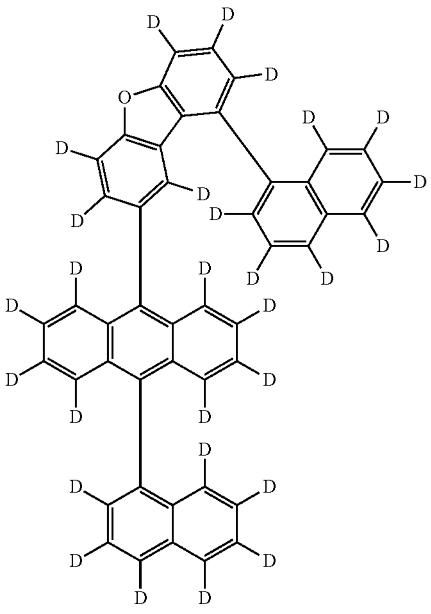

BH-26

<26-a> Preparation of Compound BH-26-H

BH-26-H was obtained by reacting 9-bromo-10-(naphthalen-1-yl)anthracene with (9-(naphthalen-1-yl)dibenzo[b,d]furan-2-yl)boronic acid in the same manner as in Synthesis Example <18-a>. (Yield 64%, MS[M+H]+=597)

<26-b> Preparation of Compound BH-26

BH-26 was obtained from BH-26-H in the same manner as in Synthesis Example <18-b>. (Yield 62%, MS[M+H]+=625)

Synthesis Example 27. Synthesis of BH-27

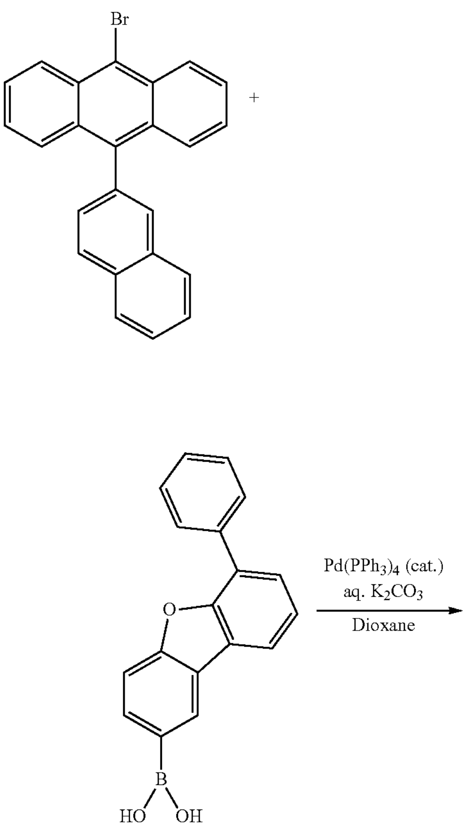

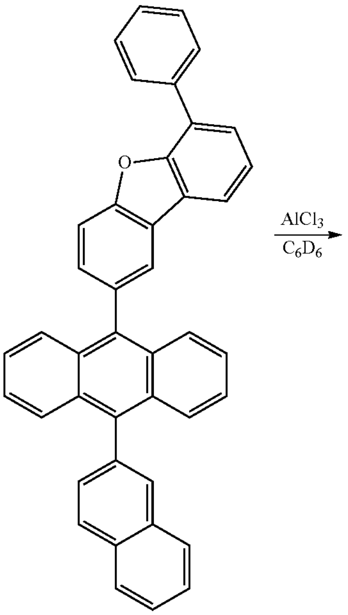

BH-27-H

-continued

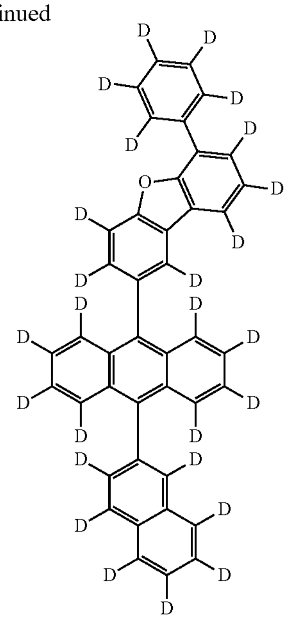

BH-27

<27-a> Preparation of Compound BH-27-H

BH-27-H was obtained by reacting 9-bromo-10-(naphthalen-2-yl)anthracene with (6-phenyldibenzo[b,d]furan-2-yl) boronic acid in the same manner as in Synthesis Example <18-a>. (Yield 67%, MS[M+H]+=547)

<27-b> Preparation of Compound BH-27

BH-27 was obtained from BH-27-H in the same manner as in Synthesis Example <18-b>. (Yield 65%, MS[M+H]+=573)

Synthesis Example 28. Synthesis of BH-28

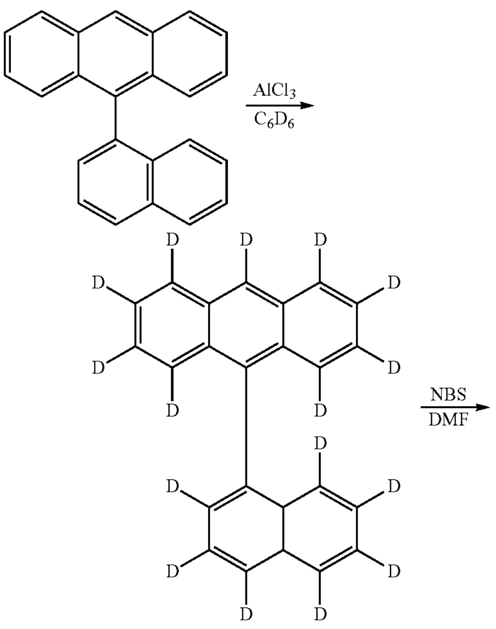

BH-28-a

-continued

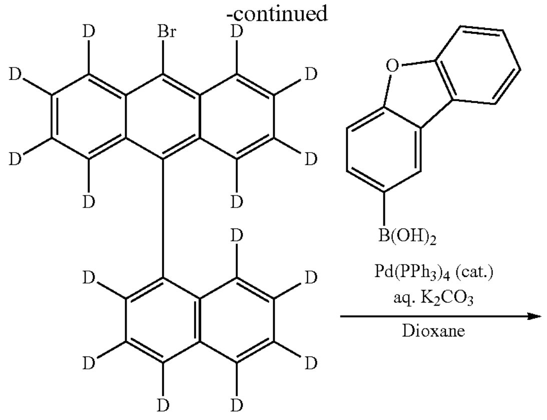

BH-28-b

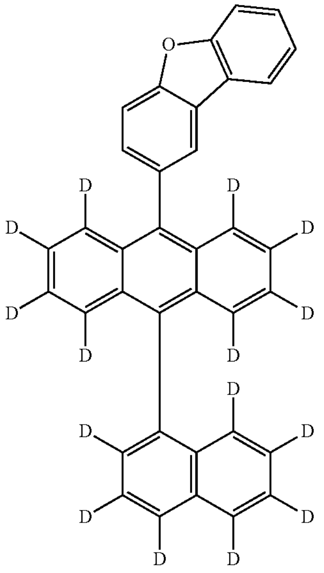

BH-28

<28-a> Preparation of Compound BH-28-a 9-(naphthalen-1-yl)anthracene (54 g) and $AlCl_3$ (9 g) were put into $C_6D_6$ (900 ml), and the resulting mixture was stirred for 2 hours. After the reaction was completed, $D_2O$ (60 ml) was added thereto, the resulting solution was stirred for 30 minutes, and then trimethylamine (6 ml) was added dropwise thereto. The reaction solution was transferred to a separatory funnel, and an extraction with water and toluene was performed. The extract was dried over $MgSO_4$, and then the residue was recrystallized with ethyl acetate to obtain BH-28-a at a yield of 67%. (MS[M+H]+=321)

<28-b> Preparation of Compound BH-28-b

After Compound BH-11-a (36 g, 112 mmol) was dispersed in 500 ml of dimethylformamide, a solution of n-bromosuccinimide (19.9 g, 111 mmol) dissolved in 50 ml of dimethylformamide was slowly added dropwise thereto. After reaction at room temperature for 2 hours, 1 L of water was added dropwise thereto. When a solid was produced, the solid was filtered, and then dissolved in ethyl acetate, and the resulting solution was put into a separatory funnel, and then washed several times with distilled water. The solution was recrystallized in ethyl acetate to obtain Compound BH-28-b (37 g, yield 83%). (MS[M+H]+=398)

<28-c> Preparation of Compound BH-28

After Compound BH-28-b (37 g, 93 mmol) and dibenzo [b,d]furan-2-ylboronic acid (19.6 g, 92 mmol) were dissolved in THF (450 ml), $Pd(PPh_3)_4$ (5.3 g, 4.6 mmol) and 100 ml of an aqueous 2M $K_2CO_3$ solution were added thereto, and the resulting solution was refluxed for 24 hours. The reaction solution was cooled, and the organic layer was extracted with ethyl acetate, and then dried over anhydrous magnesium sulfate. The organic solvent was removed under reduced pressure, and the residue was purified using column chromatography to obtain Compound BH-28 (25 g, yield 62%). (MS[M+H]+=486)

Synthesis Example 29. Synthesis of BH-29

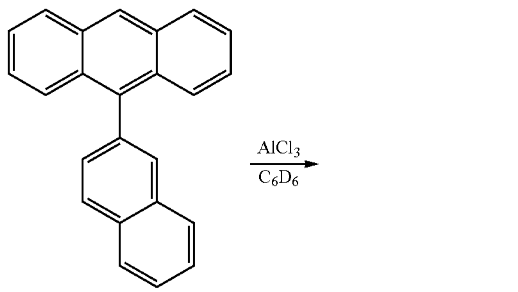

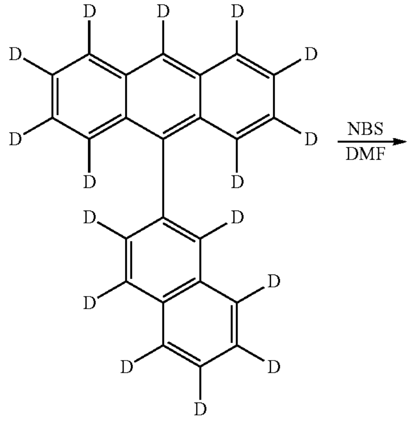

BH-29-a

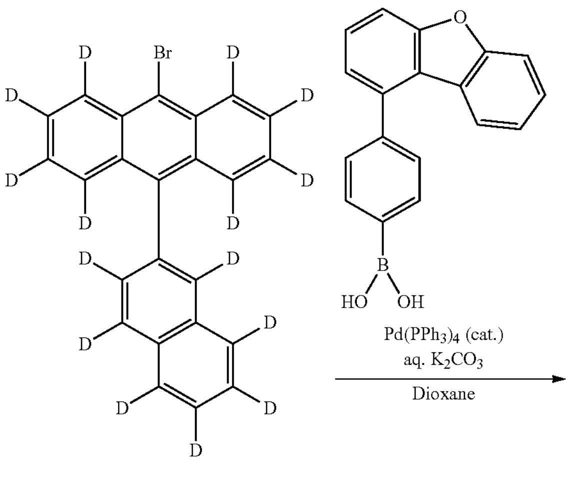

BH-29-b

-continued

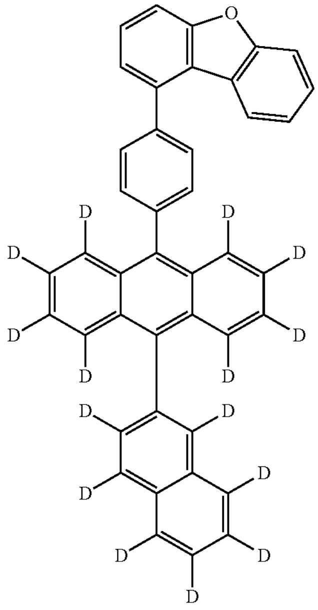

BH-29

<29-a> Preparation of Compound BH-29-a

BH-29-a was obtained from 9-(naphthalen-2-yl)anthracene in the same manner as in Synthesis Example <28-a>. (Yield 69%, MS[M+H]+=321)

<29-b> Preparation of Compound BH-29-b

BH-29-b was obtained from BH-29-a in the same manner as in Synthesis Example <28-b>. (Yield 79%, MS[M+H]+=398)

<29-b> Preparation of Compound BH-29

BH-29 was obtained from BH-29-b and (4-(dibenzo[b,d]furan-1-yl)phenyl)boronic acid in the same manner as in Synthesis Example <28-c>. (Yield 61%, MS[M+H]+=562)

Synthesis Example 31. Synthesis of BH-31

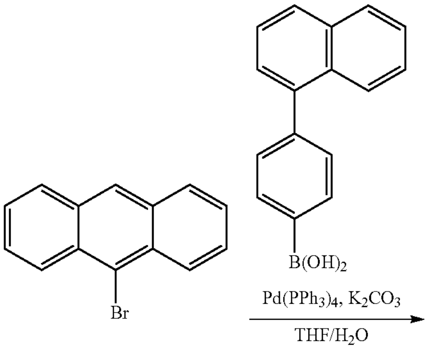

-continued

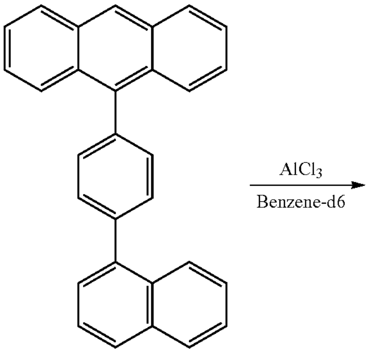

BH-31-a

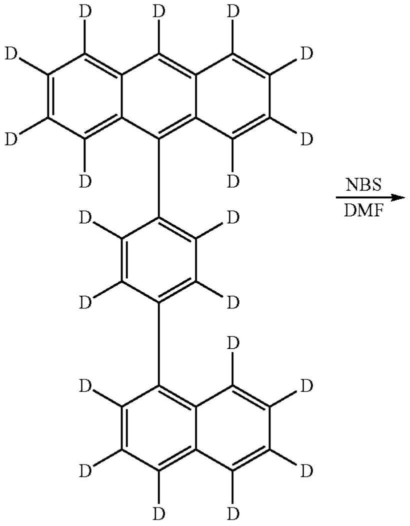

BH-31-b

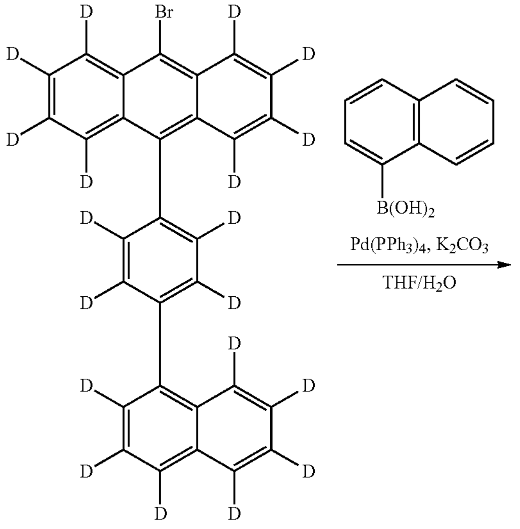

BH-31-c

-continued

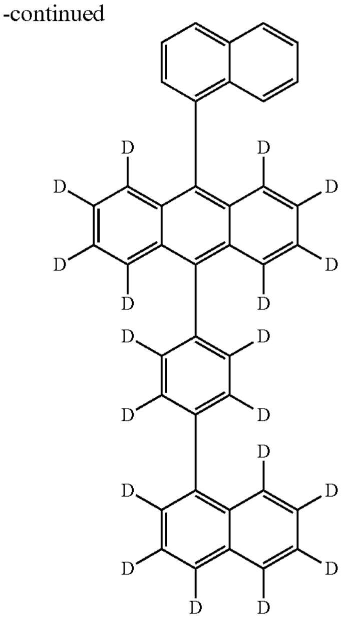

BH-31

<31-a> Preparation of Compound BH-31-a

After 9-bromoanthracene (70 g, 272.2 mmol) and (4-(naphthalen-1-yl)phenyl)boronic acid were dissolved in THF (1400 ml), $Pd(PPh_3)_4$ (15.7 g, 13.6 mmol) and 300 ml of an aqueous 2M $K_2CO_3$ solution were added thereto, and the resulting solution was refluxed for 8 hours. The reaction solution was cooled, and the organic layer was extracted with ethyl acetate, and then dried over anhydrous magnesium sulfate. The organic solvent was removed under reduced pressure, and the residue was purified using column chromatography to obtain Compound BH-31-a (72.5 g, yield 70%). MS: [M+H]+=381

<31-b> Preparation of Compound BH-31-b

Compound BH-31-a (50 g, 131.4 mmol) and $AlCl_3$ (8.6 g, 65.7 mmol) were put into $C_6D_6$ (1000 ml), and the resulting solution was stirred for 2 hours. After the reaction was completed, $D_2O$ (100 ml) was added thereto, the resulting solution was stirred for 30 minutes, and then trimethylamine (10 ml) was added dropwise thereto. The reaction solution was transferred to a separatory funnel, and an extraction with water and toluene was performed. After the extracted reaction solution was dried over anhydrous magnesium sulfate, the organic solvent was removed under reduced pressure, and the residue was purified using column chromatography to obtain Compound BH-31-b (33.1 g, yield 63%). MS: [M+H]+=401

<31-c> Preparation of Compound BH-31-c

After Compound 31-b (30 g, 74.9 mmol) was dispersed in 500 ml of dimethylformamide, a solution of n-bromosuccinimide (13.4 g, 74.9 mmol) dissolved in 50 ml of dimethylformamide was slowly added dropwise thereto. After reaction at room temperature for 2 hours, 1 L of water was added dropwise thereto. When a solid was produced, the solid was filtered, and then dissolved in ethyl acetate, and the resulting solution was put into a separatory funnel, and then washed several times with distilled water. The solution was recrystallized in ethyl acetate to obtain Compound BH-31-c (23.3 g, yield 65%). MS: [M+H]+=479

<31-d> Preparation of Compound BH-31

Compound BH-31 was obtained by performing synthesis and purification in the same manner as in Synthesis Example 31-a, except that 9-bromoanthracene was changed into Compound BH-31-c, and (4-(naphthalen-1-yl)phenyl)boronic acid was changed into naphthalene-1-ylboronic acid. MS: [M+H]+=526

Synthesis Example 32. Synthesis of BH-32

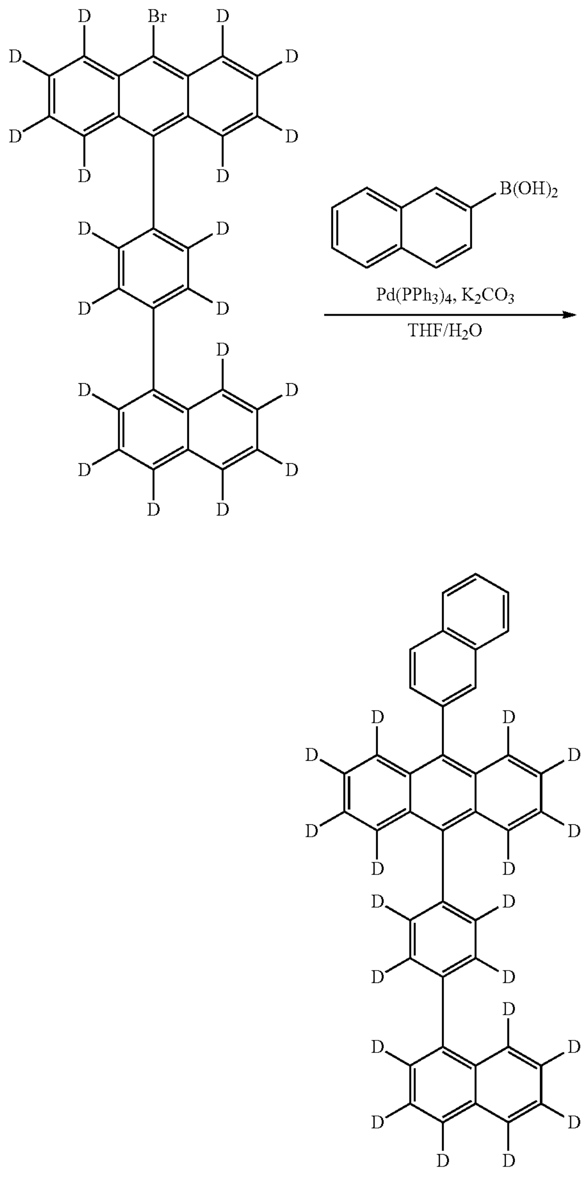

BH-32

<32-a> Preparation of Compound BH-32

Compound BH-32 was obtained by performing synthesis and purification in the same manner as in Synthesis Example 31-a, except that 9-bromoanthracene was changed into Compound BH-31-c, and (4-(naphthalen-1-yl)phenyl)boronic acid was changed into naphthalene-2-ylboronic acid. MS: [M+H]+=526

Synthesis Example 33. Synthesis of BH-33

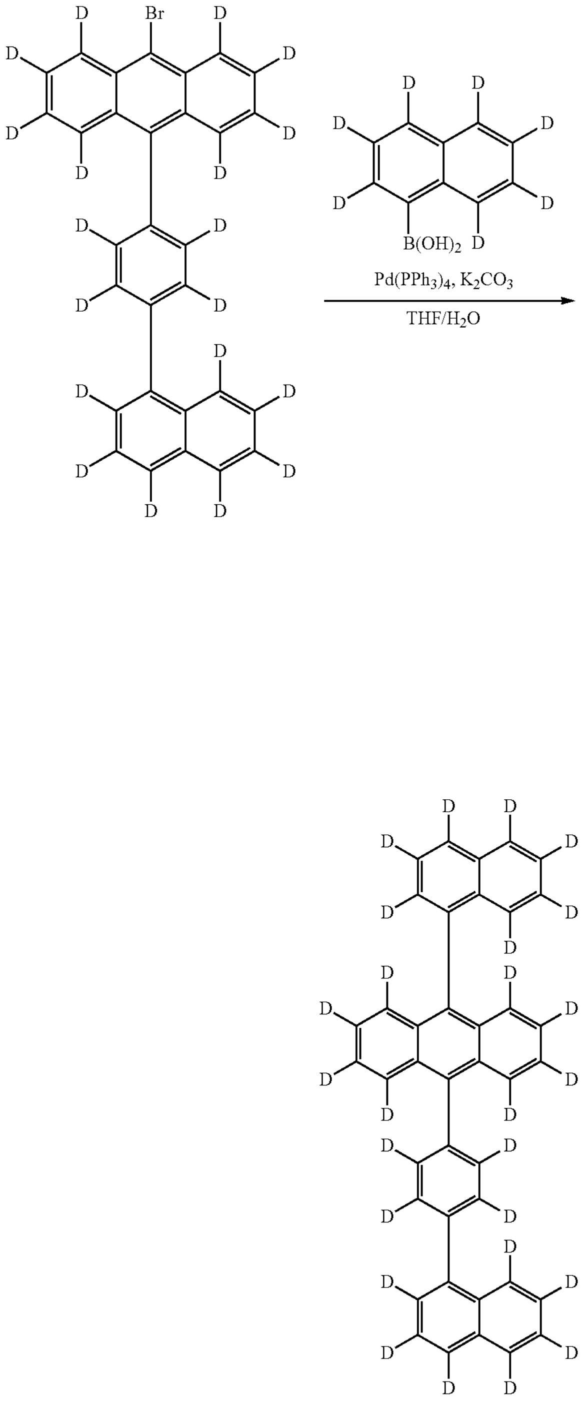

BH-33

<33-a> Preparation of Compound BH-33

Compound BH-33 was obtained by performing synthesis and purification in the same manner as in Synthesis Example 31-a, except that 9-bromoanthracene was changed into Compound BH-31-c, and (4-(naphthalen-1-yl)phenyl)boronic acid was changed into B-(1-naphthalenyl-2,3,4,5,6,7,8-d7)-boronic acid. MS: [M+H]+=533

Synthesis Example 34. Synthesis of BH-34

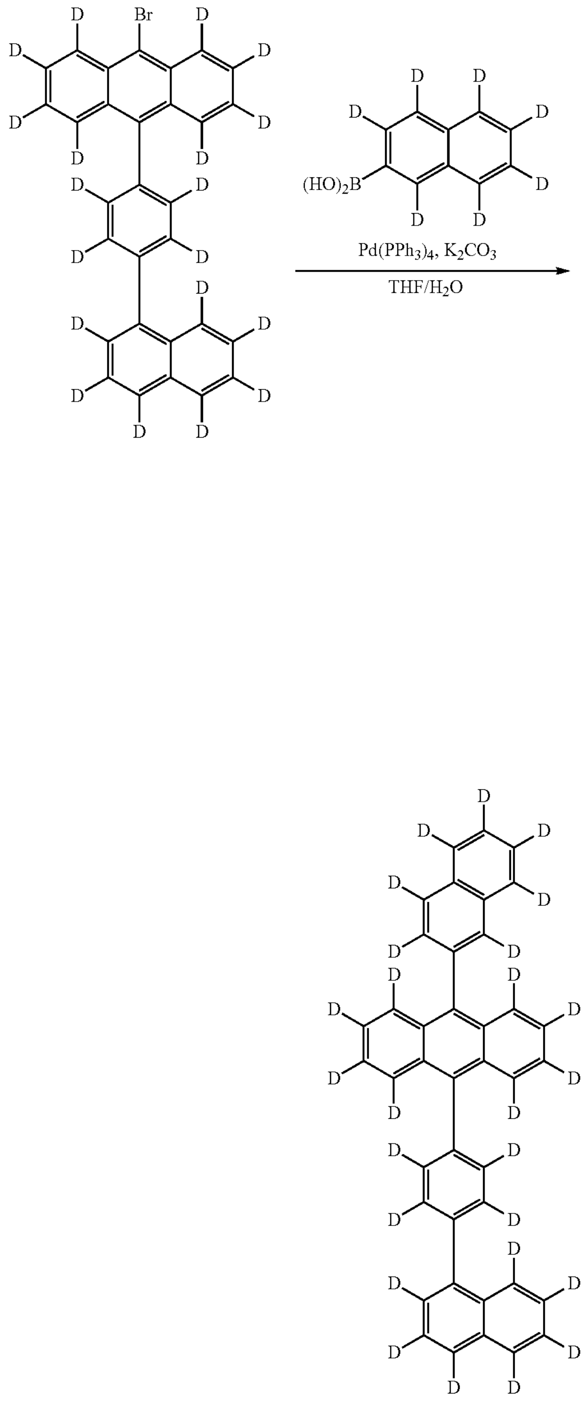

BH-34

<34-a> Preparation of Compound BH-34

Compound BH-34 was obtained by performing synthesis and purification in the same manner as in Synthesis Example 31-a, except that 9-bromoanthracene was changed into Compound BH-31-c, and (4-(naphthalen-1-yl)phenyl)boronic acid was changed into B-(2-naphthalenyl-1,3,4,5,6,7,8-d7)-boronic acid. MS: [M+H]+=533

Synthesis Example 35. Synthesis of BH-35

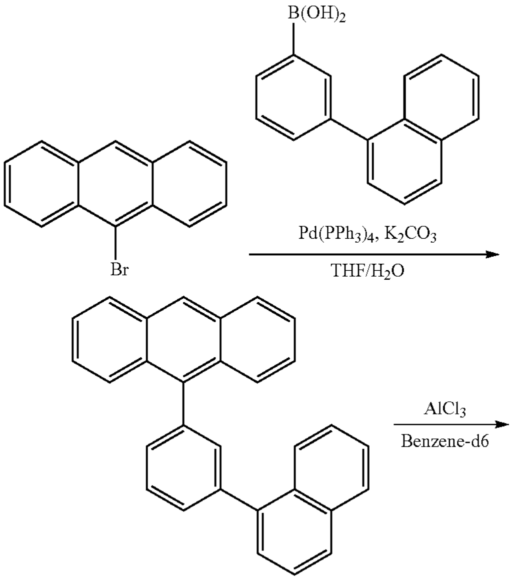

BH-35-a

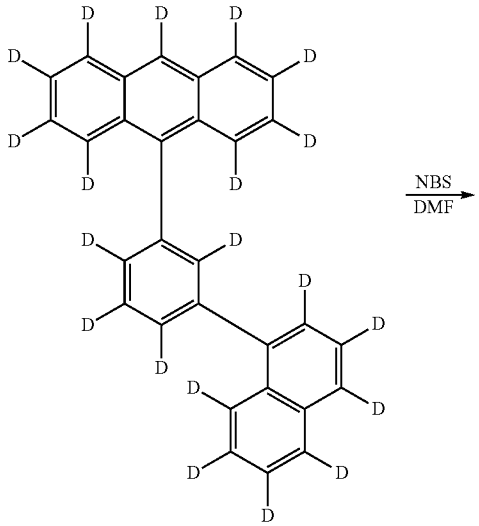

BH-35-b

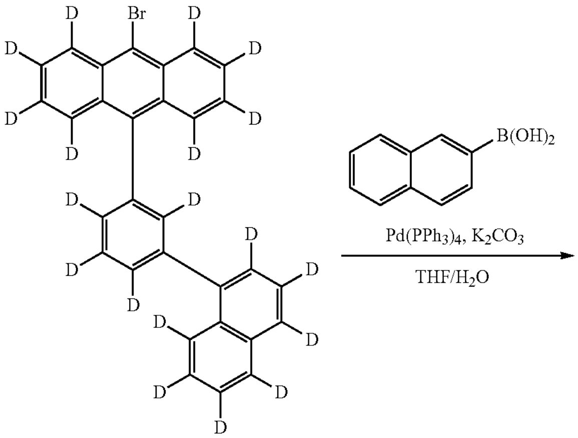

BH-35-c

-continued

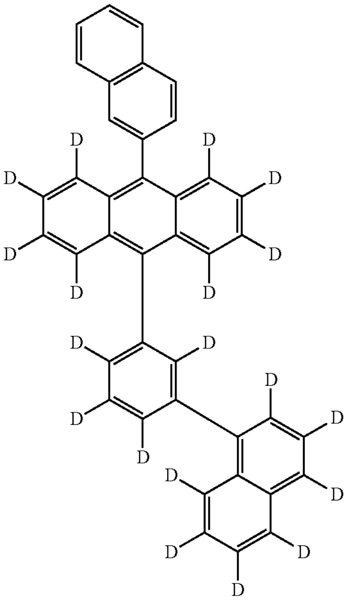

BH-35

<35-a> Preparation of Compound BH-35-a

Compound BH-35-a was obtained by performing synthesis and purification in the same manner as in Synthesis Example 31-a, except that (4-(naphthalen-1-yl)phenyl)boronic acid was changed into (3-(naphthalen-1-yl)phenyl) boronic acid. MS: [M+H]+=381

<35-b> Preparation of Compound BH-35-b

Compound BH-35-b was obtained by performing synthesis and purification in the same manner as in Synthesis Example 31-b, except that Compound BH-31-a was changed into Compound BH-35-a. MS: [M+H]+=401

<35-c> Preparation of Compound BH-35-c

Compound BH-35-c was obtained by performing synthesis and purification in the same manner as in Synthesis Example 31-c, except that Compound BH-31-b was changed into Compound BH-35-b. MS: [M+H]+=479

<35-d> Preparation of Compound BH-35

Compound BH-35 was obtained by performing synthesis and purification in the same manner as in Synthesis Example 31-a, except that 9-bromoanthracene was changed into Compound BH-35-c, and (4-(naphthalen-1-yl)phenyl)boronic acid was changed into naphthalene-2-ylboronic acid. MS: [M+H]+=526

Synthesis Example 36. Synthesis of BH-36

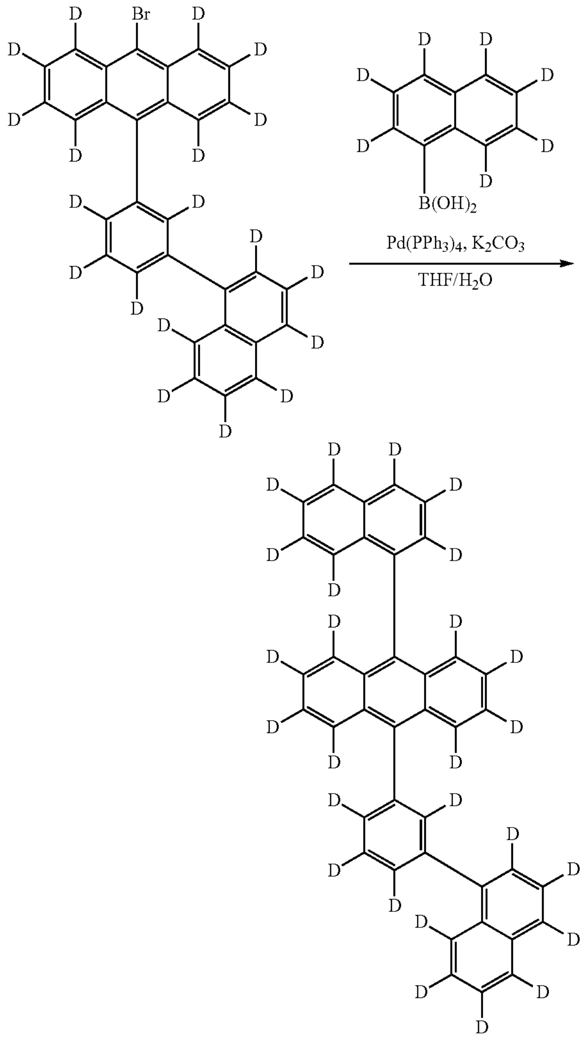

BH-36

<36-a> Preparation of Compound BH-36

Compound BH-36 was obtained by performing synthesis and purification in the same manner as in Synthesis Example 31-a, except that 9-bromoanthracene was changed into Compound B5-35-c, and (4-(naphthalen-1-yl)phenyl)boronic acid was changed into B-(2-naphthalenyl-2,3,4,5,6,7,8-d7)-boronic acid. MS: [M+H]+=533

Synthesis Example 37. Synthesis of BH-37

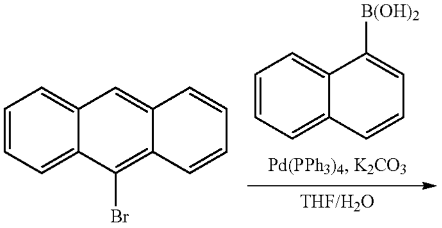

-continued

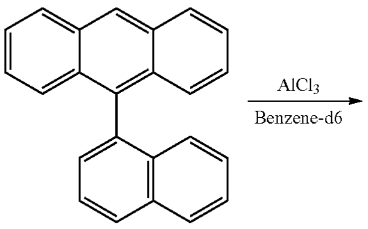

BH-37-a

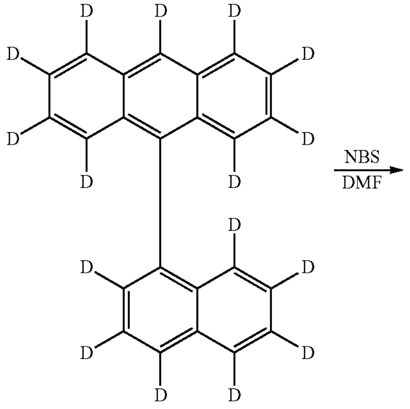

BH-37-b

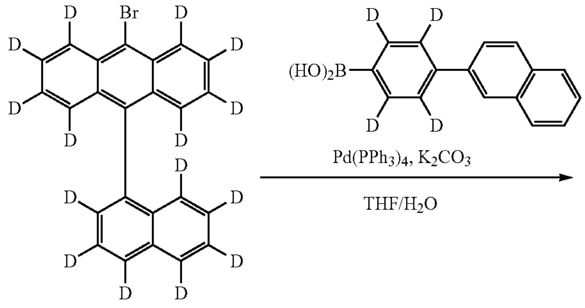

BH-37-c

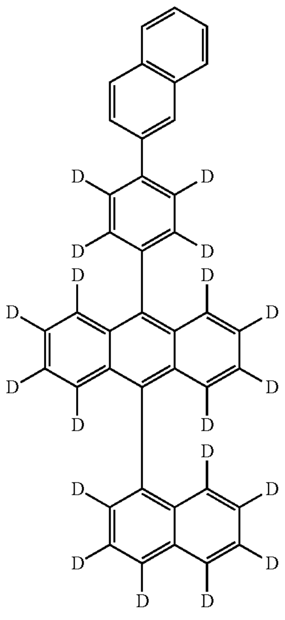

BH-37

<37-a> Preparation of Compound BH-37-a

Compound BH-37-a was obtained by performing synthesis and purification in the same manner as in Synthesis Example 31-a, except that (4-(naphthalen-1-yl)phenyl)boronic acid was changed into naphthalene-1-ylboronic acid. MS: [M+H]+=305

<37-b> Preparation of Compound BH-37-b

Compound BH-37-b was obtained by performing synthesis and purification in the same manner as in Synthesis Example 31-b, except that Compound BH-31-a was changed into Compound BH-37-a. MS: [M+H]+=321

<37-c> Preparation of Compound BH-37-c

Compound BH-37-c was obtained by performing synthesis and purification in the same manner as in Synthesis Example 31-c, except that Compound BH-31-b was changed into Compound BH-37-b. MS: [M+H]+=399

<37-d> Preparation of Compound BH-37

Compound BH-37 was obtained by performing synthesis and purification in the same manner as in Synthesis Example 31-a, except that 9-bromoanthracene was changed into Compound BH-37-c, and (4-(naphthalen-1-yl)phenyl)boronic acid was changed into (4-(naphthalen-2-yl)phenyl-2,3,5,6-d4)-boronic acid. MS: [M+H]+=526

Synthesis Example 38. Synthesis of BH-38

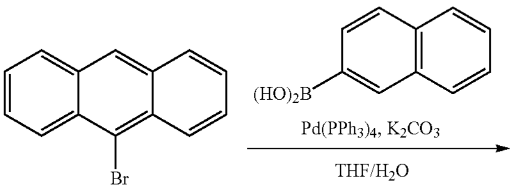

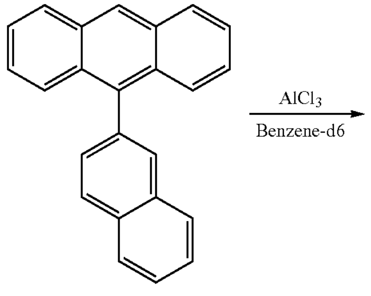

BH-38-a

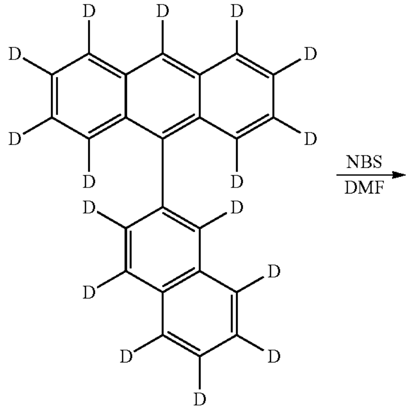

BH-38-b

-continued

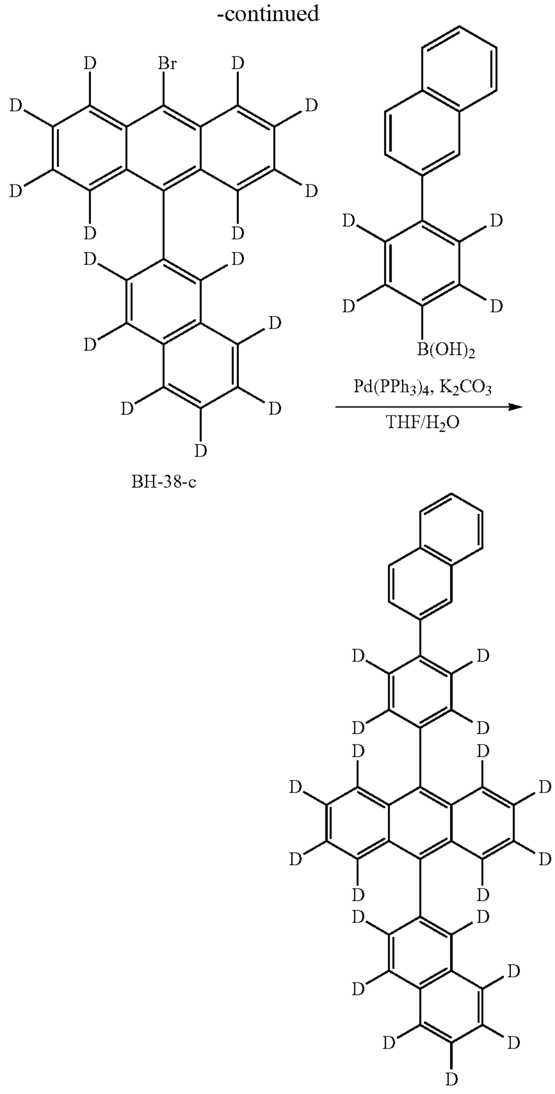

BH-38-c

BH-38

<38-a> Preparation of Compound BH-38-a

Compound BH-38-a was obtained by performing synthesis and purification in the same manner as in Synthesis Example 31-a, except that (4-(naphthalen-1-yl)phenyl)boronic acid was changed into naphthalene-2-ylboronic acid. MS: [M+H]+=305

<38-b> Preparation of Compound BH-38-b

Compound BH-38-b was obtained by performing synthesis and purification in the same manner as in Synthesis Example 31-b, except that Compound BH-31-a was changed into Compound BH-38-a. MS: [M+H]+=321

<38-c> Preparation of Compound BH-38-c

Compound BH-38-c was obtained by performing synthesis and purification in the same manner as in Synthesis Example 31-c, except that Compound BH-31-b was changed into Compound BH-38-b. MS: [M+H]+=399

<38-d> Preparation of Compound BH-38

Compound BH-38 was obtained by performing synthesis and purification in the same manner as in Synthesis Example 31-a, except that 9-bromoanthracene was changed into Compound BH-37-c, and (4-(naphthalen-1-yl)phenyl)boronic acid was changed into (4-(naphthalen-2-yl)phenyl-2,3,5,6-d4)-boronic acid. MS: [M+H]+=526

Synthesis Example 39. Synthesis of BH-39

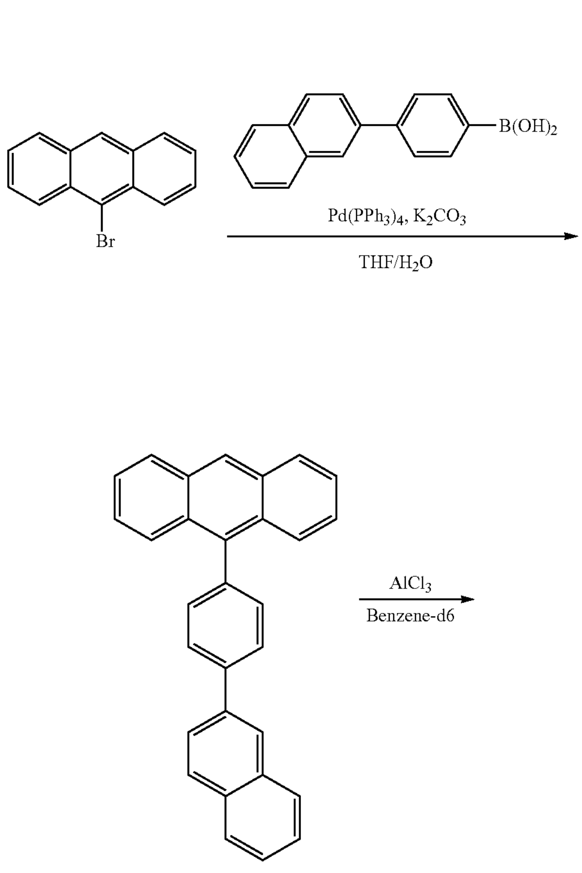

BH-39-a

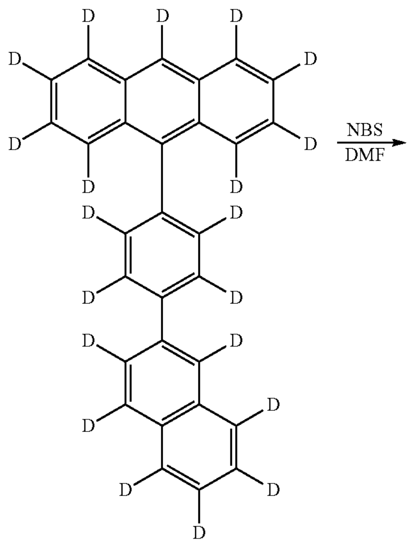

BH-39-b

-continued

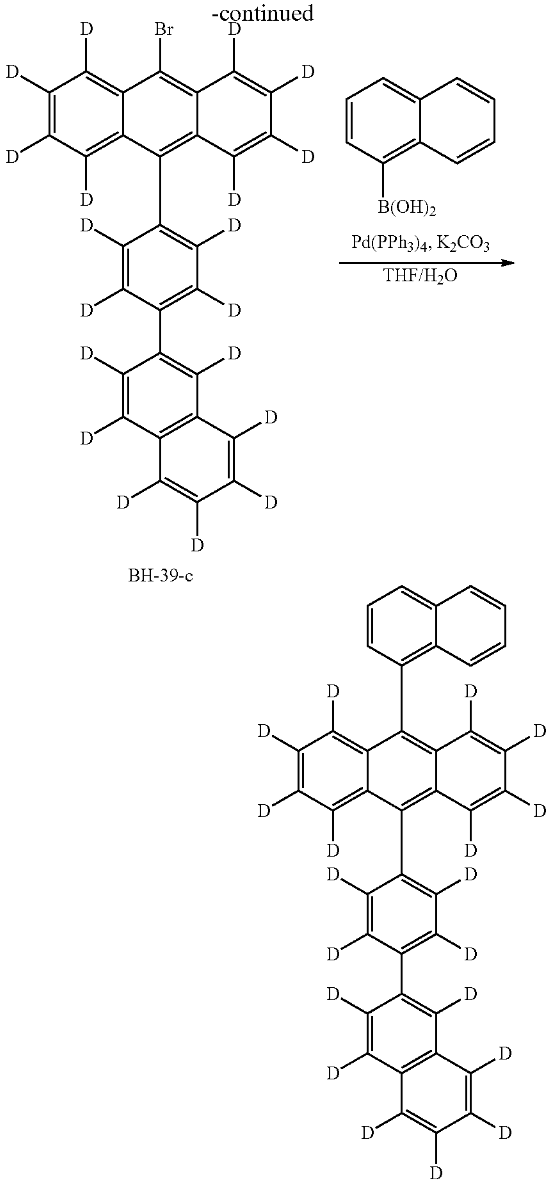

BH-39-c

BH-39

<39-a> Preparation of Compound BH-39-a

Compound BH-39-a was obtained by performing synthesis and purification in the same manner as in Synthesis Example 31-a, except that (4-(naphthalen-1-yl)phenyl)boronic acid was changed into (4-(naphthalen-2-yl)phenyl) boronic acid. MS: [M+H]+=381

<39-b> Preparation of Compound BH-39-b

Compound BH-39-b was obtained by performing synthesis and purification in the same manner as in Synthesis Example 31-b, except that Compound BH-31-a was changed into Compound BH-8-a. MS: [M+H]+=401

<39-c> Preparation of Compound BH-39-c

Compound BH-39-c was obtained by performing synthesis and purification in the same manner as in Synthesis Example 31-c, except that Compound BH-31-b was changed into Compound BH-38-b. MS: [M+H]+=479

<39-d> Preparation of Compound BH-39

Compound BH-39 was obtained by performing synthesis and purification in the same manner as in Synthesis Example 31-a, except that 9-bromoanthracene was changed into Compound BH-38-c, and (4-(naphthalen-1-yl)phenyl)boronic acid was changed into naphthalene-1-ylboronic acid. MS: [M+H]+=526

Synthesis Example 40. Synthesis of BH-40

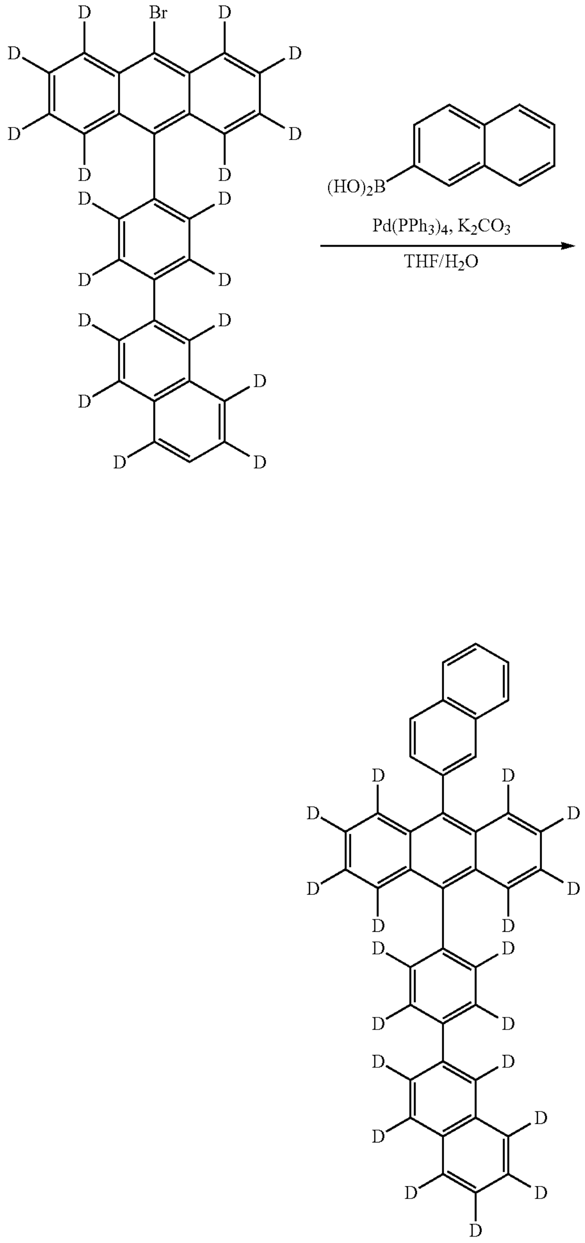

BH-40

<40-a> Preparation of Compound BH-40

Compound BH-40 was obtained by performing synthesis and purification in the same manner as in Synthesis Example 31-a, except that 9-bromoanthracene was changed into Compound BH-39-c, and (4-(naphthalen-1-yl)phenyl)boronic acid was changed into naphthalene-2-ylboronic acid. MS: [M+H]+=526

Synthesis Example 41. Synthesis of BH-41

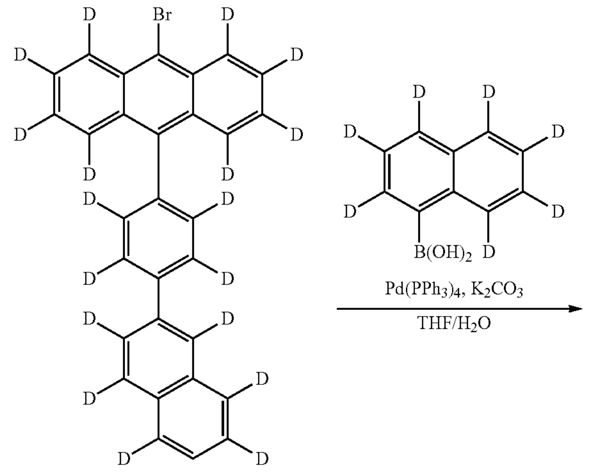

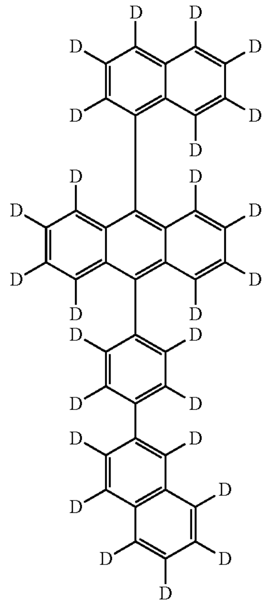

BH-41

<41-a> Preparation of Compound BH-41

Compound BH-41 was obtained by performing synthesis and purification in the same manner as in Synthesis Example 31-a, except that 9-bromoanthracene was changed into Compound BH-39-c, and (4-(naphthalen-1-yl)phenyl)boronic acid was changed into B-(1-naphthalenyl-2,3,4,5,6,7,8-d7)-boronic acid. MS: [M+H]+=533

Synthesis Example 42. Synthesis of BH-42

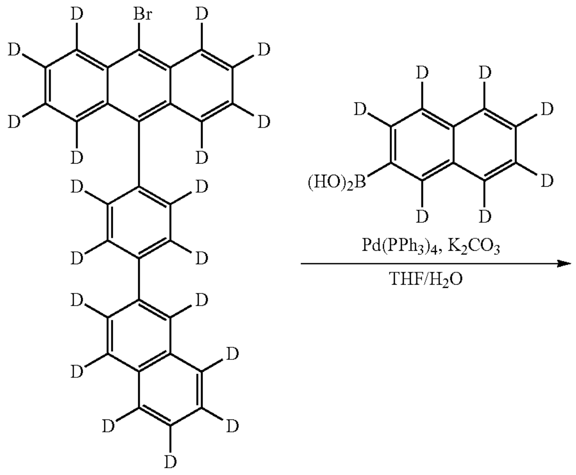

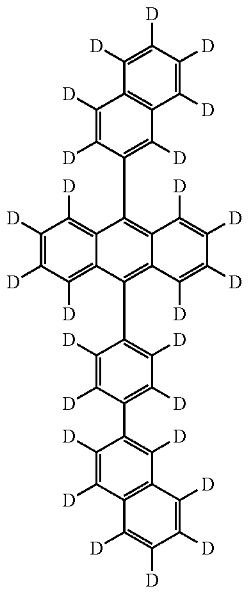

BH-42

<42-a> Preparation of Compound BH-42

Compound BH-42 was obtained by performing synthesis and purification in the same manner as in Synthesis Example 31-a, except that 9-bromoanthracene was changed into Compound BH-39-c, and (4-(naphthalen-1-yl)phenyl)boronic acid was changed into B-(2-naphthalenyl-1,3,4,5,6,7,8-d7)-boronic acid. MS: [M+H]+=533

Synthesis Example 43. Synthesis of BH-43

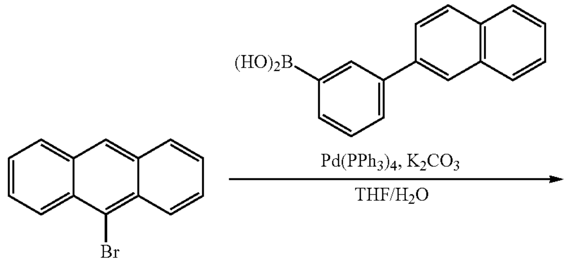

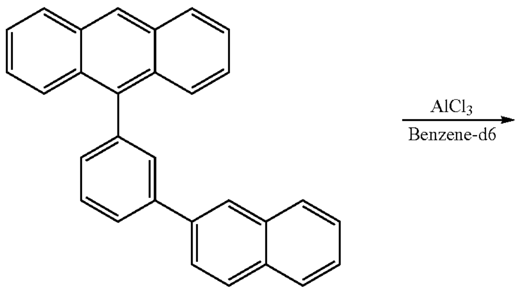

BH-43-a

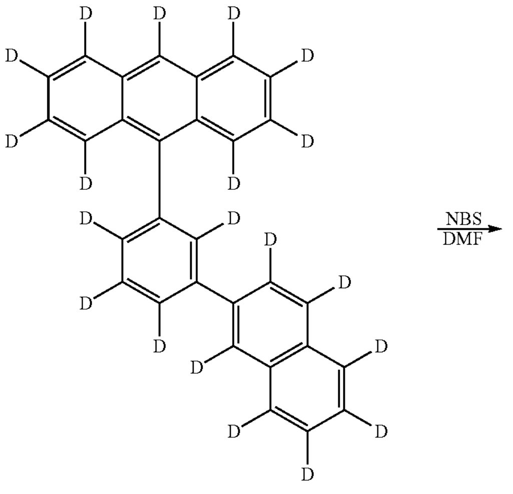

BH-43-b

-continued

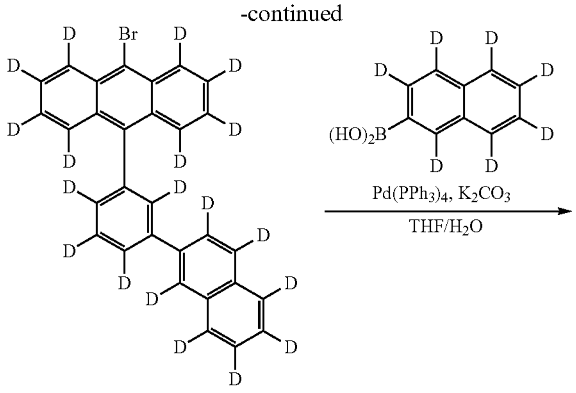

BH-43-c

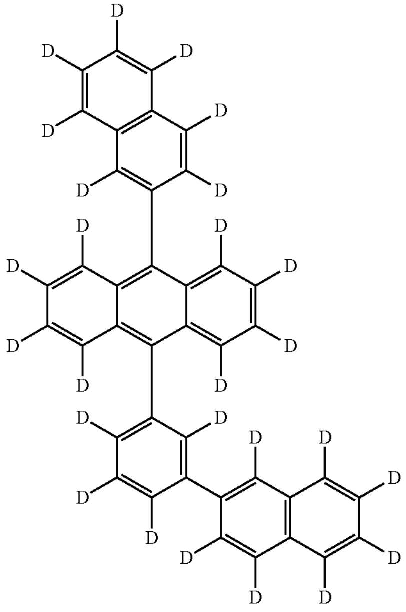

BH-43

<43-a> Preparation of Compound BH-43-a

Compound BH-43-a was obtained by performing synthesis and purification in the same manner as in Synthesis Example 31-a, except that (4-(naphthalen-1-yl)phenyl)boronic acid was changed into (3-(naphthalen-2-yl)phenyl) boronic acid. MS: [M+H]+=381

<43-b> Preparation of Compound BH-43-b

Compound BH-43-b was obtained by performing synthesis and purification in the same manner as in Synthesis Example 31-b, except that Compound BH-31-a was changed into Compound BH-43-a. MS: [M+H]+=401

<43-c> Preparation of Compound BH-43-c

Compound BH-43-c was obtained by performing synthesis and purification in the same manner as in Synthesis Example 31-c, except that Compound BH-31-b was changed into Compound BH-43-b. MS: [M+H]+=479

<43-d> Preparation of Compound BH-43

Compound BH-43 was obtained by performing synthesis and purification in the same manner as in Synthesis Example 31-a, except that 9-bromoanthracene was changed into Compound BH-43-c, and (4-(naphthalen-1-yl)phenyl)boronic acid was changed into B-(2-naphthalenyl-1,3,4,5,6,7,8-d7)-boronic acid. MS: [M+H]+=533

Synthesis Example 44. Synthesis of BH-44

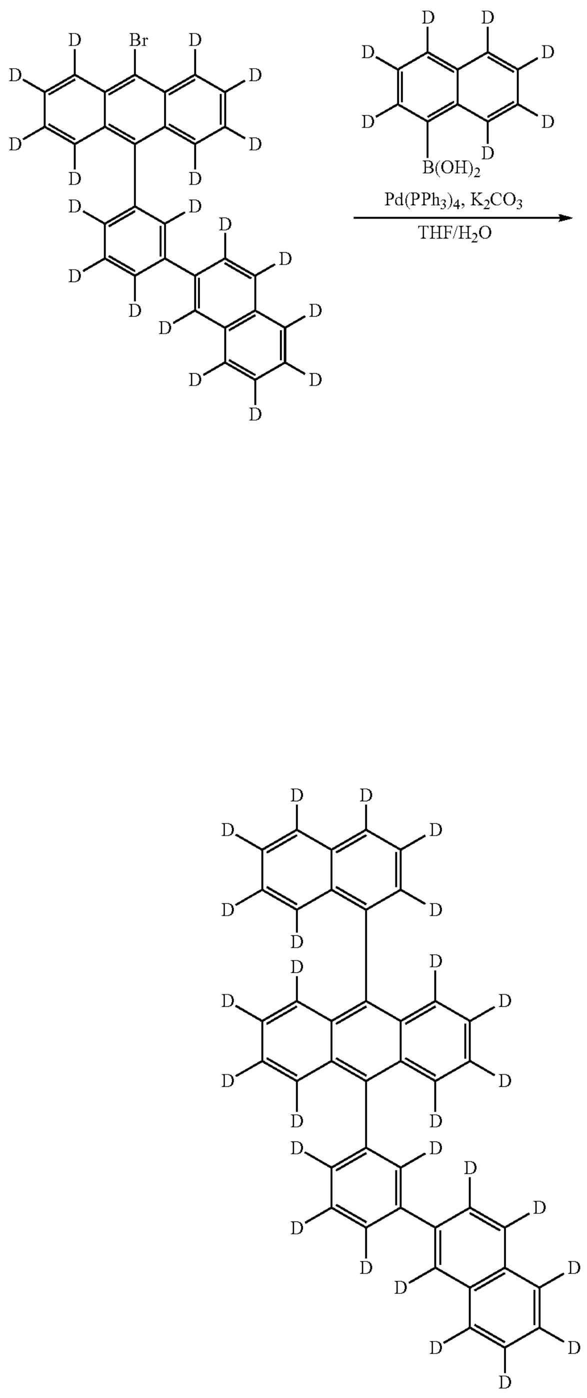

BH-44

<44-a> Preparation of Compound BH-44

Compound BH-44 was obtained by performing synthesis and purification in the same manner as in Synthesis Example 31-a, except that 9-bromoanthracene was changed into Compound BH-43-c, and (4-(naphthalen-1-yl)phenyl)boronic acid was changed into B-(1-naphthalenyl-2,3,4,5,6,7,8-d7)-boronic acid. MS: [M+H]+=533

Synthesis Example 45. Synthesis of BH-45

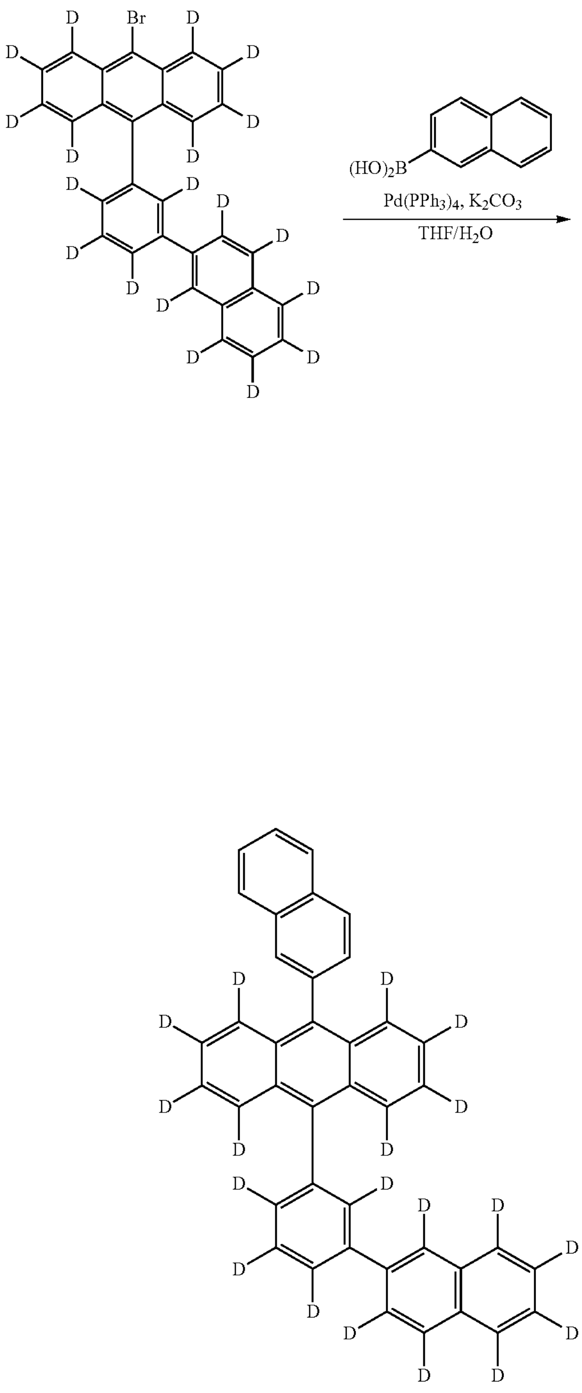

BH-45

<45-a> Preparation of Compound BH-45

Compound BH-45 was obtained by performing synthesis and purification in the same manner as in Synthesis Example 31-a, except that 9-bromoanthracene was changed into Compound BH-43-c, and (4-(naphthalen-1-yl)phenyl)boronic acid was changed into naphthalene-2-ylboronic acid. MS: [M+H]+=526

Synthesis Example 46. Synthesis of BH-46

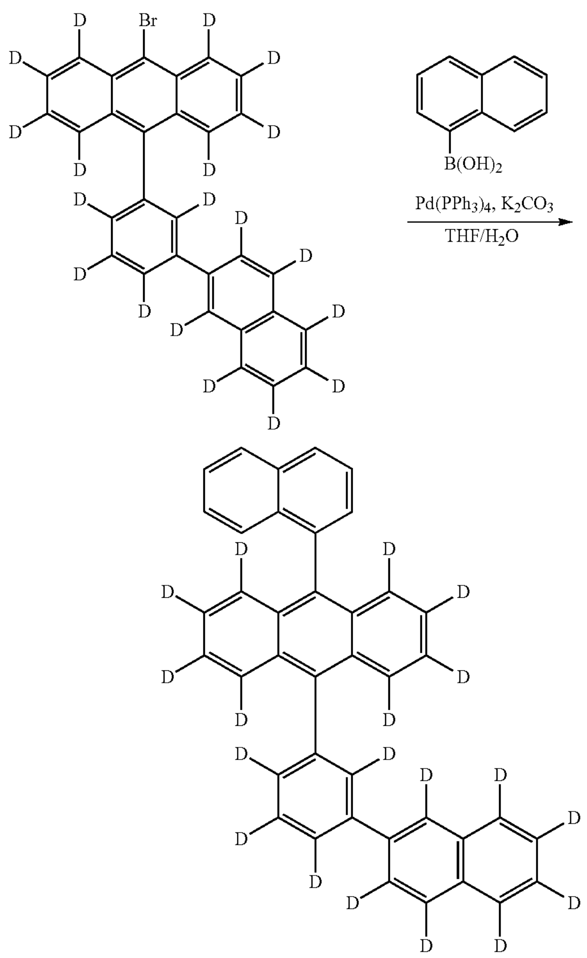

BH-46

<46-a> Preparation of Compound BH-46

Compound BH-46 was obtained by performing synthesis and purification in the same manner as in Synthesis Example 31-a, except that 9-bromoanthracene was changed into Compound BH-43-c, and (4-(naphthalen-1-yl)phenyl)boronic acid was changed into naphthalene-1-ylboronic acid. MS: [M+H]+=526

Synthesis Example 47. Synthesis of BH-47

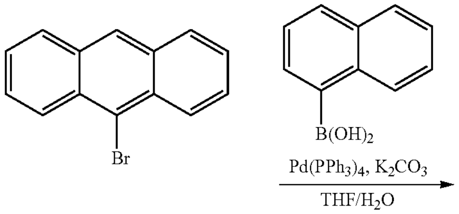

-continued

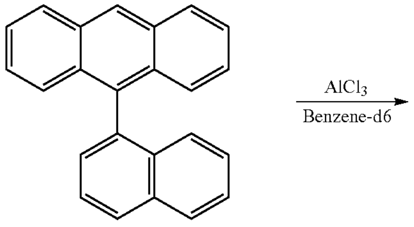

BH-47-a

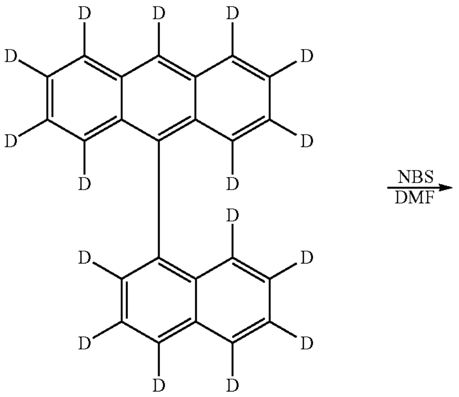

BH-47-b

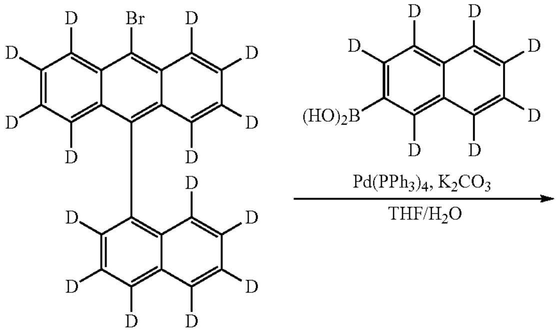

BH-47-c

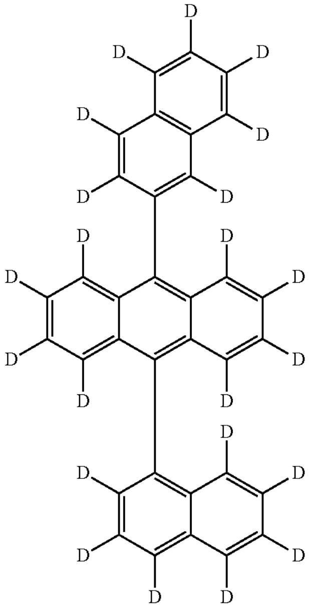

BH-47

<47-a> Preparation of Compound BH-47-a

Compound BH-47-a was obtained by performing synthesis and purification in the same manner as in Synthesis Example 31-a, except that (4-(naphthalen-1-yl)phenyl)boronic acid was changed into naphthalene-1-ylboronic acid. MS: [M+H]+=305

<47-b> Preparation of Compound BH-47-b

Compound BH-47-b was obtained by performing synthesis and purification in the same manner as in Synthesis Example 31-b, except that Compound BH-31-a was changed into Compound BH-47-a. MS: [M+H]+=321

<47-c> Preparation of Compound BH-47-c

Compound BH-47-c was obtained by performing synthesis and purification in the same manner as in Synthesis Example 31-c, except that Compound BH-31-b was changed into Compound BH-47-b. MS: [M+H]+=399

<47-d> Preparation of Compound BH-47

Compound BH-47 was obtained by performing synthesis and purification in the same manner as in Synthesis Example 31-a, except that 9-bromoanthracene was changed into Compound BH-47-c, and (4-(naphthalen-1-yl)phenyl)boronic acid was changed into B-(2-naphthalenyl-1,3,4,5,6,7,8-d7)-boronic acid. MS: [M+H]+=453

Synthesis Example 48. Synthesis of BH-48

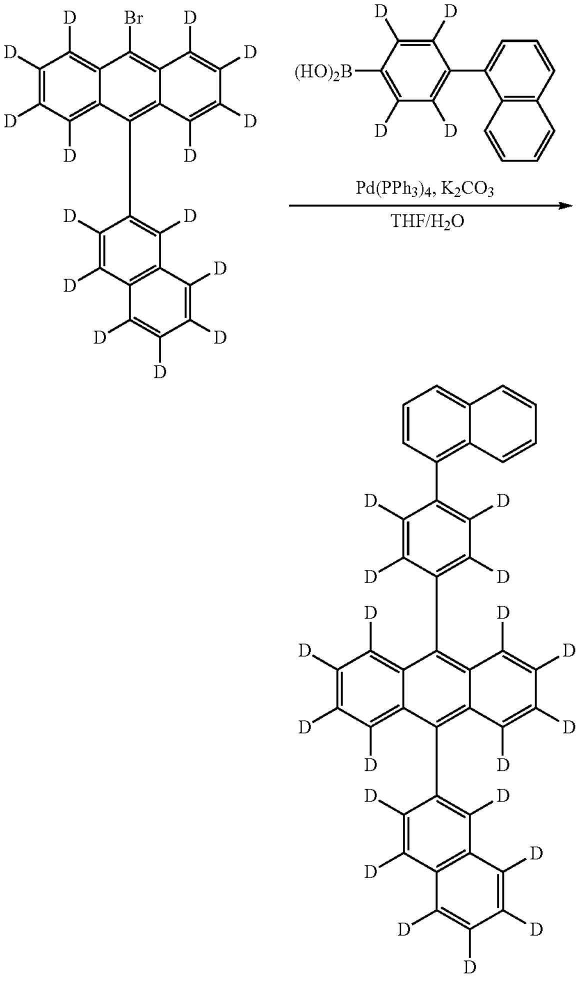

BH-48

<48-a> Preparation of Compound BH-48

Compound BH-48 was obtained by performing synthesis and purification in the same manner as in Synthesis Example 31-a, except that 9-bromoanthracene was changed into Compound BH-38-c, and (4-(naphthalen-1-yl)phenyl)boronic acid was changed into B-[4-(1-naphthalenyl)phenyl-2,3,5,6-d4]-boronic acid. MS: [M+H]+=526

Synthesis Example 49. Synthesis of BH-49

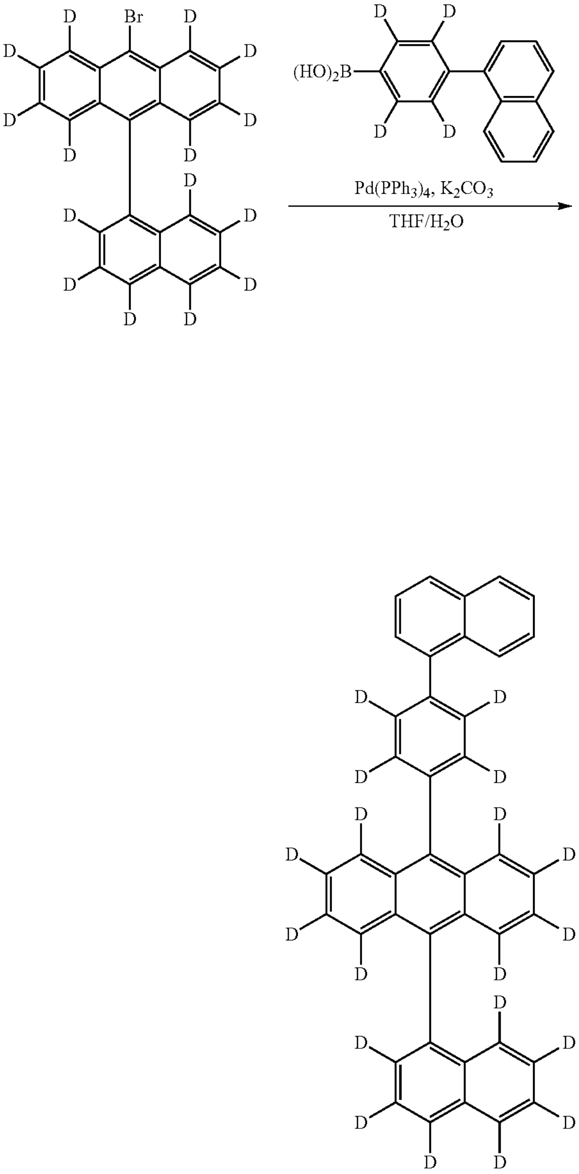

BH-49

<49-a> Preparation of Compound BH-49

Compound BH-49 was obtained by performing synthesis and purification in the same manner as in Synthesis Example 31-a, except that 9-bromoanthracene was changed into Compound BH-37-c, and (4-(naphthalen-1-yl)phenyl)boronic acid was changed into (4-(naphthalen-1-yl)phenyl-2,3,5,6-d4)-boronic acid. MS: [M+H]+=526

Synthesis Example 50. Synthesis of BH-50

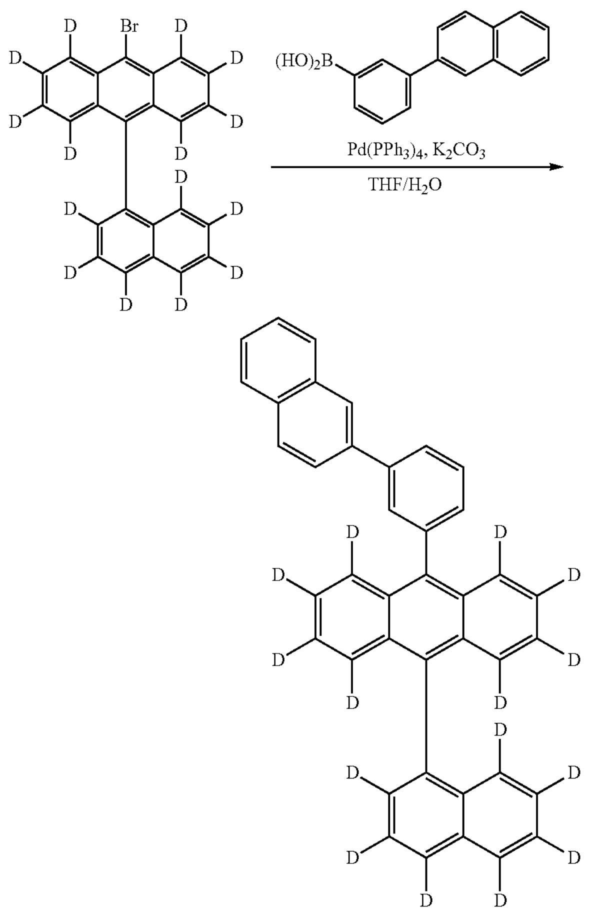

BH-50

<50-a> Preparation of Compound BH-50

Compound BH-50 was obtained by performing synthesis and purification in the same manner as in Synthesis Example 31-a, except that 9-bromoanthracene was changed into Compound BH-37-c, and (4-(naphthalen-1-yl)phenyl)boronic acid was changed into (3-(naphthalen-2-yl)phenyl)-boronic acid. MS: [M+H]+=522

Synthesis Example 51. Synthesis of BH-51

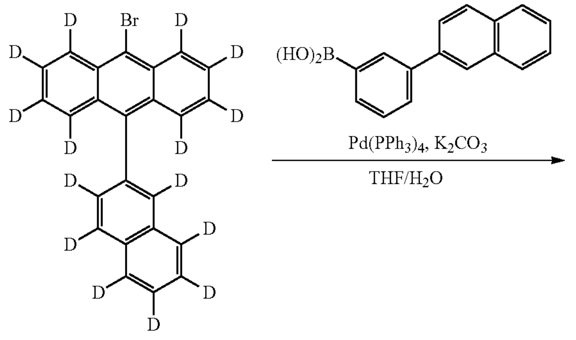

-continued

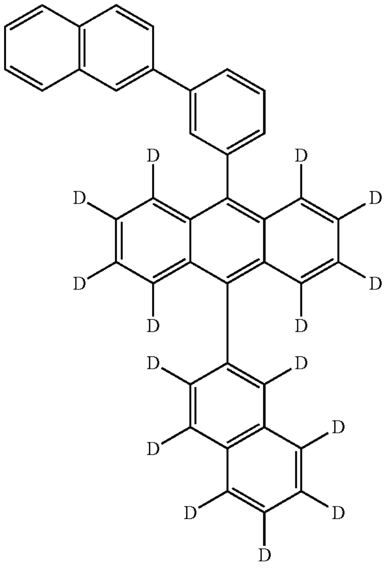

BH-51

<51-a> Preparation of Compound BH-51

Compound BH-51 was obtained by performing synthesis and purification in the same manner as in Synthesis Example 31-a, except that 9-bromoanthracene was changed into Compound BH-38-c, and (4-(naphthalen-1-yl)phenyl)boronic acid was changed into (3-(naphthalen-2-yl)phenyl)-boronic acid. MS: [M+H]+=522

Synthesis Example 52. Synthesis of BH-52

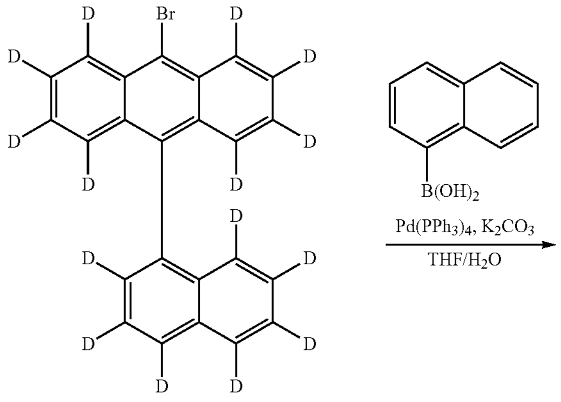

-continued

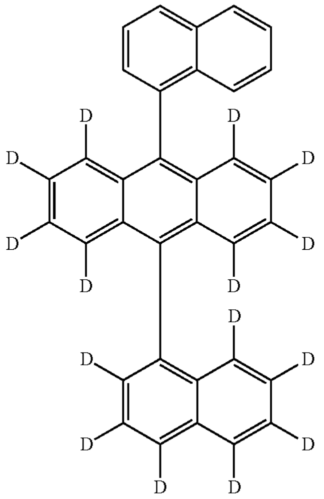

BH-52

<52-a> Preparation of Compound BH-52

Compound BH-52 was obtained by performing synthesis and purification in the same manner as in Synthesis Example 31-a, except that 9-bromoanthracene was changed into Compound BH-37-c, and (4-(naphthalen-1-yl)phenyl)boronic acid was changed into naphthalene-1-ylboronic acid. MS: [M+H]+=446

Synthesis Example 53. Synthesis of BH-53

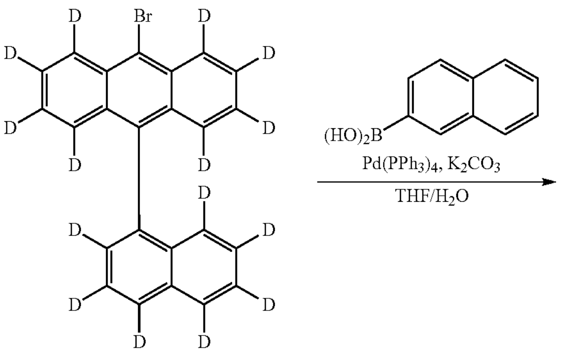

-continued

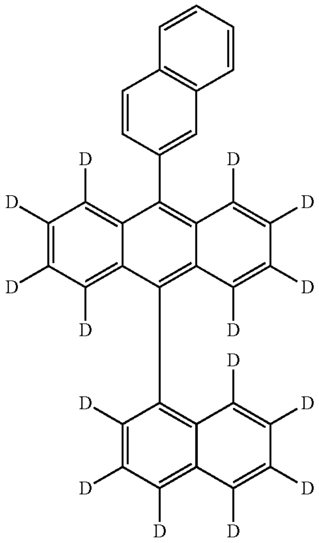

BH-53

<53-a> Preparation of Compound BH-53

Compound BH-53 was obtained by performing synthesis and purification in the same manner as in Synthesis Example 31-a, except that 9-bromoanthracene was changed into Compound BH-37-c, and (4-(naphthalen-1-yl)phenyl)boronic acid was changed into naphthalene-2-ylboronic acid. MS: [M+H]+=446

Synthesis Example 54. Synthesis of BH-54

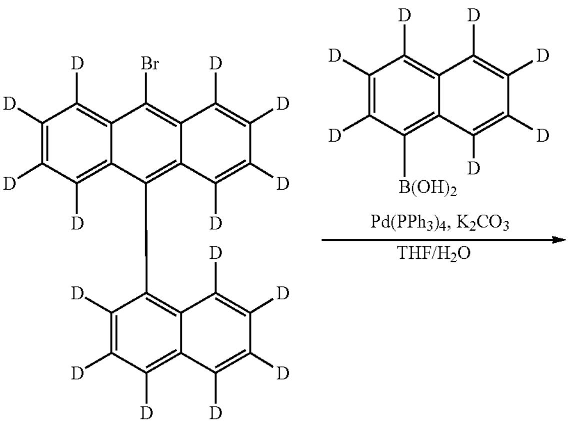

-continued

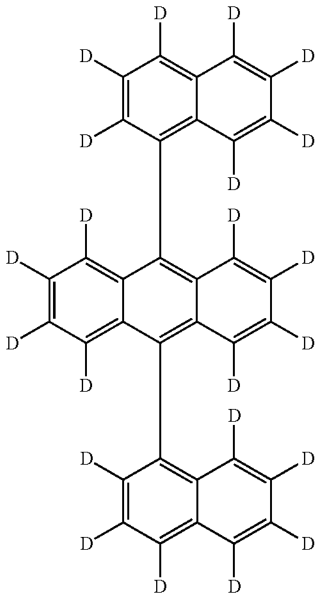

BH-54

<54-a> Preparation of Compound BH-54

Compound BH-54 was obtained by performing synthesis and purification in the same manner as in Synthesis Example 31-a, except that 9-bromoanthracene was changed into Compound BH-37-c, and (4-(naphthalen-1-yl)phenyl)boronic acid was changed into (naphthalen-1-yl-d7)boronic acid. MS: [M+H]+=453

Synthesis Example 55. Synthesis of BH-55

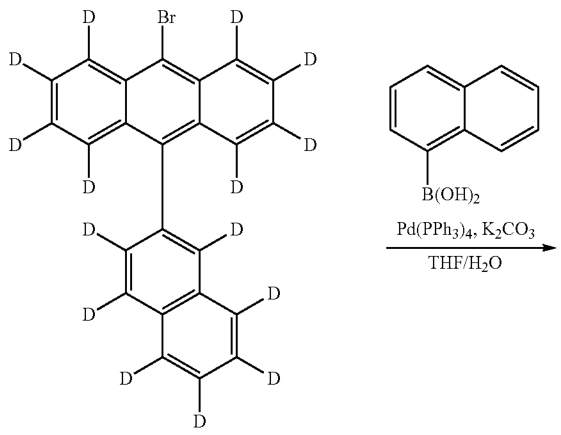

-continued

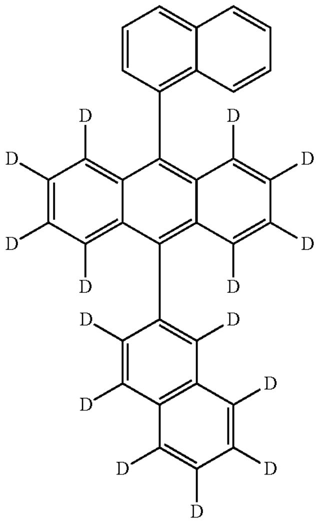

BH-55

<55-a> Preparation of Compound BH-55

Compound BH-55 was obtained by performing synthesis and purification in the same manner as in Synthesis Example 31-a, except that 9-bromoanthracene was changed into Compound BH-38-c, and (4-(naphthalen-1-yl)phenyl)boronic acid was changed into naphthalene-1-ylboronic acid. MS: [M+H]+=456

Synthesis Example 56. Synthesis of BH-56

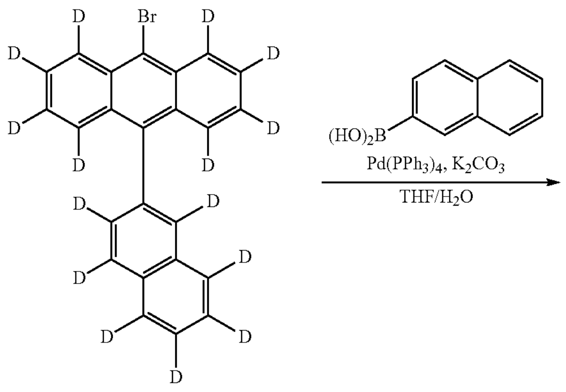

-continued

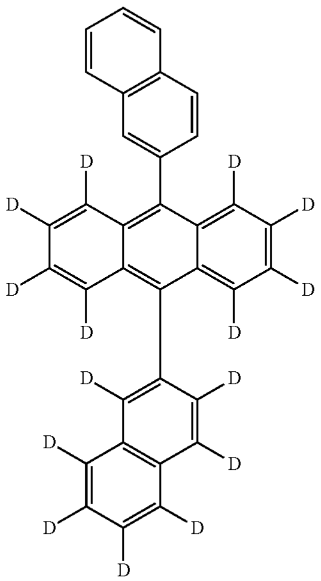

BH-56

<56-a> Preparation of Compound BH-56

Compound BH-56 was obtained by performing synthesis and purification in the same manner as in Synthesis Example 31-a, except that 9-bromoanthracene was changed into Compound BH-38-c, and (4-(naphthalen-1-yl)phenyl)boronic acid was changed into naphthalene-2-ylboronic acid. MS: [M+H]+=456

Synthesis Example 57. Synthesis of BH-57

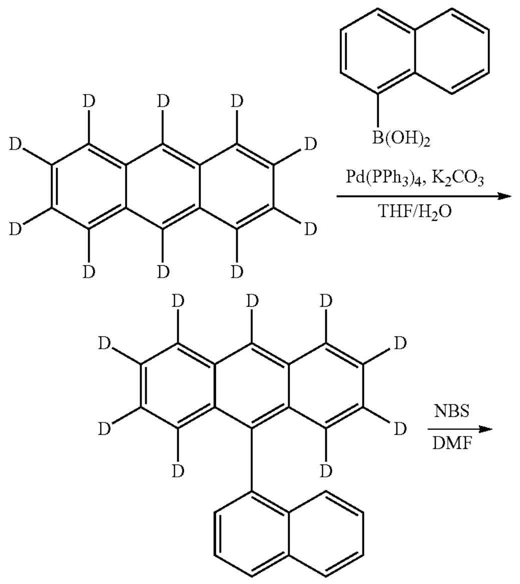

BH-57-a

-continued

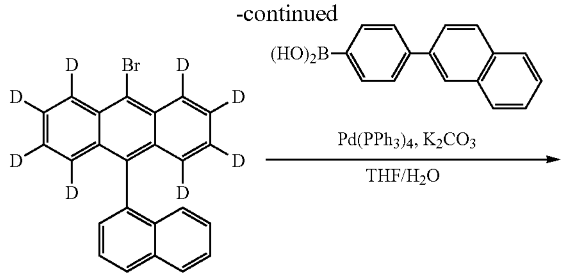

BH-57-b

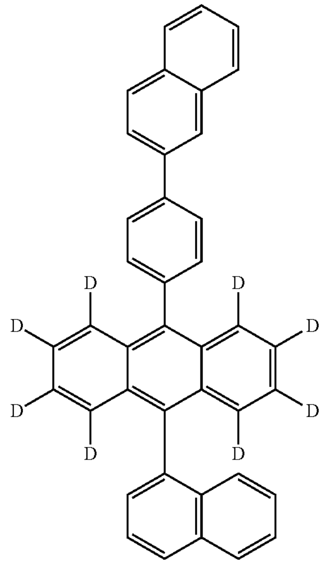

BH-57

<57-a> Preparation of Compound BH-57-a

Compound BH-57-a was obtained by performing synthesis and purification in the same manner as in Synthesis Example 31-a, except that 9-bromoanthracene was changed into 9-bromoanthracene-1,2,3,4,5,6,7,8,10-d9, and (4-(naphthalen-1-yl)phenyl)boronic acid was changed into naphthalene-1-ylboronic acid. MS: [M+H]+=314

<57-b> Preparation of Compound BH-57-b

Compound BH-57-b was obtained by performing synthesis and purification in the same manner as in Synthesis Example 31-c, except that Compound BH-31-b was changed into Compound BH-57-a. MS: [M+H]+=392

<57-c> Preparation of Compound BH-57

Compound BH-57 was obtained by performing synthesis and purification in the same manner as in Synthesis Example 31-a, except that 9-bromoanthracene was changed into Compound BH-57-b, and (4-(naphthalen-1-yl)phenyl)boronic acid was changed into (4-(naphthalen-2-yl)phenyl)boronic acid. MS: [M+H]+=515

Synthesis Example 58. Synthesis of BH-58

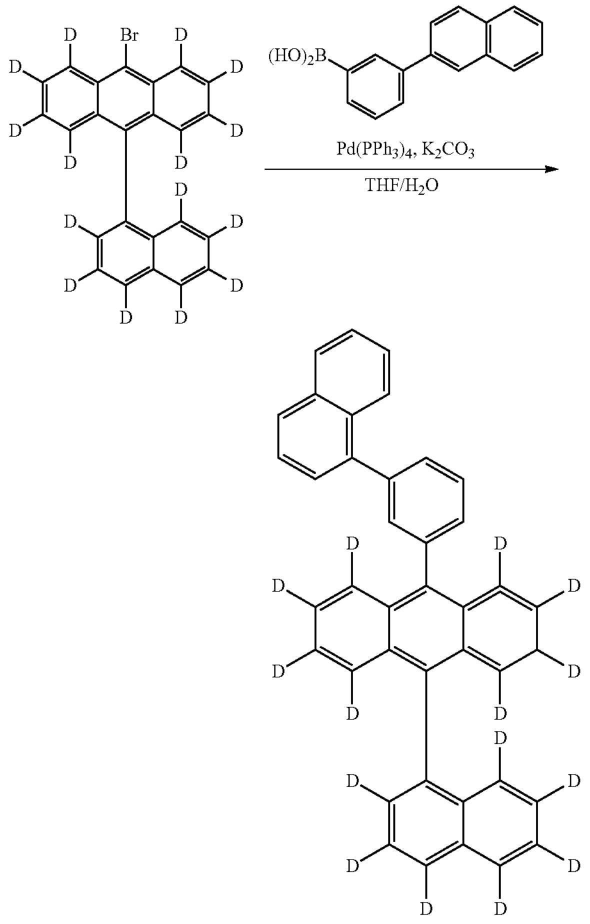

BH-58

<58-a> Preparation of Compound BH-58

Compound BH-58 was obtained by performing synthesis and purification in the same manner as in Synthesis Example 31-a, except that 9-bromoanthracene was changed into Compound BH-37-c, and (4-(naphthalen-1-yl)phenyl)boronic acid was changed into (3-(naphthalen-1-yl)phenyl)-boronic acid. MS: [M+H]+=522

Synthesis Example 59. Synthesis of BH-59

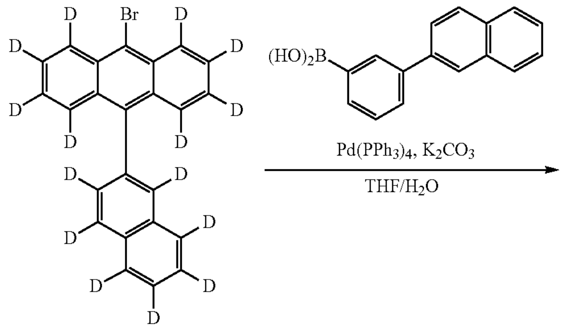

-continued

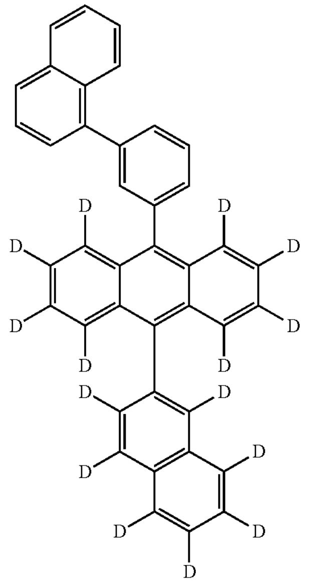

BH-59

<59-a> Preparation of Compound BH-59

Compound BH-59 was obtained by performing synthesis and purification in the same manner as in Synthesis Example 31-a, except that 9-bromoanthracene was changed into Compound BH-38-c, and (4-(naphthalen-1-yl)phenyl)boronic acid was changed into (3-(naphthalen-1-yl)phenyl)-boronic acid. MS: [M+H]+=522

Synthesis Example 60. Synthesis of BD-1

1) Synthesis of Intermediate 1

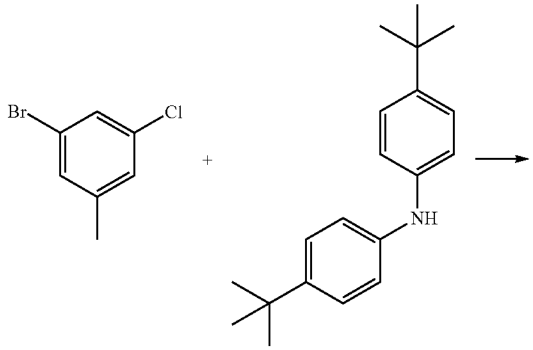

-continued

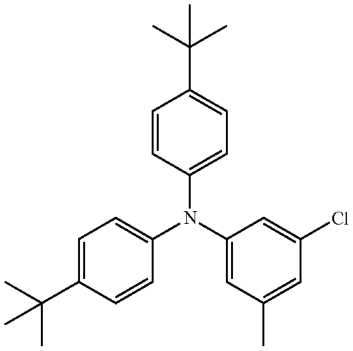

1

After 40 g of 1-bromo-3-chloro-5-methylbenzene, 54.8 g of bis(4-(tert-butyl)phenyl)amine, 56.1 g of sodium-tert-butoxide, and 1.0 g of bis(tri-tert-butylphosphine)palladium (0) were put into 600 ml of toluene under a nitrogen atmosphere, the resulting mixture was stirred under reflux for 2 hours. After the completion of the reaction, the resulting product was extracted, and then recrystallized to obtain 65 g of Intermediate 1. (Yield 82%). MS[M+H]+=407

2) Synthesis of Intermediate 2

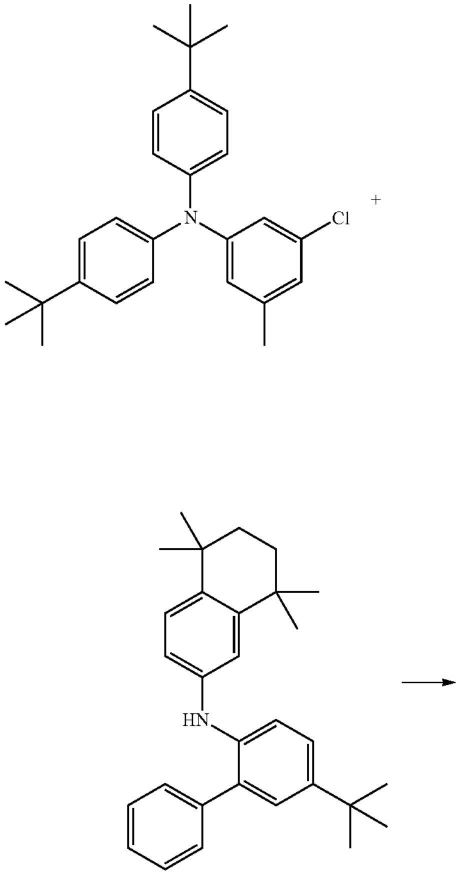

-continued

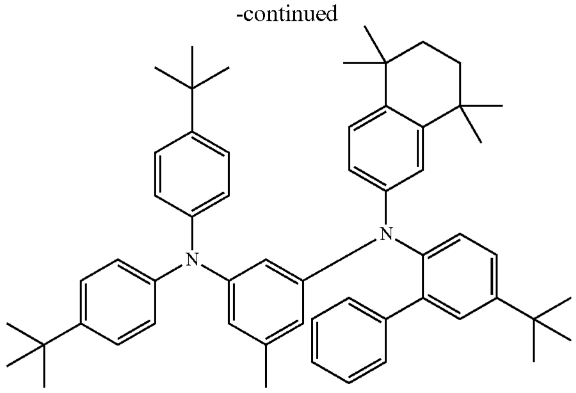

2

After 30 g of Intermediate 1, 30.5 g of N-(5-(tert-butyl)-[1,1'-biphenyl]-2-yl)-5,5,8,8-tetramethyl-5,6,7,8-tetrahydronaphthalen-2-amine, 14.2 g of sodium-tert-butoxide, and 0.4 g of bis(tri-tert-butylphosphine)palladium(0) were put into 450 ml of toluene under a nitrogen atmosphere, the resulting mixture was stirred under reflux for 2 hours. After the completion of the reaction, the resulting product was extracted, and then recrystallized to obtain 45 g of Intermediate 2. (Yield 78%). MS[M+H]+=782

3) Synthesis of BD-1

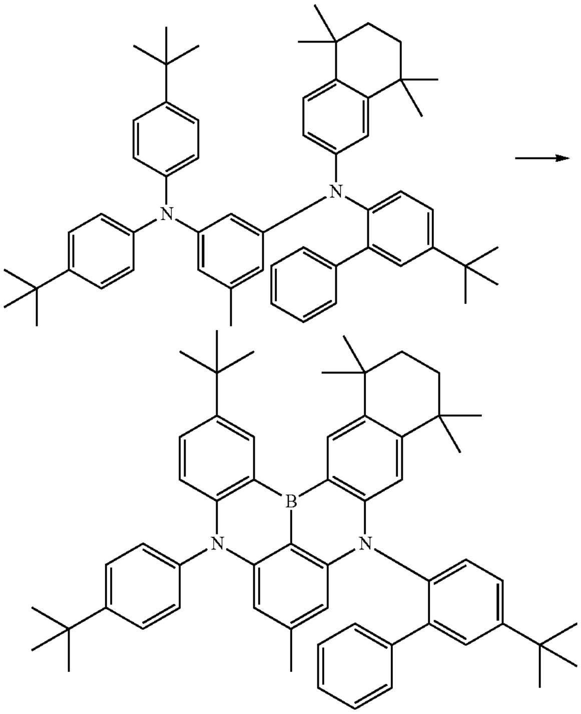

BD-1

After 25 g of Intermediate 2 and 21.3 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 8 g of BD-1 (yield 32%). MS[M+H]+=789

Synthesis Example 61. Synthesis of BD-2

1) Synthesis of Intermediate 3

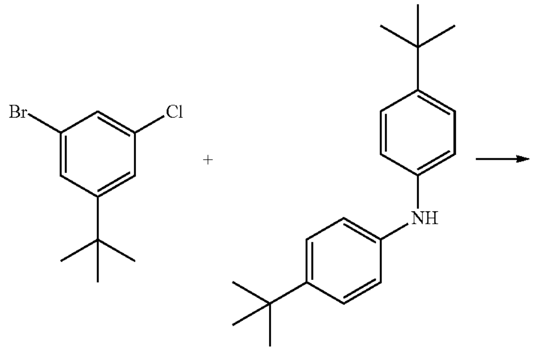

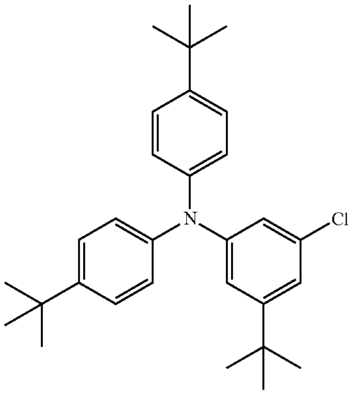

1

40 g of 1-bromo-3-(tert-butyl)-5-chlorobenzene instead of 1-bromo-3-chloro-5-methylbenzene, and the same material and equivalent weight as in the synthesis method of Intermediate 1 were used and then recrystallized to obtain 60 g of Intermediate 3. (Yield 83%). MS[M+H]+=449

2) Synthesis of Intermediate 4

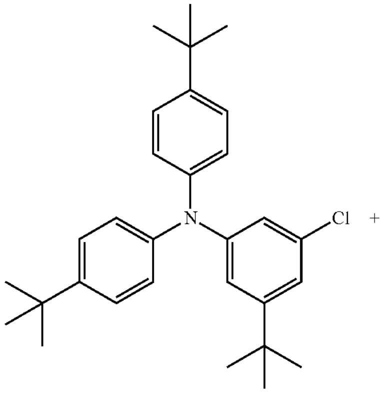

-continued

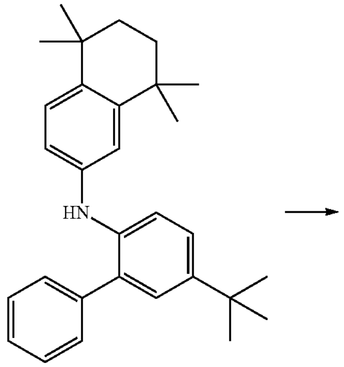

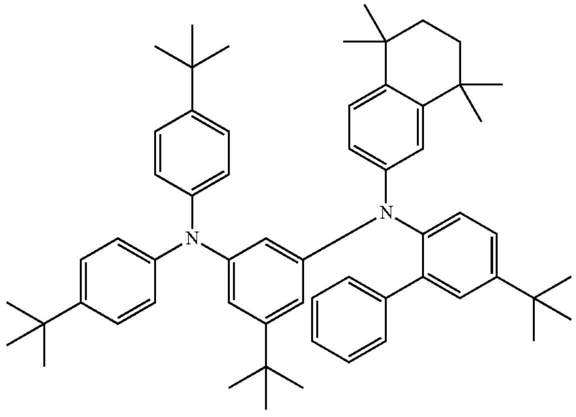

4

30 g of Intermediate 3, 27.5 g of N-(5-(tert-butyl)-[1,1'-biphenyl]-2-yl)-5,5,8,8-tetramethyl-5,6,7,8-tetrahydronaphthalen-2-amine, and the same material and equivalent weight as in the synthesis method of Intermediate 2 were used and then recrystallized to obtain 43 g of Intermediate 4. (Yield 78%). MS[M+H]+=824

3) Synthesis of BD-2

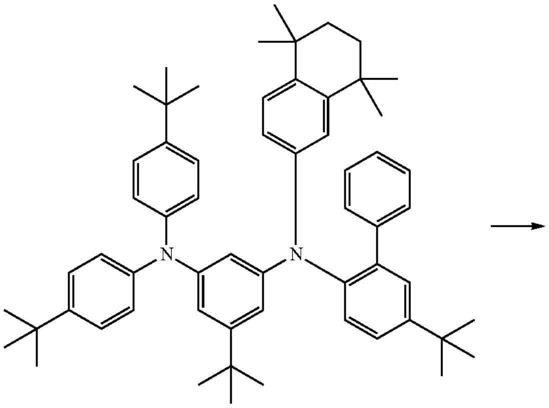

-continued

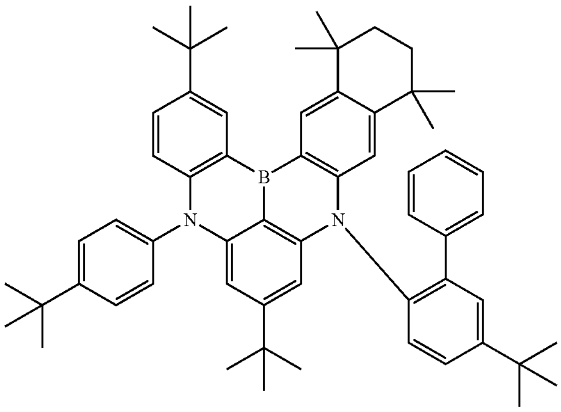

BD-2

After 25 g of Intermediate 4 and 20.2 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 8.4 g of BD-2 (yield 33%). MS[M+H]+=832

Synthesis Example 62. Synthesis of BD-3

1) Synthesis of Intermediate 5

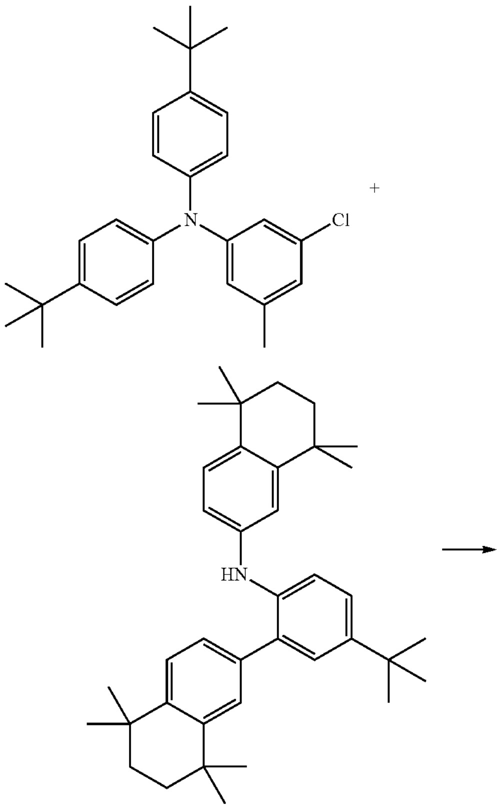

-continued

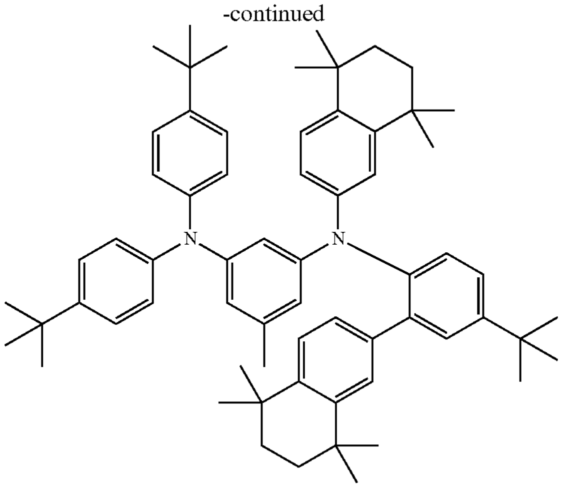

5

30 g of Intermediate 1, 38.6 g of N-(4-(tert-butyl)-2-(5,5,8,8-tetramethyl-5,6,7,8-tetrahydronaphthalen-2-yl)phenyl)-5,5,8,8-tetramethyl-5,6,7,8-tetrahydronaphthalen-2-amine, and the same material and equivalent weight as in the synthesis method of Intermediate 2 were used and then recrystallized to obtain 46 g of Intermediate 5. (Yield 70%). MS[M+H]+=892

2) Synthesis of BD-3

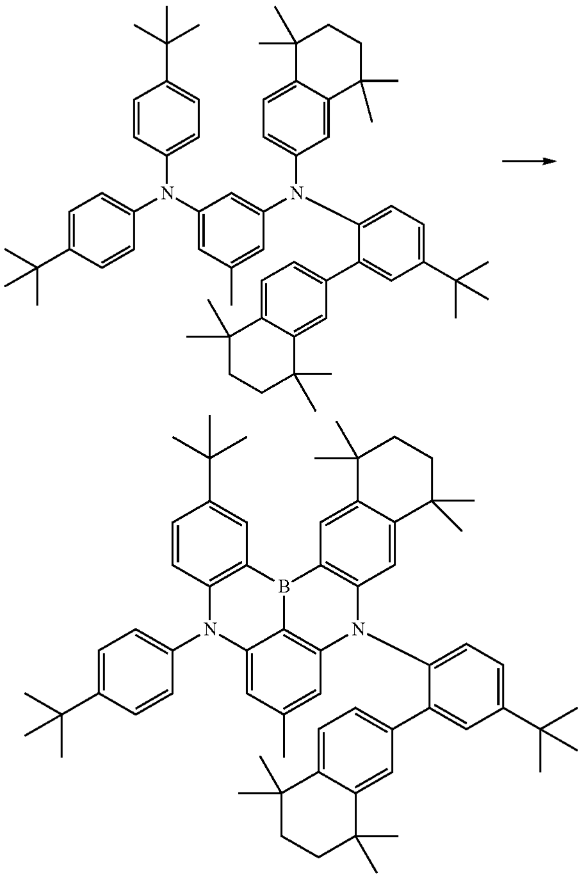

BD-3

After 25 g of Intermediate 5 and 20.2 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 8.1 g of BD-3 (yield 31%). MS[M+H]+=900

Synthesis Example 63. Synthesis of BD-4

1) Synthesis of Intermediate 6

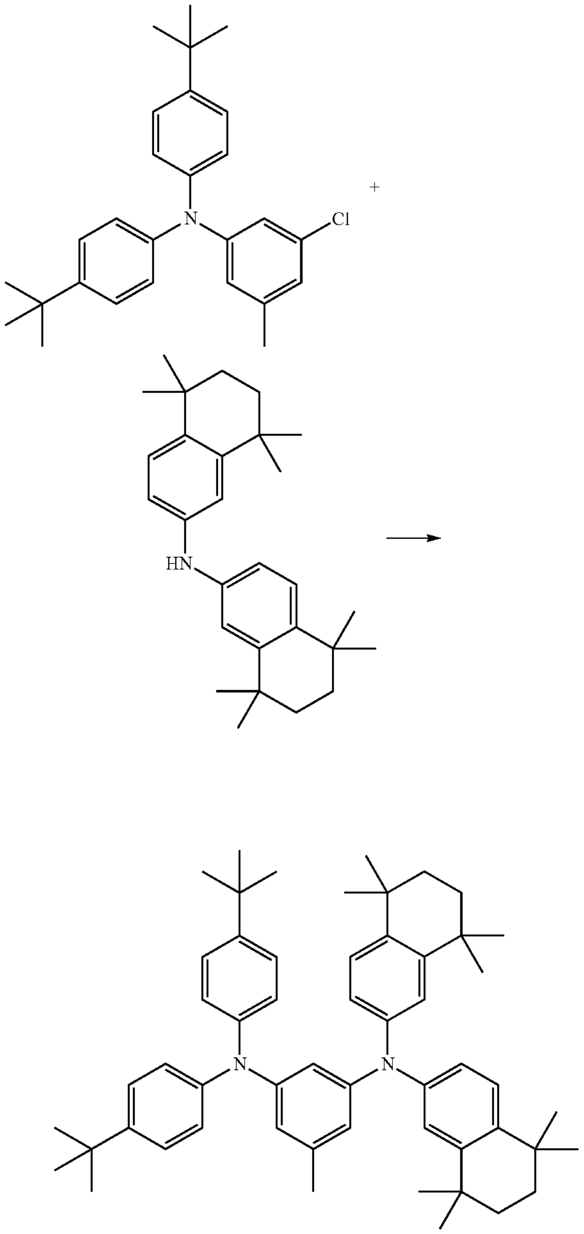

6

30 g of Intermediate 1, 28.8 g of bis(5,5,8,8-tetramethyl-5,6,7,8-tetrahydronaphthalen-2-yl)amine, and the same material and equivalent weight as in the synthesis method of Intermediate 2 were used and then recrystallized to obtain 42 g of Intermediate 6. (Yield 75%). MS[M+H]+=760

2) Synthesis of BD-4

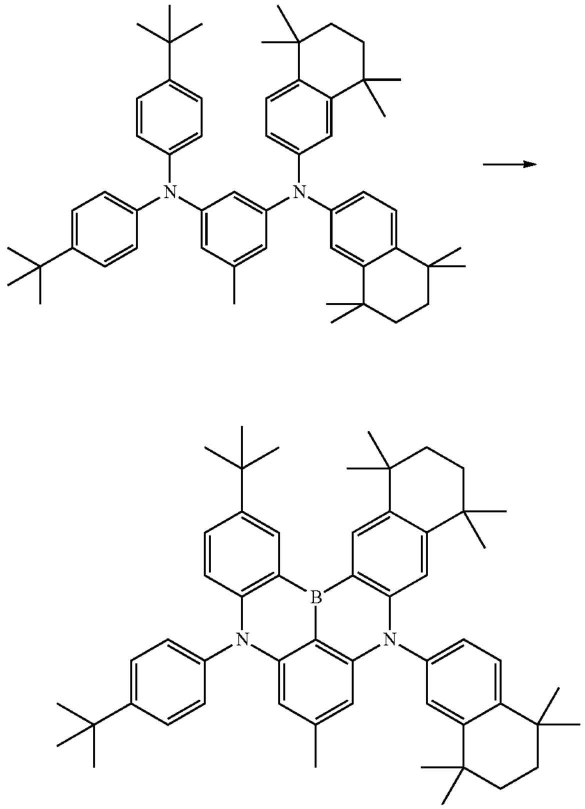

BD-4

After 25 g of Intermediate 6 and 21.9 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.9 g of BD-4 (yield 31%). MS[M+H]+=767

Synthesis Example 64. Synthesis of BD-5

1) Synthesis of Intermediate 7

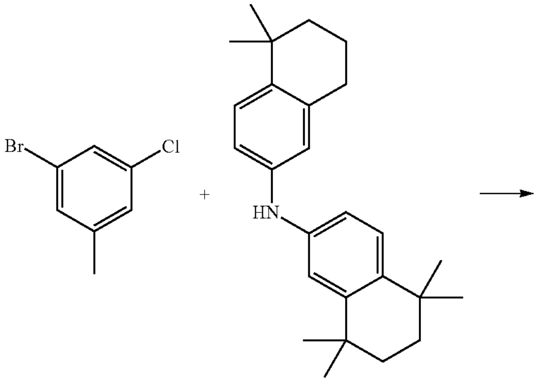

-continued

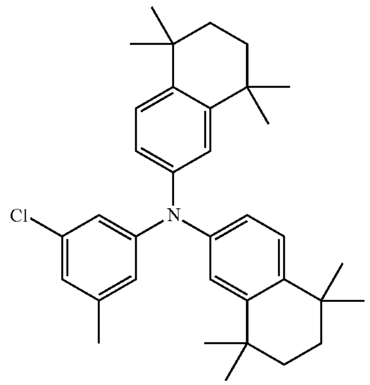

7

40 g of 1-bromo-3-chloro-5-methylbenzene, 75.8 g of bis(5,5,8,8-tetramethyl-5,6,7,8-tetrahydronaphthalen-2-yl) amine, and the same material and equivalent weight as in the synthesis method of Intermediate 1 were used and then recrystallized to obtain 72 g of Intermediate 7. (Yield 72%). MS[M+H]+=515

2) Synthesis of Intermediate 8

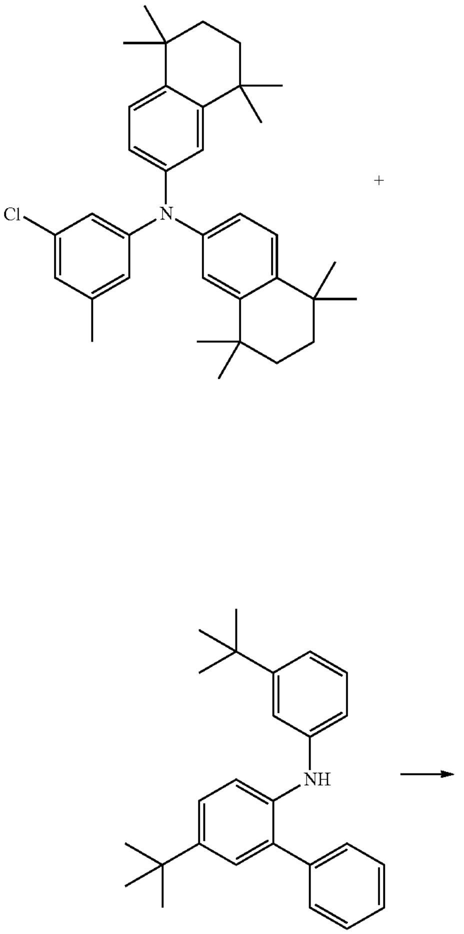

-continued

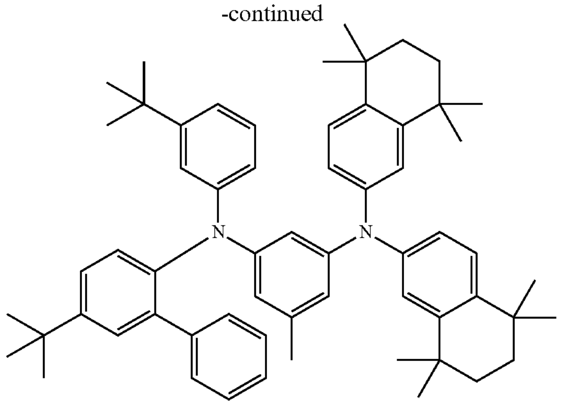

8

30 g of Intermediate 7, 20.9 g of 5-(tert-butyl)-N-(3-(tert-butyl)phenyl)-[1,1'-biphenyl]-2-amine, and the same material and equivalent weight as in the synthesis method of Intermediate 2 were used and then recrystallized to obtain 39 g of Intermediate 8. (Yield 80%). MS[M+H]+=836

3) Synthesis of BD-5

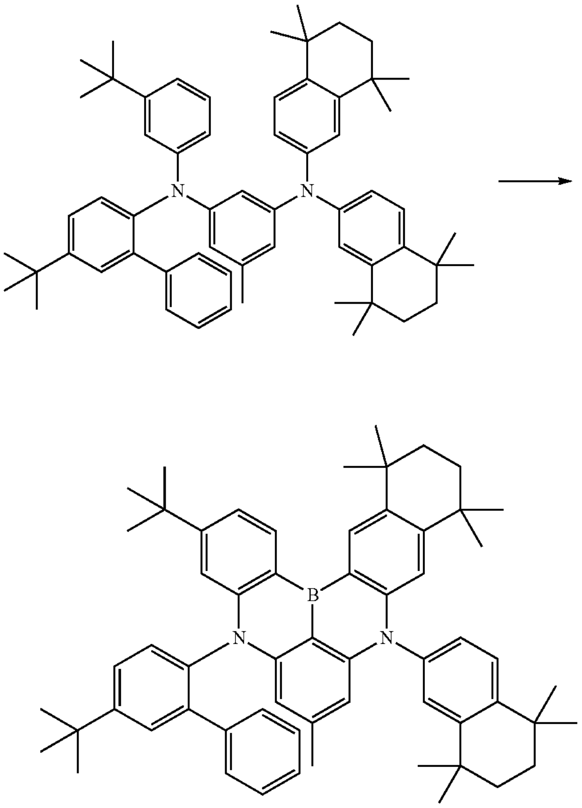

BD-5

After 25 g of Intermediate 8 and 19.9 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 8.1 g of BD-5 (yield 32%). MS[M+H]+=844

Synthesis Example 65. Synthesis of BD-6

1) Synthesis of Intermediate 9

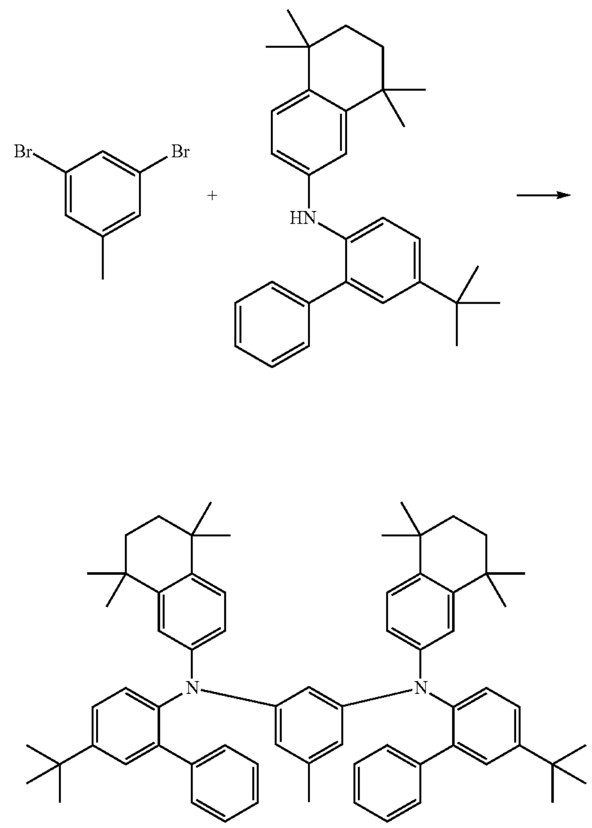

9

After 40 g of 1,3-dibromo-5-methylbenzene, 98.8 g of N-(5-(tert-butyl)-[1,1'-biphenyl]-2-yl)-5,5,8,8-tetramethyl-5,6,7,8-tetrahydronaphthalen-2-amine, 92 g of sodium-tert-butoxide, and 0.6 g of bis(tri-tert-butylphosphine)palladium (0) were put into 1,000 ml of toluene, the resulting mixture was stirred under reflux for 2 hours. After the completion of the reaction, the resulting product was extracted, and then recrystallized to obtain 80 g of Intermediate 9. (Yield 73%). MS[M+H]+=912

2) Synthesis of BD-6

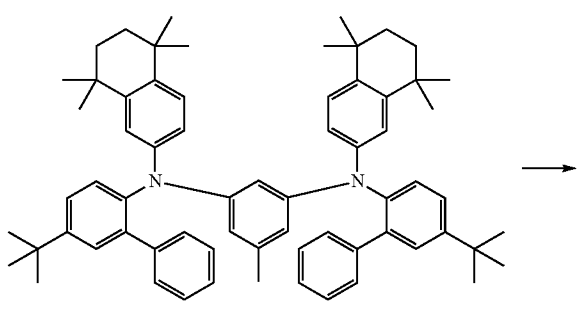

-continued

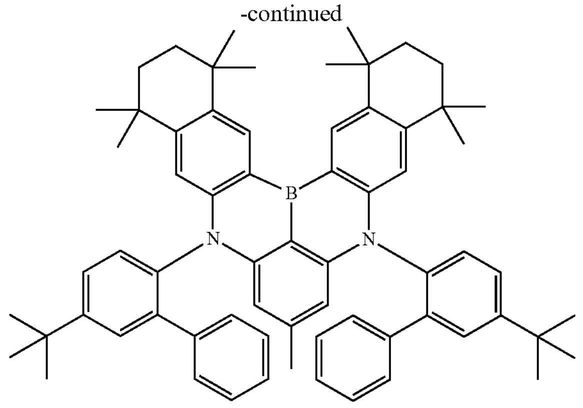

BD-6

After 25 g of Intermediate 9 and 18.3 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.8 g of BD-6 (yield 31%). MS[M+H]+=920

Synthesis Example 66. Synthesis of BD-7

1) Synthesis of Intermediate 11

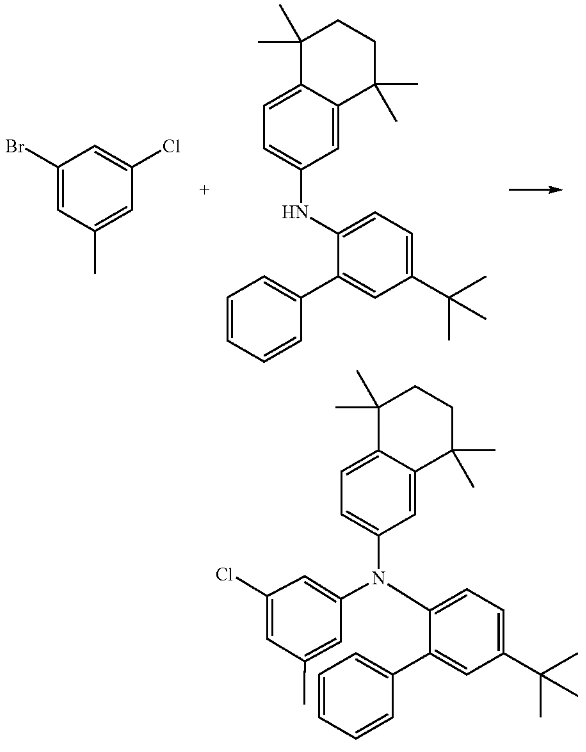

11

40 g of 1-bromo-3-chloro-5-methylbenzene, 80.1 g of N-(5-(tert-butyl)-[1,1'-biphenyl]-2-yl)-5,5,8,8-tetramethyl-5,6,7,8-tetrahydronaphthalen-2-amine, and the same material and equivalent weight as in the synthesis method of Intermediate 1 were used and then recrystallized to obtain 77 g of Intermediate 11. (Yield 74%). MS[M+H]+=537

2) Synthesis of Intermediate 12

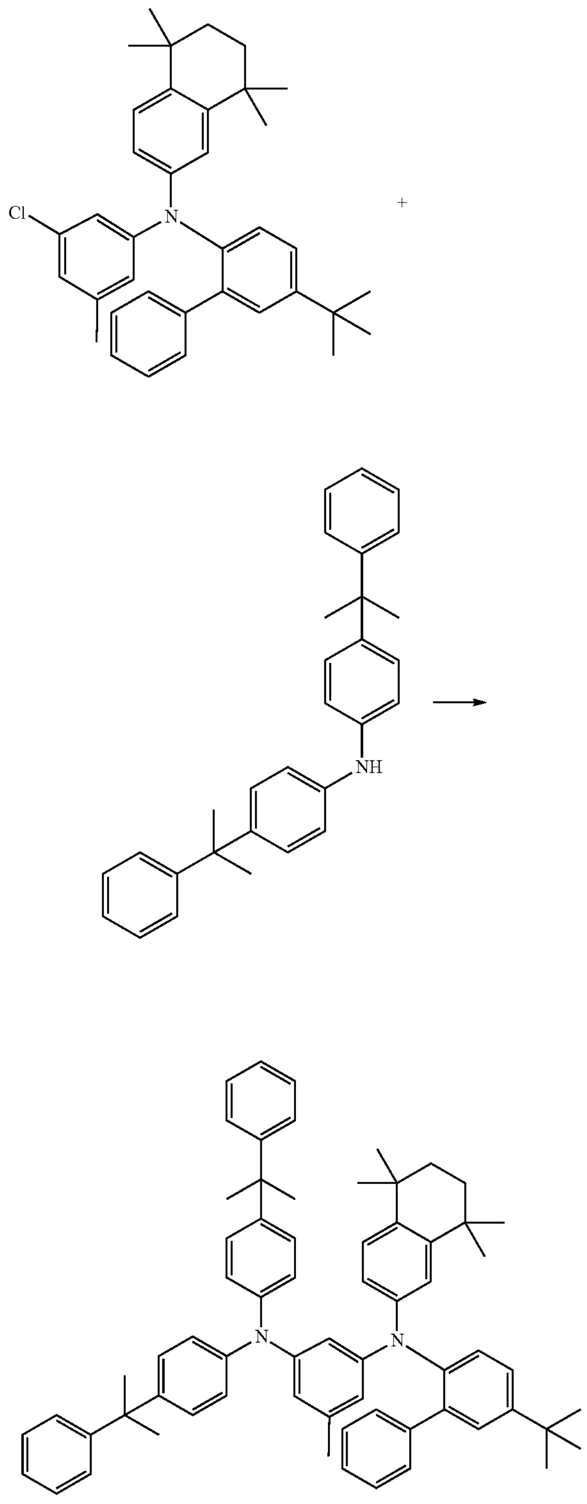

12

30 g of Intermediate 11, 22.7 g of bis(4-(2-phenylpropan-2-yl)phenyl)amine, and the same material and equivalent weight as in the synthesis method of Intermediate 2 were used and then recrystallized to obtain 33 g of Intermediate 12. (Yield 65%). MS[M+H]+=906

3) Synthesis of BD-7

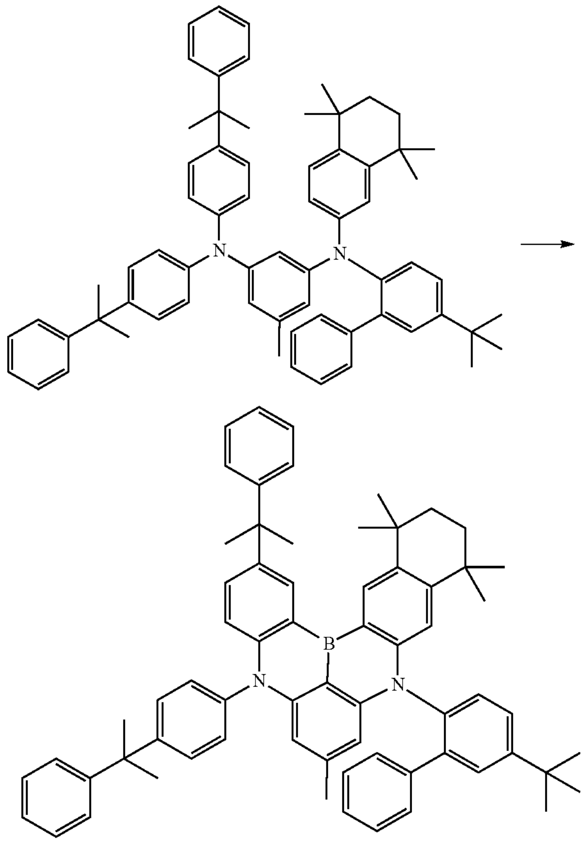

BD-7

After 25 g of Intermediate 12 and 18.4 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.5 g of BD-7 (yield 30%). MS[M+H]+=914

Synthesis Example 67. Synthesis of BD-8

1) Synthesis of Intermediate 13

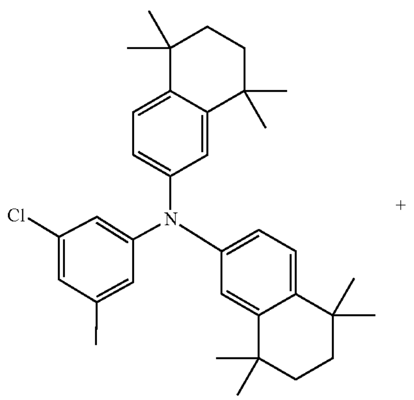

-continued

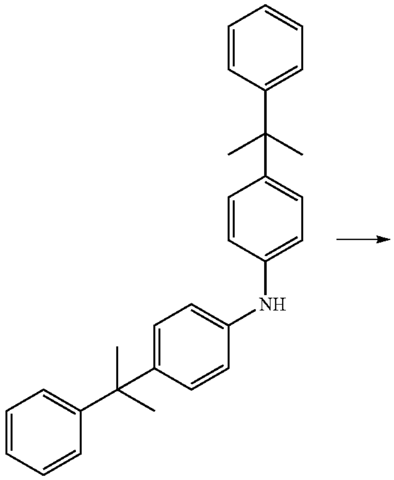

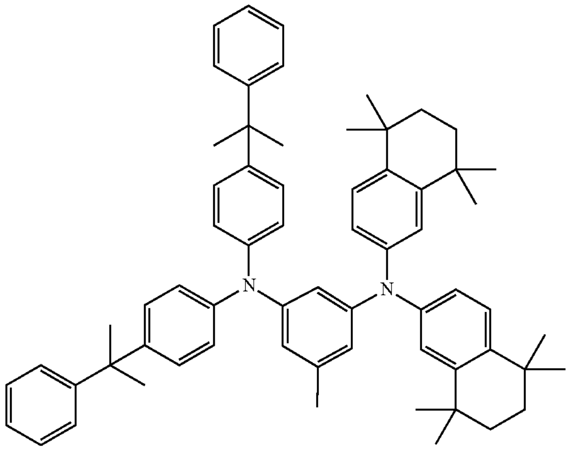

13

30 g of Intermediate 7, 23.7 g of bis(4-(2-phenylpropan-2-yl)phenyl)amine, and the same material and equivalent weight as in the synthesis method of Intermediate 2 were used and then recrystallized to obtain 36 g of Intermediate 13. (Yield 70%). MS[M+H]+=884

2) Synthesis of BD-8

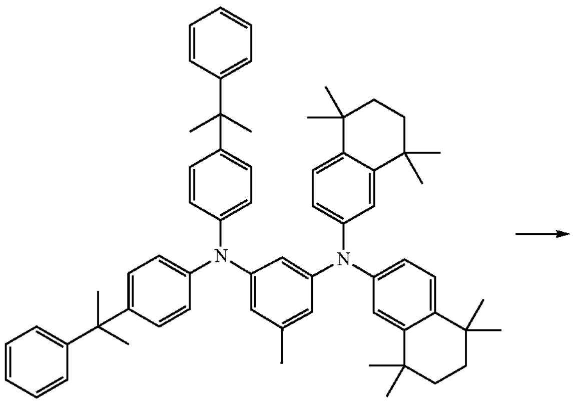

-continued

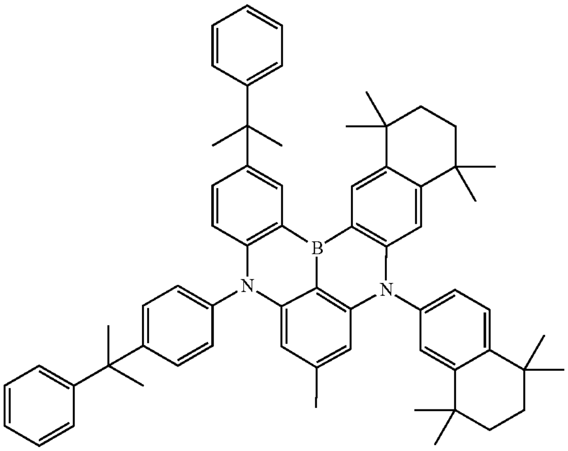

BD-8

After 25 g of Intermediate 13 and 18.8 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.6 g of BD-8 (yield 30%). MS[M+H]+=892

Synthesis Example 68. Synthesis of BD-9

1) Synthesis of Intermediate 14

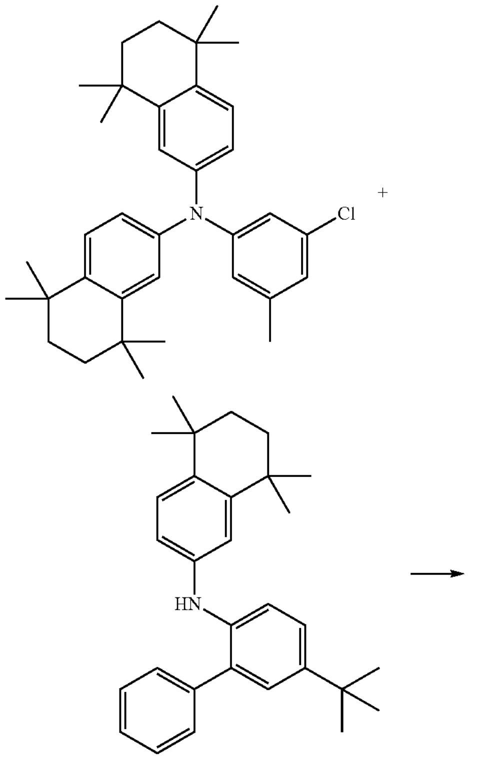

-continued

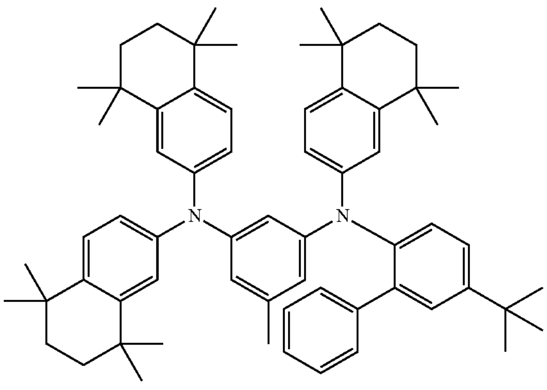

14

30 g of Intermediate 7, 24.7 g of N-(5-(tert-butyl)-[1,1'-biphenyl]-2-yl)-5,5,8,8-tetramethyl-5,6,7,8-tetrahydronaphthalen-2-amine and the same material and equivalent weight as in the synthesis method of Intermediate 2 were used and then recrystallized to obtain 39 g of Intermediate 14. (Yield 75%). MS[M+H]+=890

2) Synthesis of BD-9

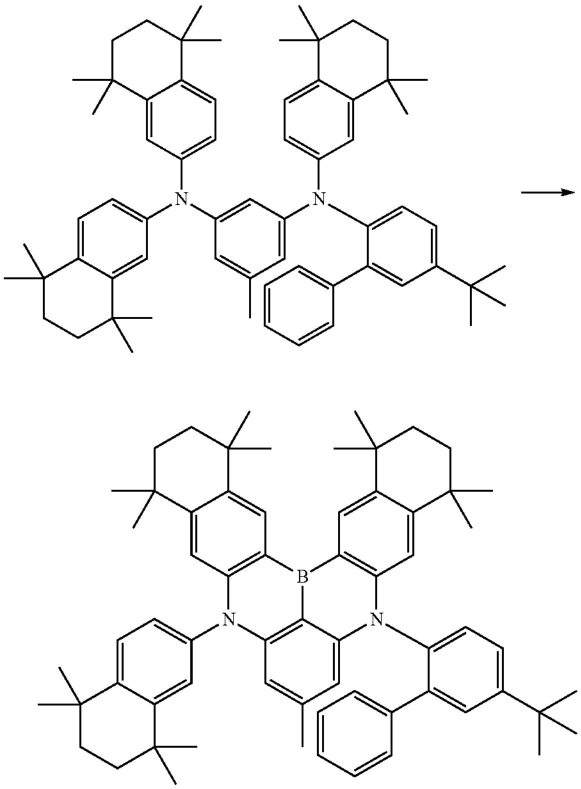

BD-9

After 25 g of Intermediate 14 and 18.7 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.2 g of BD-9 (yield 29%). MS[M+H]+=898

Synthesis Example 69. Synthesis of BD-10

1) Synthesis of Intermediate 15

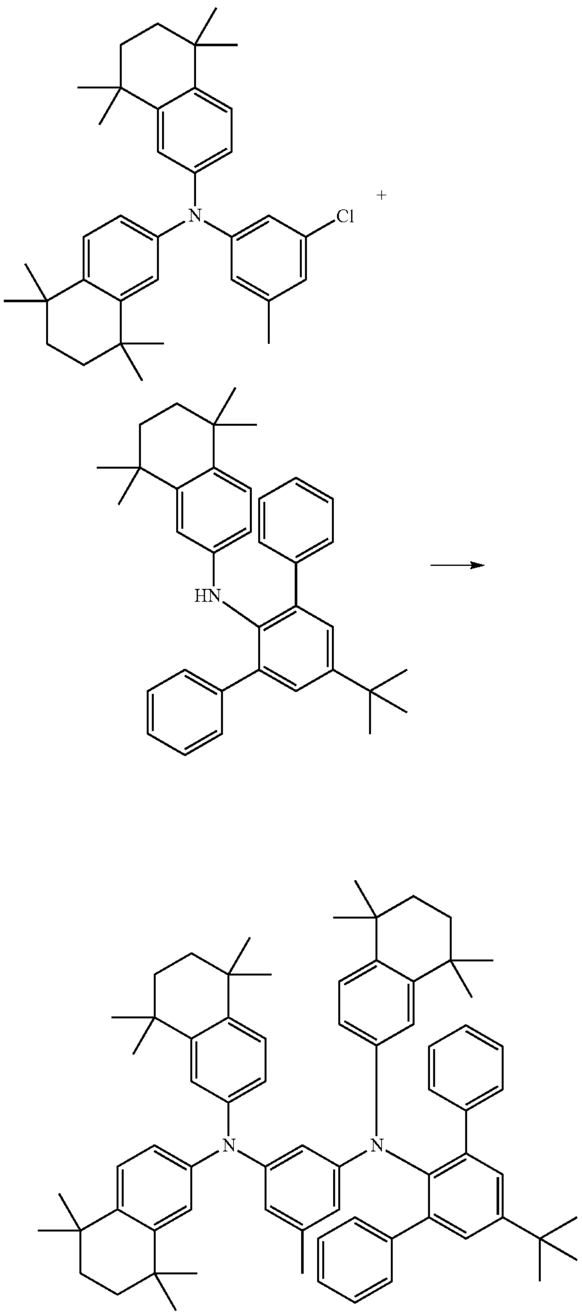

15

30 g of Intermediate 7, 28.5 g of N-(5'-(tert-butyl)-[1,1':3',1''-terphenyl]-2'-yl)-5,5,8,8-tetramethyl-5,6,7,8-tetrahydronaphthalen-2-amine, and the same material and equivalent weight as in the synthesis method of Intermediate 2 were used and then recrystallized to obtain 42 g of Intermediate 15. (Yield 75%). MS[M+H]+=966

2) Synthesis of BD-10

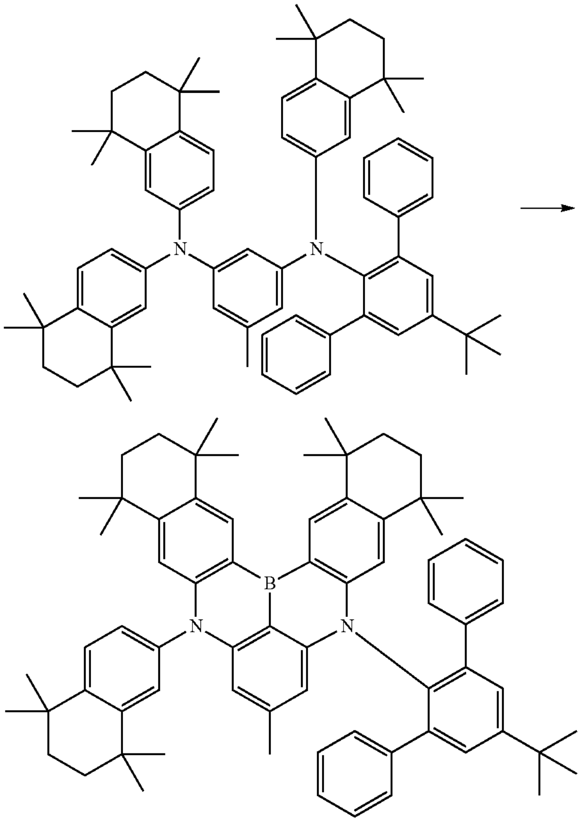

BD-10

After 25 g of Intermediate 15 and 17.3 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.6 g of BD-10 (yield 30%). MS[M+H]+=974

Synthesis Example 70. Synthesis of BD-11

1) Synthesis of Intermediate 16

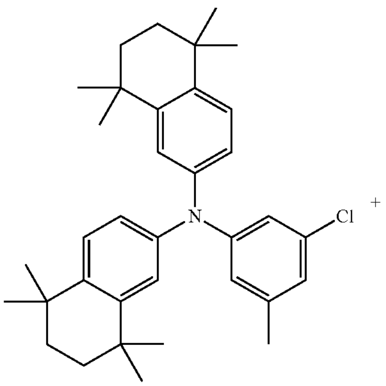

-continued

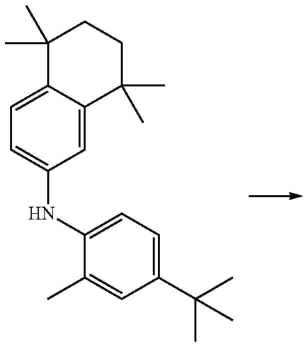

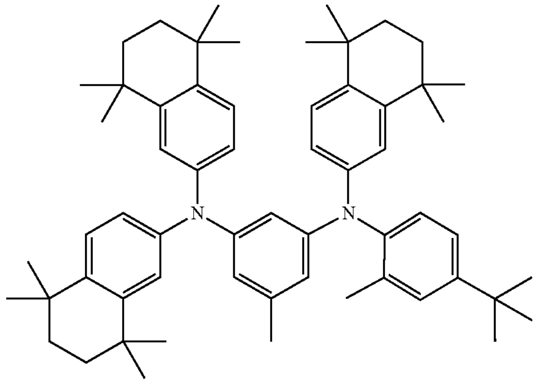

16

30 g of Intermediate 7, 20.4 g of N-(4-(tert-butyl)-2-methylphenyl)-5,5,8,8-tetramethyl-5,6,7,8-tetrahydronaphthalen-2-amine, and the same material and equivalent weight as in the synthesis method of Intermediate 2 were used and then recrystallized to obtain 33 g of Intermediate 16. (Yield 68%). MS[M+H]+=828

2) Synthesis of BD-11

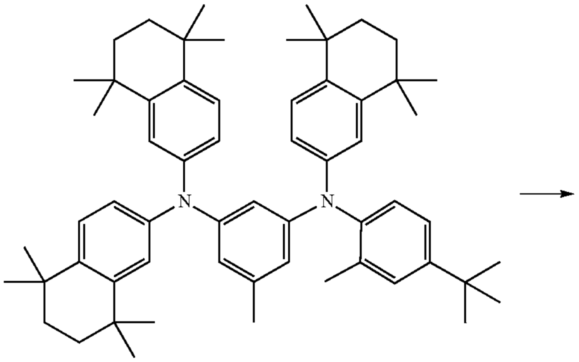

-continued

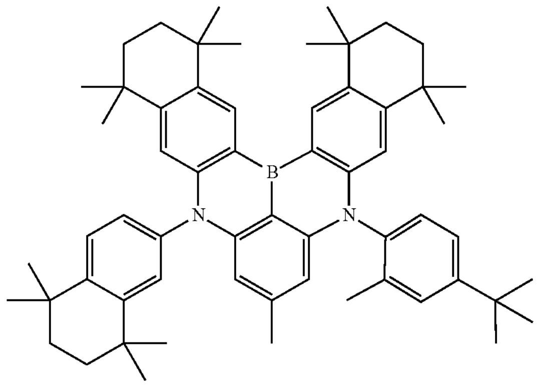

BD-11

After 25 g of Intermediate 16 and 20.1 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.7 g of BD-11 (yield 31%). MS[M+H]+=836

Synthesis Example 71. Synthesis of BD-12

1) Synthesis of Intermediate 17

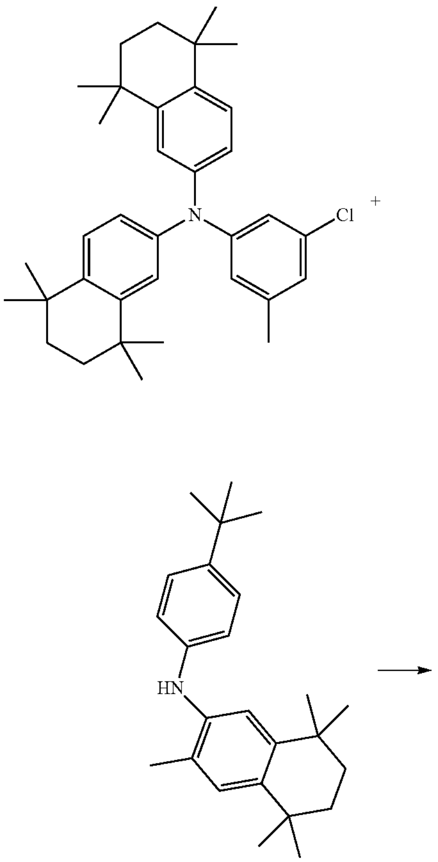

-continued

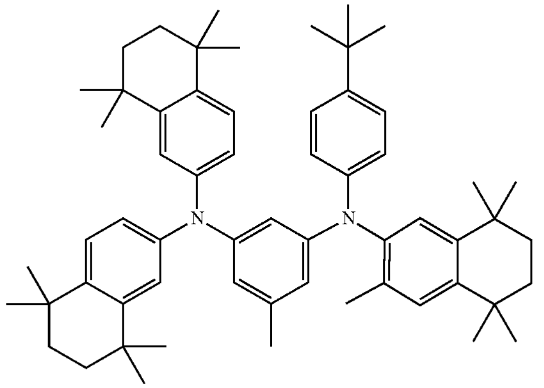

17

30 g of Intermediate 7, 20.4 g of N-(4-(tert-butyl)phenyl)-3,5,5,8,8-pentamethyl-5,6,7,8-tetrahydronaphthalen-2-amine, and the same material and equivalent weight as in the synthesis method of Intermediate 2 were used and then recrystallized to obtain 32 g of Intermediate 17. (Yield 66%). MS[M+H]+=828

2) Synthesis of BD-12

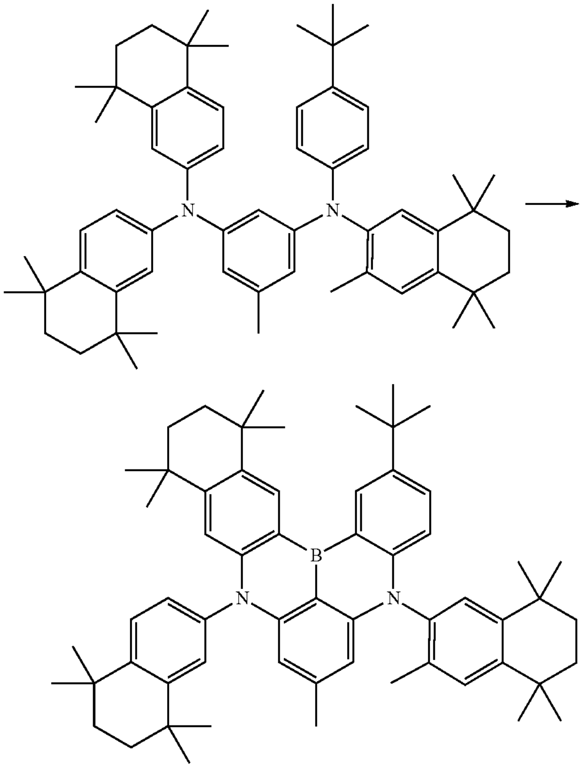

BD-12

After 25 g of Intermediate 17 and 20.1 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.5 g of BD-12 (yield 30%). MS[M+H]+=836

Synthesis Example 72. Synthesis of BD-13

1) Synthesis of Intermediate 18

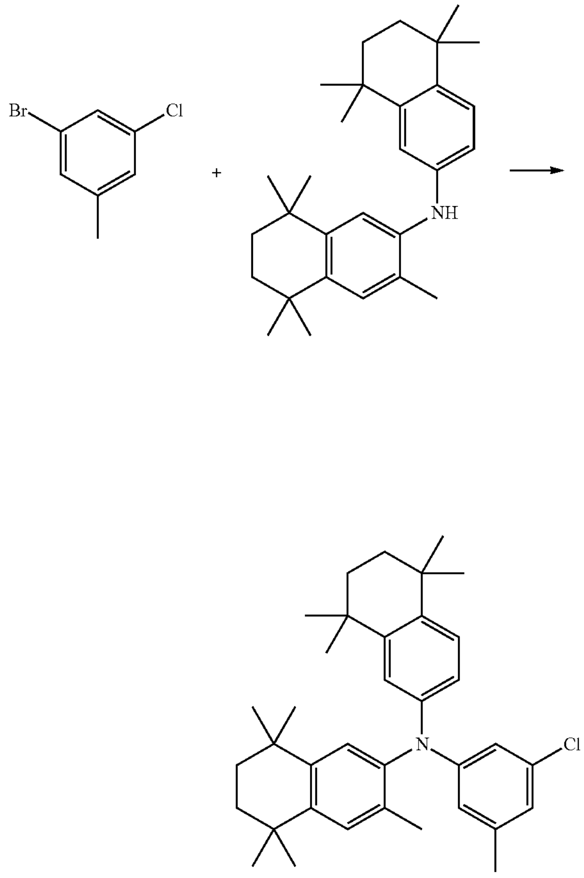

18

40 g of 1-bromo-3-chloro-5-methylbenzene, 78.6 g of 3,5,5,8,8-pentamethyl-N-(5,5,8,8-tetramethyl-5,6,7,8-tetrahydronaphthalen-2-yl)-5,6,7,8-tetrahydronaphthalen-2-amine, and the same material and equivalent weight as in the synthesis method of Intermediate 1 were used and then recrystallized to obtain 78 g of Intermediate 18. (Yield 76%). MS[M+H]+=529

2) Synthesis of Intermediate 19

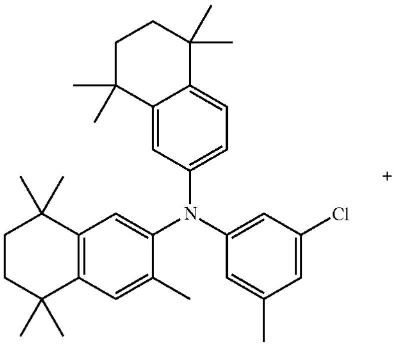

-continued

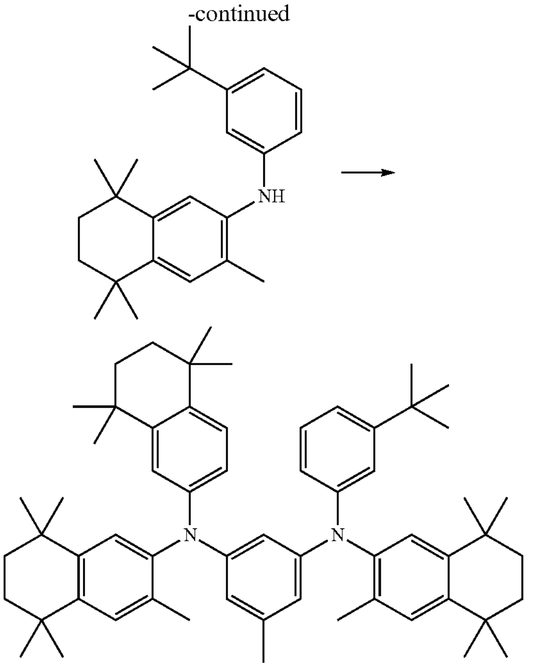

19

30 g of Intermediate 18, 19.9 g of N-(3-(tert-butyl)phenyl)-3,5,5,8,8-pentamethyl-5,6,7,8-tetrahydronaphthalen-2-amine, and the same material and equivalent weight as in the synthesis method of Intermediate 2 were used and then recrystallized to obtain 32 g of Intermediate 19. (Yield 68%). MS[M+H]+=828

3) Synthesis of BD-13

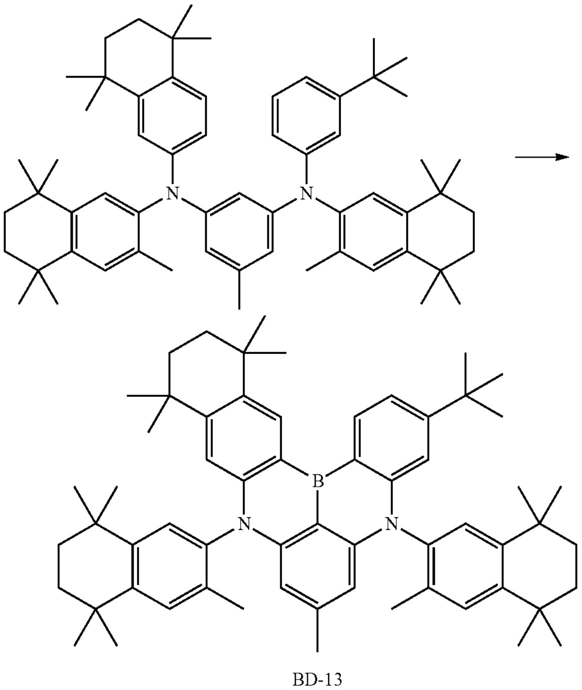

BD-13

After 25 g of Intermediate 19 and 20.1 g of boron triiodide were put into 250 ml of 1,2-dichlorobenzene under a nitrogen atmosphere, the resulting mixture was stirred at 160° C.

for 4 hours. After the completion of the reaction, the resulting product was extracted, and then recrystallized to obtain 7.8 g of BD-13 (yield 31%). MS[M+H]+=836

Synthesis Example 73. Synthesis of BD-14

1) Synthesis of Intermediate 20

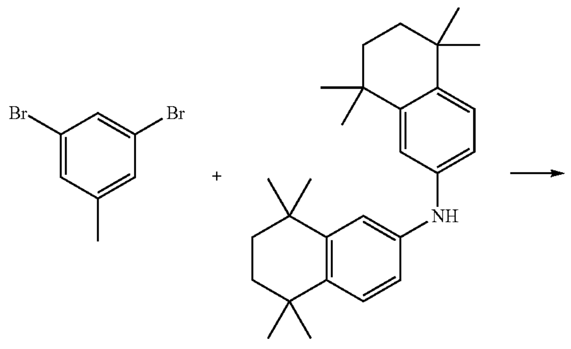

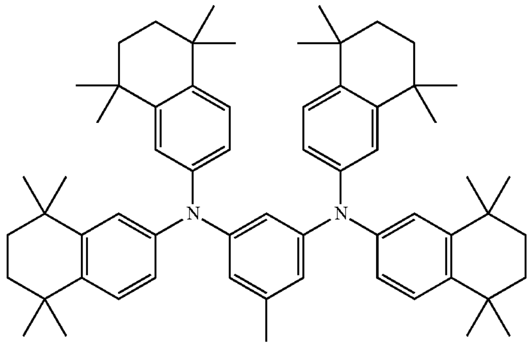

20

30 g of 1,3-dibromo-5-methylbenzene and 93.5 g of bis(5,5,8,8-tetramethyl-5,6,7,8-tetrahydronaphthalen-2-yl) amine, and the same material and equivalent weight as in the synthesis method of Intermediate 2 were used and then recrystallized to obtain 77 g of Intermediate 20. (Yield 74%). MS[M+H]+=868

2) Synthesis of BD-14

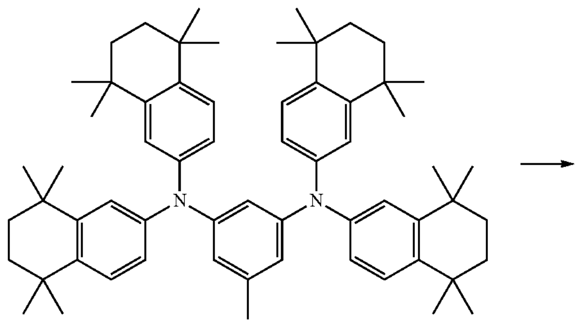

-continued

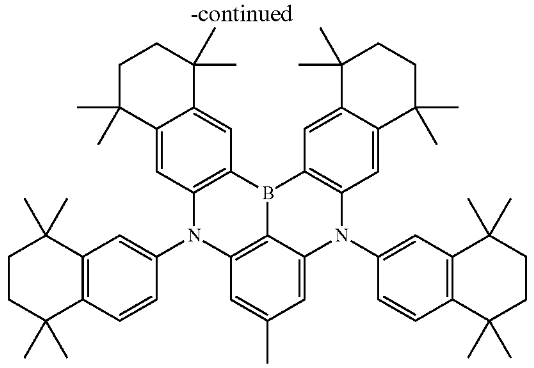

BD-14

After 25 g of Intermediate 20 and 19.2 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.8 g of BD-14 (yield 31%). MS[M+H]+=876

Synthesis Example 74. Synthesis of BD-15

1) Synthesis of Intermediate 21

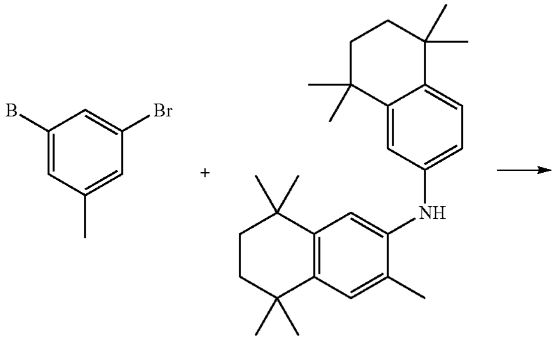

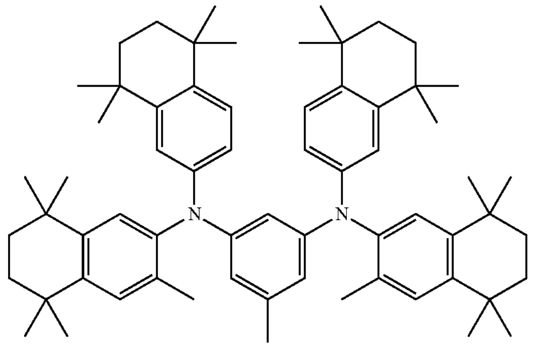

21

30 g of 1,3-dibromo-5-methylbenzene and 100.2 g of bis(3,5,5,8,8-pentamethyl-5,6,7,8-tetrahydronaphthalen-2-yl)amine the same material and equivalent weight as in the synthesis method of Intermediate 2 were used and then recrystallized to obtain 74 g of Intermediate 21. (Yield 69%). MS[M+H]+=896

2) Synthesis of BD-15

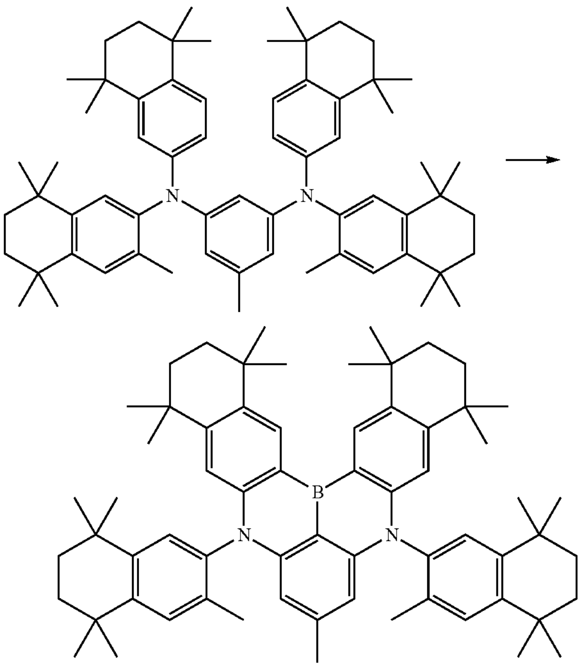

BD-15

After 25 g of Intermediate 21 and 18.6 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.7 g of BD-15 (yield 31%). MS[M+H]+=904

Synthesis Example 75. Synthesis of BD-16

1) Synthesis of Intermediate 22

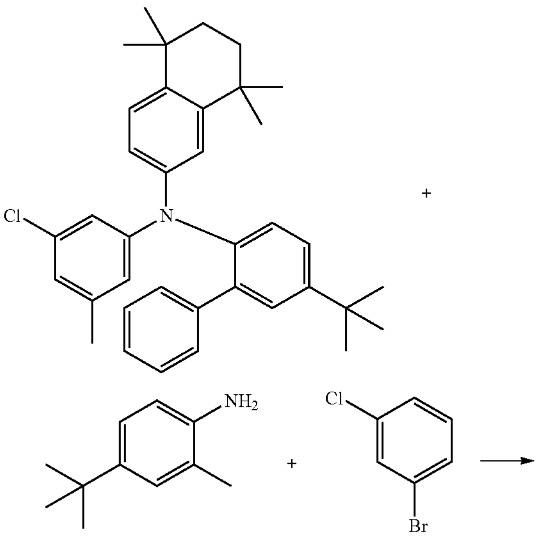

-continued

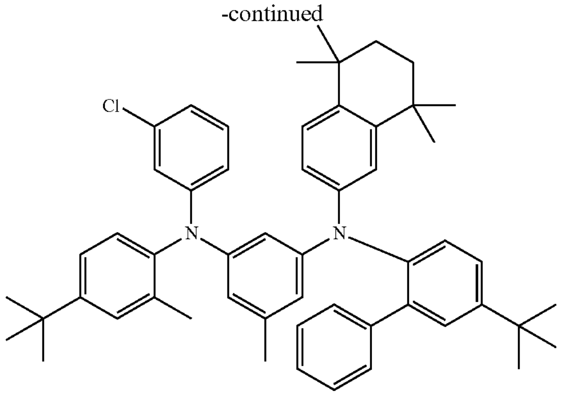

22

After 40 g of Intermediate 11, 12.2 g of 4-(tert-butyl)-2-methylaniline, 21.5 g of sodium-tert-butoxide, and 0.4 g of bis(tri-tert-butylphosphine)palladium(0) were put into 600 ml of toluene, the resulting mixture was refluxed for 1 hour, whether the reaction proceeded was confirmed, and then 14.3 g of 1-bromo-3-chlorobenzene was added thereto during the reflux reaction, and the reflux reaction was performed for an additional 1 hour. After the completion of the reaction, the resulting product was extracted, and then recrystallized to obtain 44 g of Intermediate 22. (Yield 76%). MS[M+H]+=774

2) Synthesis of Intermediate 23

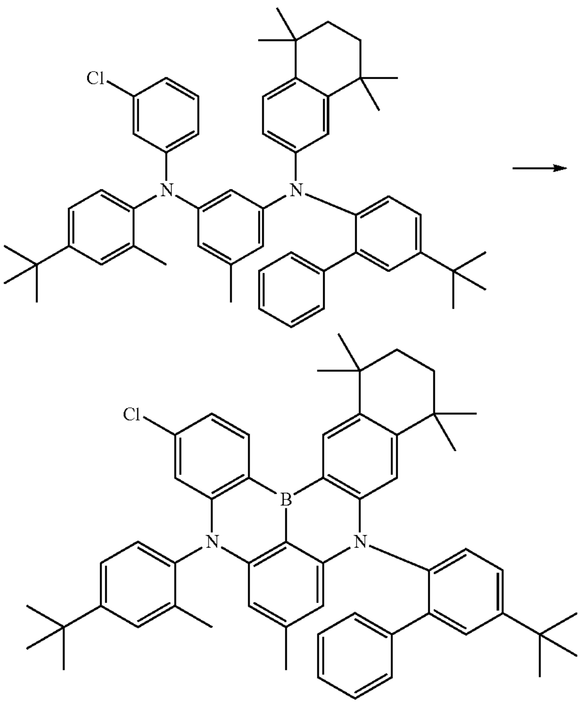

After 25 g of Intermediate 22 and 21.5 g of boron triiodide were put into 250 ml of 1,2-dichlorobenzene, the resulting mixture was stirred at 160° C. for 4 hours. After the completion of the reaction, the resulting product was extracted, and then recrystallized to obtain 7.6 g of Intermediate 23 (yield 30%). MS[M+H]+=876

3) Synthesis of BD-16

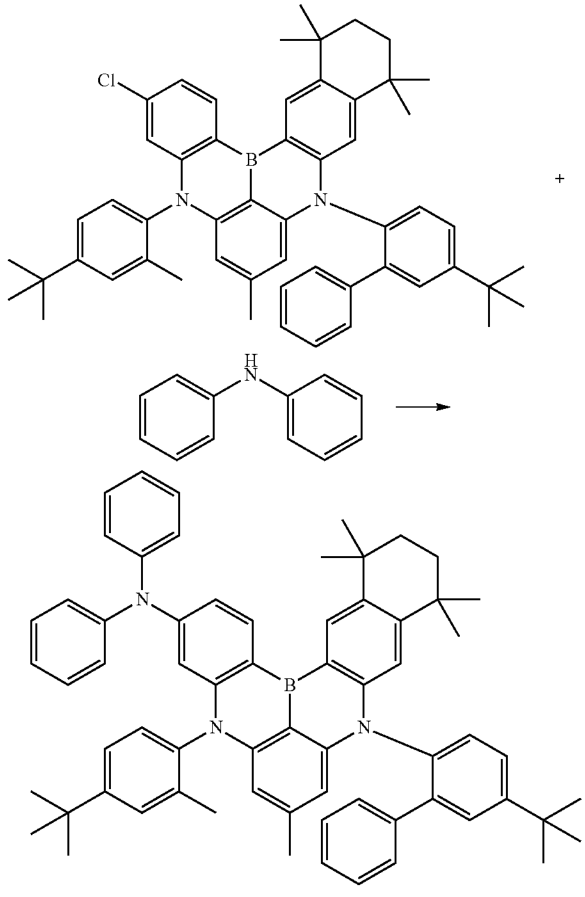

BD-16

After 7 g of Intermediate 23, 1.52 g of diphenylamine, 1.7 g of sodium-tert-butoxide, and 0.05 g of bis(tri-tert-butylphosphine)palladium(0) were put into 80 ml of xylene under a nitrogen atmosphere, the resulting mixture was stirred under reflux for 5 hours. After the completion of the reaction, the resulting product was extracted, and then recrystallized to obtain 7 g of BD-16. (Yield 85%). MS[M+H]+=915

Synthesis Example 76. Synthesis of BD-17

1) Synthesis of BD-17

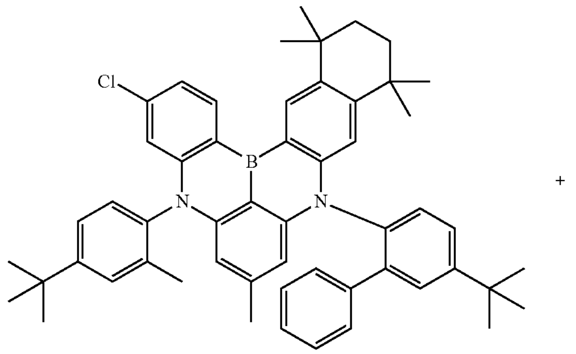

-continued

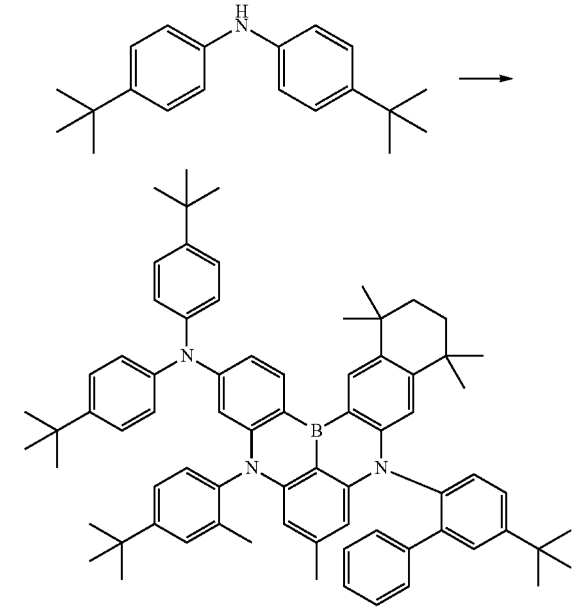

BD-17

After 7 g of Intermediate 23, 1.52 g of bis(4-(tert-butyl)phenyl)amine, 2.6 g of sodium-tert-butoxide, and 0.05 g of bis(tri-tert-butylphosphine)palladium(0) were put into 80 ml of xylene under a nitrogen atmosphere, the resulting mixture was stirred under reflux for 5 hours. After the completion of the reaction, the resulting product was extracted, and then recrystallized to obtain 7.7 g of BD-17. (Yield 84%). MS[M+H]+=1027

Synthesis Example 77. Synthesis of BD-18

1) Synthesis of BD-18

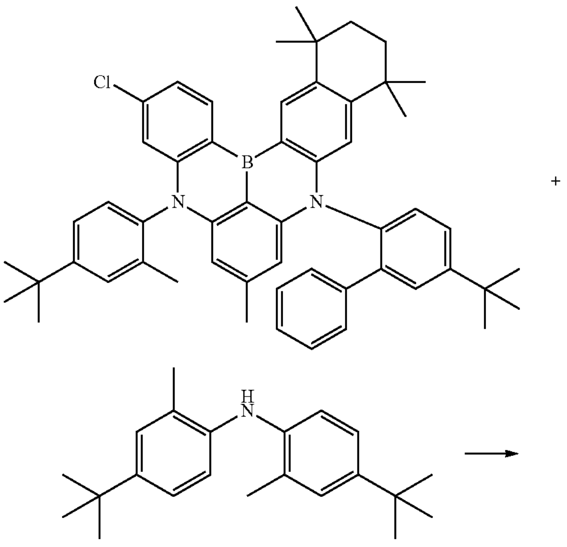

-continued

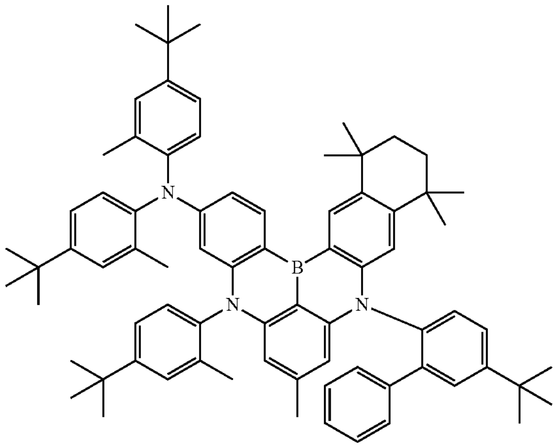

BD-18

After 7 g of Intermediate 23, 2.77 g of bis(4-(tert-butyl)-2-methylphenyl)amine, 2.7 g of sodium-tert-butoxide, and 0.5 g of bis(tri-tert-butylphosphine)palladium(0) were put into 80 ml of xylene under a nitrogen atmosphere, the resulting mixture was stirred under reflux for 5 hours. After the completion of the reaction, the resulting product was extracted, and then recrystallized to obtain 7.8 g of BD-18. (Yield 83%). MS[M+H]+=1055

Synthesis Example 78. Synthesis of BD-19

1) Synthesis of Intermediate 24

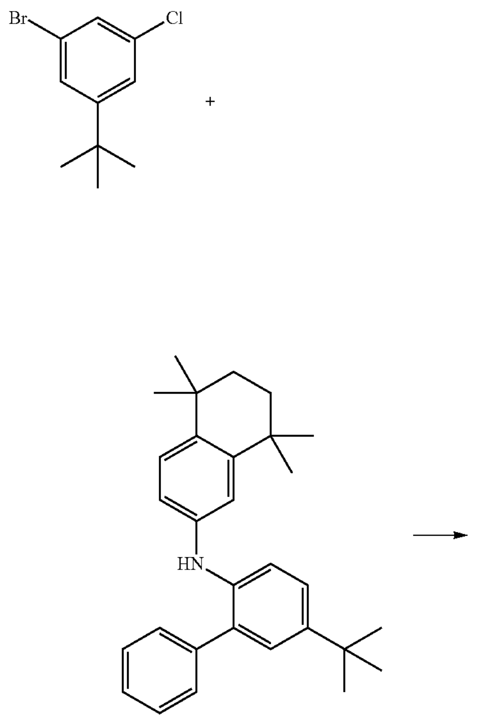

-continued

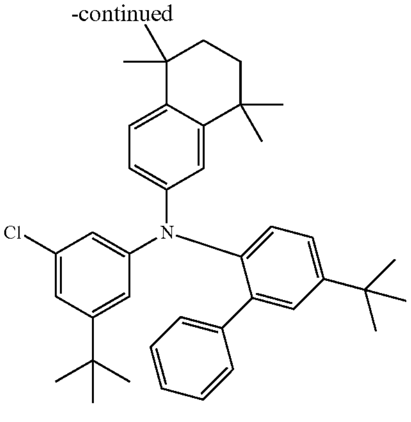

24

40 g of 1-bromo-3-(tert-butyl)-5-chlorobenzene, 66.5 g of N-(5-(tert-butyl)-[1,1'-biphenyl]-2-yl)-5,5,8,8-tetramethyl-5,6,7,8-tetrahydronaphthalen-2-amine, and the same material and equivalent weight as in the synthesis method of Intermediate 1 were used and then recrystallized to obtain 75 g of Intermediate 24. (Yield 80%). MS[M+H]+=579

2) Synthesis of Intermediate 25

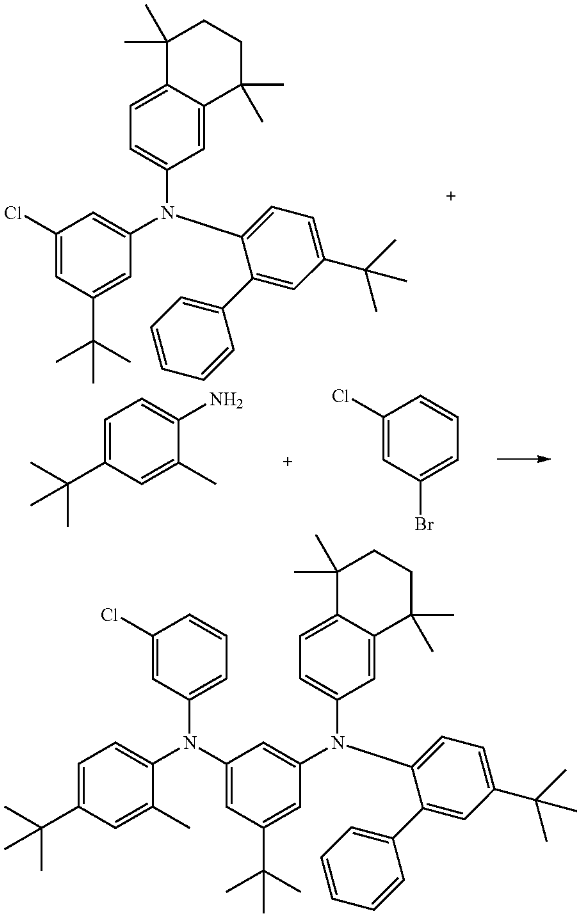

25

After 40 g of Intermediate 24, 11.3 g of 4-(tert-butyl)-2-methylaniline, 19.9 g of sodium-tert-butoxide, and 0.4 g of bis(tri-tert-butylphosphine)palladium(0) were put into 600 ml of toluene, the resulting mixture was refluxed for 1 hour, whether the reaction proceeded was confirmed, and then 13.2 g of 1-bromo-3-chlorobenzene was added thereto during the reflux reaction, and the reflux reaction was performed for an additional 1 hour. After the completion of the reaction, the resulting product was extracted, and then recrystallized to obtain 42 g of Intermediate 25. (Yield 74%). MS[M+H]+=816

3) Synthesis of Intermediate 26

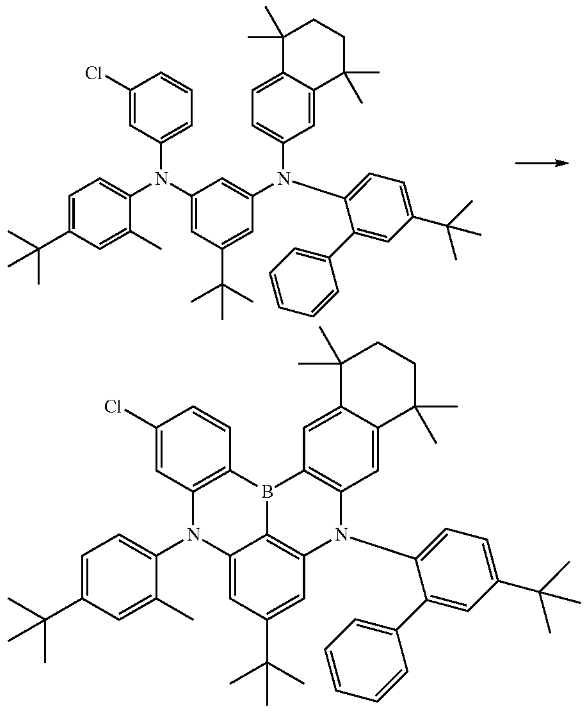

26

After 25 g of Intermediate 25 and 20.4 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 8.1 g of Intermediate 26 (yield 32%). MS[M+H]+=825

4) Synthesis of BD-19

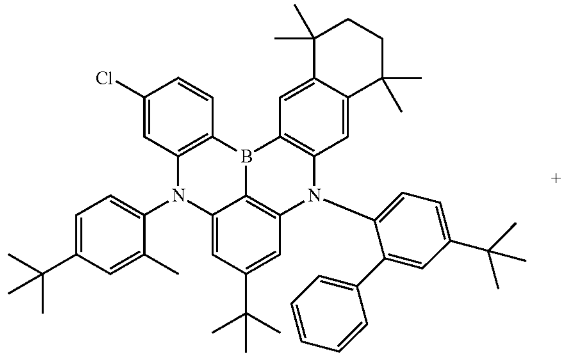

-continued

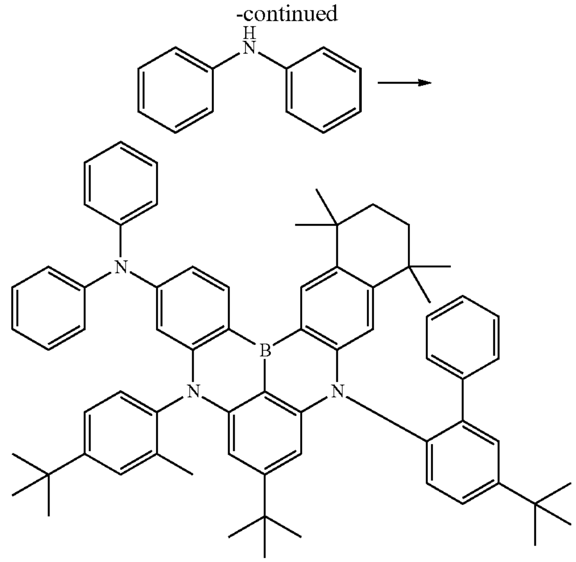

BD-19

After 7 g of Intermediate 26, 1.5 g of diphenylamine, 1.7 g of sodium-tert-butoxide, and 0.05 g of bis(tri-tert-butylphosphine)palladium(0) were put into 80 ml of xylene, the resulting mixture was stirred under reflux for 5 hours. After the completion of the reaction, the resulting product was extracted, and then recrystallized to obtain 6.5 g of BD-19. (Yield 80%). MS[M+H]+=957

Synthesis Example 79. Synthesis of BD-20

1) Synthesis of Intermediate 27

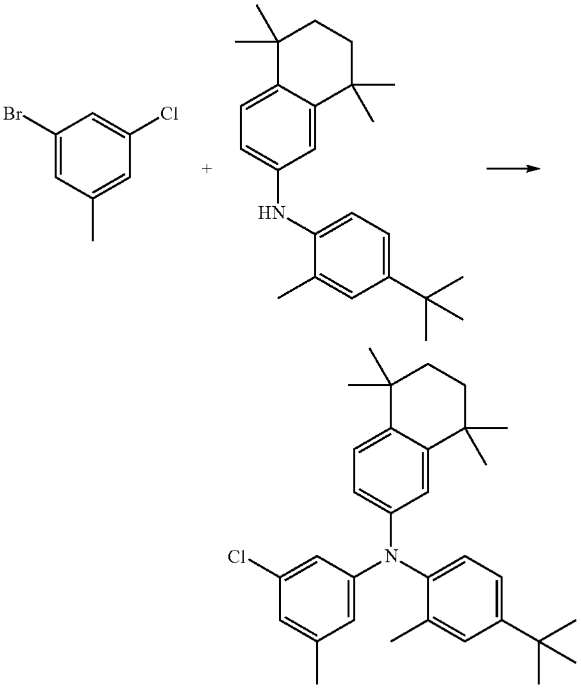

27

40 g of 1-bromo-3-chloro-5-methylbenzene, 56.5 g of N-(4-(tert-butyl)-2-methylphenyl)-5,5,8,8-tetramethyl-5,6, 7,8-tetrahydronaphthalen-2-amine, and the same material and equivalent weight as in the synthesis method of Intermediate 1 were used and then recrystallized to obtain 55 g of Intermediate 27. (Yield 72%). MS[M+H]+=475

2) Synthesis of Intermediate 28

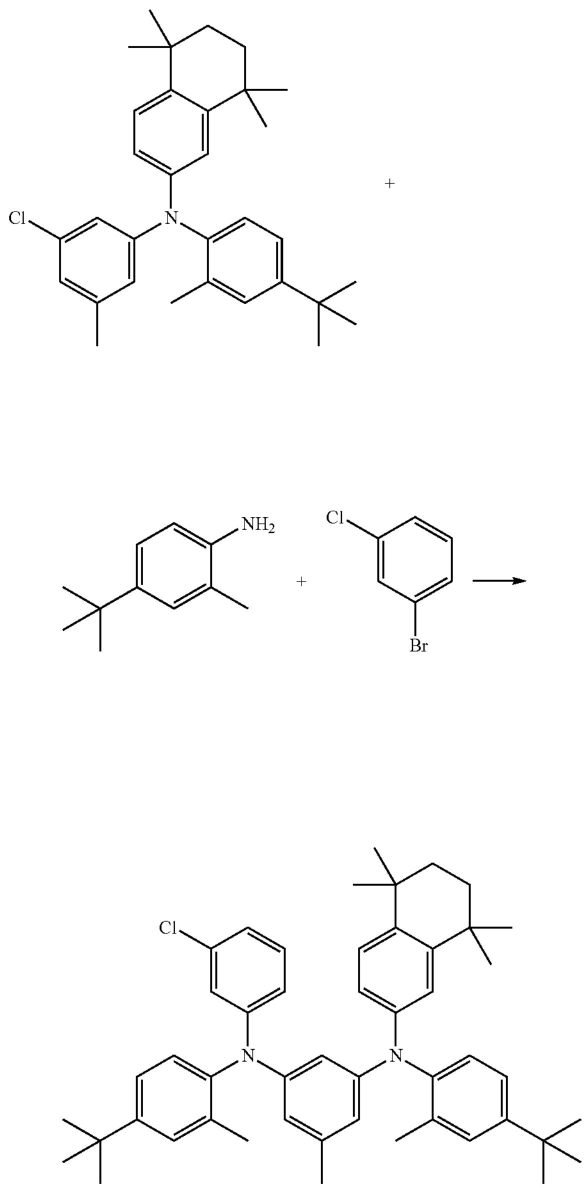

28

After 40 g of Intermediate 27, 13.8 g of 4-(tert-butyl)-2-methylaniline, 24.3 g of sodium-tert-butoxide, and 0.4 g of bis(tri-tert-butylphosphine)palladium(0) were put into 600 ml of toluene, the resulting mixture was refluxed for 1 hour, whether the reaction proceeded was confirmed, and then 16.2 g of 1-bromo-3-chlorobenzene was added thereto during the reflux reaction, and the reflux reaction was performed for an additional 1 hour. After the completion of the reaction, the resulting product was extracted, and then recrystallized to obtain 44 g of Intermediate 28. (Yield 73%). MS[M+H]+=712

3) Synthesis of Intermediate 29

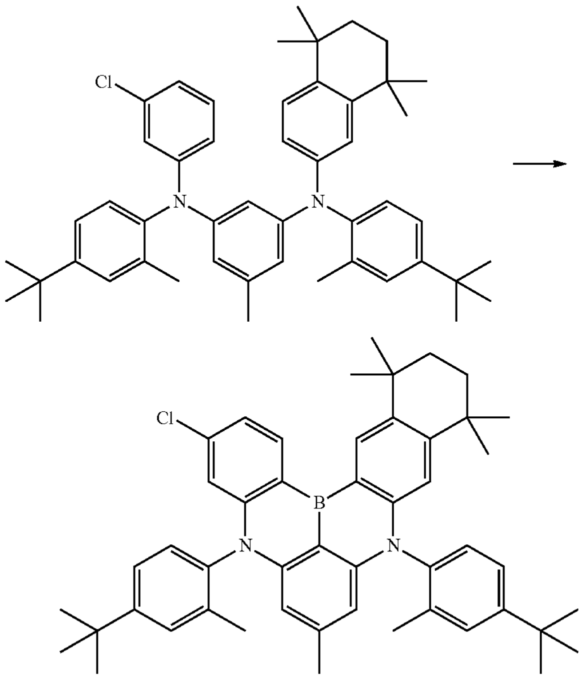

29

After 25 g of Intermediate 28 and 23.4 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 8.2 g of Intermediate 29 (yield 32%). MS[M+H]+ =720

4) Synthesis of BD-20

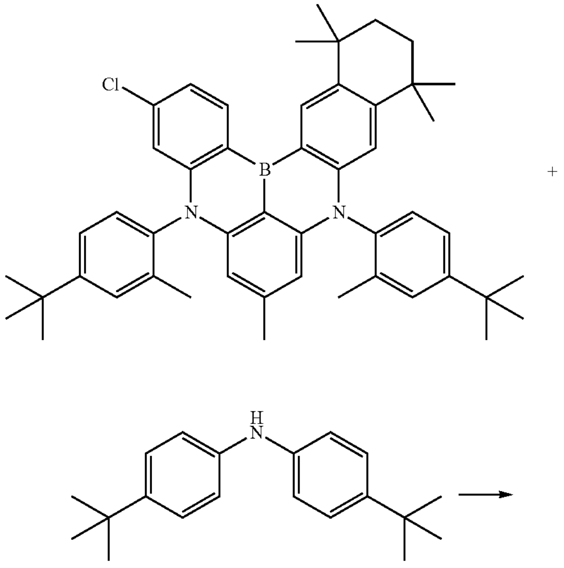

-continued

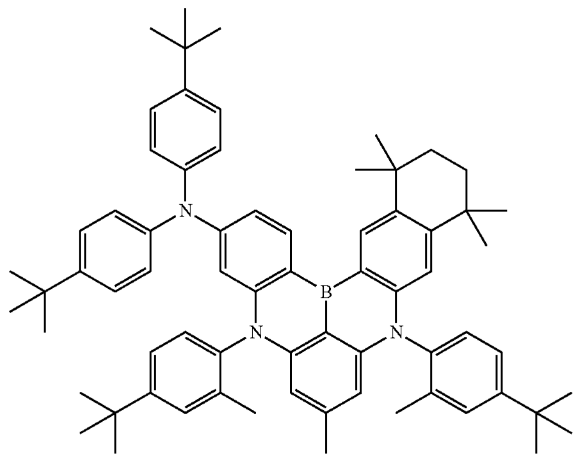

BD-20

After 7 g of Intermediate 29, 1.7 g of diphenylamine, 1.8 g of sodium-tert-butoxide, and 0.05 g of bis(tri-tert-butylphosphine)palladium(0) were put into 80 ml of xylene, the resulting mixture was stirred under reflux for 5 hours. After the completion of the reaction, the resulting product was extracted, and then recrystallized to obtain 6.6 g of BD-20. (Yield 70%). MS[M+H]+=965

Synthesis Example 80. Synthesis of BD-21

1) Synthesis of Intermediate 30

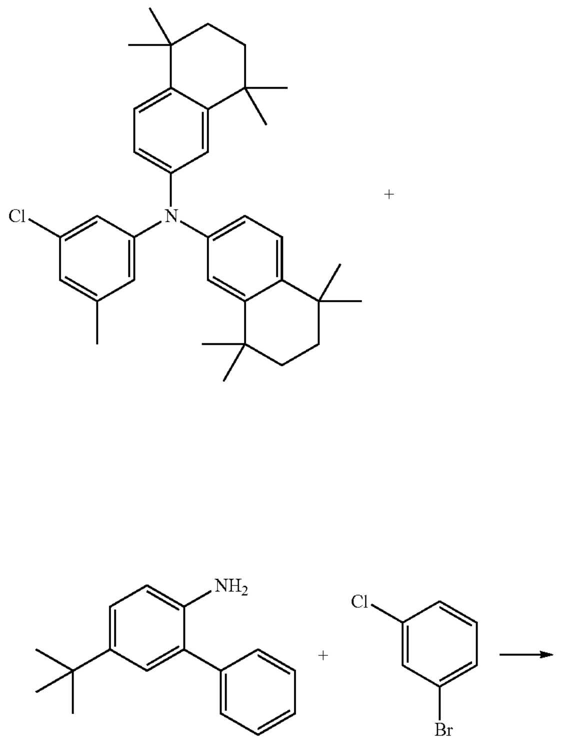

-continued

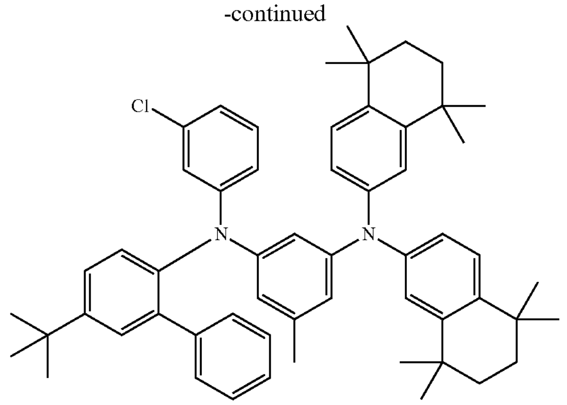

30

After 40 g of Intermediate 7, 17.6 g of 5-(tert-butyl)-[1, 1'-biphenyl]-2-amine, 22.4 g of sodium-tert-butoxide, and 0.4 g of bis(tri-tert-butylphosphine)palladium(0) were put into 600 ml of toluene, the resulting mixture was refluxed for 1 hour, whether the reaction proceeded was confirmed, and then 14.9 g of 1-bromo-3-chlorobenzene was added thereto during the reflux reaction, and the reflux reaction was performed for an additional 1 hour. After the completion of the reaction, the resulting product was extracted, and then recrystallized to obtain 45 g of Intermediate 30. (Yield 71%). MS[M+H]+=814

2) Synthesis of Intermediate 31

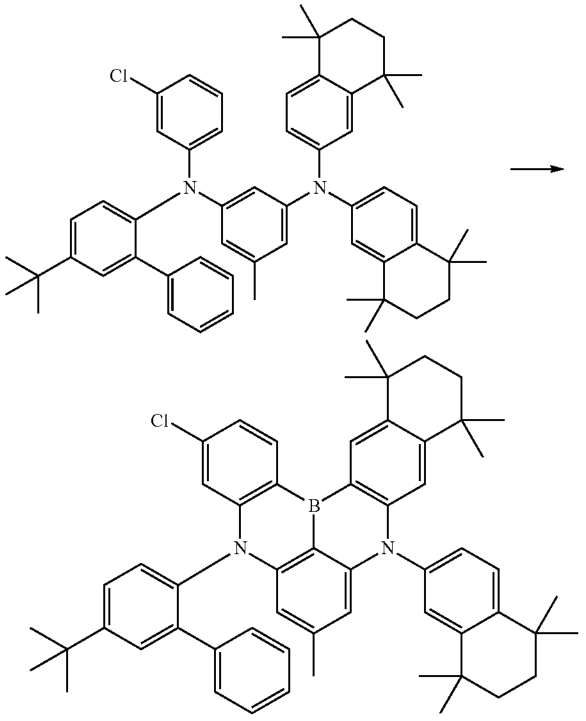

31

After 25 g of Intermediate 30 and 20.4 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 8.3 g of Intermediate 31 (yield 33%). MS[M+H]+ =822

3) Synthesis of BD-21

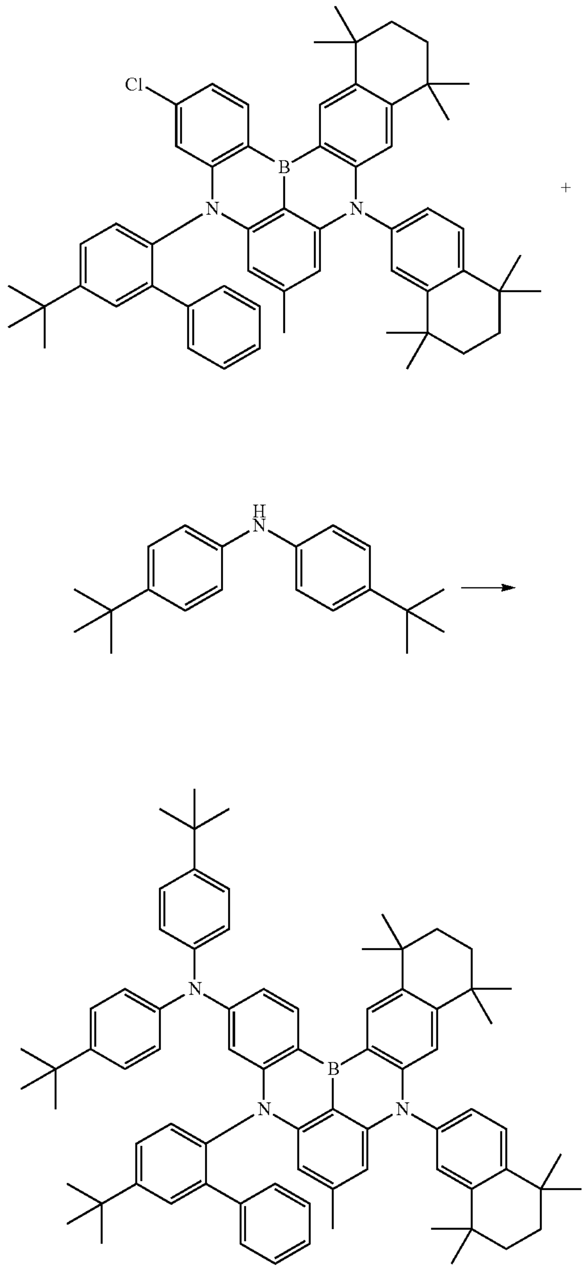

BD-21

After 7 g of Intermediate 31, 2.4 g of bis(4-(tert-butyl) phenyl)amine, 1.7 g of sodium-tert-butoxide, and 0.05 g of bis(tri-tert-butylphosphine)palladium(0) were put into 80 ml of xylene, the resulting mixture was stirred under reflux for 5 hours. After the completion of the reaction, the resulting product was extracted, and then recrystallized to obtain 6.5 g of BD-21. (Yield 72%). MS[M+H]+=1067

Synthesis Example 81. Synthesis of BD-22

3) Synthesis of BD-22

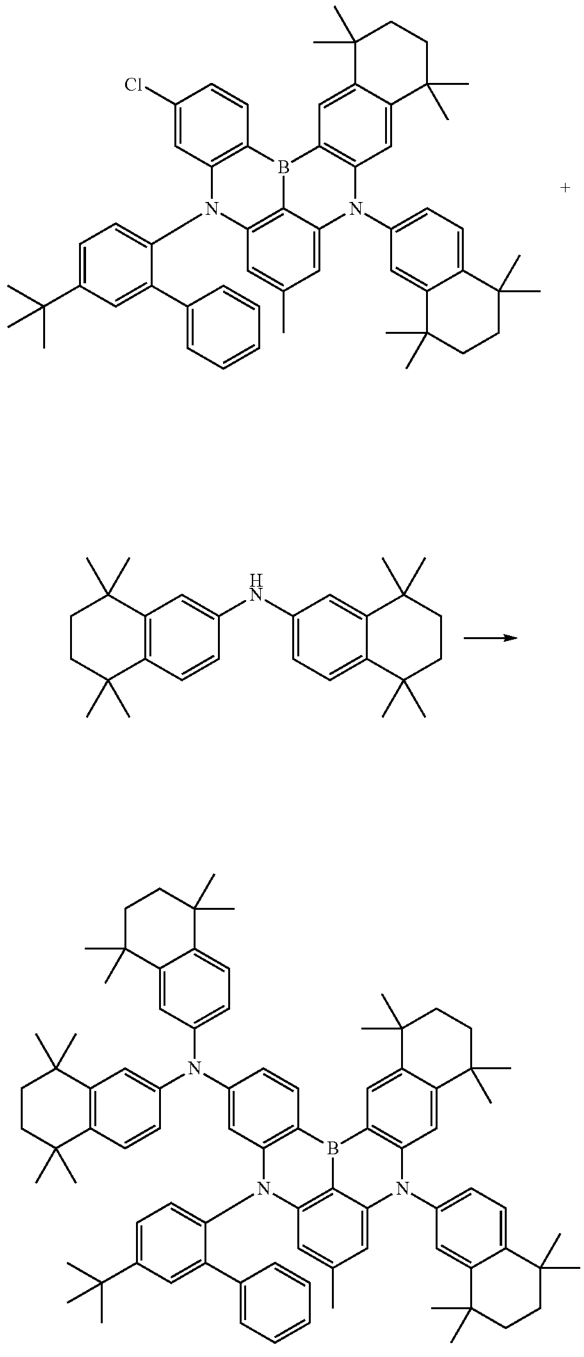

BD-22

After 7 g of Intermediate 31, 3.4 g of bis(5,5,8,8-tetramethyl-5,6,7,8-tetrahydronaphthalen-2-yl)amine, 1.7 g of sodium-tert-butoxide, and 0.05 g of bis(tri-tert-butylphosphine)palladium(0) were put into 80 ml of xylene, the resulting mixture was stirred under reflux for 5 hours. After the completion of the reaction, the resulting product was extracted, and then recrystallized to obtain 7.4 g of BD-22. (Yield 74%). MS[M+H]+=1175

Synthesis Example 82. Synthesis of BD-23

1) Synthesis of Intermediate 32

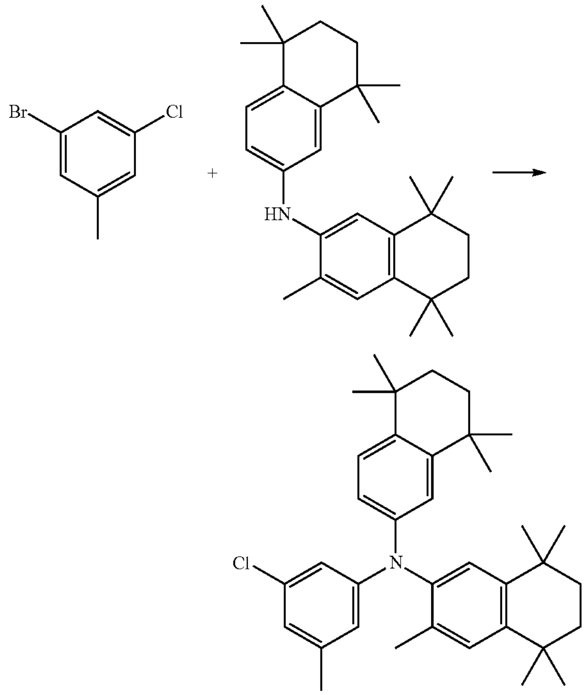

32

40 g of 1-bromo-3-chloro-5-methylbenzene, 78.6 g of 1,5,5,8,8-pentamethyl-N-(5,5,8,8-tetramethyl-5,6,7,8-tetrahydronaphthalen-2-yl)-5,6,7,8-tetrahydronaphthalen-2-amine, and the same material and equivalent weight as in the synthesis method of Intermediate 1 were used and then recrystallized to obtain 72 g of Intermediate 32. (Yield 70%). MS[M+H]+=529

2) Synthesis of Intermediate 33

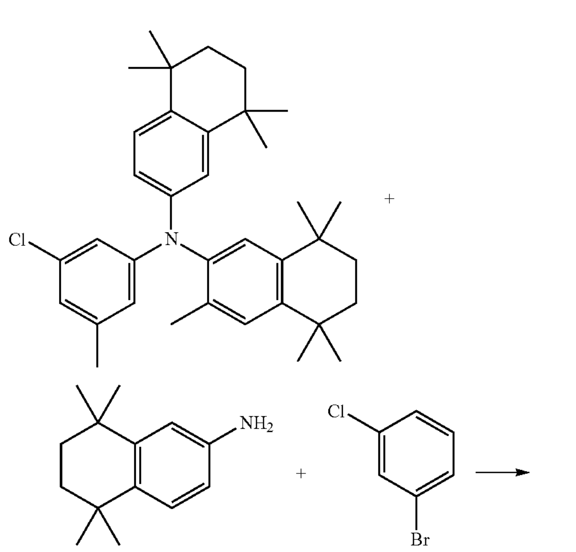

-continued

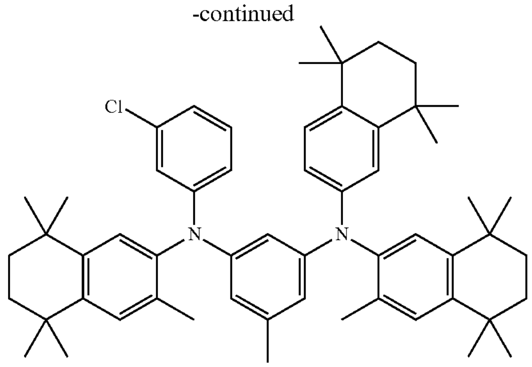

33

After 40 g of Intermediate 32, 16.5 g of 3,5,5,8,8-pentamethyl-5,6,7,8-tetrahydronaphthalen-2-amine, 14.5 g of sodium-tert-butoxide, and 0.4 g of bis(tri-tert-butylphosphine)palladium(0) were put into 600 ml of toluene, the resulting mixture was refluxed for 1 hour, whether the reaction proceeded was confirmed, and then 14.5 g of 1-bromo-3-chlorobenzene was added thereto during the reflux reaction, and the reflux reaction was performed for an additional 1 hour. After the completion of the reaction, the resulting product was extracted, and then recrystallized to obtain 46 g of Intermediate 33. (Yield 74%). MS[M+H]+=820

3) Synthesis of Intermediate 34

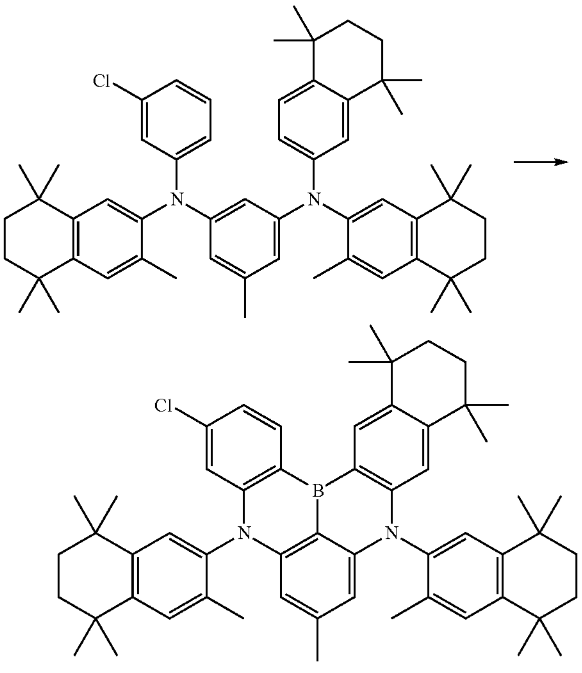

34

After 25 g of Intermediate 33 and 20.3 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.7 g of Intermediate 34 (yield 31%). MS[M+H]+=828

4) Synthesis of BD-23

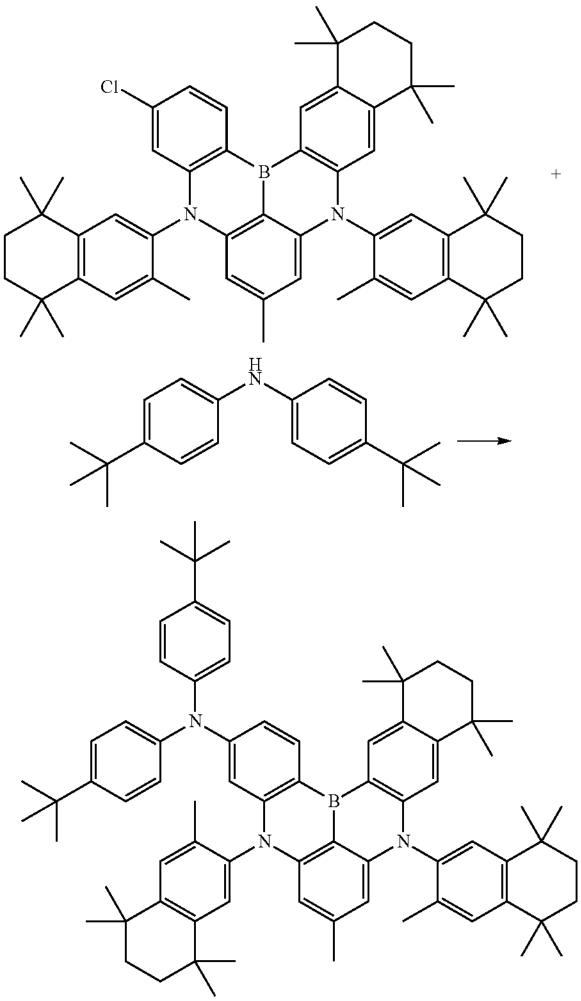

BD-23

After 7 g of Intermediate 34, 2.4 g of bis(4-(tert-butyl) phenyl)amine, 1.7 g of sodium-tert-butoxide, and 0.05 g of bis(tri-tert-butylphosphine)palladium(0) were put into 80 ml of xylene, the resulting mixture was stirred under reflux for 5 hours. After the completion of the reaction, the resulting product was extracted, and then recrystallized to obtain 6.8 g of BD-23. (Yield 75%). MS[M+H]+=1073

Synthesis Example 83. Synthesis of BD-24

1) Synthesis of Intermediate 35

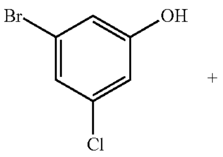

-continued

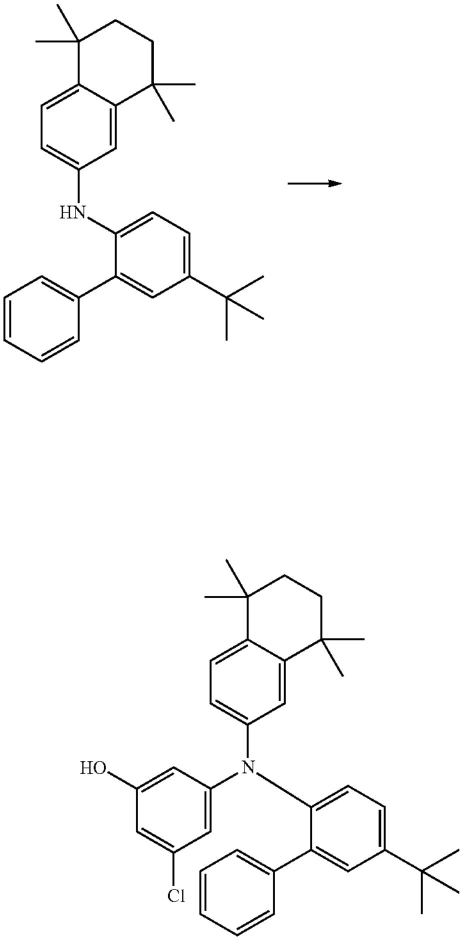

35

40 g of 3-bromo-5-chlorophenol, 79.4 g of N-(5-(tert-butyl)-[1,1'-biphenyl]-2-yl)-5,5,8,8-tetramethyl-5,6,7,8-tetrahydronaphthalen-2-amine, and the same material and equivalent weight as in the synthesis method of Intermediate 1 were used and then recrystallized to obtain 70 g of Intermediate 35. (Yield 57%). MS[M+H]+=539

2) Synthesis of Intermediate 36

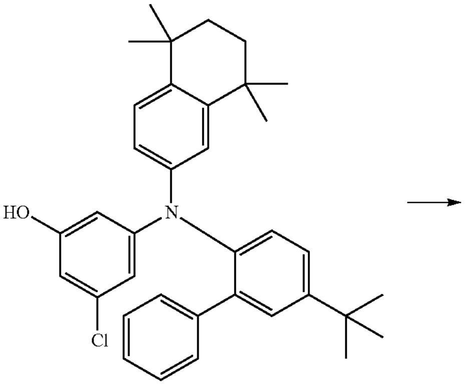

-continued

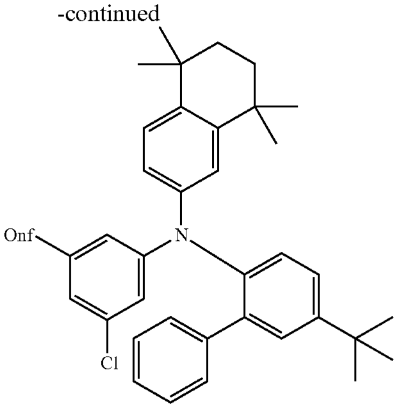

36

After 40 g of Intermediate 35, 20 ml of 1,1,2,2,3,3,4,4,4-nonafluorobutane-1-sulfonyl fluoride, and 30 g of potassium carbonate were put into 400 ml of tetrahydrofuran and 200 ml of water, the resulting mixture was reacted for 3 hours, and then the resulting product was extracted after the completion of the reaction, and then the solution was removed to obtain 58 g of Intermediate 36. (Yield 97%). MS[M+H]+=805

3) Synthesis of Intermediate 37

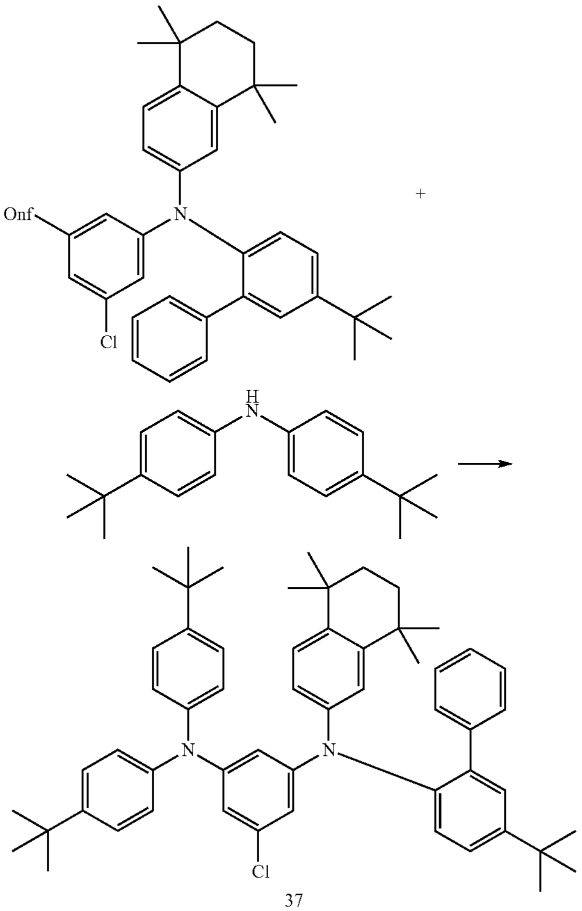

37

After 40 g of Intermediate 36, 14 g of bis(4-(tert-butyl)phenyl)amine, 0.85 g of $Pd(dba)_2$, 1.42 g of Xphos, and 48.6 g of cesium carbonate were put into 500 ml of xylene under a nitrogen atmosphere, the resulting mixture was stirred under reflux for 24 hours. After the completion of the reaction, the resulting product was extracted, and then recrystallized to obtain 31 g of Intermediate 37 (yield 78%). MS[M+H]+=802

4) Synthesis of Intermediate 38

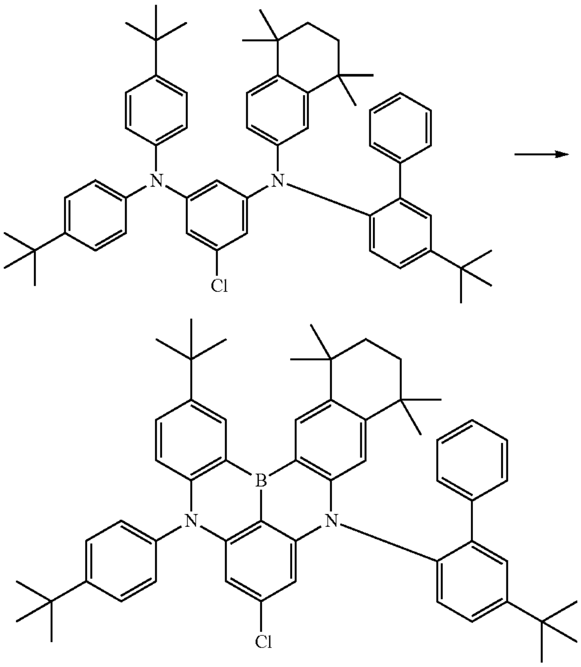

38

After 25 g of Intermediate 37 and 20.8 g of boron triiodide were put into 250 ml of 1,2-dichlorobenzene, the resulting mixture was stirred at 160° C. for 4 hours. After the completion of the reaction, the resulting product was extracted, and then recrystallized to obtain 7.9 g of Intermediate 38 (yield 31%). MS[M+H]+=810

5) Synthesis of BD-24

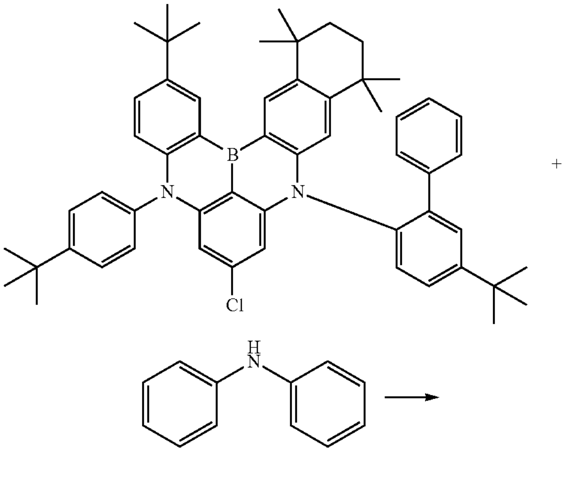

-continued

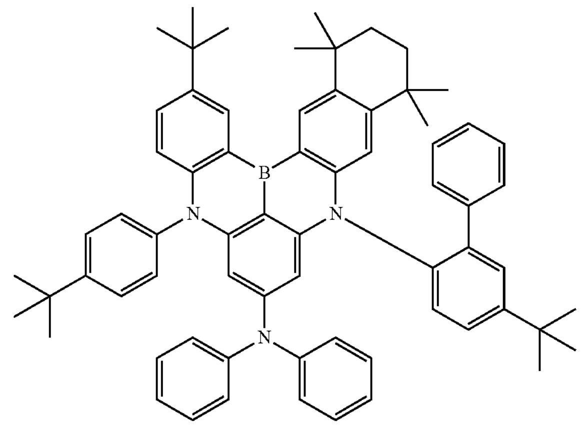

BD-24

After 7 g of Intermediate 38, 1.46 g of diphenylamine, 2.5 g of sodium-tert-butoxide, and 0.05 g of bis(tri-tert-butylphosphine)palladium(0) were put into 80 ml of xylene, the resulting mixture was stirred under reflux for 5 hours.

After the completion of the reaction, the resulting product was extracted, and then recrystallized to obtain 6.2 g of BD-24. (Yield 76%). MS[M+H]+=943

Synthesis Example 84. Synthesis of BD-25

5) Synthesis of BD-25

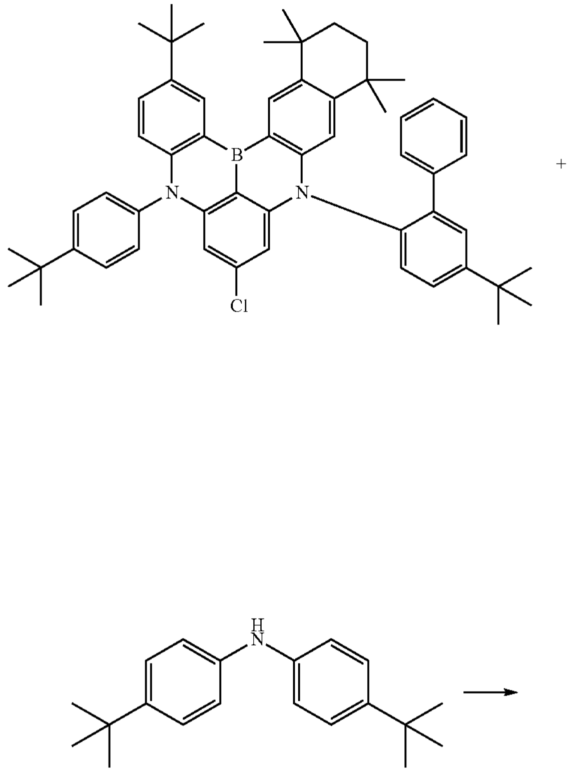

-continued

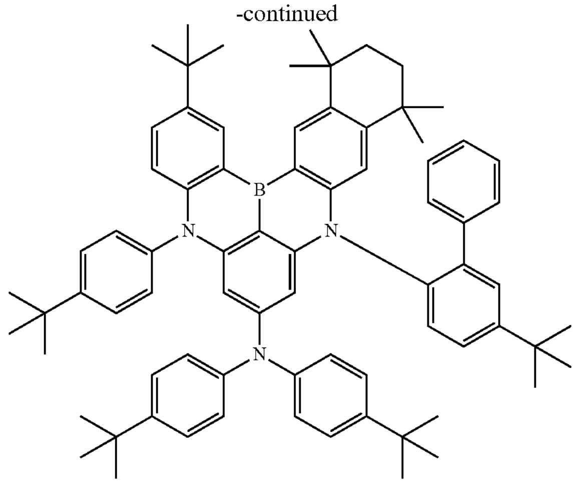

BD-25

After 7 g of Intermediate 38, 2.43 g of bis(4-(tert-butyl)phenyl)amine, 2.5 g of sodium-tert-butoxide, and 0.05 g of bis(tri-tert-butylphosphine)palladium(0) were put into 80 ml of xylene, the resulting mixture was stirred under reflux for 5 hours. After the completion of the reaction, the resulting product was extracted, and then recrystallized to obtain 6.7 g of BD-25. (Yield 73%). MS[M+H]+=1055

Synthesis Example 85. Synthesis of BD-26

1) Synthesis of Intermediate 41

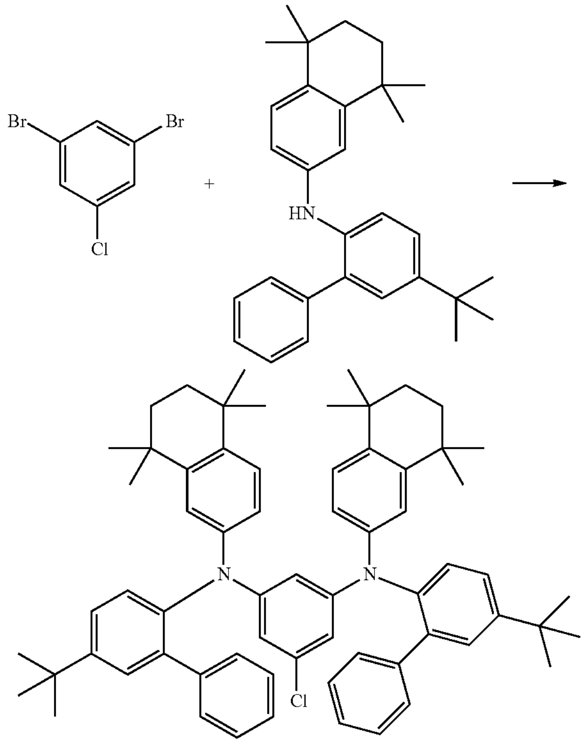

41

After 40 g of 1,3-dibromo-5-chlorobenzene, 121.8 g of N-(5-(tert-butyl)-[1,1'-biphenyl]-2-yl)-5,5,8,8-tetramethyl-5,6,7,8-tetrahydronaphthalen-2-amine, 56.9 g of sodiumtert-butoxide, and 0.8 g of bis(tri-tert-butylphosphine)palladium(0) were put into 1,200 ml of toluene under a nitrogen atmosphere, the resulting mixture was refluxed for 1 hour, the resulting product was extracted after the completion of the reaction, and then recrystallized to obtain 99 g of Intermediate 41. (Yield 72%). MS[M+H]+=932

2) Synthesis of Intermediate 42

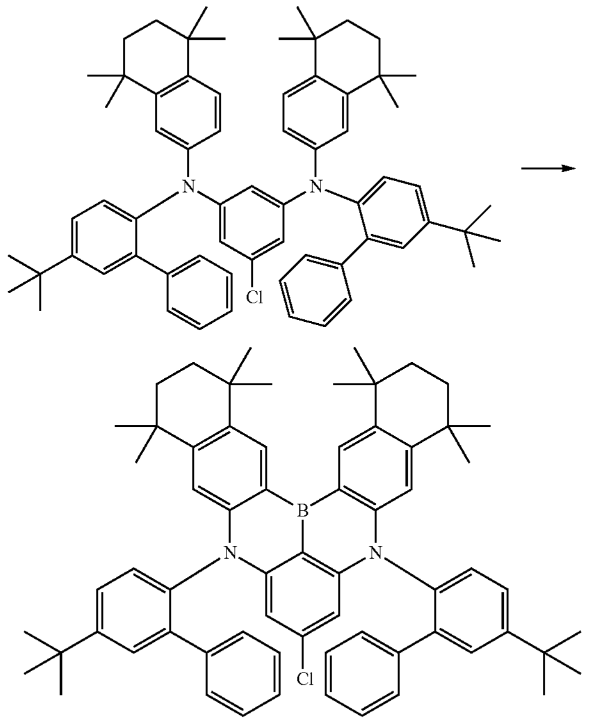

42

After 25 g of Intermediate 41 and 17.9 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.7 g of Intermediate 42 (yield 31%). MS[M+H]+=940

3) Synthesis of BD-26

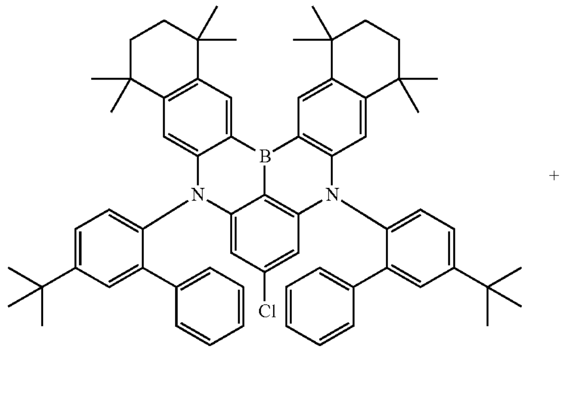

-continued

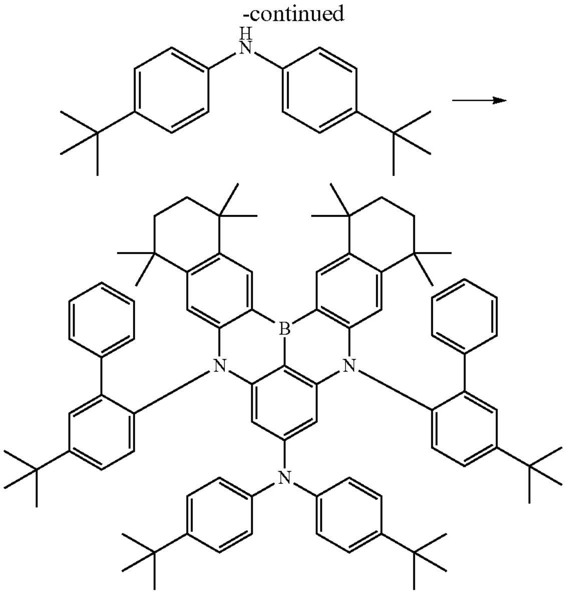

BD-26

After 7 g of Intermediate 42, 2.1 g of bis(4-(tert-butyl)phenyl)amine, 1.5 g of sodium-tert-butoxide, and 0.04 g of bis(tri-tert-butylphosphine)palladium(0) were put into 80 ml of xylene, the resulting mixture was stirred under reflux for 5 hours. After the completion of the reaction, the resulting product was extracted, and then recrystallized to obtain 6.4 g of BD-26. (Yield 72%). MS[M+H]+=1185

Synthesis Example 86. Synthesis of BD-27

1) Synthesis of Intermediate 43

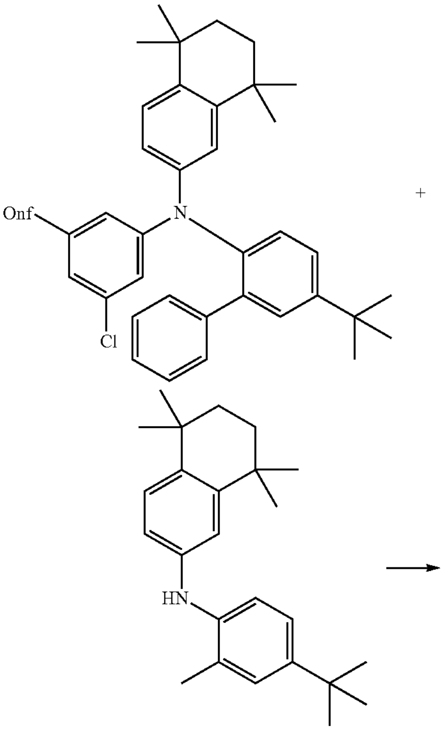

-continued

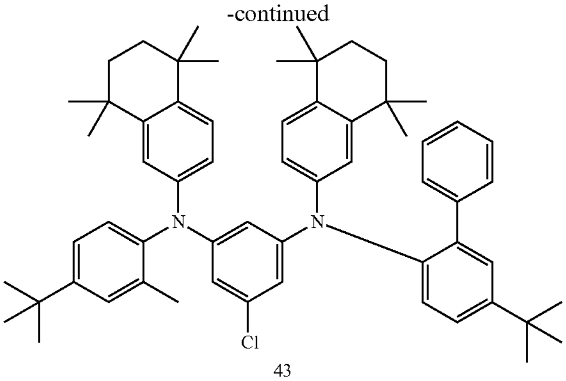

43

40 g of Intermediate 36, 17.4 g of N-(4-(tert-butyl)-2-methylphenyl)-5,5,8,8-tetramethyl-5,6,7,8-tetrahydronaphthalen-2-amine, and the same material and equivalent weight as in the synthesis method of Intermediate 37 were used and then recrystallized to obtain 35 g of Intermediate 43. (Yield 81%). MS[M+H]+=870

2) Synthesis of Intermediate 44

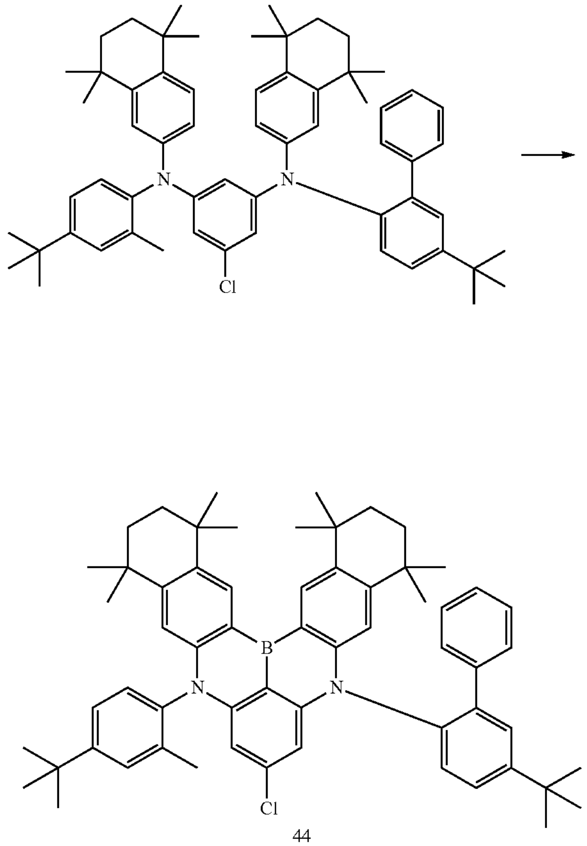

44

After 25 g of Intermediate 43 and 19.1 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.8 g of Intermediate 44 (yield 31%). MS[M+H]+=878

3) Synthesis of BD-27

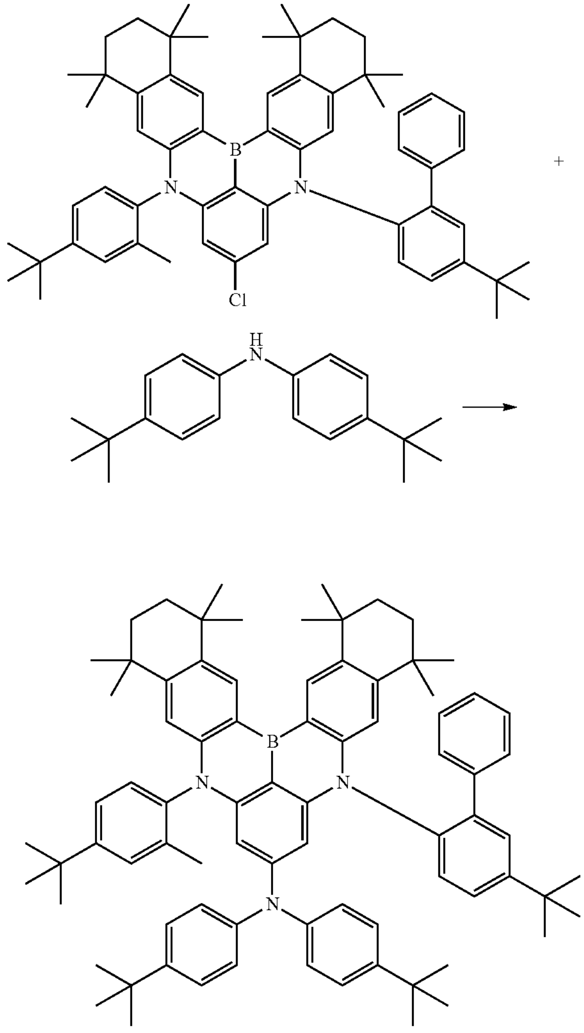

BD-27

After 7 g of Intermediate 44, 2.2 g of bis(4-(tert-butyl)phenyl)amine, 1.5 g of sodium-tert-butoxide, and 0.04 g of bis(tri-tert-butylphosphine)palladium(0) were put into 80 ml of xylene, the resulting mixture was stirred under reflux for 5 hours. After the completion of the reaction, the resulting product was extracted, and then recrystallized to obtain 6.6 g of BD-27. (Yield 74%). MS[M+H]+=1123

Synthesis Example 87. Synthesis of BD-28

1) Synthesis of Intermediate 45

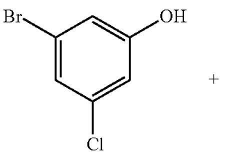

-continued

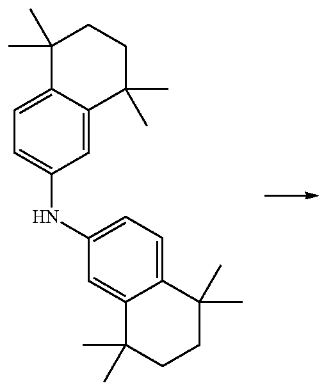

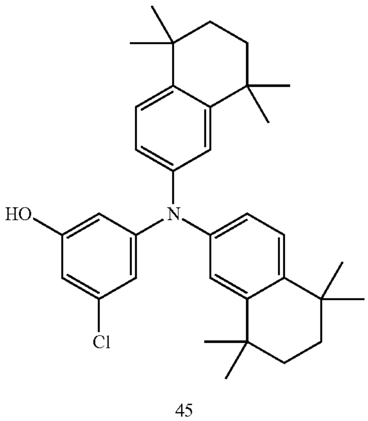

45

40 g of 3-bromo-5-chlorophenol, 75.2 g of bis(5,5,8,8-tetramethyl-5,6,7,8-tetrahydronaphthalen-2-yl)amine, and the same material and equivalent weight as in the synthesis method of Intermediate 35 were used and then recrystallized to obtain 70 g of Intermediate 45. (Yield 70%). MS[M+H]+=517

2) Synthesis of Intermediate 46

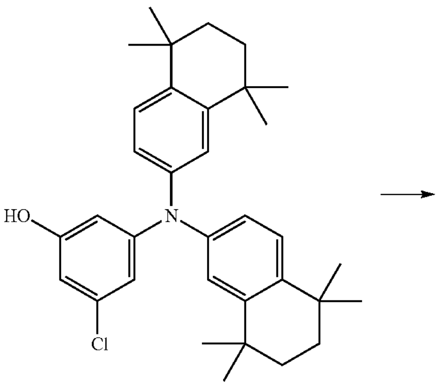

-continued

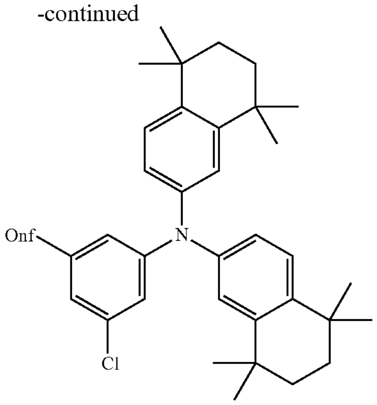

46

40 g of Intermediate 45 and the same material and equivalent weight as in the synthesis method of Intermediate 36 was used and then recrystallized to obtain 56 g of Intermediate 46. (Yield 92%). MS[M+H]+=783

3) Synthesis of Intermediate 47

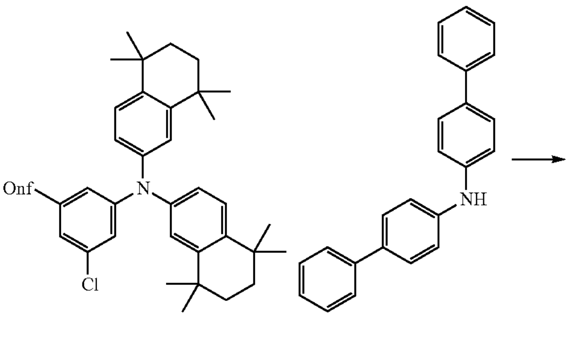

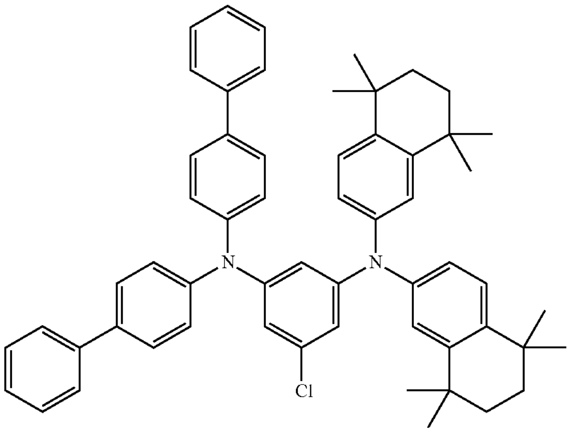

47

Under a nitrogen atmosphere, 40 g of Intermediate 46, 16.4 g of di([1,1'-biphenyl]-4-yl)amine, and the same material and equivalent weight as in the synthesis method of Intermediate 37 were used and then recrystallized to obtain 34 g of Intermediate 47 (yield 81%). MS[M+H]+=820

4) Synthesis of Intermediate 48

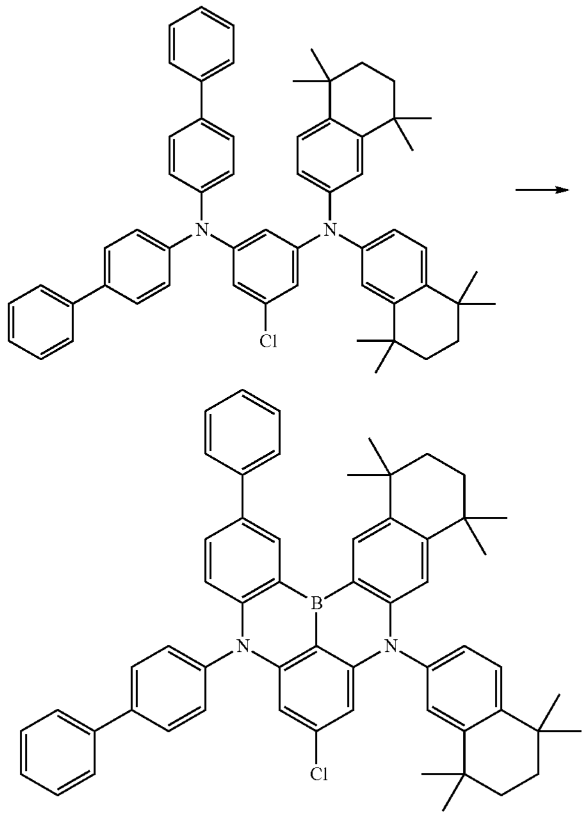

48

25 g of Intermediate 47, and the same material and equivalent weight as in the synthesis method of Intermediate 38 were used and then recrystallized to obtain 7.5 g of Intermediate 48 (yield 30%). MS[M+H]+=828

5) Synthesis of BD-28

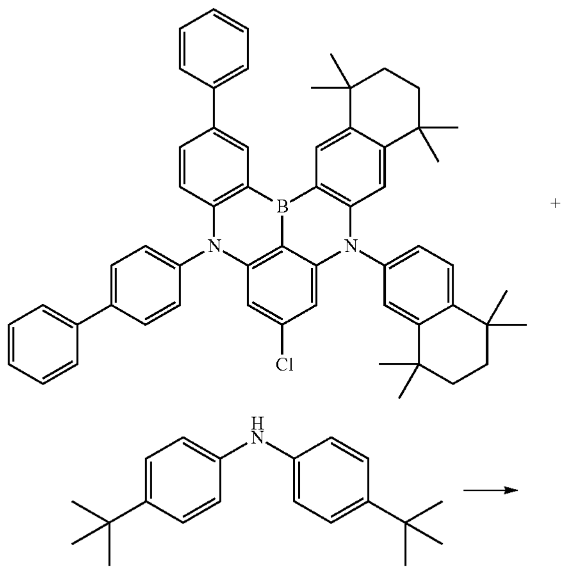

-continued

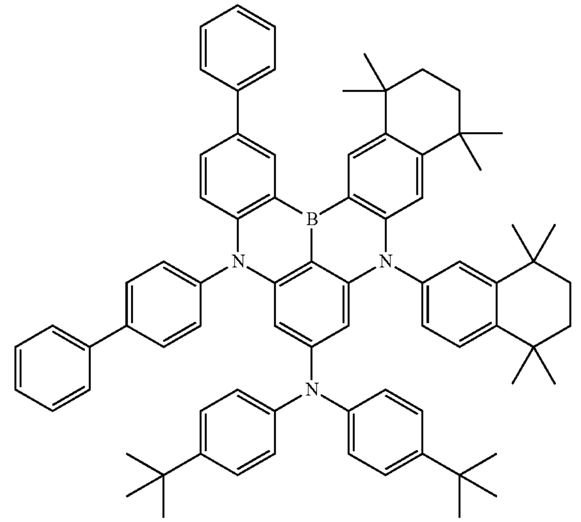

BD-28

After 7 g of Intermediate 48, 1.46 g of bis(4-(tert butyl) phenyl)amine, 1.5 g of sodium-tert-butoxide, and 0.05 g of bis(tri-tert-butylphosphine)palladium(0) were put into 80 ml of xylene, the resulting mixture was stirred under reflux for 5 hours. After the completion of the reaction, the resulting product was extracted, and then recrystallized to obtain 6.7 g of BD-28. (Yield 78%). MS[M+H]+=1073

Synthesis Example 88. Synthesis of BD-29

1) Synthesis of Intermediate 49

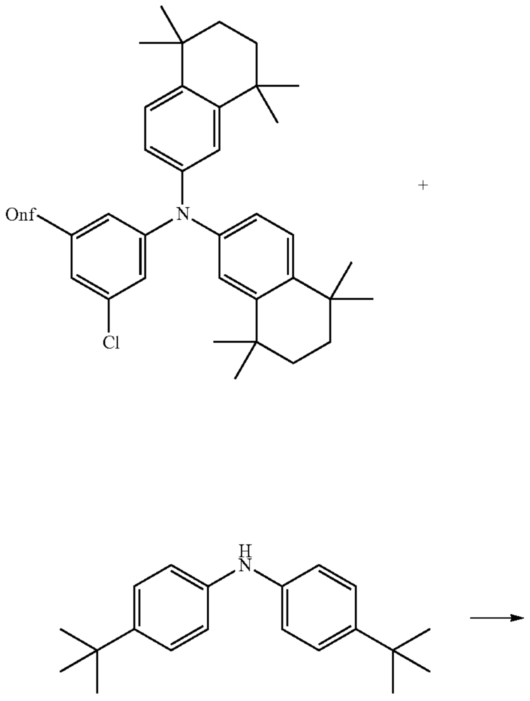

-continued

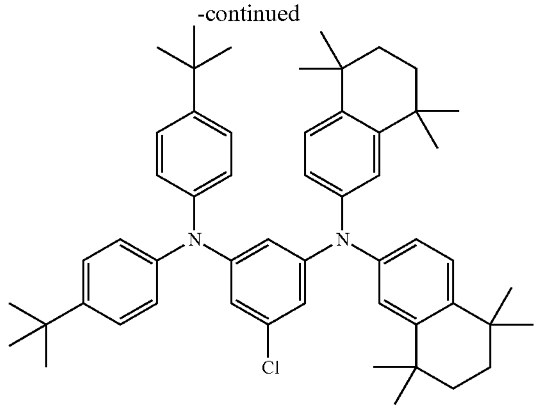

49

Under a nitrogen atmosphere, 40 g of Intermediate 46, 14 g of bis(4-(tert-butyl)phenyl)amine, and the same material and equivalent weight as in the synthesis method of Intermediate 37 were used and then recrystallized to obtain 32 g of Intermediate 49. (Yield 83%). MS[M+H]+=780

2) Synthesis of Intermediate 50

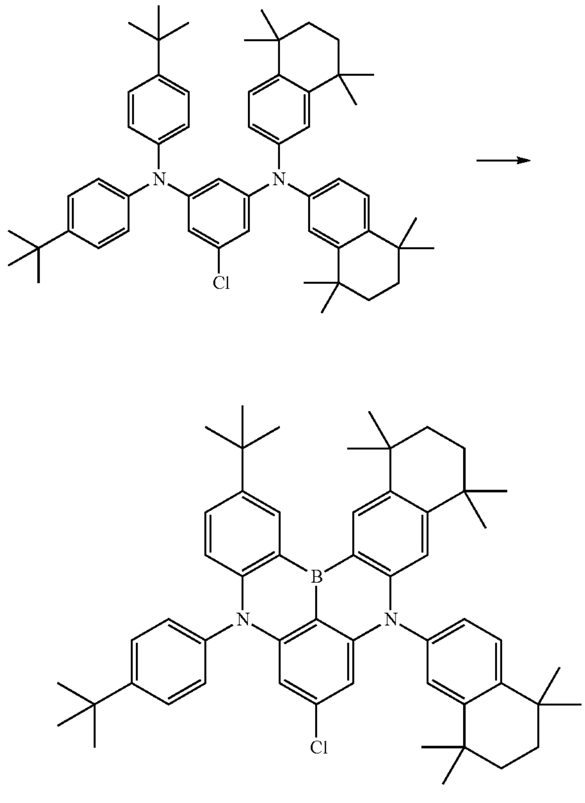

50

After 25 g of Intermediate 49 and 21.3 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.5 g of Intermediate 50 (yield 30%). MS[M+H]+=788

3) Synthesis of BD-29

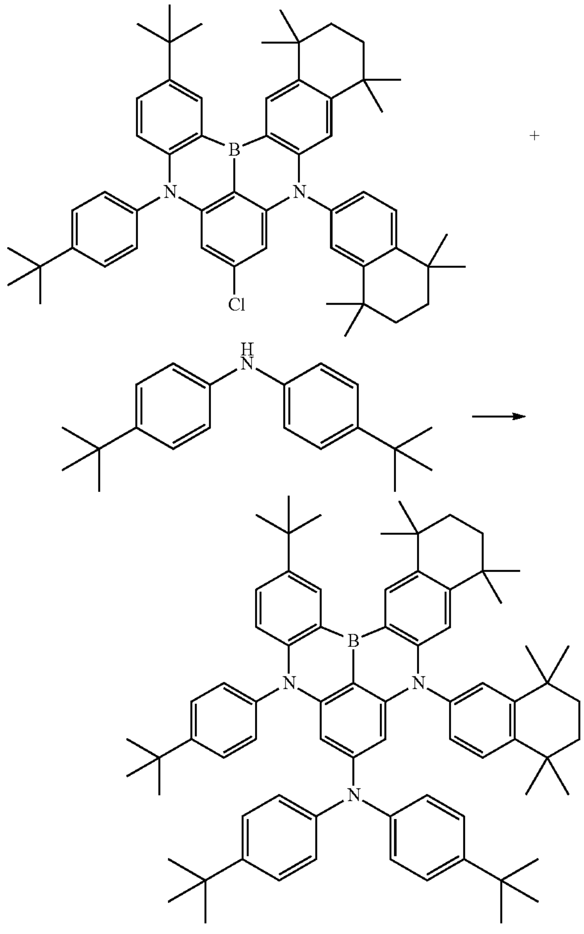

BD-29

After 7 g of Intermediate 50, 2.5 g of bis(4-(tert-butyl)phenyl)amine, 1.7 g of sodium-tert-butoxide, and 0.05 g of bis(tri-tert-butylphosphine)palladium(0) were put into 80 ml of xylene, the resulting mixture was stirred under reflux for 5 hours. After the completion of the reaction, the resulting product was extracted, and then recrystallized to obtain 6.5 g of BD-29. (Yield 71%). MS[M+H]+=1033

Synthesis Example 89. Synthesis of BD-30

1) Synthesis of Intermediate 51

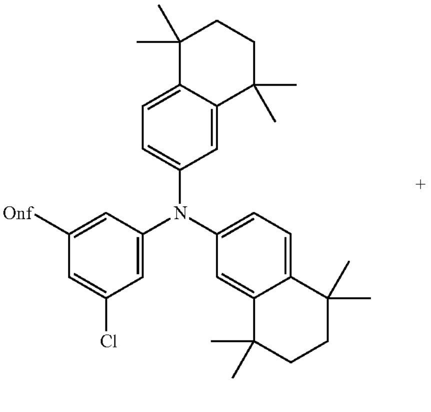

-continued

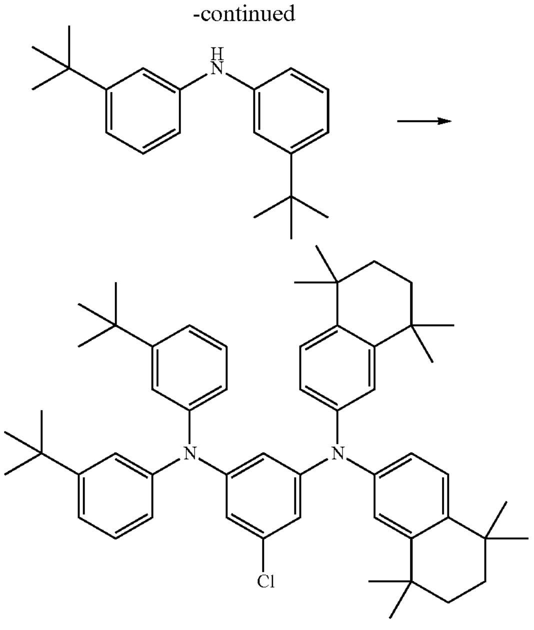

51

Under a nitrogen atmosphere, 40 g of Intermediate 46, 14 g of bis(3-(tert-butyl)phenyl)amine, and the same material and equivalent weight as in the synthesis method of Intermediate 37 were used and then recrystallized to obtain 30 g of Intermediate 51. (Yield 81%). MS[M+H]+=780

2) Synthesis of Intermediate 52

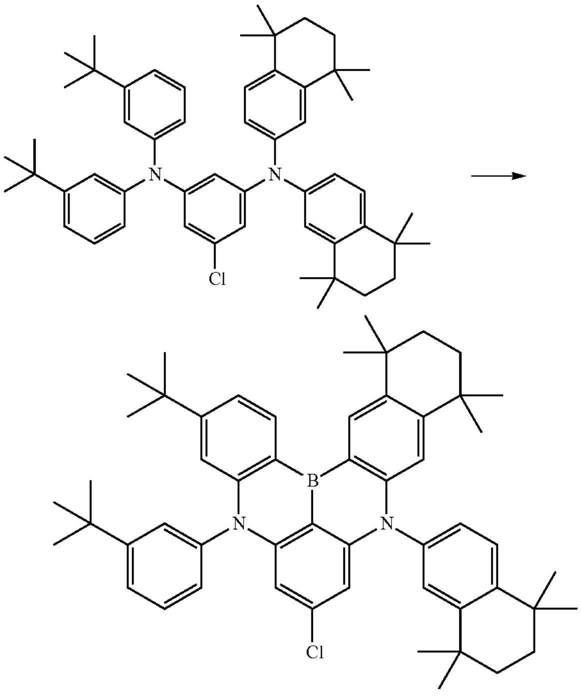

52

After 25 g of Intermediate 51 and 21.3 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.4 g of Intermediate 52 (yield 30%). MS[M+H]+=788

3) Synthesis of BD-30

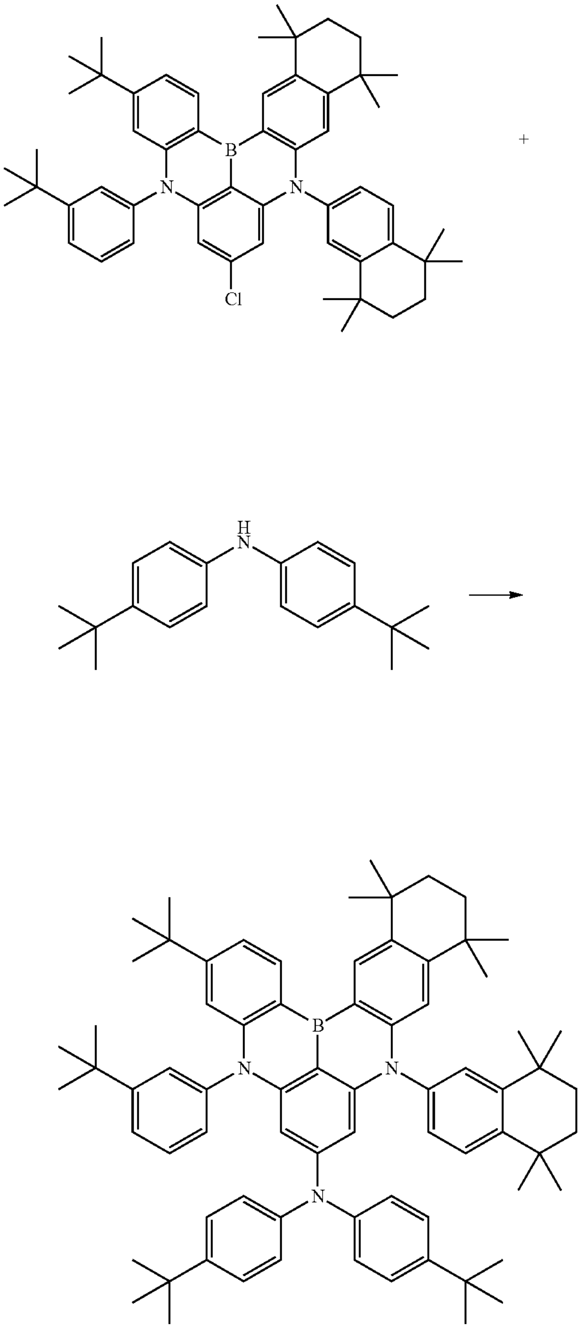

BD-30

After 7 g of Intermediate 52, 2.5 g of bis(4-(tert-butyl)phenyl)amine, 1.7 g of sodium-tert-butoxide, and 0.05 g of bis(tri-tert-butylphosphine)palladium(0) were put into 80 ml of xylene, the resulting mixture was stirred under reflux for 5 hours. After the completion of the reaction, the resulting product was extracted, and then recrystallized to obtain 6.6 g of BD-30. (Yield 72%). MS[M+H]+=1033

Synthesis Example 90. Synthesis of BD-31

1) Synthesis of Intermediate 53

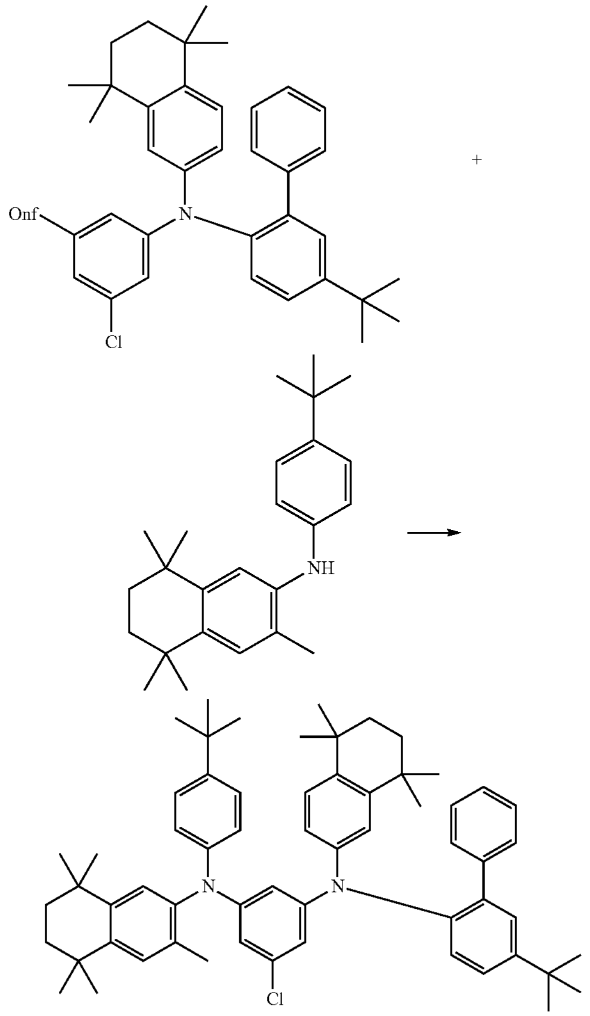

53

Under a nitrogen atmosphere, 40 g of Intermediate 35, 17.4 g of N-(4-(tert-butyl)phenyl)-3,5,5,8,8-pentamethyl-5,6,7,8-tetrahydronaphthalen-2-amine, and the same material and equivalent weight as in the synthesis method of Intermediate 37 were used and then recrystallized to obtain 34 g of Intermediate 53. (Yield 79%). MS[M+H]+=870

2) Synthesis of Intermediate 54

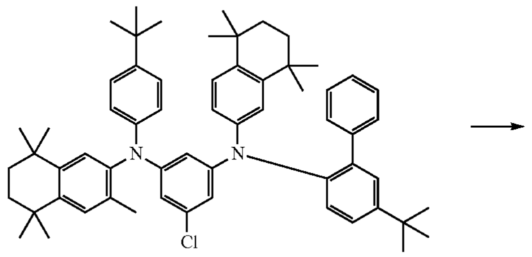

-continued

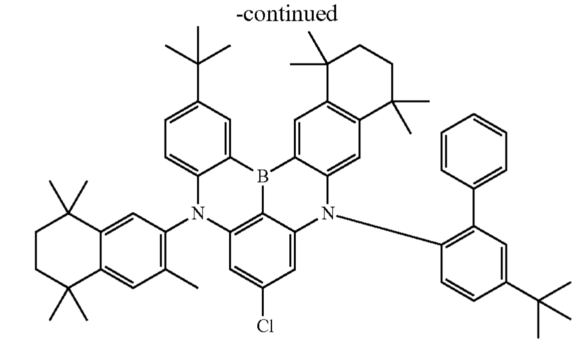

54

After 25 g of Intermediate 53 and 19.2 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.1 g of Intermediate 54 (yield 28%). MS[M+H]+=878

3) Synthesis of BD-31

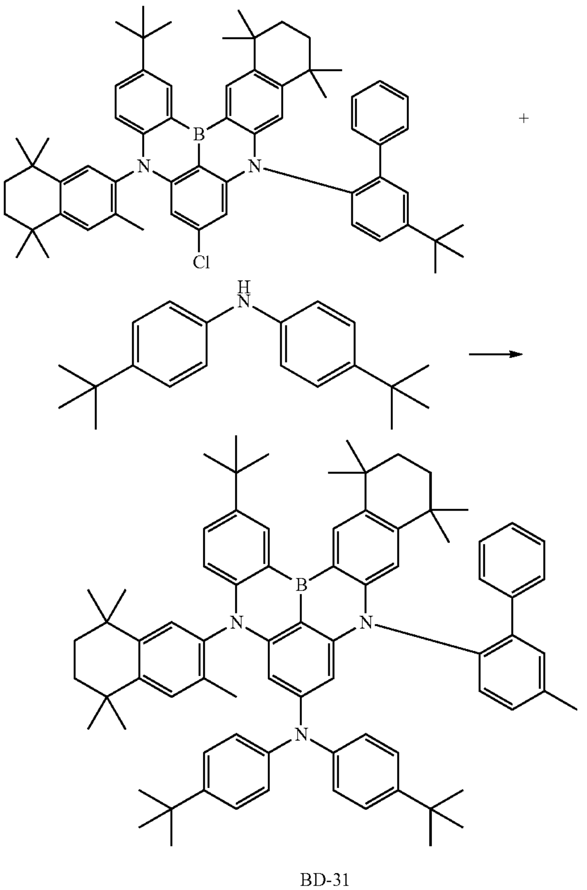

BD-31

After 7 g of Intermediate 54, 2.3 g of bis(4-(tert-butyl)phenyl)amine, 1.5 g of sodium-tert-butoxide, and 0.05 g of bis(tri-tert-butylphosphine)palladium(0) were put into 80 ml of xylene, the resulting mixture was stirred under reflux for 5 hours. After the completion of the reaction, the resulting product was extracted, and then recrystallized to obtain 6.6 g of BD-31. (Yield 74%). MS[M+H]+=1123

Synthesis Example 91. Synthesis of BD-32

1) Synthesis of Intermediate 55

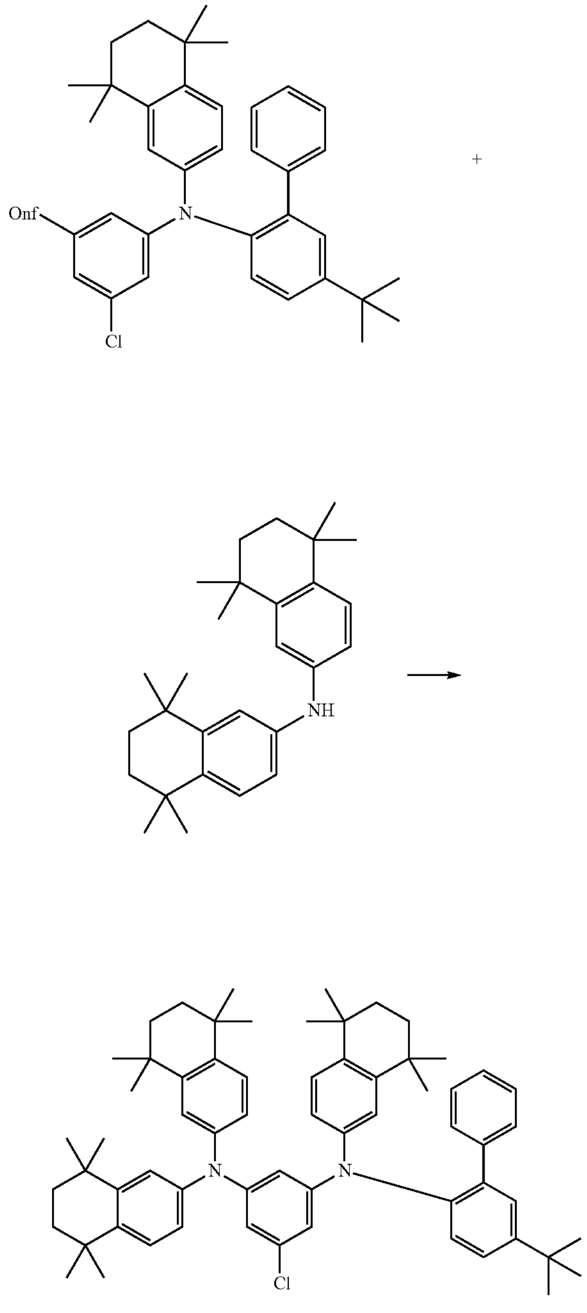

55

Under a nitrogen atmosphere, 40 g of Intermediate 35, 19.4 g of bis(5,5,8,8-tetramethyl-5,6,7,8-tetrahydronaphthalen-2-yl)amine, and same material and equivalent weight as in the synthesis method of Intermediate 37 were used and then recrystallized to obtain 35 g of Intermediate 55. (Yield 77%). MS[M+H]+=910

2) Synthesis of Intermediate 56

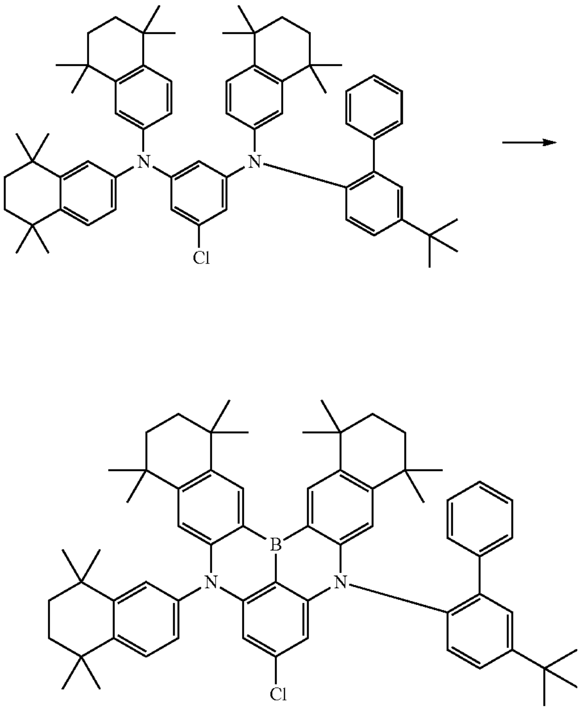

56

After 25 g of Intermediate 55 and 18.3 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.4 g of Intermediate 56 (yield 29%). MS[M+H]+=918

3) Synthesis of BD-32

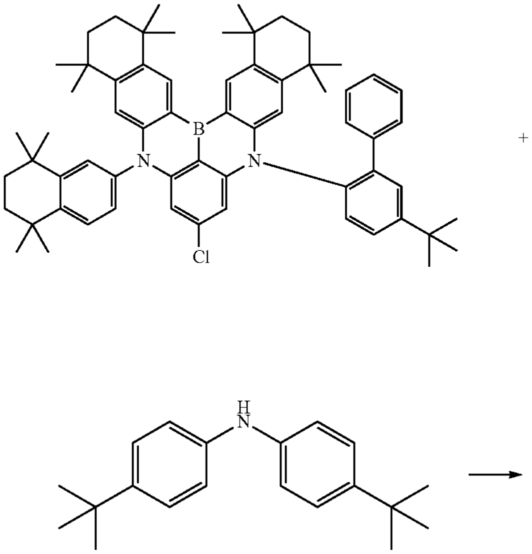

-continued

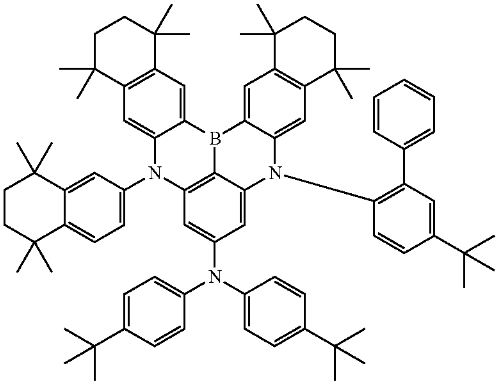

BD-32

After 7 g of Intermediate 56, 2.1 g of bis(4-(tert-butyl) phenyl)amine, 1.5 g of sodium-tert-butoxide, and 0.05 g of bis(tri-tert-butylphosphine)palladium(0) were put into 80 ml of xylene, the resulting mixture was stirred under reflux for 5 hours. After the completion of the reaction, the resulting product was extracted, and then recrystallized to obtain 6.5 g of BD-32. (Yield 73%). MS[M+H]+=1163

Synthesis Example 92. Synthesis of BD-33

1) Synthesis of Intermediate 57

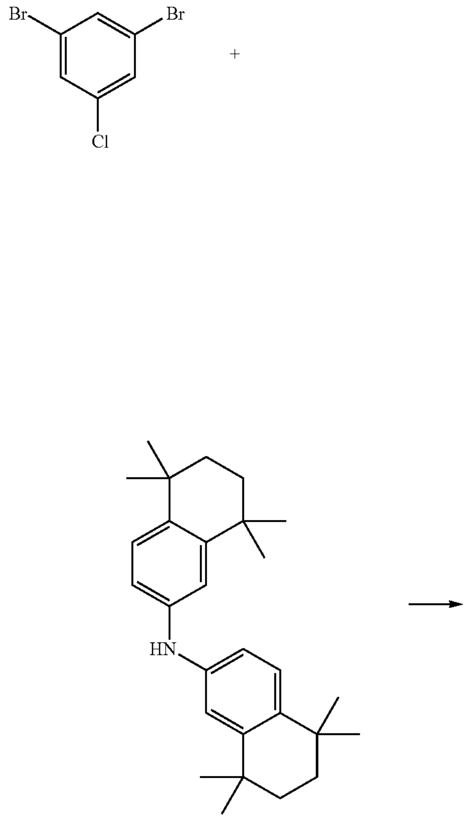

-continued

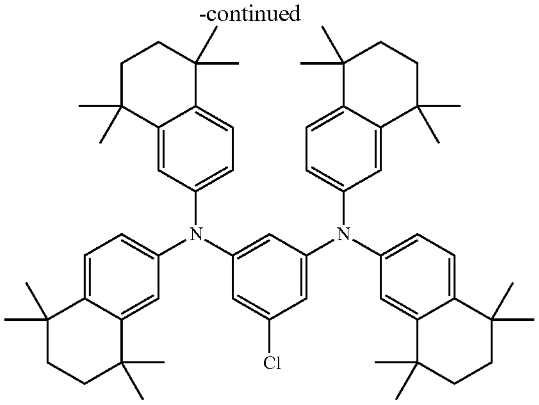

57

Under a nitrogen atmosphere 40 g of 1,3-dibromo-5-chlorobenzene, 115.3 g of bis(5,5,8,8-tetramethyl-5,6,7,8-tetrahydronaphthalen-2-yl)amine, and the same material and equivalent weight as in the synthesis method of Intermediate 41 were used and then recrystallized to obtain 99 g of Intermediate 57. (Yield 75%). MS[M+H]+=888

2) Synthesis of Intermediate 58

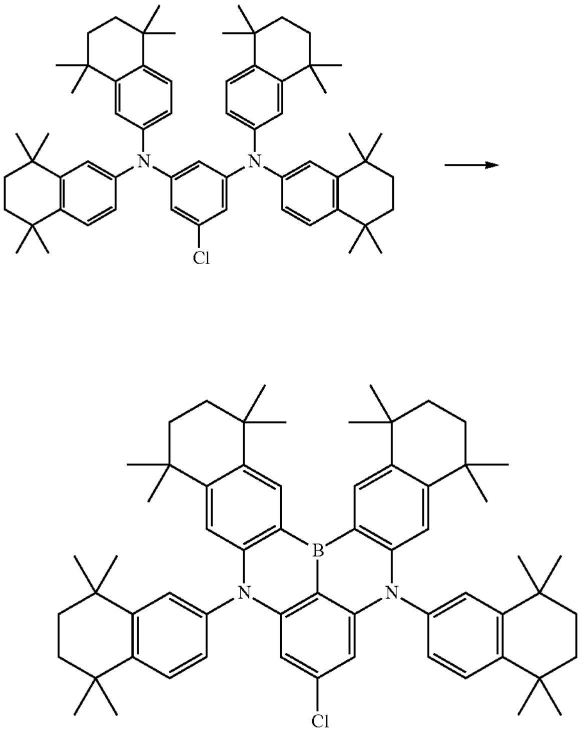

58

After 25 g of Intermediate 57 and 18.7 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.7 g of Intermediate 58 (yield 31%). MS[M+H]+=896

3) Synthesis of BD-33

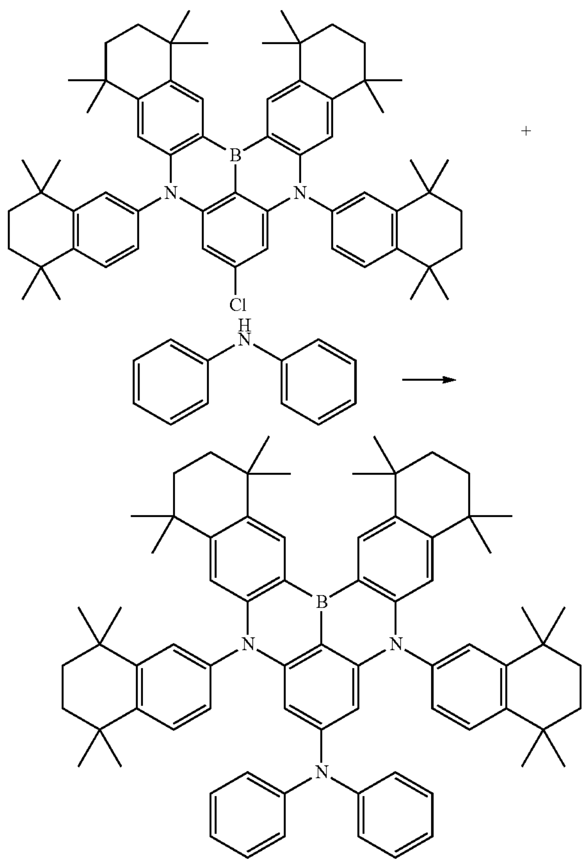

BD-33

After 7 g of Intermediate 58, 1.4 g of diphenylamine, 1.5 g of sodium-tert-butoxide, and 0.05 g of bis(tri-tert-butylphosphine)palladium(0) were put into 80 ml of xylene, the resulting mixture was stirred under reflux for 5 hours. After the completion of the reaction, the resulting product was extracted, and then recrystallized to obtain 6.3 g of BD-33. (Yield 78%). MS[M+H]+=1029

Synthesis Example 93. Synthesis of BD-34

1) Synthesis of Compound 37

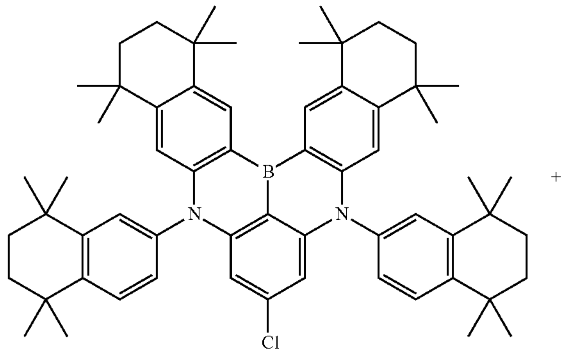

-continued

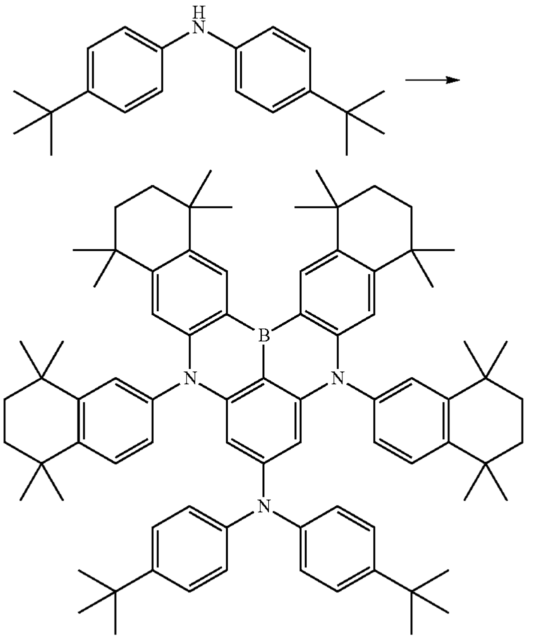

BD-34

After 7 g of Intermediate 58, 2.2 g of bis(4-(tert-butyl) phenyl)amine, 1.5 g of sodium-tert-butoxide, and 0.05 g of bis(tri-tert-butylphosphine)palladium(0) were put into 80 ml of xylene, the resulting mixture was stirred under reflux for 5 hours. After the completion of the reaction, the resulting product was extracted, and then recrystallized to obtain 6.5 g of BD-34. (Yield 73%). MS[M+H]+=1141

Synthesis Example 94. Synthesis of BD-35

1) Synthesis of Intermediate 59

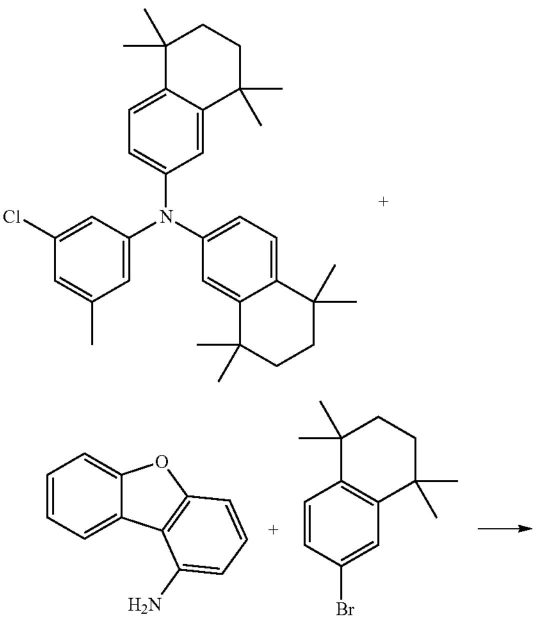

-continued

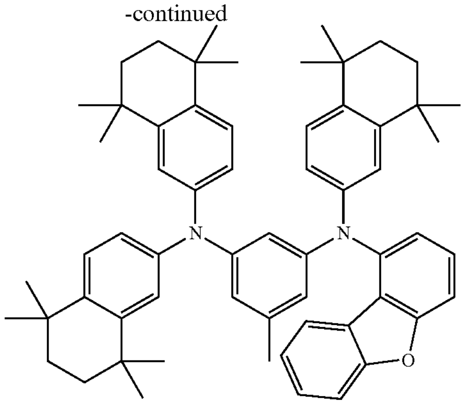

59

After 40 g of Intermediate 7, 14.3 g of dibenzo[b,d]furan-1-amine, 22.4 g of sodium-tert-butoxide, and 0.4 g of bis(tri-tert-butylphosphine)palladium(0) were put into 600 ml of toluene, the resulting mixture was refluxed for 1 hour, whether the reaction proceeded was confirmed, and then 20.8 g of 6-bromo-1,1,4,4-tetramethyl-1,2,3,4-tetrahydronaphthalene was added thereto during the reflux reaction, and the reflux reaction was performed for an additional 1 hour. After the completion of the reaction, the resulting product was extracted, and then recrystallized to obtain 54 g of Intermediate 59. (Yield 82%). MS[M+H]+=848

2) Synthesis of BD-35

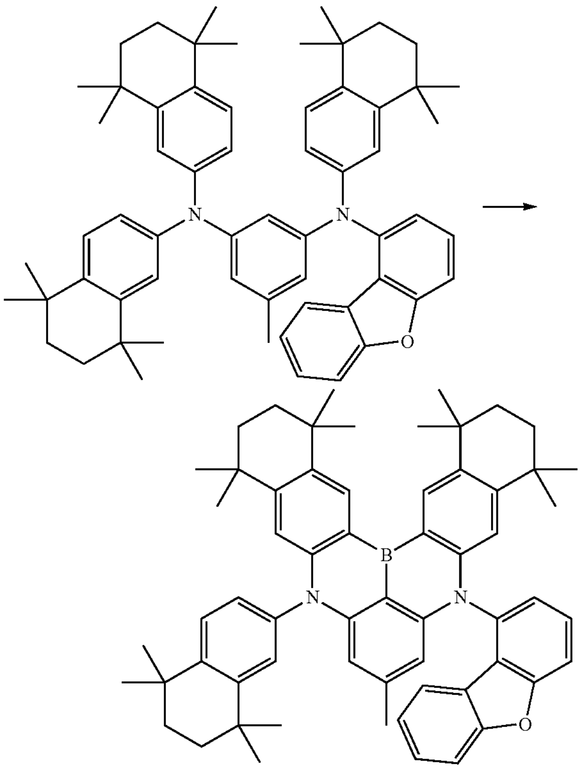

BD-35

After 25 g of Intermediate 59 and 19.7 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.5 g of BD-35 (yield 30%). MS[M+H]+=856

Synthesis Example 95. Synthesis of BD-36

1) Synthesis of Intermediate 60

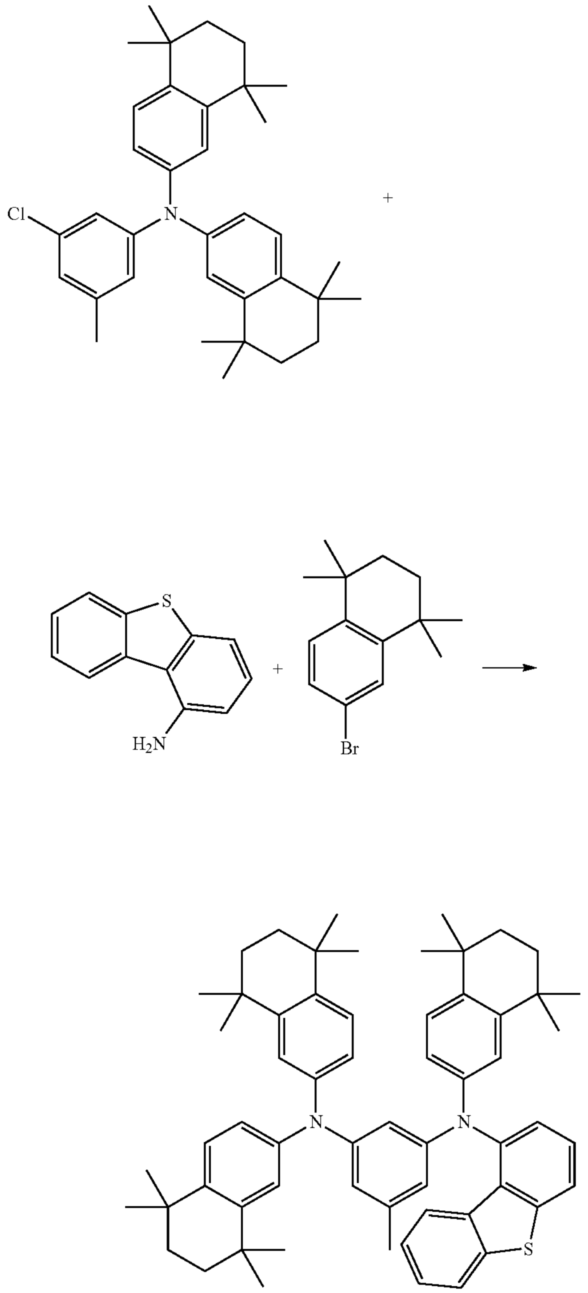

60

40 g of Intermediate 7 and 15.5 g of dibenzo[b,d]thiophen-1-amine were recrystallized using the same material and equivalent weight as in the synthesis method of Intermediate 59 to obtain 52 g of Intermediate 60. (Yield 77%). MS[M+H]+=864

2) Synthesis of BD-36

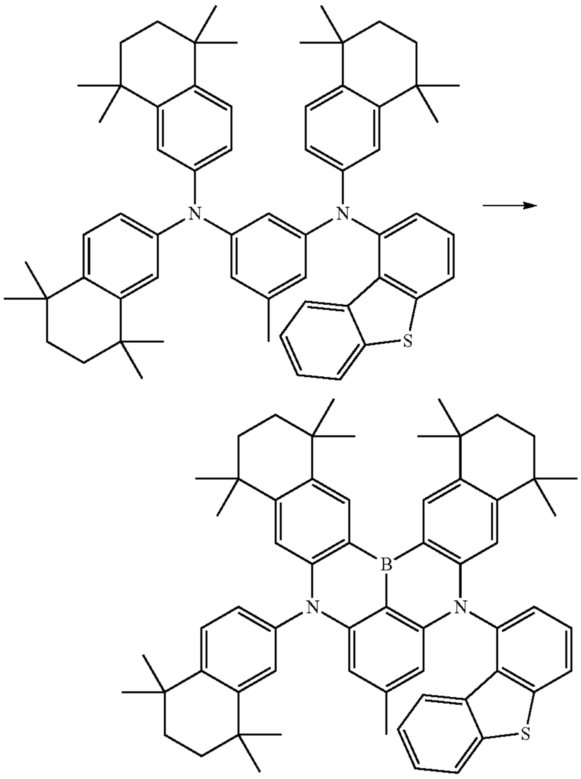

BD-36

After 25 g of Intermediate 60 and 19.3 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.7 g of BD-36 (yield 31%). MS[M+H]+=872

Synthesis Example 96. Synthesis of BD-37

1) Synthesis of Intermediate 61

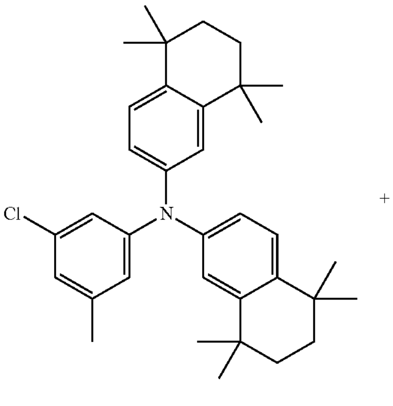

-continued

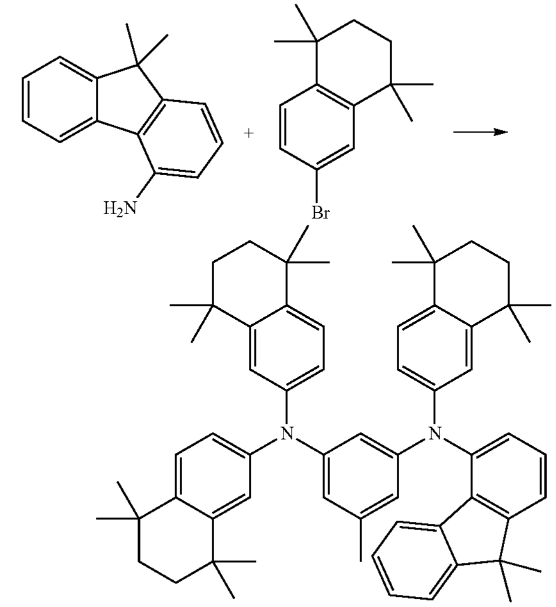

61

40 g of Intermediate 7, 16.3 g of 9,9-dimethyl-9H-fluoren-4-amine, and the same material and equivalent weight as in the synthesis method of Intermediate 59 were used and then to obtain 54 g of Intermediate 61. (Yield 79%). MS[M+H]+=874

2) Synthesis of BD-37

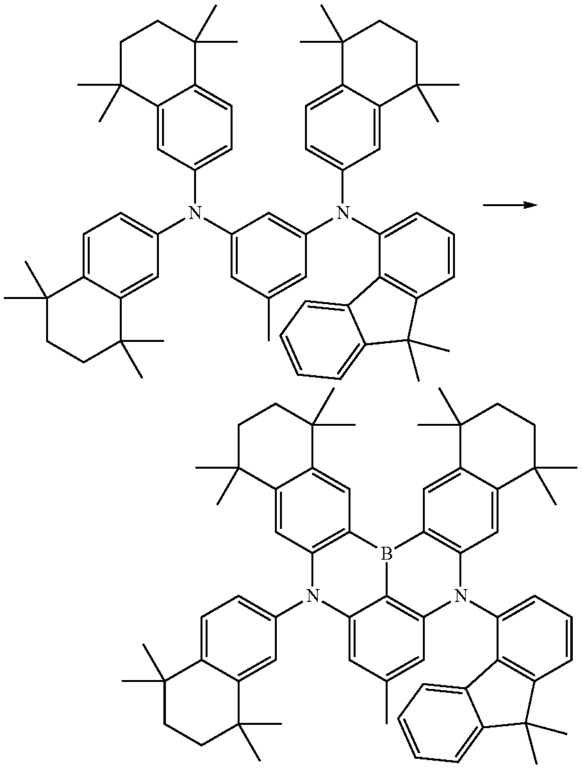

BD-37

After 25 g of Intermediate 61 and 19.1 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.5 g of BD-37 (yield 30%). MS[M+H]+=882

Synthesis Example 97. Synthesis of BD-38

1) Synthesis of Intermediate 62

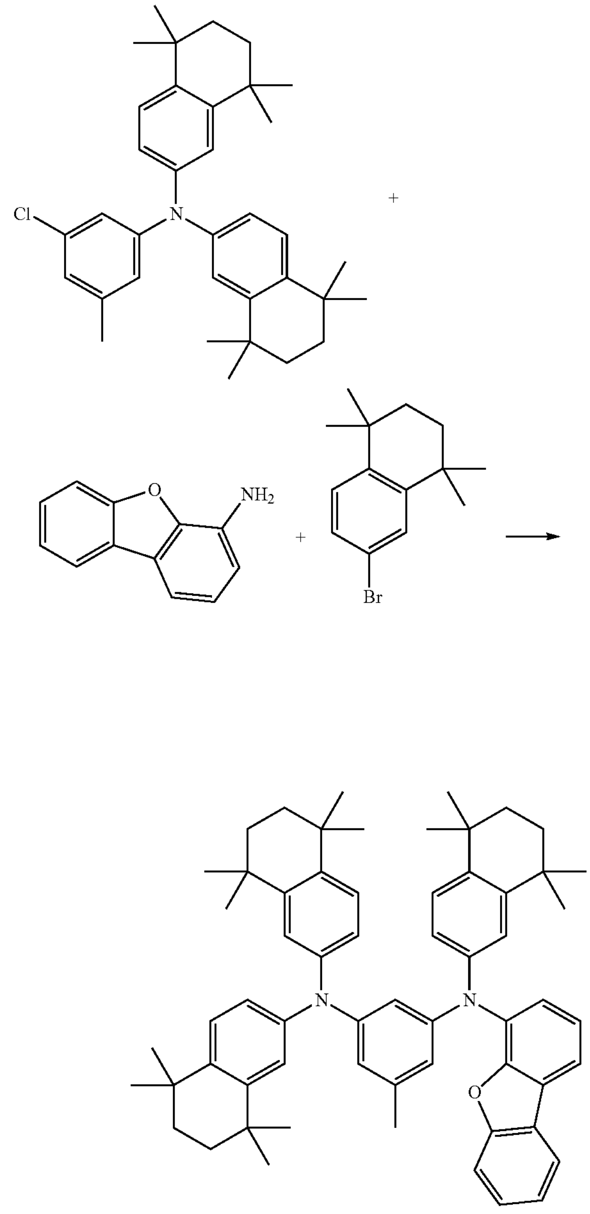

62

40 g of Intermediate 7, 14.3 g of dibenzo[b,d]furan-4-amine, and the same material and equivalent weight as in the synthesis method of Intermediate 59 were used and then recrystallized to obtain 53 g of Intermediate 62. (Yield 77%). MS[M+H]+=848

2) Synthesis of BD-38

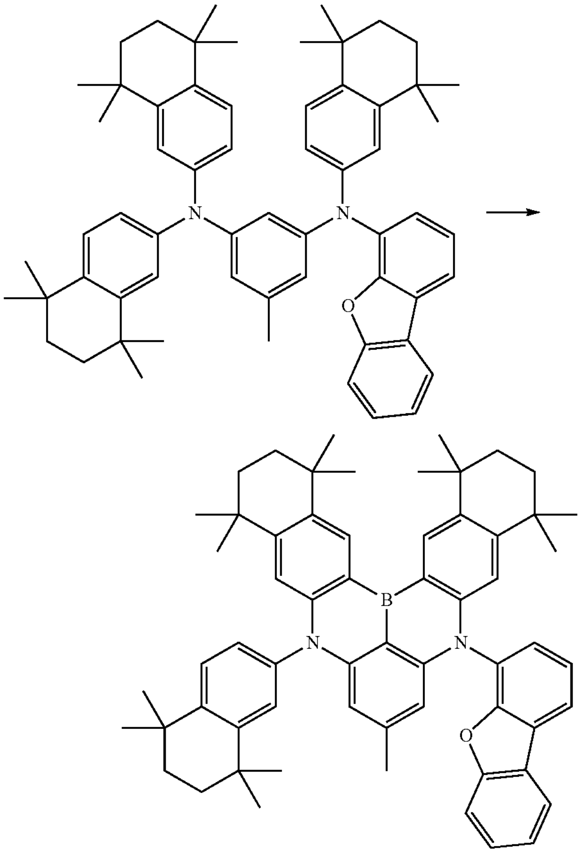

BD-38

After 25 g of Intermediate 62 and 19.7 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.7 g of BD-38 (yield 31%). MS[M+H]+=856

Synthesis Example 98. Synthesis of BD-39

1) Synthesis of Intermediate 63

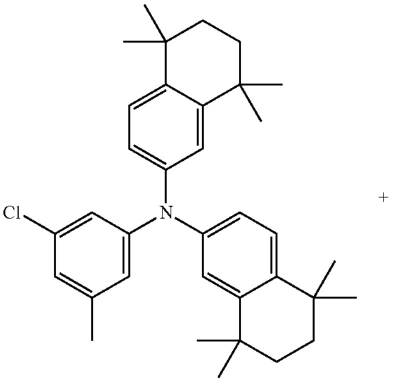

-continued

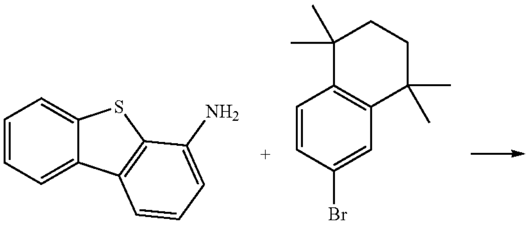

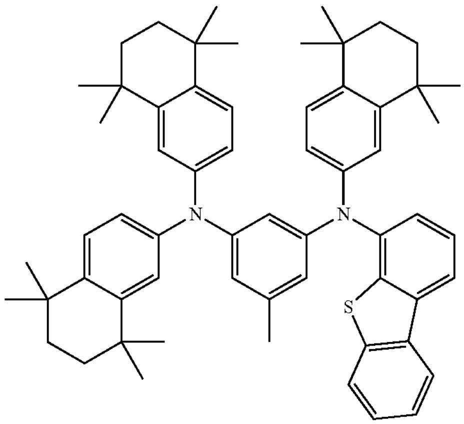

63

40 g of Intermediate 7, 15.5 g of dibenzo[b,d]thiophen-4-amine, and the same material and equivalent weight as in the synthesis method of Intermediate 59 were used and then recrystallized to obtain 54 g of Intermediate 63. (Yield 78%). MS[M+H]+=864

2) Synthesis of BD-39

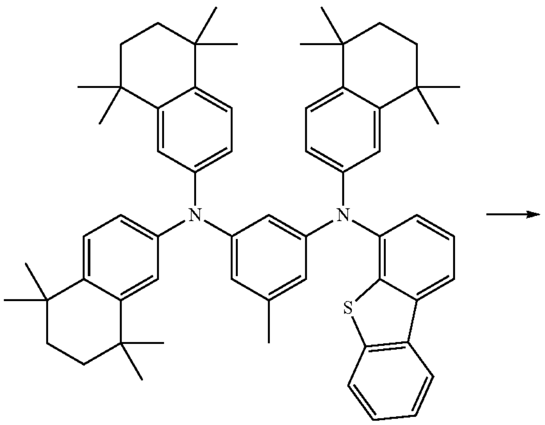

-continued

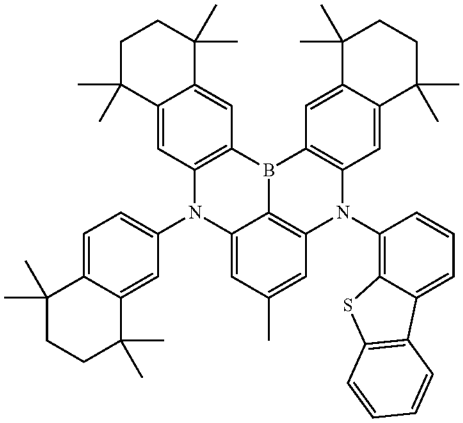

BD-39

After 25 g of Intermediate 63 and 19.3 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.6 g of BD-39 (yield 31%). MS[M+H]+=872

Synthesis Example 99. Synthesis of BD-40

1) Synthesis of Intermediate 64

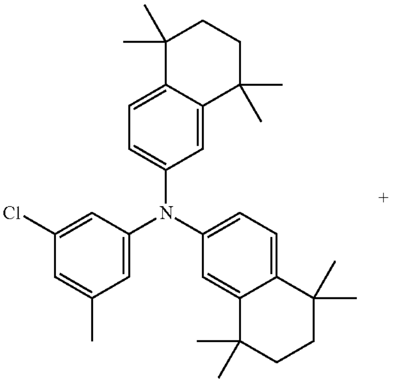

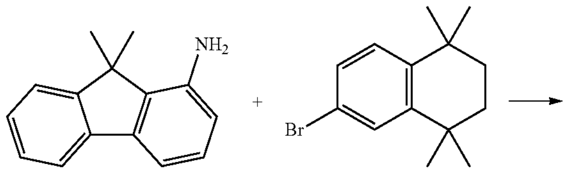

-continued

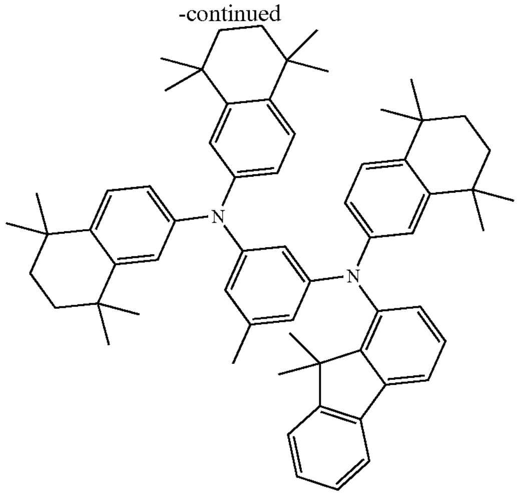

64

40 g of Intermediate 7, 16.3 g of 9,9-dimethyl-9H-fluoren-1-amine, and the same material and equivalent weight as in the synthesis method of Intermediate 59 were used and then recrystallized to obtain 51 g of Intermediate 64. (Yield 77%). MS[M+H]+=874

2) Synthesis of BD-40

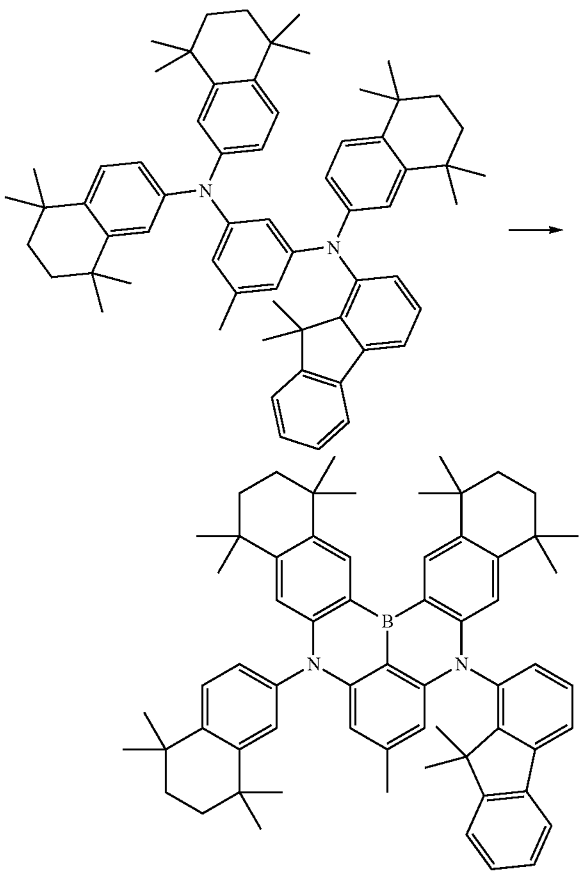

BD-40

After 25 g of Intermediate 64 and 19.1 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.2 g of BD-40 (yield 28%). MS[M+H]+=882

Synthesis Example 100. Synthesis of BD-41

1) Synthesis of Intermediate 65

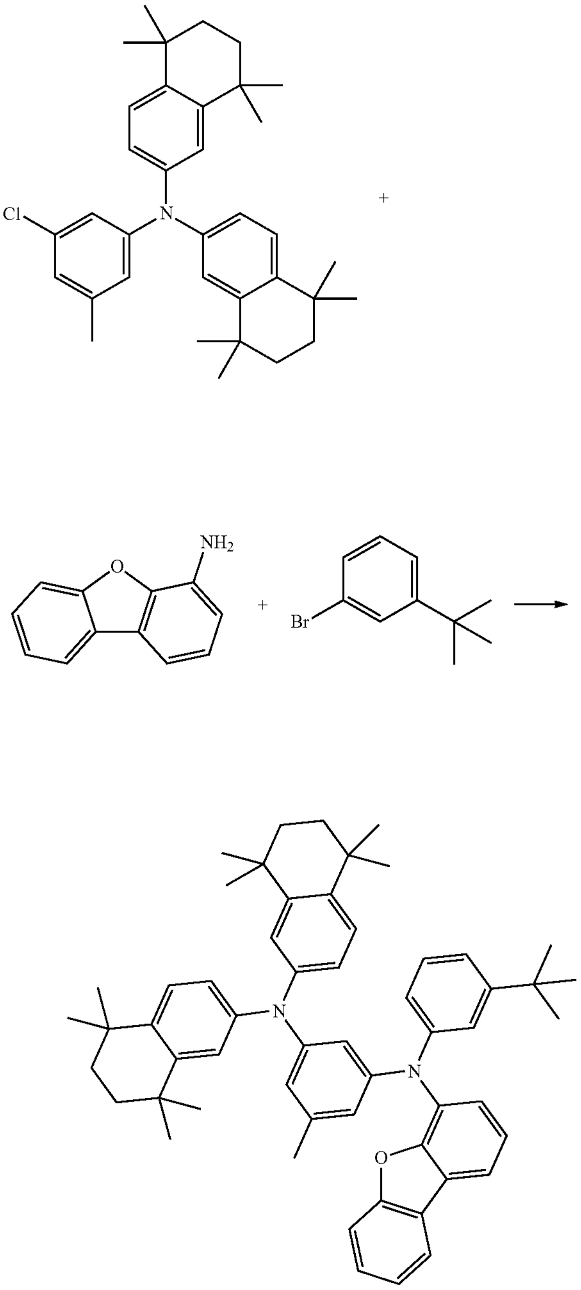

65

40 g of Intermediate 7, 14.3 g of dibenzo[b,d]furan-4-amine, 16.6 g of 1-bromo-3-(tert-butyl)benzene, and the same material and equivalent weight as in the synthesis method of Intermediate 59 were used and then recrystallized to obtain 47 g of Intermediate 65. (Yield 76%). MS[M+H]+= 794

2) Synthesis of BD-41

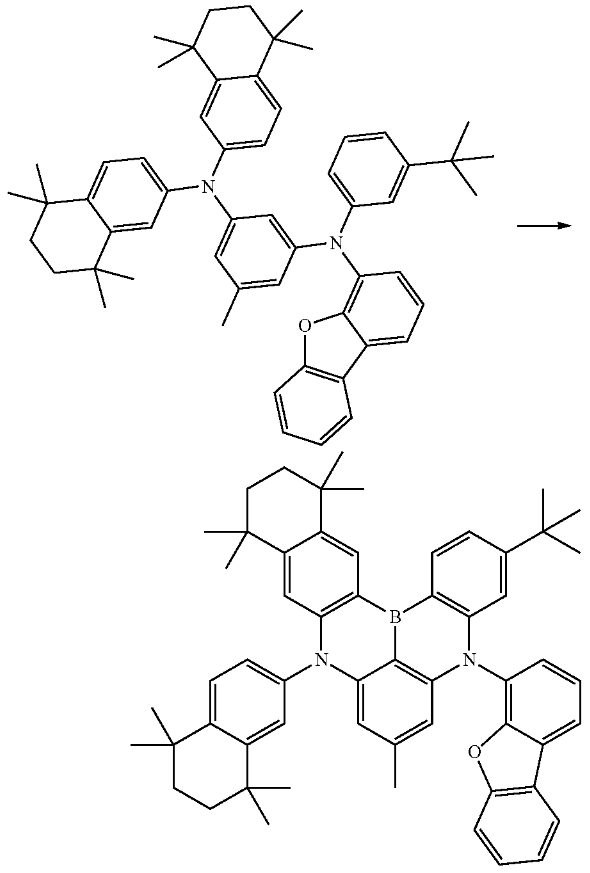

BD-41

After 25 g of Intermediate 65 and 21 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.8 g of BD-41 (yield 31%). MS[M+H]+=801

Synthesis Example 101. Synthesis of BD-42

1) Synthesis of Intermediate 66

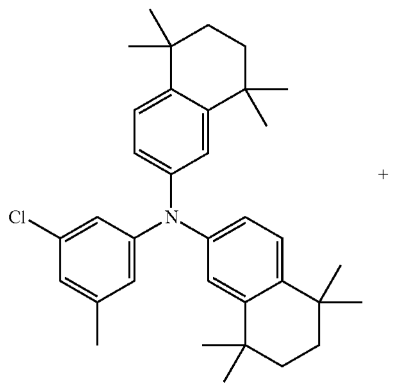

-continued

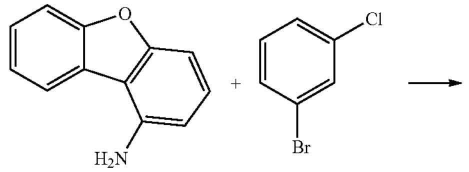

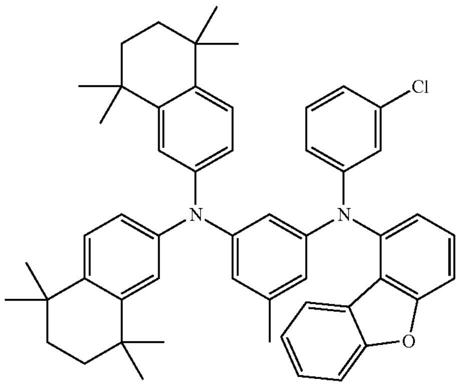

66

After 40 g of Intermediate 7, 14.3 g of dibenzo[b,d]furan-1-amine, 22.4 g of sodium-tert-butoxide, and 0.4 g of bis(tri-tert-butylphosphine)palladium(0) were put into 600 ml of toluene, the resulting mixture was refluxed for 1 hour, whether the reaction proceeded was confirmed, and then 14.9 g of 1-bromo-3-chlorobenzene was added thereto during the reflux reaction, and the reflux reaction was performed for an additional 1 hour. After the completion of the reaction, the resulting product was extracted, and then recrystallized to obtain 46 g of Intermediate 66. (Yield 77%). MS[M+H]+=771

2) Synthesis of Intermediate 67

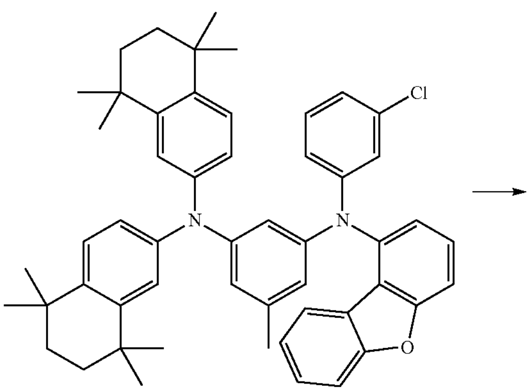

-continued

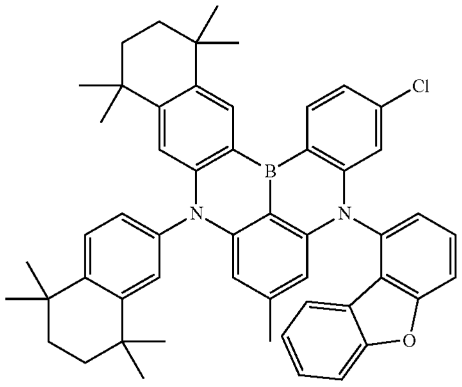

67

After 25 g of Intermediate 66 and 21.6 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.8 g of Intermediate 67 (yield 31%). MS[M+H]+ =780

3) Synthesis of BD-42

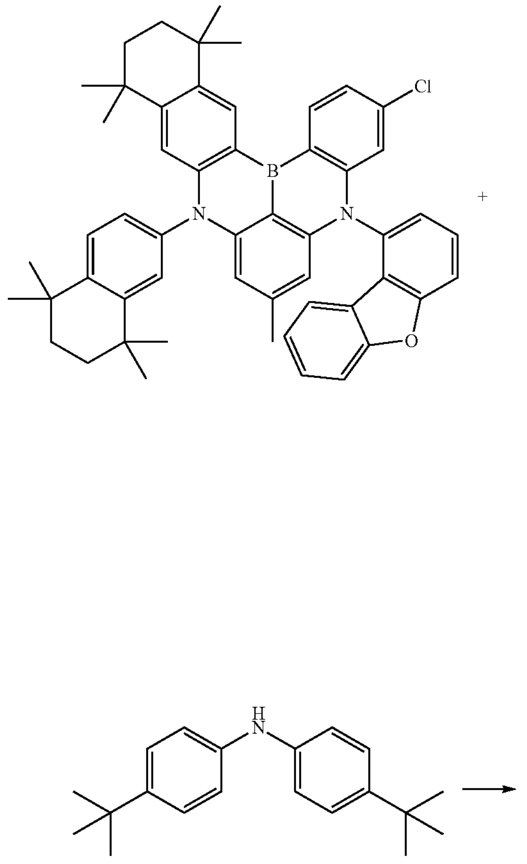

-continued

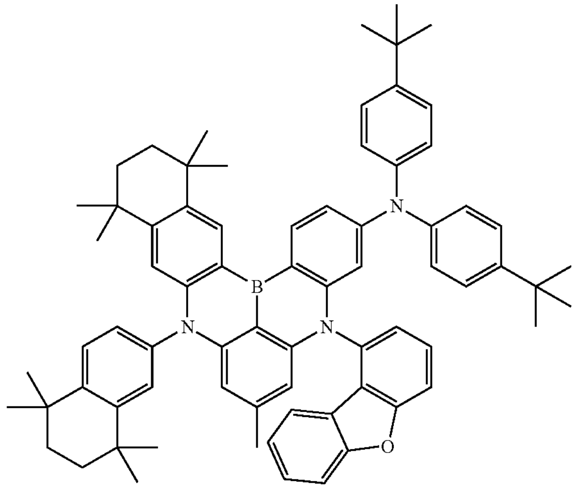

BD-42

After 7 g of Intermediate 67, 2.5 g of bis(4-(tert-butyl)phenyl)amine, 1.7 g of sodium-tert-butoxide, and 0.05 g of bis(tri-tert-butylphosphine)palladium(0) were put into 80 ml of xylene, the resulting mixture was stirred under reflux for 5 hours. After the completion of the reaction, the resulting product was extracted, and then recrystallized to obtain 6.6 g of BD-42. (Yield 72%). MS[M+H]+=1025

Synthesis Example 102. Synthesis of BD-43

1) Synthesis of Intermediate 68

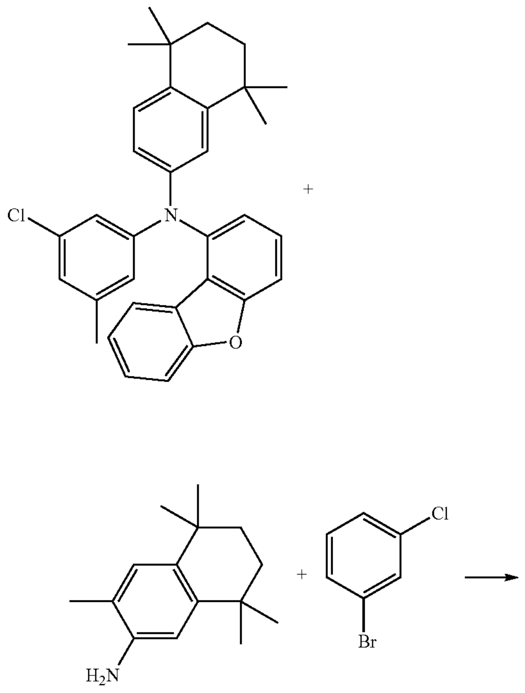

-continued

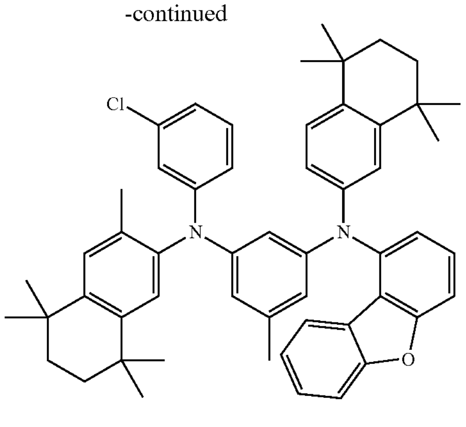

68

After 40 g of N-(3-chloro-5-methylphenyl)-N-(5,5,8,8-tetramethyl-5,6,7,8-tetrahydronaphthalen-2-yl)dibenzo[b,d]furan-1-amine, 16.6 g of 3,5,5,8,8-pentamethyl-5,6,7,8-tetrahydronaphthalen-2-amine, 23.3 g of sodium-tert-butoxide, and 0.4 g of bis(tri-tert-butylphosphine)palladium(0) were put into 600 ml of toluene, the resulting mixture was refluxed for 1 hour, whether the reaction proceeded was confirmed, and then 15.5 g of 1-bromo-3-chlorobenzene was added thereto during the reflux reaction, and the reflux reaction was performed for an additional 1 hour. After the completion of the reaction, the resulting product was extracted, and then recrystallized to obtain 47 g of Intermediate 68. (Yield 74%). MS[M+H]+=786

2) Synthesis of Intermediate 69

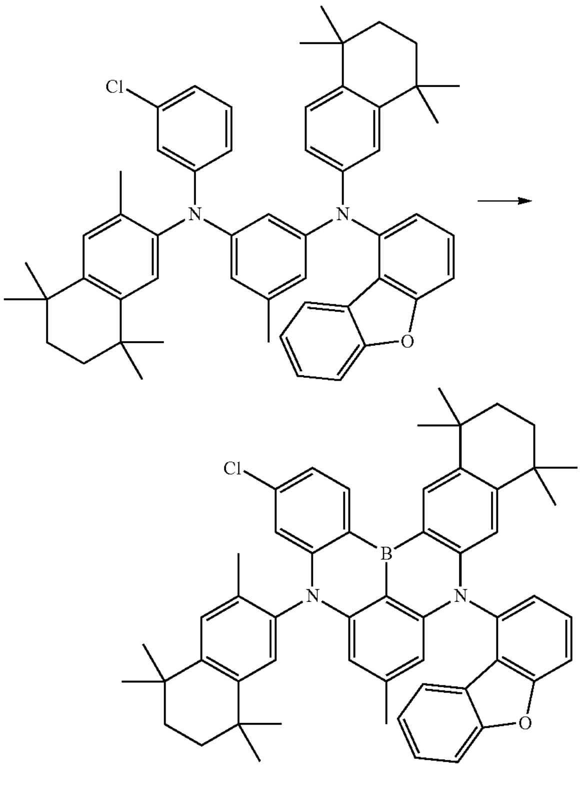

69

After 25 g of Intermediate 68 and 21.2 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.7 g of Intermediate 69 (yield 30%). MS[M+H]+=794

3) Synthesis of BD-43

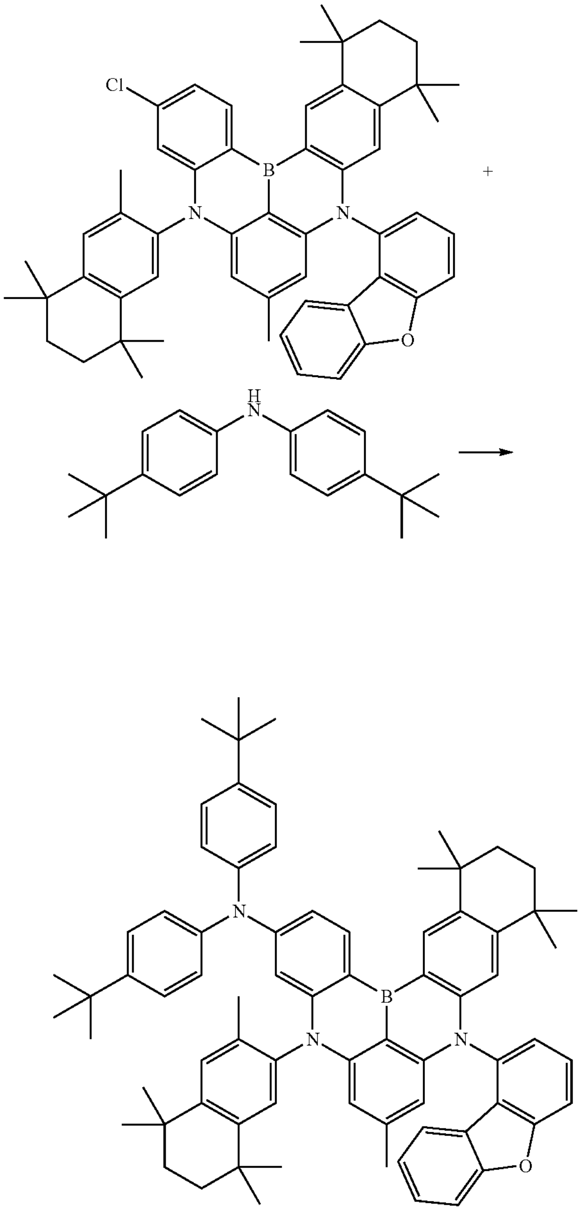

BD-43

After 7 g of Intermediate 69, 2.5 g of bis(4-(tert-butyl)phenyl)amine, 1.7 g of sodium-tert-butoxide, and 0.05 g of bis(tri-tert-butylphosphine)palladium(0) were put into 80 ml of xylene, the resulting mixture was stirred under reflux for 5 hours. After the completion of the reaction, the resulting product was extracted, and then recrystallized to obtain 6.8 g of BD-43. (Yield 74%). MS[M+H]+=1039

Synthesis Example 103. Synthesis of BD-44

1) Synthesis of Intermediate 70

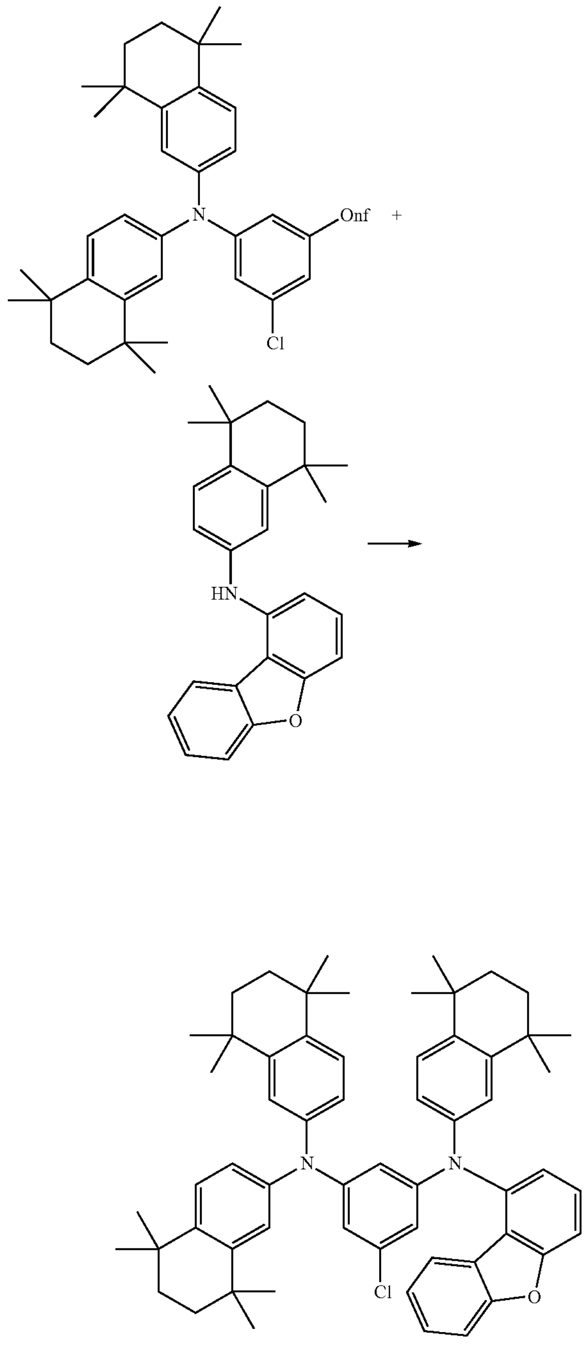

70

After the completion of a reaction of 40 g of Intermediate 46 with 18.9 g of N-(5,5,8,8-tetramethyl-5,6,7,8-tetrahydronapthalen-2-yl)dibenzo[b,d]furan-1-amine using the same material and equivalent weight as in the synthesis method of Intermediate 47, the resulting product was extracted, and then recrystallized to obtain 34 g of Intermediate 70. (Yield 77%). MS[M+H]+=868

2) Synthesis of Intermediate 71

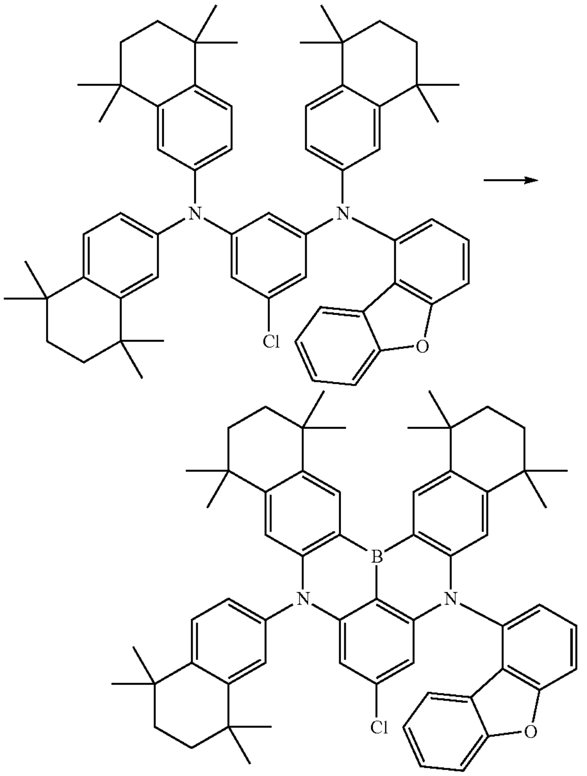

71

After 25 g of Intermediate 71 and 19.2 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.5 g of Intermediate 71 (yield 30%). MS[M+H]+=876

3) Synthesis of BD-44

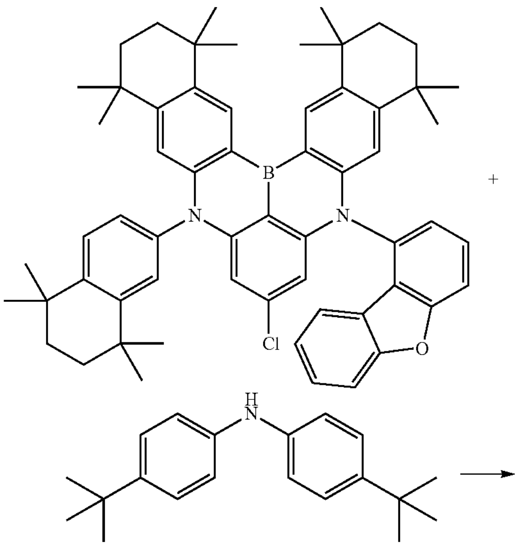

-continued

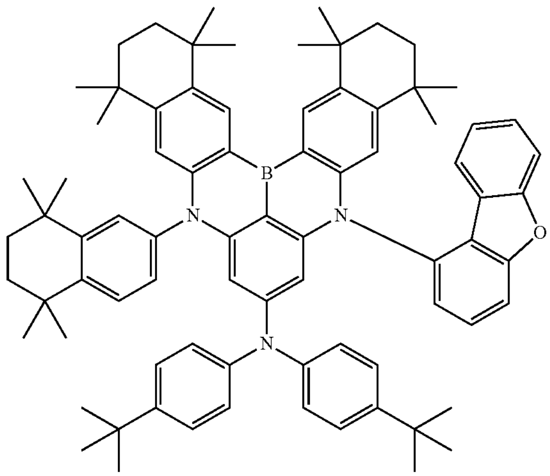

BD-44

After 7 g of Intermediate 71, 2.5 g of bis(4-(tert-butyl)phenyl)amine, 1.7 g of sodium-tert-butoxide, and 0.05 g of bis(tri-tert-butylphosphine)palladium(0) were put into 80 ml of xylene, the resulting mixture was stirred under reflux for 5 hours. After the completion of the reaction, the resulting product was extracted, and then recrystallized to obtain 6.9 g of BD-44. (Yield 70%). MS[M+H]+=1120

Synthesis Example 104. Synthesis of BD-45

1) Synthesis of Intermediate 72

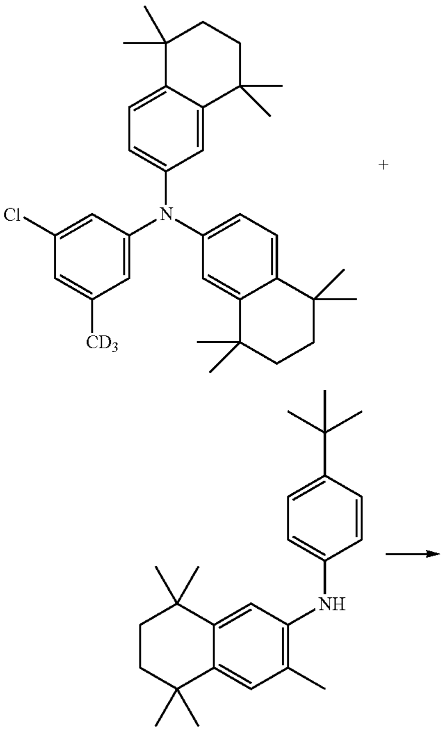

-continued

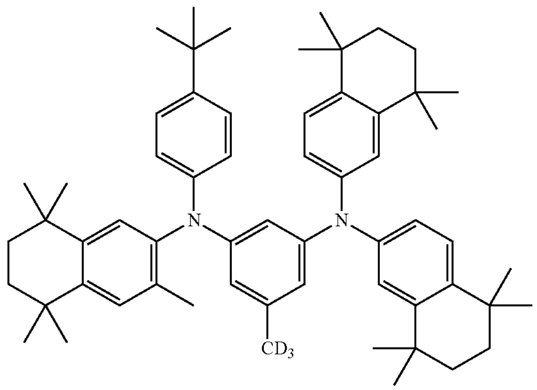

72

30 g of N-(3-chloro-5-(methyl-d3)phenyl)-5,5,8,8-tetramethyl-N-(5,5,8,8-tetramethyl-5,6,7,8-tetrahydronapthalen-2-yl)-5,6,7,8-tetrahydronaphthalen-2-amine, 20.4 g of N-(4-(tert-butyl)phenyl)-3,5,5,8,8-pentamethyl-5,6,7,8-tetrahydronaphthalen-2-amine, and the same material and equivalent weight as in the synthesis method of Intermediate 2 were used and then recrystallized to obtain 33 g of Intermediate 72. (Yield 69%). MS[M+H]+=831

2) Synthesis of BD-45

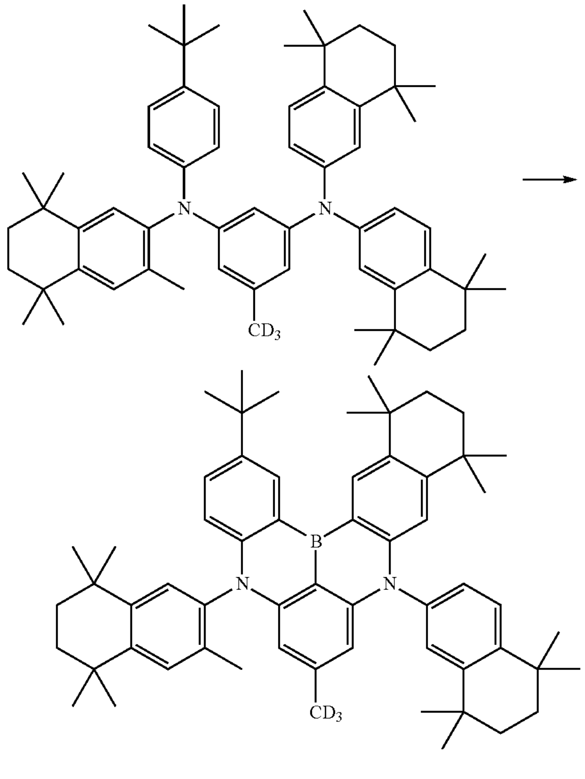

BD-45

After 25 g of Intermediate 72 and 20.4 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.4 g of BD-45 (yield 29%). MS[M+H]+=839

Synthesis Example 105. Synthesis of BD-46

1) Synthesis of Intermediate 73

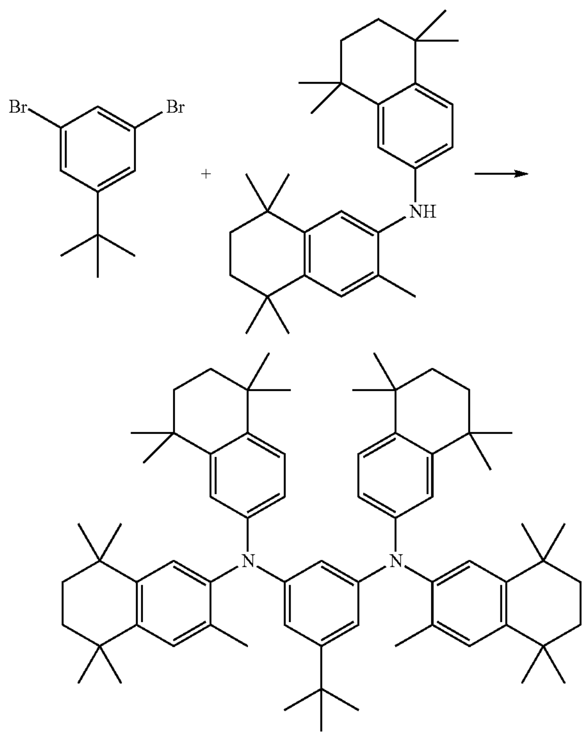

73

30 g of 1,3-dibromo-5-(tert-butyl)benzene, 83 g of 3,5,5,8,8-pentamethyl-N-(5,5,8,8-tetramethyl-5,6,7,8-tetrahydronaphthalen-2-yl)-5,6,7,8-tetrahydronaphthalen-2-amine, and the same material and equivalent weight as in the synthesis method of Intermediate 20 were used and then recrystallized to obtain 66 g of Intermediate 73. (Yield 69%). MS[M+H]+=938

2) Synthesis of BD-46

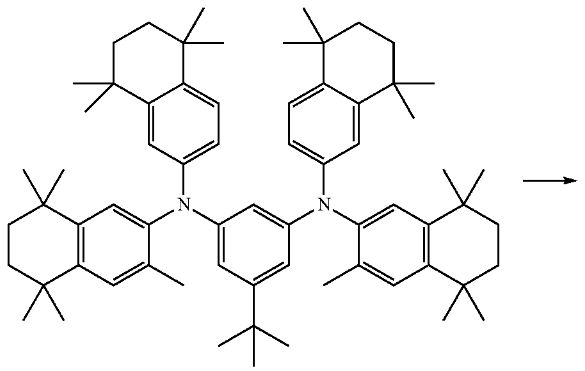

-continued

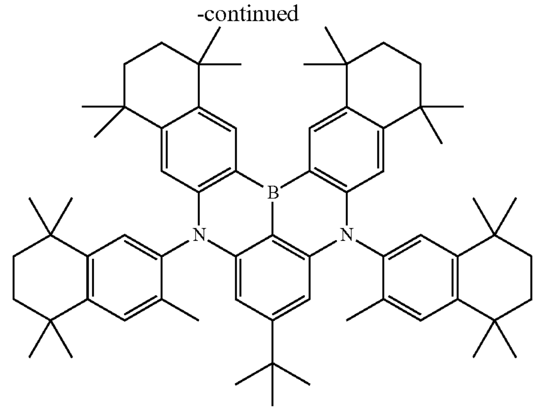

BD-46

After 25 g of Intermediate 73 and 17.7 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.6 g of BD-46 (yield 30%). MS[M+H]+=946

Synthesis Example 106. Synthesis of BD-47

1) Synthesis of Intermediate 74

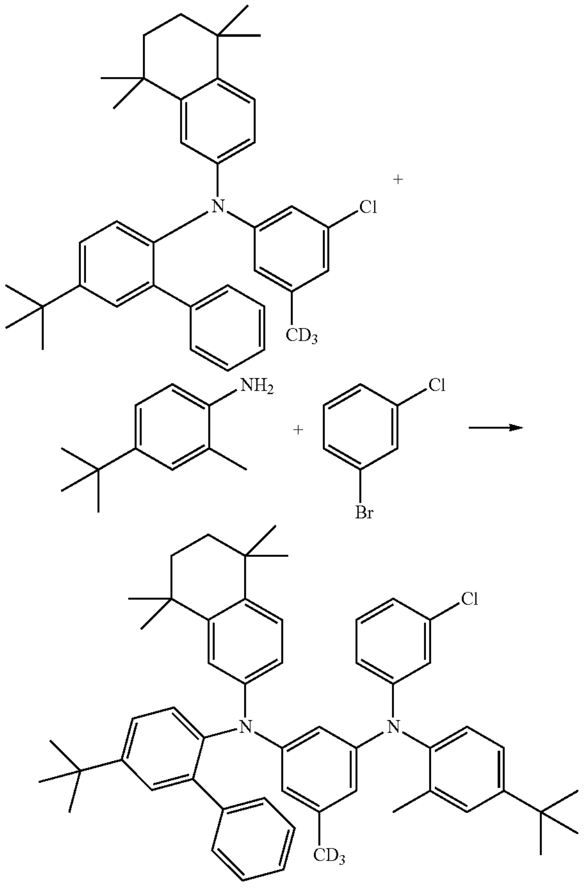

74

After 40 g of N-(5-(tert-butyl)-[1,1'-biphenyl]-2-yl)-N-(3-chloro-5-(methyl-d3)phenyl)-5,5,8,8-tetramethyl-5,6,7,8-tetrahydronaphthalen-2-amine, 12.1 g of 4-(tert-butyl)-2-methylaniline, 21.4 g of sodium-tert-butoxide, and 0.4 g of bis(tri-tert-butylphosphine)palladium(0) were put into 600 ml of toluene, the resulting mixture was refluxed for 1 hour, whether the reaction proceeded was confirmed, and then 14.2 g of 1-bromo-3-chlorobenzene was added thereto during the reflux reaction, and the reflux reaction was performed for an additional 1 hour. After the completion of the reaction, the resulting product was extracted, and then recrystallized to obtain 42 g of Intermediate 74. (Yield 73%). MS[M+H]+=777

2) Synthesis of Intermediate 75

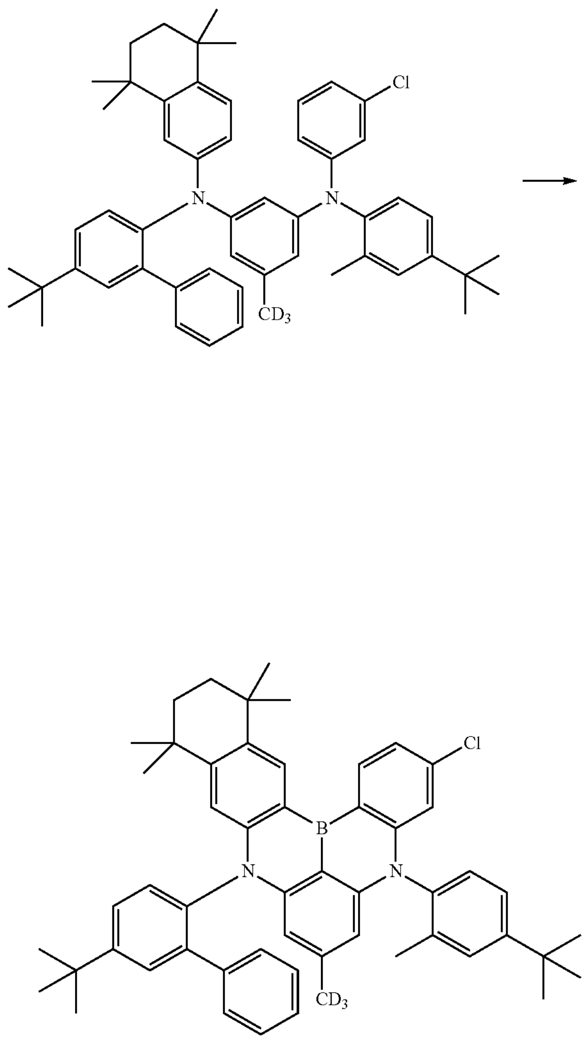

75

After 25 g of Intermediate 74 and 21.4 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.5 g of Intermediate 75 (yield 30%). MS[M+H]+=785

3) Synthesis of BD-47

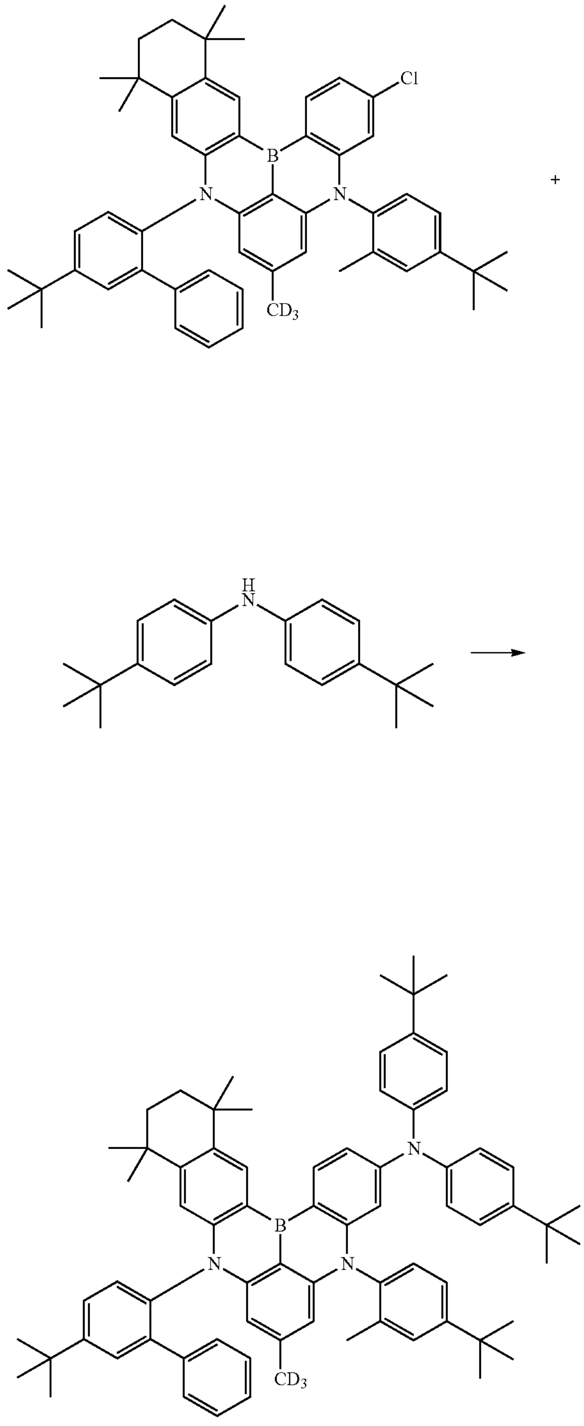

BD-47

After 7 g of Intermediate 75, 2.5 g of bis(4-(tert-butyl)phenyl)amine, 1.7 g of sodium-tert-butoxide, and 0.05 g of bis(tri-tert-butylphosphine)palladium(0) were put into 80 ml of xylene, the resulting mixture was stirred under reflux for 5 hours. After the completion of the reaction, the resulting product was extracted, and then recrystallized to obtain 7.1 g of BD-47. (Yield 77%). MS[M+H]+=1030

Synthesis Example 107. Synthesis of BD-48

1) Synthesis of Intermediate 76

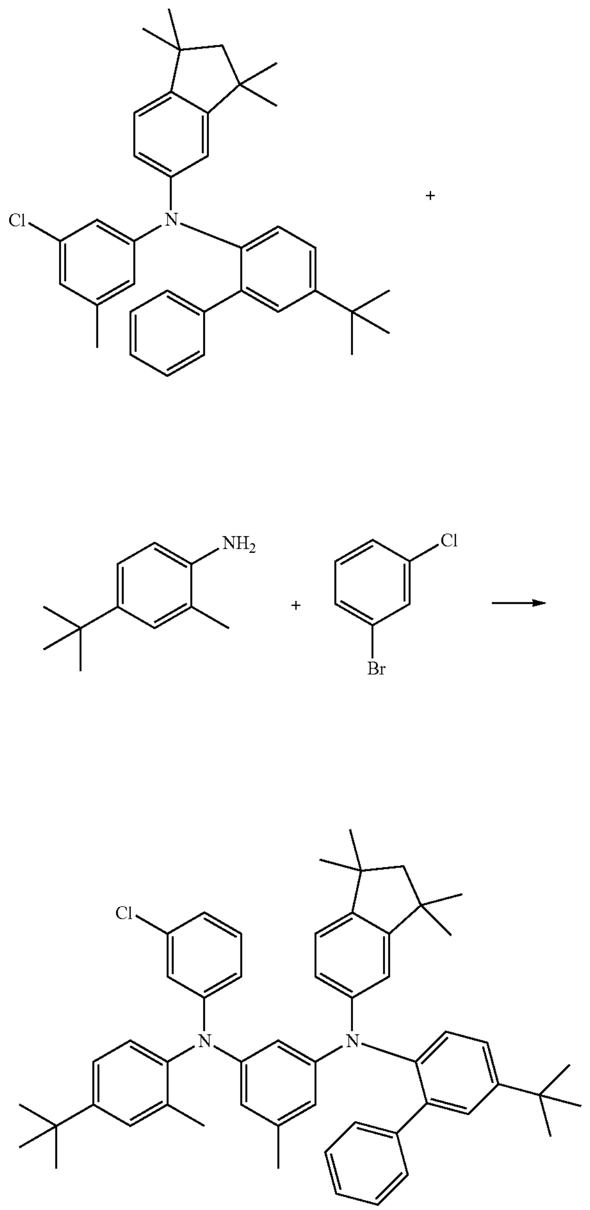

76

After 40 g of N-(5-(tert-butyl)-[1,1'-biphenyl]-2-yl)-N-(3-chloro-5-methylphenyl)-1,1,3,3-tetramethyl-2,3-dihydro-1H-inden-5-amine, 12.1 g of 4-(tert-butyl)-2-methylaniline, 22.1 g of sodium-tert-butoxide, and 0.4 g of bis(tri-tert-butylphosphine)palladium(0) were put into 600 ml of toluene, the resulting mixture was refluxed for 1 hour, whether the reaction proceeded was confirmed, and then 14.6 g of 1-bromo-3-chlorobenzene was added thereto during the reflux reaction, and the reflux reaction was performed for an additional 1 hour. After the completion of the reaction, the resulting product was extracted, and then recrystallized to obtain 43 g of Intermediate 76. (Yield 74%). MS[M+H]+=760

2) Synthesis of Intermediate 77

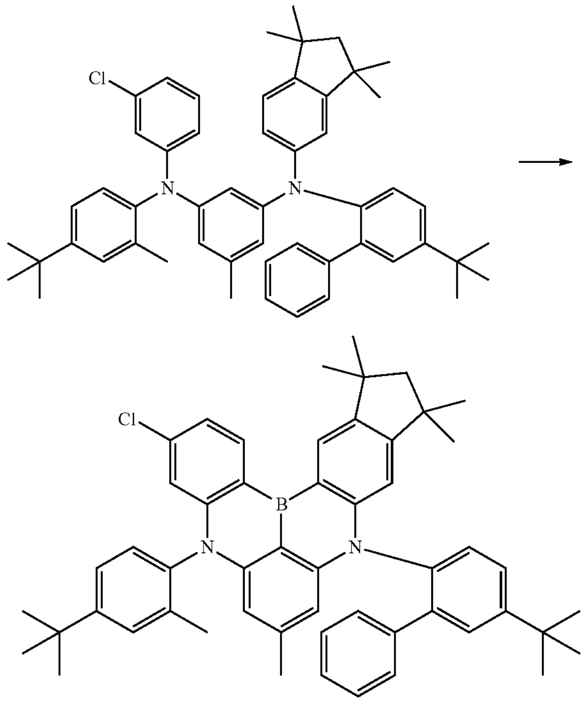

77

After 25 g of Intermediate 76 and 21.9 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.1 g of Intermediate 77 (yield 28%). MS[M+H]+=768

3) Synthesis of BD-48

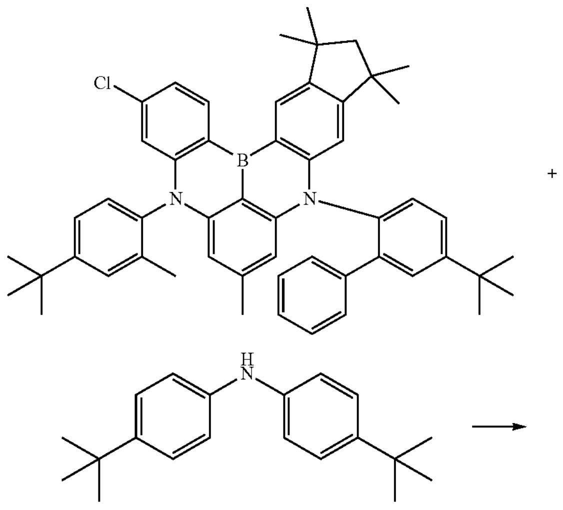

-continued

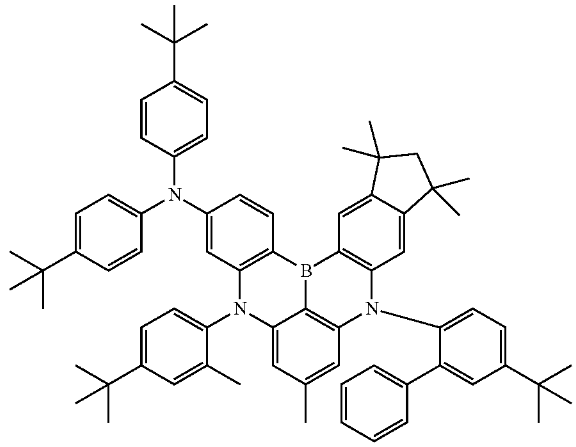

BD-48

After 7 g of Intermediate 77, 2.5 g of bis(4-(tert-butyl)phenyl)amine, 1.7 g of sodium-tert-butoxide, and 0.05 g of bis(tri-tert-butylphosphine)palladium(0) were put into 80 ml of xylene, the resulting mixture was stirred under reflux for 5 hours. After the completion of the reaction, the resulting product was extracted, and then recrystallized to obtain 6.5 g of BD-48. (Yield 72%). MS[M+H]+=1013

Synthesis Example 108. Synthesis of BD-49

1) Synthesis of Intermediate 78

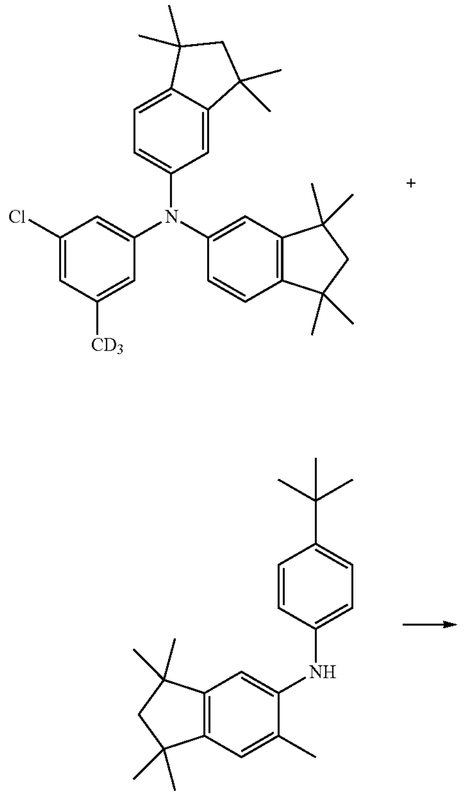

-continued

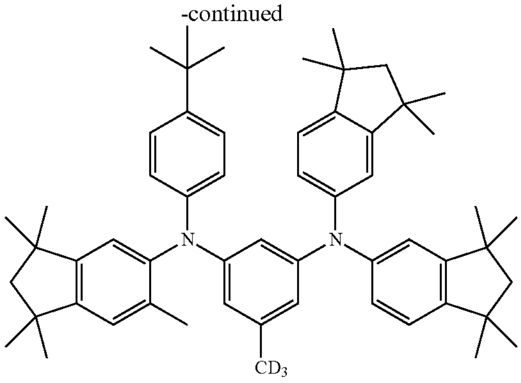

78

30 g of N-(3-chloro-5-(methyl-d3)phenyl)-1,1,3,3-tetramethyl-N-(1,1,3,3-tetramethyl-2,3-dihydro-1H-inden-5-yl)-2,3-dihydro-1H-inden-5-amine, 27.4 g of N-(4-(tert-butyl)phenyl)-1,1,3,3,6-pentamethyl-2,3-dihydro-1H-inden-5-amine, and the same material and equivalent weight as in the synthesis method of Intermediate 2 were used and then recrystallized to obtain 33 g of Intermediate 78. (Yield 78%). MS[M+H]+=789

2) Synthesis of BD-49

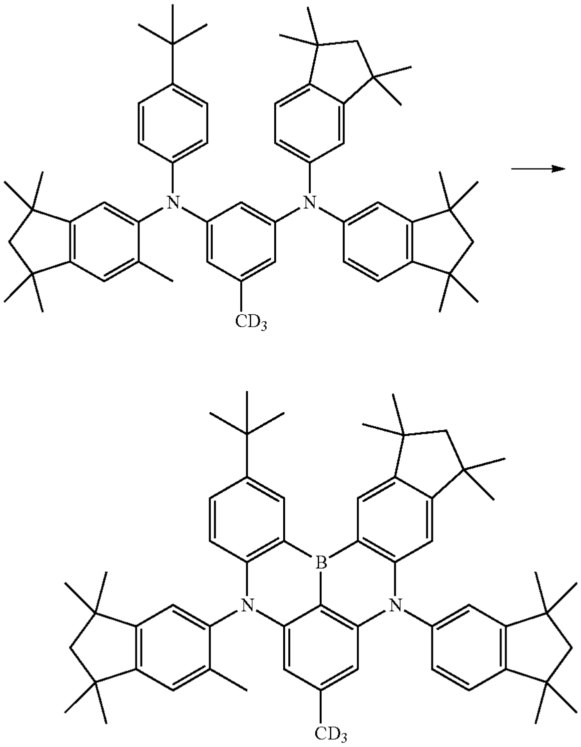

BD-49

After 25 g of Intermediate 78 and 21.1 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.5 g of BD-49 (yield 30%). MS[M+H]+=797

Synthesis Example 109. Synthesis of BD-50

1) Synthesis of Intermediate 79

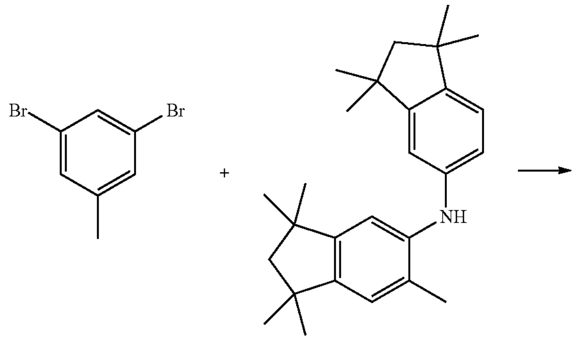

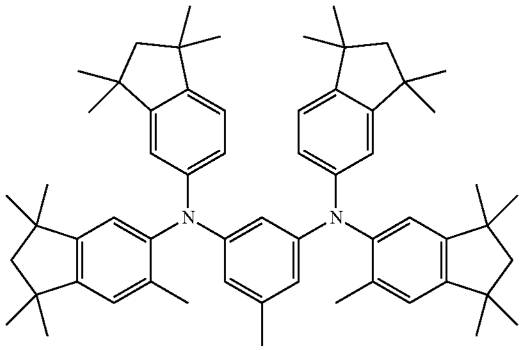

79

30 g of 1,3-dibromo-5-methylbenzene, 90.1 g of 1,1,3,3,6-pentamethyl-N-(1,1,3,3-tetramethyl-2,3-dihydro-1H-inden-5-yl)-2,3-dihydro-1H-inden-5-amine, and the same material and equivalent weight as in the synthesis method of Intermediate 20 were used and then recrystallized to obtain 66 g of Intermediate 79. (Yield 66%). MS[M+H]+=840

2) Synthesis of BD-50

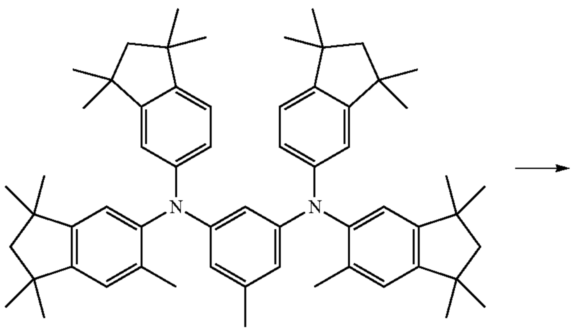

-continued

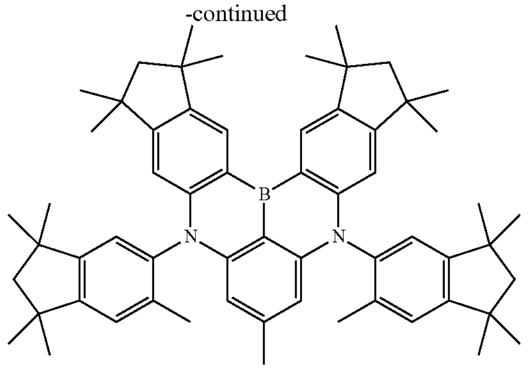

BD-50

After 25 g of Intermediate 79 and 19.8 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.3 g of BD-50 (yield 29%). MS[M+H]+=848

Synthesis Example 110. Synthesis of BD-51

1) Synthesis of Intermediate 80

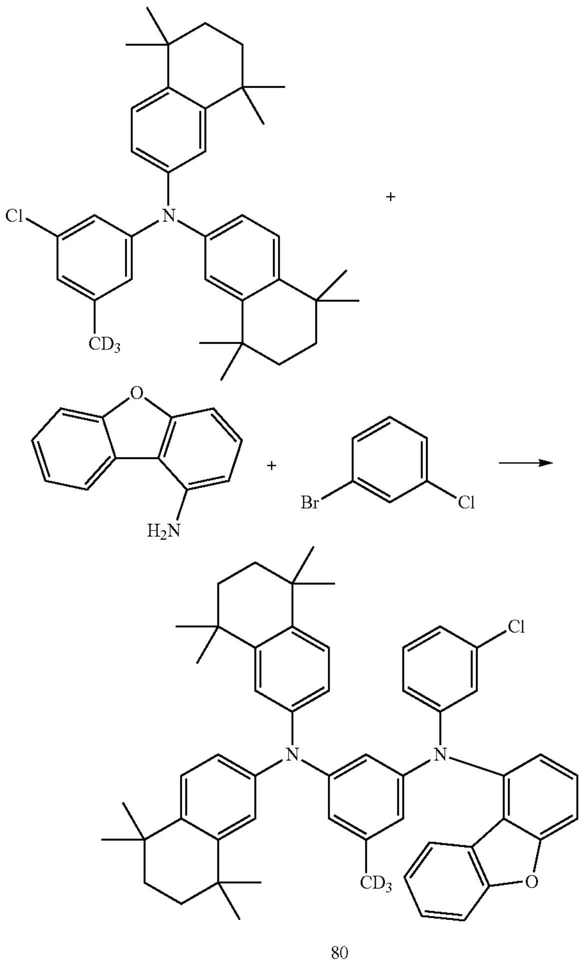

80

After 40 g of N-(3-chloro-5-(methyl-d3)phenyl)-5,5,8,8-tetramethyl-N-(5,5,8,8-tetramethyl-5,6,7,8-tetrahydronaphthalen-2-yl)-5,6,7,8-tetrahydronaphthalen-2-amine, 14.2 g of dibenzo[b,d]furan-1-amine, 22.3 g of sodium-tert-butoxide, and 0.4 g of bis(tri-tert-butylphosphine)palladium(0) were put into 600 ml of toluene, the resulting mixture was refluxed for 1 hour, whether the reaction proceeded was confirmed, and then 14.1 g of 1-bromo-3-chlorobenzene was added thereto during the reflux reaction, and the reflux reaction was performed for an additional 1 hour. After the completion of the reaction, the resulting product was extracted, and then recrystallized to obtain 41 g of Intermediate 80. (Yield 68%). MS[M+H]+=775

2) Synthesis of Intermediate 81

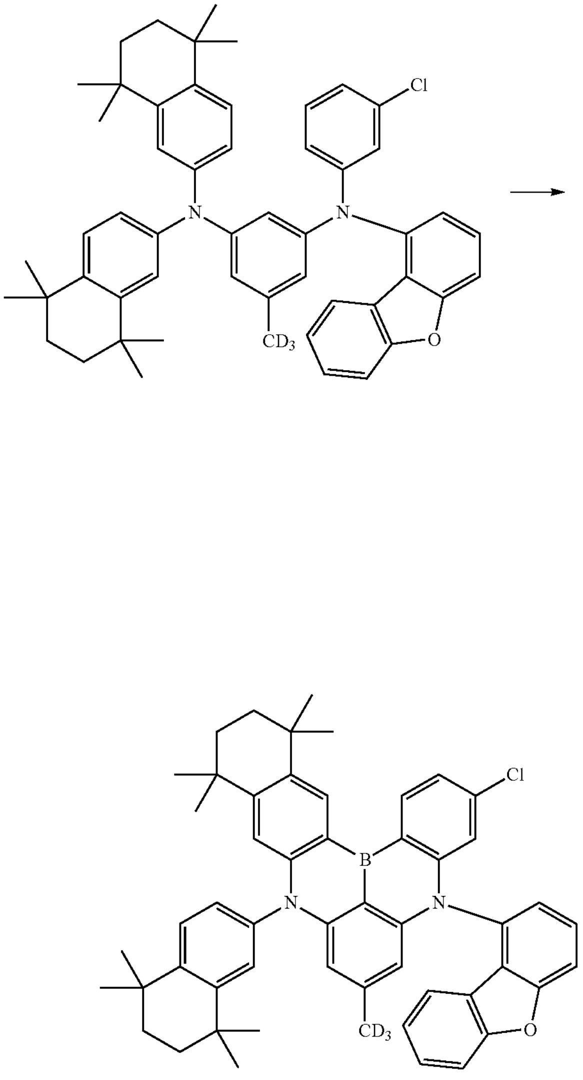

81

After 25 g of Intermediate 80 and 21.5 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.5 g of Intermediate 81 (yield 30%). MS[M+H]+=783

3) Synthesis of BD-51

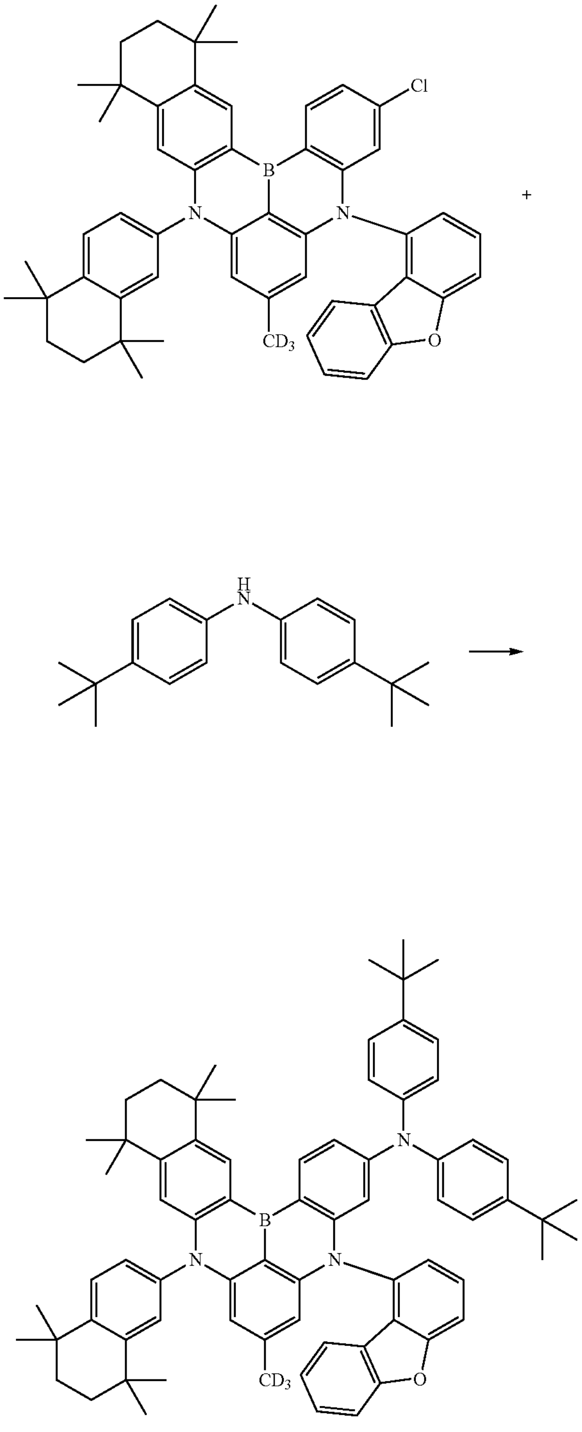

BD-51

After 7 g of Intermediate 81, 2.5 g of bis(4-(tert-butyl)phenyl)amine, 1.7 g of sodium-tert-butoxide, and 0.05 g of bis(tri-tert-butylphosphine)palladium(0) were put into 80 ml of xylene, the resulting mixture was stirred under reflux for 5 hours. After the completion of the reaction, the resulting product was extracted, and then recrystallized to obtain 6.6 g of BD-51. (Yield 72%). MS[M+H]+=1028

Synthesis Example 111. Synthesis of BD-52

1) Synthesis of Intermediate 82

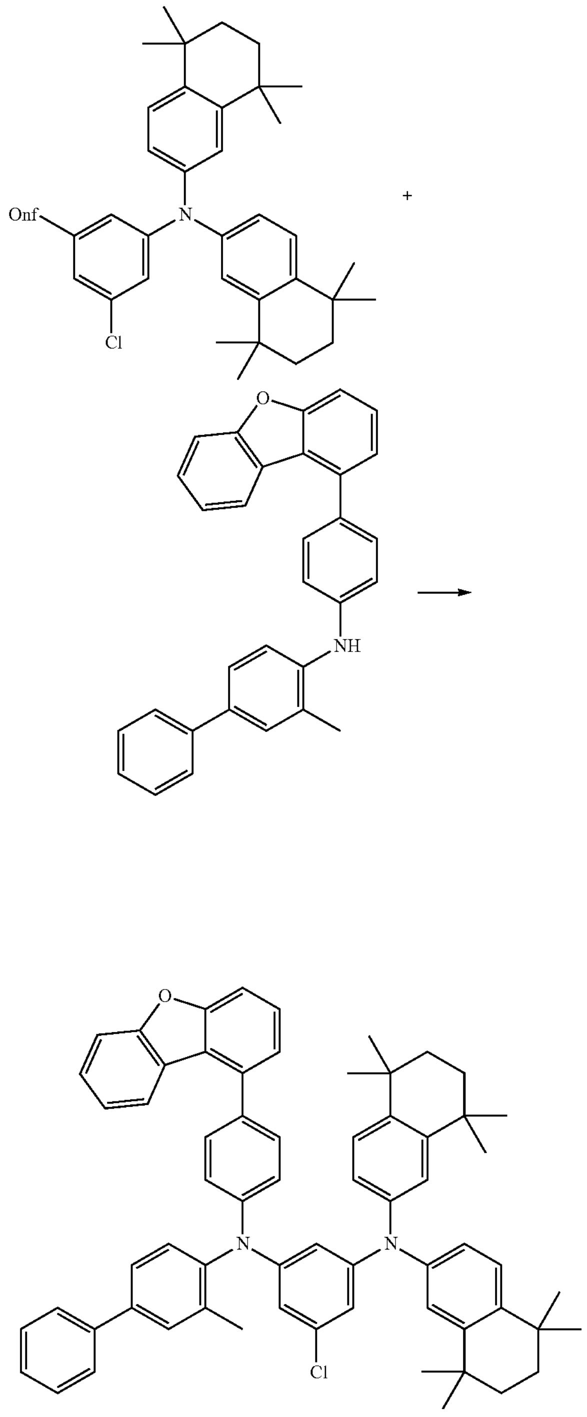

82

40 g of Intermediate 46, 31 g of N-(4-(dibenzo[b,d]furan-1-yl)phenyl)-3-methyl-[1,1'-biphenyl]-4-amine, and the same material and equivalent weight as in the synthesis method of Intermediate 37 were recrystallized to obtain 55 g of Intermediate 82. (Yield 78%). MS[M+H]+=924

2) Synthesis of Intermediate 83

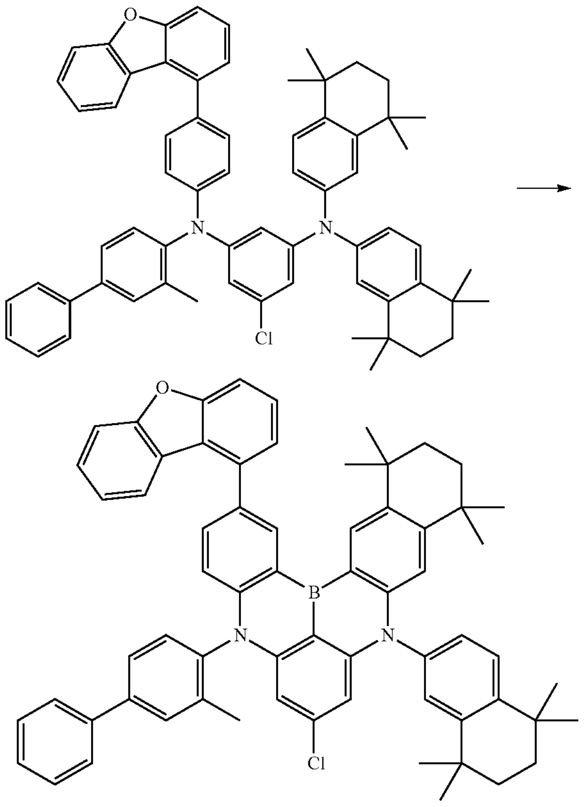

83

After 25 g of Intermediate 82 and 18 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.2 g of Intermediate 83 (yield 29%). MS[M+H]+=932

3) Synthesis of BD-52

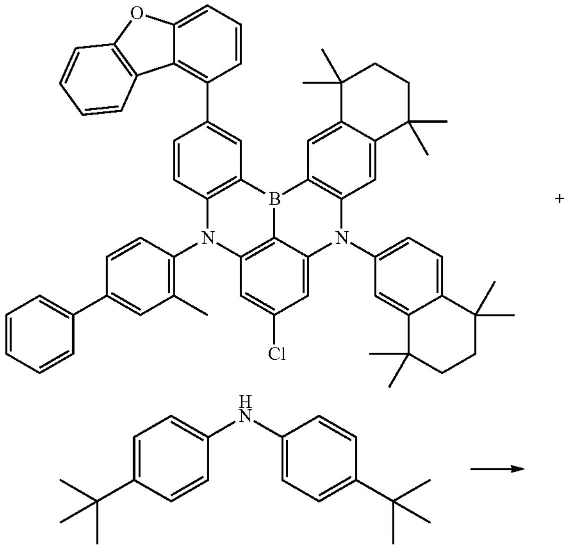

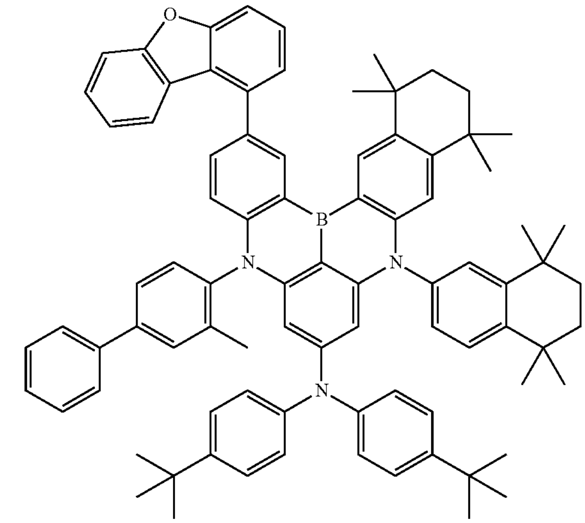

BD-52

After 7 g of Intermediate 83, 2.1 g of bis(4-(tert-butyl)phenyl)amine, 1.7 g of sodium-tert-butoxide, and 0.05 g of bis(tri-tert-butylphosphine)palladium(0) were put into 80 ml of xylene, the resulting mixture was stirred under reflux for 5 hours. After the completion of the reaction, the resulting product was extracted, and then recrystallized to obtain 6.4 g of BD-52. (Yield 72%). MS[M+H]+=1177

Synthesis Example 112. Synthesis of BD-53

1) Synthesis of Intermediate 84

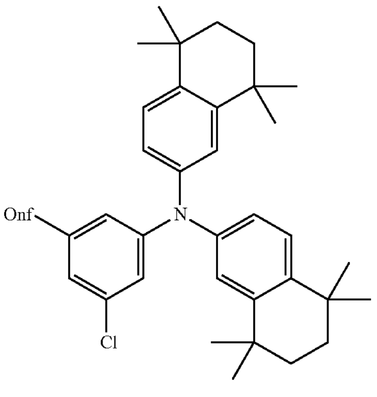

+

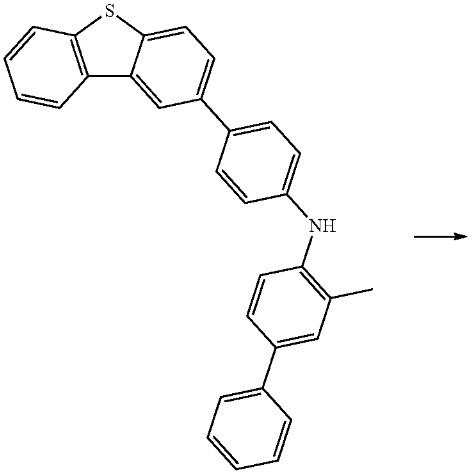

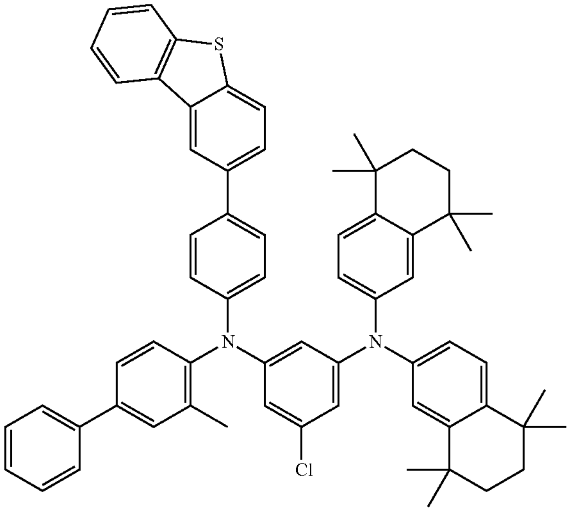

84

40 g of Intermediate 46, 34 g of N-(4-(dibenzo[b,d]thiophen-2-yl)phenyl)-3-methyl-[1,1'-biphenyl]-4-amine, and the same material and equivalent weight as in the synthesis method of Intermediate 37 were used and then recrystallized to obtain 54 g of Intermediate 84. (Yield 74%). MS[M+H]+=940

2) Synthesis of Intermediate 85

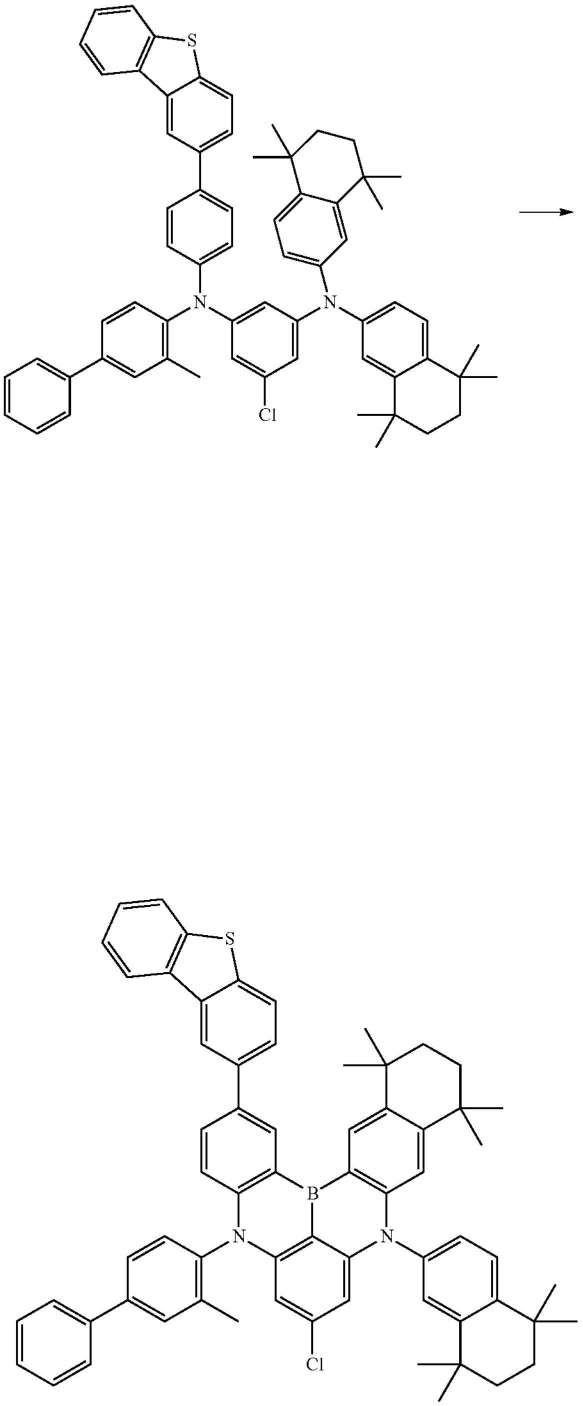

85

After 25 g of Intermediate 84 and 17.7 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.5 g of Intermediate 85 (yield 30%). MS[M+H]+=948

3) Synthesis of BD-53

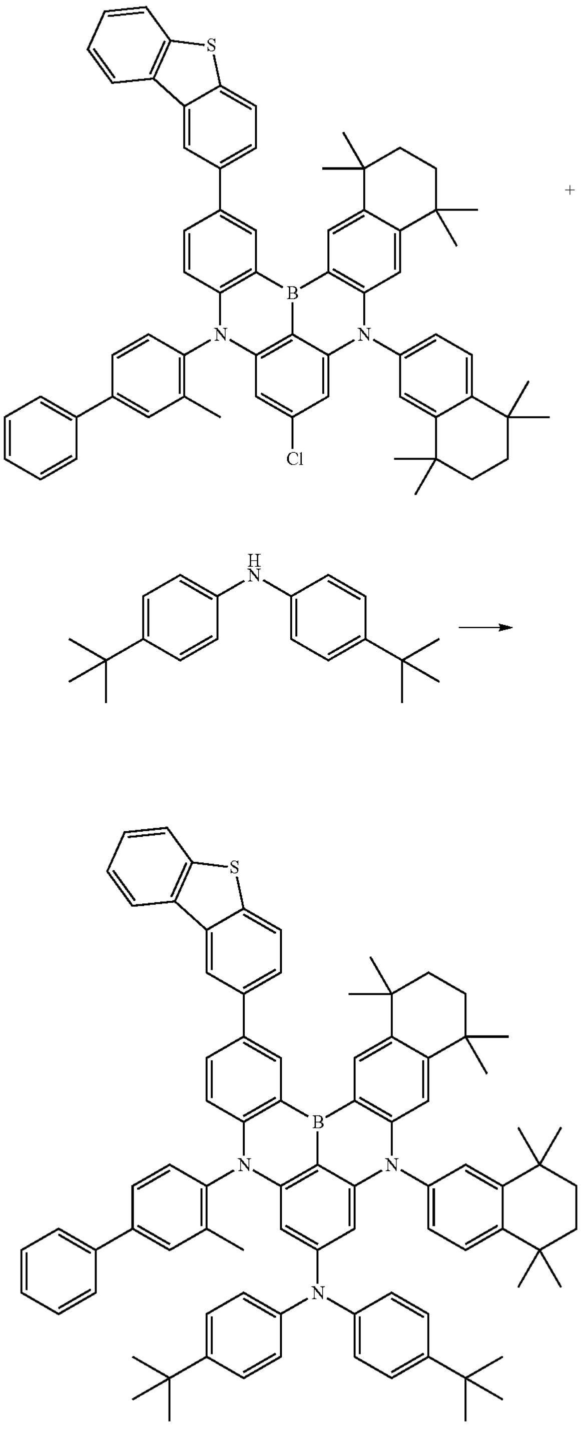

BD-53

After 7 g of Intermediate 85, 2.1 g of bis(4-(tert-butyl)phenyl)amine, 1.7 g of sodium-tert-butoxide, and 0.05 g of bis(tri-tert-butylphosphine)palladium(0) were put into 80 ml of xylene, the resulting mixture was stirred under reflux for 5 hours. After the completion of the reaction, the resulting product was extracted, and then recrystallized to obtain 6.6 g of BD-53. (Yield 72%). MS[M+H]+=1235

Synthesis Example 113. Synthesis of BD-54

1) Synthesis of Intermediate 86

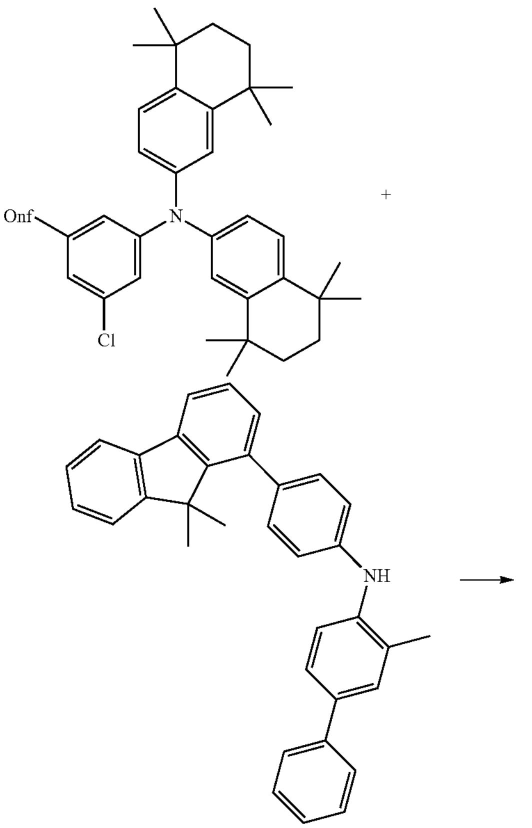

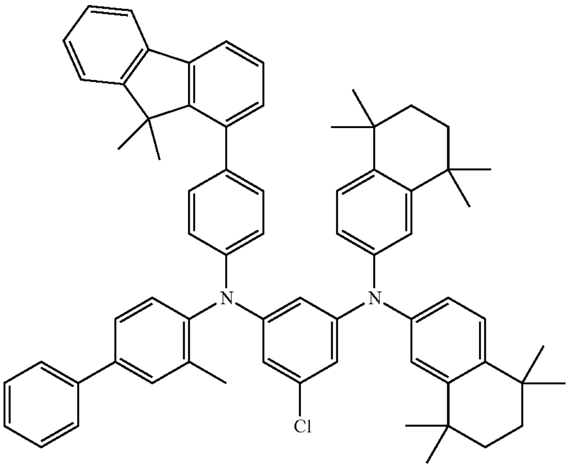

86

40 g of Intermediate 46, 35 g of N-(4-(9,9-dimethyl-9H-fluoren-1-yl)phenyl)-3-methyl-[1,1'-biphenyl]-4-amine, and the same material and equivalent weight as in the synthesis method of Intermediate 37 were used and then recrystallized to obtain 53 g of Intermediate 86. (Yield 72%). MS[M+H]+= 950

2) Synthesis of Intermediate 87

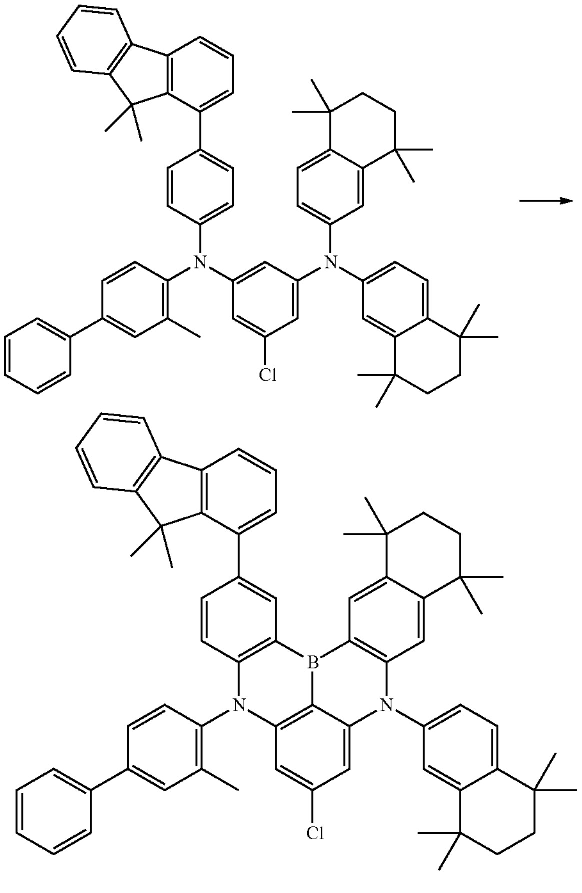

87

After 25 g of Intermediate 86 and 17.5 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.7 g of Intermediate 87 (yield 31%). MS[M+H]+= 958

3) Synthesis of BD-54

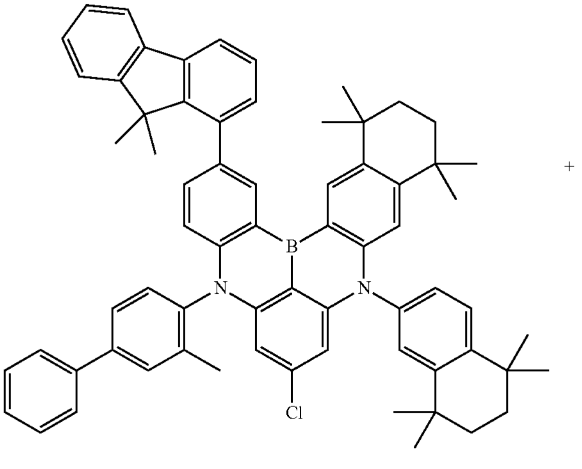

-continued

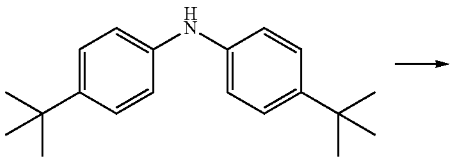

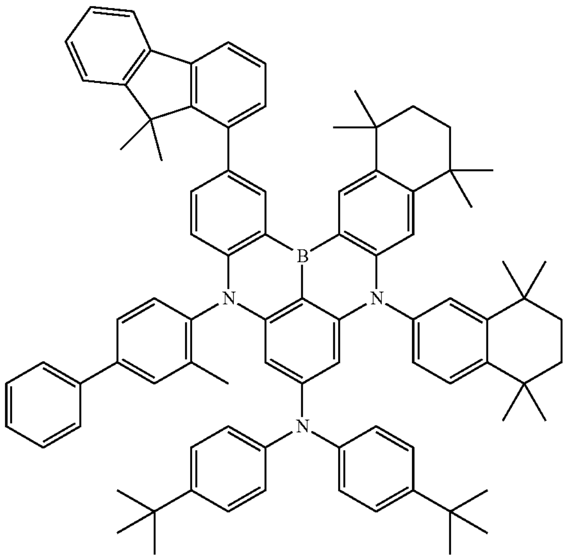

BD-54

After 7 g of Intermediate 87, 2.1 g of bis(4-(tert-butyl)phenyl)amine, 1.7 g of sodium-tert-butoxide, and 0.05 g of bis(tri-tert-butylphosphine)palladium(0) were put into 80 ml of xylene, the resulting mixture was stirred under reflux for 5 hours. After the completion of the reaction, the resulting product was extracted, and then recrystallized to obtain 6.8 g of BD-54. (Yield 75%). MS[M+H]+=1245

Synthesis Example 114. Synthesis of BD-55

1) Synthesis of Intermediate 88

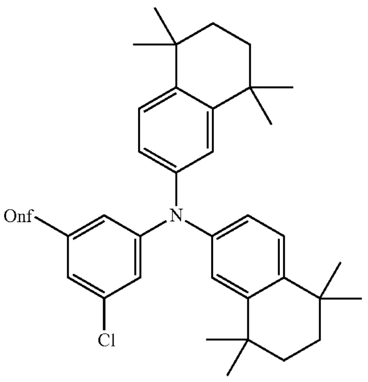

+

-continued

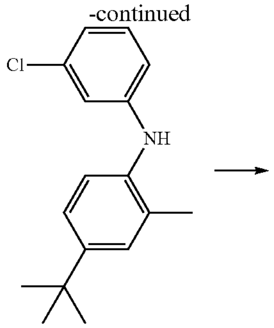

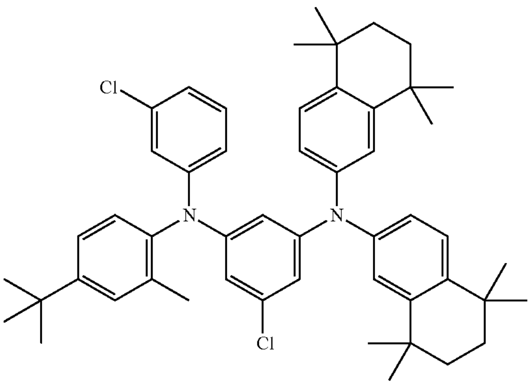

88

40 g of Intermediate 46, 15 g of 4-(tert-butyl)-N-(3-chlorophenyl)-2-methylaniline, and the same material and equivalent weight as in the synthesis method of Intermediate 37 were used and then recrystallized to obtain 31 g of Intermediate 88. (Yield 79%). MS[M+H]+=772

2) Synthesis of Intermediate 89

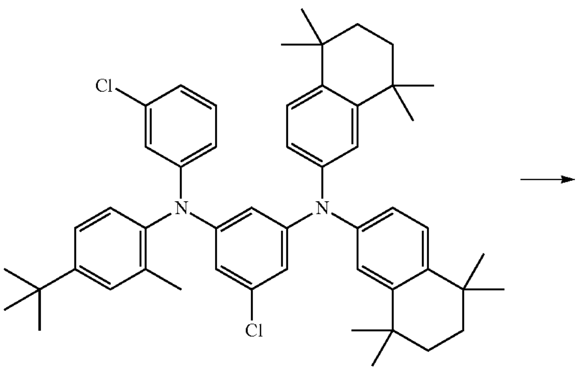

-continued

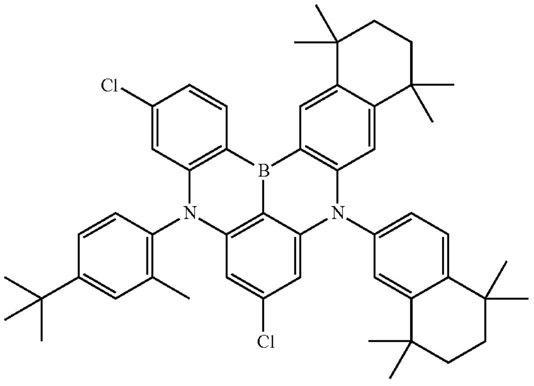

89

After 25 g of Intermediate 88 and 21.6 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.6 g of Intermediate 89 (yield 30%). MS[M+H]+ =780

3) Synthesis of BD-55

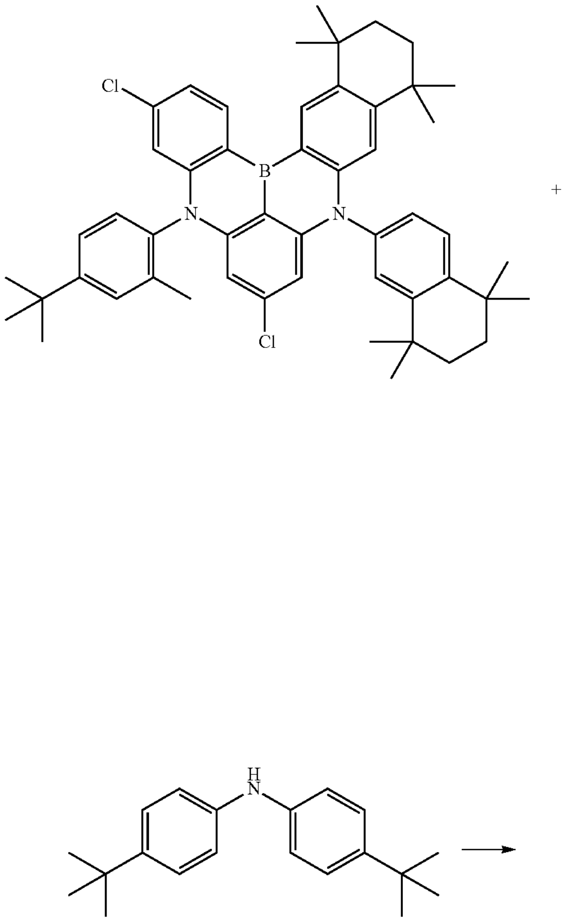

-continued

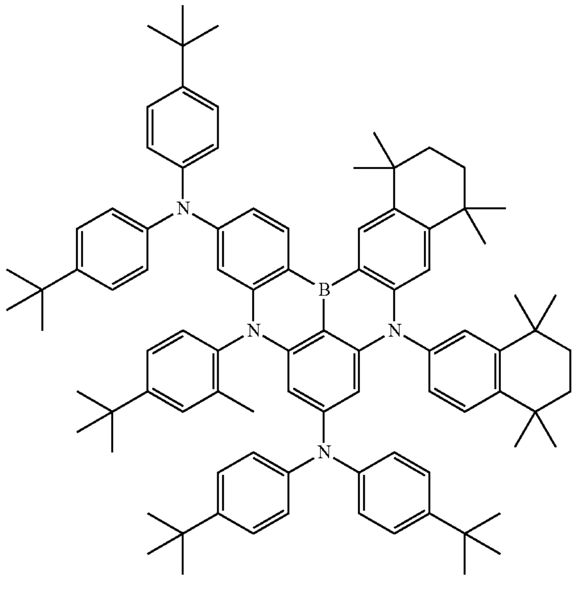

BD-55

After 7 g of Intermediate 89, 4.3 g of bis(4-(tert-butyl) phenyl)amine, 2.1 g of sodium-tert-butoxide, and 0.05 g of bis(tri-tert-butylphosphine)palladium(0) were put into 80 ml of xylene, the resulting mixture was stirred under reflux for 5 hours. After the completion of the reaction, the resulting product was extracted, and then recrystallized to obtain 7.2 g of BD-55. (Yield 78%). MS[M+H]+=1270

Synthesis Example 115. Synthesis of BD-56

1) Synthesis of BD-56

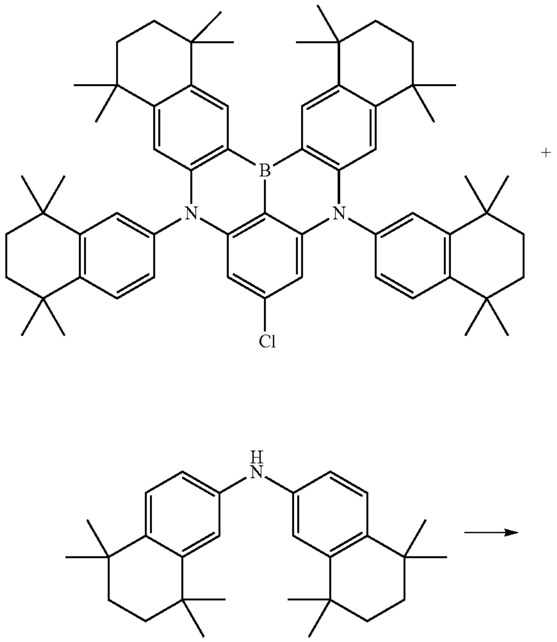

-continued

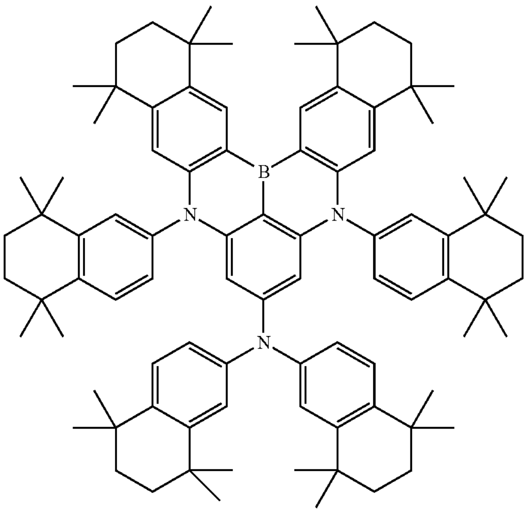

BD-56

After 7 g of Intermediate 58, 3 g of bis(5,5,8,8-tetramethyl-5,6,7,8-tetrahydronaphthalen-2-yl)amine, 1.5 g of sodium-tert-butoxide, and 0.04 g of bis(tri-tert-butylphosphine)palladium(0) were put into 80 ml of xylene, the resulting mixture was stirred under reflux for 5 hours.

After the completion of the reaction, the resulting product was extracted, and then recrystallized to obtain 7.1 g of BD-56. (Yield 73%). MS[M+H]+=1249

Synthesis Example 116. Synthesis of BD-57

1) Synthesis of Intermediate 90

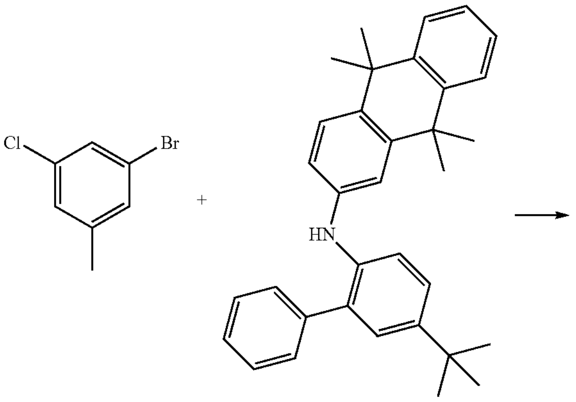

-continued

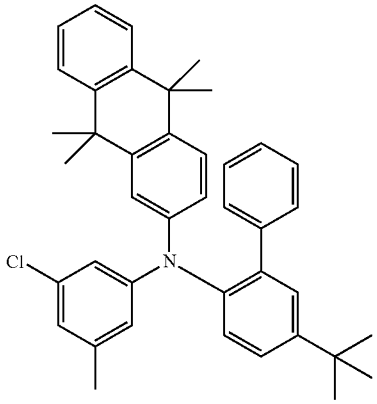

90

After 40 g of 1-bromo-3-chloro-5-methylbenzene, 89.5 g of N-(5-(tert-butyl)-[1,1'-biphenyl]-2-yl)-9,9,10,10-tetramethyl-9,10-dihydronanthracen-2-amine, 56.1 g of sodium-tert-butoxide, and 1.0 g of bis(tri-tert-butylphosphine)palladium(0) were put into 600 ml of toluene under a nitrogen atmosphere, the resulting mixture was stirred under reflux for 2 hours. After the completion of the reaction, the resulting product was extracted, and then recrystallized to obtain 88 g of Intermediate 90. (Yield 77%). MS[M+H]+=585

2) Synthesis of Intermediate 91

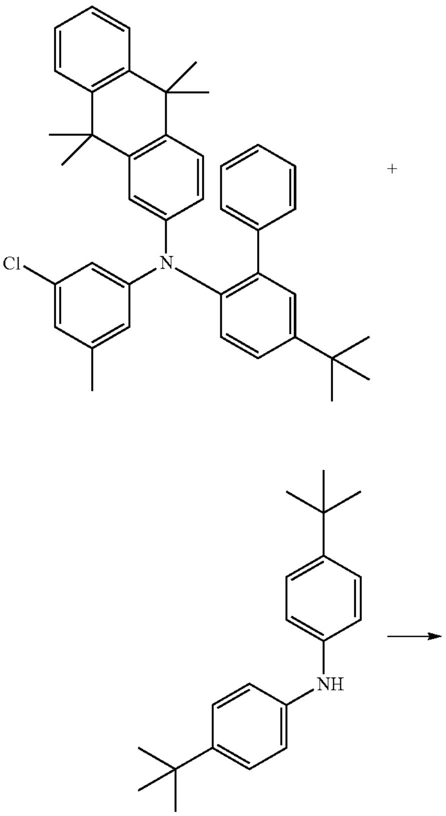

-continued

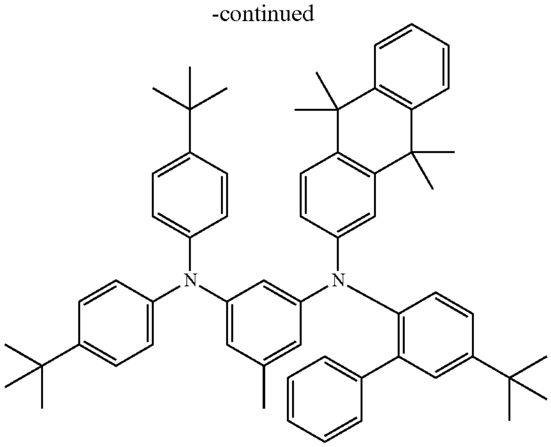

91

After 30 g of Intermediate 90, 14.5 g of bis(4-(tert-butyl)phenyl)amine, 9.9 g of sodium-tert-butoxide, and 0.3 g of bis(tri-tert-butylphosphine)palladium(0) were put into 450 ml of toluene under a nitrogen atmosphere, the resulting mixture was stirred under reflux for 2 hours. After the completion of the reaction, the resulting product was extracted, and then recrystallized to obtain 34 g of Intermediate 91. (Yield 80%). MS[M+H]+=830

3) Synthesis of BD-57

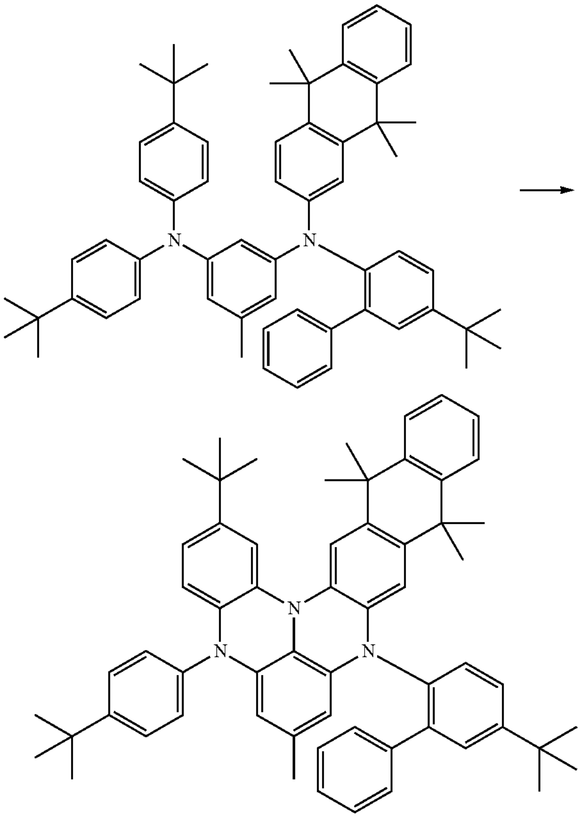

BD-57

After 25 g of Intermediate 91 and 20.1 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.5 g of BD-57 (yield 30%). MS[M+H]+=838

Synthesis Example 117. Synthesis of BD-58

1) Synthesis of Intermediate 92

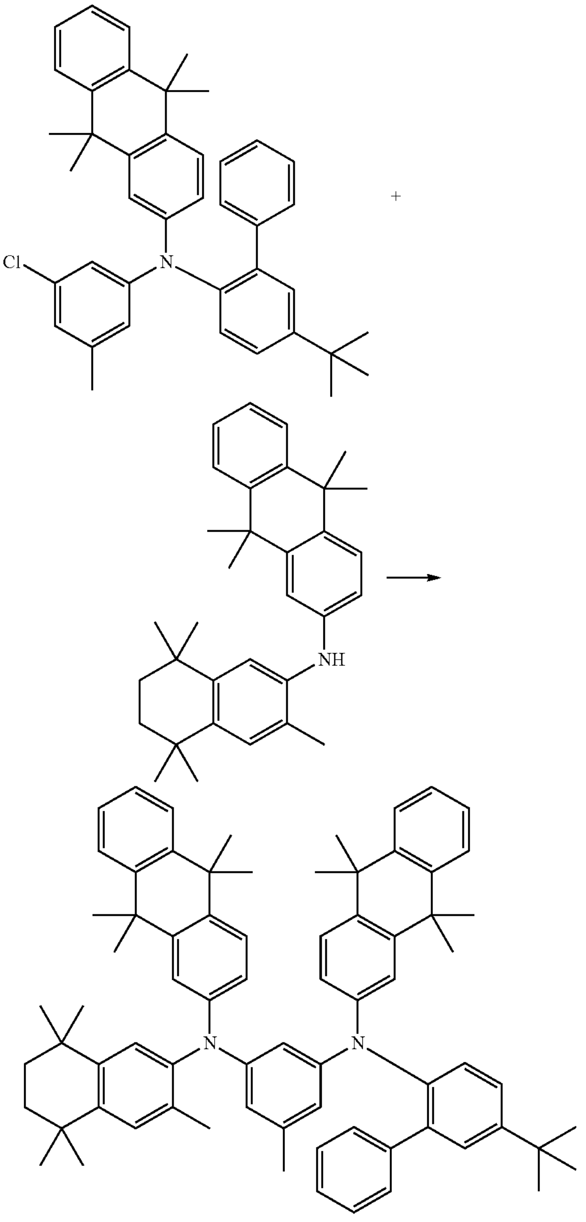

92

After 30 g of Intermediate 90, 23.2 g of 9,9,10,10-tetramethyl-N-(3,5,5,8,8-pentamethyl-5,6,7,8-tetrahydronapthalen-2-yl)-9,10-dihydroanthracen-2-amine, 9.9 g of sodium-tert-butoxide, and 0.3 g of bis(tri-tert-butylphosphine)palladium(0) were put into 450 ml of toluene under a nitrogen atmosphere, the resulting mixture was stirred under reflux for 2 hours. After the completion of the reaction, the resulting product was extracted, and then recrystallized to obtain 38 g of Intermediate 92. (Yield 74%). MS[M+H]+=1000

2) Synthesis of BD-58

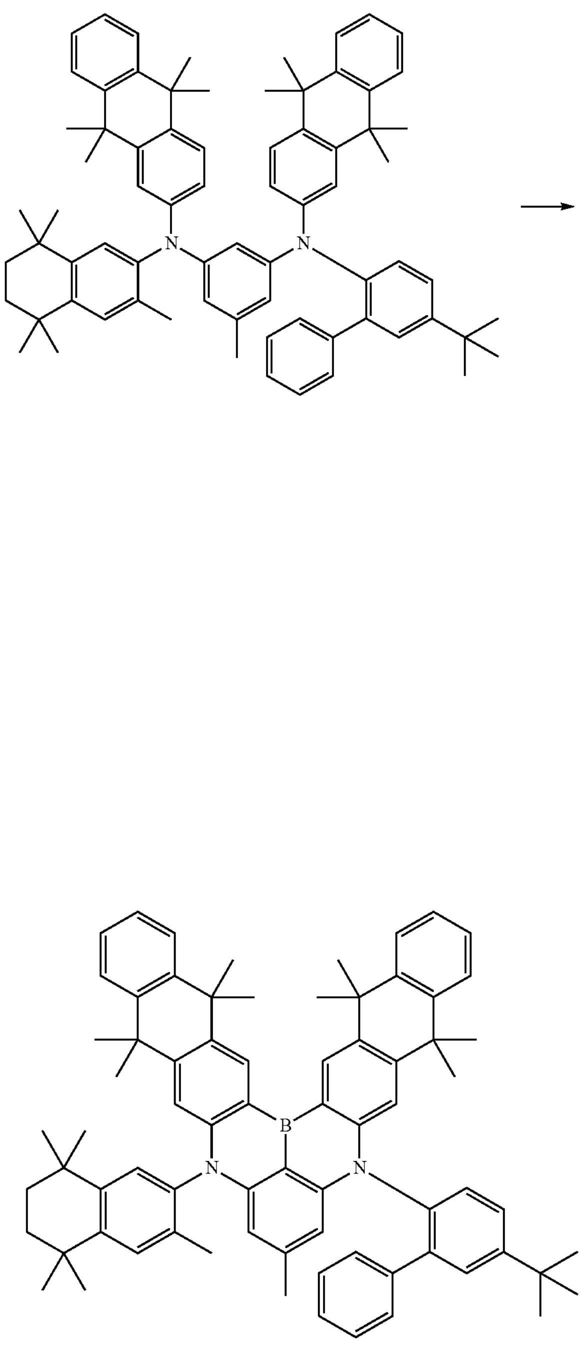

BD-58

After 25 g of Intermediate 92 and 20.1 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.6 g of BD-58 (yield 30%). MS[M+H]+=1008

Synthesis Example 118. Synthesis of BD-59

1) Synthesis of Intermediate 93

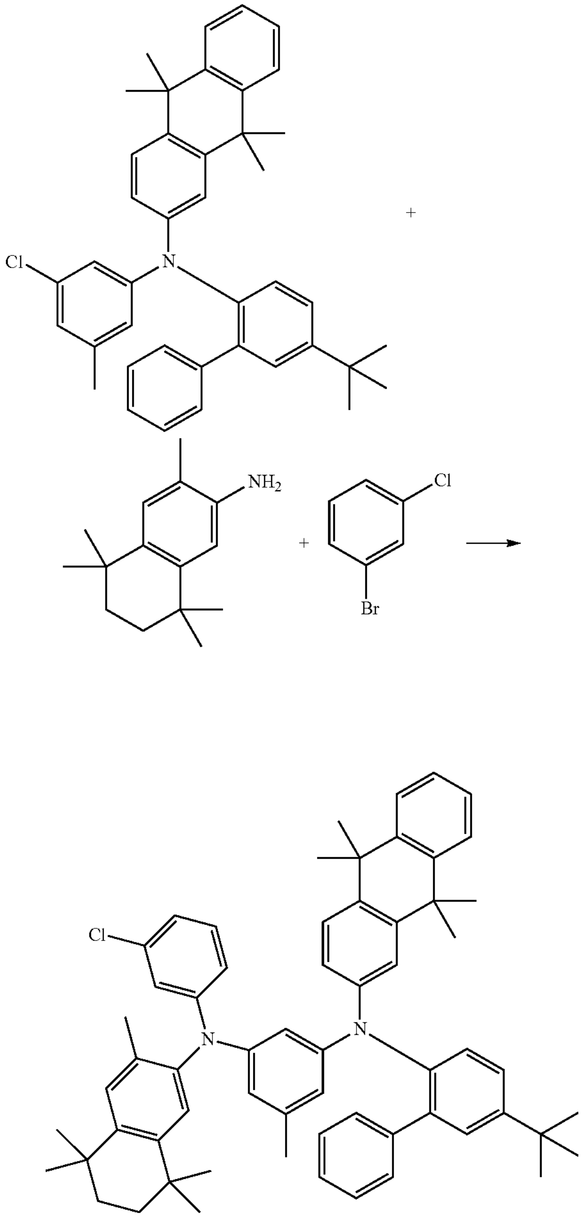

93

After 30 g of Intermediate 90, 14.9 g of 3,5,5,8,8-pentamethyl-5,6,7,8-tetrahydronaphthalen-2-amine, 19.8 g of sodium-tert-butoxide, and 0.4 g of bis(tri-tert-butylphosphine)palladium(0) were put into 600 ml of toluene under a nitrogen atmosphere, the resulting mixture was refluxed for 1 hour, whether the reaction proceeded was confirmed, and then 13.1 g of 1-bromo-3-chlorobenzene was added thereto during the reflux reaction, and the reflux reaction was performed for an additional 1 hour. After the completion of the reaction, the resulting product was extracted, and then recrystallized to obtain 44 g of Intermediate 93. (Yield 73%). MS[M+H]+=876 (Yield 77%). MS[M+H]+=585

2) Synthesis of Intermediate 94

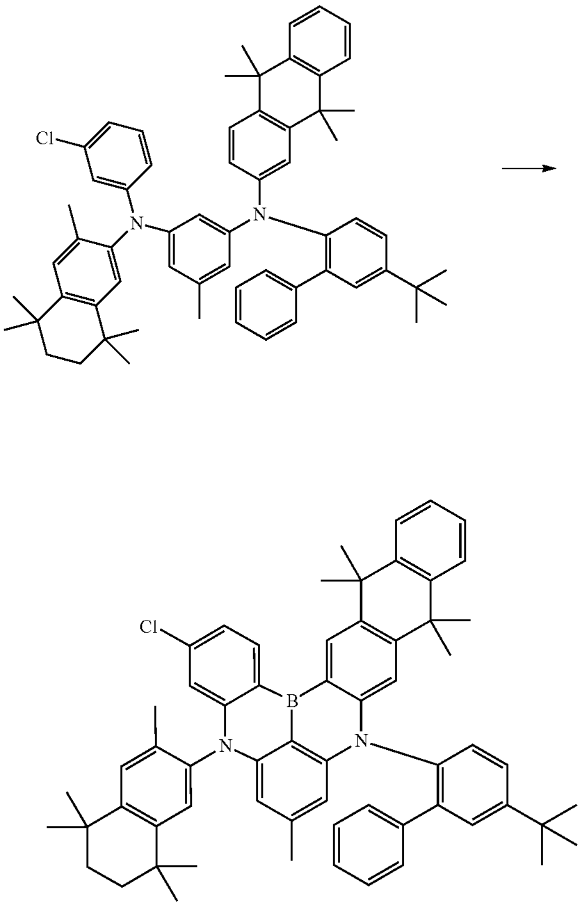

94

After 25 g of Intermediate 93 and 19 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 8.0 g of Intermediate 94 (yield 32%). MS[M+H]+=884

3) Synthesis of BD-59

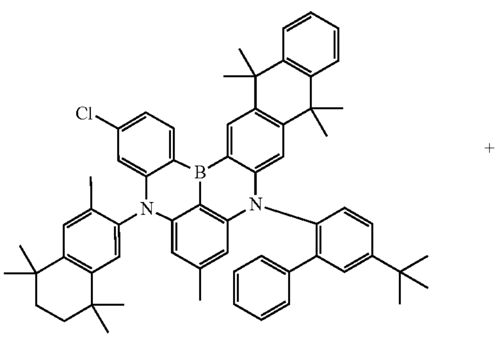

-continued

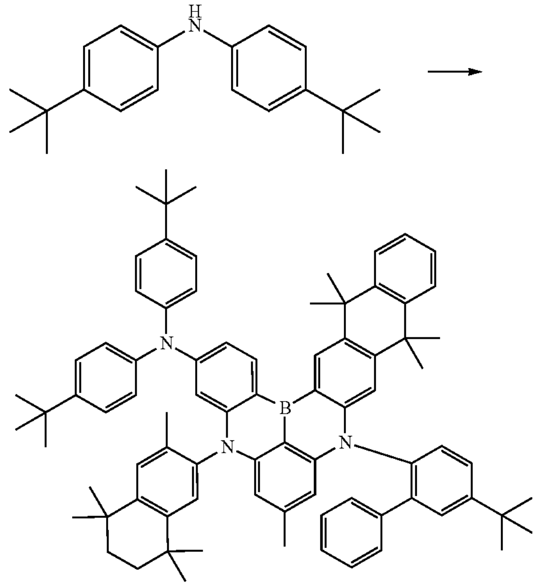

BD-59

After 7 g of Intermediate 94, 14.5 g of bis(4-(tert-butyl)phenyl)amine, 9.9 g of sodium-tert-butoxide, and 0.3 g of bis(tri-tert-butylphosphine)palladium(0) were put into 150 ml of toluene under a nitrogen atmosphere, the resulting mixture was stirred under reflux for 2 hours. After the completion of the reaction, the resulting product was extracted, and then recrystallized to obtain 6.9 g of BD-59. (Yield 77%). MS[M+H]+=1129

Synthesis Example 119. Synthesis of BD-60

1) Synthesis of Intermediate 95

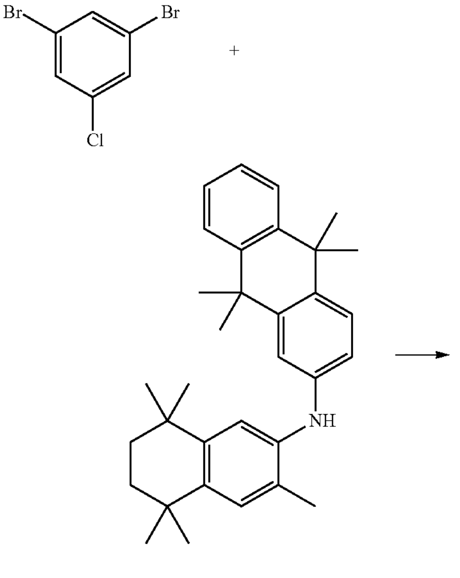

-continued

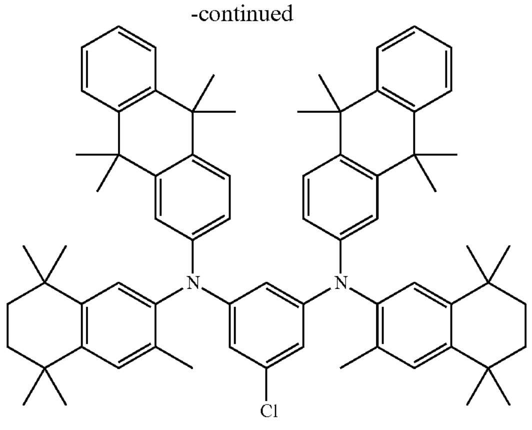

95

After 30 g of 1,3-dibromo-5-methylbenzene, 108 g of 9,9,10,10-tetramethyl-N-(3,5,5,8,8-pentamethyl-5,6,7,8-tetrahydronapthalen-2-yl)-9,10-dihydroanthracen-2-amine, 70 g of sodium-tert-butoxide, and 1.2 g of bis(tri-tert-butylphosphine)palladium(0) were put into 600 ml of toluene under a nitrogen atmosphere, the resulting mixture was stirred under reflux for 2 hours. After the completion of the reaction, the resulting product was extracted, and then recrystallized to obtain 88 g of Intermediate 95. (Yield 72%). MS[M+H]+=1012

2) Synthesis of Intermediate 96

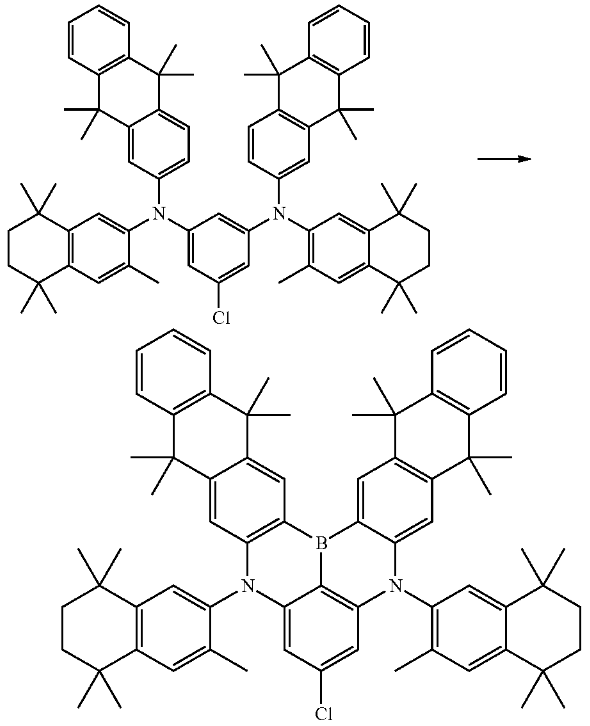

96

After 25 g of Intermediate 95 and 16.4 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.9 g of Intermediate 96 (yield 31%). MS[M+H]+=1020

3) Synthesis of BD-60

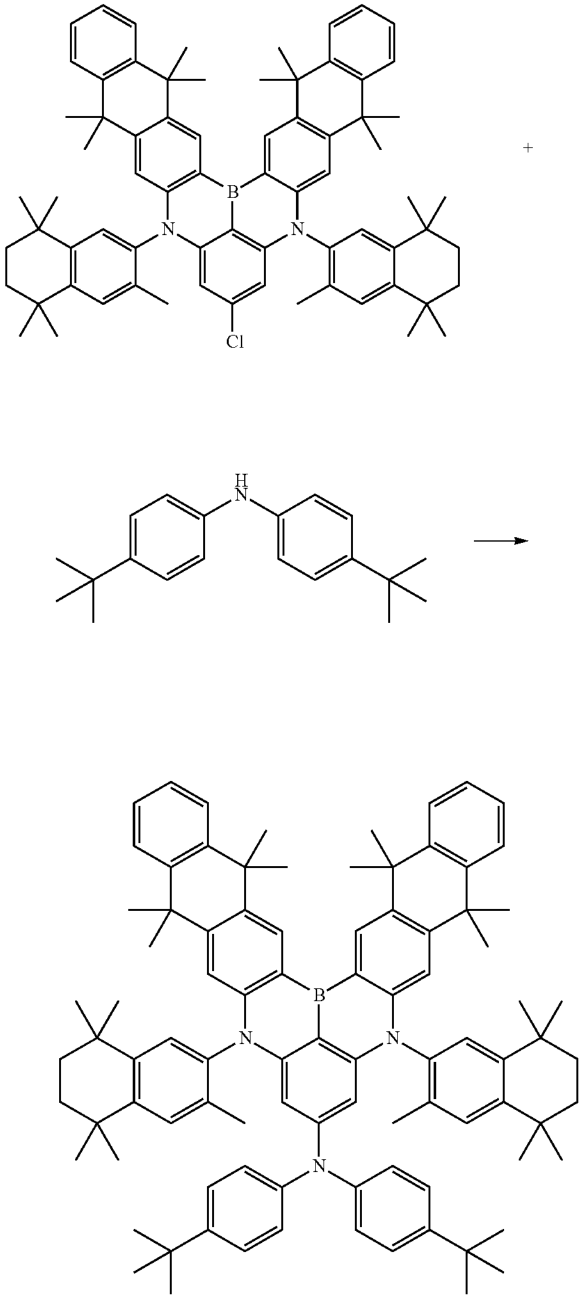

BD-60

After 7 g of Intermediate 96, 1.93 g of bis(4-(tert-butyl)phenyl)amine, 1.32 g of sodium-tert-butoxide, and 0.03 g of bis(tri-tert-butylphosphine)palladium(0) were put into 80 ml of xylene under a nitrogen atmosphere, the resulting mixture was stirred under refluxed for 5 hours.

After the completion of the reaction, the resulting product was extracted, and then recrystallized to obtain 6.9 g of BD-60. (Yield 79%). MS[M+H]+=1265

Synthesis Example 120. Synthesis of BD-61

1) Synthesis of BD-61

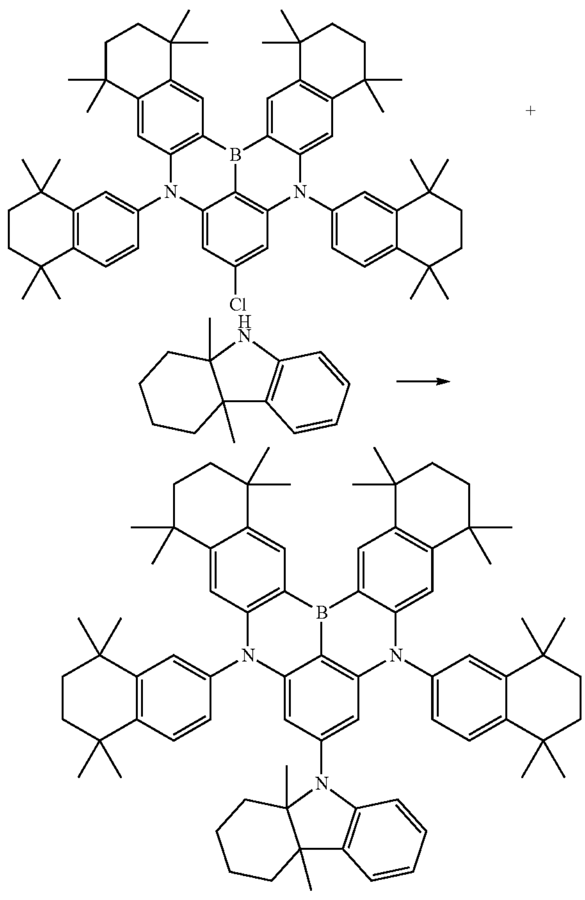

BD-61

After 7 g of Intermediate 58, 1.93 g of 4a,9a-dimethyl-2,3,4,4a,9,9a-hexahydro-1H-carbazole, 1.52 g of sodium-tert-butoxide, and 0.04 g of bis(tri-tert-butylphosphine)palladium(0) were put into 80 ml of xylene under a nitrogen atmosphere, the resulting mixture was stirred under reflux for 5 hours. After the completion of the reaction, the resulting product was extracted, and then recrystallized to obtain 6.5 g of BD-61. (Yield 78%). MS[M+H]+=1061

Synthesis Example 121. Synthesis of BD-62

1) Synthesis of BD-62

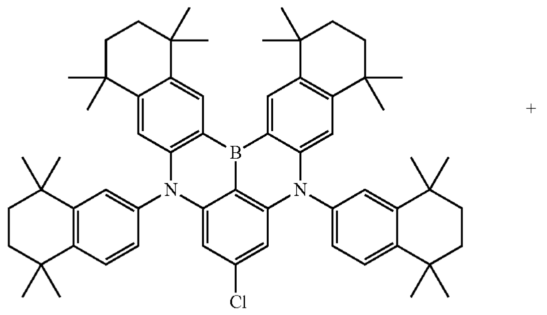

-continued

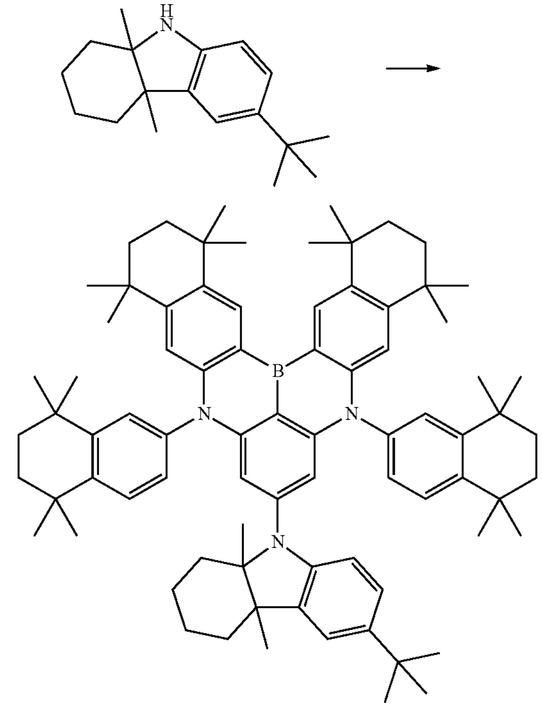

BD-62

After 7 g of Intermediate 58, 2.05 g of 6-(tert-butyl)-4a,9a-dimethyl-2,3,4,4a,9,9a-hexahydro-1H-carbazole, 1.52 g of sodium-tert-butoxide, and 0.04 g of bis(tri-tert-butylphosphine)palladium(0) were put into 80 ml of xylene under a nitrogen atmosphere, the resulting mixture was stirred under reflux for 5 hour. After the completion of the reaction, the resulting product was extracted, and then recrystallized to obtain 6.7 g of BD-62. (Yield 77%). MS[M+H]+=1117

Synthesis Example 122. Synthesis of BD-63

1) Synthesis of Compound BD-63

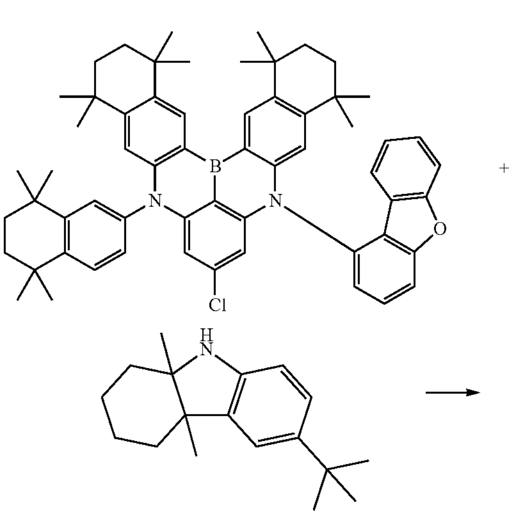

-continued

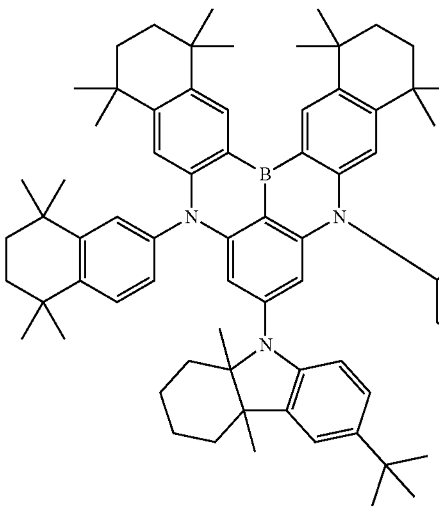

BD-63

After 7 g of Intermediate 71, 2.06 g of 6-(tert-butyl)-4a, 9a-dimethyl-2,3,4,4a,9,9a-hexahydro-1H-carbazole, 1.55 g of sodium-tert-butoxide, and 0.04 g of bis(tri-tert-butylphosphine)palladium(0) were put into 80 ml of xylene under a nitrogen atmosphere, the resulting mixture was stirred under reflux for 5 hours. After the completion of the reaction, the resulting product was extracted, and then recrystallized to obtain 6.9 g of BD-63. (Yield 79%). MS[M+H]+=1097

Synthesis Example 123. Synthesis of BD-64

1) Synthesis of Intermediate 97

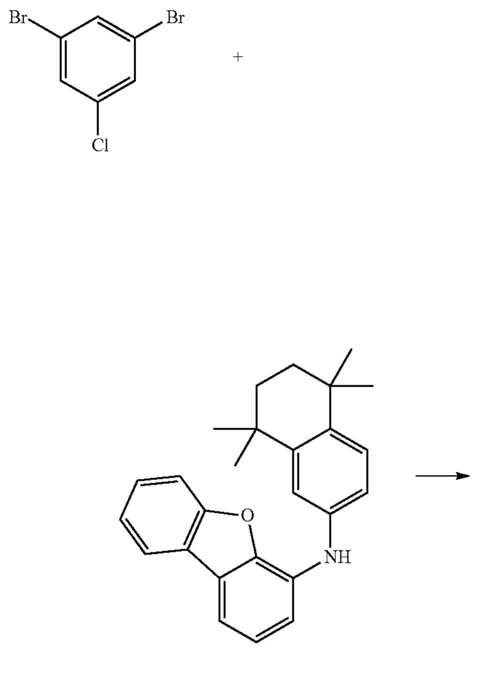

-continued

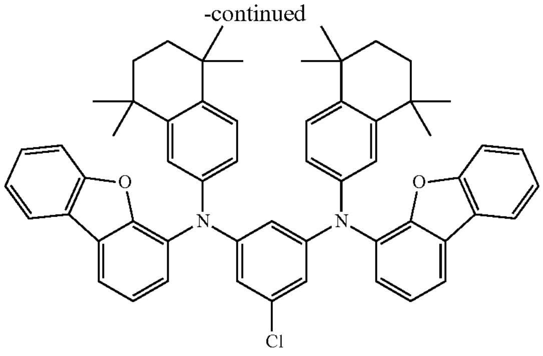

97

After 30 g of 1,3-dibromo-5-chlorobenzene, 82 g of N-(5,5,8,8-tetramethyl-5,6,7,8-tetrahydronaphthalen-2-yl) dibenzo[b,d]furan-4-amine, 64 g of sodium-tert-butoxide, and 0.6 g of bis(tri-tert-butylphosphine)palladium(0) were put into 600 ml of toluene under a nitrogen atmosphere, the resulting mixture was stirred under reflux for 2 hours. After the completion of the reaction, the resulting product was extracted, and then recrystallized to obtain 69 g of Intermediate 97. (Yield 73%). MS[M+H]+=848

2) Synthesis of Intermediate 98

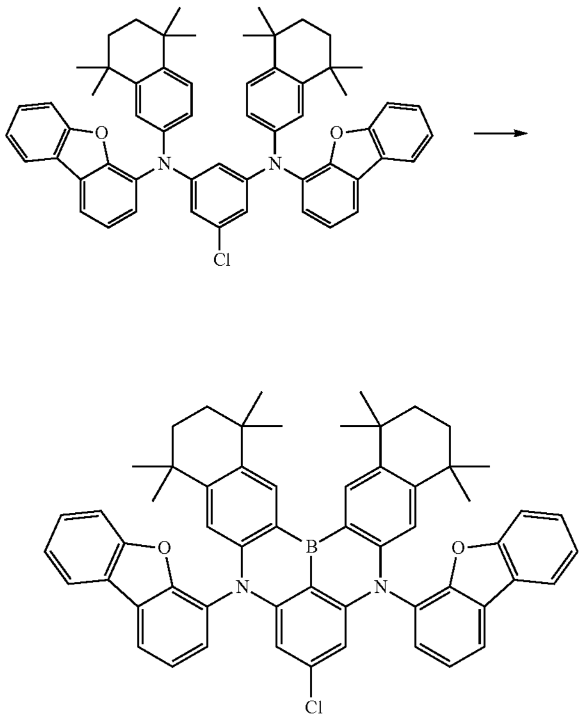

98

After 25 g of Intermediate 97 and 19.6 g of boron triiodide were put into 250 ml of 1,2-dichlorobenzene under a nitrogen atmosphere, the resulting mixture was stirred at 160° C. for 4 hours. After the completion of the reaction, the resulting product was extracted, and then recrystallized to obtain 7.2 g of Intermediate 98 (yield 29%). MS[M+H]+=856

3) Synthesis of BD-64

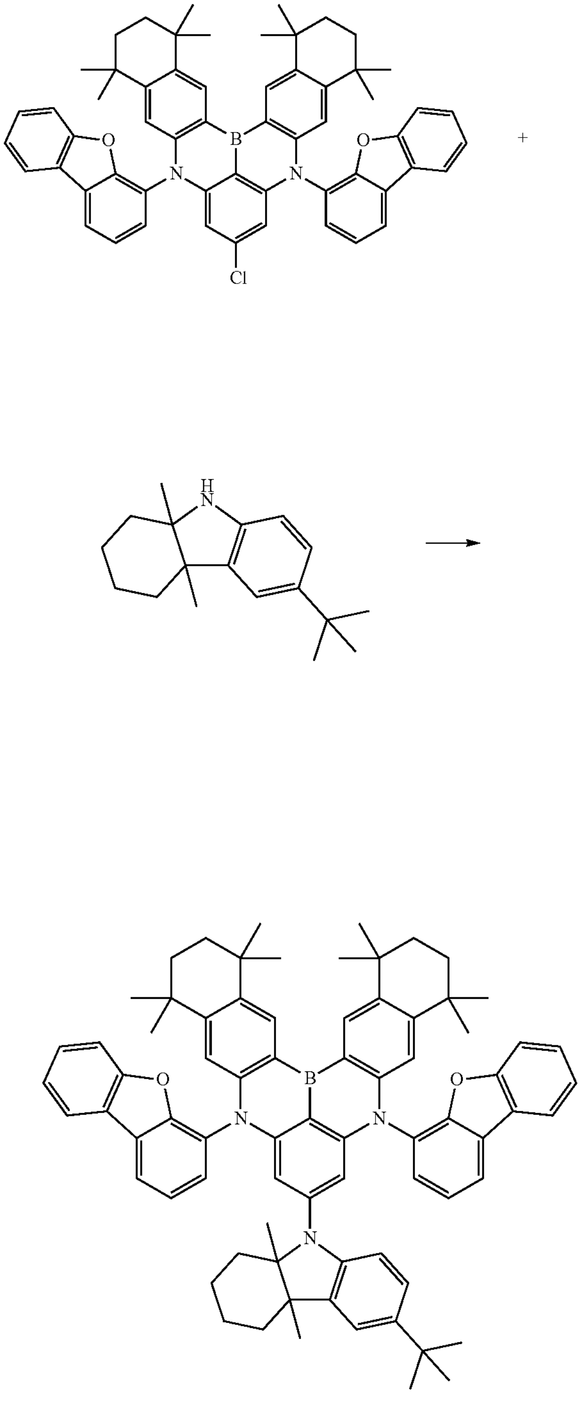

BD-64

After 7 g of Intermediate 98, 2.1 g of 6-(tert-butyl)-4a,9a-dimethyl-2,3,4,4a,9,9a-hexahydro-1H-carbazole, 1.6 g of sodium-tert-butoxide, and 0.04 g of bis(tri-tert-butylphosphine)palladium(0) were put into 80 ml of xylene under a nitrogen atmosphere, the resulting mixture was stirred under reflux for 5 hours. After the completion of the reaction, the resulting product was extracted, and then recrystallized to obtain 7.0 g of BD-64. (Yield 79%). MS[M+H]+=1077

Synthesis Example 124. Synthesis of BD-65

1) Synthesis of BD-65

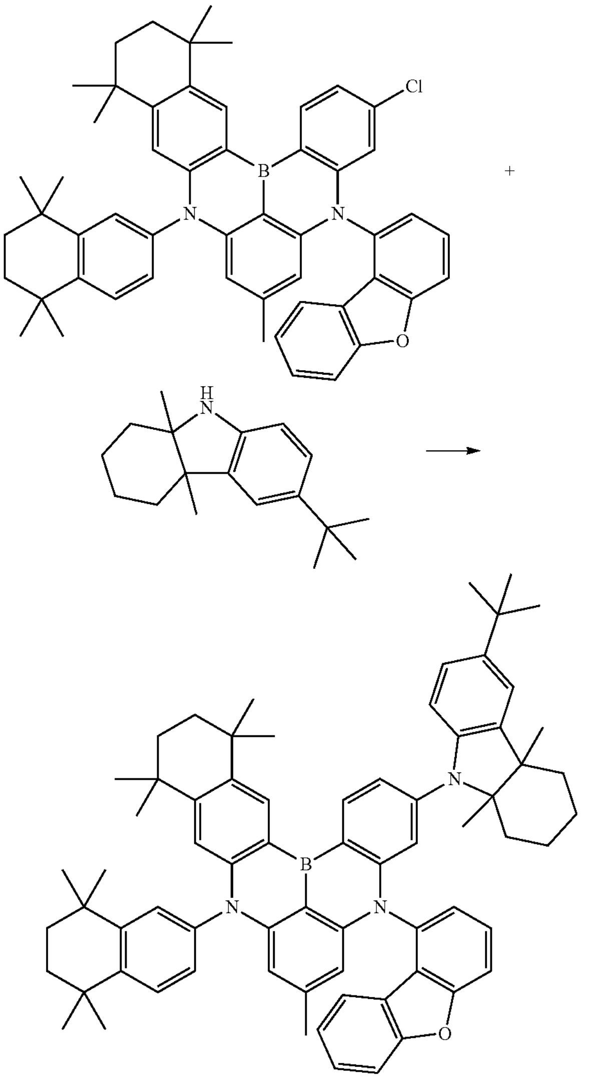

BD-65

After 7 g of Intermediate 67, 2.31 g of 6-(tert-butyl)-4a,9a-dimethyl-2,3,4,4a,9,9a-hexahydro-1H-carbazole, 1.8 g of sodium-tert-butoxide, and 0.05 g of bis(tri-tert-butylphosphine)palladium(0) were put into 80 ml of xylene under a nitrogen atmosphere, the resulting mixture was stirred under reflux for 5 hours. After the completion of the reaction, the resulting product was extracted, and then recrystallized to obtain 7.1 g of BD-65. (Yield 79%). MS[M+H]+=1001

Experimental Example 1: Device Example

Example 1

A glass substrate thinly coated with indium tin oxide (ITO) to have a thickness of 1,400 Å was put into distilled water in which a detergent was dissolved, and ultrasonically washed. In this case, a product manufactured by Fischer Co., was used as the detergent, and distilled water, which had been filtered twice with a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted by using isopropyl alcohol, acetone, and methanol solvents, and the resulting product was dried and then transported to a plasma washing machine. Furthermore, the substrate was cleaned by using oxygen plasma for 5 minutes, and then was transported to a vacuum deposition machine.

The following HI-A and LG-101 were thermally vacuum deposited to have a thickness of 645 Å and 55 Å, respectively, on the ITO transparent electrode prepared as described, thereby forming first and second hole injection layers. The following HT-A was vacuum deposited to have a thickness of 615 Å on the hole injection layer, thereby forming a hole transport layer. The following HT-B was vacuum deposited to have a thickness of 35 Å on the hole transport layer, thereby forming an electron blocking layer.

Subsequently, the following compound BD-1 as a blue light emitting dopant was vacuum deposited at 4 wt % based on a total weight of the light emitting layer and the following BH-1 as a host was vacuum deposited at 96 wt % based on a total weight of the light emitting layer to a thickness of 190 Å on the electron blocking layer, thereby forming a light emitting layer.

Next, the following compound ET-A as a first electron transport layer was vacuum deposited to have a thickness of 50 Å on the light emitting layer, and subsequently, the following ET-B and LiQ were vacuum deposited at a weight ratio of 1:1, thereby forming a second electron transport layer having a thickness of 360 Å. LiQ was vacuum deposited to have a thickness of 5 Å on the second electron transport layer, thereby forming an electron injection layer. Aluminum and silver were deposited at a weight ratio of 10:1 to have a thickness of 220 Å on the electron injection layer, and aluminum was deposited to have a thickness of 1,000 Å thereon, thereby forming a cathode.

In the aforementioned procedure, the deposition rates of the organic material were maintained at 0.4 to 0.9 Å/sec, the deposition rate of aluminum of the cathode was maintained at 2 Å/sec, and the degree of vacuum during the deposition was maintained at $1\times10^{-7}$ to $5\times10^{-8}$ torr, thereby manufacturing an organic light emitting device.

HI-A

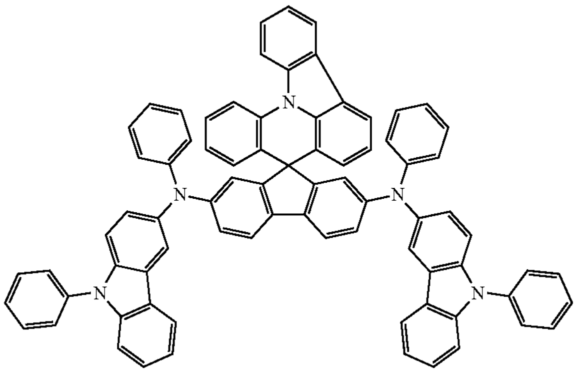

-continued

LG-101

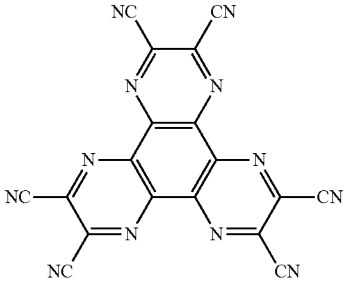

HT-A

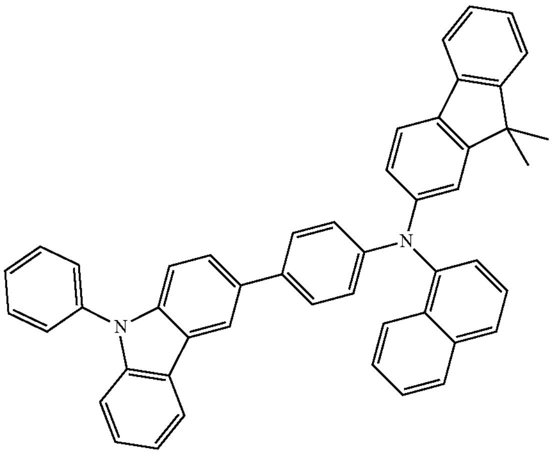

HT-B

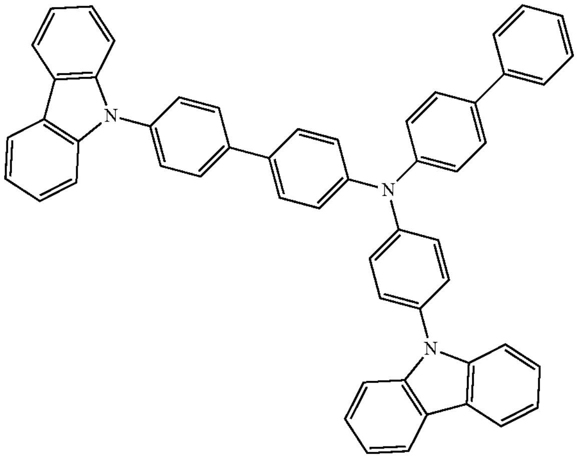

-continued

BH-1

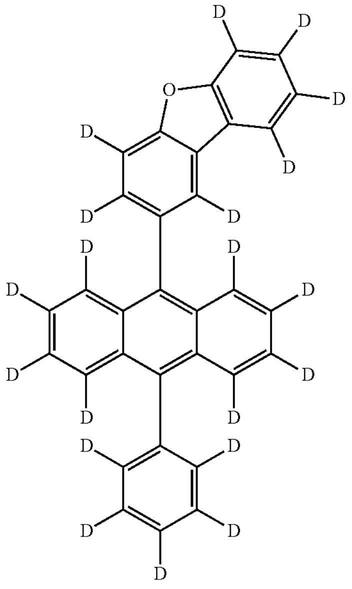

BD-1

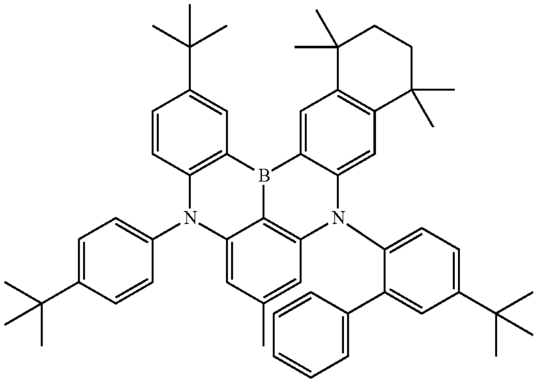

ET-A

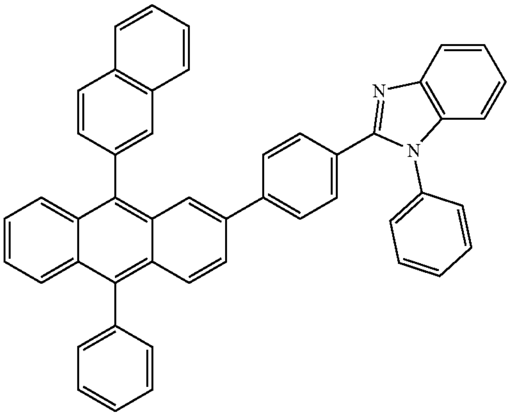

-continued

ET-B

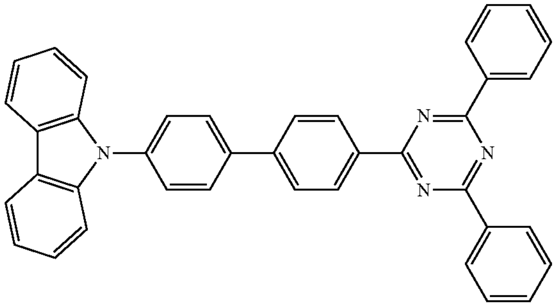

LiQ

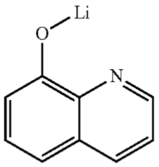

Examples 2 to 92 and 94 to 122

Organic light emitting devices of Examples 2 to 92 and 94 to 122 were each manufactured in the same manner as in Example 1, except that in Example 1, compounds described in the following Table 1 were used as dopants of the light emitting layer instead of Compound BD-1, and compounds described in the following Table 1 were used as host materials instead of BH-1.

BH-1

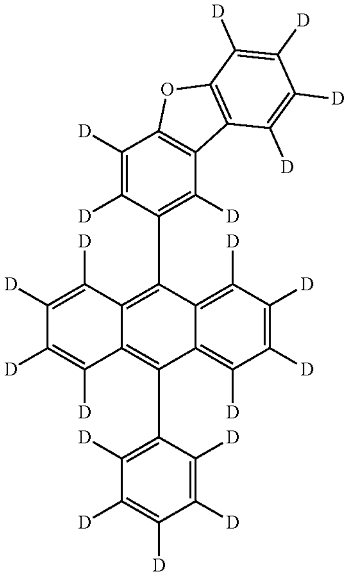

-continued
BH-2
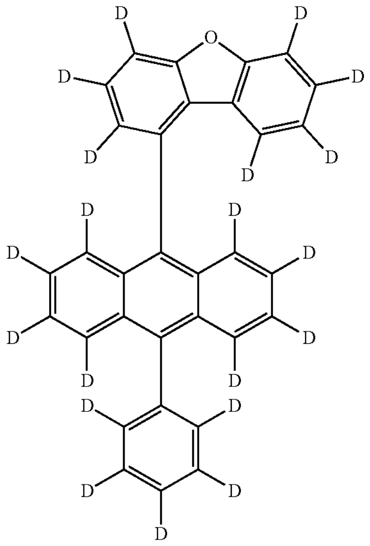
BH-3
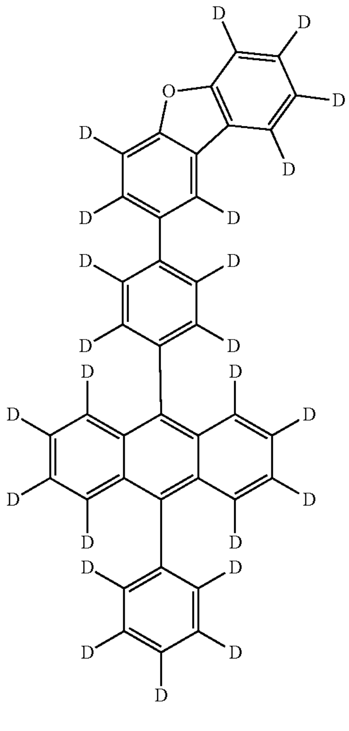
-continued
BH-4
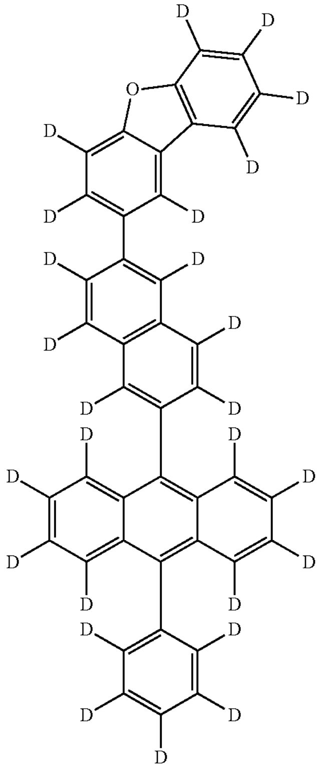
BH-5
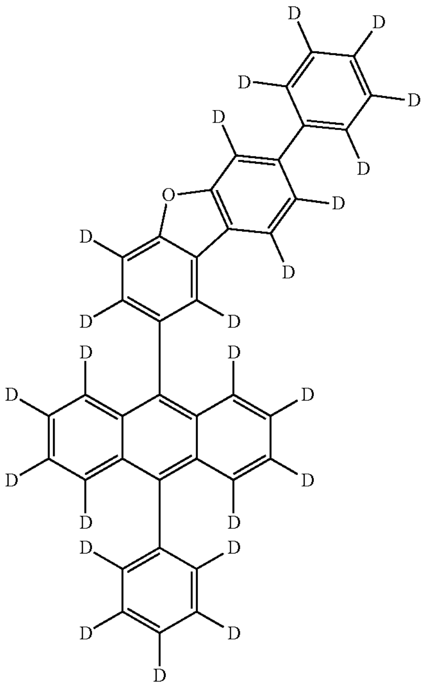

-continued
BH-6
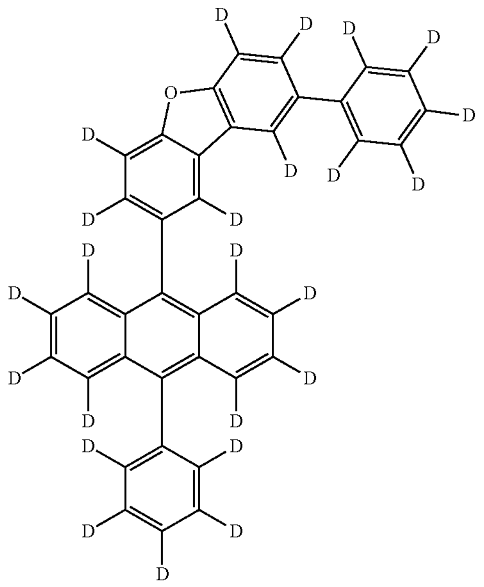
BH-8
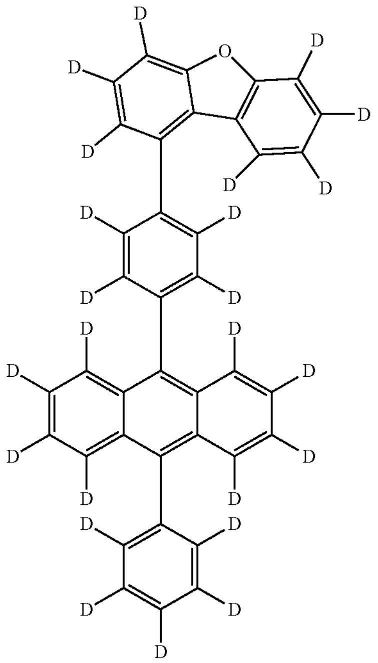
-continued
BH-9
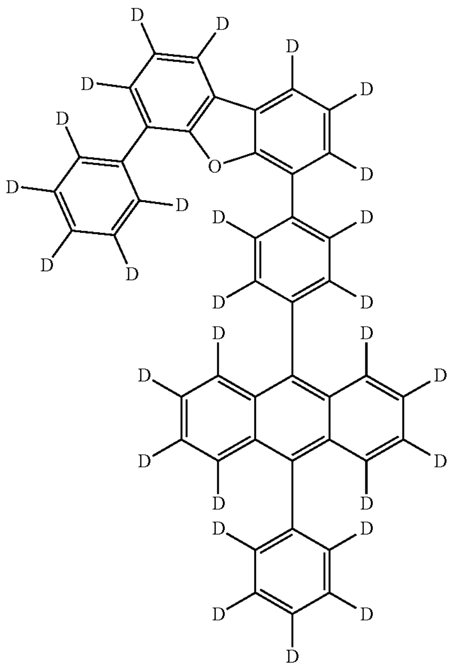
BH-10
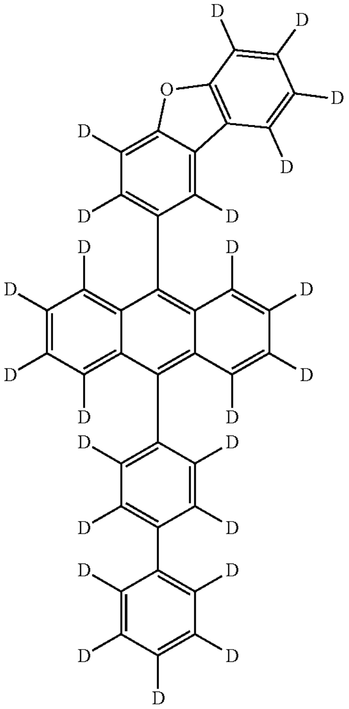

BH-11
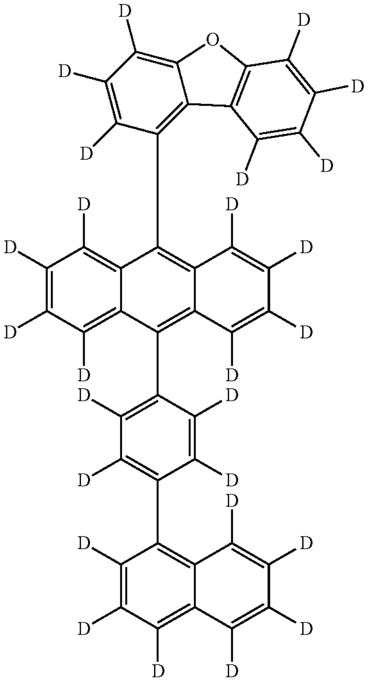
BH-12
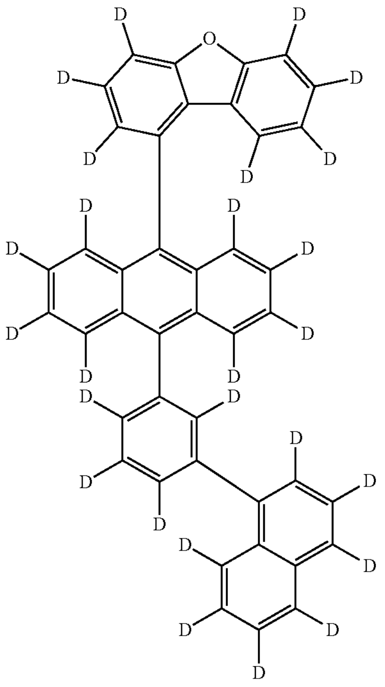
BH-13
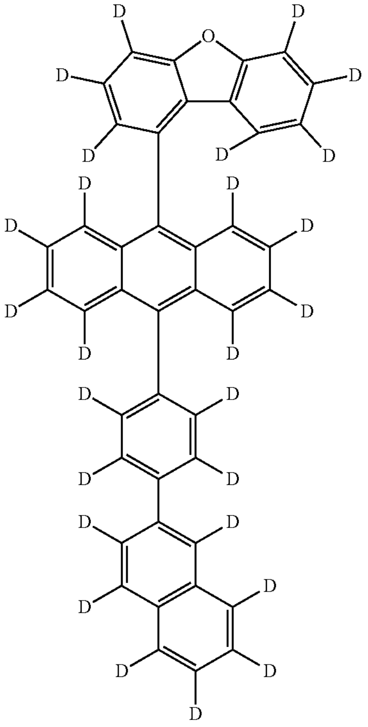
BH-14
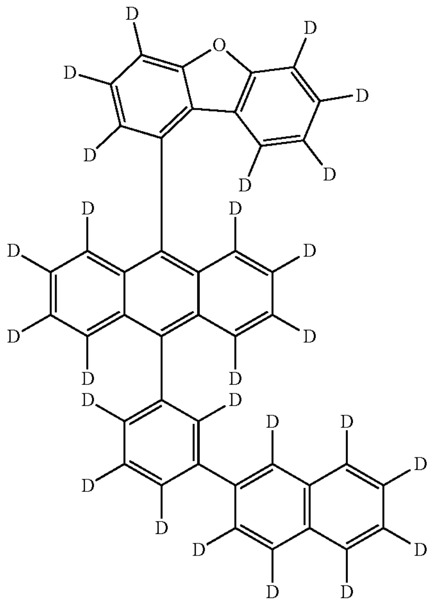

-continued
BH-15
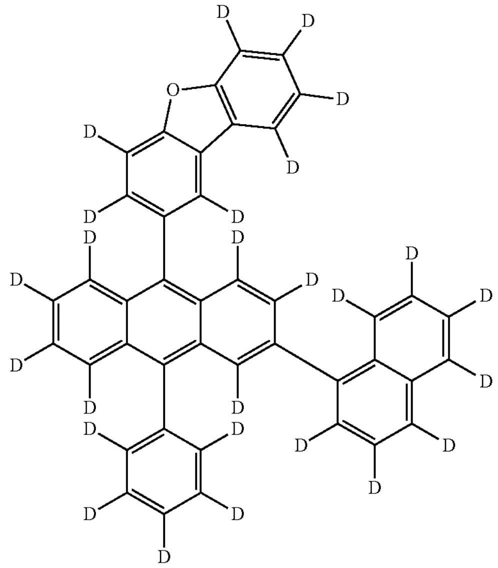
BH-16
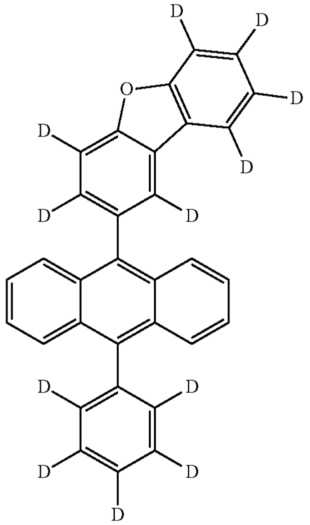
BH-17
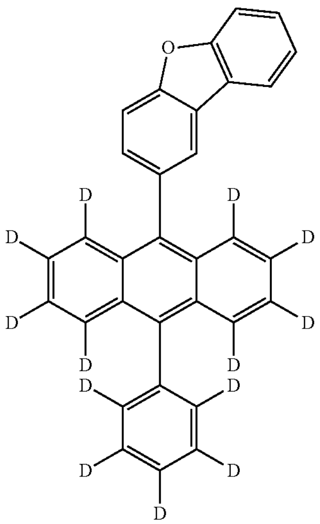
BH-18
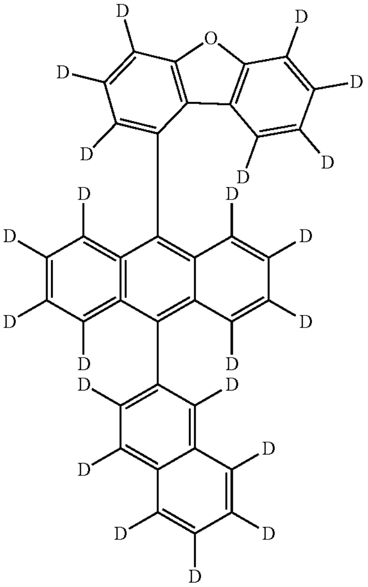
BH-19
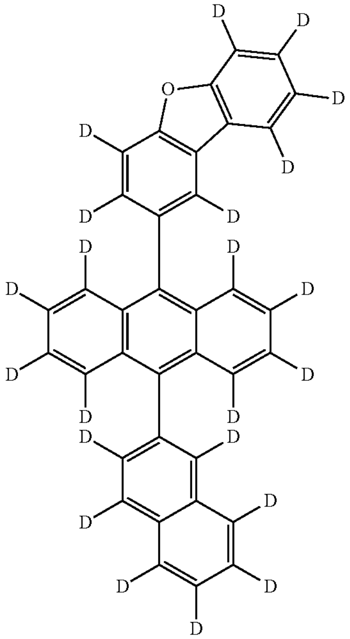

BH-20
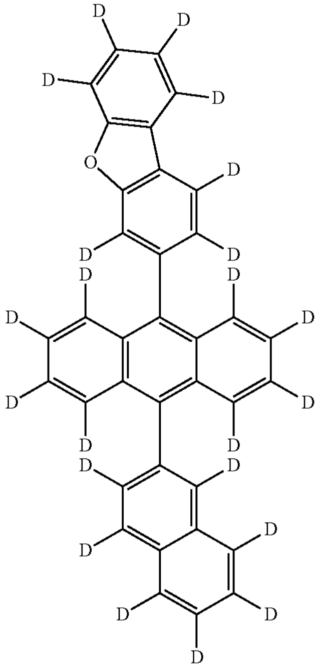
BH-21
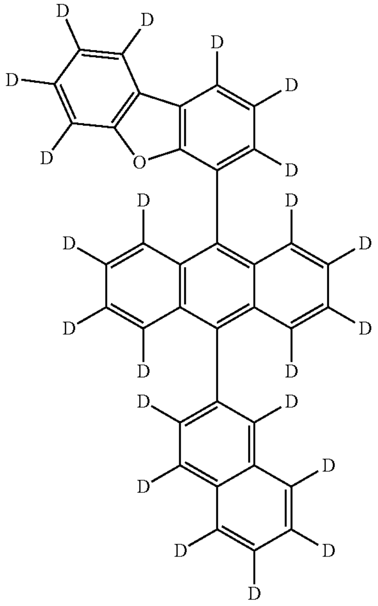
BH-22
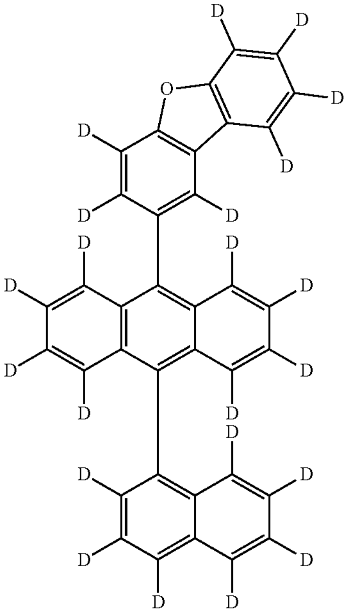
BH-23
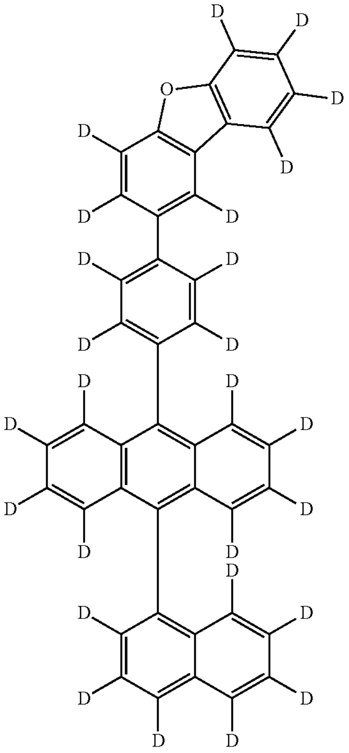

-continued
BH-24
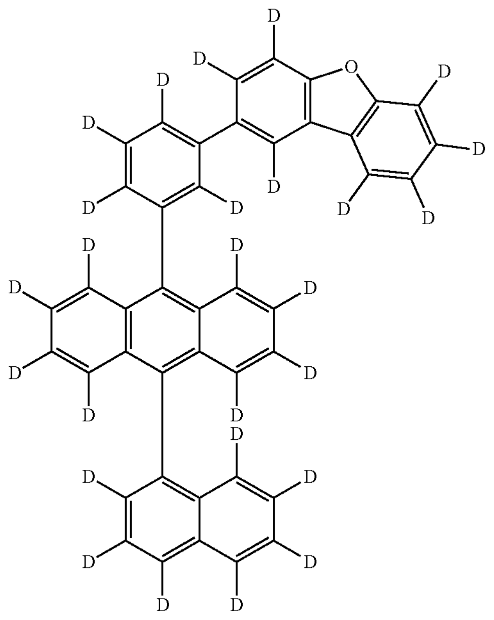
BH-25
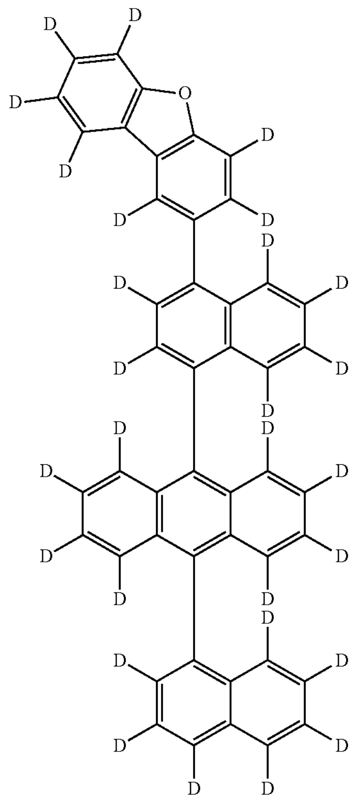
-continued
BH-26
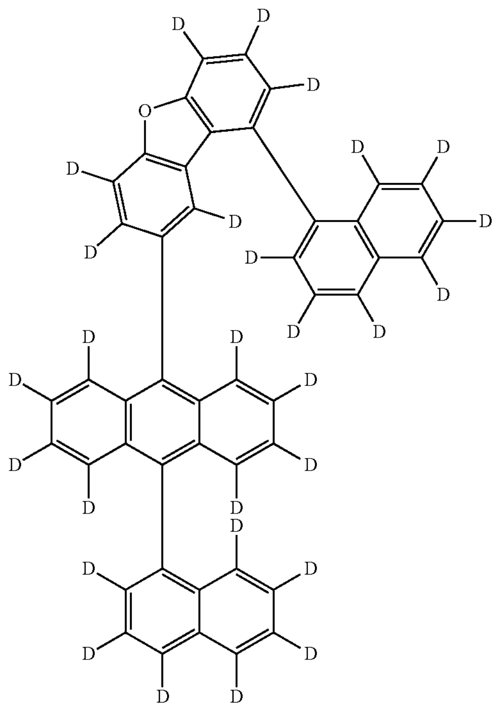
BH-27
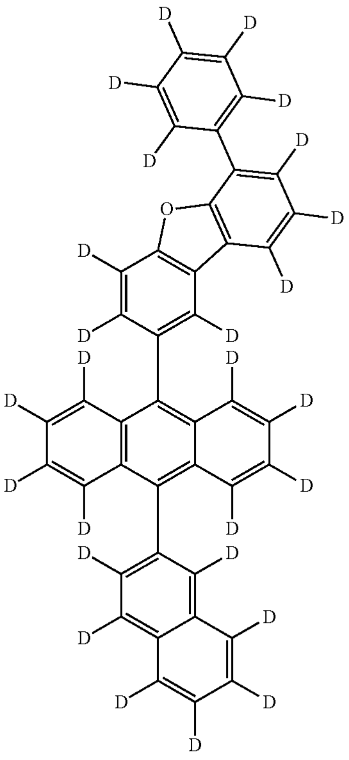

-continued
BH-28
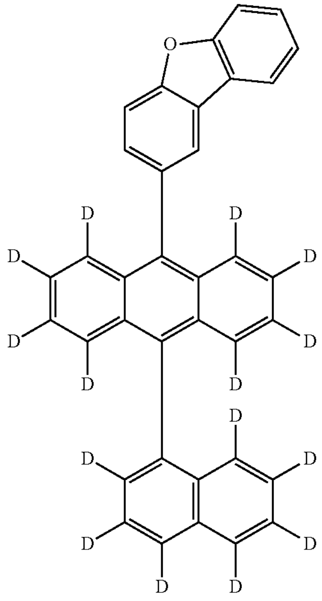
BH-29
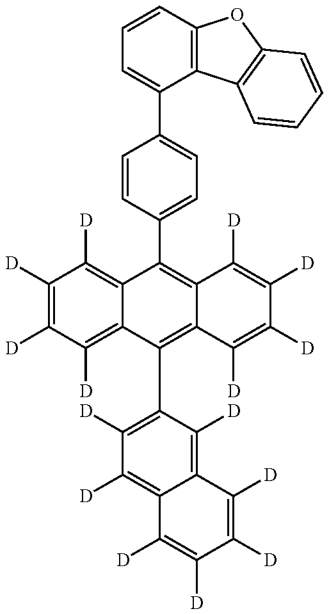
-continued
BH-31
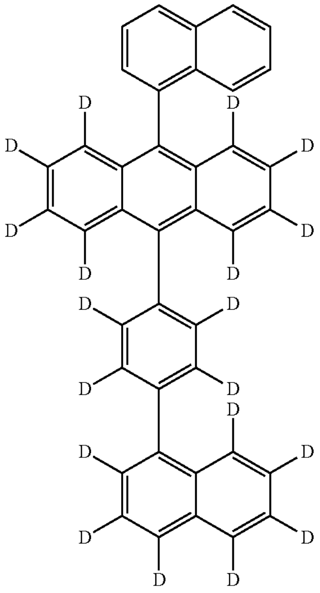
BH-32
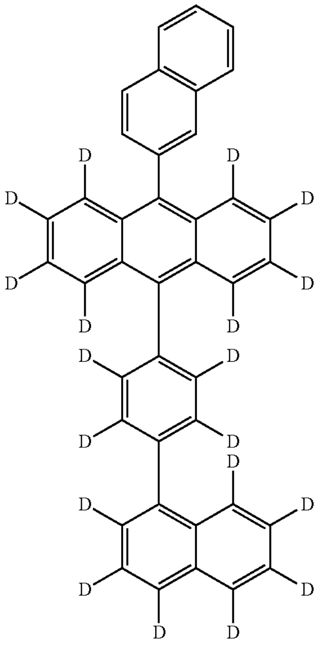

-continued
BH-33
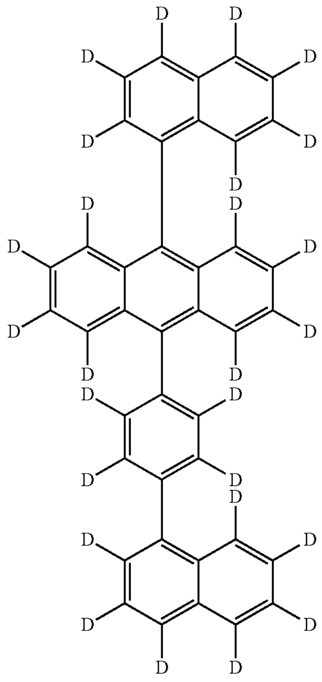
BH-34
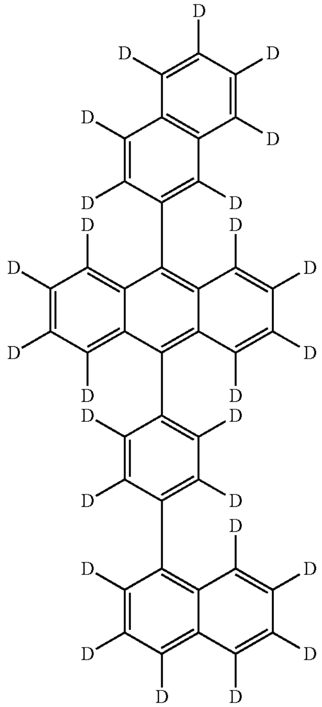
-continued
BH-35
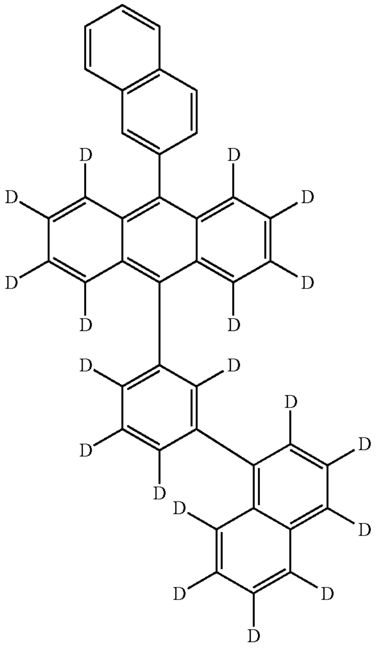
BH-36
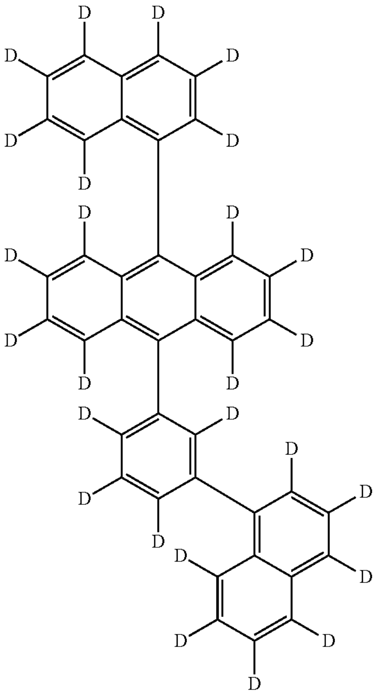

-continued
BH-37
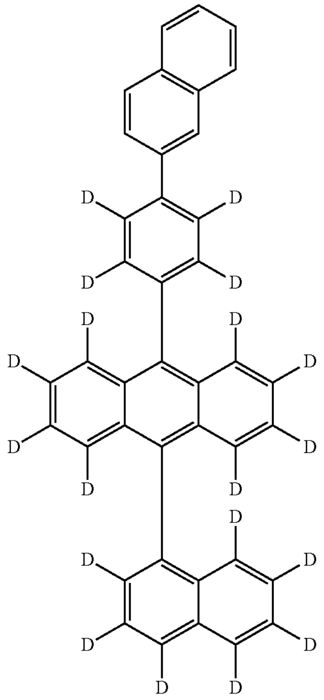
BH-38
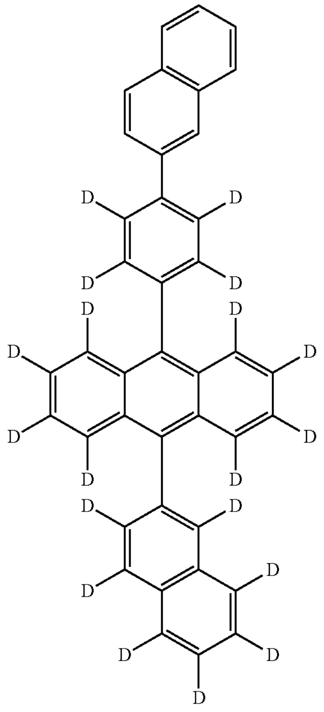
-continued
BH-39
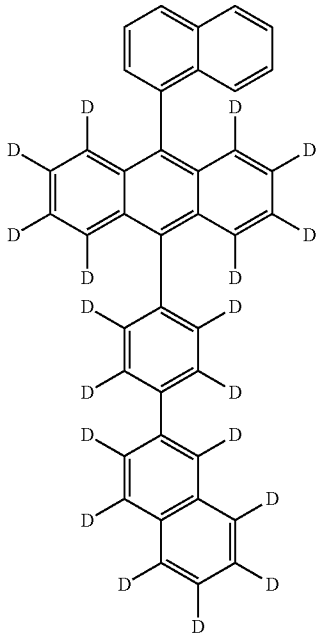
BH-40
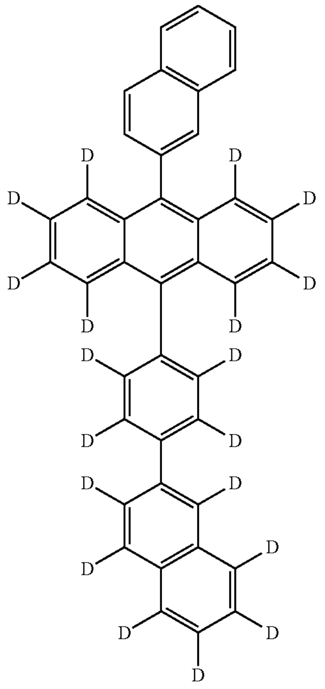

-continued
BH-41
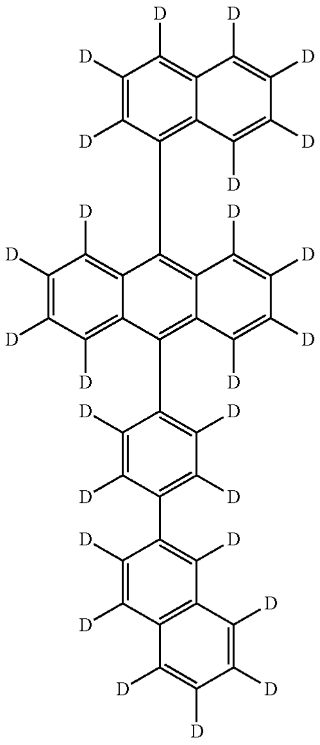
BH-42
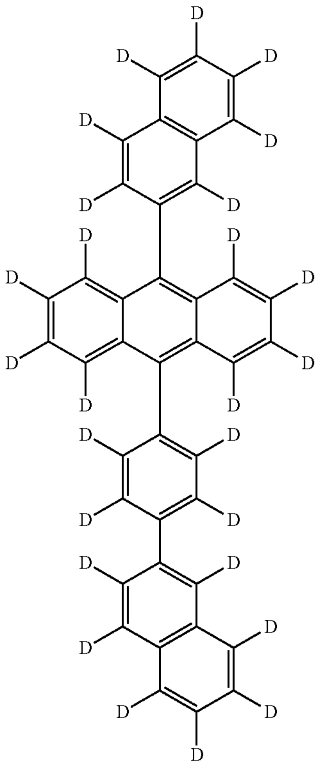
-continued
BH-43
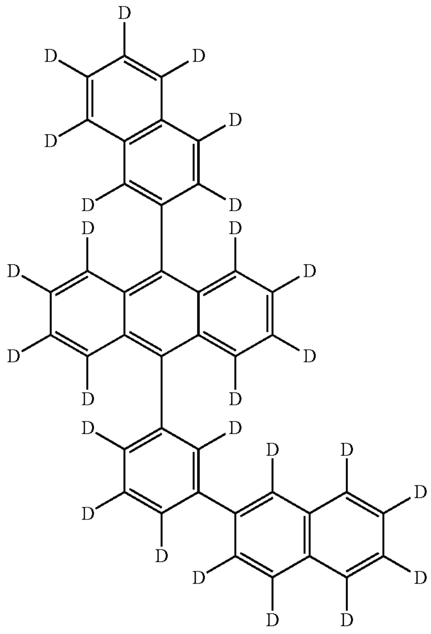
BH-44
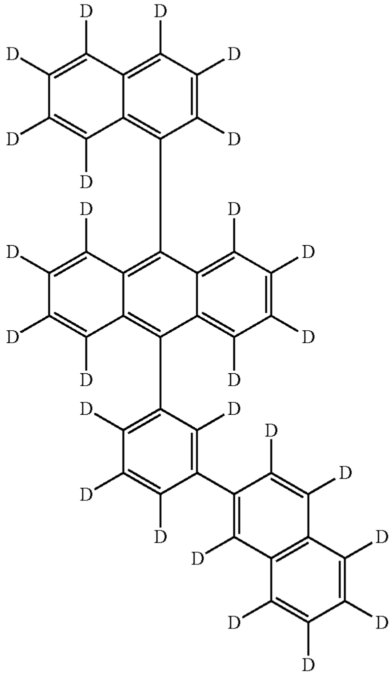

-continued
BH-45
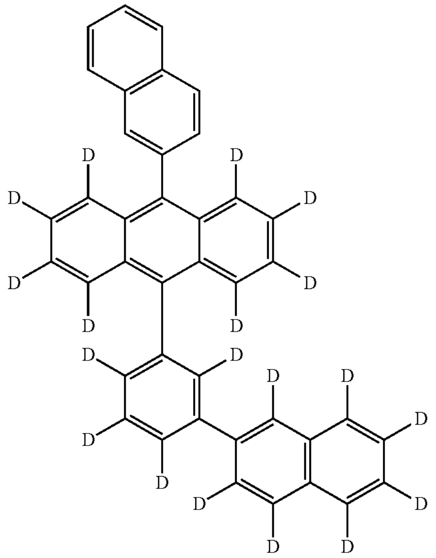
BH-46
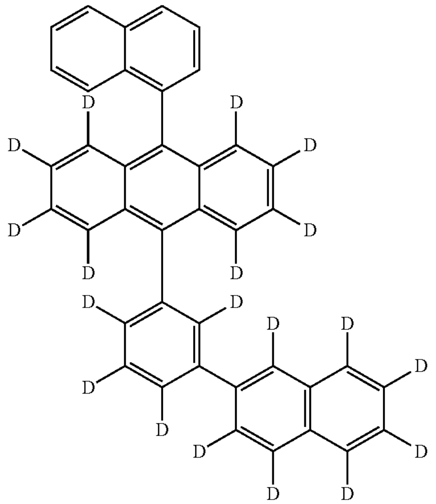
BH-47
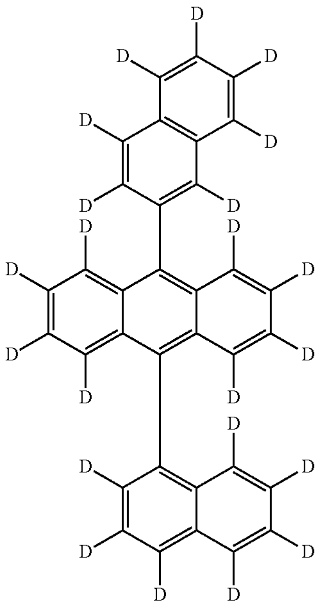
-continued
BH-48
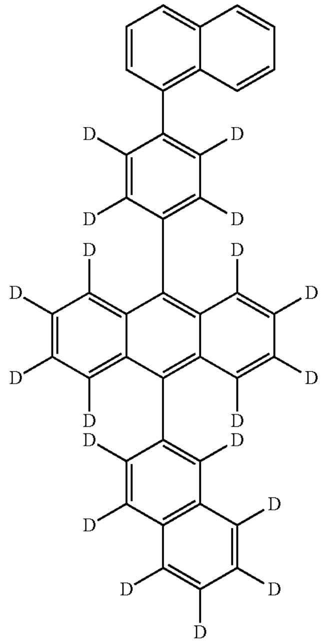
BH-49
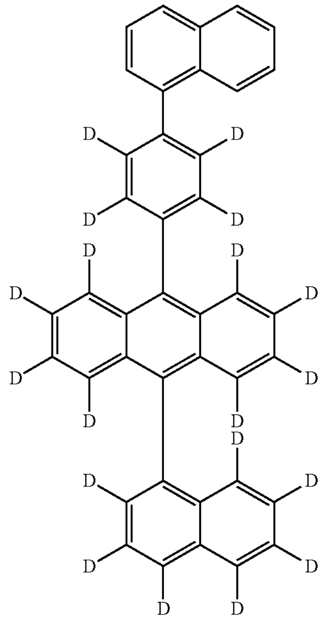

BH-50
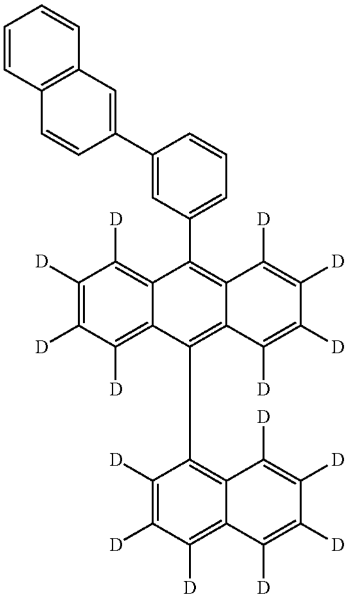
BH-51
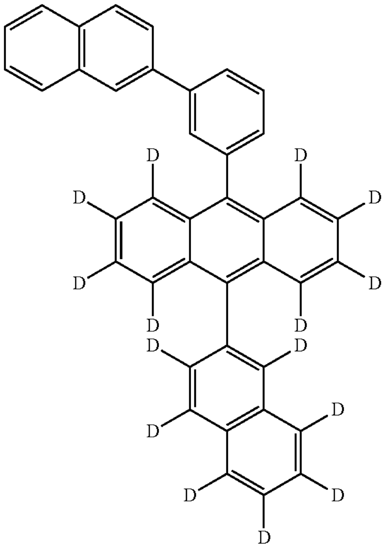
BH-52
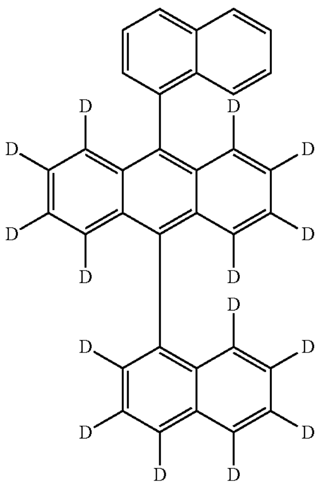
BH-53
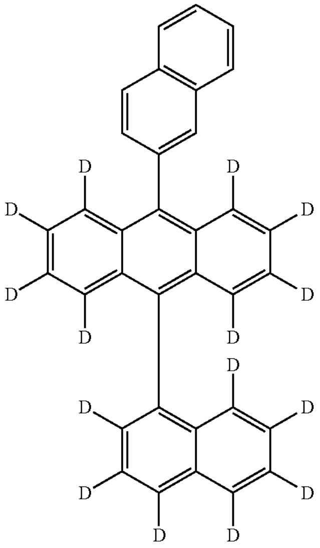
BH-54
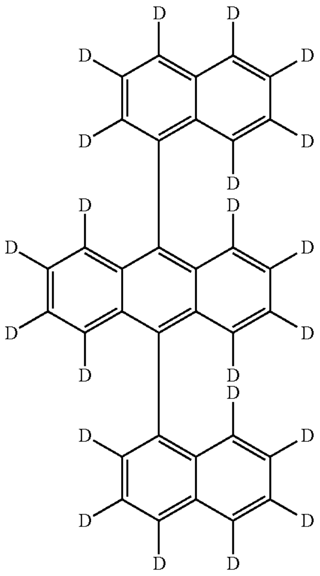
BH-55
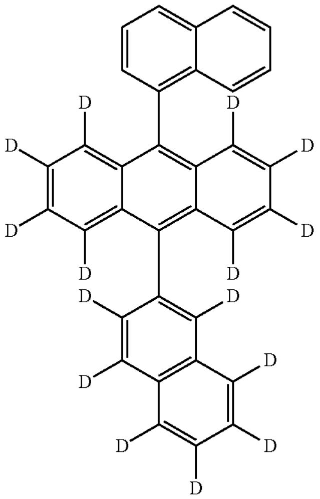

-continued
BH-56
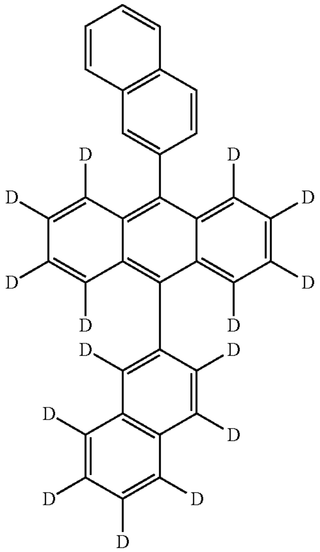
BH-57
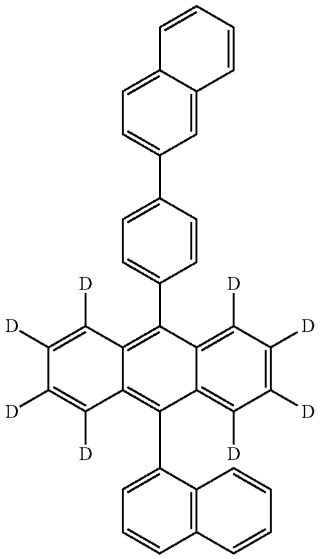
-continued
BH-58
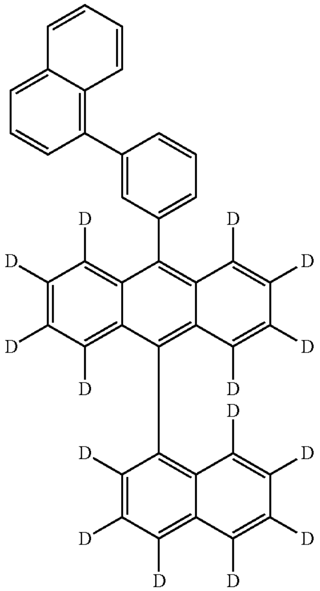
BH-59
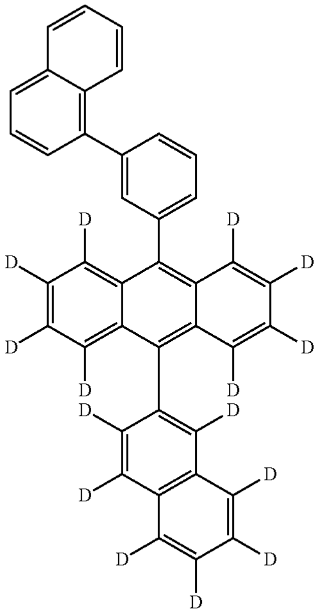
BD-1
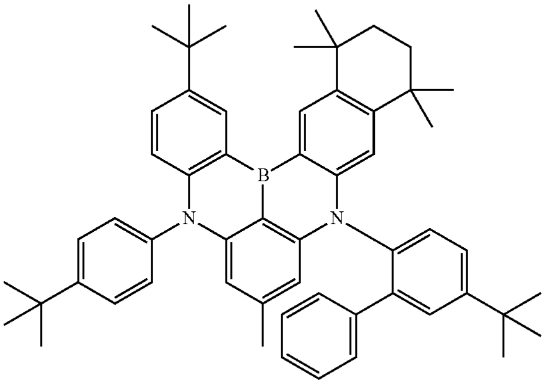

-continued
BD-2
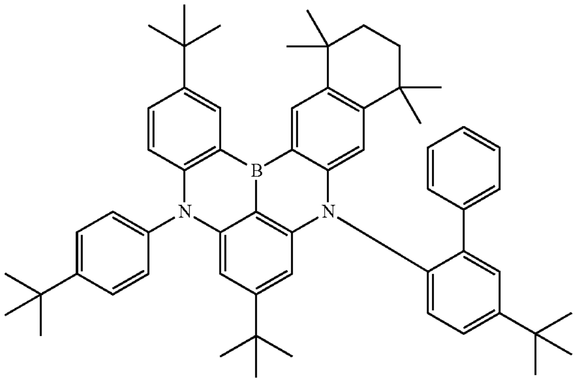
BD-3
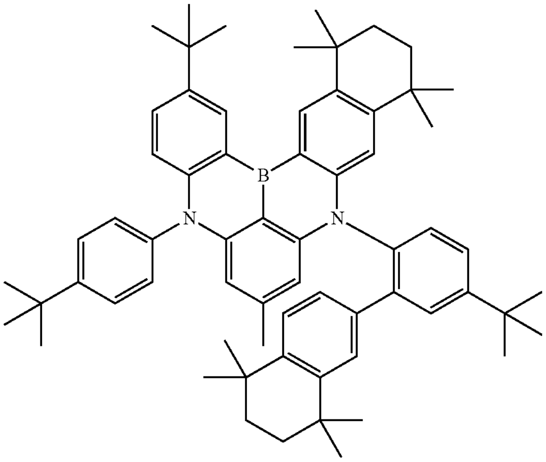
BD-4
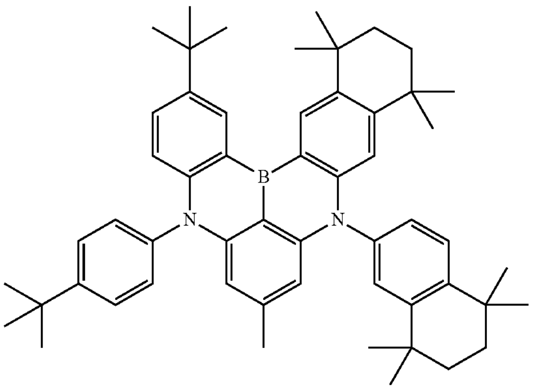
-continued
BD-5
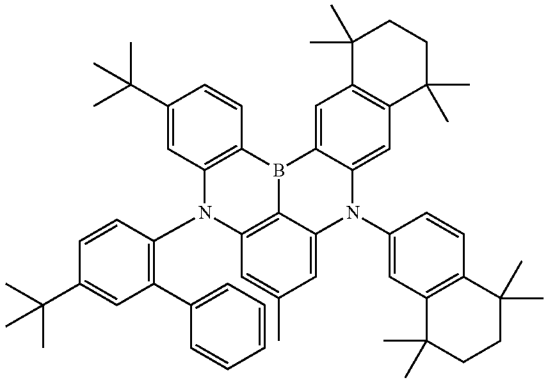
BD-6
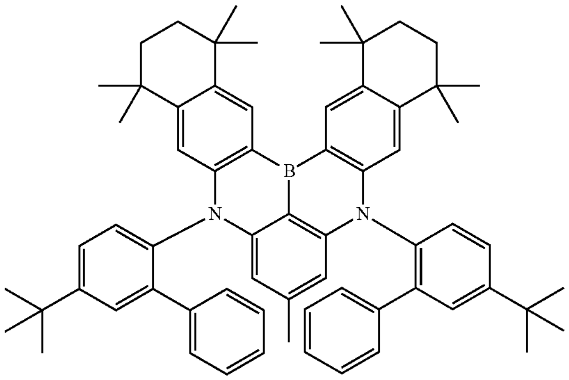
BD-7
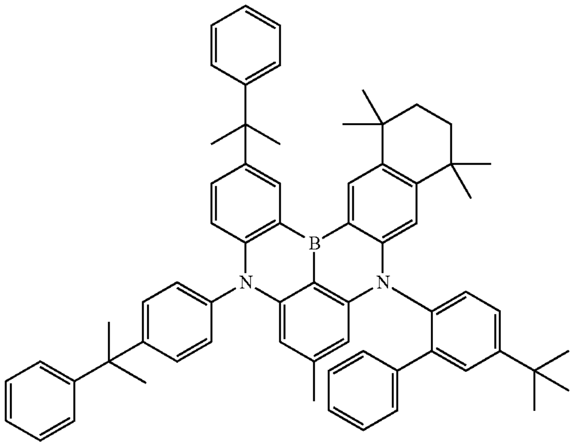

-continued
BD-8
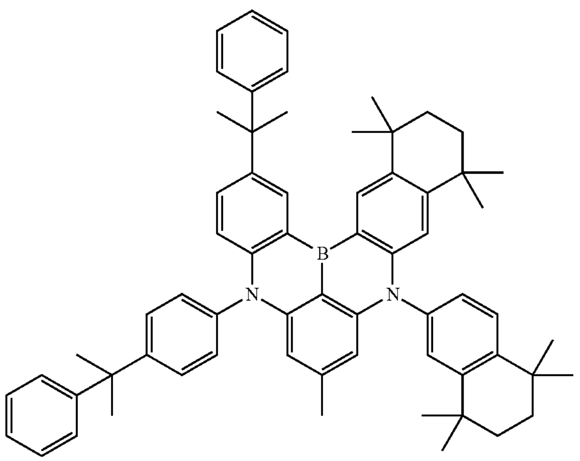
BD-9
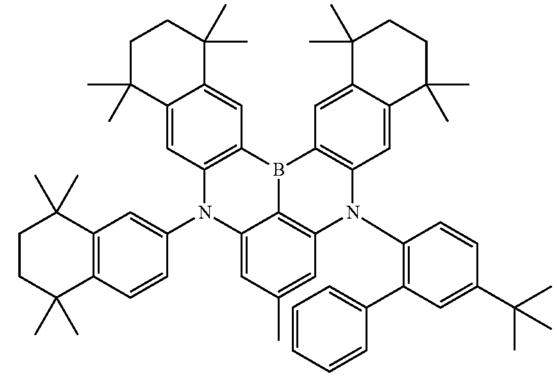
BD-10
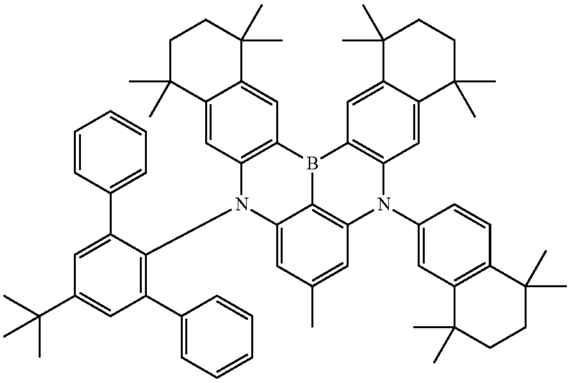
BD-11
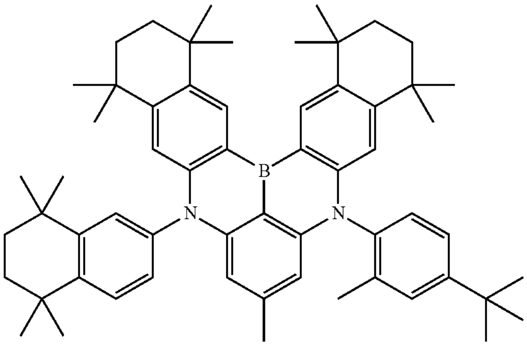
-continued
BD-12
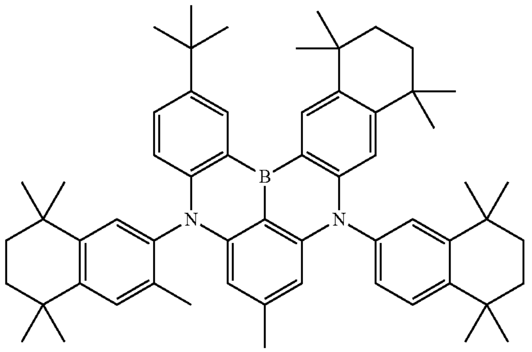
BD-13
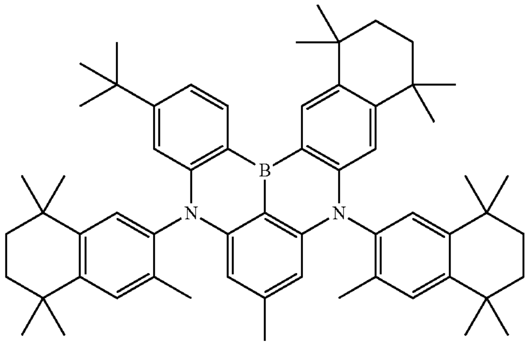
BD-14
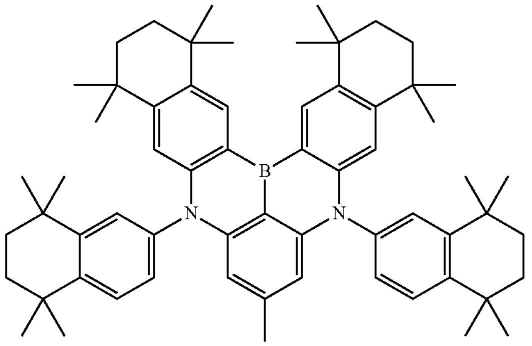
BD-15
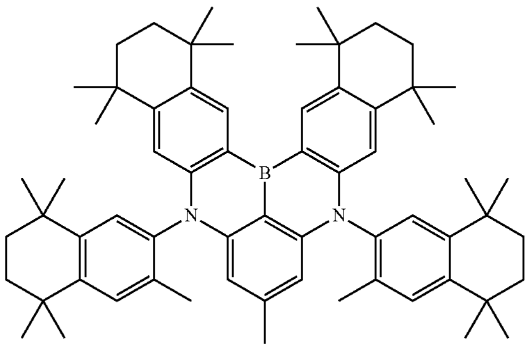

-continued
BD-16
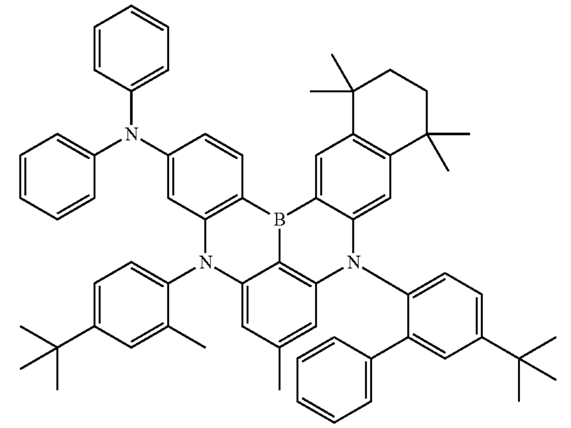
BD-17
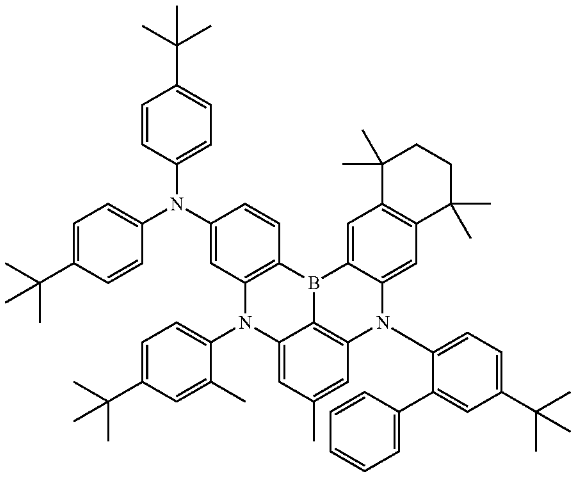
BD-18
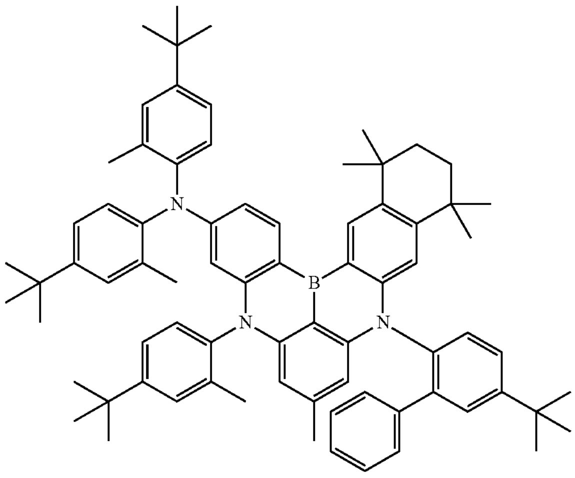
-continued
BD-19
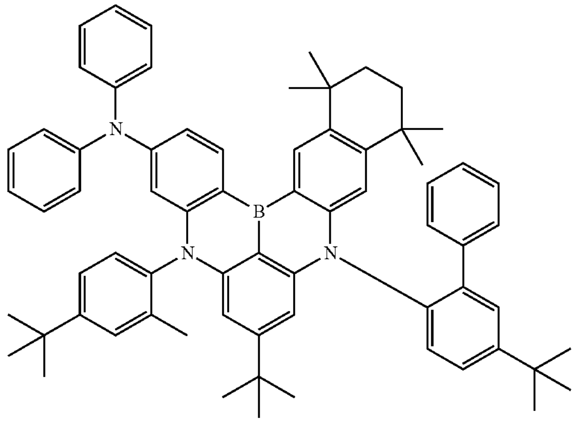
BD-20
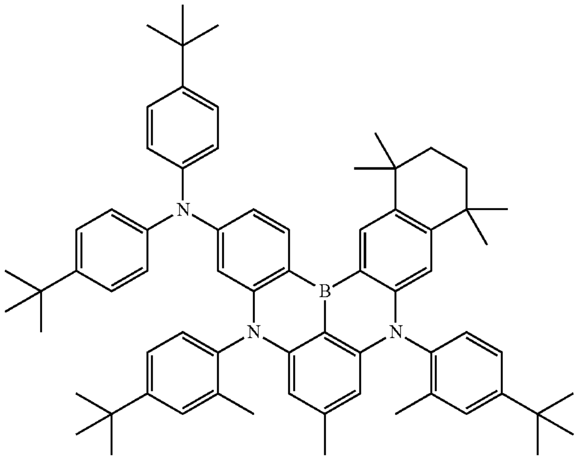
BD-41
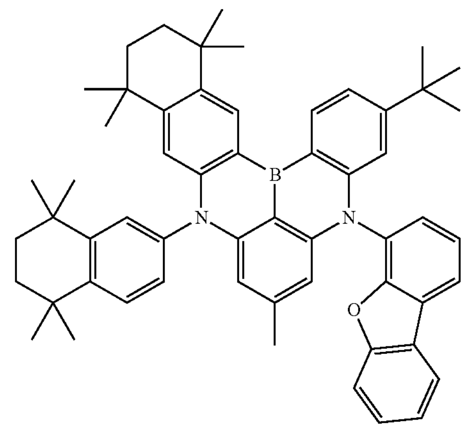

-continued
BD-42
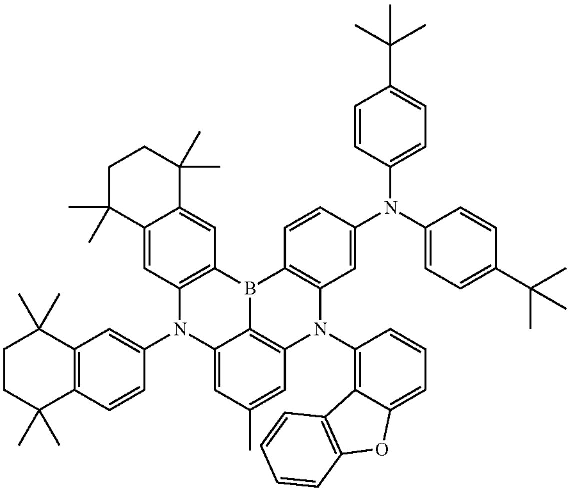
BD-43
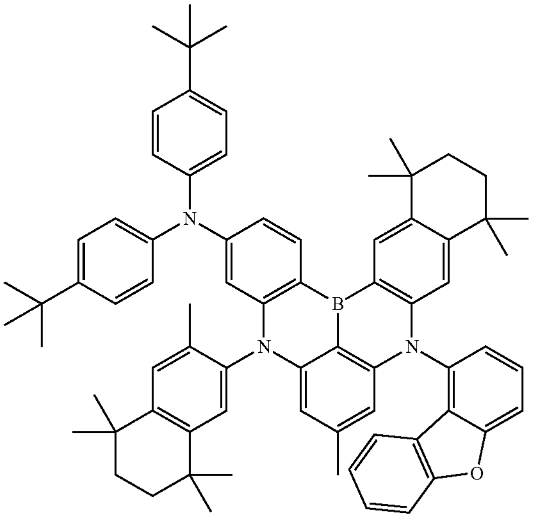
BD-44
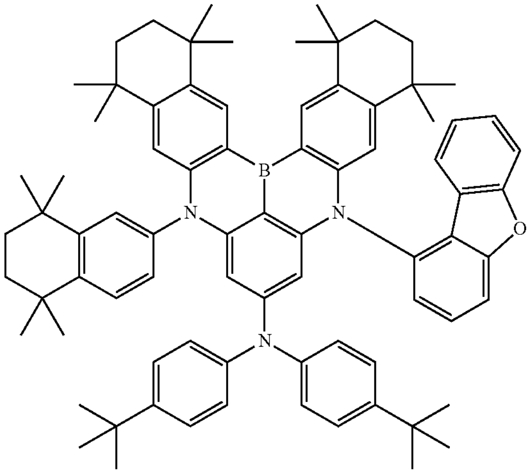
-continued
BD-45
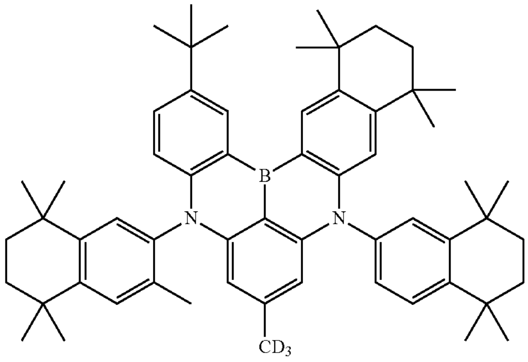
BD-46
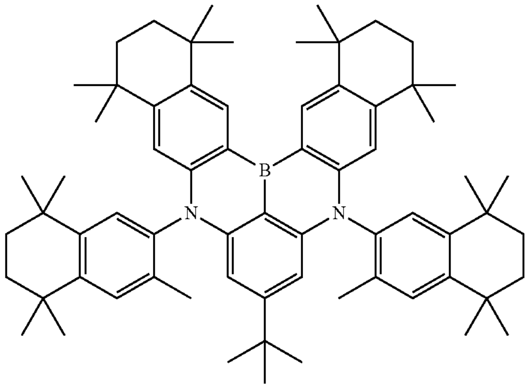
BD-47
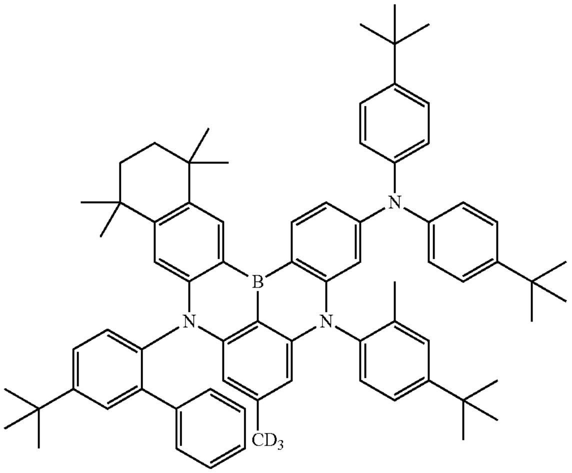

-continued
BD-48
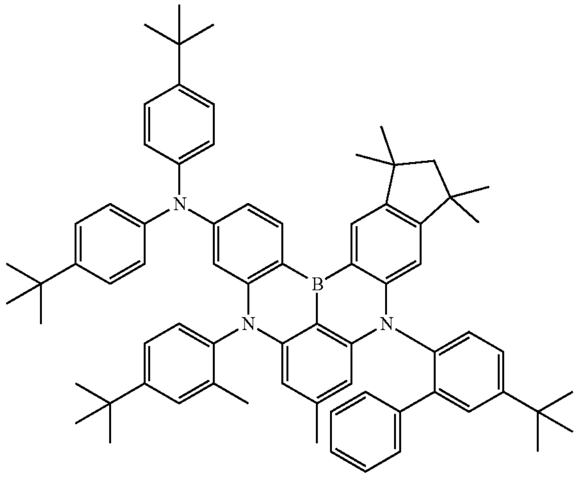
BD-49
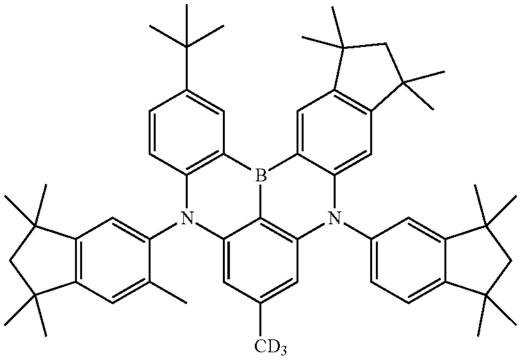
BD-50
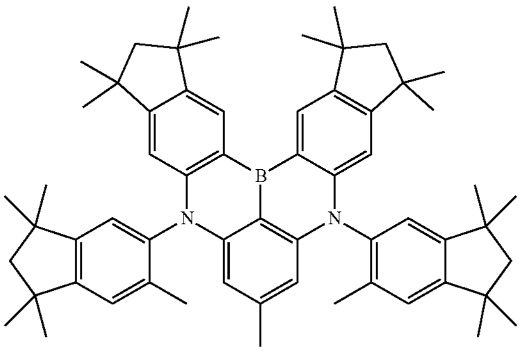
-continued
BD-51
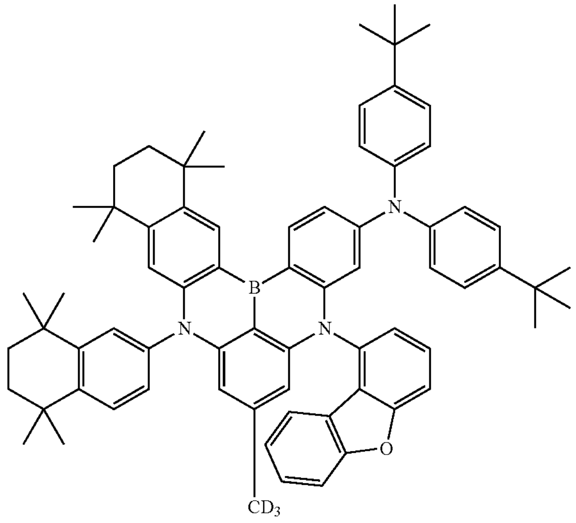
BD-52
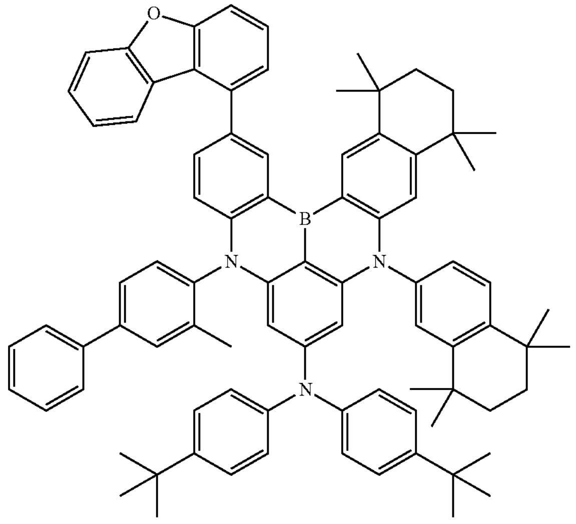

-continued
BD-53
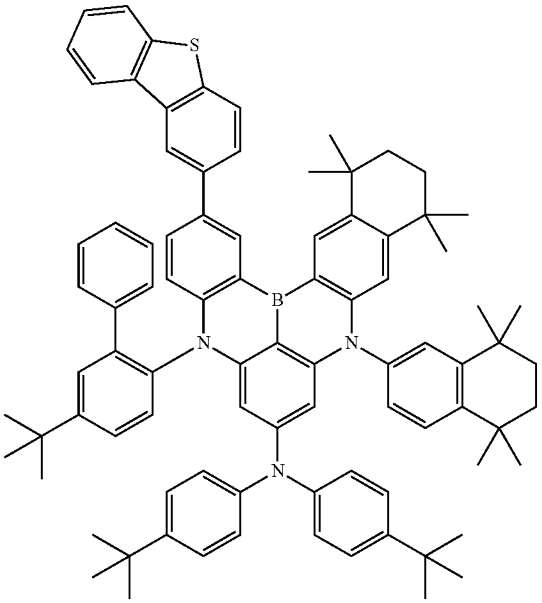
BD-54
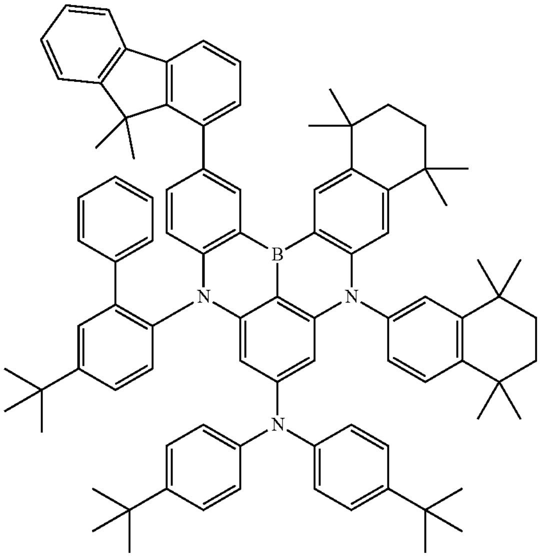
-continued
BD-55
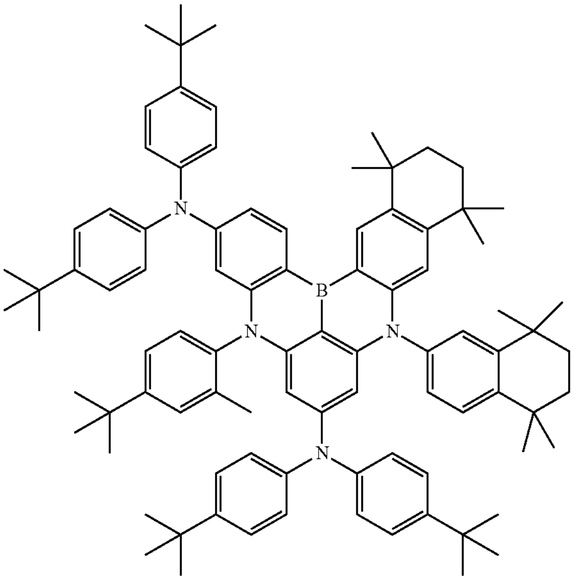
BD-56
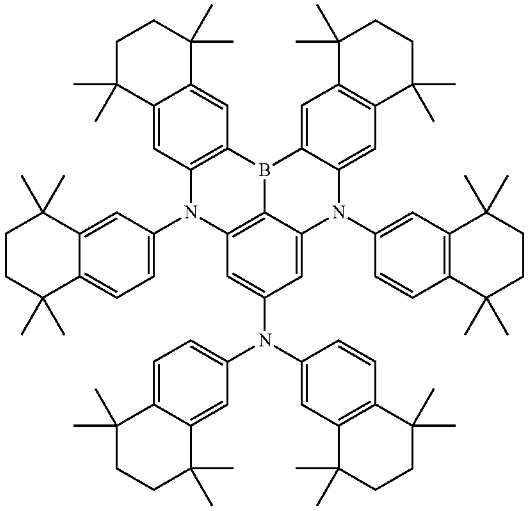
BD-57
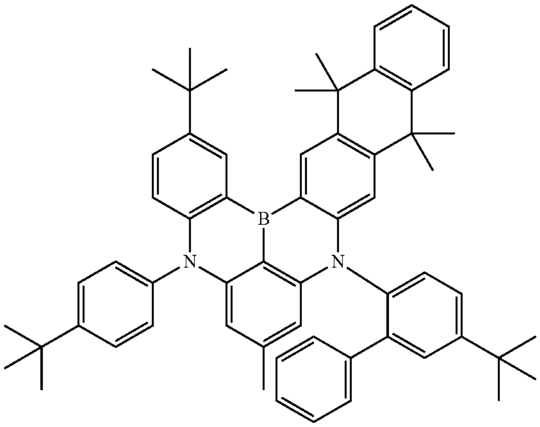

-continued
BD-58
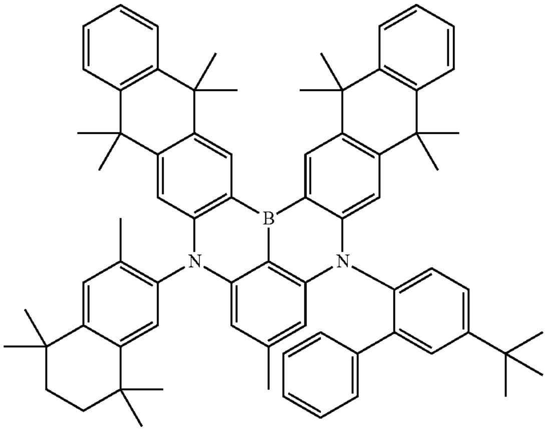
BD-59
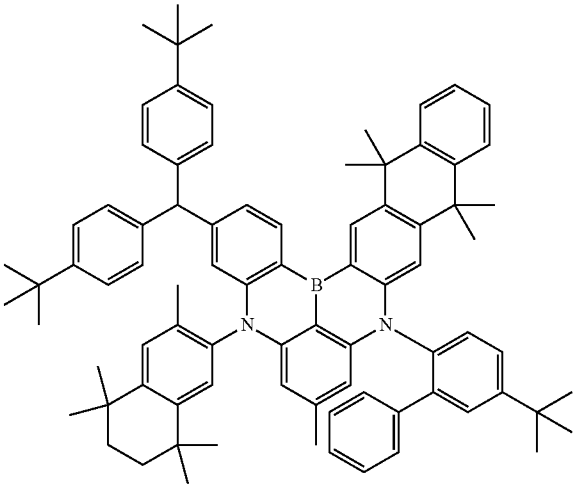
BD-60
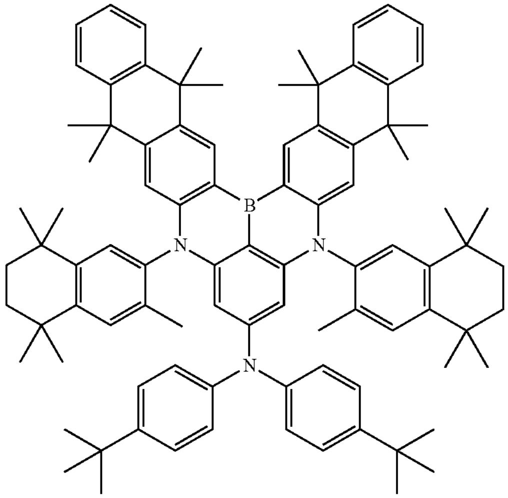
-continued
BD-61
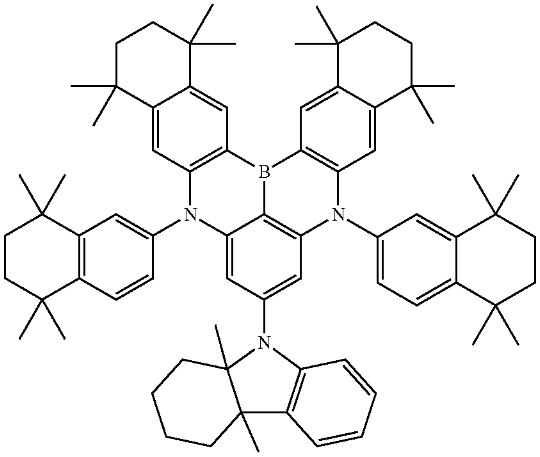
BD-62
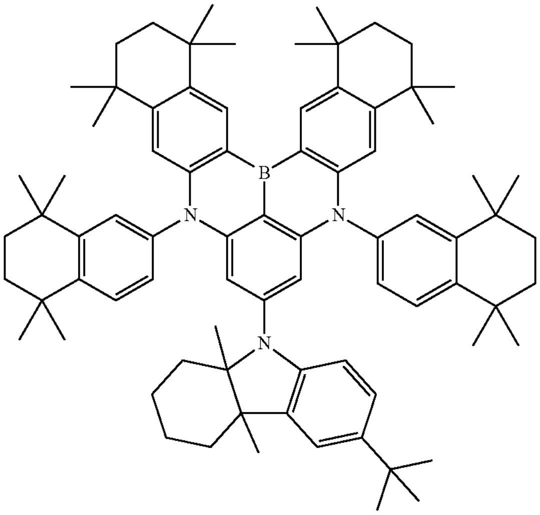
BD-63
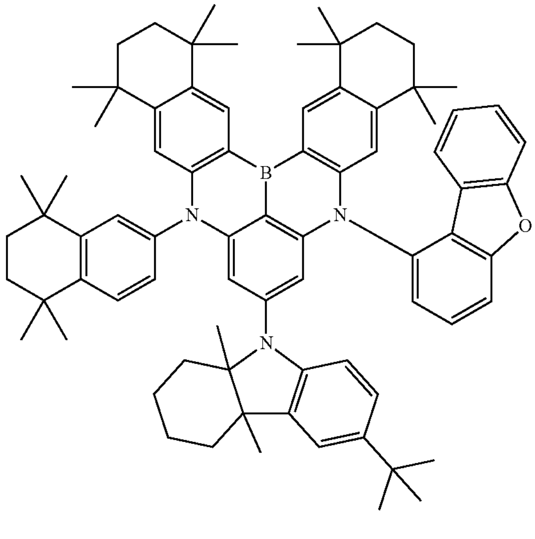

-continued

BD-64

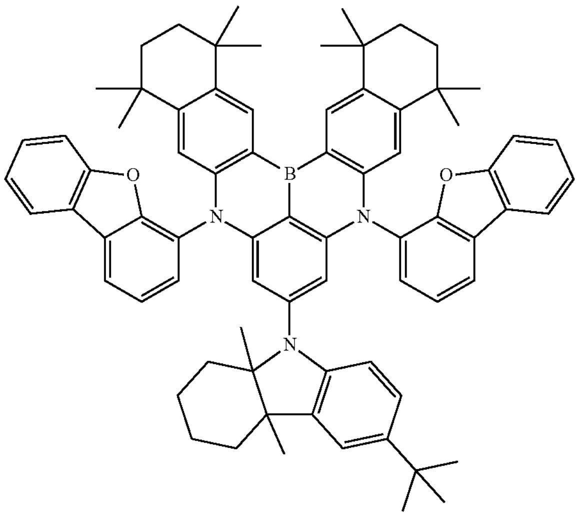

BD-65

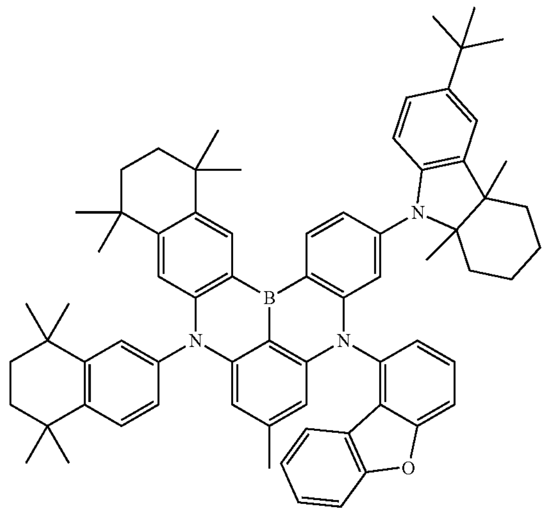

Comparative Examples 1 to 4

Organic light emitting devices of Comparative Examples 1 to 4 were each manufactured in the same manner as in Example 1, except that in Example 1, compounds described in the following Table 1 were used as dopants of the light emitting layer instead of Compound BD-1, and compounds described in the following Table 1 were used as host materials instead of BH-1.

BH-A

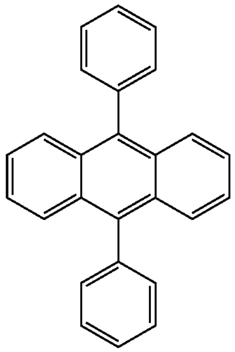

BH-B

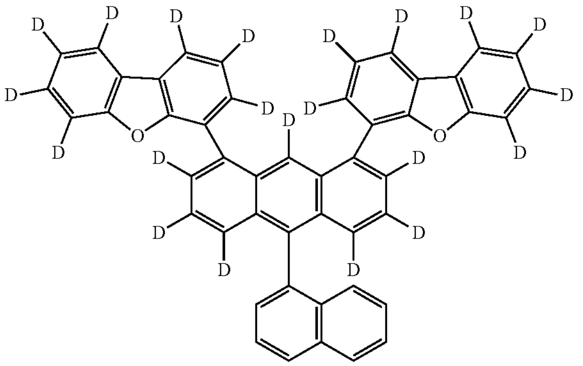

BH-C

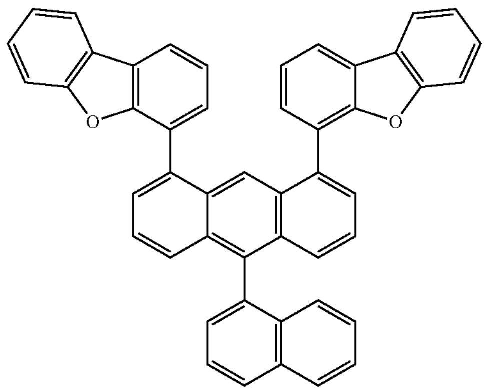

BD-A

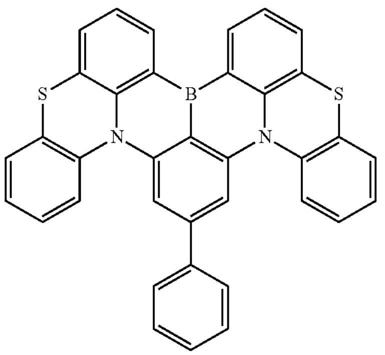

Voltages and efficiencies (cd/A/y) when a current density of 10 mA/$cm^2$ was applied to the organic light emitting devices in Examples 1 to 122 and Comparative Examples 1 to 4 and service lives ($T_{95}$) when a current density of 20 mA/$cm^2$ was applied to the devices were measured, and the results are shown in the following Table 1. In this case, for $LT_{95}$, a time taken for the luminance to decrease to 95% when the initial luminance at the current density of 20 $mA/cm^2$ is set to 100% was shown as the ratio based on Comparative Example 1.

| | Light emitting layer | | 10 mA/cm² | | |
|---|---|---|---|---|---|
| | Host | Dopant | Driving voltage (V) | Conversion efficiency (cd/A/y) | 20 mA/cm² LT95 (%) |
| Example 1 | BH-1 | BD-1 | 3.73 | 43.6 | 254 |
| Example 2 | BH-1 | BD-2 | 3.75 | 42.1 | 235 |
| Example 3 | BH-2 | BD-3 | 3.71 | 41.8 | 221 |
| Example 4 | BH-1 | BD-4 | 3.75 | 45.6 | 239 |
| Example 5 | BH-6 | BD-5 | 3.84 | 45.0 | 189 |
| Example 6 | BH-6 | BD-6 | 3.81 | 45.7 | 191 |
| Example 7 | BH-10 | BD-7 | 3.75 | 40.2 | 190 |
| Example 8 | BH-11 | BD-8 | 3.80 | 41.9 | 192 |
| Example 9 | BH-12 | BD-9 | 3.86 | 45.1 | 214 |
| Example 10 | BH-1 | BD-10 | 3.87 | 40.5 | 230 |
| Example 11 | BH-1 | BD-11 | 3.73 | 45.2 | 259 |
| Example 12 | BH-2 | BD-12 | 3.71 | 42.3 | 235 |
| Example 13 | BH-13 | BD-13 | 3.73 | 41.2 | 194 |
| Example 14 | BH-1 | BD-14 | 3.72 | 45.3 | 255 |
| Example 15 | BH-41 | BD-15 | 3.82 | 41.5 | 207 |
| Example 16 | BH-41 | BD-16 | 3.83 | 40.1 | 199 |
| Example 17 | BH-14 | BD-17 | 3.81 | 45.0 | 182 |
| Example 18 | BH-13 | BD-18 | 3.88 | 46.3 | 179 |
| Example 19 | BH-1 | BD-19 | 3.83 | 41.8 | 215 |
| Example 20 | BH-1 | BD-20 | 3.82 | 40.8 | 214 |
| Example 21 | BH-1 | BD-21 | 3.73 | 43.2 | 222 |
| Example 22 | BH-1 | BD-22 | 3.80 | 40.7 | 216 |
| Example 23 | BH-1 | BD-23 | 3.79 | 40.5 | 217 |
| Example 24 | BH-6 | BD-24 | 3.83 | 41.9 | 188 |
| Example 25 | BH-6 | BD-25 | 3.82 | 42.1. | 187 |
| Example 26 | BH-6 | BD-26 | 3.85 | 41.2 | 187 |
| Example 27 | BH-12 | BD-27 | 3.84 | 44.2 | 192 |
| Example 28 | BH-12 | BD-28 | 3.83 | 44.2 | 190 |
| Example 29 | BH-12 | BD-29 | 3.85 | 44.7 | 195 |
| Example 30 | BH-11 | BD-30 | 3.86 | 43.2 | 190 |
| Example 31 | BH-10 | BD-31 | 3.75 | 40.0 | 185 |
| Example 32 | BH-10 | BD-32 | 3.74 | 40.1 | 187 |
| Example 33 | BH-1 | BD-33 | 3.75 | 42.0 | 211 |
| Example 34 | BH-1 | BD-34 | 3.77 | 44.2 | 236 |
| Example 35 | BH-2 | BD-35 | 3.86 | 44.9 | 209 |
| Example 36 | BH-1 | BD-36 | 3.88 | 42.5 | 198 |
| Example 37 | BH-1 | BD-37 | 3.80 | 40.7 | 216 |
| Example 38 | BH-6 | BD-38 | 3.72 | 42.9 | 170 |
| Example 39 | BH-6 | BD-39 | 3.75 | 41.6 | 172 |
| Example 40 | BH-6 | BD-40 | 3.72 | 42.2 | 165 |
| Example 41 | BH-6 | BD-41 | 3.73 | 41.8 | 166 |
| Example 42 | BH-1 | BD-42 | 3.92 | 40.9 | 159 |
| Example 43 | BH-1 | BD-43 | 3.91 | 41.0 | 161 |
| Example 44 | BH-1 | BD-44 | 3.88 | 40.8 | 171 |
| Example 45 | BH-1 | BD-45 | 3.85 | 45.1 | 213 |
| Example 46 | BH-1 | BD-46 | 3.75 | 46.9 | 250 |
| Example 47 | BH-41 | BD-47 | 3.85 | 43.1 | 212 |
| Example 48 | BH-41 | BD-48 | 3.84 | 42.5 | 211 |
| Example 49 | BH-41 | BD-49 | 3.86 | 40.3 | 220 |
| Example 50 | BH-41 | BD-50 | 3.88 | 40.1 | 210 |
| Example 51 | BH-41 | BD-51 | 3.89 | 41.7 | 210 |
| Example 52 | BH-41 | BD-52 | 3.88 | 39.9 | 199 |
| Example 53 | BH-41 | BD-53 | 3.84 | 38.3 | 182 |
| Example 54 | BH-41 | BD-54 | 3.86 | 35.2 | 180 |
| Example 55 | BH-13 | BD-55 | 3.88 | 40.1 | 207 |
| Example 56 | BH-14 | BD-56 | 3.83 | 46.3 | 220 |
| Example 57 | BH-14 | BD-57 | 3.84 | 43.5 | 190 |
| Example 58 | BH-13 | BD-58 | 3.88 | 43.3 | 186 |
| Example 59 | BH-10 | BD-59 | 3.72 | 41.8 | 193 |
| Example 60 | BH-6 | BD-60 | 3.76 | 44.0 | 200 |
| Example 61 | BH-12 | BD-61 | 3.73 | 41.5 | 201 |
| Example 62 | BH-41 | BD-62 | 3.86 | 41.7 | 269 |
| Example 63 | BH-41 | BD-63 | 3.92 | 40.8 | 232 |
| Example 64 | BH-11 | BD-64 | 3.88 | 38.8 | 169 |
| Example 65 | BH-11 | BD-65 | 3.87 | 39.1 | 170 |
| Example 66 | BH-2 | BD-2 | 3.77 | 41.1 | 221 |
| Example 67 | BH-3 | BD-1 | 3.70 | 41.5 | 217 |
| Example 68 | BH-4 | BD-1 | 3.88 | 42.1 | 216 |

-continued

| | Light emitting layer | | 10 mA/cm² | | |
|---|---|---|---|---|---|
| | Host | Dopant | Driving voltage (V) | Conversion efficiency (cd/A/y) | 20 mA/cm² LT95 (%) |
| Example 69 | BH-5 | BD-14 | 3.62 | 43.3 | 220 |
| Example 70 | BH-6 | BD-10 | 3.88 | 41.0 | 207 |
| Example 71 | BH-8 | BD-4 | 3.80 | 42.5 | 210 |
| Example 72 | BH-9 | BD-1 | 3.84 | 42.0 | 207 |
| Example 73 | BH-10 | BD-1 | 3.723 | 44.8 | 211 |
| Example 74 | BH-11 | BD-33 | 3.52 | 43.6 | 210 |
| Example 75 | BH-12 | BD-32 | 3.49 | 42.7 | 208 |
| Example 76 | BH-13 | BD-2 | 3.44 | 43.8 | 216 |
| Example 77 | BH-14 | BD-3 | 3.42 | 46.7 | 221 |
| Example 78 | BH-15 | BD-1 | 3.61 | 41.1 | 217 |
| Example 79 | BH-16 | BD-11 | 3.72 | 42.9 | 152 |
| Example 80 | BH-17 | BD-1 | 3.70 | 43.2 | 197 |
| Example 81 | BH-18 | BD-21 | 3.71 | 40.5 | 220 |
| Example 82 | BH-19 | BD-14 | 3.68 | 44.4 | 222 |
| Example 83 | BH-20 | BD-34 | 3.70 | 42.5 | 192 |
| Example 84 | BH-21 | BD-34 | 3.71 | 42.1 | 199 |
| Example 85 | BH-22 | BD-34 | 3.75 | 42.0 | 213 |
| Example 86 | BH-23 | BD-62 | 3.72 | 41.9 | 207 |
| Example 87 | BH-24 | BD-62 | 3.75 | 41.5 | 200 |
| Example 88 | BH-25 | BD-1 | 3.75 | 43.5 | 201 |
| Example 89 | BH-26 | BD-1 | 3.77 | 45.1 | 193 |
| Example 90 | BH-27 | BD-9 | 3.77 | 41.1 | 181 |
| Example 91 | BH-28 | BD-1 | 3.73 | 43.3 | 183 |
| Example 92 | BH-29 | BD-2 | 3.73 | 43.3 | 159 |
| Example 94 | BH-31 | BD-14 | 3.92 | 43.1 | 176 |
| Example 95 | BH-32 | BD-1 | 3.98 | 42.1 | 171 |
| Example 96 | BH-33 | BD-35 | 3.96 | 40.5 | 245 |
| Example 97 | BH-34 | BD-1 | 3.99 | 42.1 | 260 |
| Example 98 | BH-35 | BD-34 | 3.97 | 42.0 | 177 |
| Example 99 | BH-36 | BD-34 | 3.96 | 42.3 | 190 |
| Example 100 | BH-37 | BD-1 | 3.93 | 42.3 | 179 |
| Example 101 | BH-38 | BD-4 | 3.91 | 42.1 | 175 |
| Example 102 | BH-39 | BD-9 | 3.89 | 42.2 | 170 |
| Example 103 | BH-40 | BD-2 | 3.88 | 43.0 | 168 |
| Example 104 | BH-41 | BD-1 | 3.92 | 43.6 | 251 |
| Example 105 | BH-42 | BD-10 | 3.89 | 40.5 | 170 |
| Example 106 | BH-43 | BD-15 | 3.90 | 42.2 | 186 |
| Example 107 | BH-44 | BD-55 | 3.87 | 43.5 | 183 |
| Example 108 | BH-45 | BD-59 | 3.86 | 44.0 | 166 |
| Example 109 | BH-46 | BD-60 | 3.88 | 44.1 | 169 |
| Example 110 | BH-47 | BD-61 | 3.85 | 42.0 | 209 |
| Example 111 | BH-48 | BD-61 | 3.90 | 42.5 | 167 |
| Example 112 | BH-49 | BD-61 | 3.90 | 42.1 | 166 |
| Example 113 | BH-50 | BD-1 | 3.93 | 41.5 | 165 |
| Example 114 | BH-51 | BD-4 | 3.87 | 41.8 | 166 |
| Example 115 | BH-52 | BD-9 | 3.83 | 42.2 | 167 |
| Example 116 | BH-53 | BD-9 | 3.85 | 42.2 | 169 |
| Example 117 | BH-54 | BD-9 | 3.85 | 42.3 | 196 |
| Example 118 | BH-55 | BD-1 | 3.88 | 40.8 | 173 |
| Example 119 | BH-56 | BD-1 | 3.86 | 41.0 | 166 |
| Example 120 | BH-57 | BD-55 | 3.84 | 40.9 | 165 |
| Example 121 | BH-58 | BD-14 | 3.88 | 42.0 | 150 |
| Example 122 | BH-59 | BD-14 | 3.87 | 42.1 | 161 |
| Comparative Example 1 | BH-A | BD-1 | 4.11 | 37.7 | 100 |
| Comparative Example 2 | BH-B | BD-4 | 4.02 | 35.4 | 110 |
| Comparative Example 3 | BH-C | BD-9 | 4.03 | 35.7 | 85 |
| Comparative Example 4 | BH-57 | BD-A | 3.93 | 30.9 | 83 |

The conversion efficiency (cd/A/y) takes a current efficiency (cd/A) to color purity (CIEy) of the material into consideration, and is an important reference value for efficiency in small and large organic light emitting devices targeting high luminance and high color gamut.

As can be seen in the device results in Table 1, when an organic light emitting device was constructed by combining a host material represented by any one of [Formula 1-1] to [Formula 1-3] according to an exemplary embodiment of the present specification and a dopant material represented by [Formula 2], the organic light emitting device was better in both the conversion efficiency and service life performance of a device than other devices which were not constructed by the combination.

Furthermore, it was confirmed that even when a host in which deuterium was partially substituted was used, a device having a long service life was constructed.

Further, from Examples 79 and 80, it could be seen that when the skeleton was the same and the deuterium substitution rate was similar, the service life when deuterium was linked to anthracene was increased.

Although the preferred exemplary embodiments of the present invention have been described above, the present invention is not limited thereto, and various modifications can be made and carried out within the scopes of the claims and the detailed description of the invention, and also fall within the scope of the invention.

The invention claimed is:

1. An organic light emitting device comprising:

an anode;

a cathode; and an organic material layer comprising a light emitting layer provided between the anode and the cathode, wherein the light emitting layer comprises one or more of compounds represented by the following Formulae 1-1 to 1-3; and a compound represented by the following Formula 2:

[Formula 1-1]

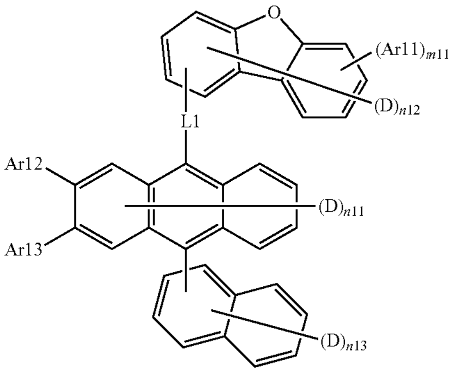

[Formula 1-2]

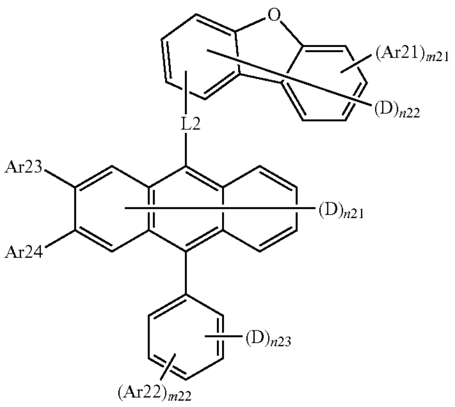

-continued

[Formula 1-3]

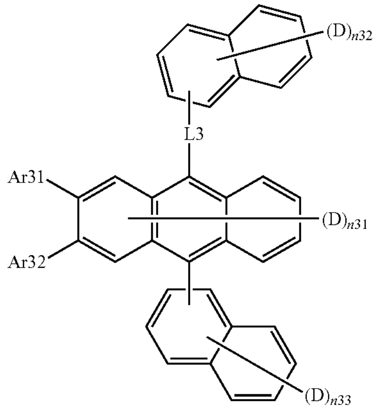

[Formula 2]

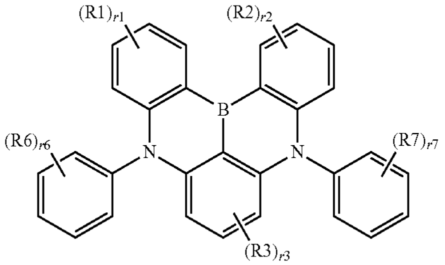

wherein, in Formulae 1-1 to 1-3 and 2,

L1 to L3 are the same as or different from each other, and are each independently a direct bond; or a substituted or unsubstituted arylene group, D is deuterium, n11, n21, and n31 are each an integer from 0 to 6, n12, n13, n22, n32, and n33 are each an integer from 0 to 7, and n23 is an integer from 0 to 5, Ar11, Ar21, and Ar22 are the same as or different from each other, and are each independently a substituted or unsubstituted aryl group, Ar12, Ar13, Ar23, Ar24, Ar31, and Ar32 are the same as or different from each other, and are each independently hydrogen; deuterium; a substituted or unsubstituted aryl group; or a substituted or unsubstituted heteroaryl group, m11 and m21 are an integer from 0 to 4, m22 is an integer from 0 to 5, and substituents in the parenthesis are the same as or different from each other provided that when m11, m21, and m22 are each 2 or higher, the compounds of Formulae 1-1 to 1-3 each have at least one or more deuteriums, R1 to R3, R6, and R7 are the same as or different from each other, and are each independently hydrogen; deuterium; a halogen group; a cyano group; a substituted or unsubstituted alkyl group; a substituted or unsubstituted cycloalkyl group; a substituted or unsubstituted silyl group; a substituted or unsubstituted alkenyl group; a substituted or unsubstituted aryl group; a substituted or unsubstituted heterocyclic group; a substituted or unsubstituted alkoxy group; a substituted or unsubstituted aryloxy group; a substituted or unsubstituted alkylthio group; a substituted or unsubstituted arylthio group; or a substituted or unsubstituted amine group, or a group represented by the following Formula 2-A or 2-B, or are bonded to an adjacent substituent to form a substituted or unsubstituted ring, r1 and r2 are an integer from 0 to 4, r3 is an integer from 0 to 3, r6 and r7 are an integer from 0 to 5, and substituents in the parenthesis are the same as or different from each other provided that when r1 to r3, r6, and r7 are each 2 or higher,

[Formula 2-A]

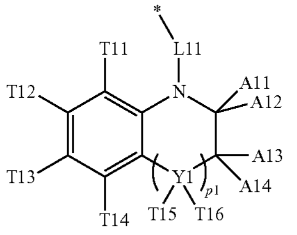

[Formula 2-B]

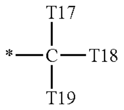

wherein, in Formulae 2-A and 2-B,

* is a bonding site,

T11 to T19 are the same as or different from each other, and are each independently hydrogen; deuterium; a halogen group; a cyano group; a substituted or unsubstituted alkyl group; a substituted or unsubstituted cycloalkyl group; a substituted or unsubstituted silyl group; a substituted or unsubstituted alkenyl group; a substituted or unsubstituted aryl group; a substituted or unsubstituted heterocyclic group; a substituted or unsubstituted alkoxy group; a substituted or unsubstituted aryloxy group; a substituted or unsubstituted alkylthio group; a substituted or unsubstituted arylthio group; or a substituted or unsubstituted amine group, or are bonded to an adjacent substituent to form a substituted or unsubstituted ring, at least one of T17 to T19 is a substituted or unsubstituted aryl group, and at least one of the remaining T17 to T19 is a substituted or unsubstituted alkyl group, A11 to A14 are the same as or different from each other, and are each independently hydrogen; deuterium; a halogen group; a cyano group; a substituted or unsubstituted alkyl group; a substituted or unsubstituted cycloalkyl group; a substituted or unsubstituted silyl group; a substituted or unsubstituted alkenyl group; a substituted or unsubstituted aryl group; a substituted or unsubstituted heterocyclic group; a substituted or unsubstituted alkoxy group; a substituted or unsubstituted aryloxy group; a substituted or unsubstituted alkylthio group; a substituted or unsubstituted arylthio group; or a substituted or unsubstituted amine group, or are bonded to an adjacent substituent to form a substituted or unsubstituted aliphatic hydrocarbon ring, L11 is a direct bond; or a substituted or unsubstituted arylene group, p1 is 0 or 1, and Y1 is C or Si, wherein one or more of R1 to R3, R6, and R7 are a group represented by Formula 2-A or 2-B, or wherein two of adjacent R1's, two of adjacent R2's, two of adjacent R3's, two of adjacent R6's, or two of adjacent R7's are bonded to each other to form a substituted or unsubstituted aliphatic hydrocarbon ring comprising 5 or more carbon atoms.

2. The organic light emitting device of claim 1, wherein the compounds of Formulae 1-1 to 1-3 are deuterated by 30% or more.

3. The organic light emitting device of claim 1, wherein n11, n21, and n31 are 1 or higher.

4. The organic light emitting device of claim 1, wherein the light emitting layer comprises two types of compounds each represented by any one of Formulae 1-1 to 1-3 as hosts.

5. The organic light emitting device of claim 1, wherein the compound of Formula 1-1 is represented by any one selected from the following Formulae 101 to 104:

[Formula 101]

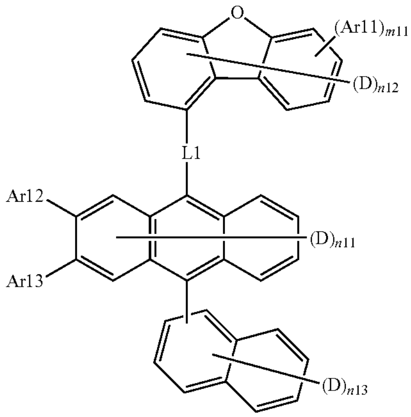

[Formula 102]

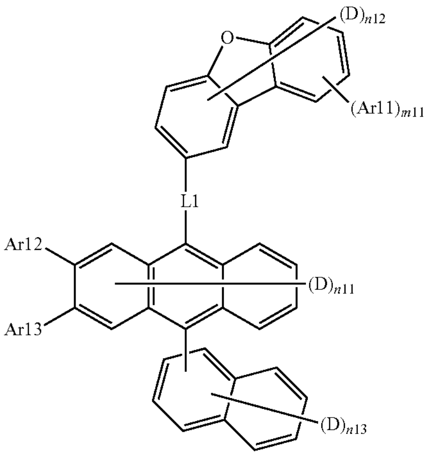

-continued

[Formula 103]

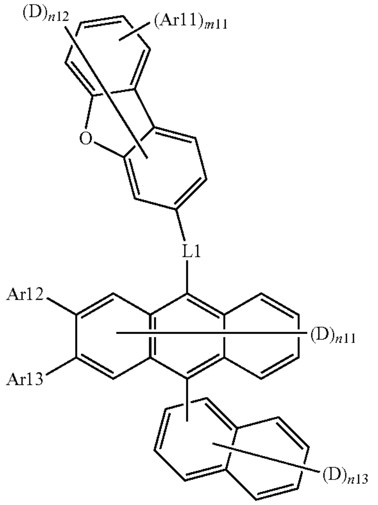

[Formula 104]

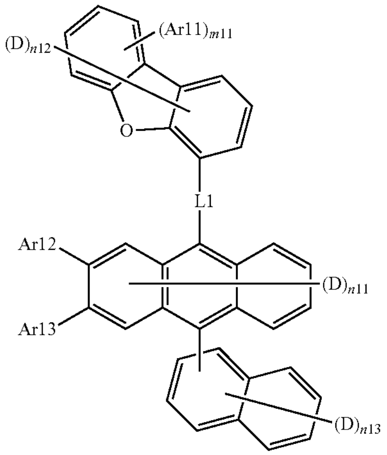

wherein, in Formulae 101 to 104, Ar11 to Ar13, D, n11 to n13, m11, and L1 are the same as defined in Formula 1-1.

6. The organic light emitting device of claim 1, wherein the compound of Formula 1-2 is represented by any one selected from the following Formulae 111 to 114:

[Formula 111]

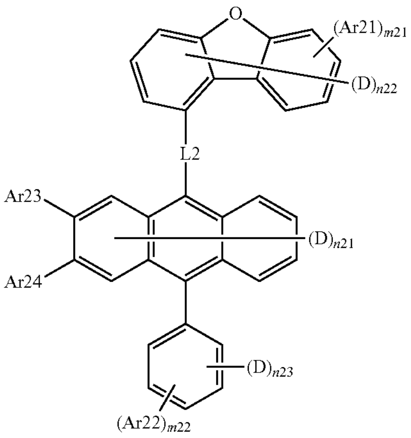

-continued

[Formula 112]

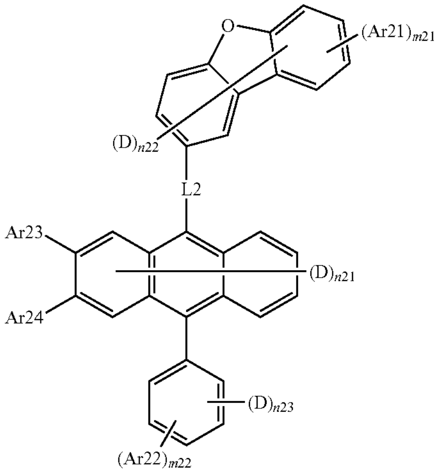

[Formula 113]

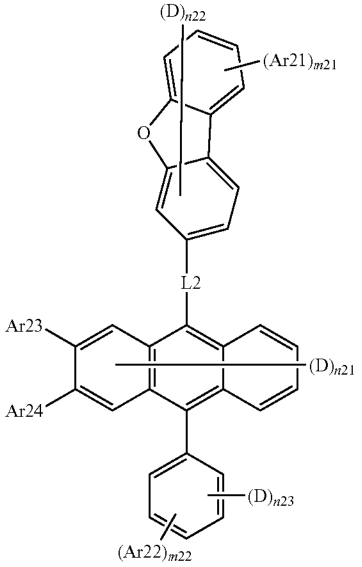

[Formula 114]

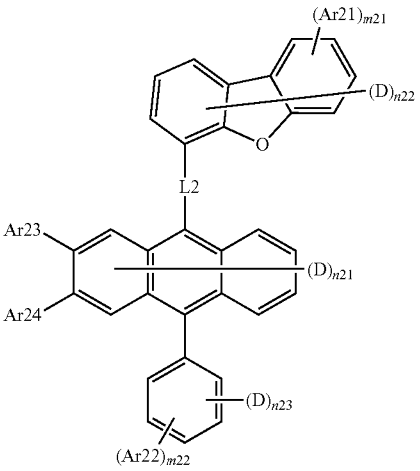

wherein, in Formulae 111 to 114, D, n21 to n23, Ar21 to Ar24, m21, m22, and L2 are the same as defined in Formula 1-2.

7. The organic light emitting device of claim 1, wherein the compound of Formula 1-3 is represented by any one selected from the following Formulae 121 to 124:

[Formula 121]

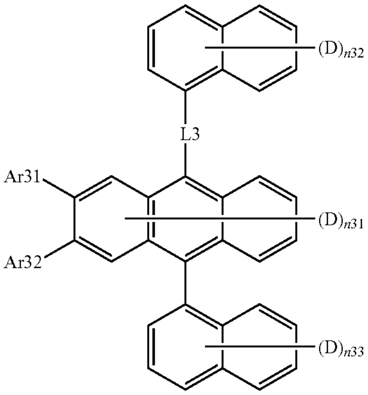

[Formula 122]

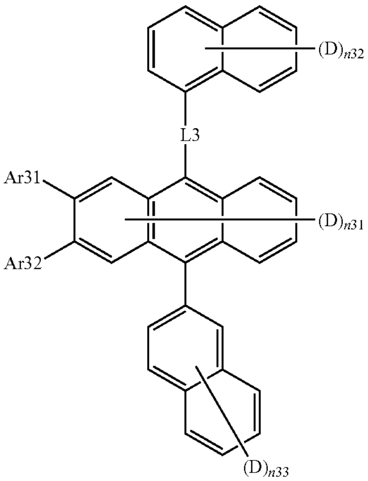

[Formula 123]

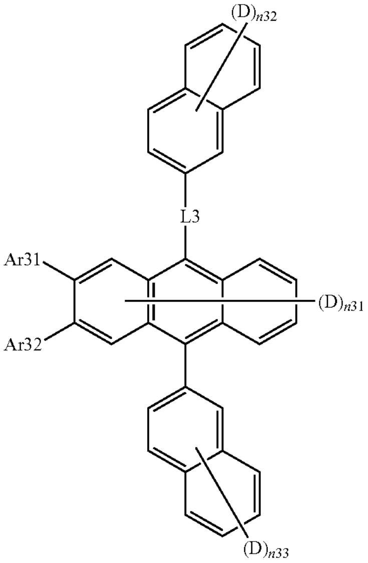

-continued

[Formula 124]

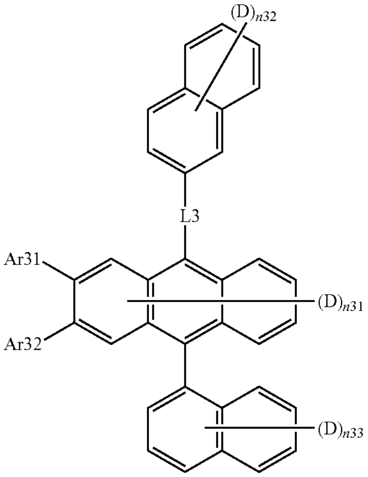

wherein, in Formulae 121 to 124, Ar31, Ar32, D, n31 to n33, and L3 are the same as defined in Formula 1-3.

8. The organic light emitting device of claim 1, wherein the compound of Formula 2 comprises at least one deuterium.

9. The organic light emitting device of claim 1, wherein the compound represented by Formula 1-1 is any one selected from the following compounds:

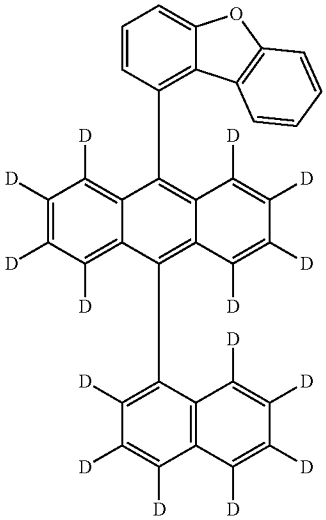

-continued
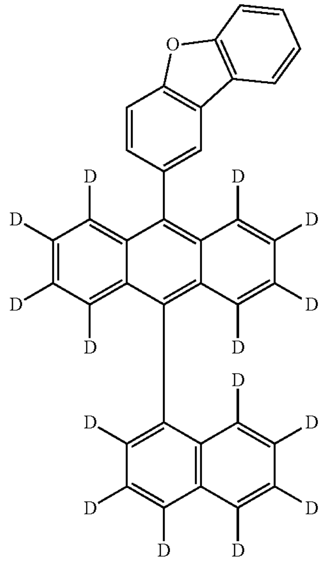
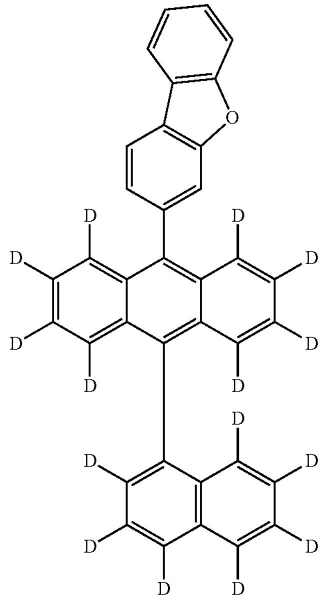
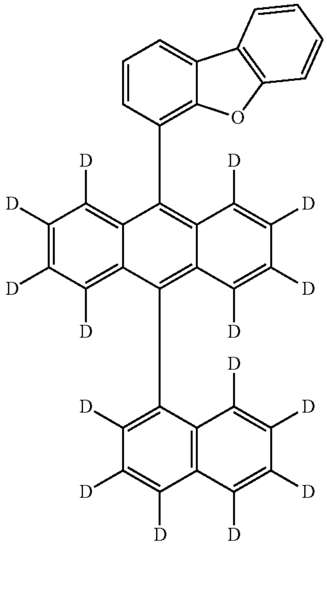
-continued
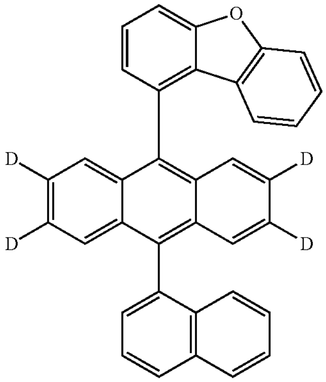
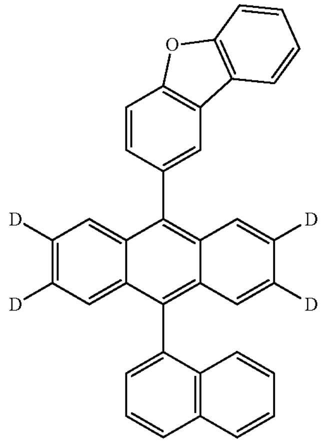
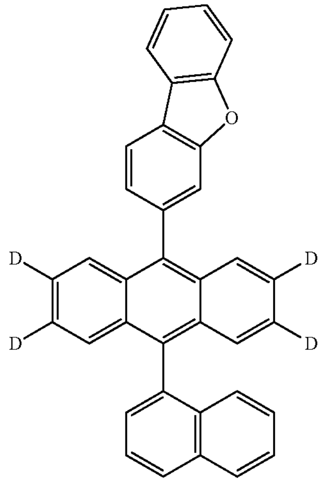
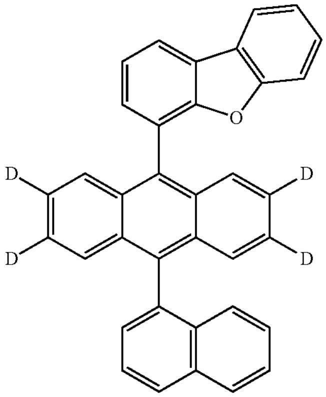

-continued
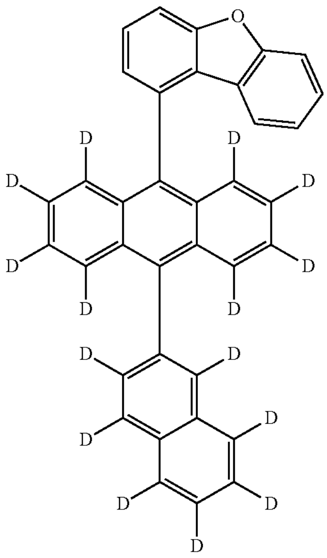
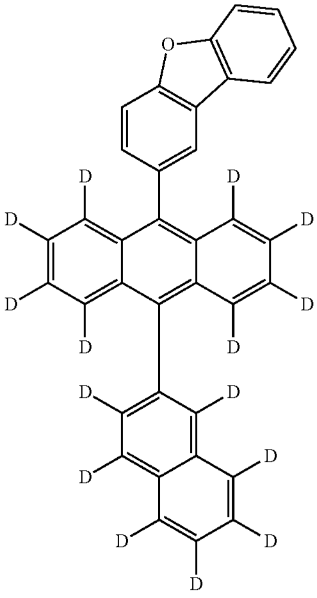
-continued
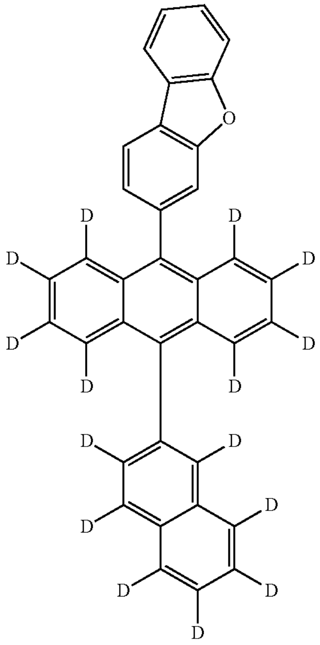
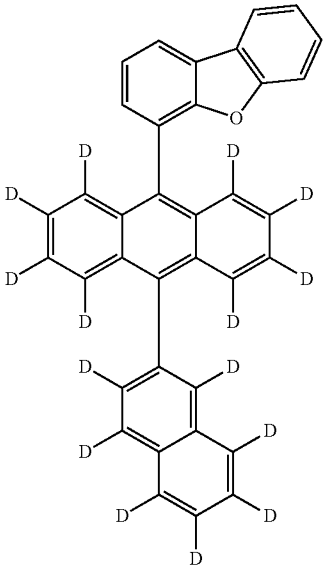
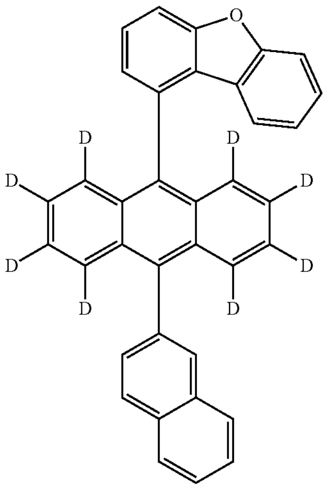

-continued
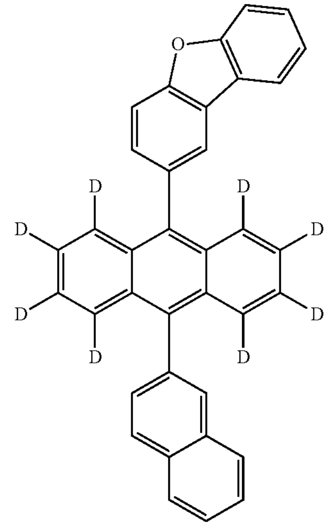
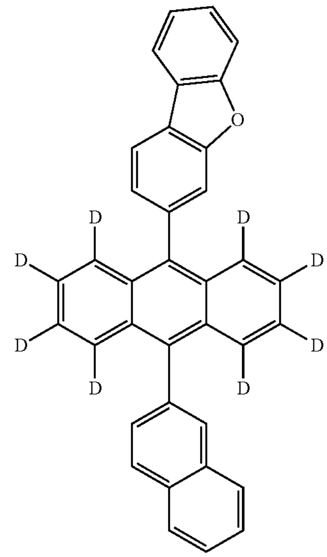
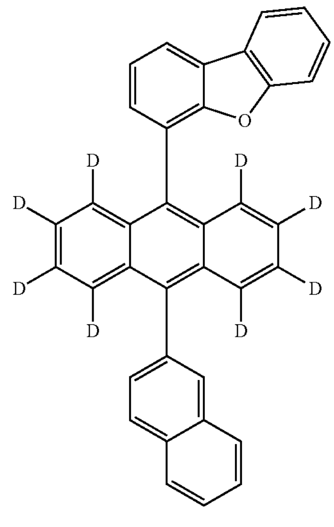
-continued
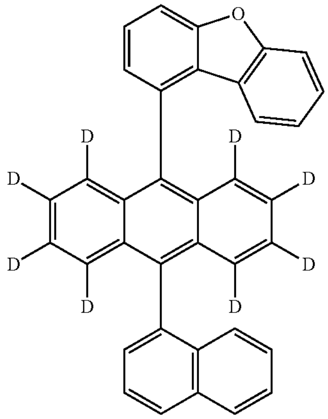
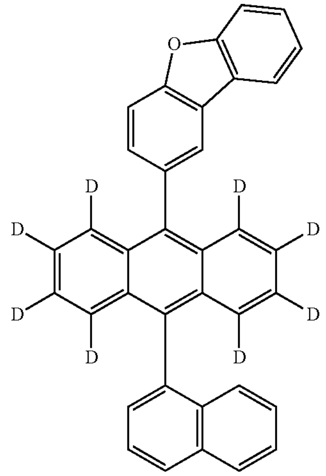
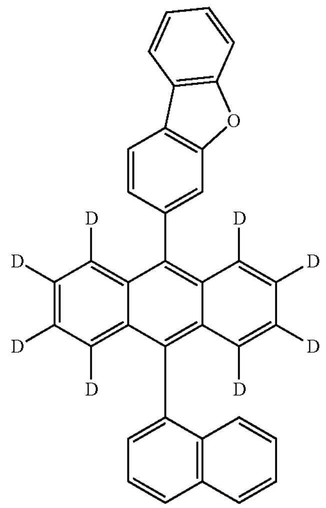

-continued
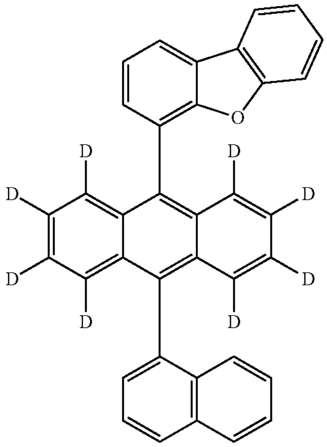
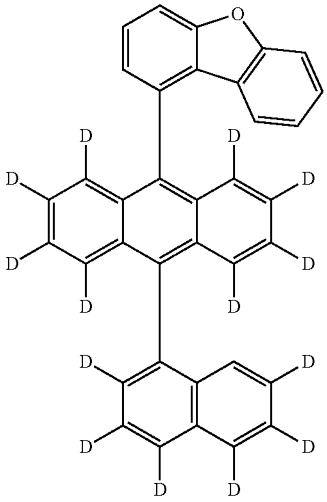
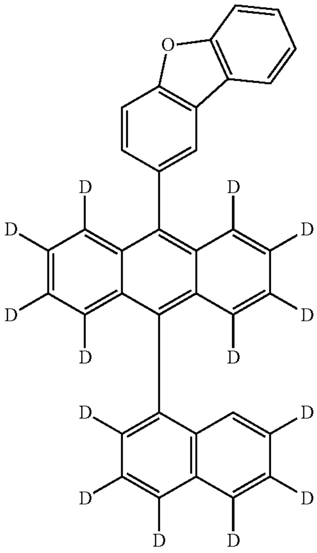
-continued
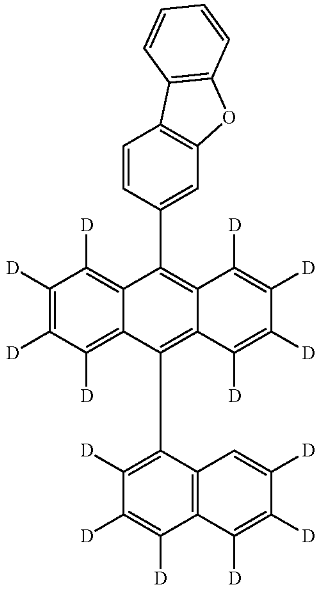
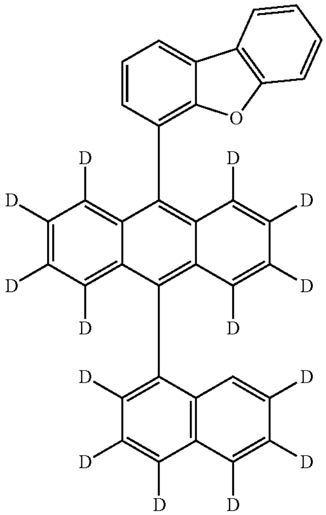
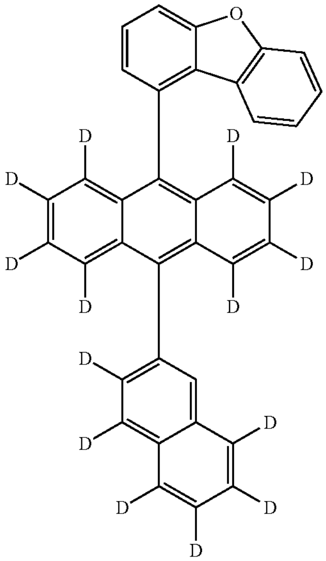

-continued
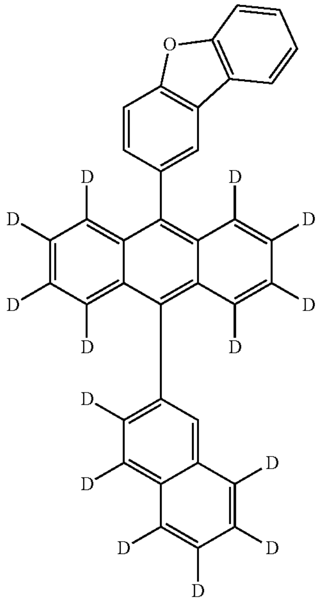
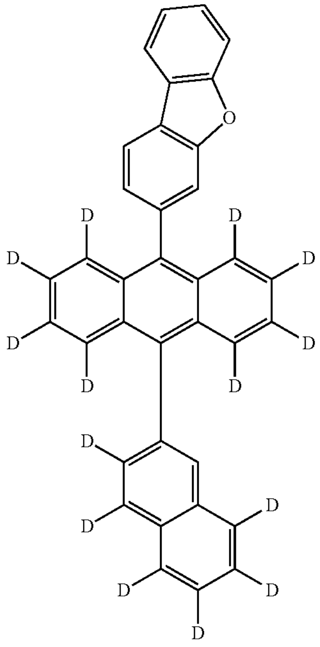
-continued
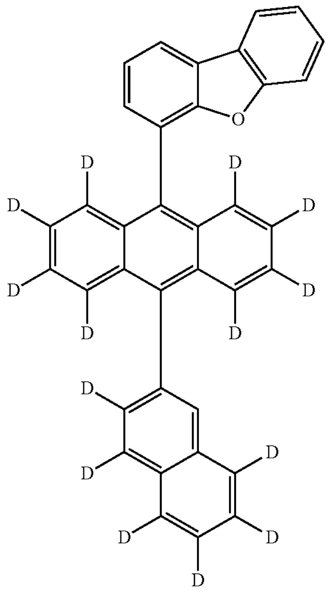
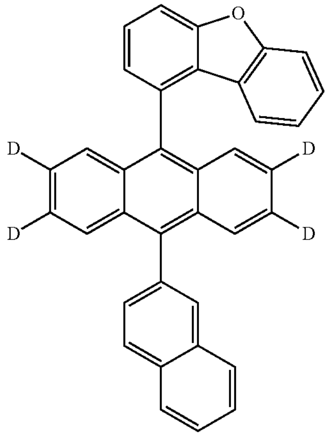
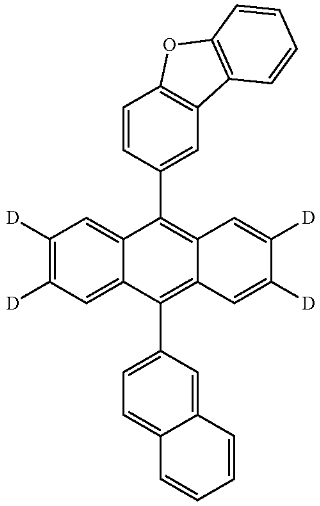

-continued
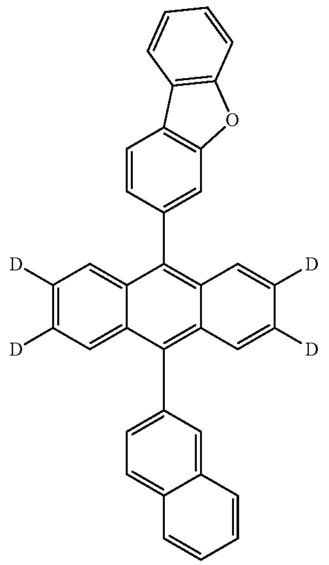
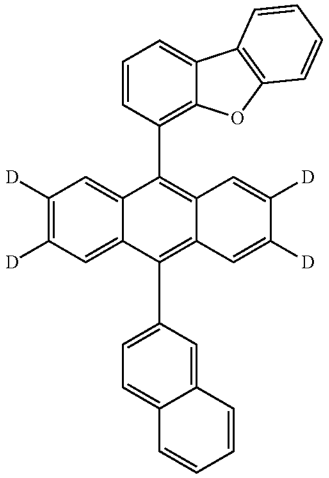
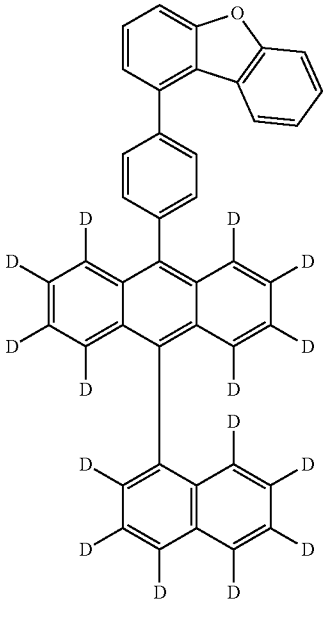
-continued
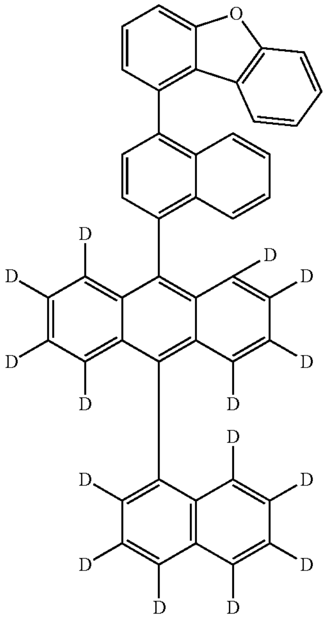
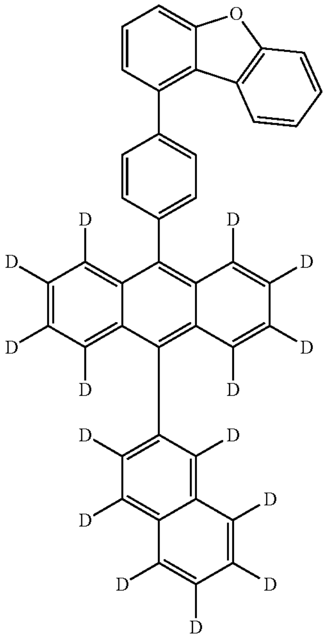

-continued
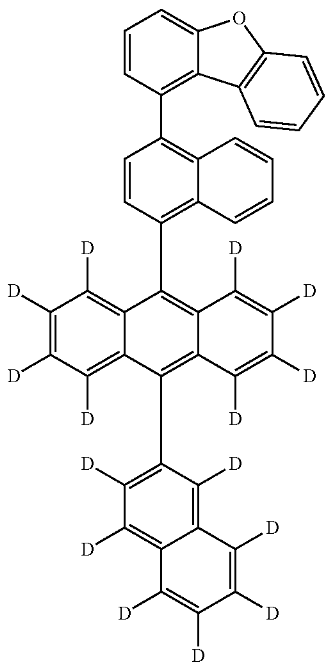
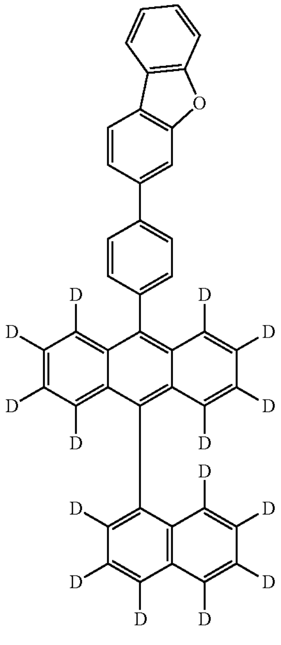
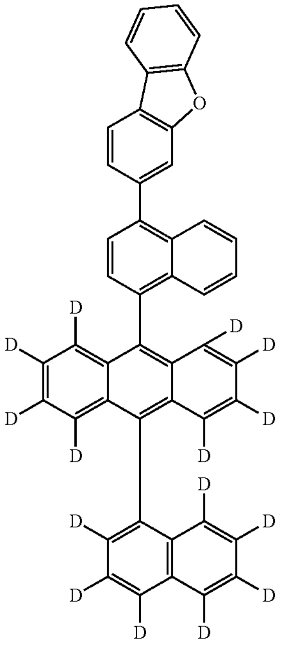
-continued
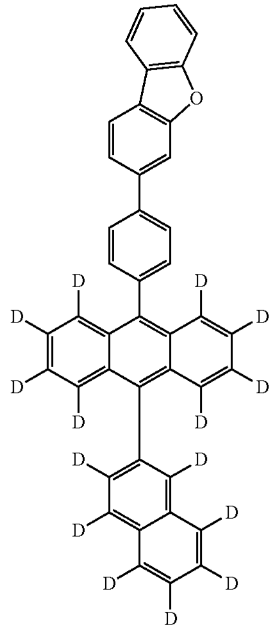
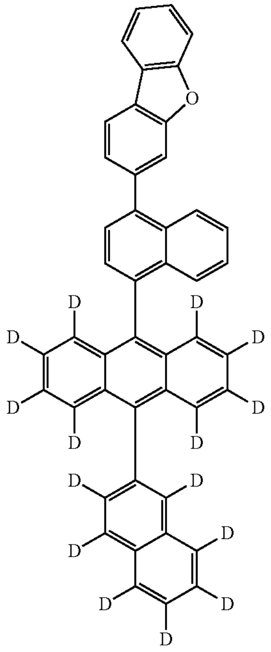
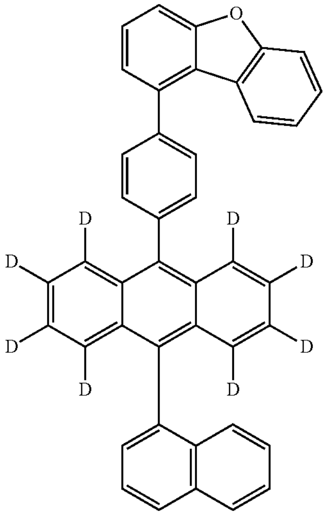
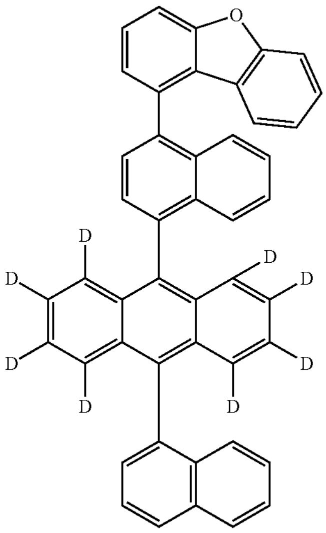

-continued
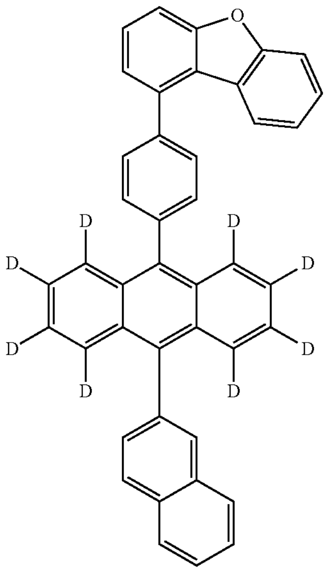
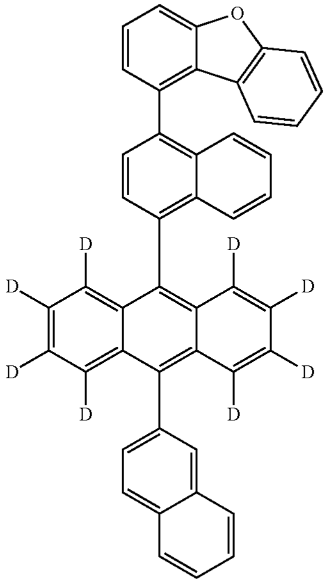
-continued
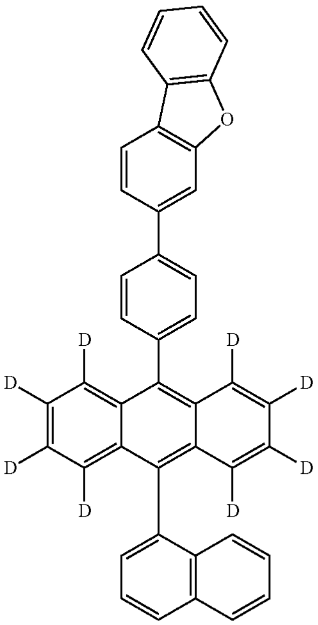
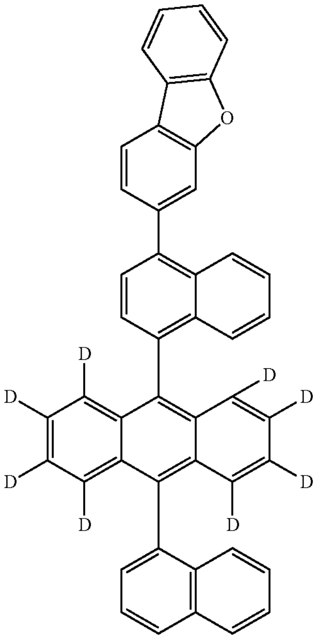

-continued
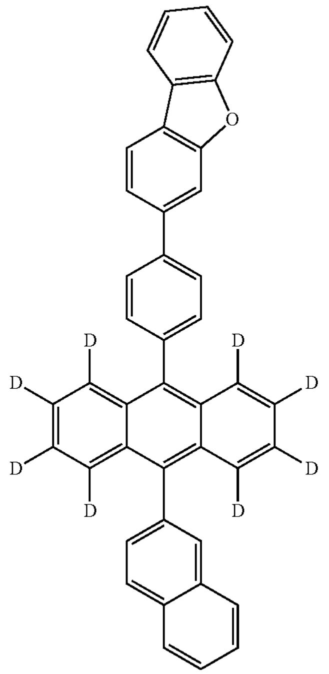
-continued
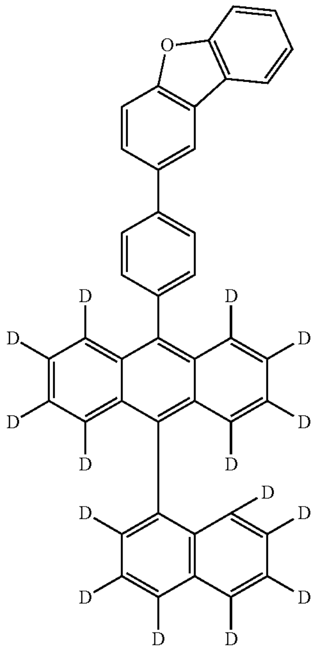
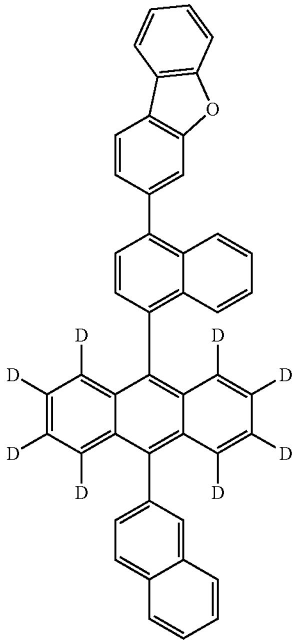
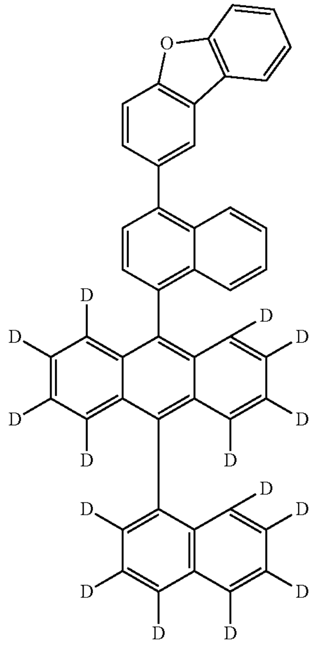

-continued
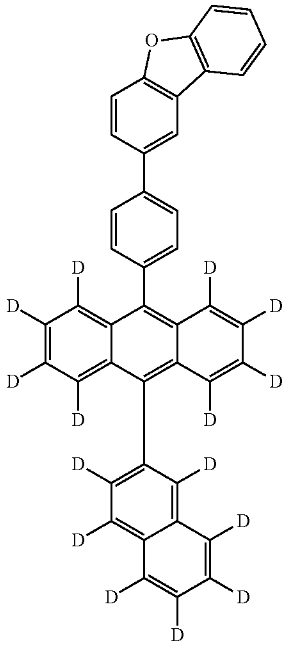
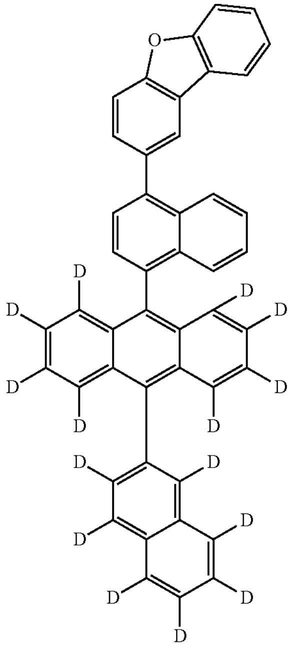
-continued
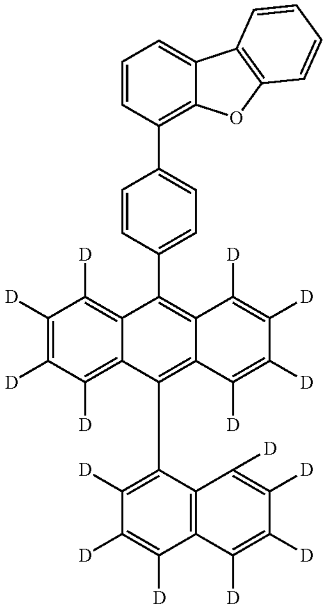
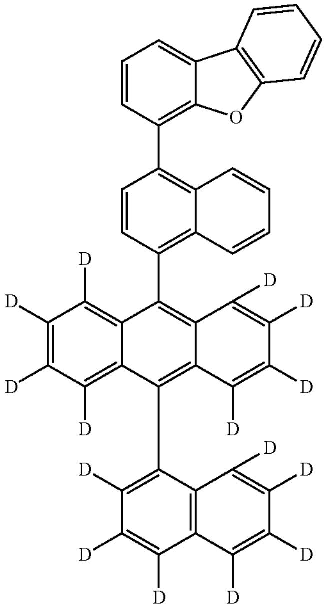

-continued
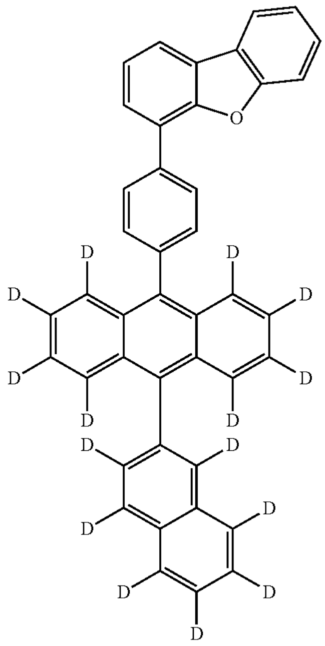
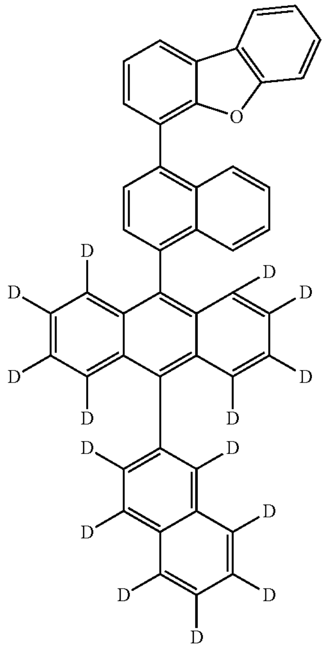
-continued
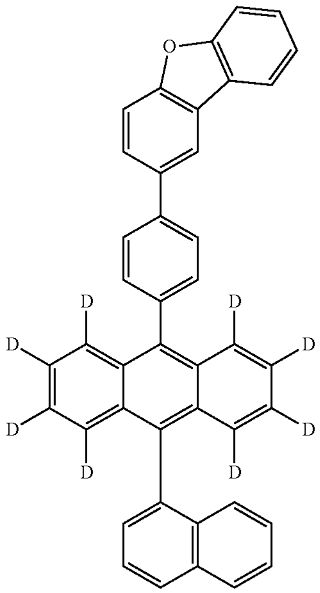
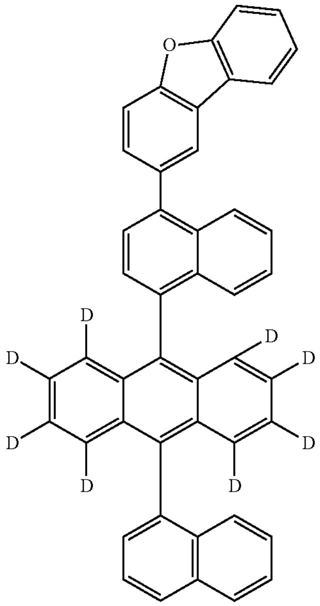

-continued
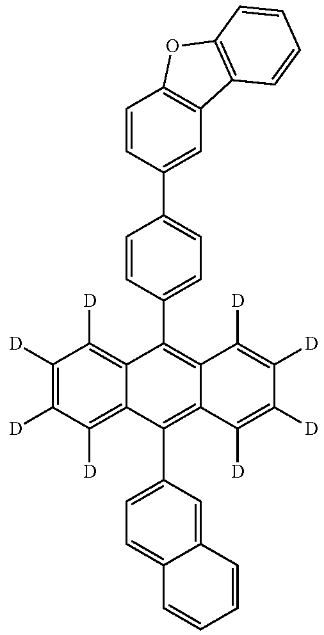
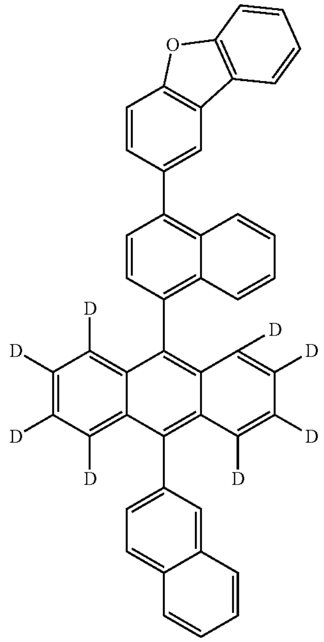
-continued
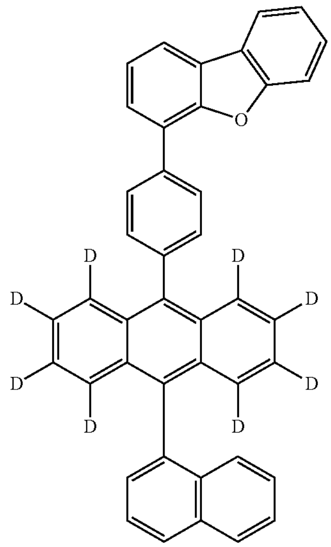
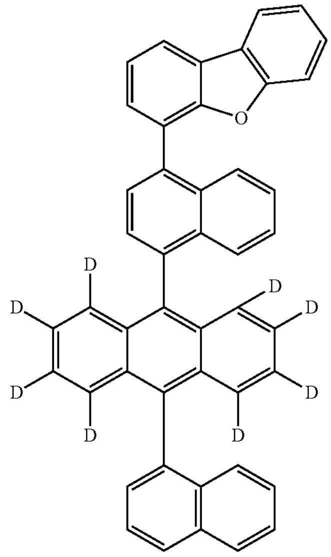
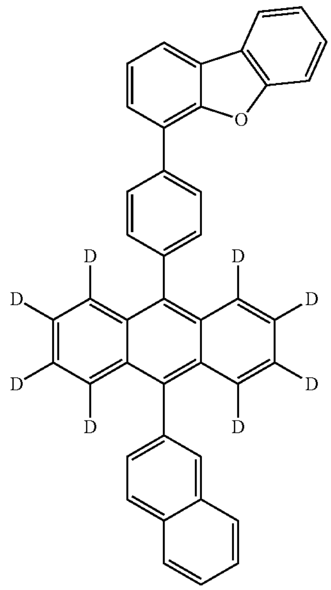

-continued
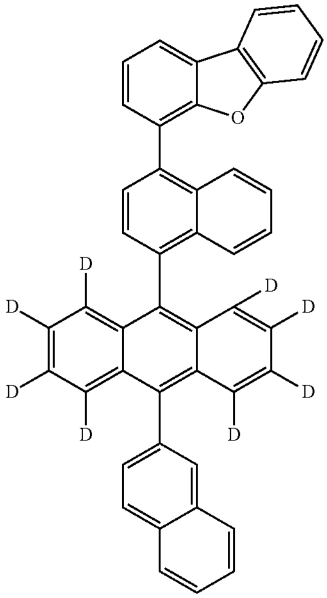
-continued
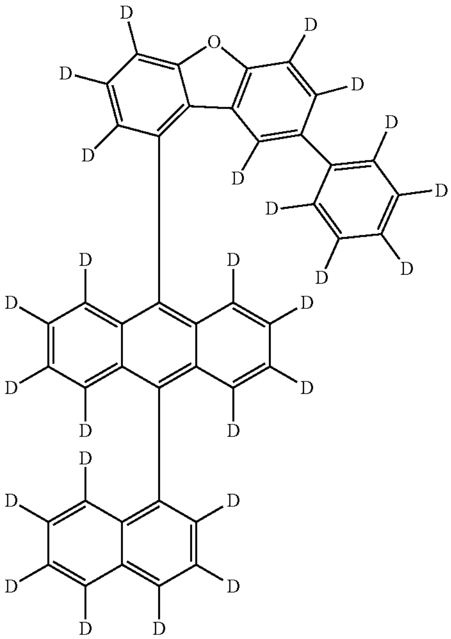
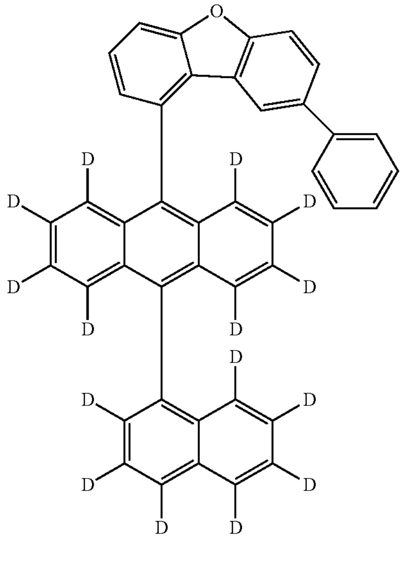
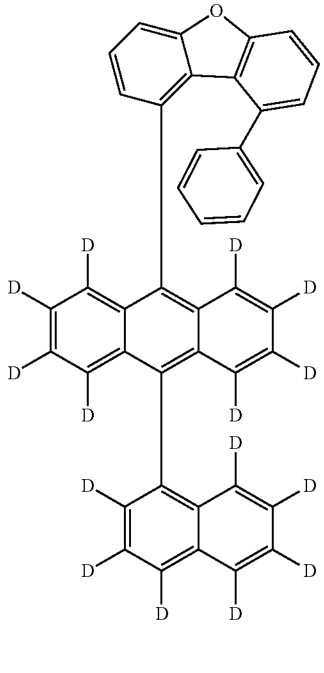

-continued
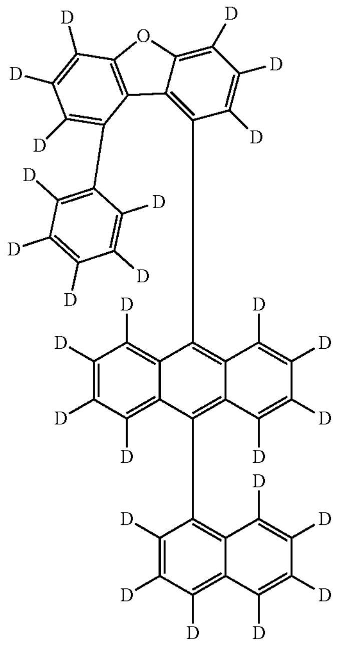
-continued
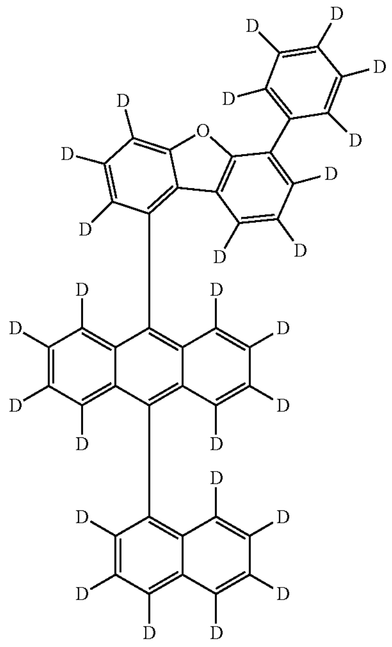
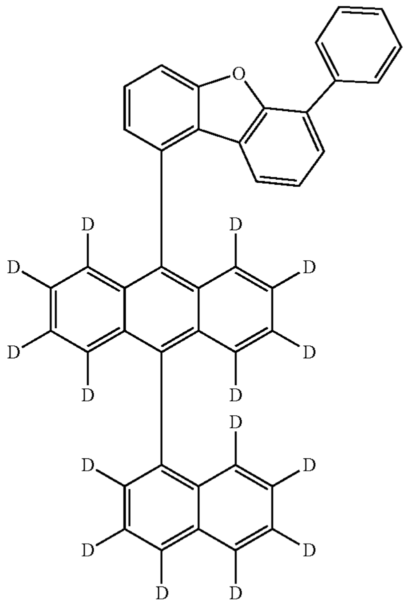
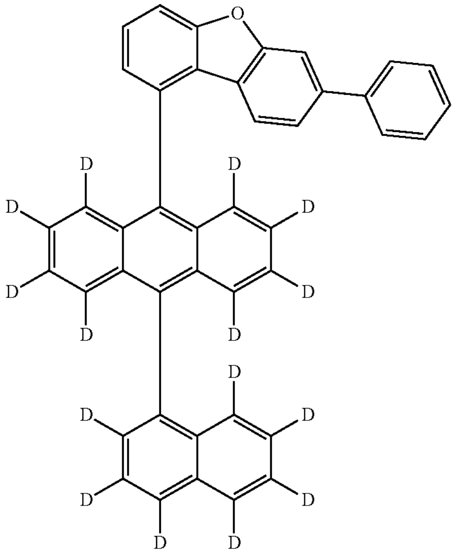

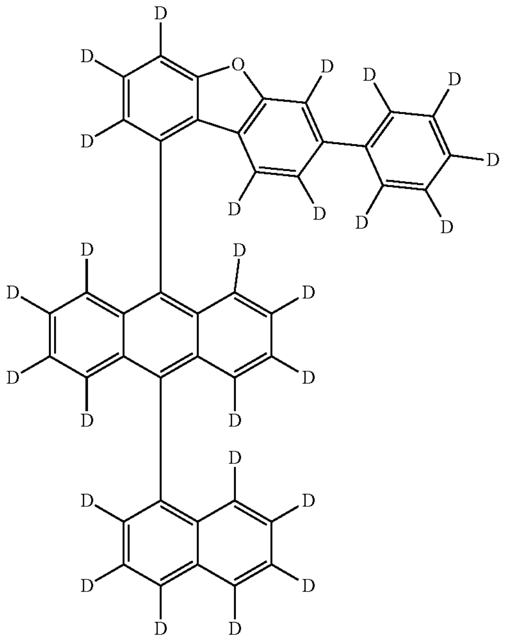
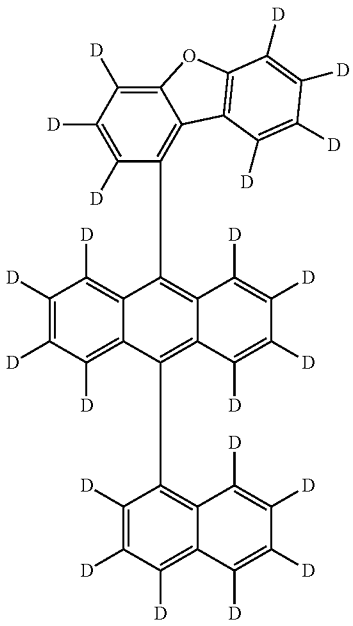
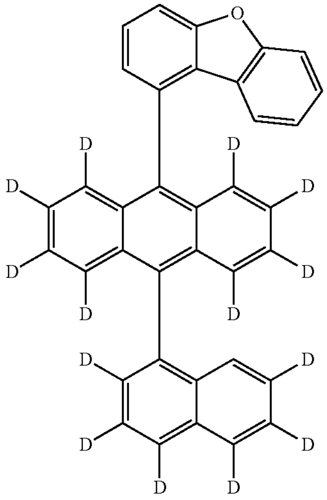
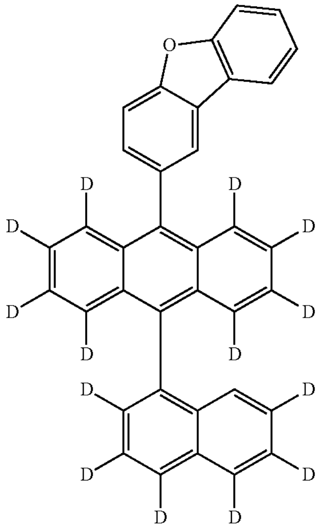

-continued
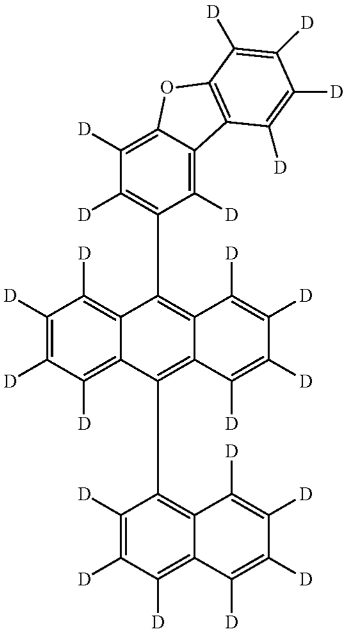
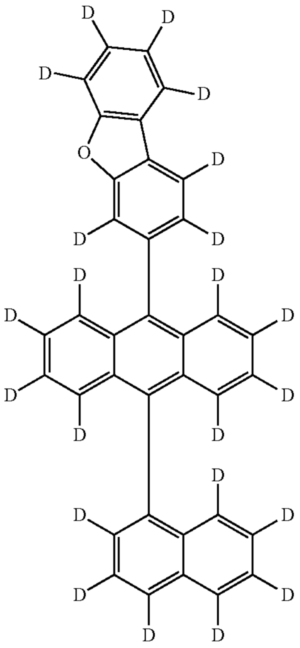
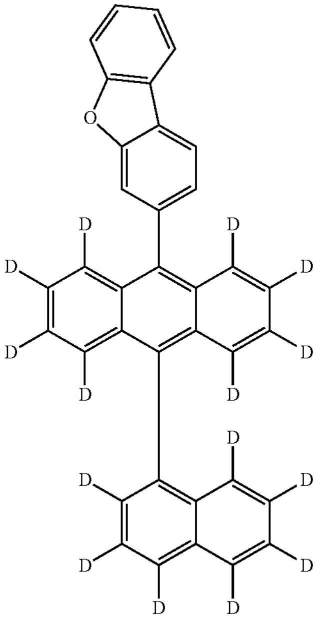
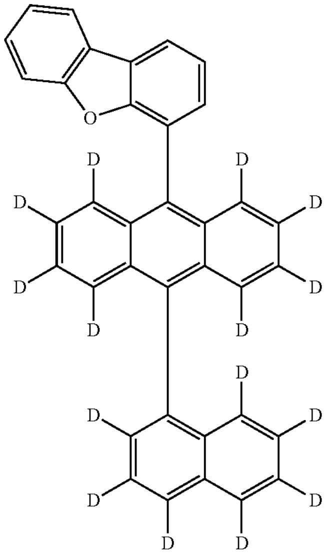

-continued
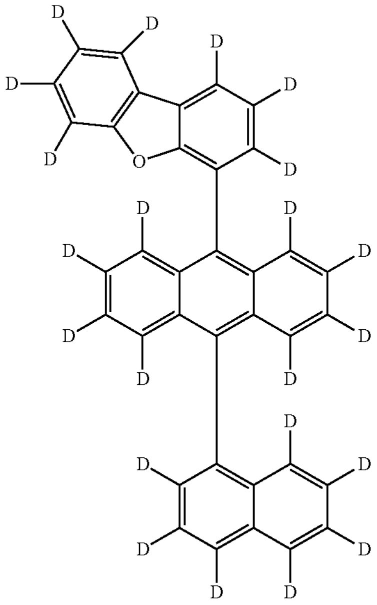
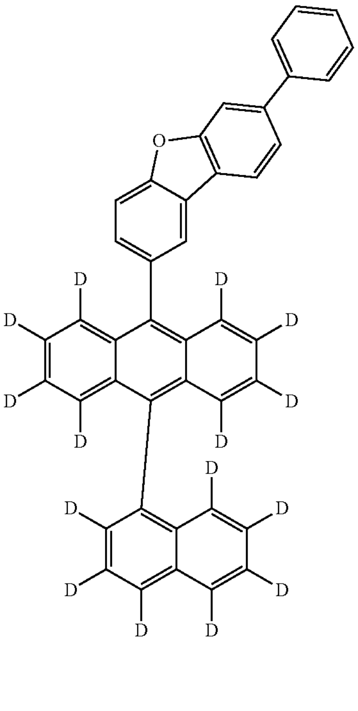
-continued
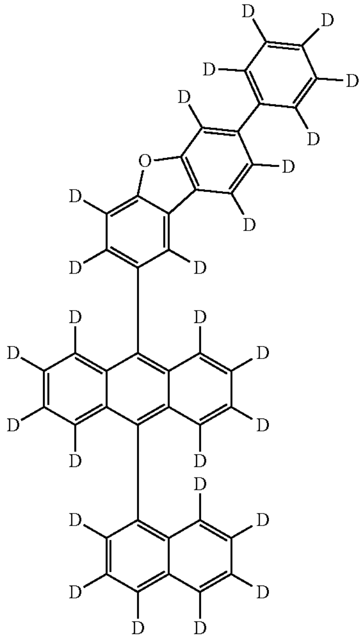
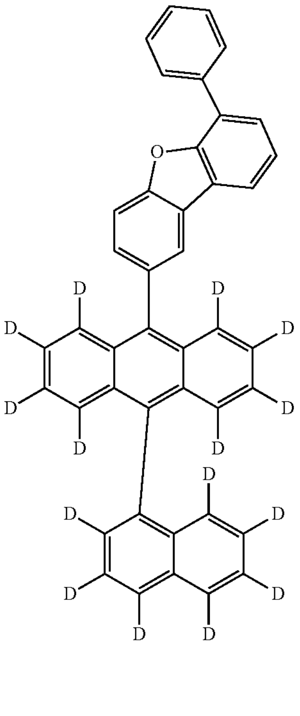

-continued
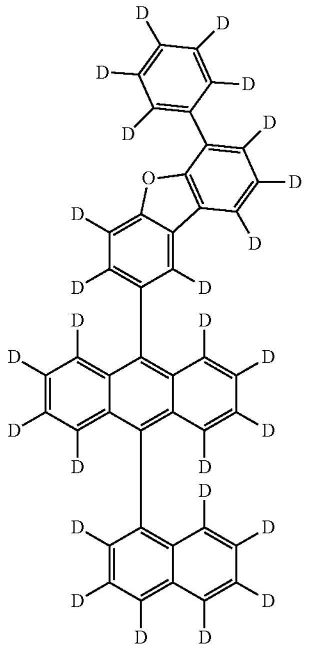
-continued
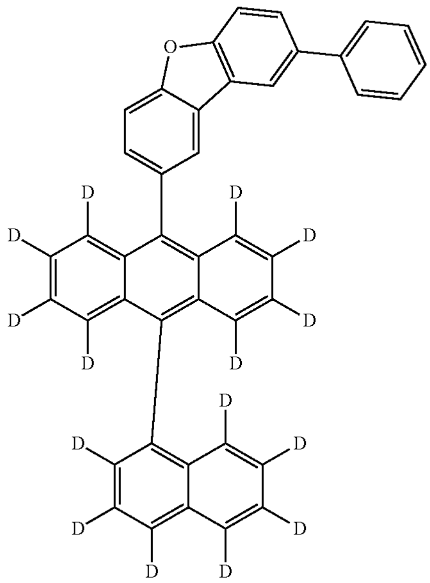
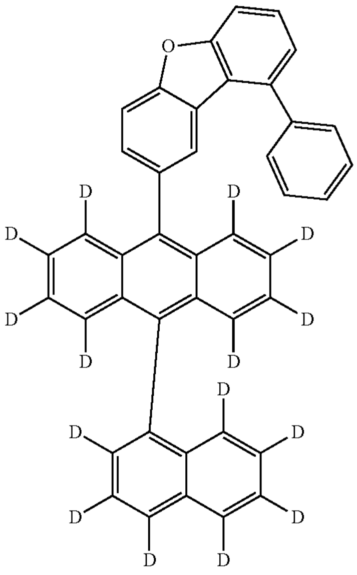
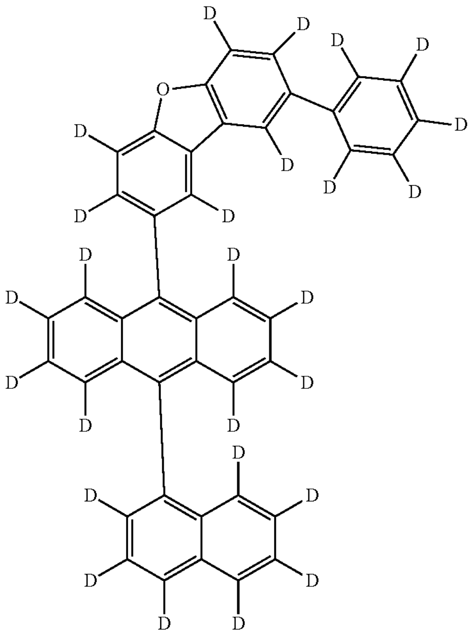 [SMILES: [2H]c1c([2H])c([2H])c(-c2c([2H])c([2H])c3oc4c([2H])c([2H])c(-c5c6c([2H])c([2H])c([2H])c([2H])c6c(-c6c([2H])c([2H])c([2H])c7c([2H])c([2H])c([2H])c([2H])c67)c6c([2H])c([2H])c([2H])c([2H])c56)c([2H])c4c3c2[2H])c([2H])c1[2H]]

-continued
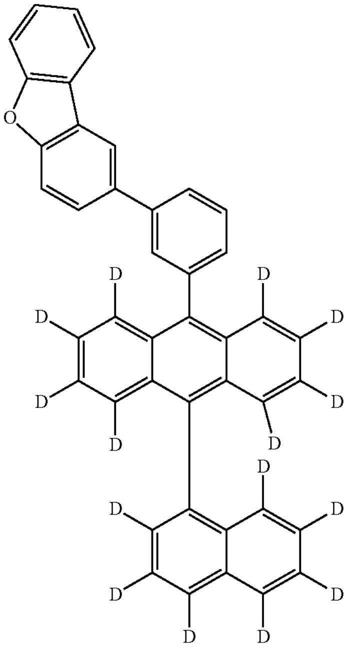
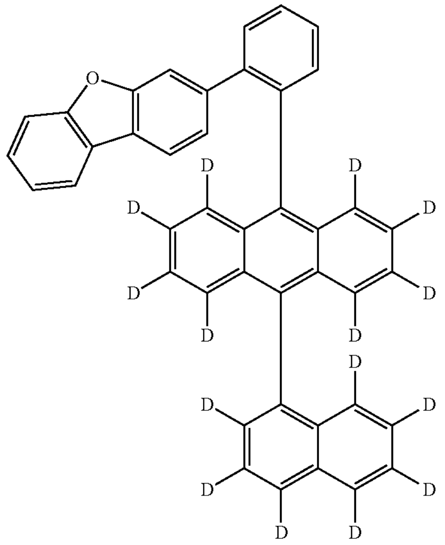
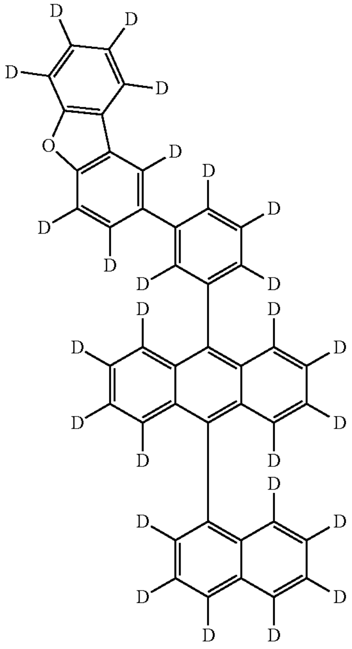
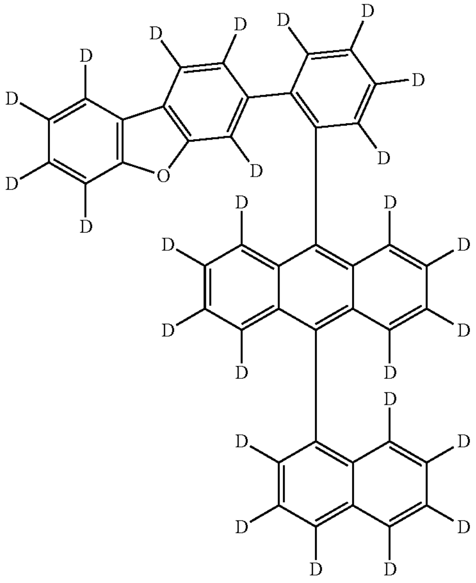

-continued
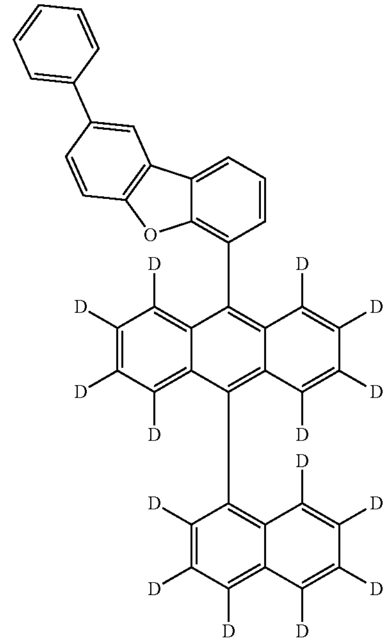
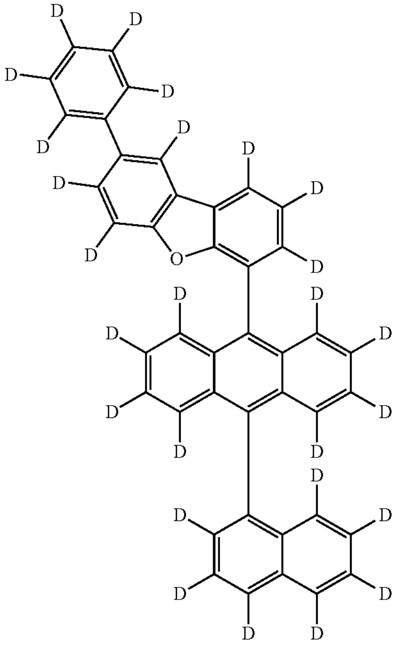
-continued
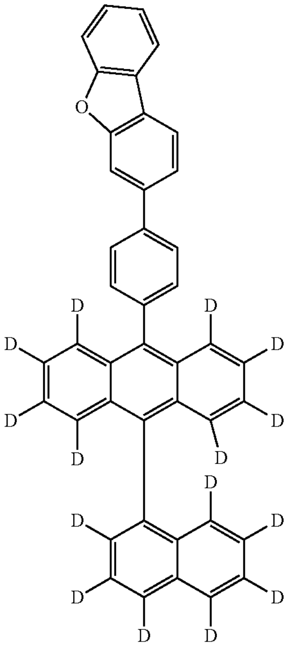
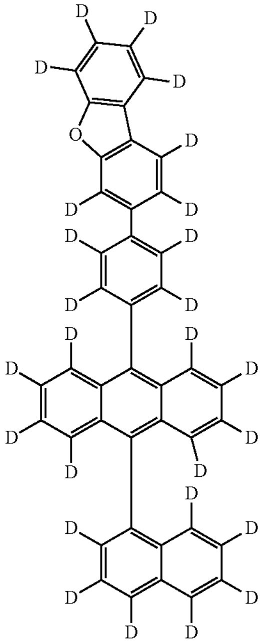
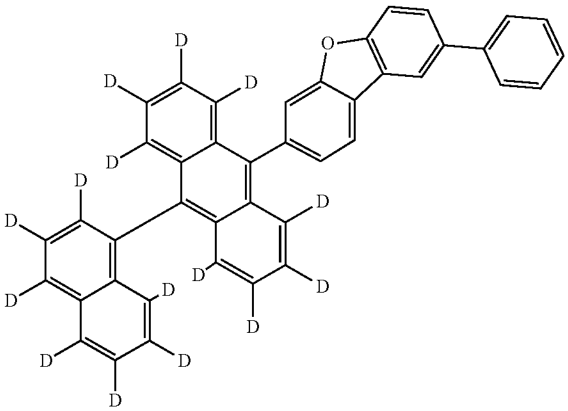

-continued
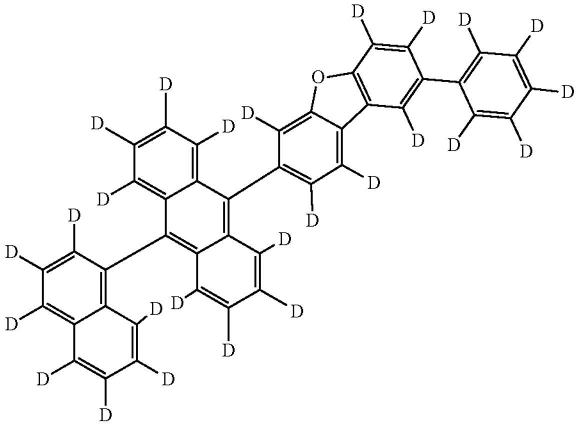
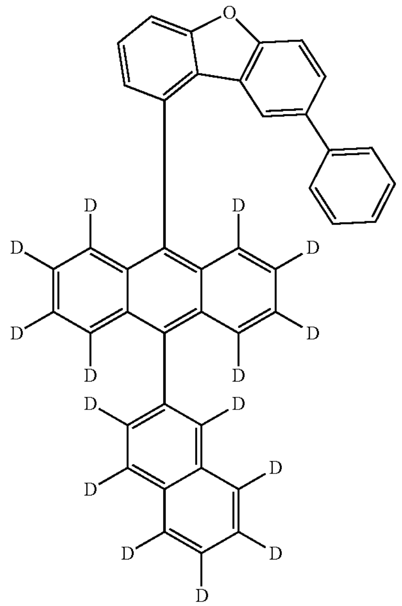
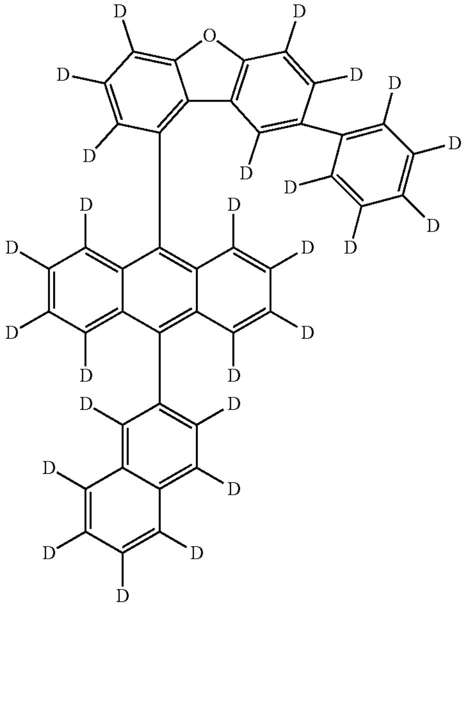
-continued
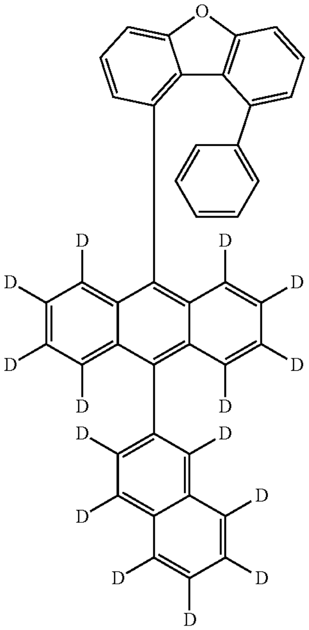
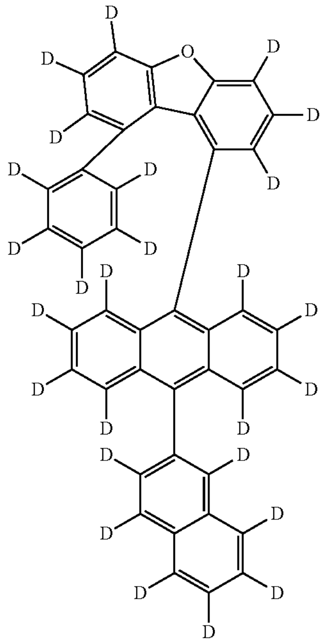

-continued
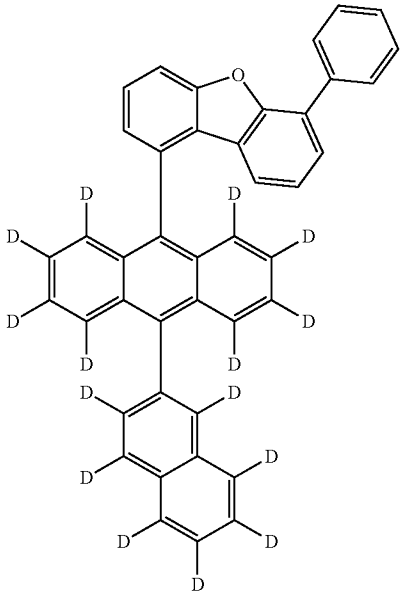
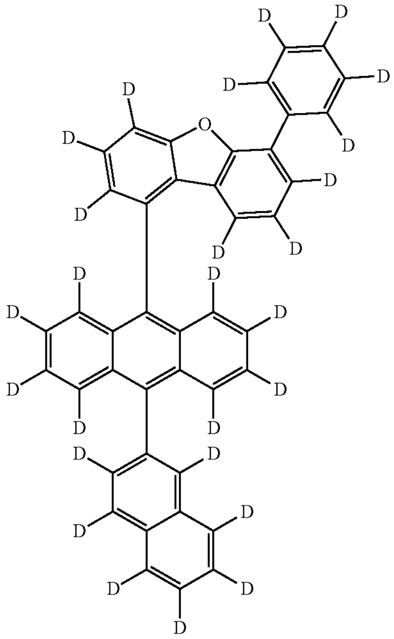
-continued
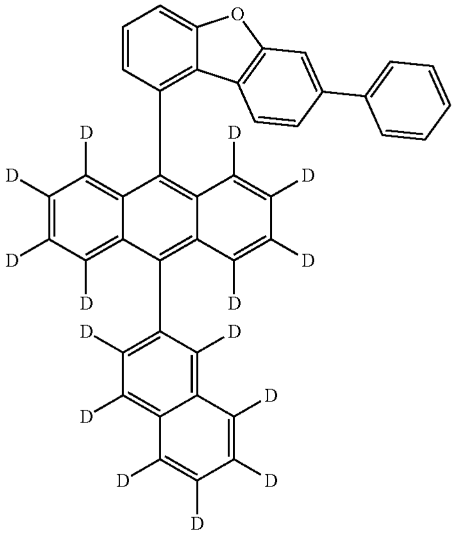
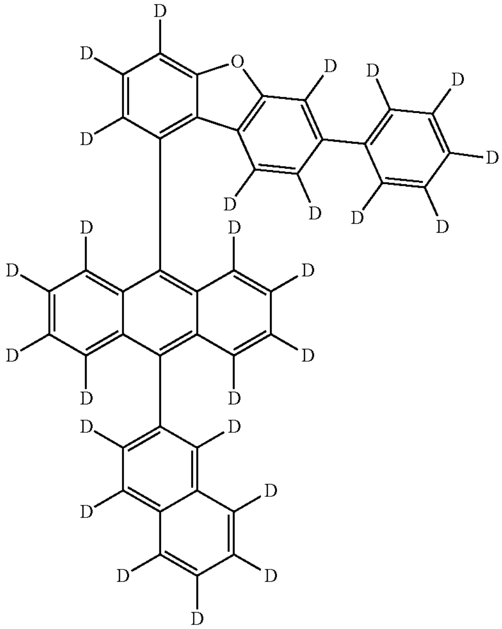
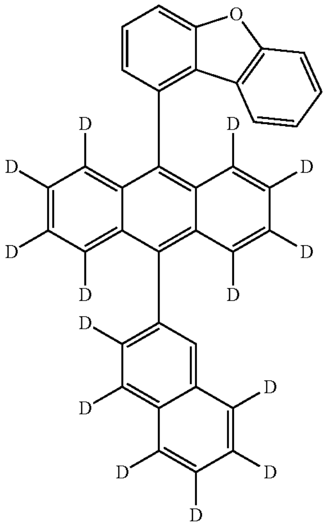

-continued
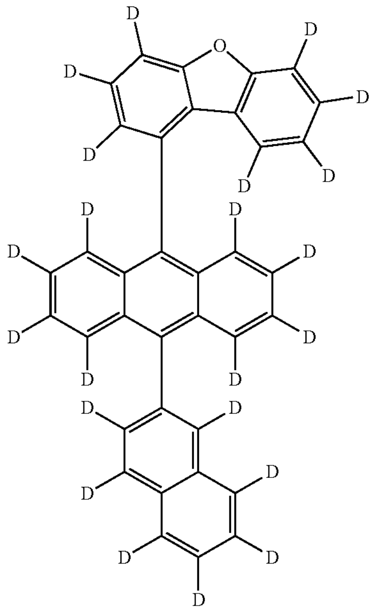
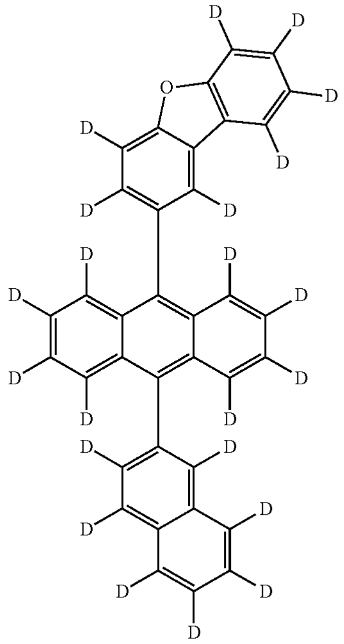
-continued
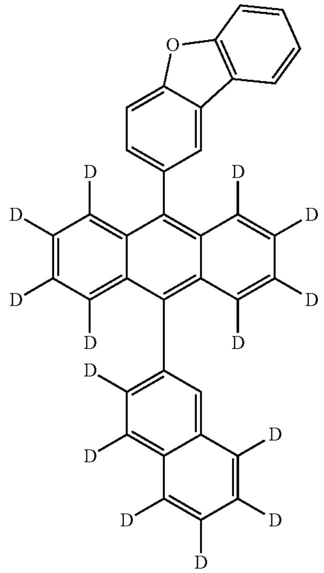
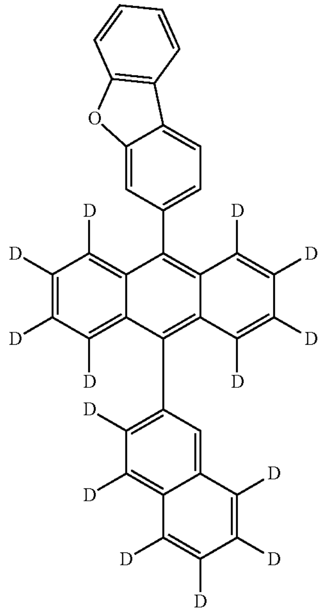

-continued
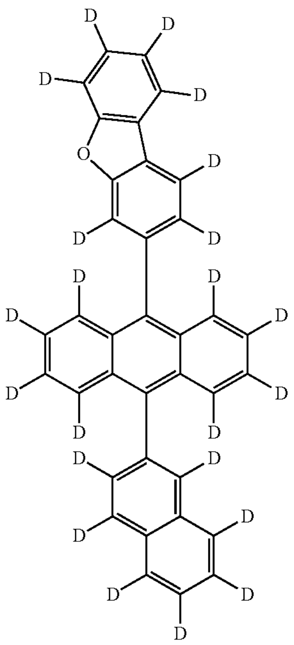
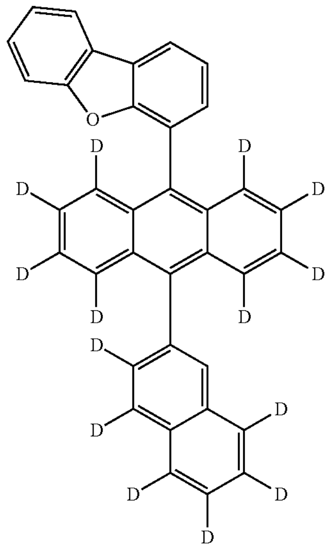
-continued
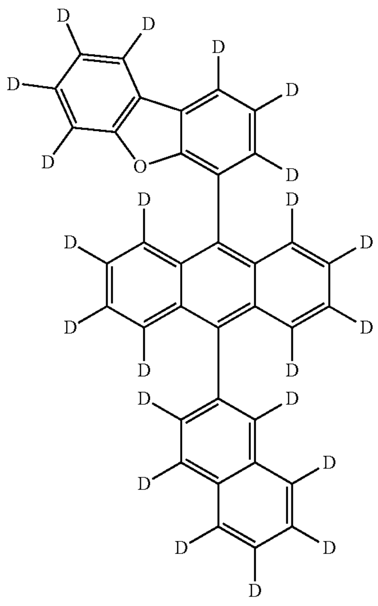
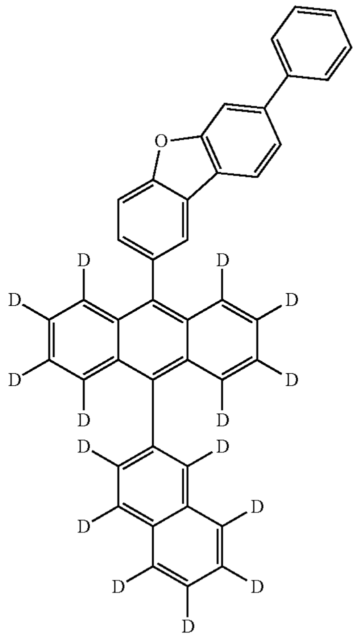

-continued
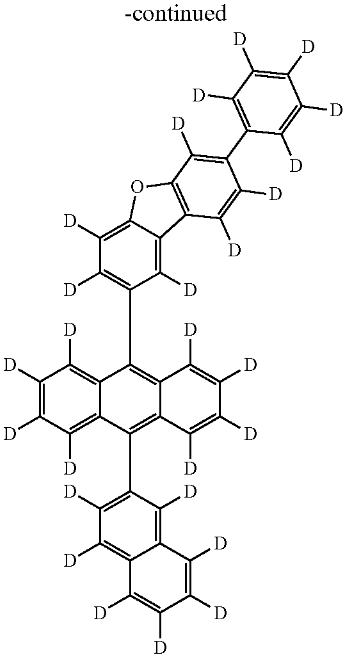
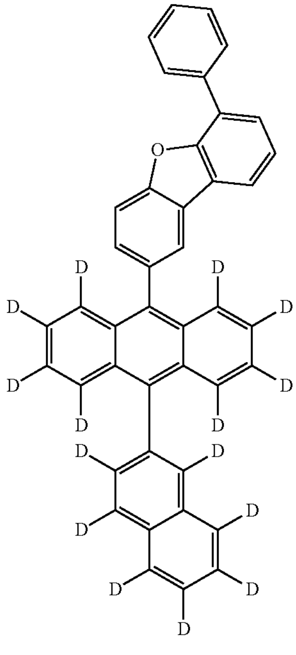
-continued
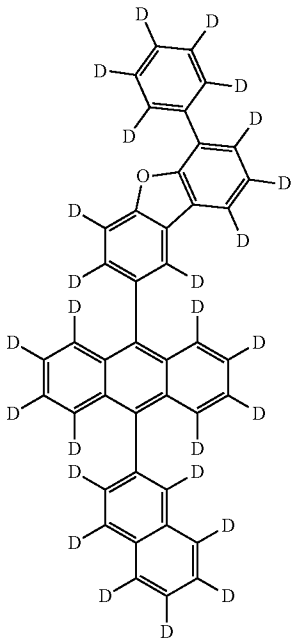
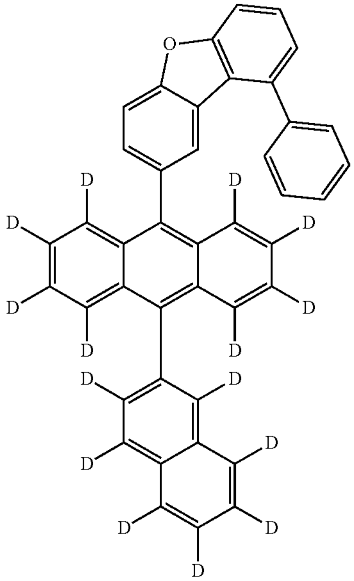

-continued
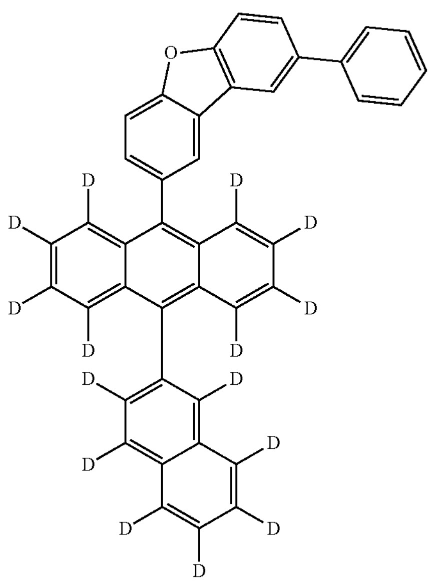
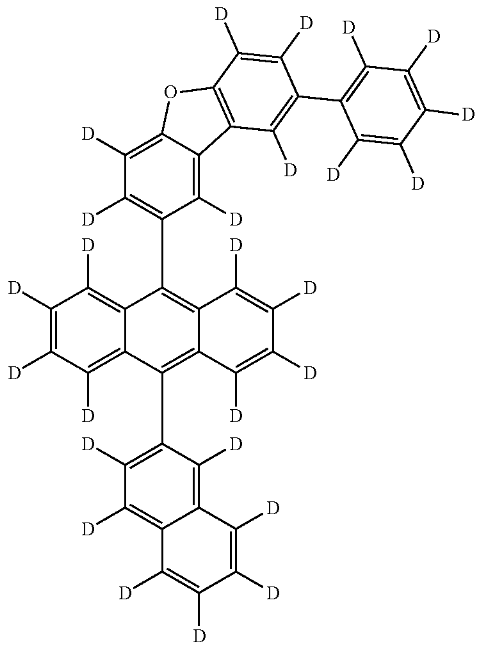
-continued
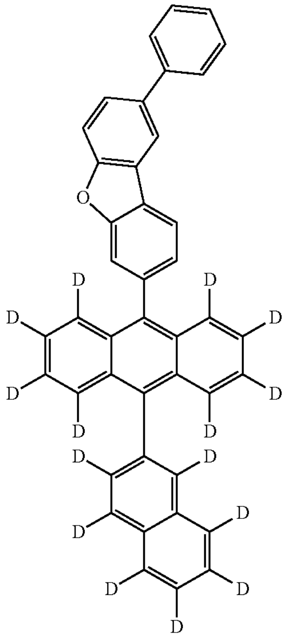
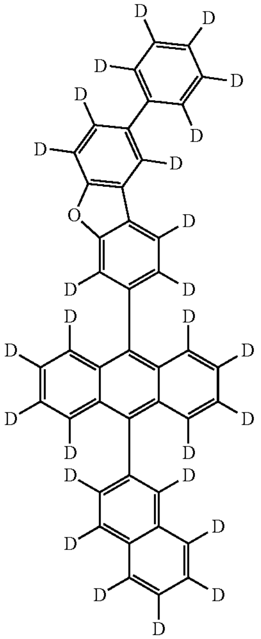

-continued
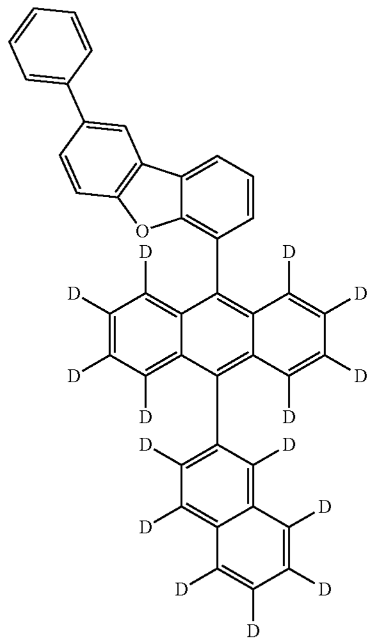
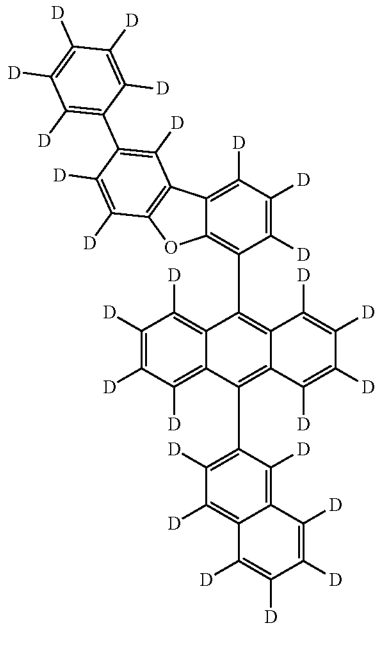
-continued
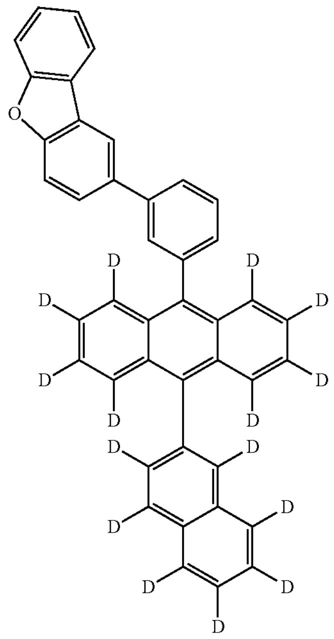
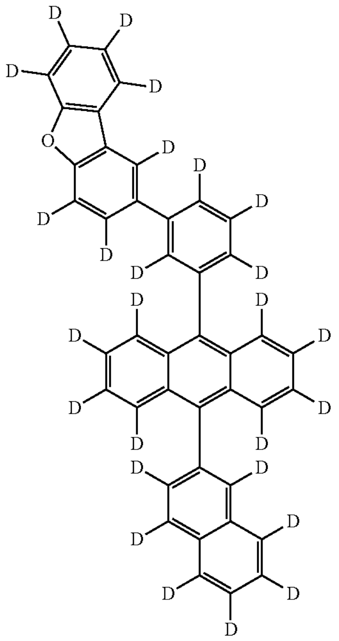

-continued
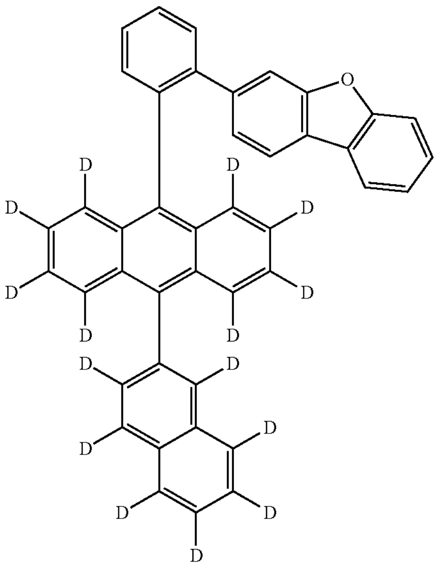
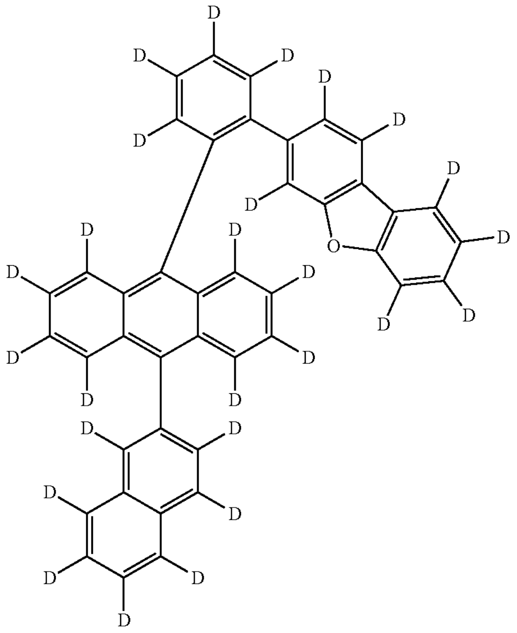
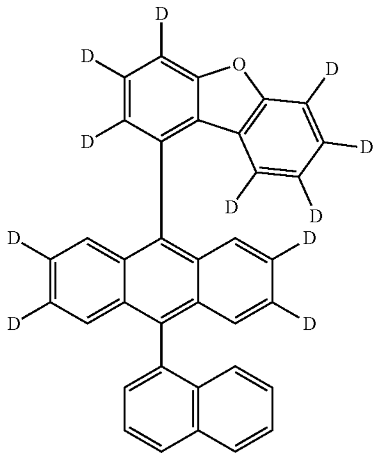
-continued
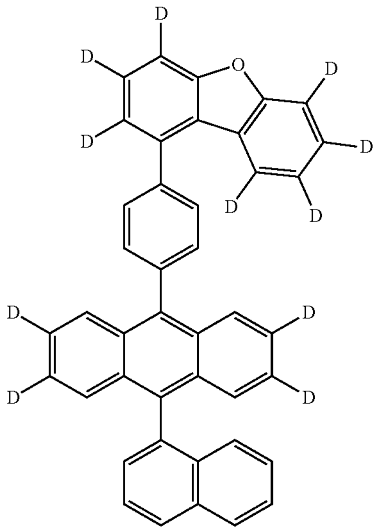
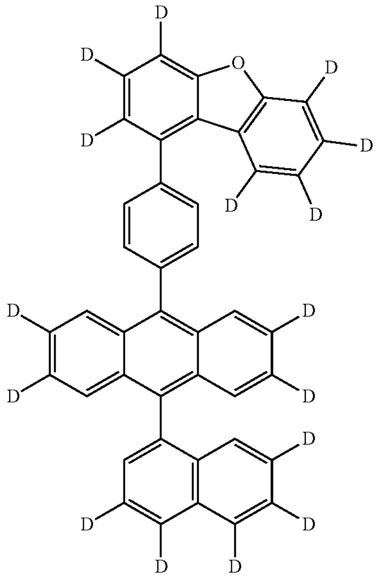
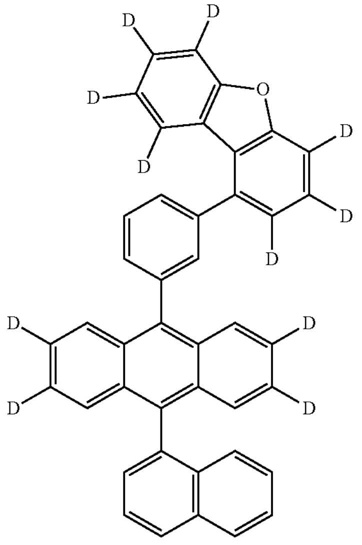

-continued
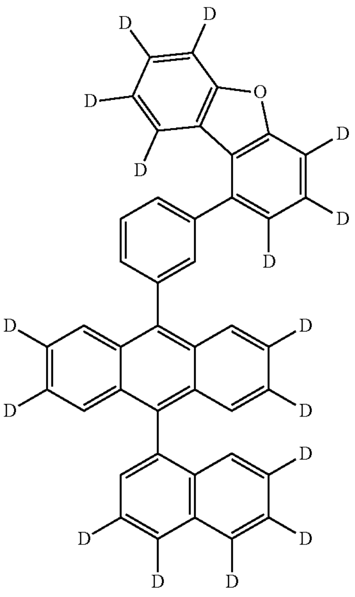
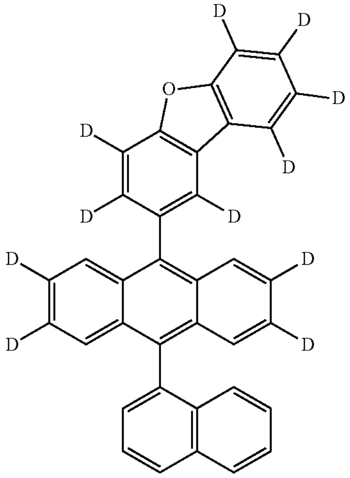
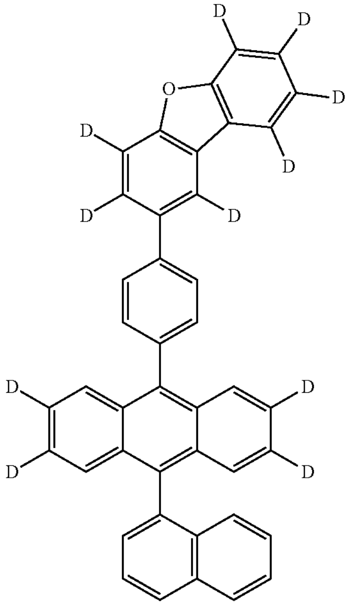
-continued
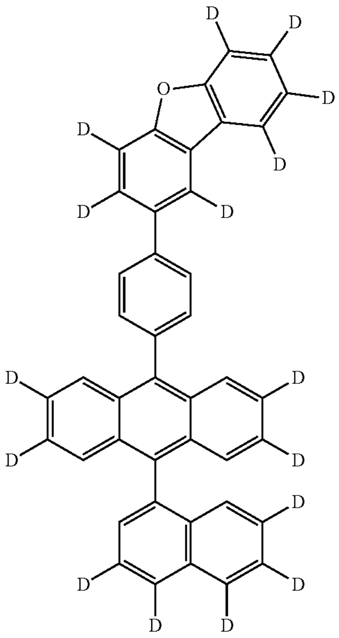
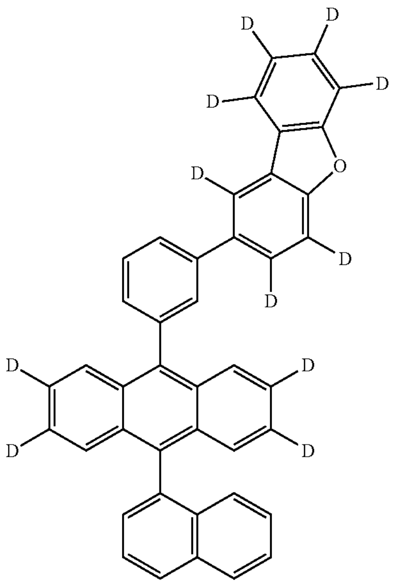

-continued
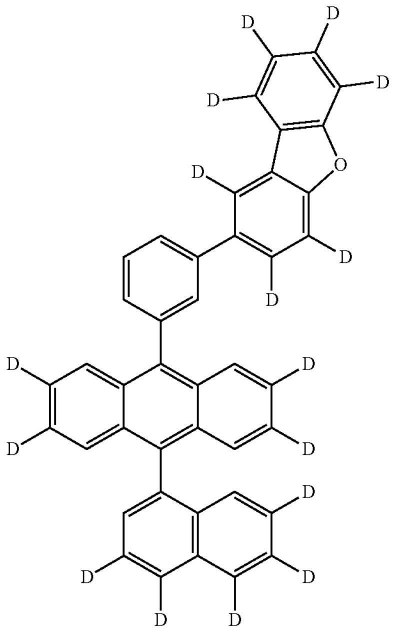
-continued
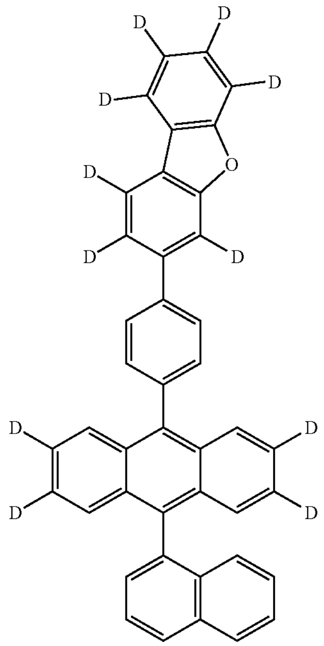
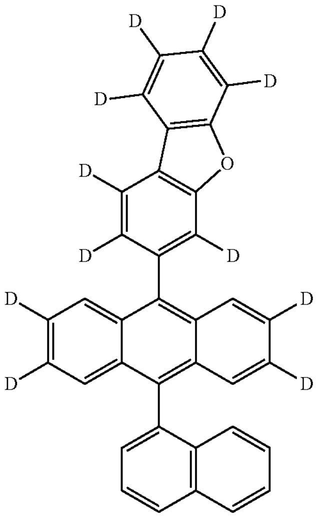
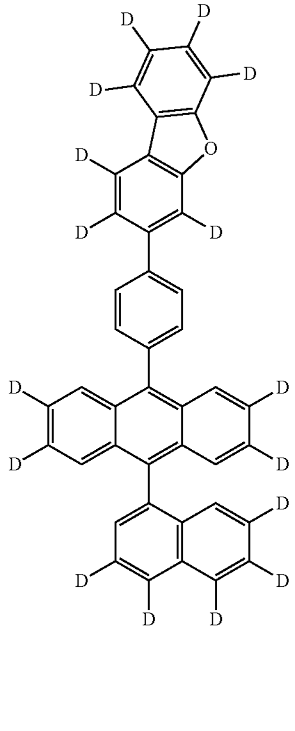

-continued
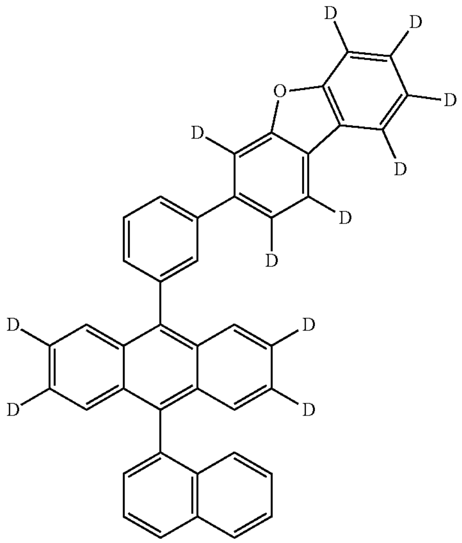
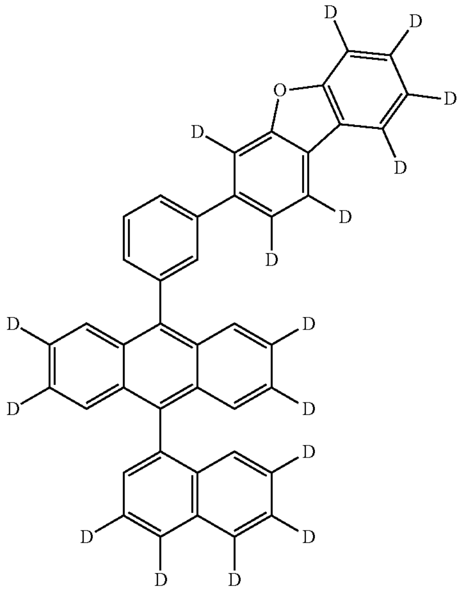
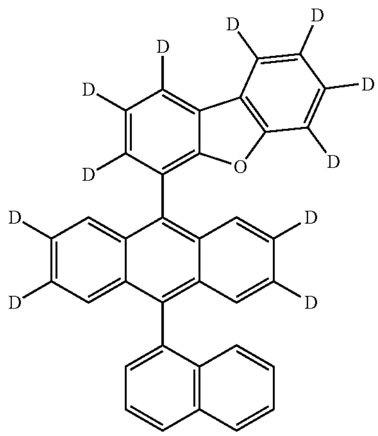
-continued
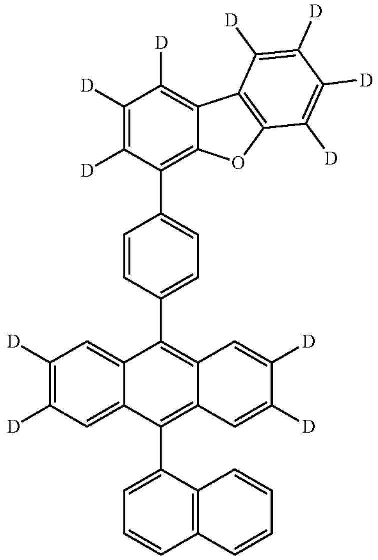
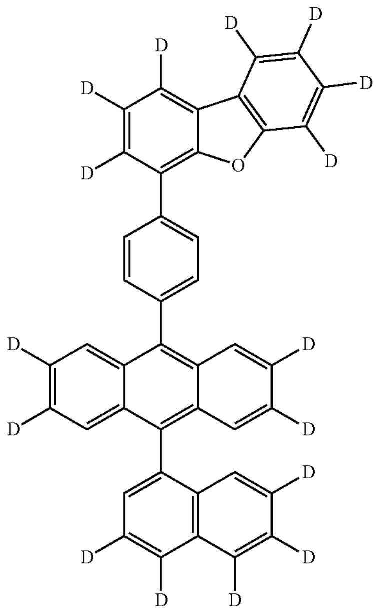

-continued
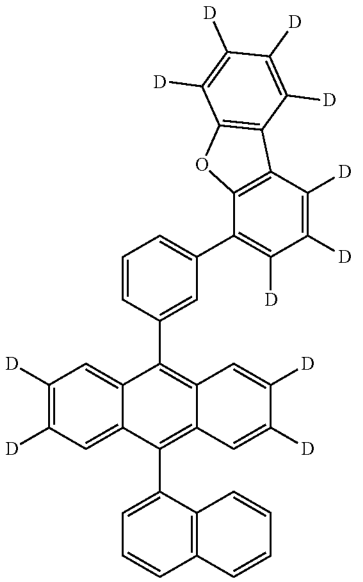
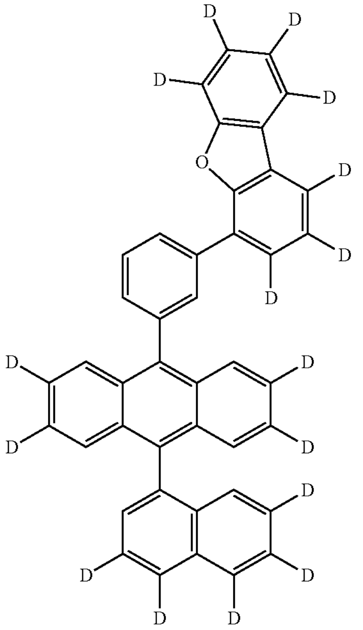
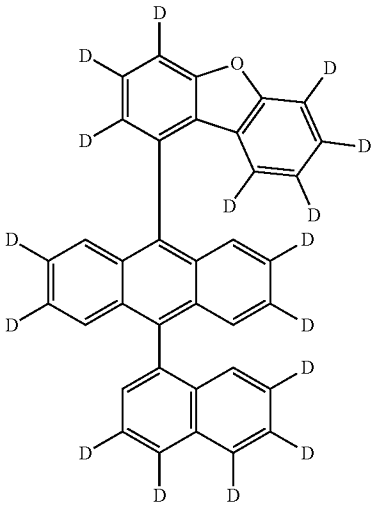
-continued
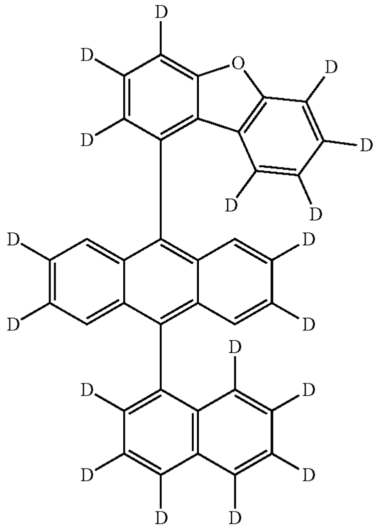
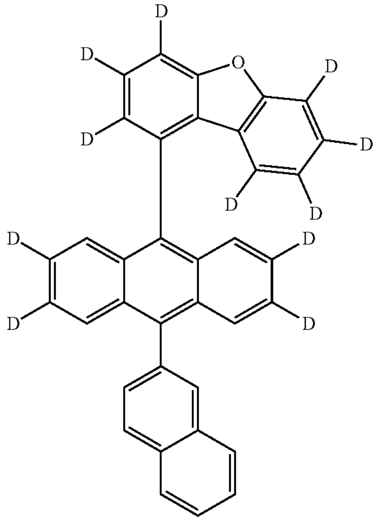
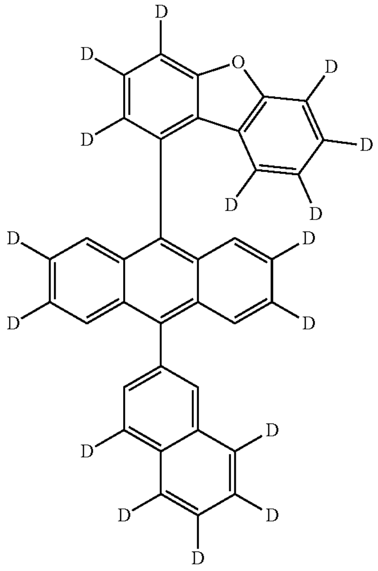

-continued
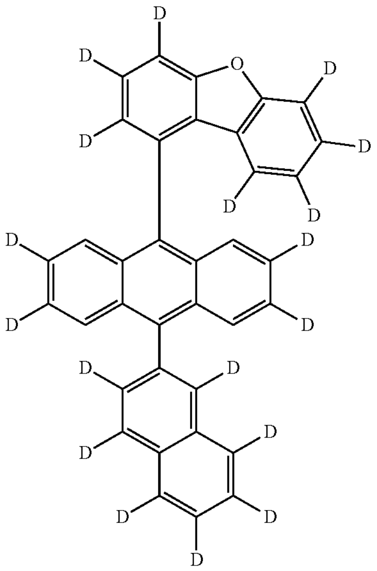
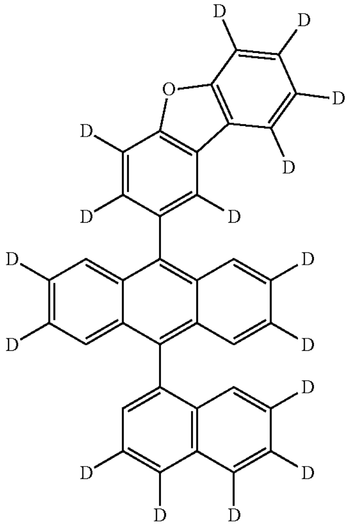
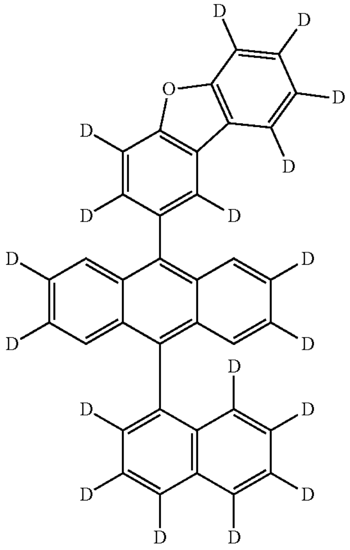
-continued
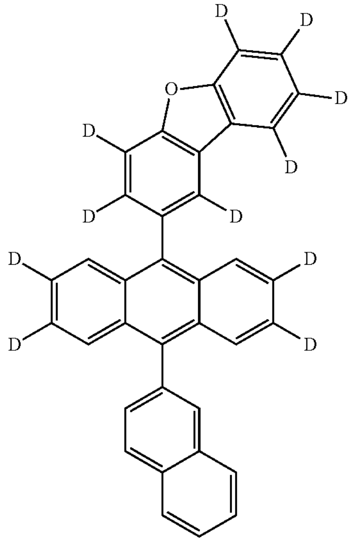
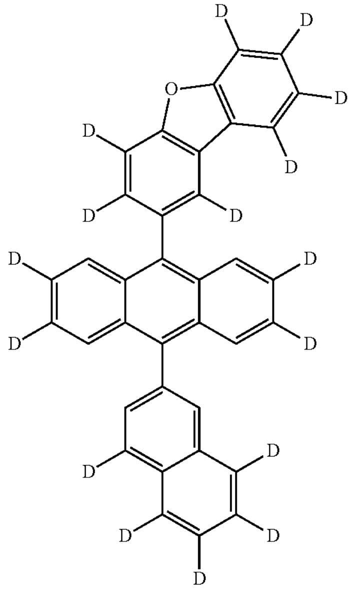
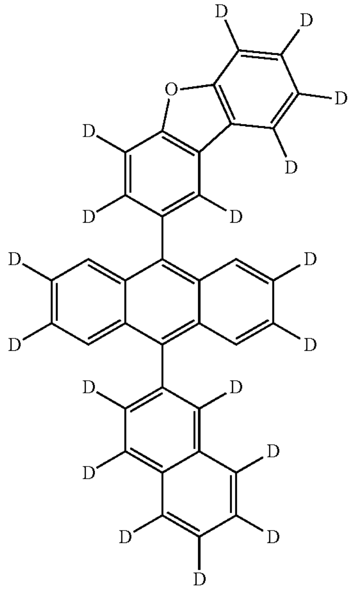

-continued
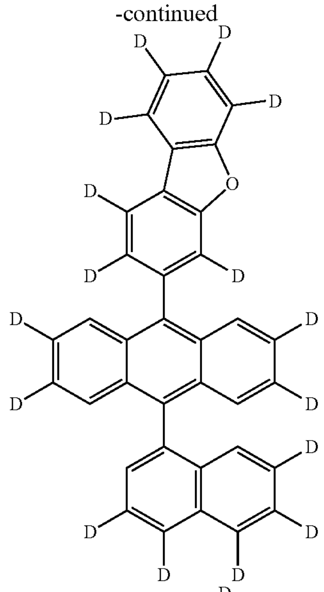
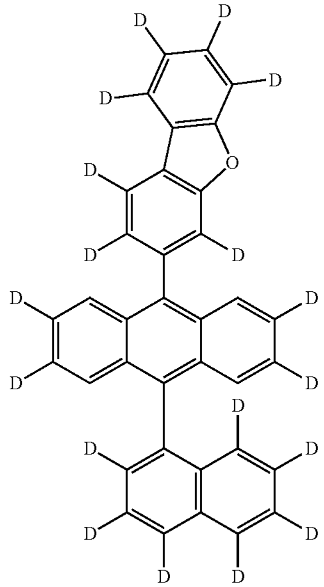
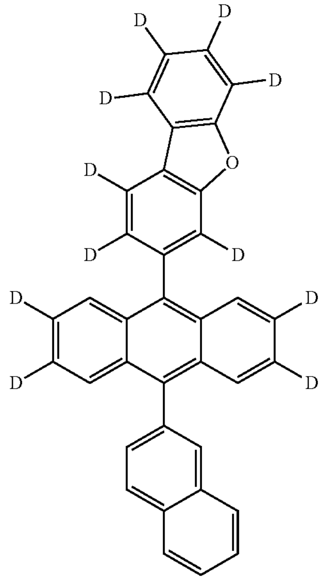
-continued
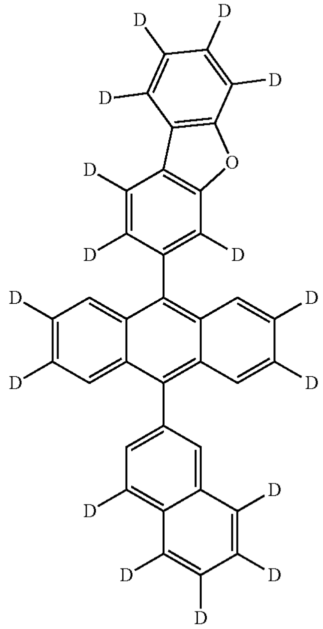
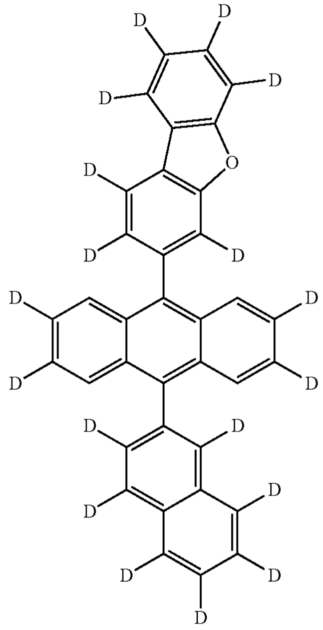

-continued
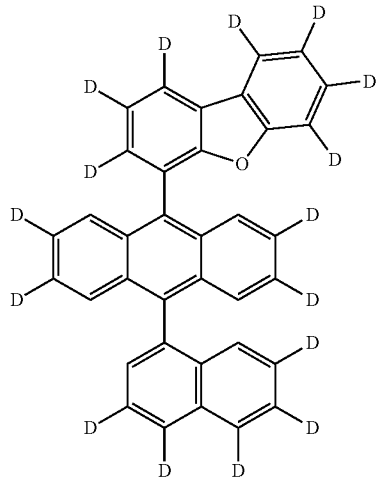
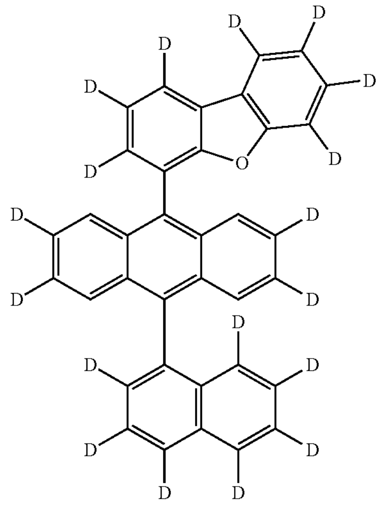
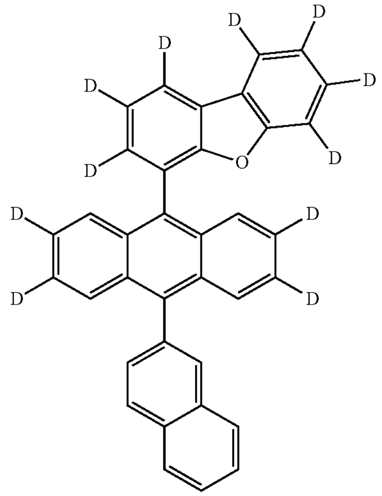
-continued
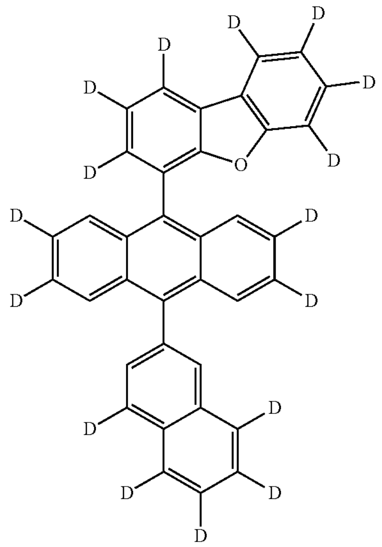
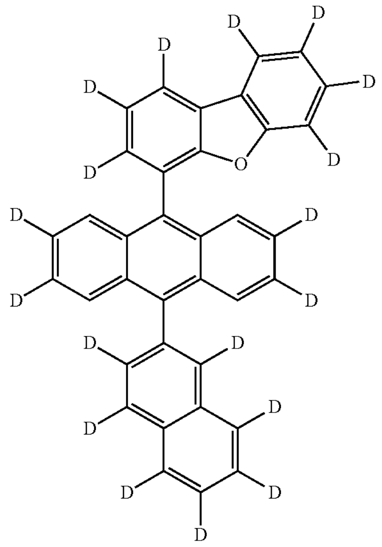
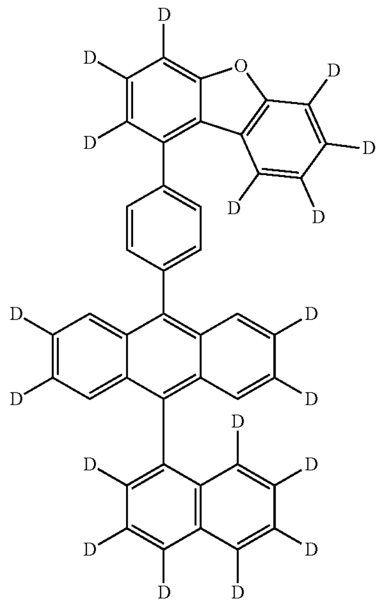

-continued
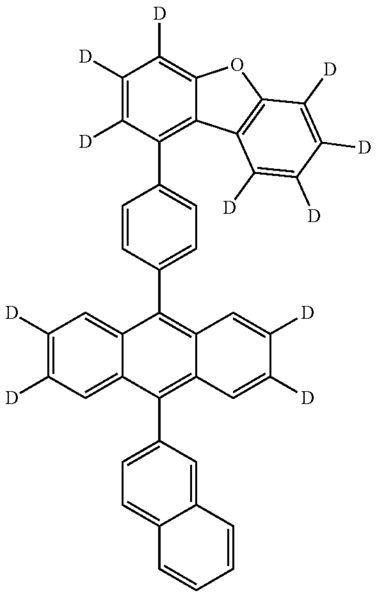
-continued
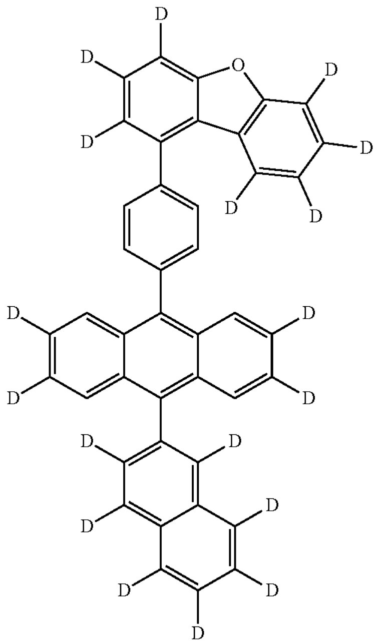
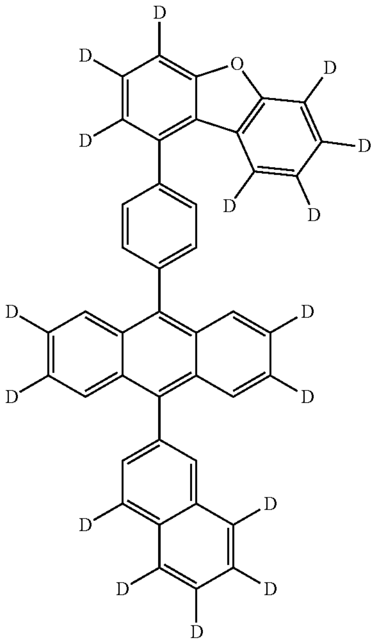
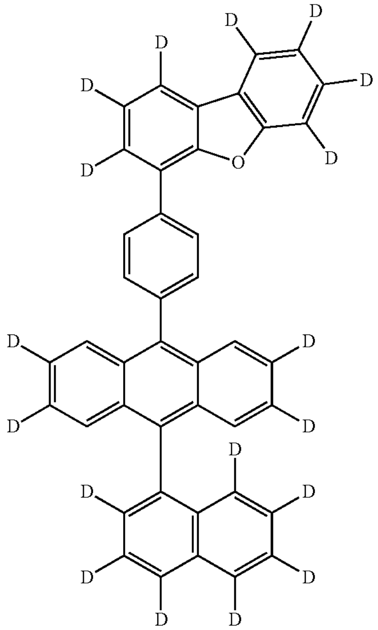

-continued
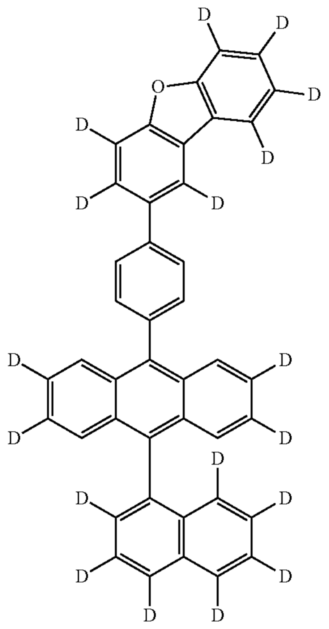
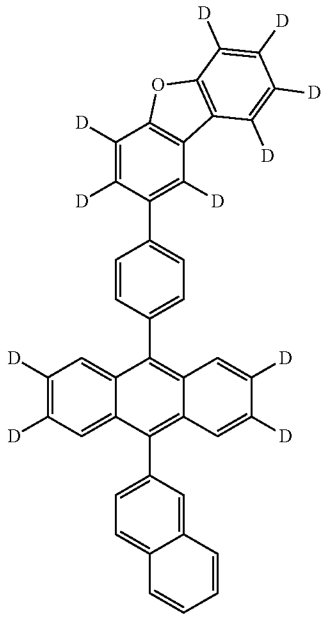
-continued
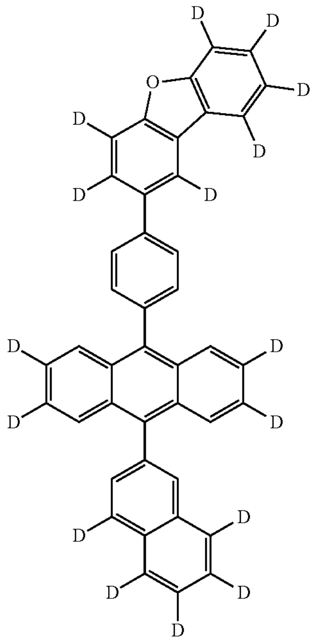
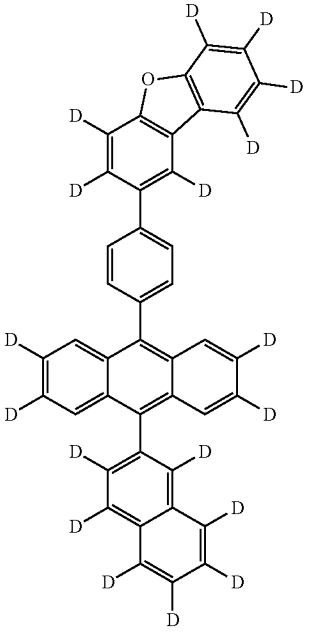

-continued
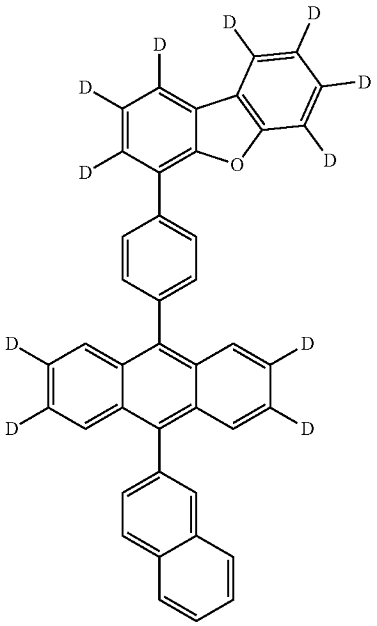
-continued
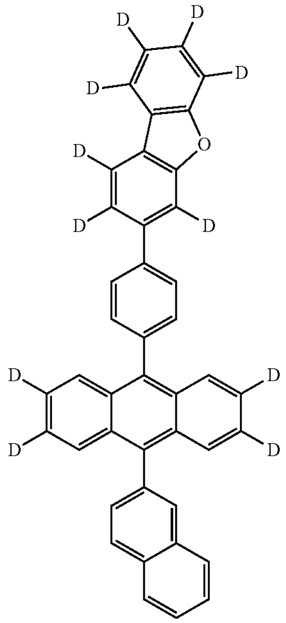
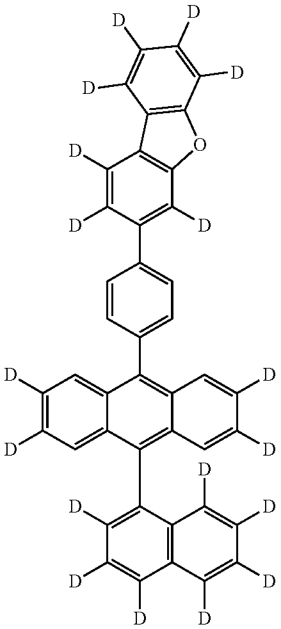
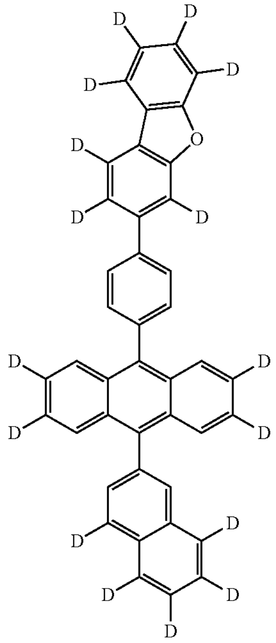

-continued
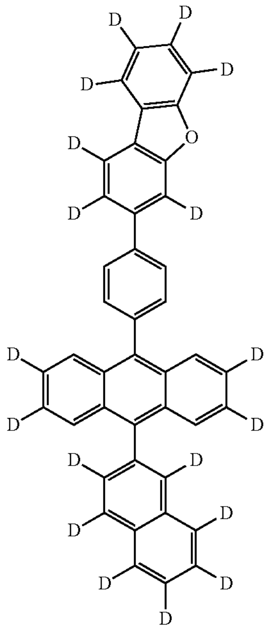
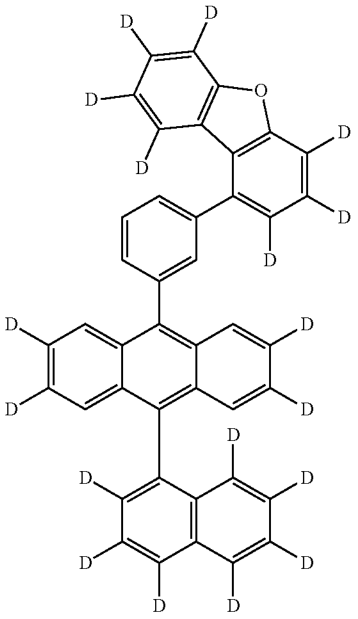
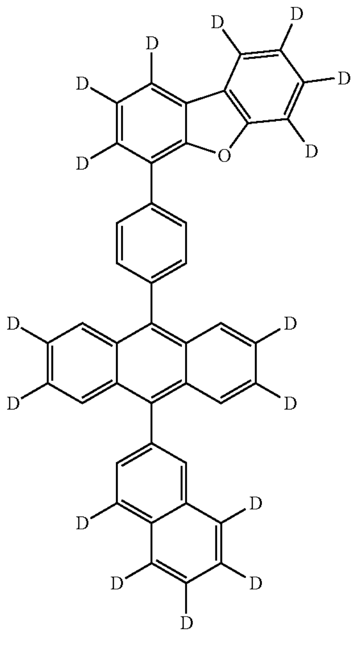
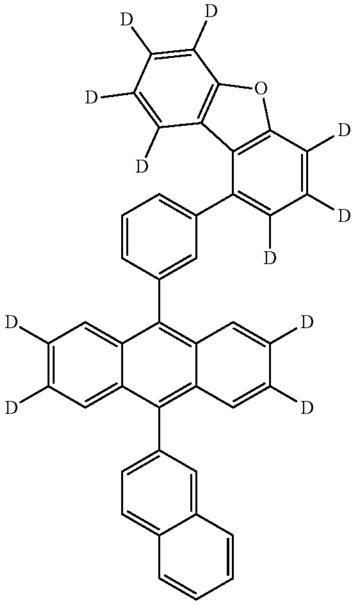

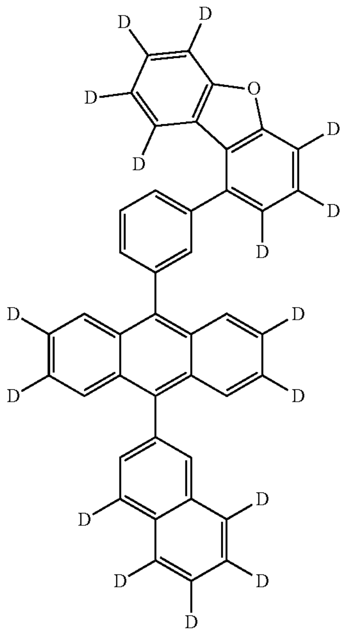
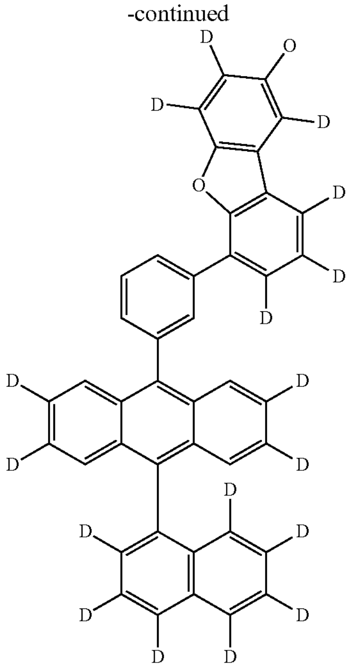
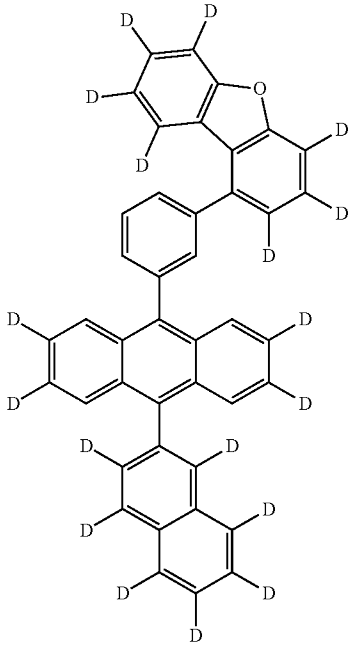
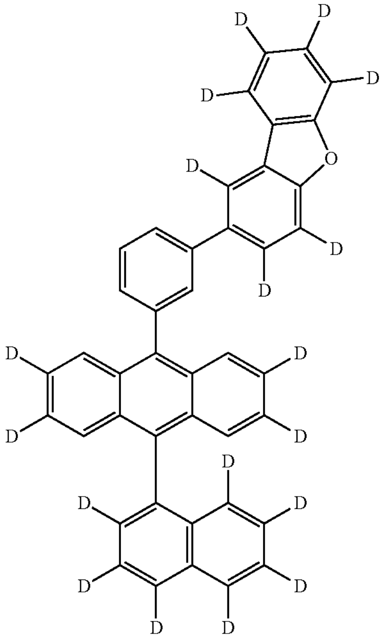

-continued
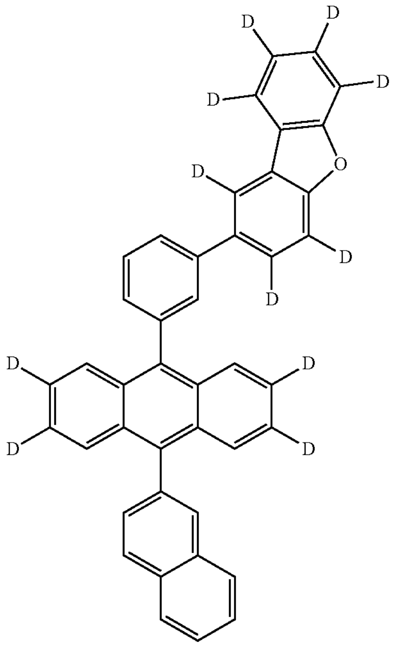
-continued
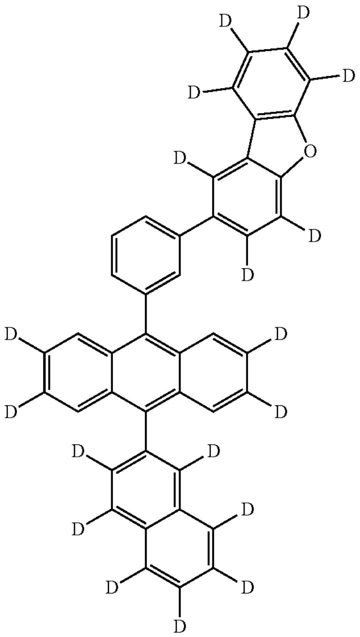
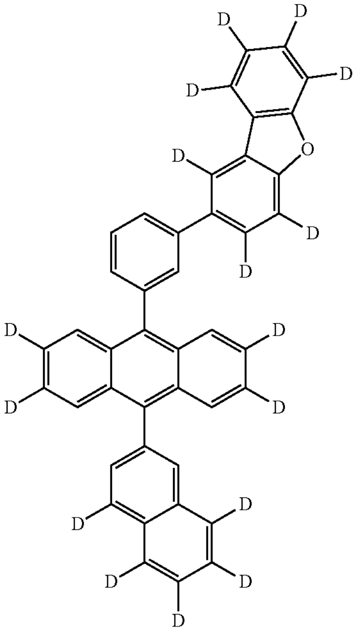
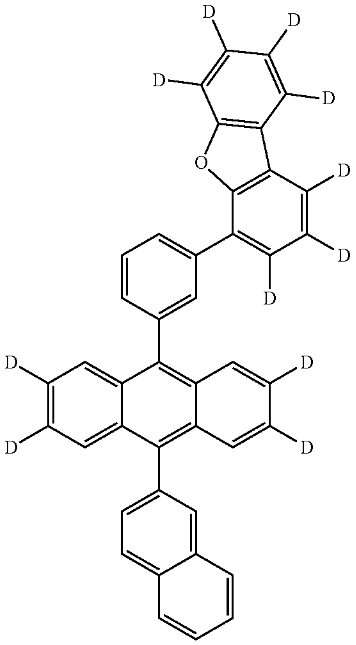

-continued
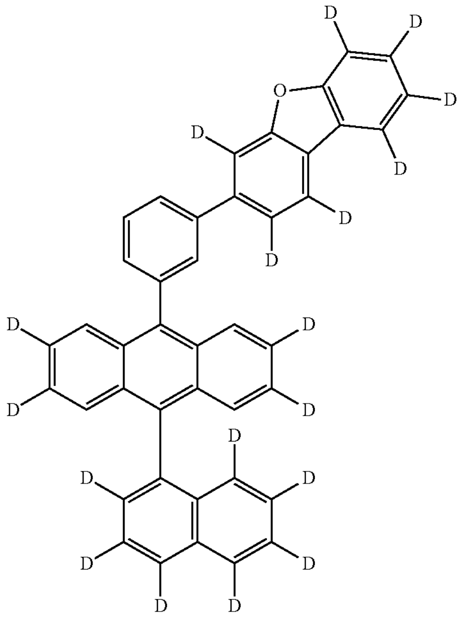
-continued
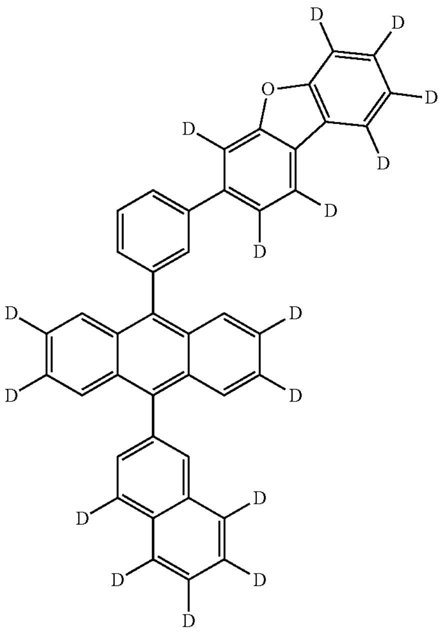
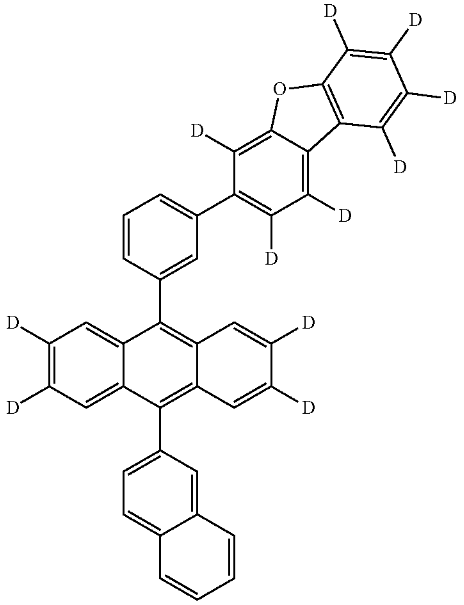
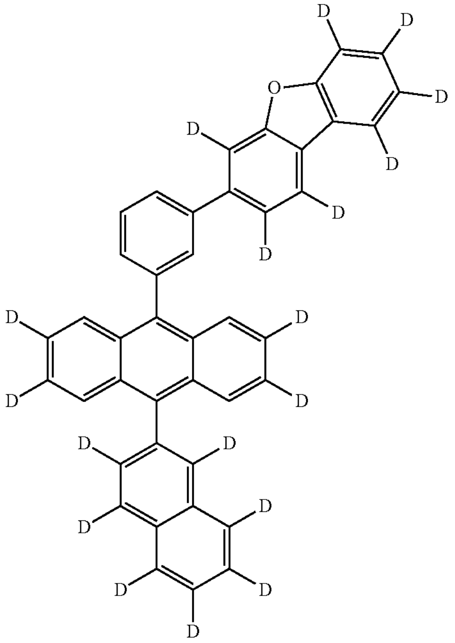

-continued
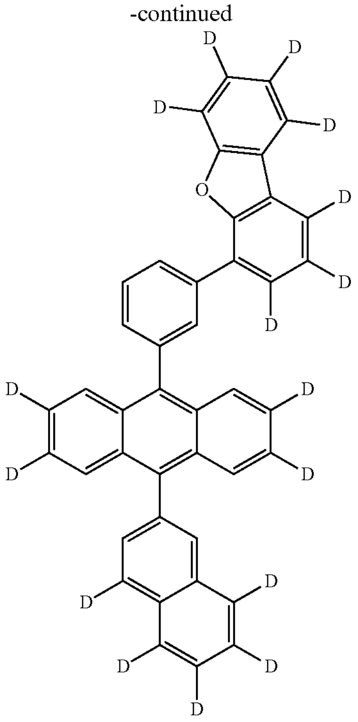
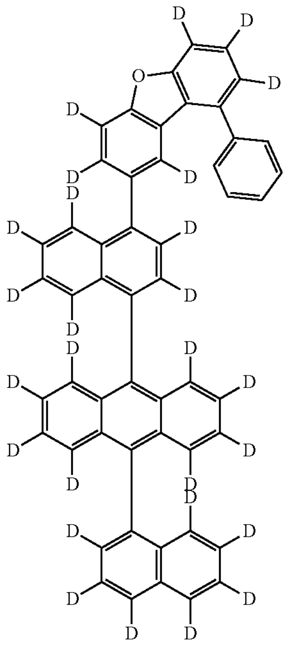
-continued
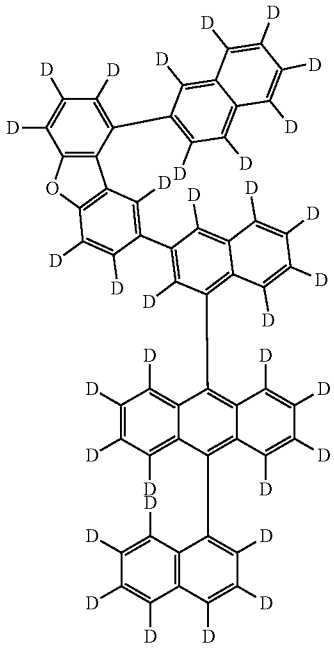
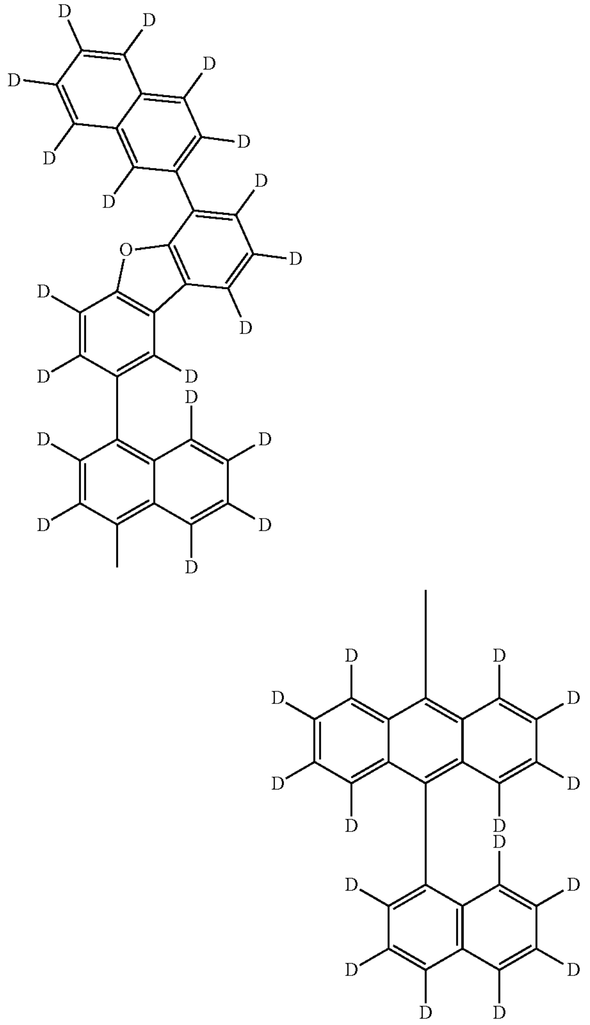

-continued
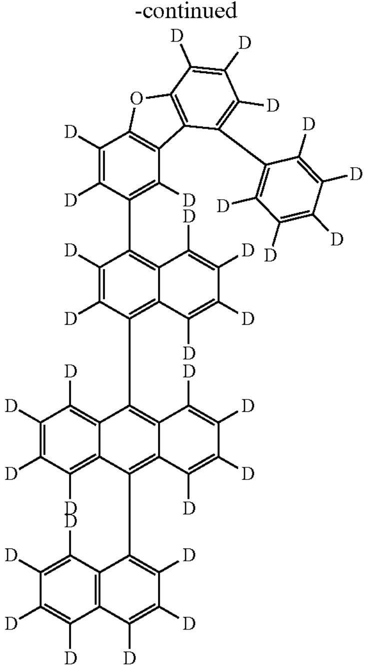
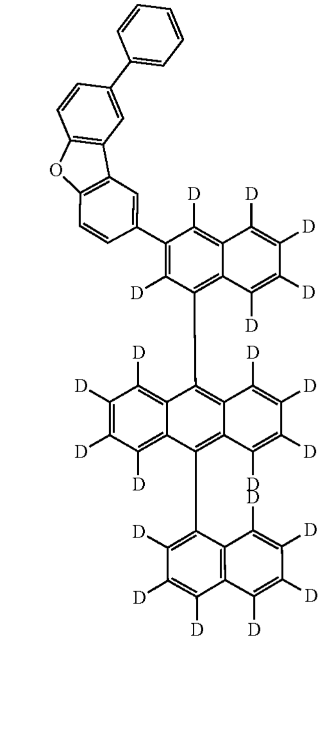
-continued
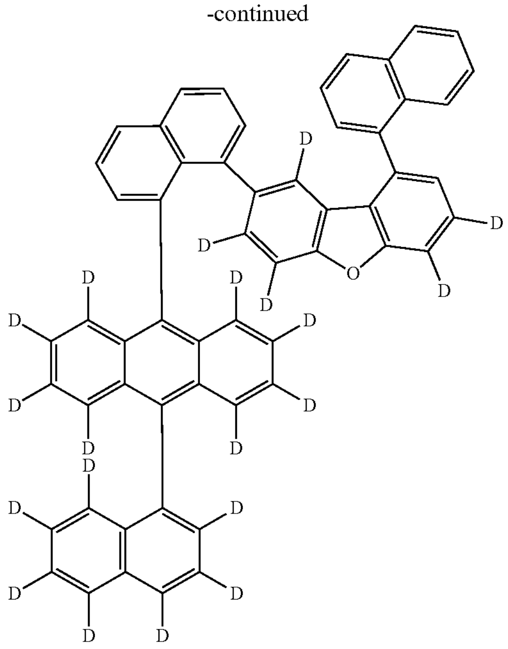
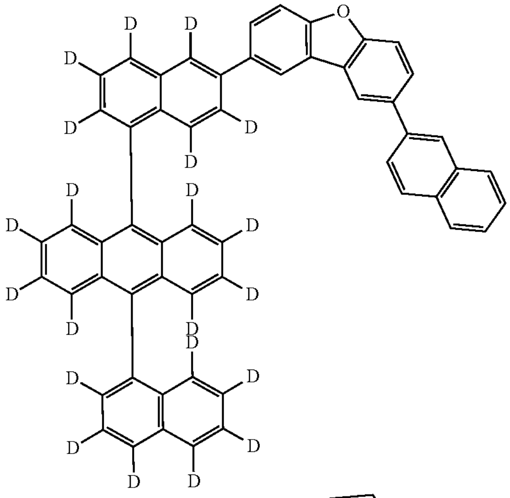
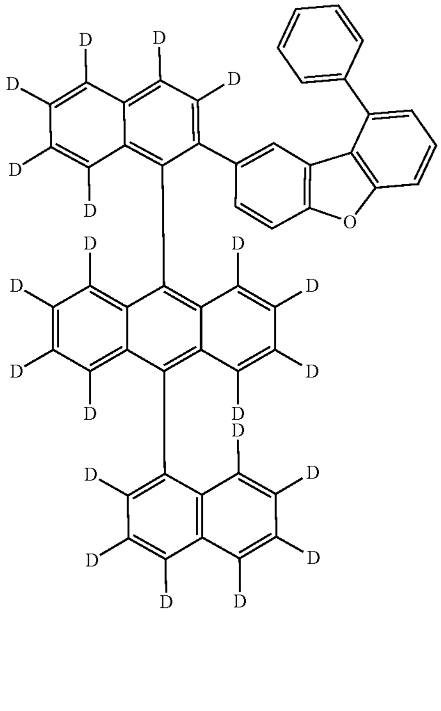

-continued
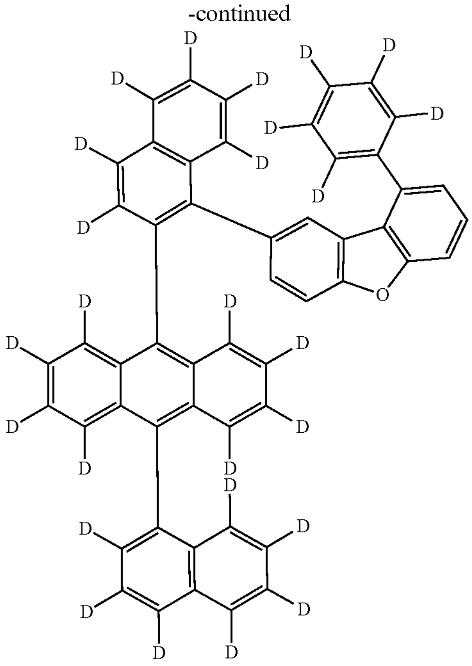
-continued
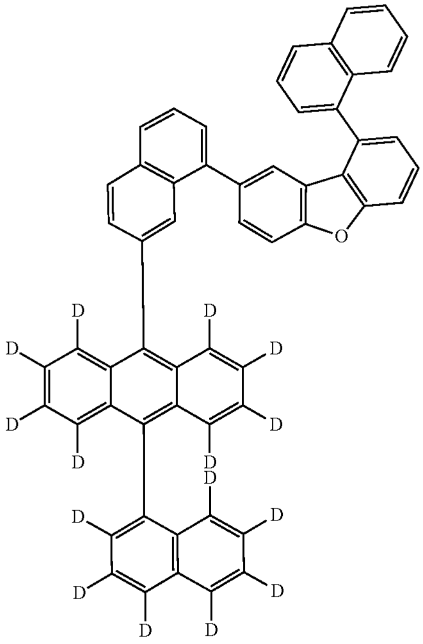
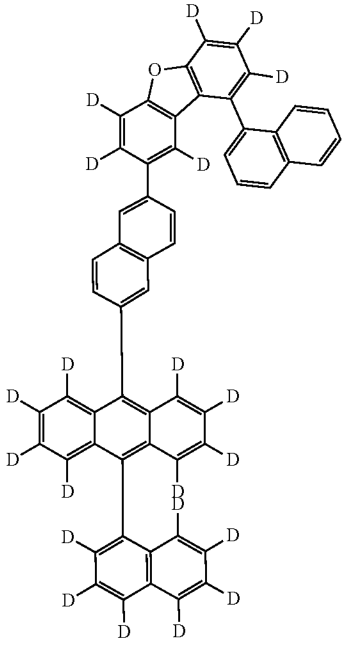
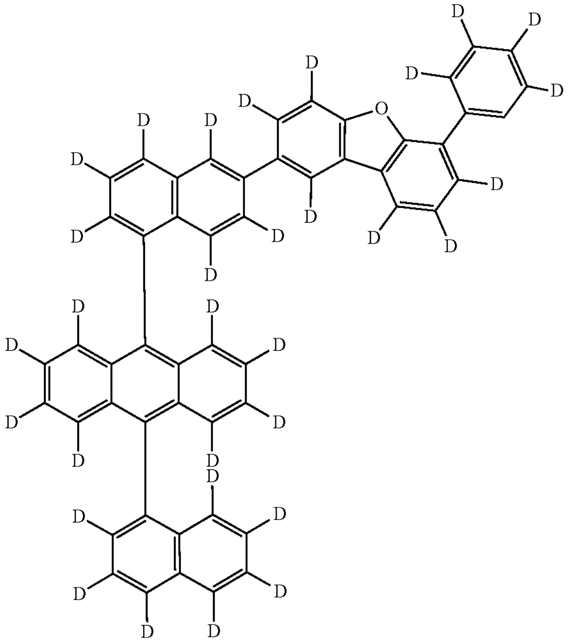

-continued
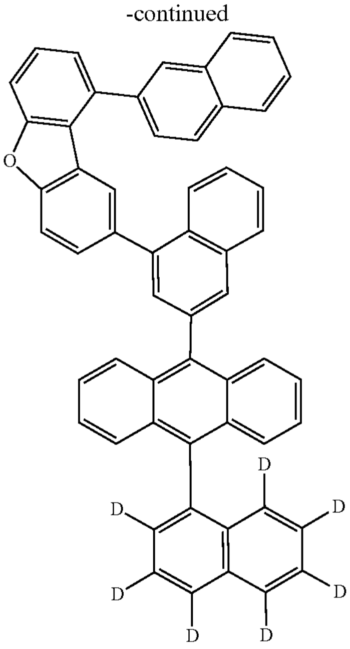
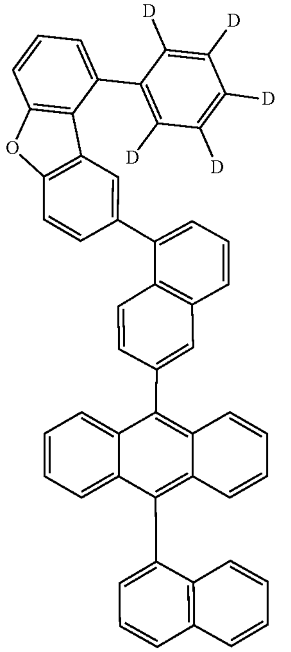
-continued
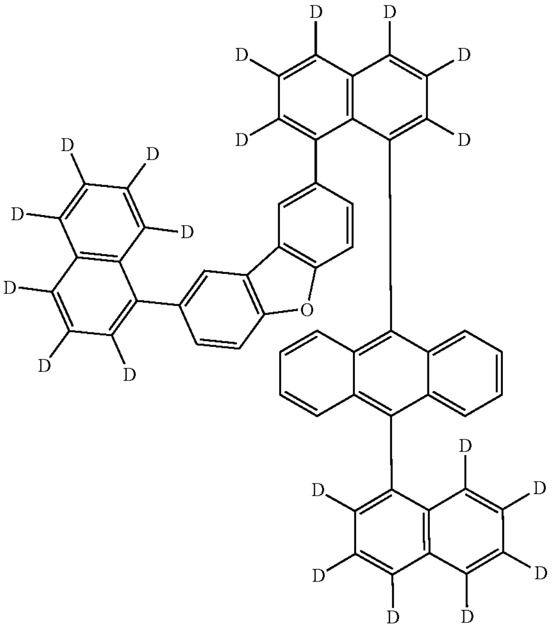
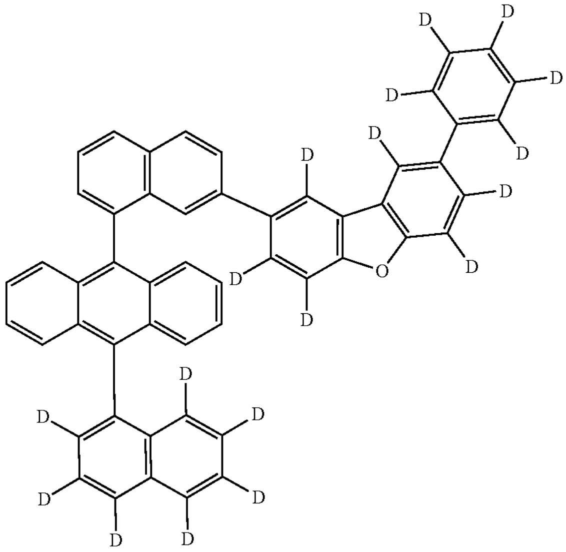

-continued
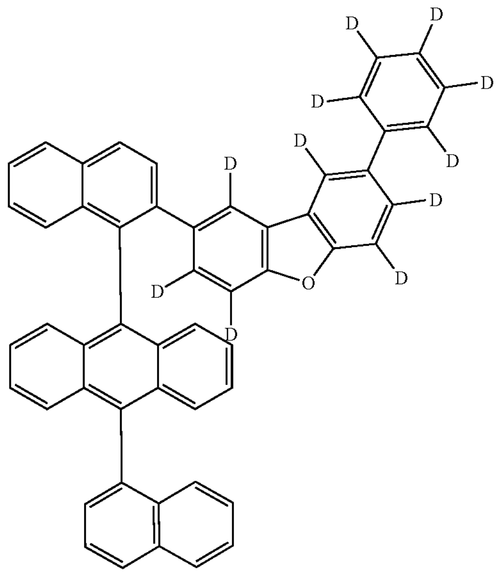
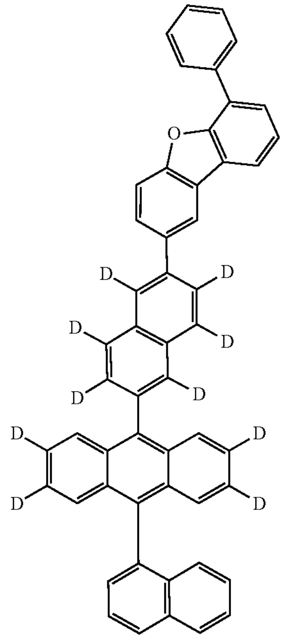
-continued
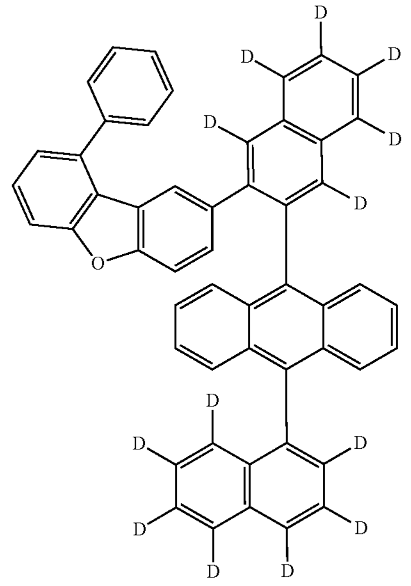
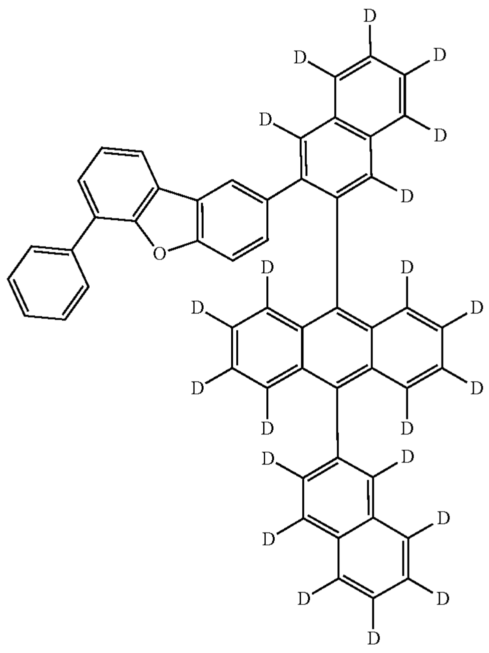

-continued
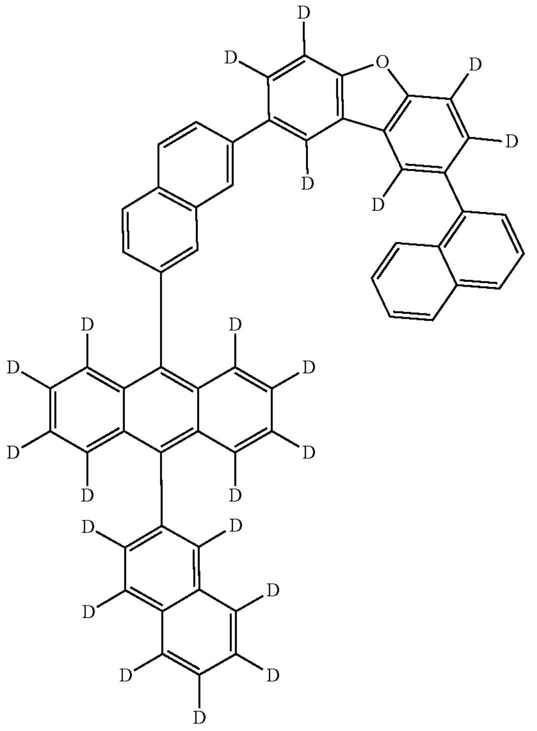
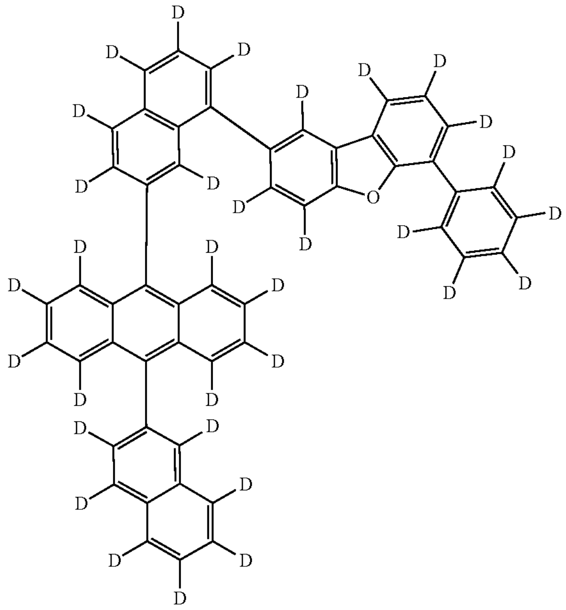
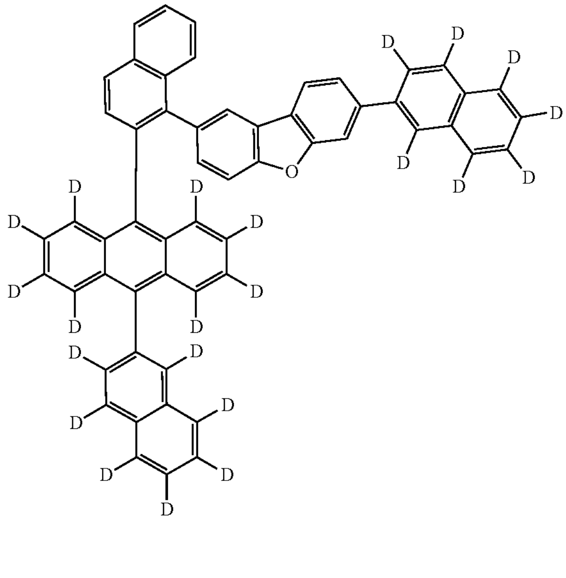
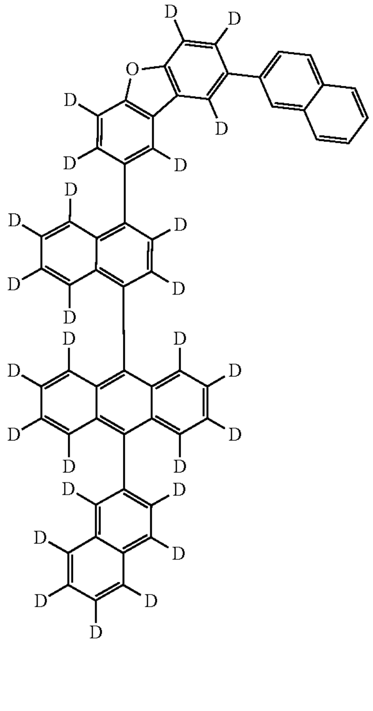

-continued
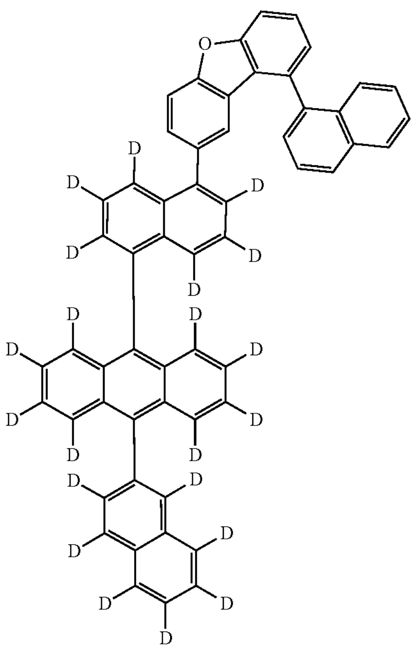
-continued
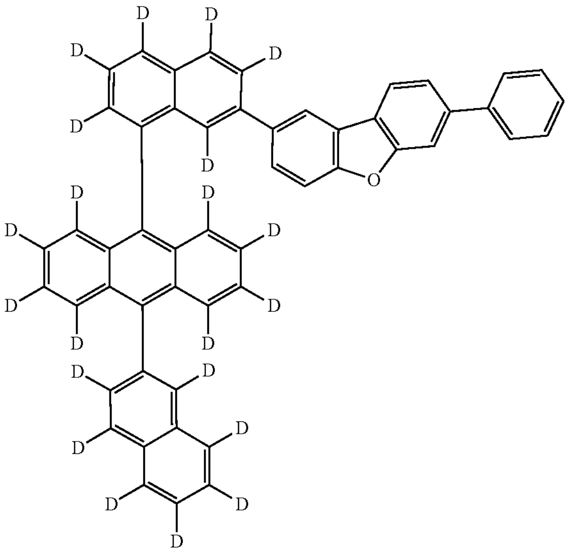
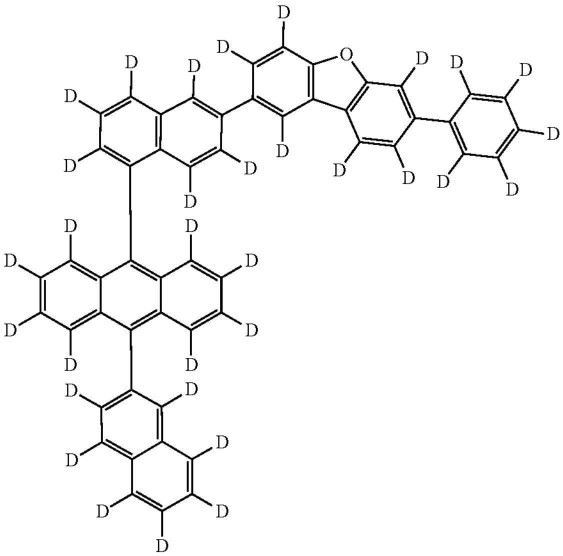
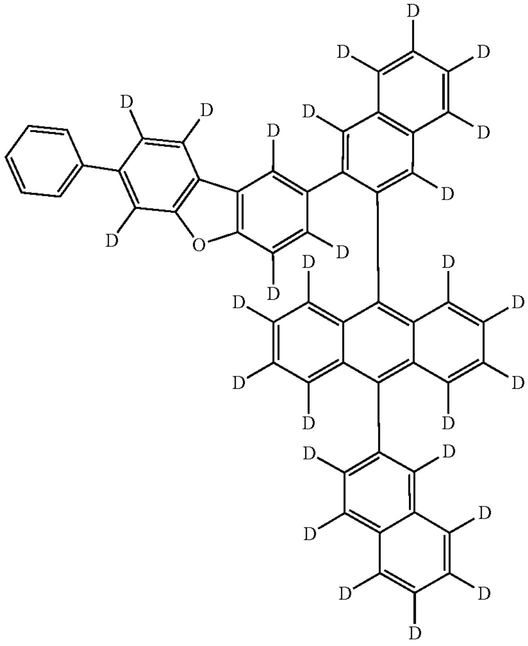

-continued
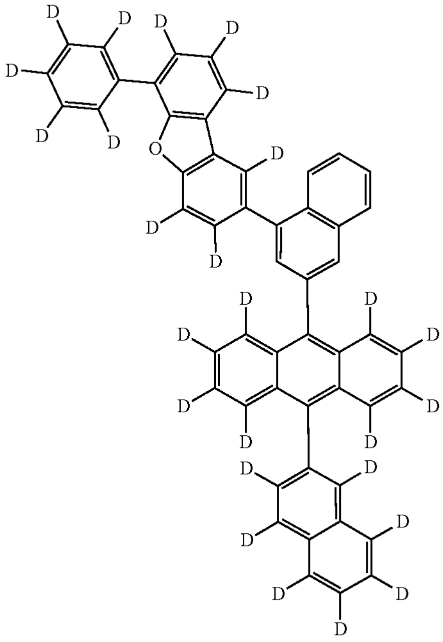
-continued
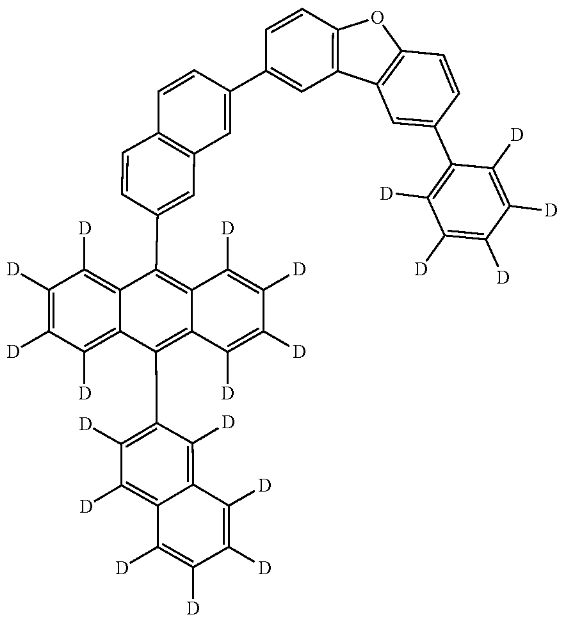
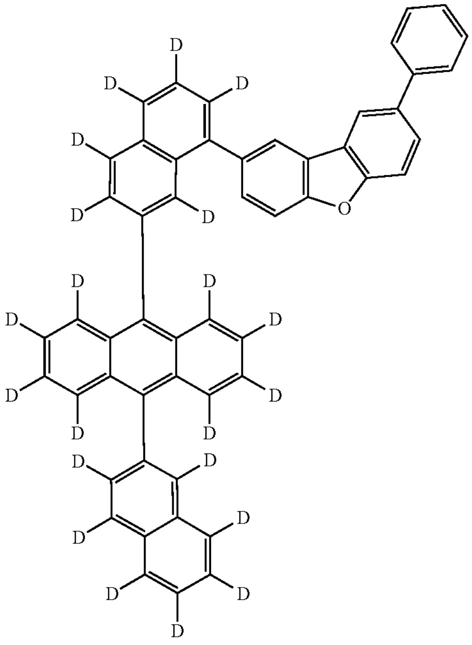
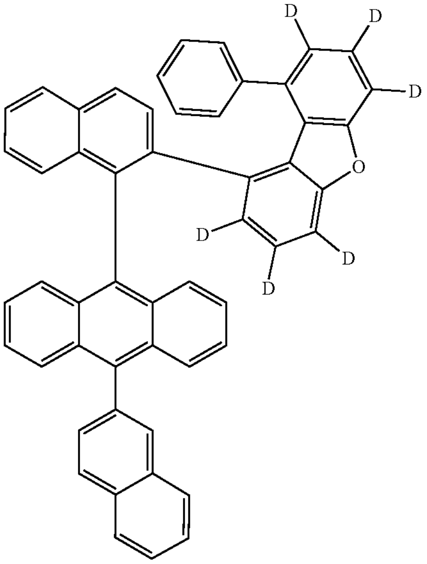

-continued
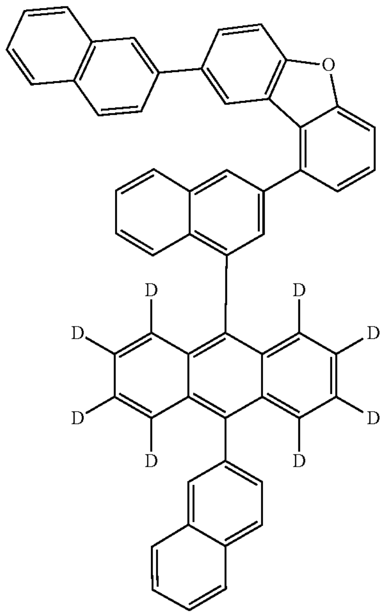
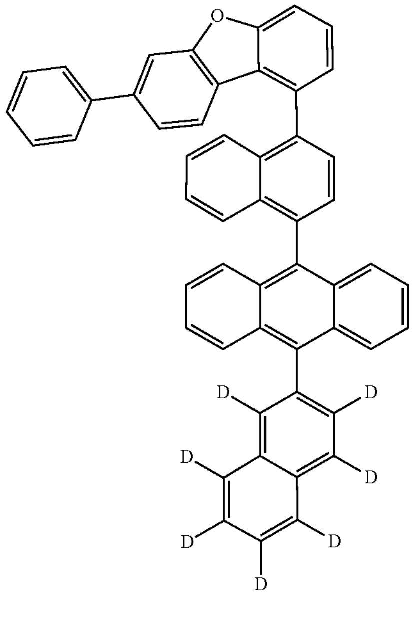
-continued
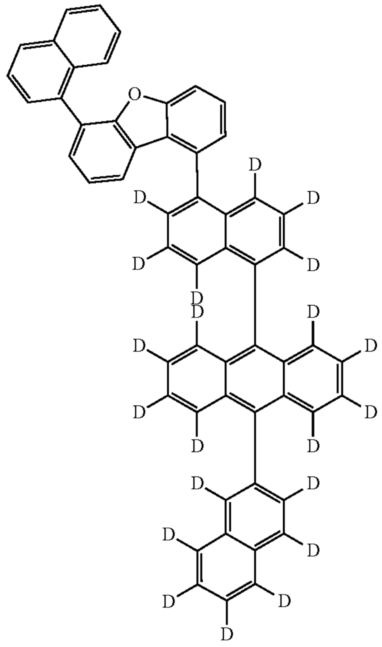
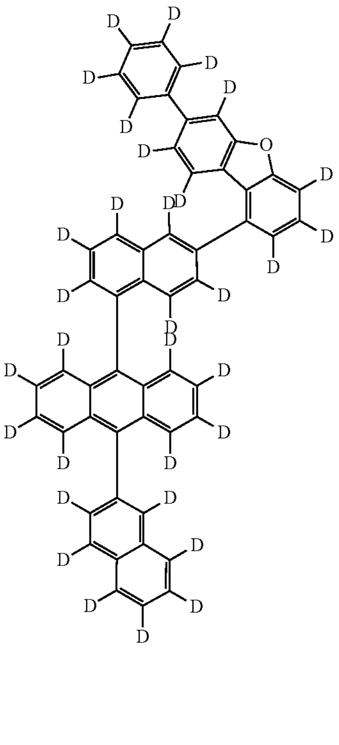

-continued
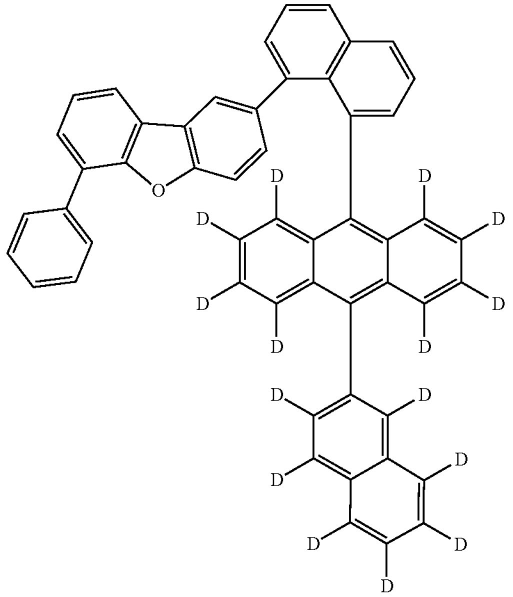
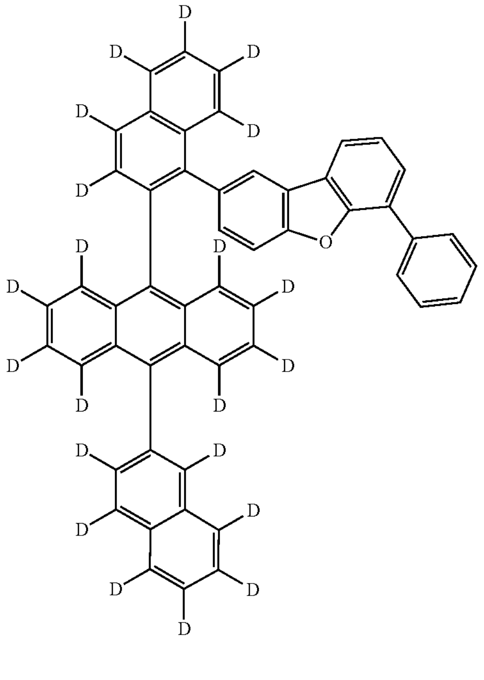
-continued
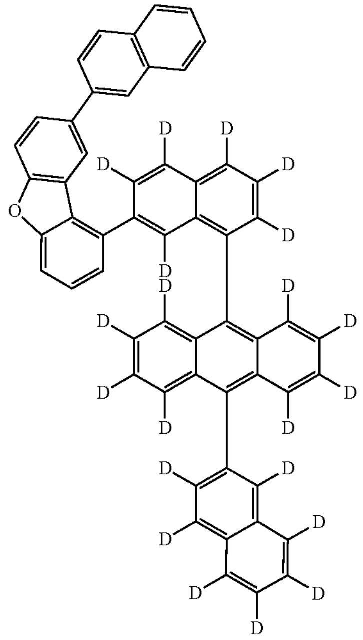
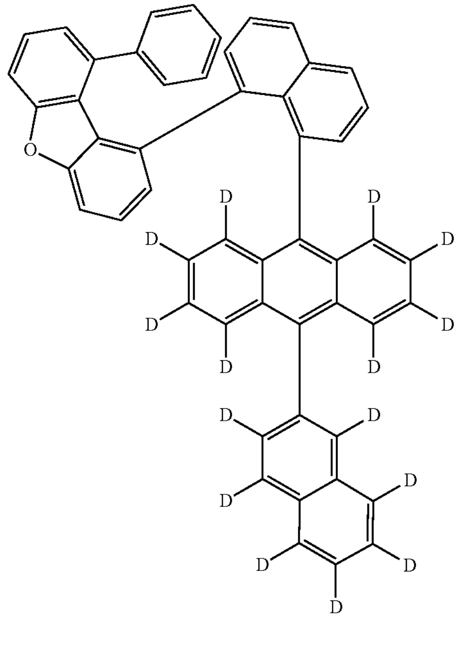

-continued
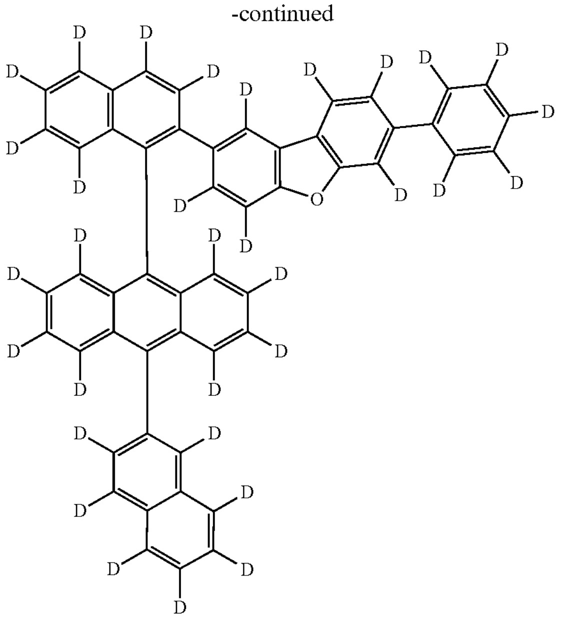
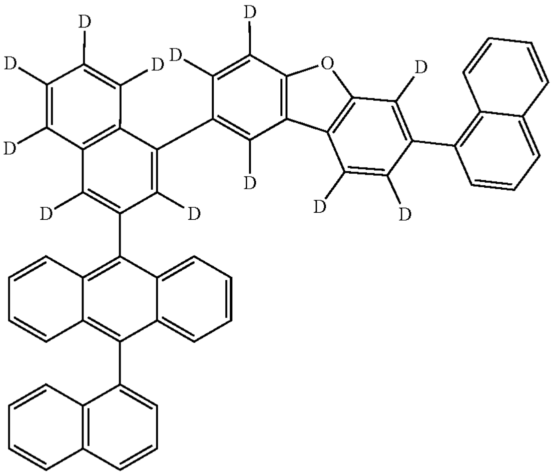
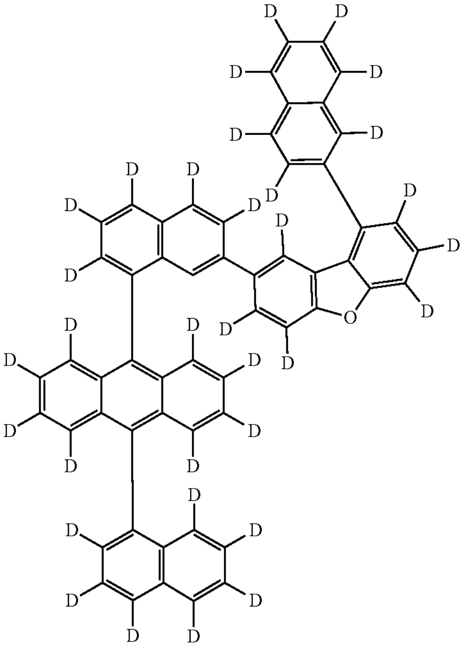
-continued
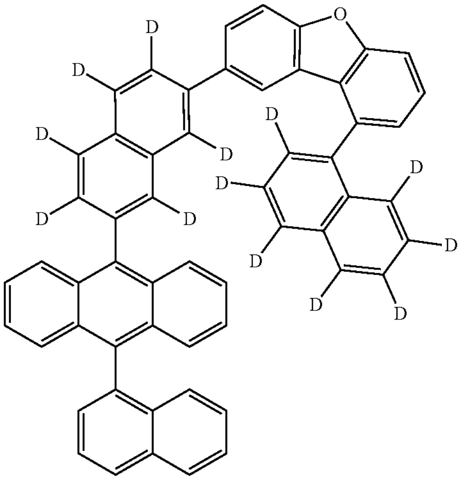
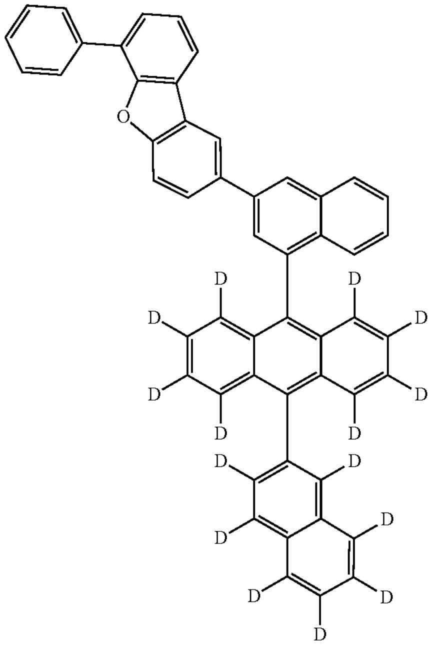

-continued
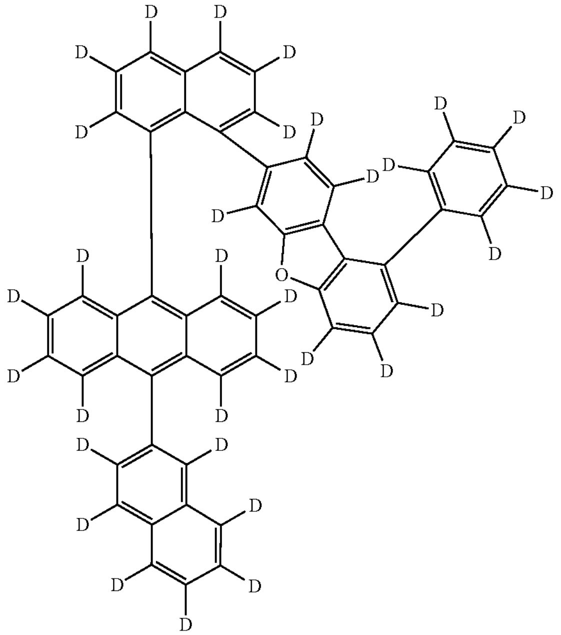
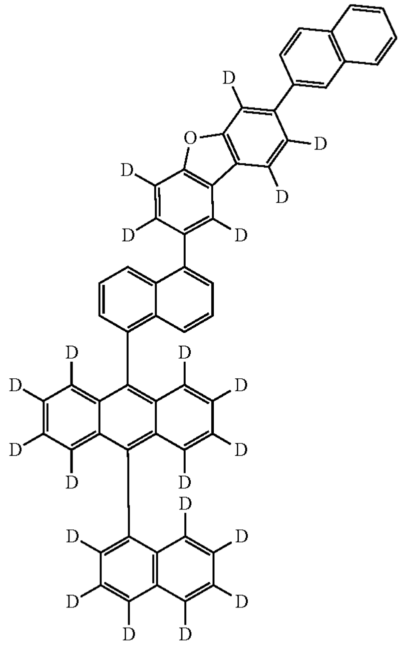
-continued
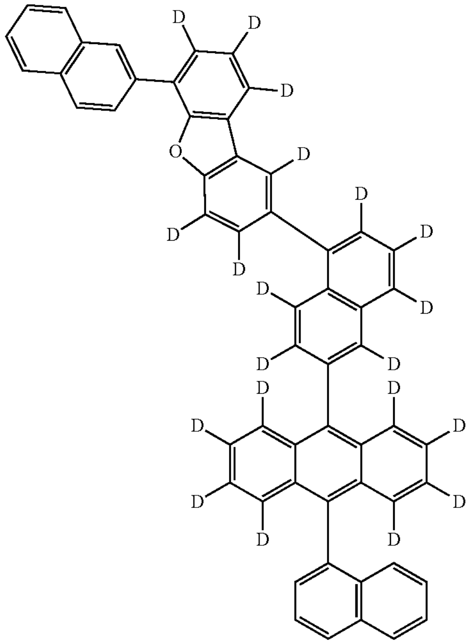
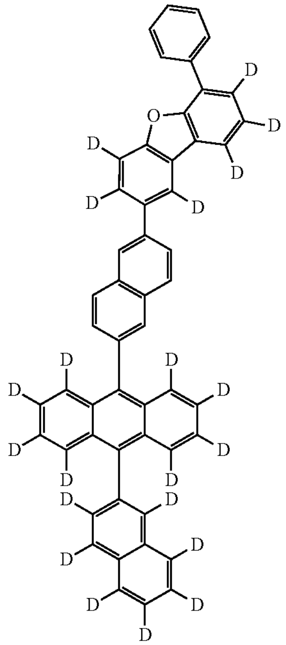

-continued
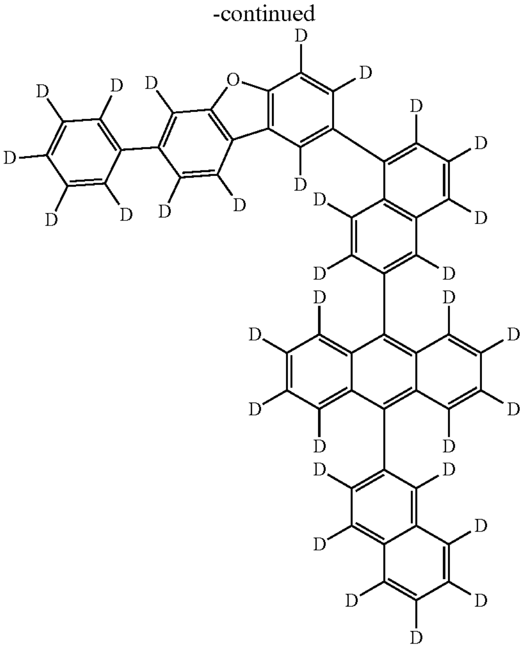
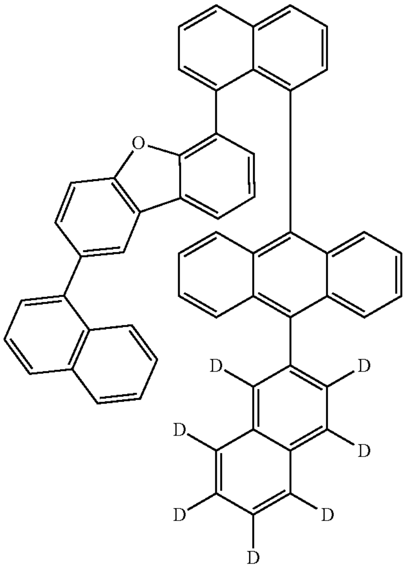
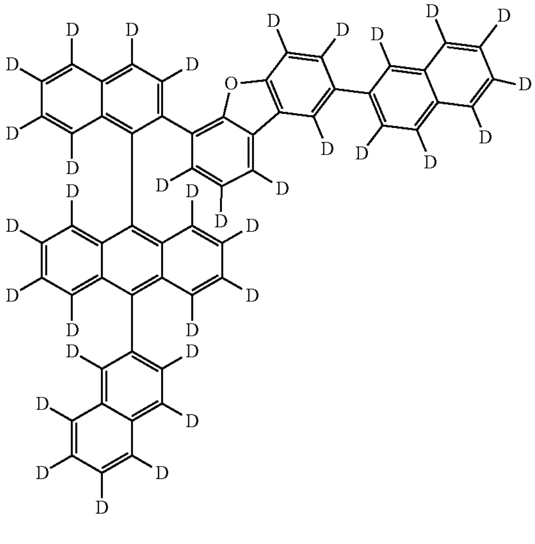
-continued
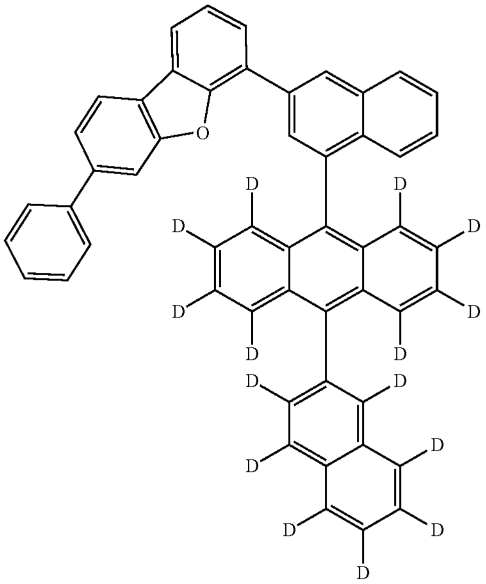
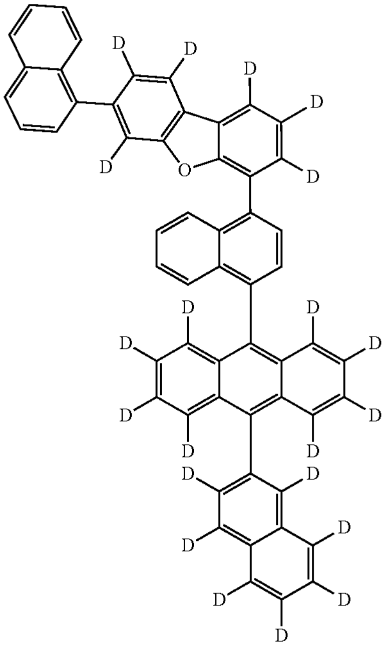

-continued
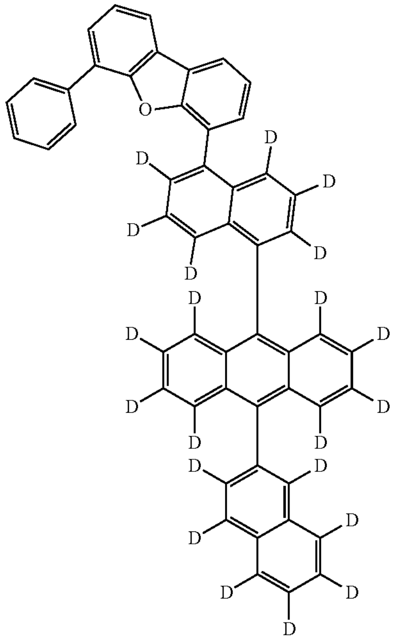
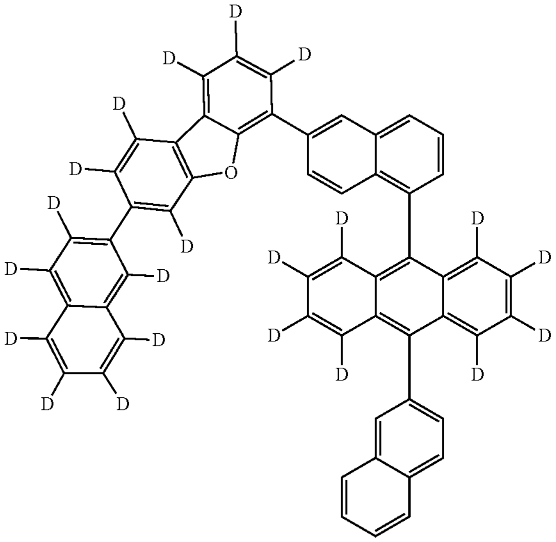
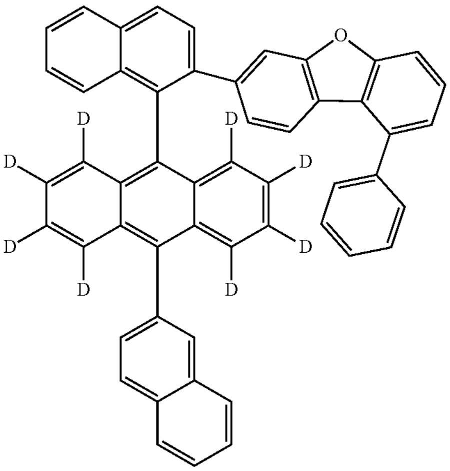
-continued
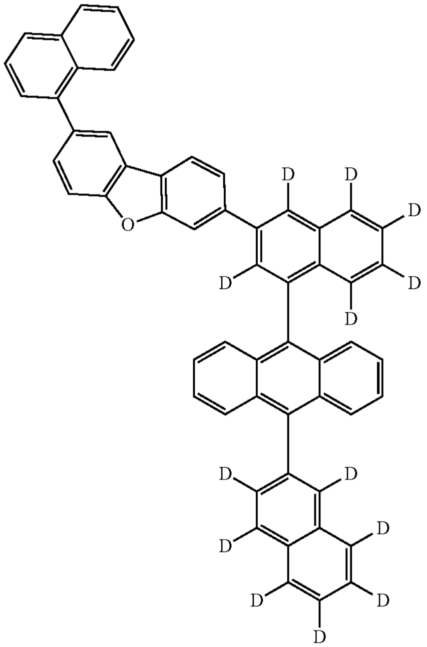
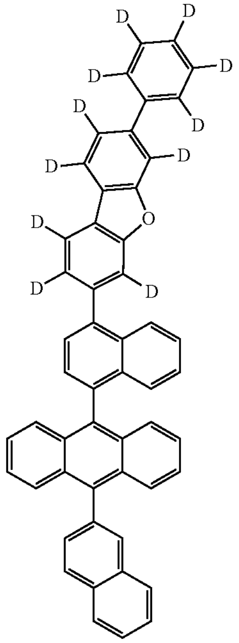

-continued
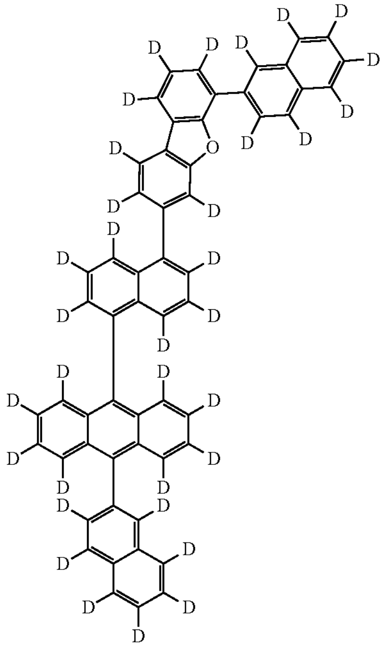
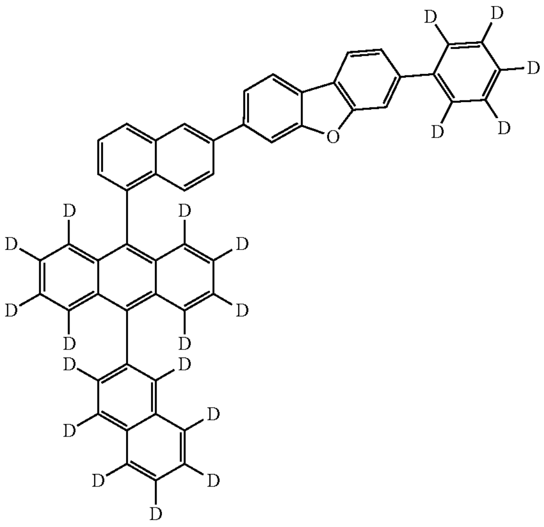
-continued
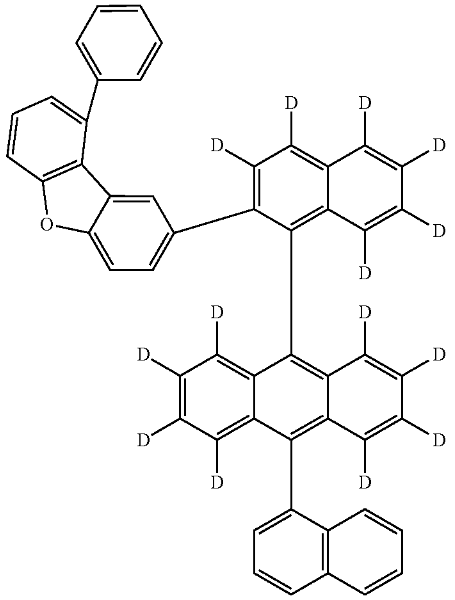
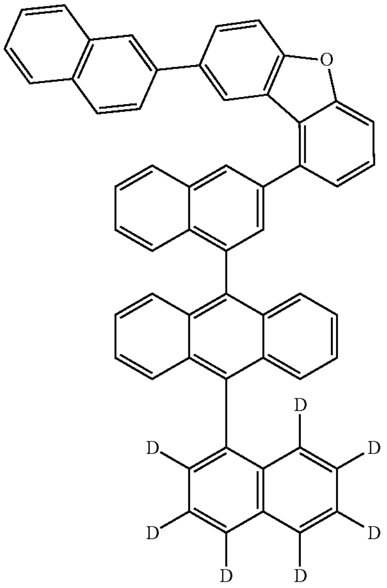

-continued
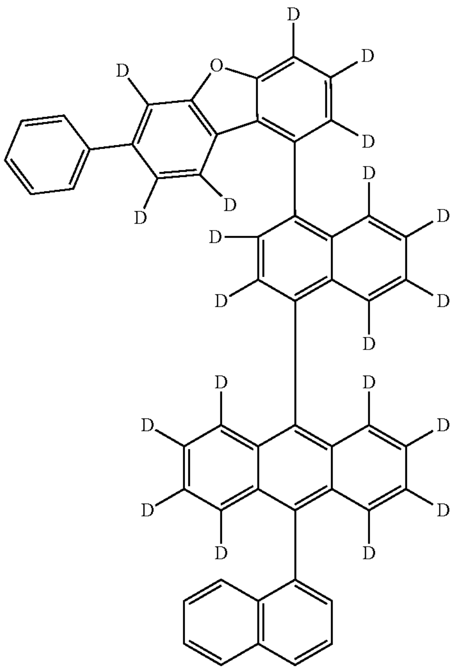
-continued
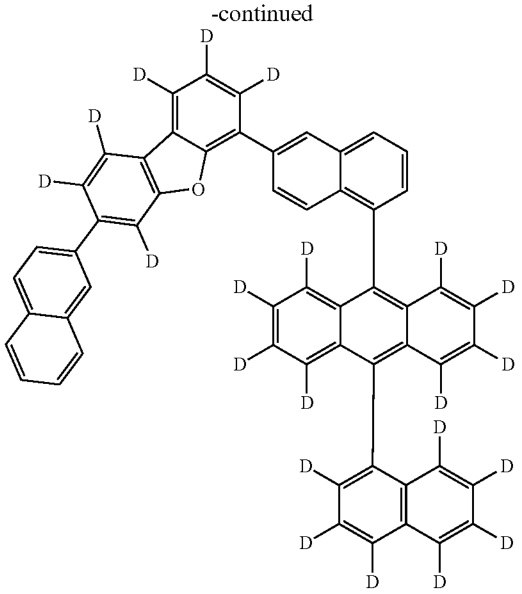
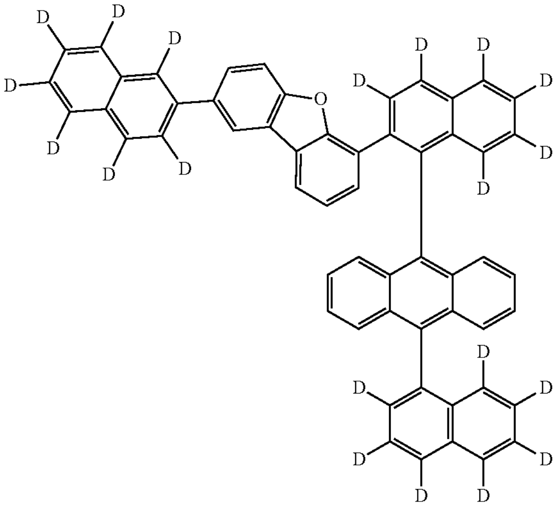
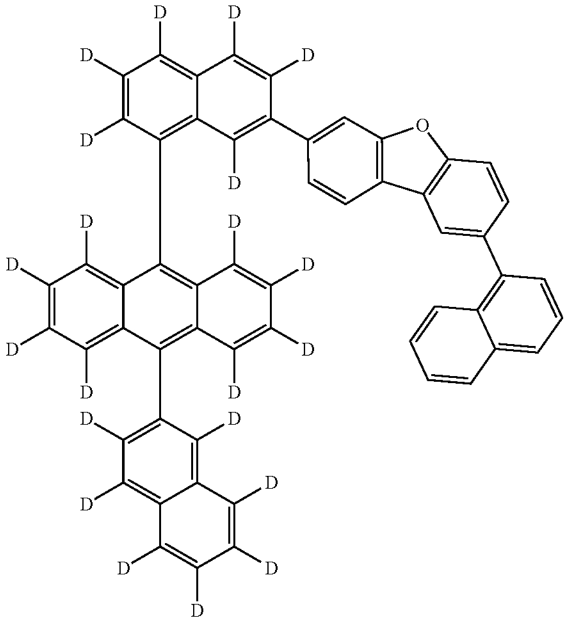

-continued
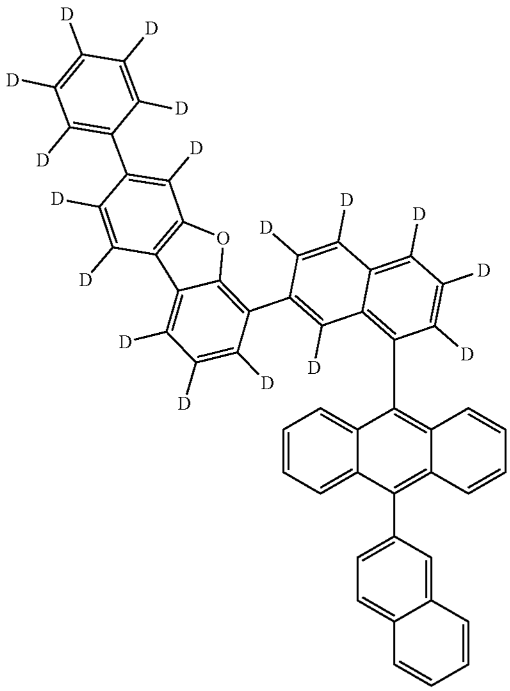
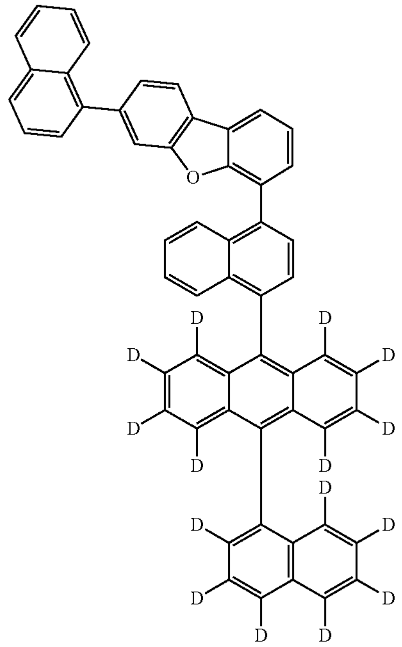
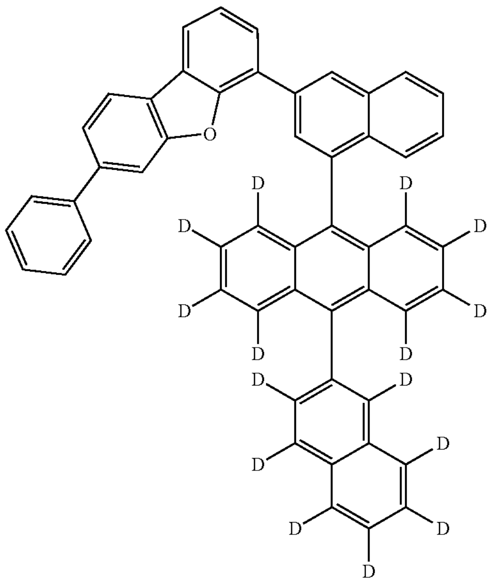
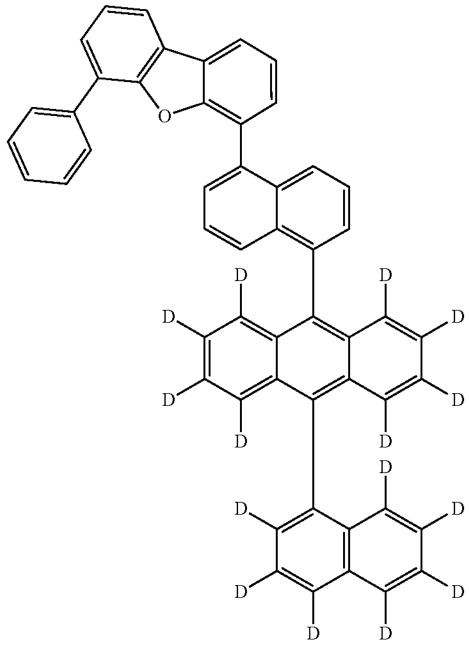

-continued
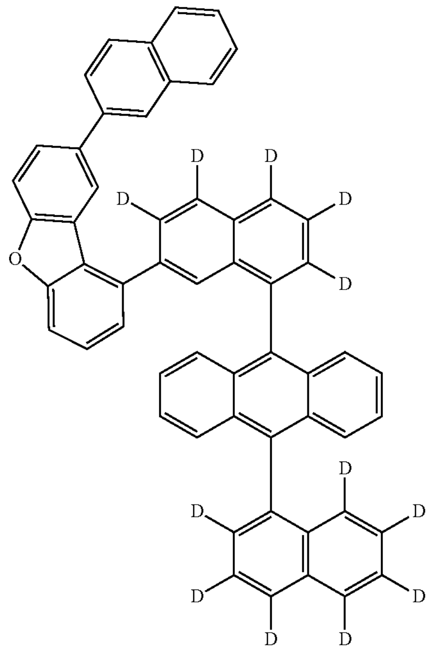
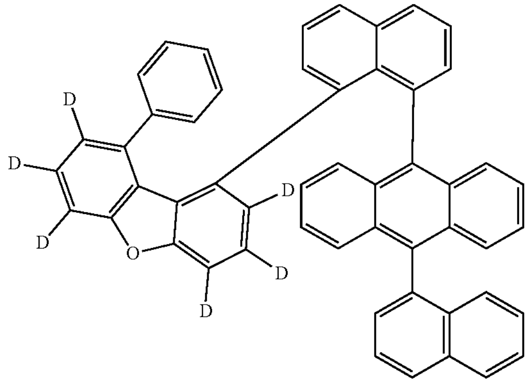
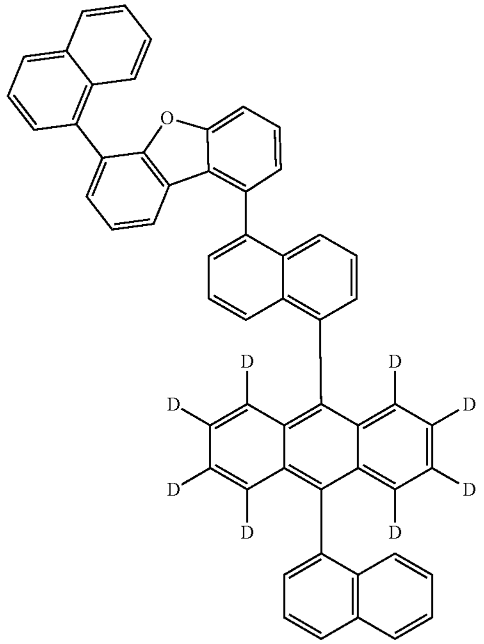
-continued
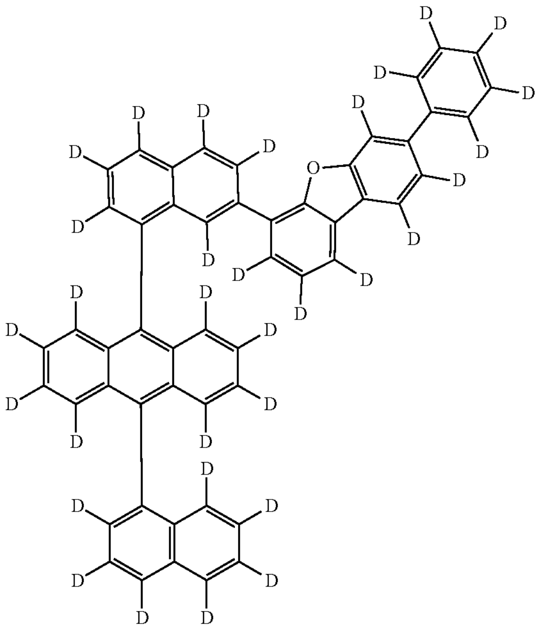
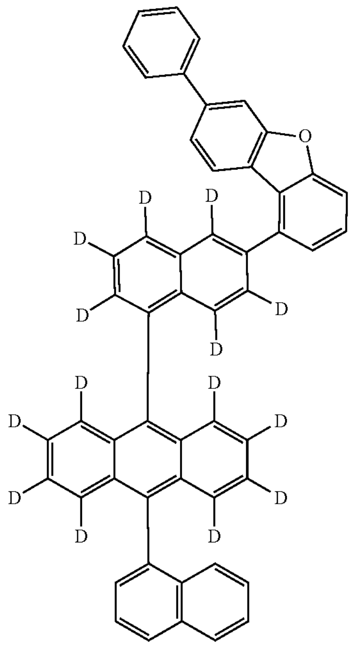
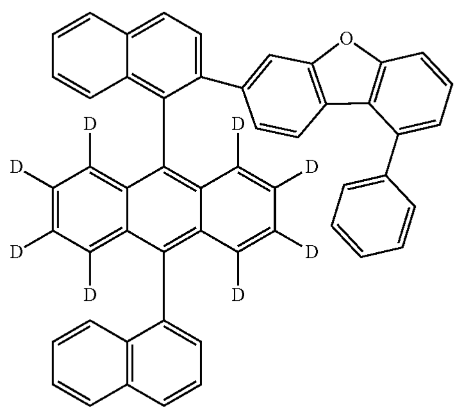

-continued
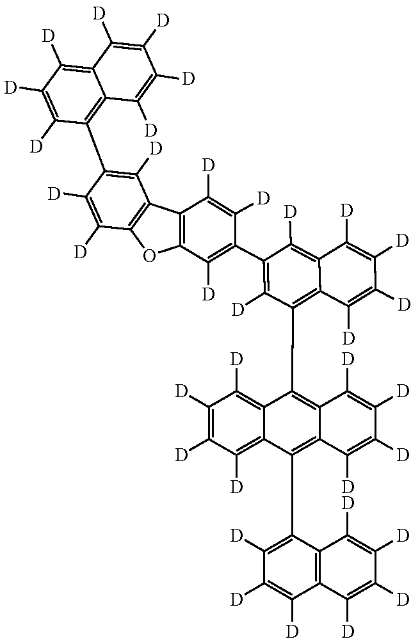
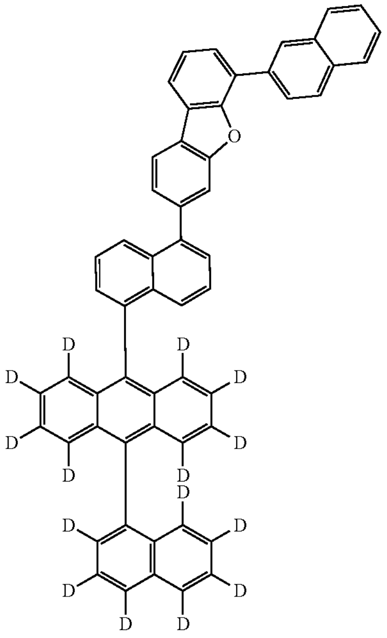
-continued
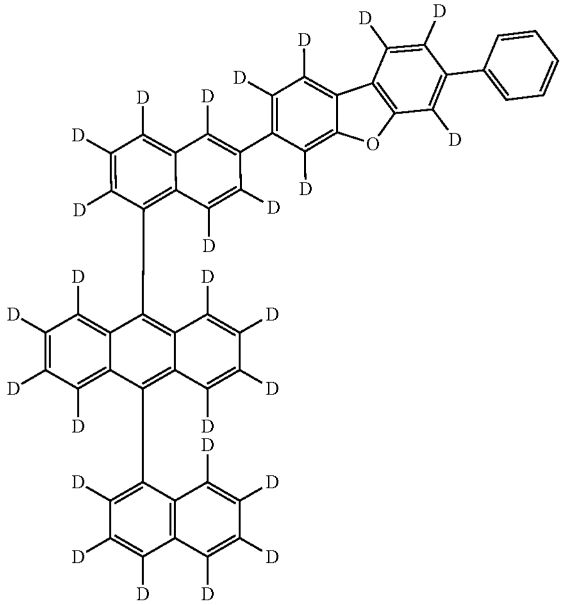
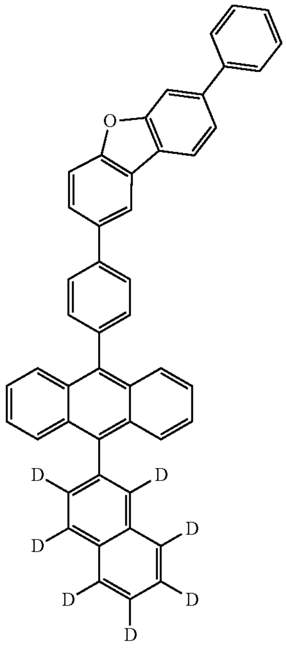

-continued
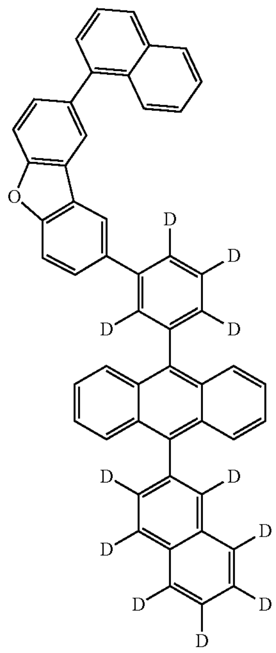
-continued
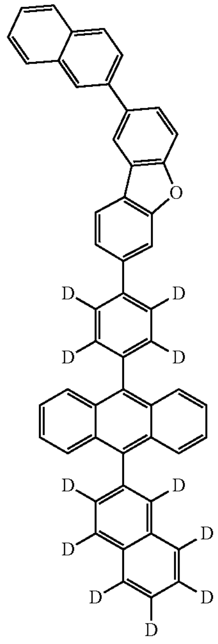
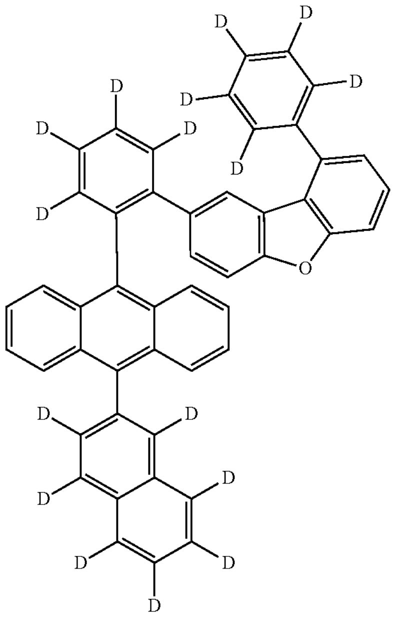
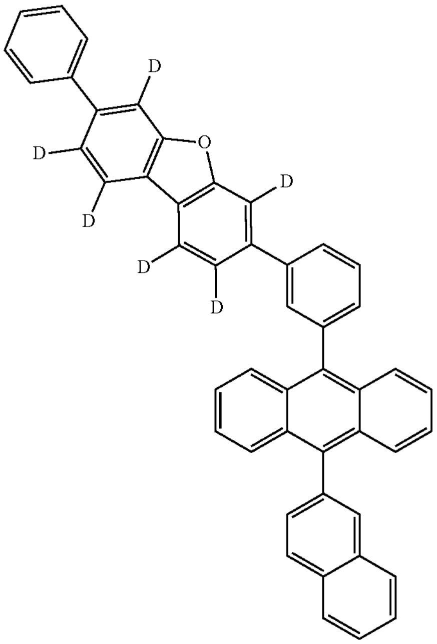

-continued
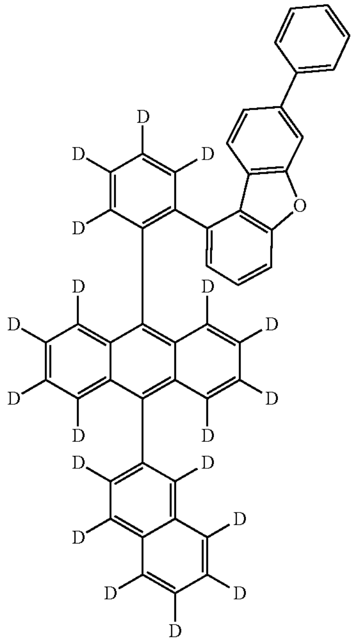
-continued
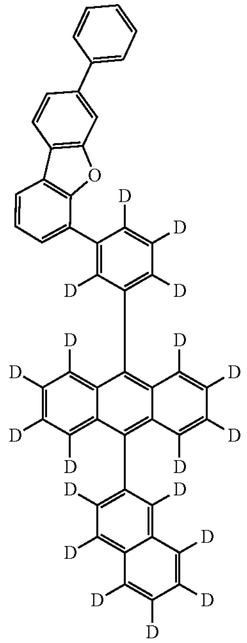
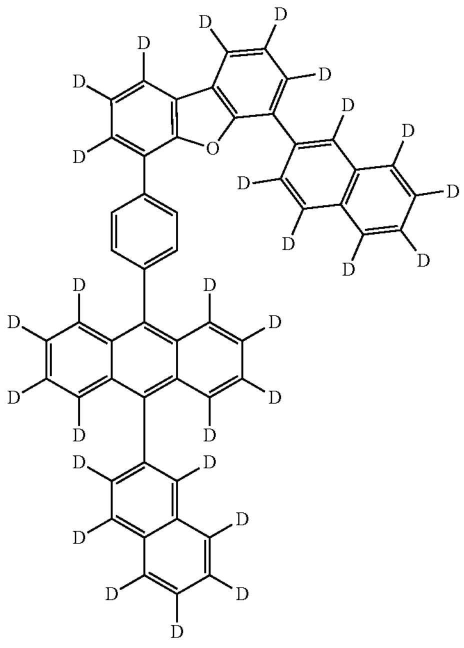
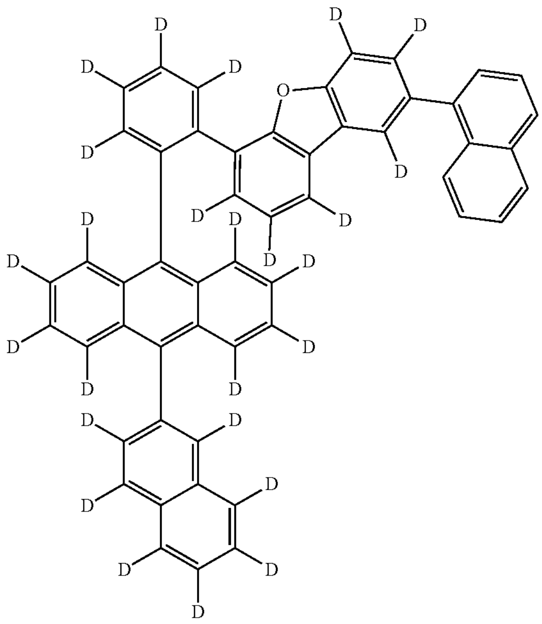

-continued
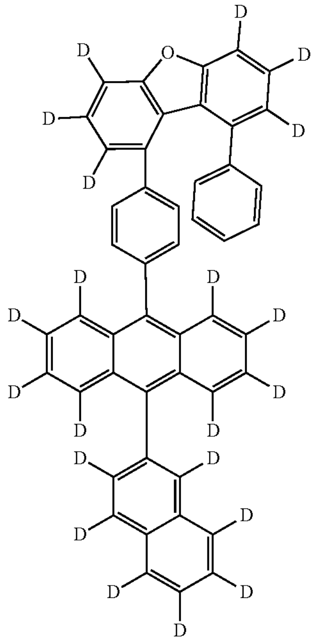
-continued
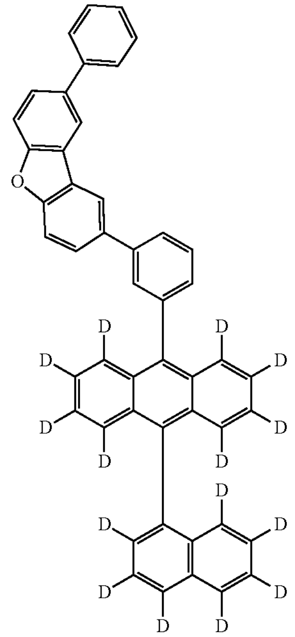
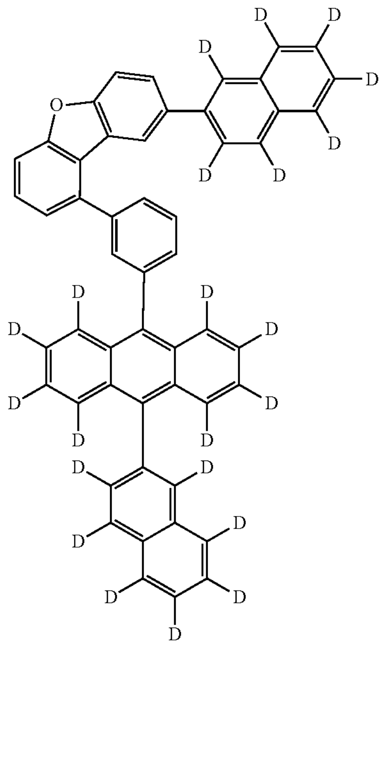
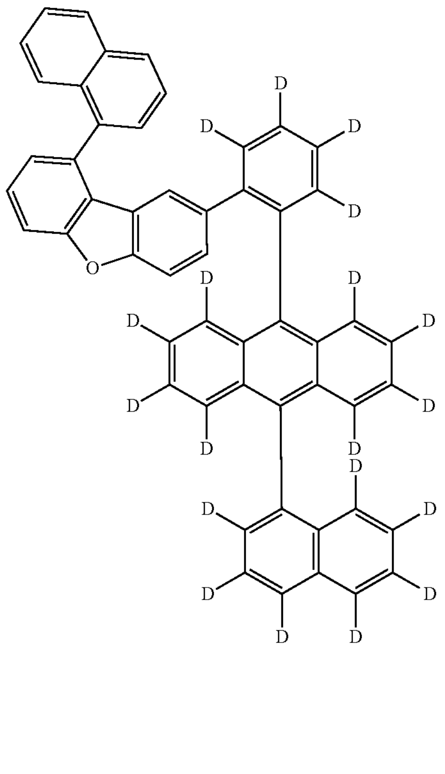

-continued
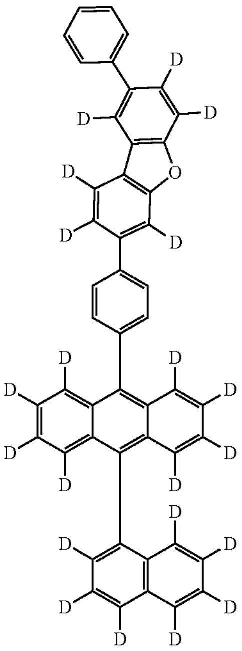
-continued
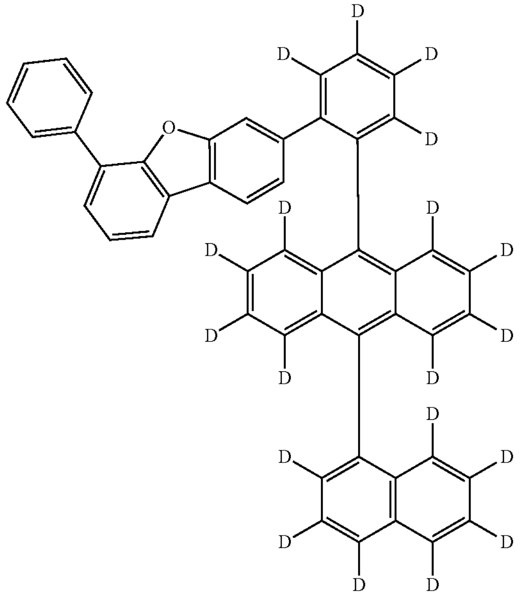
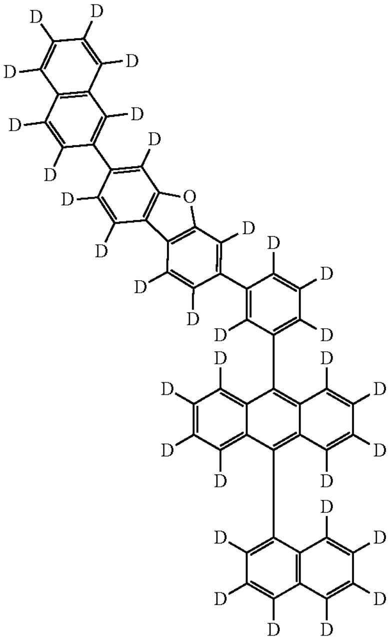
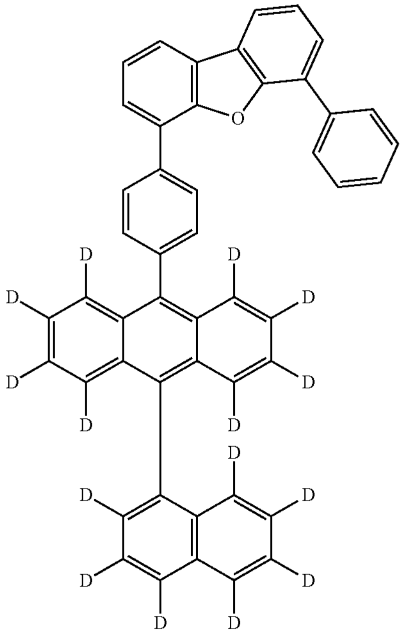

-continued
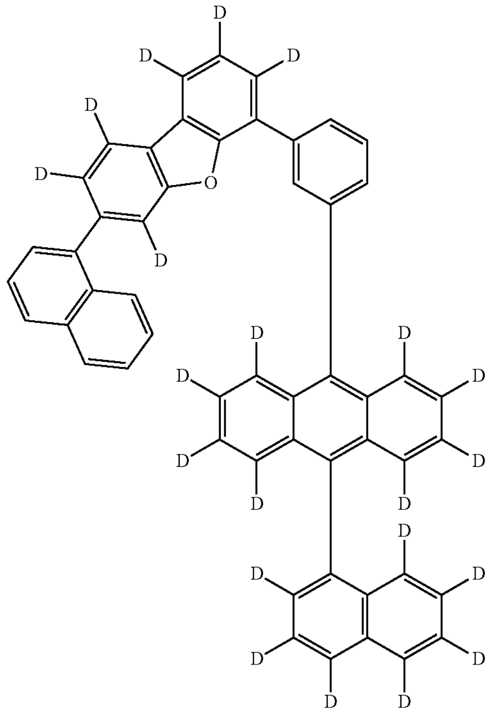
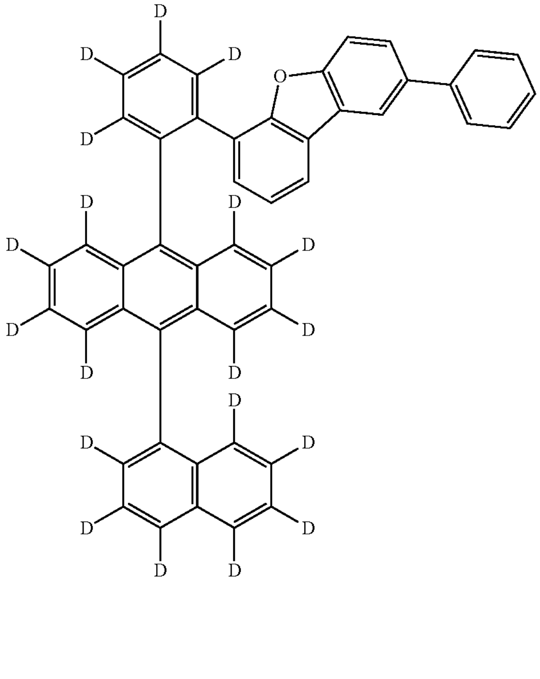
-continued
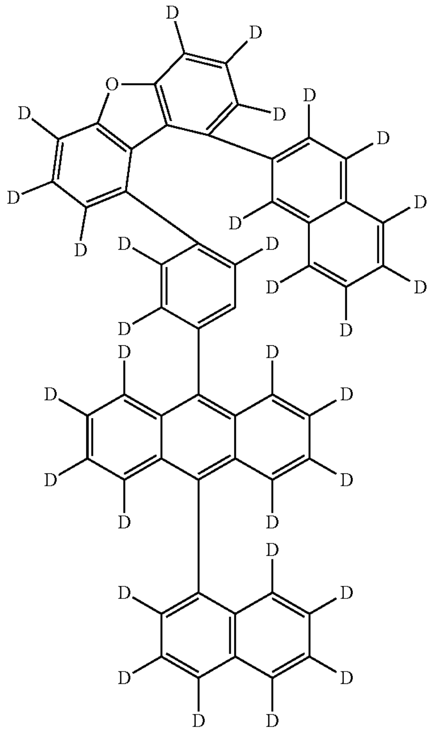
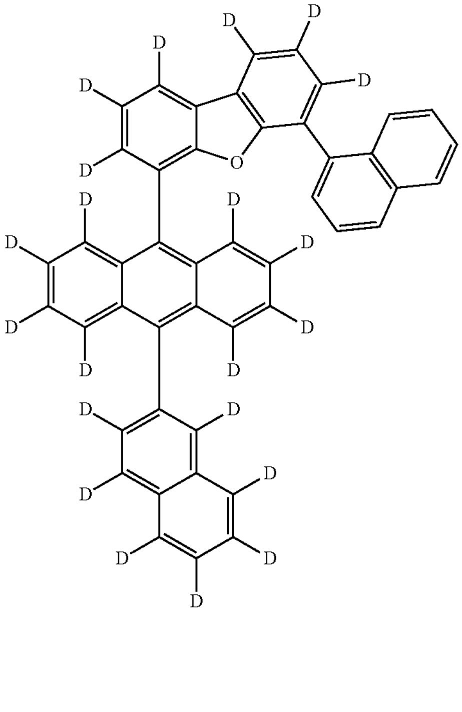 [SMILES: [2H]c1c([2H])c([2H])c2c(oc3c(-c4c5c([2H])c([2H])c([2H])c([2H])c5c(-c5c([2H])c([2H])c6c([2H])c([2H])c([2H])c([2H])c6c5[2H])c5c([2H])c([2H])c([2H])c([2H])c45)c([2H])c([2H])c([2H])c32)c1-c1cccc2ccccc12]

-continued
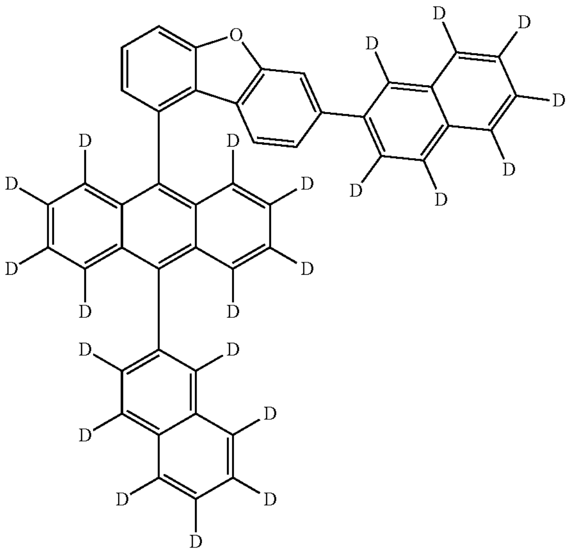
-continued
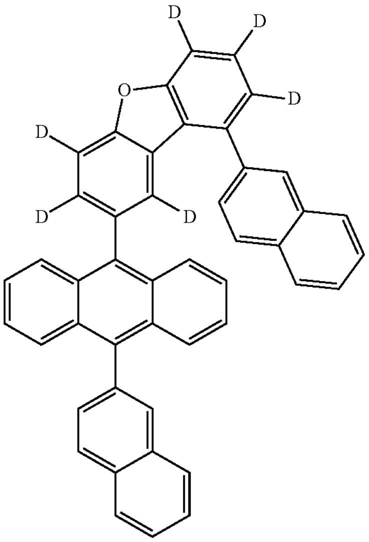
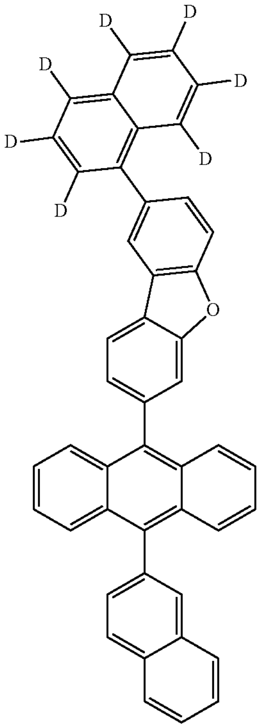
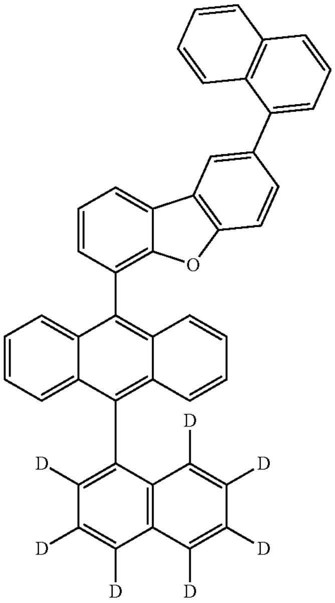

-continued
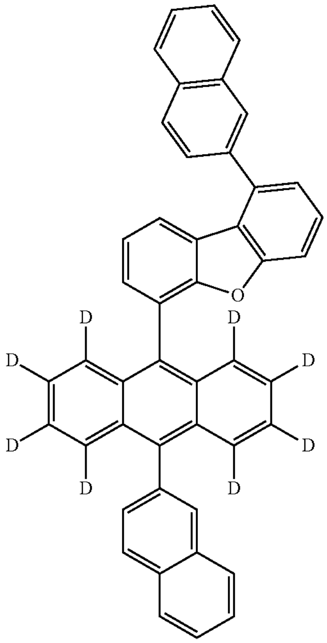
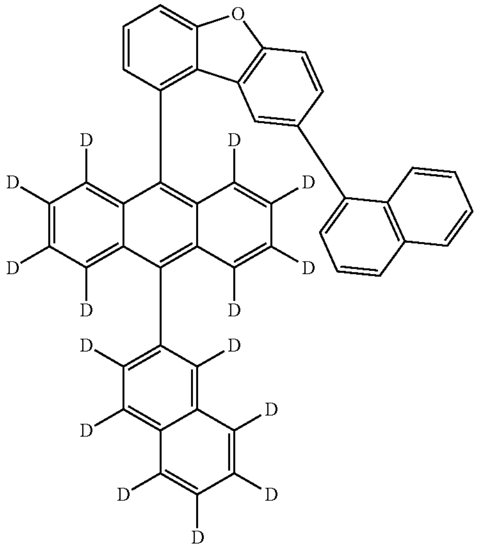
-continued
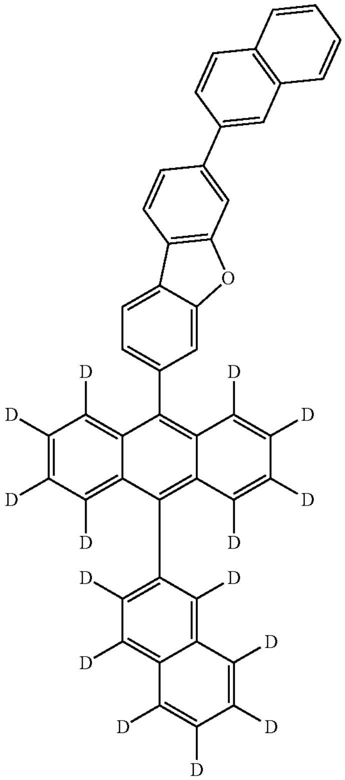
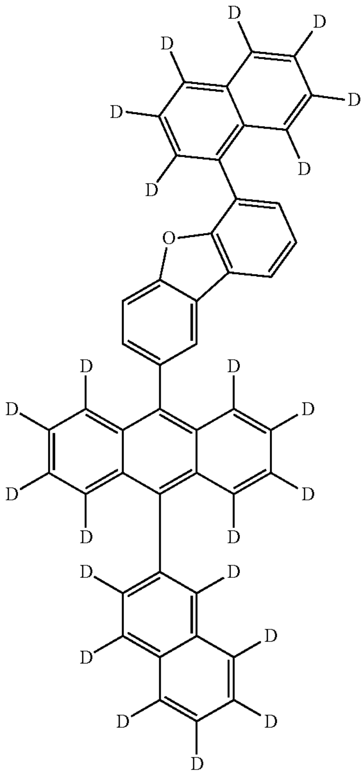

-continued
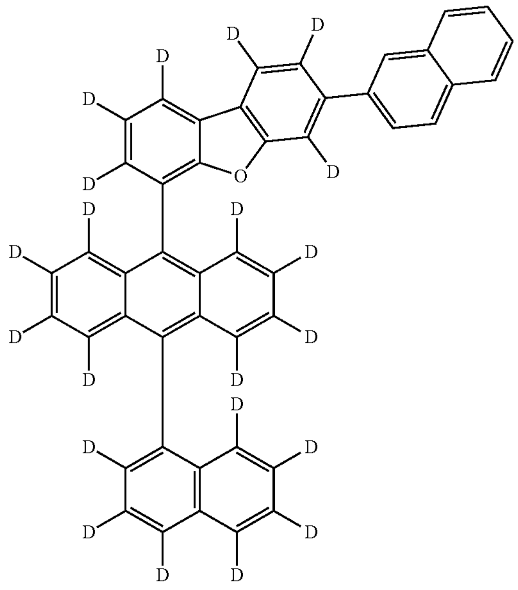
-continued
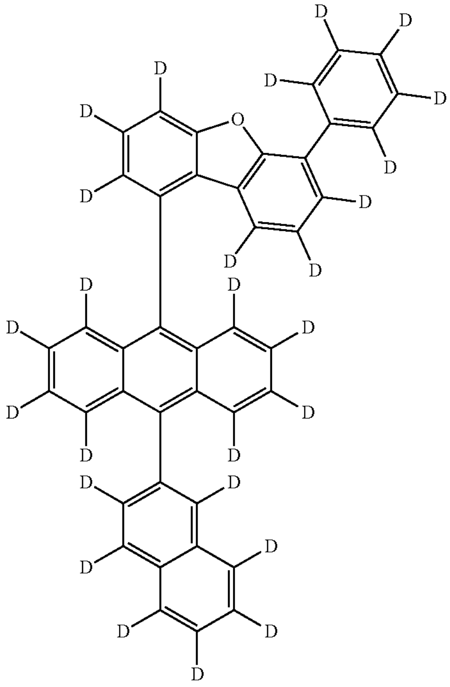
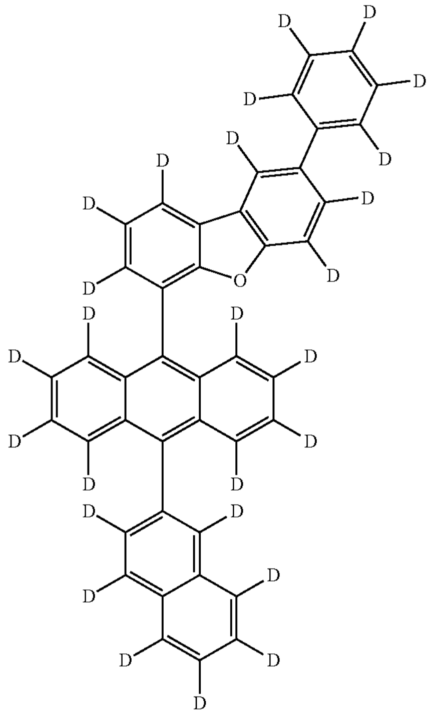
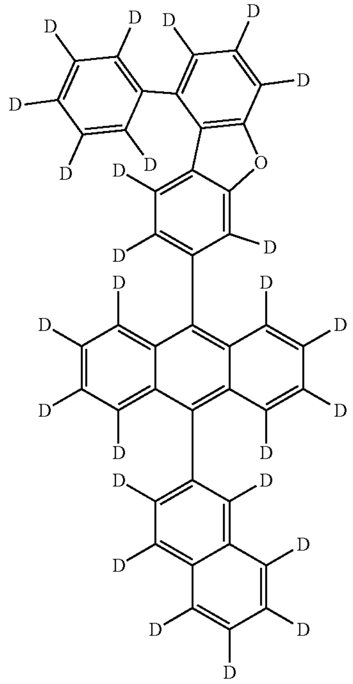

-continued
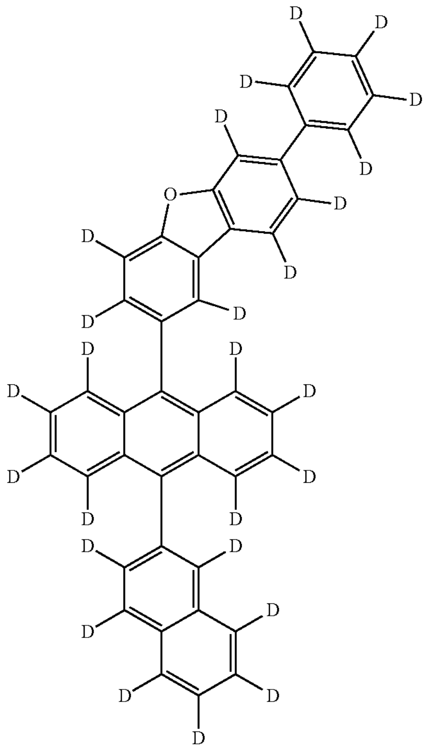
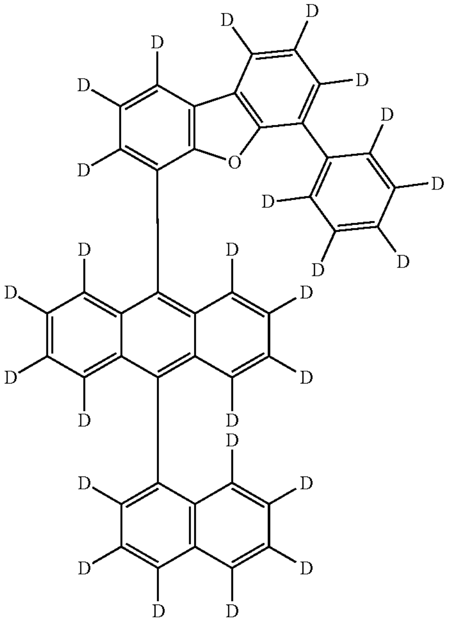
-continued
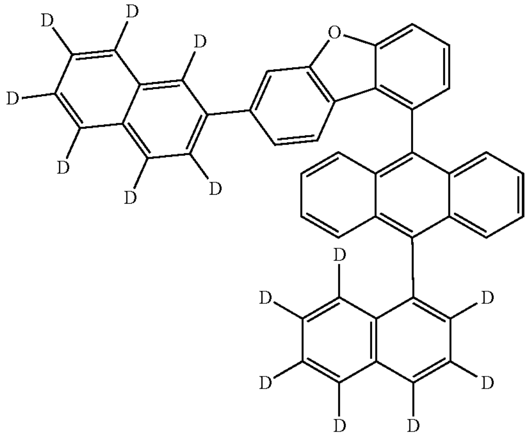
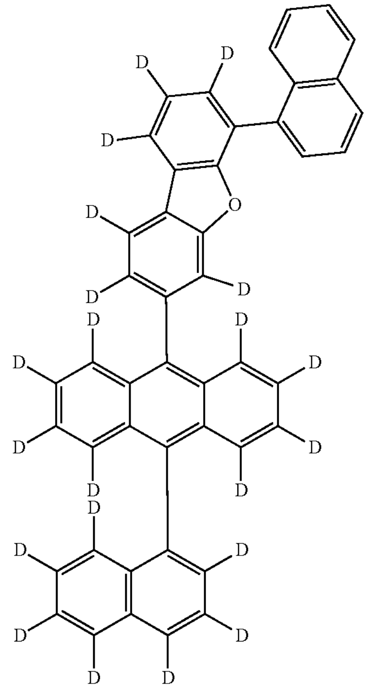
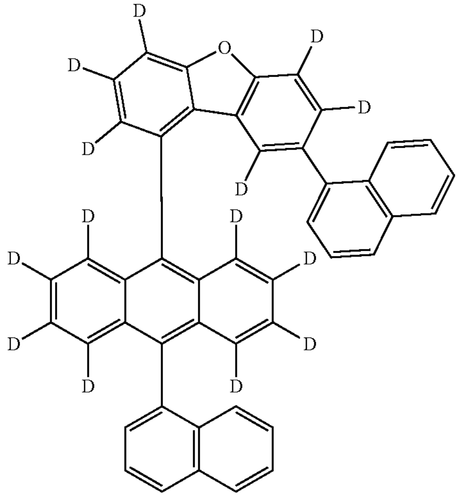

-continued
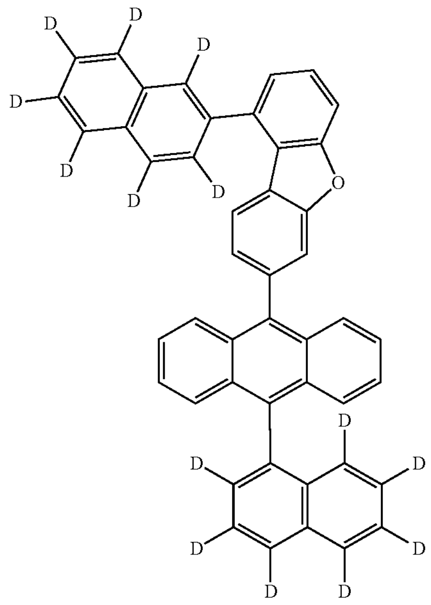
-continued
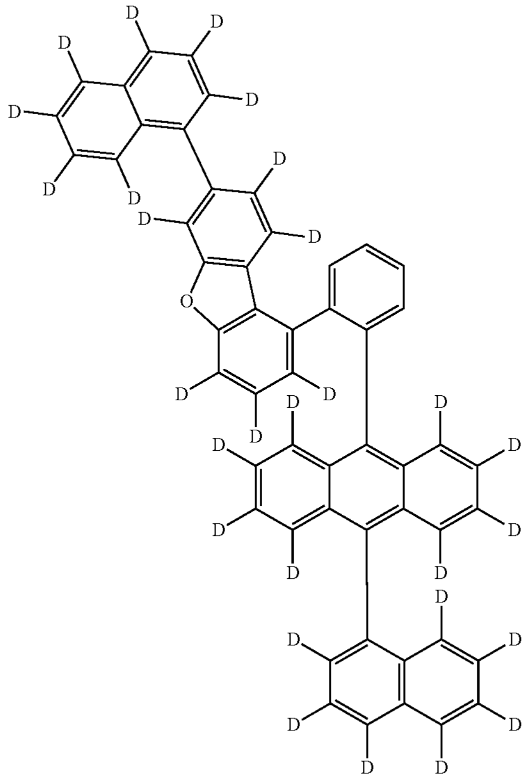
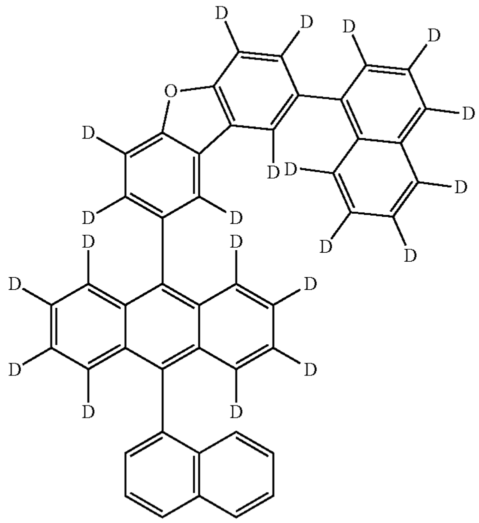
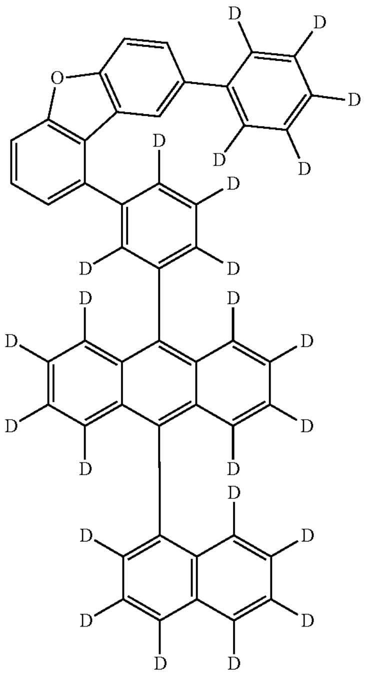

-continued
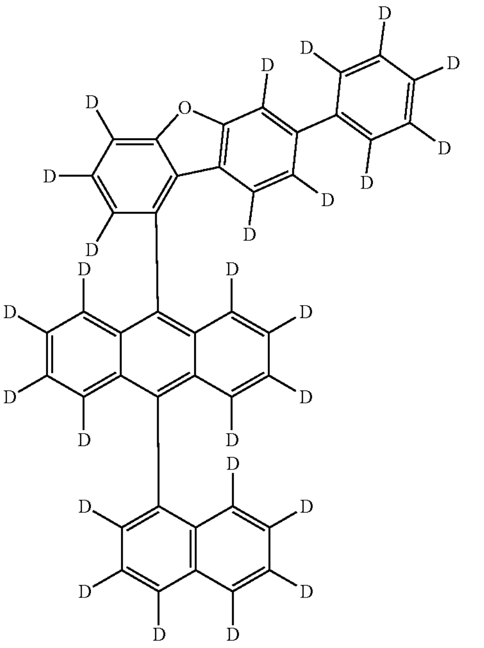
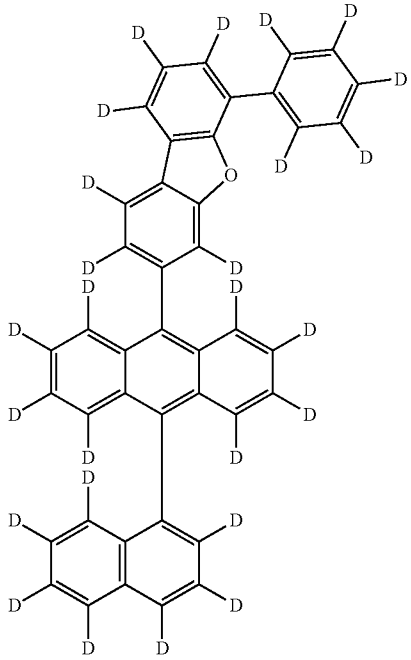
-continued
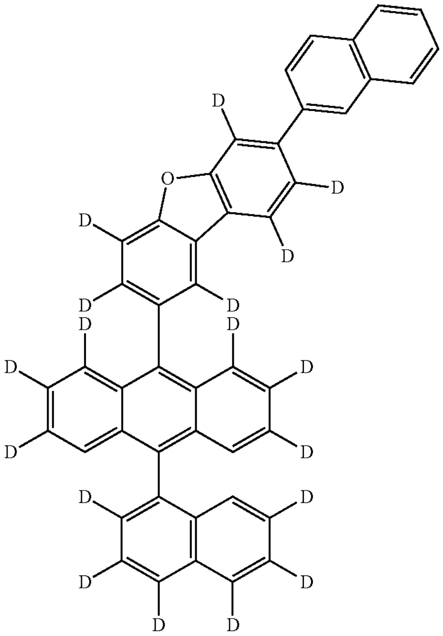
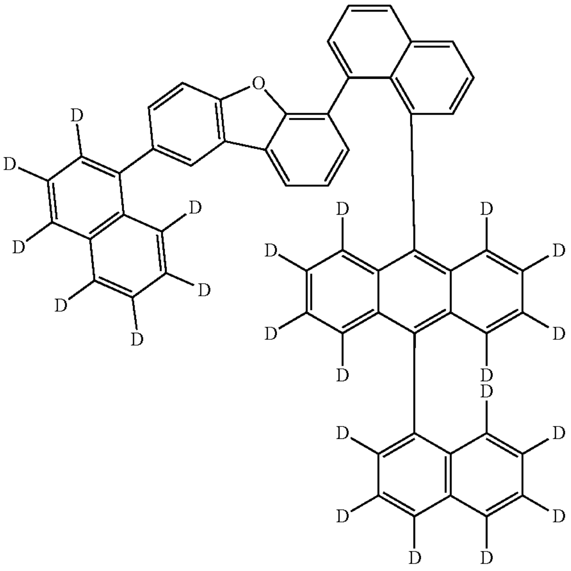

-continued
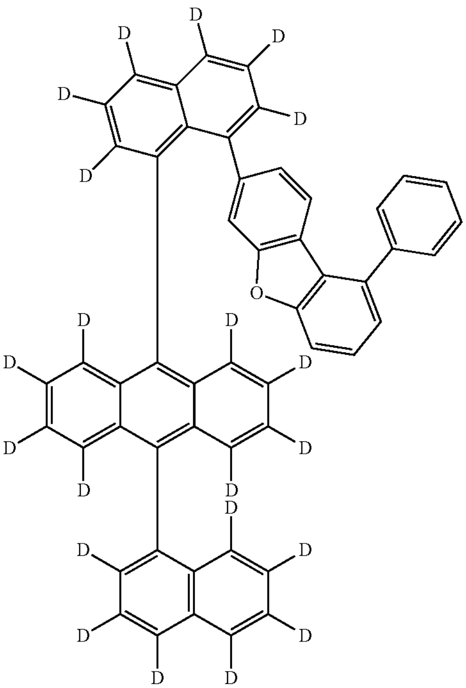
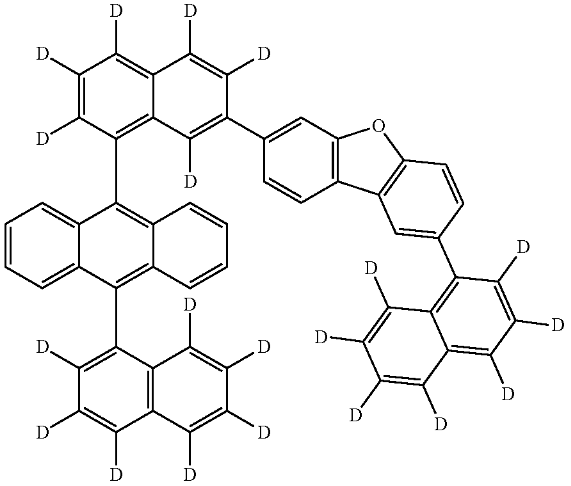
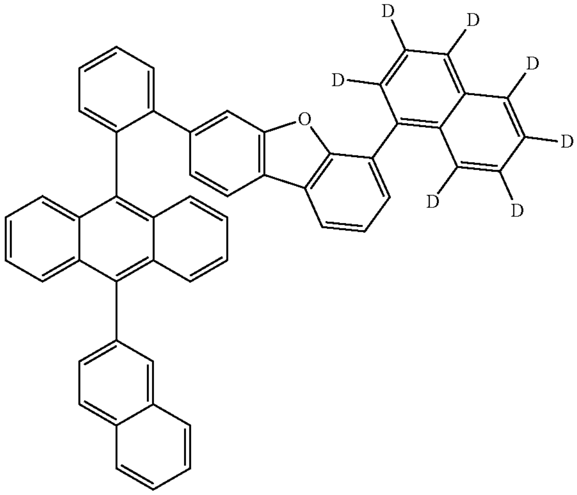
-continued
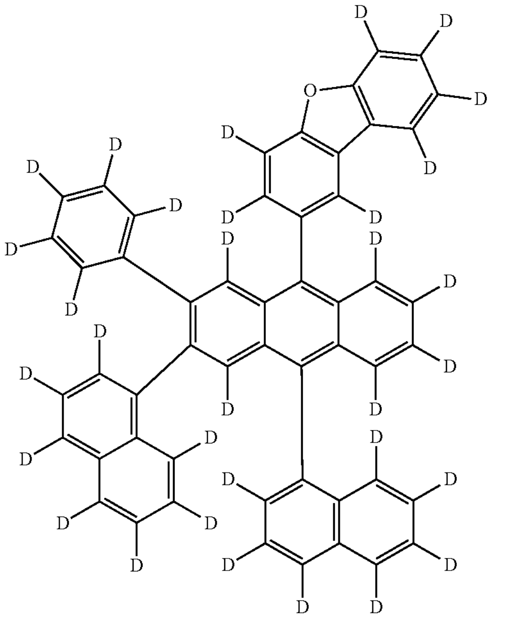
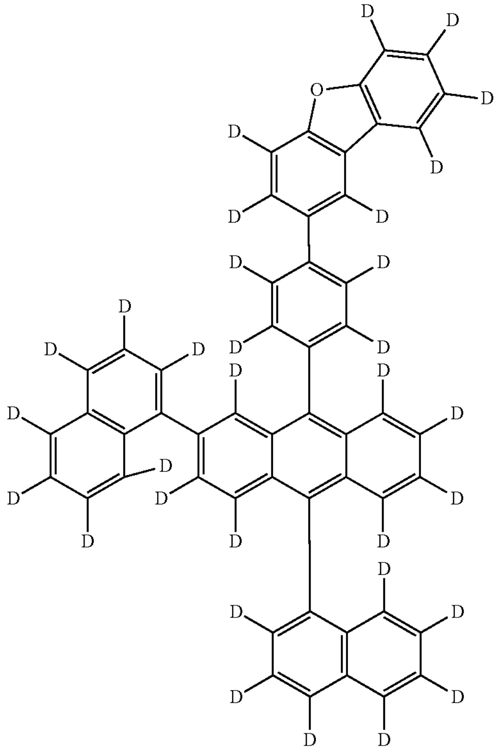

-continued
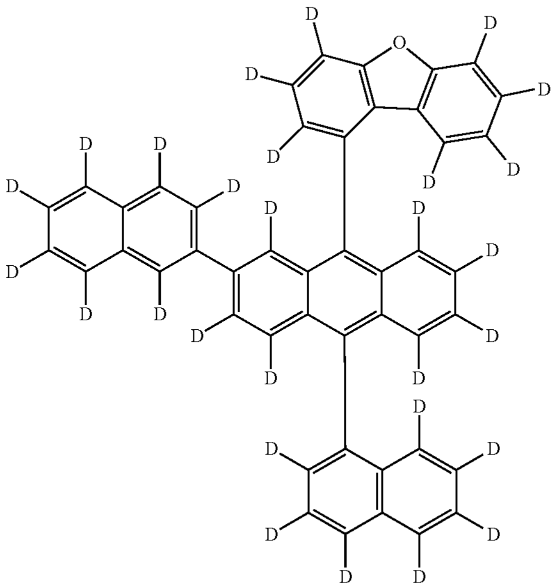
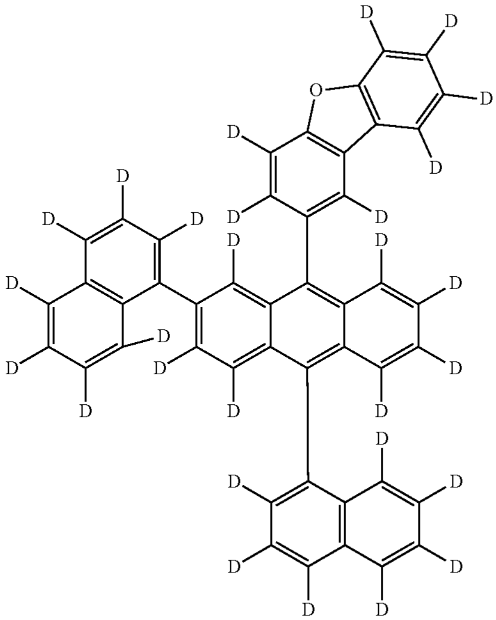
-continued
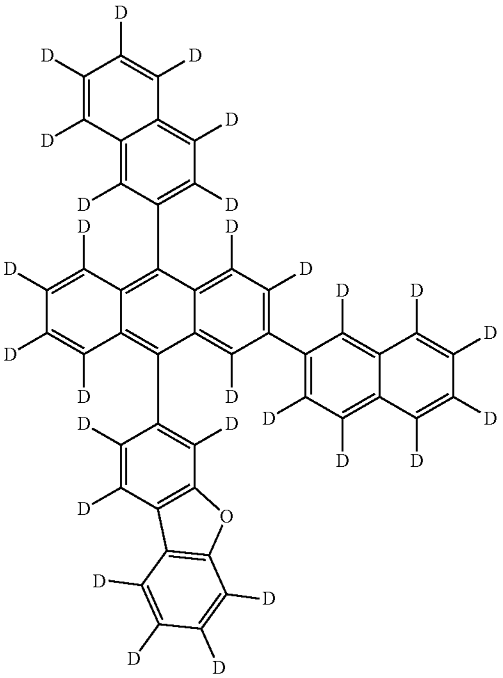
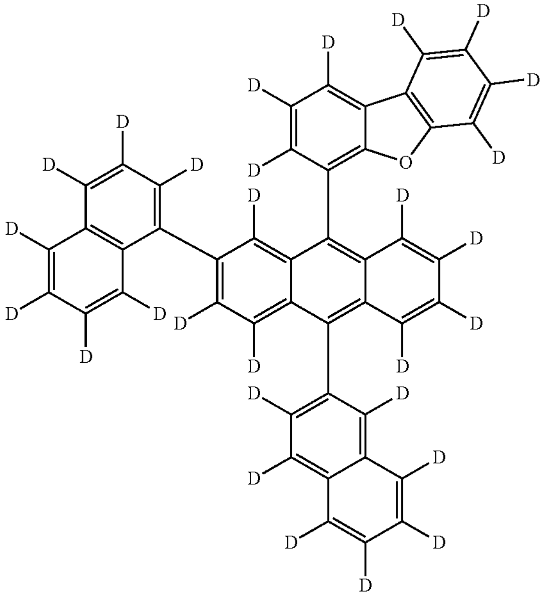

-continued
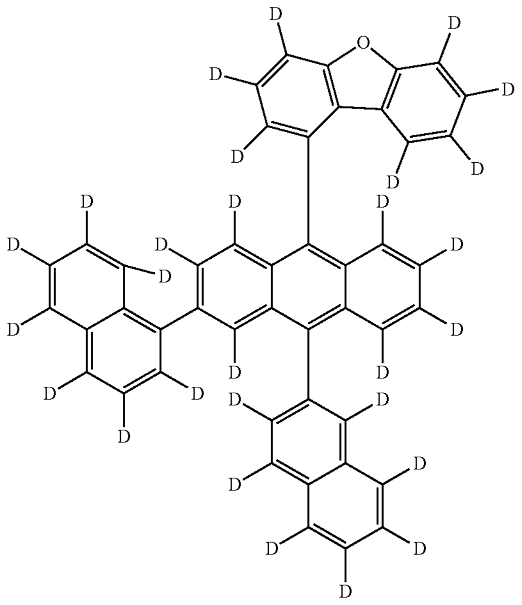
-continued
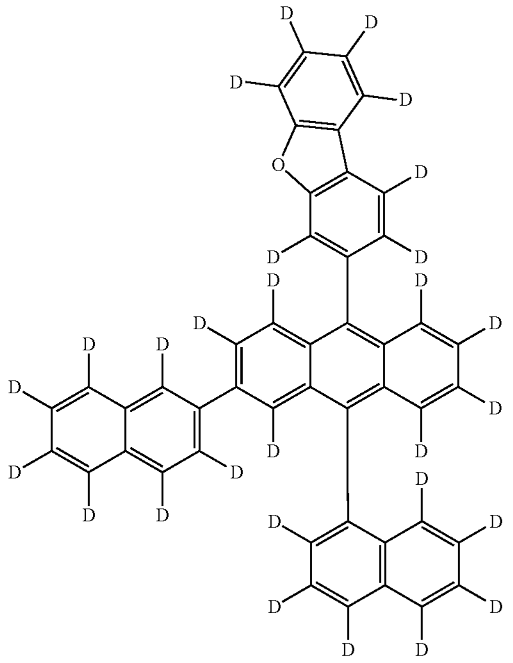
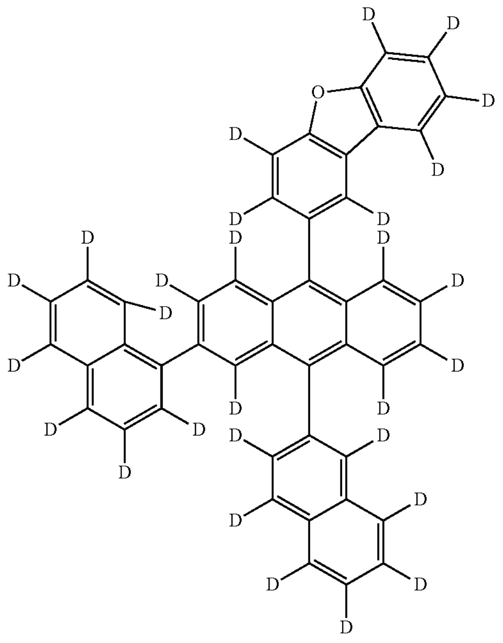
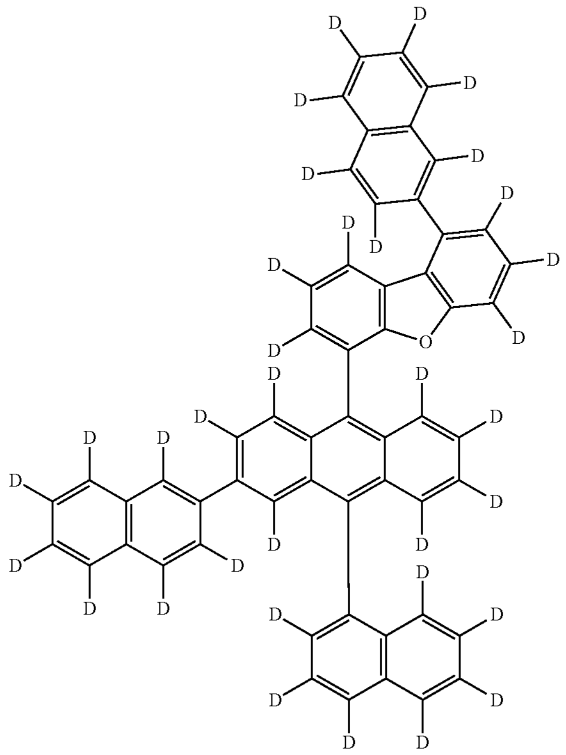

-continued
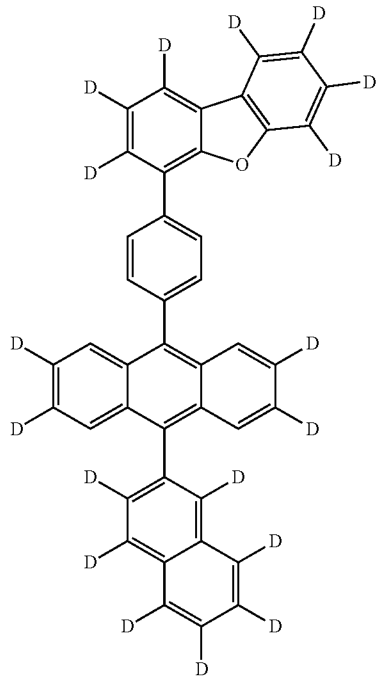
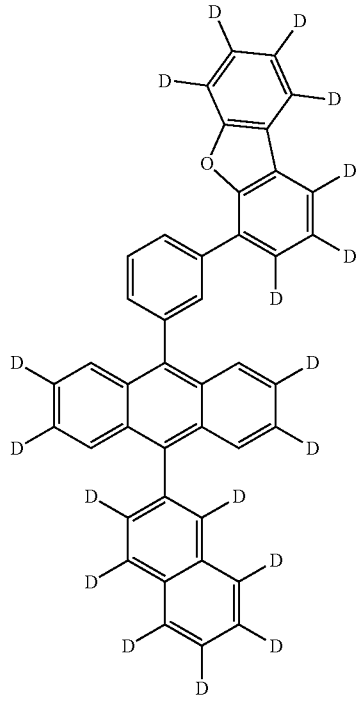
-continued
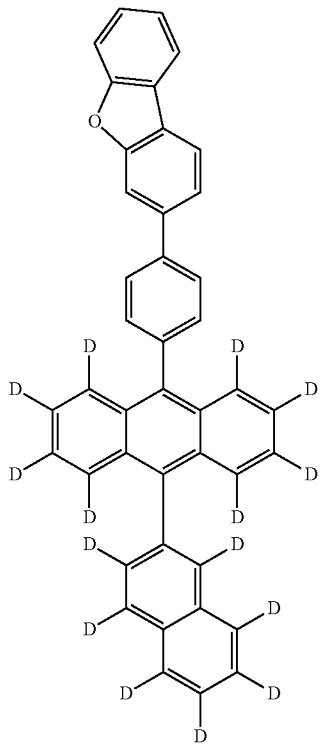
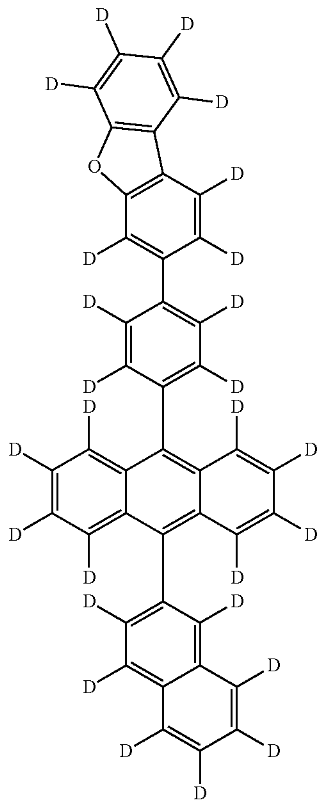

-continued
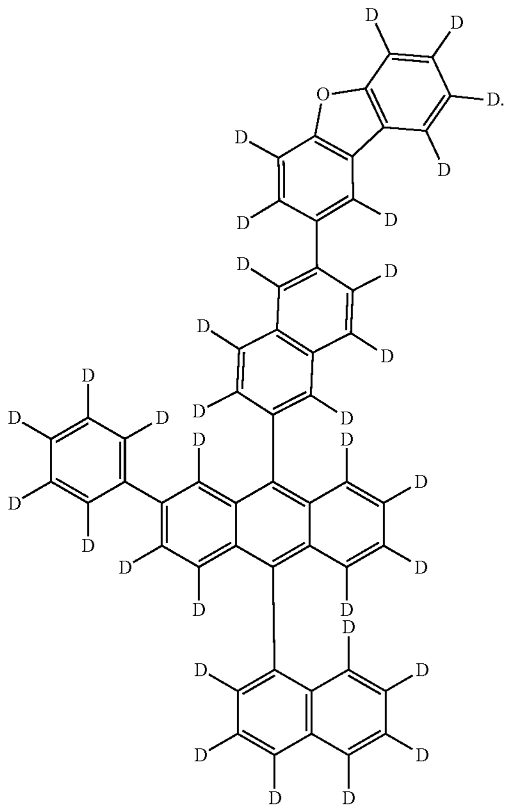
10. The organic light emitting device of claim 1, wherein the compound represented by Formula 1-2 is any one selected from the following compounds:
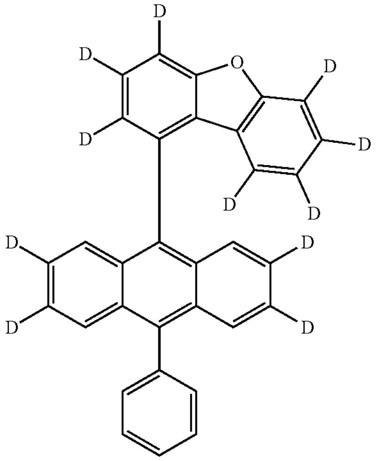
-continued
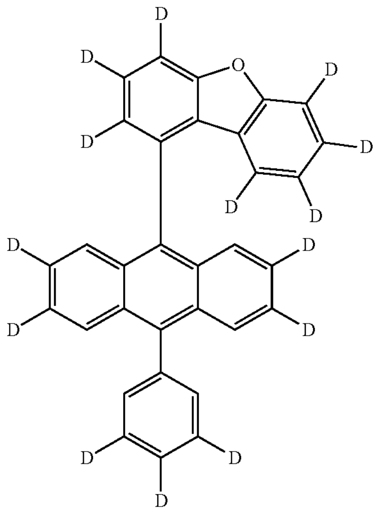
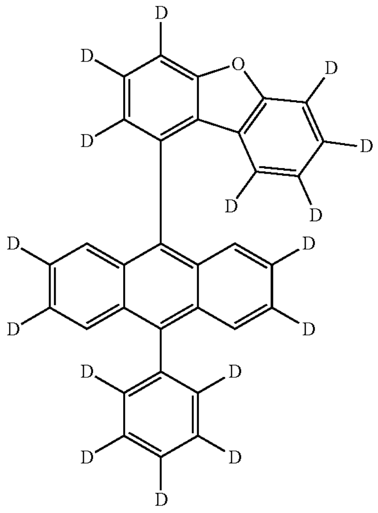
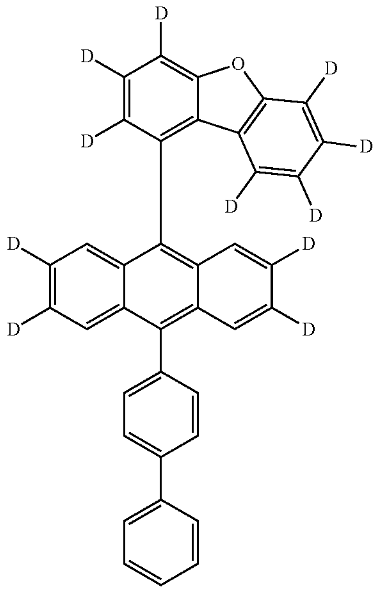

-continued
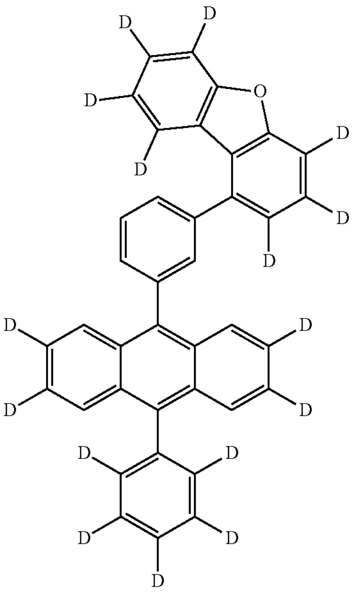
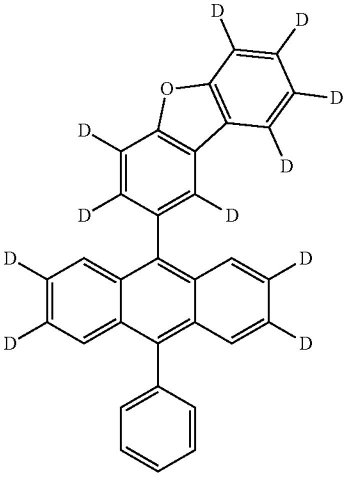
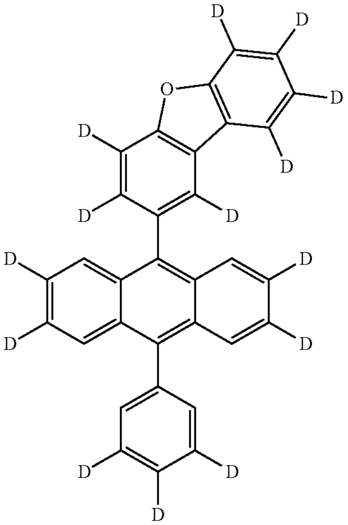
-continued
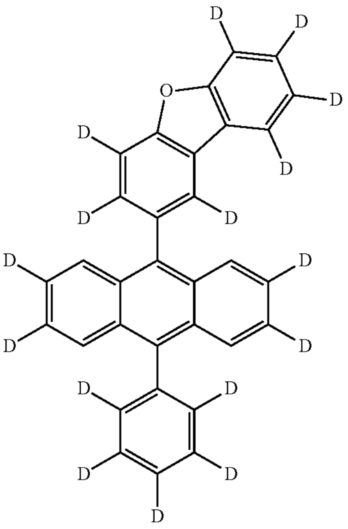
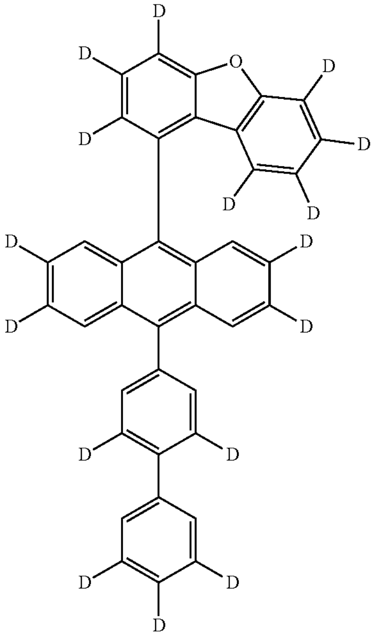

-continued
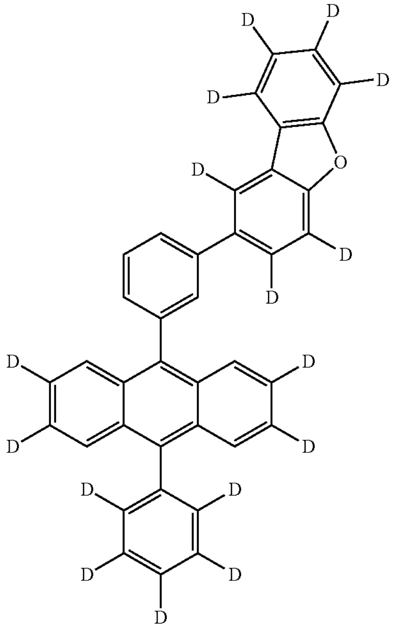
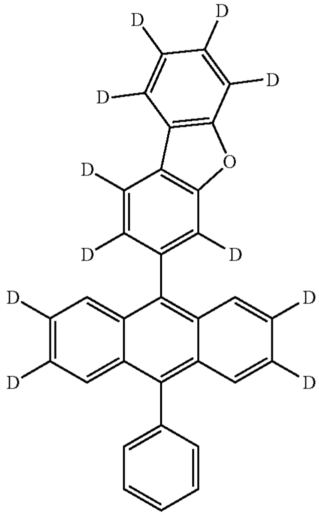
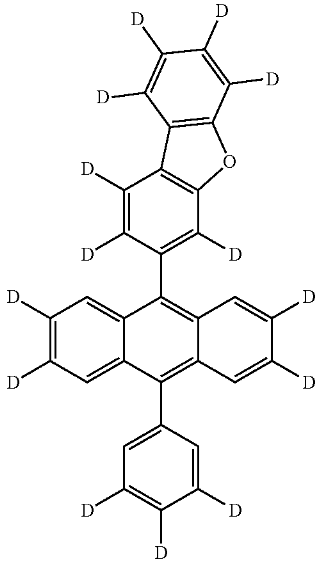
-continued
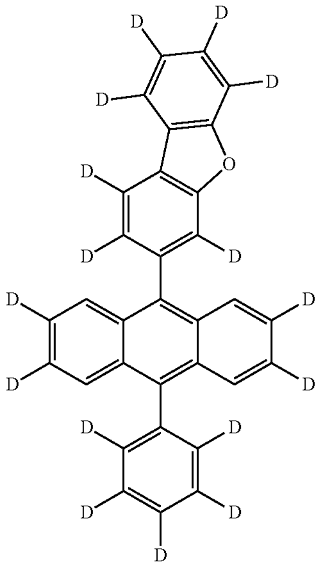
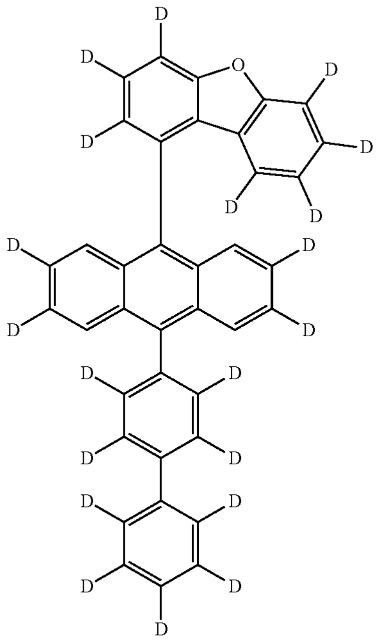

-continued
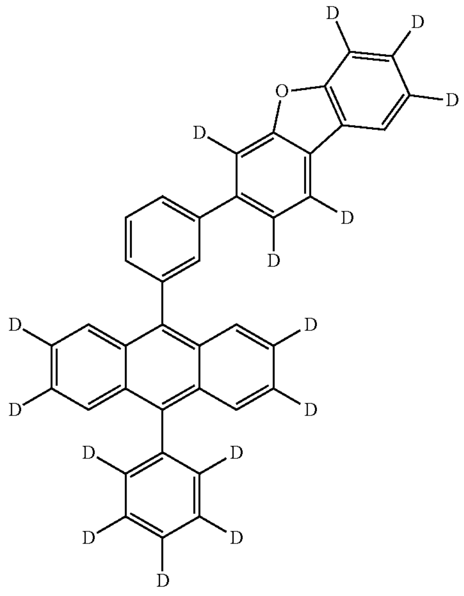
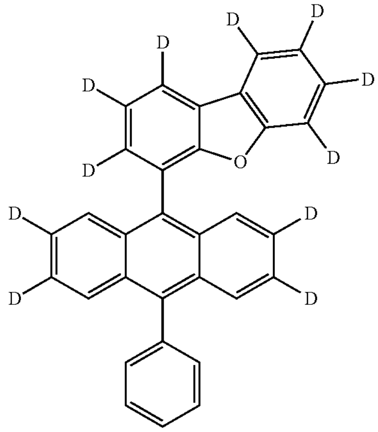
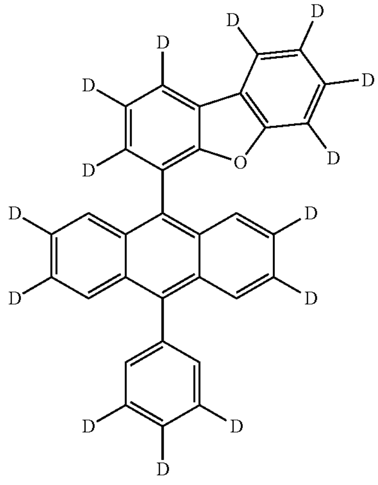
-continued
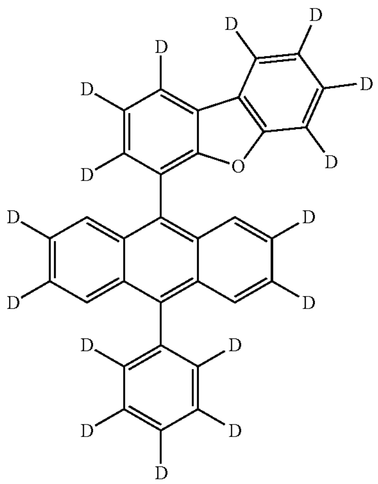
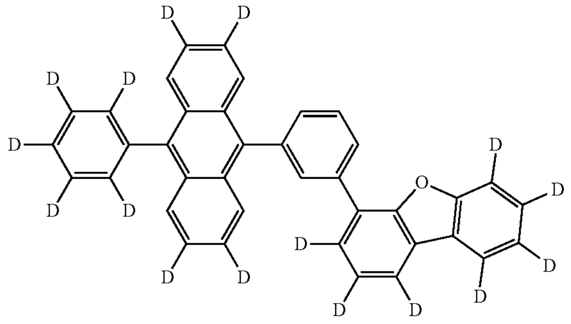
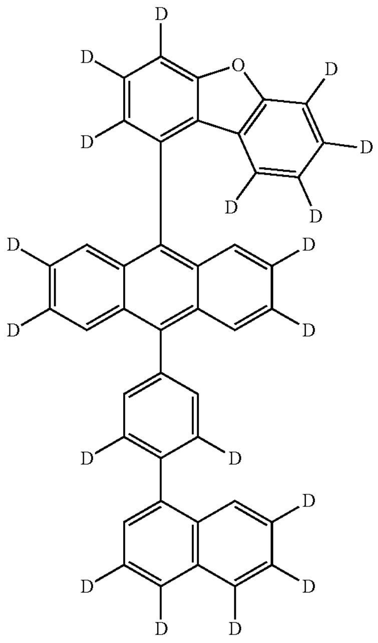

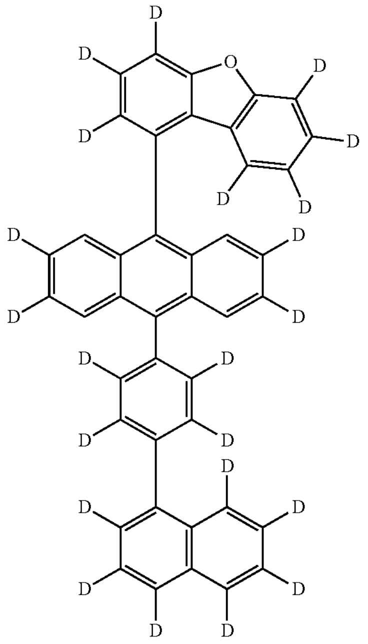
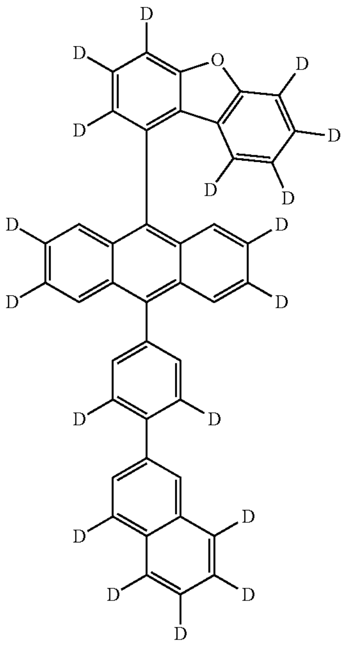
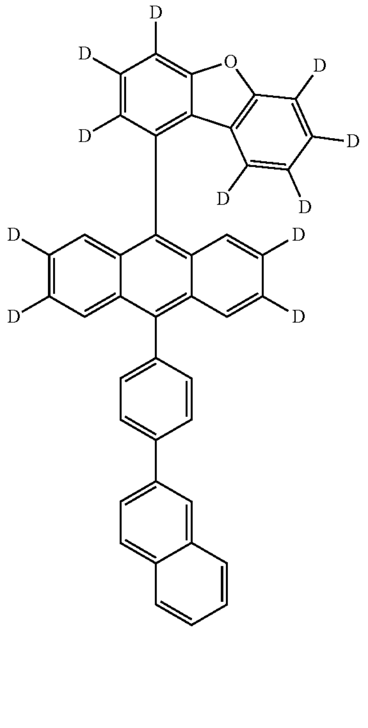
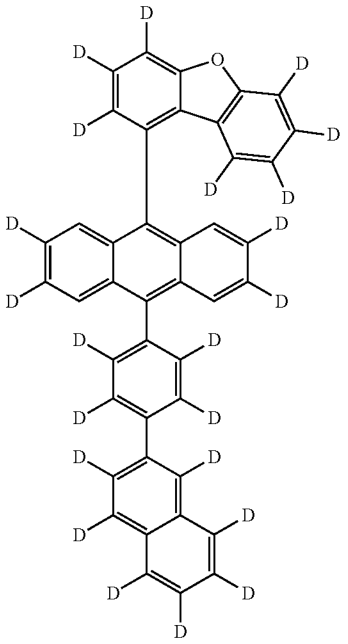

-continued
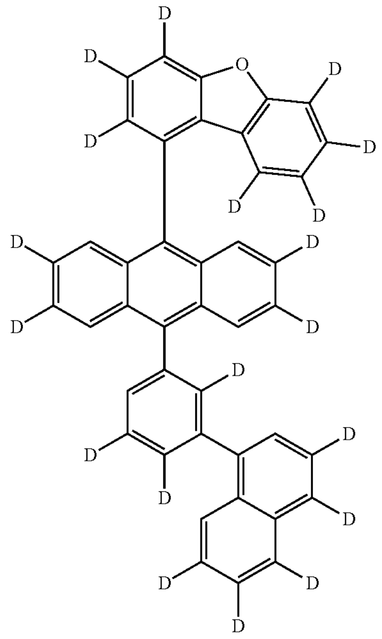
-continued
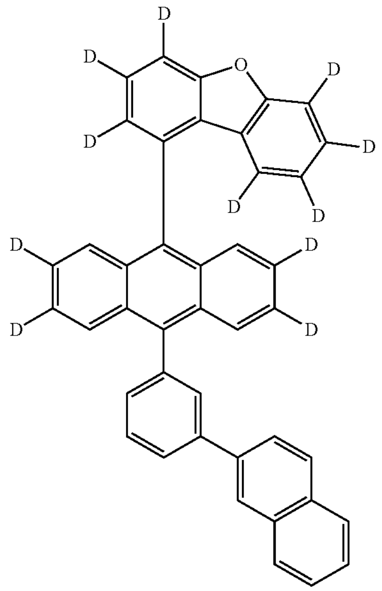
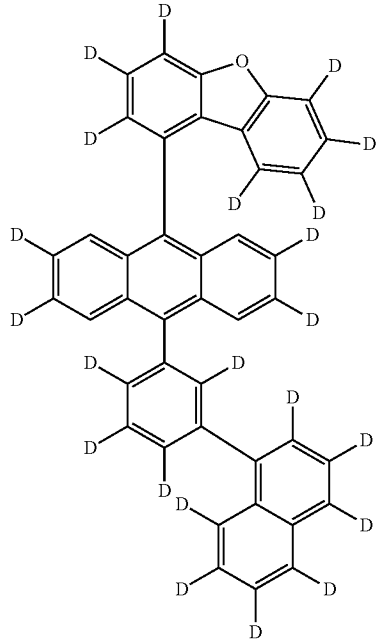
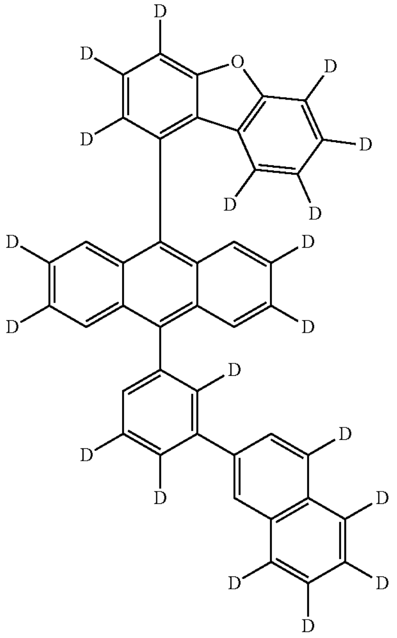

-continued
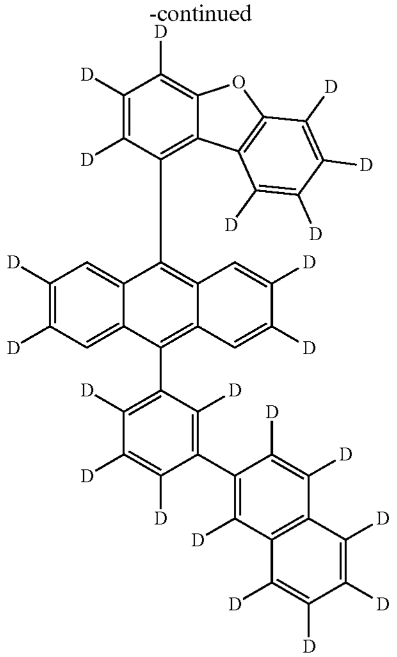
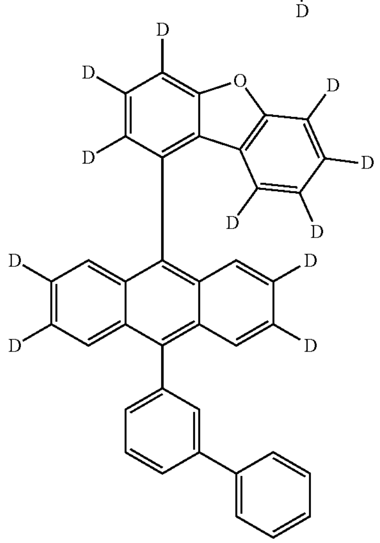
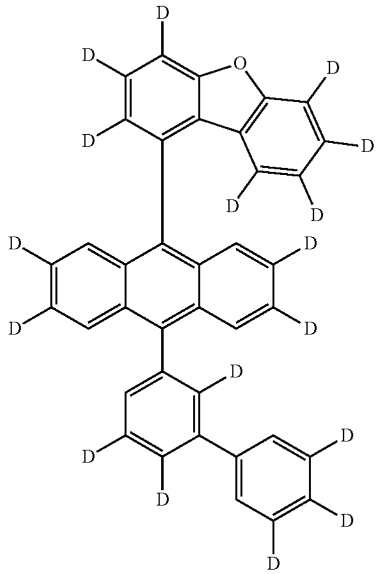
-continued
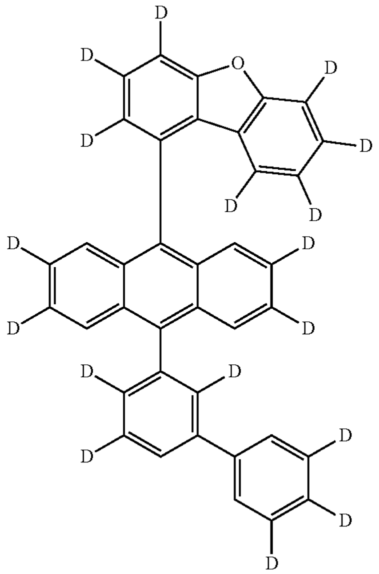
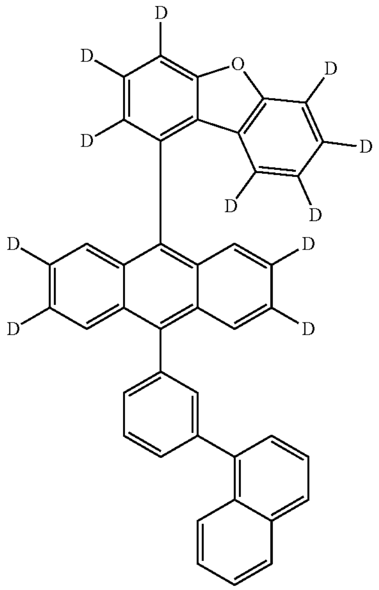

-continued
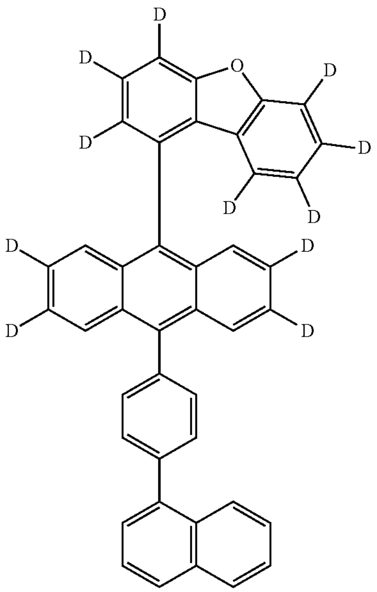
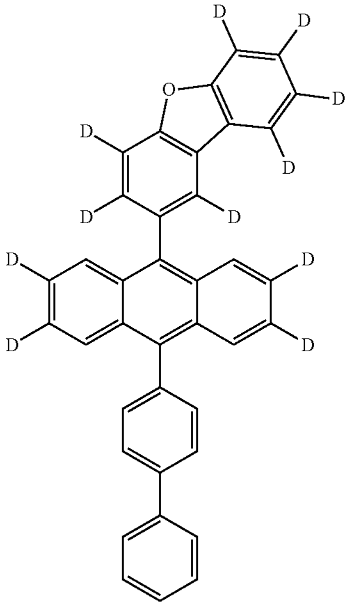
-continued
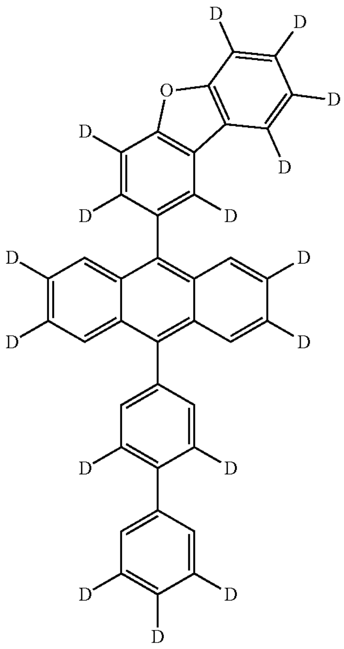
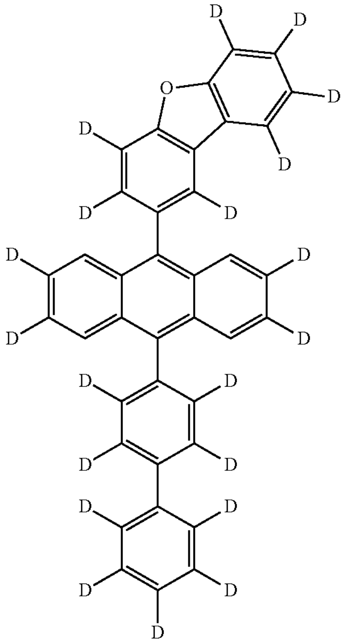

-continued
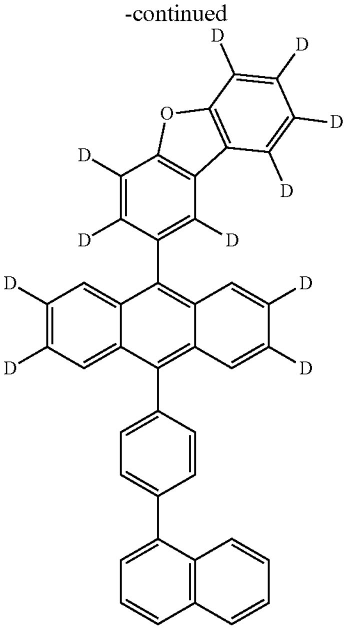
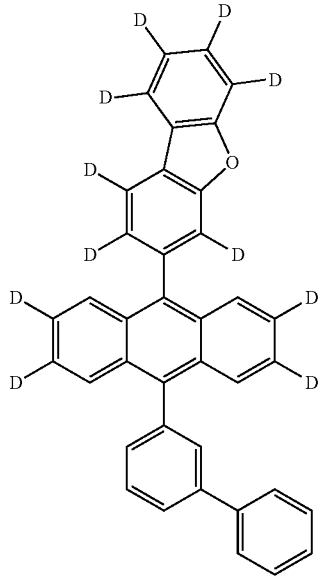
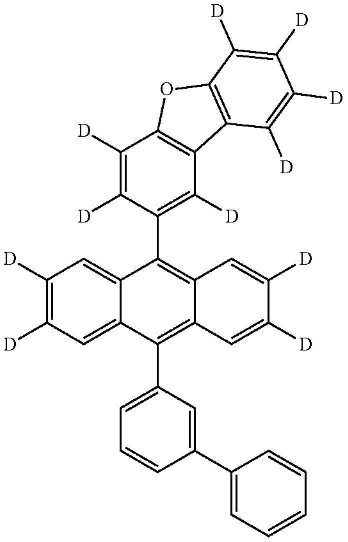 [SMILES: [2H]c1cc2c(-c3cccc(-c4ccccc4)c3)c3cc([2H])c([2H])cc3c(-c3c([2H])c([2H])c4oc5c([2H])c([2H])c([2H])c([2H])c5c4c3[2H])c2cc1[2H]]
-continued
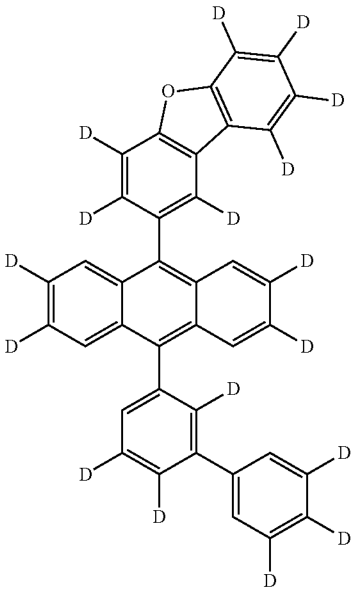
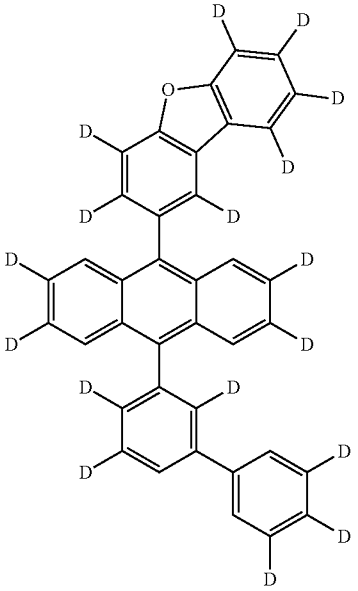

-continued
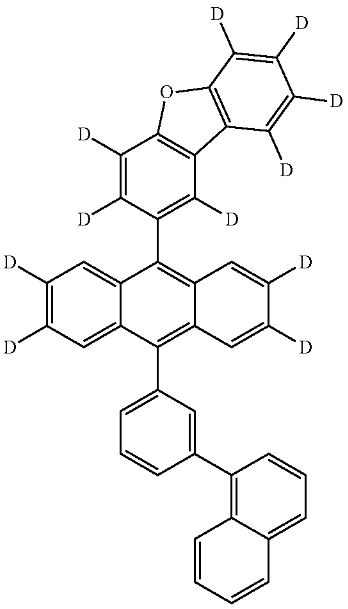
-continued
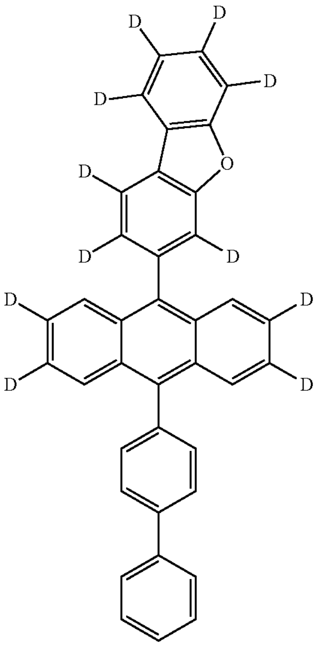
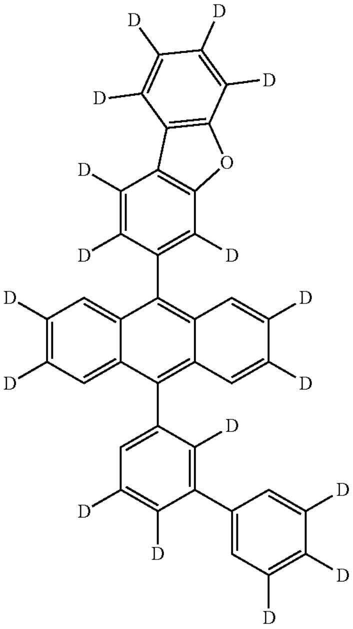
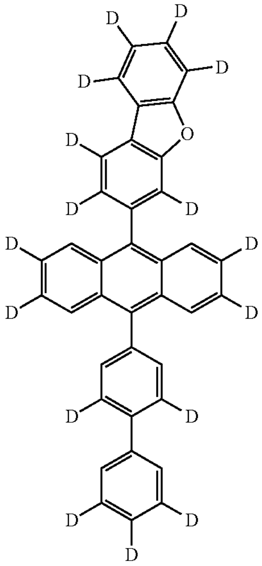

-continued
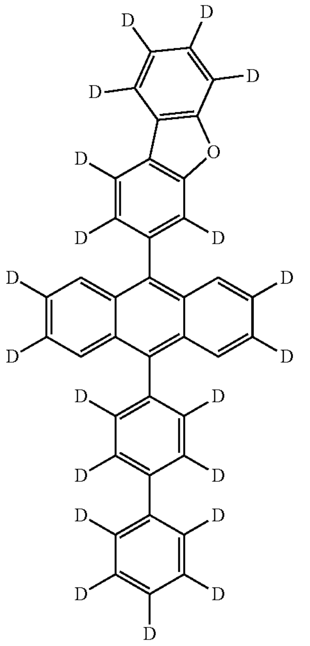
-continued
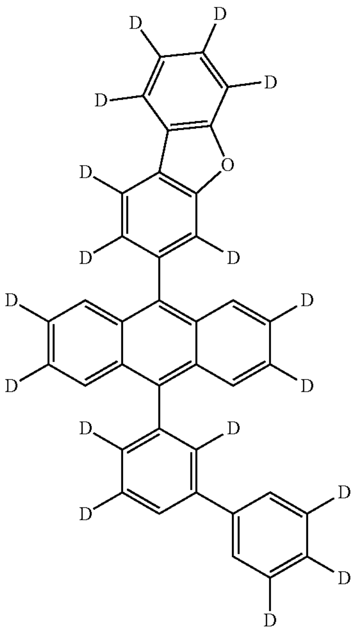
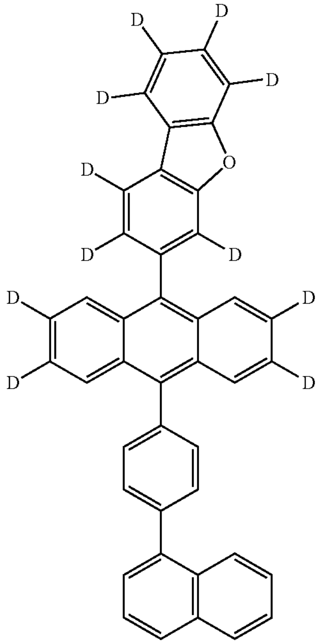
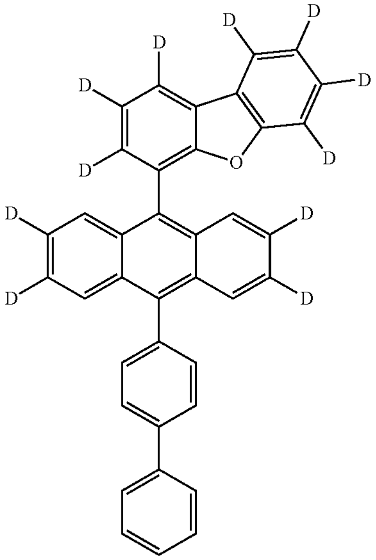

-continued
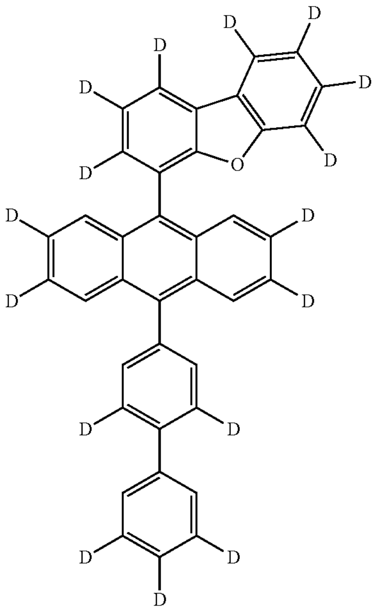
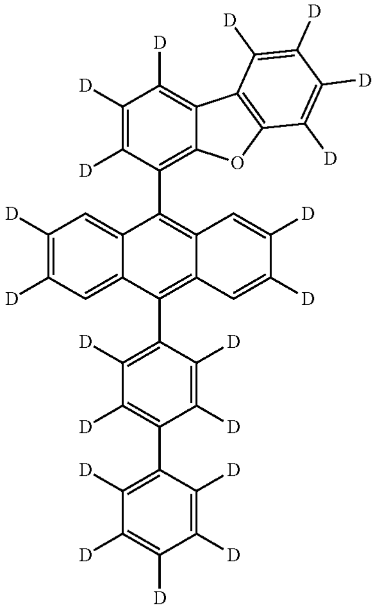
-continued
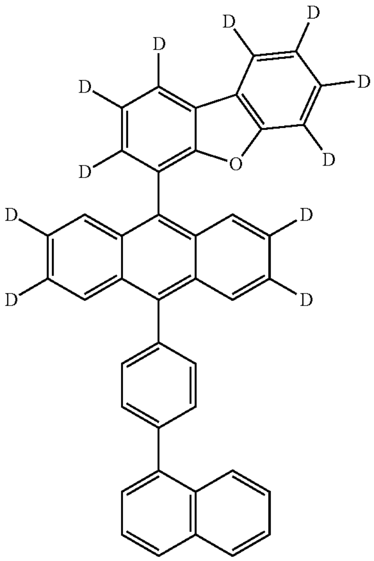
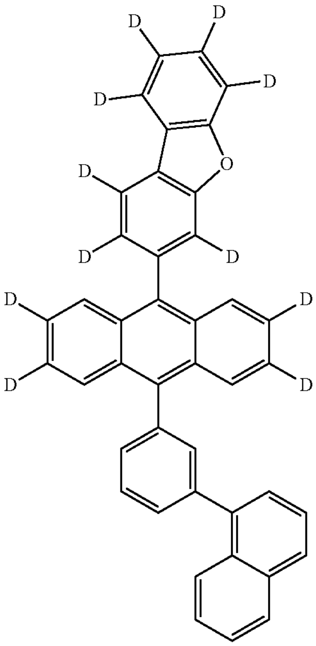

-continued
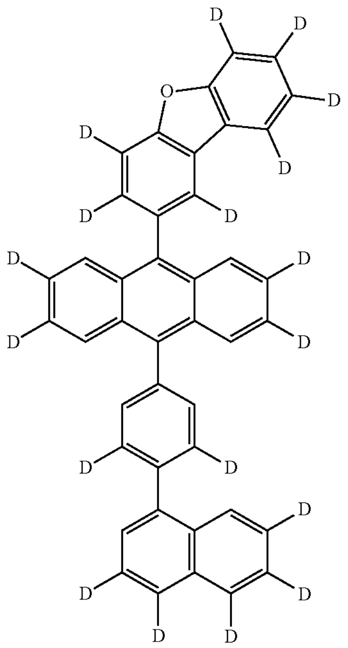
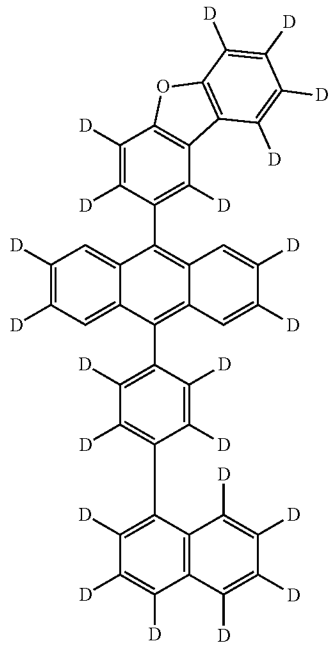
-continued
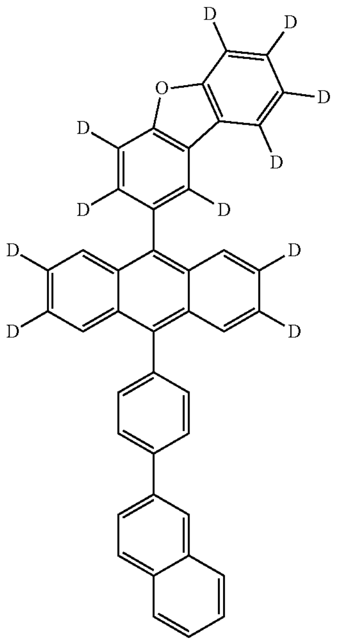
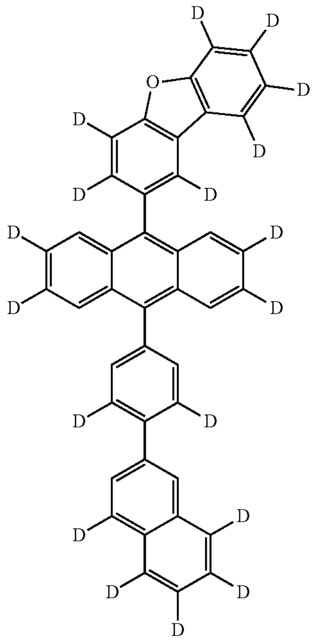

-continued
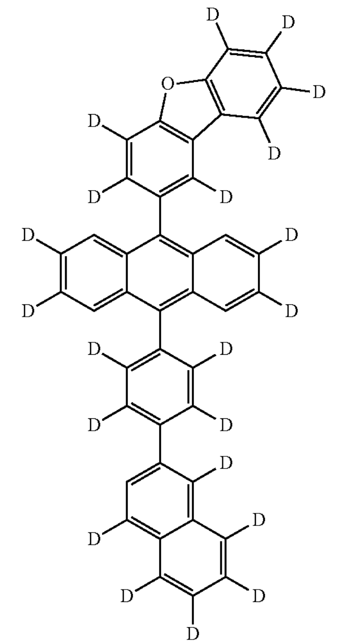
-continued
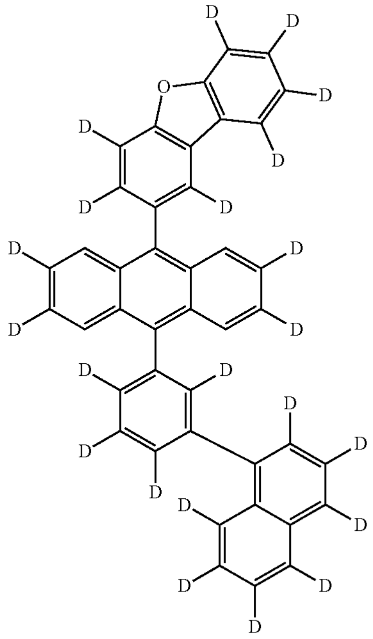
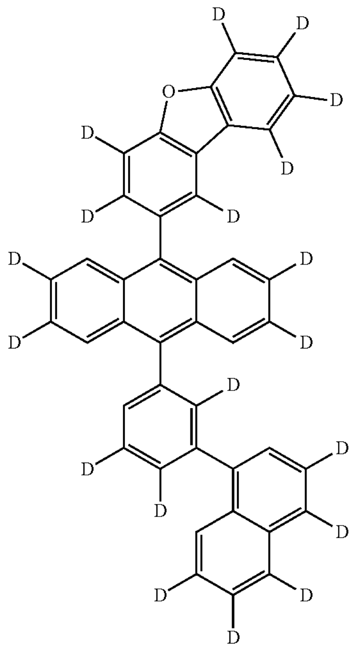
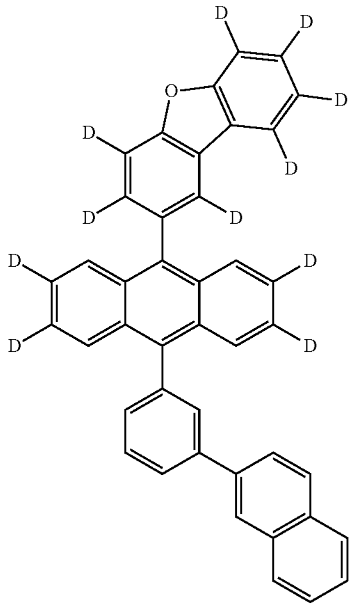

-continued
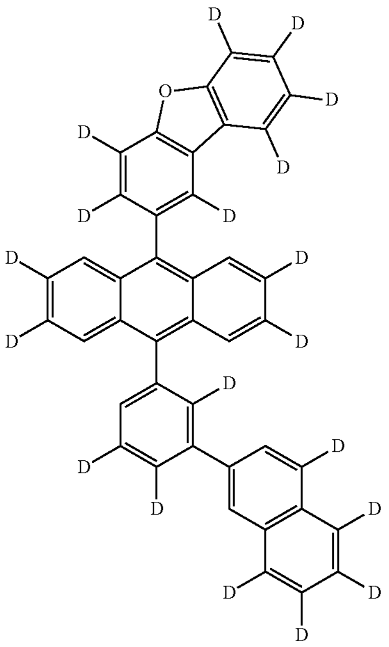
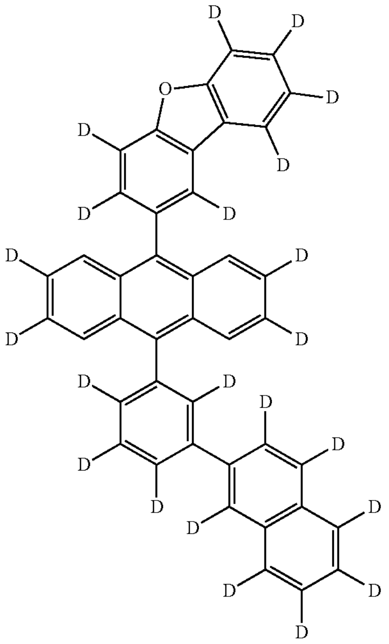
-continued
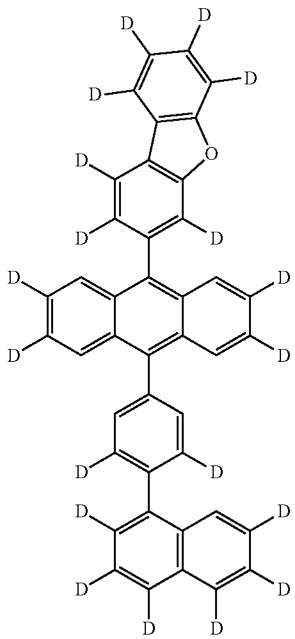
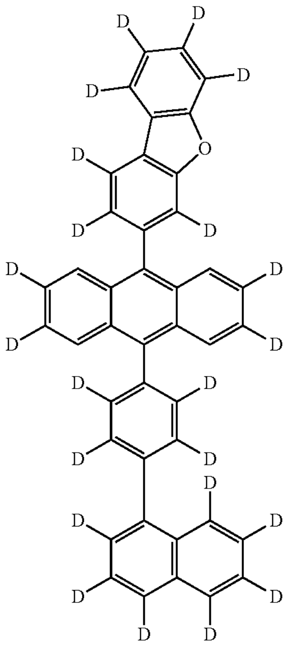

-continued
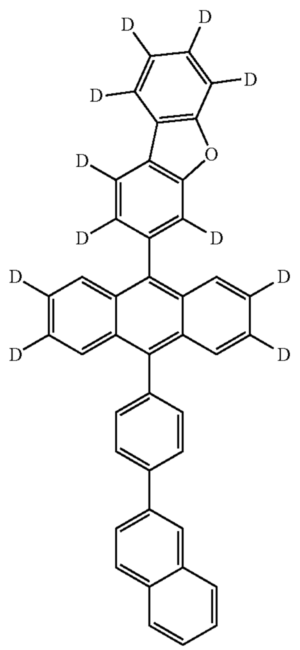
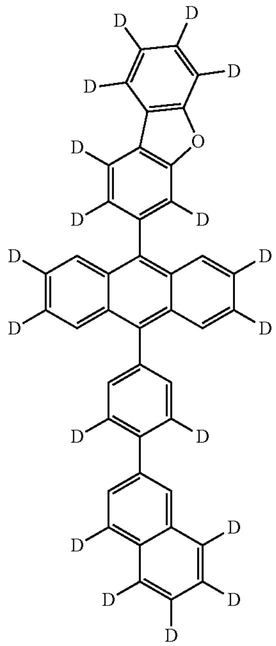
-continued
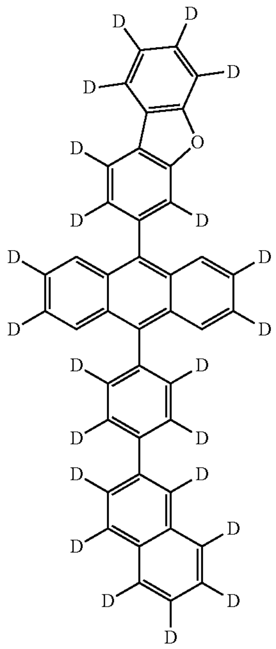
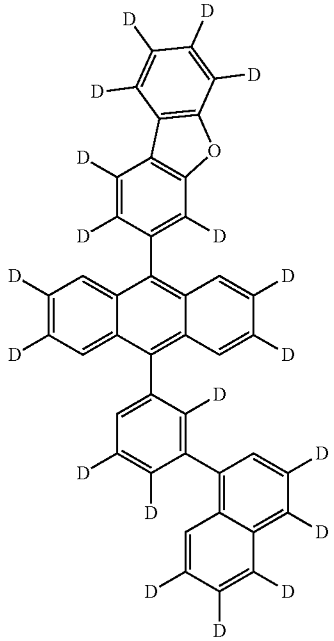

-continued
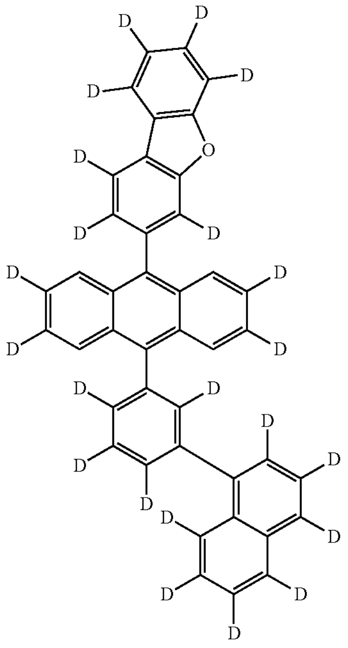
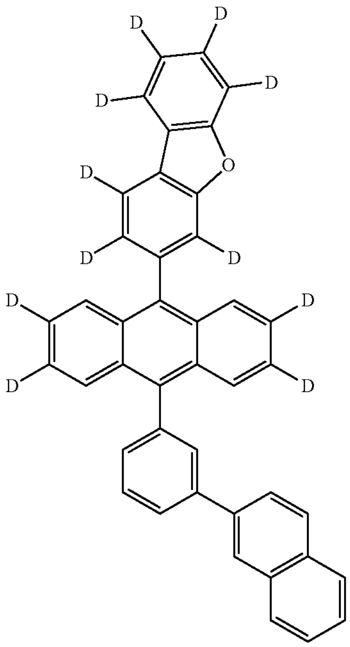
-continued
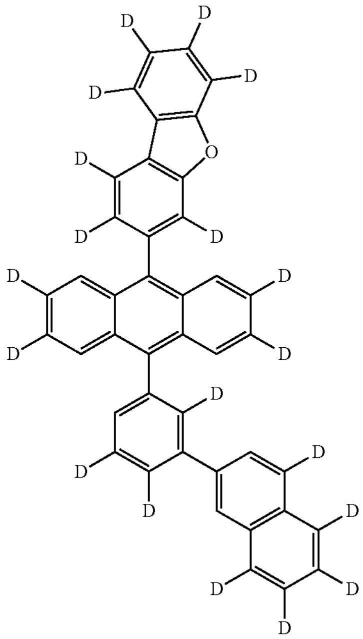
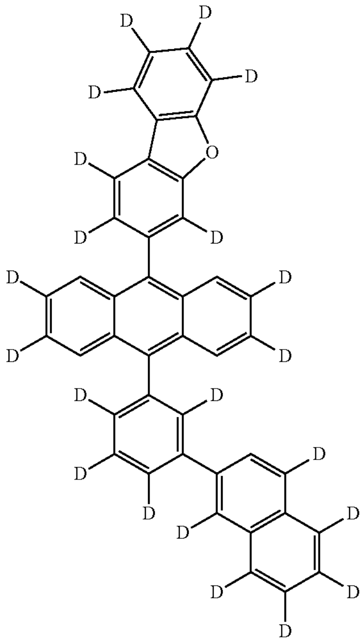 [SMILES: [2H]c1cc2c(-c3c([2H])c([2H])c([2H])c(-c4cc([2H])c5c([2H])c([2H])c([2H])c([2H])c5c4[2H])c3[2H])c3cc([2H])c([2H])cc3c(-c3c([2H])c([2H])c4c(oc5c([2H])c([2H])c([2H])c([2H])c54)c3[2H])c2cc1[2H]]

-continued
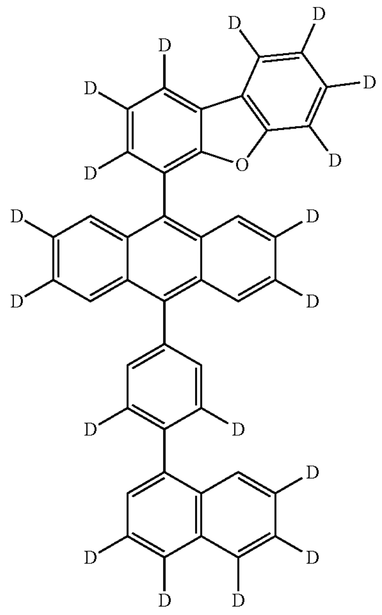
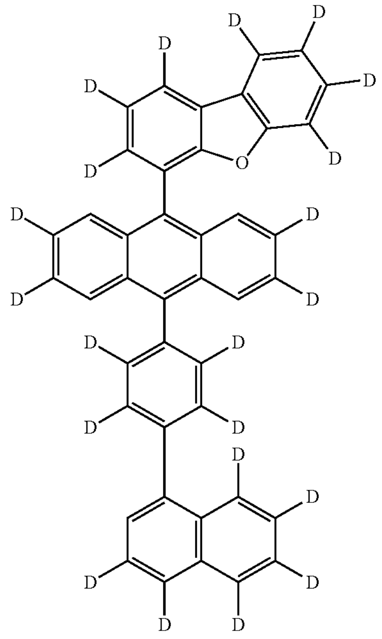
-continued
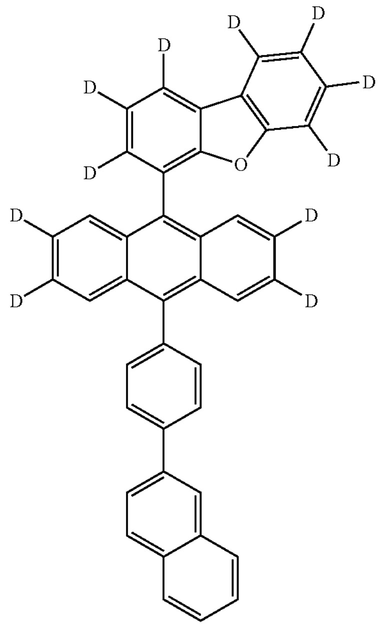
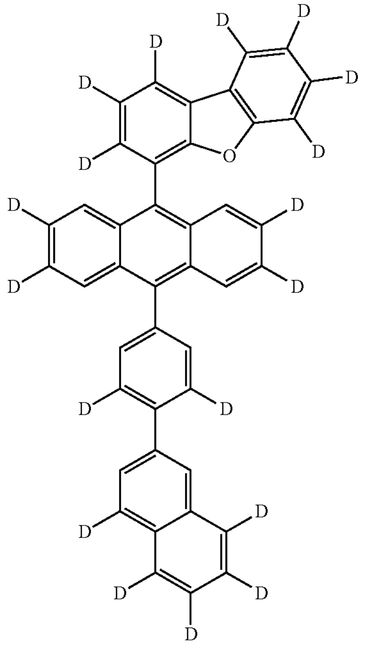

-continued
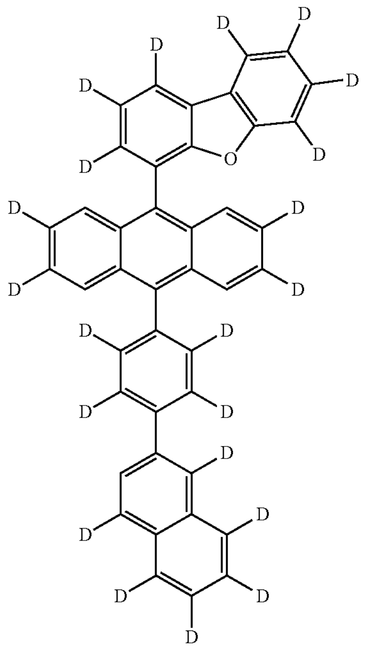
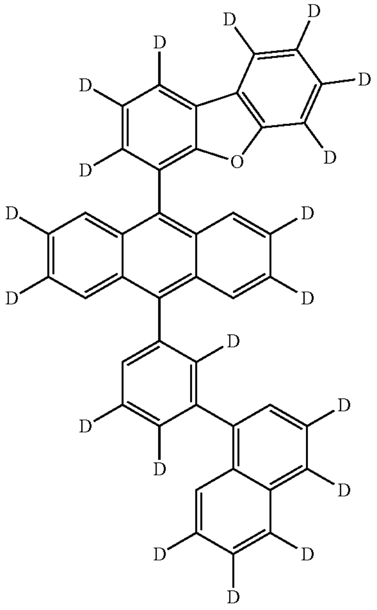
-continued
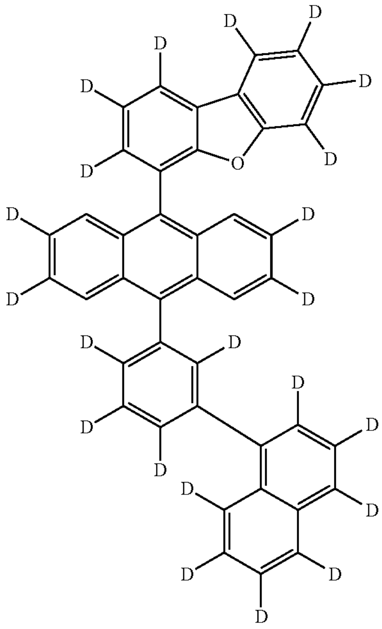
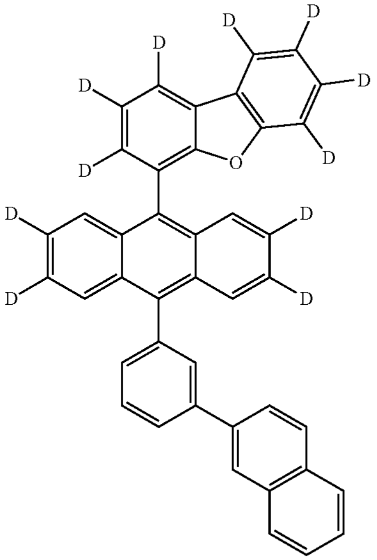

-continued
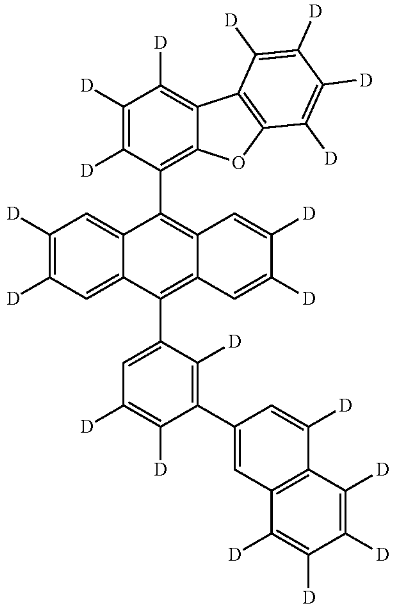
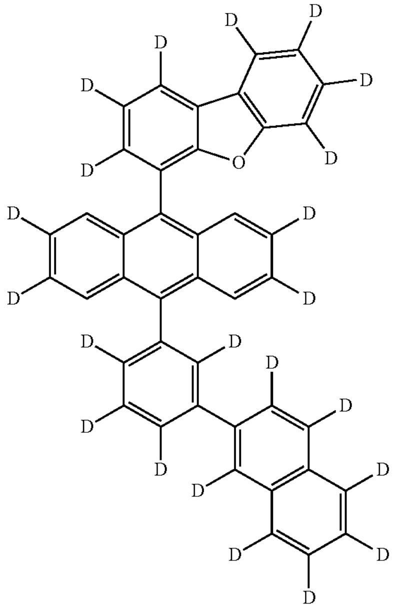
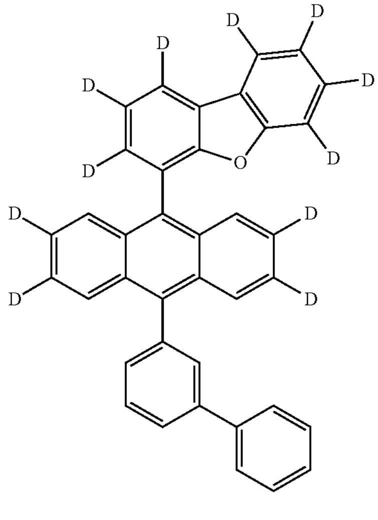
-continued
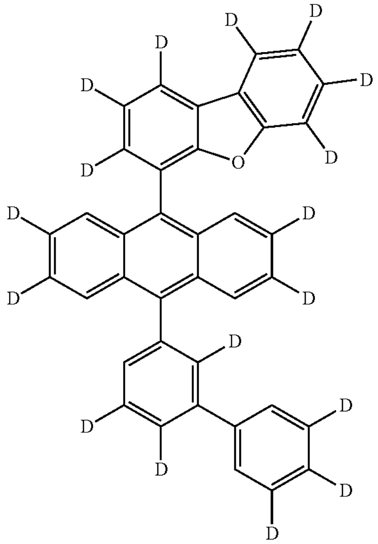
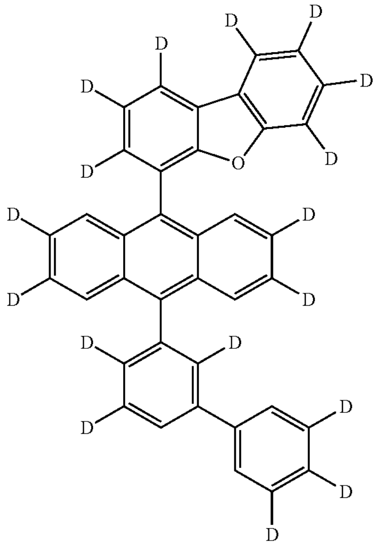
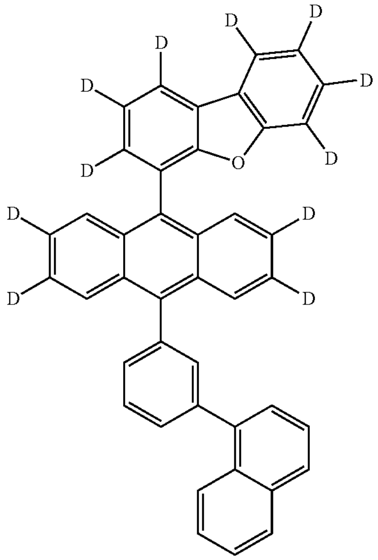 [SMILES: [2H]c1cc2c(-c3cccc(-c4cccc5ccccc45)c3)c3cc([2H])c([2H])cc3c(-c3c([2H])c([2H])c([2H])c4c3oc3c([2H])c([2H])c([2H])c([2H])c34)c2cc1[2H]]

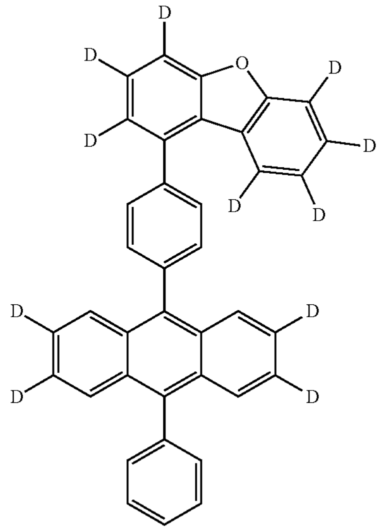
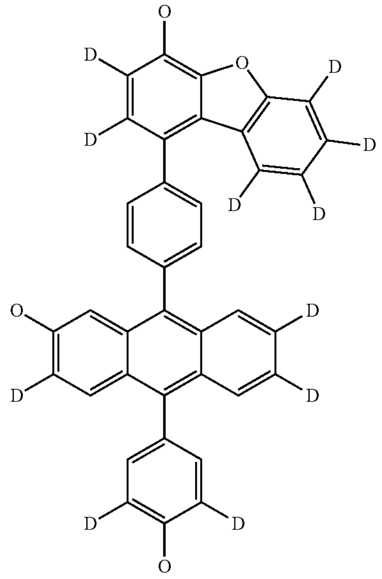
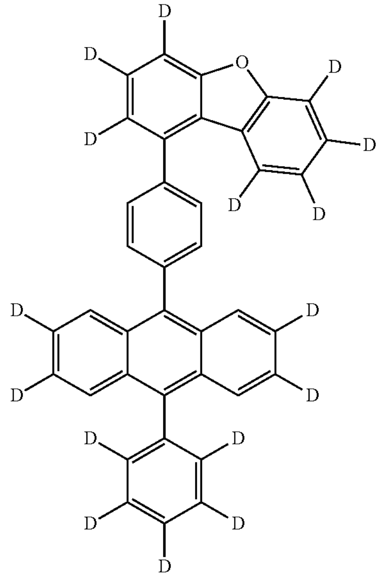
-continued
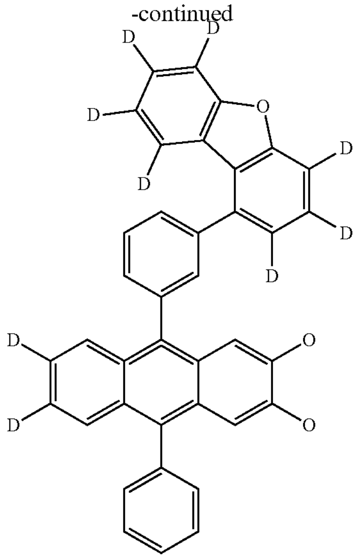
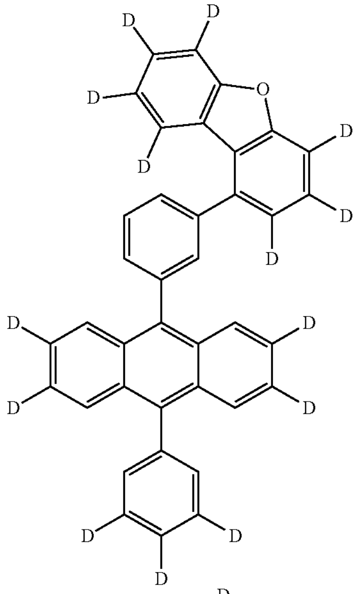
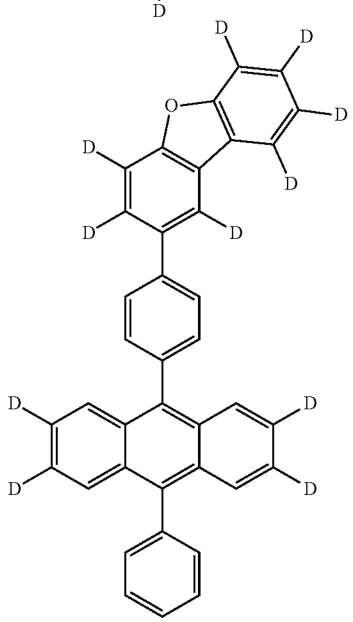

-continued
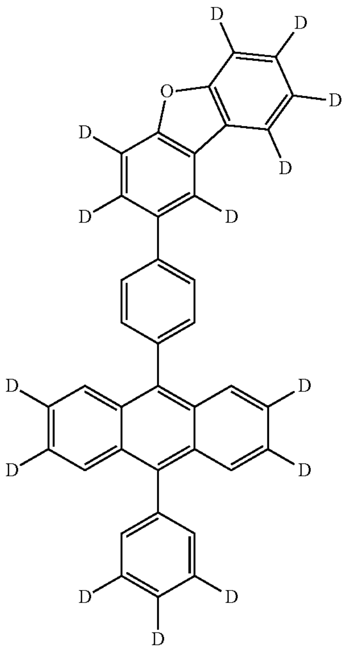
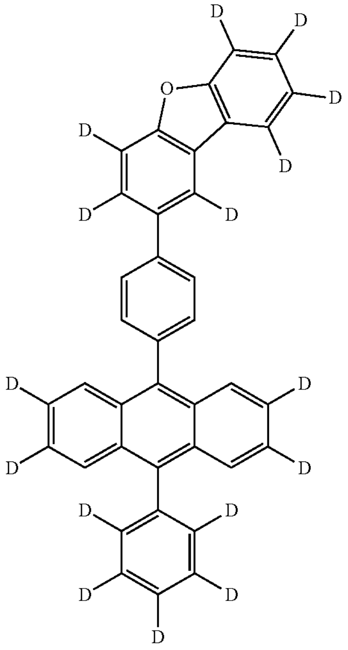
-continued
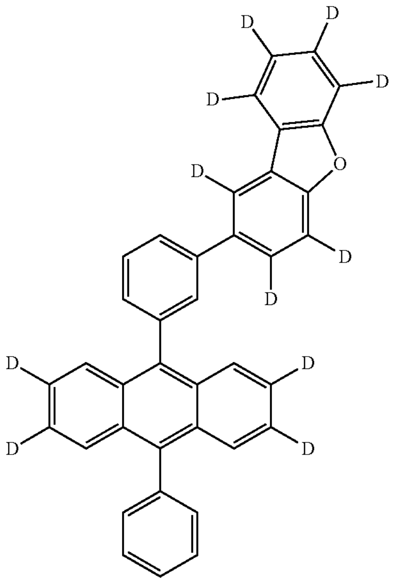
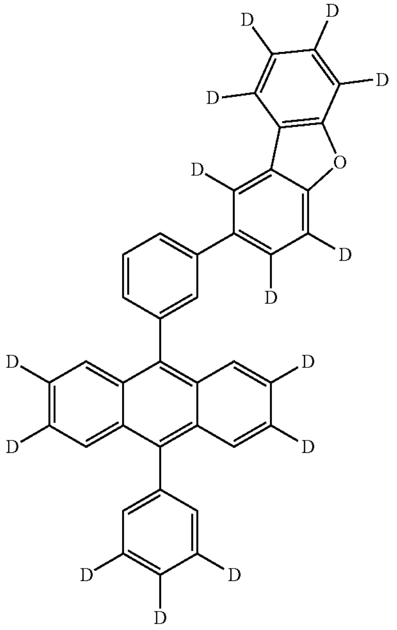

-continued
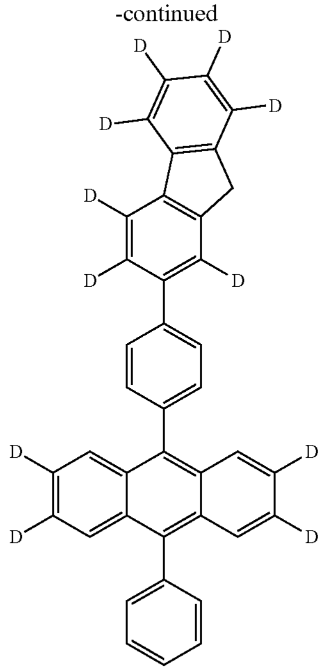
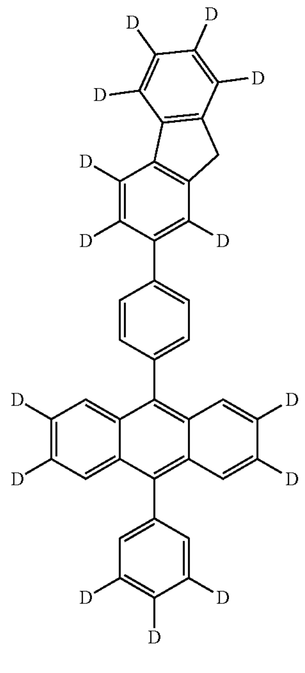
-continued
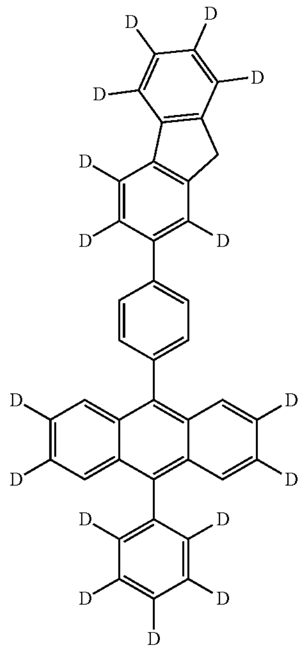
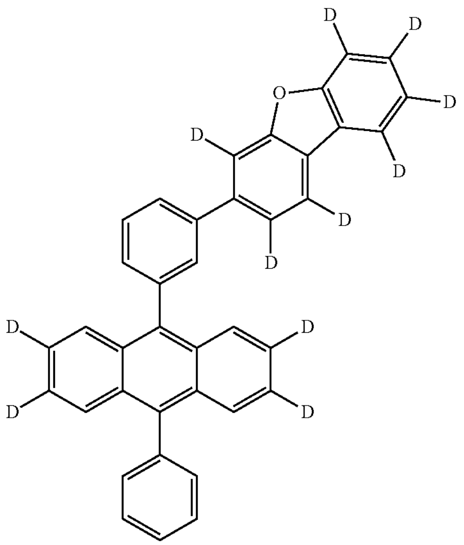

-continued
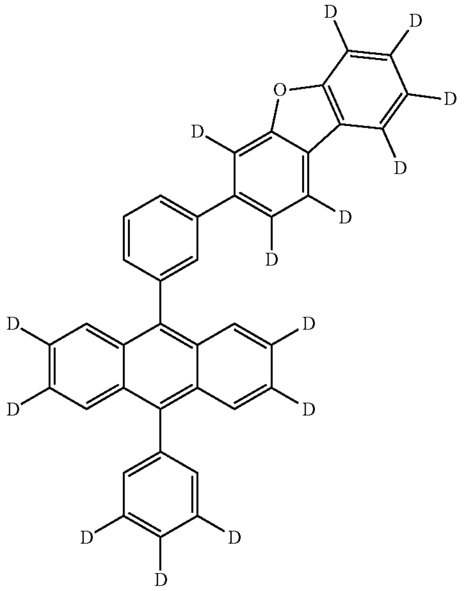
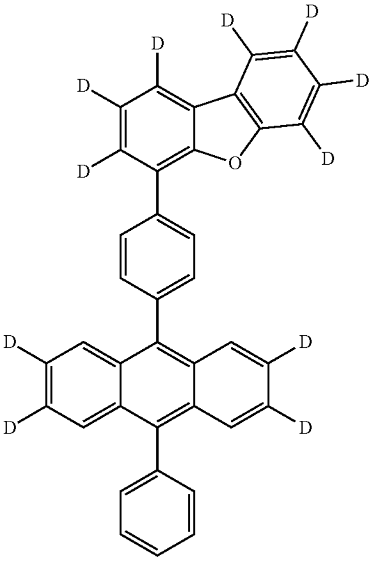
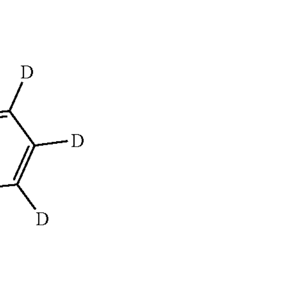
-continued
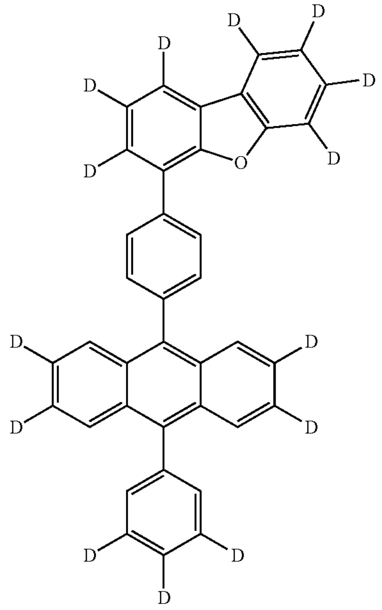
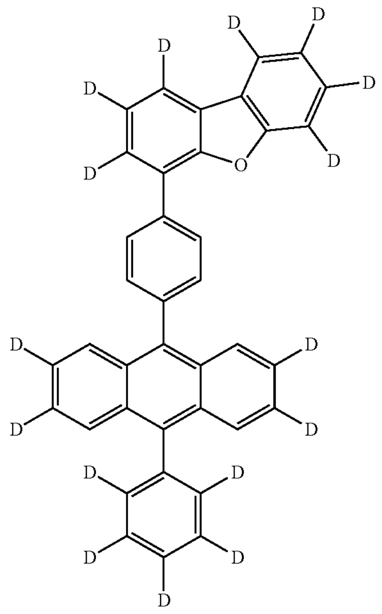

-continued
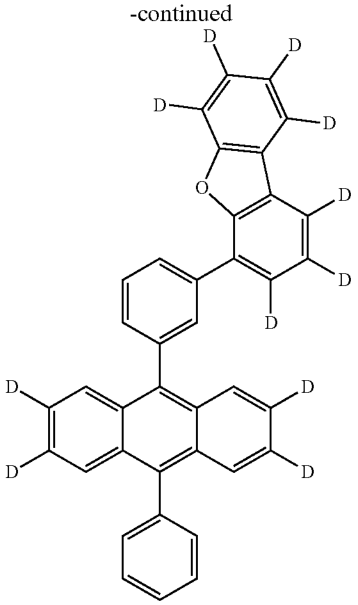
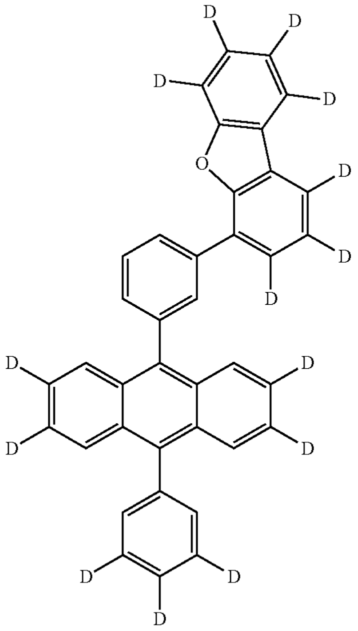
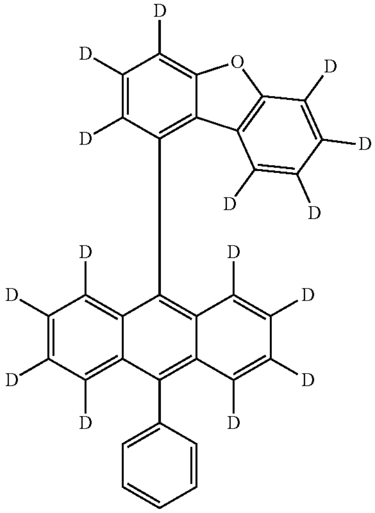
-continued
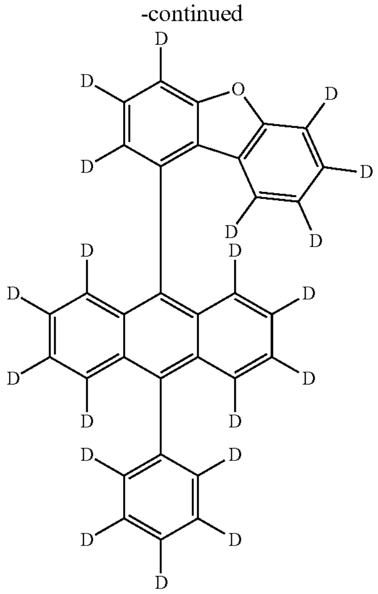
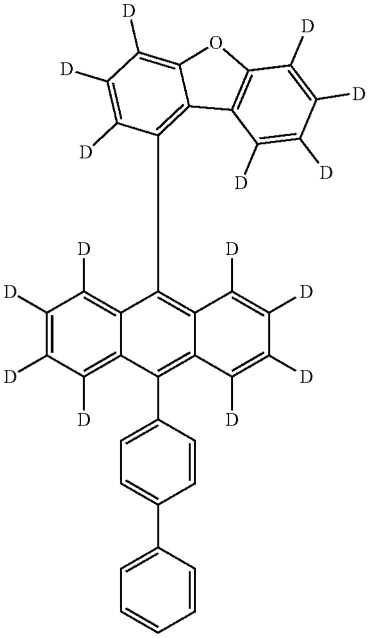

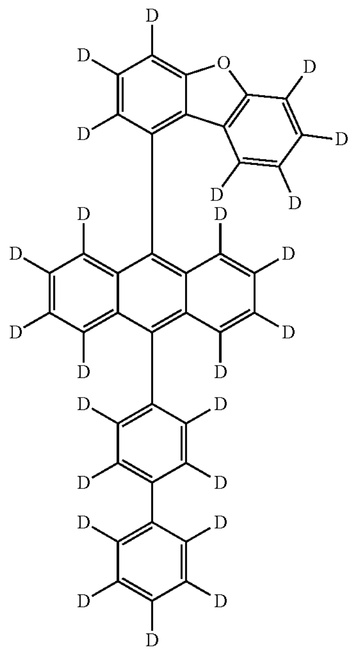
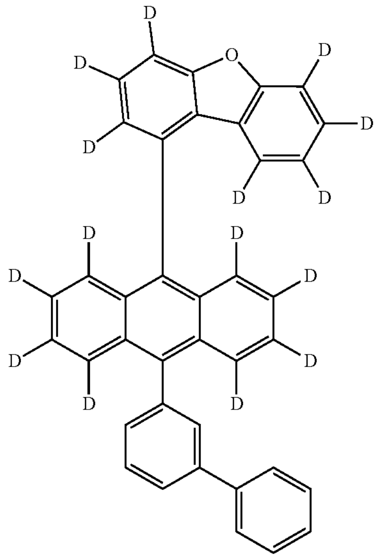
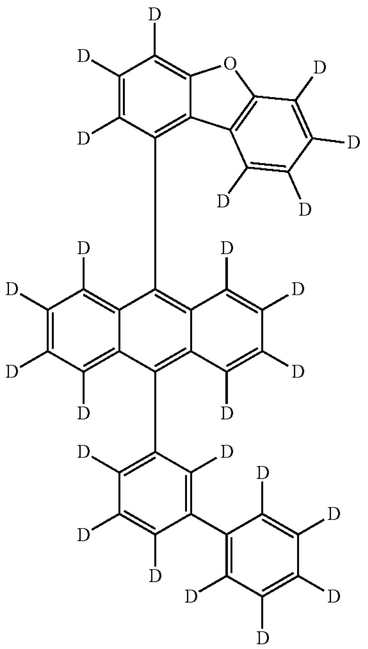
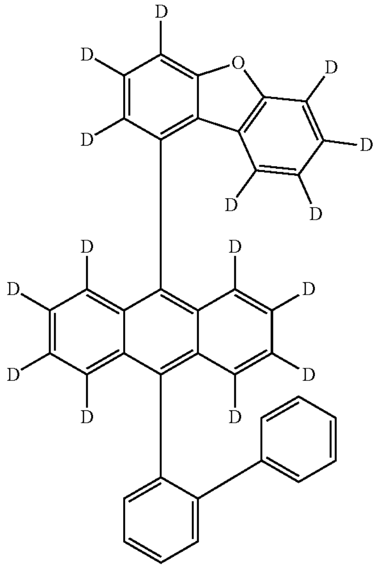

-continued
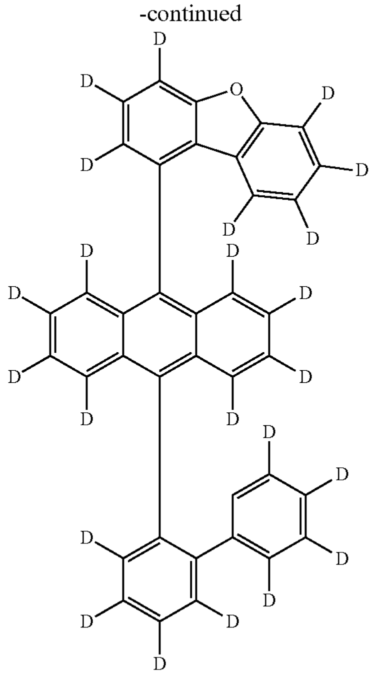
-continued
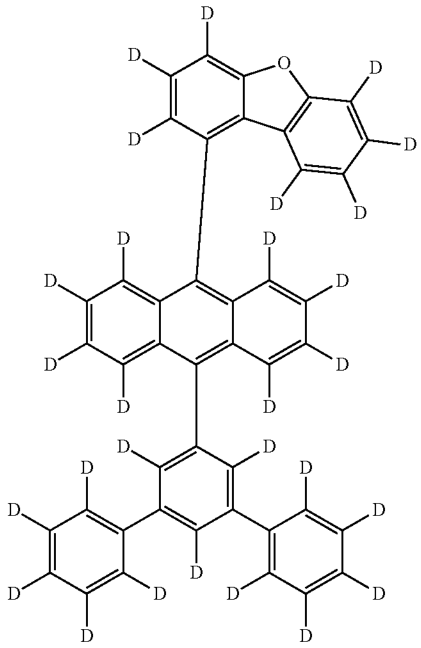
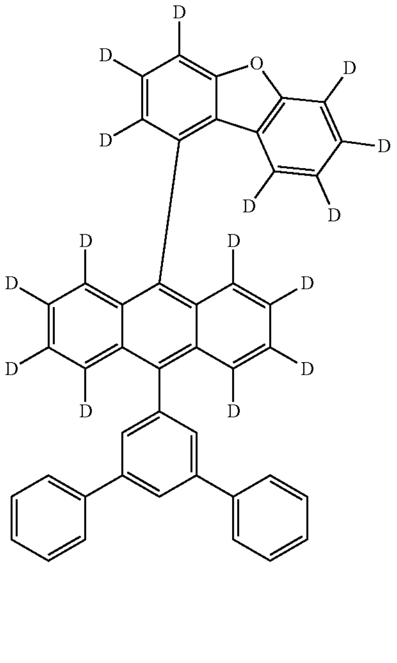
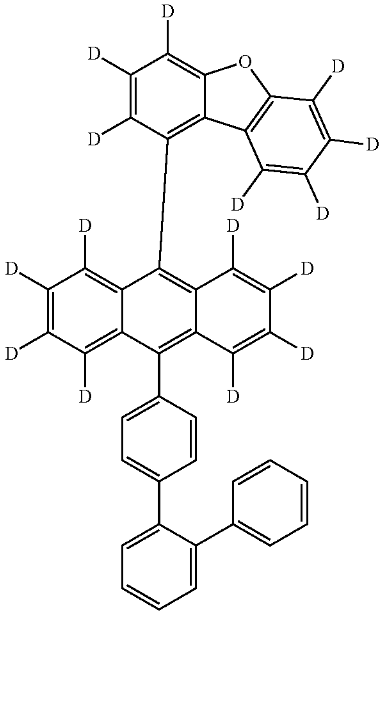

-continued
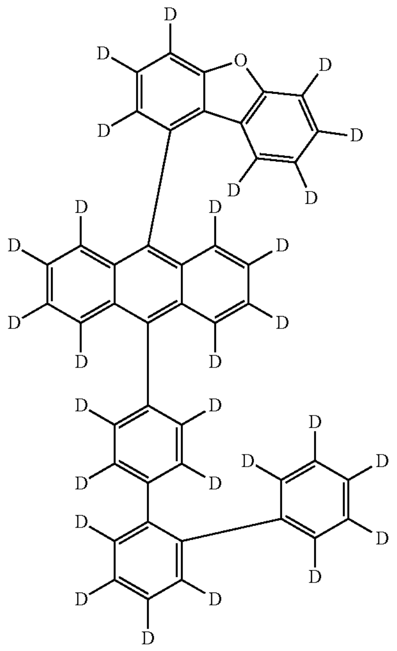
-continued
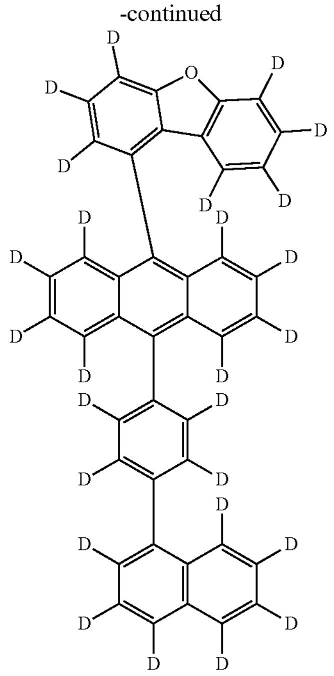
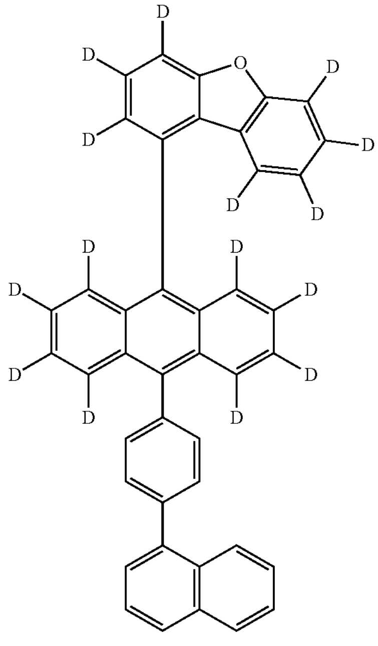
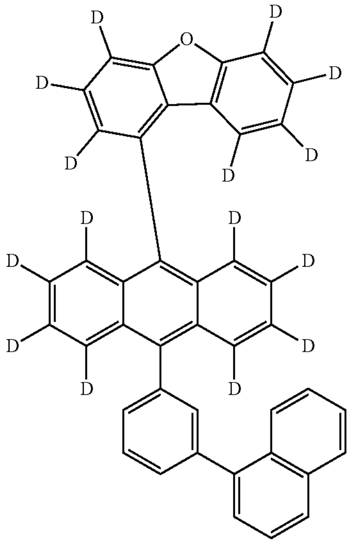

-continued
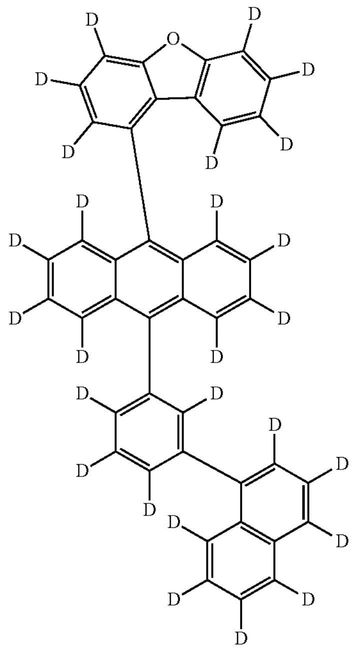
-continued
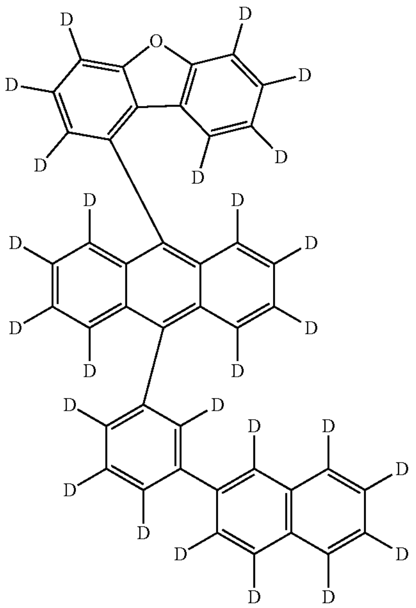
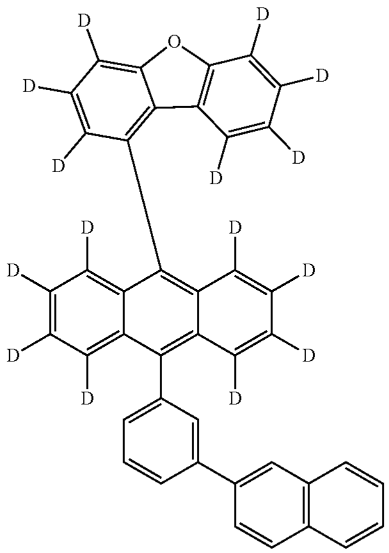
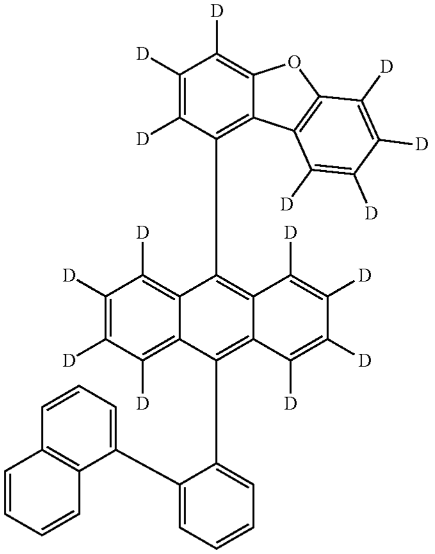

-continued
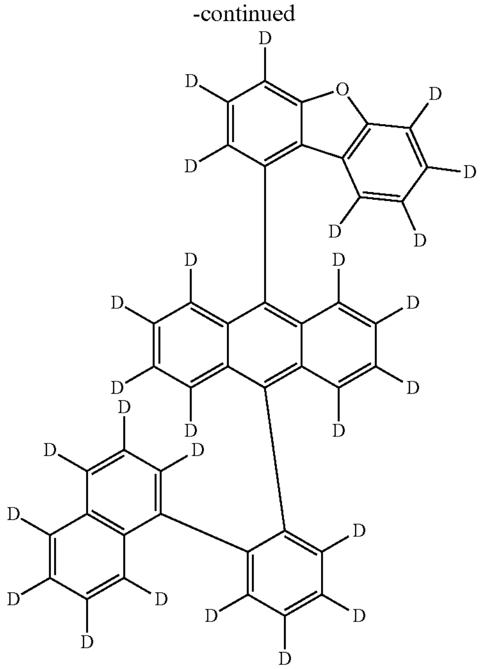
-continued
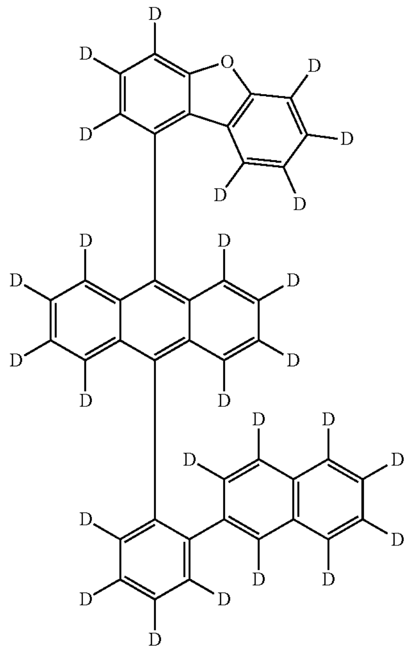
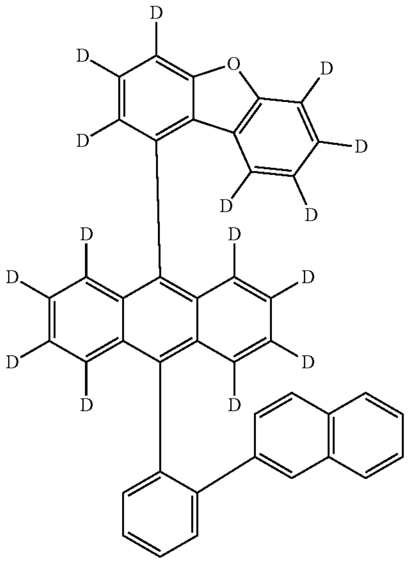
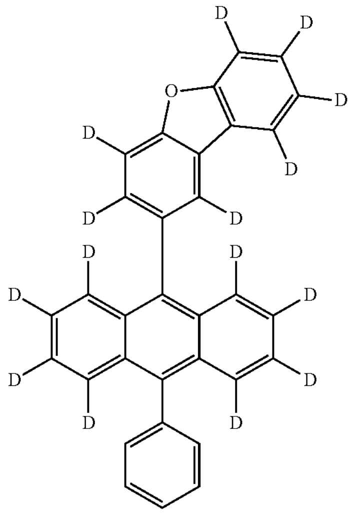

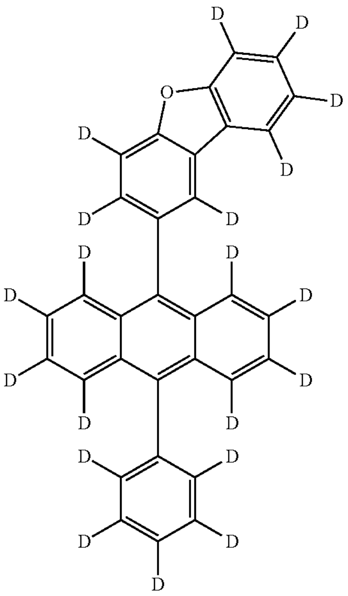
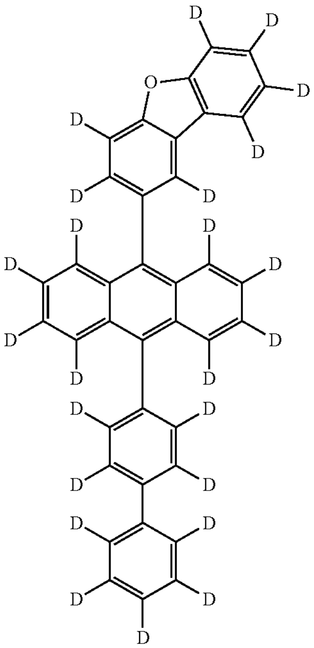
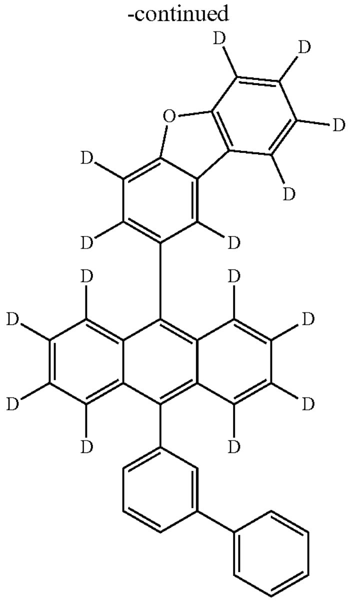
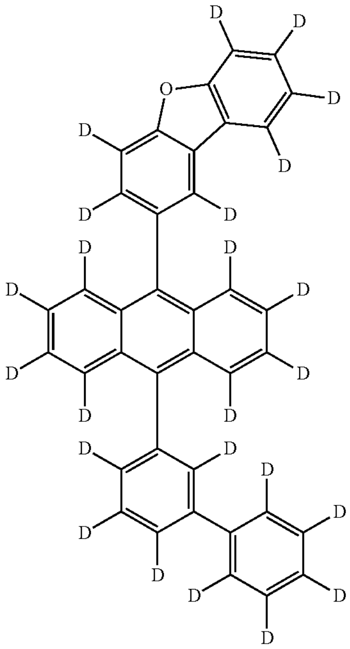

-continued
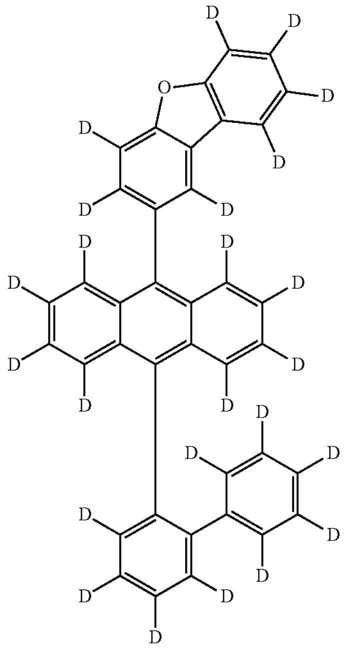
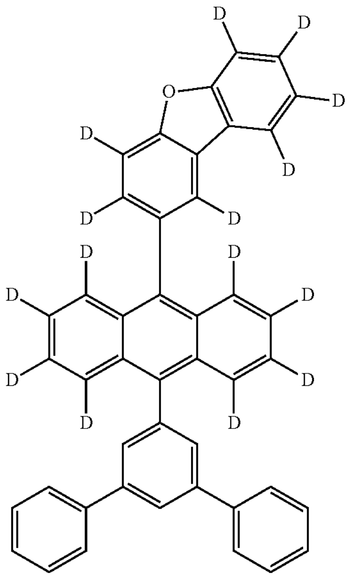
-continued
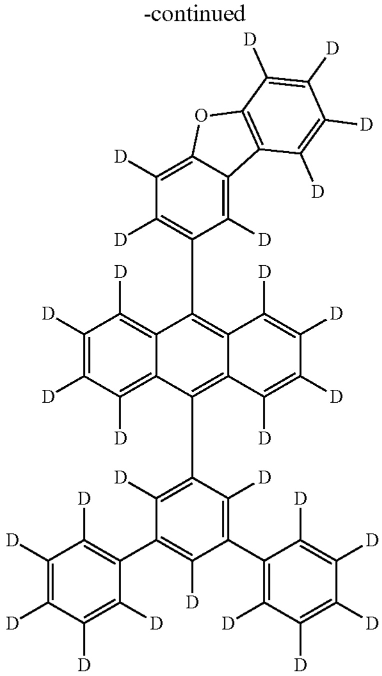
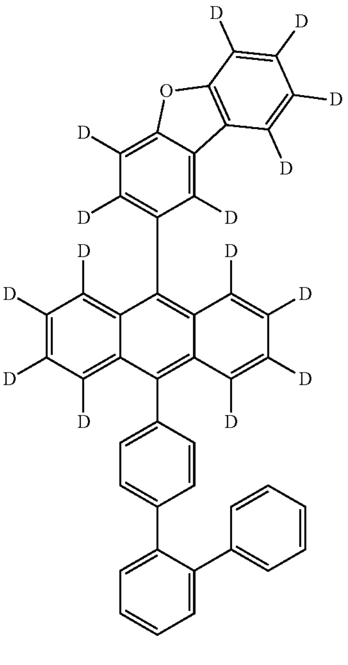

-continued
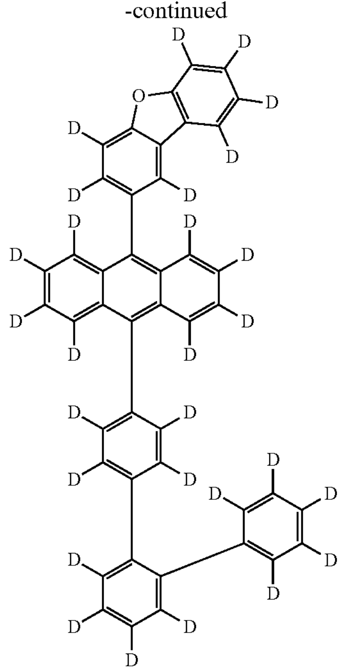
-continued
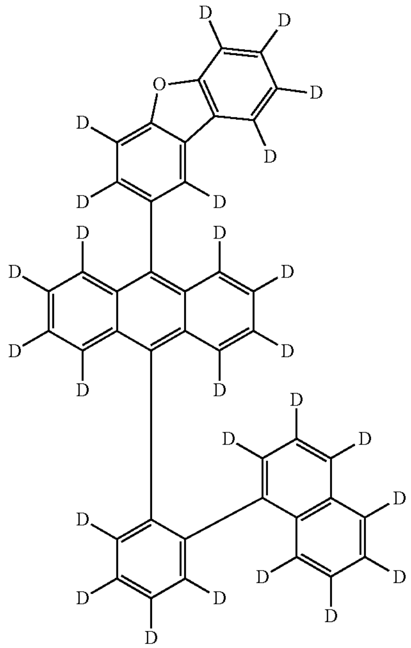
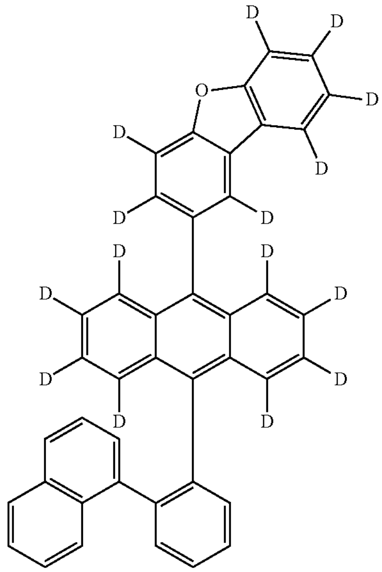
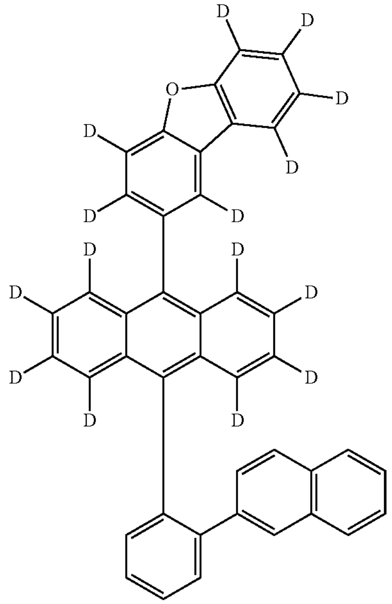

-continued
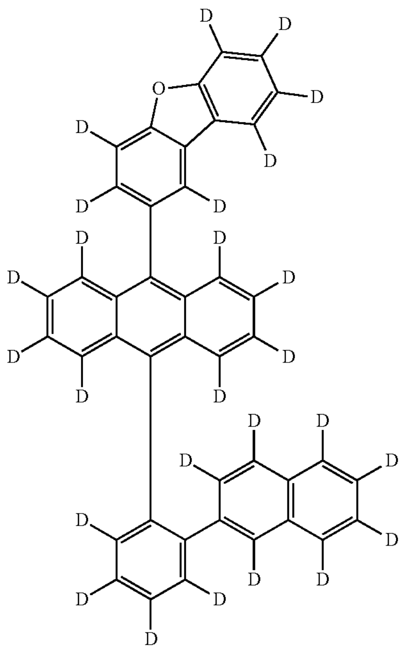
-continued
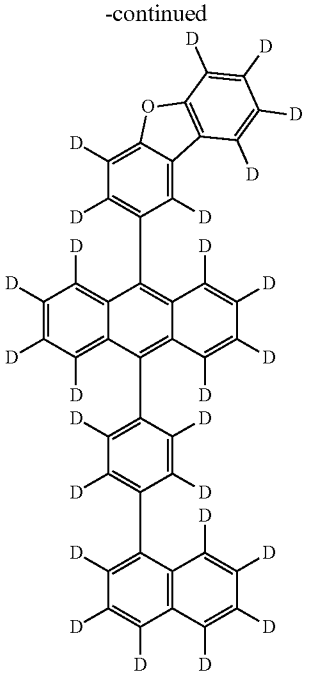
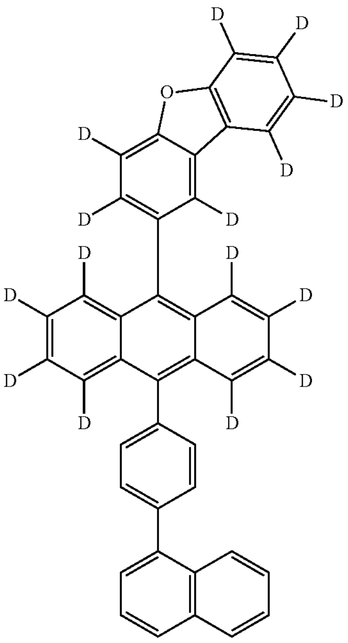
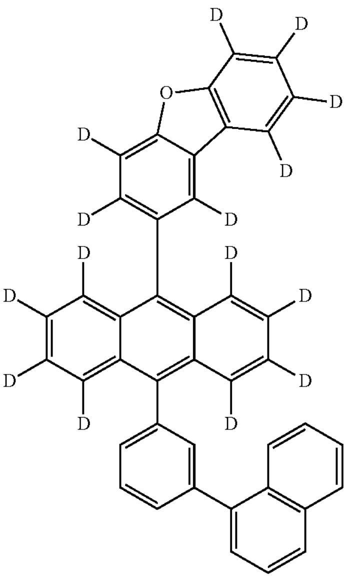

-continued
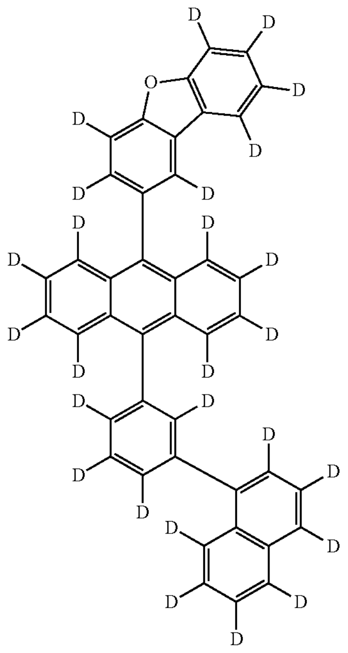
-continued
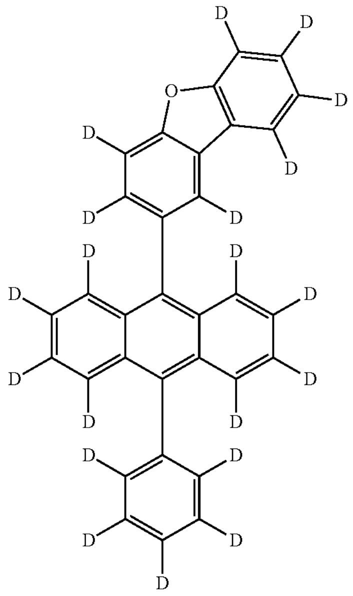
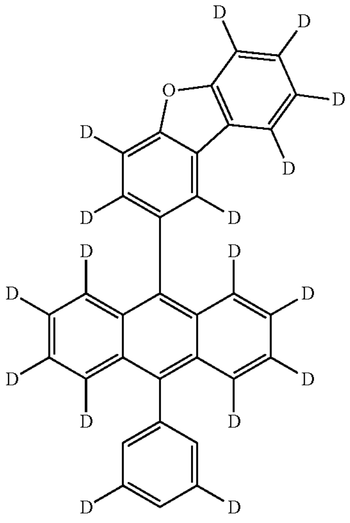
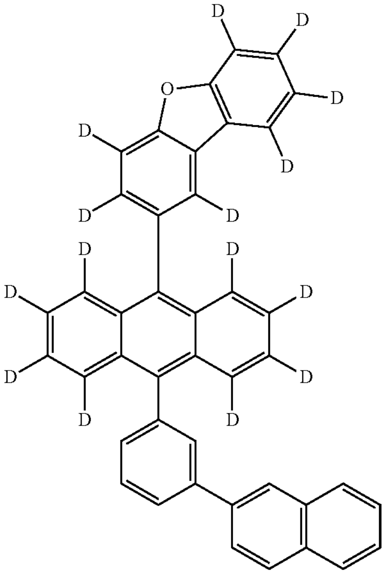

-continued
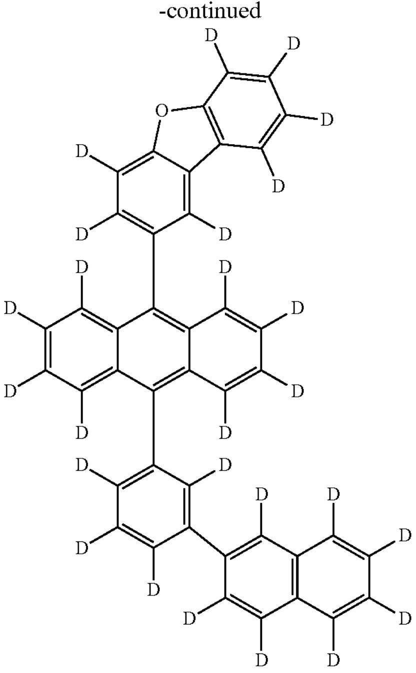
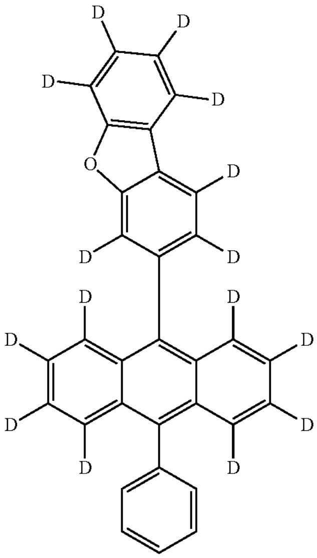
-continued
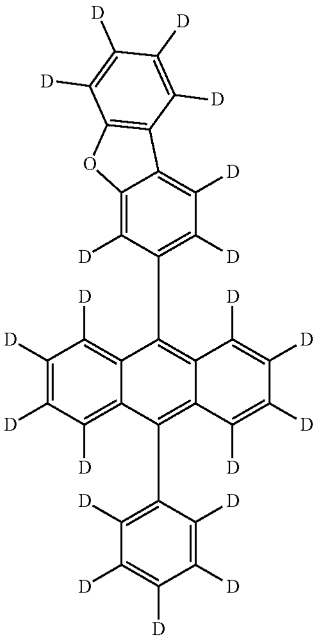
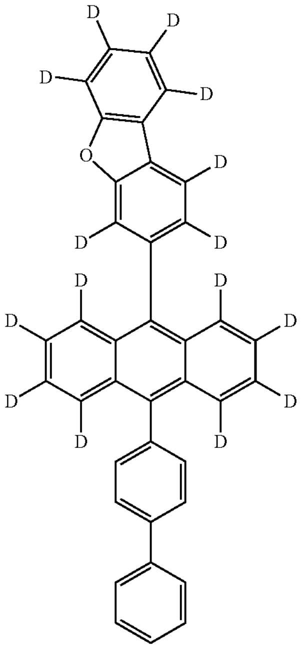

-continued
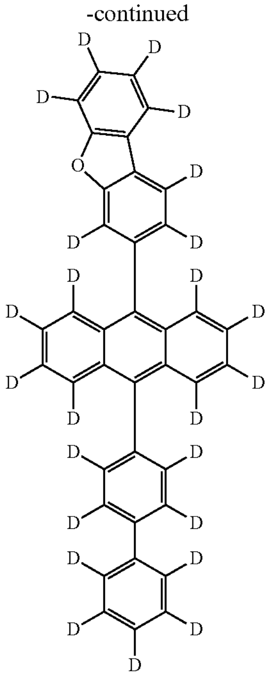
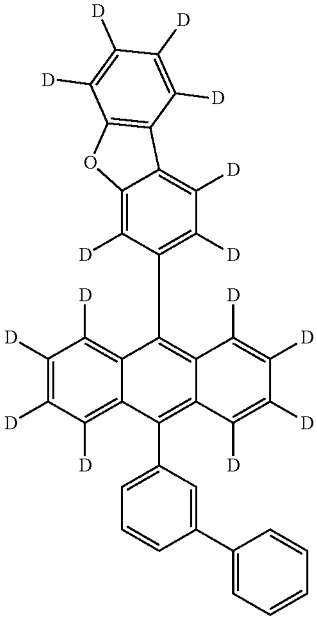
-continued
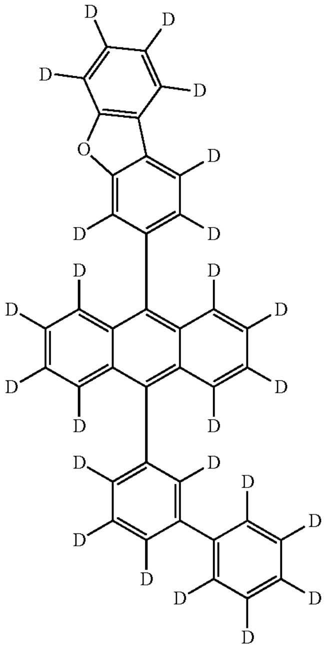
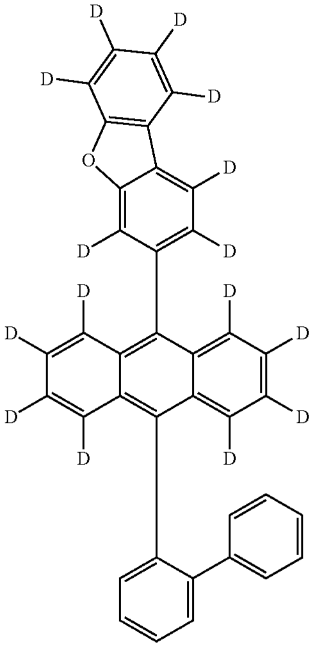

-continued
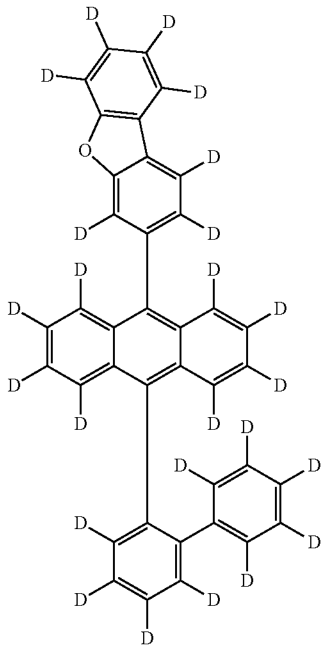
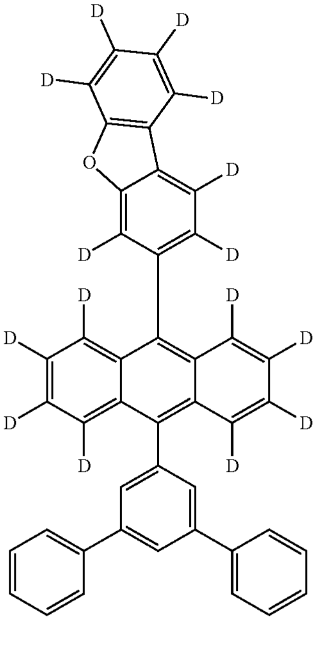
-continued
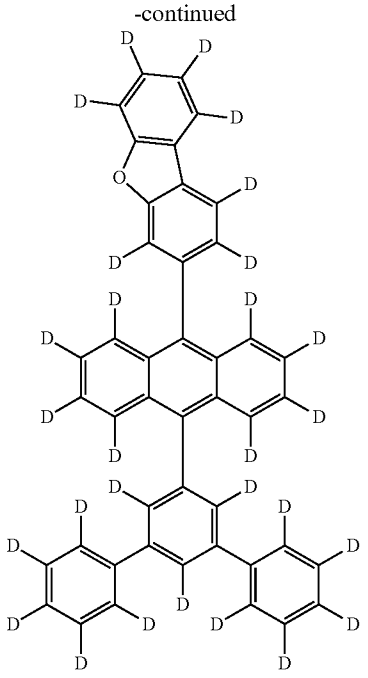
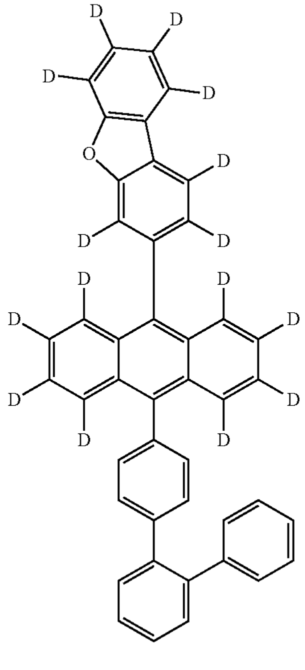

-continued
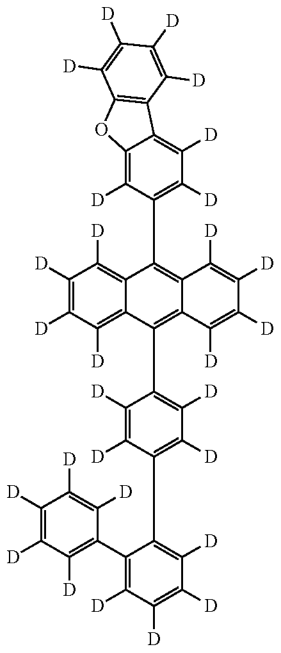 [SMILES: [2H]c1c([2H])c([2H])c(-c2c([2H])c([2H])c([2H])c([2H])c2-c2c([2H])c([2H])c(-c3c4c([2H])c([2H])c([2H])c([2H])c4c(-c4c([2H])c([2H])c5c(oc6c([2H])c([2H])c([2H])c([2H])c65)c4[2H])c4c([2H])c([2H])c([2H])c([2H])c34)c([2H])c2[2H])c([2H])c1[2H]]
-continued
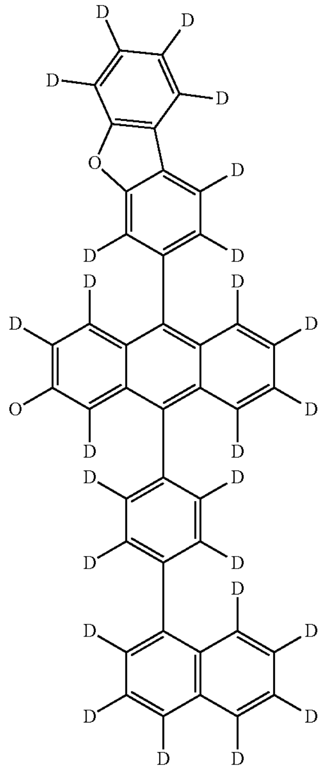
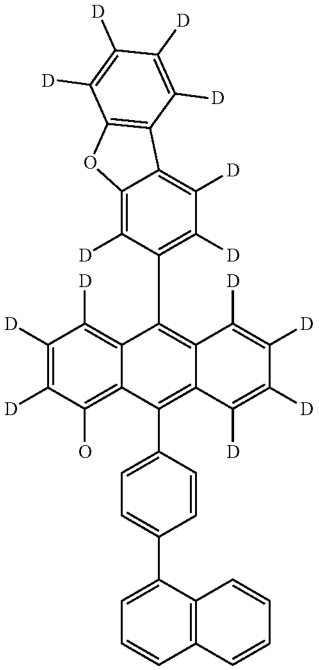
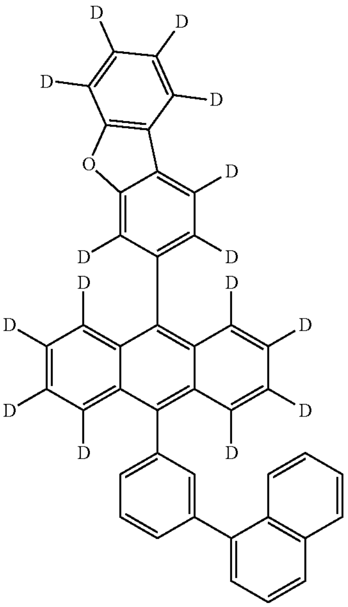

-continued
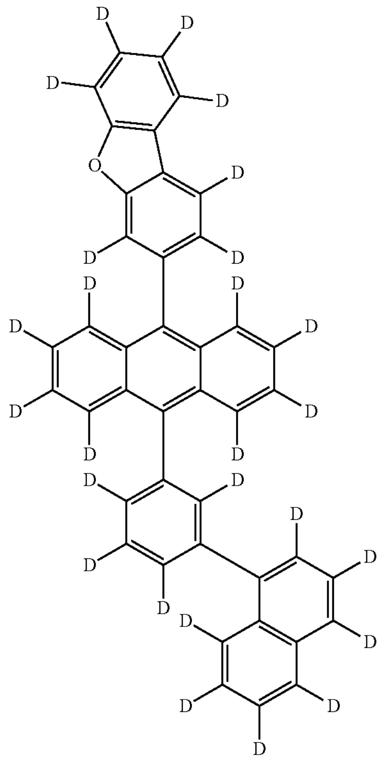
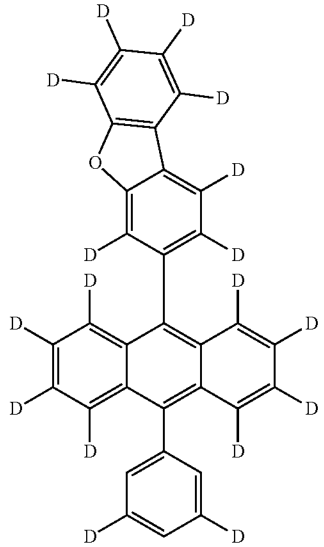
-continued
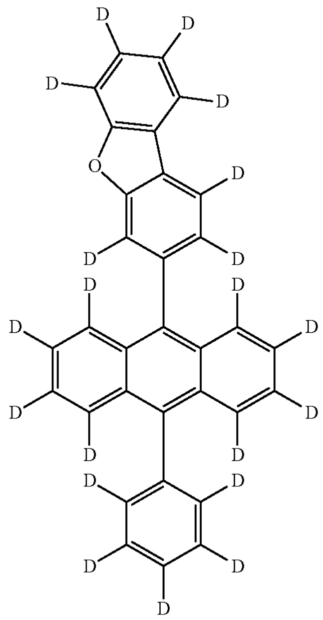
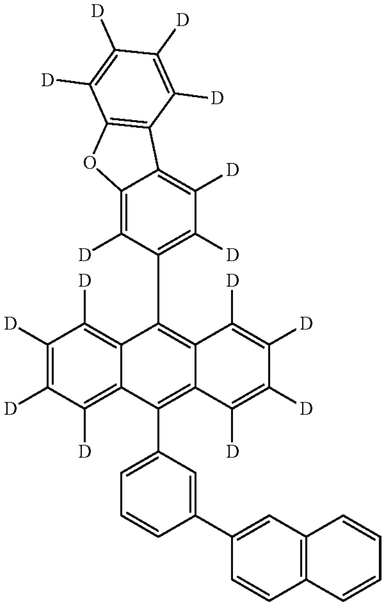

-continued
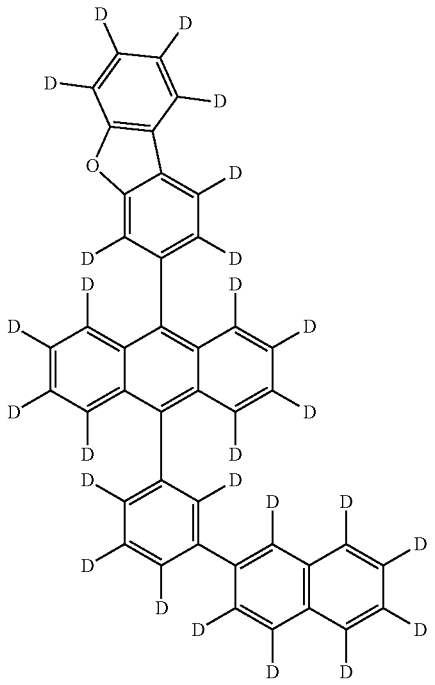
-continued
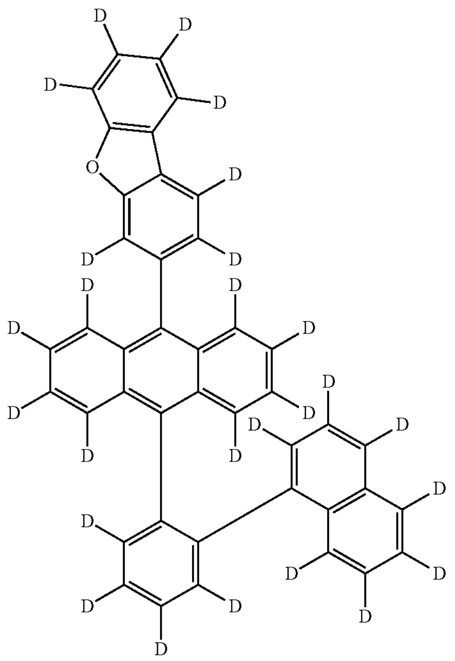
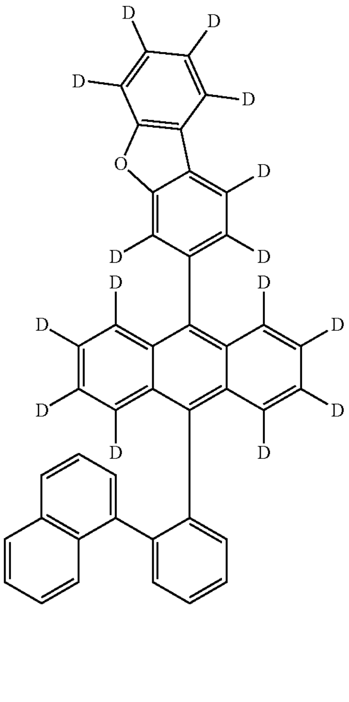
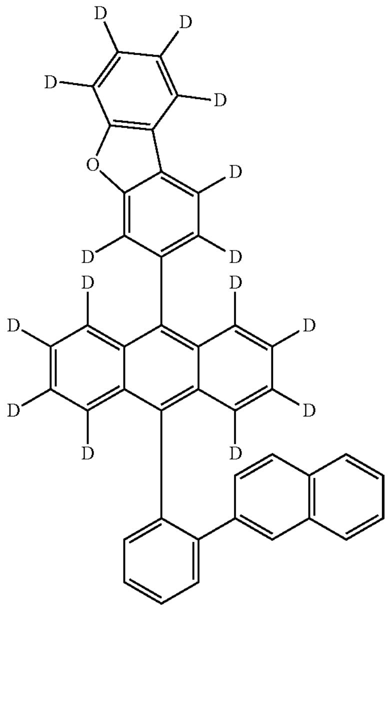

-continued
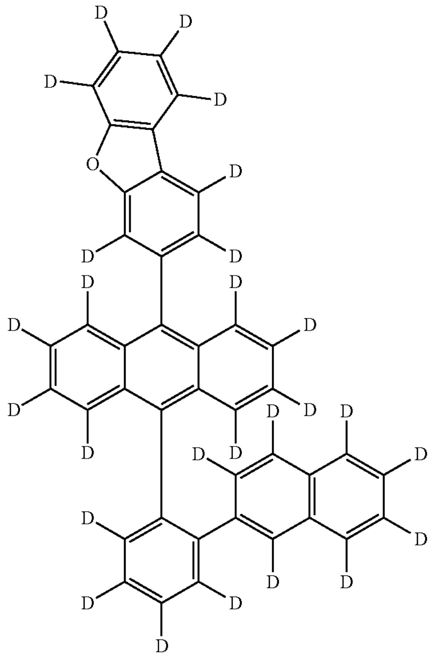
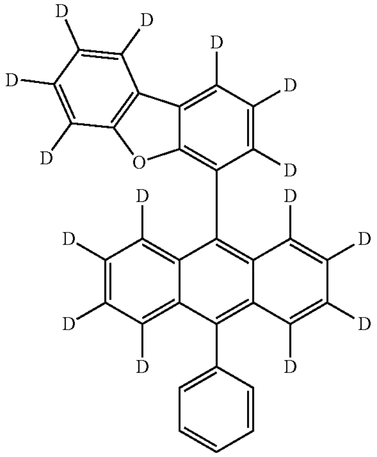
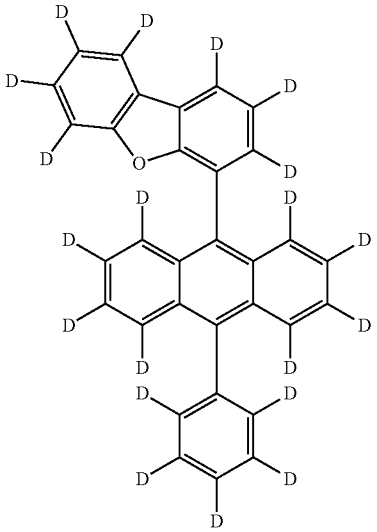
-continued
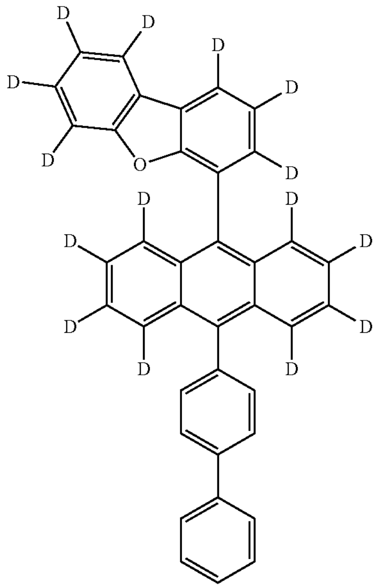
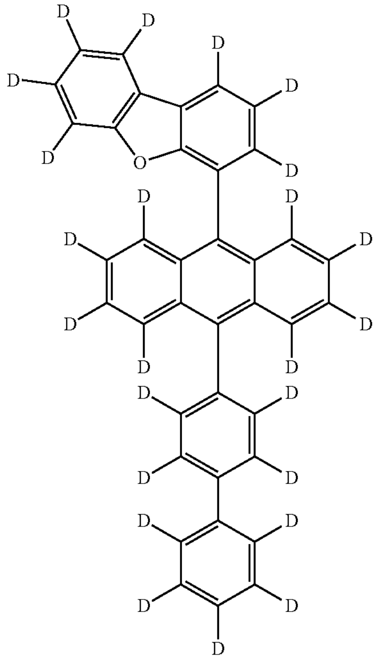

-continued
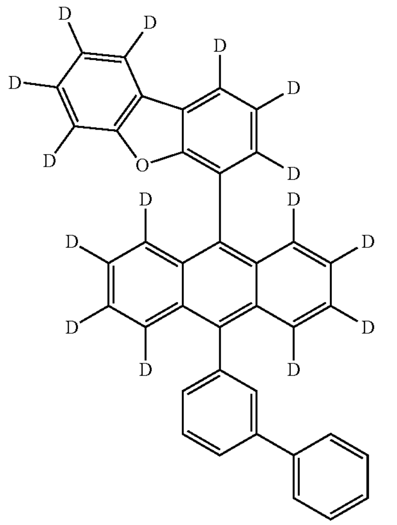
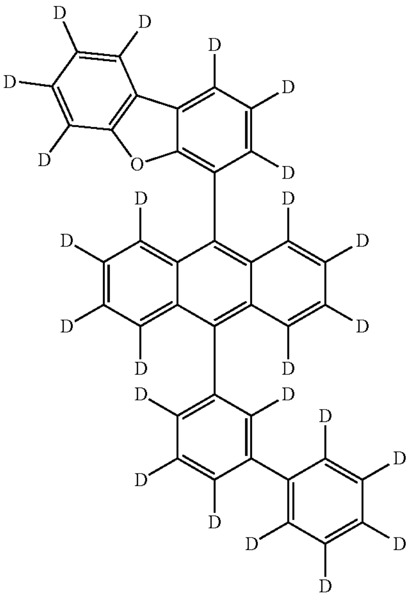
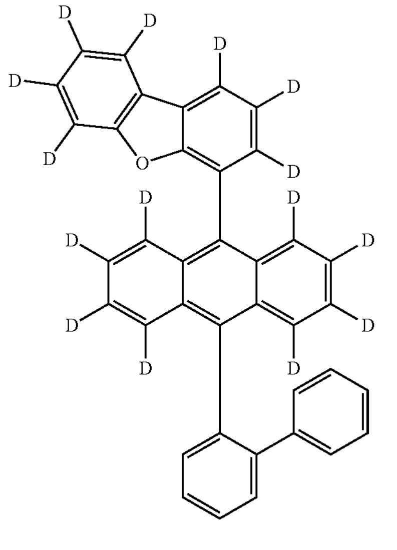
-continued
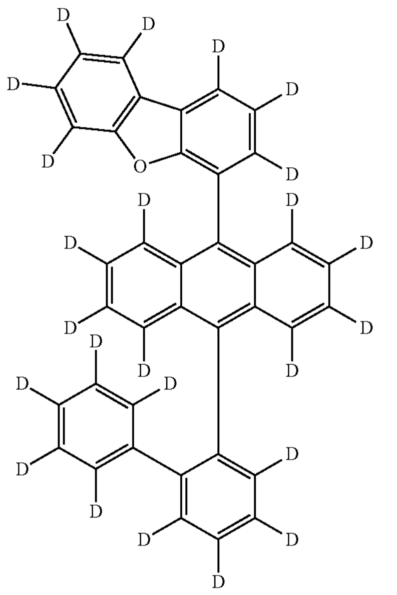
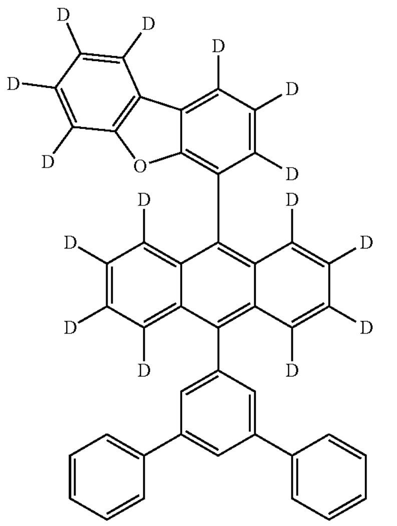
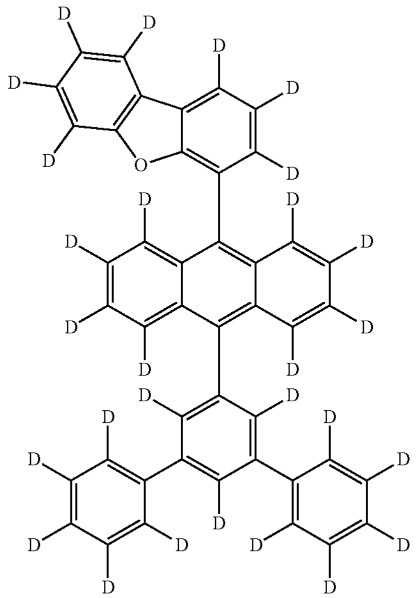

-continued
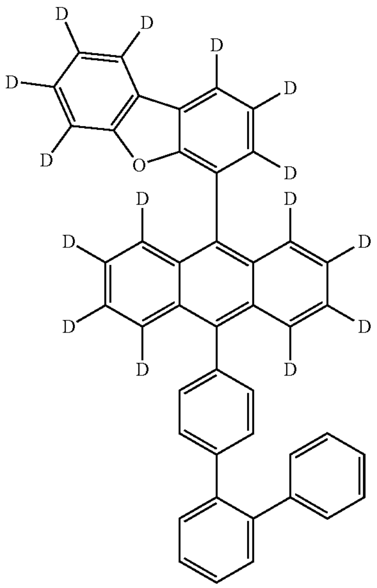
-continued
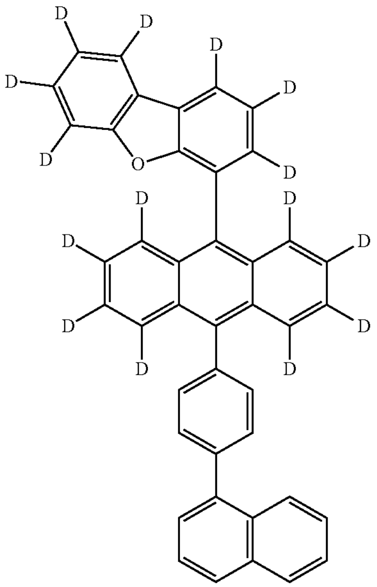
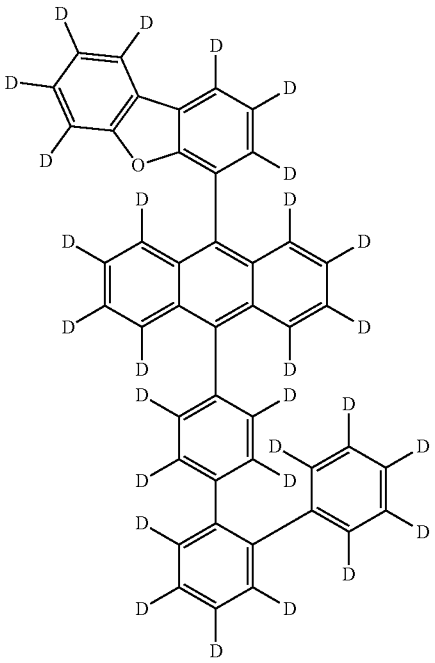
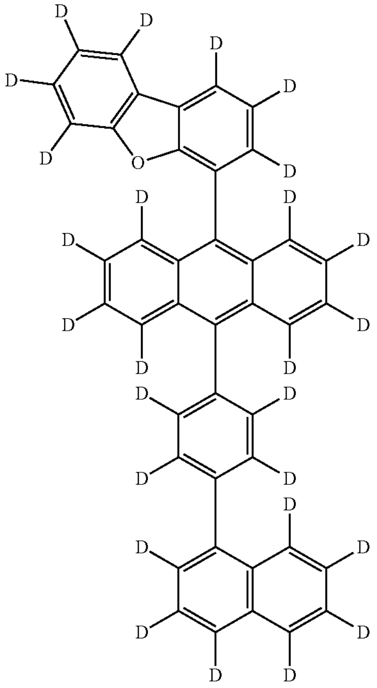

-continued
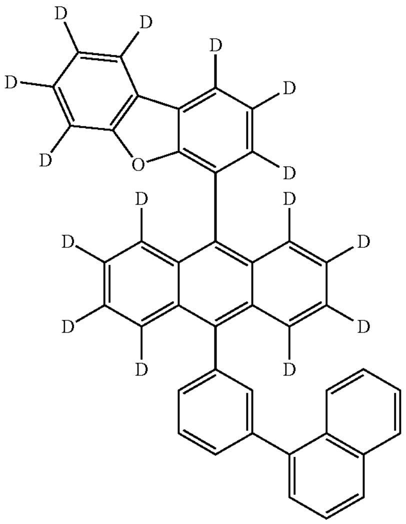
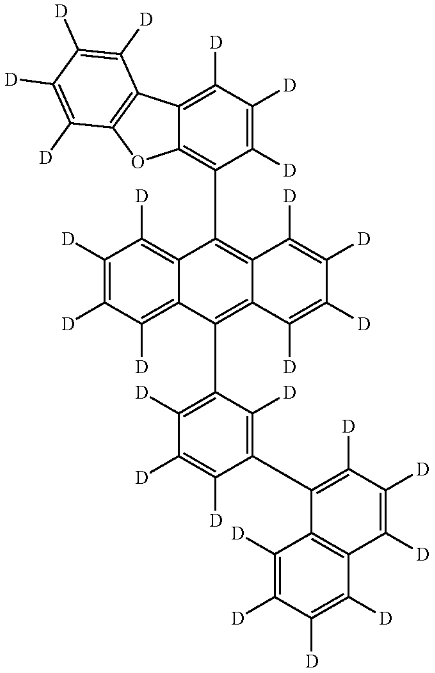
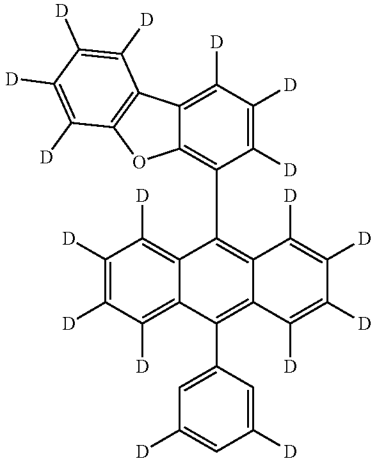
-continued
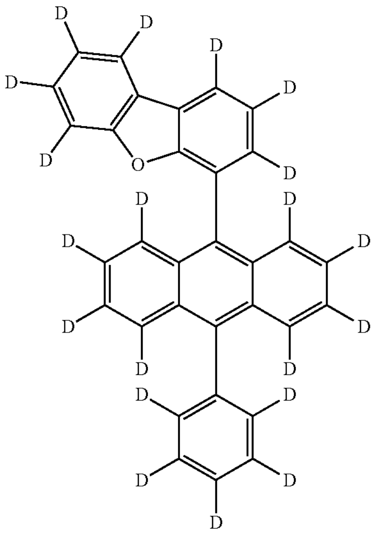
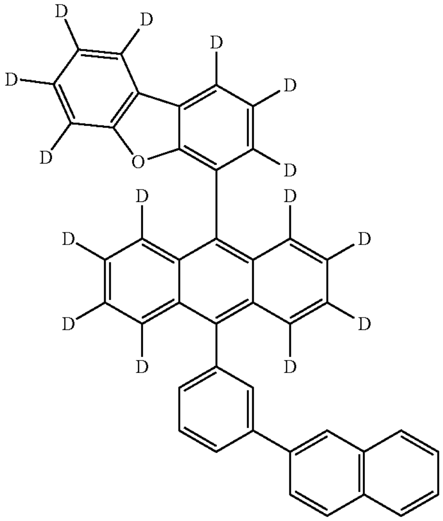
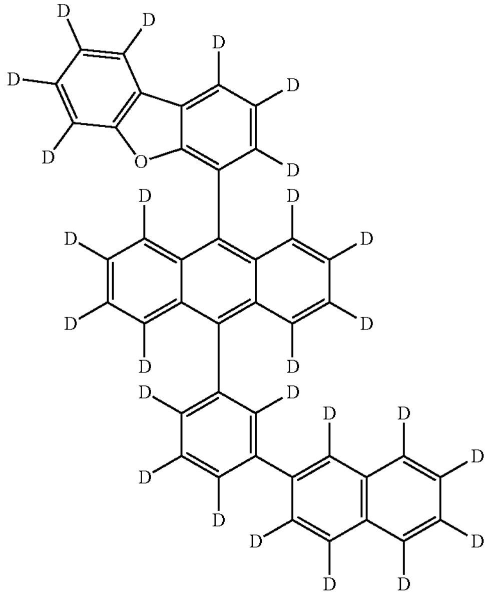

-continued
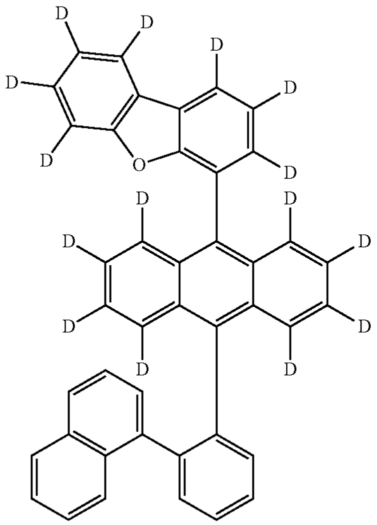
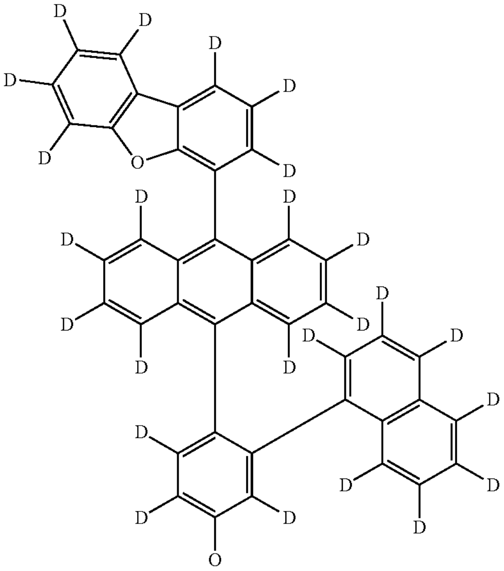
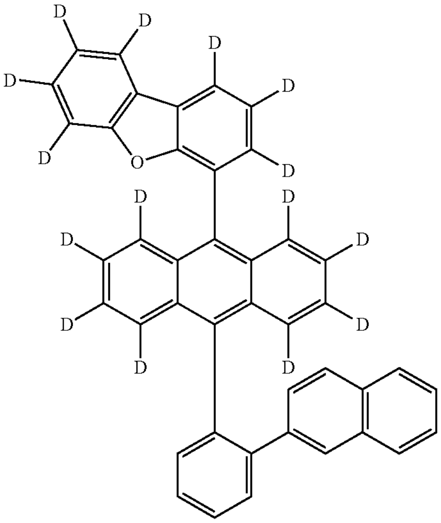
-continued
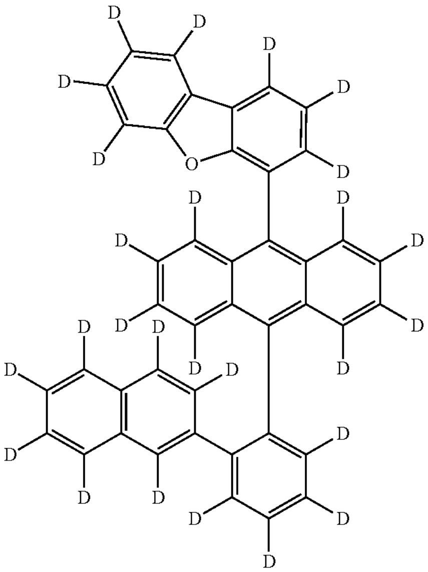
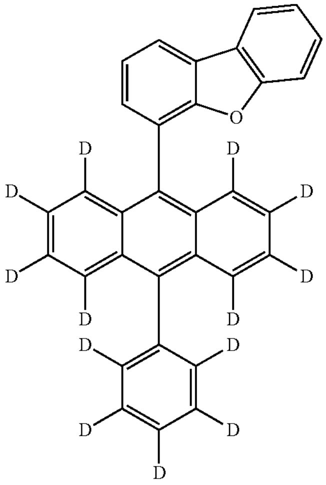
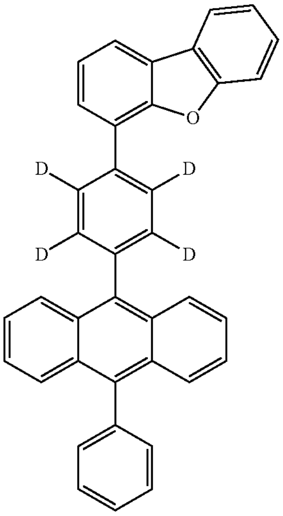

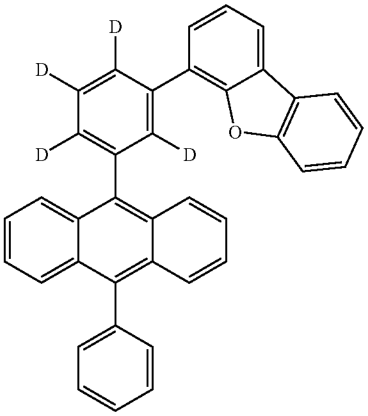
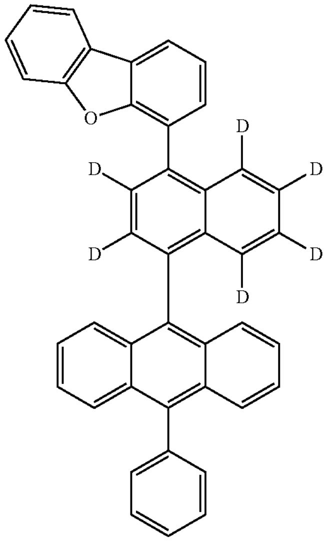
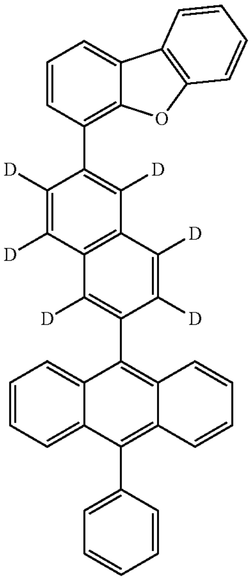
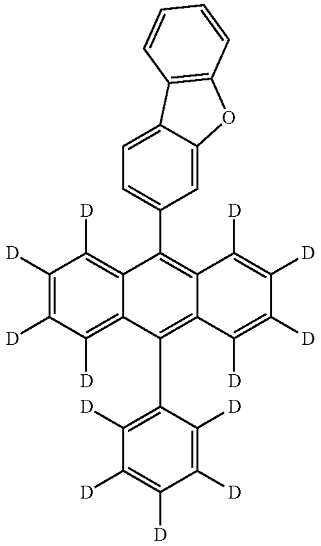
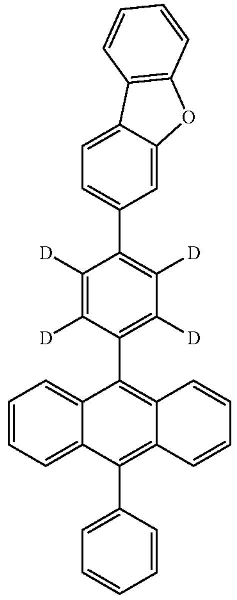
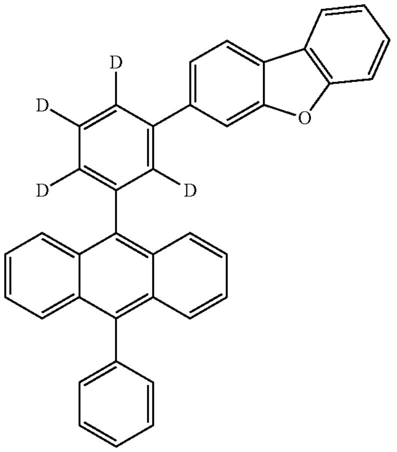

-continued
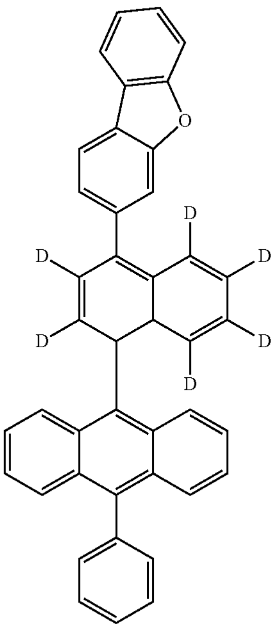
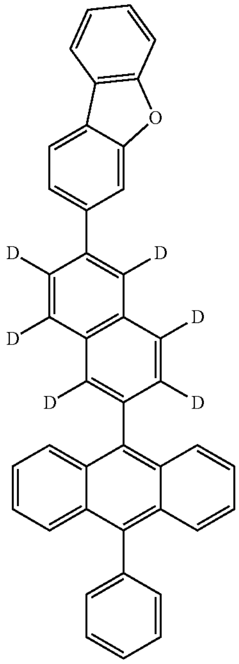
-continued
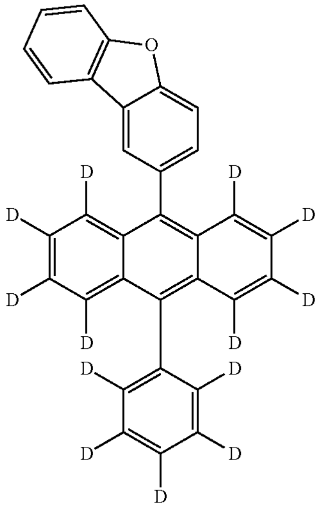
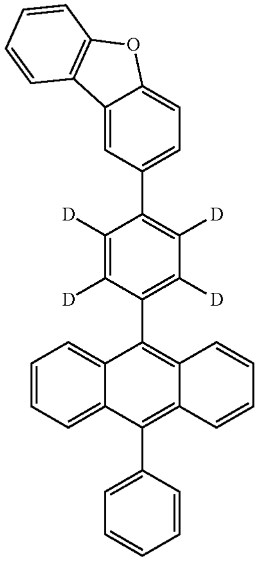
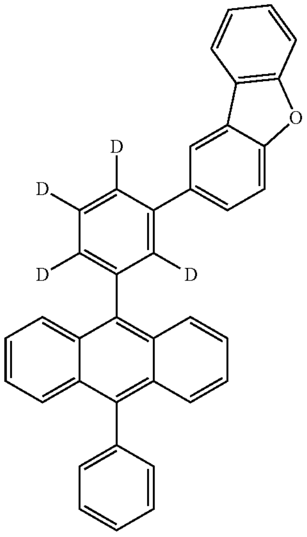

-continued
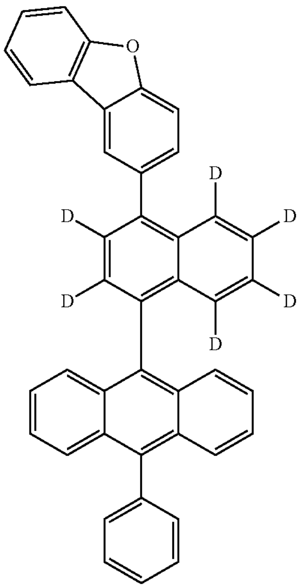
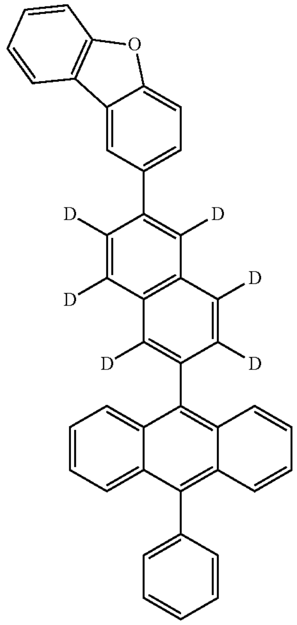
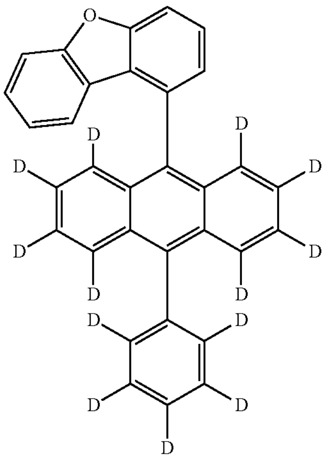
-continued
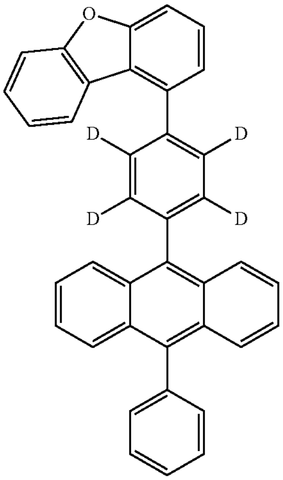
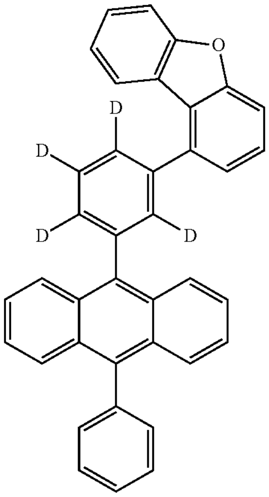
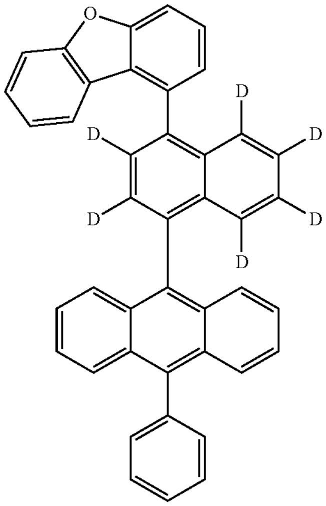

-continued
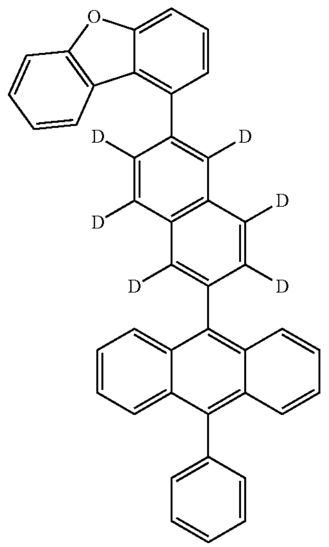
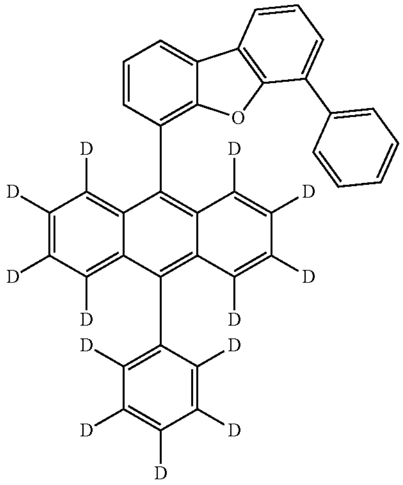
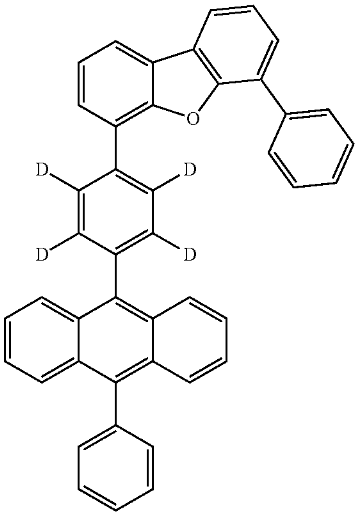
-continued
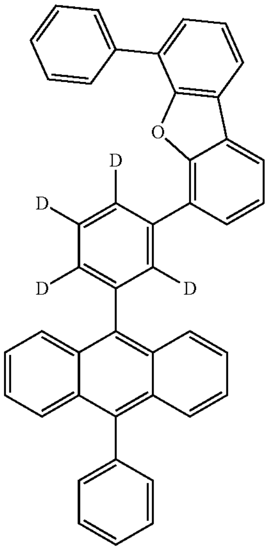
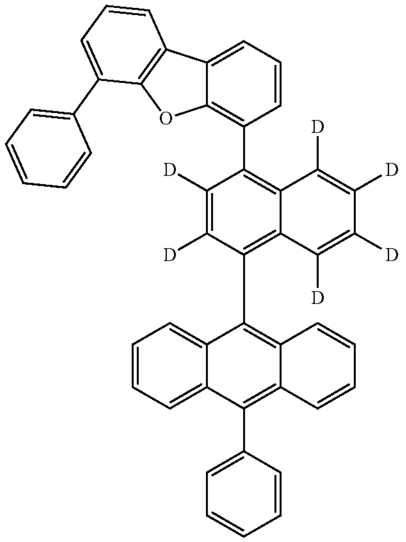
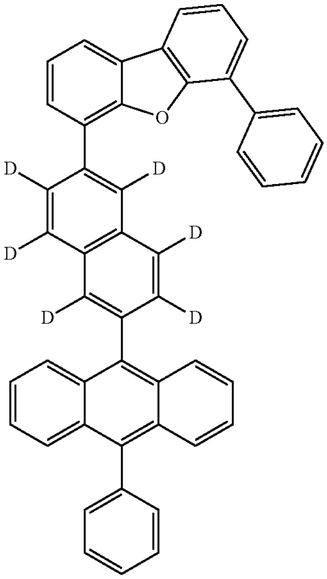

-continued
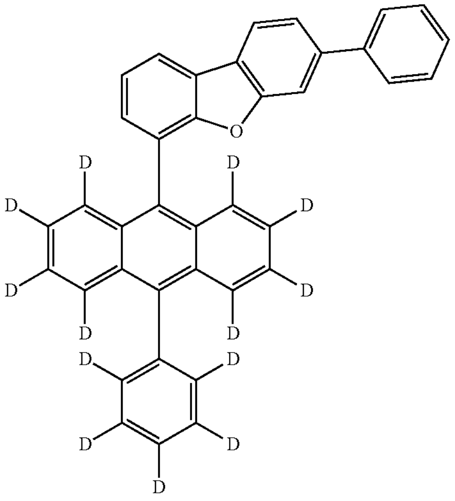
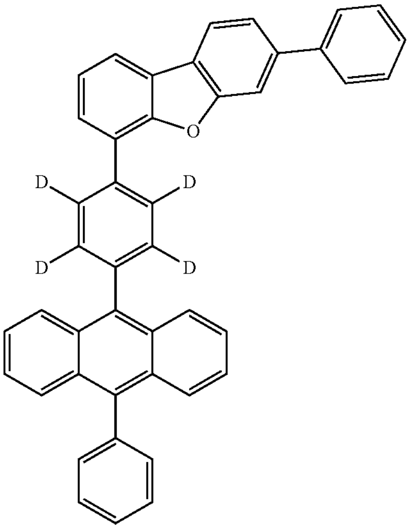
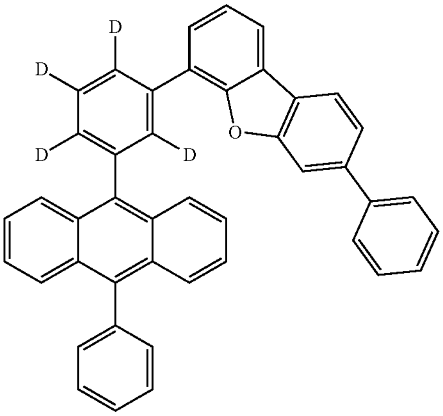
-continued
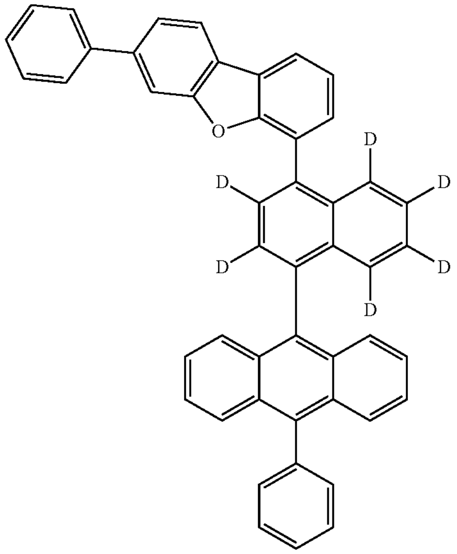
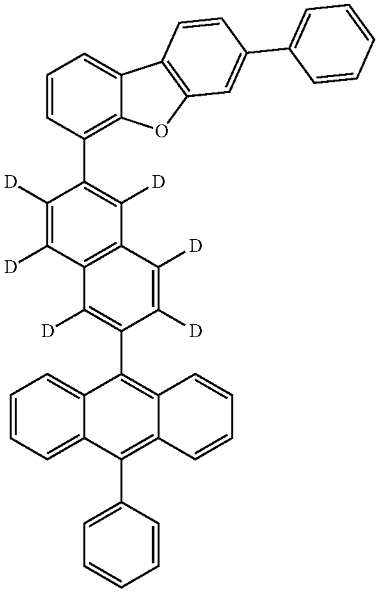

-continued
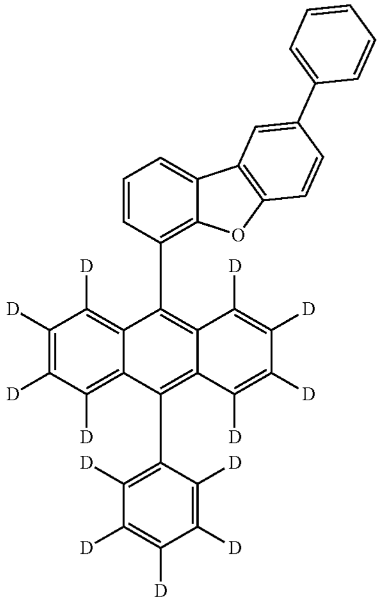
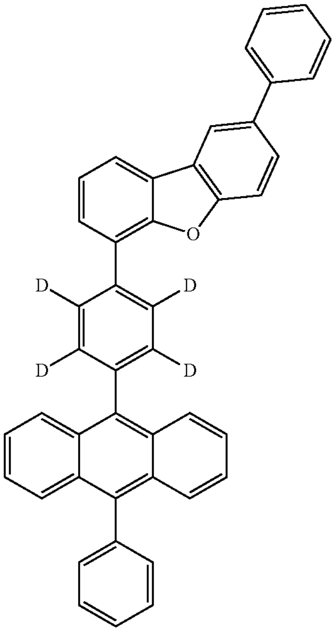
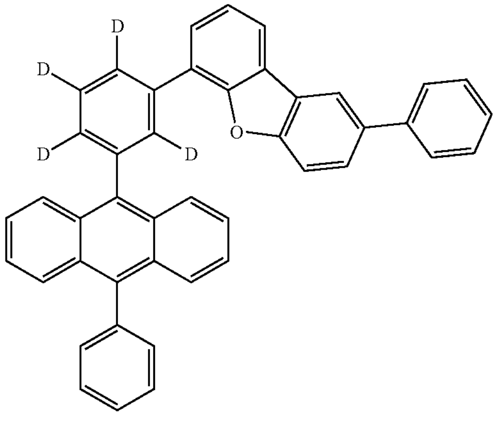
-continued
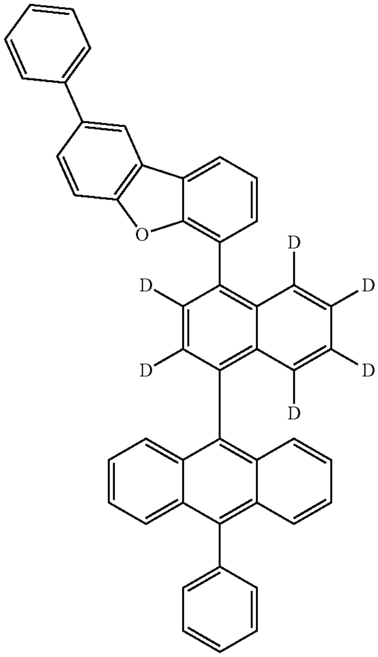
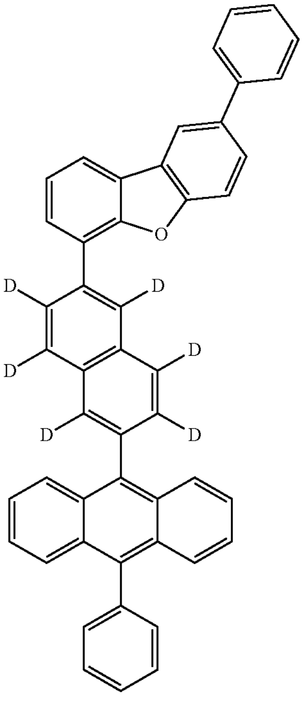

-continued
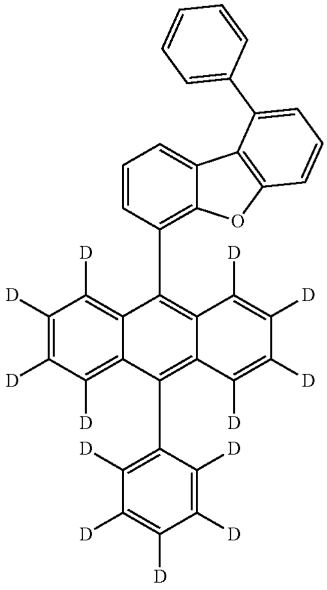
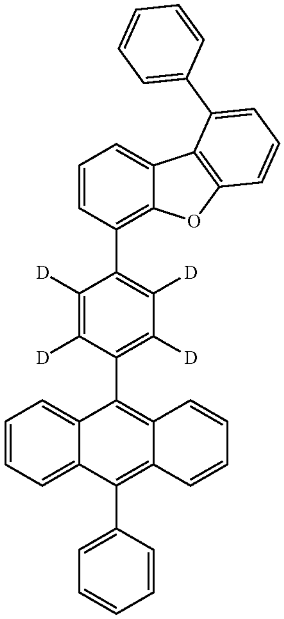
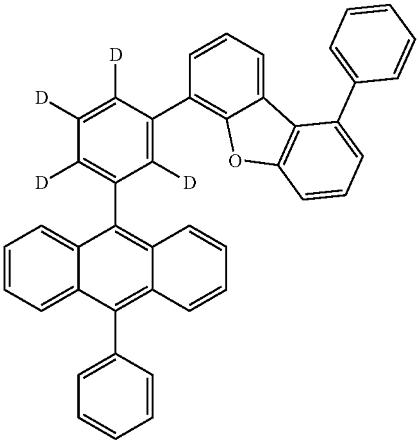
-continued
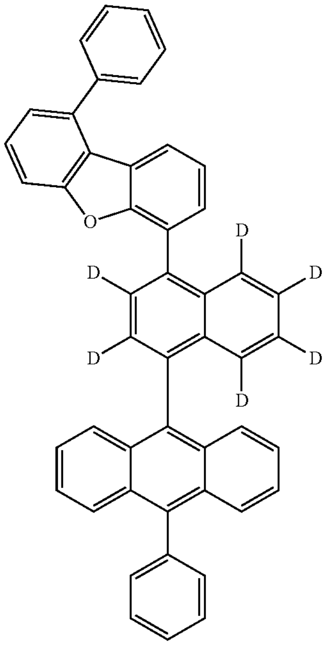
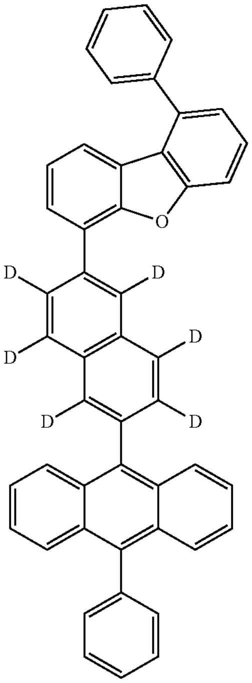

-continued
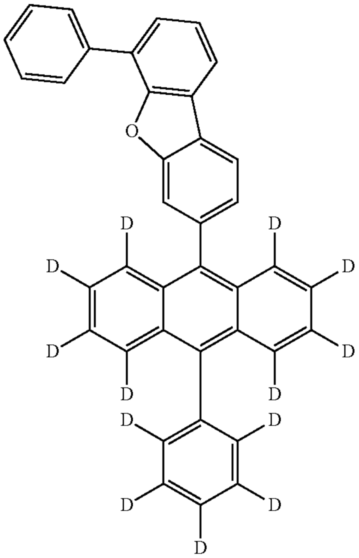
-continued
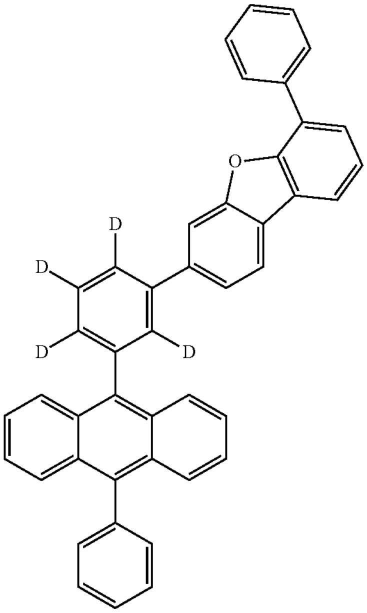
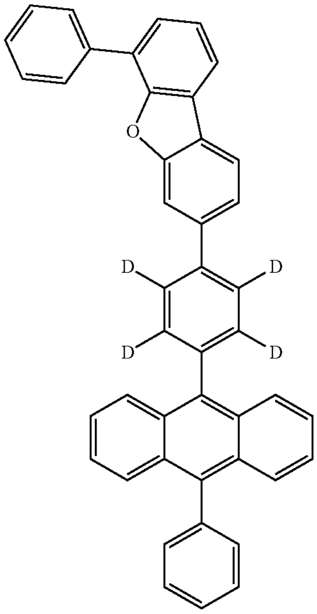
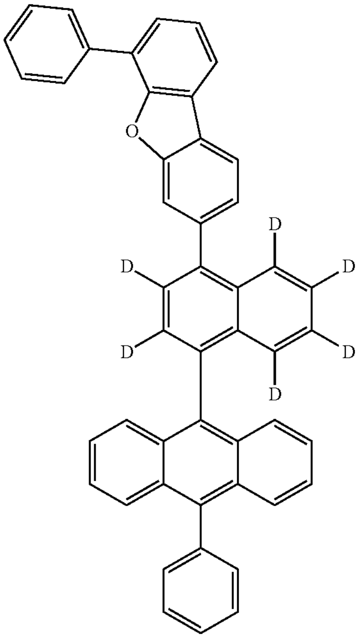

-continued
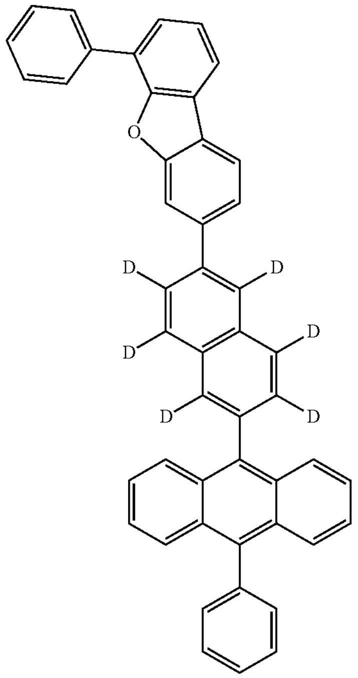
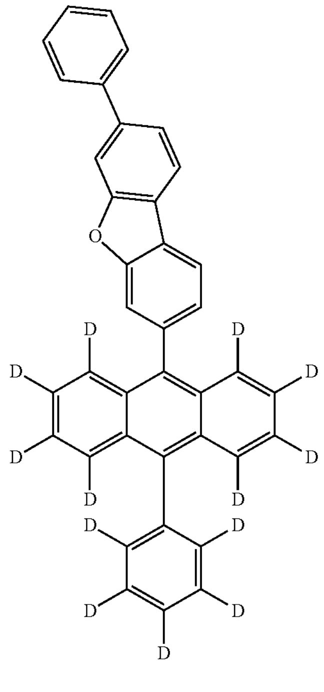
-continued
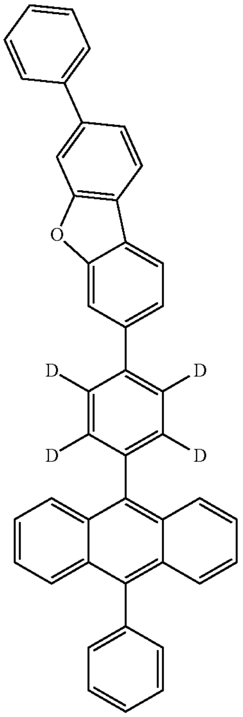
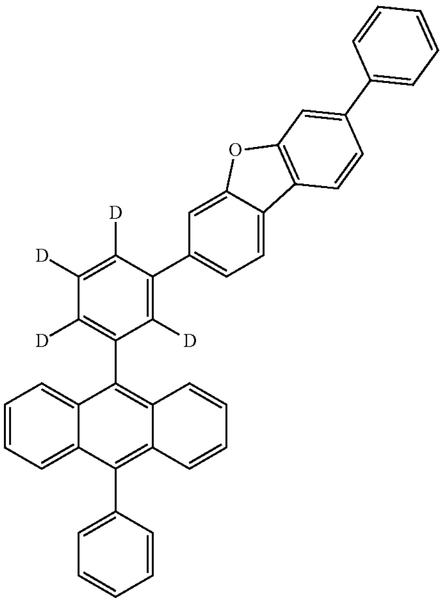

-continued
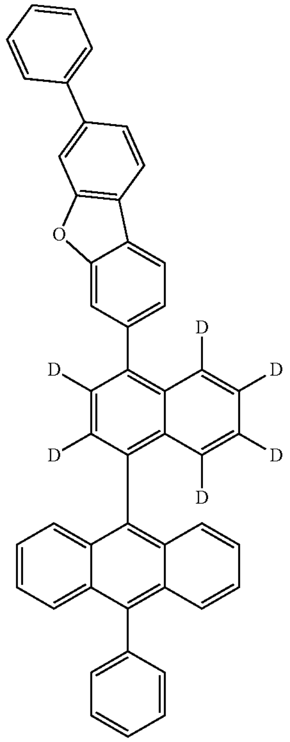
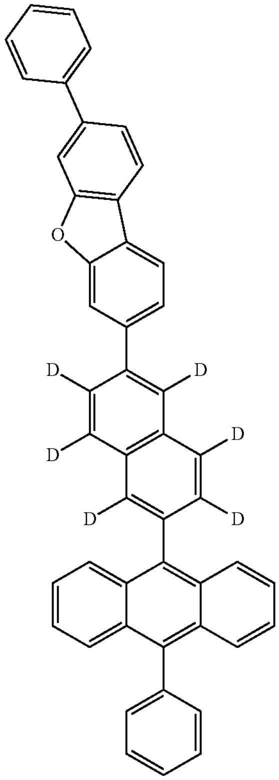
-continued
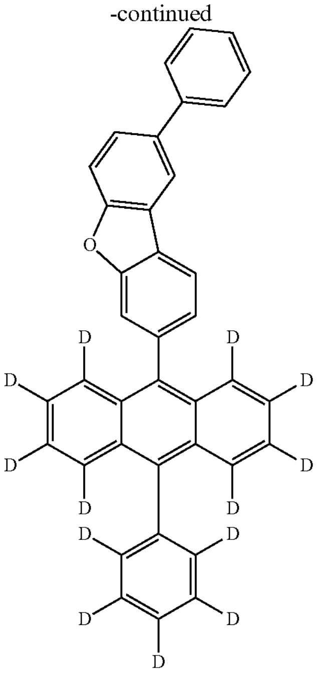
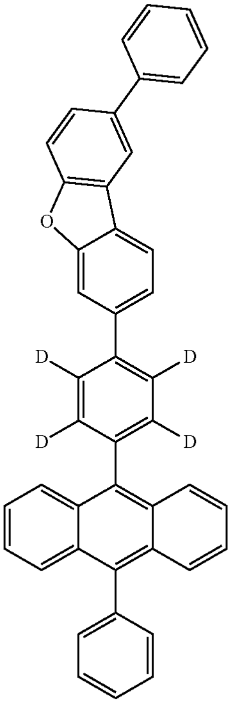

-continued
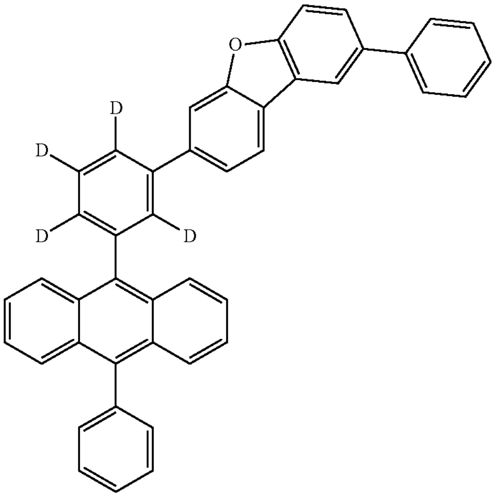
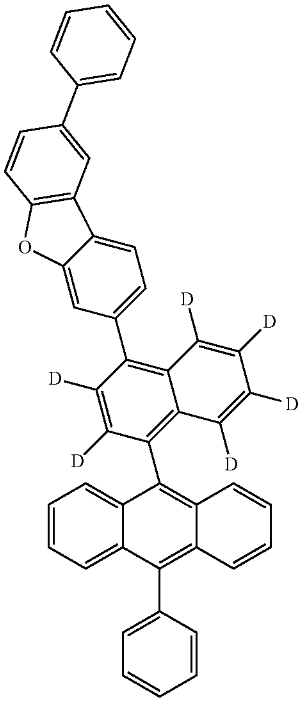
-continued
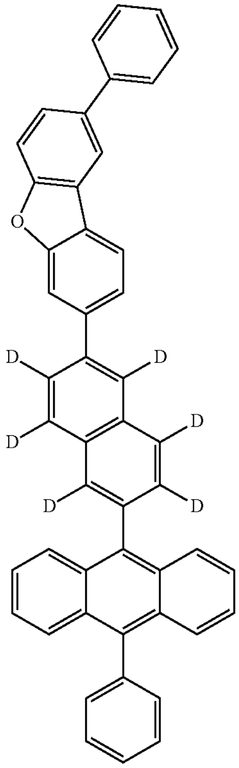
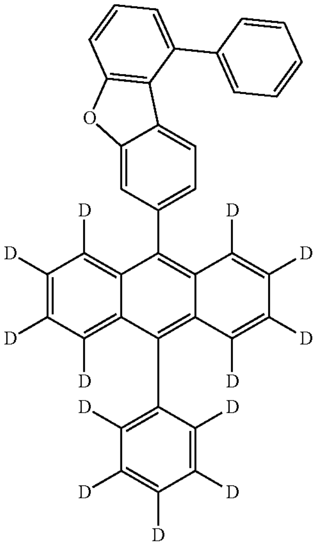

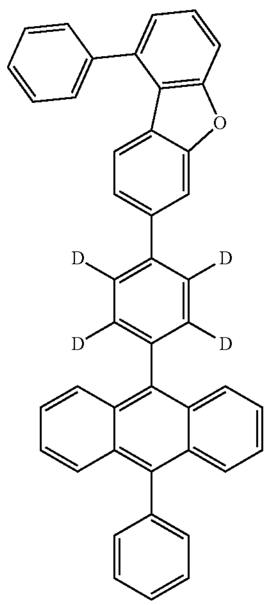
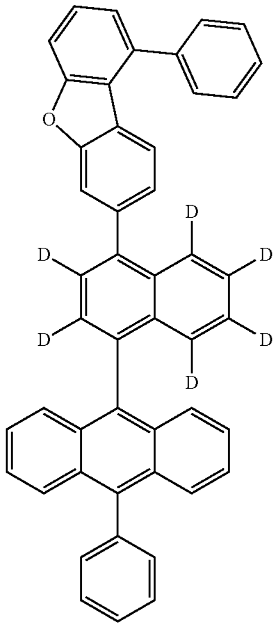
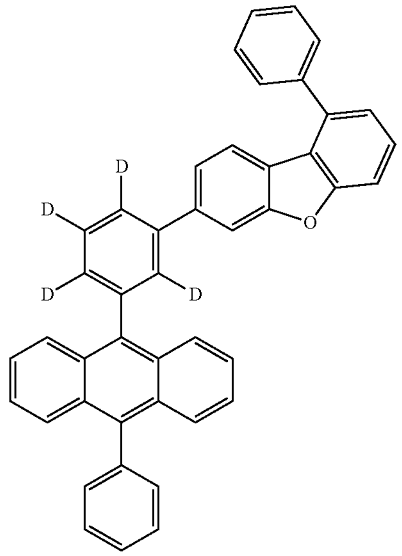
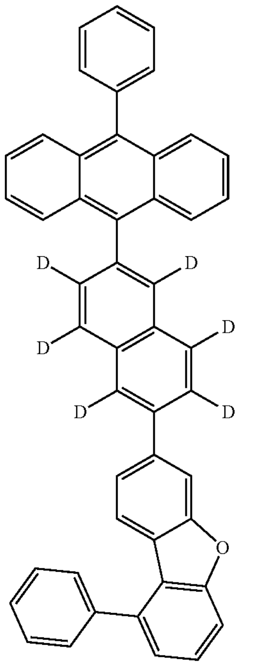

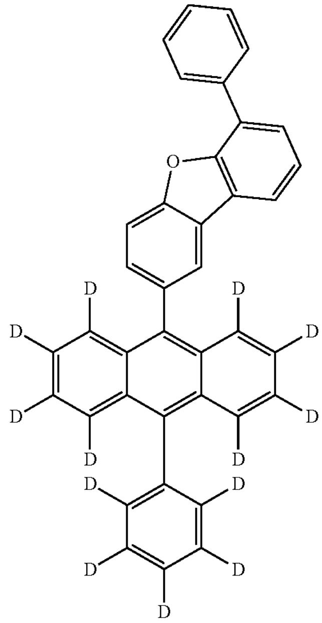
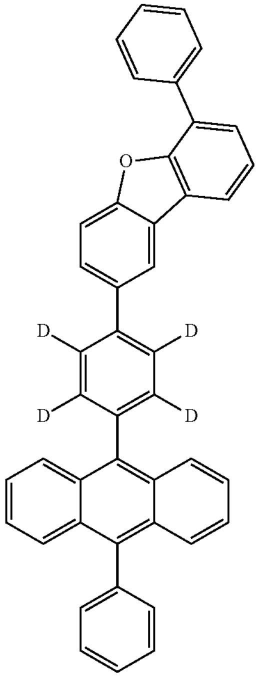
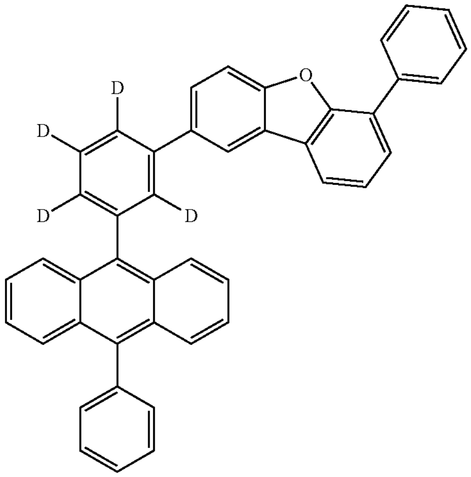
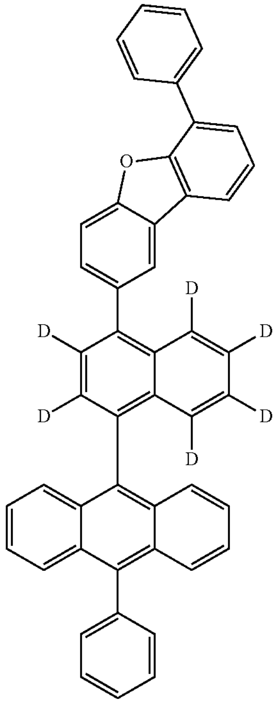

-continued
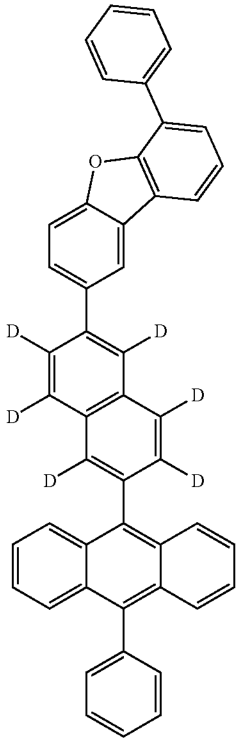
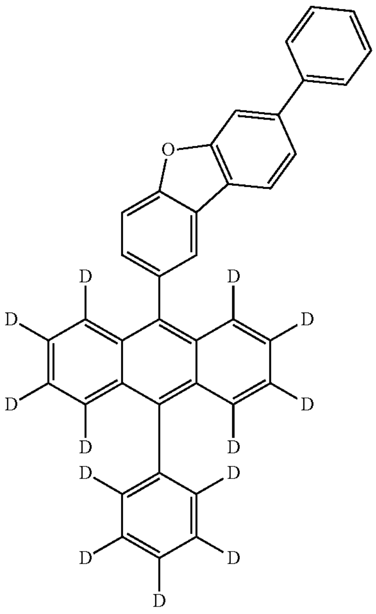
-continued
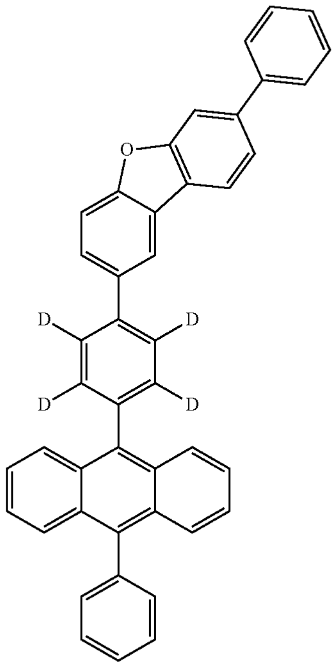
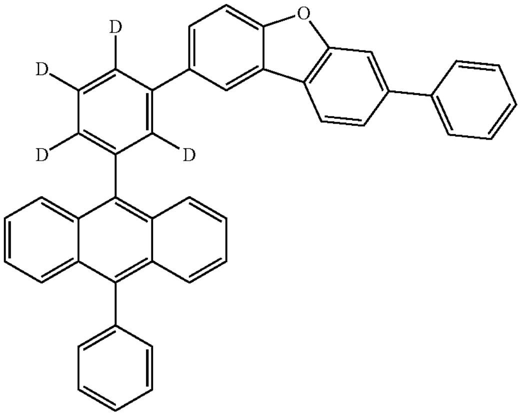

-continued
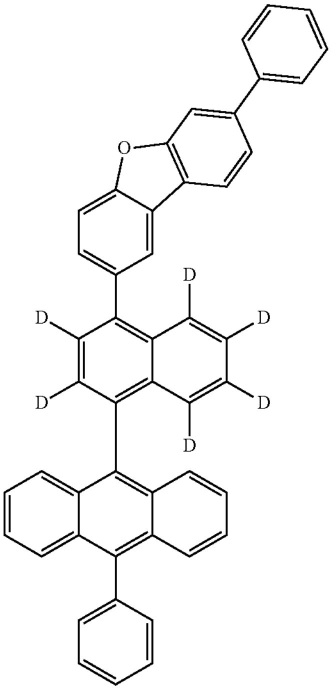
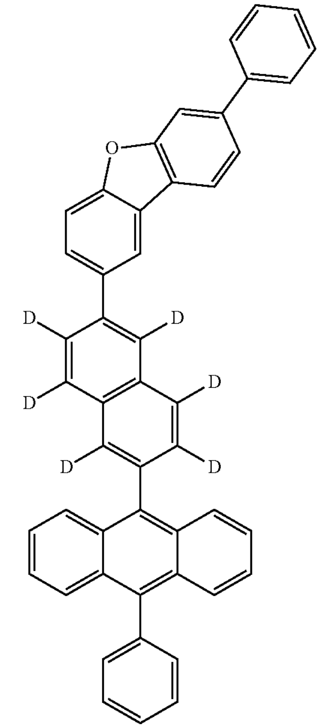
-continued
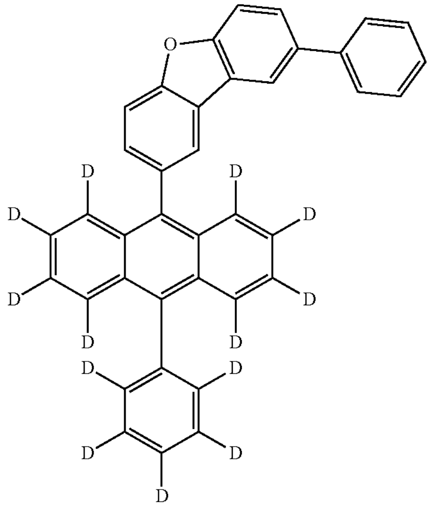
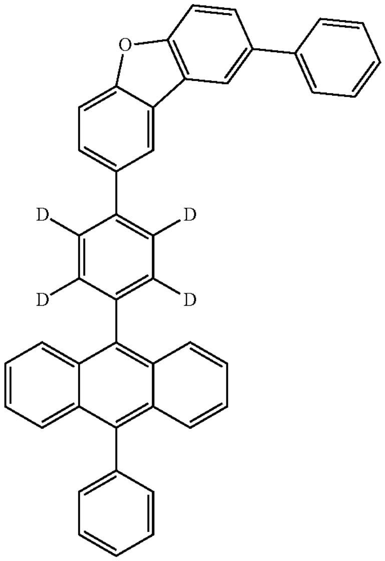
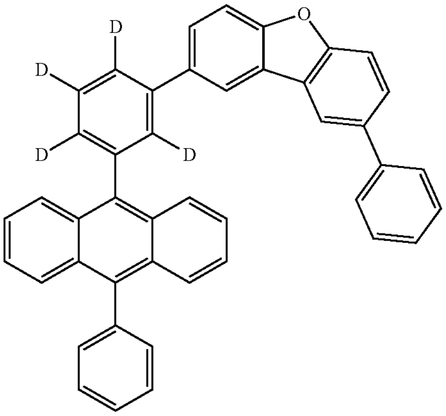

-continued
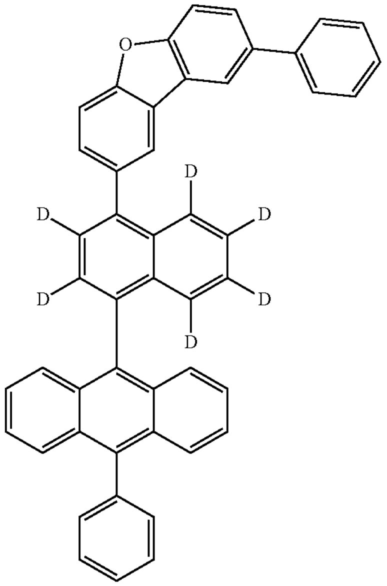
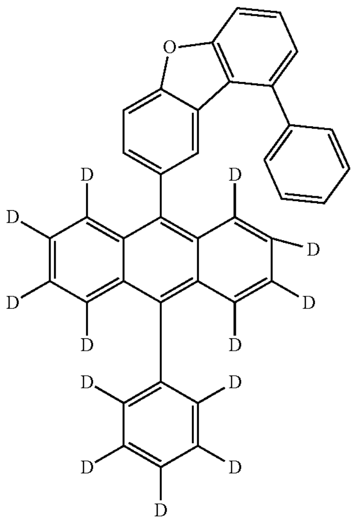
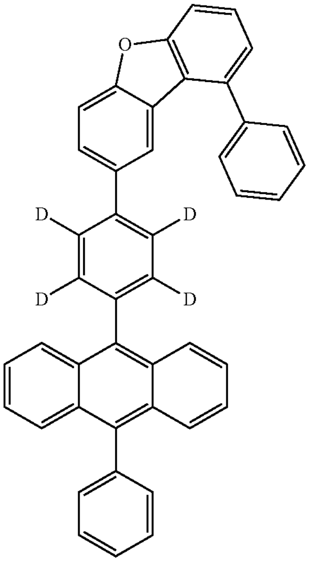
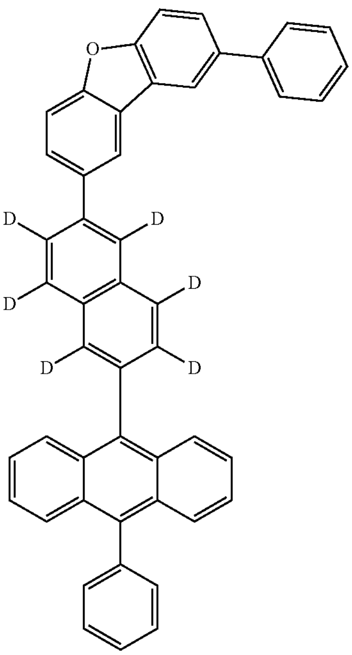 [SMILES: [2H]c1c(-c2c3ccccc3c(-c3ccccc3)c3ccccc23)c([2H])c2c([2H])c([2H])c(-c3ccc4oc5ccc(-c6ccccc6)cc5c4c3)c([2H])c2c1[2H]]
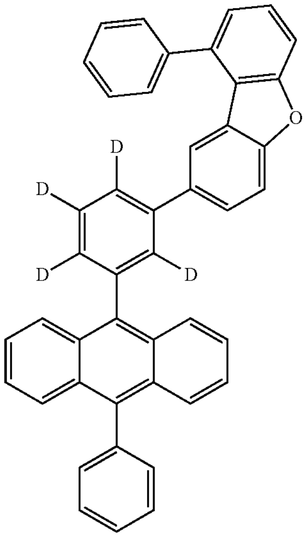

-continued
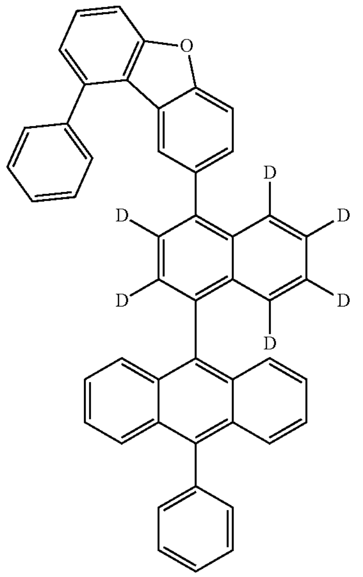
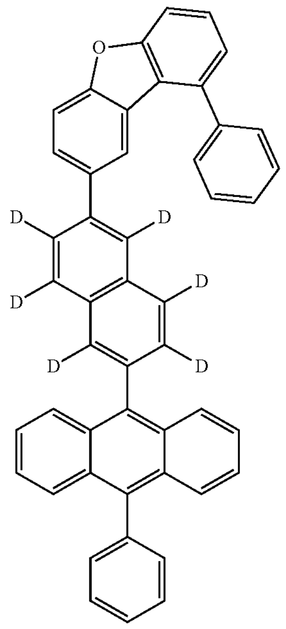
-continued
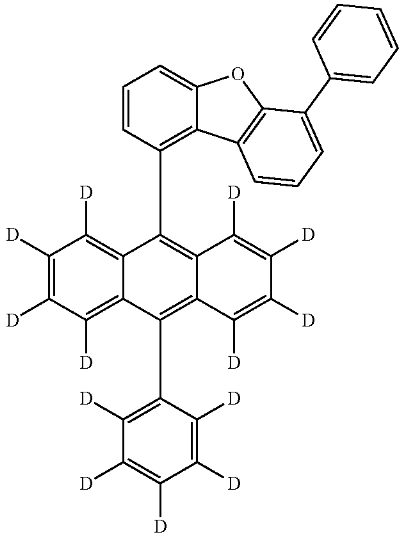
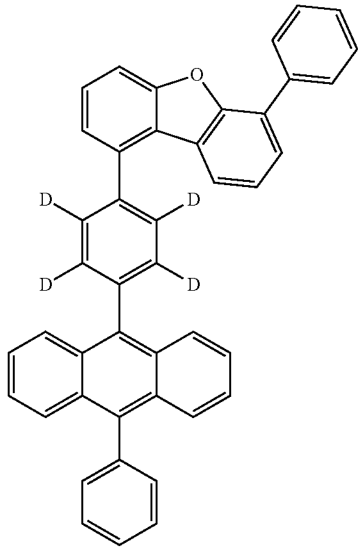
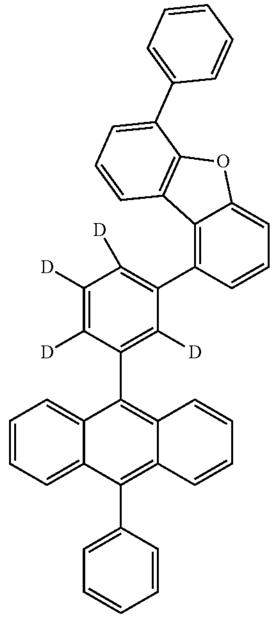

-continued
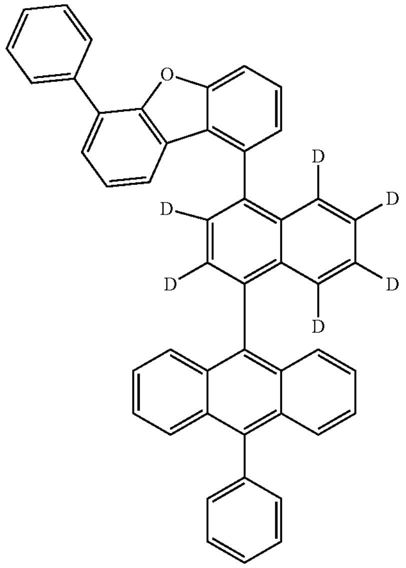
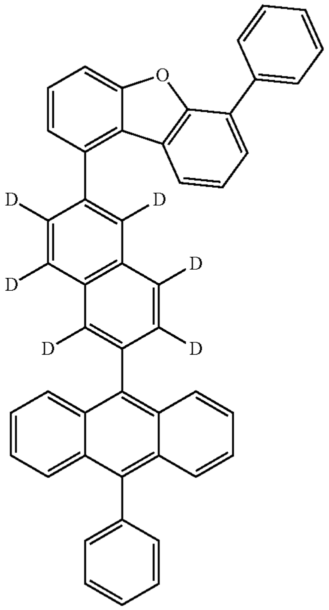
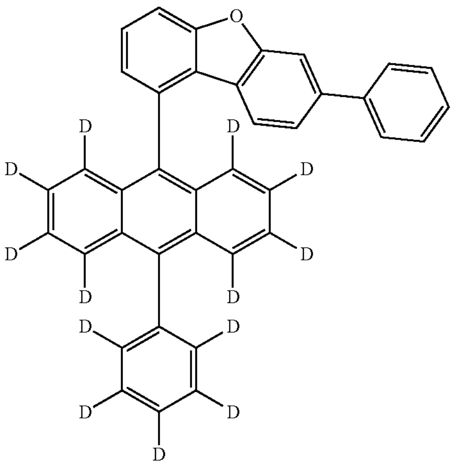
-continued
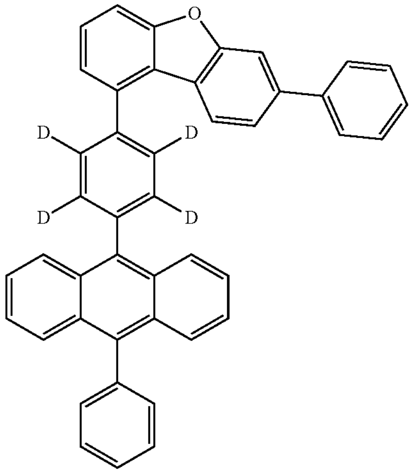
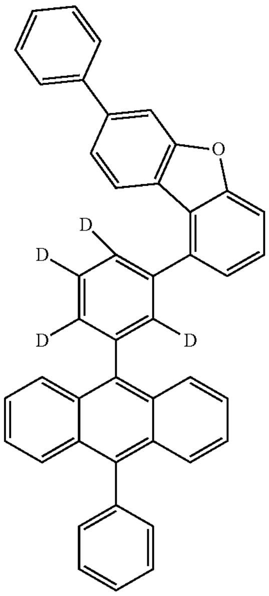
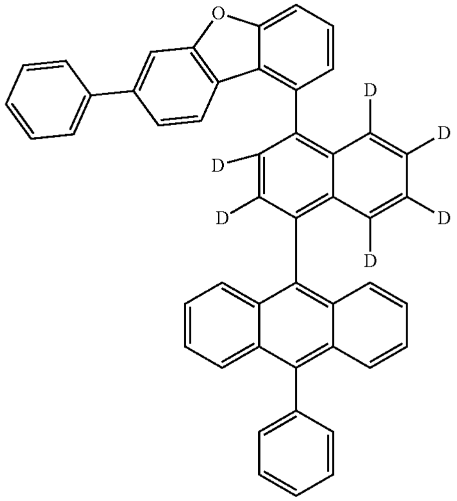

-continued
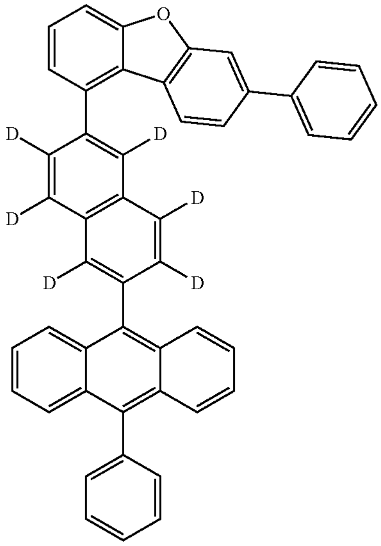
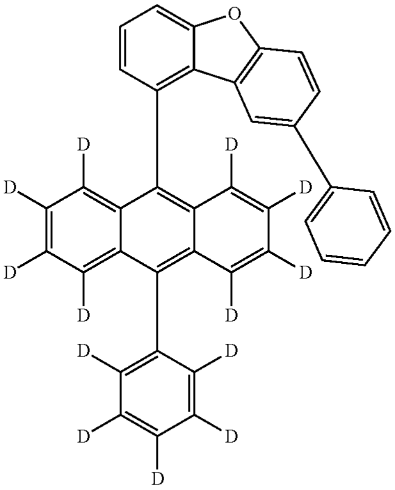
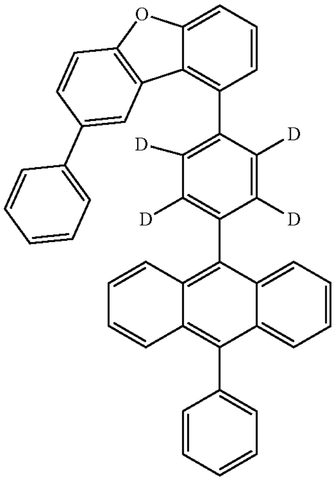
-continued
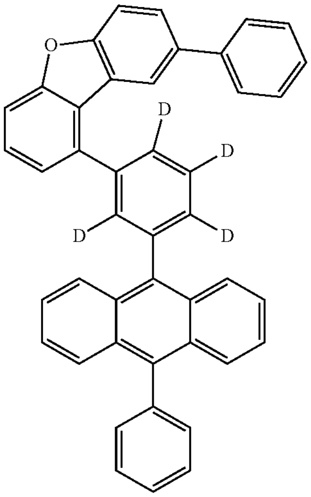
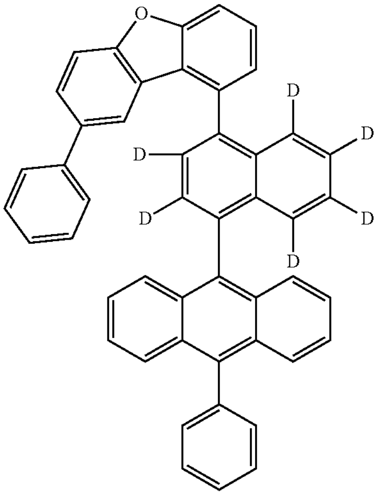
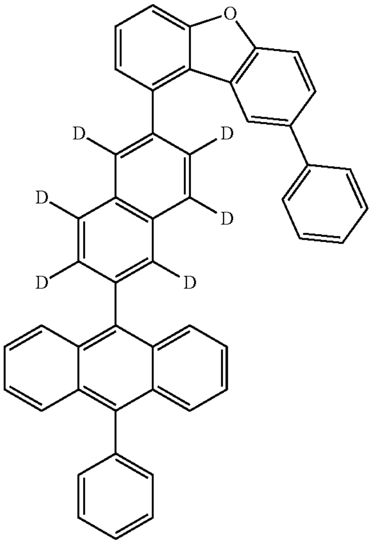

-continued
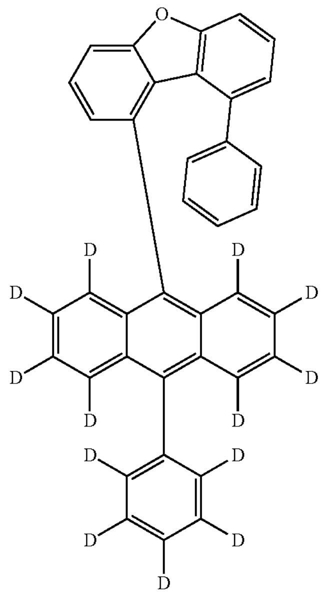
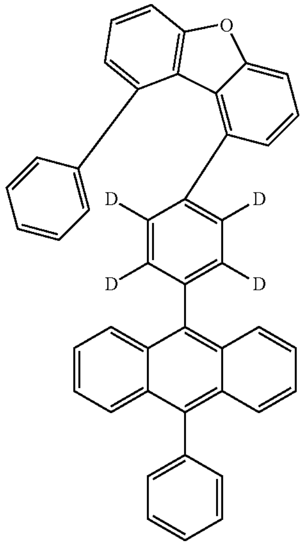
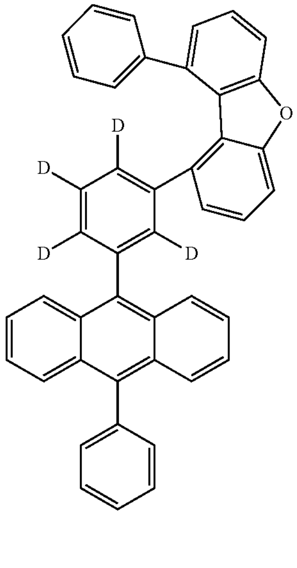
-continued
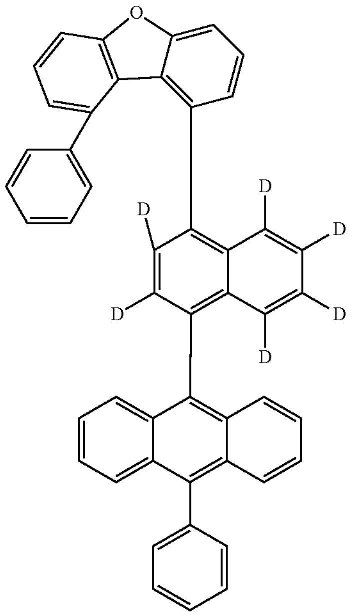
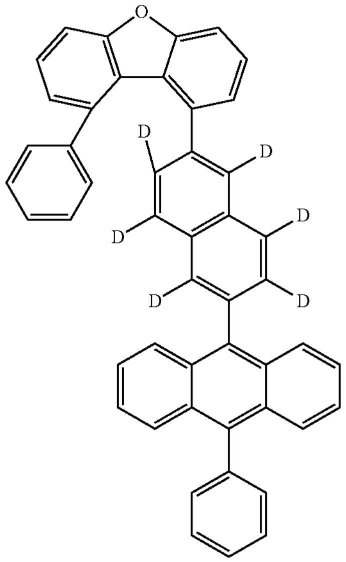

-continued
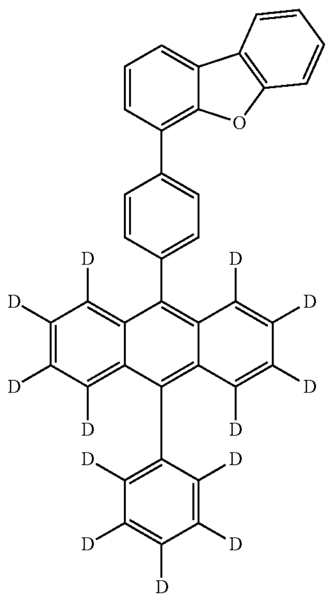
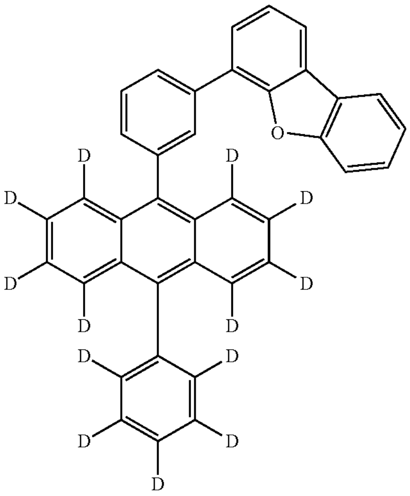
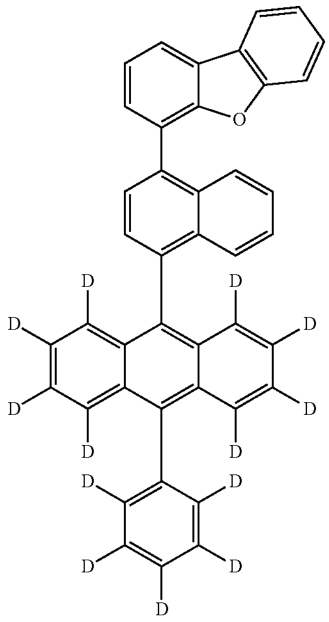
-continued
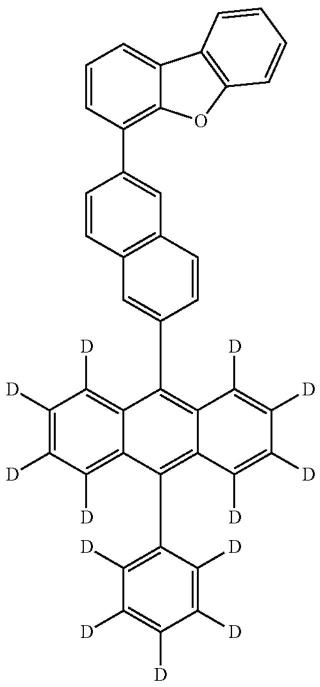
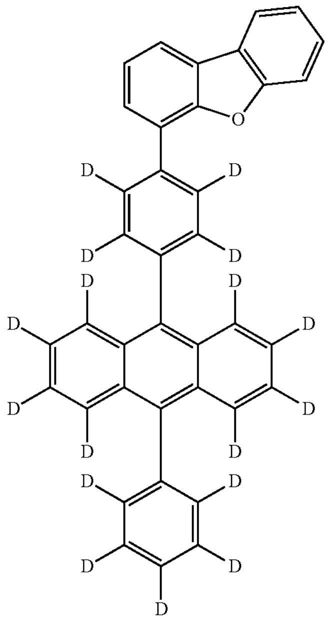

-continued
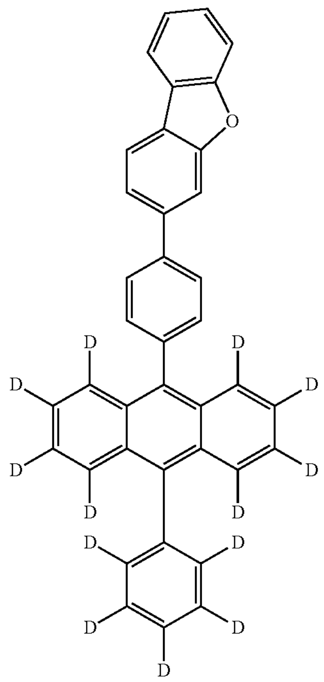
-continued
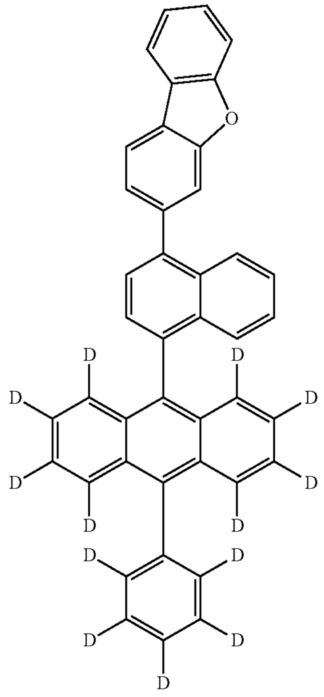
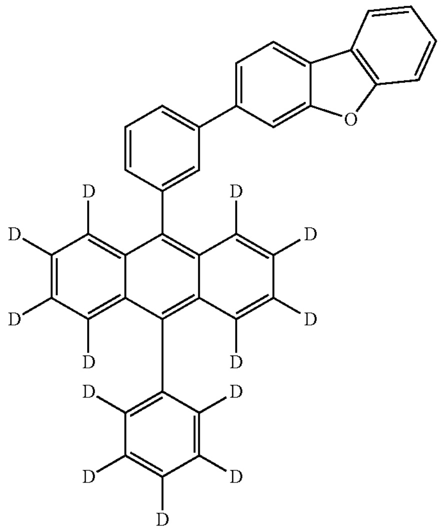
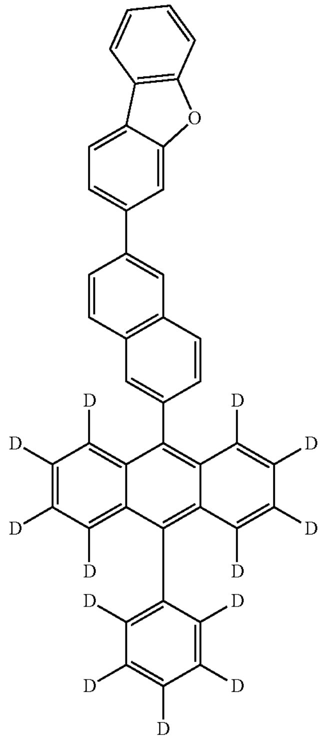

-continued
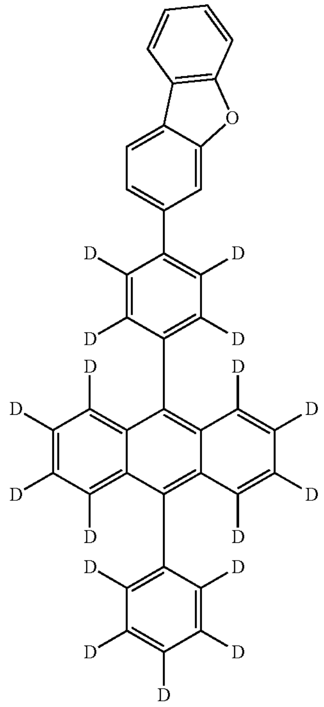
-continued
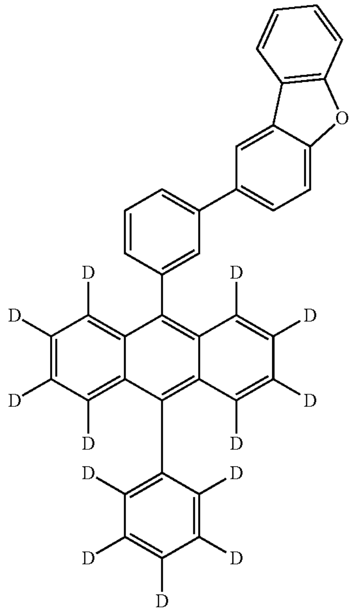
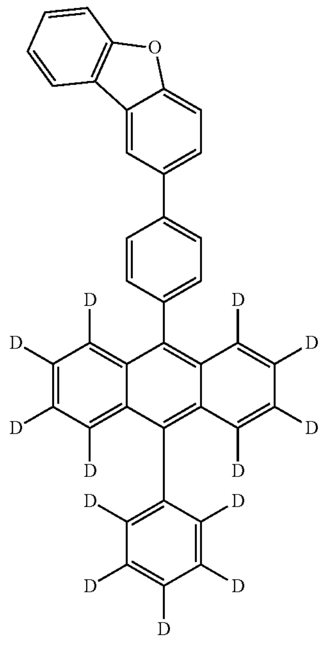
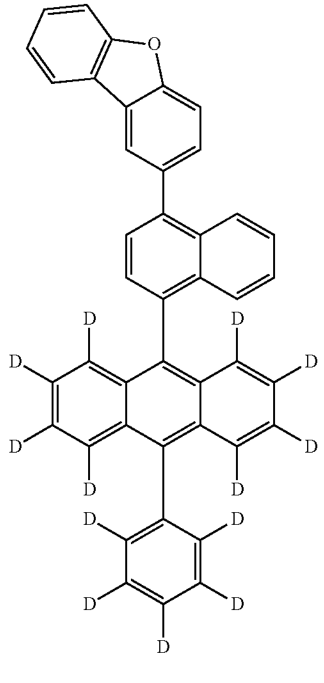

-continued
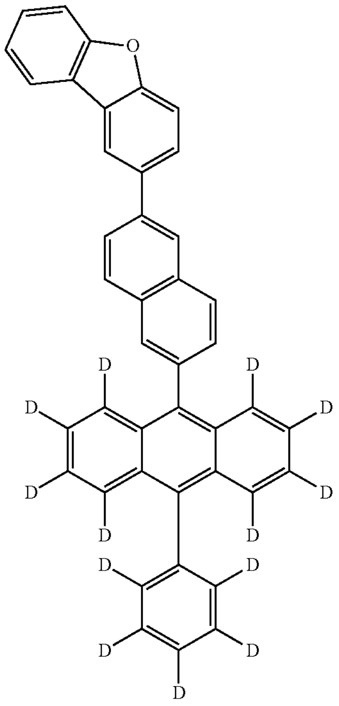
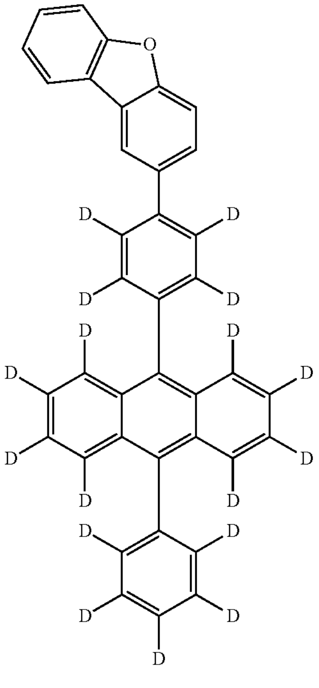
-continued
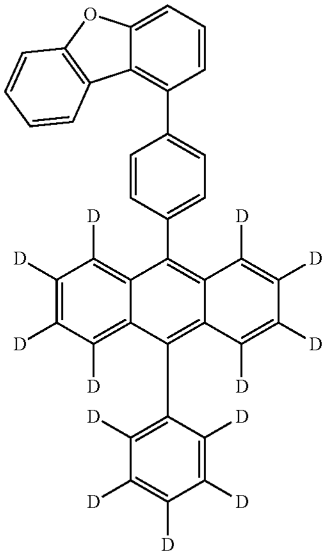
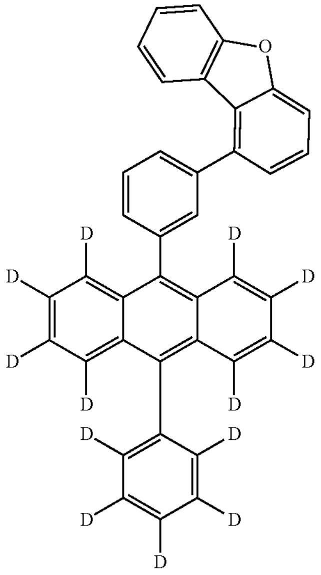
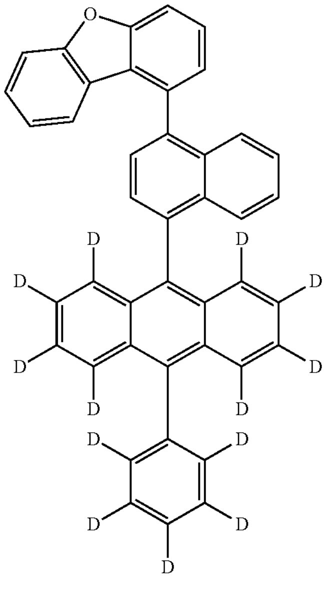

-continued
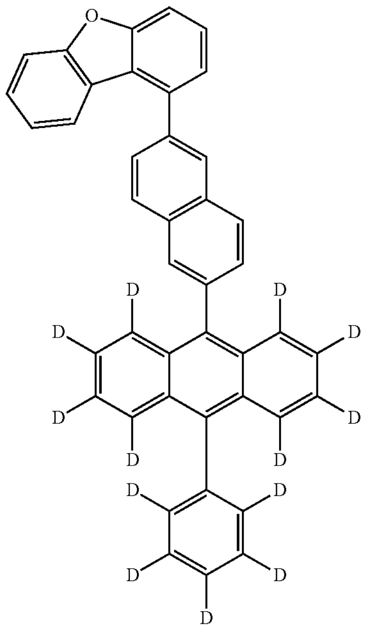
-continued
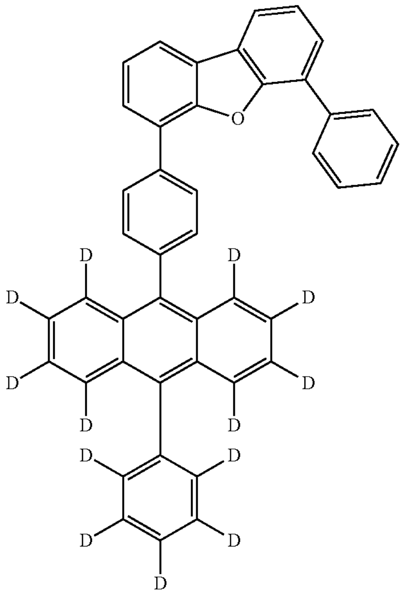
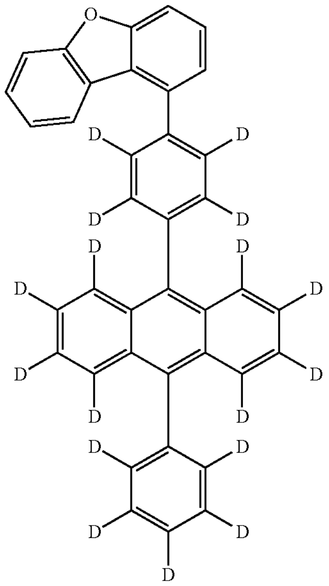
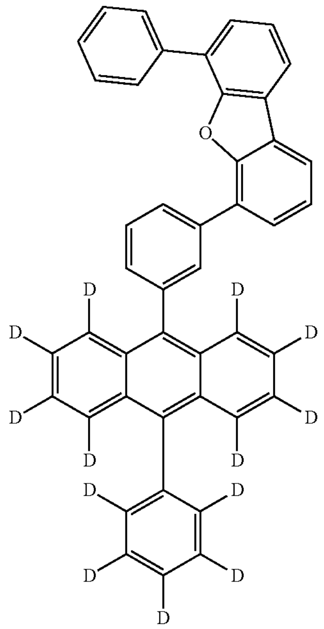

-continued
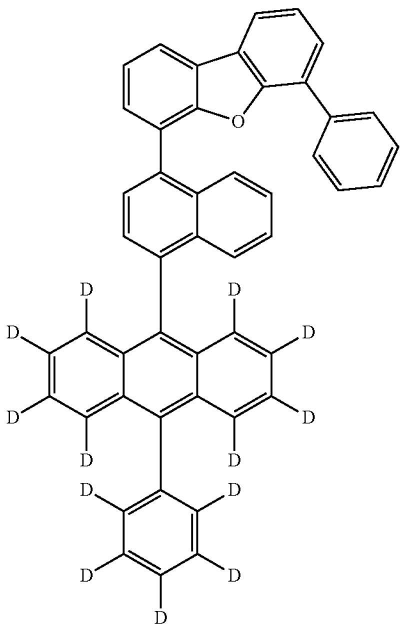
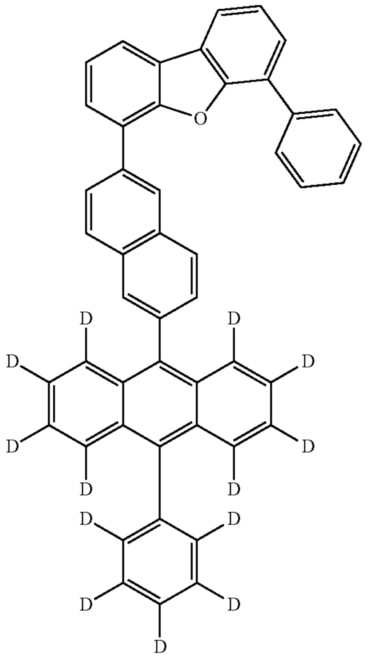
-continued
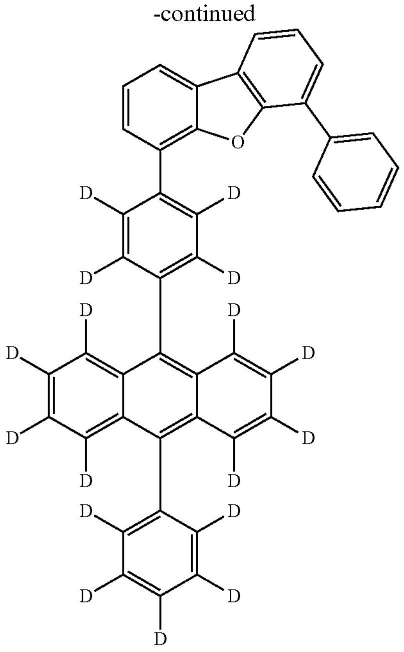
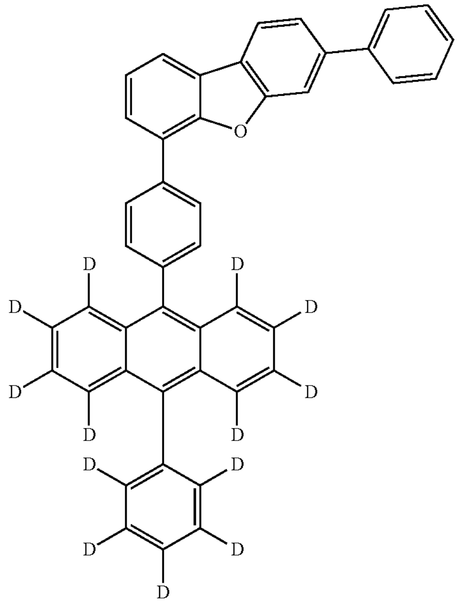
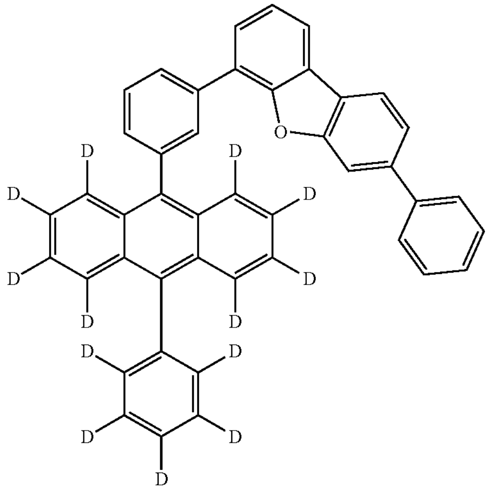

-continued
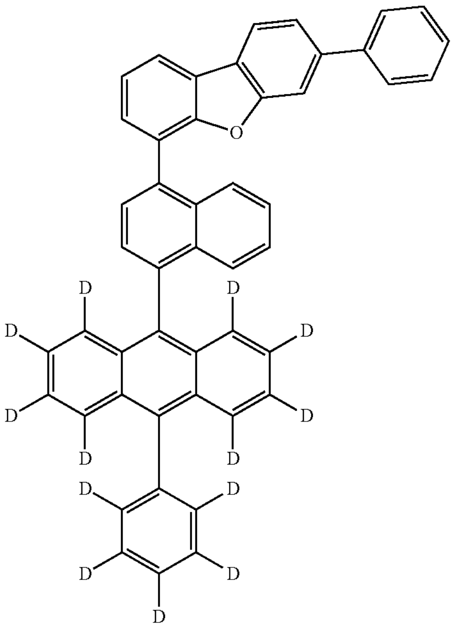
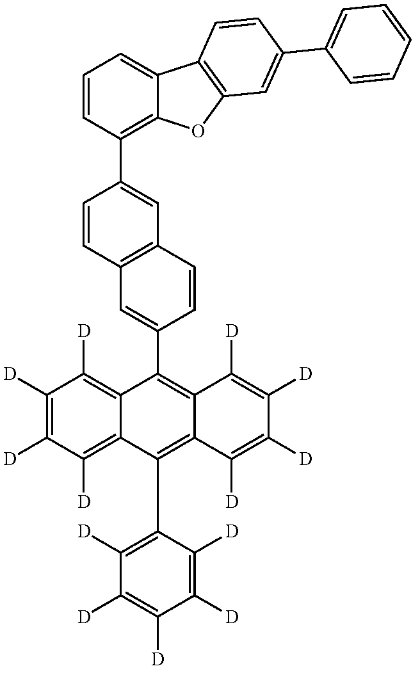
-continued
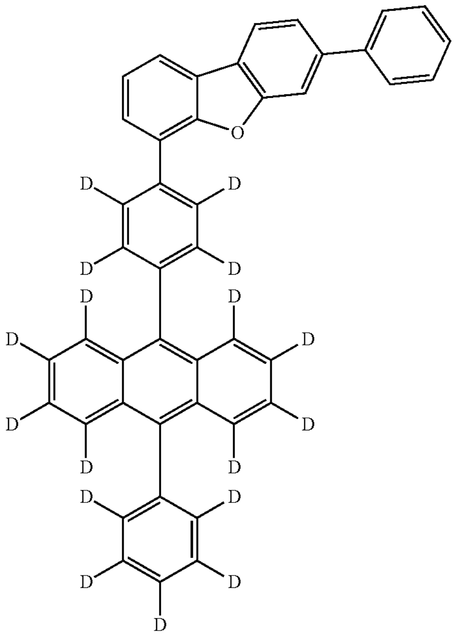
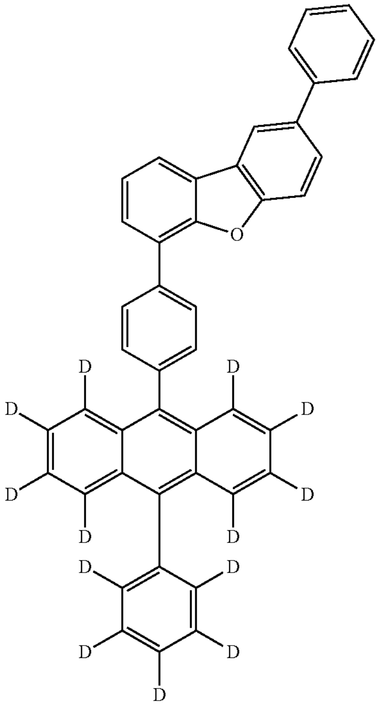

-continued
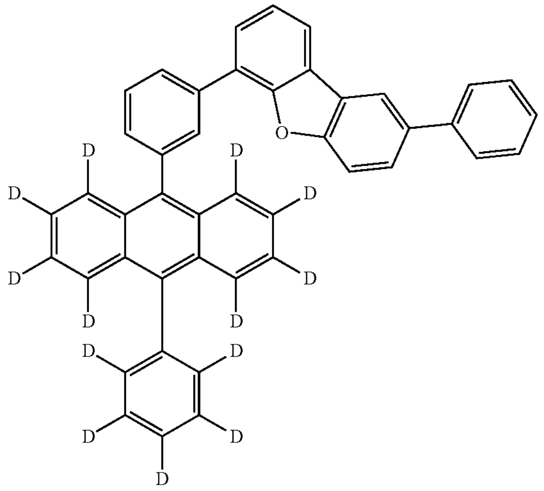
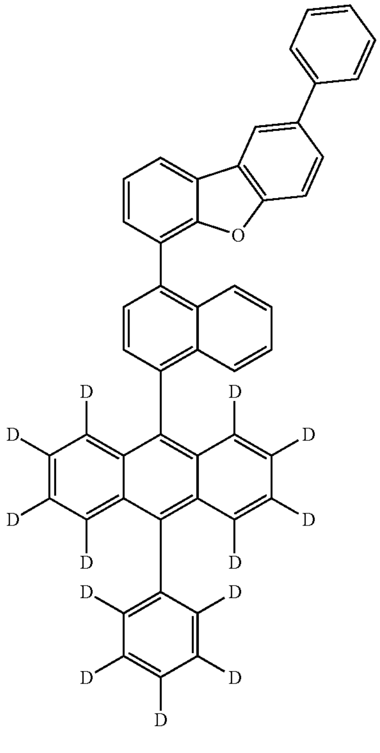
-continued
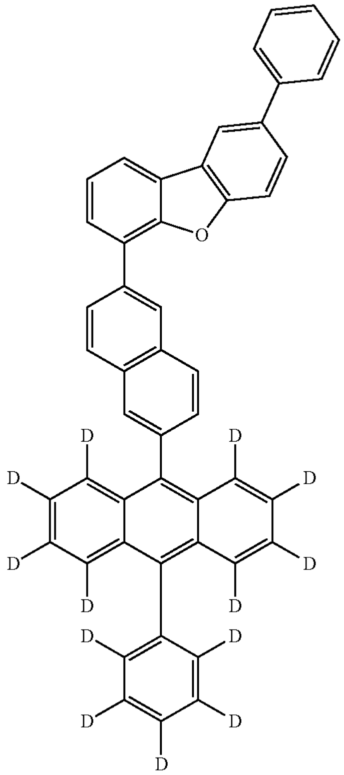
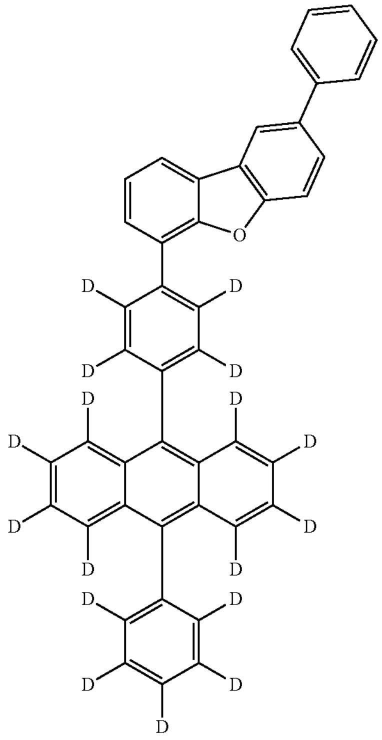

-continued
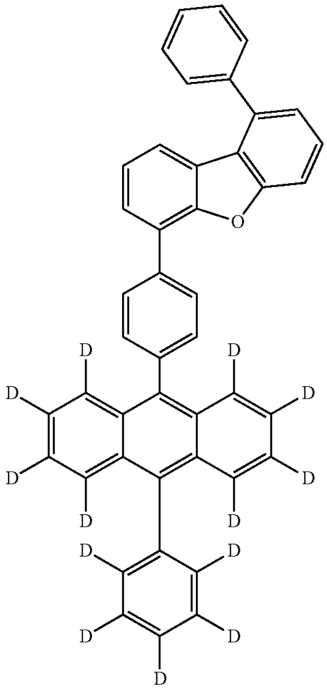
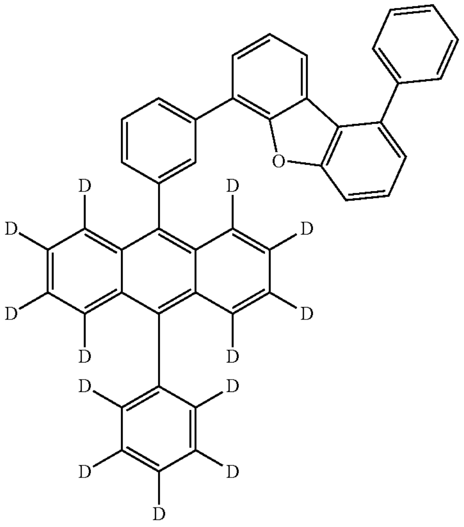
-continued
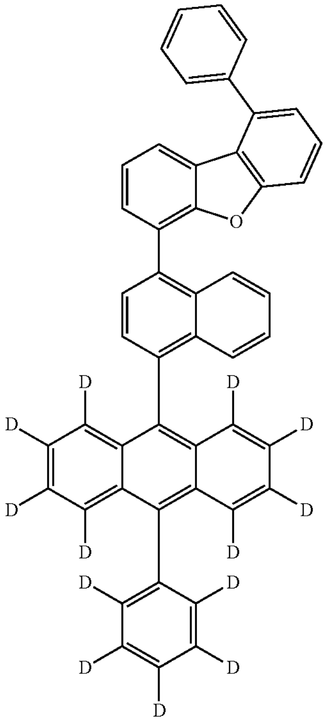
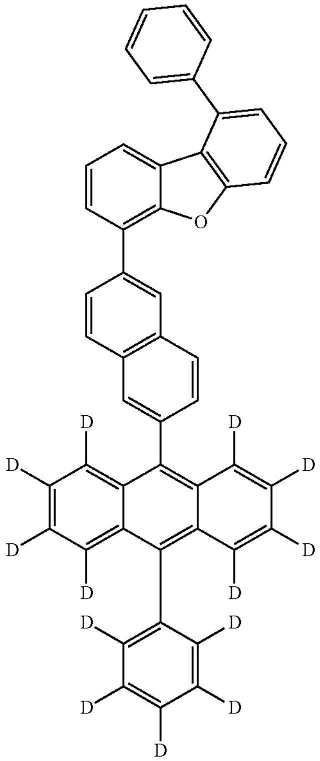

-continued
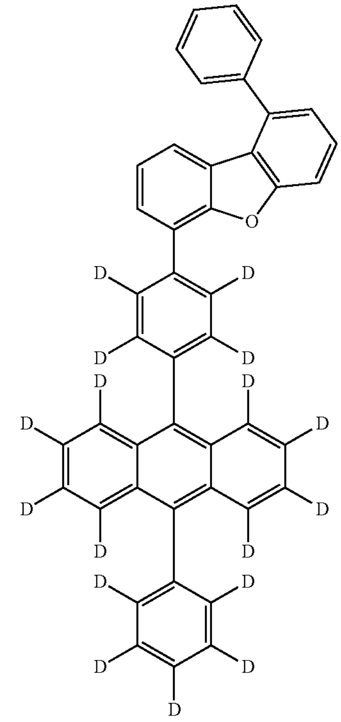
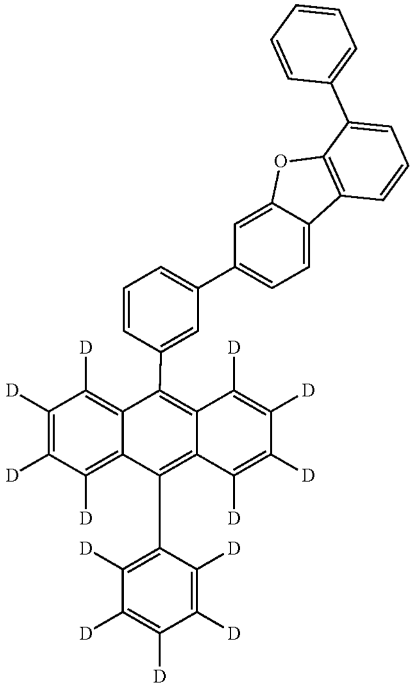
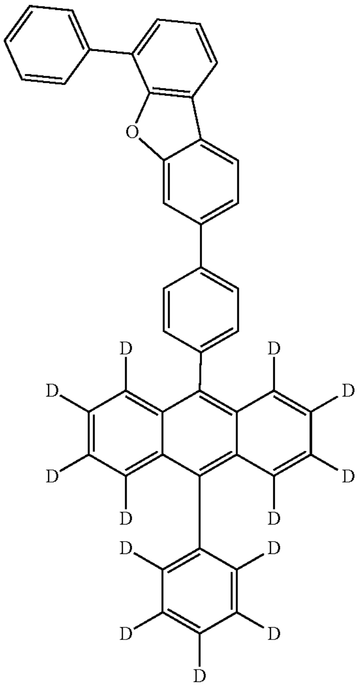
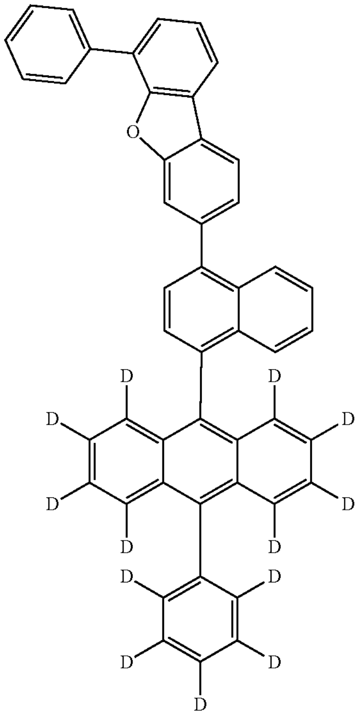

-continued
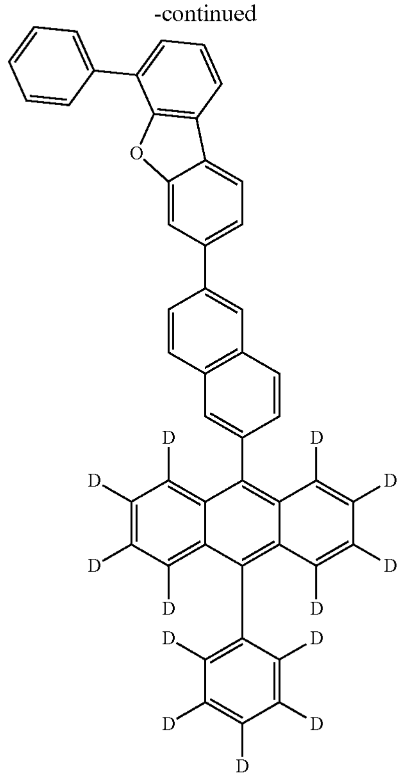
-continued
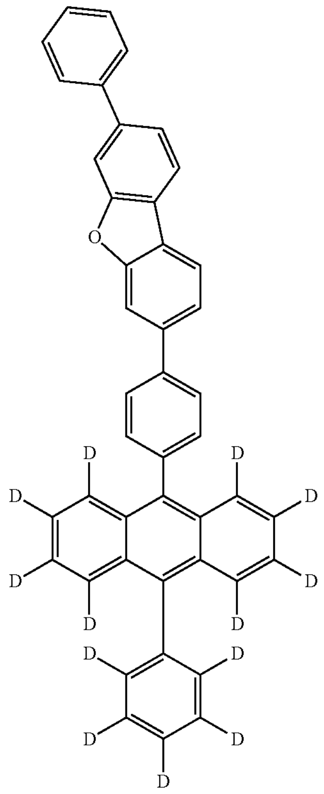
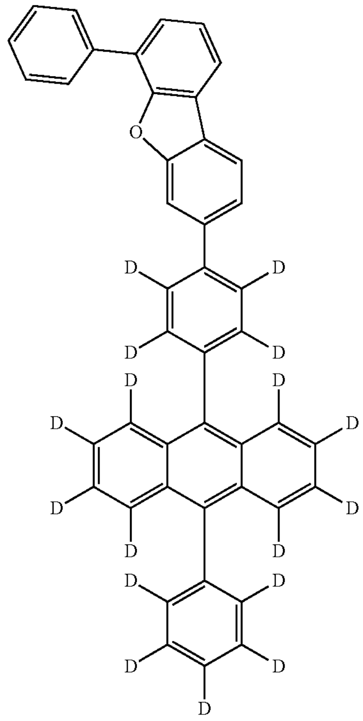
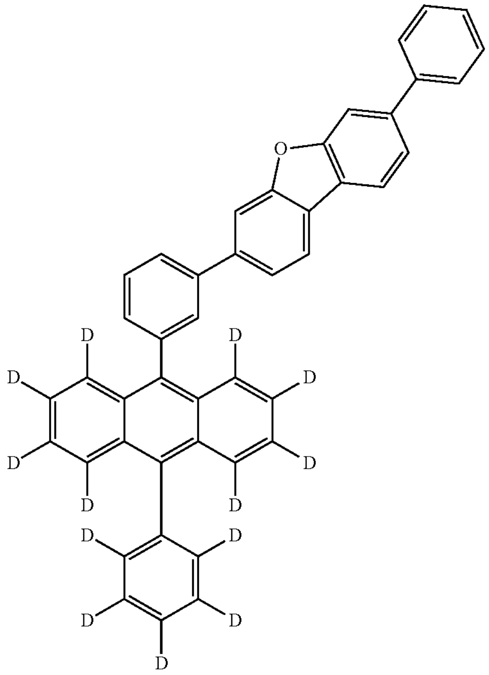

-continued
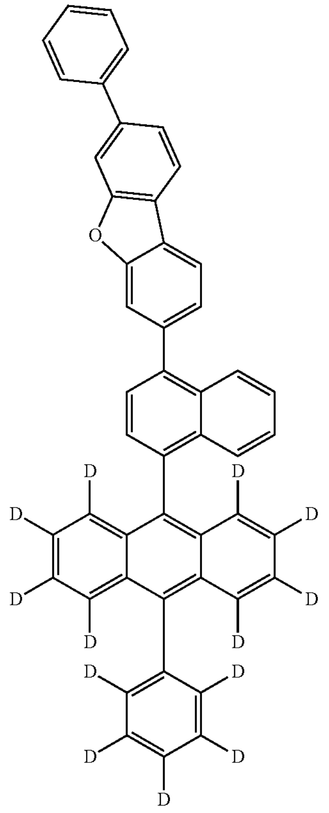
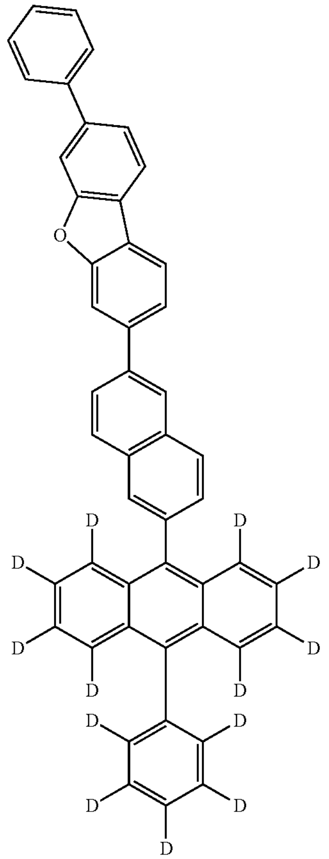
-continued
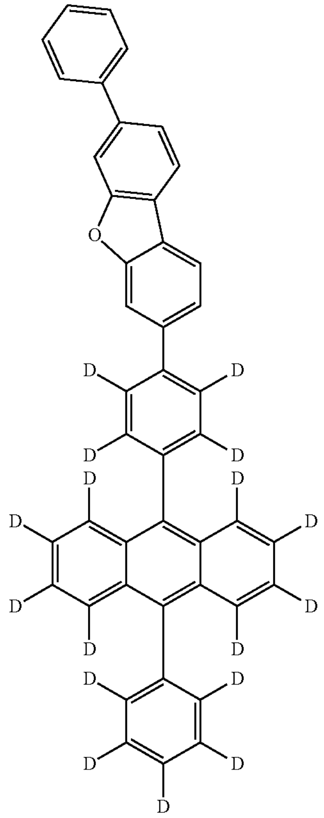
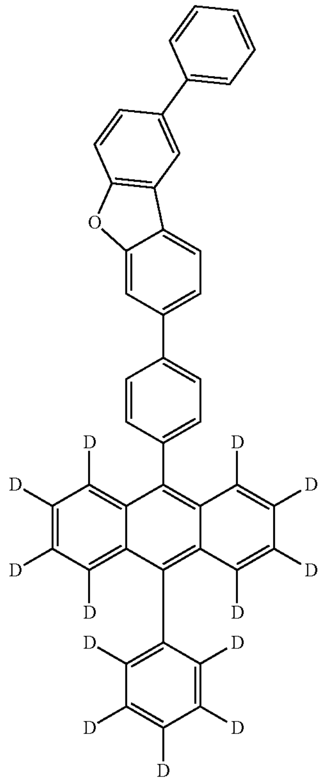

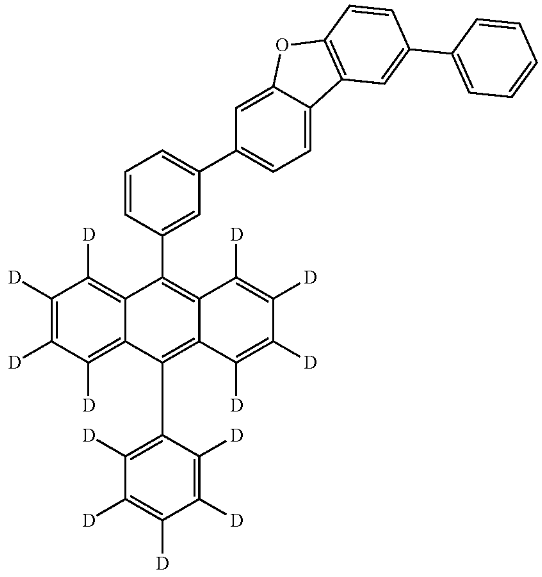
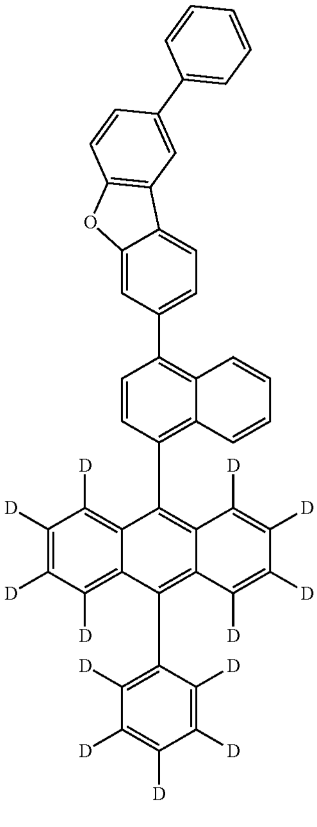
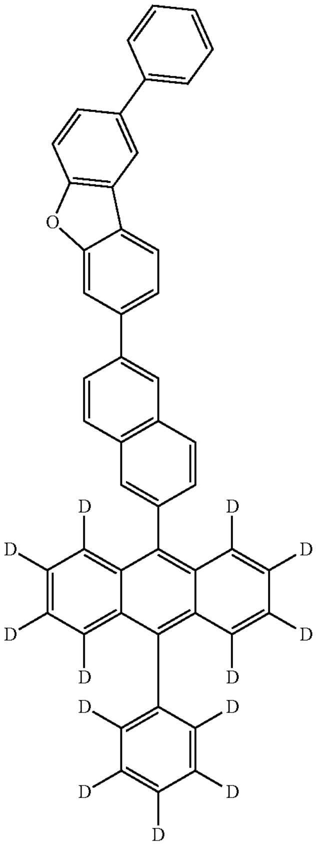
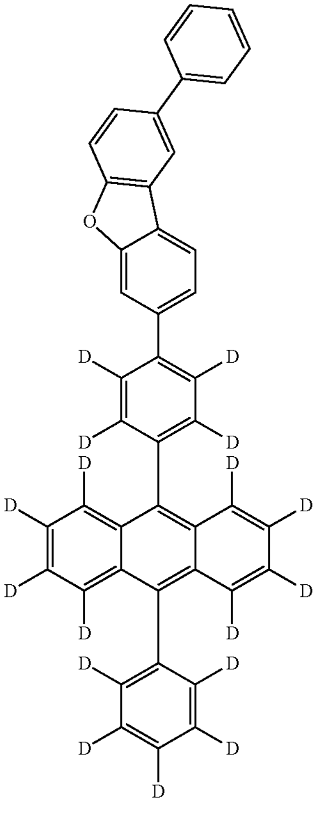

-continued
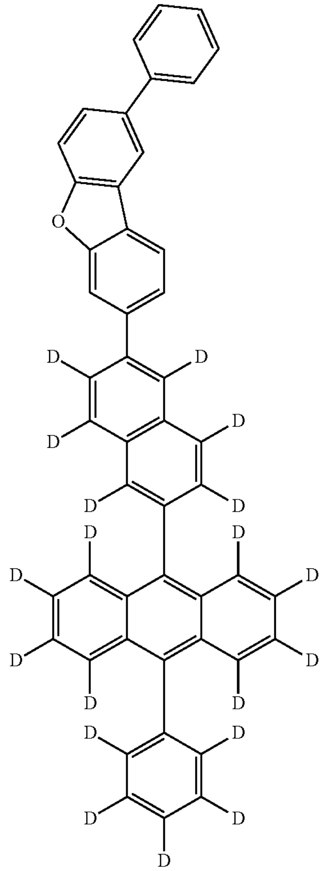
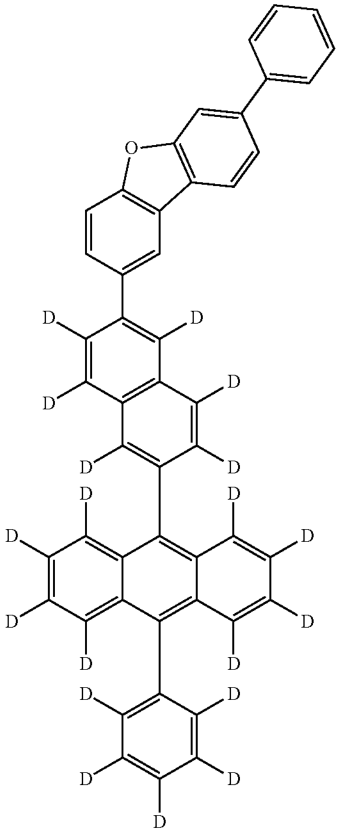
-continued
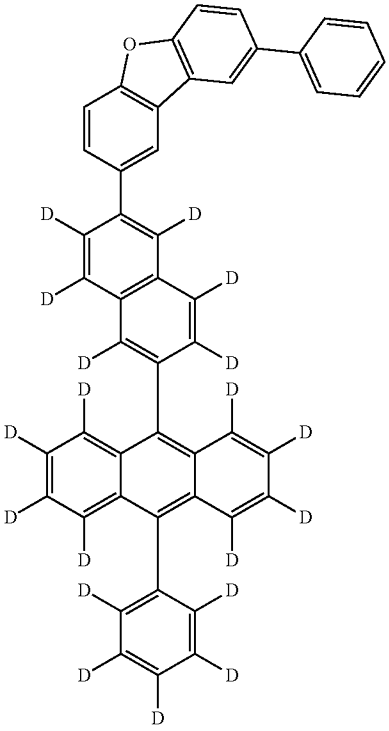
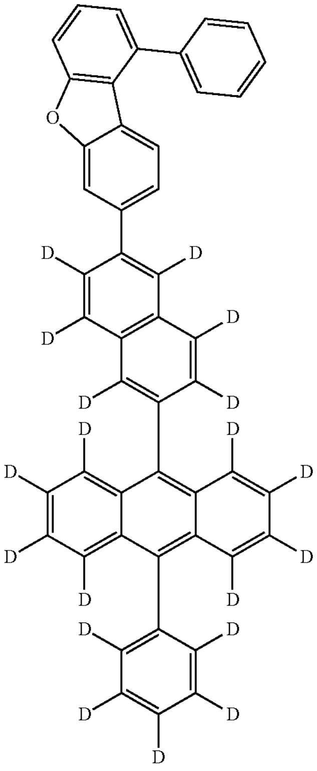

-continued
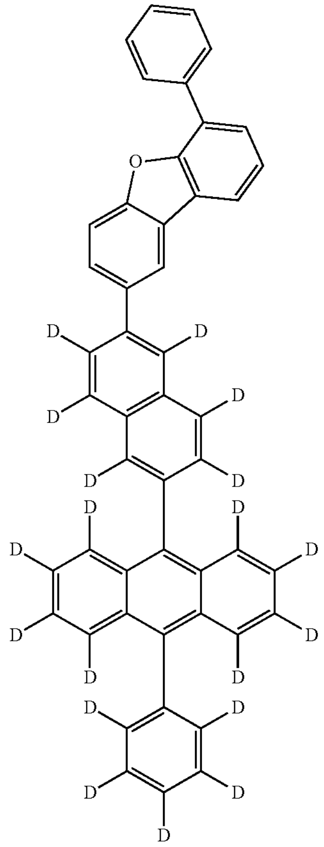
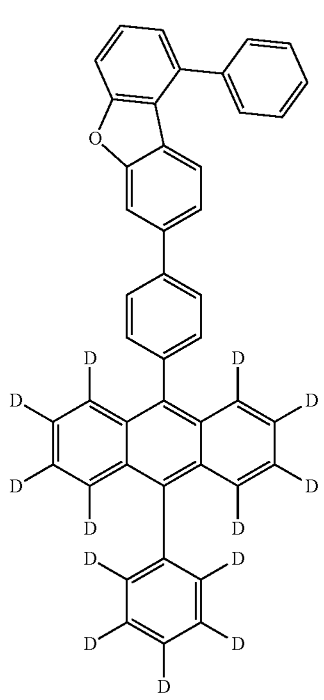
-continued
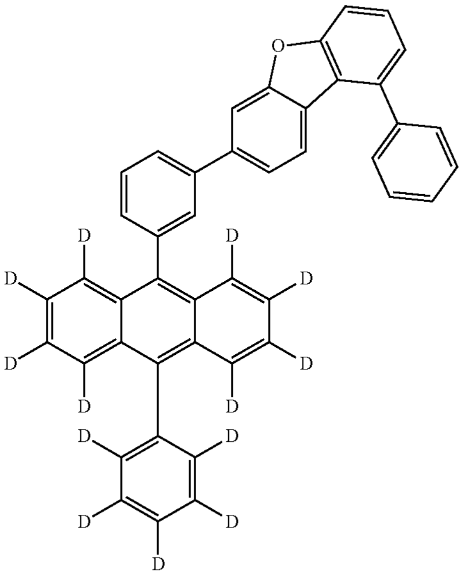
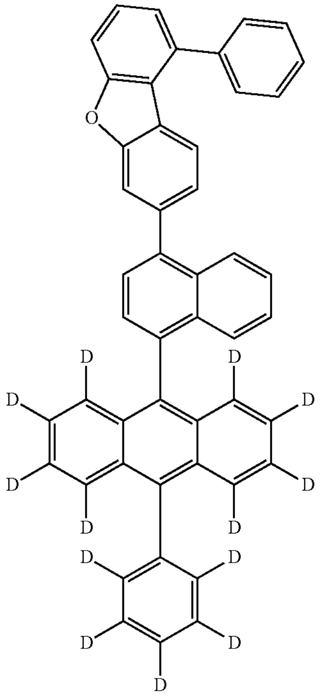

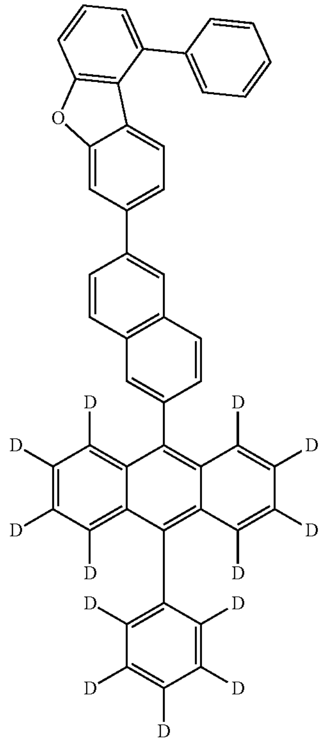
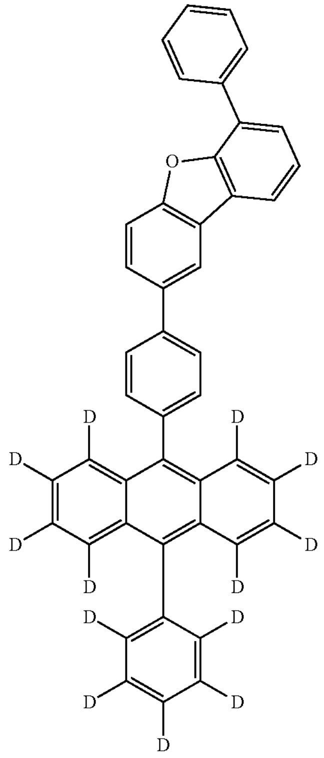
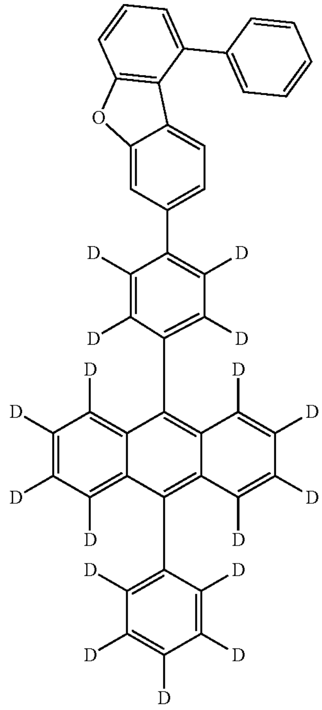
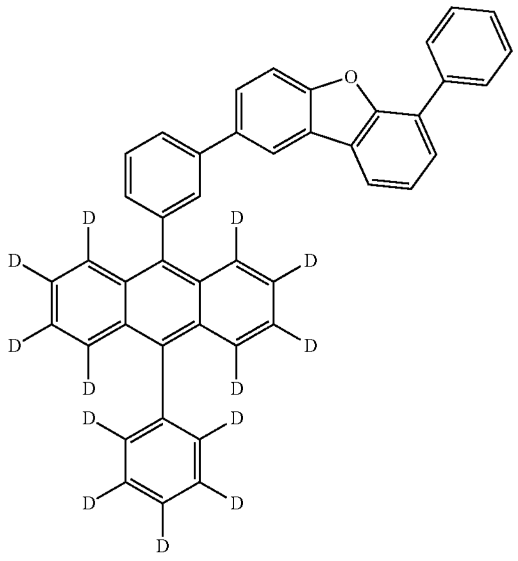

-continued
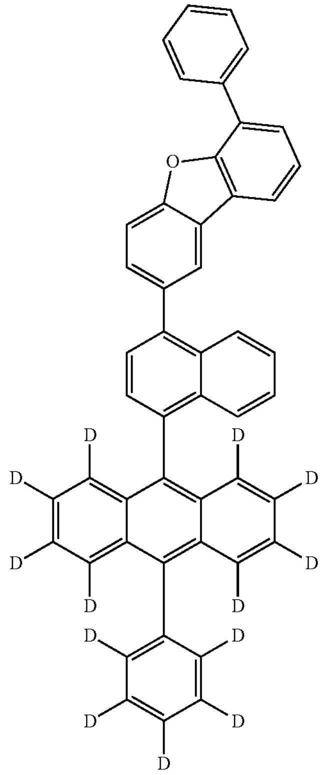
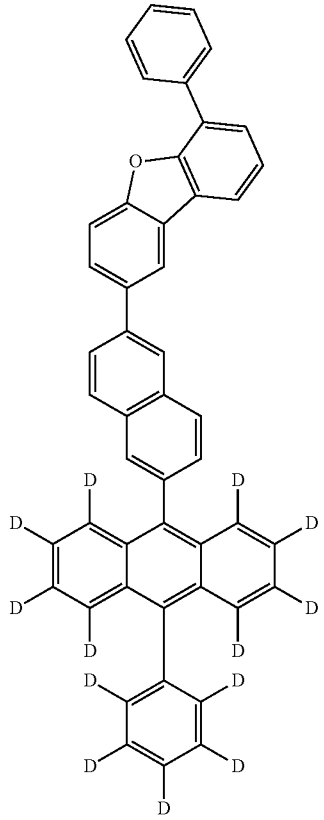
-continued
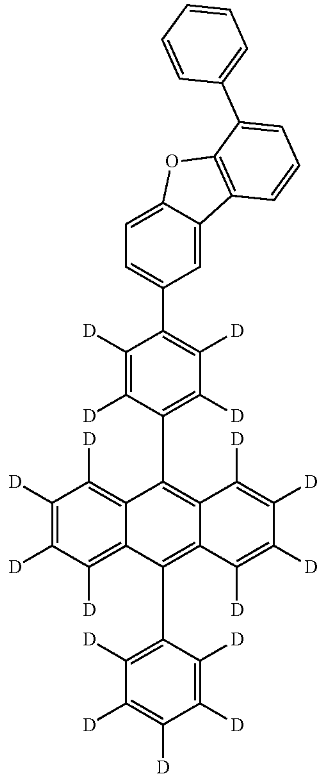
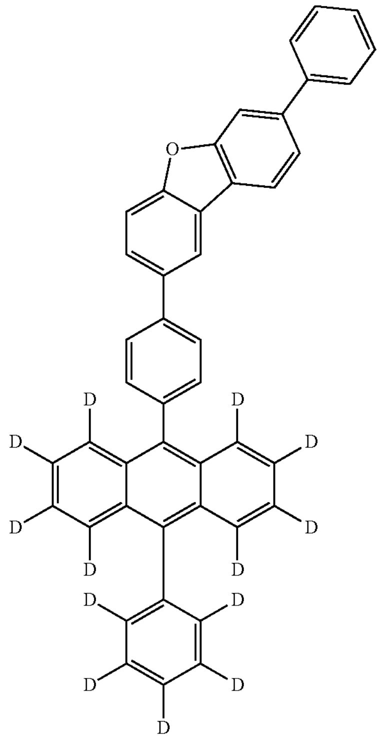

-continued
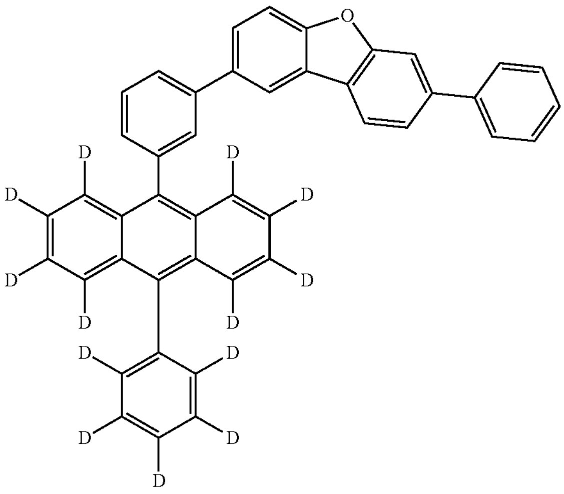
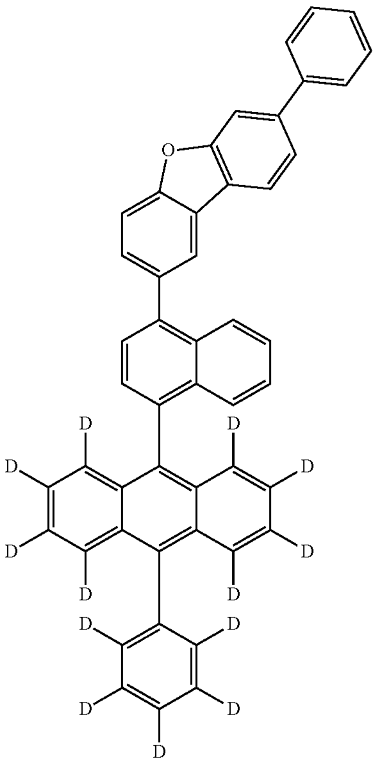
-continued
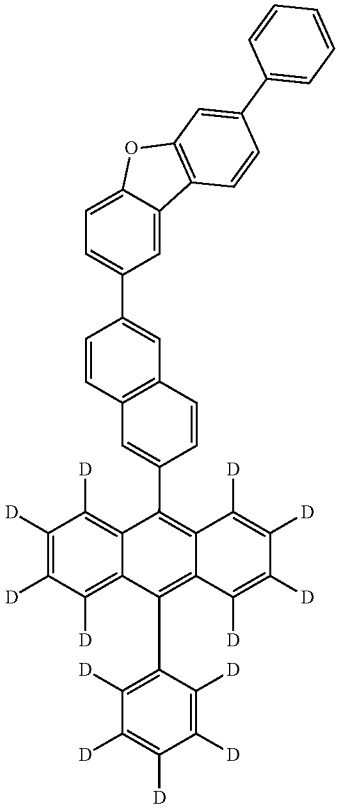
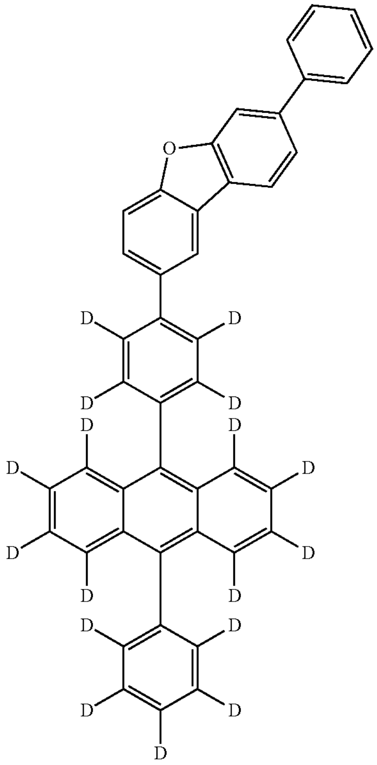

-continued
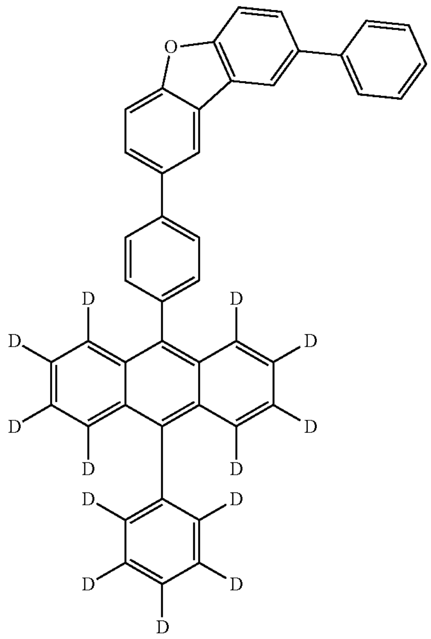
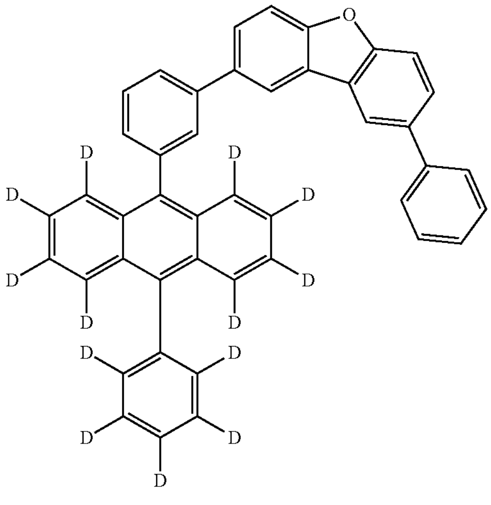
-continued
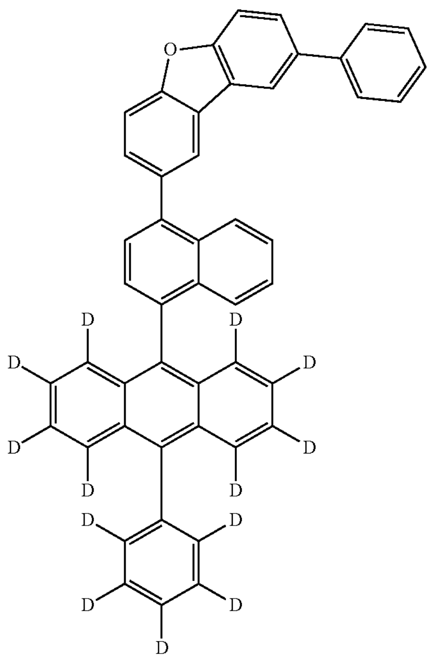
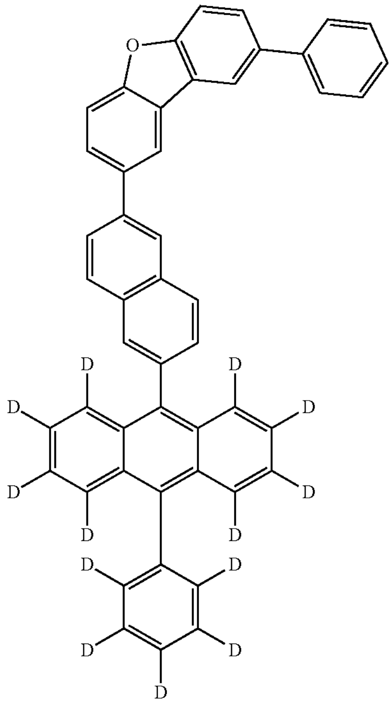

-continued
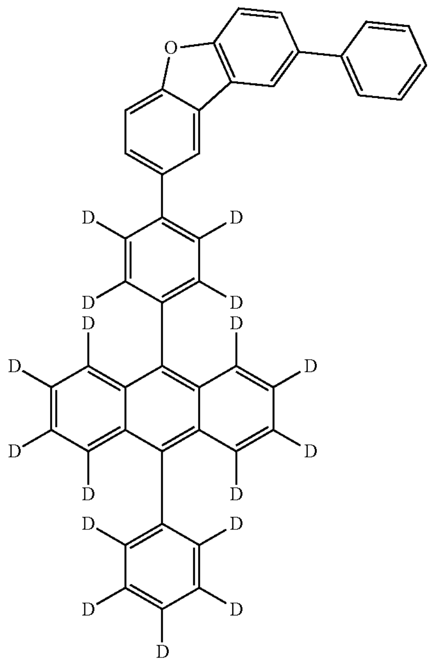
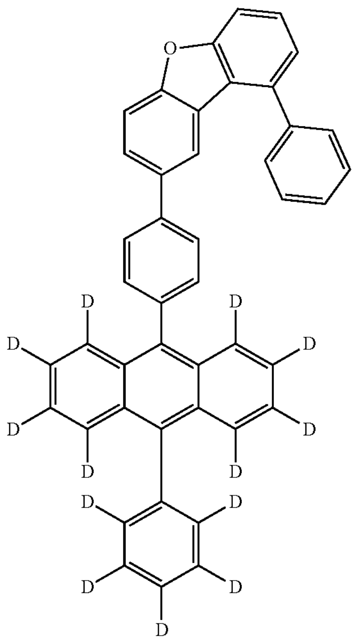
-continued
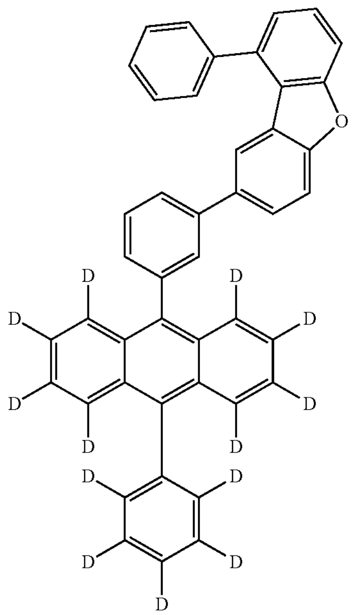
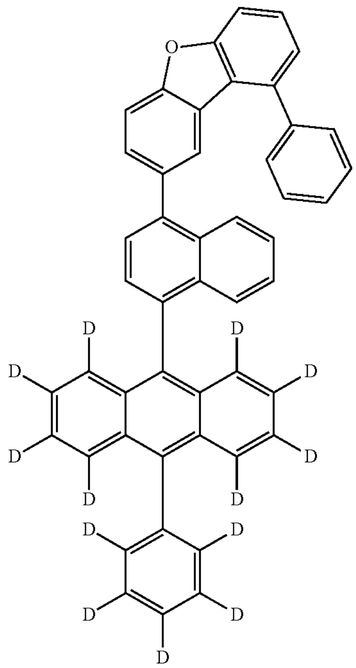

-continued
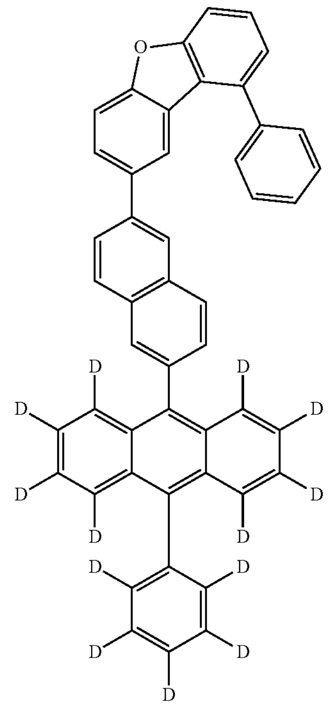
-continued
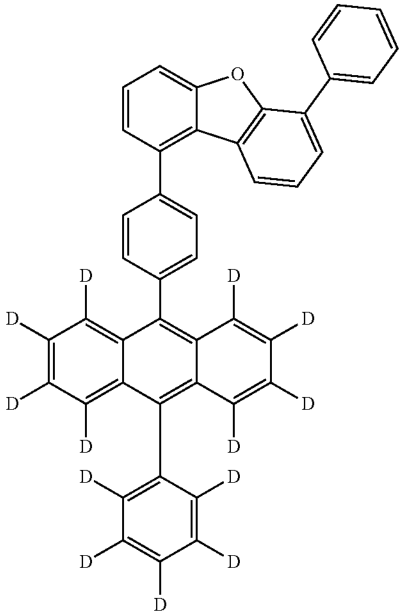
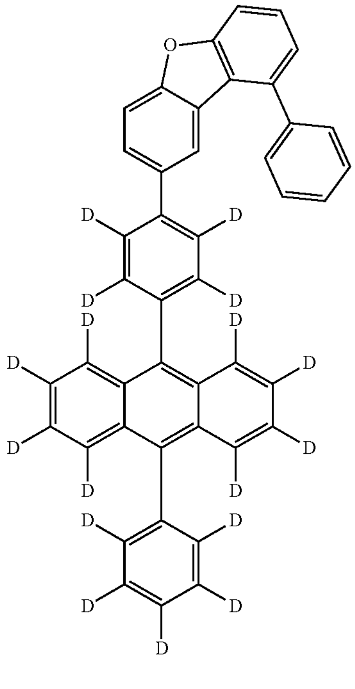
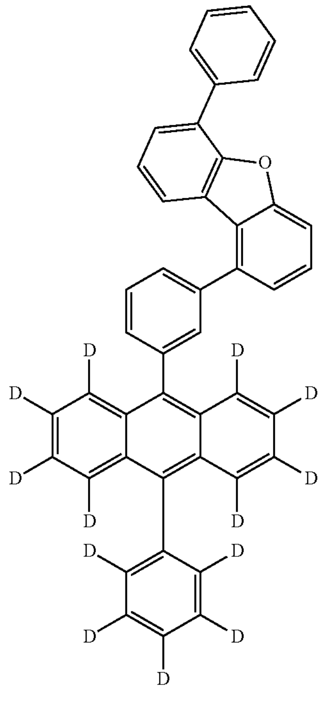

-continued
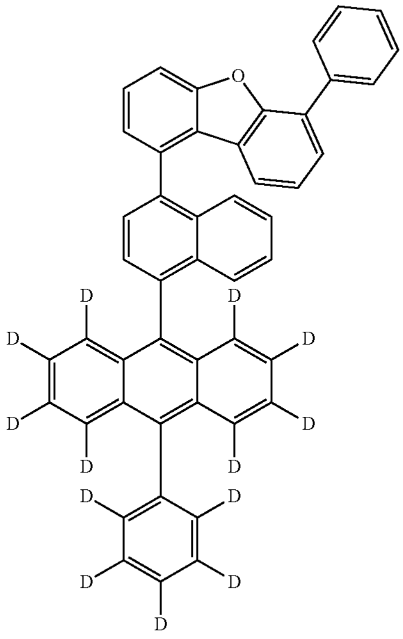
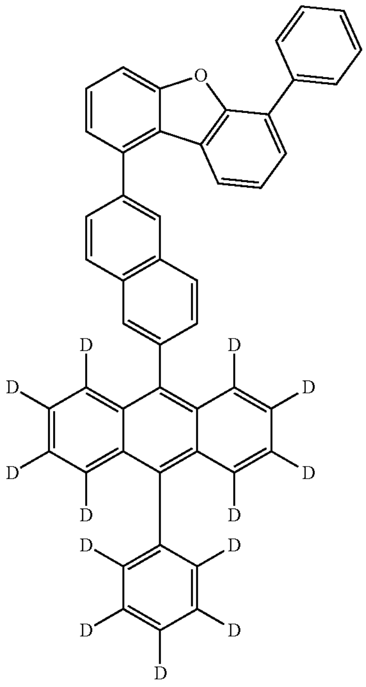
-continued
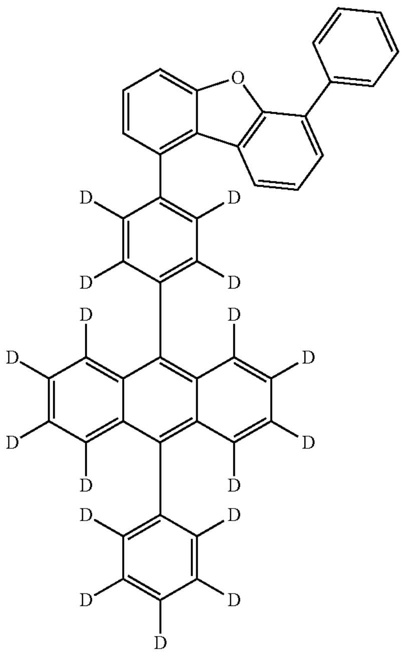
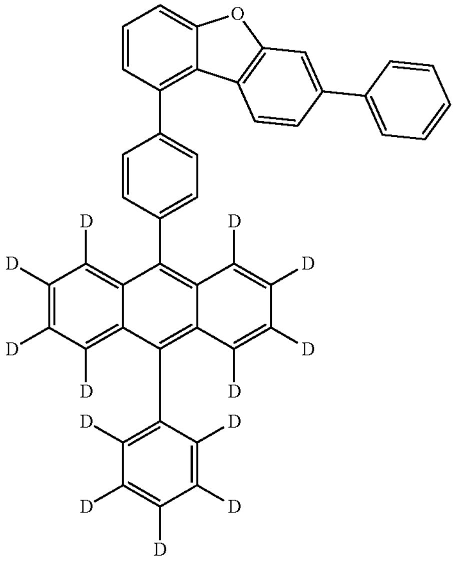

-continued
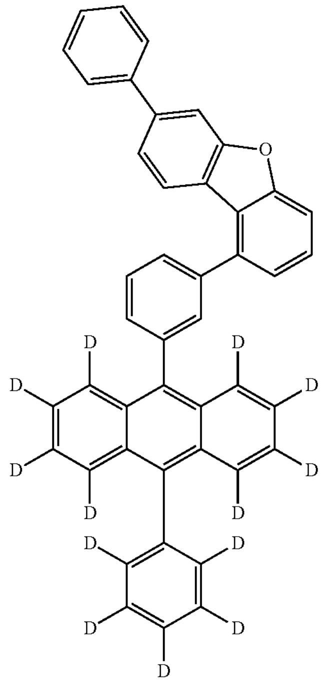
-continued
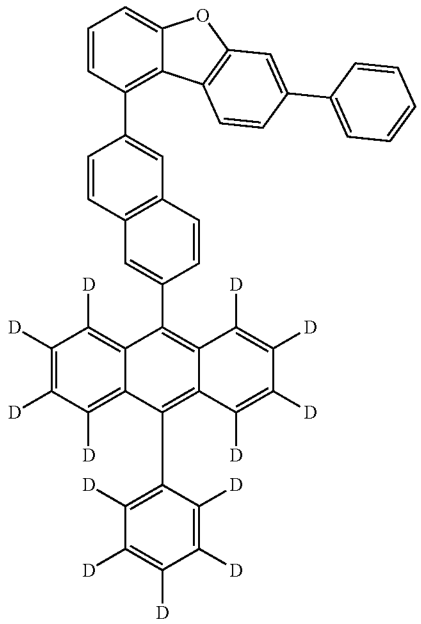
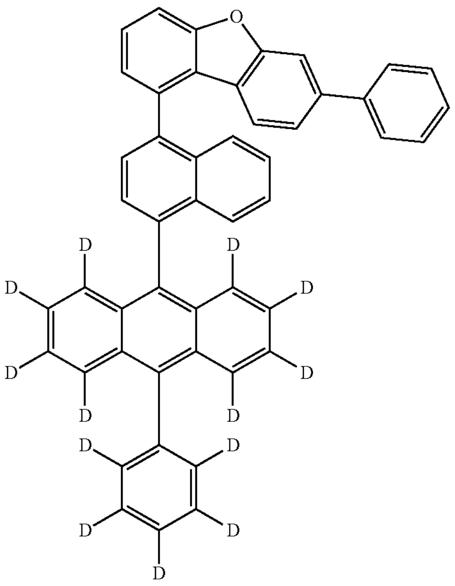
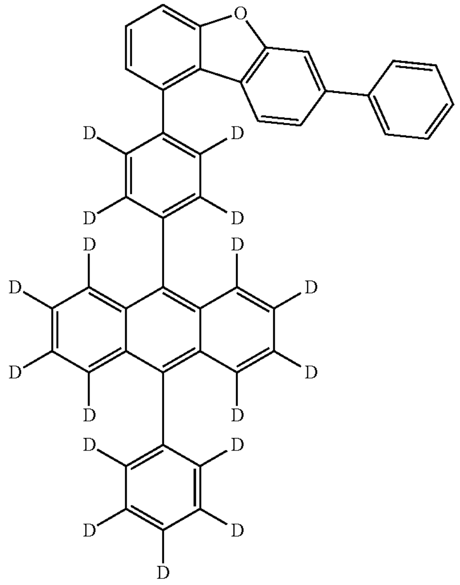

-continued
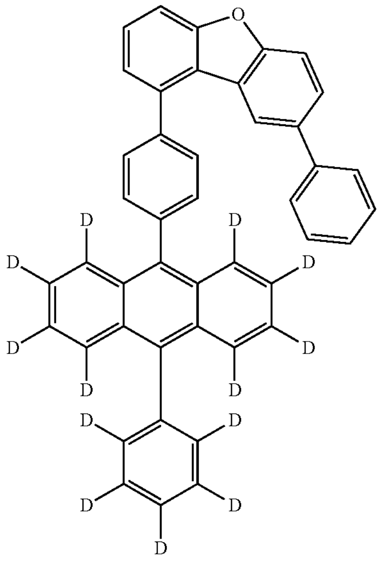
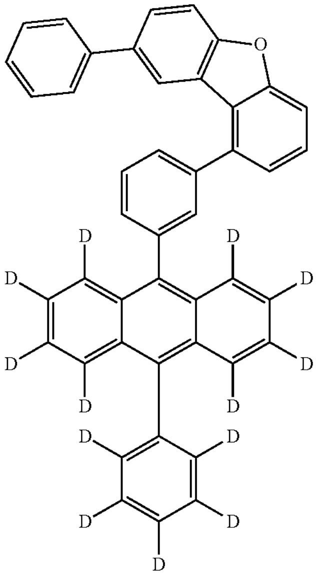
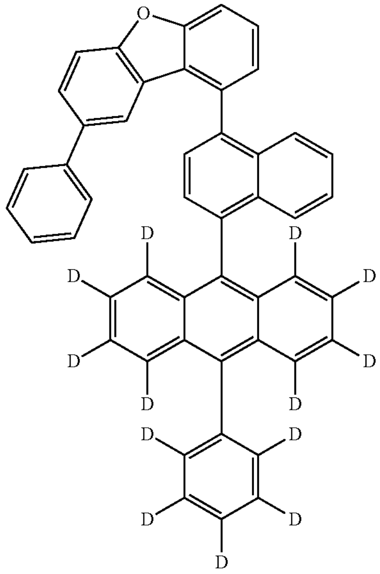
-continued
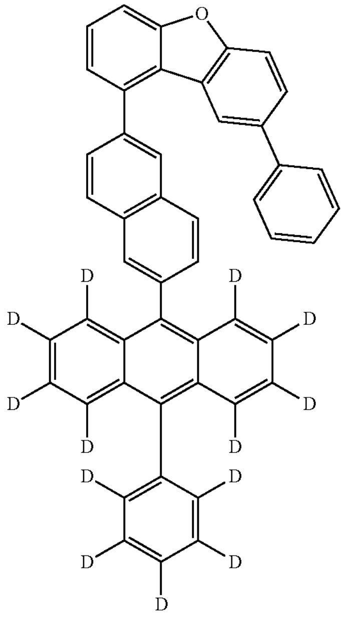
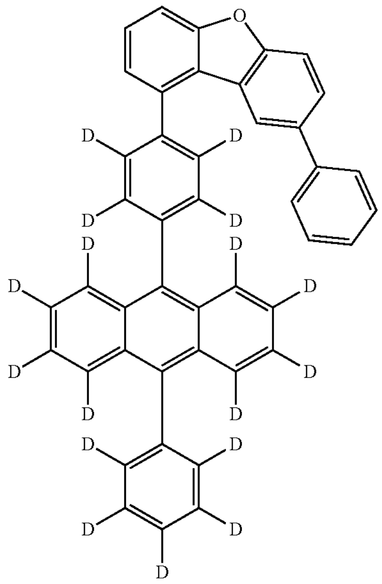

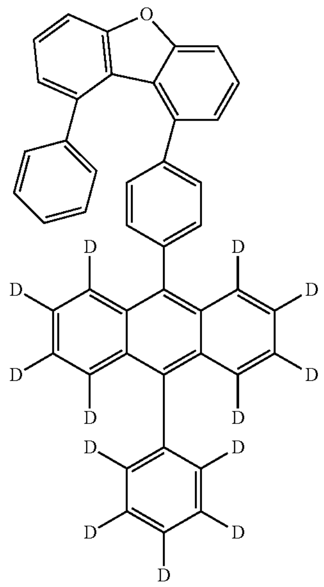
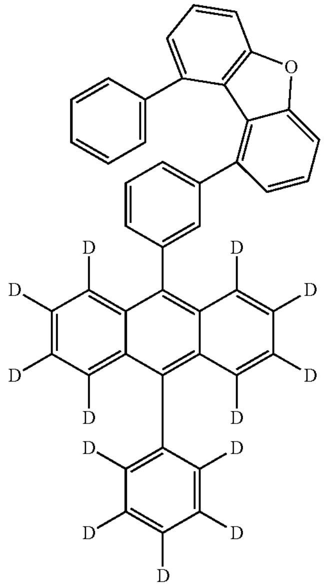
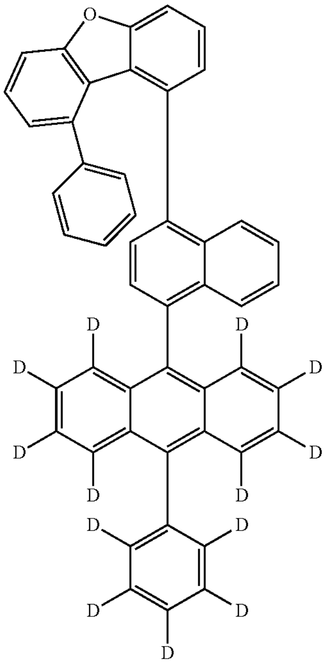
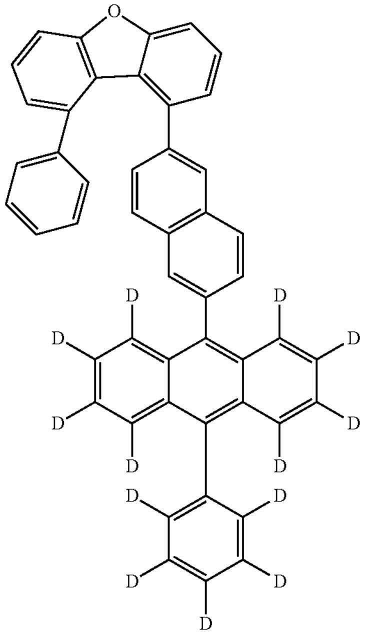

-continued
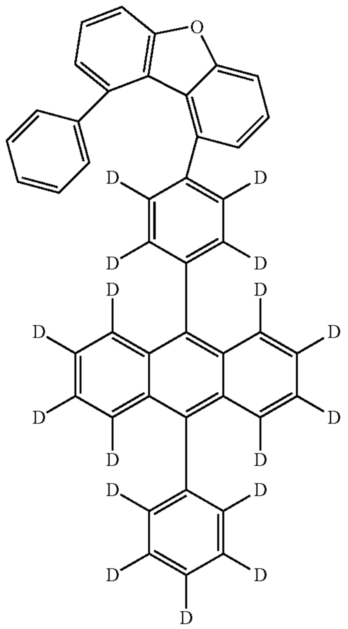 [SMILES: [2H]c1c([2H])c([2H])c(-c2c3c([2H])c([2H])c([2H])c([2H])c3c(-c3c([2H])c([2H])c(-c4cccc5oc6cccc(-c7ccccc7)c6c45)c([2H])c3[2H])c3c([2H])c([2H])c([2H])c([2H])c23)c([2H])c1[2H]]
-continued
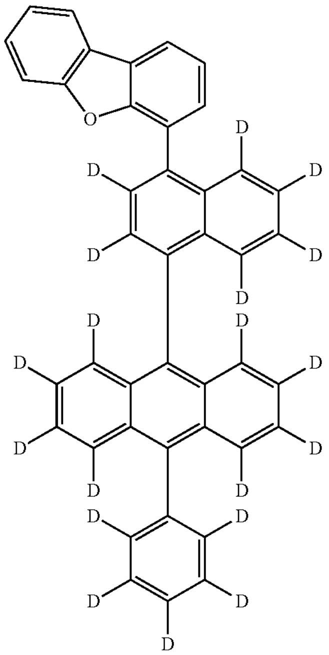
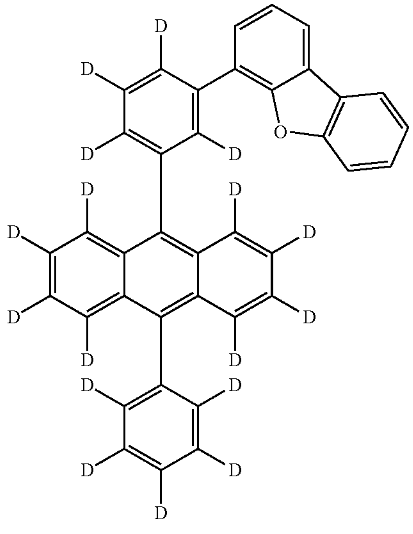
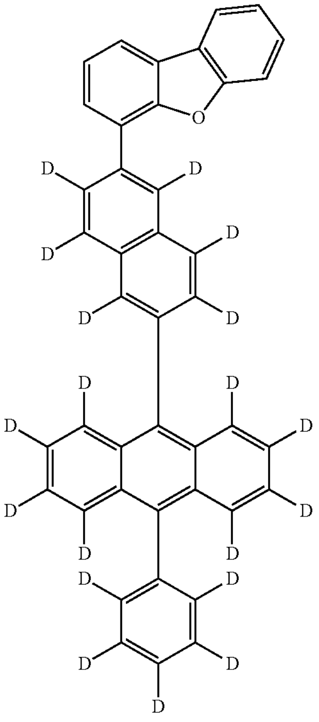

-continued
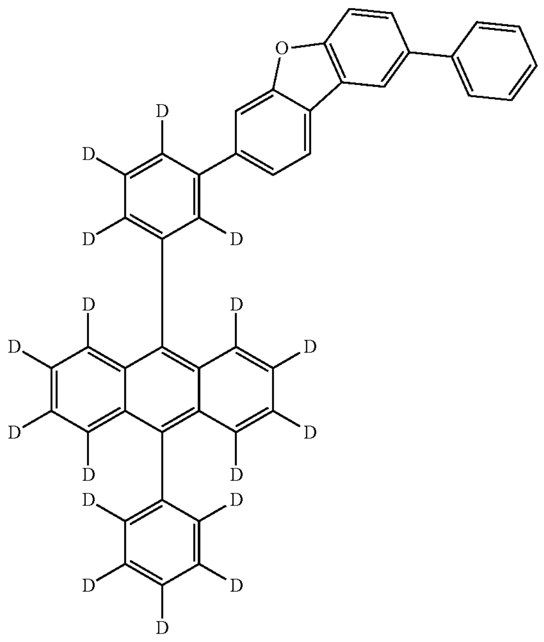
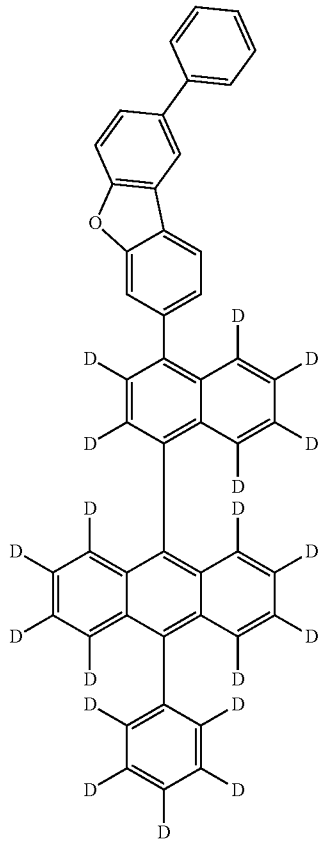
-continued
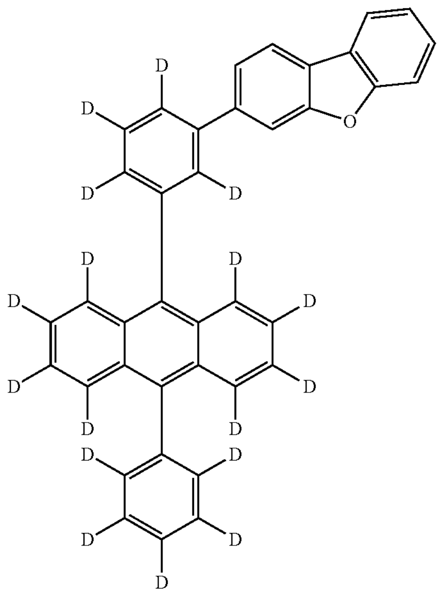
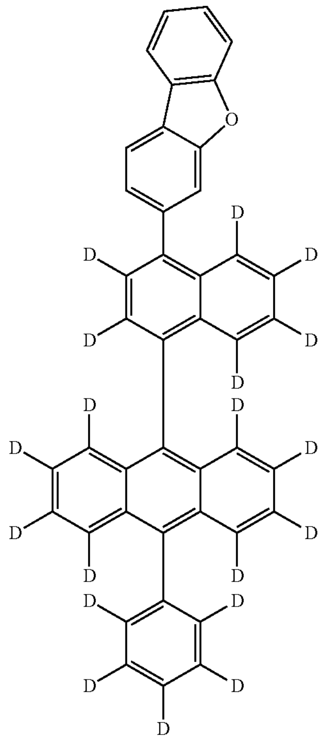

-continued
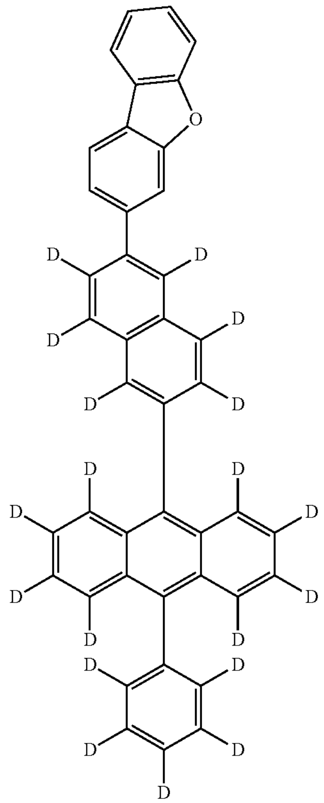
-continued
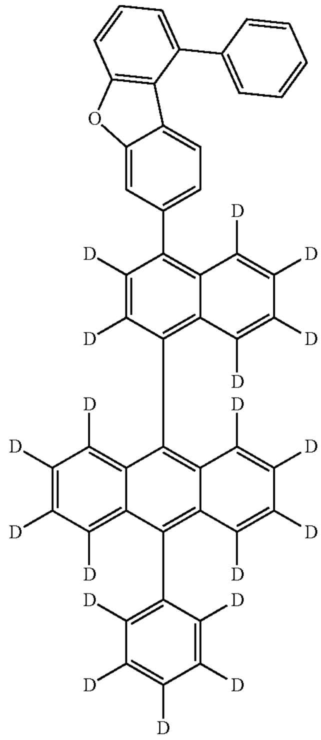
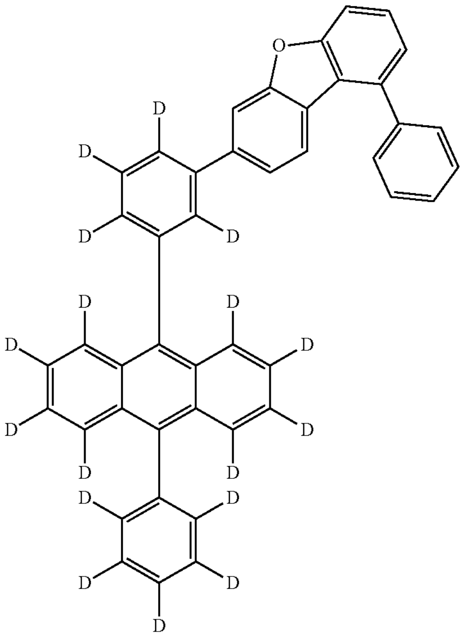
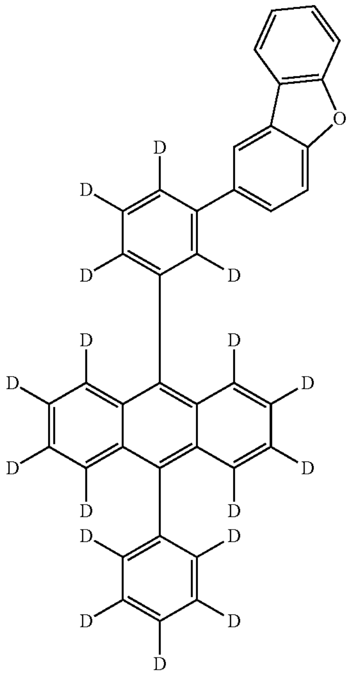

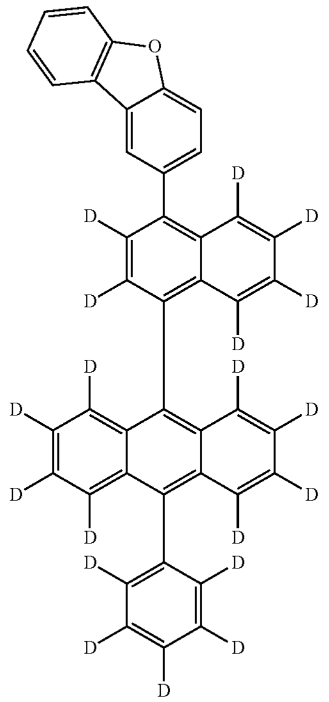
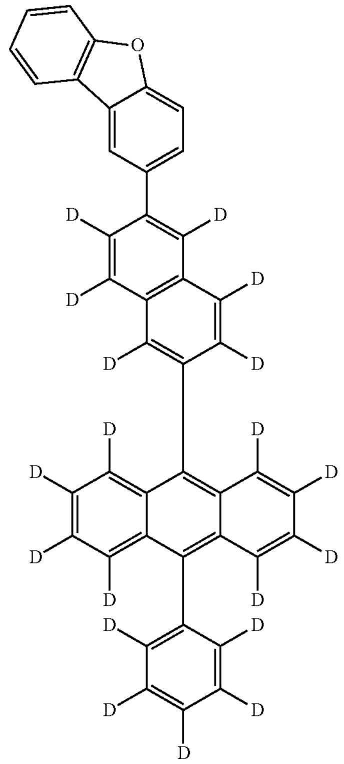
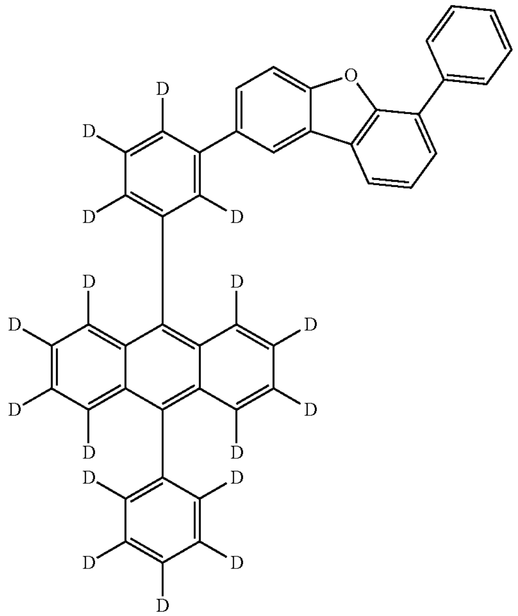
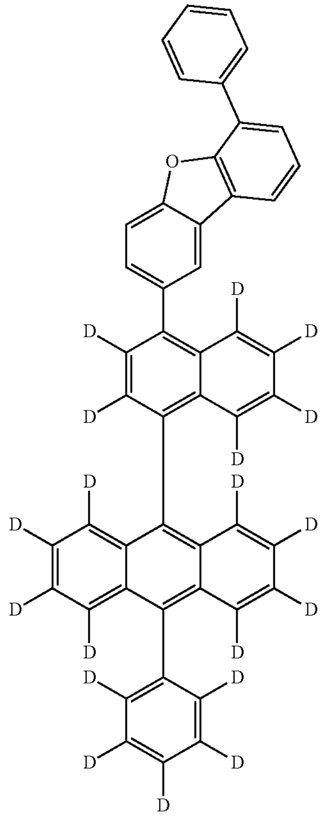

-continued
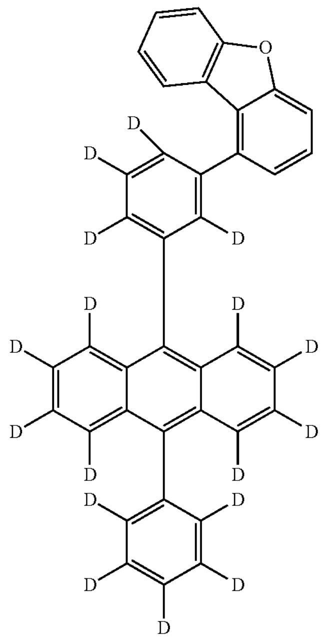
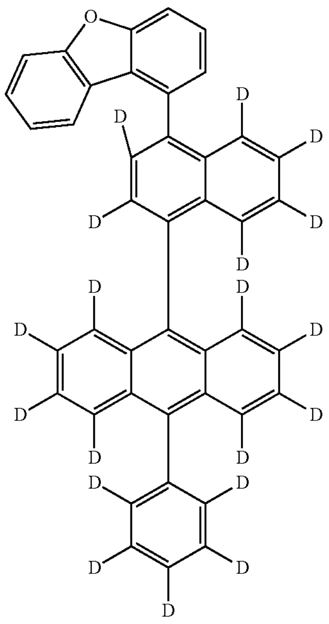
-continued
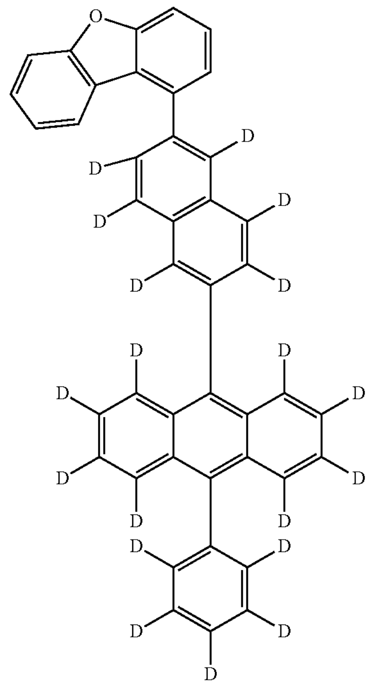
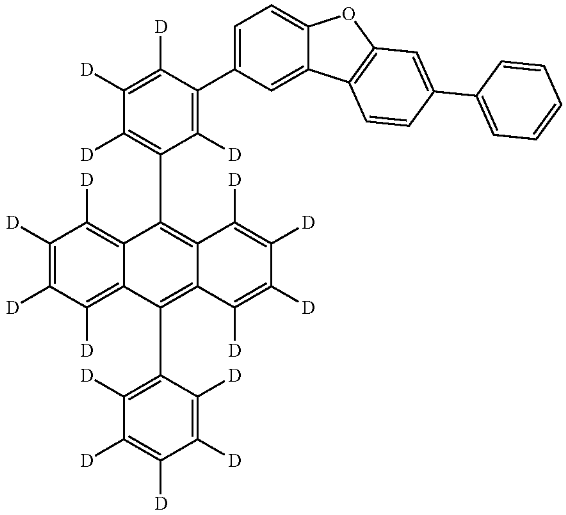

-continued
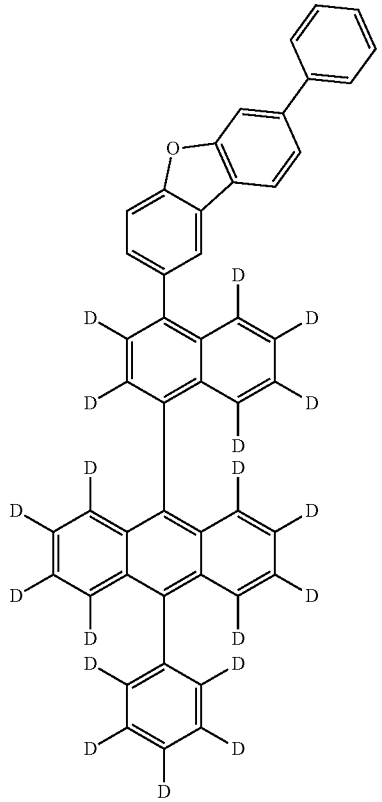
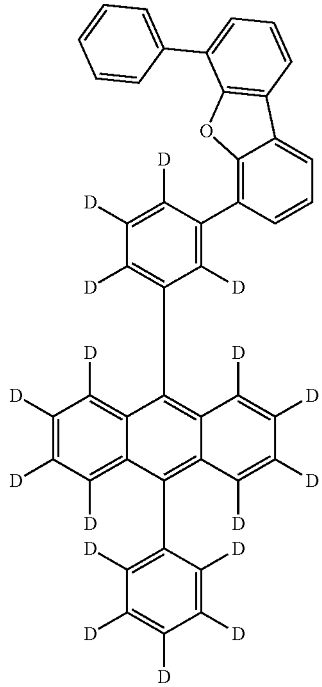
-continued
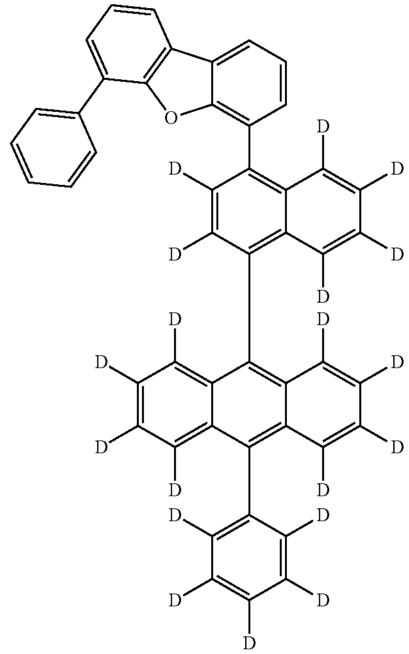
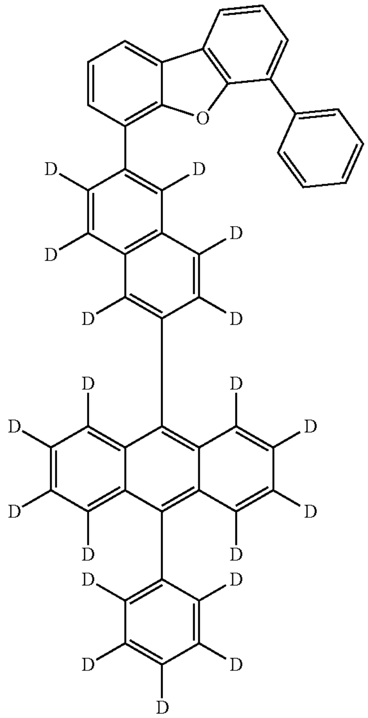

-continued
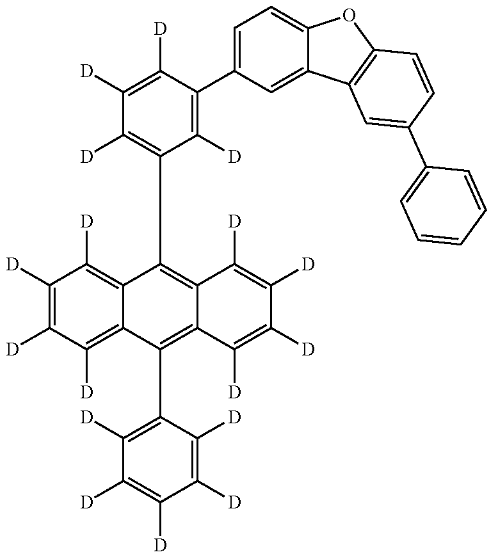
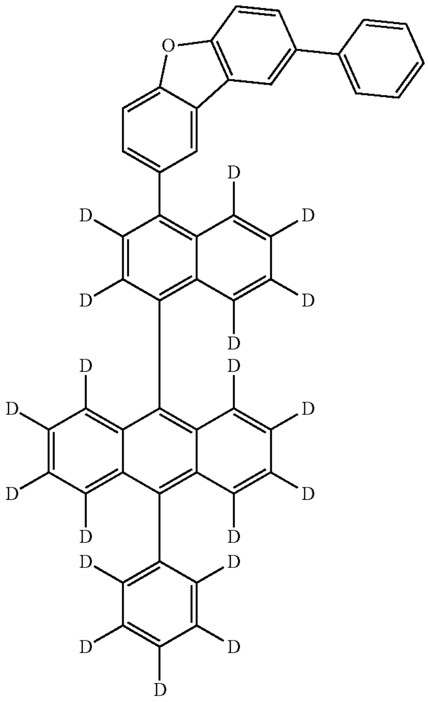
-continued
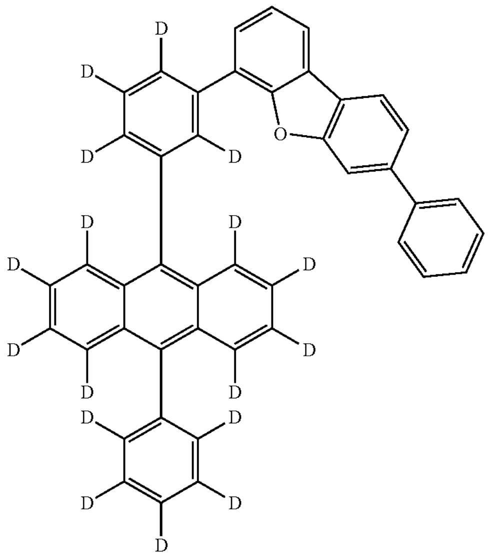
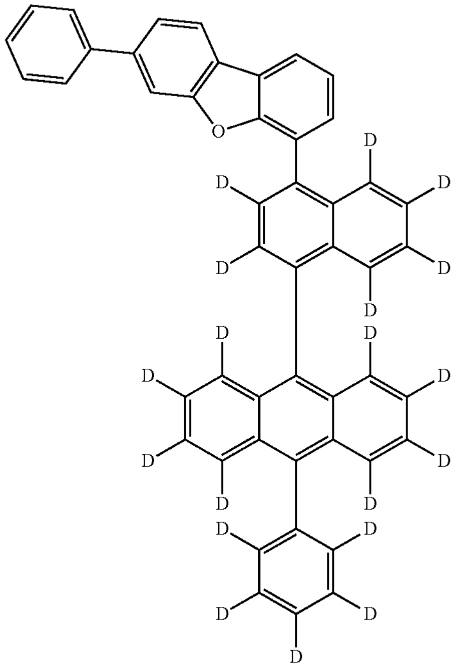

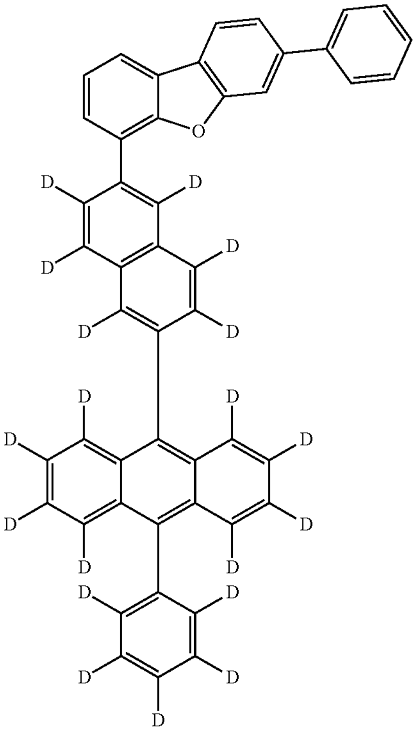
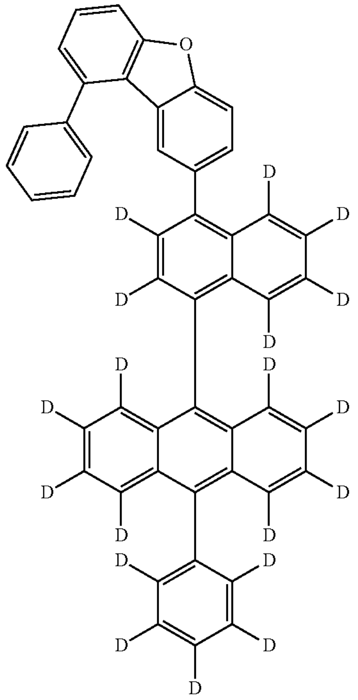
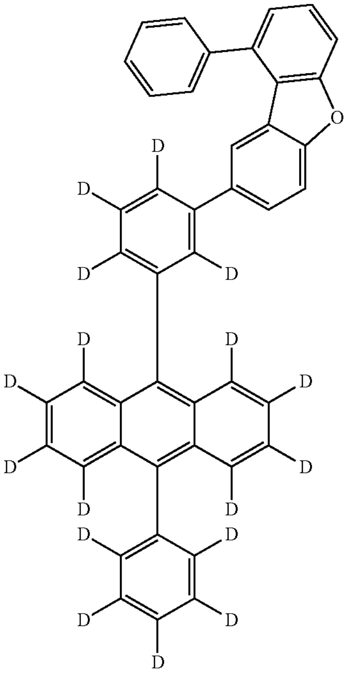
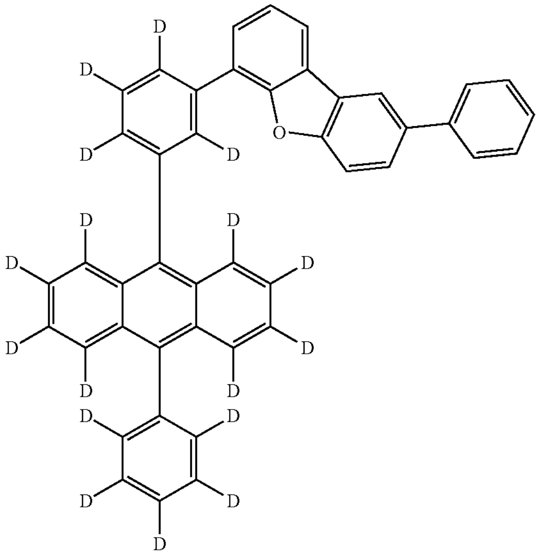

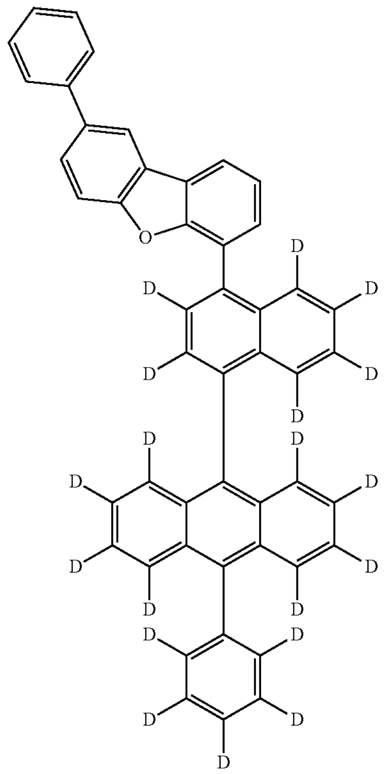
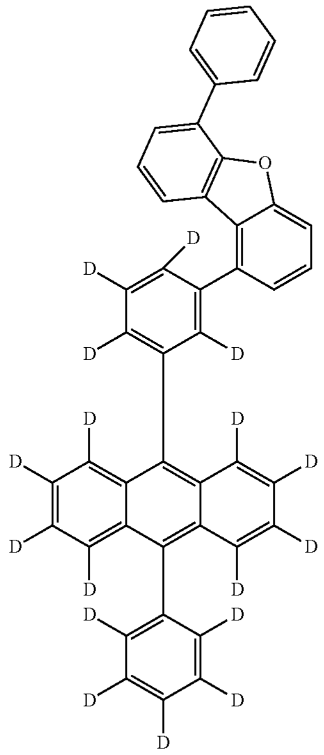
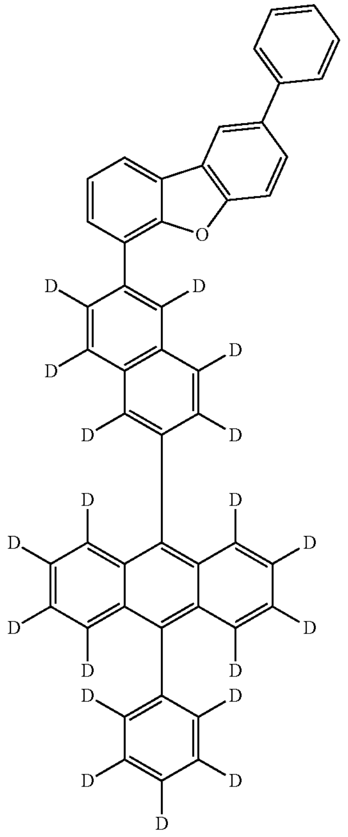
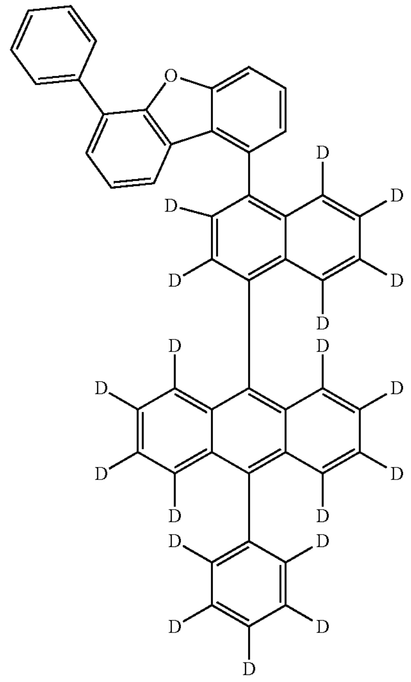

-continued
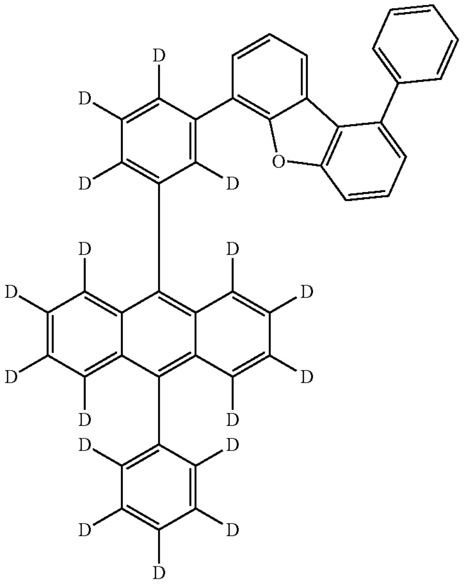
-continued
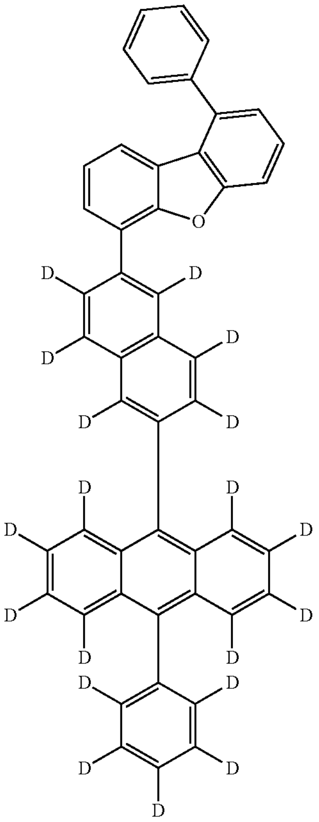
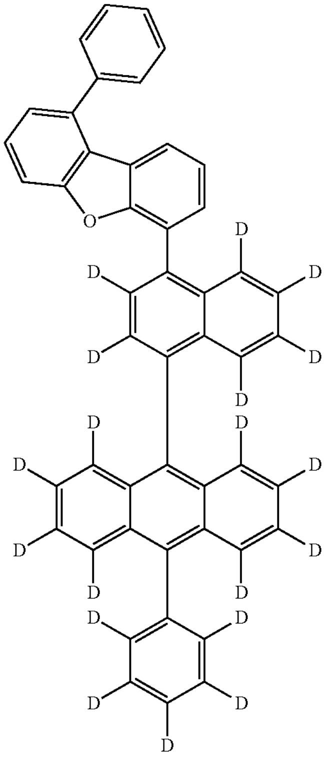
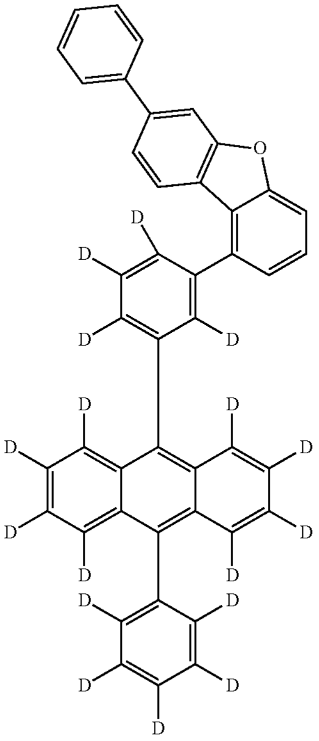

-continued
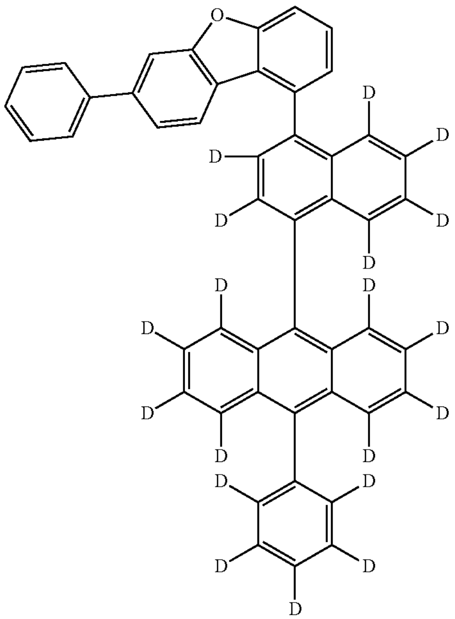
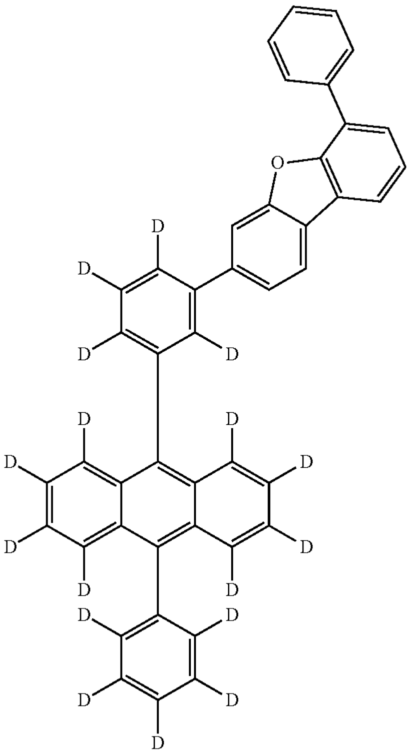
-continued
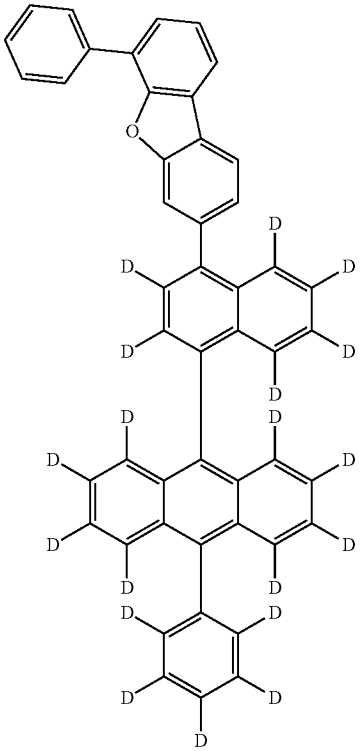
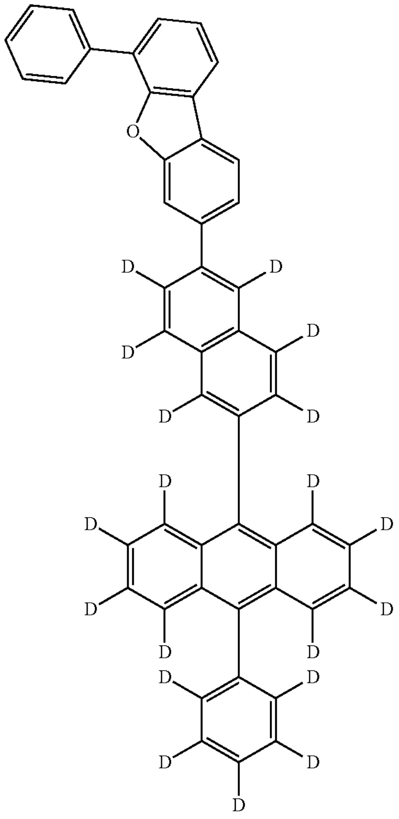

-continued
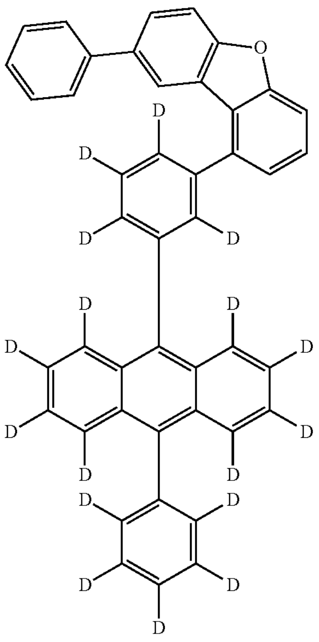
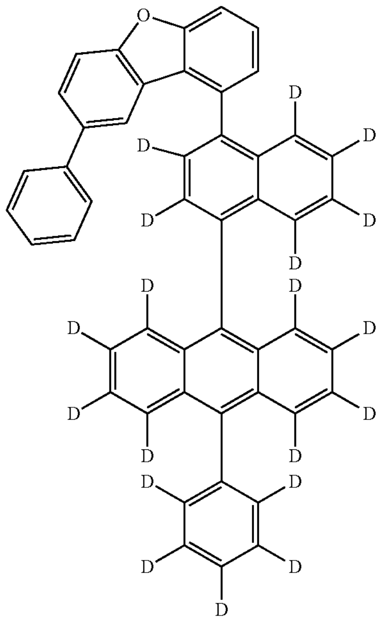
-continued
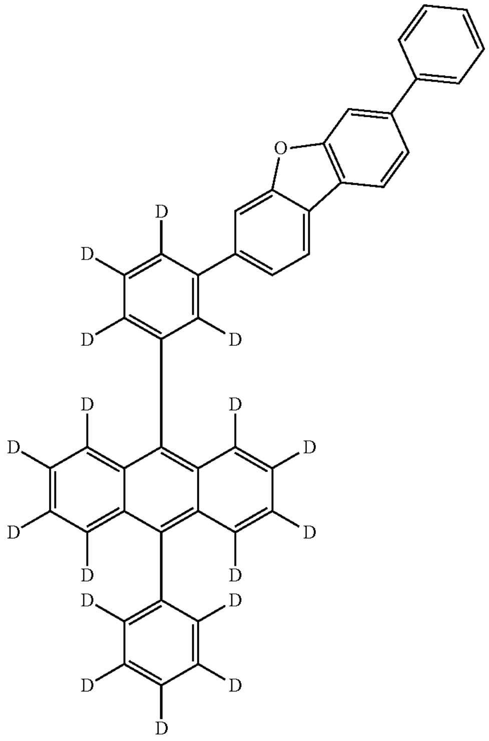
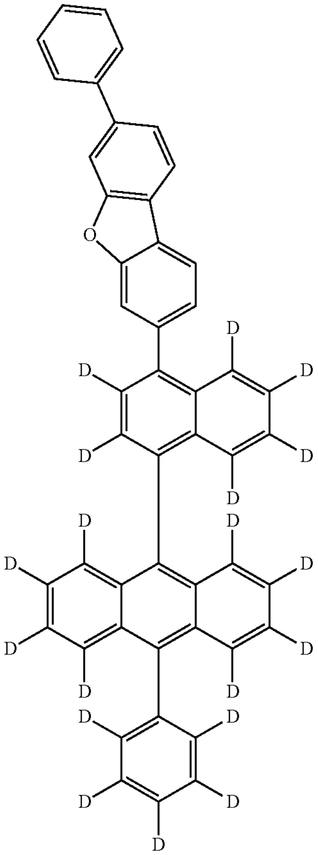

-continued
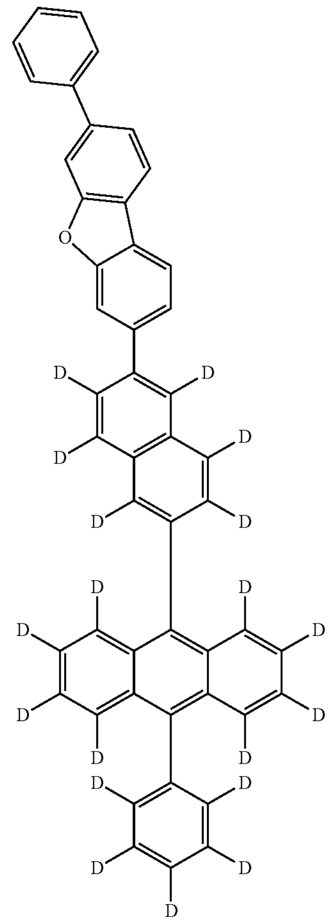
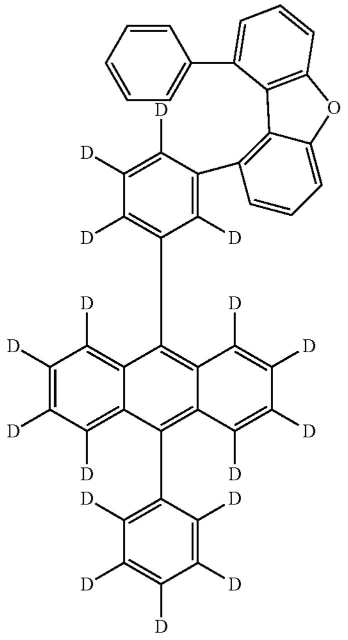
-continued
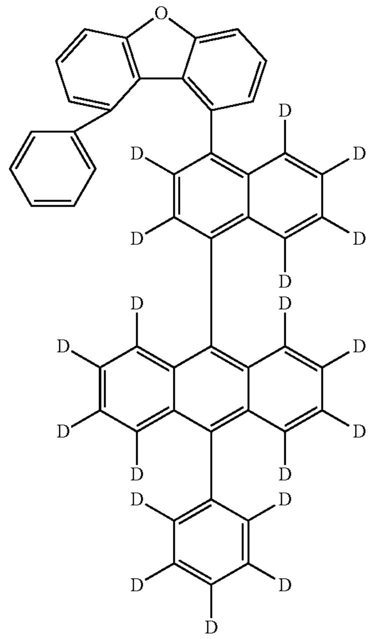
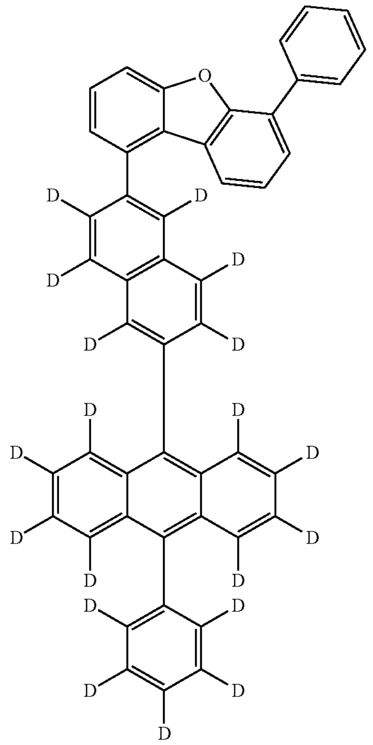

-continued
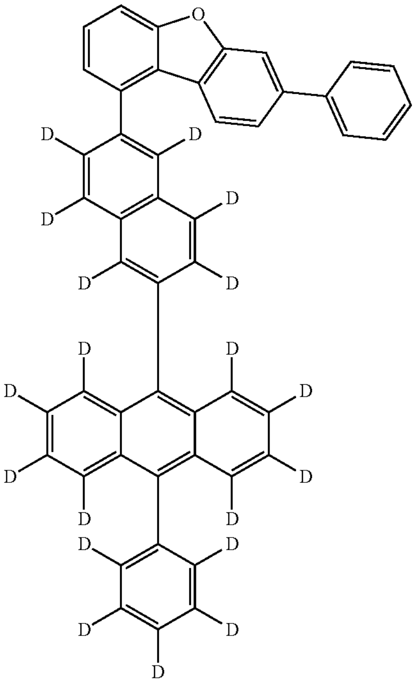
-continued
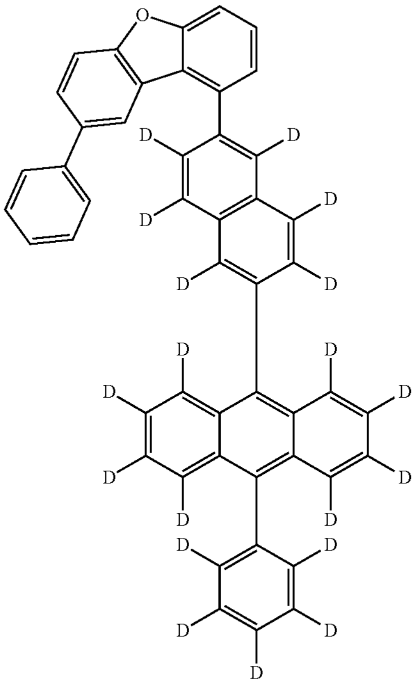
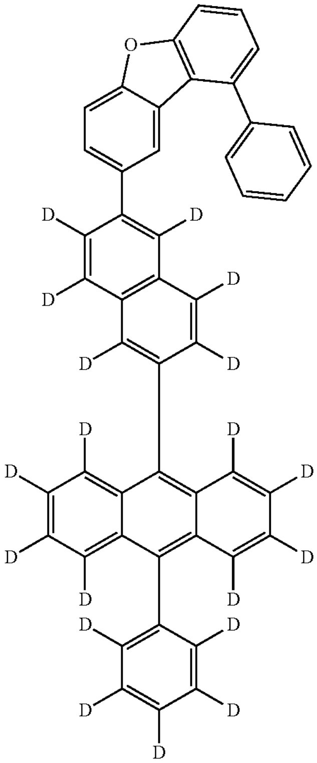
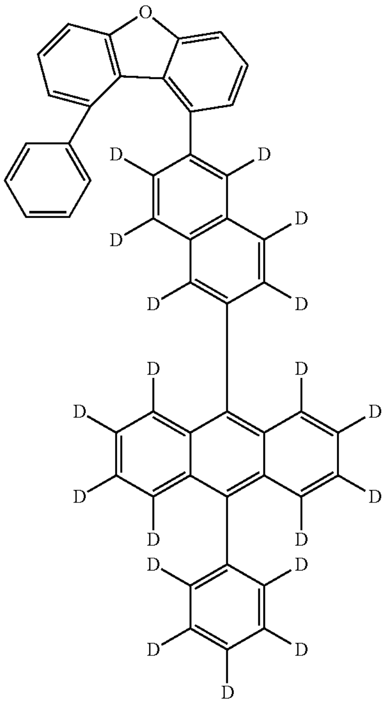

-continued
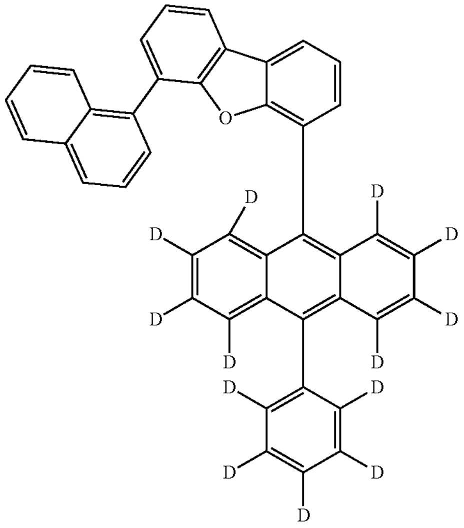
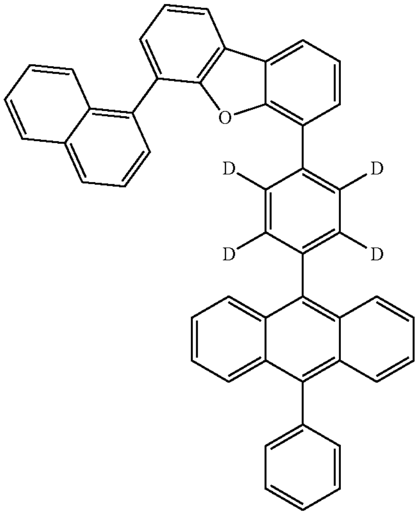
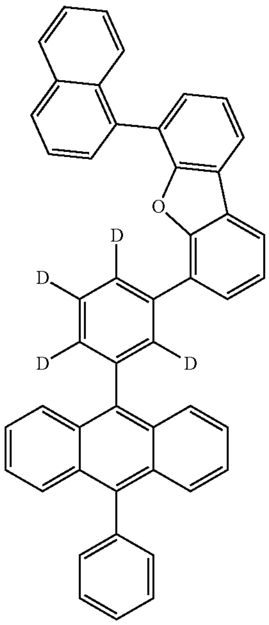
-continued
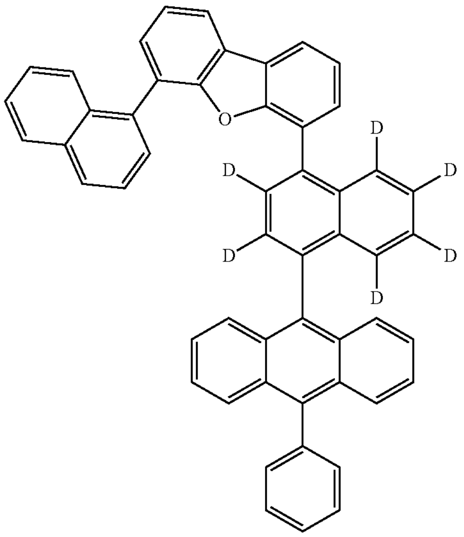
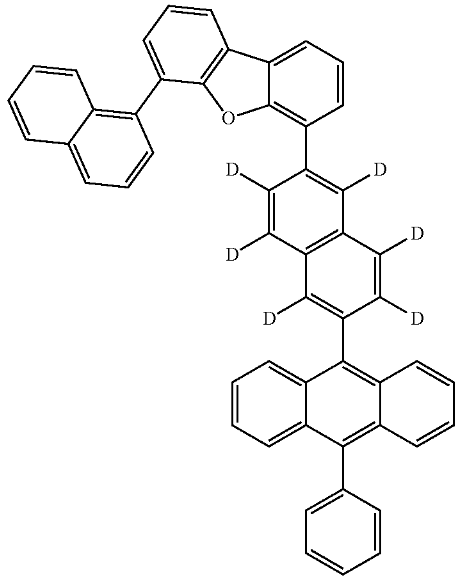
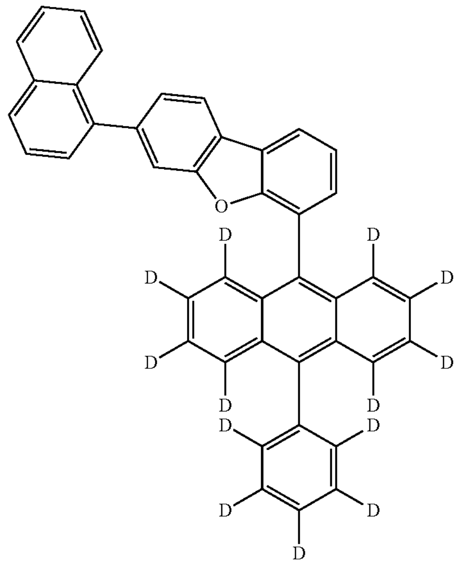

-continued
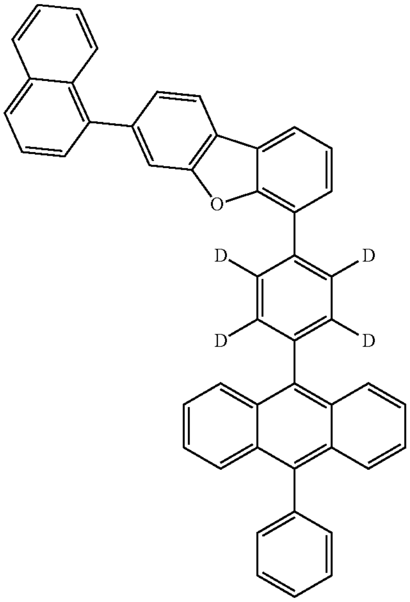
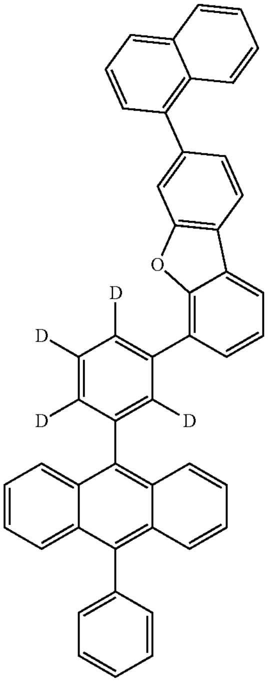
-continued
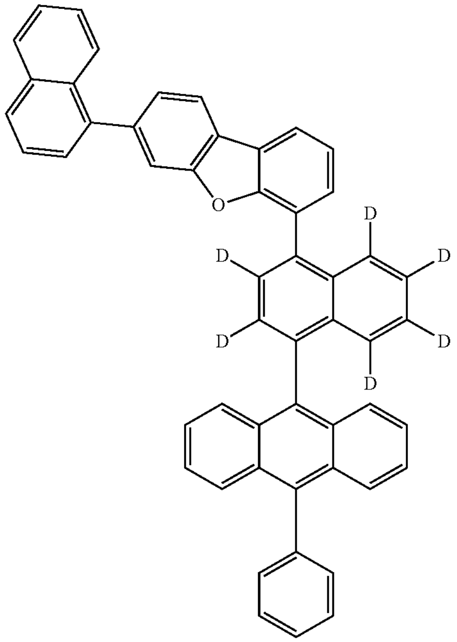
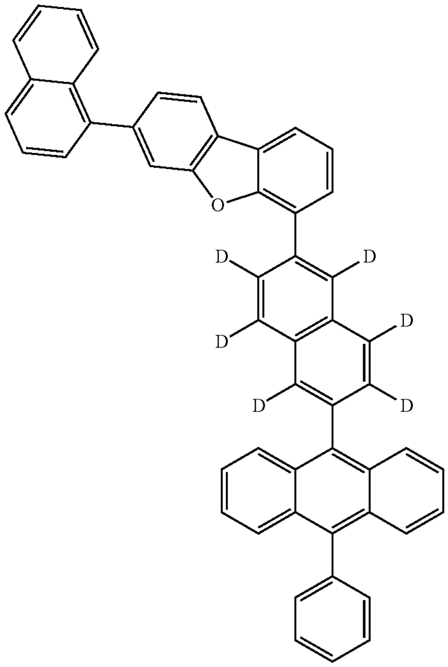

-continued
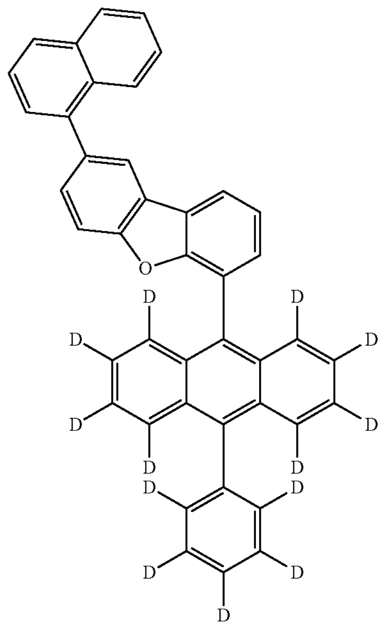
-continued
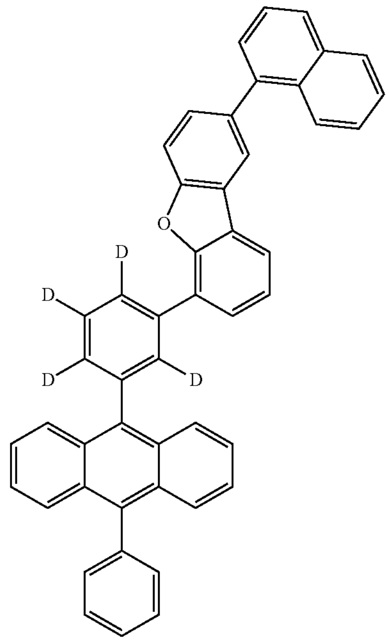
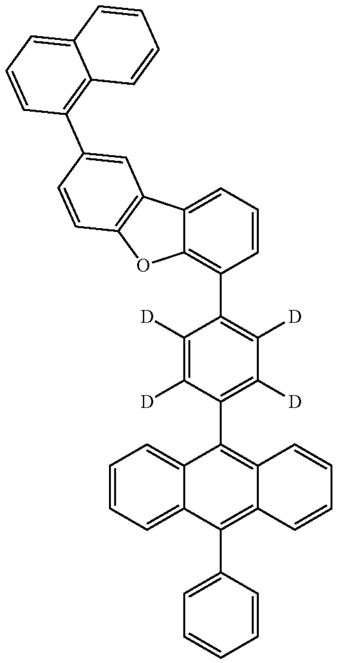
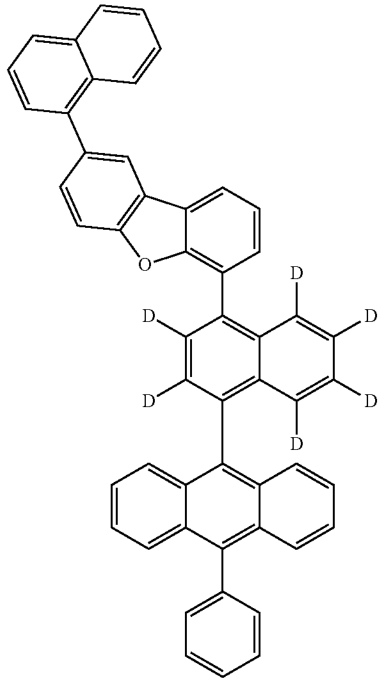

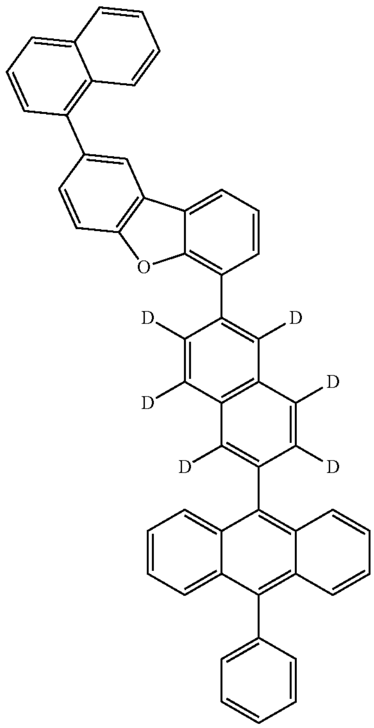
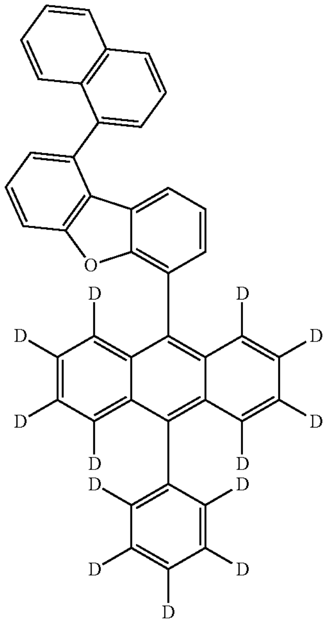
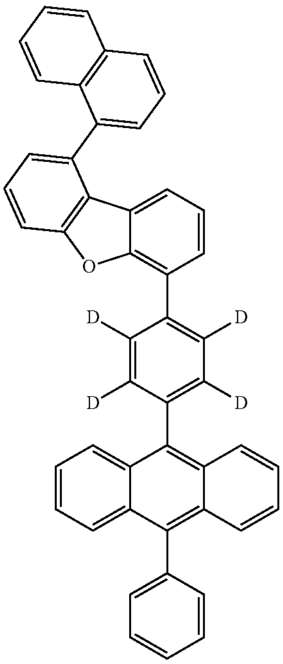
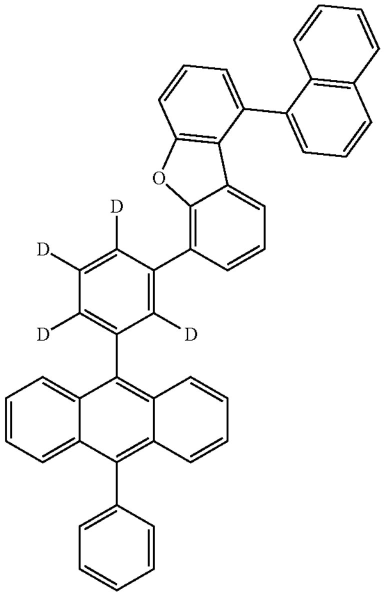

-continued
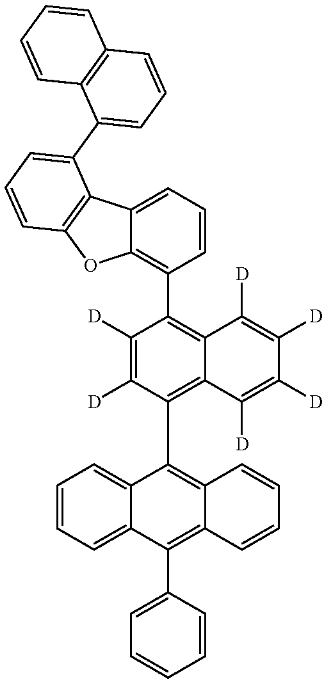
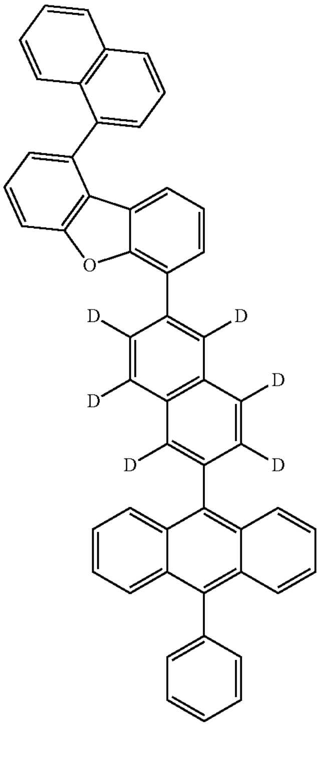
-continued
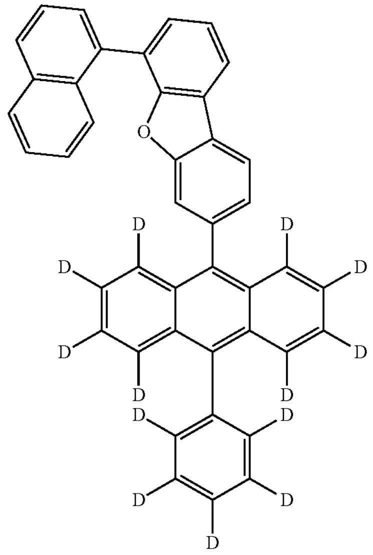
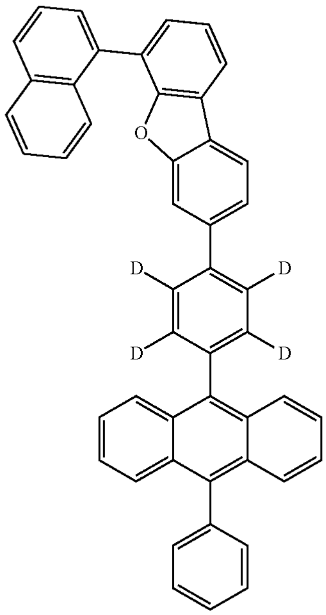

-continued
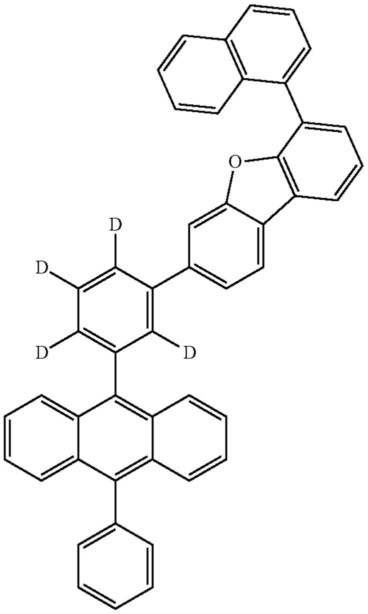
-continued
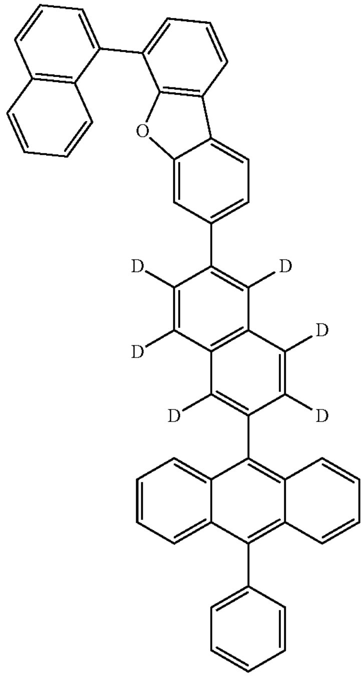
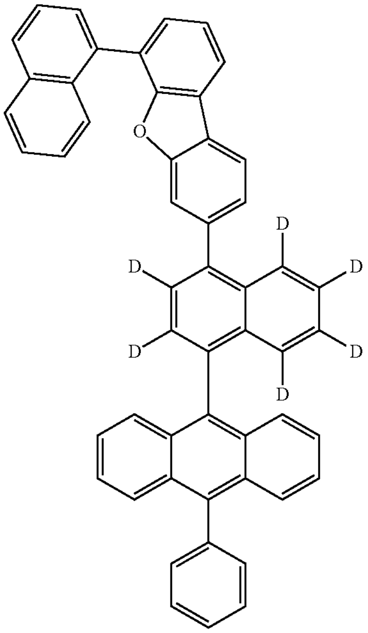
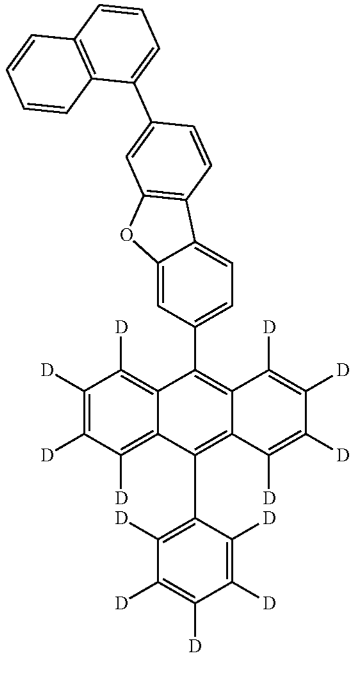

-continued
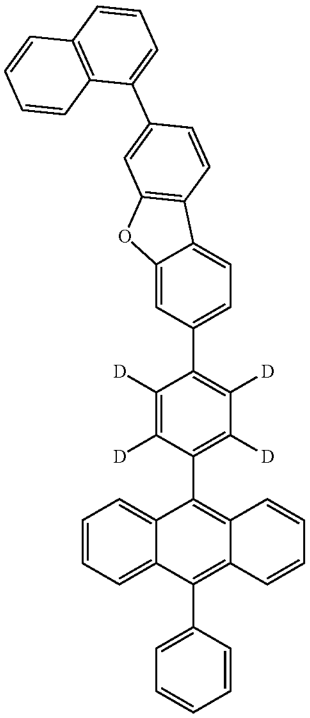
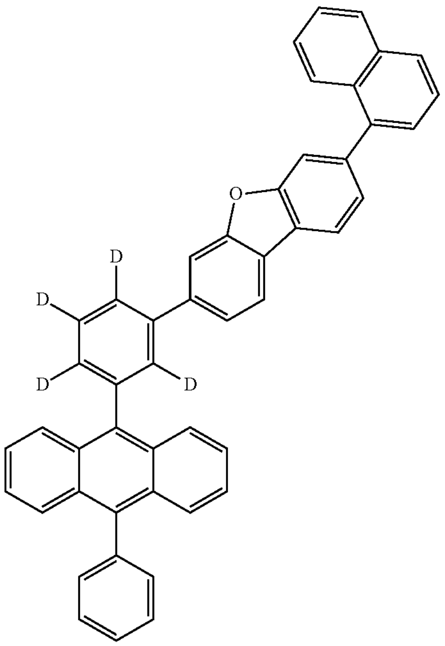
-continued
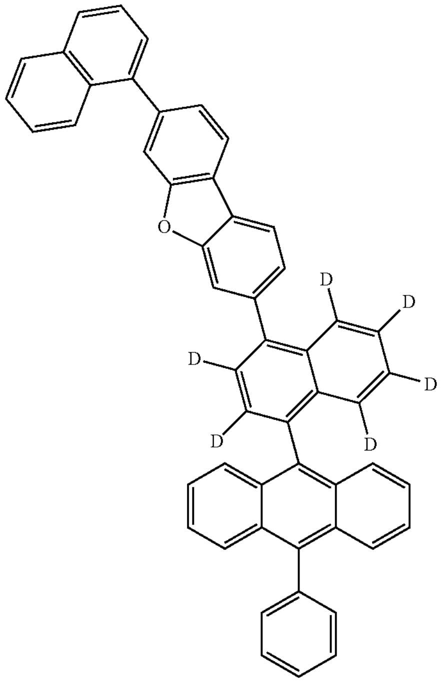
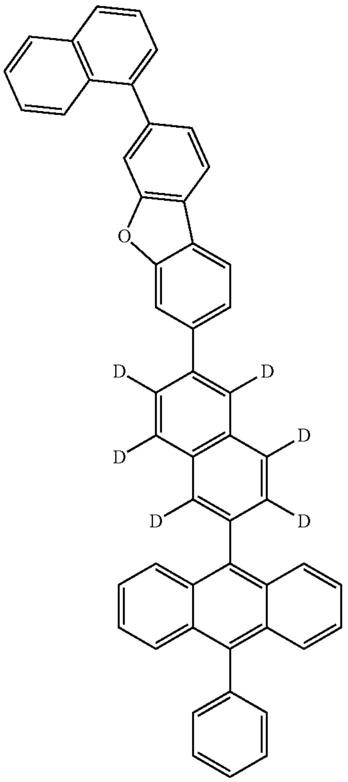

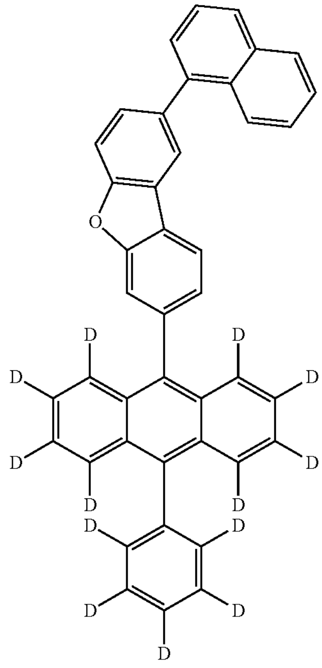
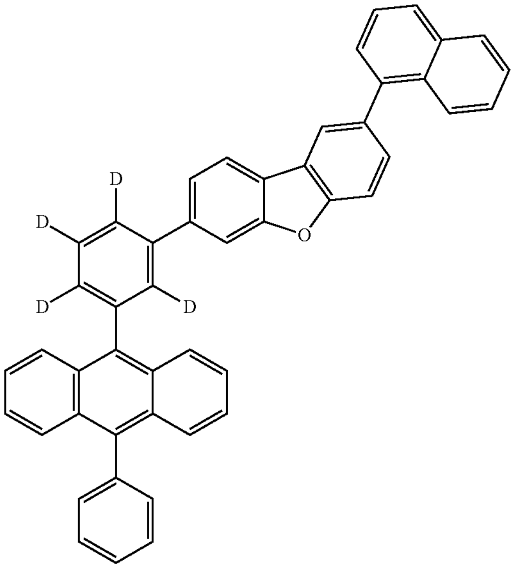
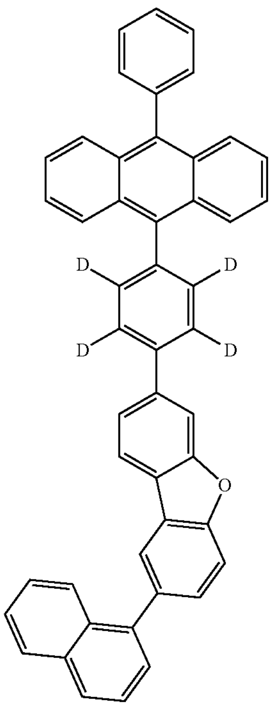
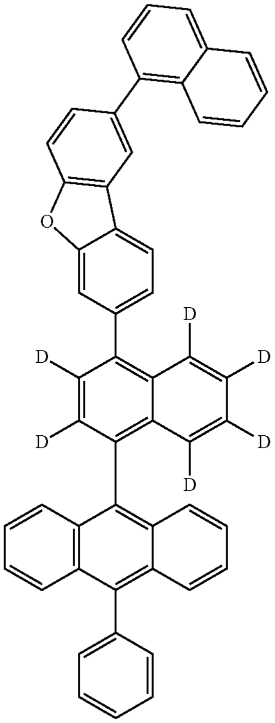

-continued
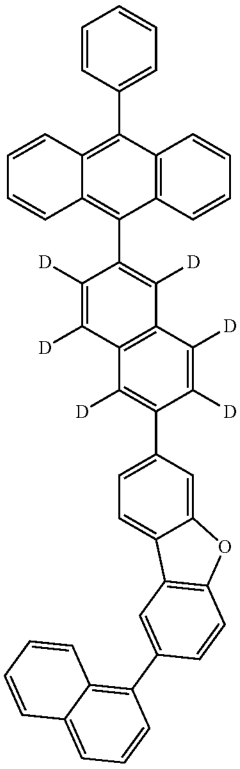
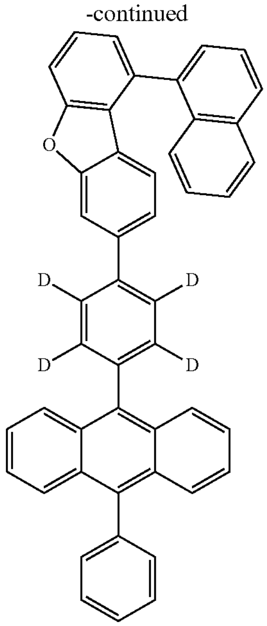
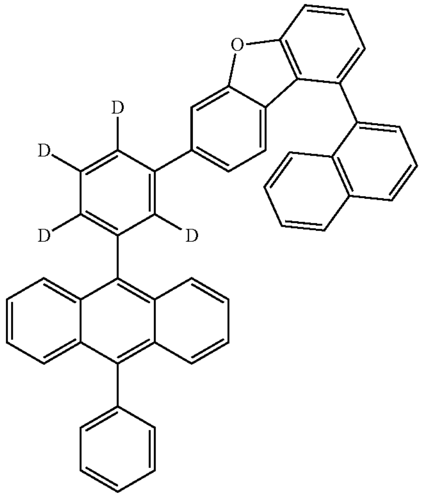
-continued
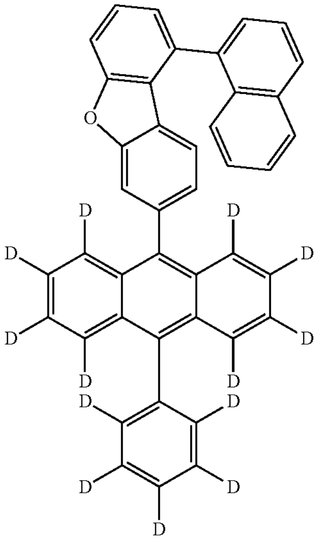
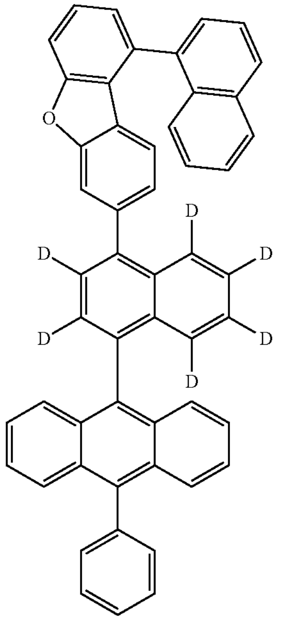

-continued
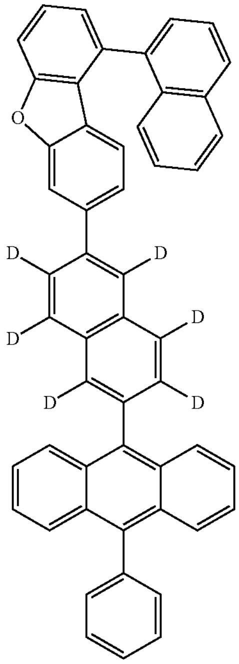
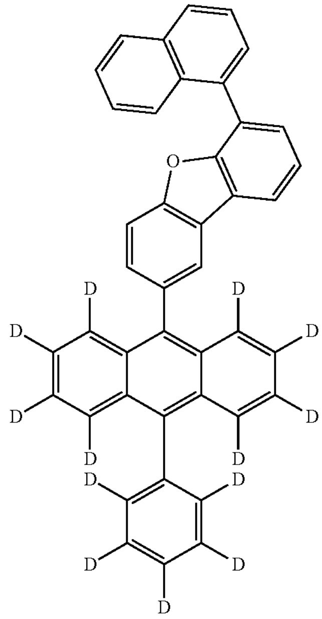
-continued
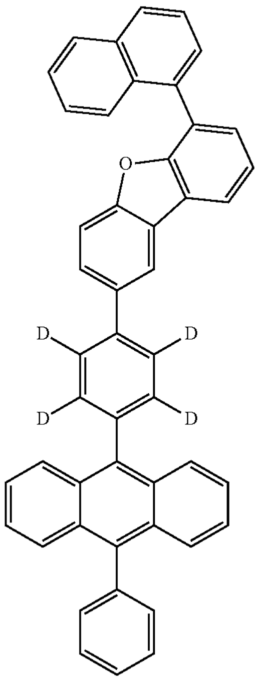
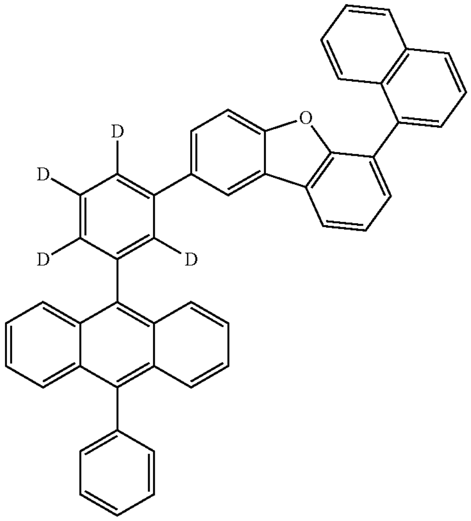

-continued
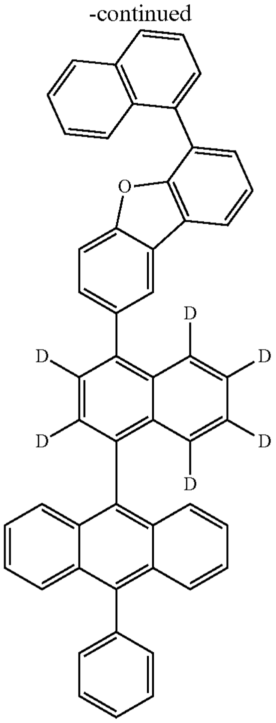
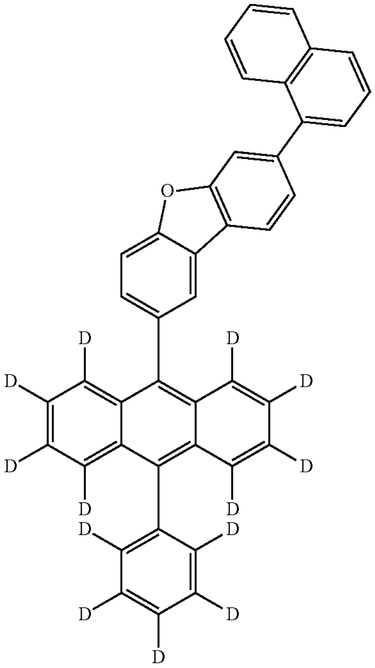
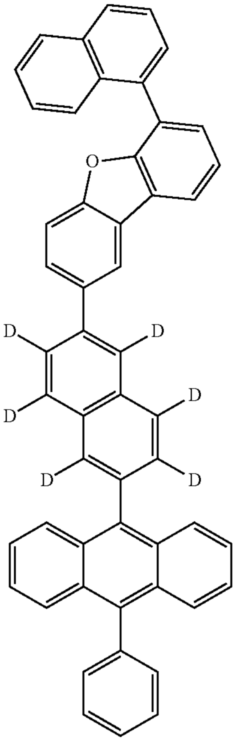
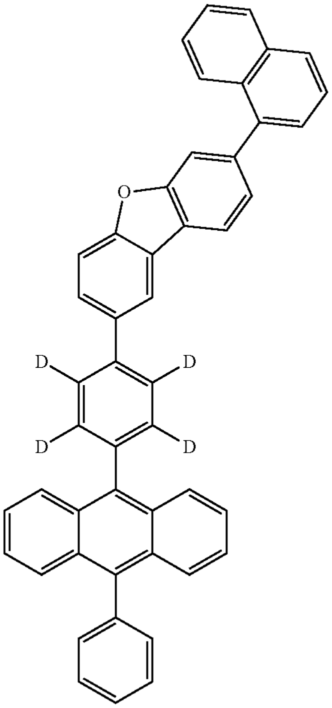
-continued

-continued
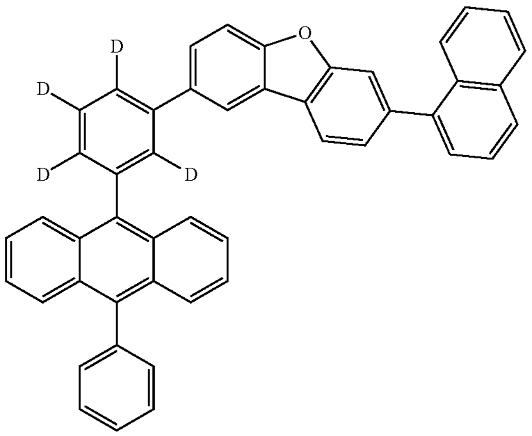
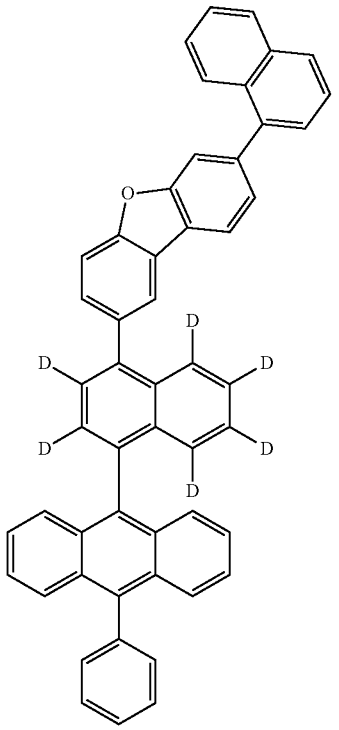
-continued
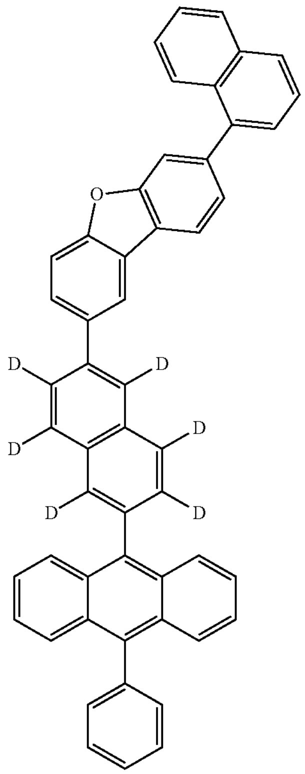 [SMILES: [2H]c1c(-c2c3ccccc3c(-c3ccccc3)c3ccccc23)c([2H])c2c([2H])c([2H])c(-c3ccc4oc5cc(-c6cccc7ccccc67)ccc5c4c3)c([2H])c2c1[2H]]
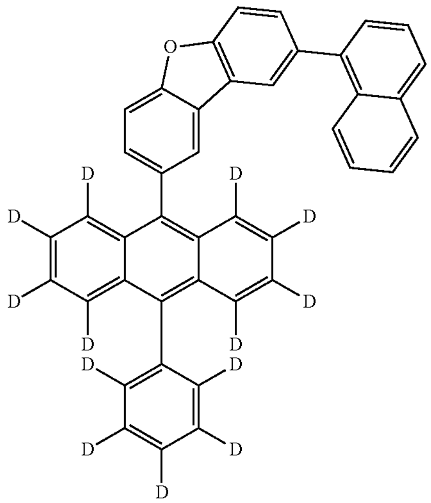

-continued
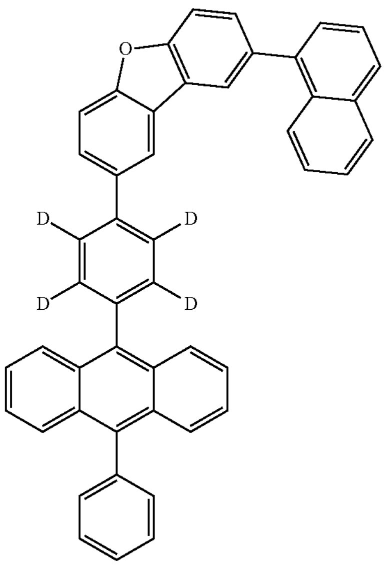
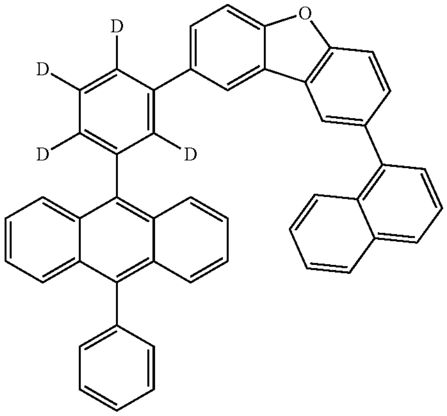
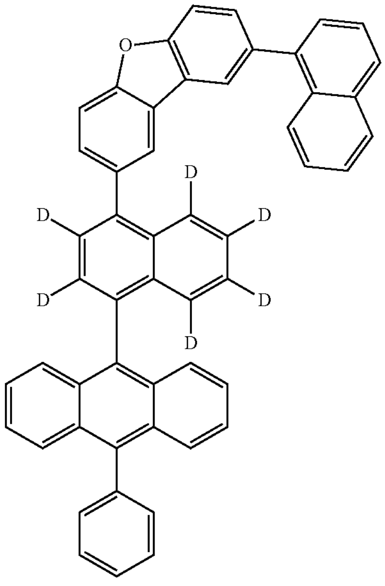
-continued
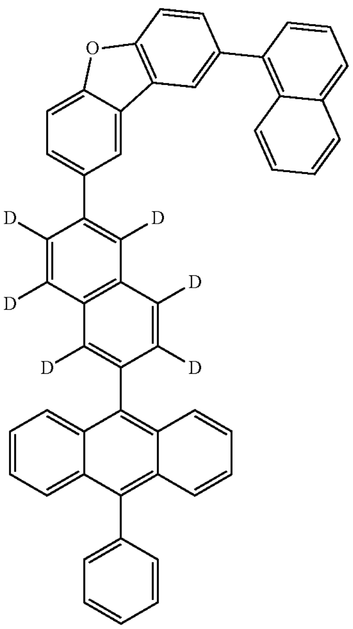
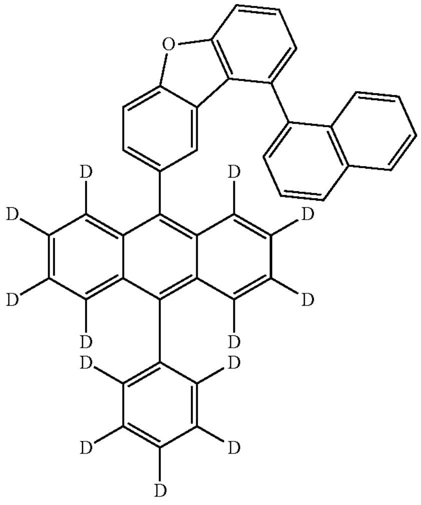
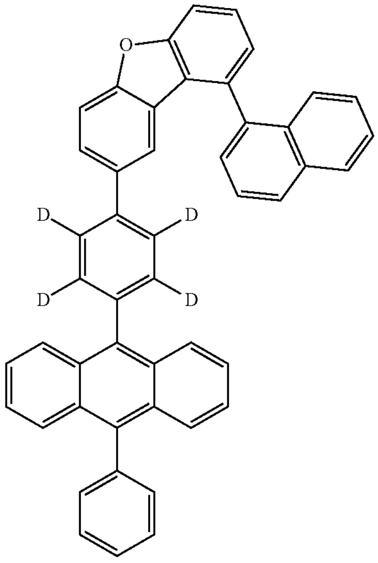

-continued
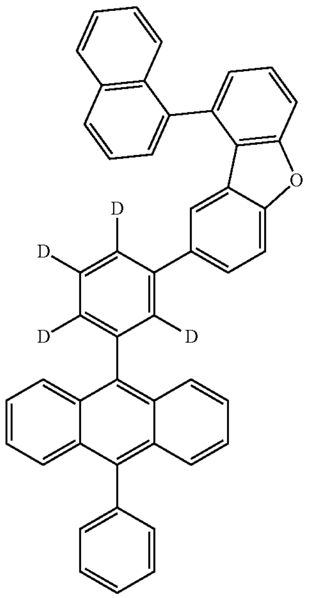
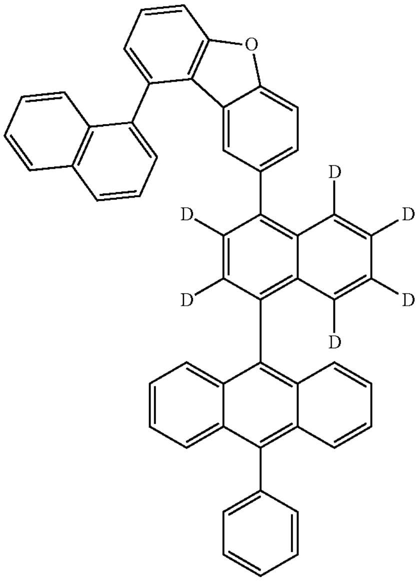
-continued
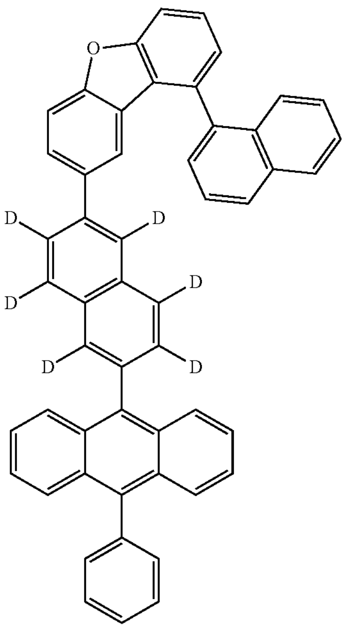
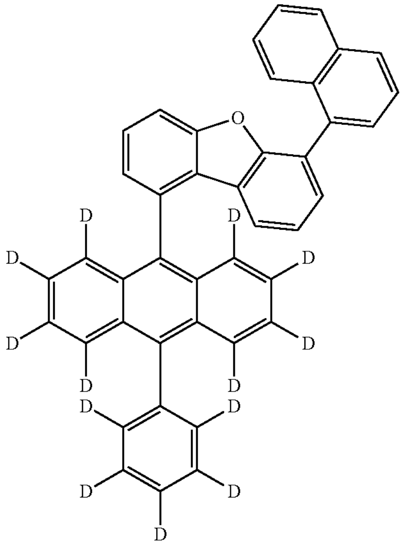

-continued
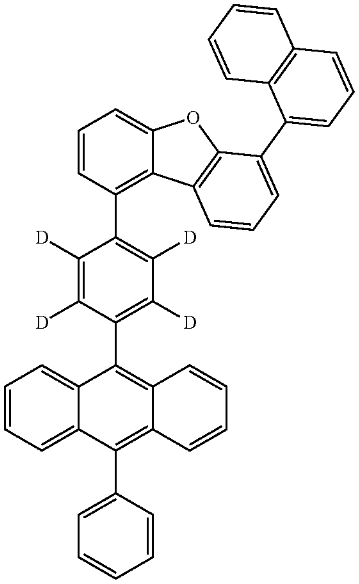
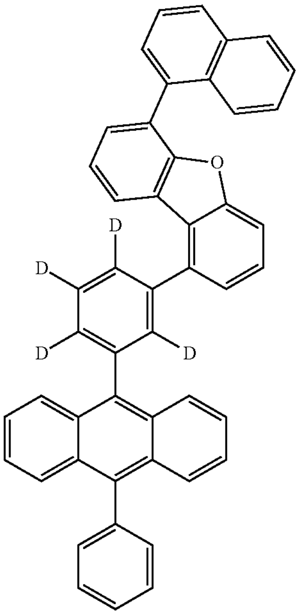
-continued
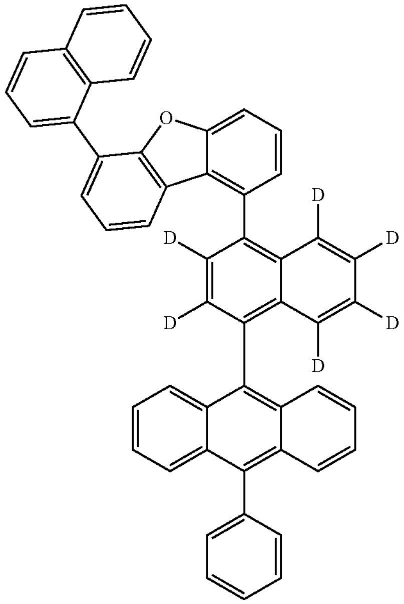
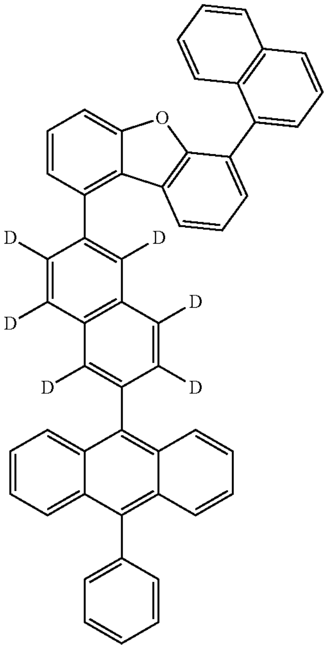
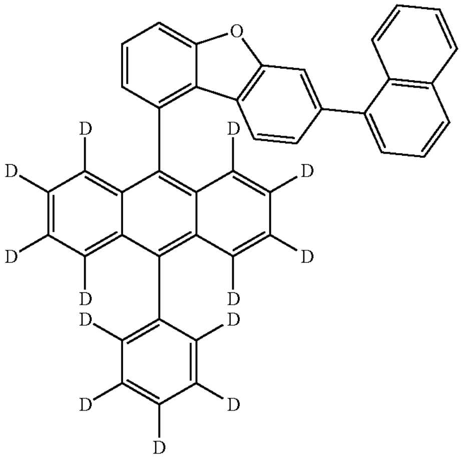 [SMILES: [2H]c1c([2H])c([2H])c(-c2c3c([2H])c([2H])c([2H])c([2H])c3c(-c3cccc4oc5cc(-c6cccc7ccccc67)ccc5c34)c3c([2H])c([2H])c([2H])c([2H])c23)c([2H])c1[2H]]

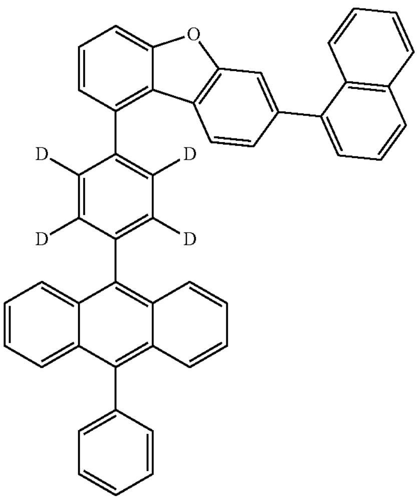
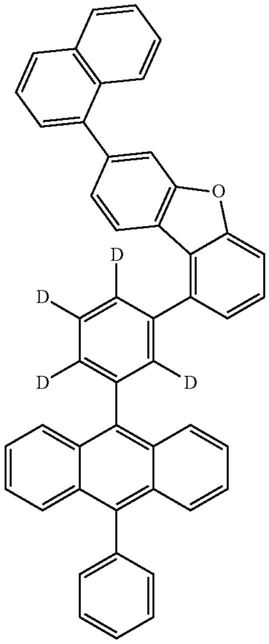
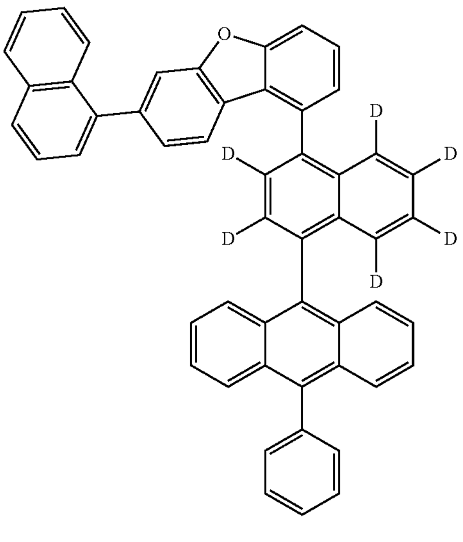
-continued
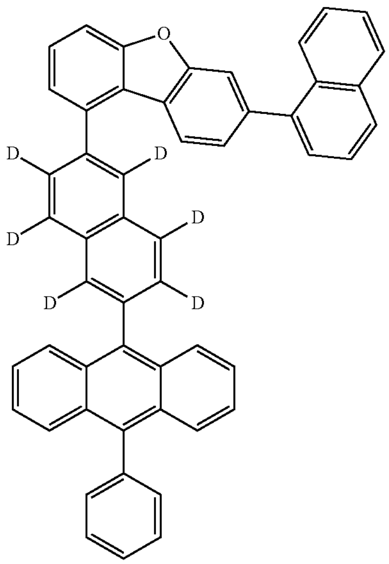
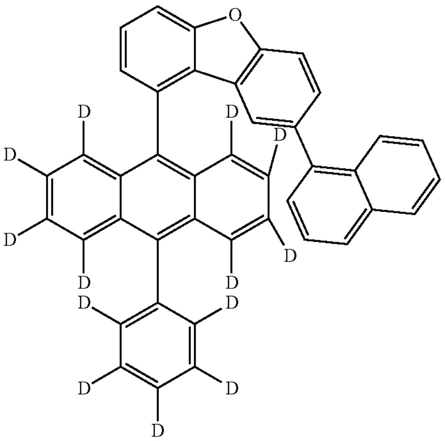
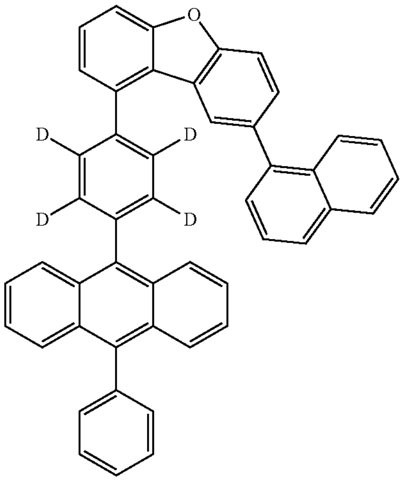

-continued
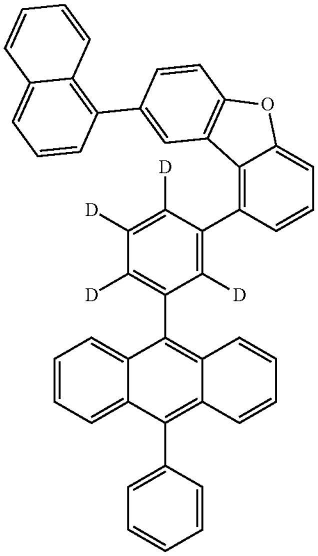
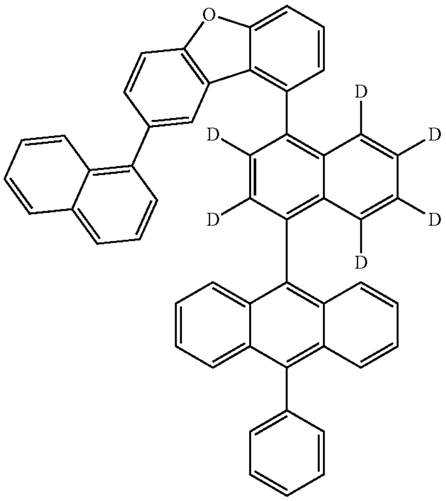
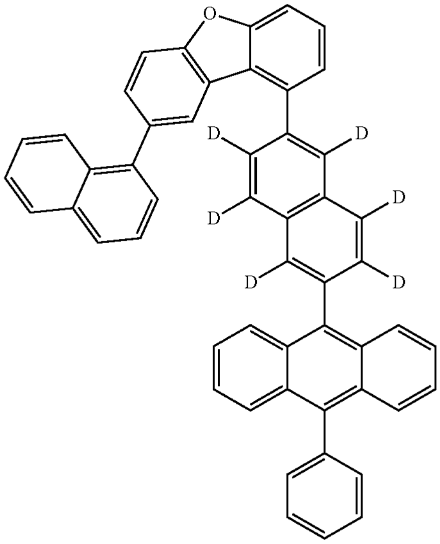
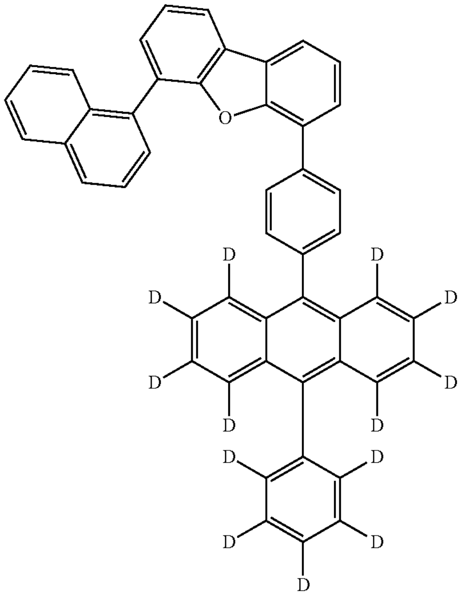
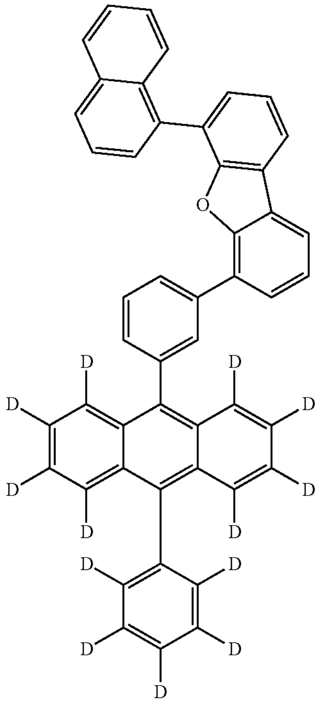

-continued
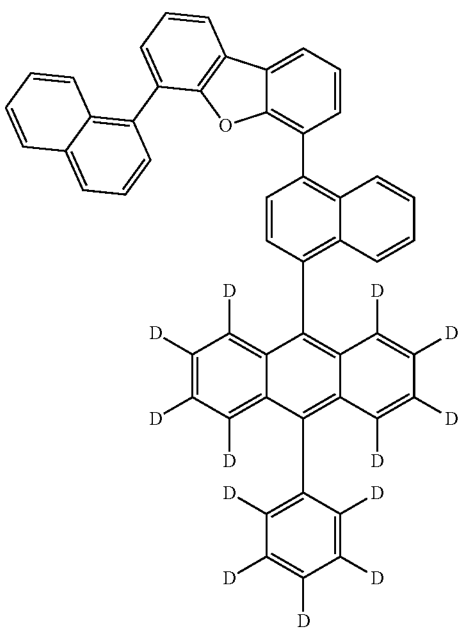
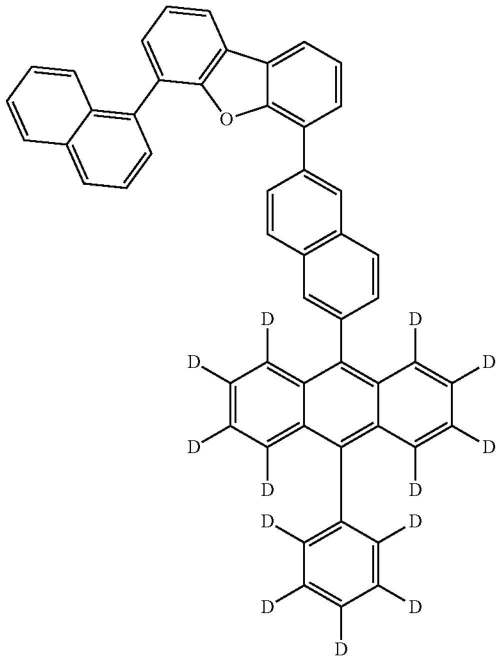
-continued
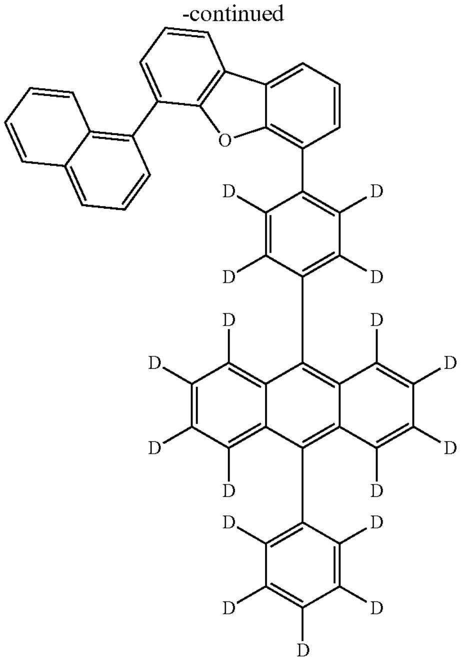
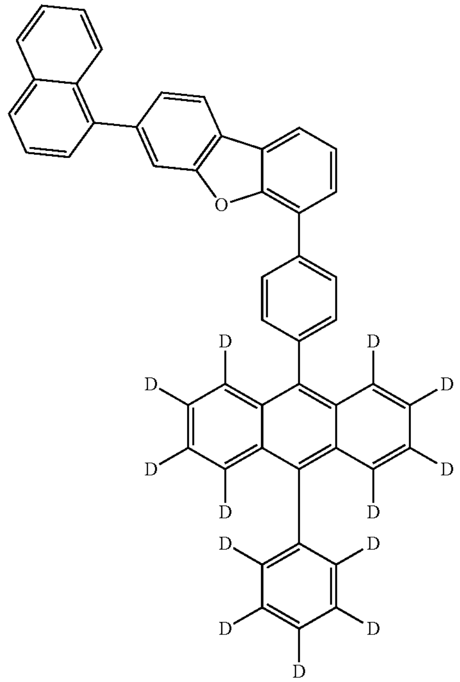

-continued
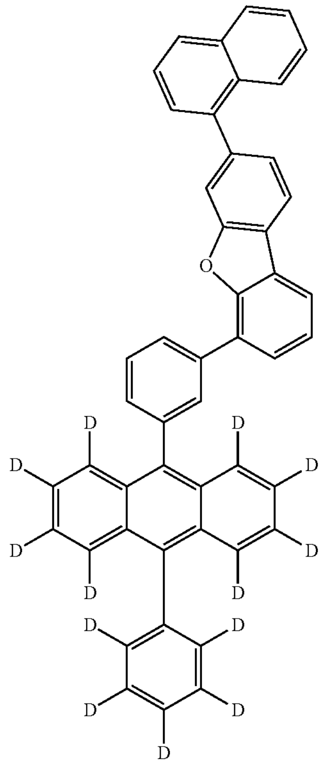
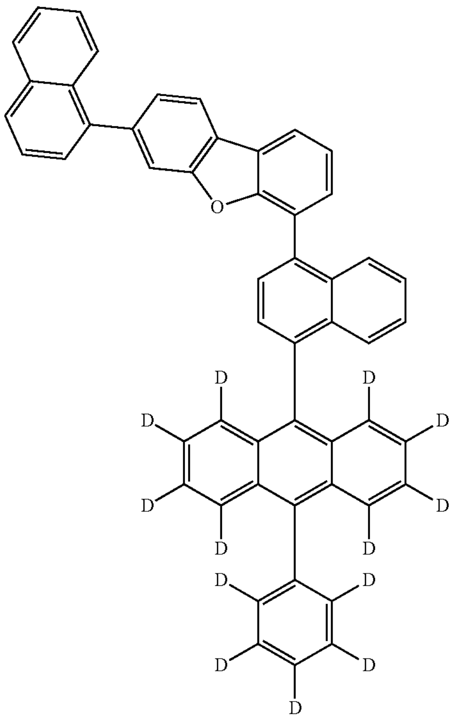
-continued
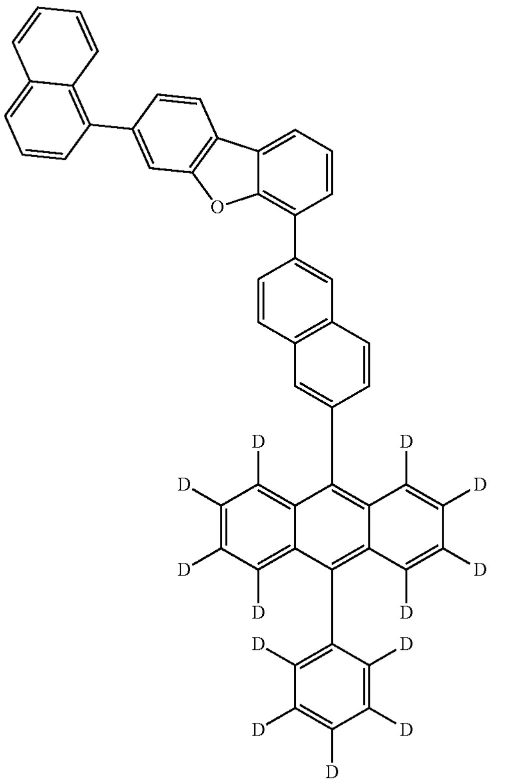
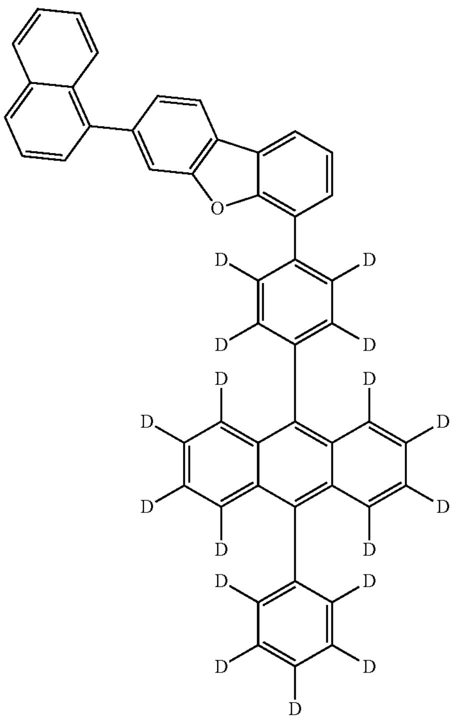

-continued
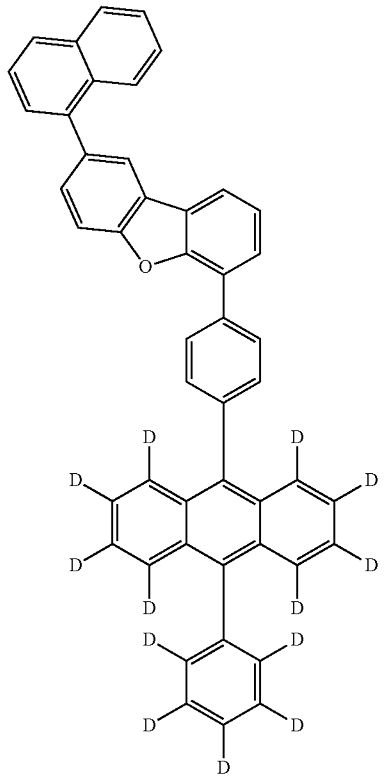
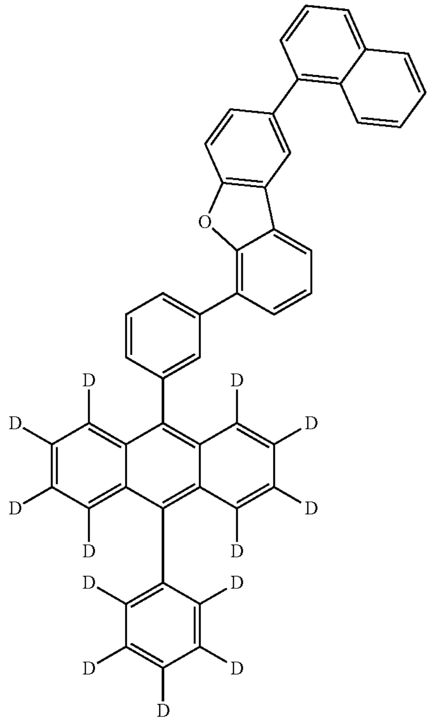
-continued
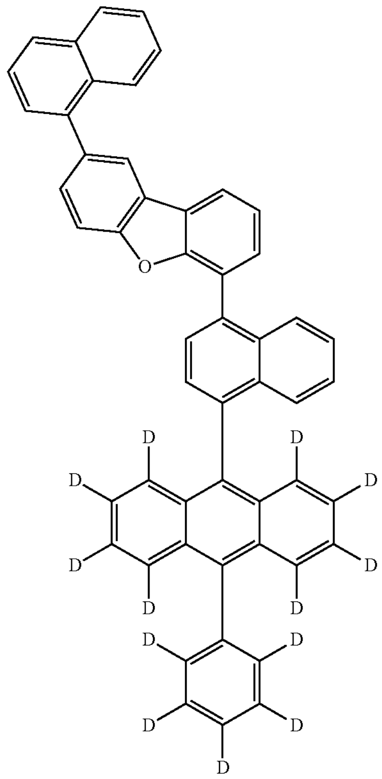
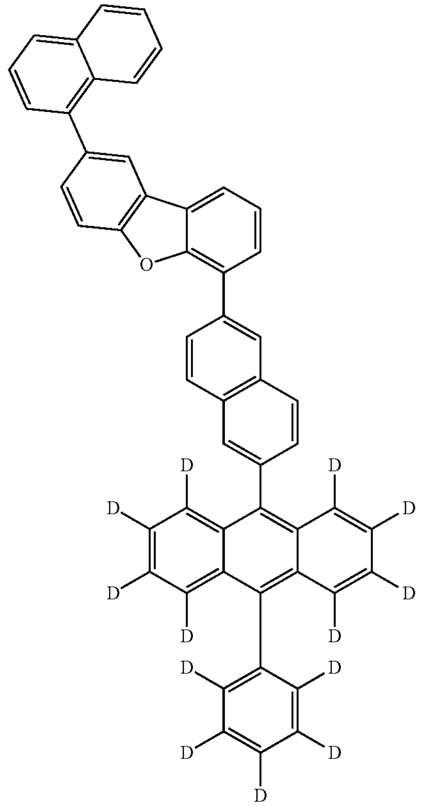

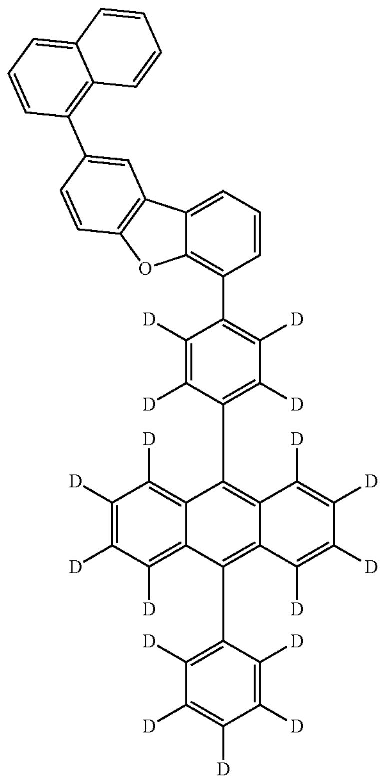
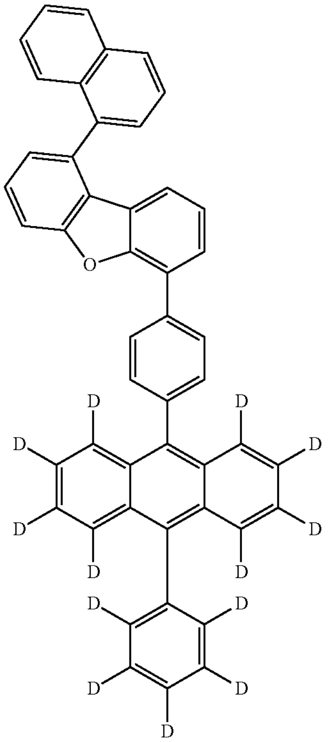
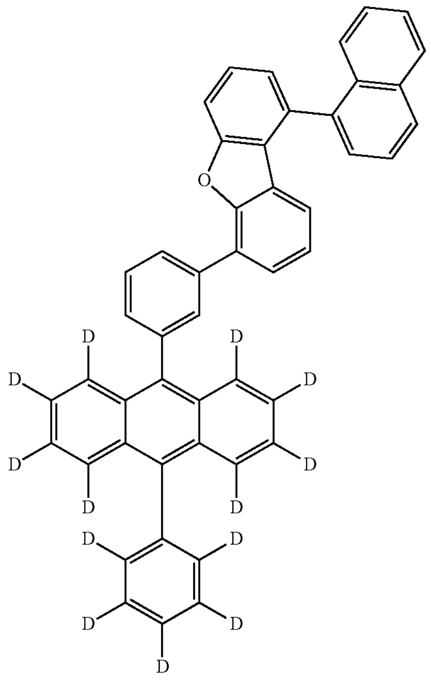
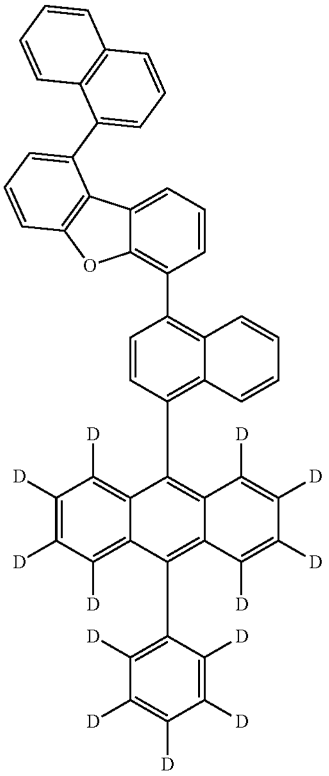

-continued
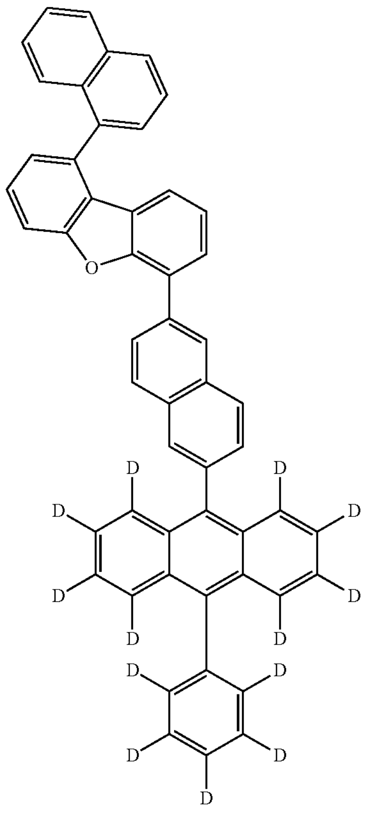 [SMILES: [2H]c1c([2H])c([2H])c(-c2c3c([2H])c([2H])c([2H])c([2H])c3c(-c3ccc4cc(-c5cccc6c5oc5cccc(-c7cccc8ccccc78)c56)ccc4c3)c3c([2H])c([2H])c([2H])c([2H])c23)c([2H])c1[2H]]
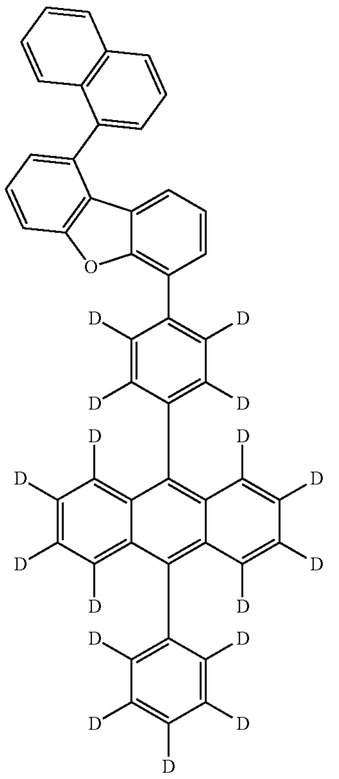
-continued
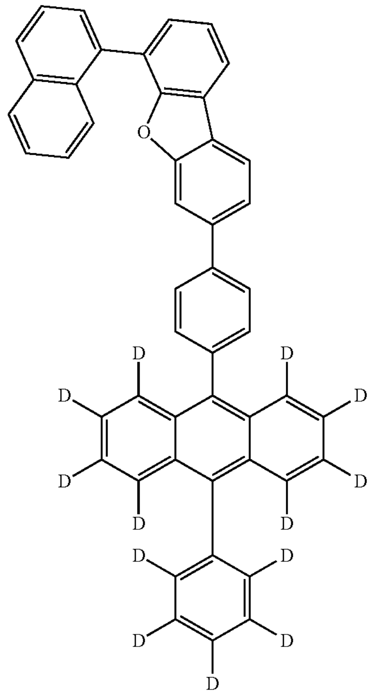
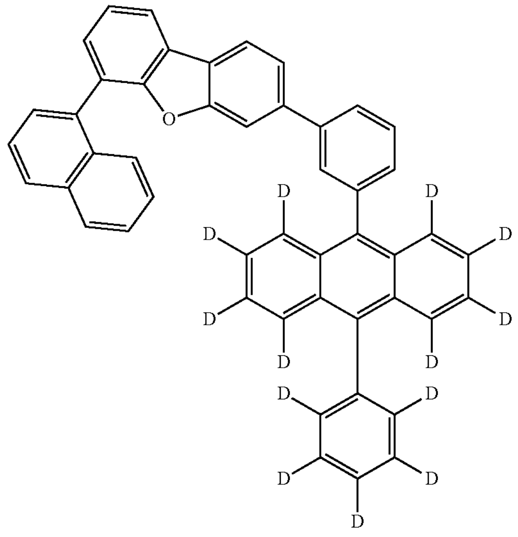

-continued
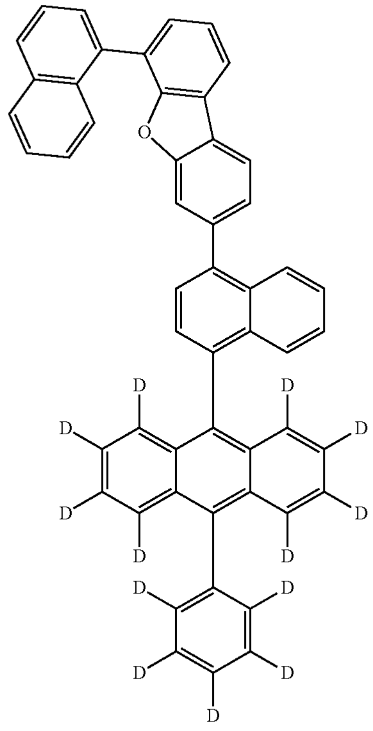
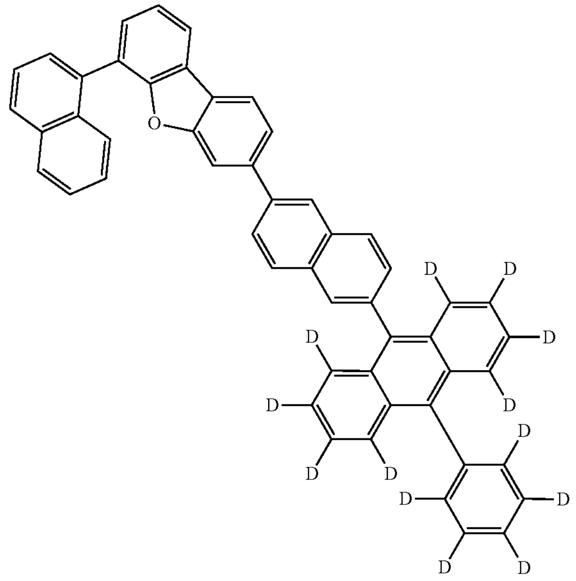
-continued
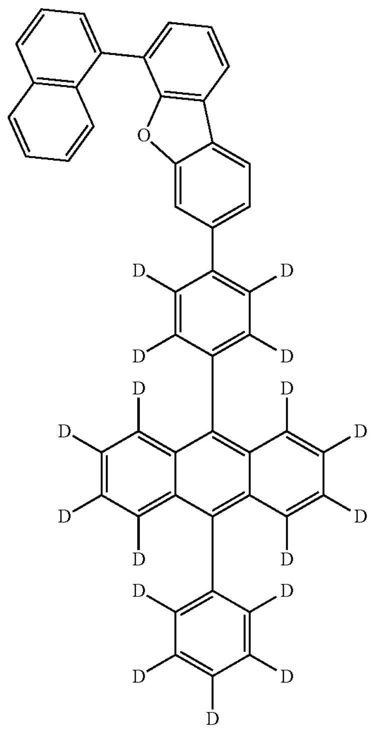
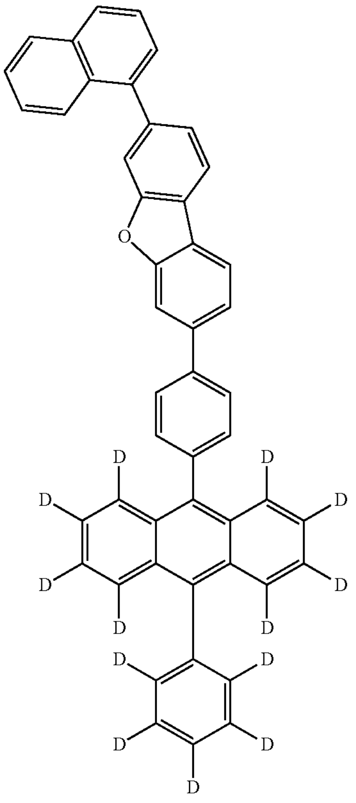

-continued
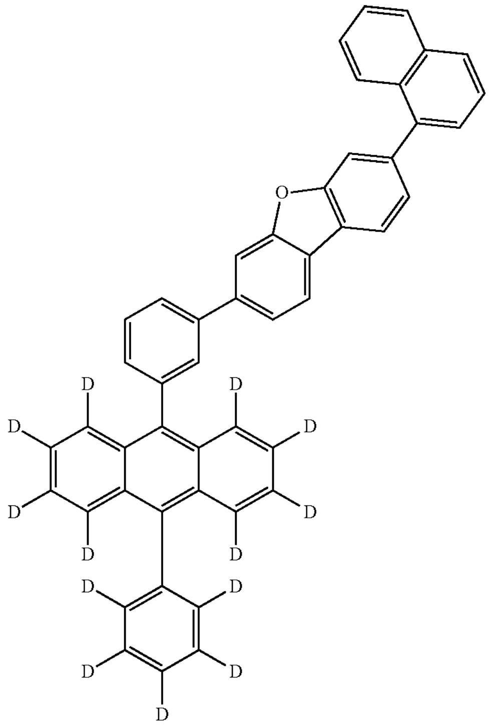
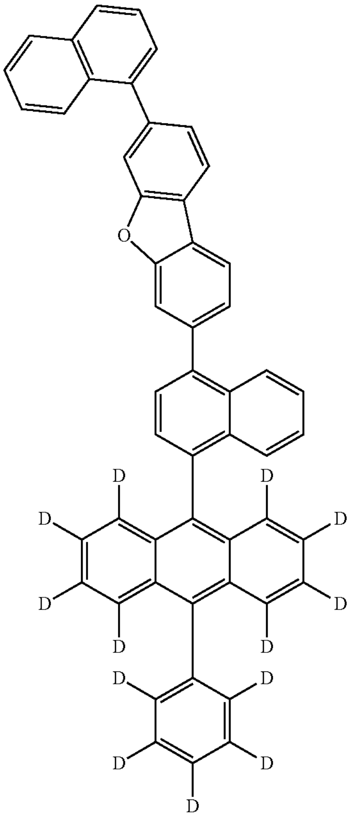
-continued
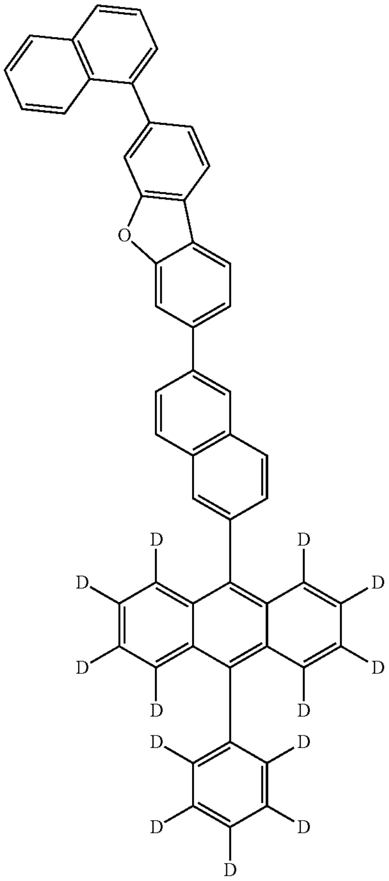
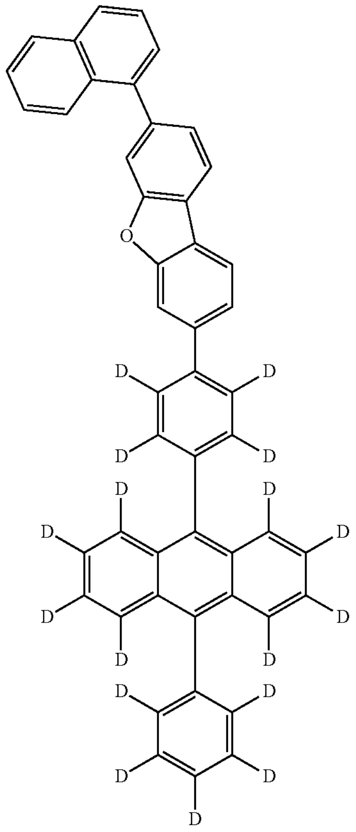

-continued
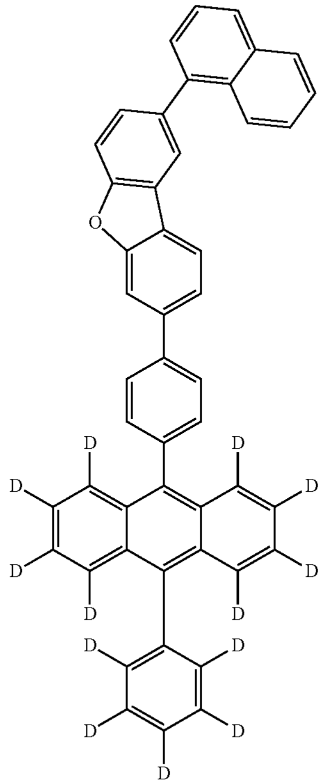
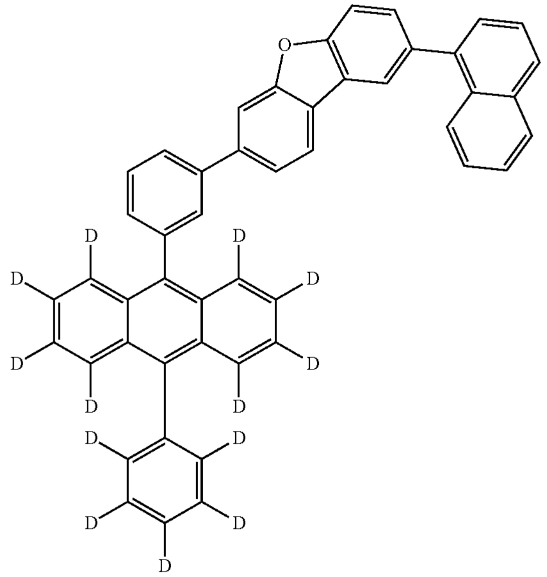
-continued
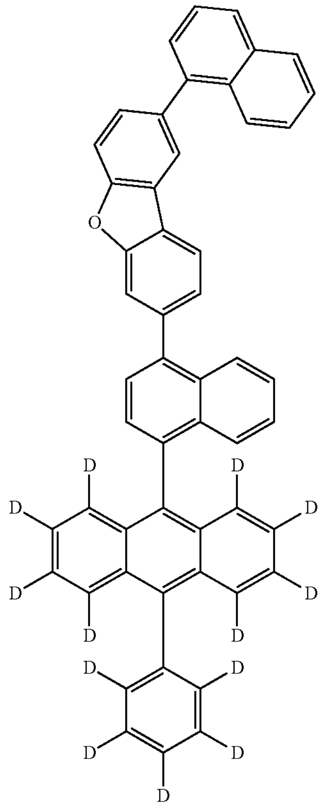
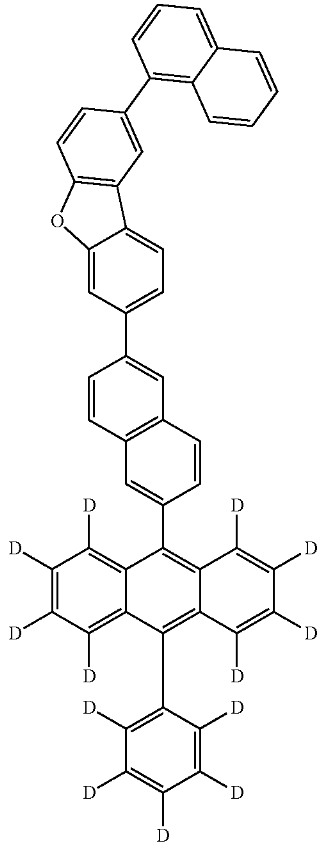

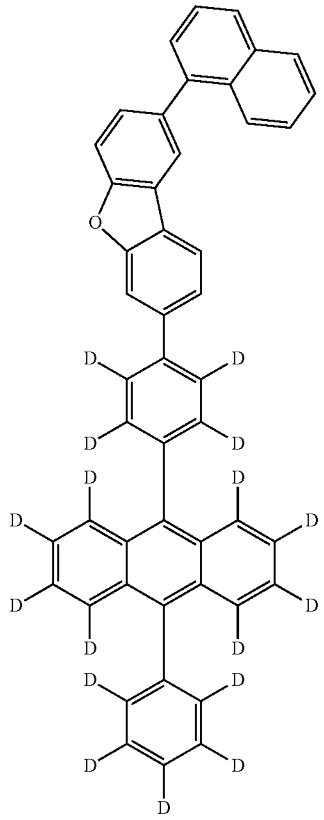
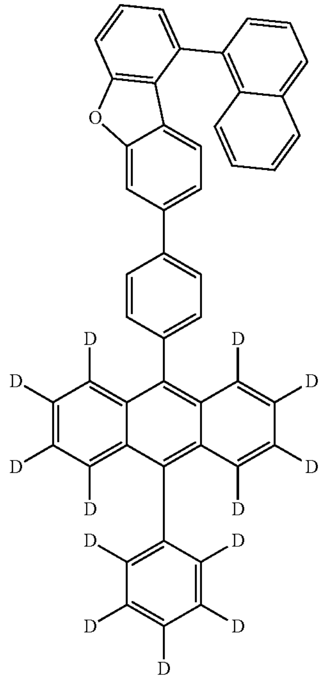
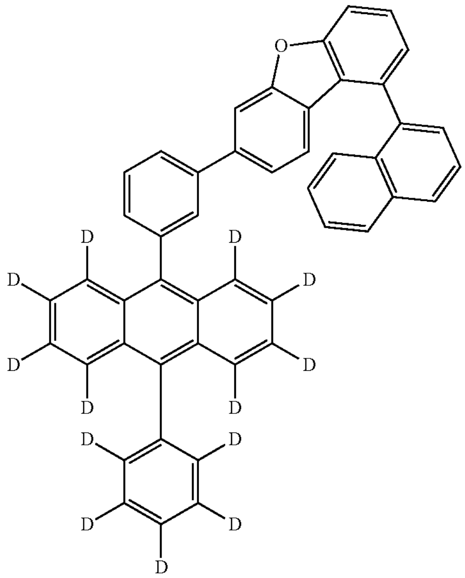
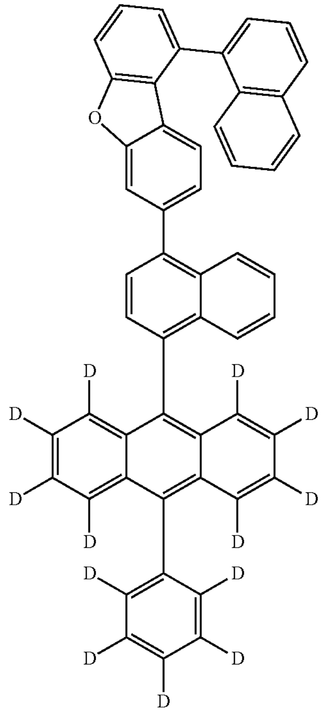

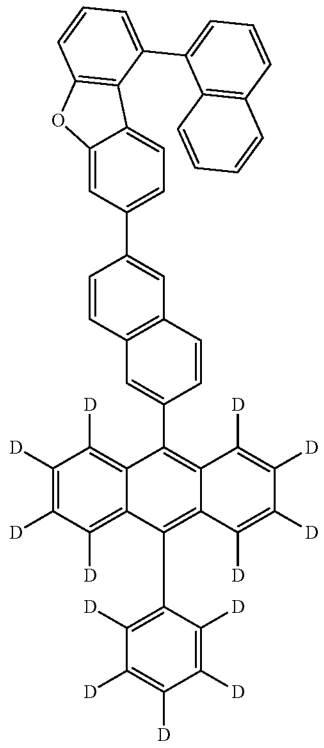
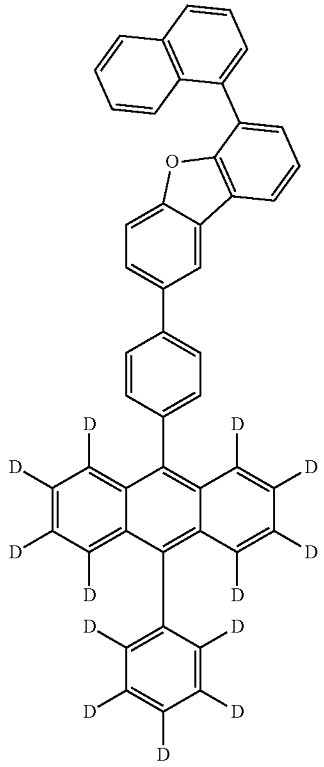
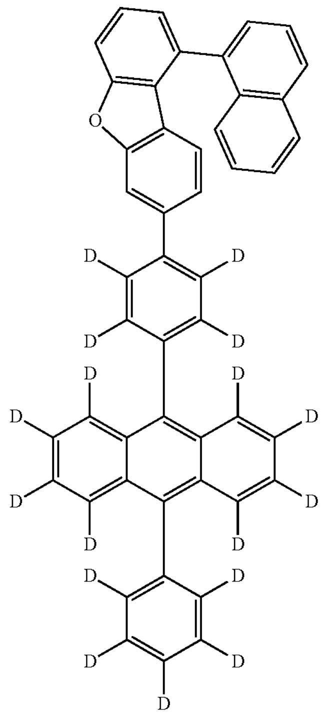
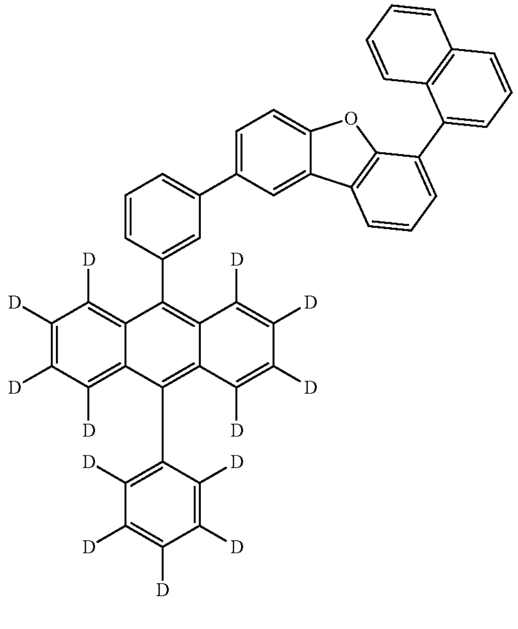

-continued
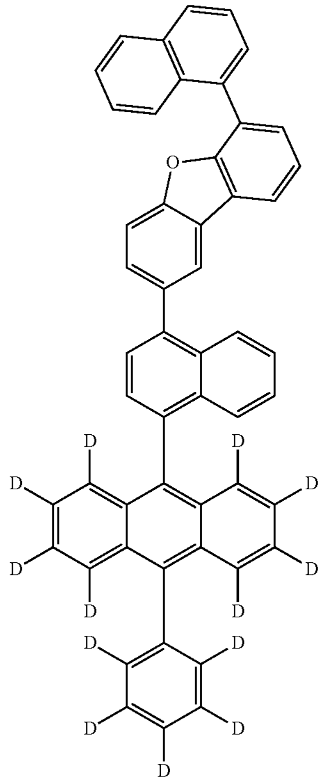
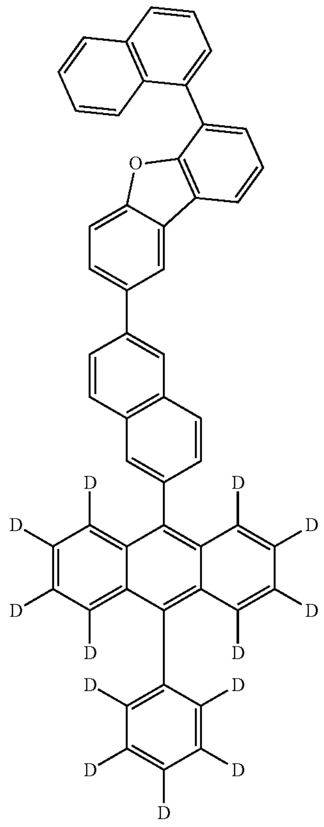
-continued
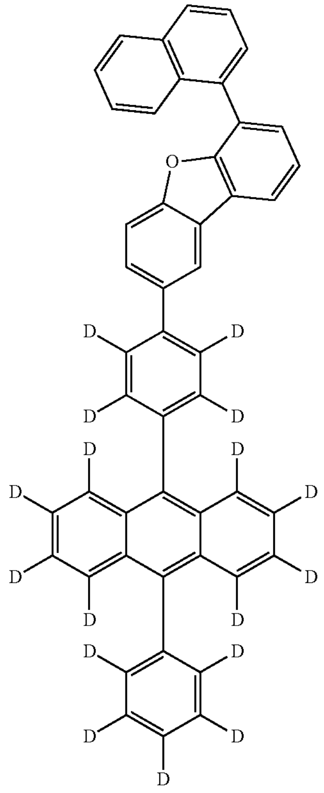
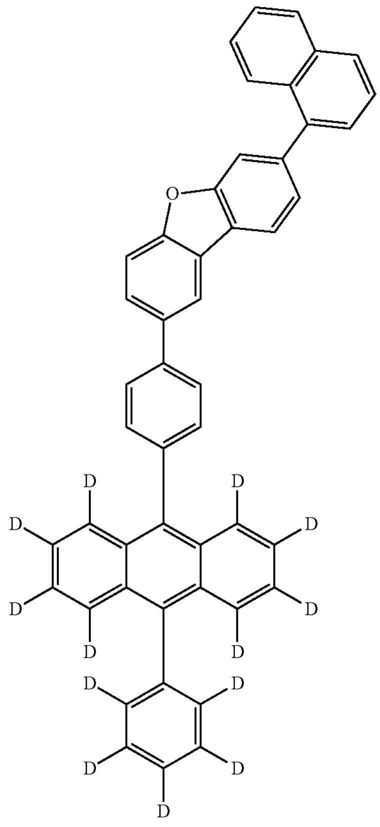

-continued
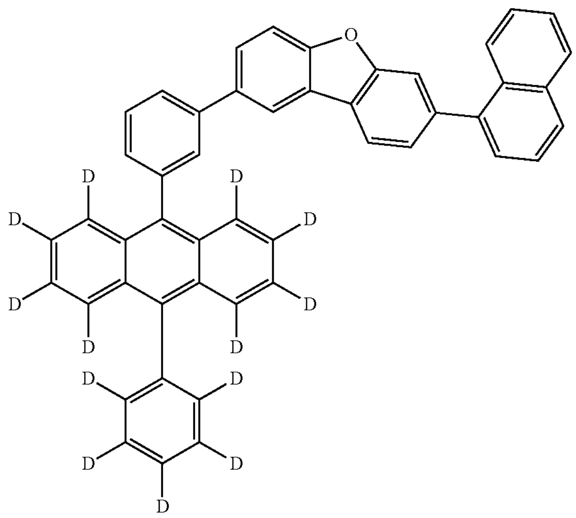
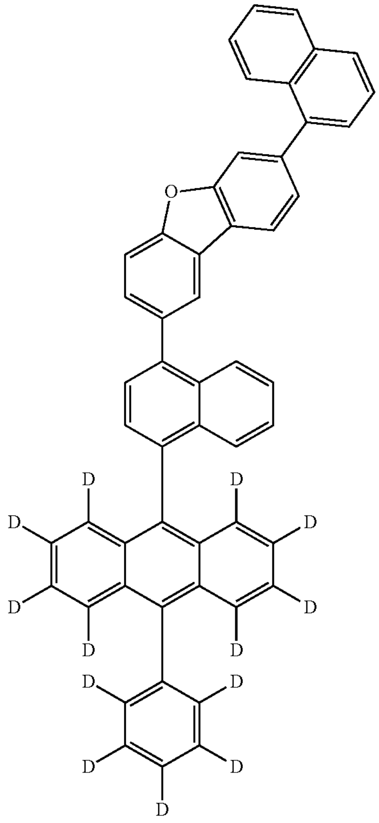
-continued
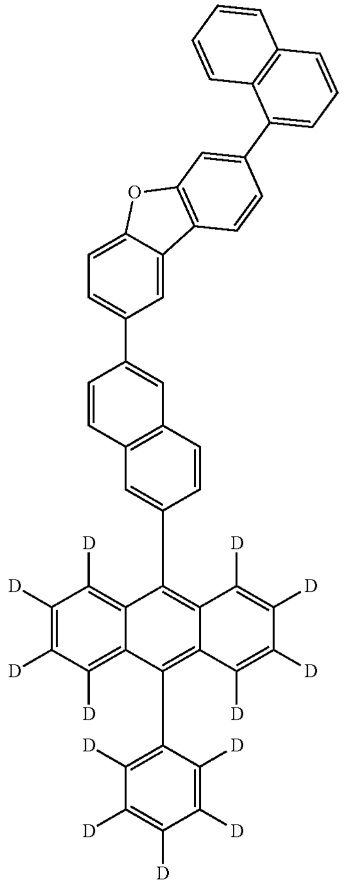
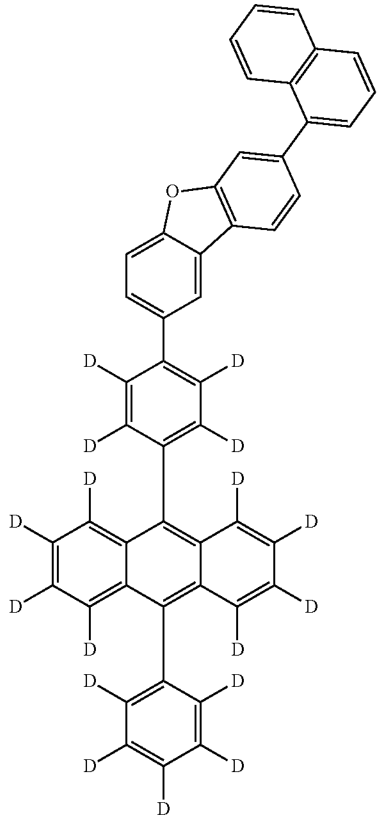

-continued
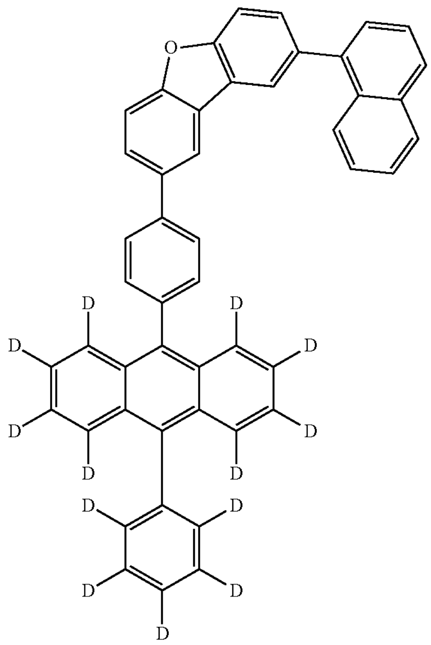
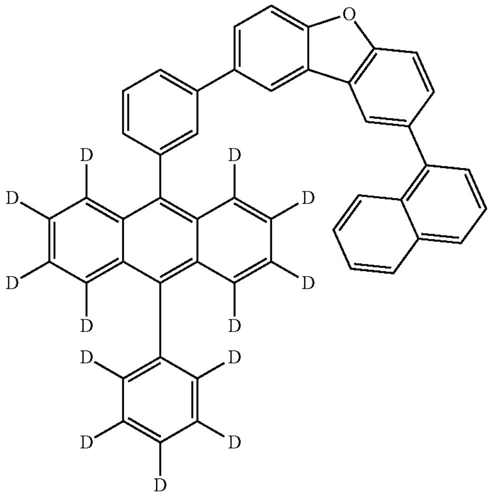
-continued
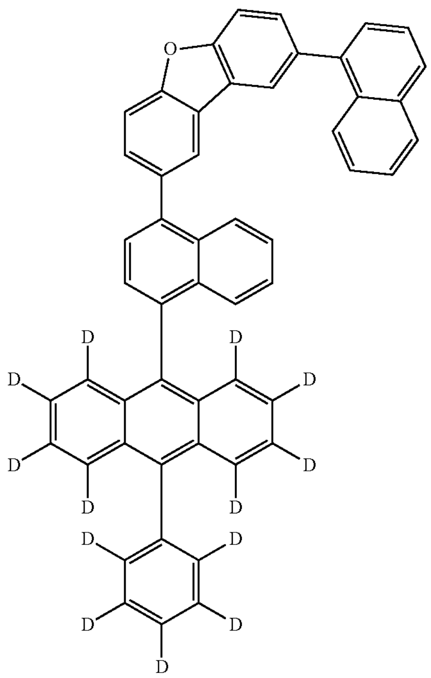
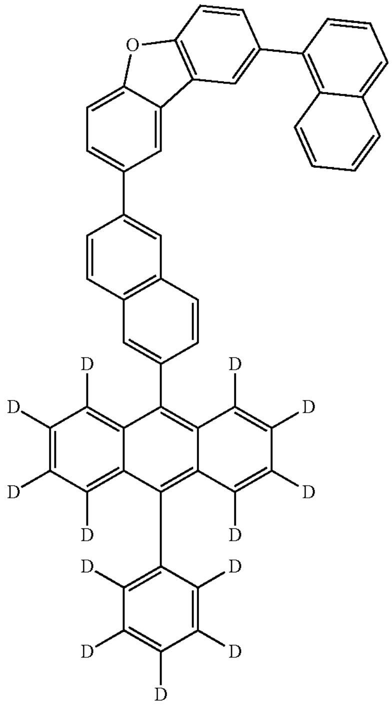

-continued
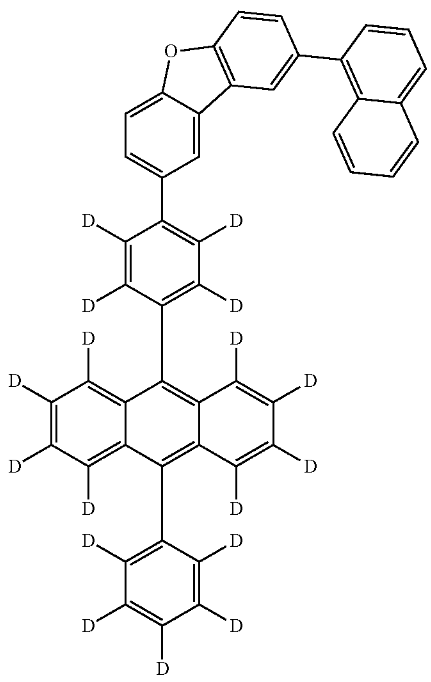
-continued
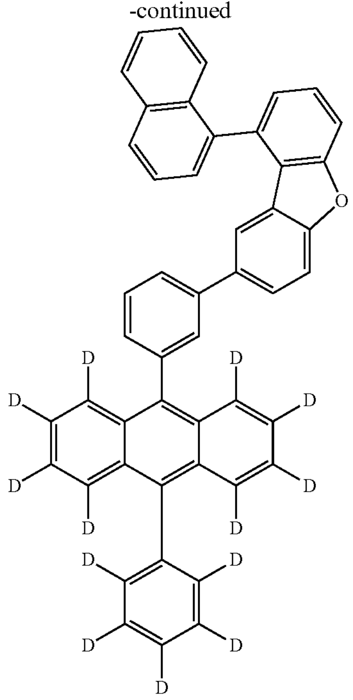
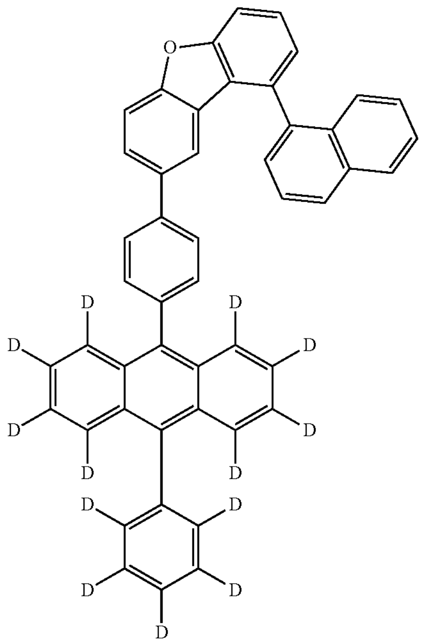
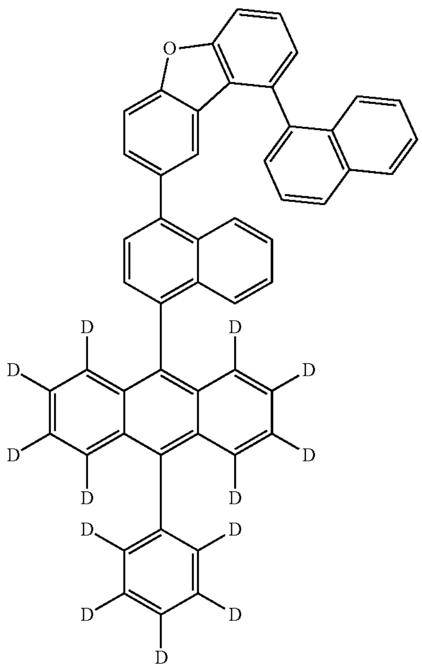

-continued
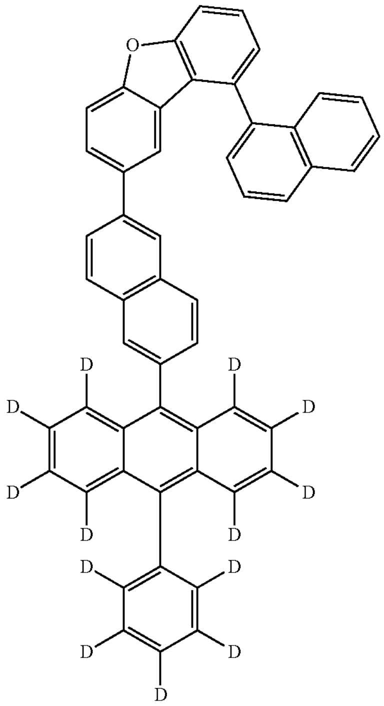
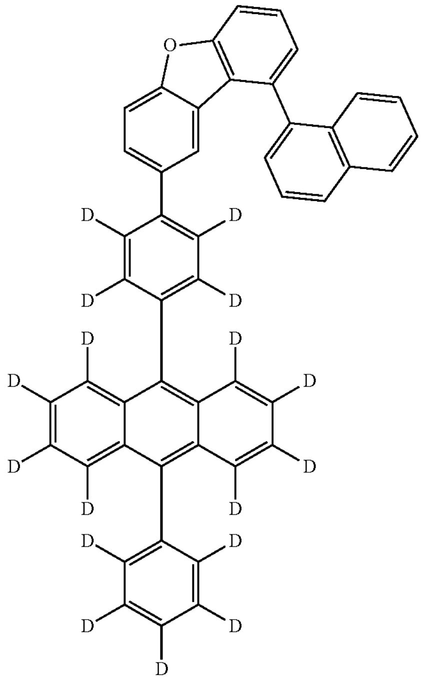
-continued
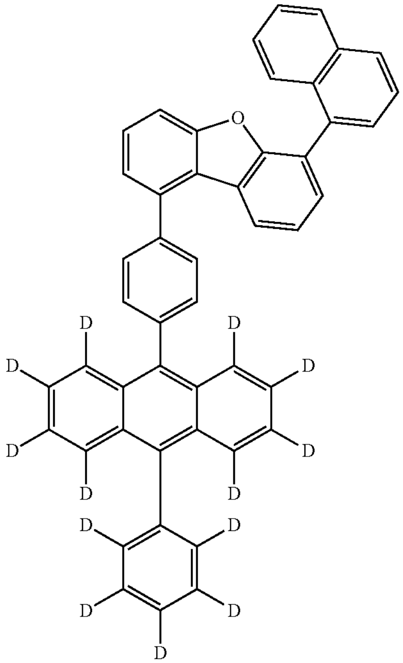
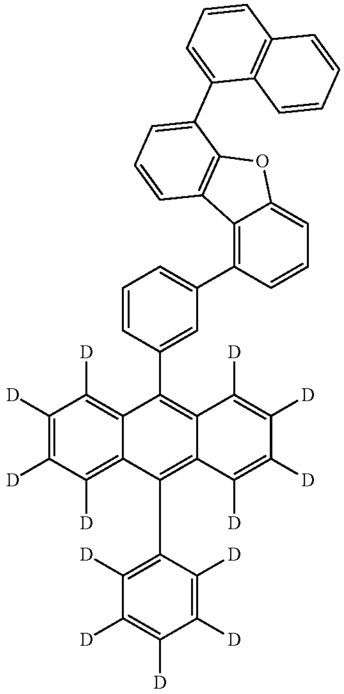

-continued
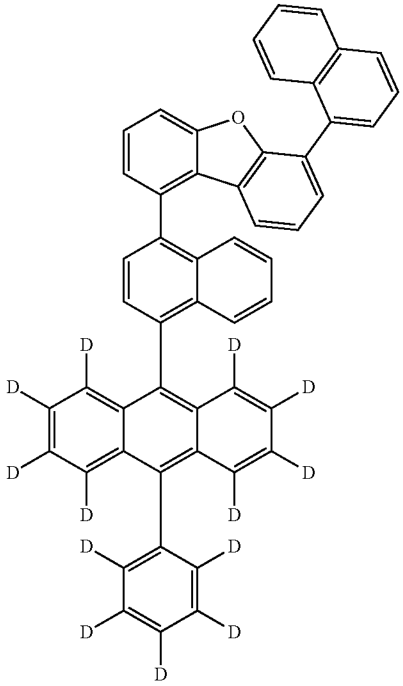
-continued
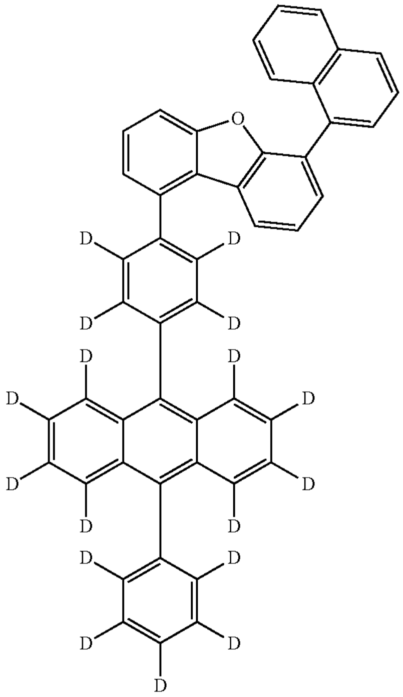
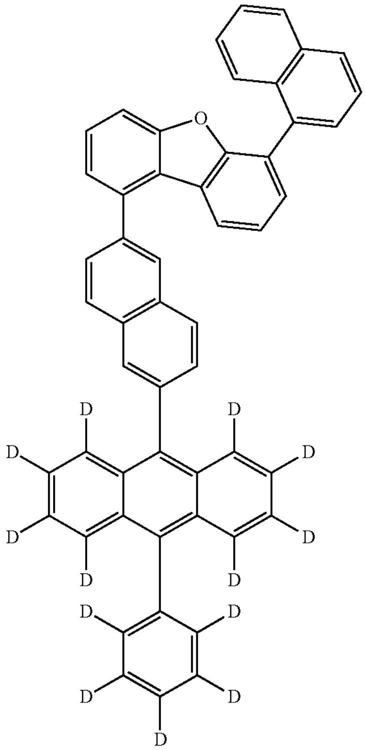
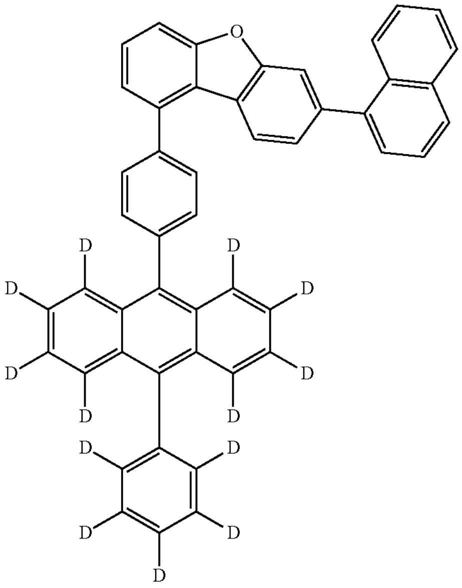

-continued
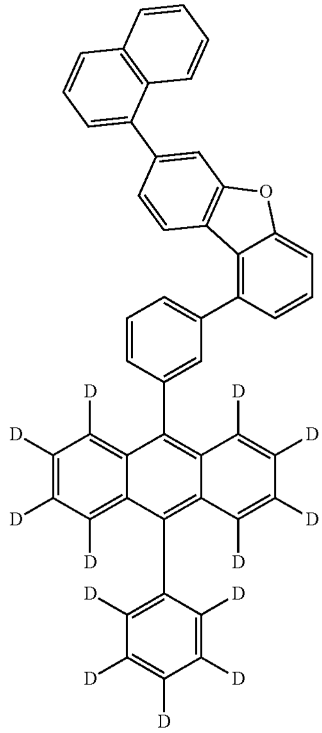
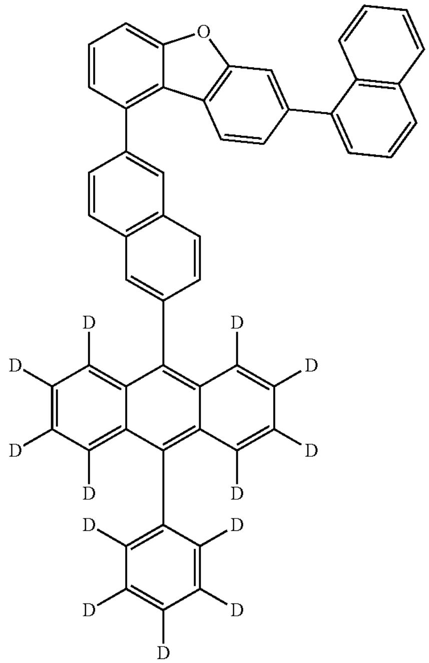
-continued
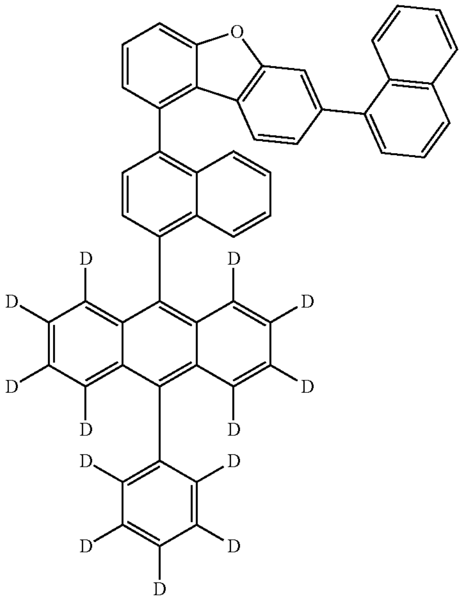
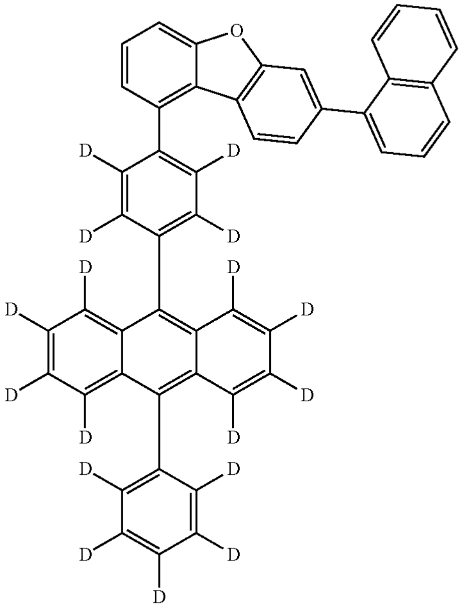

-continued
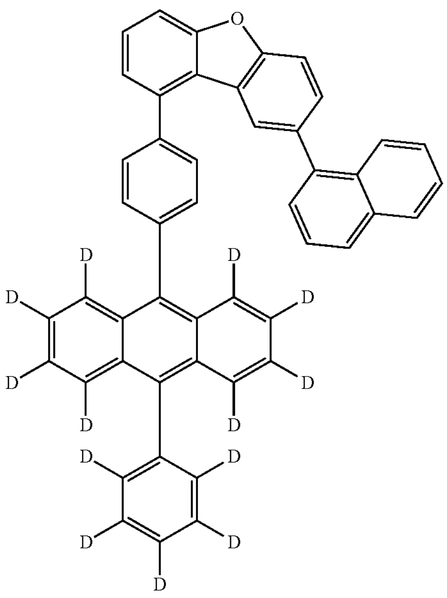
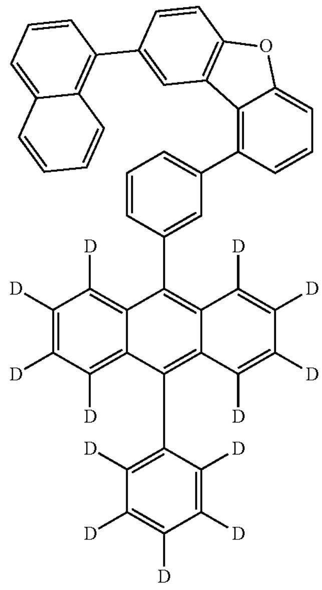
-continued
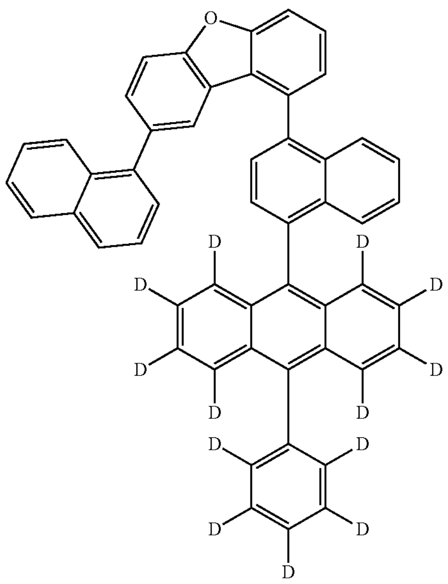
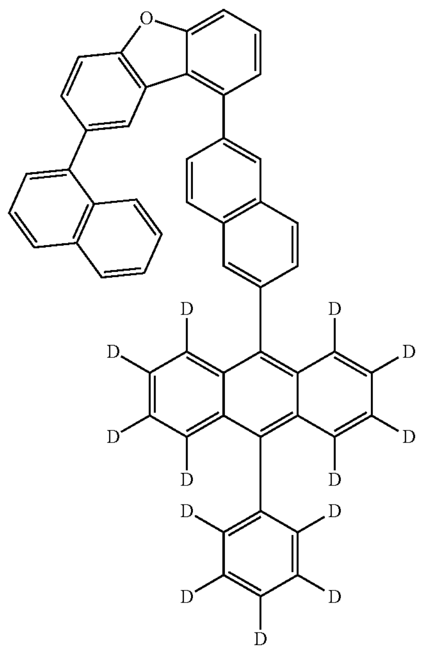

-continued
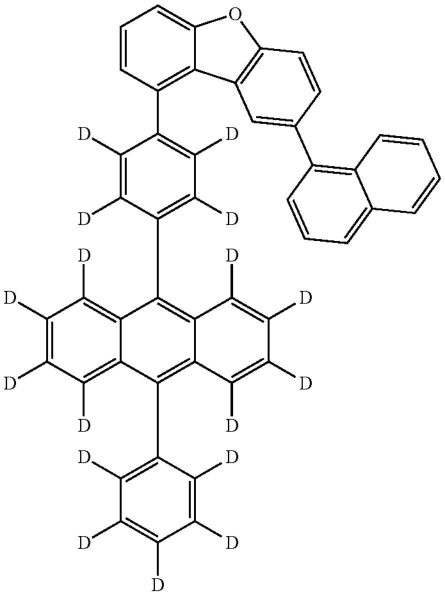
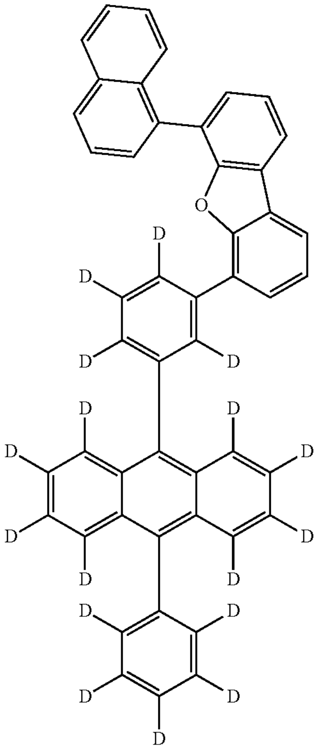
-continued
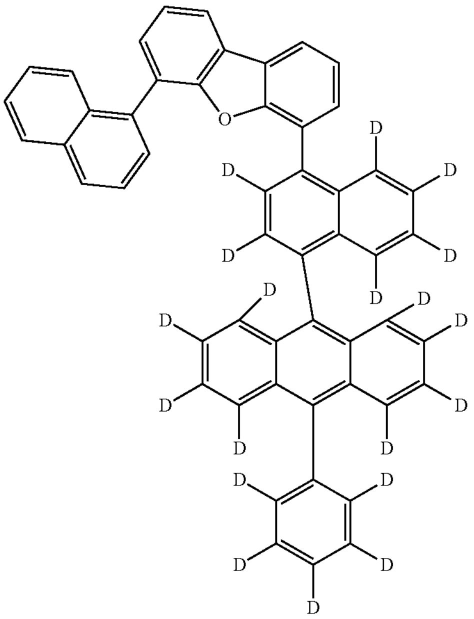
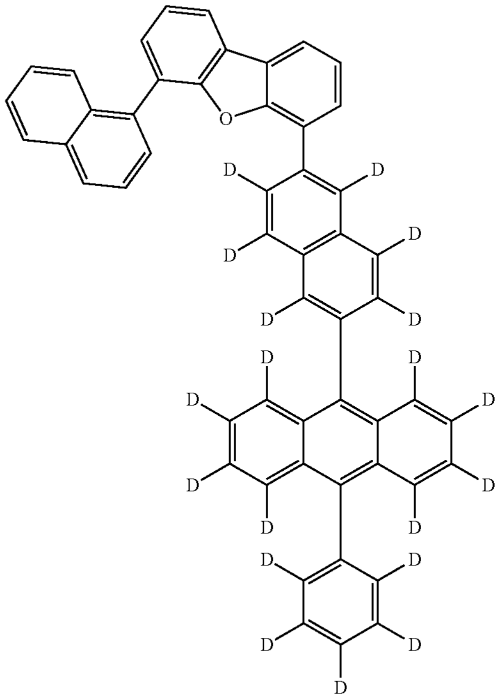

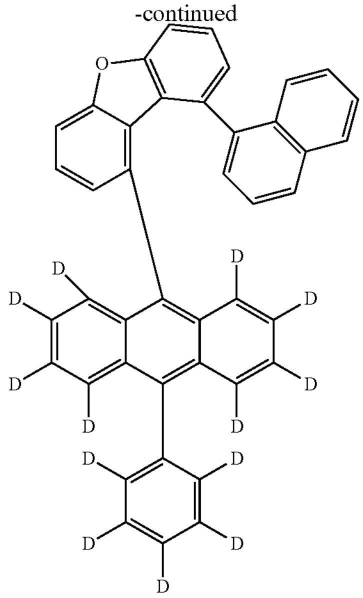
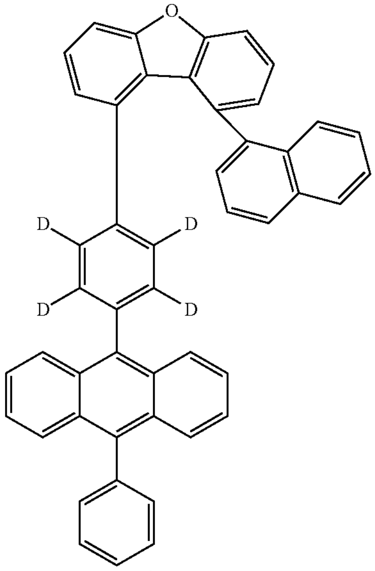
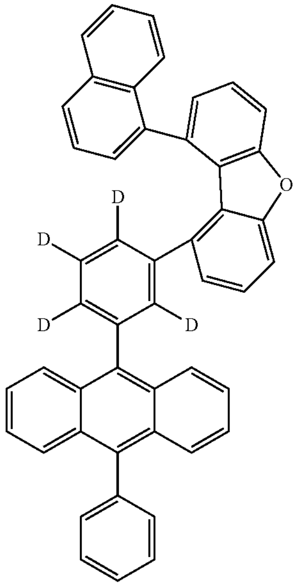
-continued
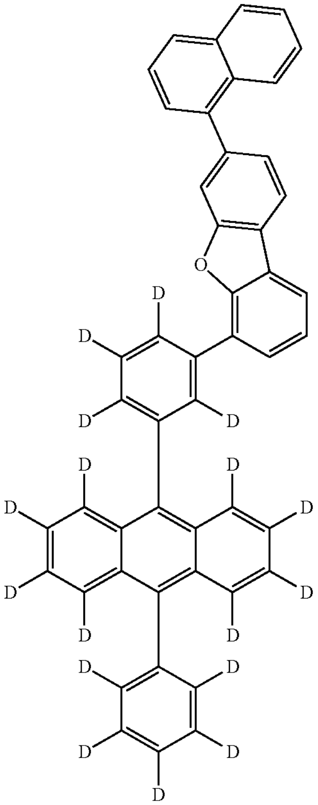
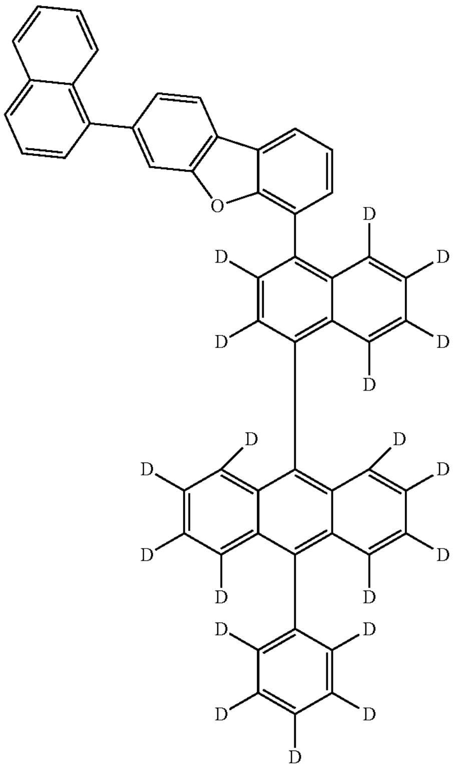

-continued
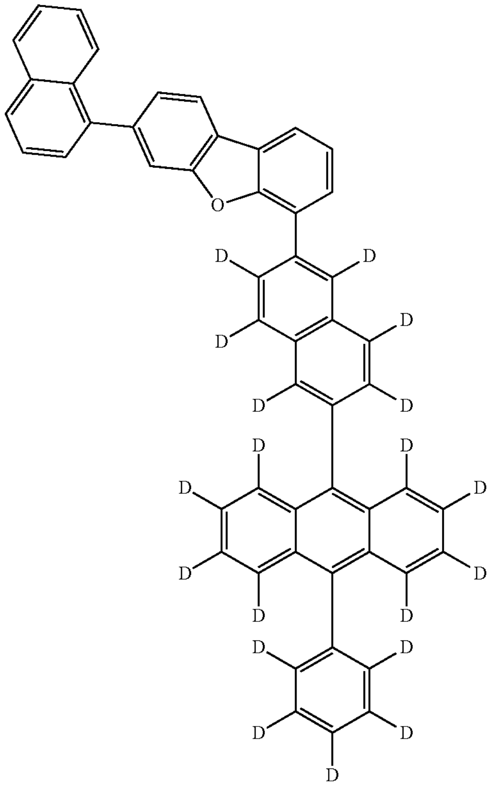
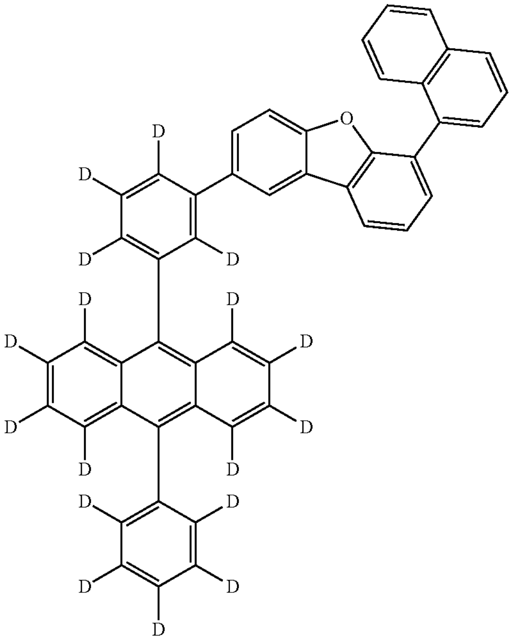
-continued
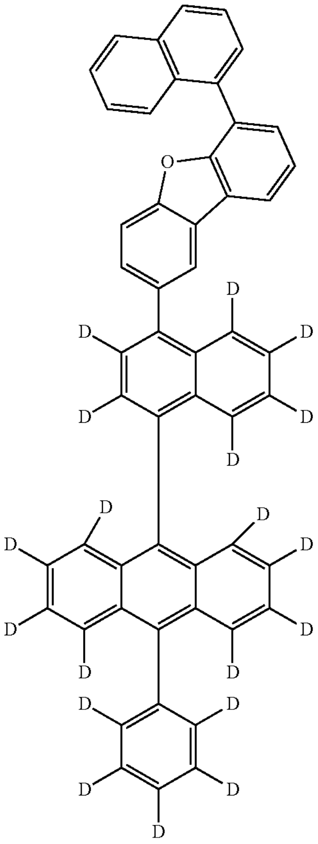
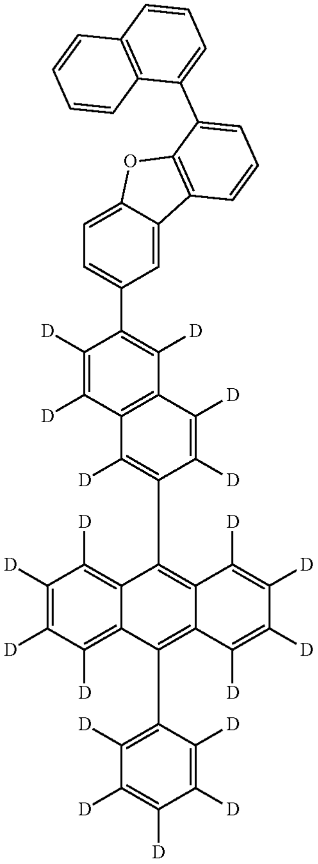

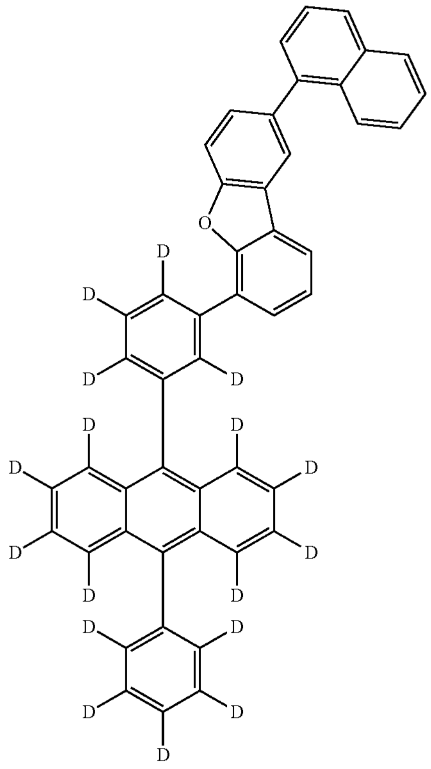
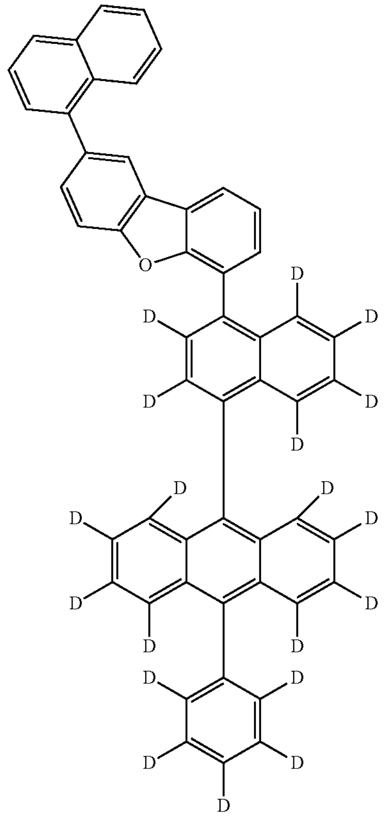
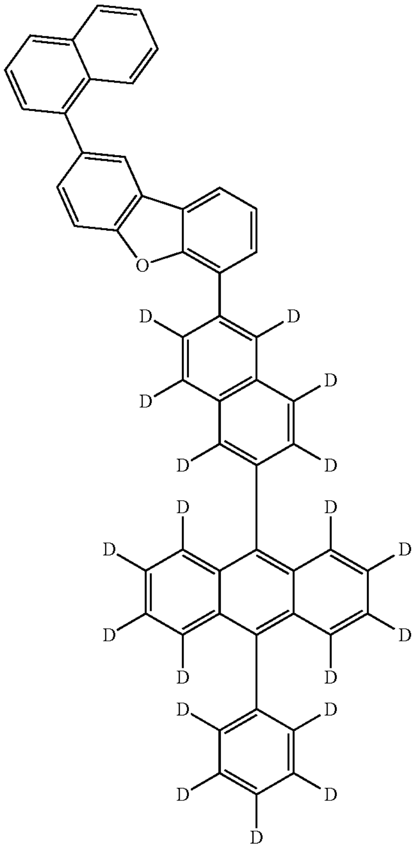
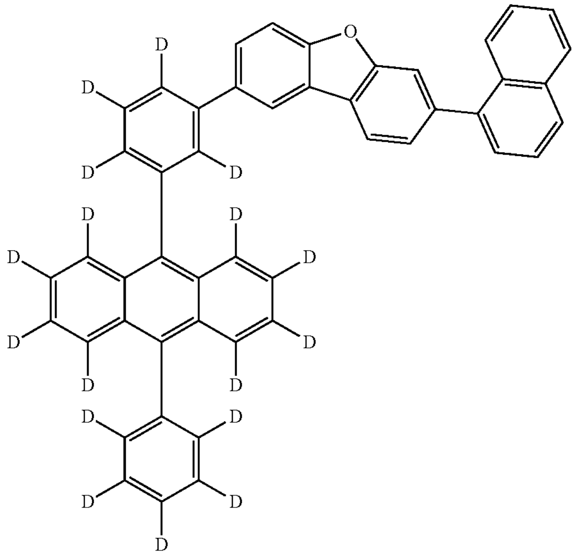

-continued
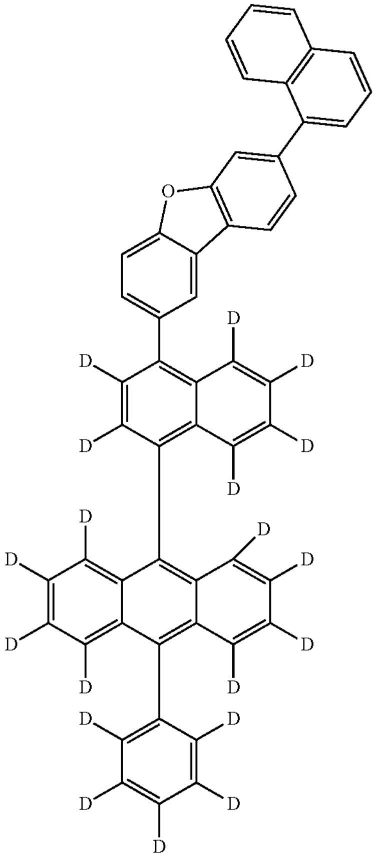
-continued
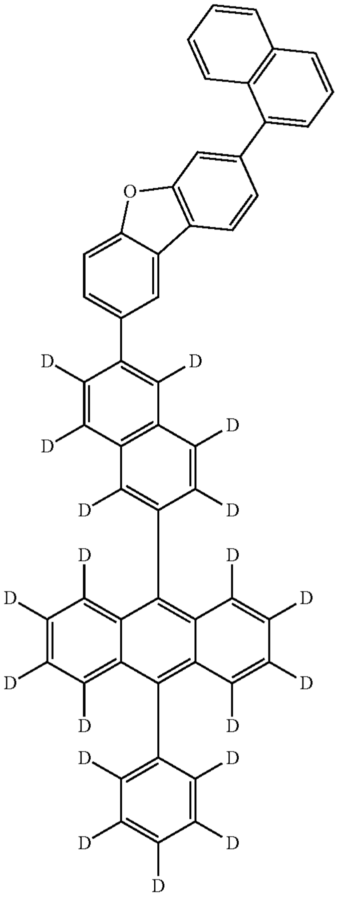
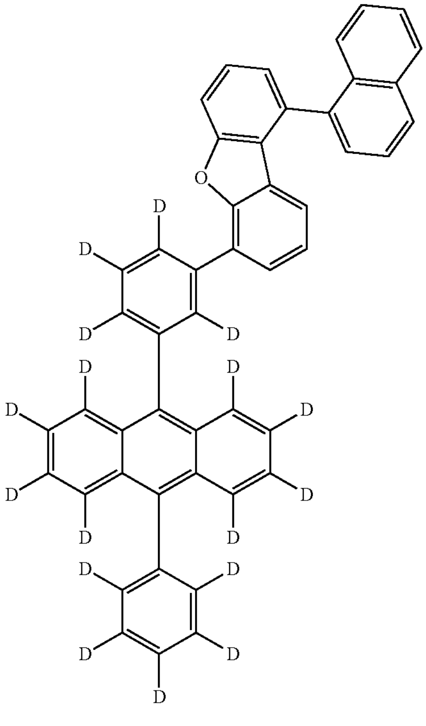

-continued
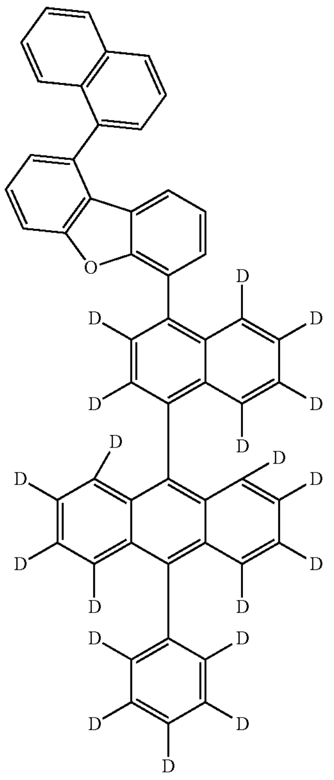
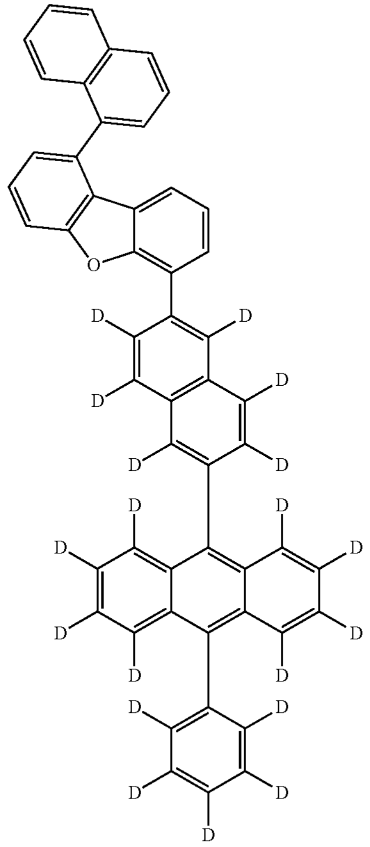
-continued
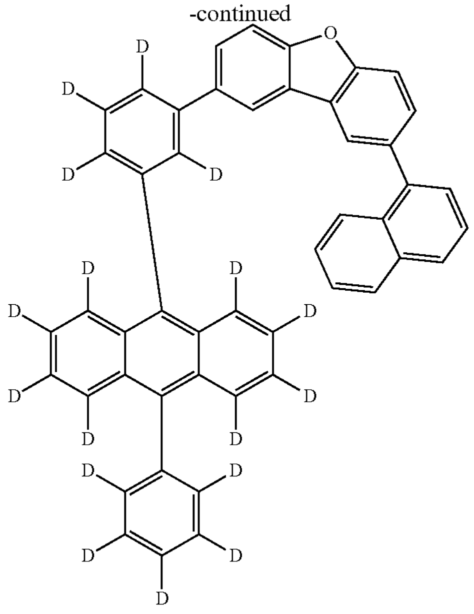
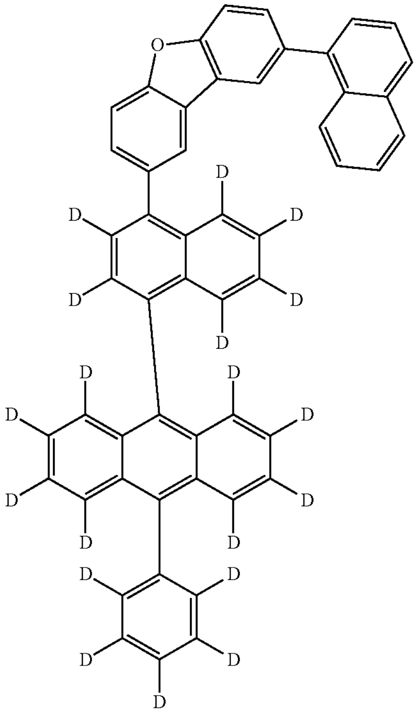

-continued
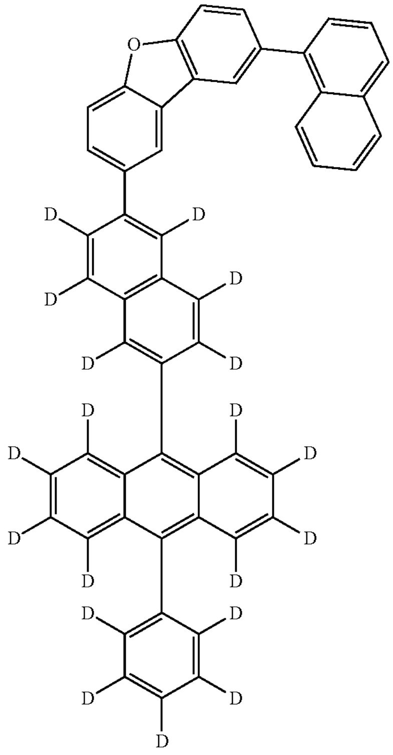
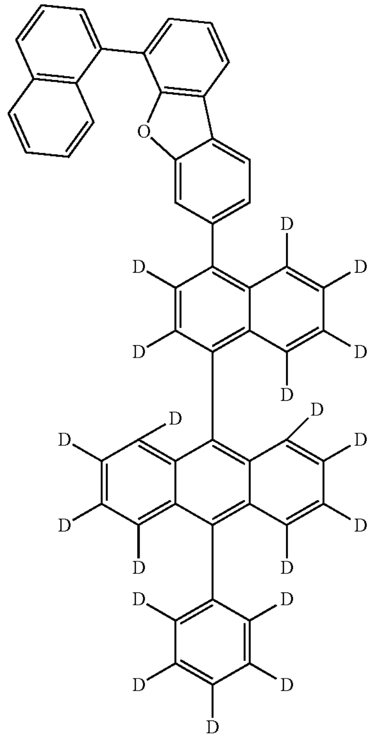
-continued
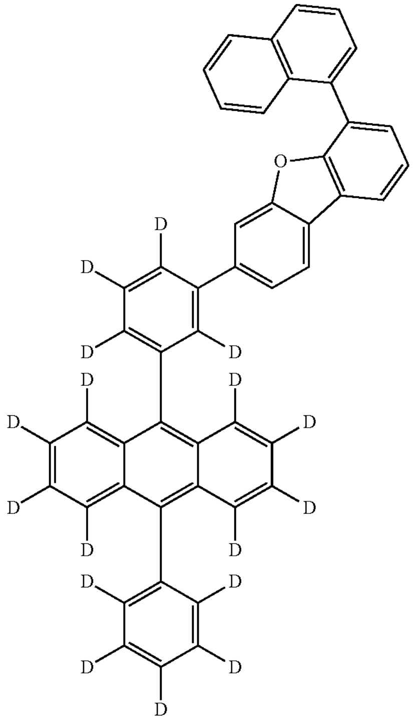
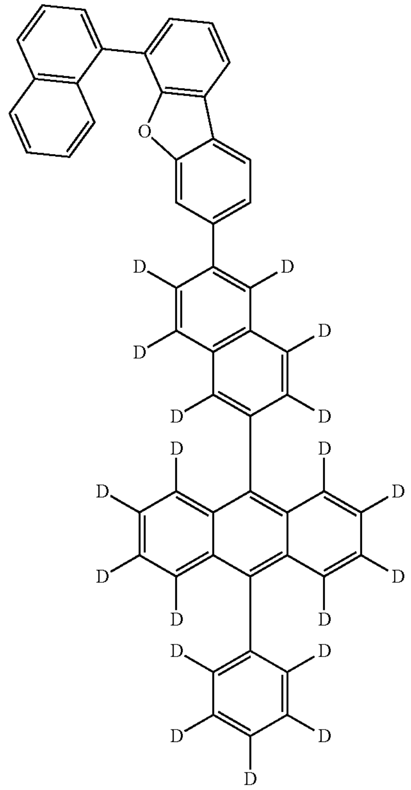

-continued
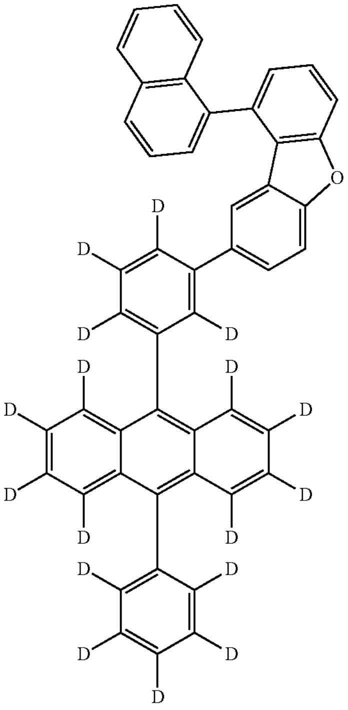
-continued
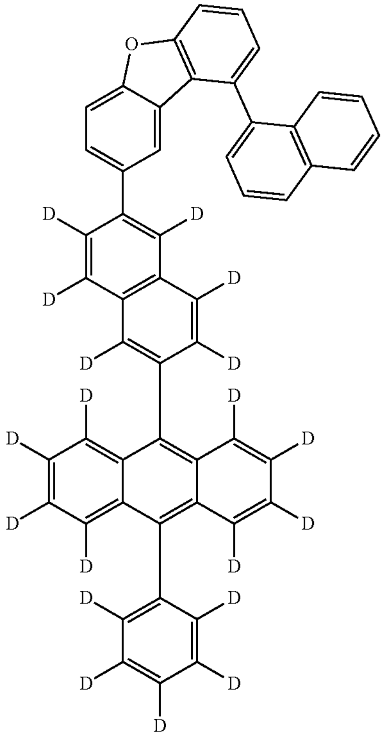
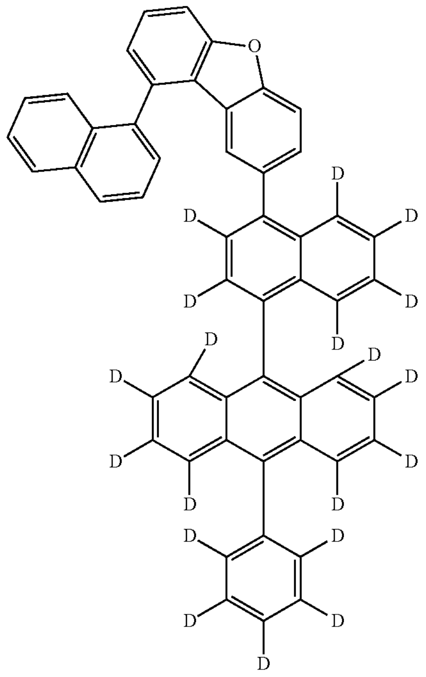
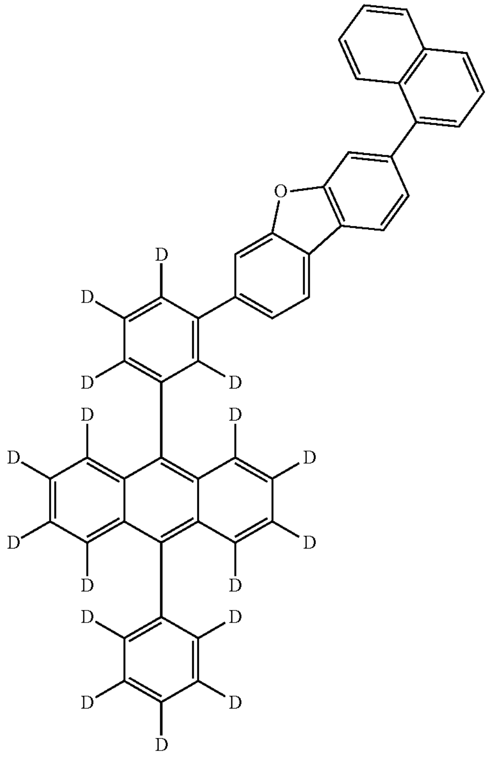

-continued
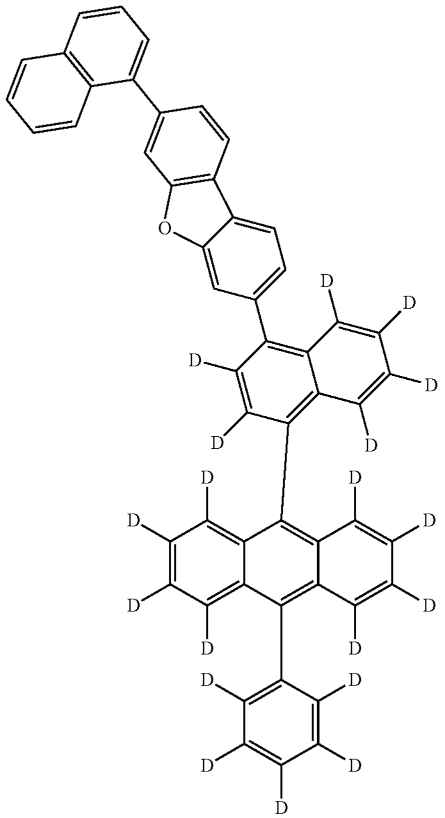
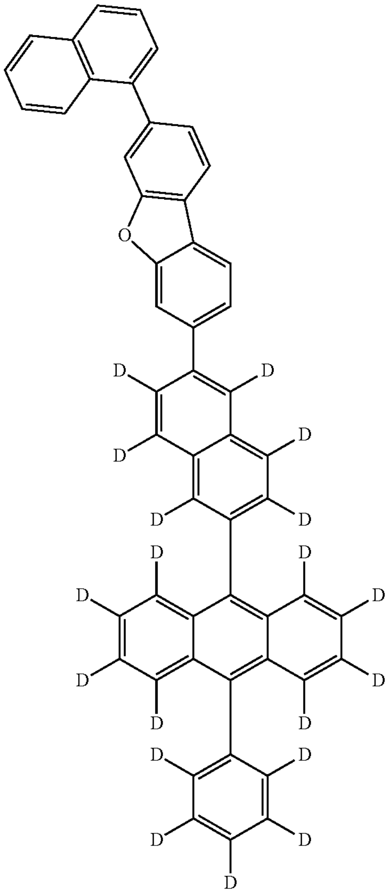
-continued
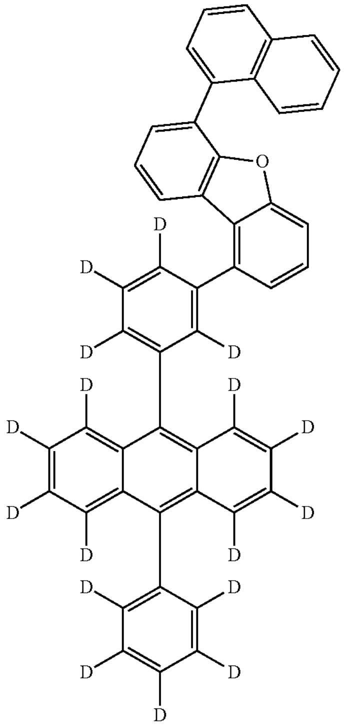
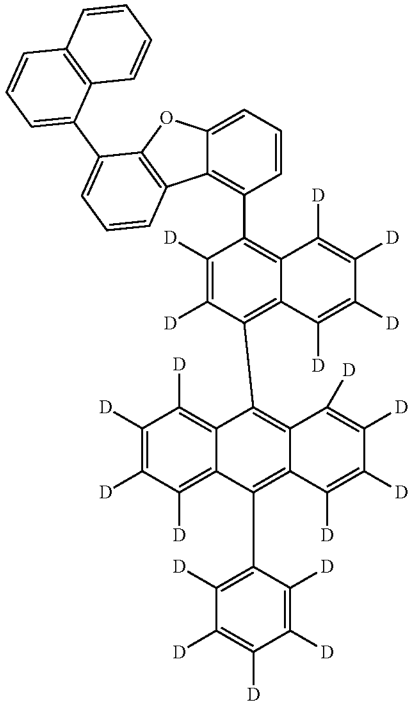

-continued
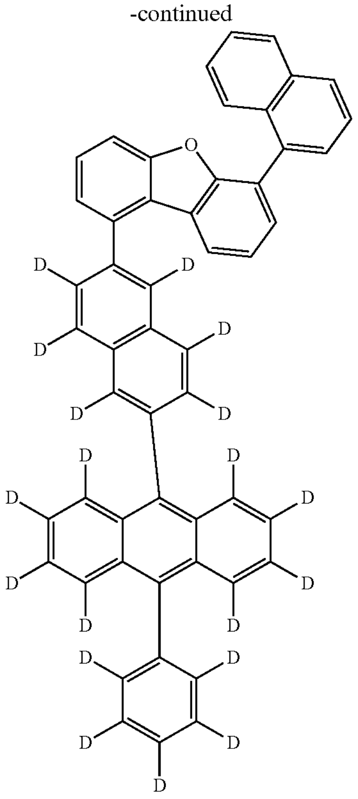
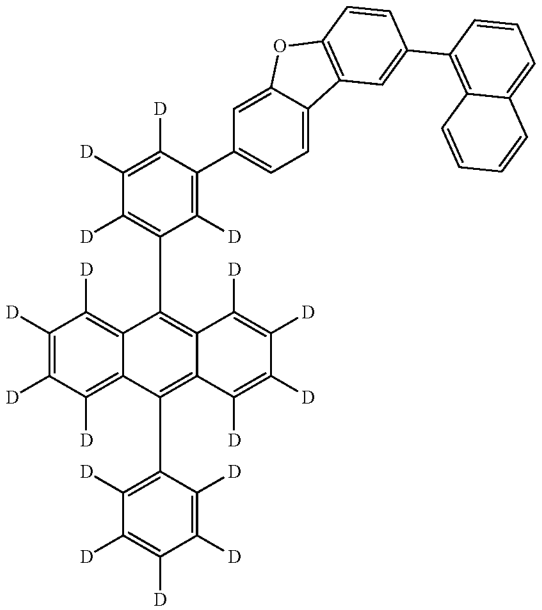
-continued
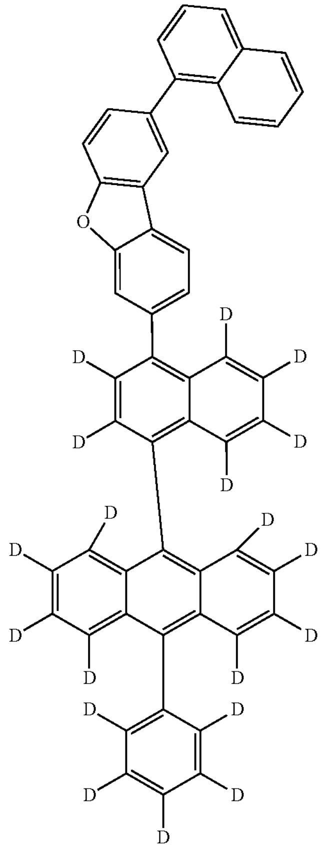

-continued
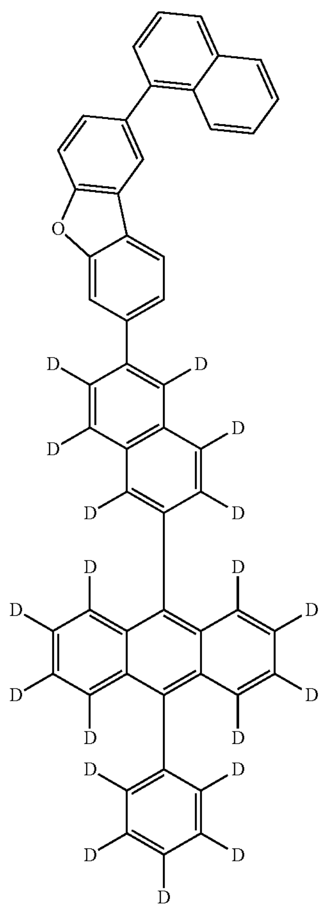
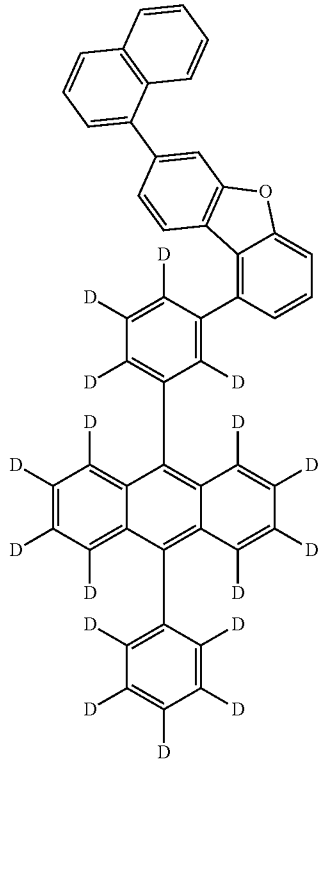
-continued
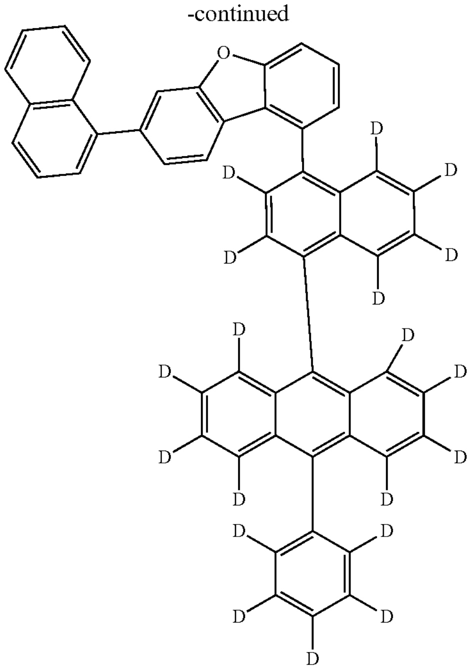
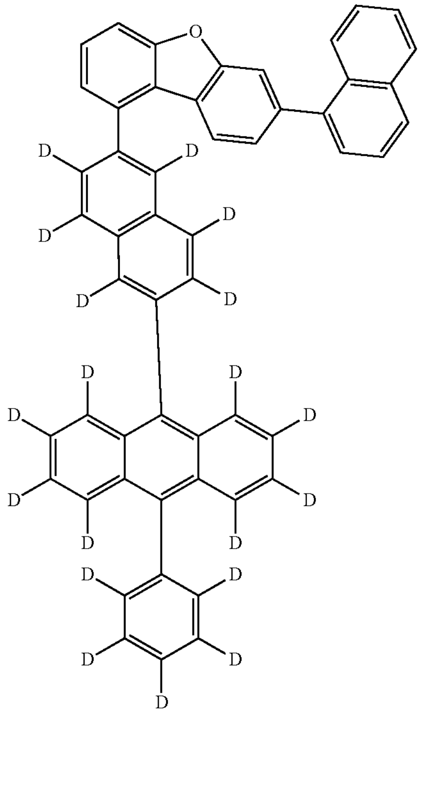

-continued
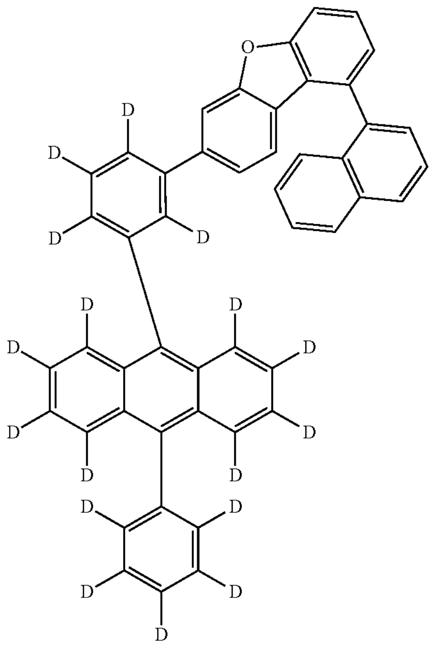
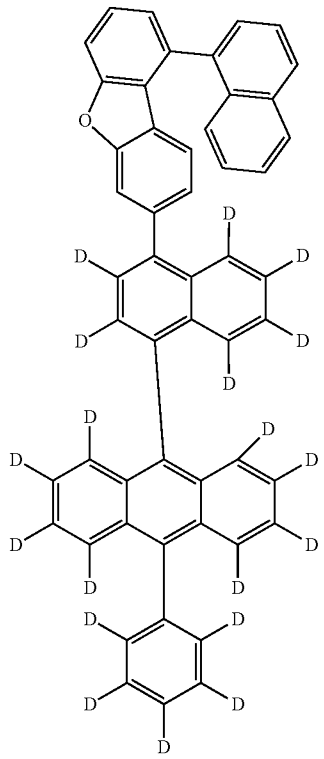
-continued
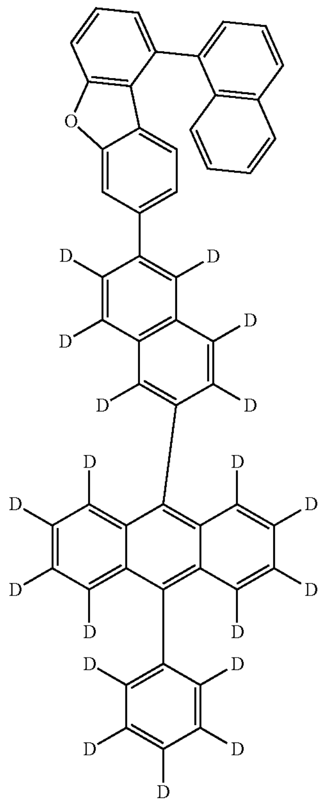
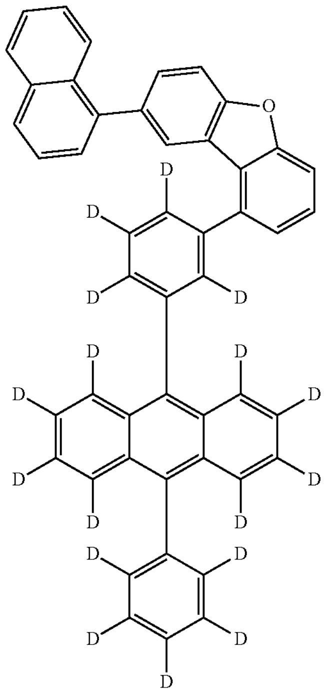

-continued
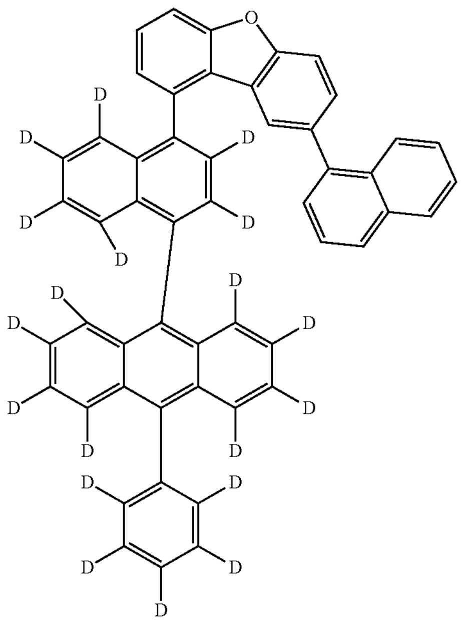
-continued
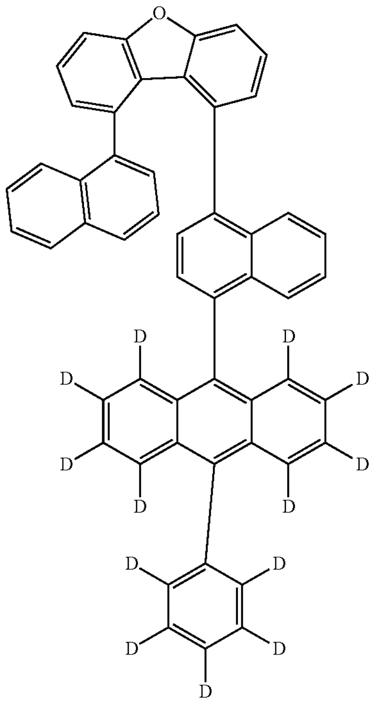
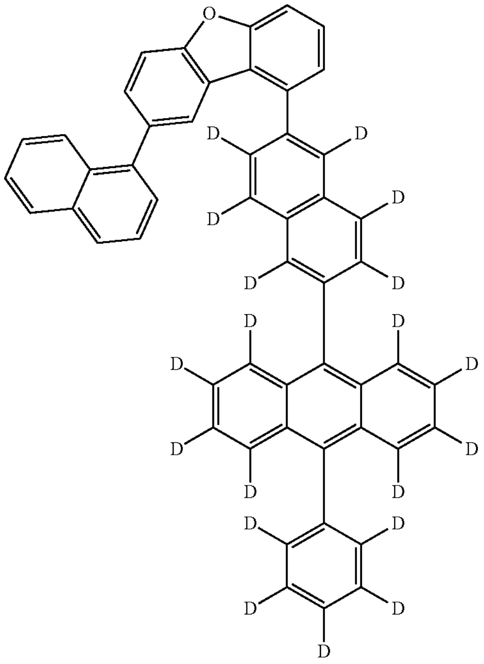
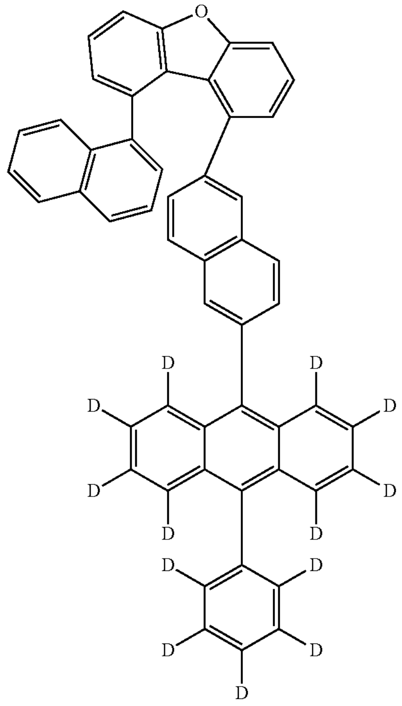

-continued
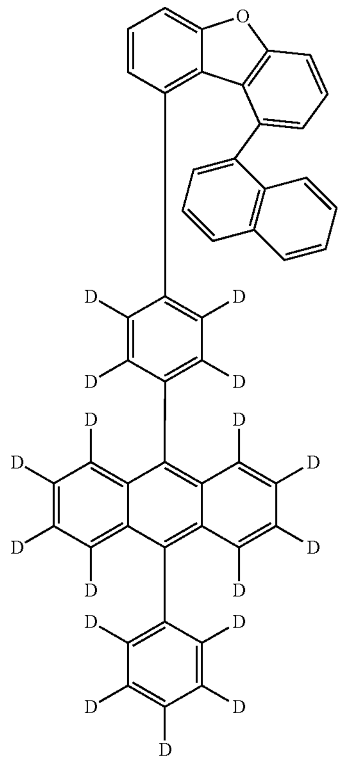
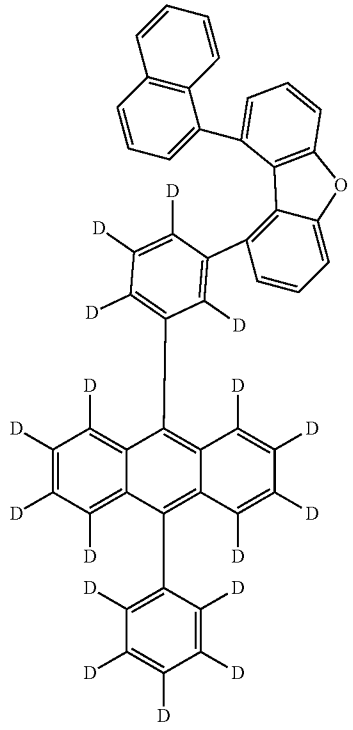
-continued
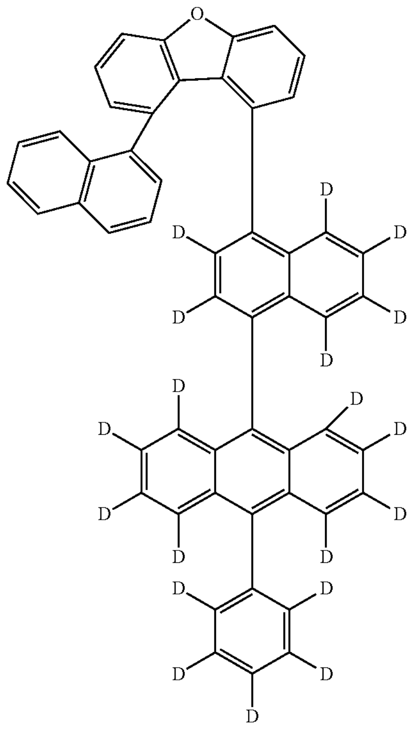
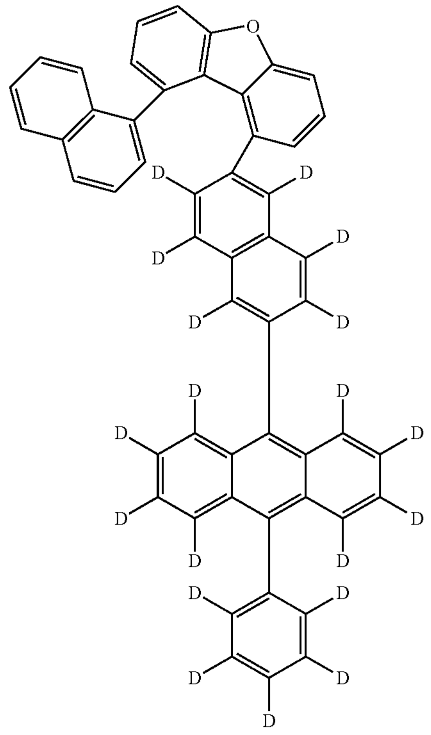

-continued
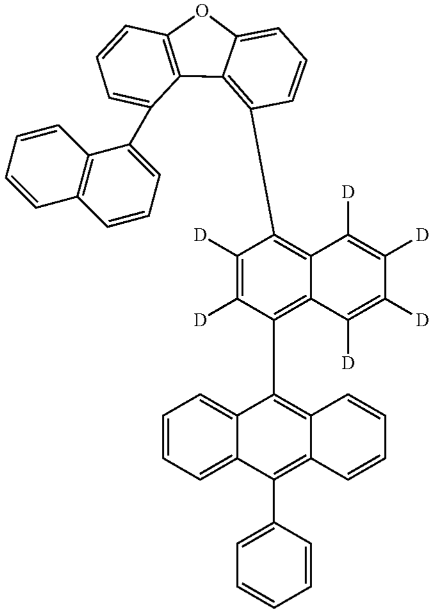
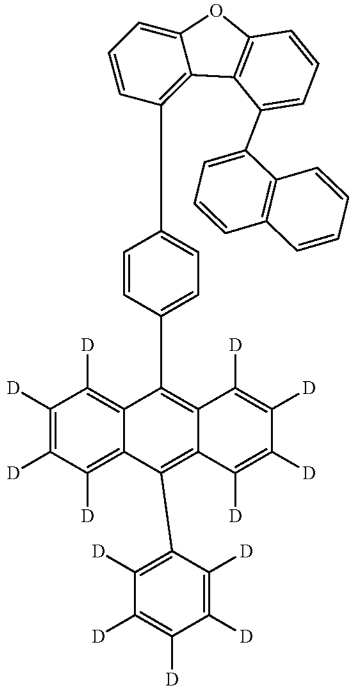
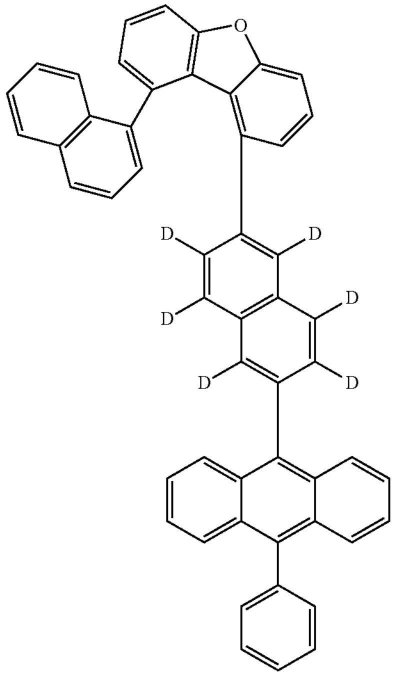
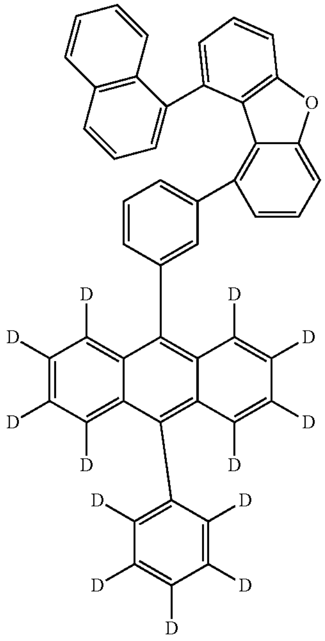

-continued
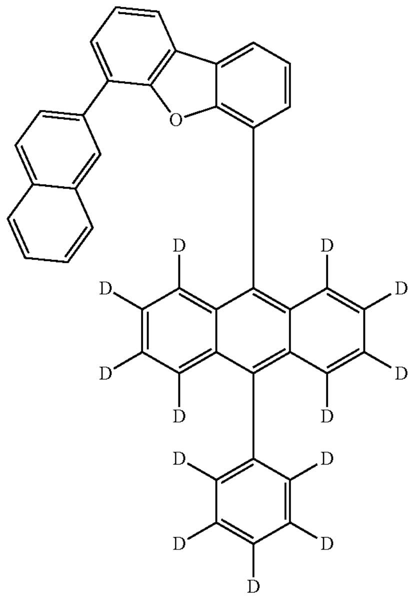
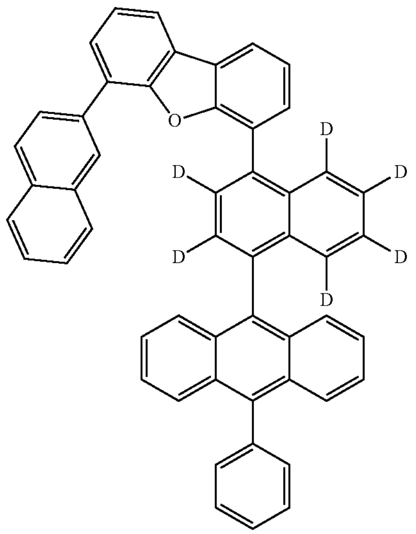
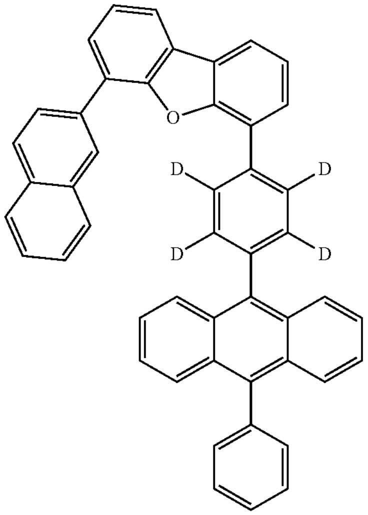
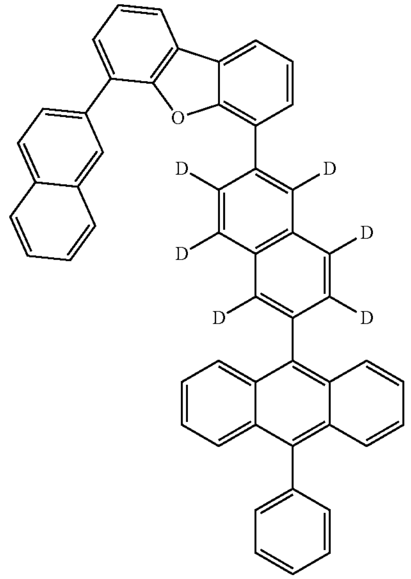
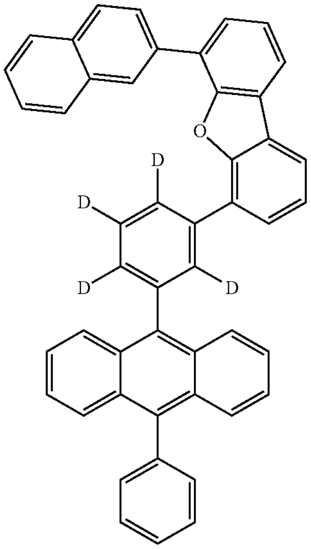
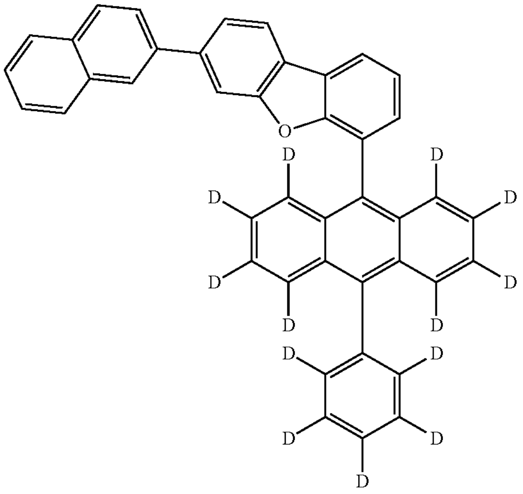

-continued
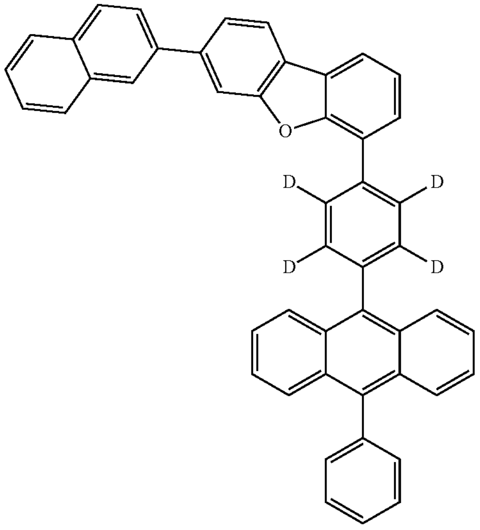
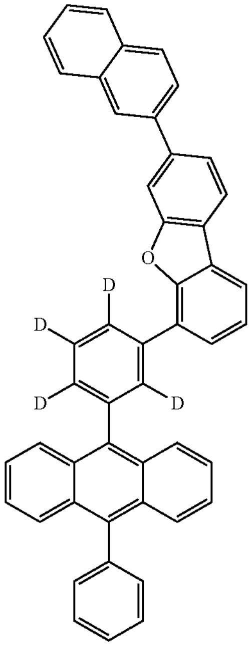
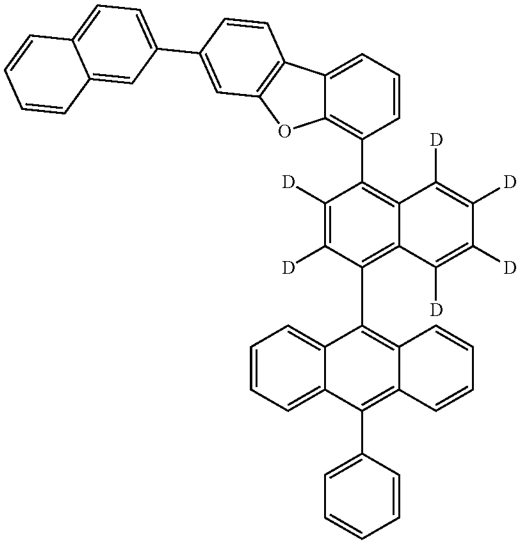
-continued
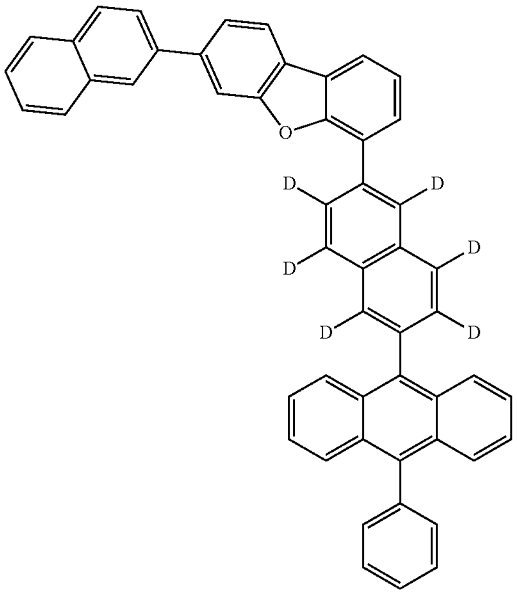
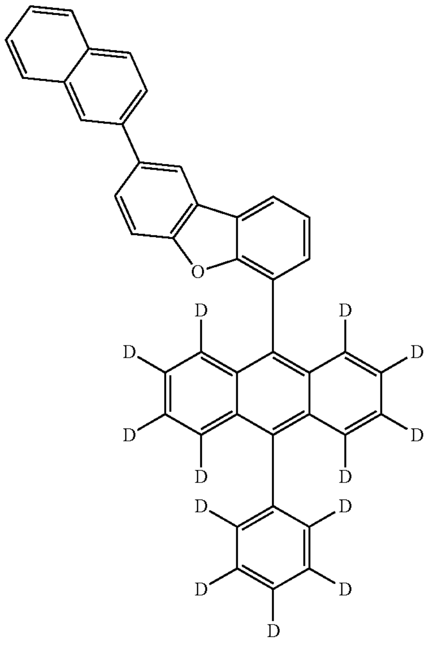

-continued
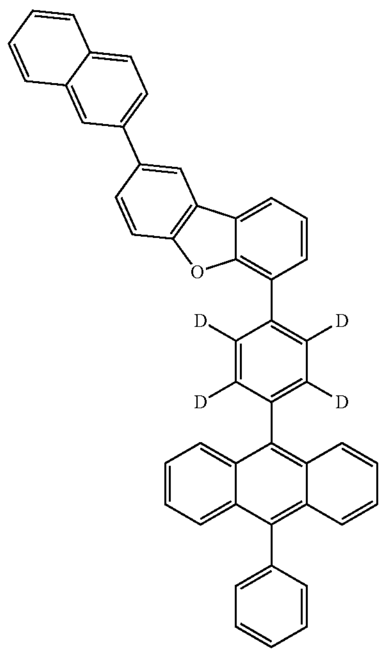
-continued
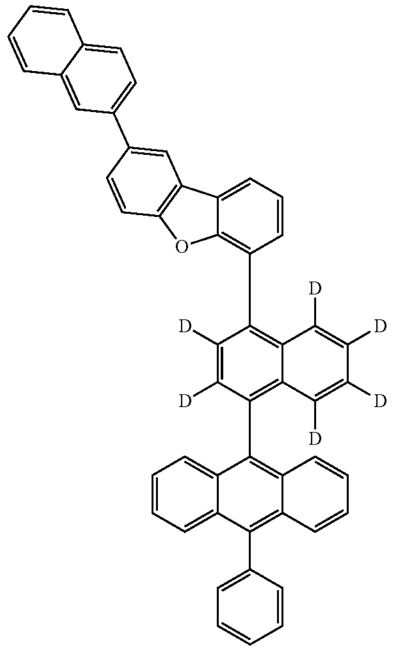
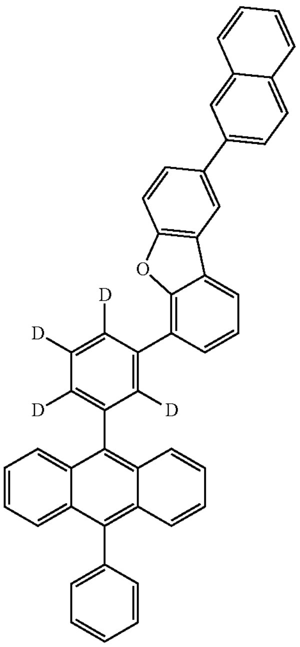
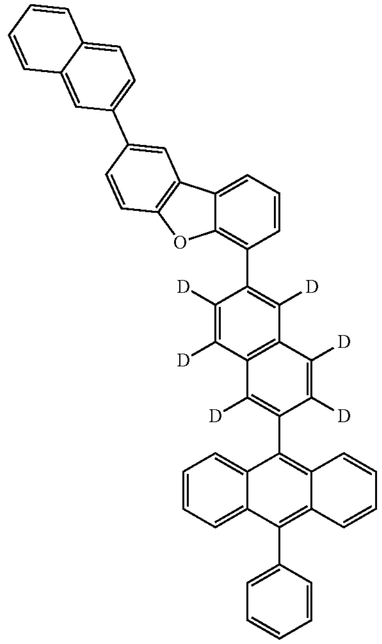

-continued
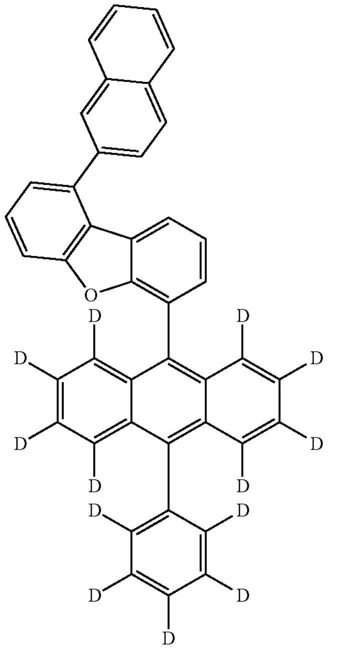
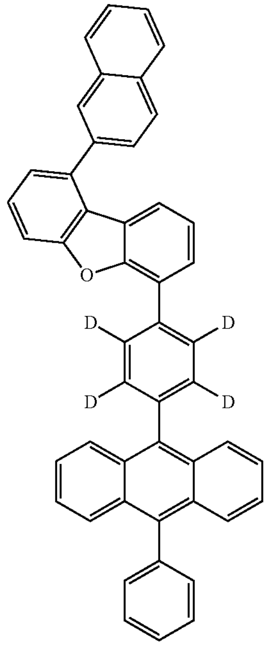
-continued
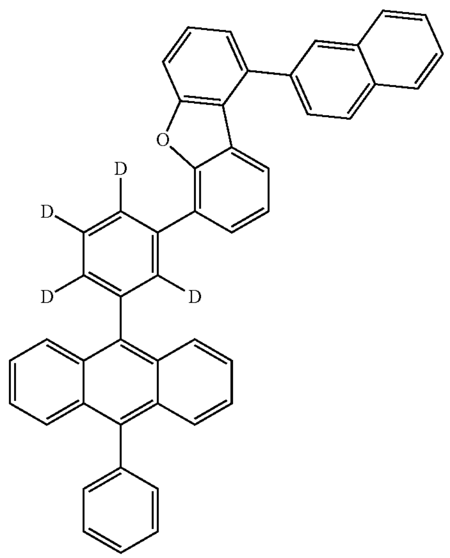
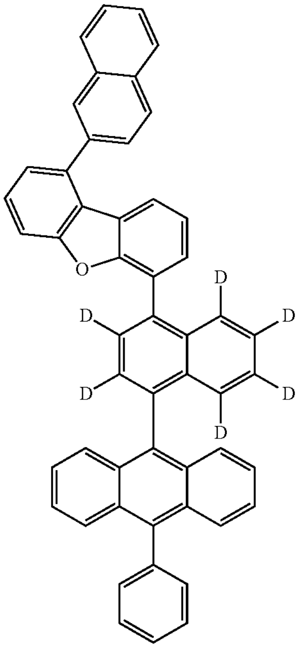

-continued
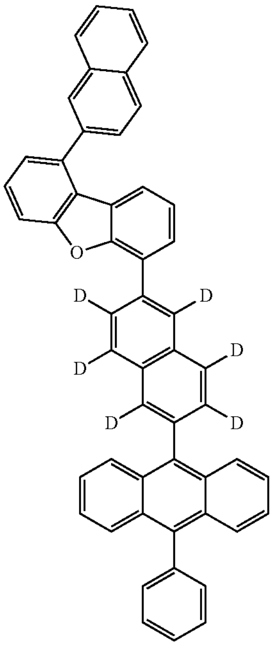
-continued
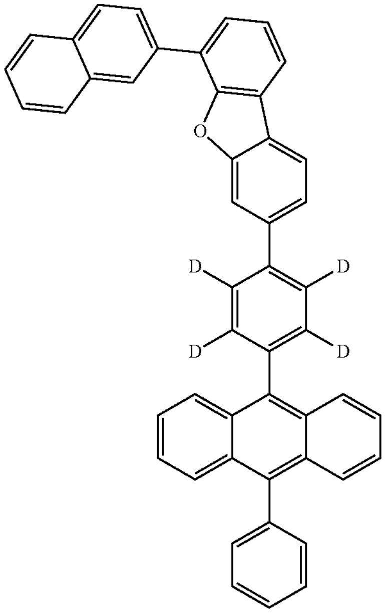
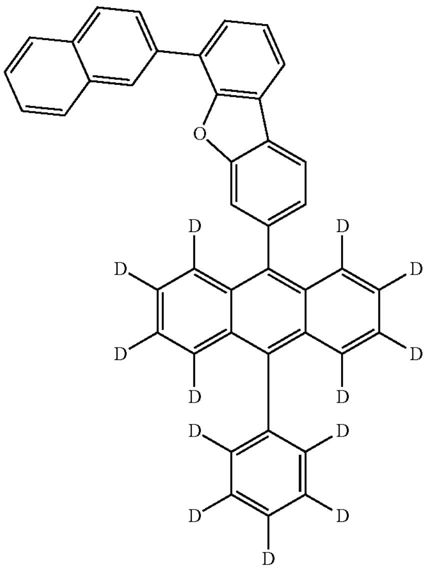
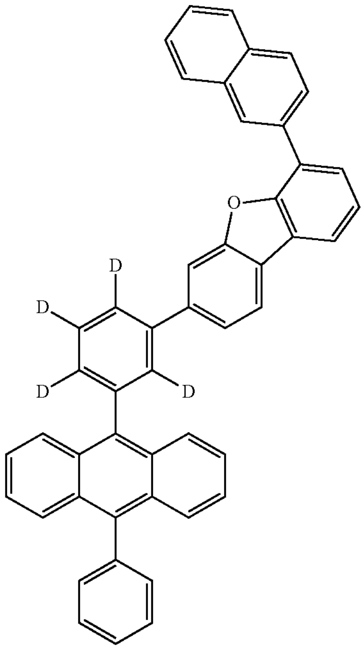

-continued
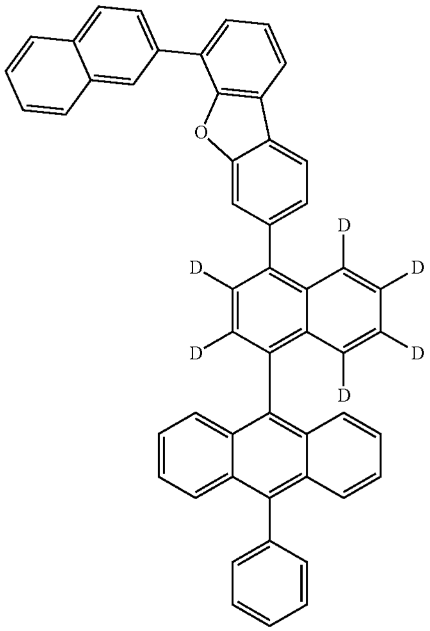
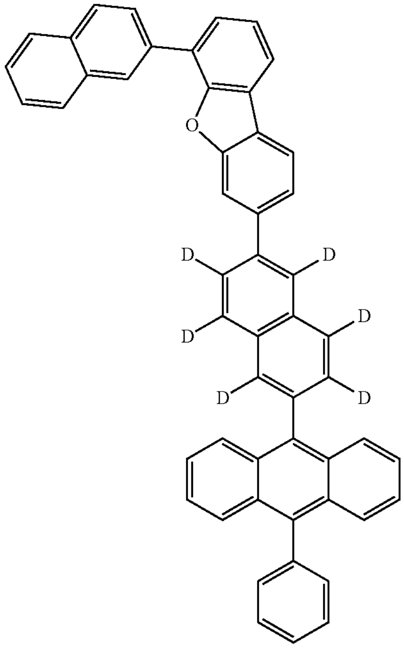
-continued
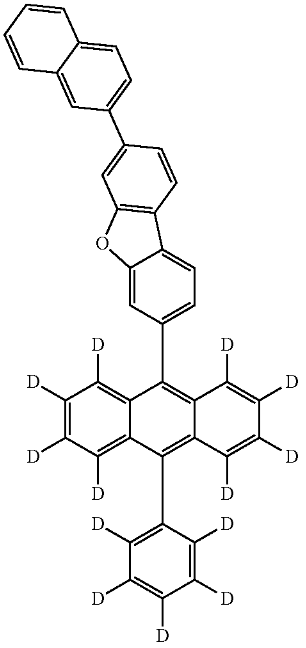
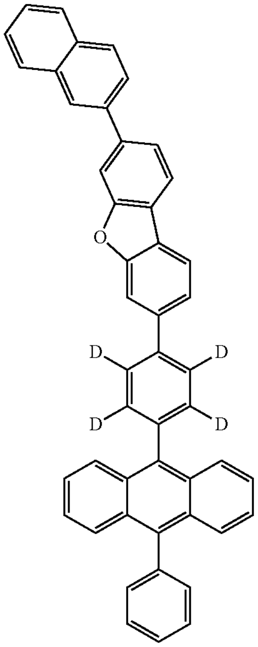
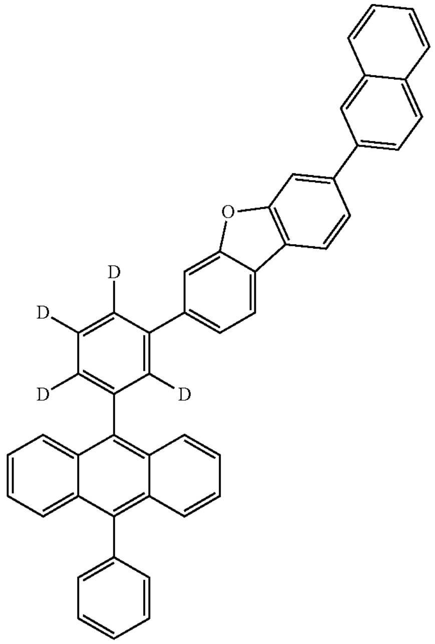

-continued
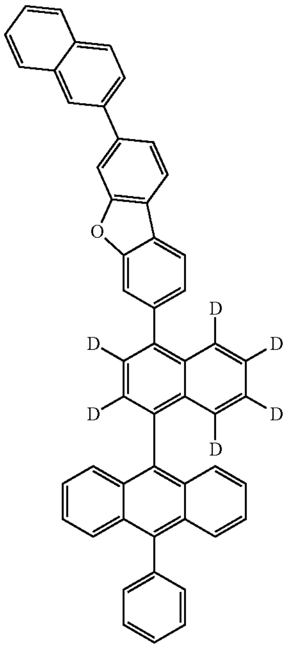
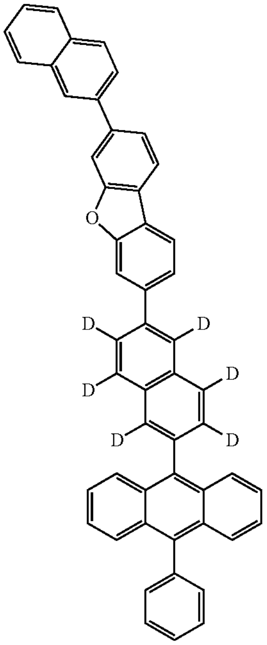
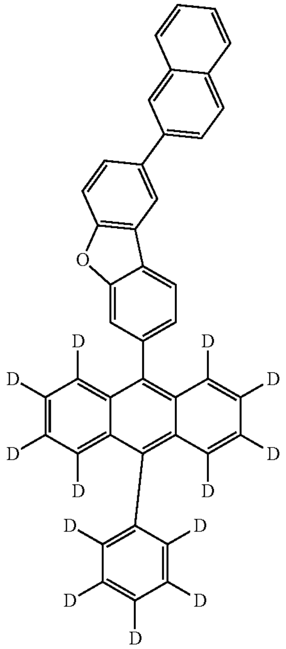
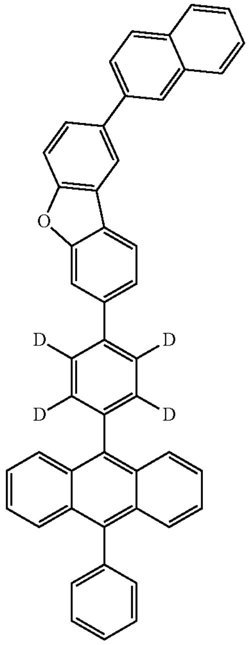
-continued
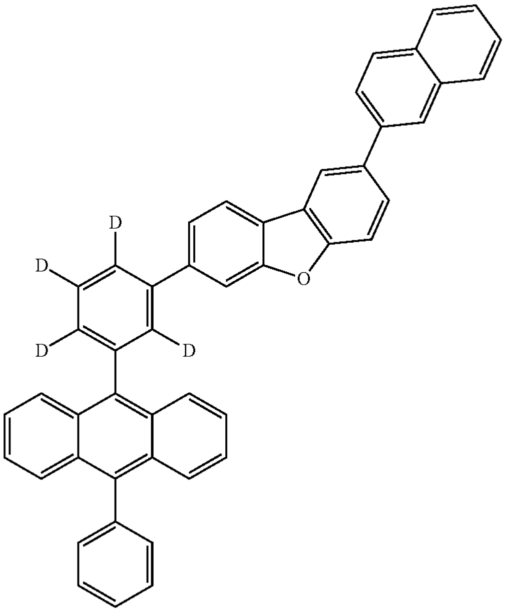 [SMILES: [2H]c1c([2H])c(-c2ccc3c(c2)oc2ccc(-c4ccc5ccccc5c4)cc23)c([2H])c(-c2c3ccccc3c(-c3ccccc3)c3ccccc23)c1[2H]]
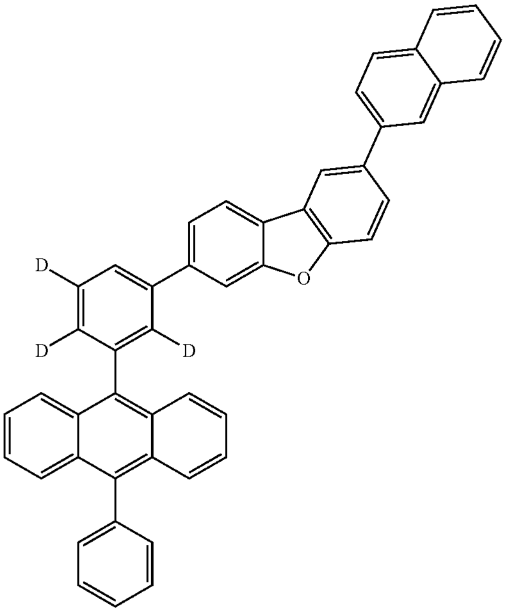

-continued
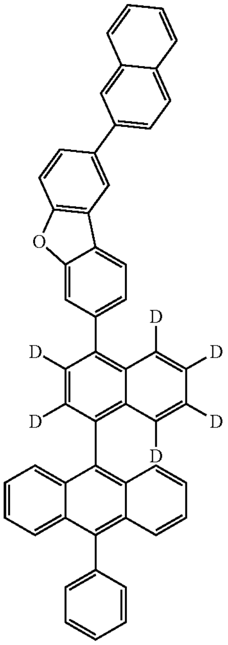
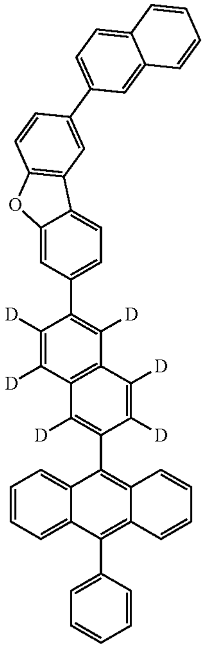
-continued
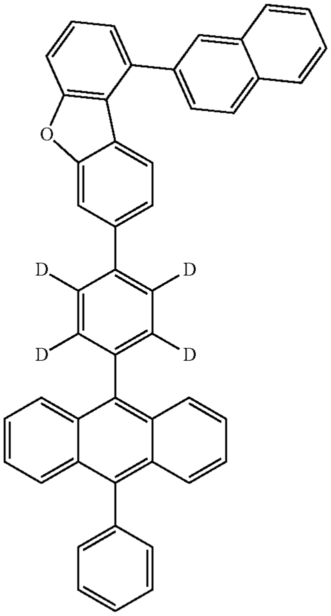
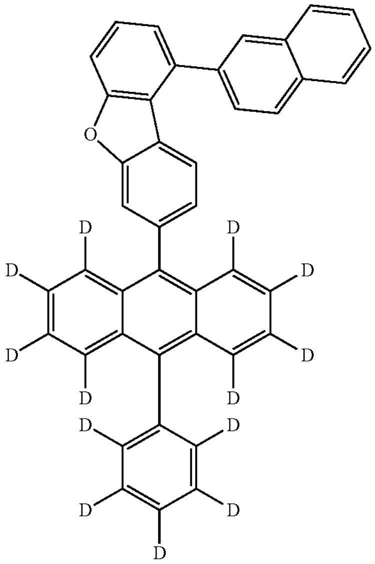
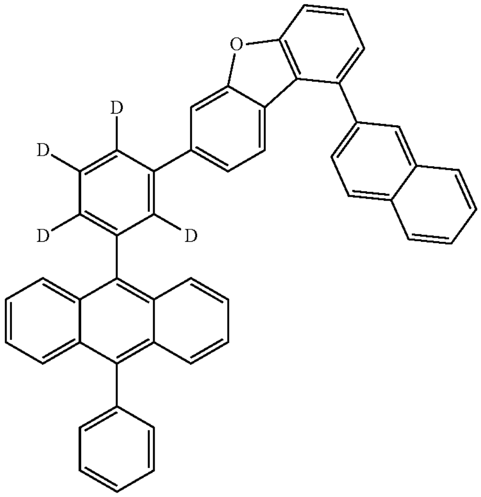

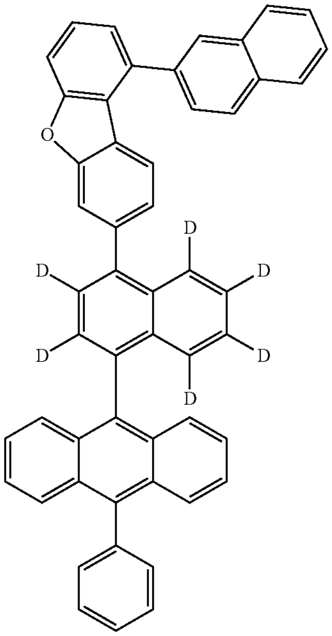
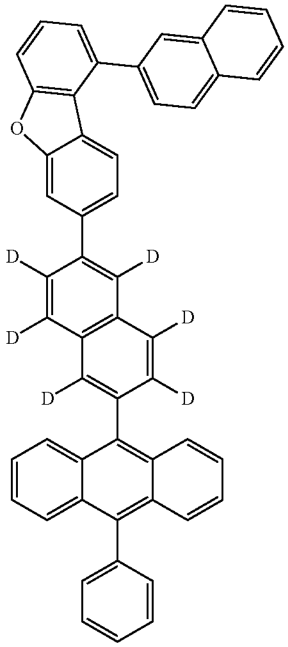
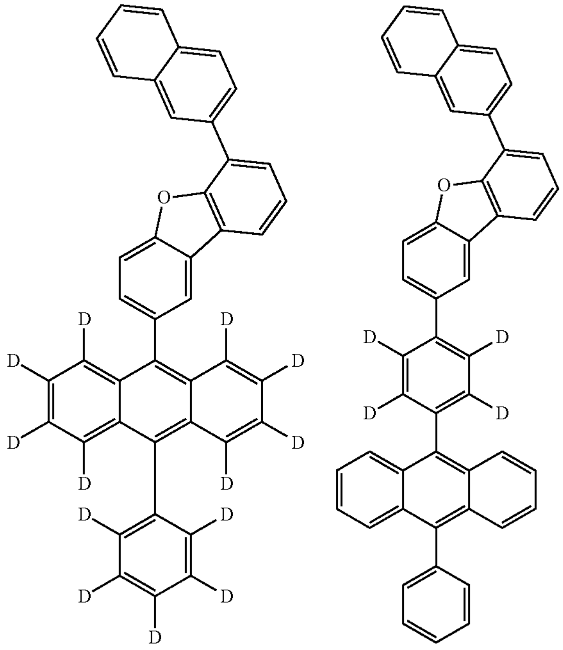
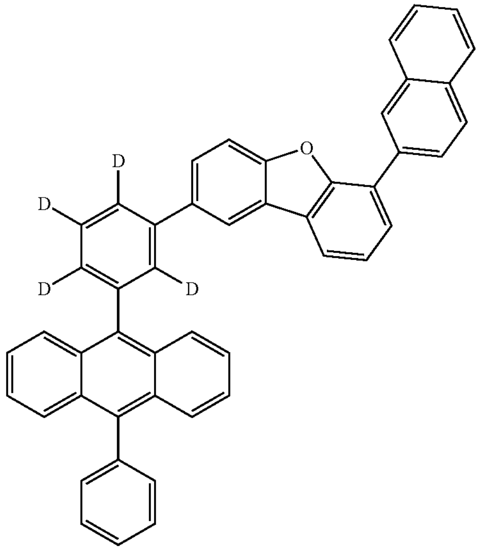

-continued
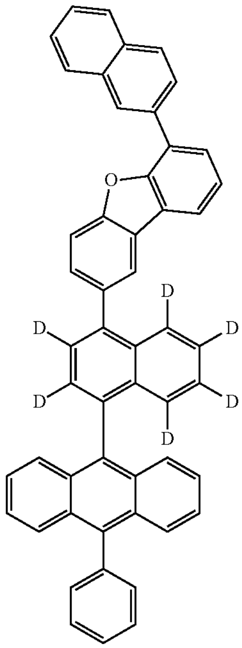
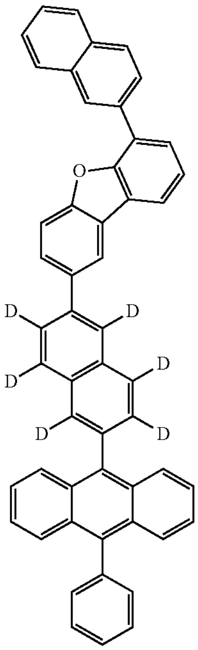
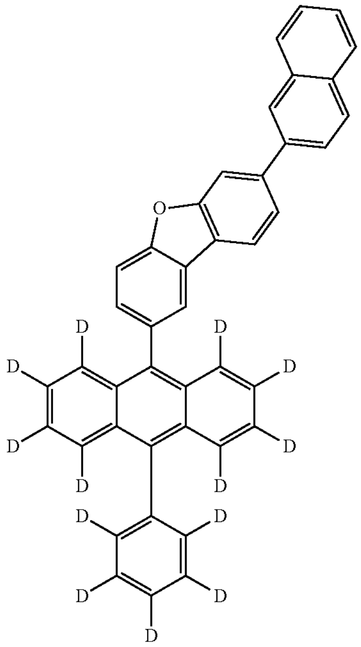
-continued
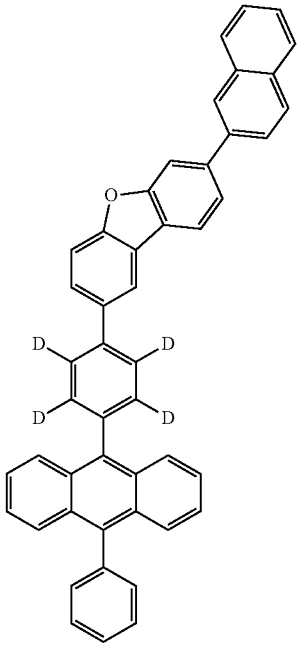
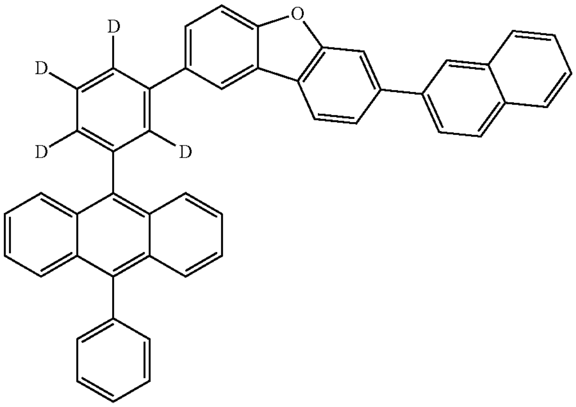
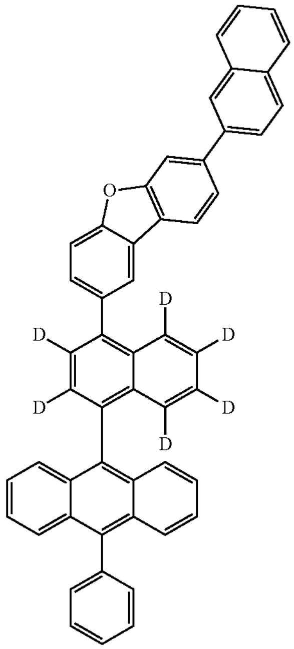
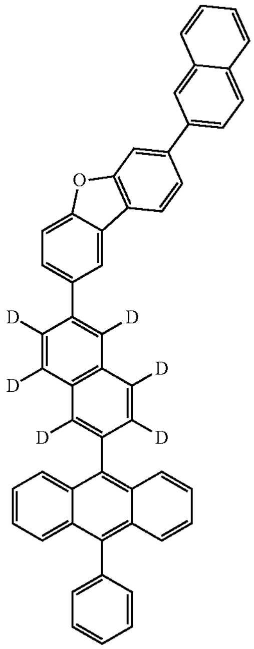

-continued
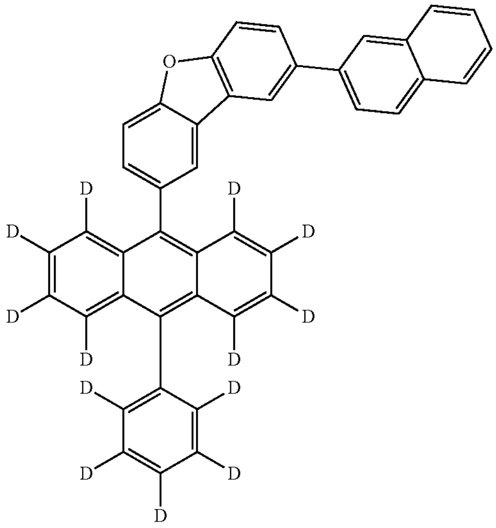
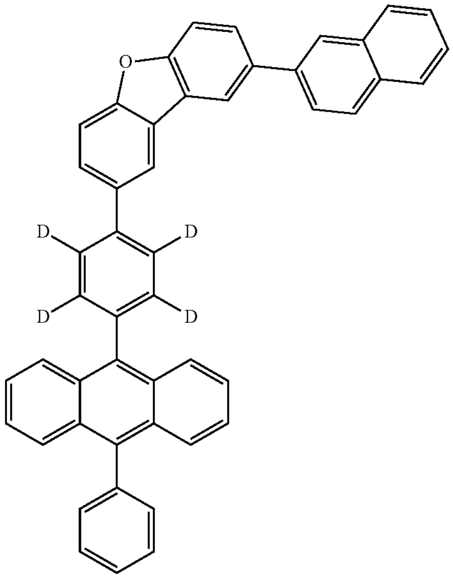
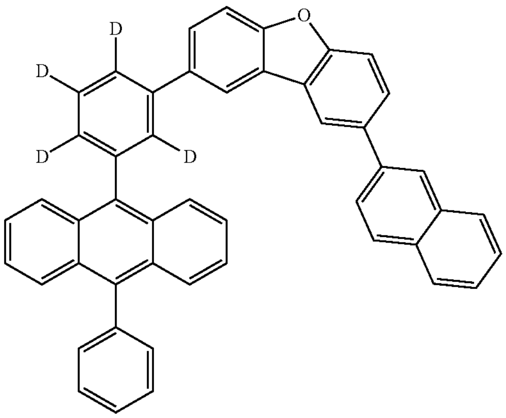
-continued
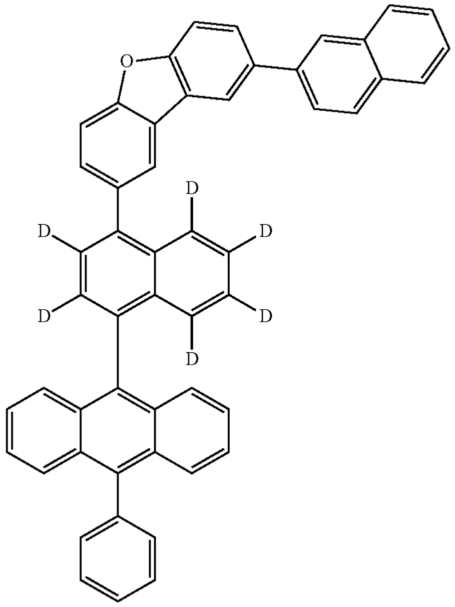
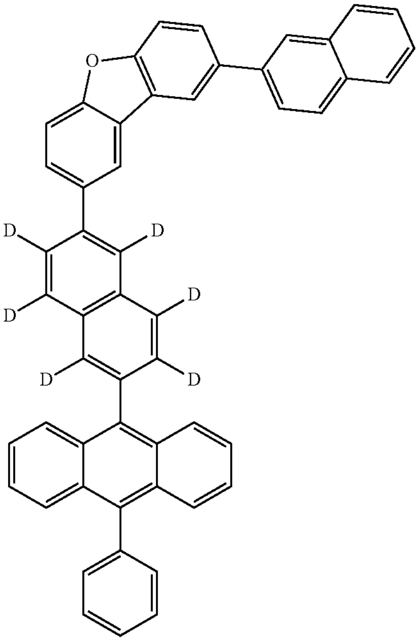

-continued
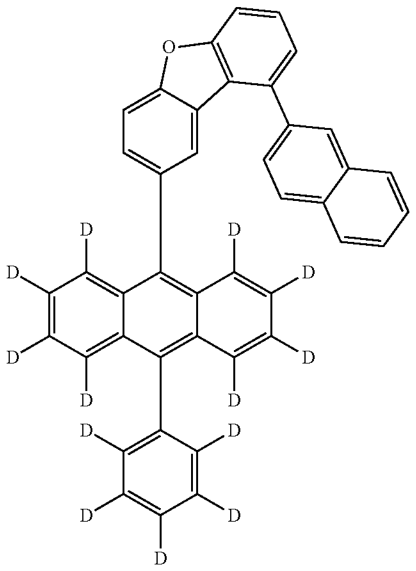
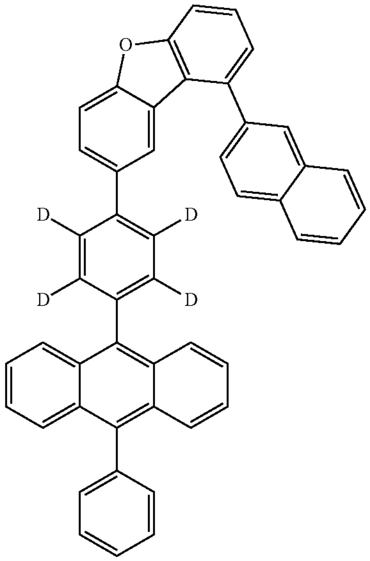
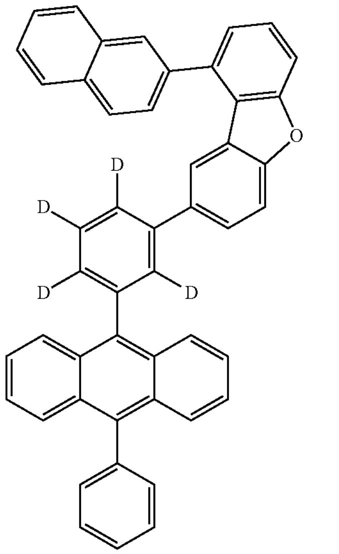
-continued
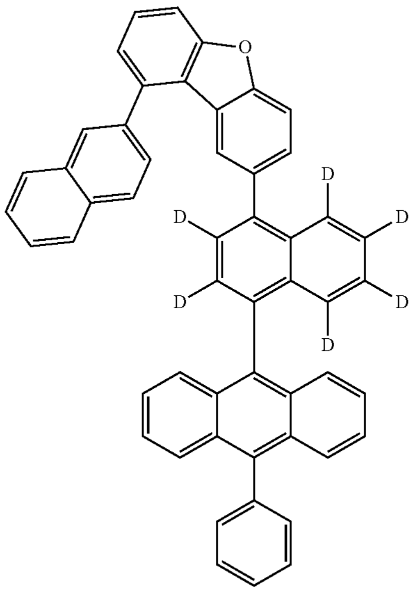
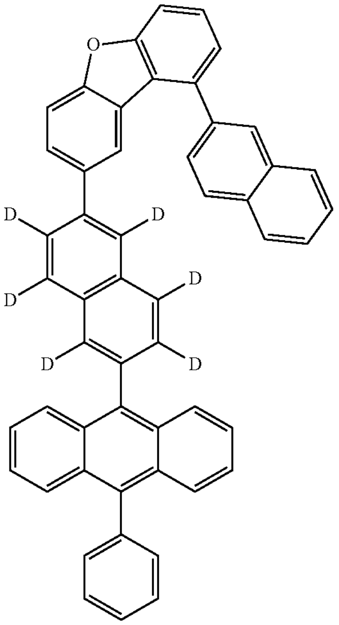

-continued
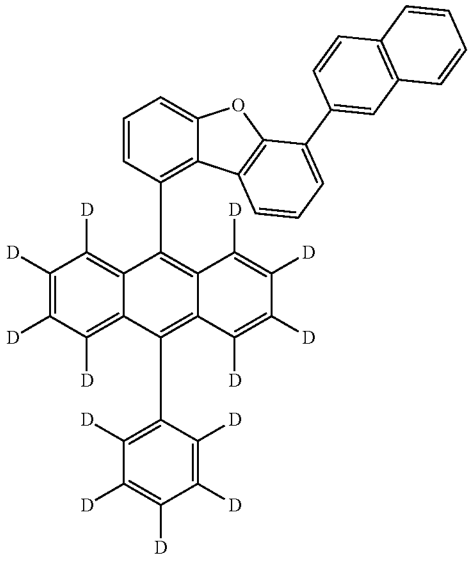
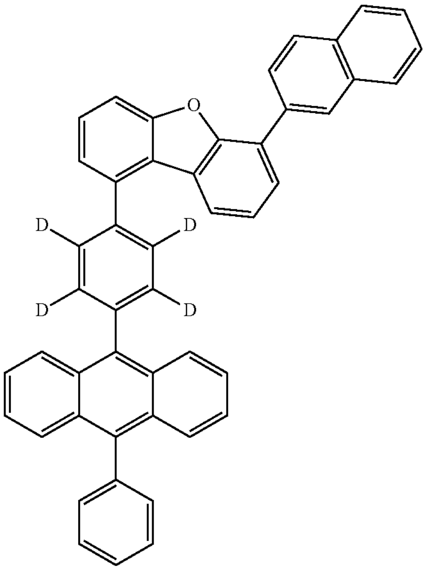
-continued
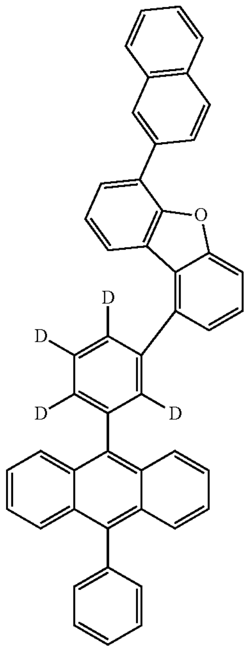
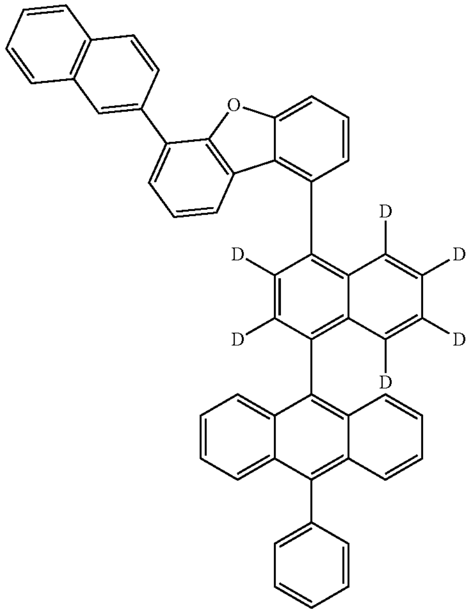

-continued
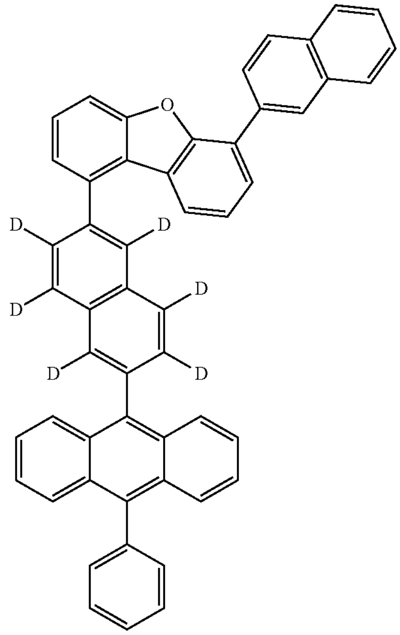
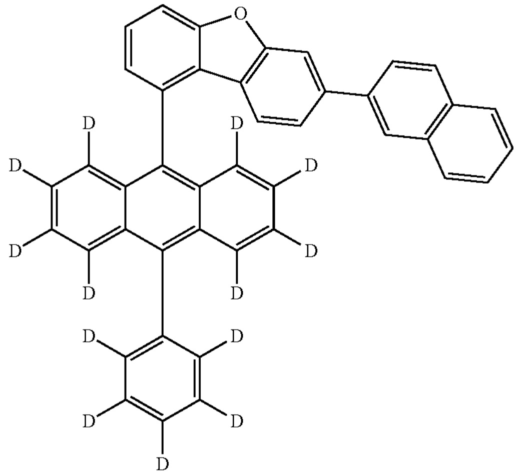
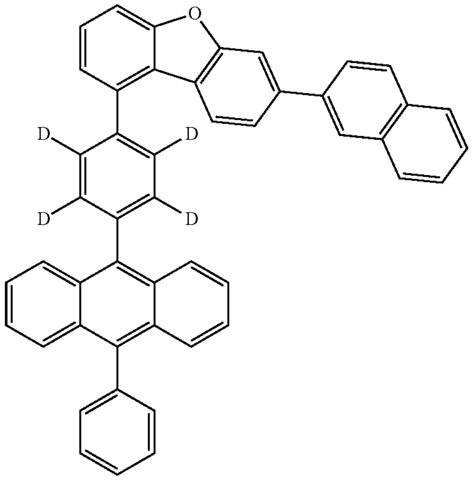
-continued
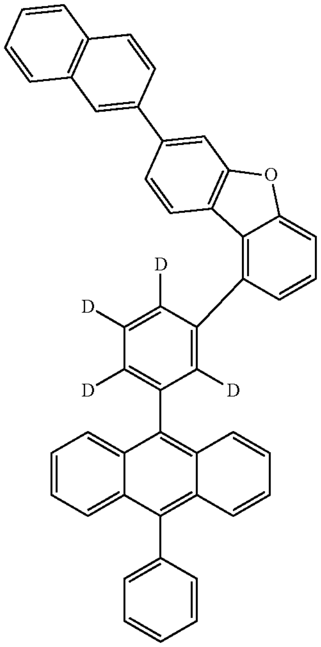
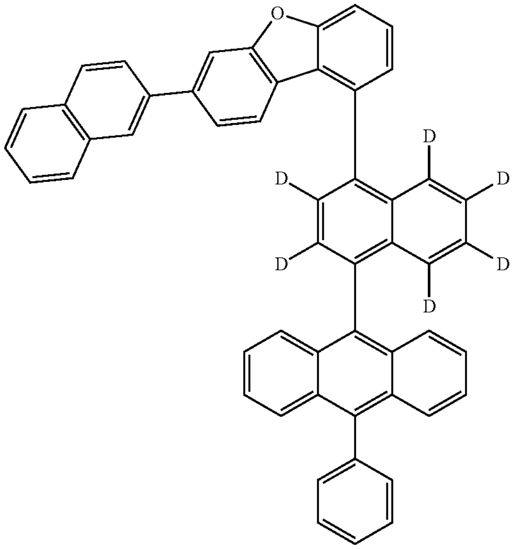

-continued
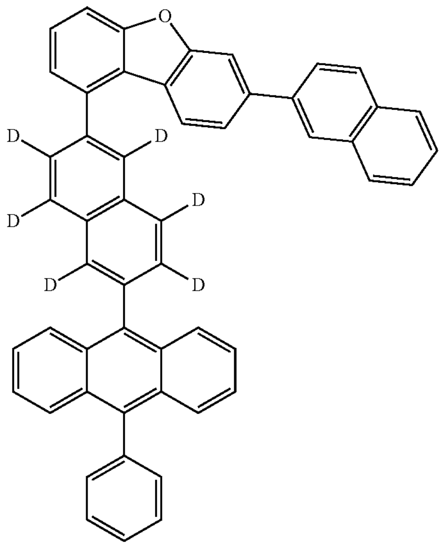
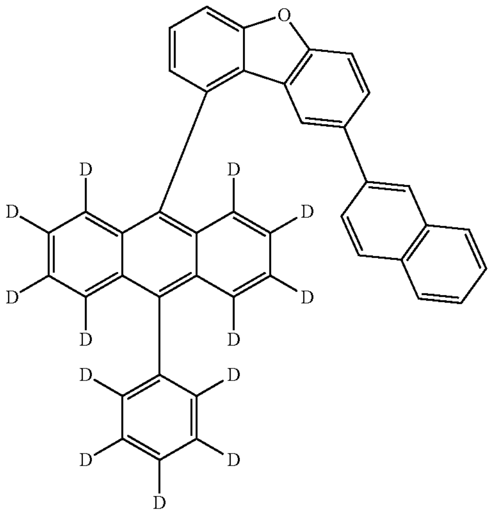
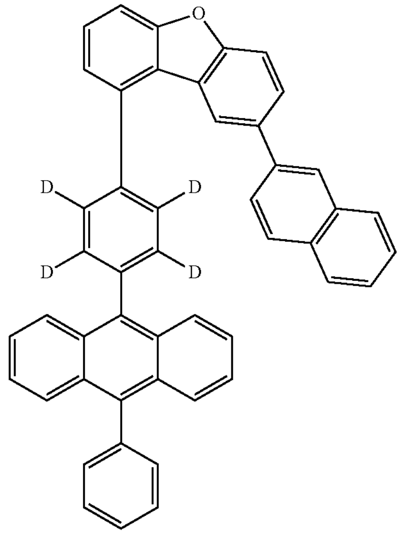
-continued
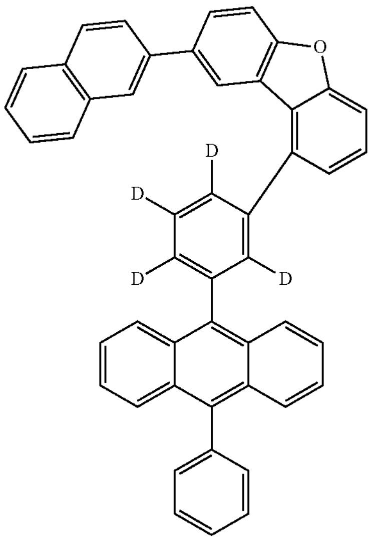
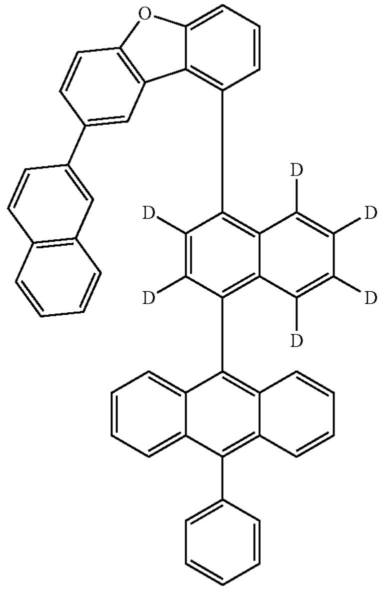

-continued
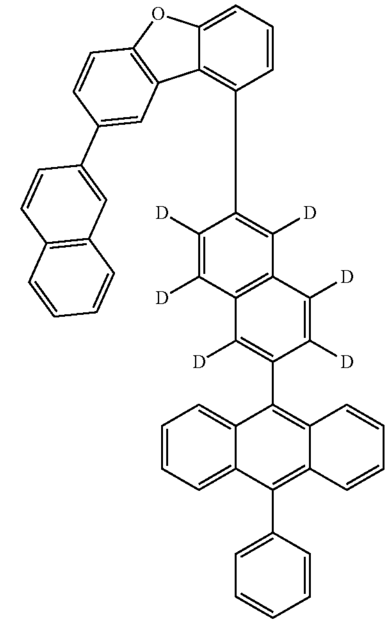
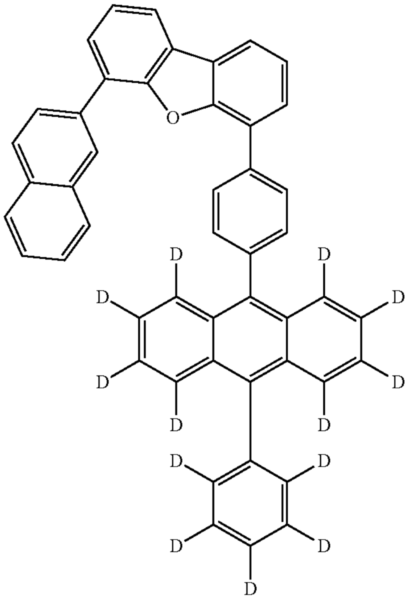
-continued
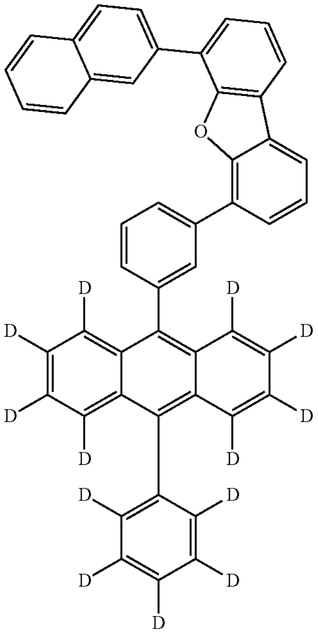
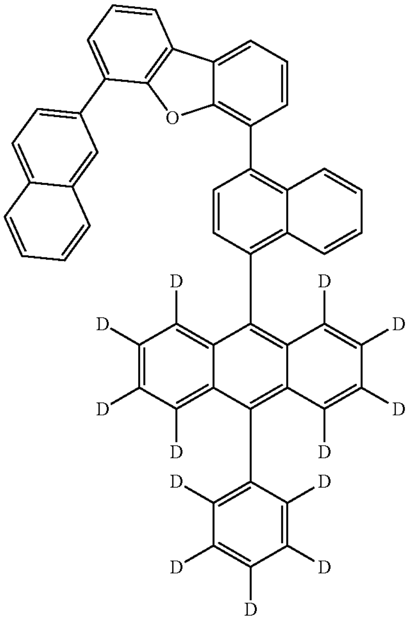

-continued
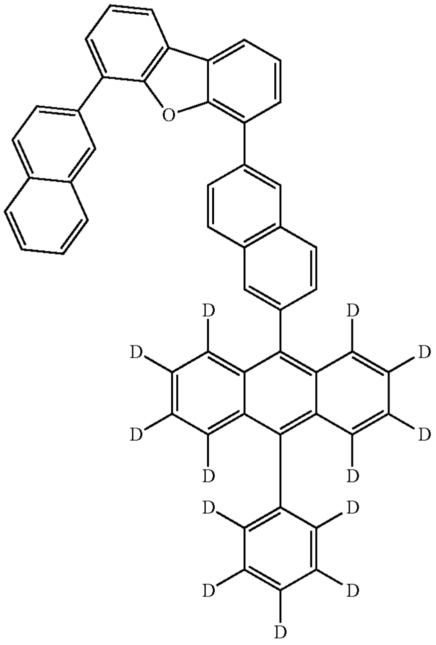
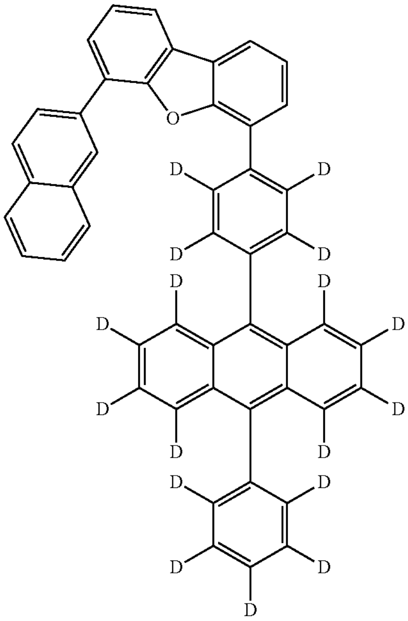 [SMILES: [2H]c1c([2H])c([2H])c(-c2c3c([2H])c([2H])c([2H])c([2H])c3c(-c3c([2H])c([2H])c(-c4cccc5c4oc4c(-c6ccc7ccccc7c6)cccc45)c([2H])c3[2H])c3c([2H])c([2H])c([2H])c([2H])c23)c([2H])c1[2H]]
-continued
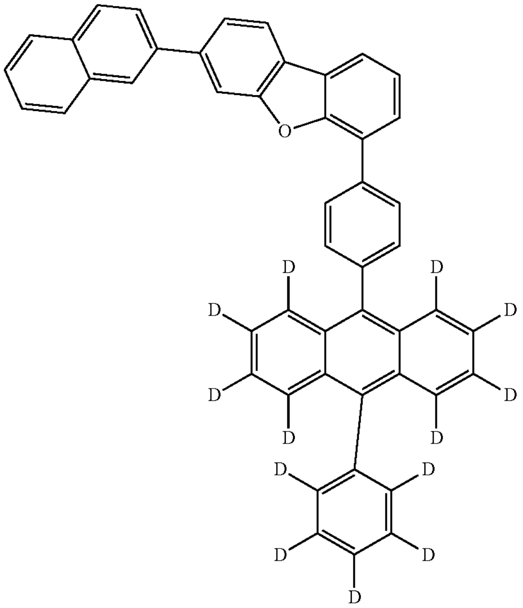
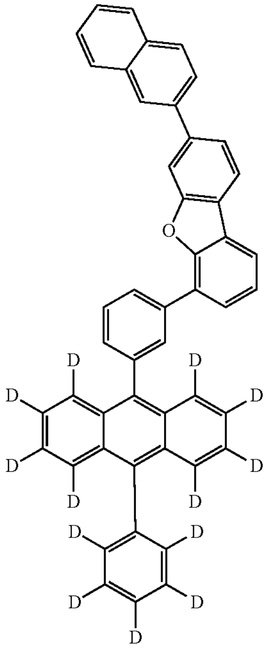

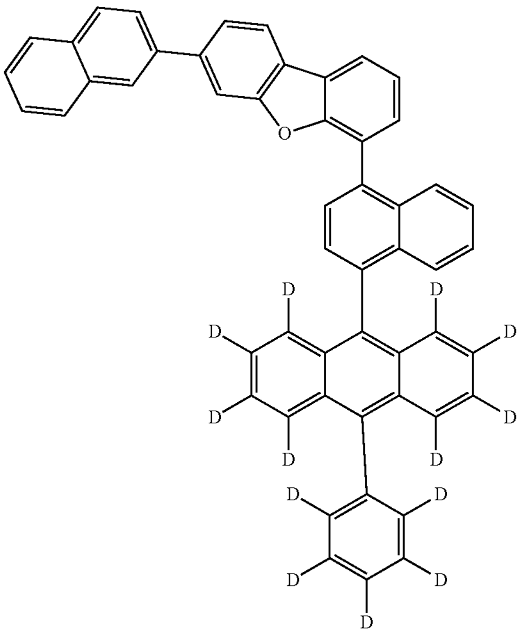
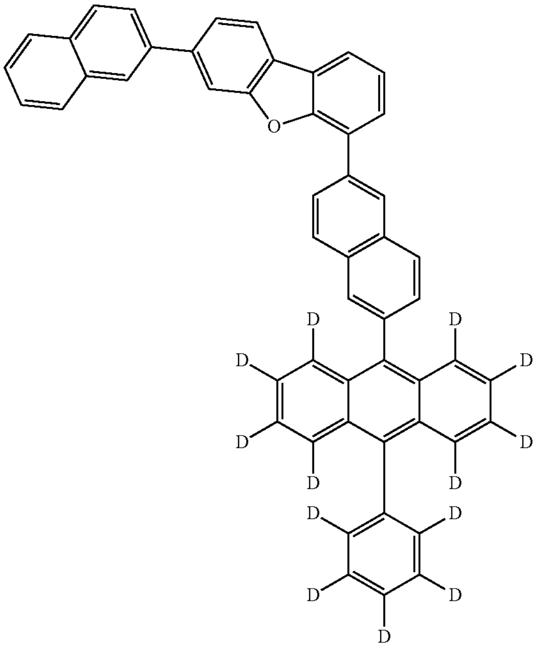
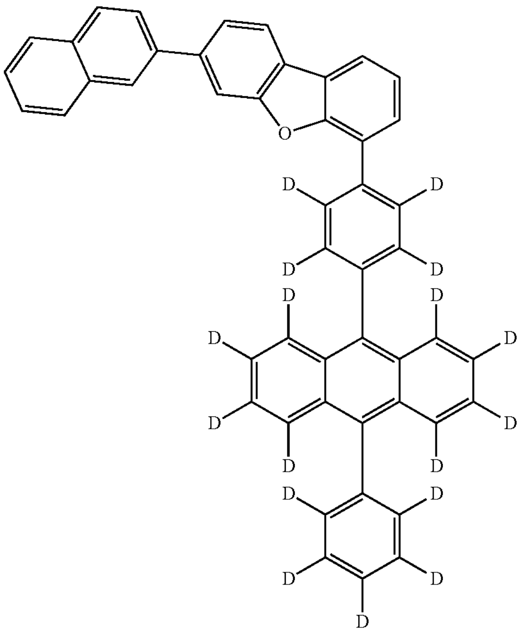
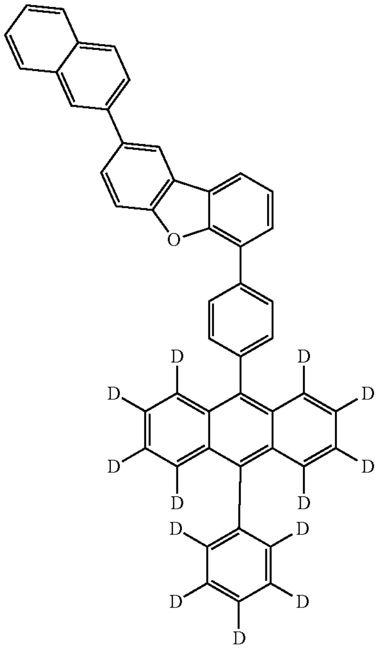

-continued
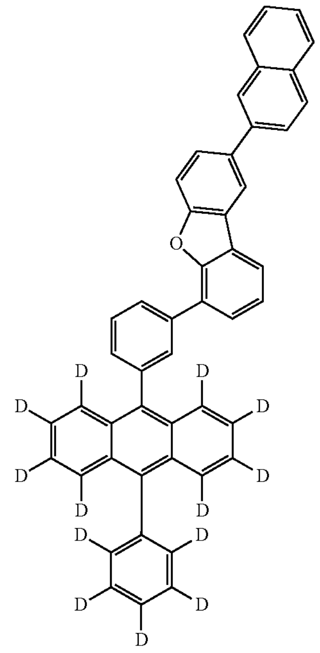
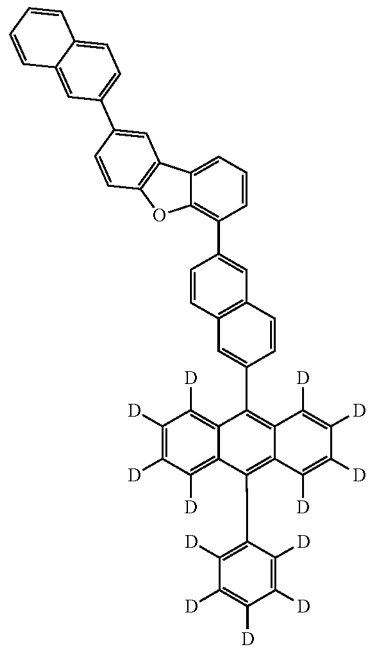
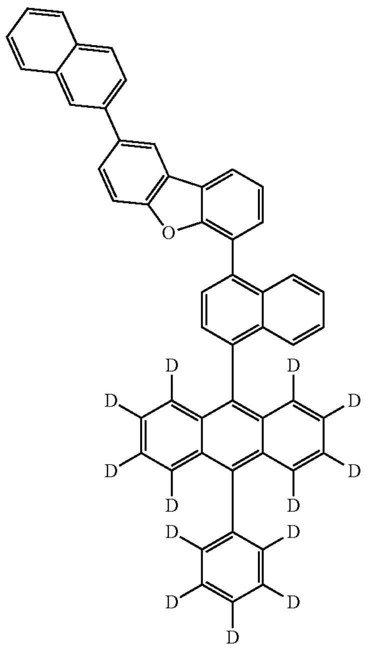
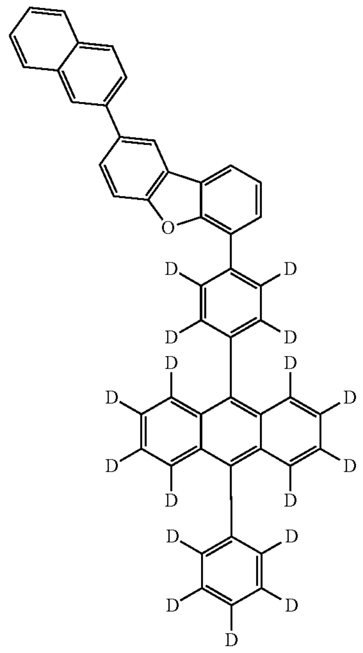
-continued

-continued
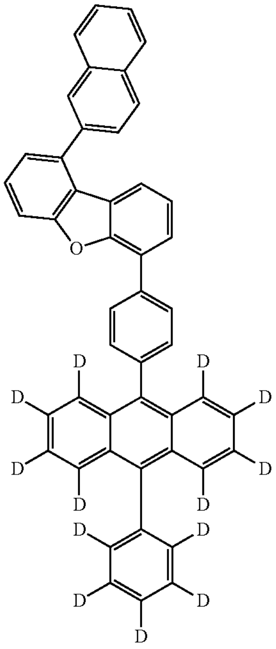
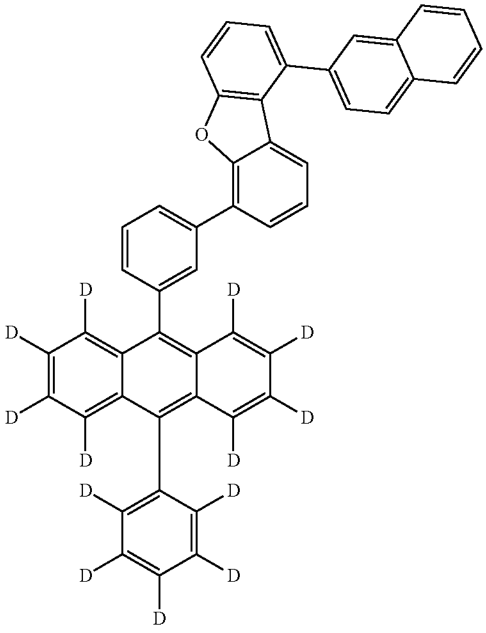
-continued
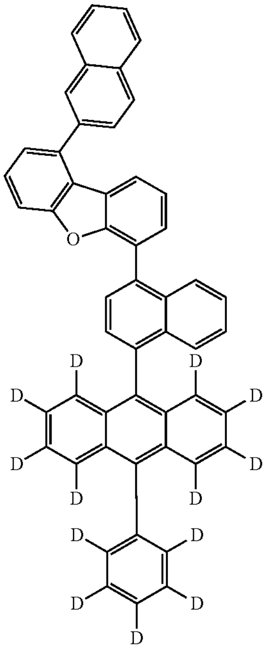
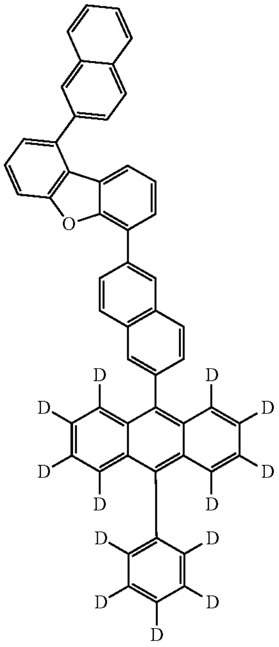
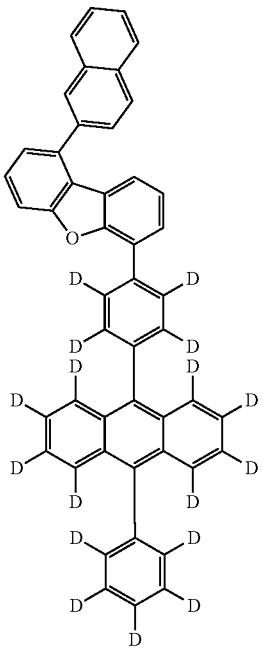

-continued
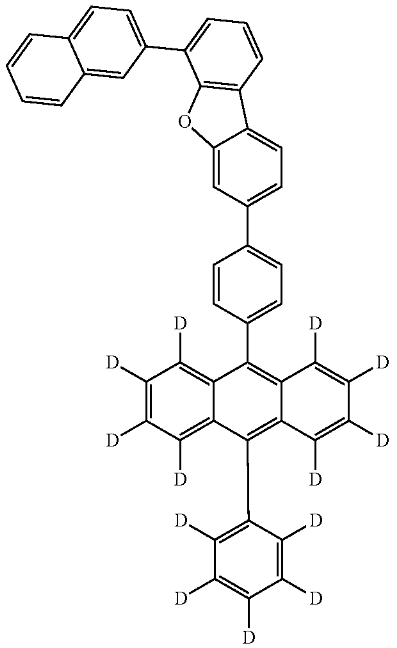
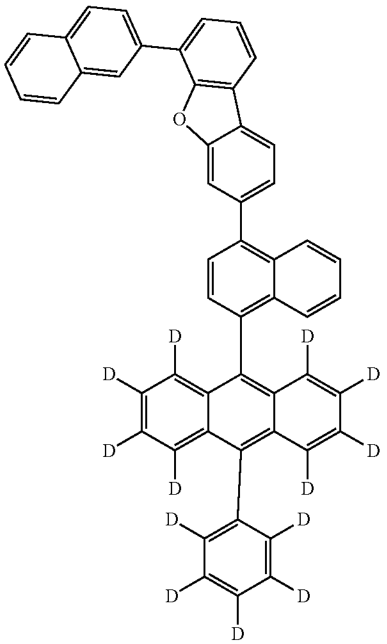
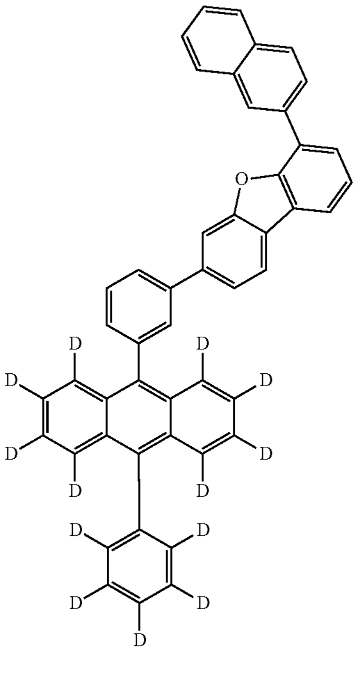 [SMILES: [2H]c1c([2H])c([2H])c(-c2c3c([2H])c([2H])c([2H])c([2H])c3c(-c3cccc(-c4ccc5c(c4)oc4c(-c6ccc7ccccc7c6)cccc45)c3)c3c([2H])c([2H])c([2H])c([2H])c23)c([2H])c1[2H]]
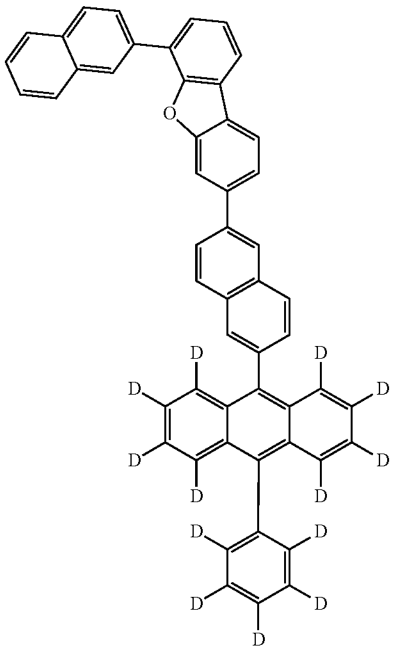
-continued

-continued
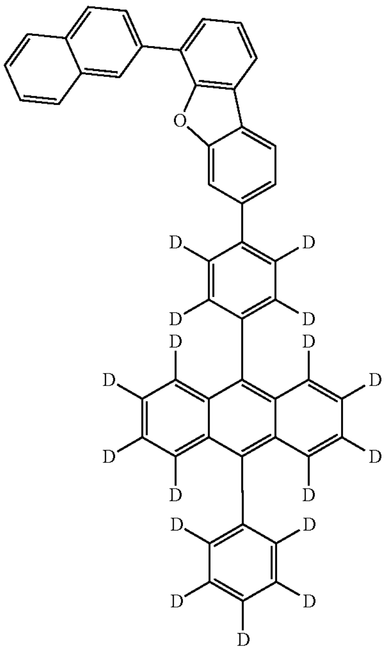
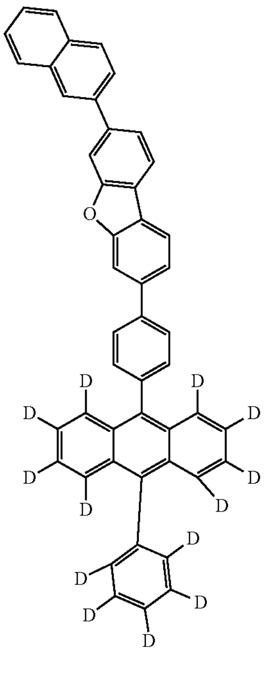
-continued
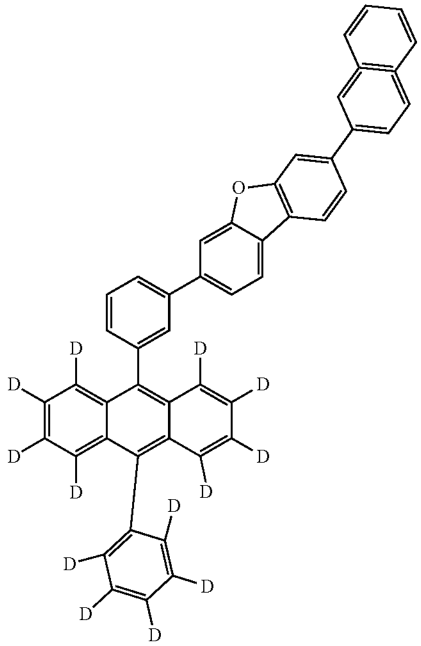
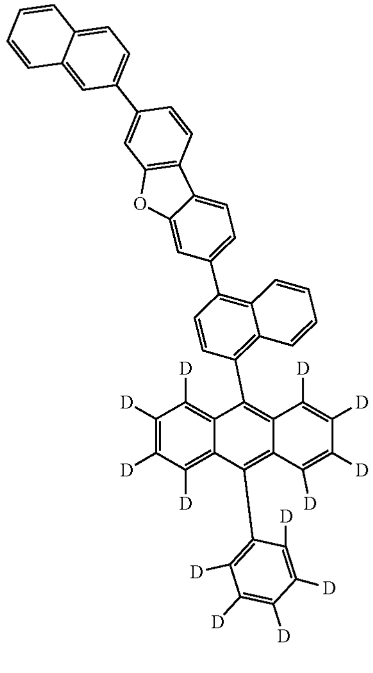

-continued
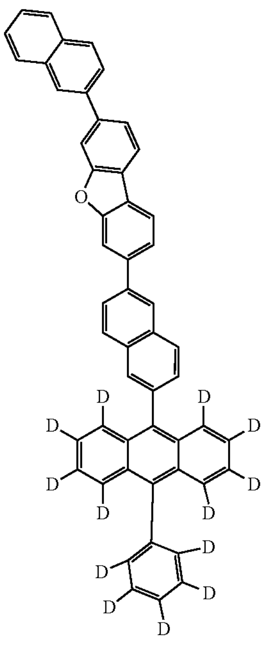
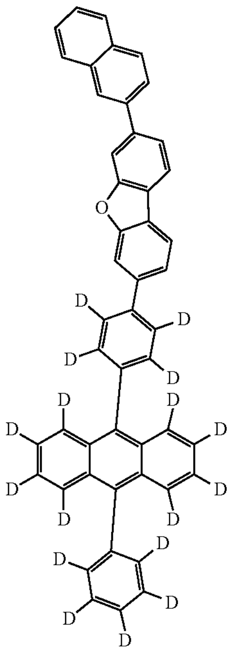
-continued
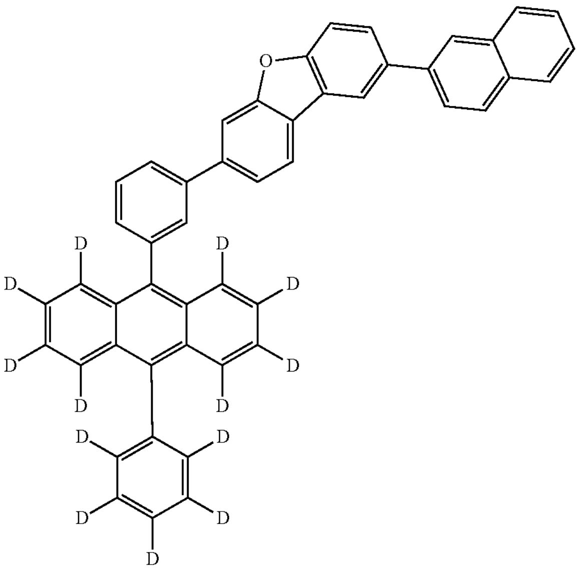
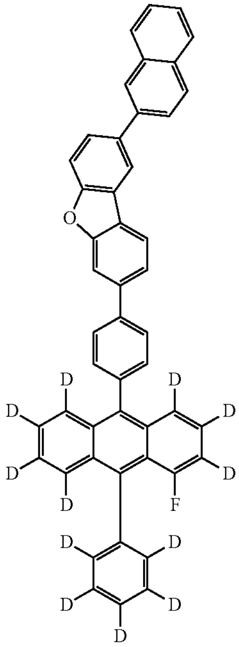
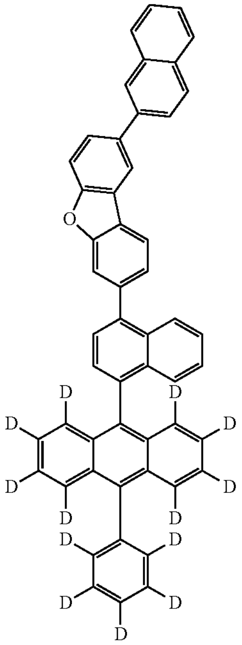
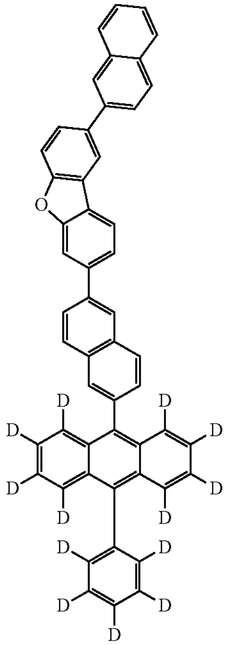

-continued
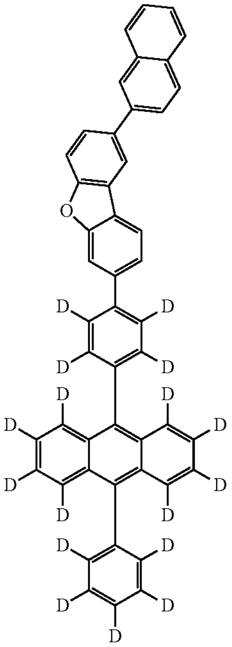
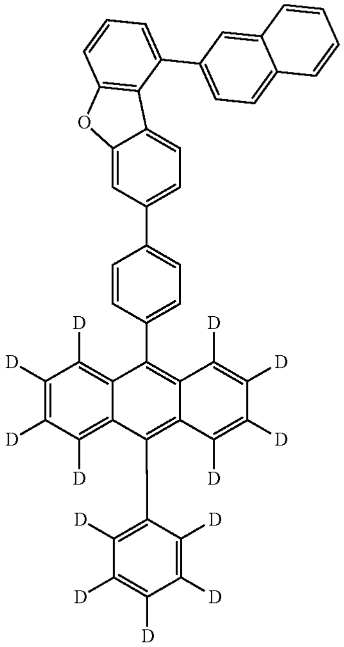
-continued
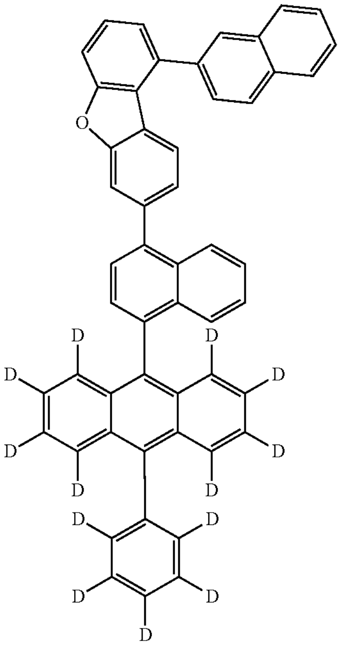
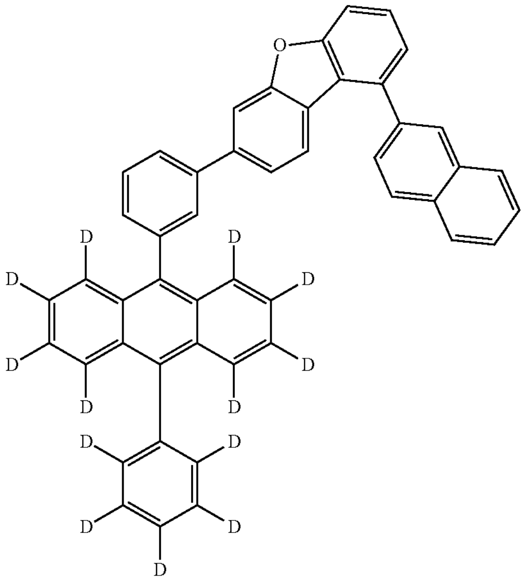 [SMILES: [2H]c1c([2H])c([2H])c(-c2c3c([2H])c([2H])c([2H])c([2H])c3c(-c3cccc(-c4ccc5c(c4)oc4cccc(-c6ccc7ccccc7c6)c45)c3)c3c([2H])c([2H])c([2H])c([2H])c23)c([2H])c1[2H]]
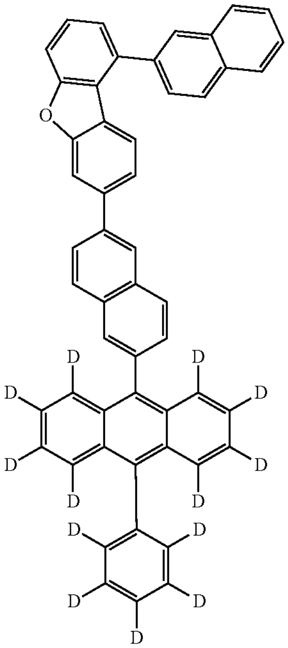

-continued
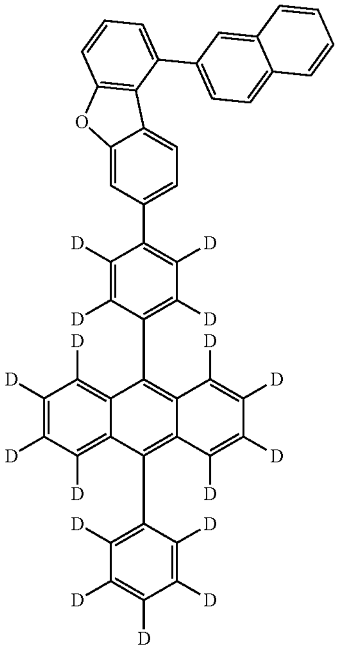
-continued
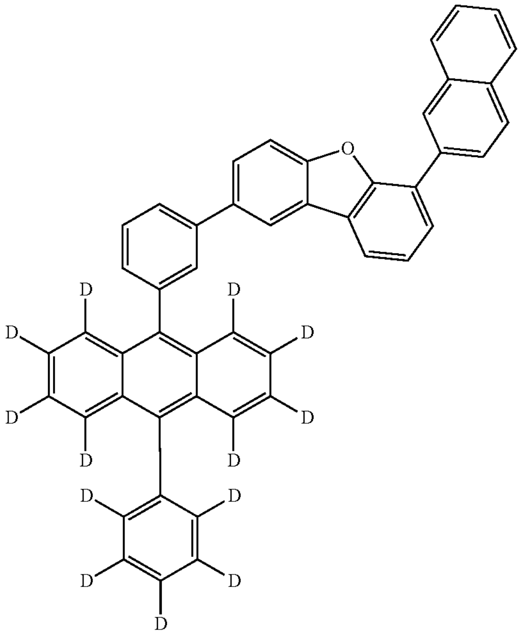
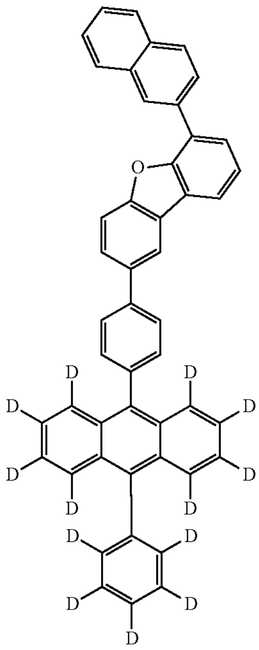
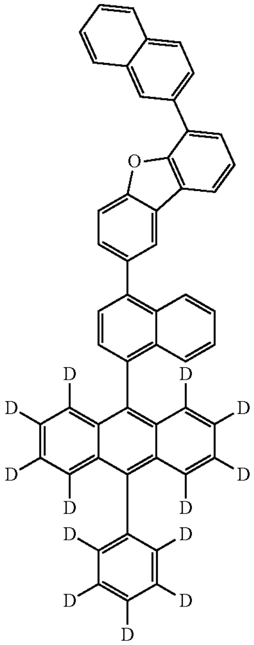
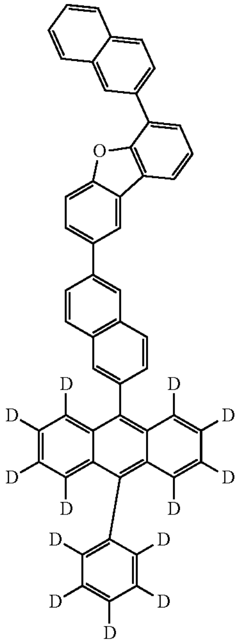

-continued
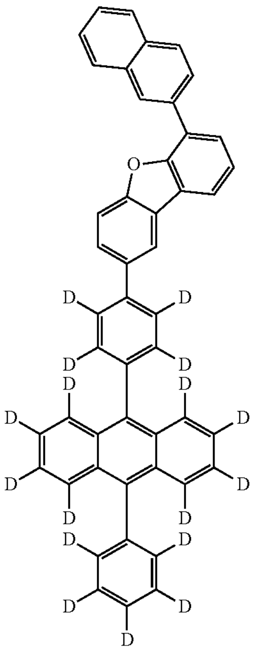
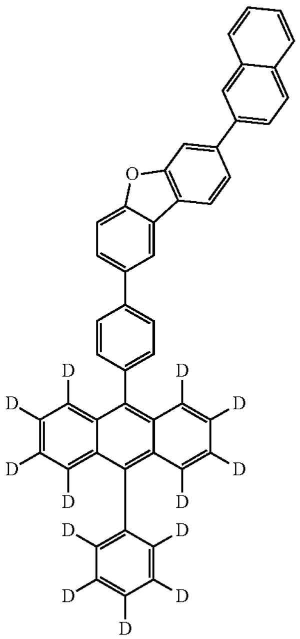
-continued
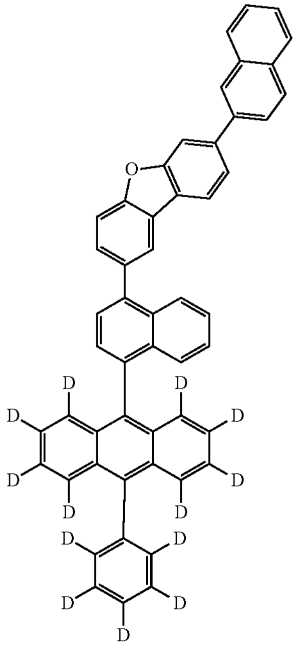
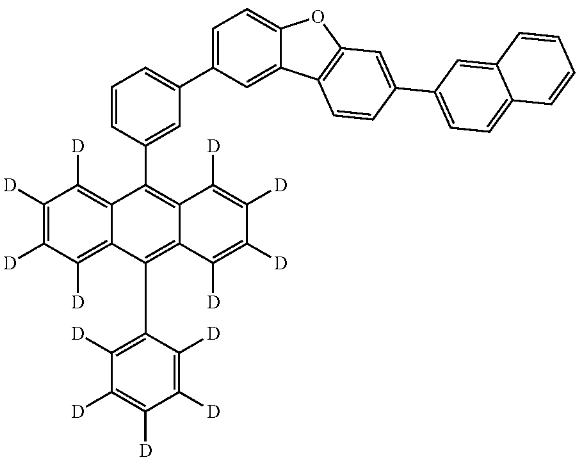
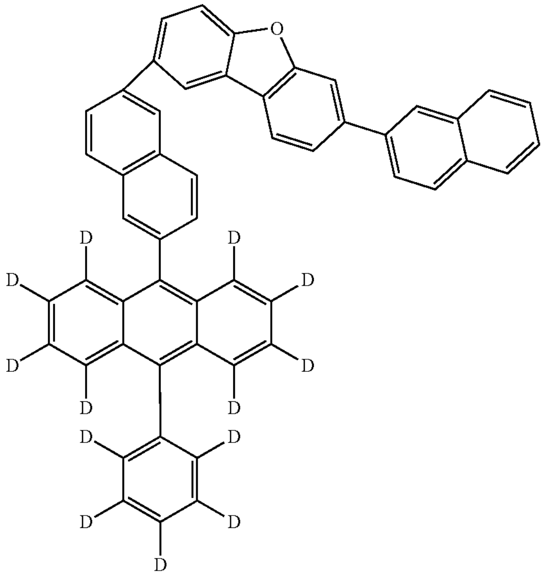

-continued
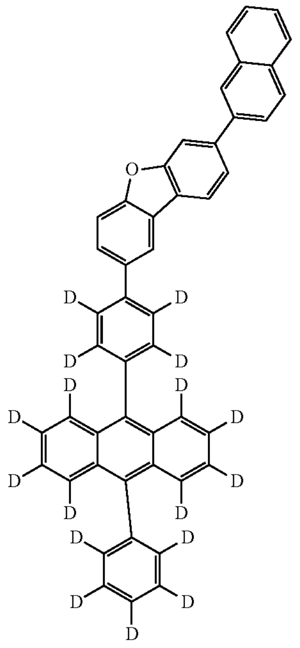
-continued
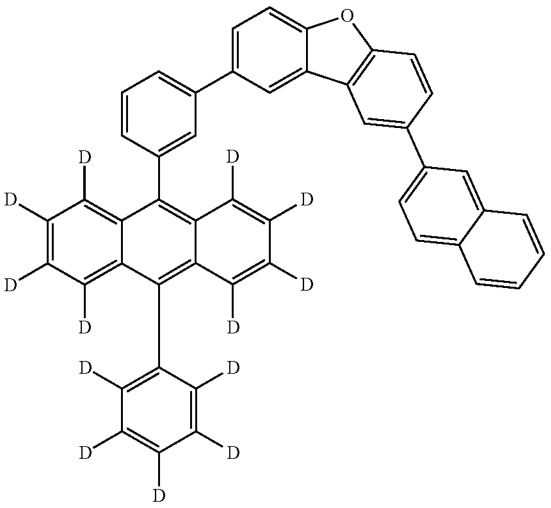
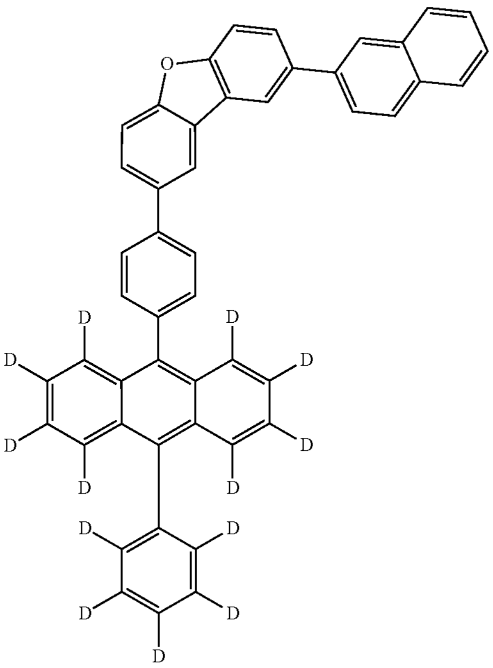
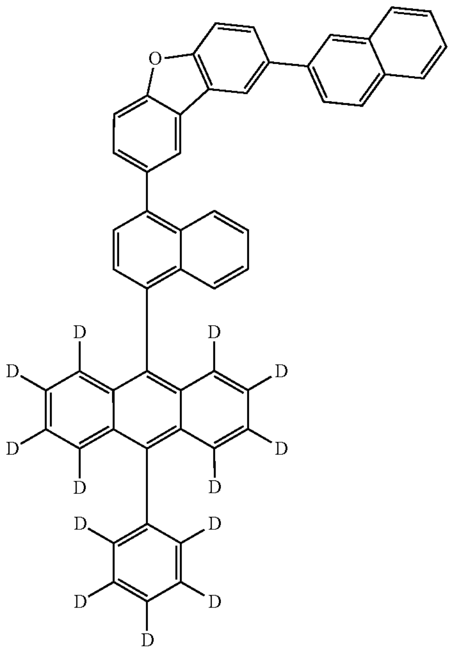

-continued
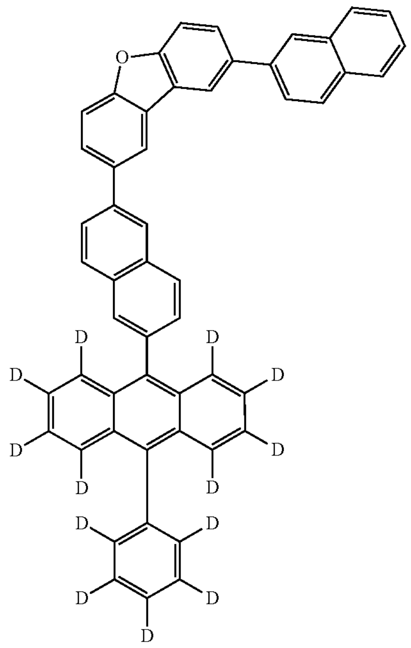
-continued
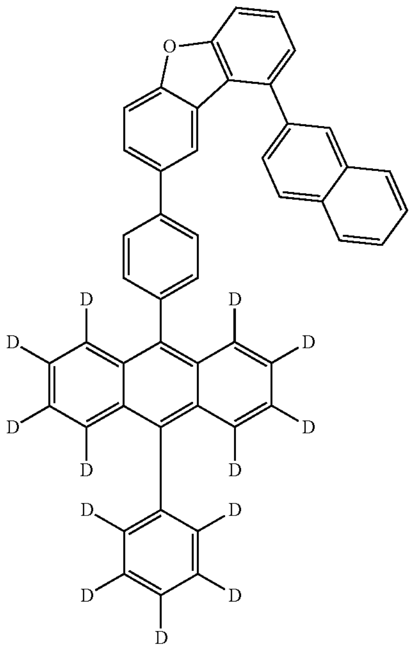
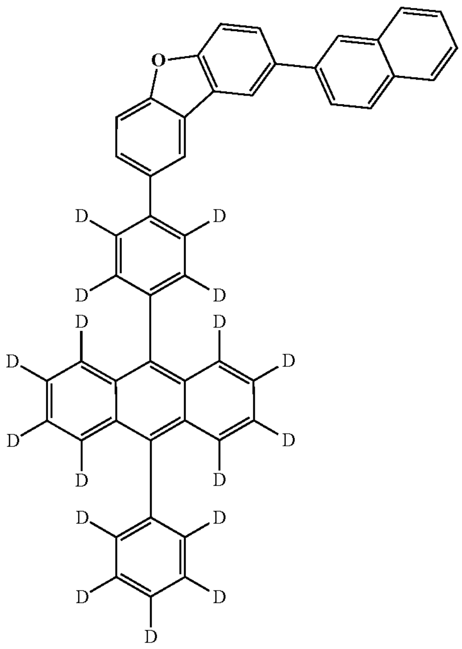
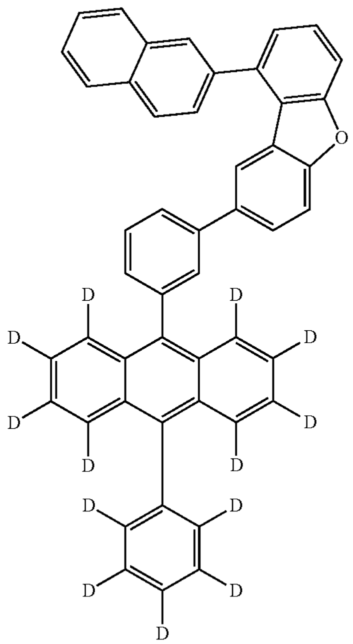

-continued
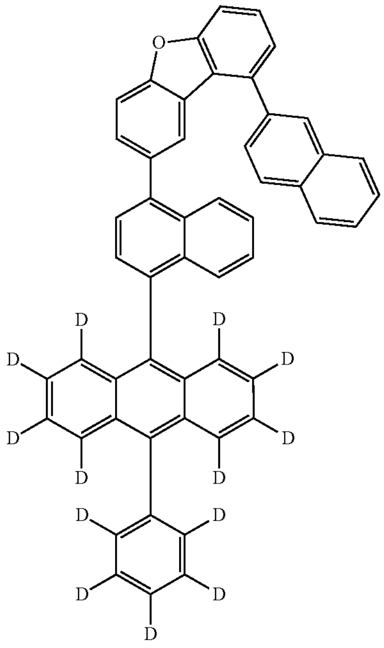
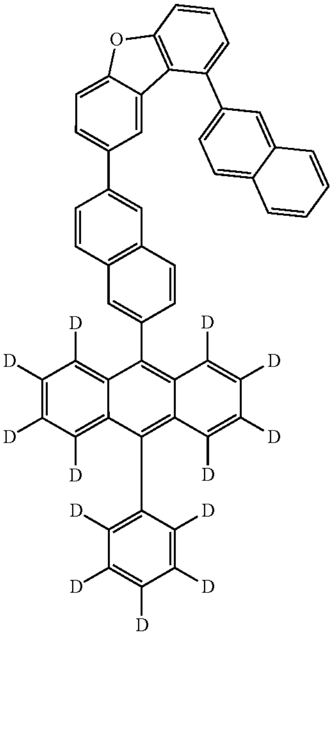
-continued
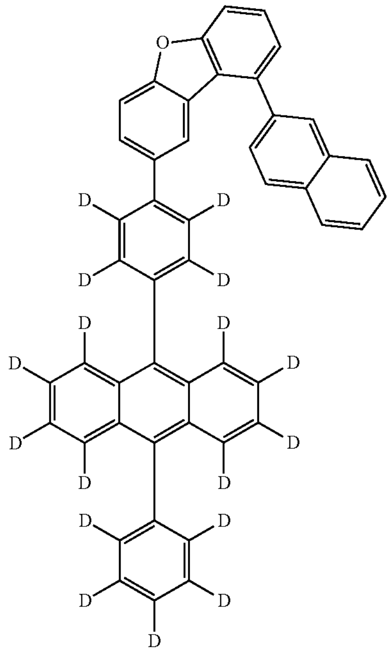
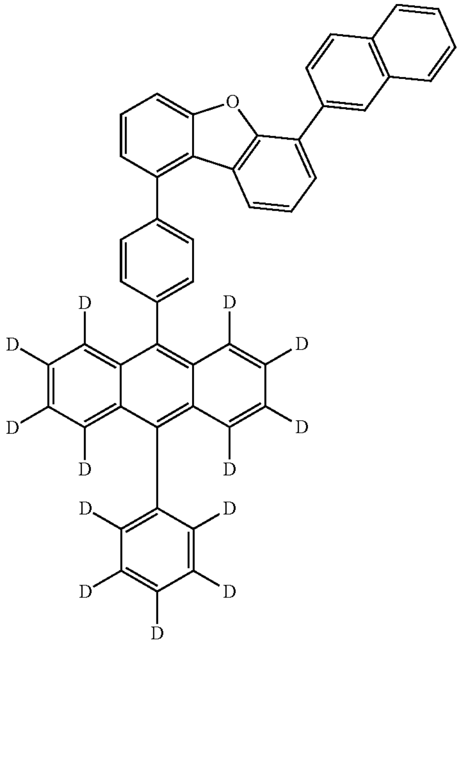

-continued
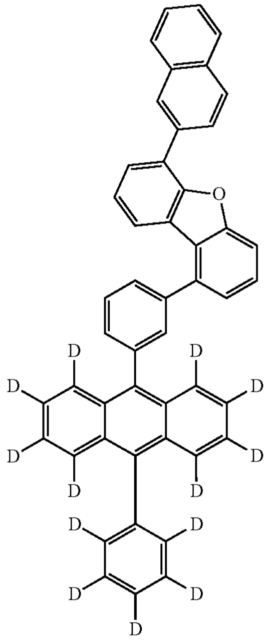
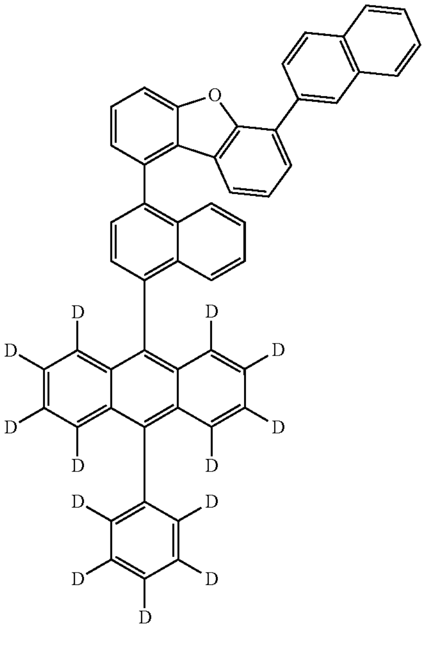
-continued
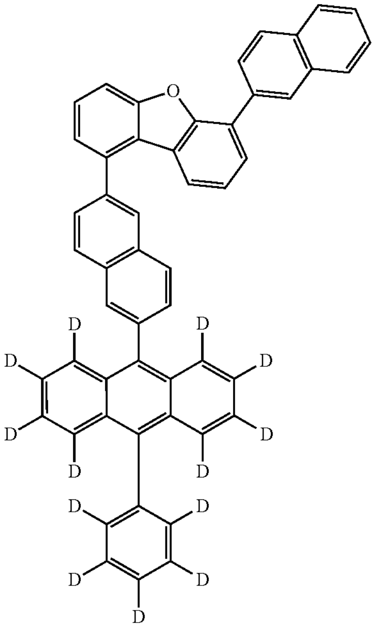
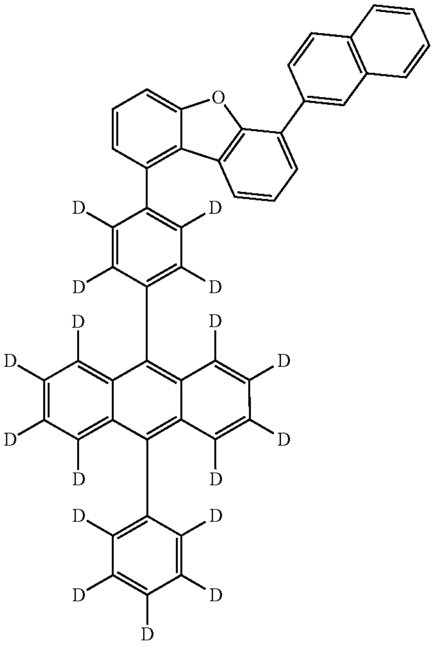

-continued
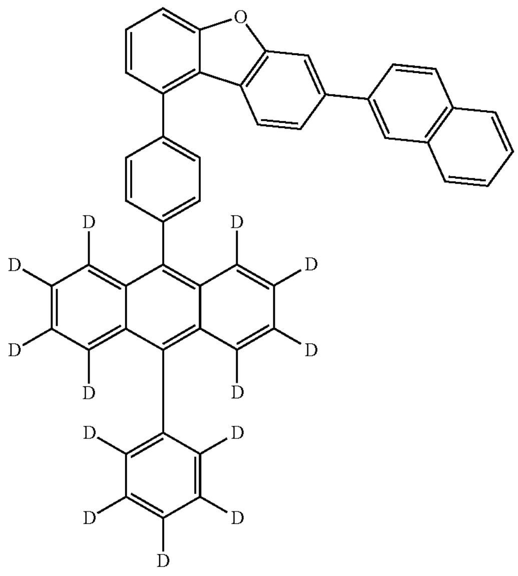
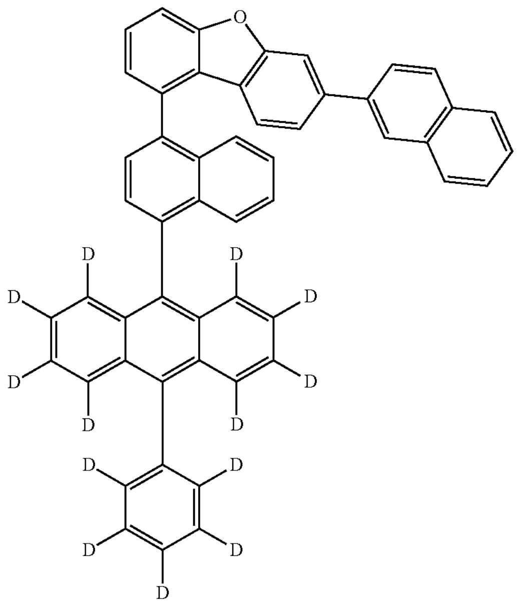
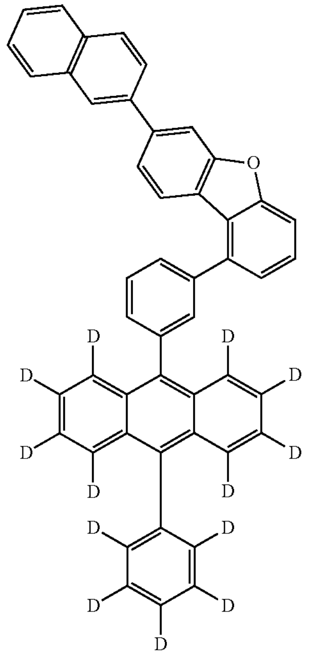
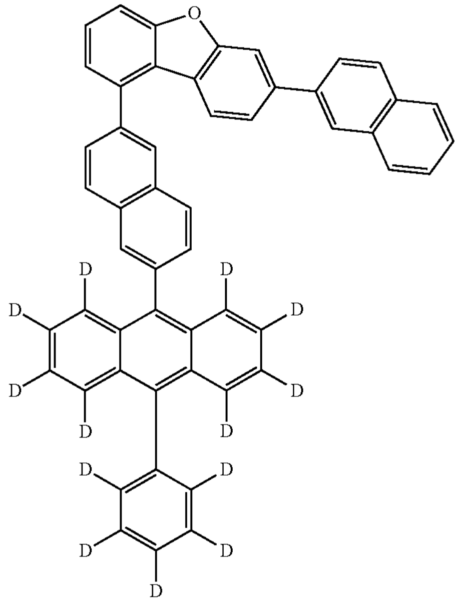

-continued
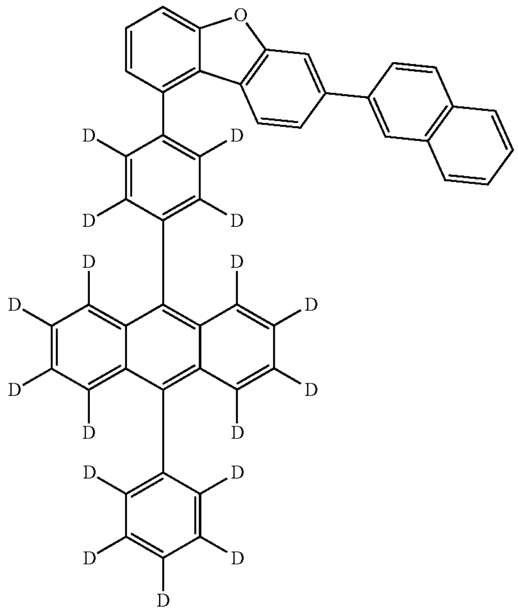
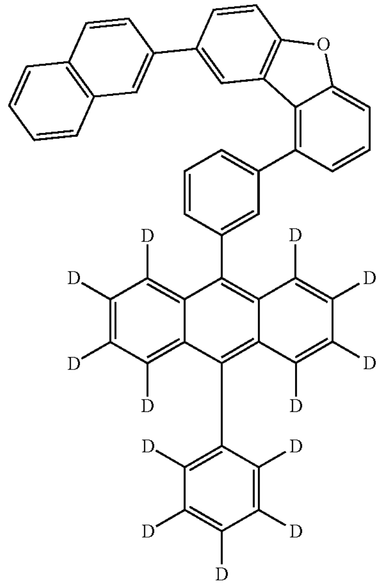
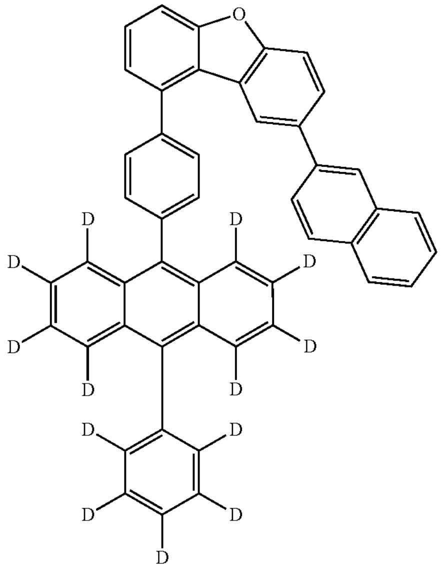
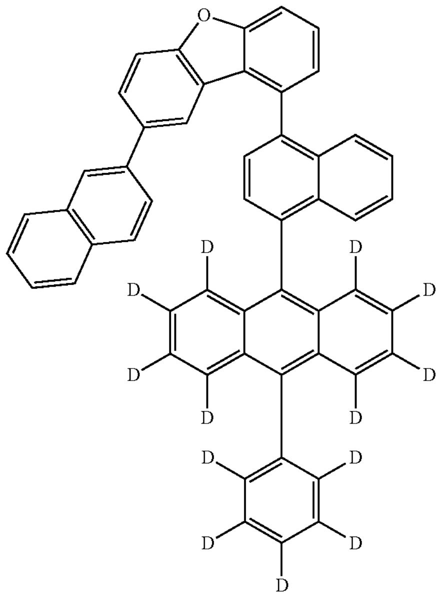

-continued
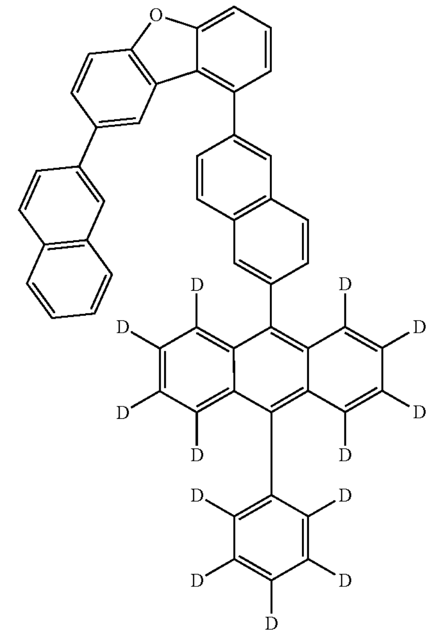
-continued
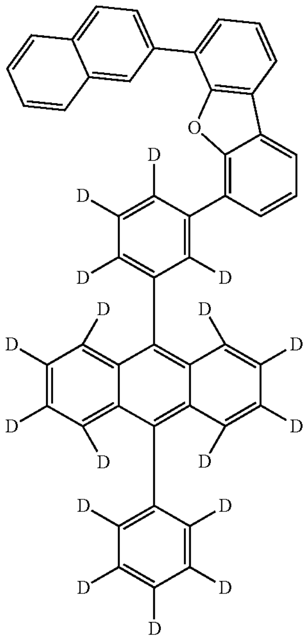
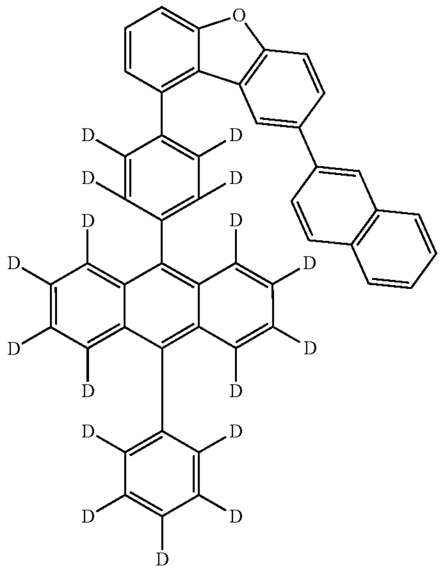
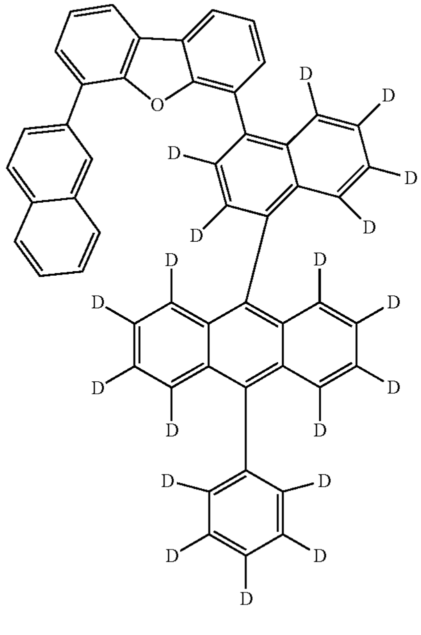

-continued
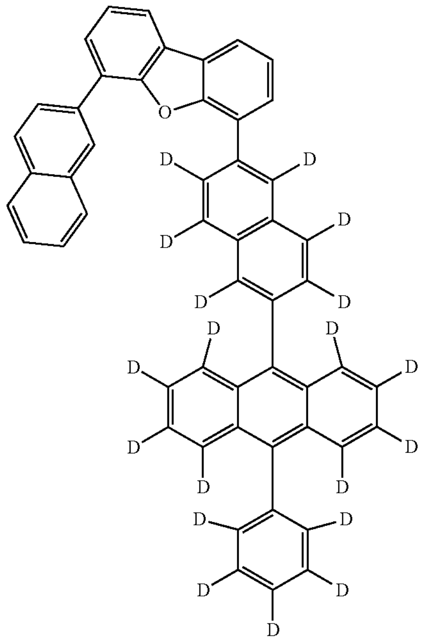
-continued
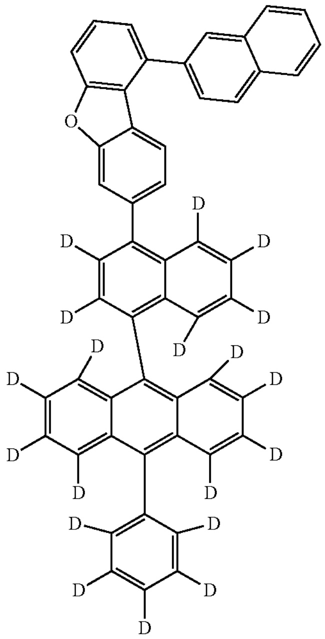
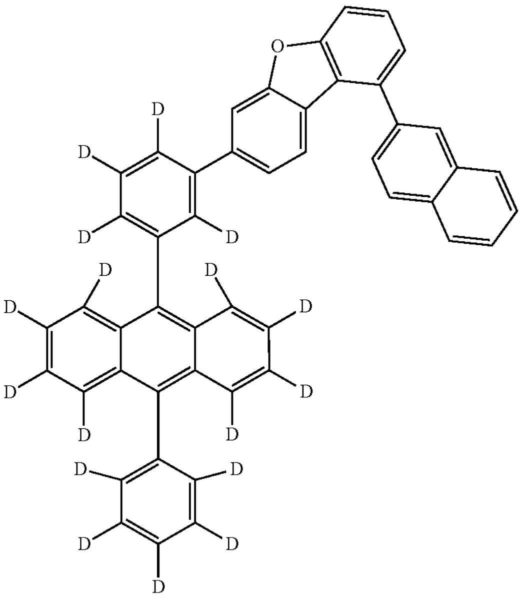
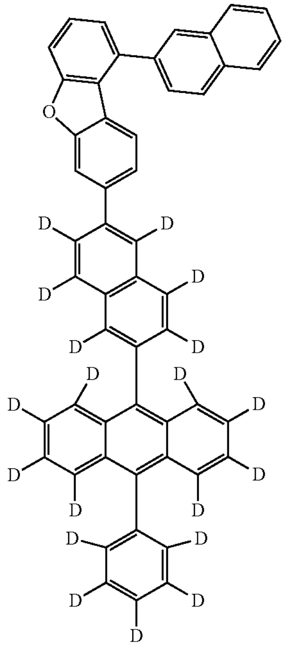

-continued
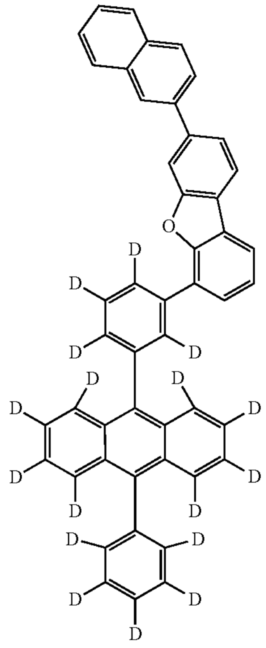
-continued
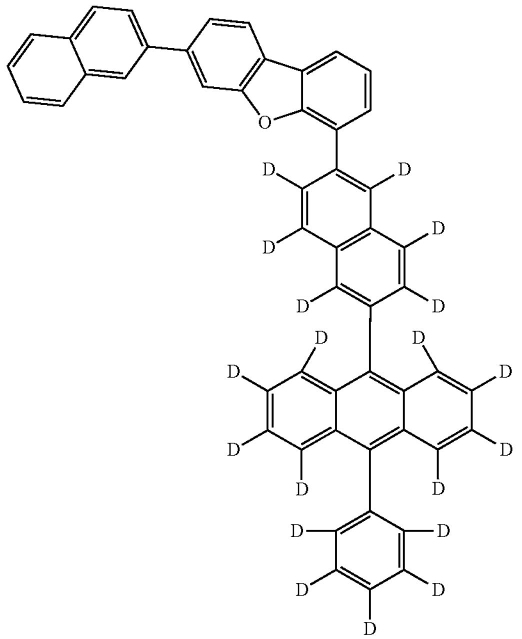
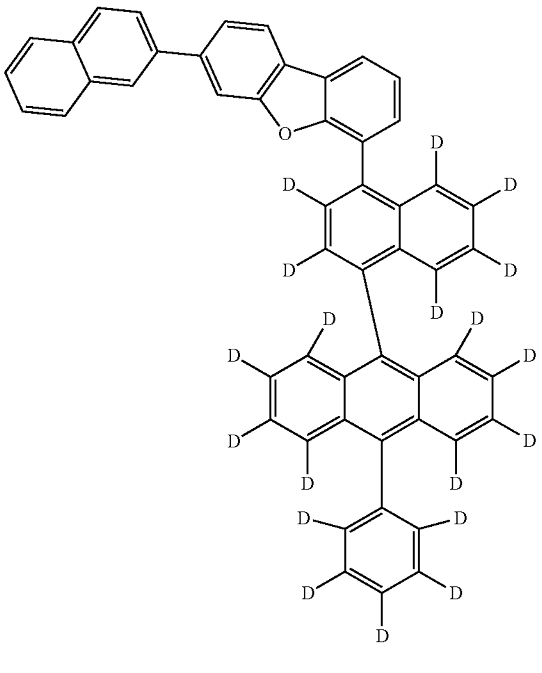
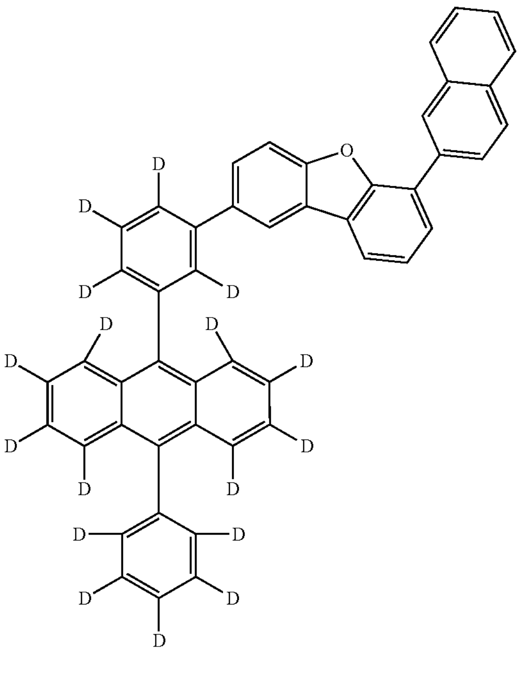

-continued
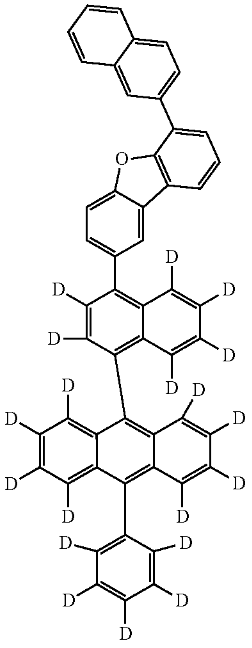
-continued
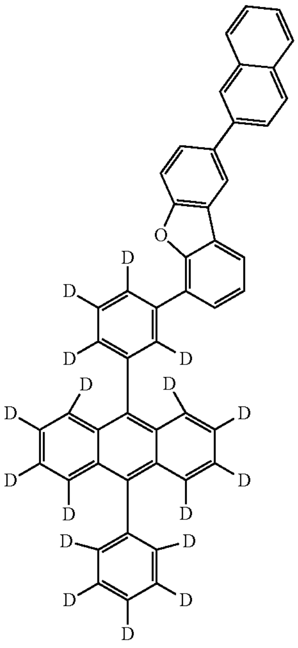
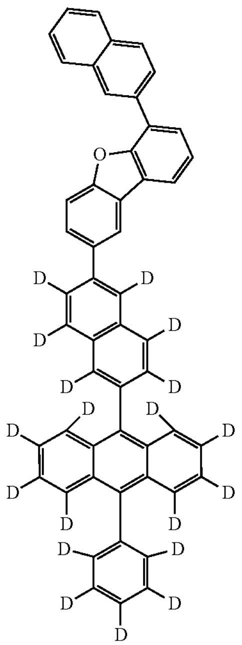
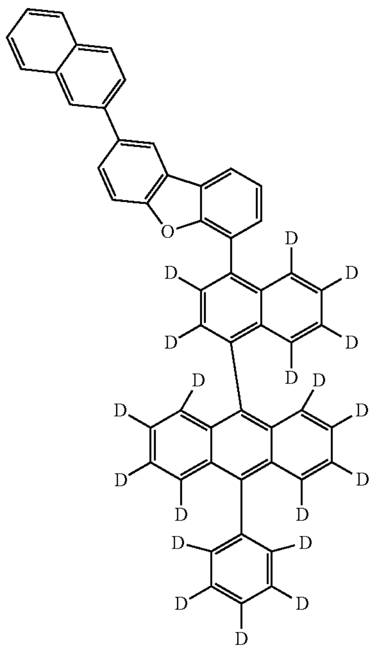

-continued
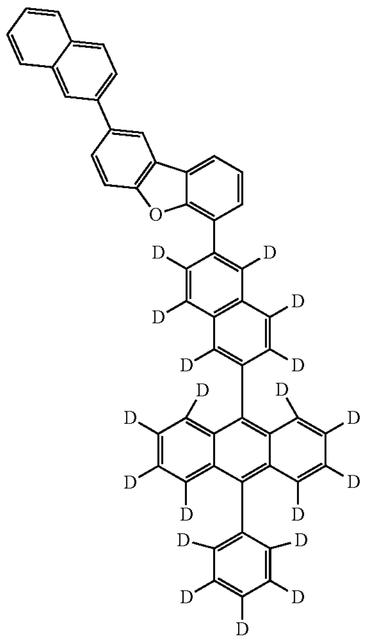
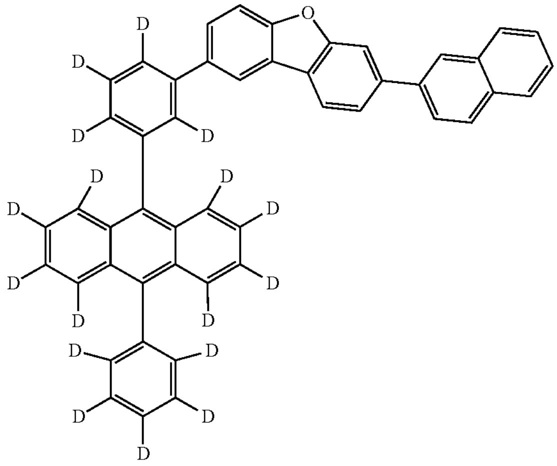
-continued
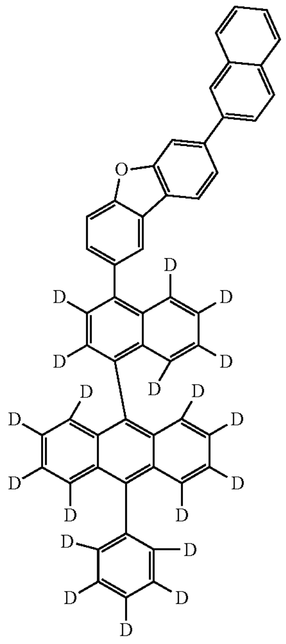
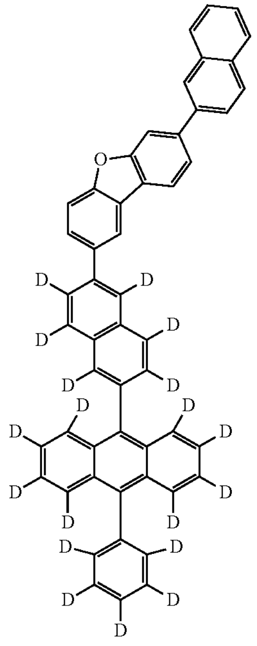

-continued
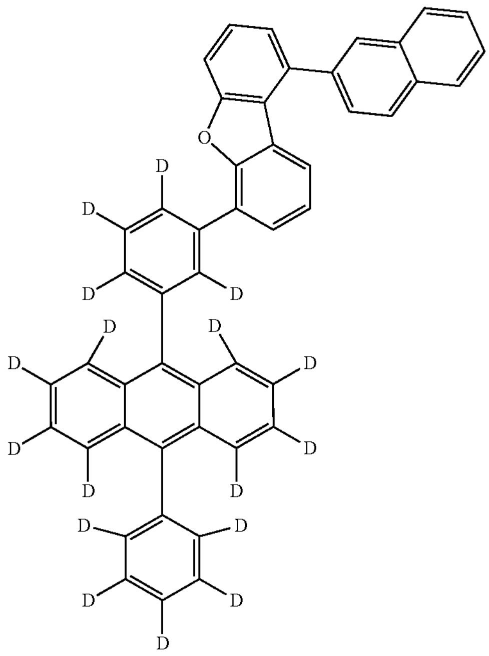
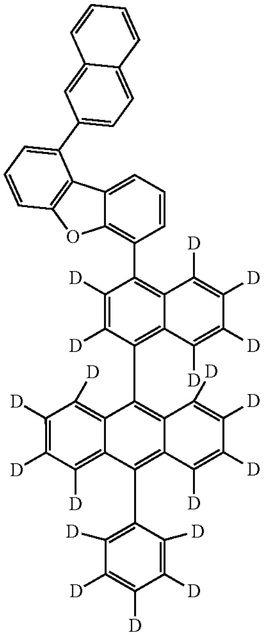
-continued
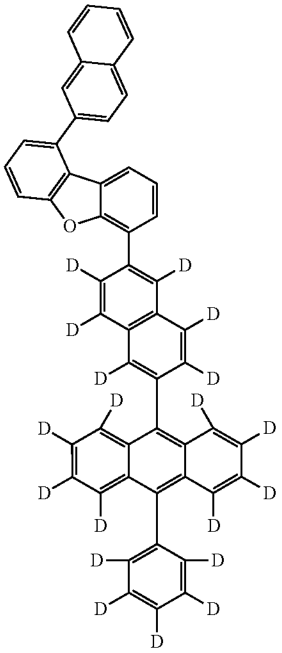
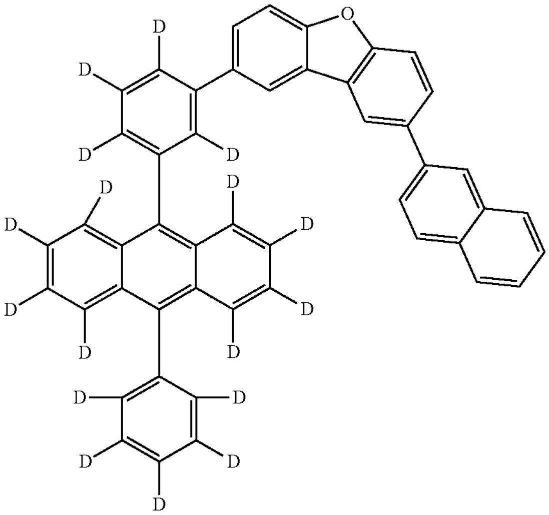

-continued
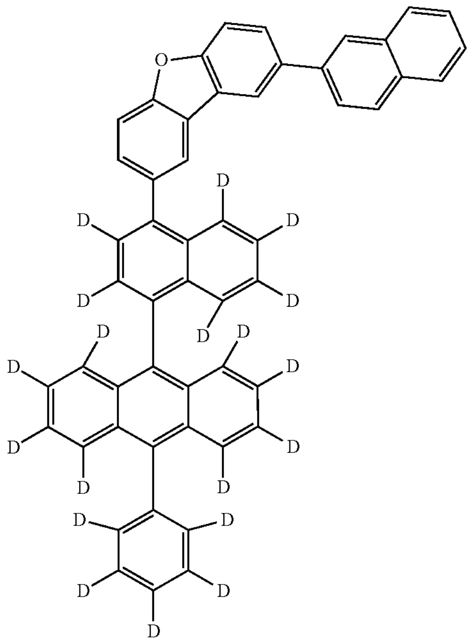
-continued
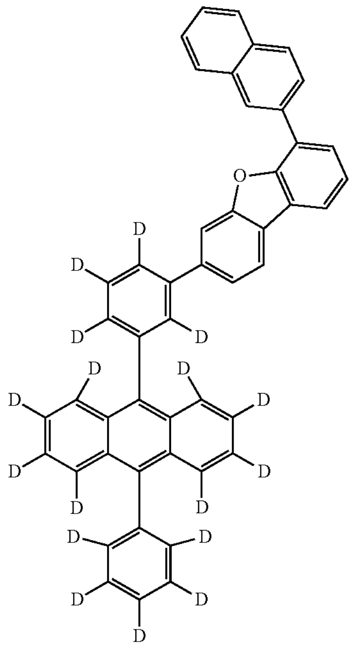
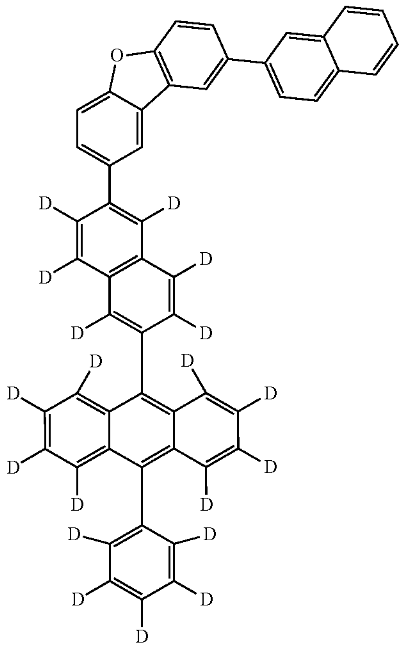
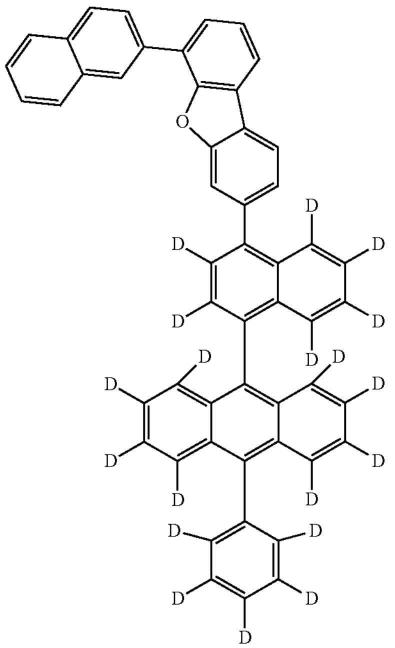

-continued
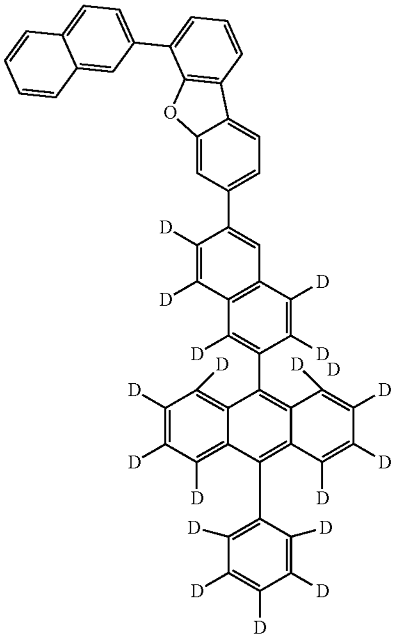
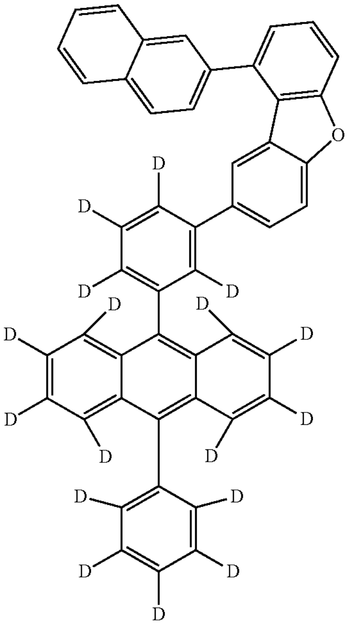
-continued
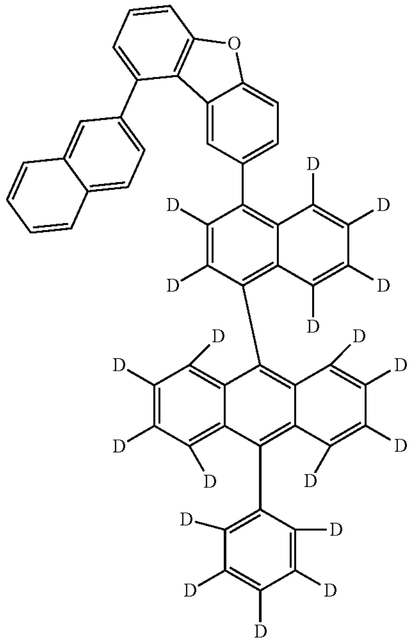
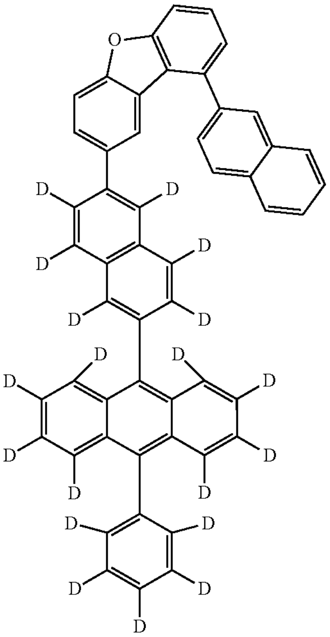

-continued
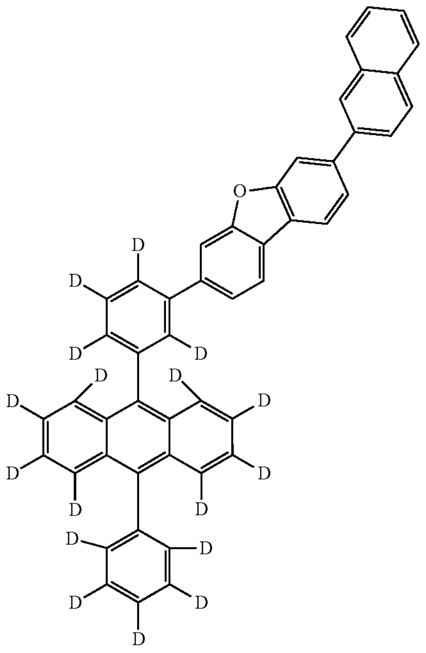
-continued
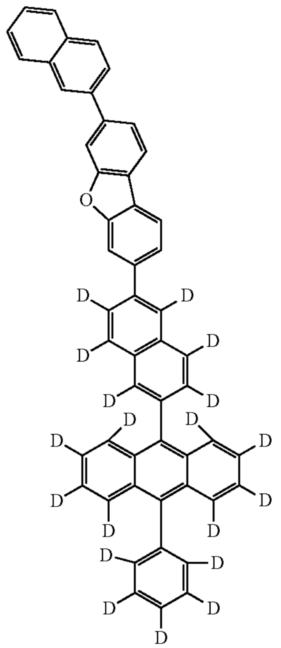
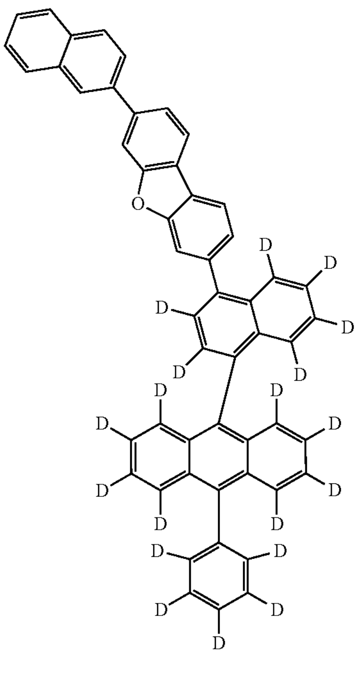
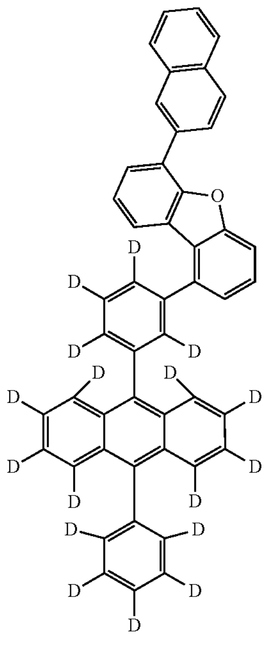

-continued
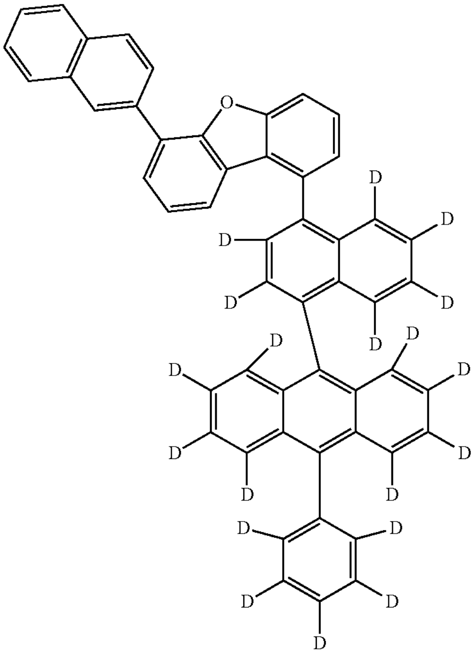
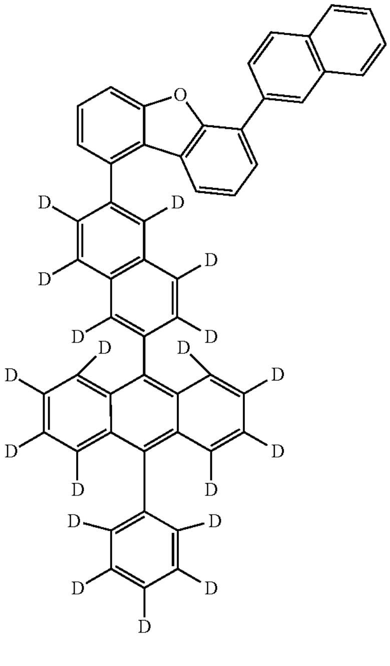
-continued
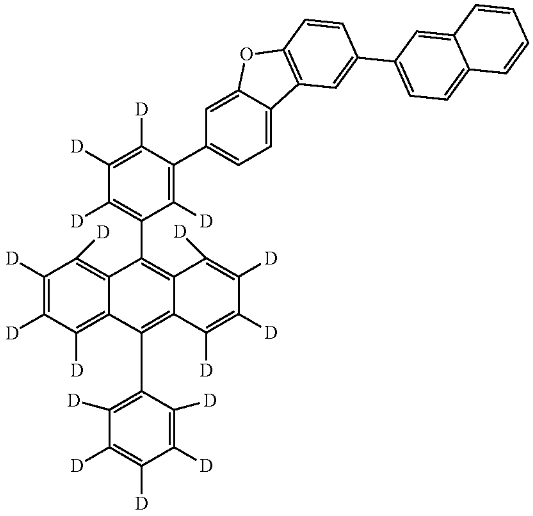
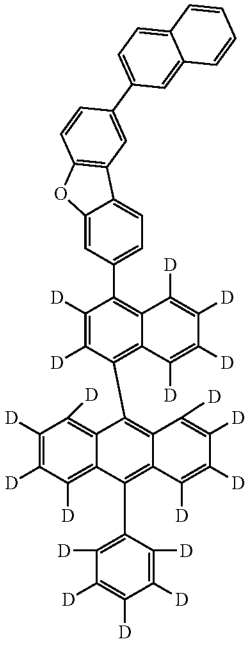

-continued
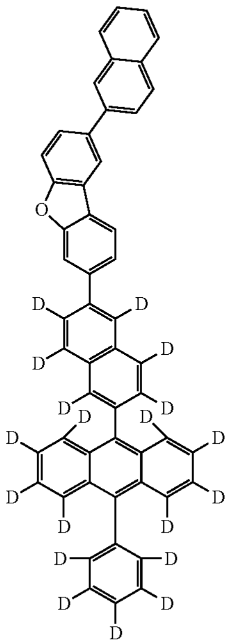
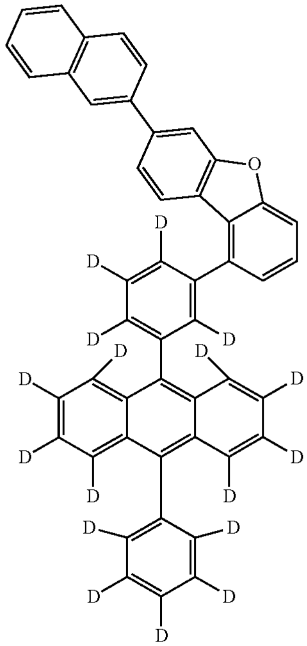
-continued
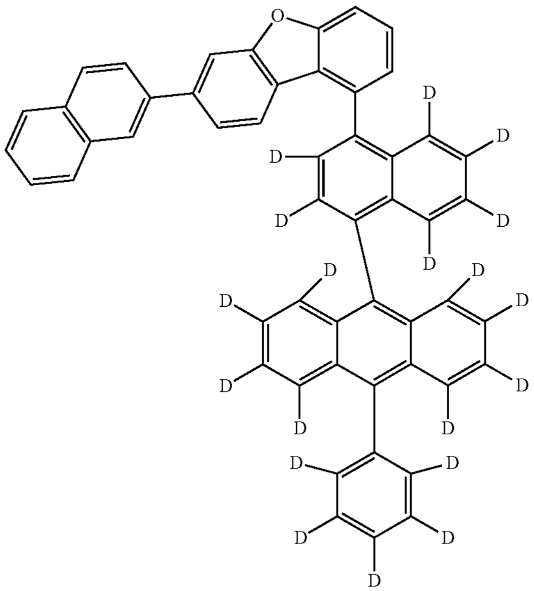
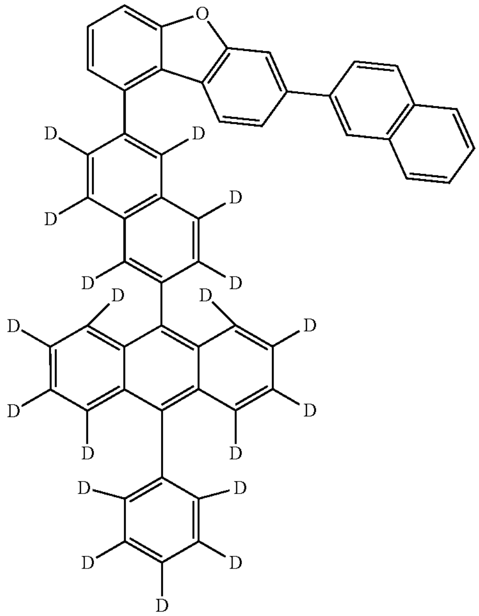

-continued
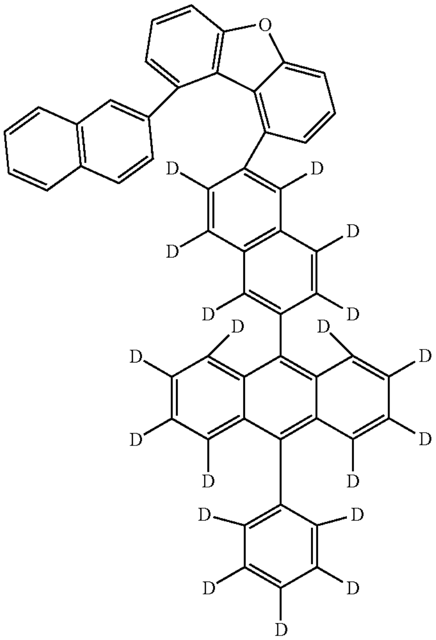
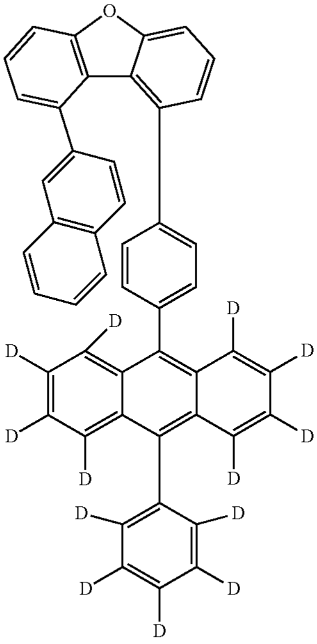
-continued
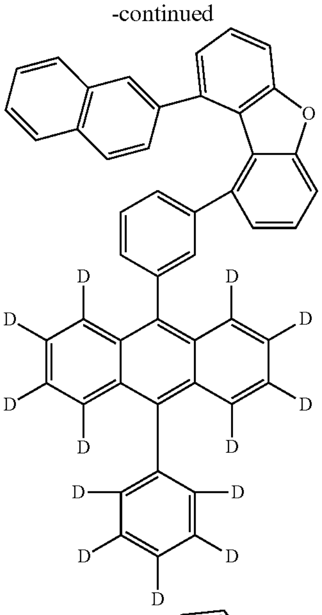
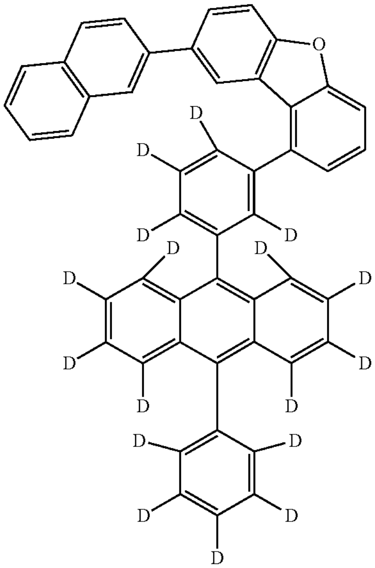
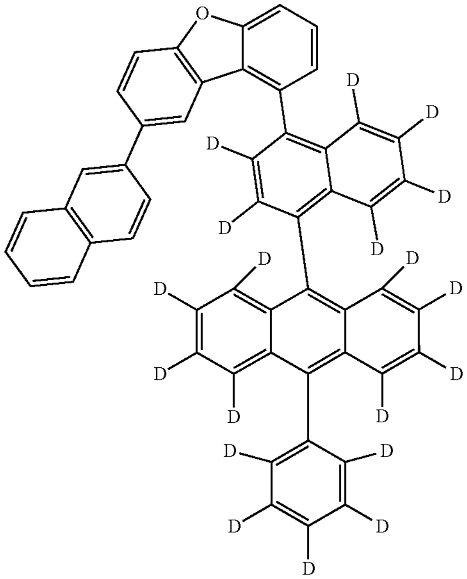

-continued
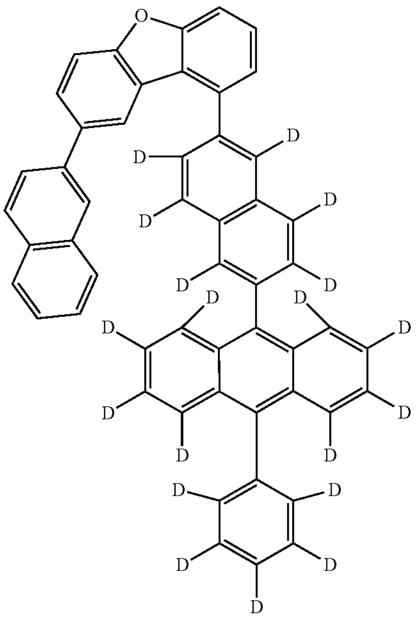
-continued
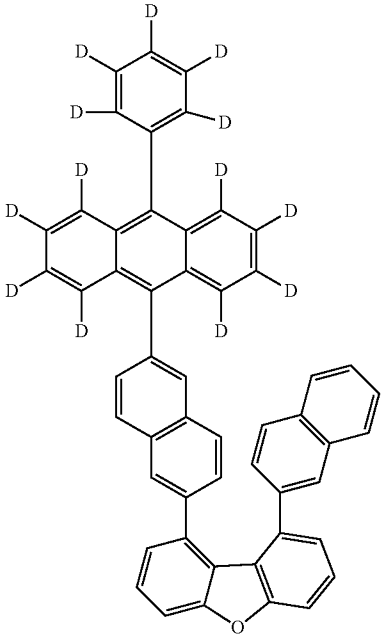
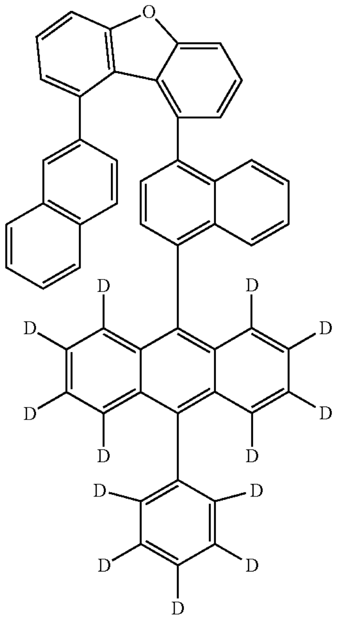
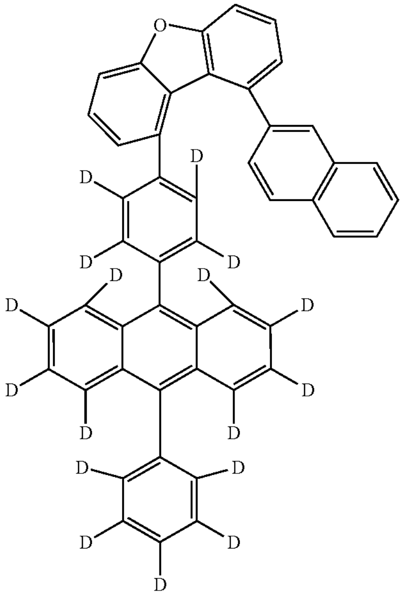

-continued
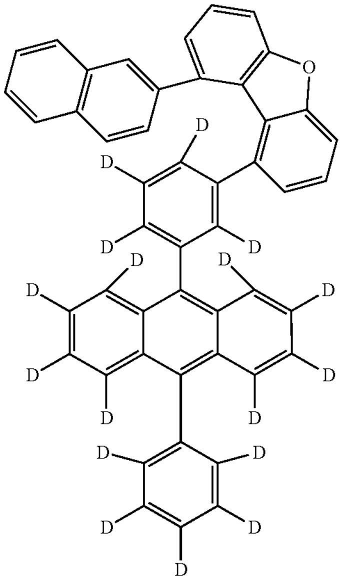
-continued
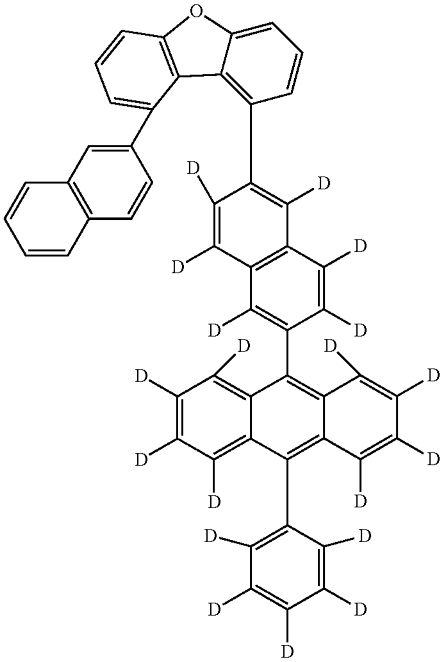
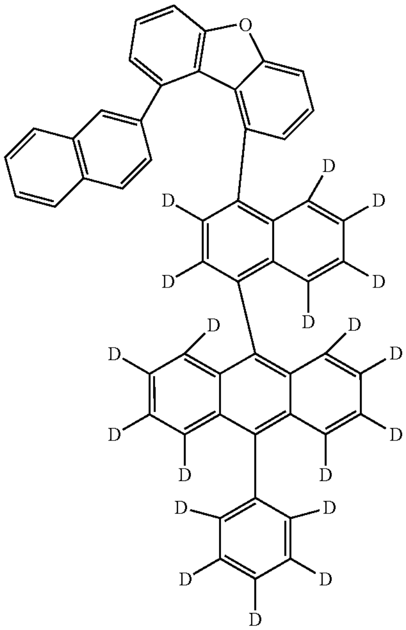
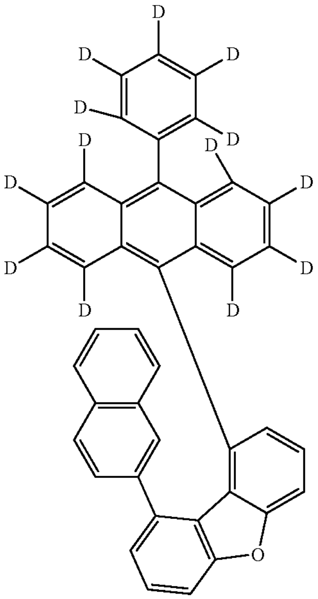

-continued
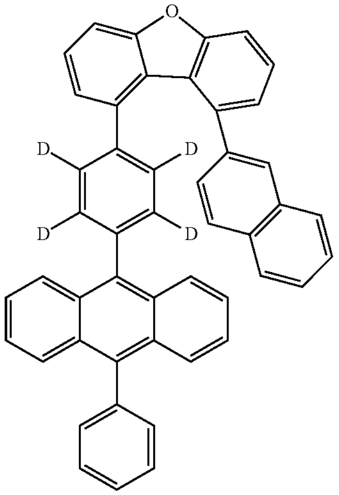
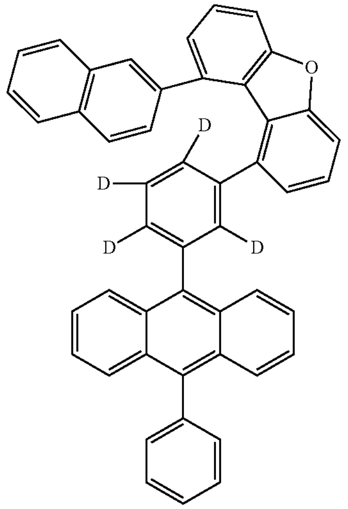
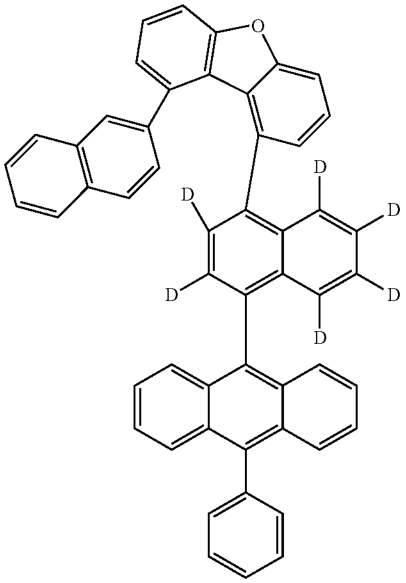
-continued
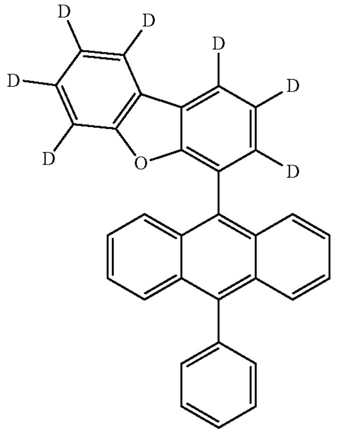
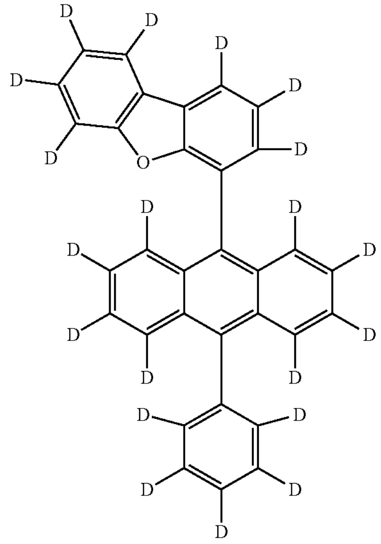
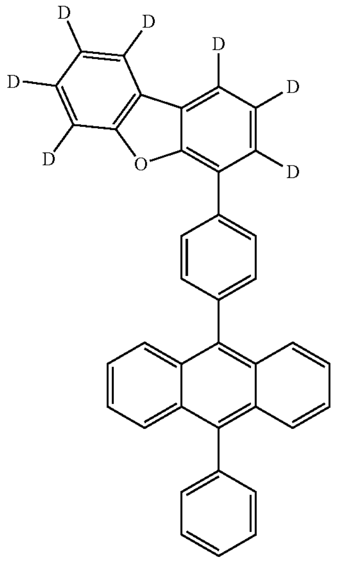

-continued
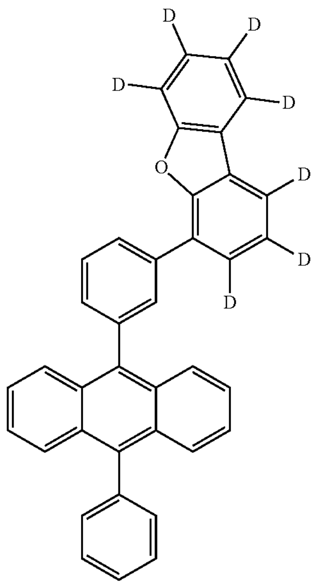
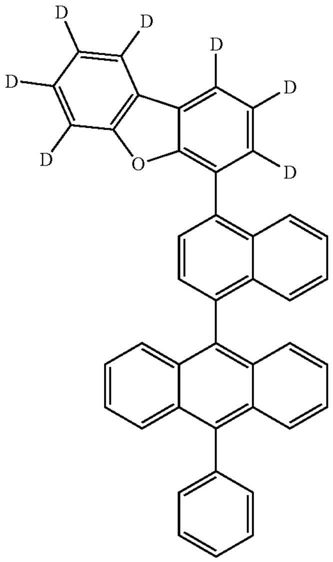
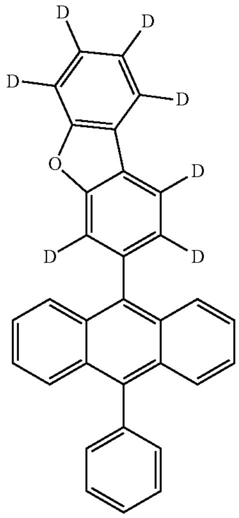
-continued
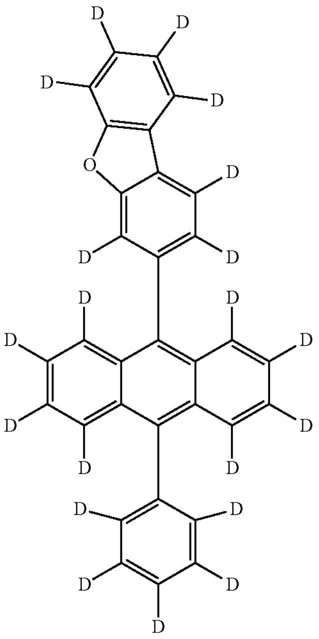
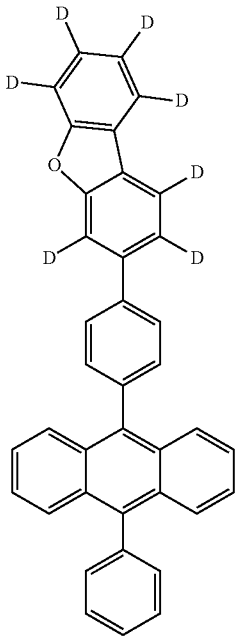

-continued
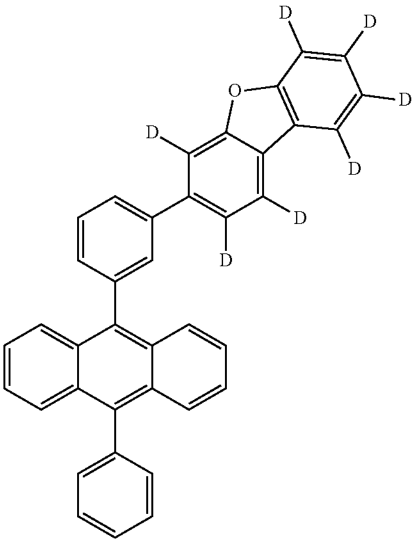
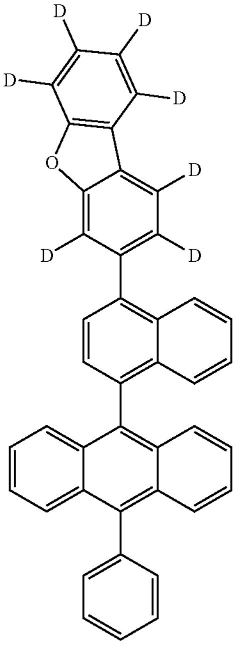
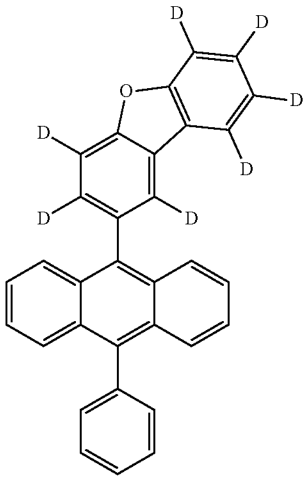
-continued
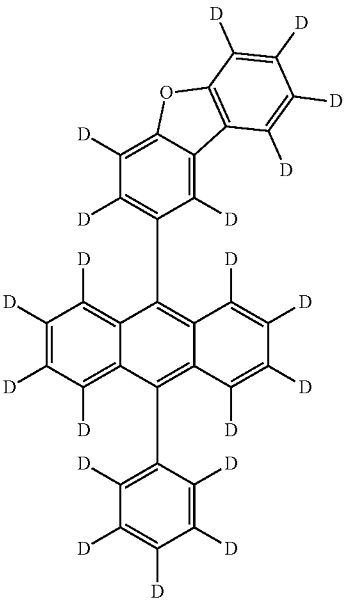
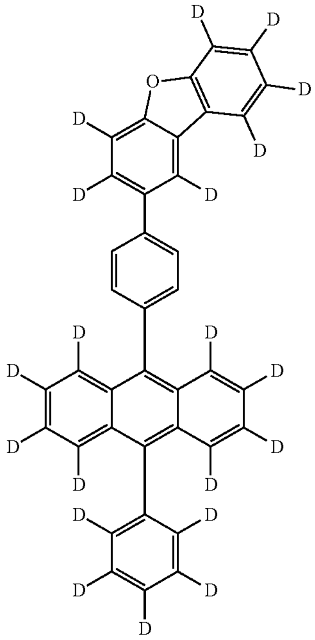
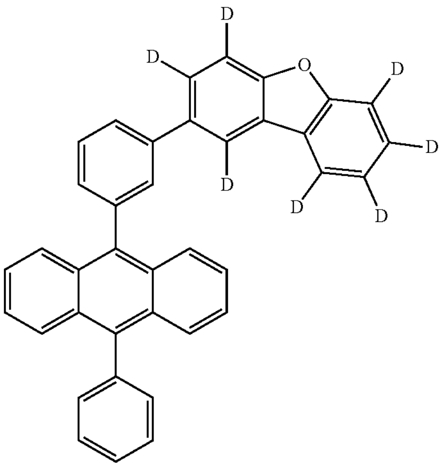

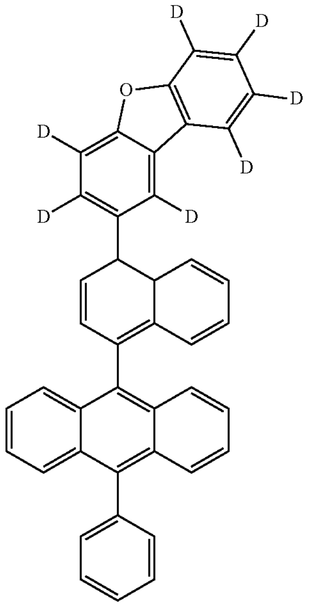
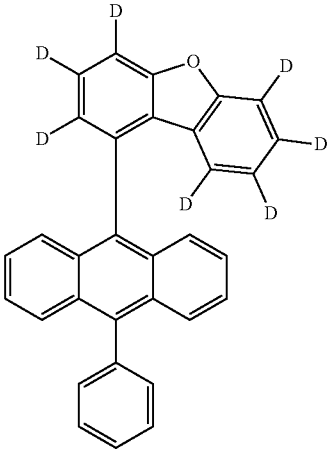
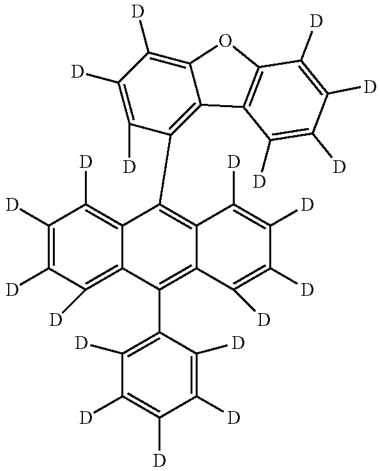
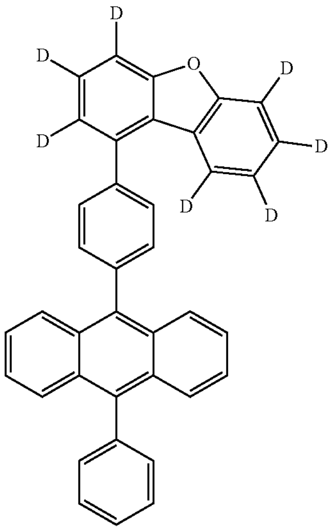
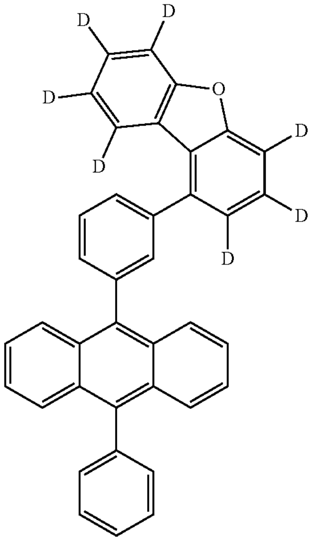
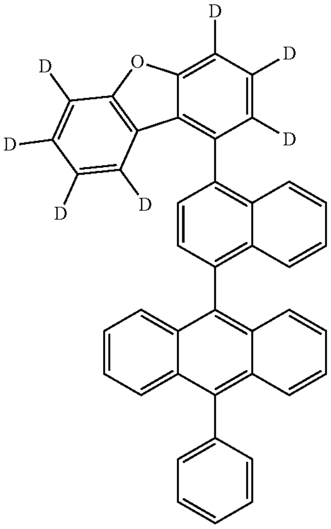

-continued
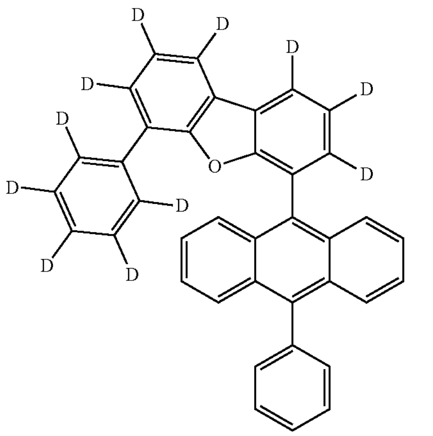
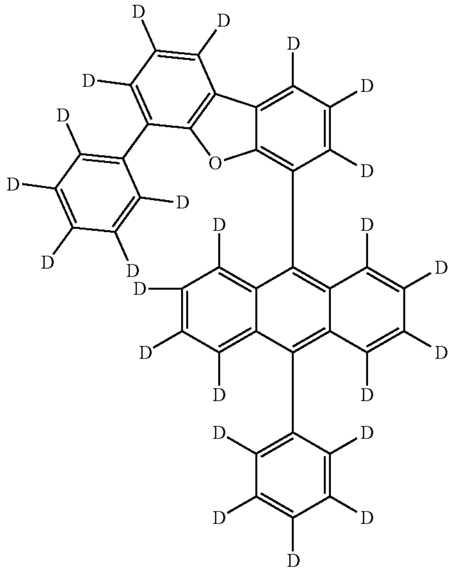
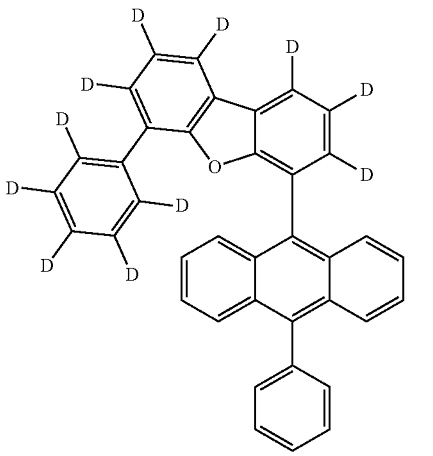
-continued
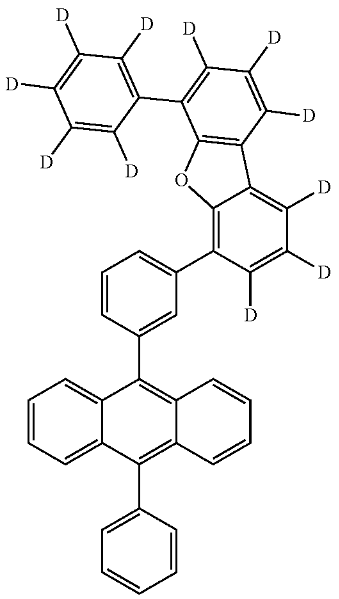
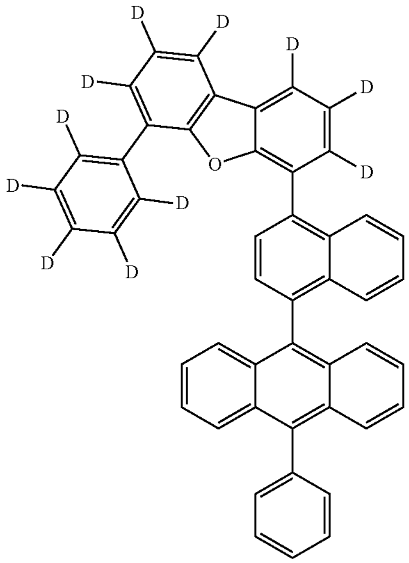

-continued
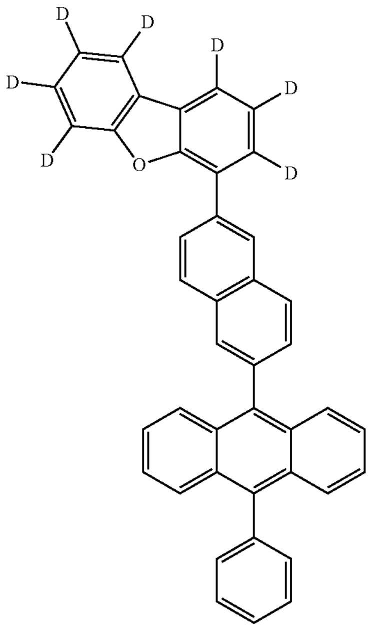
-continued
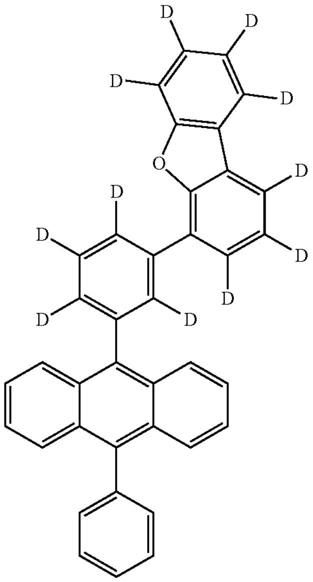
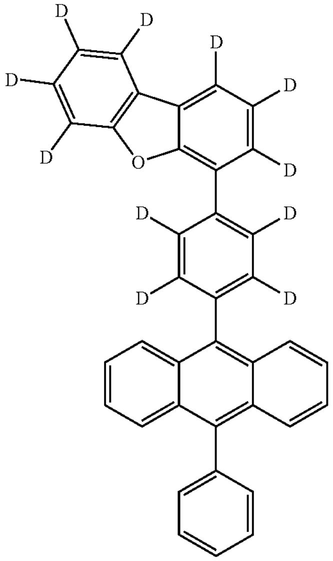
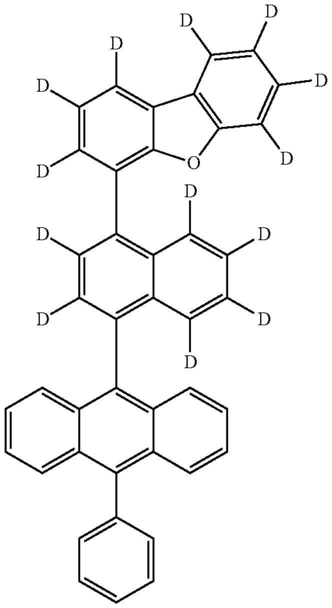

-continued
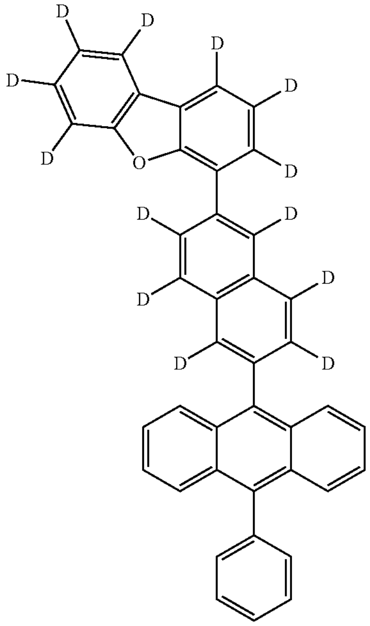
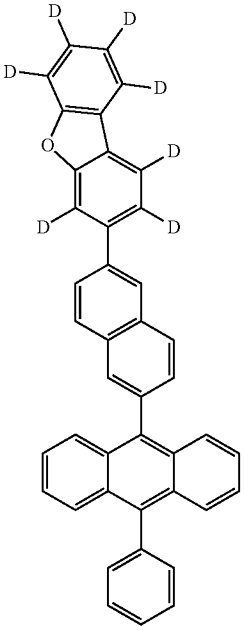
-continued
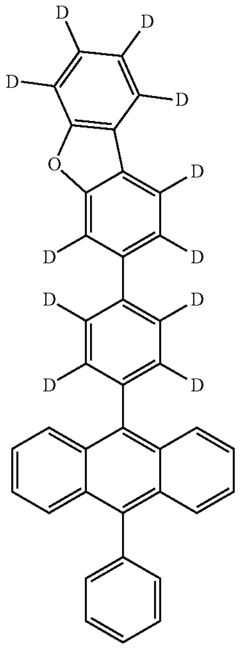
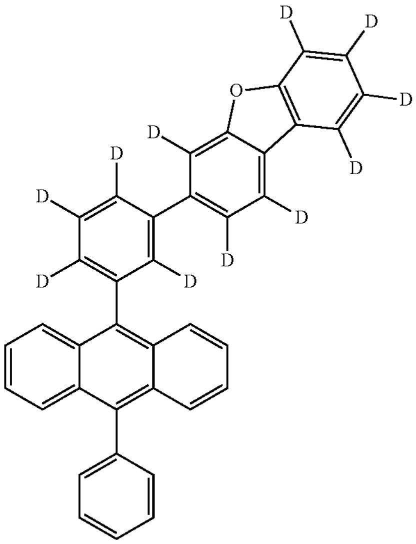

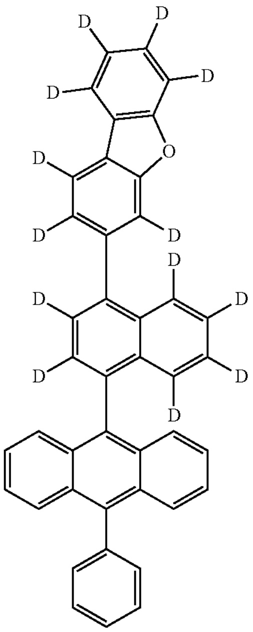
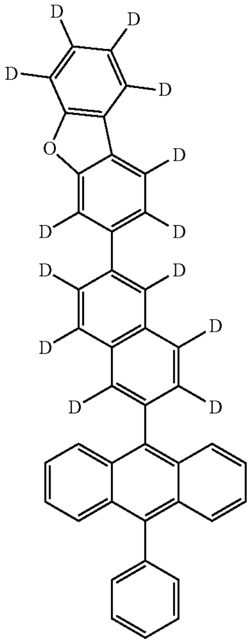
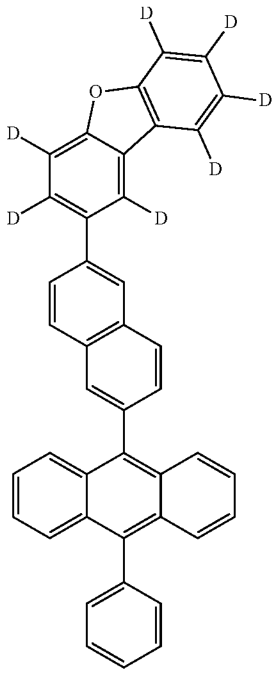
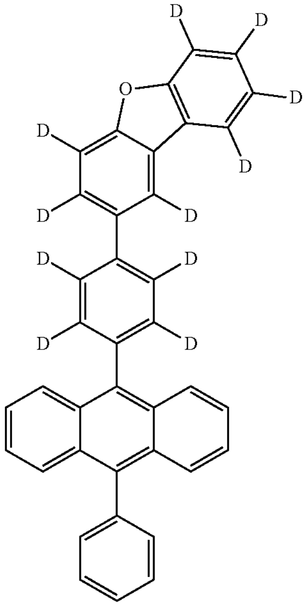

-continued
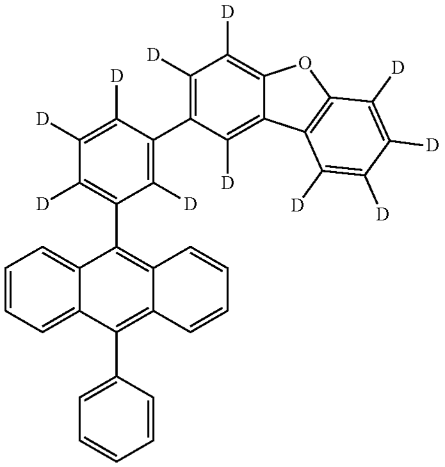
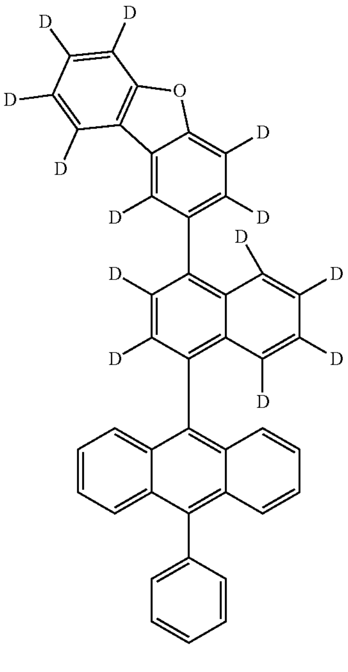
-continued
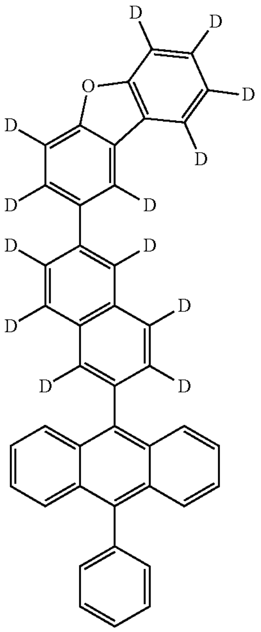
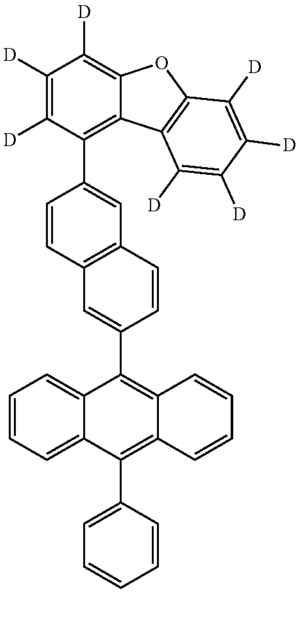

-continued
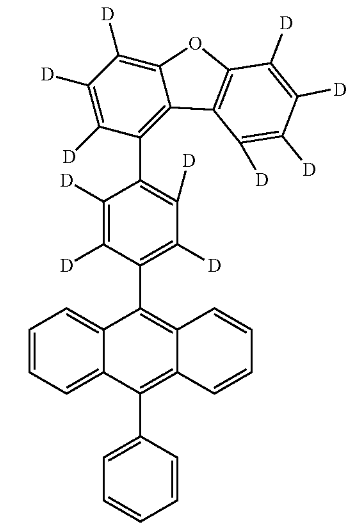
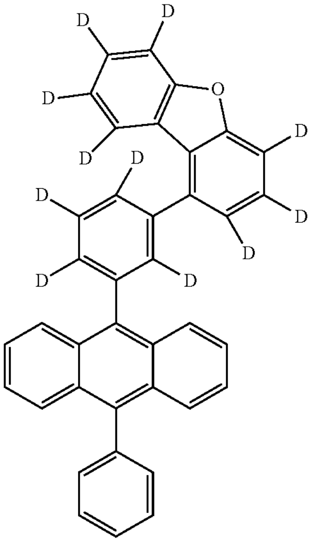
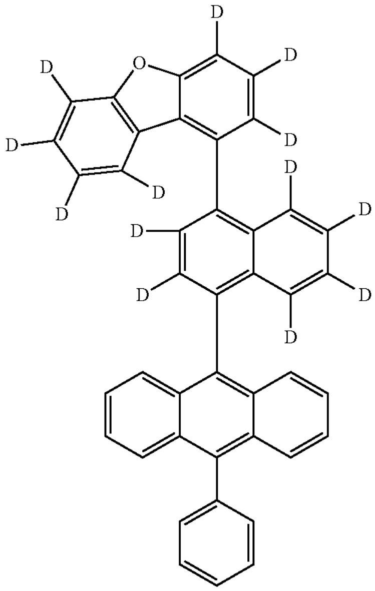
-continued
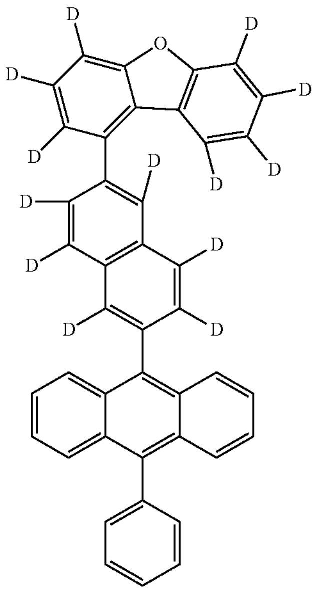
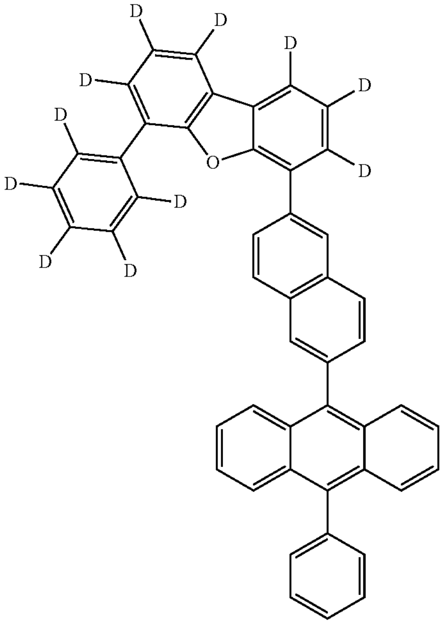

-continued
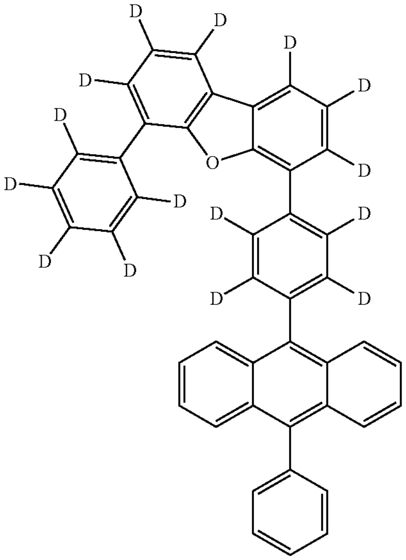
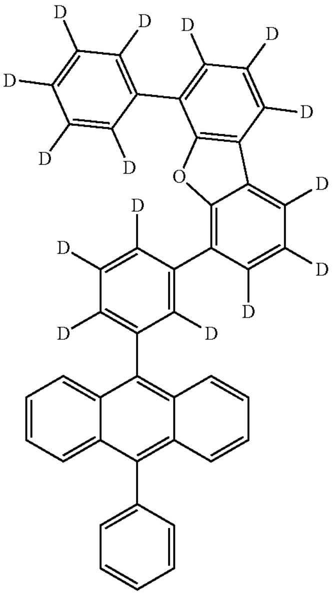
-continued
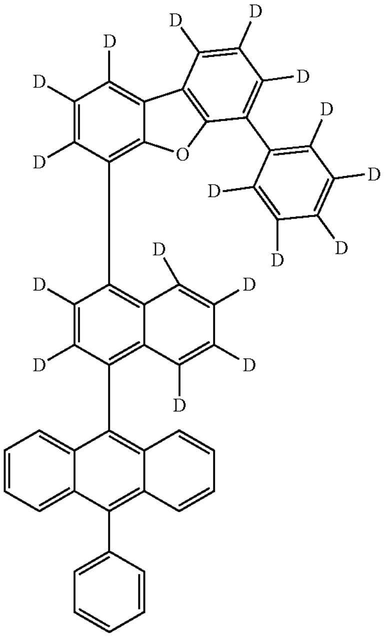
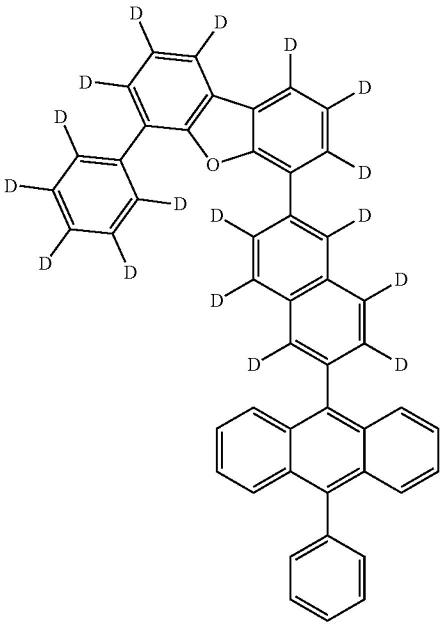 [SMILES: [2H]c1c([2H])c([2H])c(-c2c([2H])c([2H])c([2H])c3c2oc2c(-c4c([2H])c([2H])c5c([2H])c(-c6c7ccccc7c(-c7ccccc7)c7ccccc67)c([2H])c([2H])c5c4[2H])c([2H])c([2H])c([2H])c23)c([2H])c1[2H]]

-continued
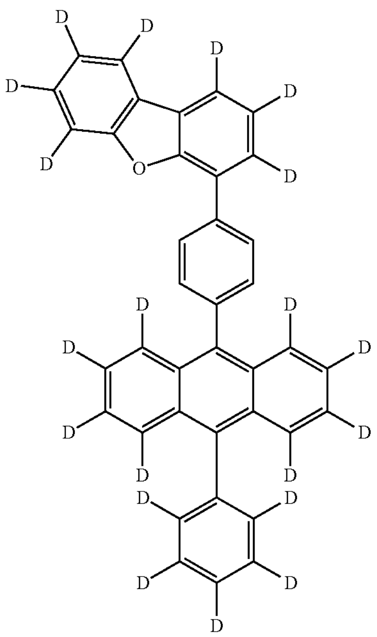
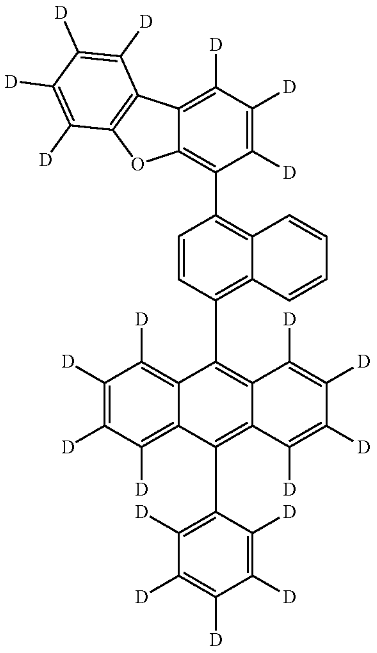
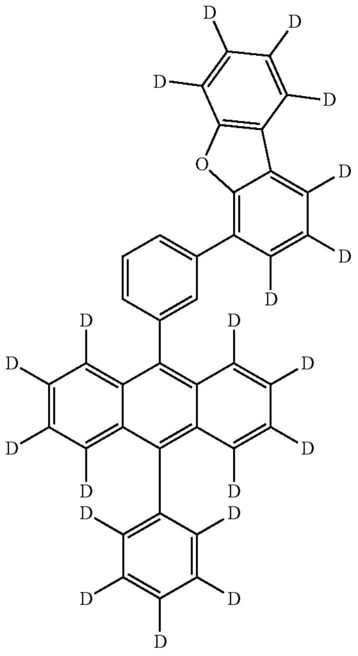
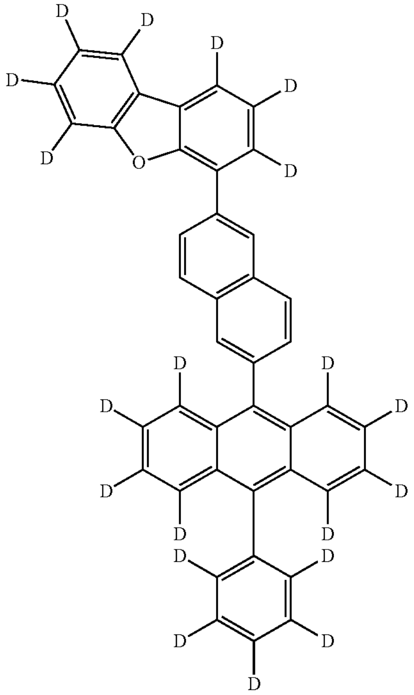

-continued
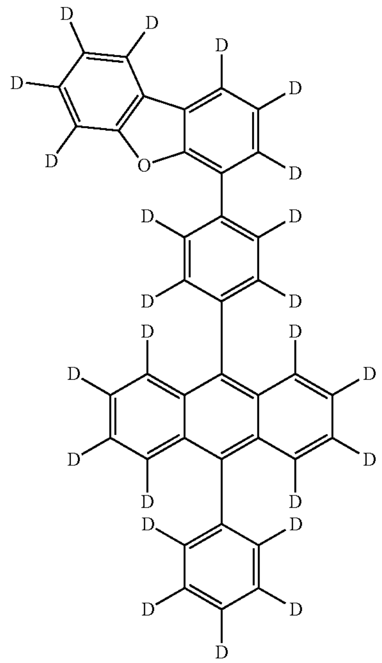
-continued
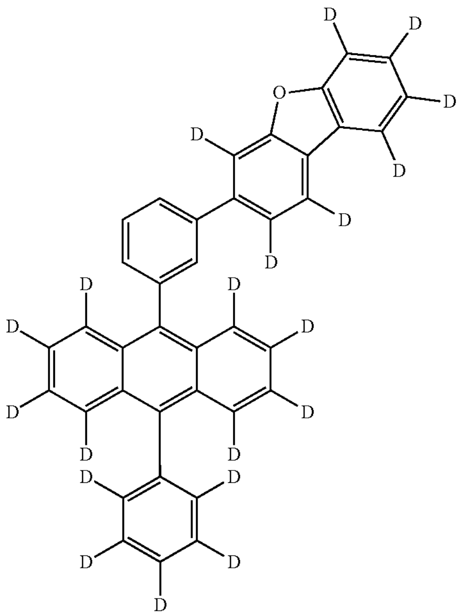
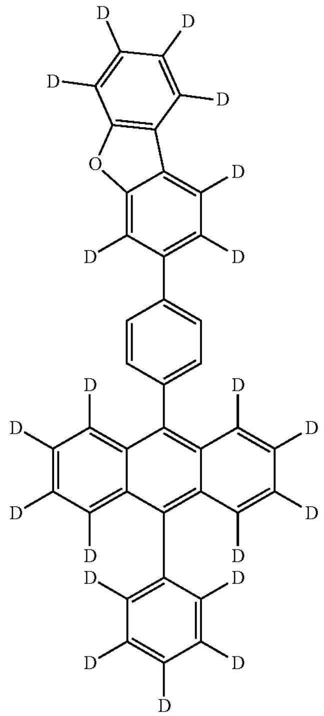
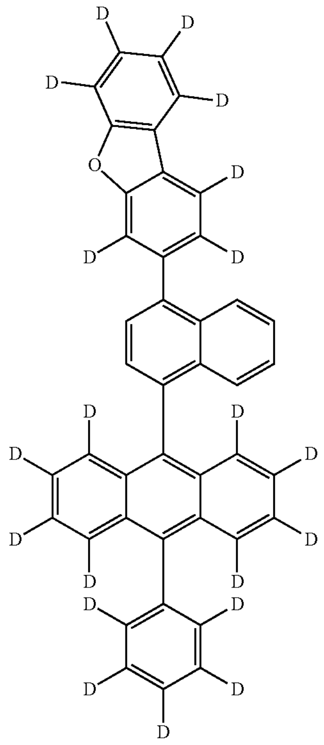

-continued
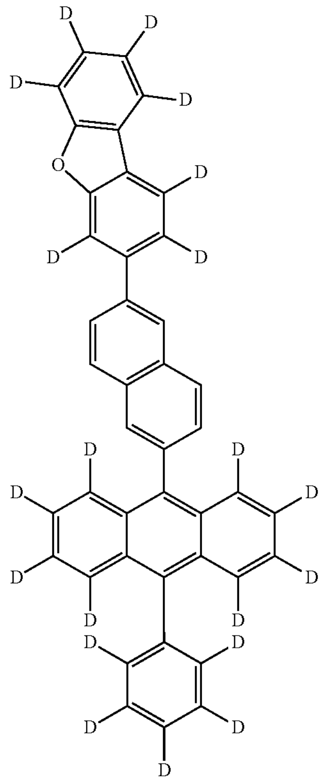
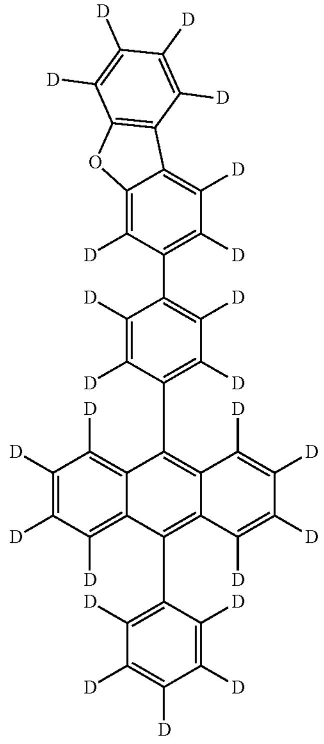
-continued
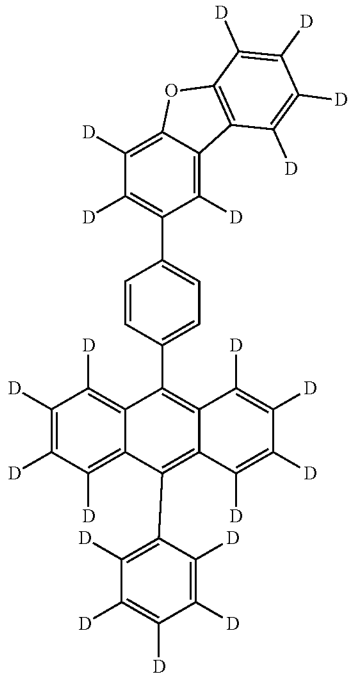
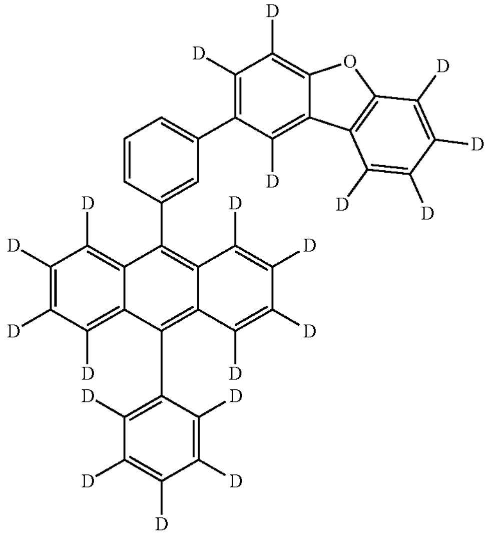

-continued
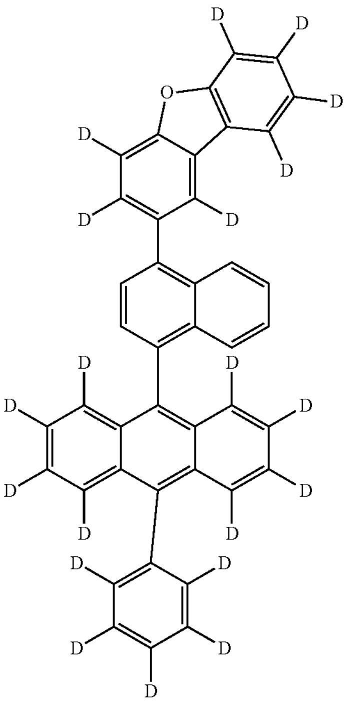
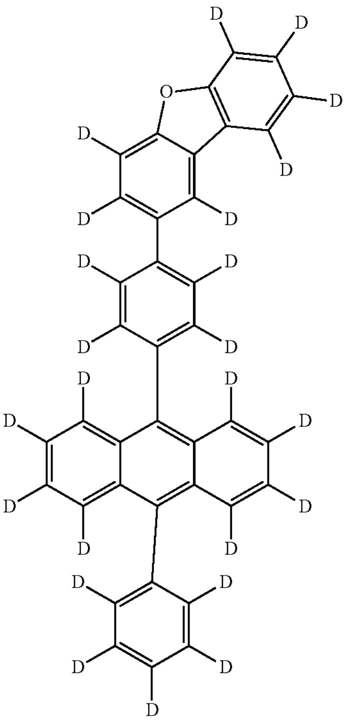
-continued
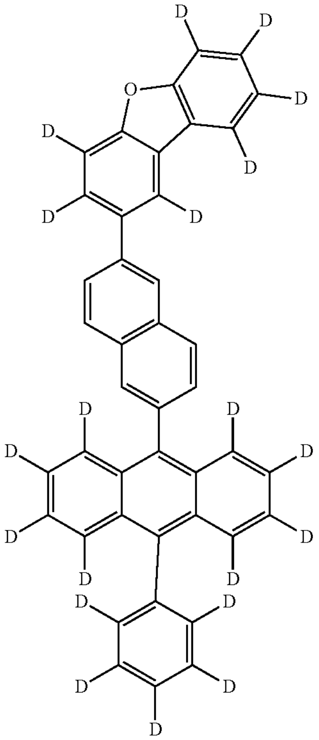
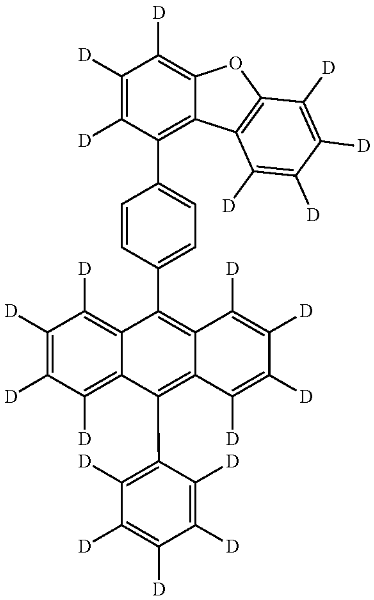

-continued
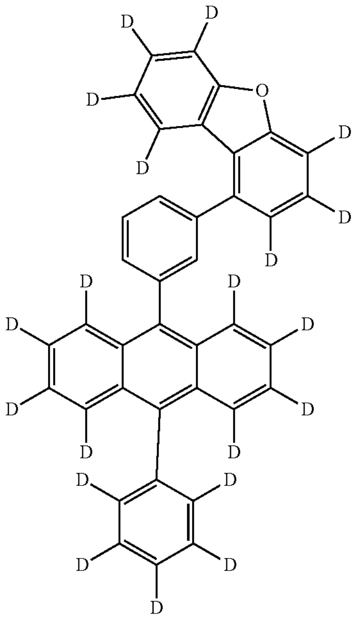
-continued
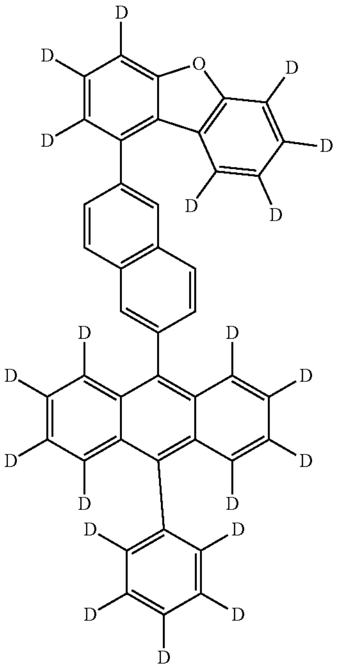
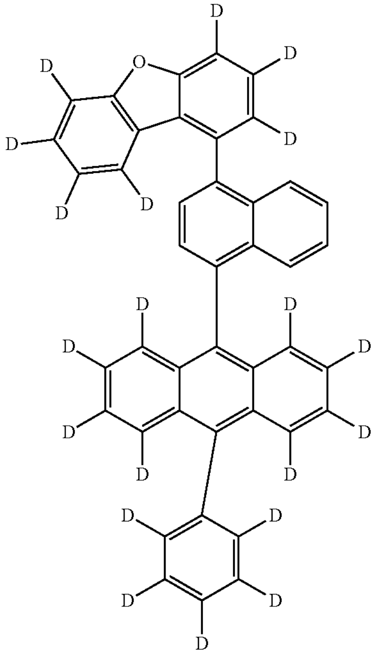
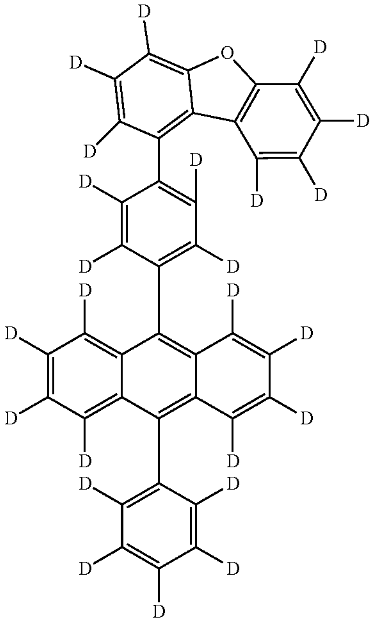

-continued
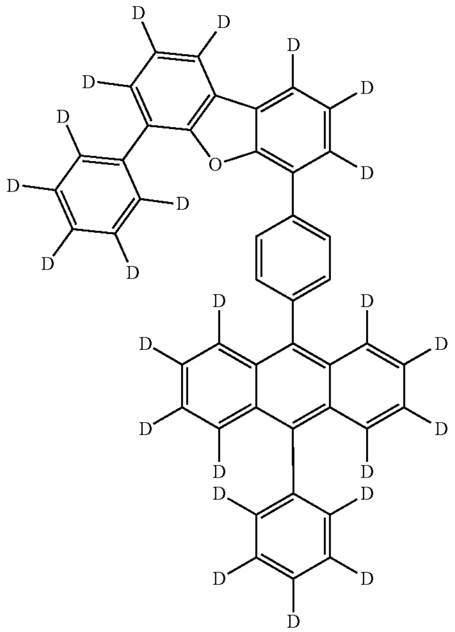
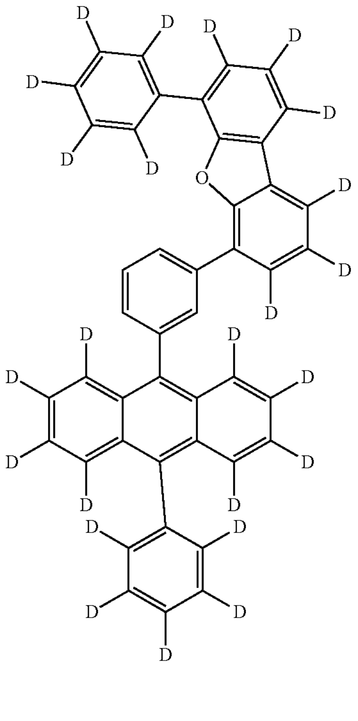
-continued
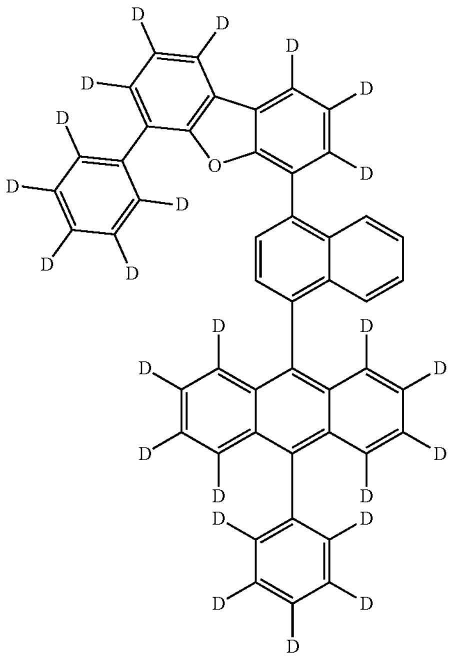
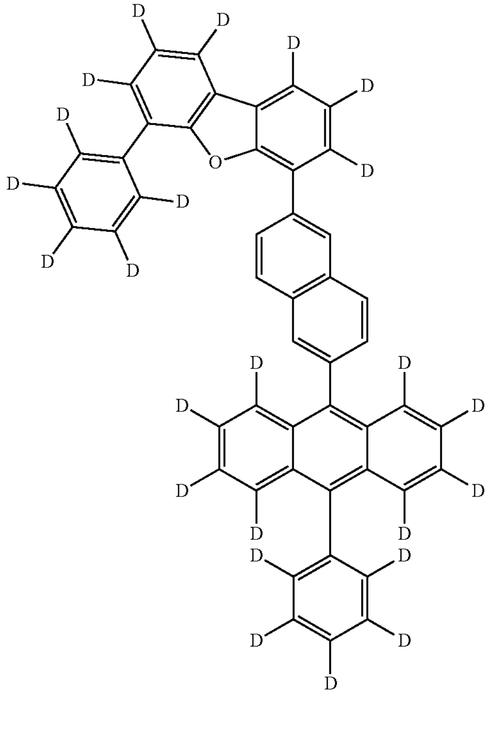

-continued
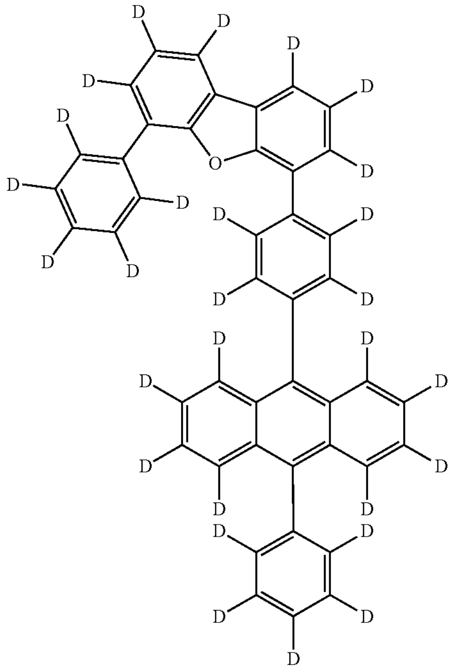
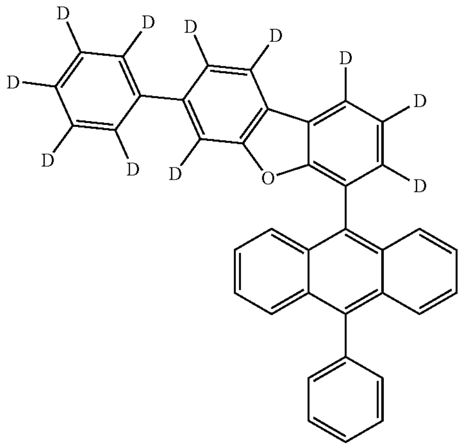
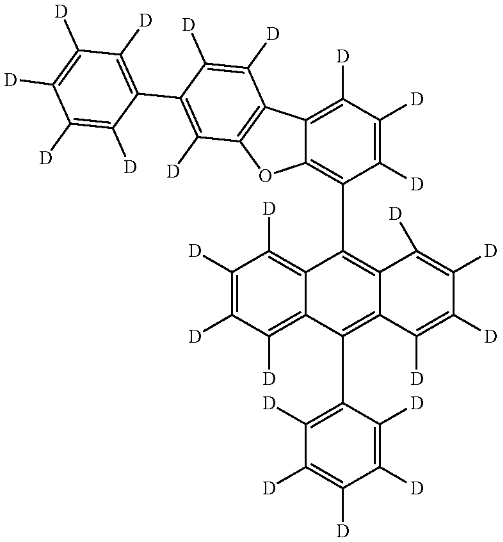
-continued
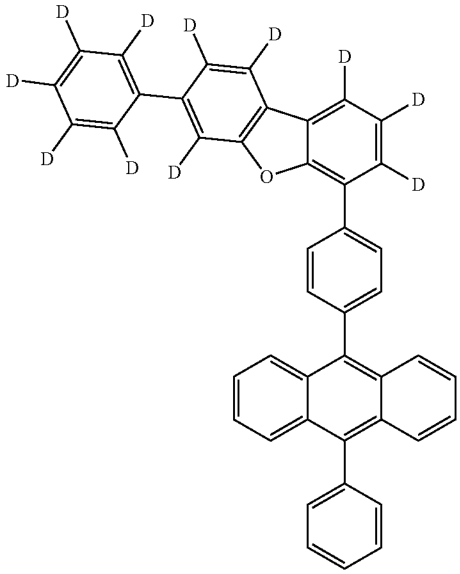
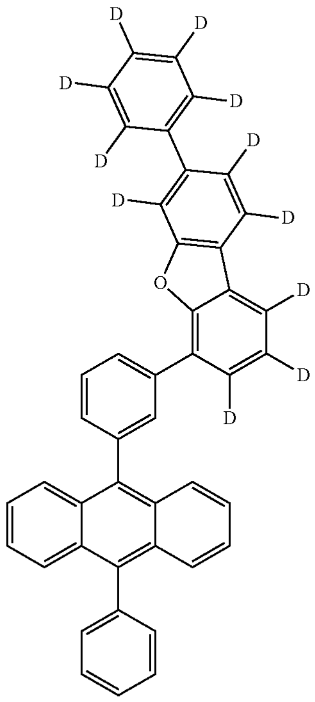

-continued
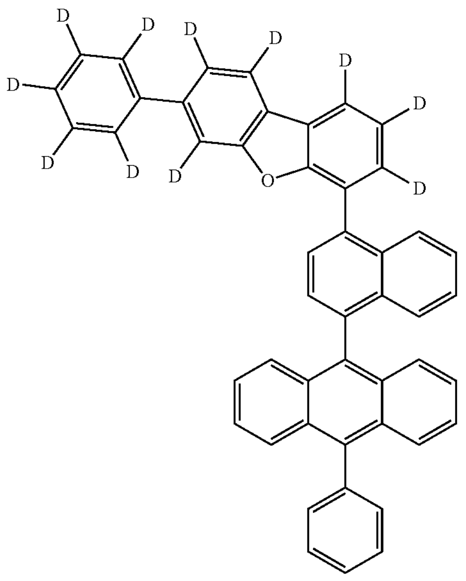
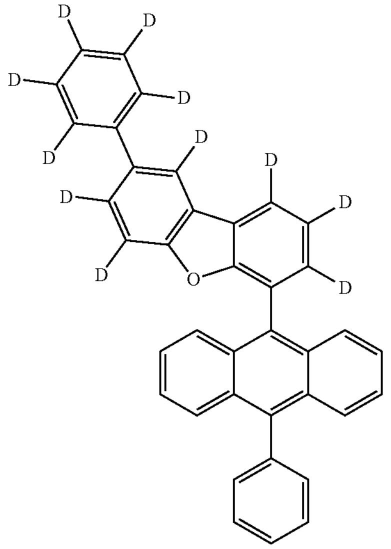
-continued
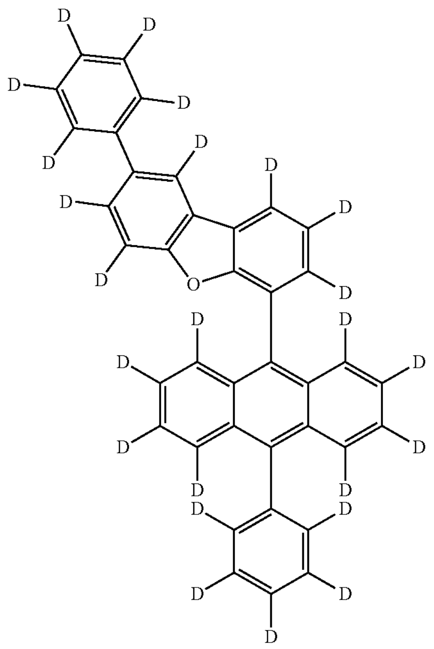
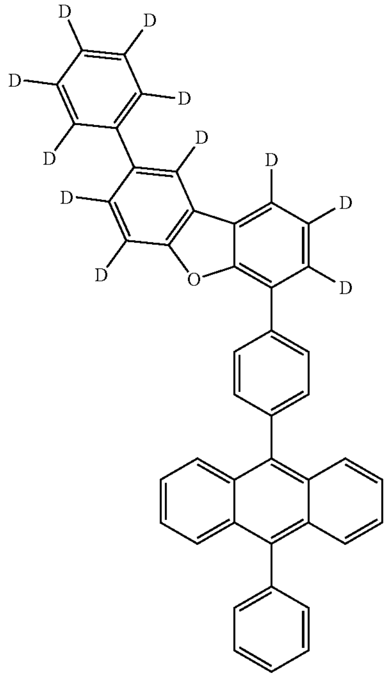

-continued
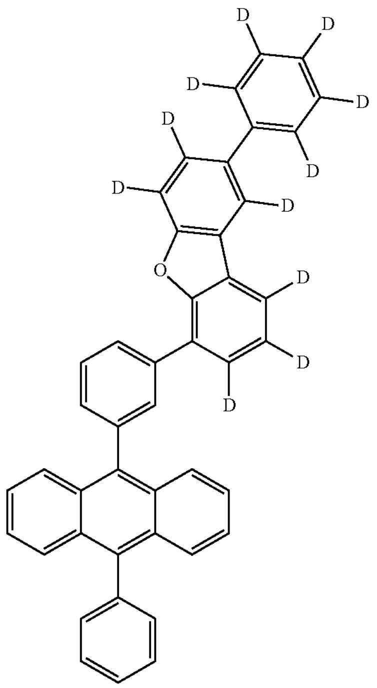
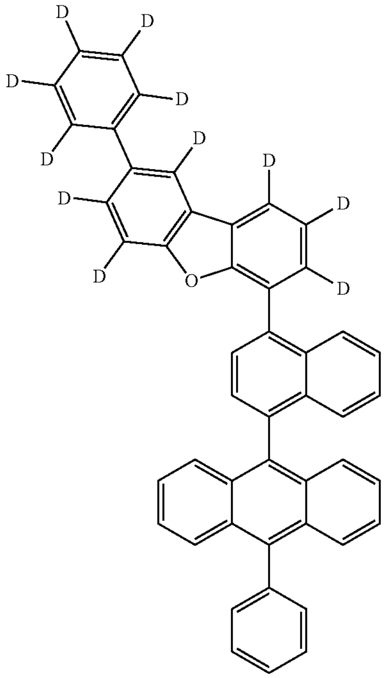
-continued
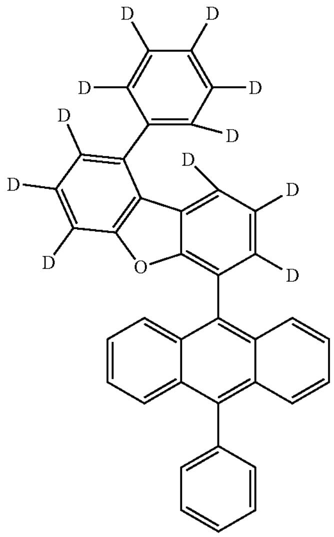
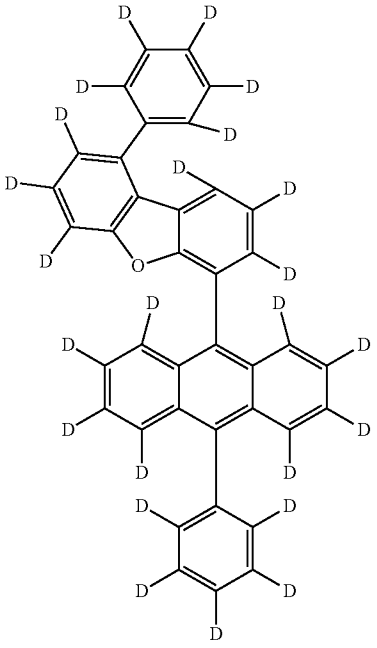

-continued
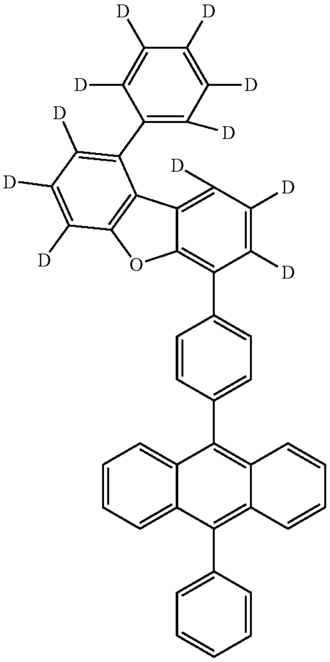
-continued
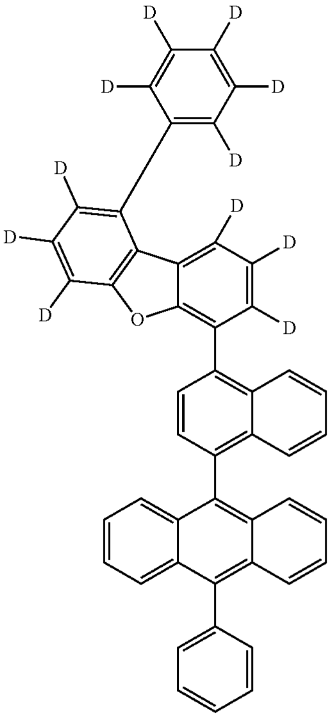
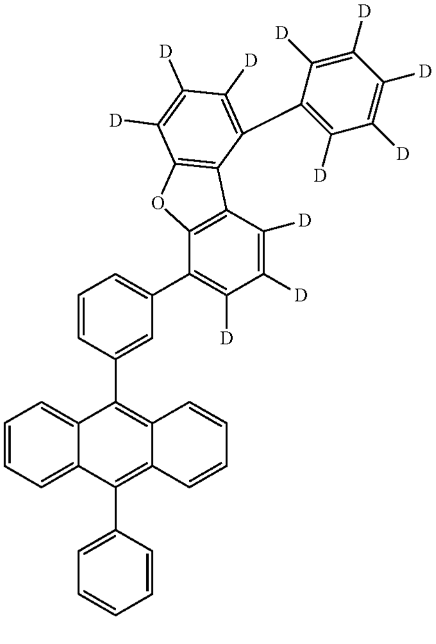
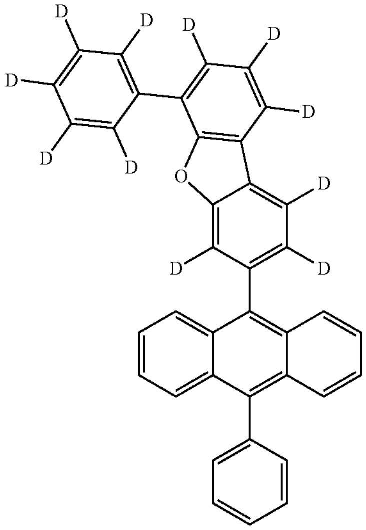

-continued
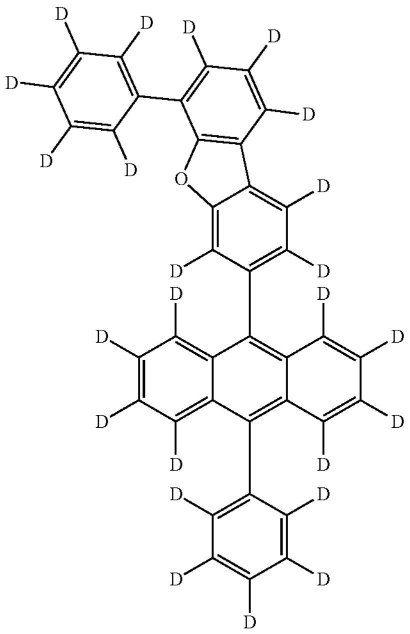
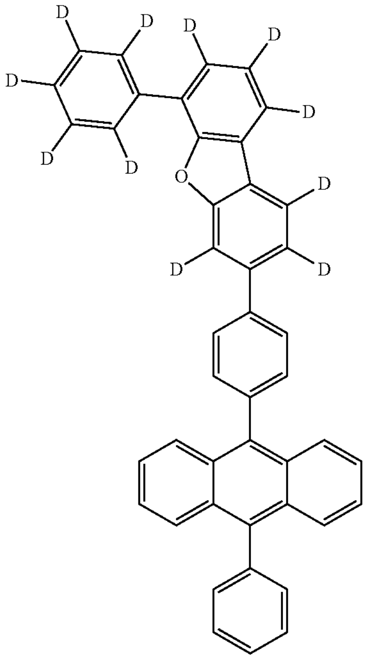
-continued
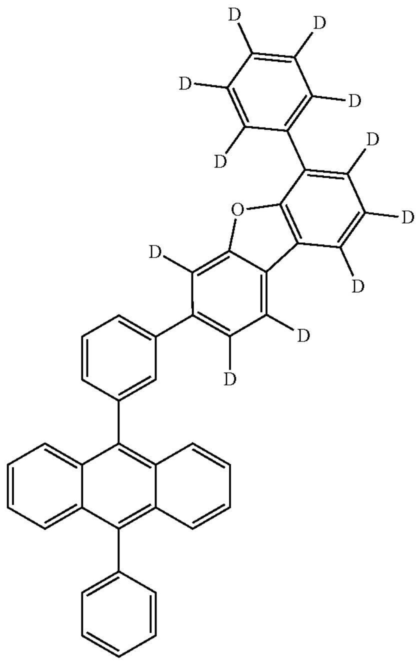
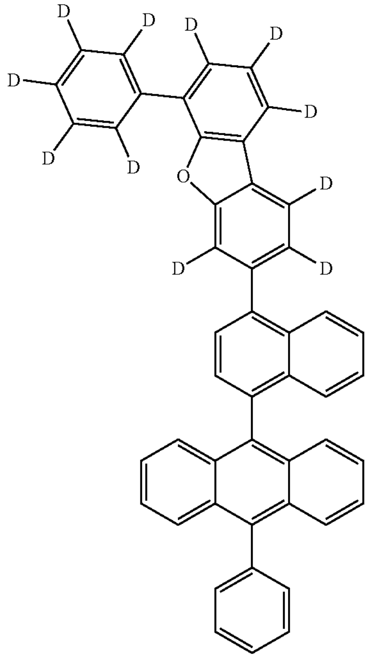

-continued
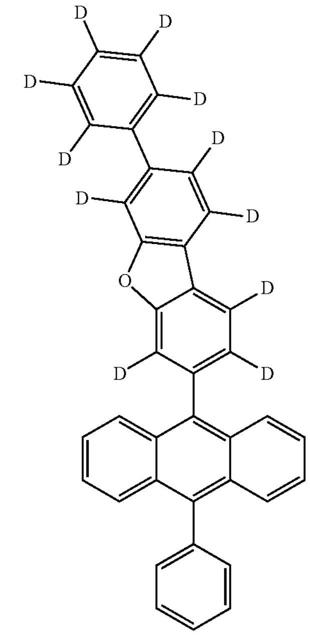
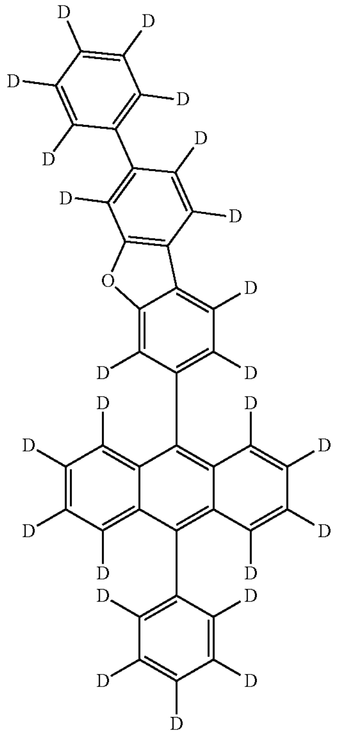
-continued
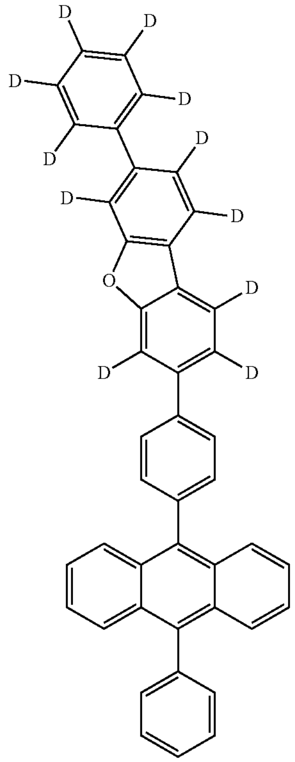
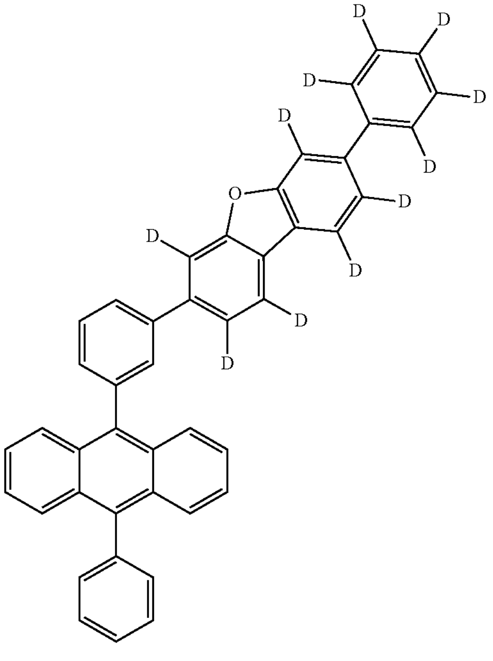

-continued
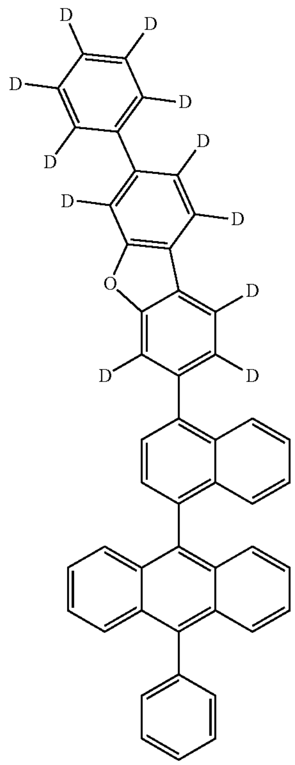
-continued
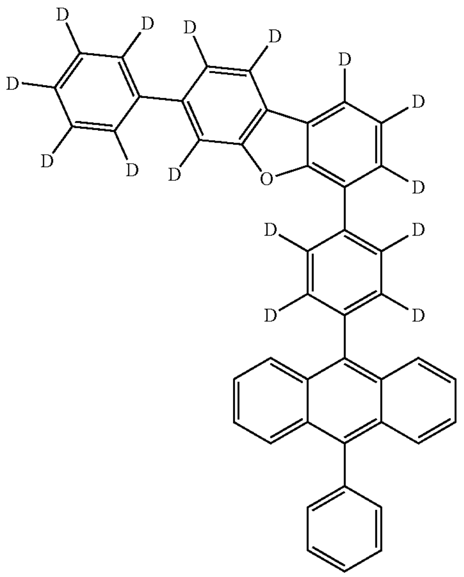
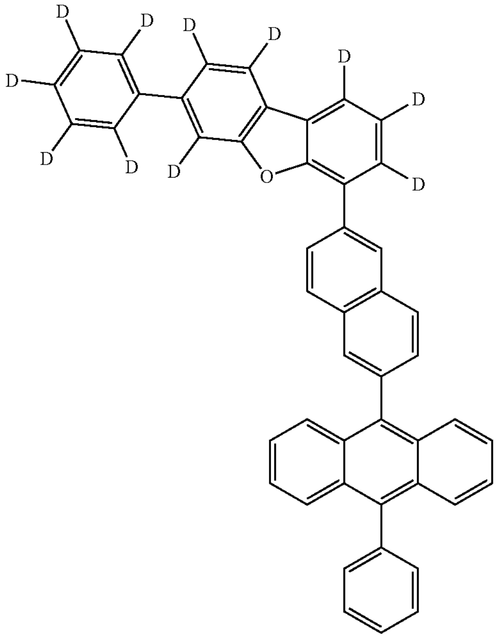
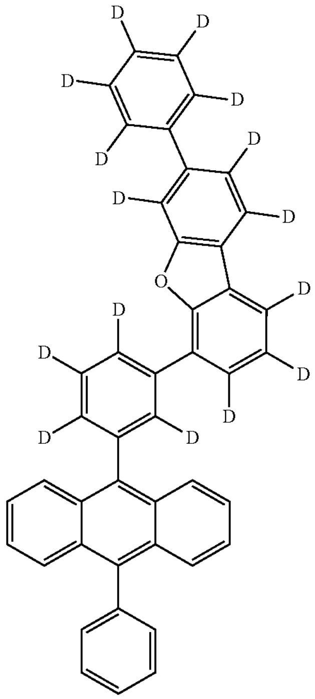

-continued
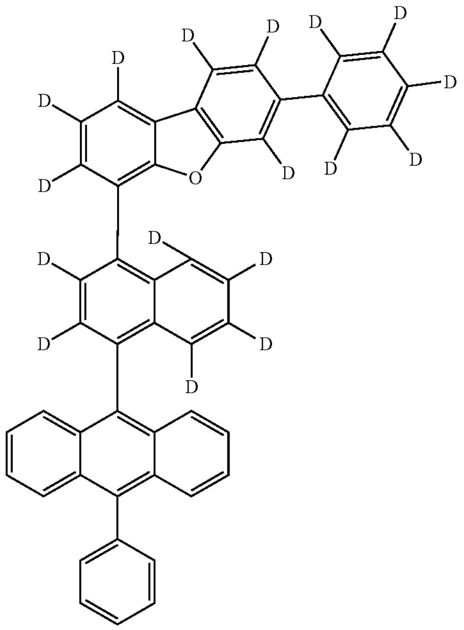
-continued
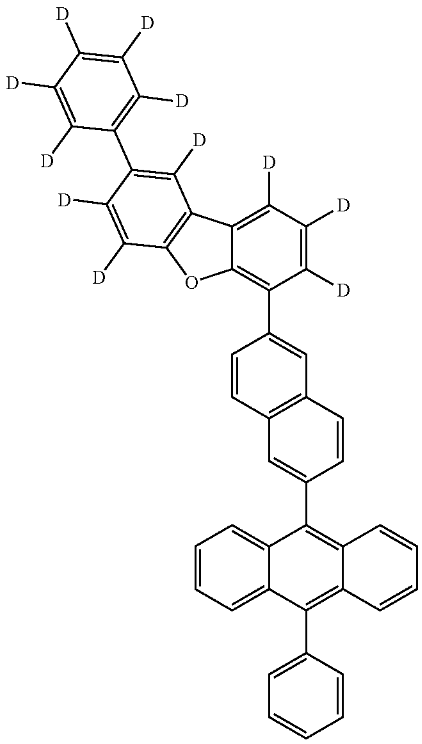
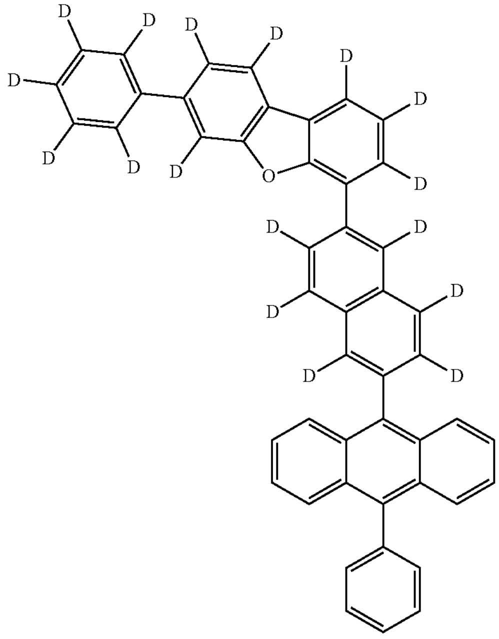
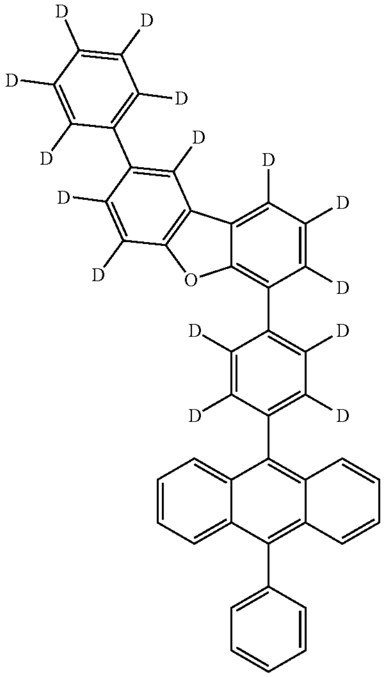

-continued
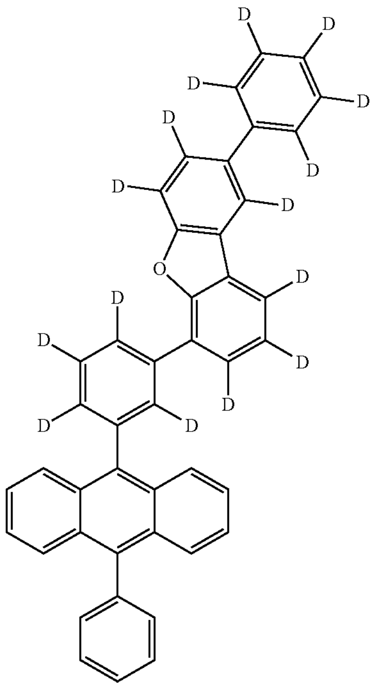
-continued
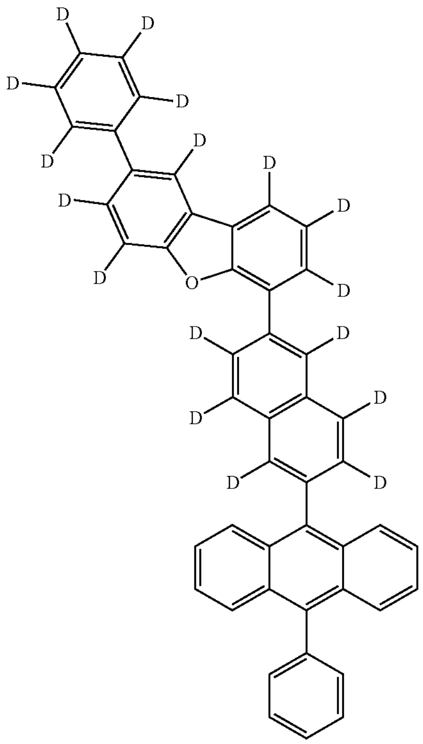
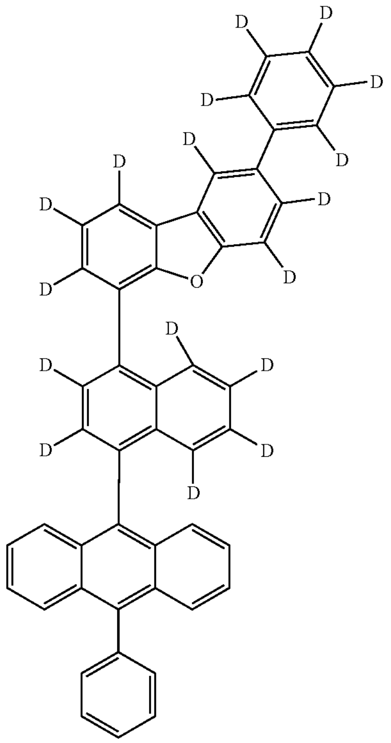
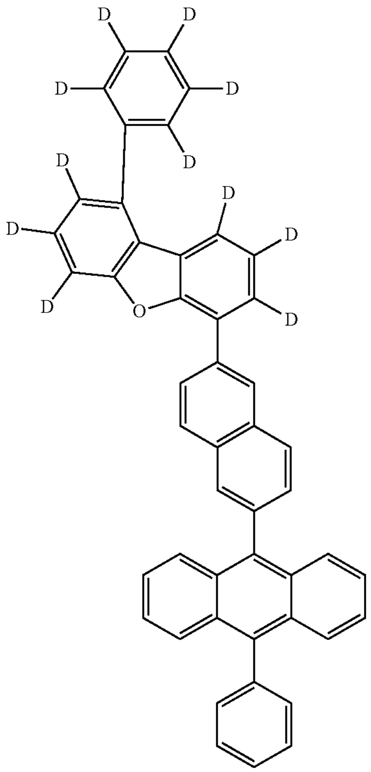

-continued
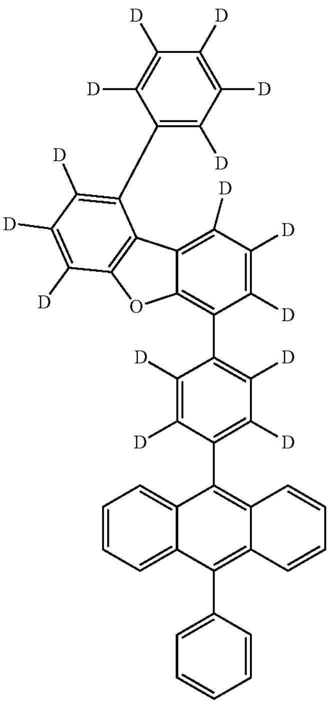
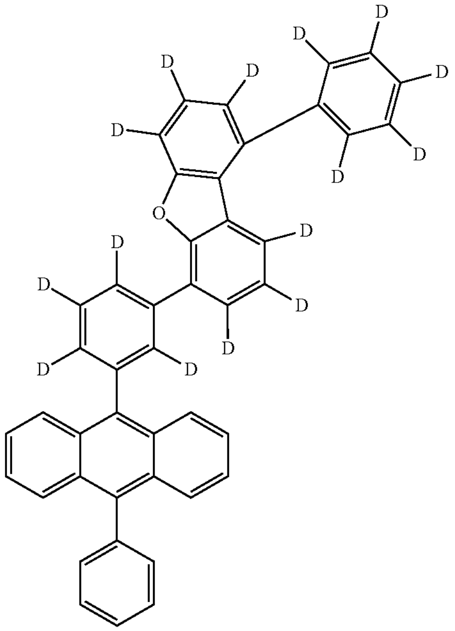
-continued
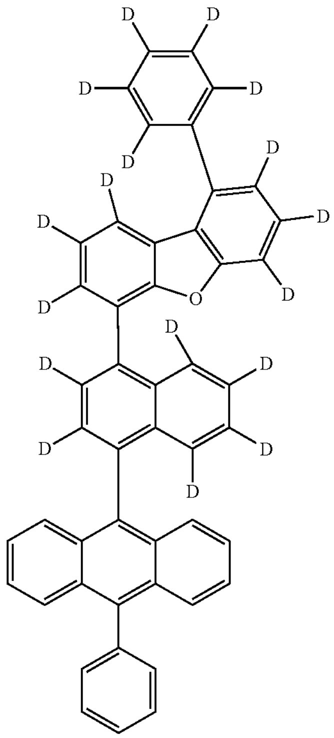
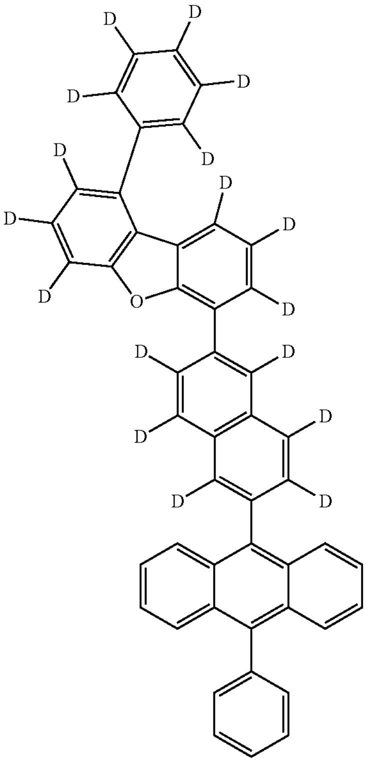

-continued
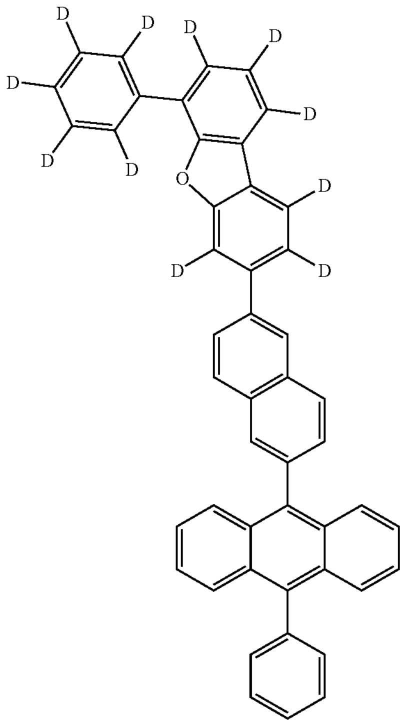
-continued
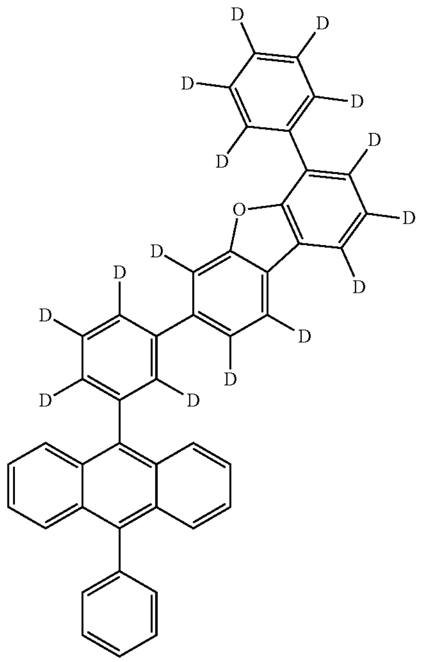
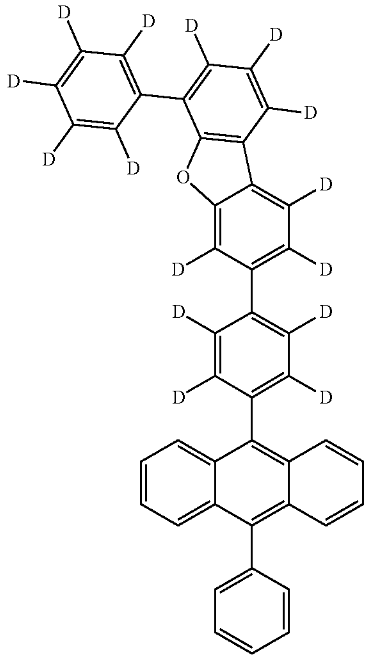
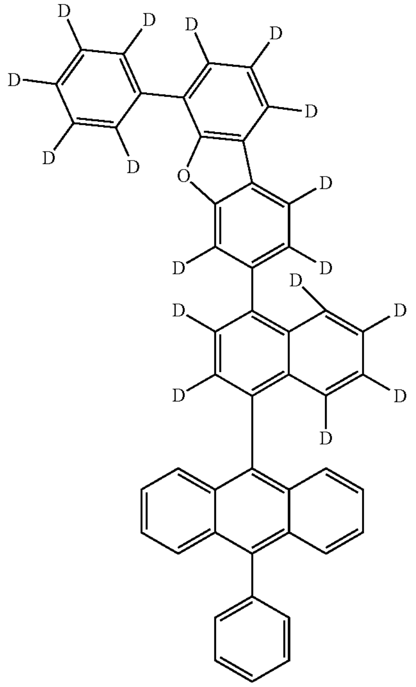

-continued
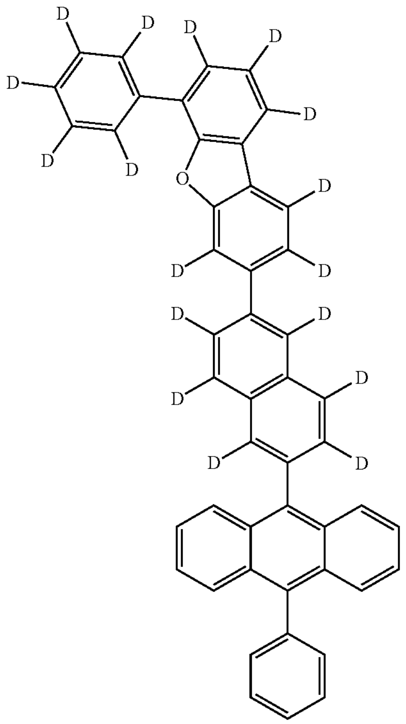
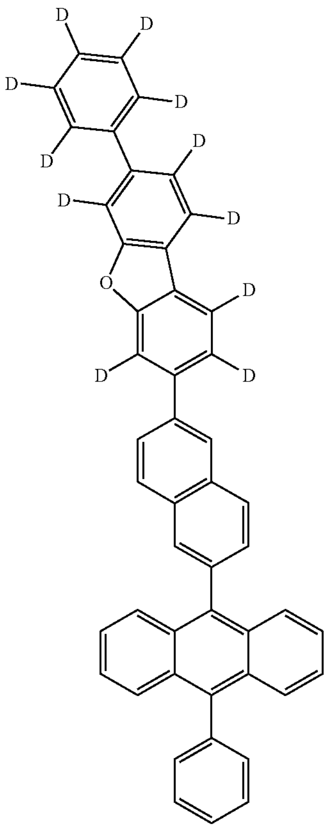
-continued
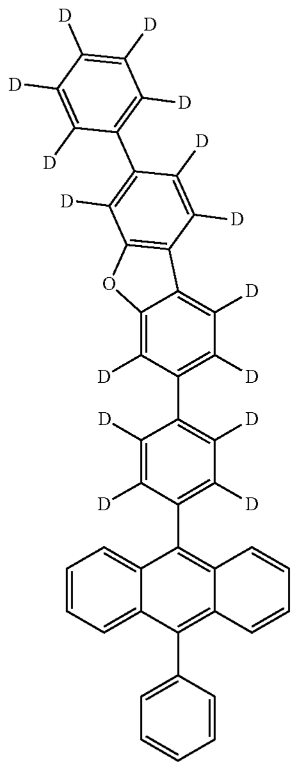
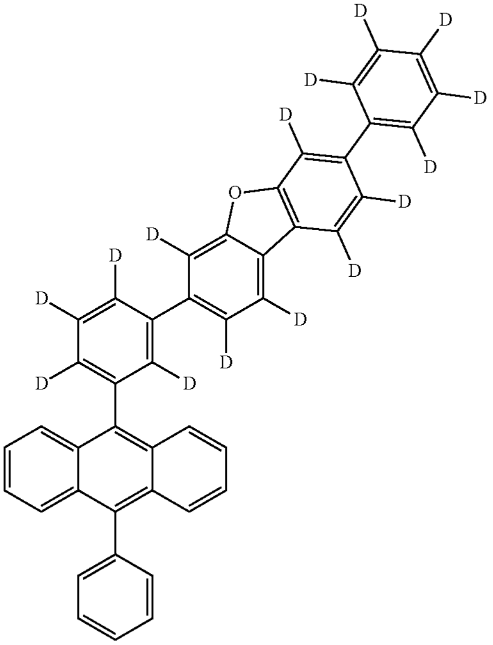

-continued
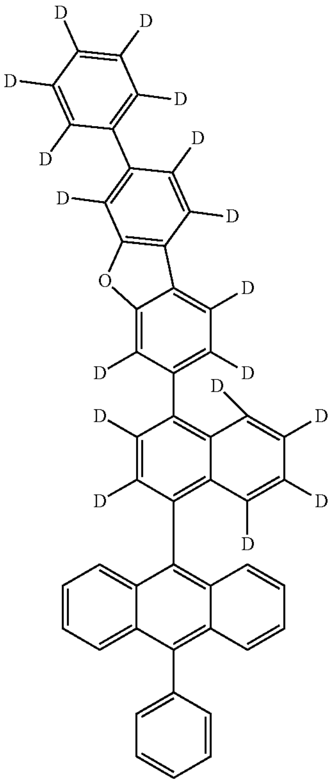
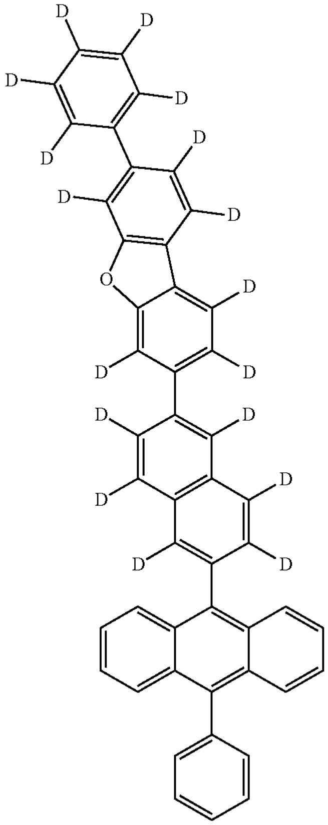
-continued
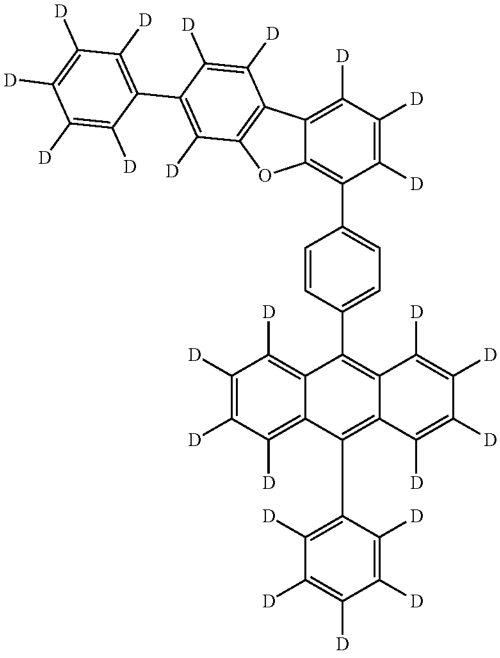
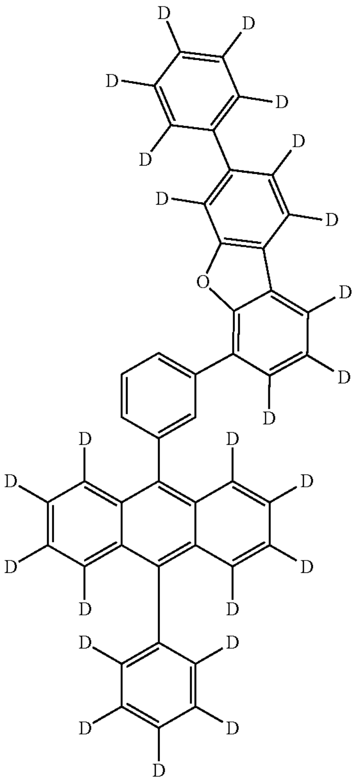

-continued
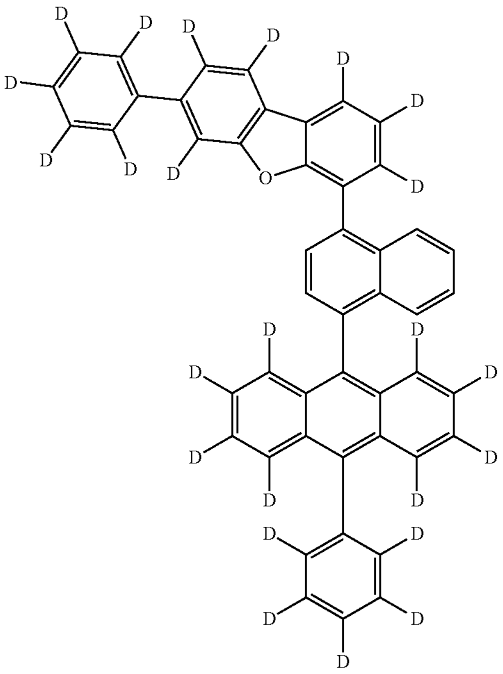
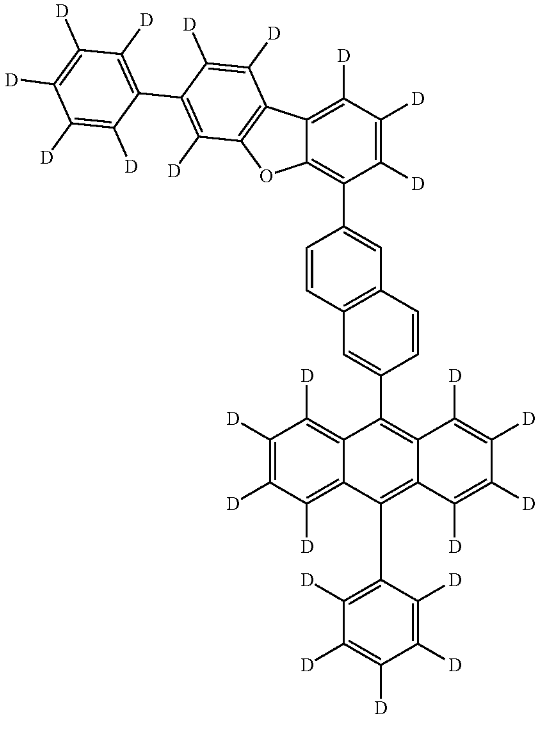
-continued
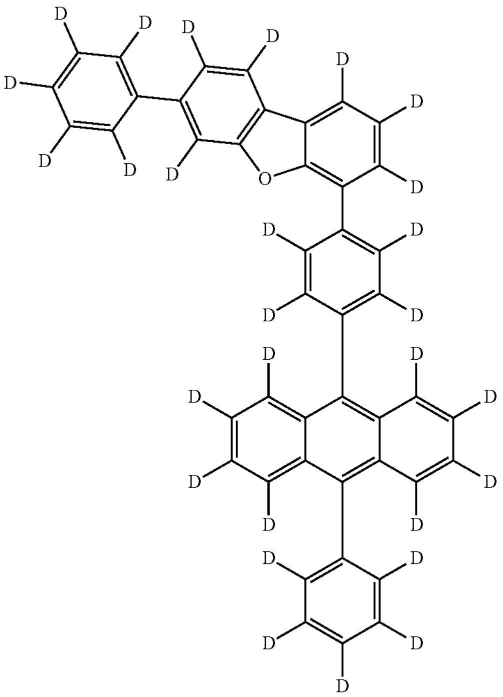
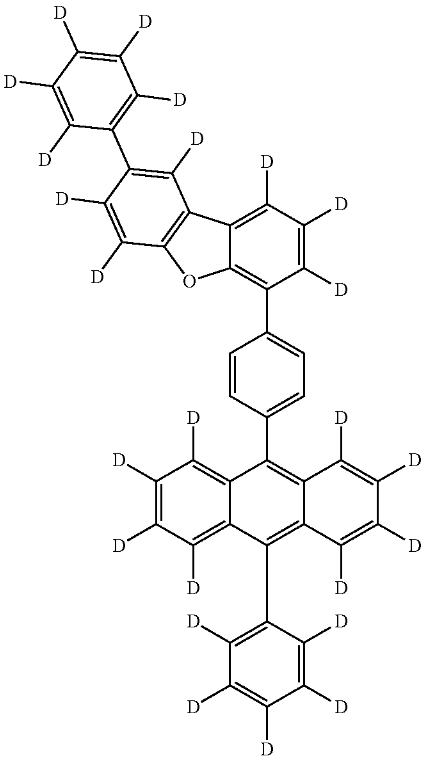

-continued
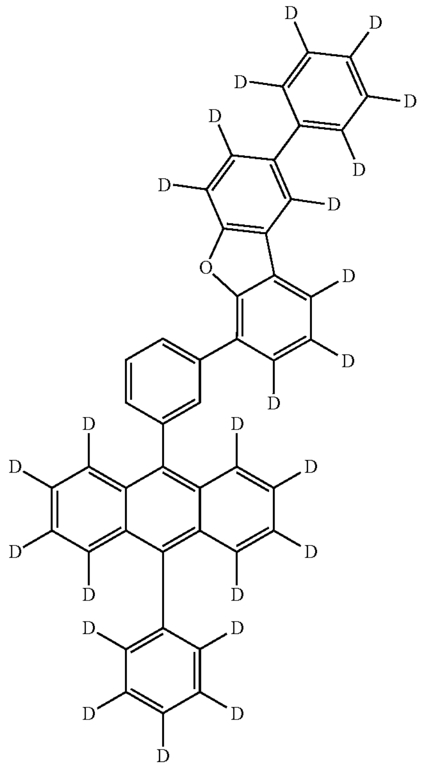
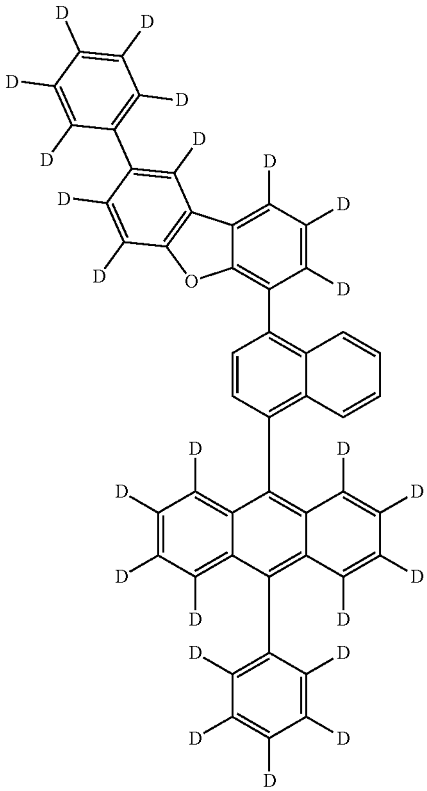
-continued
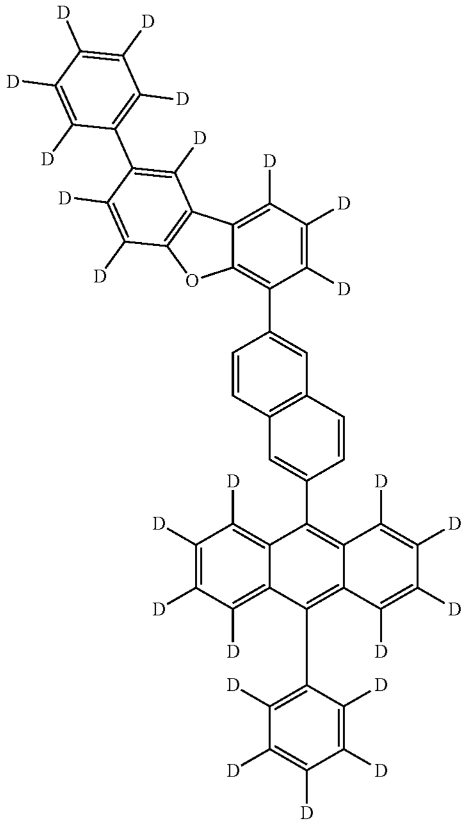
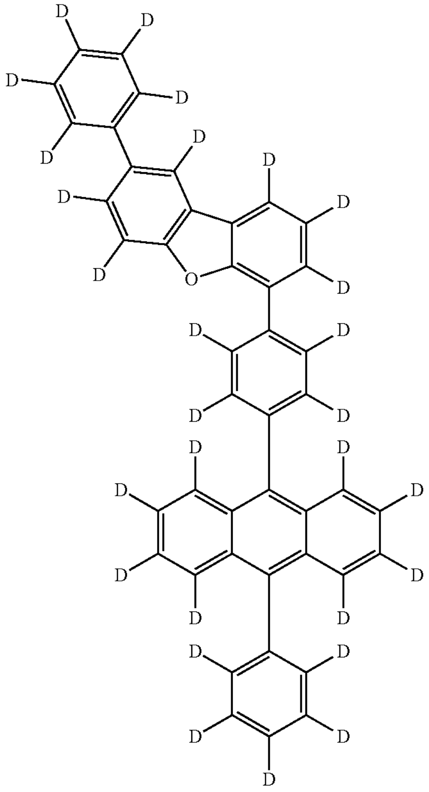

-continued
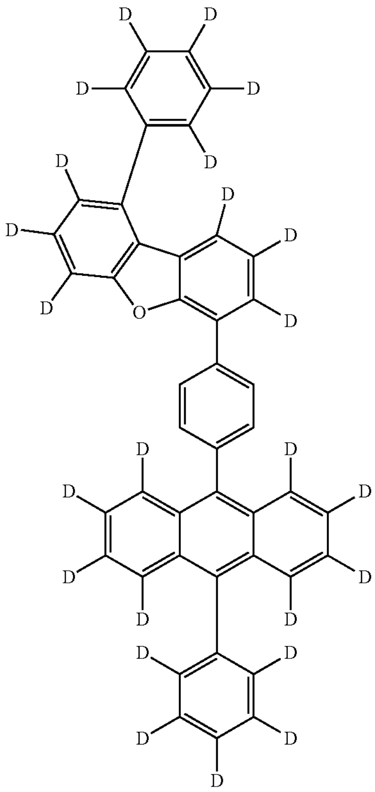
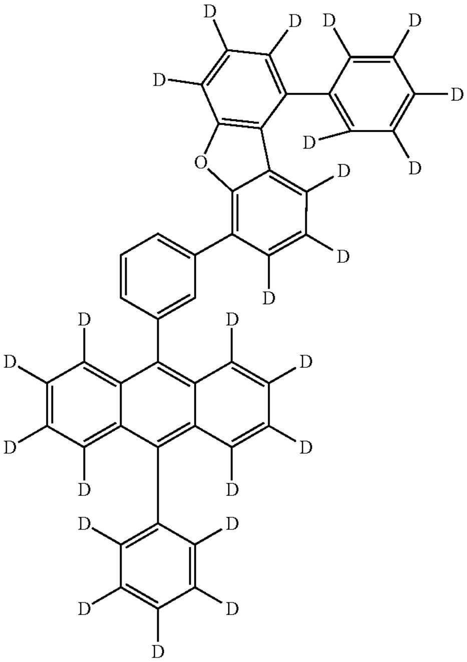
-continued
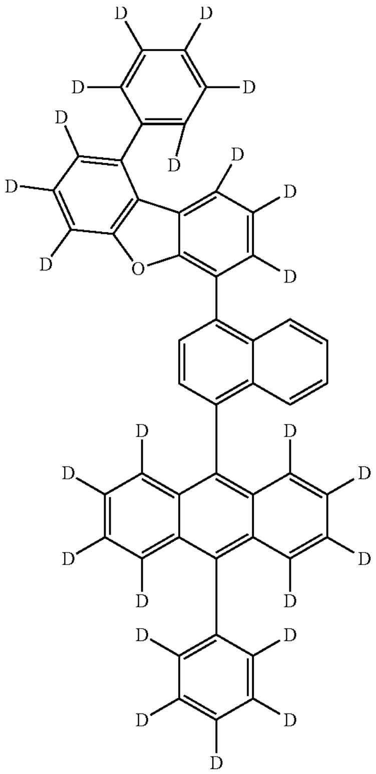
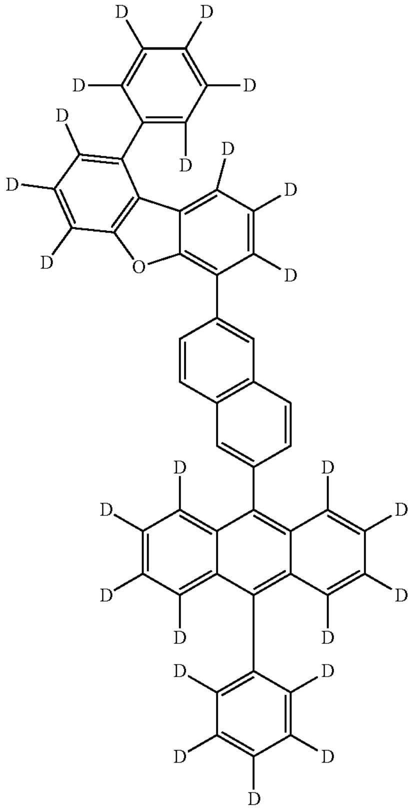

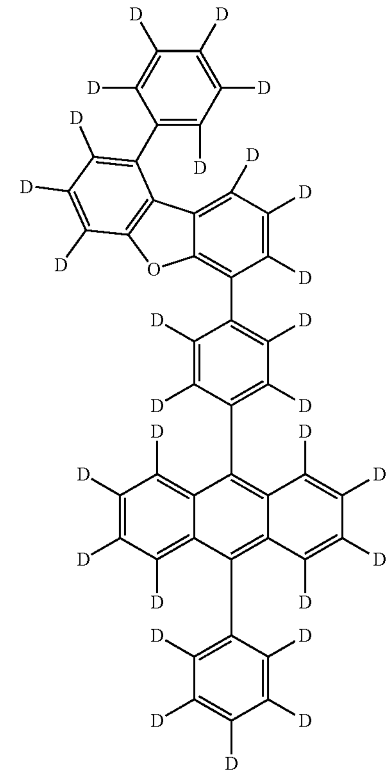
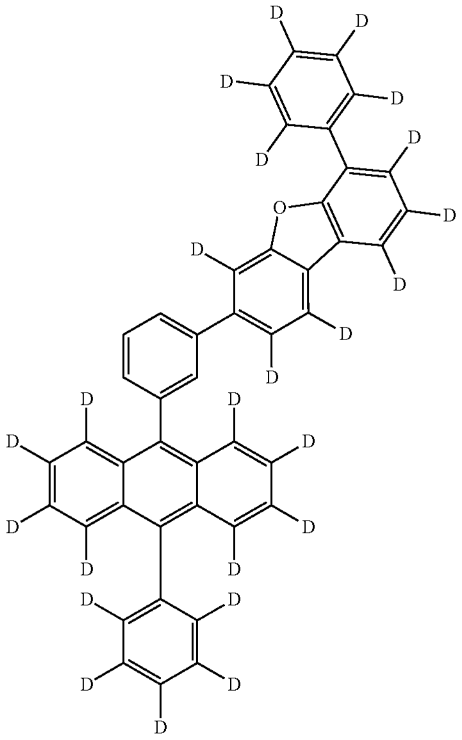
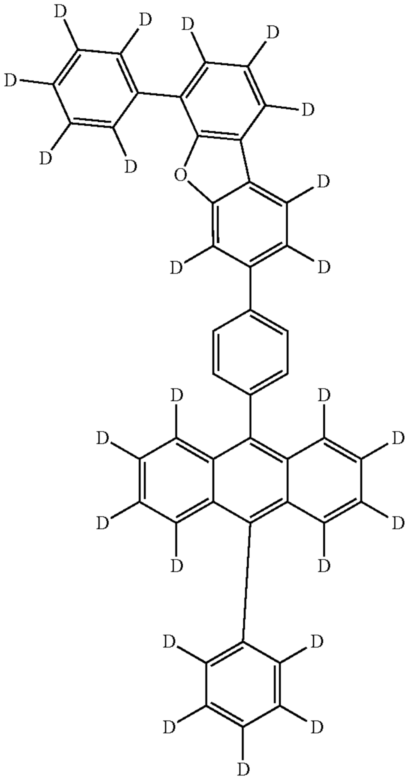
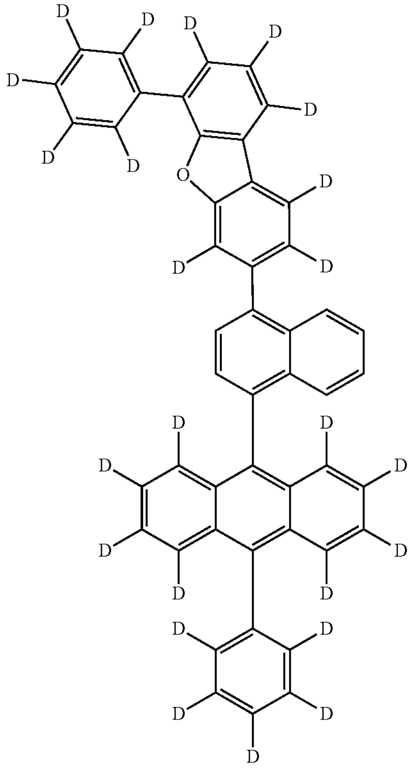

-continued
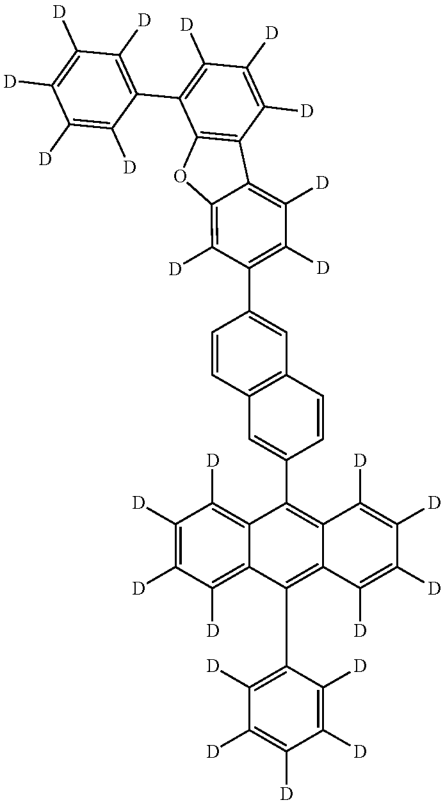
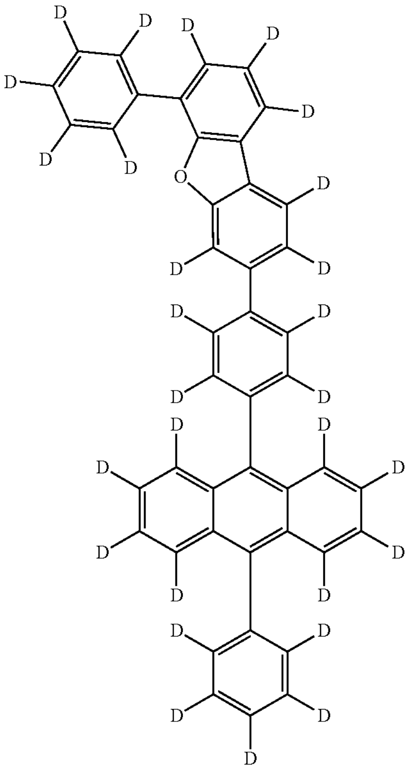 [SMILES: [2H]c1c([2H])c([2H])c(-c2c([2H])c([2H])c([2H])c3c2oc2c([2H])c(-c4c([2H])c([2H])c(-c5c6c([2H])c([2H])c([2H])c([2H])c6c(-c6c([2H])c([2H])c([2H])c([2H])c6[2H])c6c([2H])c([2H])c([2H])c([2H])c56)c([2H])c4[2H])c([2H])c([2H])c23)c([2H])c1[2H]]
-continued
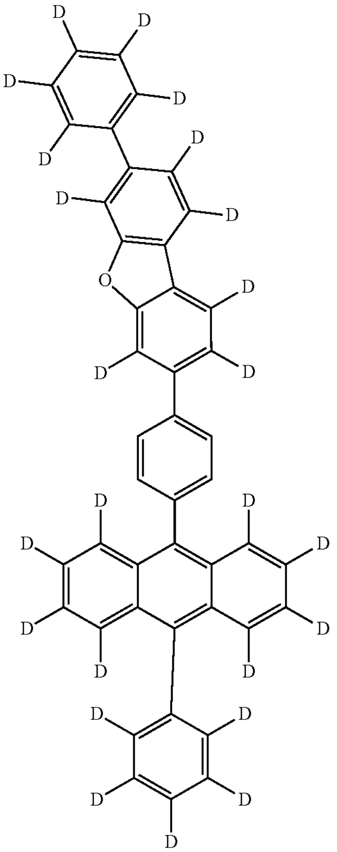
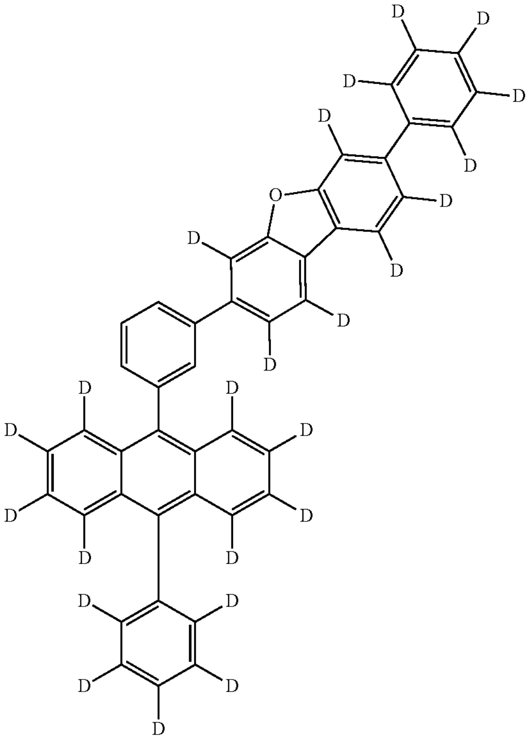

-continued
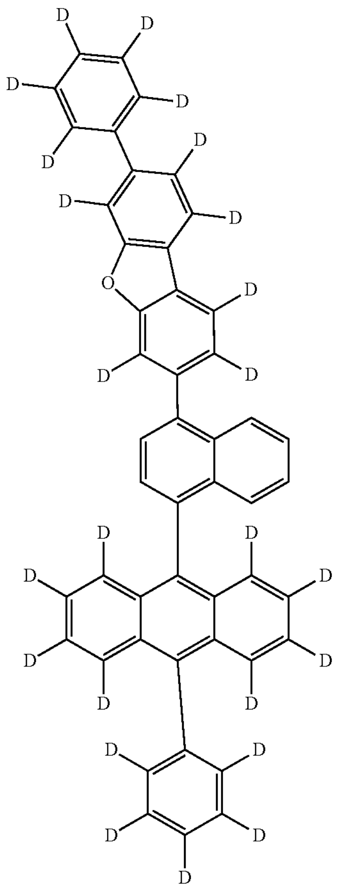
-continued
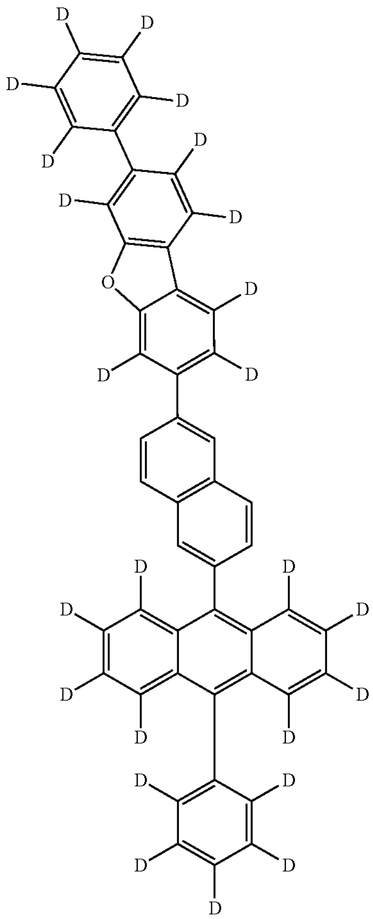

-continued
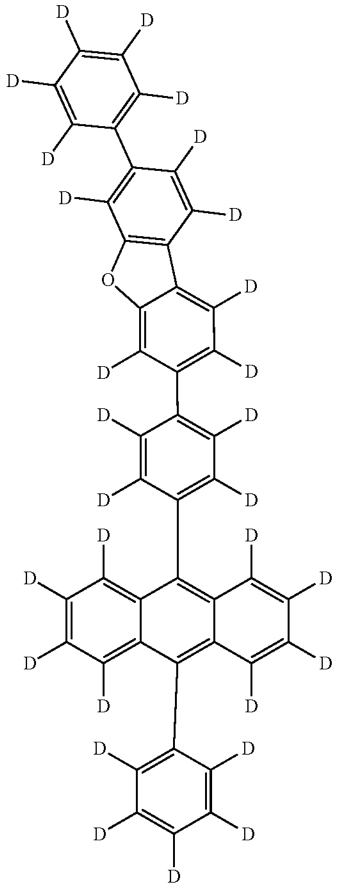
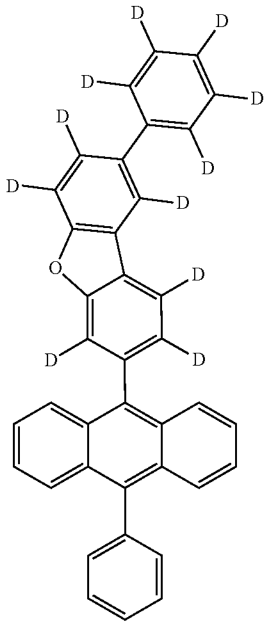
-continued
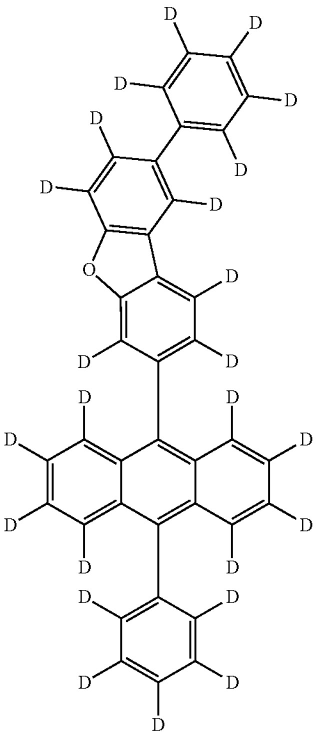
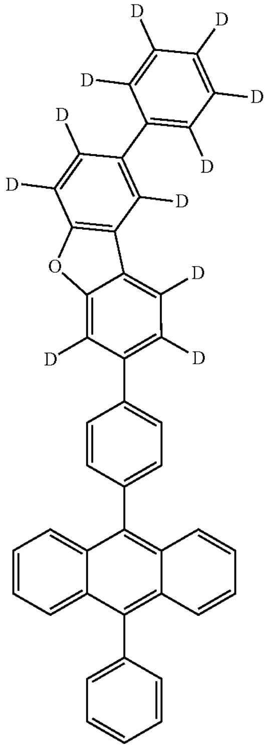

-continued
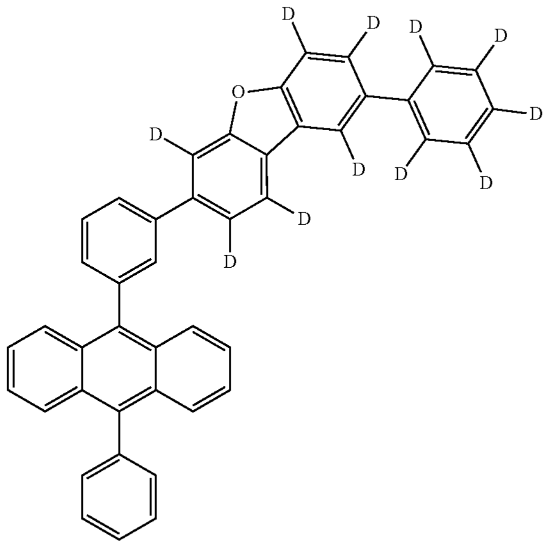
-continued
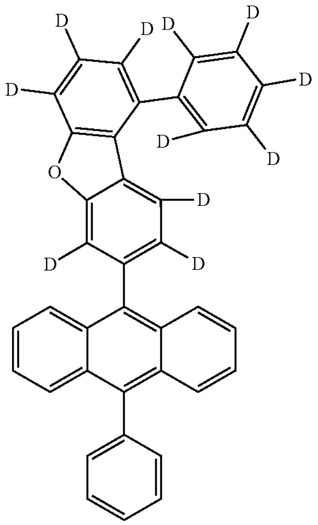
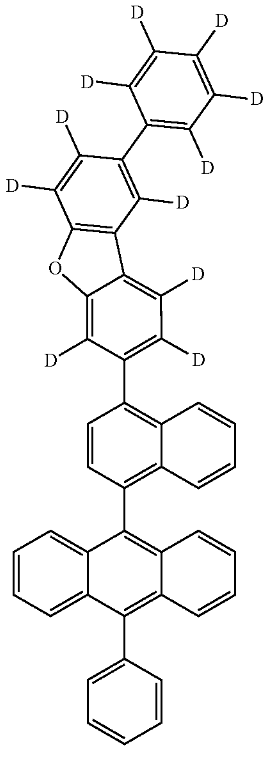
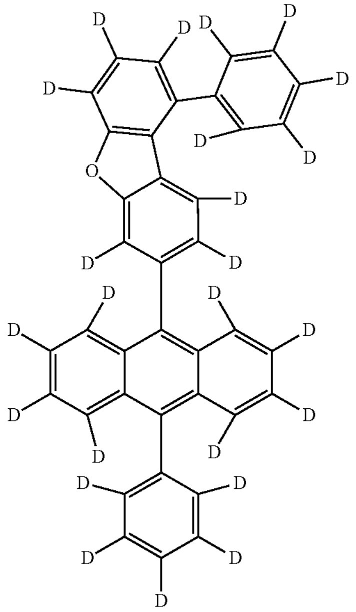

-continued
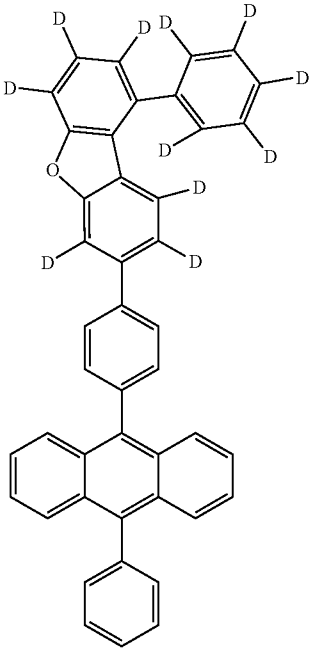
-continued
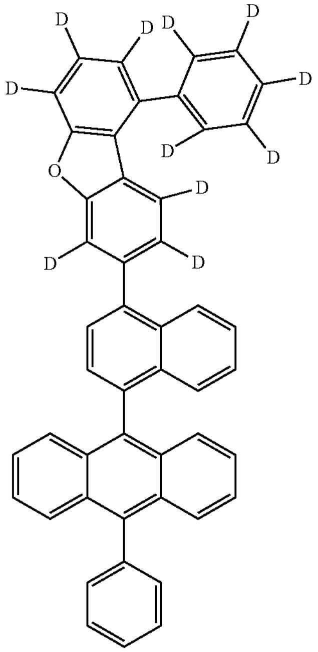
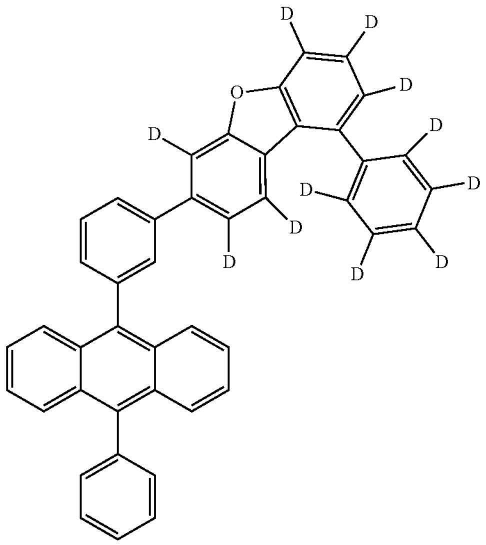
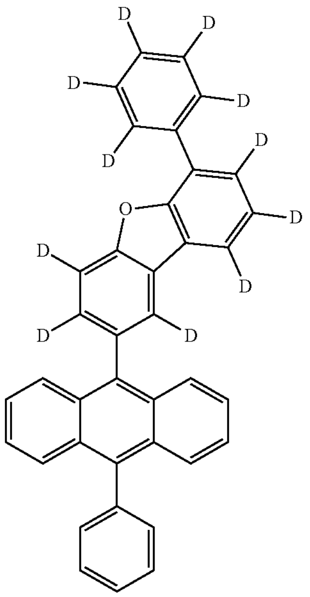

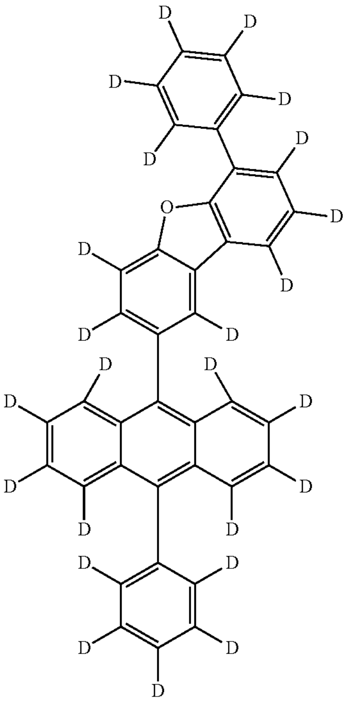
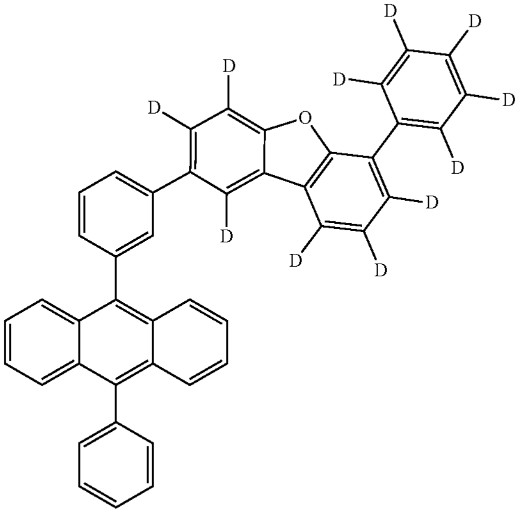
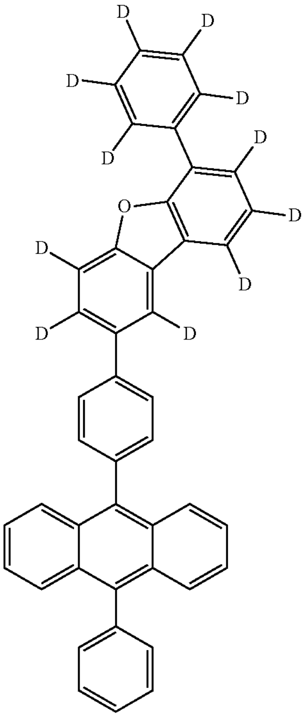
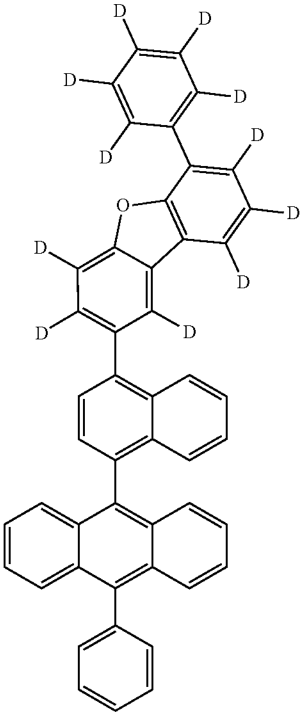

-continued
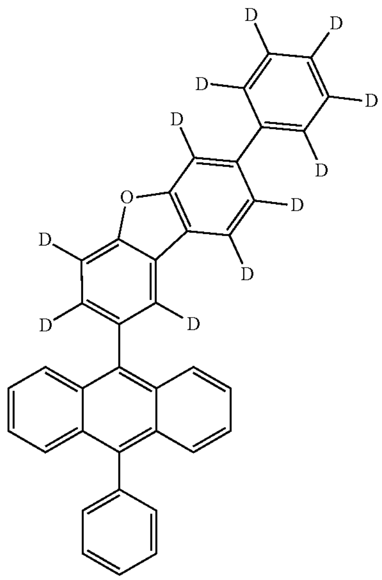
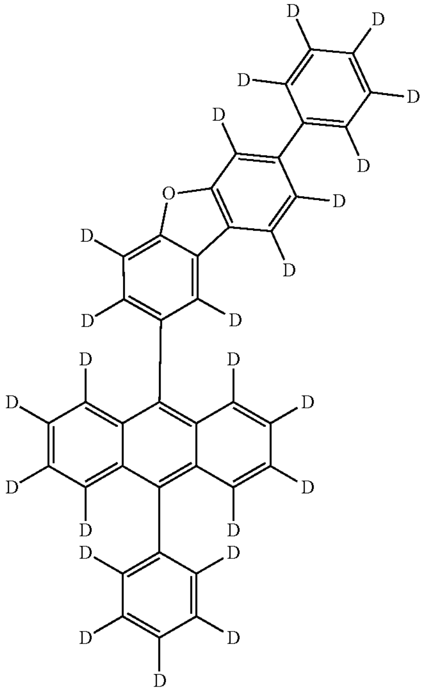
-continued
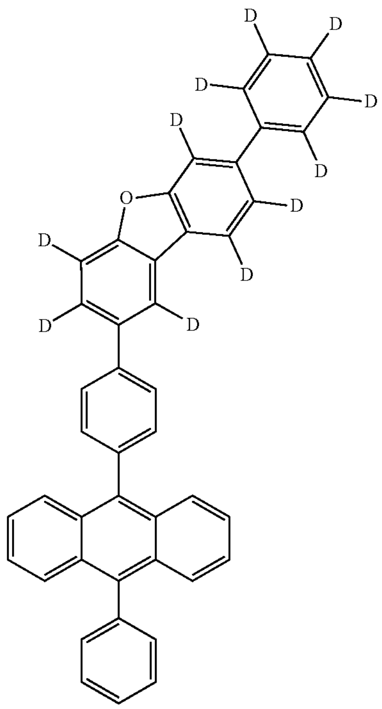
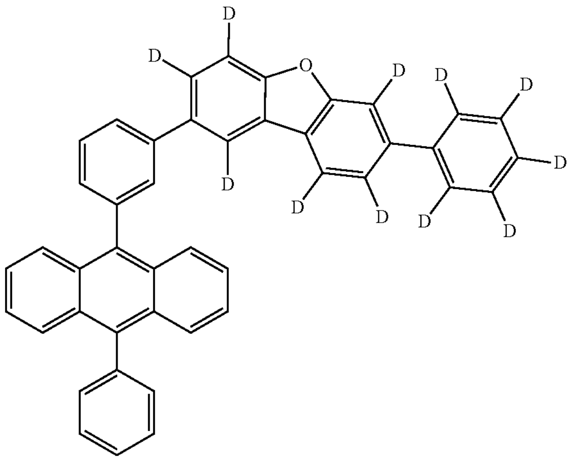

-continued
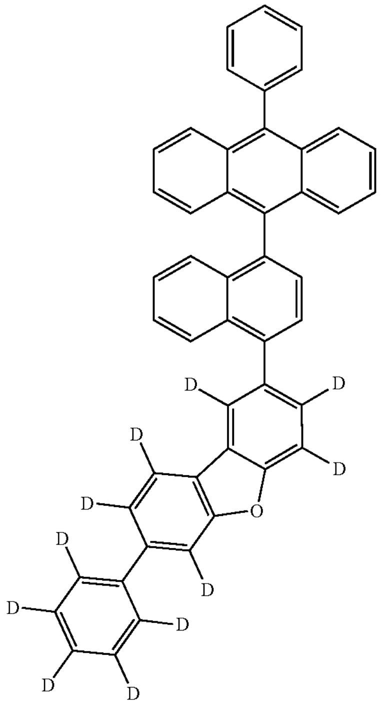
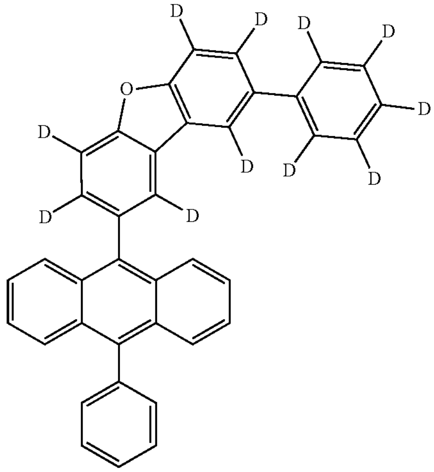
-continued
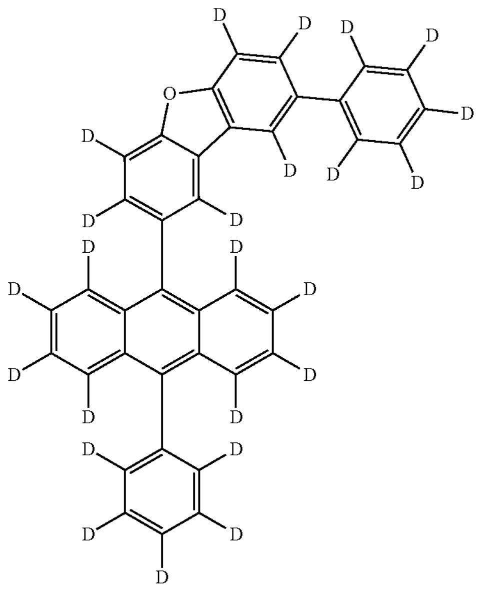
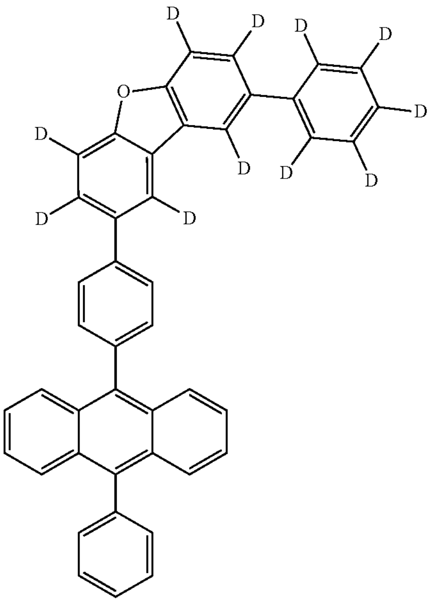
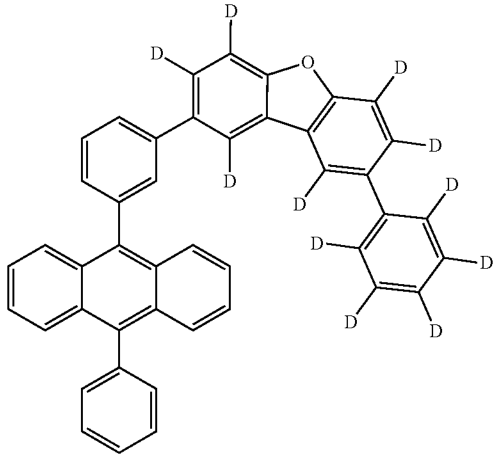

-continued
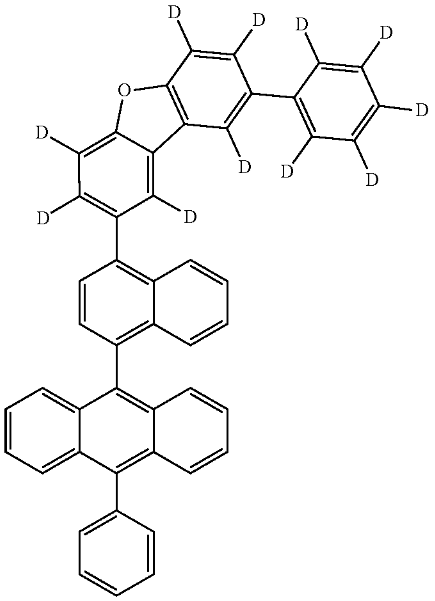
-continued
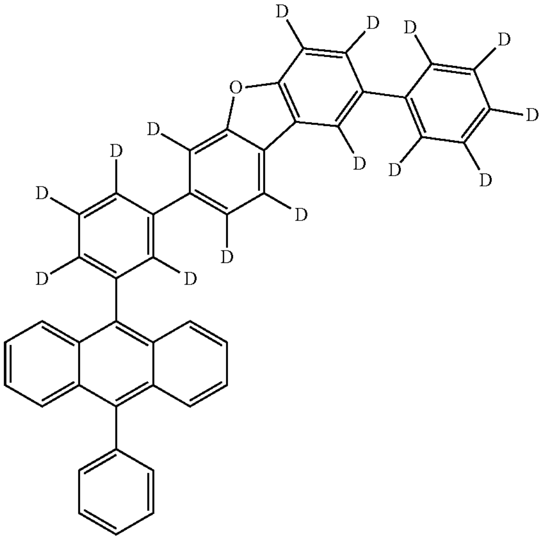
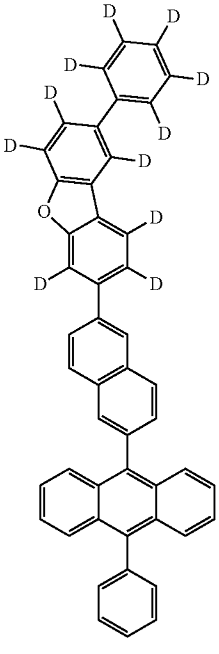
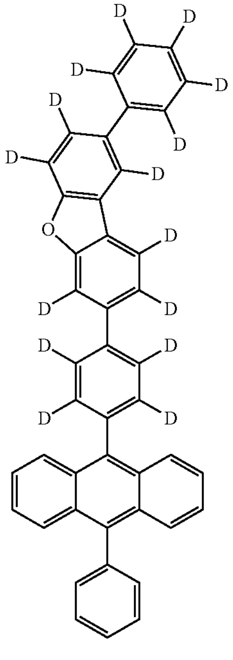
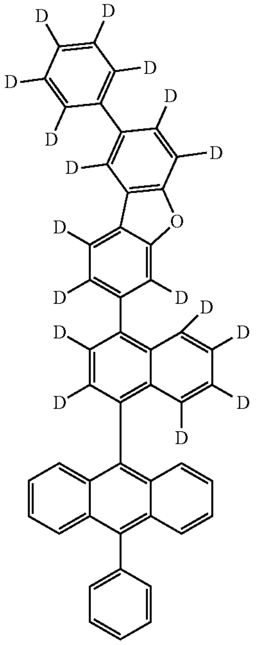
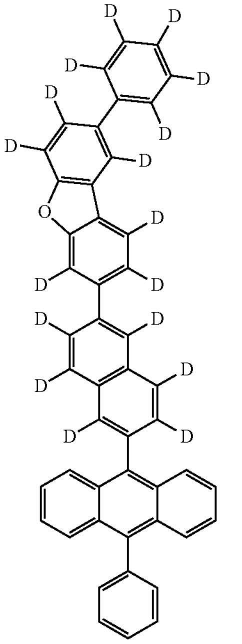

-continued
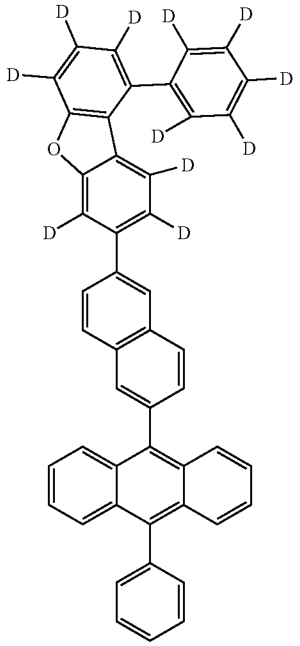
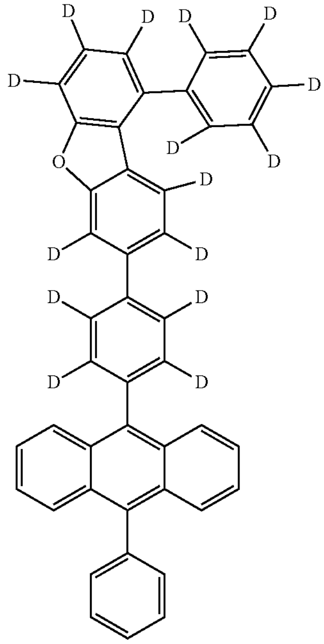
-continued
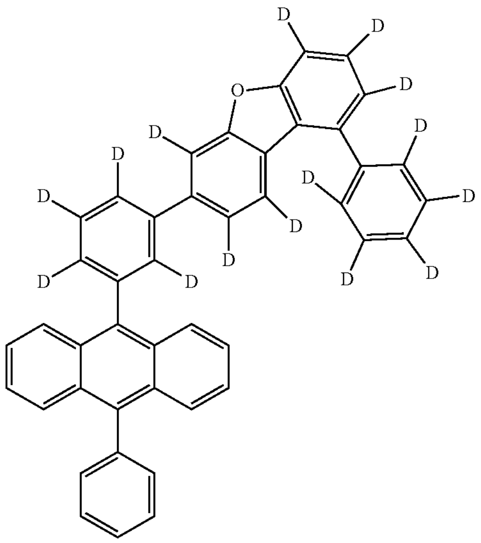
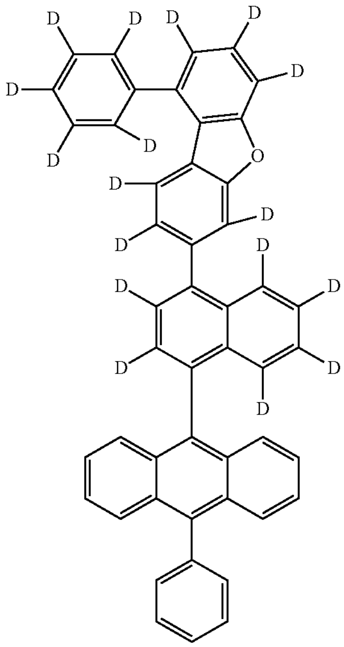

-continued
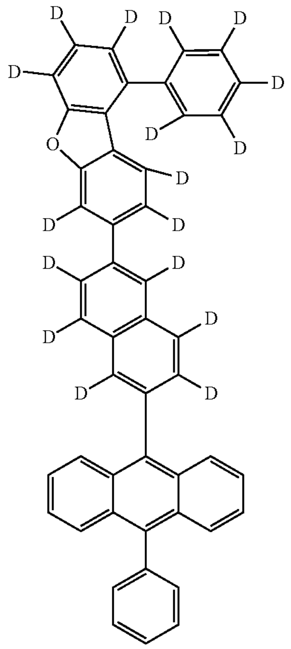
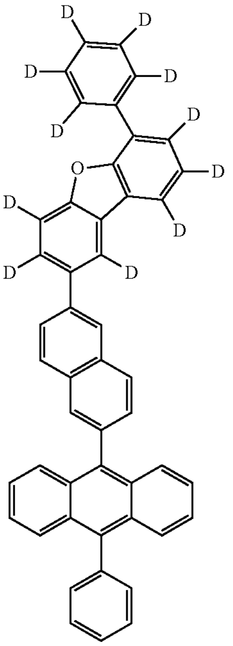
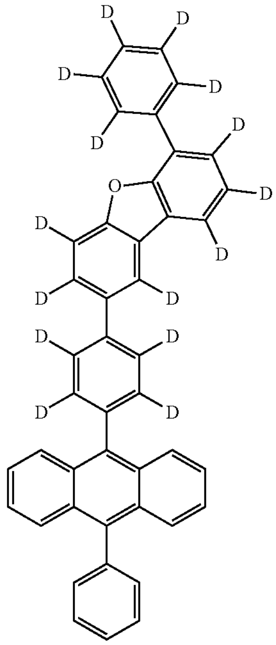
-continued
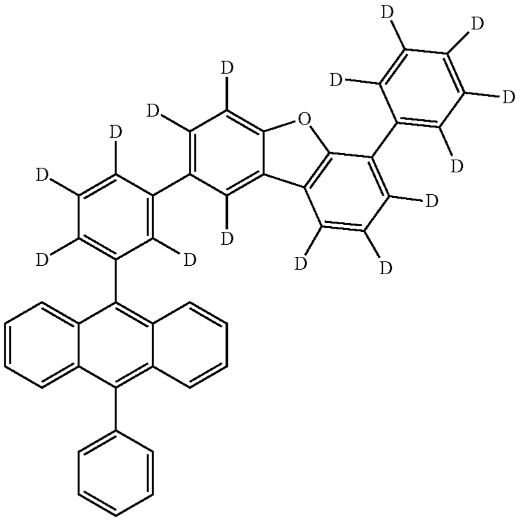
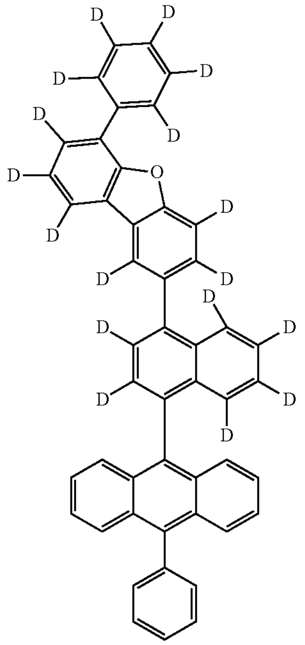
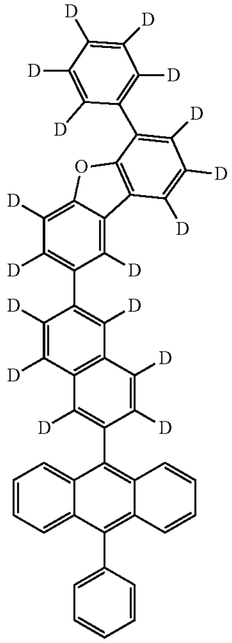

-continued
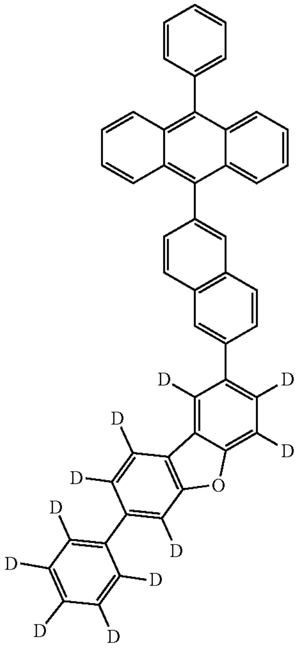
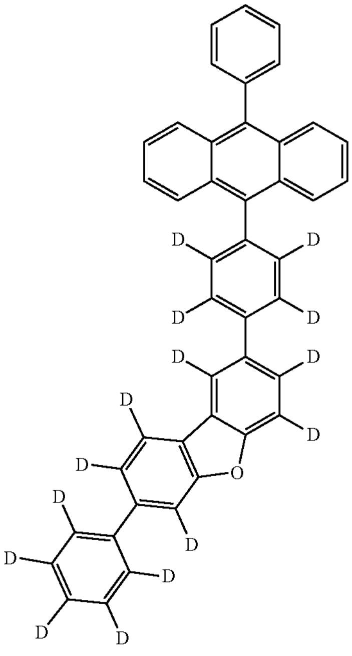
-continued
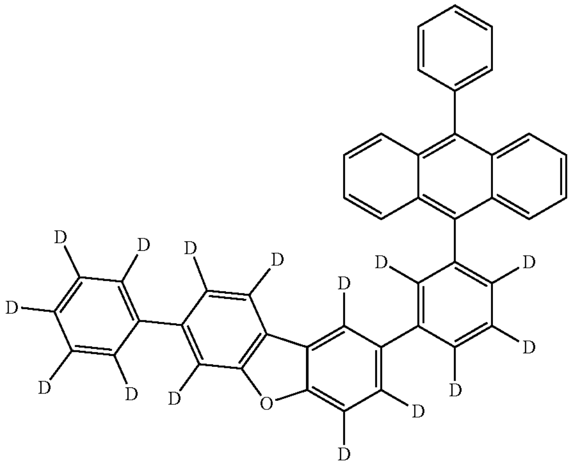
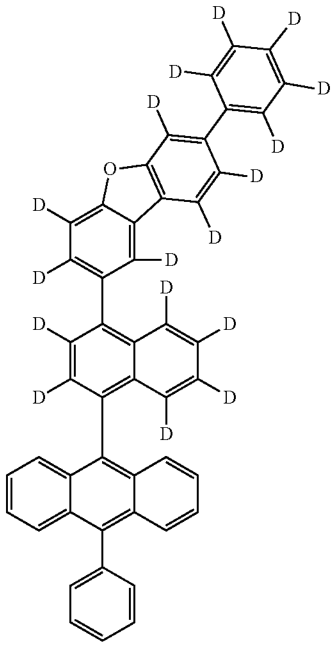

-continued
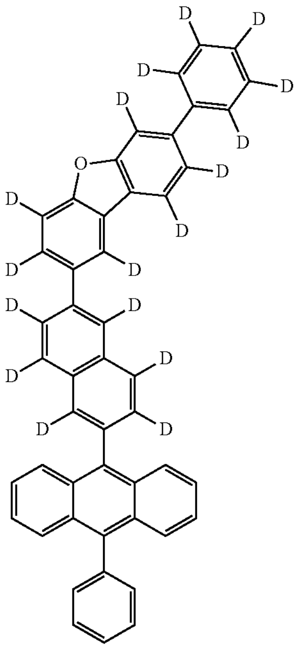
-continued
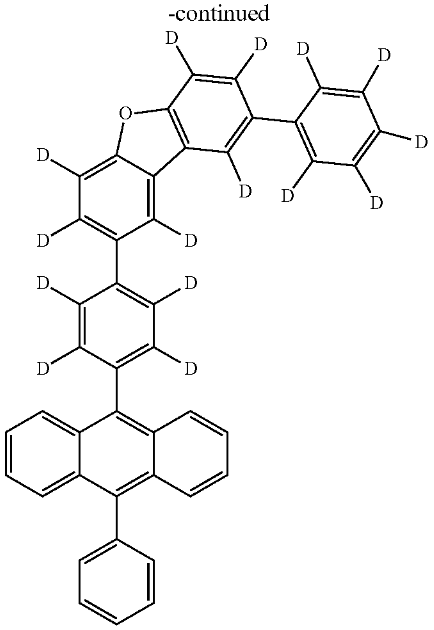
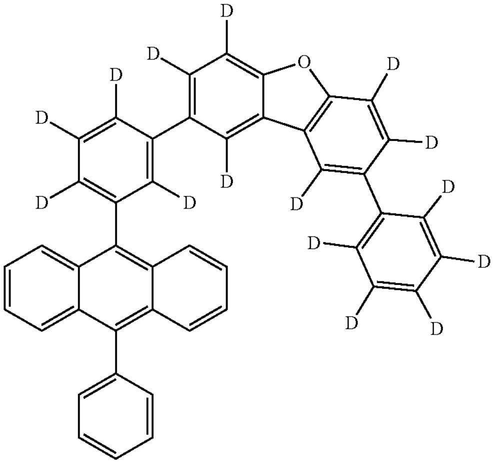
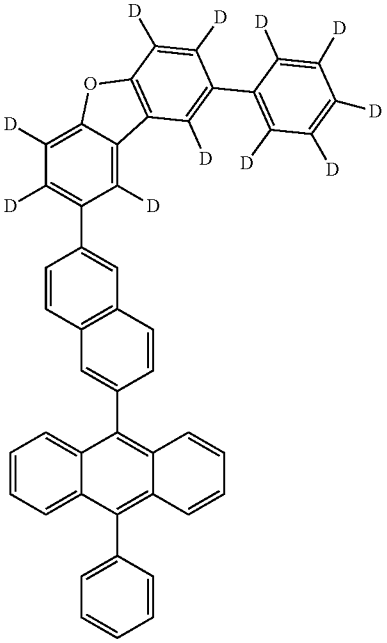
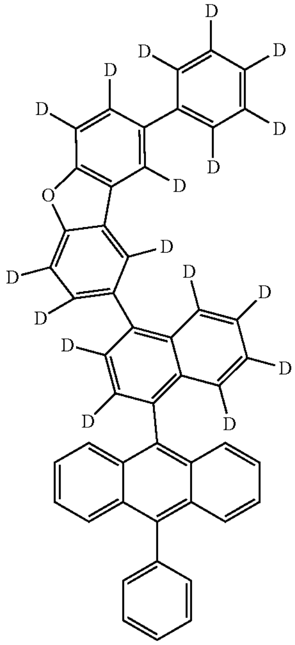

-continued
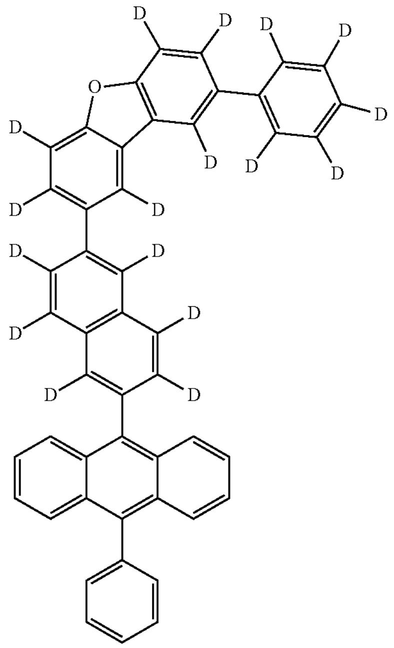
-continued
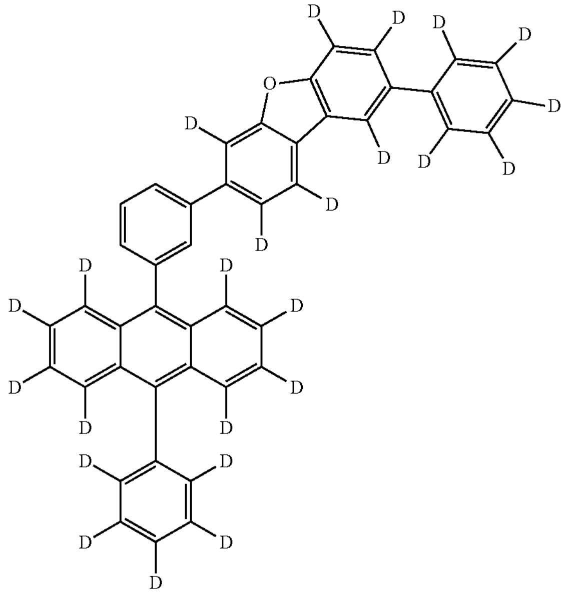
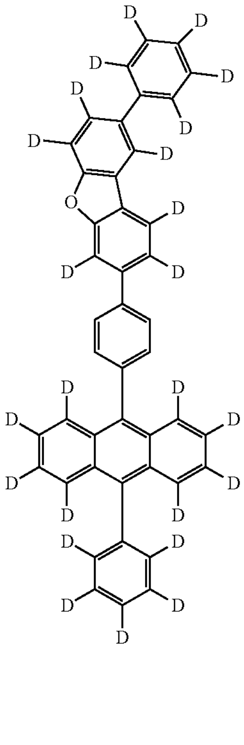
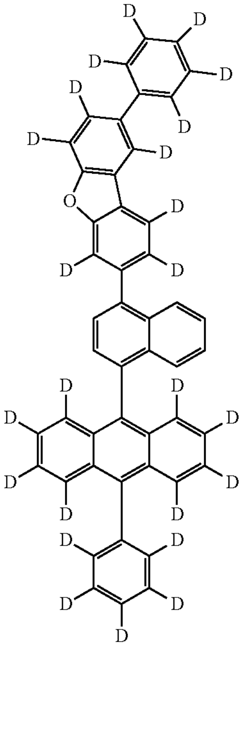
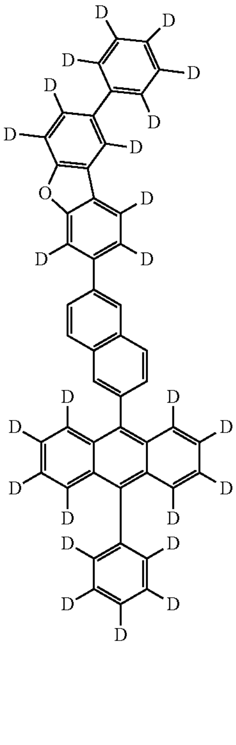

-continued
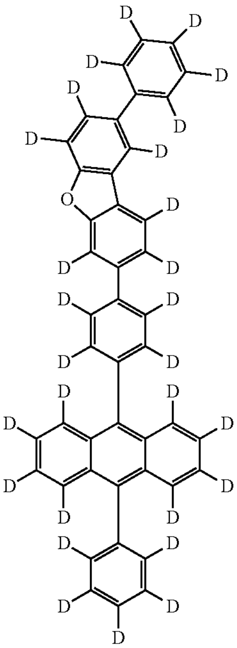
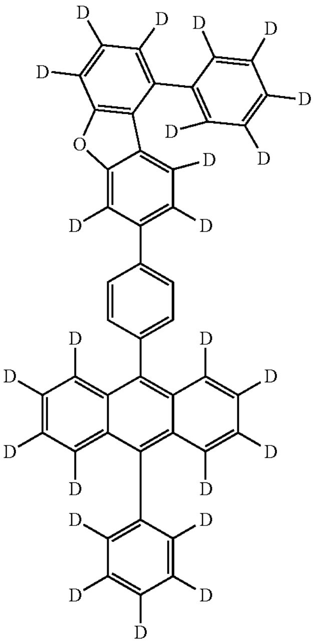
-continued
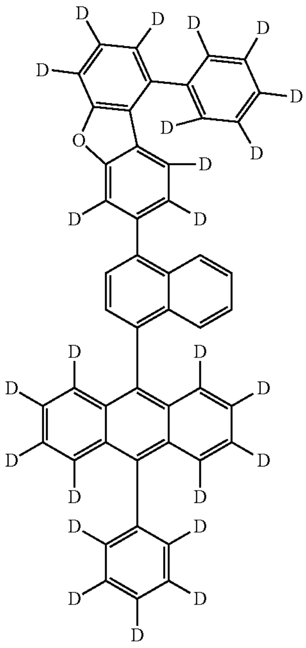
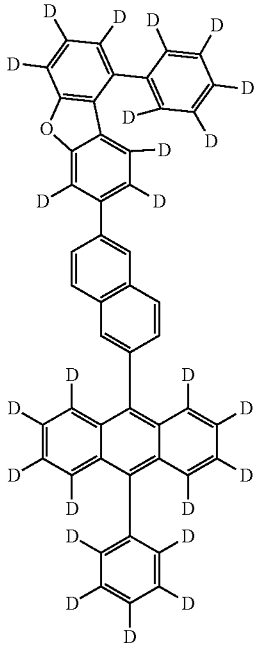
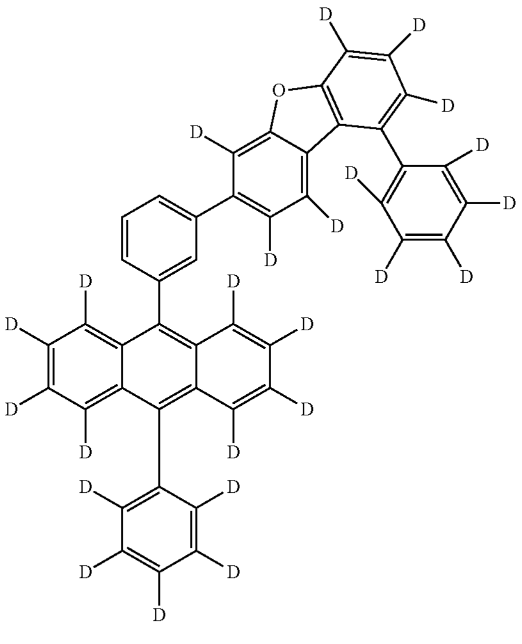
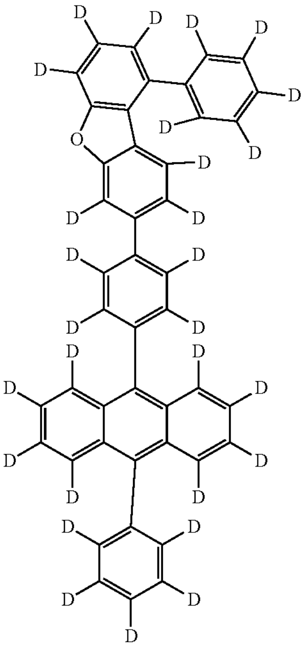

-continued
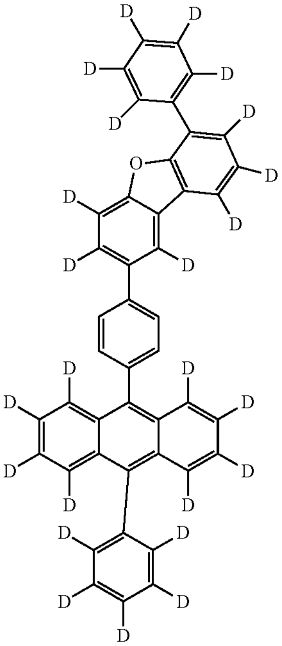
-continued
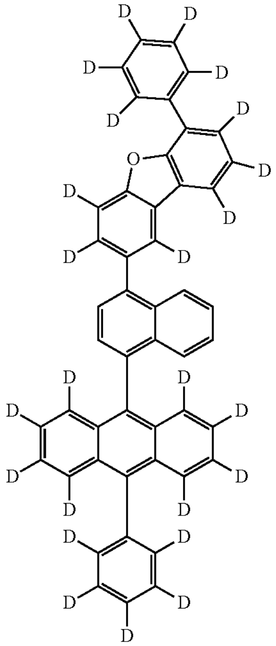
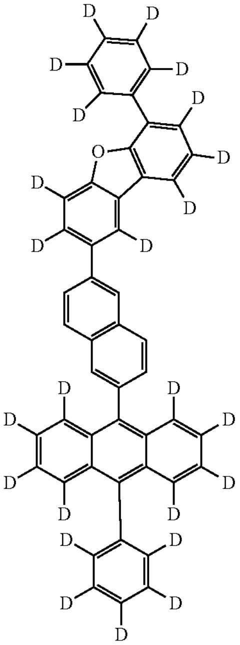
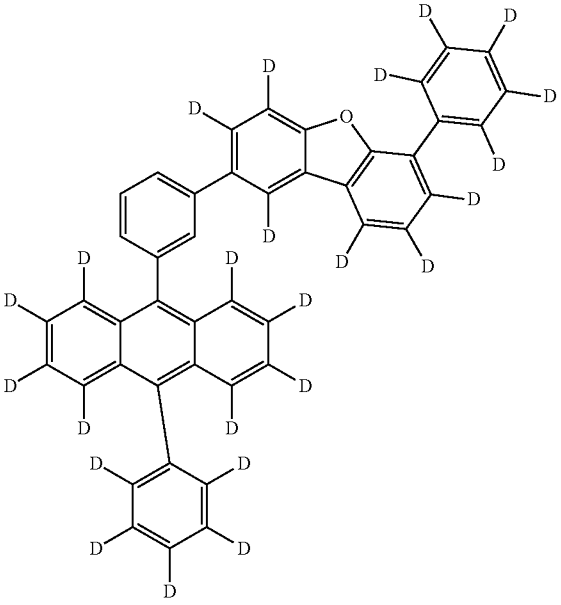
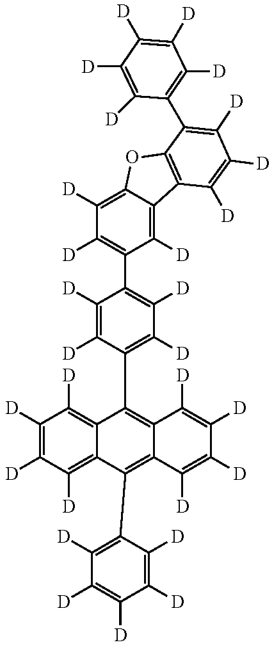

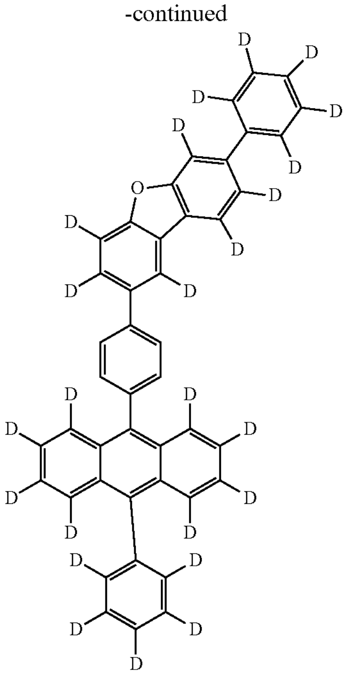
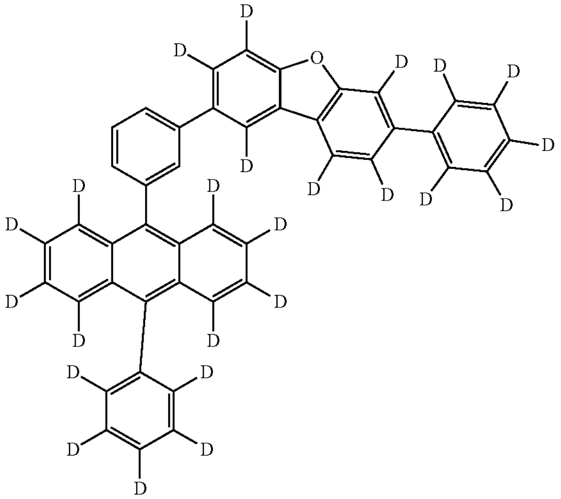
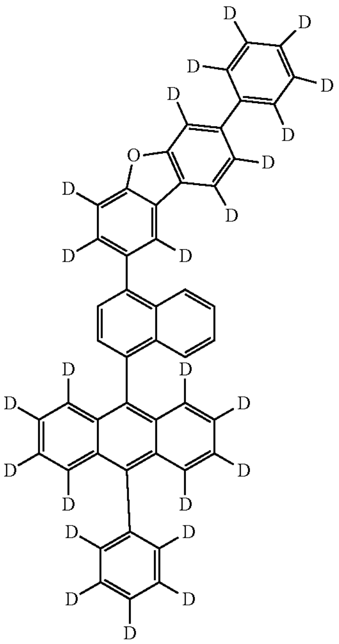
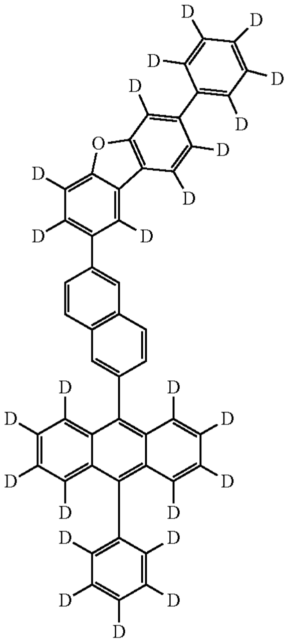

-continued
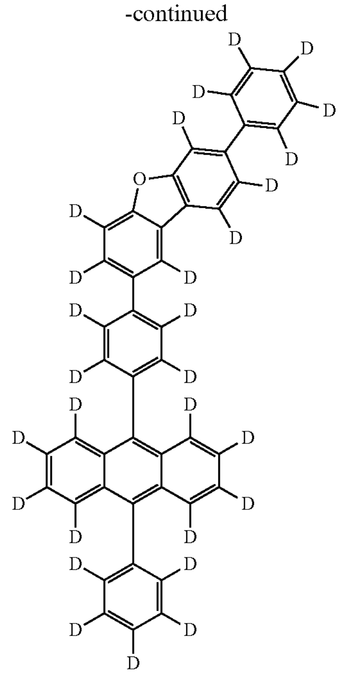
-continued
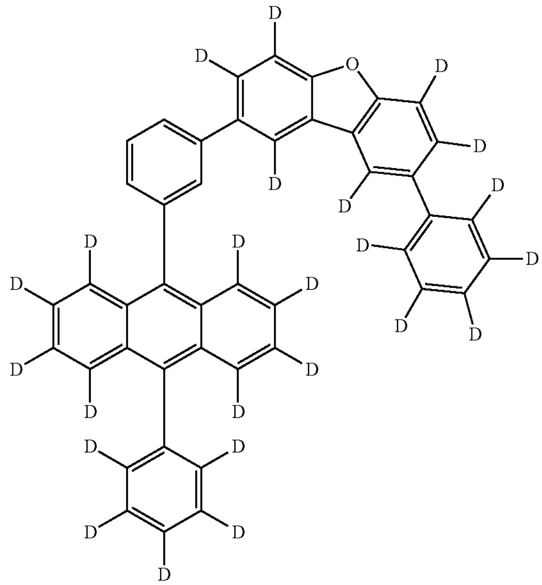
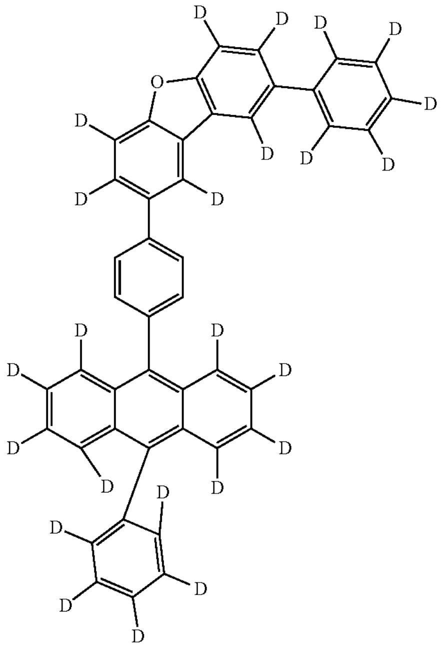
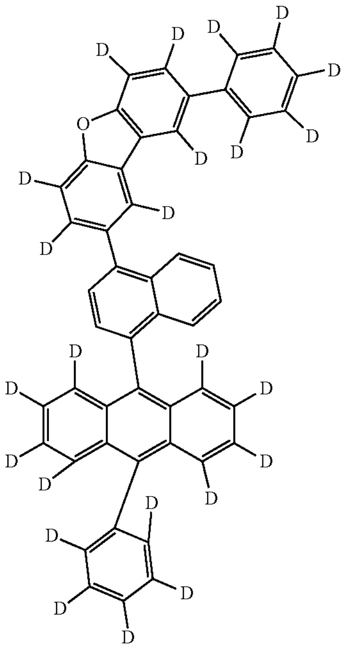

-continued
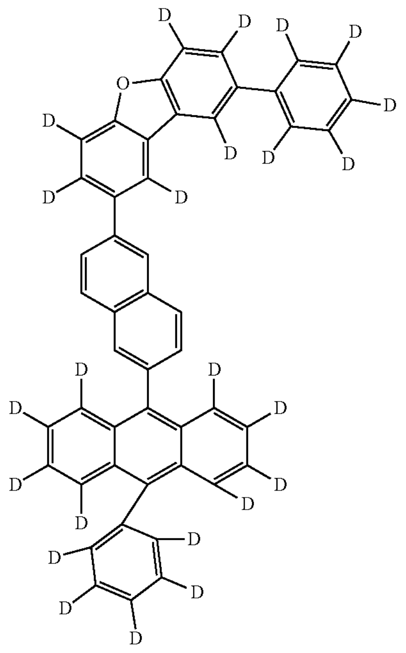
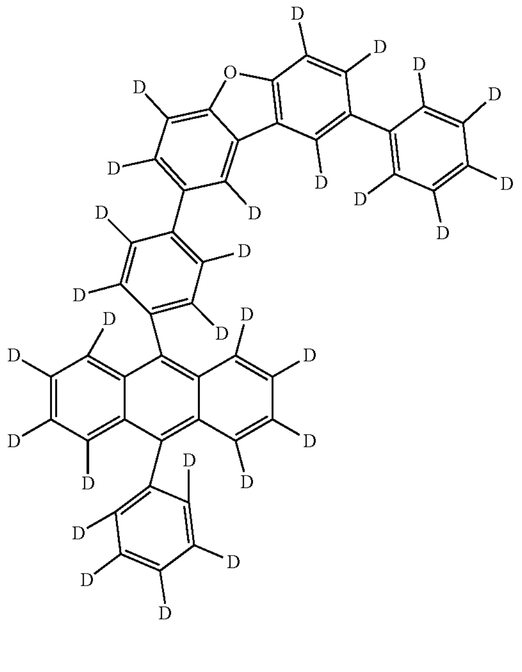
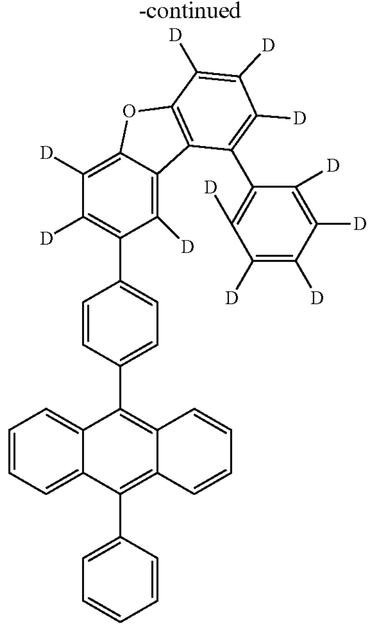
-continued
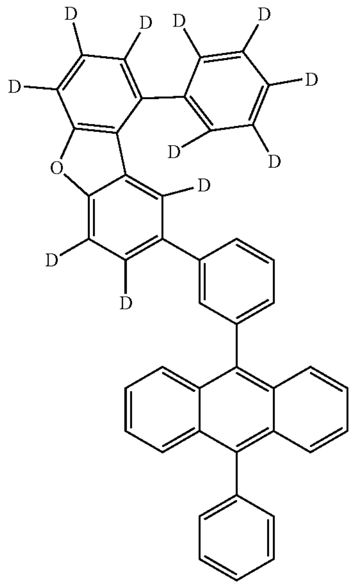

-continued
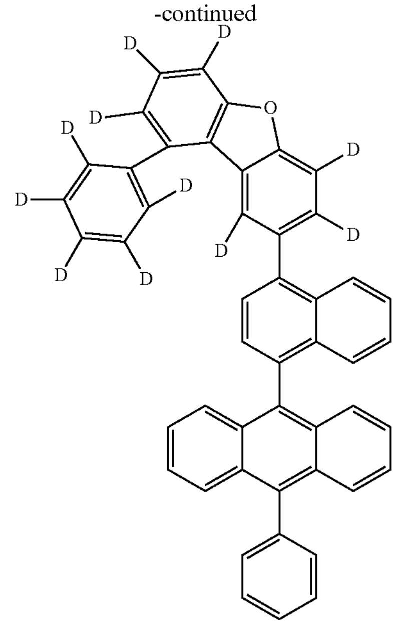
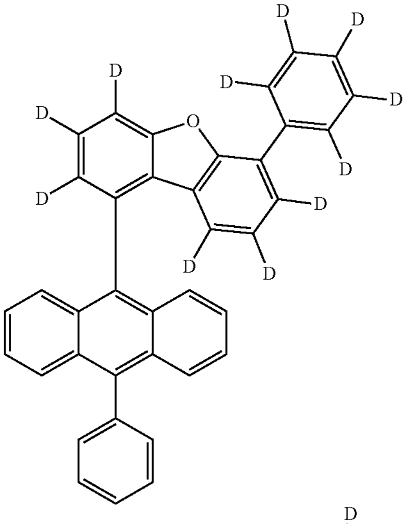
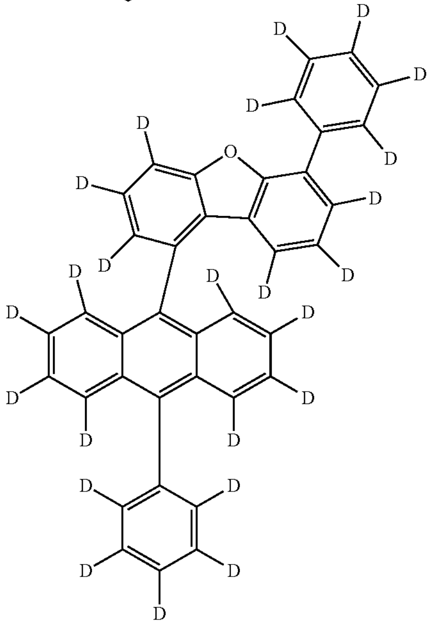
-continued
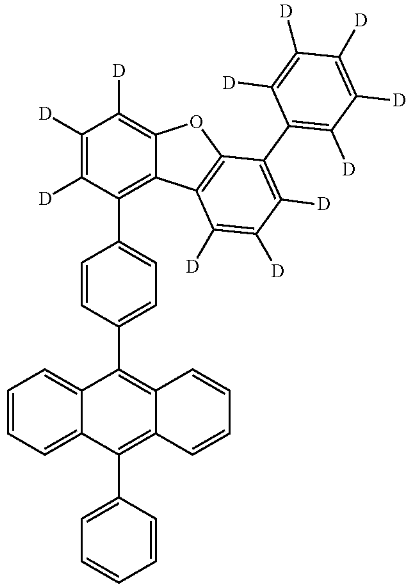
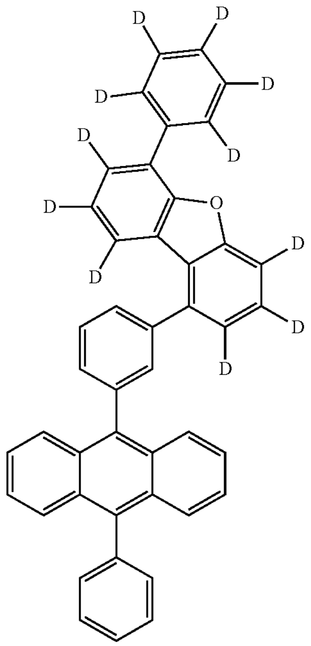

-continued
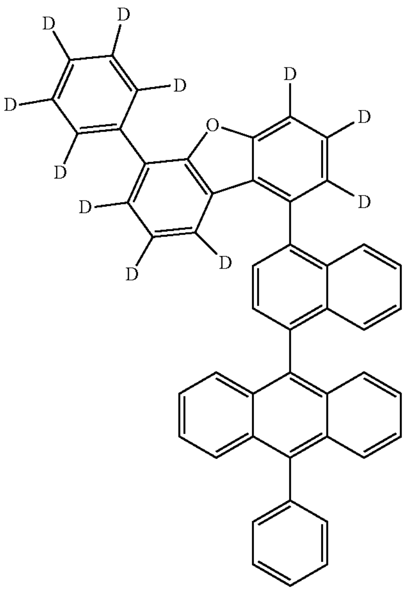
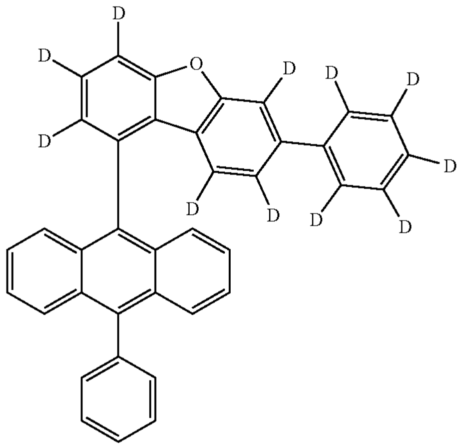
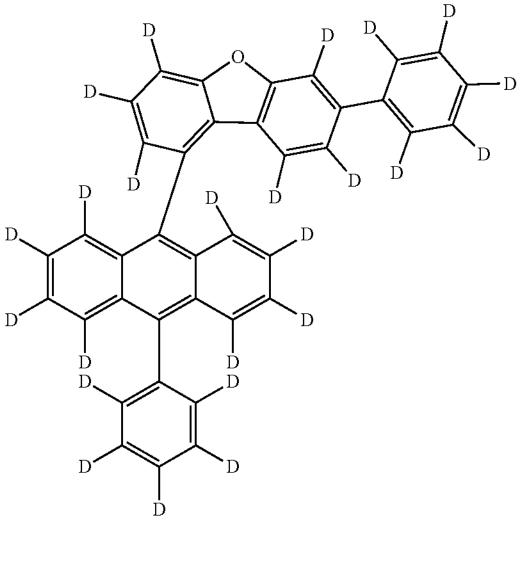
-continued
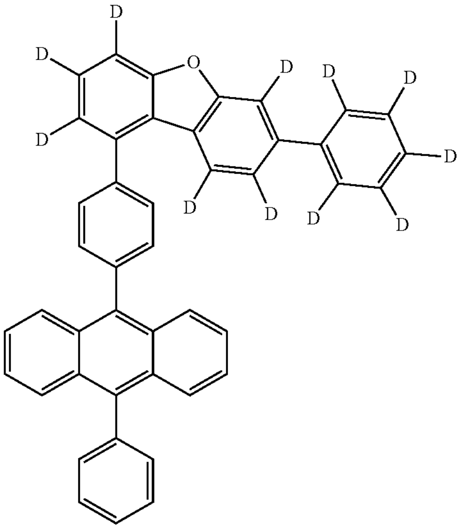
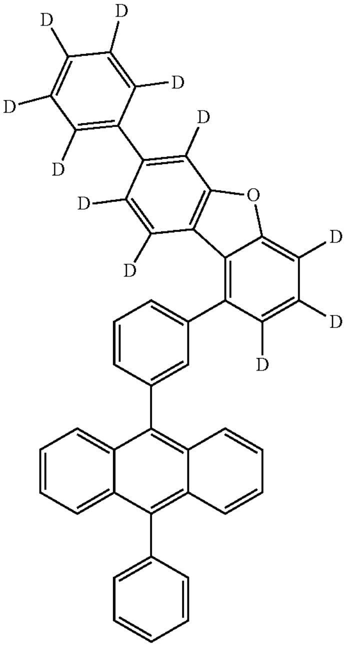
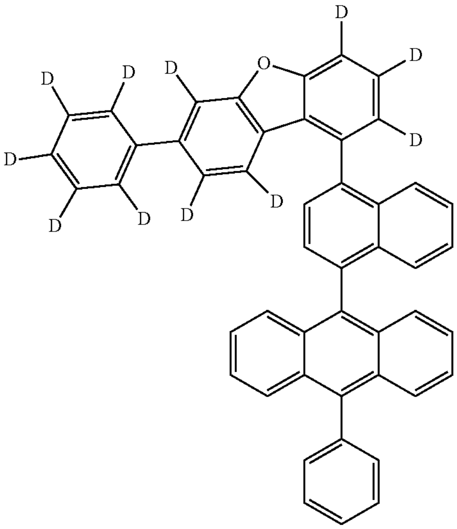

-continued
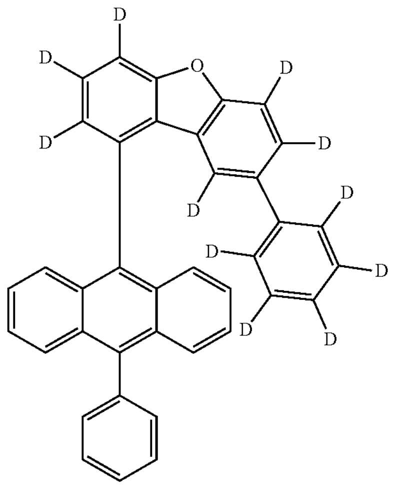
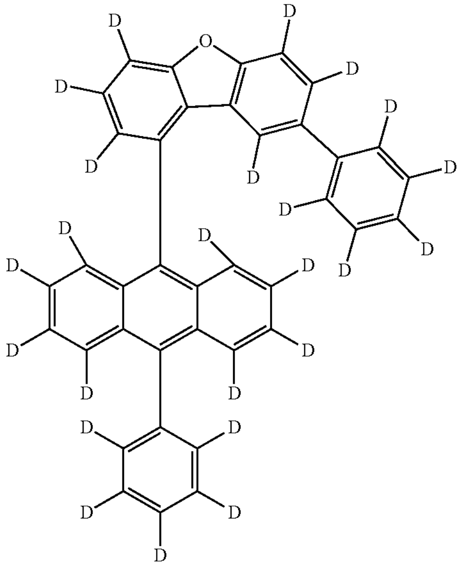
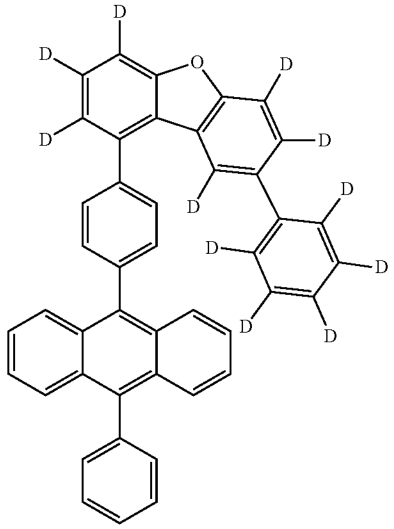
-continued
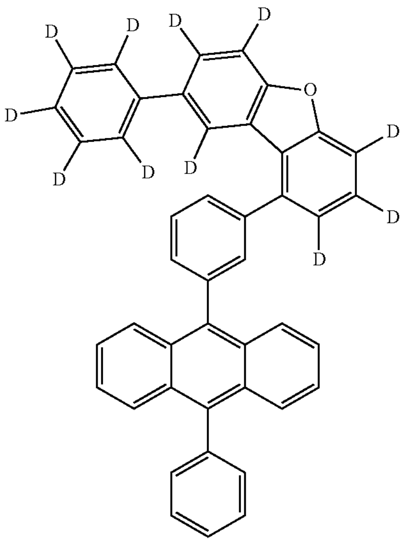
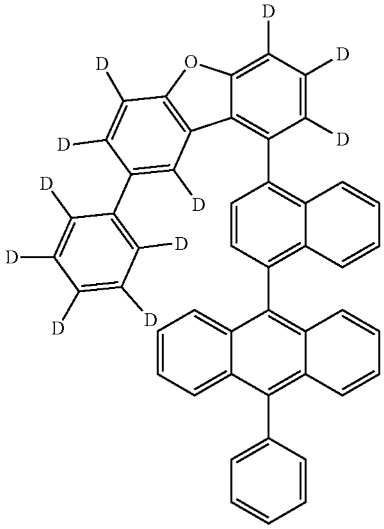
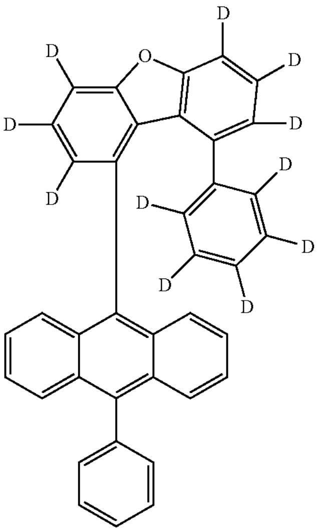

-continued
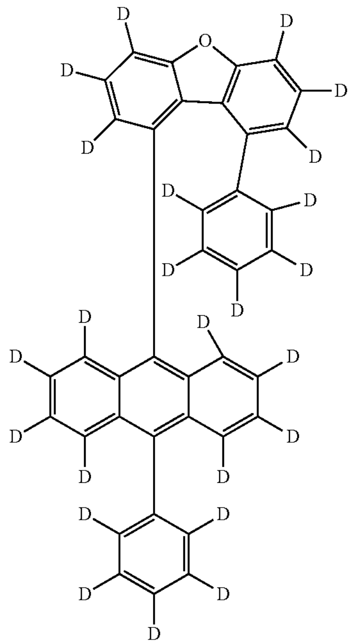
-continued
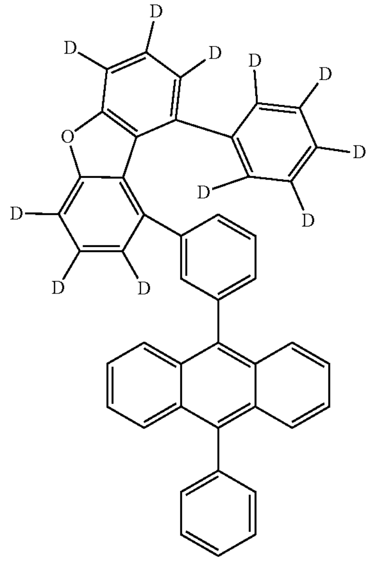
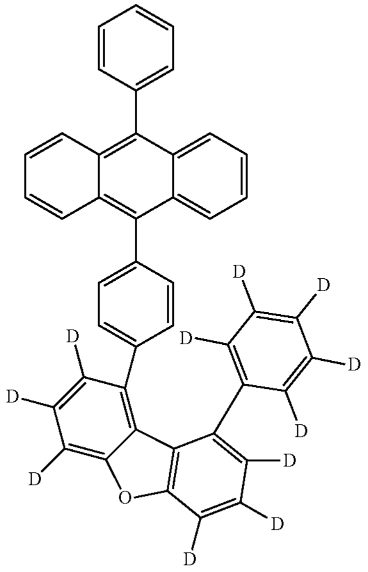
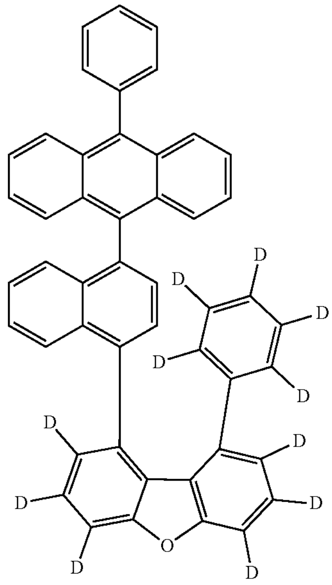

-continued
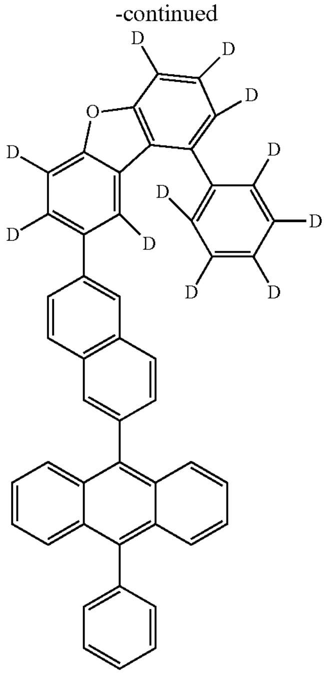
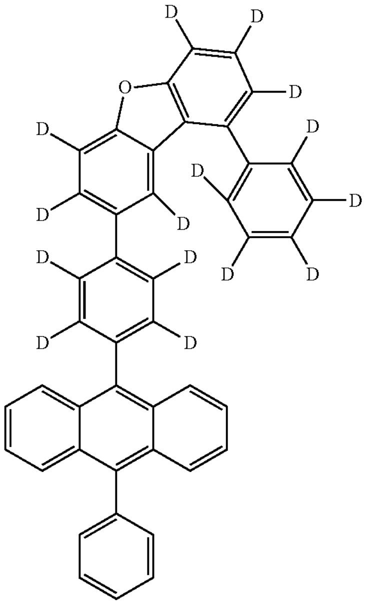
-continued
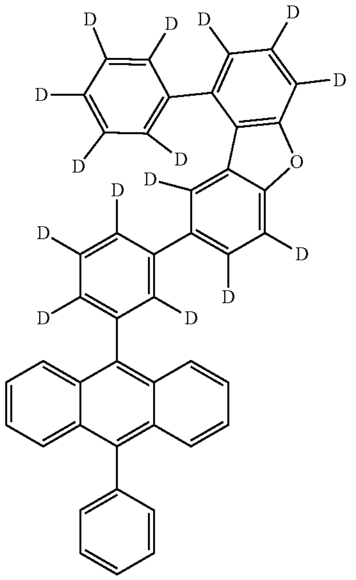
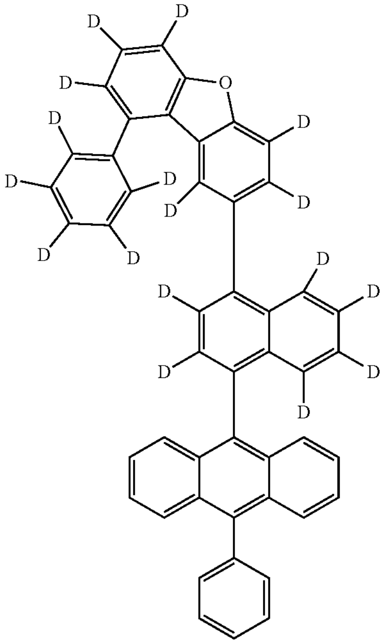

-continued
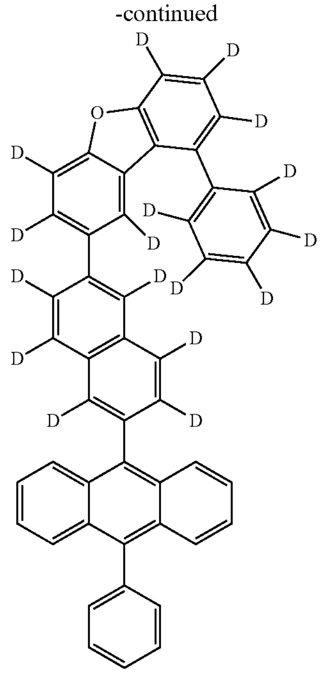
-continued
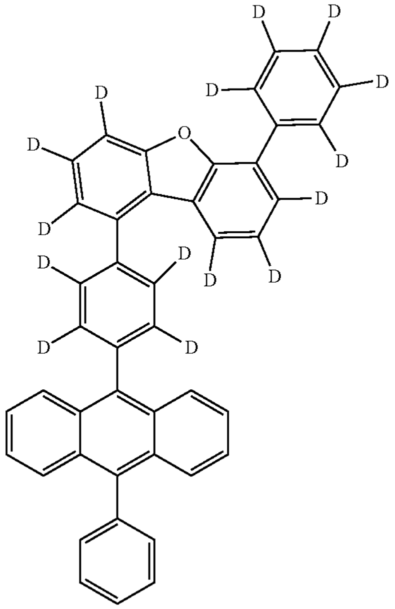
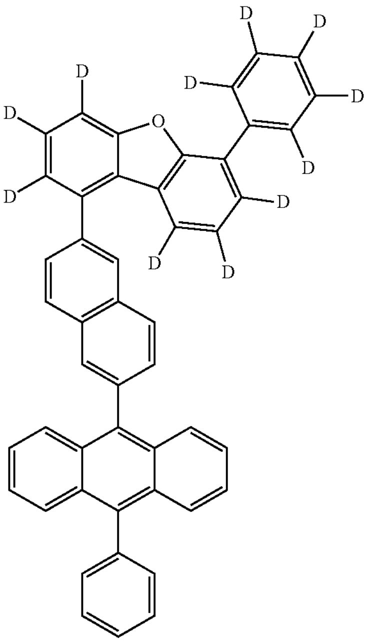
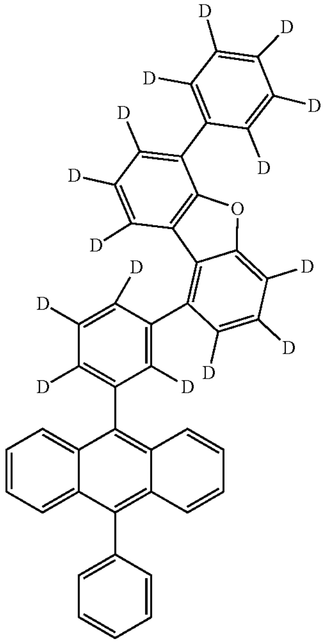

-continued
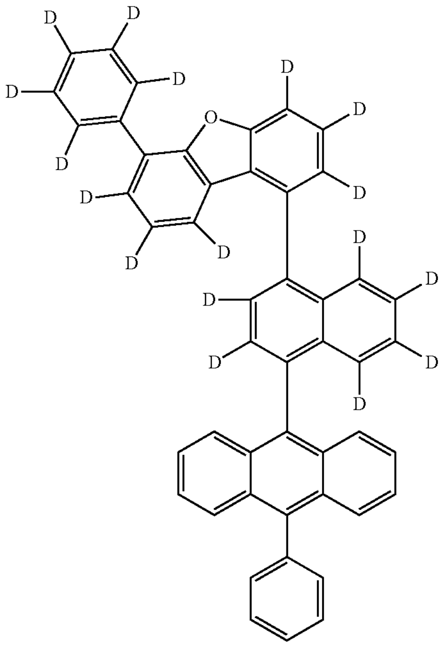
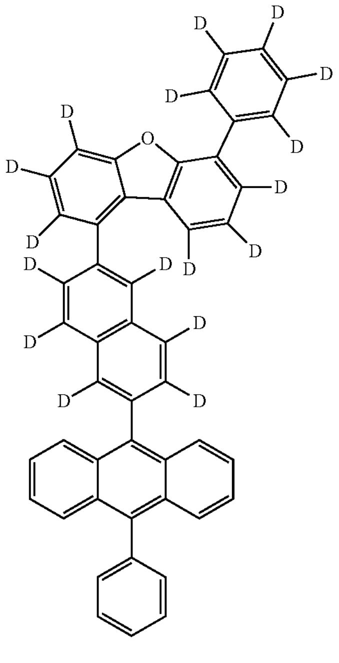
-continued
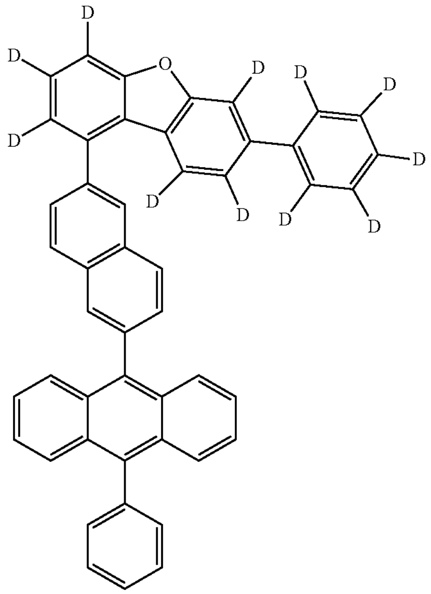
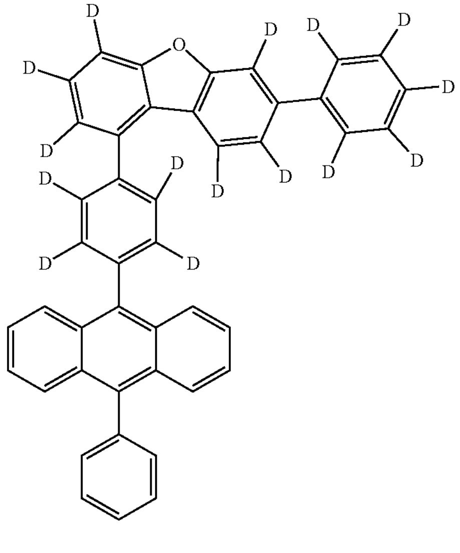

-continued
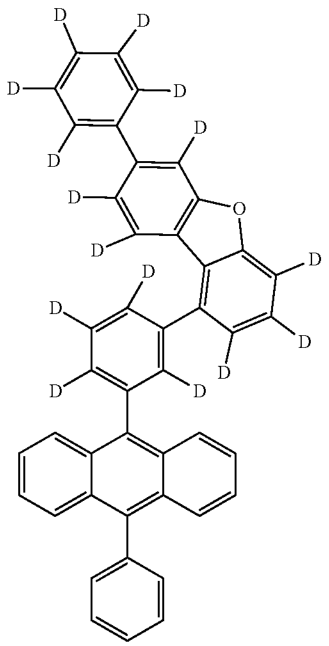
-continued
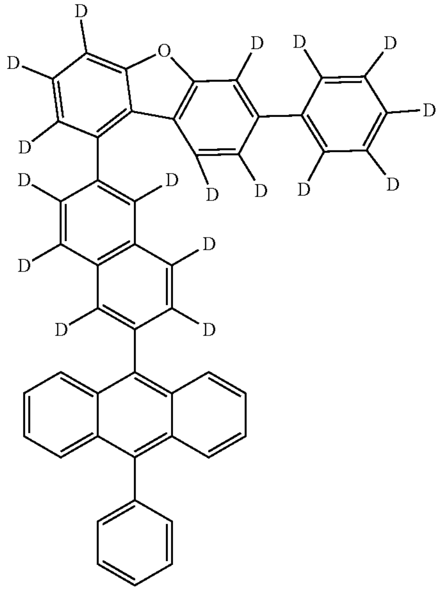
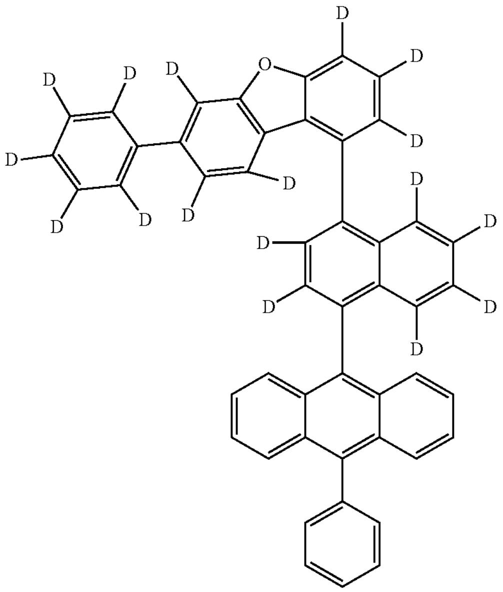
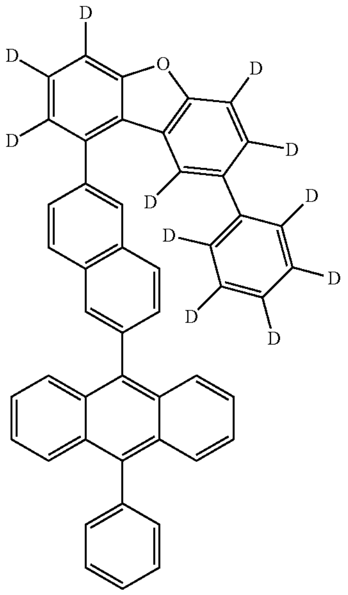

-continued
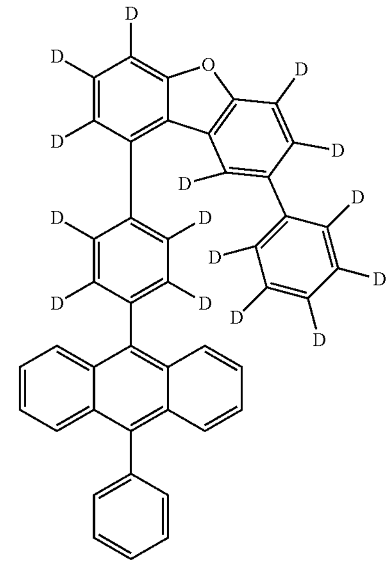
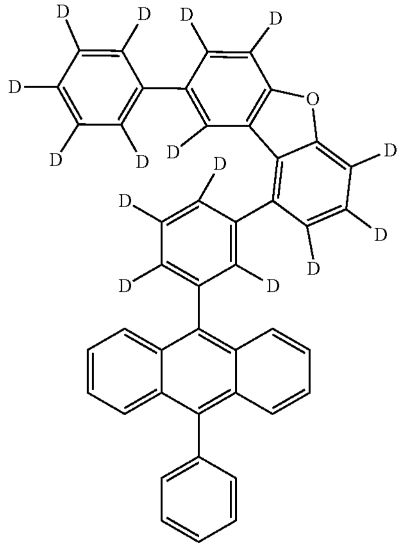
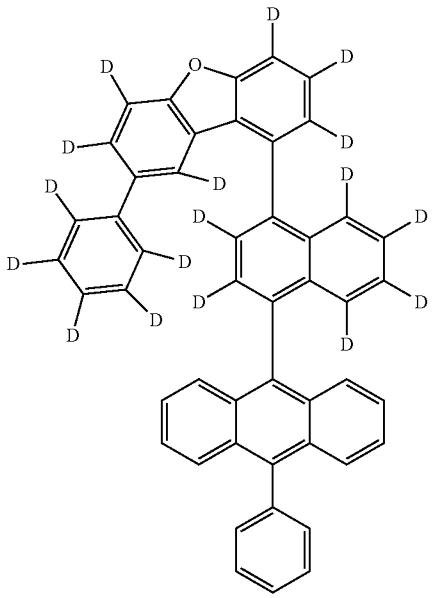
-continued
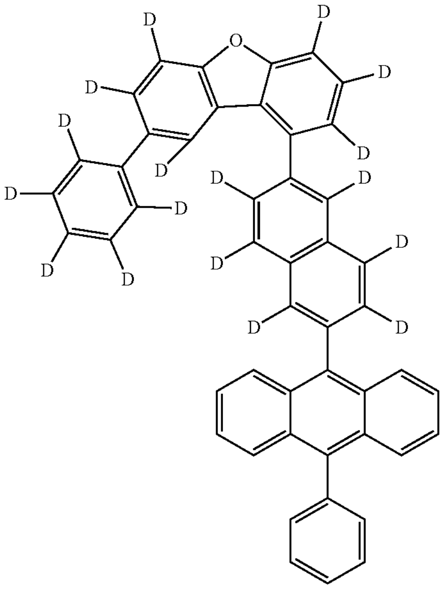
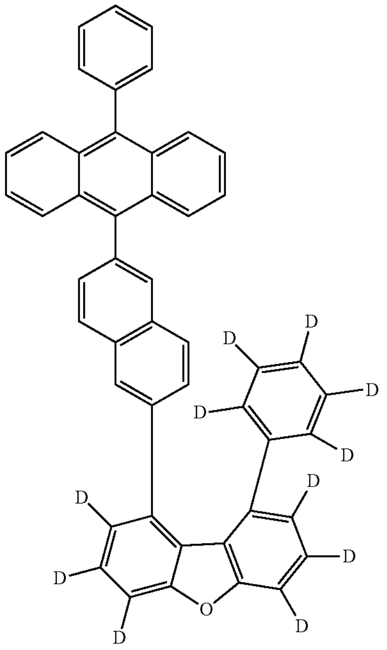

-continued
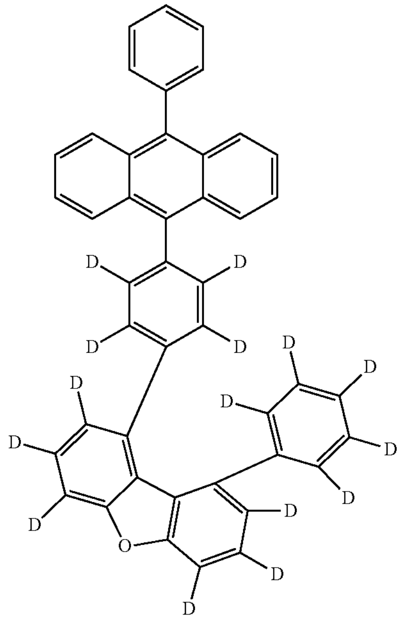
-continued
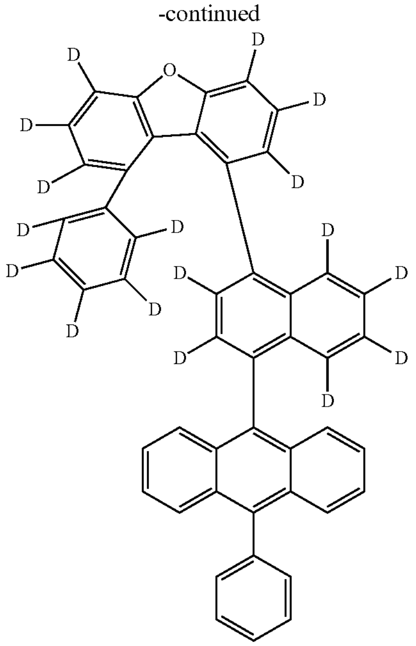
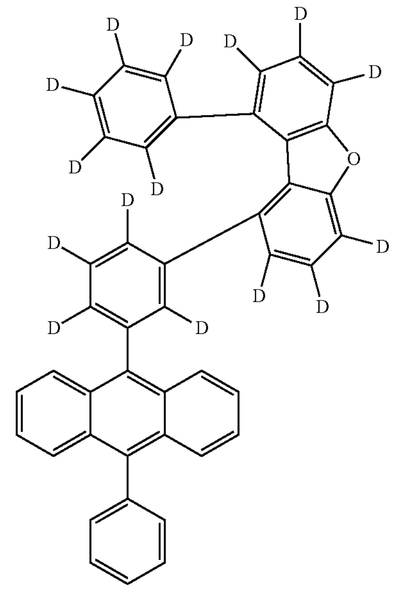
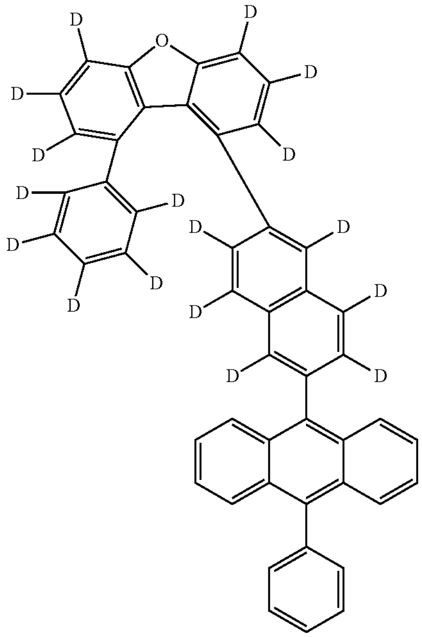

-continued
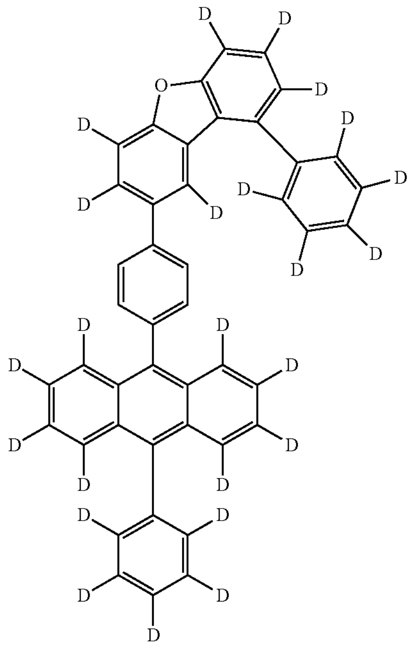
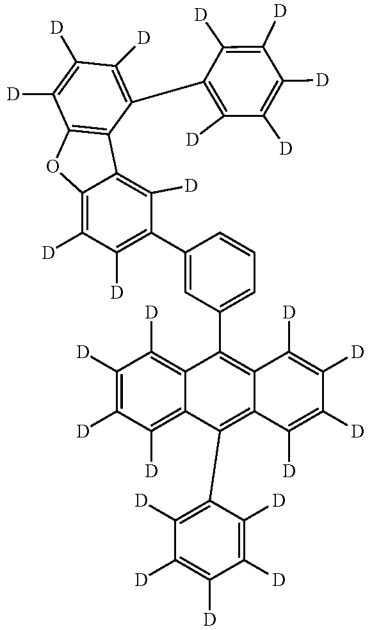
-continued
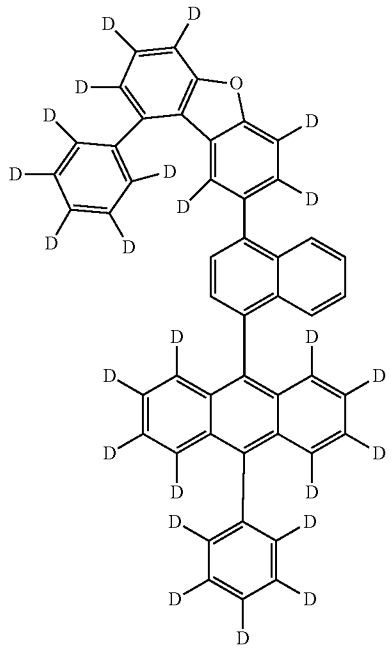
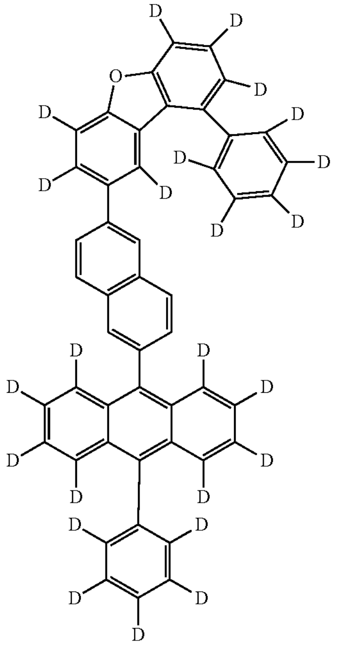

-continued
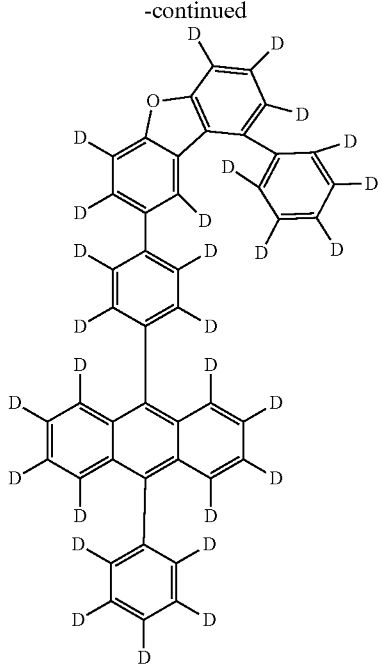
-continued
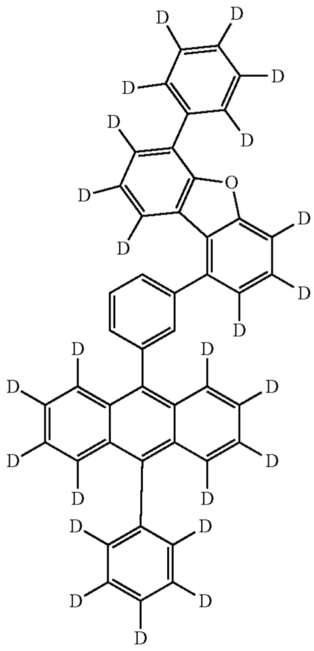
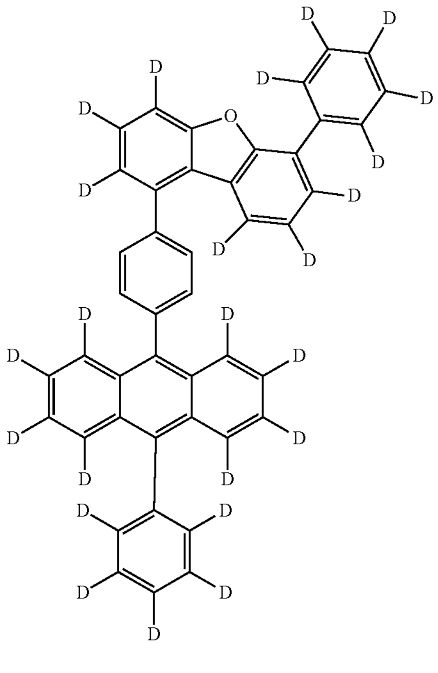
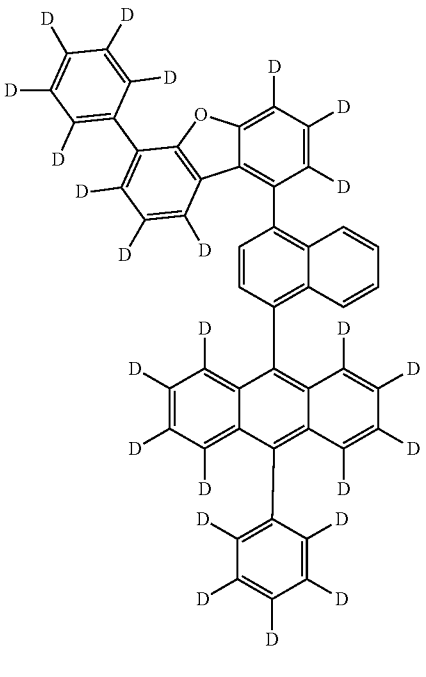

-continued
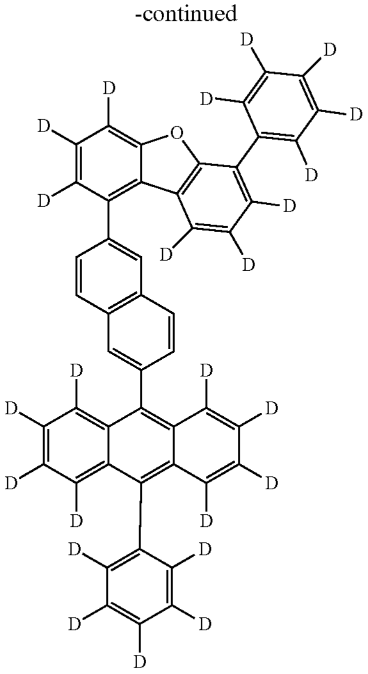
-continued
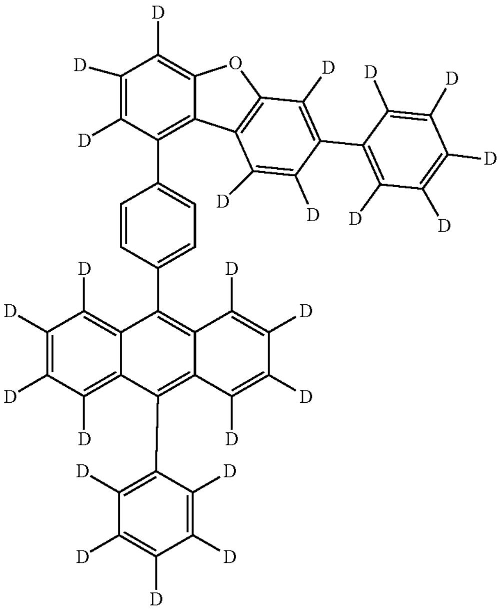
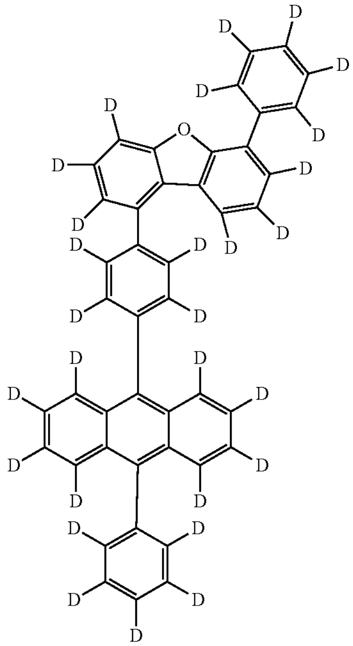
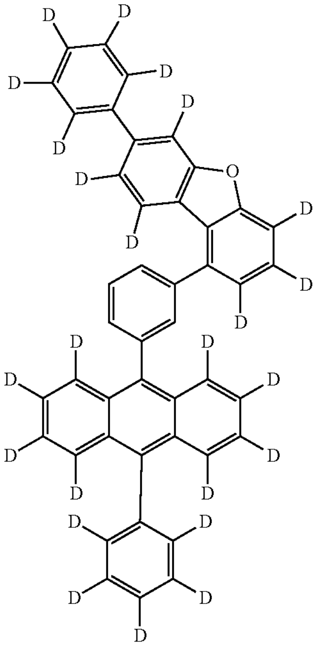

-continued
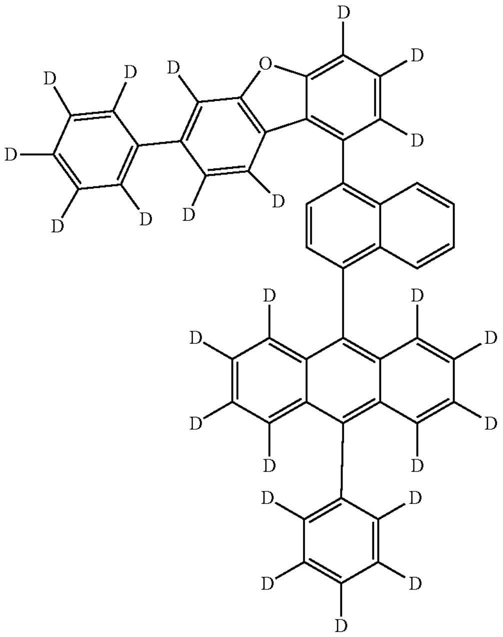
-continued
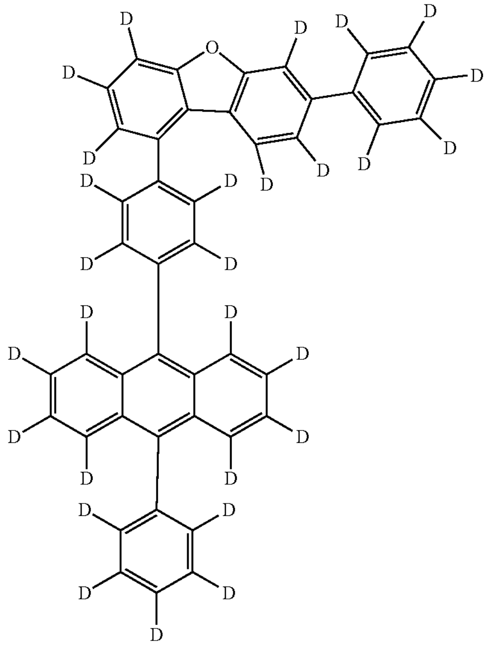
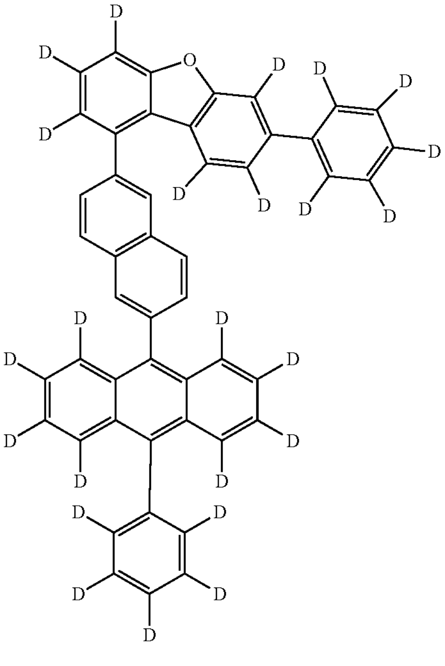
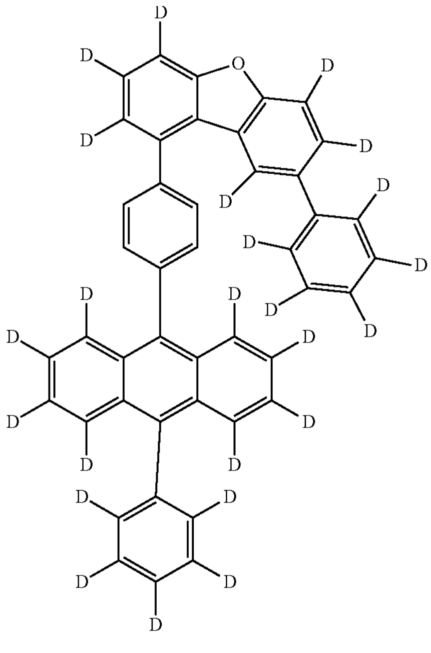

-continued
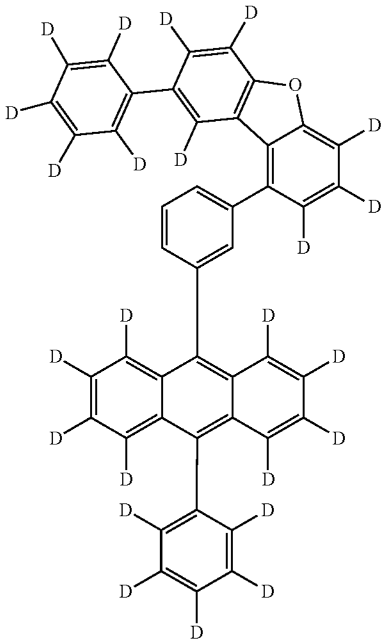
-continued
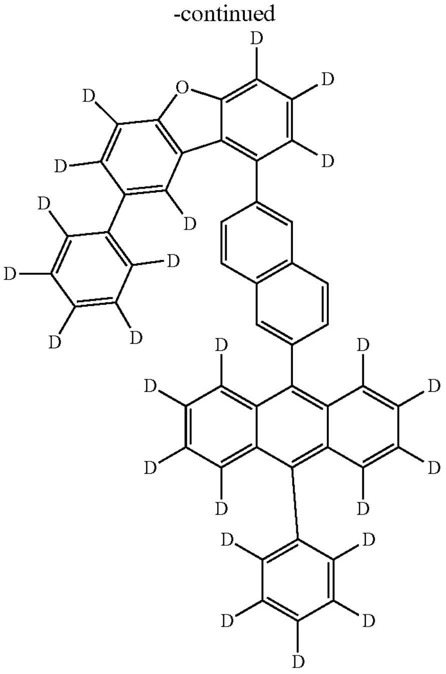
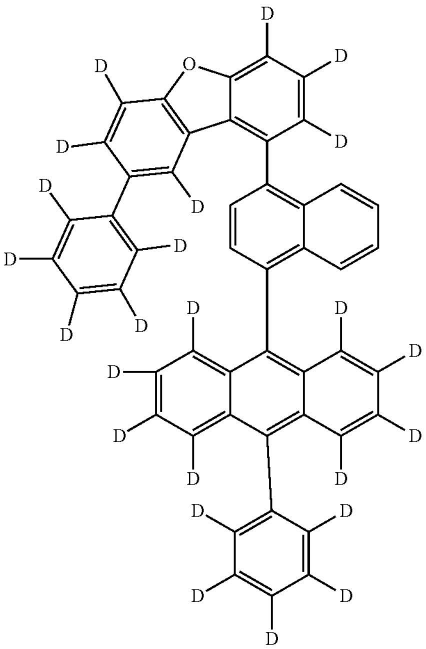
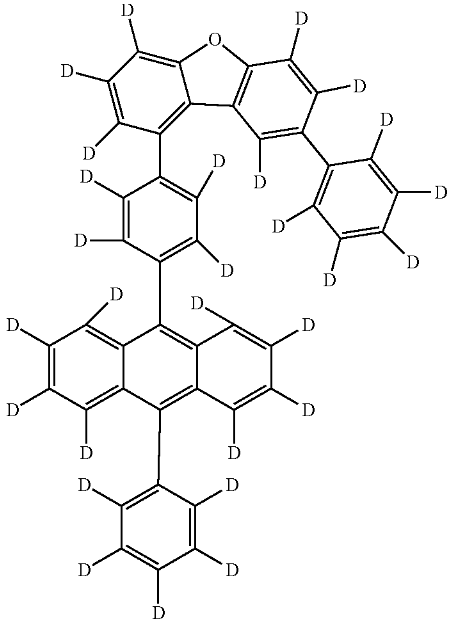

-continued
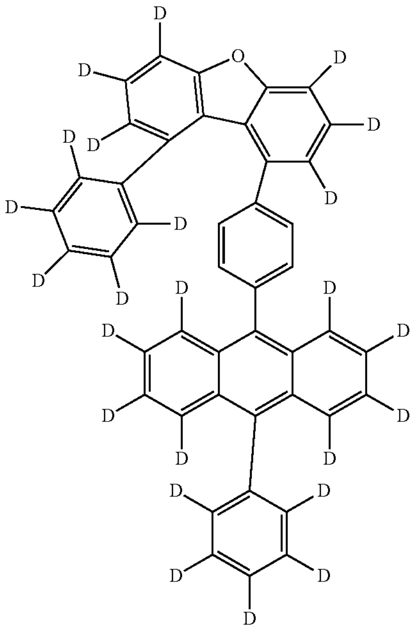
-continued
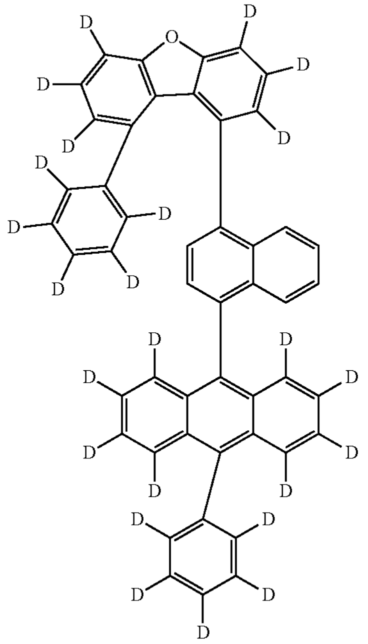
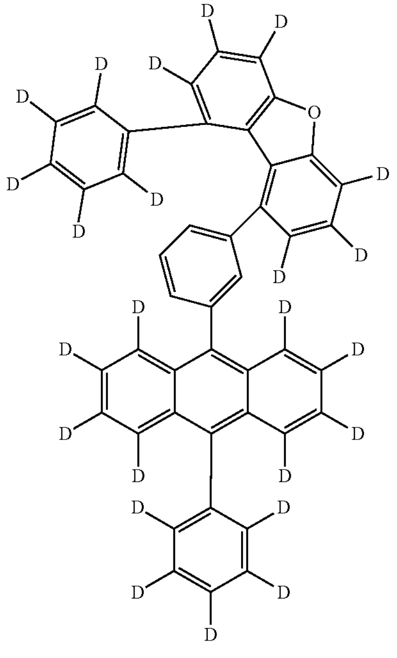
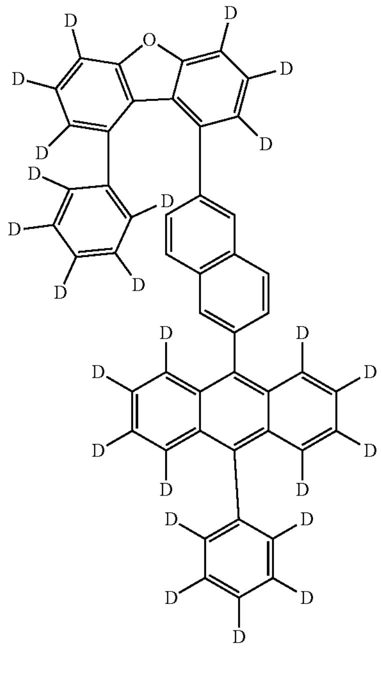

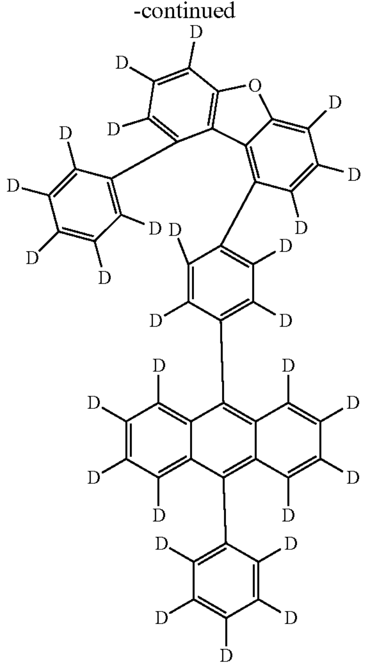
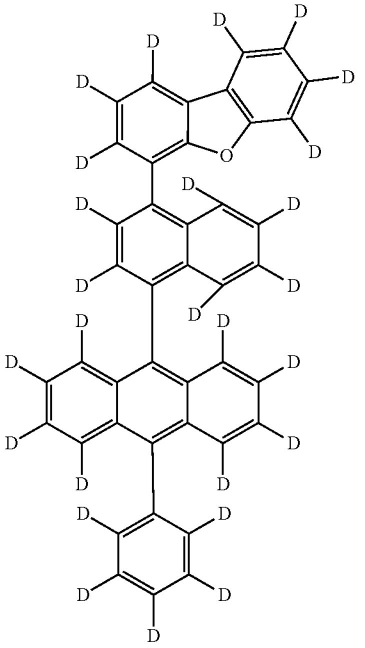
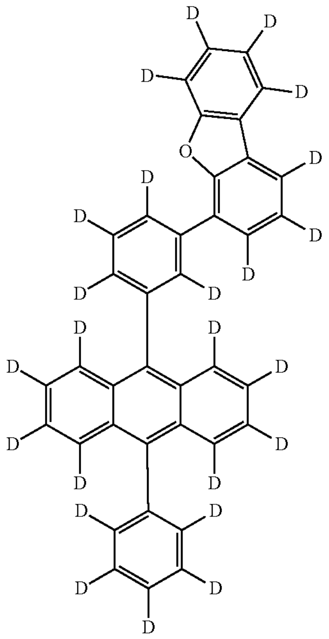
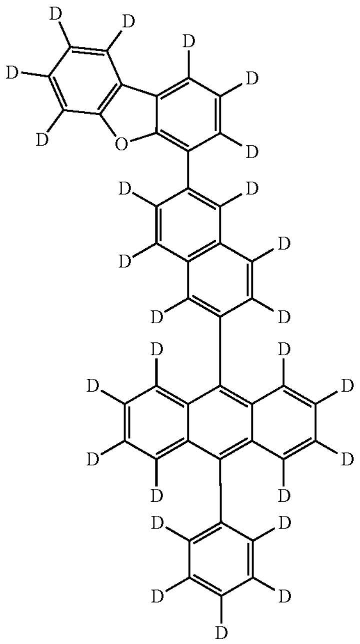

-continued
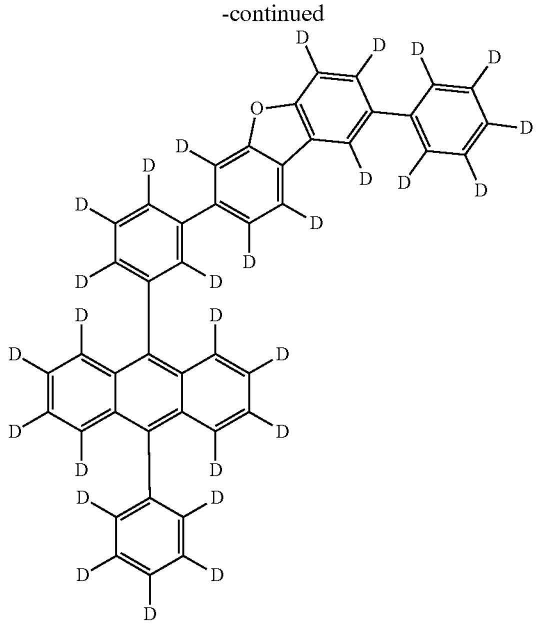
-continued
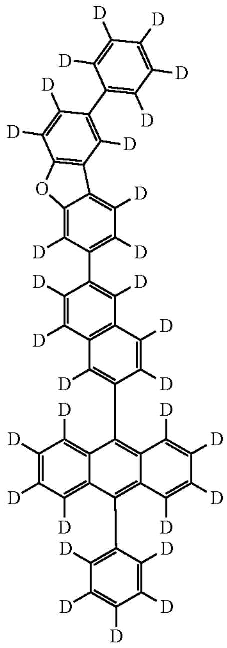
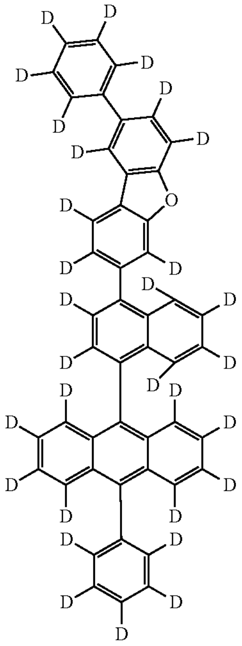
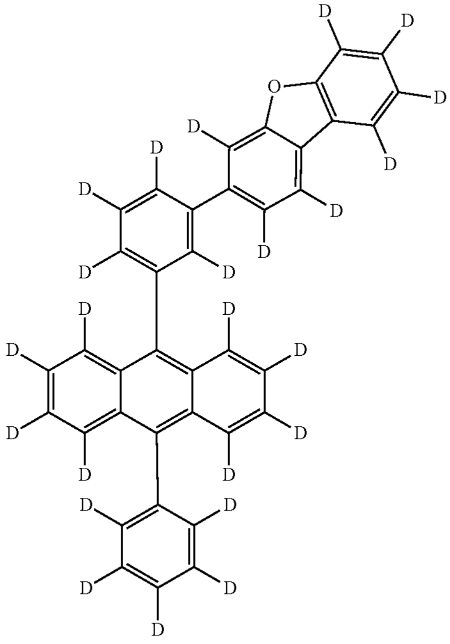

-continued
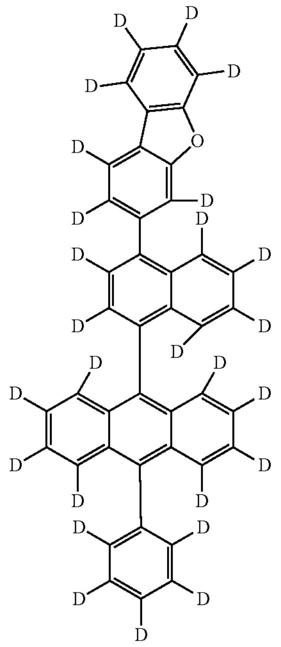
-continued
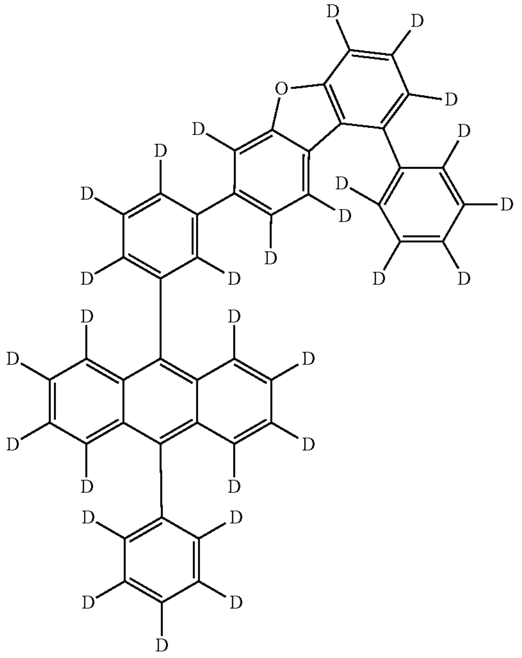
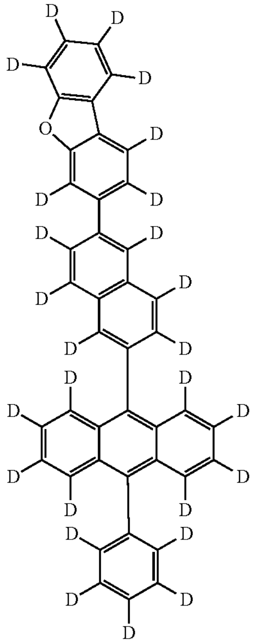
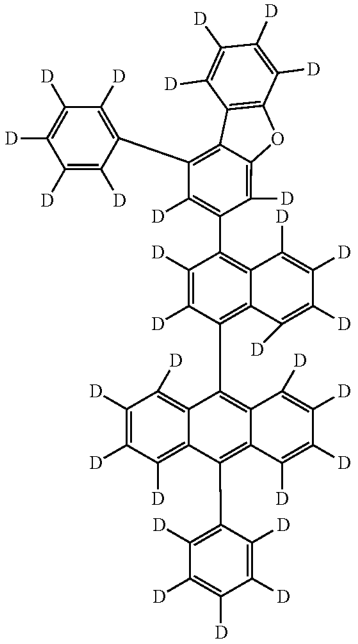

-continued
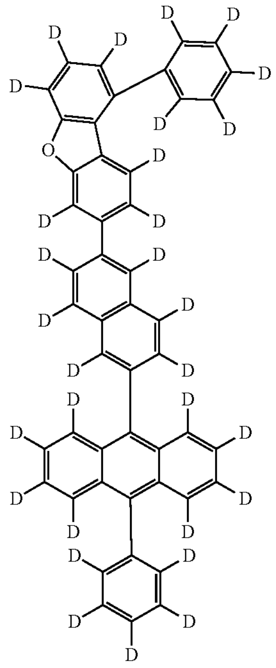
-continued
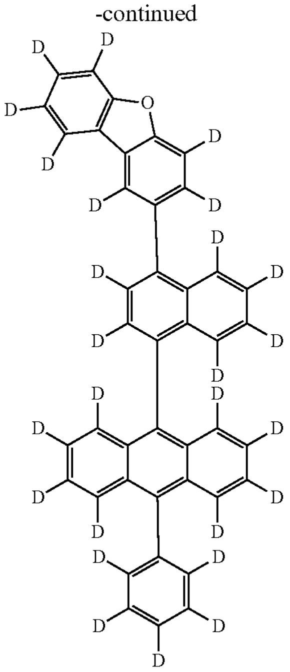
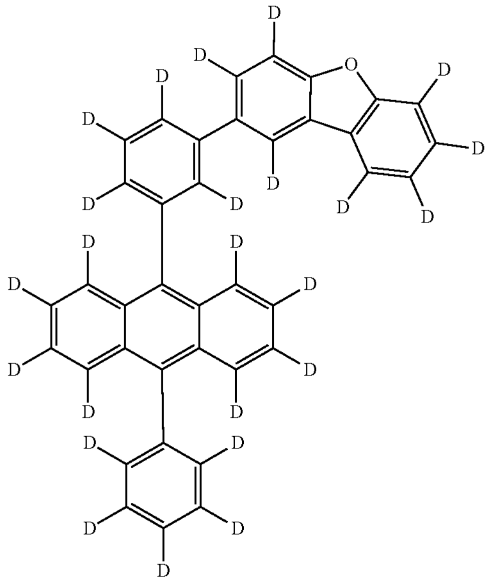
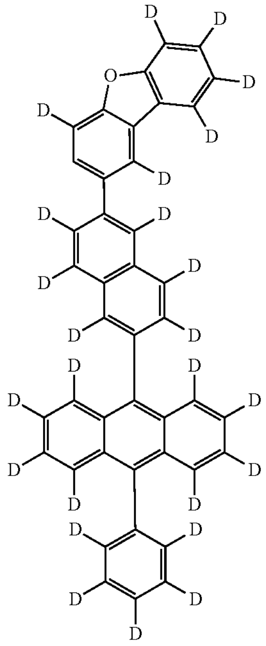

-continued
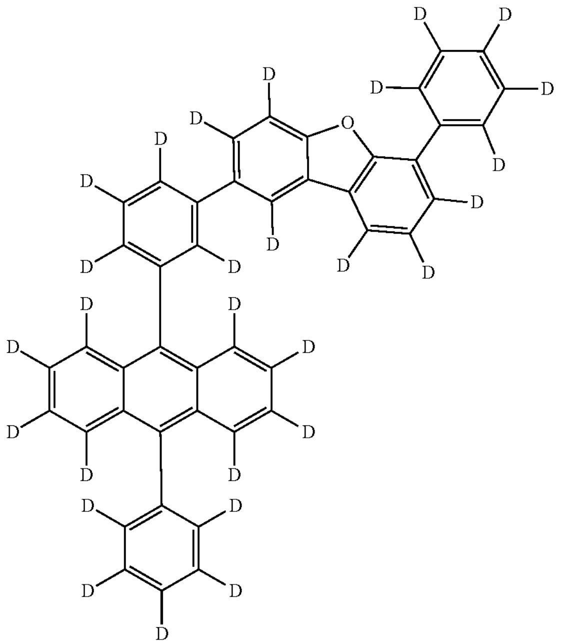
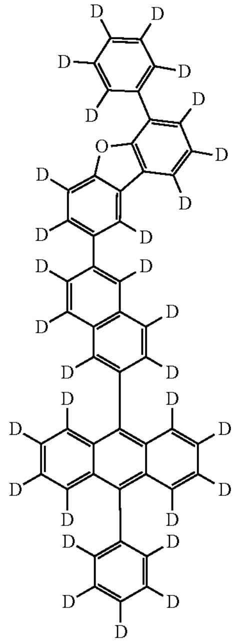
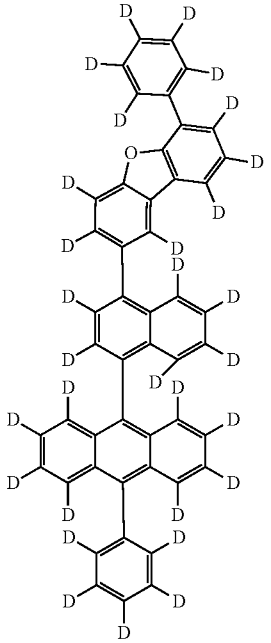
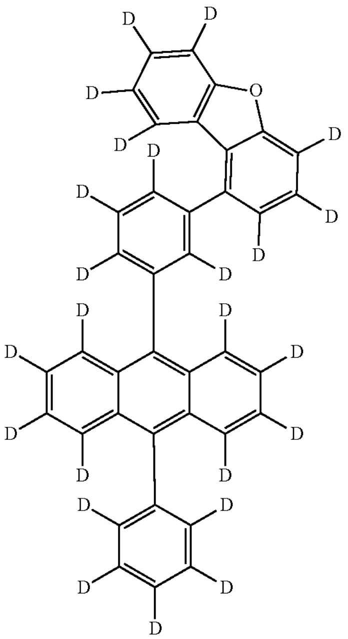

-continued
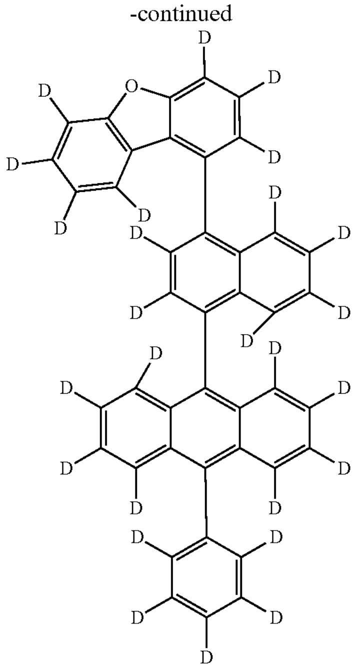
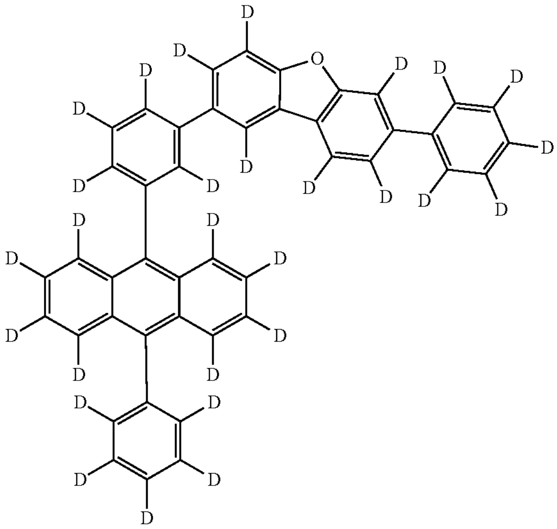
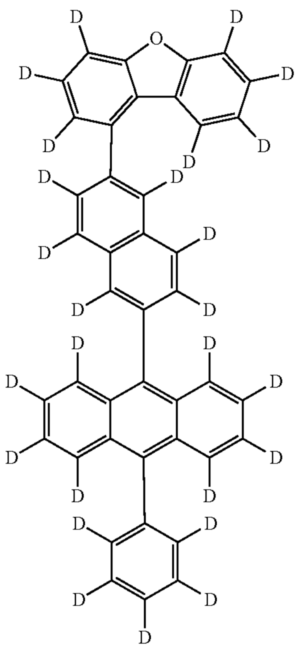
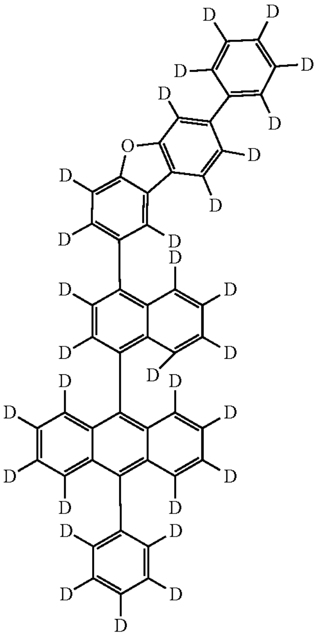

-continued
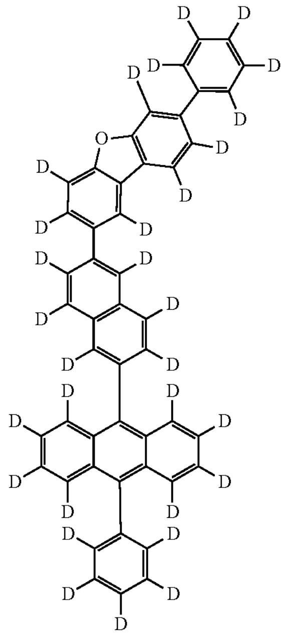
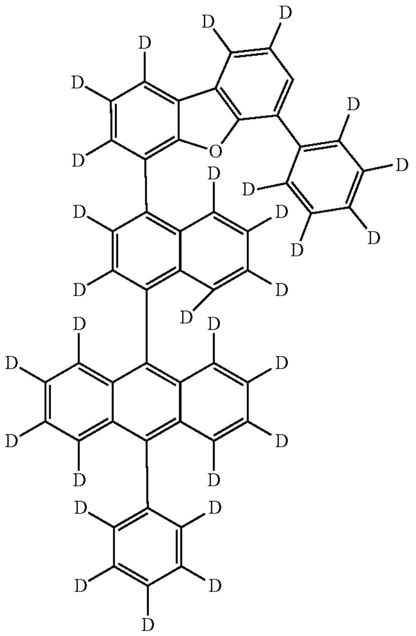
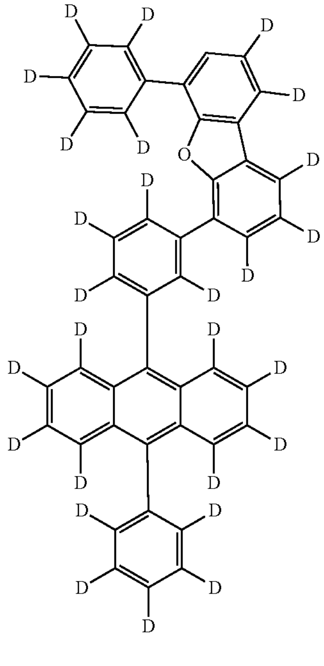
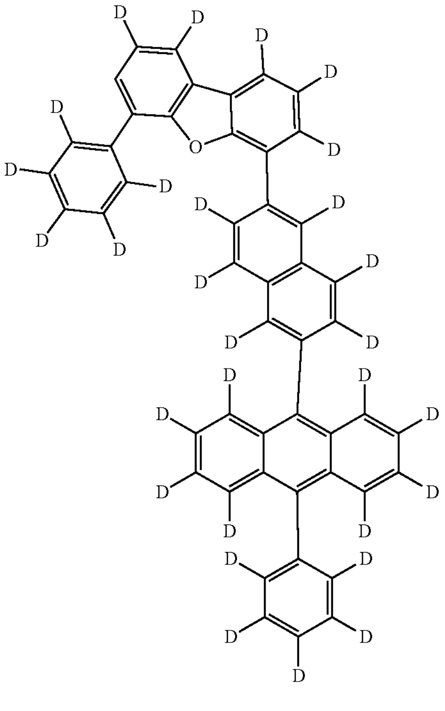

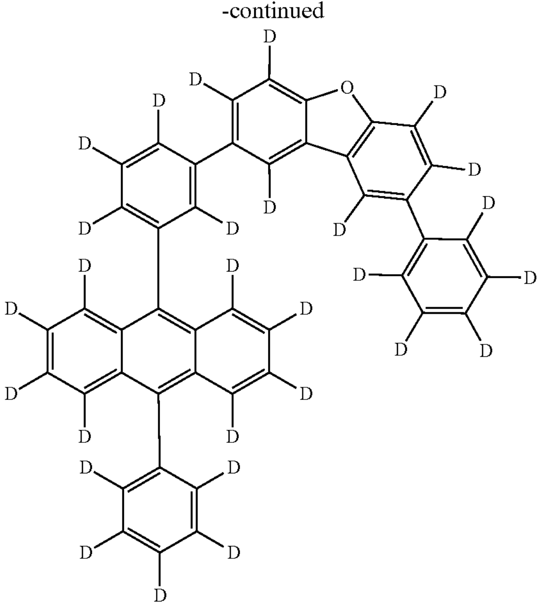
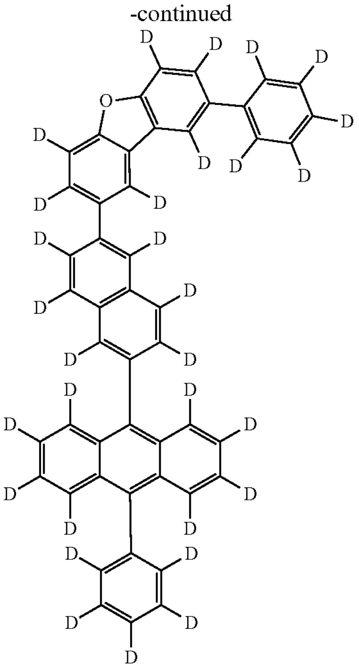
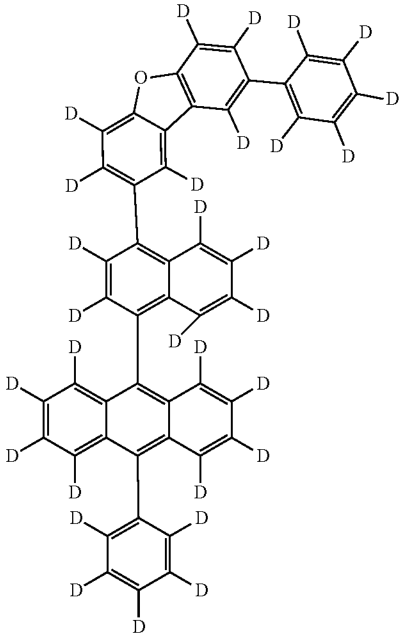
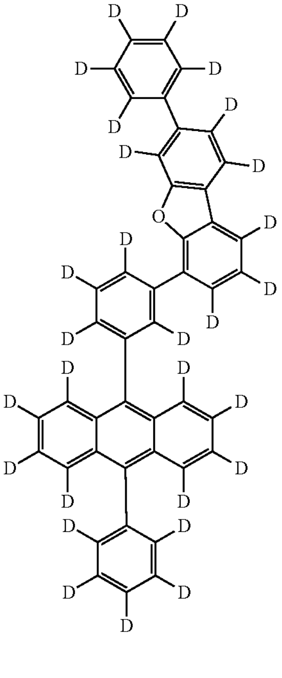

-continued
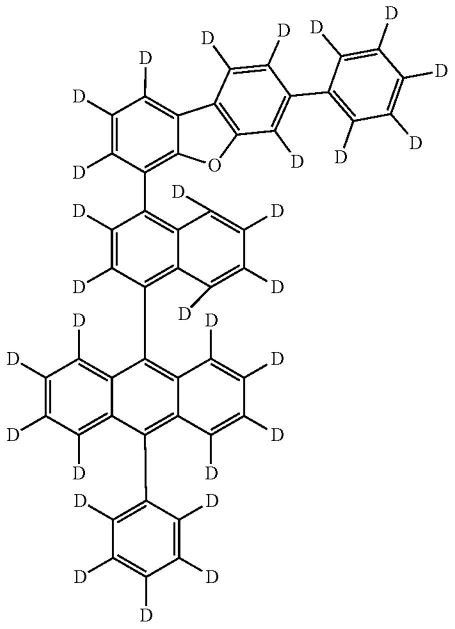
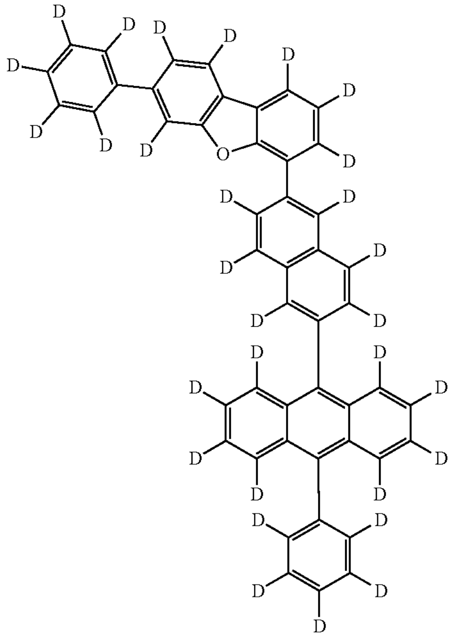
-continued
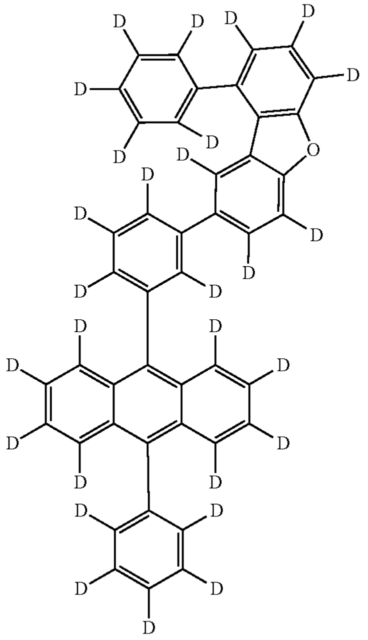
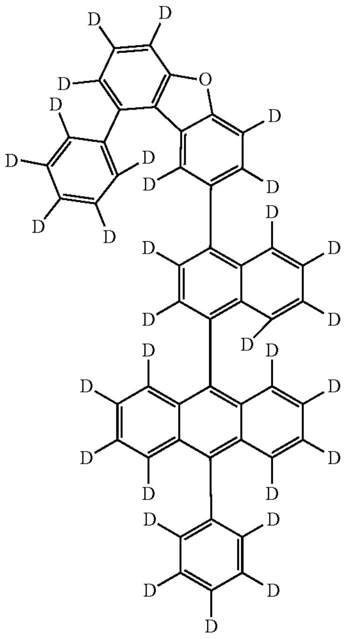

-continued
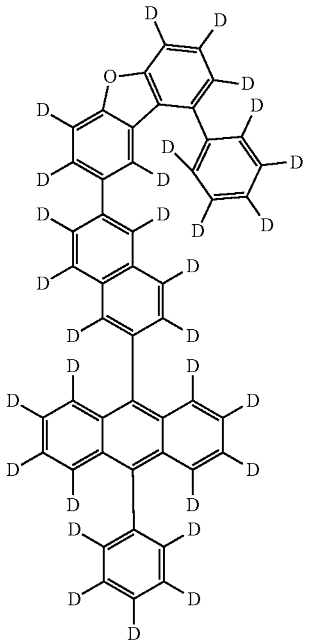 [SMILES: [2H]c1c([2H])c([2H])c(-c2c3c([2H])c([2H])c([2H])c([2H])c3c(-c3c([2H])c([2H])c4c([2H])c(-c5c([2H])c([2H])c6oc7c([2H])c([2H])c([2H])c(-c8c([2H])c([2H])c([2H])c([2H])c8[2H])c7c6c5[2H])c([2H])c([2H])c4c3[2H])c3c([2H])c([2H])c([2H])c([2H])c23)c([2H])c1[2H]]
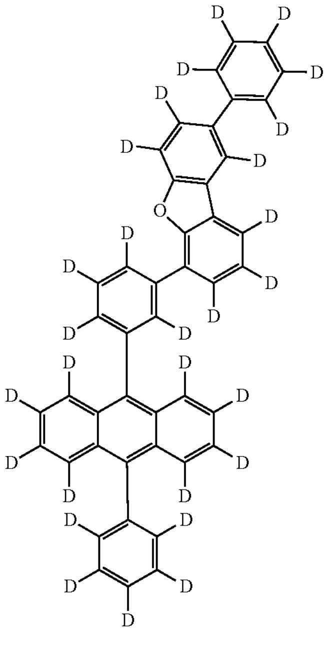
-continued
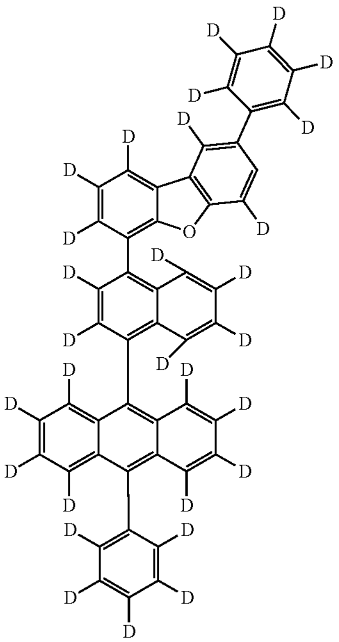
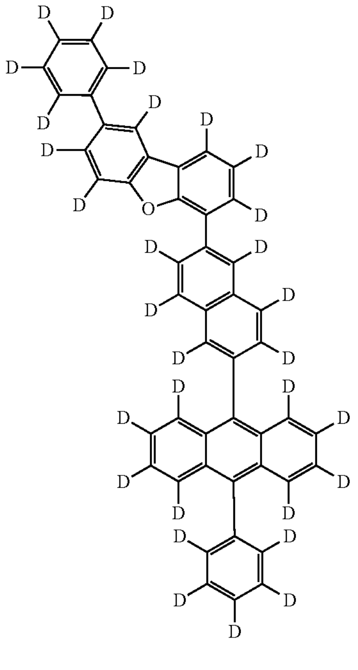

-continued
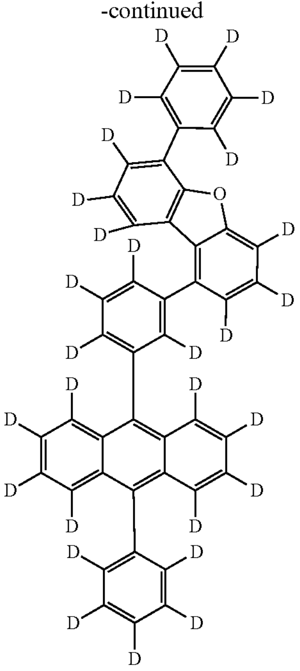
-continued
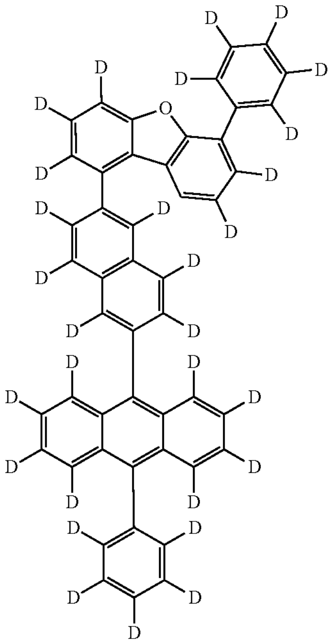 [SMILES: [2H]c1cc2c(oc3c([2H])c([2H])c([2H])c(-c4c([2H])c([2H])c5c([2H])c(-c6c7c([2H])c([2H])c([2H])c([2H])c7c(-c7c([2H])c([2H])c([2H])c([2H])c7[2H])c7c([2H])c([2H])c([2H])c([2H])c67)c([2H])c([2H])c5c4[2H])c32)c(-c2c([2H])c([2H])c([2H])c([2H])c2[2H])c1[2H]]
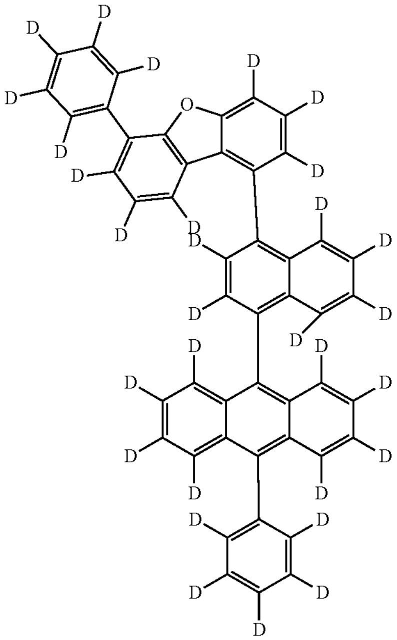
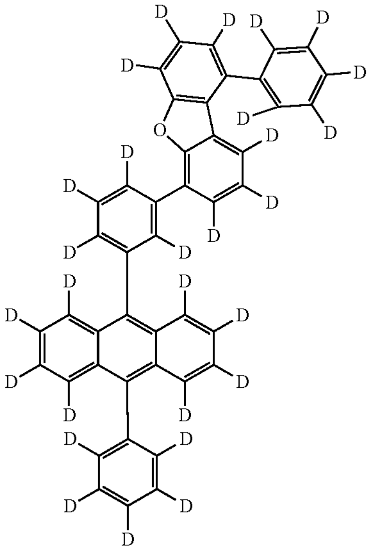

-continued
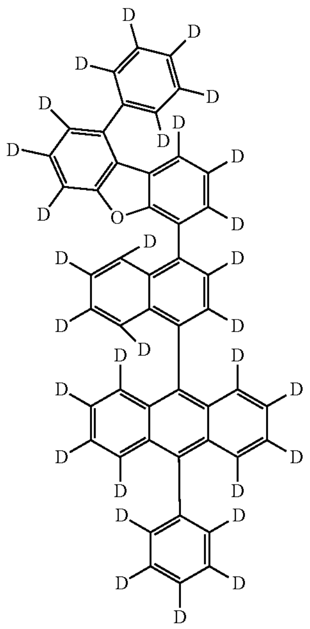
-continued
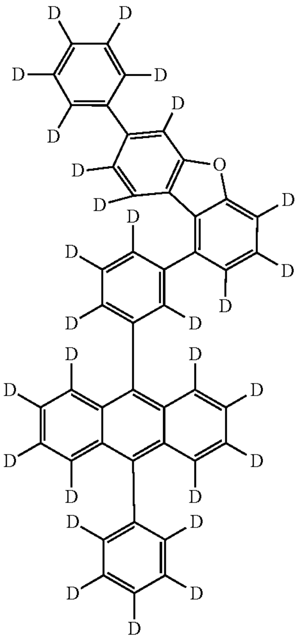
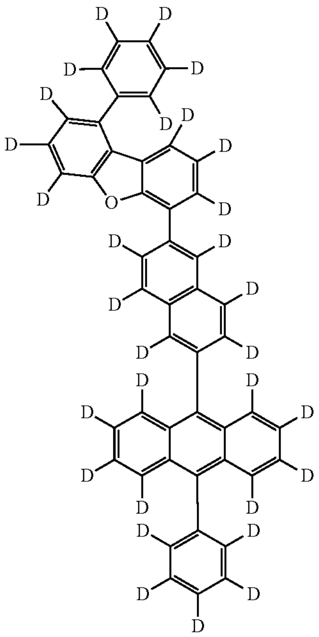
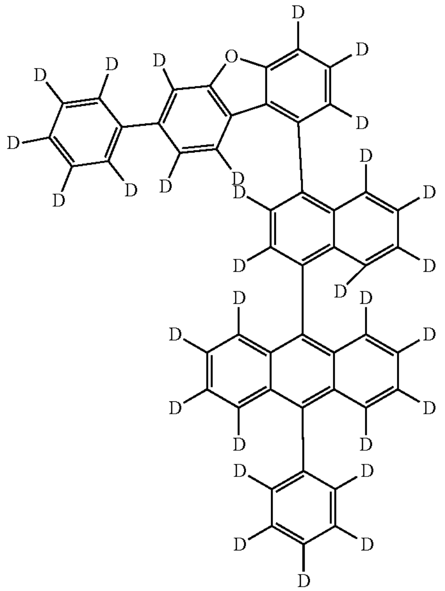

-continued
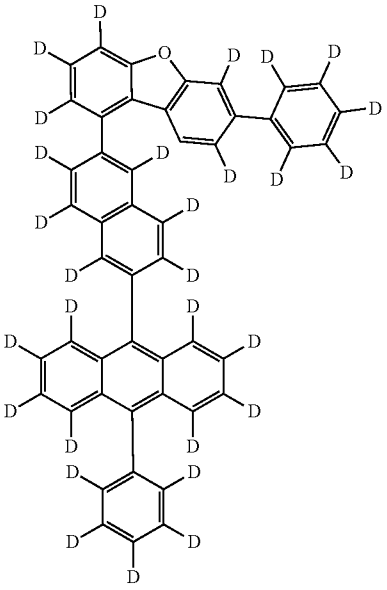 [SMILES: [2H]c1cc2c(oc3c([2H])c([2H])c([2H])c(-c4c([2H])c([2H])c5c([2H])c(-c6c7c([2H])c([2H])c([2H])c([2H])c7c(-c7c([2H])c([2H])c([2H])c([2H])c7[2H])c7c([2H])c([2H])c([2H])c([2H])c67)c([2H])c([2H])c5c4[2H])c32)c([2H])c1-c1c([2H])c([2H])c([2H])c([2H])c1[2H]]
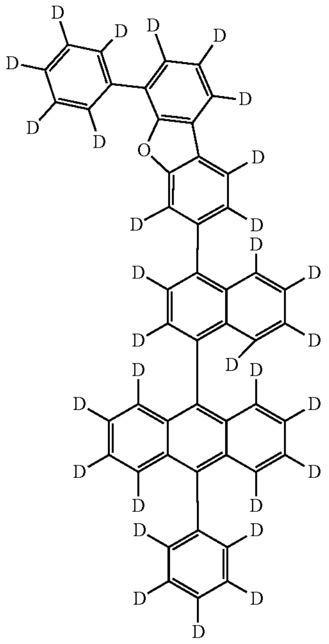
-continued
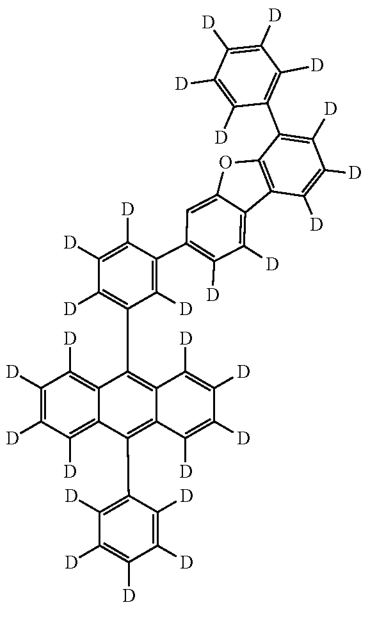
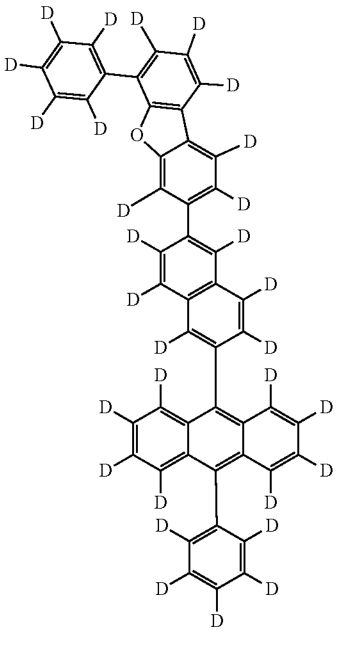

-continued
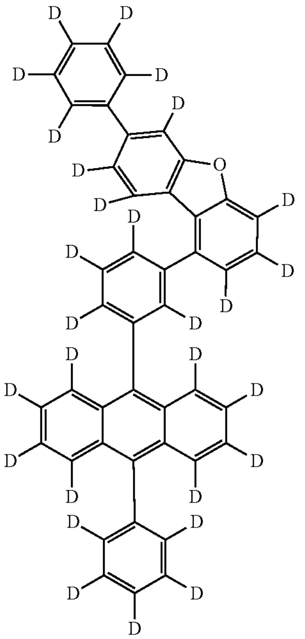
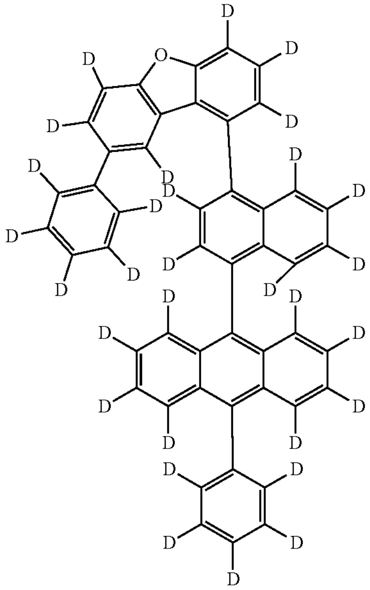
-continued
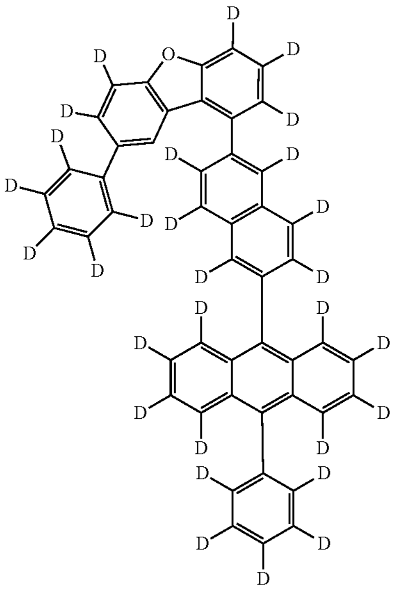 [SMILES: [2H]c1c([2H])c([2H])c(-c2cc3c(oc4c([2H])c([2H])c([2H])c(-c5c([2H])c([2H])c6c([2H])c(-c7c8c([2H])c([2H])c([2H])c([2H])c8c(-c8c([2H])c([2H])c([2H])c([2H])c8[2H])c8c([2H])c([2H])c([2H])c([2H])c78)c([2H])c([2H])c6c5[2H])c43)c([2H])c2[2H])c([2H])c1[2H]]
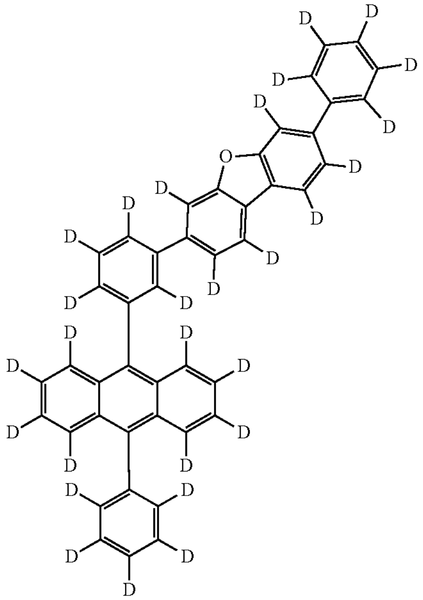

-continued
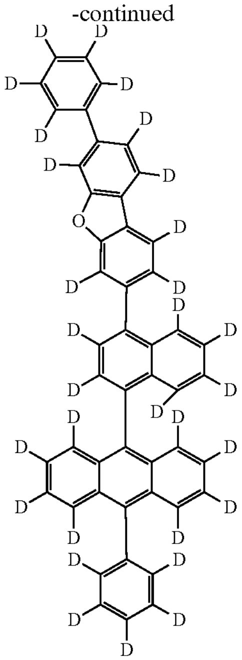
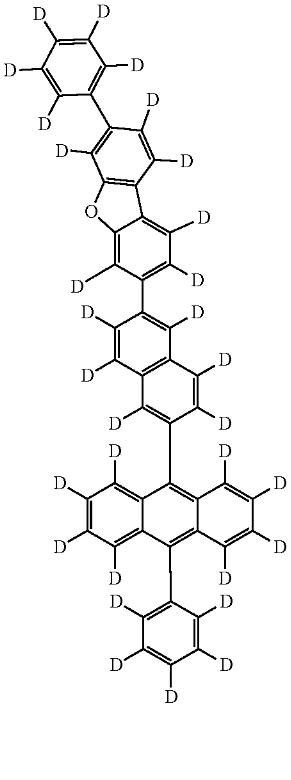
-continued
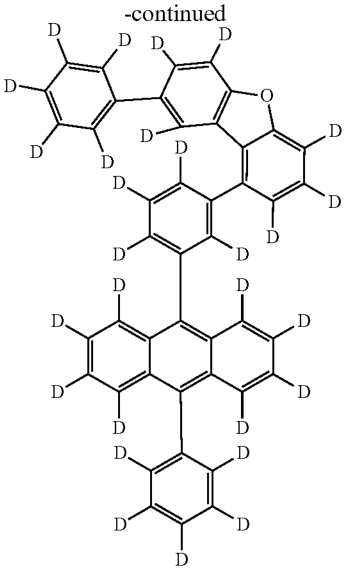
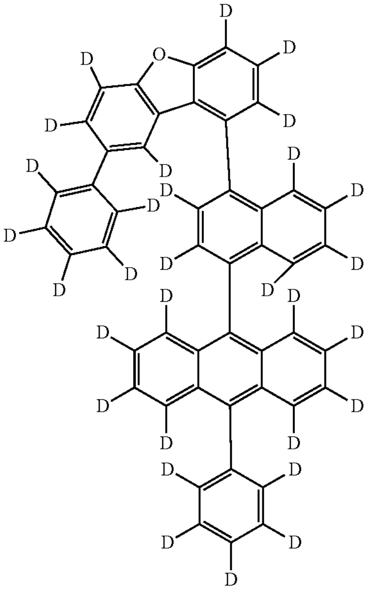
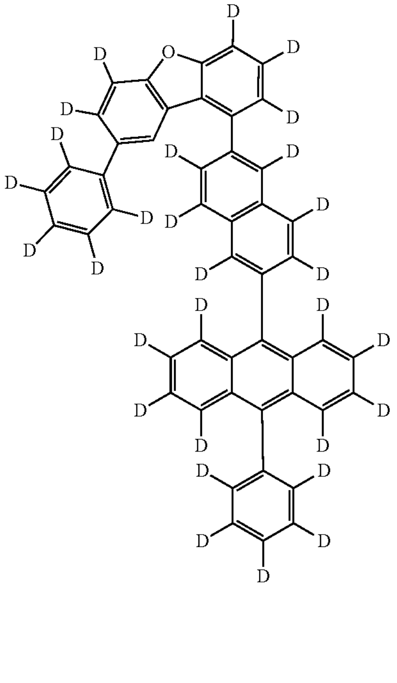 [SMILES: [2H]c1c([2H])c([2H])c(-c2cc3c(oc4c([2H])c([2H])c([2H])c(-c5c([2H])c([2H])c6c([2H])c(-c7c8c([2H])c([2H])c([2H])c([2H])c8c(-c8c([2H])c([2H])c([2H])c([2H])c8[2H])c8c([2H])c([2H])c([2H])c([2H])c78)c([2H])c([2H])c6c5[2H])c43)c([2H])c2[2H])c([2H])c1[2H]]

-continued
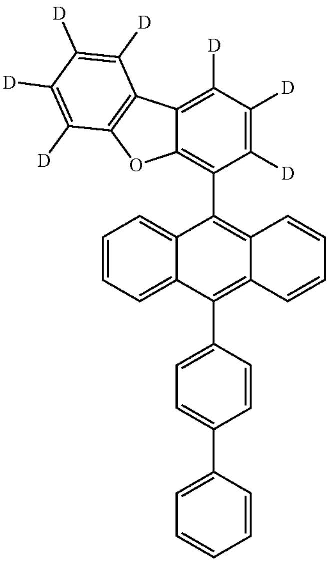
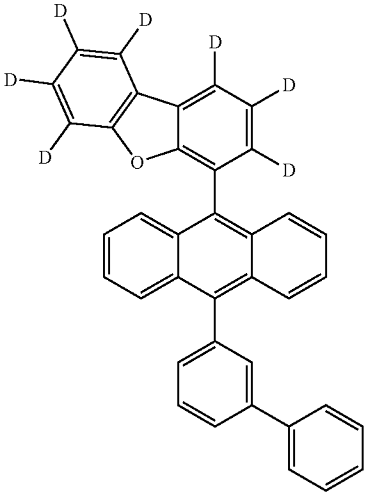
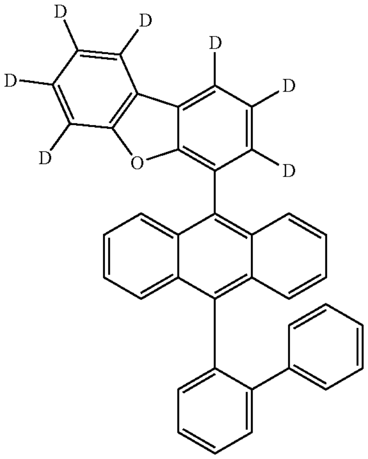
-continued
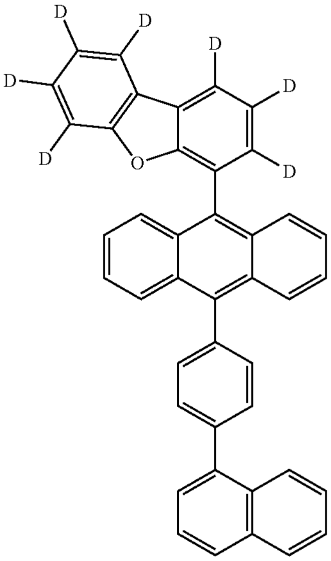
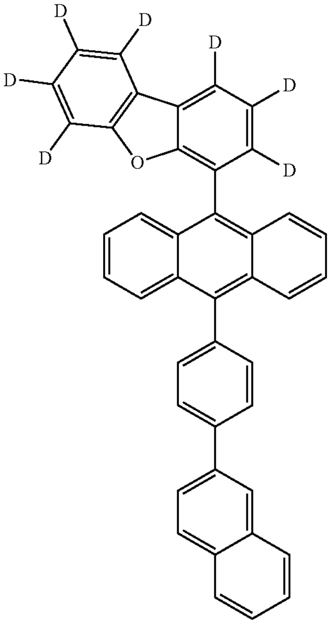

-continued
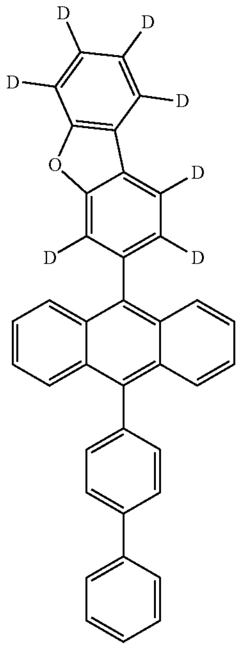
-continued
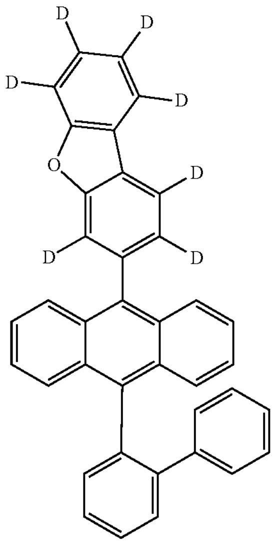
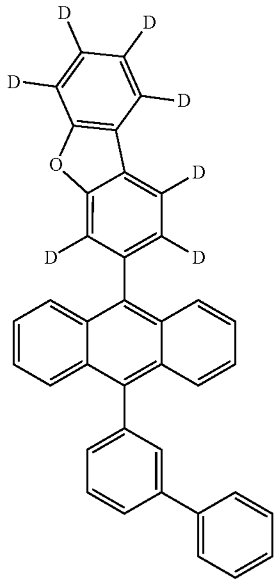
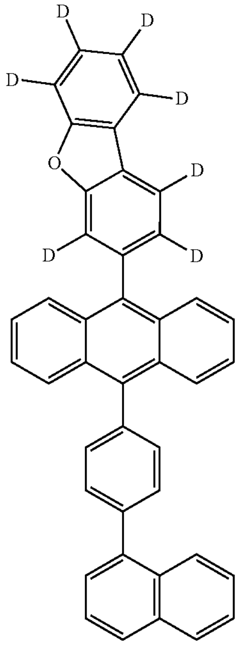

-continued
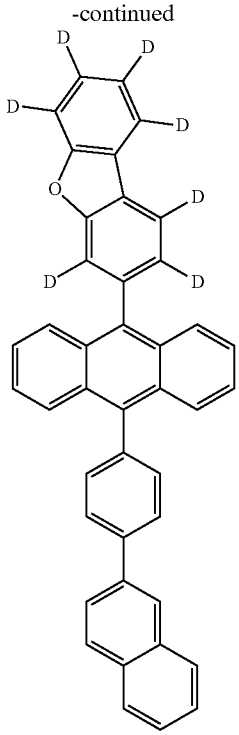
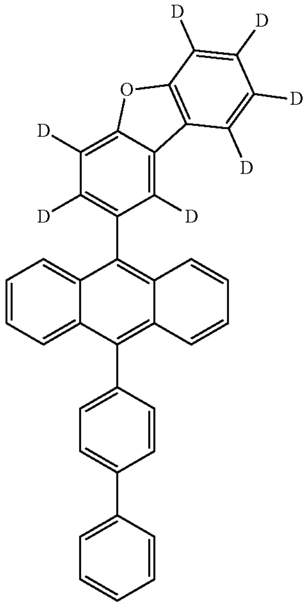
-continued
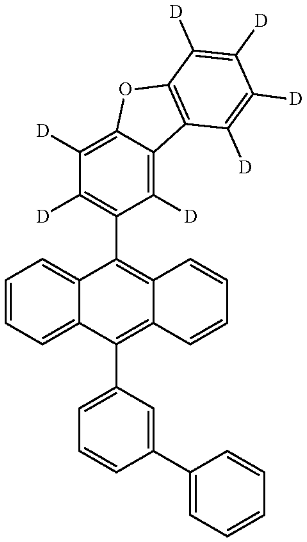
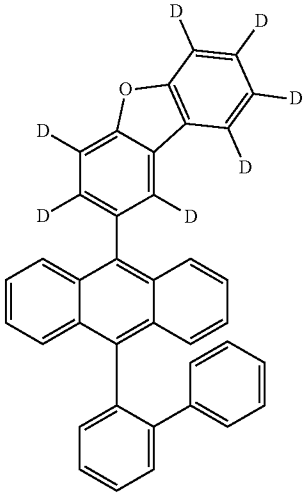
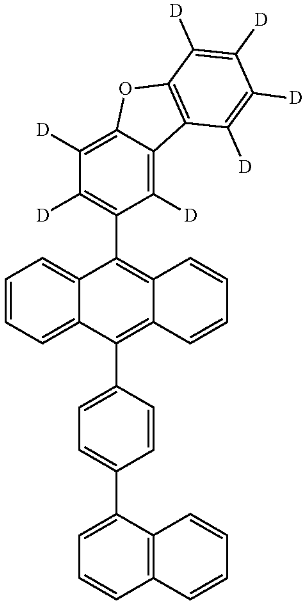

-continued
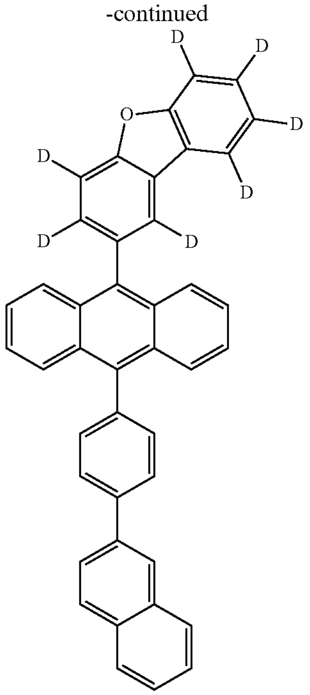
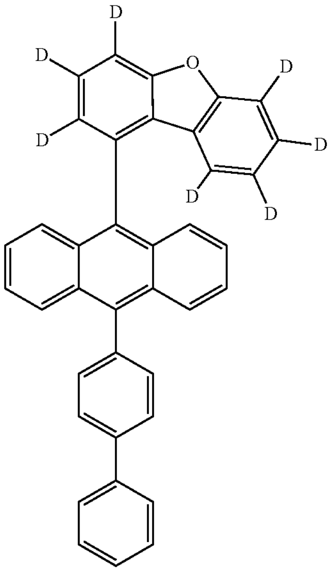
-continued
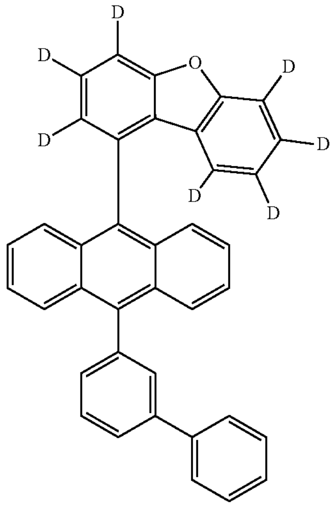
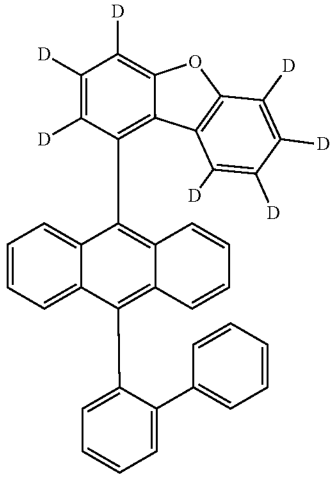
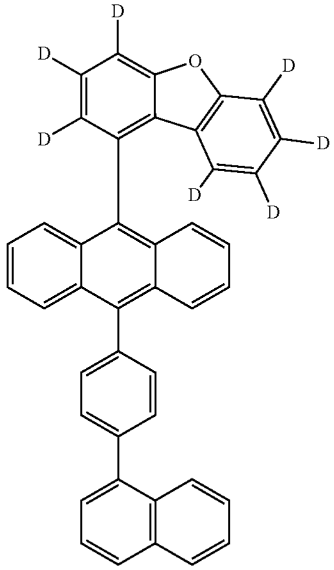

-continued
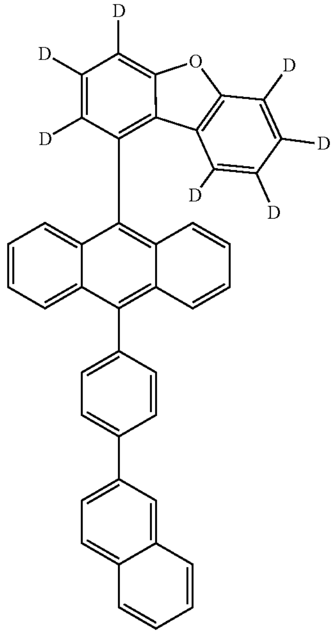
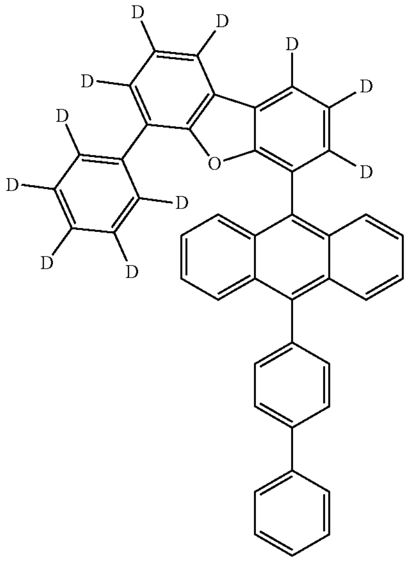
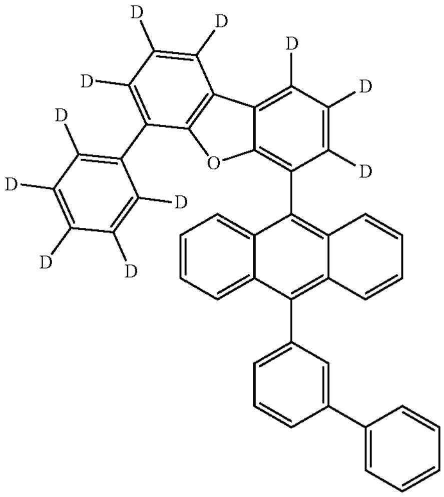
-continued
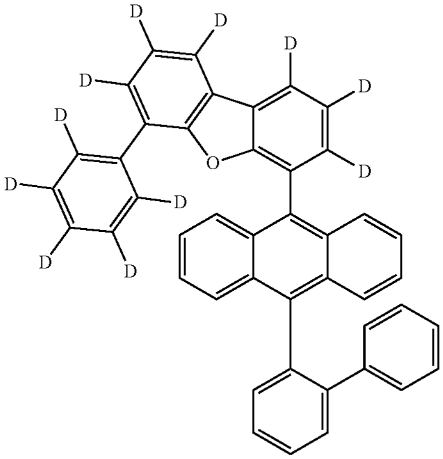
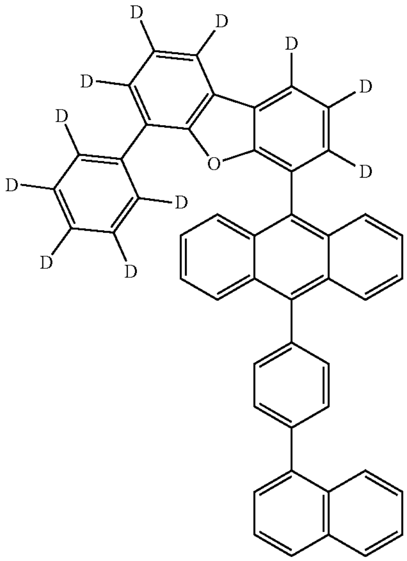
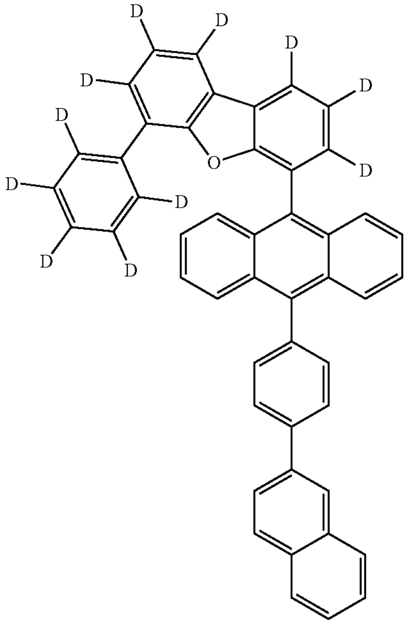

-continued
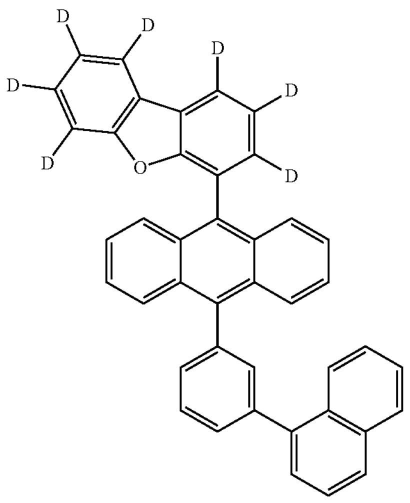
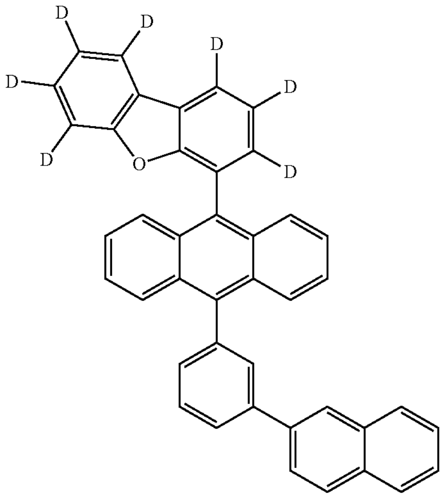
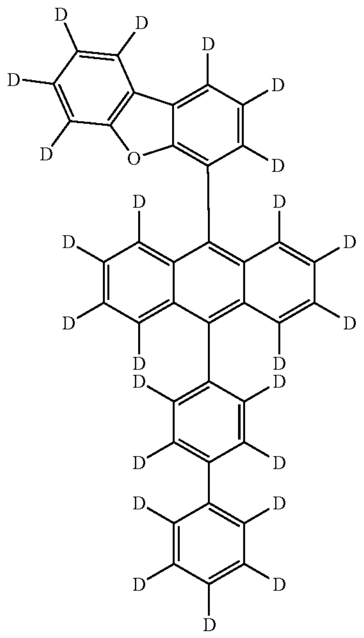
-continued
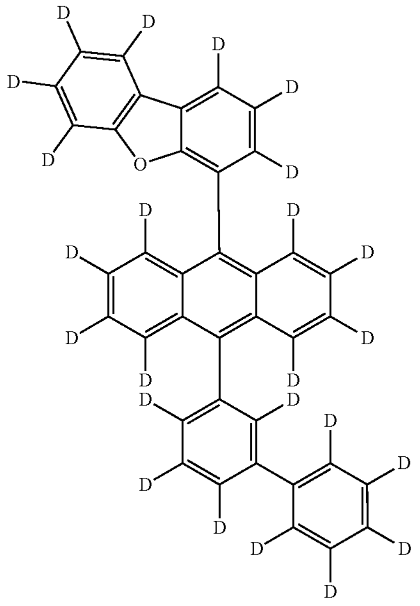
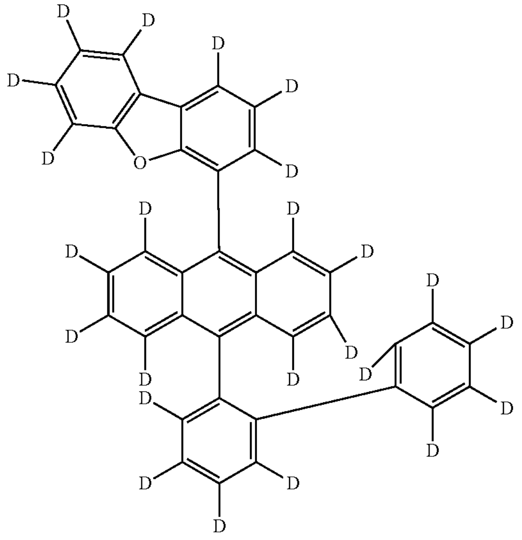
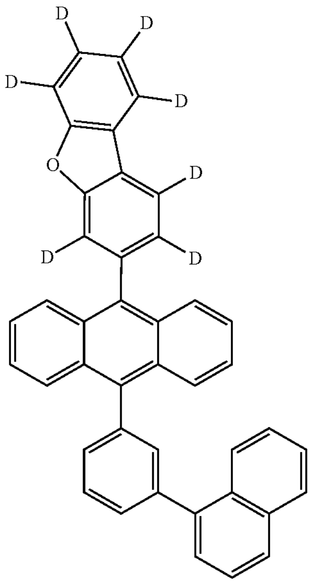

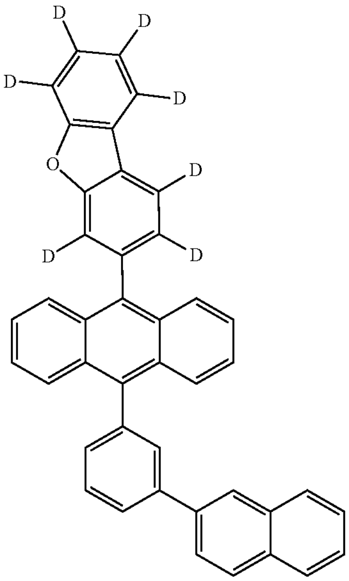
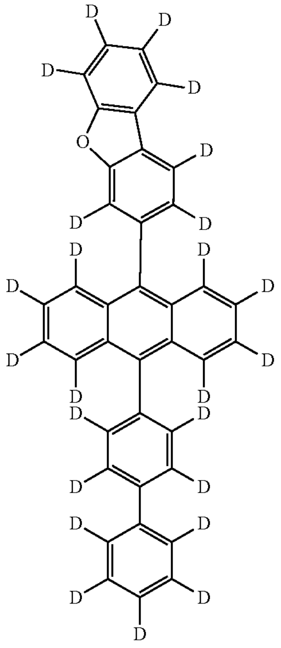
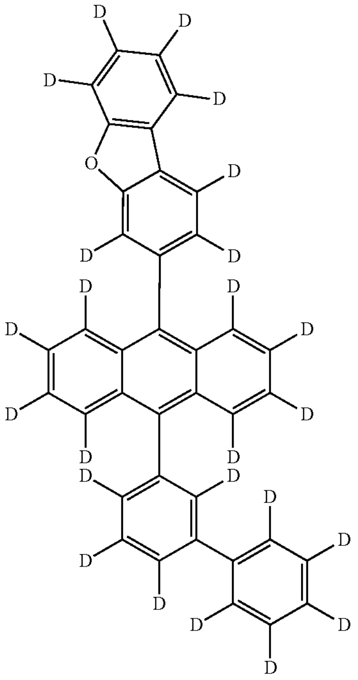
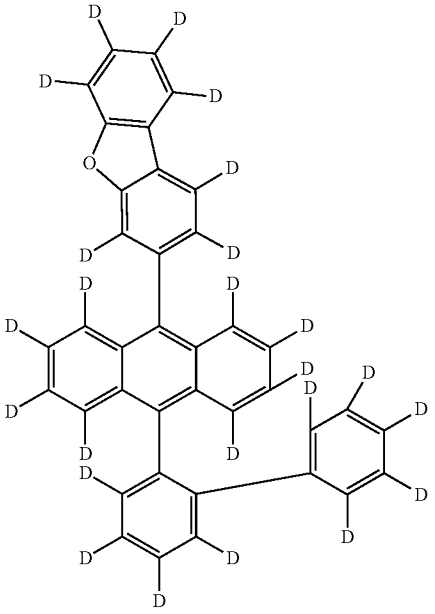

-continued
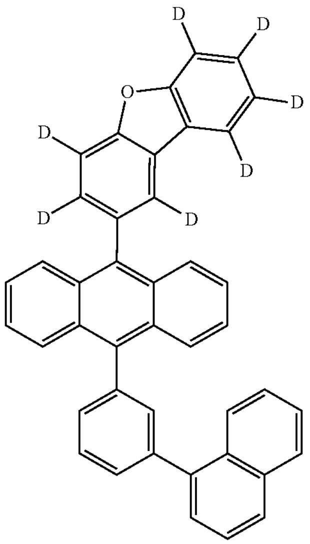
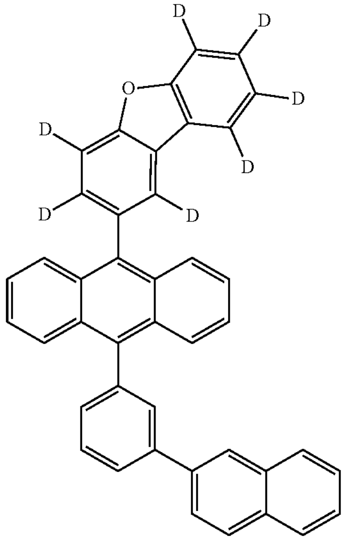
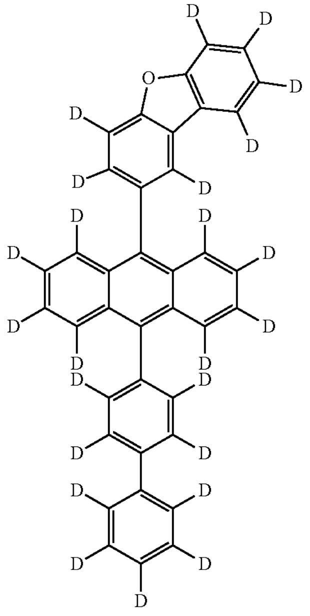
-continued
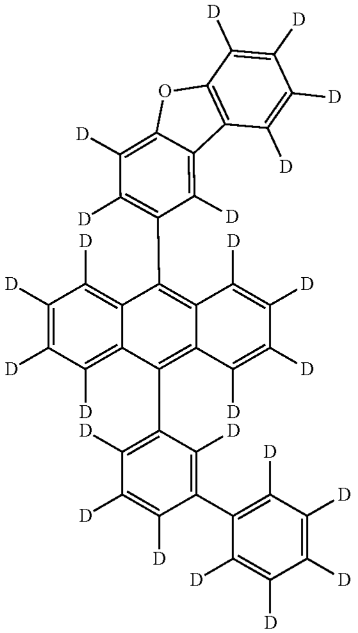
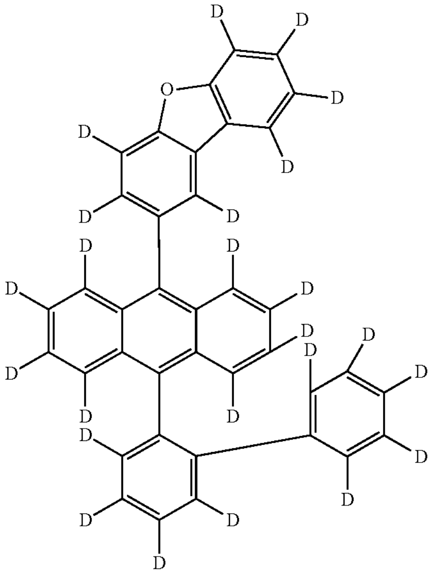
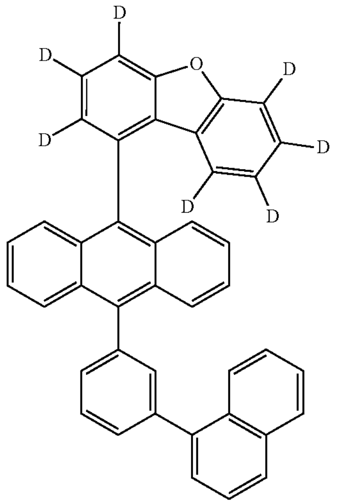

2223
-continued
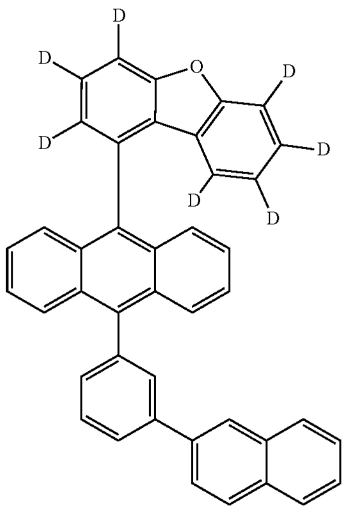
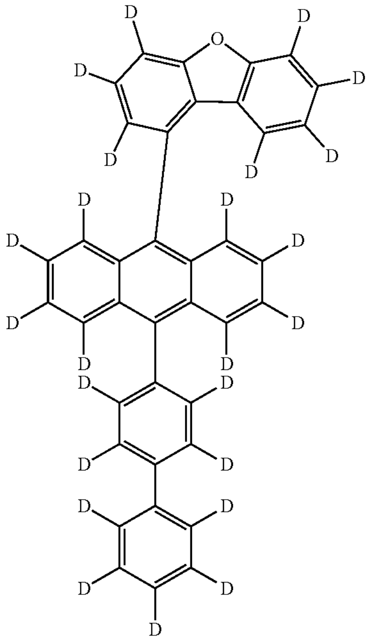
2224
-continued
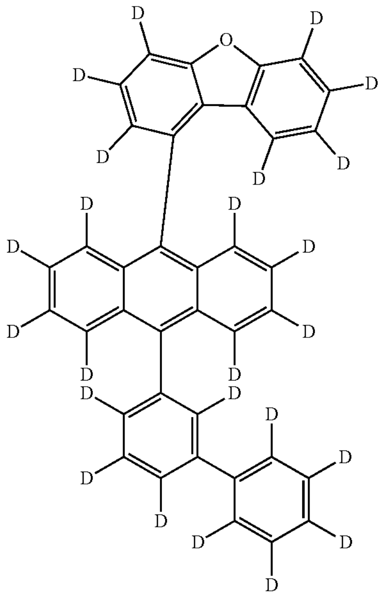
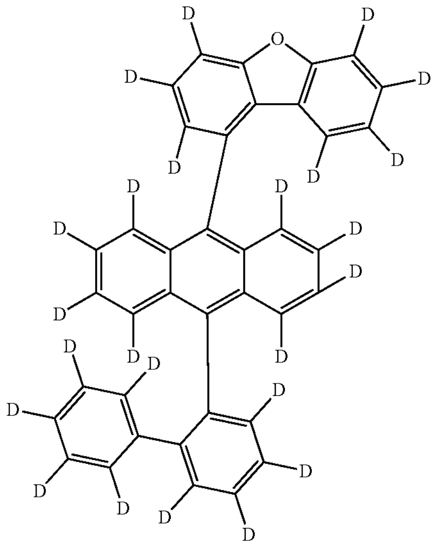
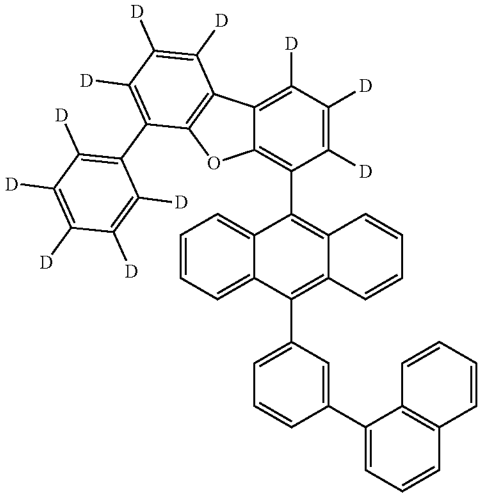

-continued
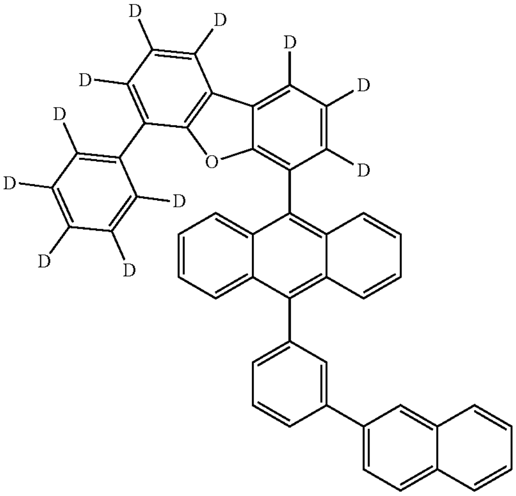
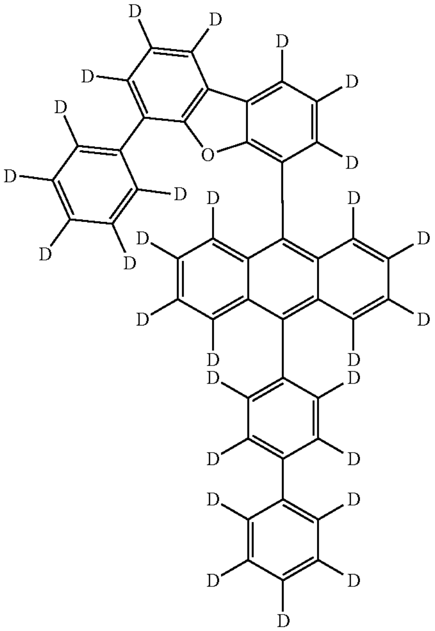
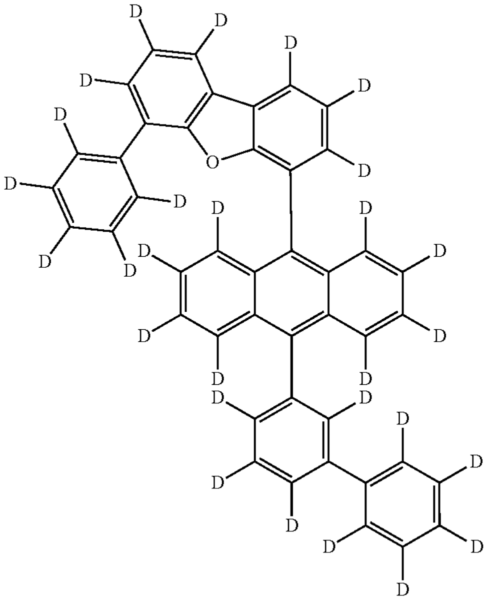
-continued
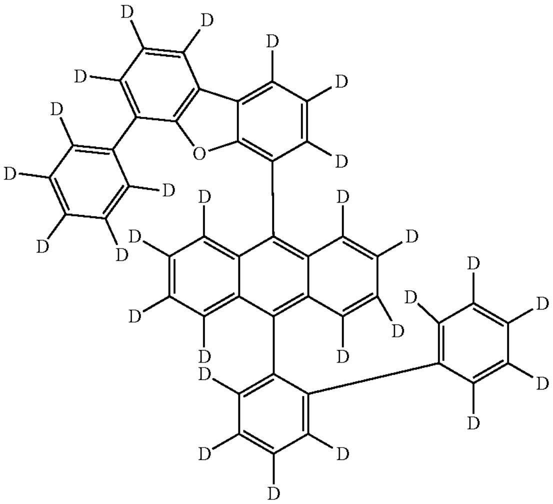
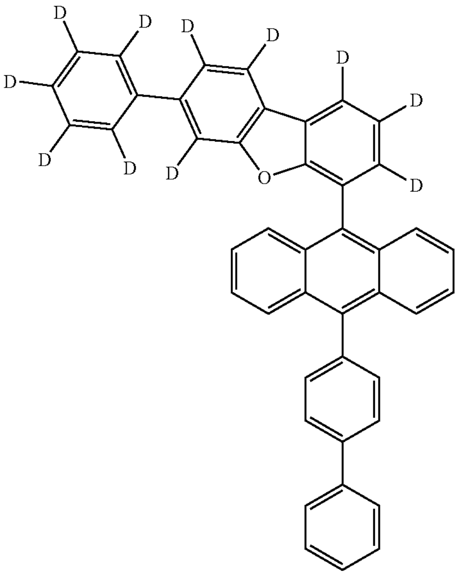
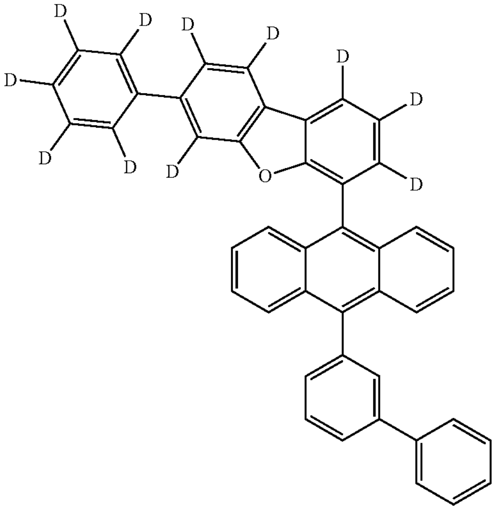

-continued
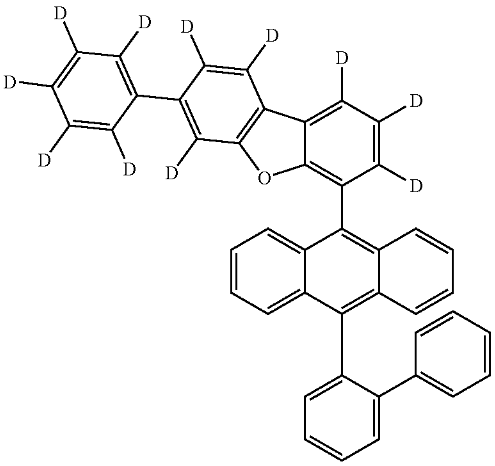
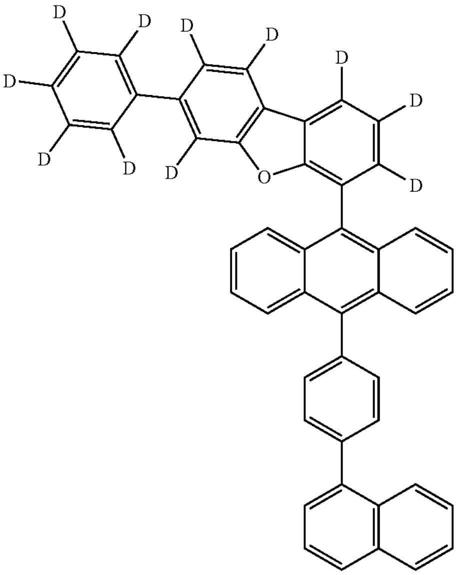
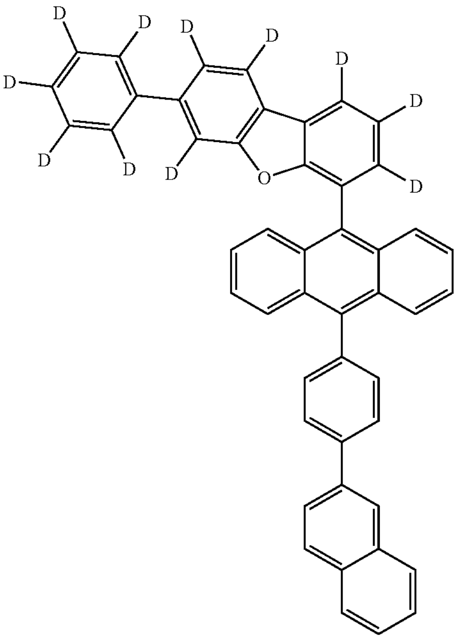
-continued
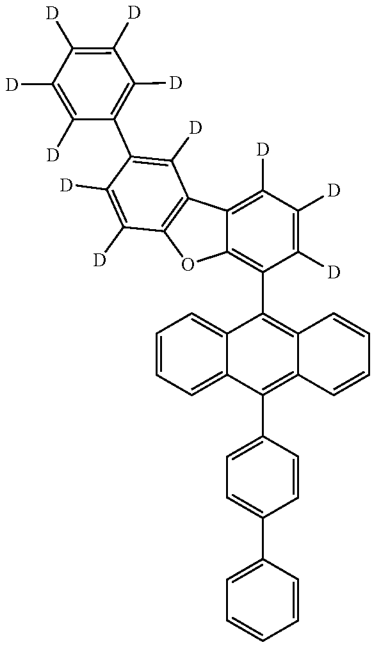
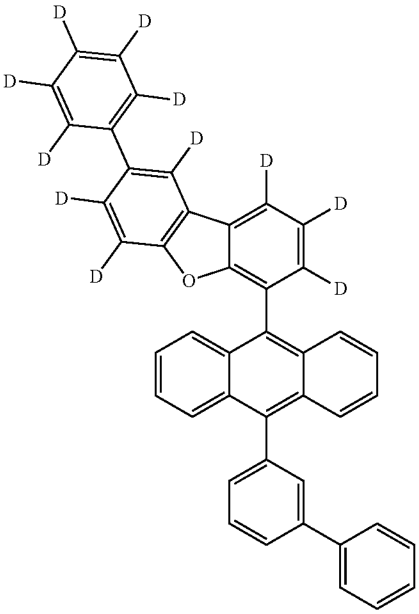

-continued
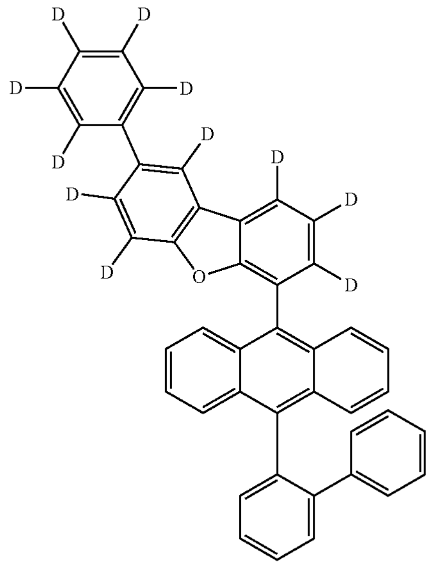
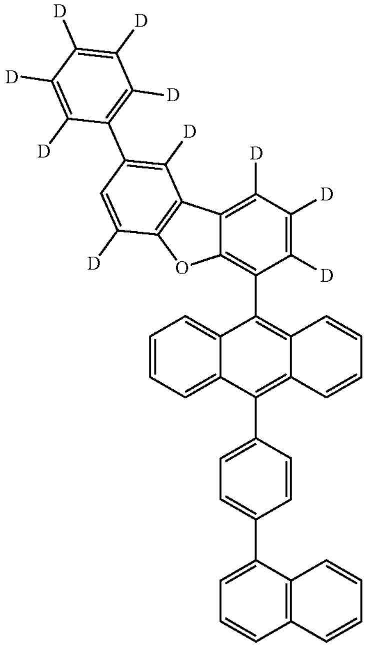
-continued
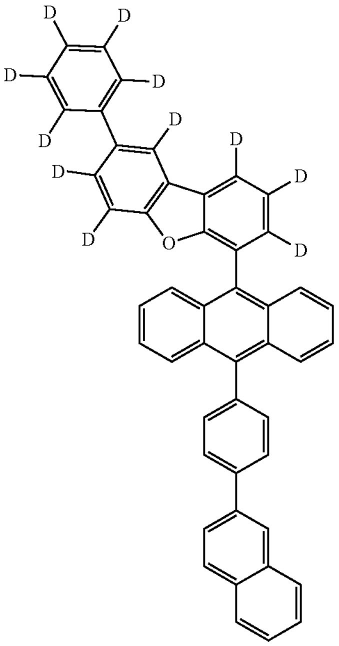
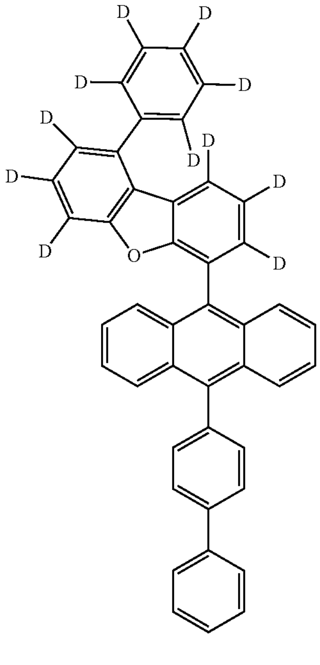

-continued
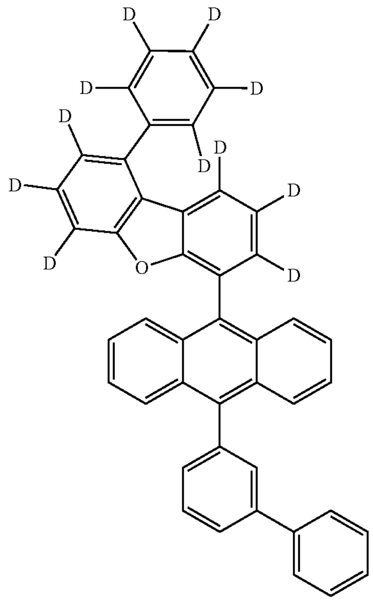
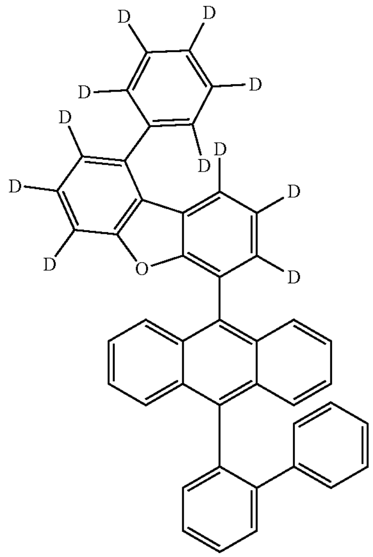
-continued
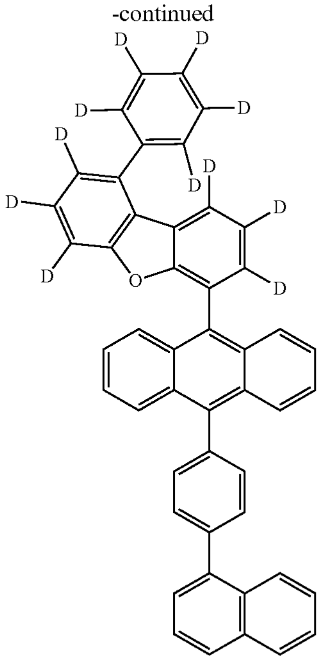
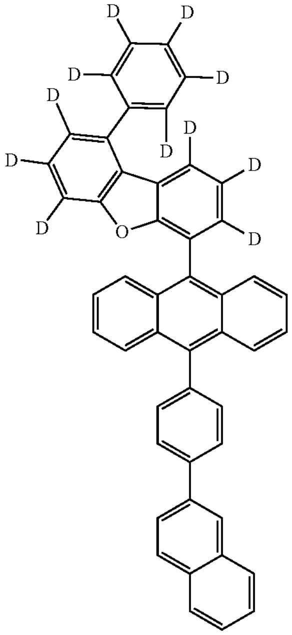

-continued
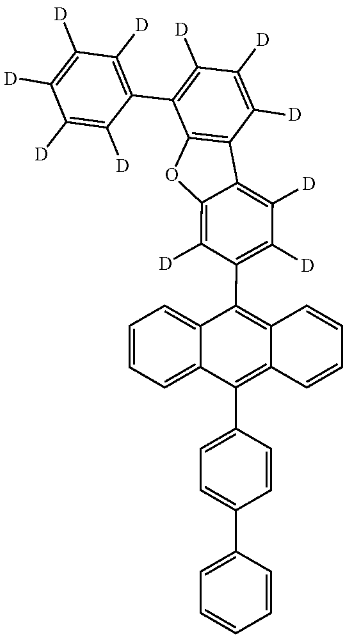
-continued
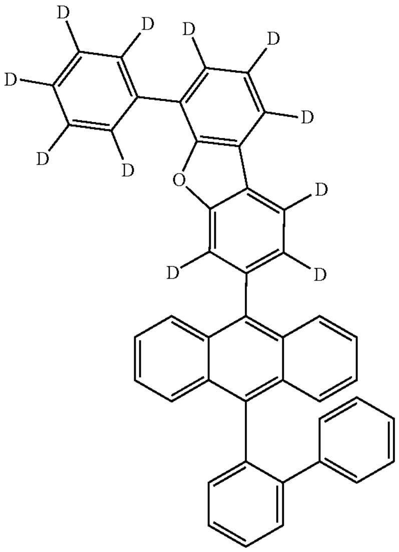
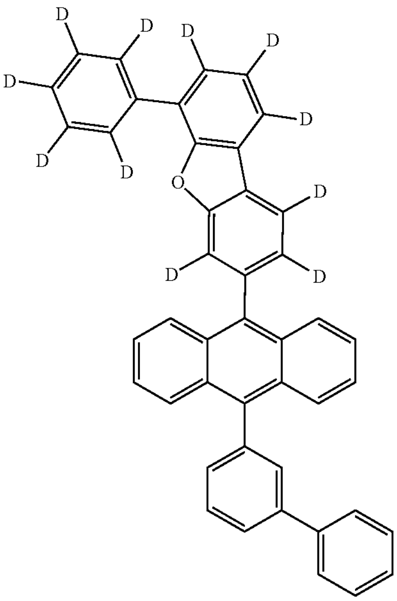
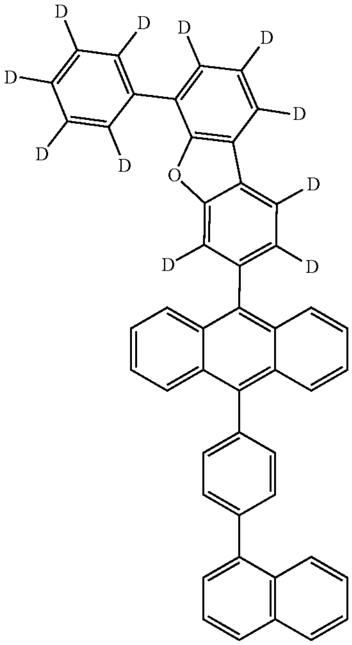

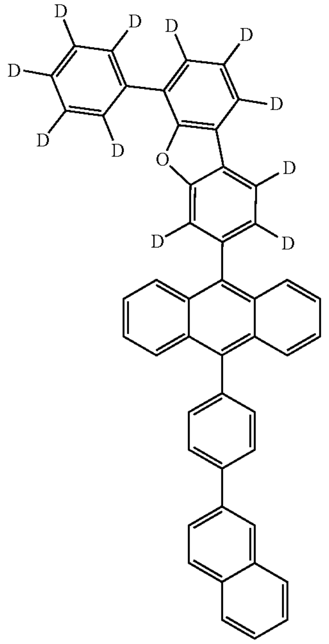
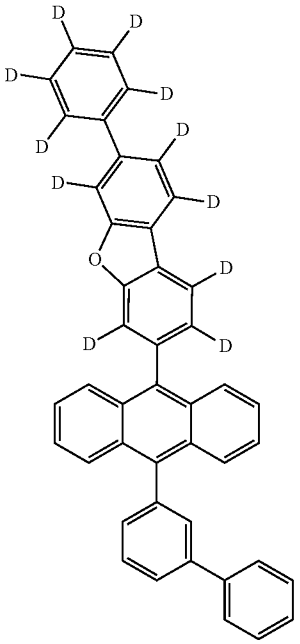
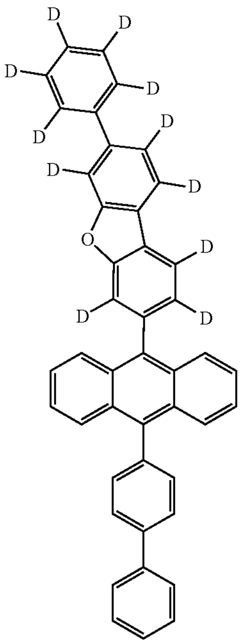
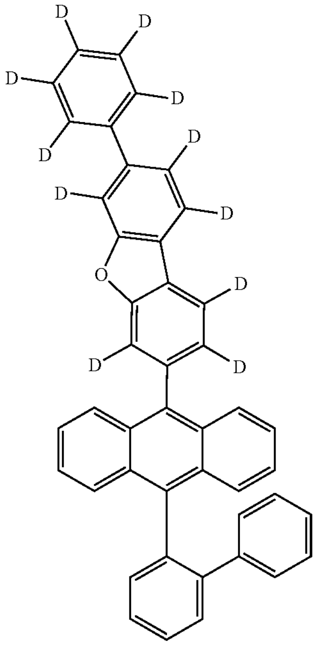

-continued
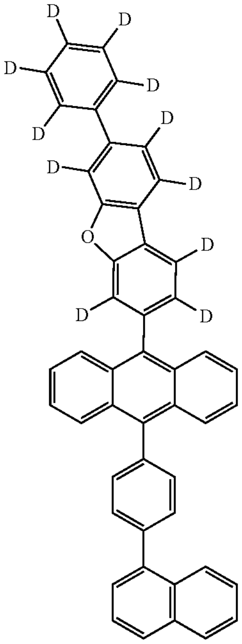
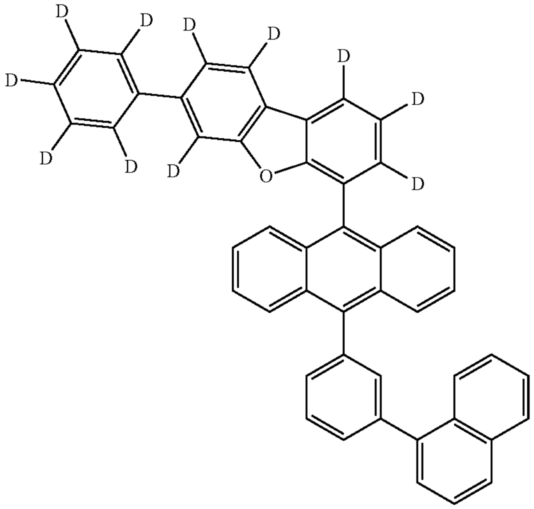
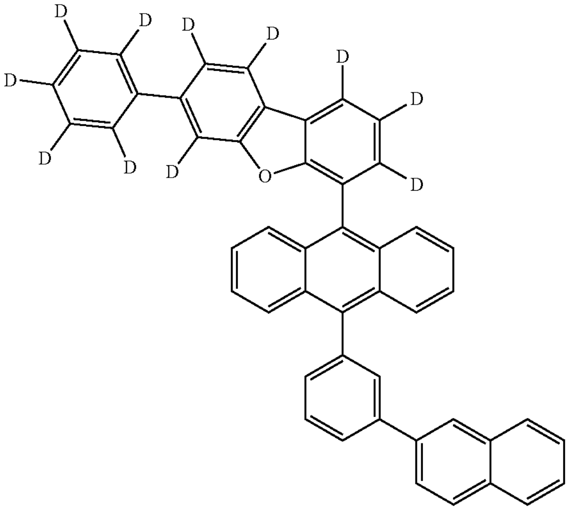
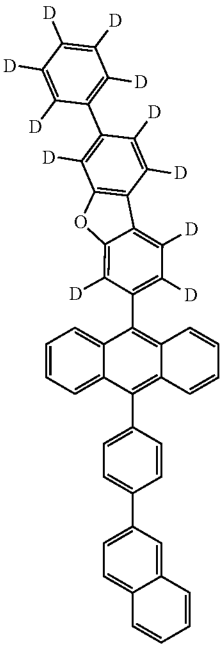
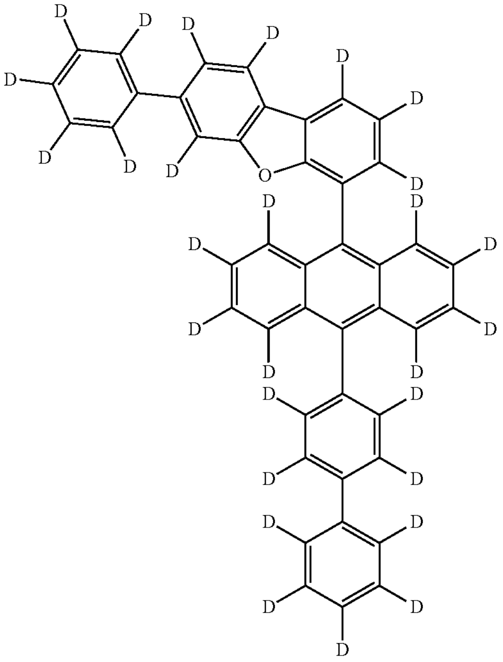

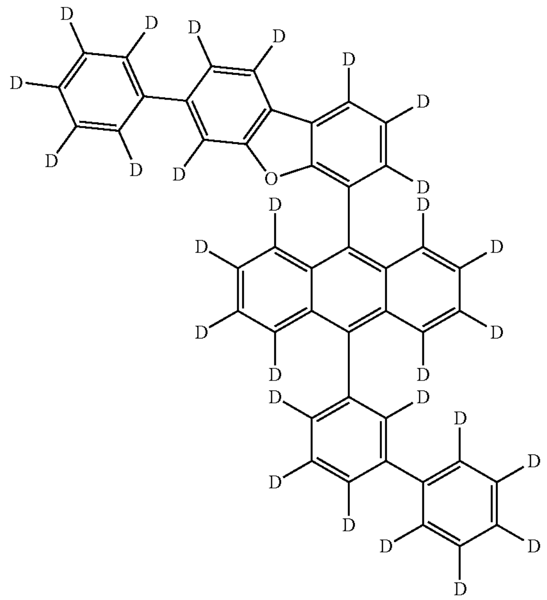
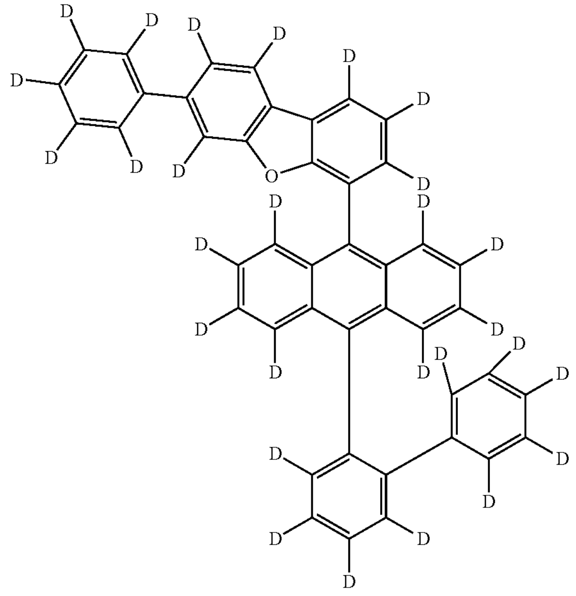
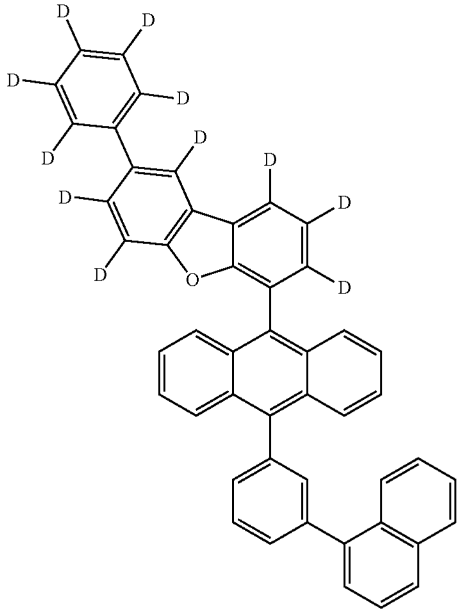
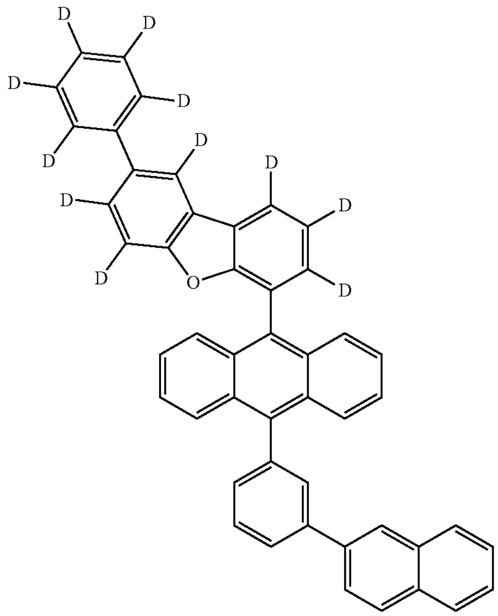

-continued
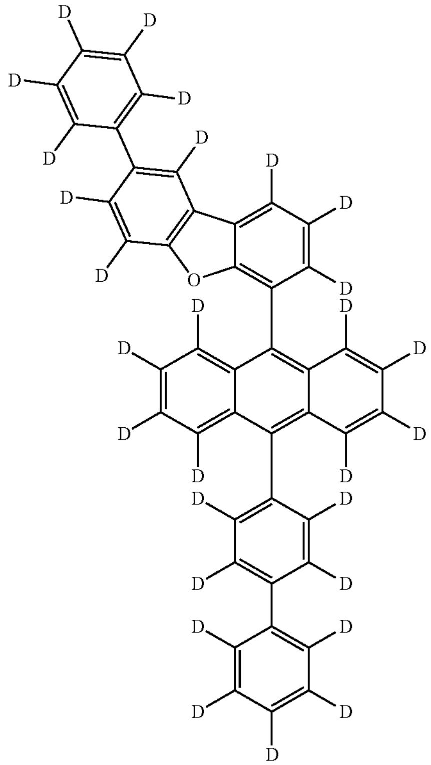
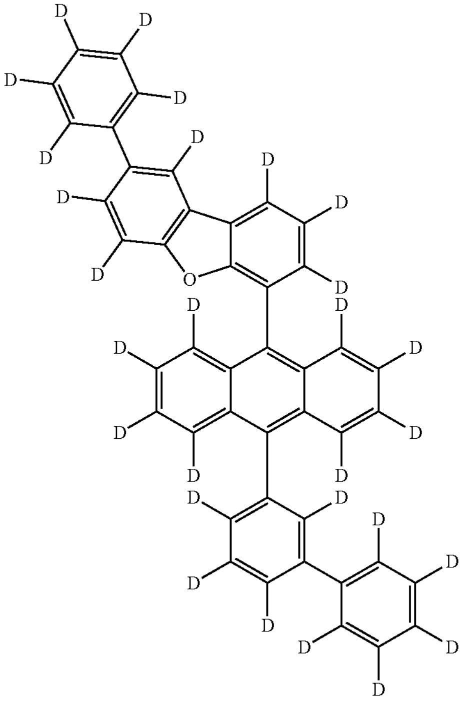
-continued
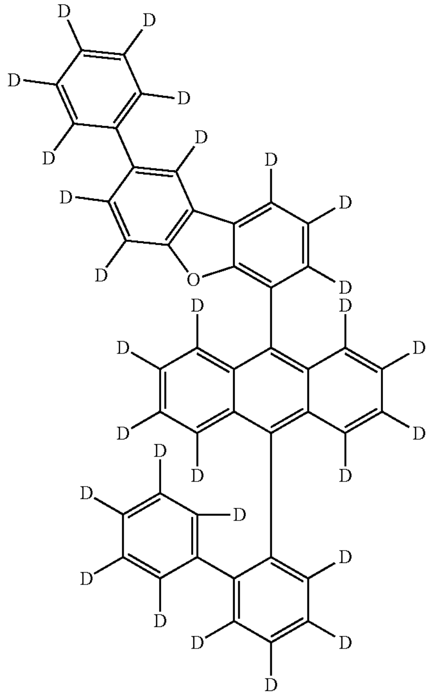
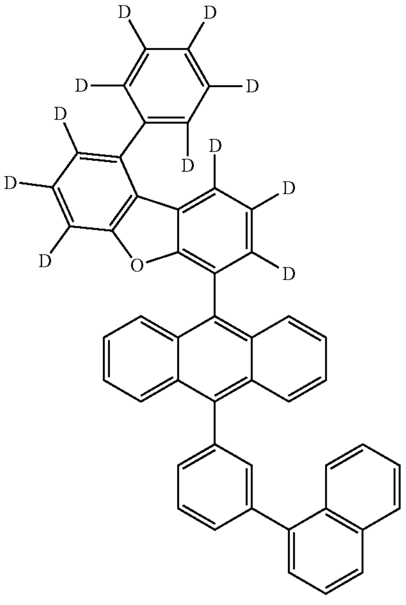

-continued
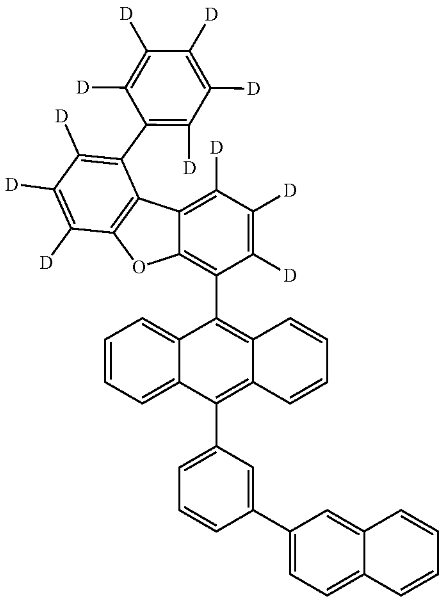
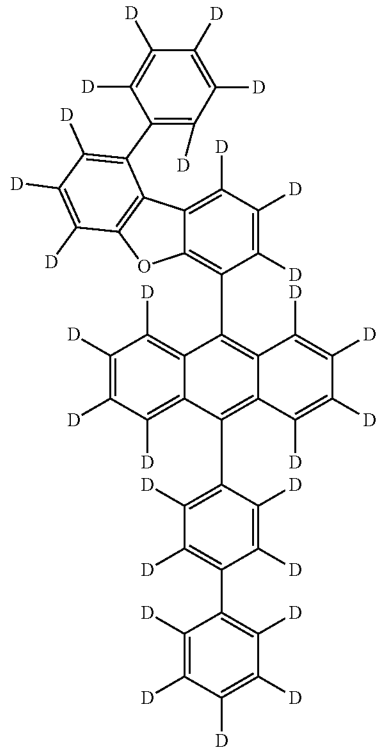
-continued
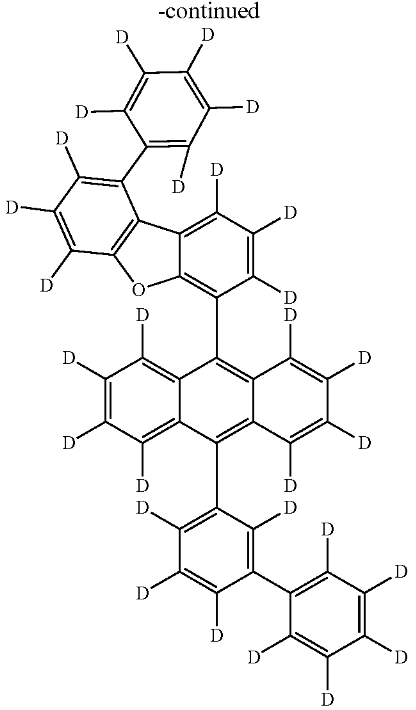
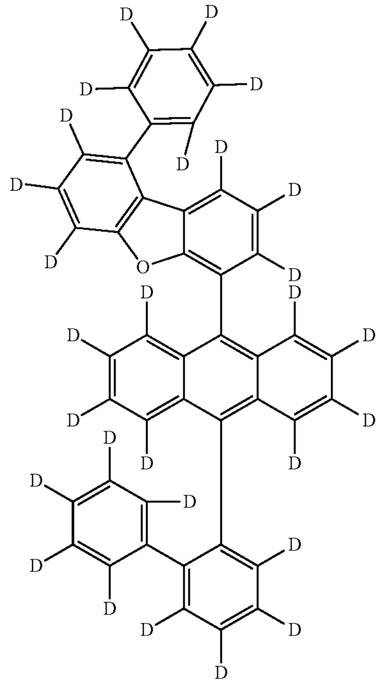

-continued
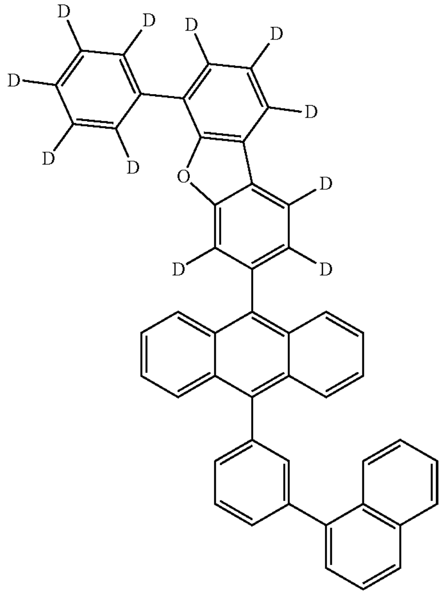
-continued
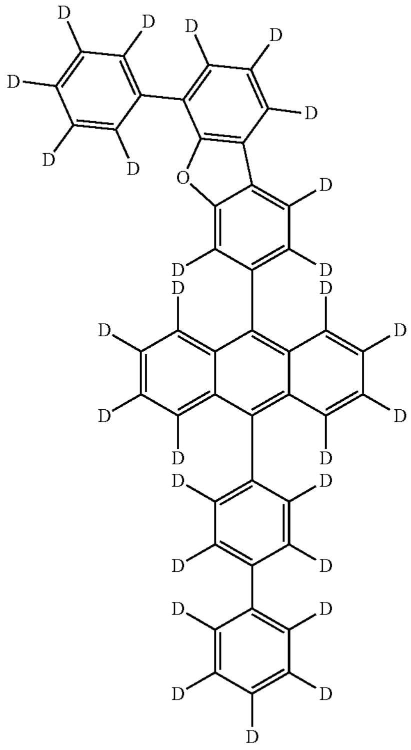
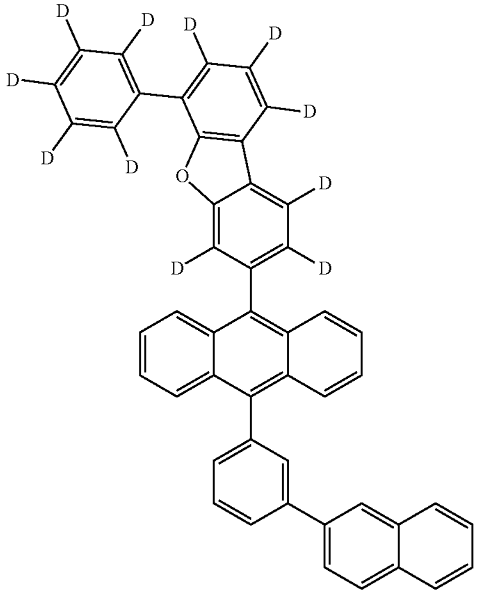
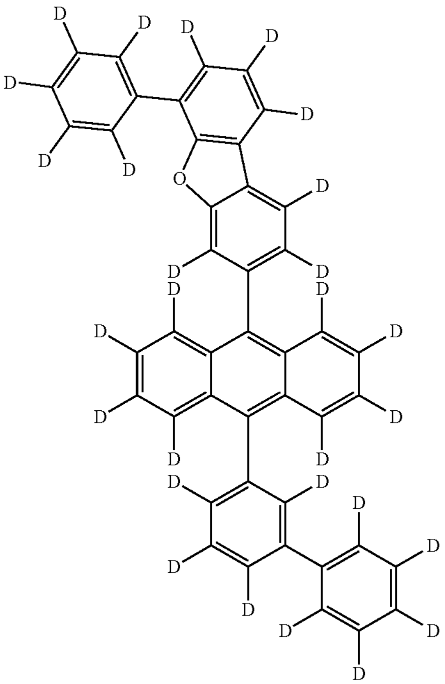

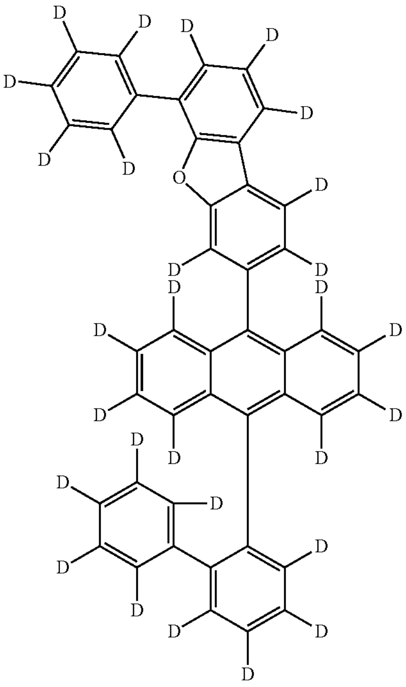 [SMILES: [2H]c1c([2H])c([2H])c(-c2c([2H])c([2H])c([2H])c([2H])c2-c2c3c([2H])c([2H])c([2H])c([2H])c3c(-c3c([2H])c([2H])c4c(oc5c(-c6c([2H])c([2H])c([2H])c([2H])c6[2H])c([2H])c([2H])c([2H])c54)c3[2H])c3c([2H])c([2H])c([2H])c([2H])c23)c([2H])c1[2H]]
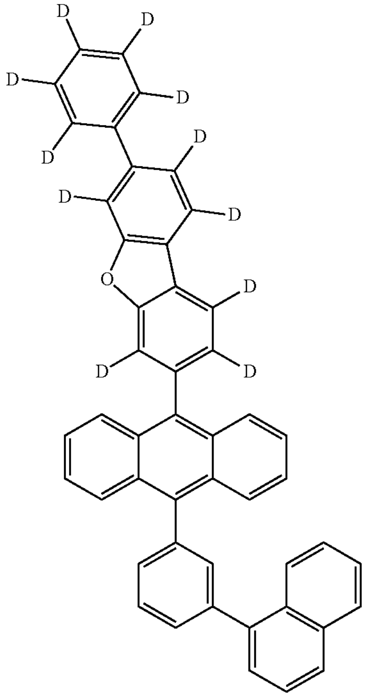
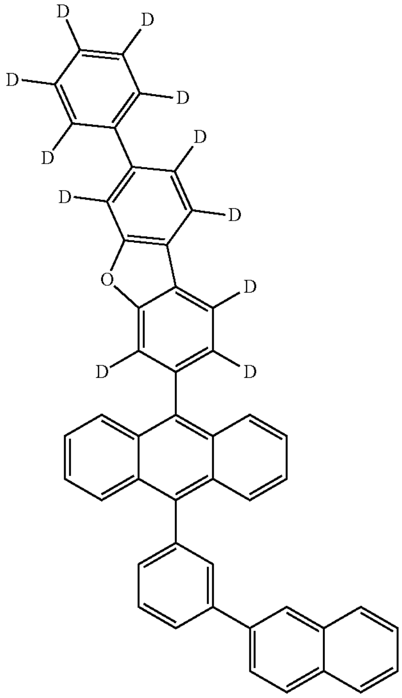
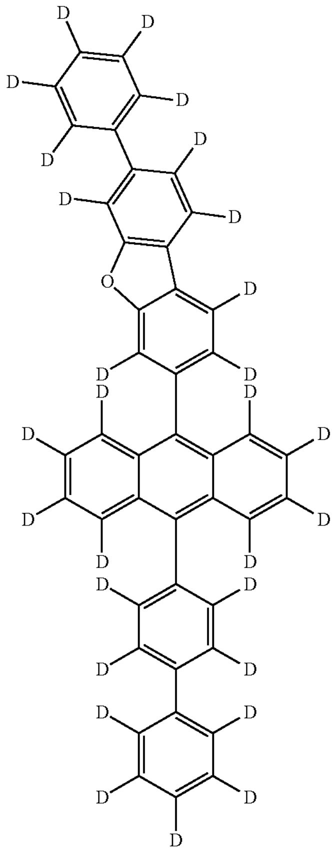

-continued
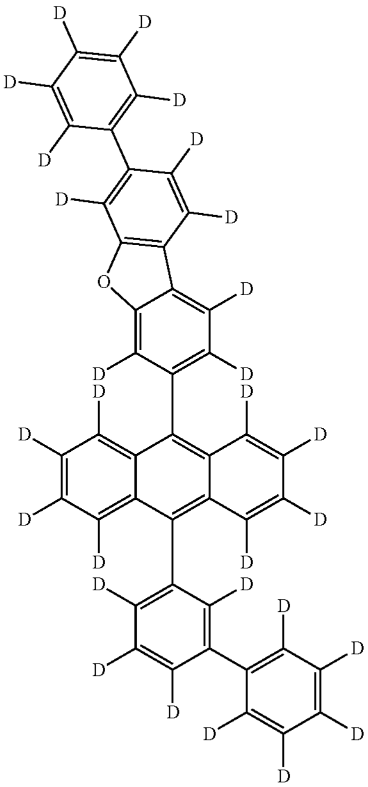
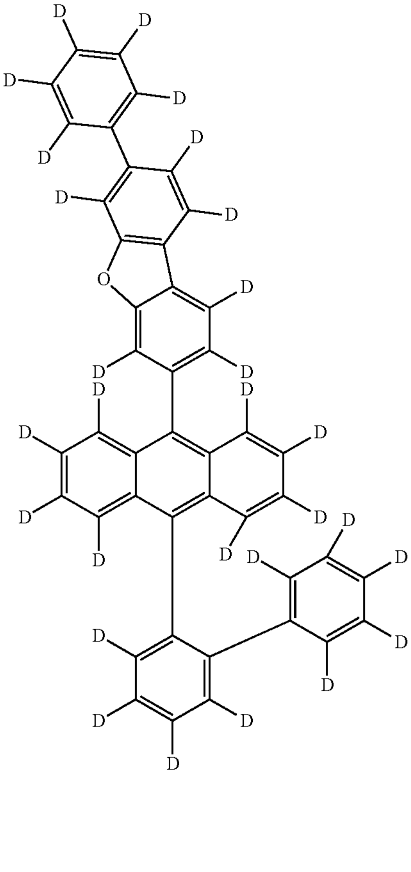
-continued
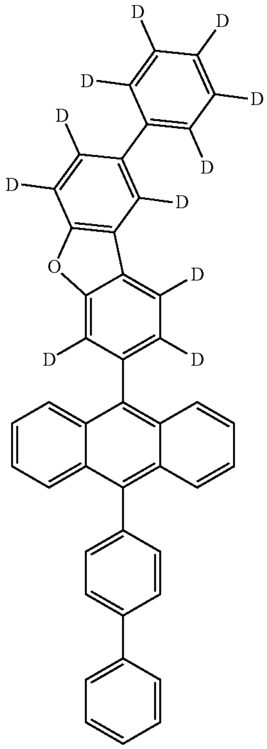
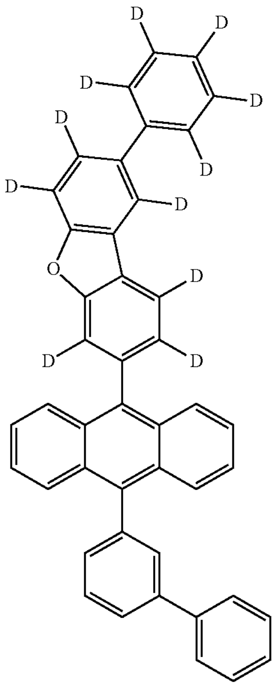

-continued
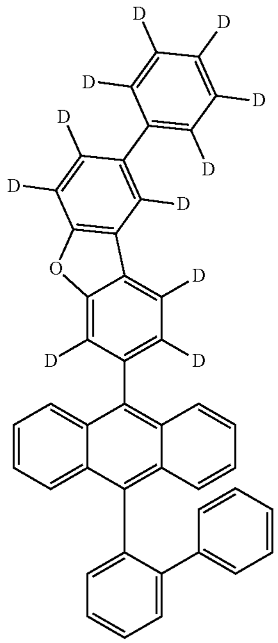
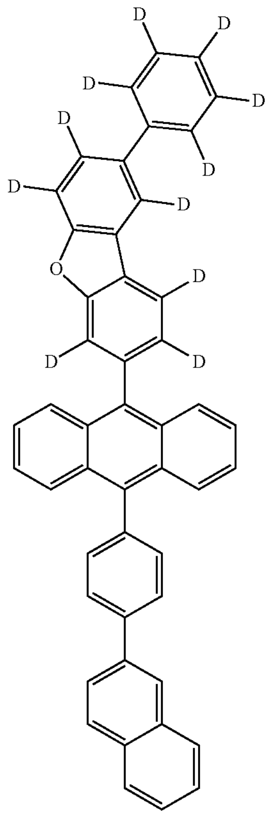
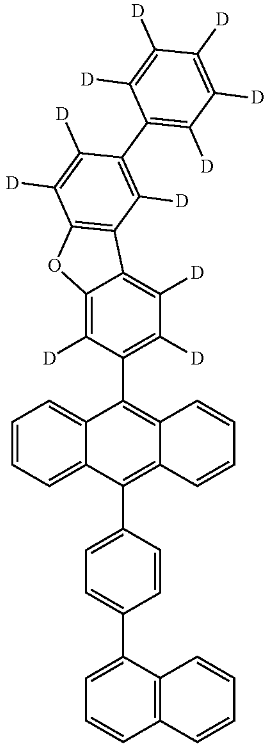
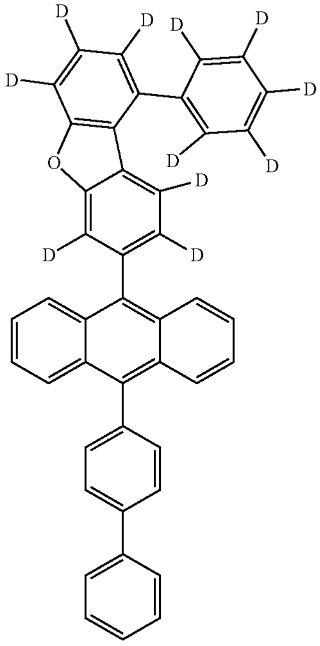

-continued
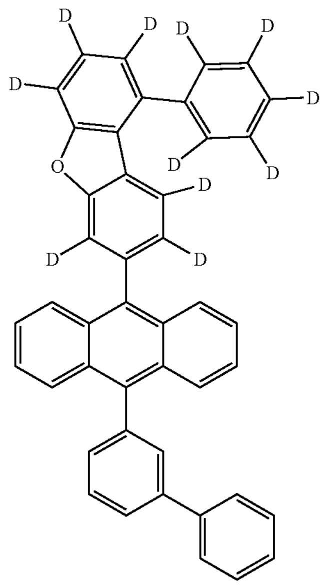
-continued
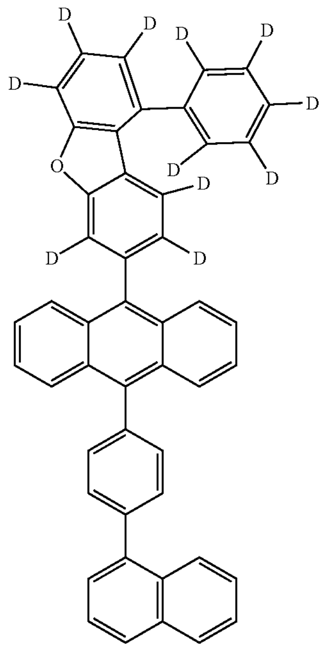
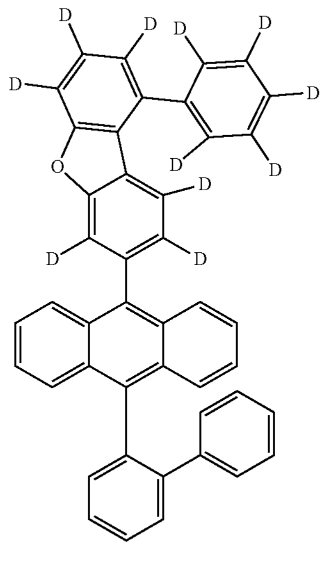
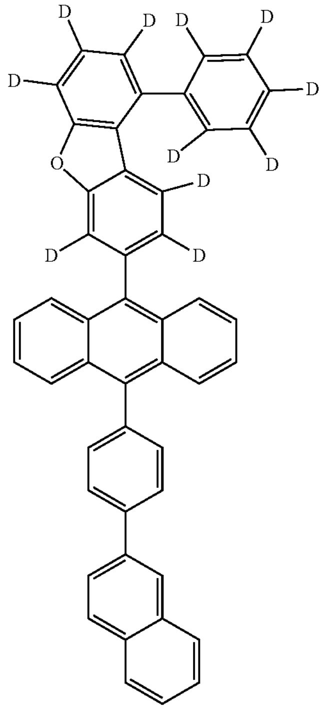

-continued
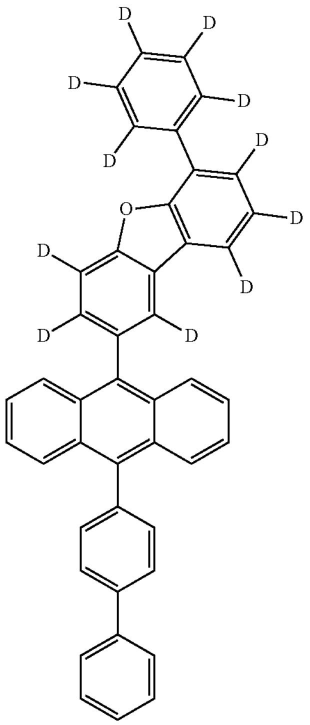
-continued
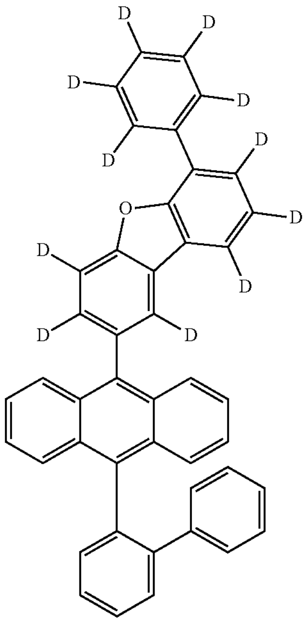
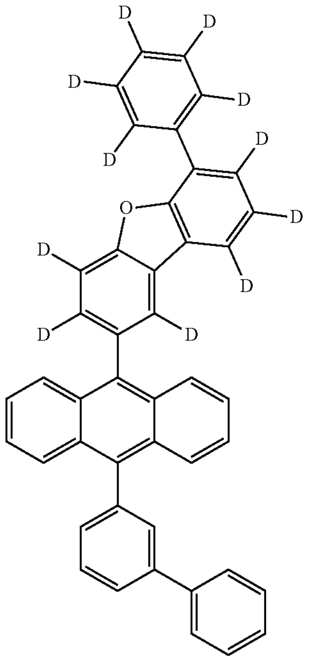
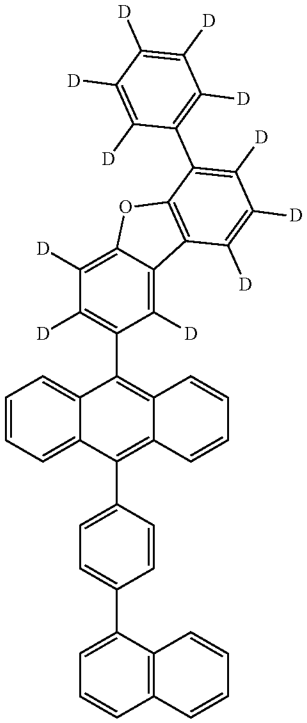

-continued
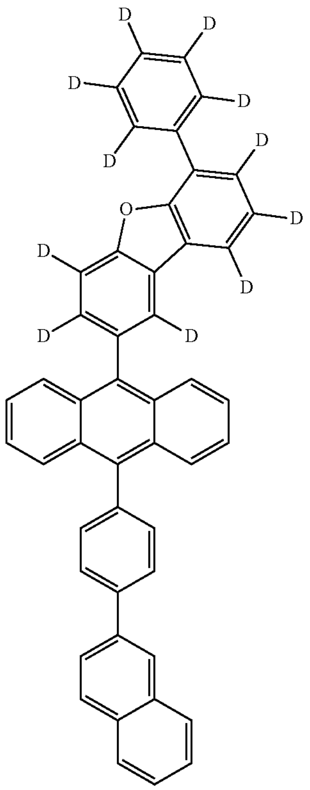
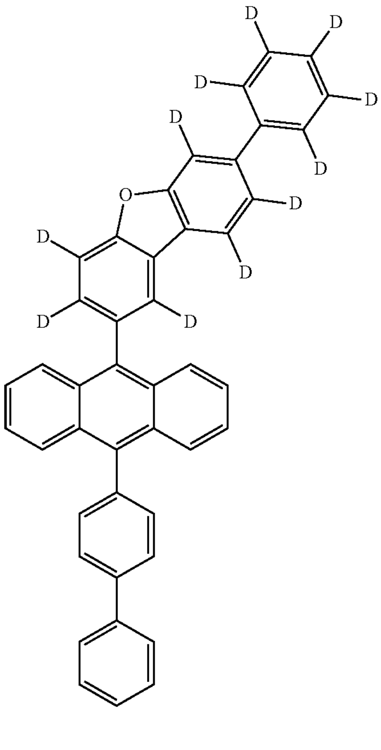
-continued
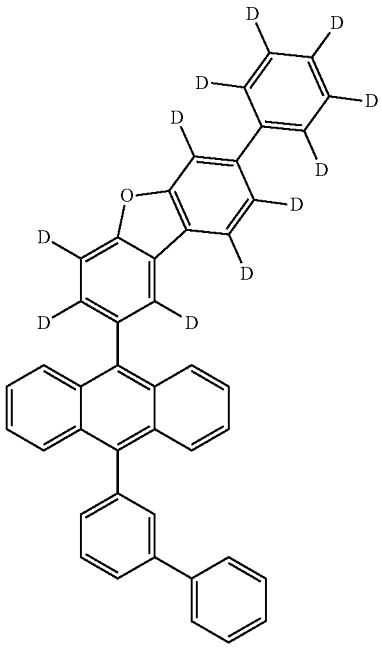
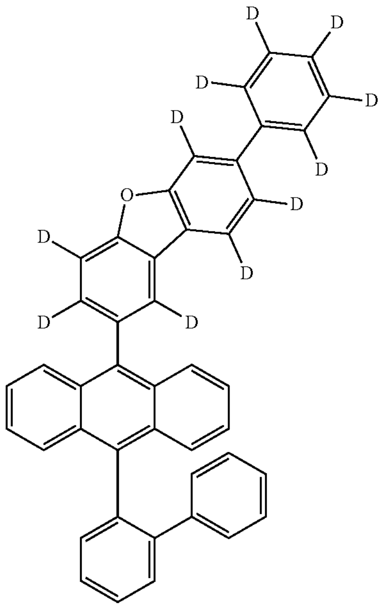

-continued
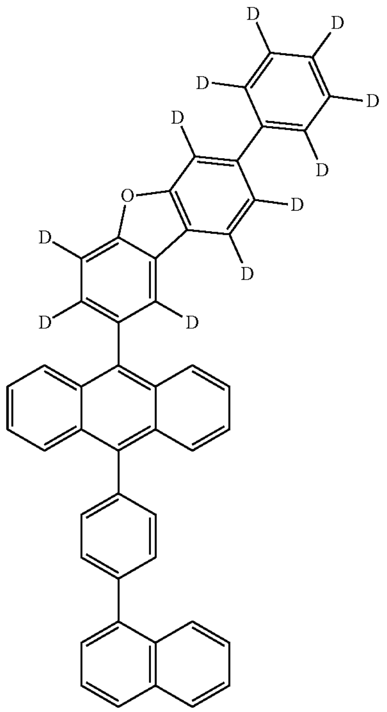
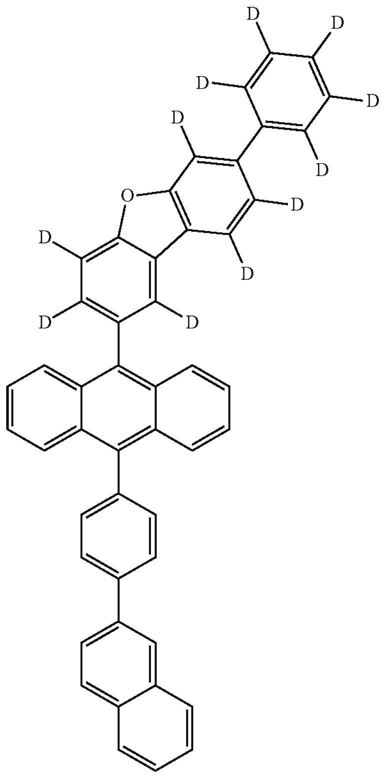
-continued
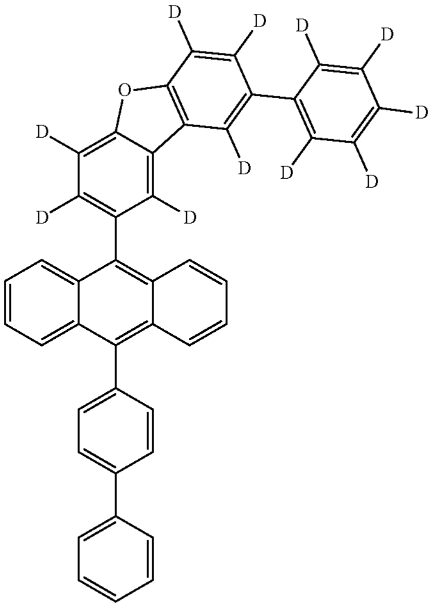
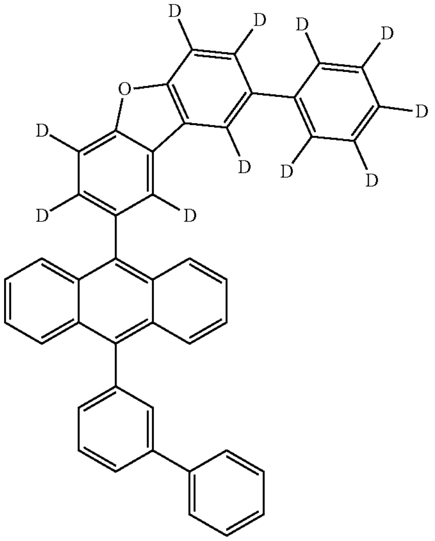
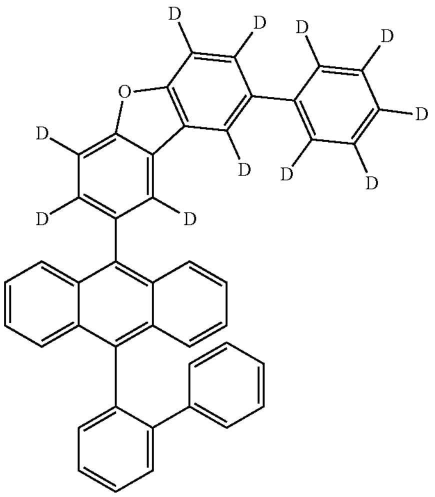

-continued
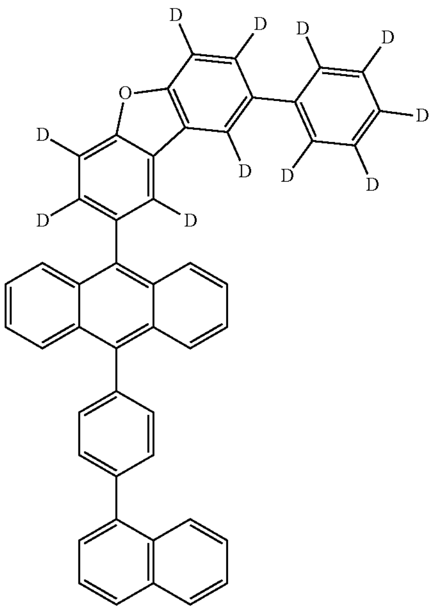
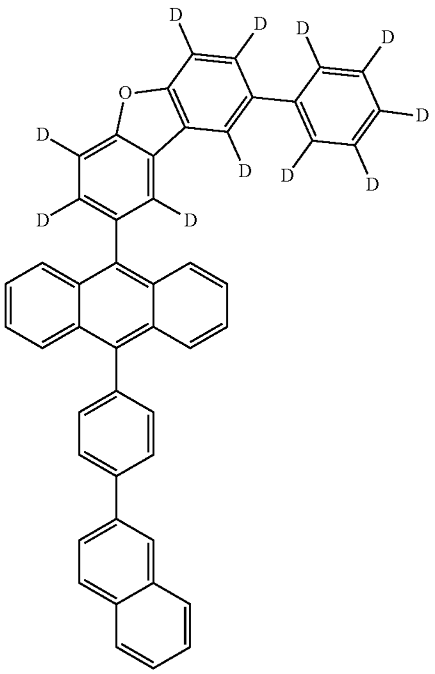
-continued
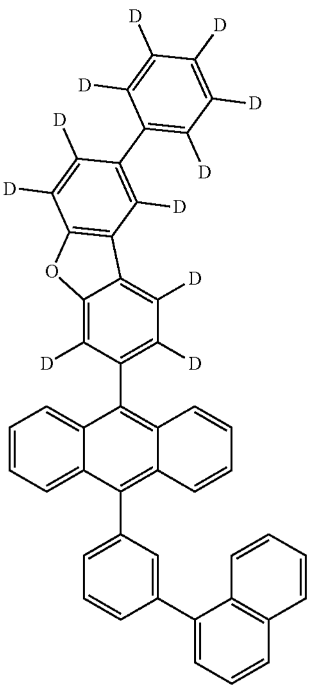
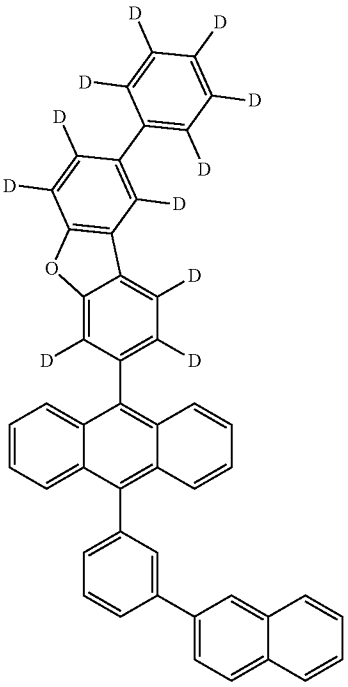

-continued
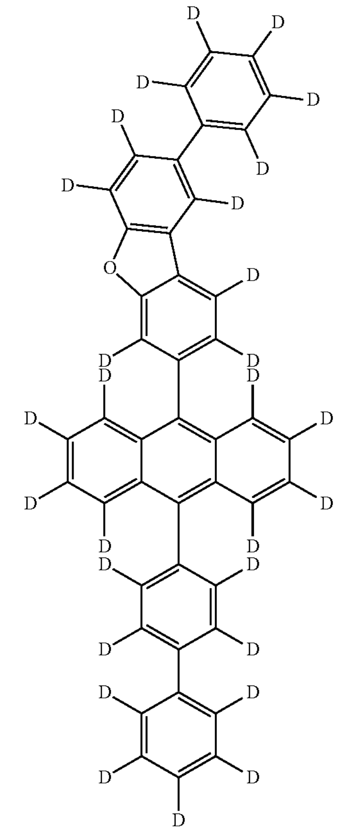
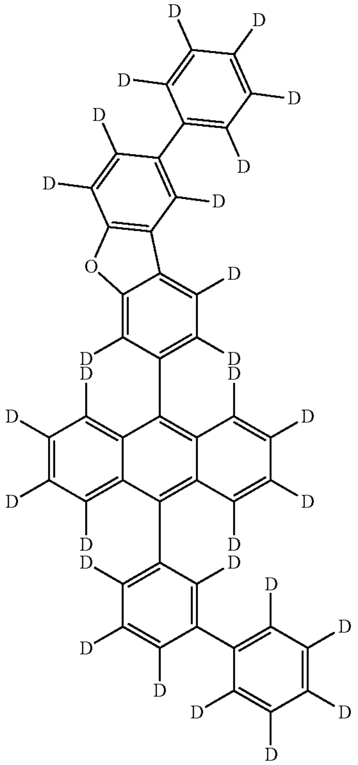
-continued
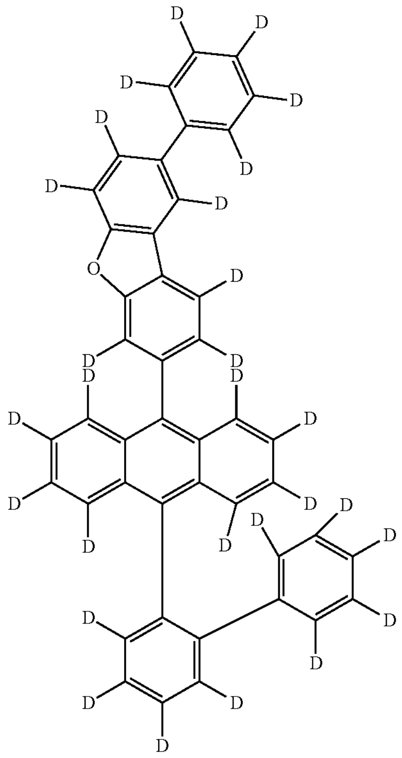
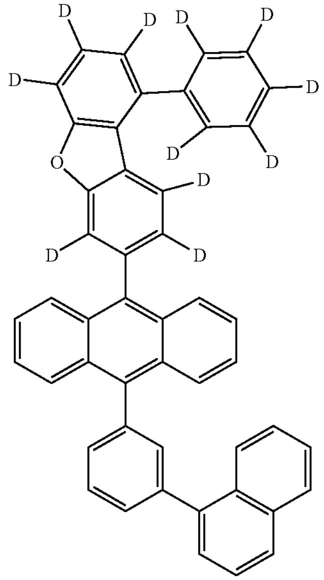

-continued
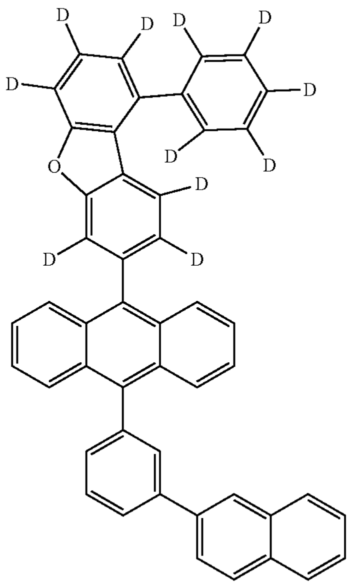
-continued
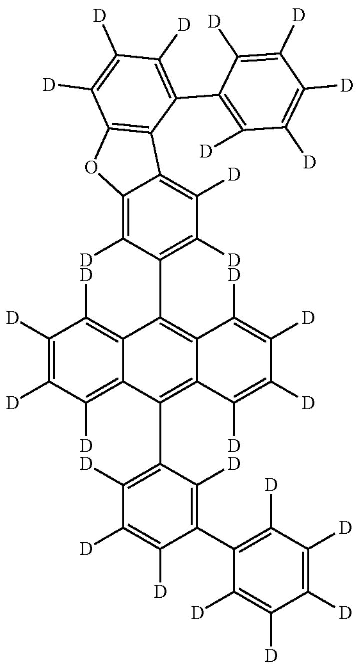
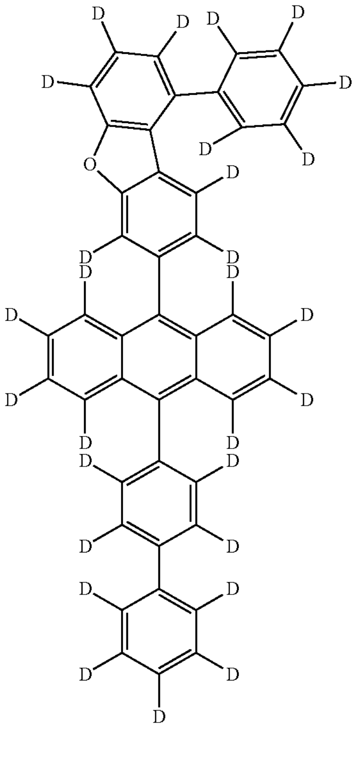
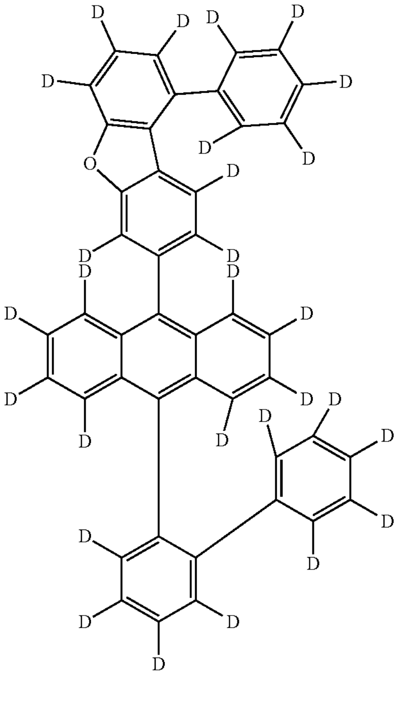

-continued
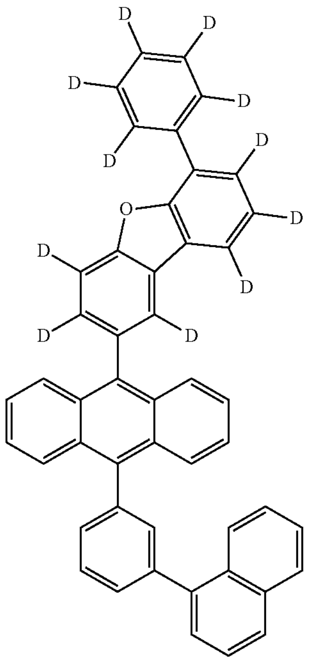
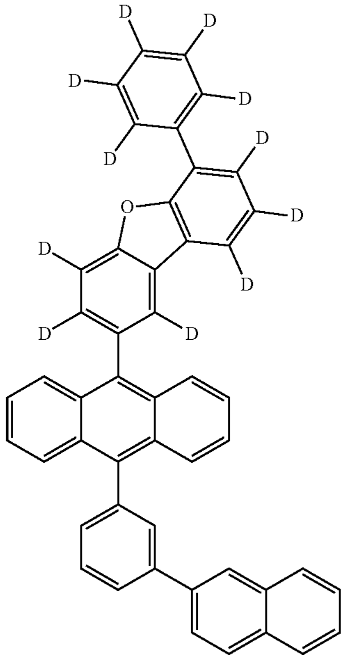
-continued
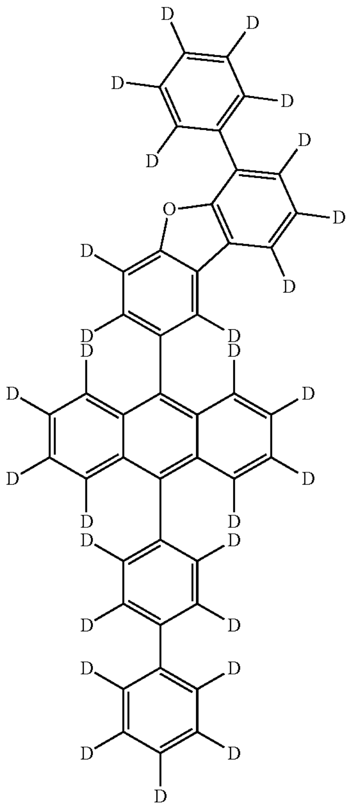
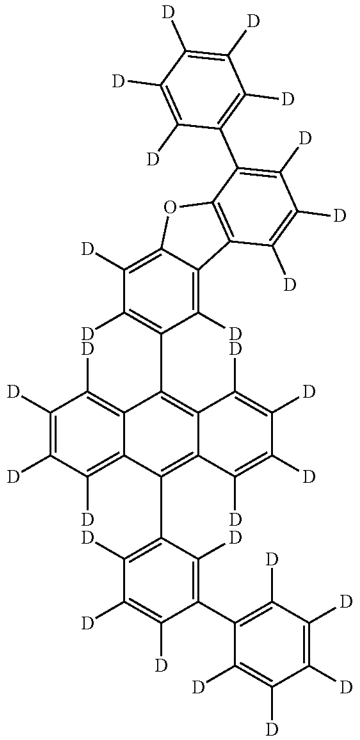

-continued
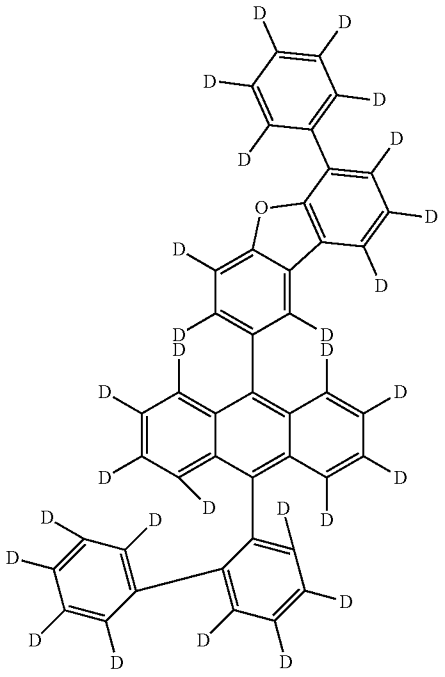
-continued
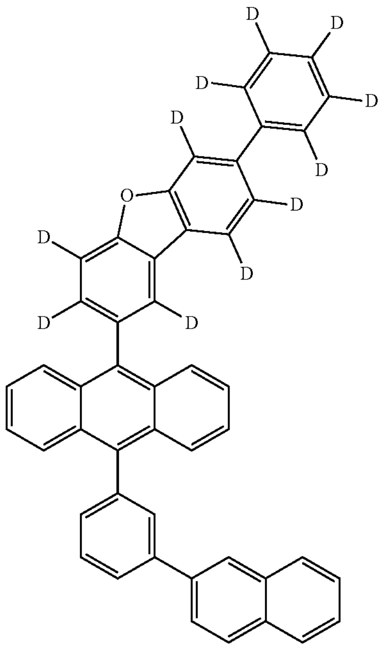
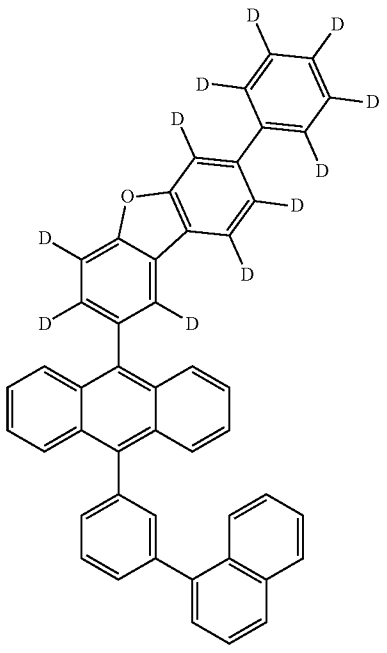
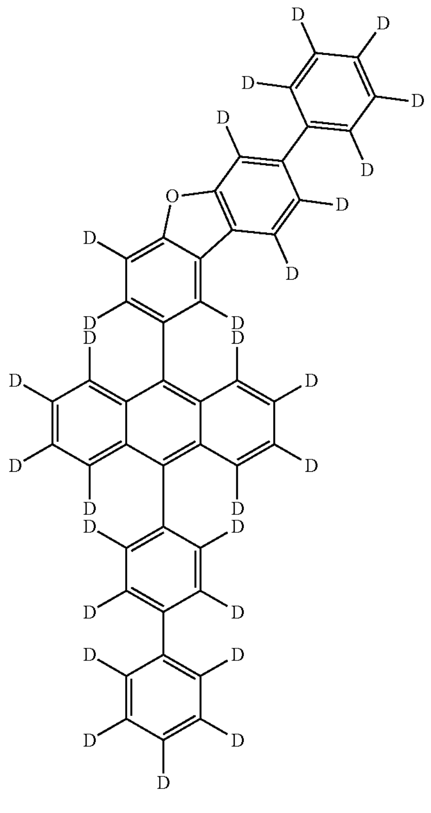

-continued
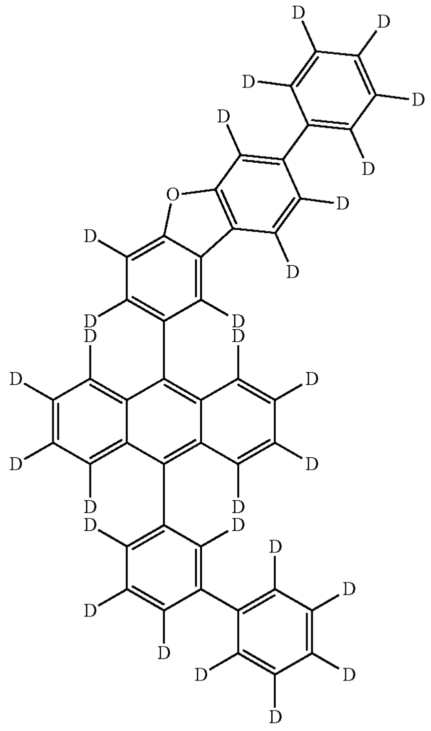
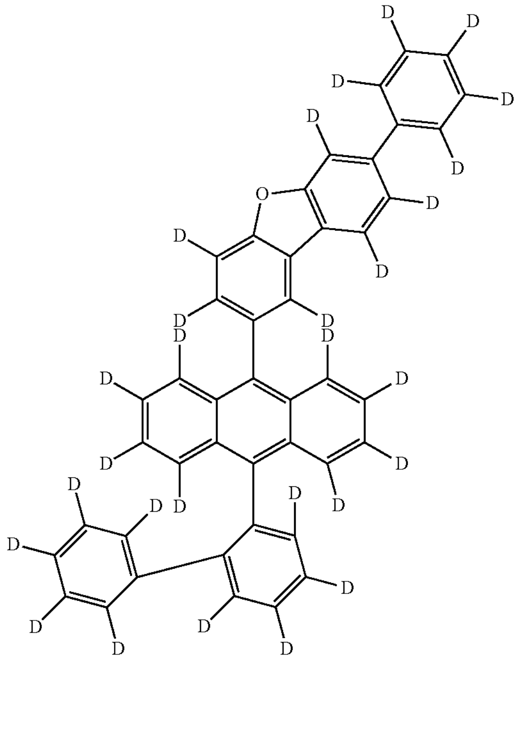
-continued
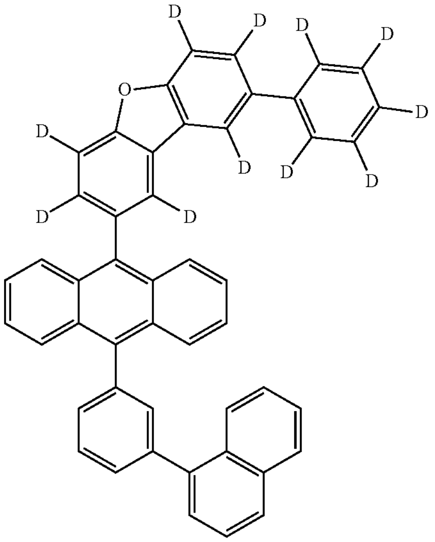
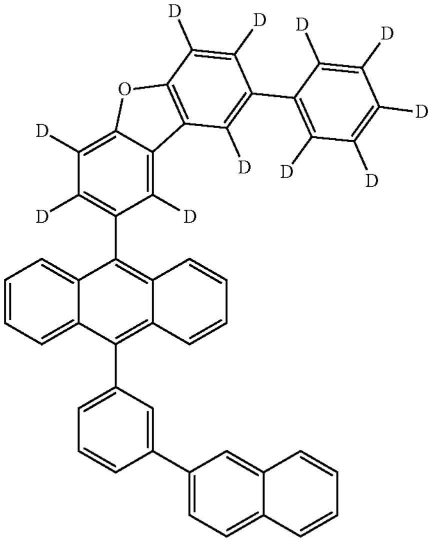

-continued
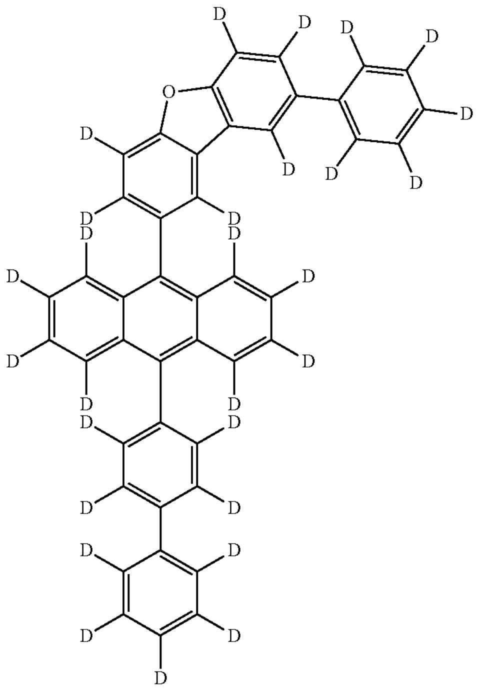
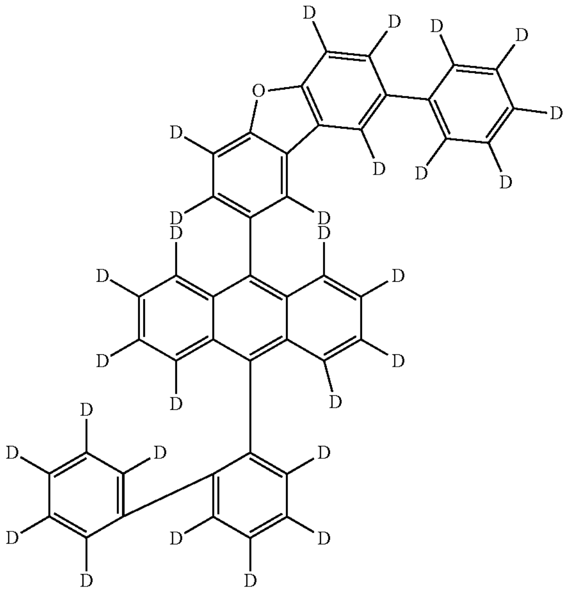
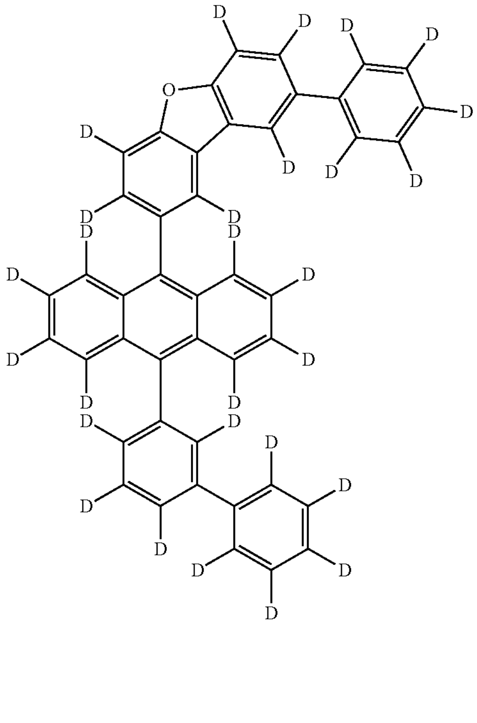
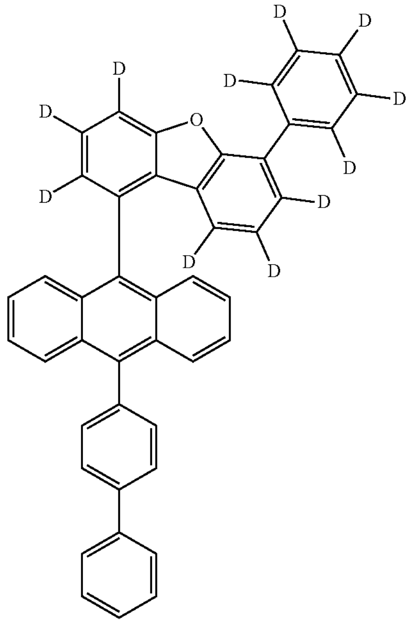
-continued

-continued
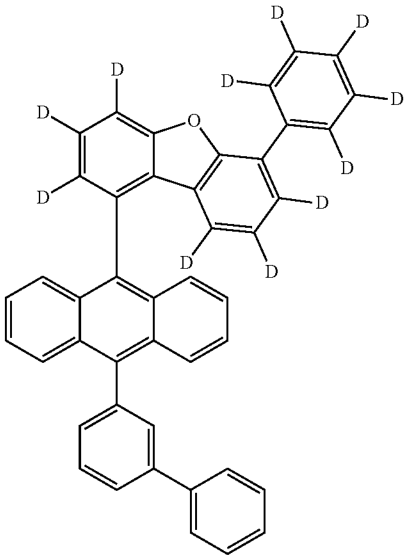
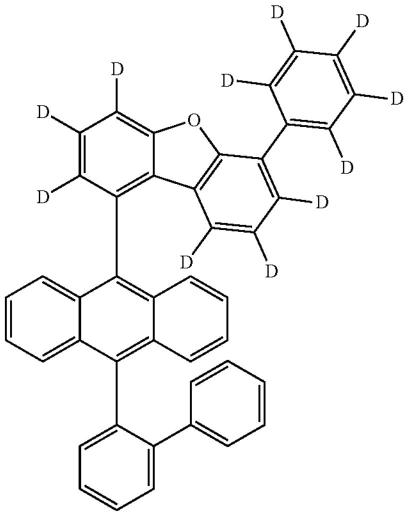
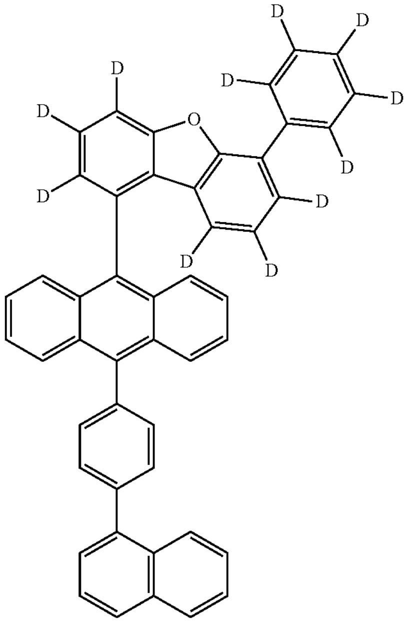
-continued
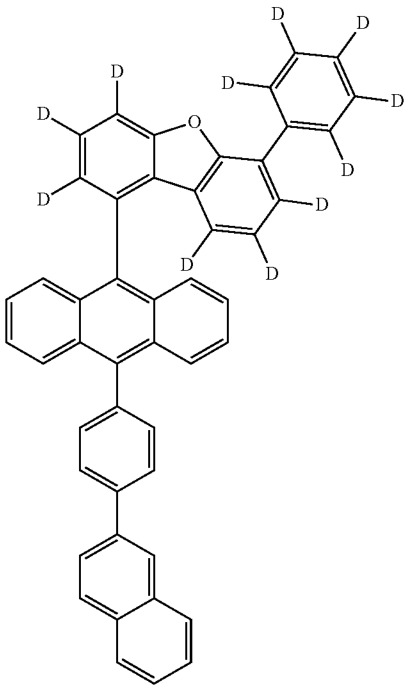
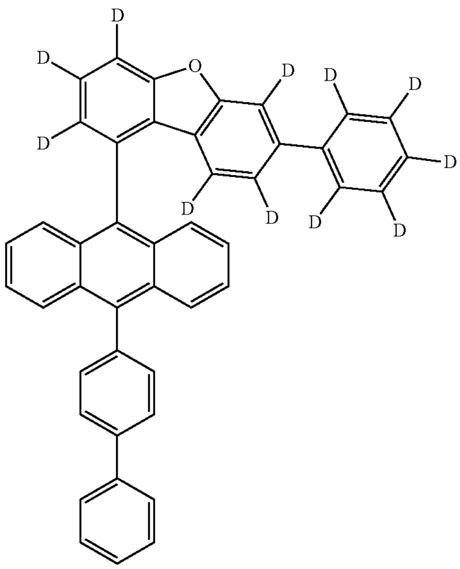

-continued
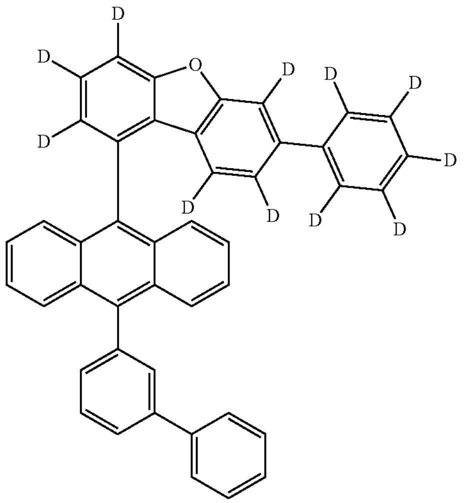
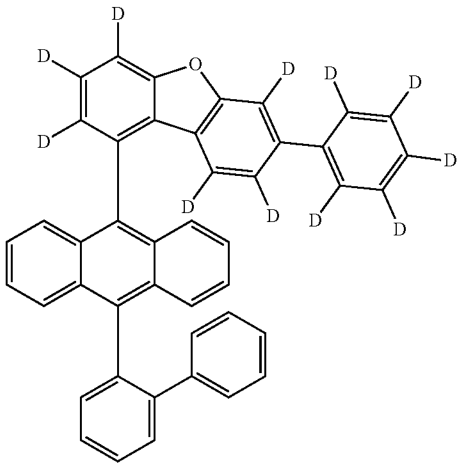
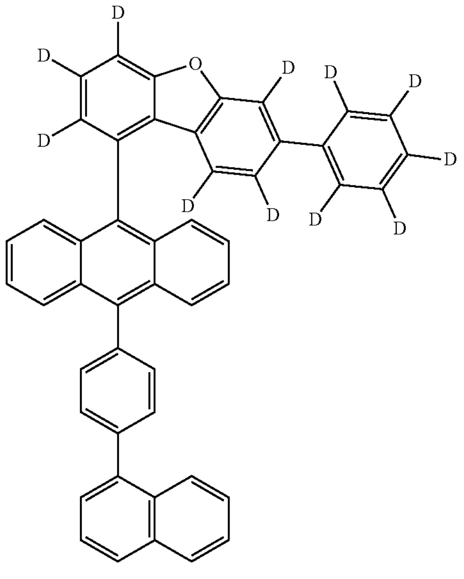
-continued
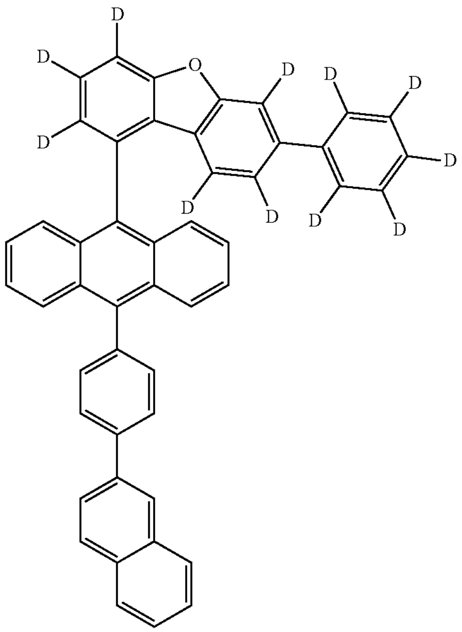
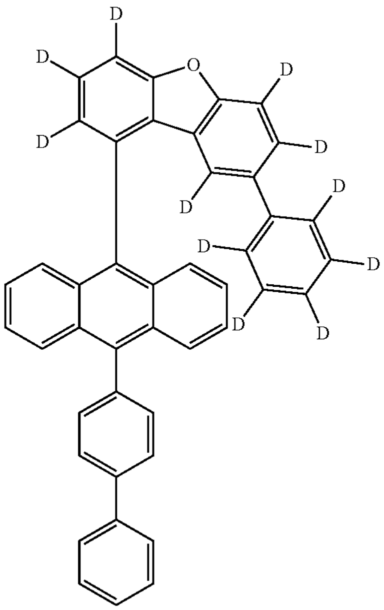

-continued
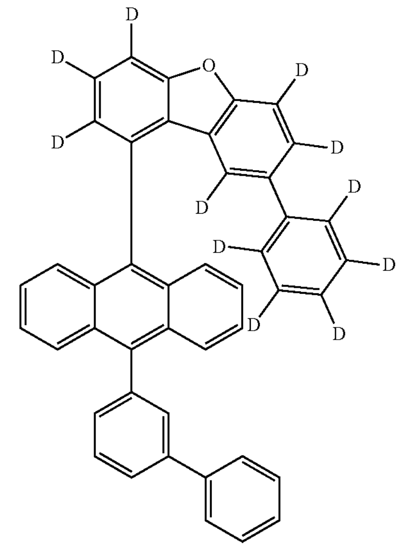
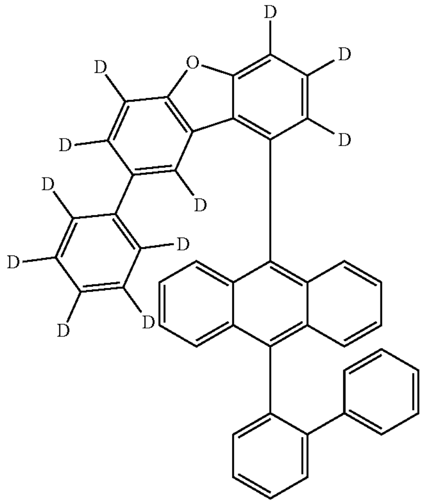
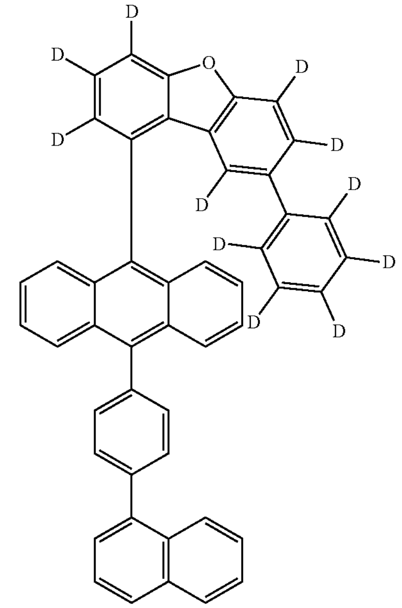
-continued
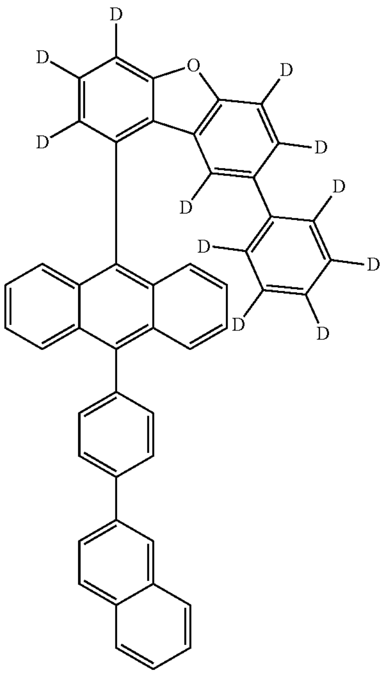
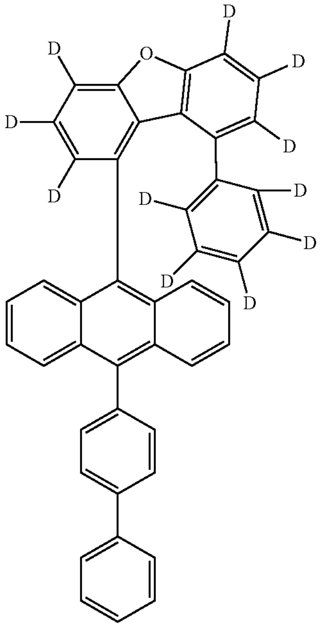

-continued
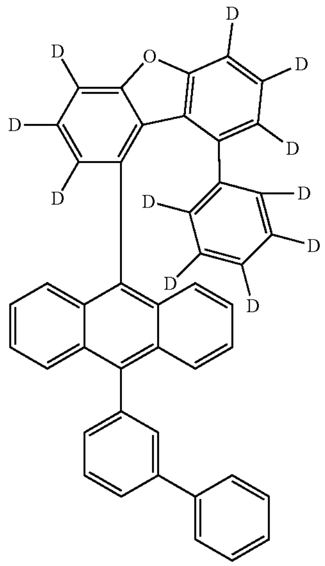
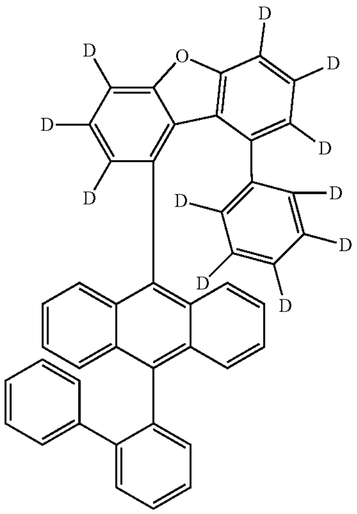
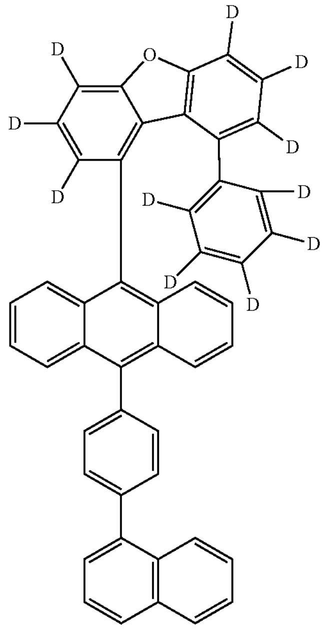
-continued
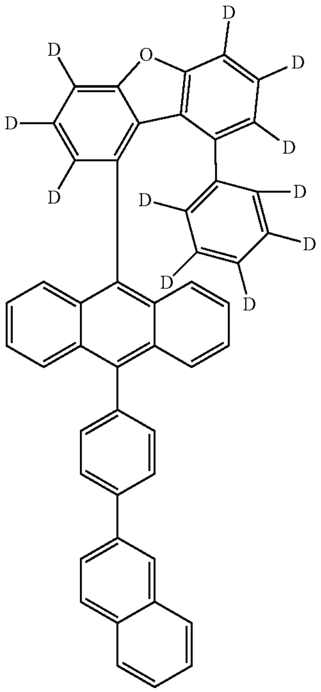
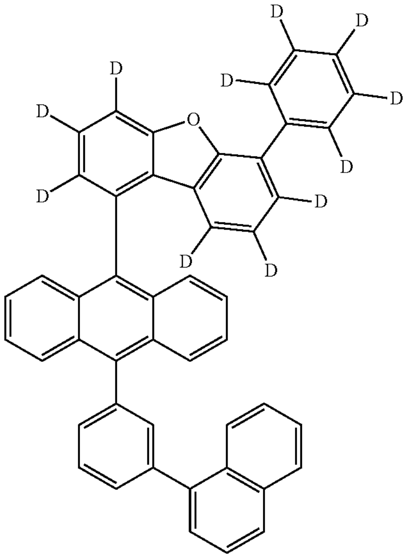

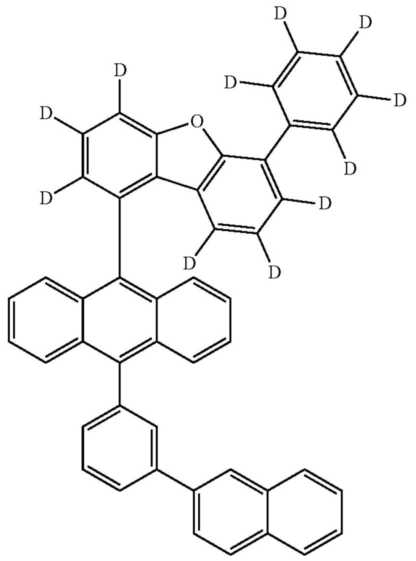
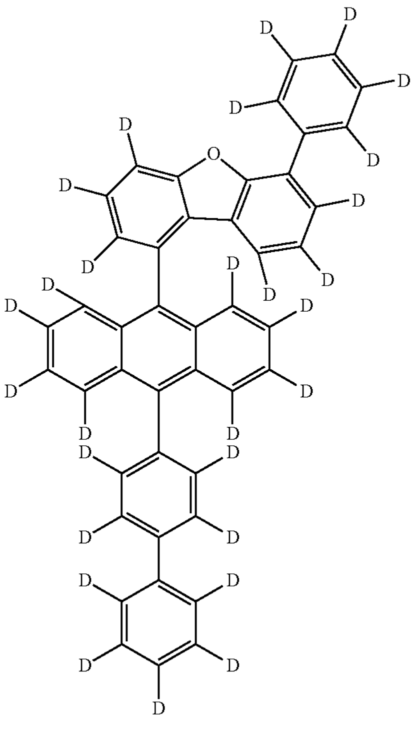
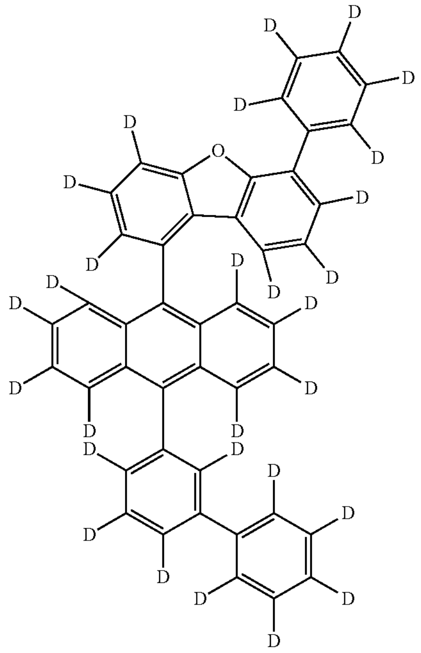
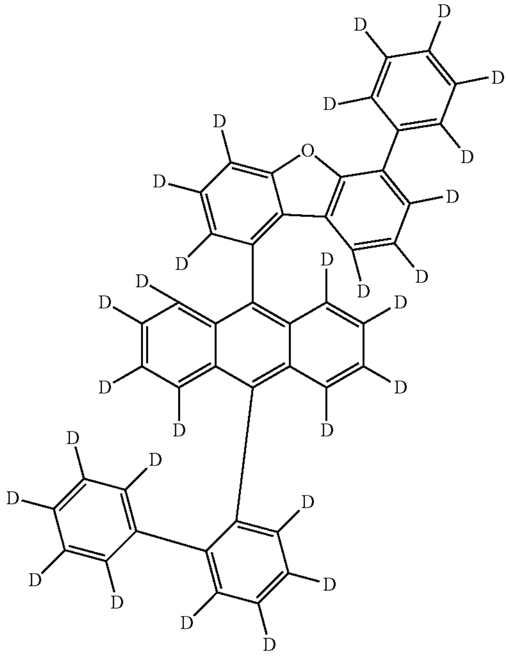

-continued
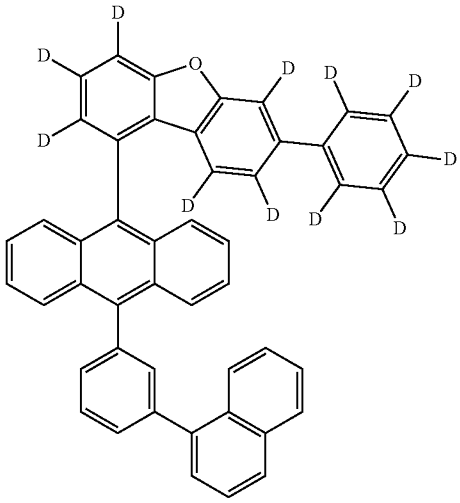
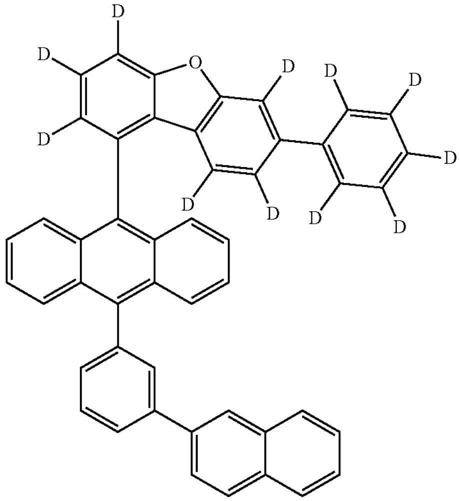
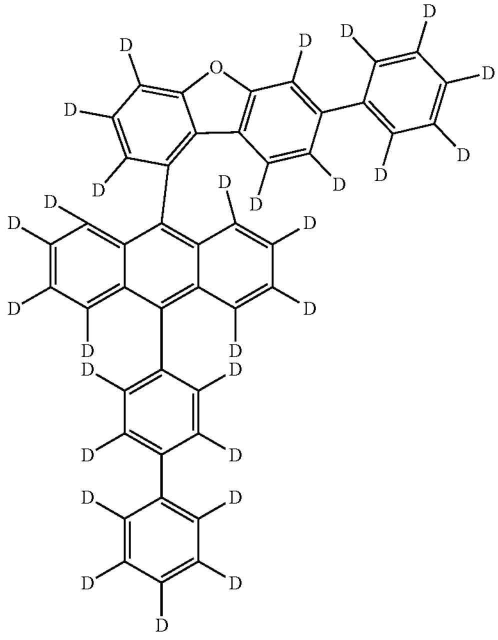
-continued
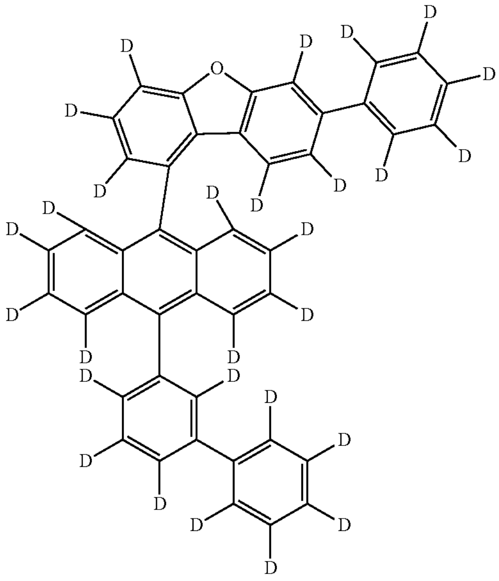
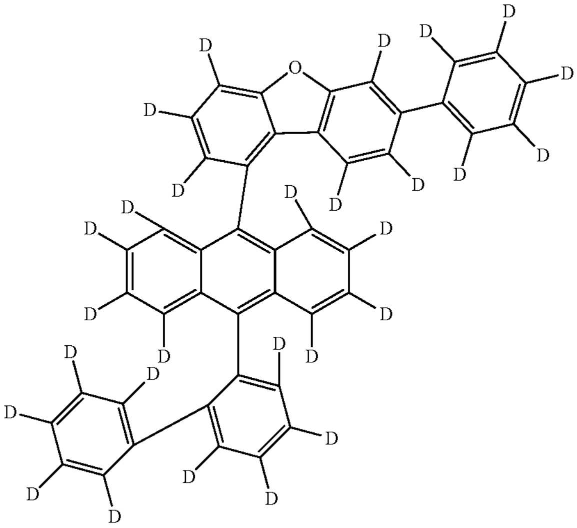
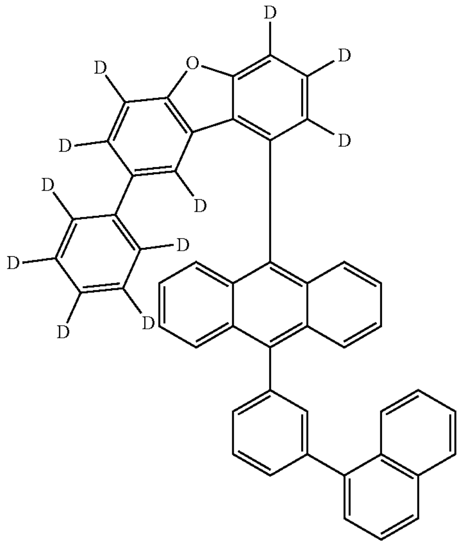

-continued
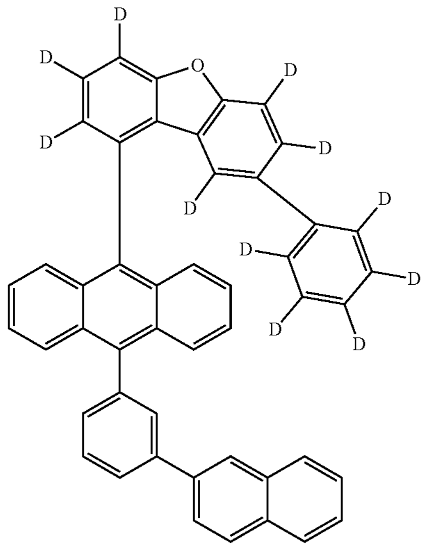
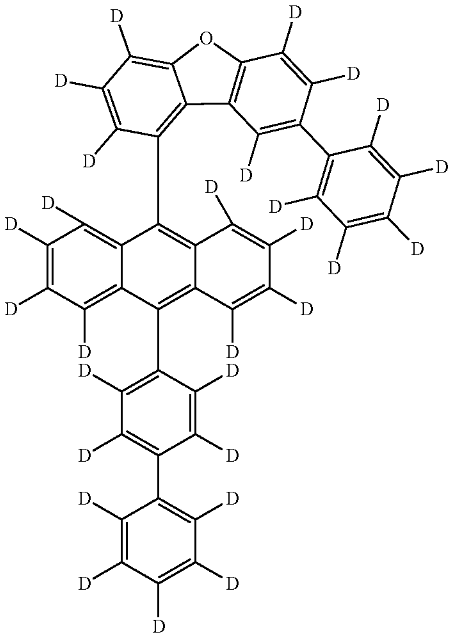
-continued
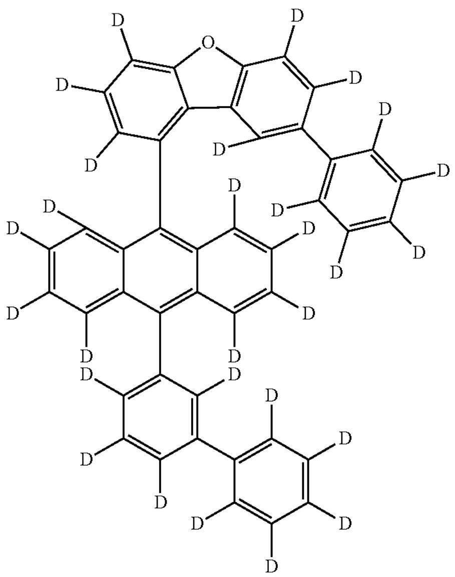
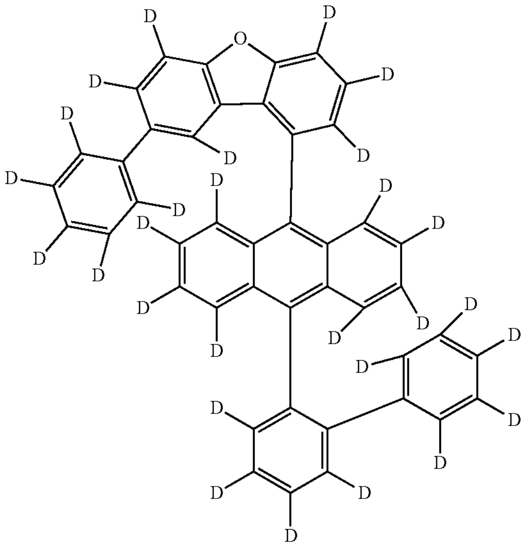
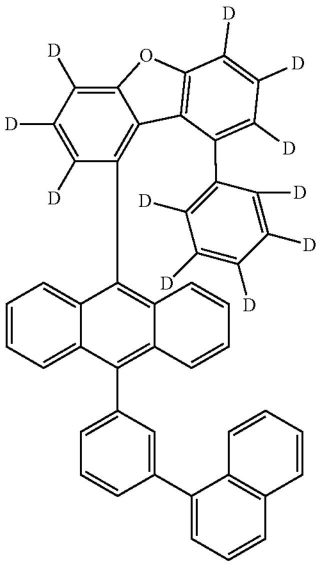

-continued
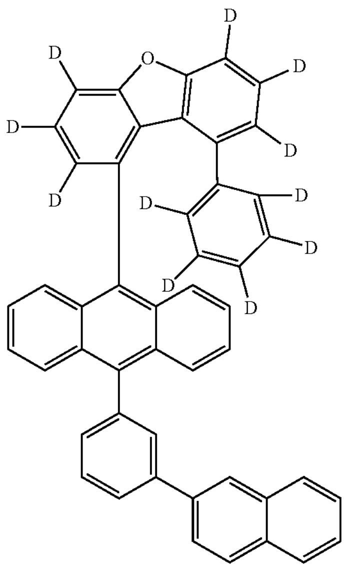
-continued
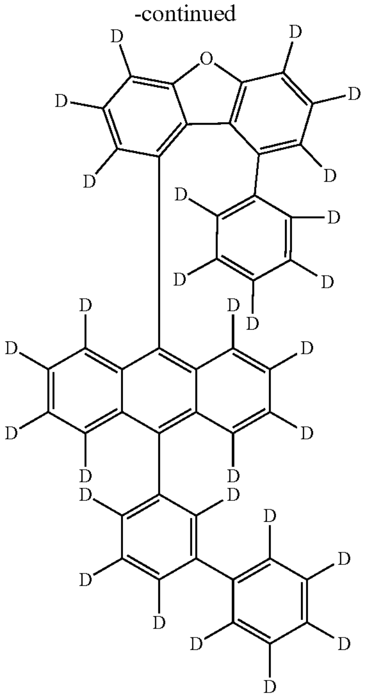
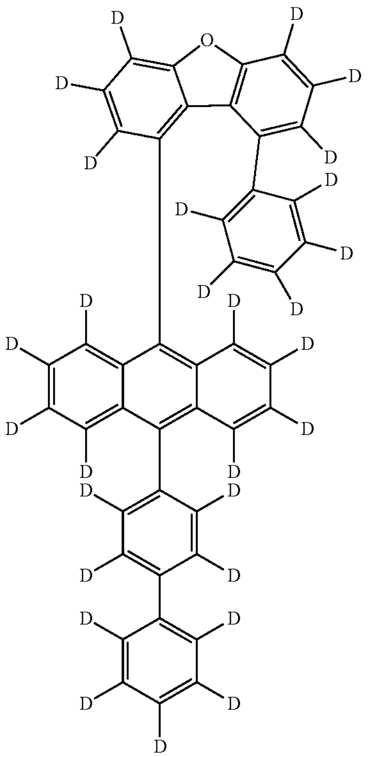
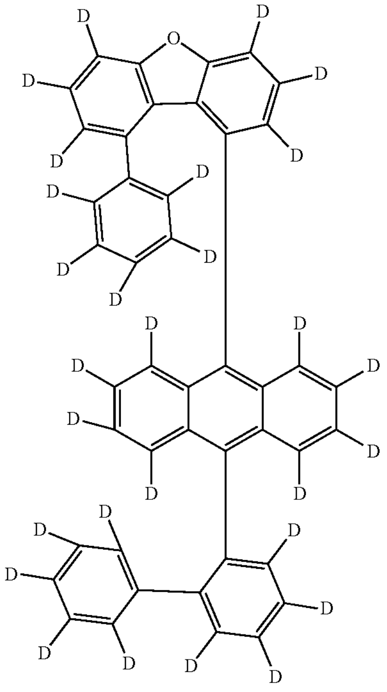 [SMILES: [2H]c1c([2H])c([2H])c(-c2c([2H])c([2H])c([2H])c([2H])c2-c2c3c([2H])c([2H])c([2H])c([2H])c3c(-c3c([2H])c([2H])c([2H])c4oc5c([2H])c([2H])c([2H])c(-c6c([2H])c([2H])c([2H])c([2H])c6[2H])c5c34)c3c([2H])c([2H])c([2H])c([2H])c23)c([2H])c1[2H]]

-continued
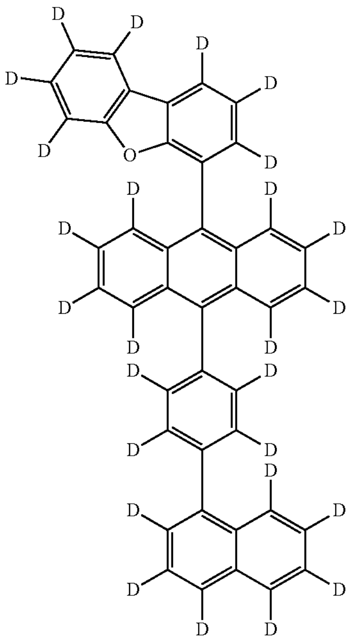
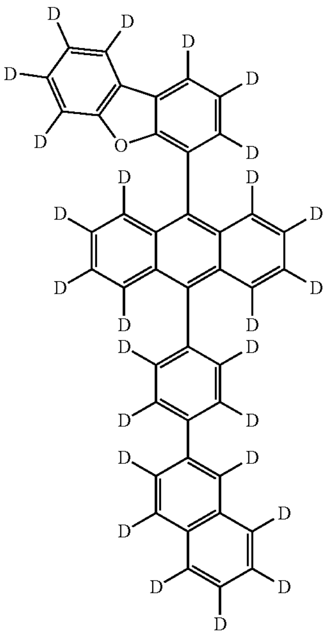
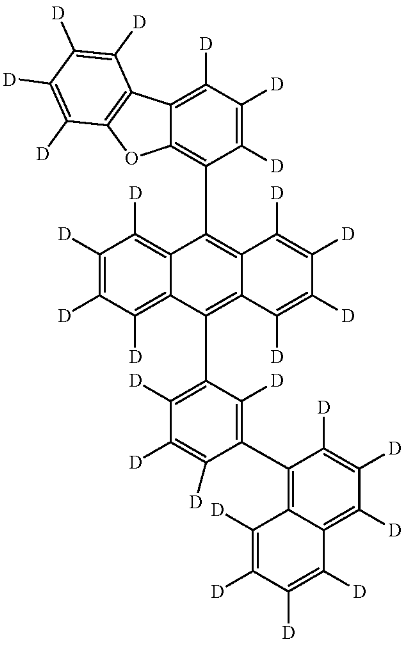
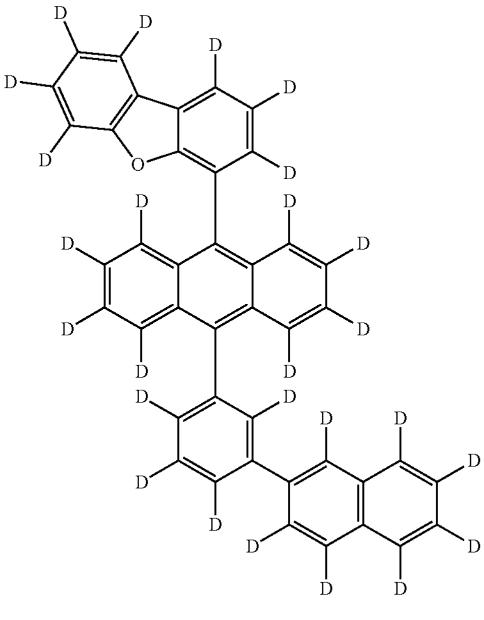

-continued
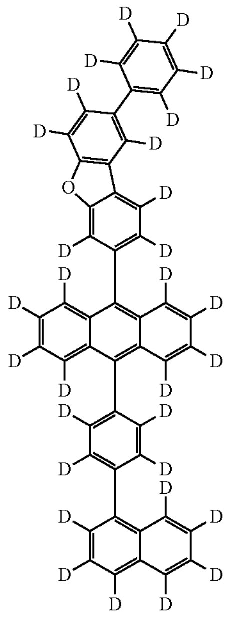
-continued
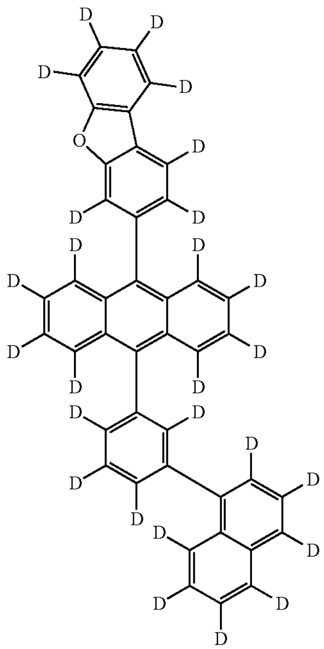
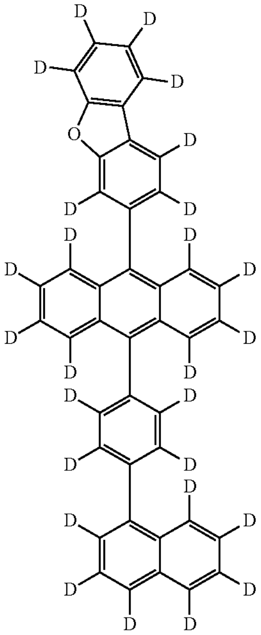
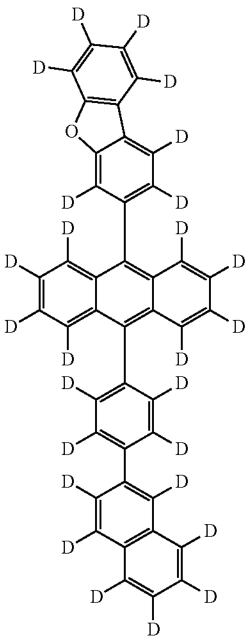

-continued
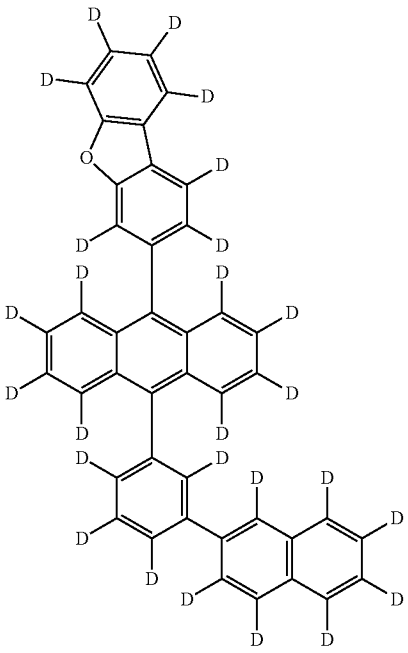
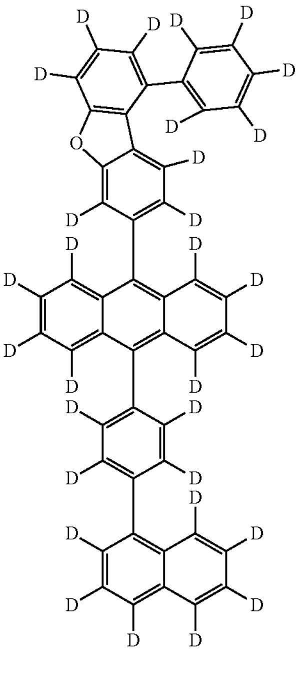
-continued
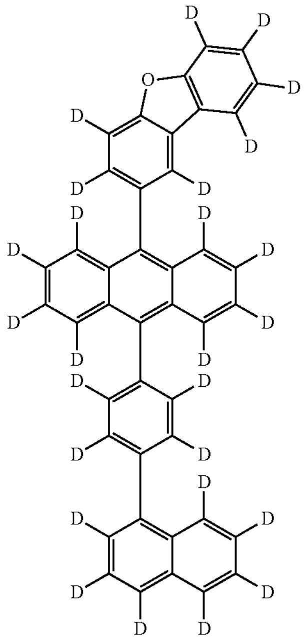
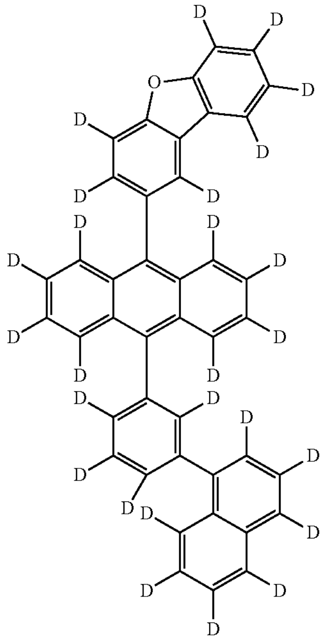

-continued
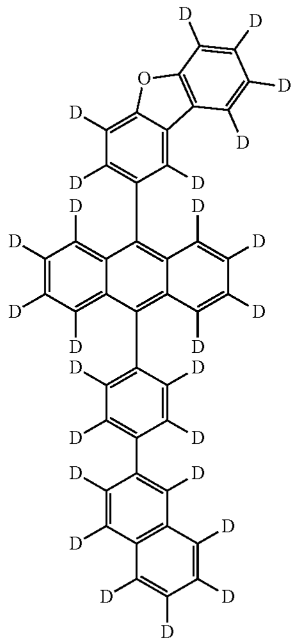
-continued
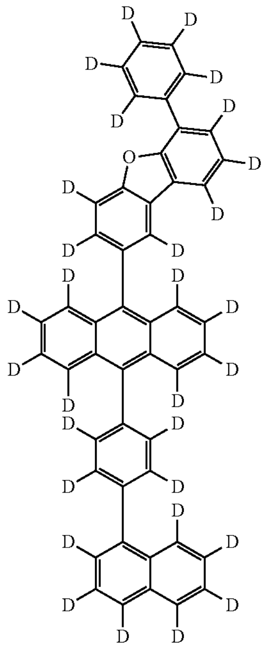
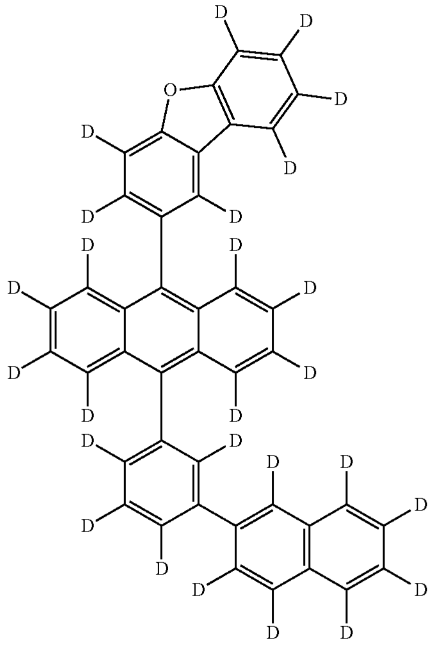
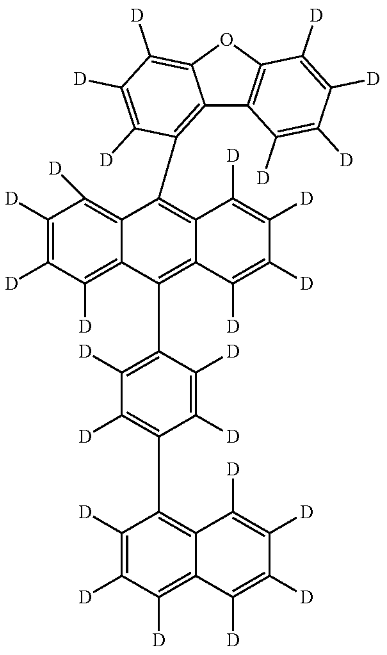

-continued
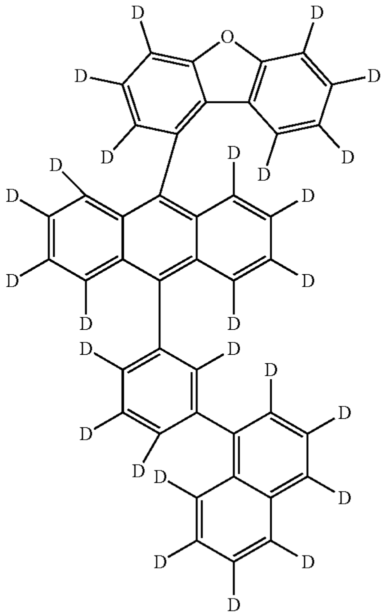
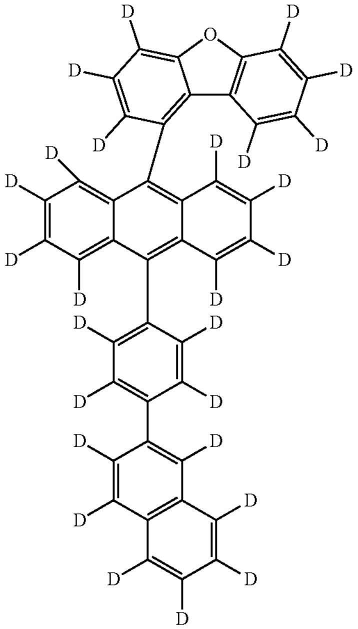
-continued
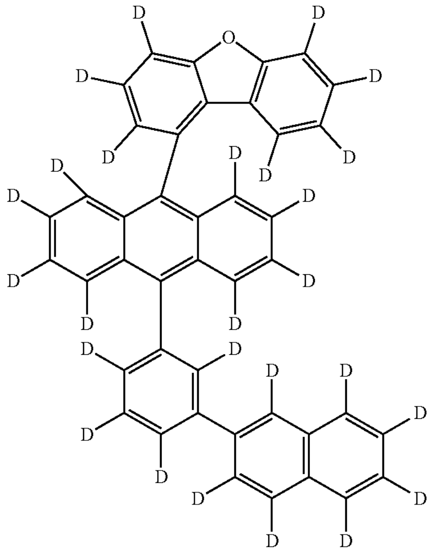
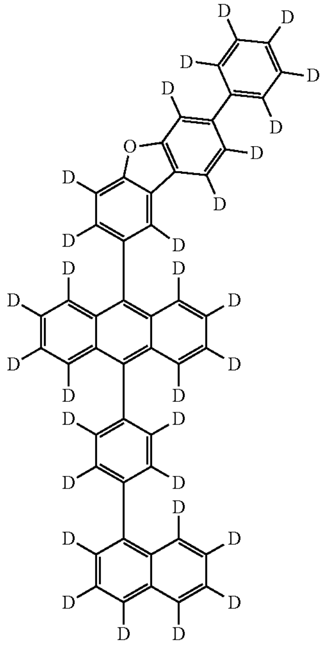

-continued
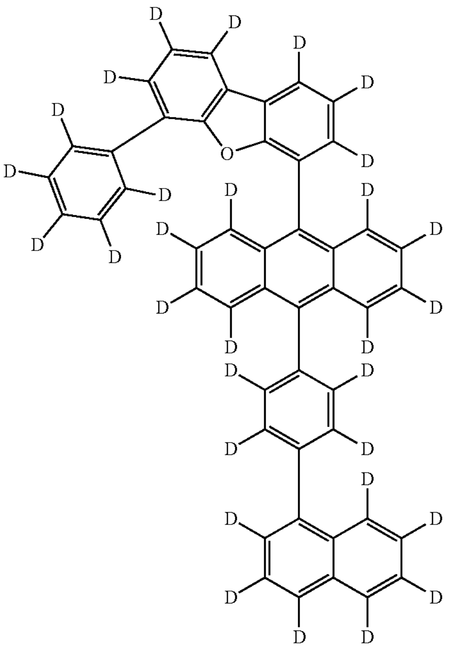
-continued
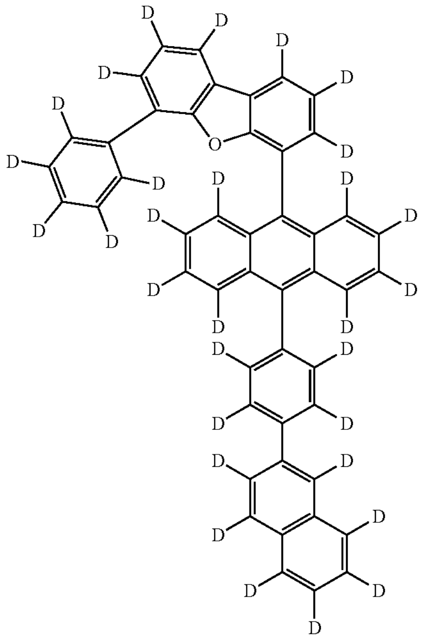
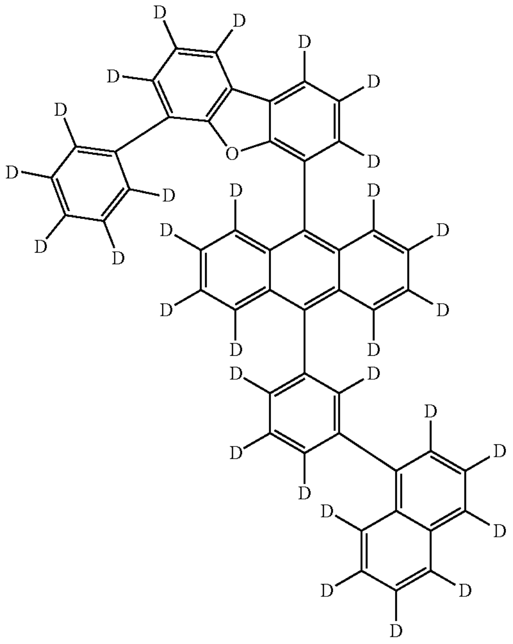
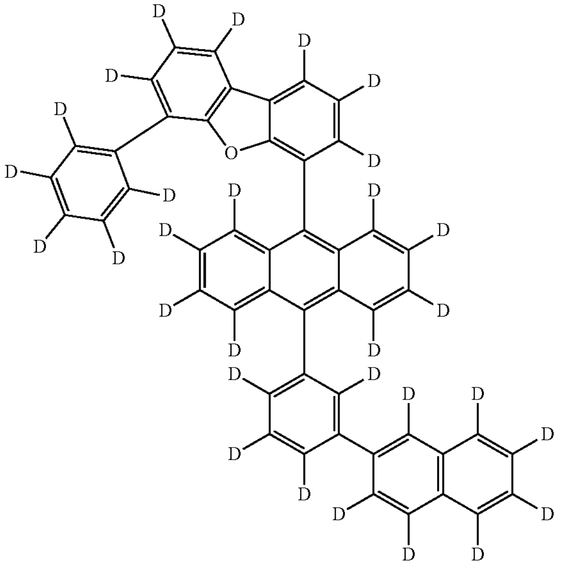

-continued
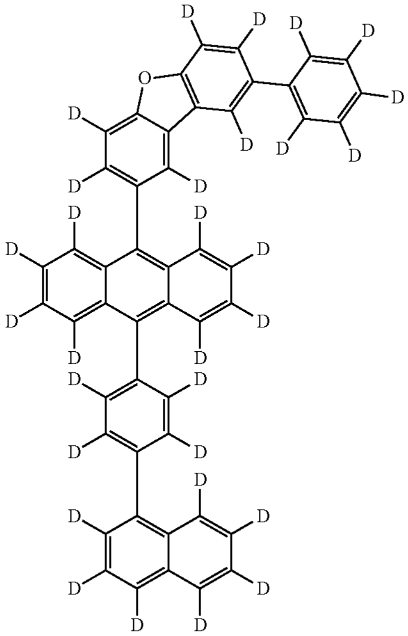
-continued
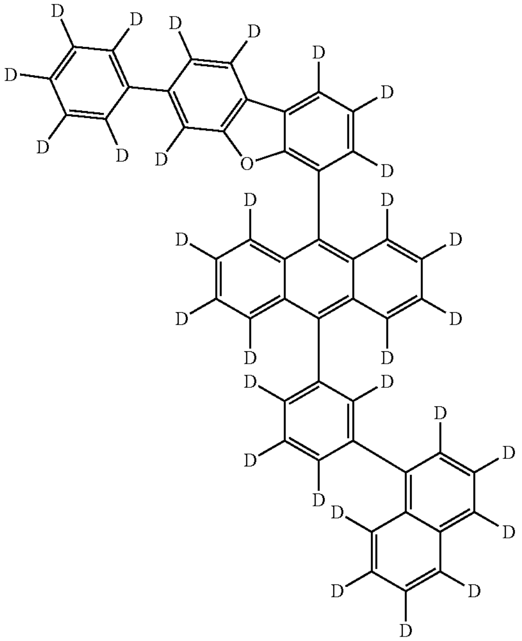
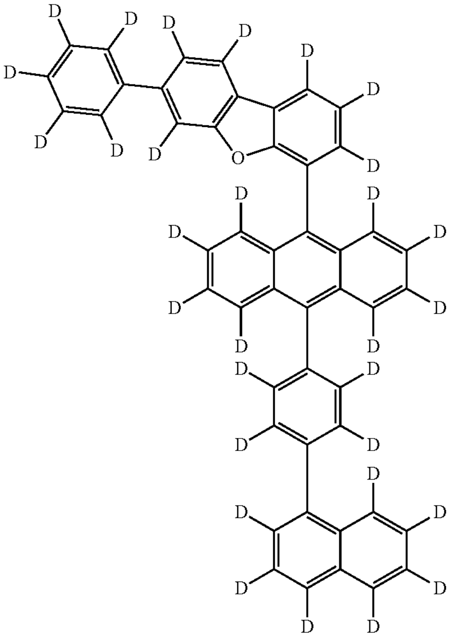
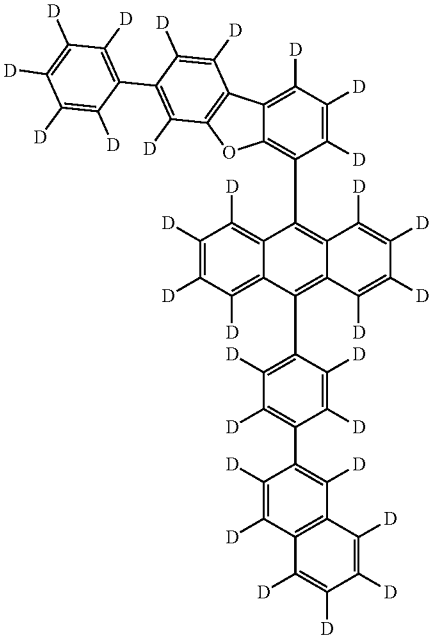

-continued
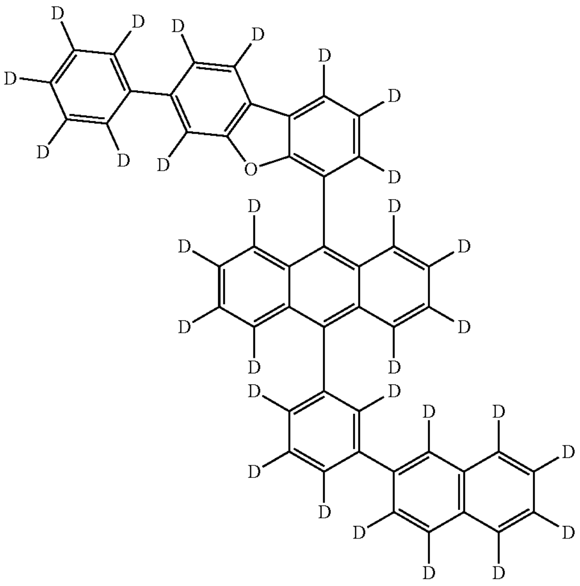
-continued
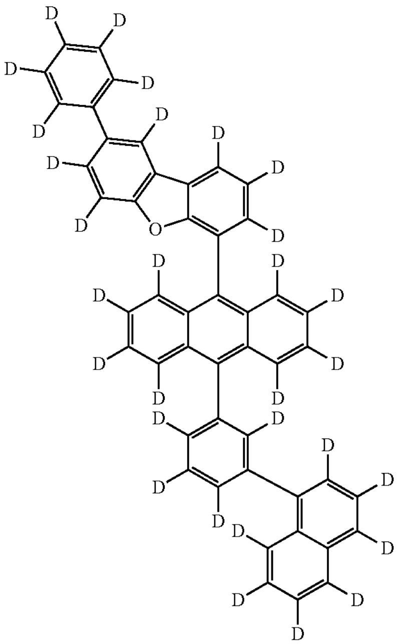
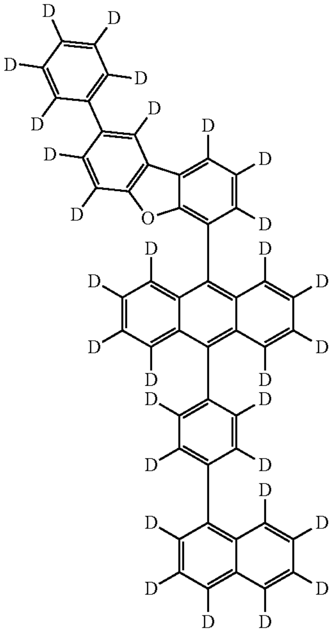
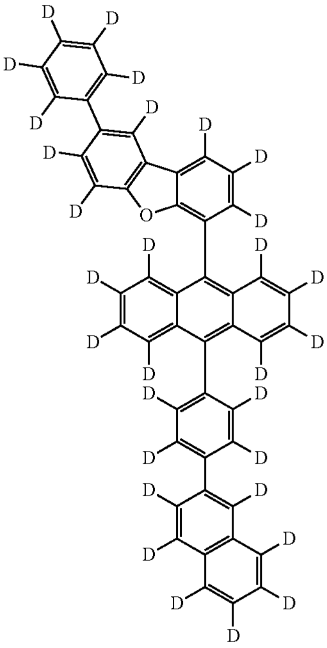

-continued
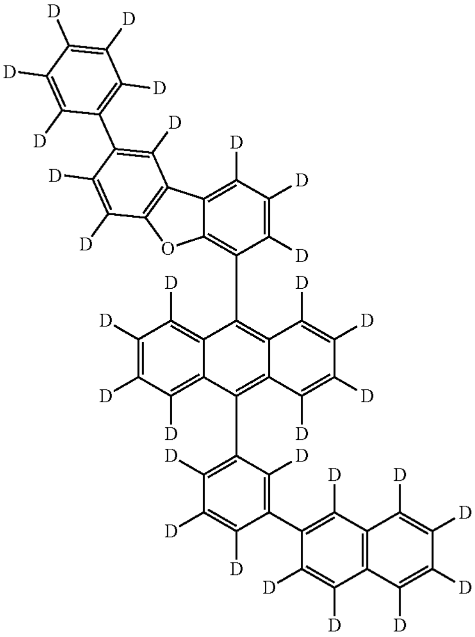
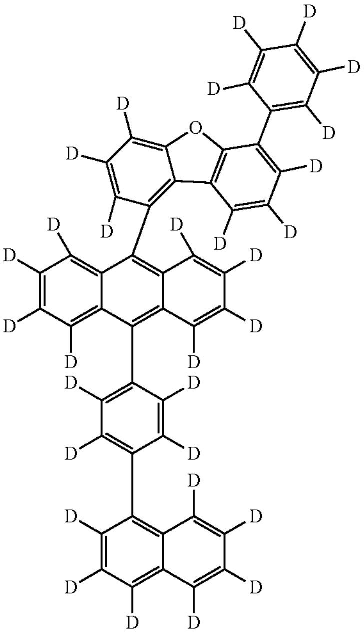
-continued
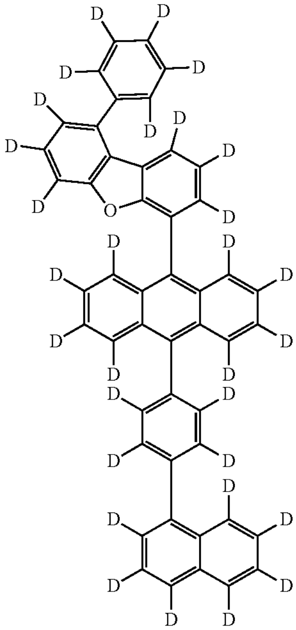
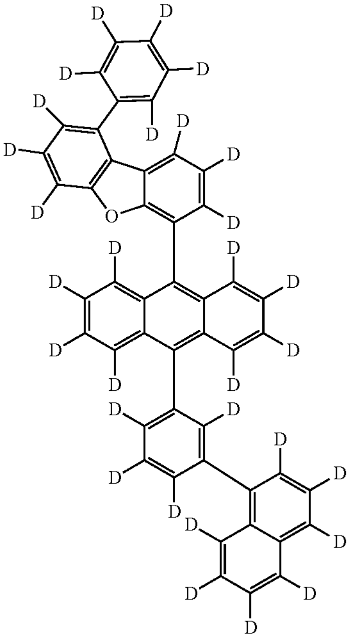

-continued
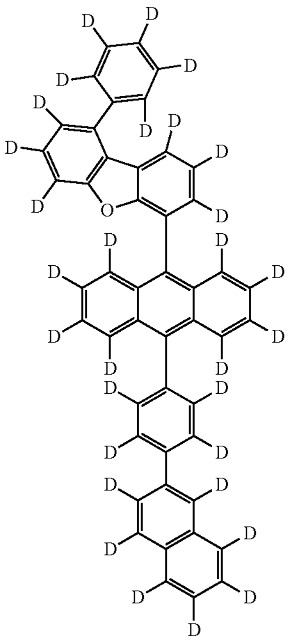
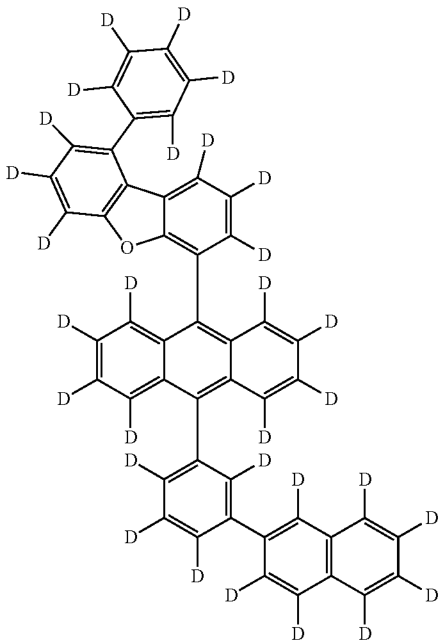
-continued
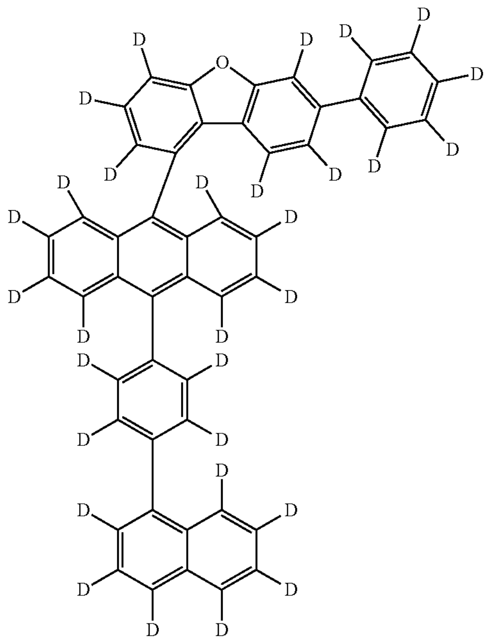
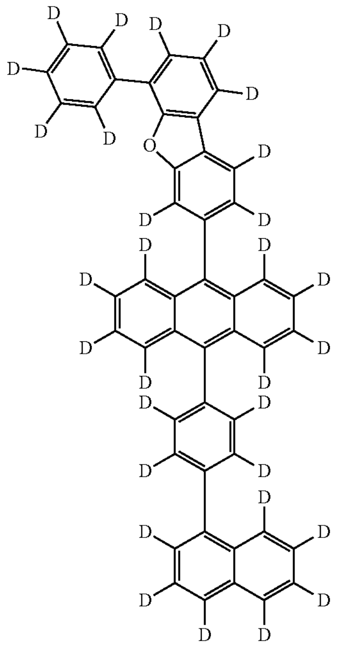

-continued
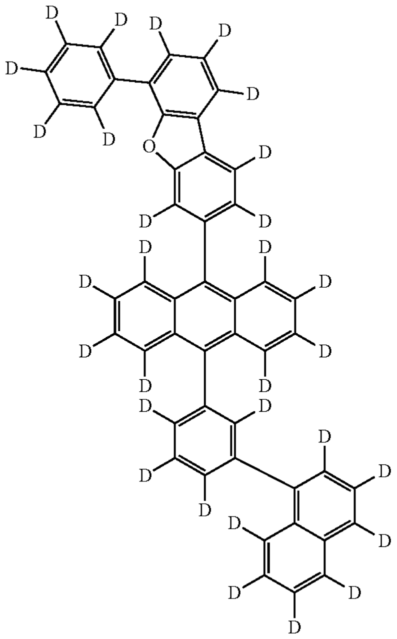
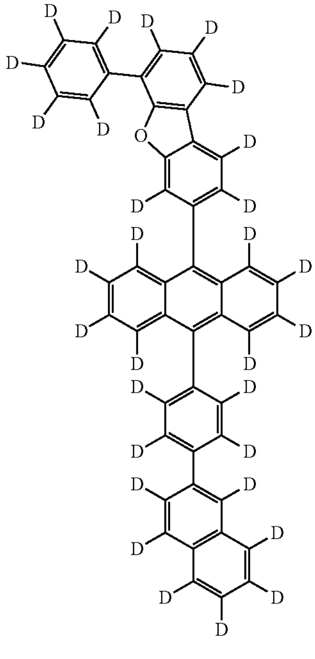
-continued
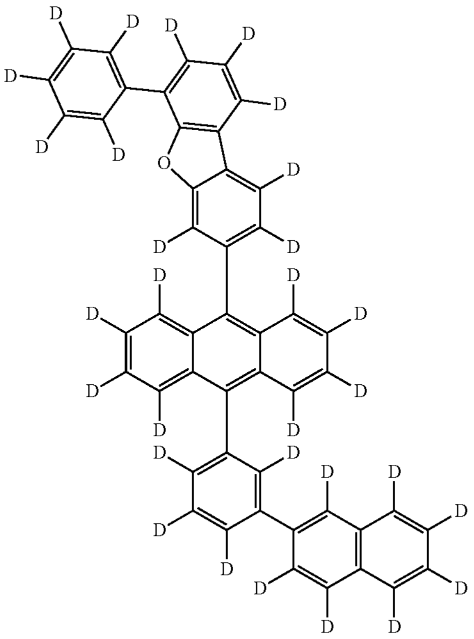
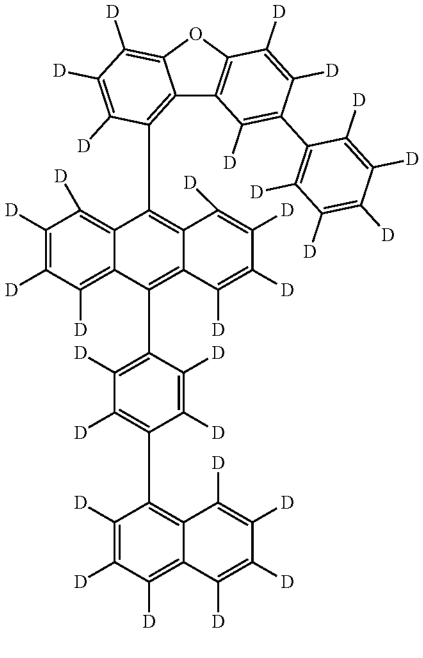

-continued
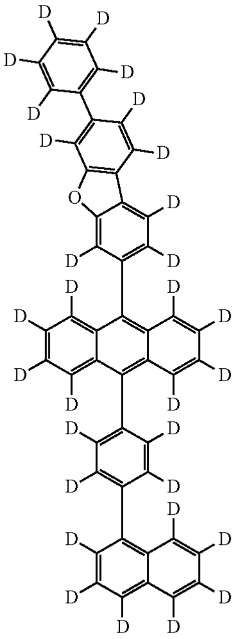
-continued
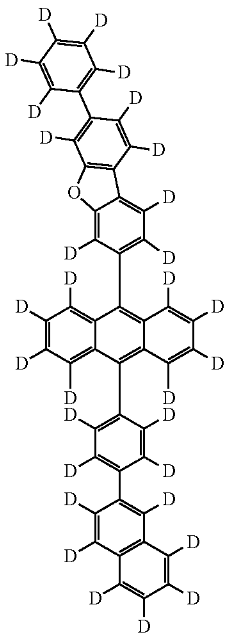
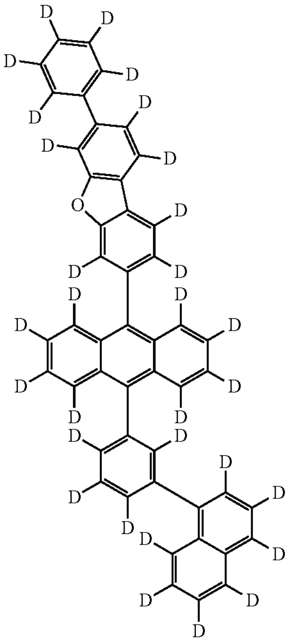
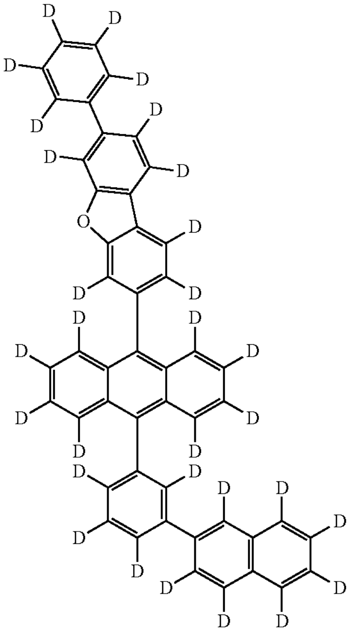

-continued
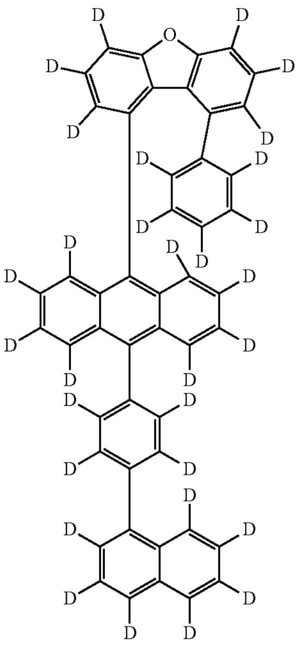 [SMILES: [2H]c1c([2H])c([2H])c(-c2c([2H])c([2H])c([2H])c3oc4c([2H])c([2H])c([2H])c(-c5c6c([2H])c([2H])c([2H])c([2H])c6c(-c6c([2H])c([2H])c(-c7c([2H])c([2H])c([2H])c8c([2H])c([2H])c([2H])c([2H])c78)c([2H])c6[2H])c6c([2H])c([2H])c([2H])c([2H])c56)c4c23)c([2H])c1[2H]]
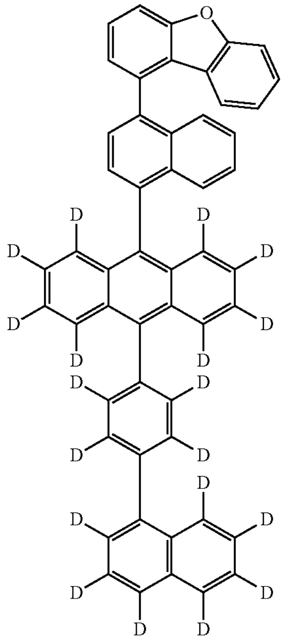
-continued
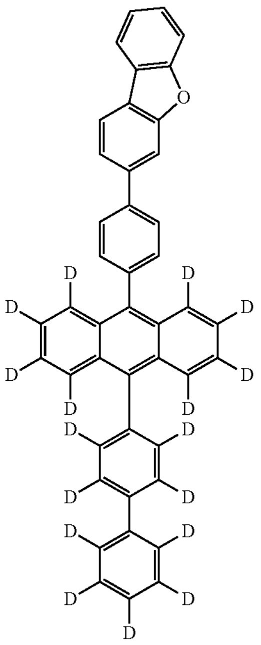
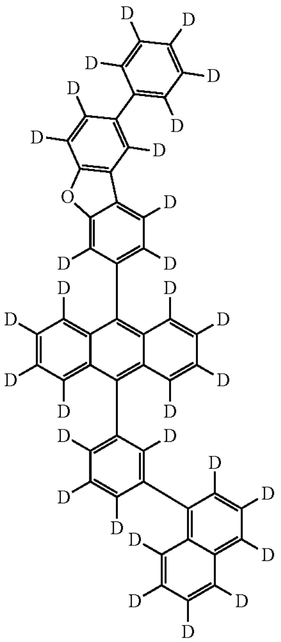

-continued
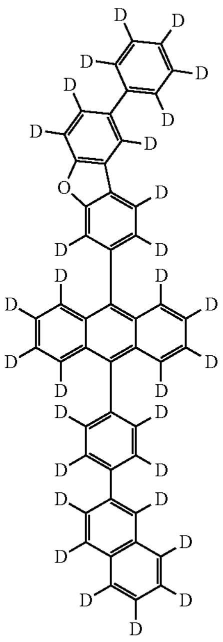
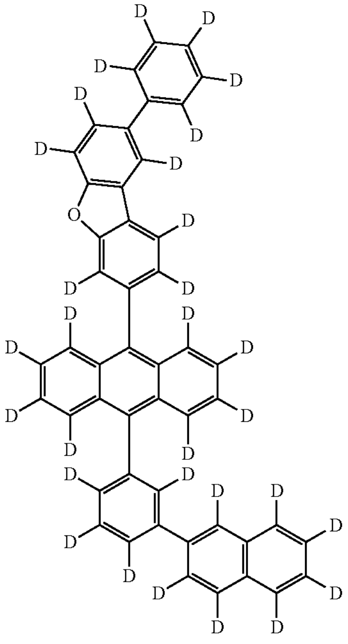
-continued
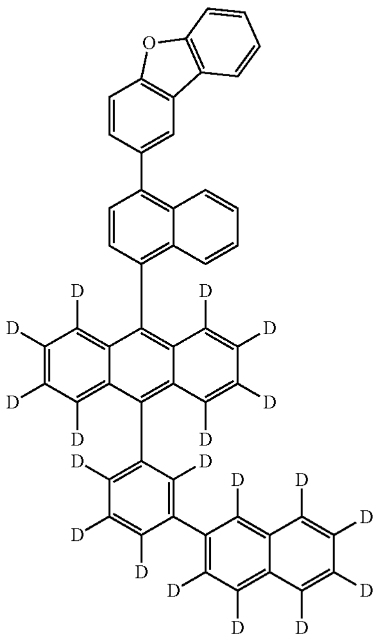
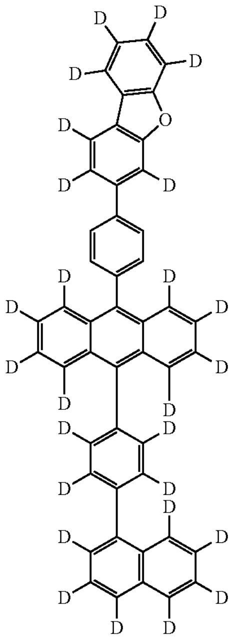

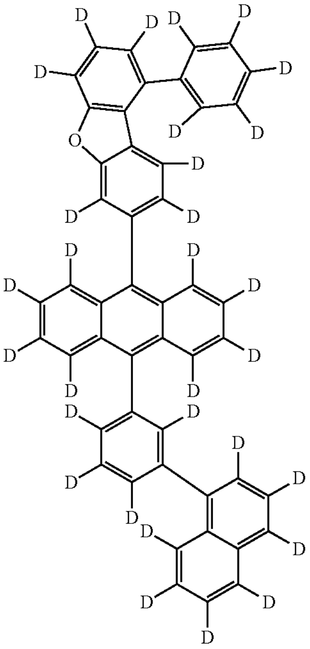
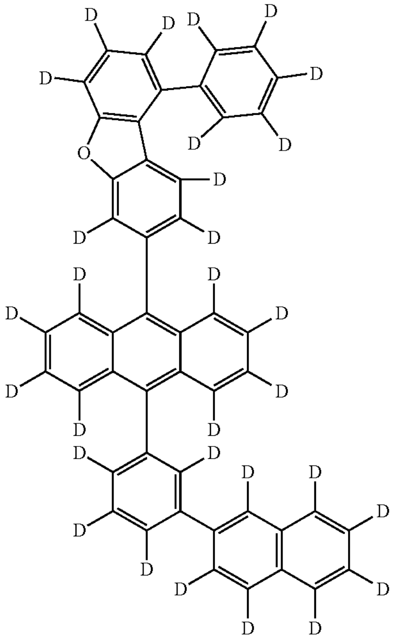
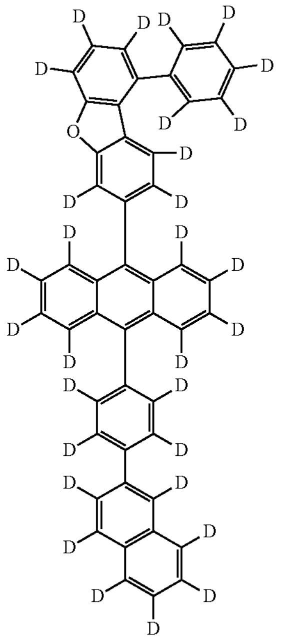
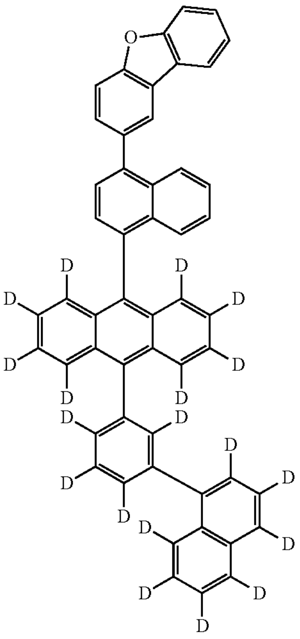

-continued
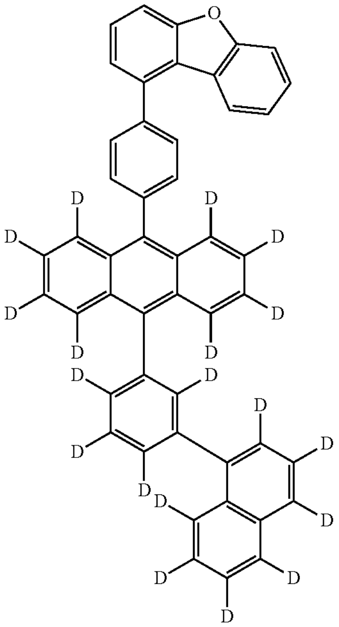
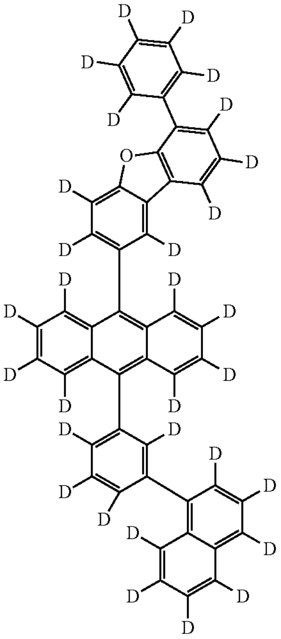
-continued
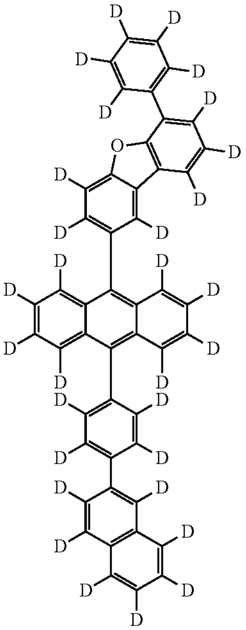
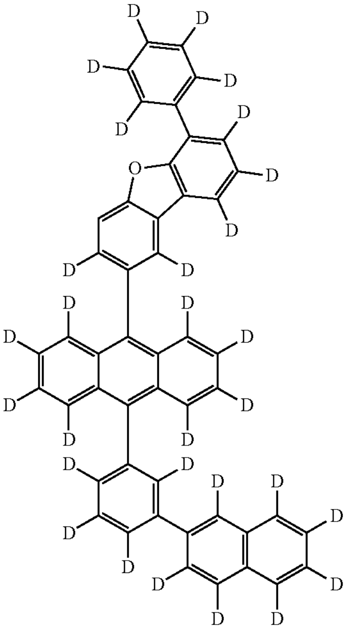

-continued
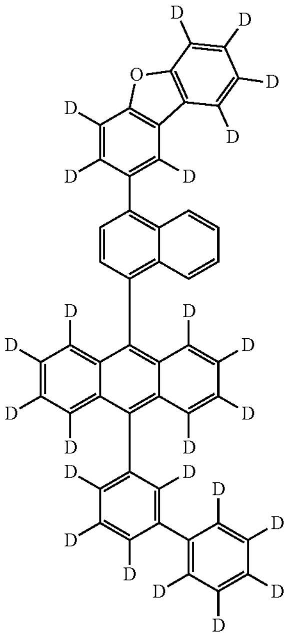
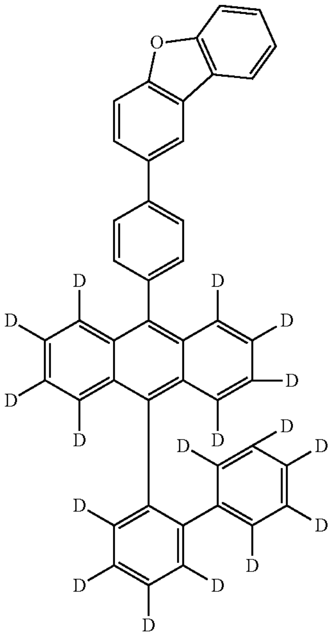
-continued
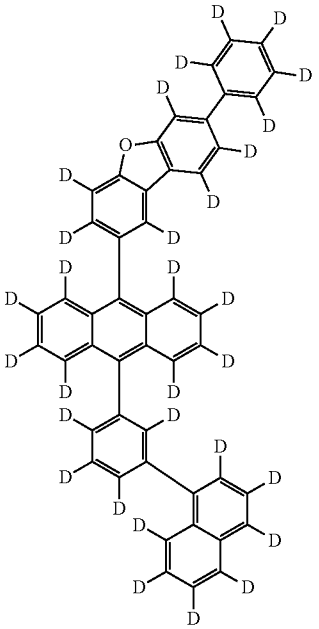
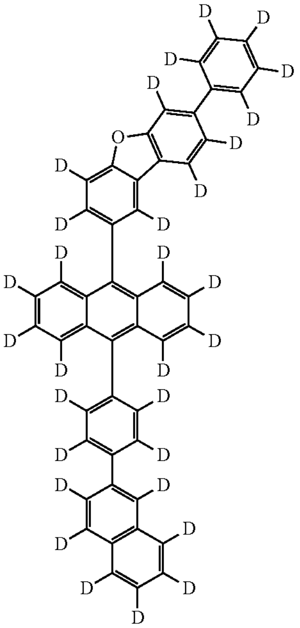

-continued
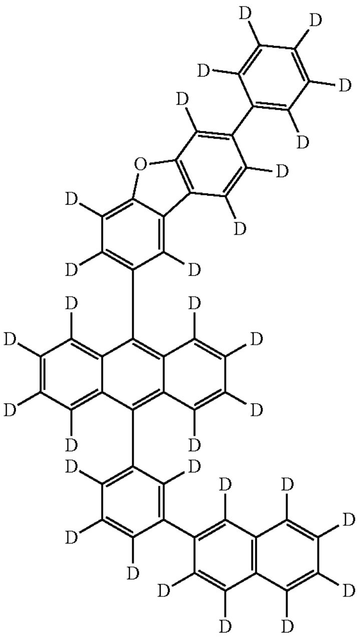
-continued
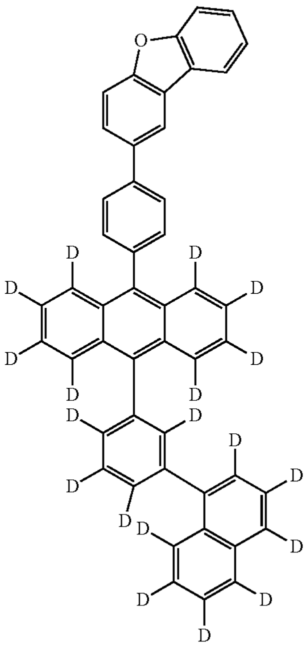
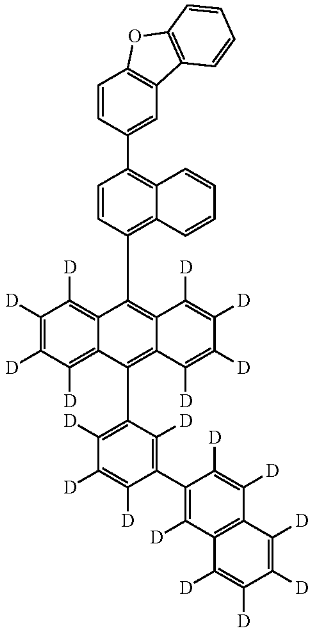
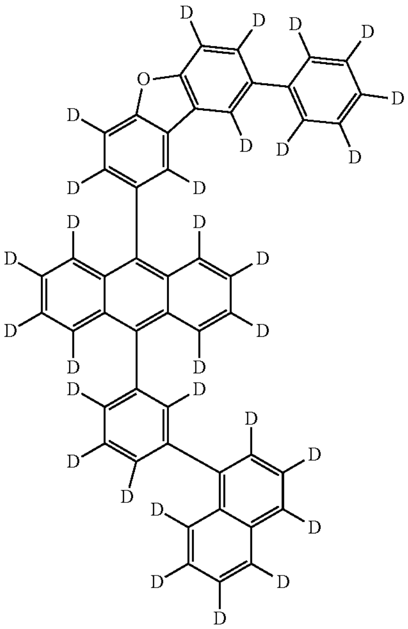

-continued
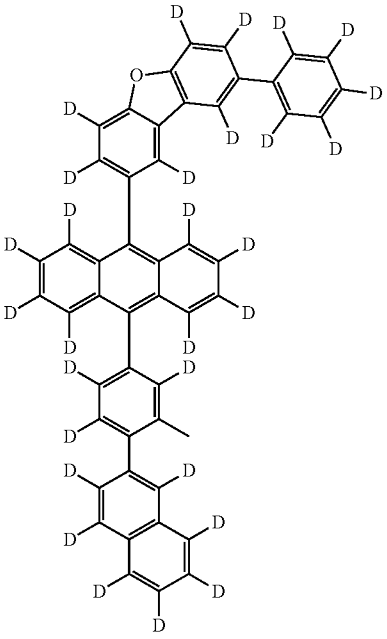
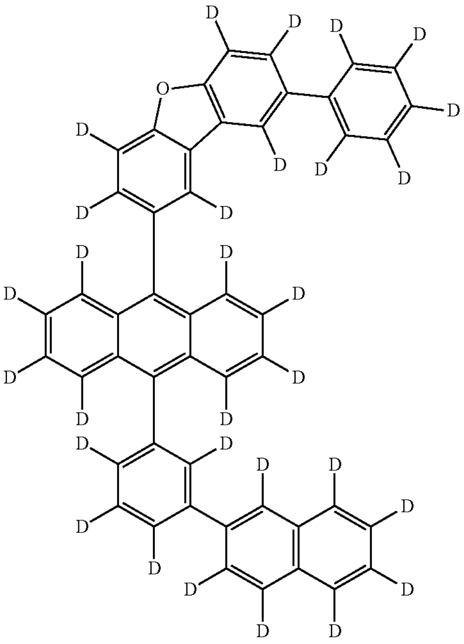 [SMILES: [2H]c1c([2H])c([2H])c(-c2c([2H])c([2H])c3oc4c([2H])c([2H])c(-c5c6c([2H])c([2H])c([2H])c([2H])c6c(-c6c([2H])c([2H])c([2H])c(-c7c([2H])c([2H])c8c([2H])c([2H])c([2H])c([2H])c8c7[2H])c6[2H])c6c([2H])c([2H])c([2H])c([2H])c56)c([2H])c4c3c2[2H])c([2H])c1[2H]]
-continued
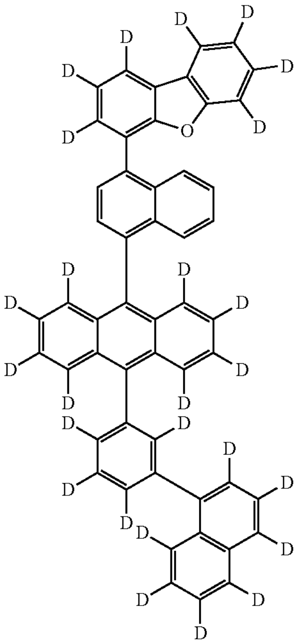
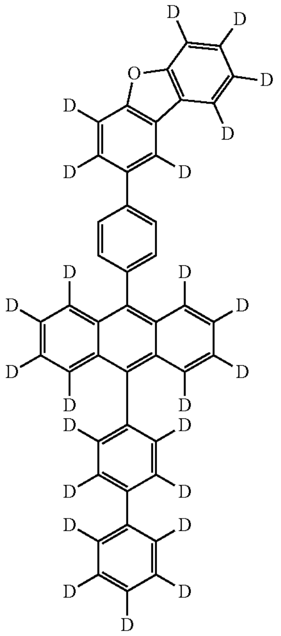

-continued
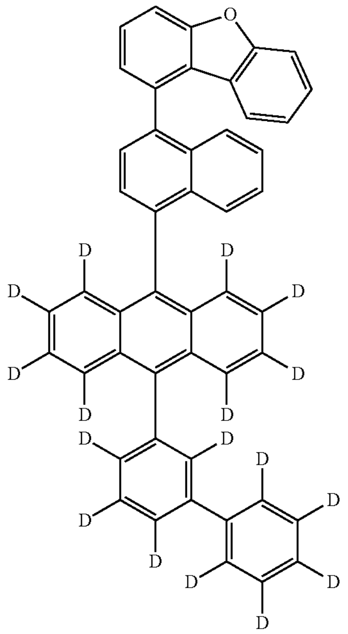
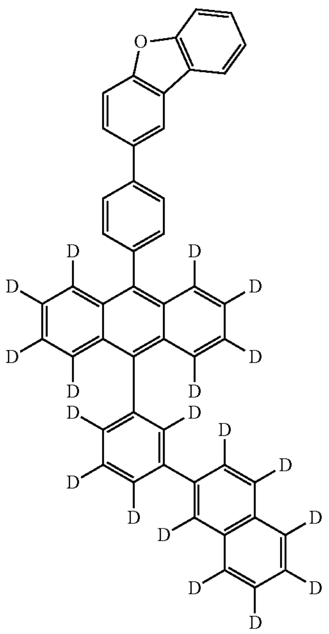
-continued
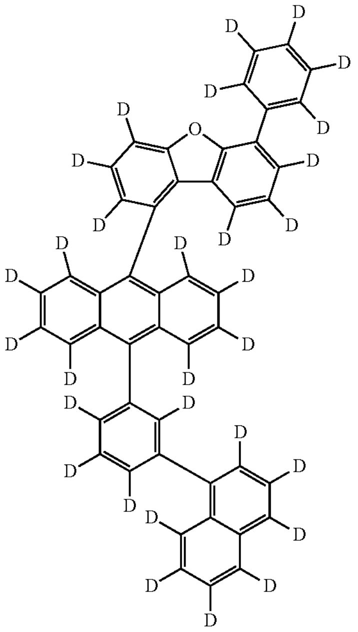
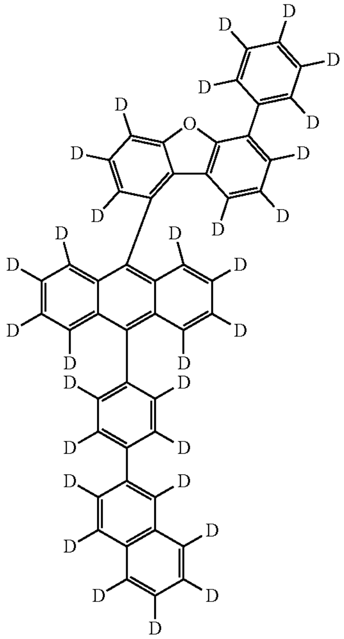

-continued
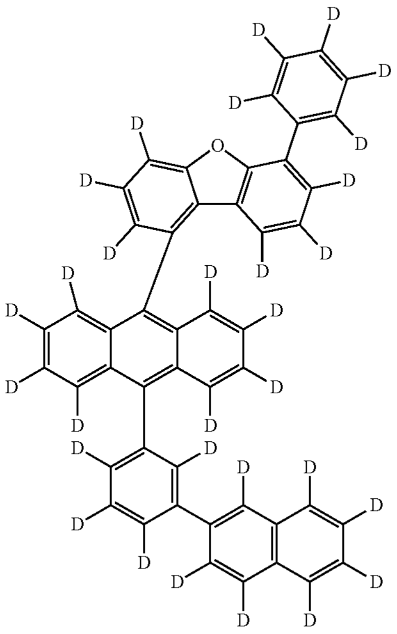
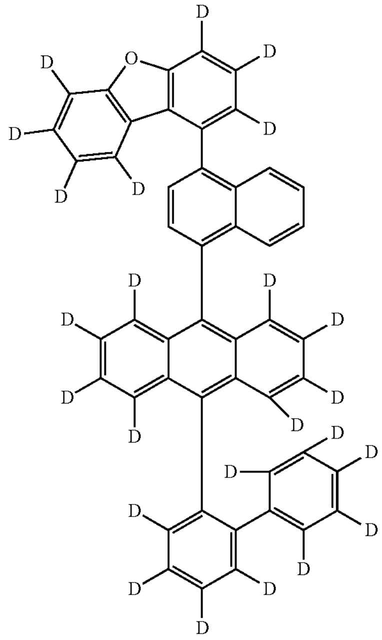
-continued
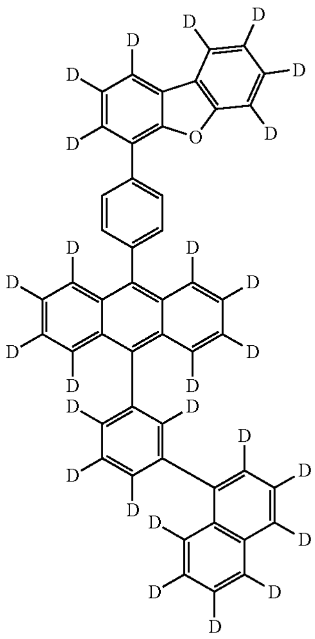
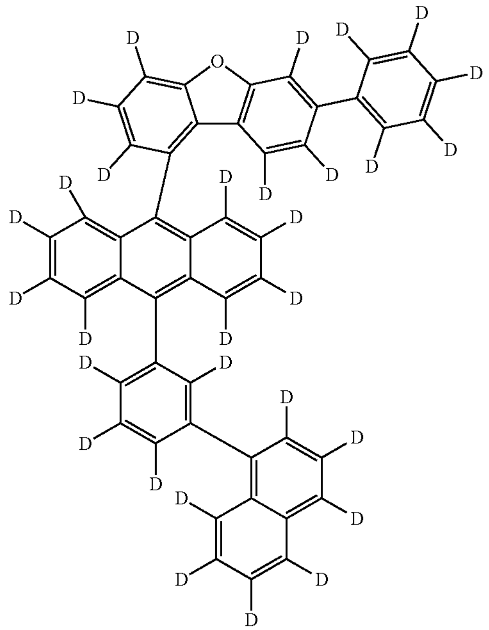

-continued
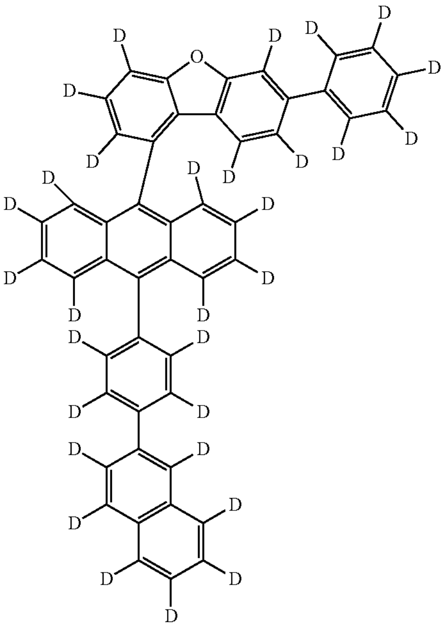
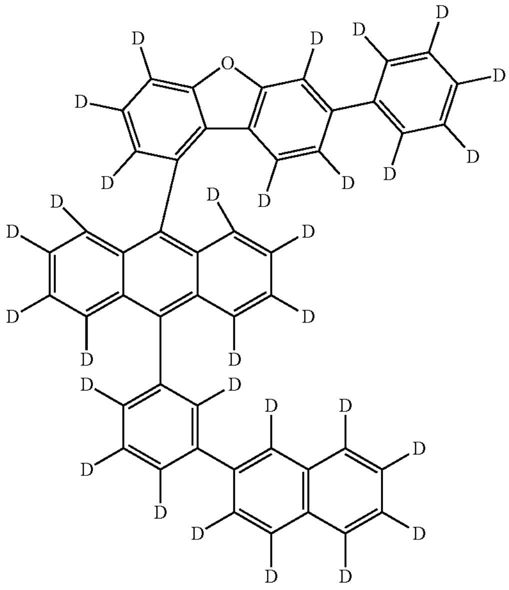
-continued
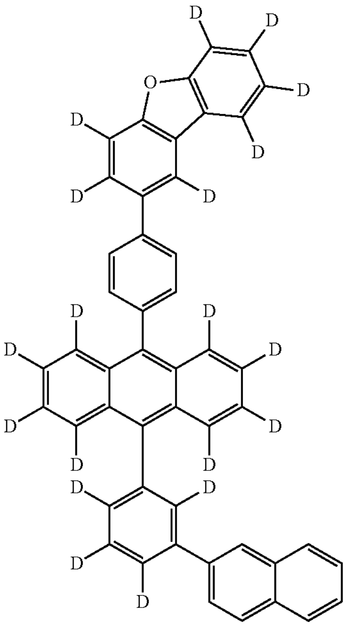
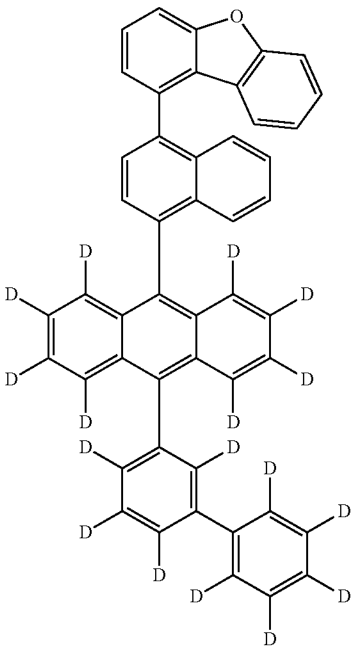

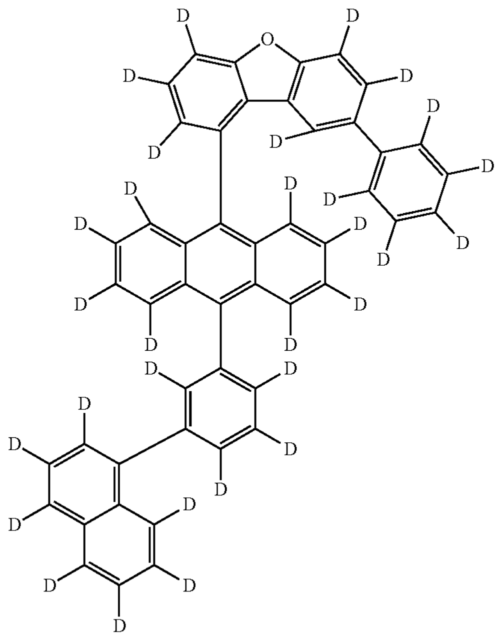
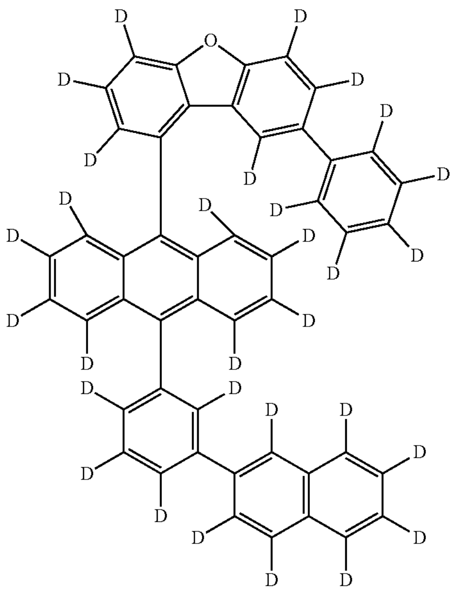
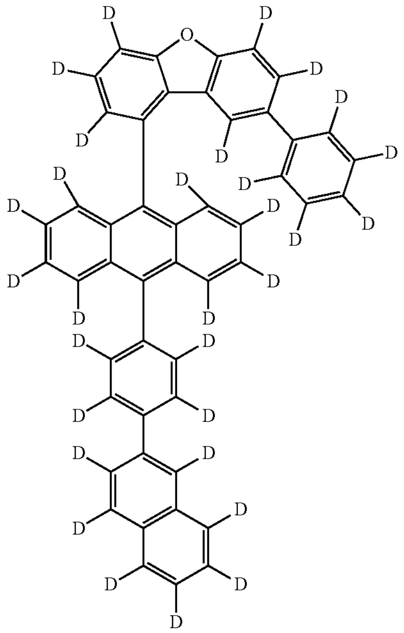
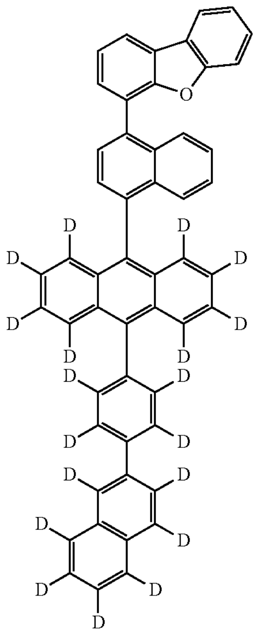

-continued
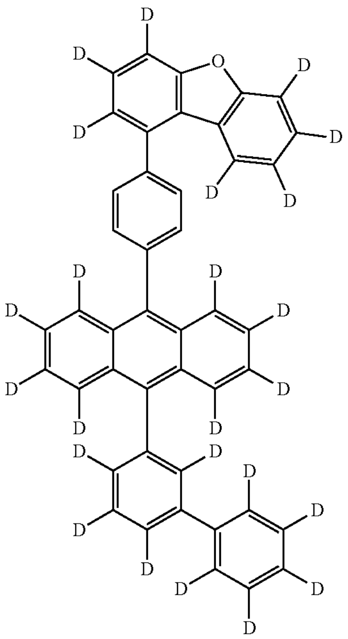
-continued
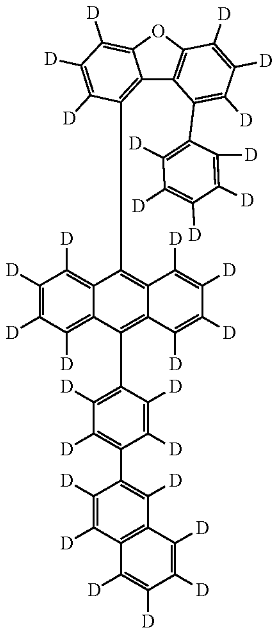
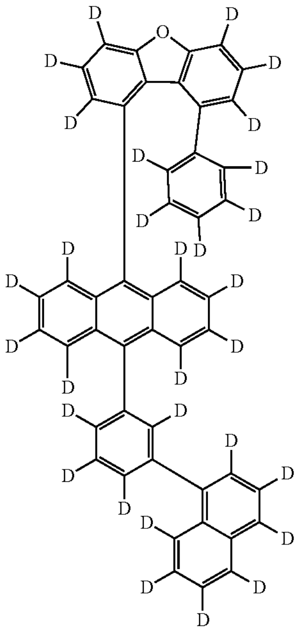
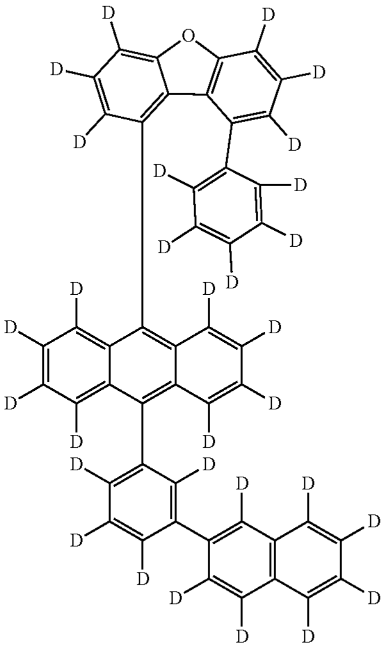

-continued
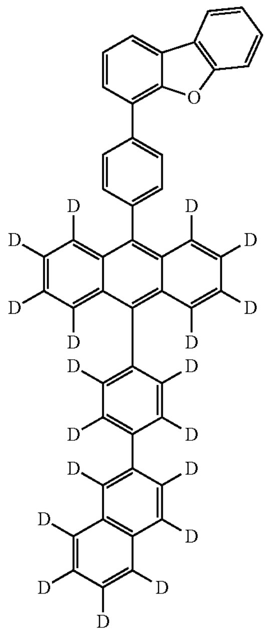
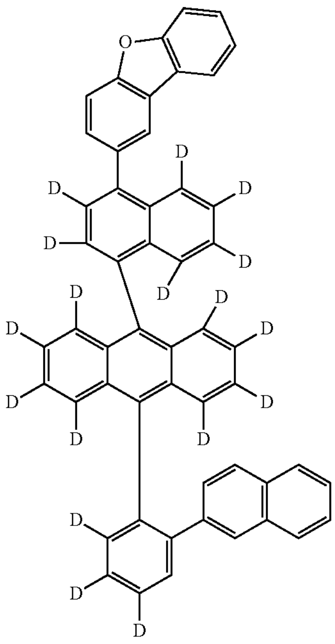
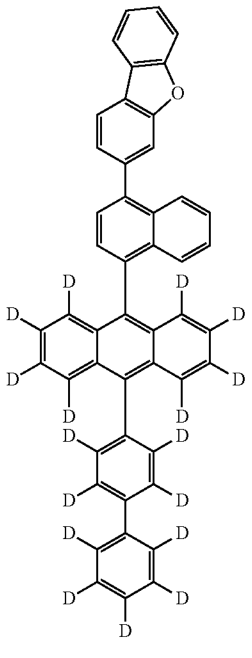
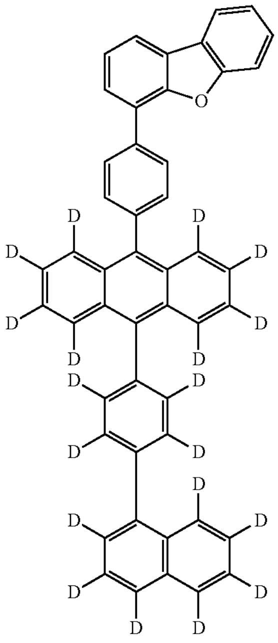

-continued
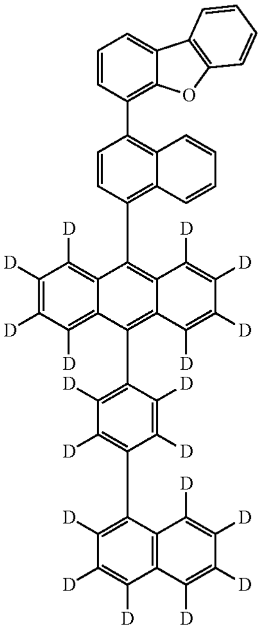
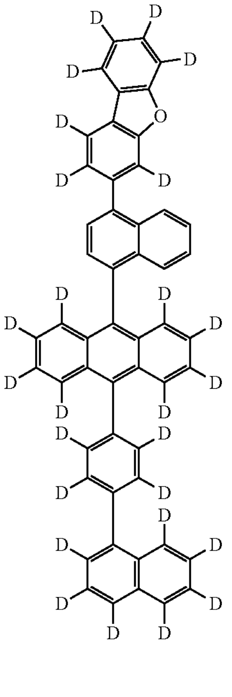
-continued
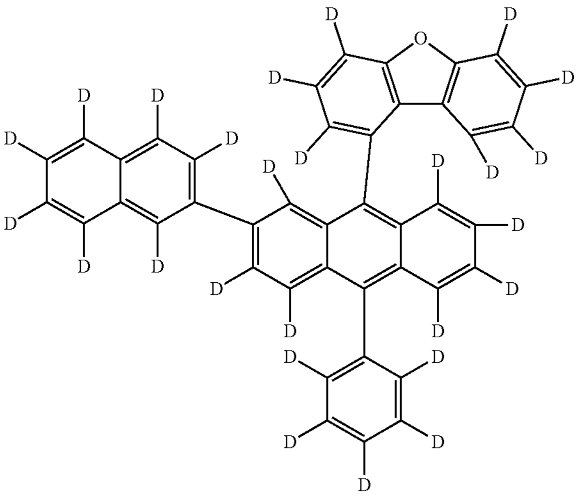
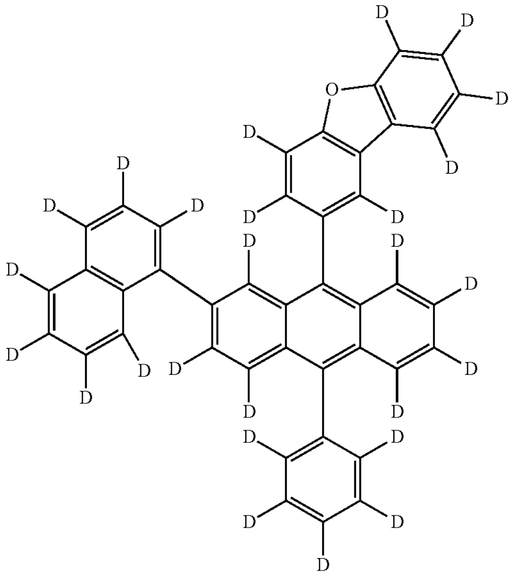
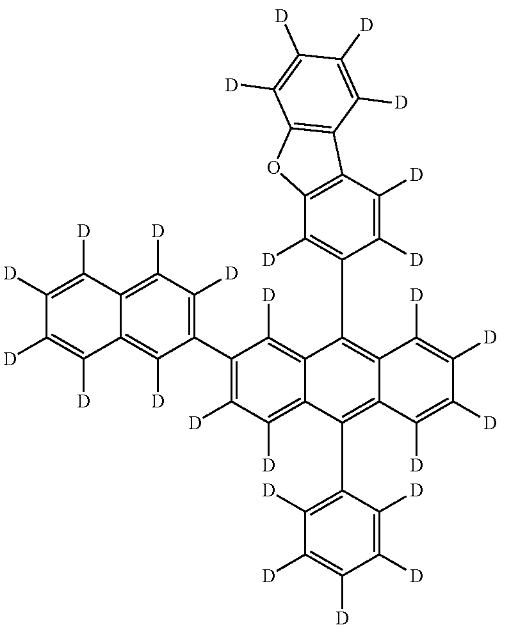

-continued
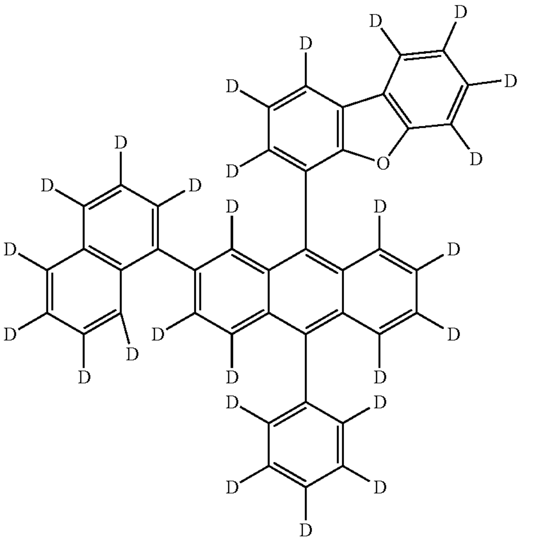
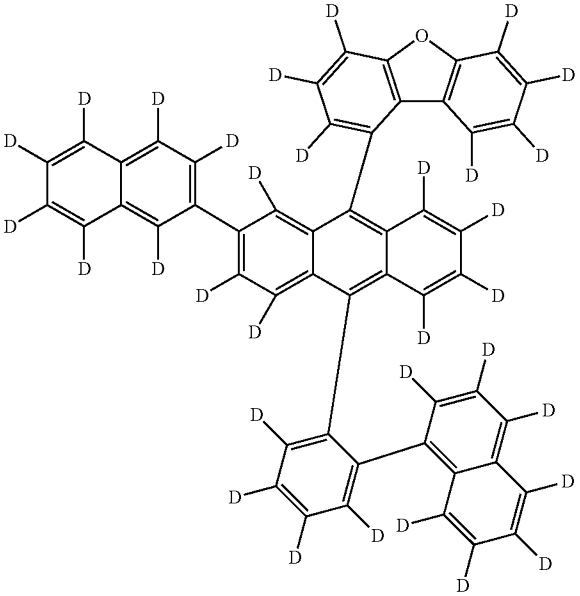
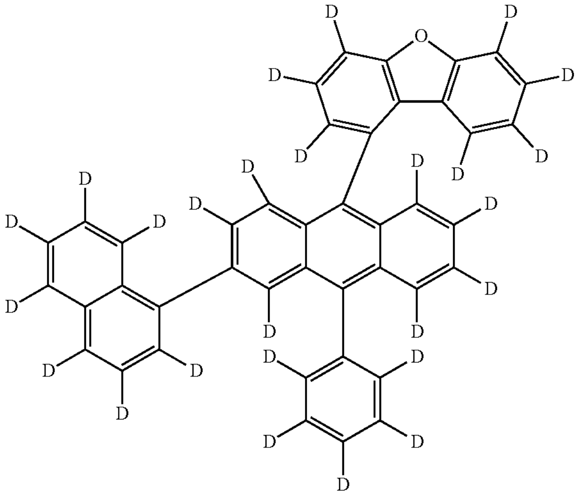
-continued
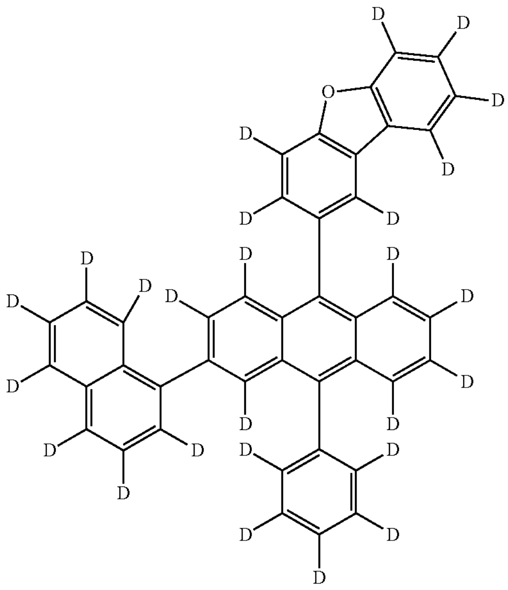
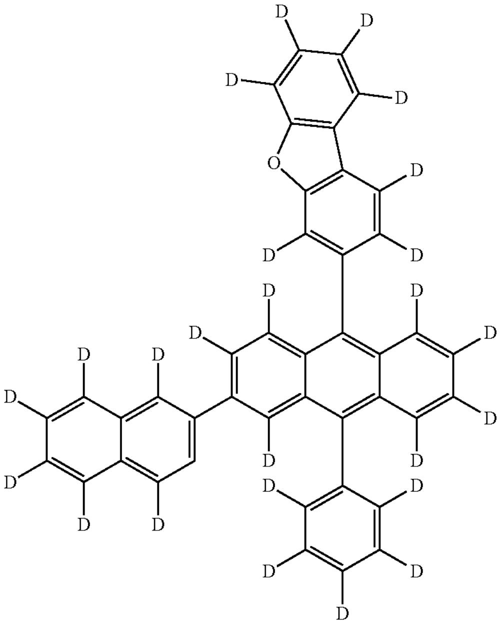

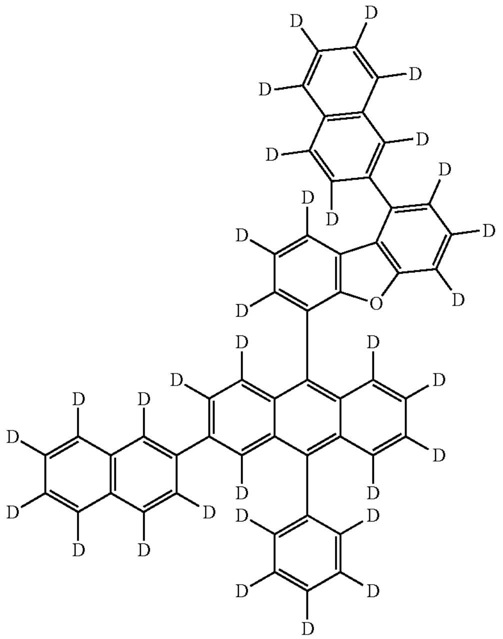
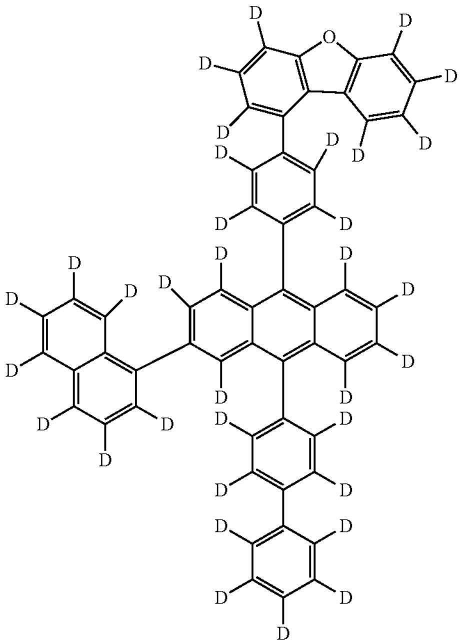
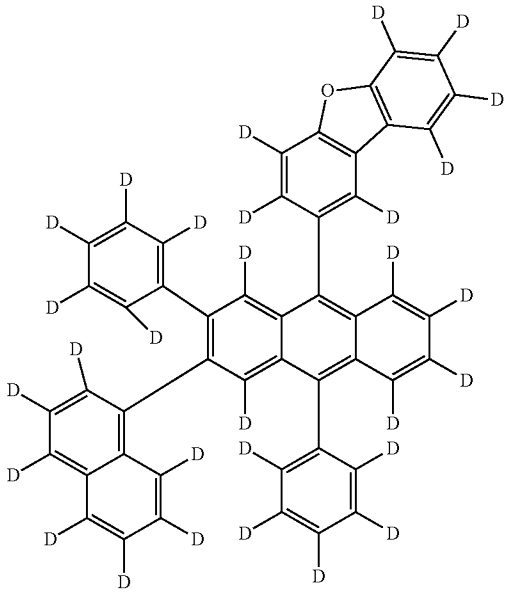
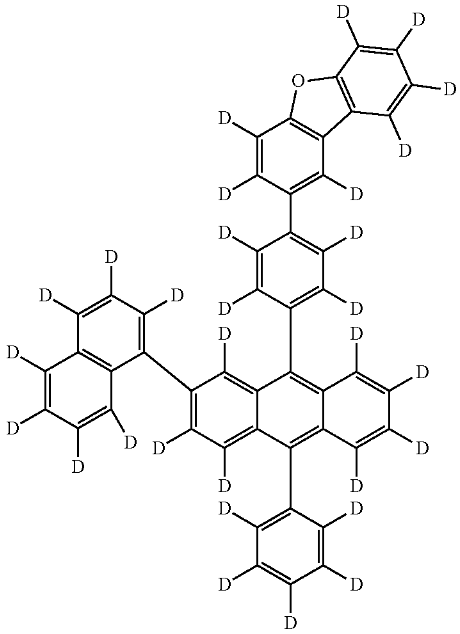

-continued
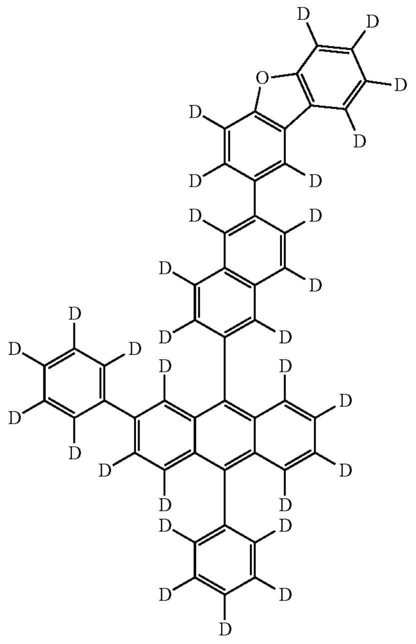 [SMILES: [2H]c1c([2H])c([2H])c(-c2c([2H])c([2H])c3c(-c4c([2H])c([2H])c([2H])c([2H])c4[2H])c4c([2H])c([2H])c([2H])c([2H])c4c(-c4c([2H])c([2H])c5c([2H])c(-c6c([2H])c([2H])c7oc8c([2H])c([2H])c([2H])c([2H])c8c7c6[2H])c([2H])c([2H])c5c4[2H])c3c2[2H])c([2H])c1[2H]]
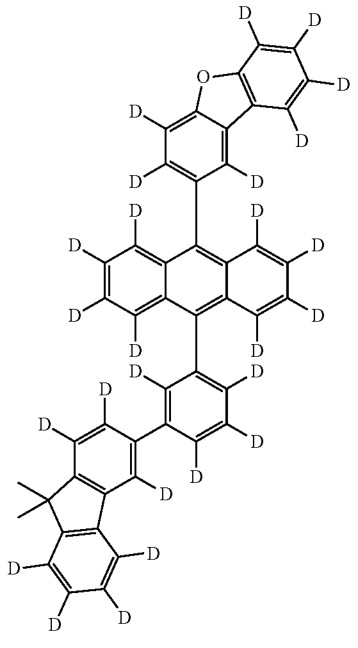
-continued
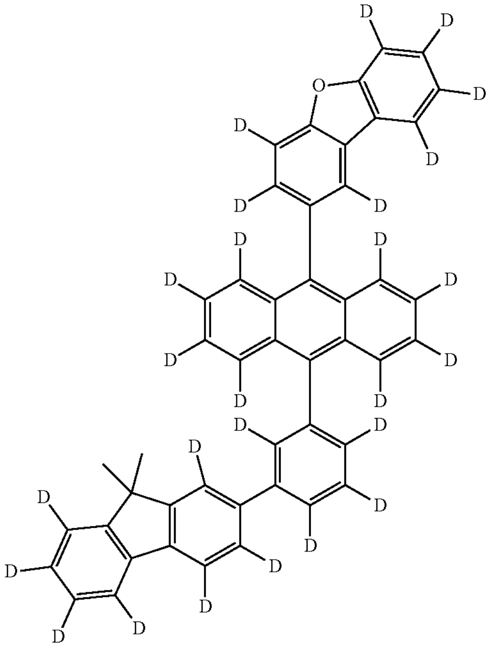
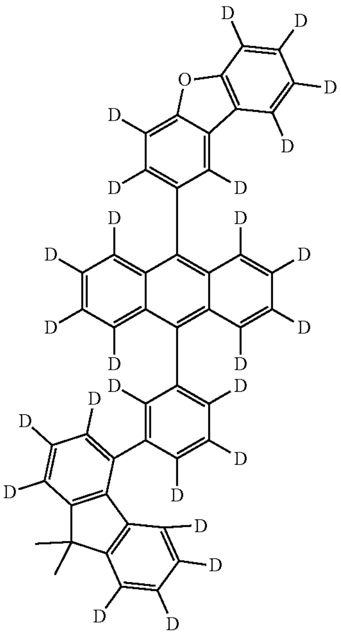

-continued
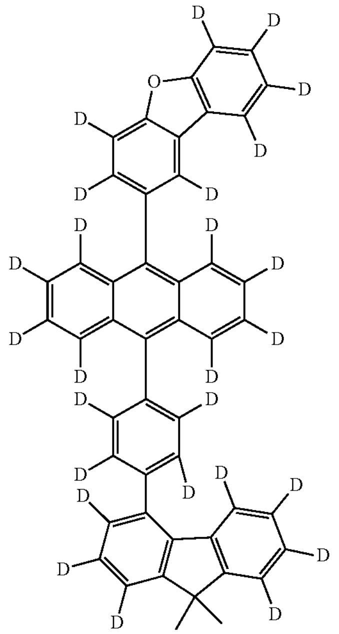
-continued
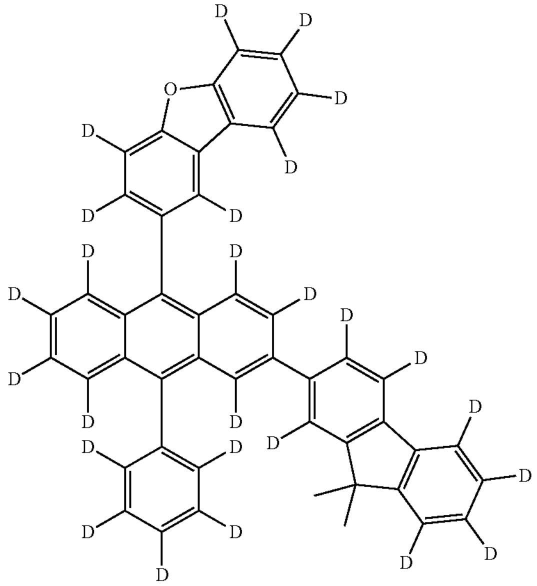
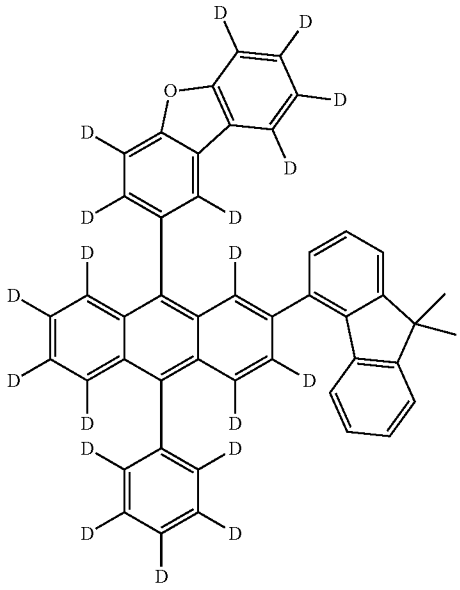
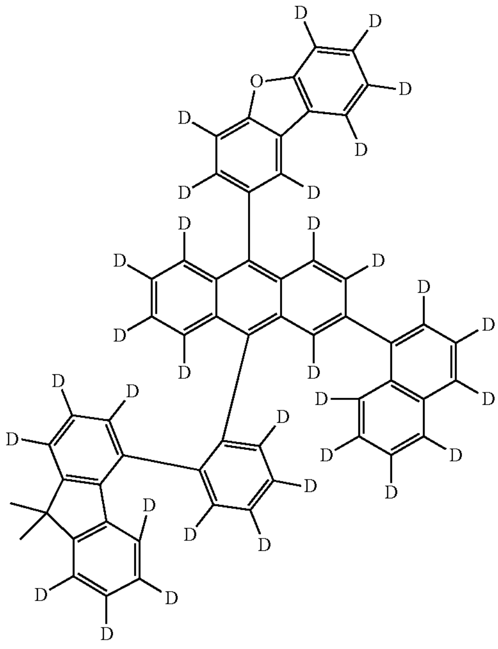

-continued
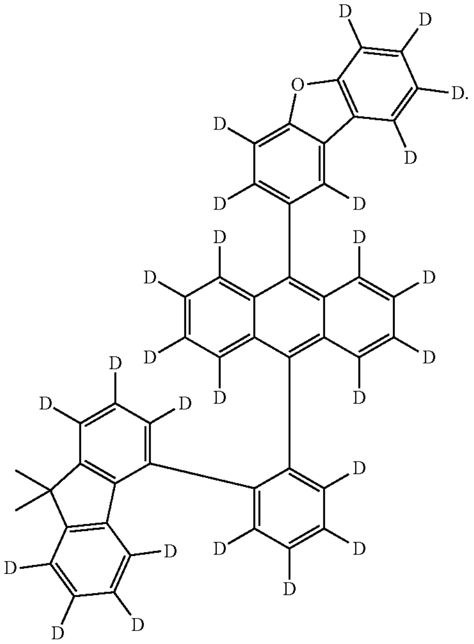
11. The organic light emitting device of claim 1, wherein the compound represented by Formula 1-3 is any one selected from the following compounds:
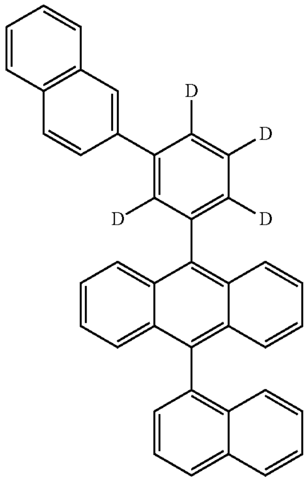
-continued
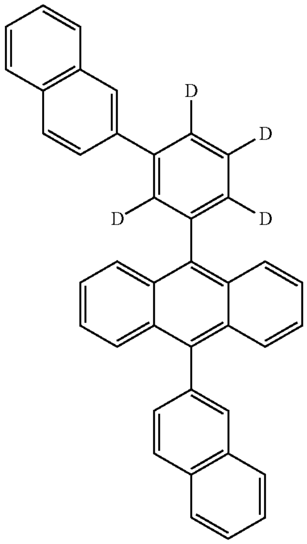
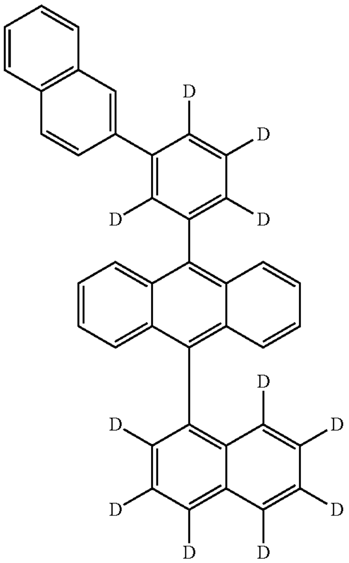
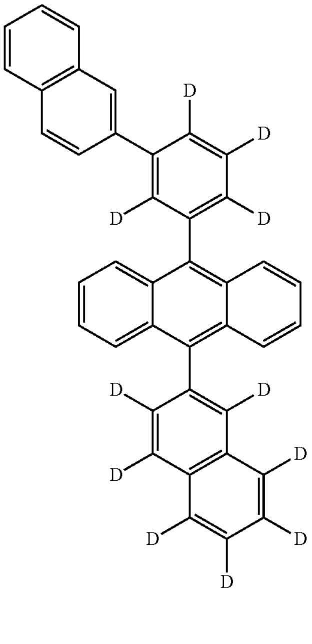

-continued
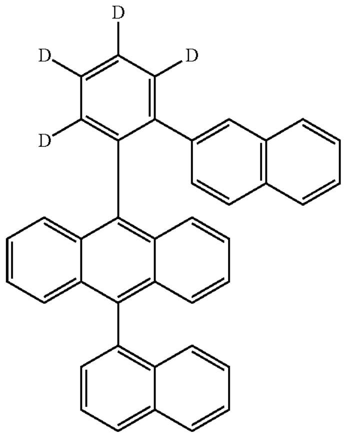
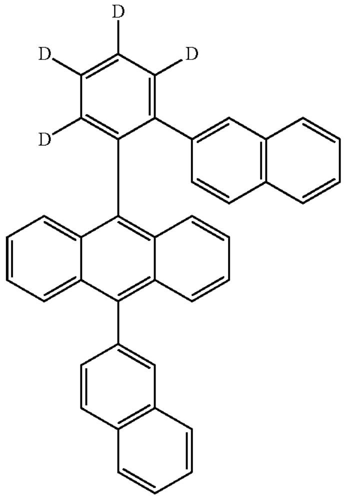
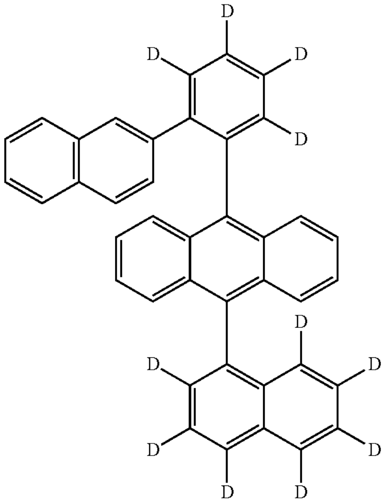
-continued
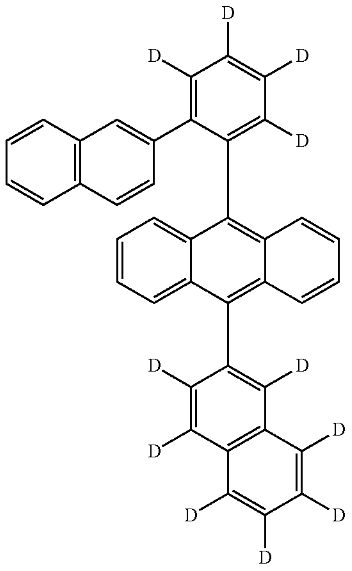
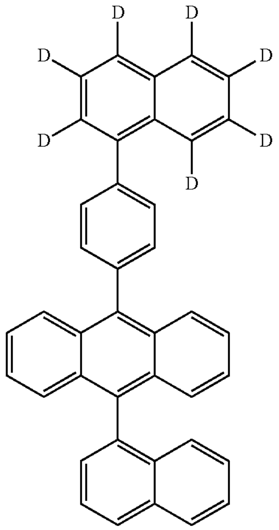
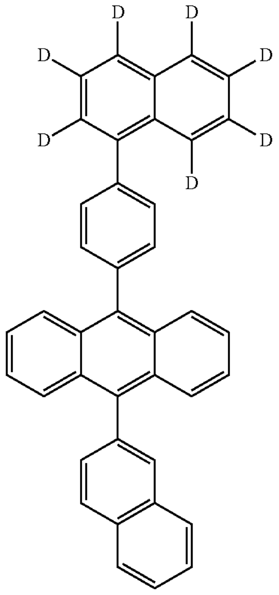

-continued
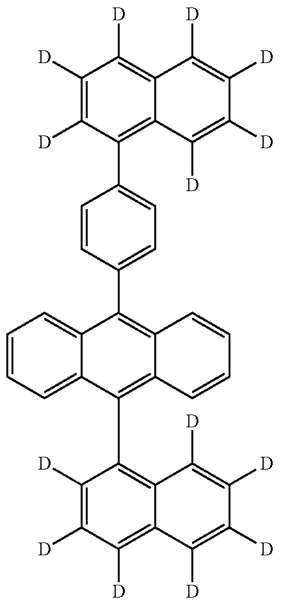
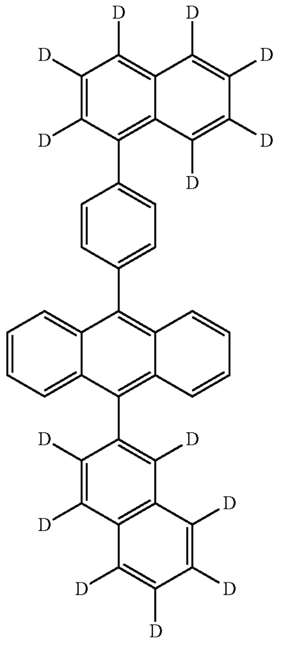
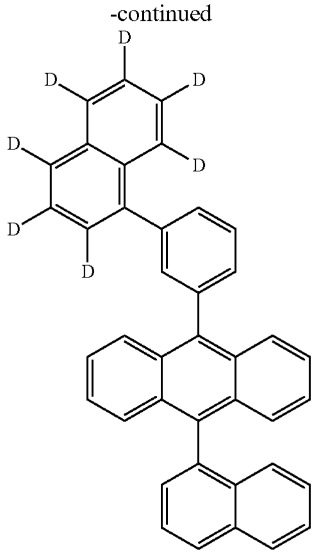
-continued
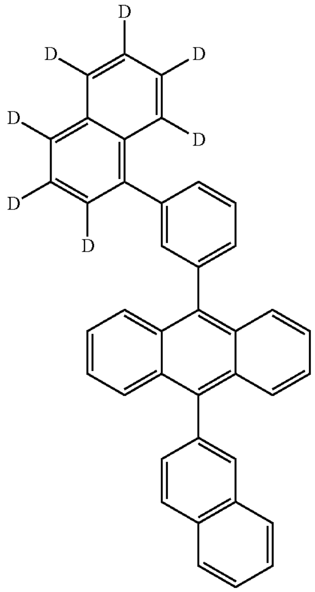
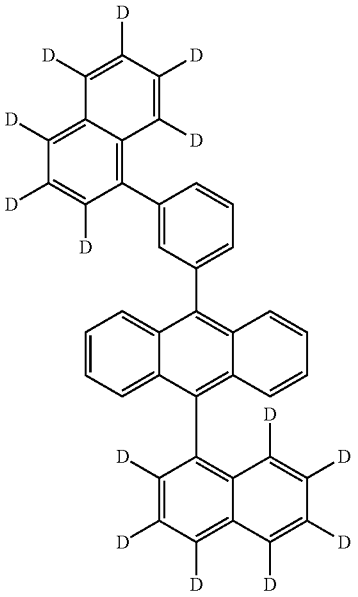

-continued
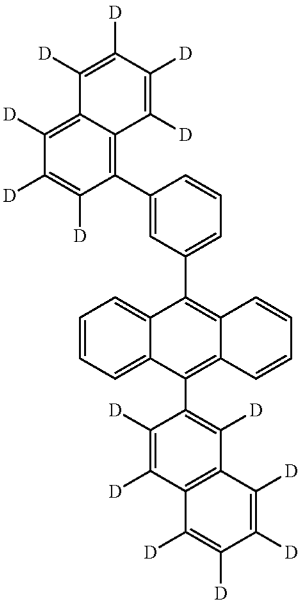
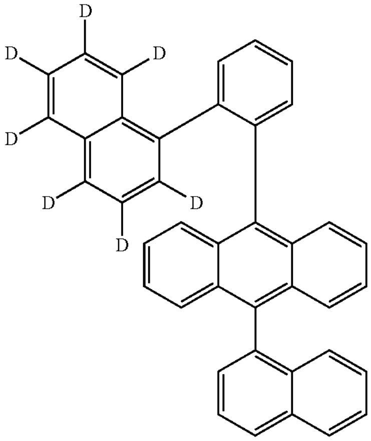
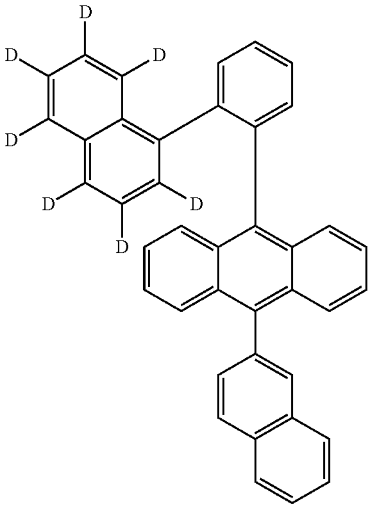
-continued
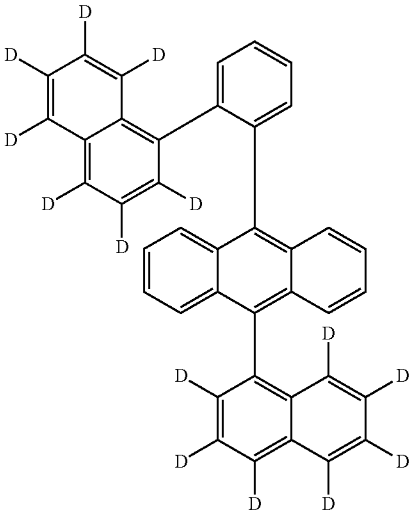
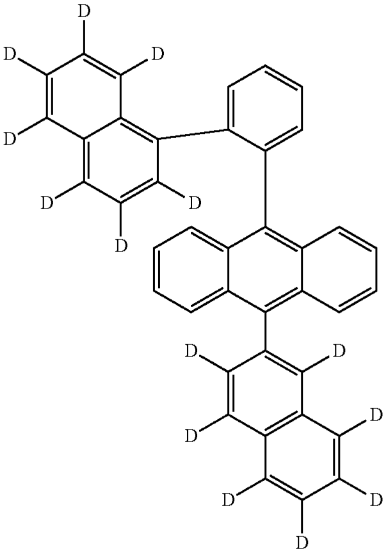
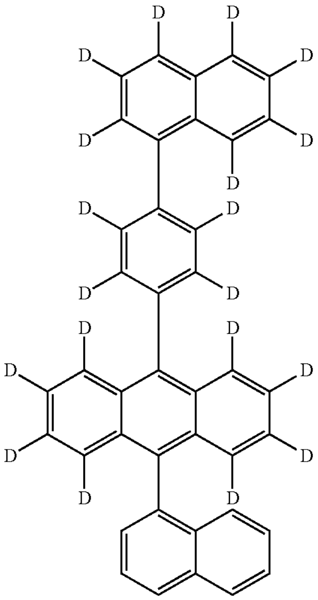

-continued
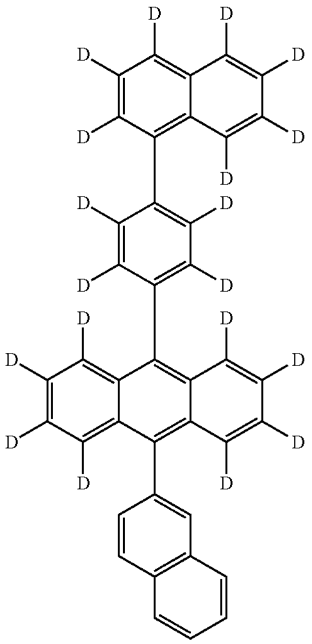
-continued
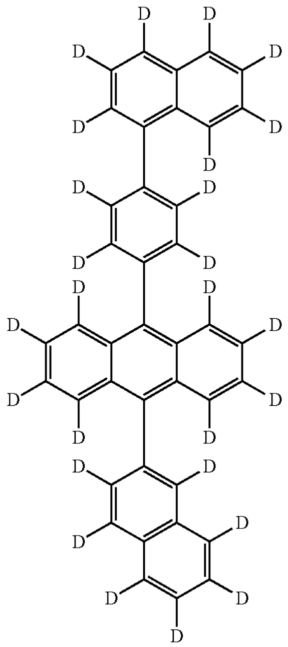
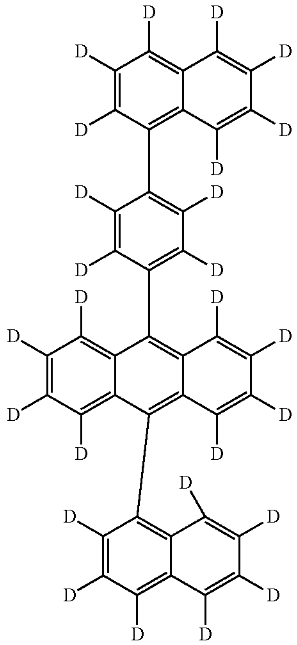
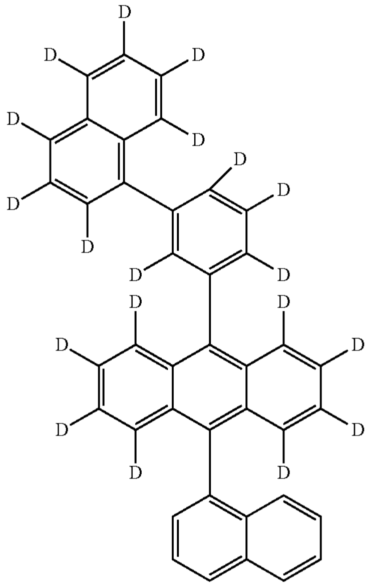

-continued
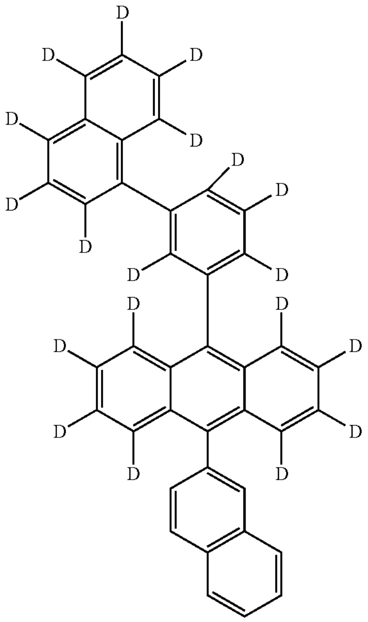
-continued
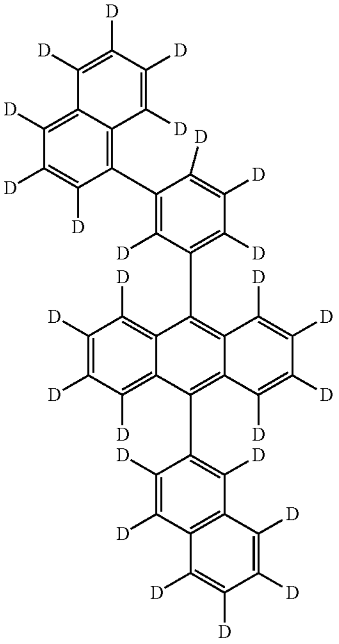
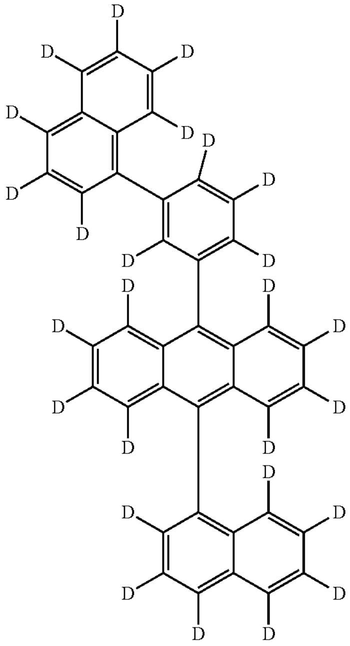
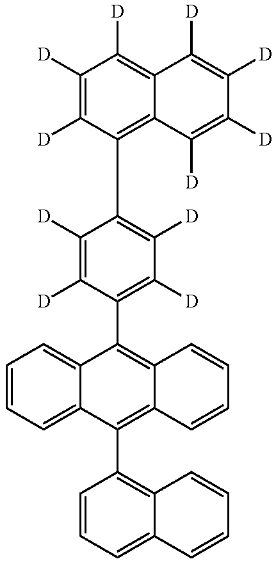
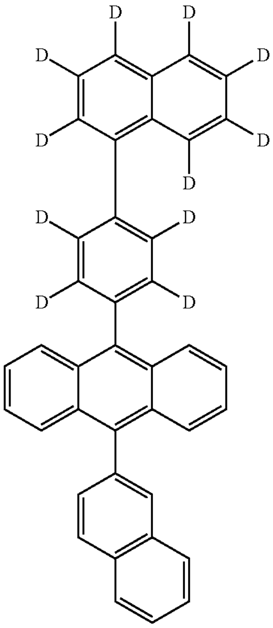

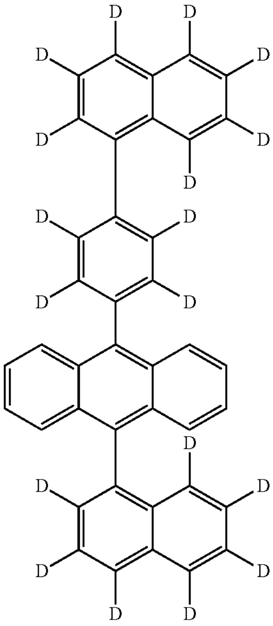
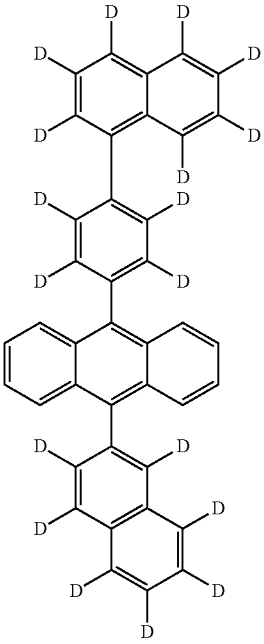
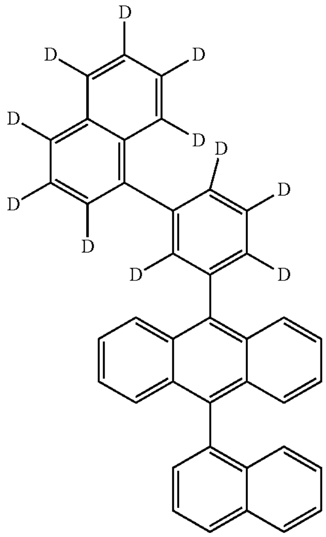
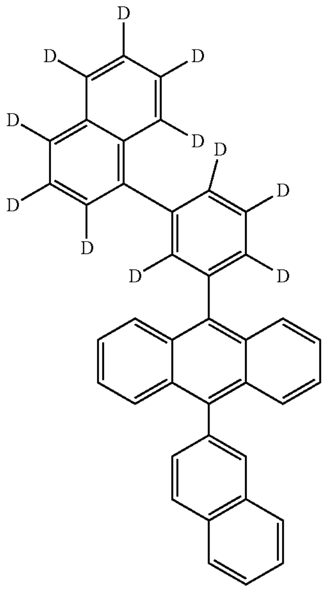
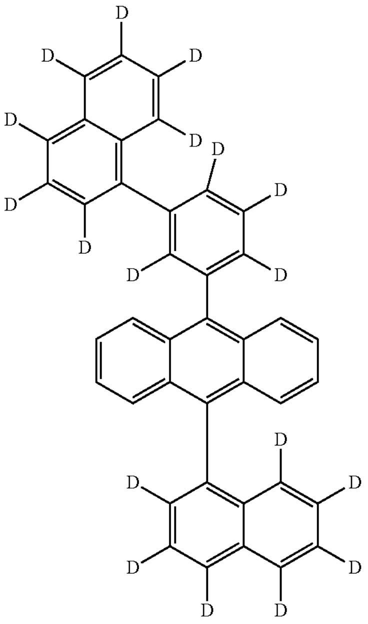

-continued
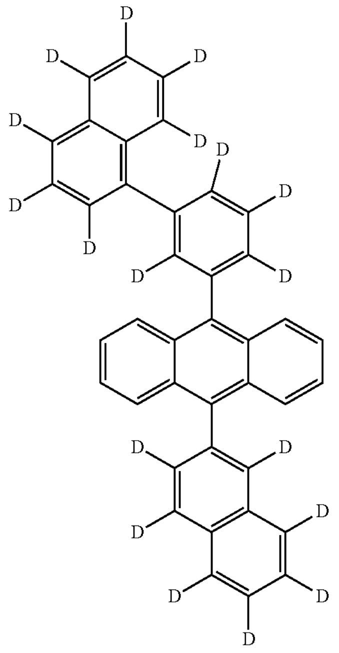
-continued
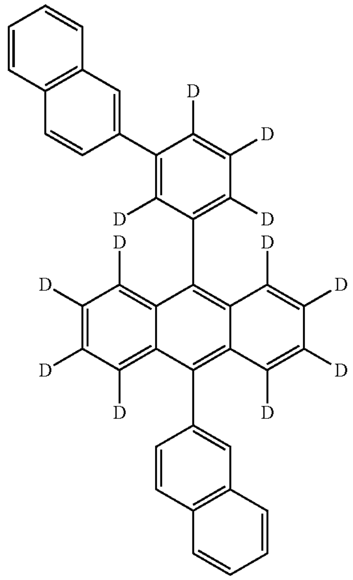
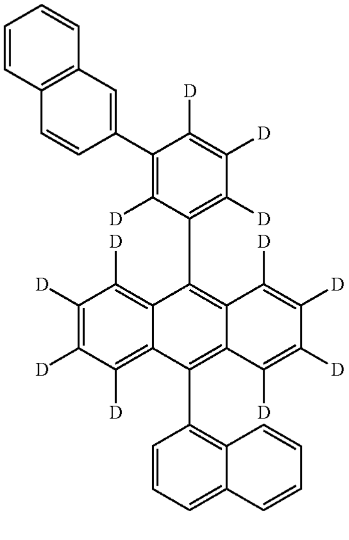
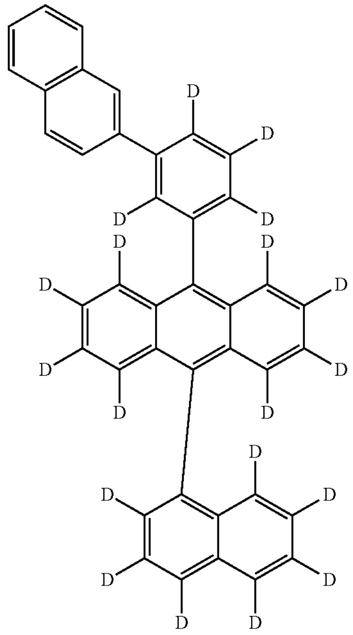

-continued
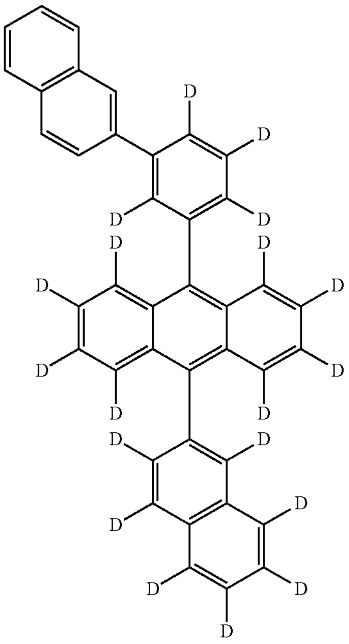
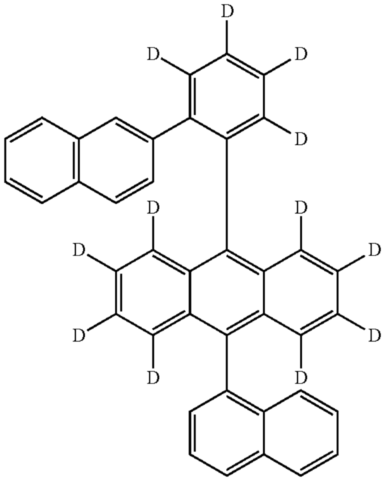
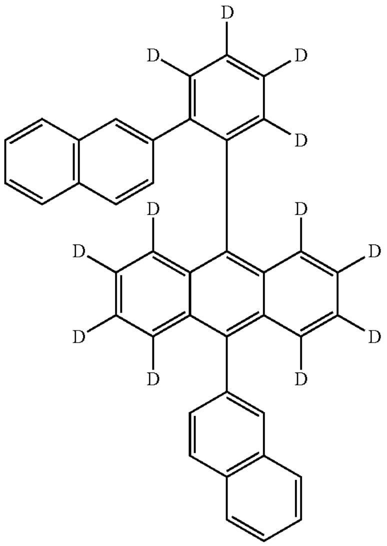
-continued
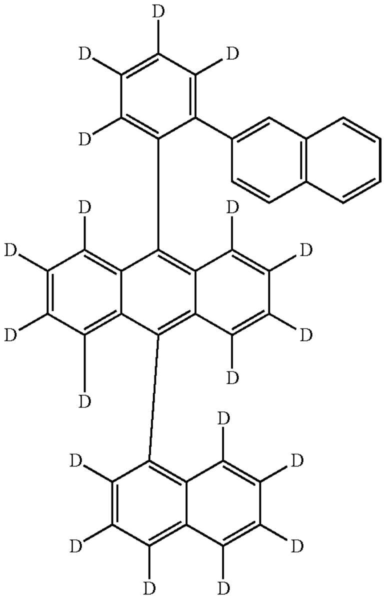
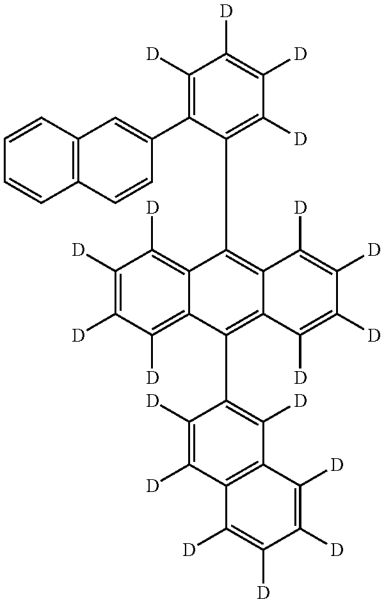

-continued
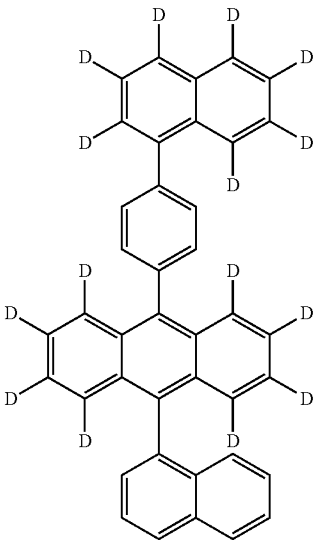
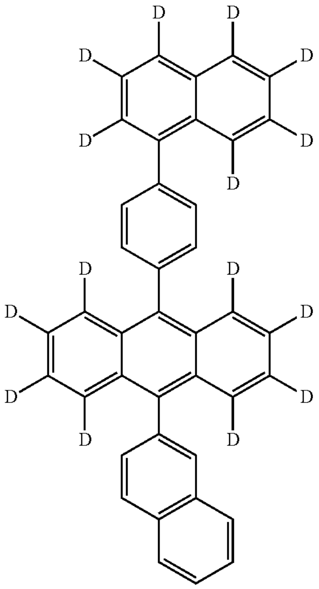
-continued
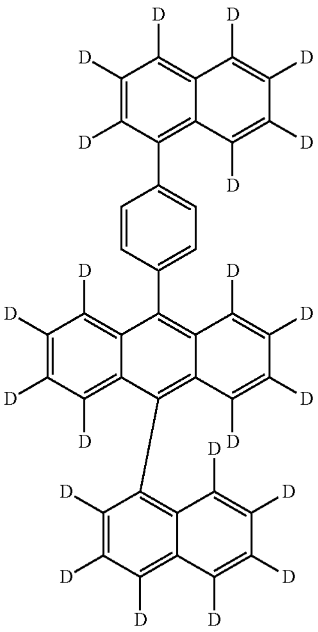
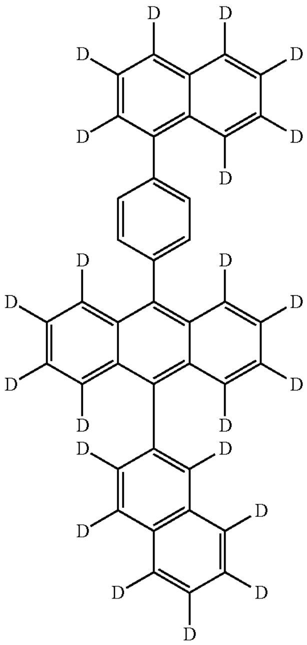

-continued
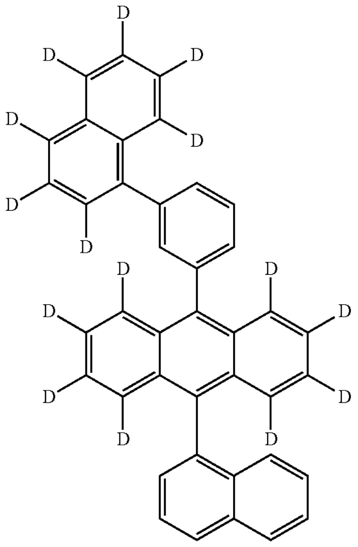
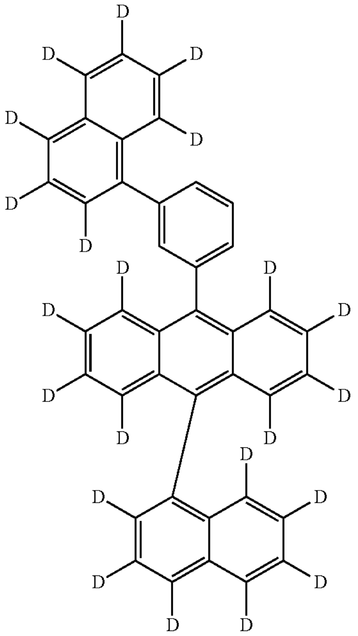
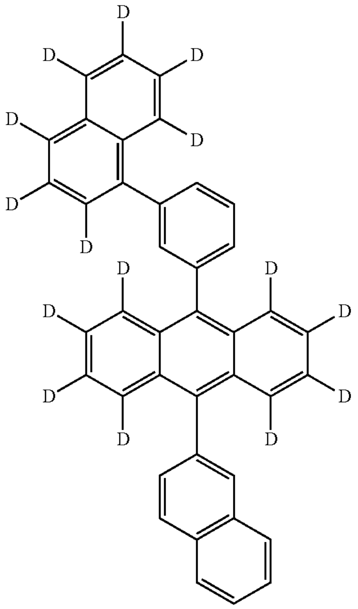
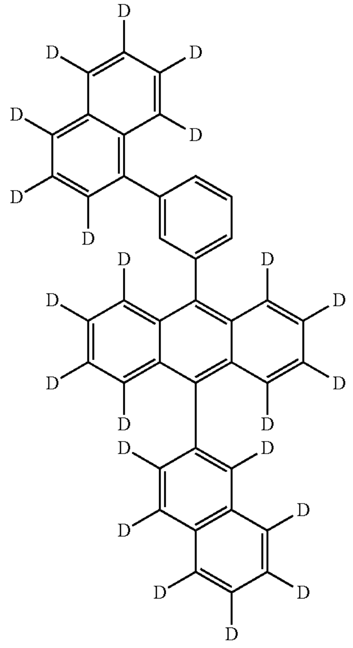
-continued

-continued
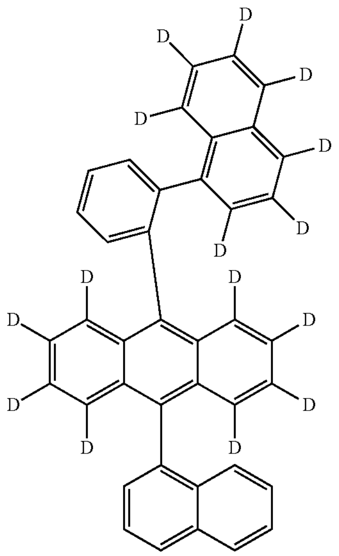
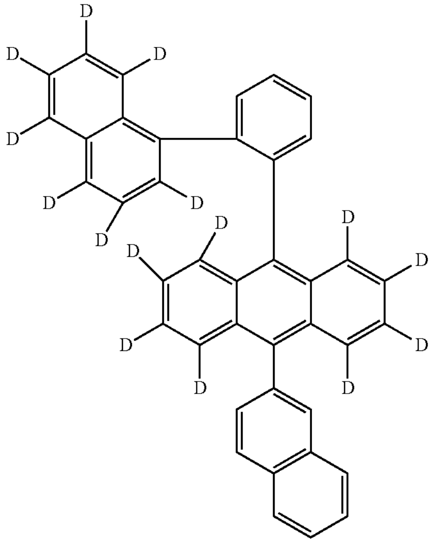
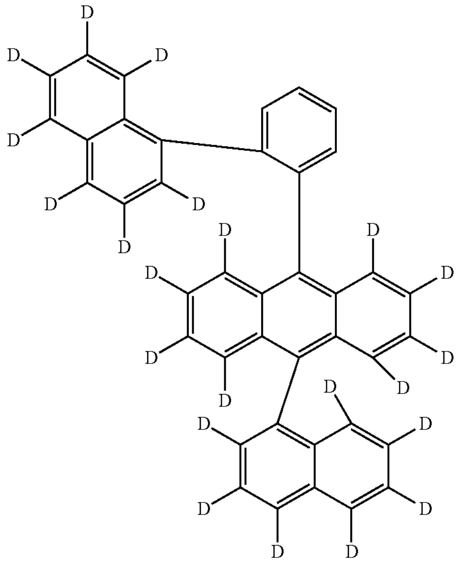
-continued
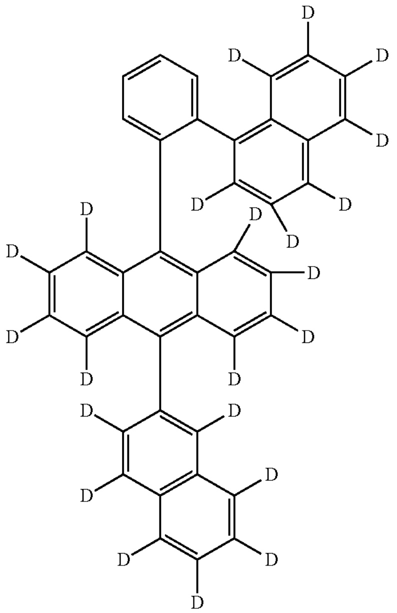
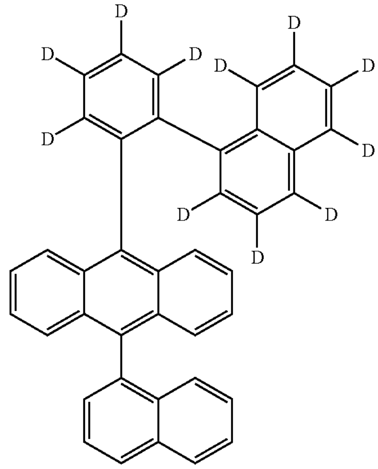
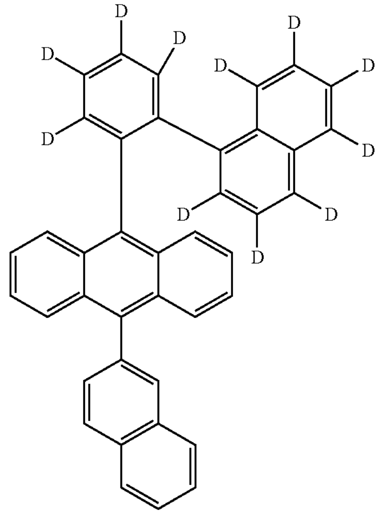

-continued
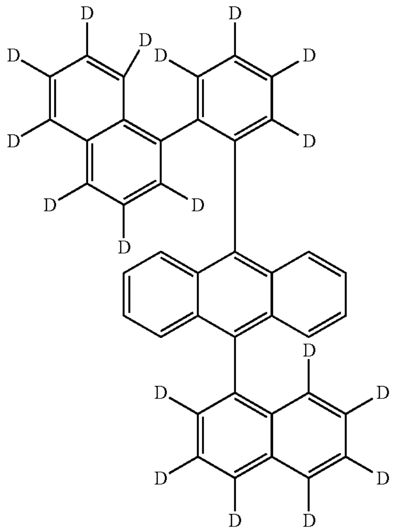
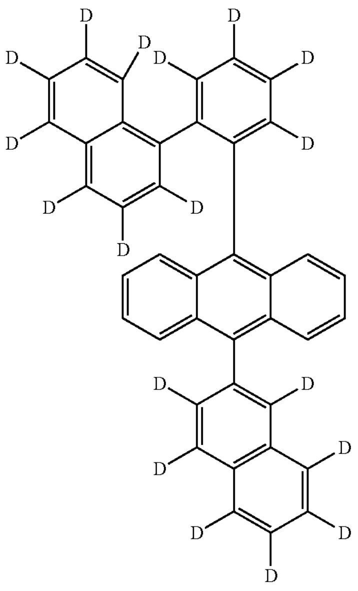
-continued
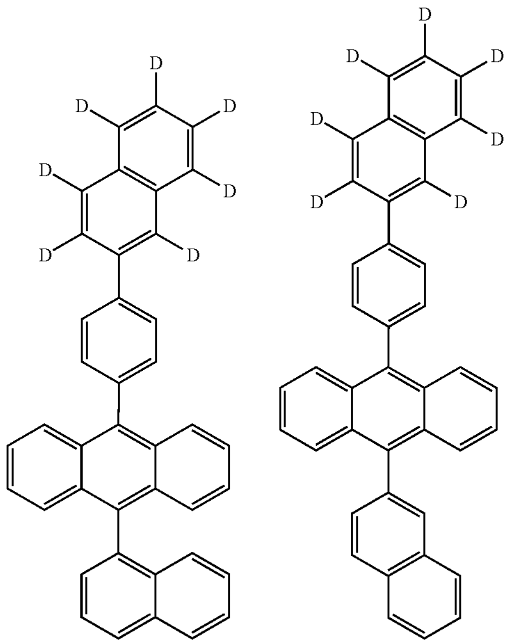
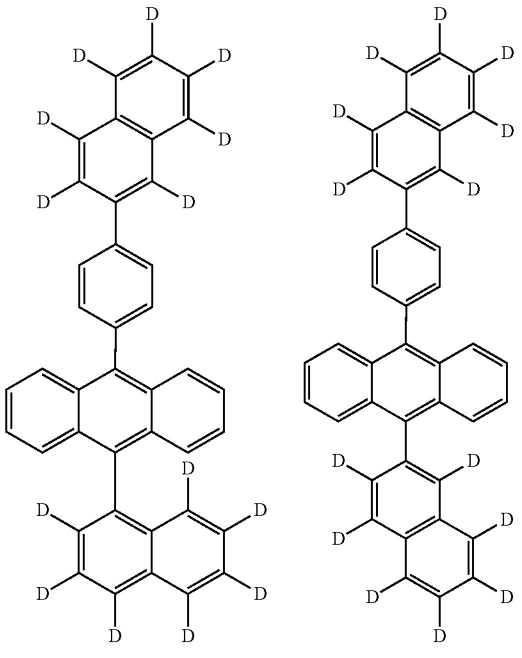

-continued
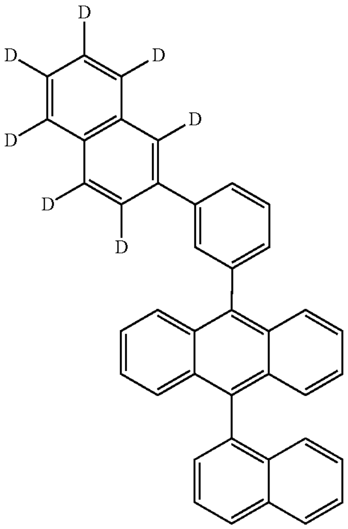
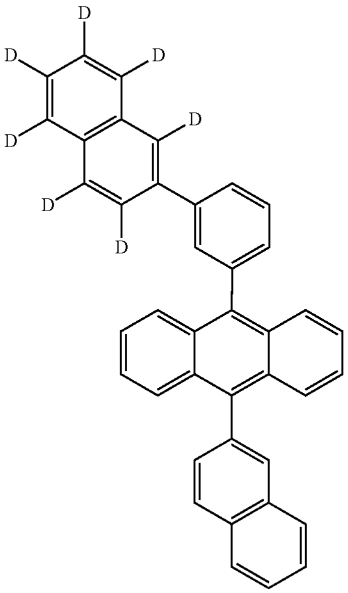
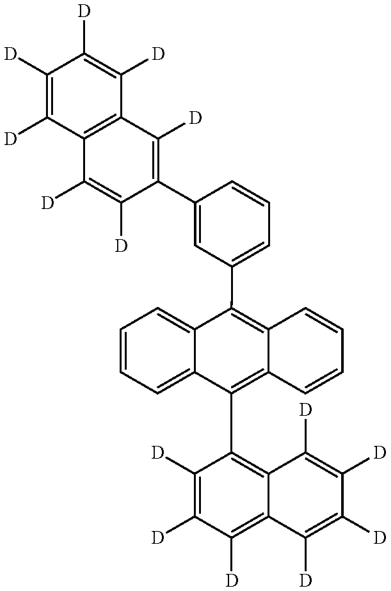
-continued
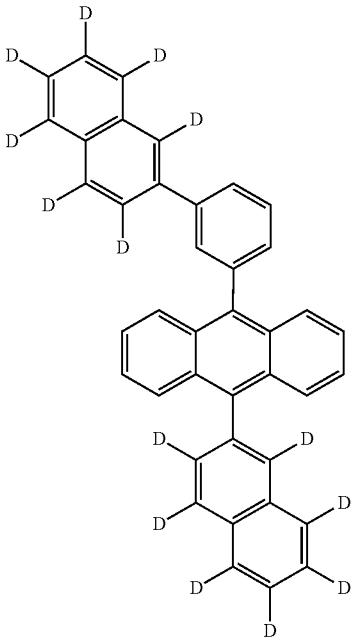
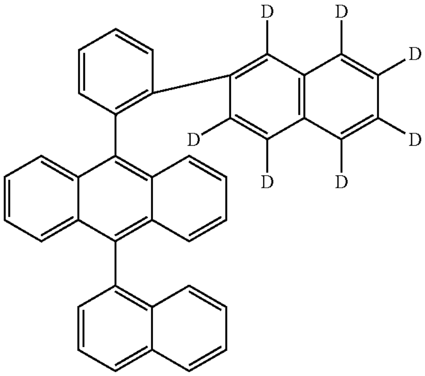
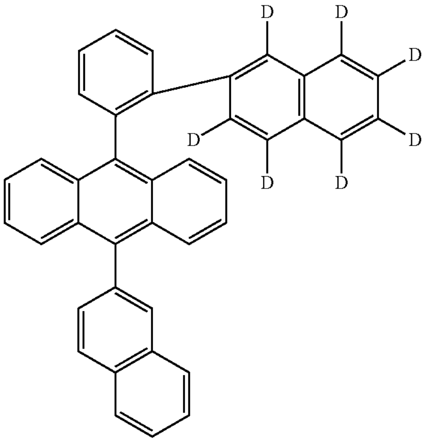

-continued
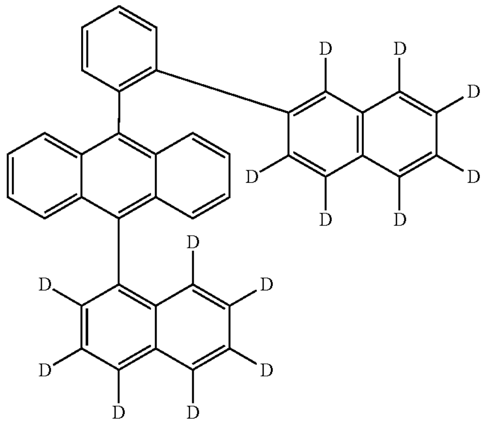
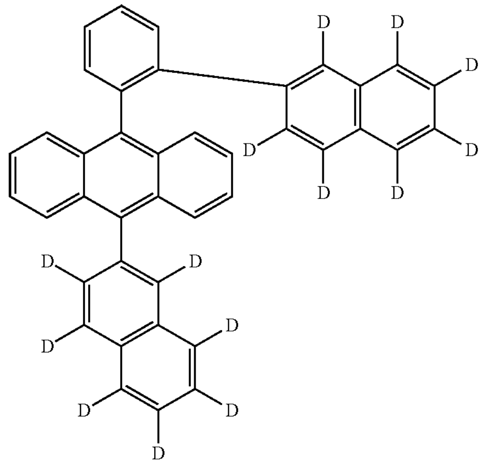
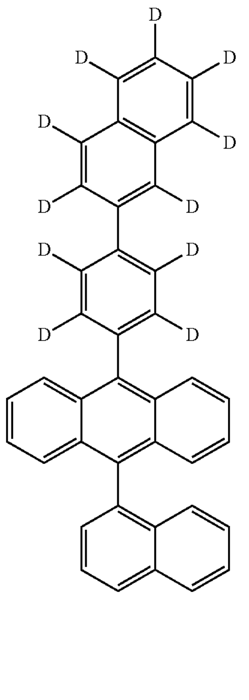
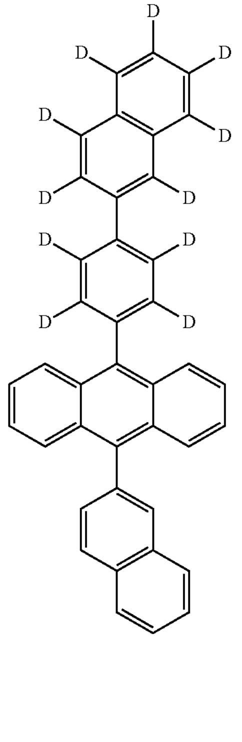
-continued
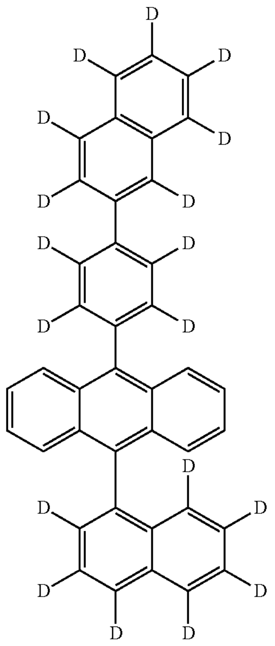
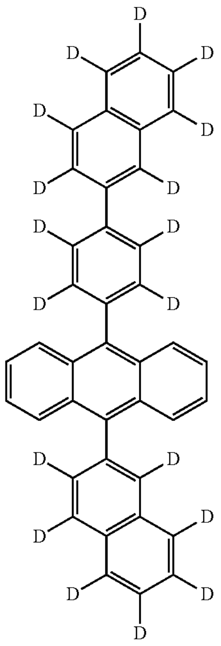
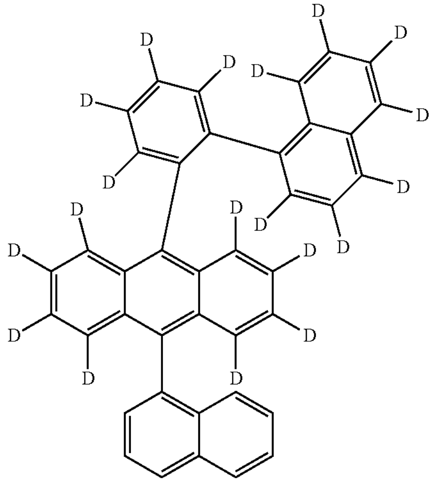
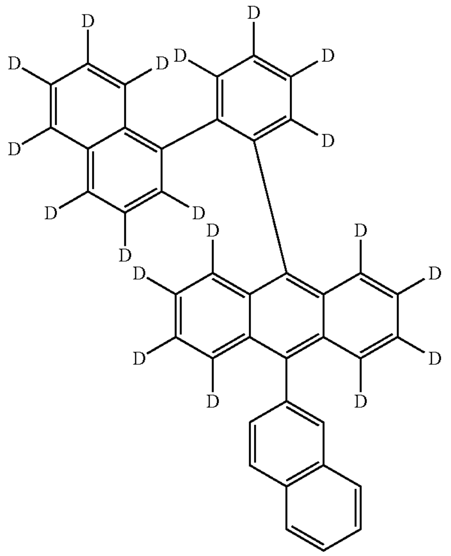

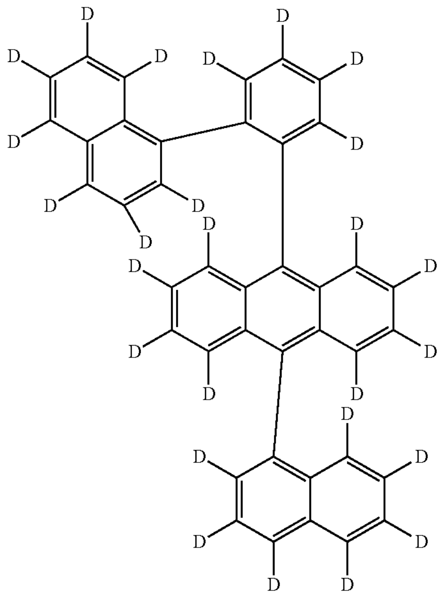
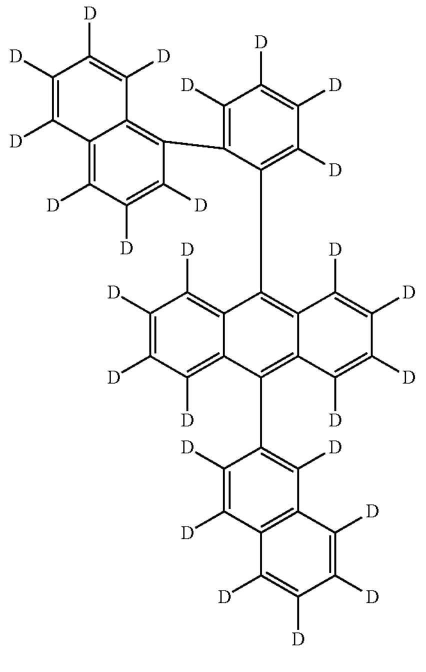
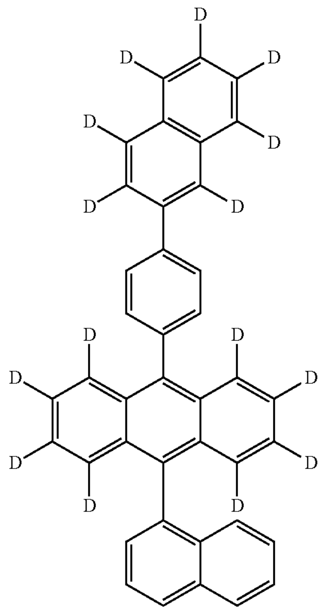
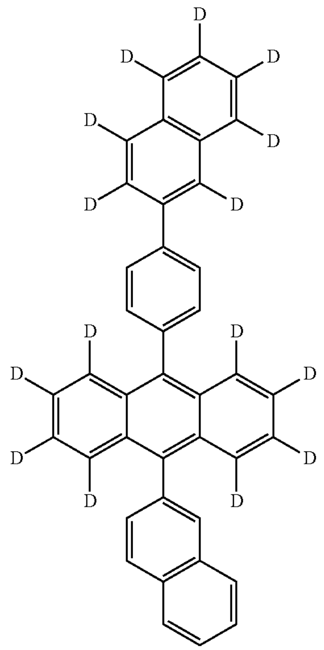

-continued
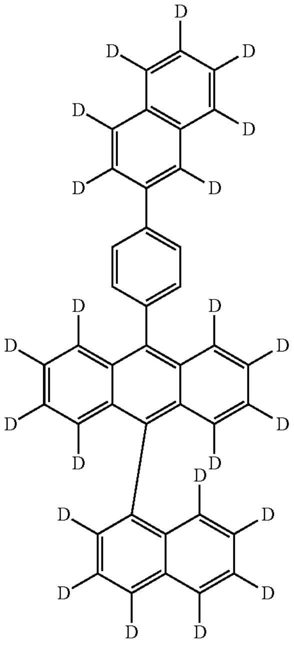
-continued
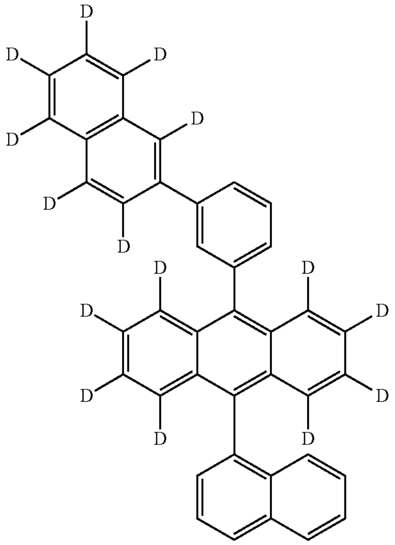
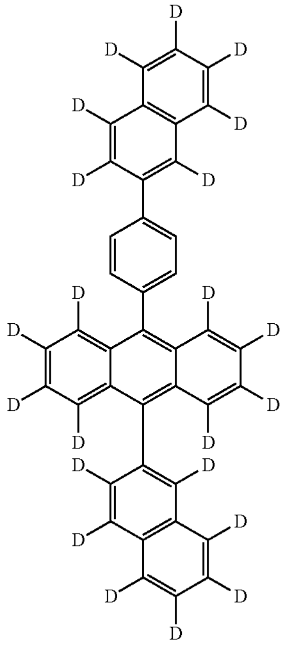
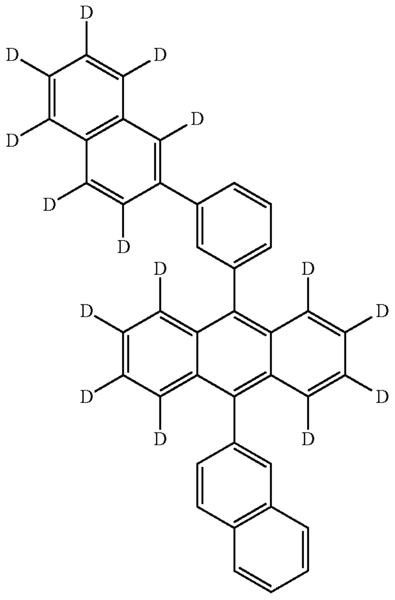

-continued
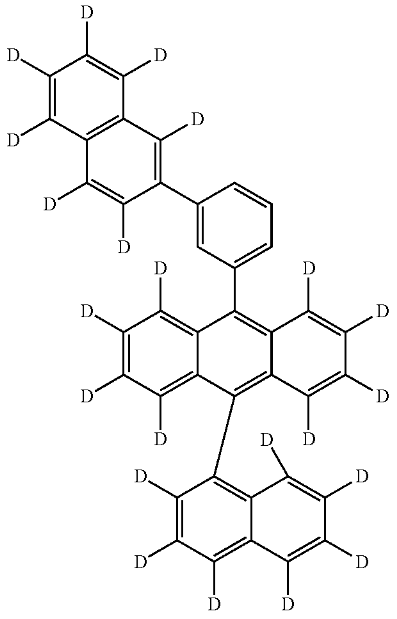
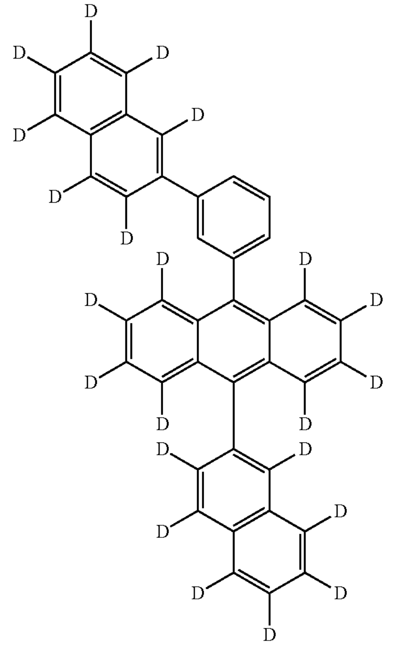
-continued
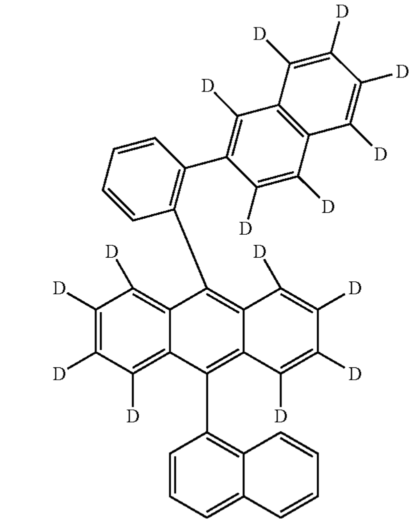
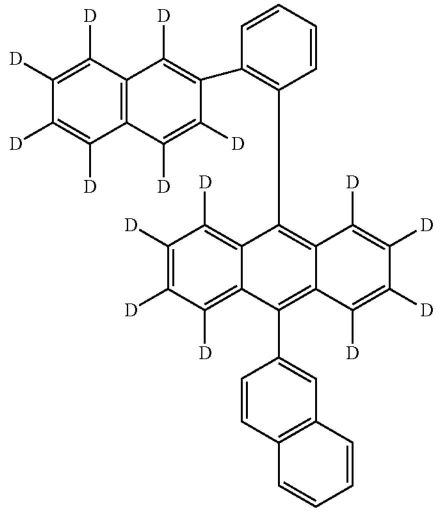
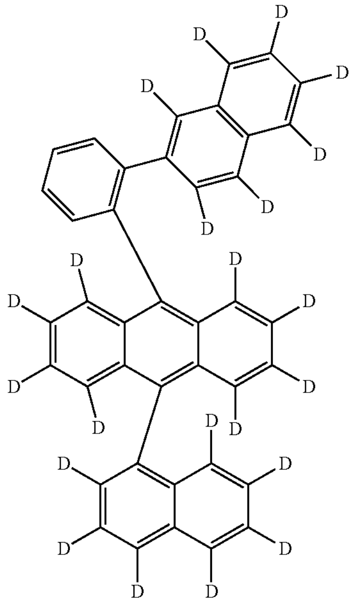

-continued
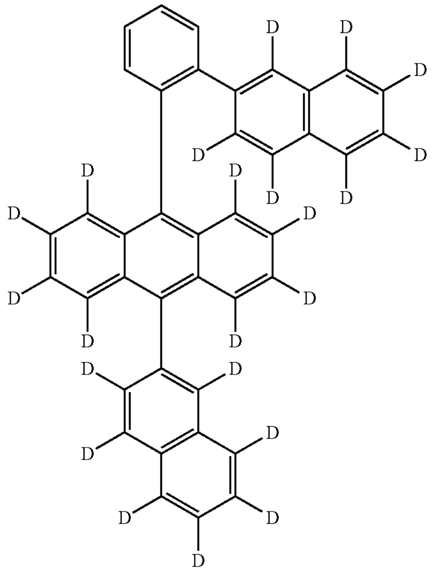
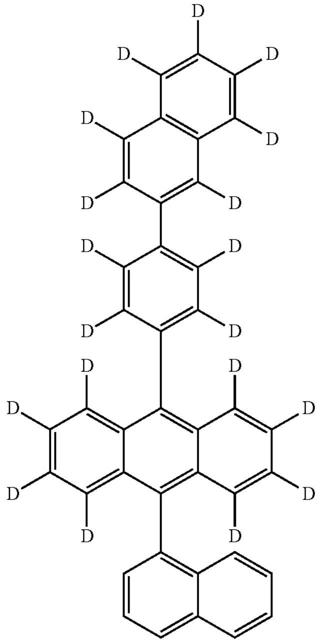
-continued
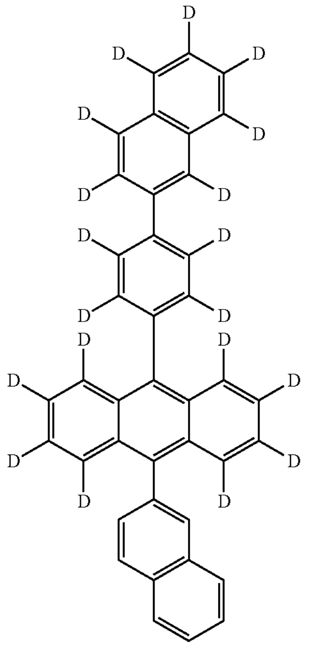
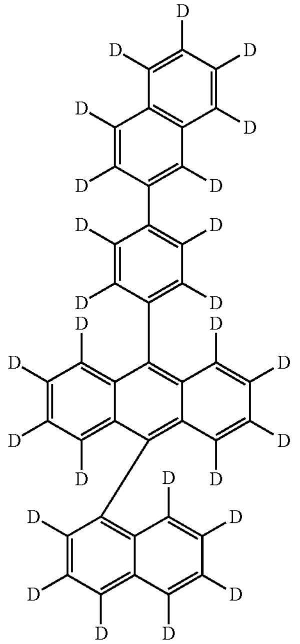

-continued
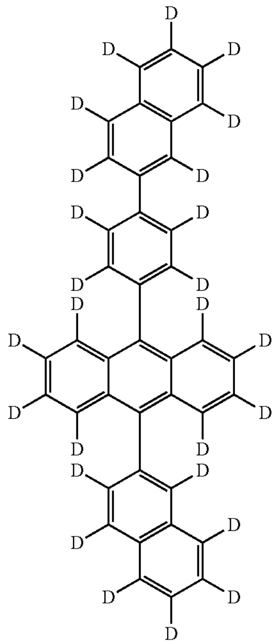
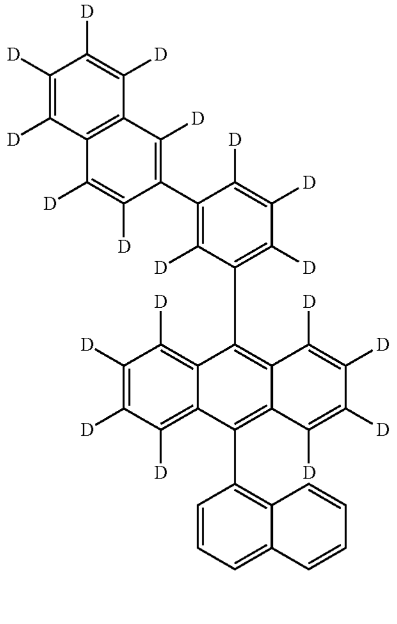
-continued
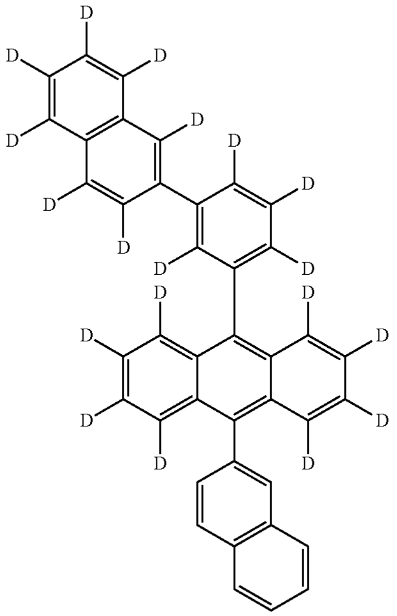
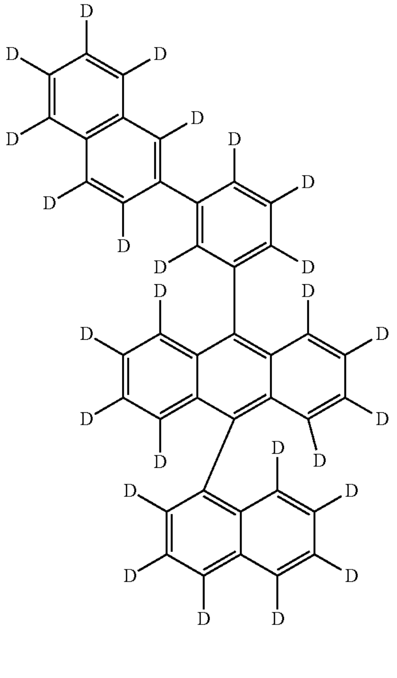

-continued
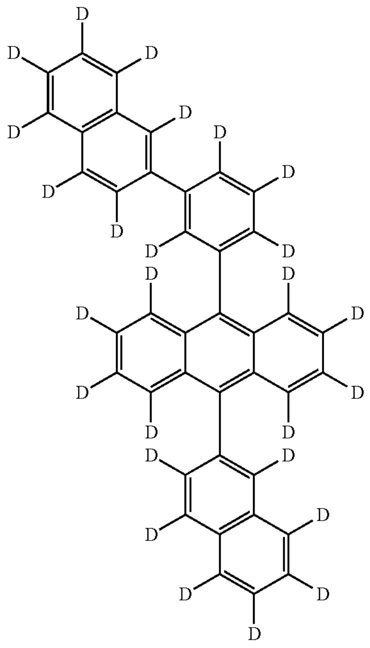
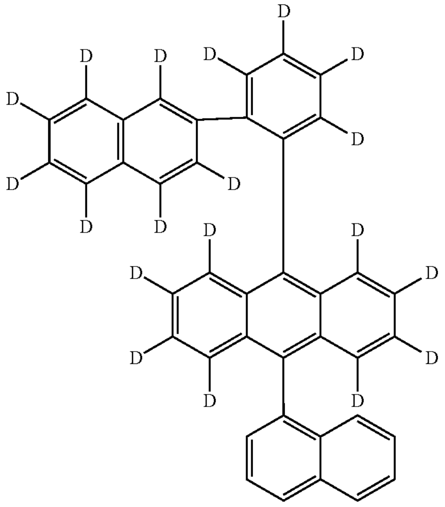
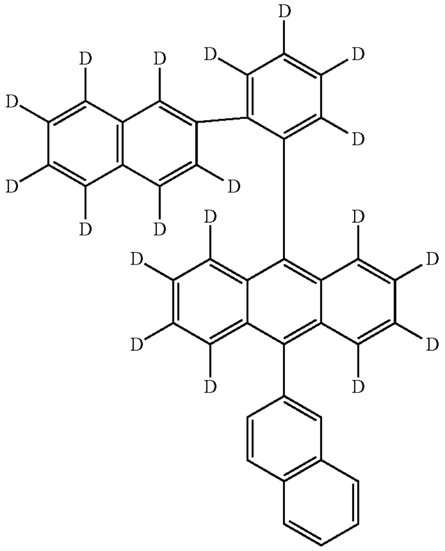
-continued
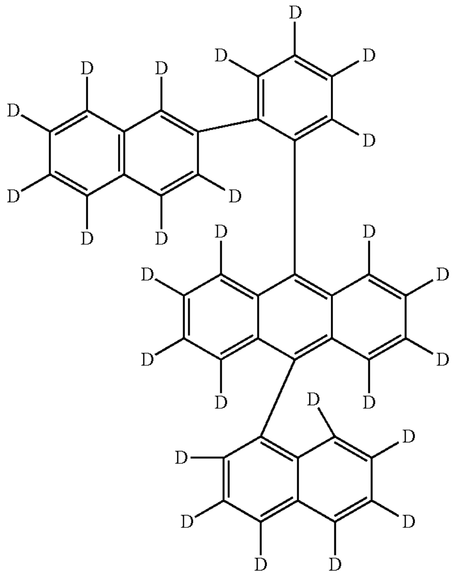
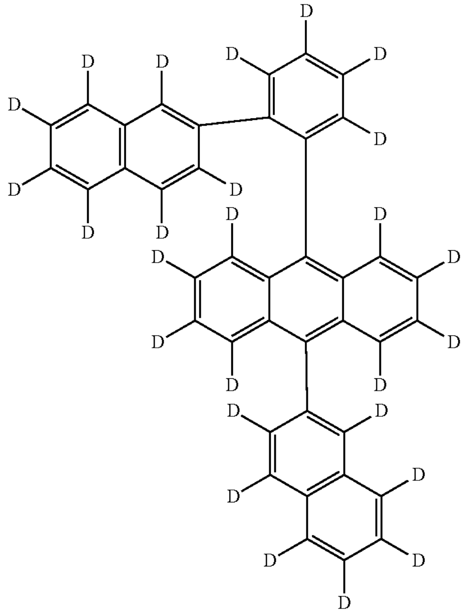
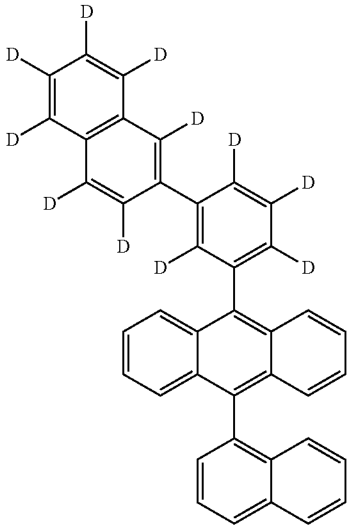

-continued
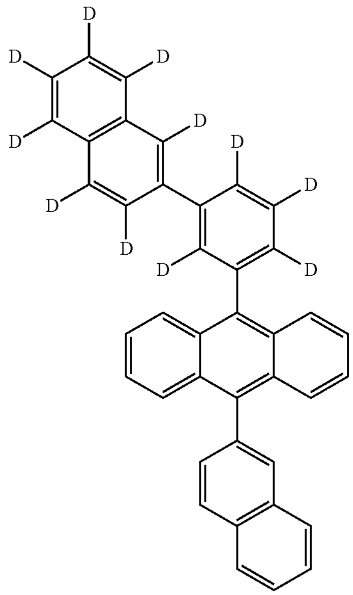
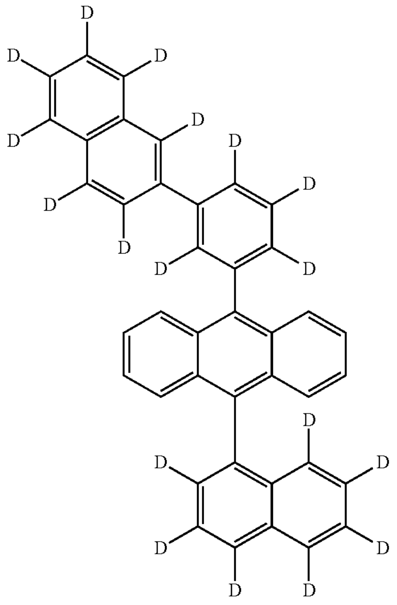
-continued
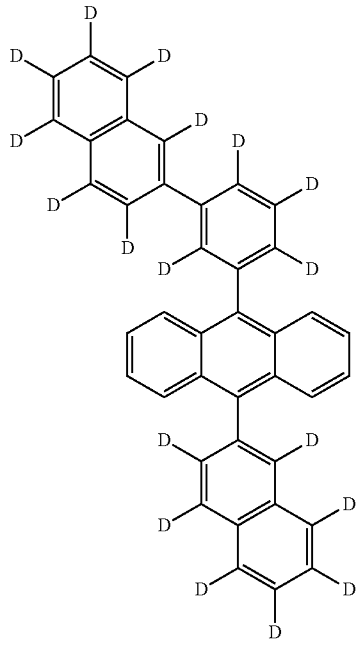
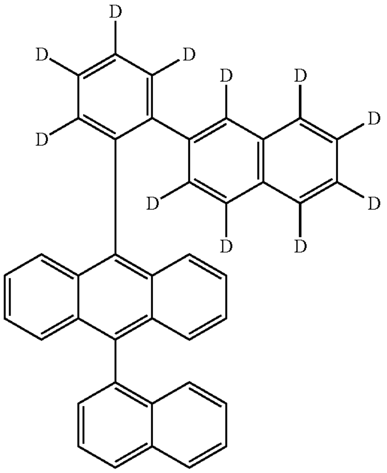
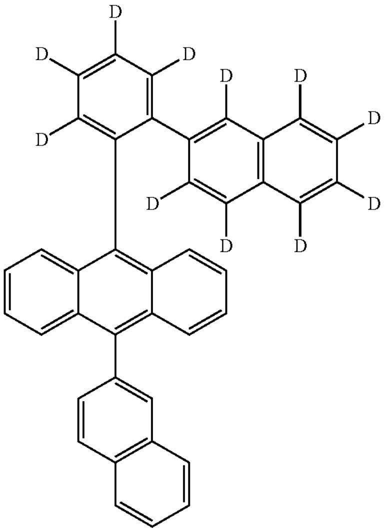

-continued
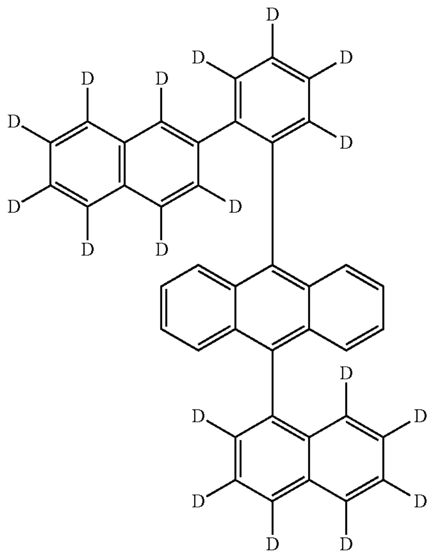
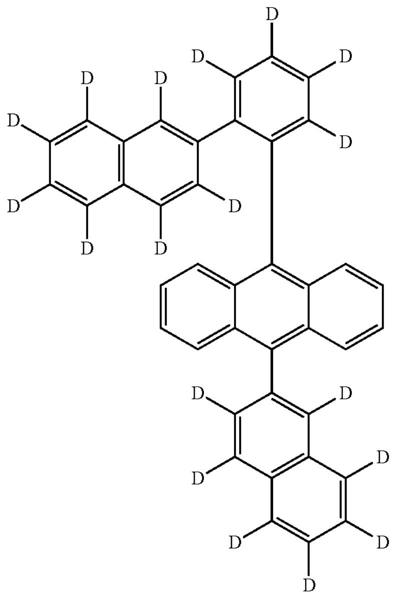
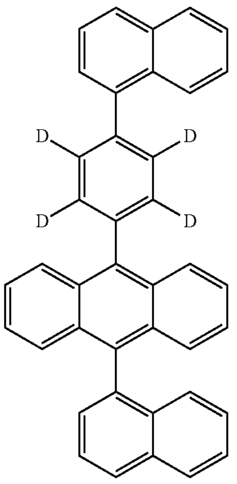
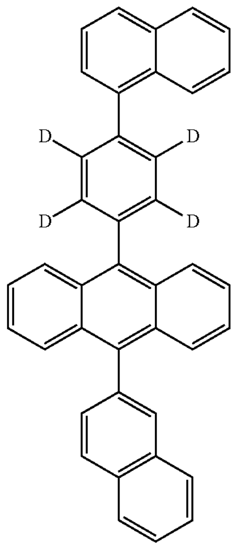
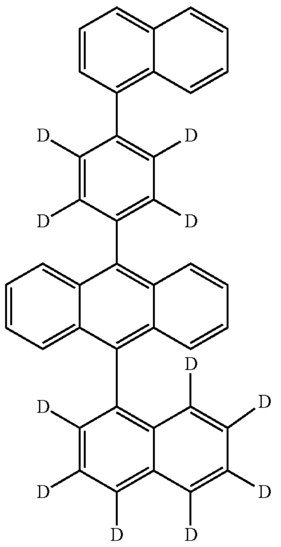
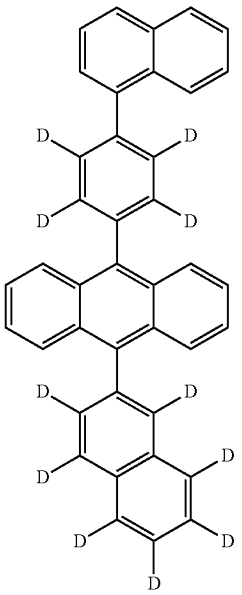
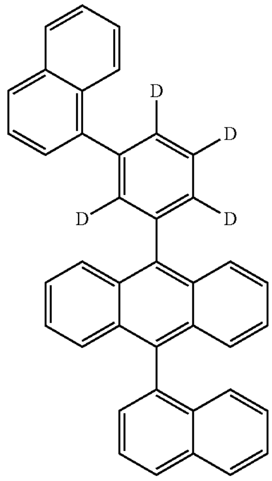
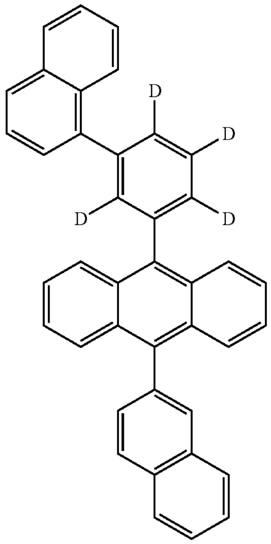

-continued
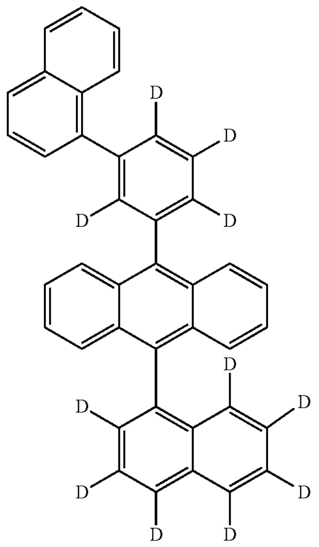
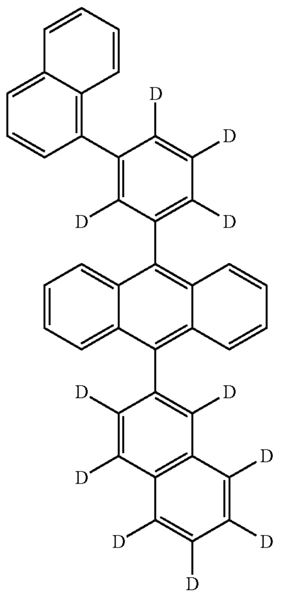
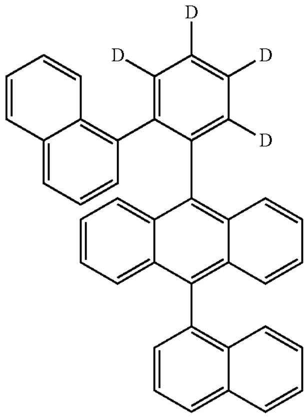
-continued
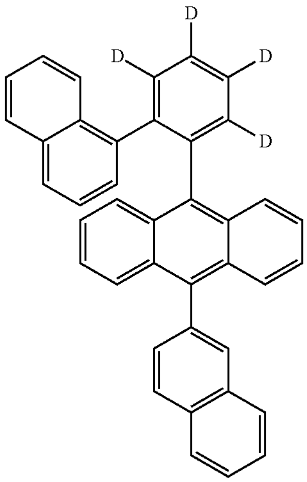
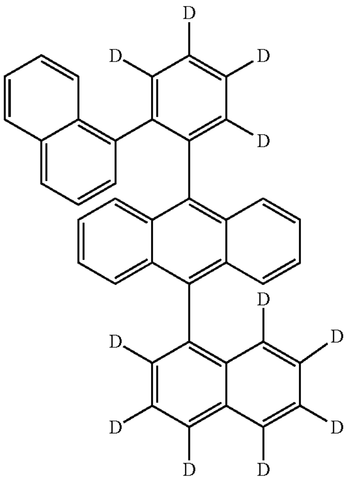
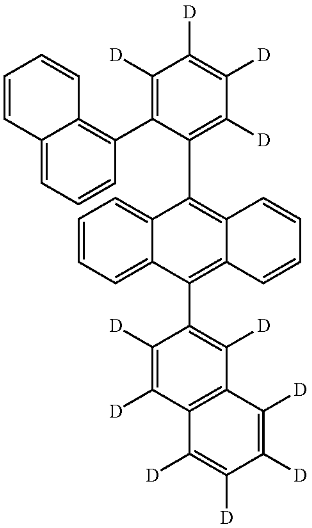

-continued
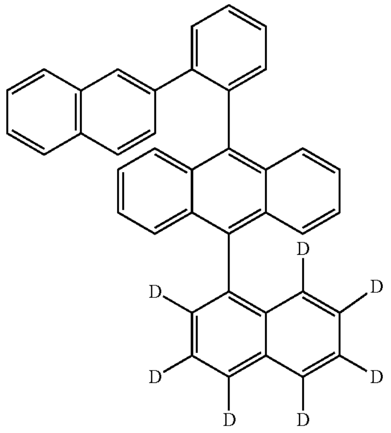
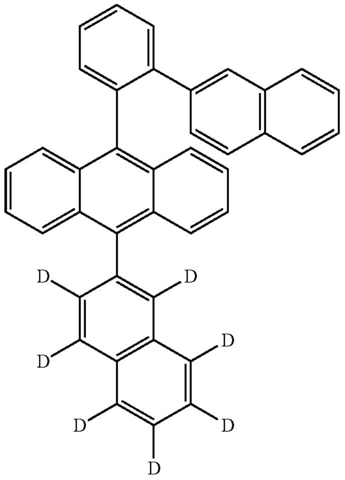
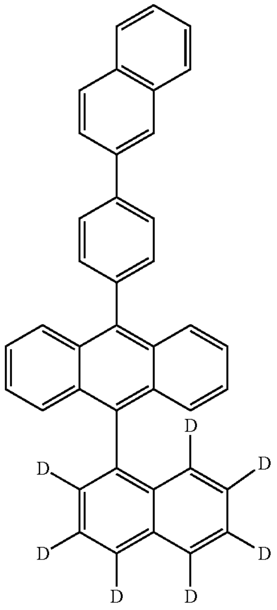
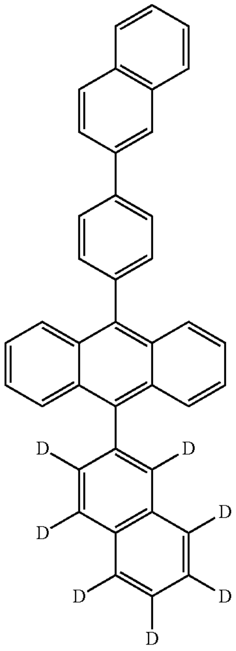
-continued
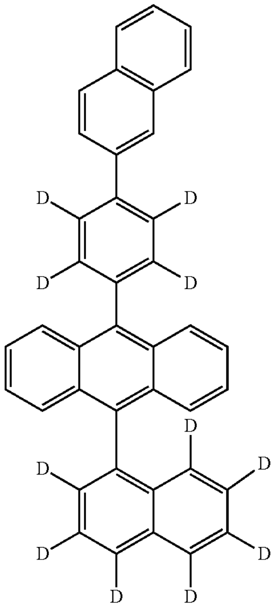
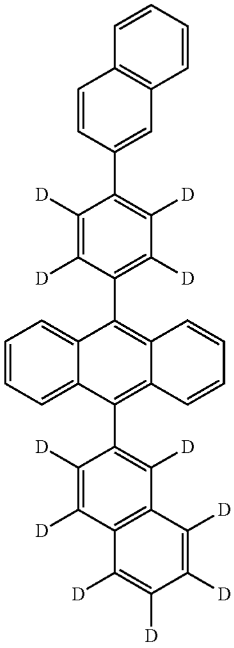
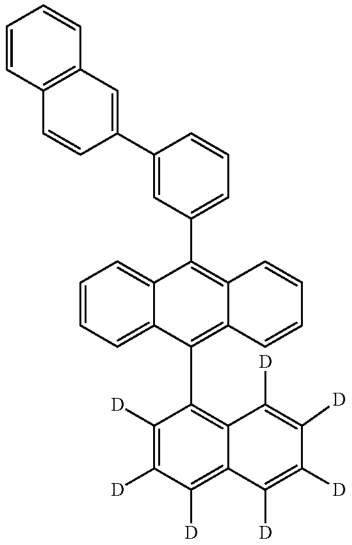

-continued
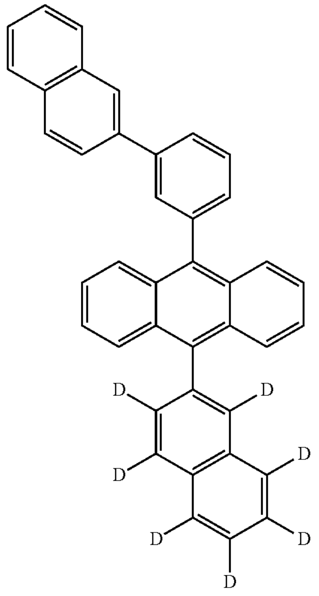
-continued
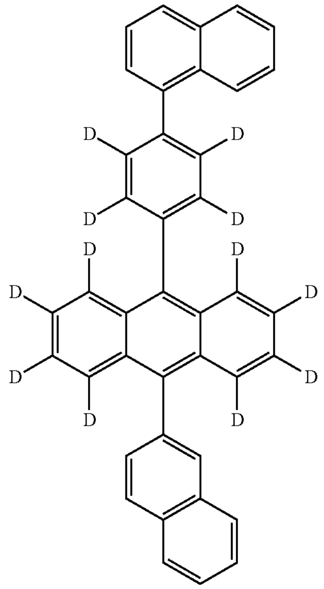
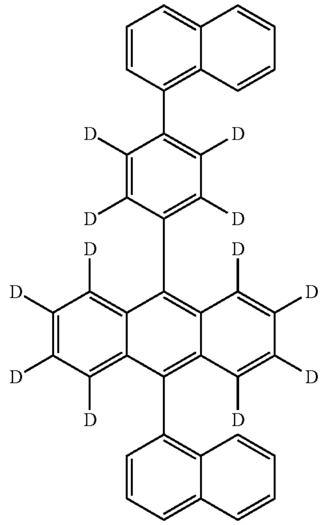
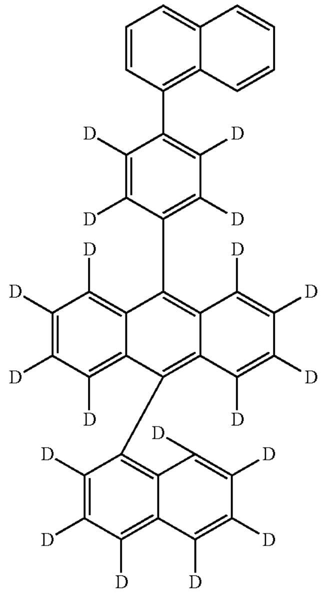

-continued
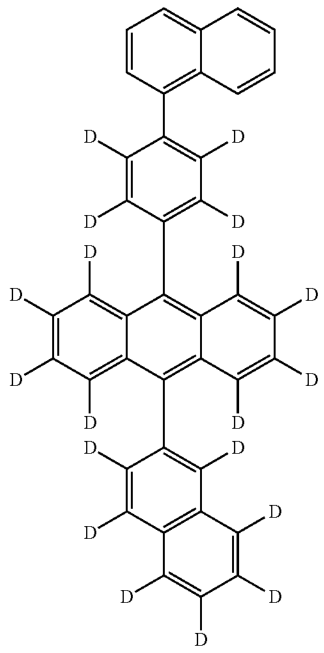
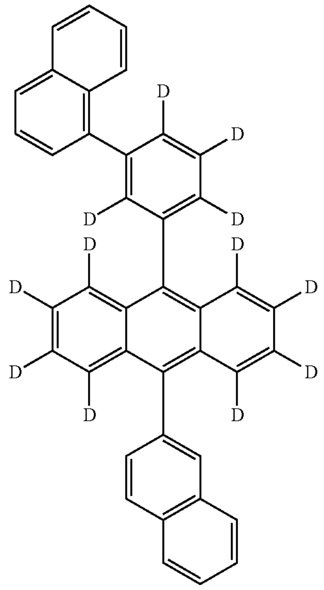
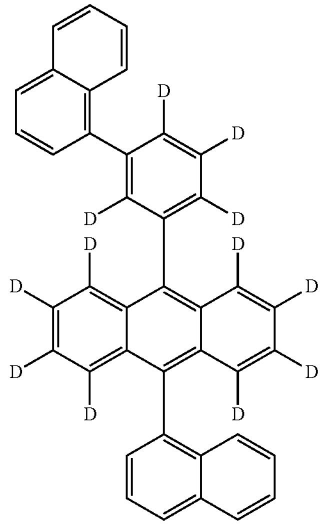
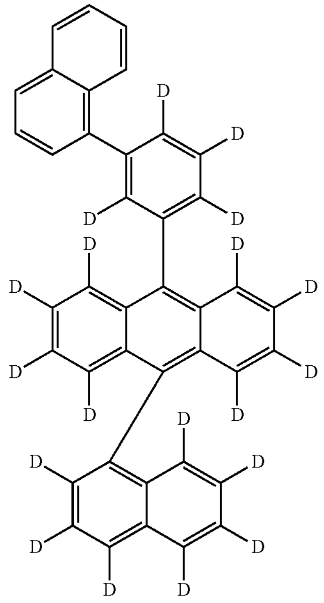
-continued

-continued
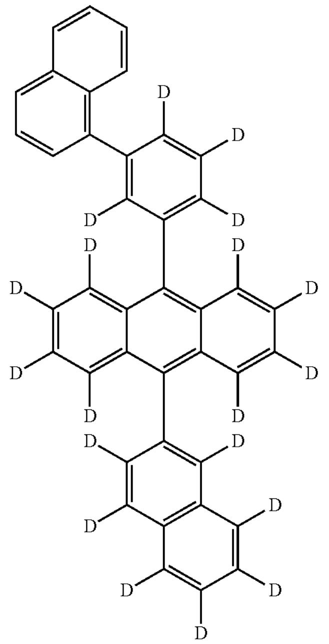
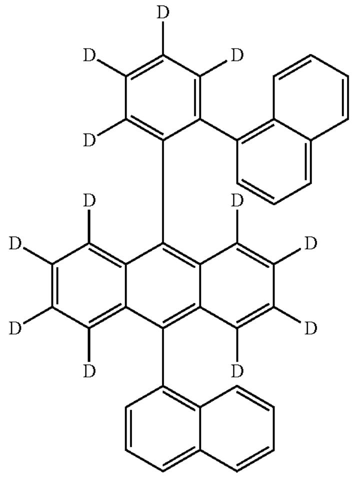
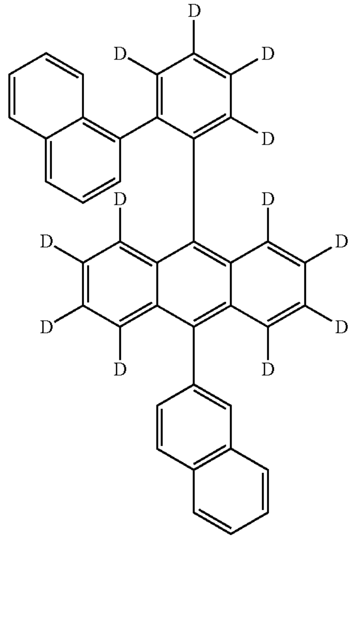
-continued
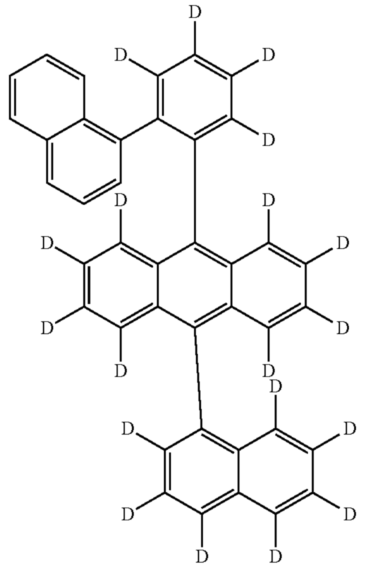
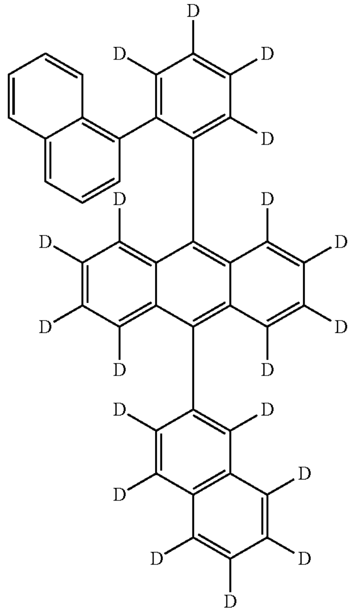

-continued
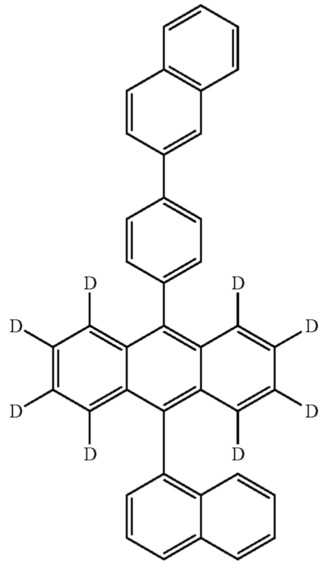
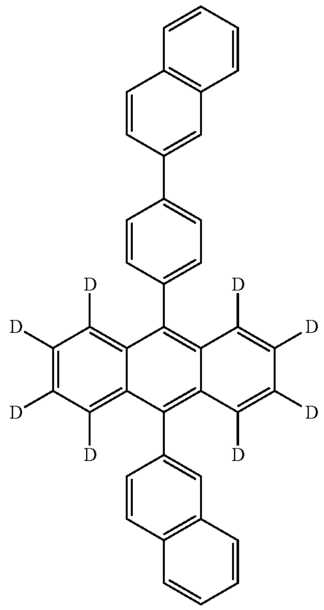
-continued
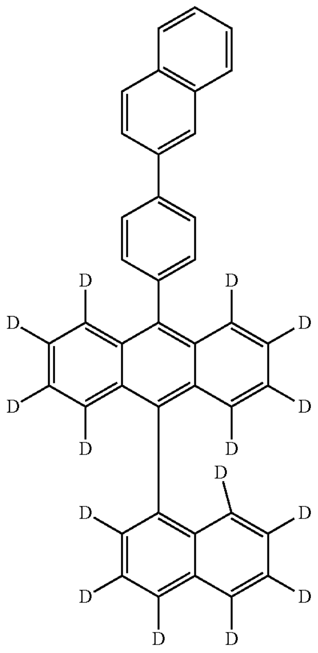
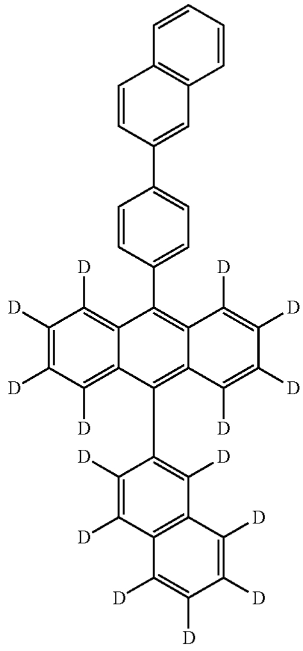

-continued
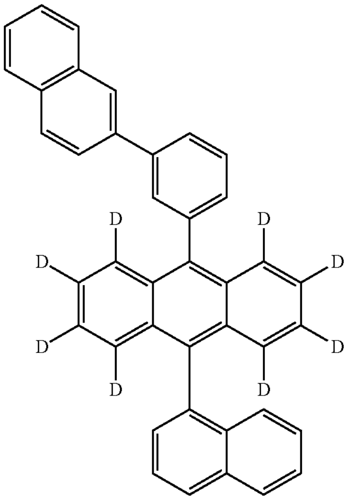
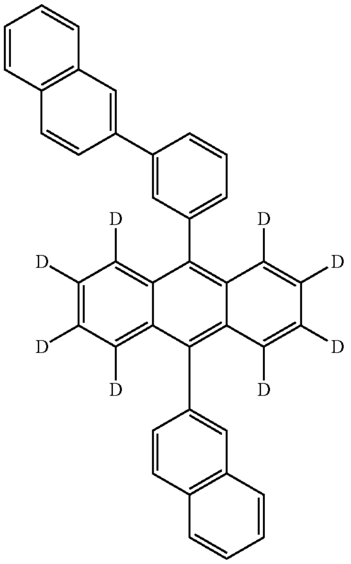
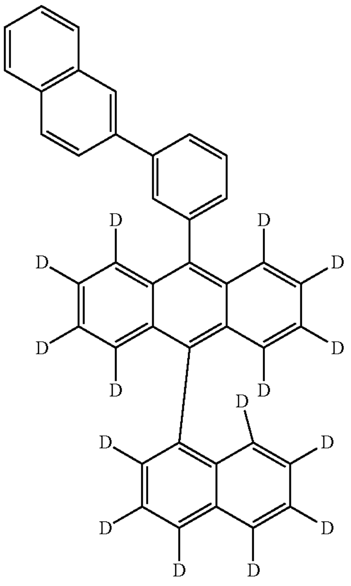
-continued
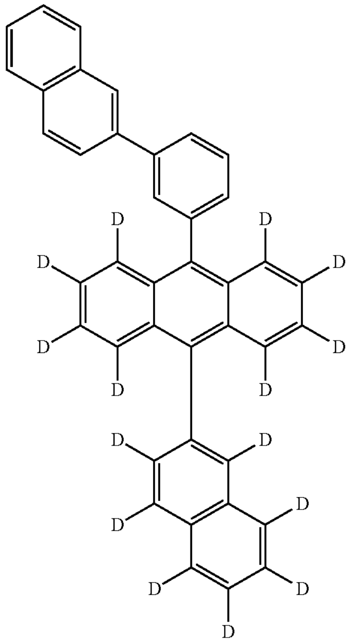
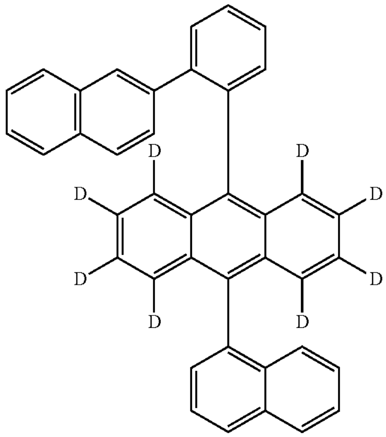
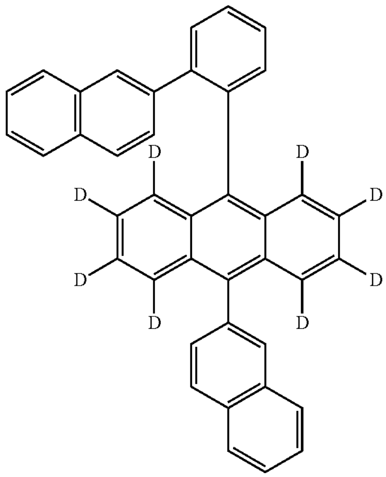

-continued
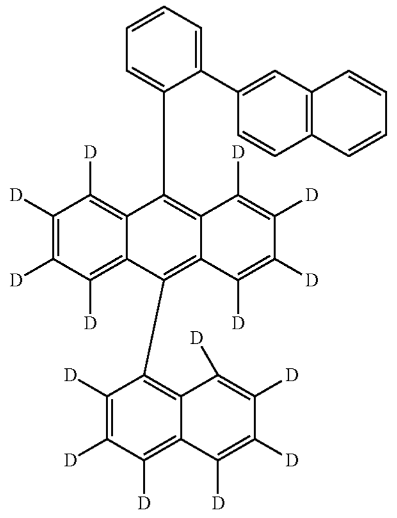
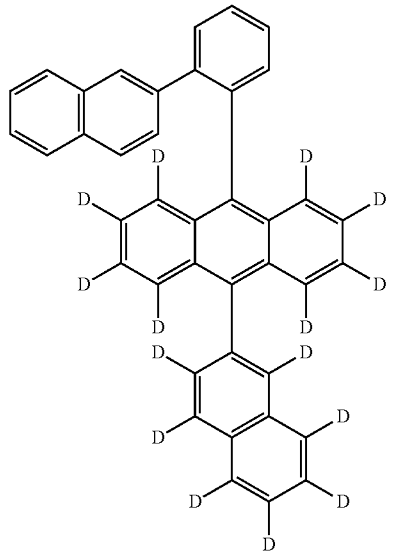
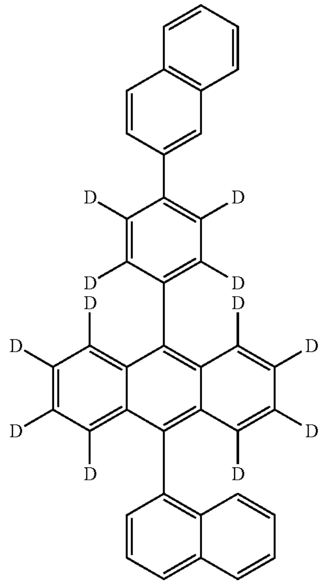
-continued
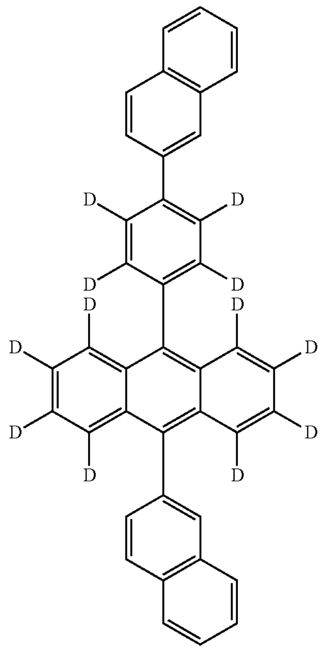
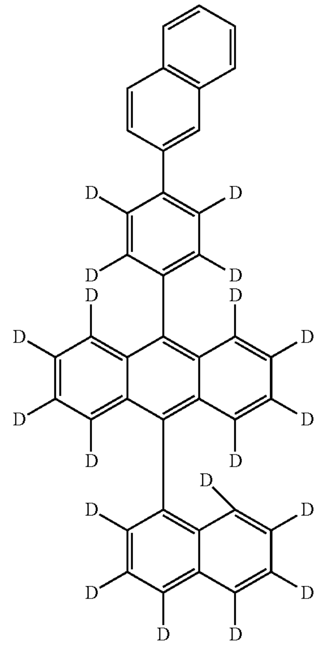

-continued
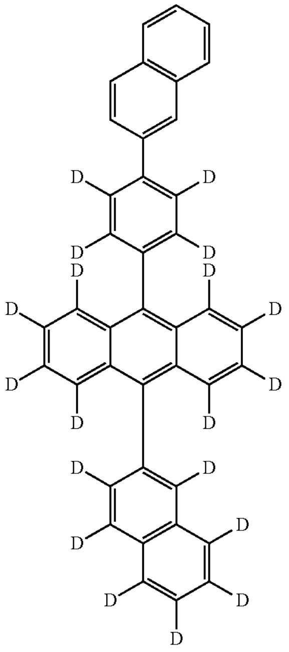
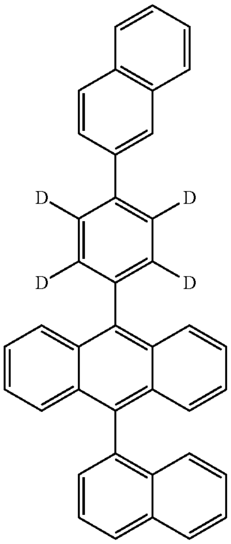
-continued
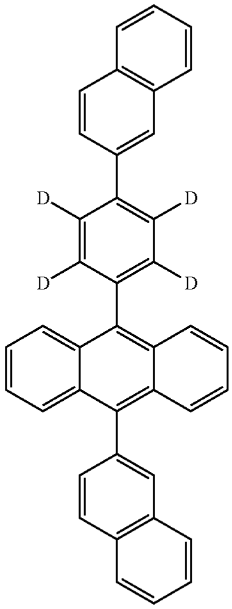
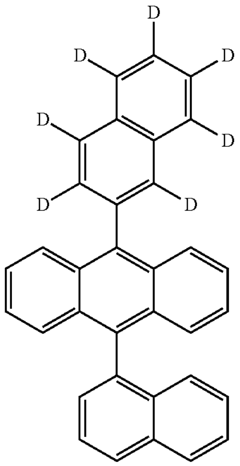
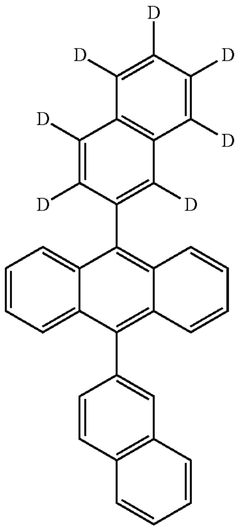

-continued
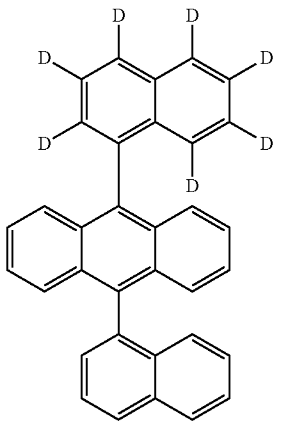
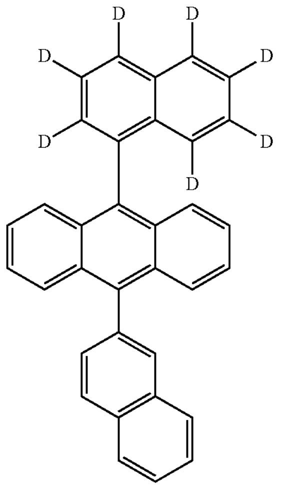
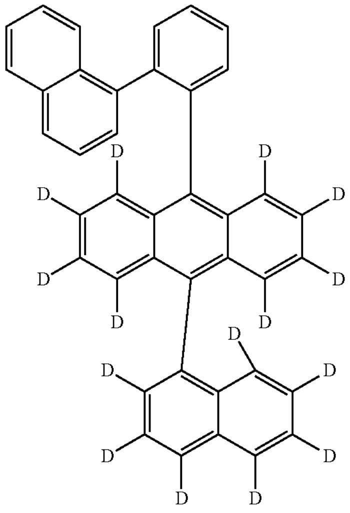
-continued
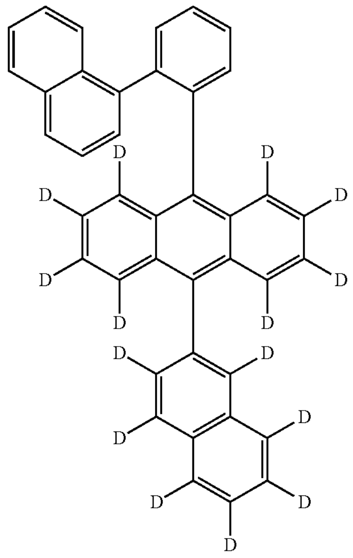
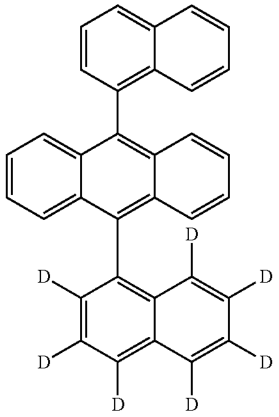
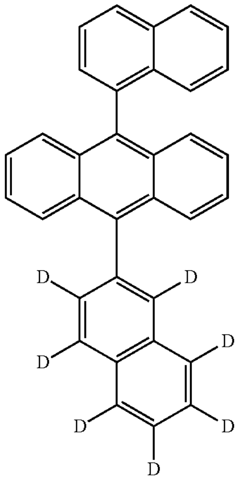

-continued
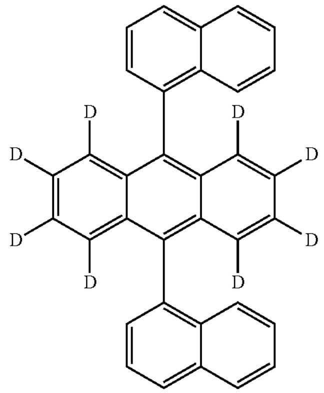
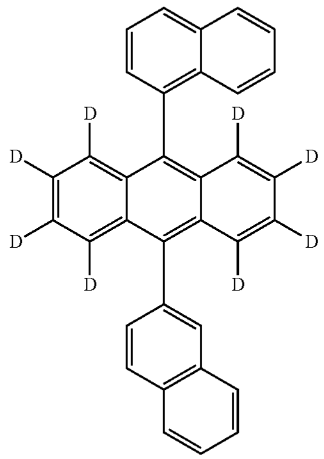
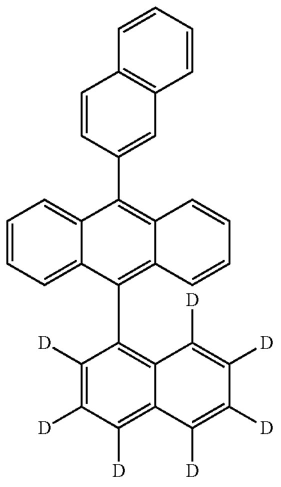
-continued
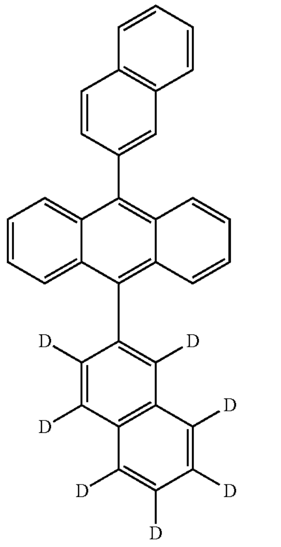
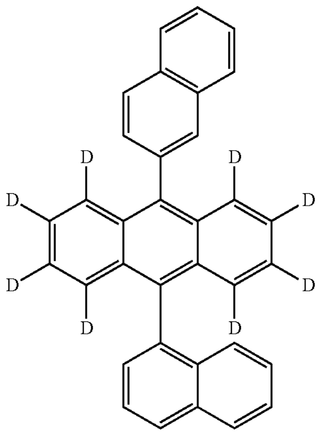
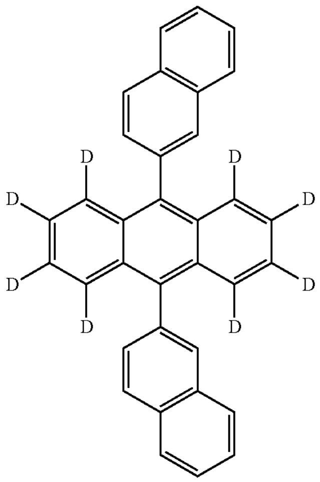

-continued
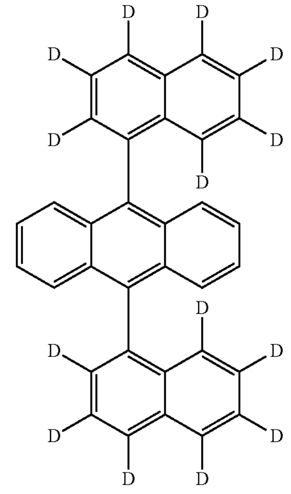
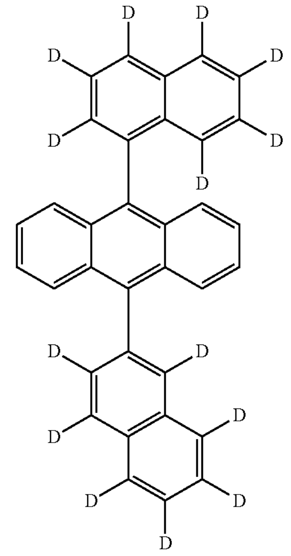
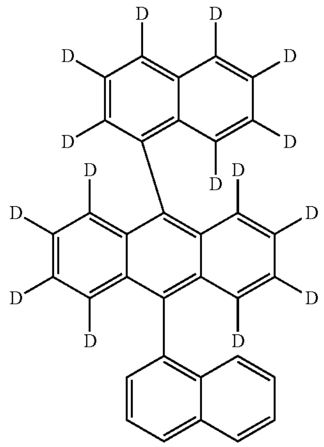
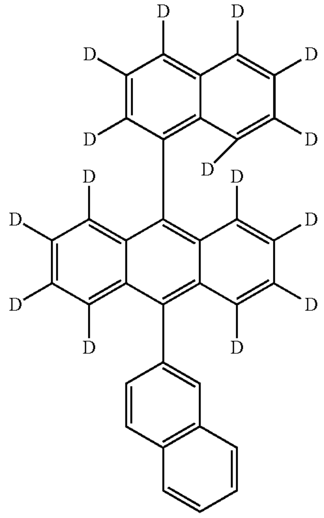
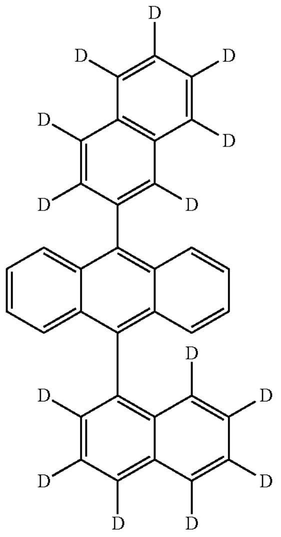
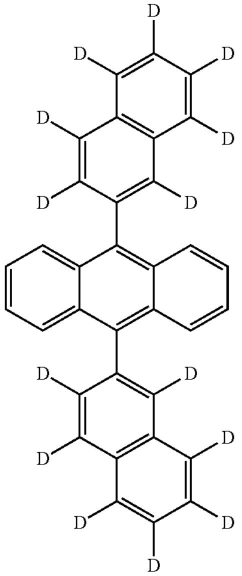

-continued
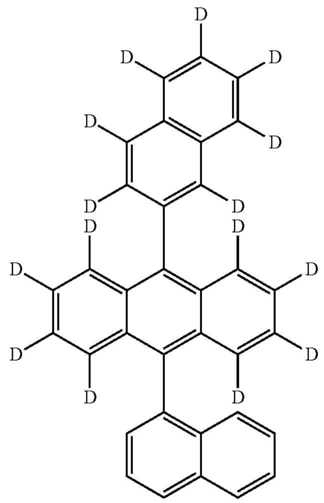
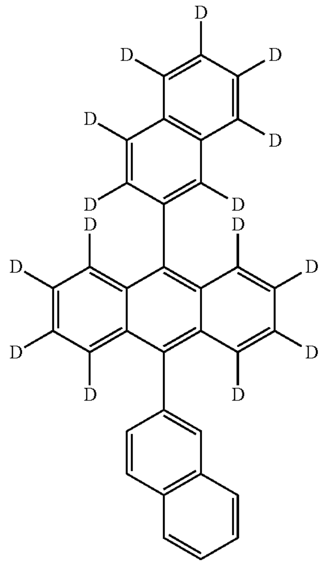
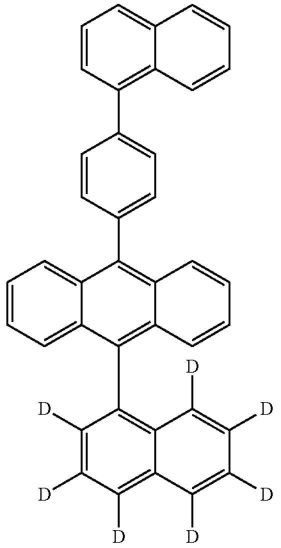
-continued
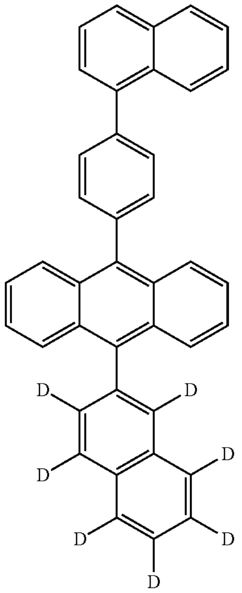
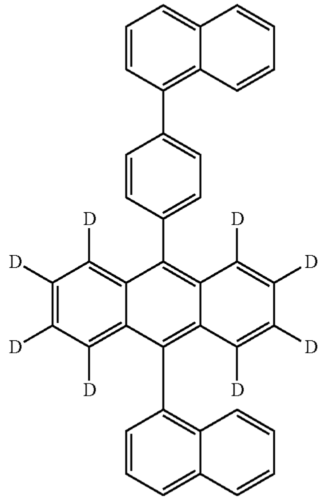
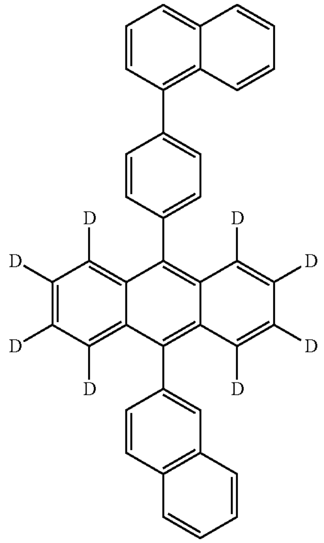

-continued
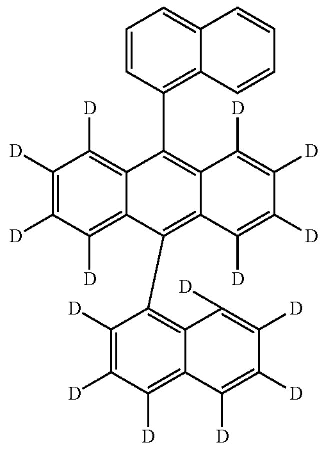
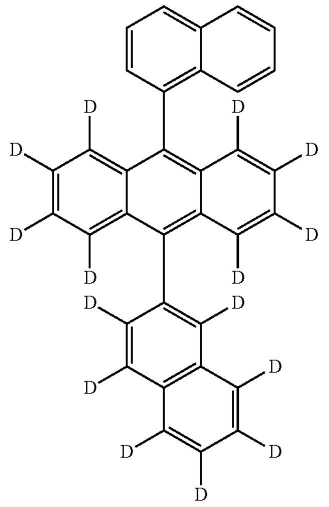
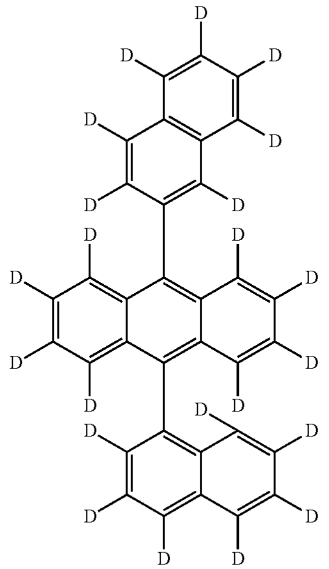
-continued
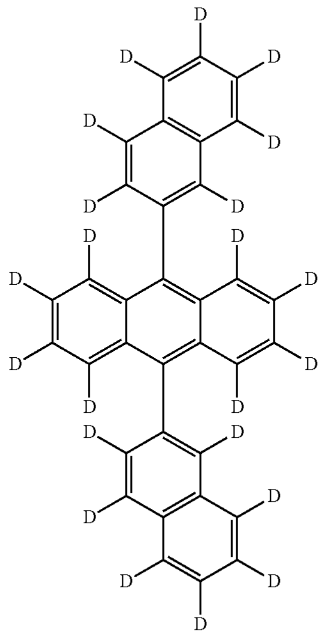
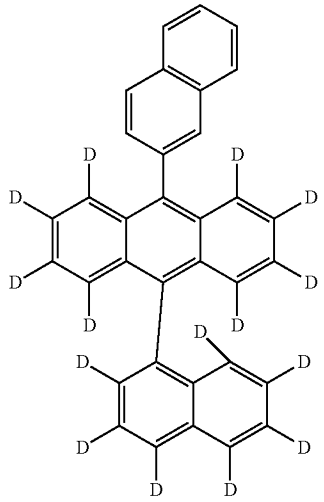
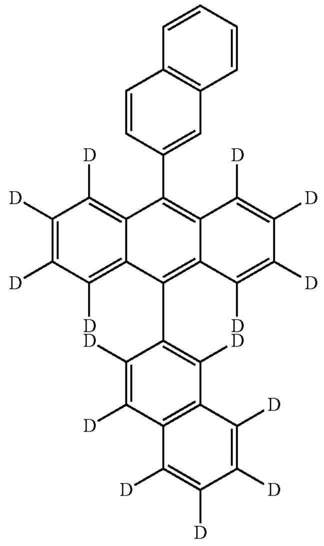

-continued
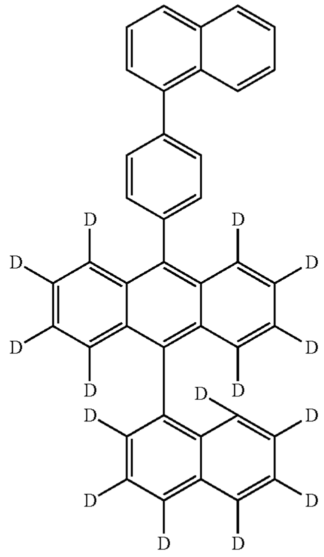
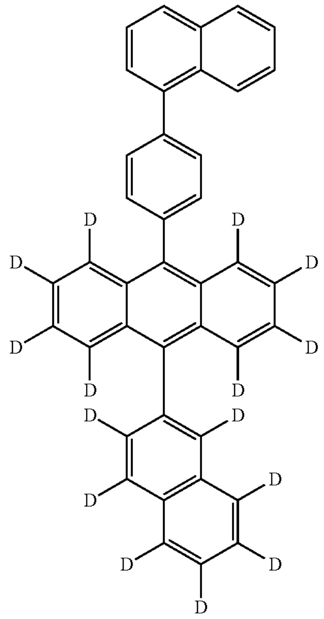
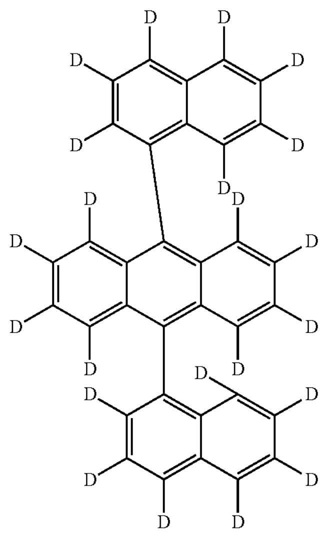
-continued
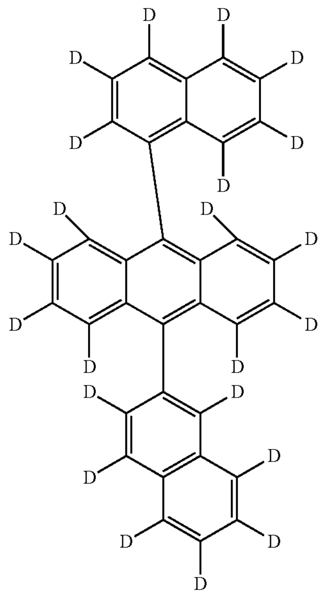
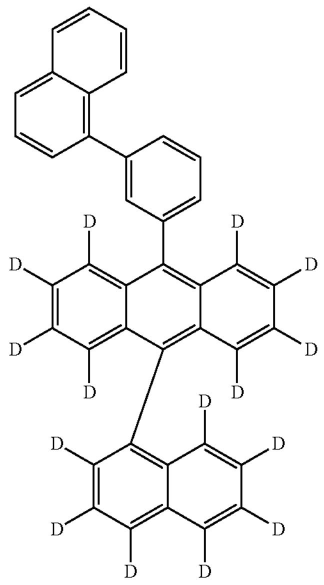

-continued
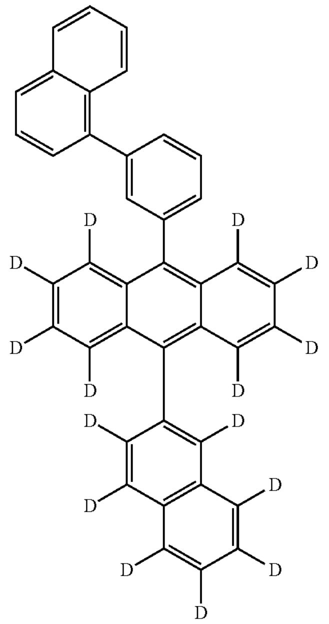
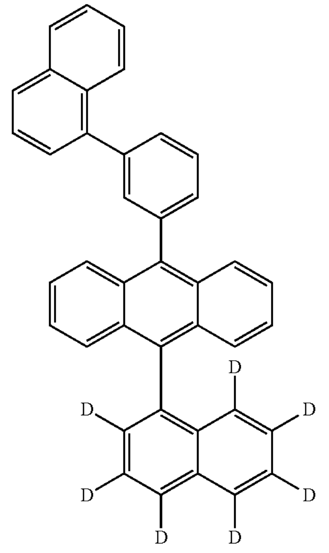
-continued
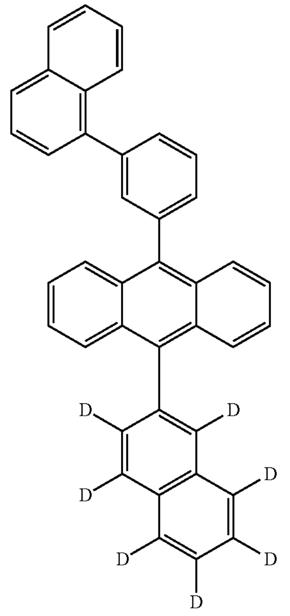
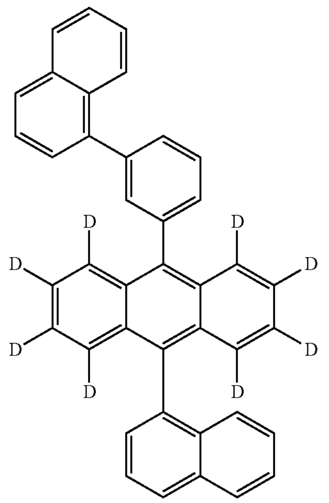
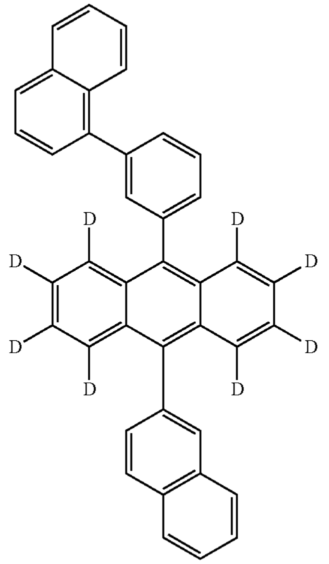

-continued
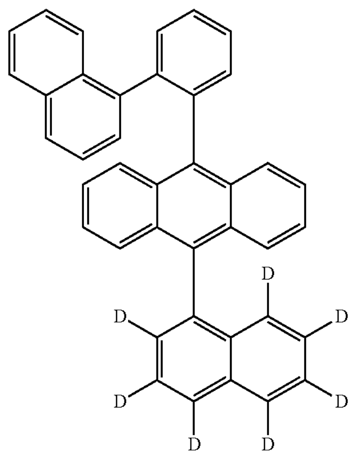
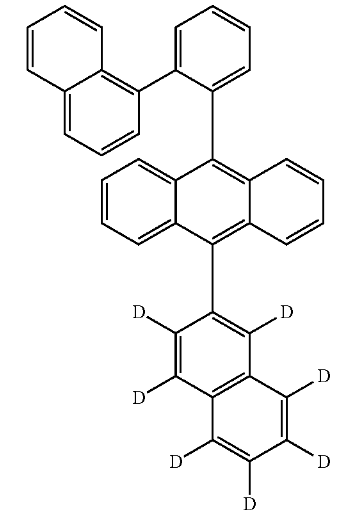
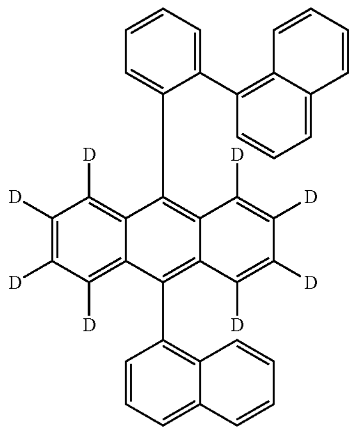
-continued
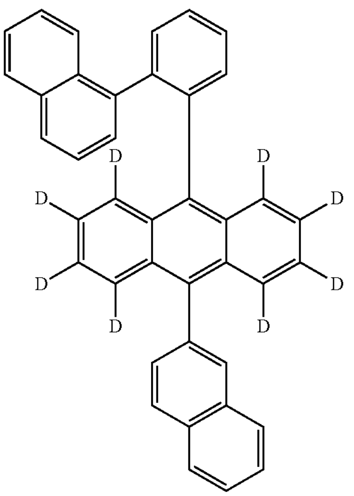
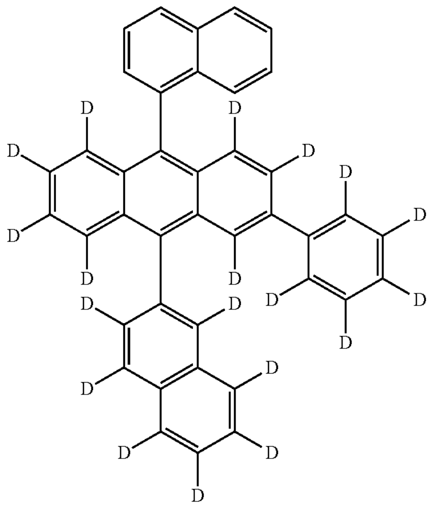
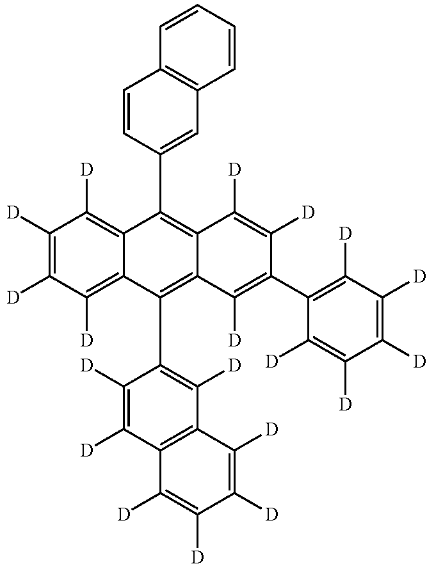

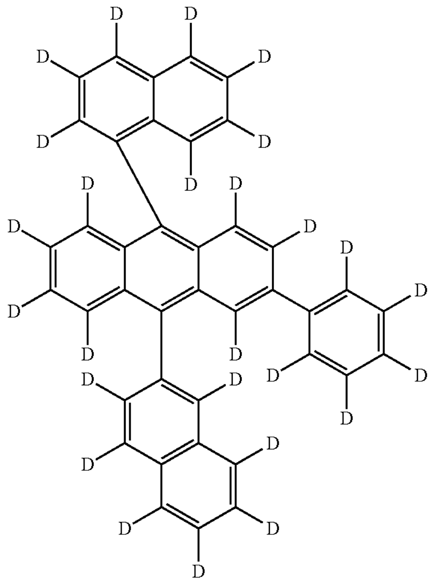
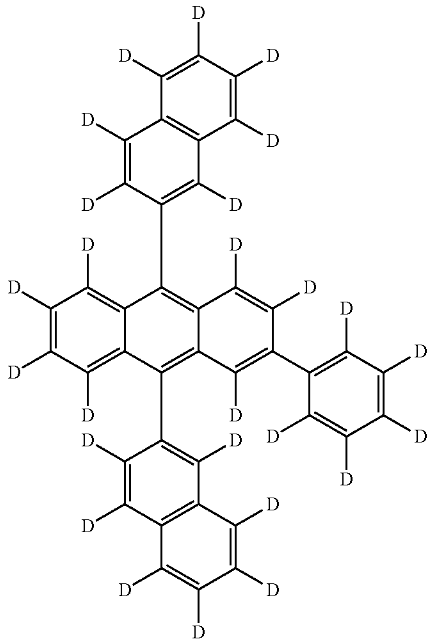
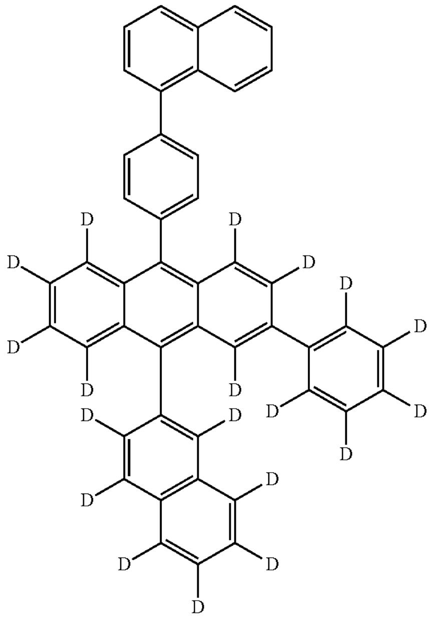
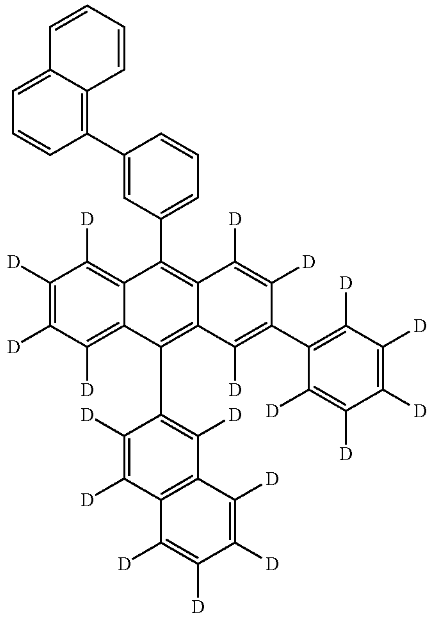

-continued
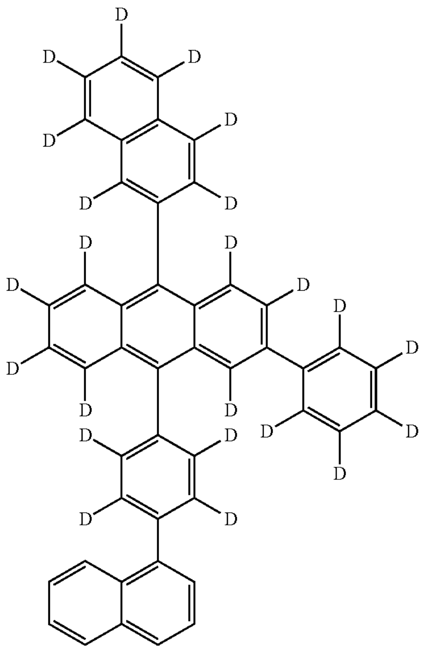
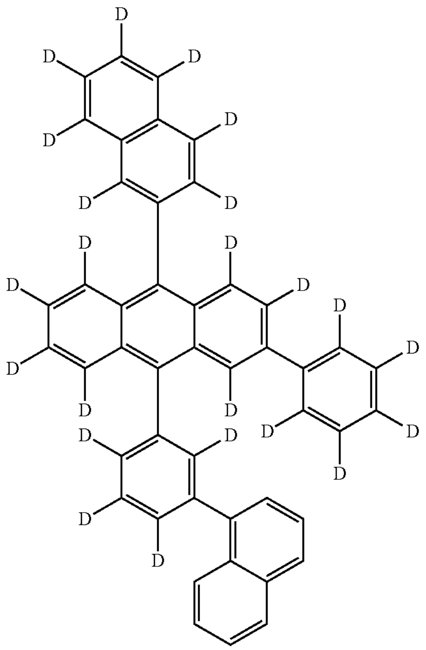
-continued
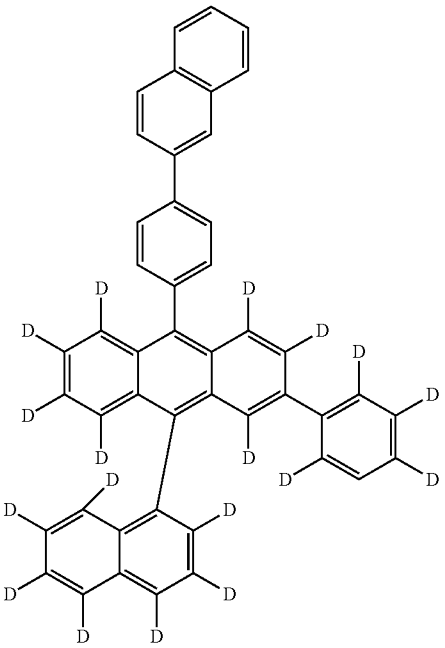
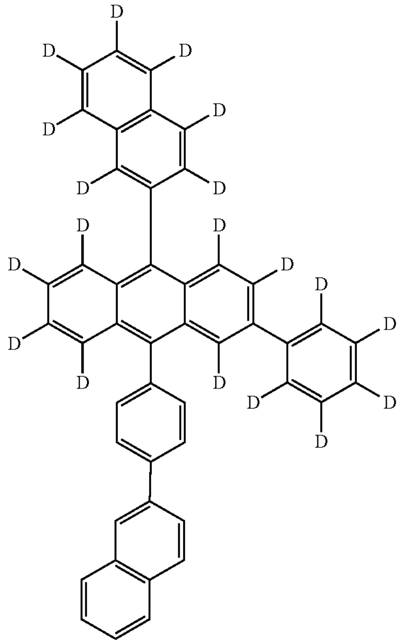

-continued
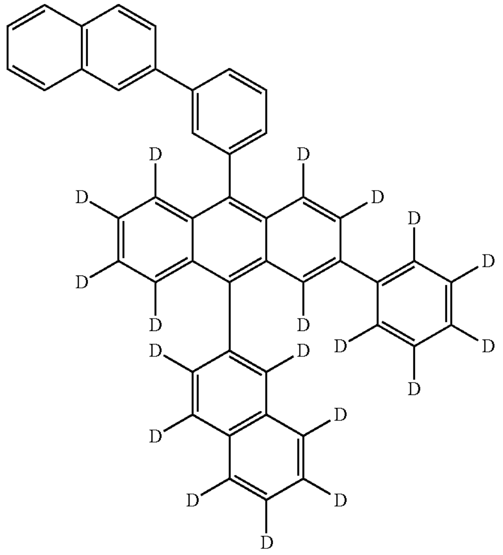
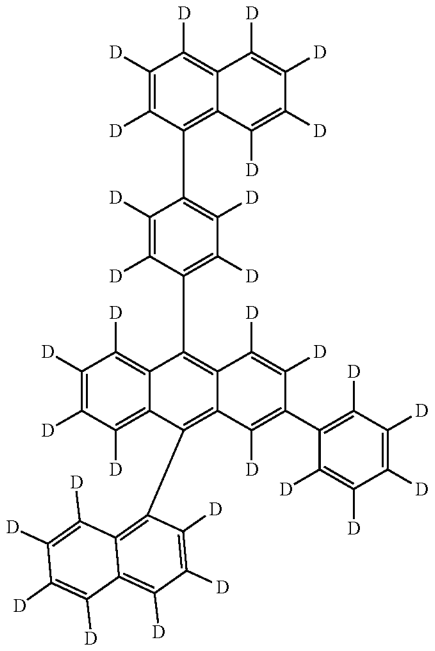
-continued
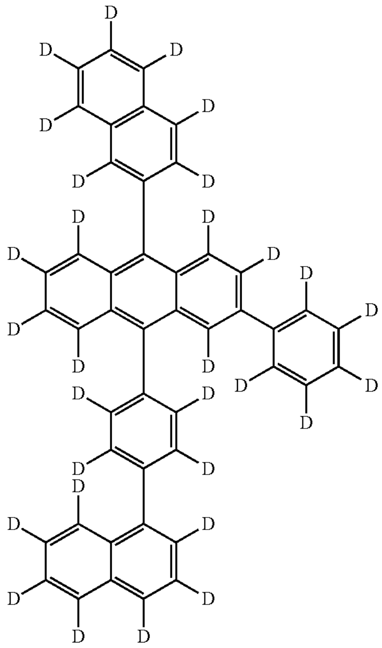
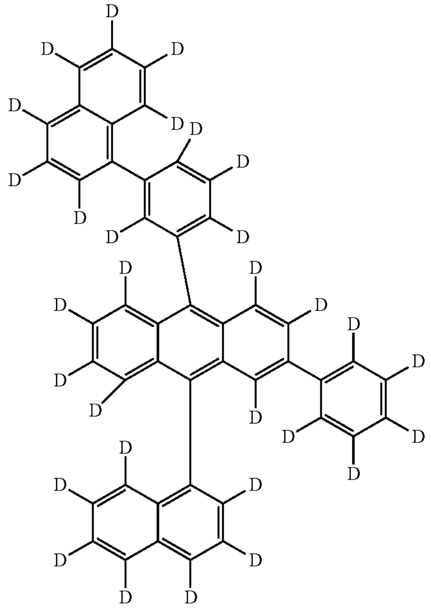

-continued
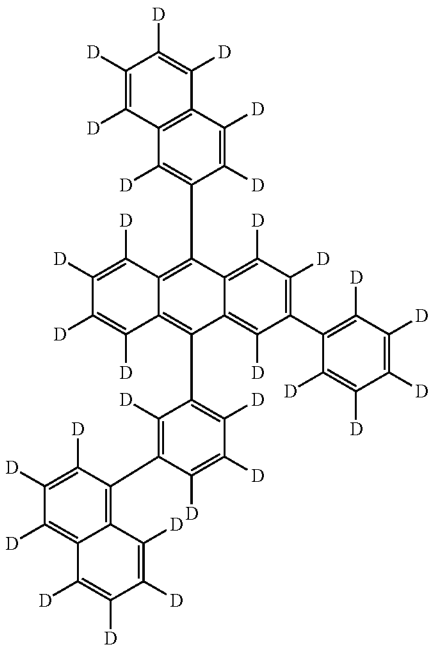
-continued
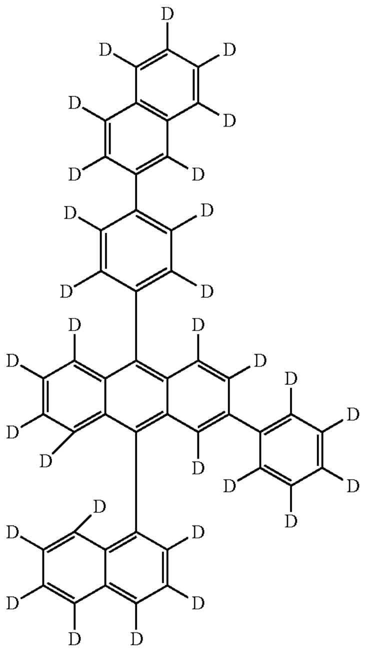
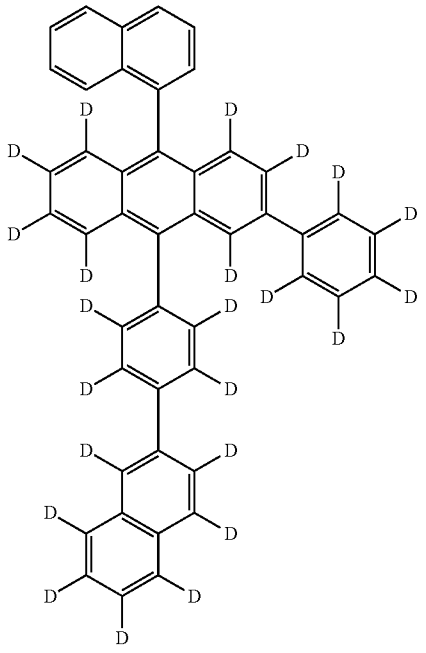
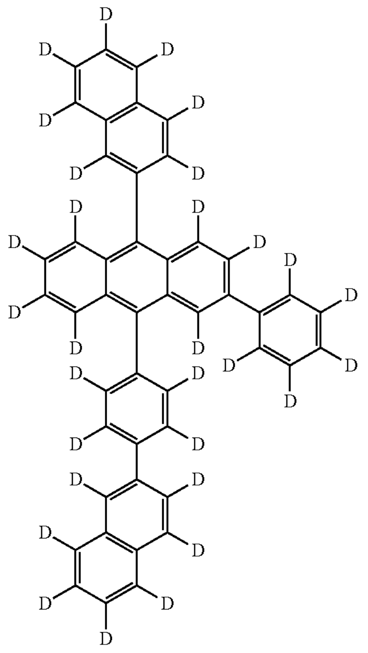

-continued
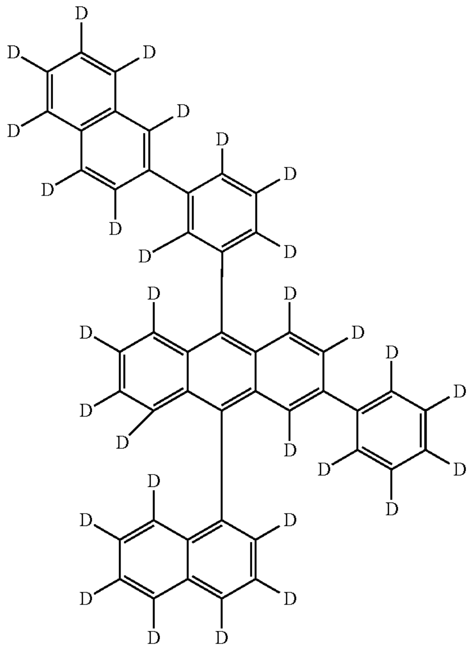
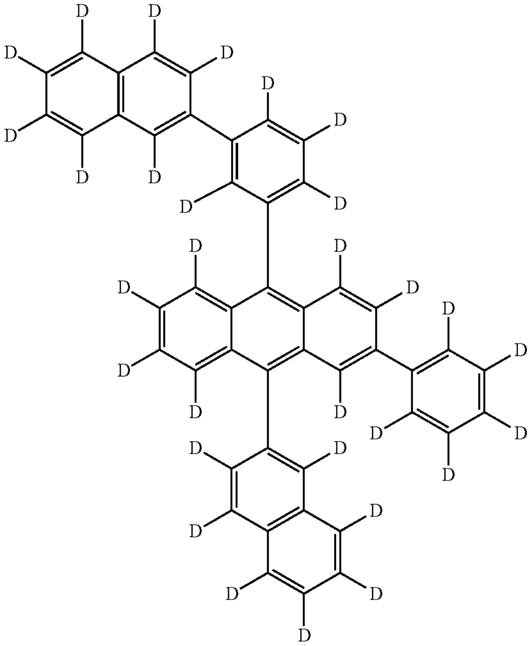
-continued
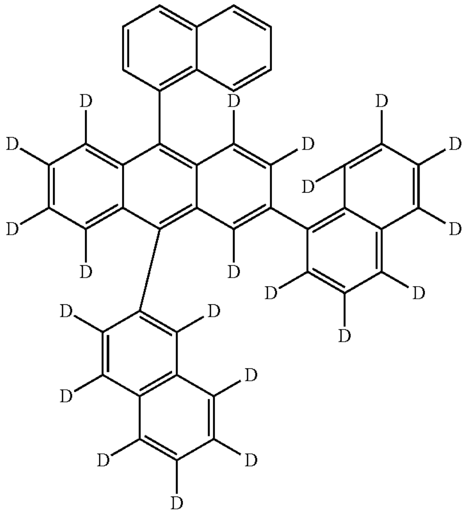
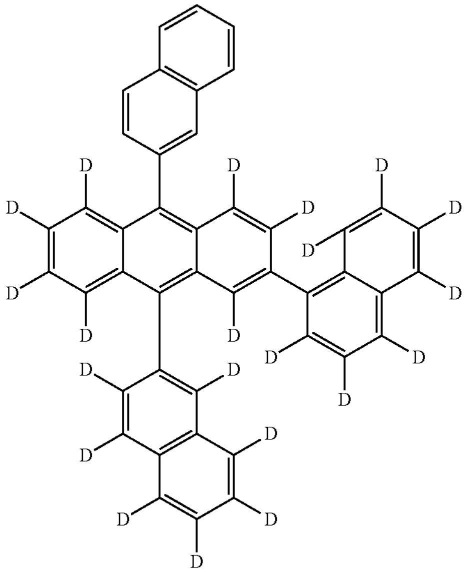
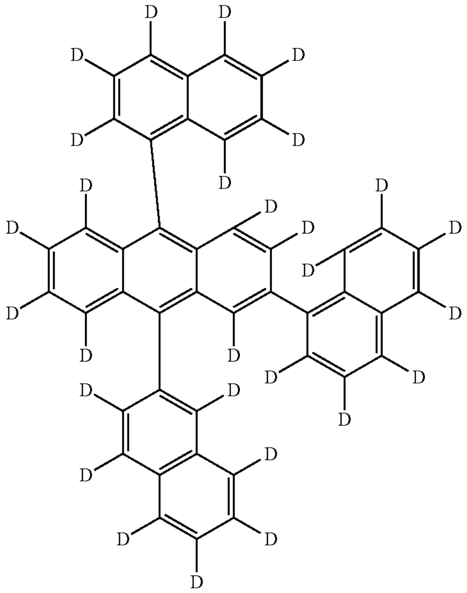

-continued
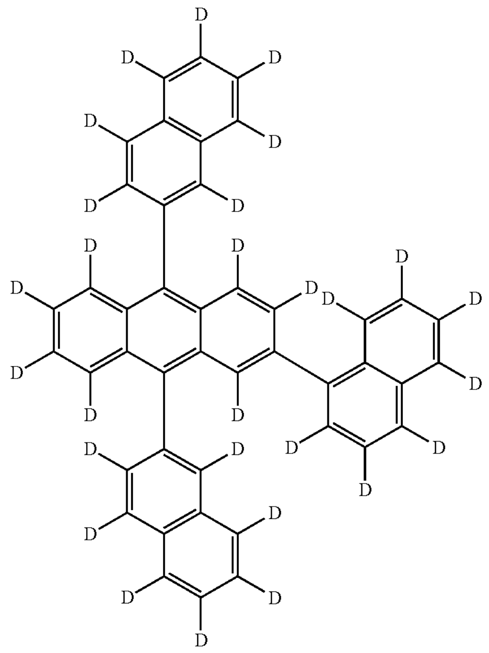
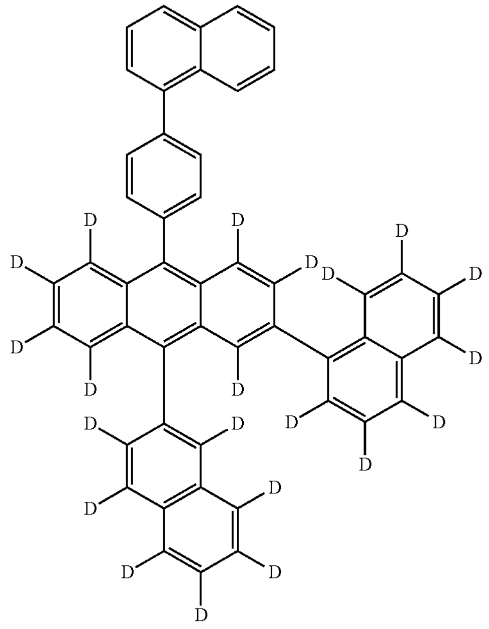
-continued
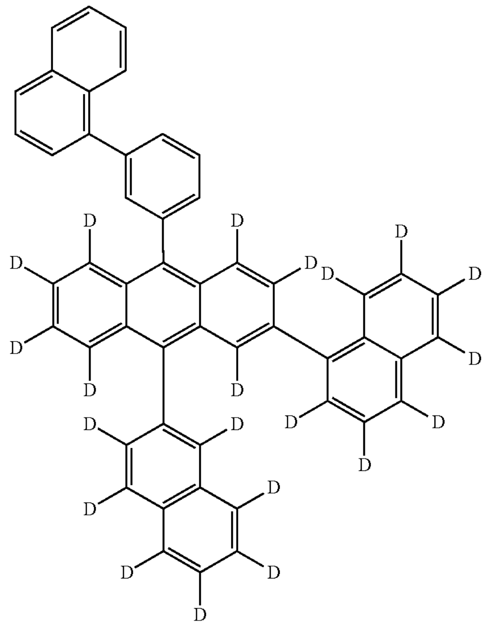
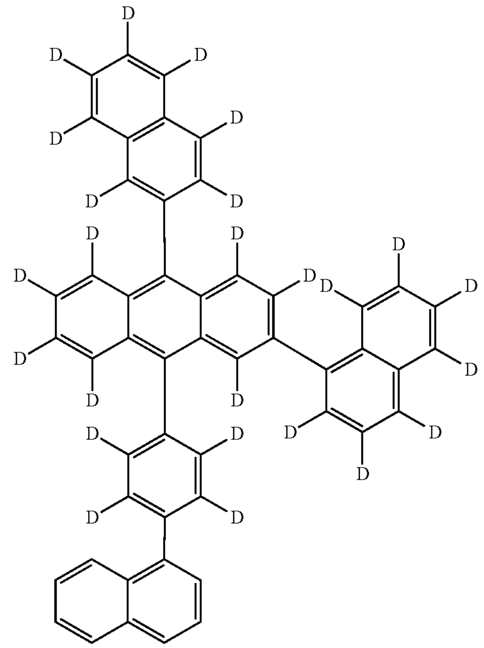

-continued
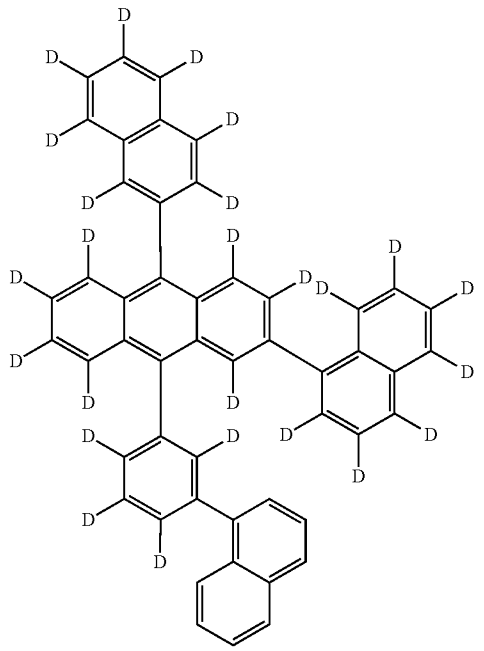
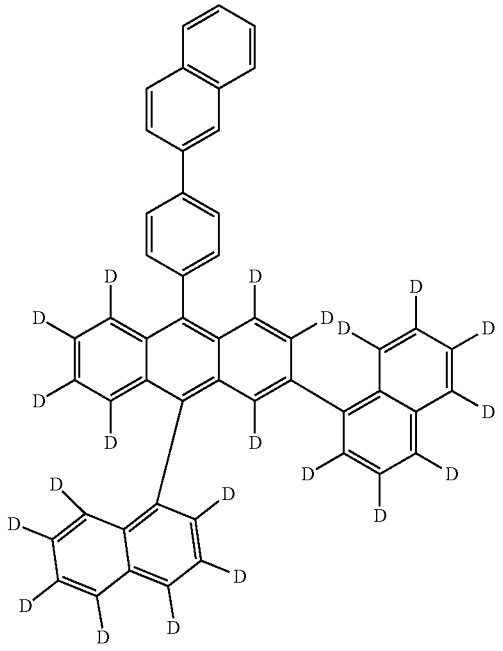
-continued
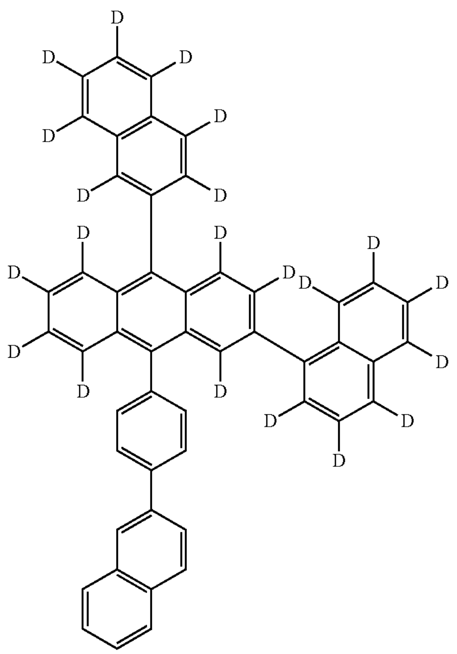
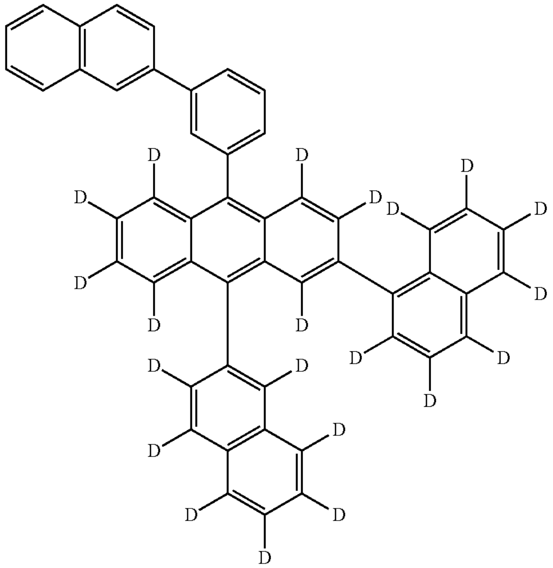

-continued
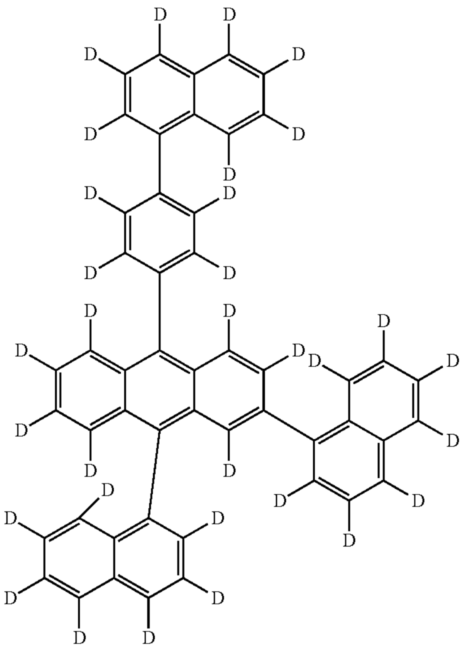
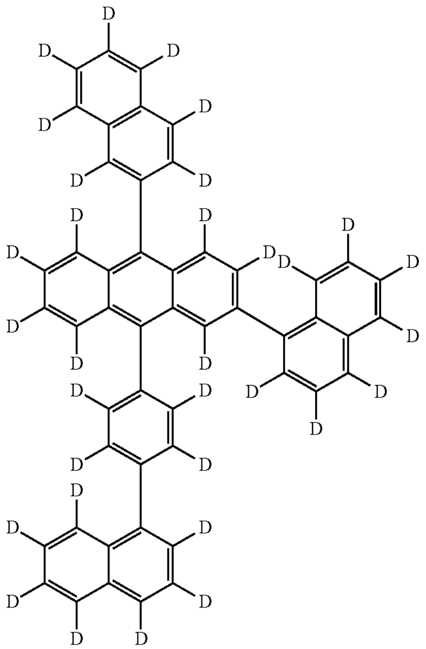
-continued
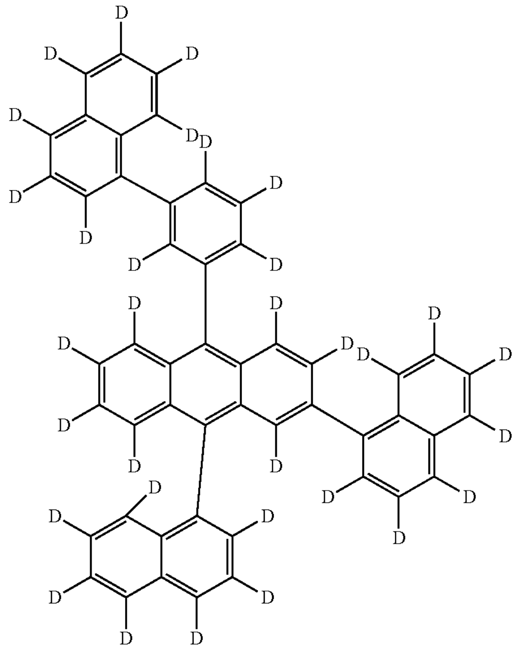
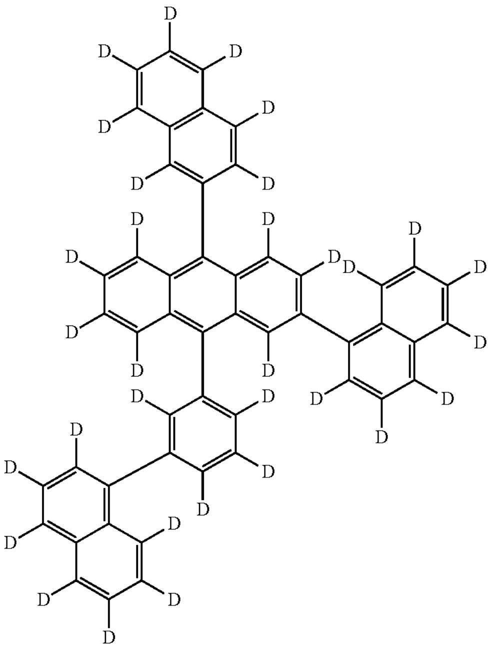

-continued
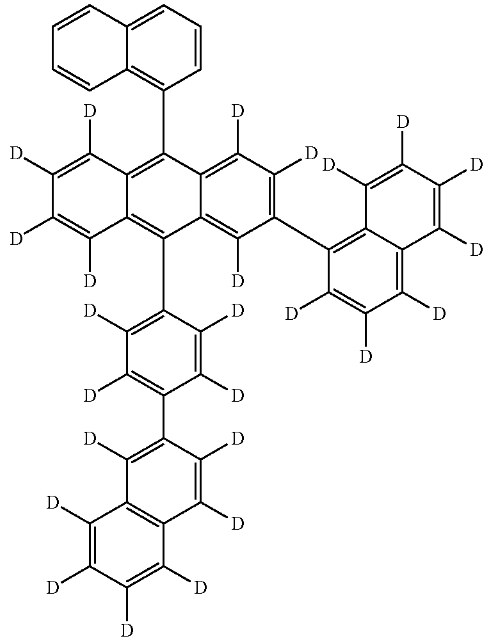
-continued
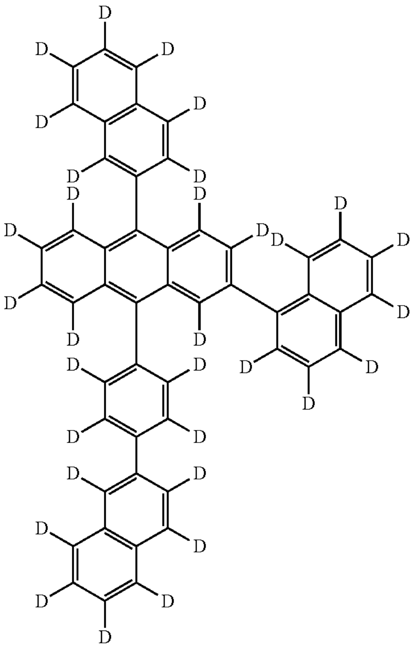
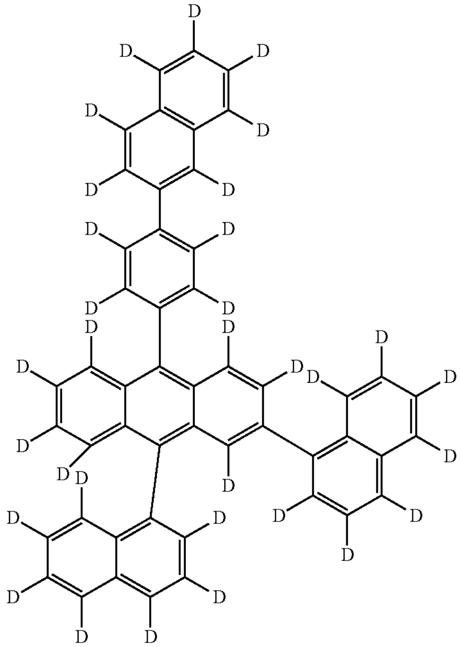
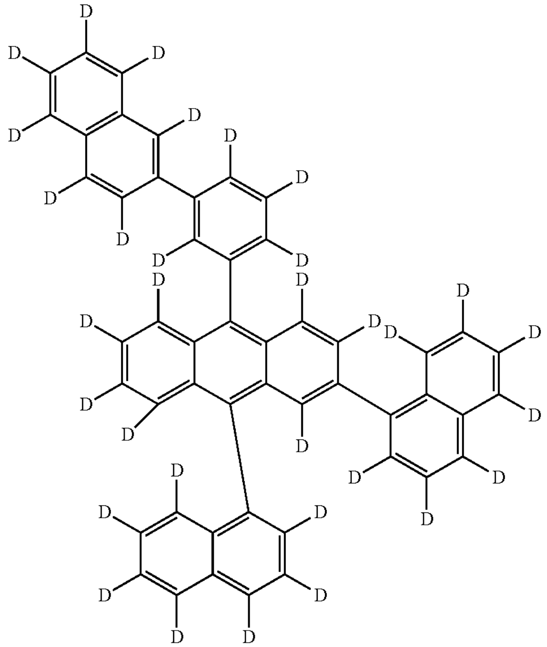

-continued
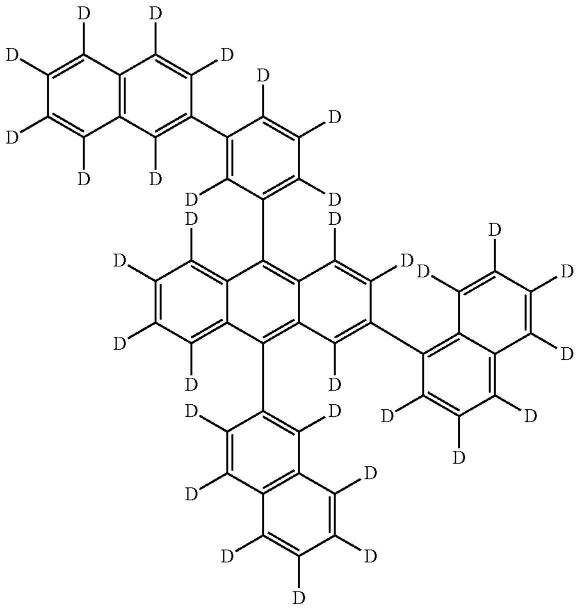 [SMILES: [2H]c1c([2H])c(-c2c([2H])c([2H])c3c([2H])c([2H])c([2H])c([2H])c3c2[2H])c([2H])c(-c2c3c([2H])c([2H])c([2H])c([2H])c3c(-c3c([2H])c([2H])c4c([2H])c([2H])c([2H])c([2H])c4c3[2H])c3c([2H])c(-c4c([2H])c([2H])c([2H])c5c([2H])c([2H])c([2H])c([2H])c45)c([2H])c([2H])c23)c1[2H]]
-continued
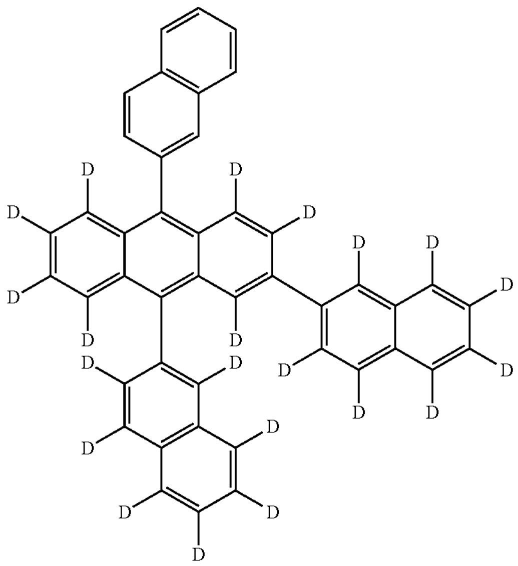
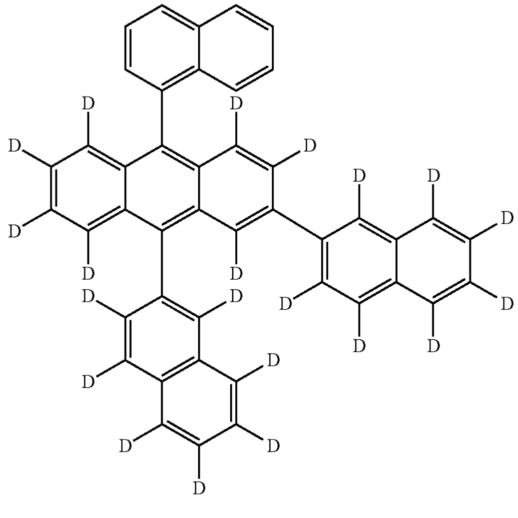
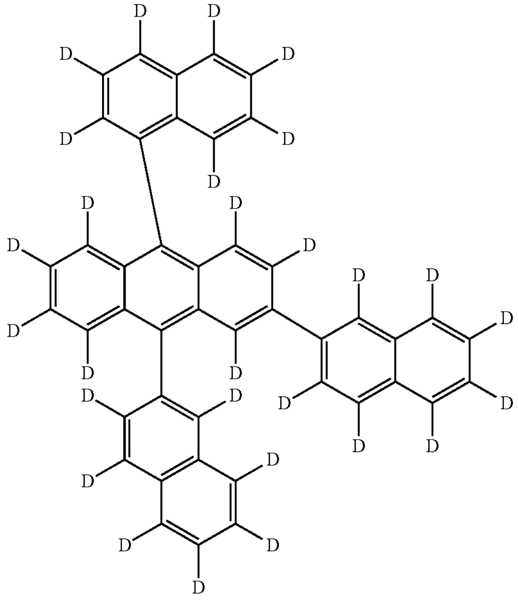

-continued
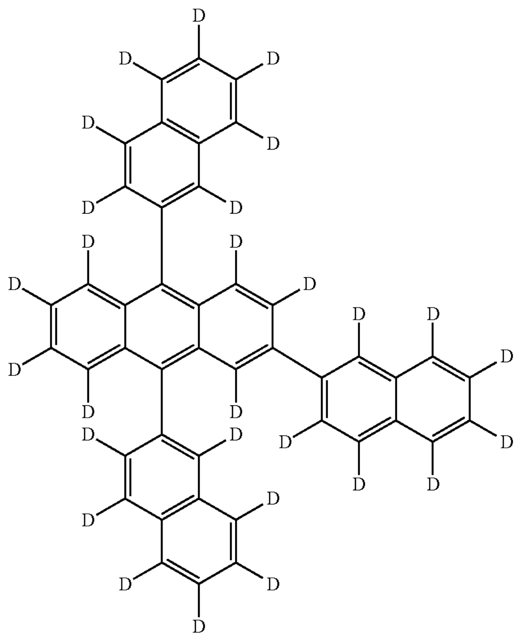
-continued
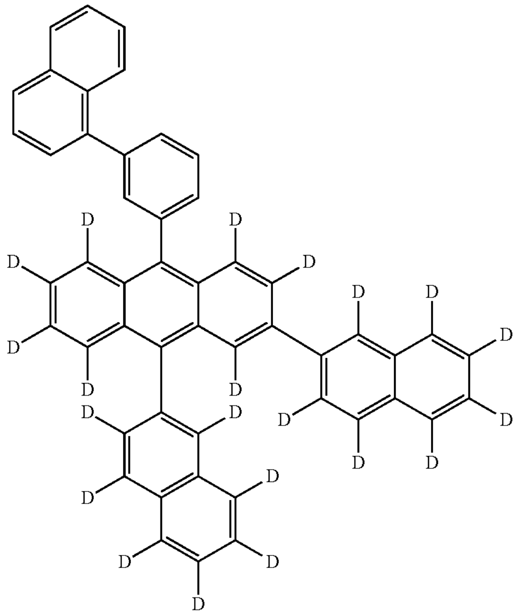
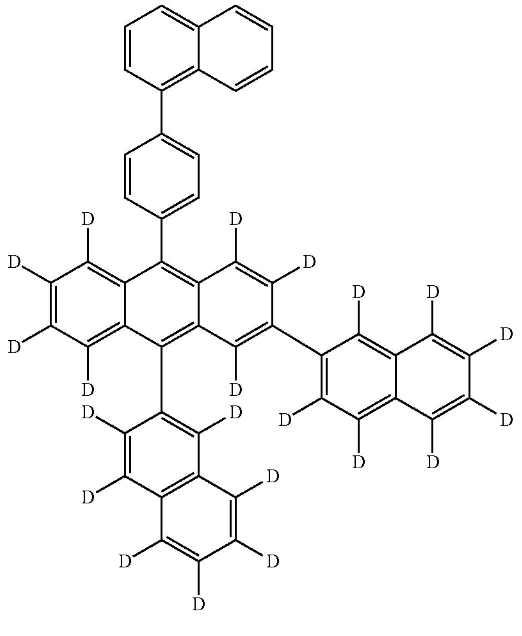
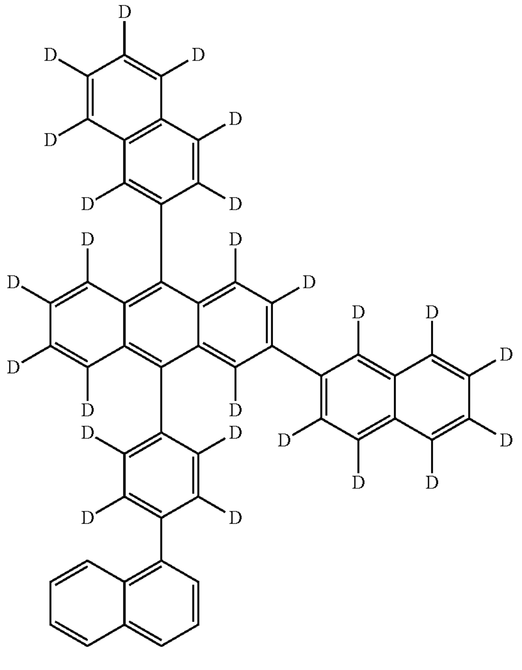

-continued
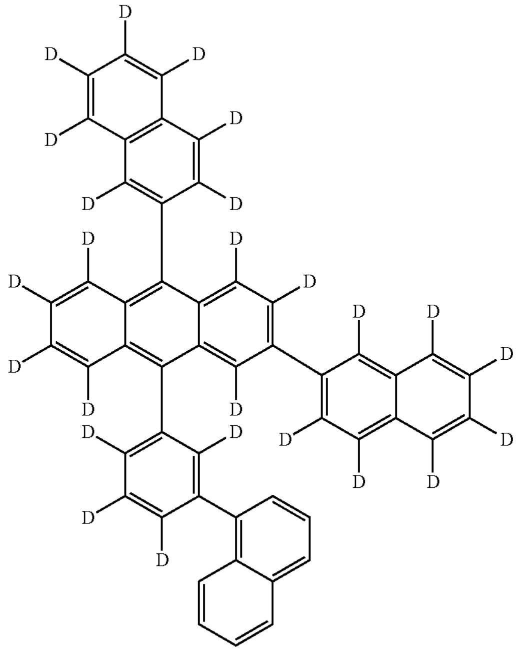
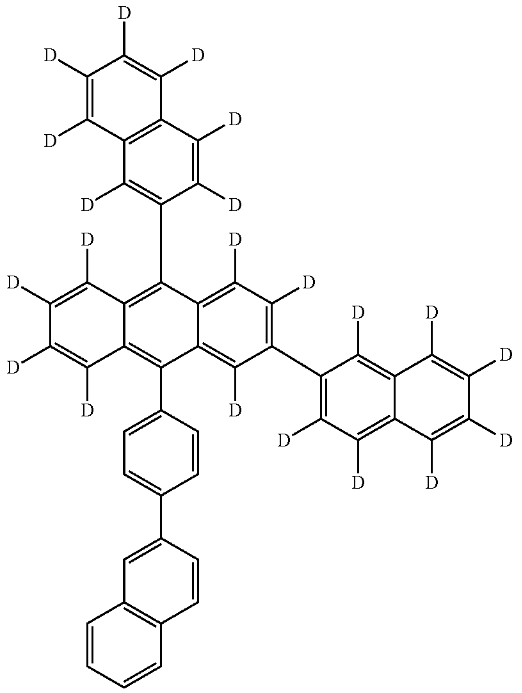
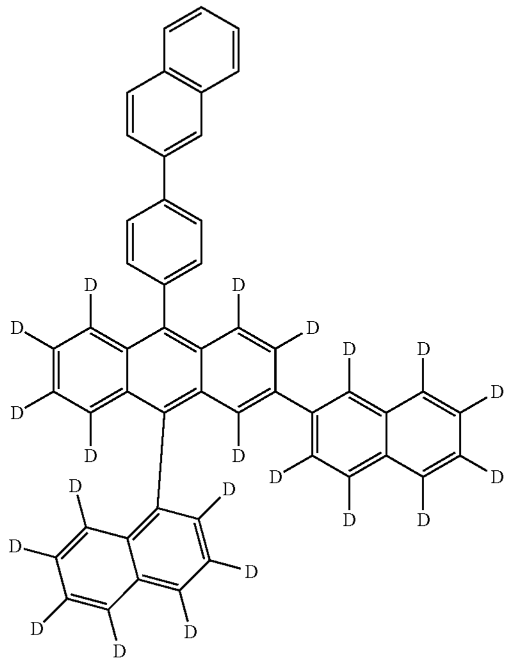
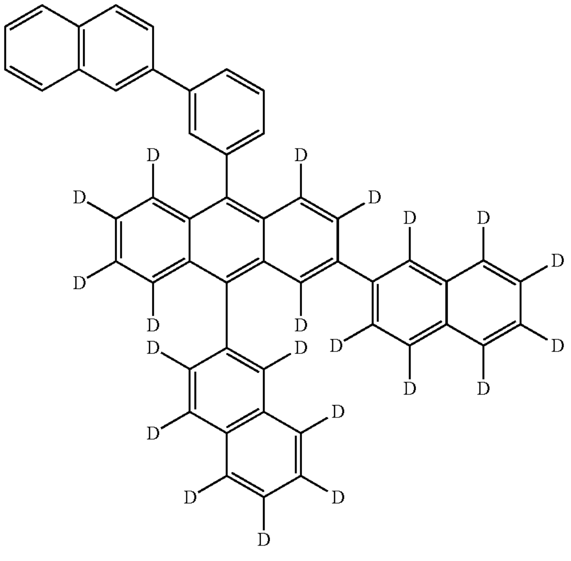

-continued
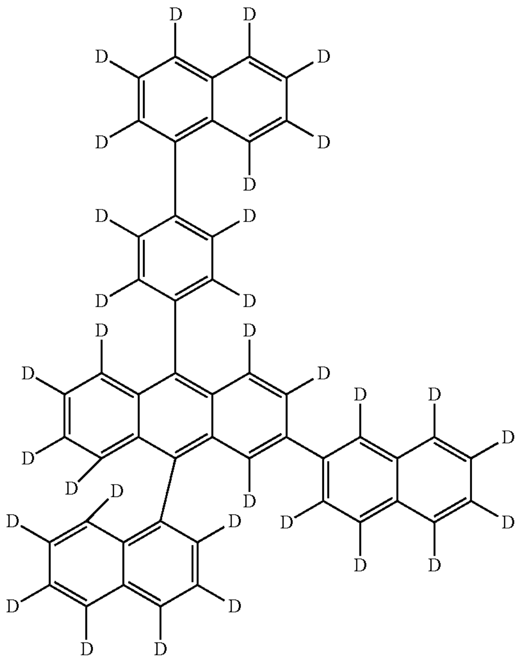
-continued
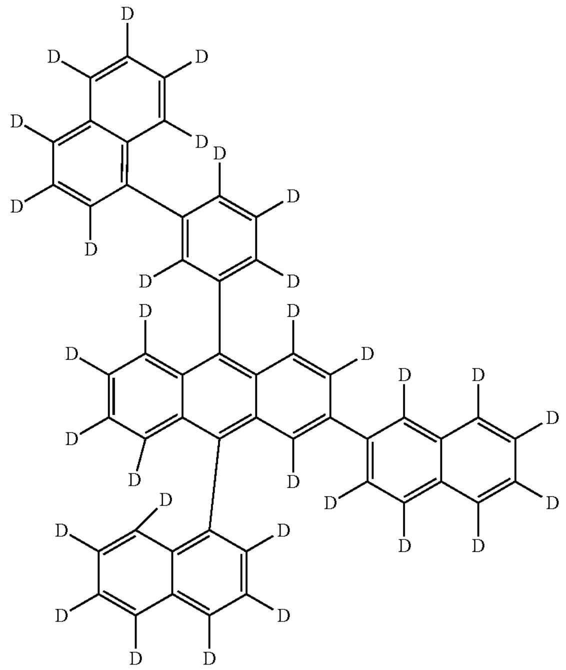
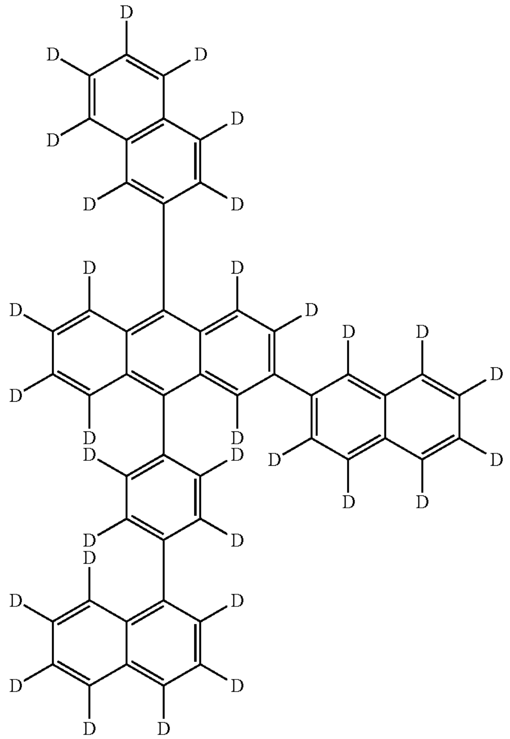
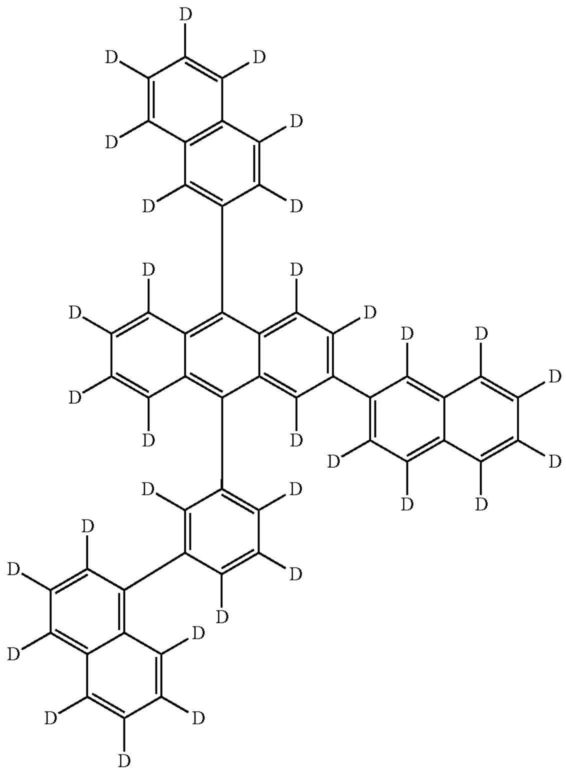

-continued
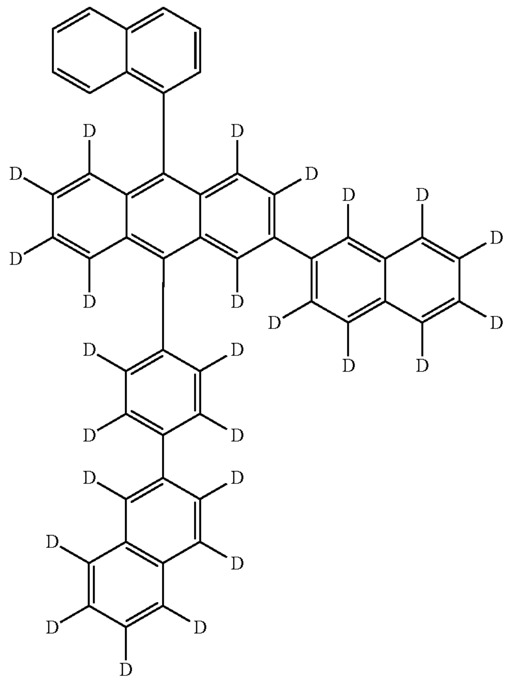
-continued
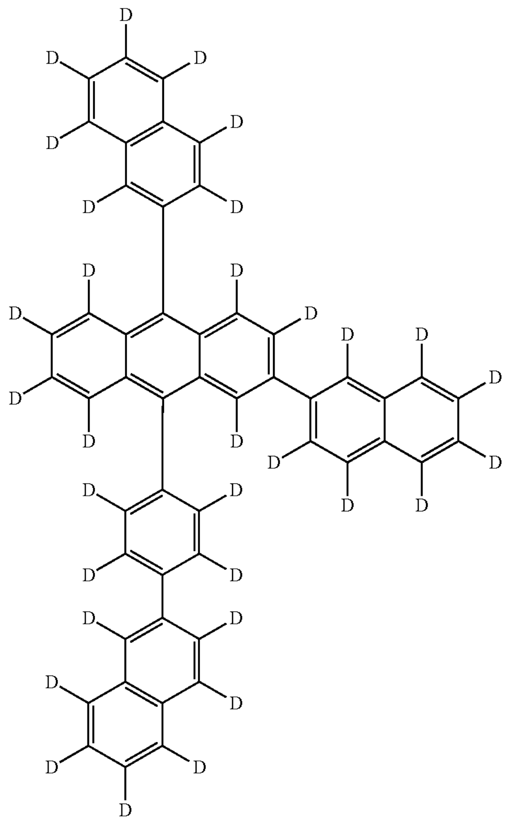
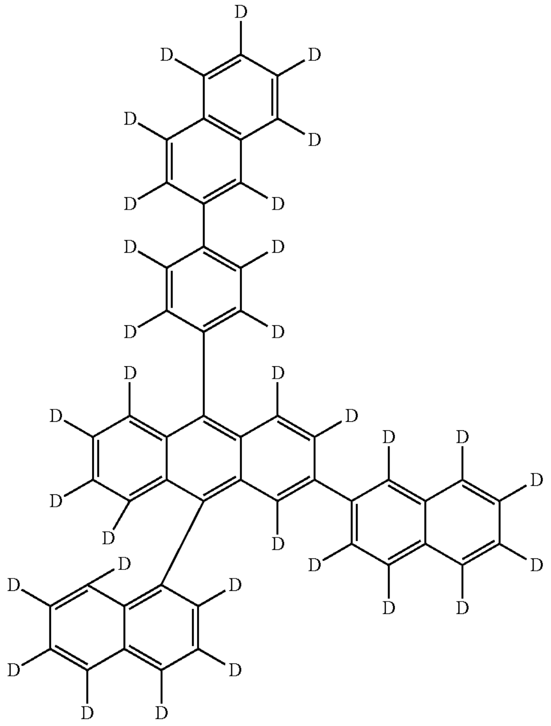
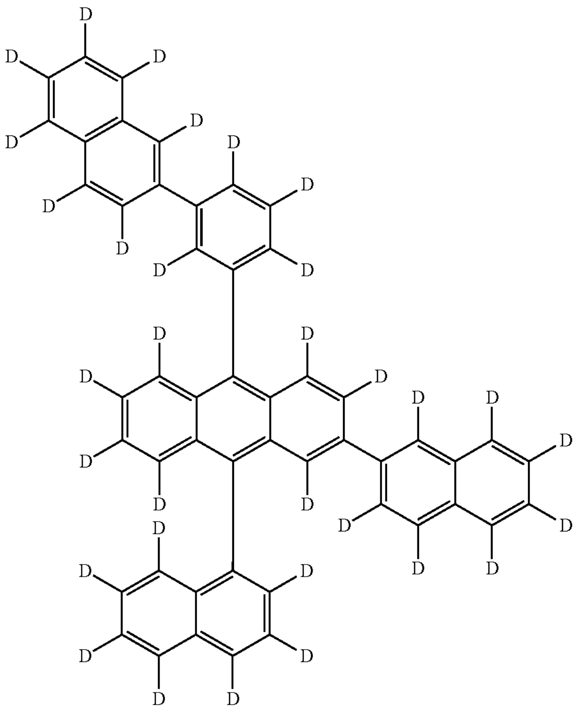

-continued
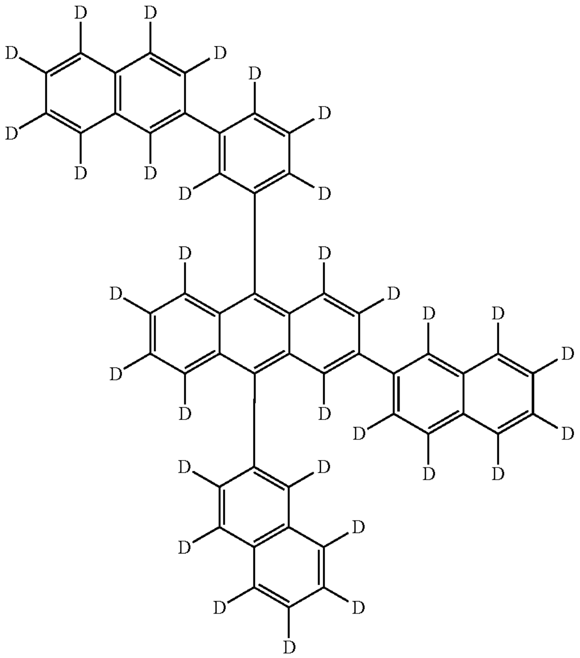 [SMILES: [2H]c1c([2H])c(-c2c([2H])c([2H])c3c([2H])c([2H])c([2H])c([2H])c3c2[2H])c([2H])c(-c2c3c([2H])c([2H])c([2H])c([2H])c3c(-c3c([2H])c([2H])c4c([2H])c([2H])c([2H])c([2H])c4c3[2H])c3c([2H])c(-c4c([2H])c([2H])c5c([2H])c([2H])c([2H])c([2H])c5c4[2H])c([2H])c([2H])c23)c1[2H]]
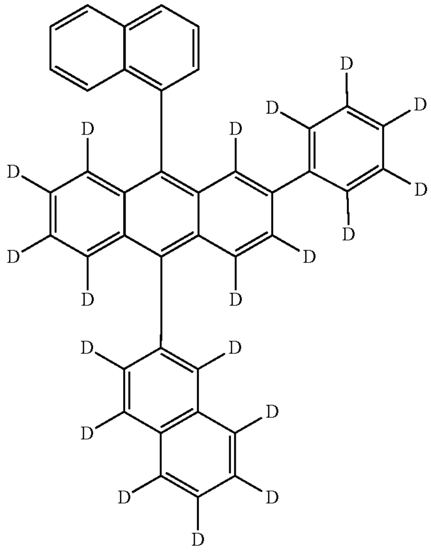
-continued
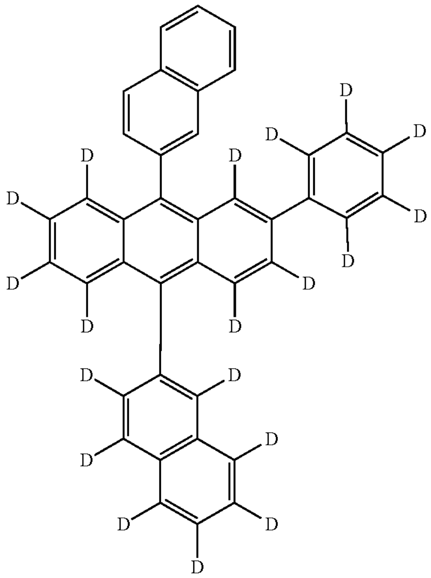
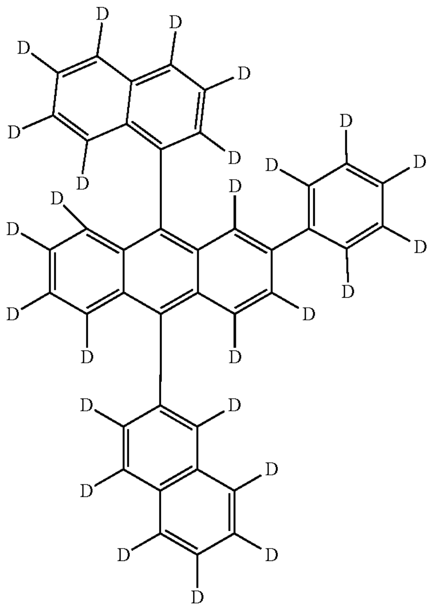

-continued
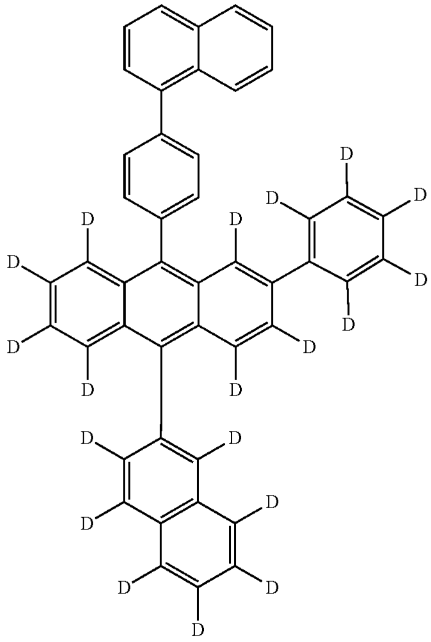
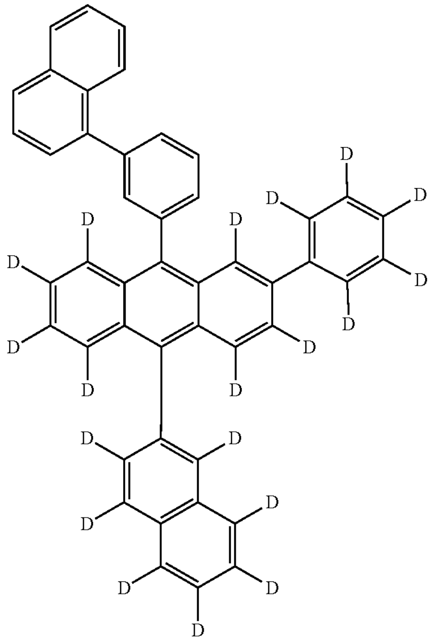
-continued
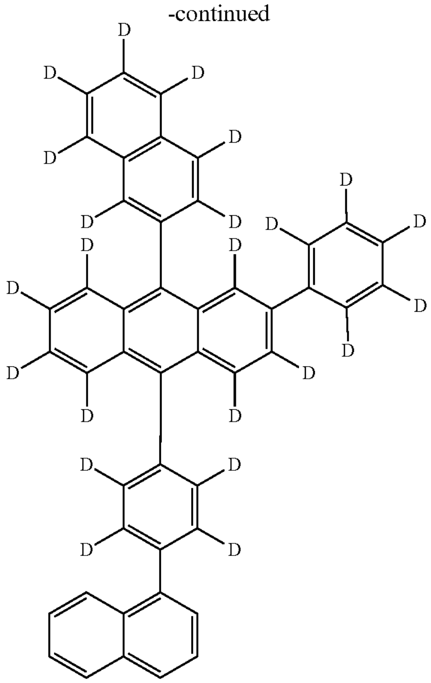
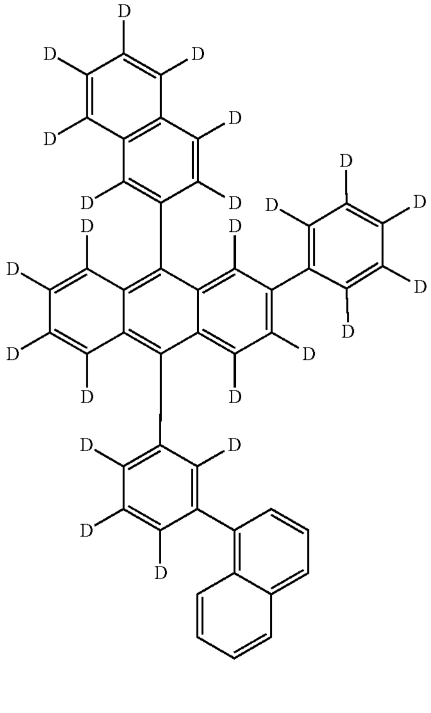

-continued
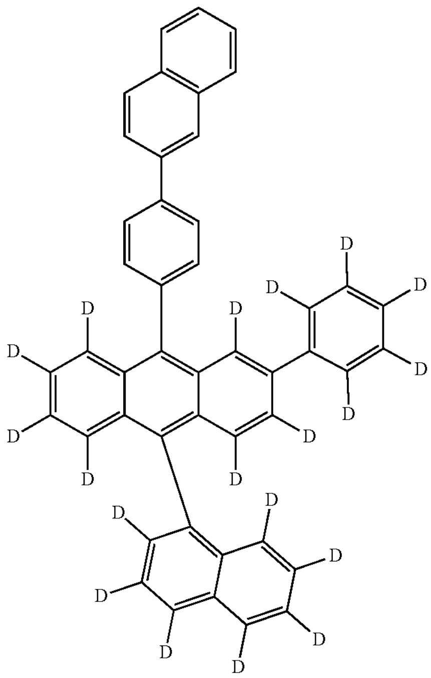
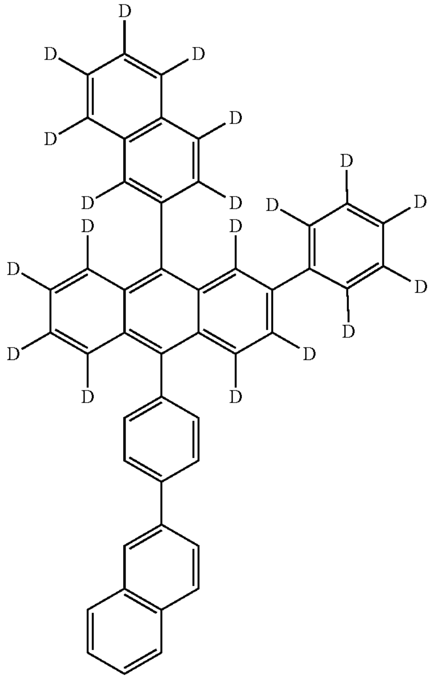
-continued
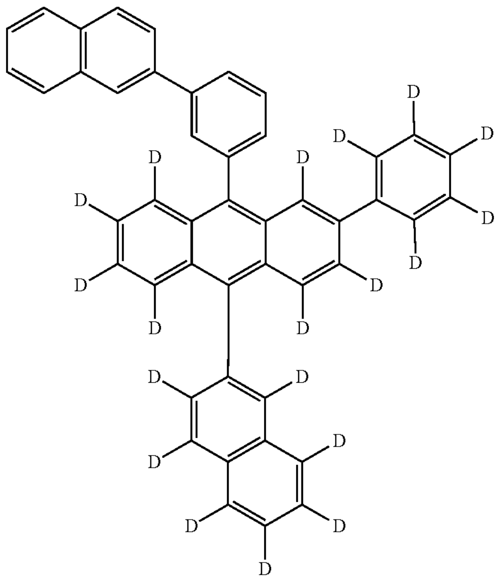
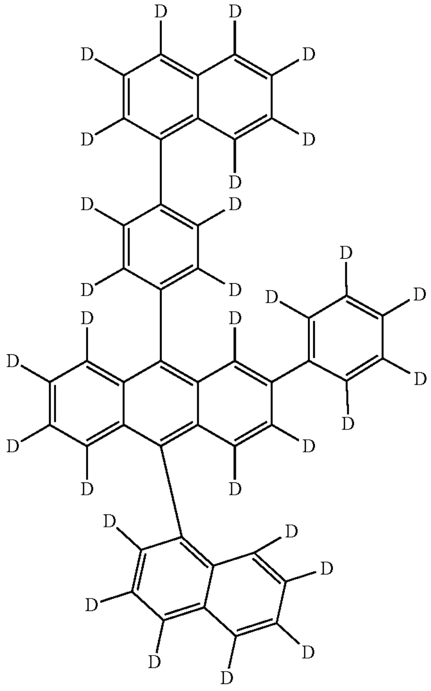

-continued
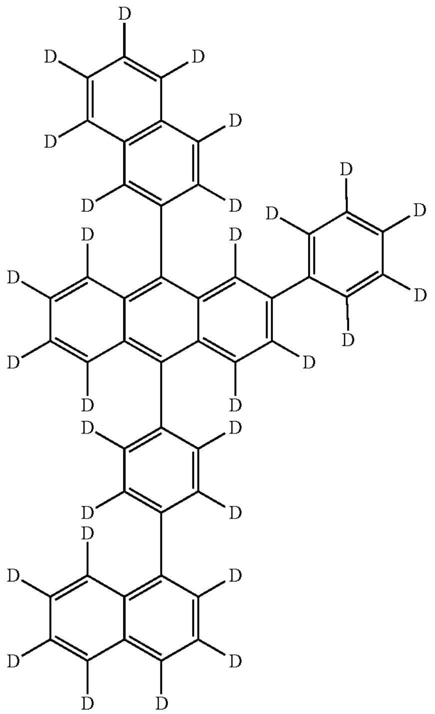
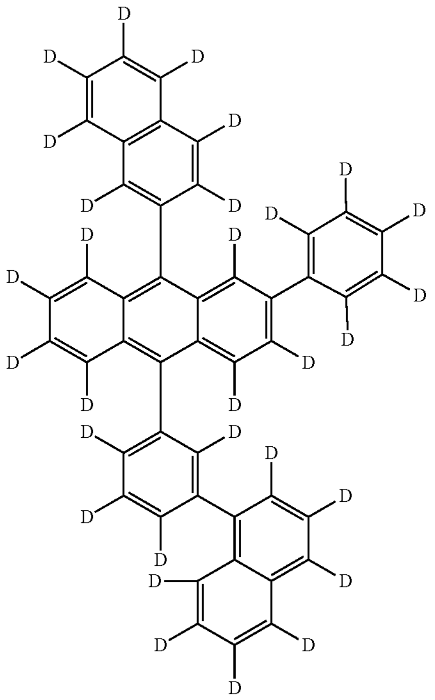
-continued
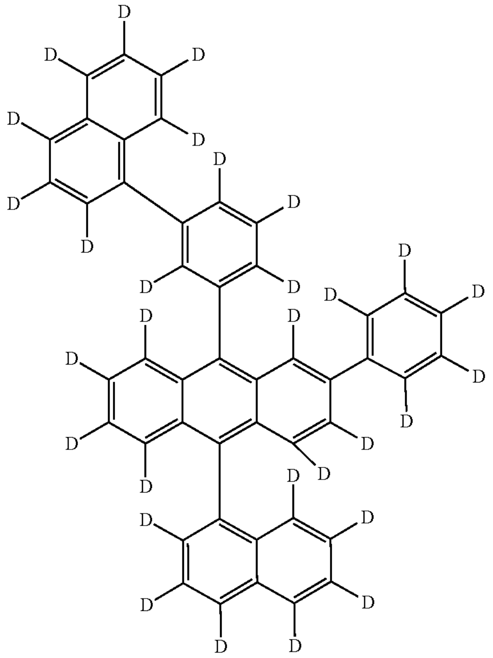
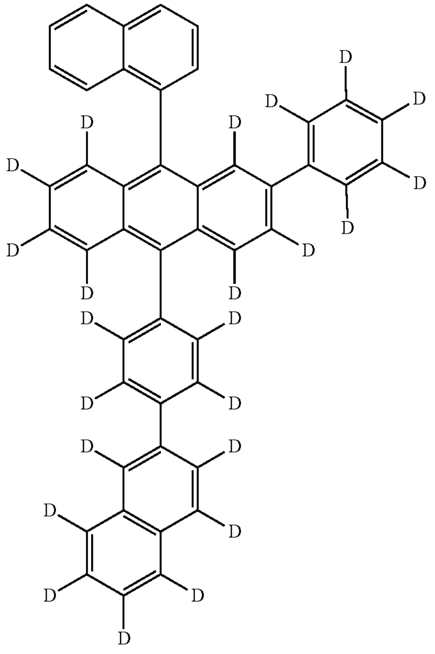

-continued
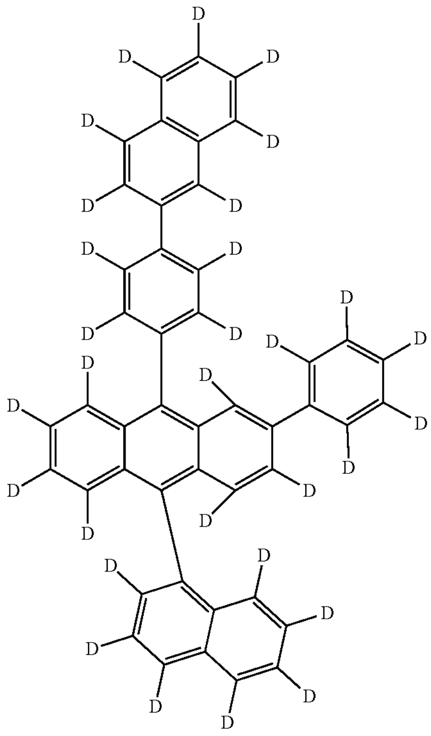
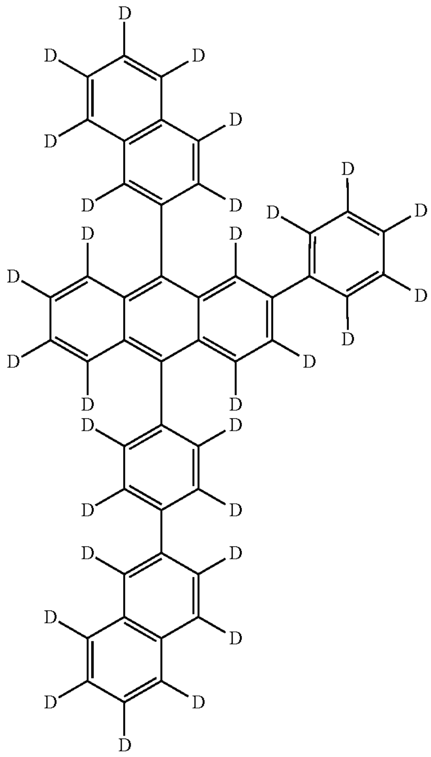
-continued
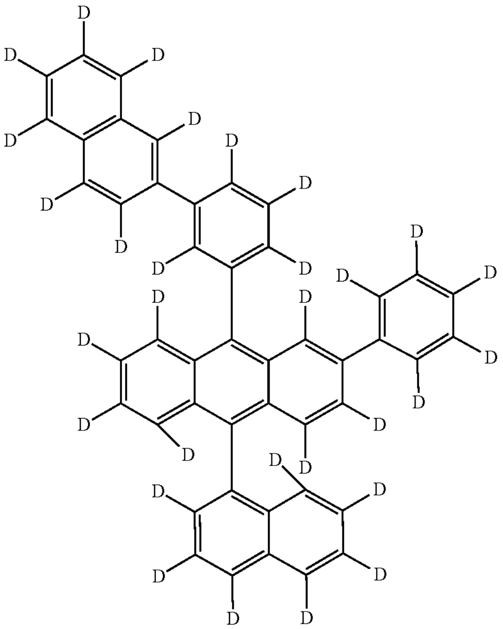
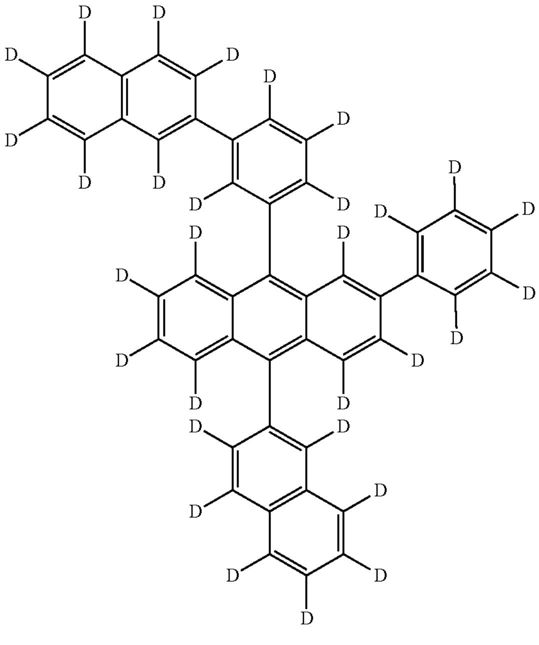

-continued
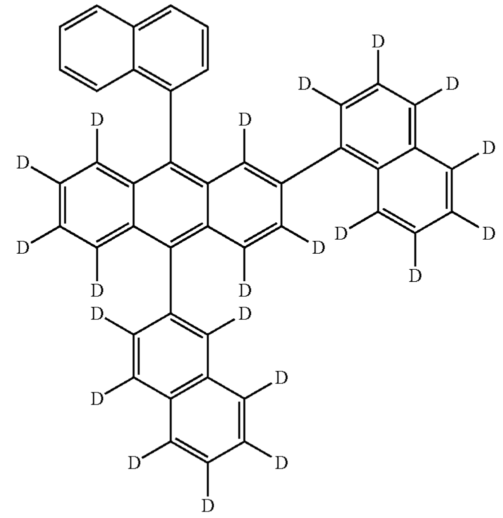
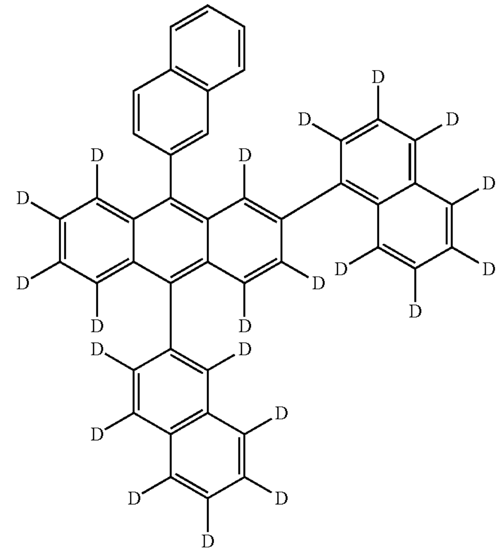
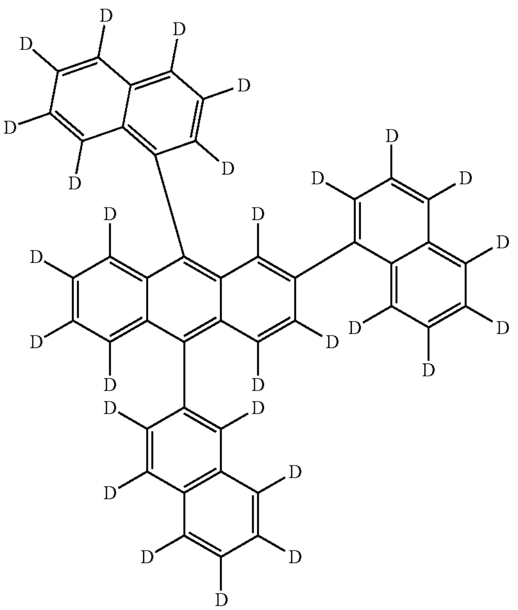
-continued
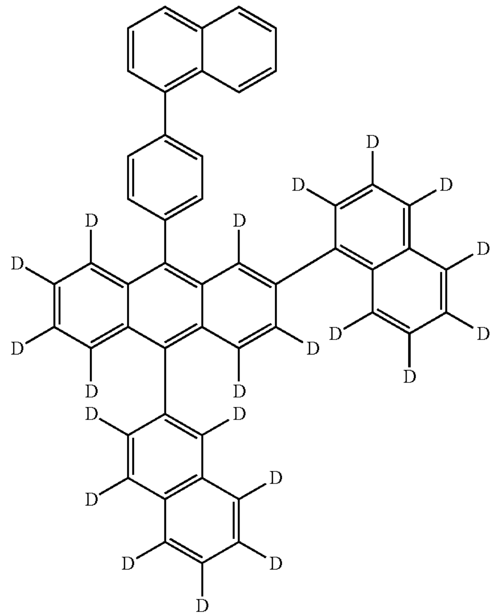
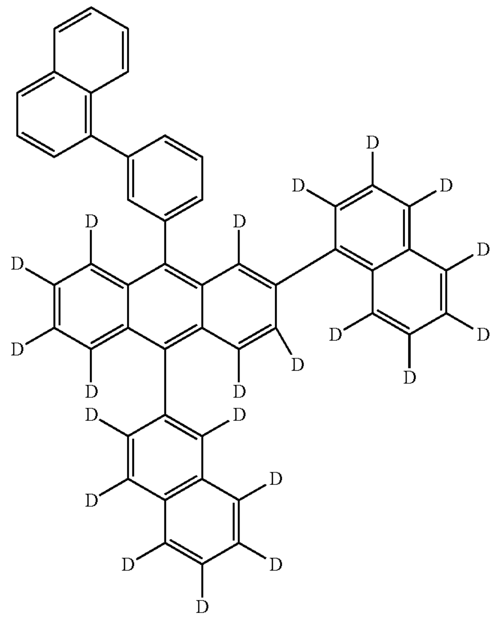

-continued
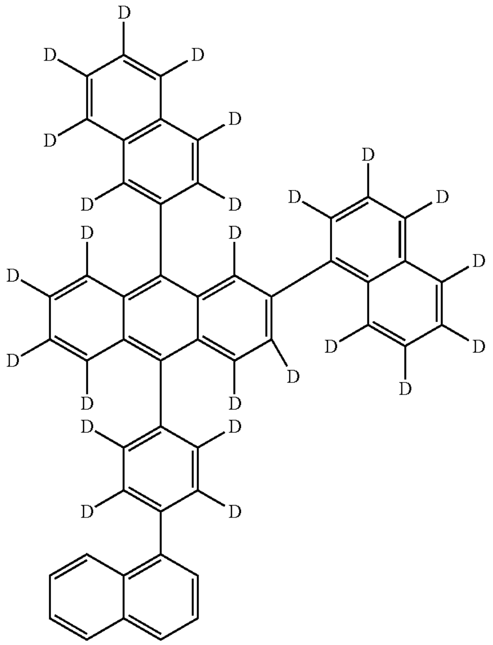
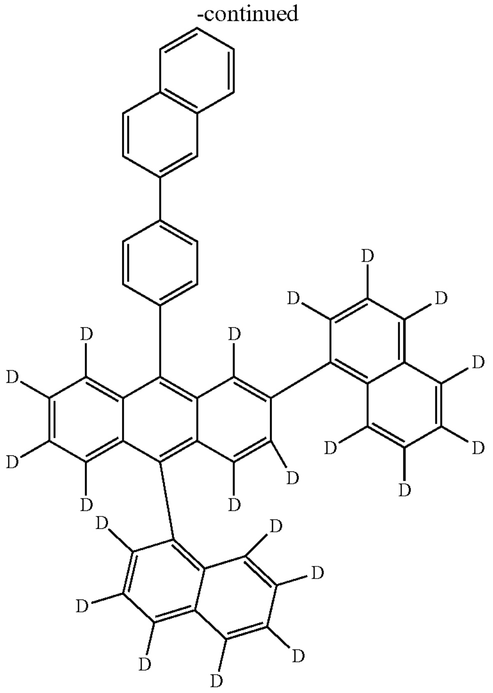
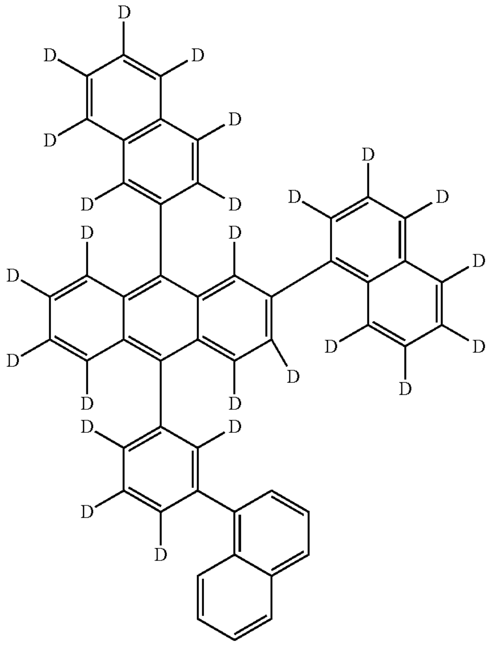
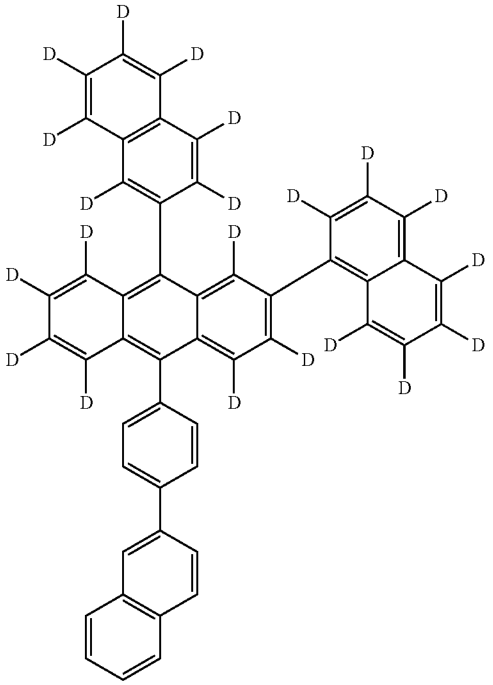

-continued
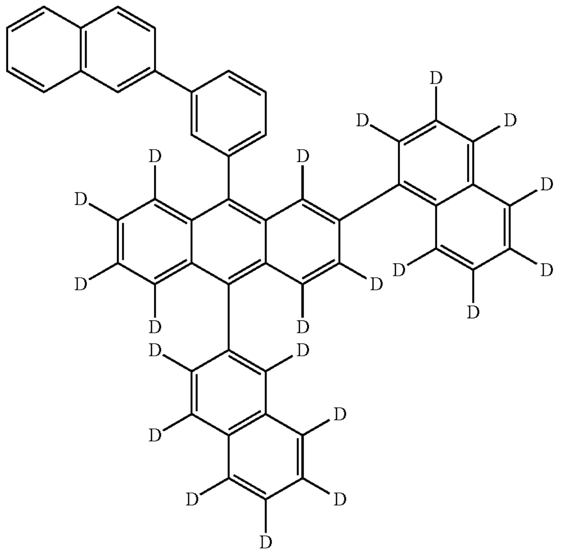
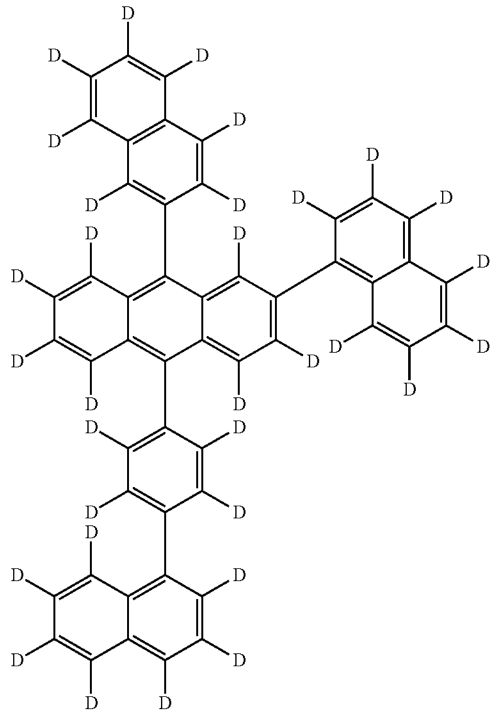
-continued
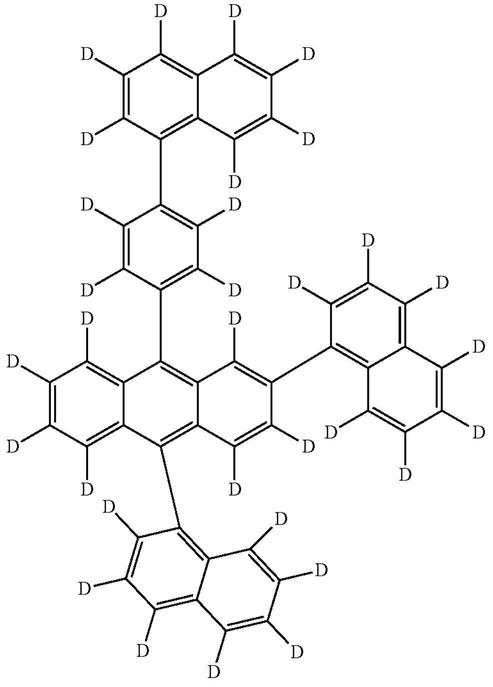
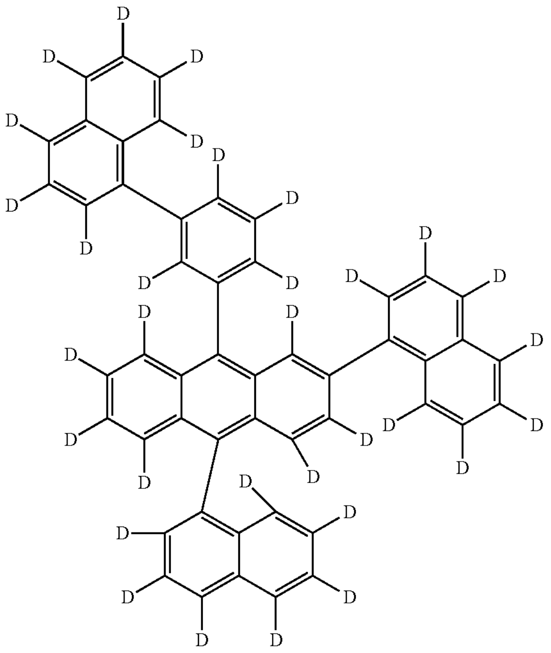

-continued
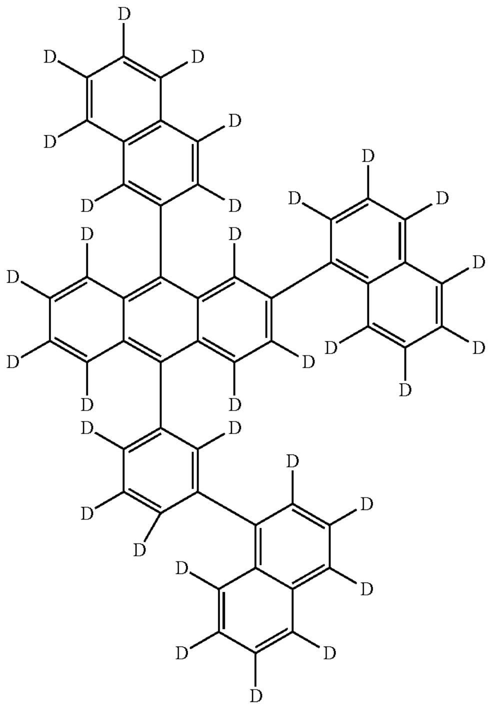
-continued
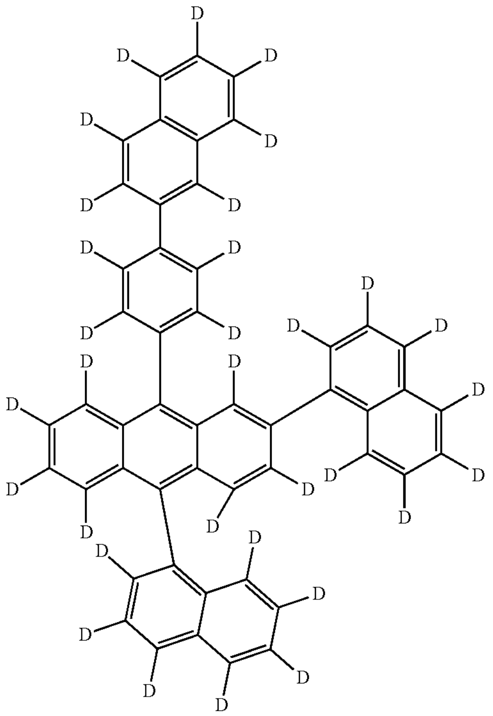
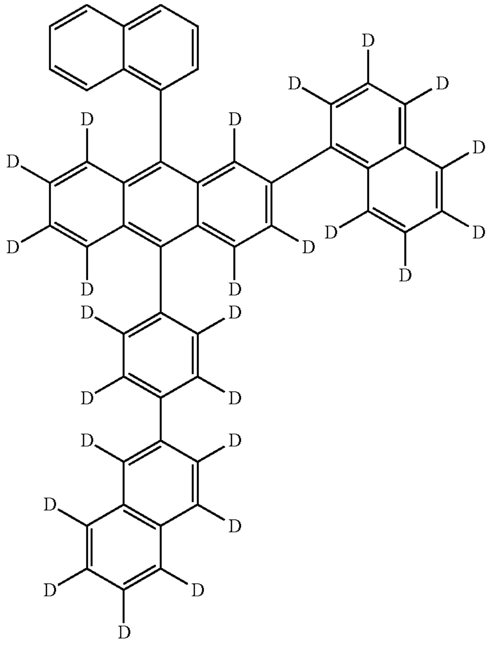
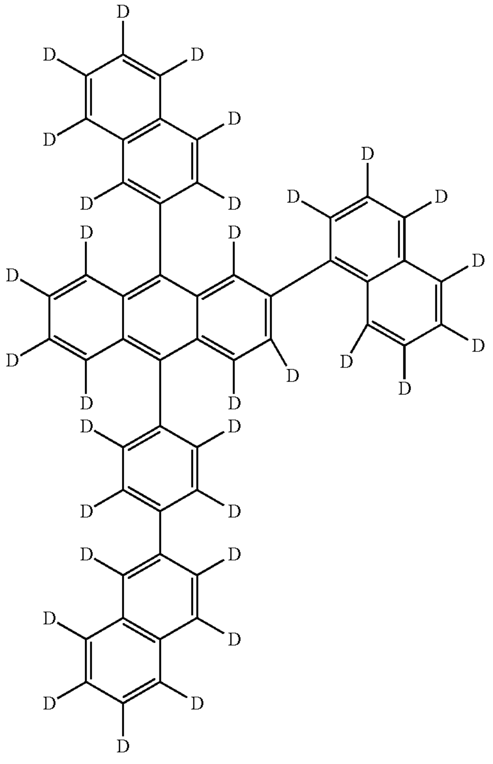

-continued
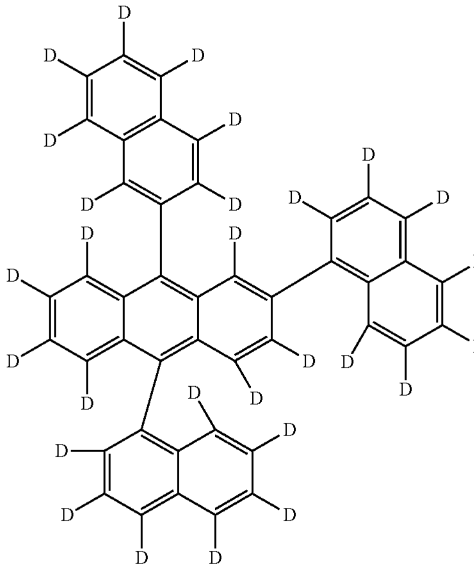
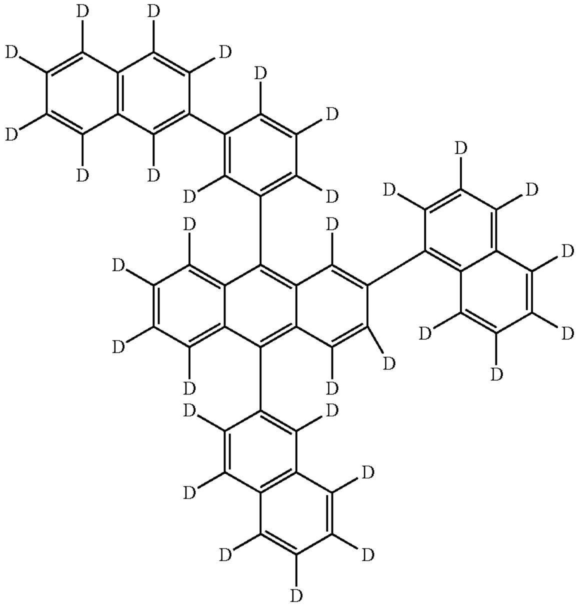
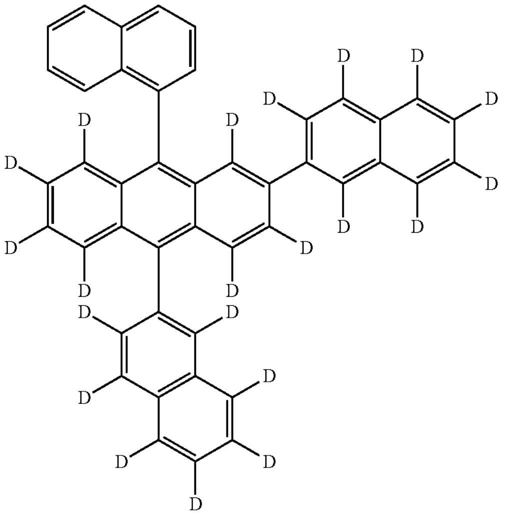
-continued
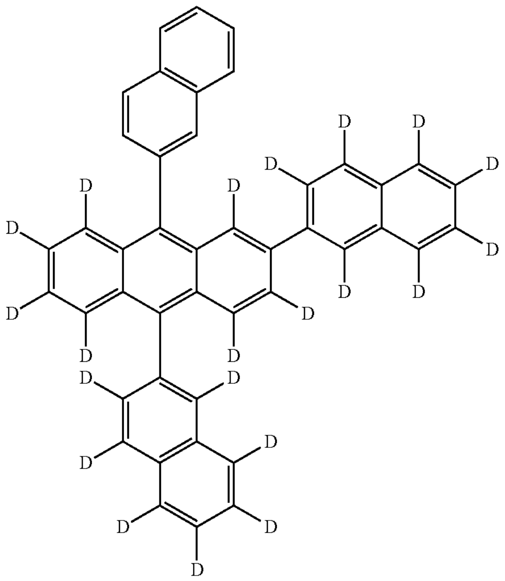
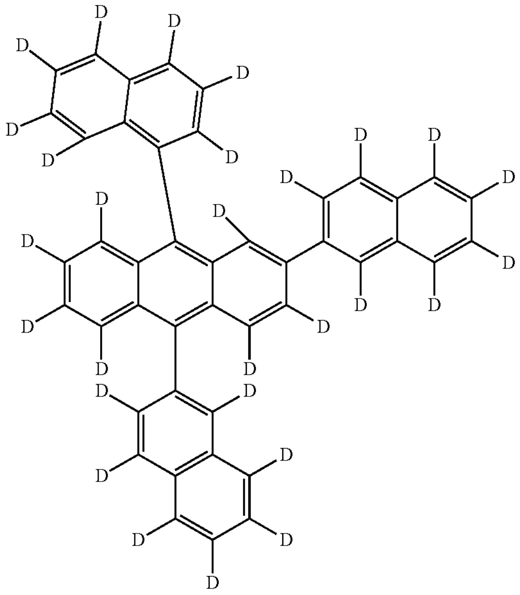

-continued
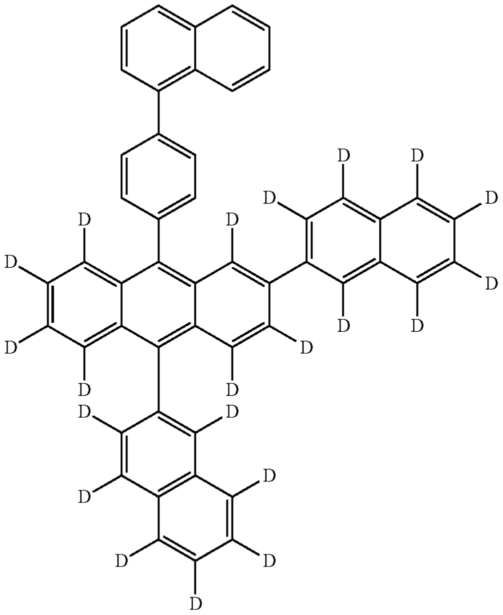
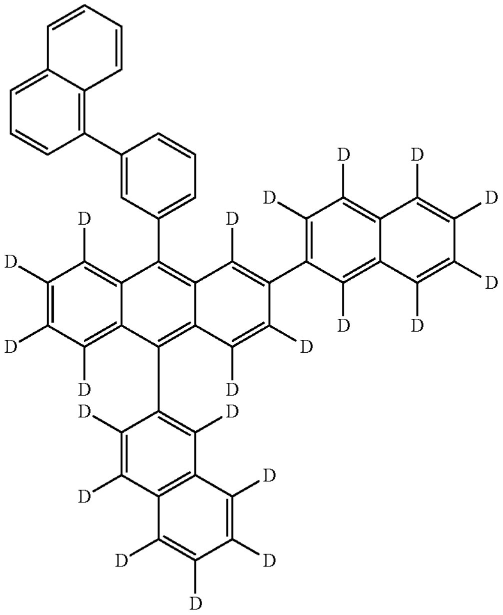
-continued
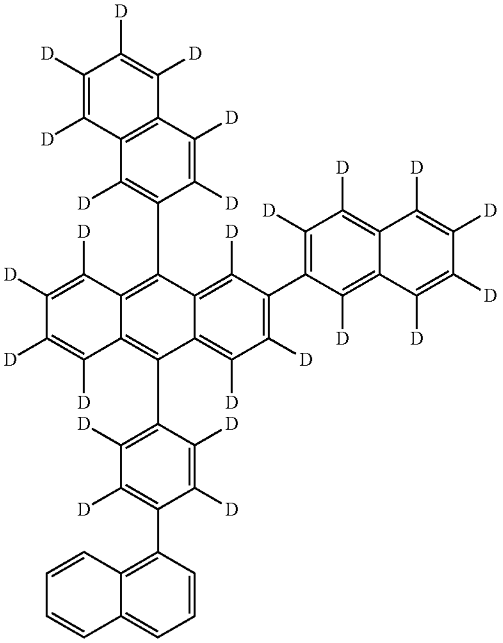
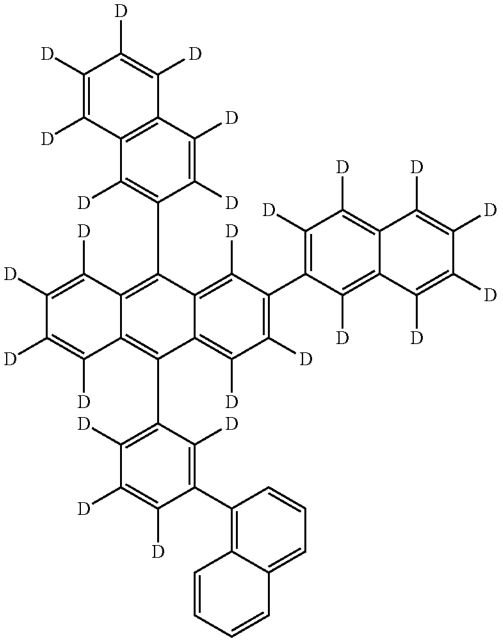

-continued
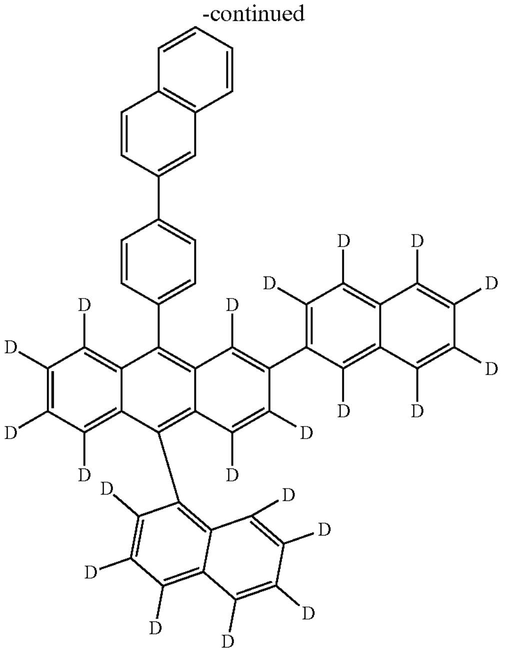
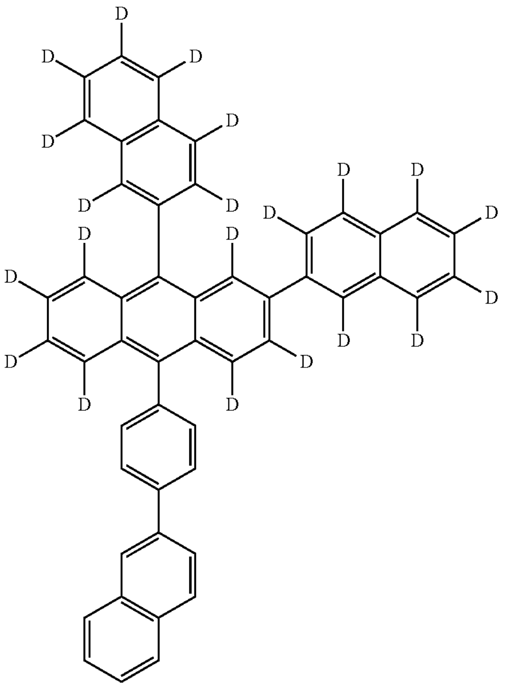
-continued
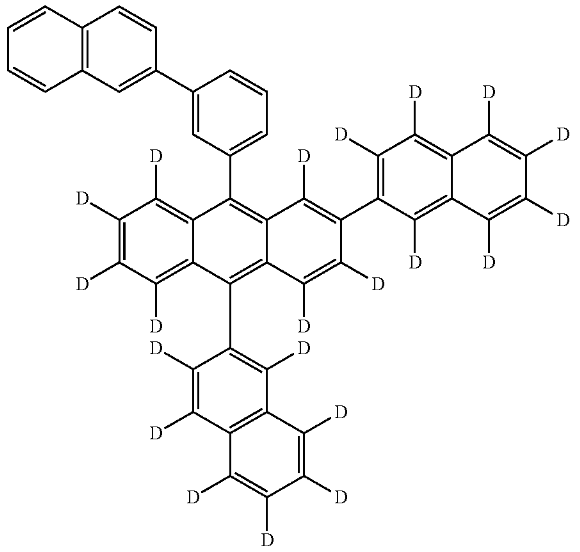
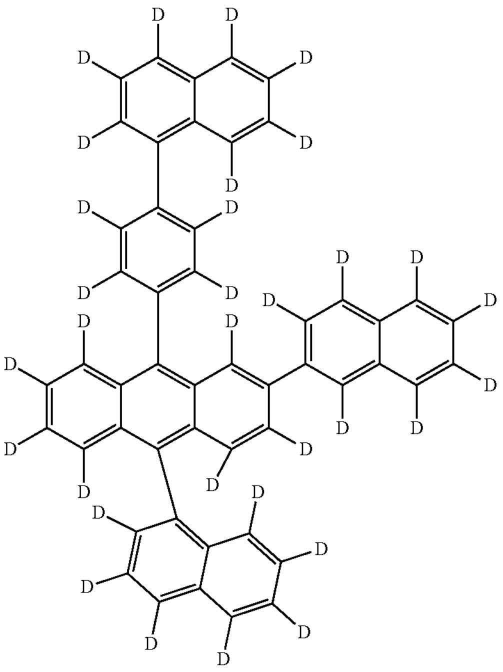

-continued
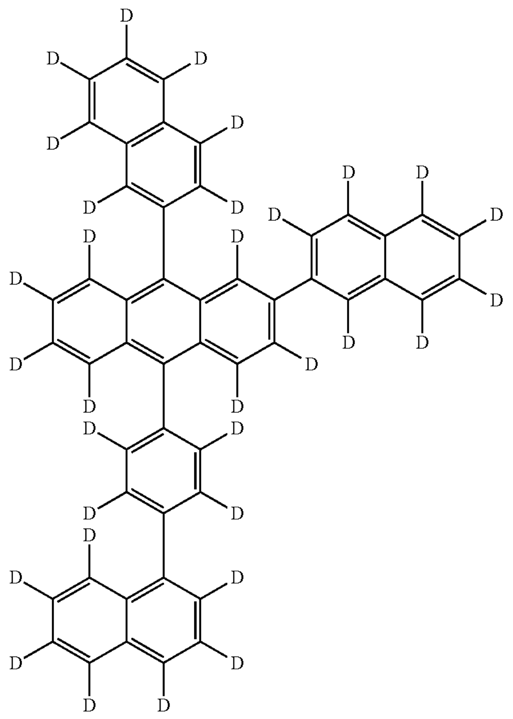
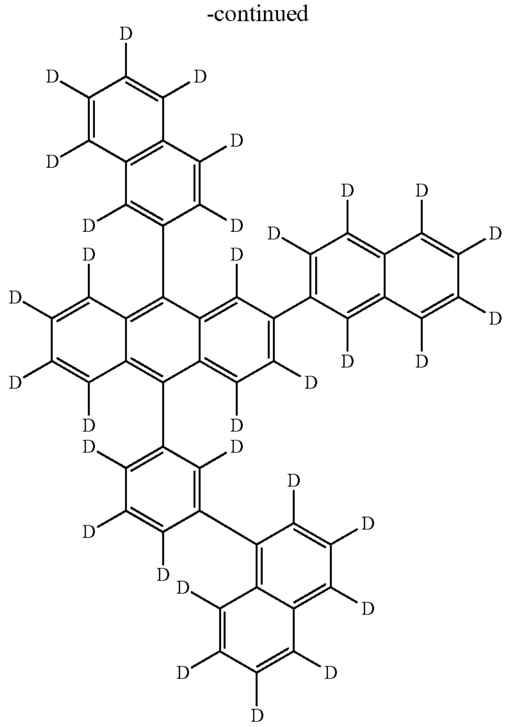
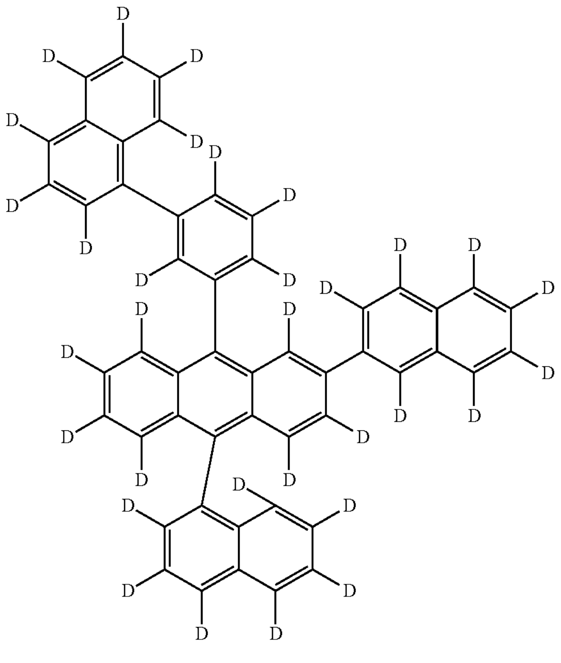
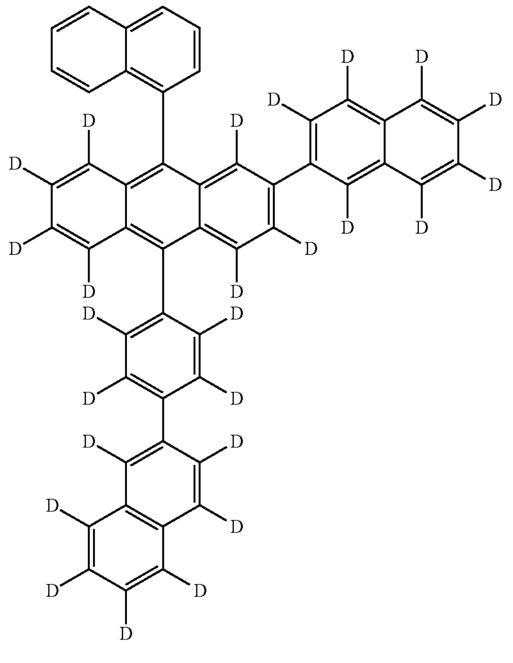

-continued
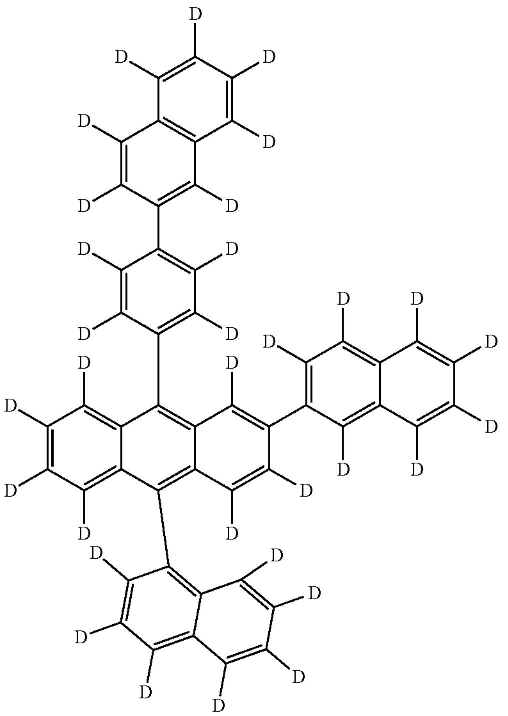
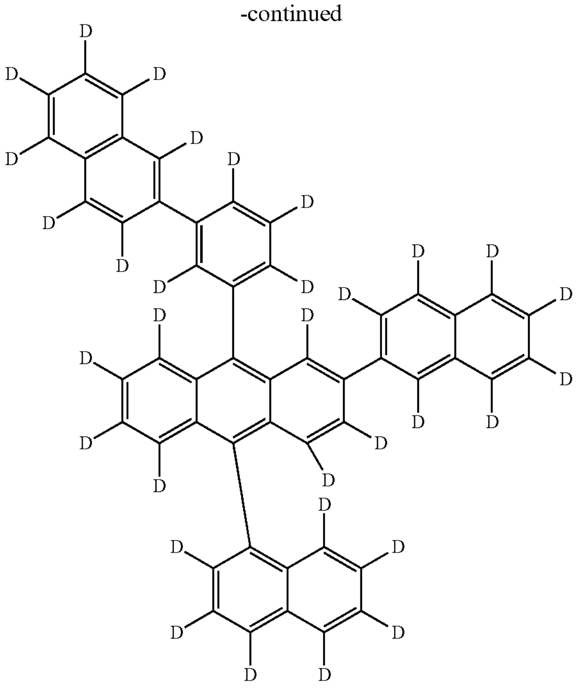
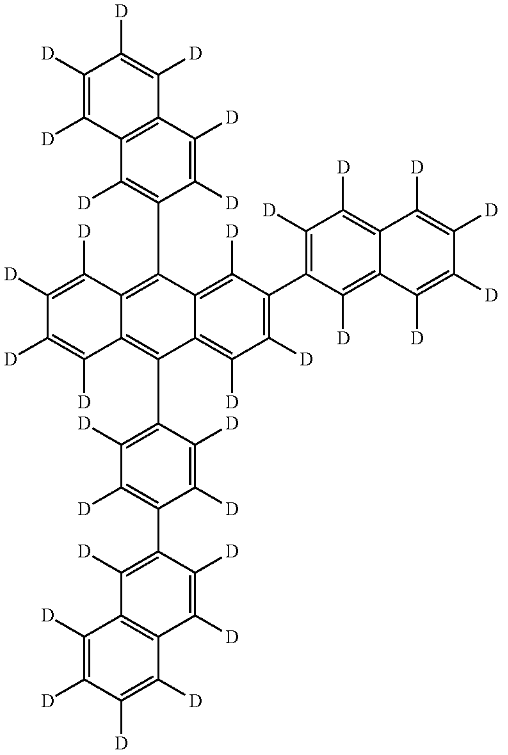
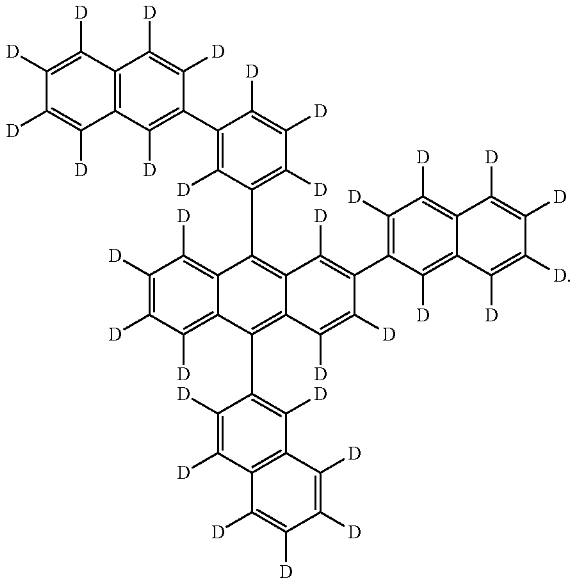
12. An organic light emitting device comprising:
an anode;
a cathode; and
an organic material layer comprising a light emitting layer provided between the anode and the cathode,
wherein the light emitting layer comprises one or more of compounds represented by the following Formulae 1-1 to 1-3; and a compound any one selected from the following Group 1:

[Formula 1-1]

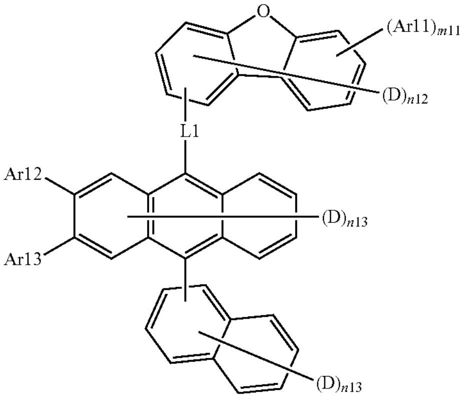

[Formula 1-2]

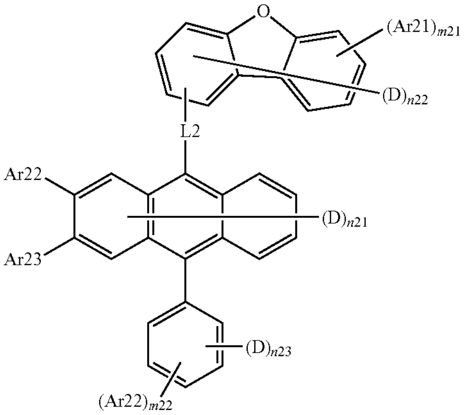

[Formula 1-3]

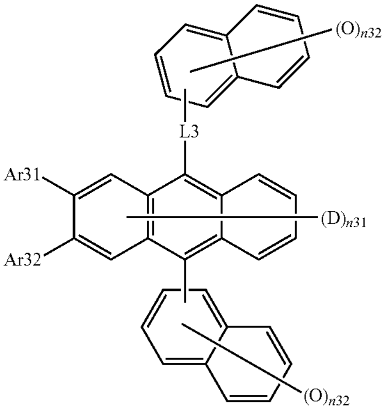

wherein, in Formulae 1-1 to 1-3,

L1 to L3 are the same as or different from each other, and are each independently a direct bond; or a substituted or unsubstituted arylene group, D is deuterium, n11, n21, and n31 are each an integer from 0 to 6, n12, n13, n22, n32, and n33 are each an integer from 0 to 7, and n23 is an integer from 0 to 5, Ar11, Ar21, and Ar22 are the same as or different from each other, and are each independently a substituted or unsubstituted aryl group, Ar12, Ar13, Ar23, Ar24, Ar31, and Ar32 are the same as or different from each other, and are each independently hydrogen; deuterium; a substituted or unsubstituted aryl group; or a substituted or unsubstituted heteroaryl group, m11 and m21 are an integer from 0 to 4, m22 is an integer from 0 to 5, and substituents in the parenthesis are the same as or different from each other provided that when m11, m21, and m22 are each 2 or higher, the compounds of Formulae 1-1 to 1-3 each have at least one or more deuteriums, and

[Group 1]

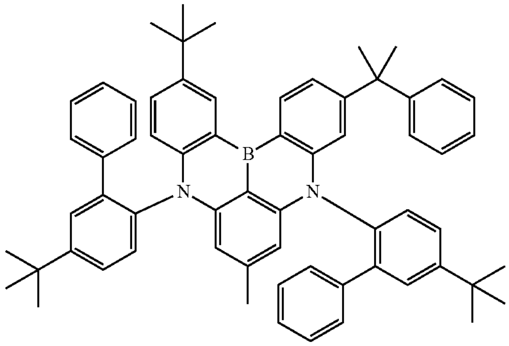

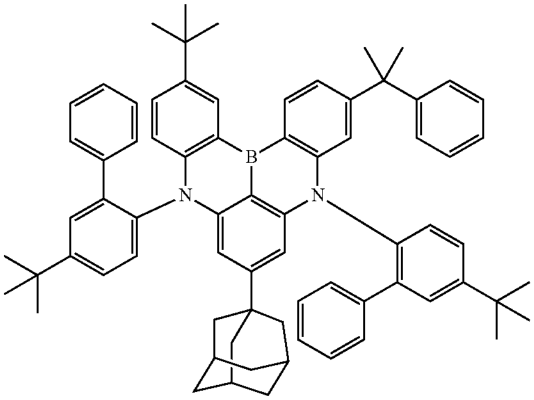

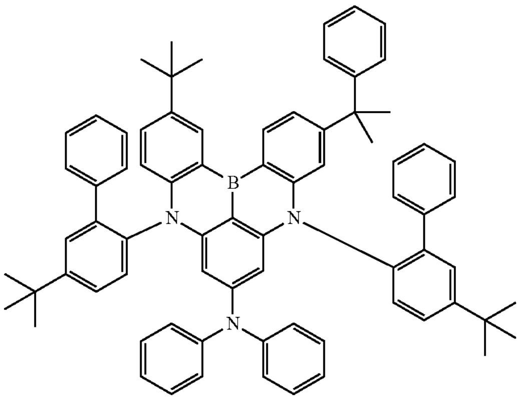

-continued
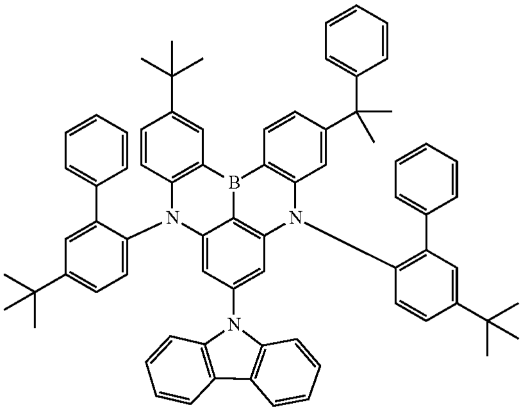
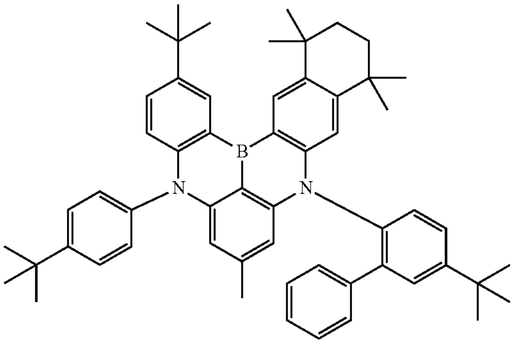
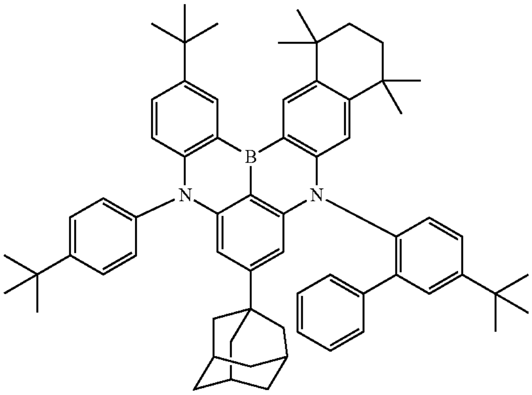
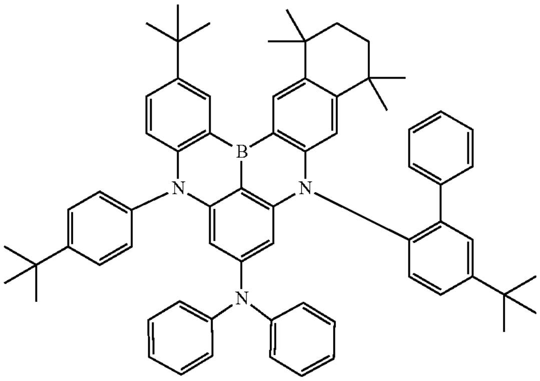
-continued
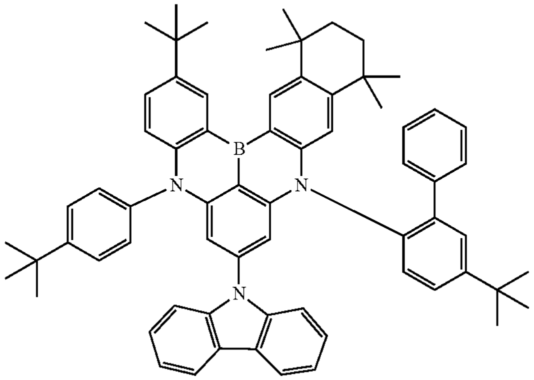
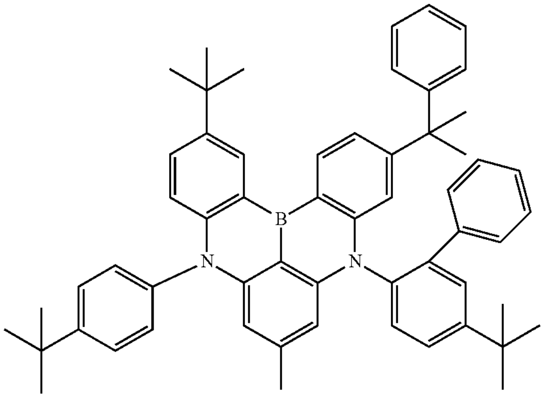
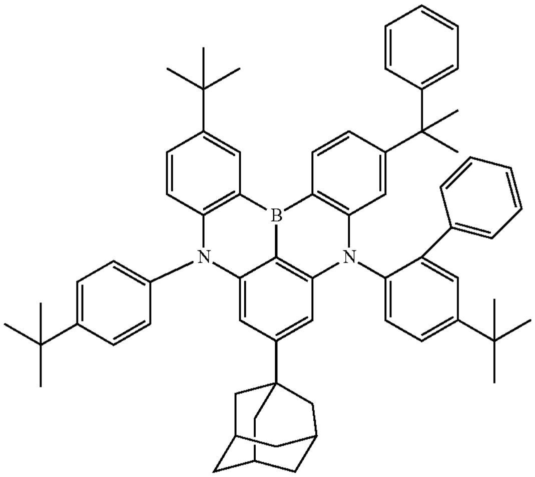
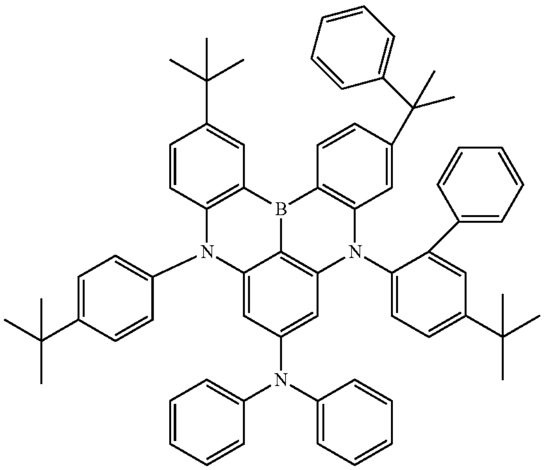

-continued
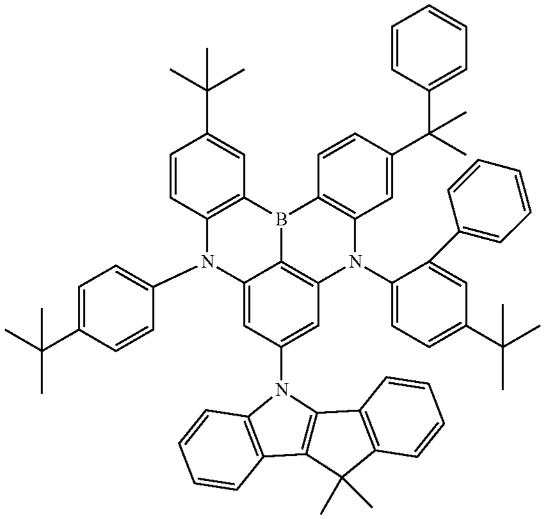
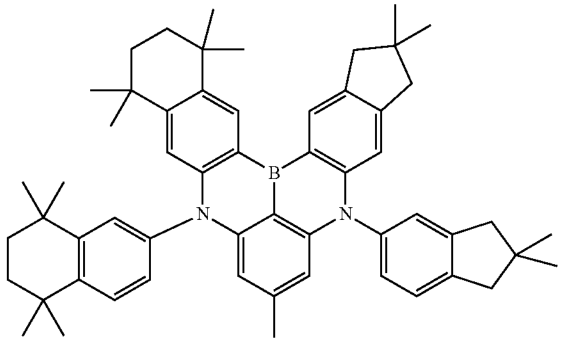
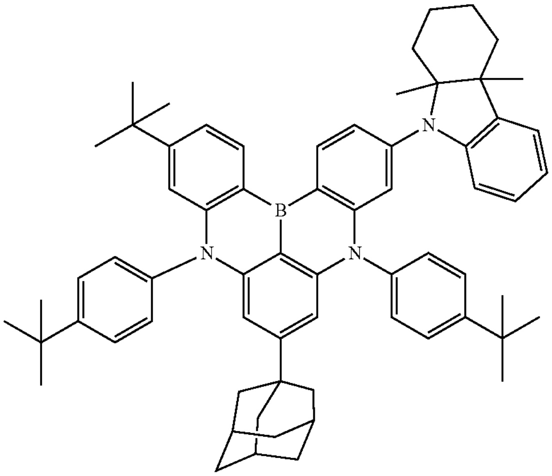
-continued
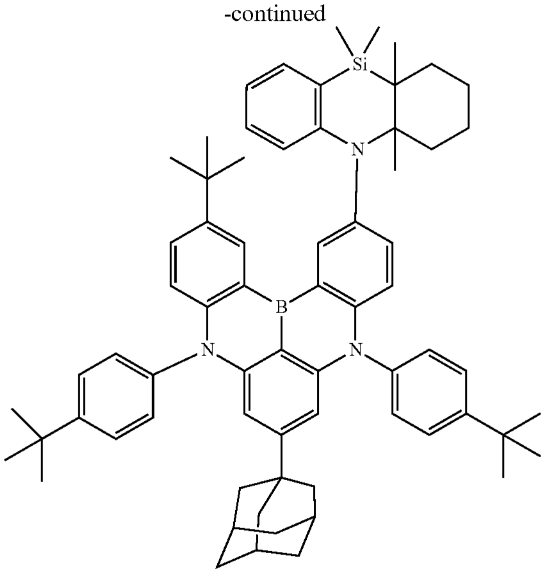
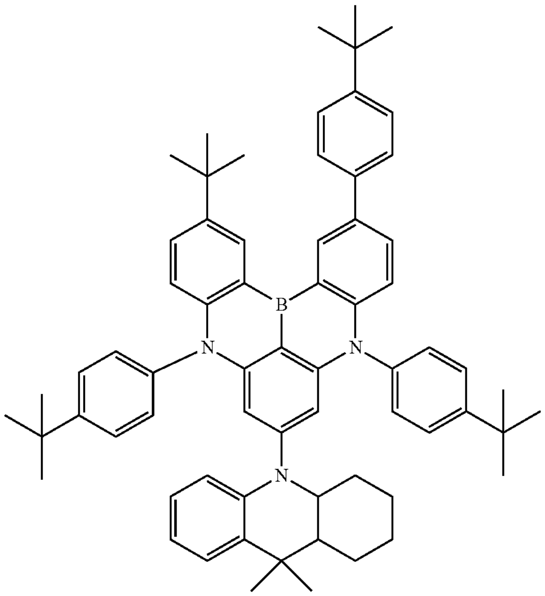
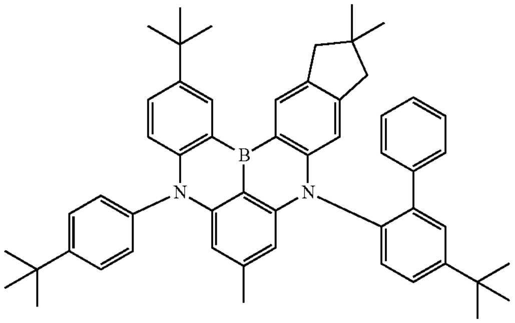

-continued
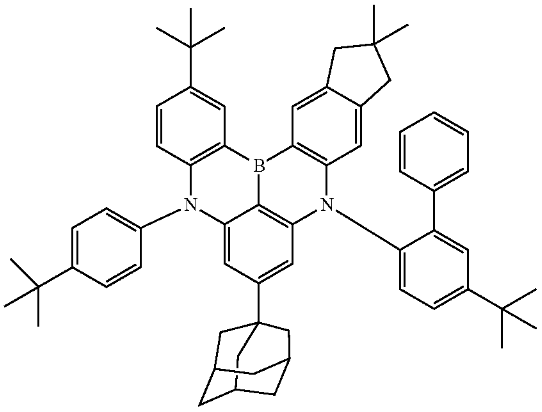
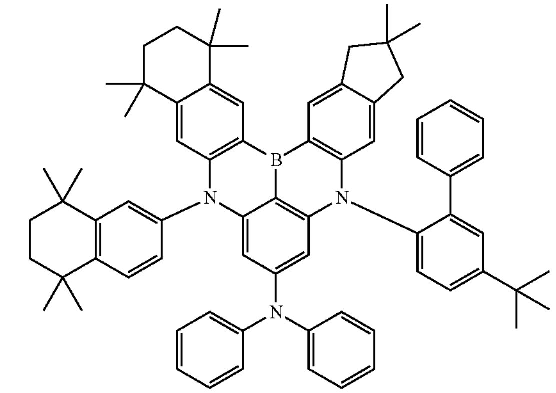
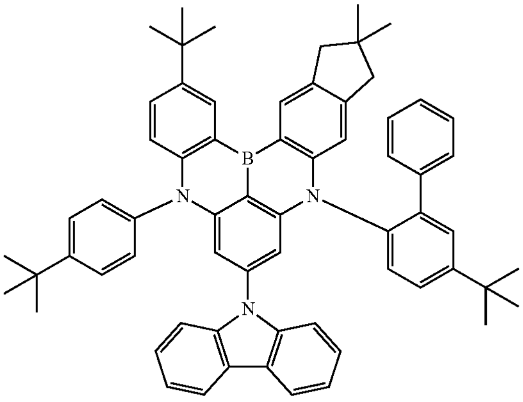
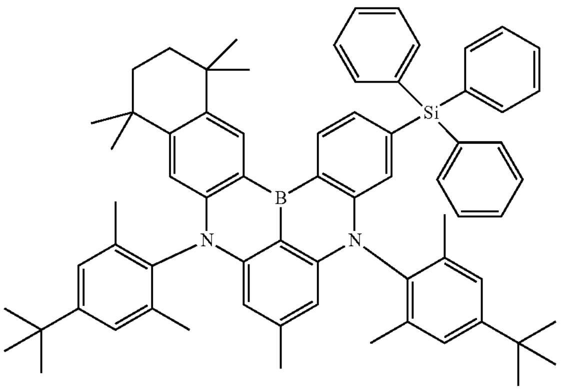
-continued
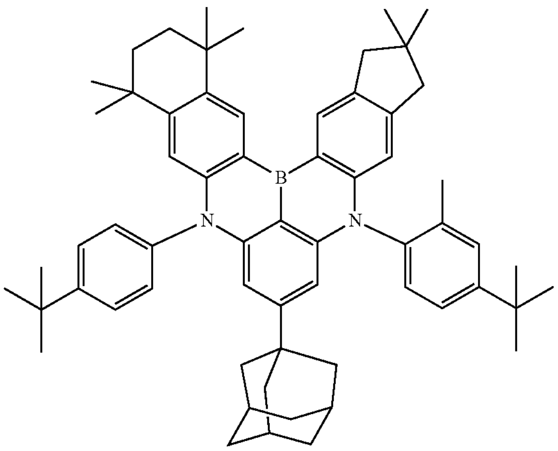
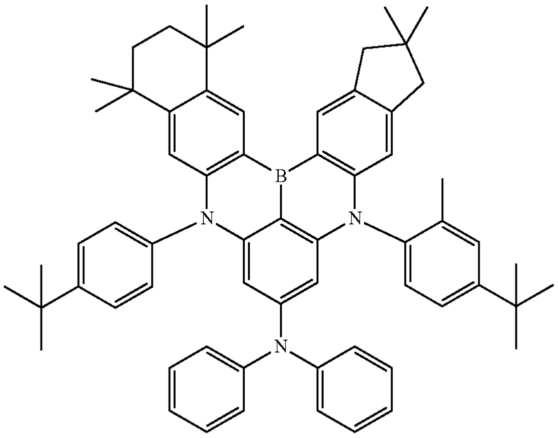
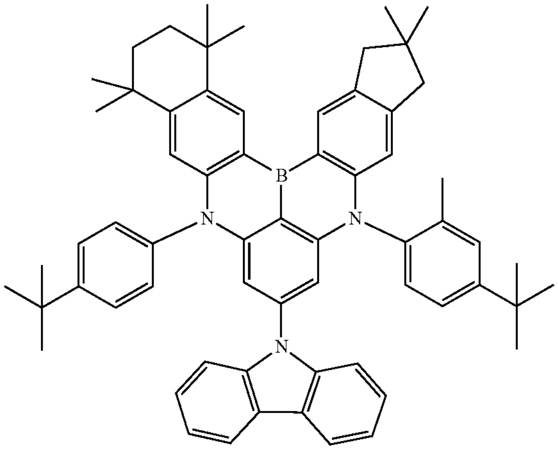
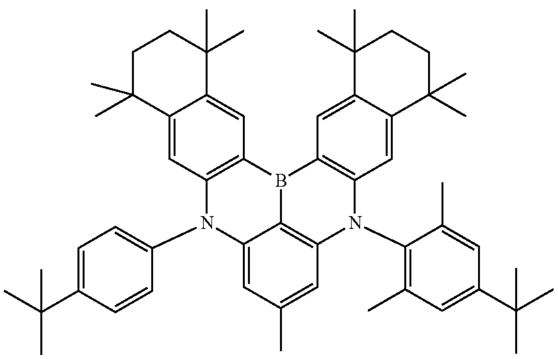

-continued
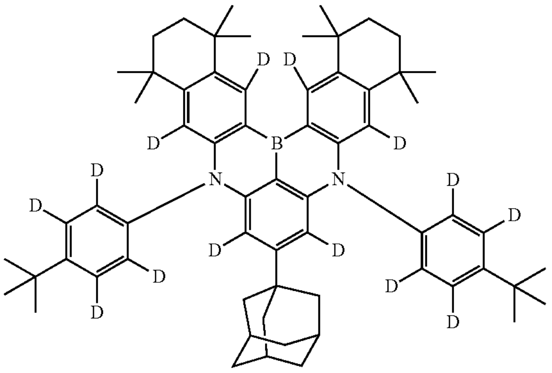
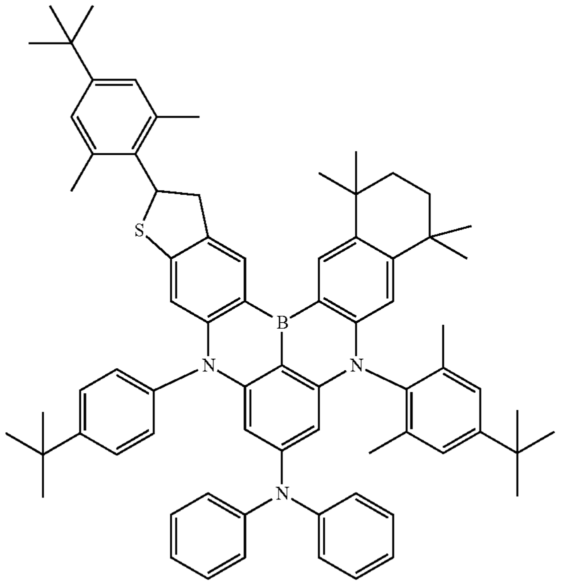
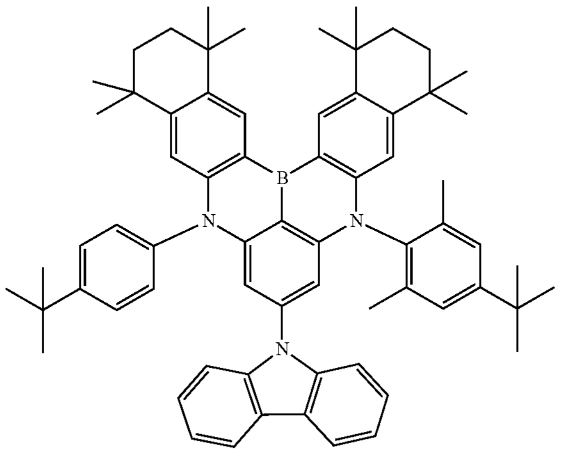
-continued
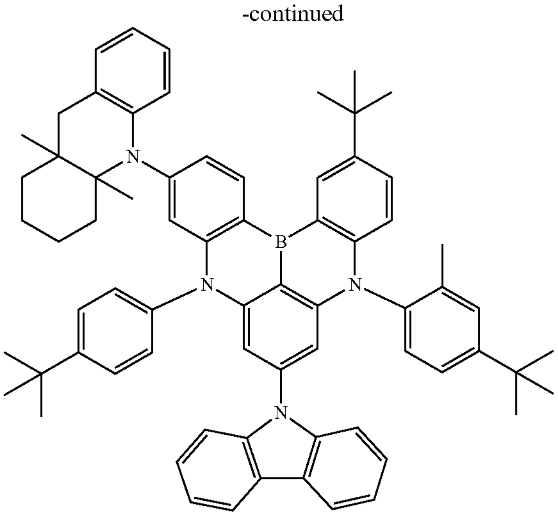
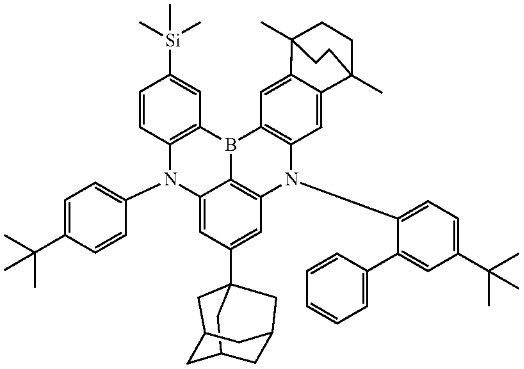
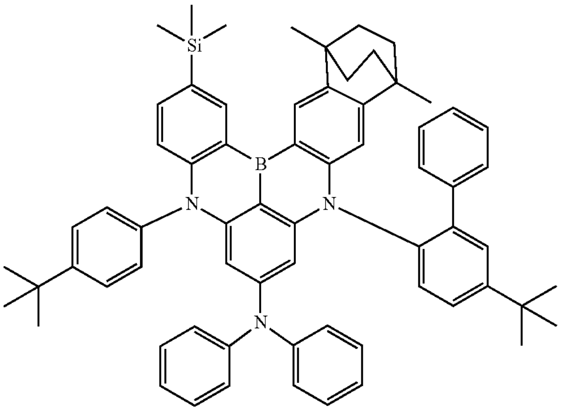
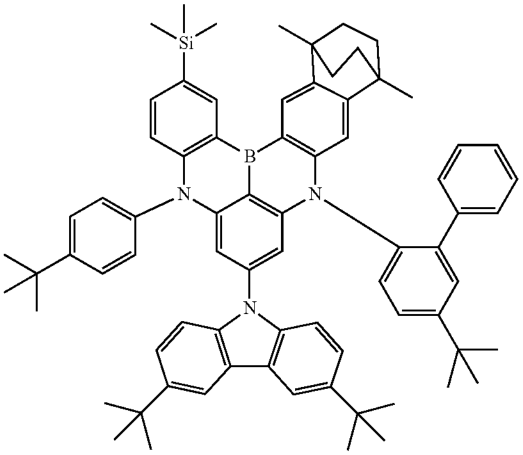

-continued
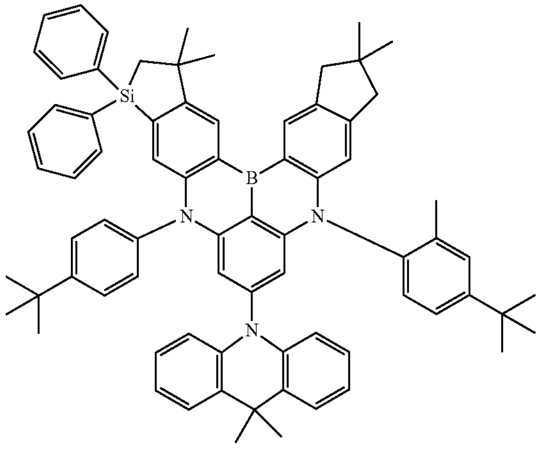
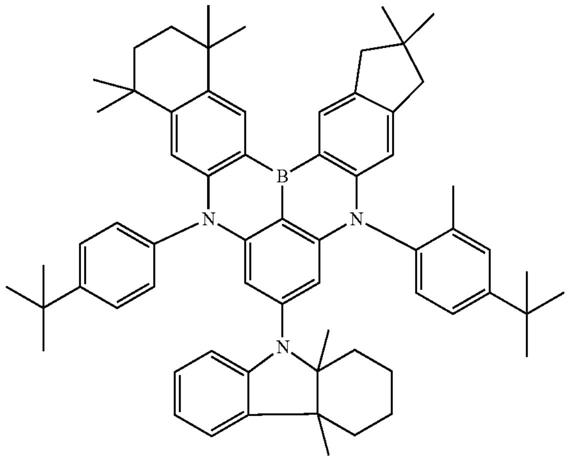
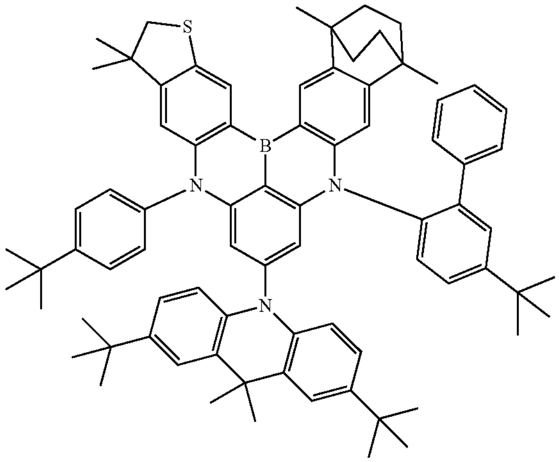
-continued
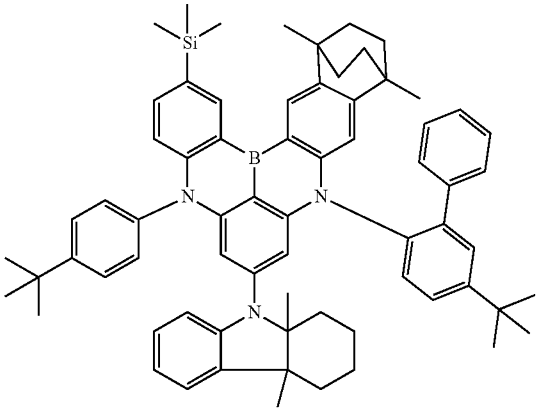
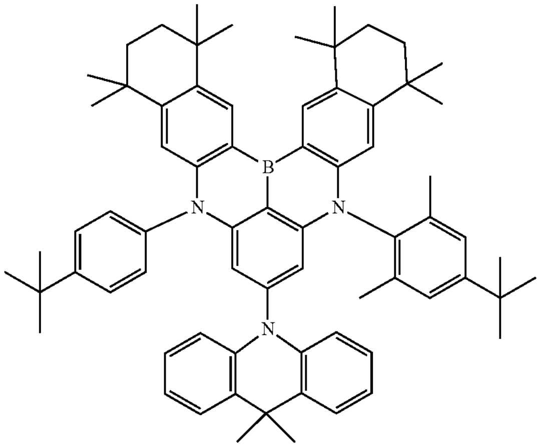
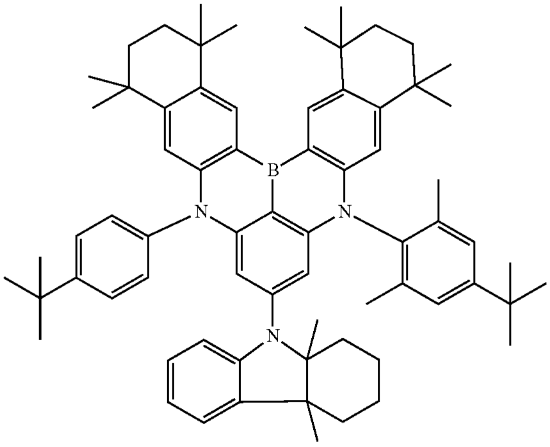
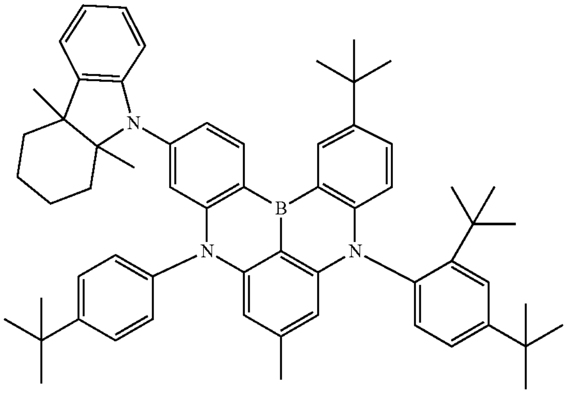

-continued
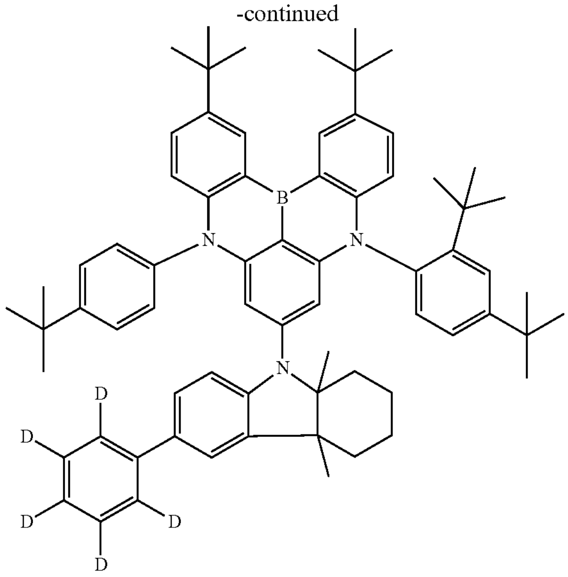
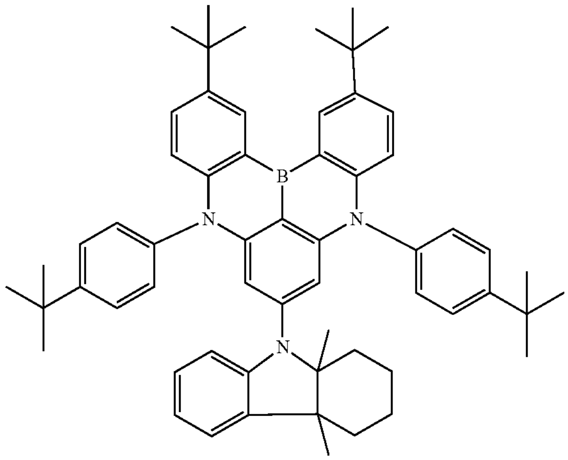
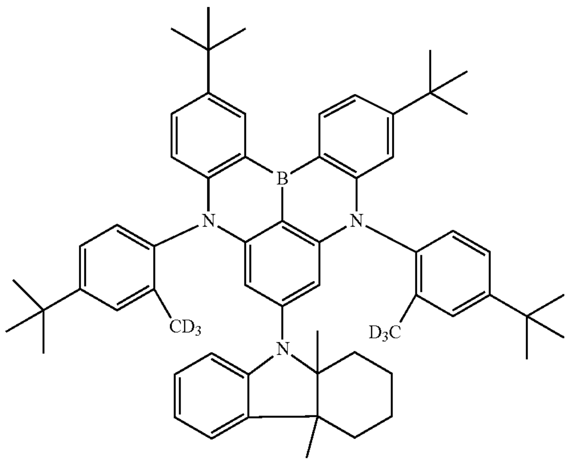
-continued
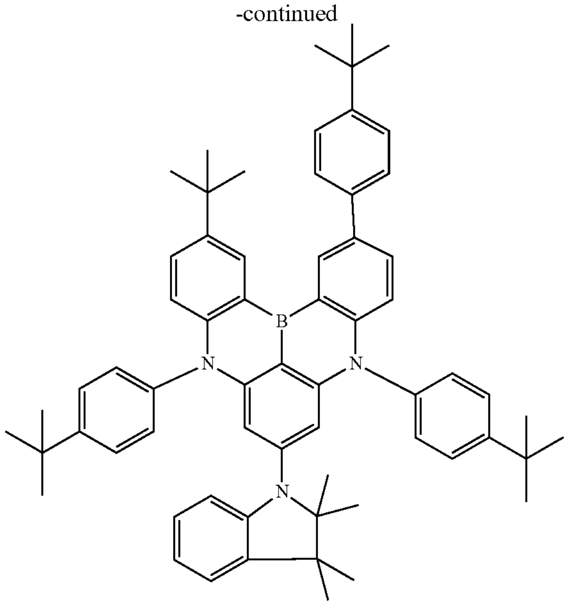
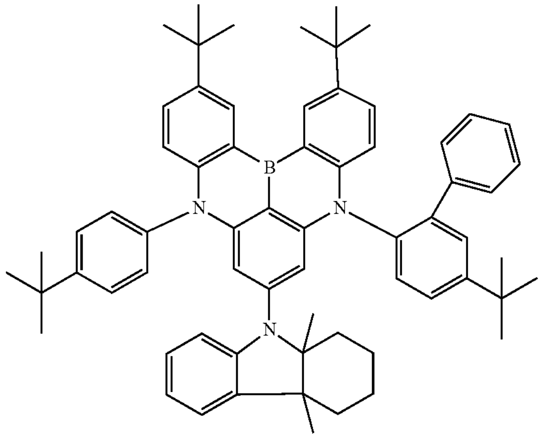
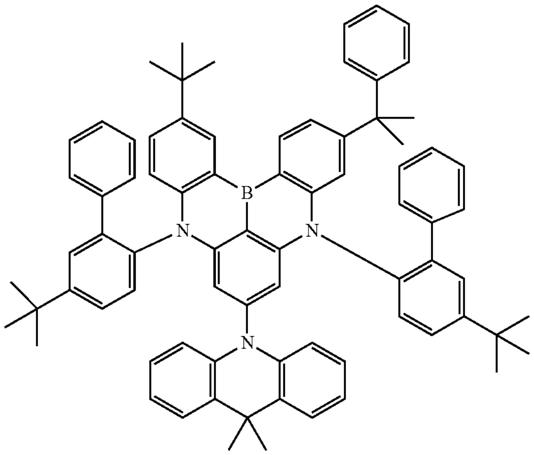

-continued
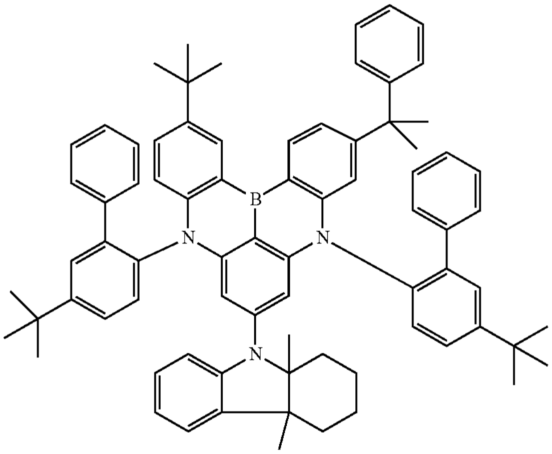
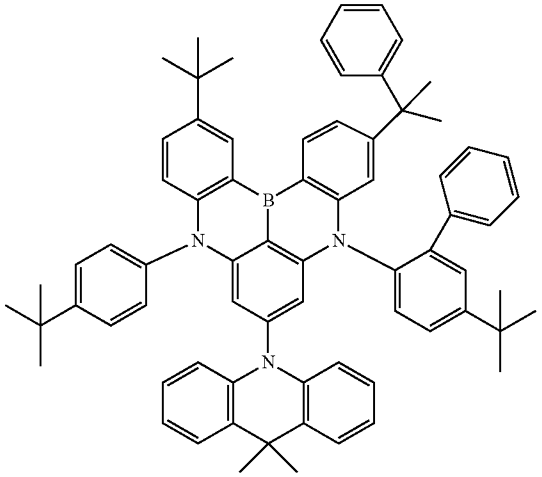
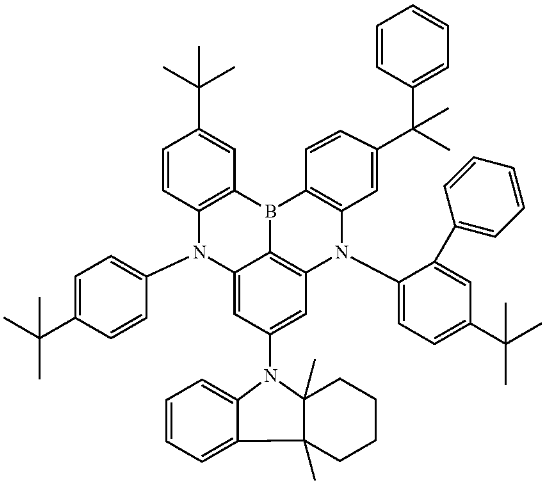
-continued
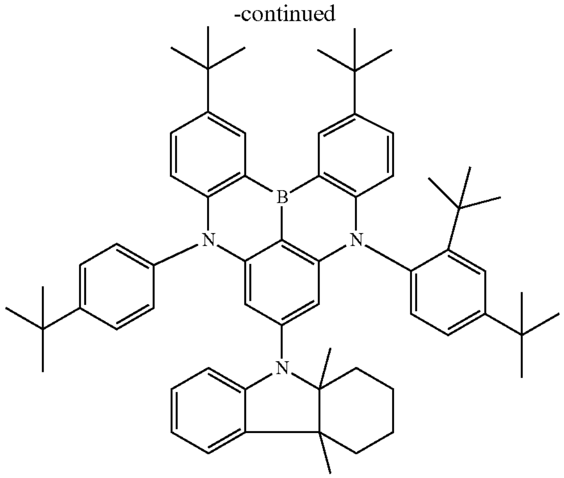
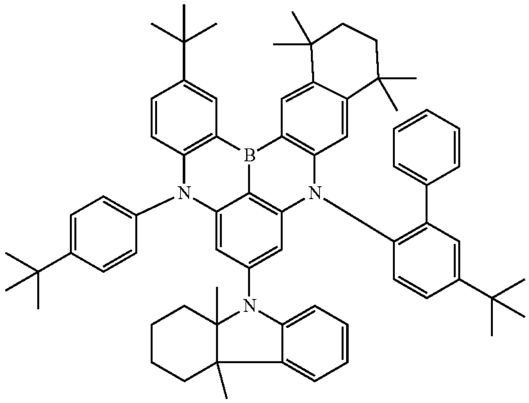
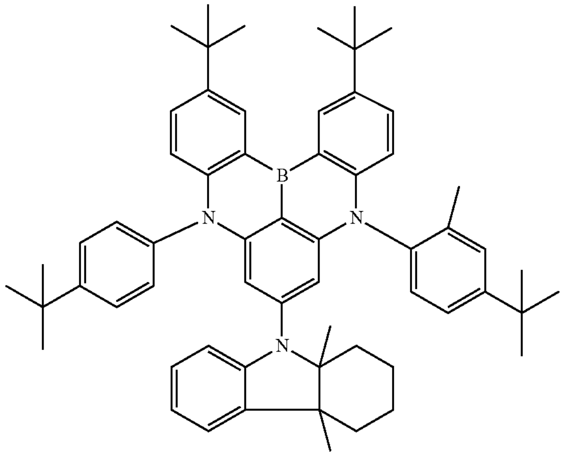
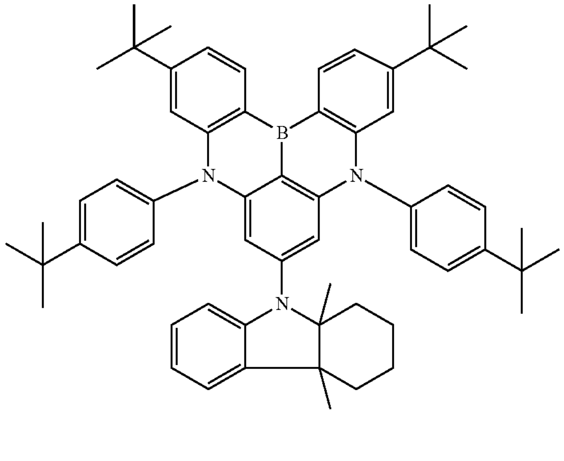

-continued
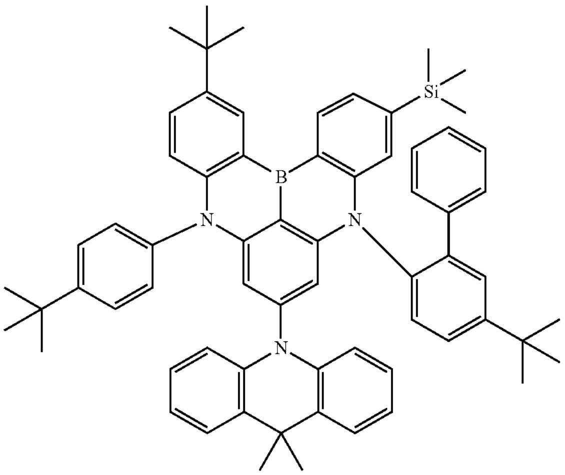
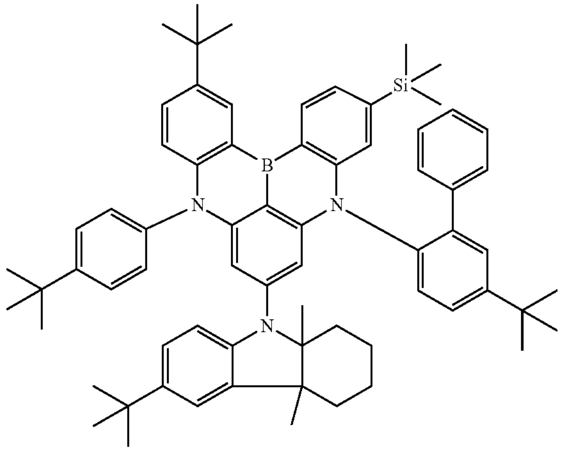
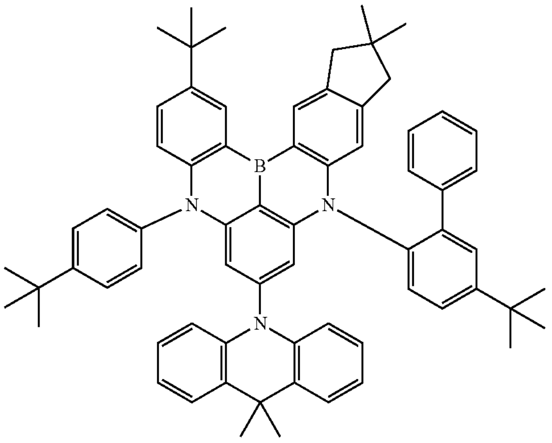
-continued
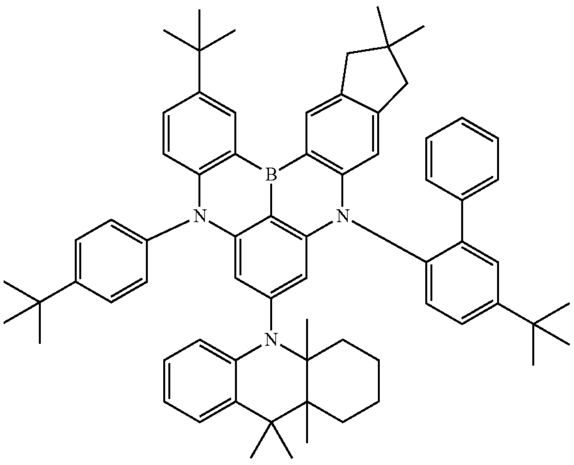
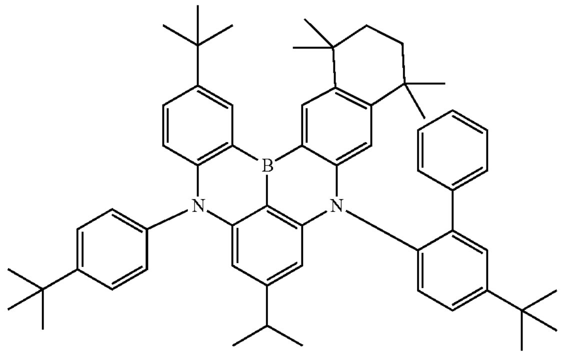
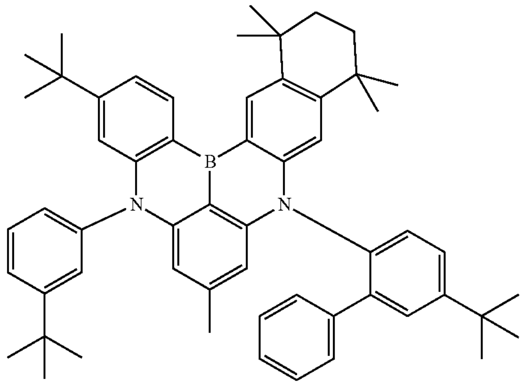
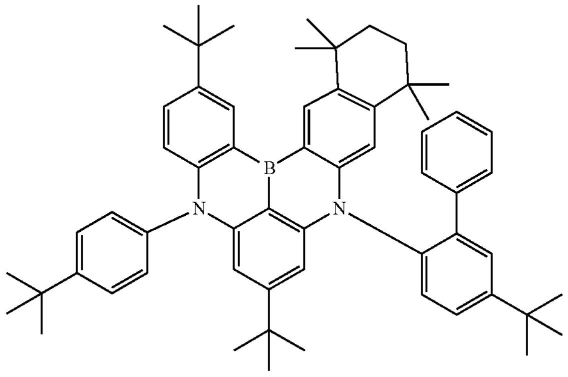

-continued
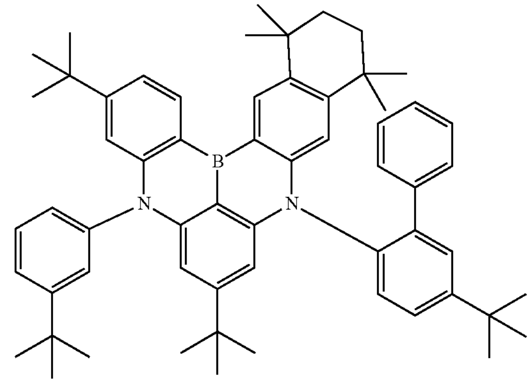
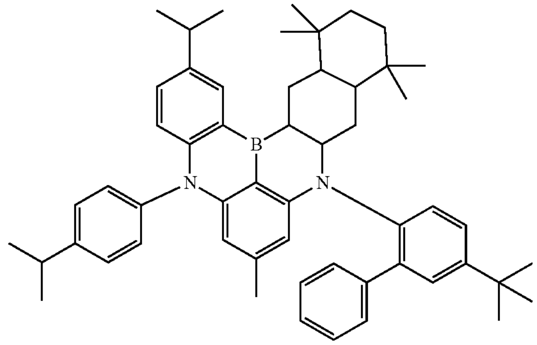
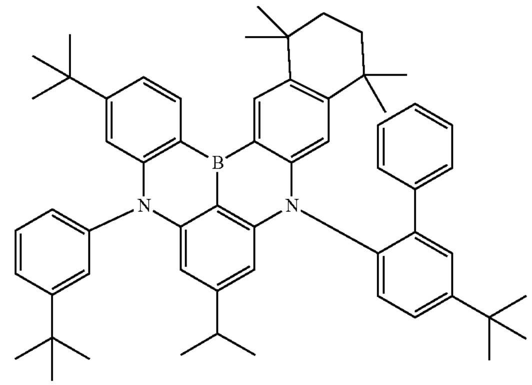
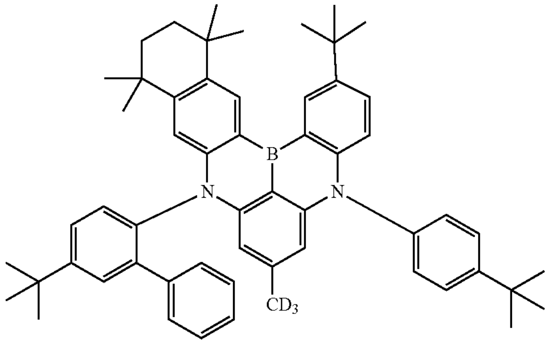
-continued
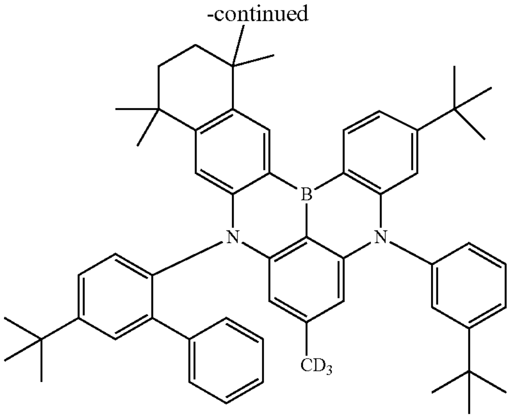
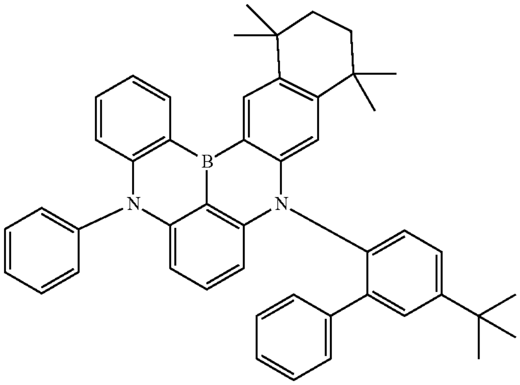
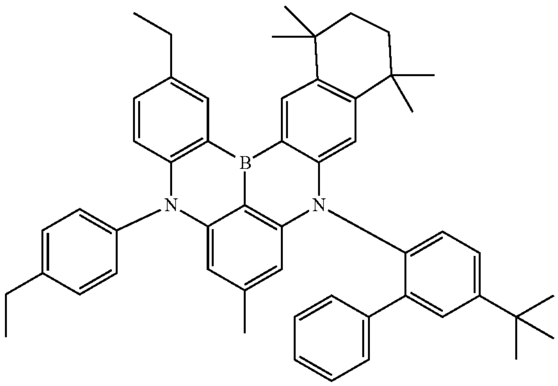
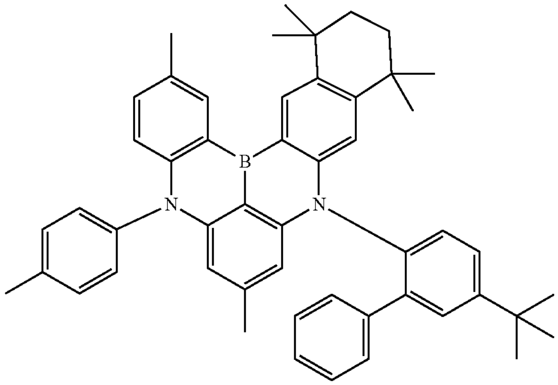

-continued
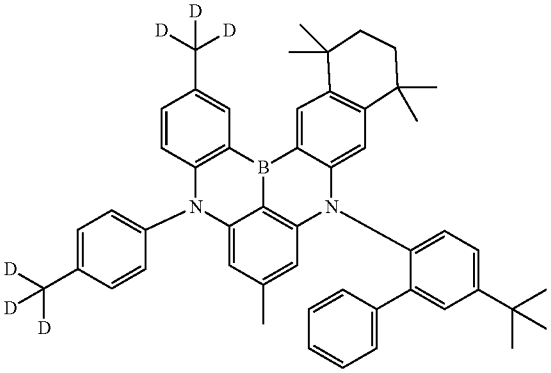
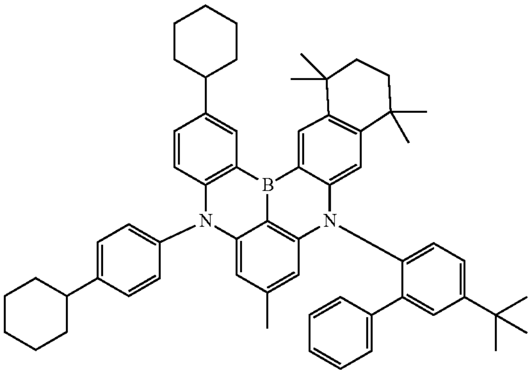
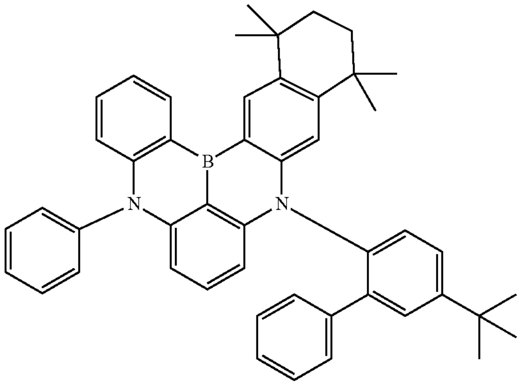
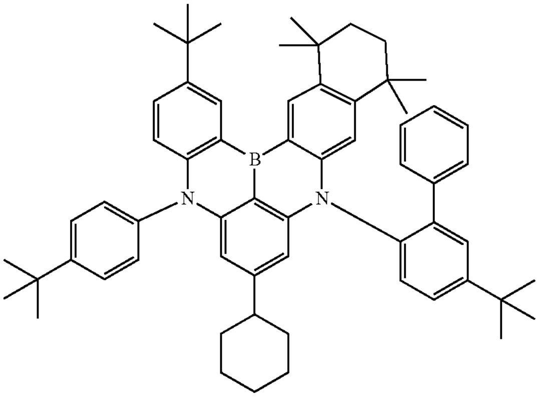
-continued
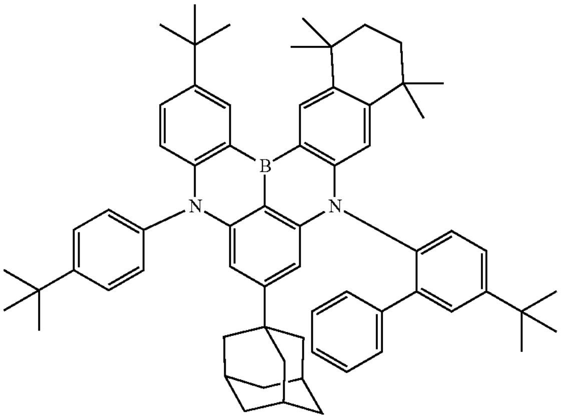
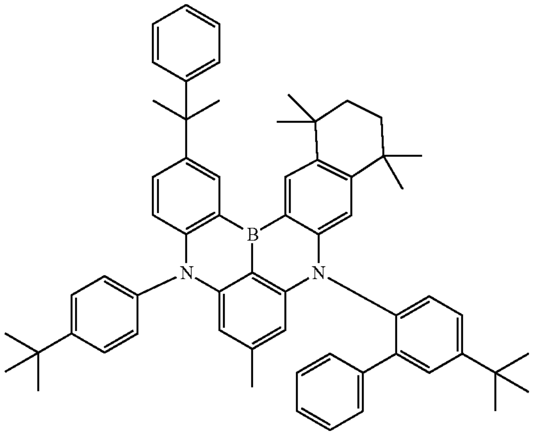
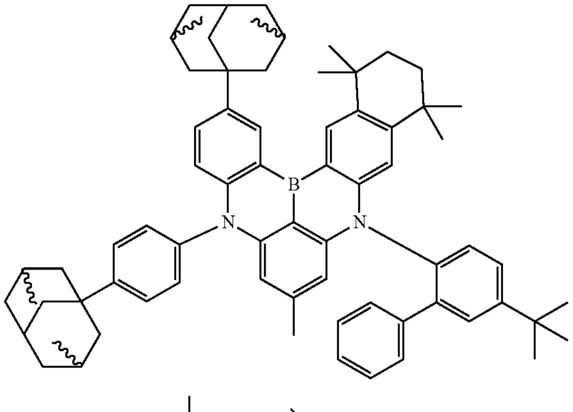
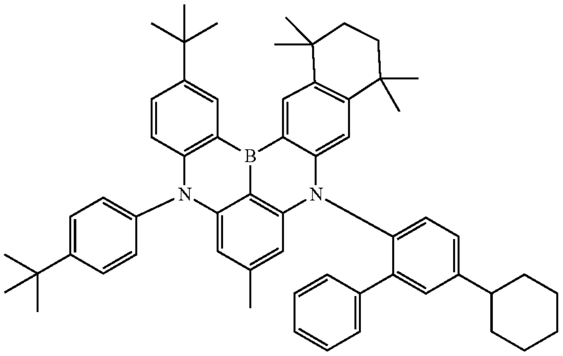

-continued
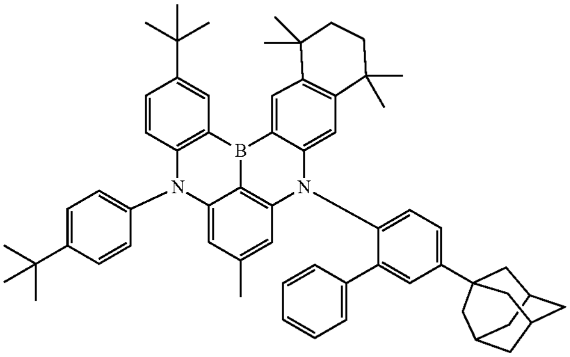
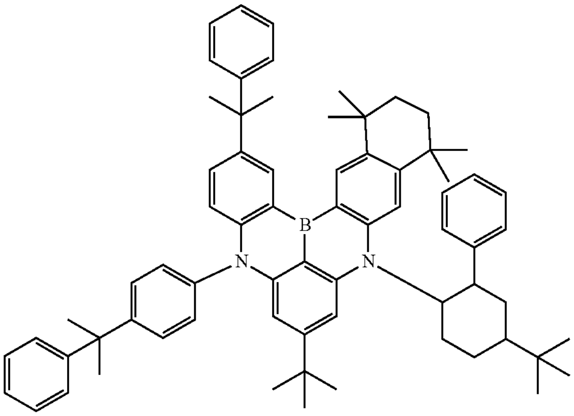
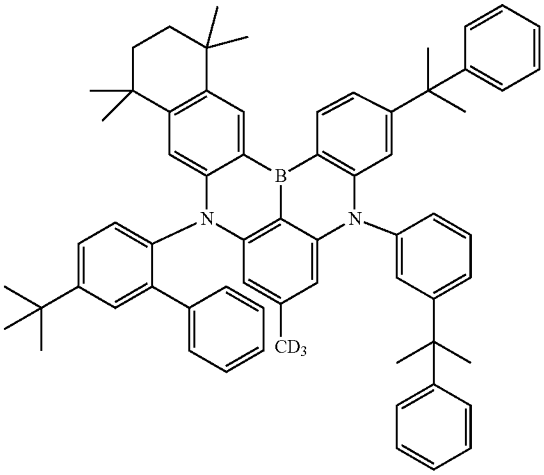
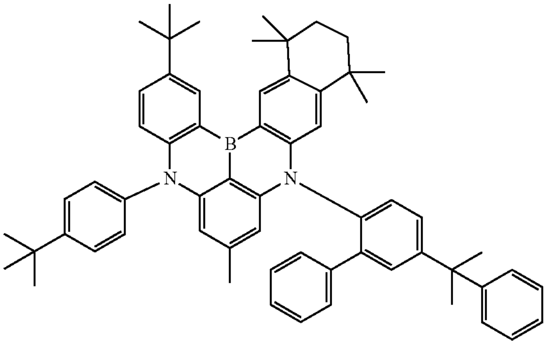
-continued
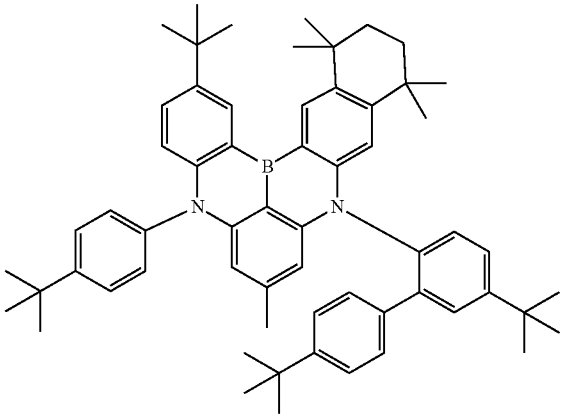
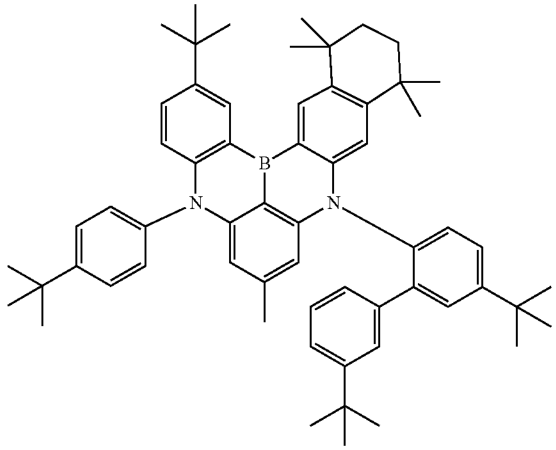
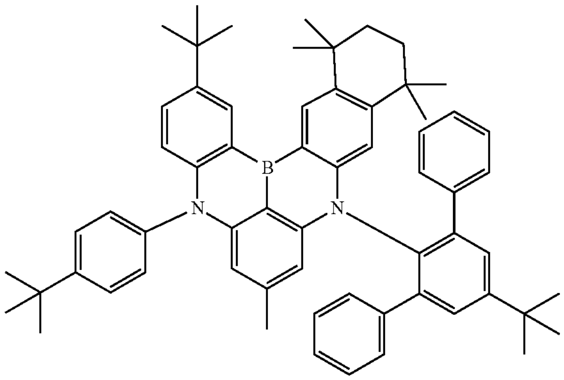
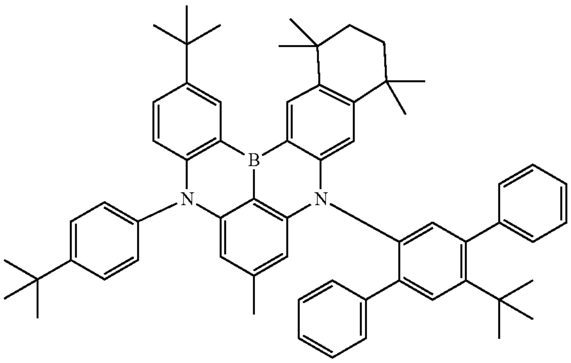

-continued
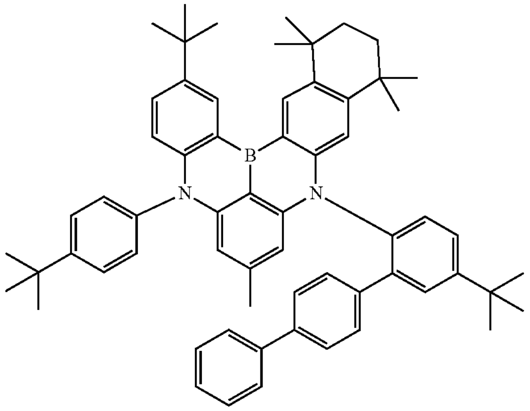
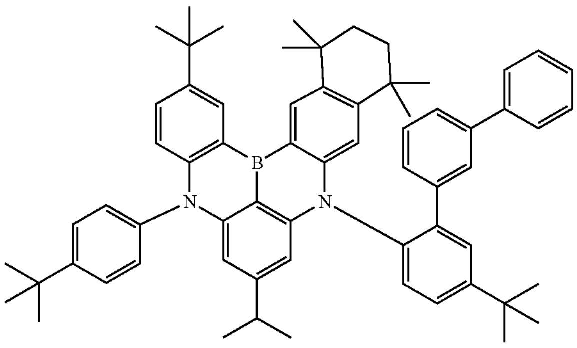
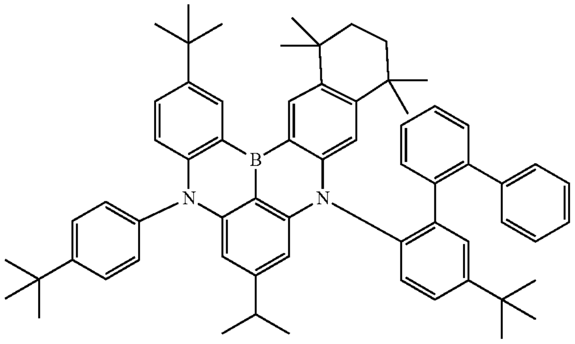
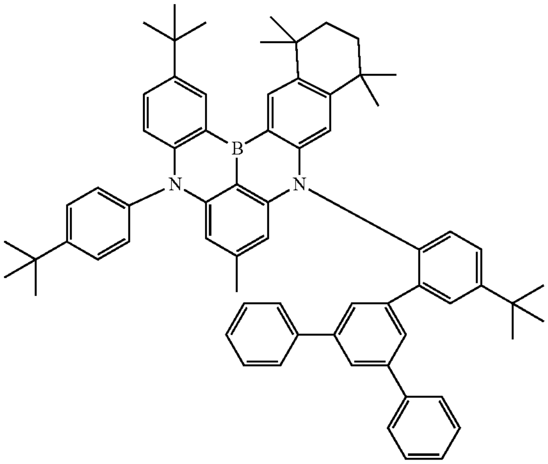
-continued
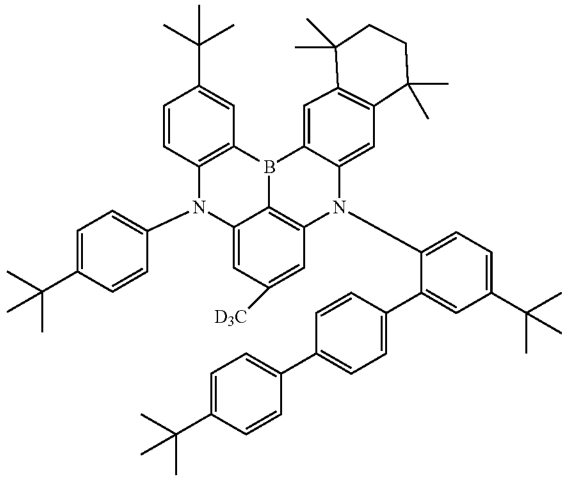
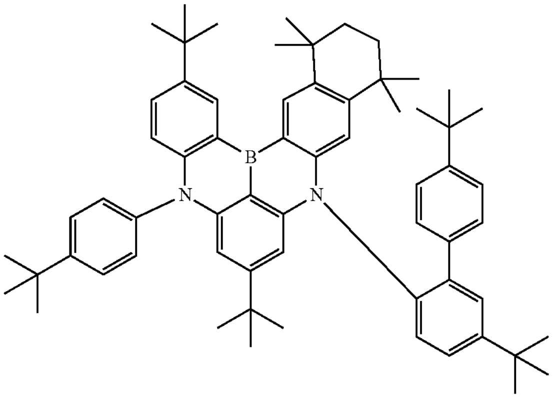
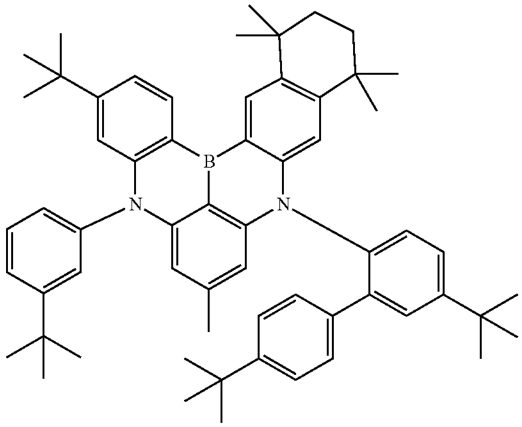
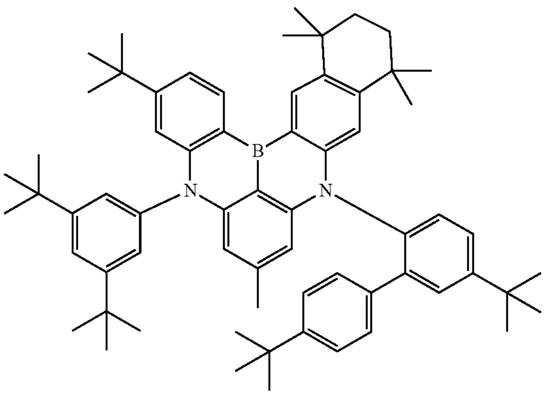

-continued
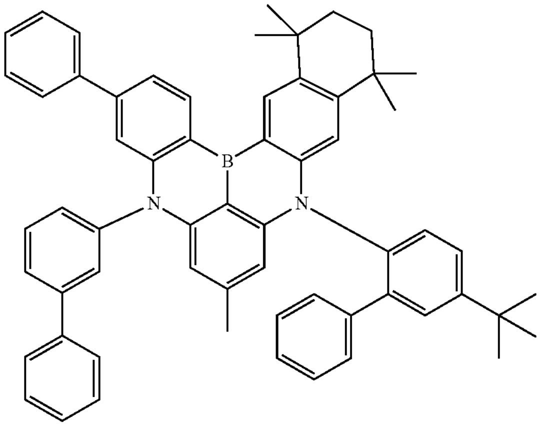
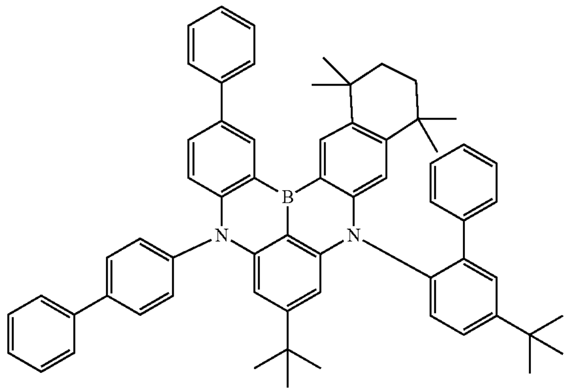
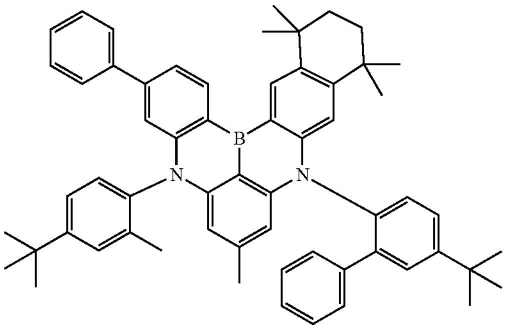
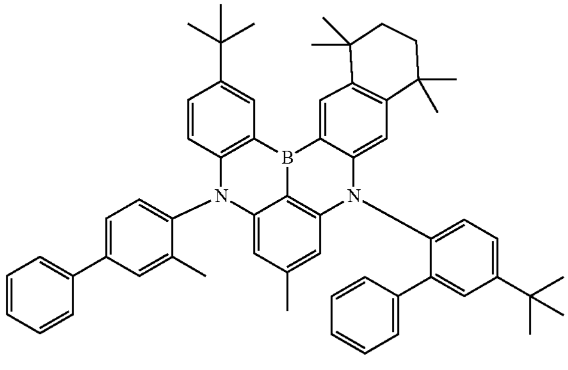
-continued
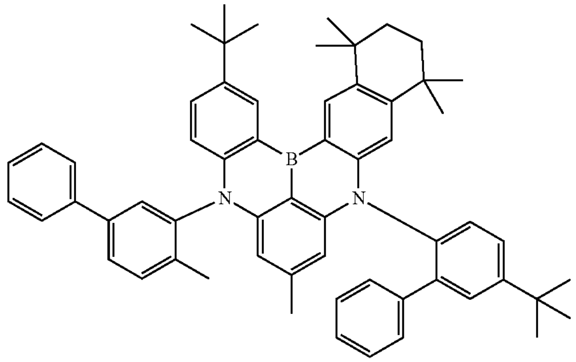
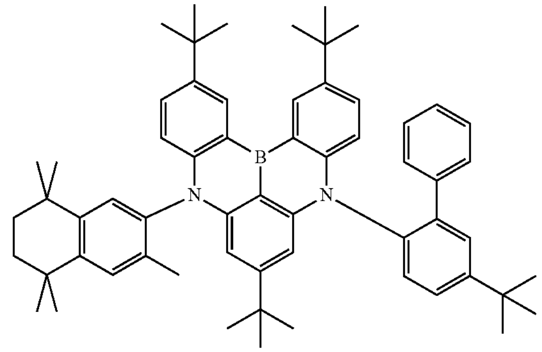
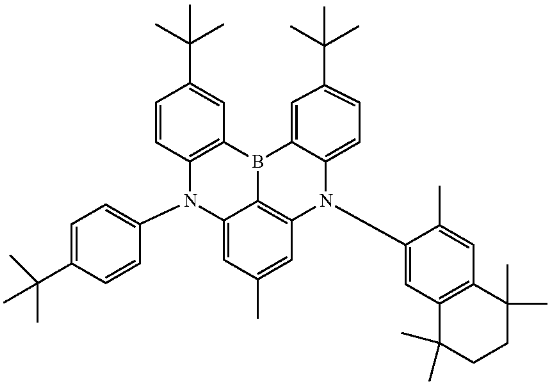
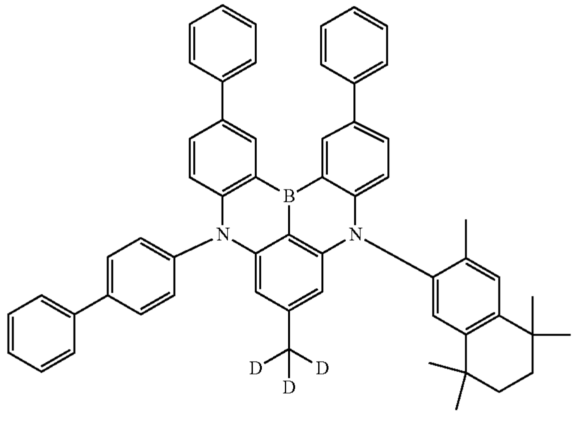

-continued
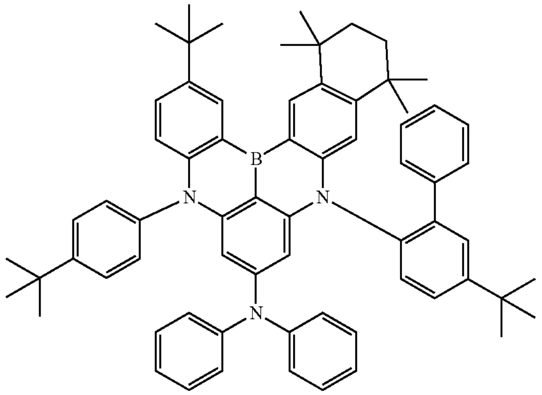
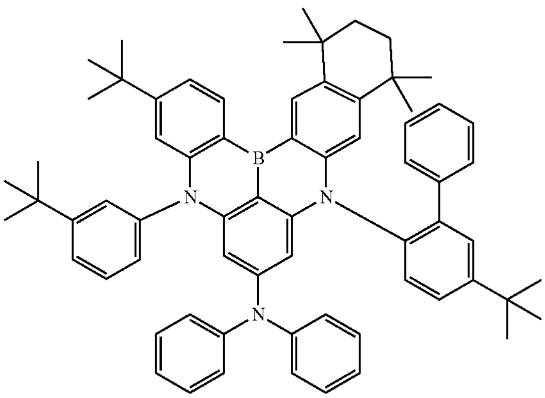
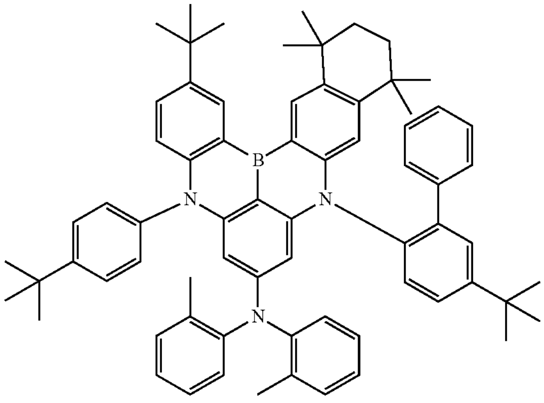
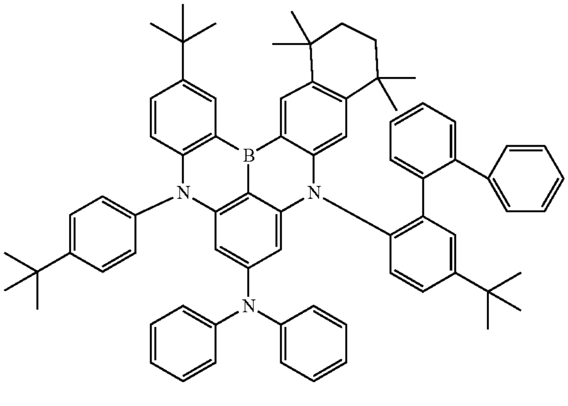
-continued
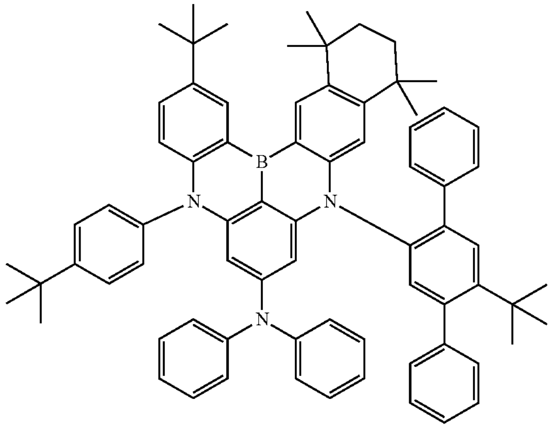
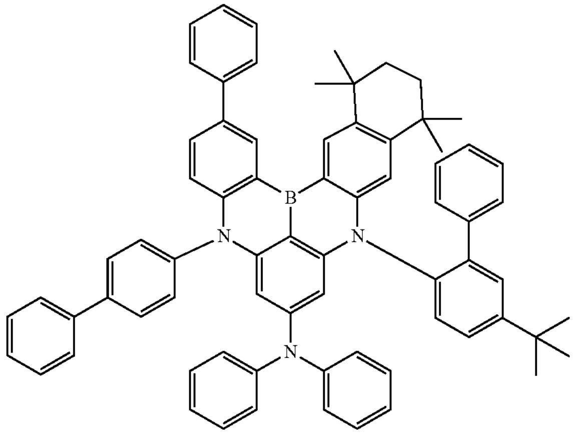
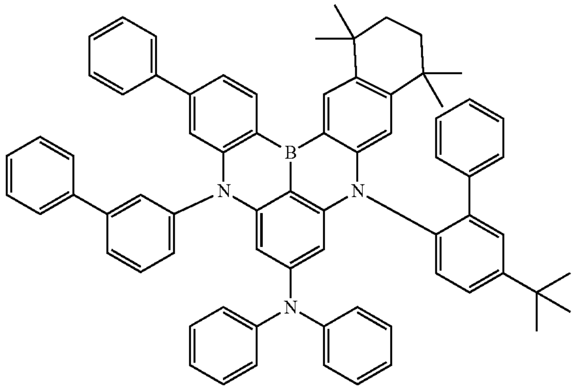
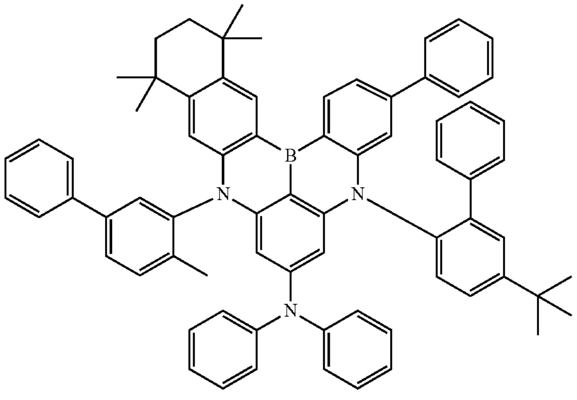

-continued
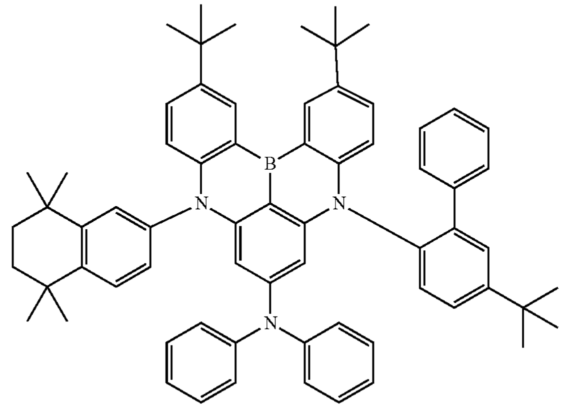
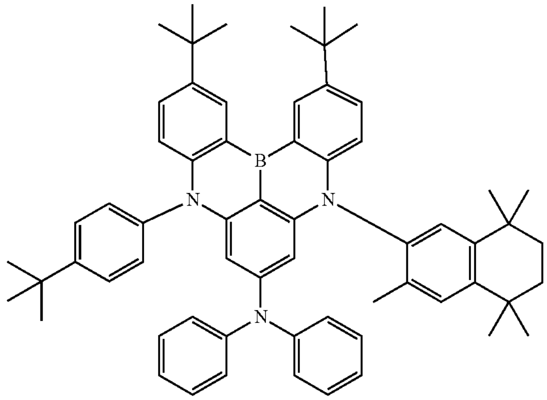
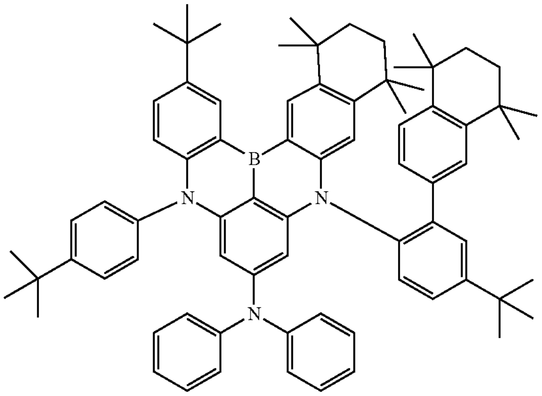
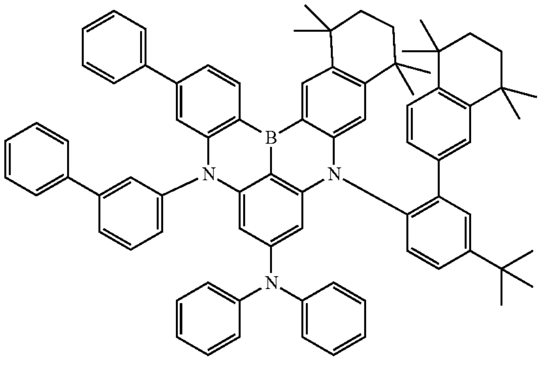
-continued
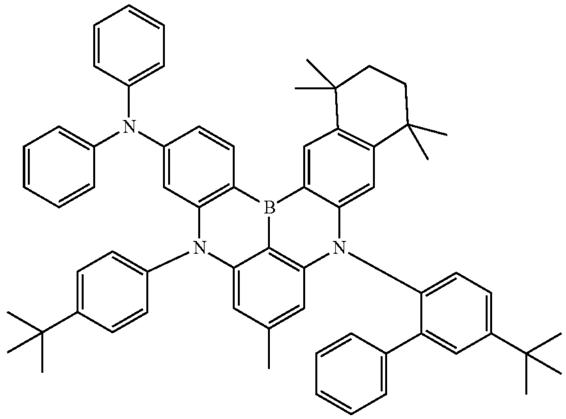
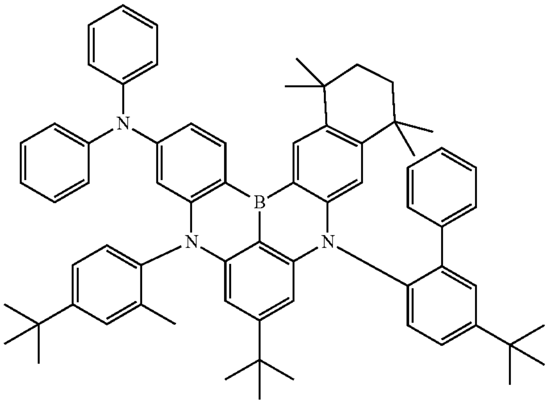
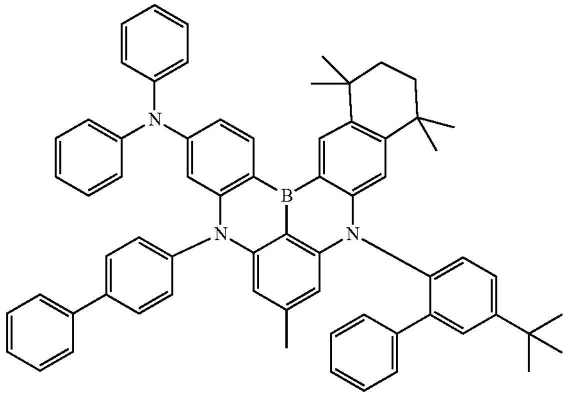
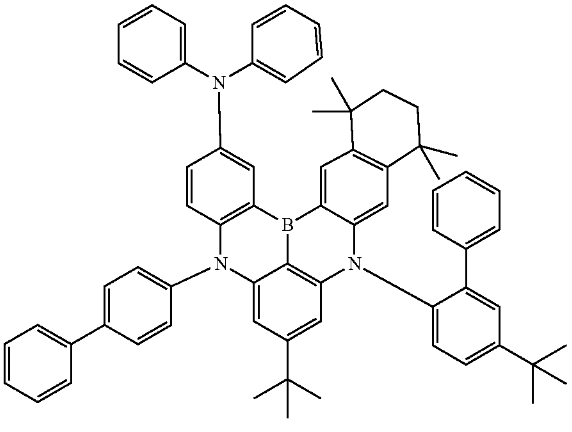

-continued
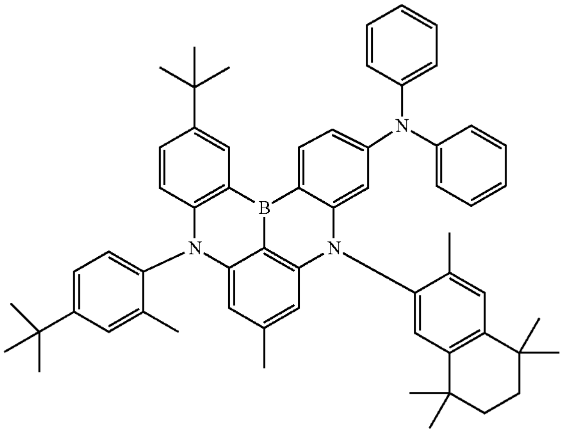
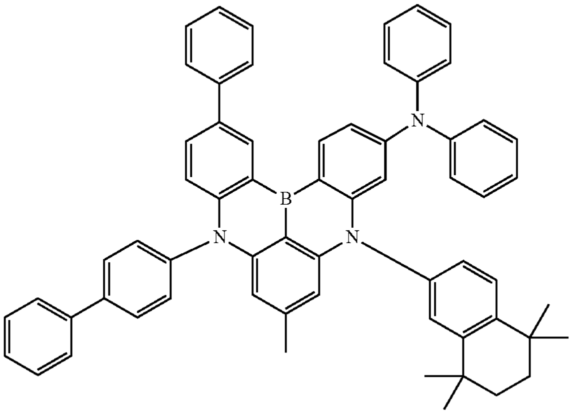
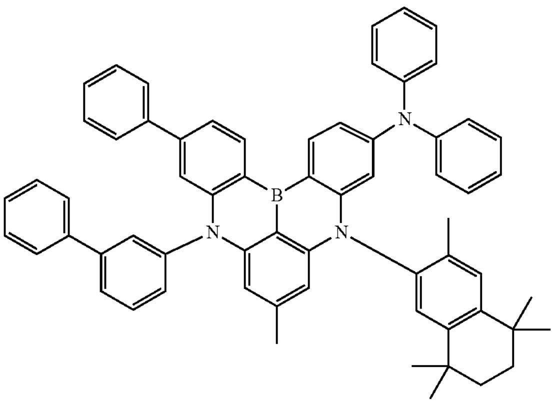
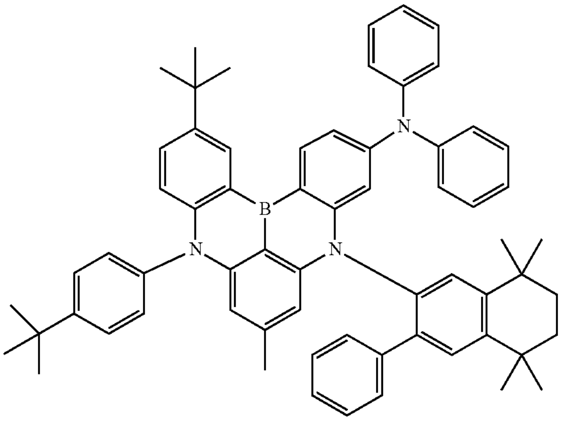
-continued
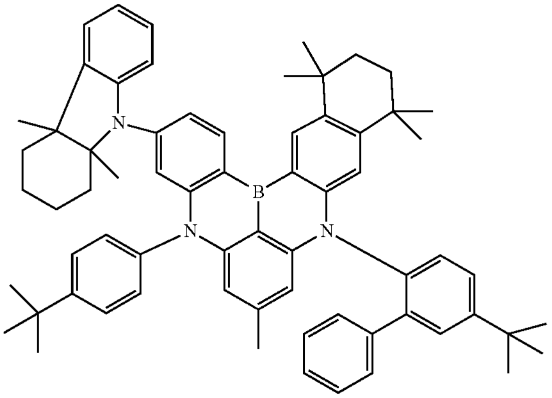
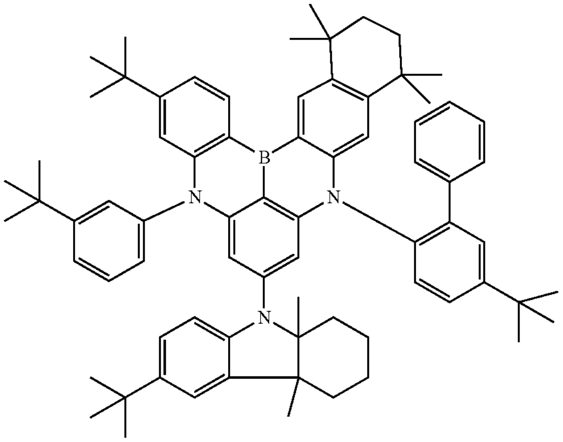
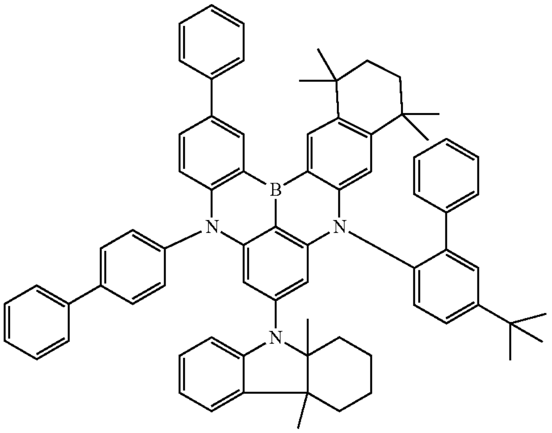
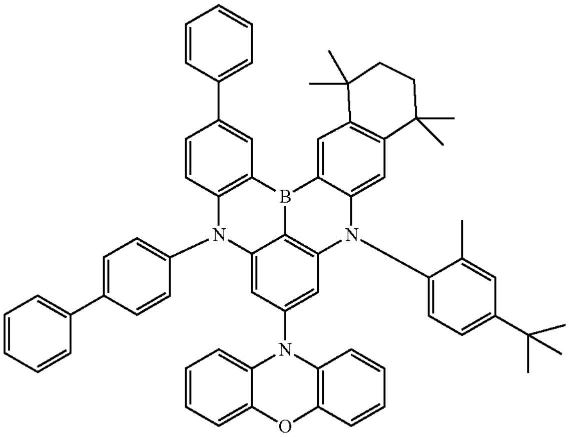

-continued
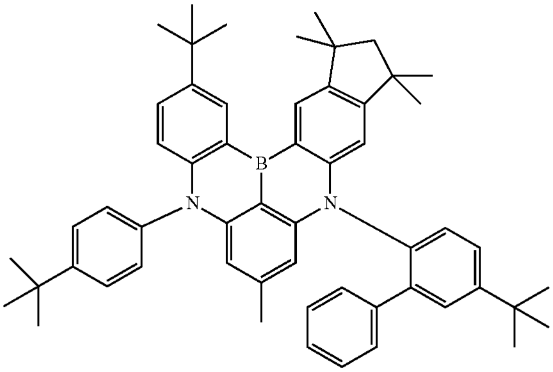
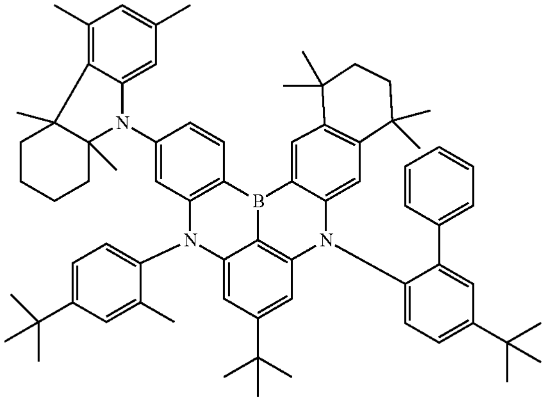
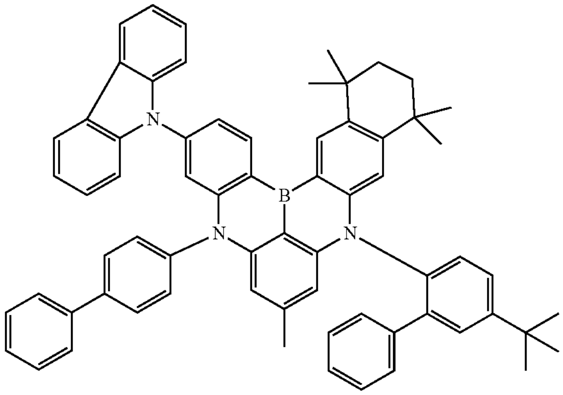
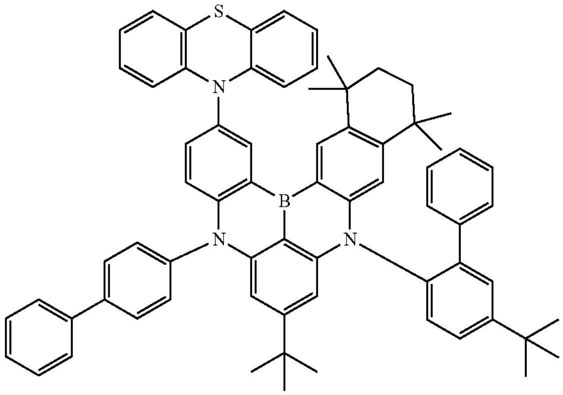
-continued
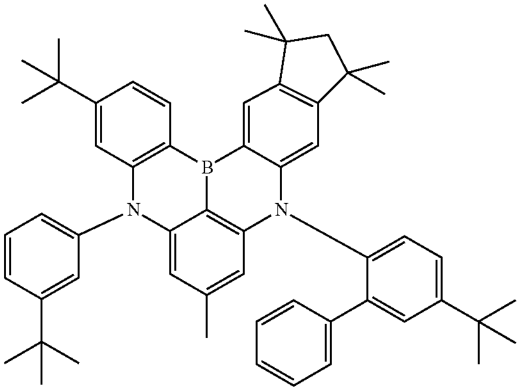
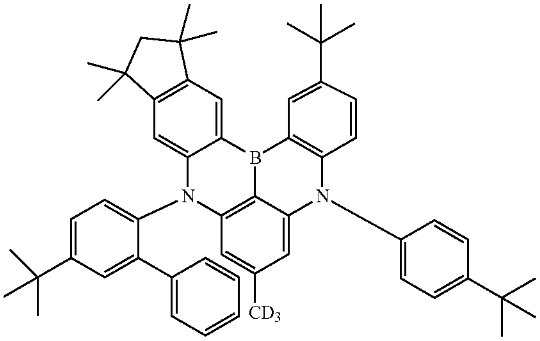
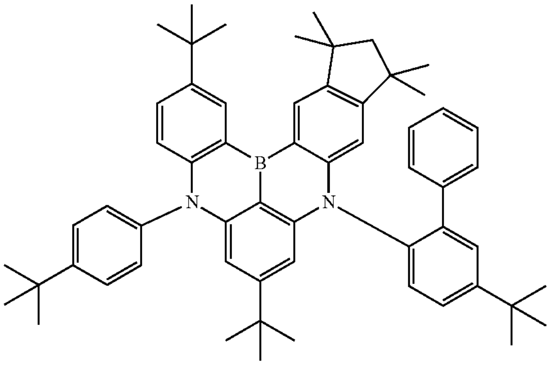
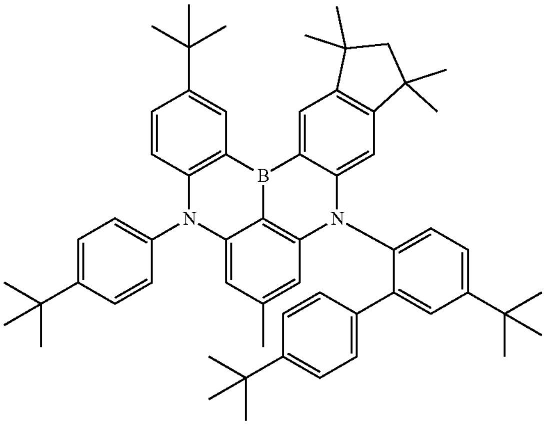

-continued
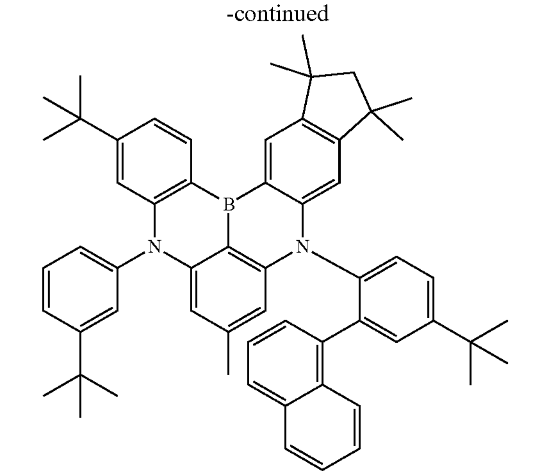
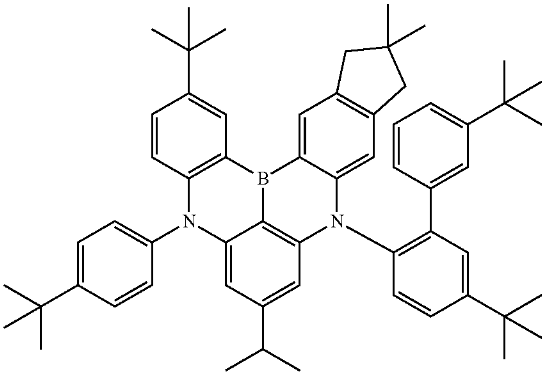
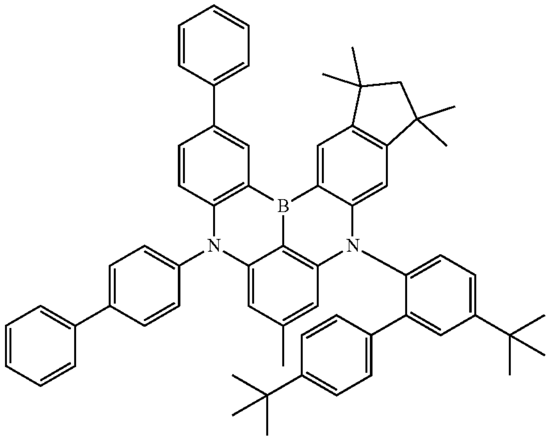
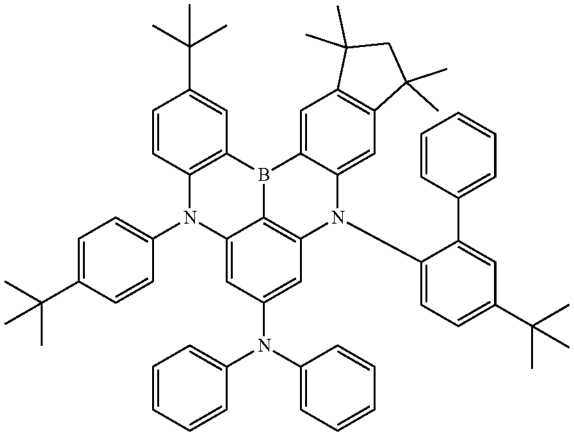
-continued
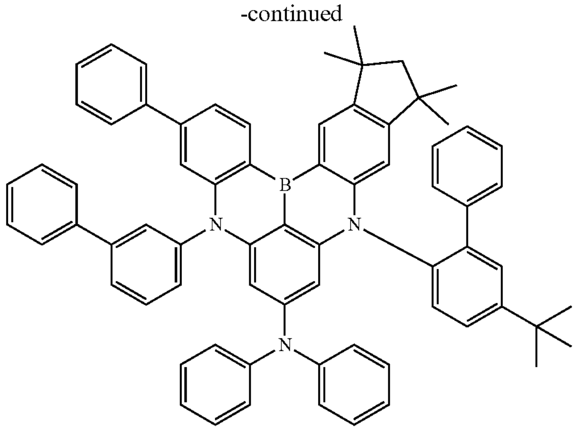
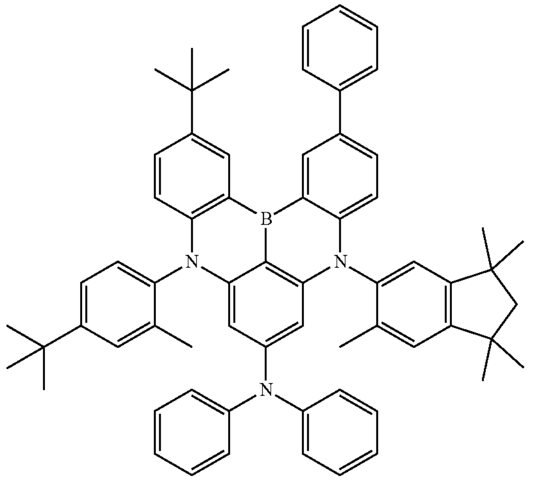
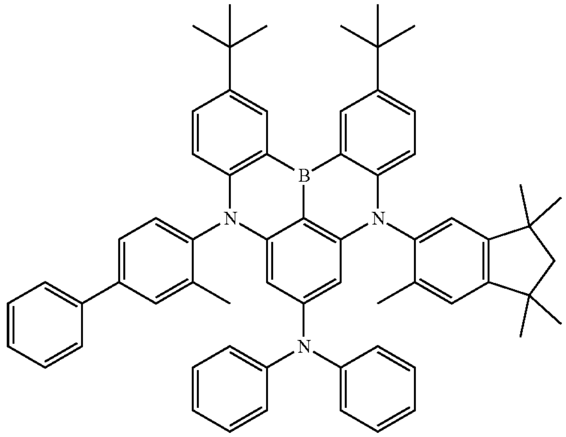 [SMILES: Cc1cc(-c2ccccc2)ccc1N1c2ccc(C(C)(C)C)cc2B2c3cc(C(C)(C)C)ccc3N(c3cc4c(cc3C)C(C)(C)CC4(C)C)c3cc(N(c4ccccc4)c4ccccc4)cc1c32]
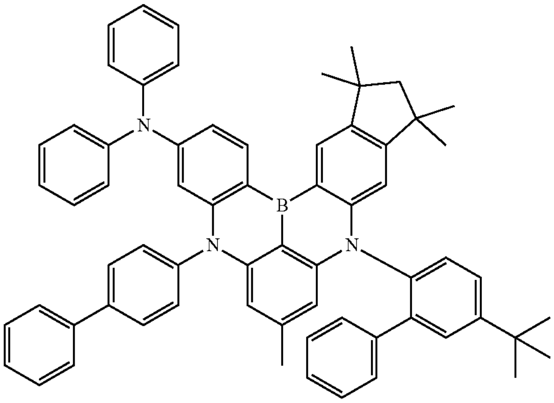

-continued
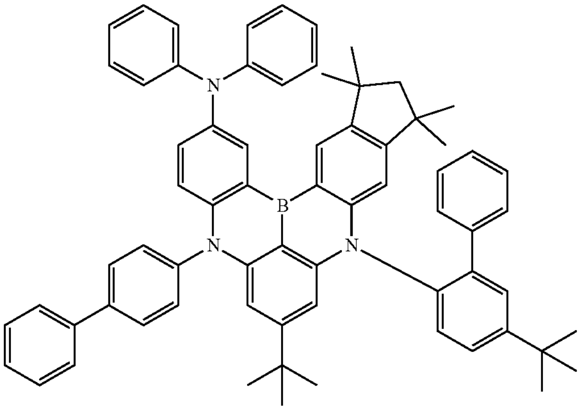
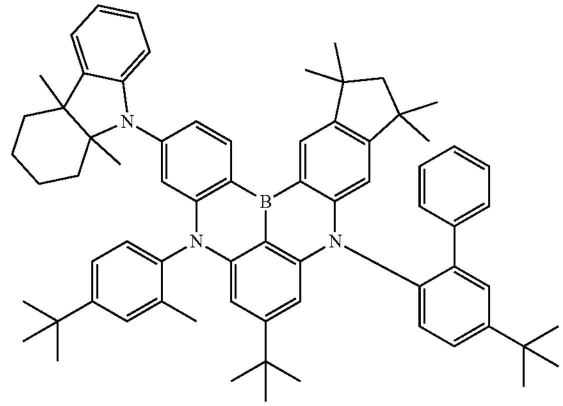
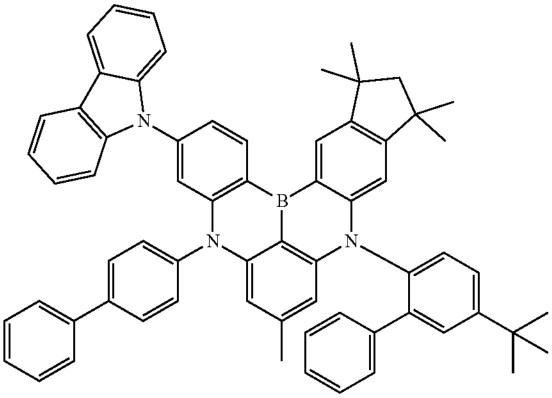
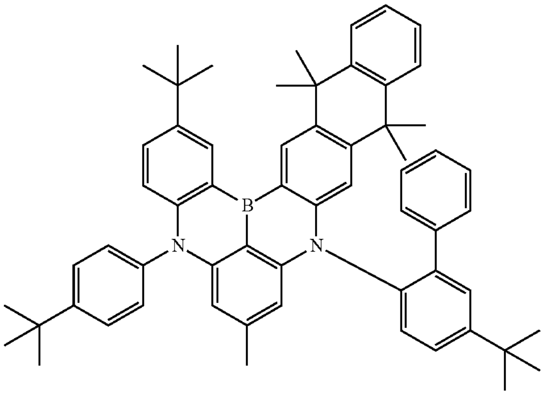
-continued
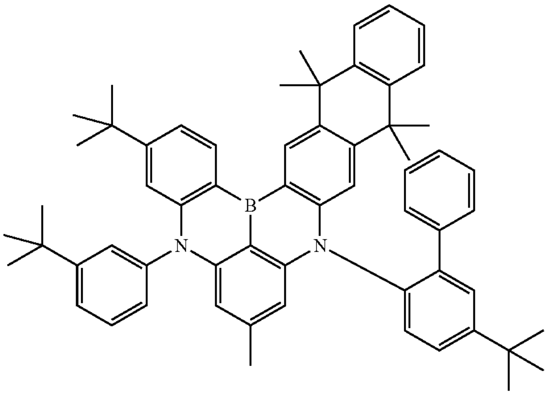
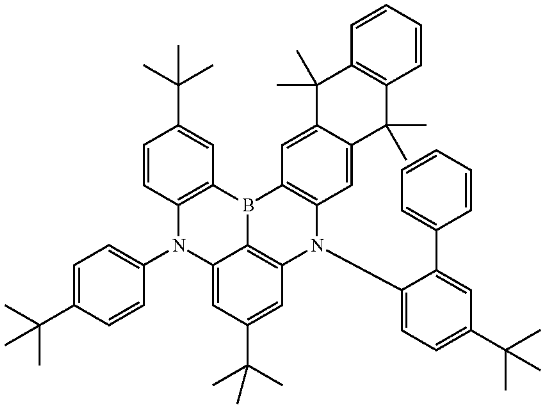
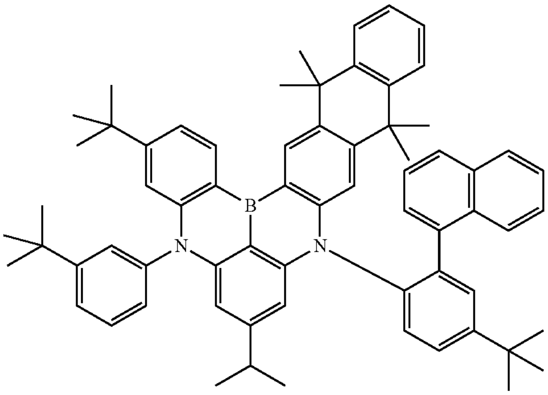
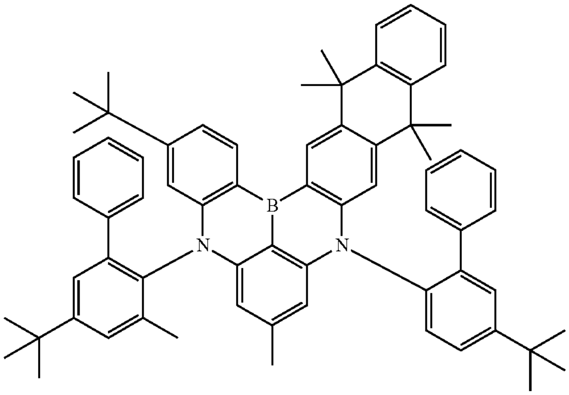

-continued
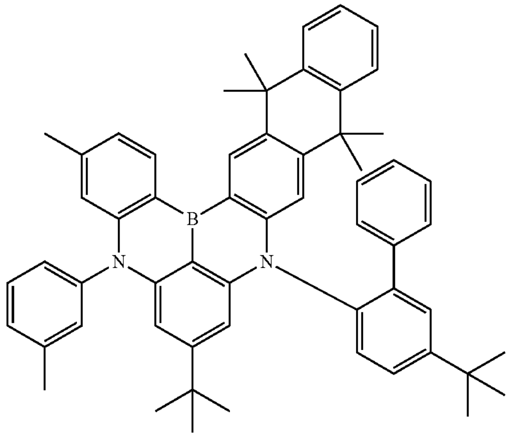
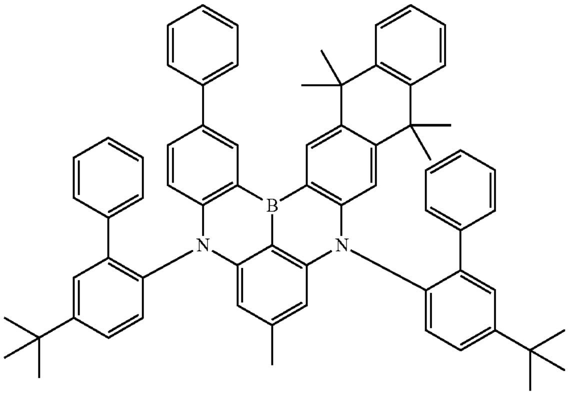
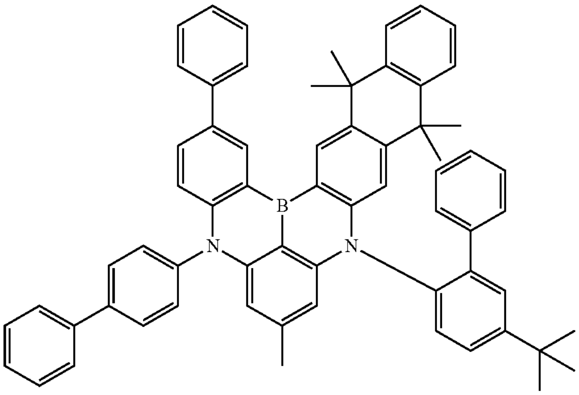
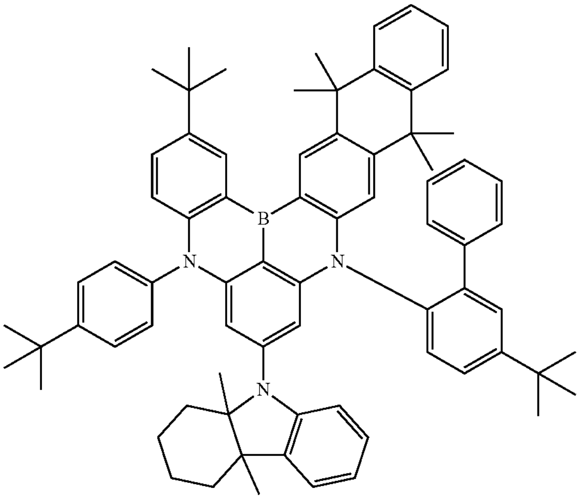
-continued
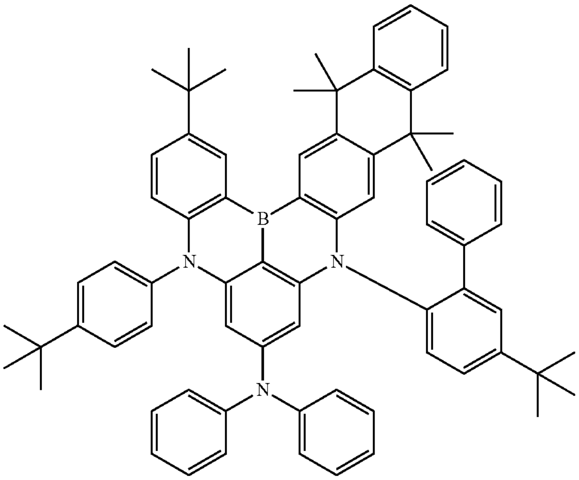
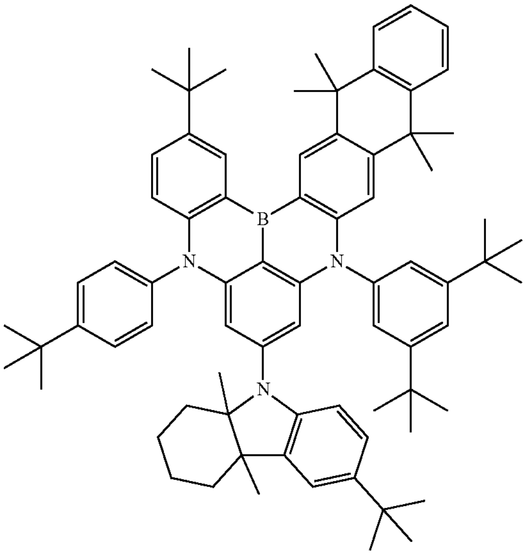
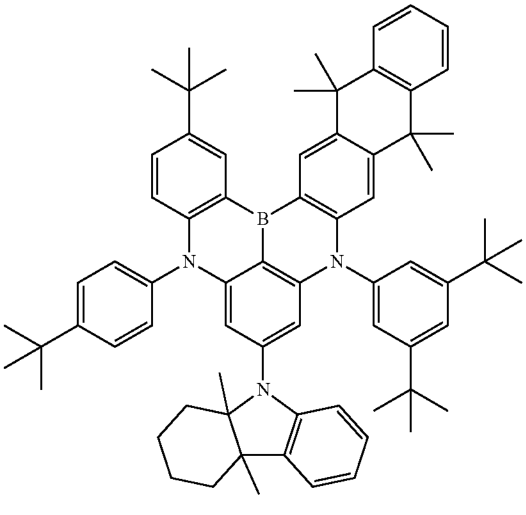

-continued
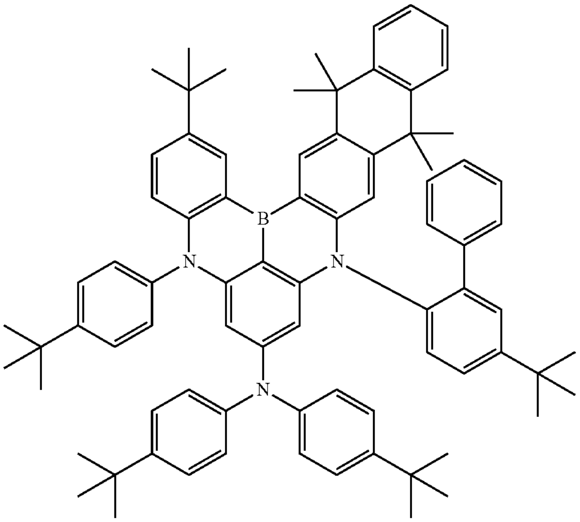
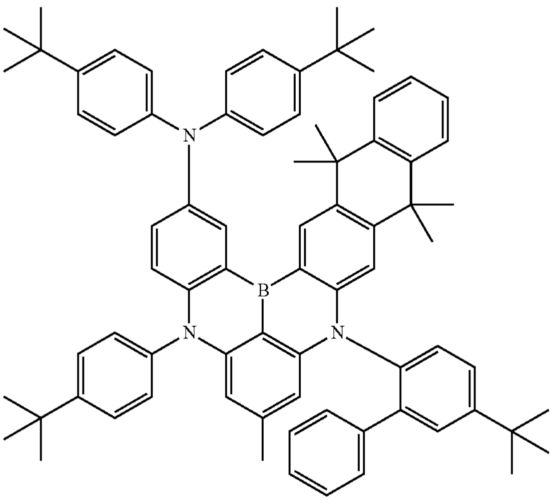
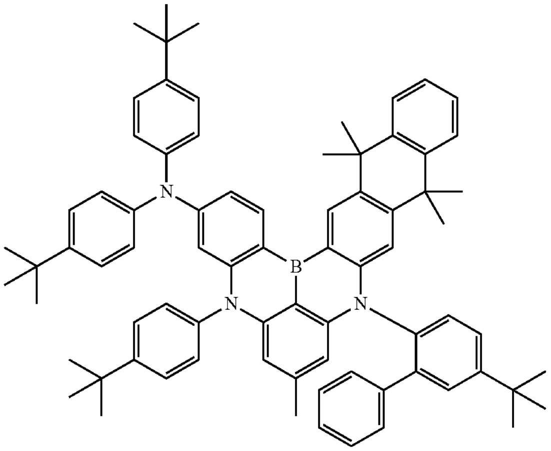 [SMILES: Cc1cc2c3c(c1)N(c1ccc(C(C)(C)C)cc1-c1ccccc1)c1cc4c(cc1B3c1ccc(N(c3ccc(C(C)(C)C)cc3)c3ccc(C(C)(C)C)cc3)cc1N2c1ccc(C(C)(C)C)cc1)C(C)(C)c1ccccc1C4(C)C]
-continued
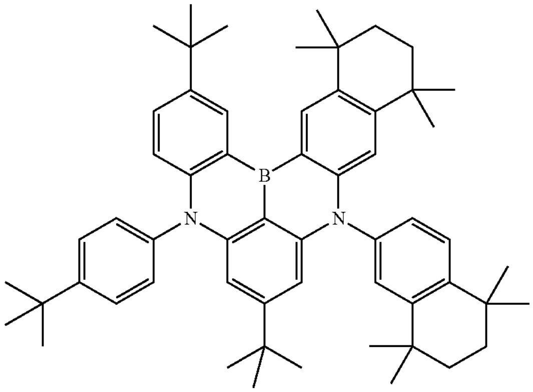
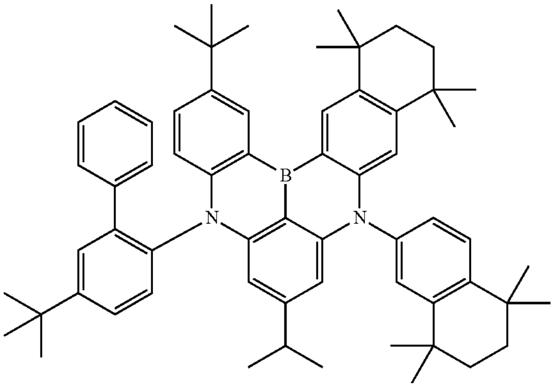
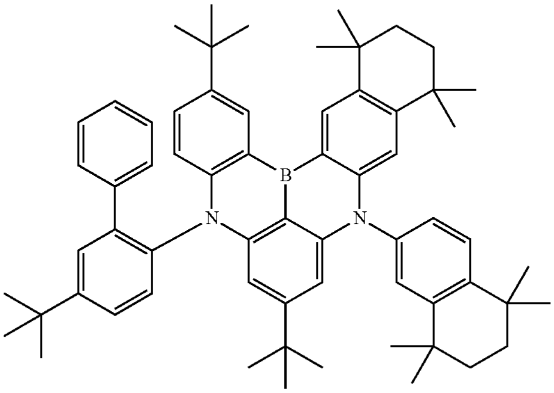
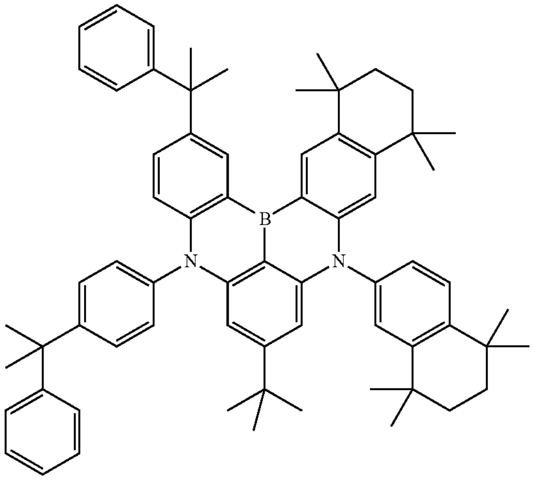

-continued
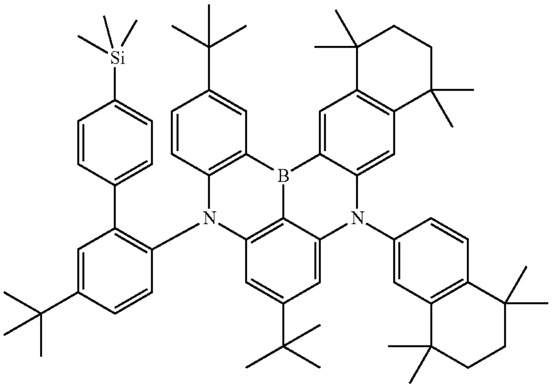
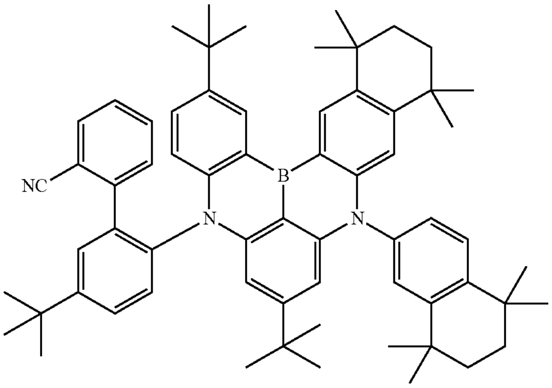
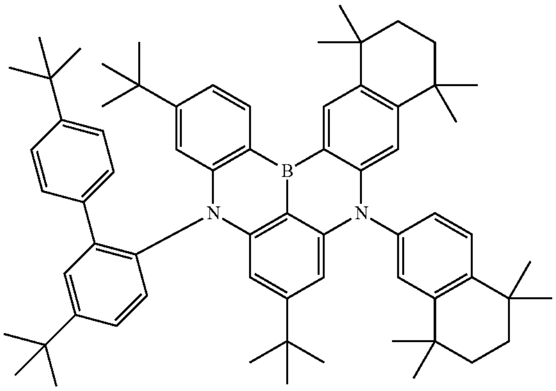
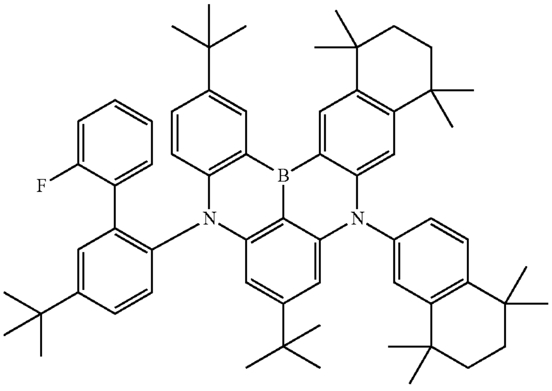
-continued
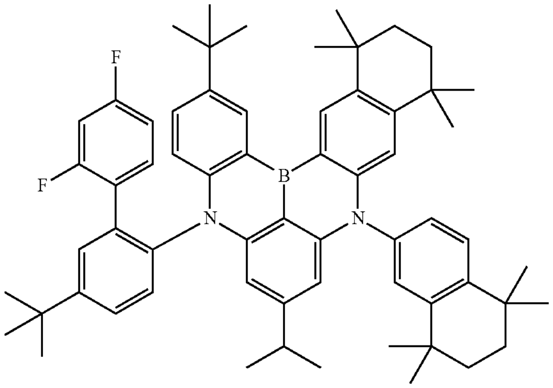
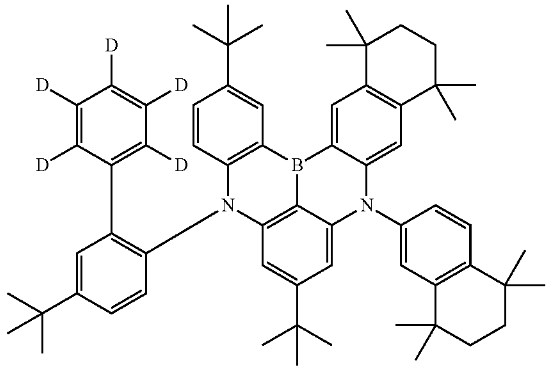
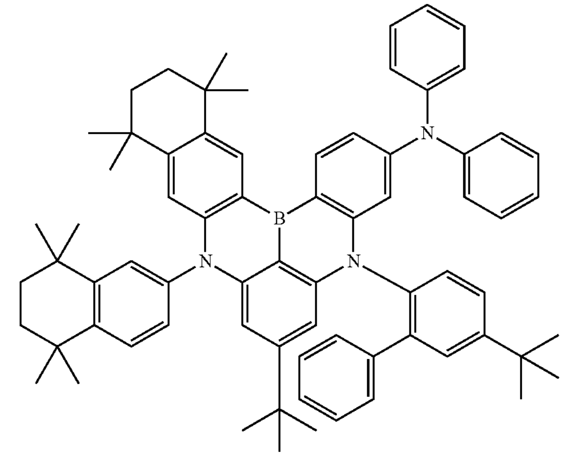
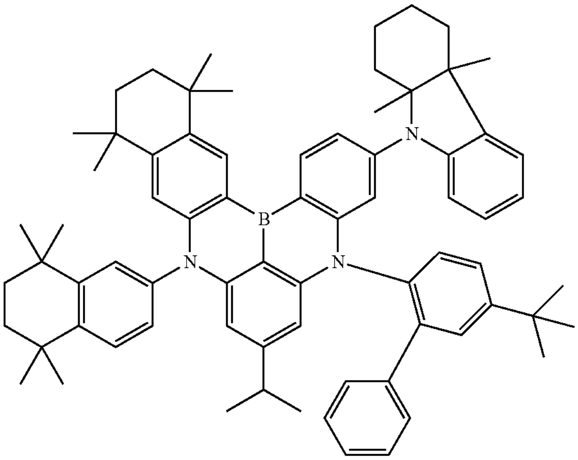

-continued
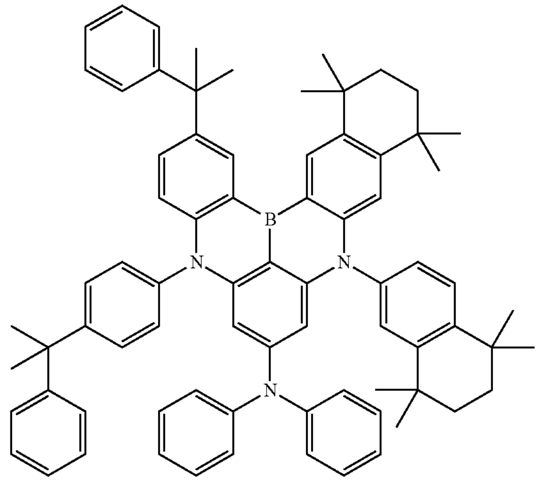
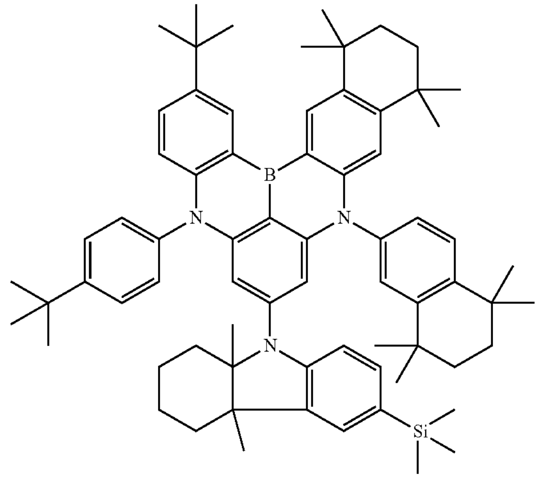
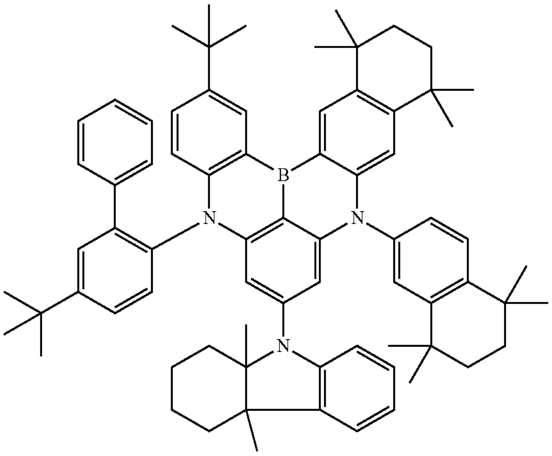
-continued
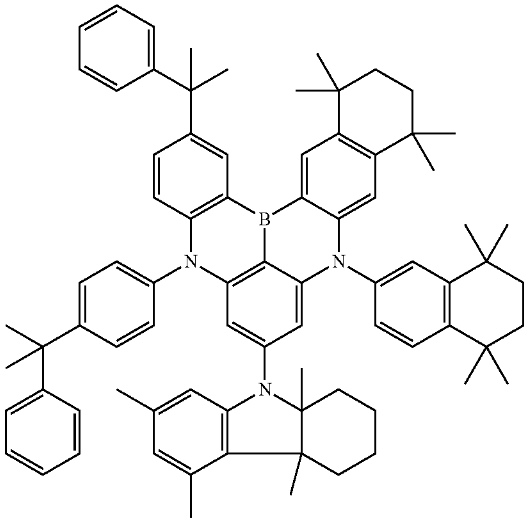 [SMILES: Cc1cc(C)c2c(c1)N(c1cc3c4c(c1)N(c1ccc5c(c1)C(C)(C)CCC5(C)C)c1cc5c(cc1B4c1cc(C(C)(C)c4ccccc4)ccc1N3c1ccc(C(C)(C)c3ccccc3)cc1)C(C)(C)CCC5(C)C)C1(C)CCCCC21C]
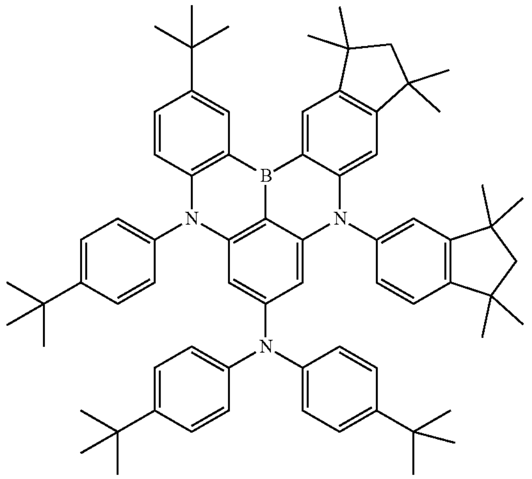
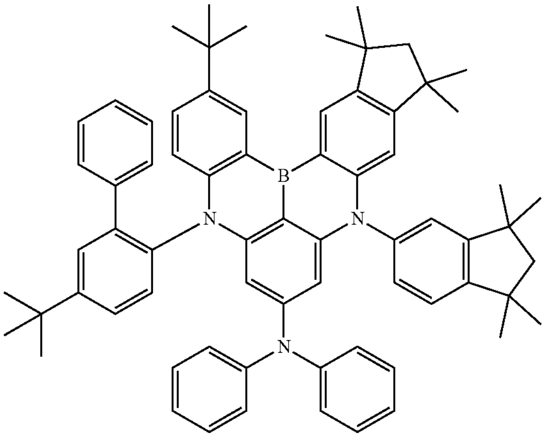

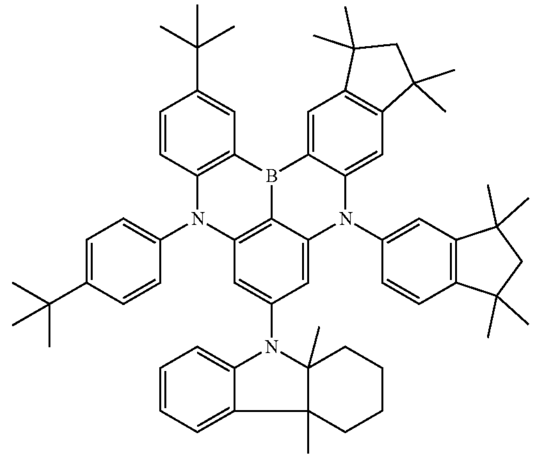
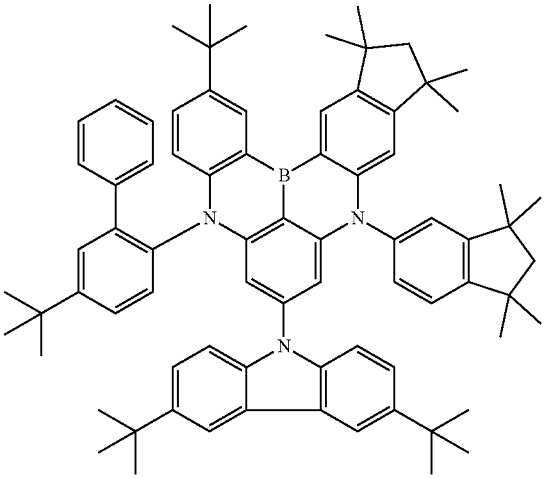
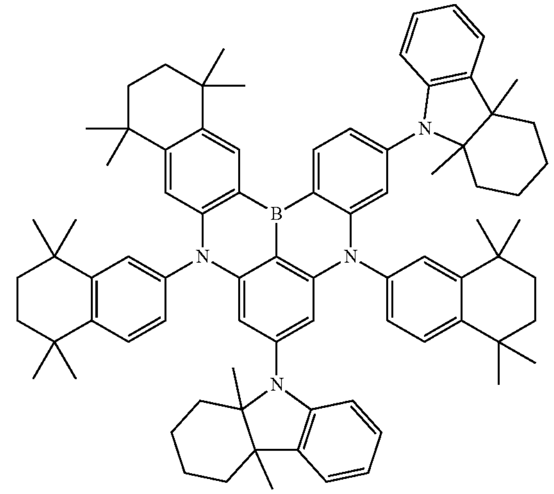
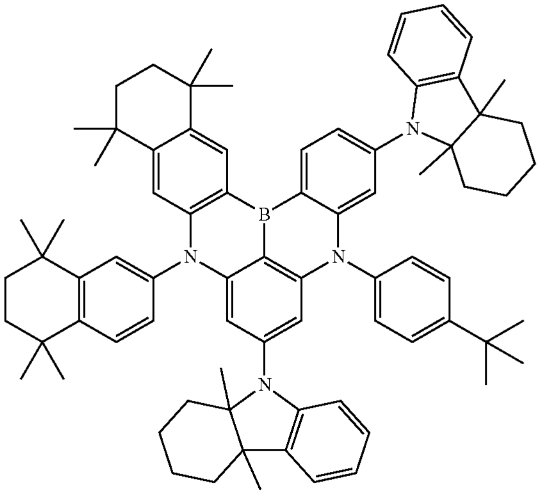
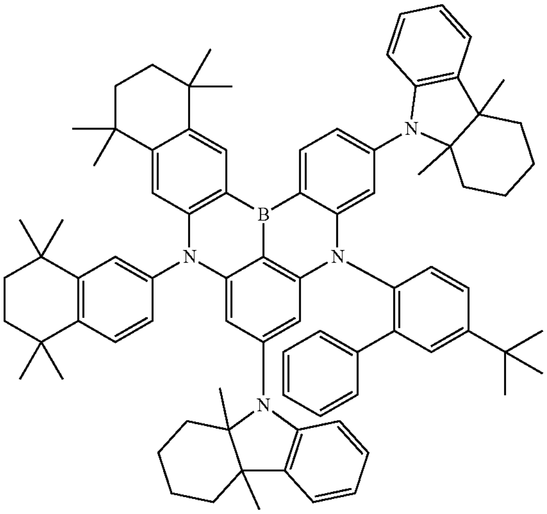
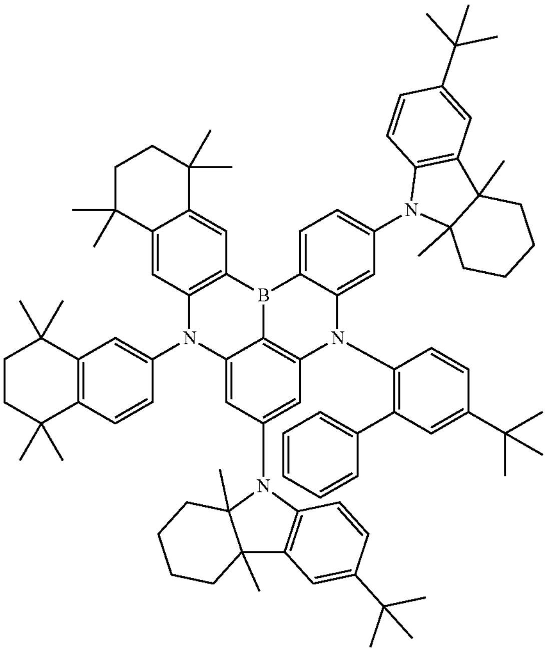 [SMILES: CC(C)(C)c1ccc(N2c3cc(N4c5ccc(C(C)(C)C)cc5C5(C)CCCCC45C)ccc3B3c4cc5c(cc4N(c4ccc6c(c4)C(C)(C)CCC6(C)C)c4cc(N6c7ccc(C(C)(C)C)cc7C7(C)CCCCC67C)cc2c43)C(C)(C)CCC5(C)C)c(-c2ccccc2)c1]

-continued
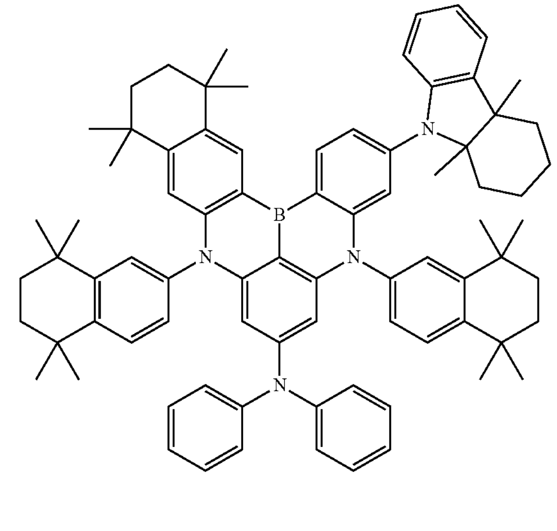
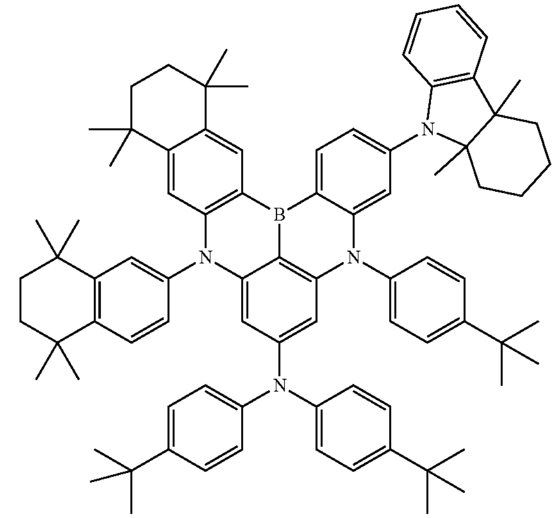
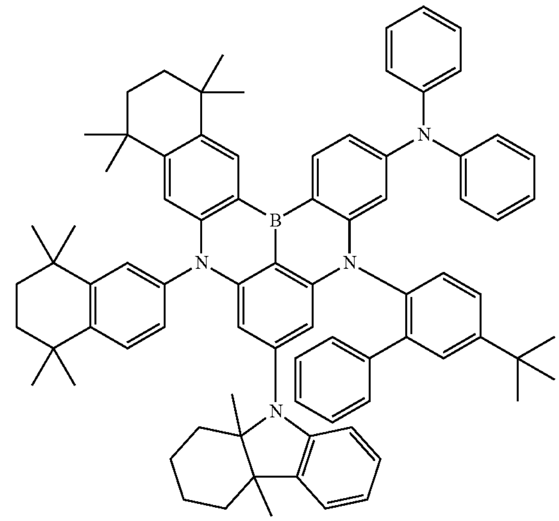
-continued
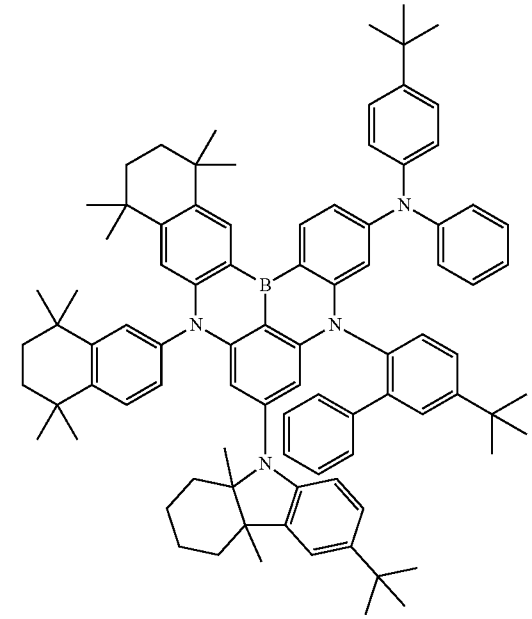 [SMILES: CC(C)(C)c1ccc(N(c2ccccc2)c2ccc3c(c2)N(c2ccc(C(C)(C)C)cc2-c2ccccc2)c2cc(N4c5ccc(C(C)(C)C)cc5C5(C)CCCCC45C)cc4c2B3c2cc3c(cc2N4c2ccc4c(c2)C(C)(C)CCC4(C)C)C(C)(C)CCC3(C)C)cc1]
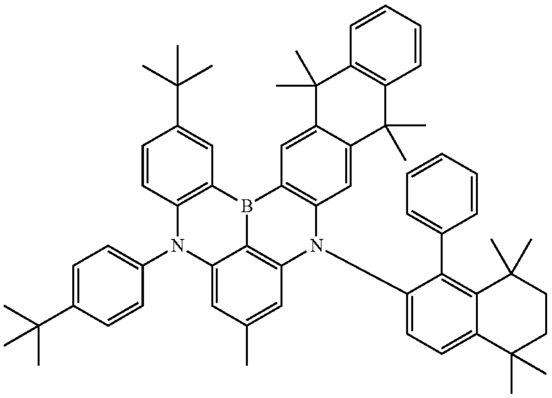
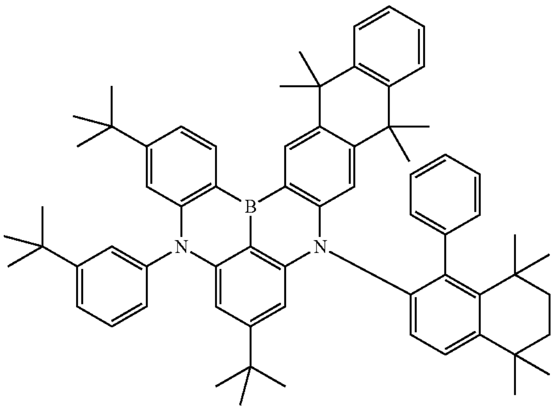

-continued
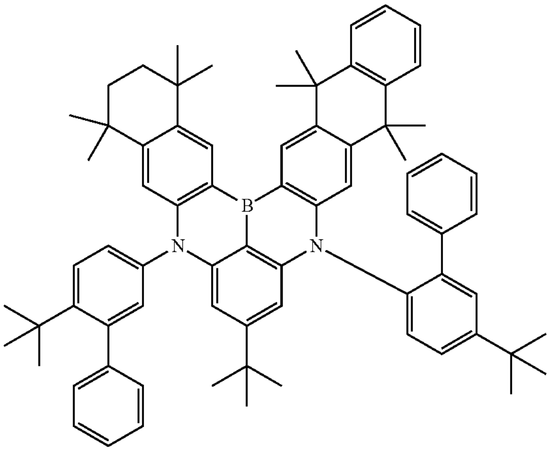
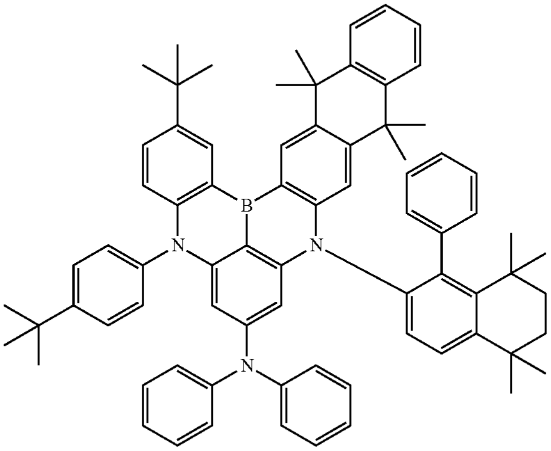
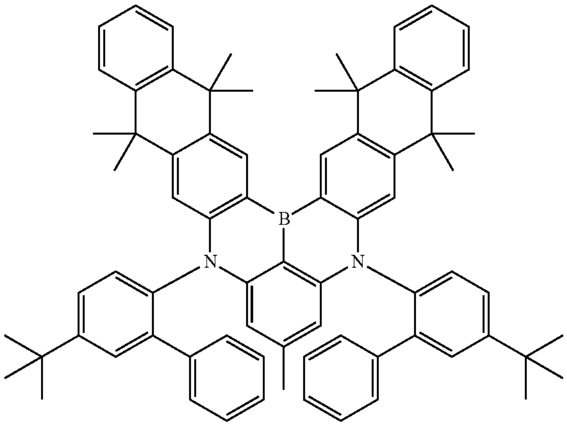
-continued
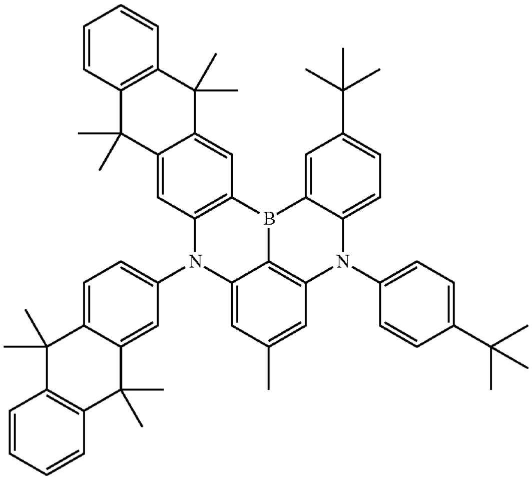
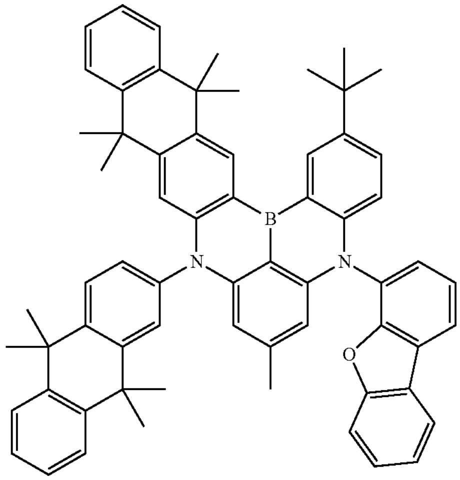
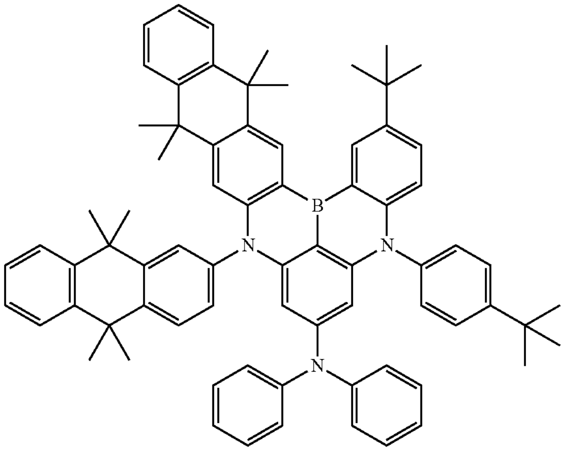 [SMILES: CC(C)(C)c1ccc(N2c3ccc(C(C)(C)C)cc3B3c4cc5c(cc4N(c4ccc6c(c4)C(C)(C)c4ccccc4C6(C)C)c4cc(N(c6ccccc6)c6ccccc6)cc2c43)C(C)(C)c2ccccc2C5(C)C)cc1]

-continued
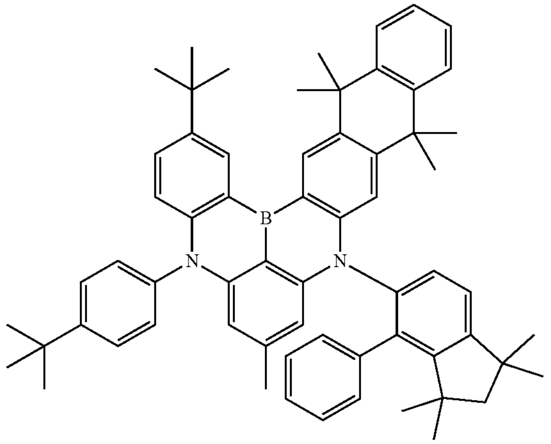
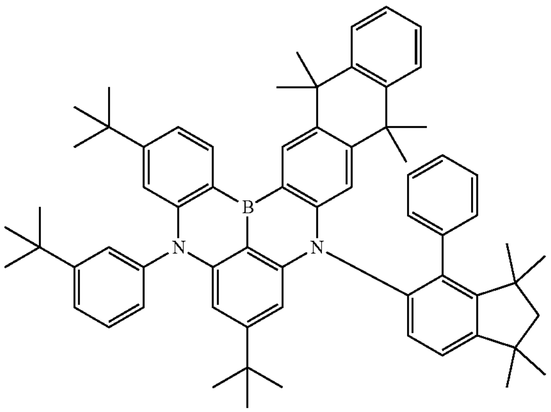
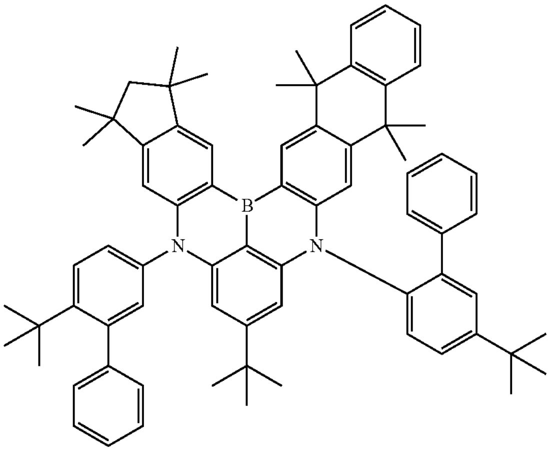
-continued
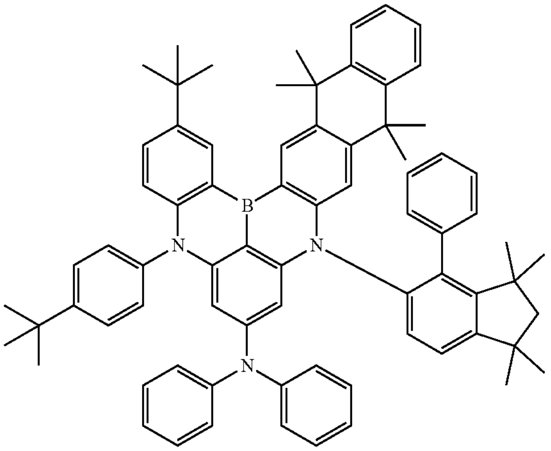
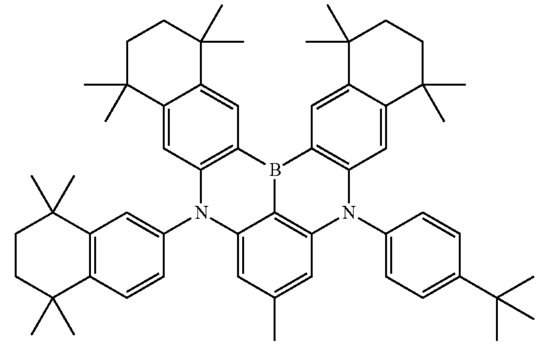
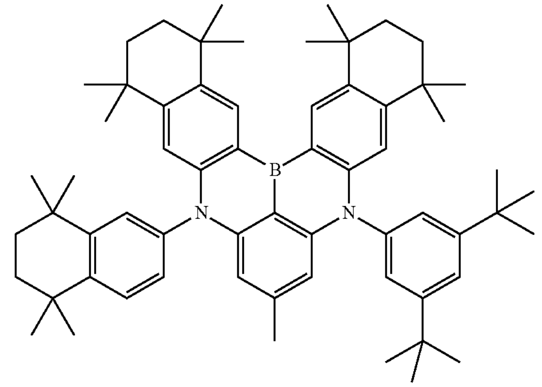
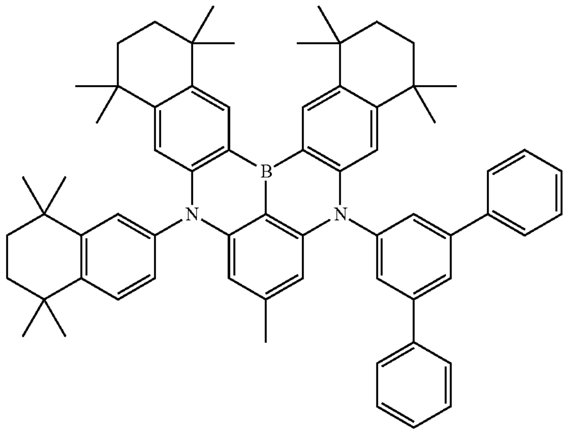

2543
-continued
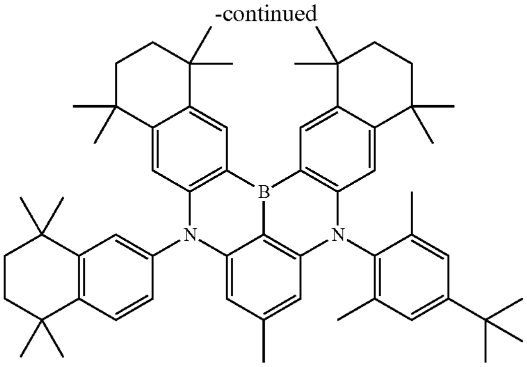
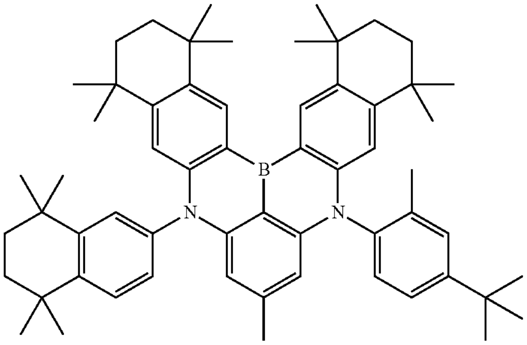
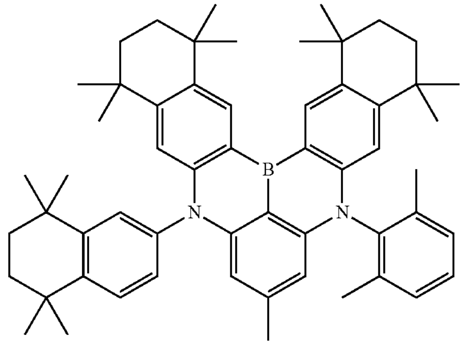
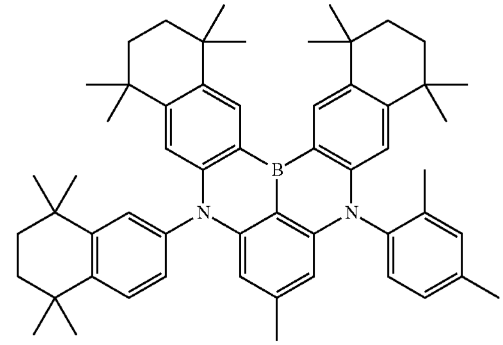
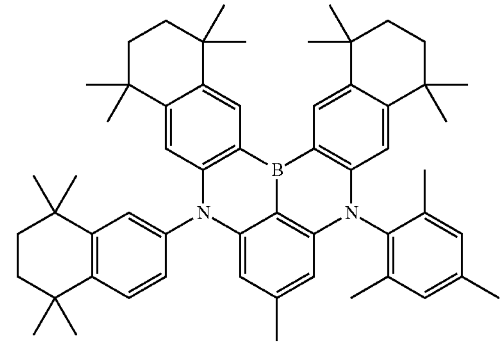
2544
-continued
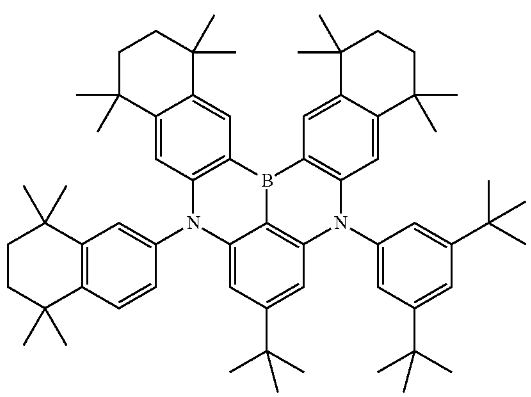
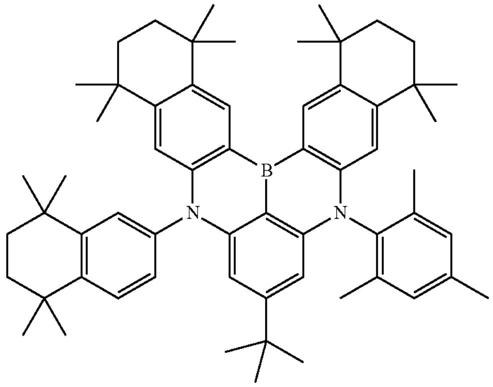
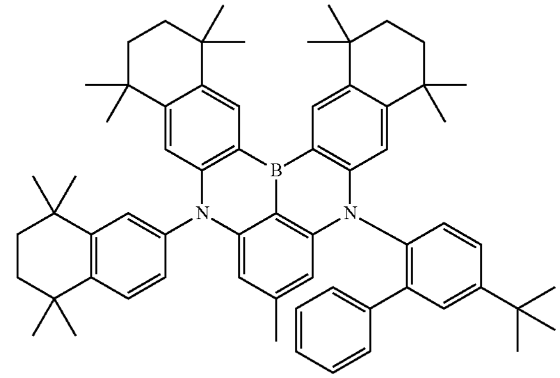
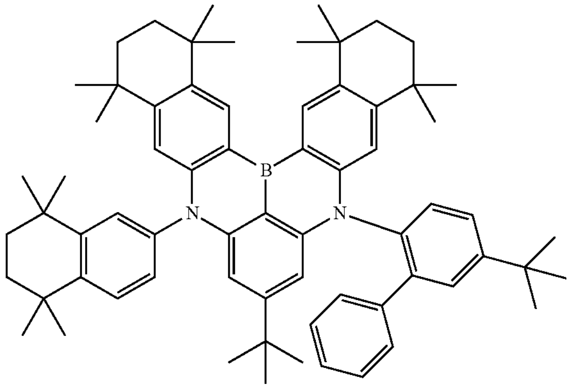

-continued
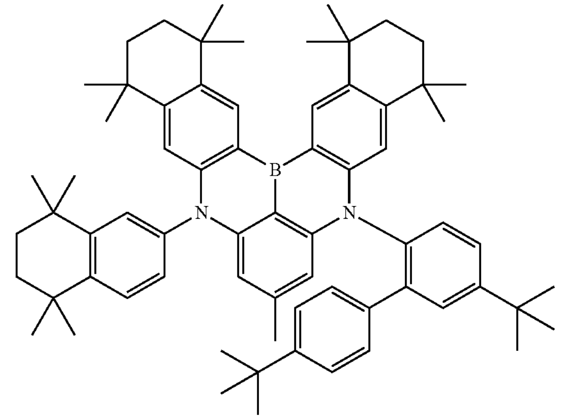
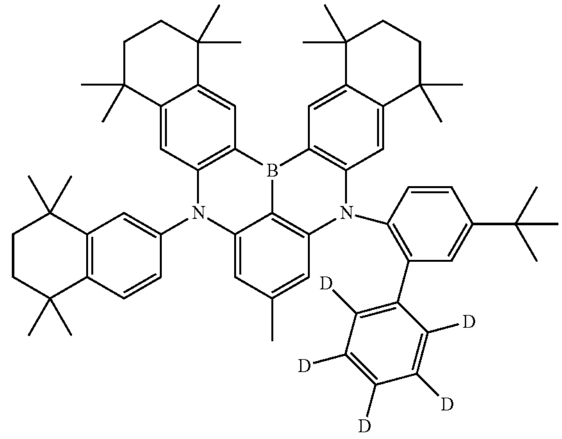
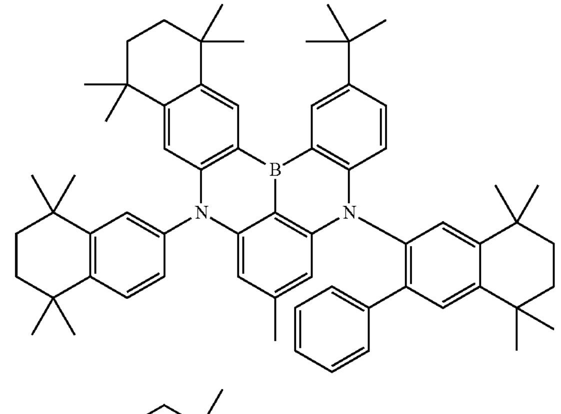
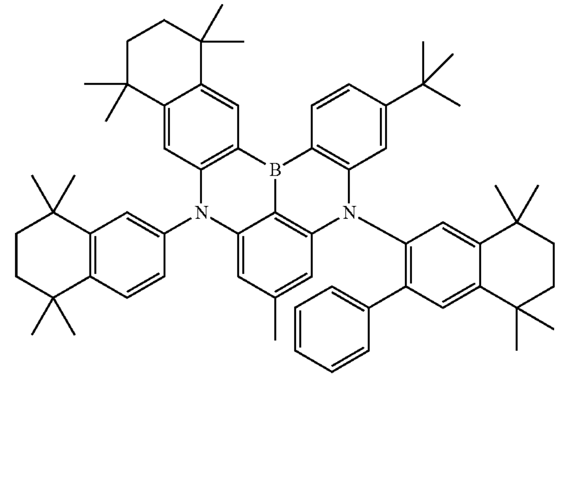
-continued
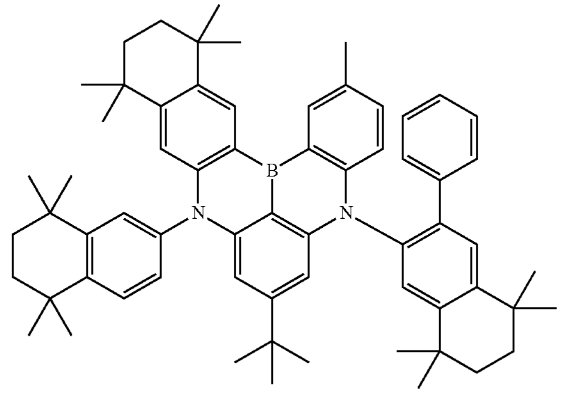
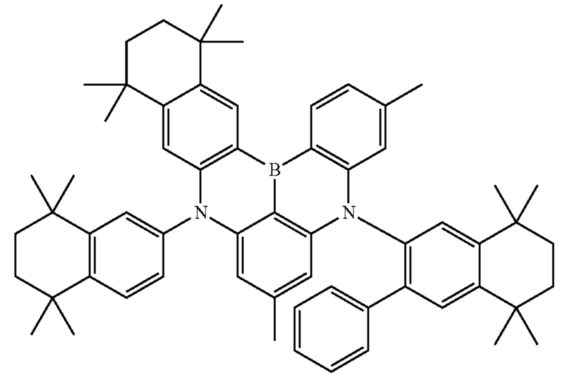
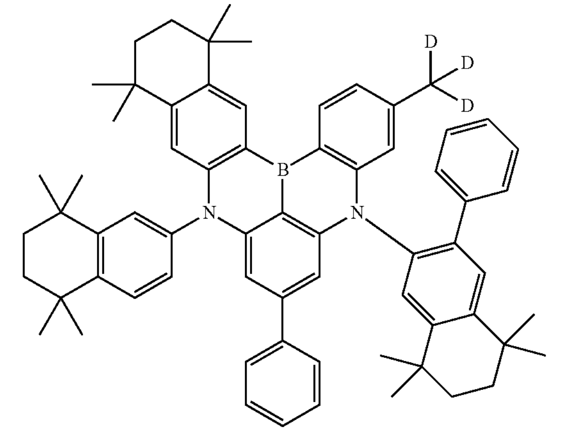
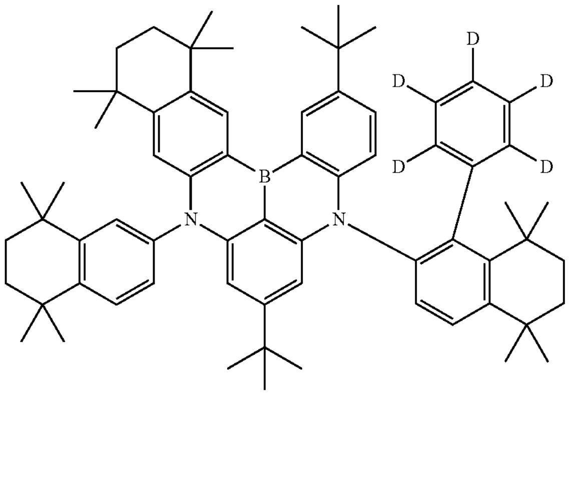

-continued
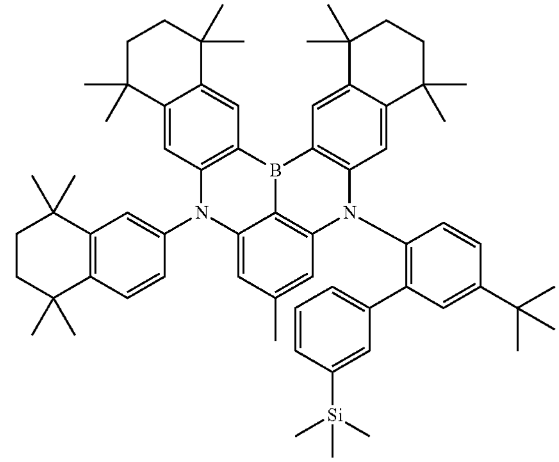
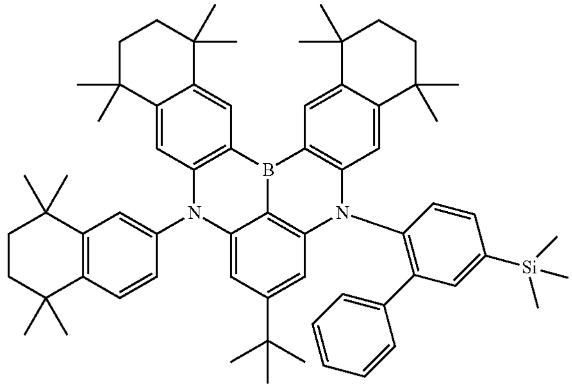
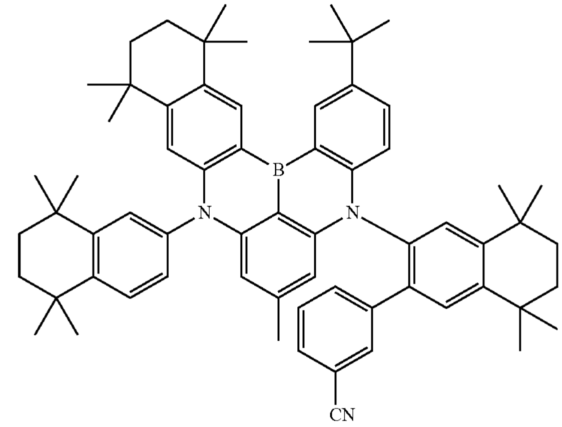
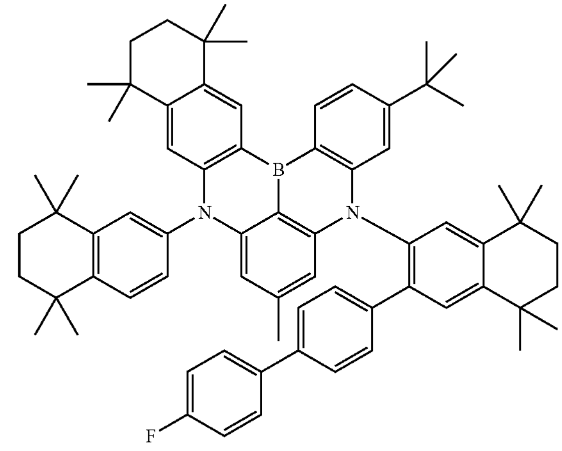 [SMILES: Cc1cc2c3c(c1)N(c1cc4c(cc1-c1ccc(-c5ccc(F)cc5)cc1)C(C)(C)CCC4(C)C)c1cc(C(C)(C)C)ccc1B3c1cc3c(cc1N2c1ccc2c(c1)C(C)(C)CCC2(C)C)C(C)(C)CCC3(C)C]
-continued
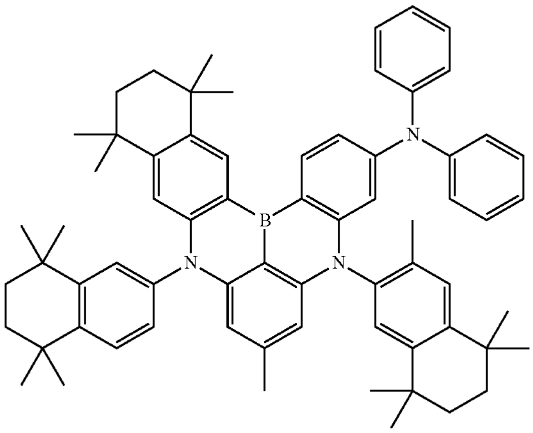
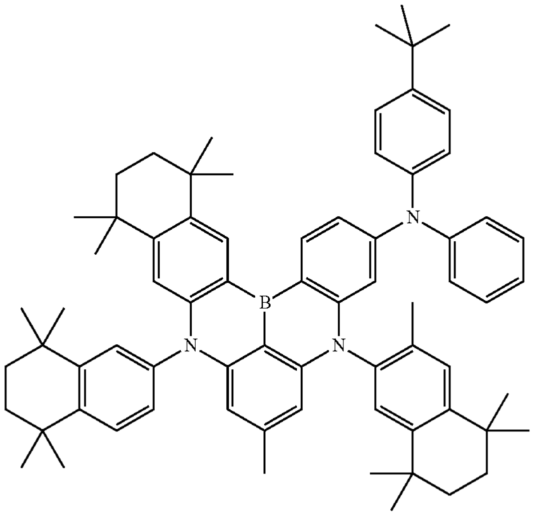
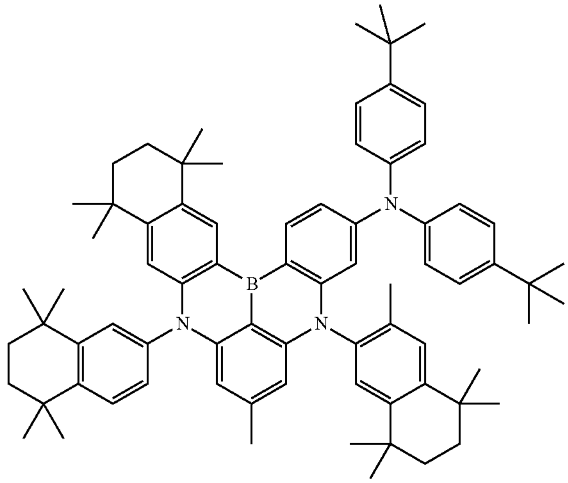

-continued
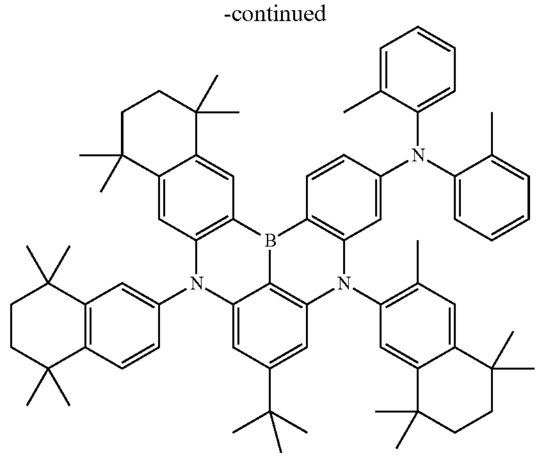
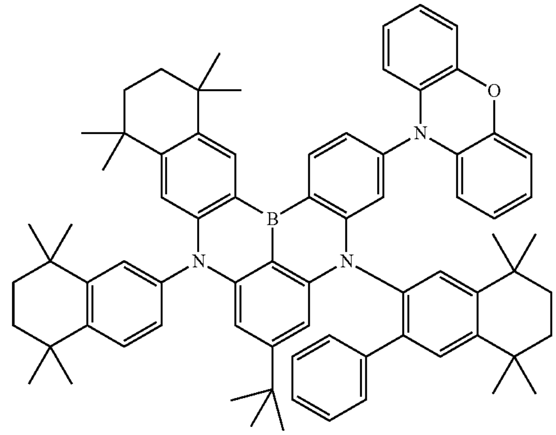
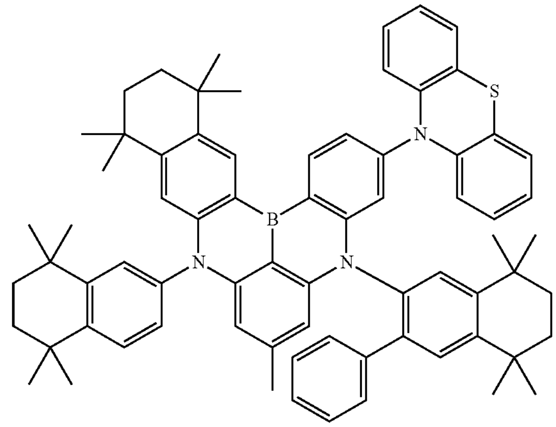
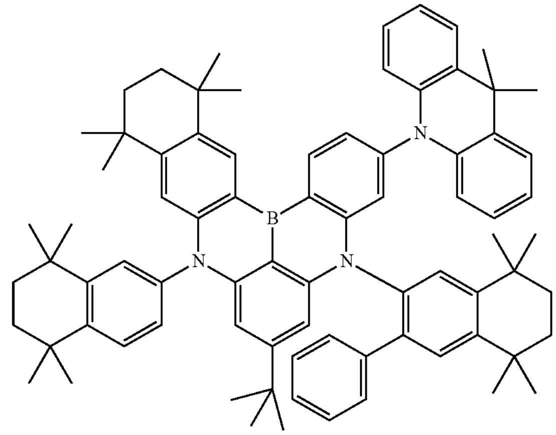
-continued
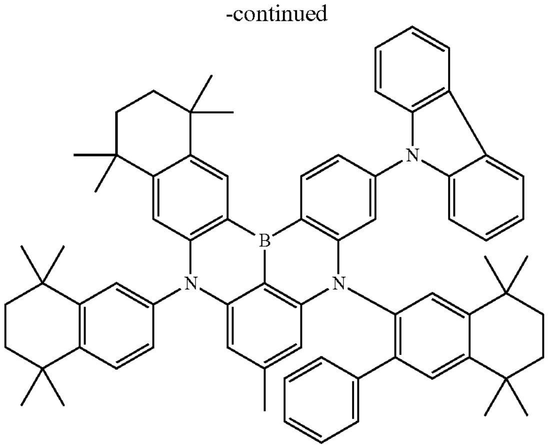
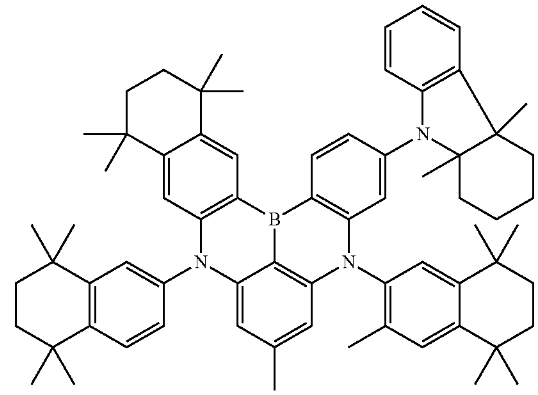
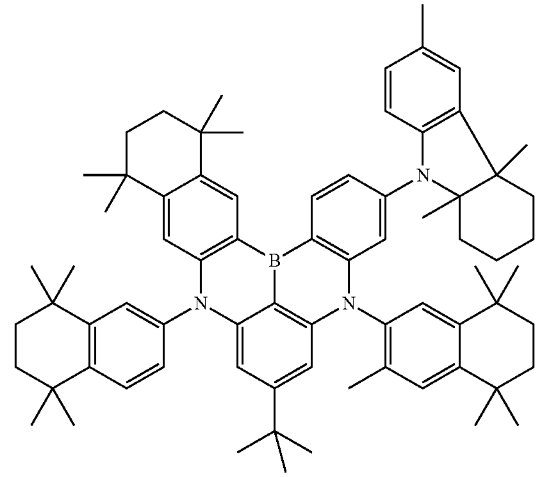
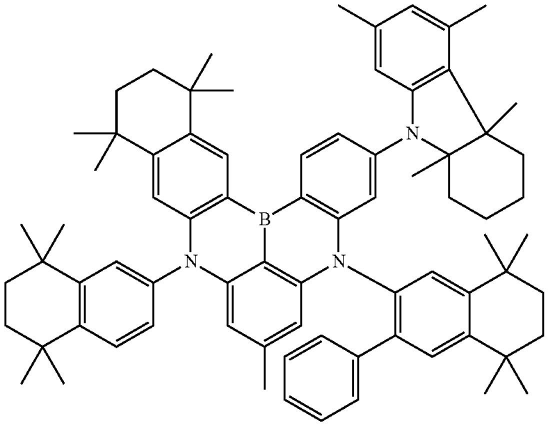

-continued
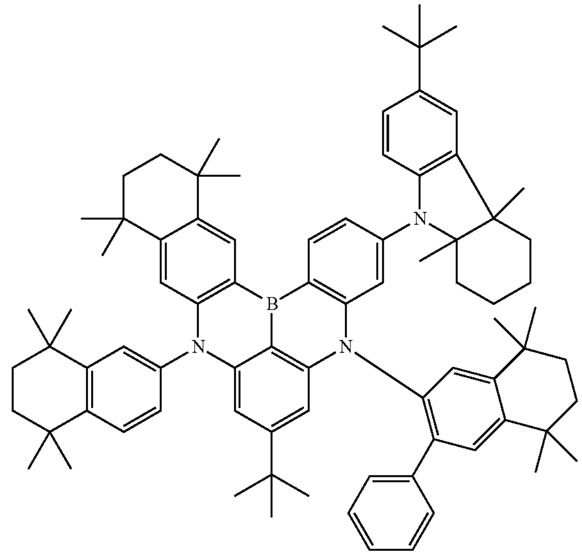 [SMILES: CC(C)(C)c1cc2c3c(c1)N(c1cc4c(cc1-c1ccccc1)C(C)(C)CCC4(C)C)c1cc(N4c5ccc(C(C)(C)C)cc5C5(C)CCCCC45C)ccc1B3c1cc3c(cc1N2c1ccc2c(c1)C(C)(C)CCC2(C)C)C(C)(C)CCC3(C)C]
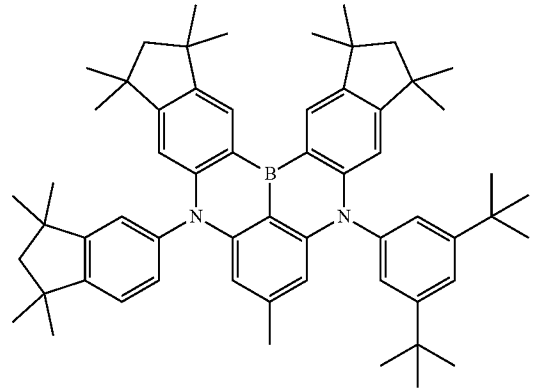
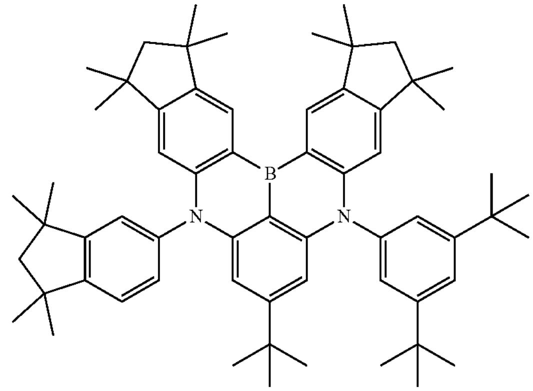
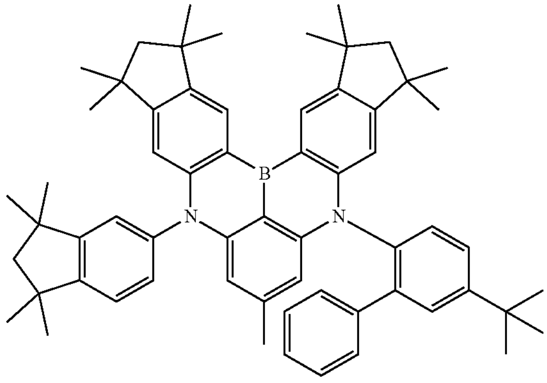
-continued
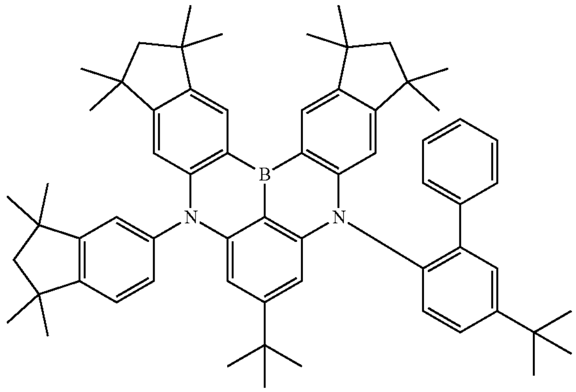
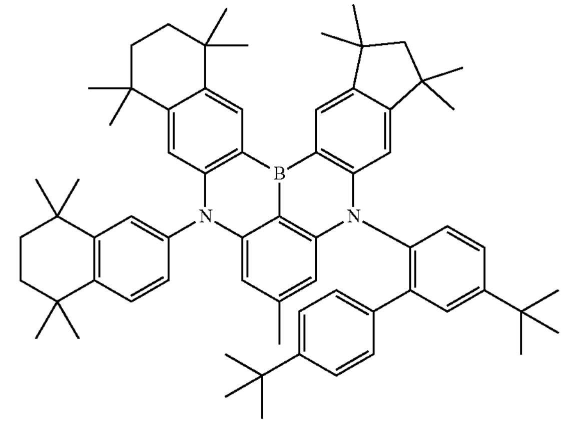
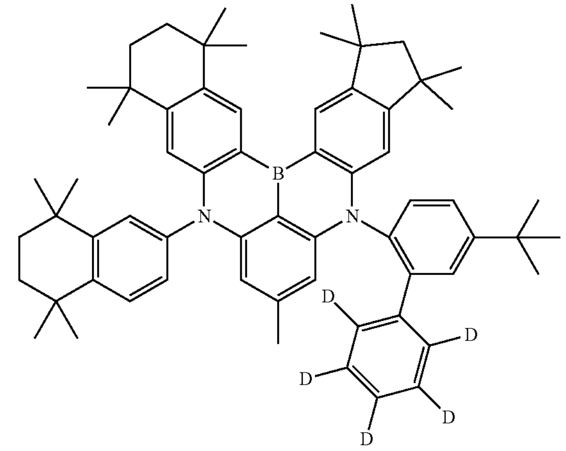
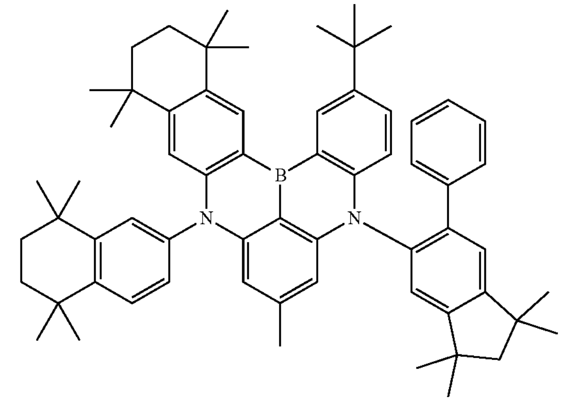

-continued
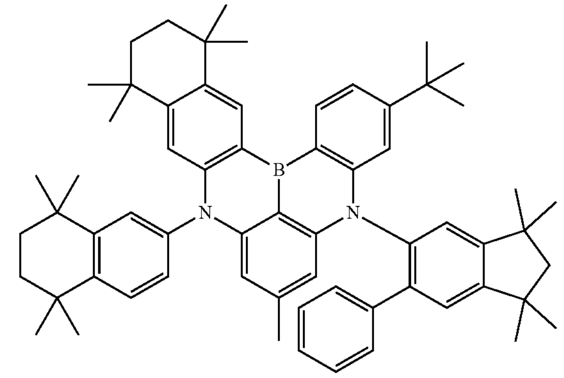
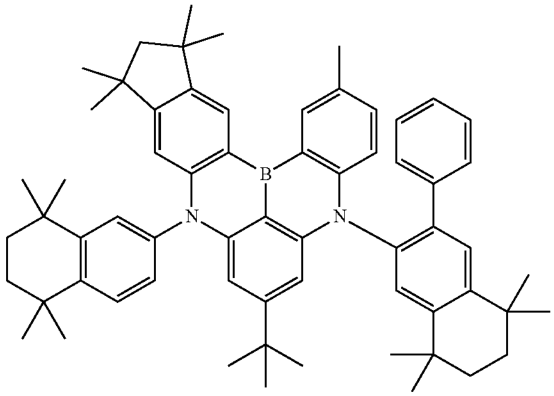
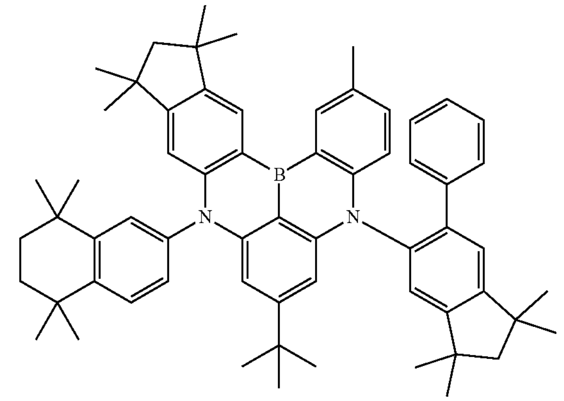
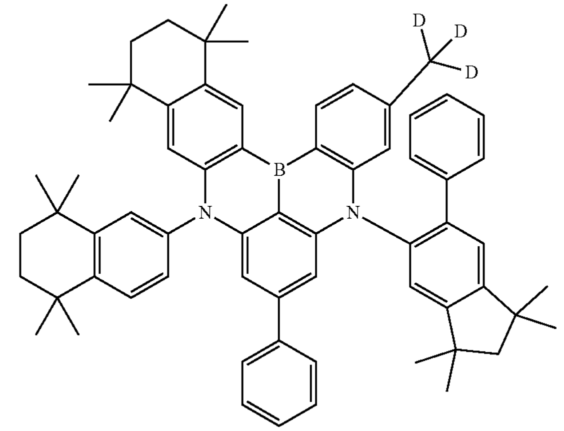
-continued
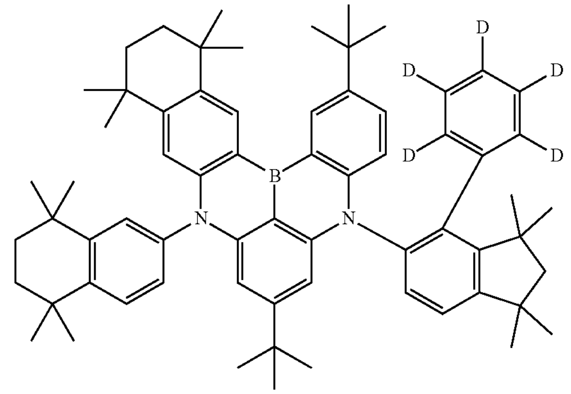
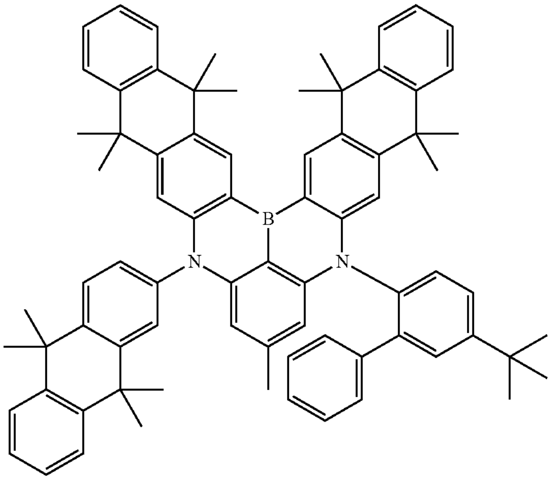
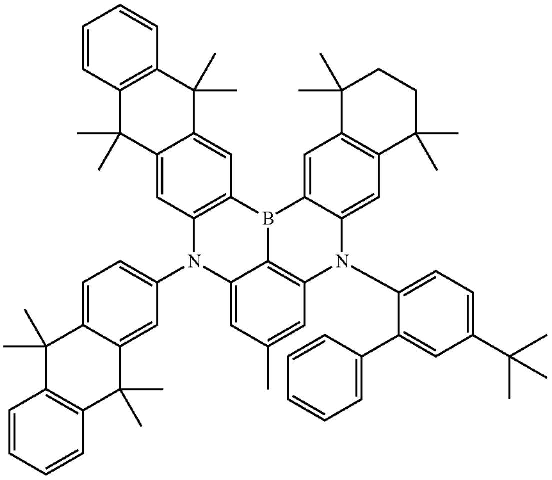

-continued
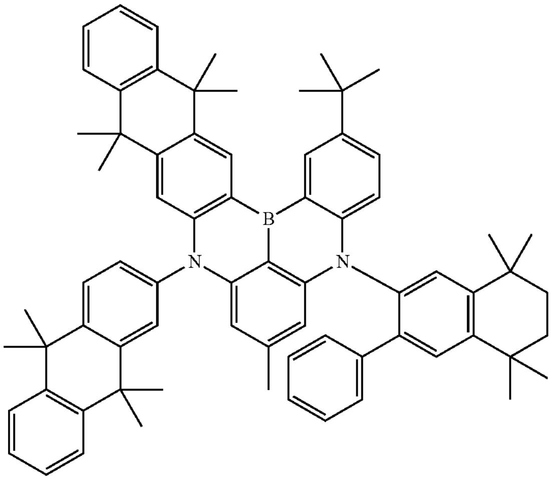
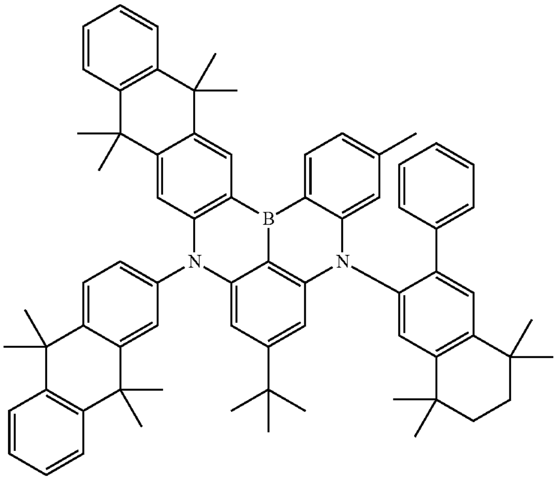
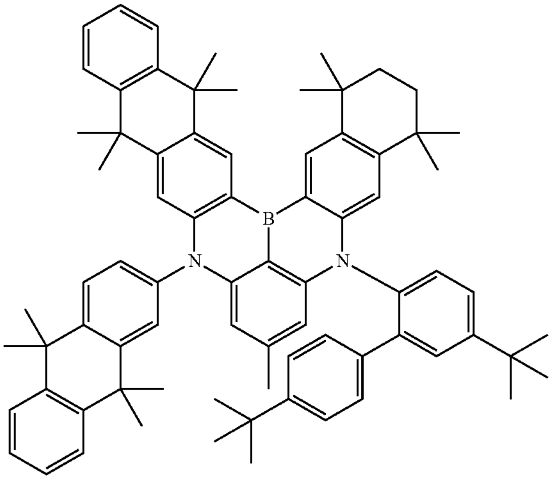
-continued
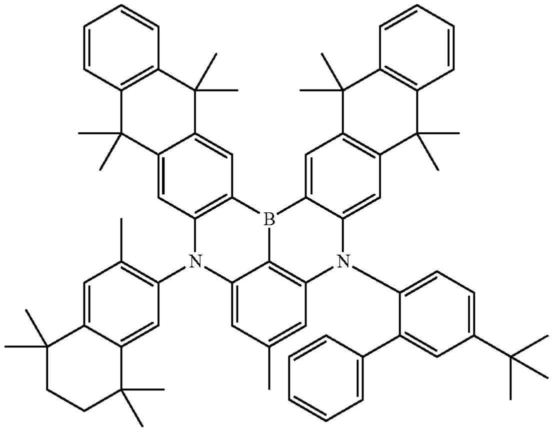
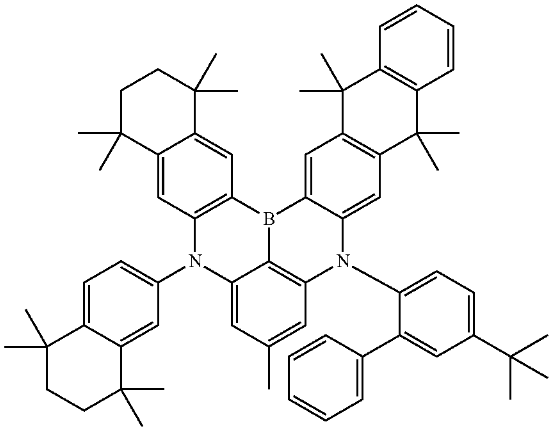
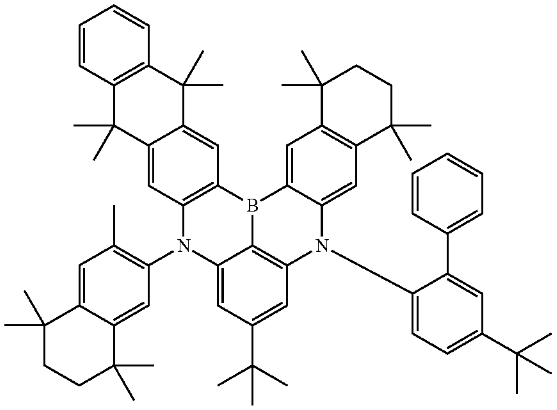 [SMILES: Cc1cc2c(cc1N1c3cc4c(cc3B3c5cc6c(cc5N(c5ccc(C(C)(C)C)cc5-c5ccccc5)c5cc(C(C)(C)C)cc1c53)C(C)(C)CCC6(C)C)C(C)(C)c1ccccc1C4(C)C)C(C)(C)CCC2(C)C]

-continued
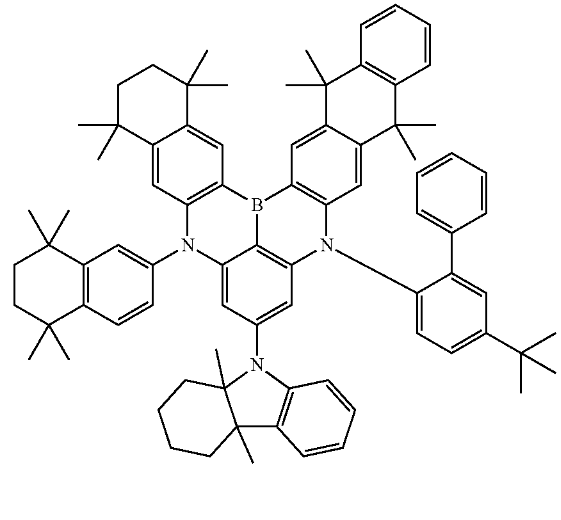
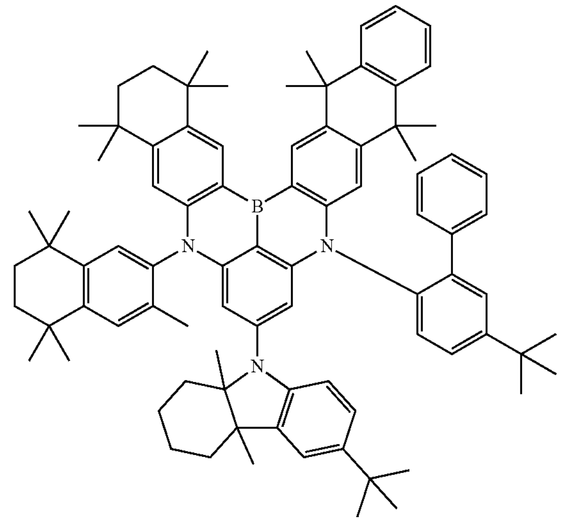
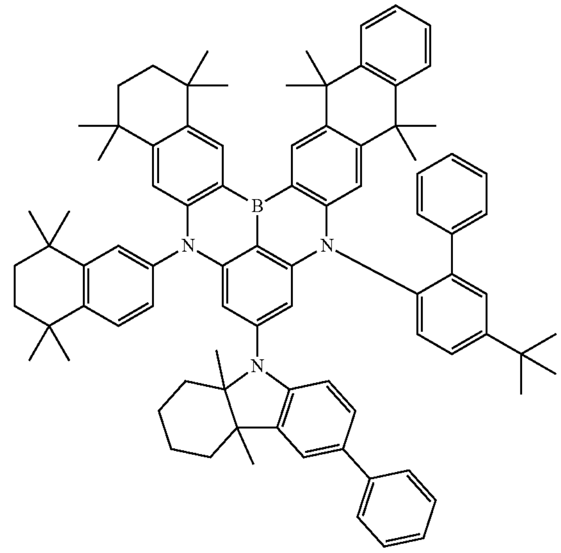
-continued
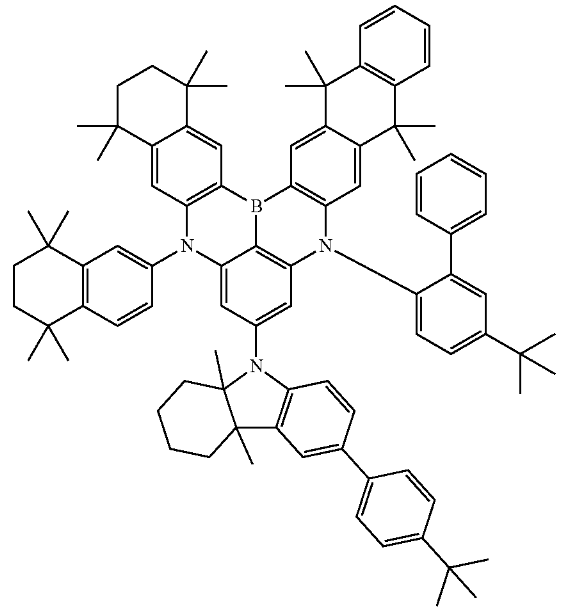 [SMILES: CC(C)(C)c1ccc(-c2ccc3c(c2)C2(C)CCCCC2(C)N3c2cc3c4c(c2)N(c2ccc(C(C)(C)C)cc2-c2ccccc2)c2cc5c(cc2B4c2cc4c(cc2N3c2ccc3c(c2)C(C)(C)CCC3(C)C)C(C)(C)CCC4(C)C)C(C)(C)c2ccccc2C5(C)C)cc1]
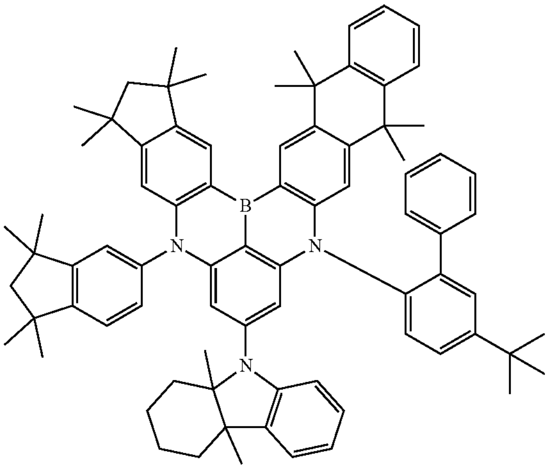
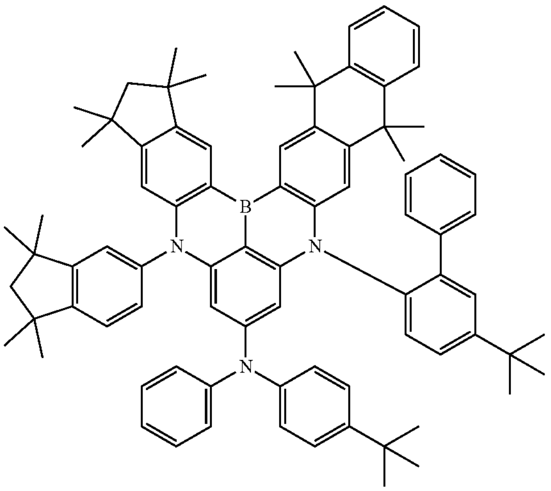

-continued
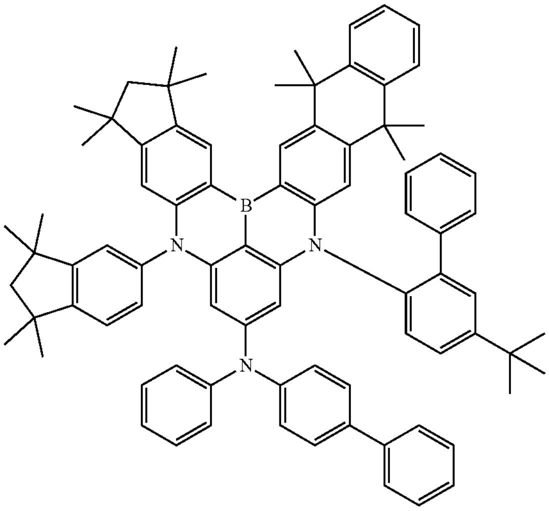
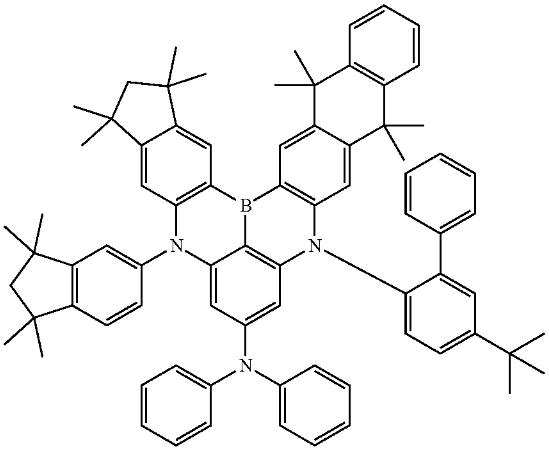 [SMILES: CC(C)(C)c1ccc(N2c3cc4c(cc3B3c5cc6c(cc5N(c5ccc7c(c5)C(C)(C)CC7(C)C)c5cc(N(c7ccccc7)c7ccccc7)cc2c53)C(C)(C)CC6(C)C)C(C)(C)c2ccccc2C4(C)C)c(-c2ccccc2)c1]
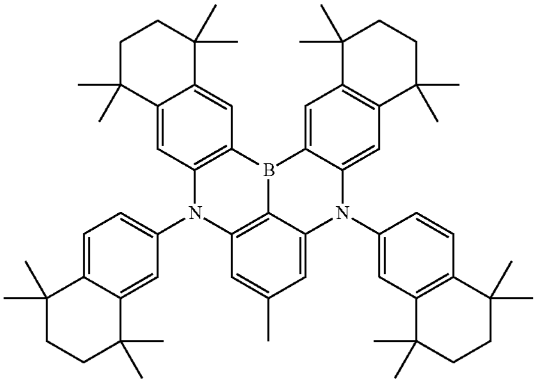
-continued
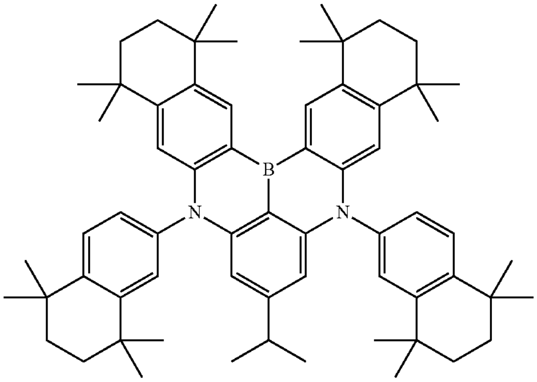
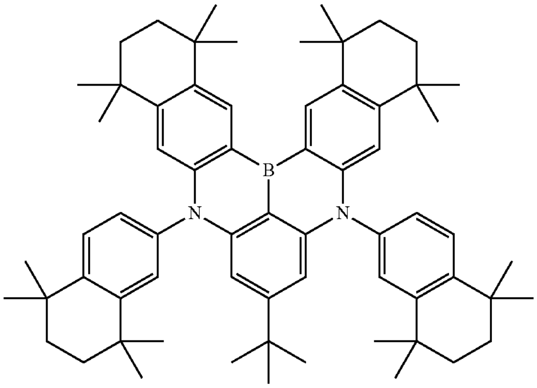
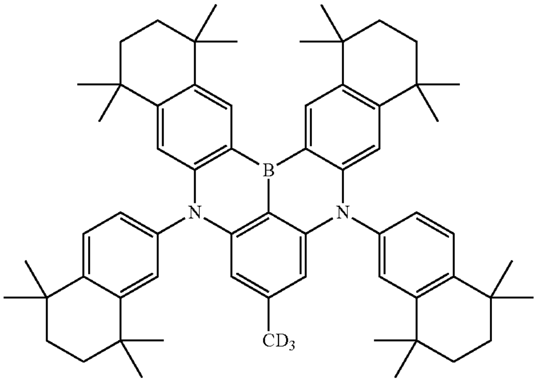
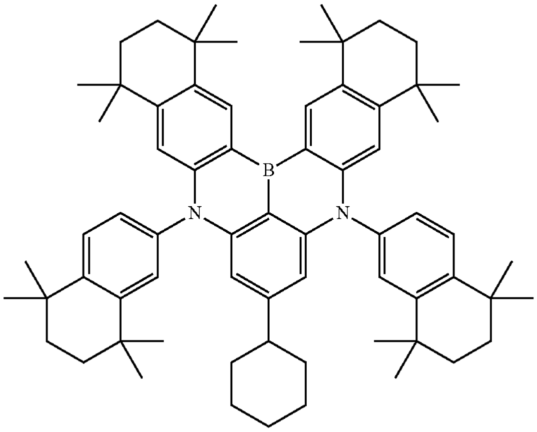

-continued
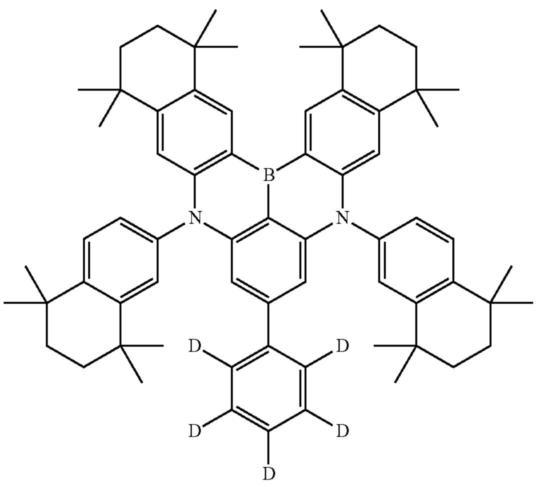
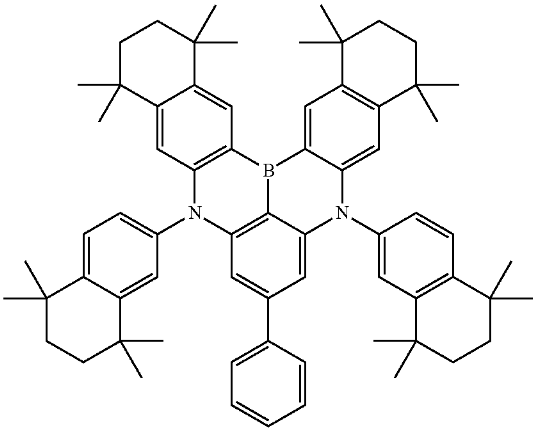
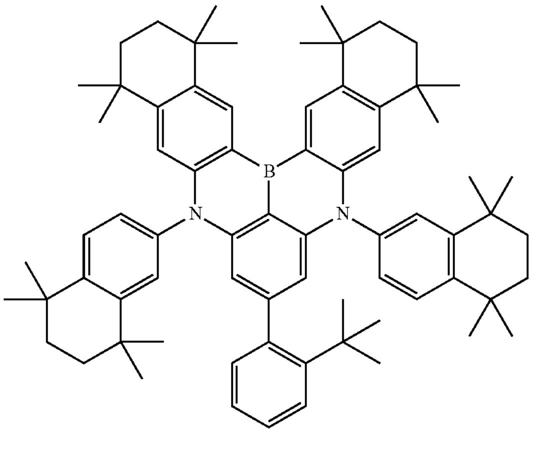
-continued
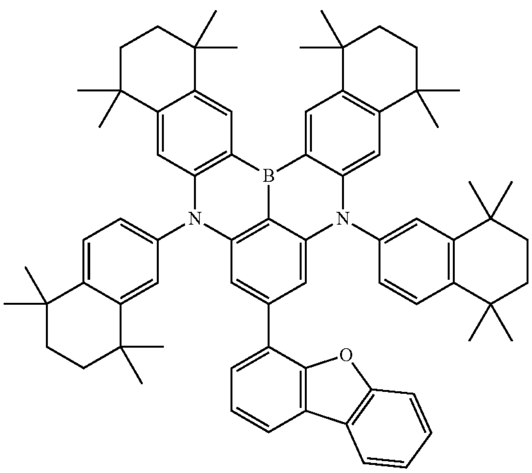
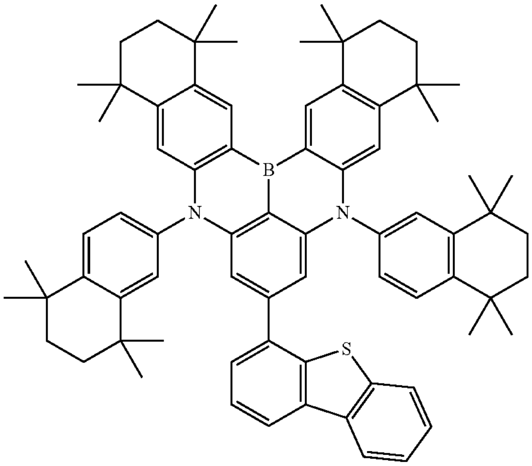
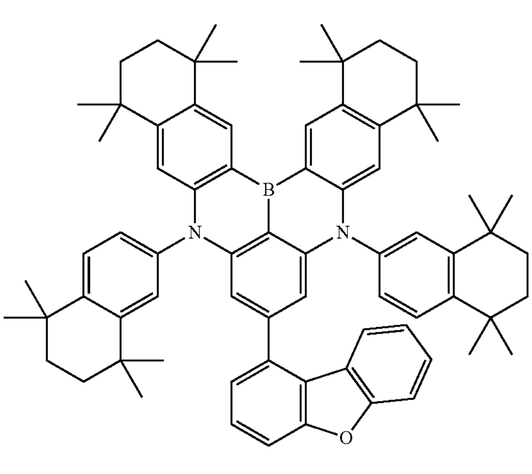

-continued
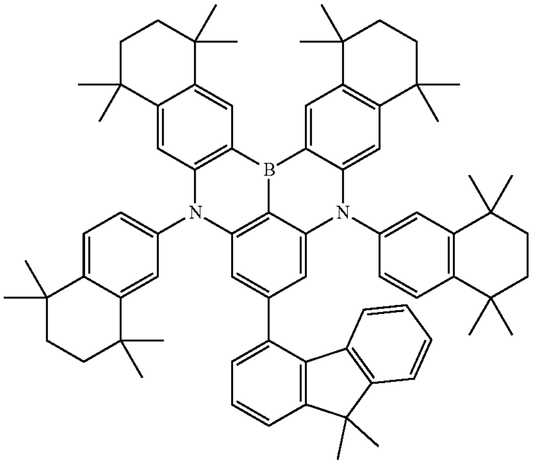
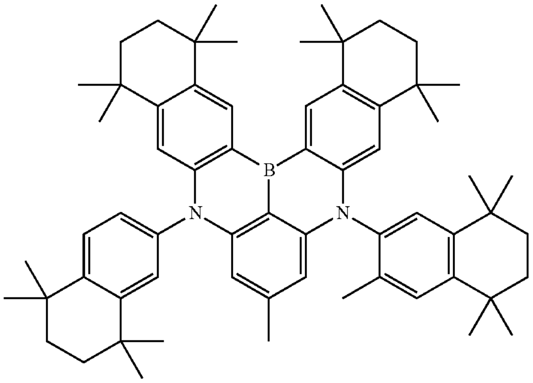
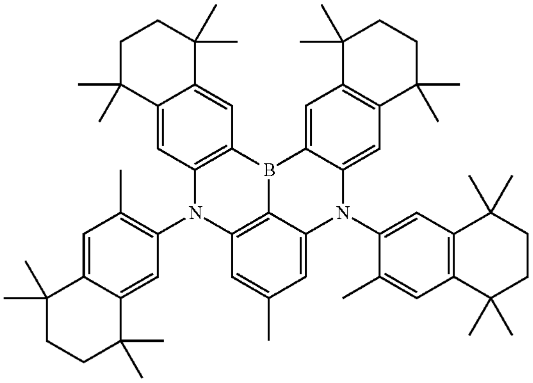
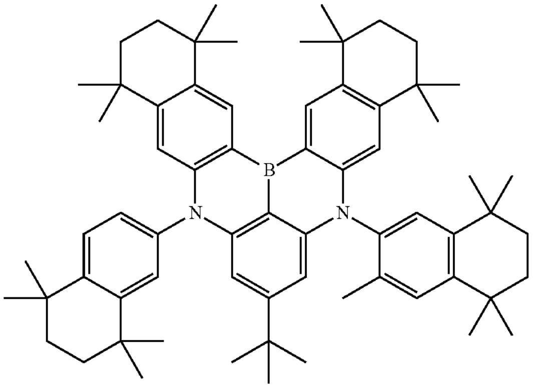
-continued
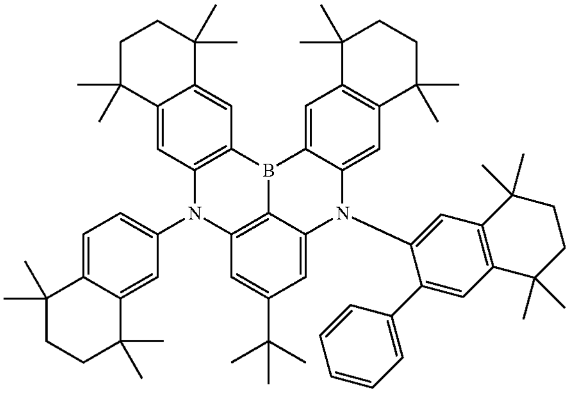
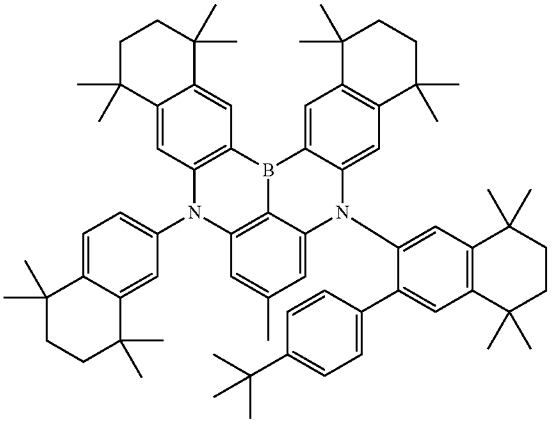
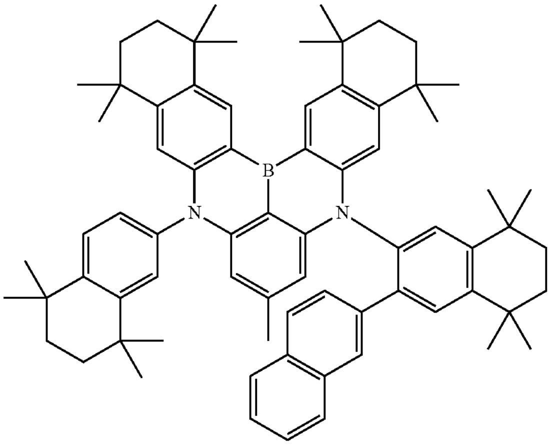
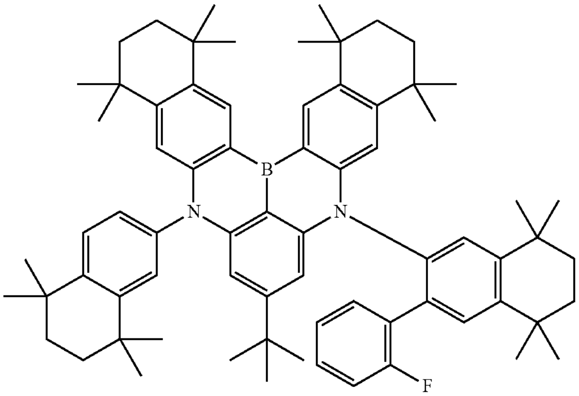

-continued
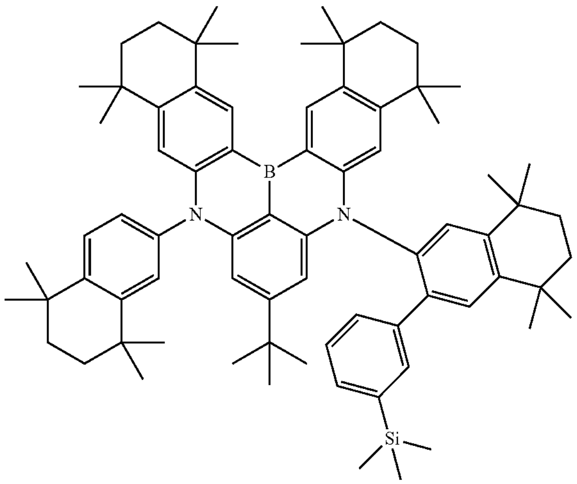
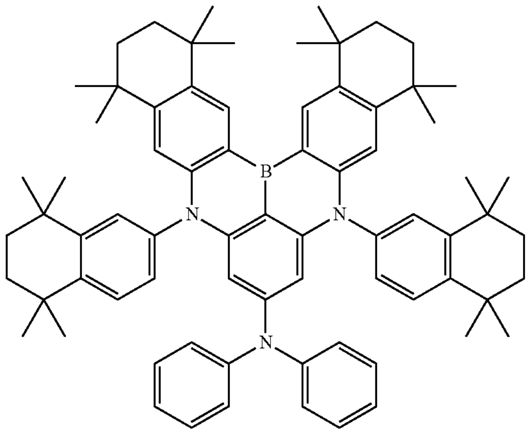
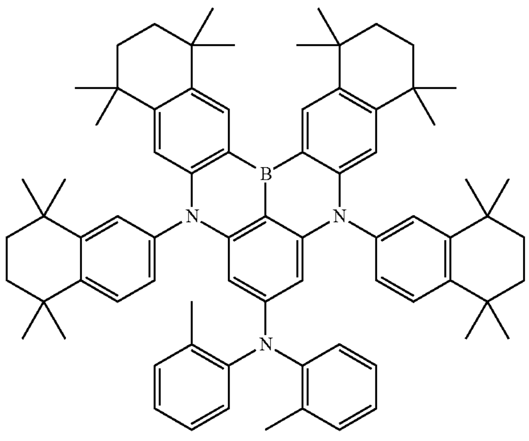
-continued
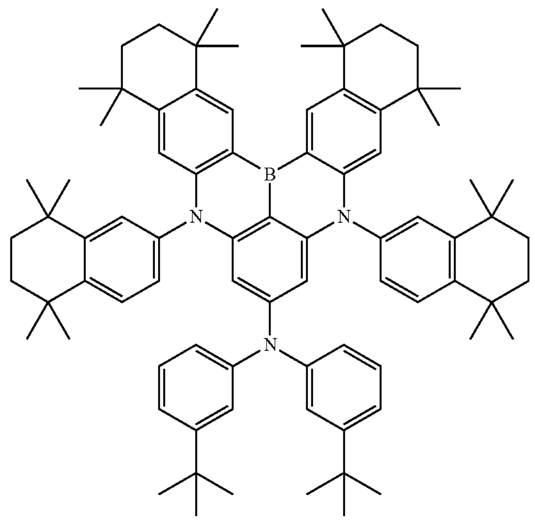
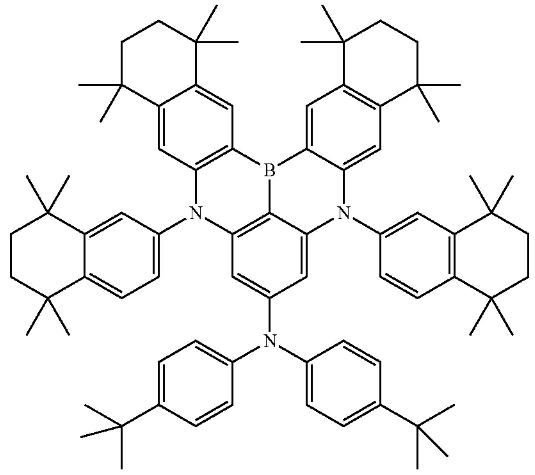
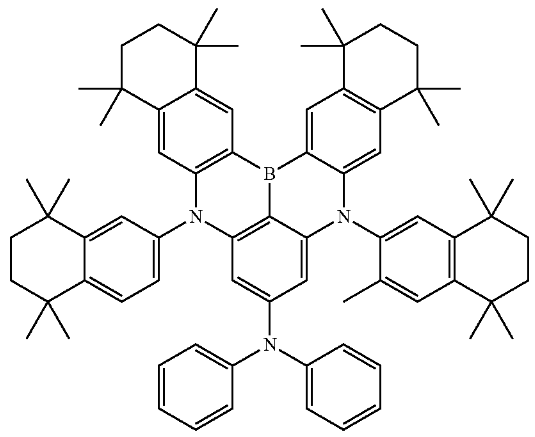

-continued
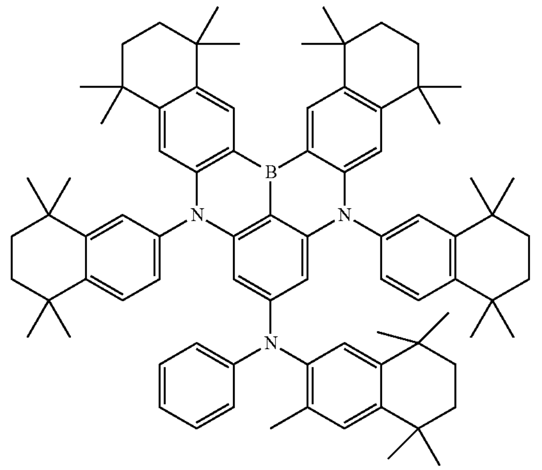
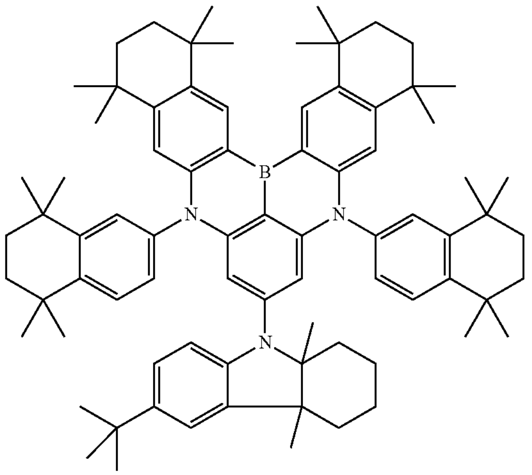
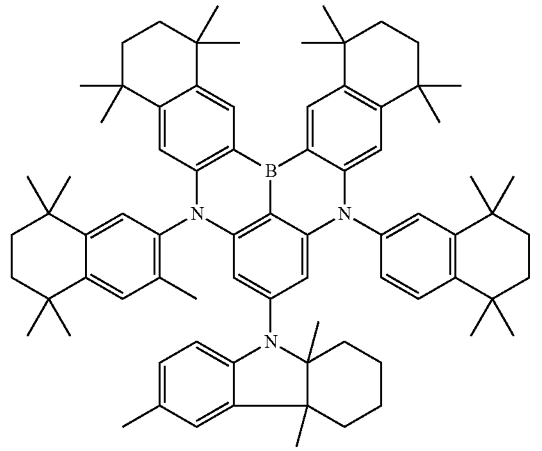
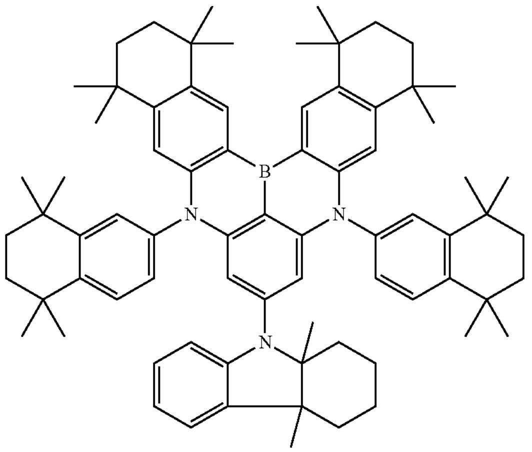
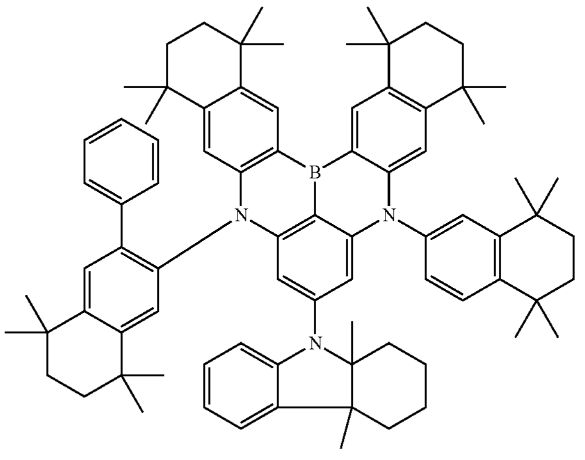
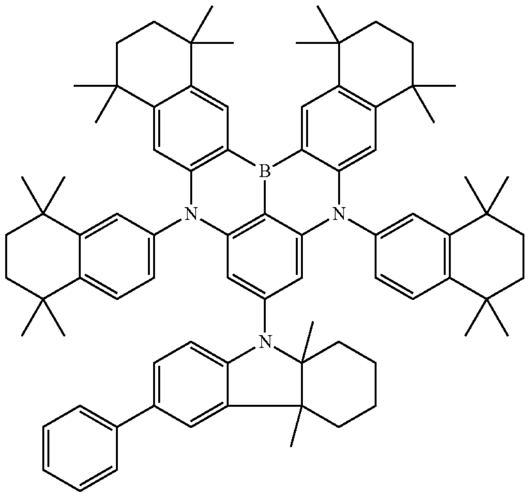
-continued -continued
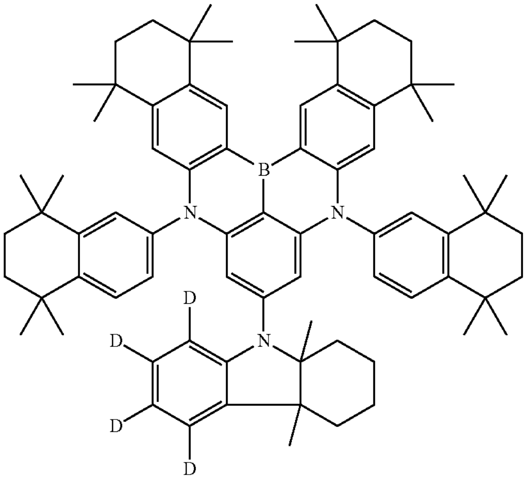
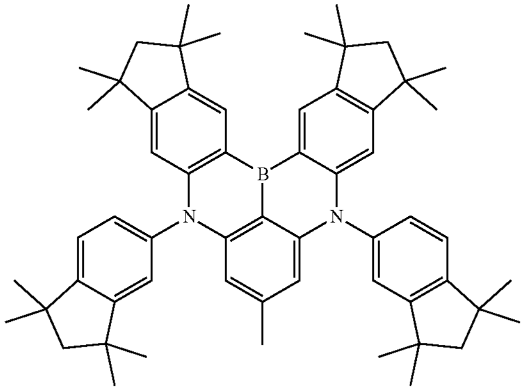
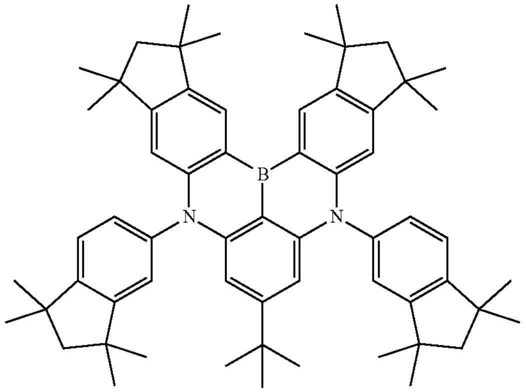
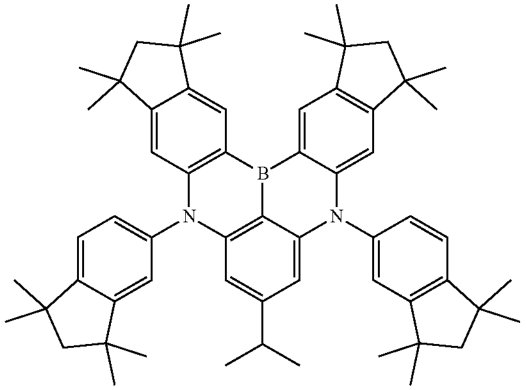
-continued
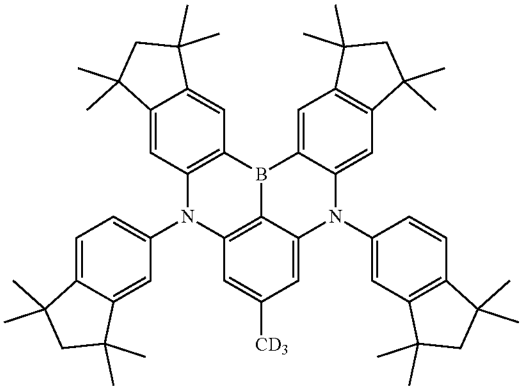
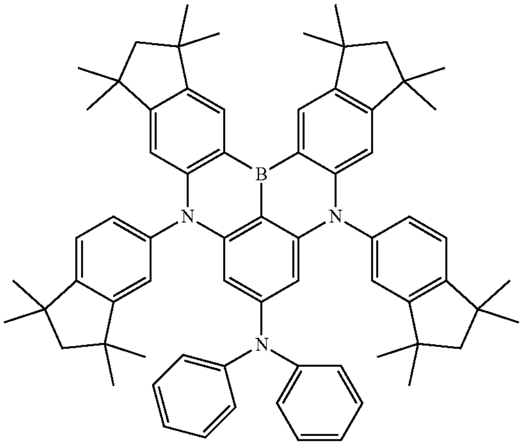
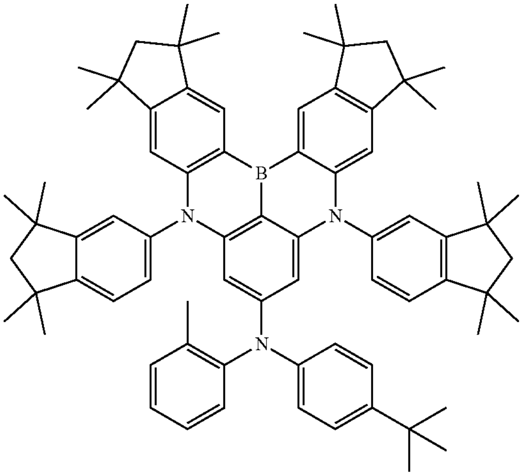

-continued
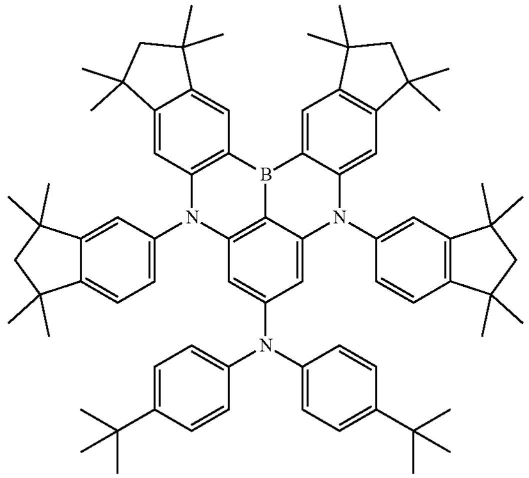
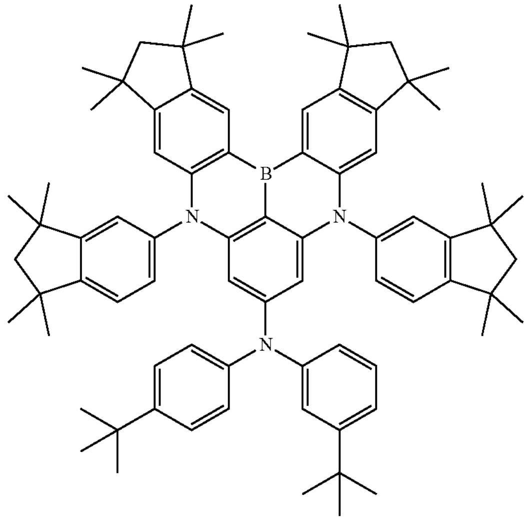
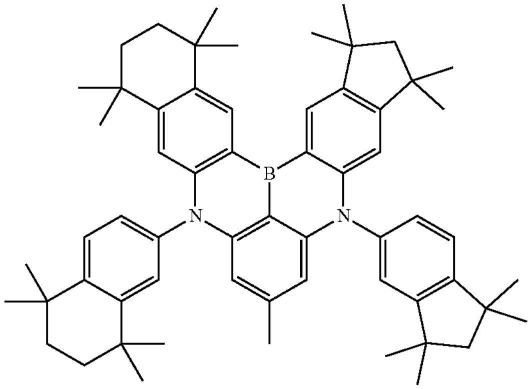
-continued
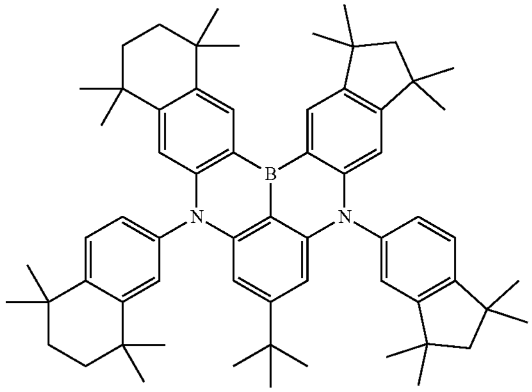
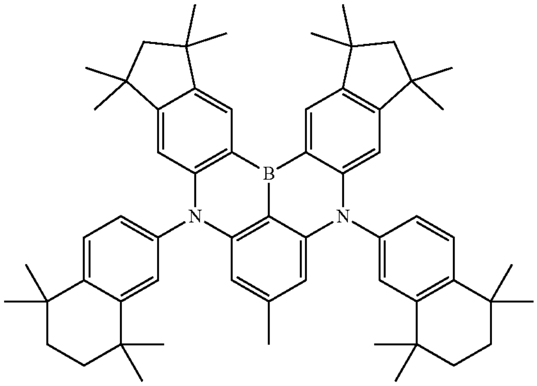
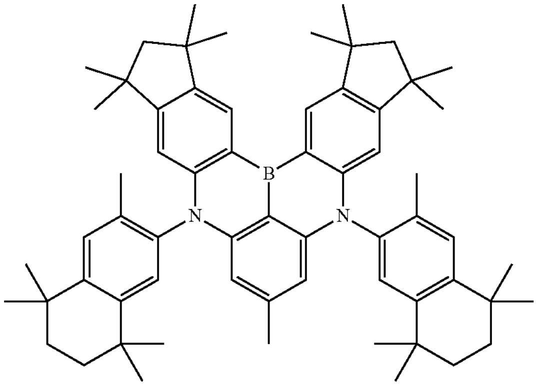
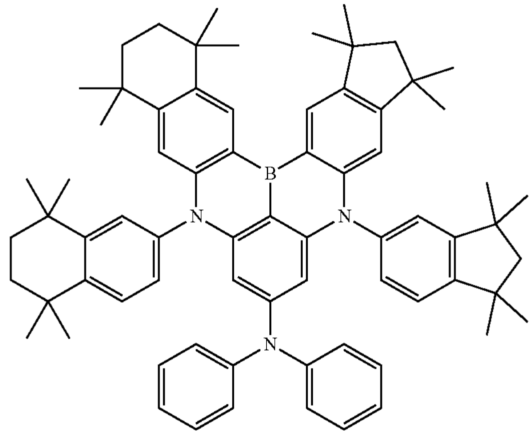

-continued
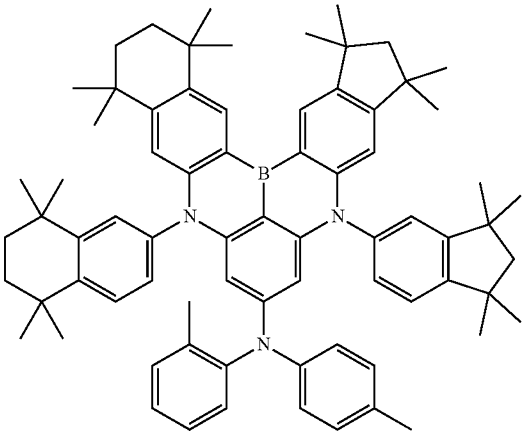
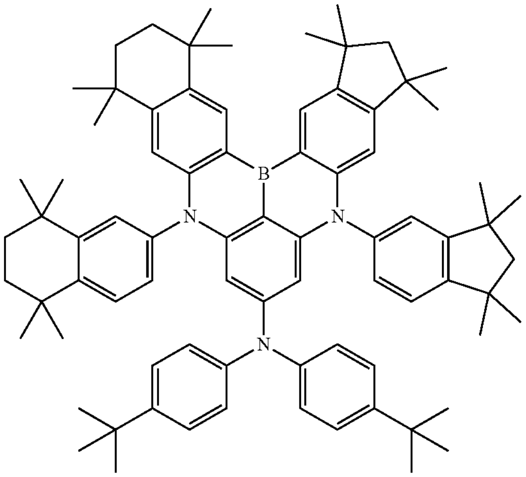
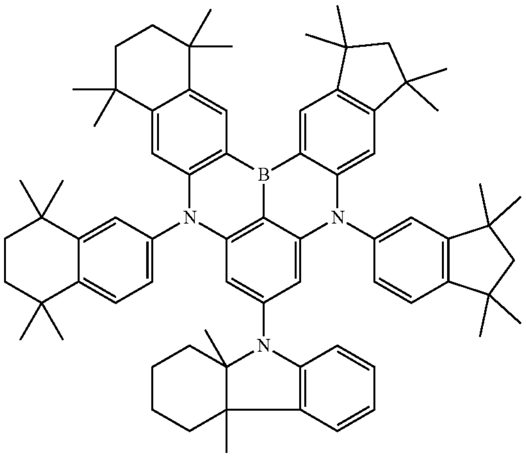
-continued
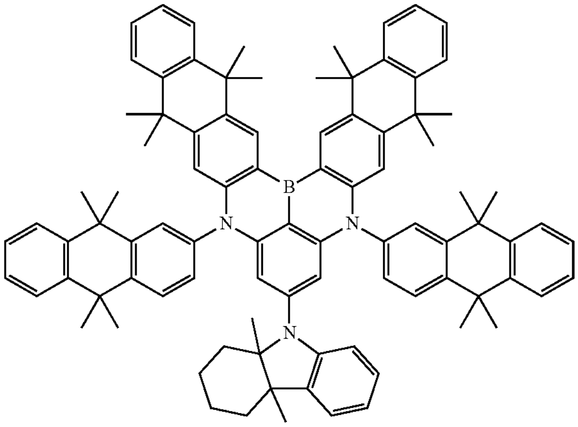
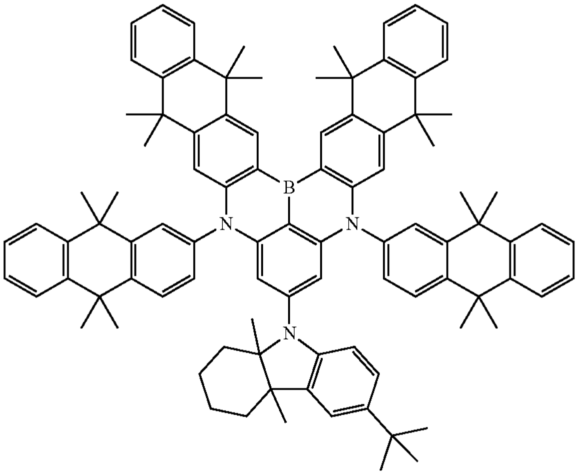
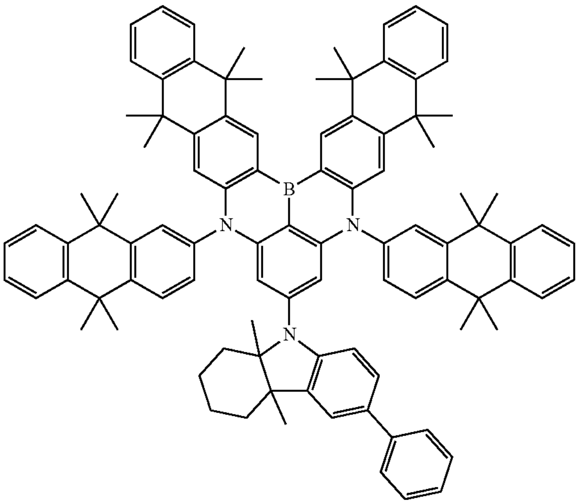

-continued
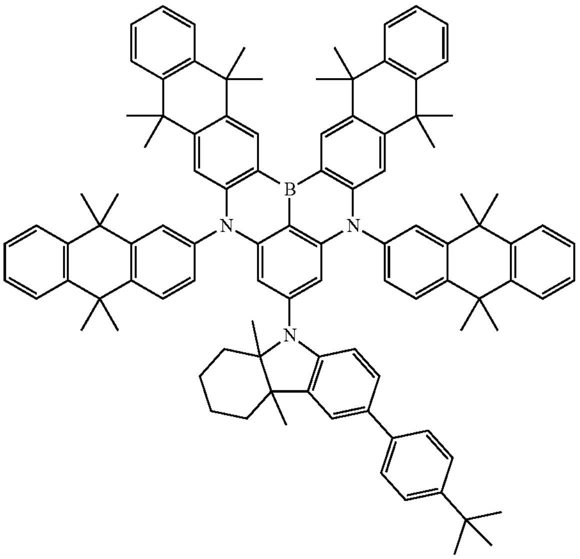
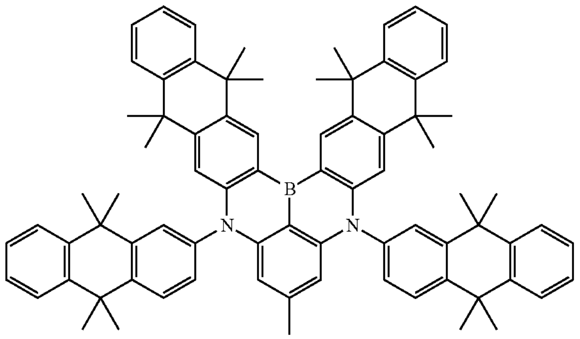
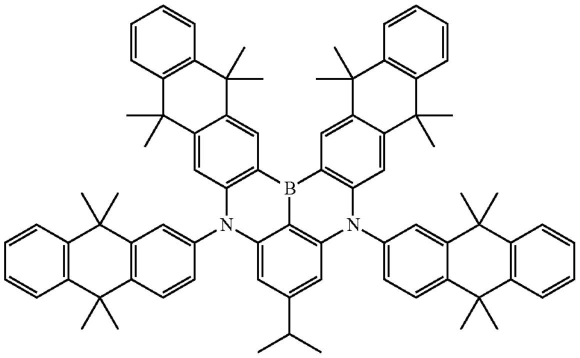
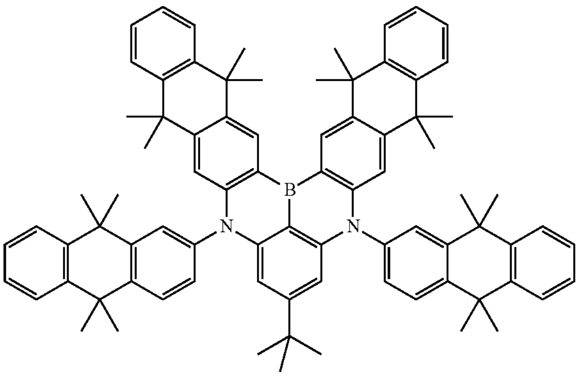
-continued
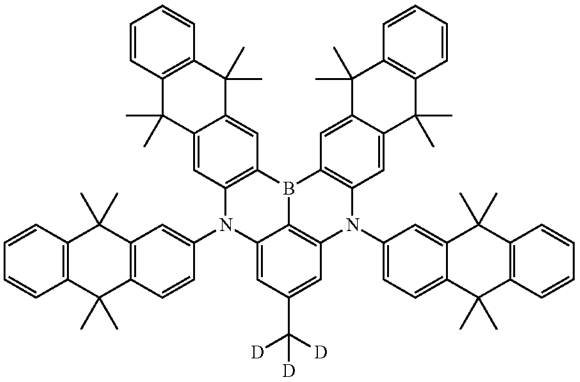
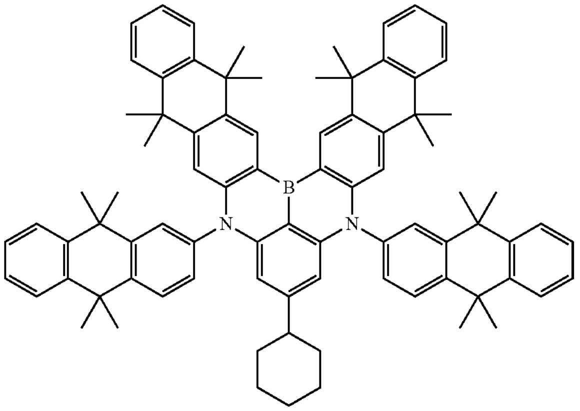
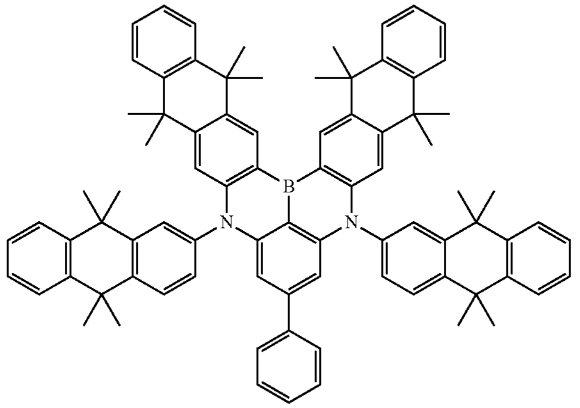
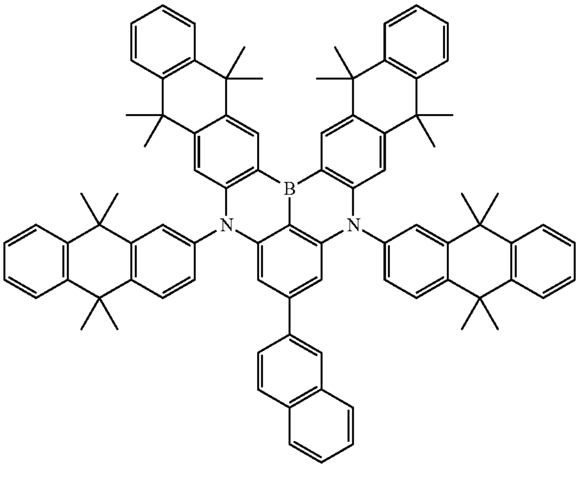

-continued
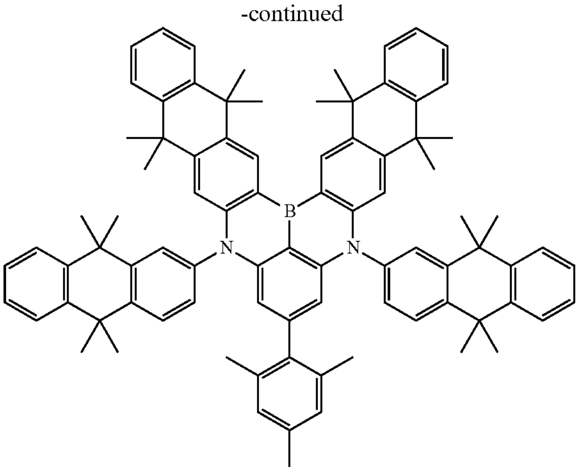
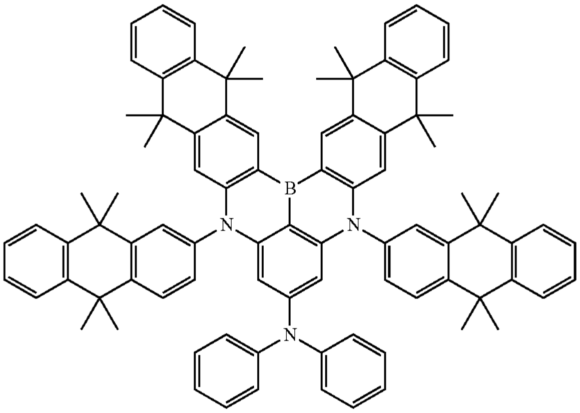
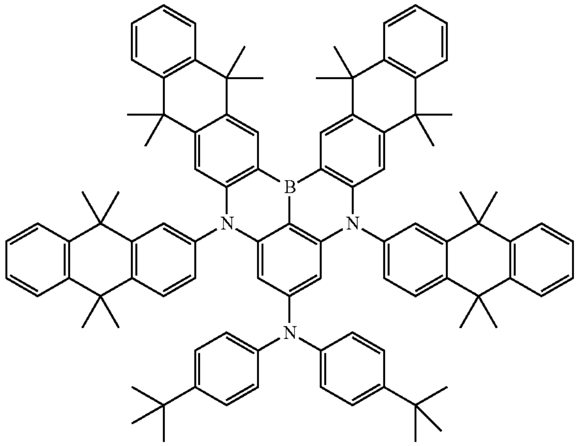
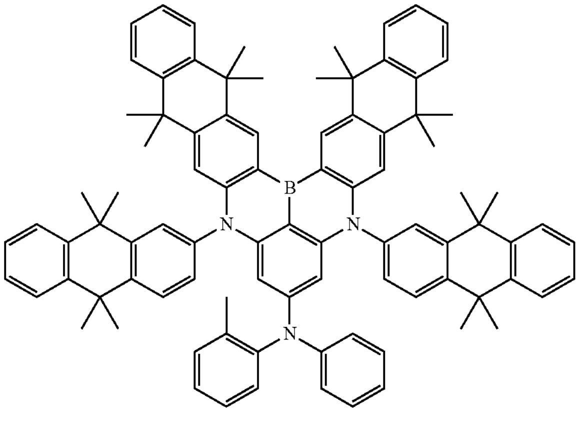
-continued
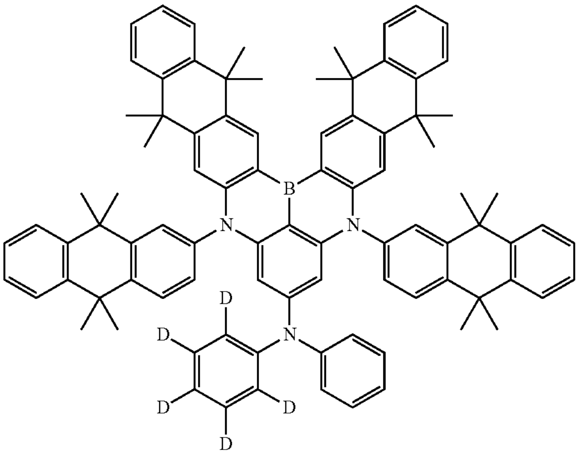
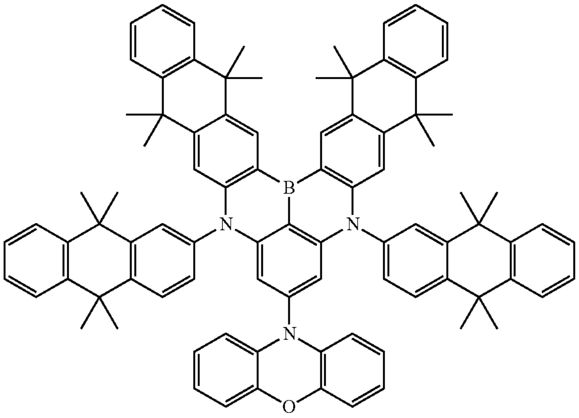
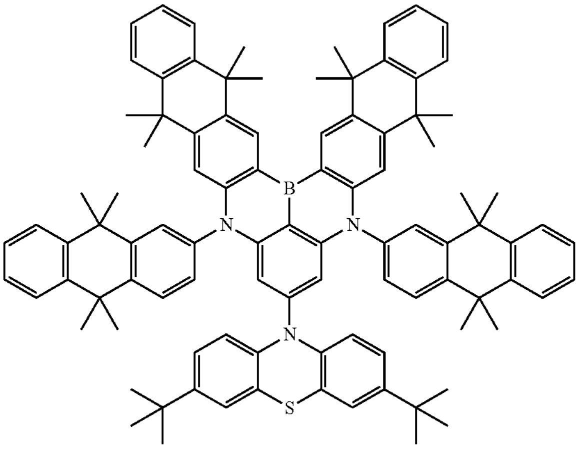

-continued
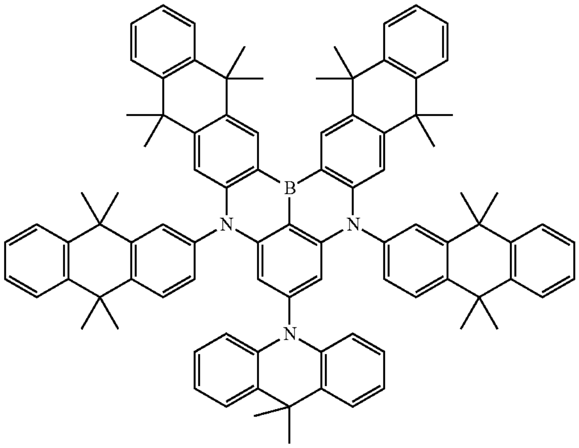
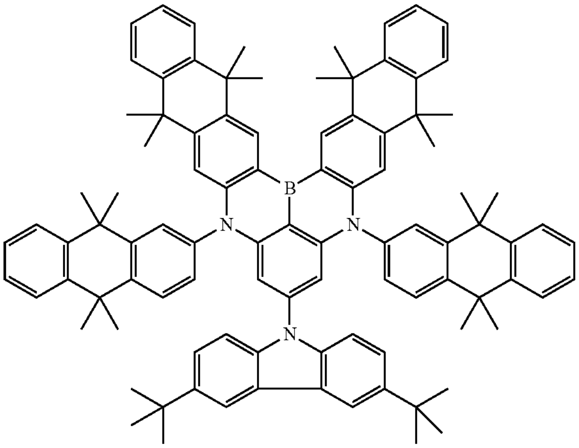
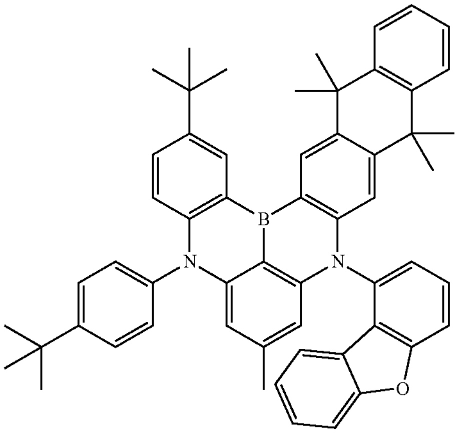
-continued
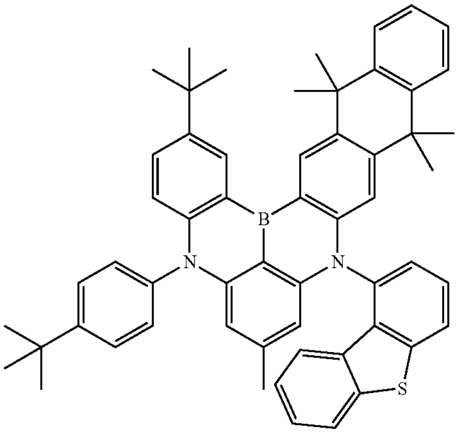
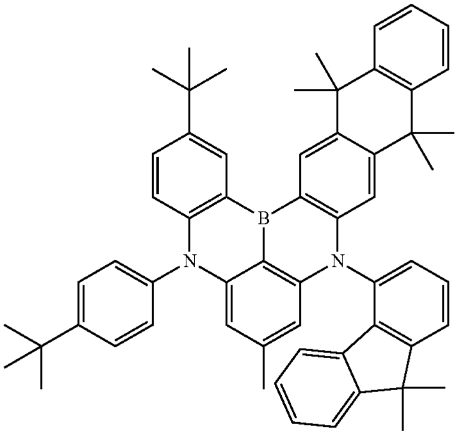
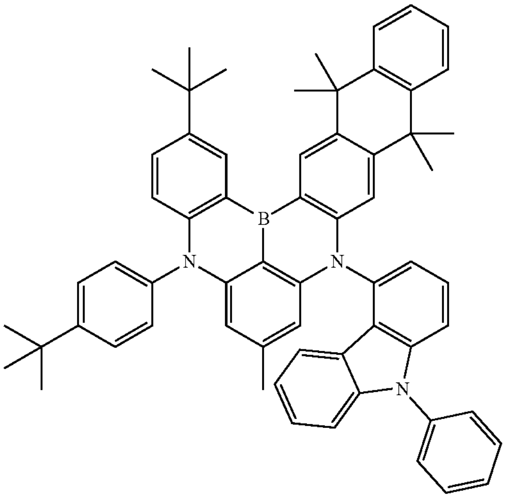

-continued
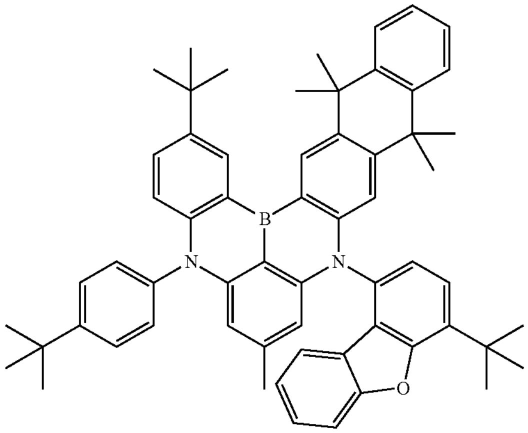
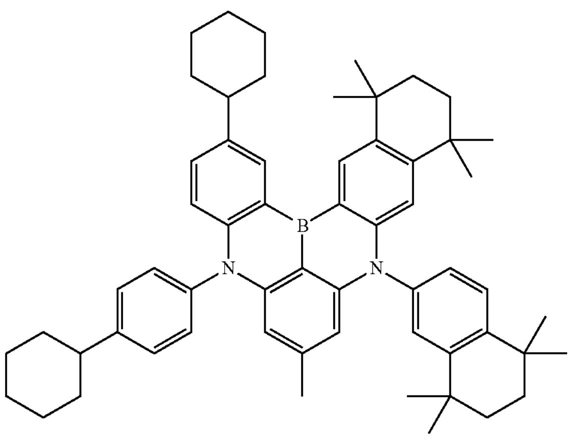
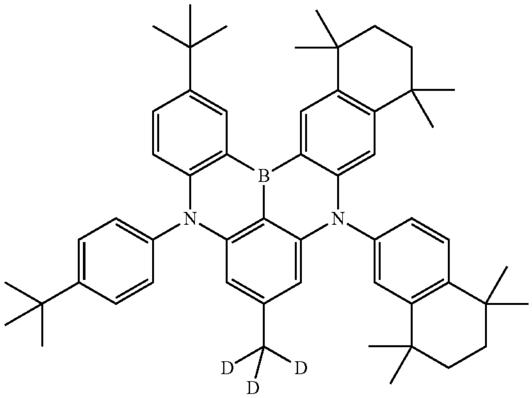
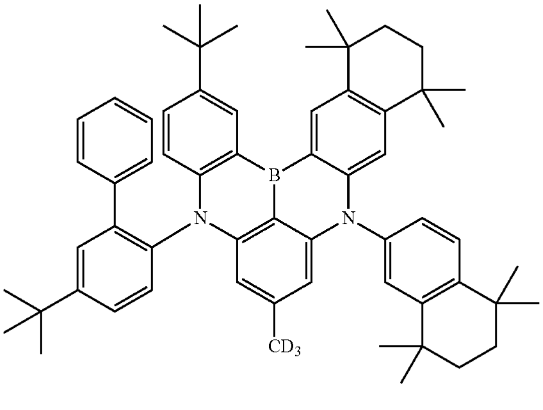
-continued
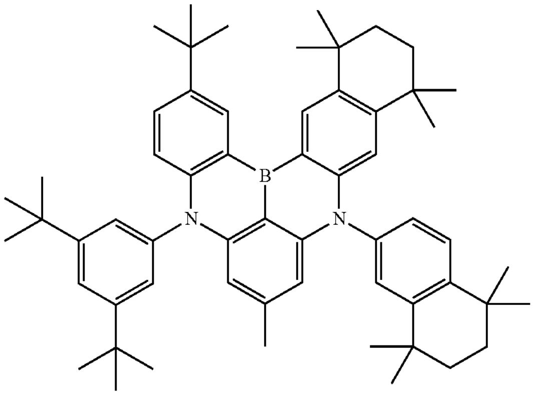
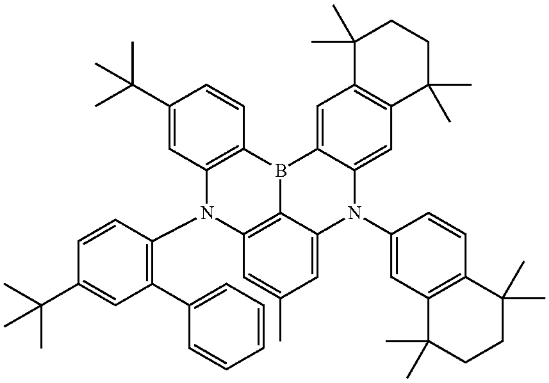
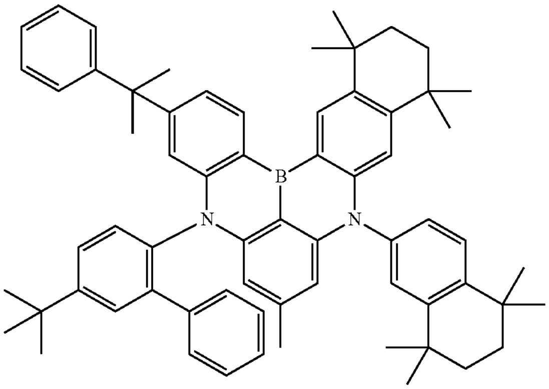
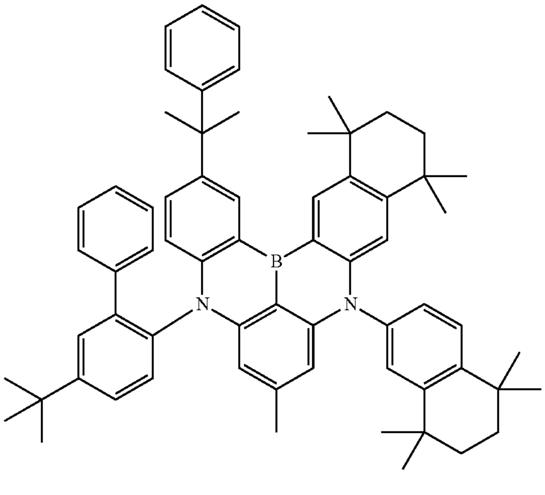

-continued
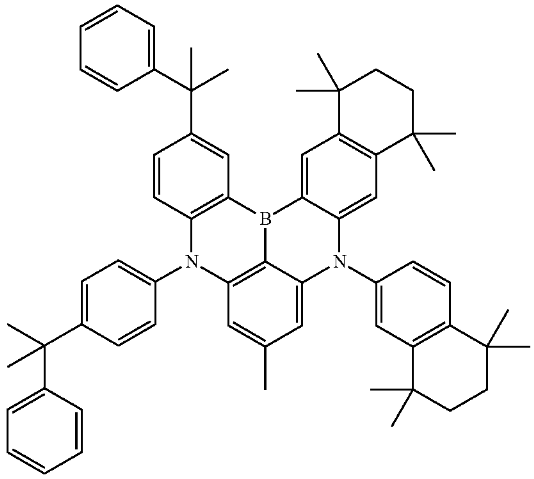
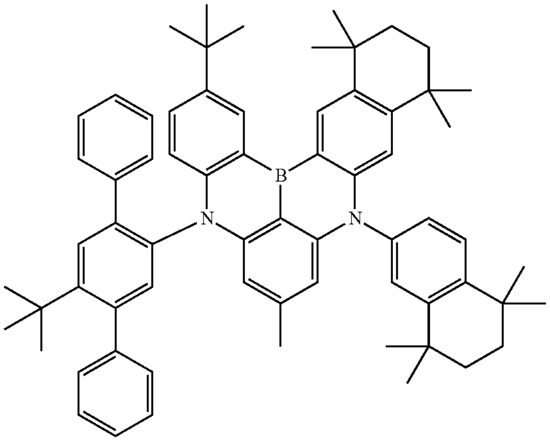
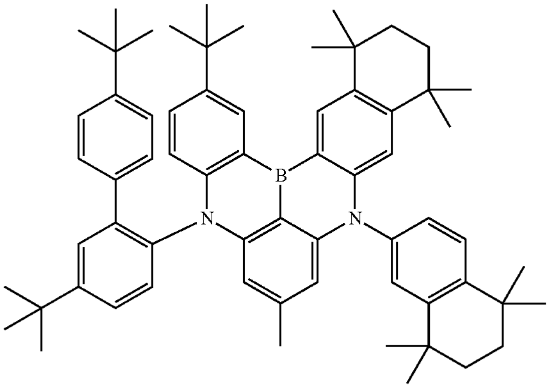
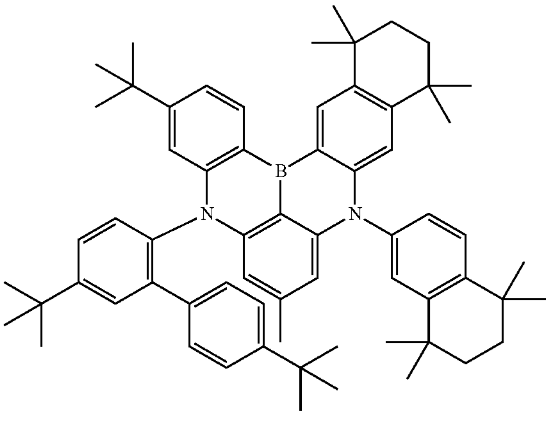
-continued
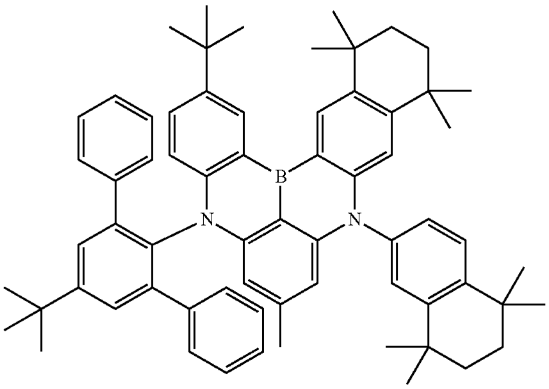
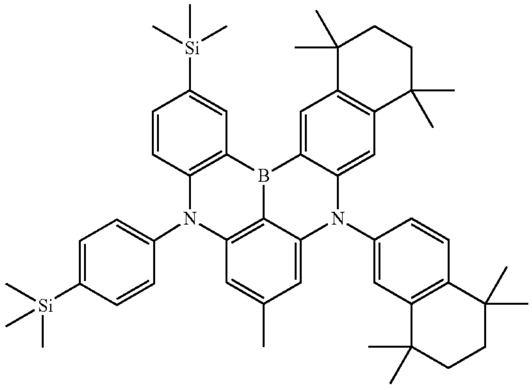
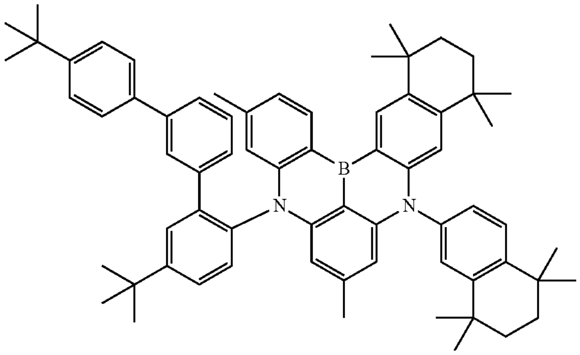
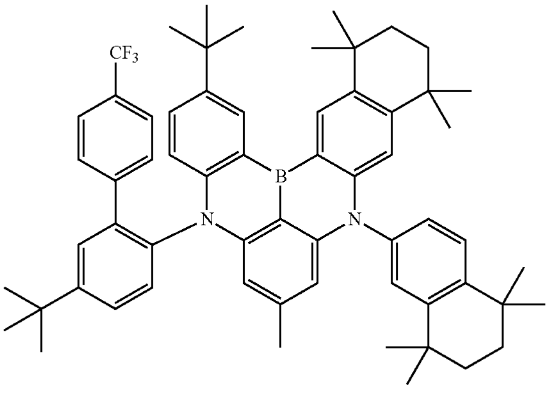

-continued
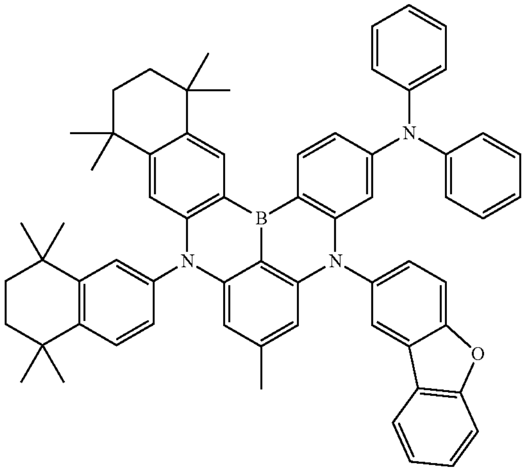
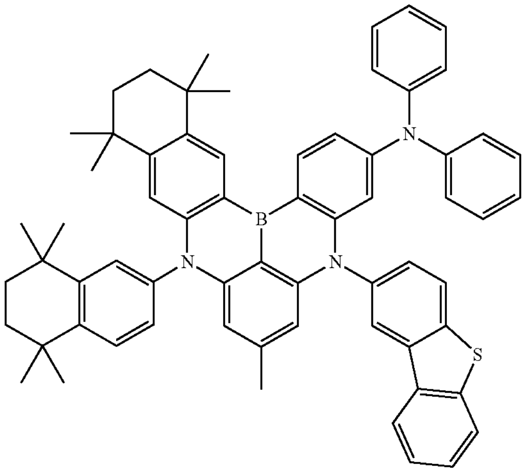
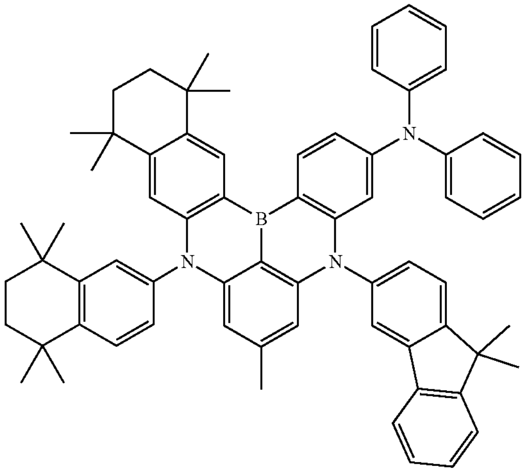
-continued
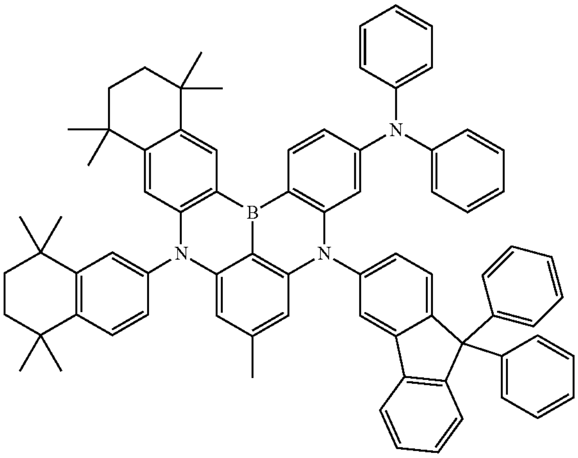
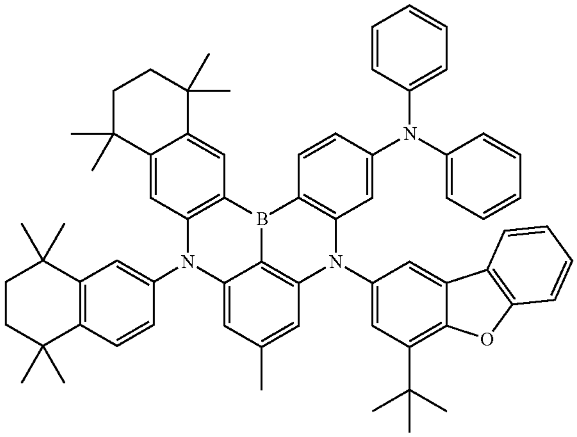
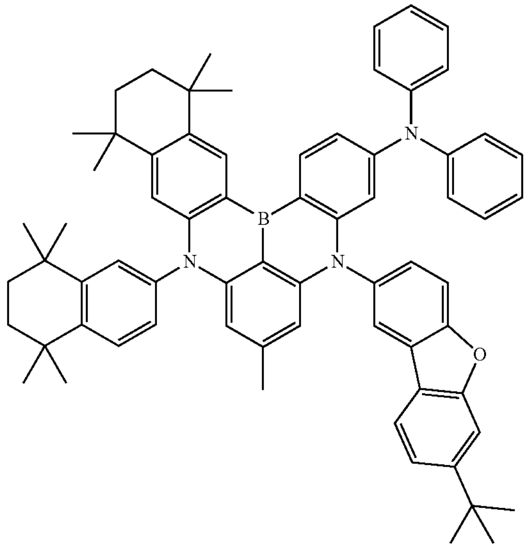

-continued
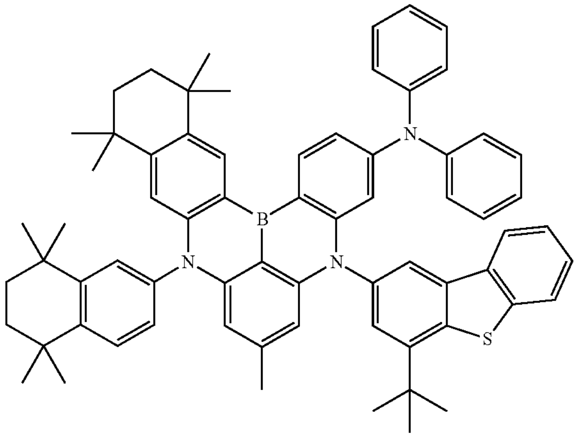
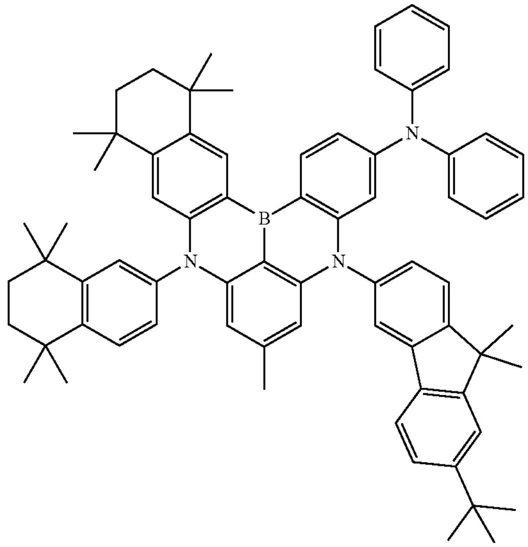
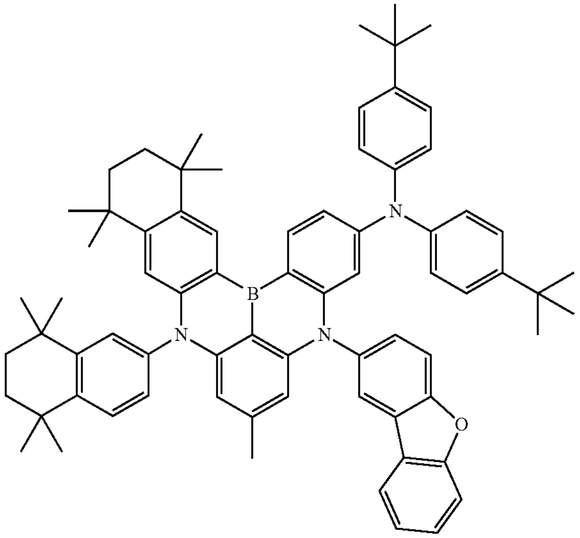
-continued
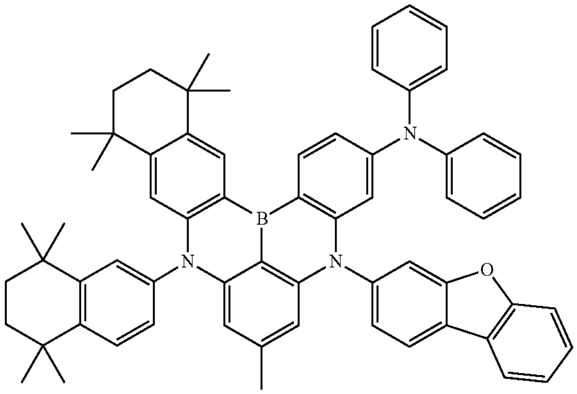
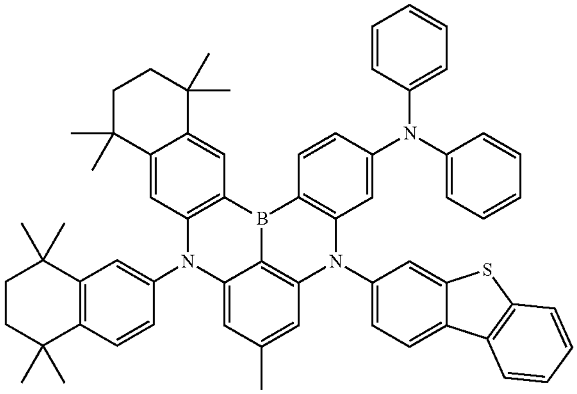
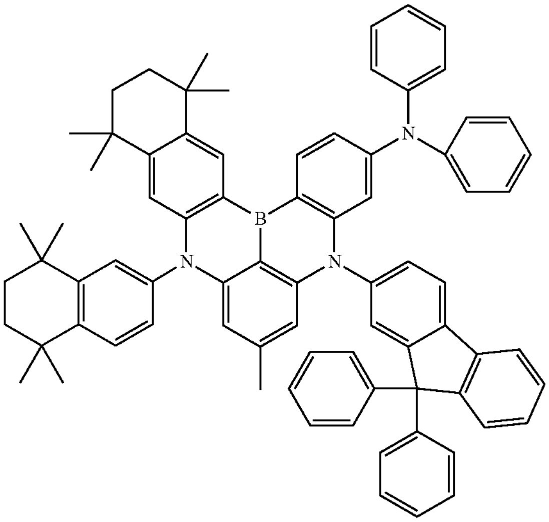

-continued
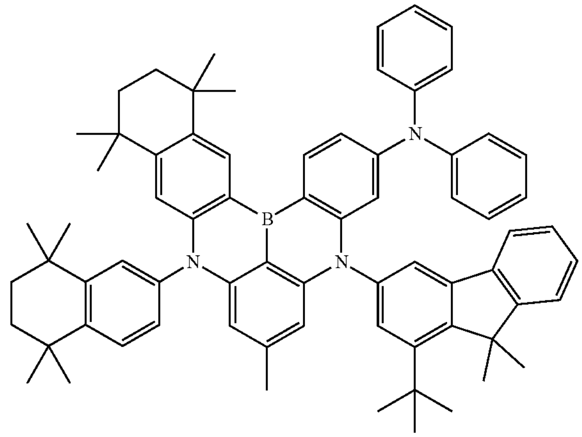
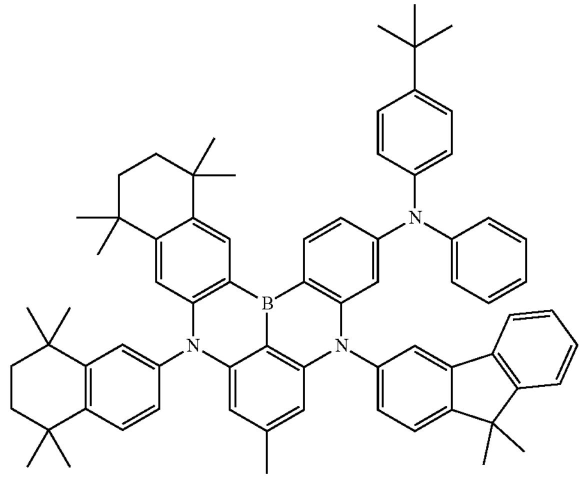
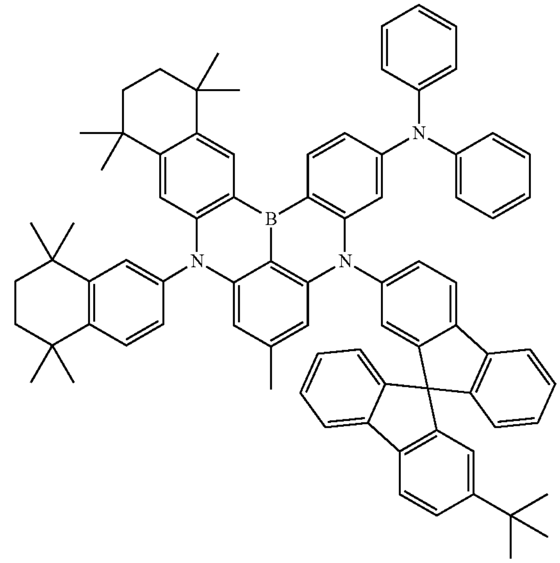
-continued
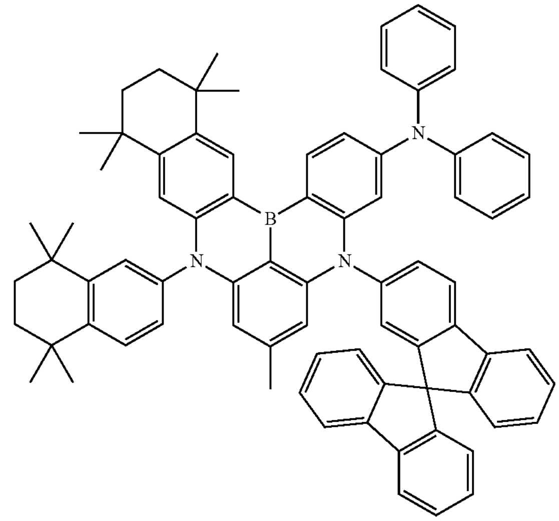
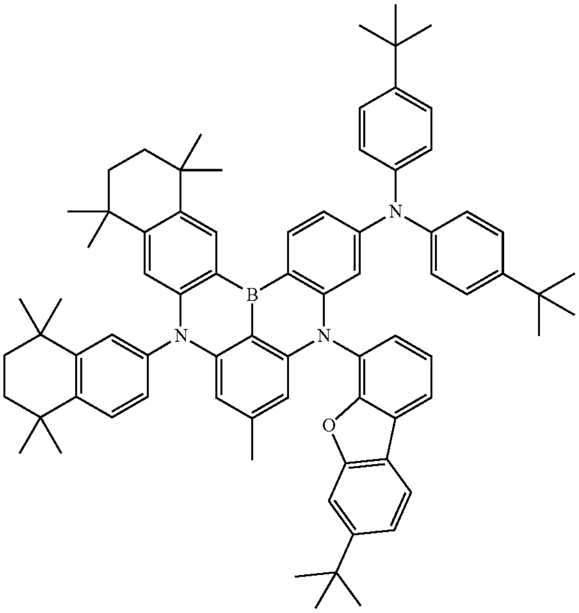
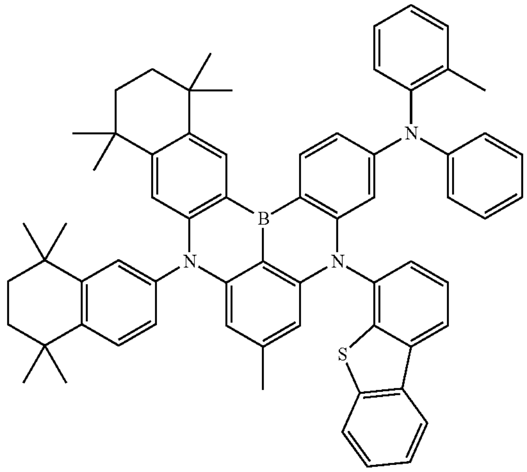

-continued
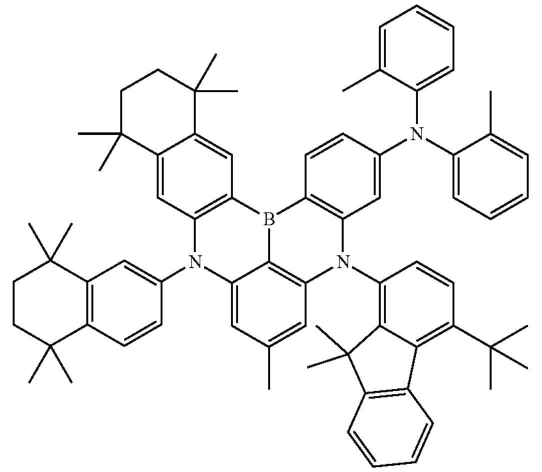
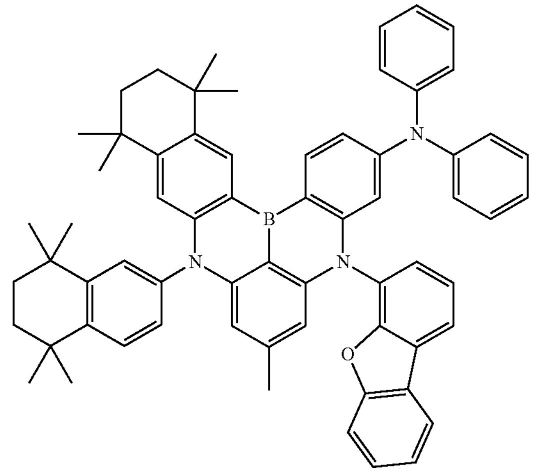
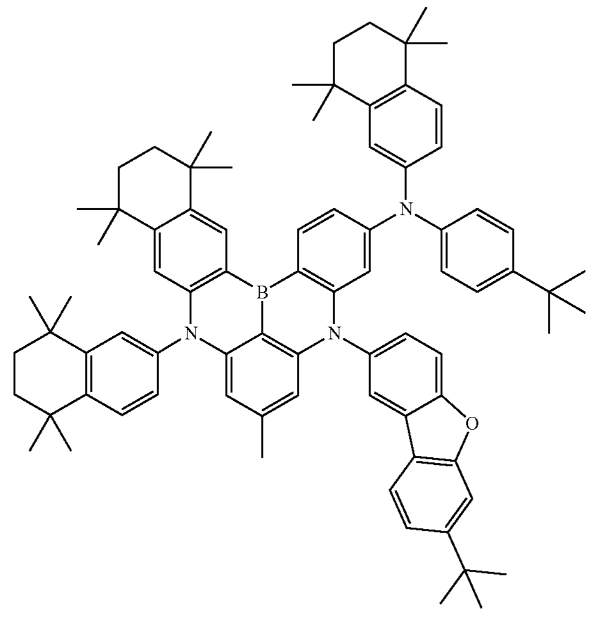
-continued
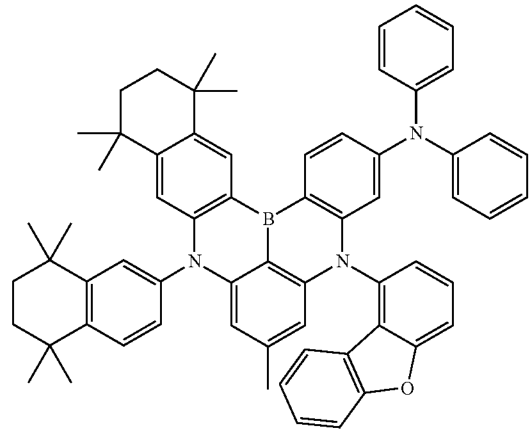
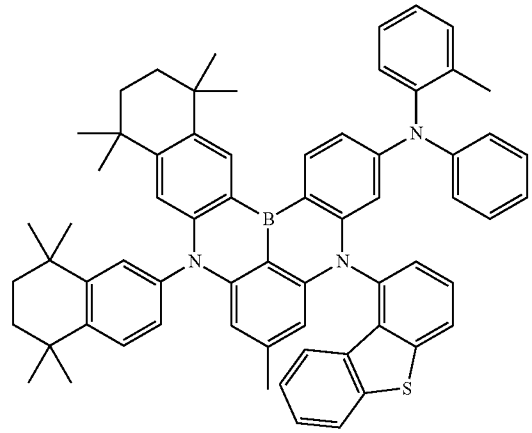
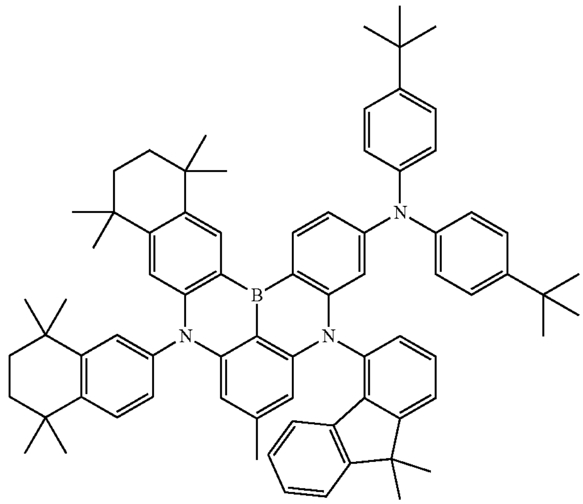

-continued
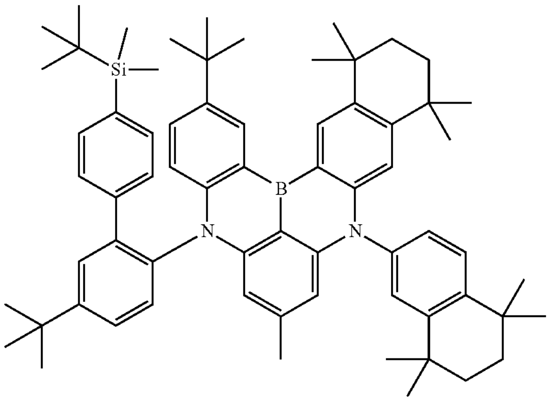
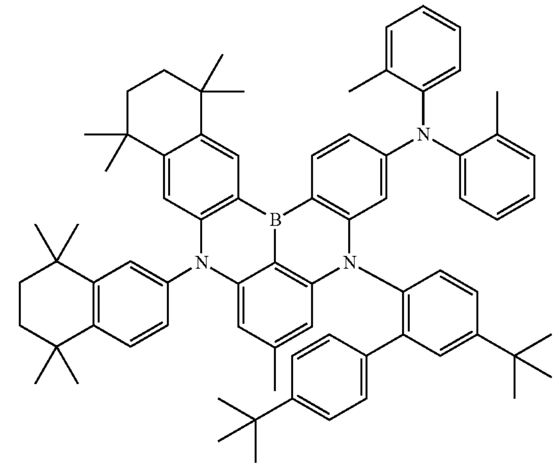
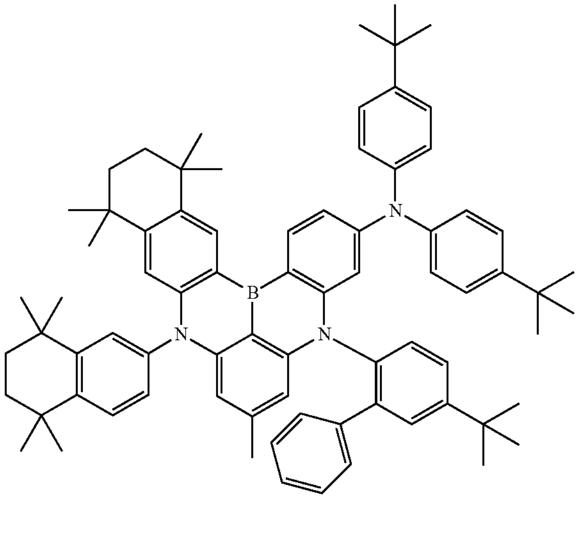
-continued
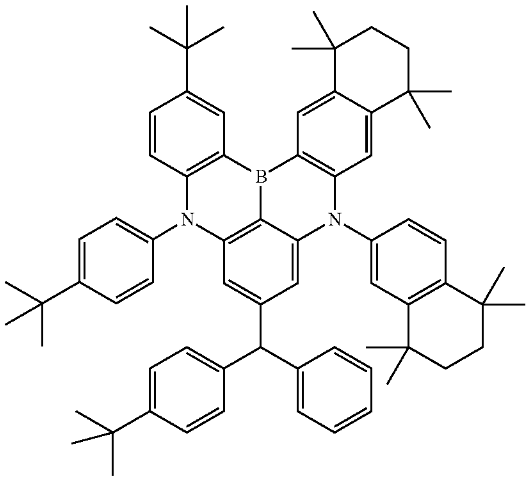
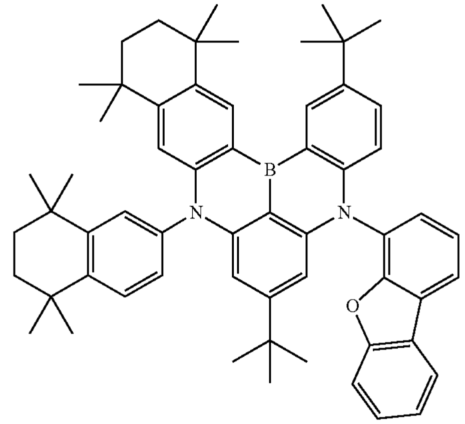
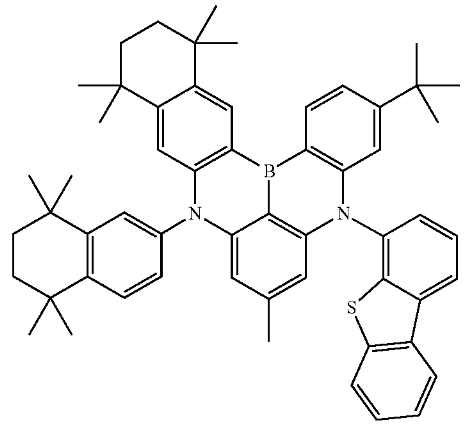

-continued
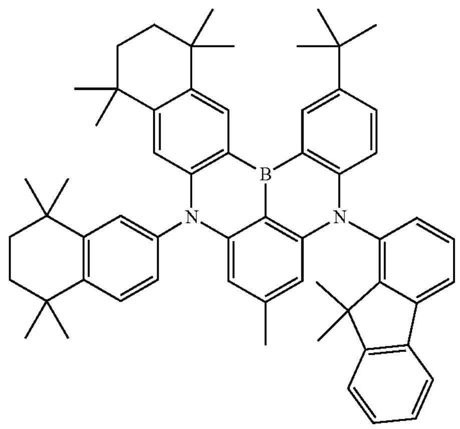
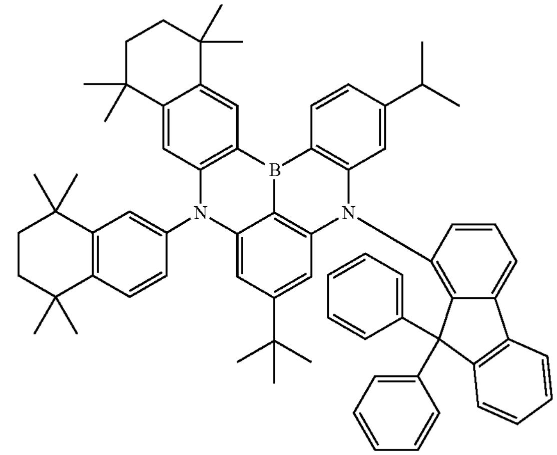
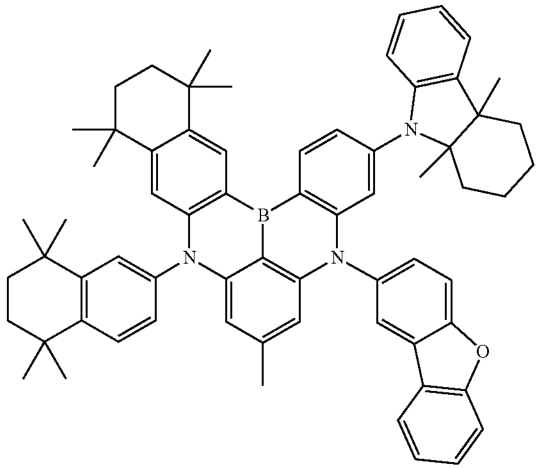
-continued
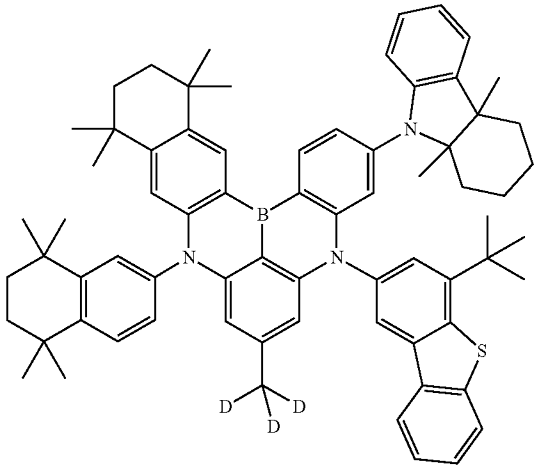
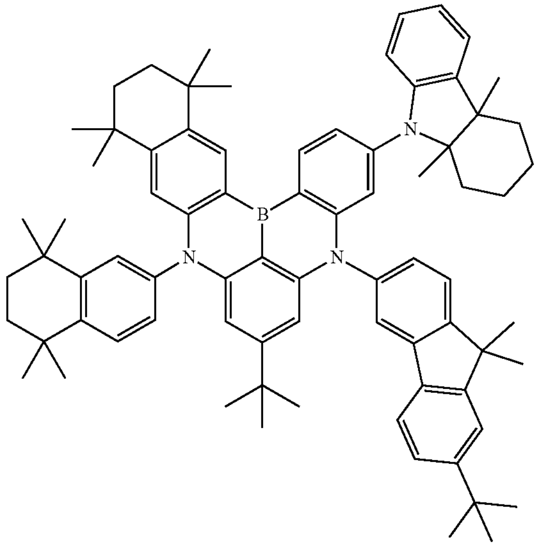
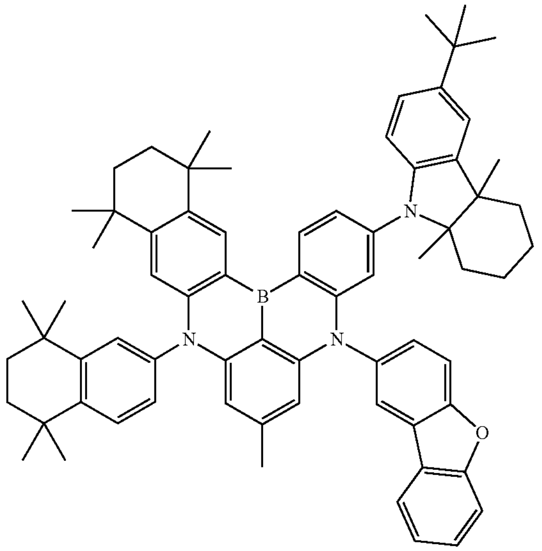

-continued
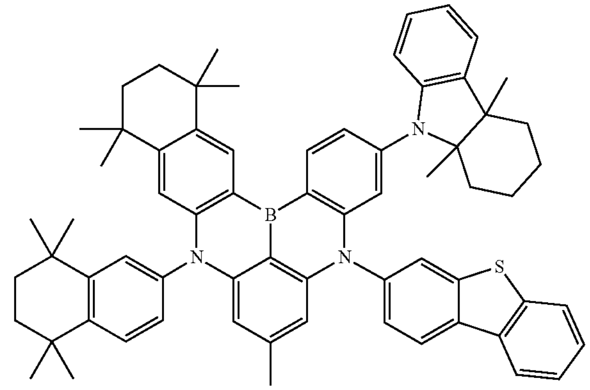
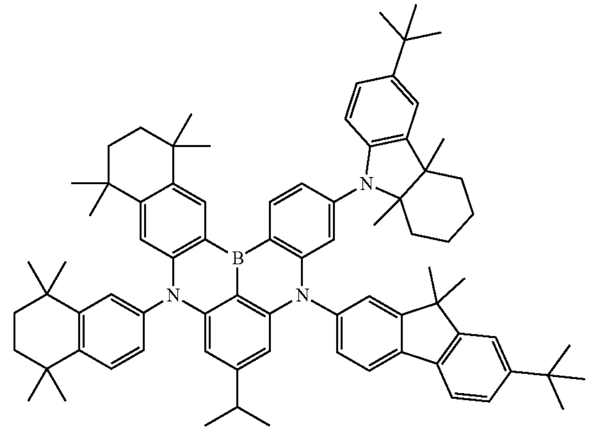
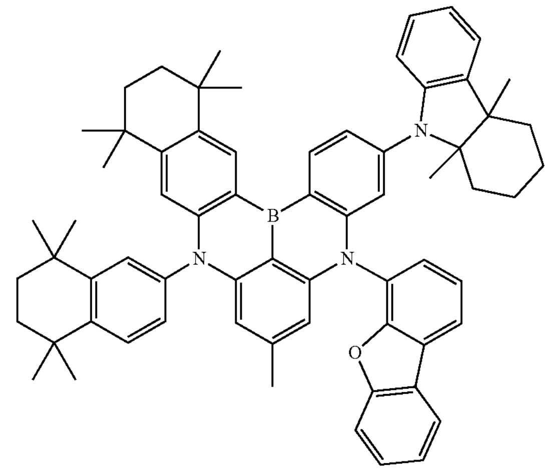
-continued
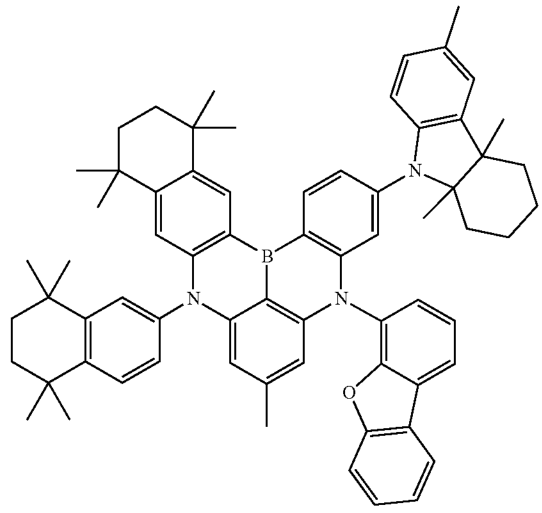
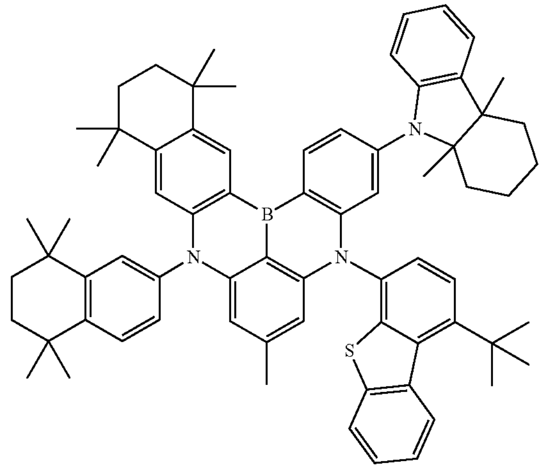
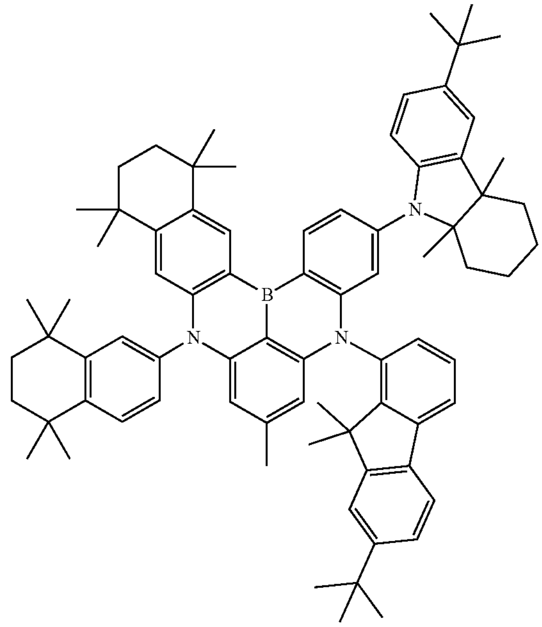

-continued
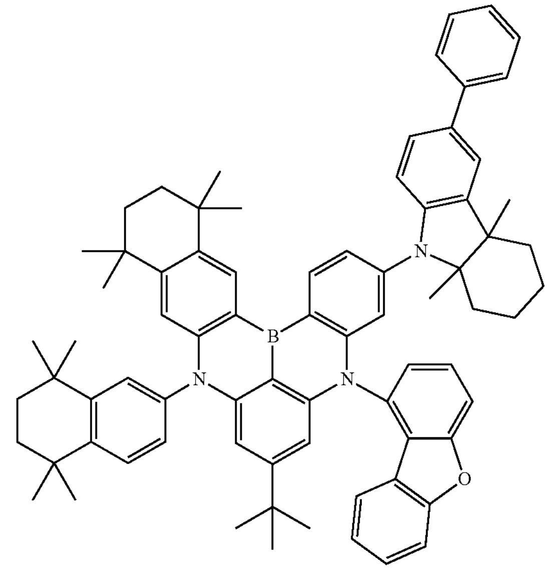
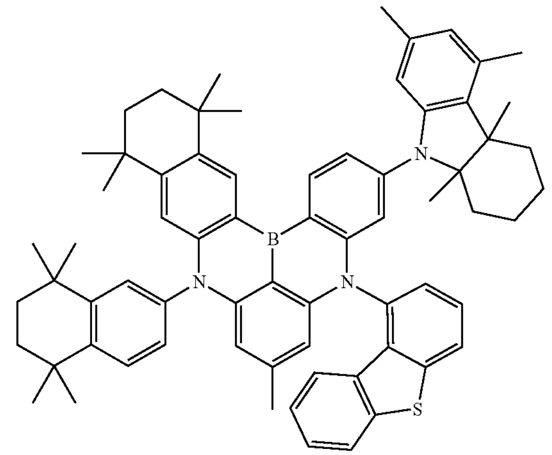
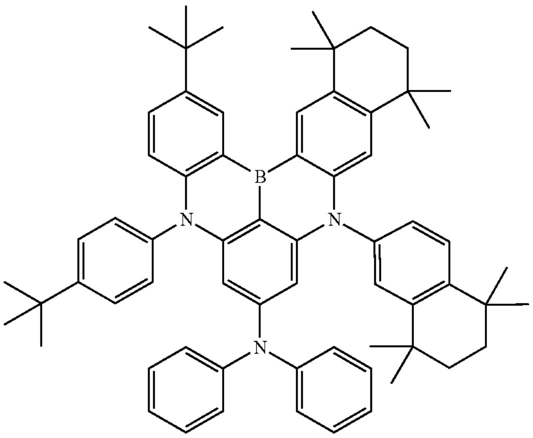
-continued
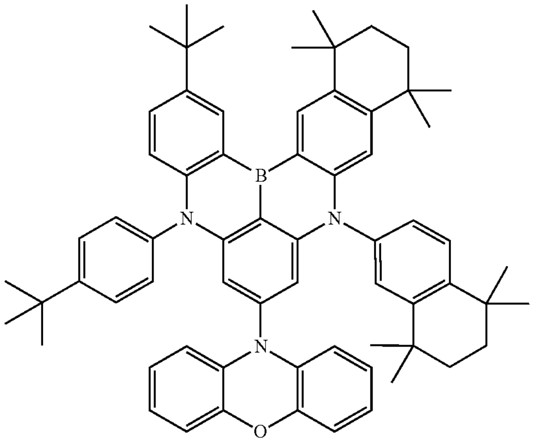
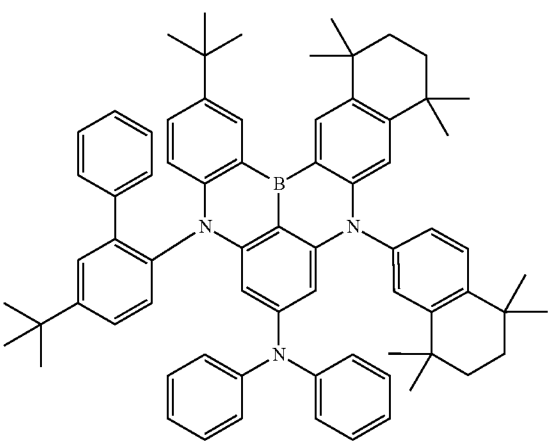
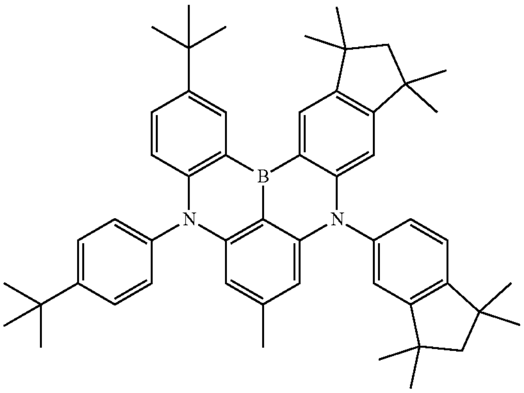

-continued
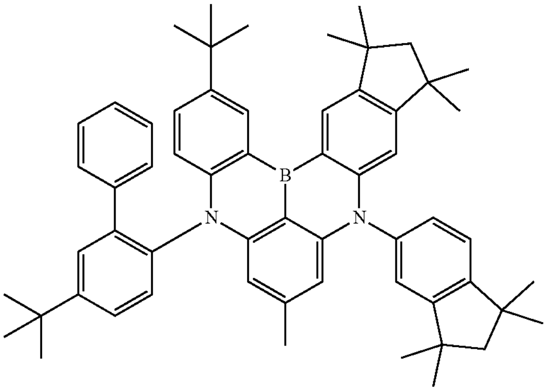
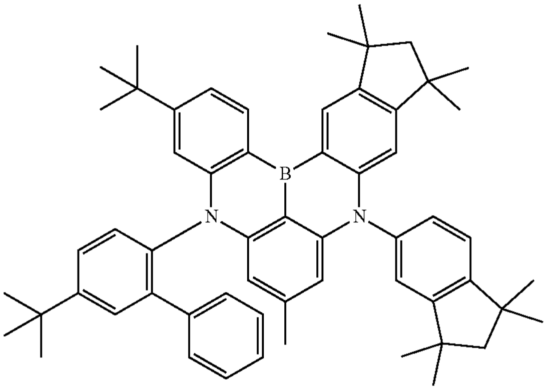
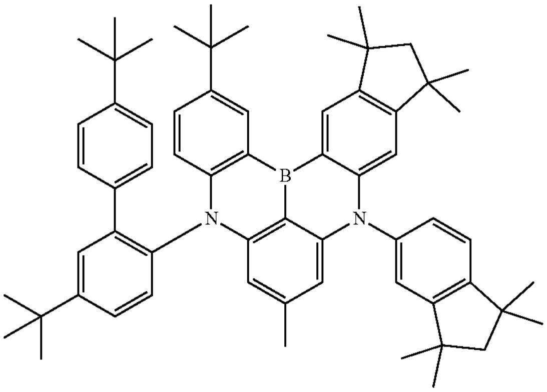
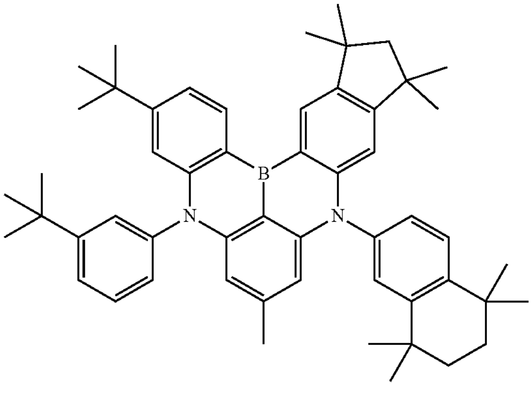
-continued
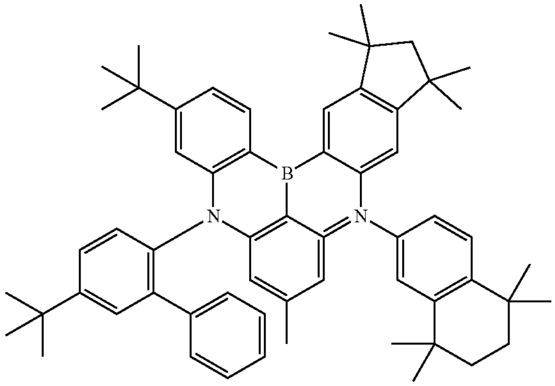
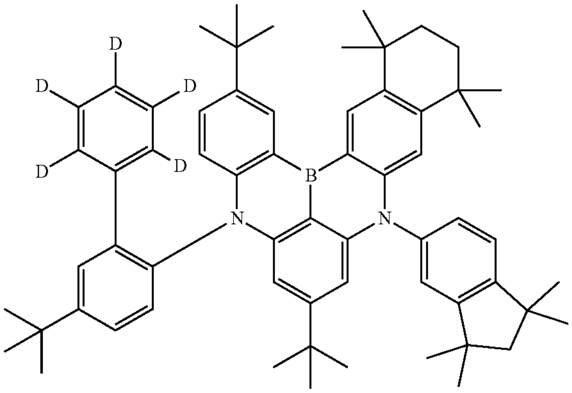
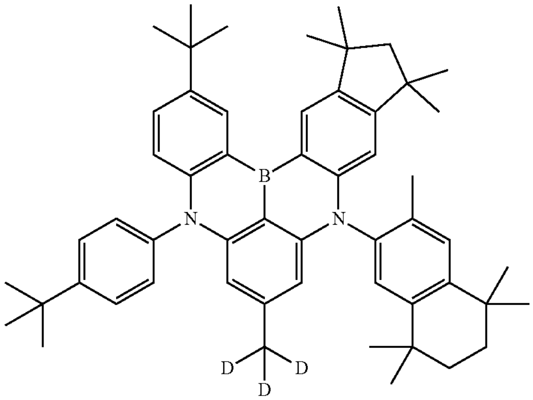
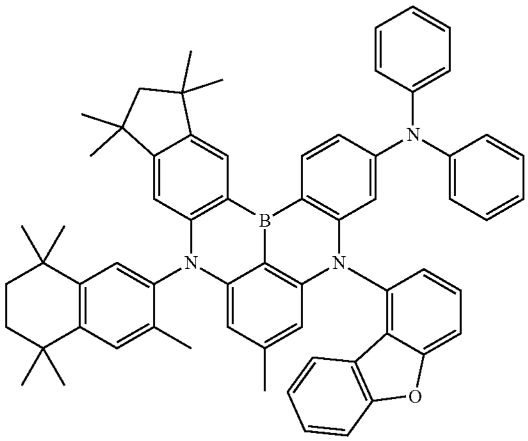

-continued
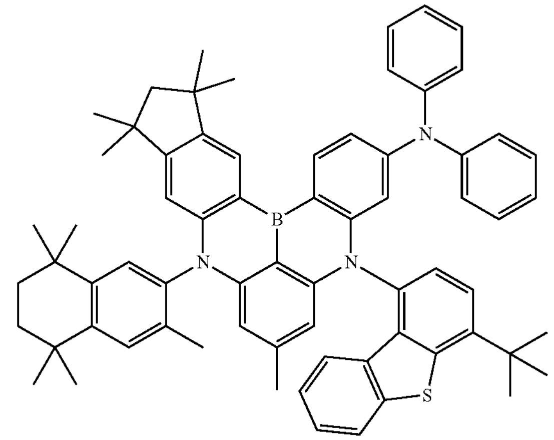
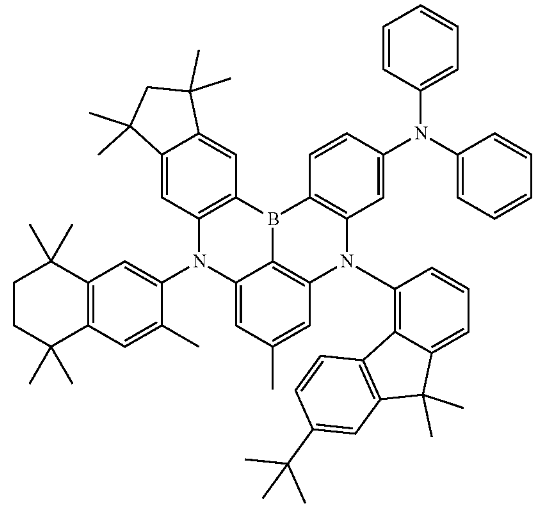
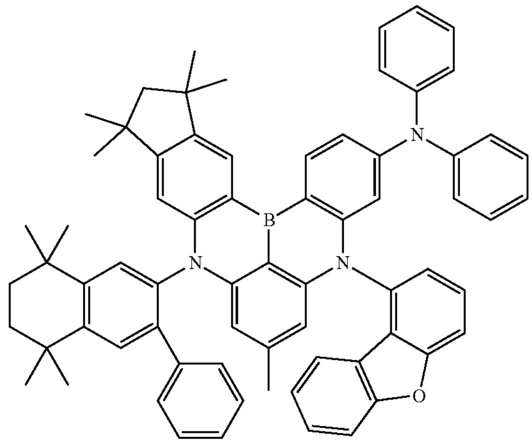
-continued
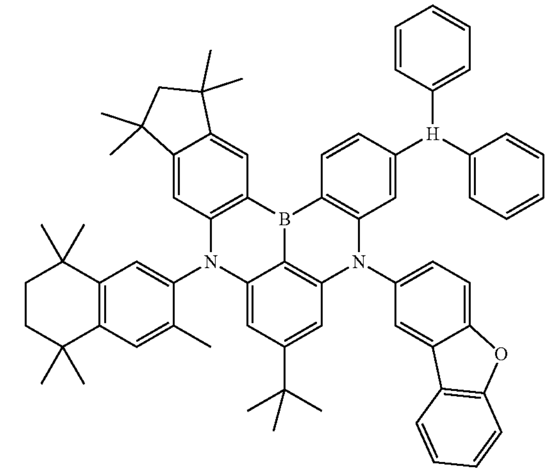
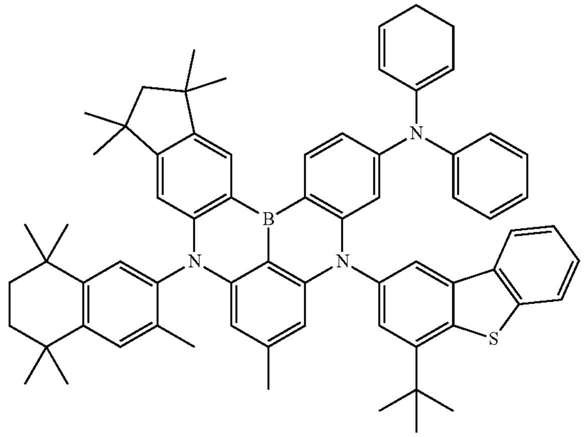
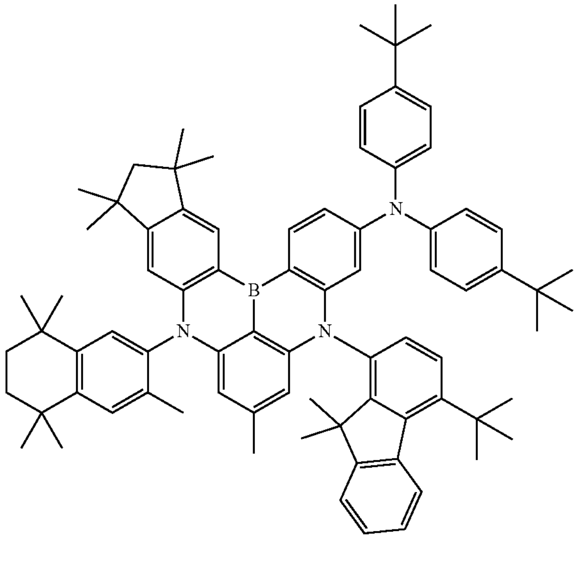

-continued
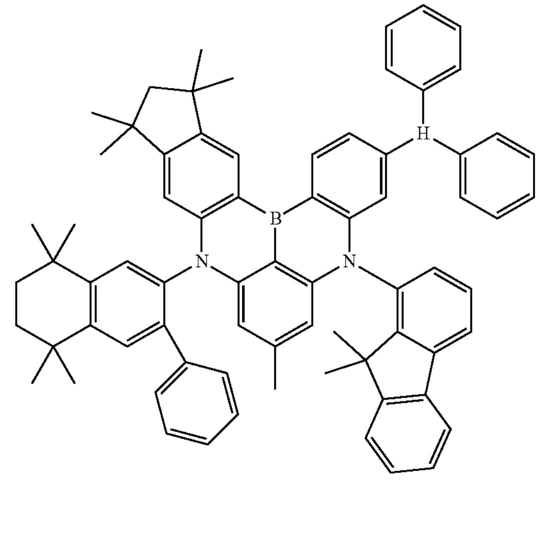
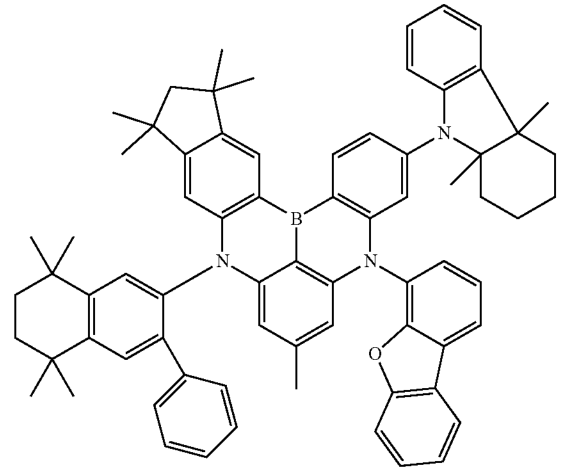
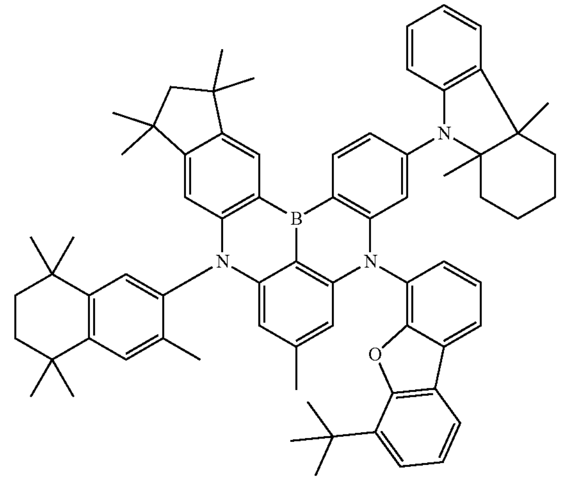
-continued
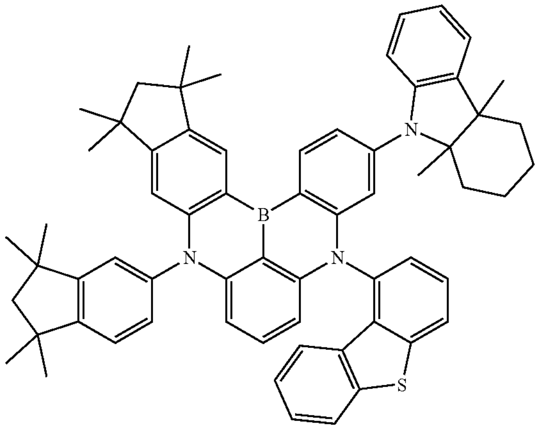
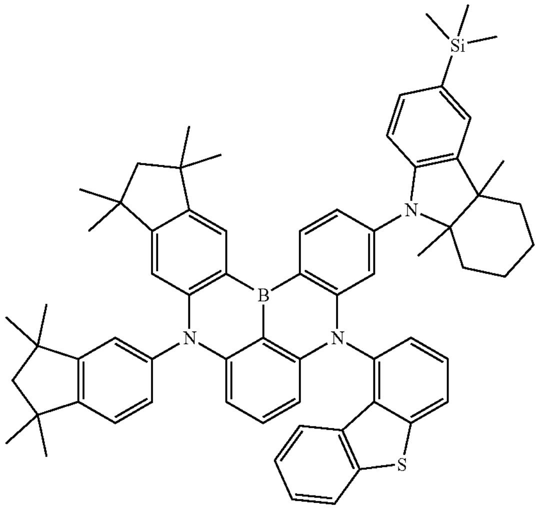
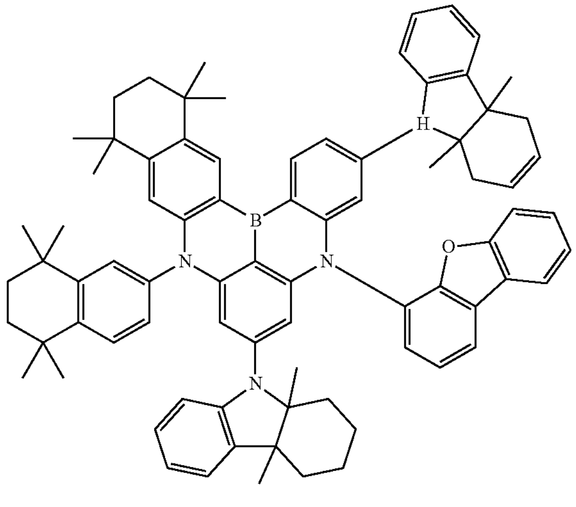

-continued
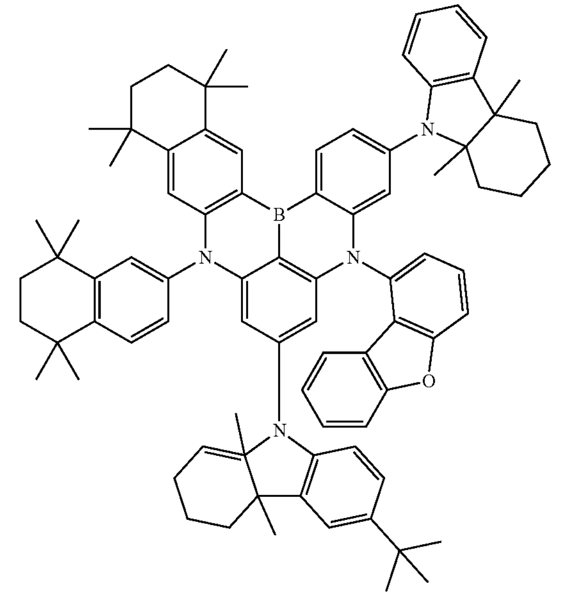
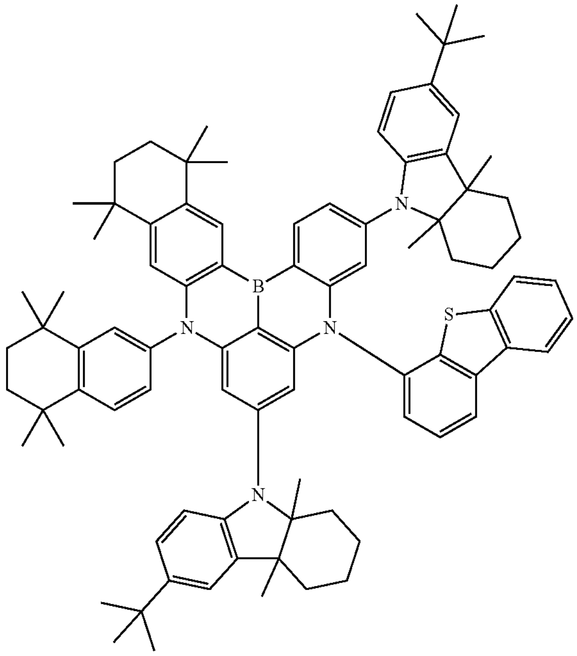
-continued
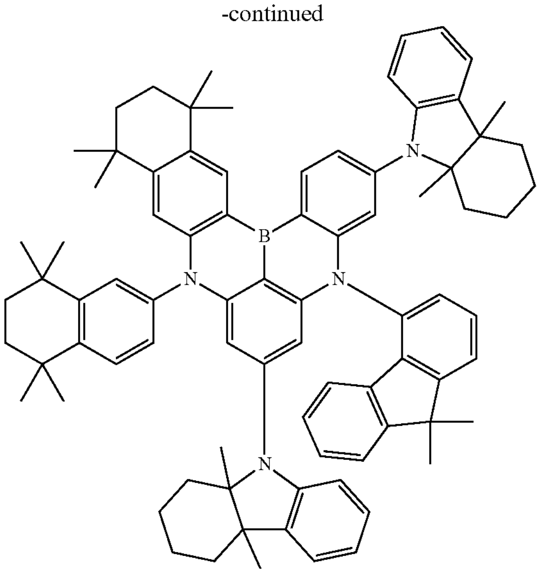
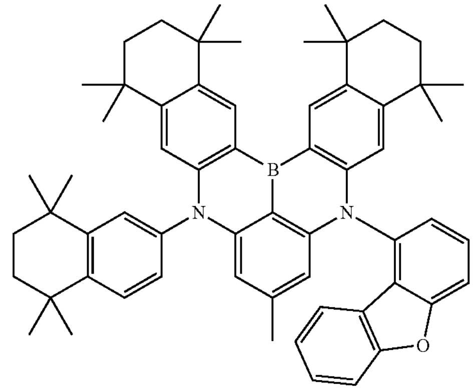
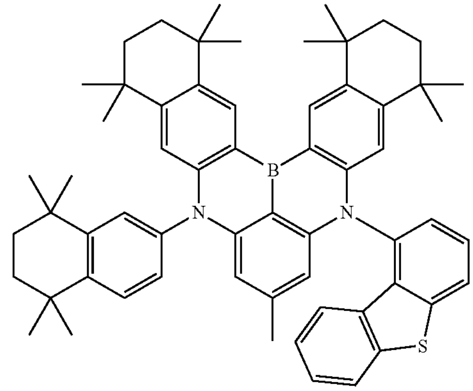
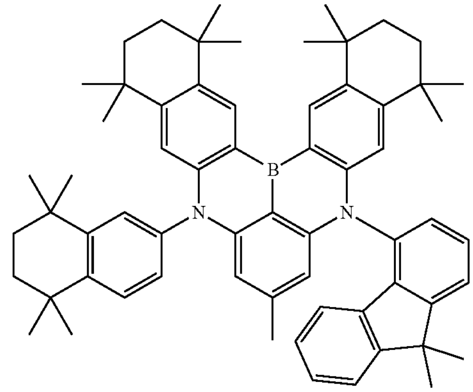

-continued
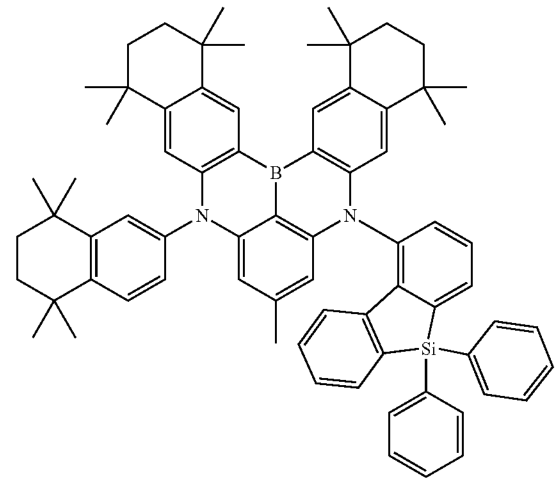
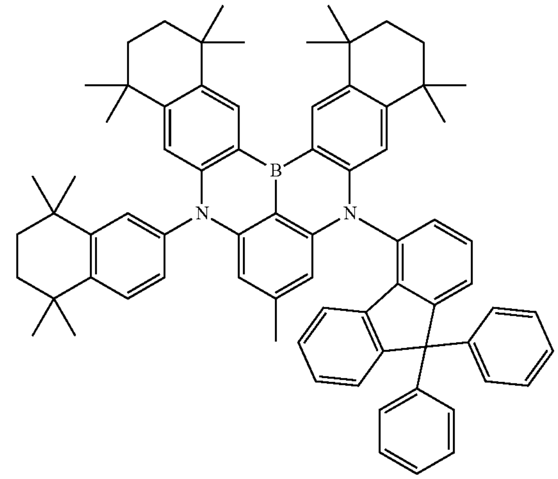
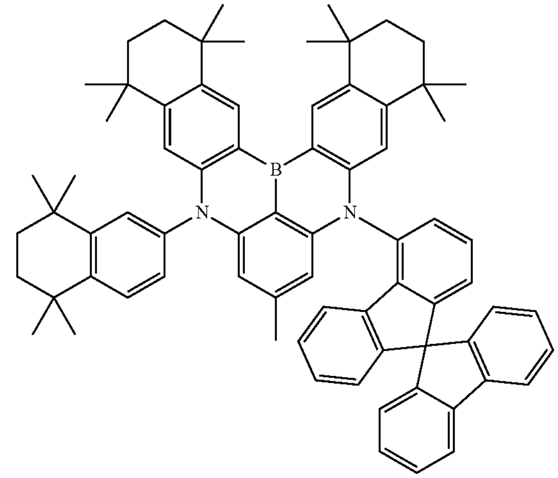
-continued
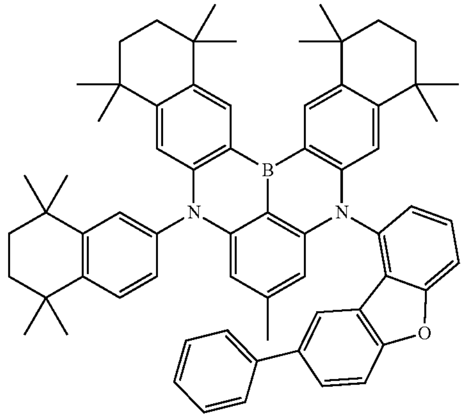
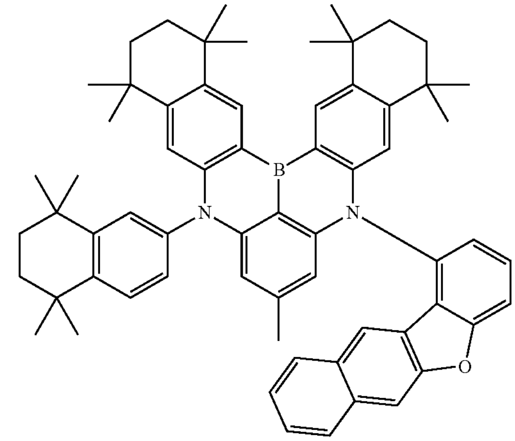
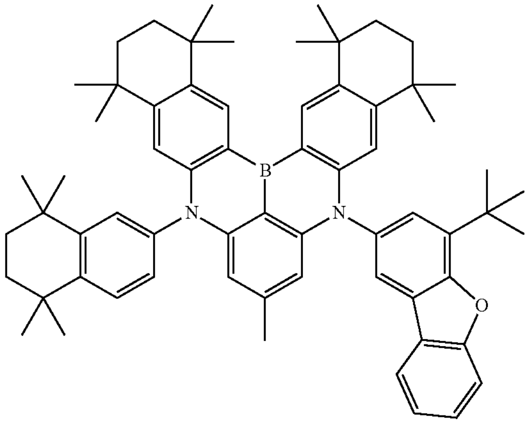
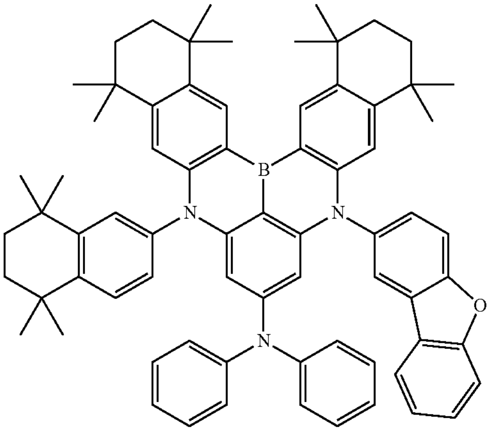

-continued
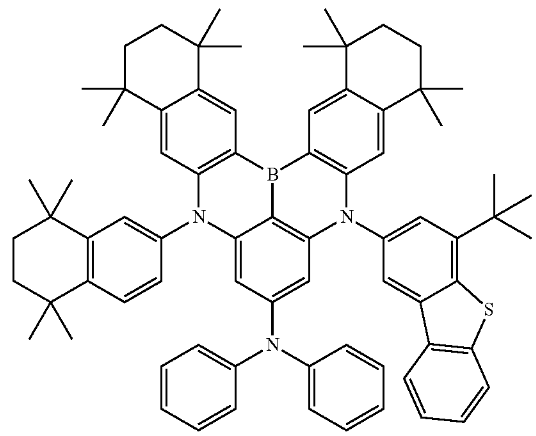
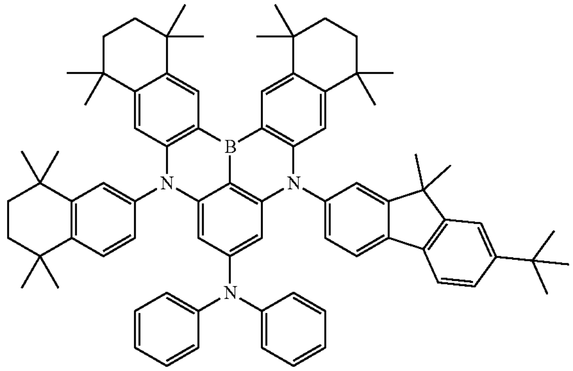
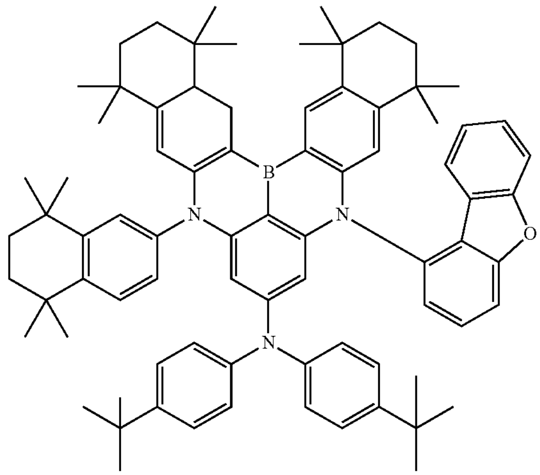
-continued
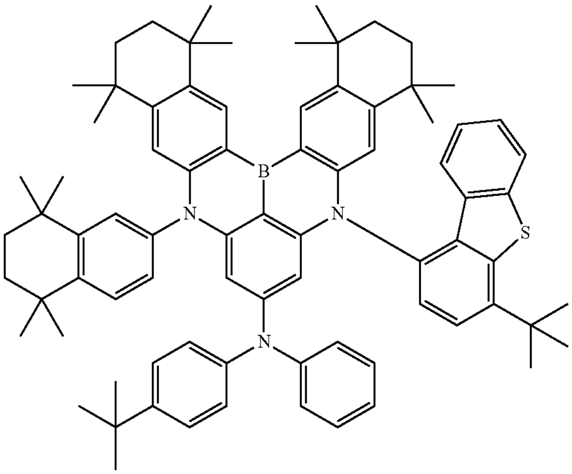
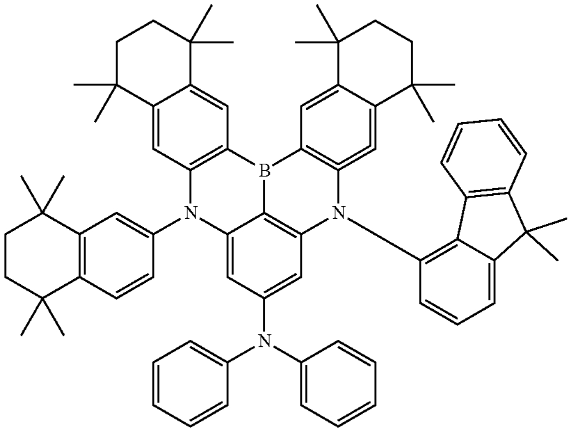
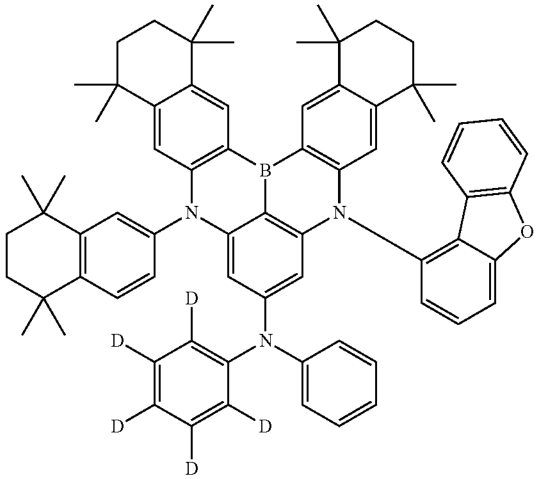

-continued
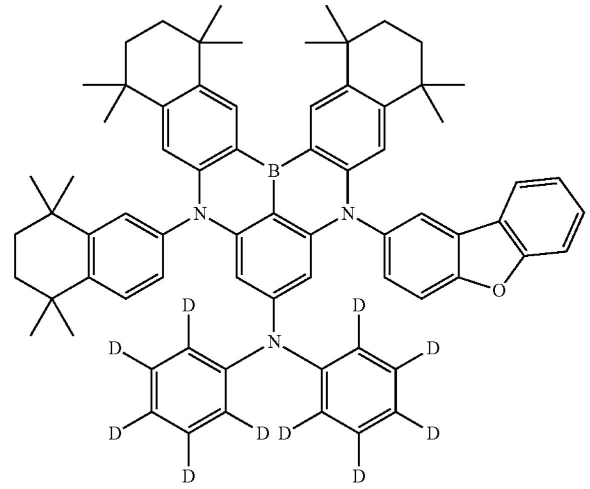
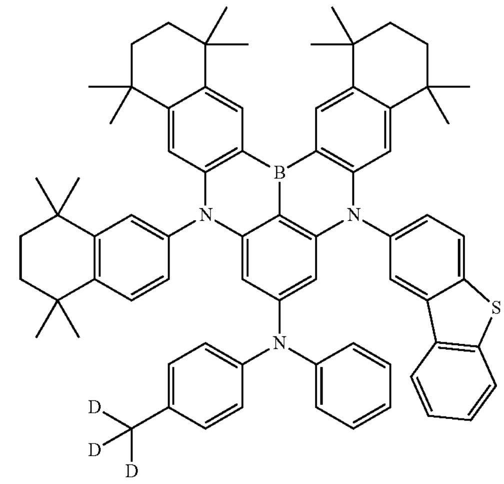
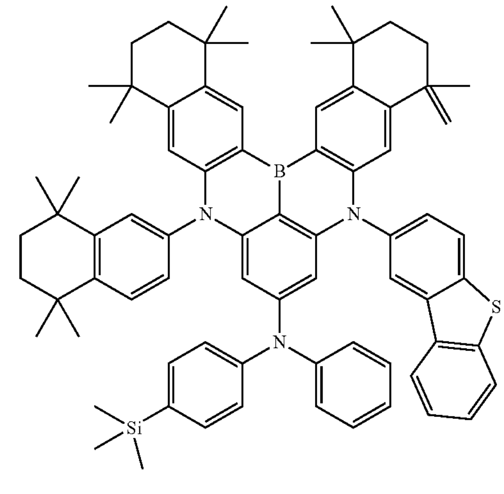
-continued
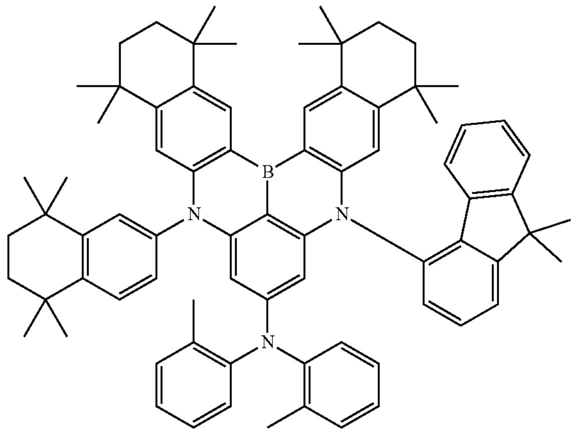
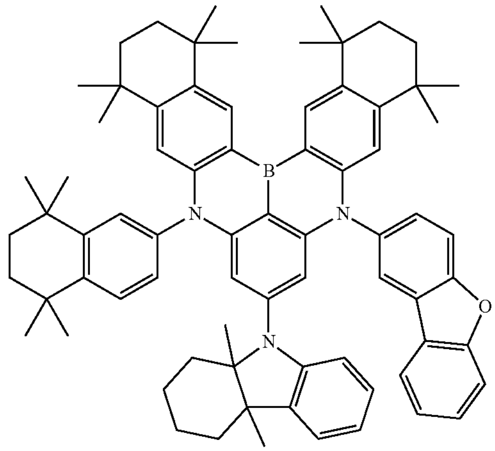
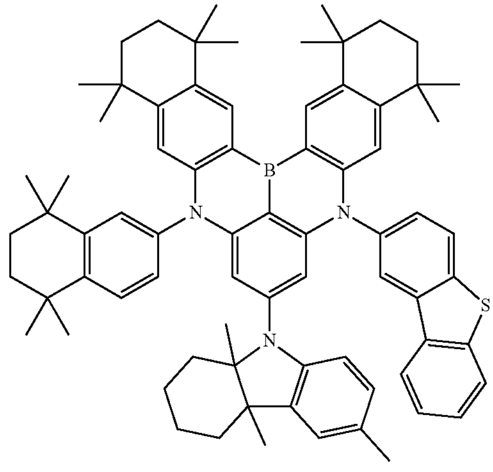

-continued
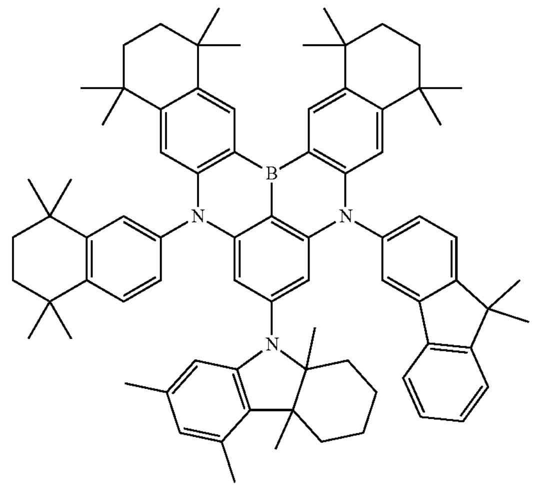
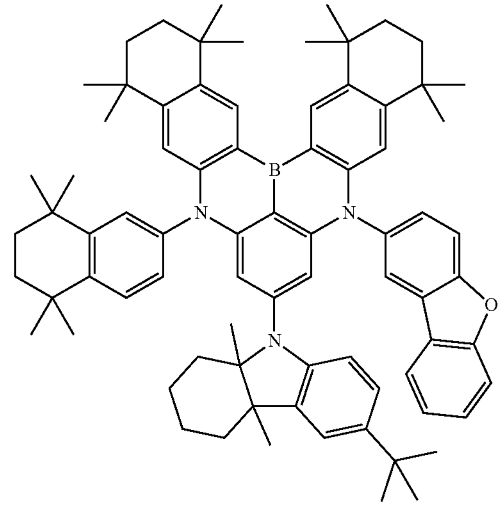
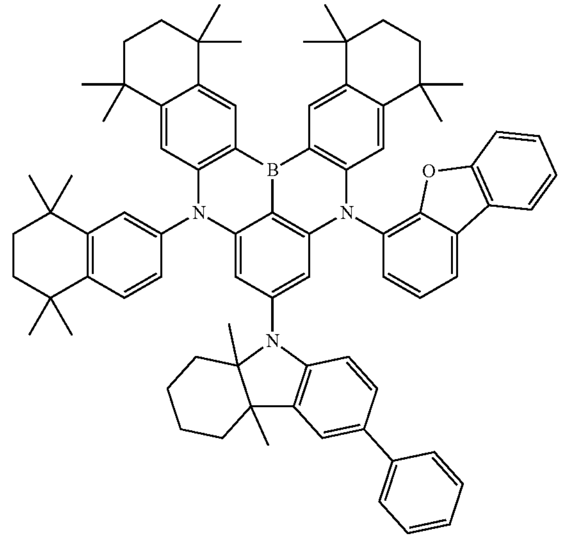
-continued
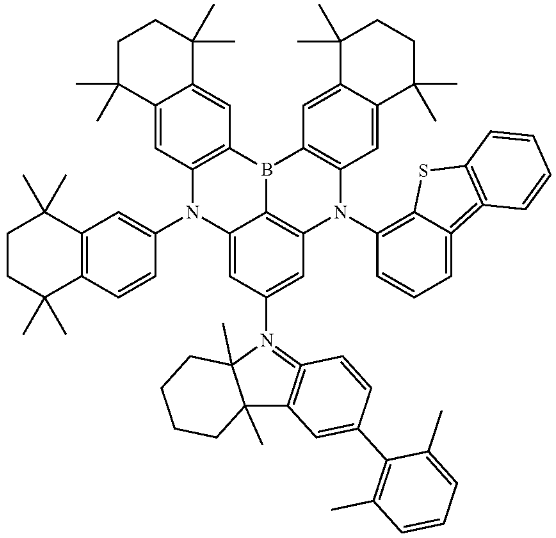
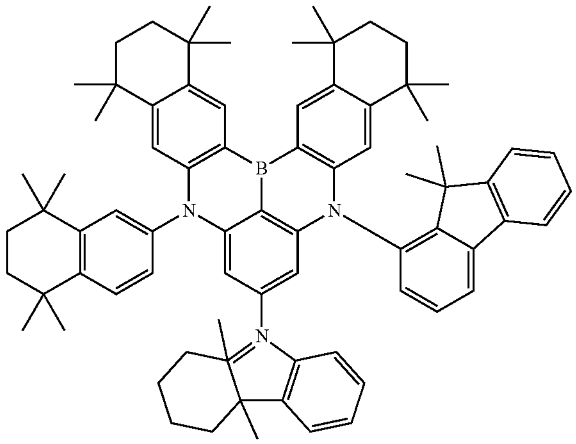
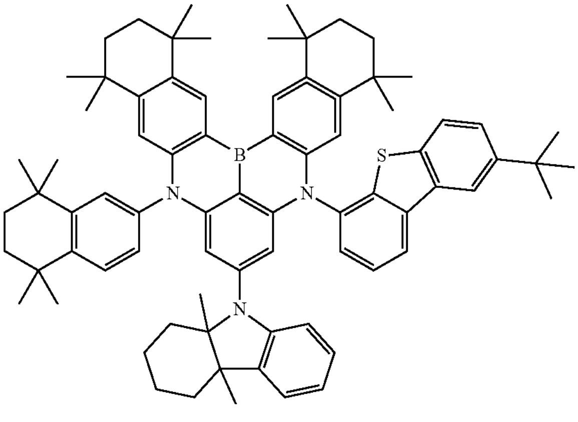

-continued
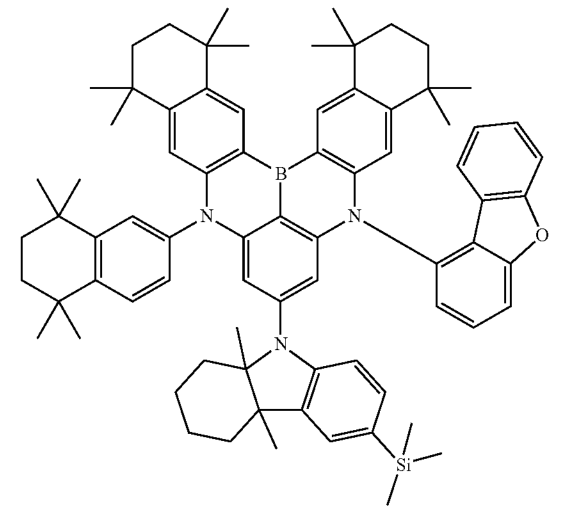
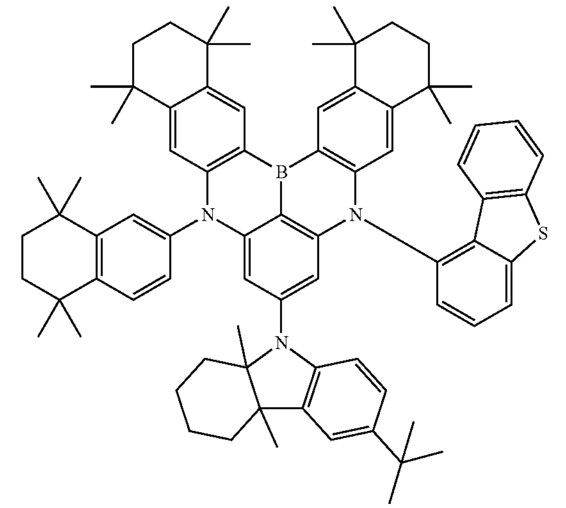
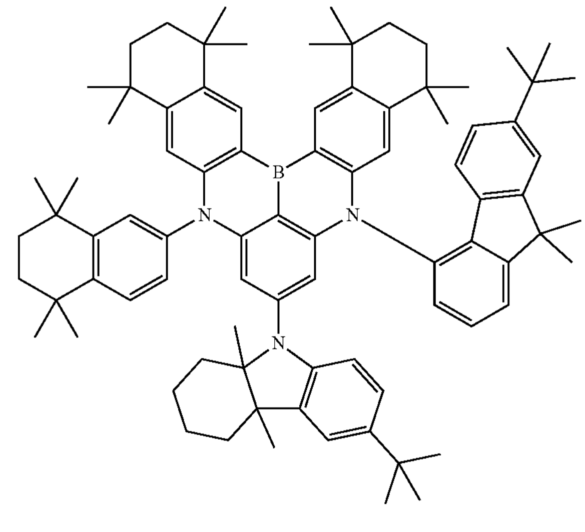
-continued
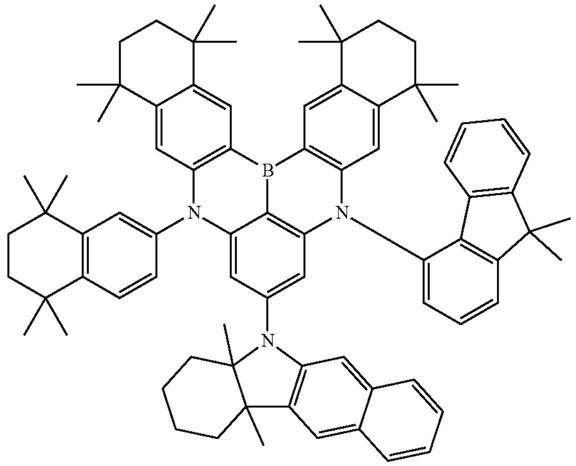
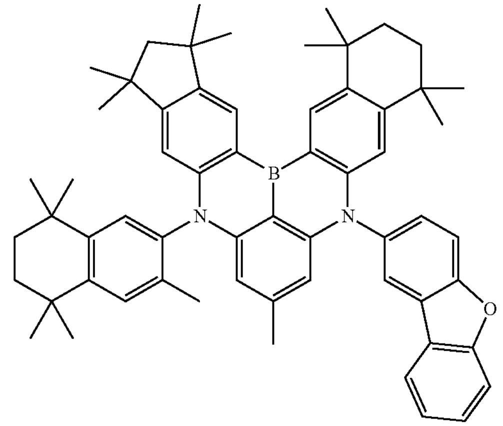
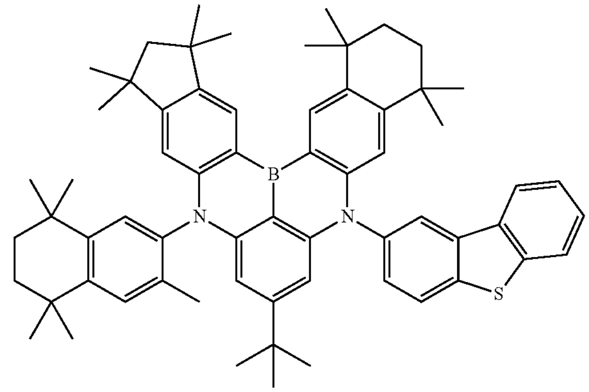
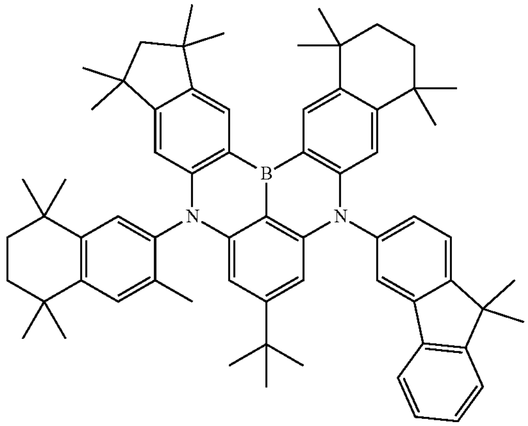

-continued
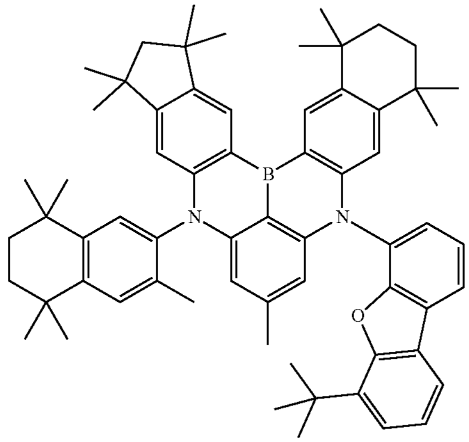
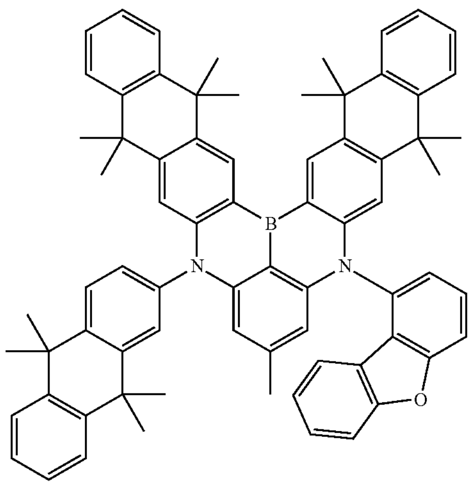
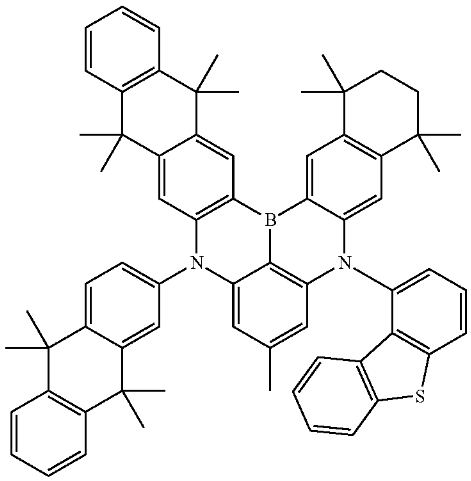
-continued
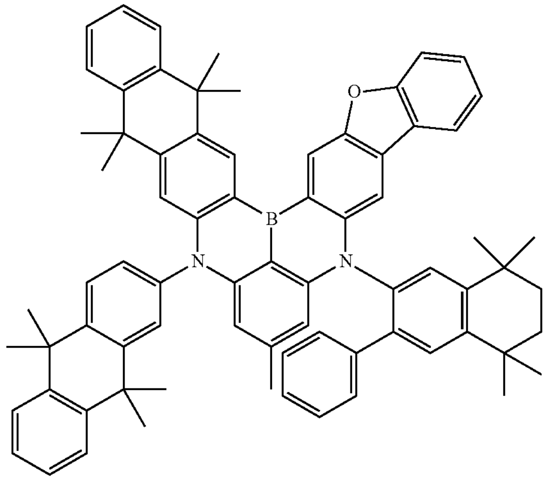
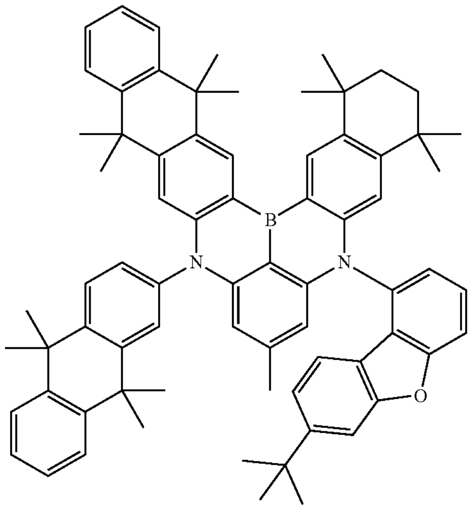
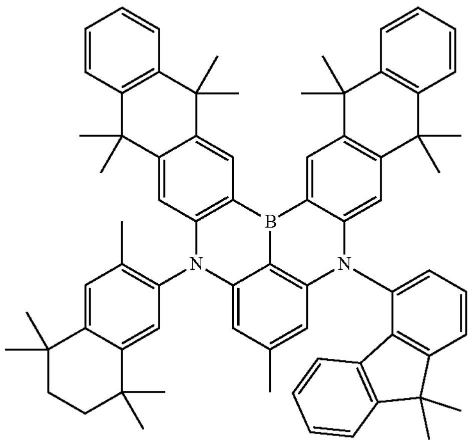

-continued
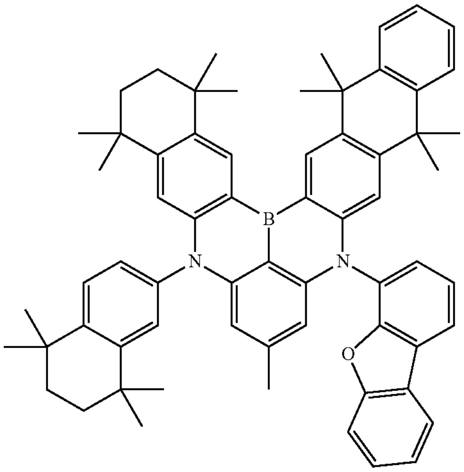
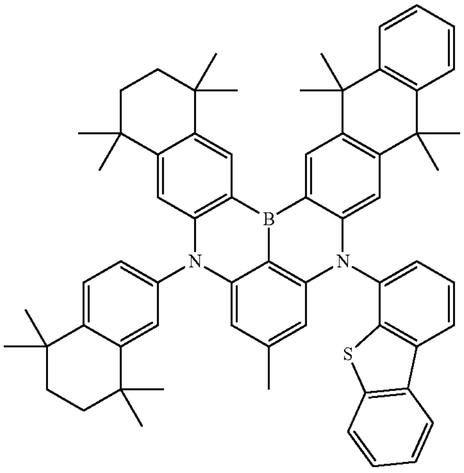
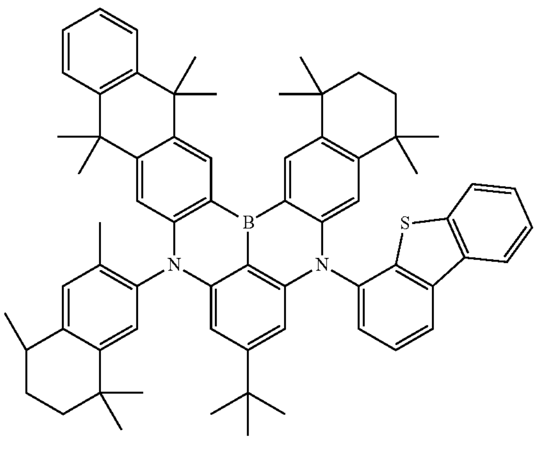
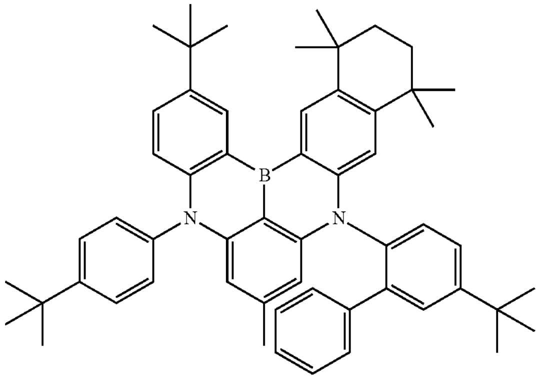
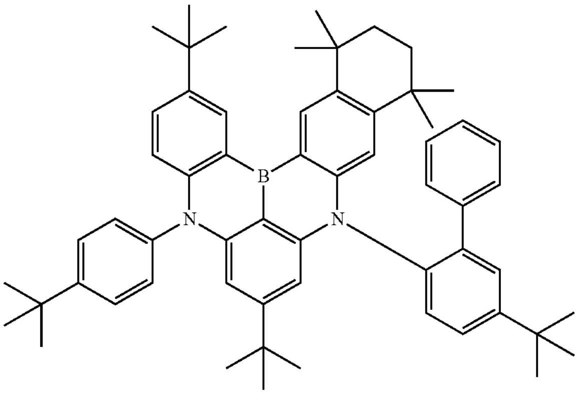
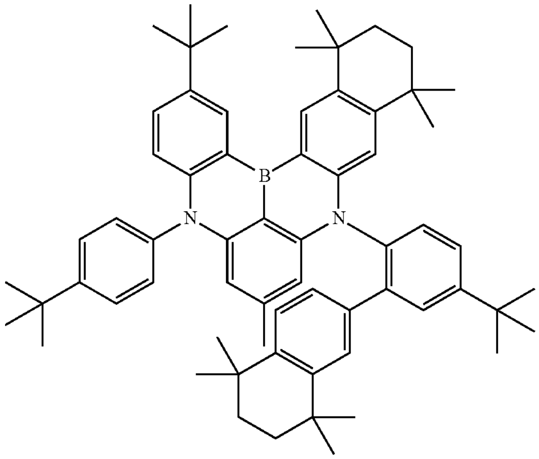
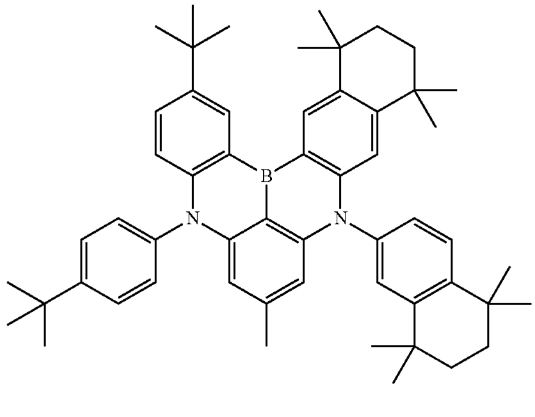

-continued
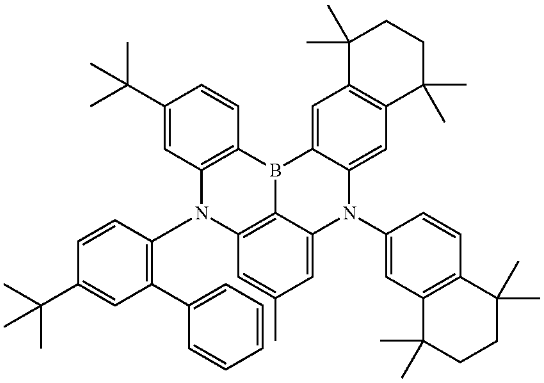
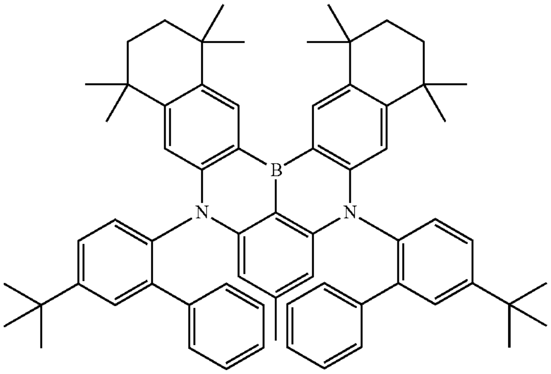
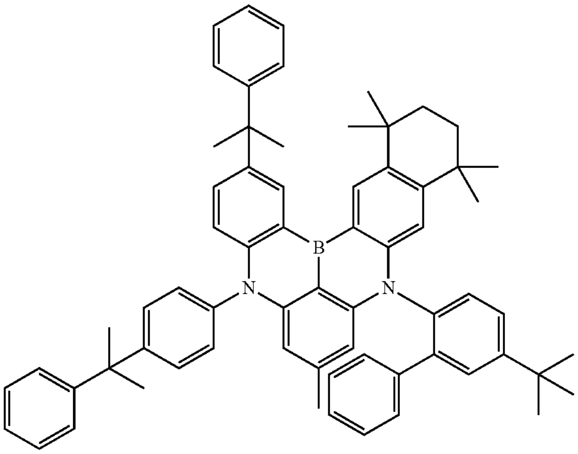
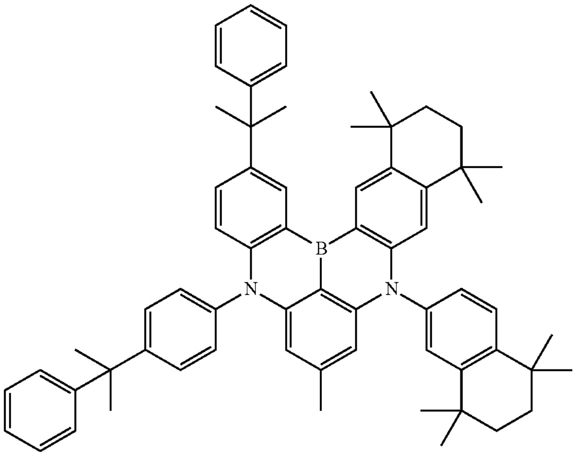
-continued
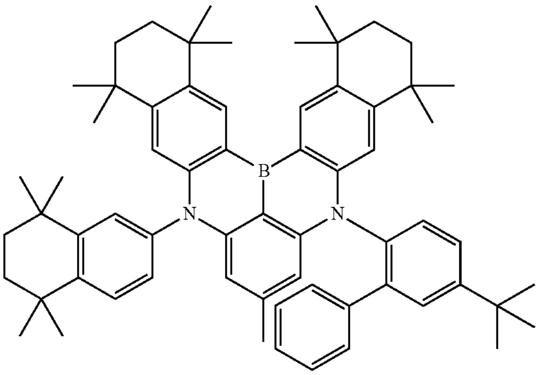
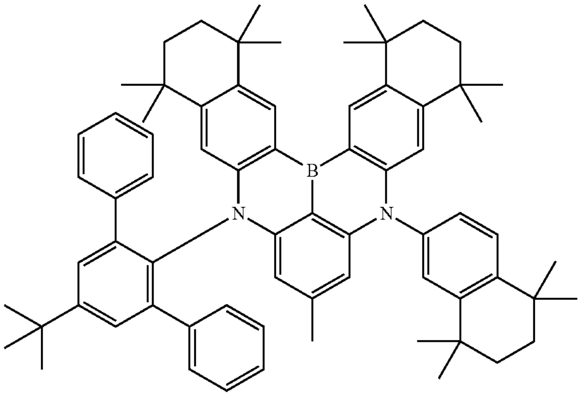
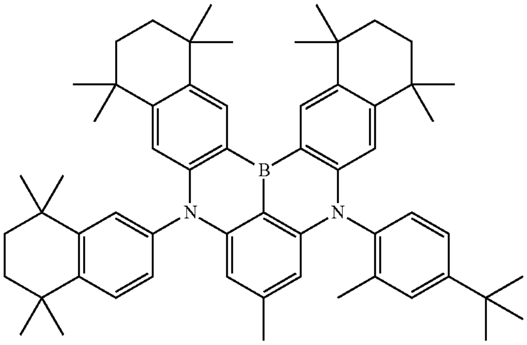
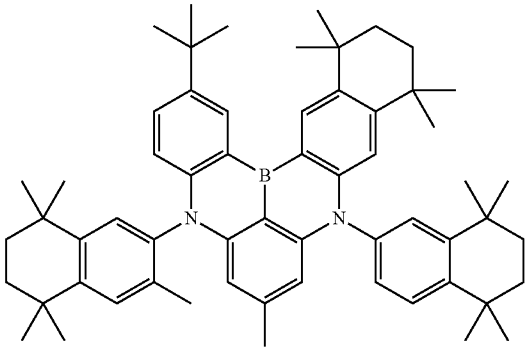

-continued
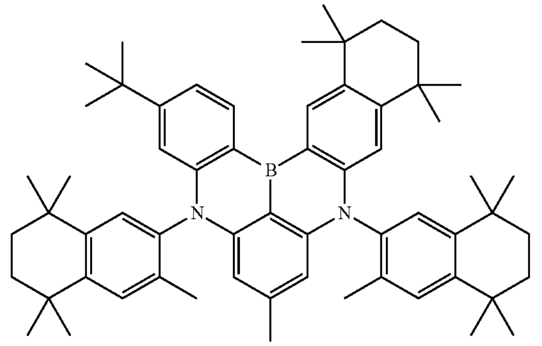
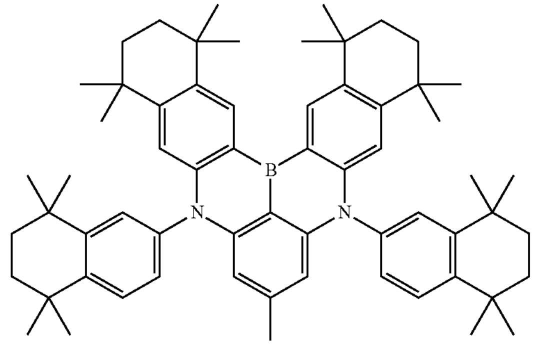
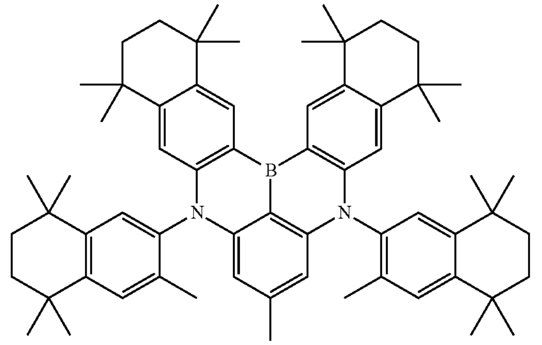
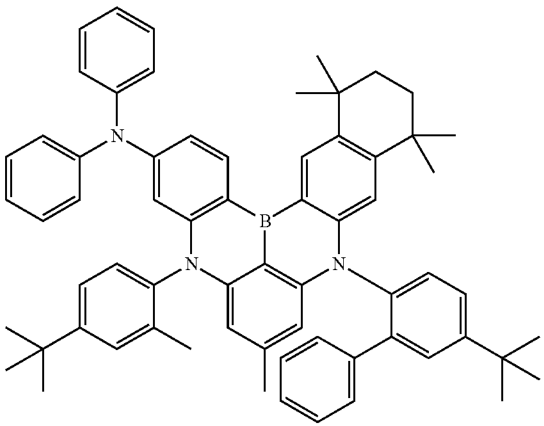
-continued
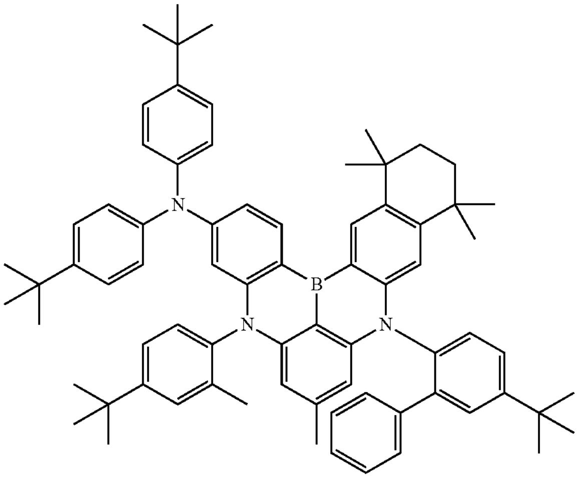
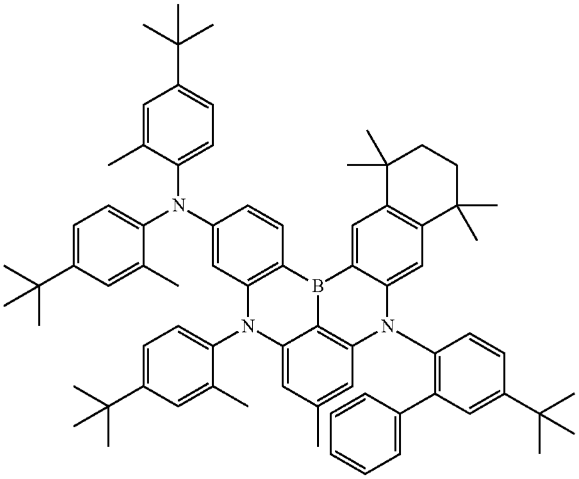
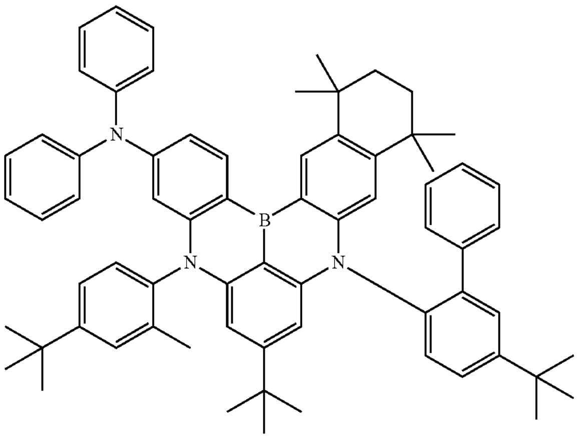

-continued
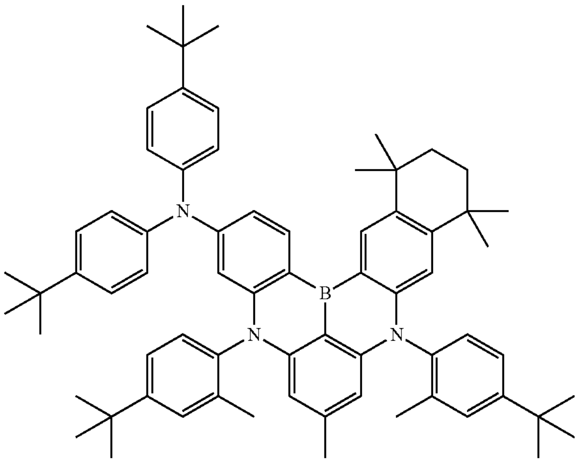
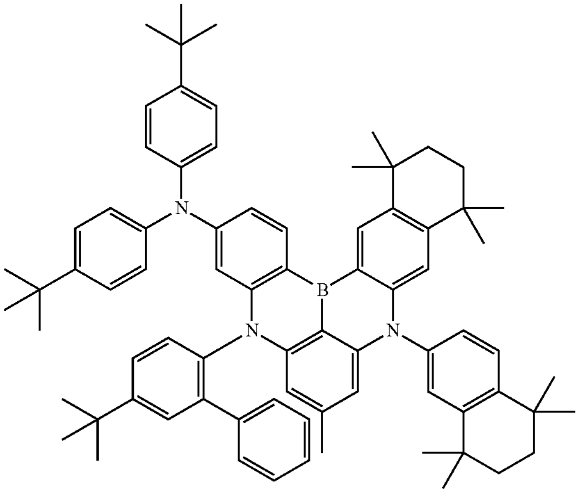
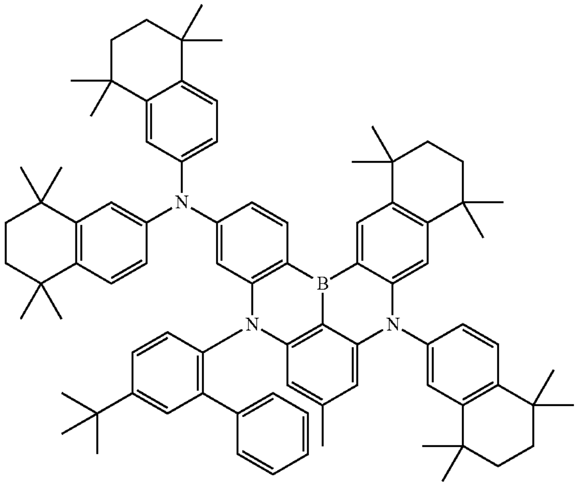
-continued
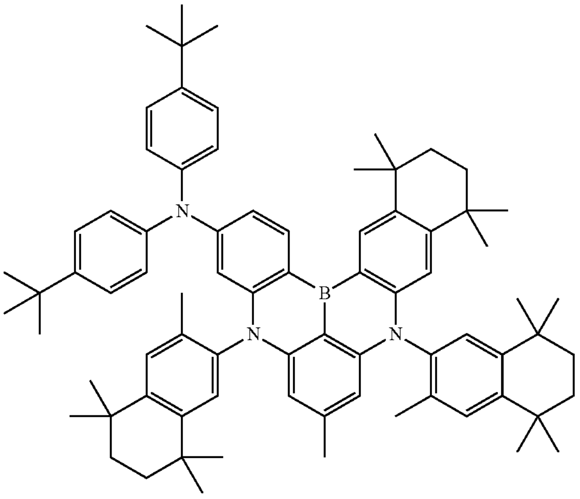
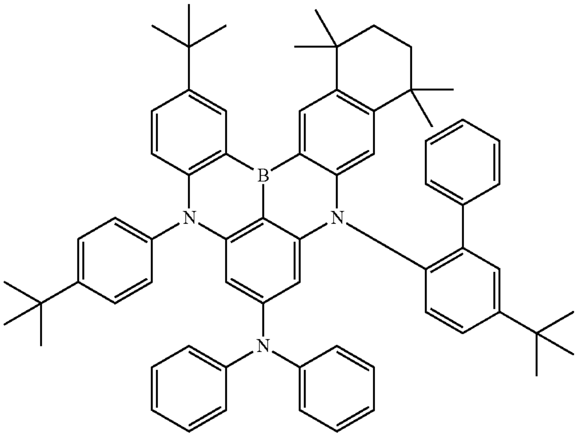
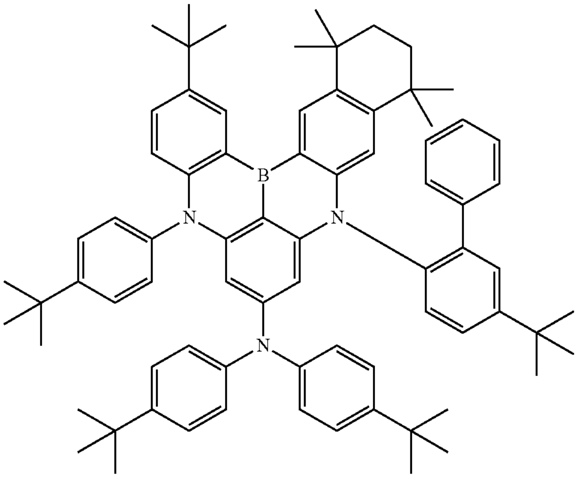

-continued
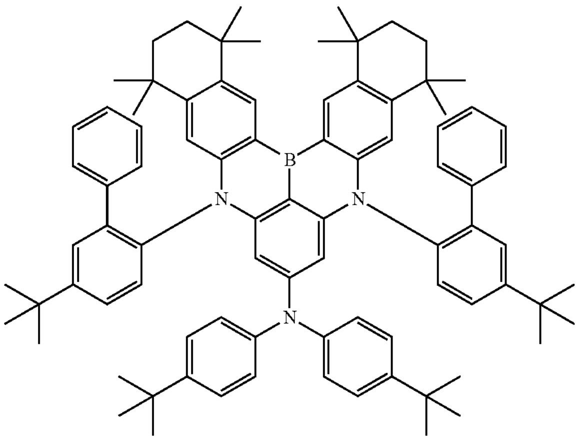
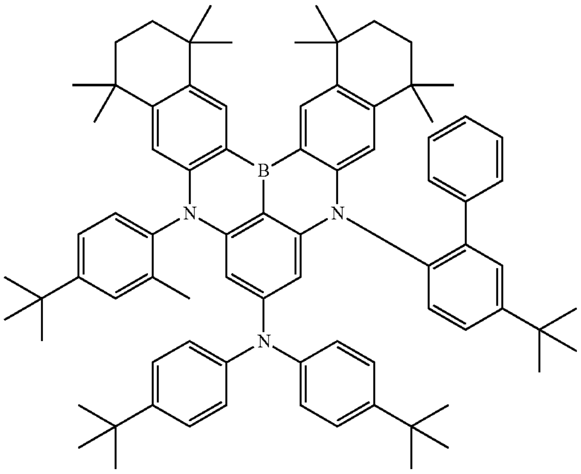
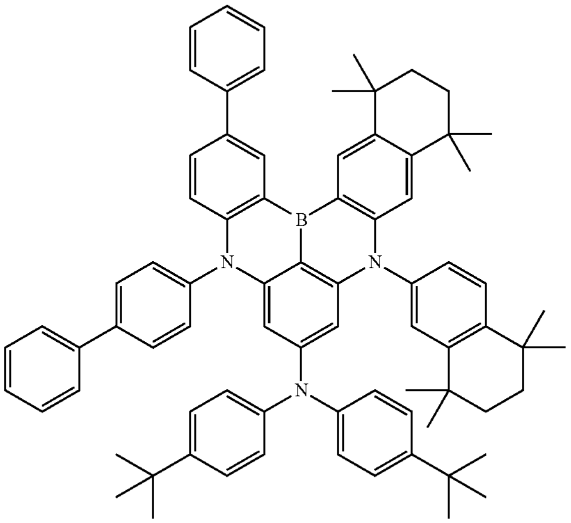
-continued
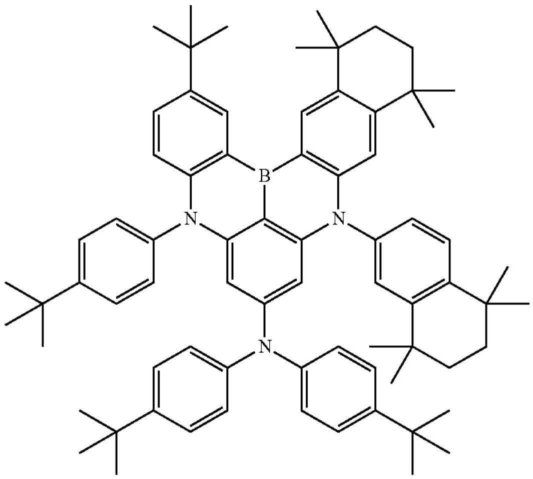
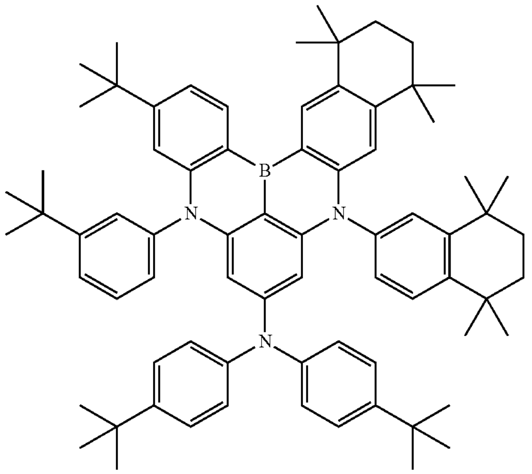
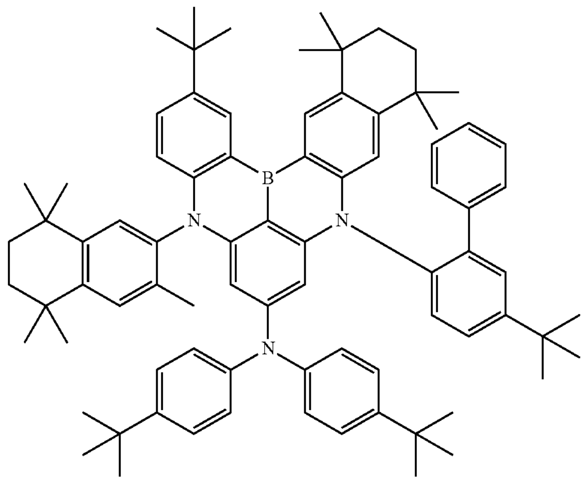

-continued
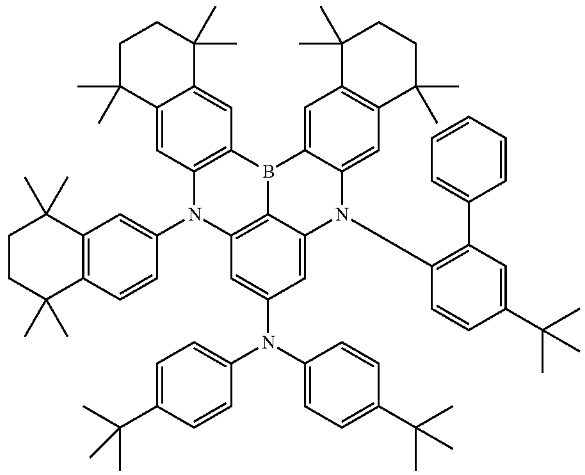
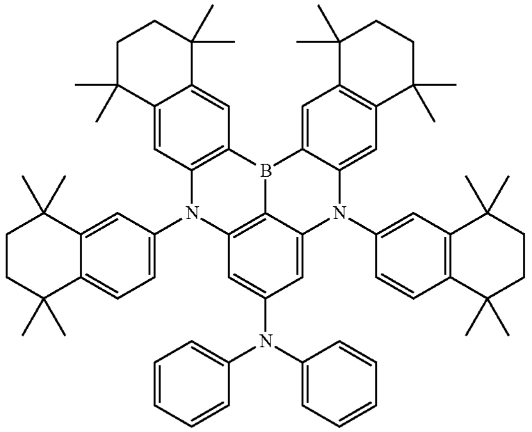
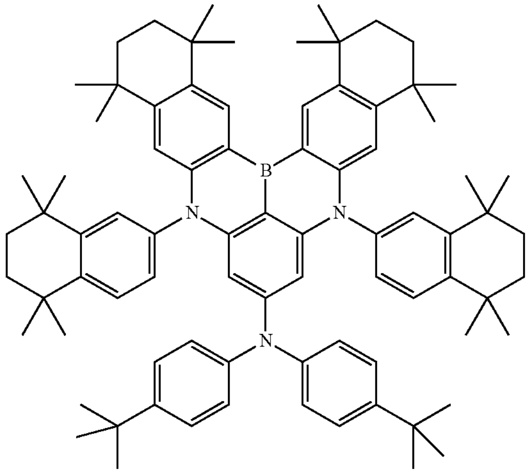
-continued
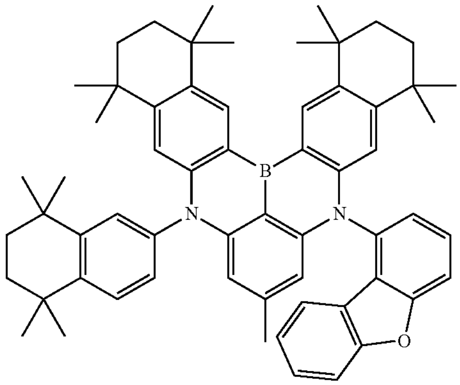
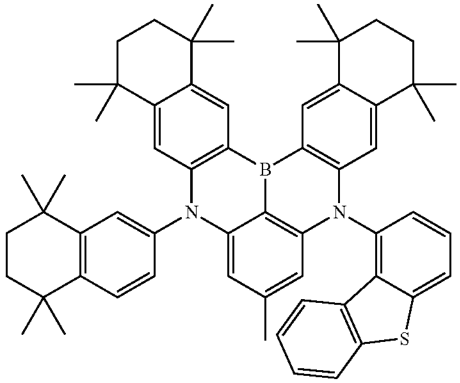
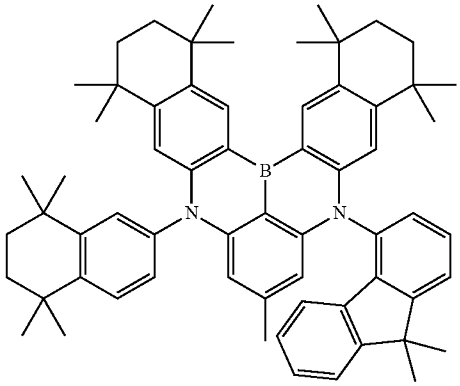
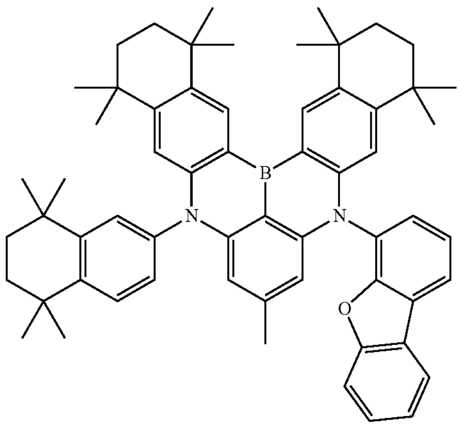

-continued
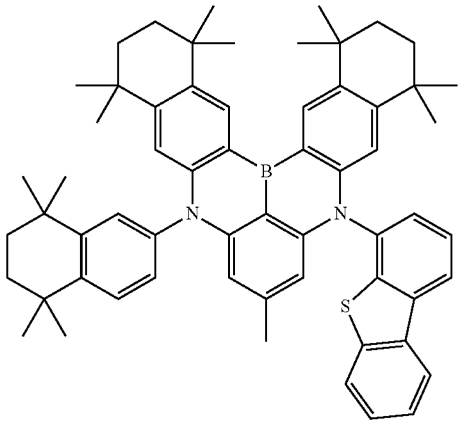
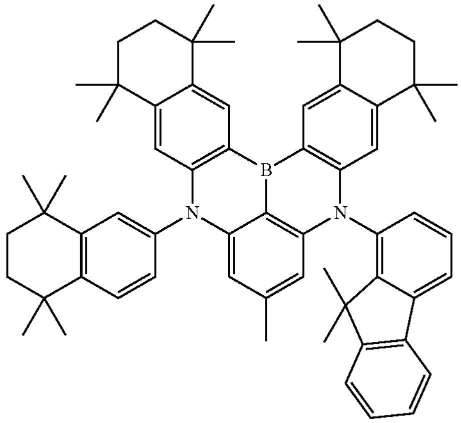
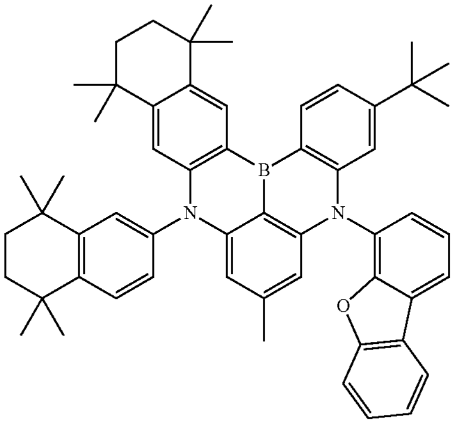
-continued
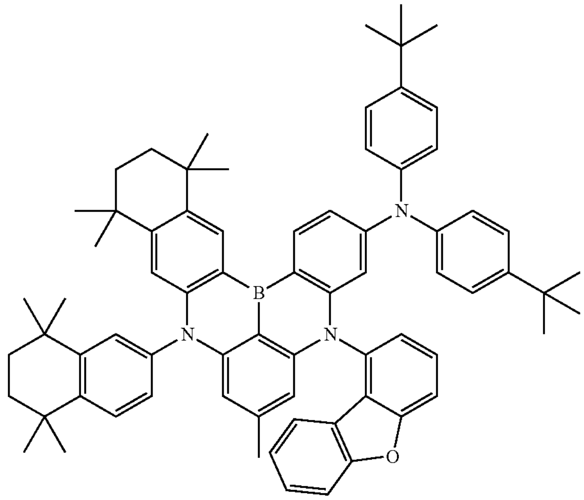
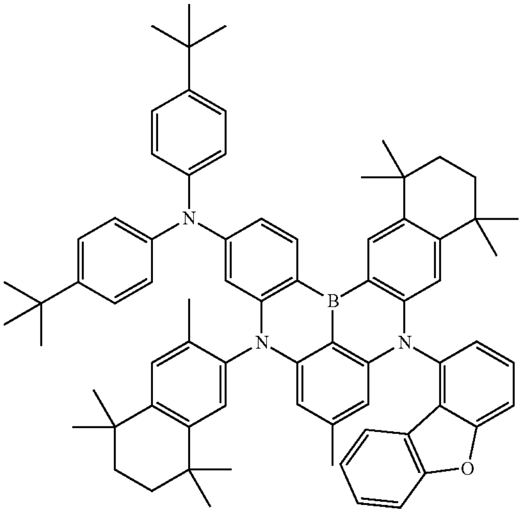
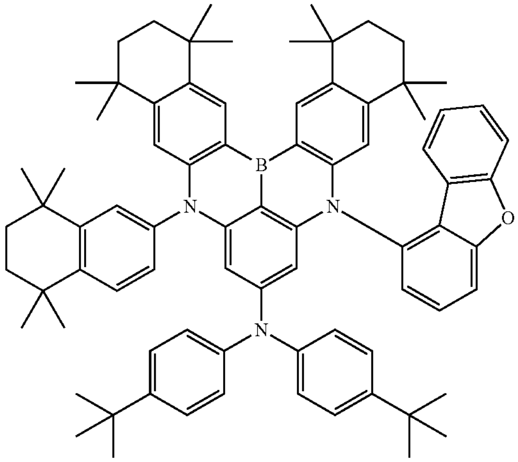

-continued
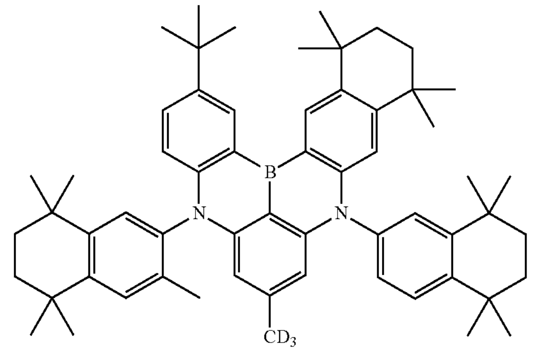
CD3
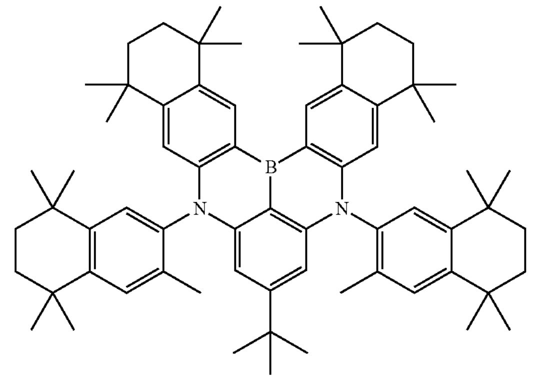
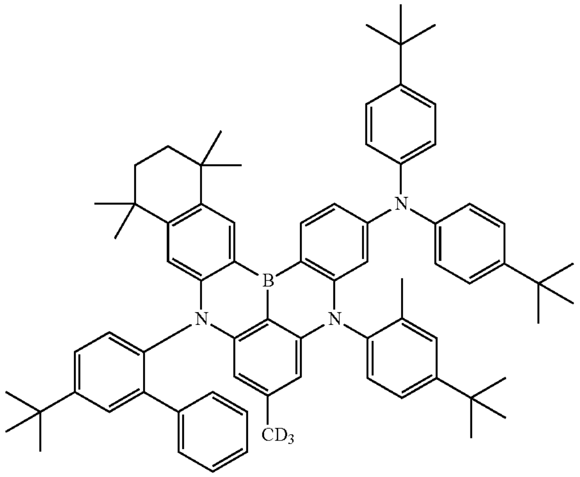
CD3
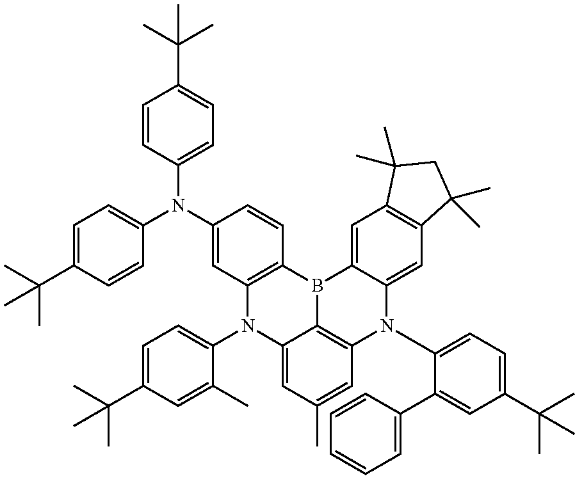
-continued
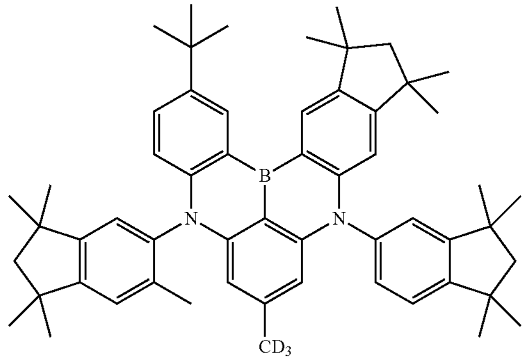
CD3
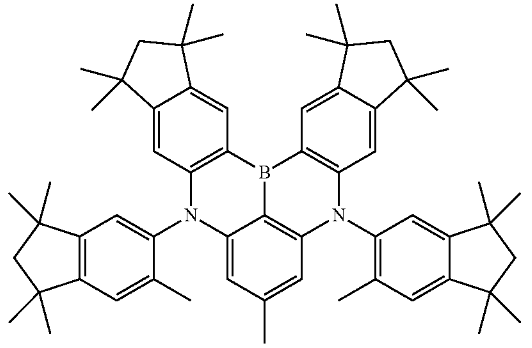
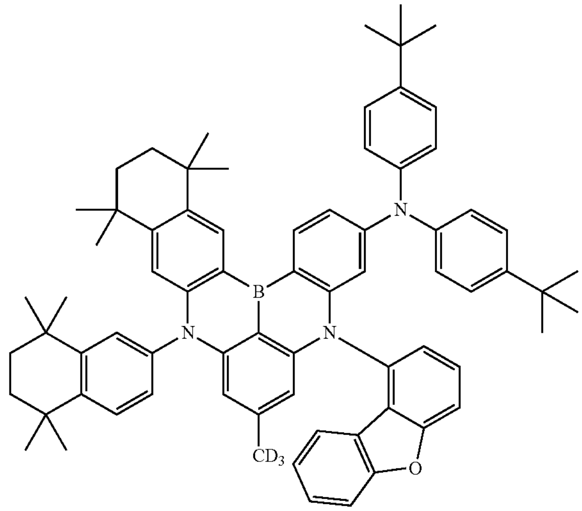
CD3

-continued
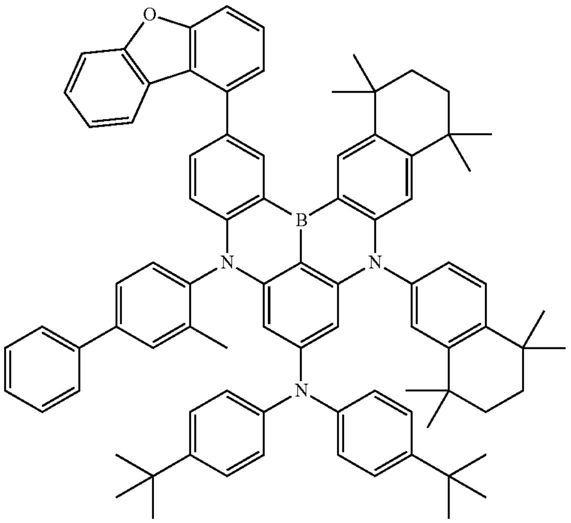
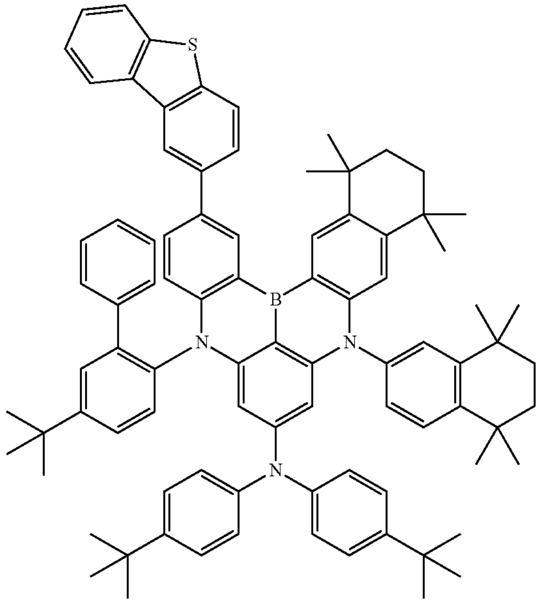
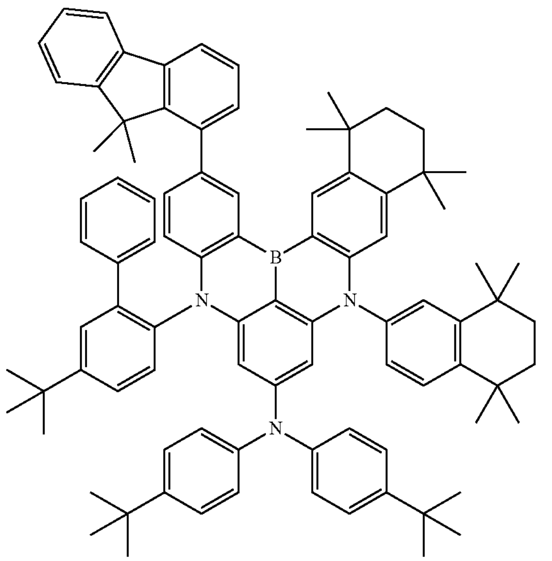
-continued
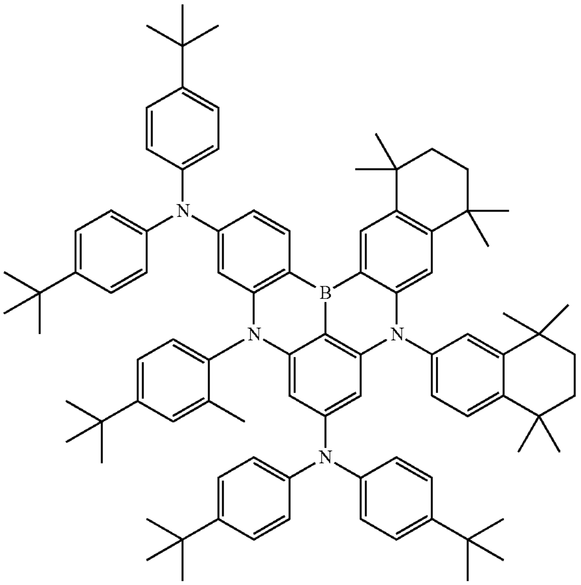
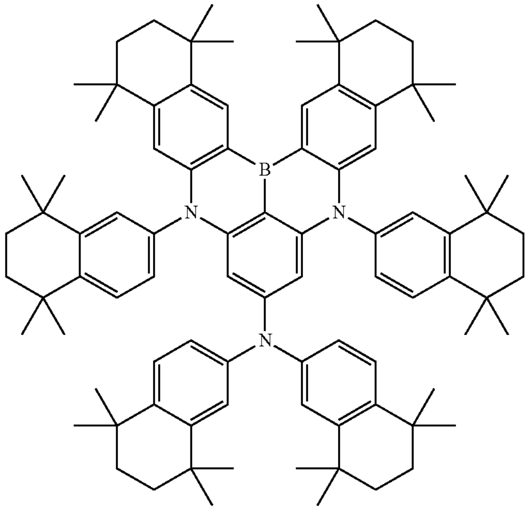
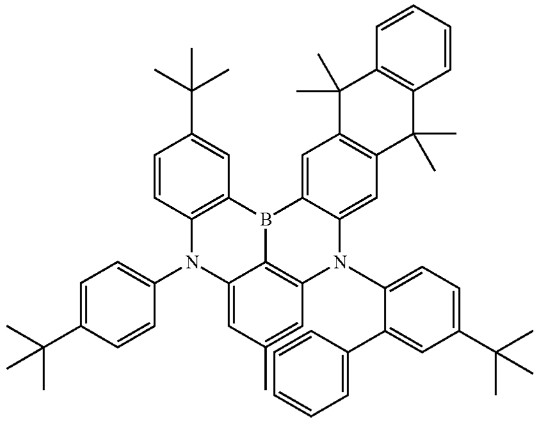

-continued
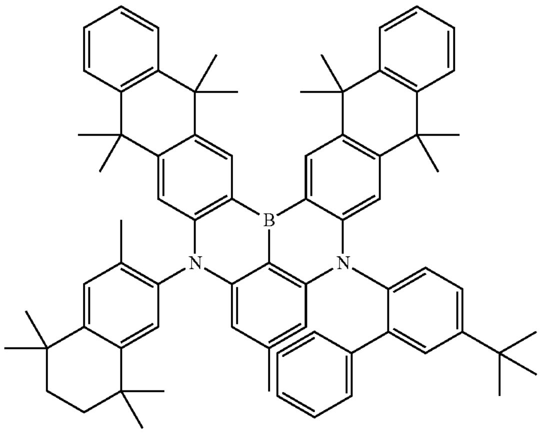
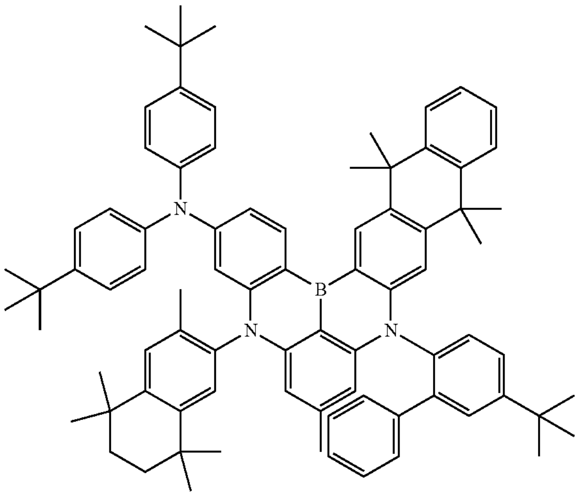
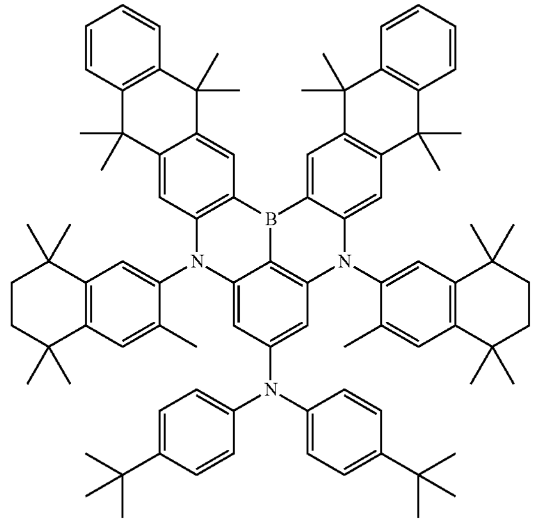
-continued
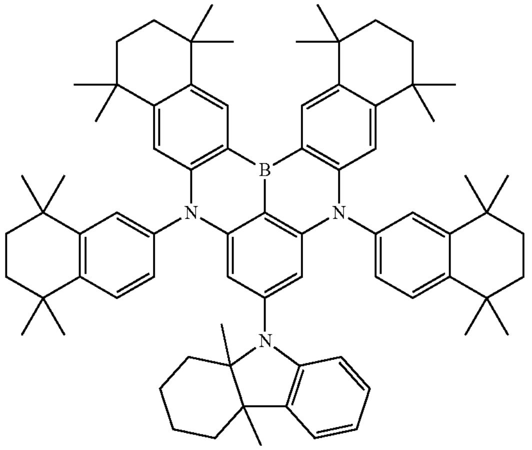
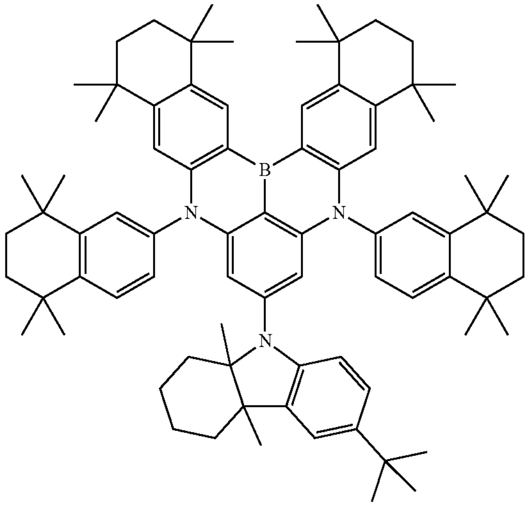
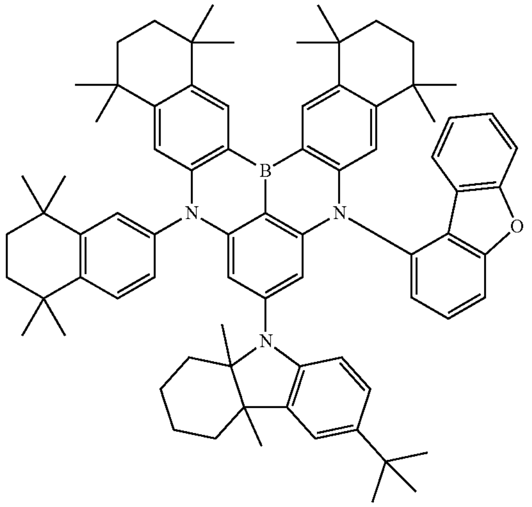

-continued
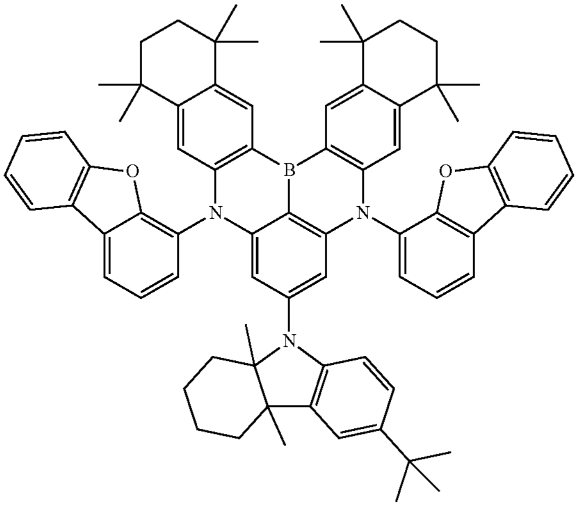
-continued
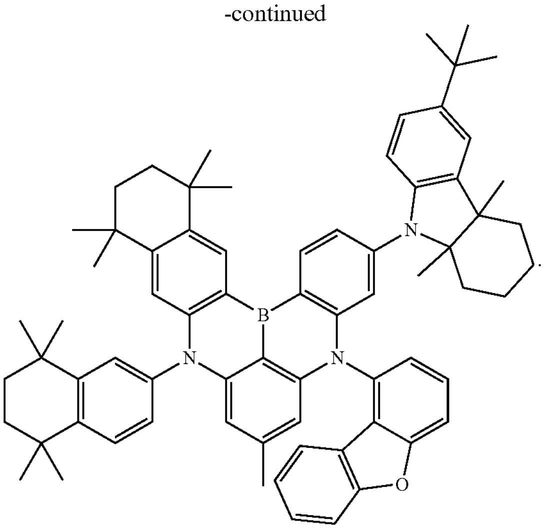
* * * * *